US012624045B2

(12) United States Patent
Korai et al.

(10) Patent No.: US 12,624,045 B2
(45) Date of Patent: May 12, 2026

(54) CONDENSED CYCLIC COMPOUND, ORGANIC LIGHT-EMITTING DEVICE INCLUDING THE SAME, AND ELECTRONIC APPARATUS INCLUDING THE ORGANIC LIGHT-EMITTING DEVICE

(71) Applicant: Samsung Electronics Co., Ltd., Suwon-si (KR)

(72) Inventors: Keisuke Korai, Kanagawa (JP); Norifumi Kishi, Kanagawa (JP); Wataru Sotoyama, Kanagawa (JP); Atsushi Imamura, Kanagawa (JP); Eigo Miyazaki, Kanagawa (JP); Jiwhan Kim, Seoul (KR); Juhyun Kim, Seoul (KR); Tomoya Hirose, Kanagawa (JP)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 991 days.

(21) Appl. No.: 17/558,957

(22) Filed: Dec. 22, 2021

(65) Prior Publication Data

US 2023/0080626 A1 Mar. 16, 2023

(30) Foreign Application Priority Data

Dec. 25, 2020 (JP) ................................ 2020-216557
Jul. 2, 2021 (KR) ........................ 10-2021-0087429

(51) Int. Cl.
*C07D 487/22* (2006.01)
*H10K 50/11* (2023.01)
(Continued)

(52) U.S. Cl.
CPC ......... *C07D 487/22* (2013.01); *H10K 85/636* (2023.02); *H10K 85/6572* (2023.02);
(Continued)

(58) Field of Classification Search
CPC ............. C07D 487/22; H10K 2101/20; H10K 2101/30; H10K 85/6572
See application file for complete search history.

(56) References Cited

U.S. PATENT DOCUMENTS 10,249,832 B1 * 4/2019 Takahashi ............ H10K 85/626
2016/0315259 A1 10/2016 Fennimore et al.
(Continued)

FOREIGN PATENT DOCUMENTS

CN 107501311 A 12/2017
CN 108084195 A 5/2018
(Continued)

OTHER PUBLICATIONS

Machine-generated English-language translation of KR-20210119032-A.*
(Continued)

*Primary Examiner* — Vu A Nguyen
(74) *Attorney, Agent, or Firm* — CANTOR COLBURN LLP

(57) ABSTRACT

Provided are a condensed cyclic compound represented by Formula 1, an organic light-emitting device including the condensed cyclic compound, and an electronic apparatus including the light-emitting device:

Formula 1

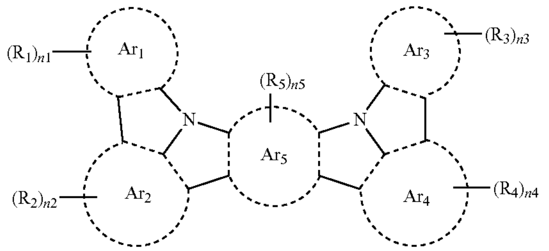

wherein details of Formula 1 are the same as described in the present specification.

18 Claims, 4 Drawing Sheets

(51) Int. Cl.

| | |
|---|---|
| ***H10K 85/60*** | (2023.01) |
| ***H10K 101/10*** | (2023.01) |
| ***H10K 101/30*** | (2023.01) |
| ***H10K 101/40*** | (2023.01) |

(52) U.S. Cl.

CPC .......... *H10K 50/11* (2023.02); *H10K 2101/10* (2023.02); *H10K 2101/30* (2023.02); *H10K 2101/40* (2023.02)

(56) References Cited

U.S. PATENT DOCUMENTS

| | | | |
|---|---|---|---|
| 2020/0212315 | A1 | 7/2020 | Takahashi et al. |
| 2021/0359221 | A1 | 11/2021 | Takahashi et al. |
| 2023/0084208 | A1 | 3/2023 | Kim et al. |
| 2023/0097942 | A1 | 3/2023 | Kim et al. |

FOREIGN PATENT DOCUMENTS

| | | | | |
|---|---|---|---|---|
| CN | 110790782 | A | 2/2020 | |
| JP | 2015153911 | A | 8/2015 | |
| JP | 5978228 | B2 | 7/2016 | |
| JP | 2020053667 | A | 4/2020 | |
| JP | 2020107742 | A | 7/2020 | |
| JP | 2021134172 | A | 9/2021 | |
| KR | 20210119032 | A | * 10/2021 | ............. C09K 11/06 |
| KR | 20220069866 | A | 5/2022 | |
| WO | 2011159872 | A1 | 12/2011 | |
| WO | 2015102118 | A1 | 7/2015 | |
| WO | 2018186404 | A1 | 10/2018 | |
| WO | 2019111971 | A1 | 6/2019 | |
| WO | 2020115933 | A1 | 6/2020 | |
| WO | 2022069453 | A1 | 4/2022 | |

OTHER PUBLICATIONS

Ha Lim Lee, et al., Narrowband and Pure Violet Organic Emitter with a FullWidth at Half Maximum of 14 nm and y Color Coordinate of Below 0.02, Small, Advanced Science News, 2020, 1907569, 5 pp.

Taisei Taniguchi, et al., "Construction of Nitrogen-containing Polycyclic Aromatic Compoundsby Intramolecular Oxidative C—H/C—H Couplingof Bis(9H-carbazol-9-yl)benzenes and Their Properties", Chem. Lett. 2019, 48, 1160-1163 | doi:10.1246/cl.190494.

Takuji Hatakeyama, et al., "Ultrapure Blue Thermally Activated Delayed FluorescenceMolecules: Efficient HOMO-LUMO Separation by theMultiple Resonance Effect", Adv. Mater. 2016, 28, 2777-2781.

Office Action issued Oct. 8, 2024 of JP Patent Application No. 2020-216557.

* cited by examiner

CONDENSED CYCLIC COMPOUND, ORGANIC LIGHT-EMITTING DEVICE INCLUDING THE SAME, AND ELECTRONIC APPARATUS INCLUDING THE ORGANIC LIGHT-EMITTING DEVICE

CROSS-REFERENCE TO RELATED APPLICATIONS

This application claims the benefit of Japanese Patent Application No. 2020-216557, filed on Dec. 25, 2020, in the Japanese Patent Office and Korean Patent Application No. 10-2021-0087429, filed on Jul. 2, 2021, in the Korean Intellectual Property Office, the disclosures of which are incorporated by reference herein in their entirety.

BACKGROUND

1. Field

The present disclosure relates to condensed cyclic compounds, organic light-emitting devices including the condensed cyclic compounds, and electronic apparatuses including the organic light-emitting devices.

2. Description of the Related Art

Organic light-emitting devices are self-emissive devices that have wide viewing angles, high contrast ratios, and short response times, exhibit excellent characteristics in terms of luminance, driving voltage, and response speed, and produce full-color images.

In an example, an organic light-emitting device includes an anode, a cathode, and an organic layer that is arranged between the anode and the cathode and includes an emission layer. A hole transport region may be arranged between the anode and the emission layer, and an electron transport region may be arranged between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transition from an excited state to a ground state, thereby generating light.

SUMMARY

Provided are condensed cyclic compounds having excellent luminescence efficiency and high color purity and organic light-emitting devices including the condensed cyclic compounds.

Additional aspects will be set forth in part in the description, which follows and, in part, will be apparent from the description, or may be learned by practice of the presented embodiments of the disclosure.

According to an aspect of an embodiment, provided is a condensed cyclic compound represented by Formula 1:

Formula 1

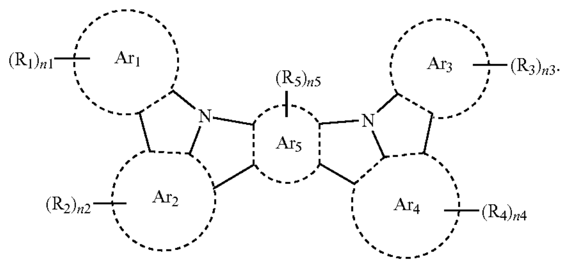

In Formula 1, $Ar_1$ to $Ar_5$ are each independently a $C_6$-$C_{60}$ carbocyclic group or a $C_1$-$C_{60}$ heterocyclic group, $R_1$ to $R_5$ are each independently hydrogen, deuterium, —F, —Cl, —Br, —I, a hydroxyl group, a cyano group, a nitro group, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$), wherein $R_1$(s) in the number of n1, $R_2$(s) in the number of n2, $R_3$(s) in the number of n3, $R_4$(s) in the number of n4, and $R_5$(s) in the number of n5 are identical to or different from each other, n1 to n5 are each independently an integer from 0 to 8, the sum of n1 to n5 is 1 or more, two of two or more $R_1$(s) when n1 is 2 or more; two of two or more $R_2$(s) when n2 is 2 or more; two of two or more $R_3$(s) when n3 is 2 or more; two of two or more $R_4$(s) when n4 is 2 or more; and two of two or more $R_5$(s) when n5 is 2 or more are respectively optionally linked to each other or linked together via a single bond to form a $C_8$-$C_{60}$ polycyclic group unsubstituted or substituted with at least one $R_{10a}$, $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, or a phenyl group, a biphenyl group, or any combination thereof.

According to an aspect of another embodiment, provided is an organic light-emitting device including: a first electrode; a second electrode; and an interlayer arranged between the first electrode and the second electrode and including an emission layer, wherein the interlayer includes at least one condensed cyclic compound.

According to an aspect of another embodiment, provided is an electronic apparatus including the organic light-emitting device.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
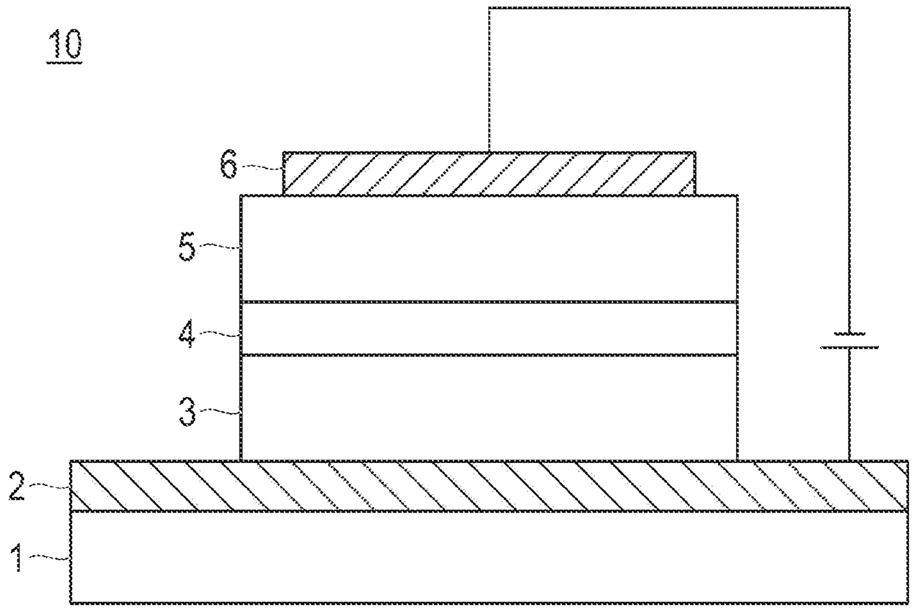
FIGS. 1 to 3 are each a schematic cross-sectional view of an organic light-emitting device according to an exemplary embodiment.

Reference will now be made in detail to embodiments, examples of which are illustrated in the accompanying drawings, wherein like reference numerals refer to like elements throughout the specification. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms These terms are only used to distinguish one element, component, region, layer or section from another element, component, region, layer or section Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or a group thereof.

Furthermore, relative terms, such as "lower" or "bottom" and "upper" or "top," may be used herein to describe one element's relationship to another element as illustrated in the Figures It will be understood that relative terms are intended to encompass different orientations of the device in addition to the orientation depicted in the Figures For example, if the device in one of the figures is turned over, elements described as being on the "lower" side of other elements would then be oriented on "upper" sides of the other elements The exemplary term "lower," can therefore, encompasses both an orientation of "lower" and "upper," depending on the particular orientation of the figure Similarly, if the device in one of the figures is turned over, elements described as "below" or "beneath" other elements would then be oriented "above" the other elements The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features Moreover, sharp angles that are illustrated may be rounded Thus, the regions illustrated in the figures are schematic in nature and their shapes are not intended to illustrate the precise shape of a region and are not intended to limit the scope of the present claims.

An aspect of the present disclosure provides a condensed cyclic compound represented by Formula 1:

Formula 1

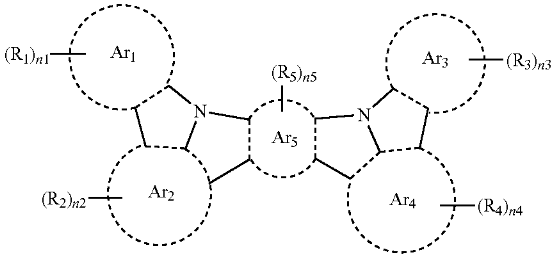

wherein, in Formula 1, $Ar_1$ to $Ar_5$ may each independendly be a $C_6$-$C_{60}$ carbocyclic group or a $C_1$-$C_{60}$ heterocyclic group.

In an embodiment, $Ar_1$ to $Ar_5$ may each independently be a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group.

In one or more embodiments, $Ar_5$ in Formula 1 may be a benzene group, a naphthalene group, an anthracene group, or any combination thereof.

In one or more embodiments, a moiety represented by

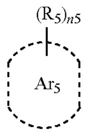

in Formula 1 may be a group represented by one of Formulae 1-1 to 1-4:

Formula 1-1

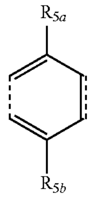

Formula 1-2

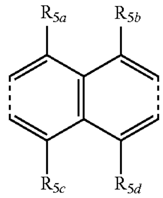

Formula 1-3

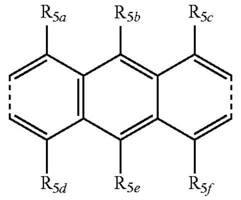

Formula 1-4

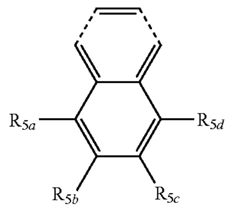

wherein, in Formulae 1-1 to 1-4, a portion indicated with a dotted line refers to bonding to a neighboring part of Formula 1, and $R_{5a}$ to $R_{5f}$ may respectively be the same as described in connection with $R_1$ to $R_5$.

In one or more embodiments, $Ar_1$ to $Ar_5$ may be a benzene group, a naphthalene group, an anthracene group, or any combination thereof.

In one or more embodiments, $Ar_1$ to $Ar_5$ may each independently be a benzene group.

In an embodiment, a group represented by

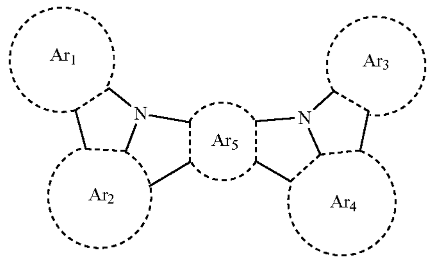

in Formula 1 may be represented by one of Formulae 1-2-1 to 1-2-19:
(1-2-1)
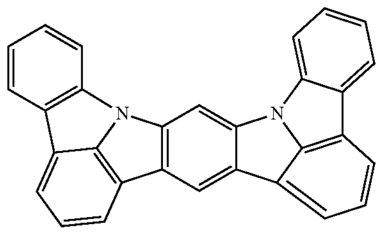
(1-2-2)
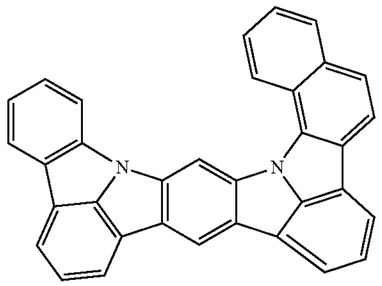
(1-2-3)
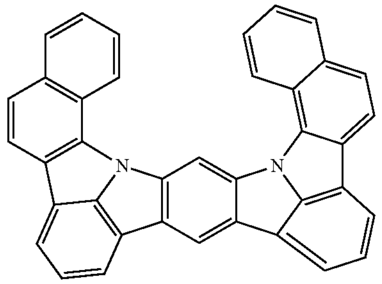
(1-2-4)
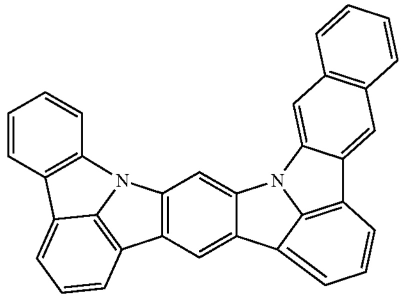
(1-2-5)
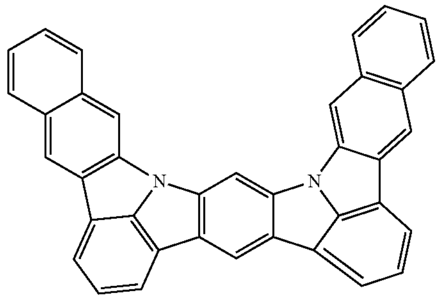
-continued
(1-2-6)
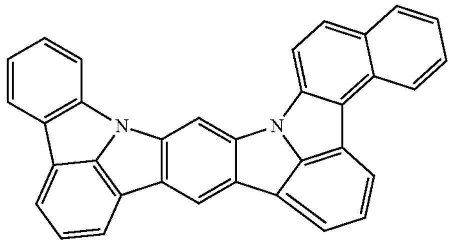
(1-2-7)
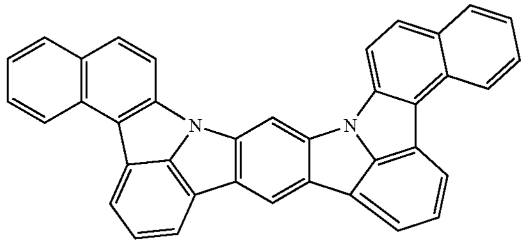
(1-2-8)
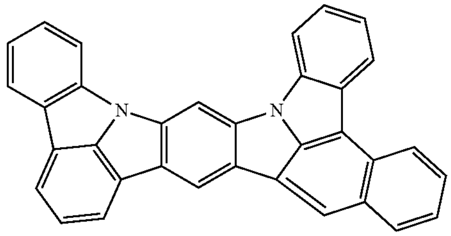
(1-2-9)
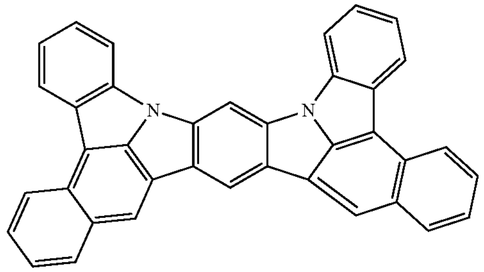
(1-2-10)
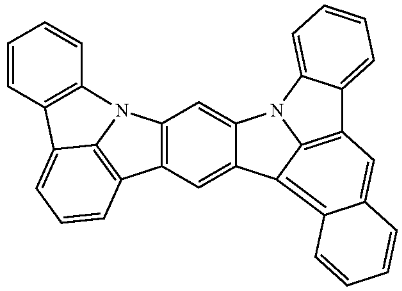

-continued
(1-2-11)
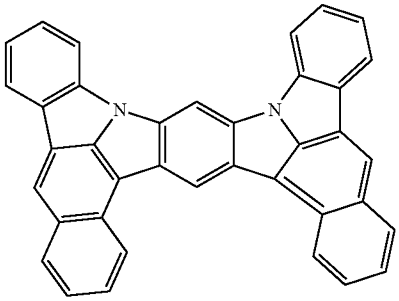
(1-2-12)
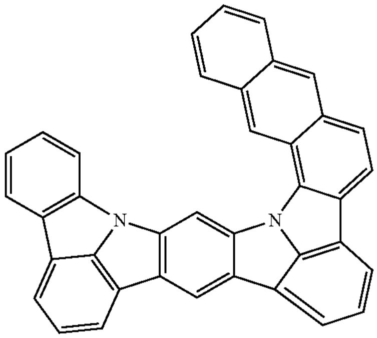
(1-2-13)
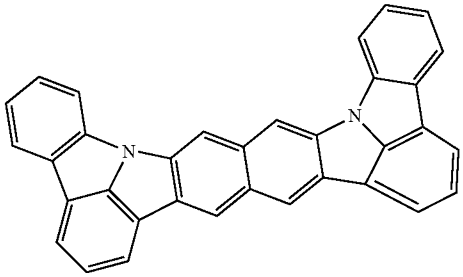
(1-2-14)
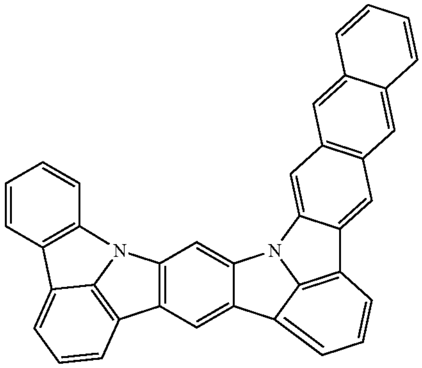
(1-2-15)
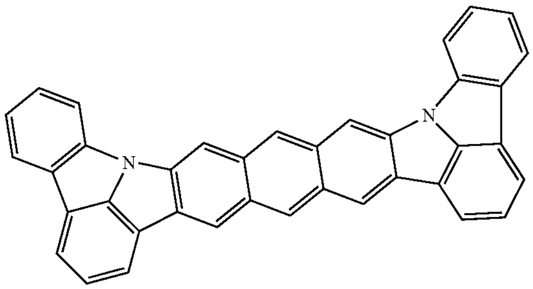
-continued
(1-2-16)
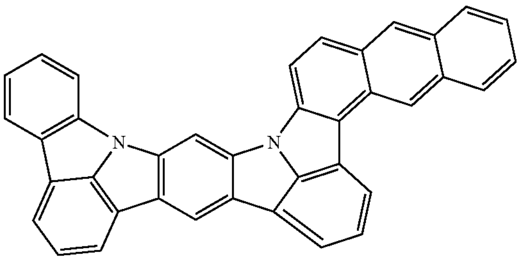
(1-2-17)
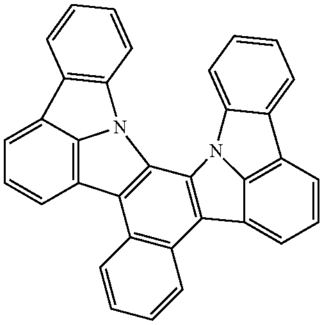
(1-2-18)
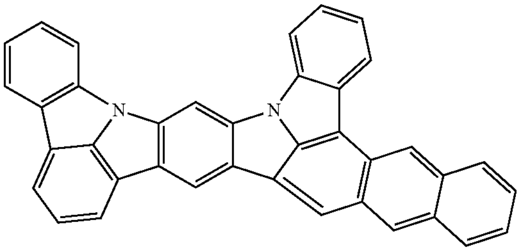
(1-2-19)
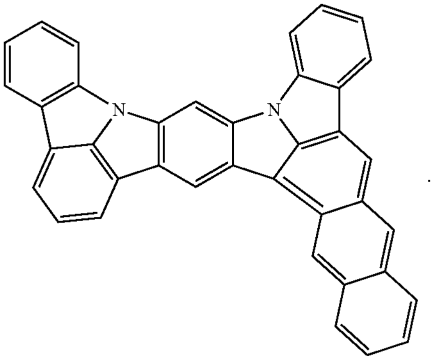
In one or more embodiments, the group represented by
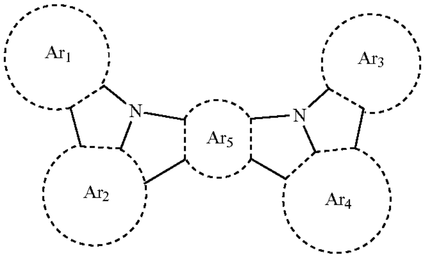

in Formula 1 may be represented by one of Formulae 1-2-1 to 1-2-12, 1-2-14, 1-2-16, 1-2-18, and 1-2-19.

In Formula 1, $R_1$ to $R_5$ may each independently be hydrogen, deuterium, —F, —Cl, —Br, —I, a hydroxyl group, a cyano group, a nitro group, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$), wherein $R_1$(s) in the number of n1, $R_2$(s) in the number of n2, $R_3$(s) in the number of n3, $R_4$(s) in the number of n4, and $R_5$(s) in the number of n5 may be identical to or different from each other. $R_{10a}$ may be the same as described herein.

$Q_1$ to $Q_3$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

In an embodiment, $R_1$ to $R_5$ may each independently be hydrogen, deuterium, —F, —Cl, —Br, —I, a hydroxyl group, a cyano group, a nitro group, a $C_3$-$C_{30}$ carbocyclic group unsubstituted or substituted with at least one $R_{10a}$, a $C_1$-$C_{30}$ heterocyclic group unsubstituted or substituted with at least one $R_{10a}$, a $C_6$-$C_{30}$ aryloxy group unsubstituted or substituted with at least one $R_{10a}$, a $C_6$-$C_{30}$ arylthio group unsubstituted or substituted with at least one $R_{10a}$, or —N($Q_1$)($Q_2$), and $Q_1$ and $Q_2$ may each independently be: hydrogen; deuterium; —F; —Cl; —Br; —I; a hydroxyl group; a cyano group; a nitro group; a $C_1$-$C_{20}$ alkyl group; a $C_2$-$C_{20}$ alkenyl group; a $C_2$-$C_{20}$ alkynyl group; a $C_1$-$C_{20}$ alkoxy group; or a $C_3$-$C_{30}$ carbocyclic group or a $C_1$-$C_{30}$ heterocyclic group, each unsubstituted or substituted with deuterium, —F, a cyano group, a $C_1$-$C_{20}$ alkyl group, a $C_1$-$C_{20}$ alkoxy group, a phenyl group, a biphenyl group, or any combination thereof. $R_{10a}$ may be the same as described herein.

In an embodiment, at least one of $R_1$ to $R_4$ may be —N($Q_1$)($Q_2$), and $Q_1$ and $Q_2$ may each independently be a benzene group or a naphthalene group, each unsubstituted or substituted with deuterium, —F, a cyano group, a $C_1$-$C_{20}$ alkyl group, a $C_1$-$C_{20}$ alkoxy group, a phenyl group, a biphenyl group, or any combination thereof.

In Formula 1, n1 to n5 may each independently be an integer from 0 to 8.

In an embodiment, n1 and n3 may each independently be an integer from 0 to 4.

In an embodiment, n2 and n4 may each independently be an integer from 0 to 3.

In an embodiment, n5 may be an integer from 0 to 2.

In Formula 1, the sum of n1 to n5 may be 1 or more.

In an embodiment, the sum of n1 to n4 may be 1 or more.

In an embodiment, n1 to n4 may each independently be 0 or 1, and n5 may be 0.

In Formula 1, two of two or more $R_1$(s) when n1 is 2 or more; two of two or more $R_2$(s) when n2 is 2 or more; two of two or more $R_3$(s) when n3 is 2 or more; two of two or more $R_4$(s) when n4 is 2 or more; and two of two or more $R_5$(s) when n5 is 2 or more may respectively be optionally linked to each other or linked together via a single bond to form a $C_8$-$C_{60}$ polycyclic group unsubstituted or substituted with at least one $R_{10a}$.

In an embodiment, the condensed cyclic compound represented by Formula 1 may be represented by Formula 2:

Formula 2

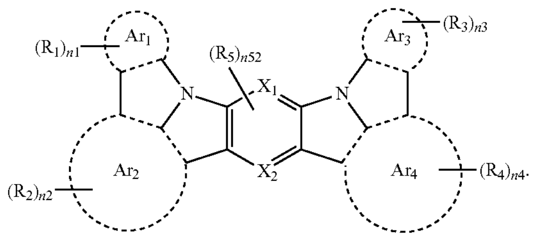

In Formula 2, $Ar_1$ to $Ar_4$, $R_1$ to $R_5$, and n1 to n4 may respectively be the same as described herein, $X_1$ and $X_2$ may each independently be C or N, n52 may be an integer from 0 to 2, the sum of n1 to n4 and n52 may be 1 or more, and two of two or more $R_1$(s) when n1 is 2 or more; two of two or more $R_2$(s) when n2 is 2 or more; two of two or more $R_3$(s) when n3 is 2 or more; two of two or more $R_4$(s) when n4 is 2 or more; and two $R_5$(s) when n52 is 2 may respectively be optionally linked to each other or linked together via a single bond to form a $C_8$-$C_{60}$ polycyclic group unsubstituted or substituted with at least one $R_{10a}$.

In an embodiment, each of $X_1$ and $X_2$ in Formula 2 may C.

In one or more embodiment, the compound represented by Formula 1 may be represented by Formula 3:

Formula 3

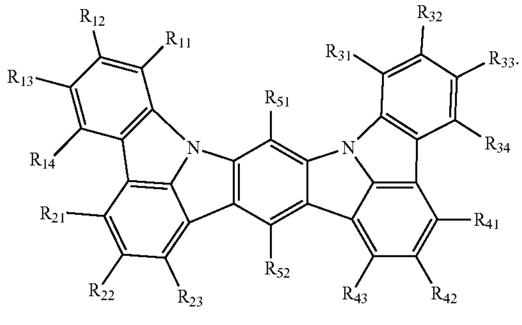

In Formula 3, $R_{11}$ to $R_{14}$ may respectively be the same as described in connection with $R_1$, $R_{21}$ to $R_{23}$ may respectively be the same as described in connection with $R_2$, $R_{31}$ to $R_{34}$ may respectively be the same as described in connection with $R_3$, $R_{41}$ to $R_{43}$ may respectively be the same as described in connection with $R_4$, $R_{51}$ and $R_{52}$ may respectively be the same as described in connection with $R_5$, at least one of $R_{11}$ to $R_{14}$, $R_{21}$ to $R_{23}$, $R_{31}$ to $R_{34}$, $R_{41}$ to $R_{43}$, $R_{51}$, and $R_{52}$ may not be hydrogen, and two of $R_{11}$ to $R_{14}$, $R_{21}$ to $R_{23}$, $R_{31}$ to $R_{34}$, $R_{41}$ to $R_{43}$, $R_{51}$, and $R_{52}$ may optionally be linked to each other or linked together via a single bond to form a $C_8$-$C_{60}$ polycyclic group unsubstituted or substituted with at least one $R_{10a}$.

In an embodiment, at least one of $R_{13}$, $R_{22}$, $R_{33}$, and $R_{42}$ in Formula 2 may not be hydrogen.

In one or more embodiments, the condensed cyclic compound represented by Formula 1 may be one of Compounds 1 to 24:

1

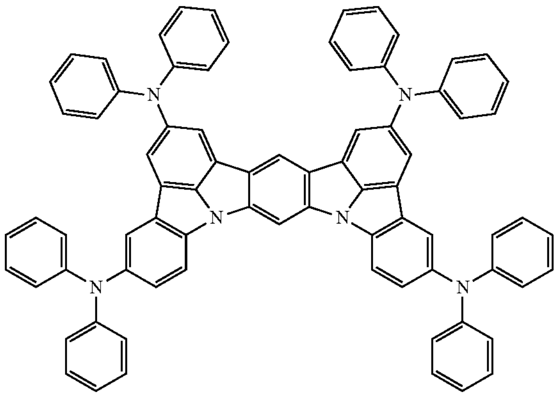

2

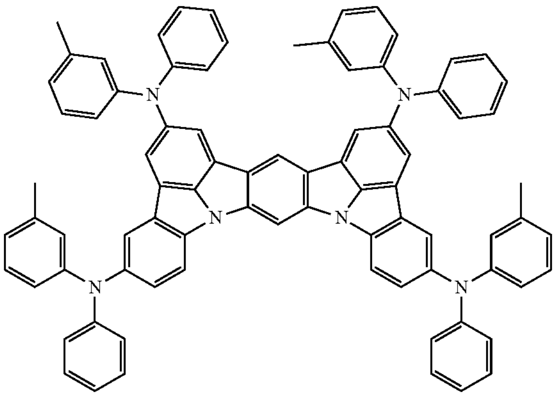

3

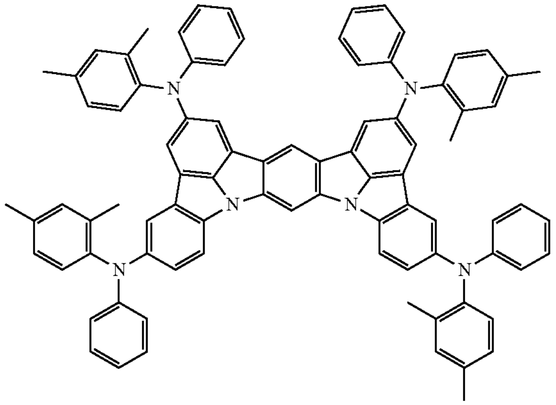

4

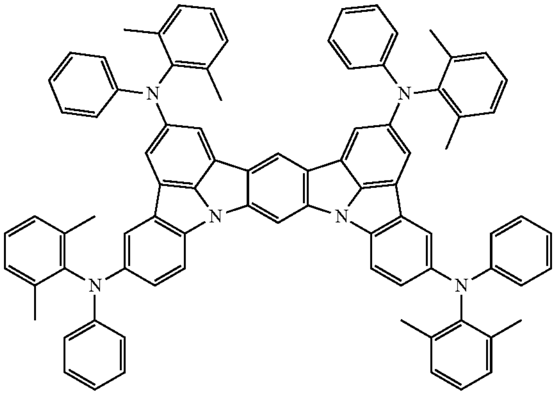

5

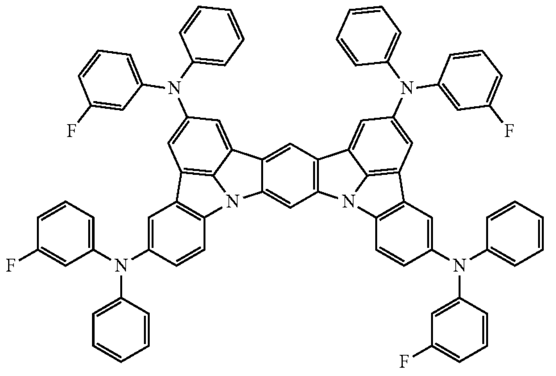

6

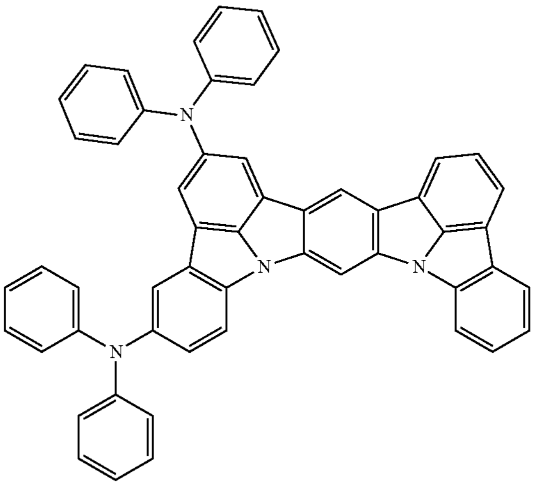

-continued
7
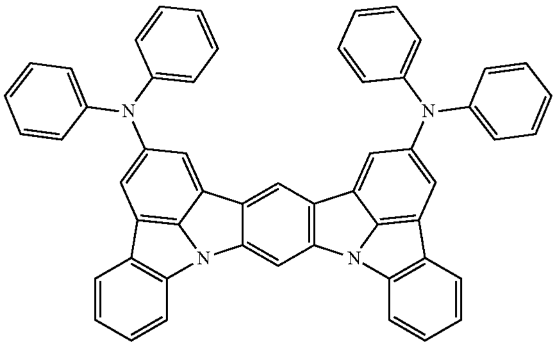
8
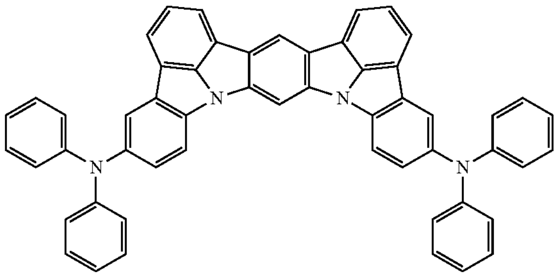
9
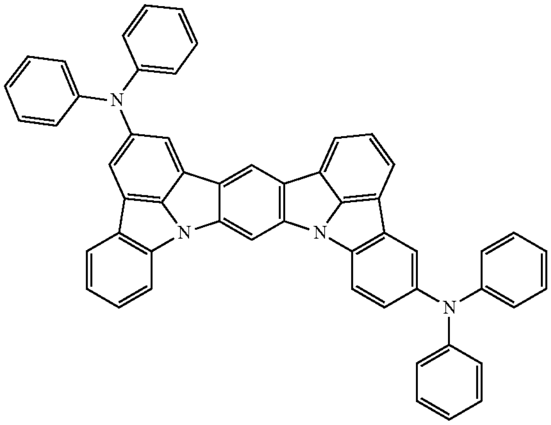
10
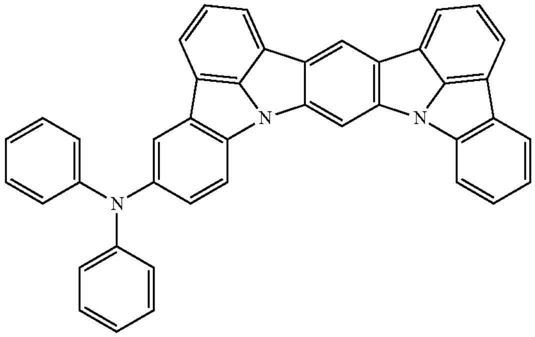
11
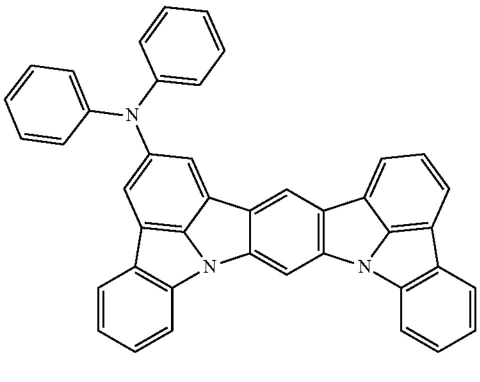
12
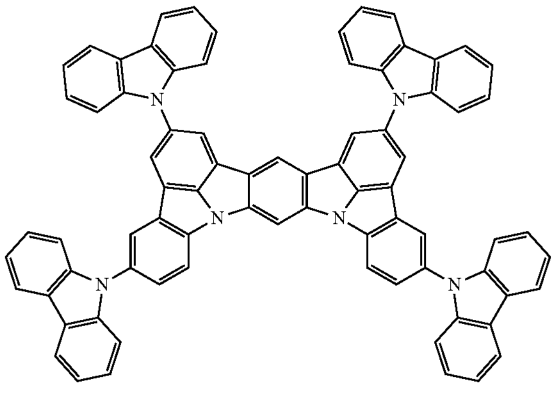

-continued
13
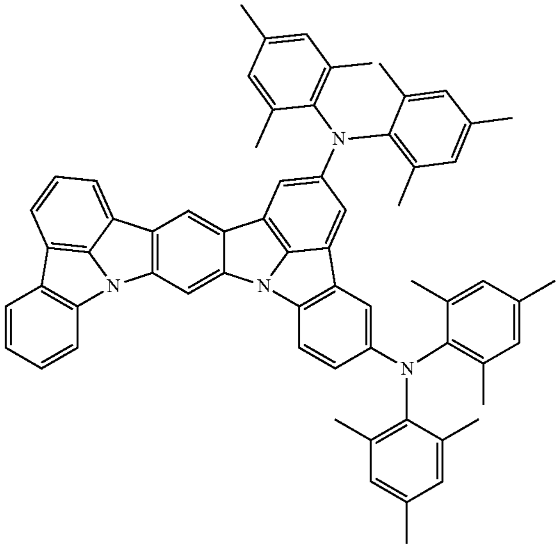
14
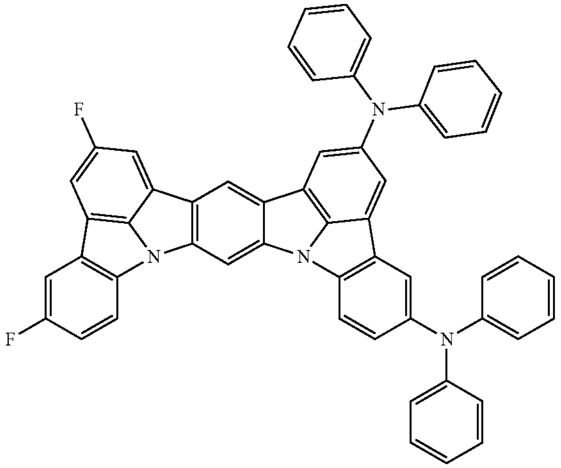
15
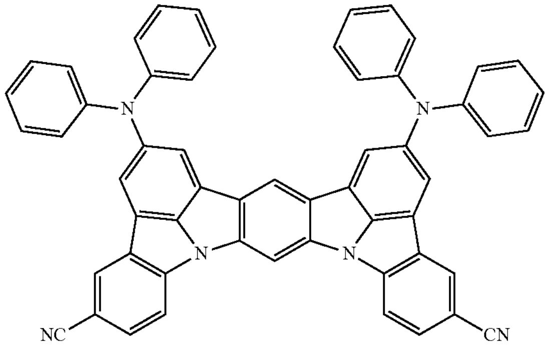
16
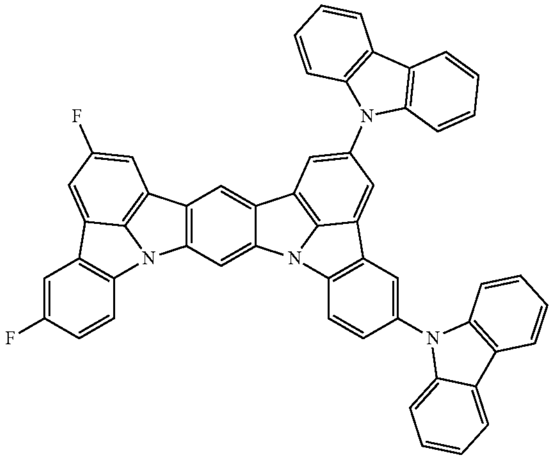
17
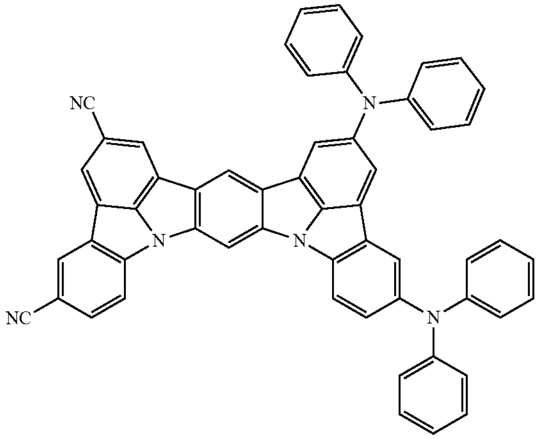
18
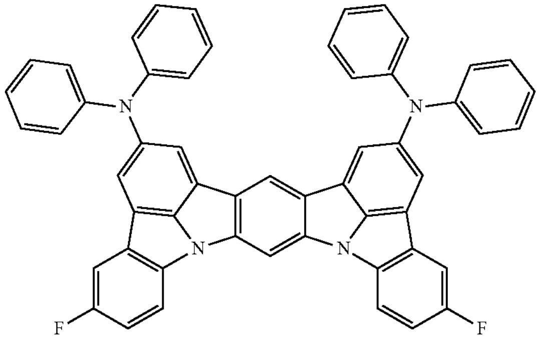

-continued
19
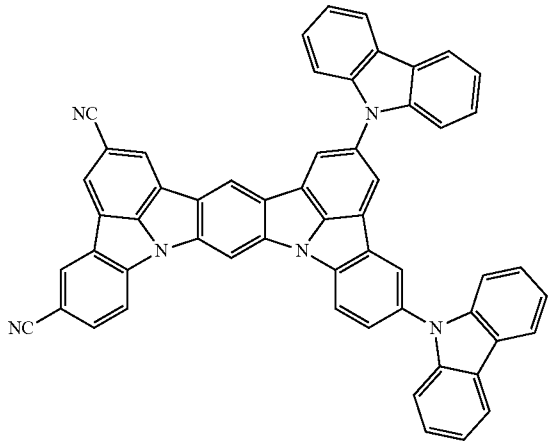
20
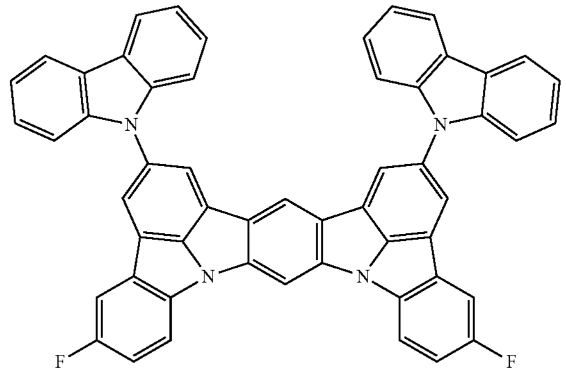
21
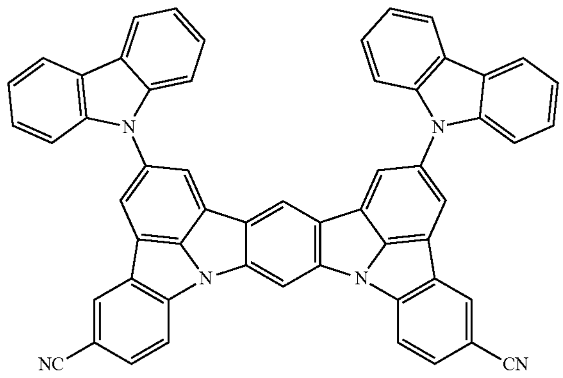
22
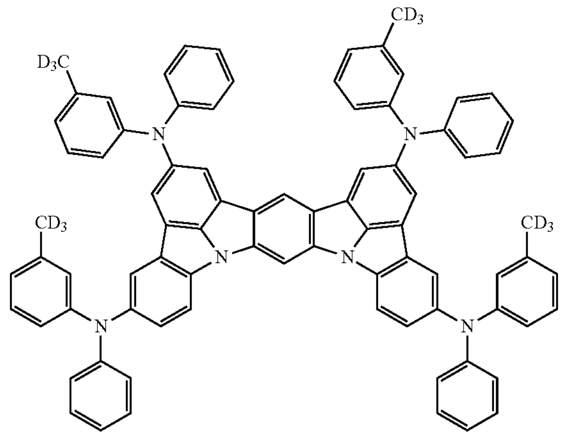
23
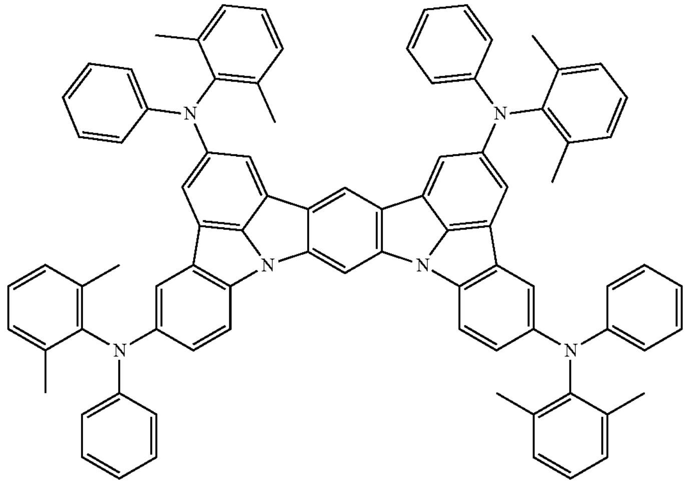

-continued

24

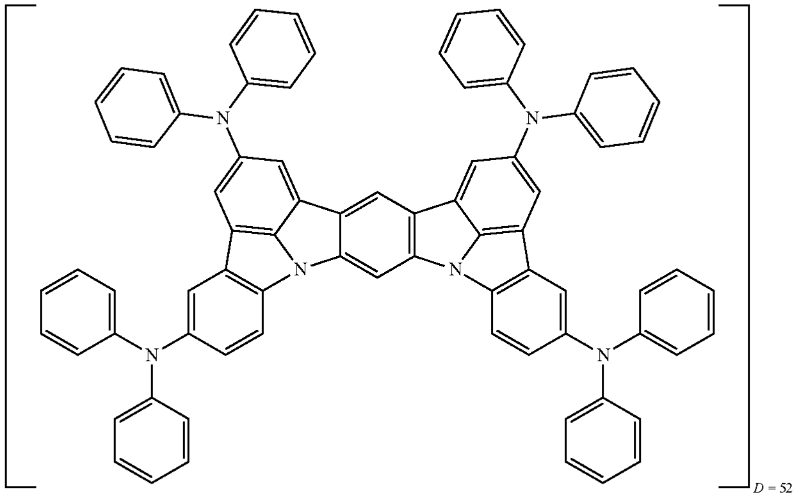

wherein D in Compound 22 is deuterium, and

"D=52" in Compound 24 means that all 52 hydrogen atoms in Compound 24 are substituted with deuterium atoms.

In an embodiment, the condensed cyclic compound represented by Formula 1 may emit blue light or cyan light.

In an embodiment, the condensed cyclic compound represented by Formula 1 may have a maximum emission wavelength in a range of about 380 nm to about 500 nm, about 380 nm to about 490 nm, about 380 nm to about 470 nm, about 400 nm to about 500 nm, about 400 nm to about 490 nm, about 400 nm to about 470 nm, about 450 nm to about 500 nm, about 450 nm to about 490 nm, or about 450 nm to about 470 nm.

In an embodiment, the condensed cyclic compound represented by Formula 1 may have a highest occupied molecular orbital (HOMO) energy level of about −6.0 eV or more and a lowest unoccupied molecular orbital (LUMO) energy level of about −2.5 eV or less, and the HOMO energy level and the LUMO energy level may be values measured a photoelectron spectrometer and a spectrophotometer, respectively.

For example, the HOMO energy level of the condensed cyclic compound represented by Formula 1 may be about −5.8 eV or more and about −5.0 eV or less.

For example, the LUMO energy level of the condensed cyclic compound represented by Formula 1 may be about −3.5 eV or more and about −2.6 eV or less.

In an embodiment, the condensed cyclic compound represented by Formula 1 may have a difference ($\Delta E_{ST}$) between a singlet ($S_1$) energy level and a triplet ($T_1$) energy level of about 0.5 eV or less.

For example, the difference $\Delta E_{ST}$ may be about 0.4 eV or less, about 0.3 eV or less, or about 0.25 eV or less.

In an embodiment, a full width at half maximum (FWHM) in the maximum emission wavelength of the condensed cyclic compound represented by Formula 1 may be about 40 nm or less, about 30 nm or less, or about 25 nm or less in a maximum emission wavelength.

Since the condensed cyclic compound represented by Formula 1 has a rigid intramolecular structure and accordingly suppresses a change in the molecular structure, a narrow emission spectrum may be obtained. In particular, when the condensation directions of the rings including N are the same, such an effect of obtaining a narrow emission spectrum may be increased. In addition, since the compound represented by Formula 1 includes $R_1$ to $R_5$, the difference $\Delta E_{ST}$ between a singlet excitation energy level and a triplet excitation energy level may be lowered. Accordingly, an organic light-emitting device employing the condensed cyclic compound represented by Formula 1 may have a relatively narrow FWHM of an emission peak in the emission spectrum, leading to high color purity and excellent luminescence efficiency.

Synthesis methods of the condensed cyclic compound represented by Formula 1 may be understood by one of ordinary skill in the art by referring to the Examples below.

Another aspect of the present disclosure provides an organic light-emitting device including: a first electrode; a second electrode; and an interlayer arranged between the first electrode and the second electrode and including an emission layer, wherein the interlayer includes at least one condensed cyclic compound.

In an embodiment, the condensed cyclic compound represented by Formula 1 may be included in the emission layer.

In an embodiment, the emission layer may further include a host, and the condensed cyclic compound represented by Formula 1 included in the emission layer may act as a light-emitting dopant. Here, in the emission layer, the amount of the host may be greater than that of the condensed cyclic compound represented by Formula 1.

In one or more embodiments, the emission layer may further include a host and a light-emitting dopant, and the condensed cyclic compound represented by Formula 1 included in the emission layer may act as a sensitizer. Here, in the emission layer, the amount of the host may be greater than the total amount of the light-emitting dopant and the sensitizer. The host will be described in detail later.

When the organic light-emitting device includes the interlayer including the condensed cyclic compound represented by Formula 1, the characteristics of high color purity, a narrow FWHM, and a high external quantum efficiency may be exhibited.

The condensed cyclic compound represented by Formula 1 may be used between a pair of electrodes of the organic light-emitting device. For example, the condensed cyclic compound represented by Formula 1 may be included in the emission layer. In this regard, the condensed cyclic compound may act as a dopant, and the emission layer may further include a host (that is, the amount of the condensed cyclic compound represented by Formula 1 may be smaller than that of the host). The emission layer may emit blue light having a maximum emission wavelength of 380 nm or more (for example, 380 nm or more and 500 nm or less).

In one or more embodiments, the condensed cyclic compound included in the emission layer of the organic light-emitting device may act as a delayed fluorescence dopant, so that delayed fluorescence may be emitted from the emission layer.

In one or more embodiments, the emission layer of the organic light-emitting device may further include a host, and the host may be a compound represented by Formula 4:

Formula 4

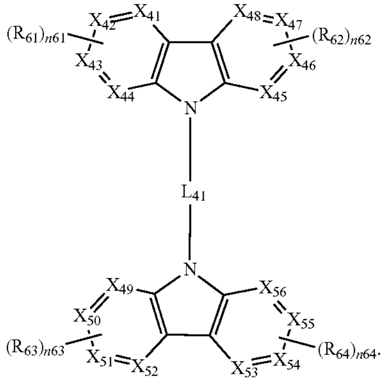

In Formula 4, $X_{41}$ to $X_{56}$ may each independently be C or N, $L_{41}$ may be a single bond, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, $R_{61}$ to $R_{64}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$, n61 to n64 may each independently be an integer from 0 to 4, $R_{10a}$ may be the same as described in the present specification, and $Q_1$ to $Q_3$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

In an embodiment, the host may be Compound H-H104, Compound HE6-203, or a combination thereof, but embodiments of the present disclosure are not limited thereto:

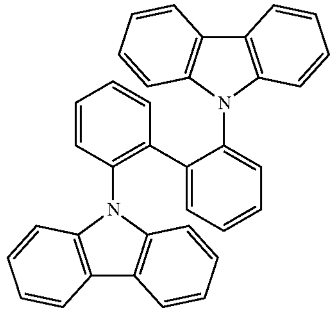

H-H104

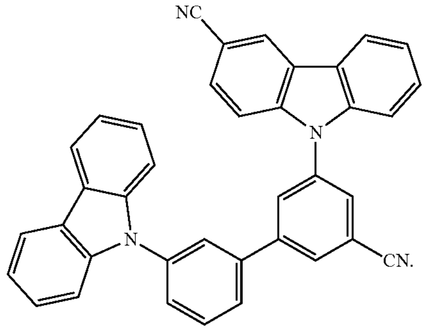

HE6-203

The expression "(the interlayer) includes a condensed cyclic compound represented by Formula 1" as used herein may be construed as meaning that "(the interlayer) includes one condensed cyclic compound belonging to the category of Formula 1" or at least two different condensed cyclic compounds belonging to the category of Formula 1."

In an embodiment, the interlayer may include, as the condensed cyclic compound, only Compound 1. In this regard, Compound 1 may be included in the emission layer of the organic light-emitting device. In one or more embodiments, the interlayer may include, as the condensed cyclic compound, Compound 1 and Compound 2. In this regard, Compound 1 and Compound 2 may exist in an identical layer (for example, Compound 1 and Compound 2 may all exist in the emission layer), or may exist in different layers (for example, Compound 1 may exist in the emission layer, and Compound 2 may exist in the electron transport region).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

For example, in the organic light-emitting device, the first electrode may be an anode, the second electrode may be a cathode, and the interlayer may further include a hole transport region between the first electrode and the emission layer and an electron transport region between the emission layer and the second electrode, wherein the hole transport region may include a hole injection layer, a hole transport layer, an emission auxiliary layer, an electron blocking layer, or any combination thereof, and the electron transport region may include a hole blocking layer, an electron transport layer, an electron injection layer, or any combination thereof.

The term "an interlayer" as used herein refers to a single layer and/or a plurality of layers arranged between the first electrode and the second electrode of the organic light-emitting device.

The term "sensitizer" as used herein refers to a compound that is included in the interlayer (for example, the emission layer) and delivers excitation energy to a light-emitting dopant compound.

Another aspect of the present disclosure provides an electronic apparatus including the organic light-emitting device.

More details of the electronic apparatus may be the same as described herein.

OLED System

An organic light-emitting device according to an embodiment of the present disclosure may include an emission layer including a host and a light-emitting dopant. In the emission layer, and the amount of the host may be greater than that of the condensed cyclic compound.

The host may include at least one of a fluorescent host, a phosphorescent host, or any combination thereof which will be described later. When the host is a mixture of two or more types of host, the host mixture may form an exciplex host.

The host will be described in detail below.

The light-emitting dopant may include the condensed-cyclic compound represented by Formula 1.

An organic light-emitting device according to another embodiment of the present disclosure may include an emission layer including a host, a sensitizer, and a light-emitting dopant. In the emission layer, the amount of the host may be greater than the total amount of the light-emitting dopant and the sensitizer.

The host will be described in detail below.

At least one of the sensitizer and the light-emitting dopant may include the condensed cyclic compound represented by Formula 1.

In an embodiment, the sensitizer may include the condensed cyclic compound represented by Formula 1, but in consideration of the relationship with the light-emitting dopant, the sensitizer may also include a compound having an energy relationship suitable for transferring excited singlet energy and/or excited triplet energy to the light-emitting dopant.

For example, the sensitizer may include the condensed cyclic compound represented by Formula 1, and the light-emitting dopant may include a phosphorescent dopant.

Singlet excitons and triplet excitons of the condensed cyclic compound may respectively be transferred to the excited singlet energy level and the excited triplet energy level of the phosphorescent dopant through a Forster resonance energy transfer (FRET) mechanism and a Dexter energy transfer (DET) mechanism. Here, triplet excitons of the phosphorescent dopant may exhibit phosphorescence emission.

For example, the sensitizer may include the condensed cyclic compound represented by Formula 1, and the light-emitting dopant may include a thermally activated delayed fluorescence (TADF) compound.

The singlet excitons and the triplet excitons of the condensed cyclic compound may respectively be transferred to the excited singlet energy level and the excited triplet energy level of the light-emitting dopant through the FRET and DET mechanisms. Here, triplet excitons of the TADF compound may be converted to singlet excitons by reverse intersystem crossing (RISC), and the accumulated singlet excitons may sequentially transition to a ground state, thereby exhibiting fluorescence.

For example, the sensitizer may include the condensed cyclic compound represented by Formula 1, wherein the condensed cyclic compound may be a TADF compound, and the light-emitting dopant may include a phosphorescent dopant or a TADF compound.

When the condensed cyclic compound is a TADF compound, triplet excitons of the condensed cyclic compound may be converted to singlet excitons by RISC, and at the same time, the energy transfer to the light-emitting dopant by the FRET and DET mechanisms may also occur.

When the sensitizer includes the condensed cyclic compound represented by Formula 1, the triplet-triplet annihilation of the triplet excitons may be suppressed such that the luminescence efficiency of the light-emitting dopant may be improved.

In an embodiment, the light-emitting dopant may include the condensed cyclic compound represented by Formula 1, and the sensitizer may include a TADF compound or an organometallic compound. However, embodiments of the present disclosure are not limited thereto, and any compound capable of transferring excitons to the condensed cyclic compound may be included.

Excitons formed in the sensitizer may be transferred to the light-emitting dopant through the DET mechanism or the FRET mechanism, and the energy of the transferred excitons in the light-emitting dopant may be transitioned to a ground state, and thus light may be emitted.

In this regard, the excitons of the sensitizer may be formed by the host through the FRET mechanism, or by the transfer of excitons generated from the host through the DET mechanism.

In an embodiment, the sensitizer may include a TADF compound.

In addition, the sensitizer may satisfy Expression 1:

$$\Delta E_{ST} \leq 0.3 \text{ eV} \quad \text{Expression 1}$$

wherein $\Delta E_{ST}$ refers to a difference between an excited singlet ($S_1$) energy level and an excited triplet ($T_1$) energy level.

The TADF compound may include singlet excitons and triplet excitons, and regarding the triplet excitons, the triplet excitons may be transferred to the singlet excitons by RISC, and the energy of the singlet excitons accumulated in an excited singlet state may be transferred to the energy of the condensed cyclic compound by the FRET mechanism and/or the DET mechanism.

In one or more embodiments, the sensitizer may include an organometallic compound. For example, the sensitizer may include an organometallic compound including platinum (Pt) as a central metal, but embodiments of the present disclosure are not limited thereto.

The organometallic compound may include singlet excitons and triplet excitons, and regarding the triplet excitons, the energy of the triplet excitons may be transferred to the excited triplet energy of the condensed cyclic compound by the DET mechanism.

The organometallic compound may also satisfy Expression 1 above, and when Expression 1 is satisfied, excitons may respectively be transferred the excited singlet energy level and the excited triplet energy level of the condensed cyclic compound by a mechanism similar to the mechanism applied to the TADF compound, that is, the FRET and/or DET mechanism.

In an embodiment, the excited singlet energy level and the excited triplet energy level of the sensitizer may be lower than the excited singlet energy level and the excited triplet energy level of the host. Thus, the transfer of the excited singlet energy and the excited triplet energy from the host to the sensitizer may easily occur.

In an embodiment, the sensitizer and the light-emitting dopant may each independently include the condensed cyclic compound represented by Formula 1.

As a result, the energy transfer between the sensitizer and the light-emitting dopant may be facilitated by the FRET and DET mechanisms, and accordingly, a high-efficiency organic light-emitting device may be easily manufactured by suppressing the triplet-triplet annihilation.

In general, triplet excitons are known to affect the decrease in lifespan of organic light-emitting devices since they stay in an excited state for a long time. However, due to the use of the condensed cyclic compound of the present disclosure, the time during which the triplet excitons of the sensitizer stays is reduced such that the lifespan of the organic light-emitting device including the condensed cyclic compound may be prolonged.

In an embodiment, the condensed cyclic compound may be a material capable of emitting fluorescence. An emission layer that emits fluorescence may be clearly distinguished from an emission layer of the related art that emits phosphorescence.

For example, the condensed cyclic compound may emit TADF.

The excited singlet and triplet energy levels of the condensed cyclic compound may be lower than the excited singlet and triplet energy levels of the host compound which will be described later. Accordingly, the transfer of the singlet excitons and/or the triplet excitons from the host compound to the condensed cyclic compound may easily occur.

The condensed cyclic compound may receive singlet excitons and/or triplet excitons from the sensitizer.

In an embodiment, when the sensitizer is a TADF compound, the excited singlet energy level of the condensed cyclic compound may be lower than the excited singlet energy level of the sensitizer, and the condensed cyclic compound may receive singlet excitons from singlet excitons of the sensitizer by the FRET mechanism and/or DET mechanism.

In one or more embodiments, when the sensitizer is an organometallic compound, the excited triplet energy level of the condensed cyclic compound may be lower than the excited triplet energy level of the sensitizer, and the condensed cyclic compound may receive triplet excitons from the sensitizer by the DET mechanism.

In one or more embodiments, when the sensitizer is a TADF compound or an organometallic compound, the condensed cyclic compound may further receive singlet excitons and/or triplet excitons from the host, and the triplet excitons received from the host may be converted to singlet energy of the condensed cyclic compound by RISC.

Due to this mechanism, the triplet-triplet annihilation may be suppressed by reducing the time during which the excitons stay in the excited triplet energy of the condensed cyclic compound, and high-efficiency fluorescence may be realized through the transition of multiple singlet excitons to the ground state.

In the emission layer, the amount of the sensitizer may be in a range of about 5 wt % to about 50 wt %. Within this range, effective energy transfer in the emission layer may be achieved, and accordingly, an organic light-emitting device having high efficiency and a long lifespan may be realized.

In an embodiment, the host, the condensed cyclic compound, and the sensitizer may satisfy Expression 2:

$$T_1(H)/S_1(H) \geq T_1(S)/S_1(S) \geq T_1(PC)/S_1(PC) \qquad \text{Expression 2}$$

wherein, in Expression 2, $T_1(H)$ is the lowest excited triplet energy level of the host;

$S_1(H)$ is the lowest excited singlet energy level of the host;

$T_1(CC)$ is the lowest excited triplet energy level of the condensed cyclic compound;

$S_1(CC)$ is the lowest excited singlet energy level of the condensed cyclic compound;

$T_1(S)$ is the lowest excited triplet energy level of the sensitizer; and $S_1(S)$ is the lowest excited singlet energy level of the sensitizer.

When the host, the condensed cyclic compound, and the sensitizer further satisfy Condition 2, triplet excitons may be effectively transferred from the emission layer to the condensed cyclic compound, and accordingly, an organic light-emitting device having improved efficiency may be obtained.

A thickness of the emission layer may be in a range of about 100 Å to about 1,000 Å, for example, about 200 Å to about 600 Å. When the thickness of the emission layer is within these ranges, excellent luminescence characteristics may be obtained without a substantial increase in driving voltage.

Description of FIG. 1

FIG. 1 is a schematic cross-sectional view of an organic light-emitting device 10 according to an exemplary embodiment. Hereinafter, a structure and a manufacturing method of an organic light-emitting device according to an example of the present disclosure will be described with reference to FIG. 1.

The organic light-emitting device 10 of FIG. 1 includes a substrate 1, a first electrode 2, a second electrode 6 facing the first electrode 2, and an emission layer 4 between the first electrode 2 and the second electrode 6.

The organic light-emitting device 10 also includes a hole transport region 3 between the first electrode 2 and the emission layer 4 and an electron transport region 5 between the emission layer 4 and the second electrode 6.

The organic light-emitting device 10 may further include the substrate 1 under the first electrode 2 or above the second electrode 6. For use as the substrate 1, any substrate that is used in organic light-emitting devices of the related art may be used, and for example, a glass substrate or a transparent plastic substrate, each having excellent mechanical strength, thermal stability, transparency, surface smoothness, ease of handling, and water resistance, may be used.

First Electrode 2

The first electrode 2 may be formed by, for example, depositing or sputtering a material for forming the first electrode 2 on the substrate 1. The first electrode 2 may be an anode. The material for forming the first electrode 11 may be a material with a high work function to facilitate hole injection.

The first electrode 2 may be a reflective electrode, a semi-transmissive electrode, or a transmissive electrode. When the first electrode 2 is a transmissive electrode, the material for forming the first electrode 2 may be indium tin oxide (ITO), indium zinc oxide (IZO), tin oxide ($SnO_2$), zinc oxide (ZnO), and any combination thereof, but embodiments of the present disclosure are not limited thereto. When the first electrode 2 is a semi-transmissive electrode or a reflective electrode, the material for forming the first electrode 2 may be magnesium (Mg), silver (Ag), aluminum (Al), aluminum-lithium (Al—Li), calcium (Ca), magnesium-indium (Mg—In), magnesium-silver (Mg—Ag), or any combination thereof, but embodiments of the present disclosure are not limited thereto.

The first electrode 2 may have a single-layered structure or a multi-layered structure including two or more layers. For example, the first electrode 2 may have a three-layered structure of ITO/Ag/ITO, but embodiments of the present disclosure are not limited thereto.

An interlayer may be arranged on the first electrode 2.

The interlayer may include: the hole transport region 3; the emission layer 4; and the electron transport region 5.

Hole Transport Region 3

In the organic light-emitting device 10, the hole transport region 3 may be arranged between the first electrode 2 and the emission layer 4.

The hole transport region 3 may have a single-layered structure or a multi-layered structure.

For example, the hole transport region 3 may consist of a hole injection layer or a hole transport layer, or have a hole injection layer/hole transport layer structure, a hole injection layer/first hole transport layer/second hole transport layer structure, a hole transport layer/interlayer structure, a hole injection layer/hole transport layer/interlayer structure, a hole transport layer/electron blocking layer structure, or a hole injection layer/hole transport layer/electron blocking layer structure. However, embodiments of the present disclosure are not limited thereto.

The hole transport region 3 may include any compound having hole-transporting properties.

For example, the hole transport region 3 may include an amine-based compound.

In an embodiment, the hole transport region 3 may include at least one compound represented by Formulae 201 to 205, but embodiments of the present disclosure are not limited thereto:

Formula 201

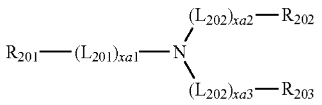

Formula 202

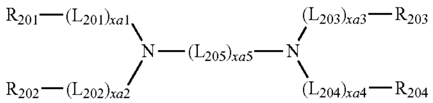

Formula 203

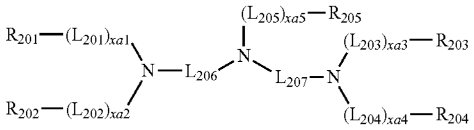

Formula 204

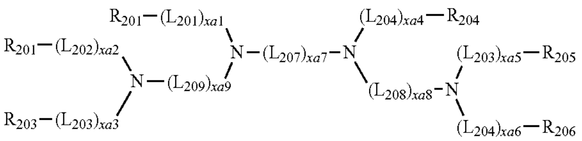

-continued

Formula 205

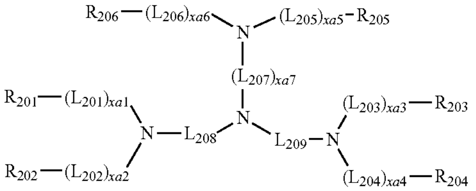

wherein, in Formulae 201 to 205, $L_{201}$ to $L_{209}$ may each independently be *—O—*', *—S—*', a substituted or unsubstituted $C_5$-$C_{60}$ carbocyclic group, or a substituted or unsubstituted $C_1$-$C_{60}$ heterocyclic group, xa1 to xa9 may each independently be an integer from 0 to 5, and $R_{201}$ to $R_{206}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, wherein two neighboring a group among $R_{201}$ to $R_{206}$ may optionally be linked to each other via a single bond, a dimethyl-methylene group, or a diphenyl-methylene group.

For example, $L_{201}$ to $L_{209}$ may each independently be a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coprogen group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, or a triindolobenzene group, each unsubstituted or substituted with deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, —Si$(Q_{11})(Q_{12})(Q_{13})$, or any combination thereof, xa1 to xa9 may each independently be 0, 1, or 2, $R_{201}$ to $R_{206}$ may each independently be a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an indenocarbazolyl group, an indolocarbazolyl group, a benzofurocarbazolyl group, or a benzothienocarbazolyl group, each unsubstituted or substituted with deuterium, —F, —Cl, —Br, —I, a hydroxyl group, a cyano group, a nitro group, an amidino group, a hydrazine group, a hydrazone group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group; a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —$Si(Q_{31})(Q_{32})(Q_{33})$, —$N(Q_{31})(Q_{32})$, or any combination thereof, and $Q_{11}$ to $Q_{13}$ and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

In an embodiment, the hole transport region 3 may include a carbazole-containing amine-based compound.

In one or more embodiments, the hole transport region 3 may include a carbazole-containing amine-based compound and a carbazole-free amine-based compound.

The carbazole-containing amine-based compound may be, for example, a compound represented by Formula 201 which include a carbazole group and which further include at least one of a dibenzofuran group, a dibenzothiophene group, a fluorene group, a spiro-bifluorene group, an indenocarbazole group, an indolocarbazole group, a benzofurocarbazole group, a benzothienocarbazole group, or any combination thereof.

The carbazole-free amine-based compound may be, for example, a compound represented by Formula 201 which do not include a carbazole group and which include at least one of a dibenzofuran group, a dibenzothiophene group, a fluorene group, a spiro-bifluorene group, an indenocarbazole group, an indolocarbazole group, a benzofurocarbazole group, a benzothienocarbazole group, or any combination thereof.

In one or more embodiments, the hole transport region 3 may include at least one compound represented by Formulae 201 and 202.

In one or more embodiments, the hole transport region 3 may include at least one compound represented by Formulae 201-1, 202-1, and 201-2, but embodiments of the present disclosure are not limited thereto:

Formula 201-1

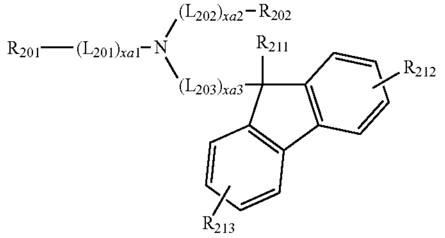

Formula 202-1

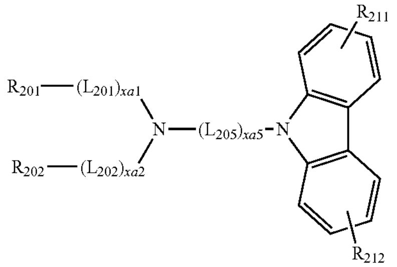

Formula 201-2

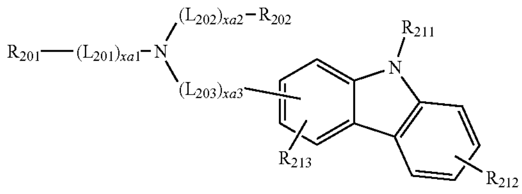

wherein, in Formulae 201-1, 202-1, and 201-2, $L_{201}$ to $L_{203}$, $L_{205}$, xa1 to xa3, xa5, $R_{201}$, and $R_{202}$ may respectively be the same as described herein, and $R_{211}$ to $R_{213}$ may each independently be hydrogen, deuterium, —F, —Cl, —Br, —I, a hydroxyl group, a cyano group, a nitro group, an amidino group, a hydrazine group, a hydrazone group, a $C_1$-$C_{20}$ alkyl group, a $C_1$-$C_{20}$ alkoxy group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a dimethylfluorenyl group, a diphenylfluorenyl group, a triphenylenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, or a pyridinyl group.

For example, the hole transport region 3 may include at least one of Compounds HT1 to HT39, but embodiments of the present disclosure are not limited thereto:

HT1
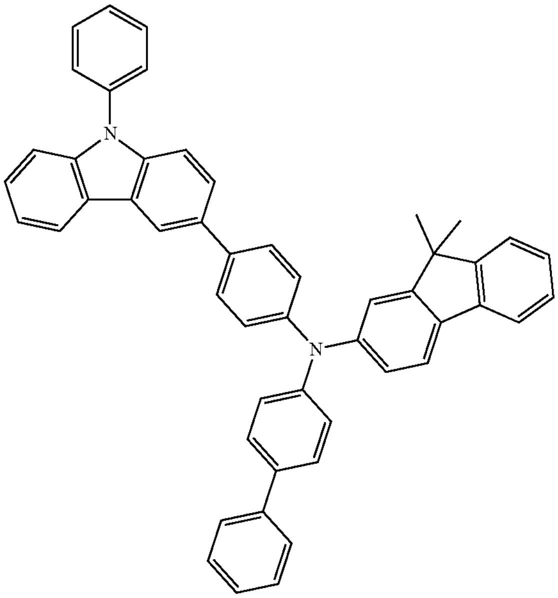
HT2
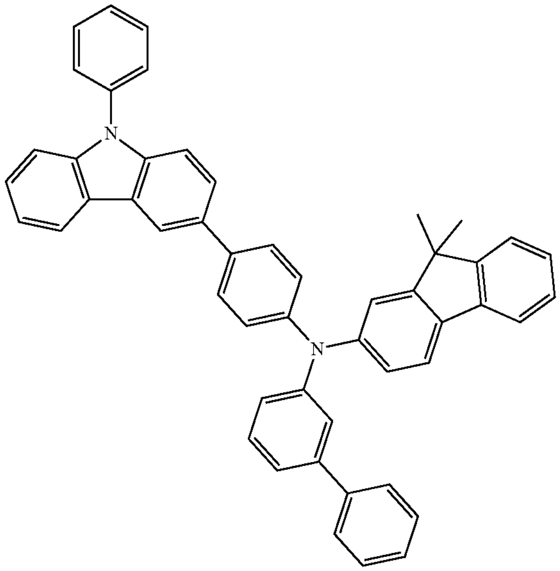
HT3
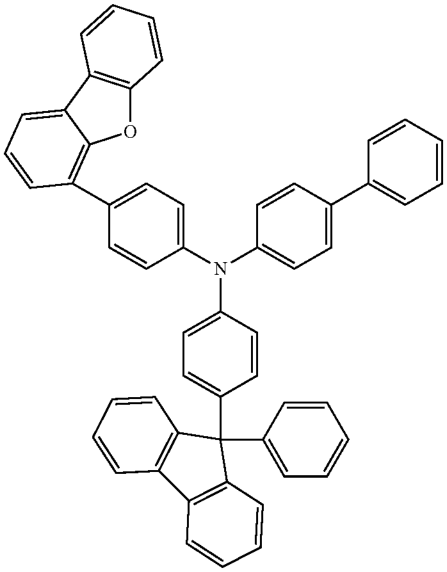
HT4
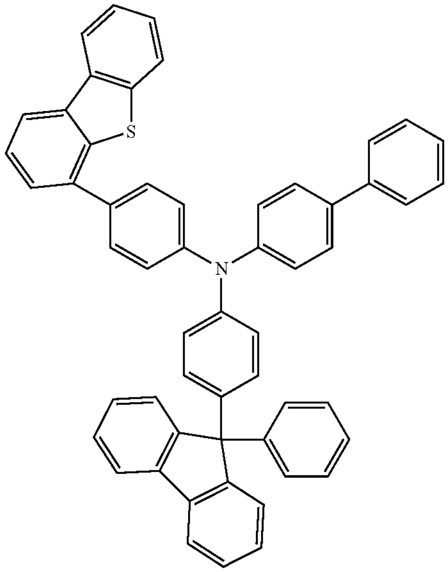

-continued
HT5
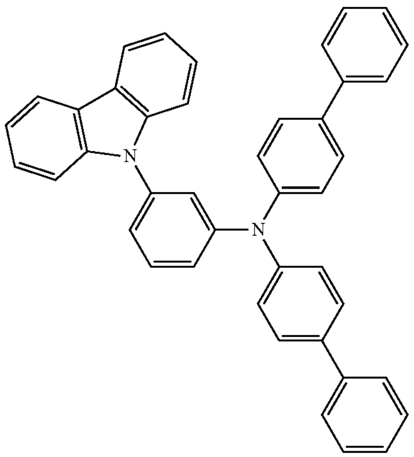
HT6
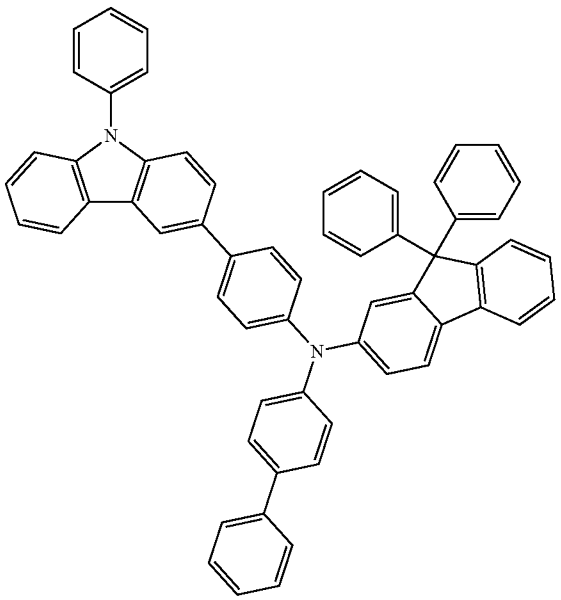
HT7
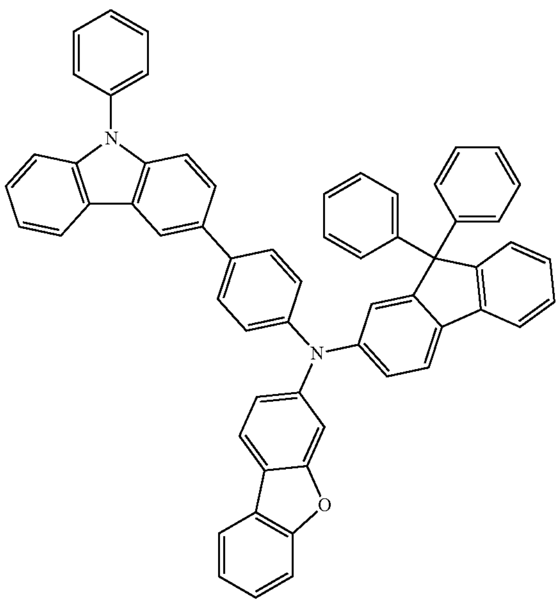
HT8
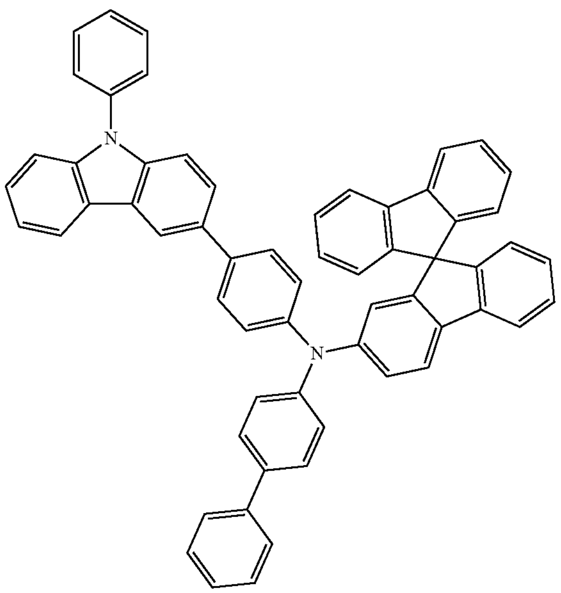

-continued
HT9
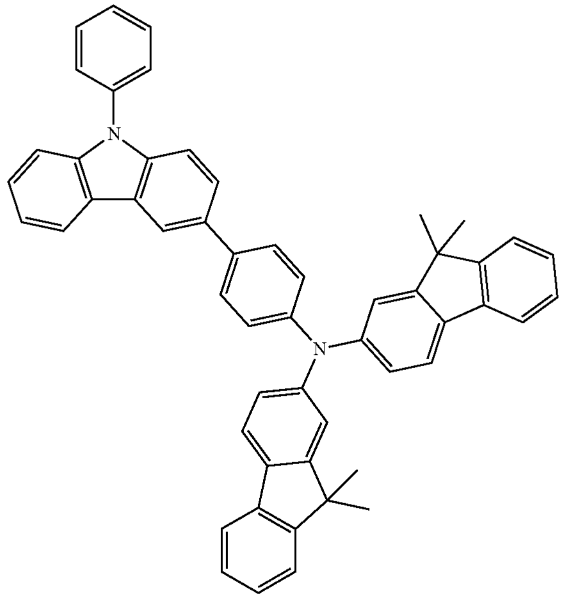
HT10
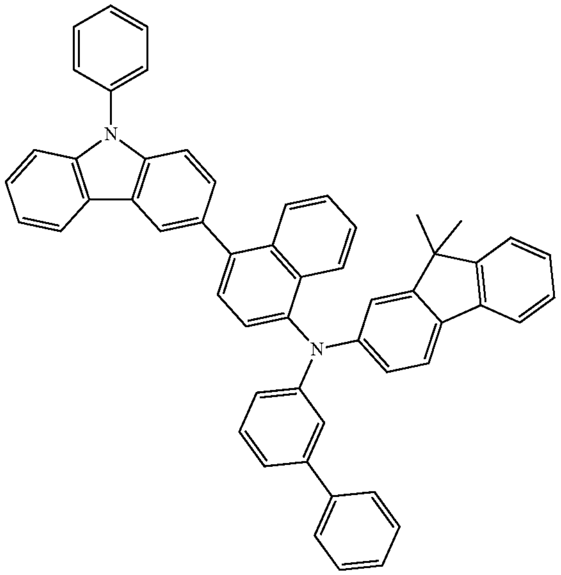
HT11
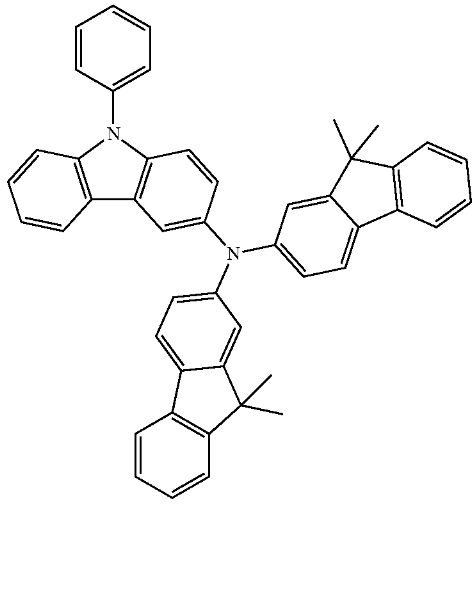
HT12
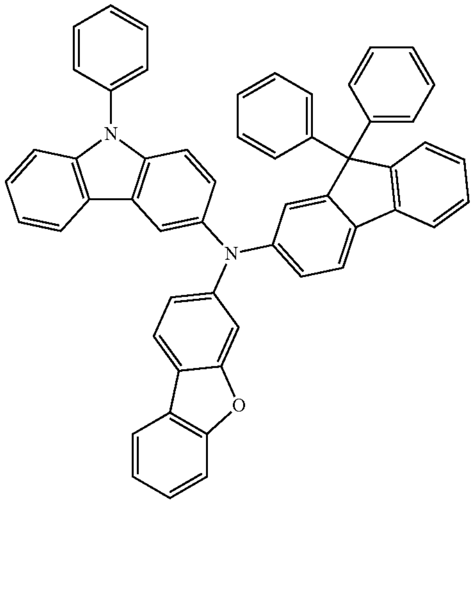

-continued
HT13
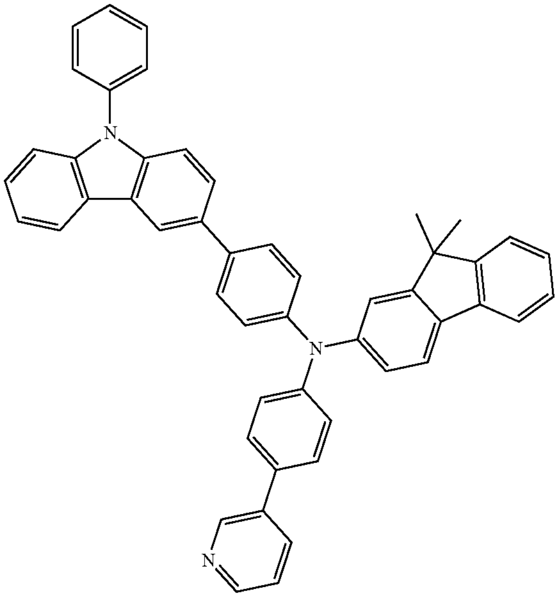
HT14
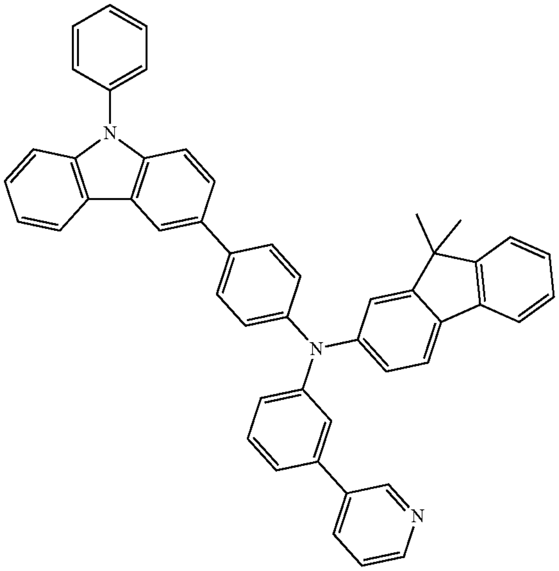
HT15
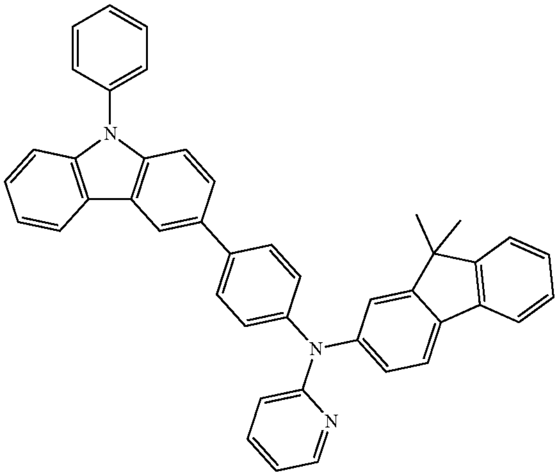
HT16
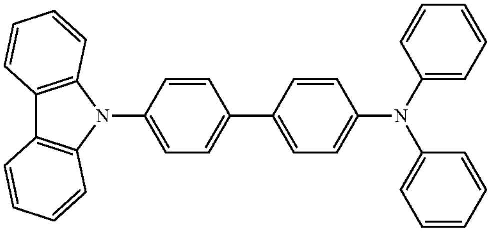
HT17
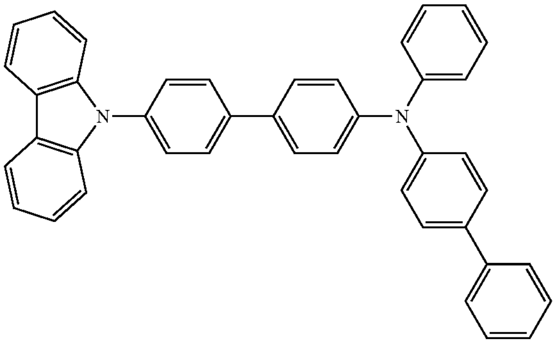
HT18
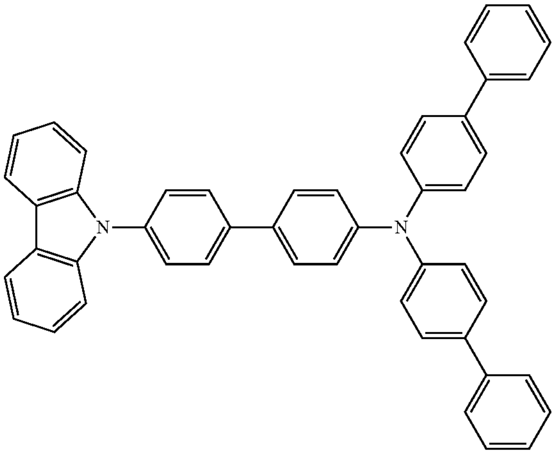

-continued
HT19
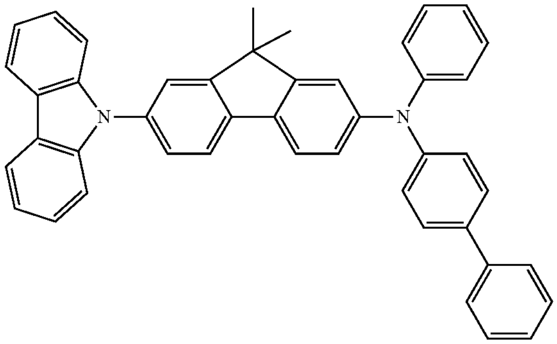
HT20
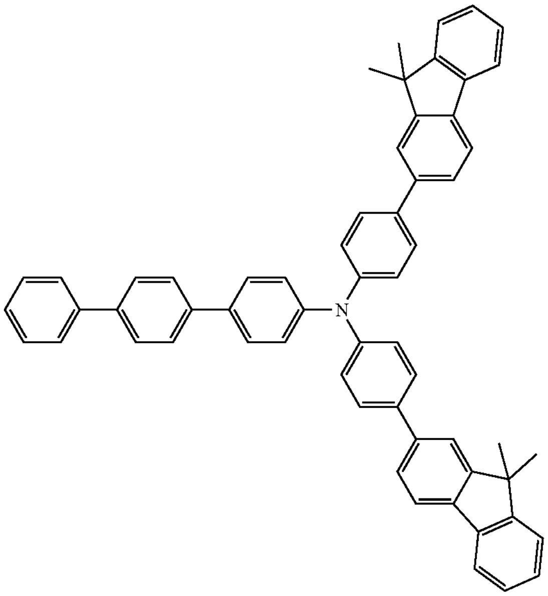
HT21
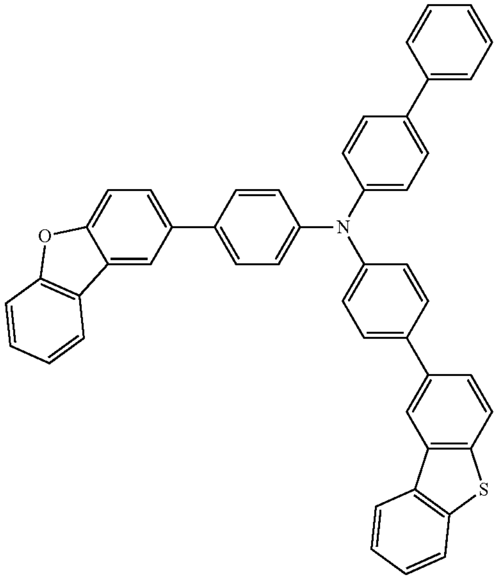
HT22
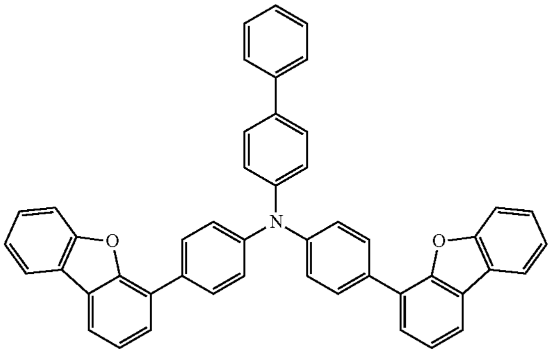

-continued
HT23
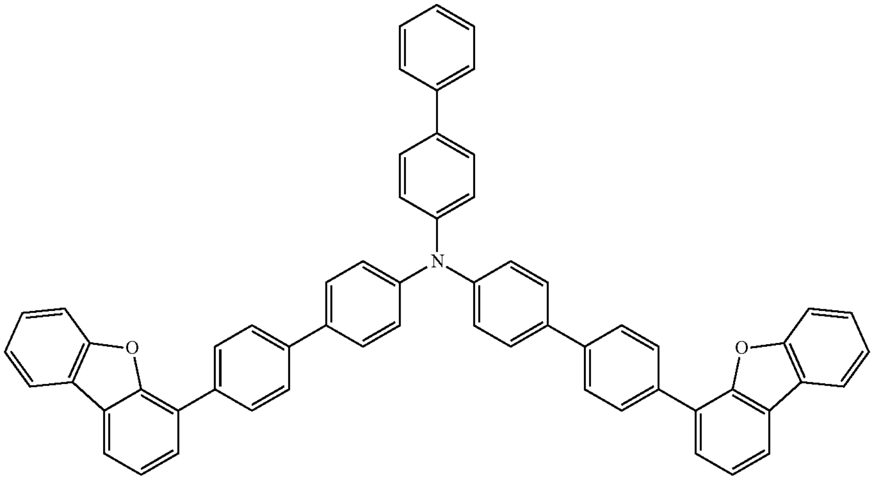
HT24
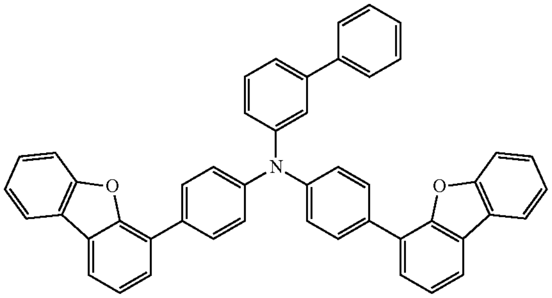
HT25
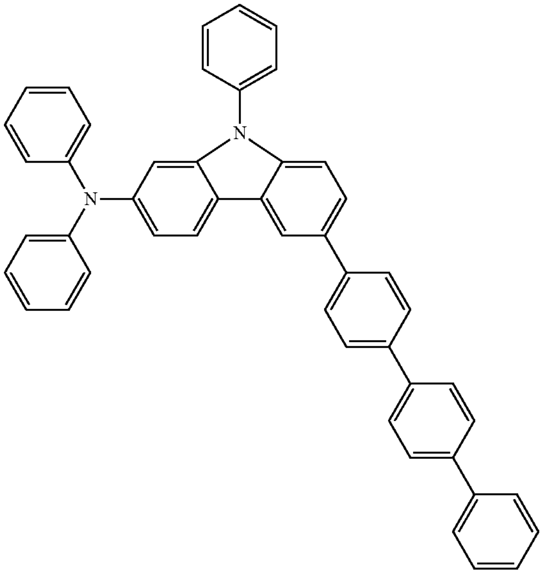
HT26
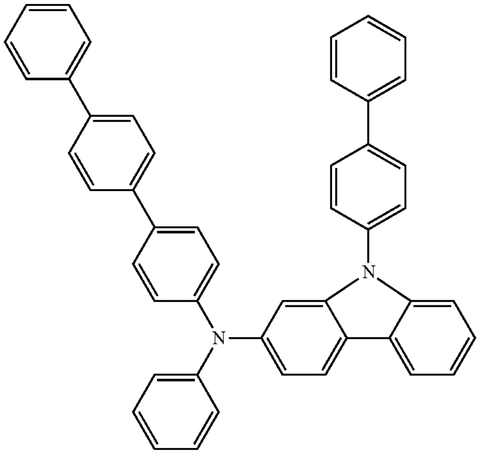
HT27
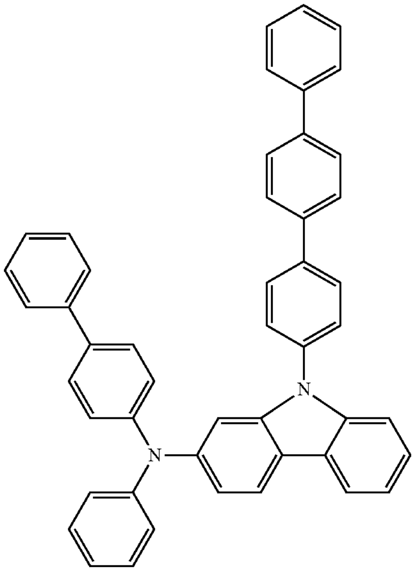

-continued
HT28
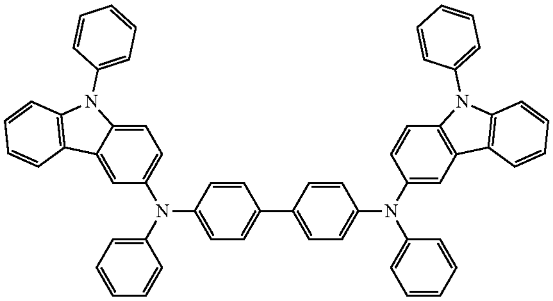
HT29
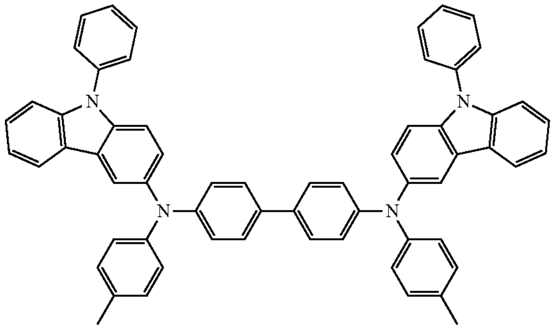
HT30
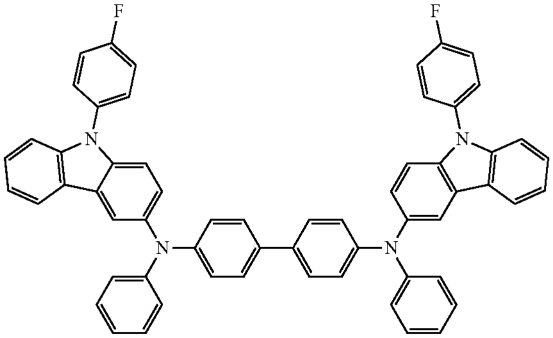
HT31
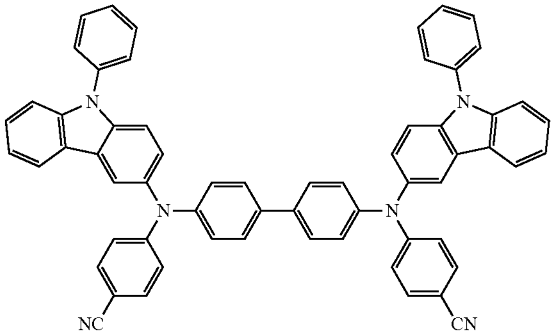
HT32
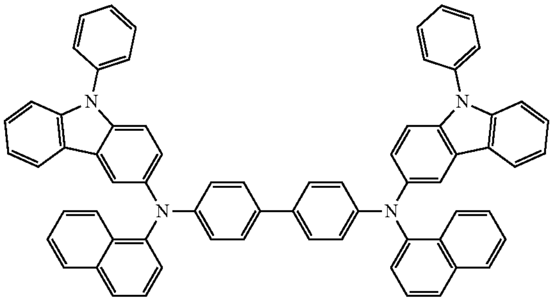
HT33
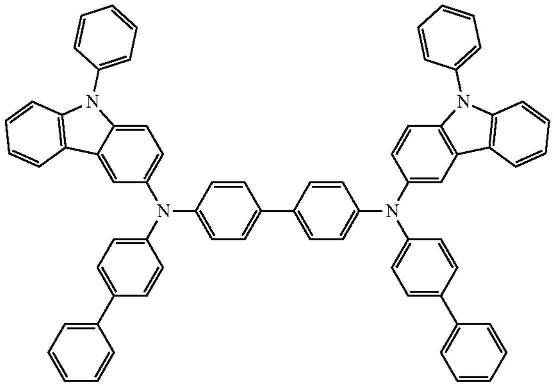
HT34
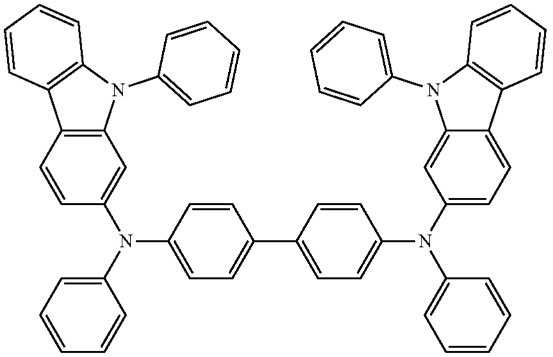
HT35
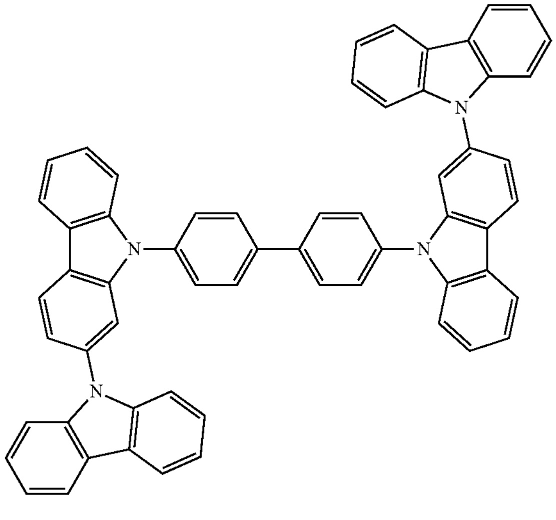

-continued

HT36

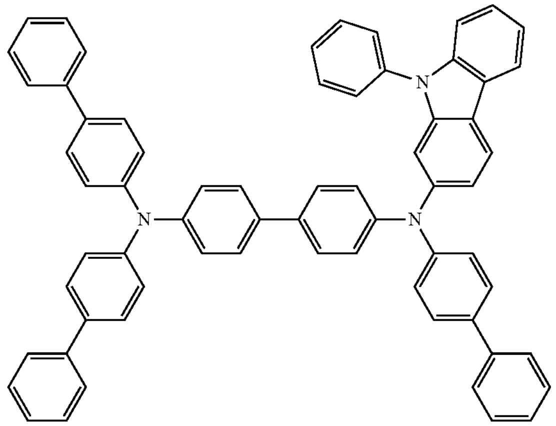

HT37

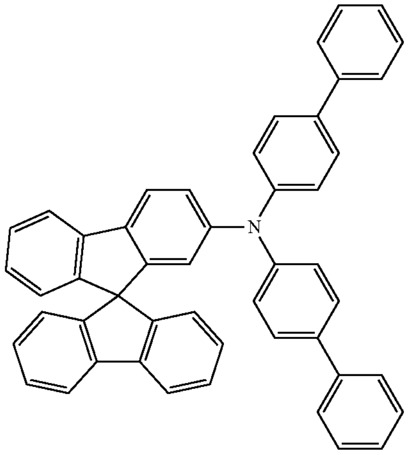

HT38

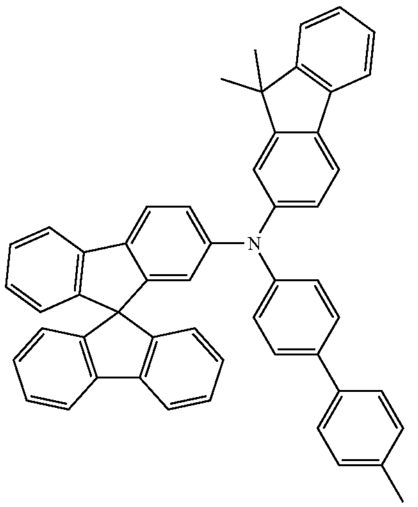

HT39

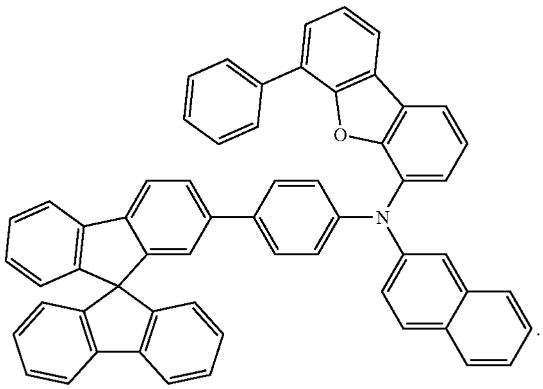

In one or more embodiments, hole transport region 3 of the organic light-emitting device 10 may further include a p-dopant. When the hole transport region 3 further includes a p-dopant, the hole transport region 3 may have a structure including a matrix (for example, at least one of compounds represented by Formulae 201 to 205) and a p-dopant included in the matrix. The p-dopant may be uniformly or non-uniformly doped in the hole transport region 3.

In an embodiment, the p-dopant may have a LUMO energy level of about −3.5 eV or less.

The p-dopant may include at least one a quinone derivative, a metal oxide, a cyano group-containing compound, or any combination thereof, but embodiments of the present disclosure are not limited thereto.

In an embodiment, the p-dopant may include at least one of:

a quinone derivative, such as tetracyanoquinodimethane (TCNQ), 2,3,5,6-tetrafluoro-7,7,8,8-tetracyanoquinodimethane (F4-TCNQ), or F6-TCNNQ;

a metal oxide, such as tungsten oxide or molybdenum oxide;

1,4,5,8,9,12-hexaazatriphenylene-hexacarbonitrile (HAT-CN); and a compound represented by Formula 221, but embodiments of the present disclosure are not limited thereto:

Formula 221

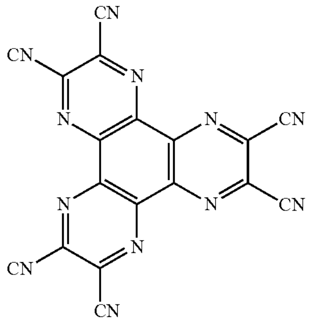

HAT-CN

-continued

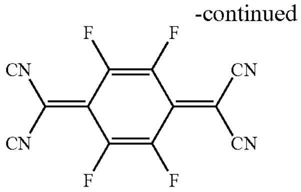

F4-TCNQ

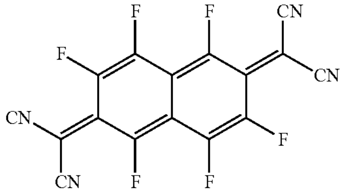

F6-TCNNQ

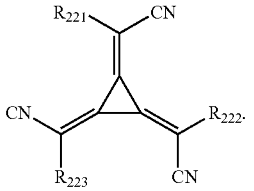

In Formula 221, $R_{221}$ to $R_{223}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, wherein at least one of $R_{221}$ to $R_{223}$ may have at least one of a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I, or any combination thereof.

The hole transport region 3 may have a thickness in a range of about 100 Å to about 10,000 Å, for example, about 400 Å to about 2,000 Å, and the emission layer 4 may have a thickness in a range of about 100 Å to about 3,000 Å, for example, about 300 Å to about 1,000 Å. When the thickness of each of the hole transport region 3 and the emission layer 4 is within these ranges, satisfactory hole transporting characteristics and/or luminescence characteristics may be obtained without a substantial increase in driving voltage.

Emission Layer 4

The emission layer 4 may be a single layer consisting of a single material or a single layer consisting of a plurality of different materials. In addition, the emission layer 4 may have a multi-layered structure including a plurality of layers including different materials.

The emission layer 4 may include the condensed-cyclic compound represented by Formula 1.

The emission layer 4 may have a thickness in a range of about 10 Å to about 1,000 Å, for example, about 100 Å to about 300 Å. When the thickness of the emission layer is within these ranges, excellent luminescence characteristics may be obtained without a substantial increase in driving voltage.

In an embodiment, the emission layer 4 of the organic light-emitting device 10 may include, in addition to the condensed cyclic compound represented by Formula 1, an anthracene derivative, a pyrene derivative, a fluoranthene derivative, a chrysene derivative, a dihydrobenzanthracene derivative, a triphenylene derivative, or any combination thereof.

The emission layer 4 may further include a host, and the light-emitting dopant may include the condensed cyclic compound represented by Formula 1. The host may not include a metal atom.

In an embodiment, the host may include a compound represented by Formula 4.

In an embodiment, the host may include one kind of host. When the host includes one kind of host, the one kind of host may be a bipolar host, an electron-transporting host, or a hole-transporting host, which will be described below.

In one or more embodiments, the host may include a mixture of two or more different hosts. For example, the host may be a mixture of an electron-transporting host and a hole-transporting host, a mixture of two types of electron-transporting hosts different from each other, or a mixture of two types of hole-transporting hosts different from each other. The electron-transporting host and the hole-transporting host will be described in detail below.

In one or more embodiments, the host may include an electron-transporting host which includes at least one electron-transporting moiety and a hole-transporting host which does not include an electron-transporting moiety.

The electron-transporting moiety may be a cyano group, a π electron-deficient nitrogen-containing cyclic group, or a group represented by one of the following formulae:

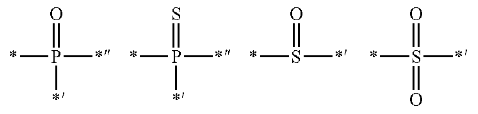

wherein *, *', and *" in the formulae above each indicate a binding site to a neighboring atom.

In one or more embodiments, the electron-transporting host included in the emission layer may include at least one of a cyano group, a π electron-deficient nitrogen-containing cyclic group, or any combination thereof.

In one or more embodiments, the electron-transporting host included in the emission layer may include at least one cyano group.

In one or more embodiments, the electron-transporting host included in the emission layer may include at least one cyano group and at least one π electron deficient nitrogen-containing cyclic group.

In one or more embodiments, the host may include an electron-transporting host and a hole-transporting host, wherein the electron-transporting host may include at least one π electron-deficient nitrogen-free cyclic group and at least one electron-transporting moiety, and the hole-transporting host may include at least one π electron-deficient nitrogen-free cyclic group and may not include an electron-transporting moiety.

The term "π electron-deficient nitrogen-containing cyclic group" as used herein refers to a cyclic group having at least one *—N=*' moiety, and for example, may be: an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; or a condensed cyclic group in which two or more π electron-efficient nitrogen-containing cyclic a group are condensed with each other.

The π electron-deficient nitrogen-free cyclic group may be: a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coprogen group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a triindolobenzene group; or a condensed cyclic group in which two or more π electron-deficient nitrogen-free cyclic a group are condensed with each other, but embodiments of the present disclosure are not limited thereto.

In one or more embodiments, the electron-transporting host may be a compound represented by Formula E-1, and the hole-transporting host may be a compound represented by Formula H-1, but embodiments of the present disclosure are not limited thereto:

$[Ar_{301}]_{xb11}\text{-}[(L_{301})_{xb1}\text{-}R_{301}]_{xb21}$ Formula E-1 wherein, in Formula E-1, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be a single bond, a group represented by one of the following formulae, a substituted or unsubstituted $C_5$-$C_{60}$ carbocyclic group, or a substituted or unsubstituted $C_1$-$C_{60}$ heterocyclic group, wherein *, *', and *" in the following formulae each indicate a binding site to a neighboring atom:

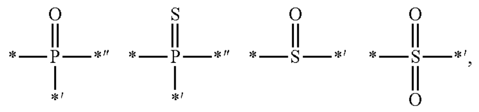

xb1 may be an integer from 1 to 5, $R_{301}$ may be hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $—Si(Q_{301})(Q_{302})(Q_{303})$, $—N(Q_{301})(Q_{302})$, $—B(Q_{301})(Q_{302})$, $—C(=O)(Q_{301})$, $—S(=O)_2(Q_{301})$, $—S(=O)(Q_{301})$, $—P(=O)(Q_{301})(Q_{302})$, or $—P(=S)(Q_{301})(Q_{302})$, xb21 may be an integer from 1 to 5, $Q_{301}$ to $Q_{303}$ may each independently be a $C_1$-$C_{10}$ alkyl group, a $C_1$-$C_{10}$ alkoxy group, a phenyl group, a biphenyl group, a terphenyl group, or a naphthyl group, and at least one of Conditions 1 to 3 may be satisfied:

Condition 1 at least one of $Ar_{301}$, $L_{301}$, $R_{301}$, or any combination thereof in Formula E-1 each independently includes a π electron-deficient nitrogen-containing cyclic group;

Condition 2

$L_{301}$ in Formula E-1 is a group represented by one of the following formulae; and

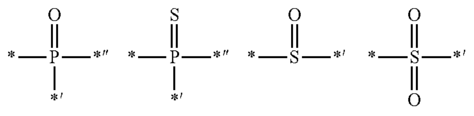

Condition 3

$R_{301}$ in Formula E-1 is a cyano group, $—S(=O)_2(Q_{301})$, $—S(=O)(Q_{301})$, $—P(=O)(Q_{301})(Q_{302})$, or $—P(=S)(Q_{301})(Q_{302})$, $Ar_{401}\text{-}(L_{401})_{xd1}\text{-}(Ar_{402})_{xd11}$ Formula H-1

11

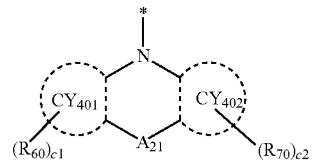

12

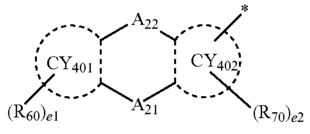

wherein, in Formulae H-1, 11, and 12, $L_{401}$ may be:

a single bond; or a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coprogen group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, and a triindolobenzene group, each unsubstituted or substituted with at least one deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, or —$Si(Q_{401})(Q_{402})(Q_{403})$, xd1 may be an integer from 1 to 10, wherein, when xd1 is 2 or more, two or more of $L_{401}$(s) may be identical to or different from each other, $Ar_{401}$ may be a group represented by Formulae 11 or 12, $Ar_{402}$ may be:

a group represented by Formulae 11 or 12, a phenyl group, a naphthyl group, a fluorenyl group, a carbazolyl group, a dibenzofuranyl group, a dibenzothiophenyl group, a biphenyl group, a terphenyl group, or a triphenylenyl group; or a phenyl group, a naphthyl group, a fluorenyl group, a carbazolyl group, a dibenzofuranyl group, a dibenzothiophenyl group, a biphenyl group, a terphenyl group, or a triphenylenyl group, each substituted with at least one deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a biphenyl group, a terphenyl group, a triphenylenyl group, or any combination thereof, xd11 may be an integer from 1 to 10, wherein, when xd11 is 2 or more, two or more of $Ar_{402}$(s) may be identical to each other or different from each other, $CY_{401}$ and $CY_{402}$ may each independently be a benzene group, a naphthalene group, a fluorene group, a carbazole group, a benzocarbazole group, an indolocarbazole group, a dibenzofuran group, a dibenzothiophene group, a dibenzosilole group, a benzonaphthofuran group, a benzonaphthothiophene group, or a benzonaphthosilole group, $A_{21}$ may be a single bond, O, S, $N(R_{51})$, $C(R_{51})(R_{52})$, or $Si(R_{51})(R_{52})$, $A_{22}$ may be a single bond, O, S, $N(R_{53})$, $C(R_{53})(R_{54})$, or $Si(R_{53})(R_{54})$, at least one of $A_{21}$, $A_{22}$, or any combination thereof in Formula 12 may not be a single bond, $R_{51}$ to $R_{54}$, $R_{60}$, and $R_{70}$ may each independently be:

hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, a dibenzothiophenyl group, or any combination thereof;

a π electron-deficient nitrogen-free cyclic group (for example, a phenyl group, a naphthyl group, a fluorenyl group, a carbazolyl group, a dibenzofuranyl group, a dibenzothiophenyl group, a biphenyl group, a terphenyl group, or a triphenylenyl group);

a π electron-deficient nitrogen-free cyclic group (for example, a phenyl group, a naphthyl group, a fluorenyl group, a carbazolyl group, a dibenzofuranyl group, a dibenzothiophenyl group, a biphenyl group, a terphenyl group, or a triphenylenyl group) substituted with at least one deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a biphenyl group, or any combination thereof; or —$Si(Q_{404})(Q_{405})(Q_{406})$, e1 and e2 may each independently be an integer from 0 to 10, $Q_{401}$ to $Q_{406}$ may each independently be hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, a dibenzothiophenyl group, a biphenyl group, a terphenyl group, or a triphenylenyl group, and

* indicates a binding site to a neighboring atom.

In an embodiment, in Formula E-1, $Ar_{301}$ and $L_{301}$ may each independently be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with at least one deuterium, —F, —Cl, —Br, —I, a hydroxyl group, a cyano group, a nitro group, an amidino group, a hydrazine group, a hydrazone group, a $C_1$-$C_{20}$ alkyl group, a $C_1$-$C_{20}$ alkoxy group, a phenyl group, a biphenyl group, a terphenyl group, a naphthyl group, a cyano-containing phenyl group, a cyano-containing biphenyl group, a cyano-containing, terphenyl group, a cyano-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl) triazinyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, —$P(=O)(Q_{31})(Q_{32})$, or any combination thereof, at least one of $L_{301}$(s) in the number of xb1 may each independently be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, or any combination thereof, each unsubstituted or substituted with at least one deuterium, —F, —Cl, —Br, —I, a hydroxyl group, a cyano group, a nitro group, an amidino group, a hydrazine group, a hydrazone group, a $C_1$-$C_{20}$ alkyl group, a $C_1$-$C_{20}$ alkoxy group, a phenyl group, a biphenyl group, a terphenyl group, a naphthyl group, a cyano-containing phenyl group, a cyano-containing biphenyl group, a cyano-containing terphenyl group, a cyano-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl)triazinyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, —$P(=O)(Q_{31})(Q_{32})$, or any combination thereof, and $R_{301}$ may be hydrogen, deuterium, —F, —Cl, —Br, —I, a hydroxyl group, a cyano group, a nitro group, an amidino group, a hydrazine group, a hydrazone group, a $C_1$-$C_{20}$ alkyl group, a $C_1$-$C_{20}$ alkoxy group, a phenyl group, a biphenyl group, a terphenyl group, a tetraphenyl group, a naphthyl group, a cyano-containing phenyl group, a cyano-containing biphenyl group, a cyano-containing terphenyl group, a cyano-containing tetraphenyl group, a cyano-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl) pyrimidinyl group, a triazinyl group, a phenyltriazinyl group, a diphenyltriazinyl group, a biphenyltriazinyl group, a di(biphenyl)triazinyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group, but embodiments of the present disclosure are not limited thereto.

In one or more embodiments, $Ar_{301}$ may be: a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, or a dibenzothiophene group, each unsubstituted or substituted with at least one deuterium, —F, —Cl, —Br, —I, a hydroxyl group, a cyano group, a nitro group, an amidino group, a hydrazine group, a hydrazone group, a $C_1$-$C_{20}$ alkyl group, a $C_1$-$C_{20}$ alkoxy group, a phenyl group, a biphenyl group, a terphenyl group, a naphthyl group, a cyano-containing phenyl group, a cyano-containing biphenyl group, a cyano-containing terphenyl group, a cyano-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl) pyrimidinyl group, a triazinyl group, a phenyltriazinyl group, a diphenyltriazinyl group, a biphenyltriazinyl group, a di(biphenyl)triazinyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$; and a group represented by one of Formulae 5-1 to 5-3 and 6-1 to 6-33, and $L_{301}$ may be a group represented by one of Formulae 5-1 to 5-3 and 6-1 to 6-33:

5-1

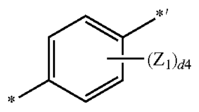

-continued
5-2
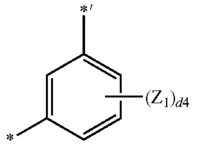
5-3
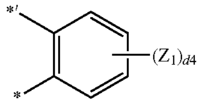
6-1
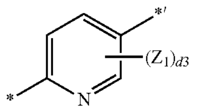
6-2
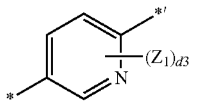
6-3
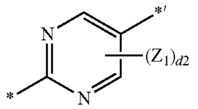
6-4
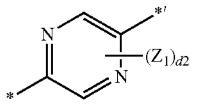
6-5
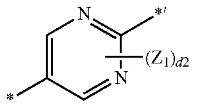
6-6
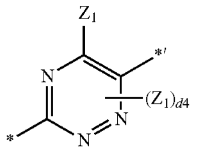
6-7
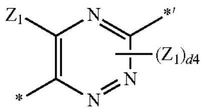
6-8
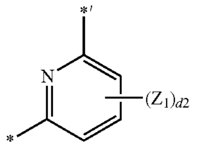
6-9
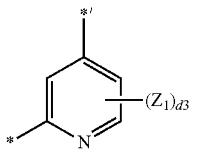
6-10
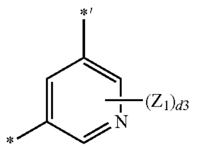
-continued
6-11
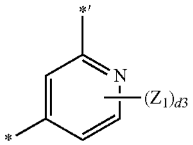
6-12
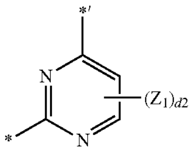
6-13
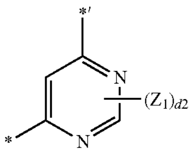
6-14
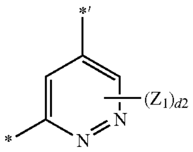
6-15
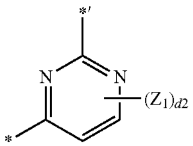
6-16
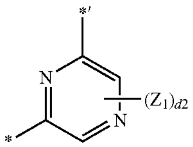
6-17
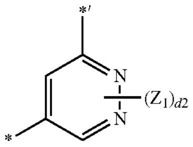
6-18
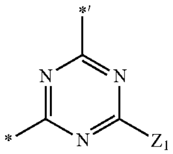
6-19
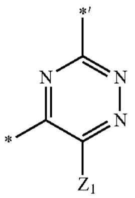

-continued 6-20

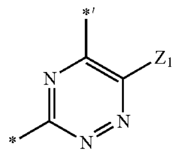

6-21

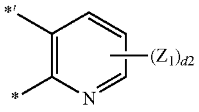

6-22

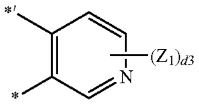

6-23

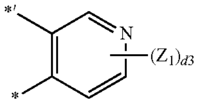

6-24

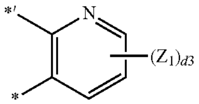

6-25

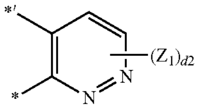

6-26

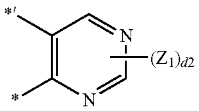

6-27

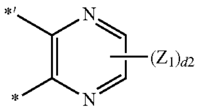

6-28

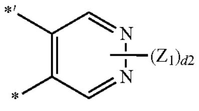

6-29

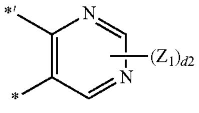

6-30

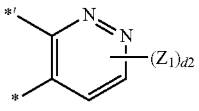

6-31

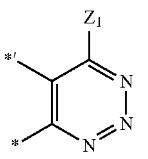

-continued 6-32

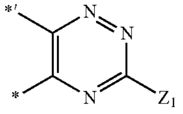

6-33

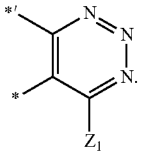

In Formulae 5-1 to 5-3 and 6-1 to 6-33, $Z_1$ may be hydrogen, deuterium, —F, —Cl, —Br, —I, a hydroxyl group, a cyano group, a nitro group, an amidino group, a hydrazine group, a hydrazone group, a $C_1$-$C_{20}$ alkyl group, a $C_1$-$C_{20}$ alkoxy group, a phenyl group, a biphenyl group, a terphenyl group, a naphthyl group, a cyano-containing phenyl group, a cyano-containing biphenyl group, a cyano-containing terphenyl group, a cyano-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), d4 may be 0, 1, 2, 3, or 4, d3 may be 0, 1, 2, or 3, d2 may be 0, 1, or 2,

* and *' each indicate a binding site to a neighboring atom, and $Q_{31}$ to $Q_{33}$ may respectively be the same as described herein.

In one or more embodiments, $L_{301}$ may be a group represented by one of Formulae 5-2, 5-3, and 6-8 to 6-33.

In one or more embodiments, $R_{301}$ may be a cyano group or a group represented by one of Formula 7-1 to 7-18, and at least one of $Ar_{402}$(s) in the number of xd11 may be a group represented by one of Formulae 7-1 to 7-18, but embodiments of the present disclosure are not limited thereto:

7-1

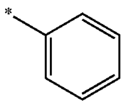

7-2

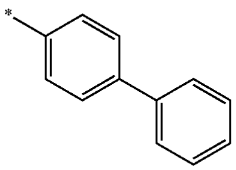

-continued
7-3
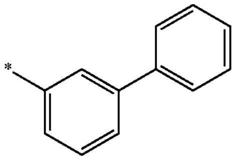
7-4
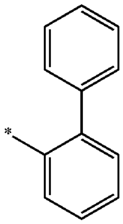
7-5
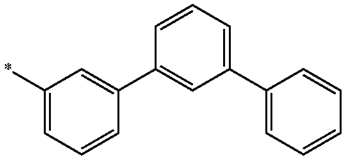
7-6
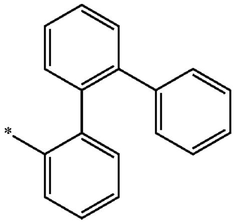
7-7
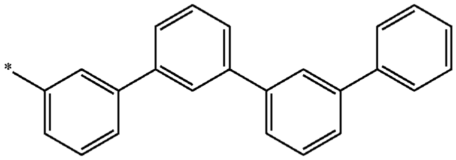
7-8
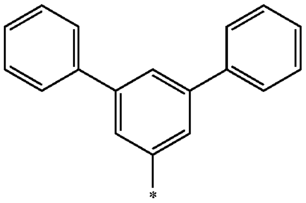
7-9
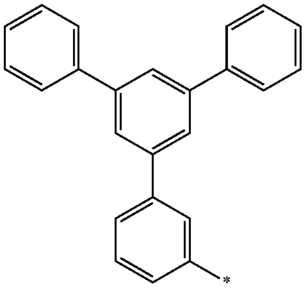
7-10
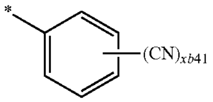
-continued
7-11
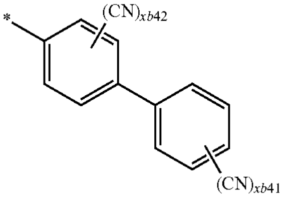
7-12
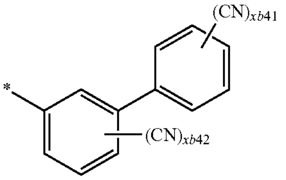
7-13
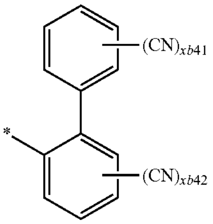
7-14
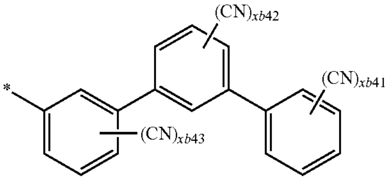
7-15
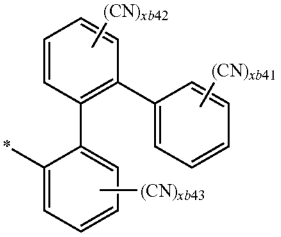
7-16
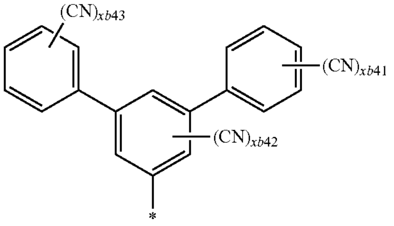
7-17
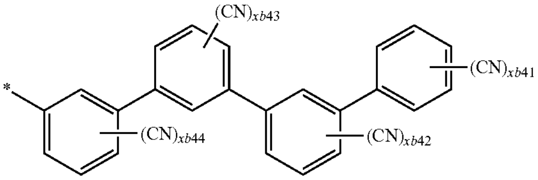

-continued 7-18

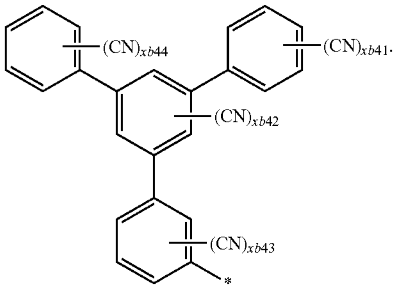

In Formulae 7-1 to 7-18, xb41 to xb44 may each be 0, 1, or 2, wherein xb41 in Formula 7-10 is not 0, the sum of xb41 and xb42 in Formulae 7-11 to 7-13 is not 0, the sum of xb41, xb42, and xb43 in Formulae 7-14 to 7-16 is not 0, the sum of xb41, xb42, xb43, and xb44 in Formulae 7-17 and 7-18 is not 0, and * indicates a binding site to a neighboring atom.

In an embodiment, two or more of $Ar_{301}$(s) in Formula E-1 may be identical to or different from each other, two or more of $L_{301}$(s) in Formula E-1 may be identical to or different from each other, two or more of $L_{401}$(s) in Formula H-1 may be identical to or different from each other, and two or more $Ar_{402}$(s) in Formula H-1 may be identical to or different from each other.

In an embodiment, the electron-transporting host may include i) at least one of a cyano group, a pyrimidine group, a pyrazine group, a triazine group, or any combination thereof, and ii) a triphenylene group, and the hole-transporting host may include a carbazole group.

In one or more embodiments, the electron-transporting host may include at least one cyano group.

The electron-transporting host may be, for example, compounds of a group HE1 to HE7 and Compound HE6-203, but embodiments of the present disclosure are not limited thereto:

HE6-203

HE6-203

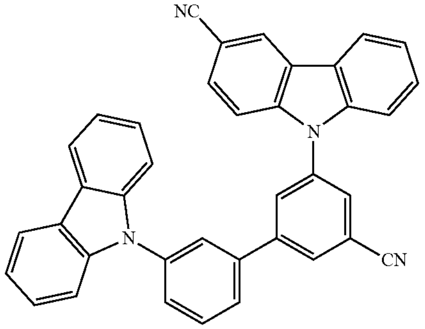

-continued

Group HE1

H-E1

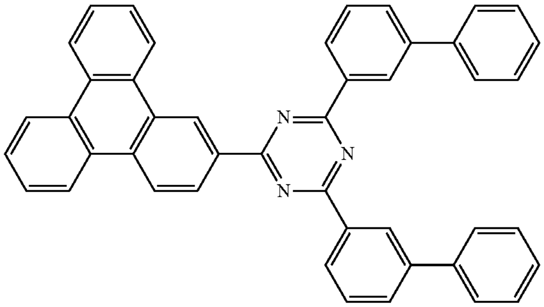

H-E2

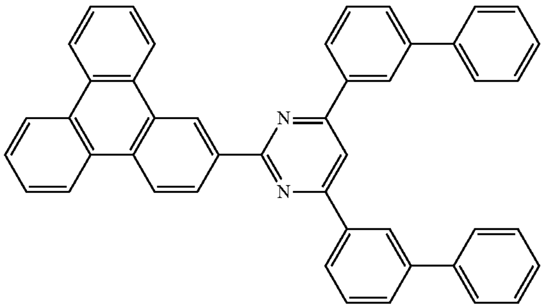

H-E3

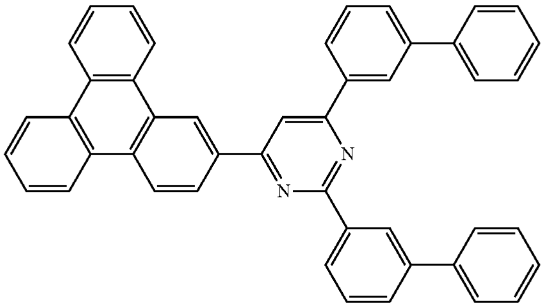

H-E4

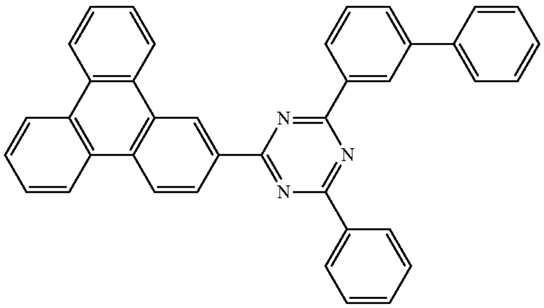

-continued
H-E5
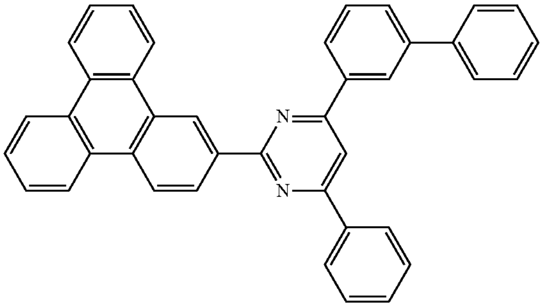
H-E6
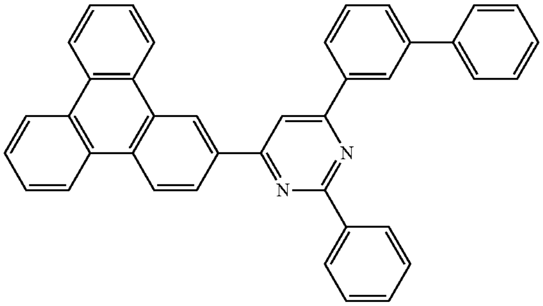
H-E7
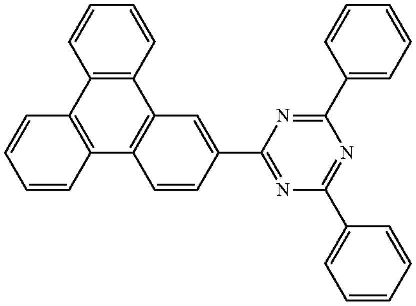
H-E8
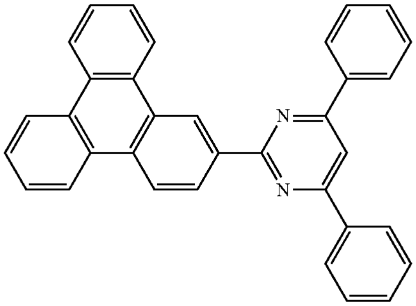
H-E9
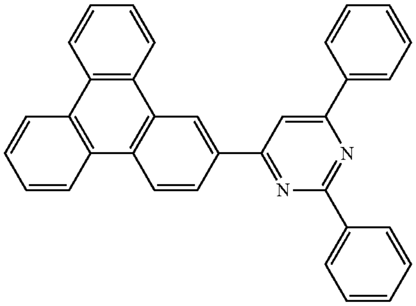
-continued
H-E10
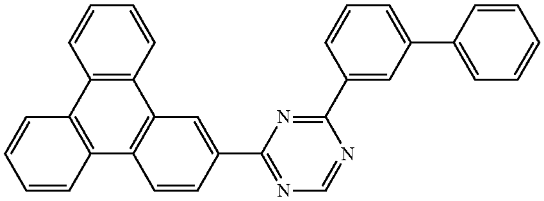
H-E11
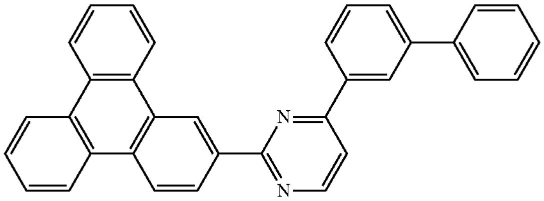
H-E12
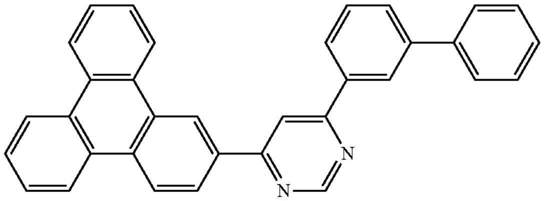
H-E13
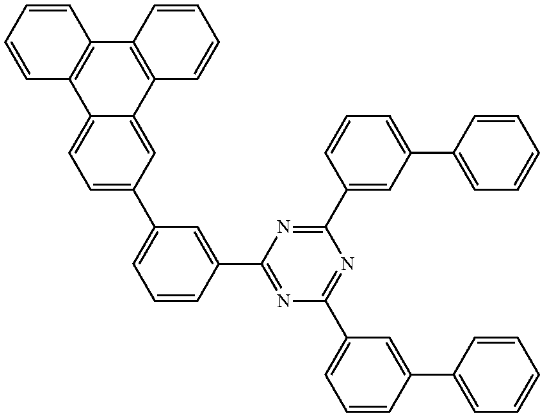
H-E14
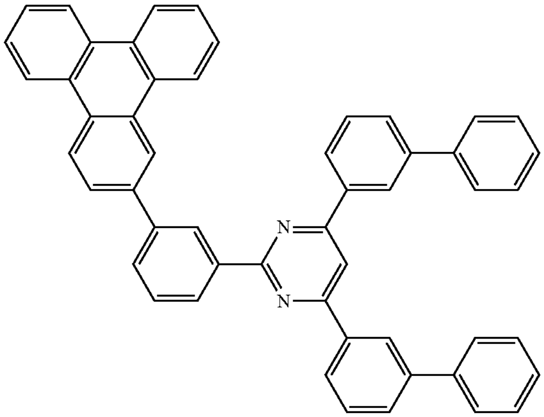

-continued
H-E15
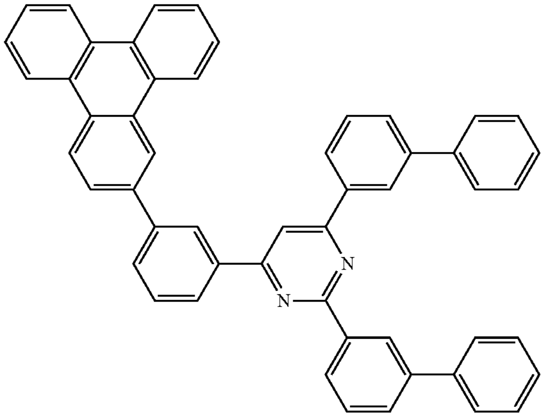
H-E16
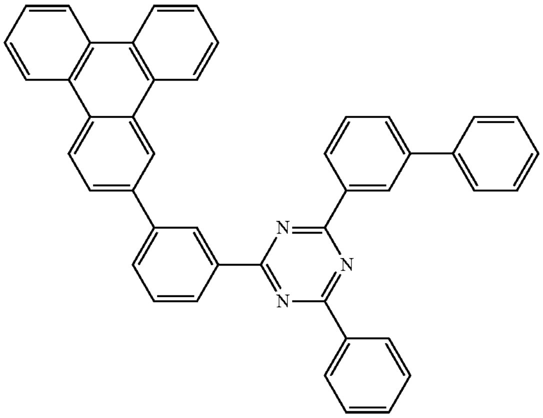
H-E17
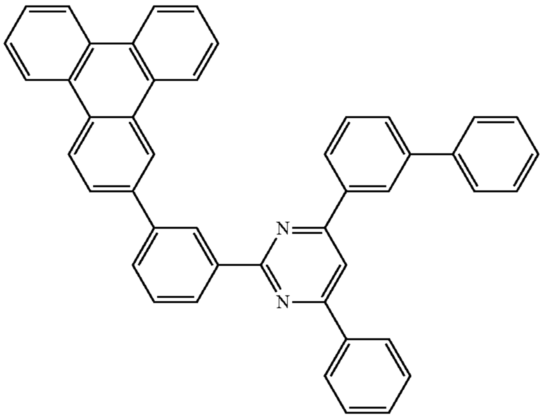
-continued
H-E18
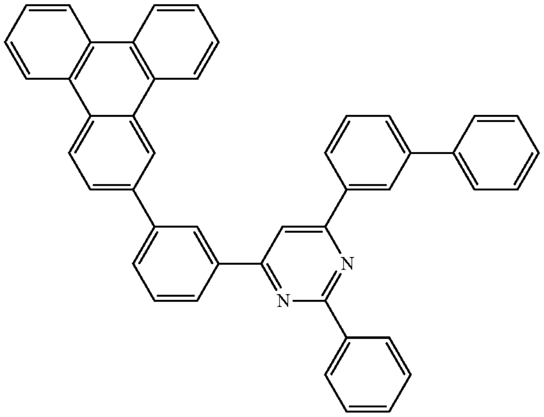
H-E19
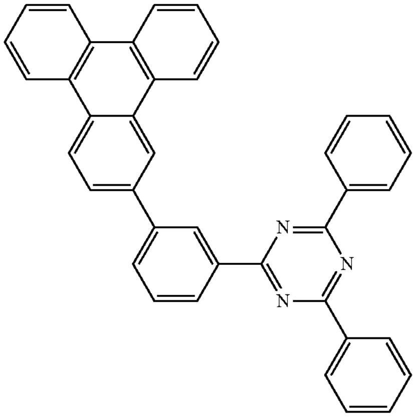
H-E20
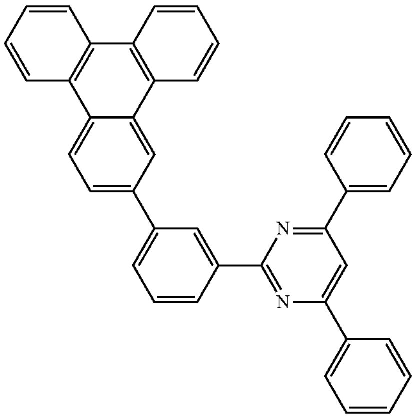

-continued
H-E21
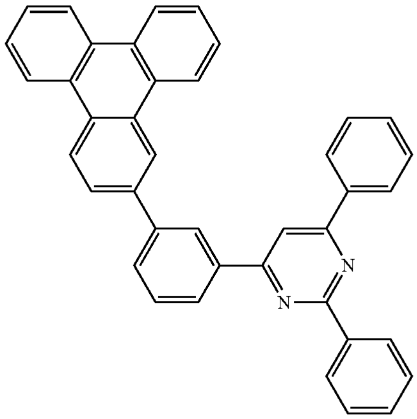
H-E22
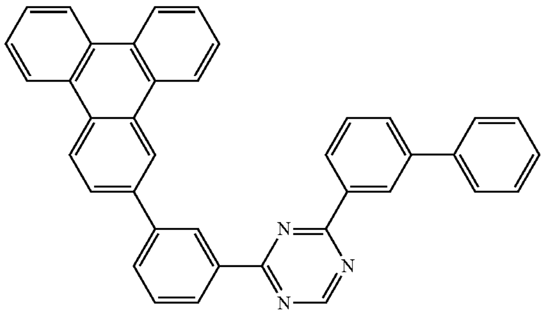
H-E23
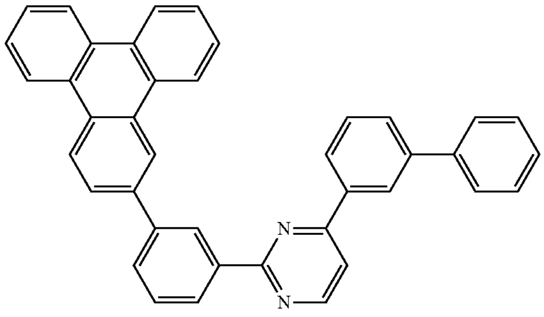
H-E24
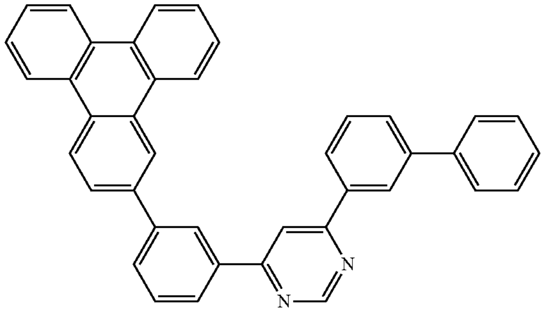
-continued
H-E25
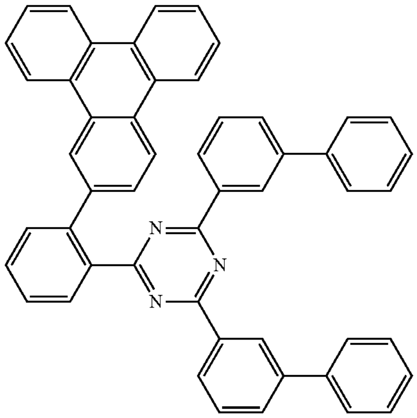
H-E26
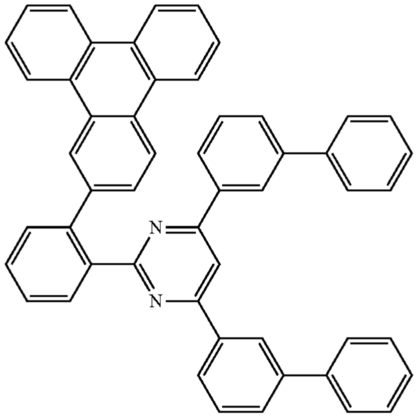
H-E27
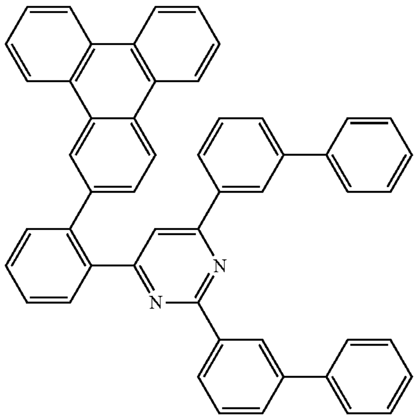

-continued
H-E28
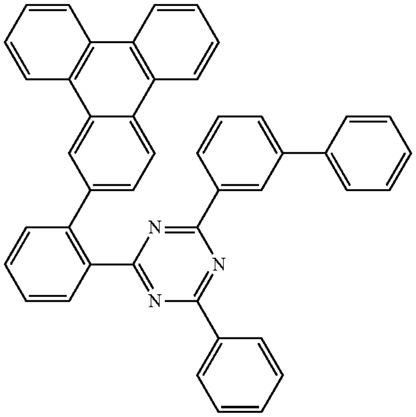
H-E29
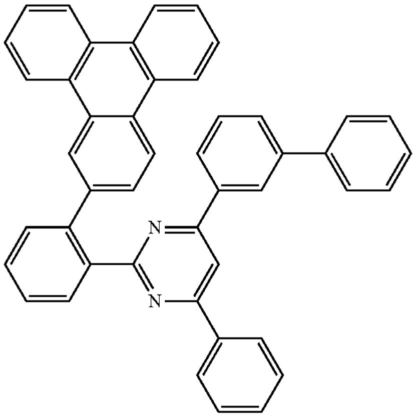
H-E30
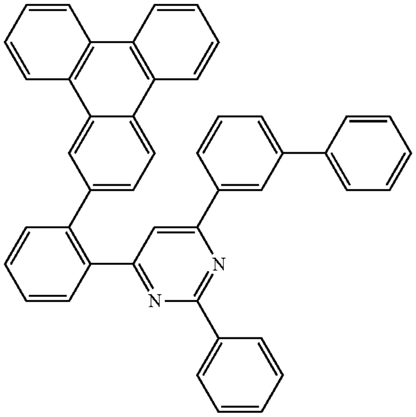
-continued
H-E31
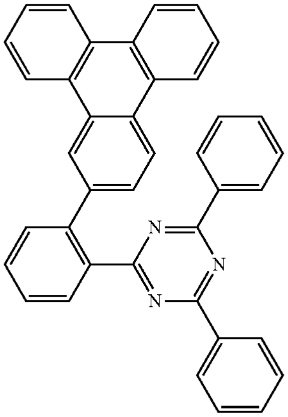
H-E32
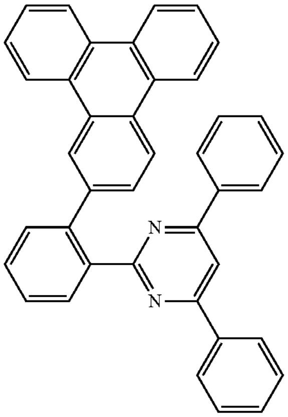
H-E33
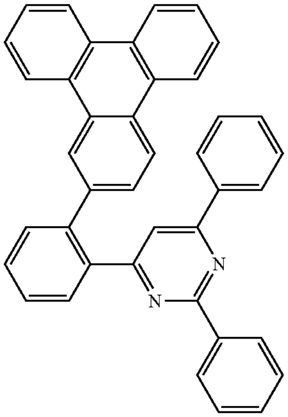
H-E34
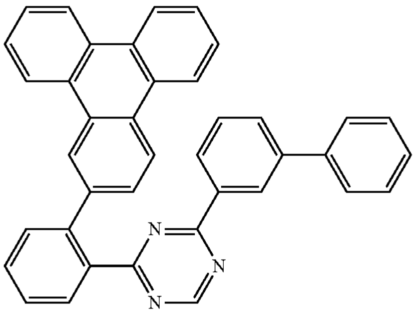

-continued
H-E35
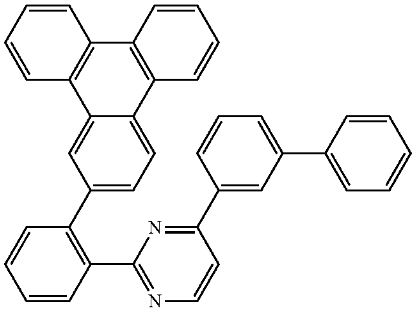
H-E36
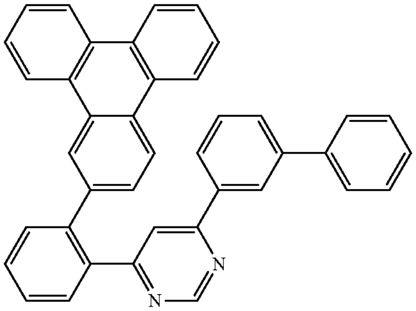
H-E37
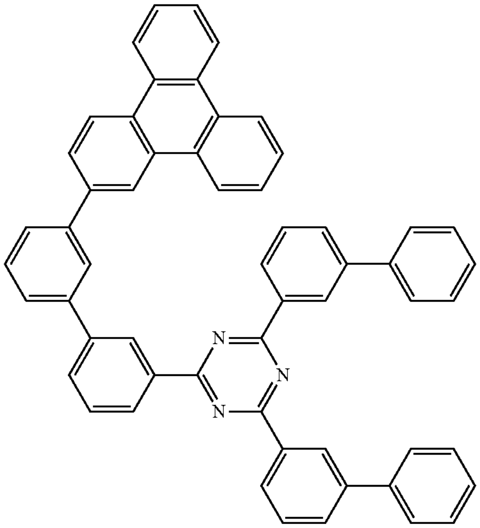
-continued
H-E38
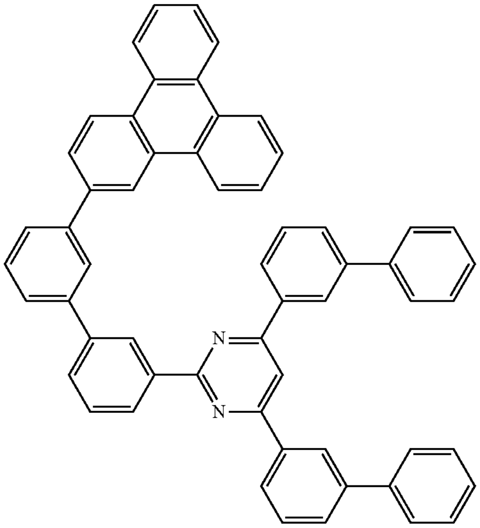
H-E39
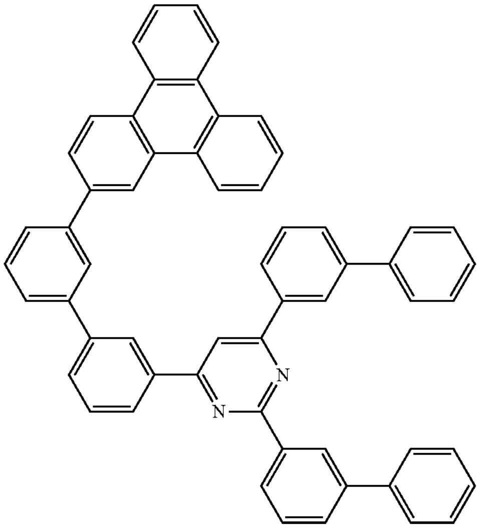
H-E40
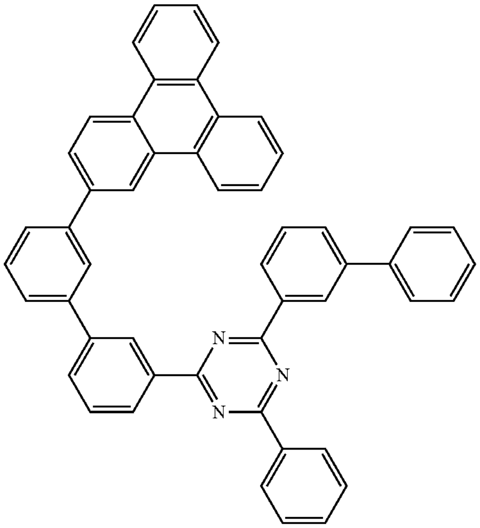

-continued
H-E41
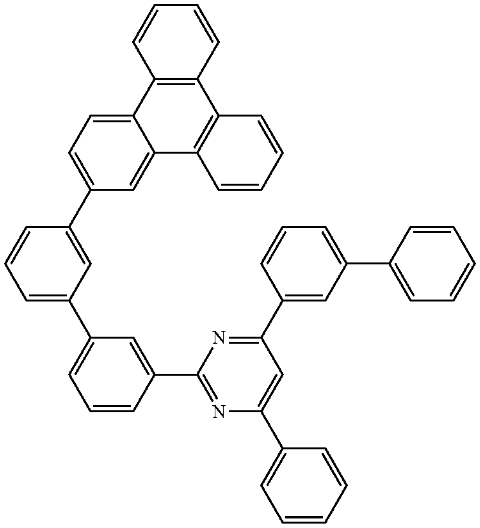
H-E42
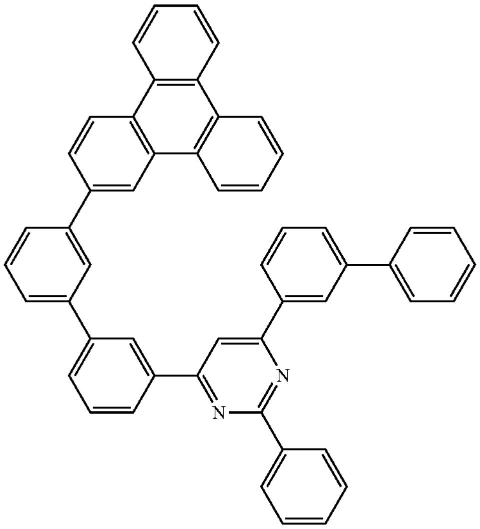
H-E43
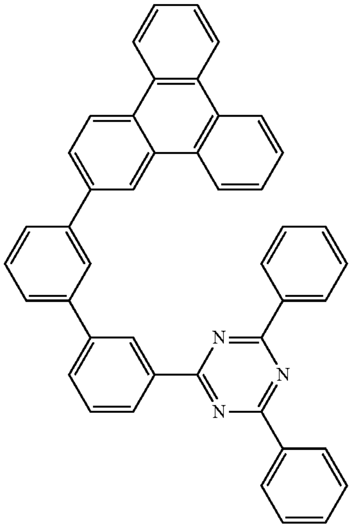
-continued
H-E44
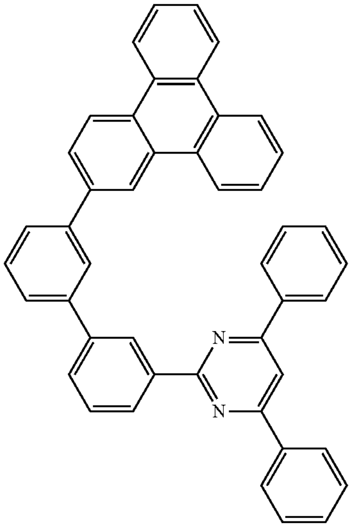
H-E45
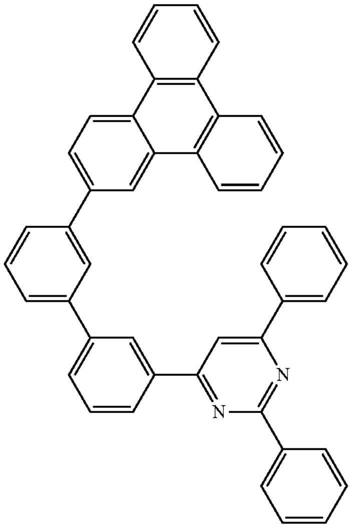
H-E46
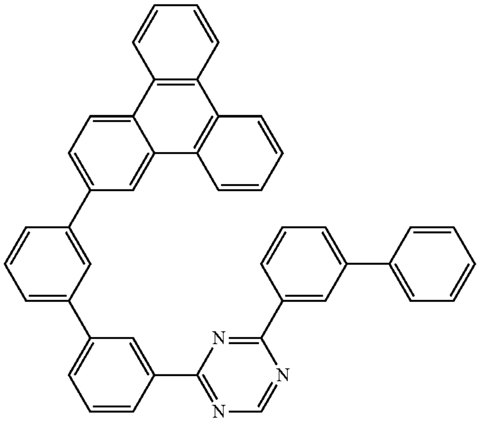

-continued
H-E47
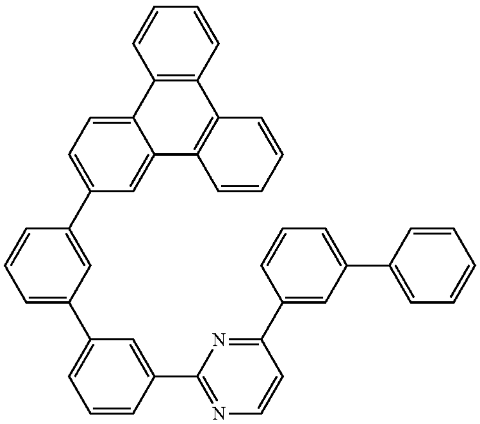
H-E48
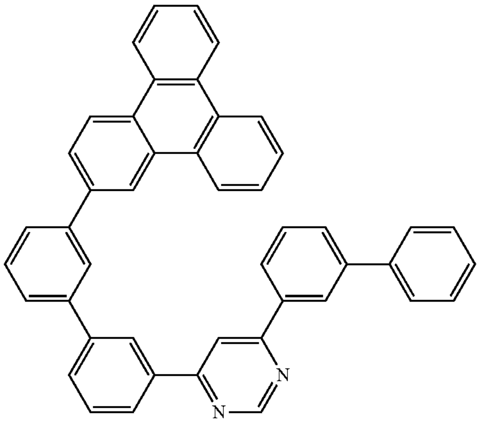
H-E49
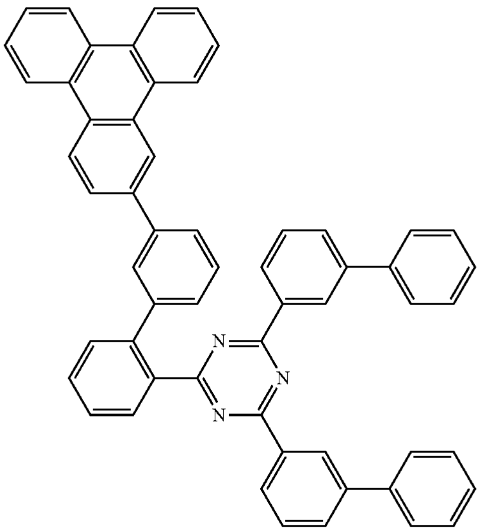
-continued
H-E50
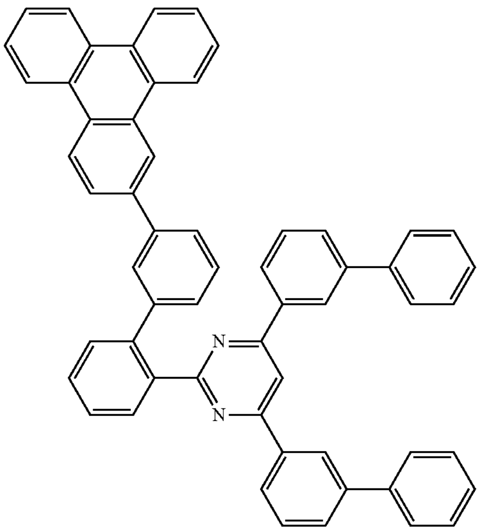
H-E51
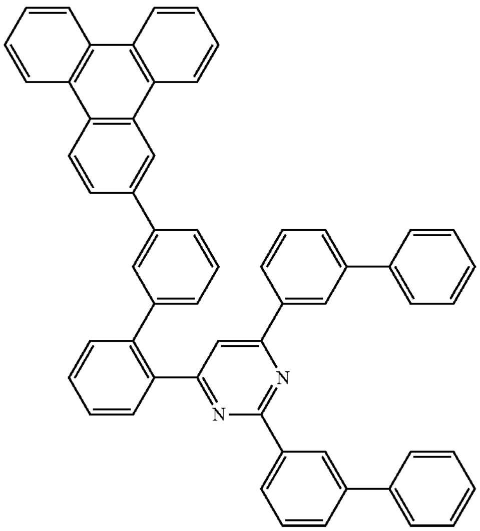
H-E52
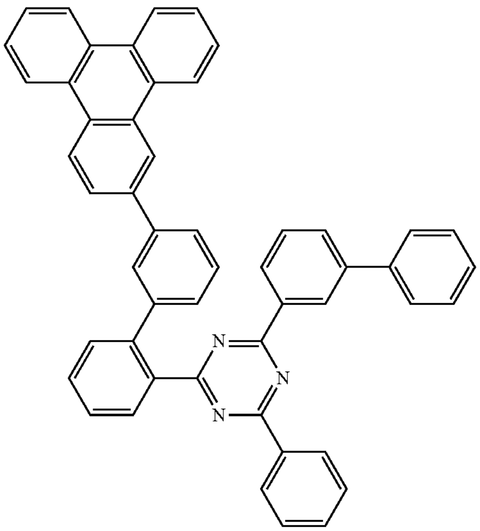

-continued
H-E53
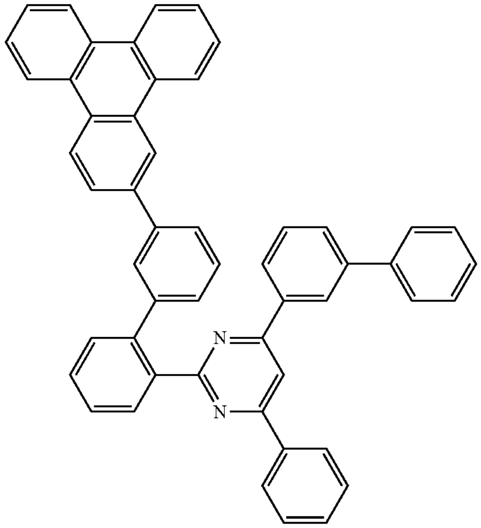
H-E54
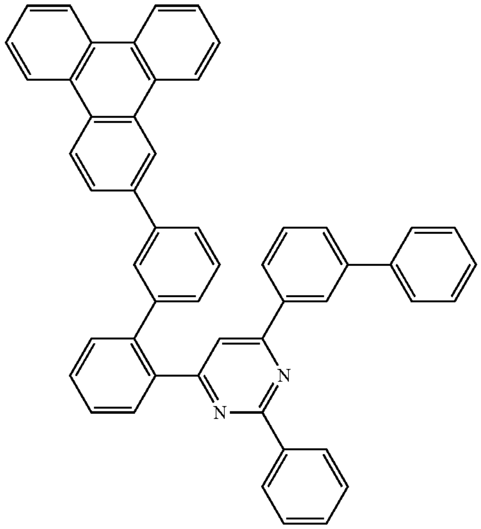
H-E55
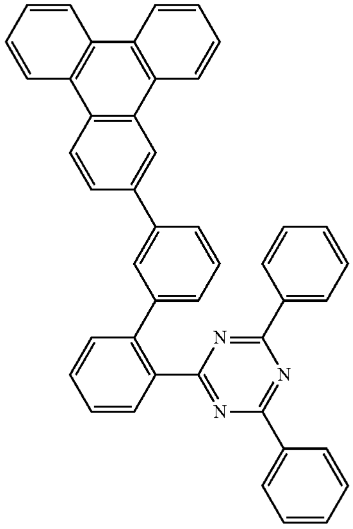
-continued
H-E56
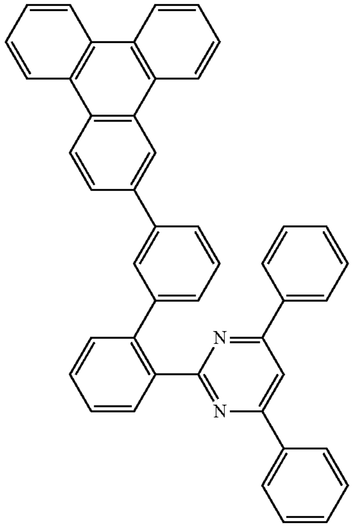
H-E57
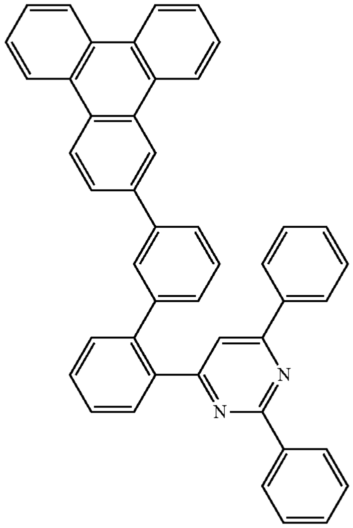
H-E58
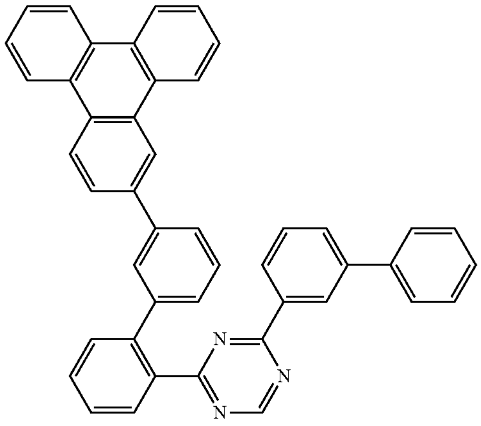

-continued
H-E59
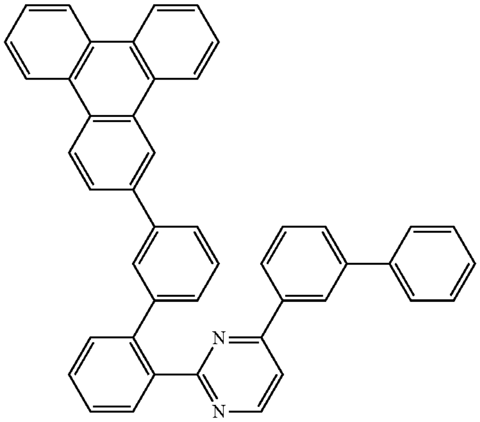
H-E60
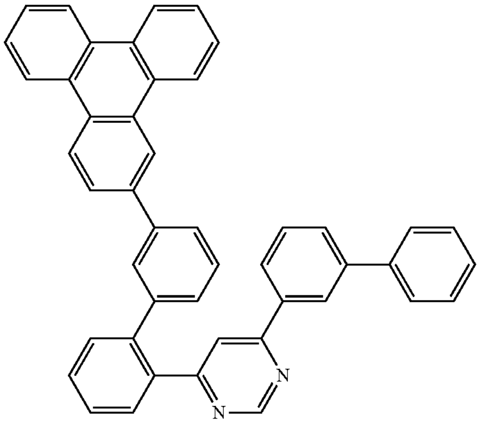
H-E61
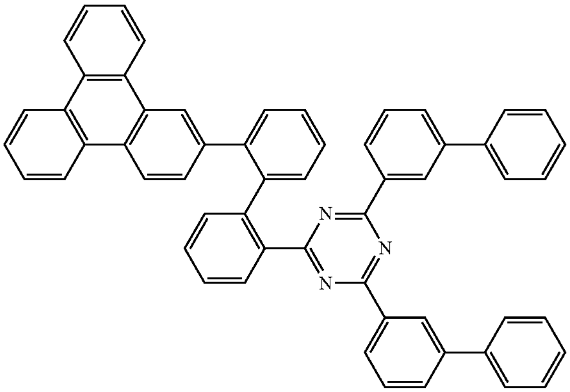
-continued
H-E62
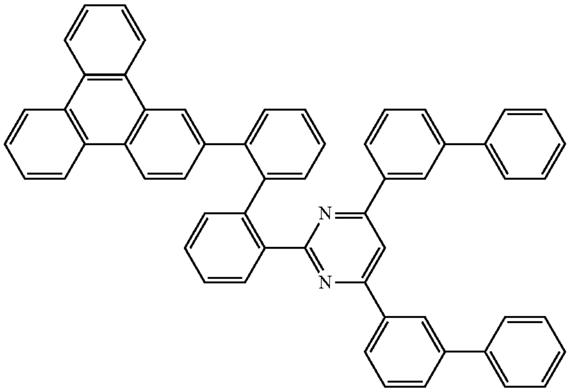
H-E63
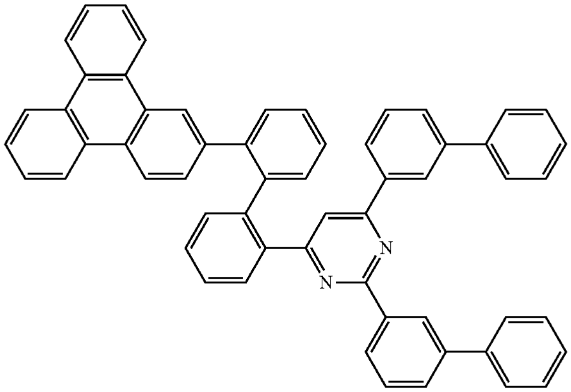
H-E64
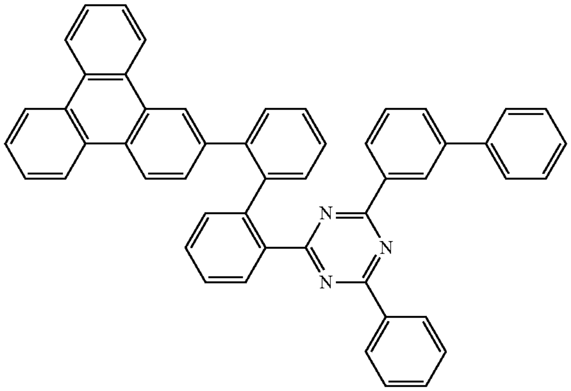
H-E65
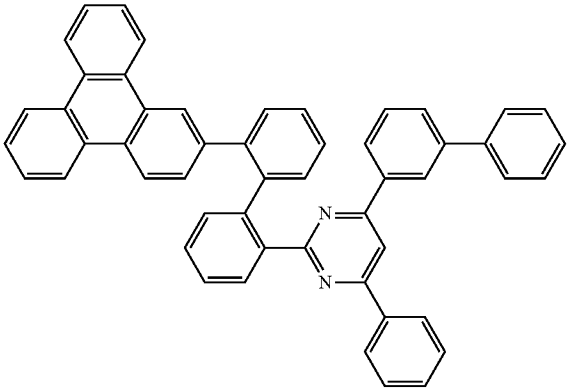

-continued
H-E66
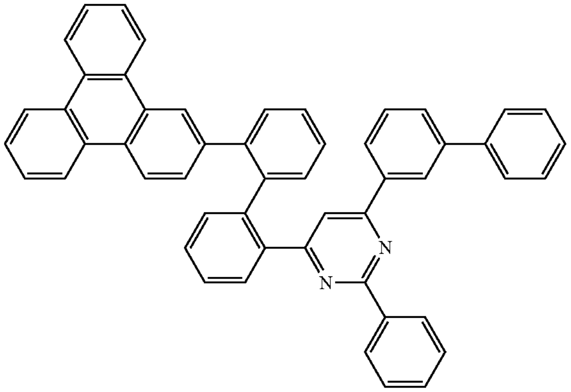
H-E67
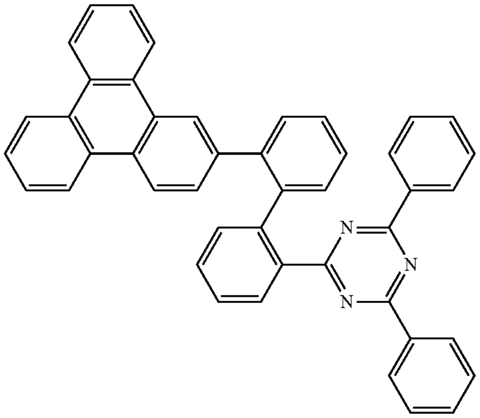
H-E68
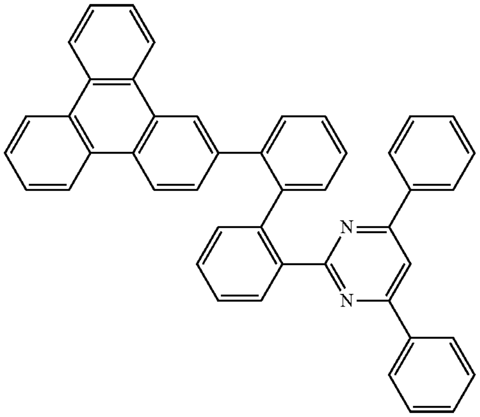
-continued
H-E69
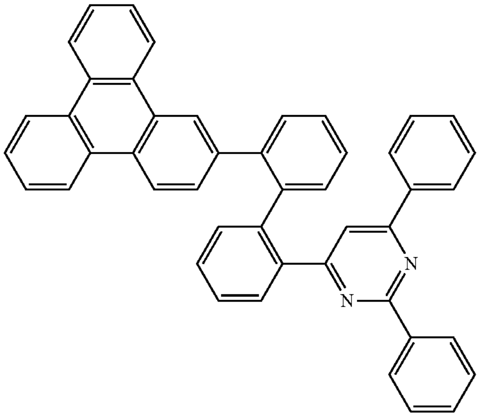
H-E70
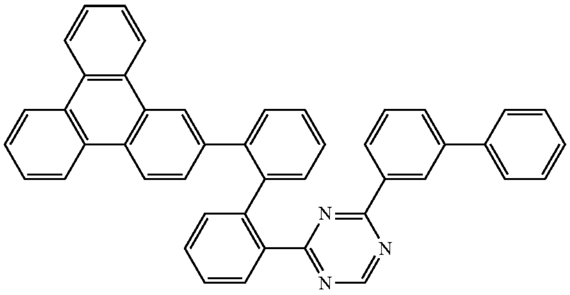
H-E71
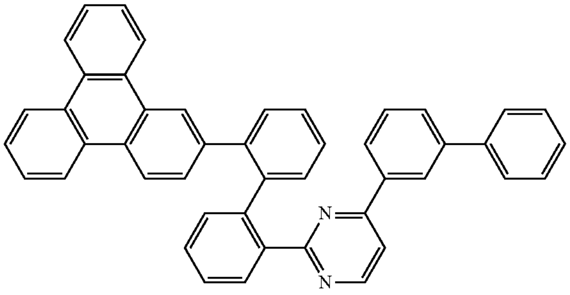
H-E72
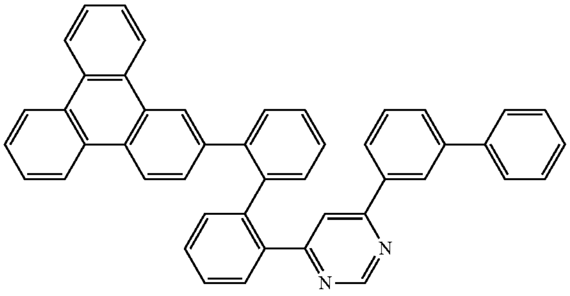

-continued
H-E73
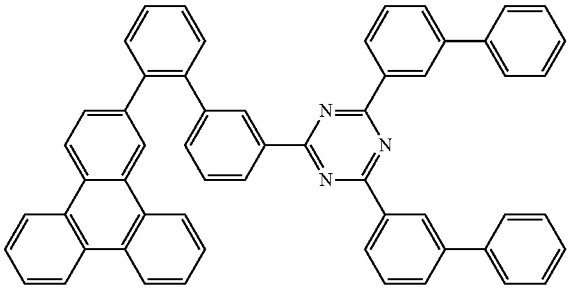
H-E74
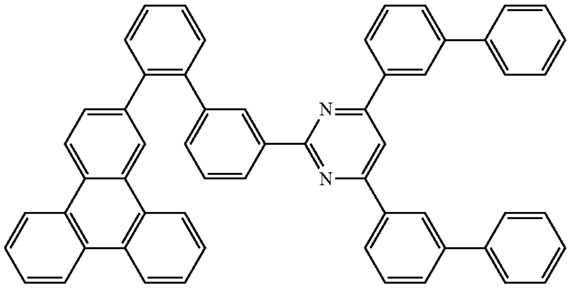
H-E75
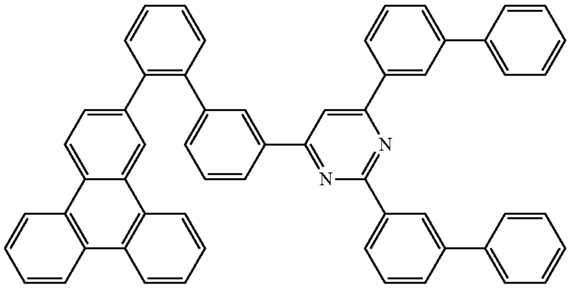
H-E76
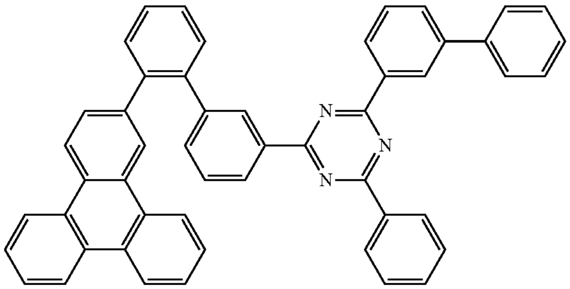
H-E77
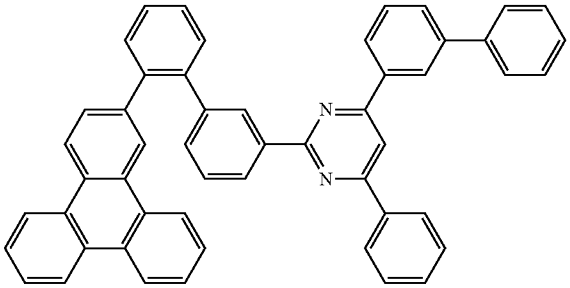
-continued
H-E78
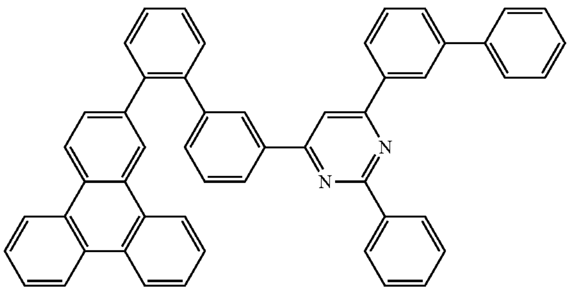
H-E79
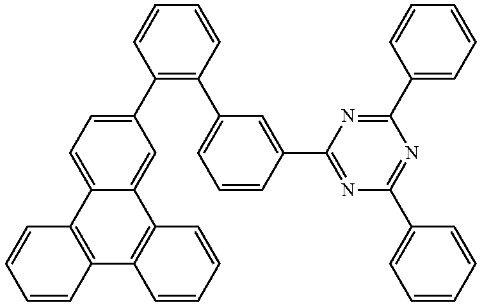
H-E80
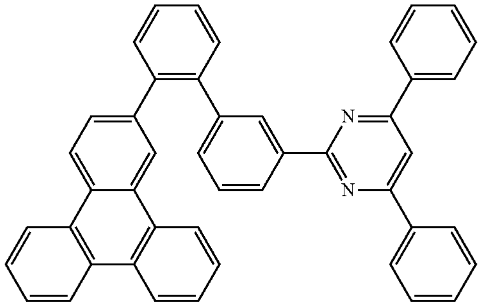
H-E81
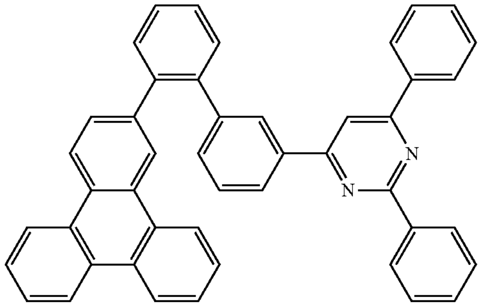
H-E82
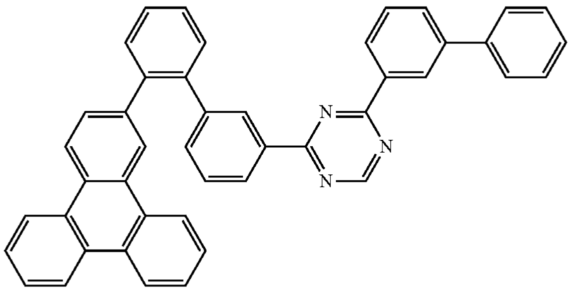

-continued
H-E83
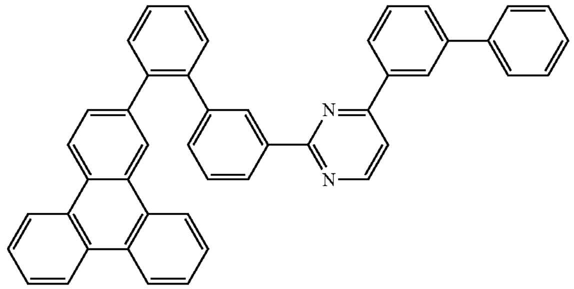
H-E84
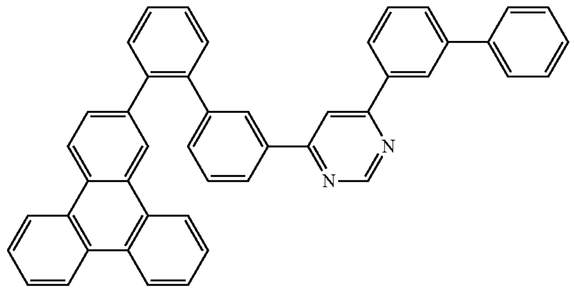
H-E(1)
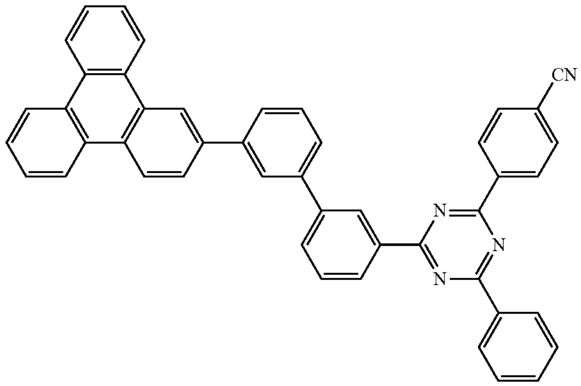
H-E(2)
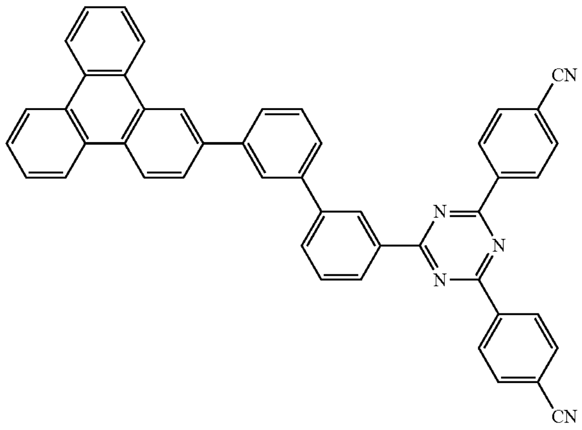
-continued
H-E(3)
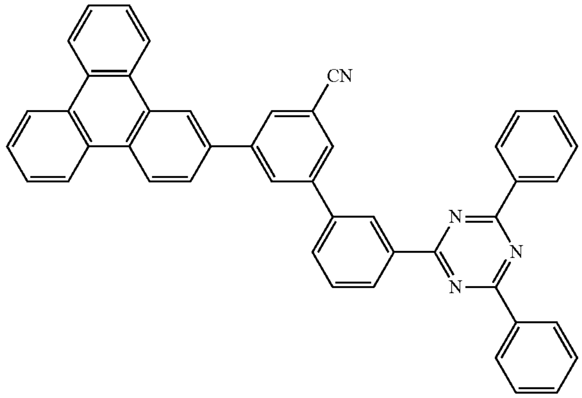
H-E(4)
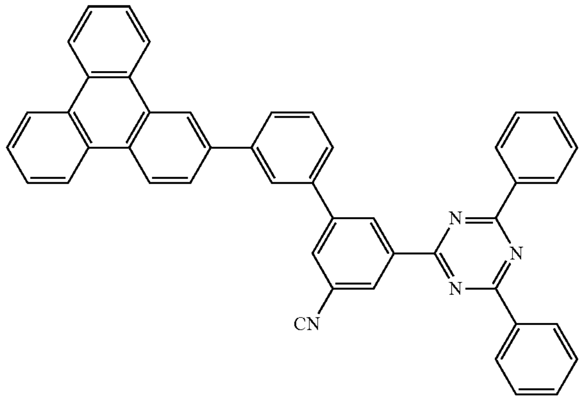
A-1
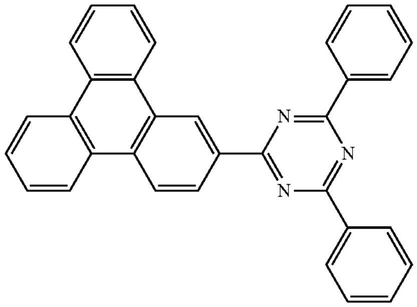
A-2
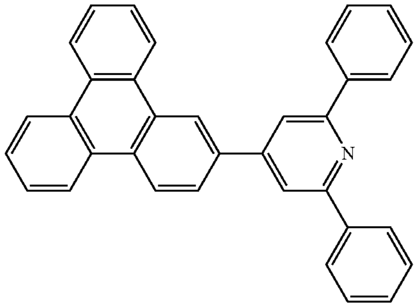

-continued
A-3
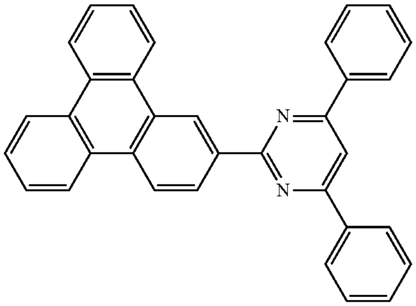
A-4
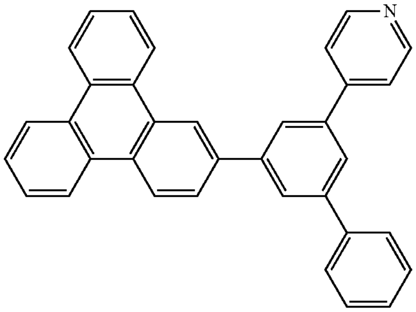
A-5
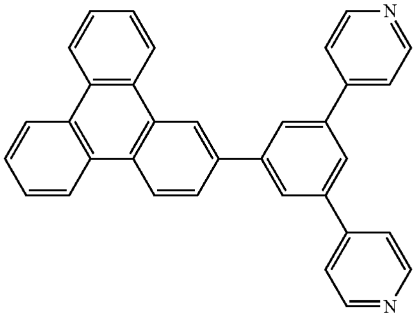
A-6
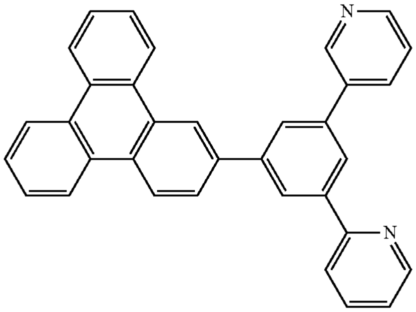
A-7
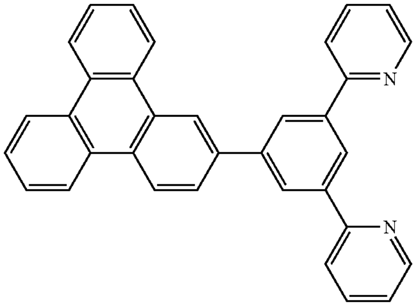
-continued
A-8
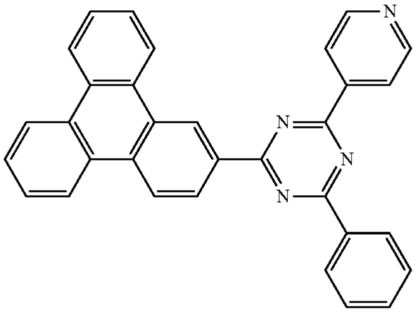
A-9
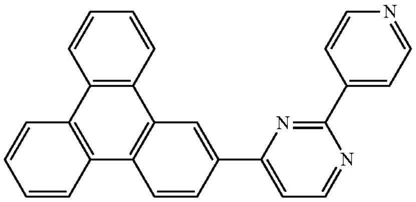
A-10
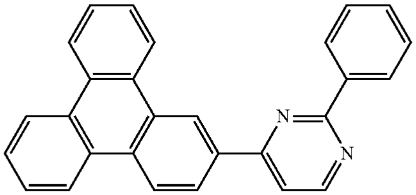
A-11
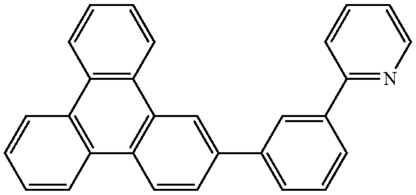
A-12
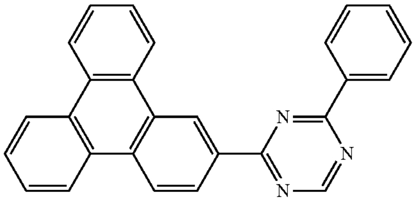
A-13
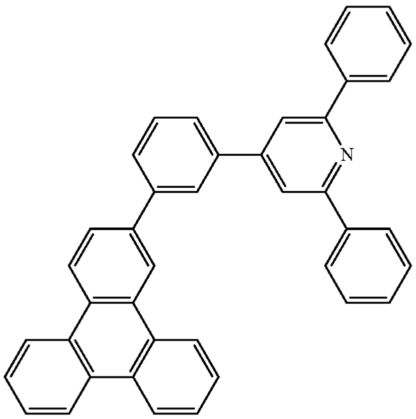

-continued
A-14
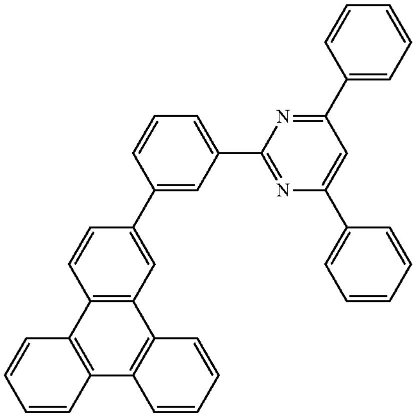
A-15
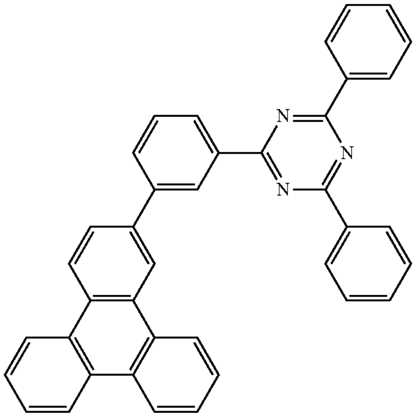
A-16
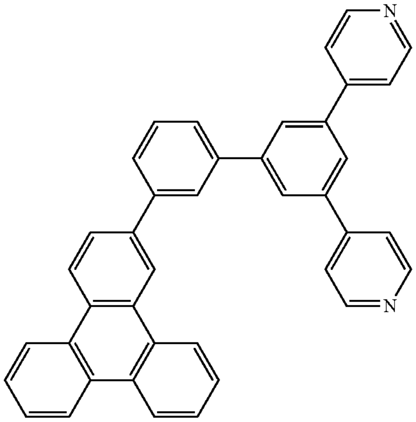
-continued
A-17
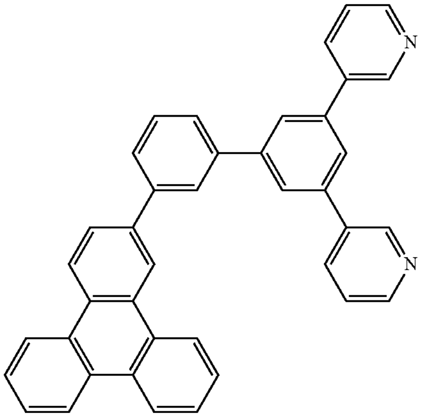
A-18
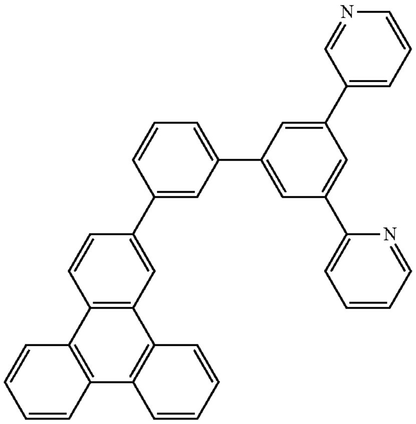
A-19
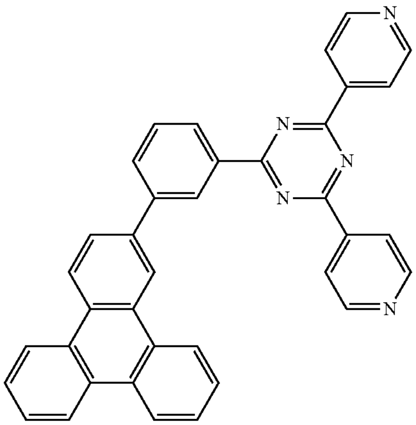

-continued
A-20
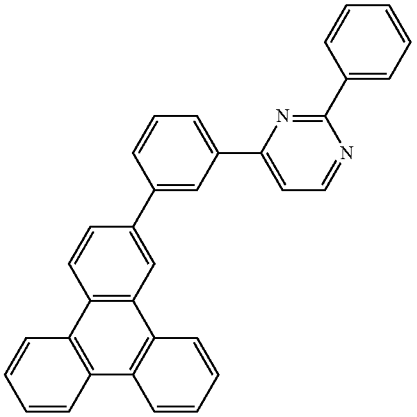
A-21
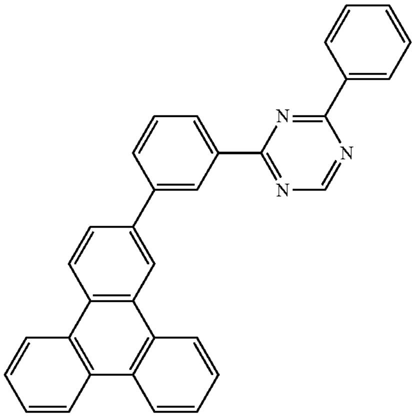
A-22
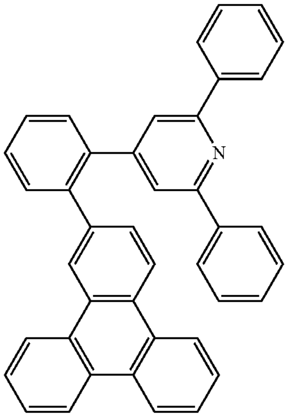
-continued
A-23
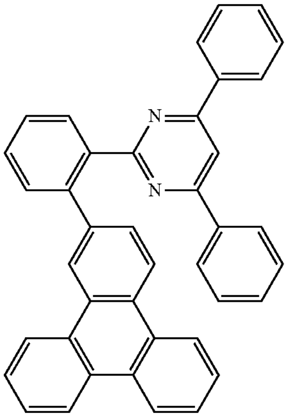
A-24
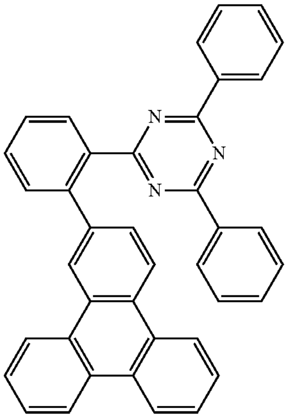
A-25
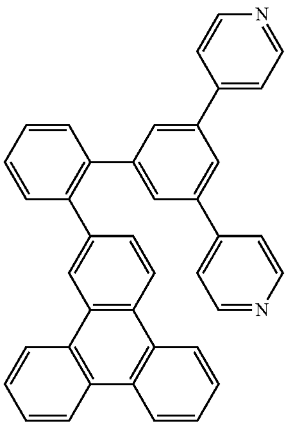

-continued
A-26
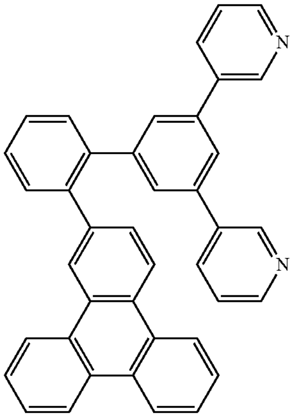
A-27
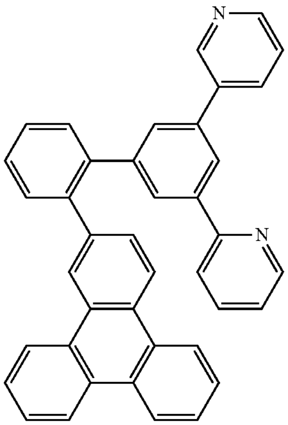
A-28
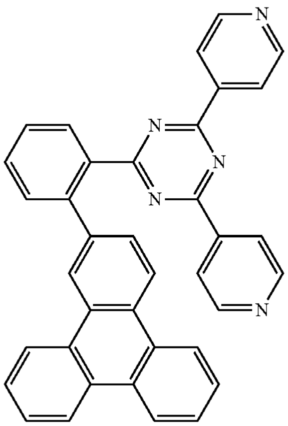
-continued
A-29
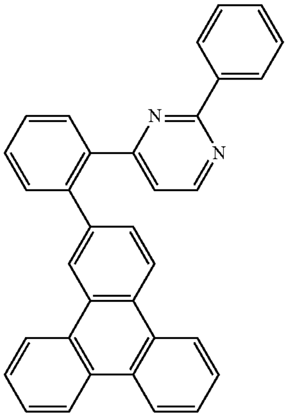
A-30
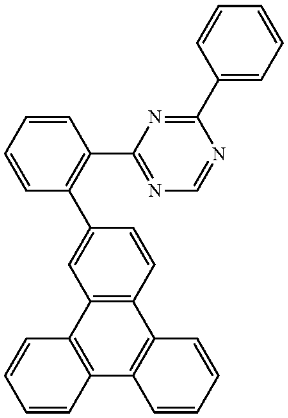
A-31
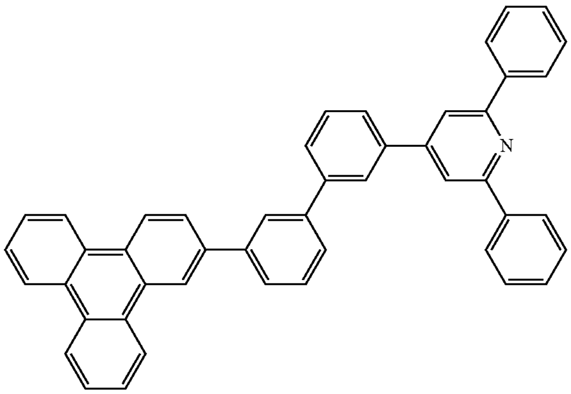

-continued
A-32
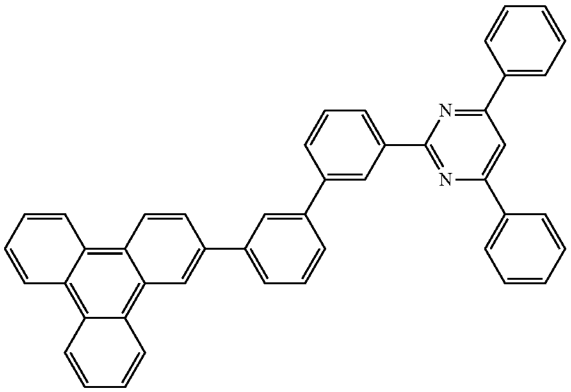
A-33
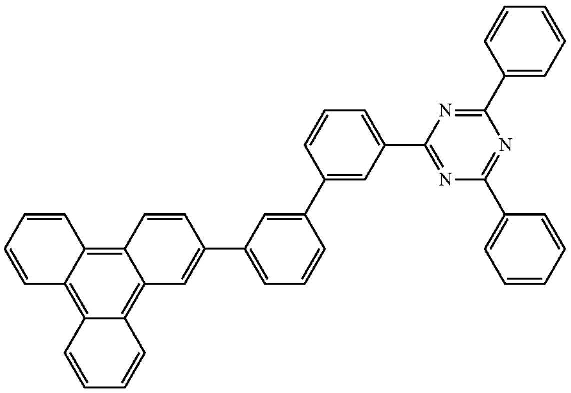
A-34
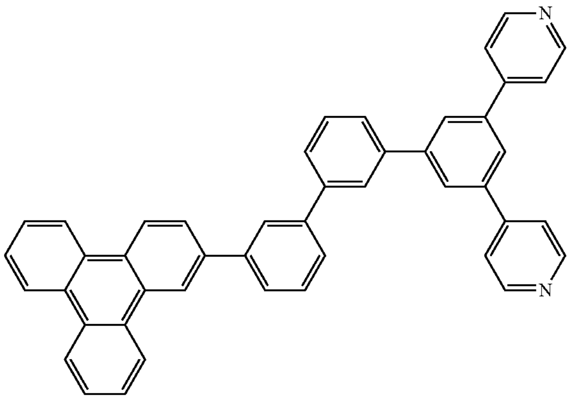
-continued
A-35
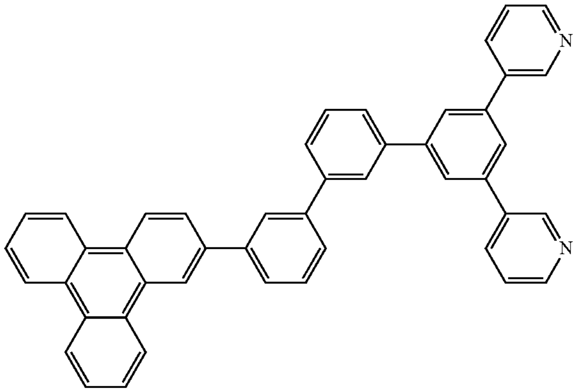
A-36
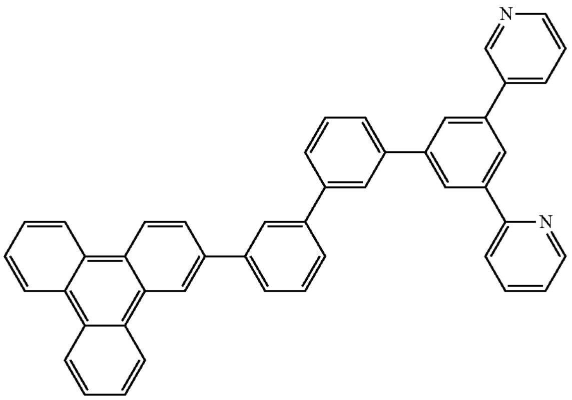
A-37
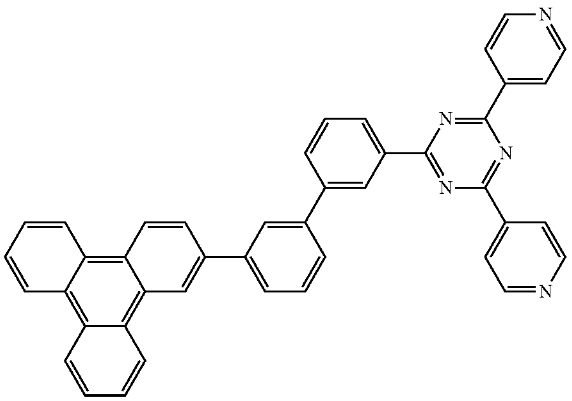

-continued
A-38
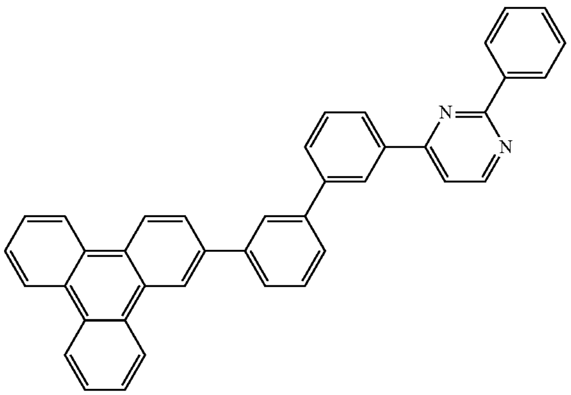
A-39
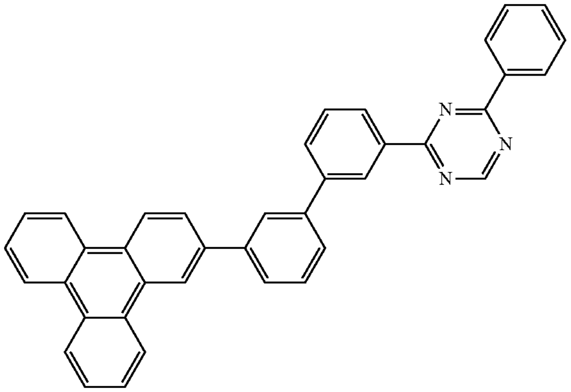
A-40
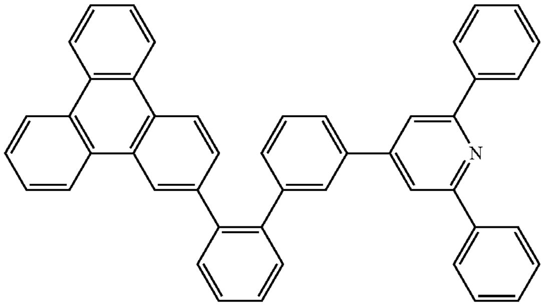
A-41
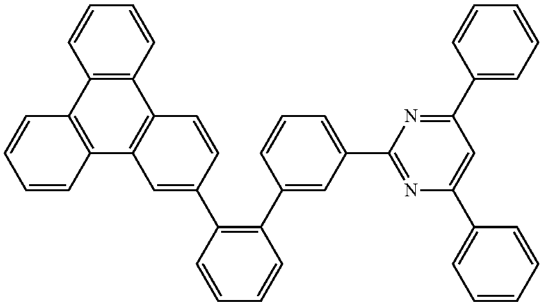
-continued
A-42
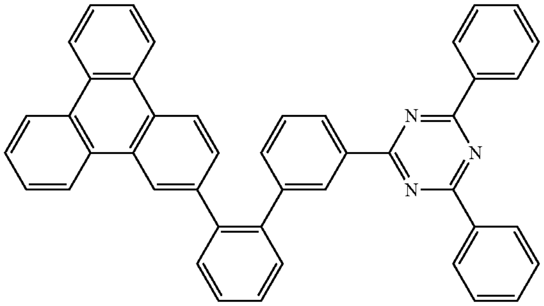
A-43
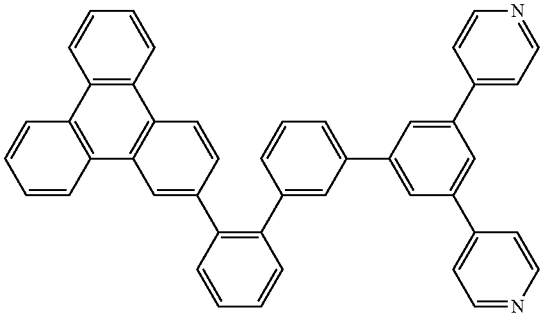
A-44
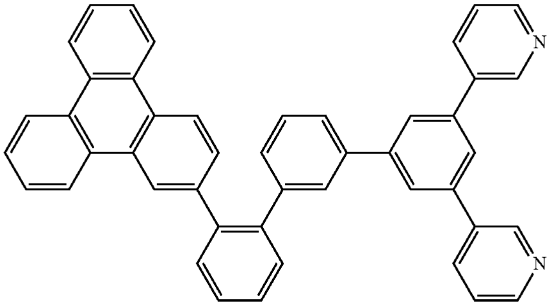
A-45
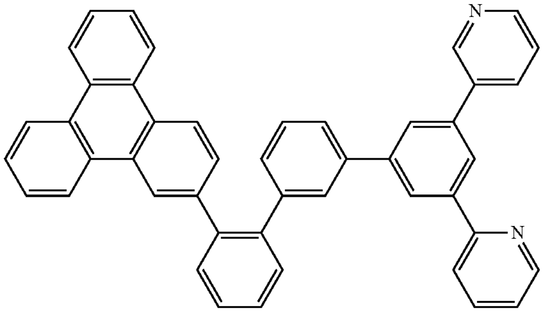

-continued
A-46
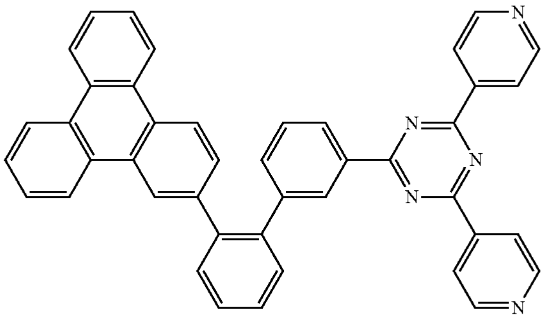
A-47
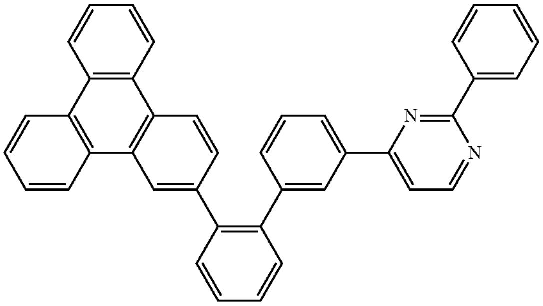
A-48
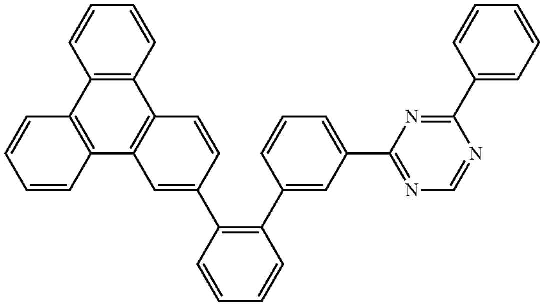
A-49
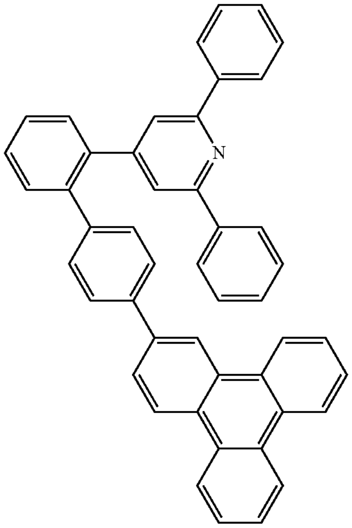
-continued
A-50
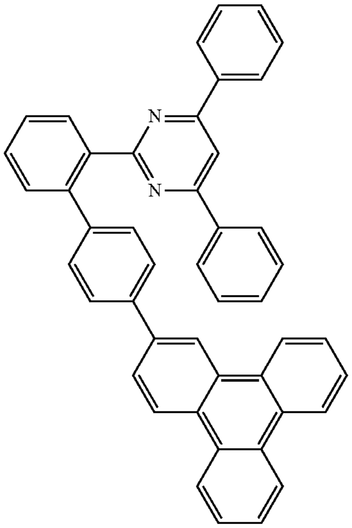
A-51
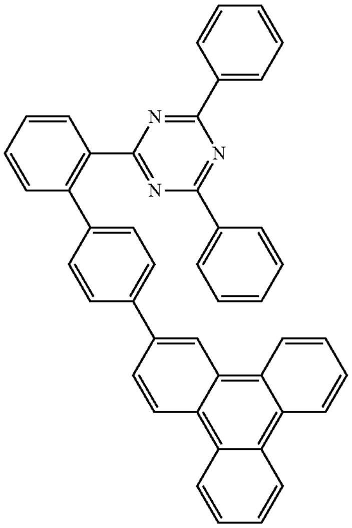
A-52
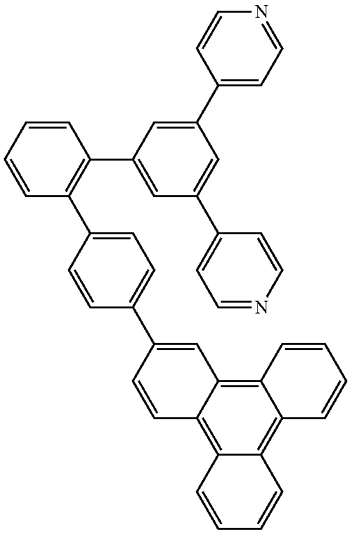

-continued
A-53
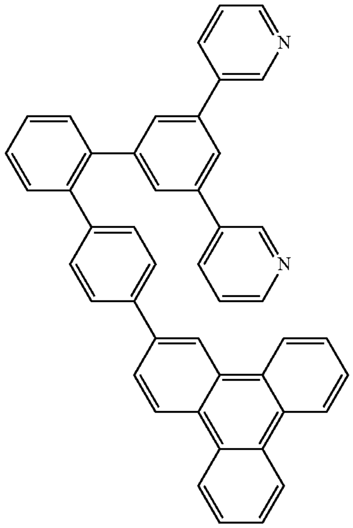
A-54
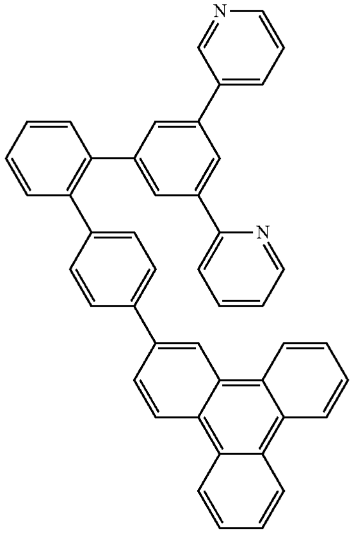
A-55
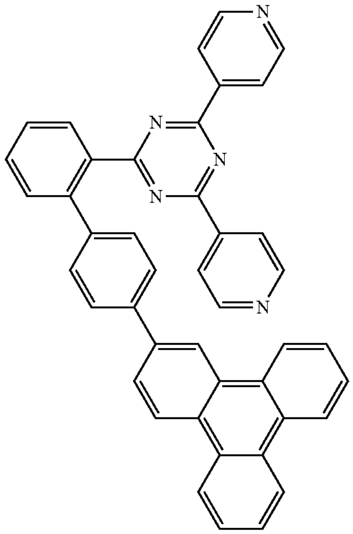
-continued
A-56
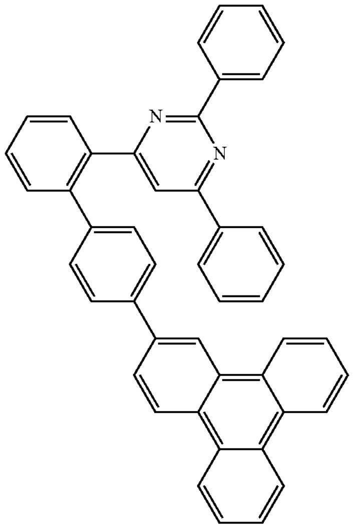
A-57
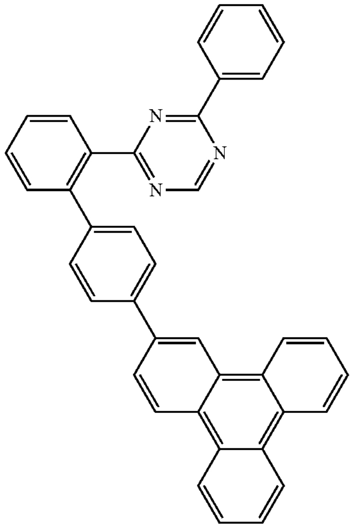
A-58
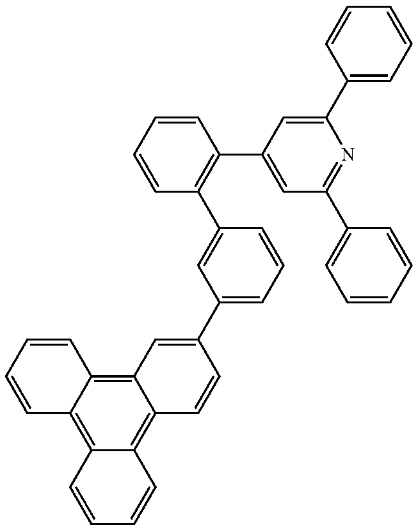

-continued
A-59
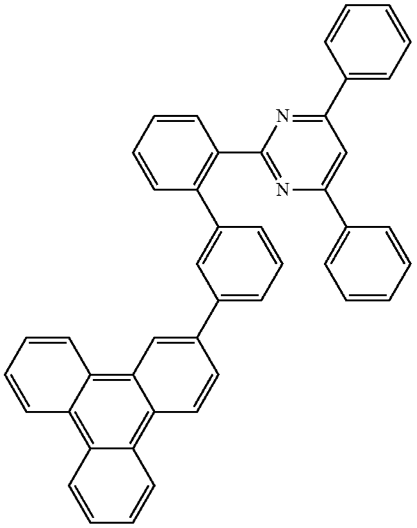
A-60
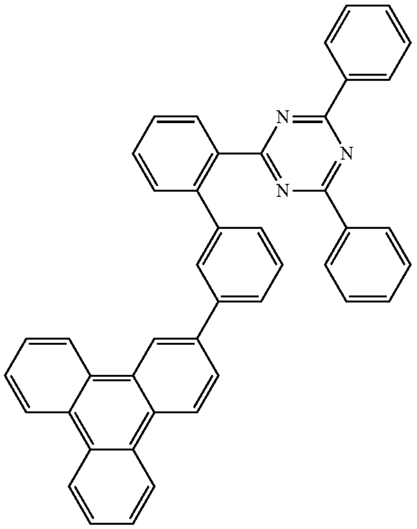
A-61
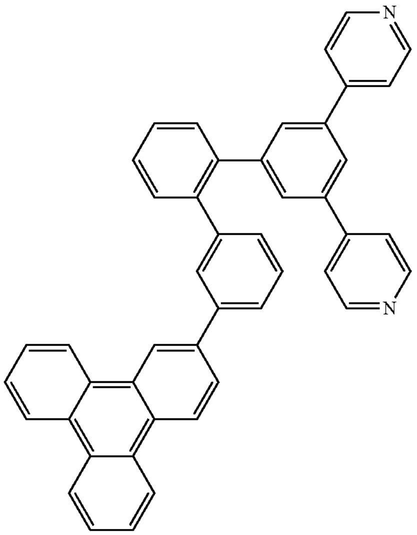
-continued
A-62
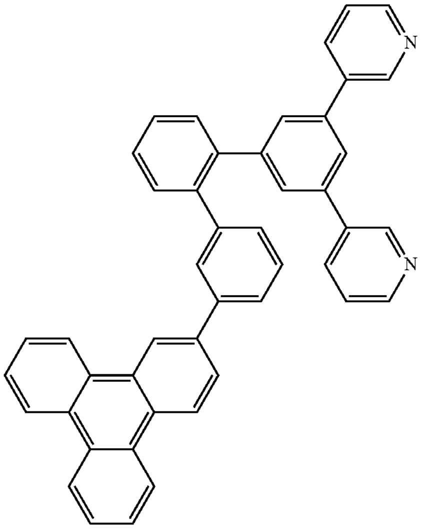
A-63
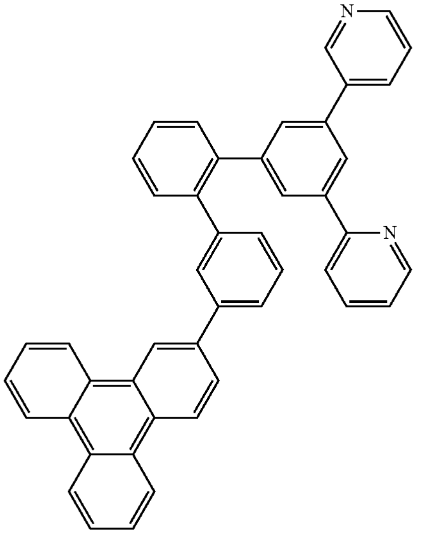
A-64
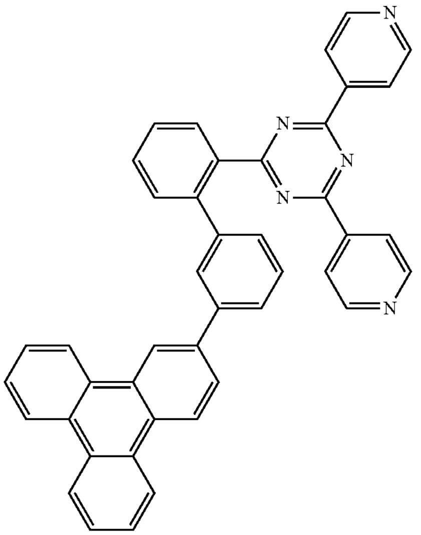

-continued
A-65
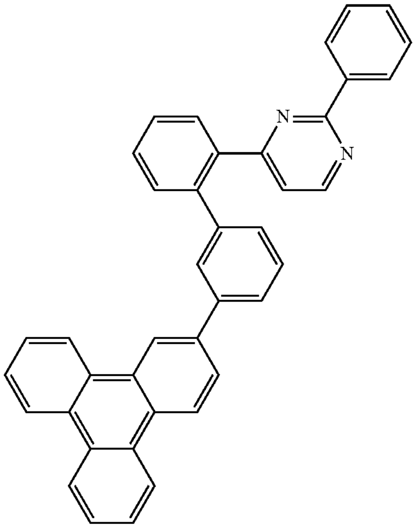
A-66
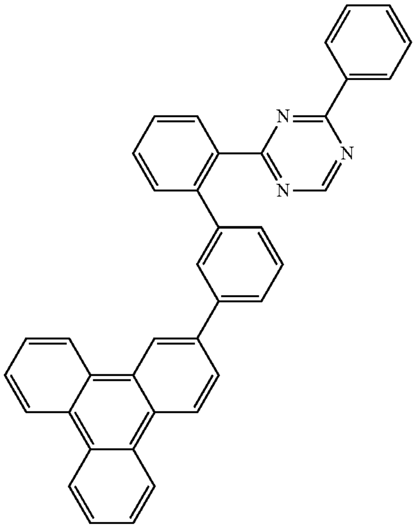
A-67
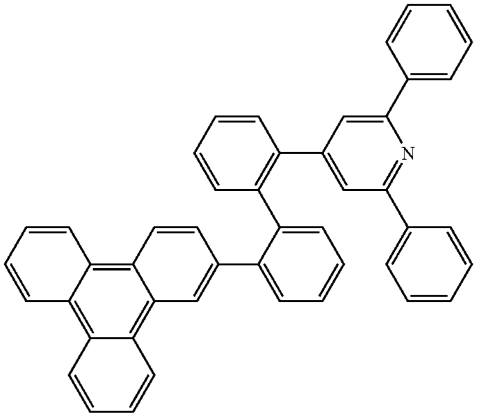
-continued
A-68
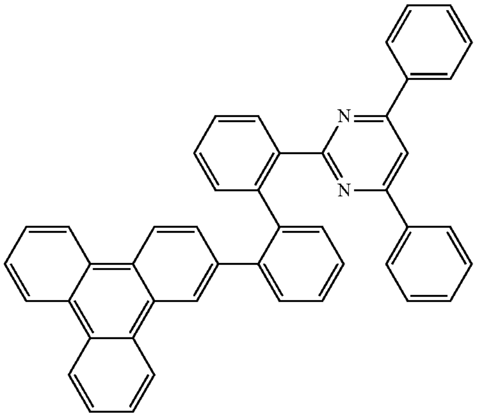
A-69
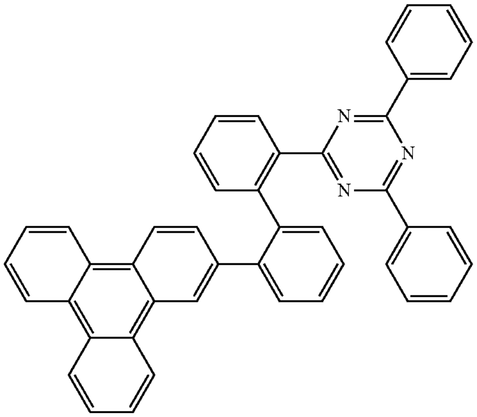
A-70
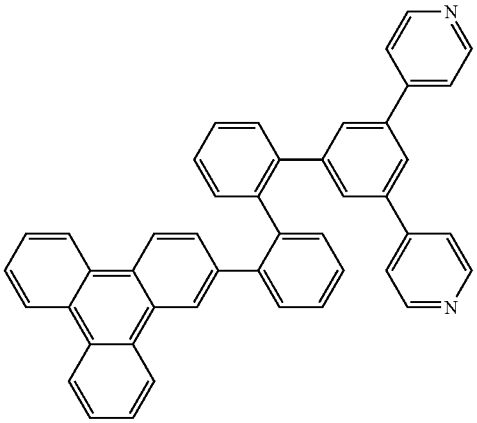

-continued
A-71
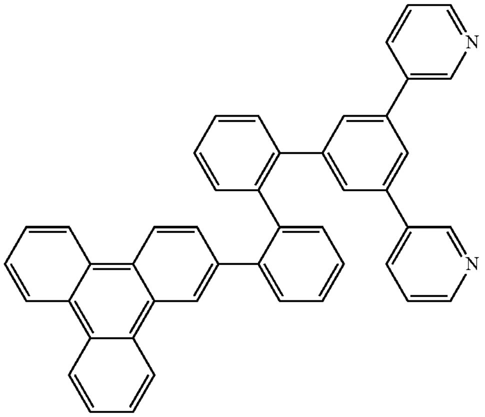
A-72
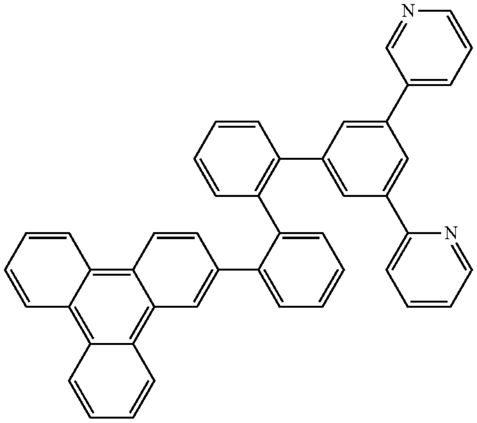
A-73
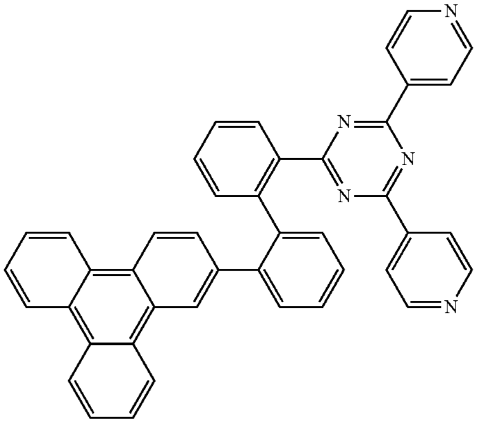
-continued
A-74
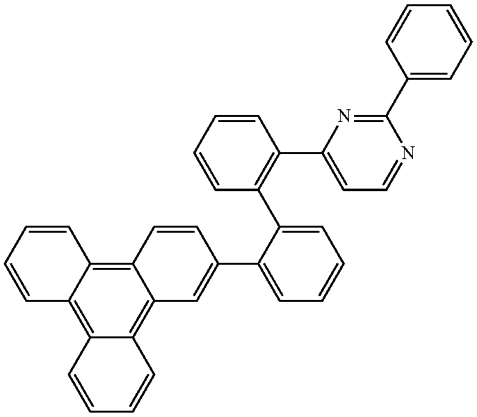
A-75
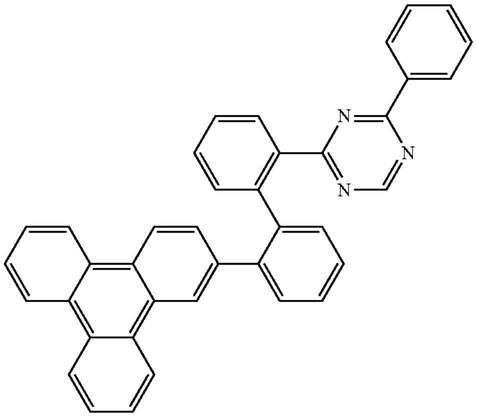
A-76
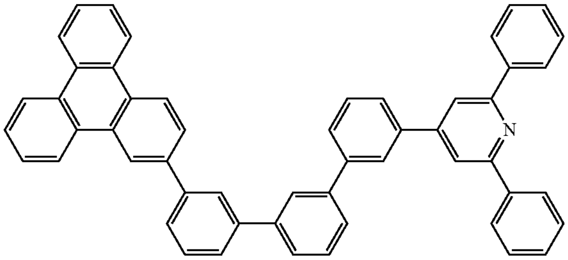
A-77
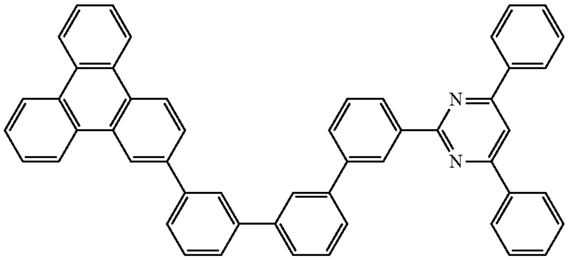

-continued
A-78
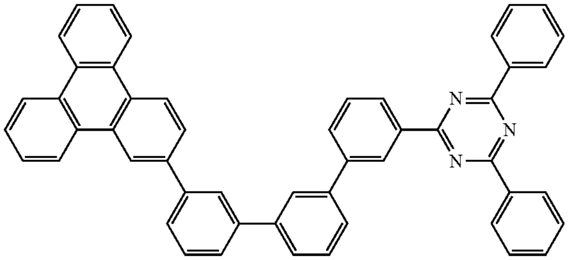
A-79
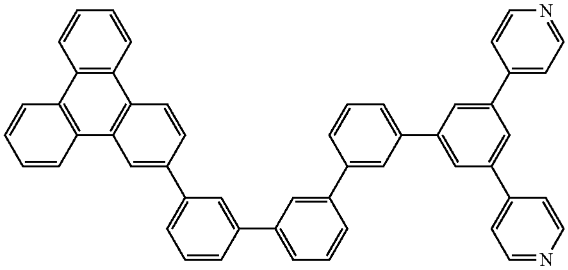
A-80
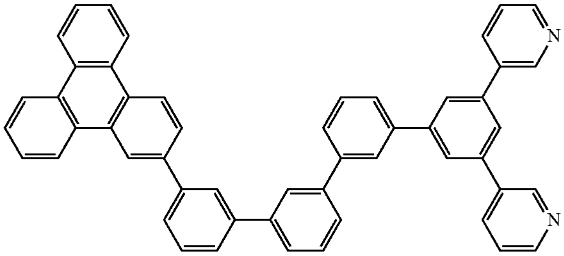
A-81
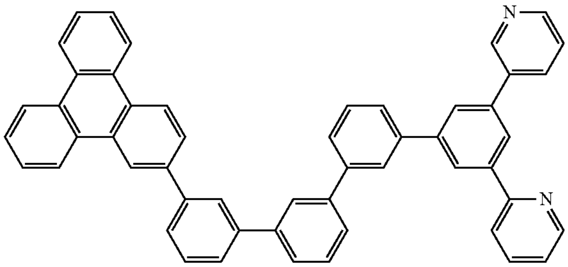
A-82
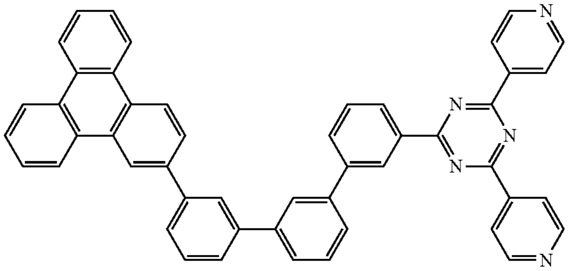
-continued
A-83
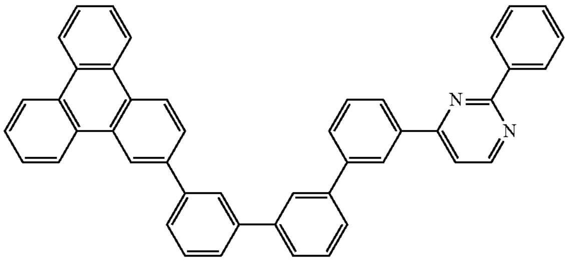
A-84
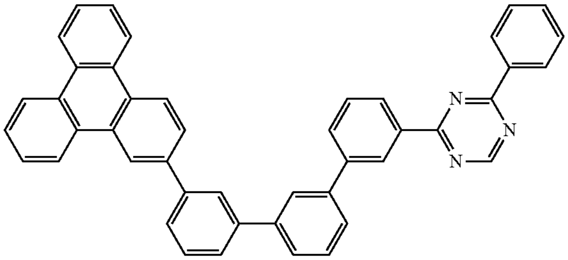
A-85
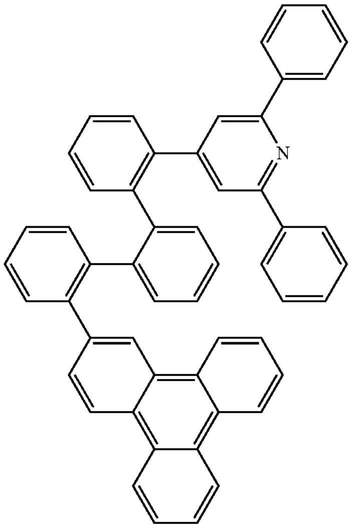
A-86
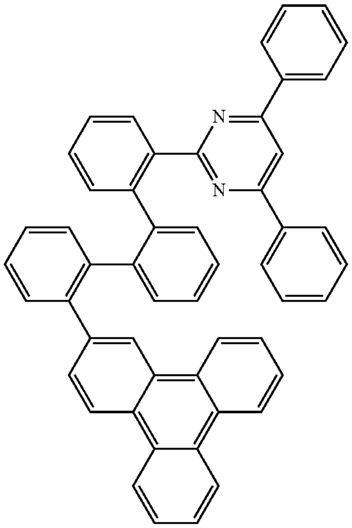

-continued
A-87
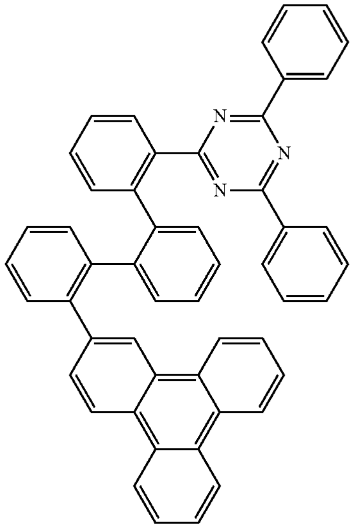
A-88
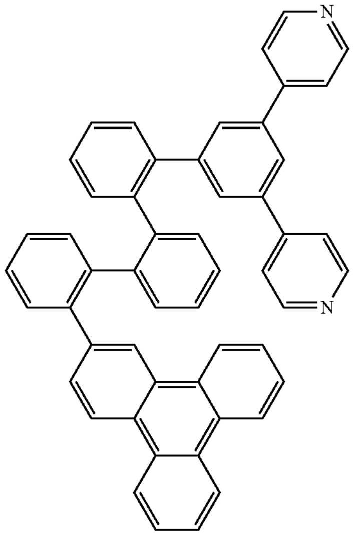
A-89
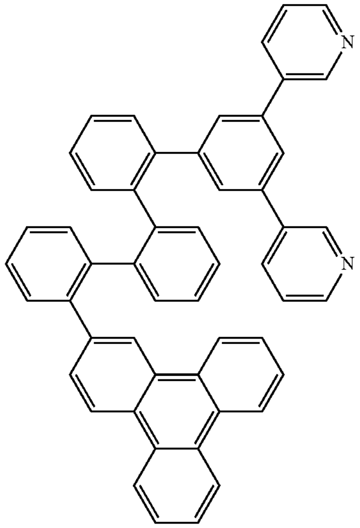
-continued
A-90
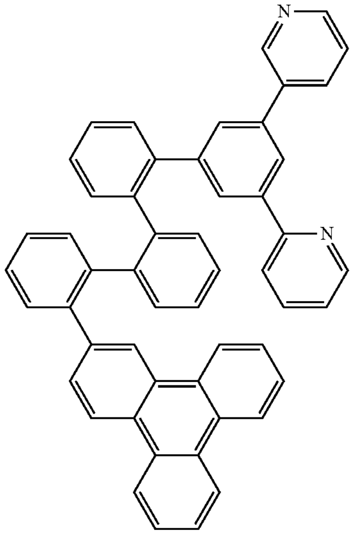
A-91
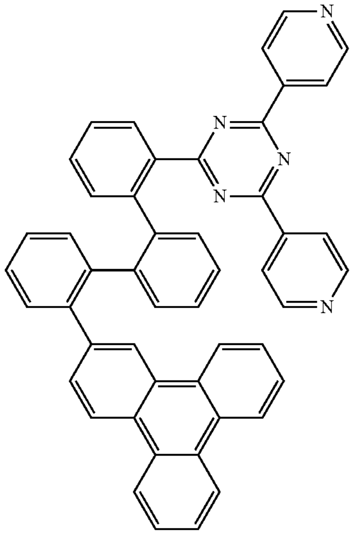
A-92
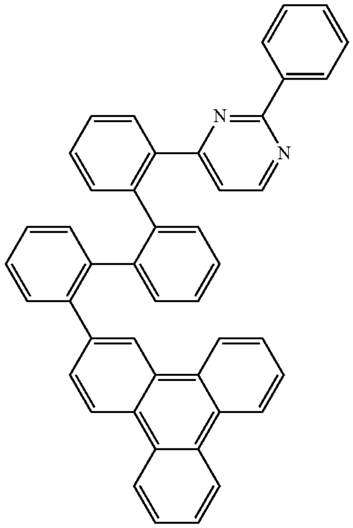

-continued
A-93
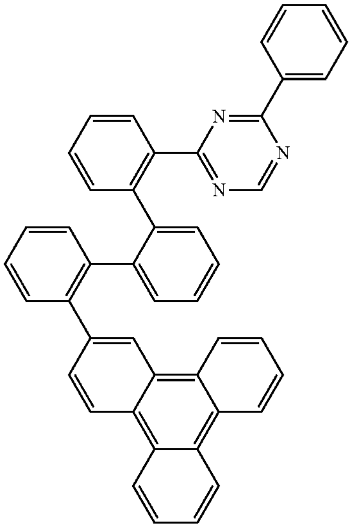
A-94
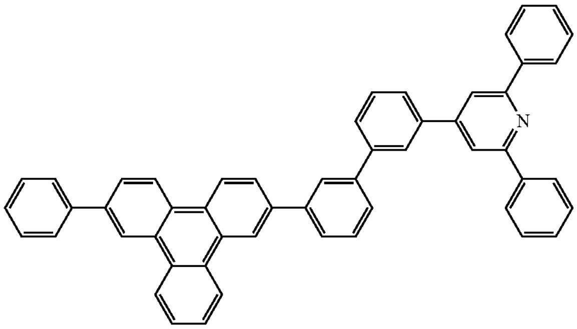
A-95
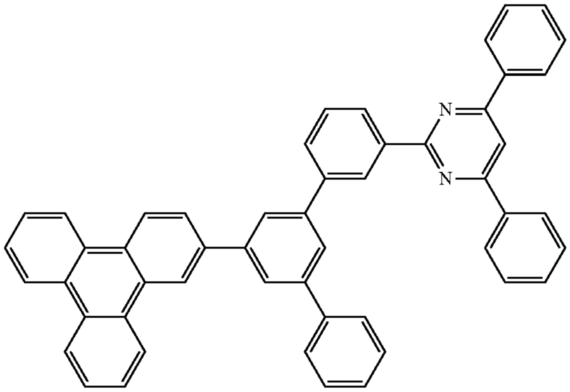
-continued
A-96
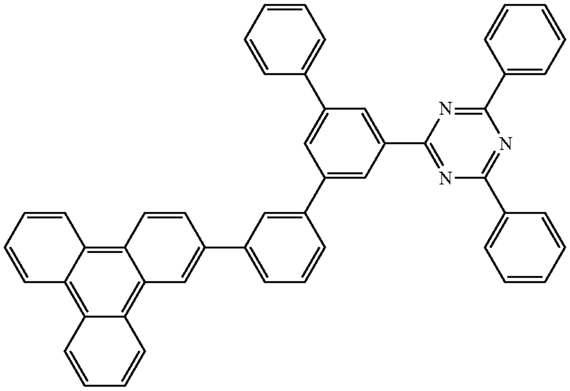
A-97
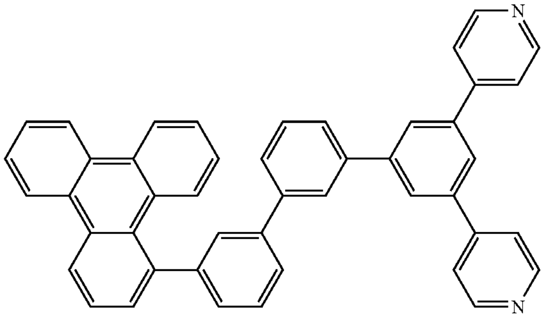
A-98
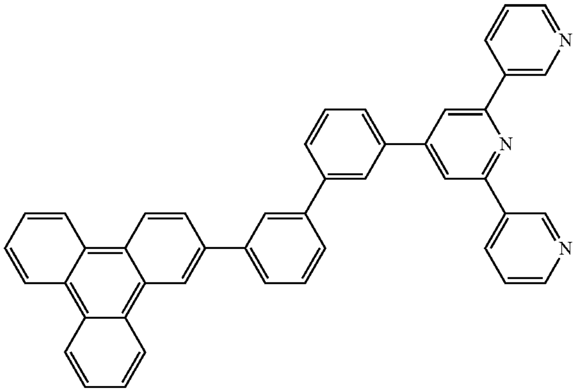
A-99
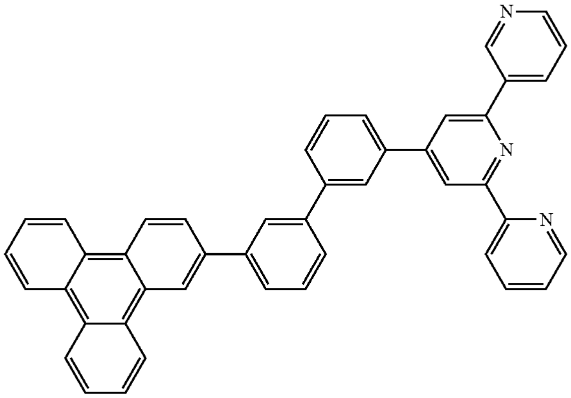

-continued
A-100
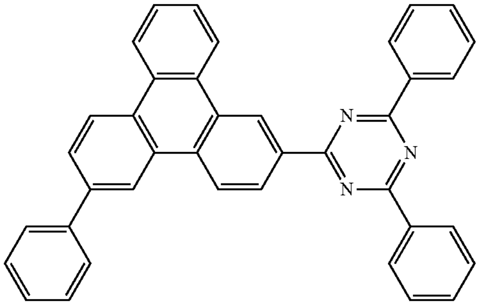
A-101
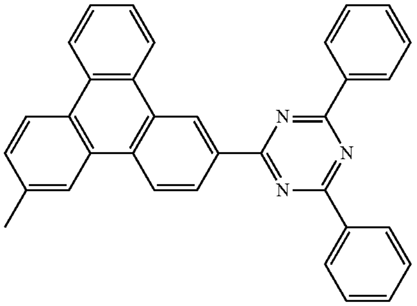
A-102
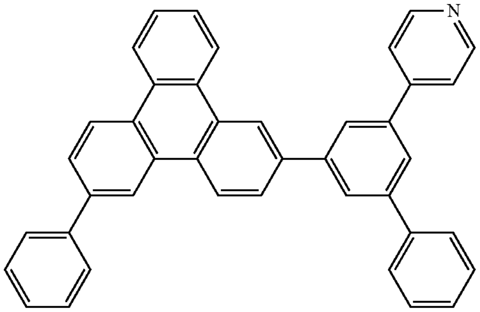
A-103
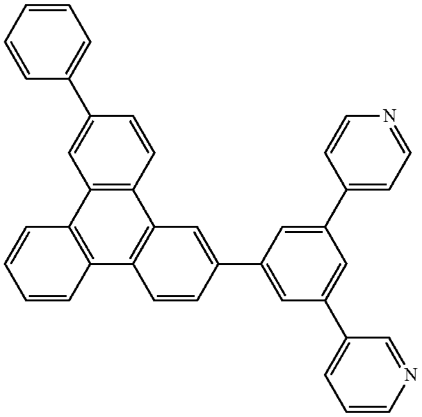
-continued
A-104
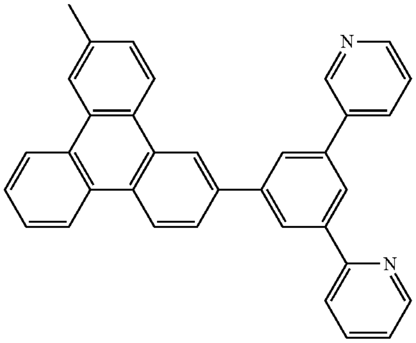
A-105
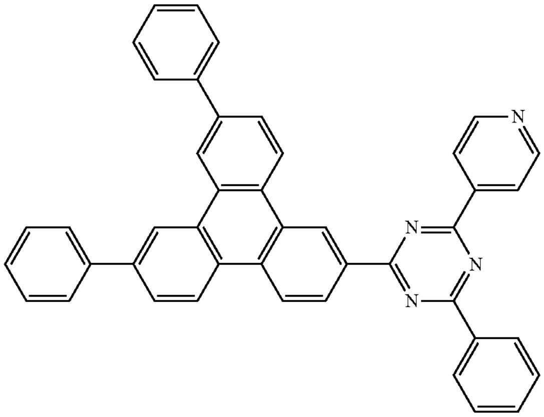
A-106
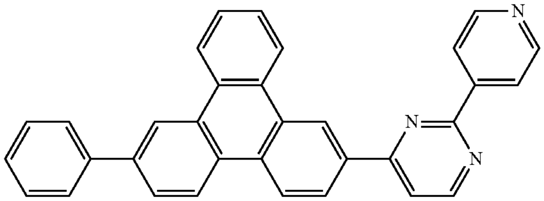
A-107
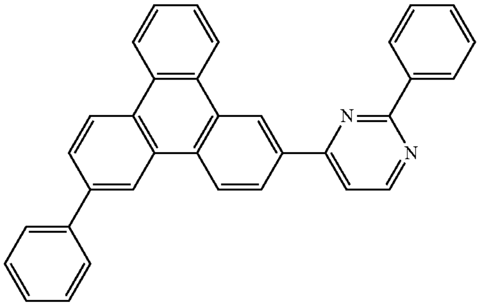

-continued
A-108
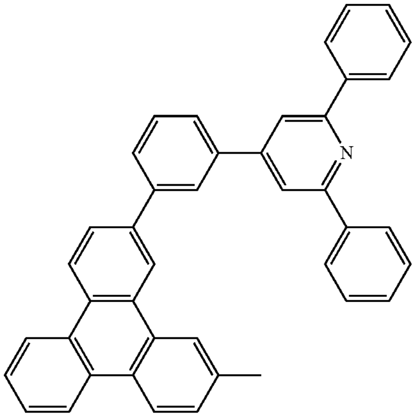
A-109
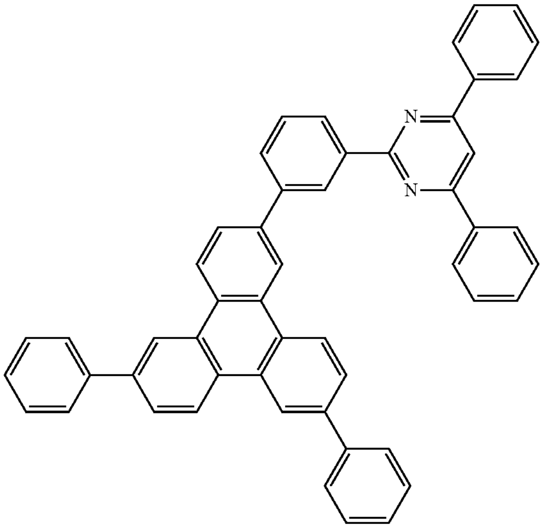
A-110
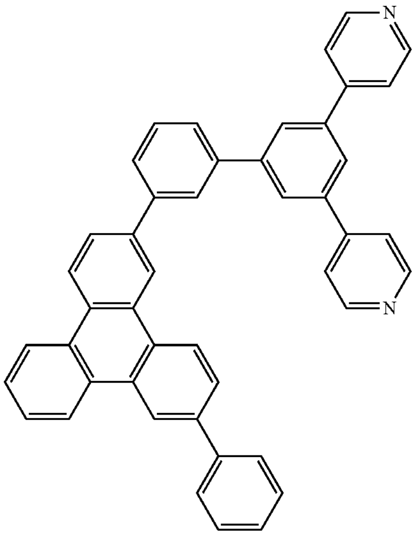
-continued
A-111
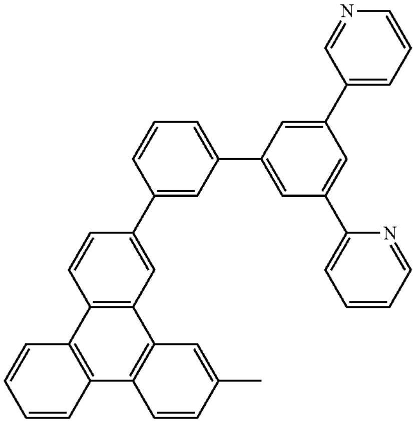
A-112
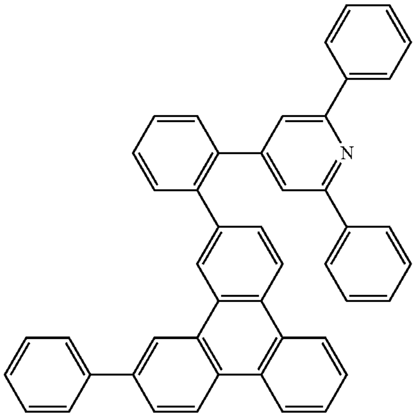
A-113
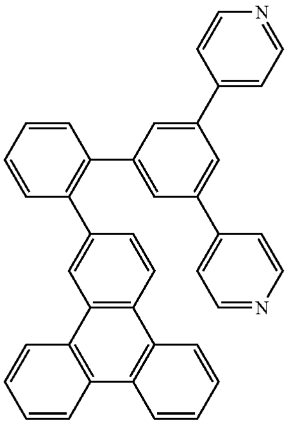

-continued
A-114
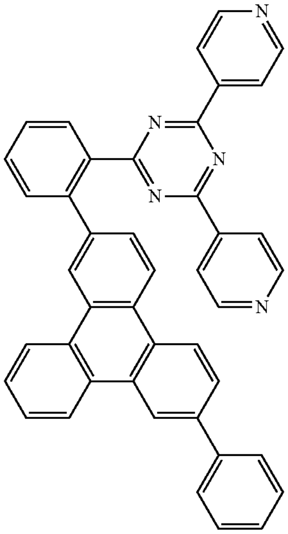
A-115
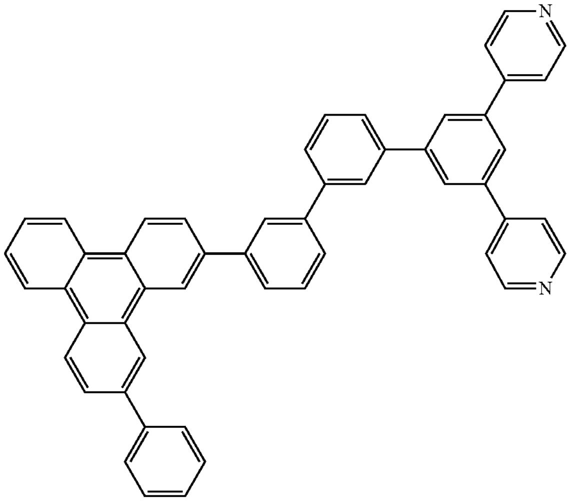
A-116
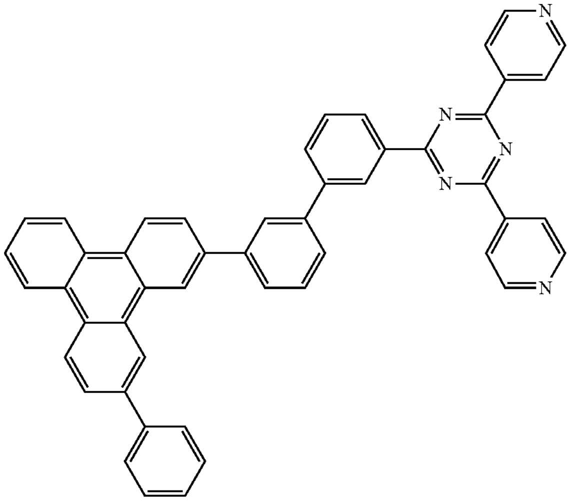
-continued
A-117
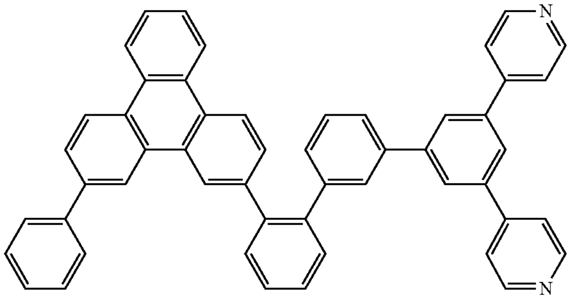
A-118
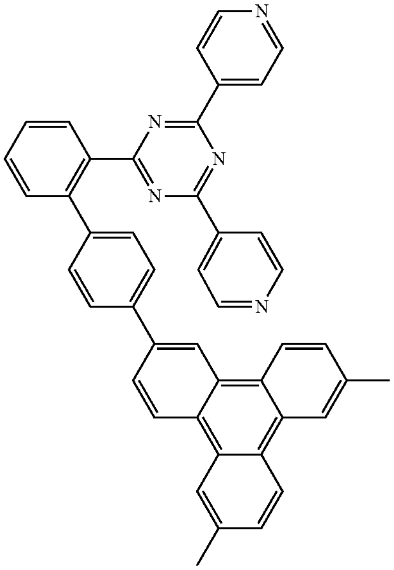
A-119
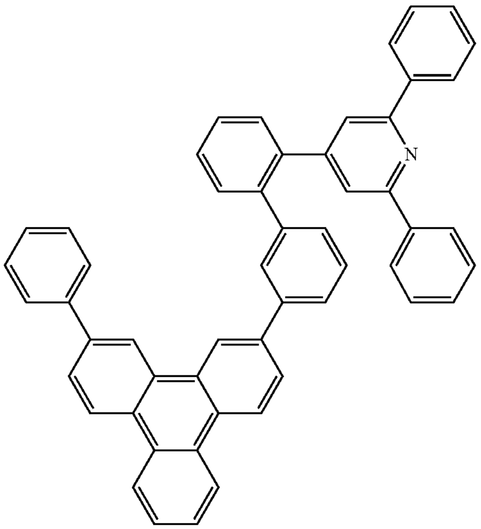

-continued
A-120
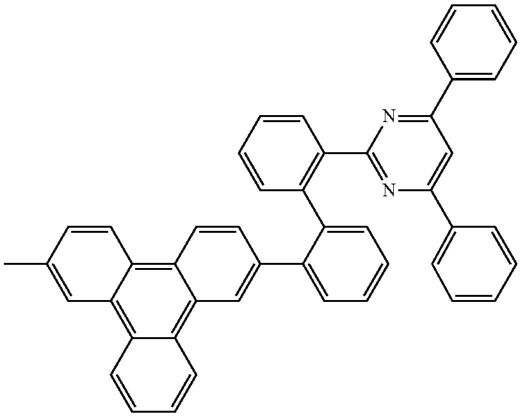
A-121
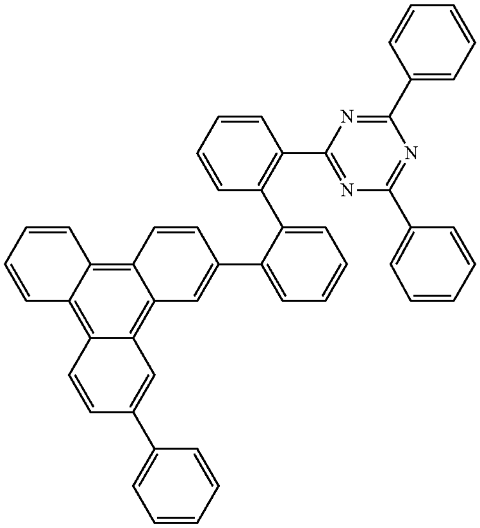
-continued
A-122
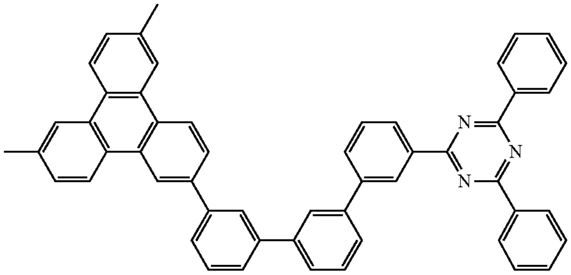
A-123
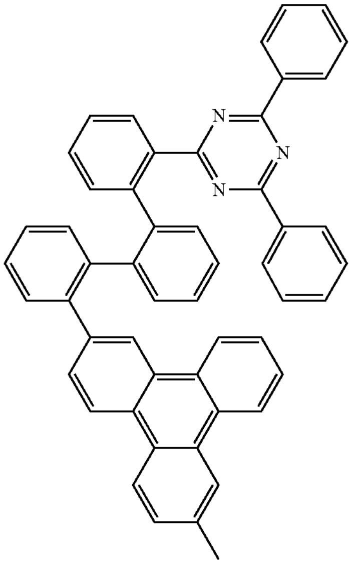
A-124
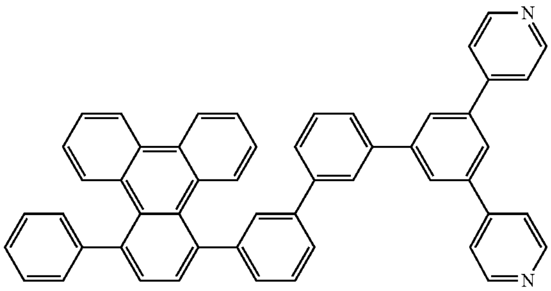
A-125
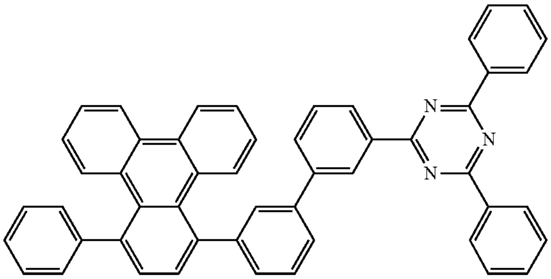

-continued
A(1)
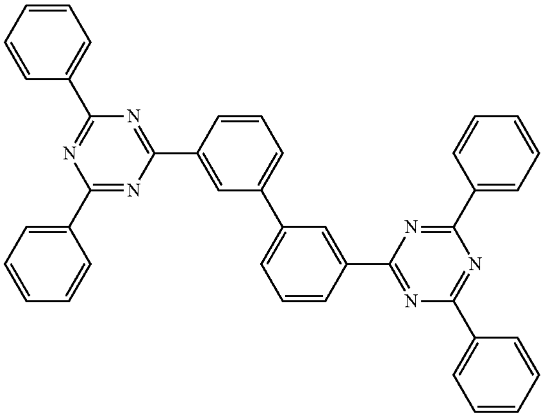
A(2)
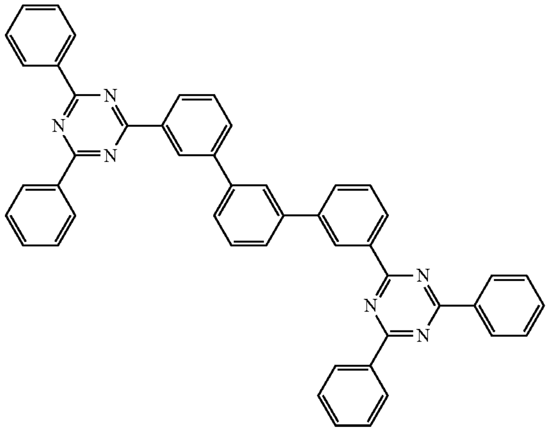
A(3)
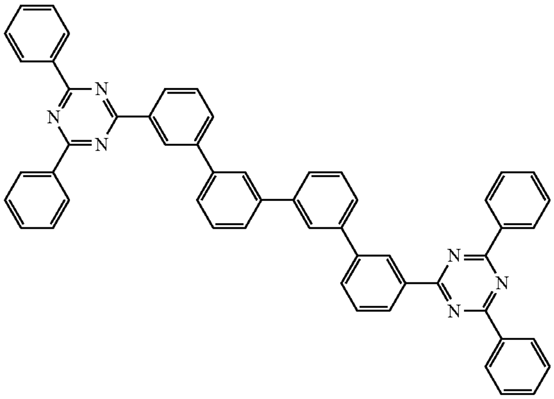
A(4)
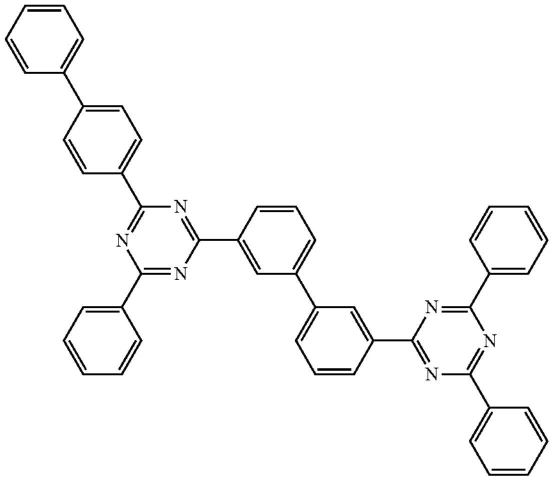
A(5)
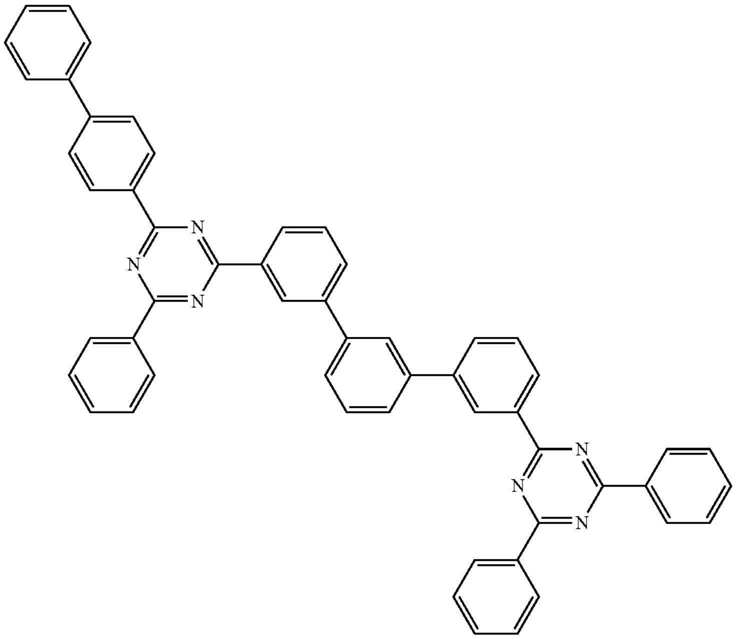

-continued
A(6)
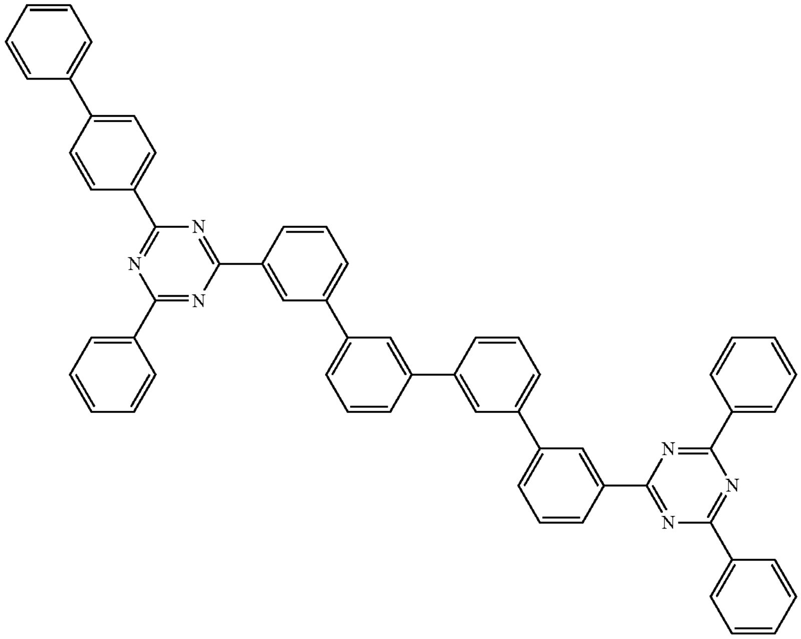
A(7)
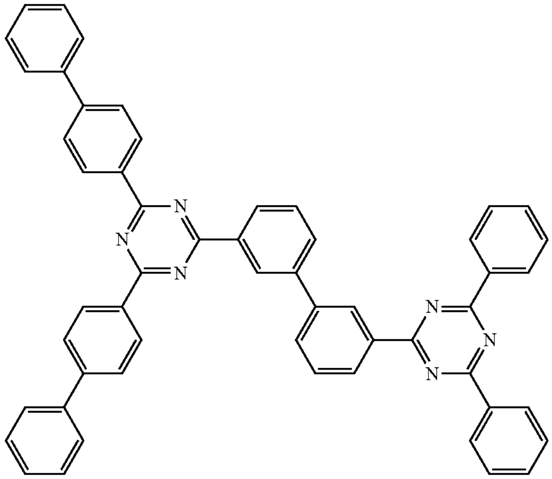
A(8)
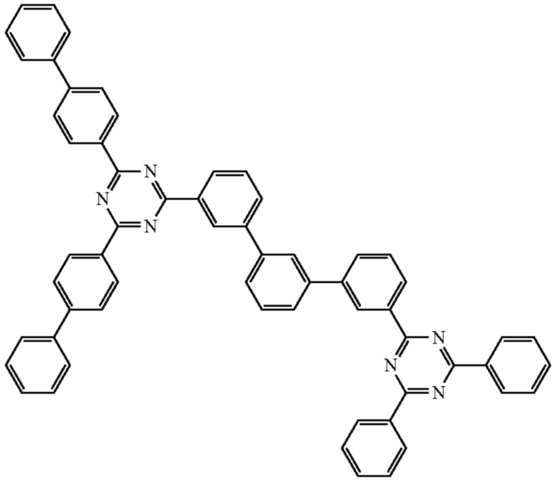

-continued
A(9)
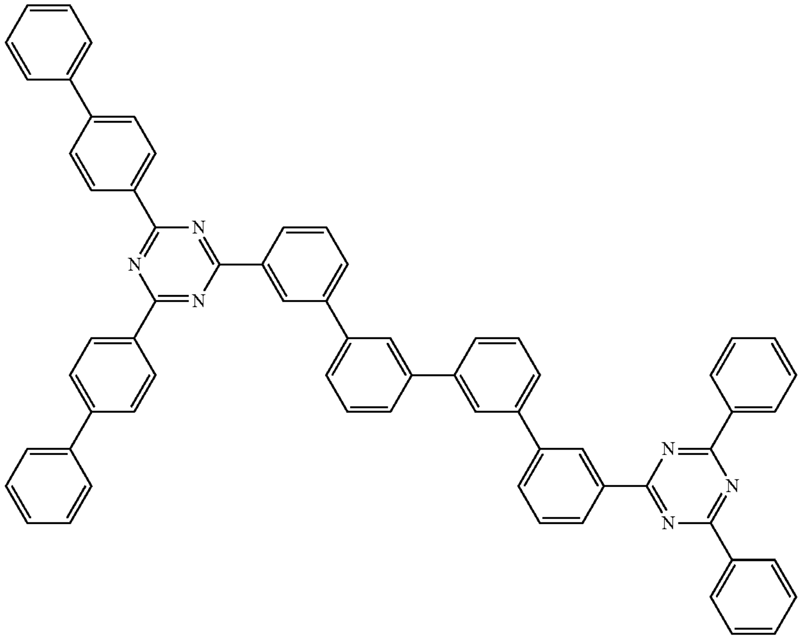
A(10)
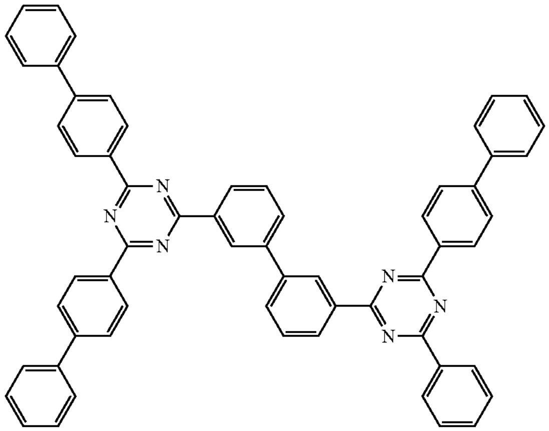
A(11)
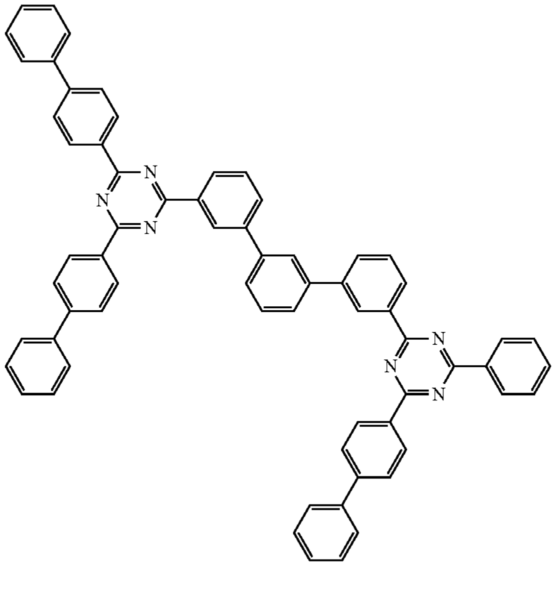

-continued
A(12)
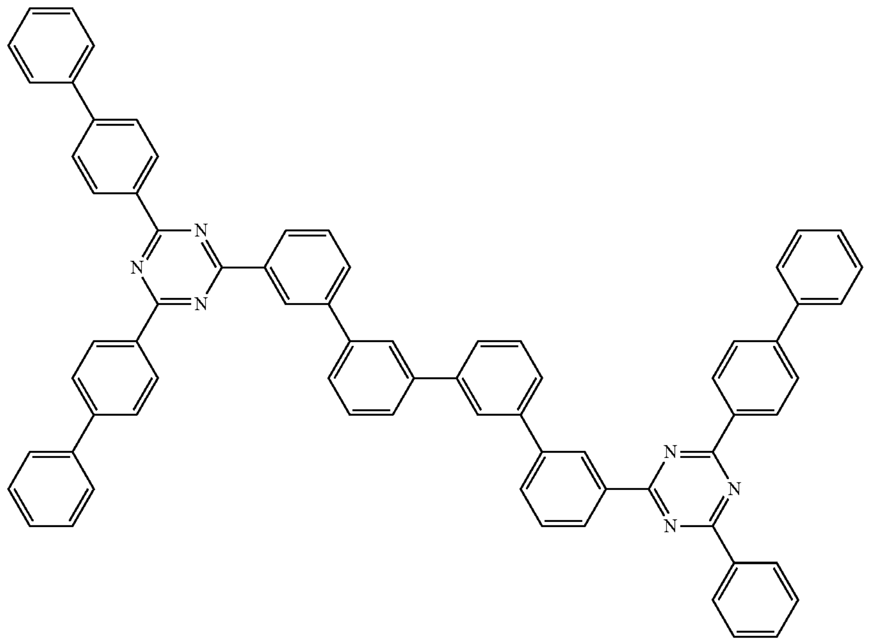
A(13)
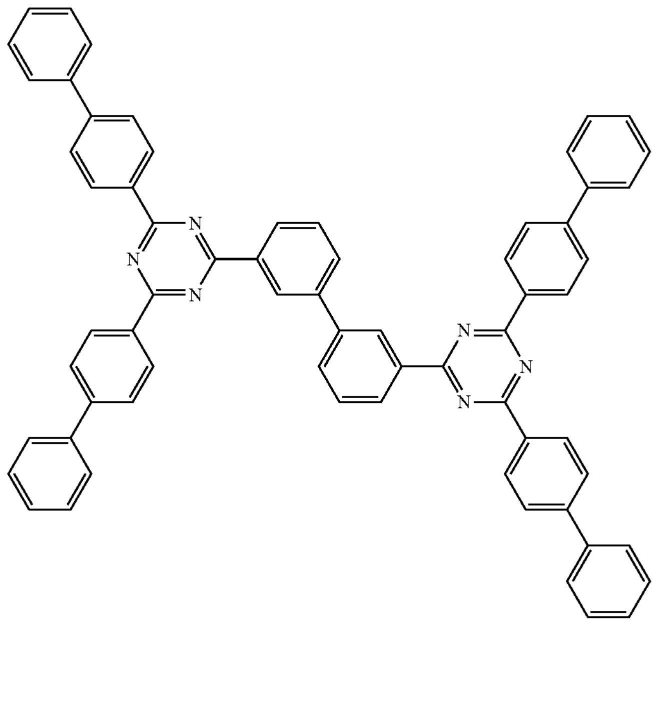

-continued
A(14)
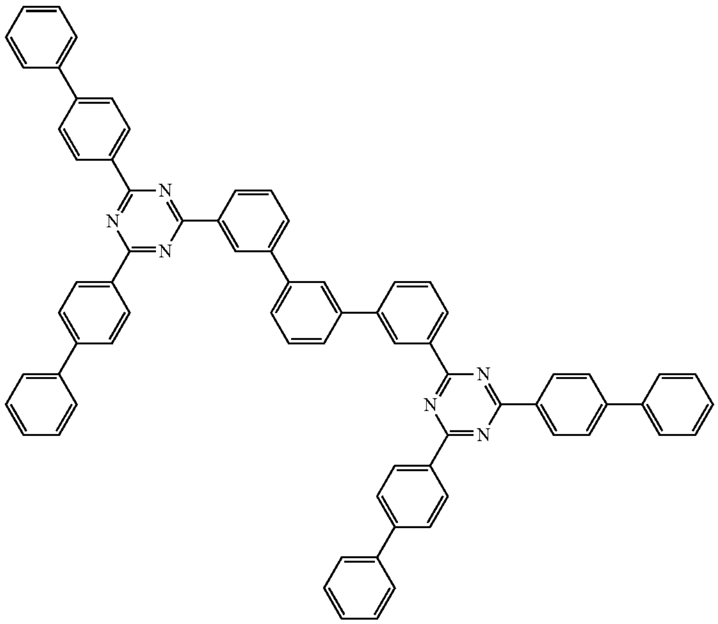
A(15)
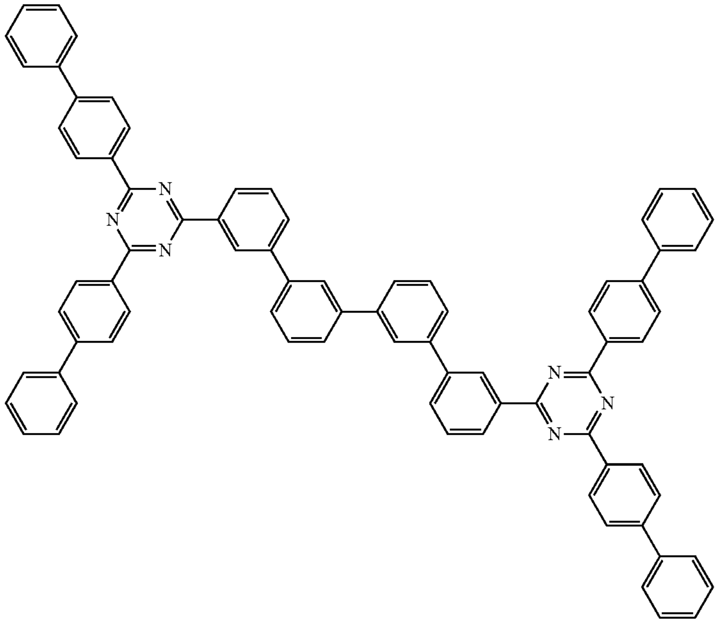
A(16)
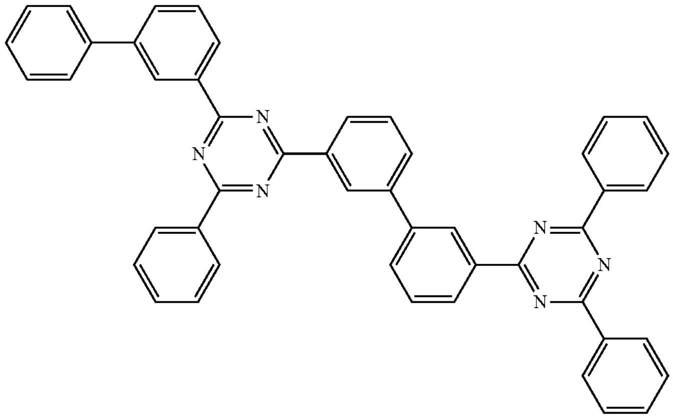

-continued
A(17)
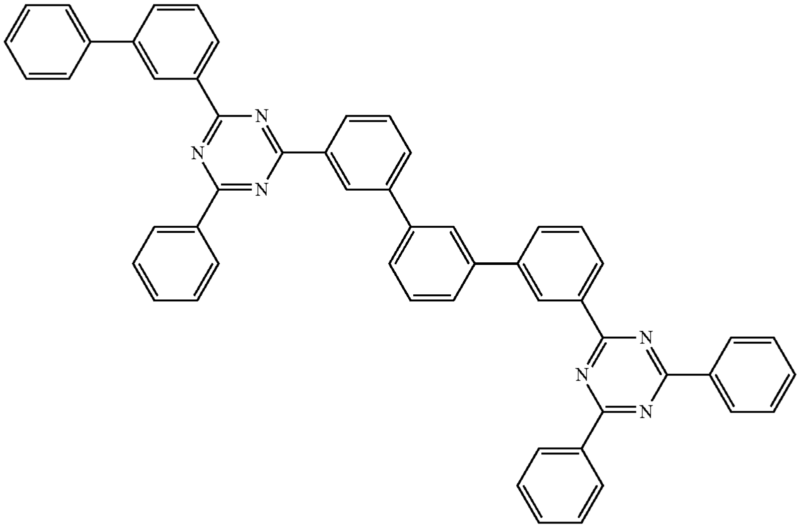
A(18)
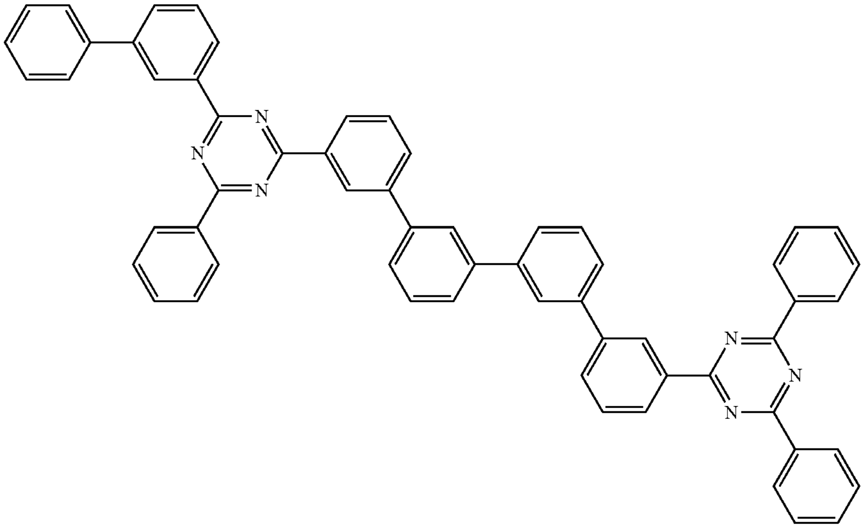
A(19)
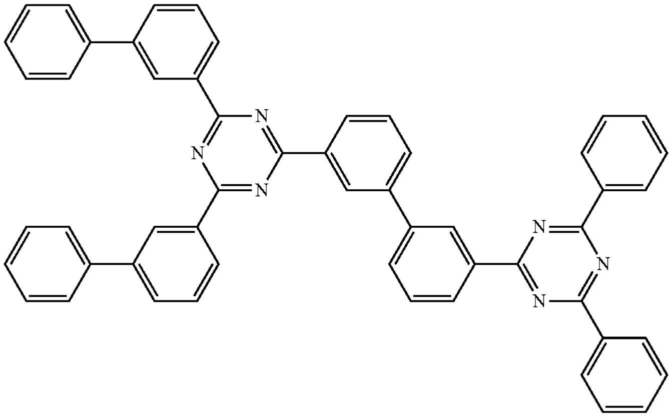

-continued
A(20)
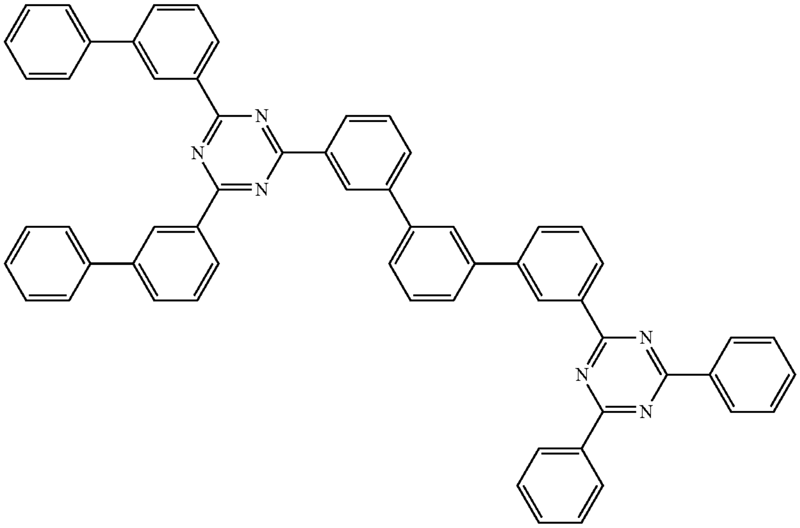
A(21)
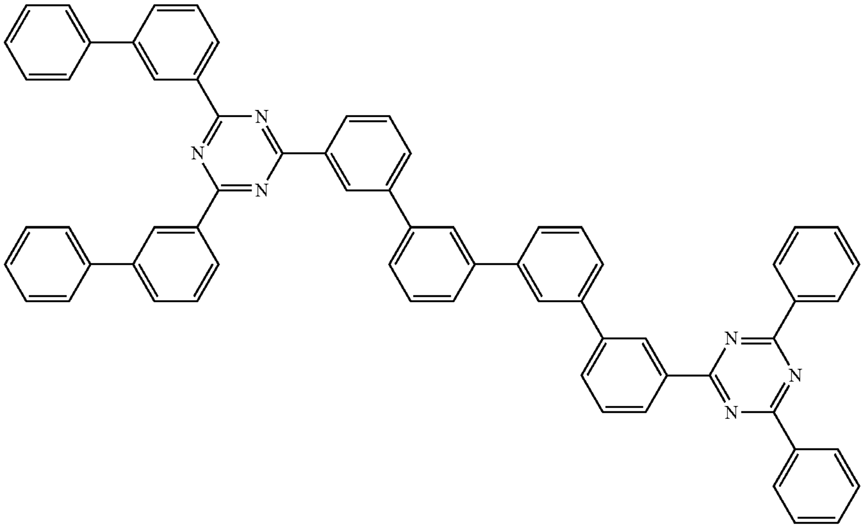
A(22)
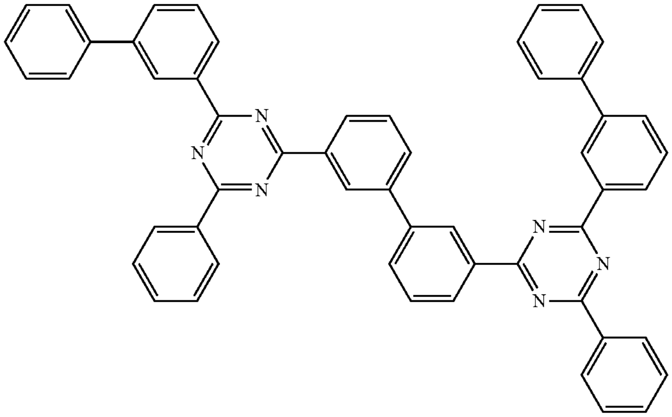

-continued
A(23)
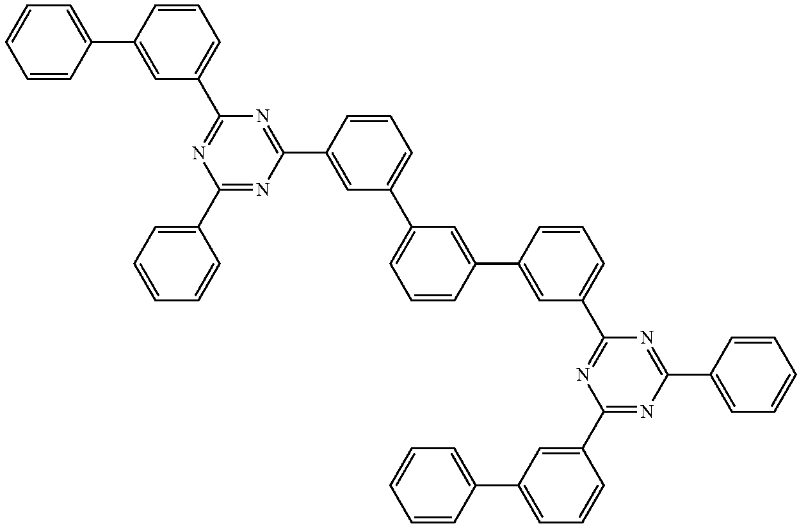
A(24)
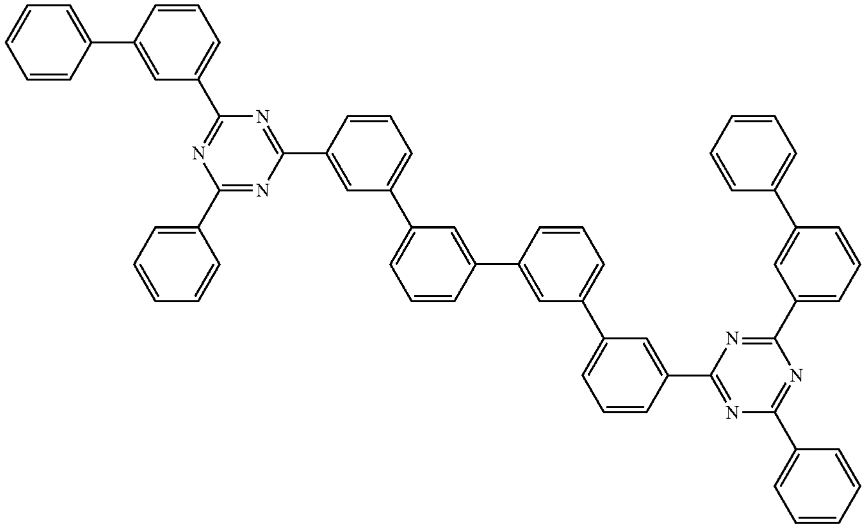
A(25)
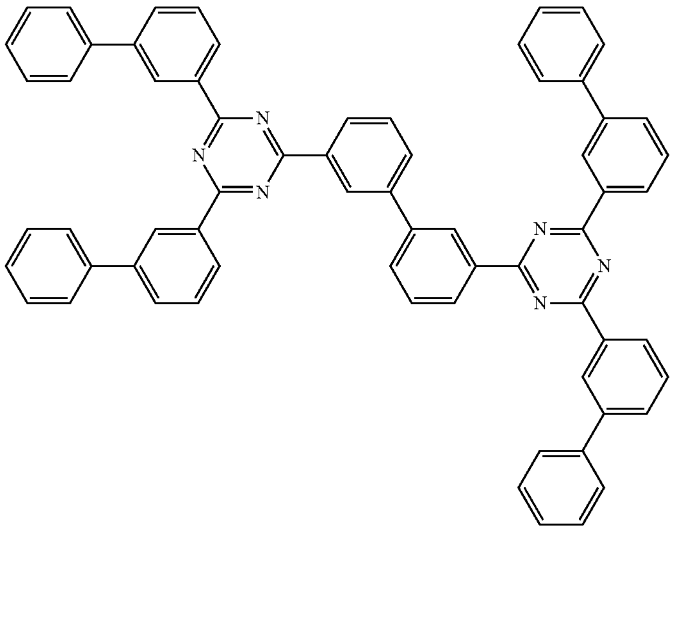

-continued
A(26)
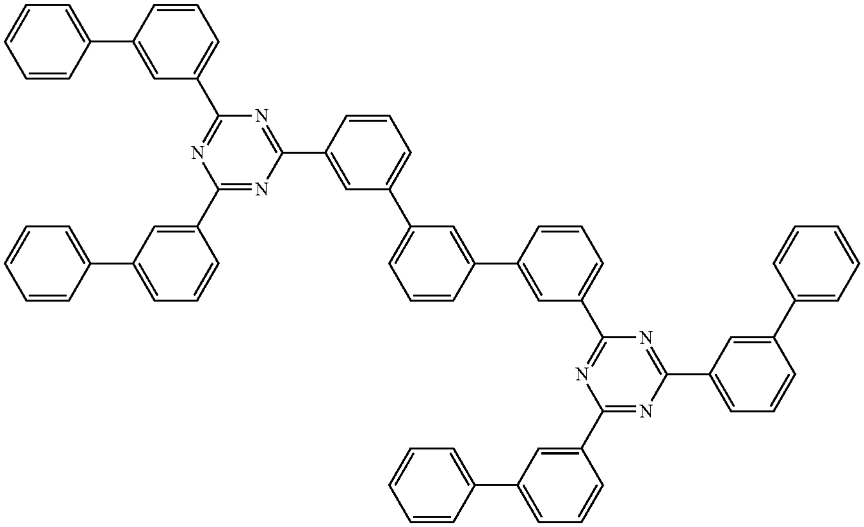
A(27)
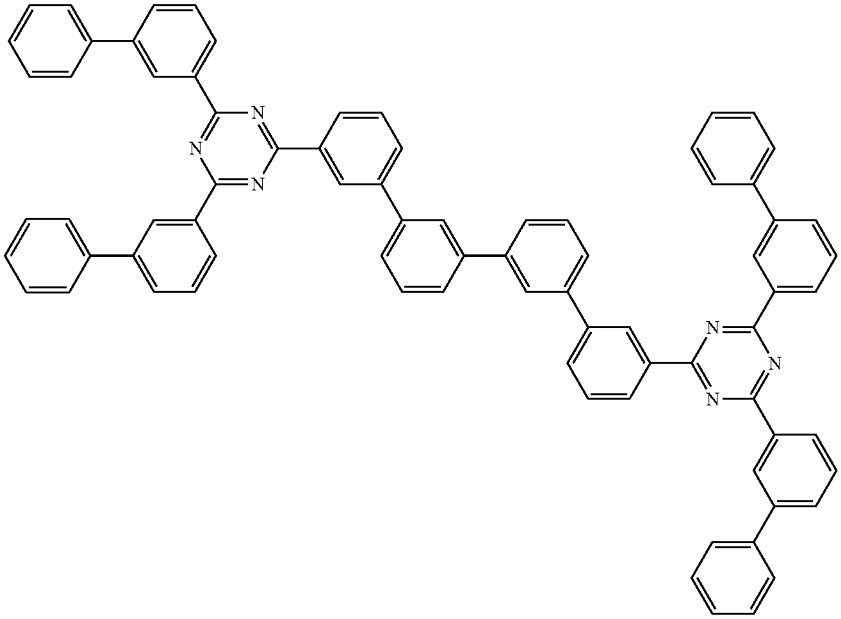
A(28)
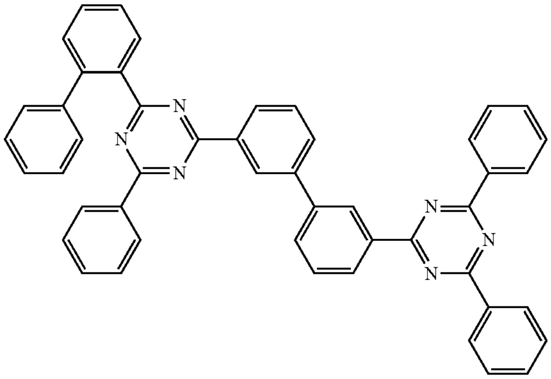
A(29)
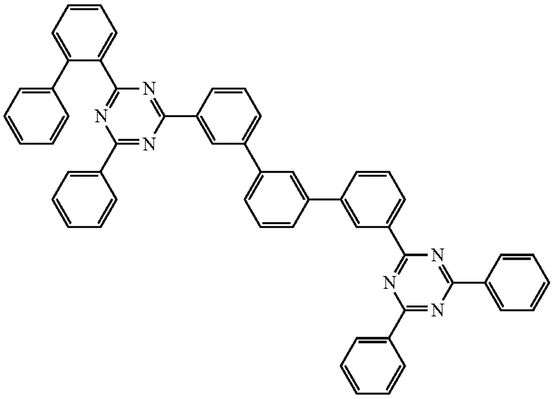

-continued
A(30)
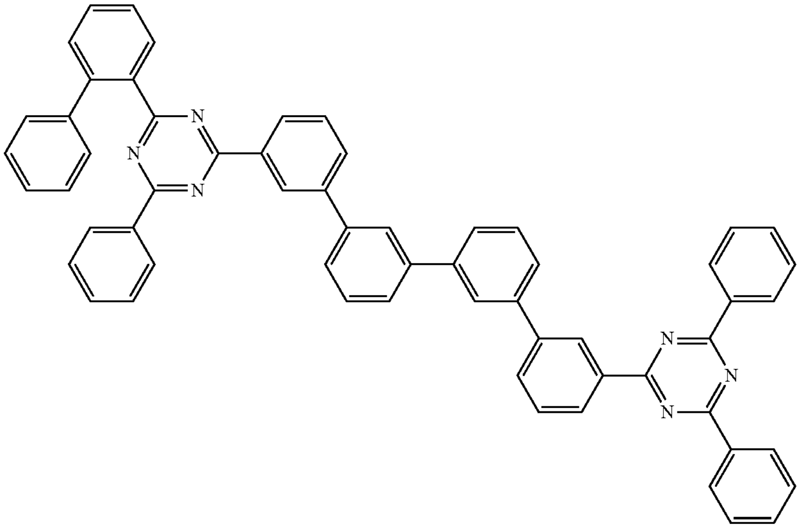
A(31)
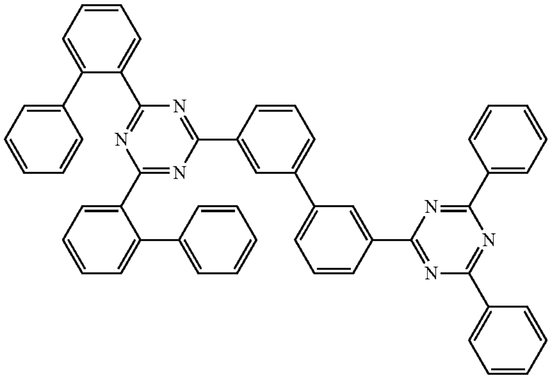
A(32)
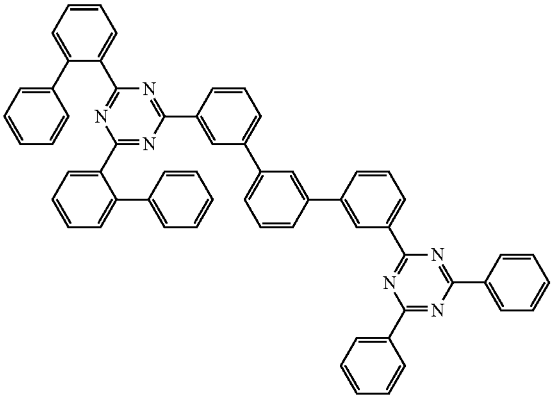
A(33)
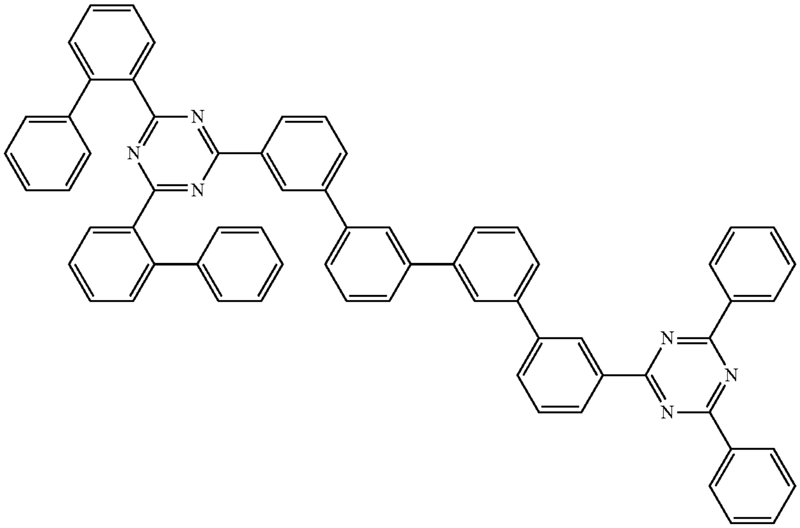

-continued
A(34)
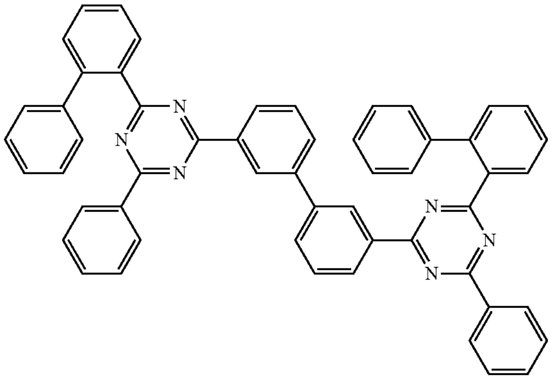
A(35)
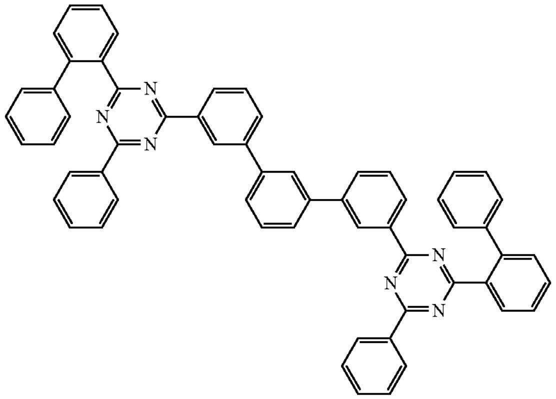
A(36)
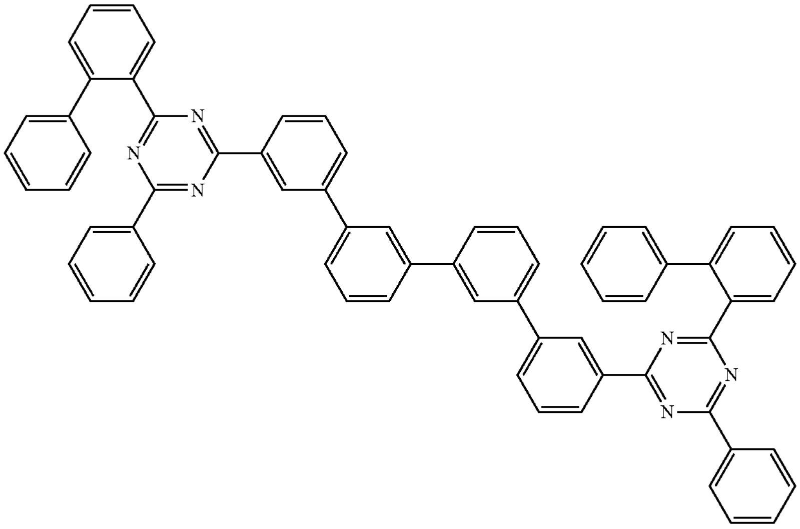
A(37)
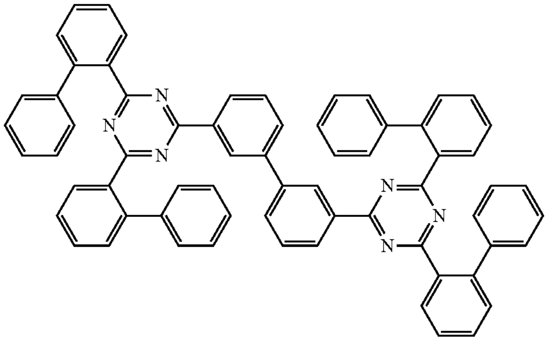
A(38)
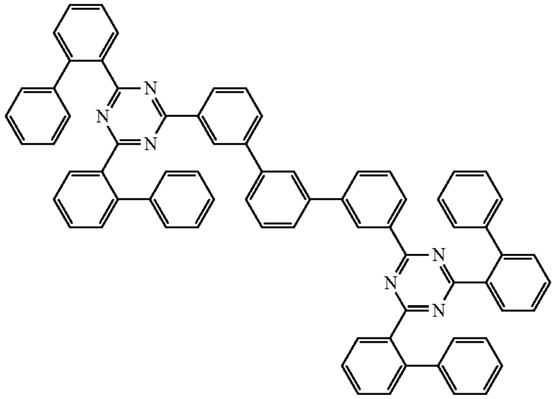

-continued
A(39)
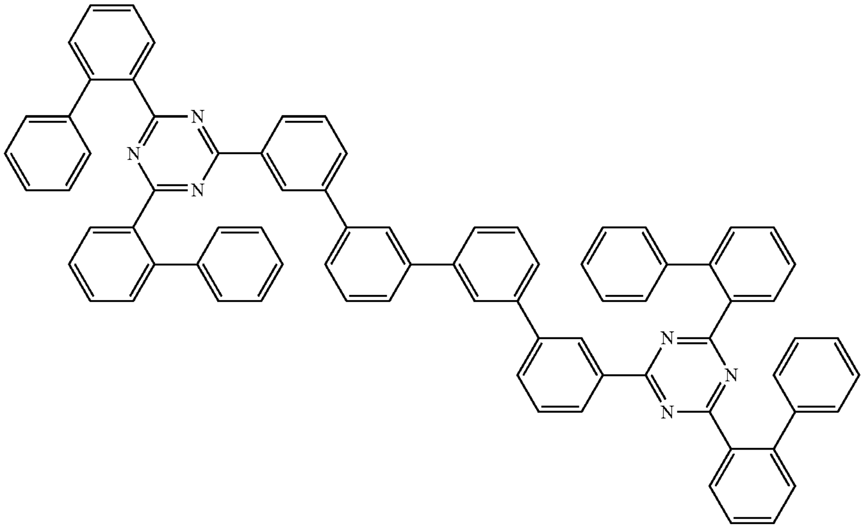
A(40)
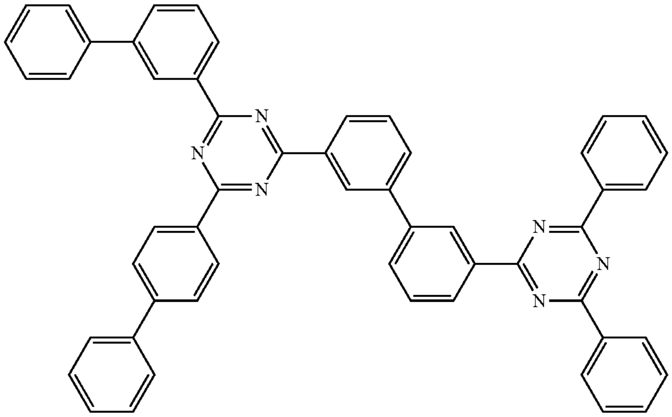
A(41)
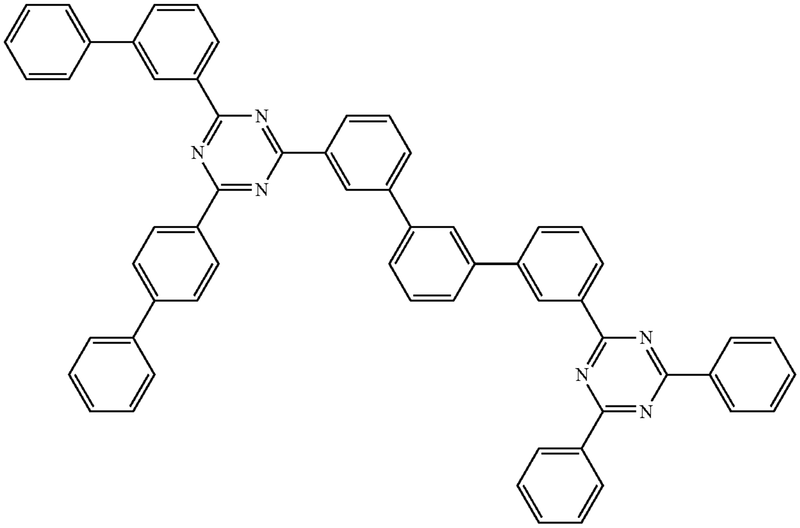

-continued
A(42)
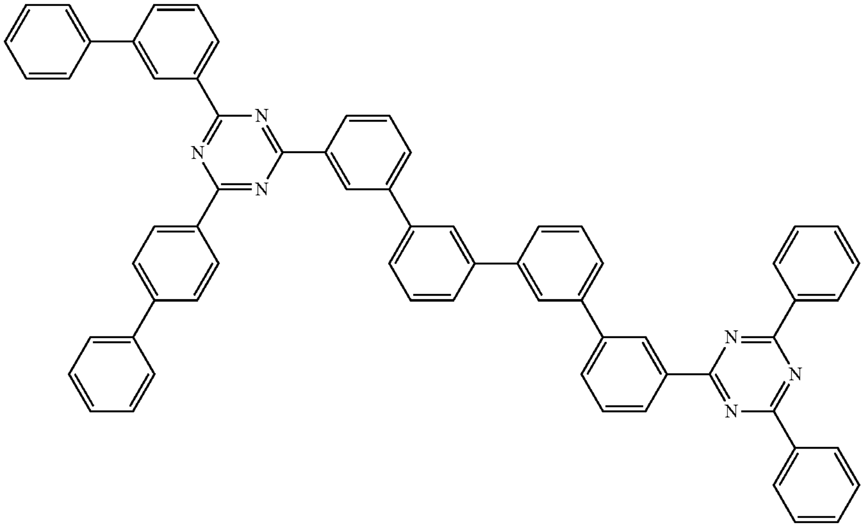
A(43)
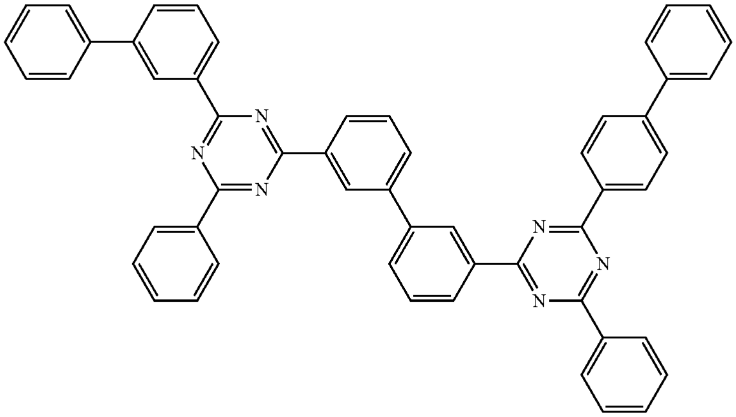
A(44)
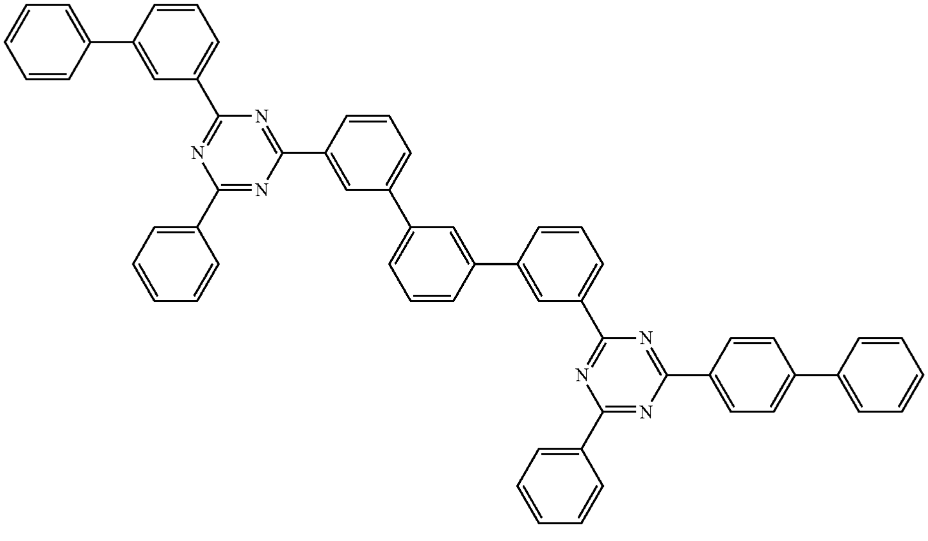

-continued
A(45)
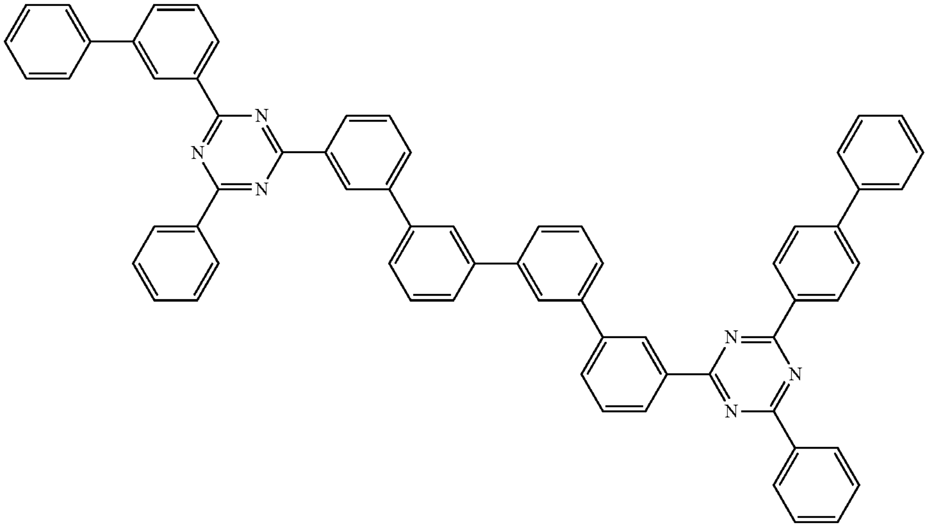
A(46)
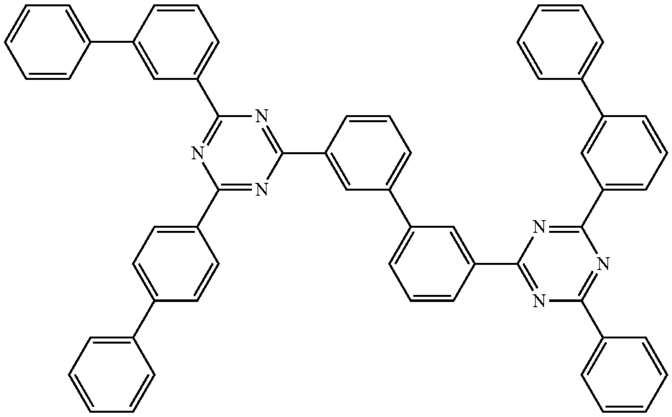
A(47)
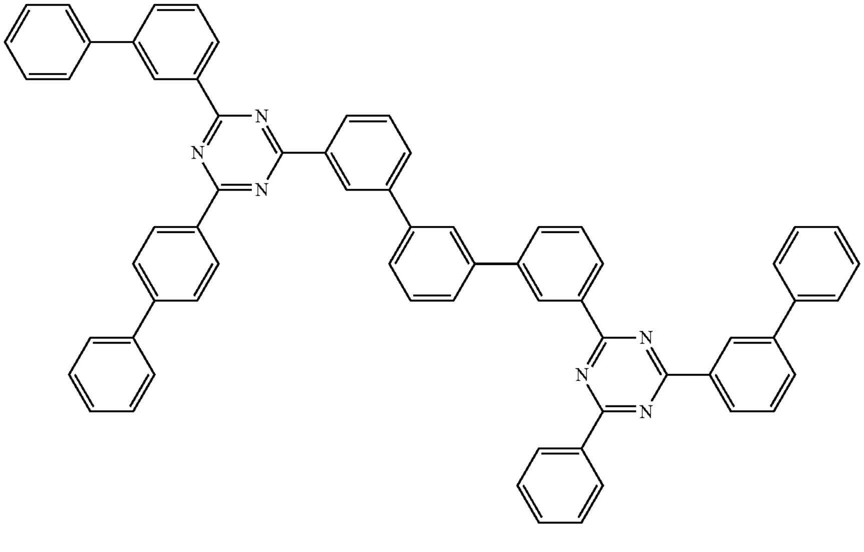

-continued
A(48)
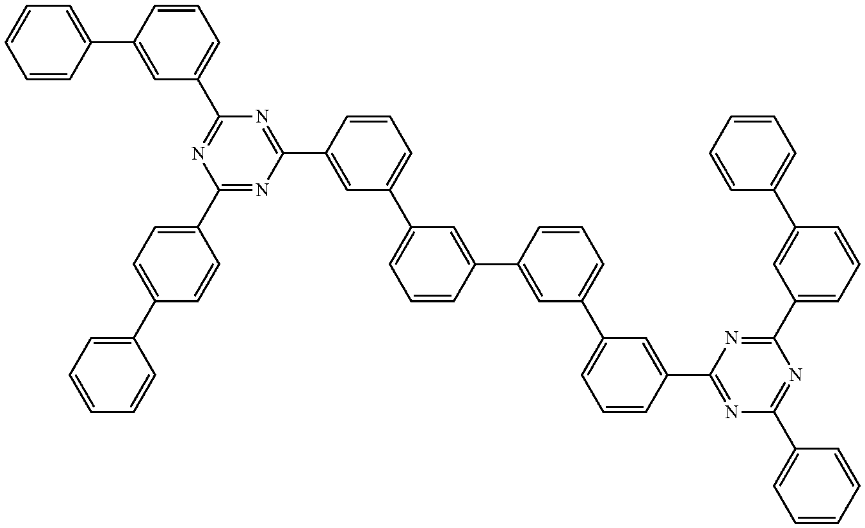
A(49)
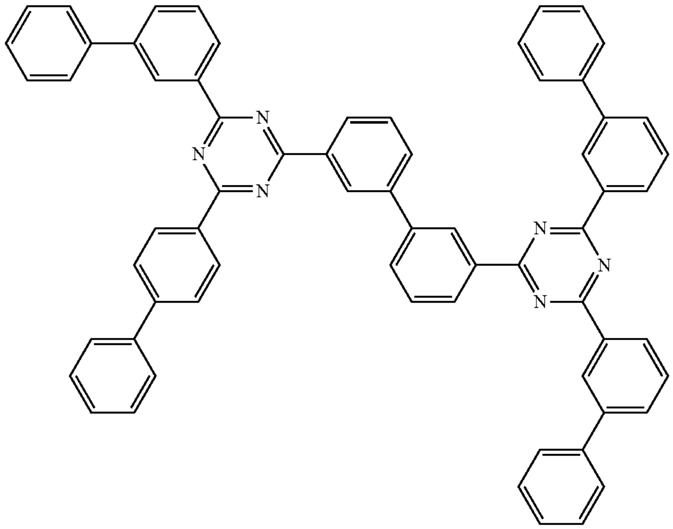
A(50)
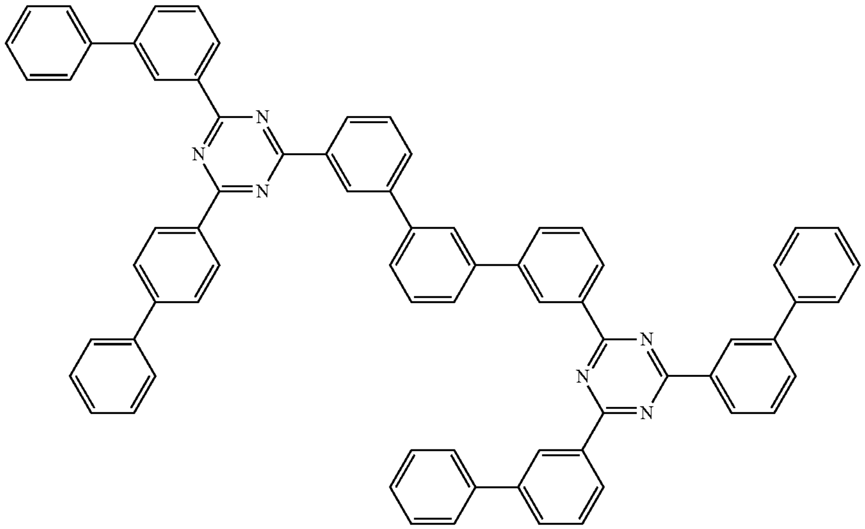

-continued
A(51)
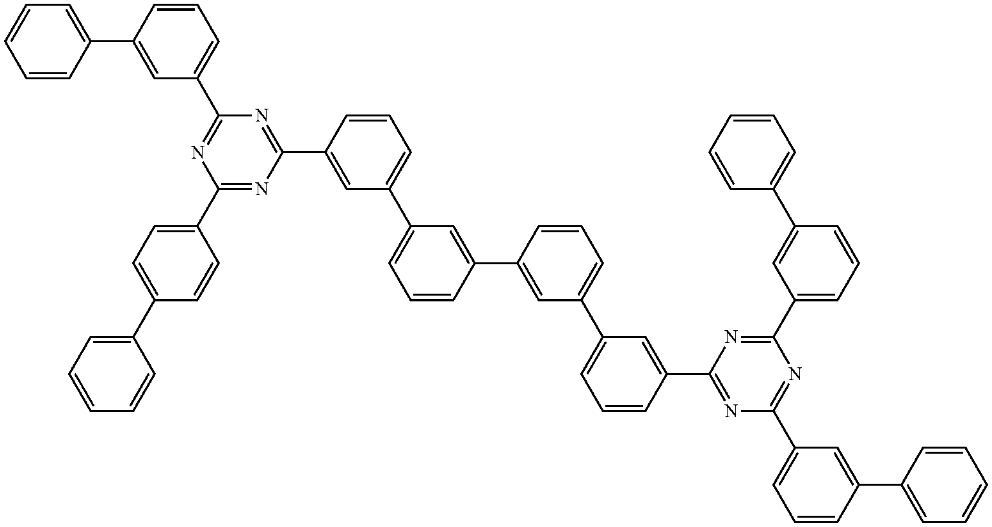
A(52)
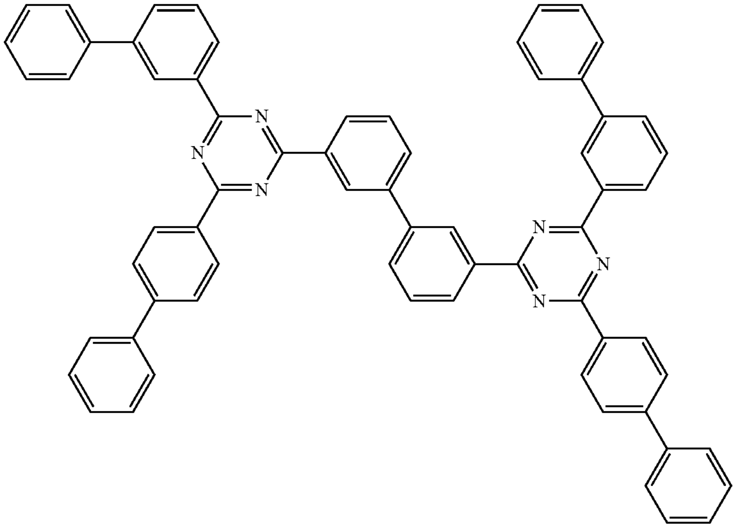

-continued
A(53)
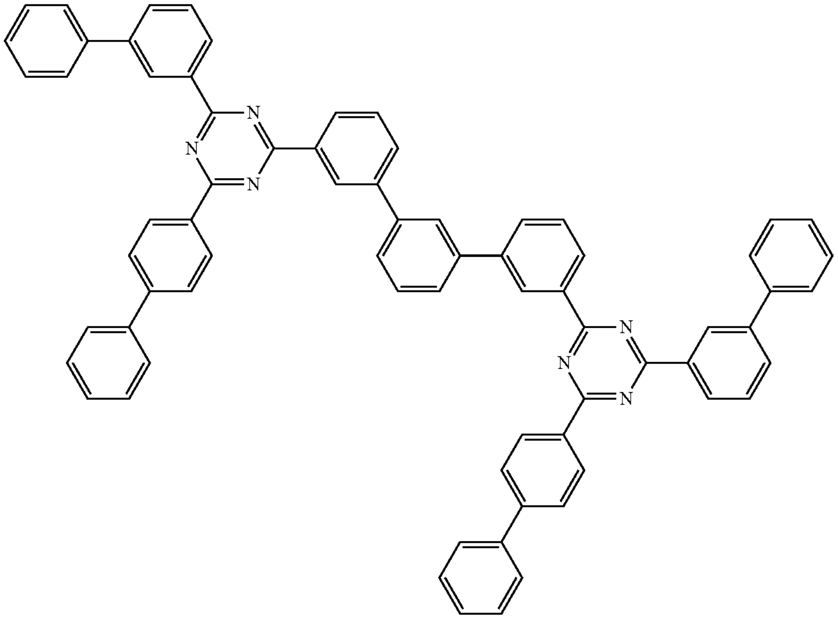
A(54)
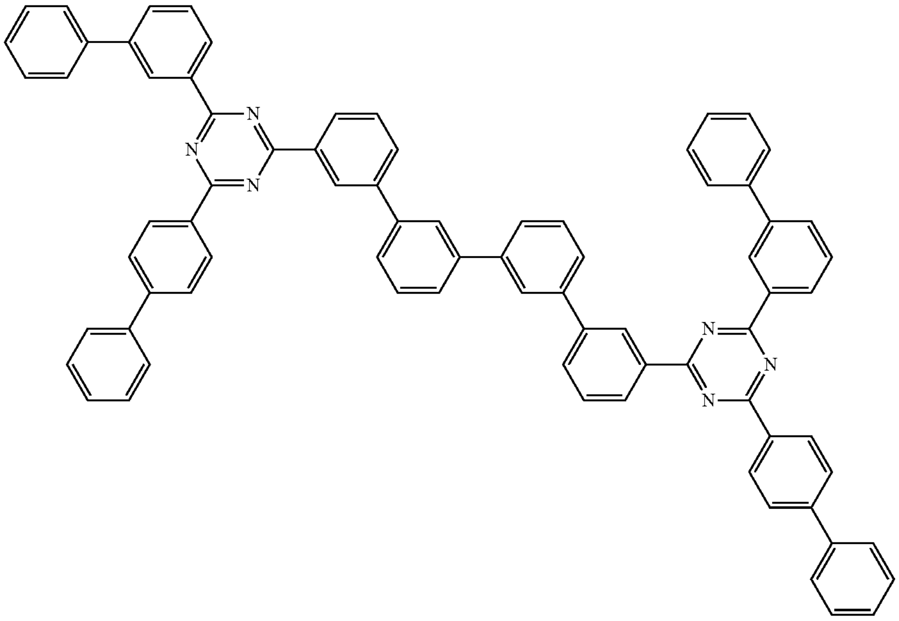

-continued
A(55)
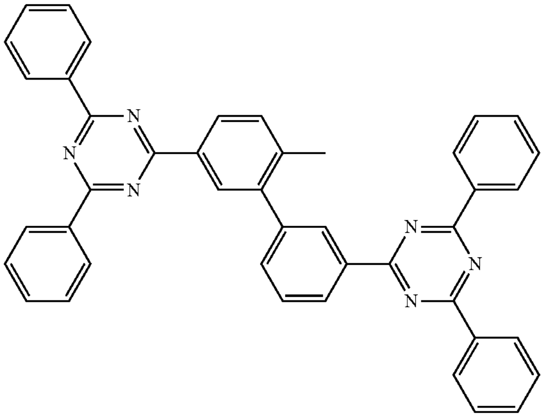
A(56)
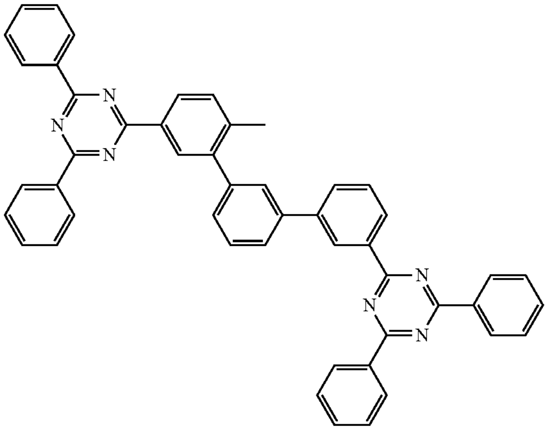
A(57)
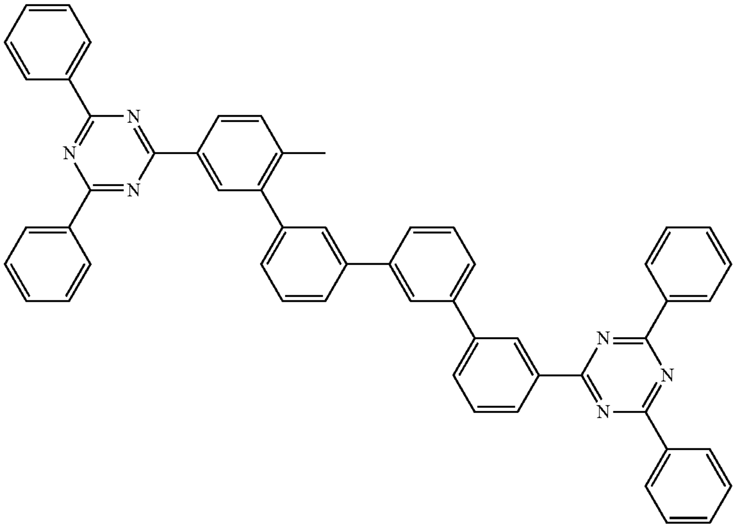
A(58)
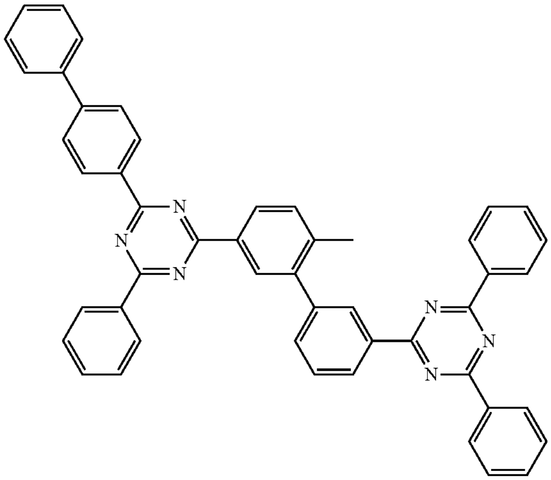
A(59)
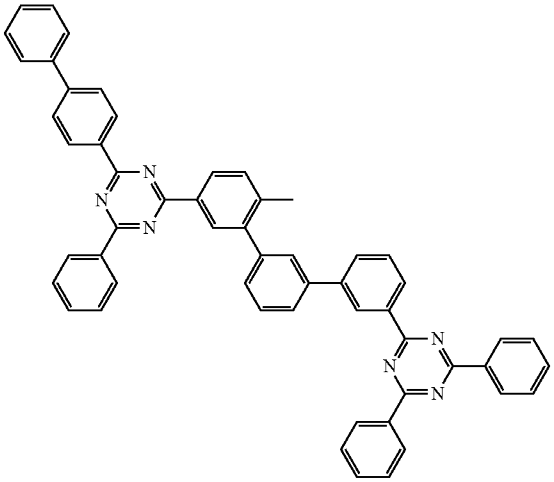

-continued
A(60)
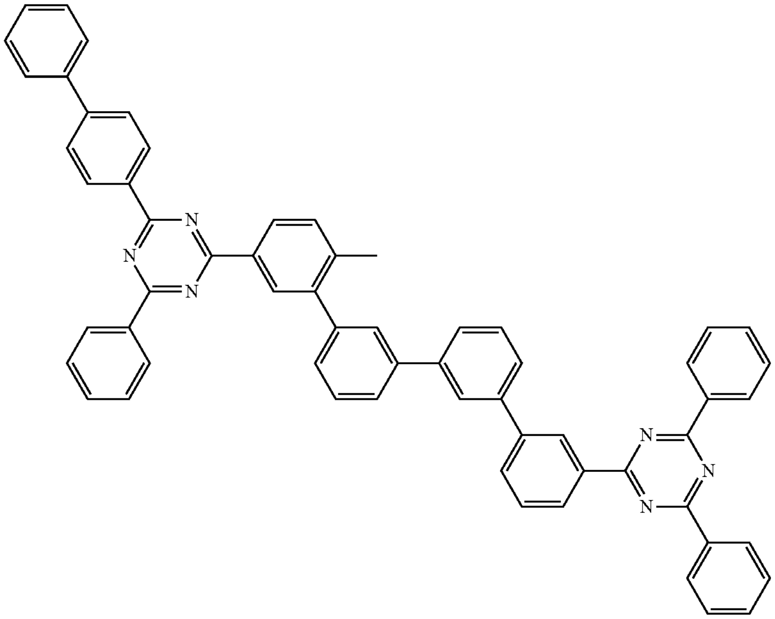
A(61)
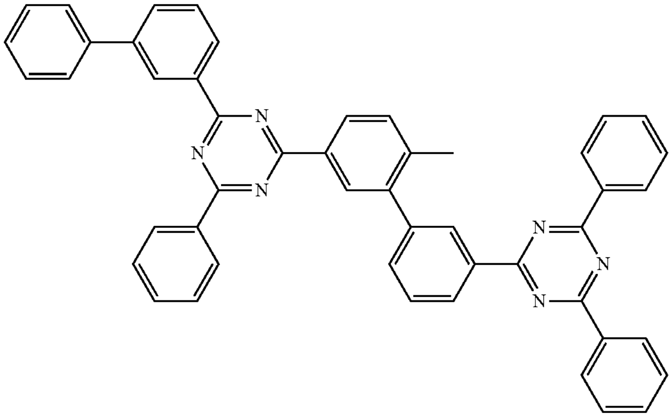
A(62)
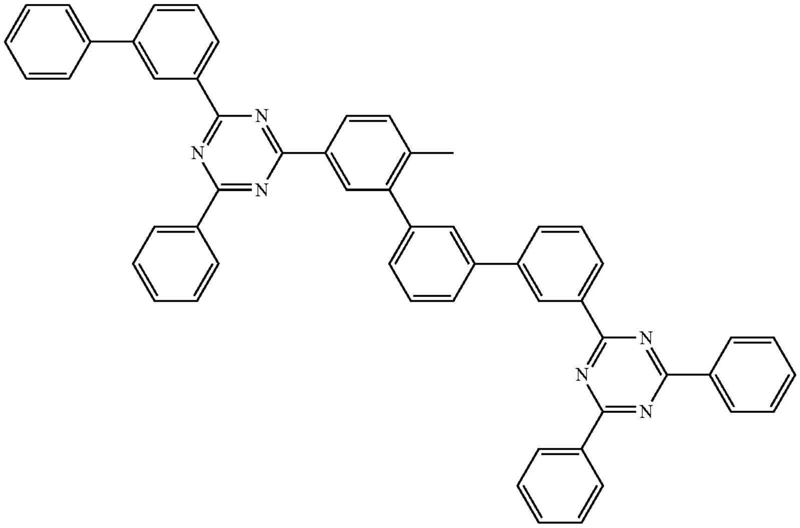

-continued
A(63)
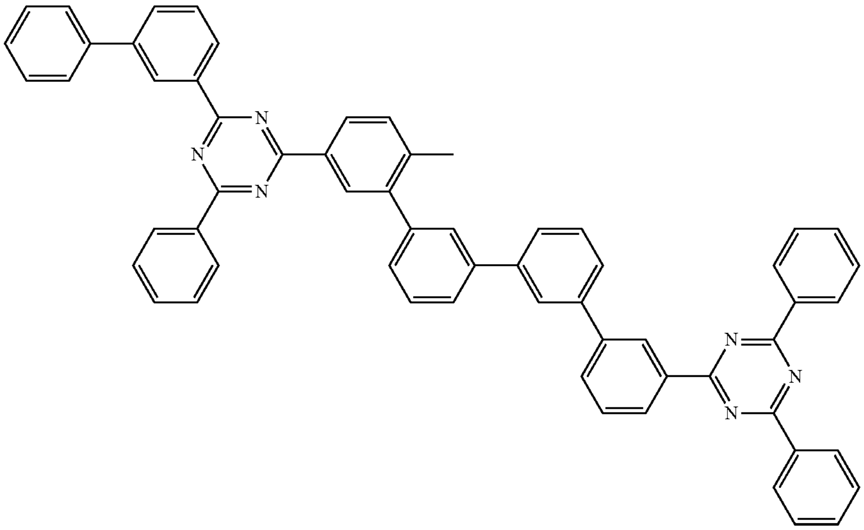
A(64)
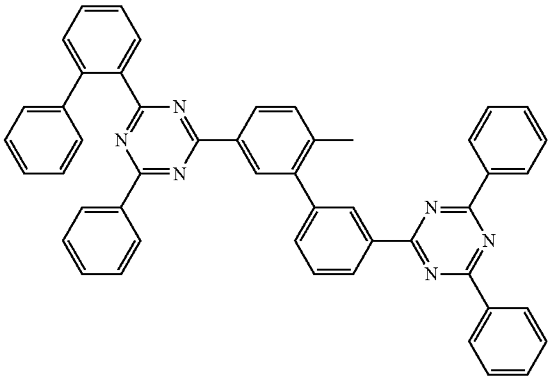
A(65)
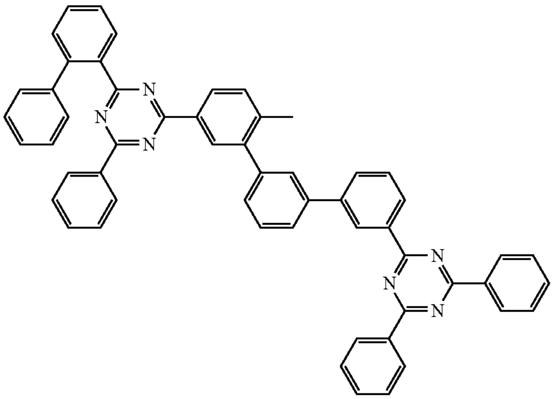
A(66)
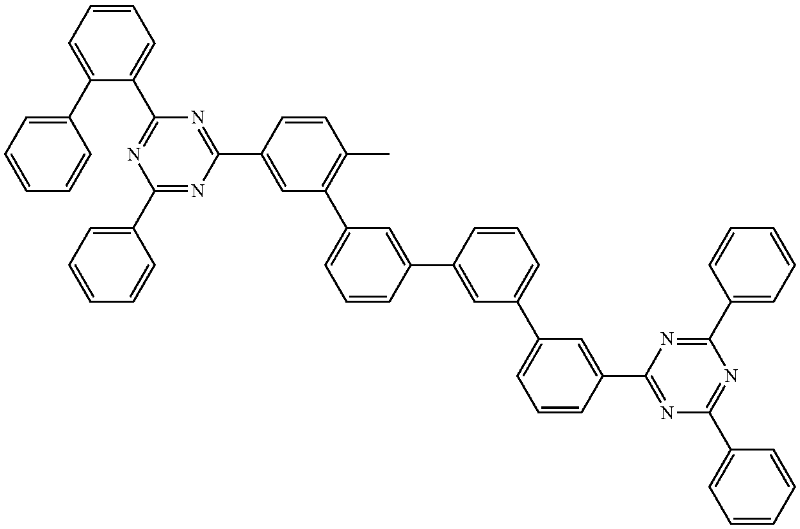

-continued
A(67)
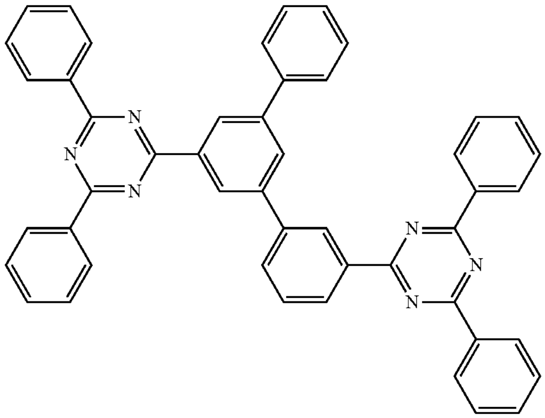
A(68)
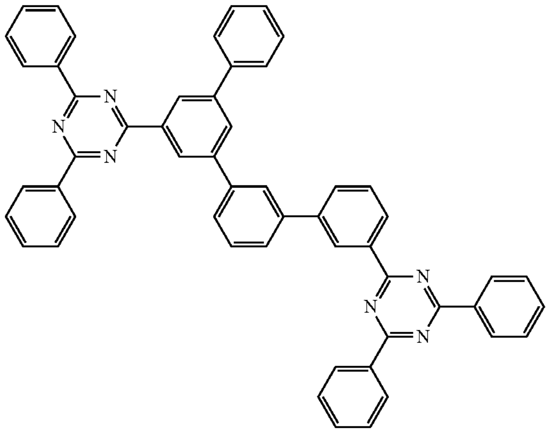
A(69)
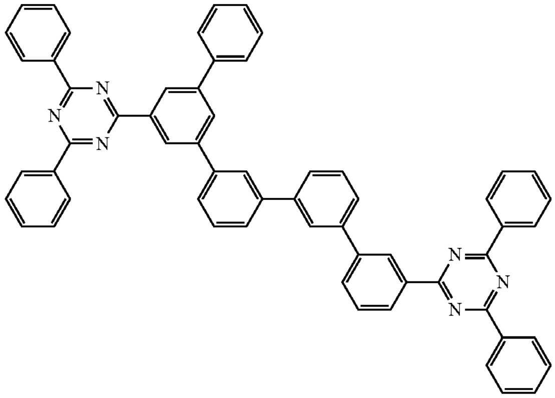
A(70)
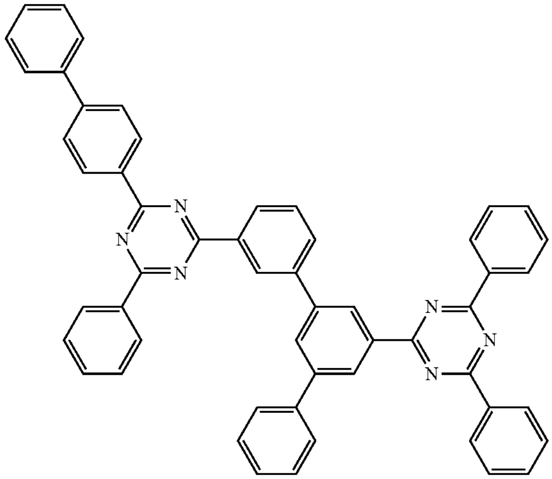
A(71)
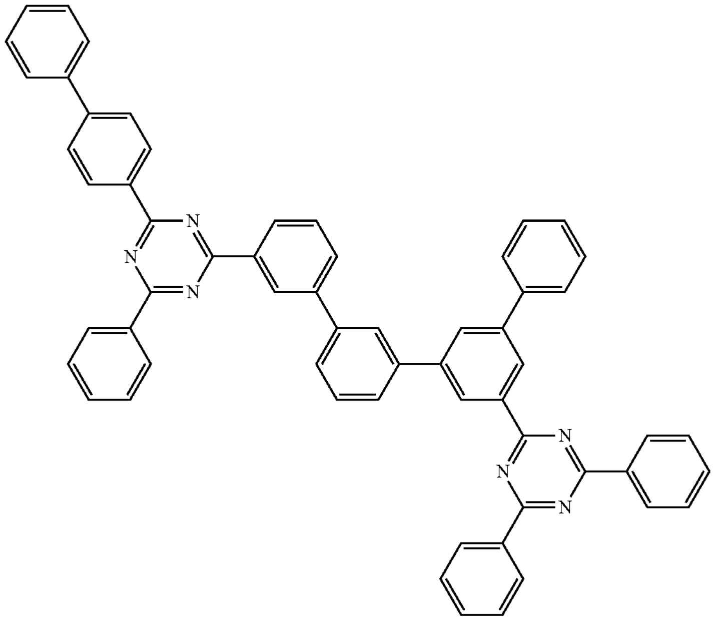

-continued
A(72)
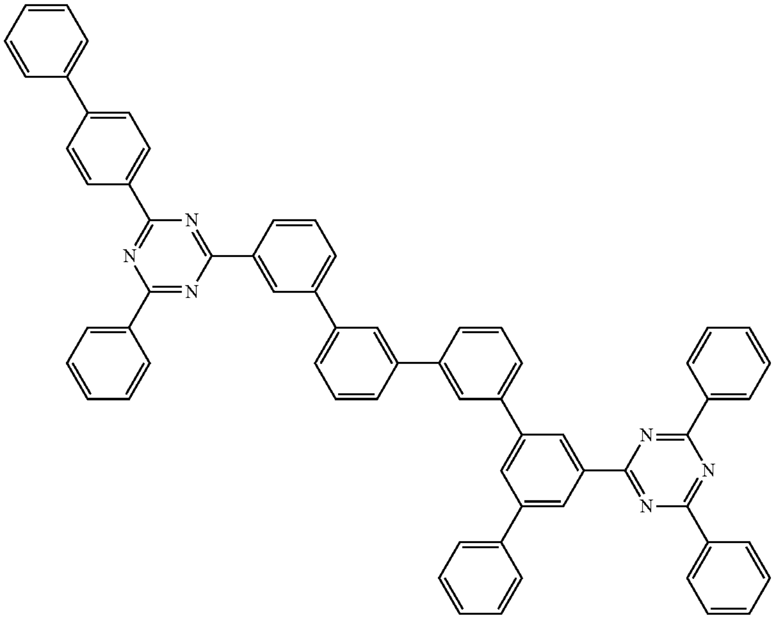
A(73)
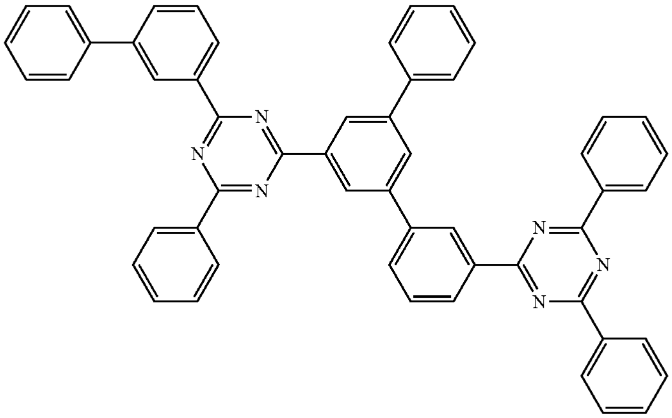
A(74)
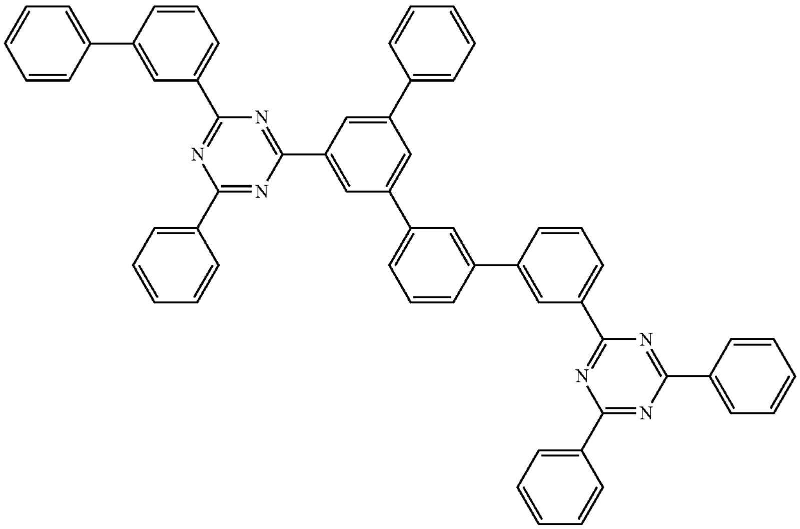

-continued
A(75)
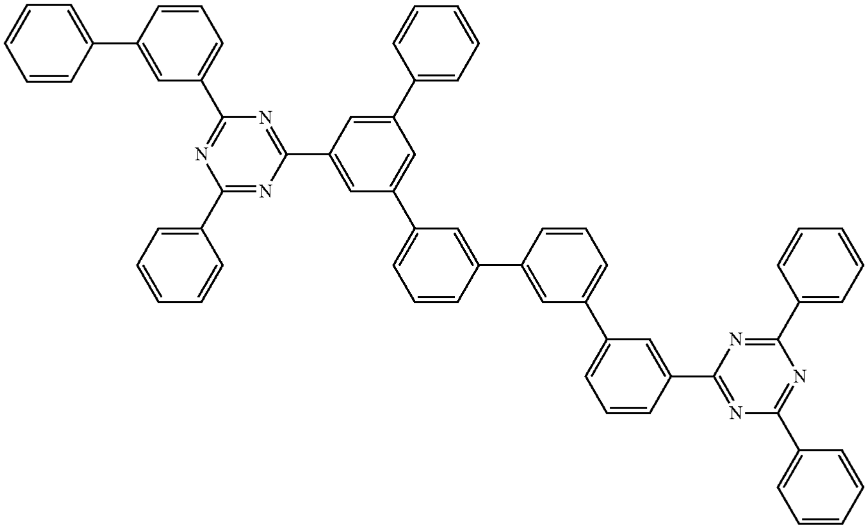
A(76)
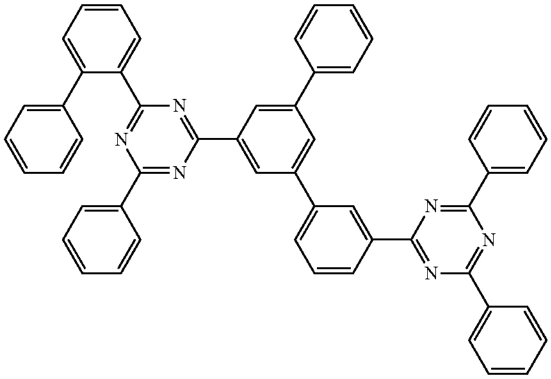
A(77)
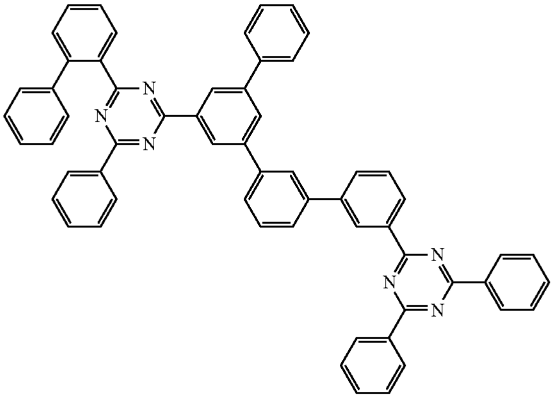
A(78)
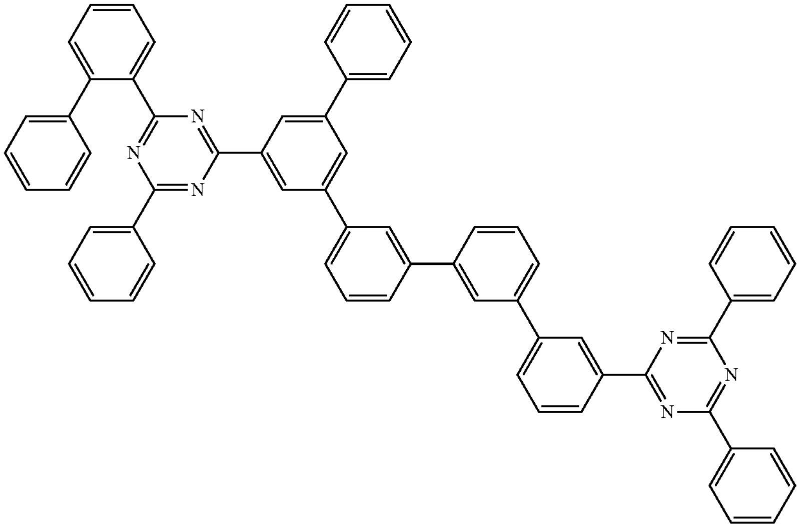

-continued
A(79)
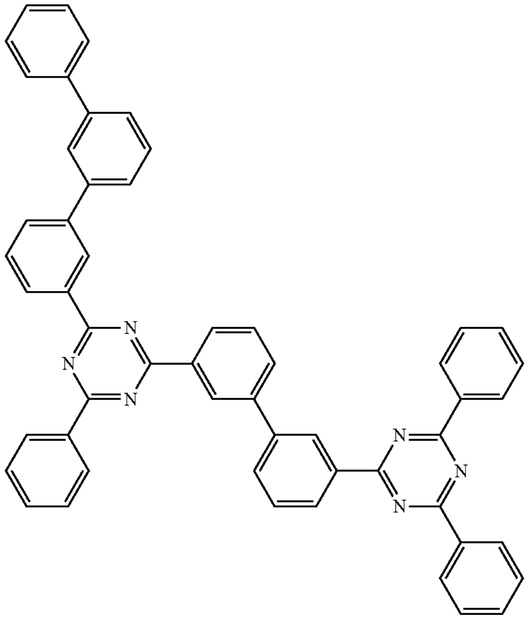
A(80)
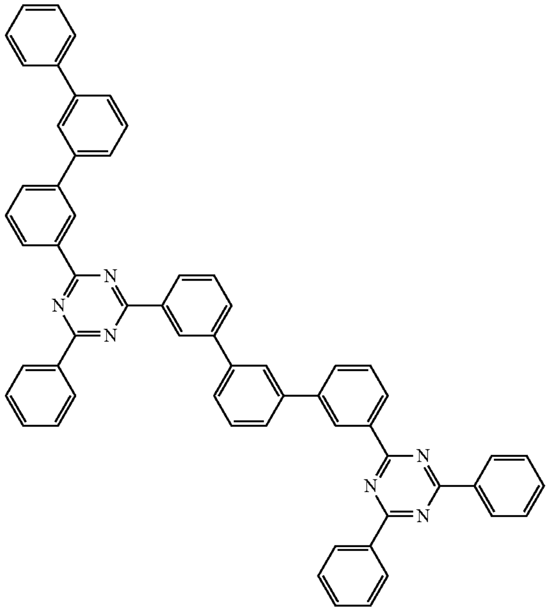
A(81)
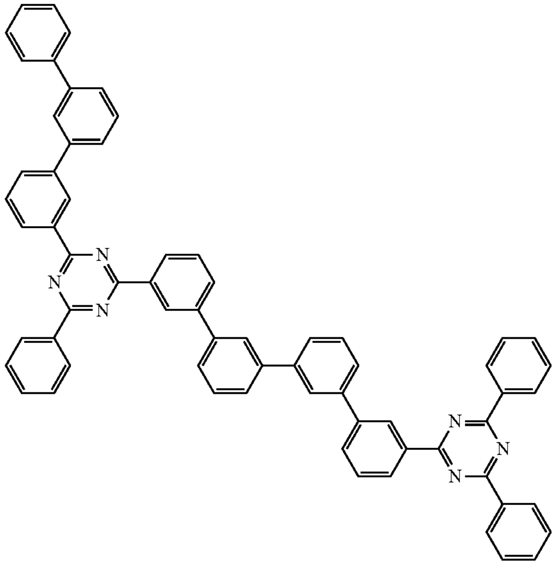
A(82)
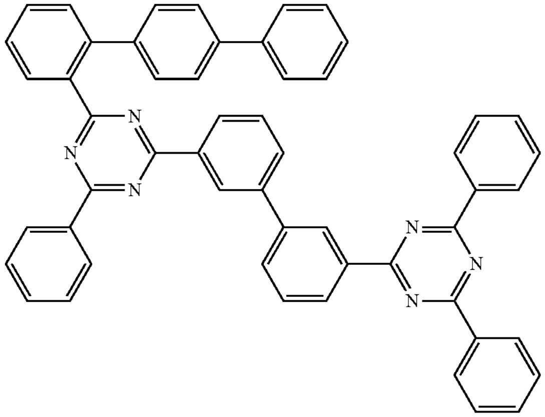

-continued
A(83)
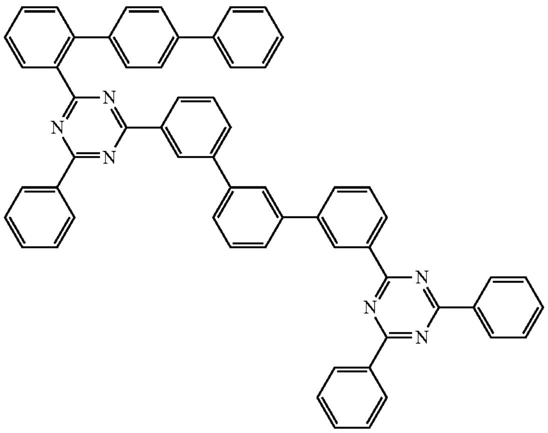
A(84)
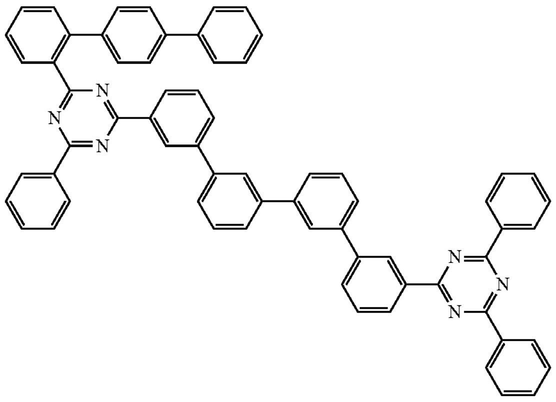
A(85)
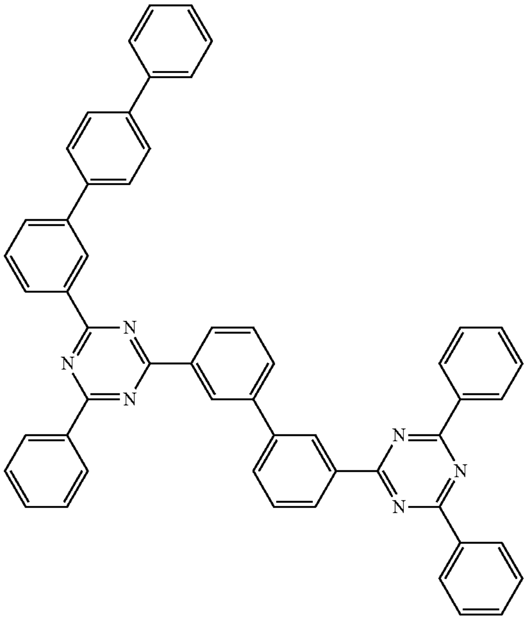
A(86)
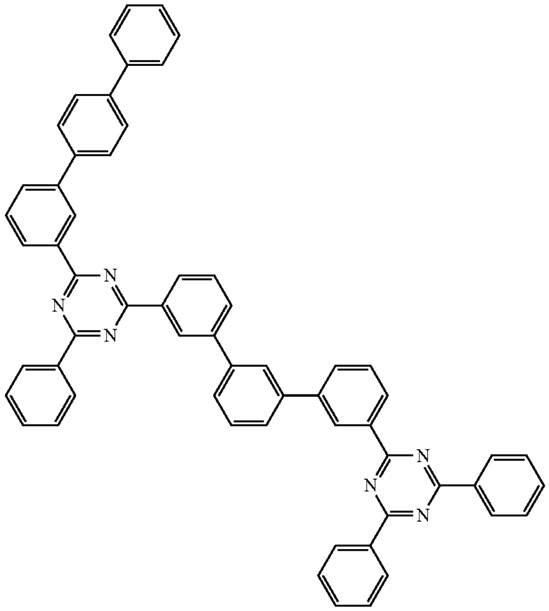

-continued
A(87)
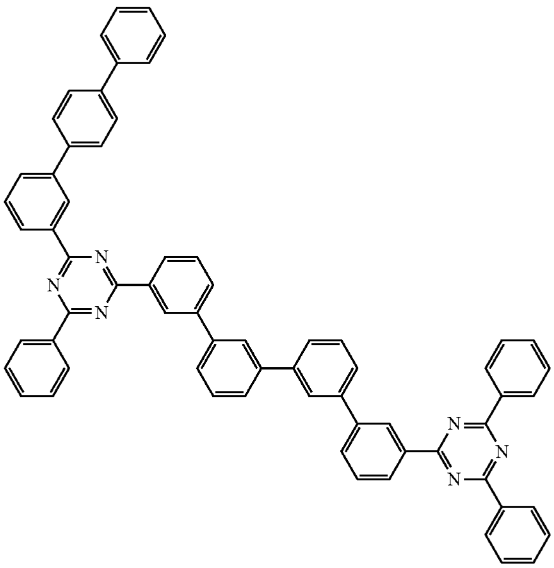
A(88)
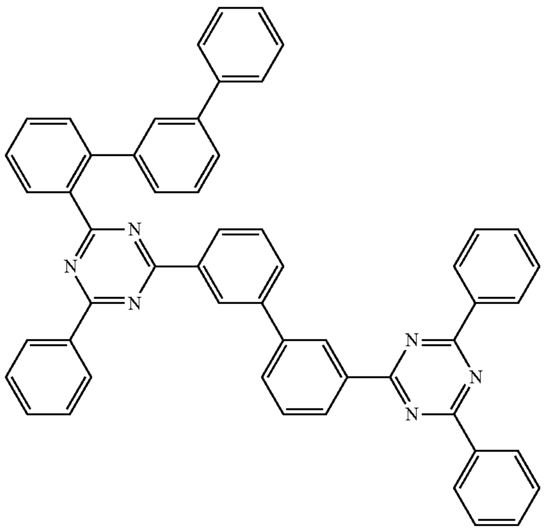
A(89)
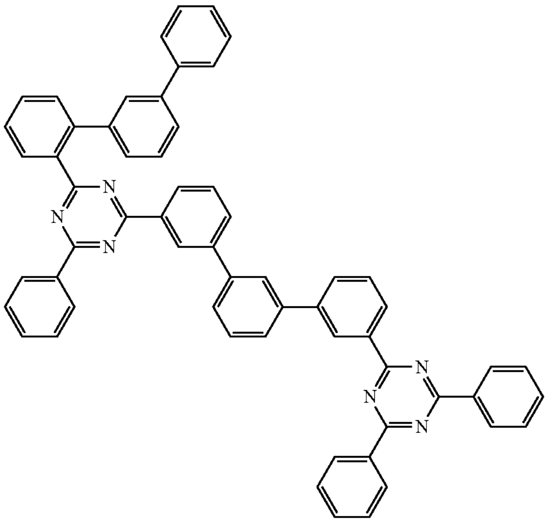
A(90)
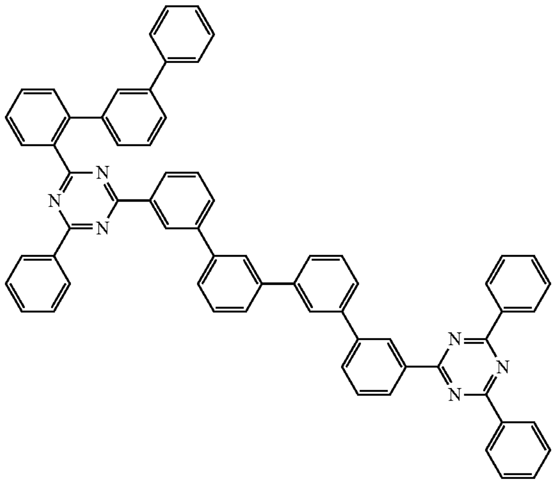
A(91)
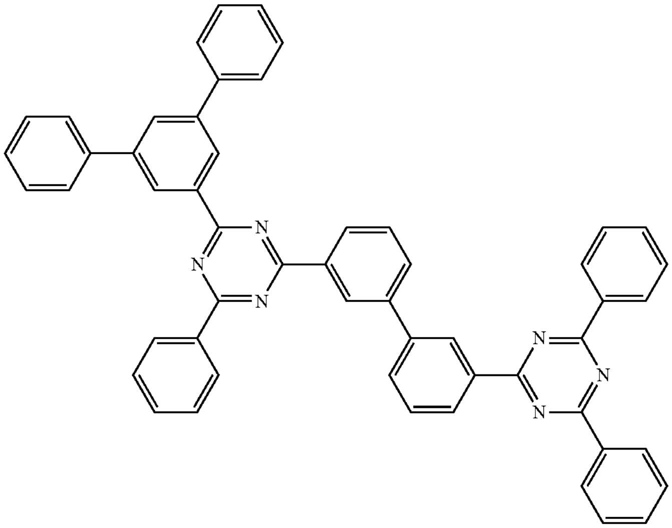

-continued
A(92)
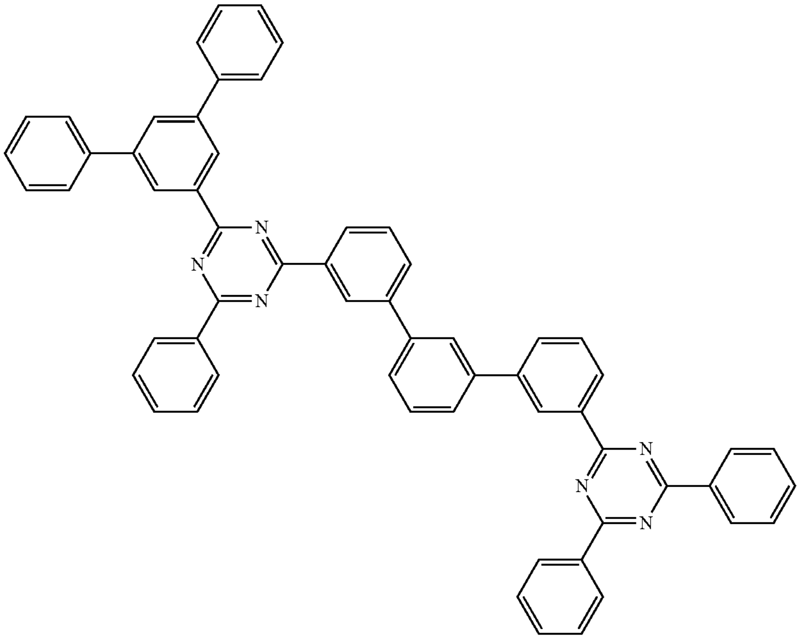
A(93)
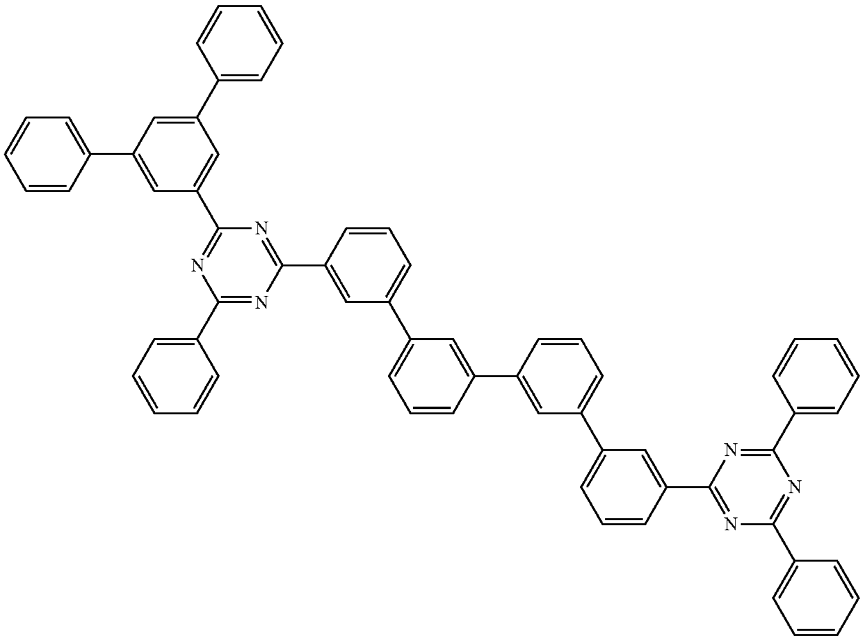

-continued
A(94)
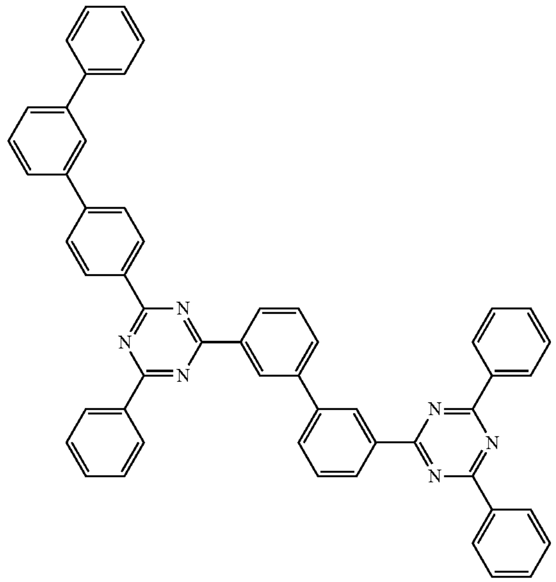
A(95)
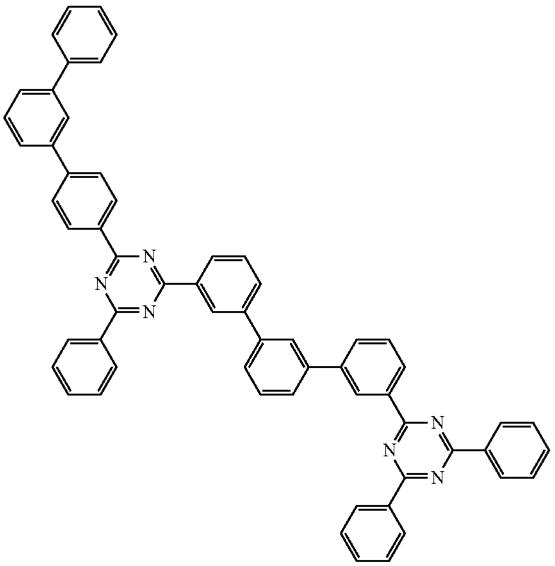
A(96)
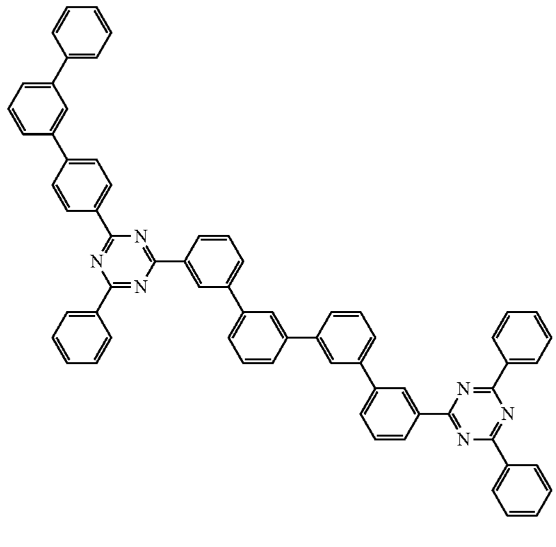
A(97)
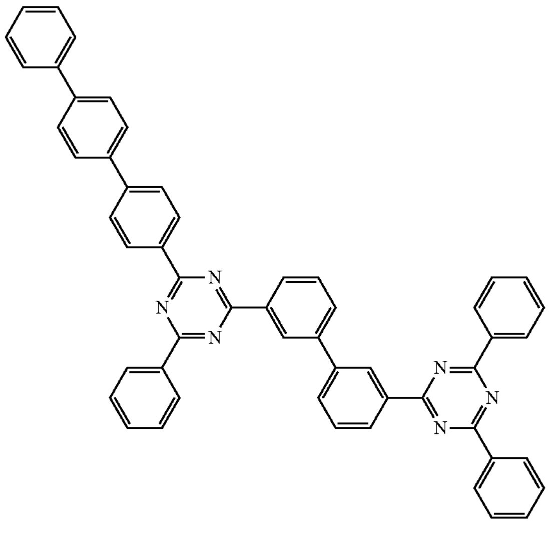

-continued
A(98)
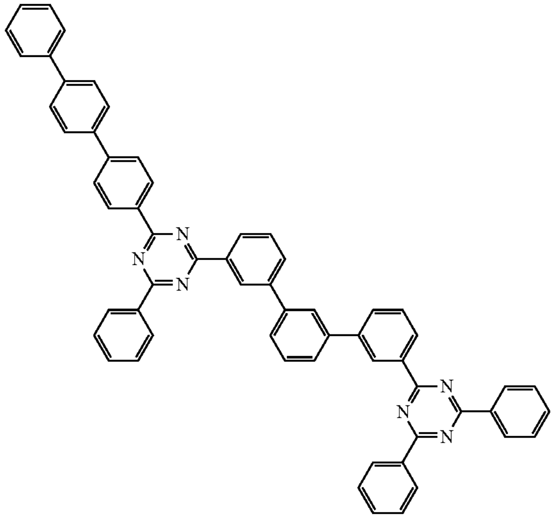
A(99)
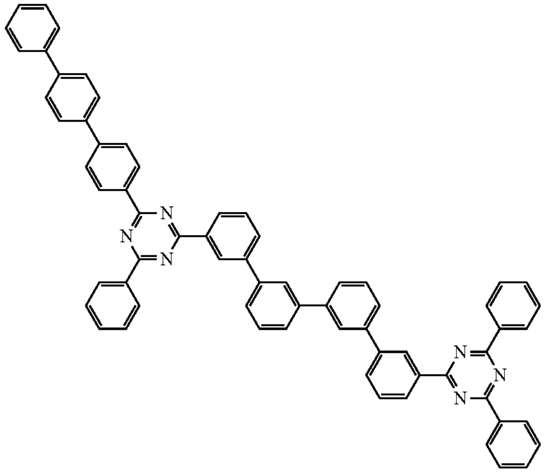
A(100)
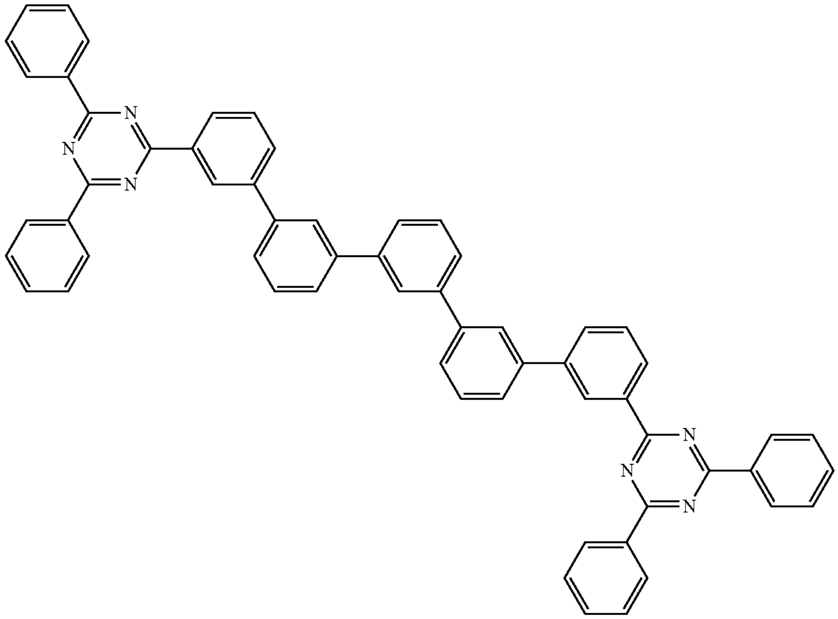

-continued
A(101)
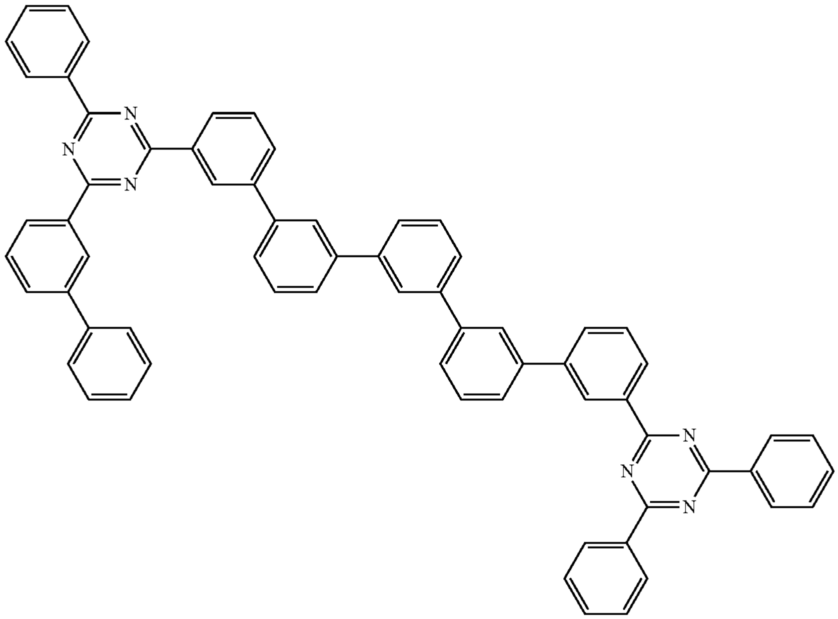
A(102)
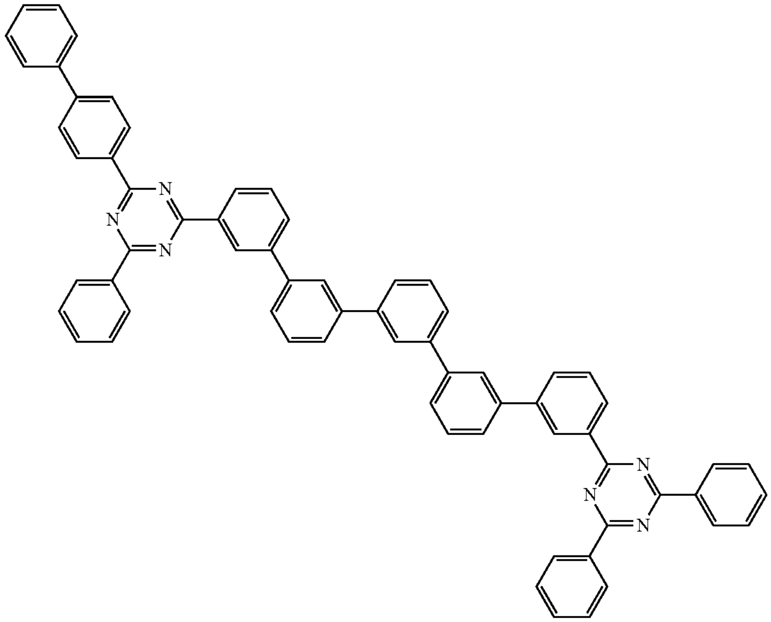

-continued
A(103)
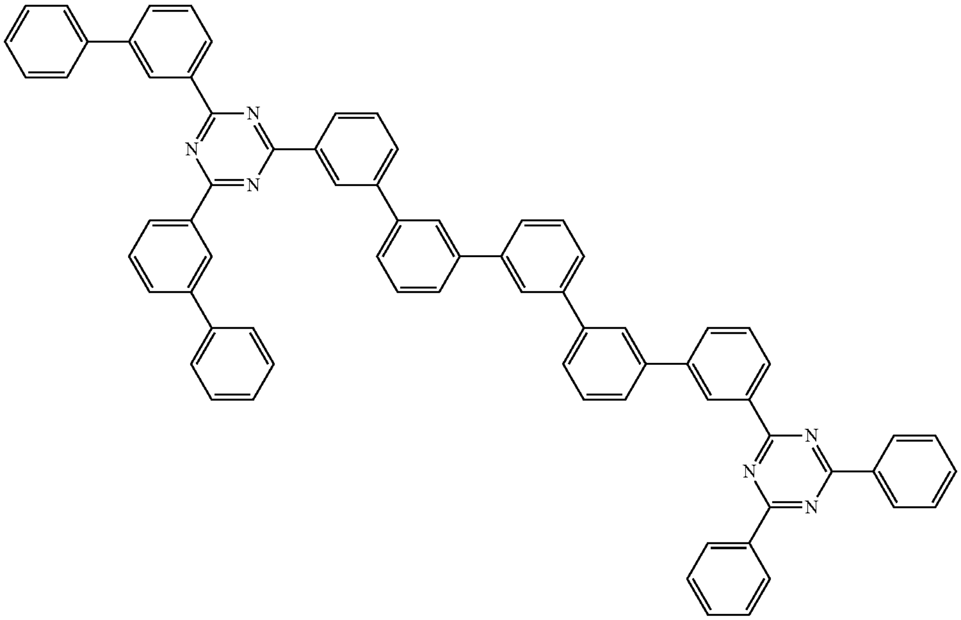
A(104)
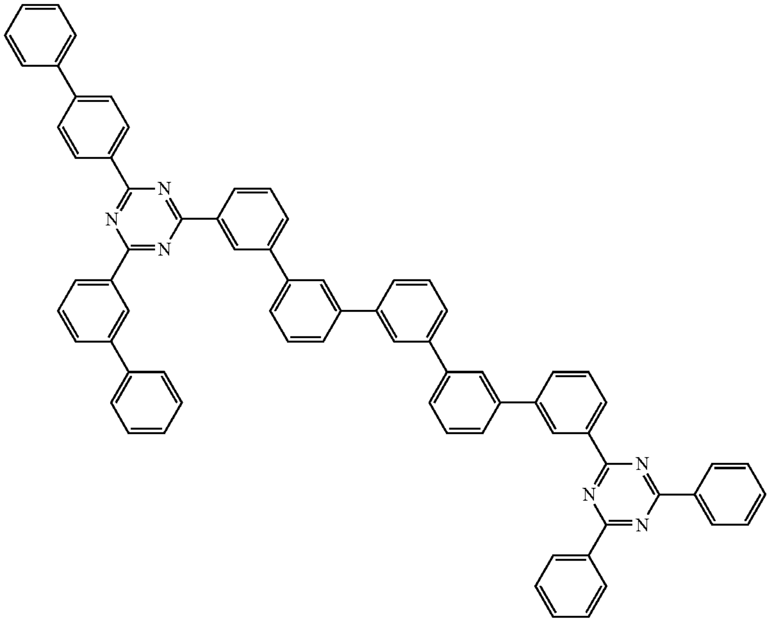

-continued
A(105)
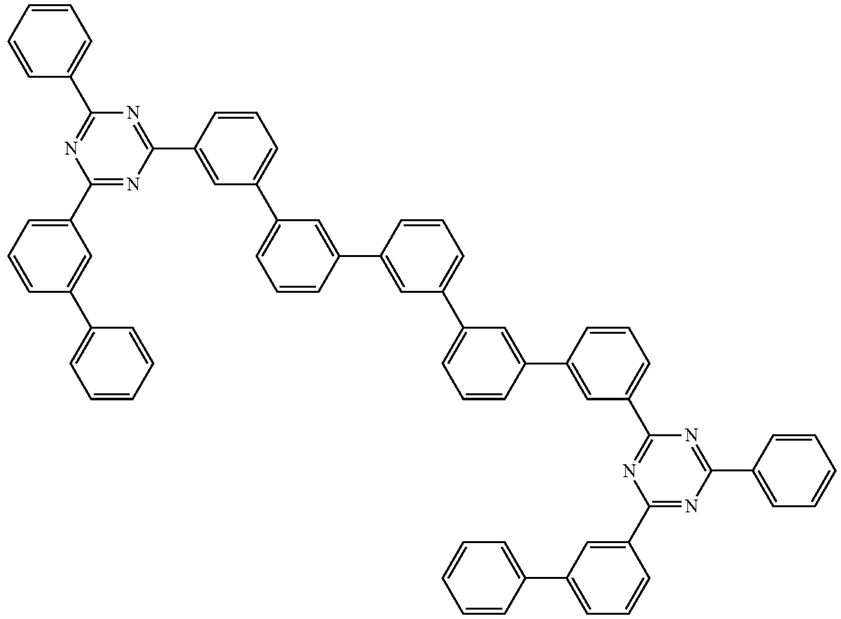
A(106)
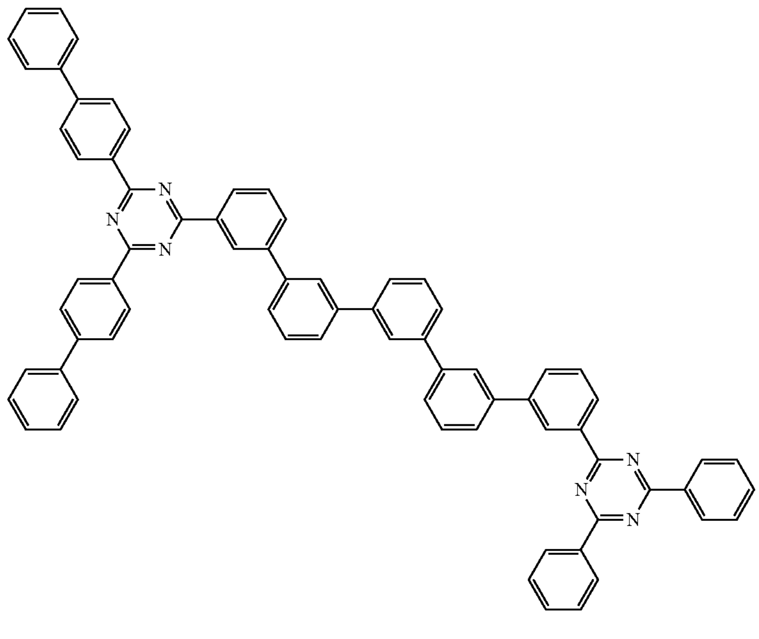

-continued
A(107)
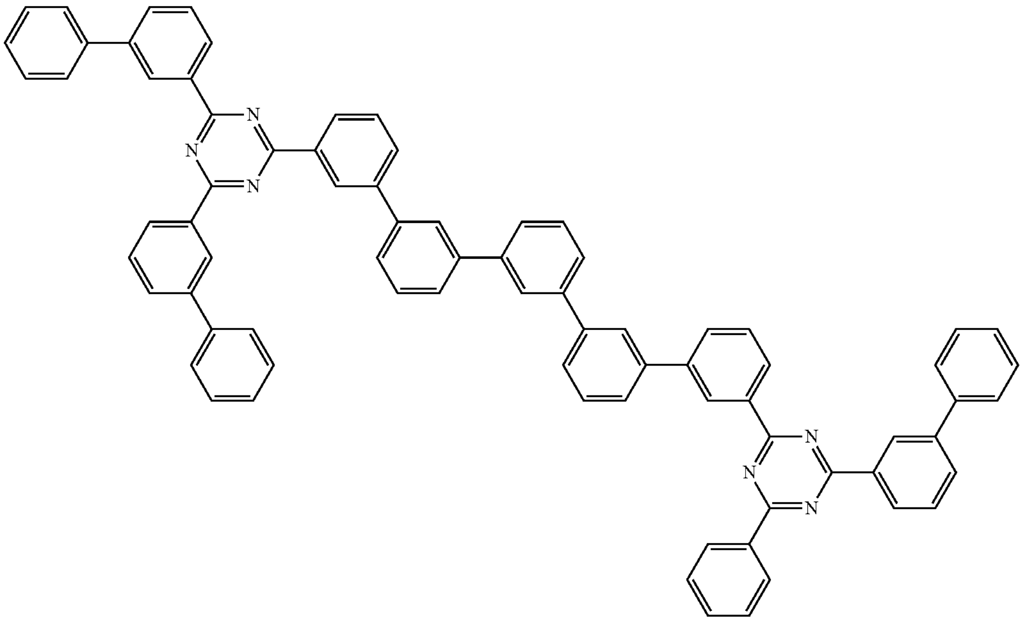
A(108)
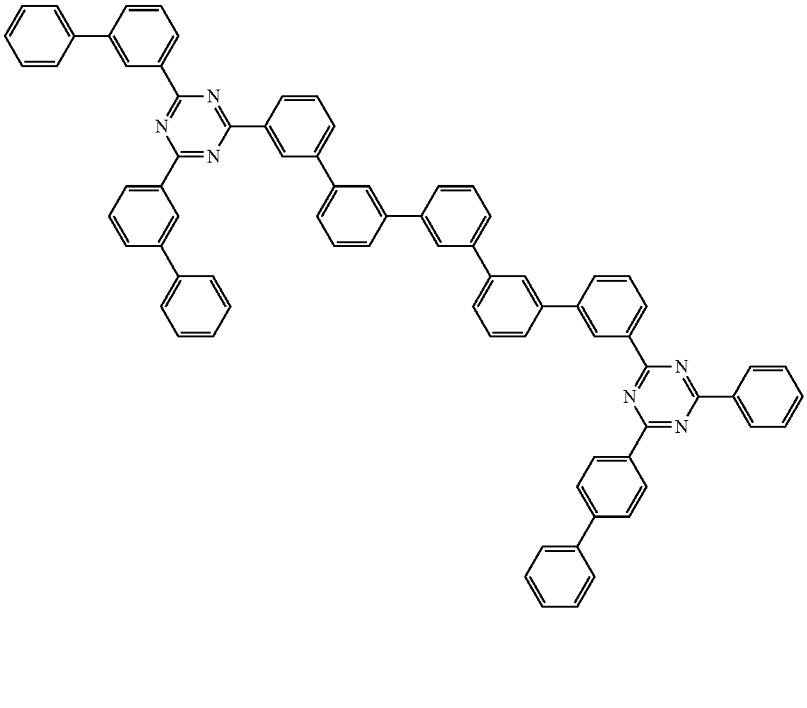

-continued
A(109)
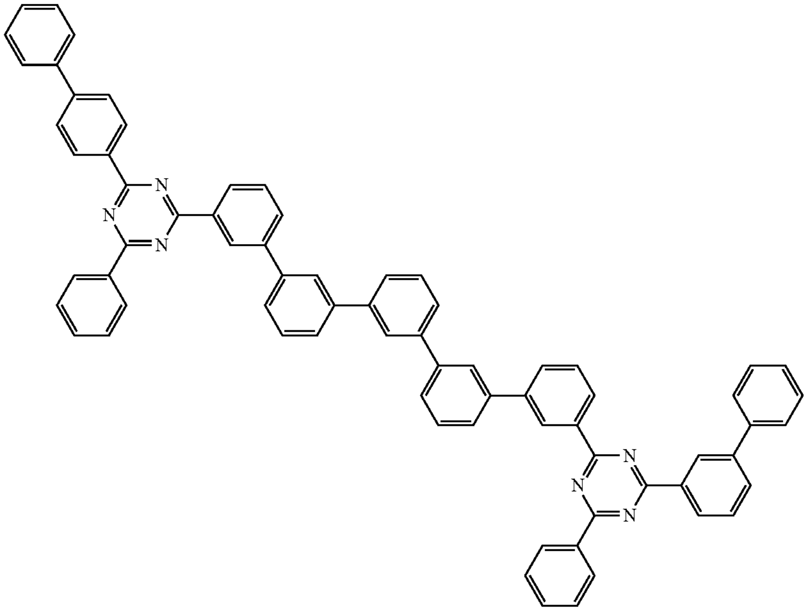
A(110)
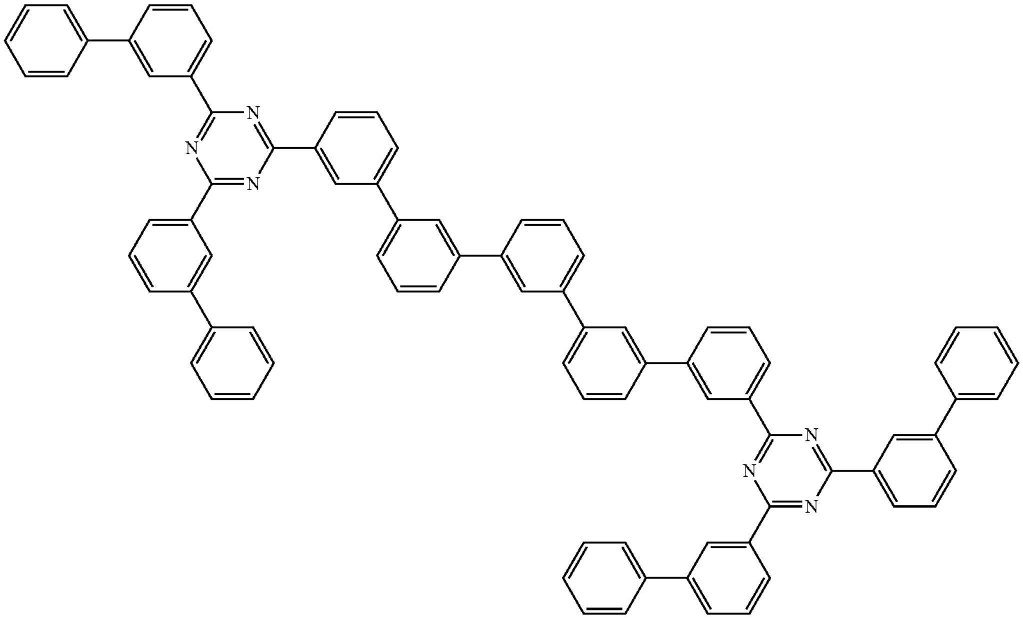

-continued
A(111)
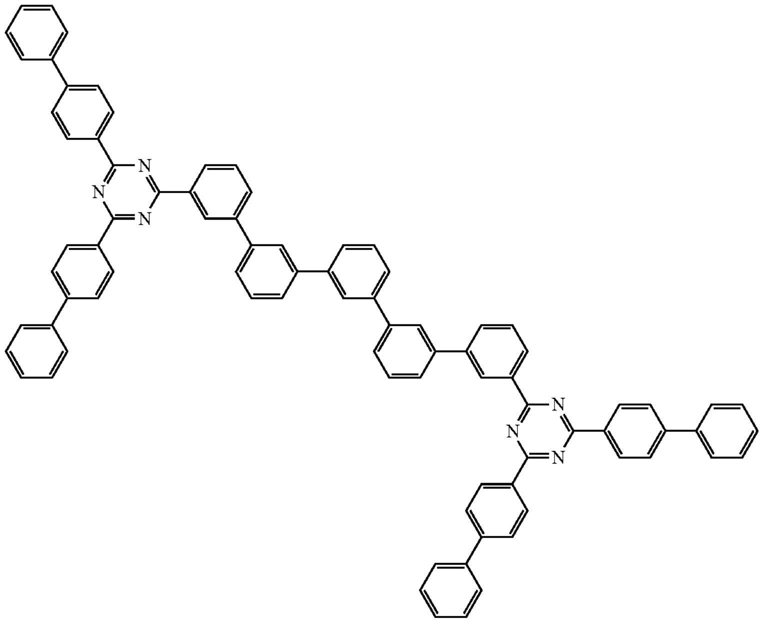
A(112)
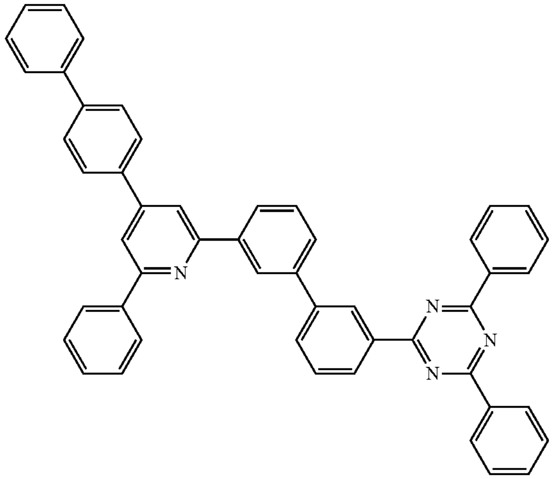
A(113)
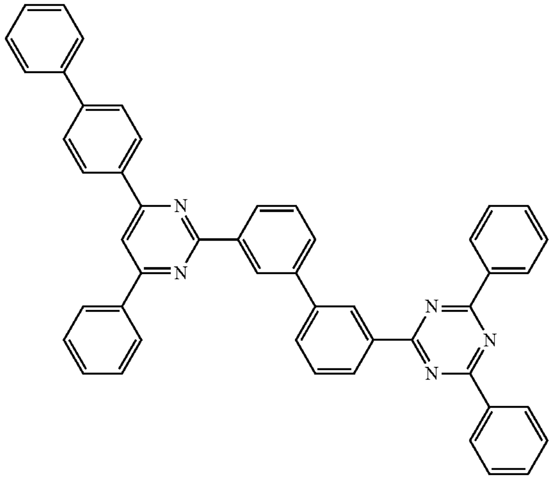
A(114)
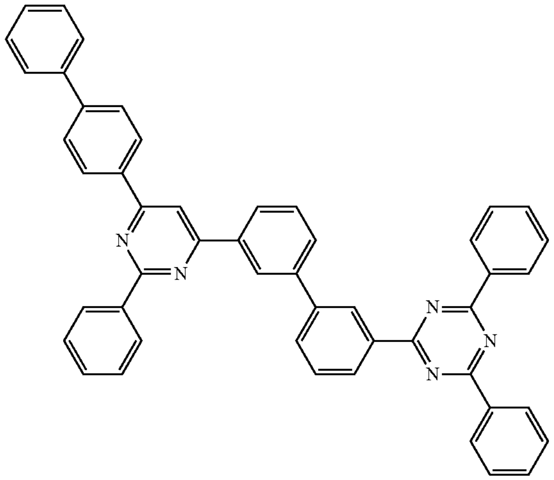
A(115)
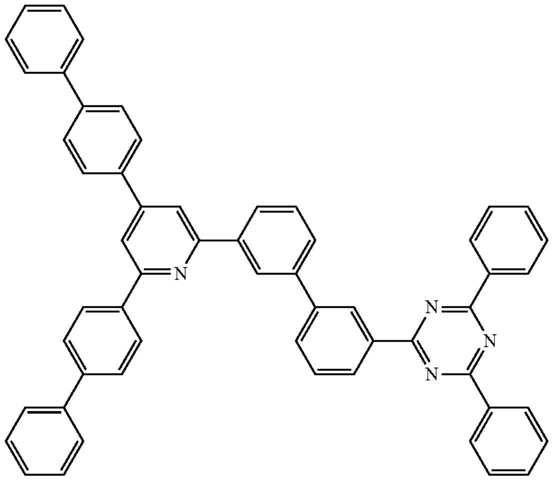

-continued
A(116)
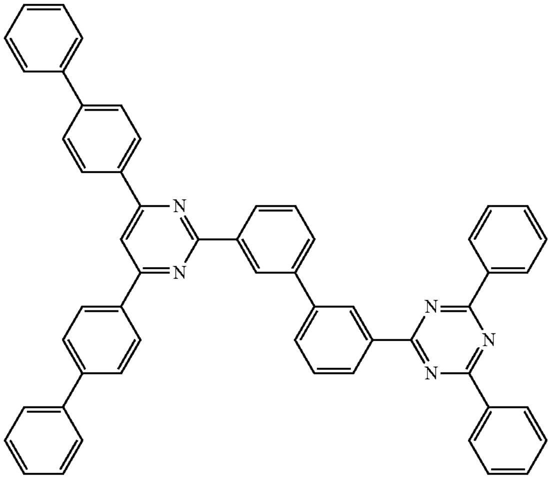
A(117)
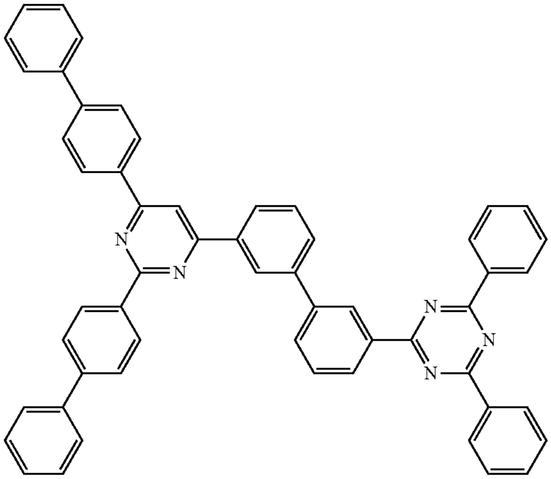
A(118)
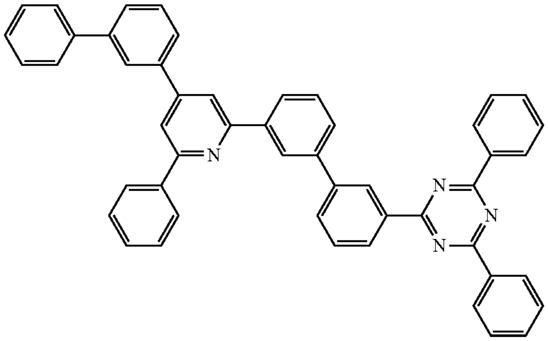
A(119)
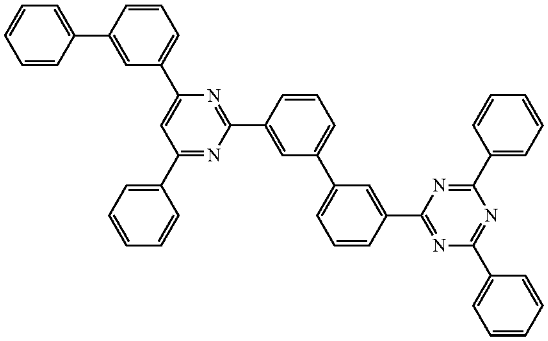
A(120)
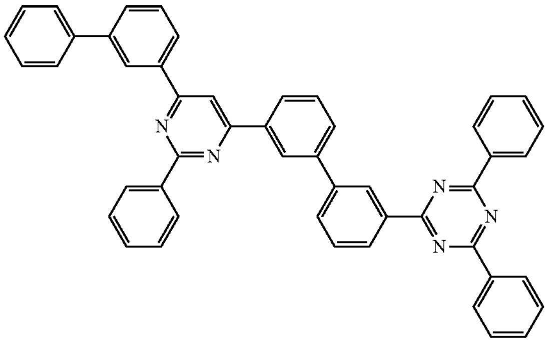
A(121)
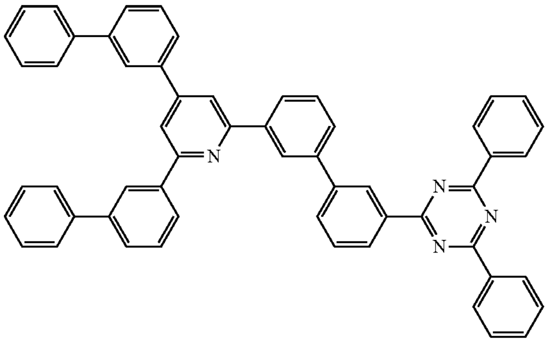

-continued
A(122)
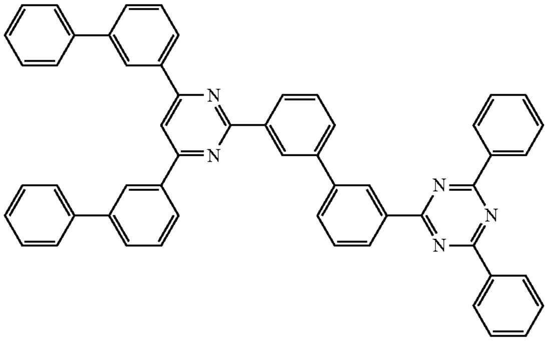
A(123)
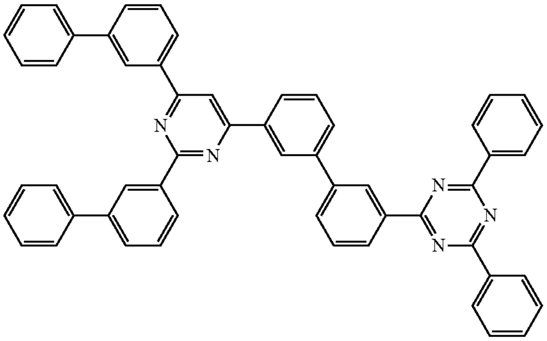
A(124)
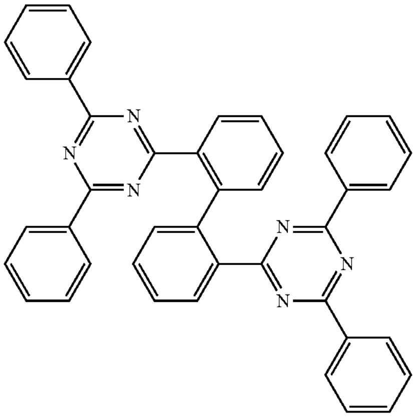
A(125)
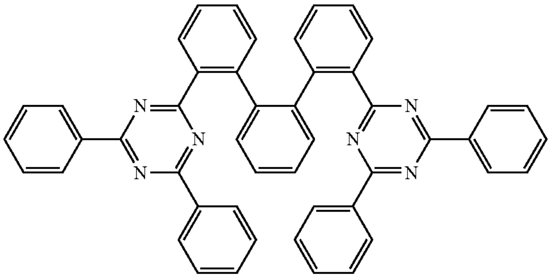
A(126)
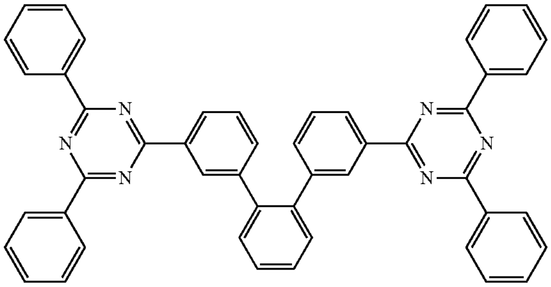
A(127)
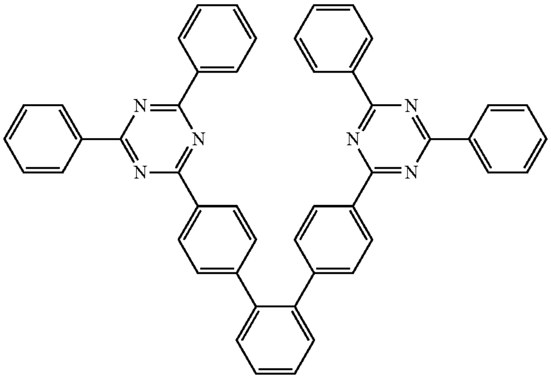

-continued
A(128)
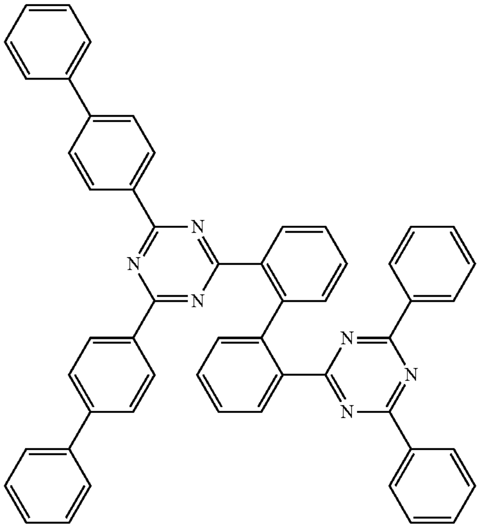
A(129)
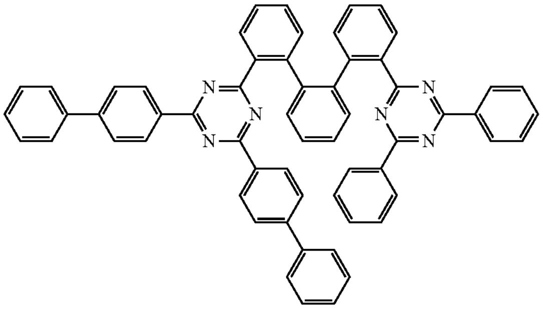
A(130)
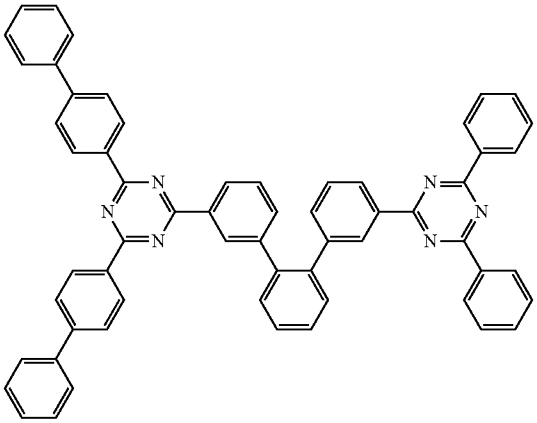
A(131)
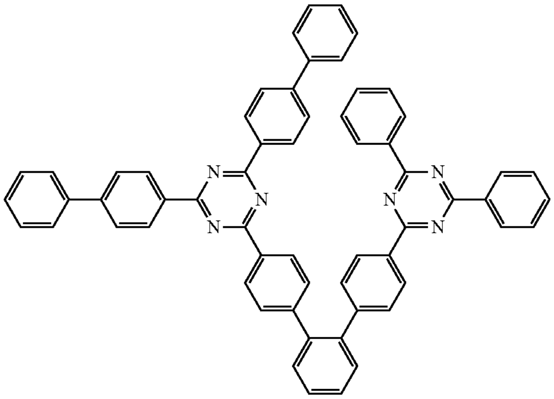
A(132)
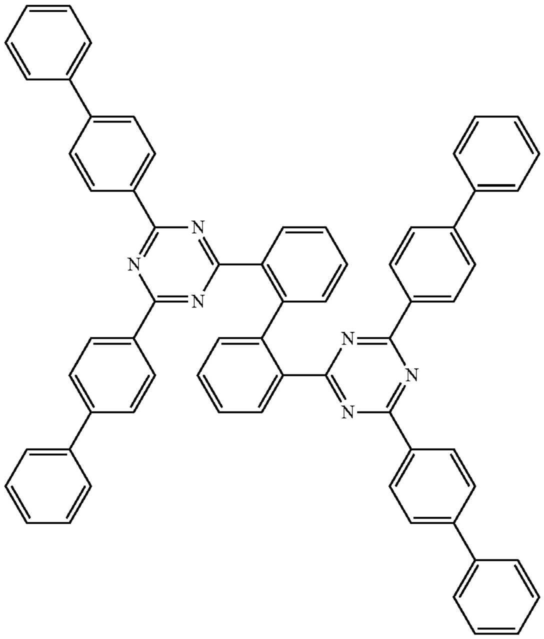
A(133)
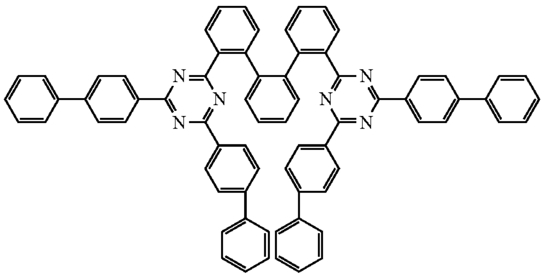

-continued
A((134)
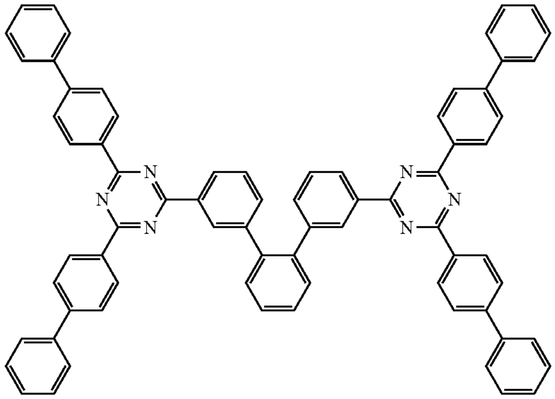
A(135)
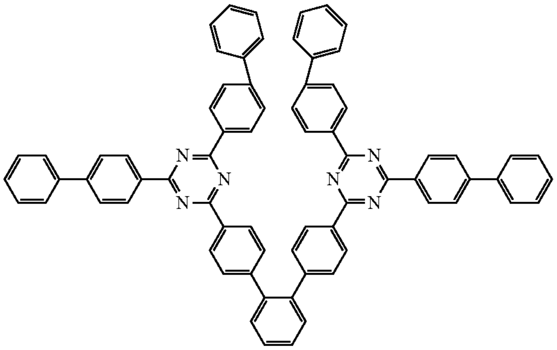
A(136)
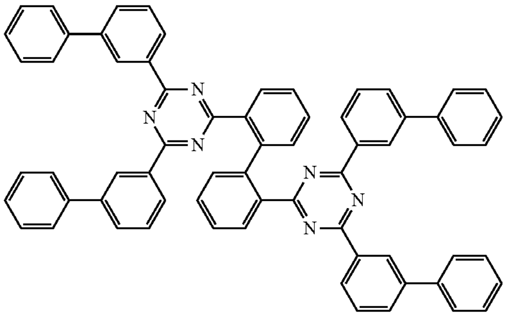
A(137)
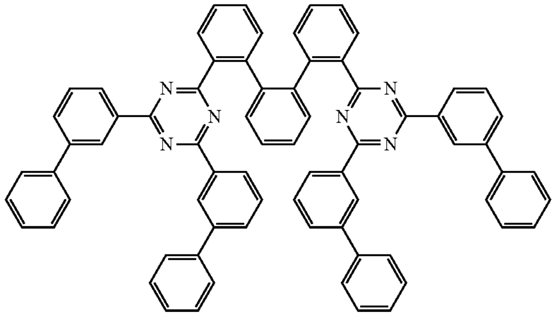
-continued
A(138)
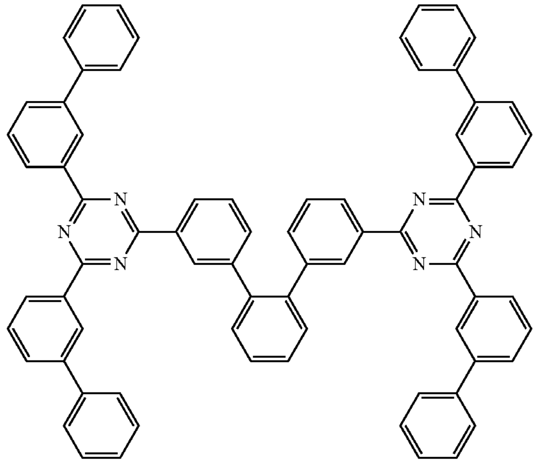
A(139)
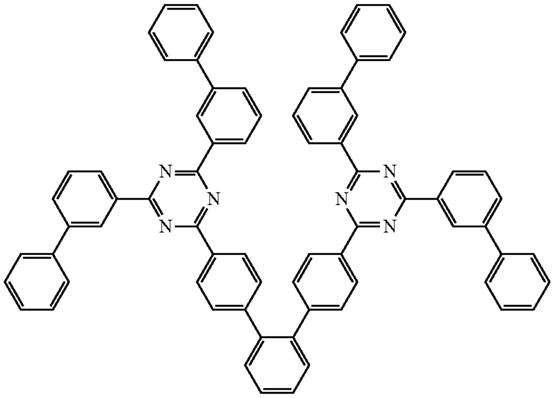
A(140)
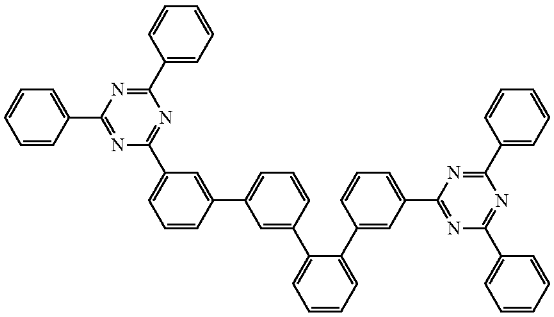
A(141)
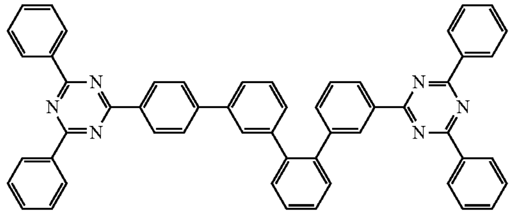

-continued
A(142)
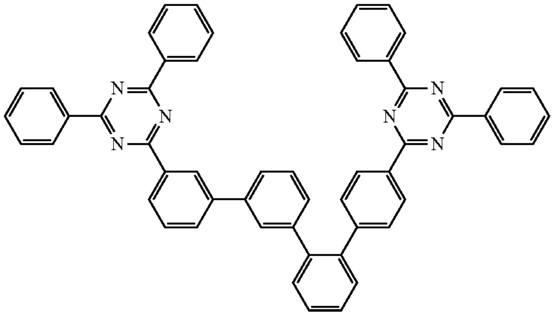
A(143)
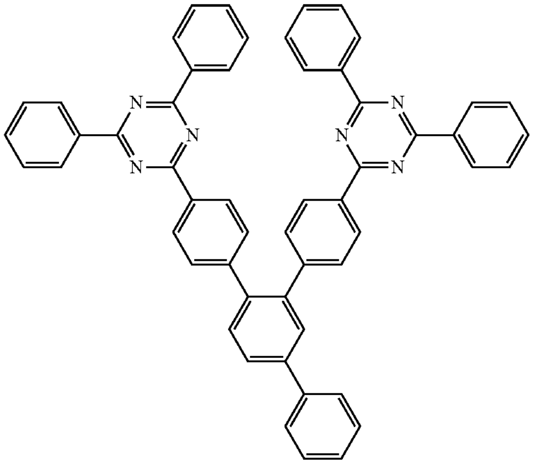
A(144)
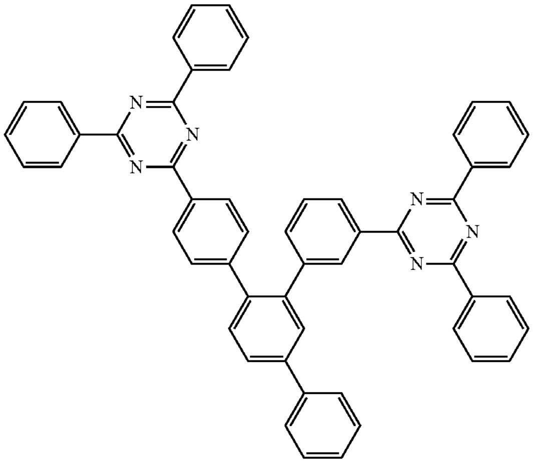
-continued
A(145)
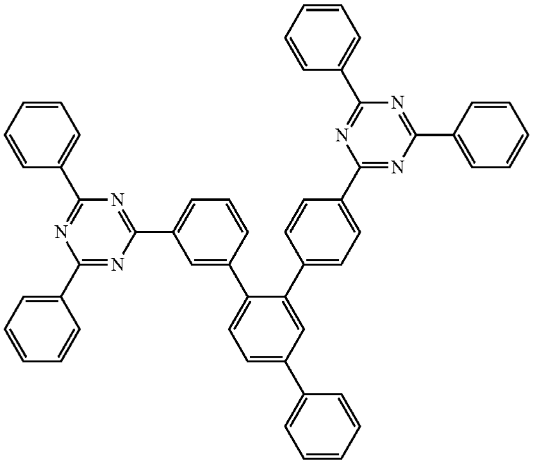
A(146)
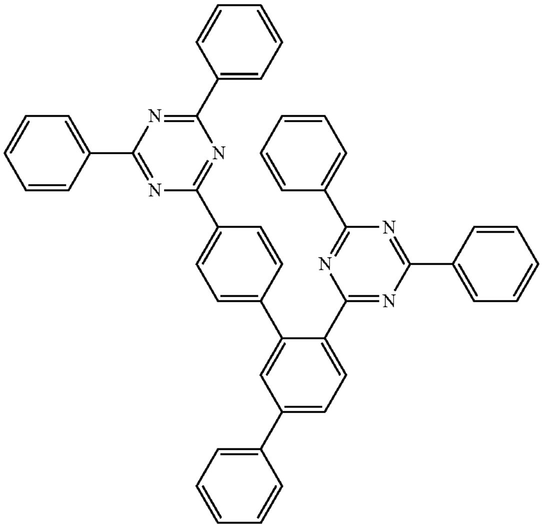
A(147)
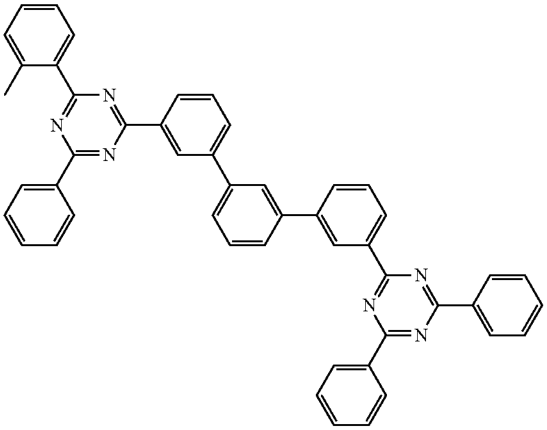

-continued
A(148)
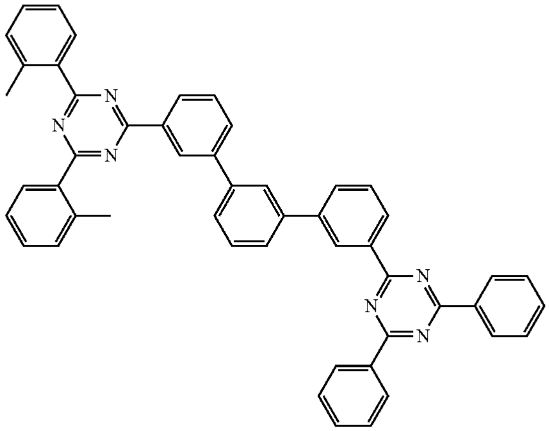
A(149)
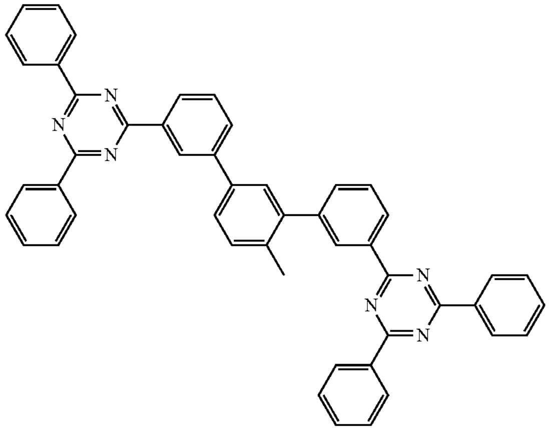
A(150)
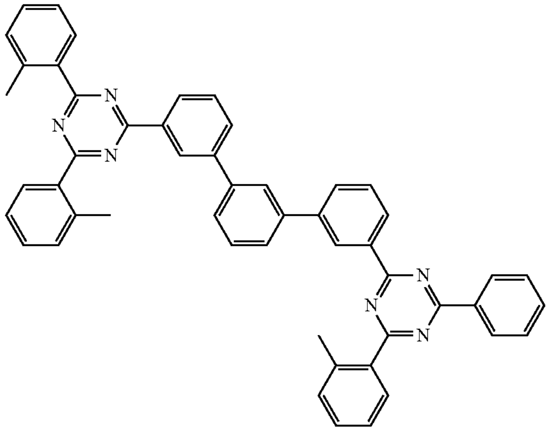
-continued
A(151)
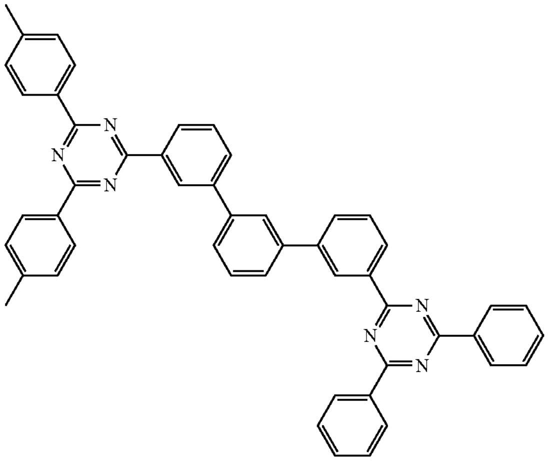
A(152)
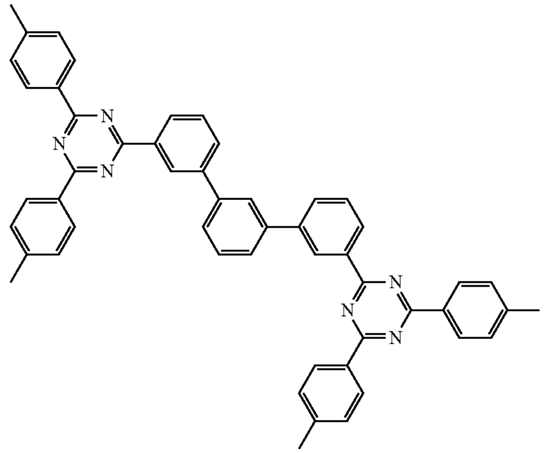
A(153)
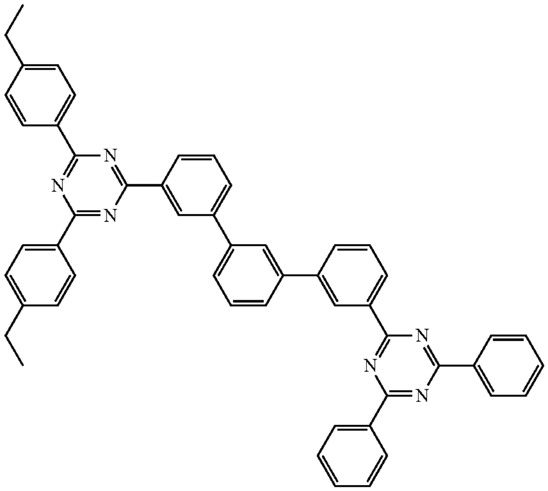

-continued
A(154)
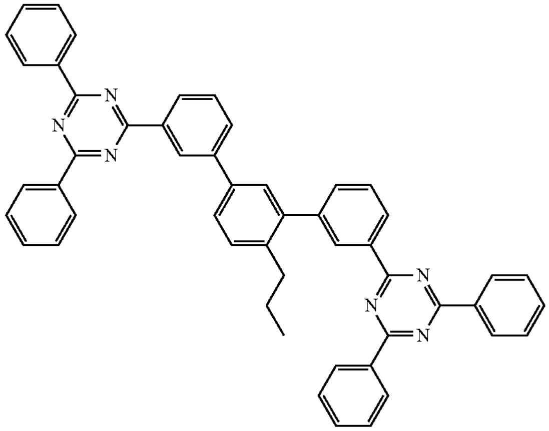
Group HE2
1
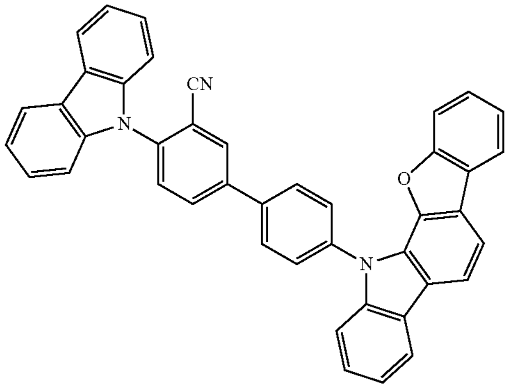
2
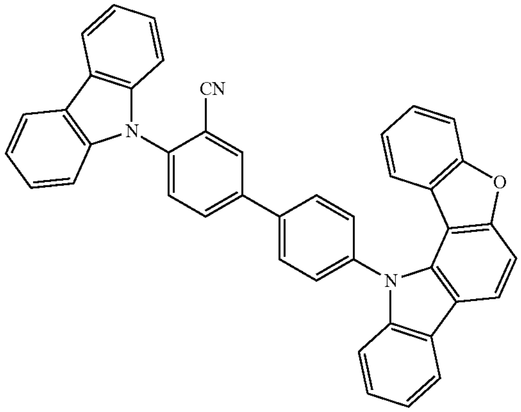
-continued
3
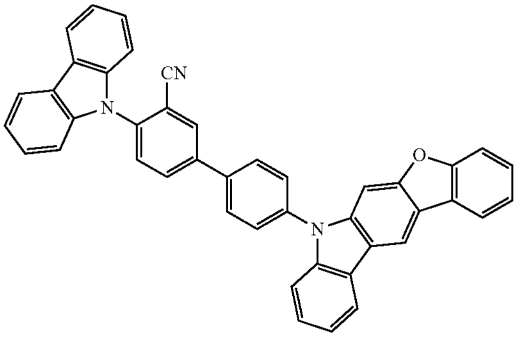
4
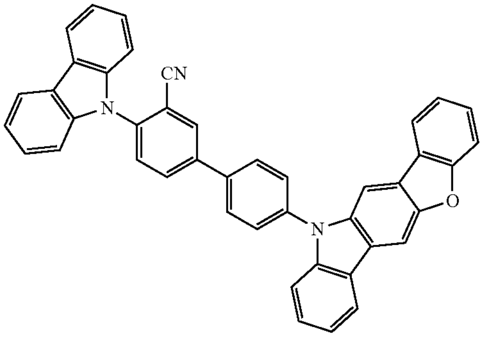
5
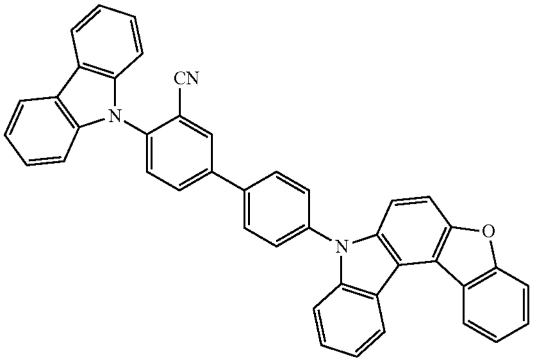
6
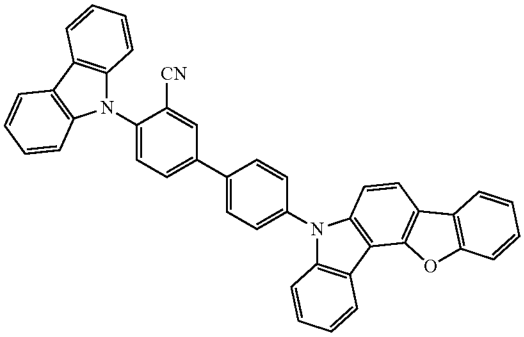

-continued
7
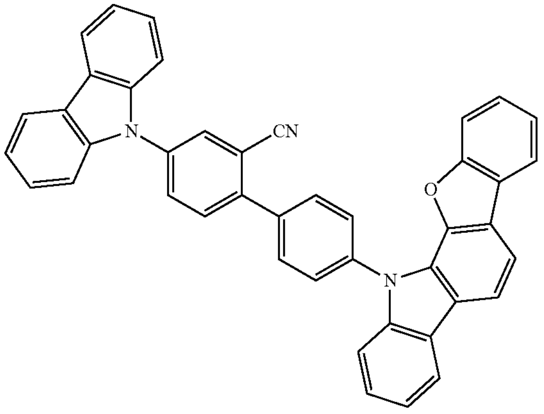
8
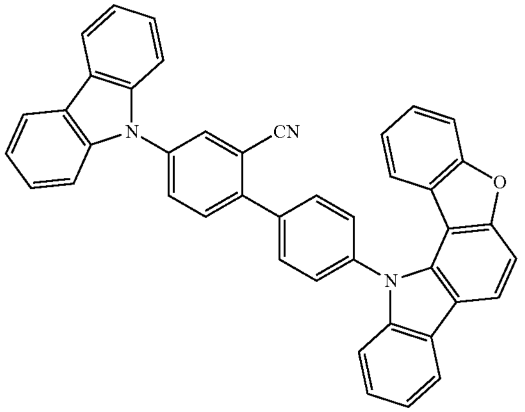
9
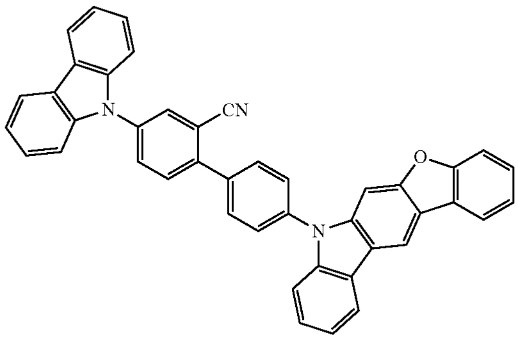
10
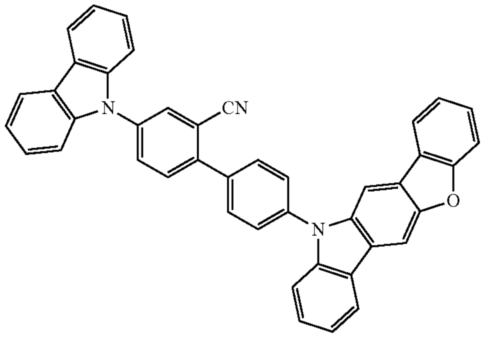
-continued
11
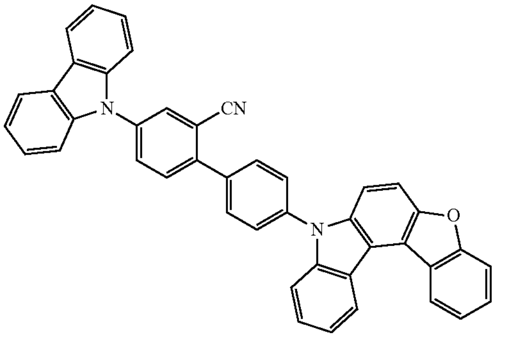
12
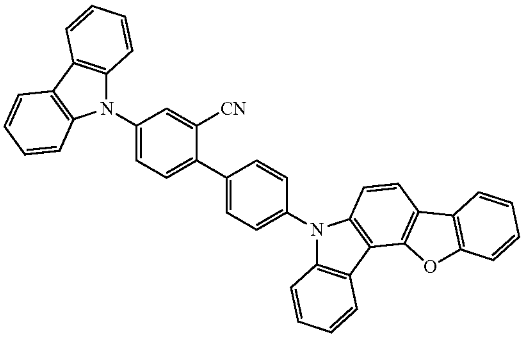
13
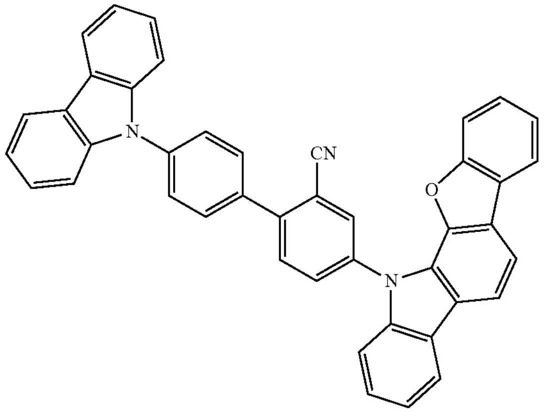
14
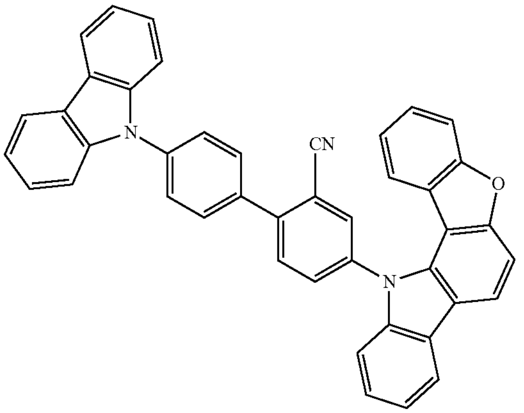

-continued
15
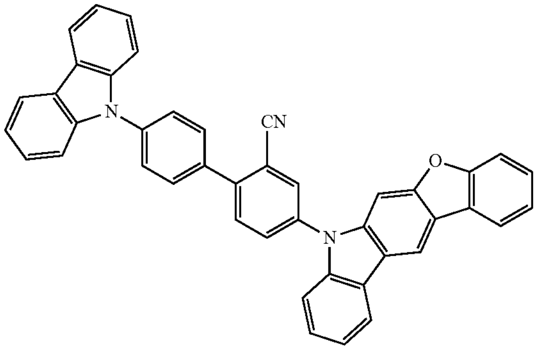
16
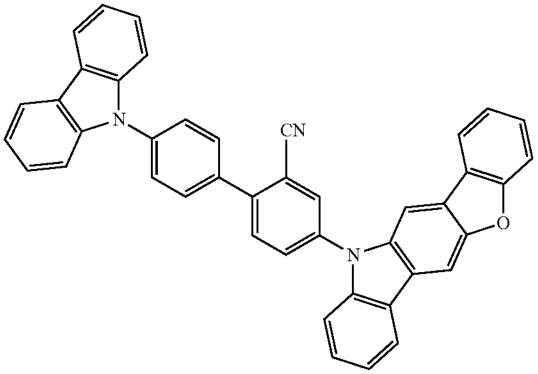
17
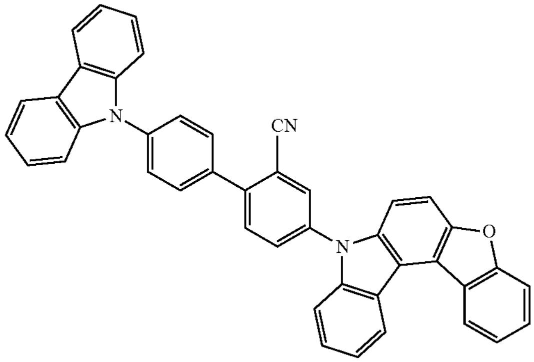
18
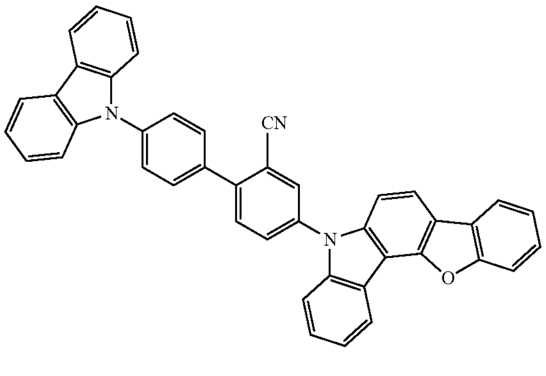
-continued
19
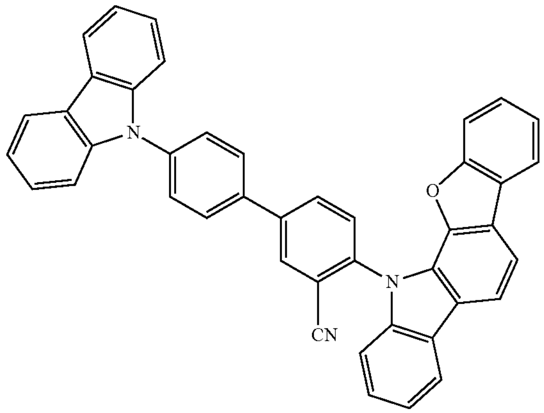
20
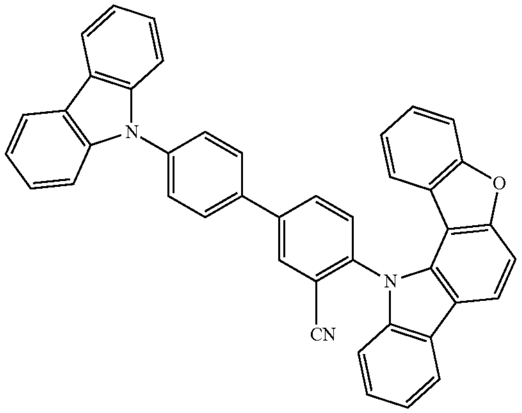
21
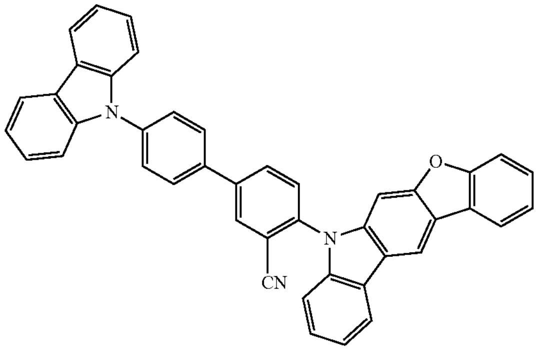
22
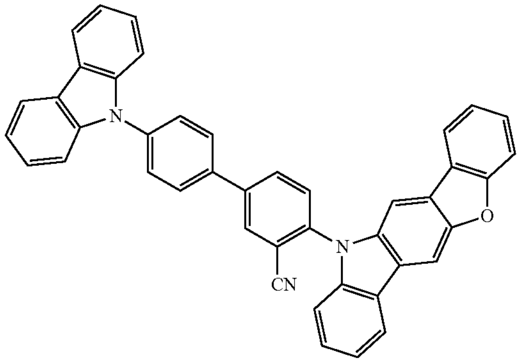

-continued
23
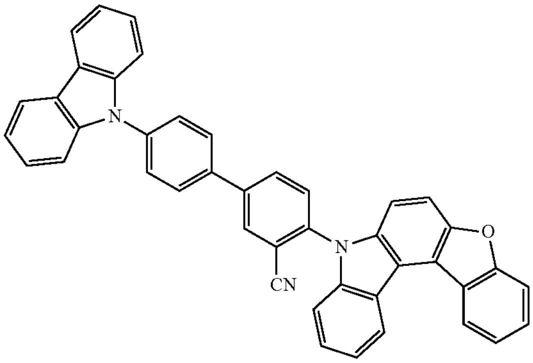
24
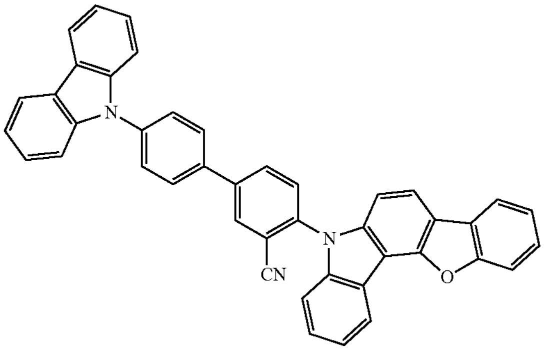
25
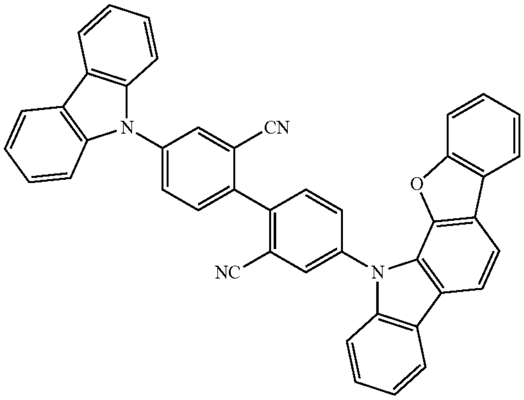
26
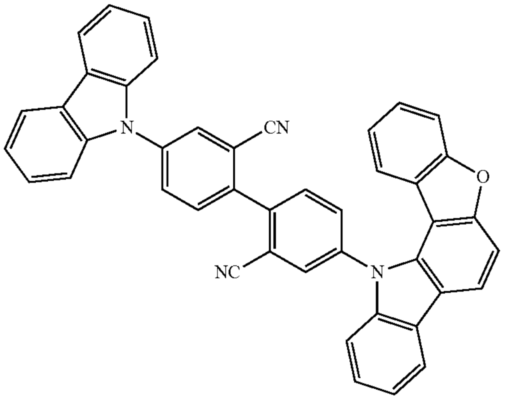
-continued
27
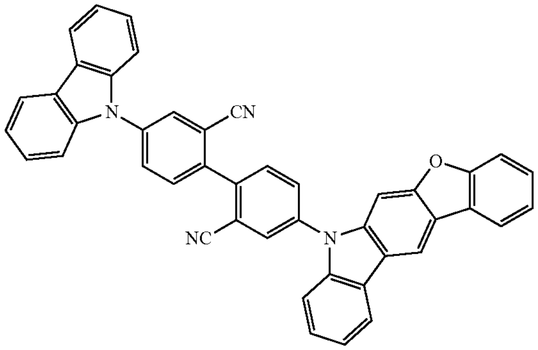
28
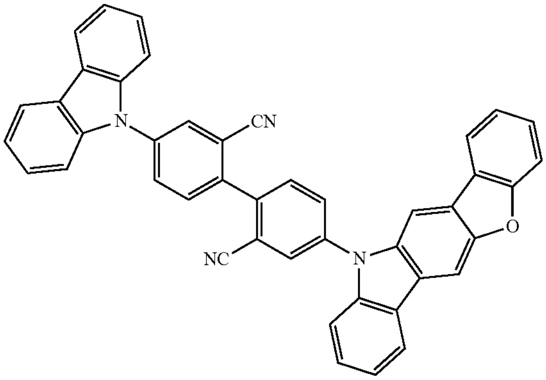
29
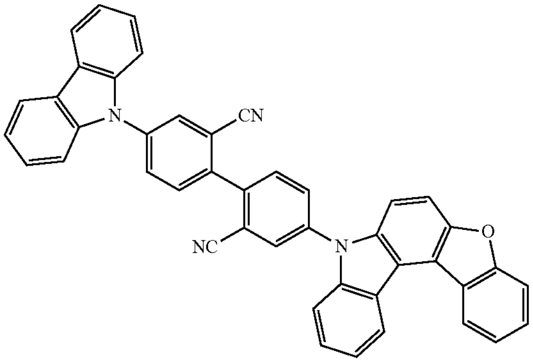
30
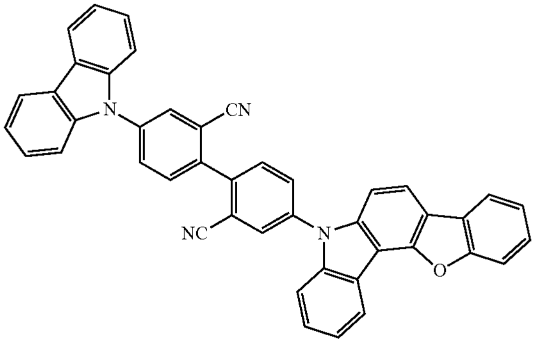

-continued
31
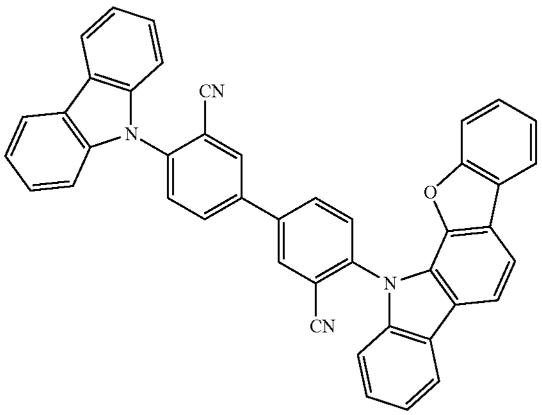
32
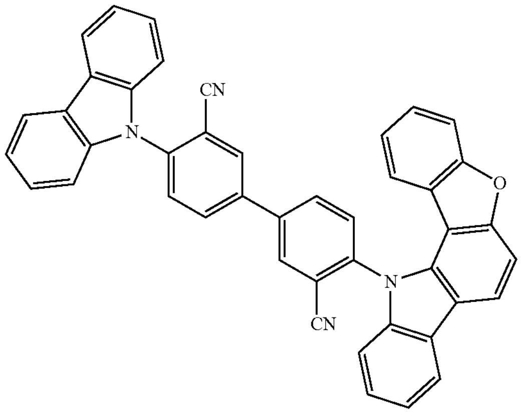
33
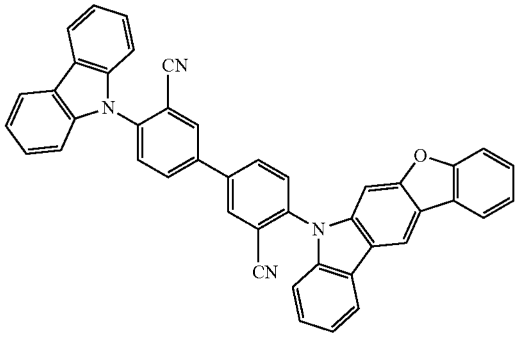
34
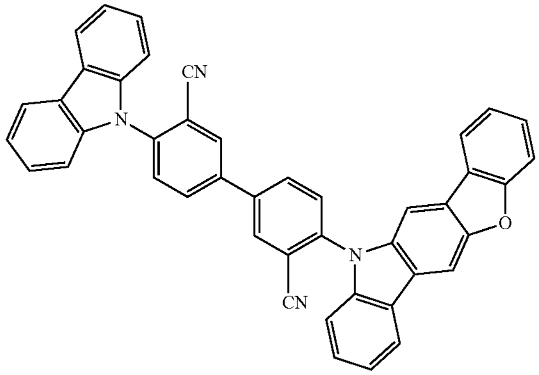
-continued
35
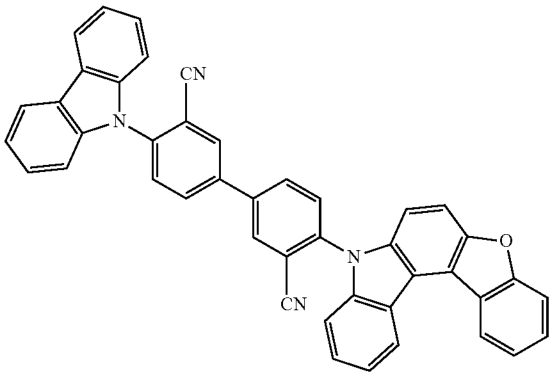
36
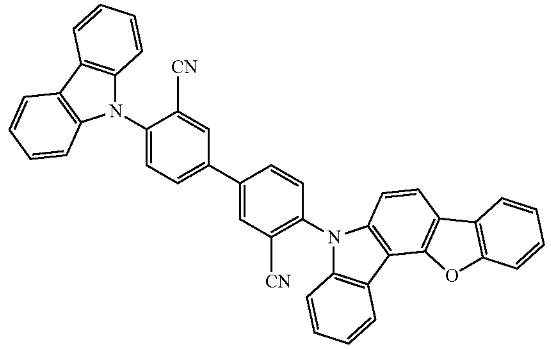
37
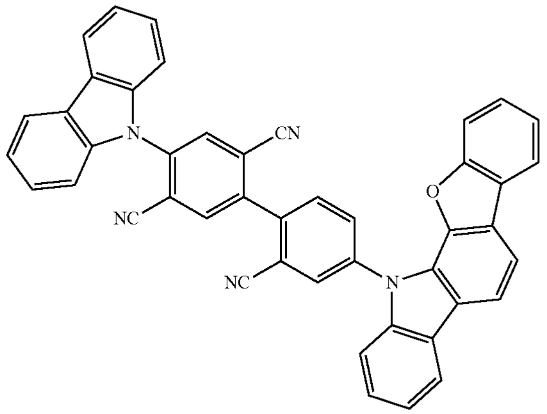
38
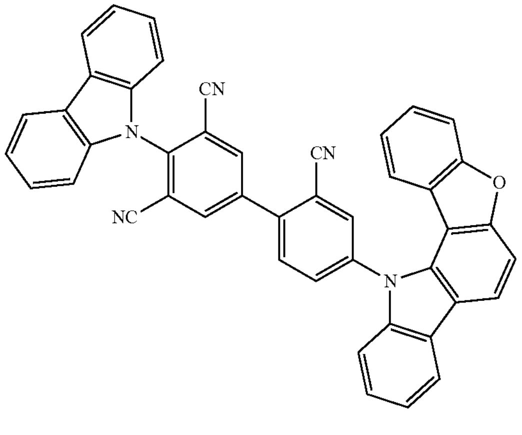

-continued
39
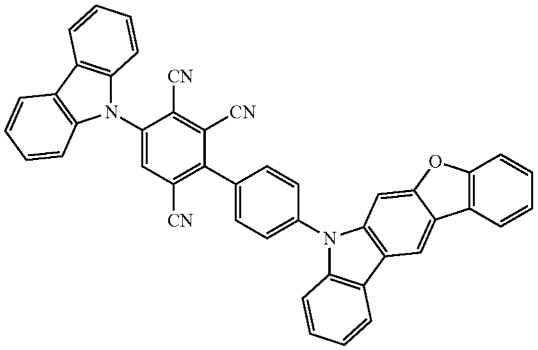
40
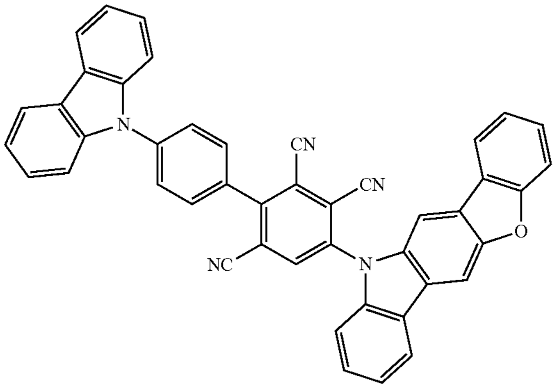
41
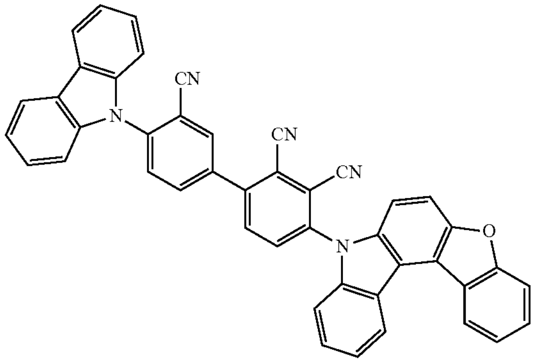
42
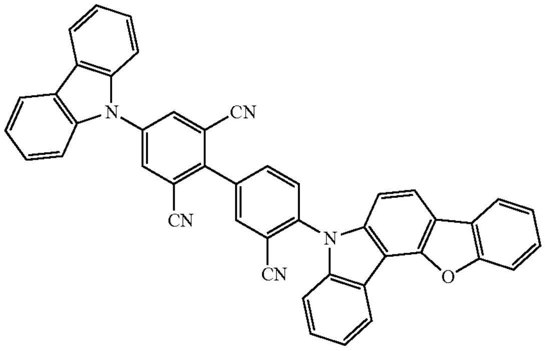
-continued
43
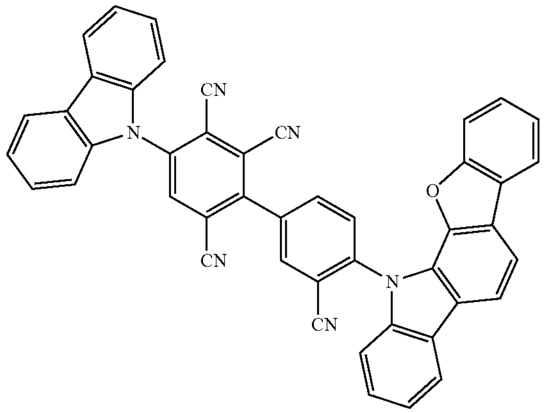
44
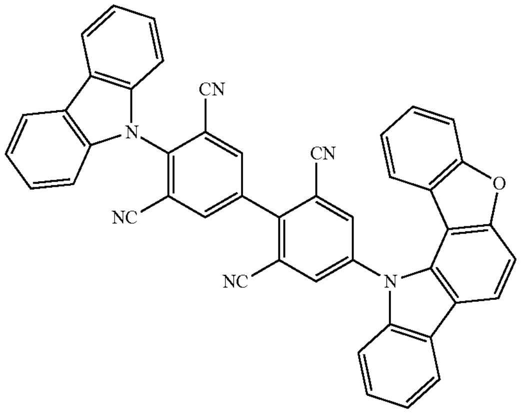
45
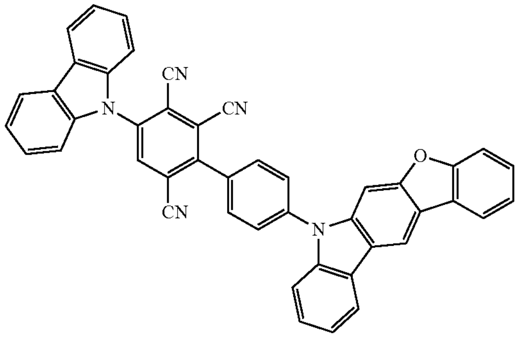
46
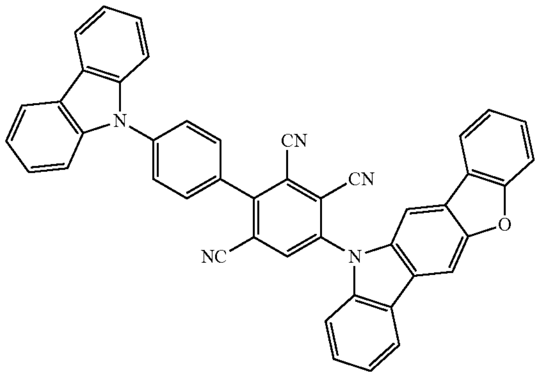

-continued
47
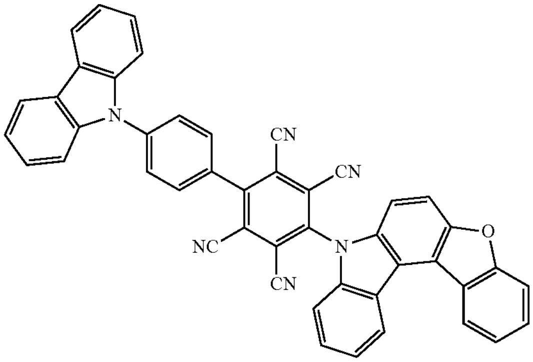
48
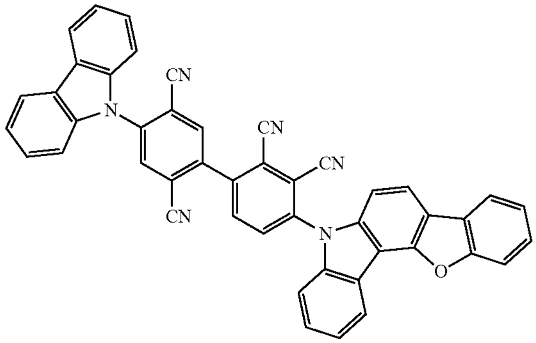
49
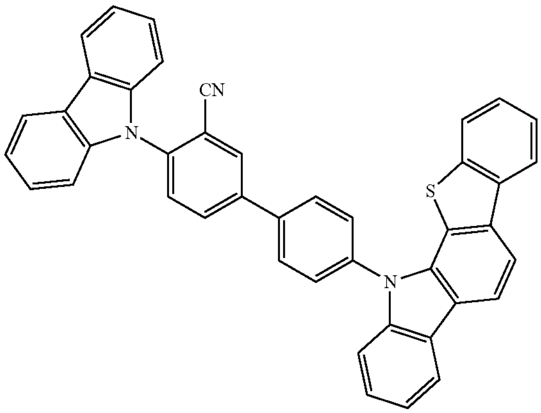
50
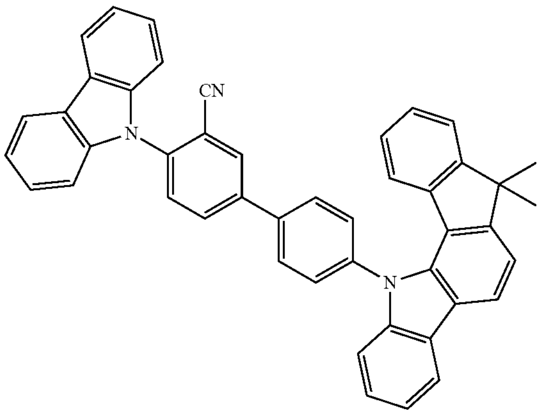
-continued
51
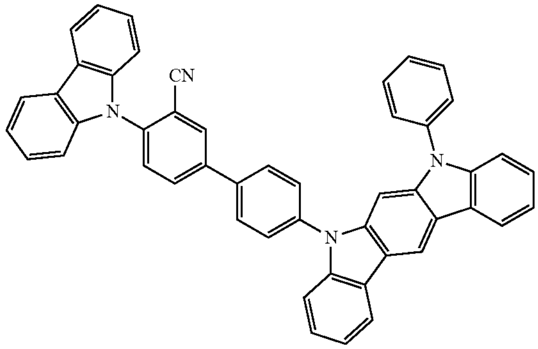
52
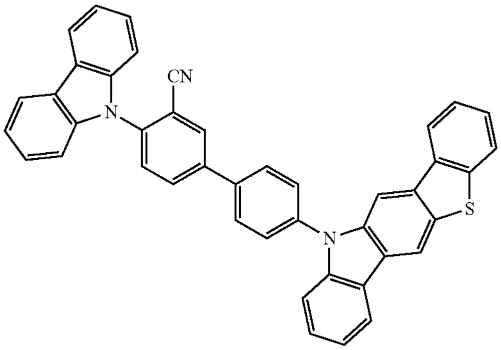
53
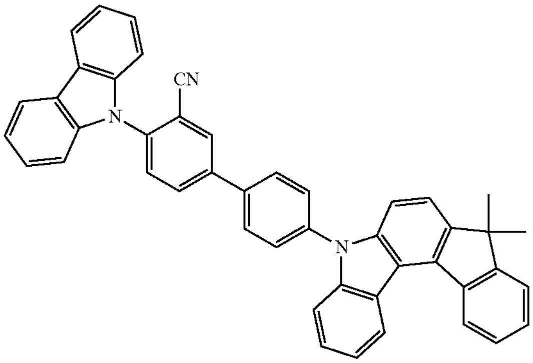
54
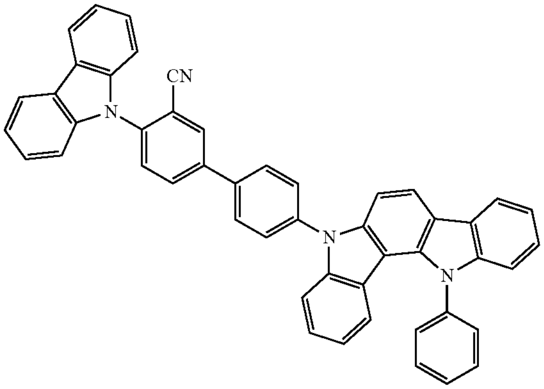

-continued
55
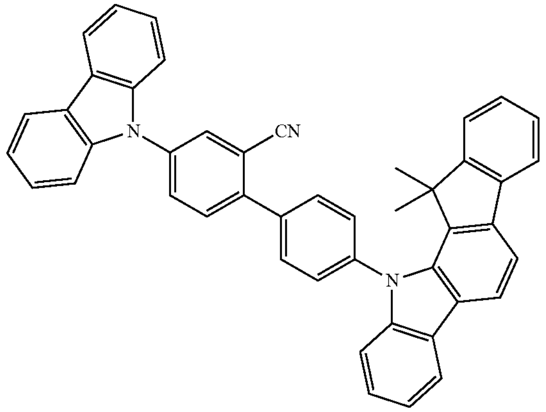
56
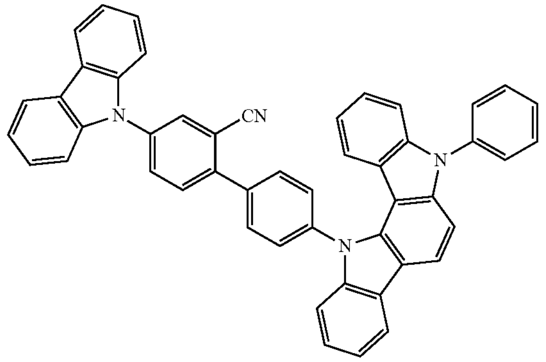
57
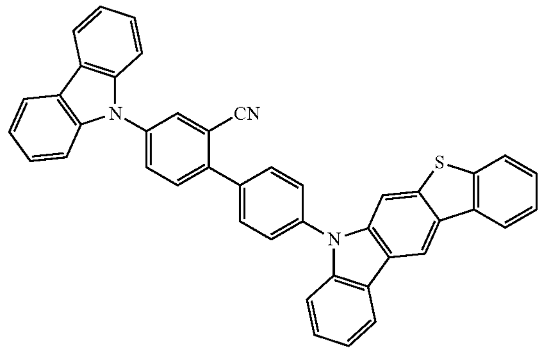
58
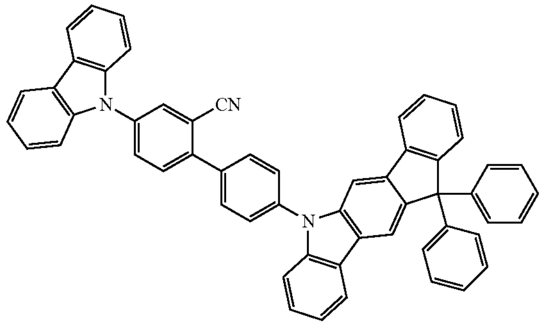
-continued
59
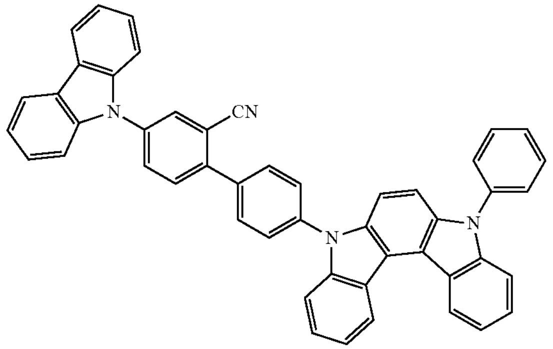
60
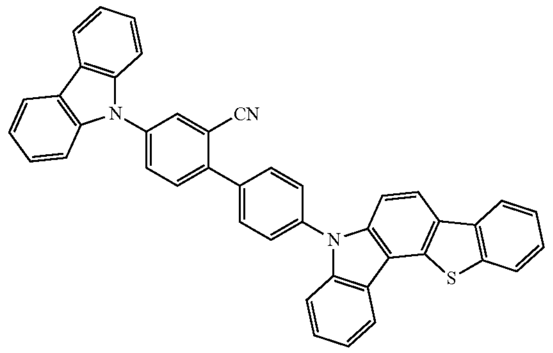
61
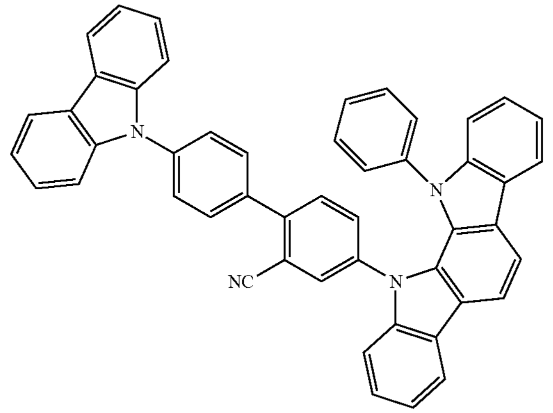
62
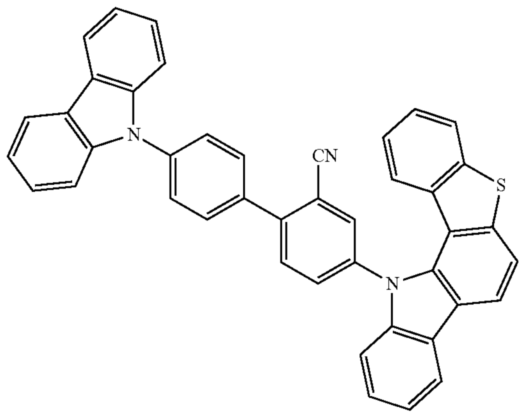

-continued
63
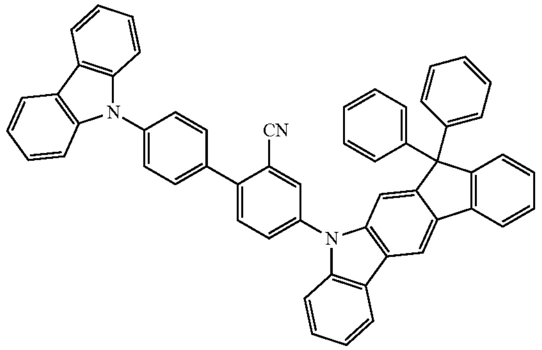
64
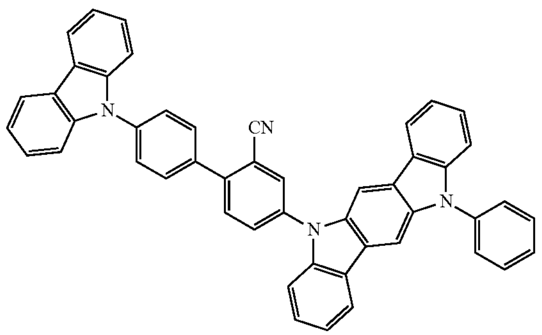
65
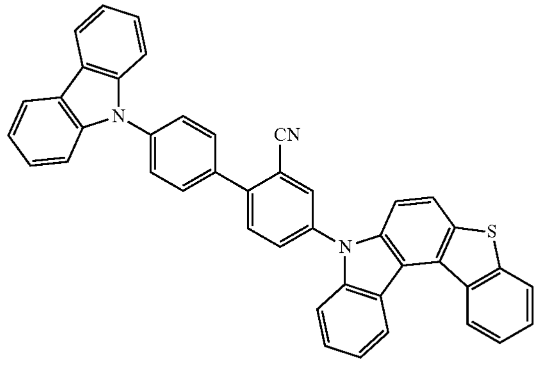
66
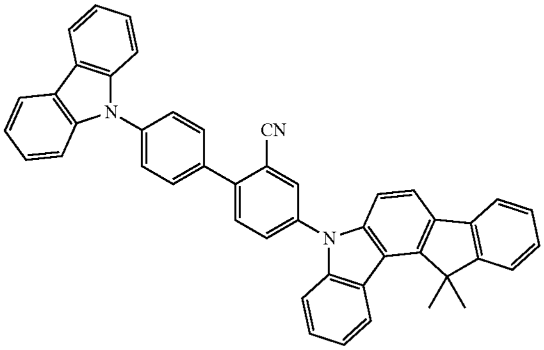
-continued
67
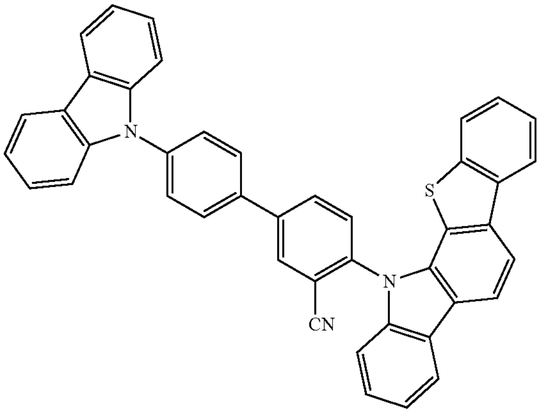
68
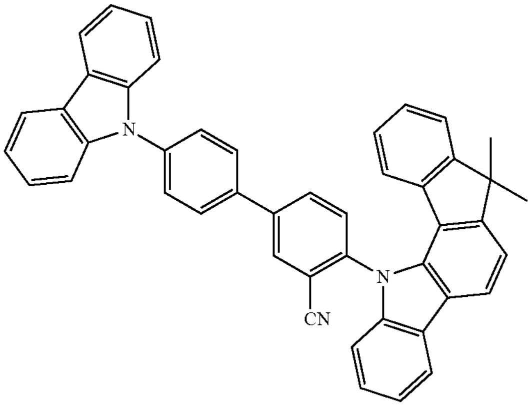
69
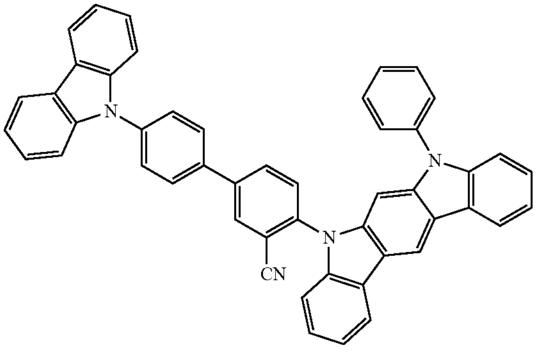
70
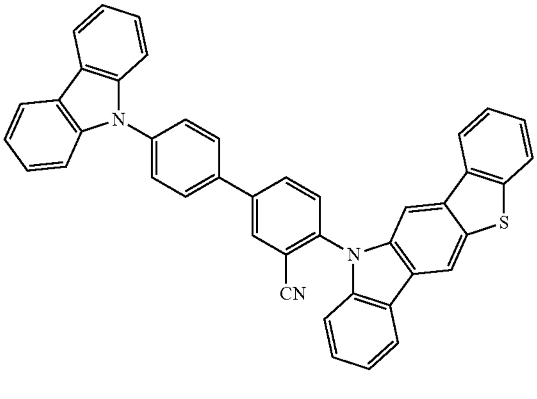

-continued
71
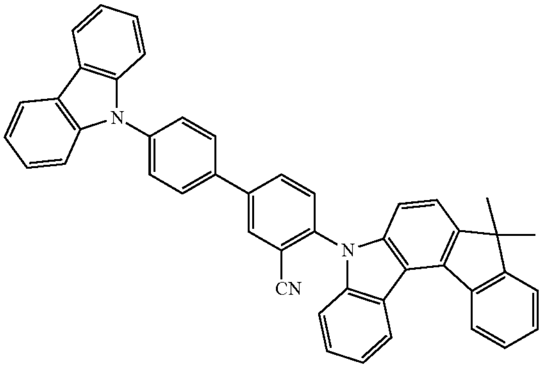
72
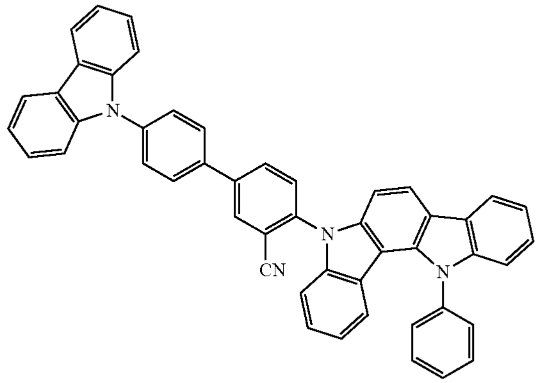
73
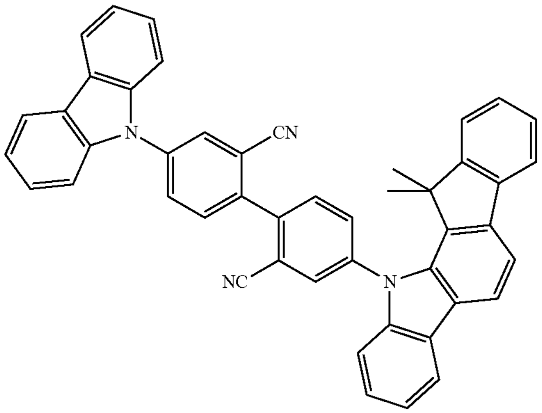
74
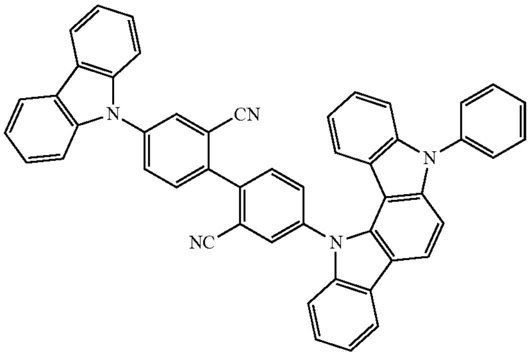
-continued
75
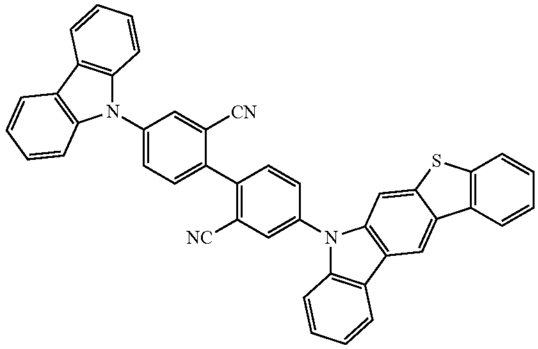
76
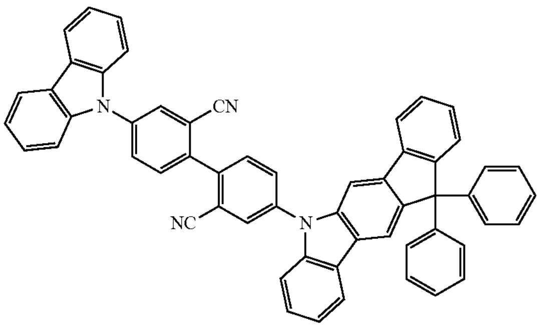
77
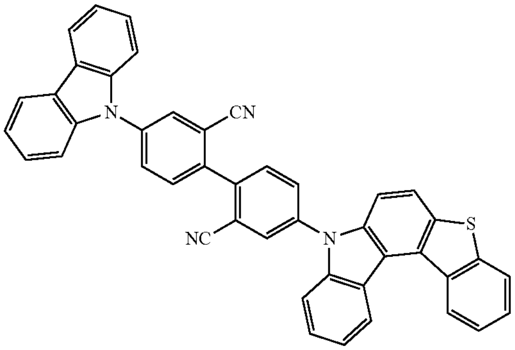
78
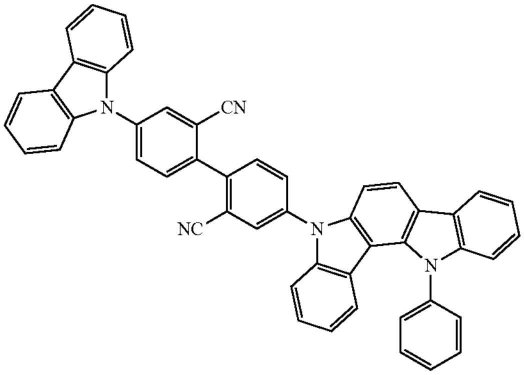

-continued
79
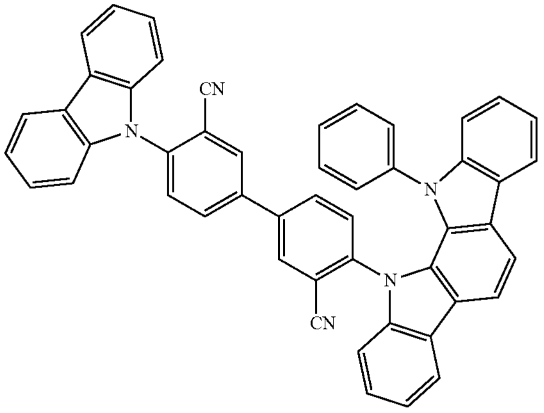
80
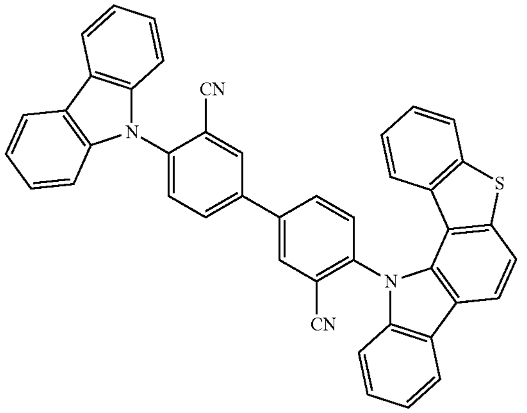
81
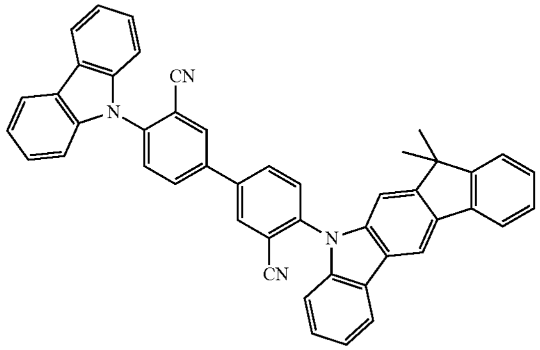
82
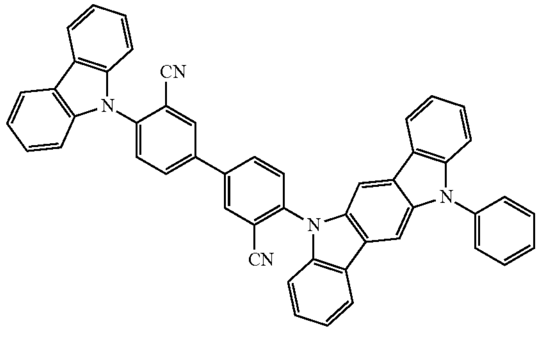
-continued
83
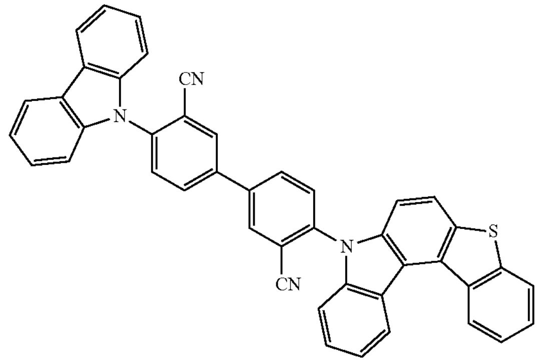
84
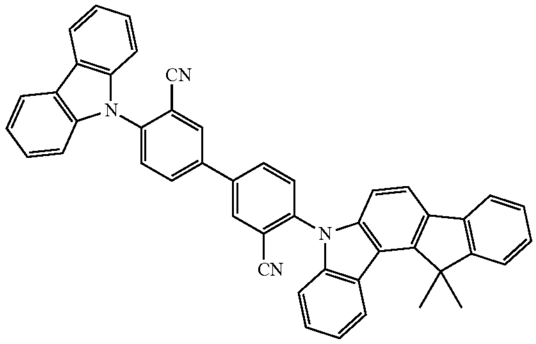
85
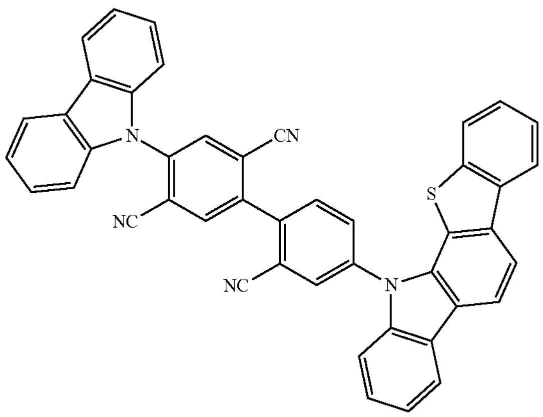
86
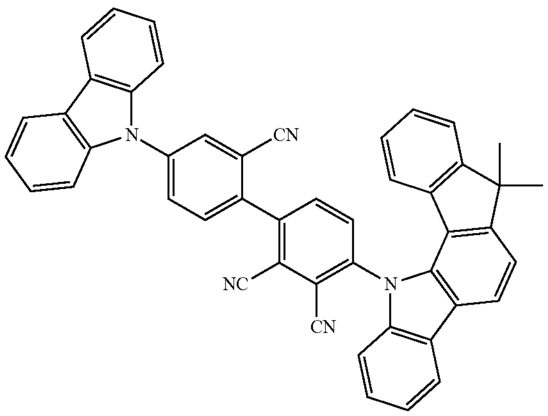

-continued
87
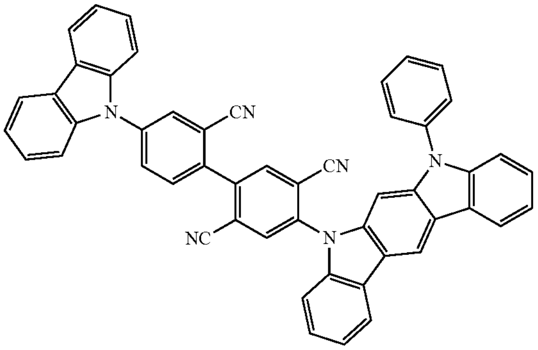
88
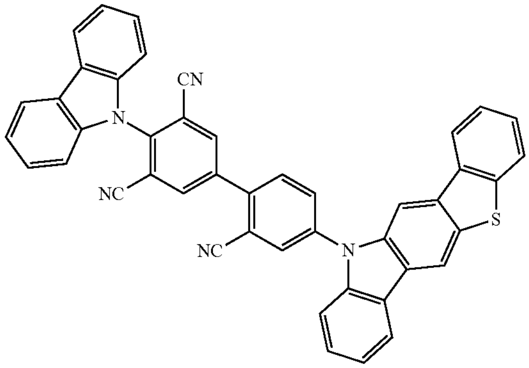
89
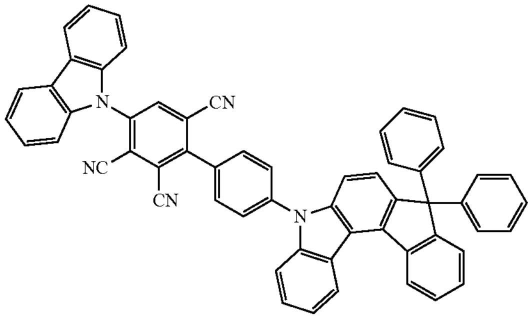
90
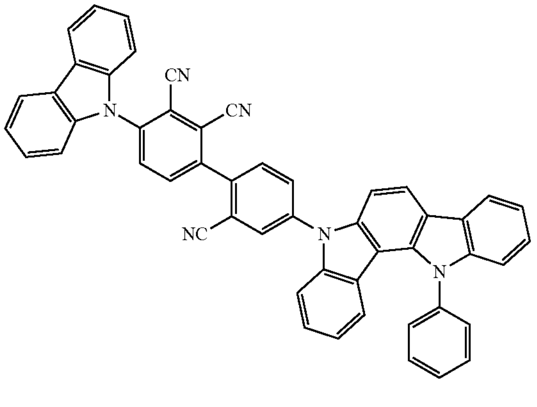
-continued
91
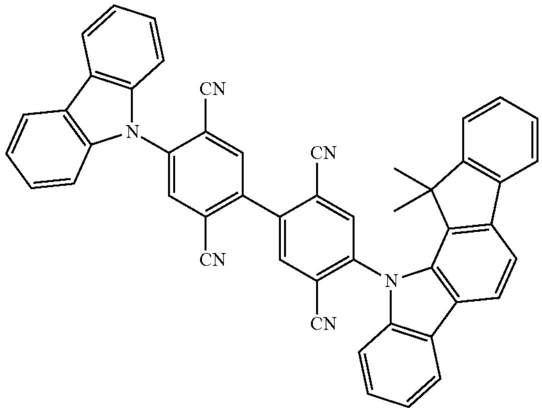
92
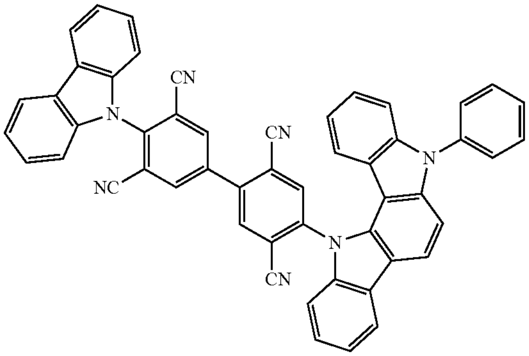
93
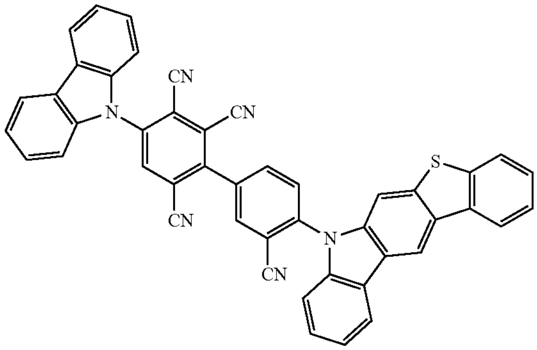
94
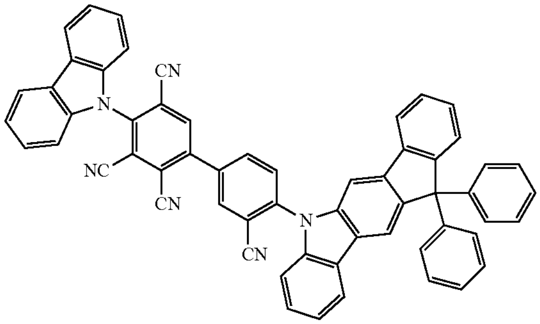

-continued
95
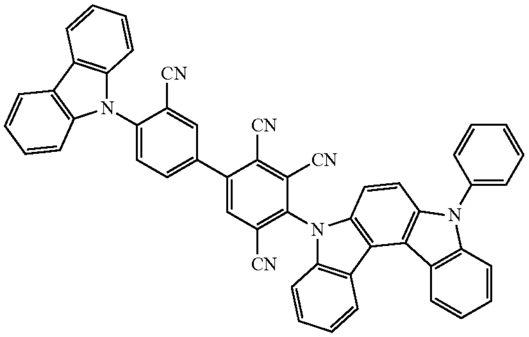
96
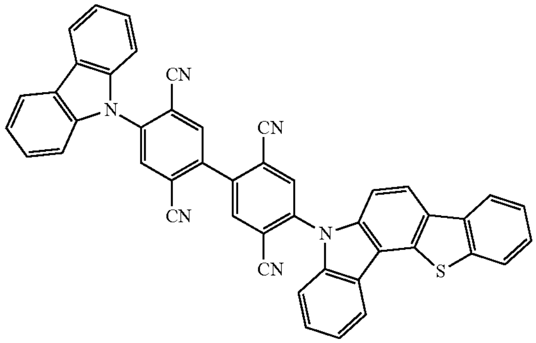
97
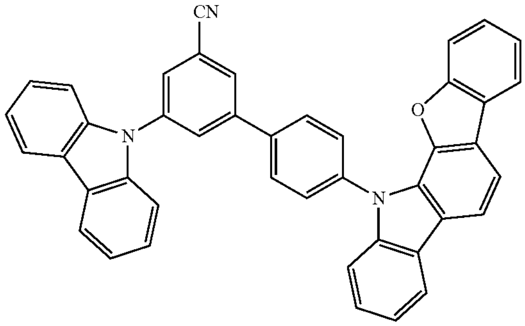
98
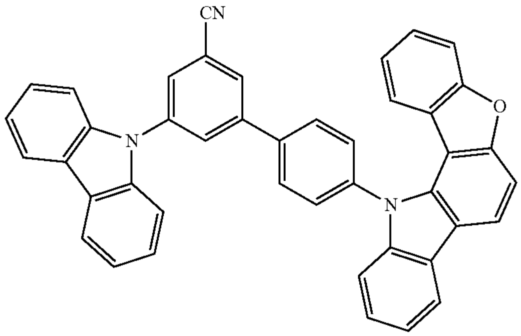
-continued
99
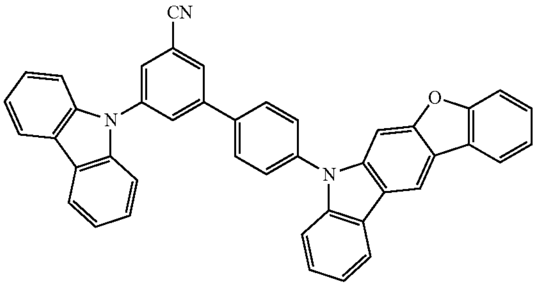
100
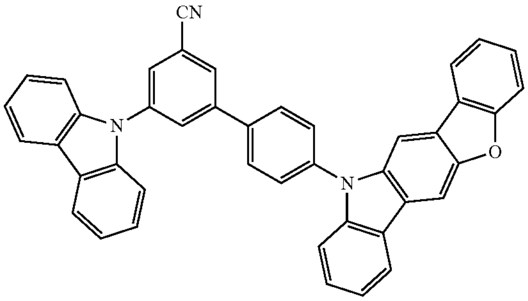
101
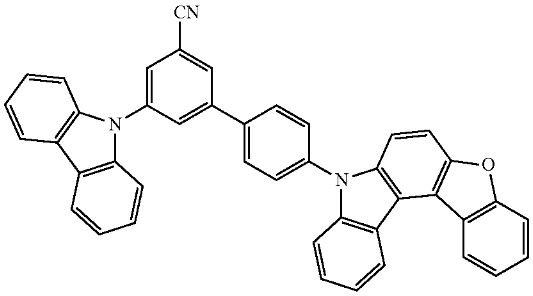
102
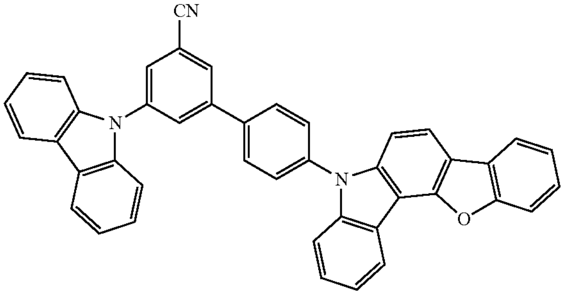
103
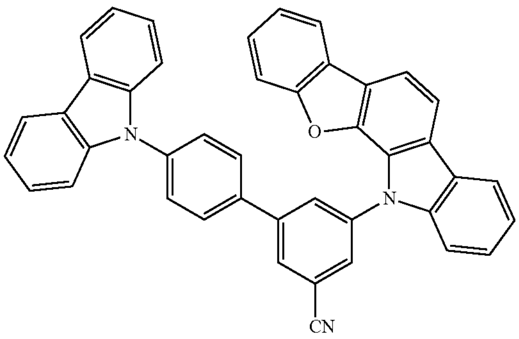

-continued
104
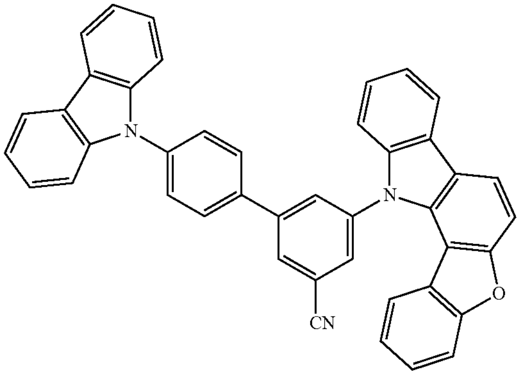
105
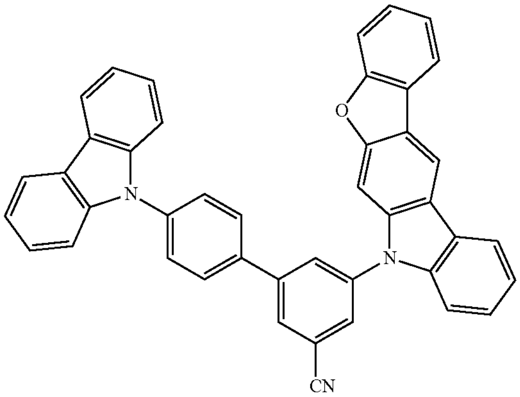
106
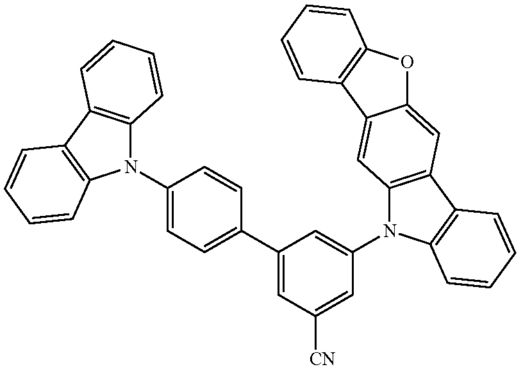
107
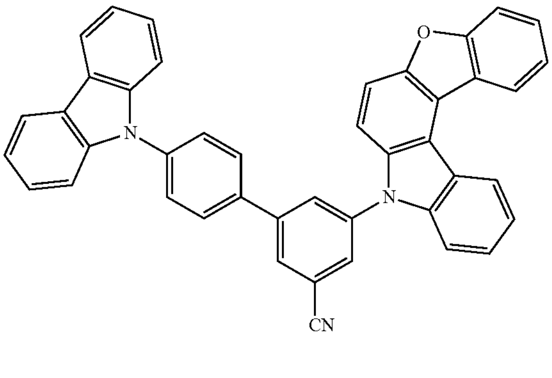
-continued
108
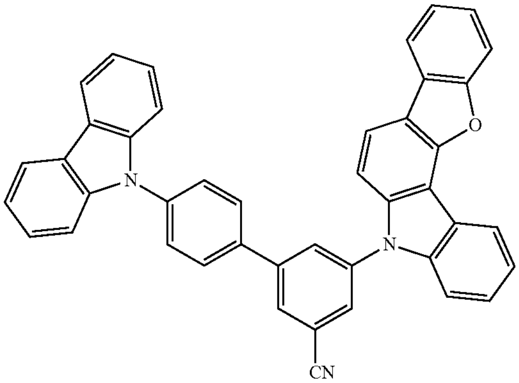
109
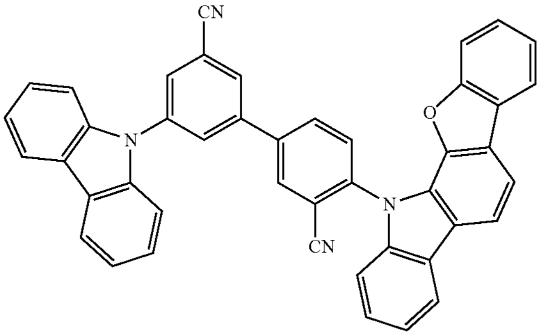
110
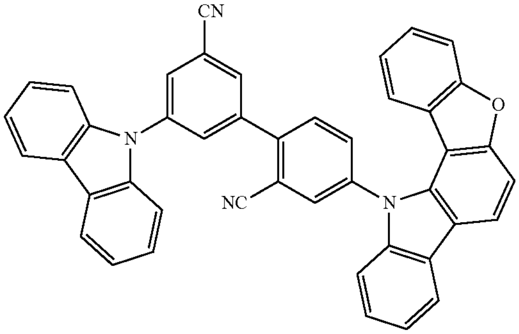
111
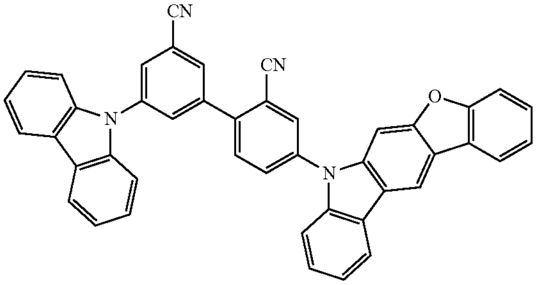

-continued
112
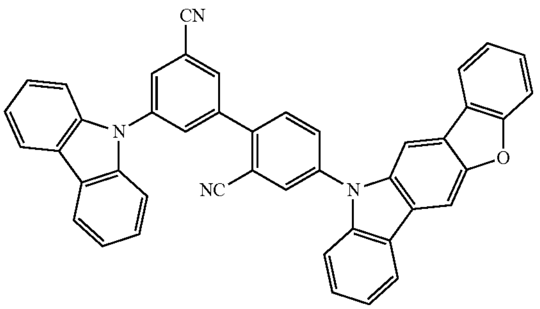
113
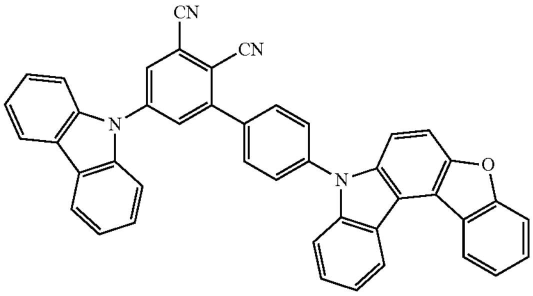
114
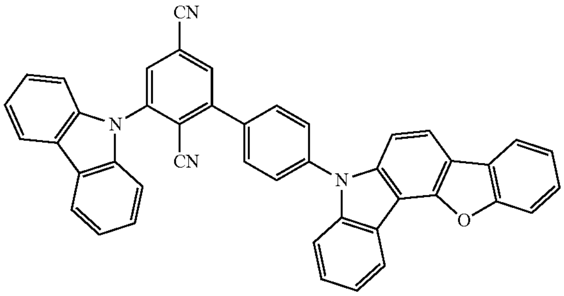
115
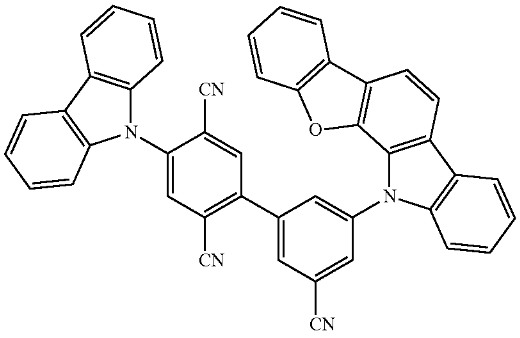
-continued
116
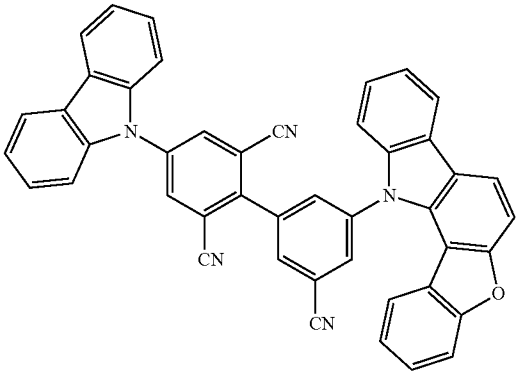
117
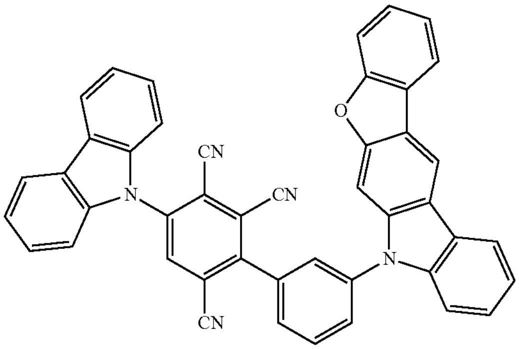
118
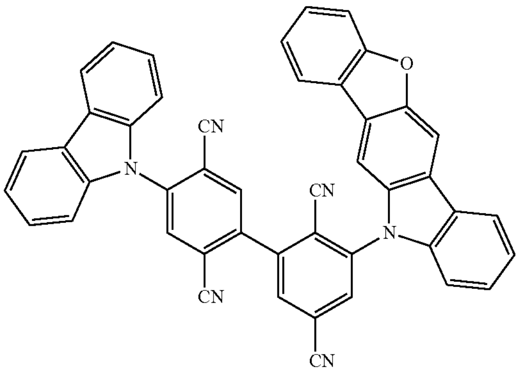
119
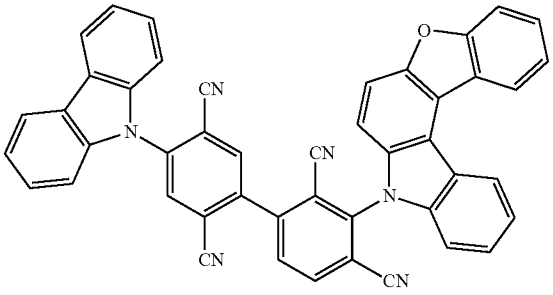

120
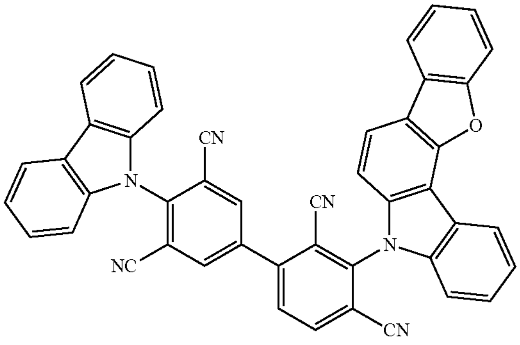
121
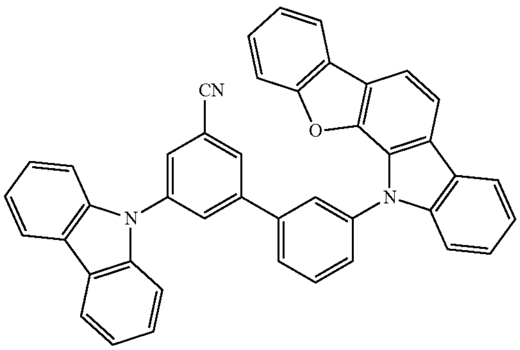
122
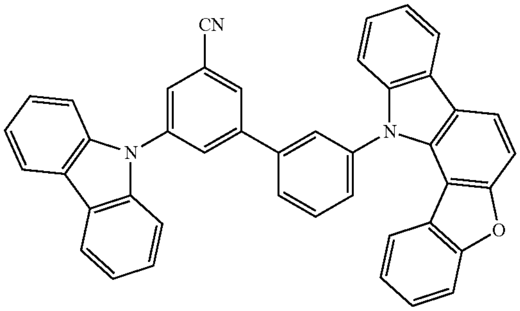
123
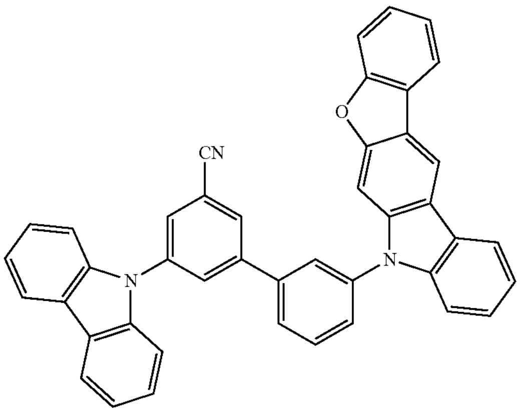
124
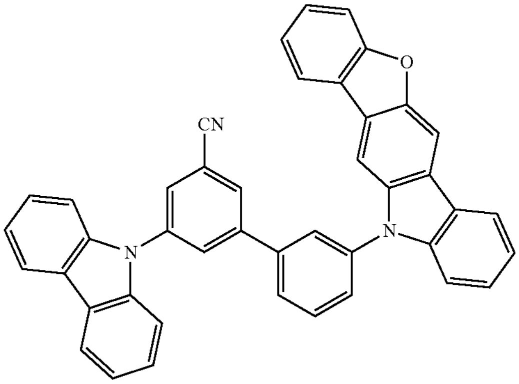
125
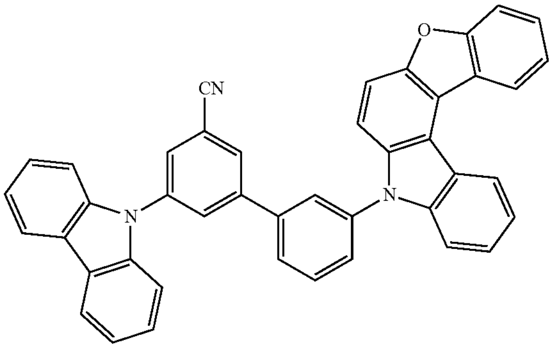
126
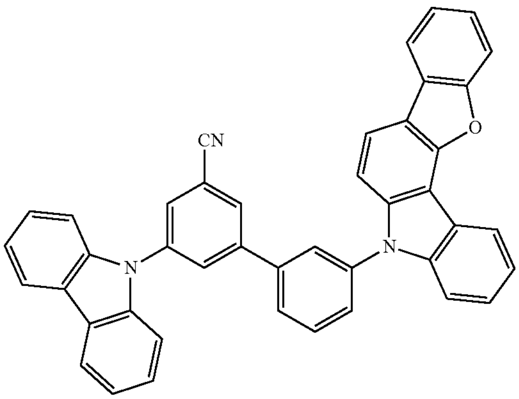
127
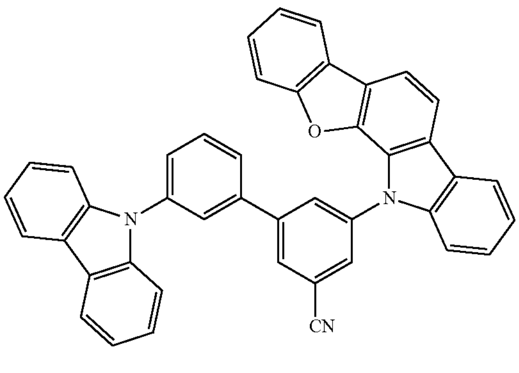

-continued
128
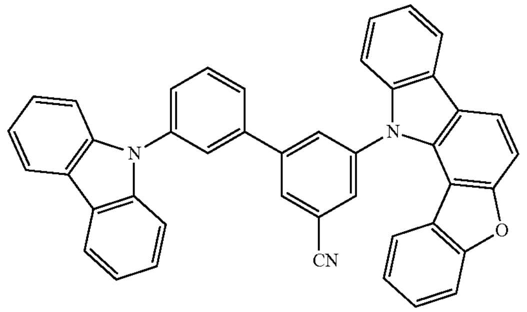
129
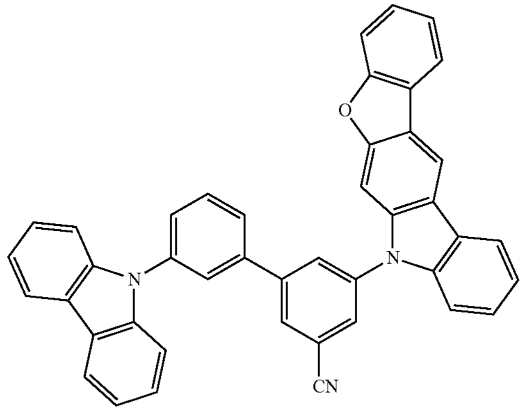
130
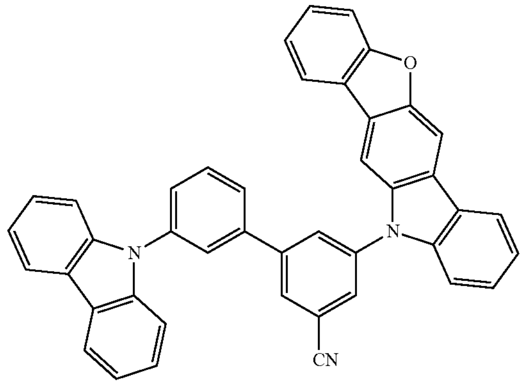
131
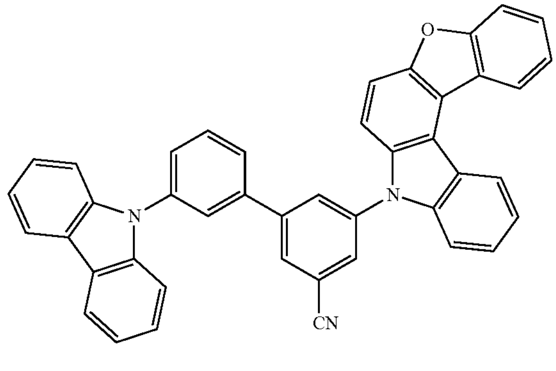
-continued
132
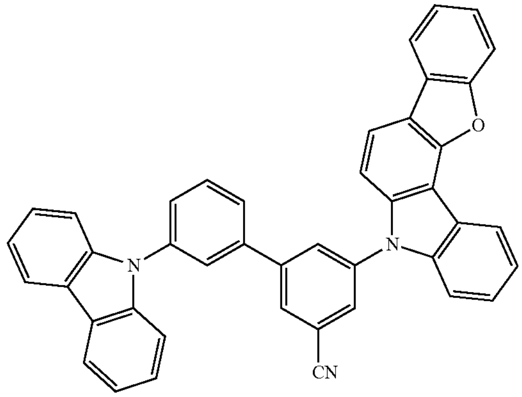
133
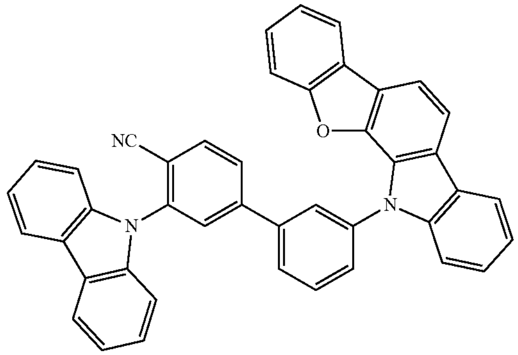
134
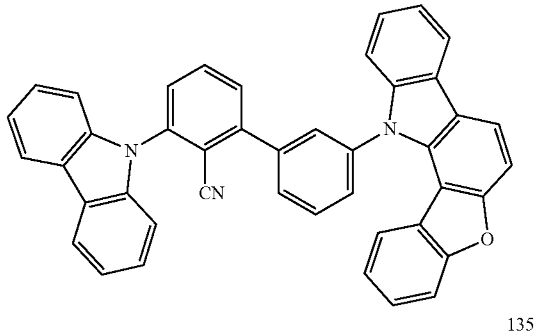
135
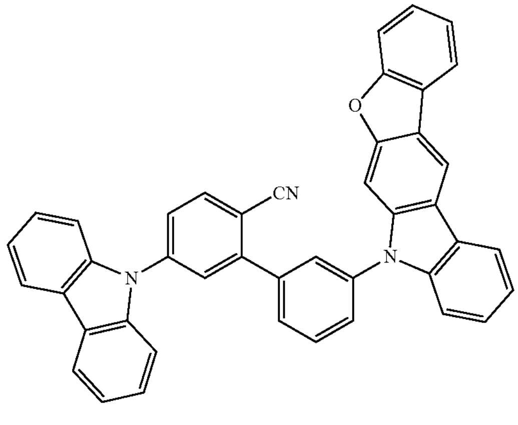

-continued
136
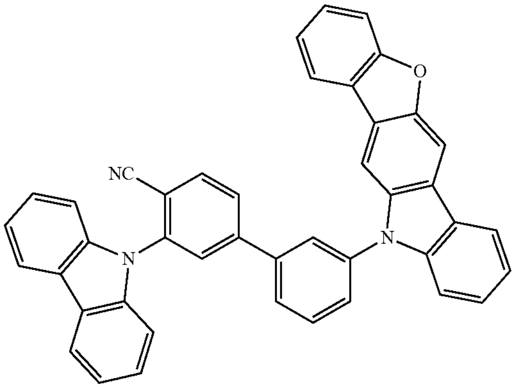
137
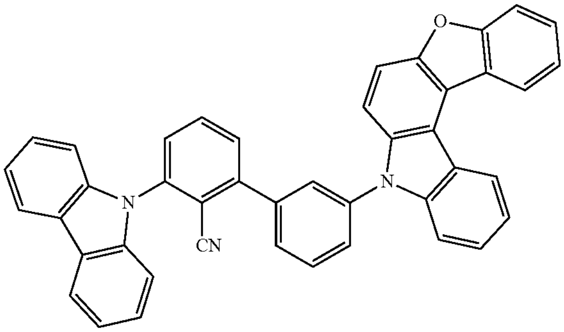
138
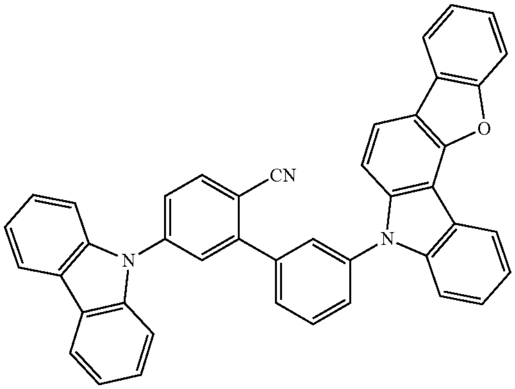
139
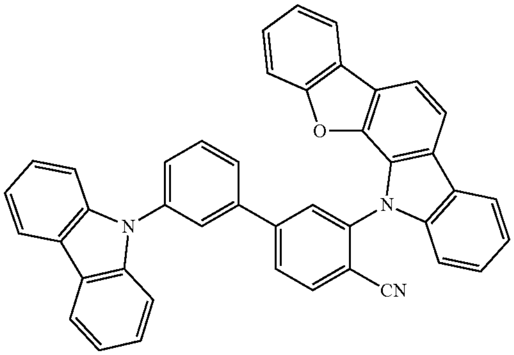
-continued
140
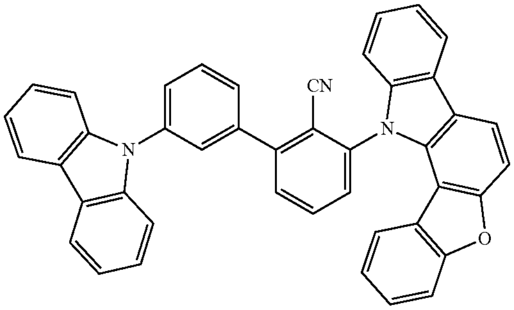
141
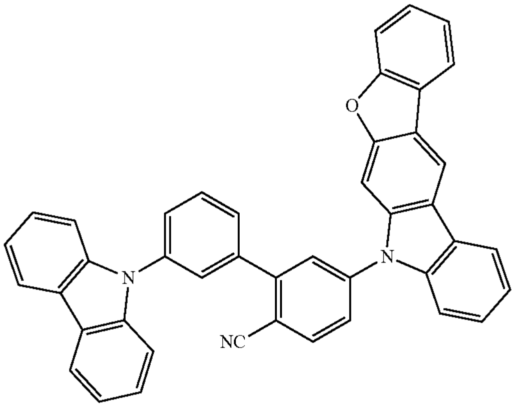
142
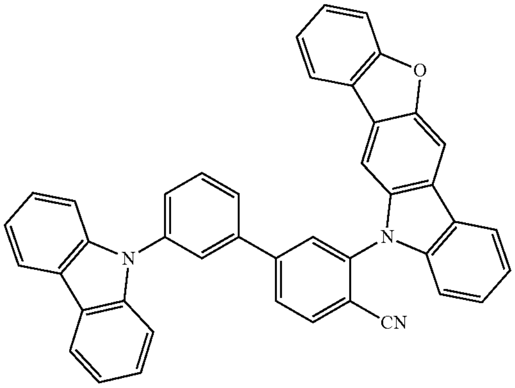
143
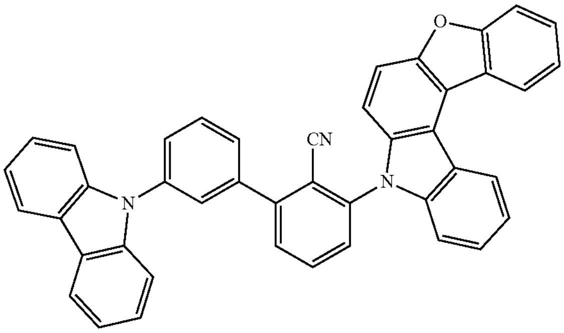

-continued
144
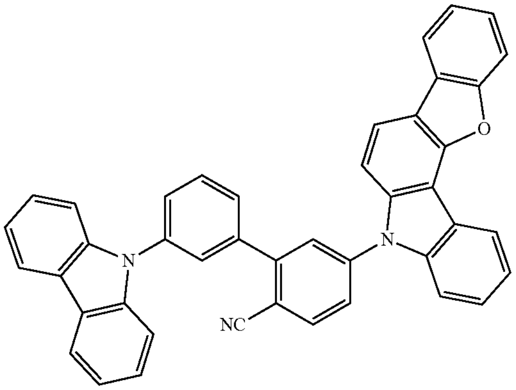
145
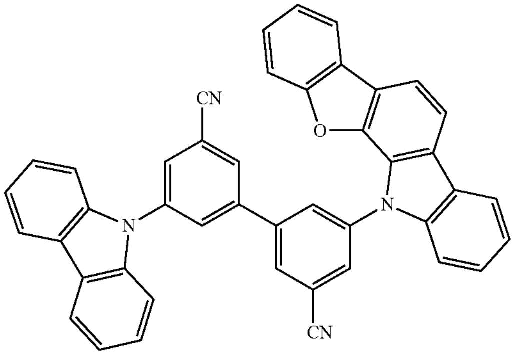
146
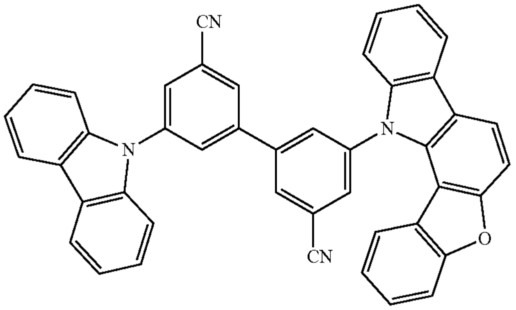
147
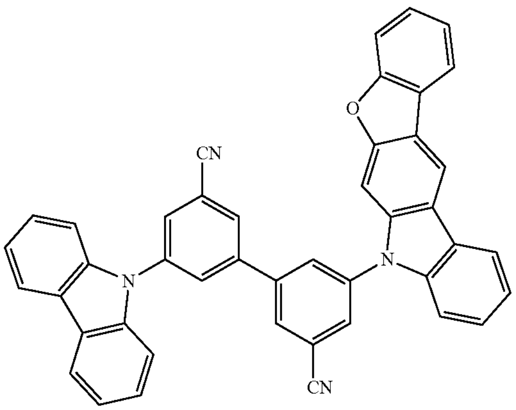
-continued
148
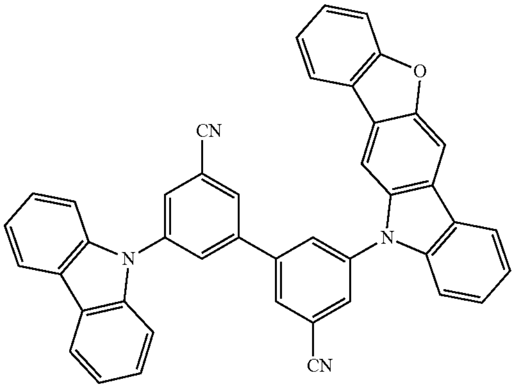
149
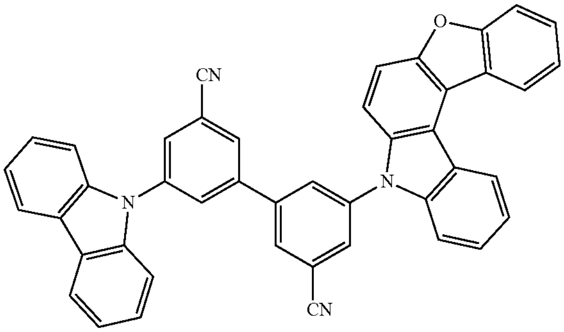
150
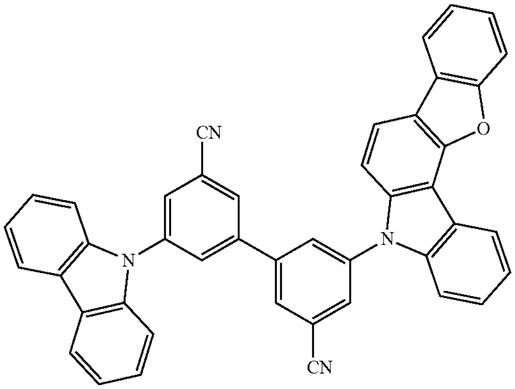
151
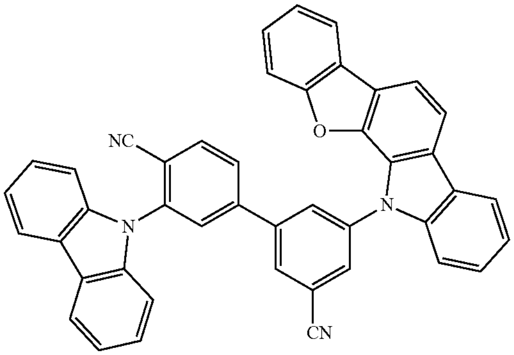

-continued
152
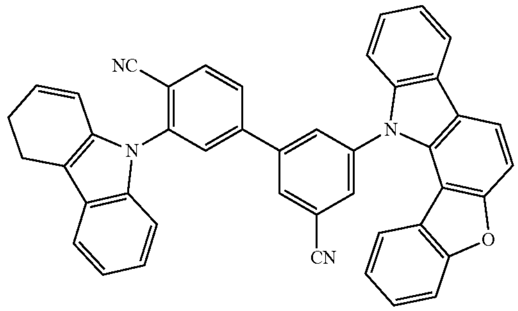
153
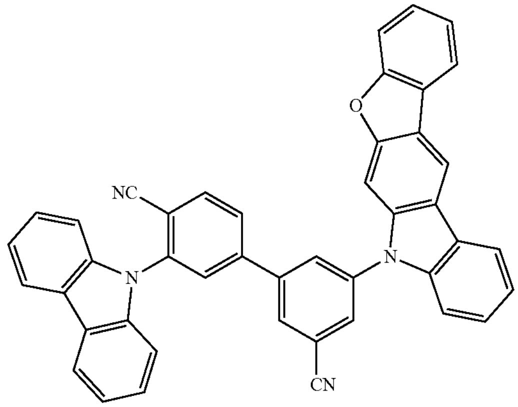
154
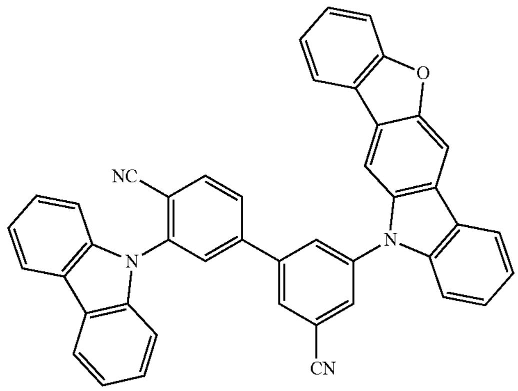
155
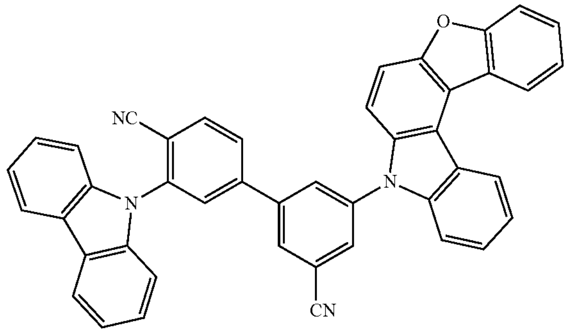
-continued
156
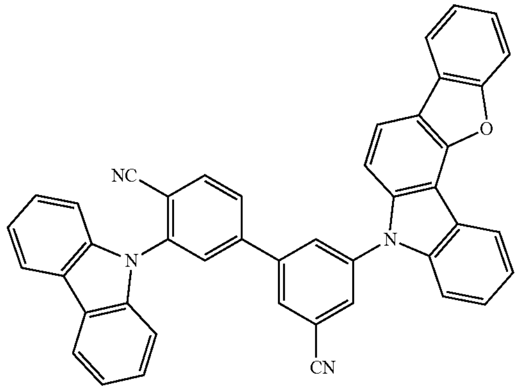
157
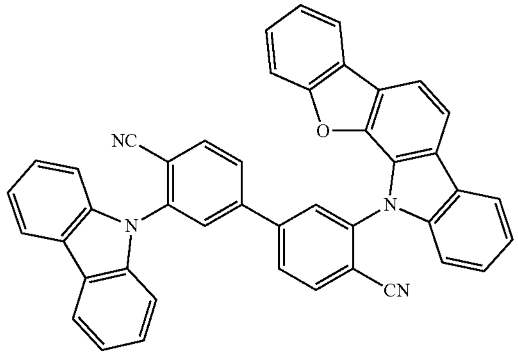
158
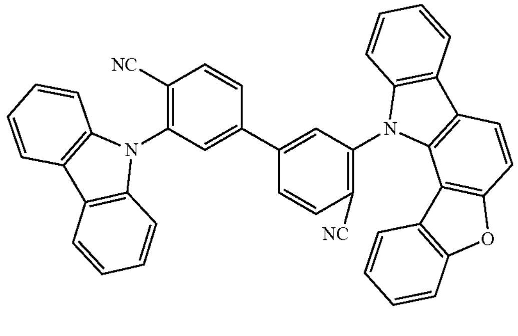
159
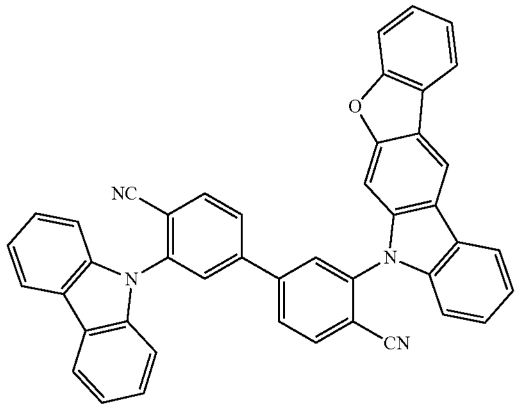

160
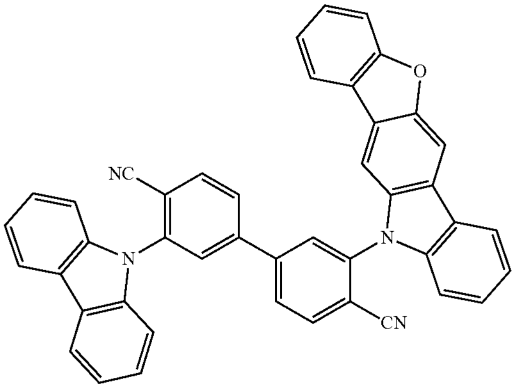
161
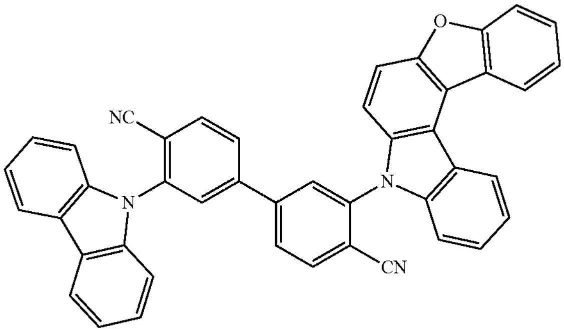
162
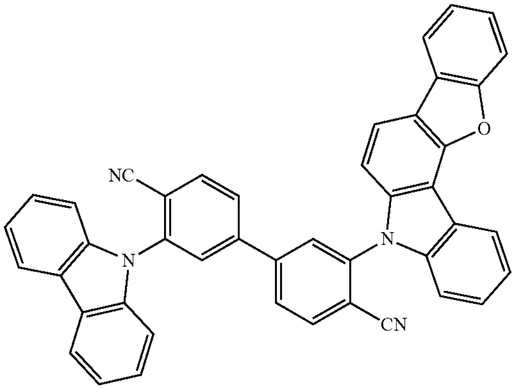
163
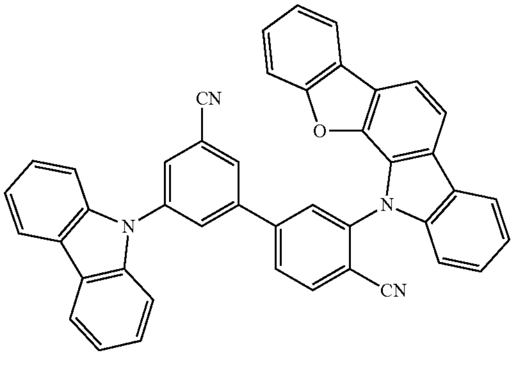
164
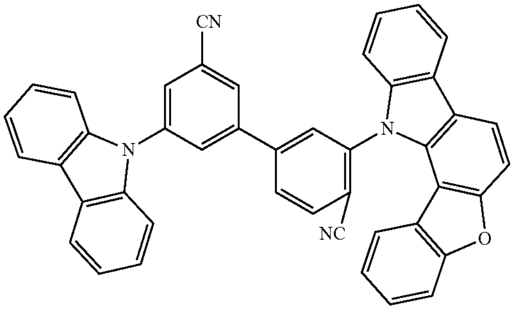
165
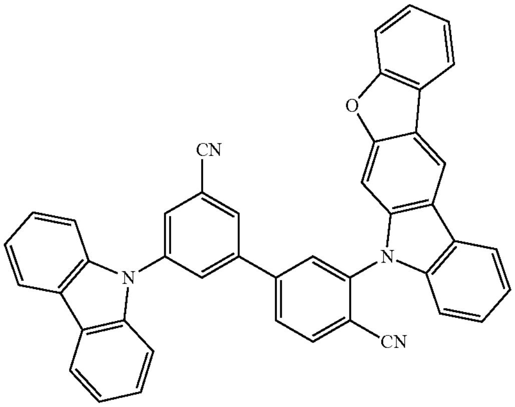
166
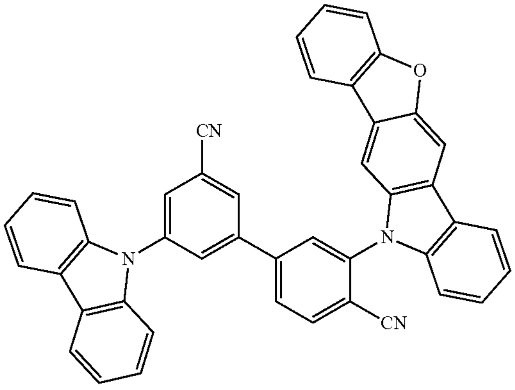
167
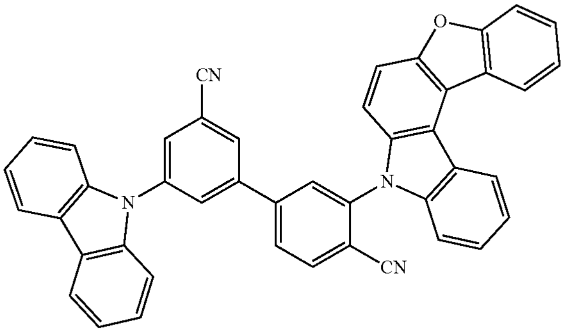

-continued
168
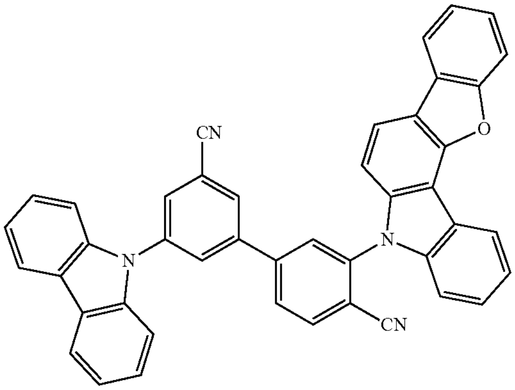
169
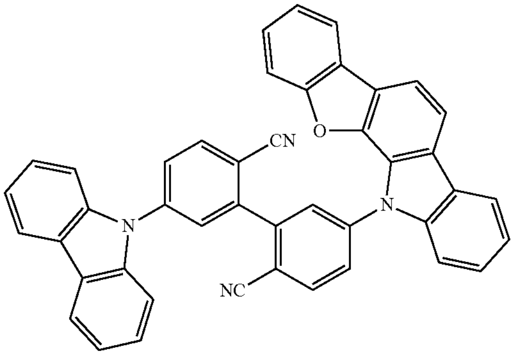
170
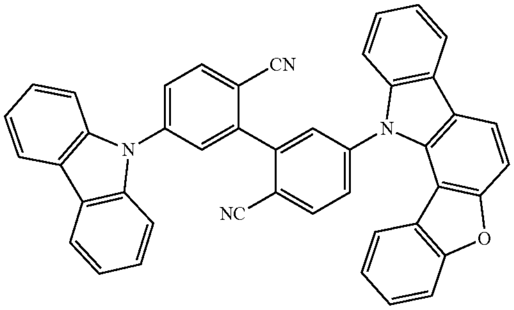
171
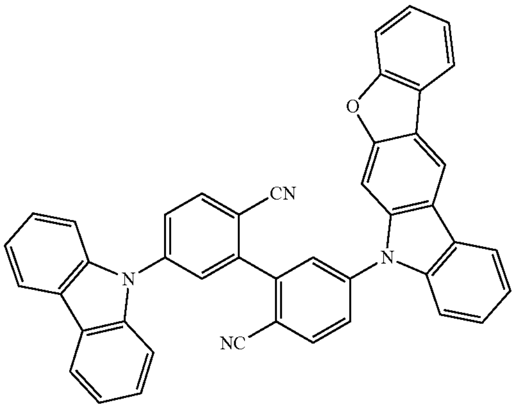
-continued
172
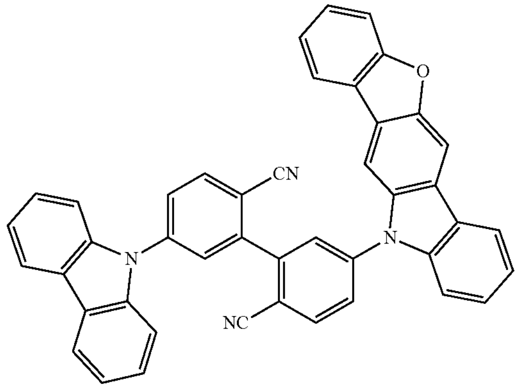
173
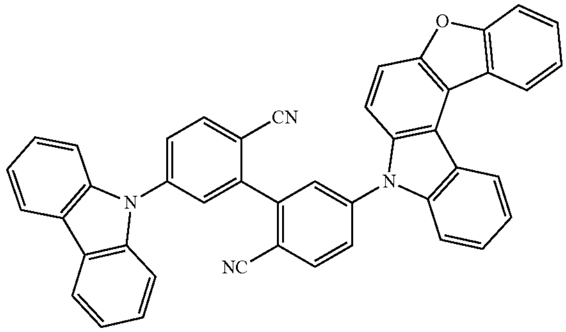
174
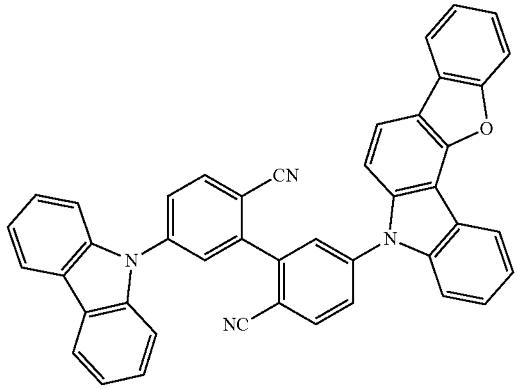
175
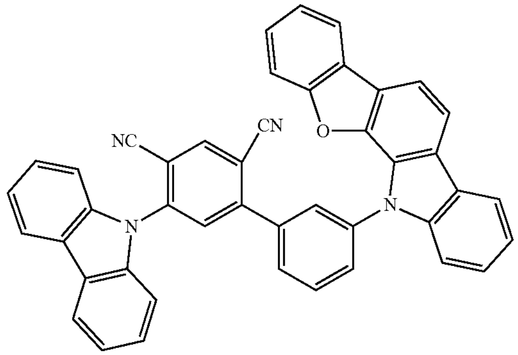

-continued
176
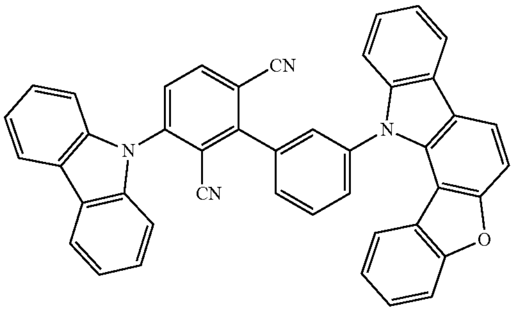
177
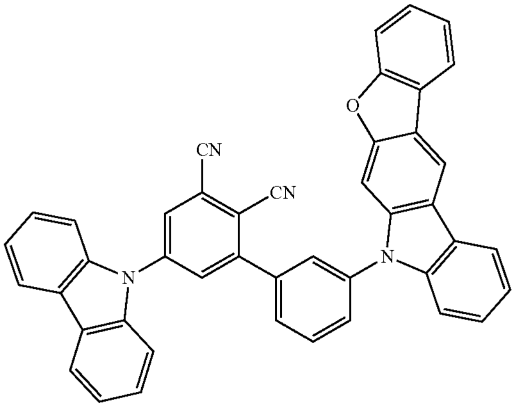
178
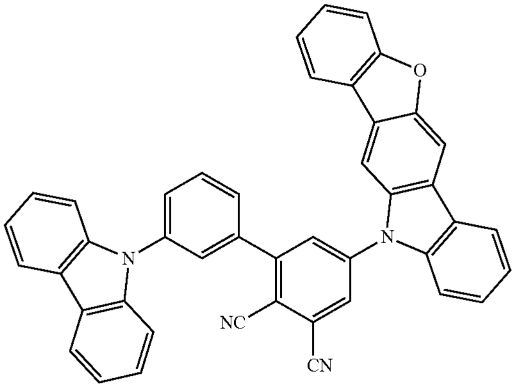
179
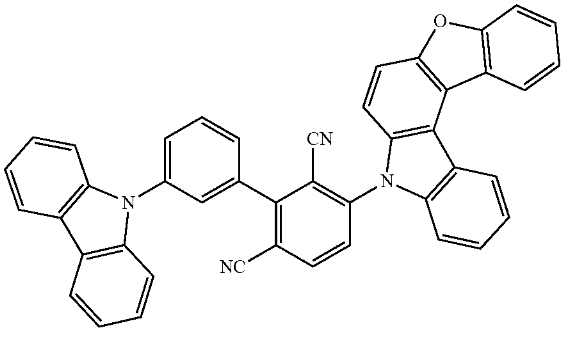
-continued
180
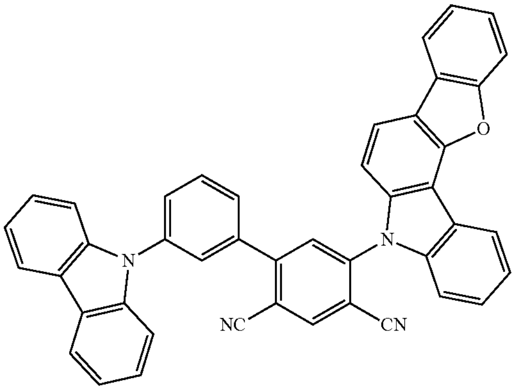
181
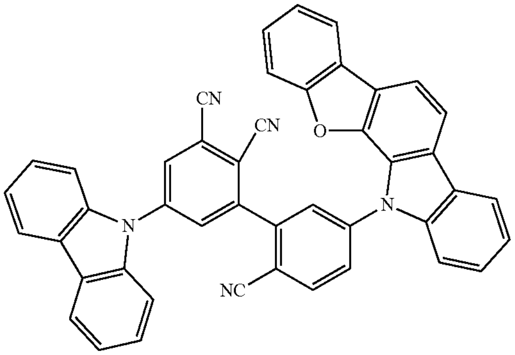
182
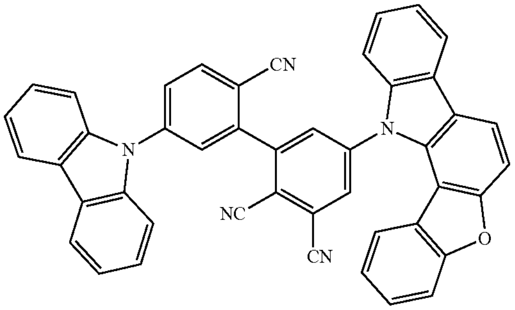
183
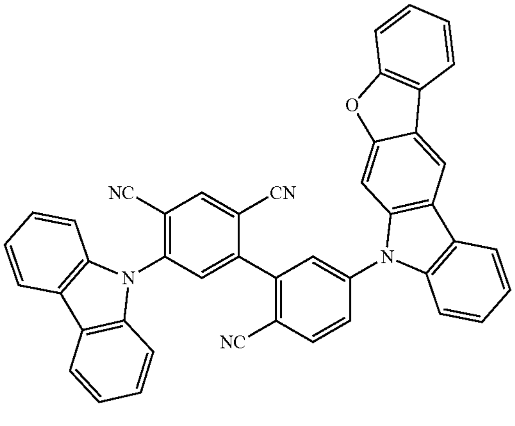

-continued
184
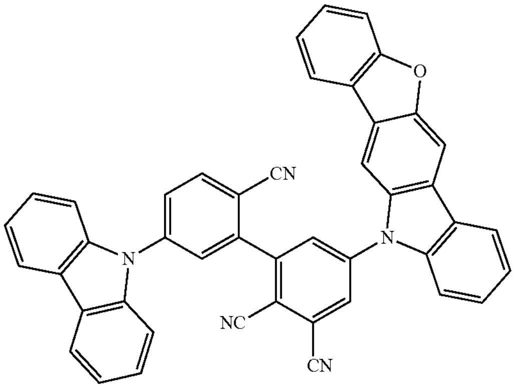
185
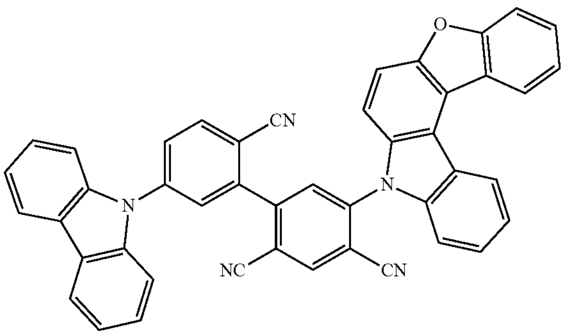
186
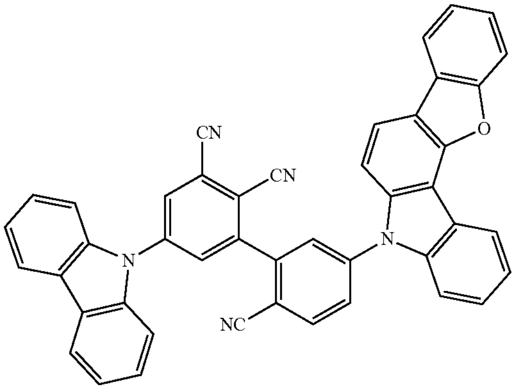
187
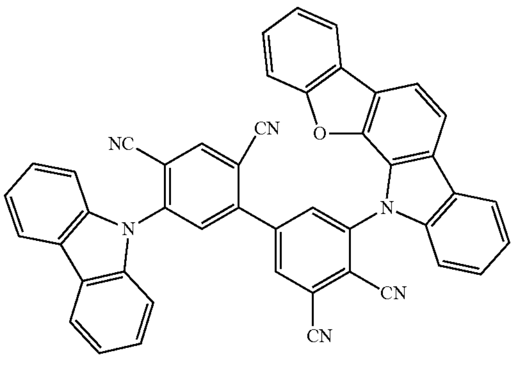
-continued
188
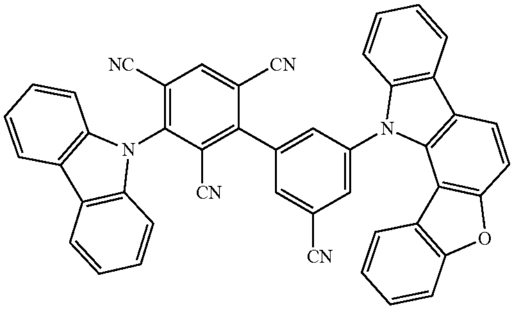
189
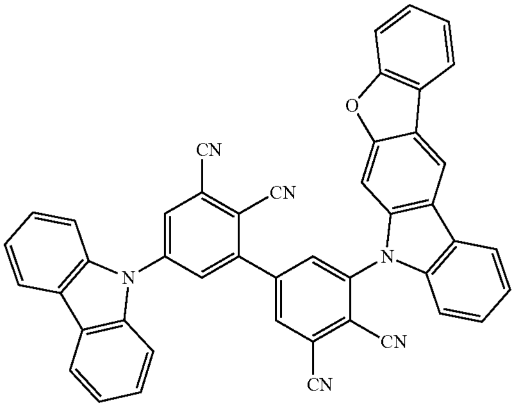
190
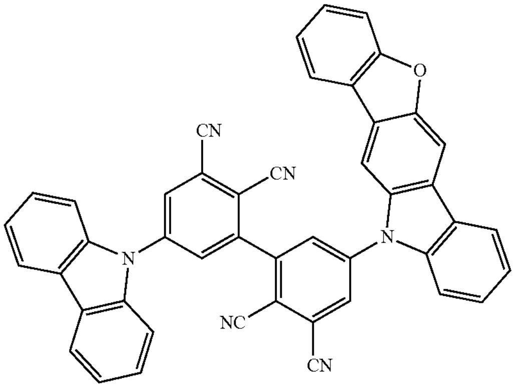
191
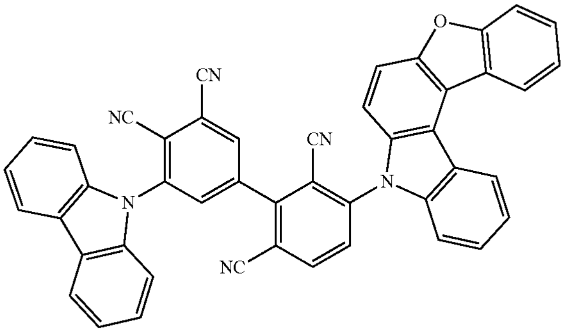

-continued
192
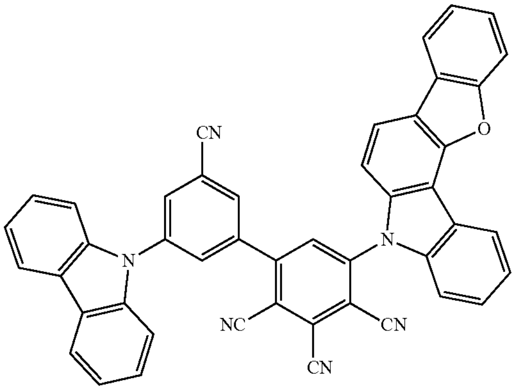
193
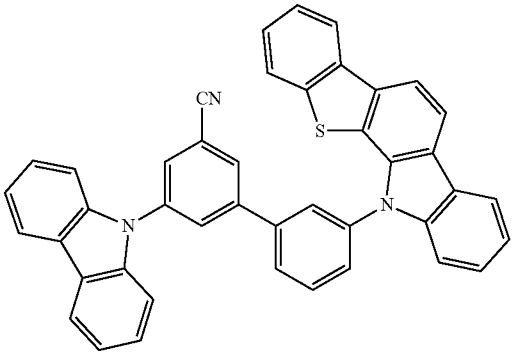
194
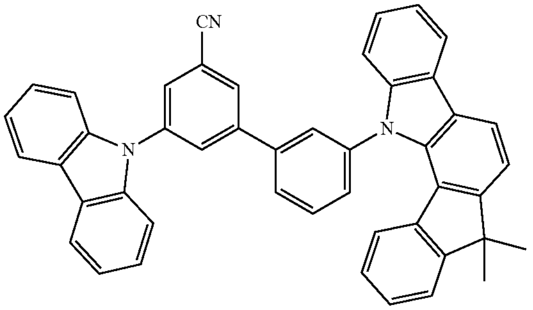
195
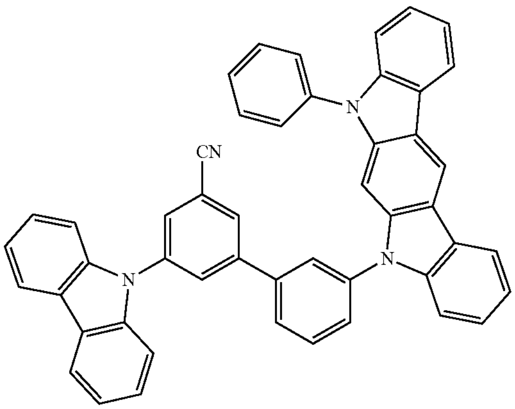
-continued
196
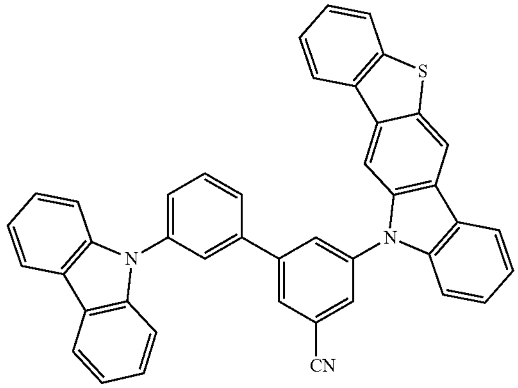
197
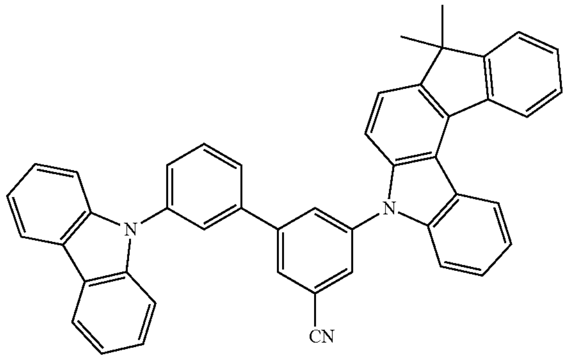
198
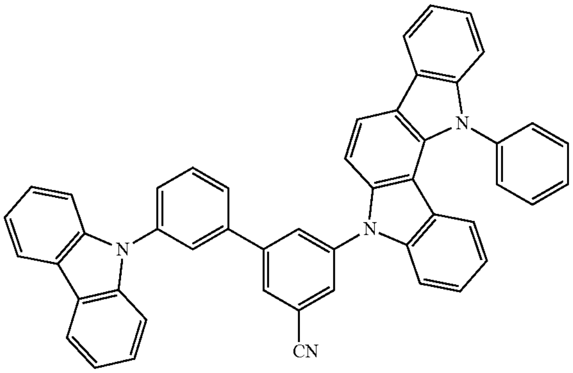
199
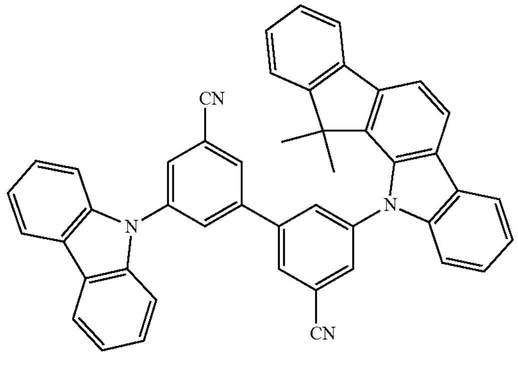

-continued
200
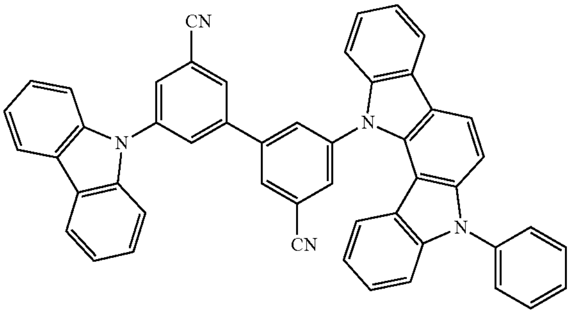
201
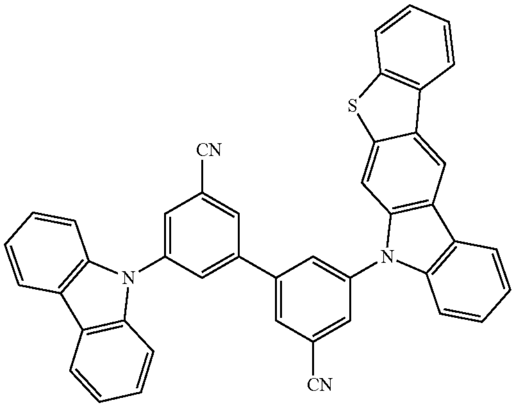
202
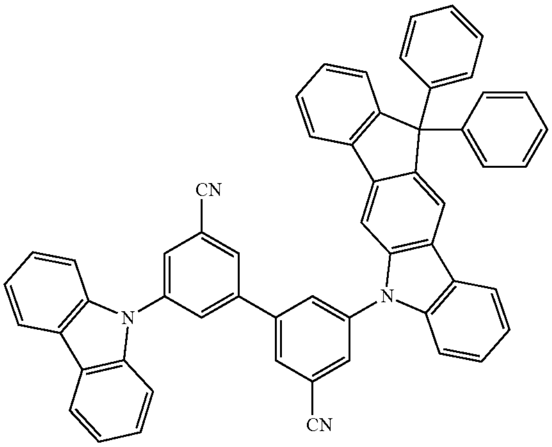
-continued
203
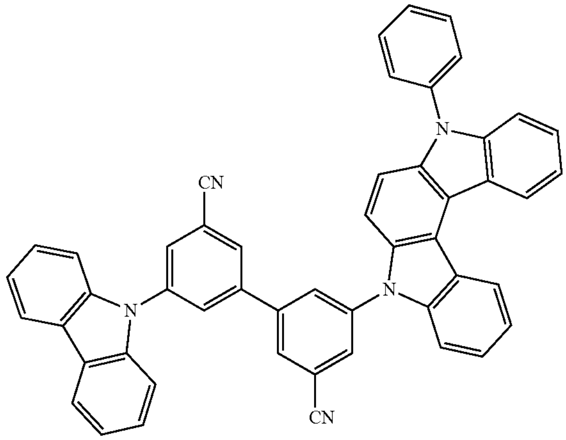
204
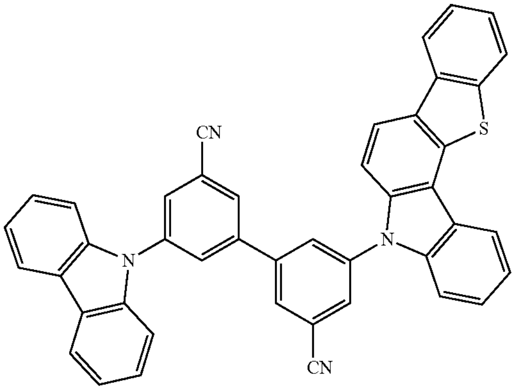
205
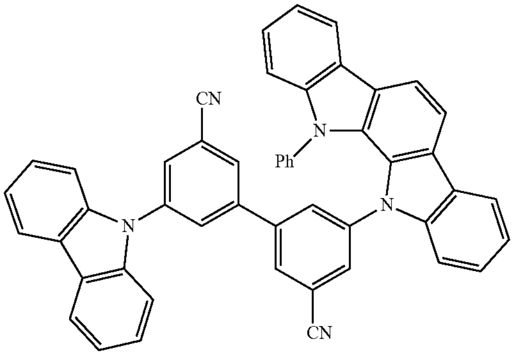
206
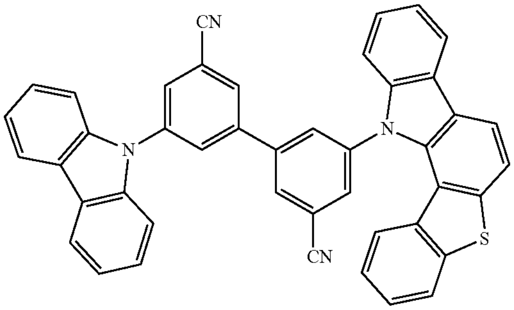

-continued
207
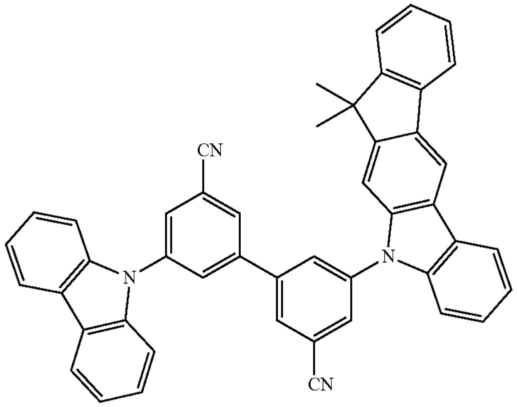
208
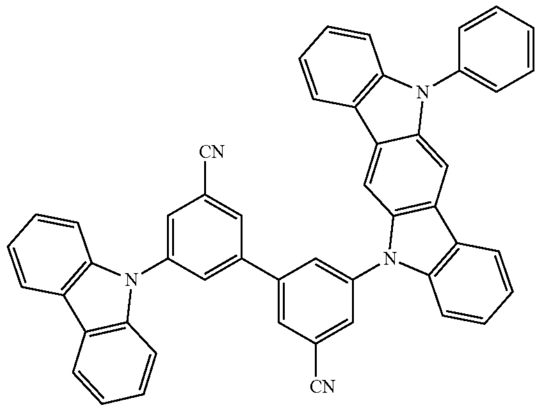
209
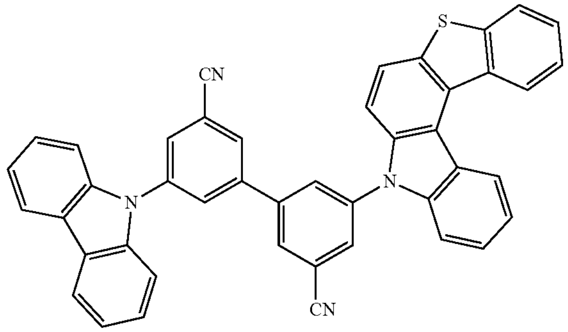
210
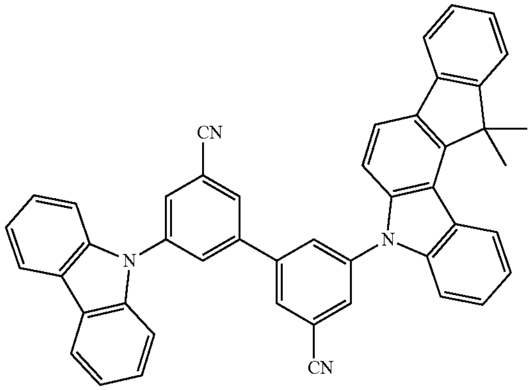
-continued
211
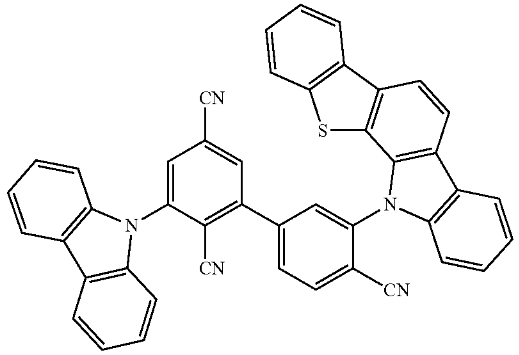
212
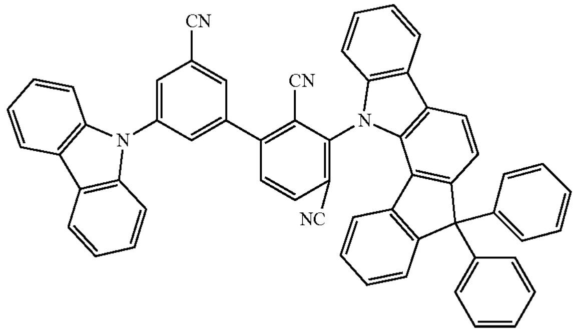
213
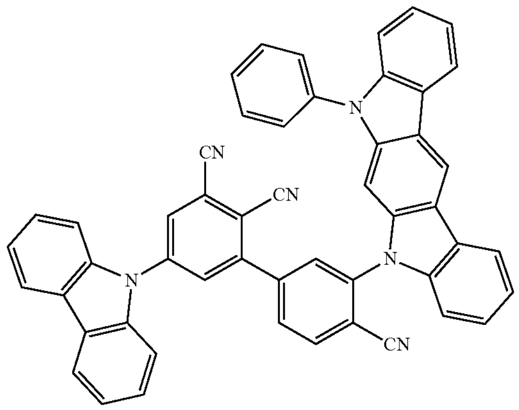
214
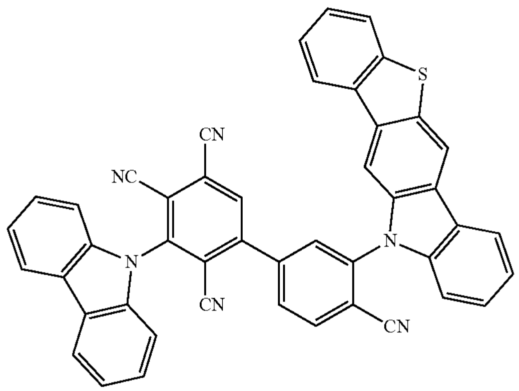

-continued
215
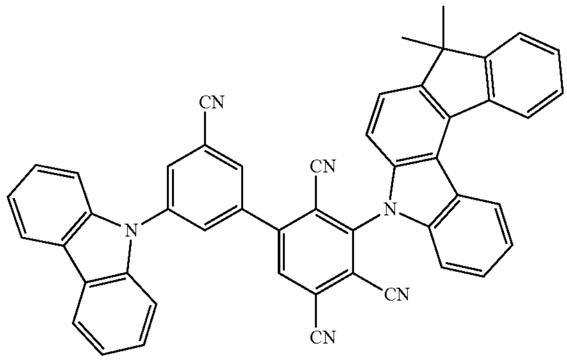
216
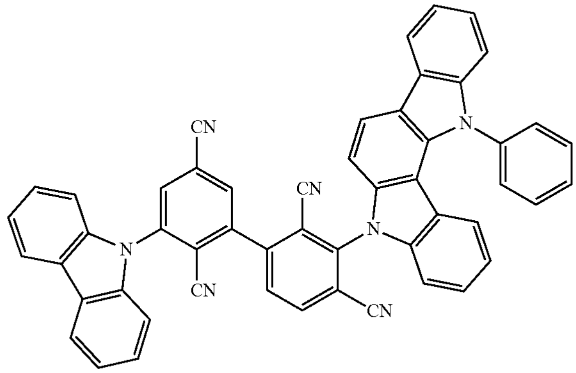
217
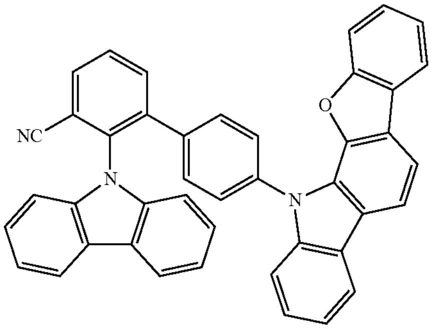
218
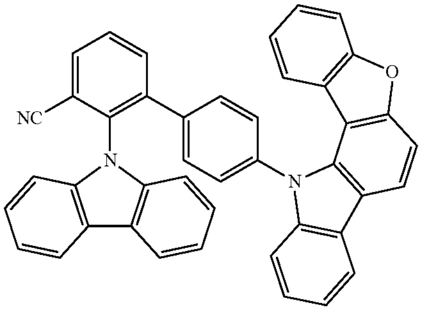
-continued
219
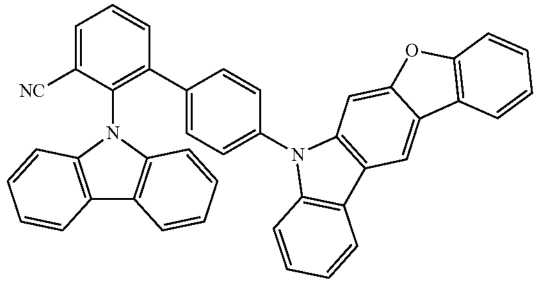
220
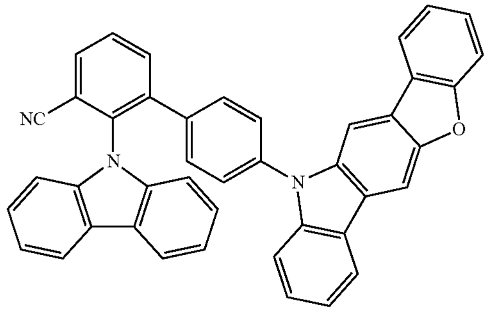
221
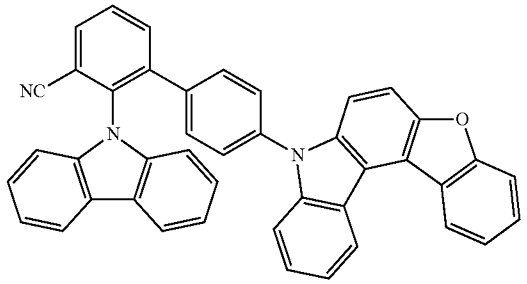
222
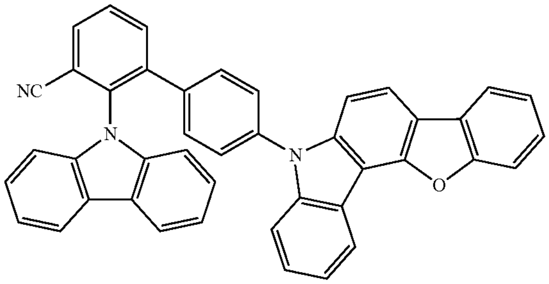
223
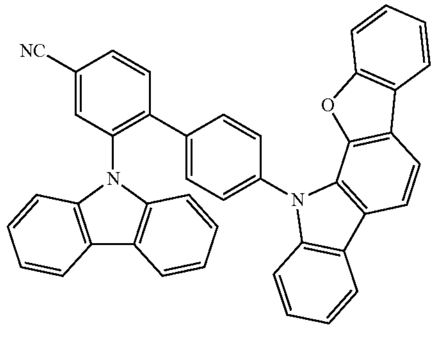

-continued
224
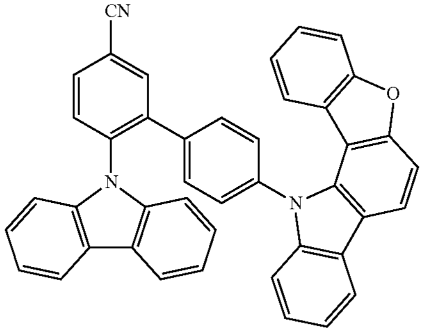
225
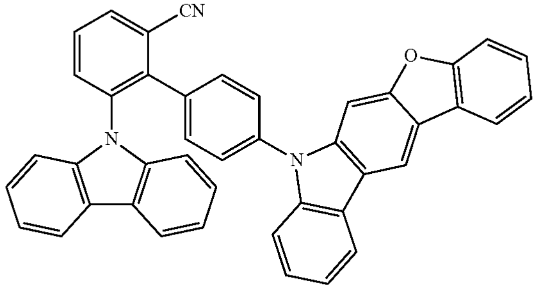
226
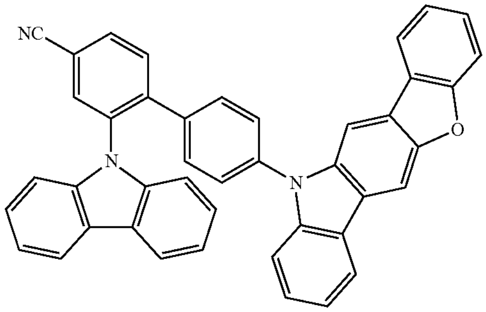
227
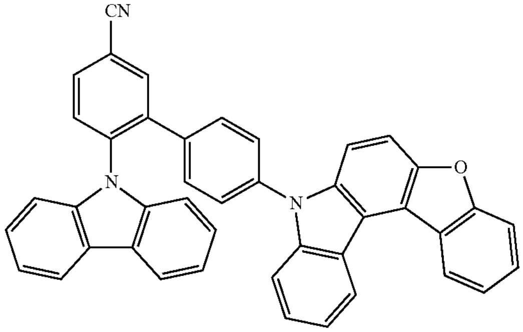
228
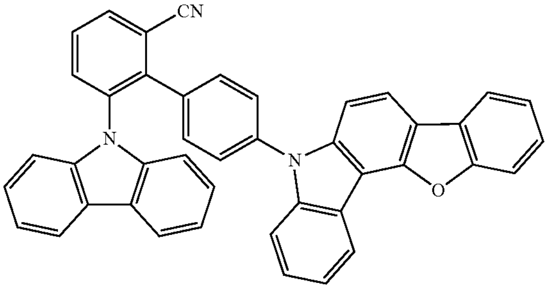
-continued
229
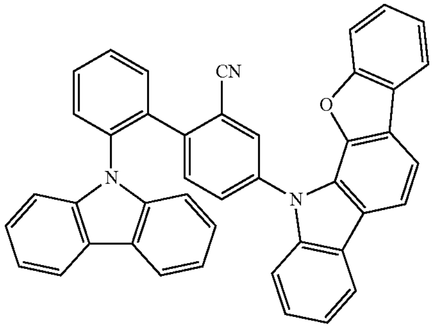
230
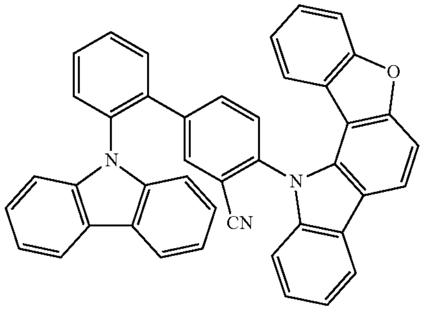
231
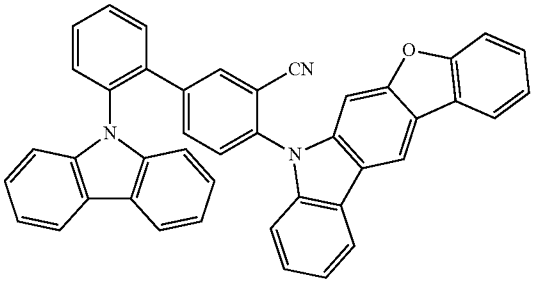
232
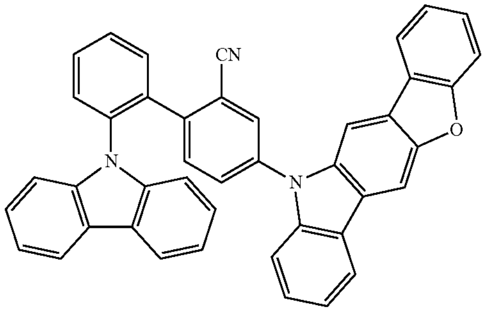
233
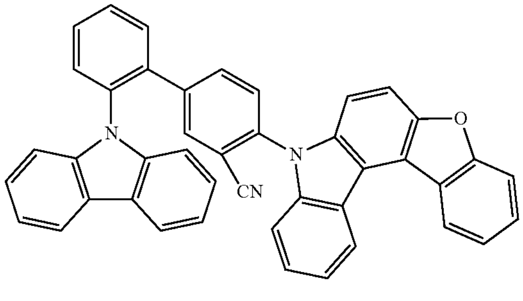

-continued
234
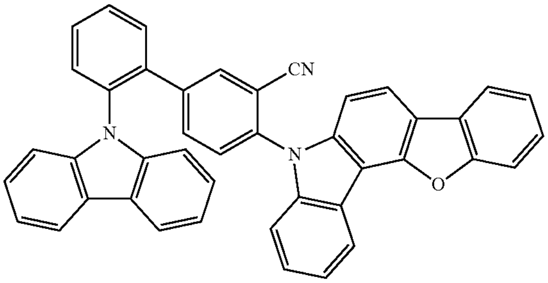
235
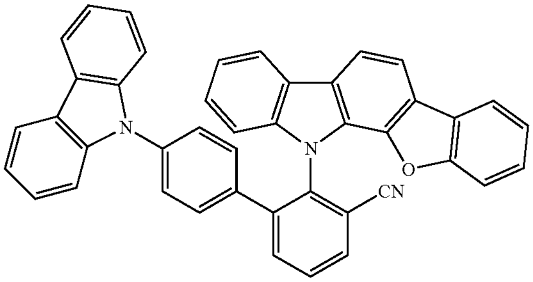
236
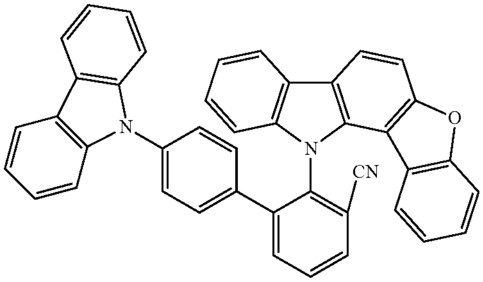
237
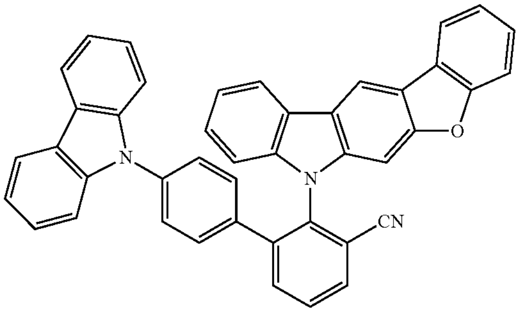
238
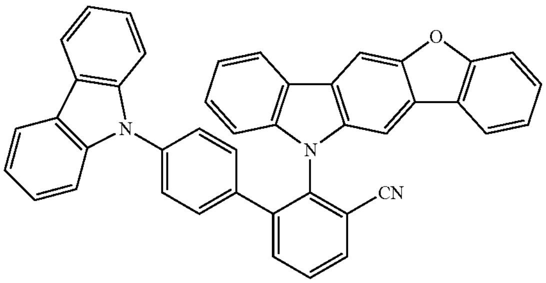
-continued
239
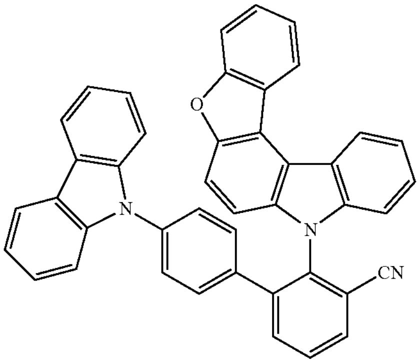
240
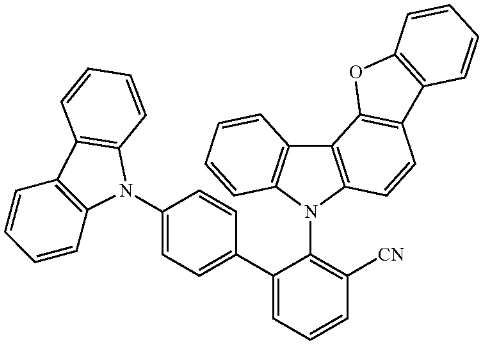
241
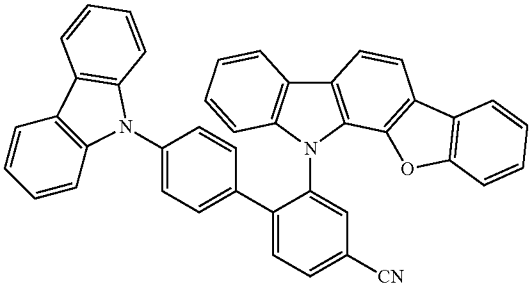
242
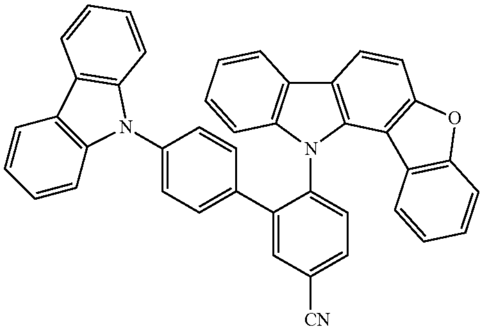

-continued
243
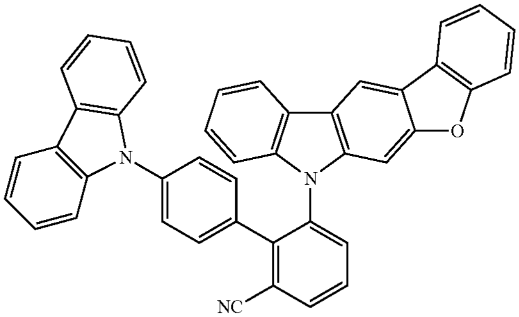
244
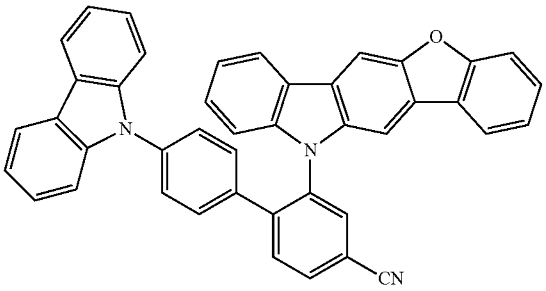
245
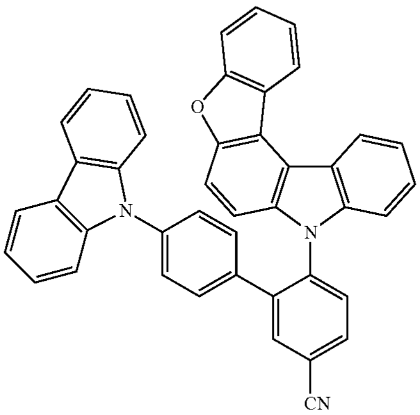
246
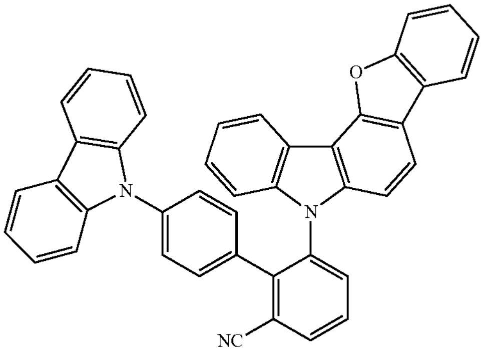
-continued
247
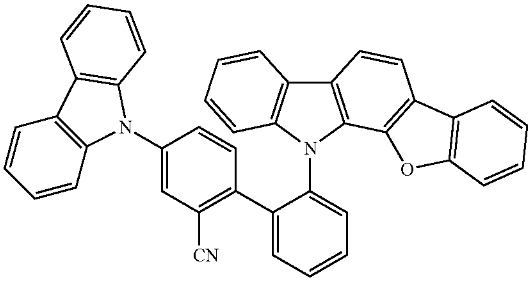
248
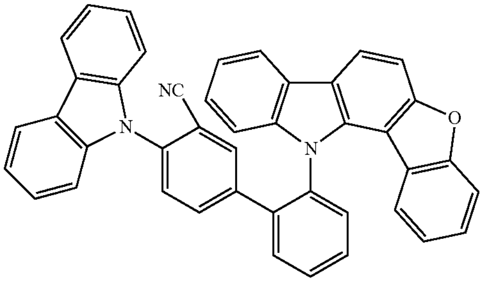
249
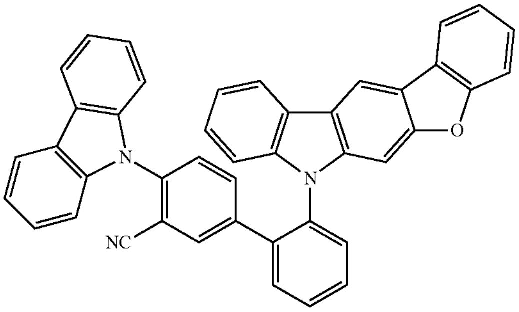
250
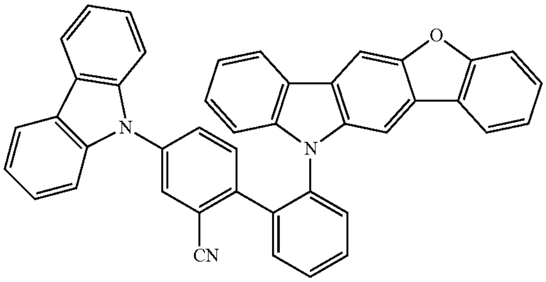
251
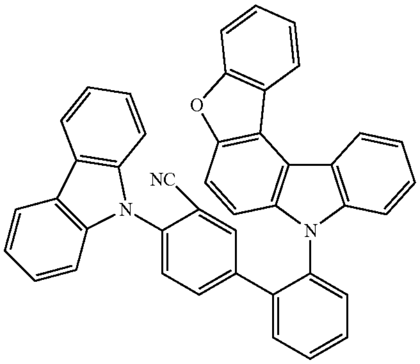

-continued
252
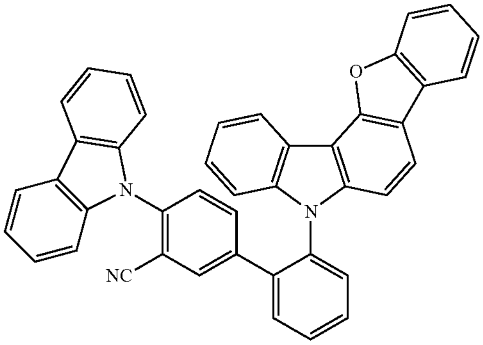
253
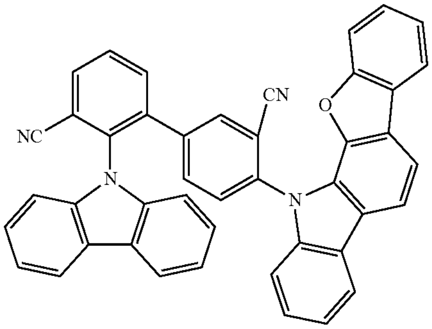
254
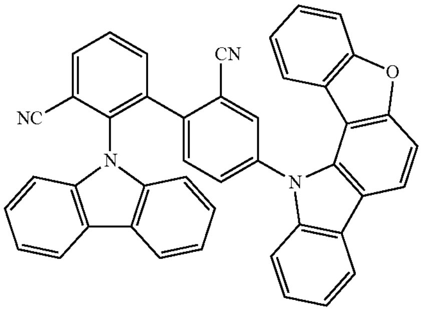
255
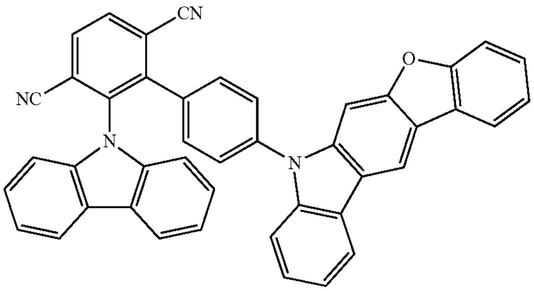
256
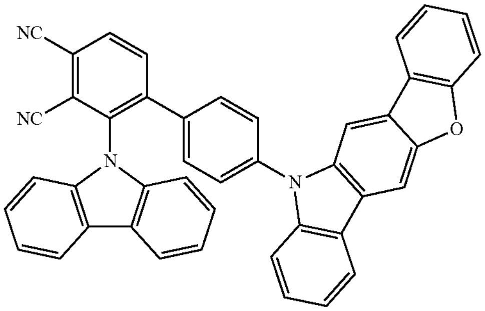
-continued
257
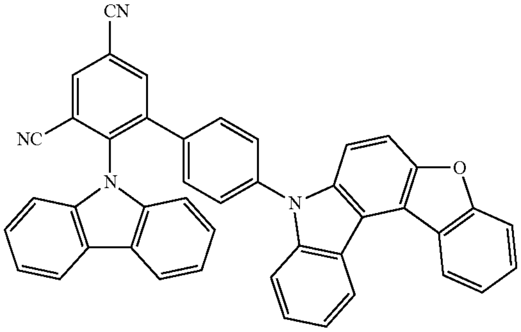
258
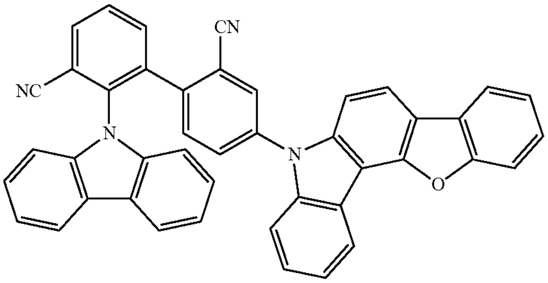
259
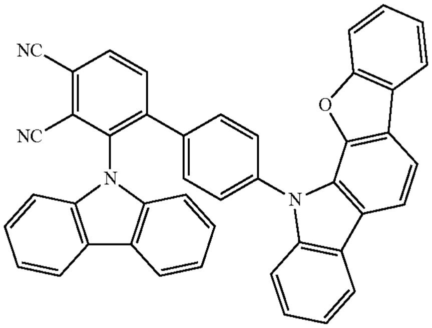
260
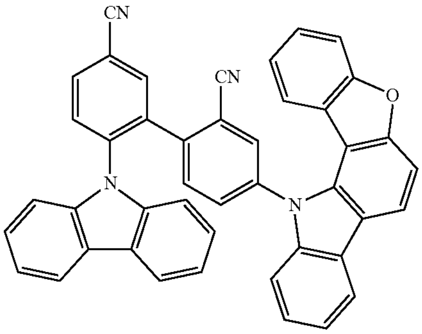
261
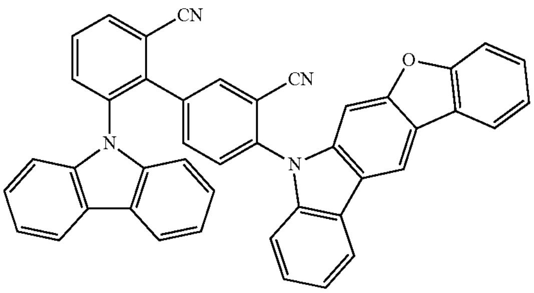

-continued
262
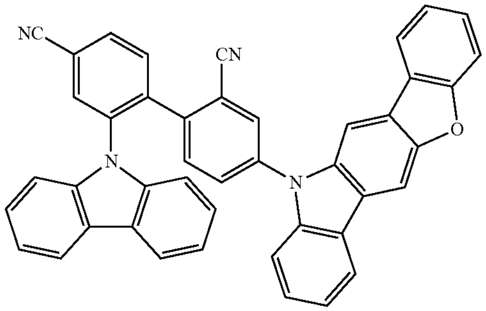
263
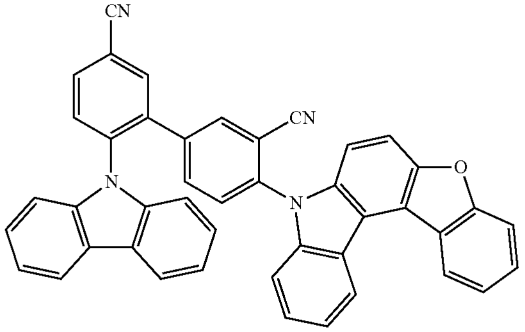
264
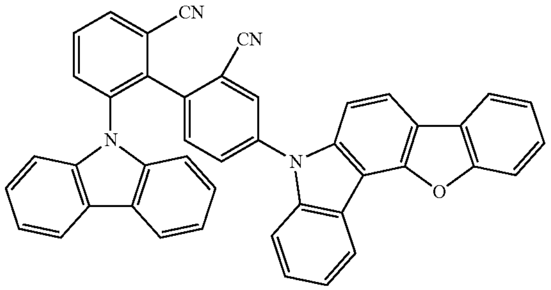
265
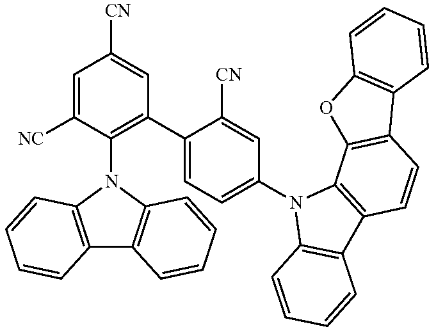
266
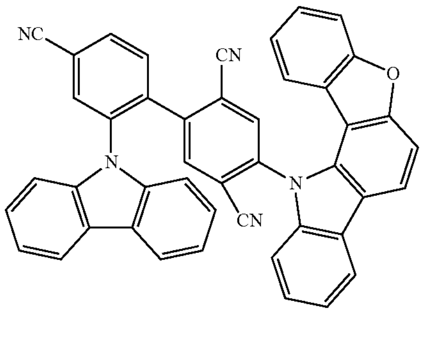
-continued
267
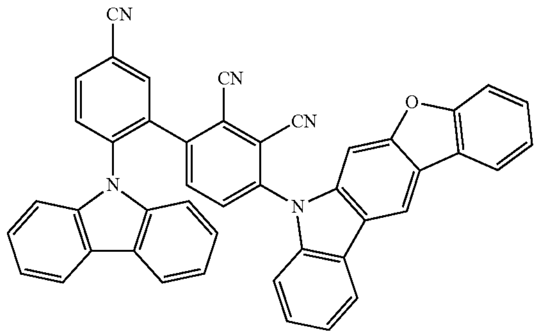
268
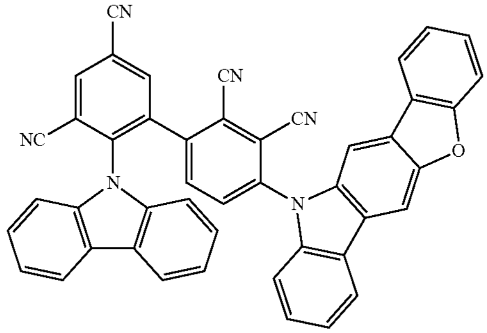
269
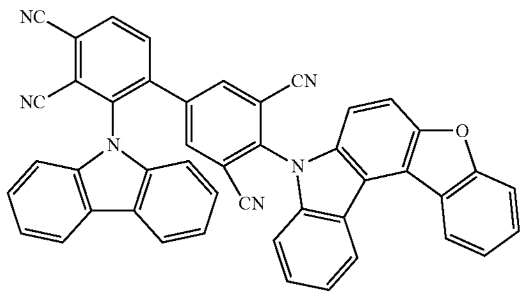
270
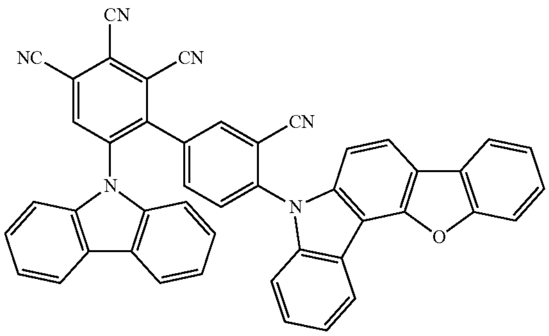

-continued
271
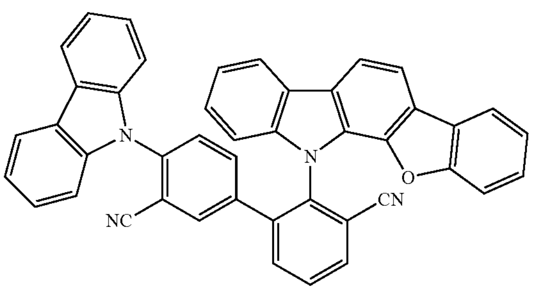
272
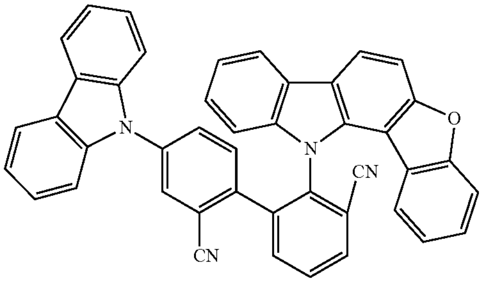
273
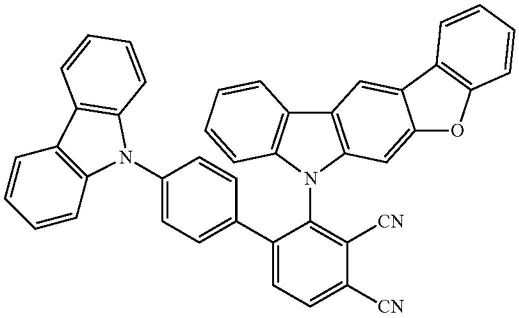
274
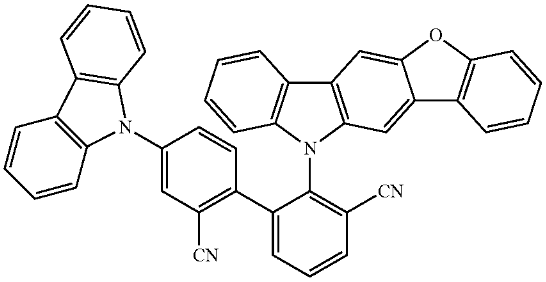
275
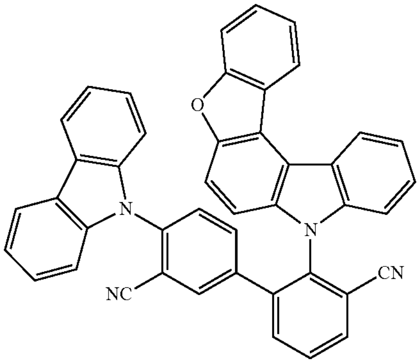
-continued
276
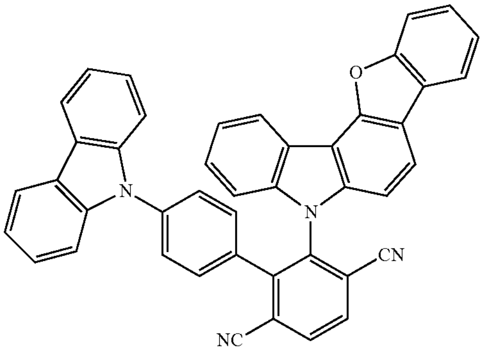
277
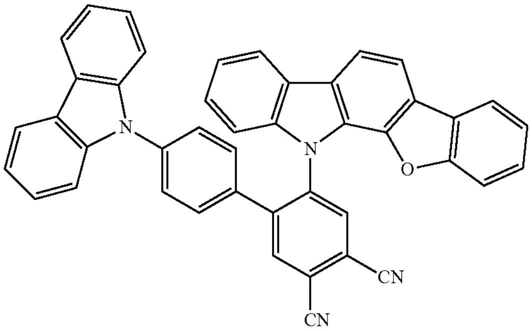
278
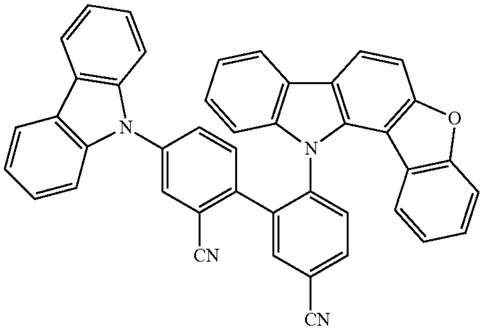
279
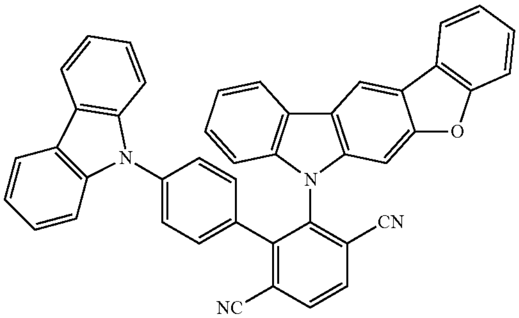

-continued
280
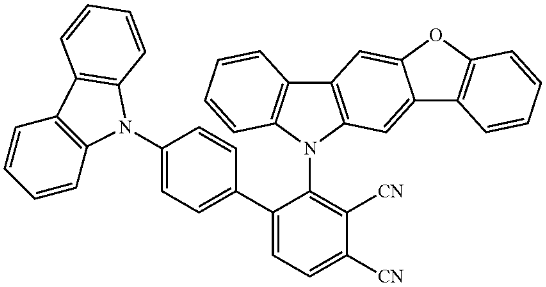
281
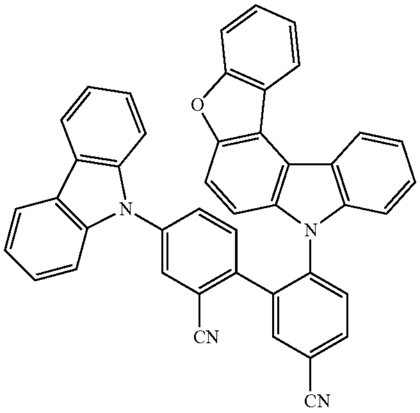
282
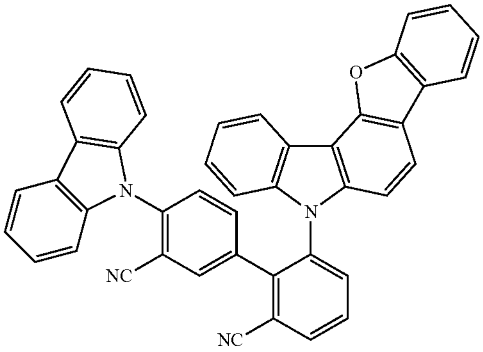
283
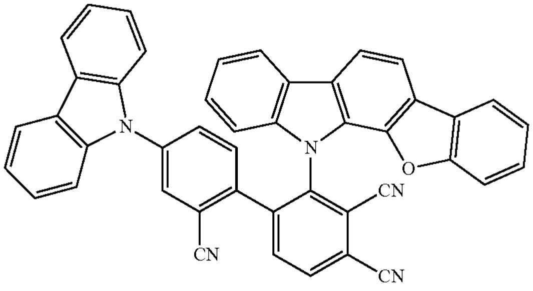
-continued
284
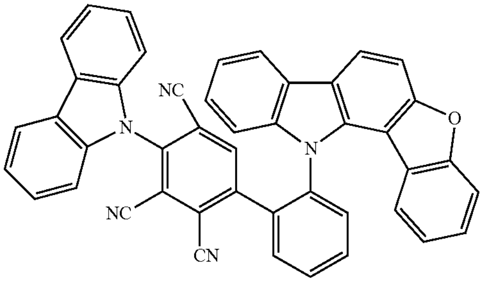
285
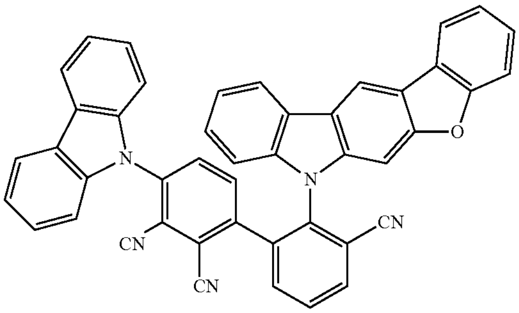
286
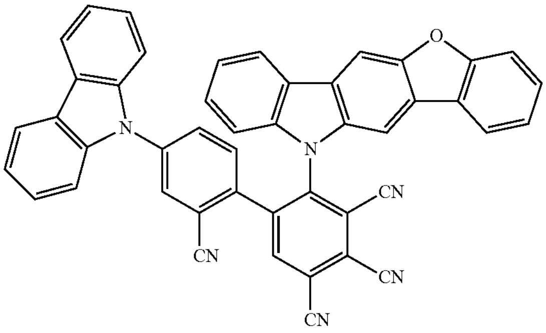
287
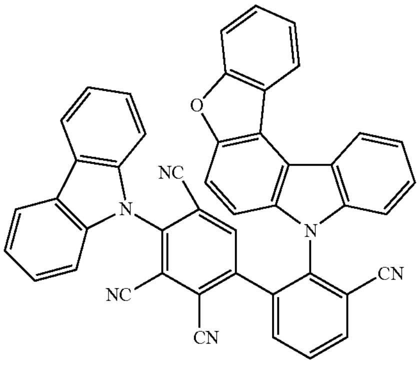

-continued
288
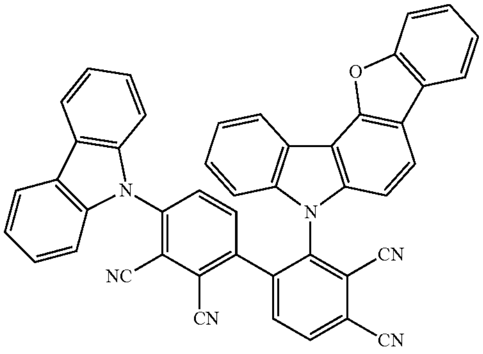
289
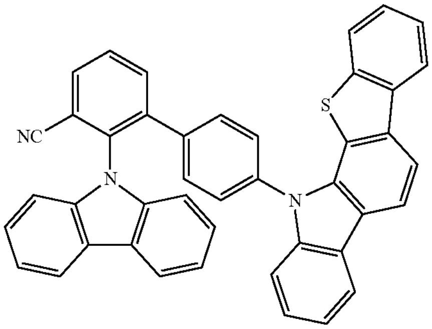
290
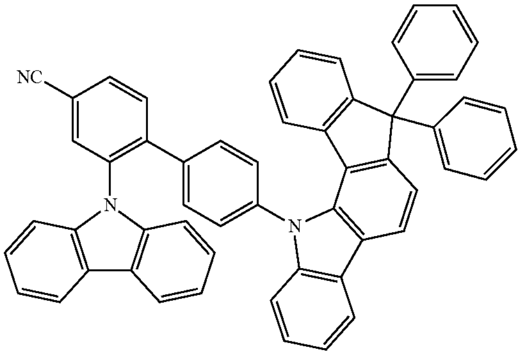
291
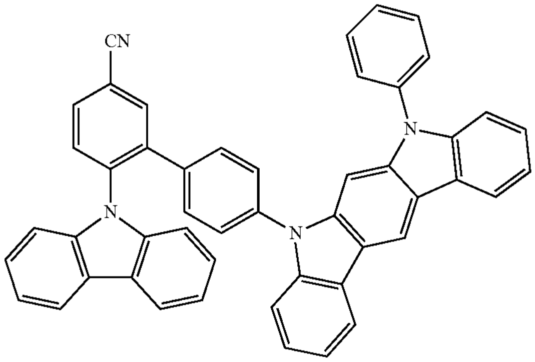
-continued
292
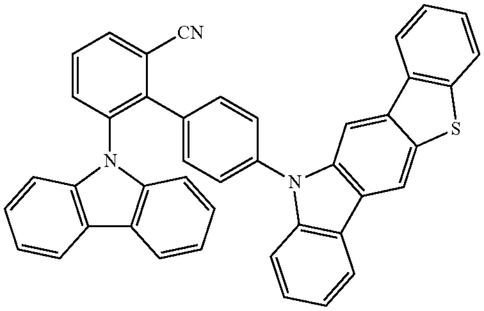
293
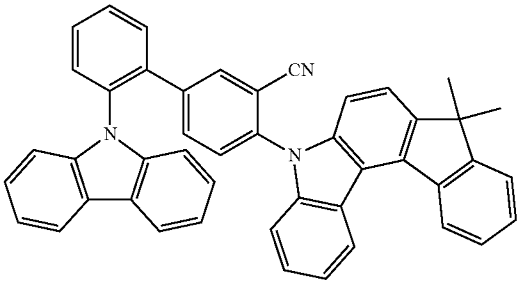
294
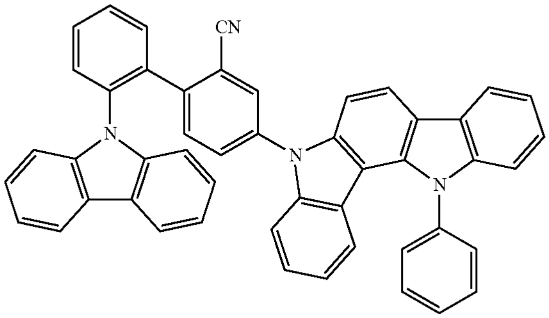
295
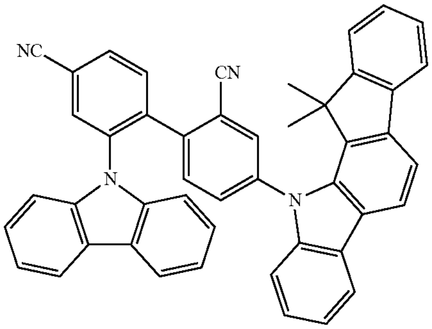

-continued
296
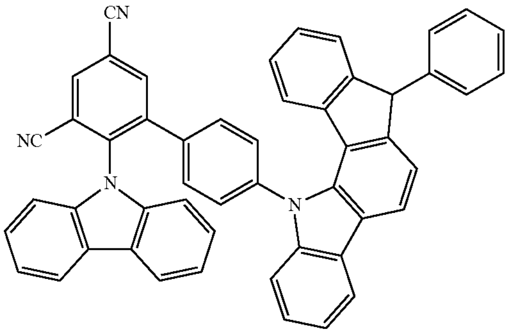
297
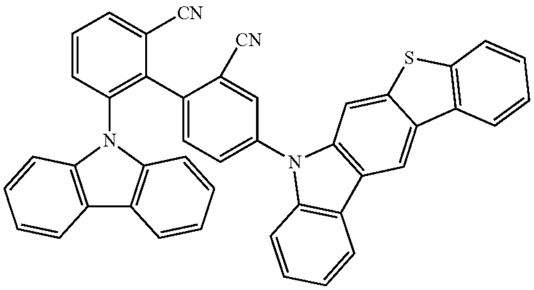
298
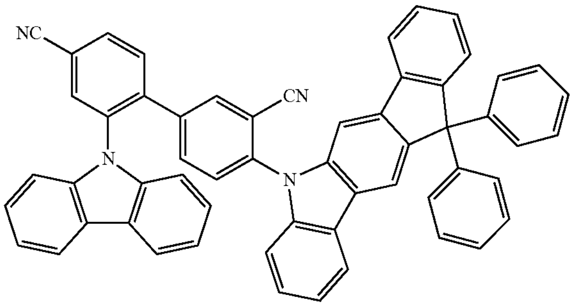
299
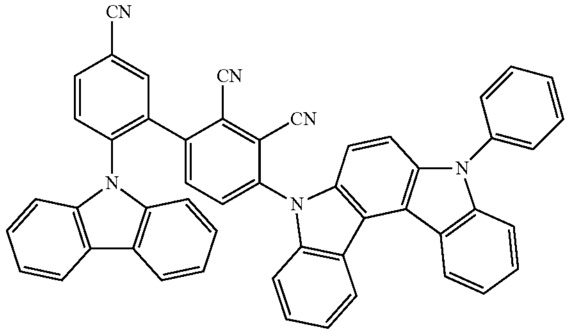
-continued
300
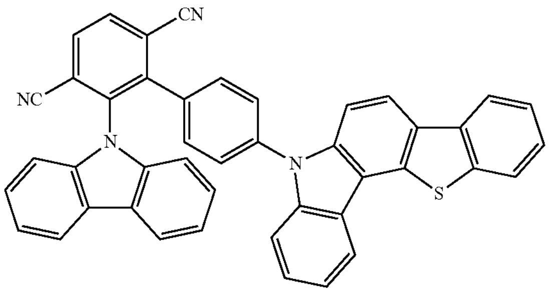
301
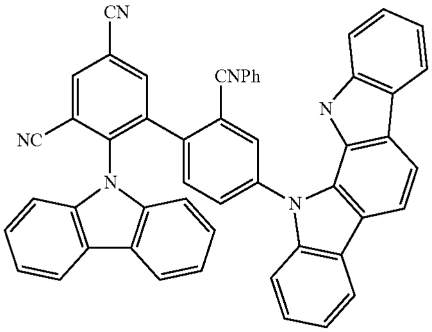
302
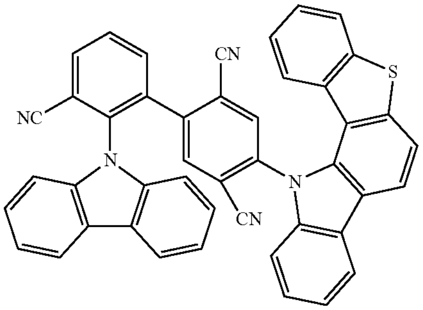
303
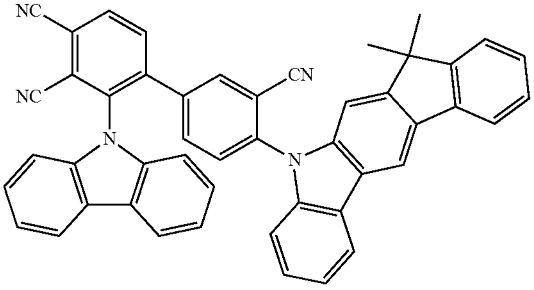
304
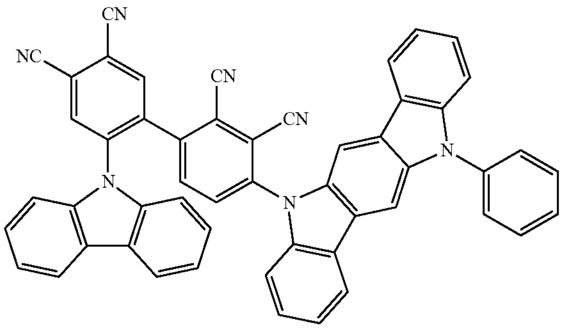

-continued
305
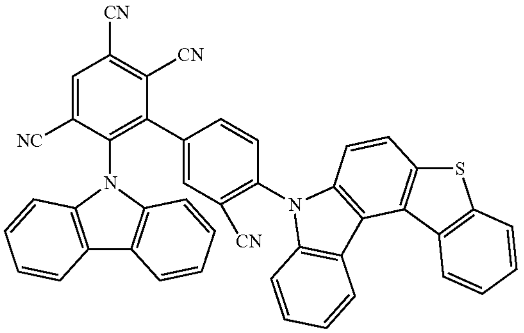
306
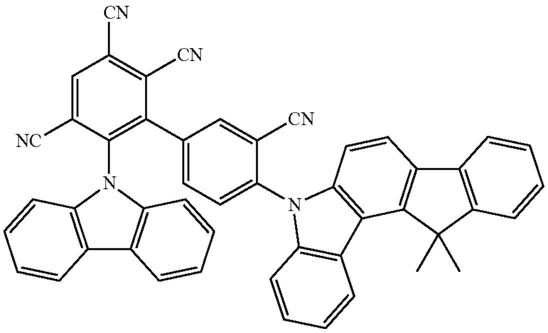
307
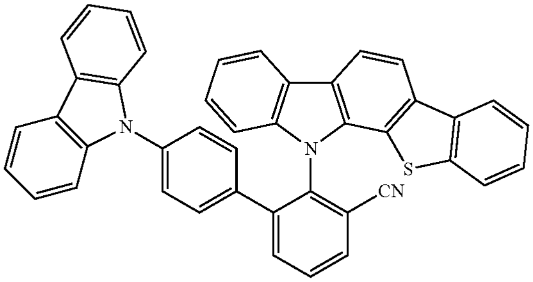
308
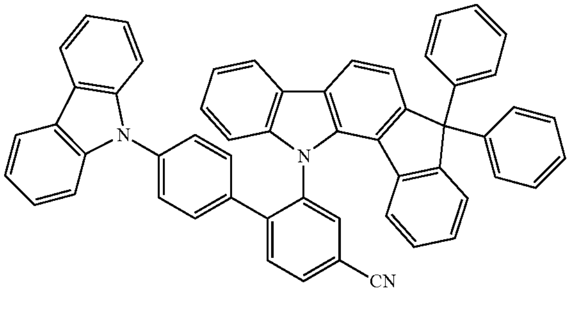
-continued
309
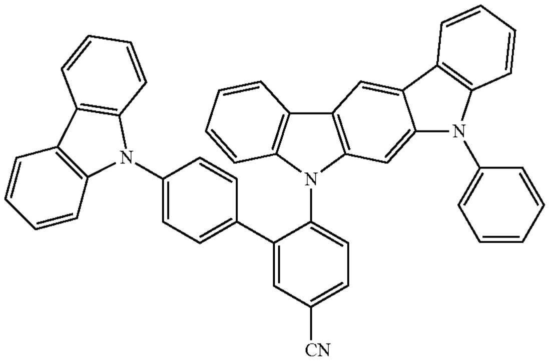
310
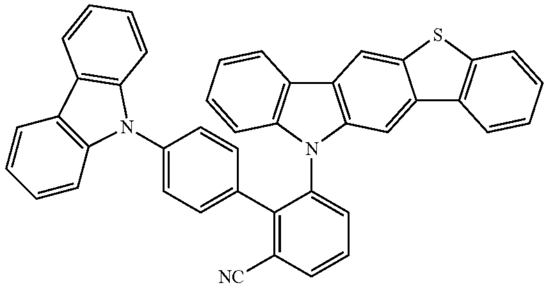
311
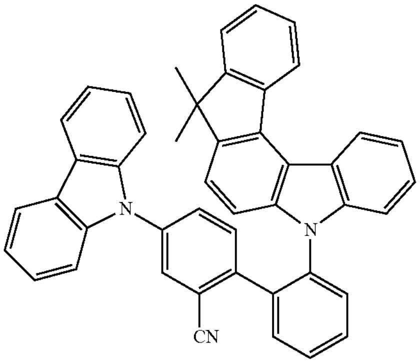
312
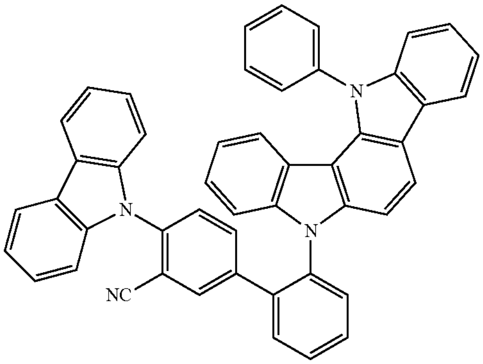

-continued
313
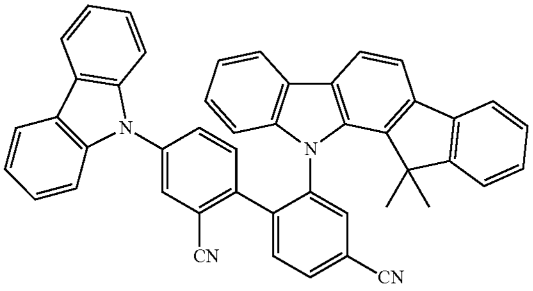
314
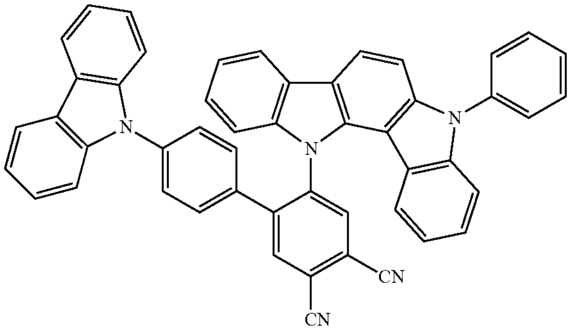
315
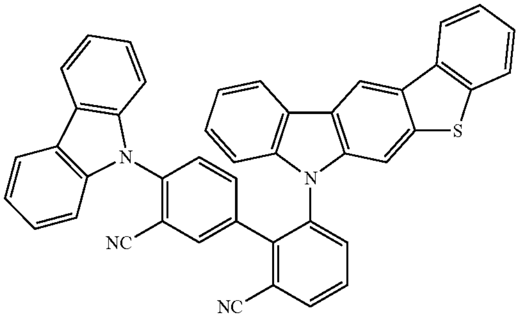
316
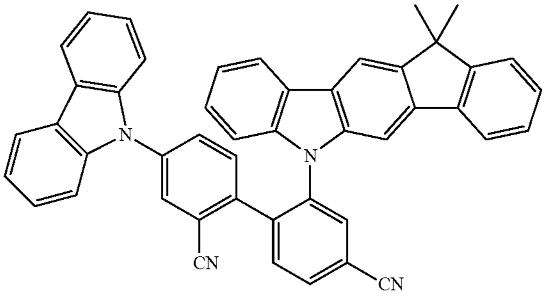
-continued
317
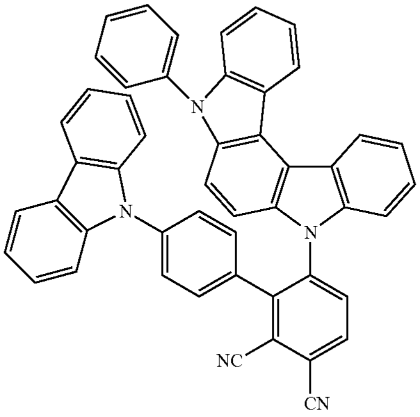
318
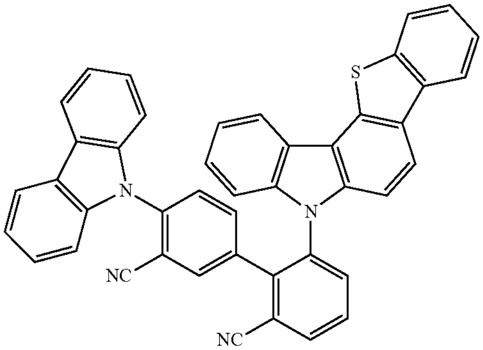
319
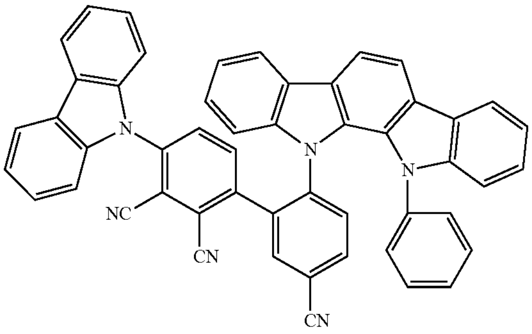
320
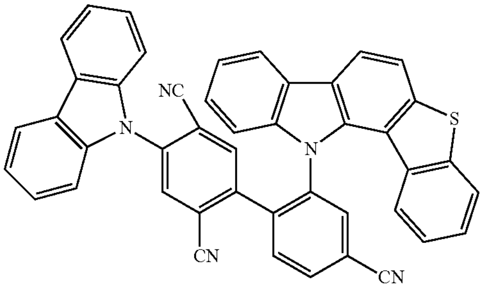

-continued
321
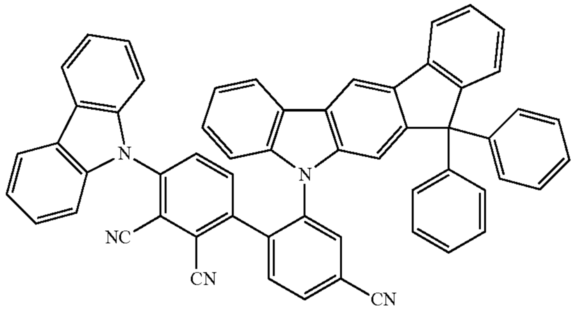
322
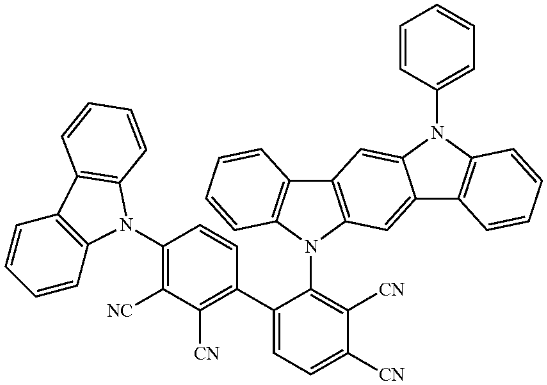
323
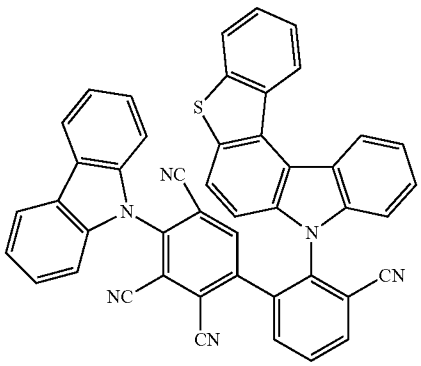
324
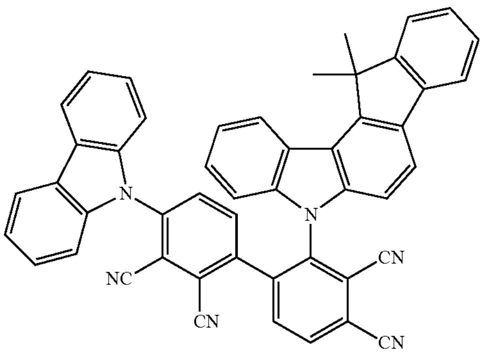
325
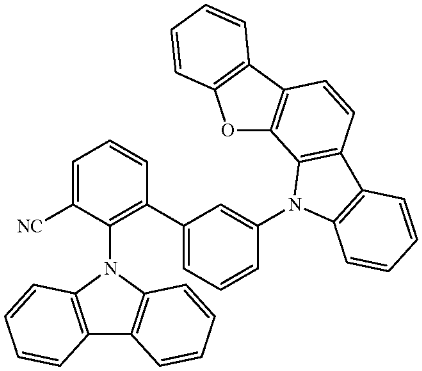
326
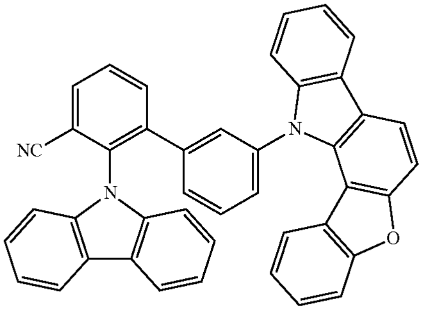
327
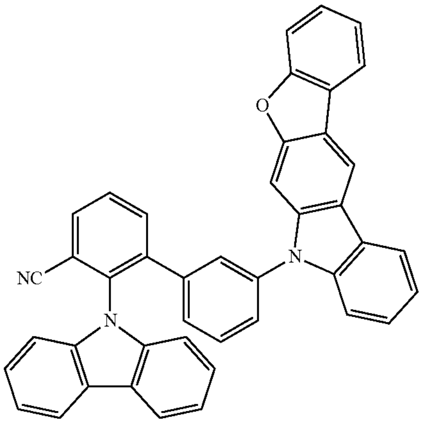
328
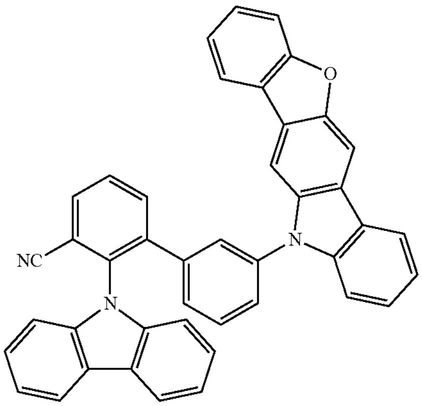

-continued
329
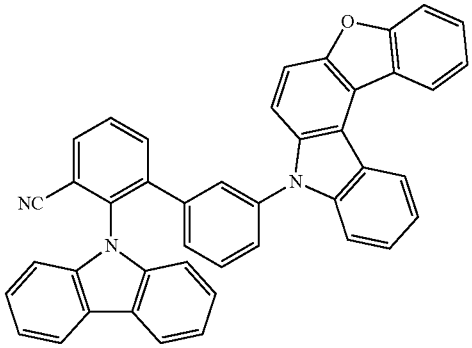
330
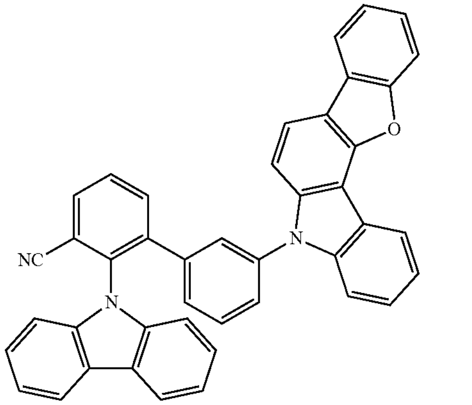
331
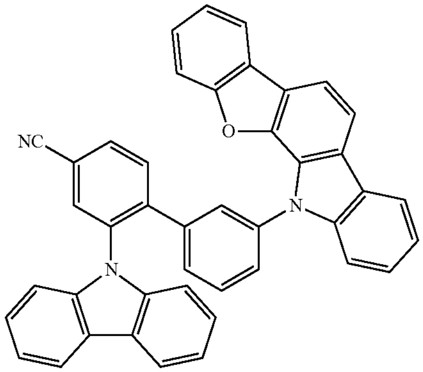
332
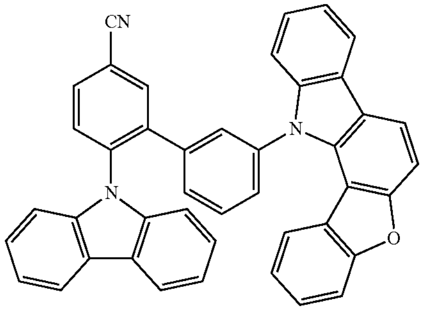
-continued
333
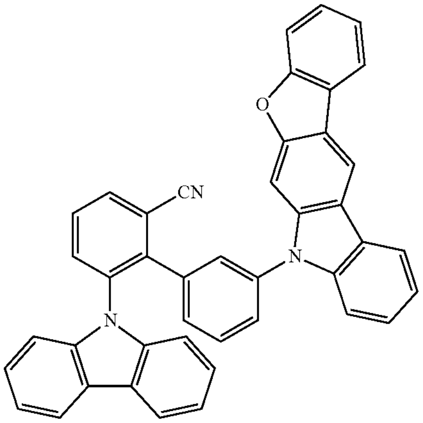
334
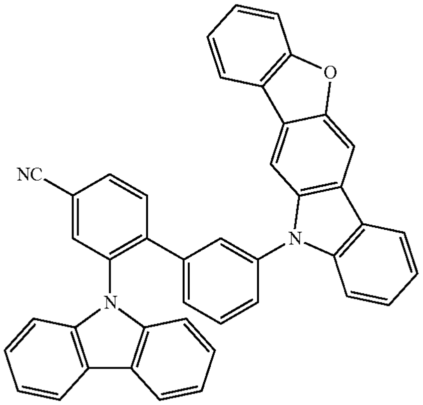
335
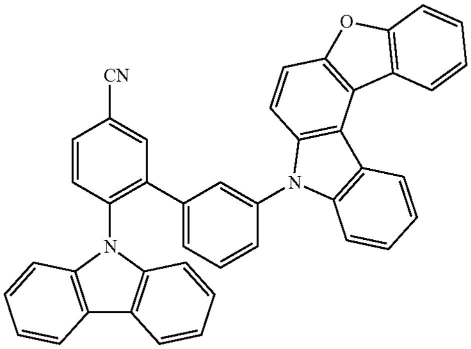
336
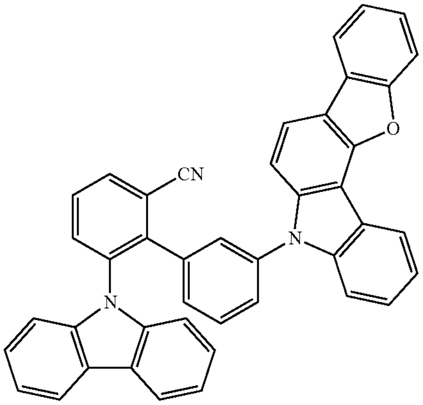

-continued
337
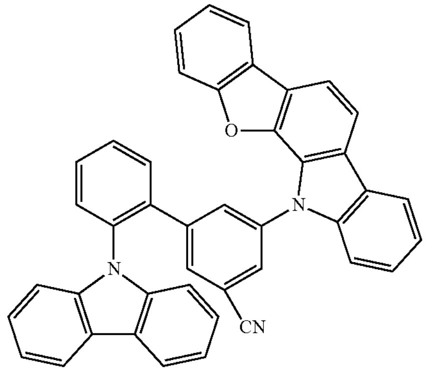
338
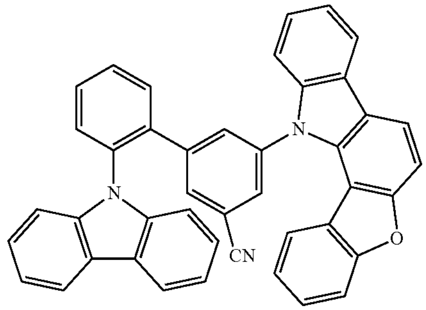
339
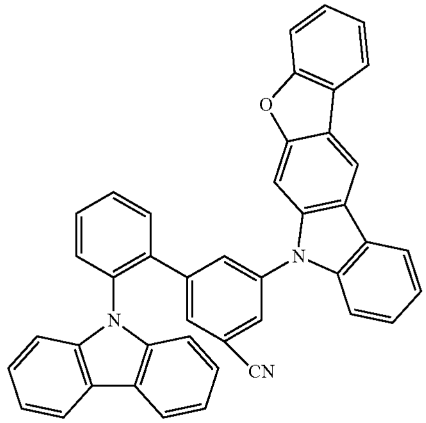
340
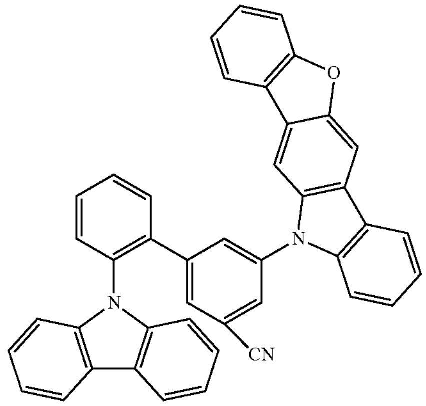
-continued
341
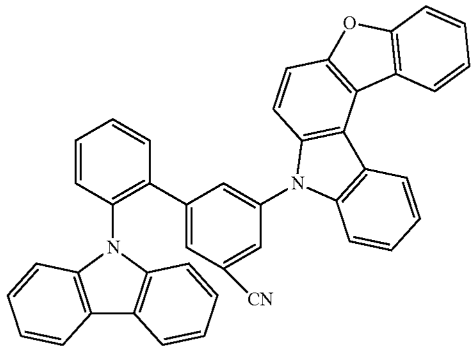
342
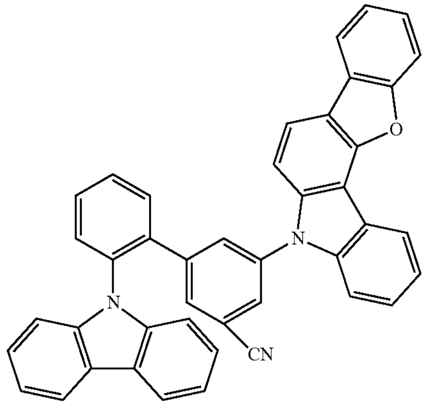
343
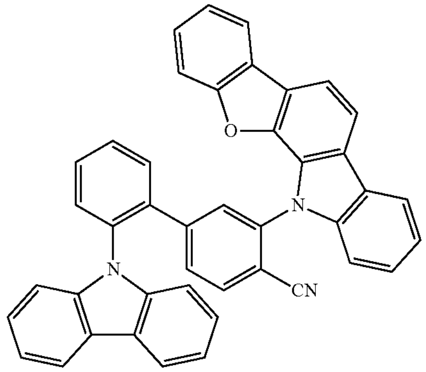
344
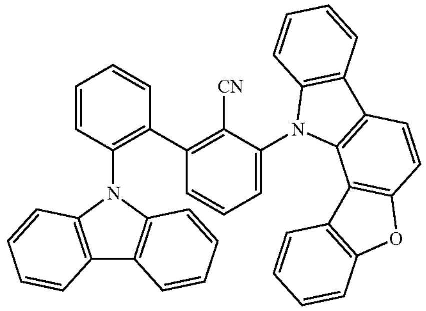

-continued
345
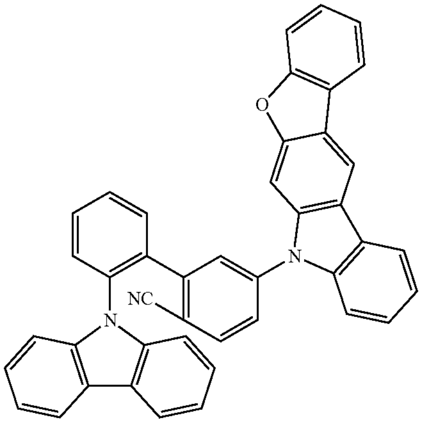
346
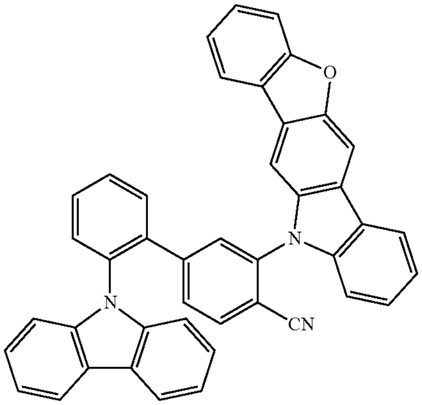
347
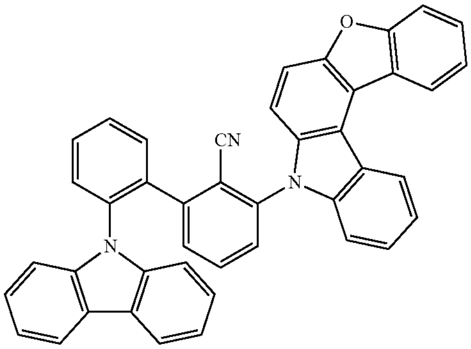
348
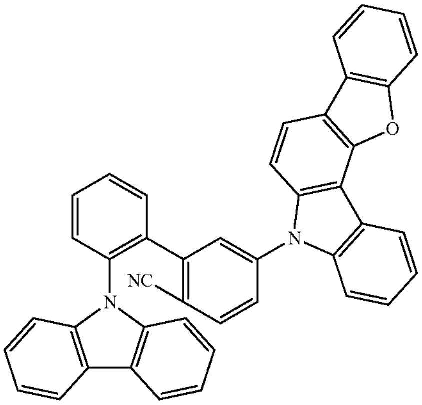
-continued
349
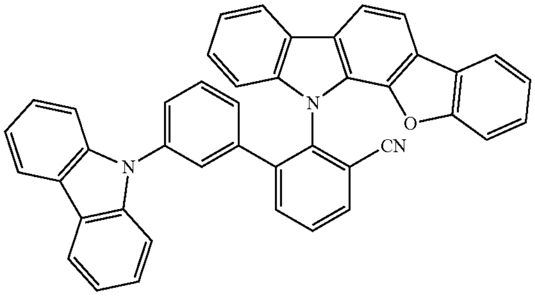
350
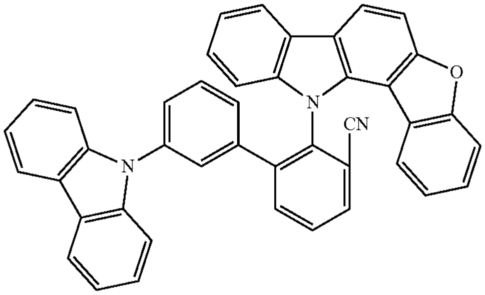
351
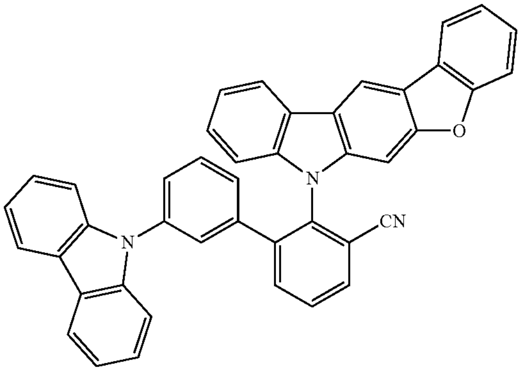
352
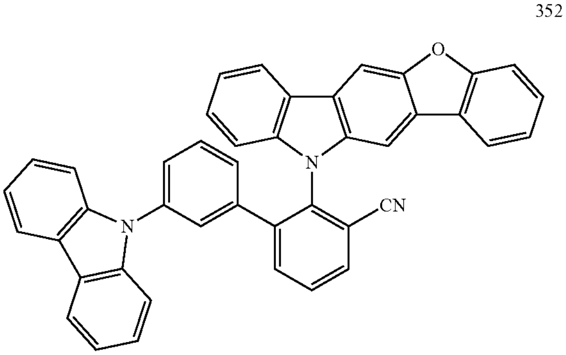

-continued
353
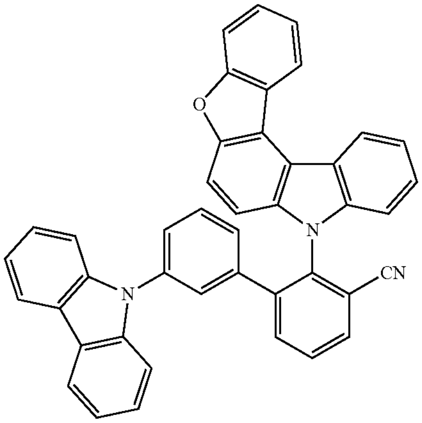
354
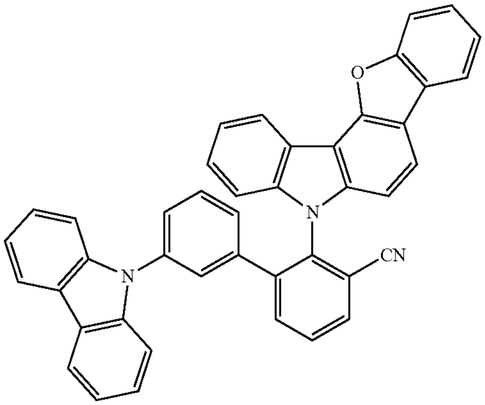
355
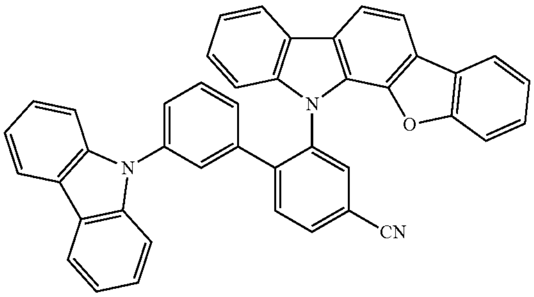
356
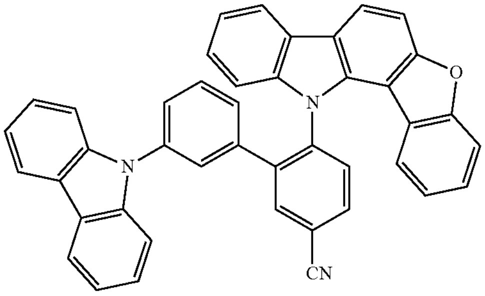
-continued
357
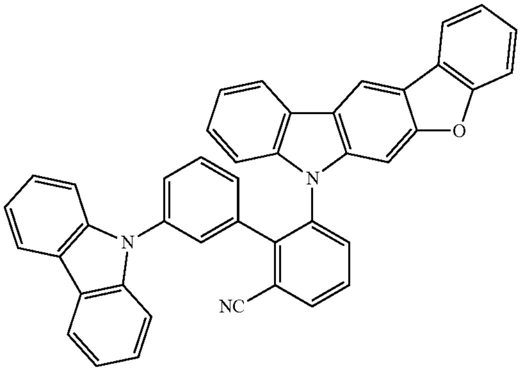
358
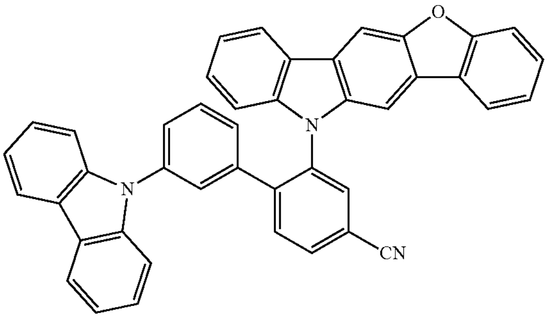
359
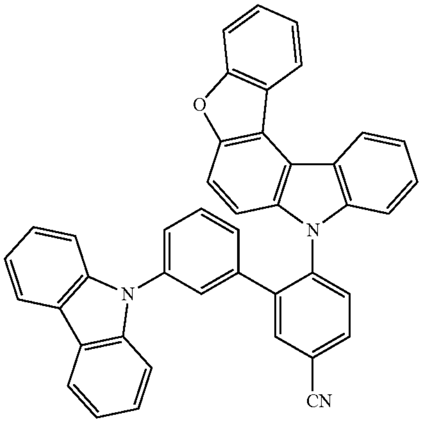
360
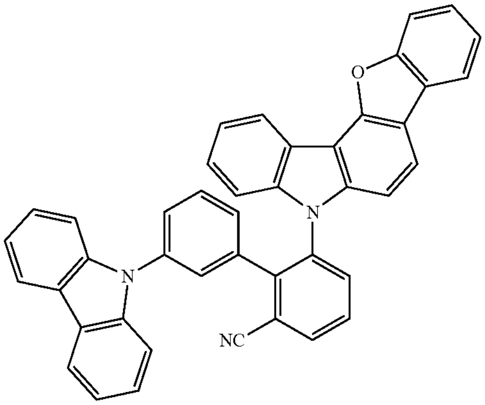

-continued
361
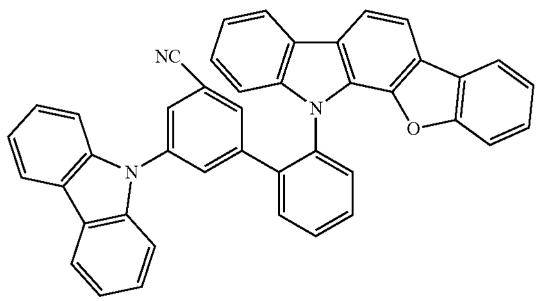
362
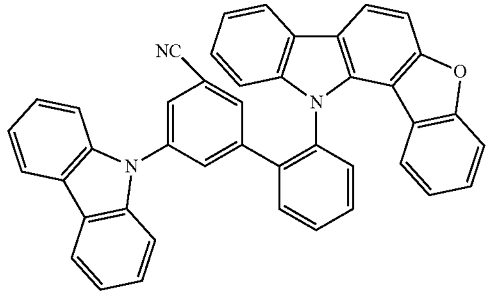
363
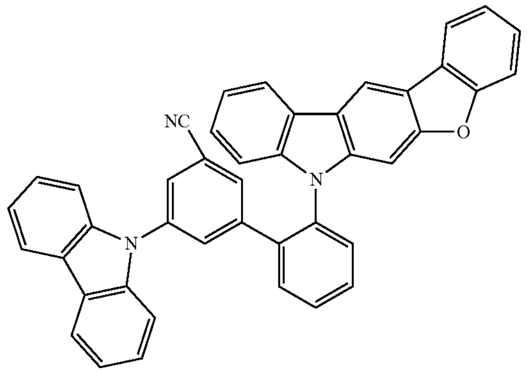
364
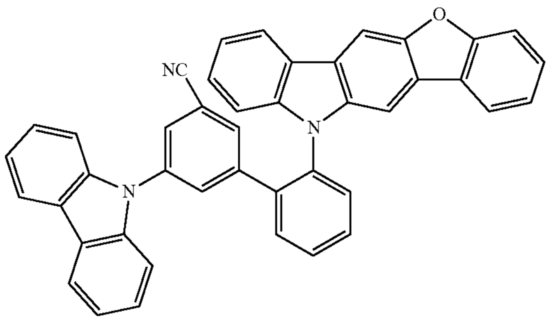
-continued
365
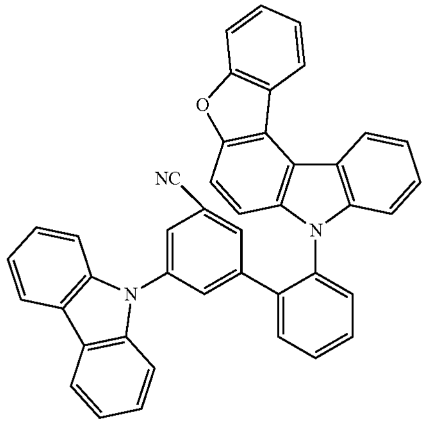
366
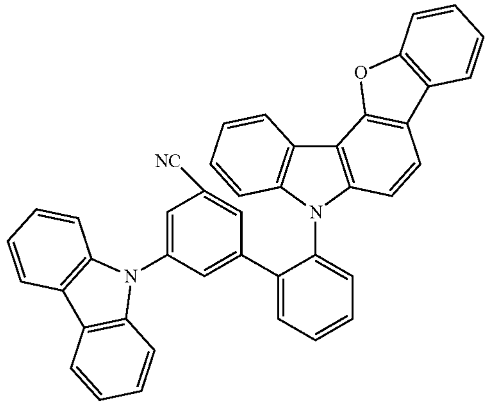
367
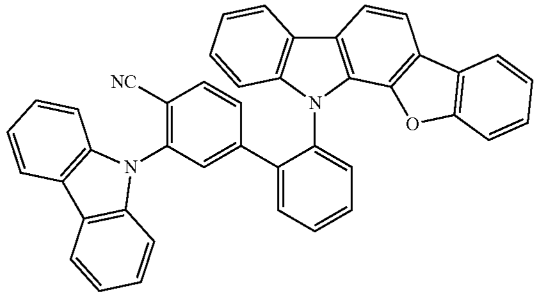
368
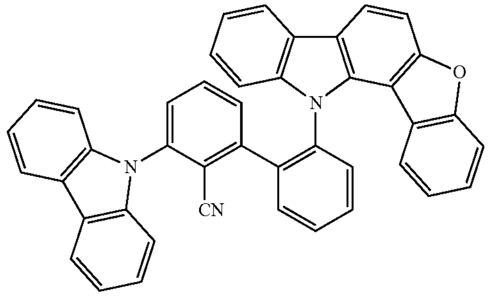

-continued
369
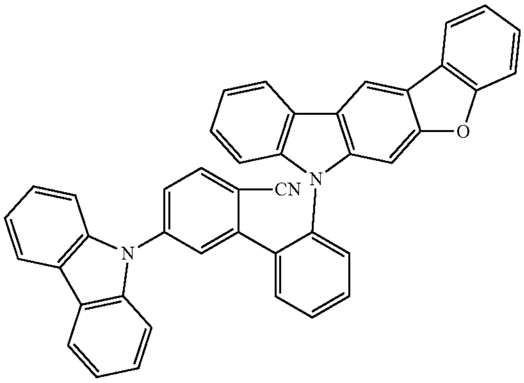
370
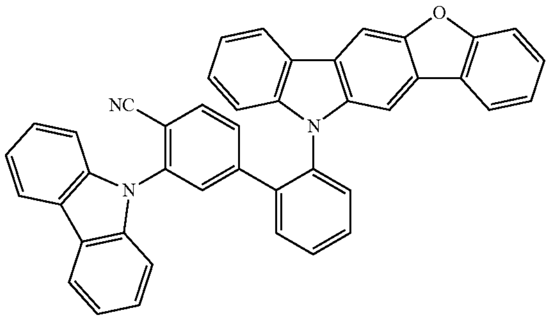
371
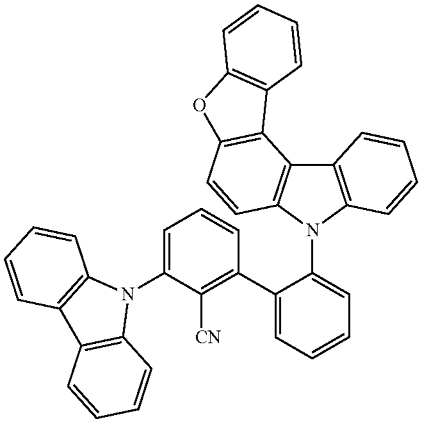
372
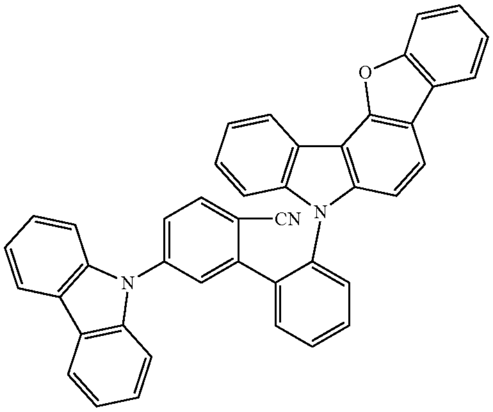
-continued
373
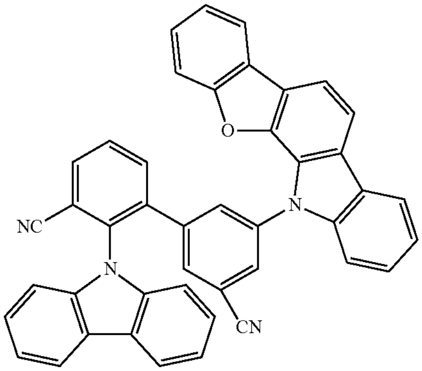
374
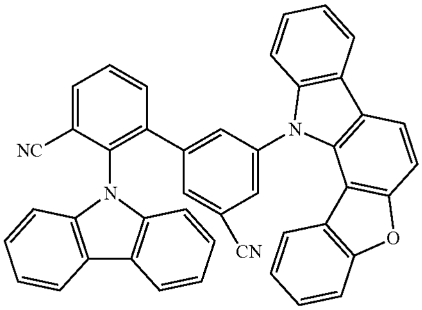
375
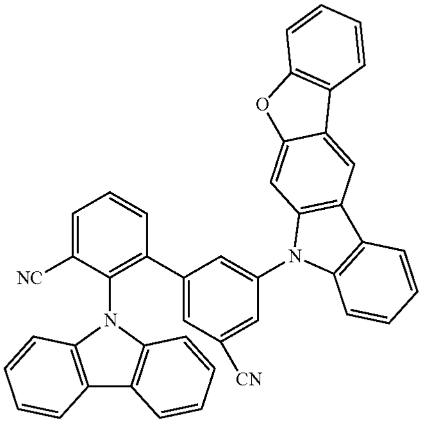
376
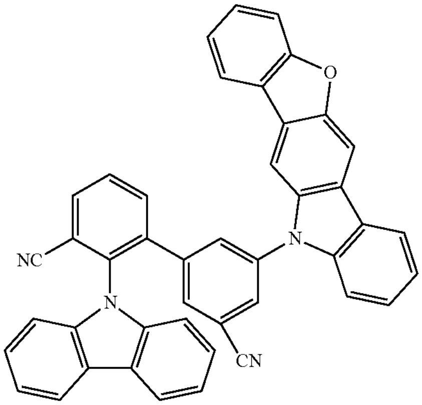

-continued
377
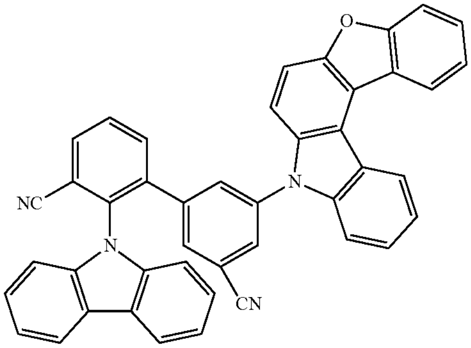
378
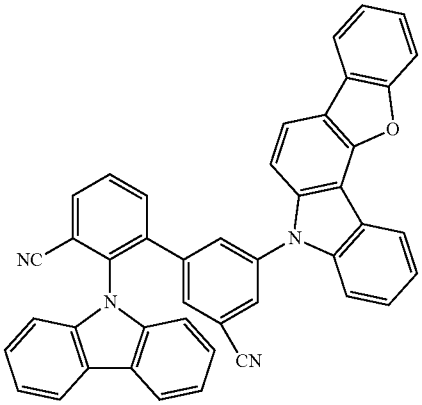
379
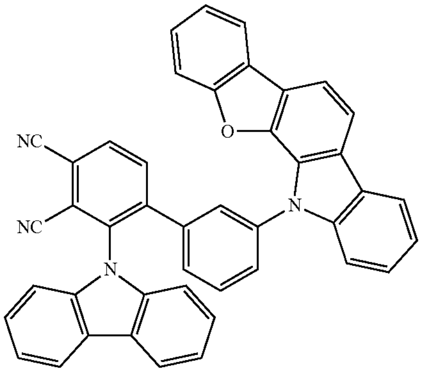
380
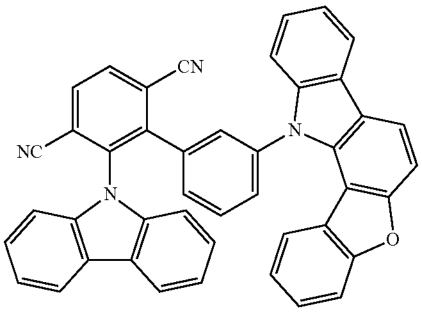
-continued
381
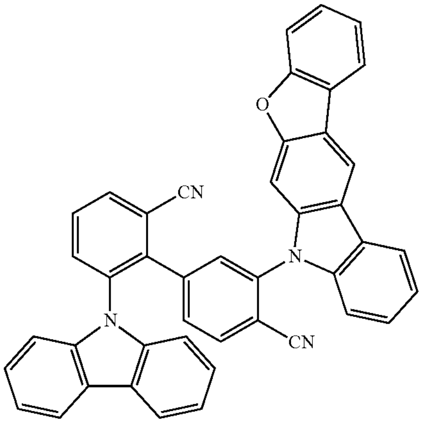
382
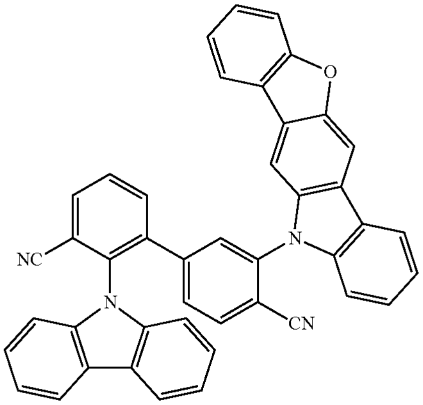
383
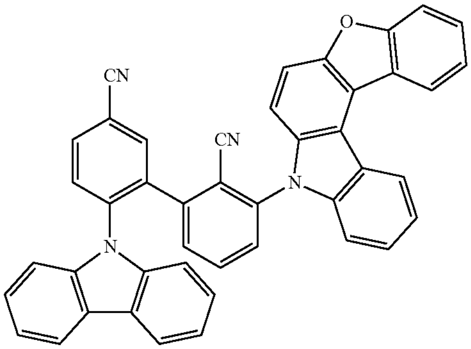
384
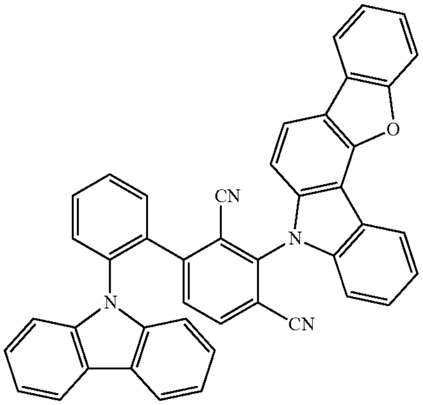

-continued
385
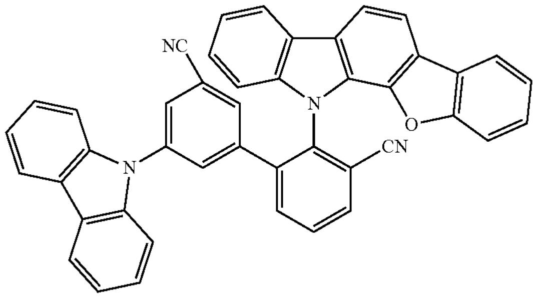
386
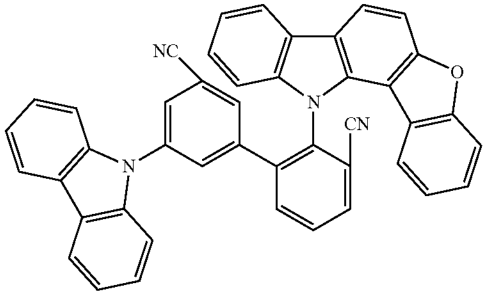
387
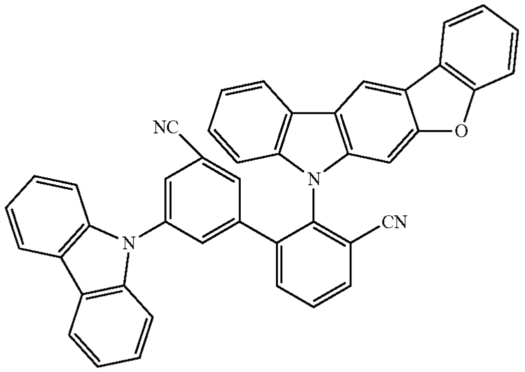
388
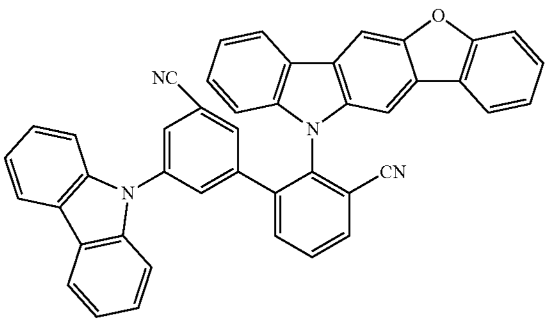
-continued
389
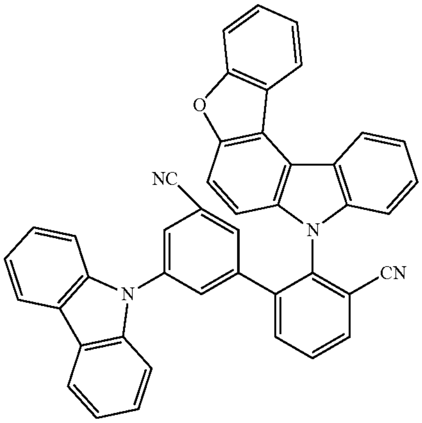
390
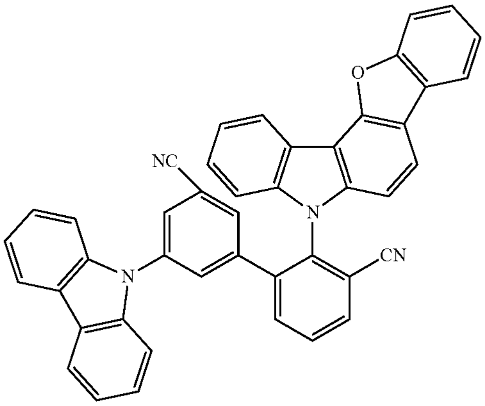
391
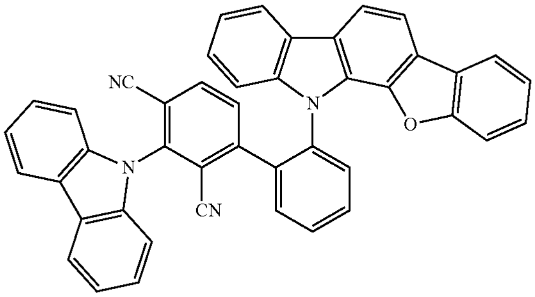
392
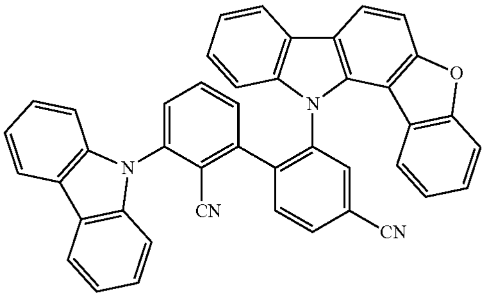

-continued
393
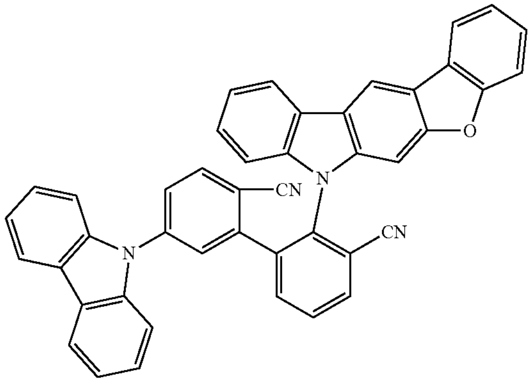
394
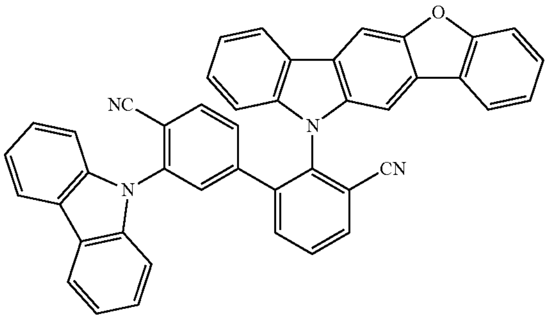
395
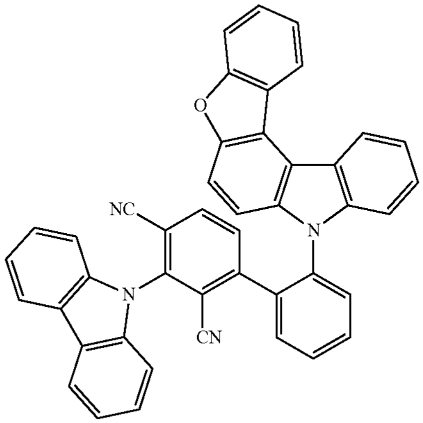
396
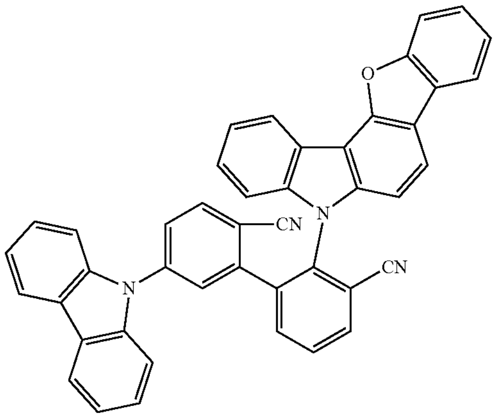
-continued
397
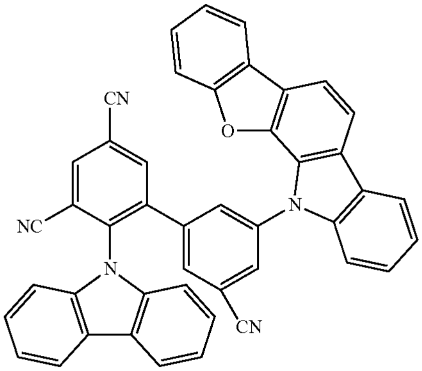
398
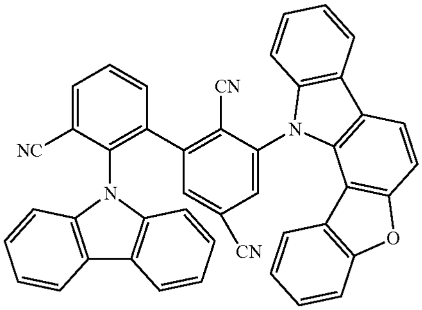
399
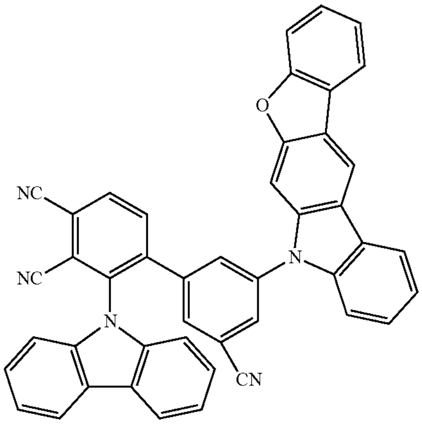
400
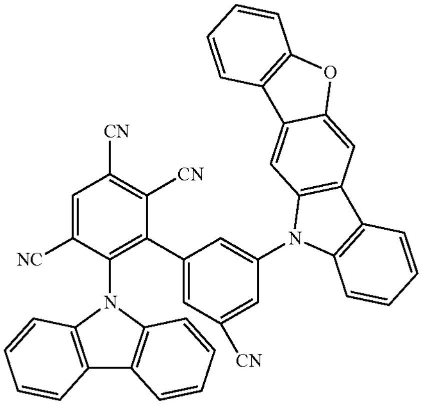

-continued
401
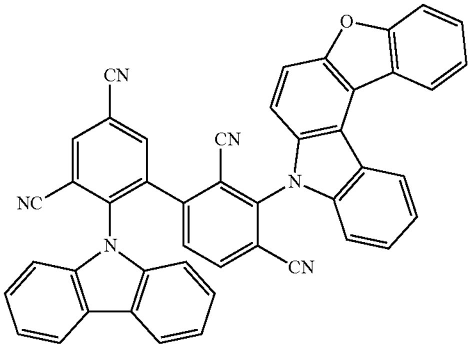
402
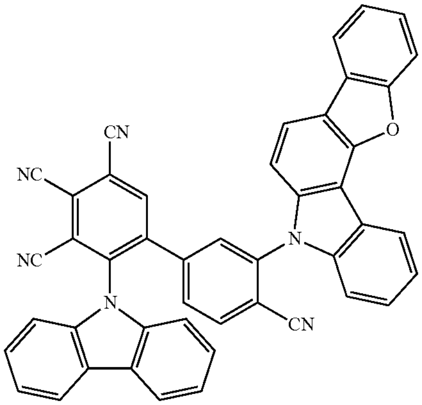
403
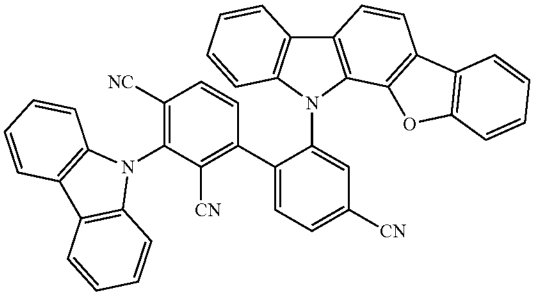
404
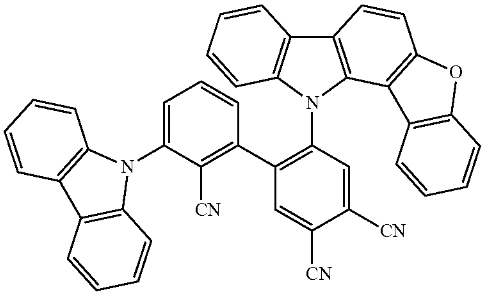
-continued
405
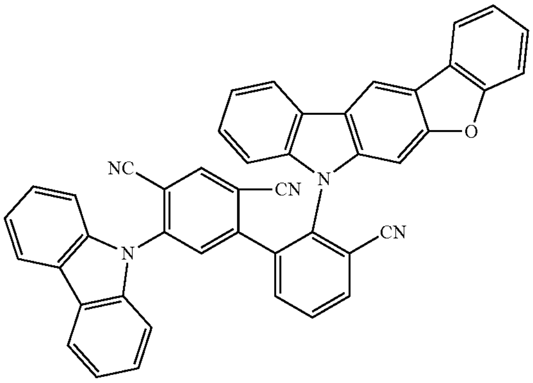
406
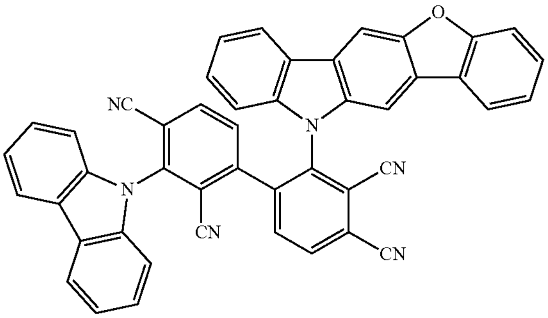
407
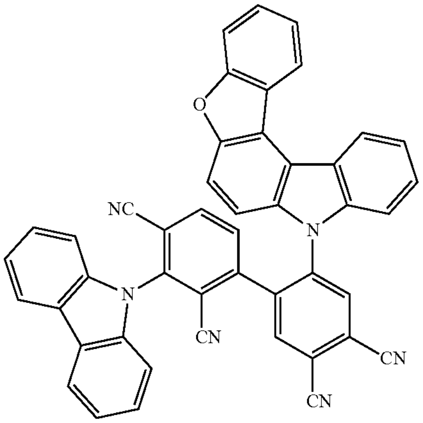
408
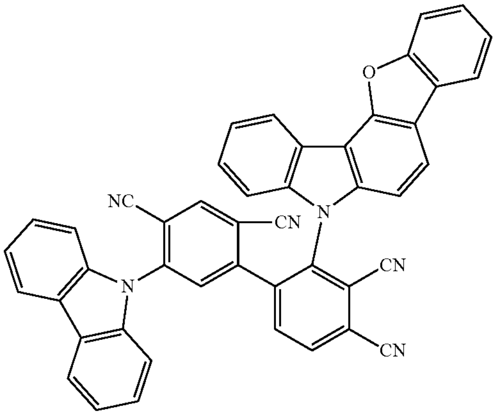

-continued
409
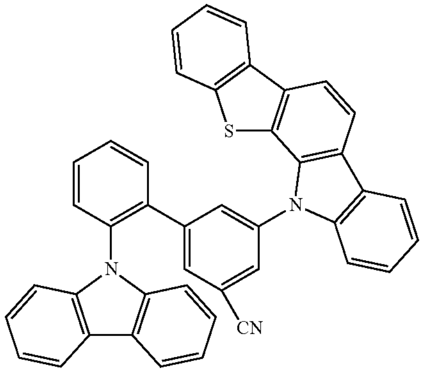
410
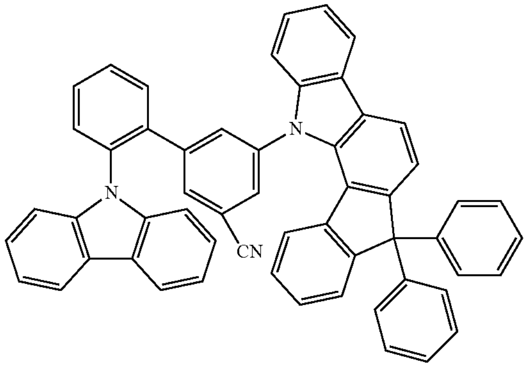
411
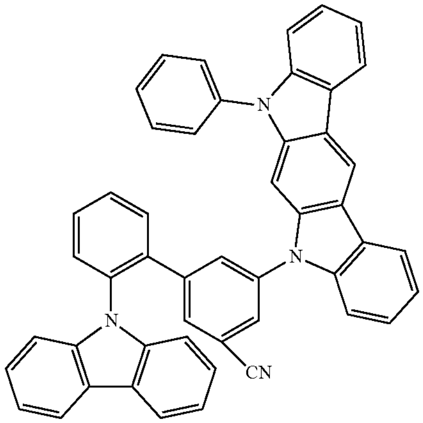
412
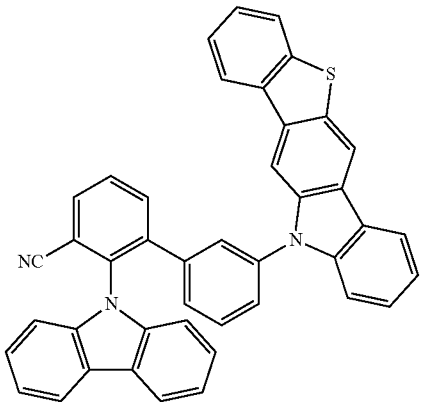
-continued
413
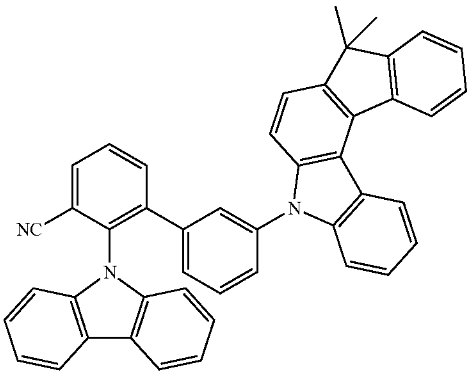
414
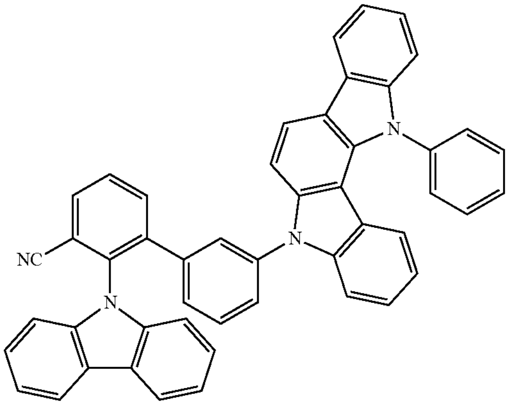
415
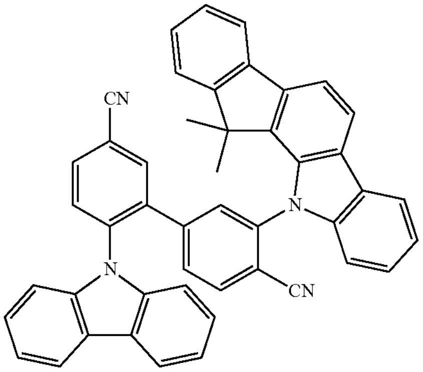
416
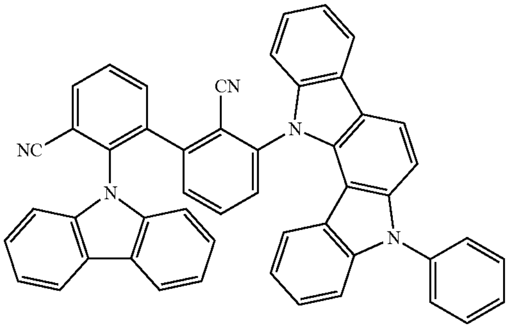

-continued
417
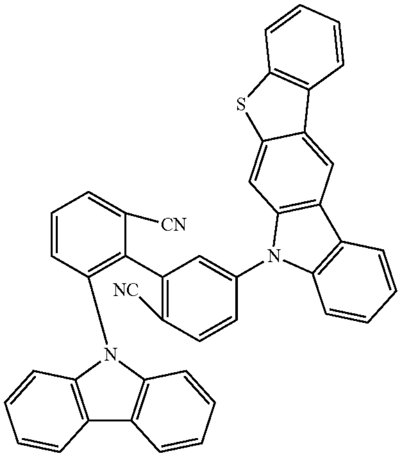
418
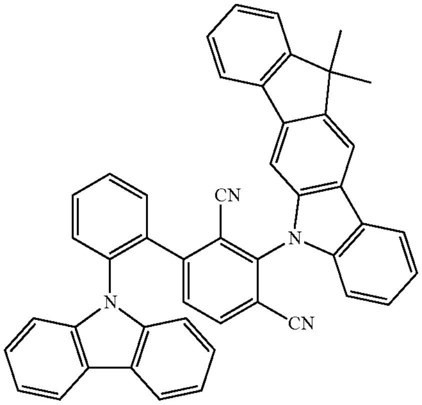
419
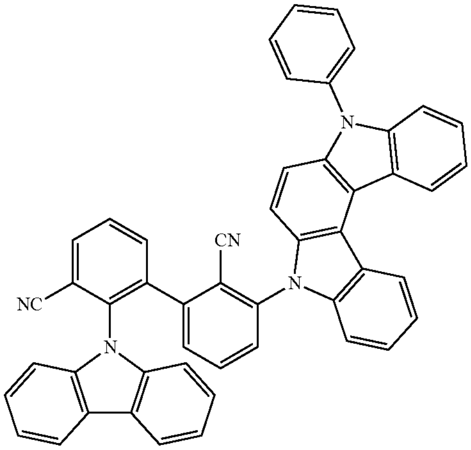
-continued
420
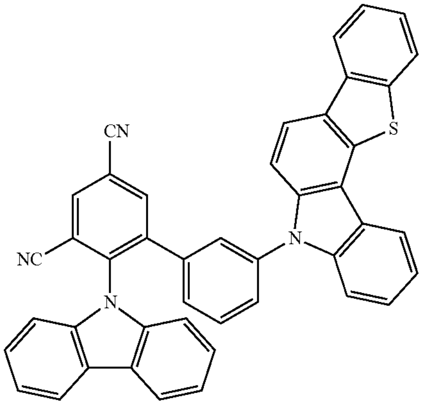
421
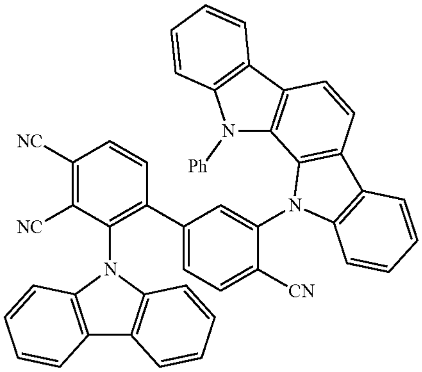
422
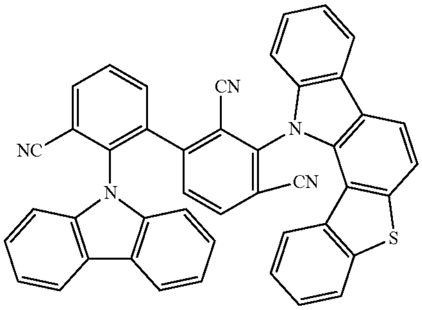
423
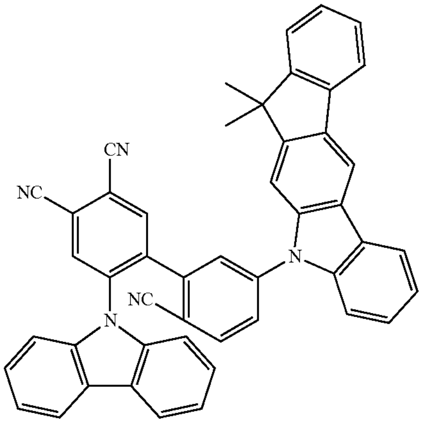

-continued
424
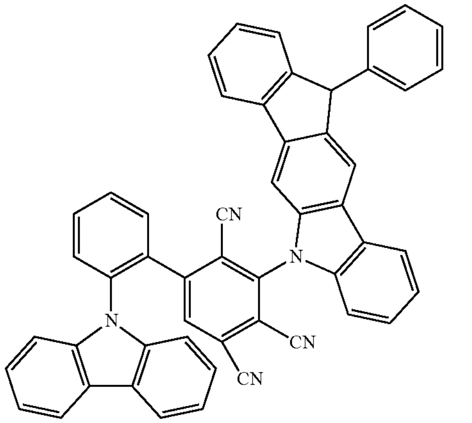
425
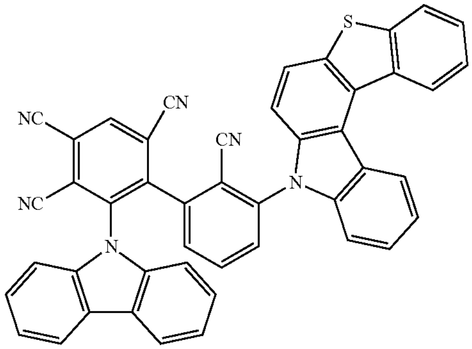
426
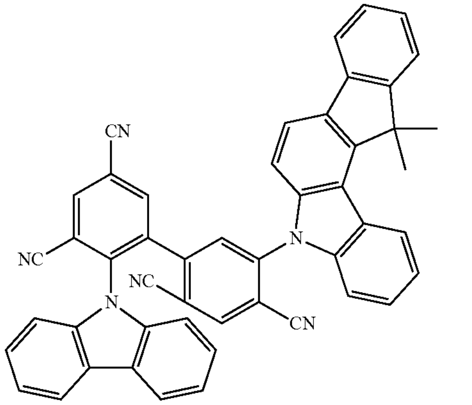
427
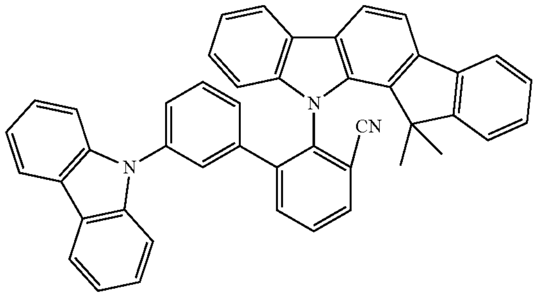
-continued
428
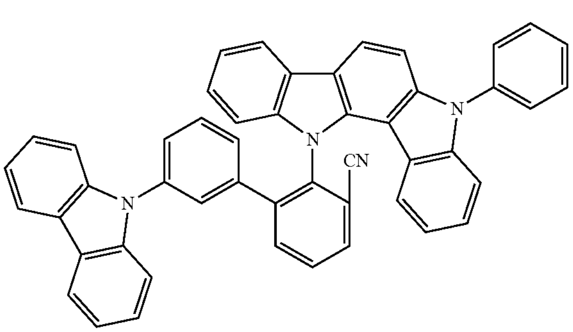
429
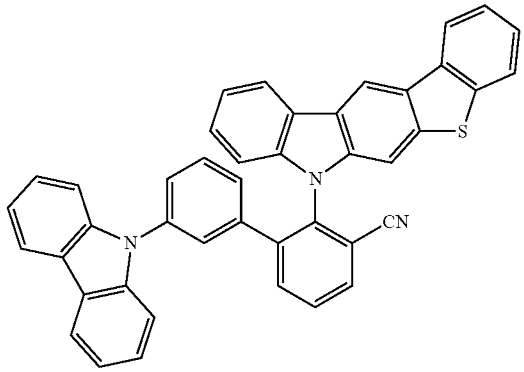
430
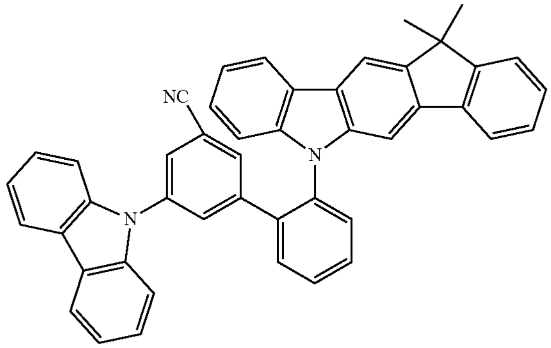
431
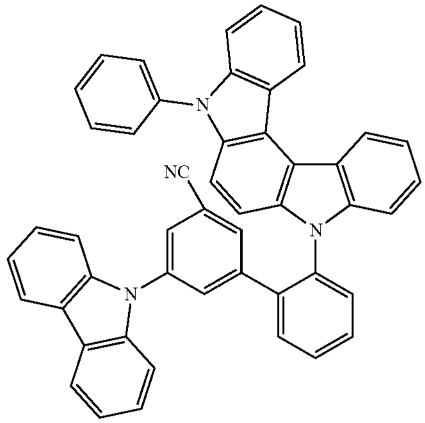

-continued
432
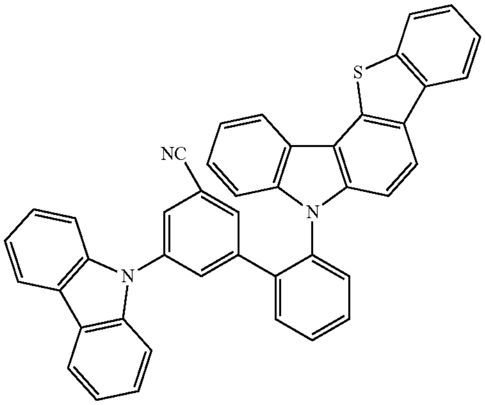
433
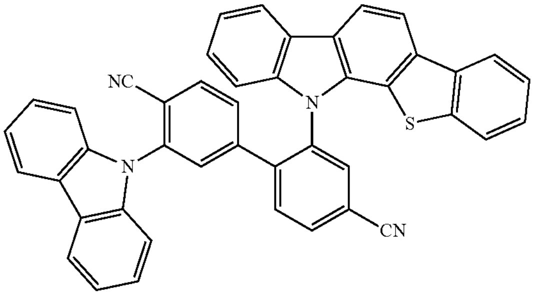
434
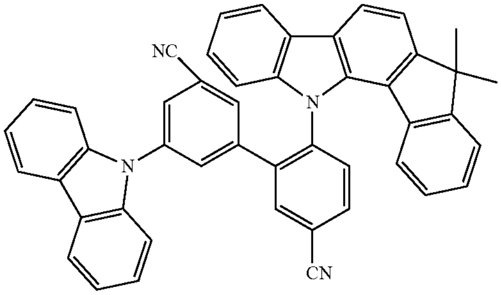
435
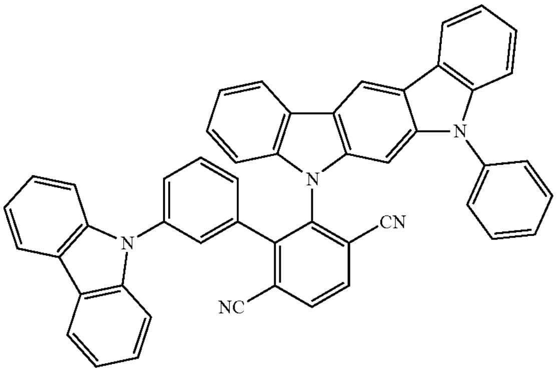
-continued
436
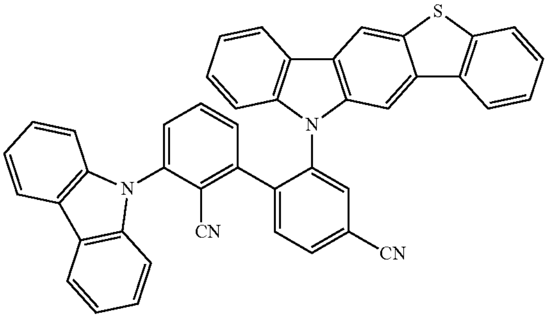
437
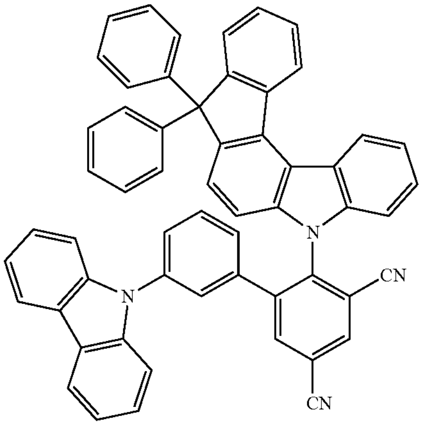
438
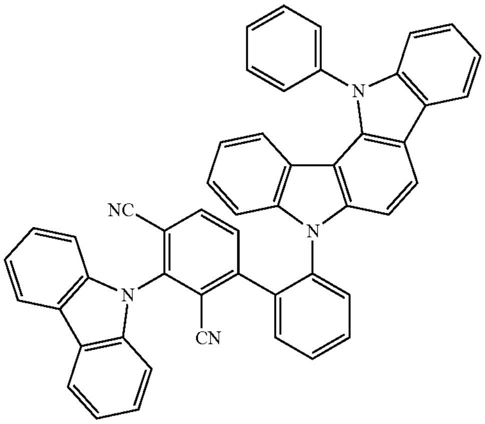
439
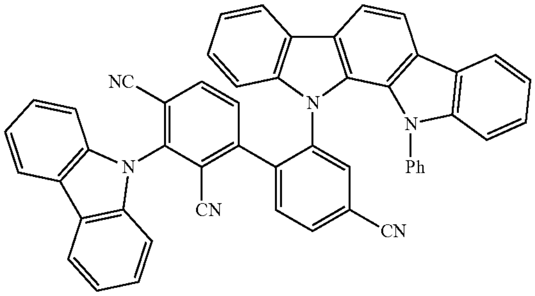

-continued
440
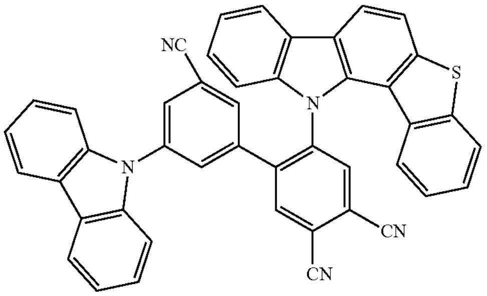
441
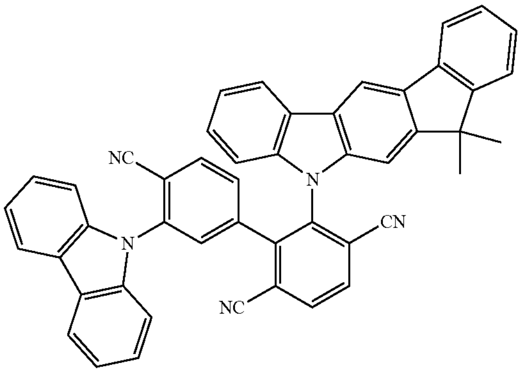
442
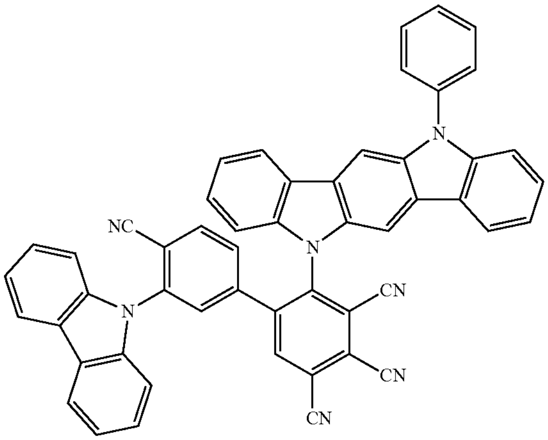
443
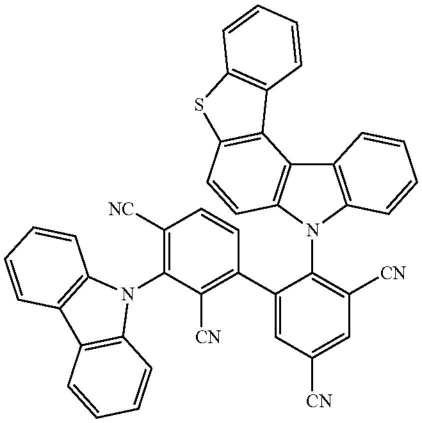
-continued
444
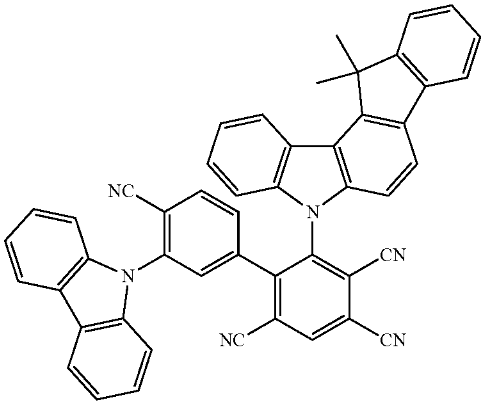
445
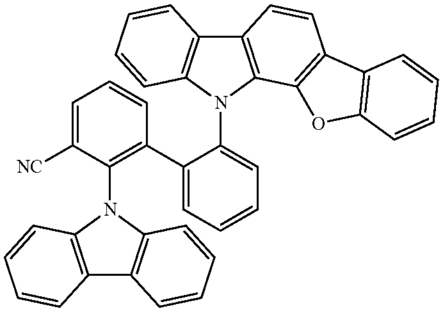
446
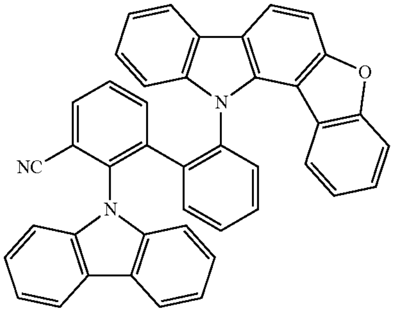
447
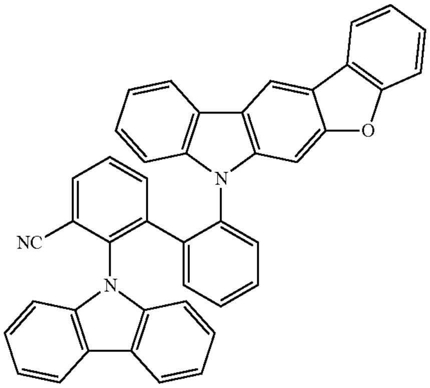

-continued
448
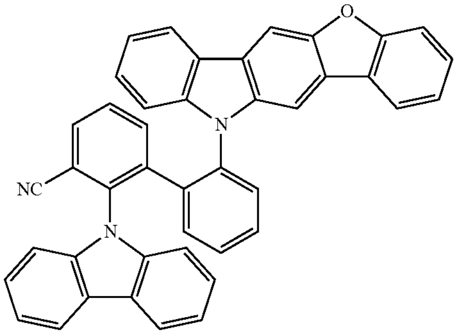
449
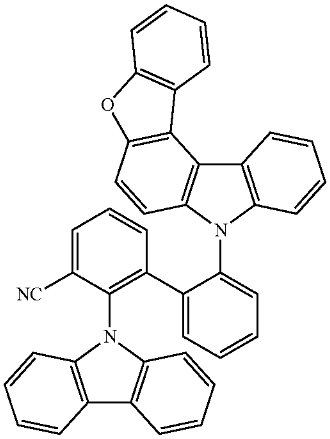
450
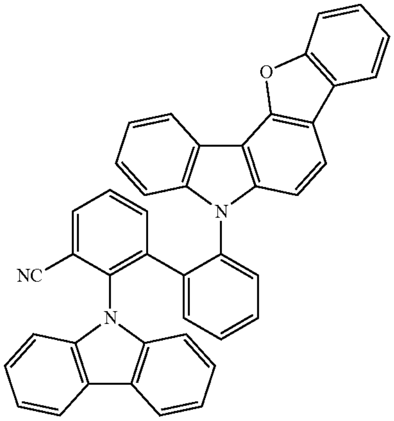
451
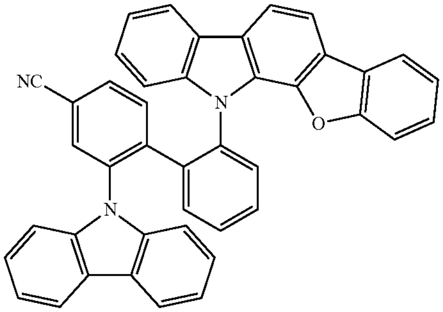
-continued
452
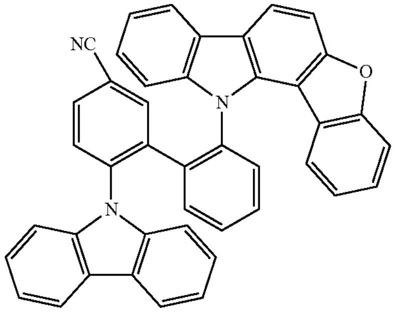
453
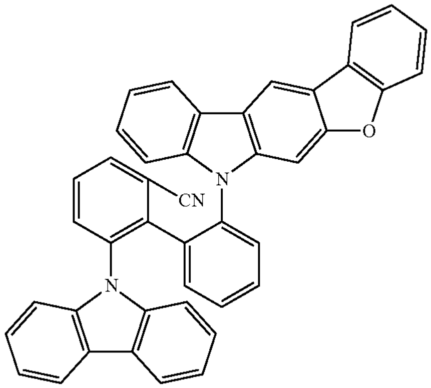
454
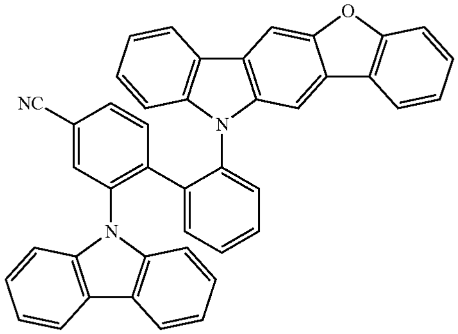
455
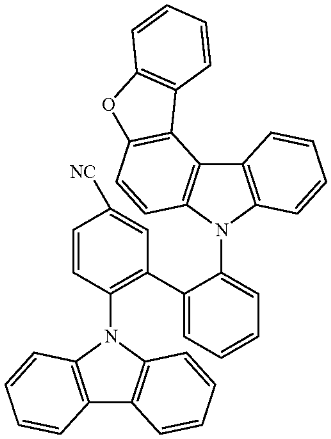

-continued
456
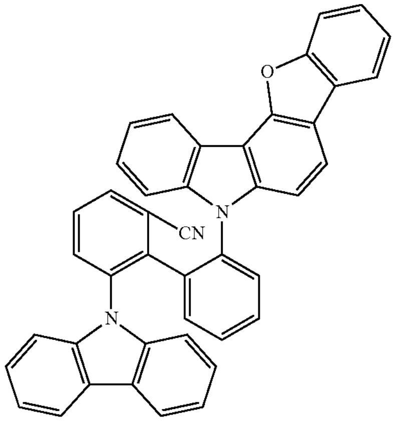
457
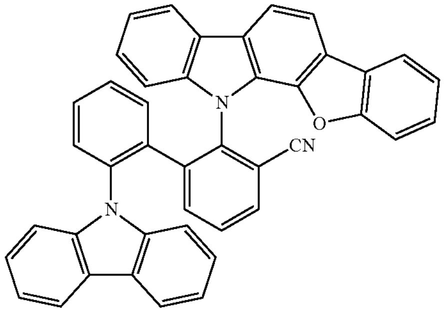
458
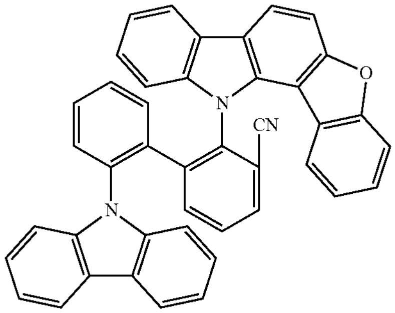
459
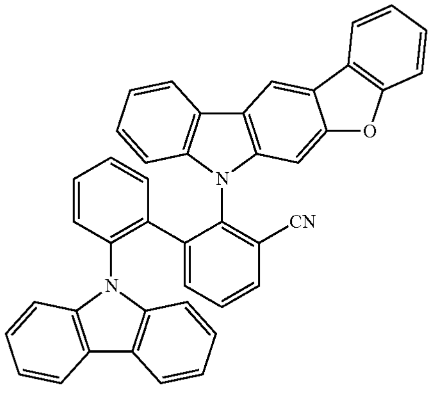
-continued
460
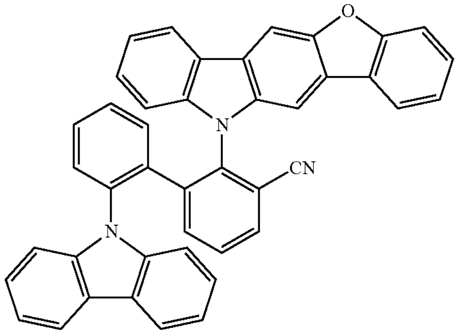
461
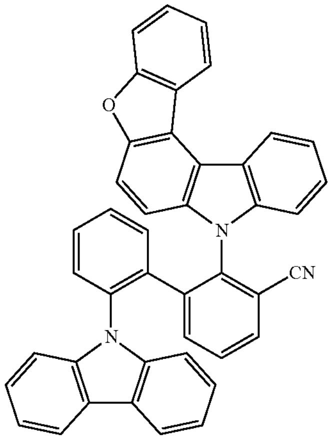
462
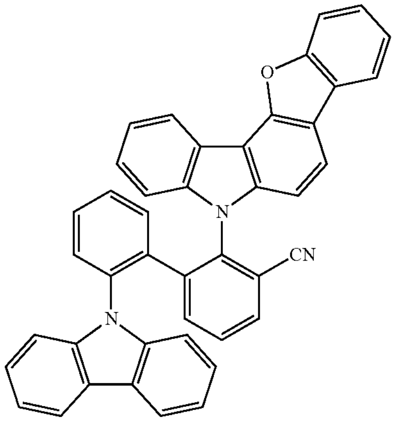
463
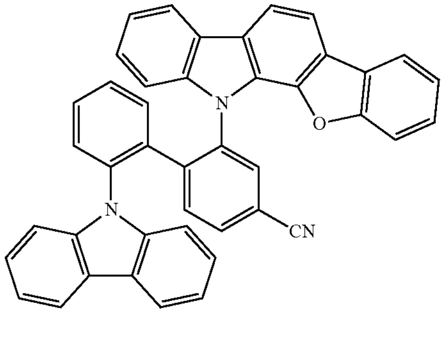

-continued
464
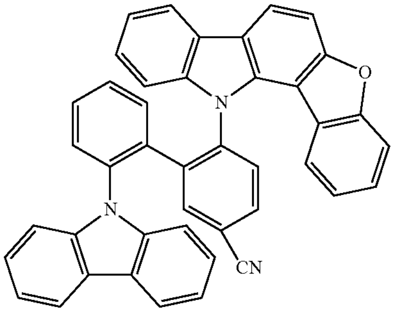
465
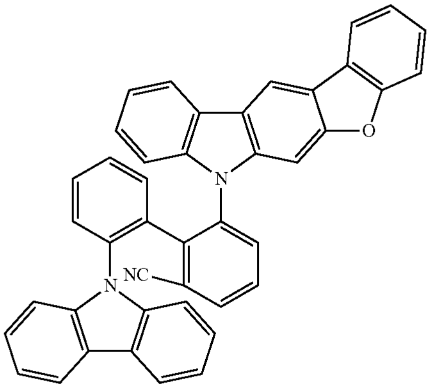
466
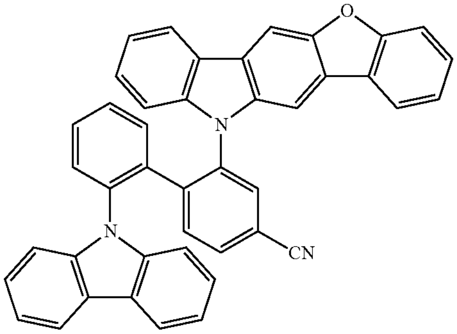
467
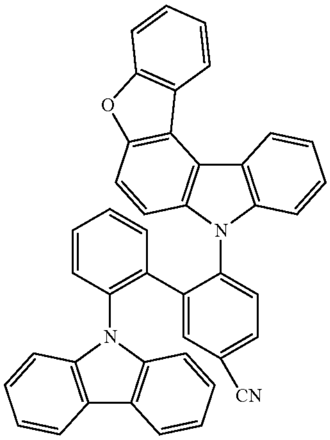
-continued
468
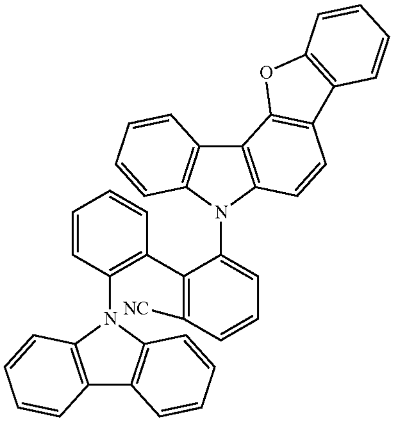
469
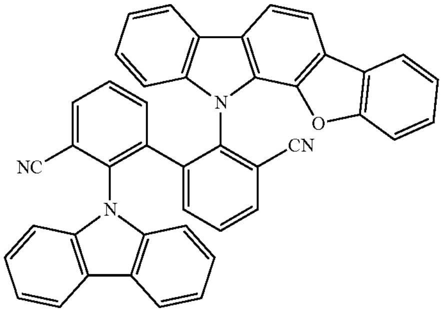
470
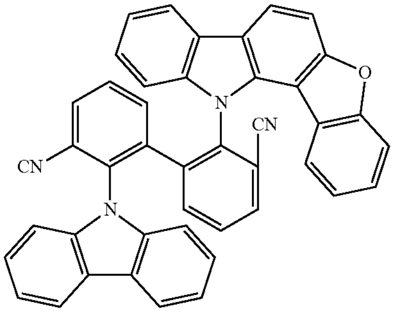
471
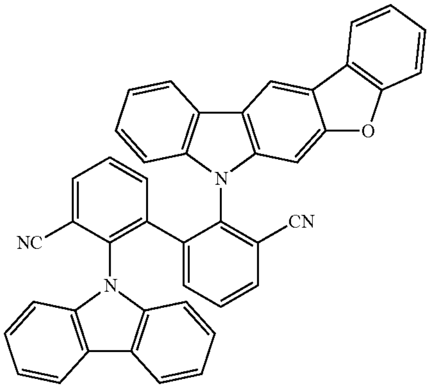

-continued
472
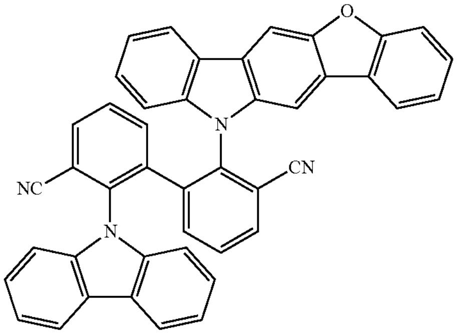
473
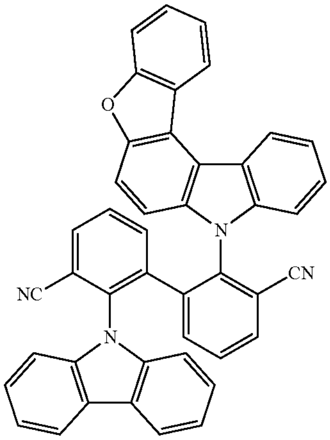
474
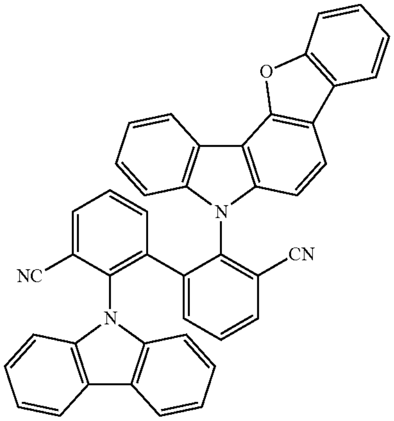
475
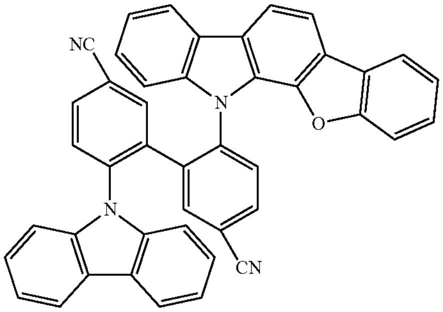
-continued
476
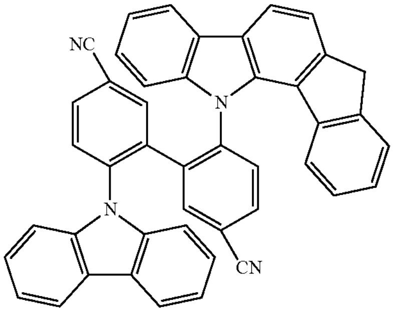
477
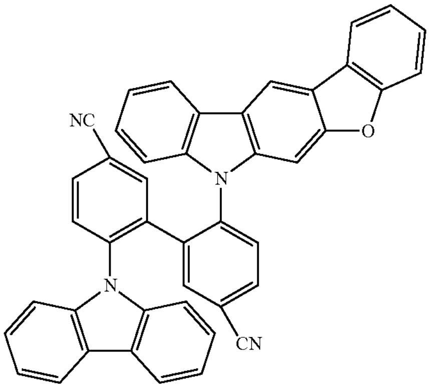
478
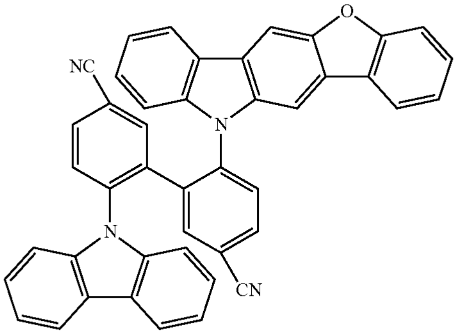
479
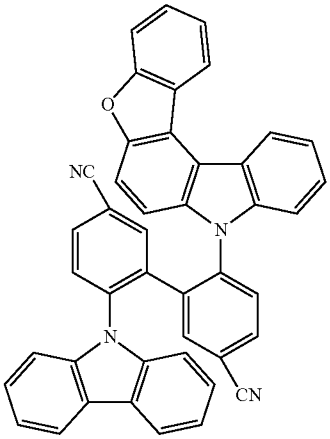

-continued
480
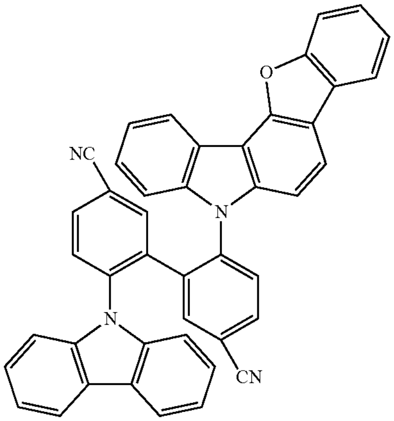
481
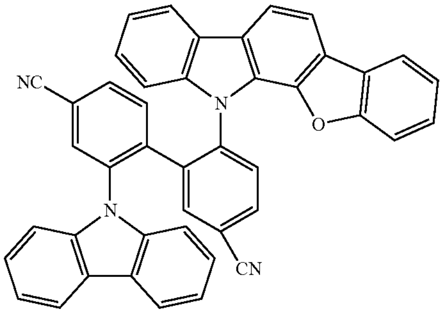
482
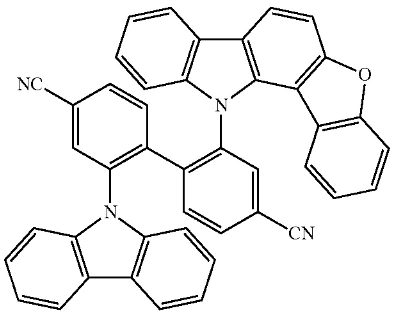
483
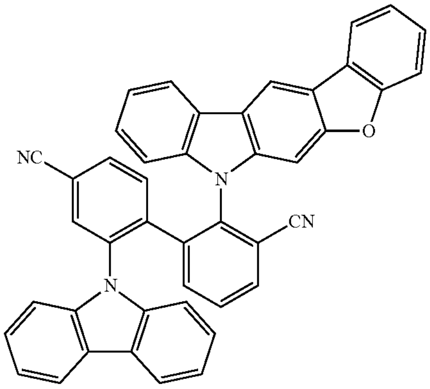
-continued
484
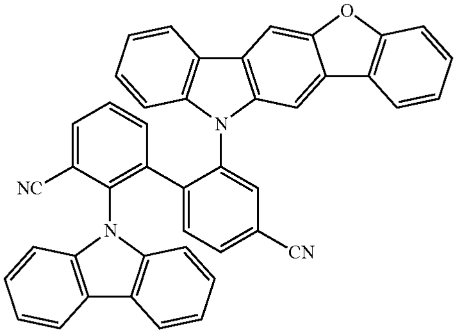
485
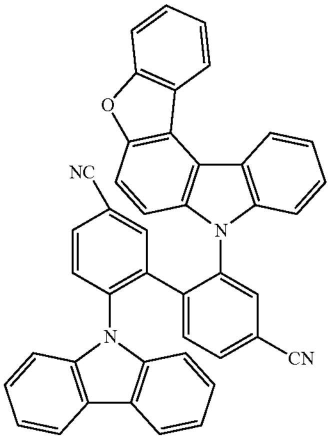
486
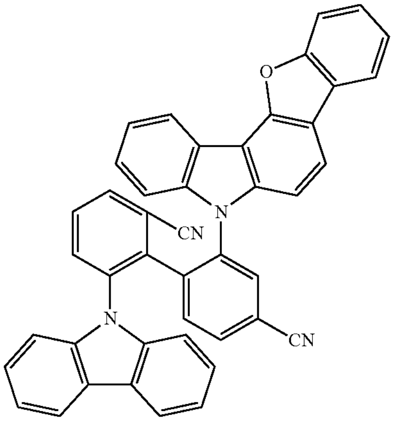
487
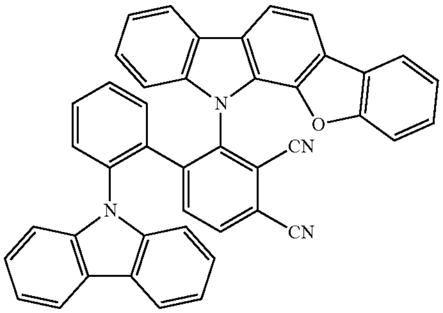

-continued
488
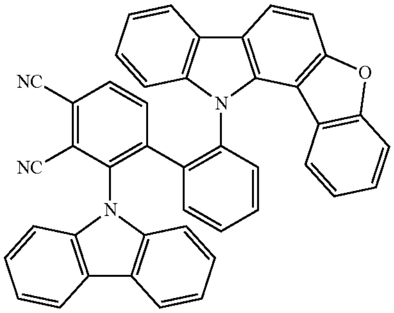
489
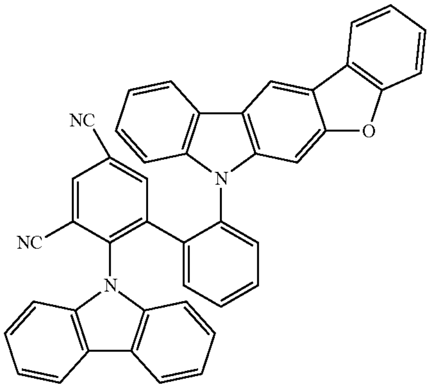
490
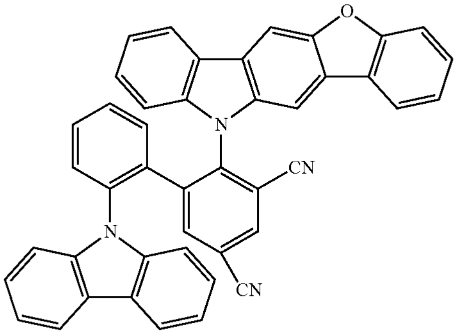
491
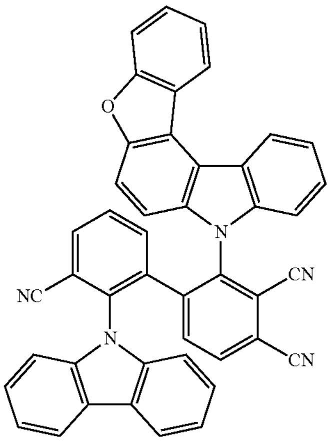
-continued
492
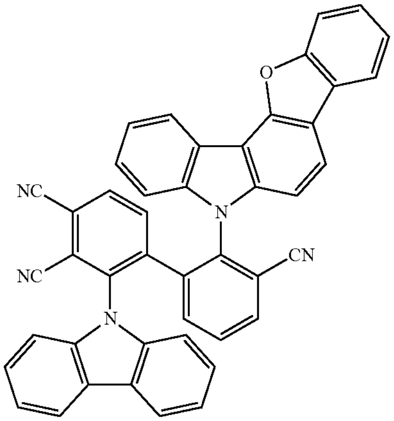
493
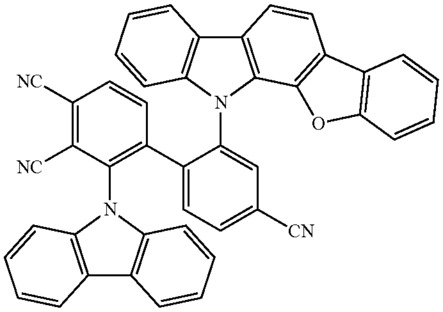
494
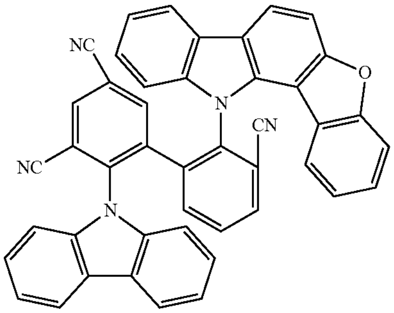
495
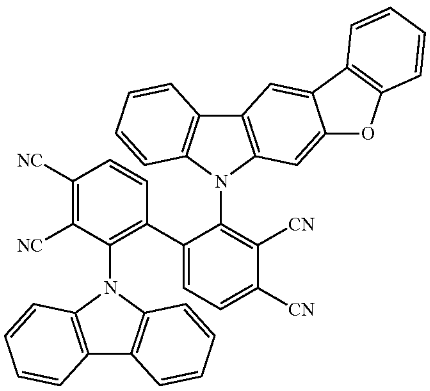

-continued
496
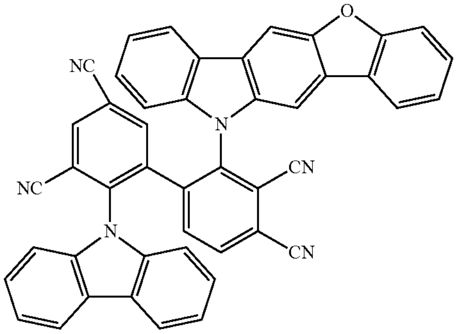
497
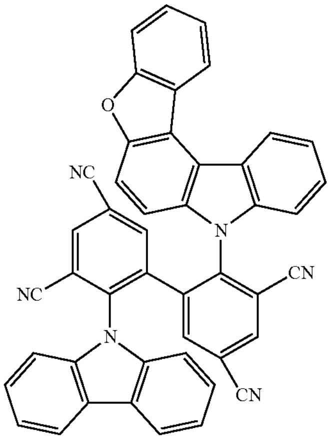
498
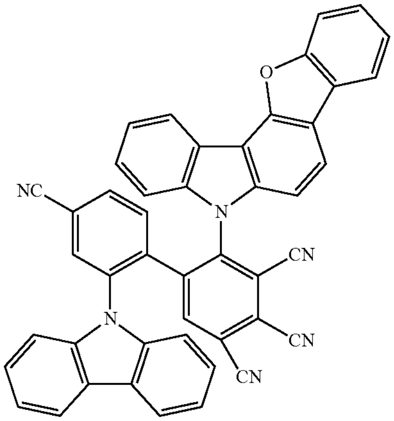
499
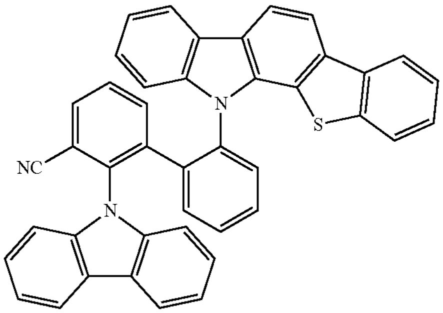
-continued
500
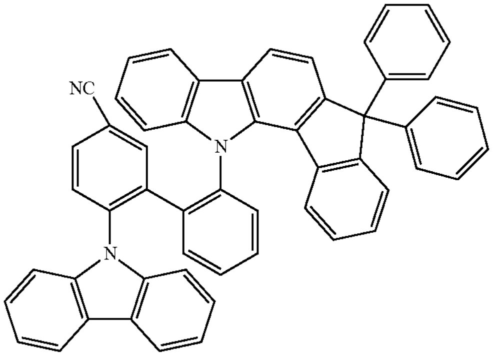
501
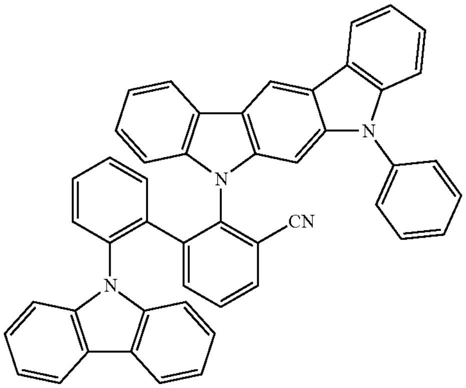
502
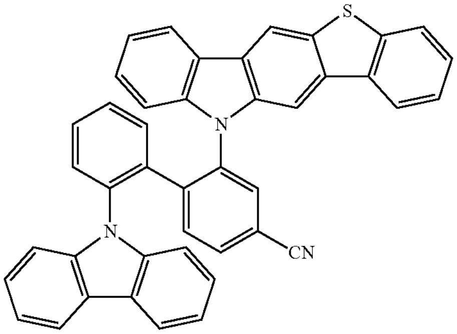
503
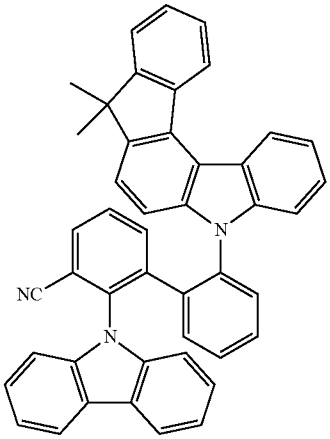

504
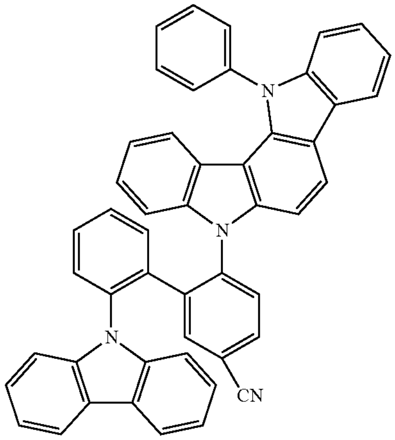
505
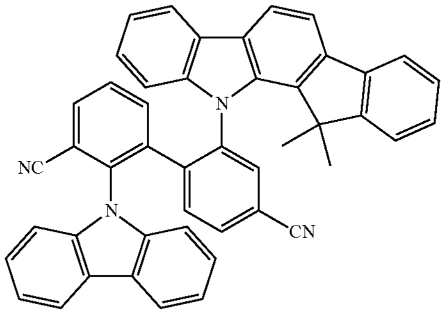
506
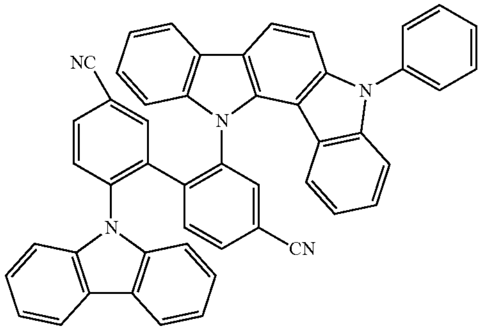
507
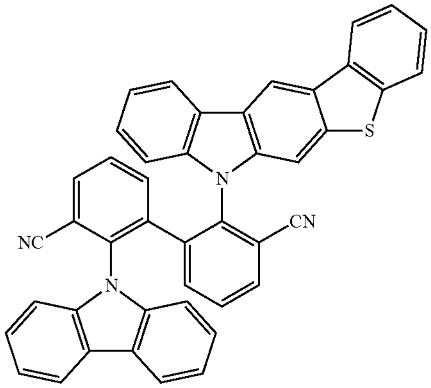
508
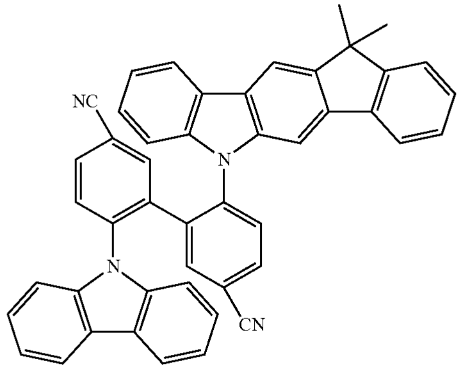
509
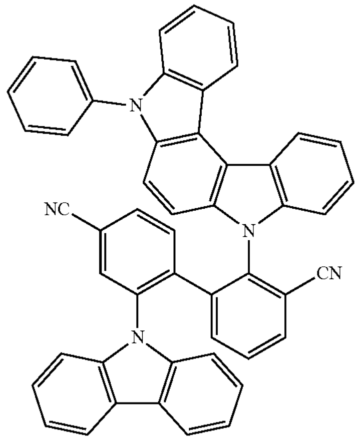
510
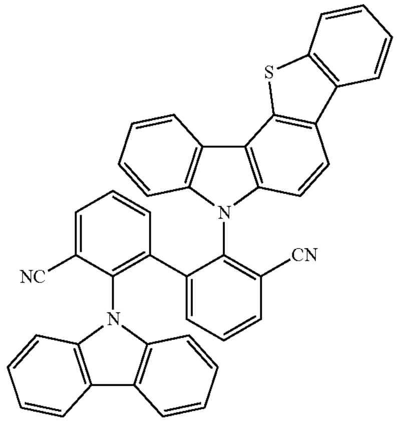
511
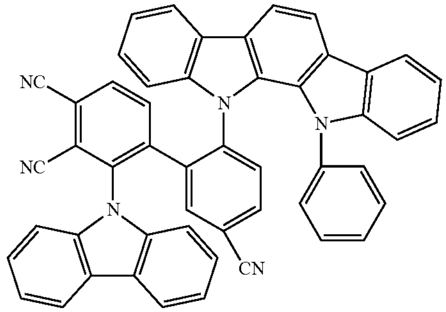

-continued
512
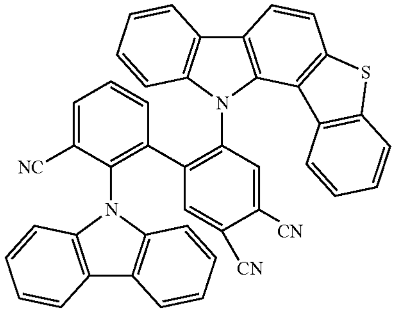
513
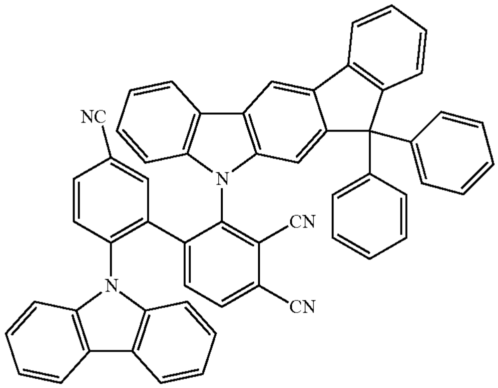
514
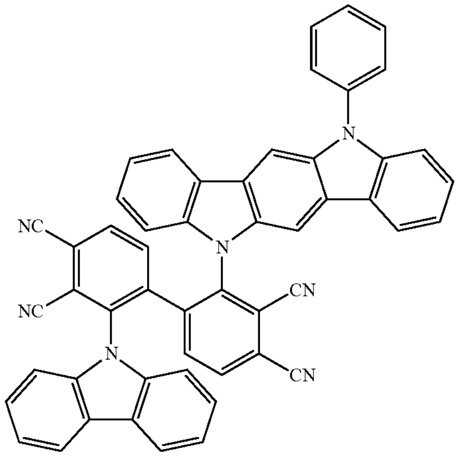
515
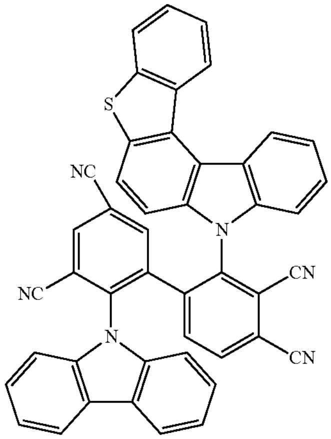
-continued
516
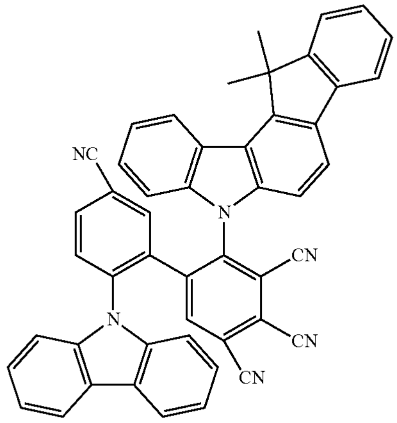
517
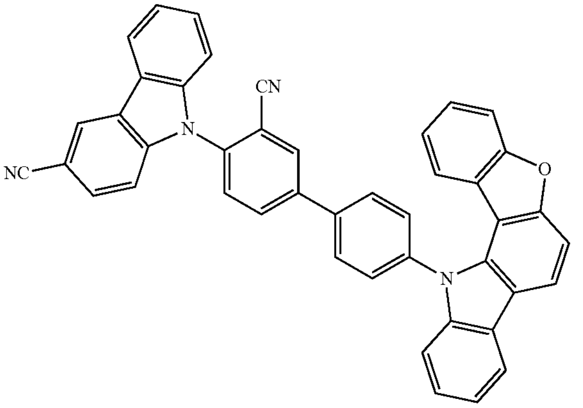
518
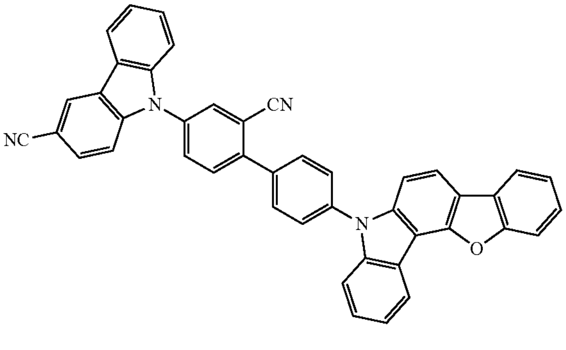

-continued
519
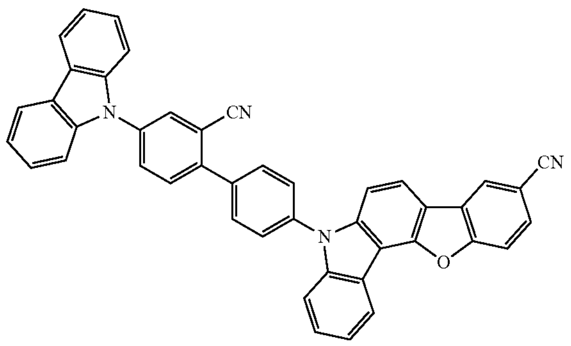
520
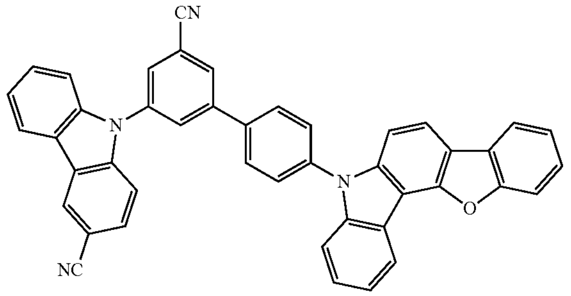
521
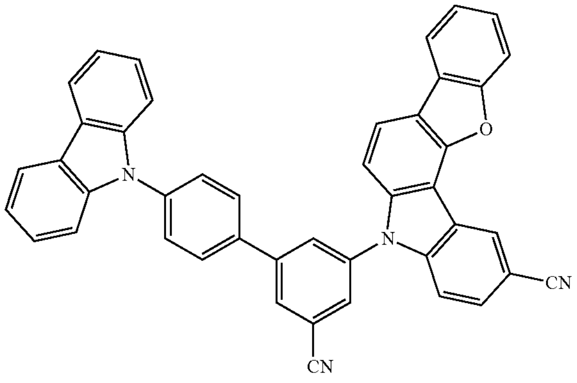
522
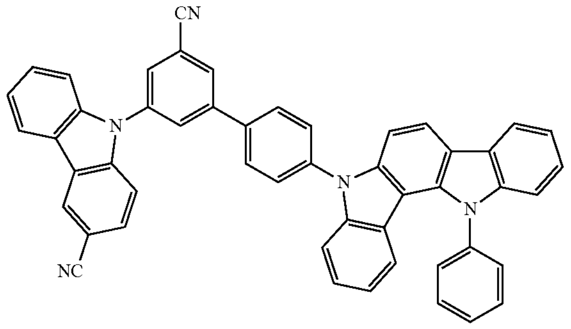
-continued
523
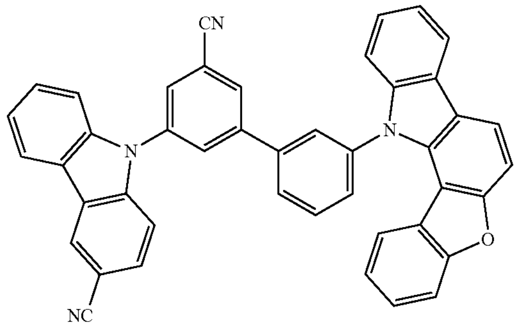
524
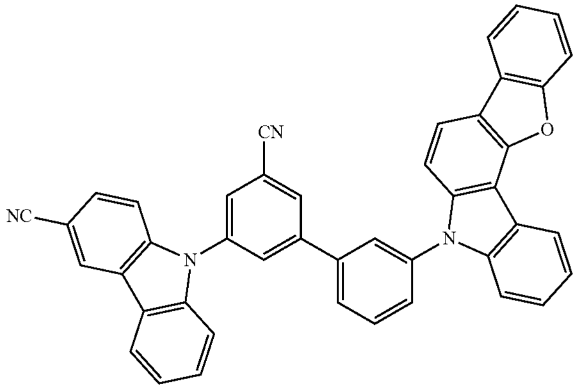
525
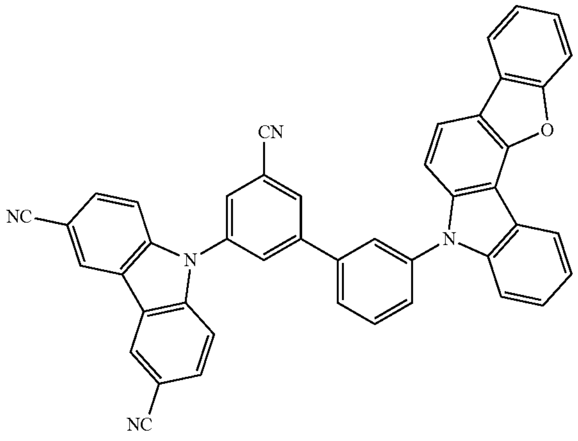
526
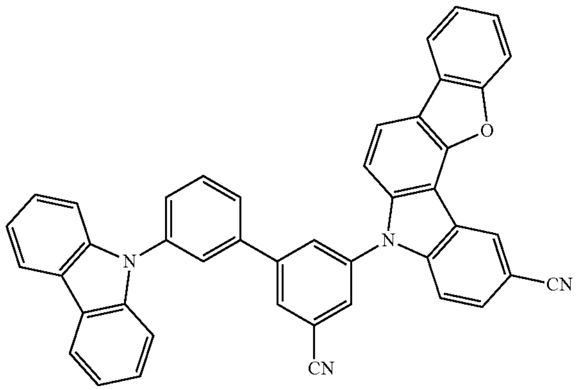

-continued
527
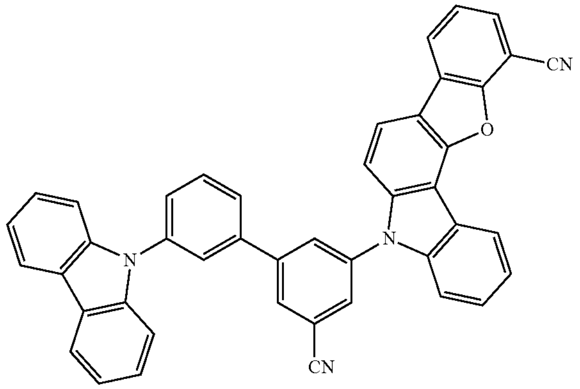
528
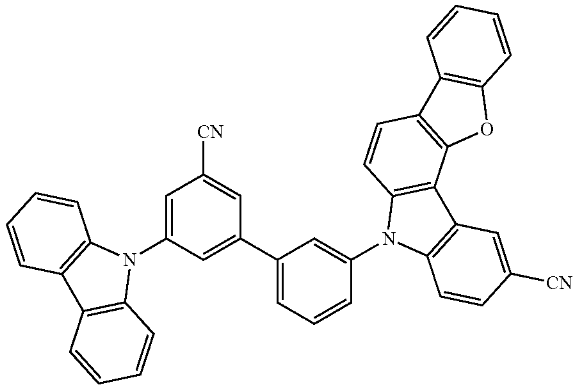
529
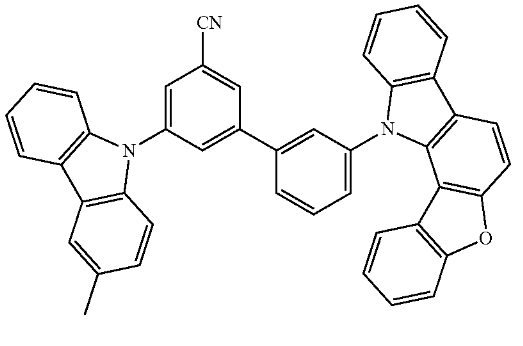
530
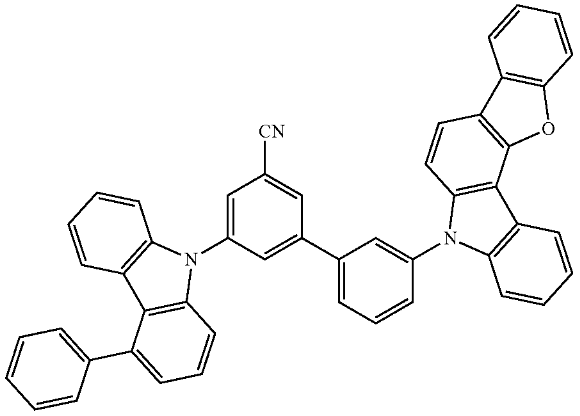
-continued
531
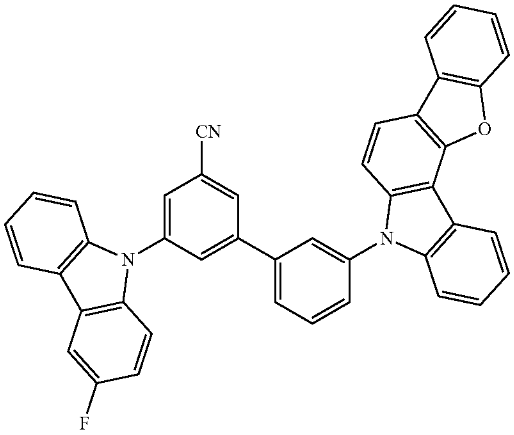
532
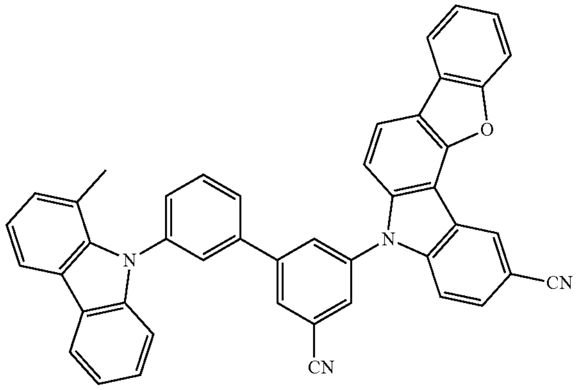
533
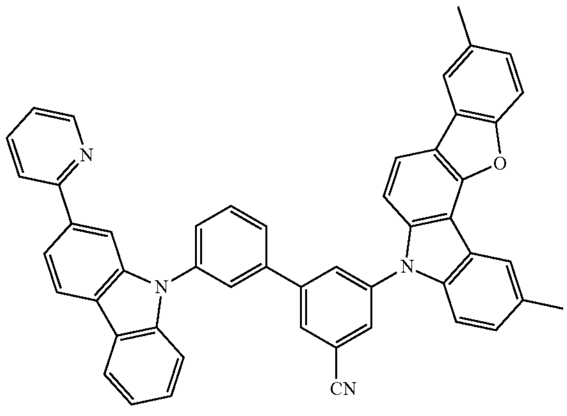
534
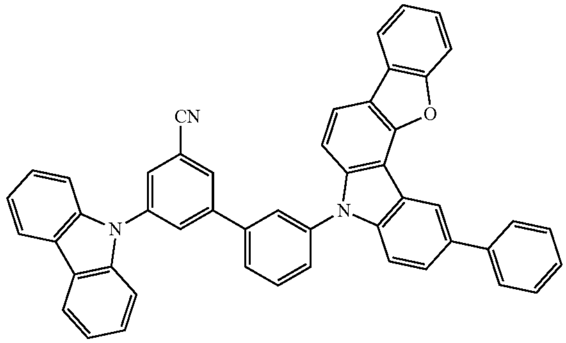

-continued
535
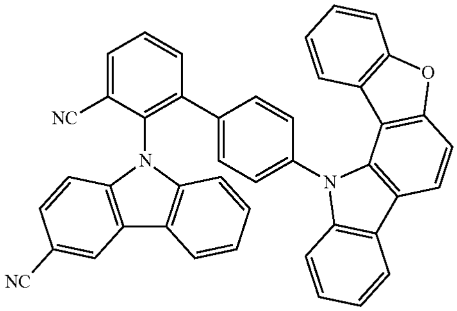
536
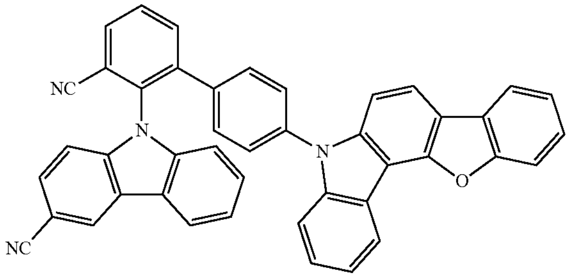
537
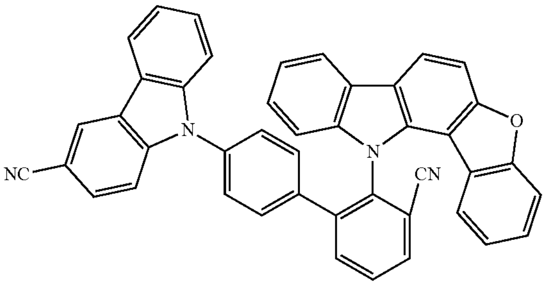
538
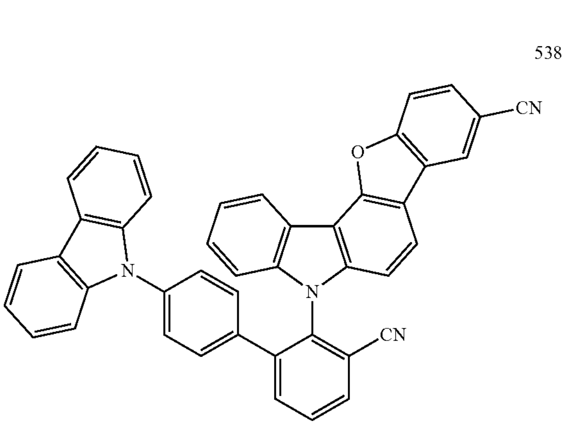
-continued
539
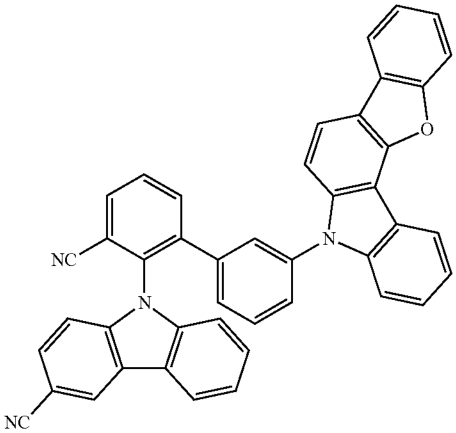
540
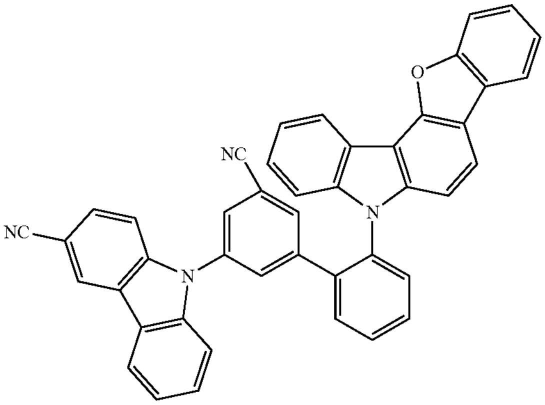
541
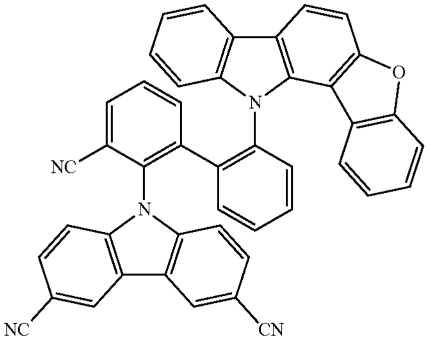

-continued
542
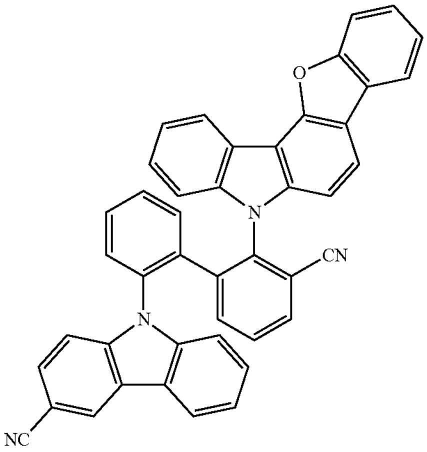
543
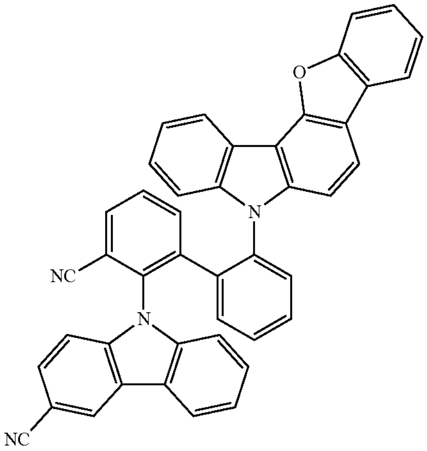
544
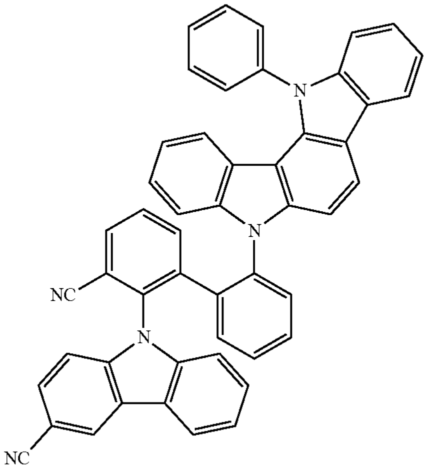
-continued
545
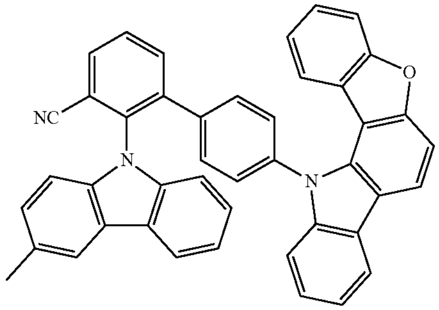
546
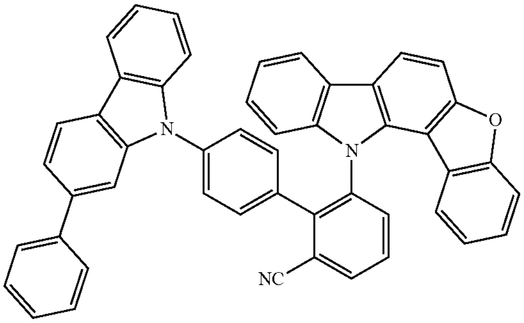
547
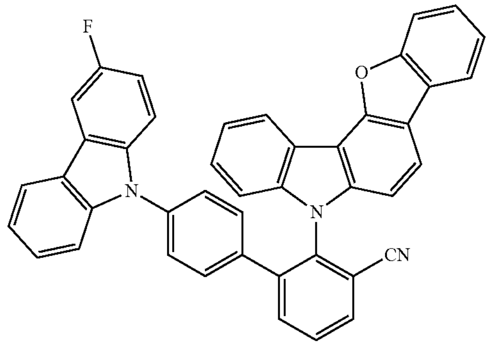
548
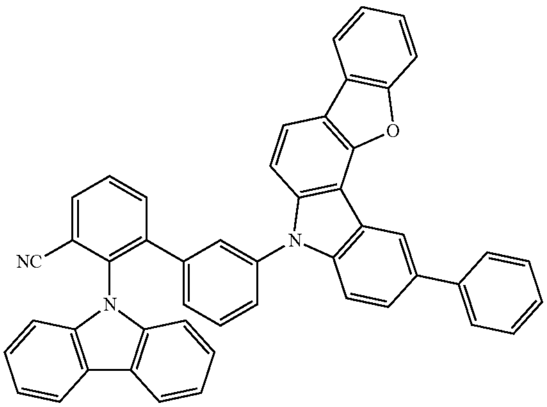

-continued
549
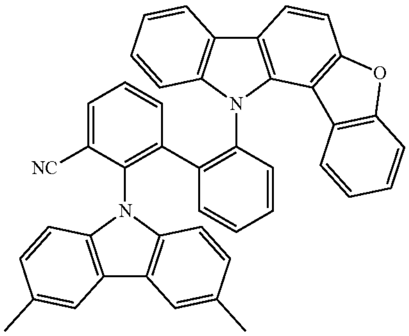
550
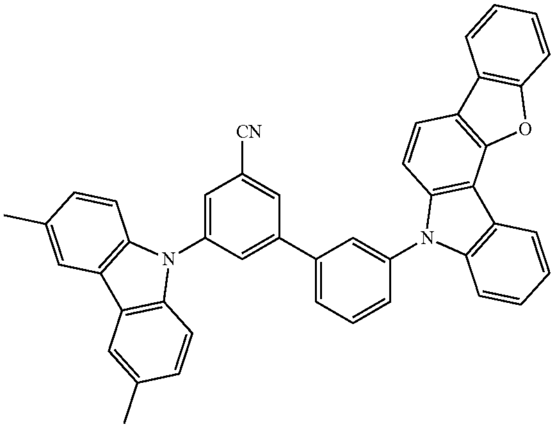
551
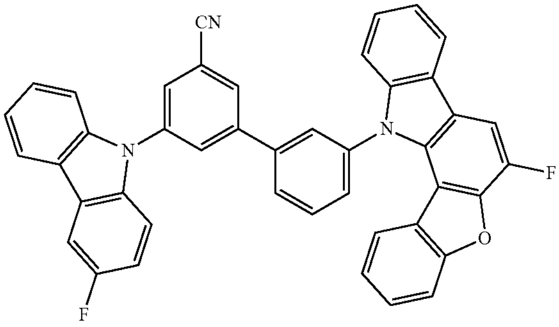
552
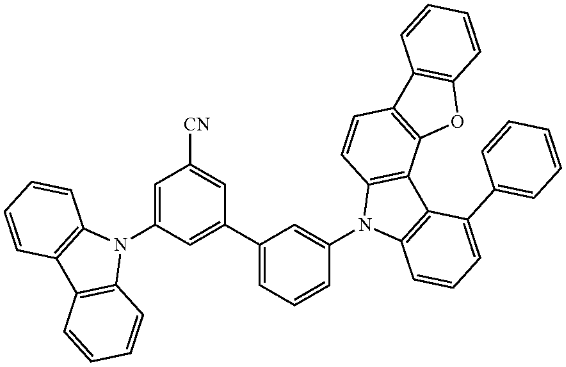
-continued
553
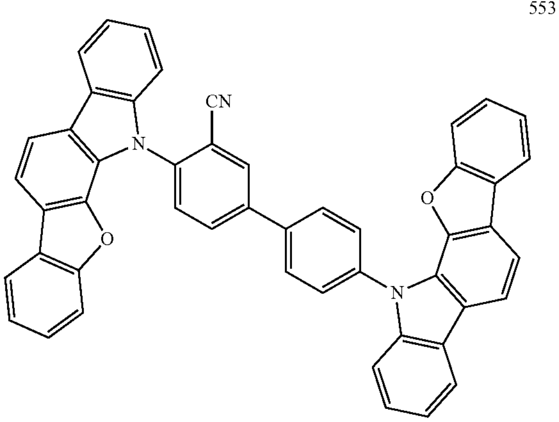
554
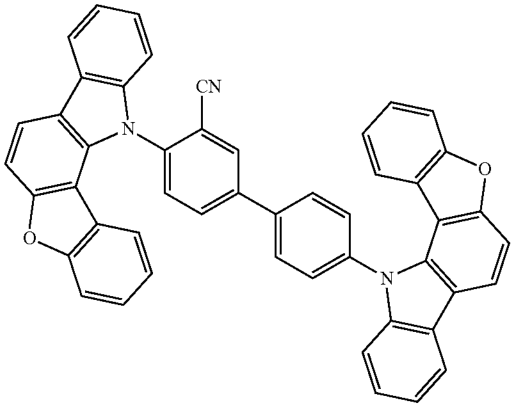
555
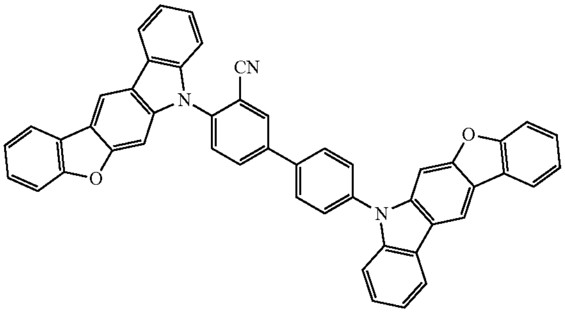
556
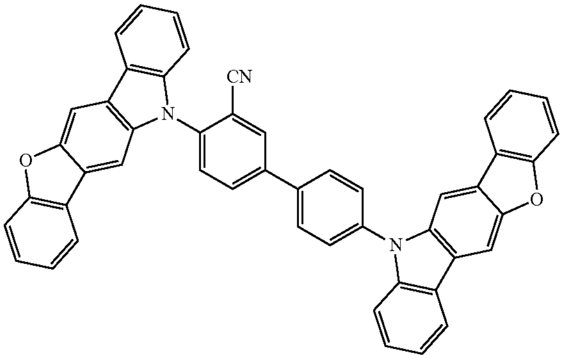

-continued
557
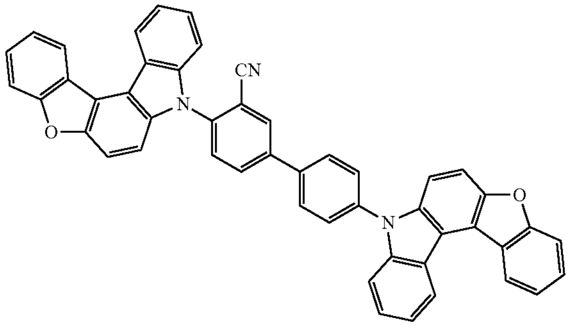
558
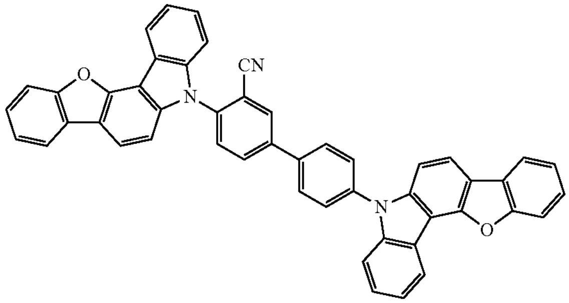
559
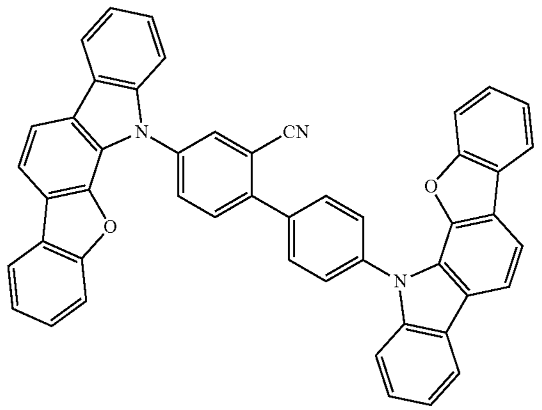
560
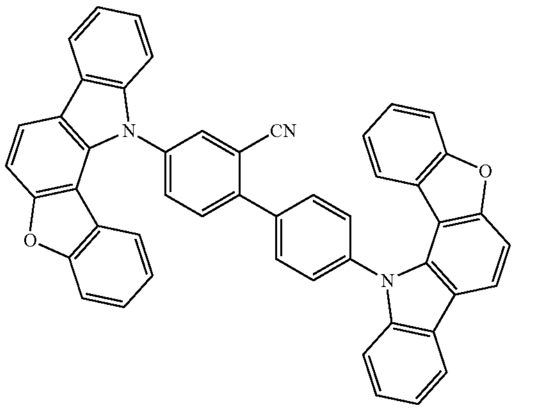
-continued
561
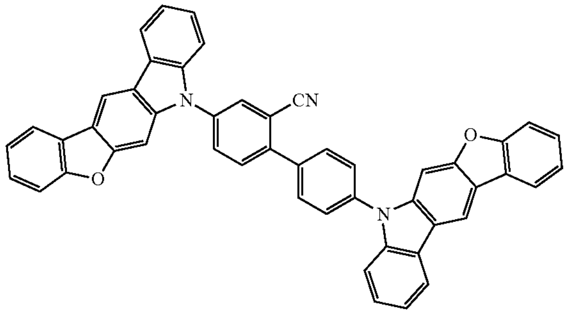
562
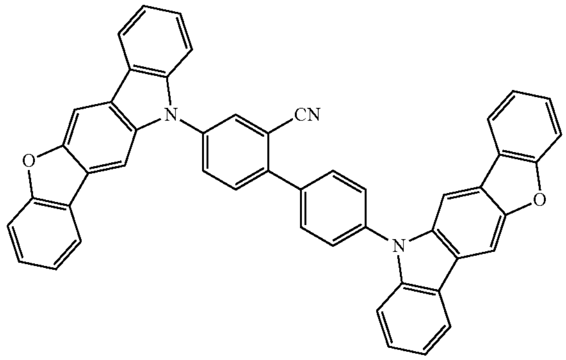
563
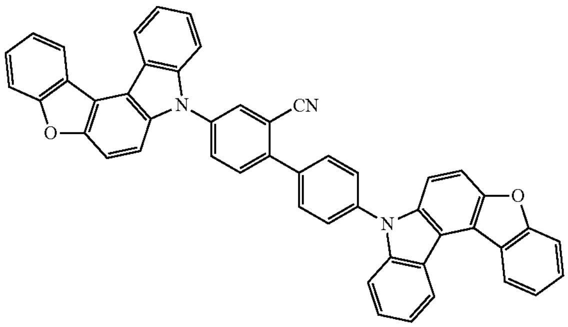
564
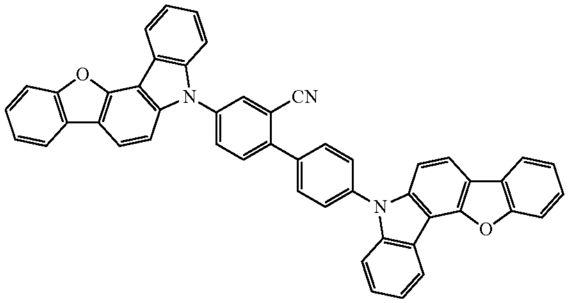

-continued
565
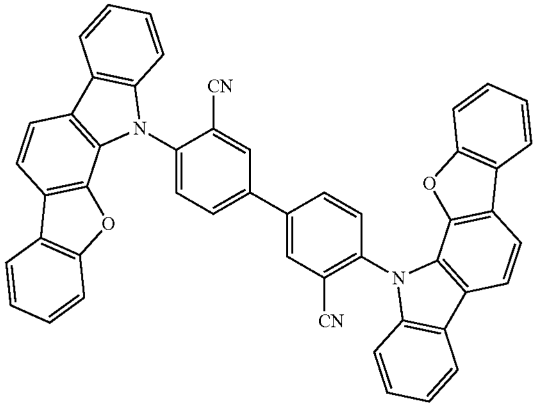
566
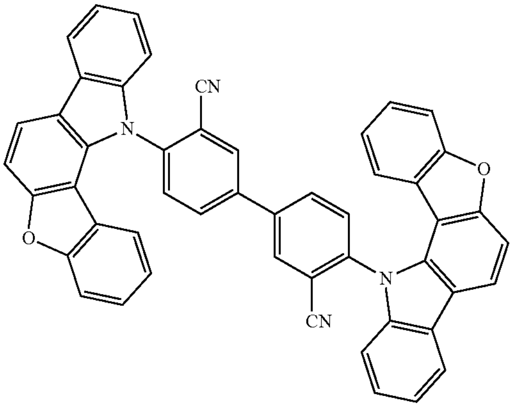
567
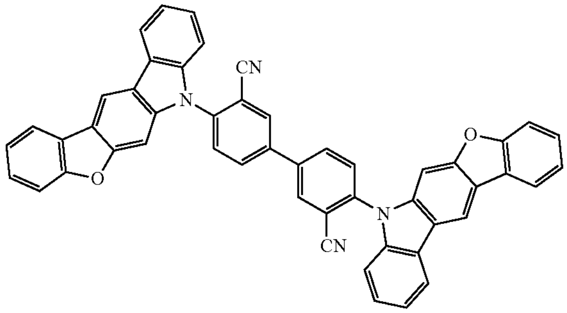
568
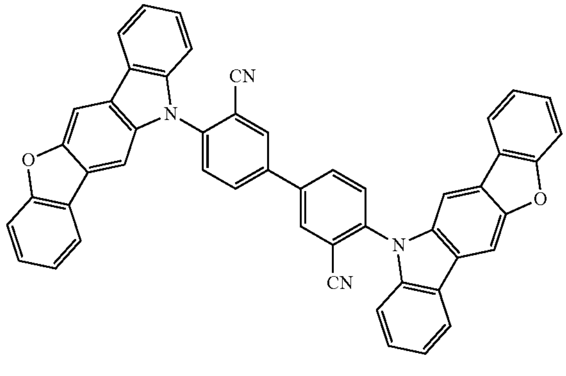
-continued
569
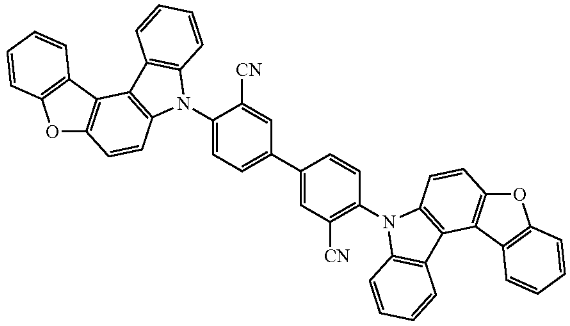
670
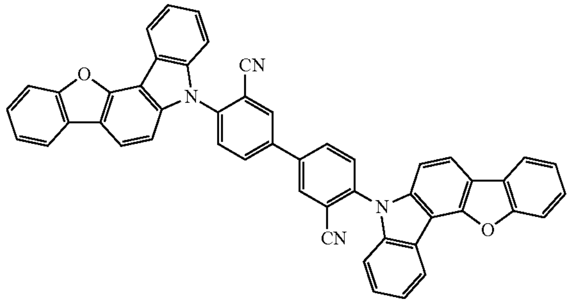
571
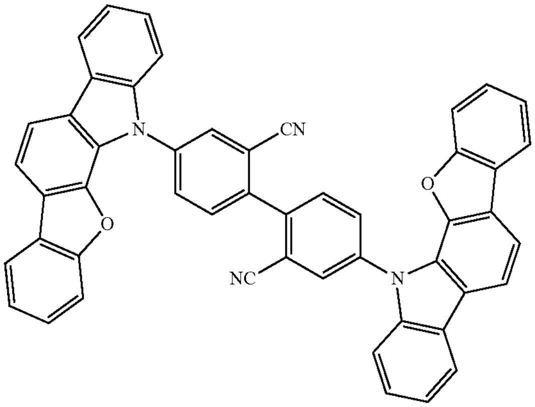
572
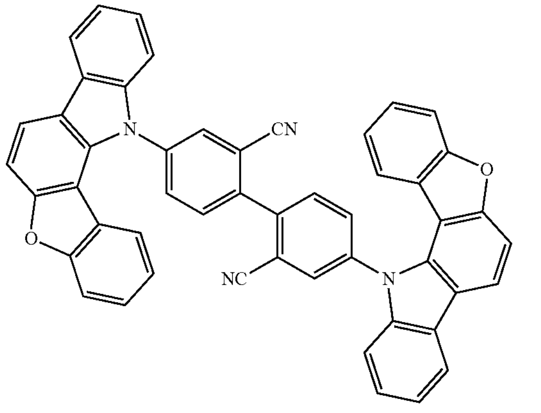

-continued
573
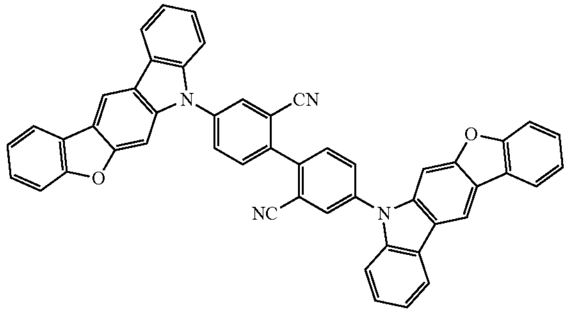
574
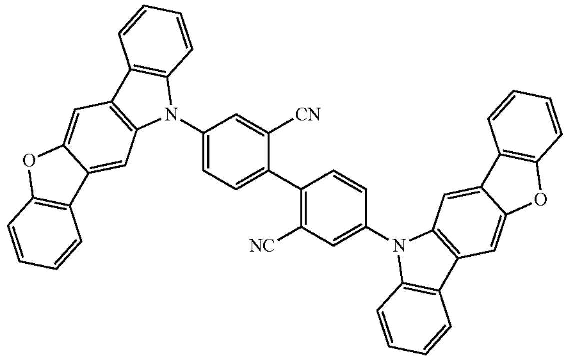
575
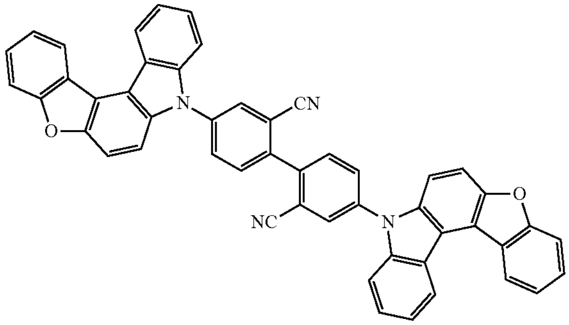
576
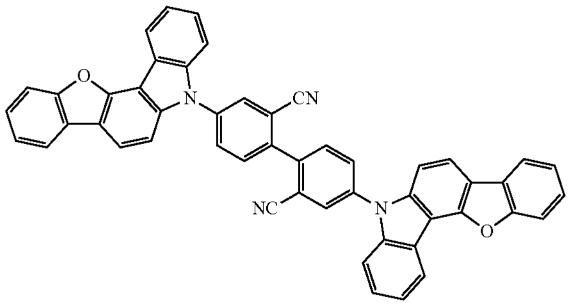
-continued
577
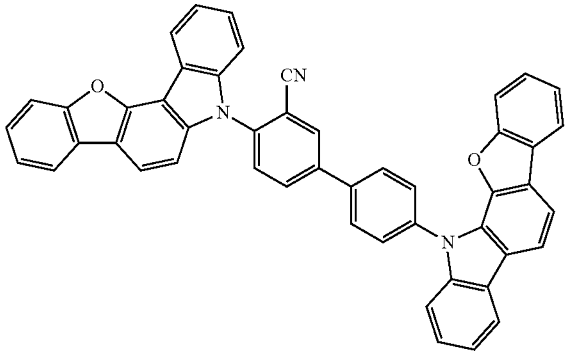
578
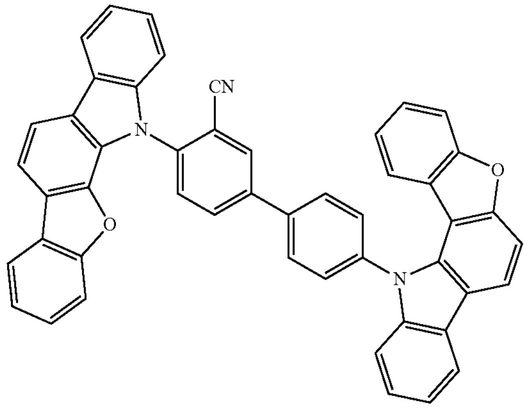
579
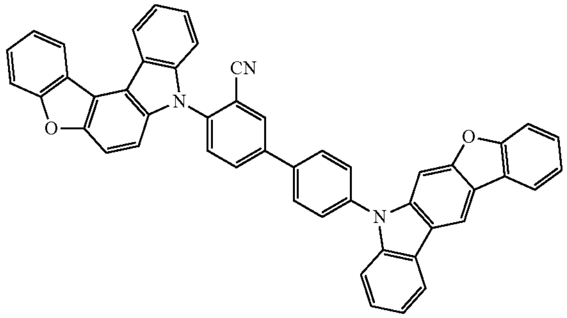
580
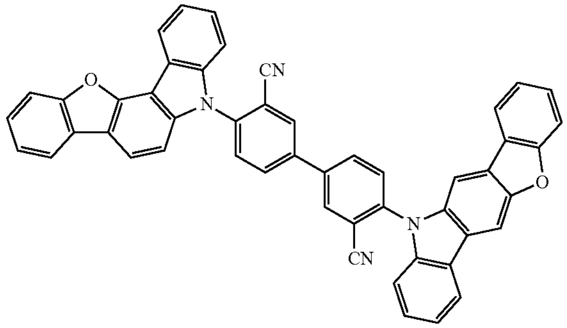

-continued
581
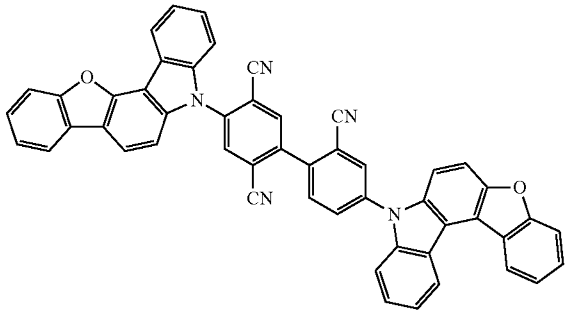
582
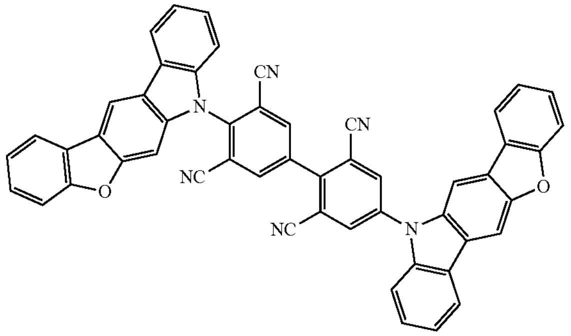
583
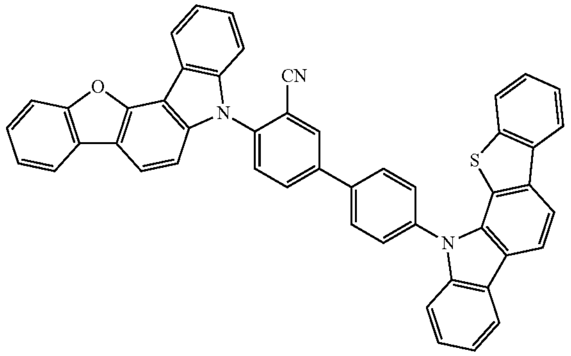
584
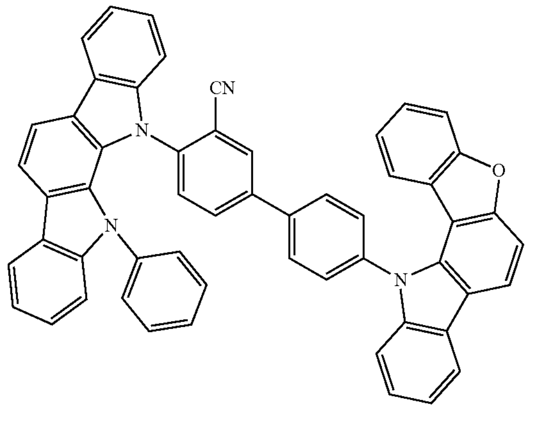
-continued
585
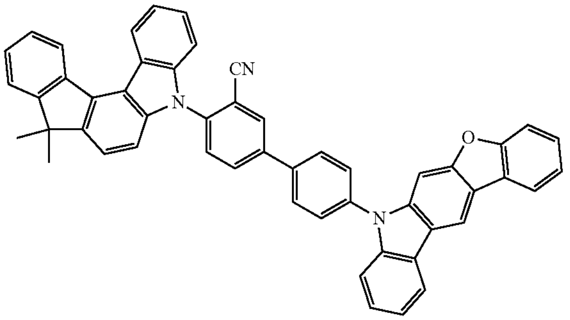
586
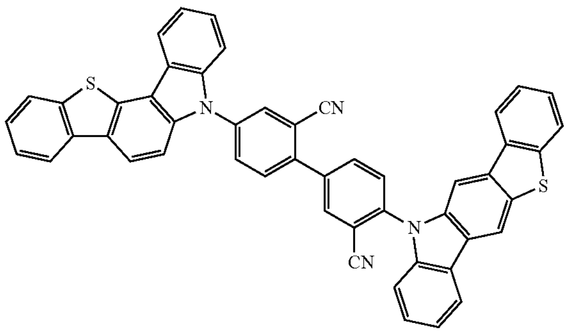
587
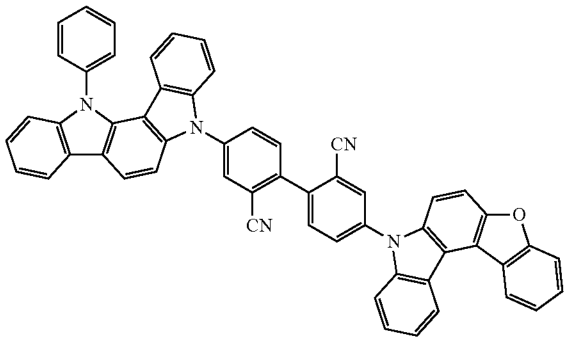
588
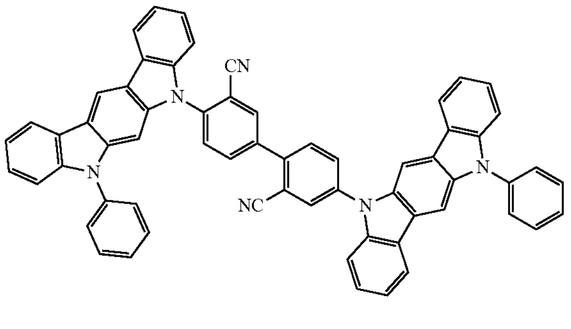

-continued
589
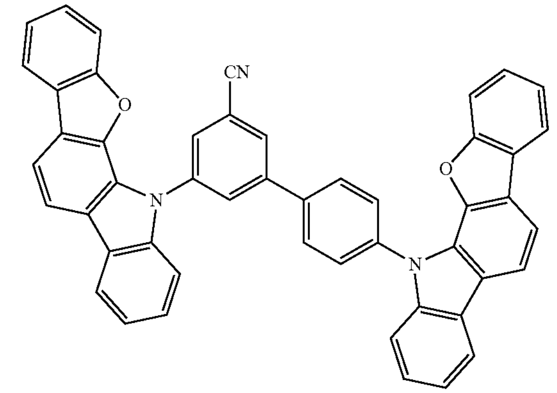
590
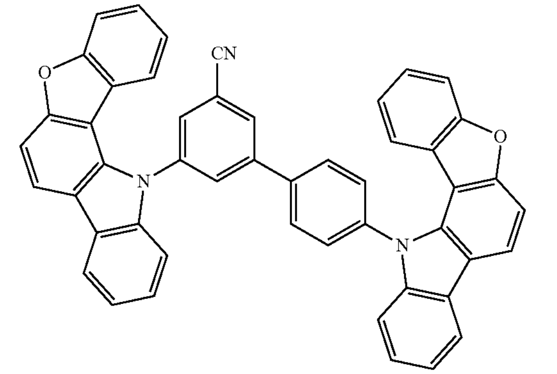
591
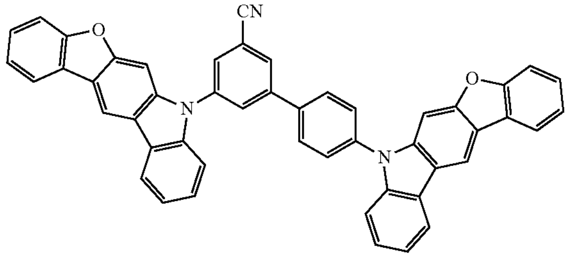
592
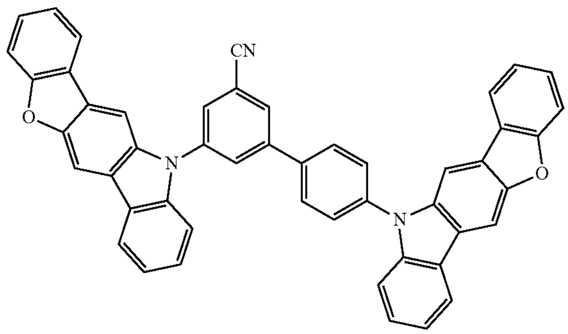
-continued
593
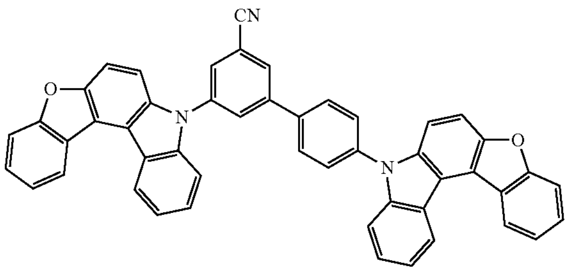
594
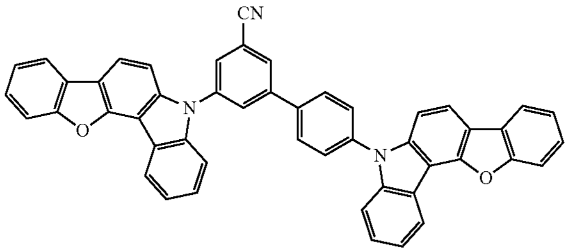
595
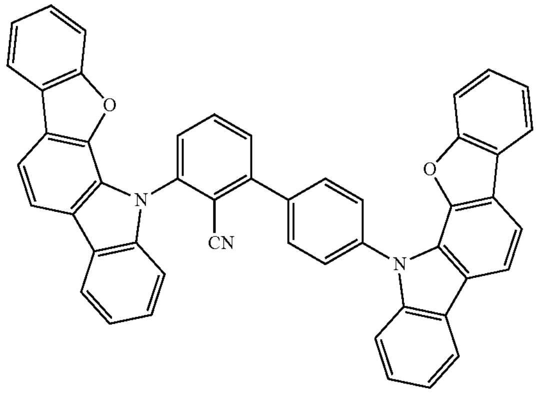
596
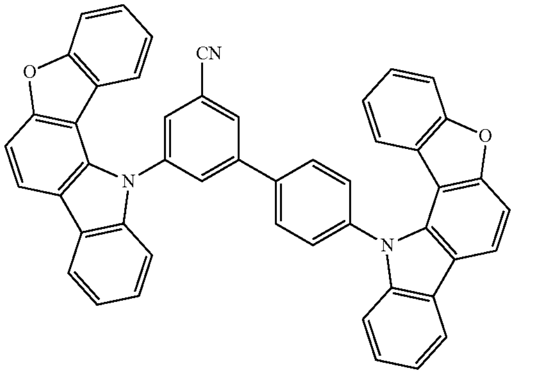
597
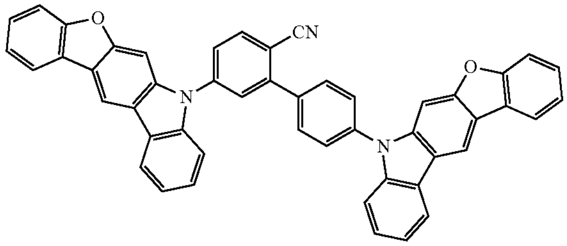

598
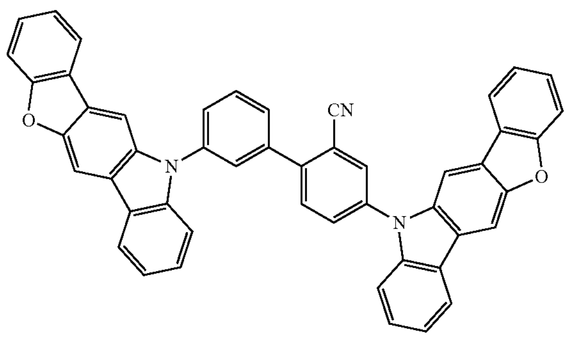
599
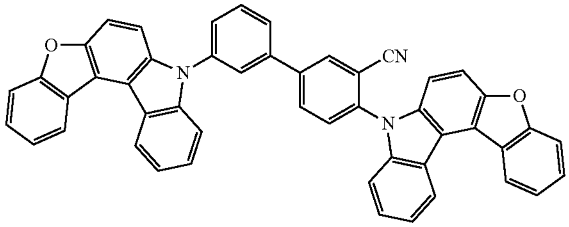
600
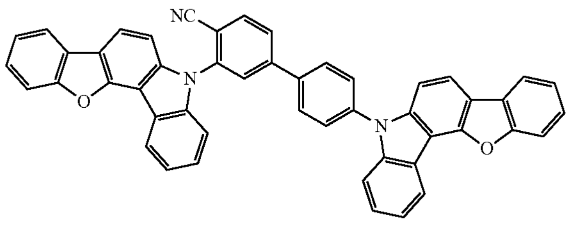
601
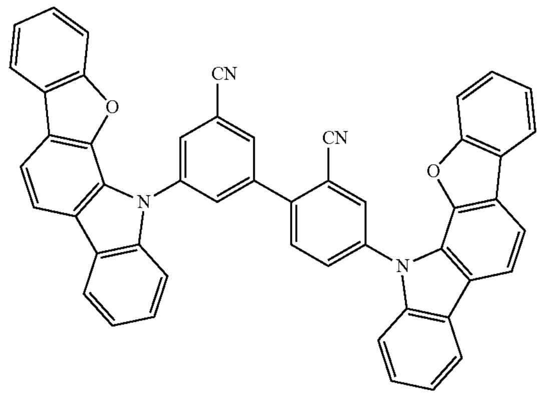
602
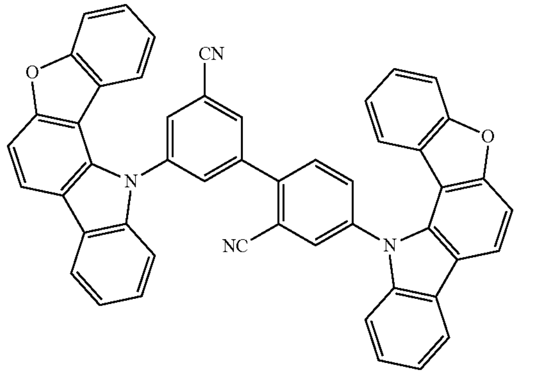
603
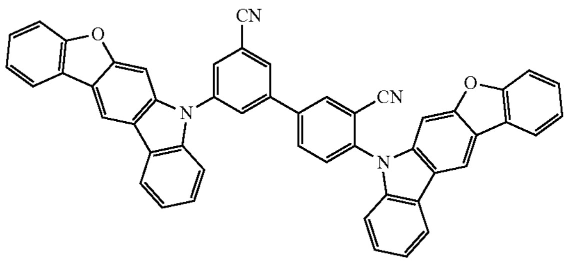
604
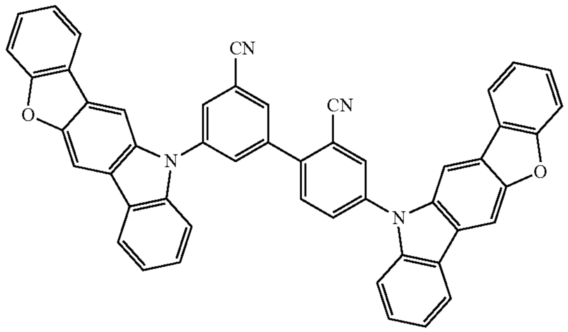
605
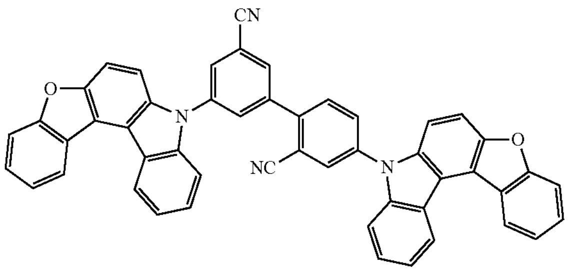
606
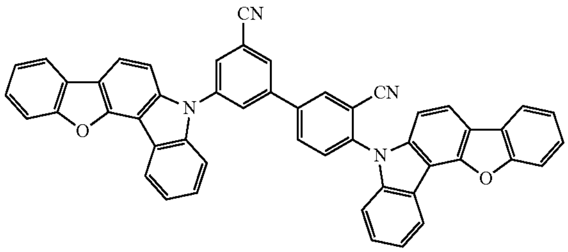
607
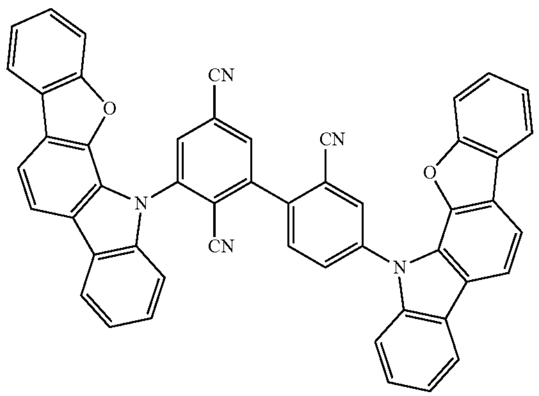

-continued
608
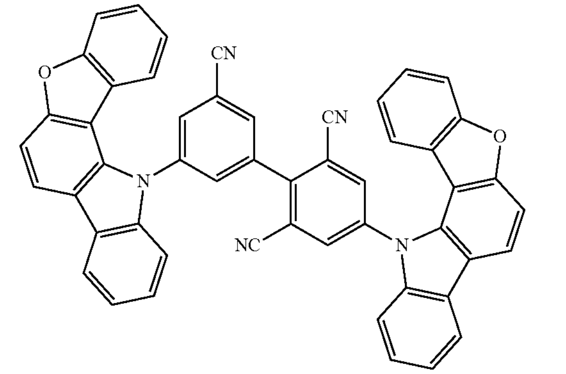
609
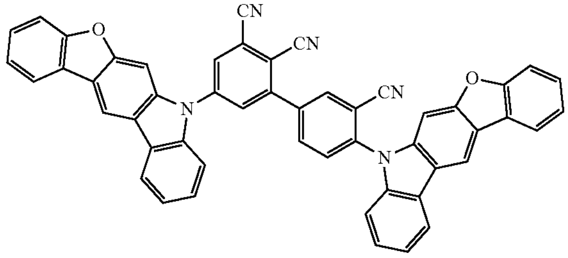
610
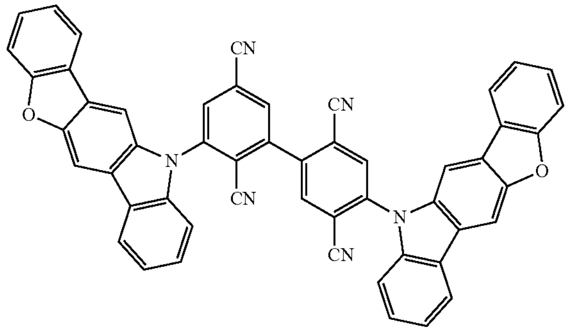
611
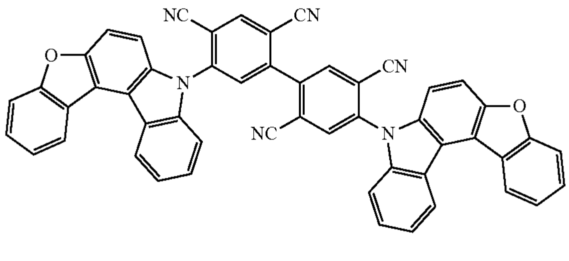
612
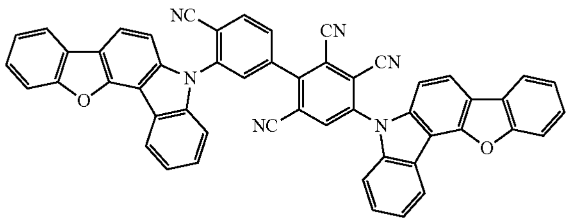
-continued
613
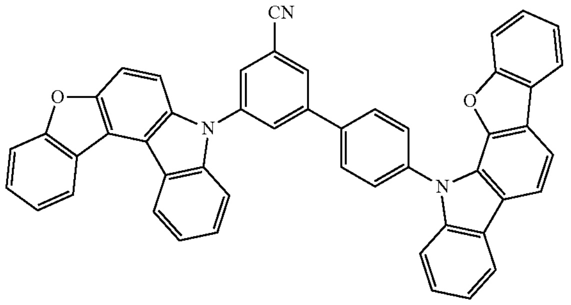
614
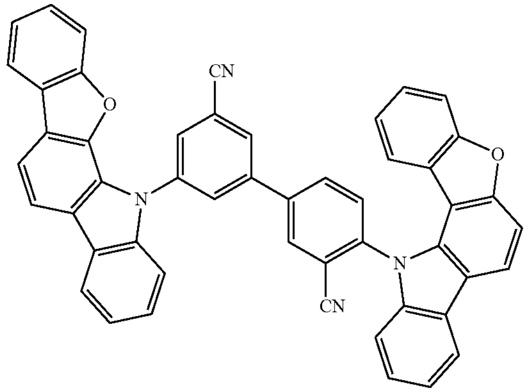
615
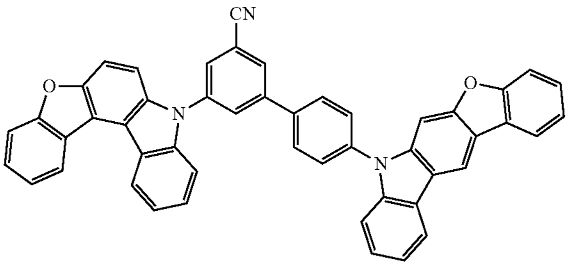
616
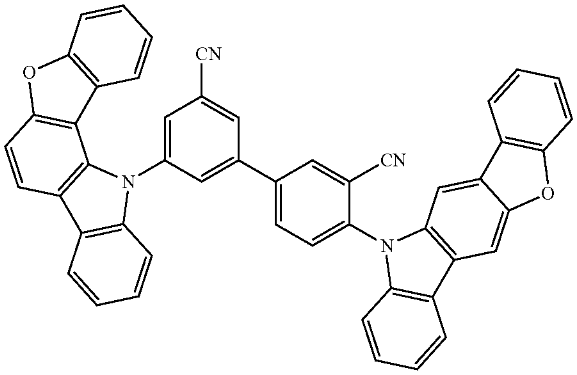

-continued
617
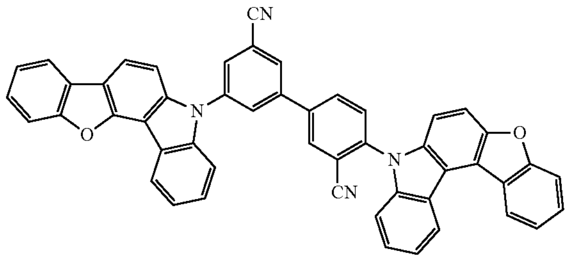
618
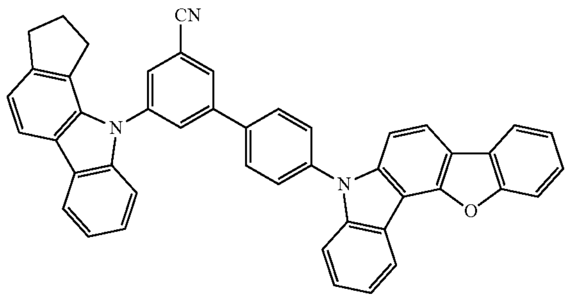
619
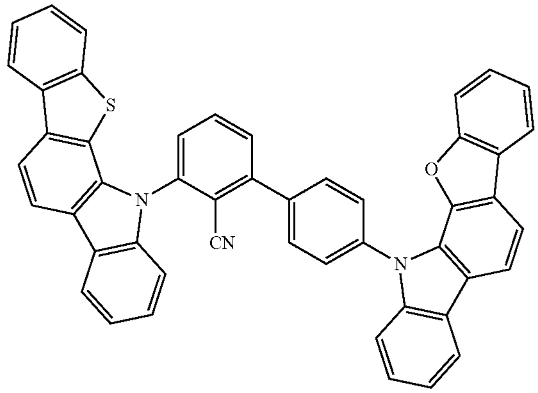
620
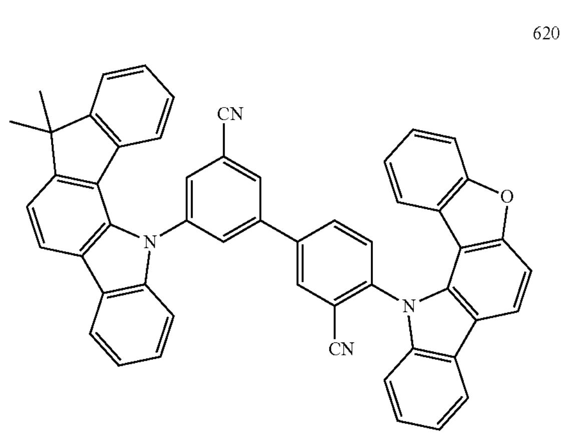
-continued
621
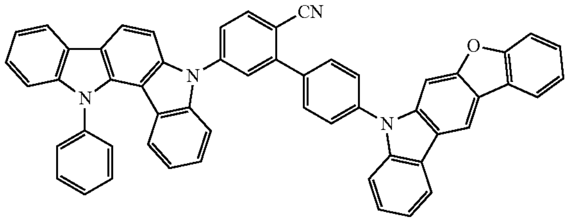
622
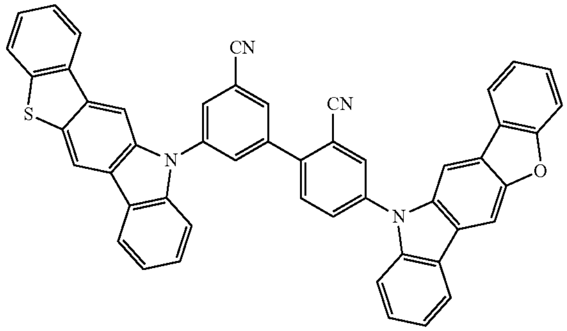
623
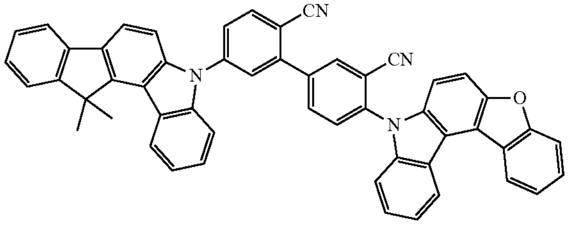
624
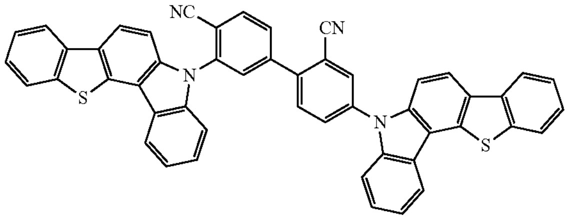
625
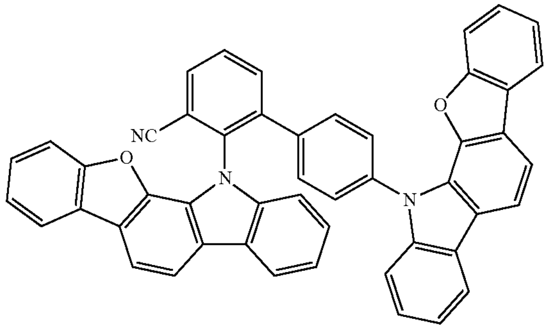

-continued
626
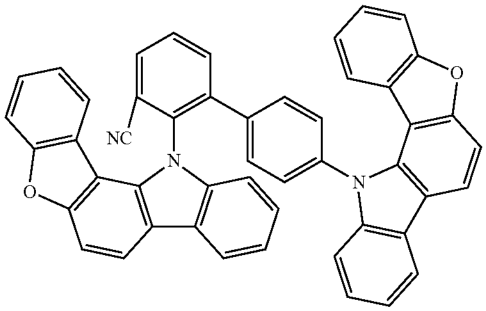
627
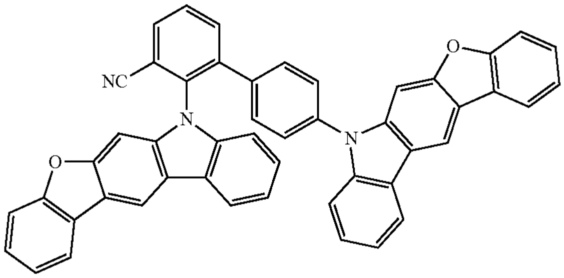
628
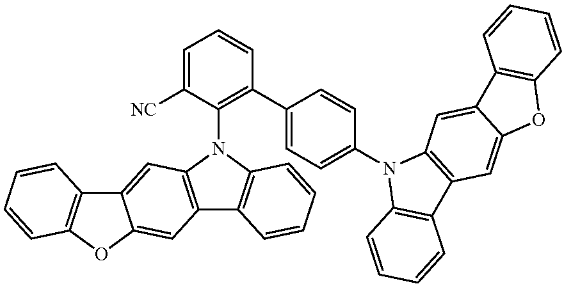
629
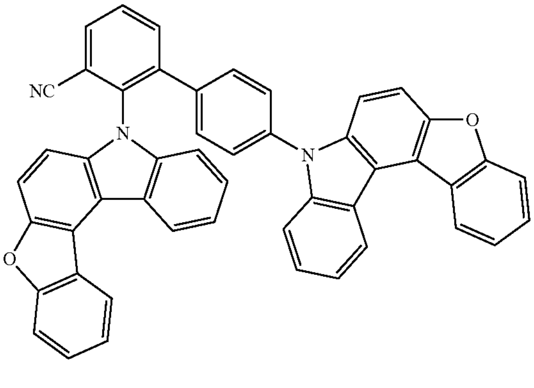
-continued
630
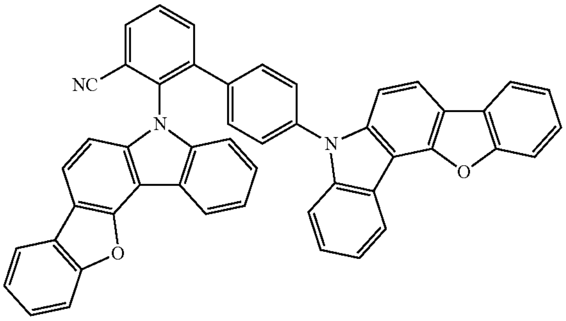
631
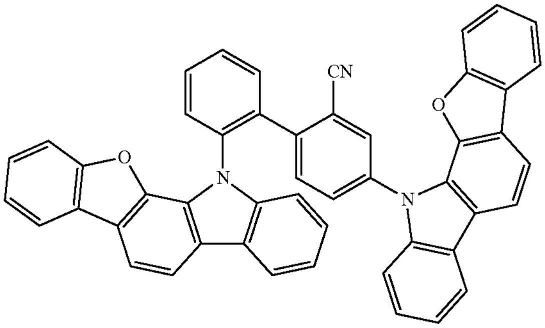
632
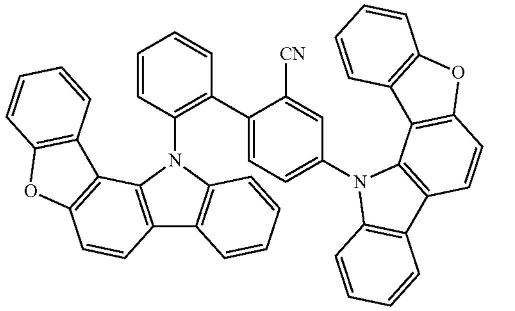
633
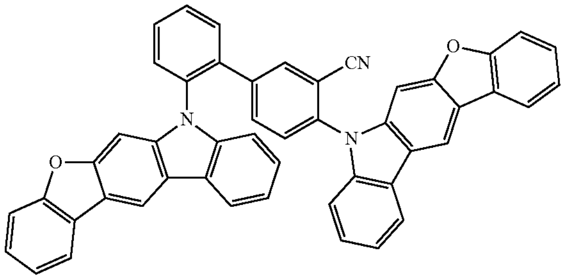
634
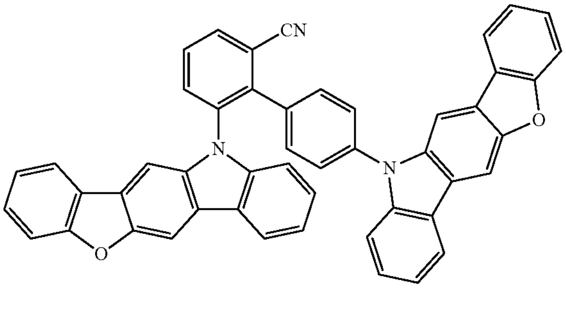

-continued
635
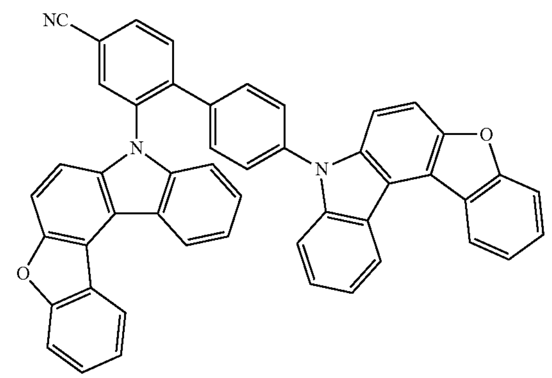
636
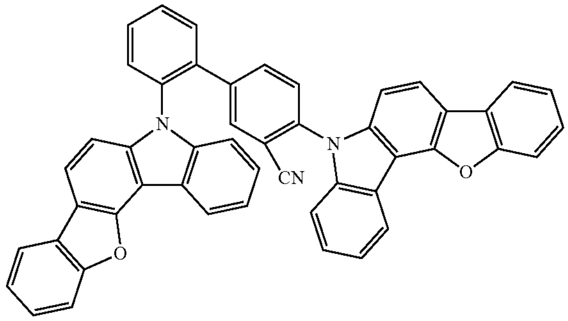
637
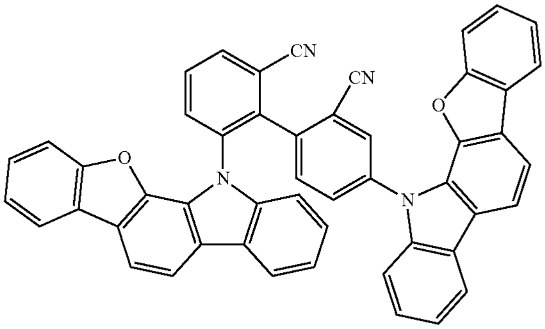
638
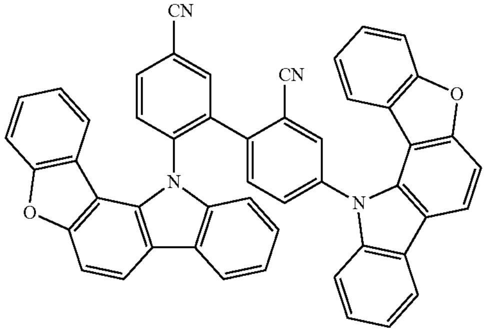
-continued
639
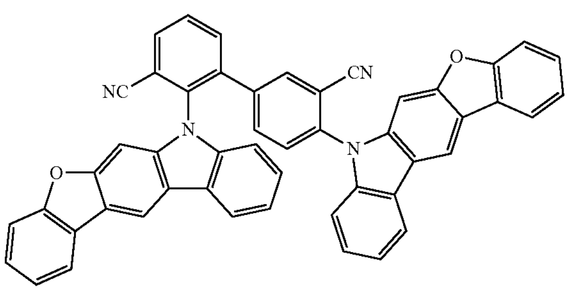
640
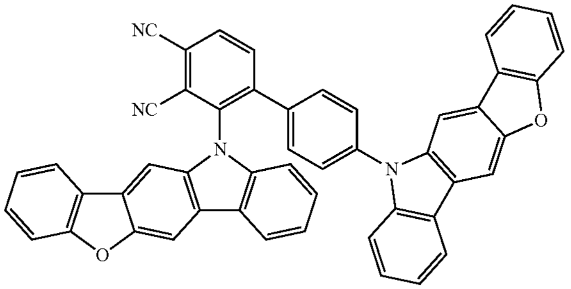
641
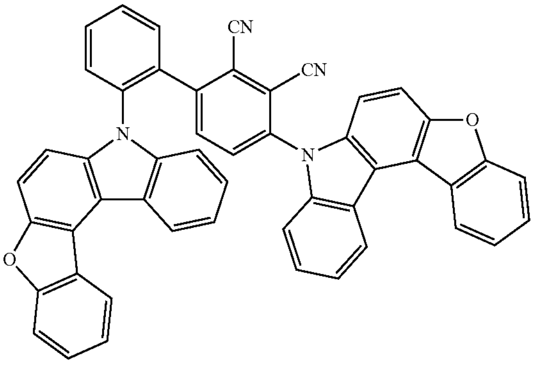
642
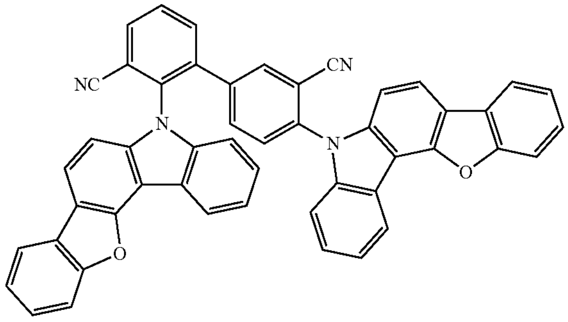

-continued
643
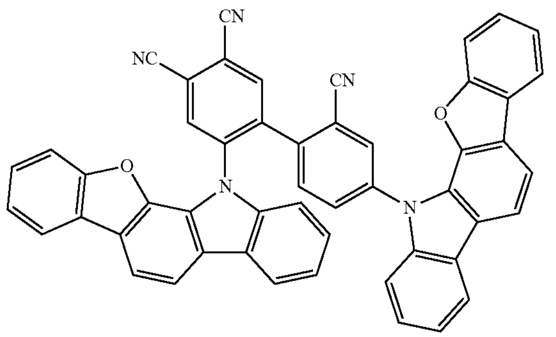
644
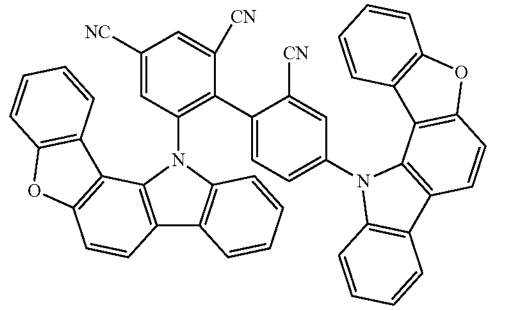
645
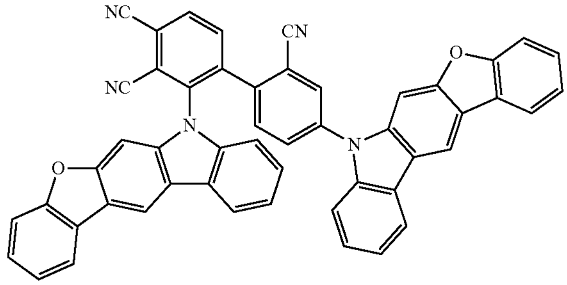
646
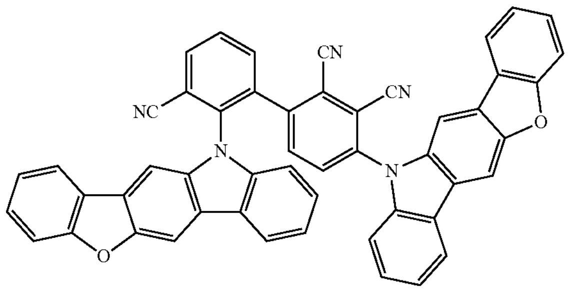
-continued
647
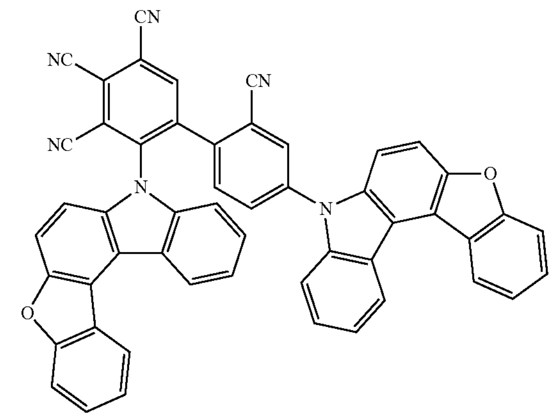
648
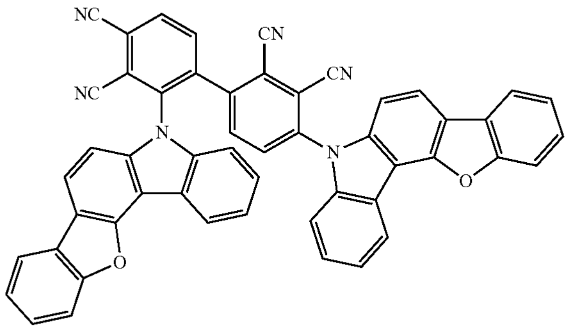
649
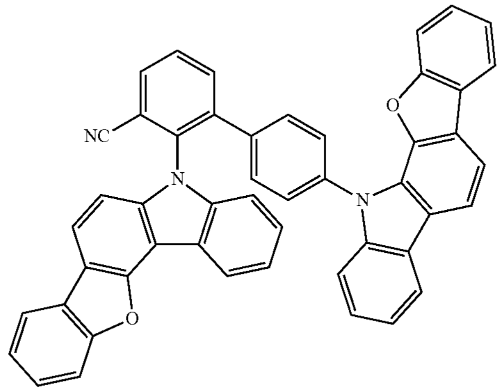
650
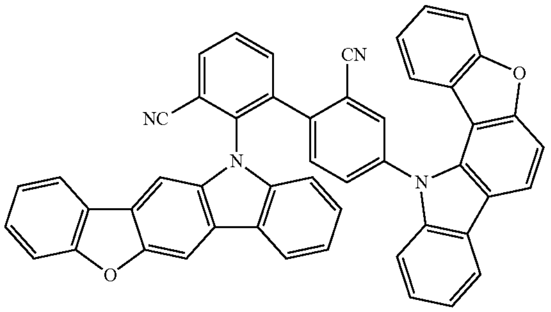

-continued
651
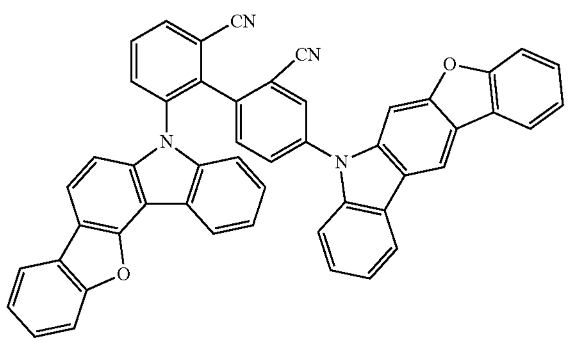
652
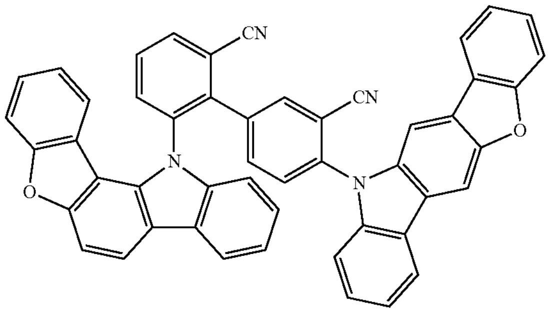
653
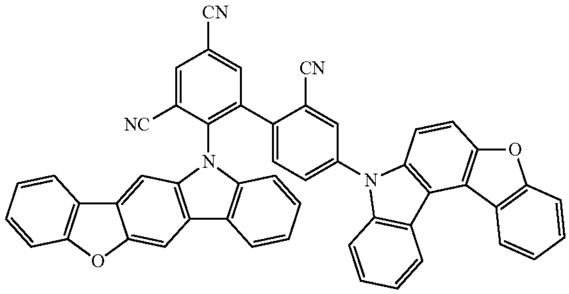
654
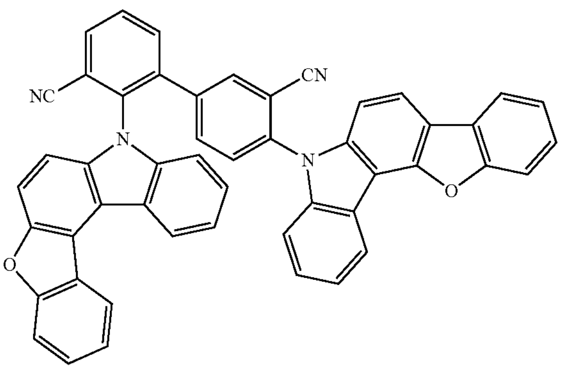
-continued
655
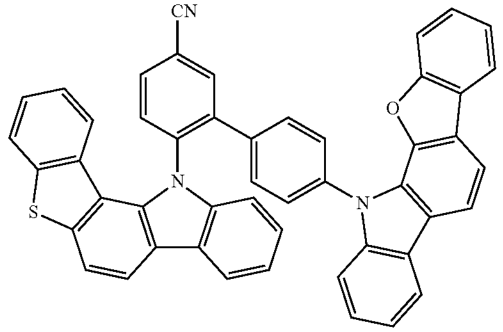
656
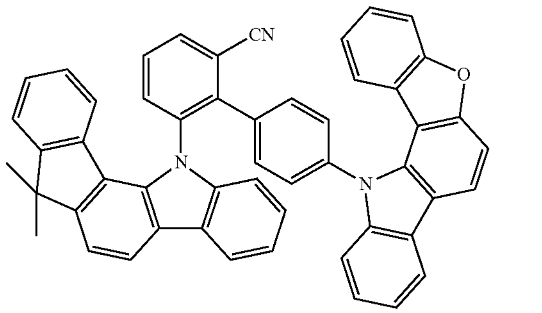
657
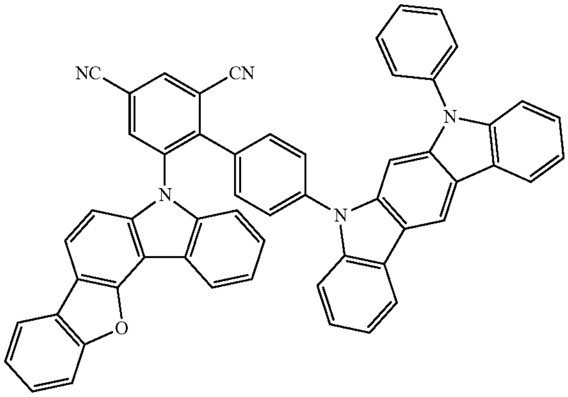
658
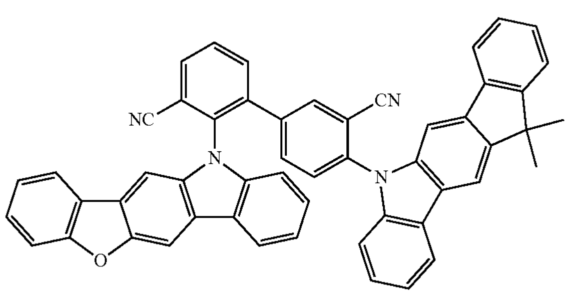

-continued
659
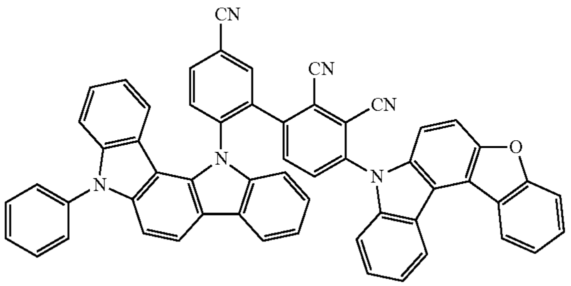
660
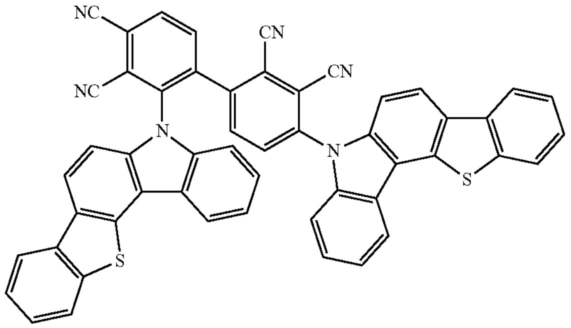
661
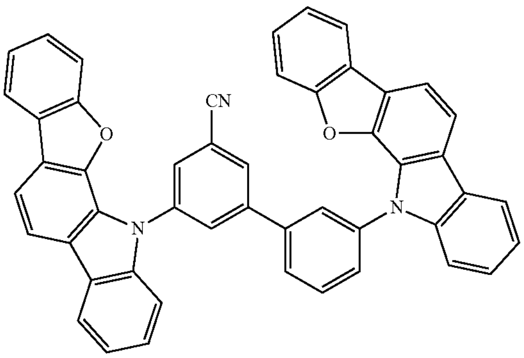
662
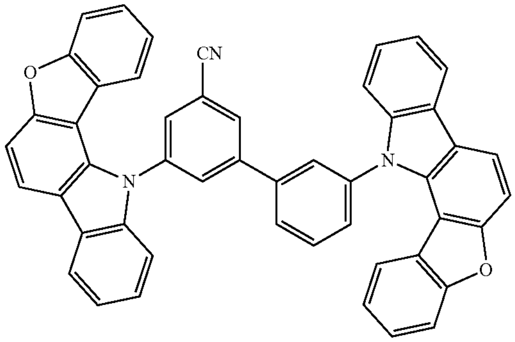
-continued
663
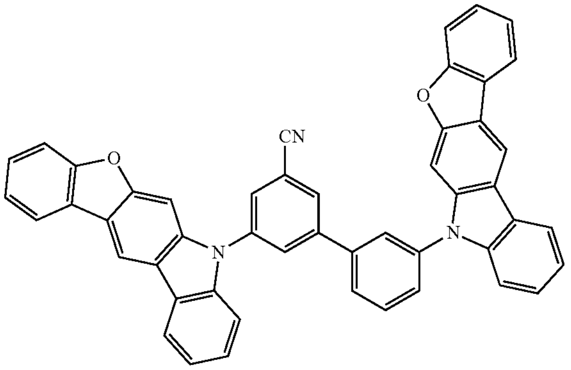
664
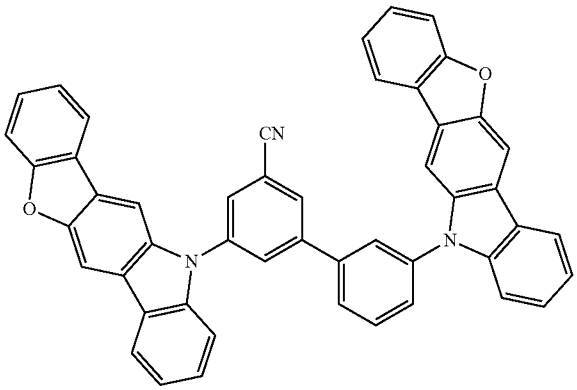
665
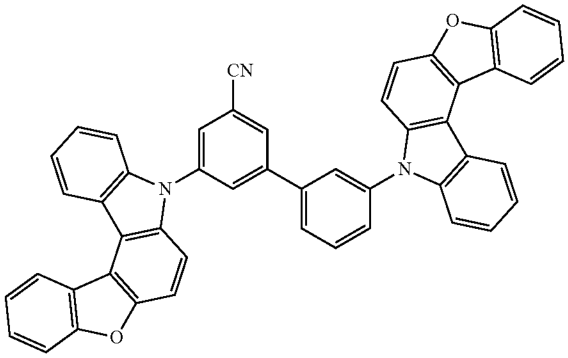

-continued
666
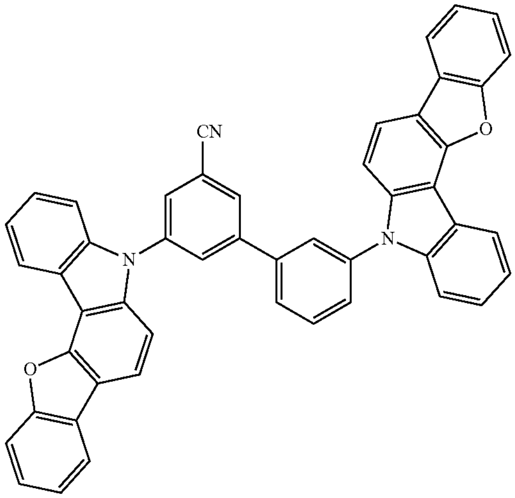
667
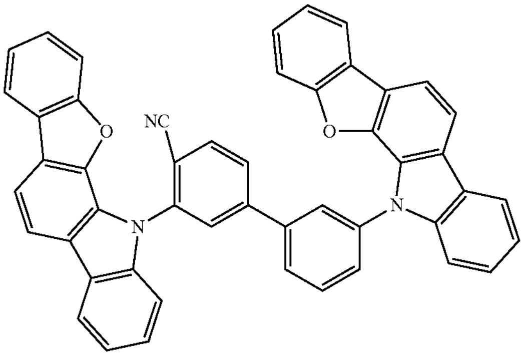
668
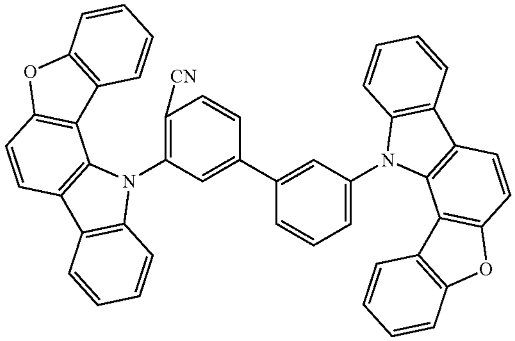
669
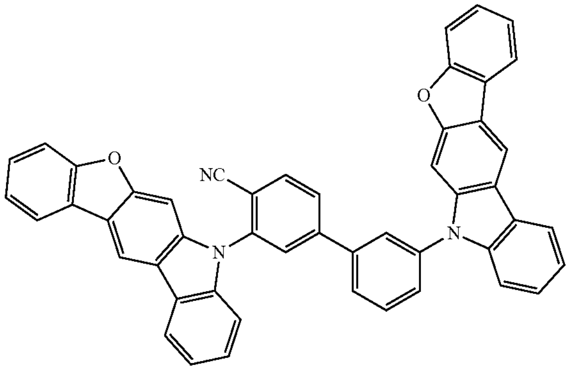
-continued
670
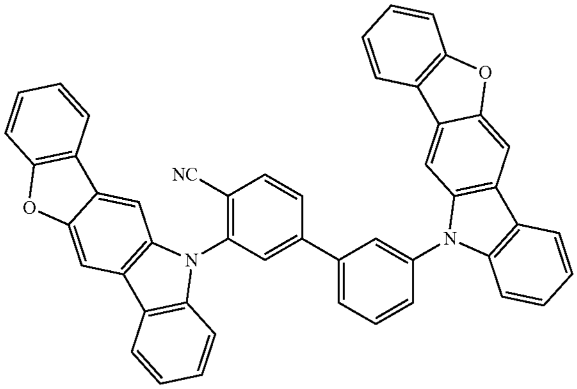
671
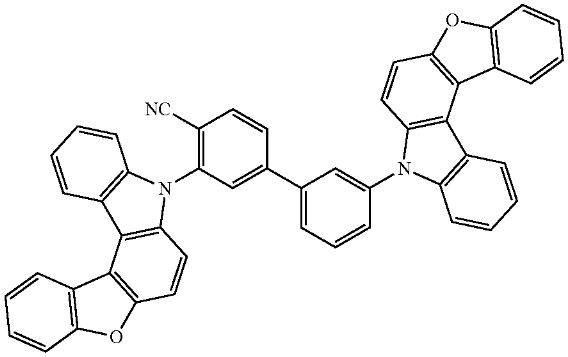
672
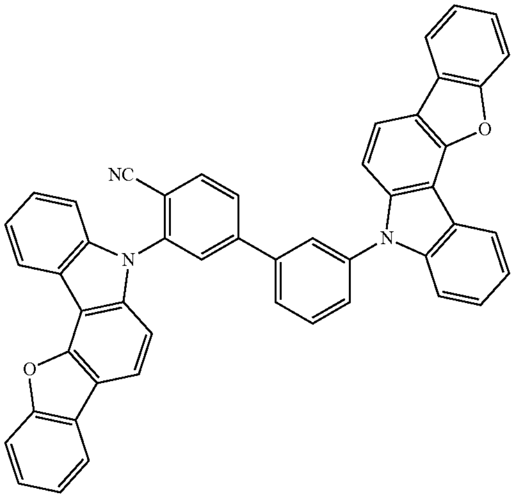

-continued
673
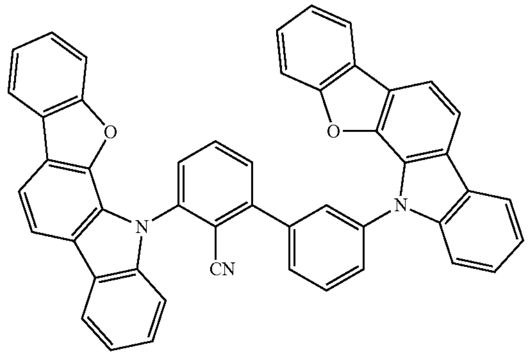
674
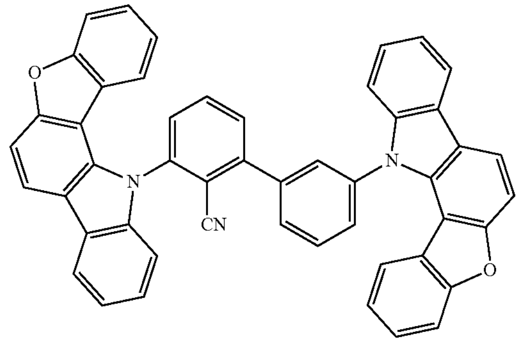
675
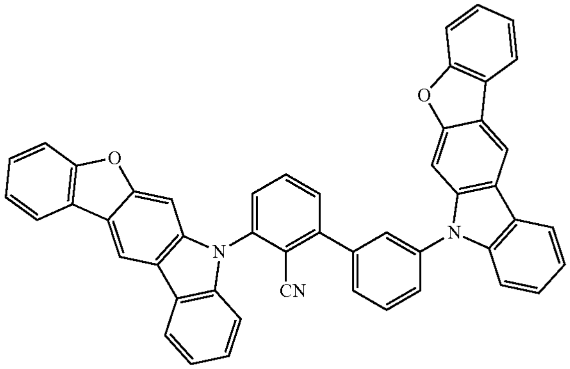
676
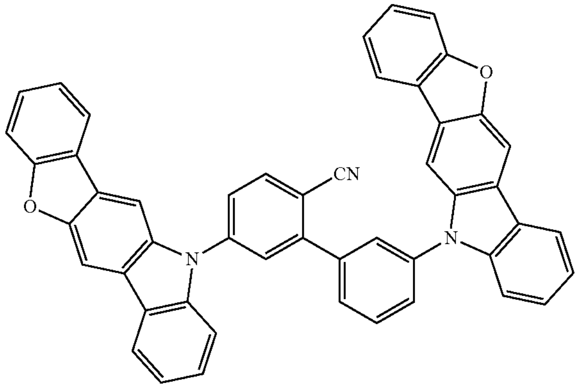
-continued
677
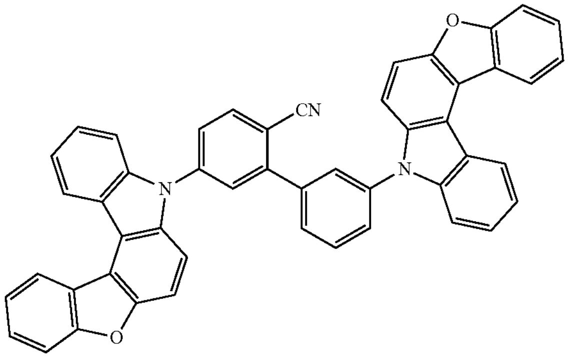
678
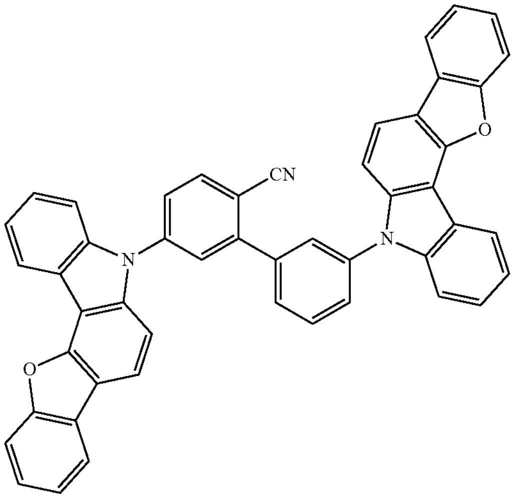
679
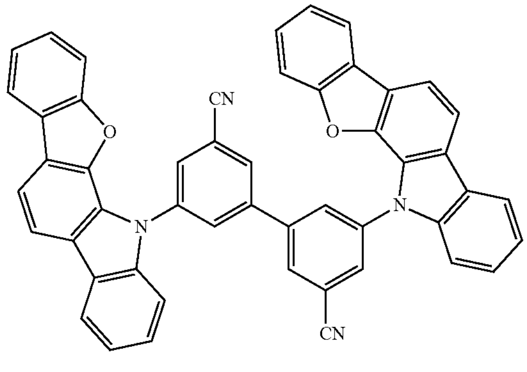
680
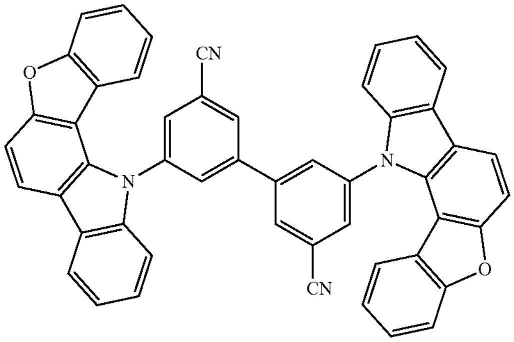

681
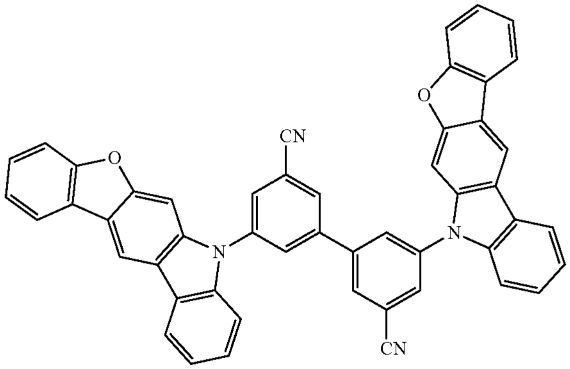
682
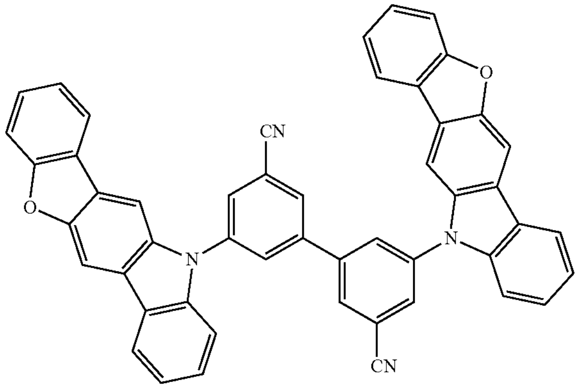
683
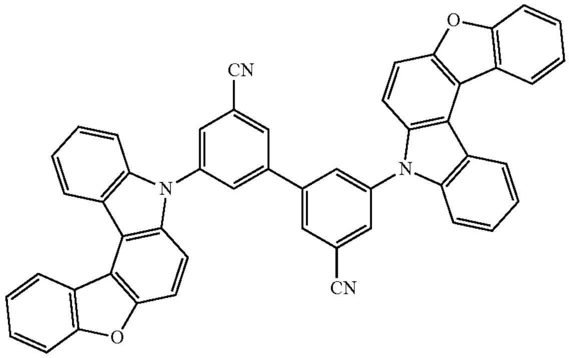
684
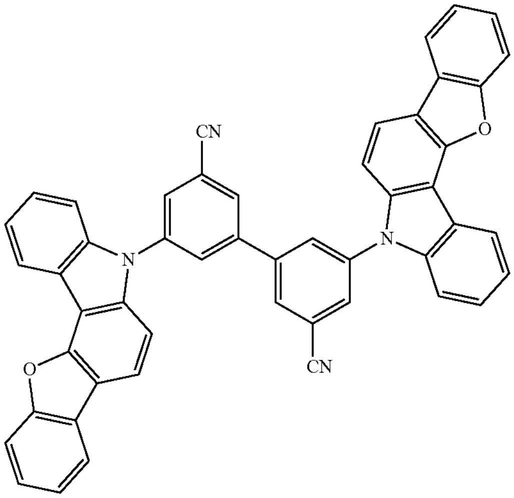
685
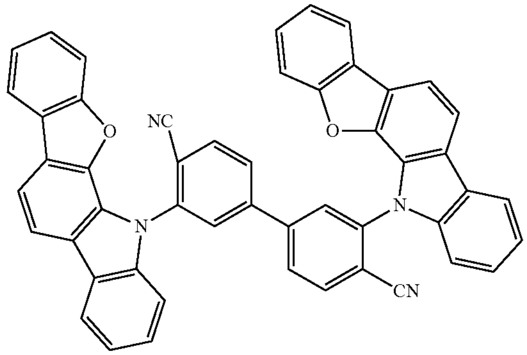
686
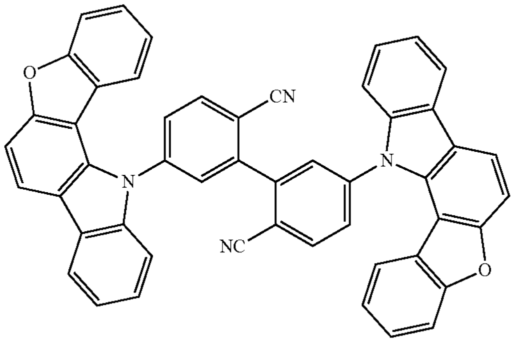

-continued
687
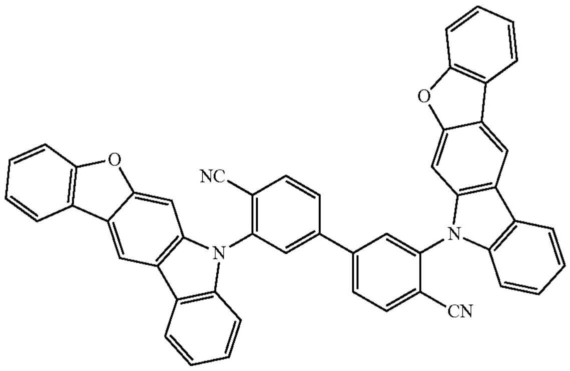
688
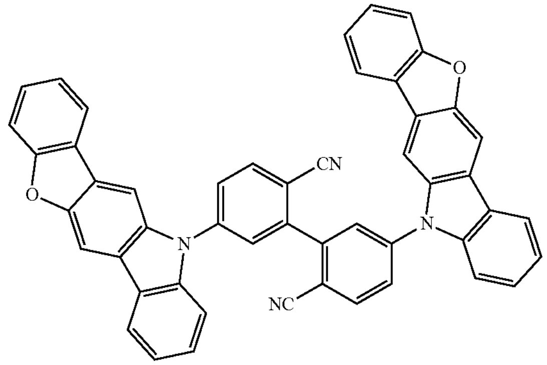
689
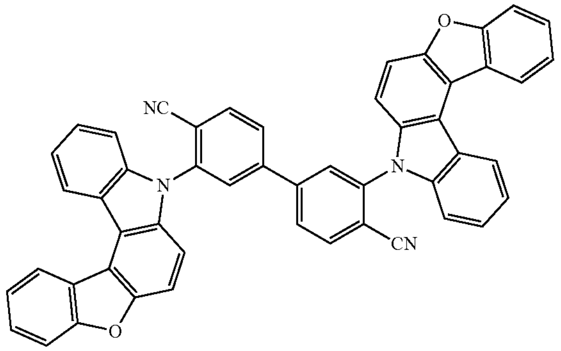
690
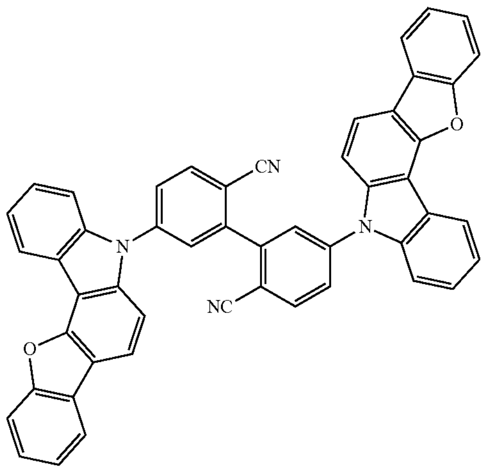
-continued
691
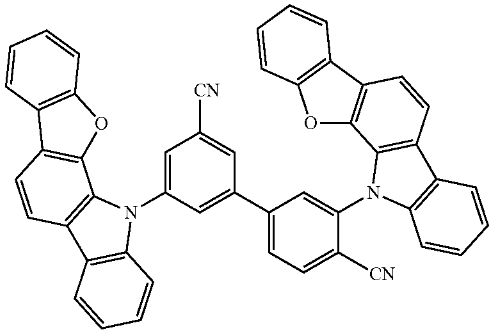
692
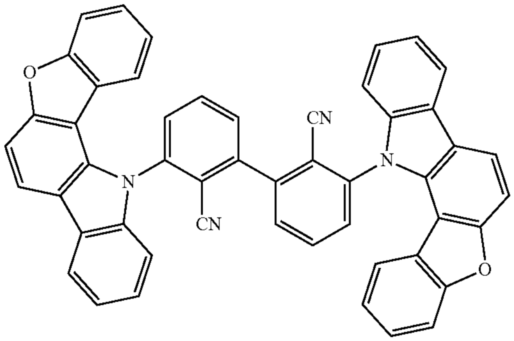
693
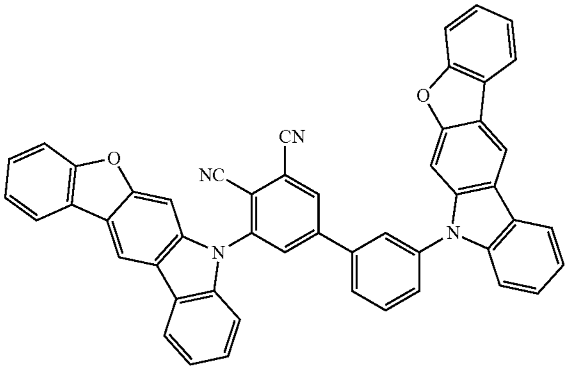
694
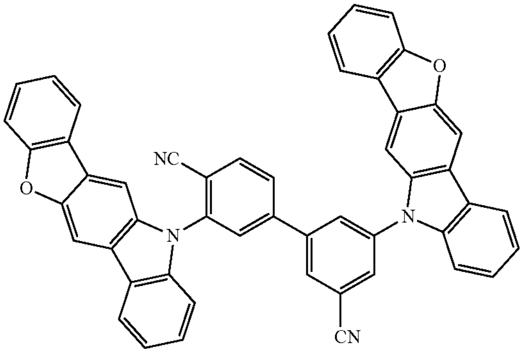

-continued
695
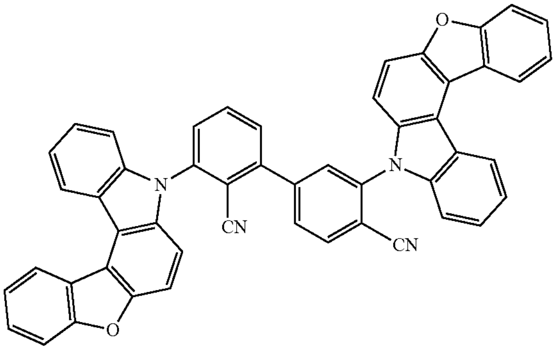
696
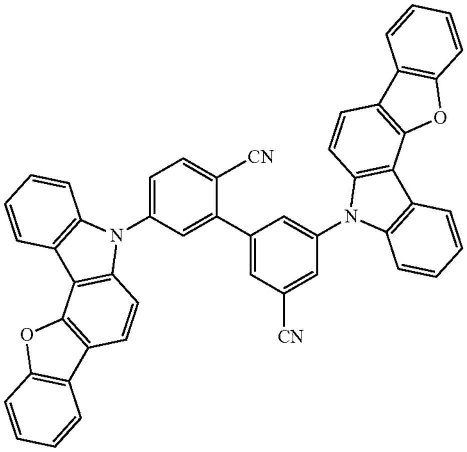
697
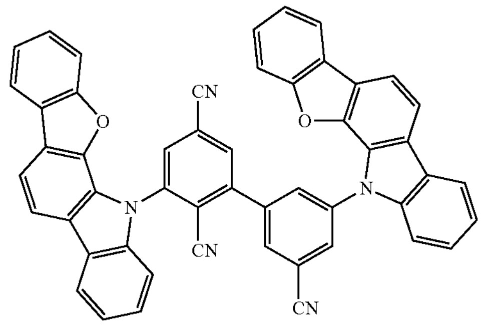
698
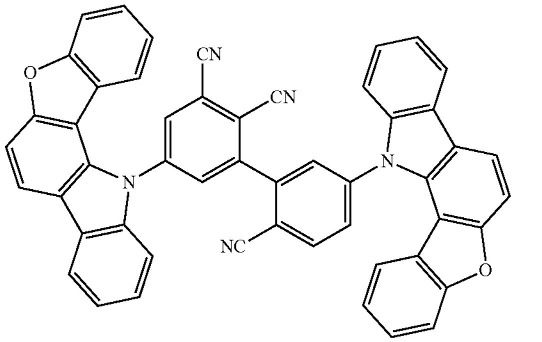
-continued
699
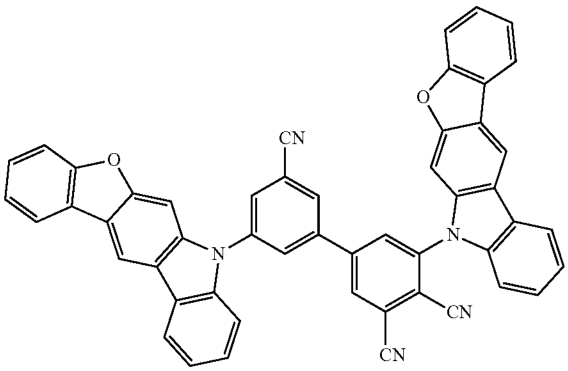
700
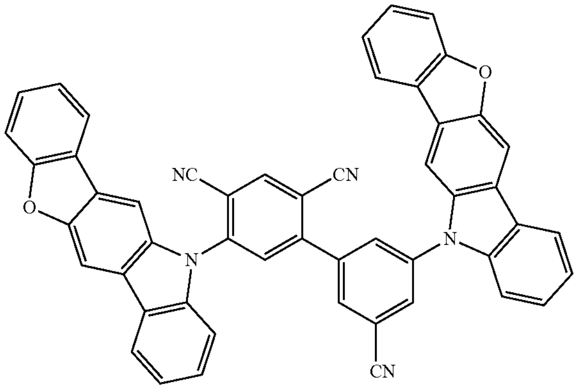
701
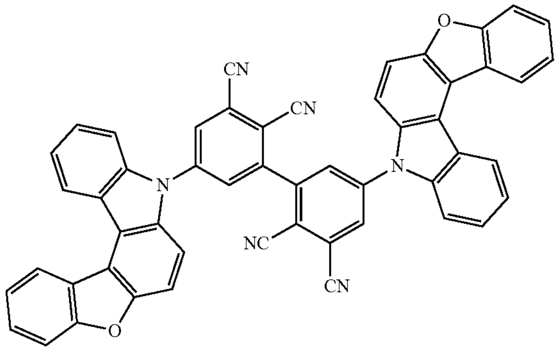

-continued
702
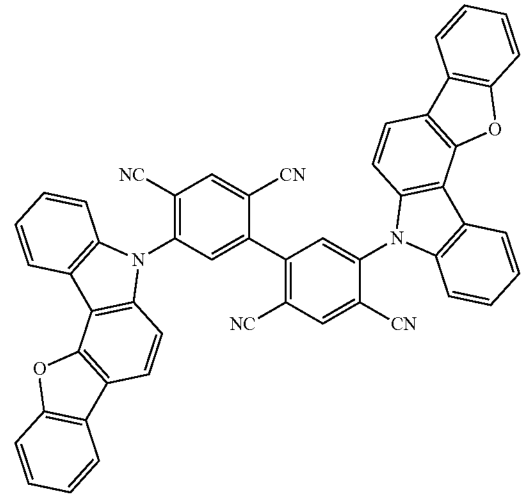
703
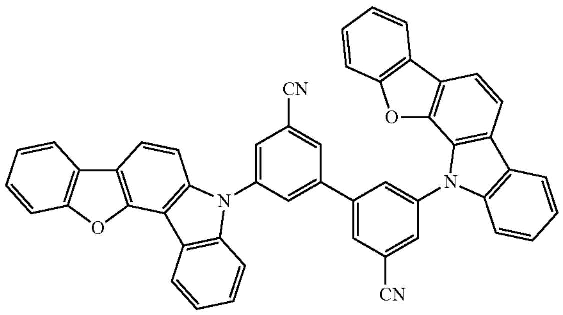
704
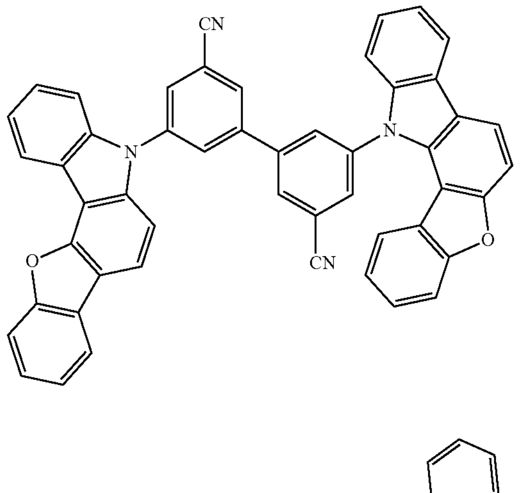
705
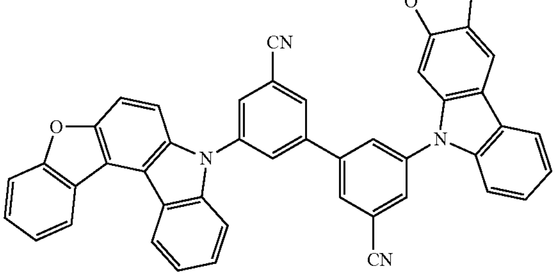
-continued
706
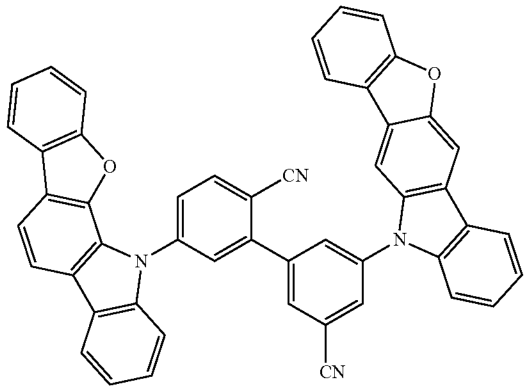
707
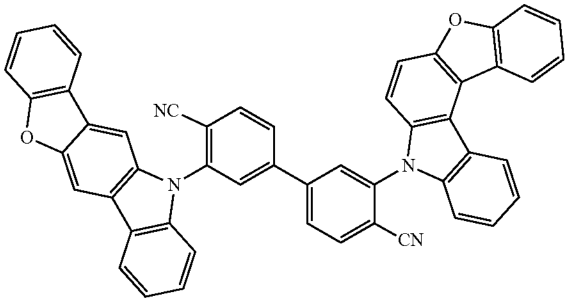
708
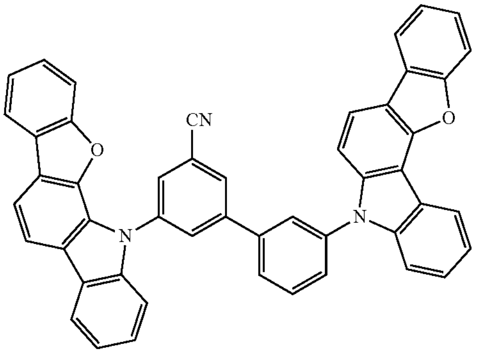
709
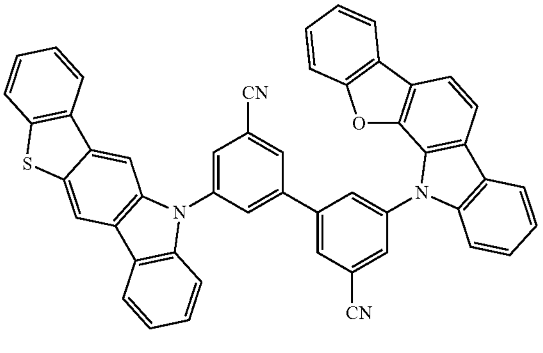

-continued
710
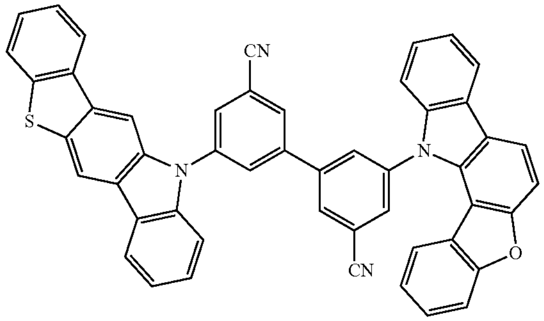
711
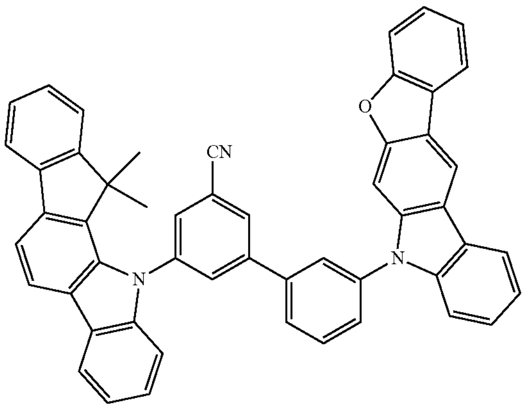
712
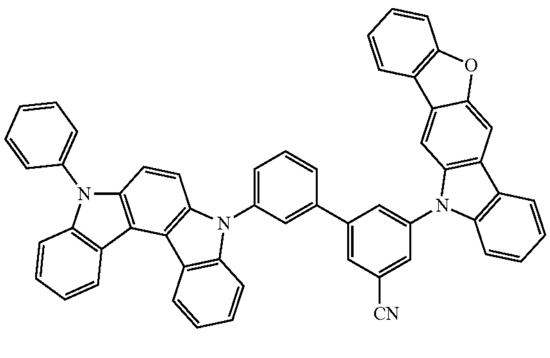
713
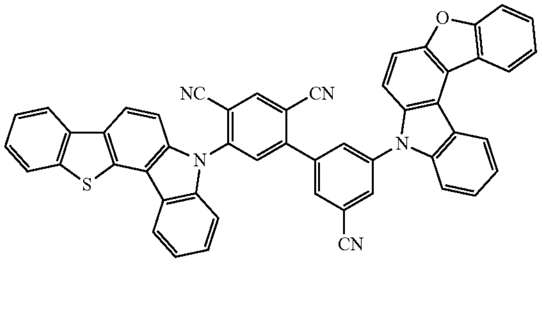
-continued
714
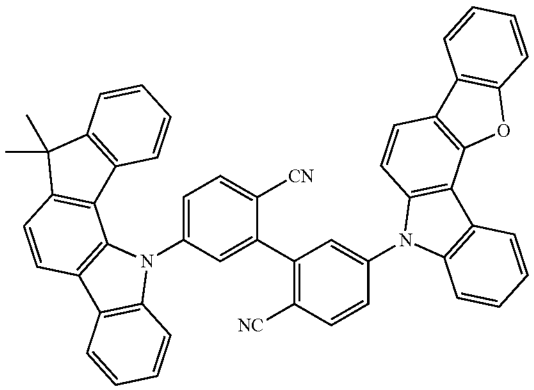
715
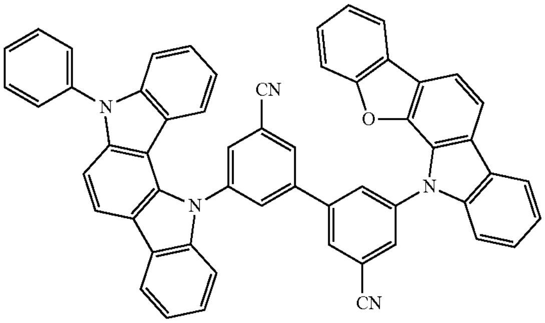
716
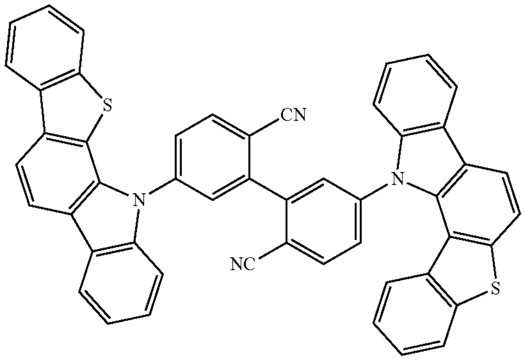
717
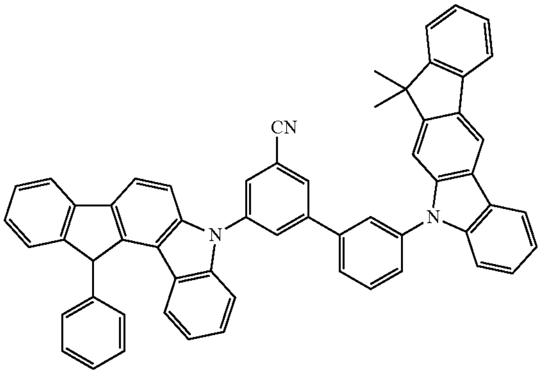

-continued
718
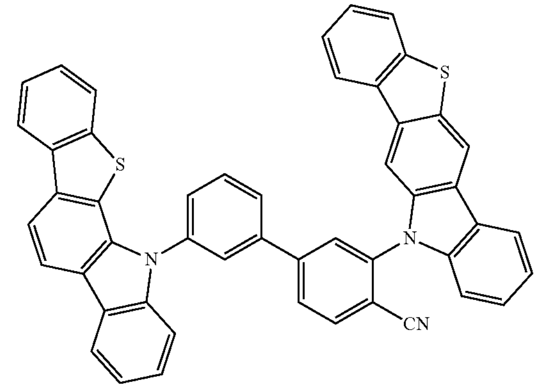
719
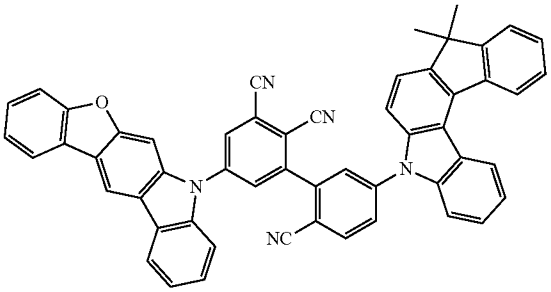
720
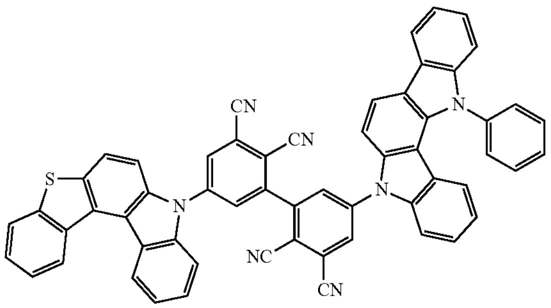
721
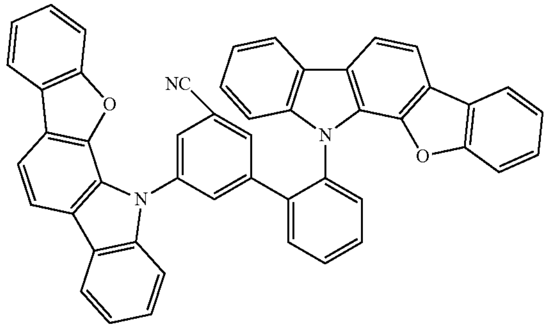
-continued
722
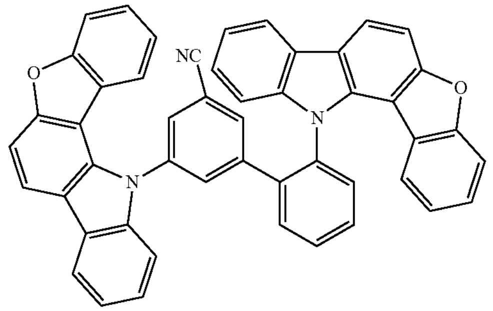
723
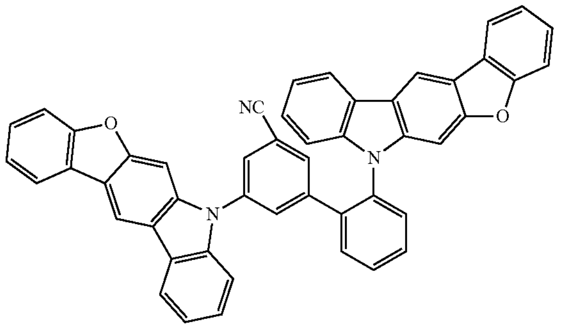
724
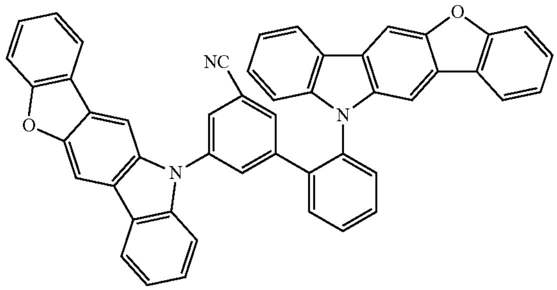
725
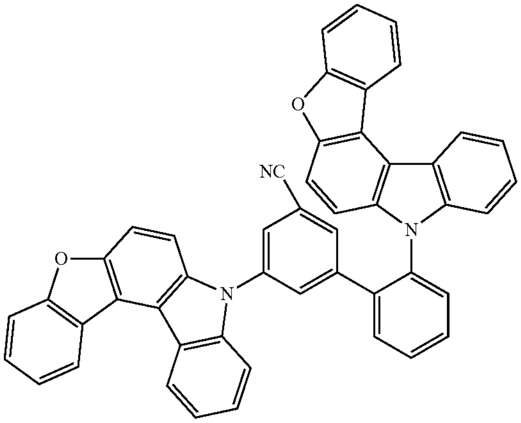

-continued
726
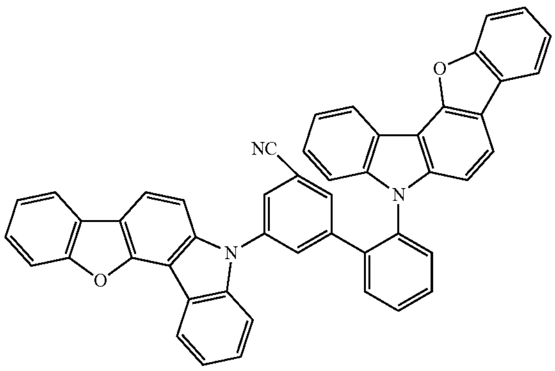
727
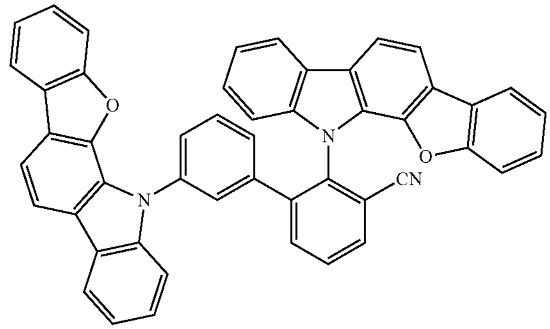
728
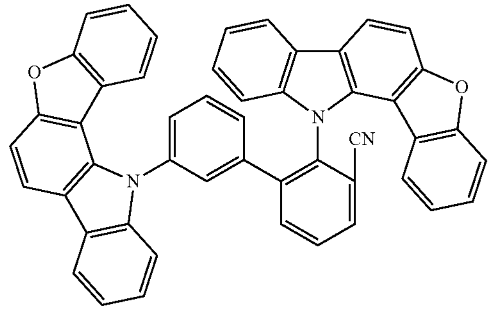
729
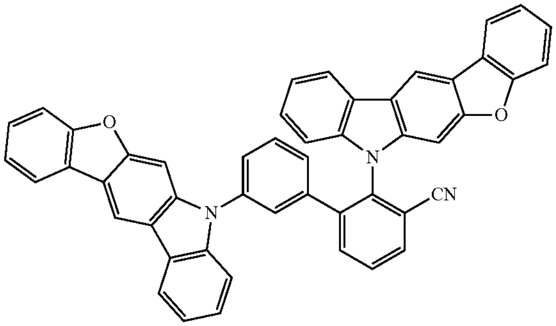
-continued
730
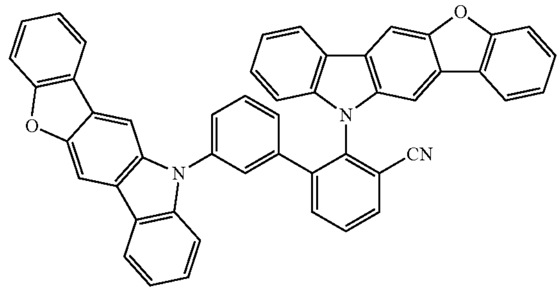
731
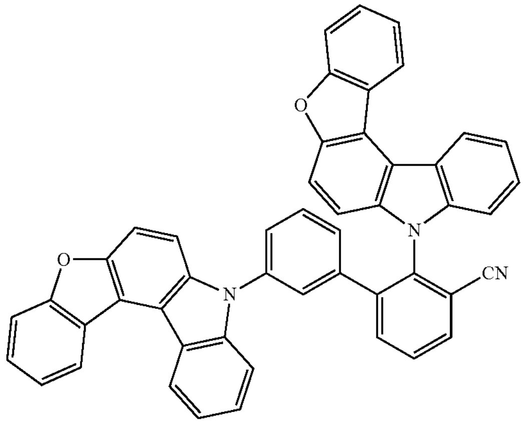
732
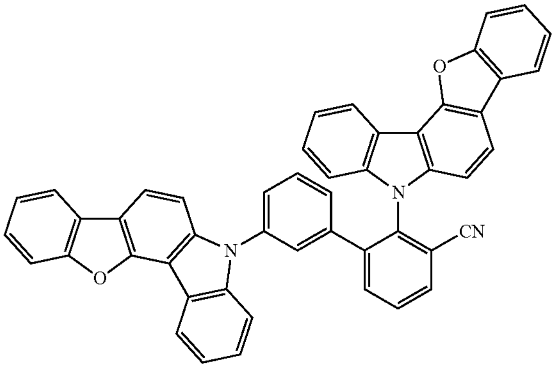
733
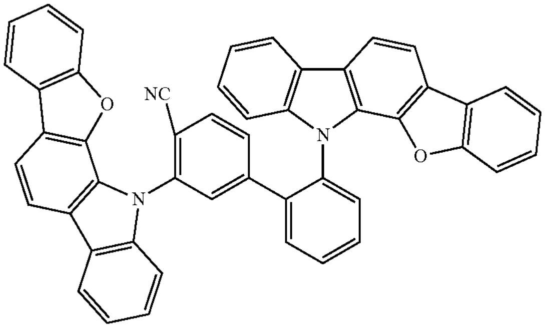

-continued
734
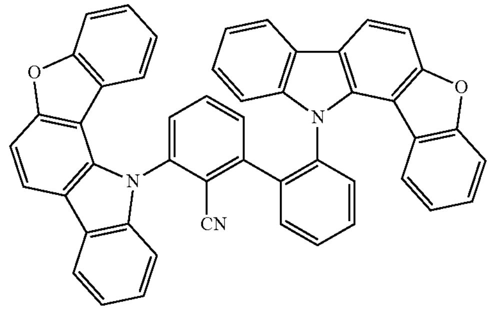
735
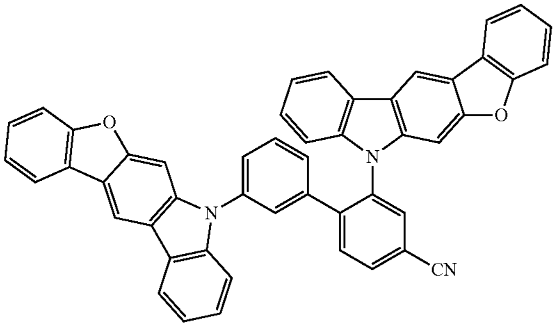
736
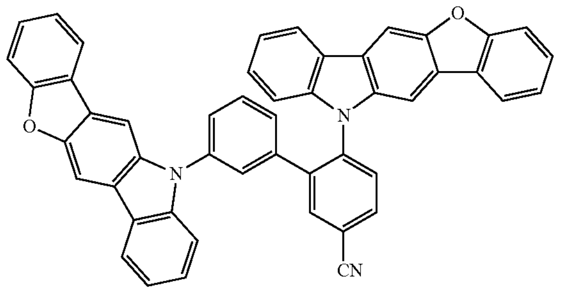
737
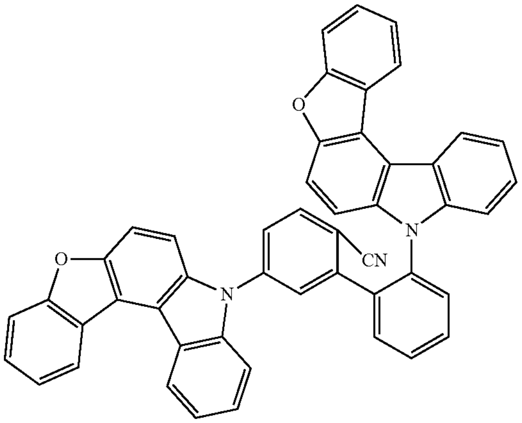
-continued
738
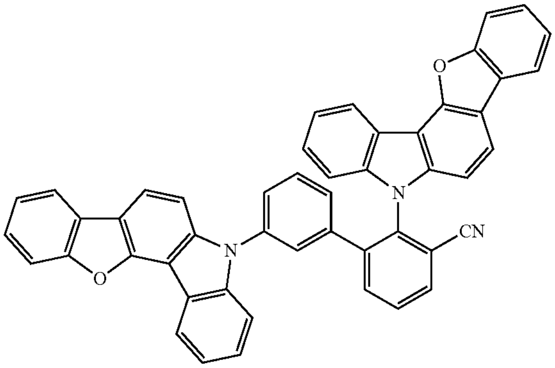
739
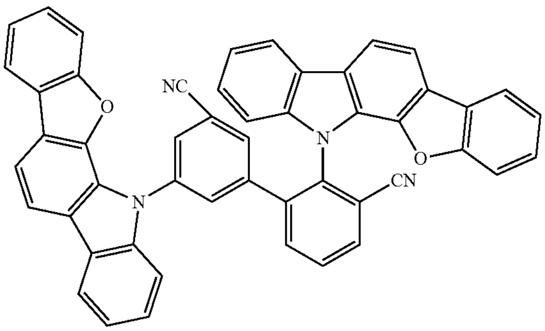
740
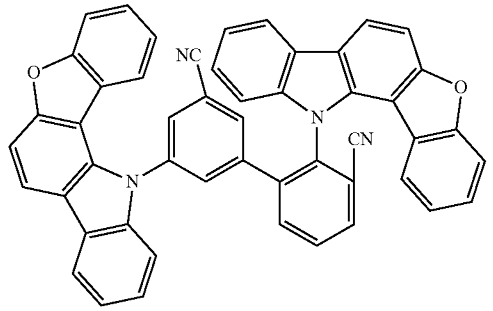
741
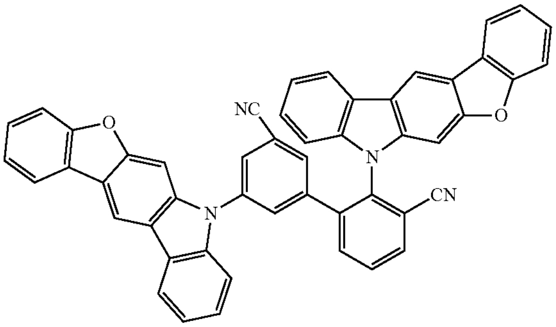

-continued
742
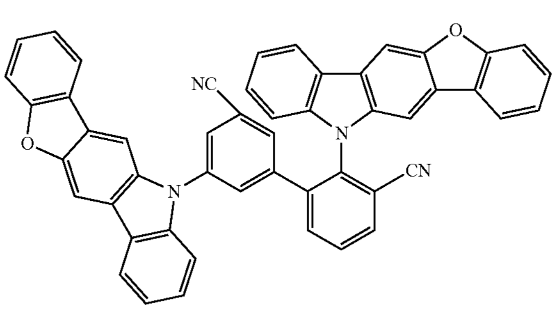
743
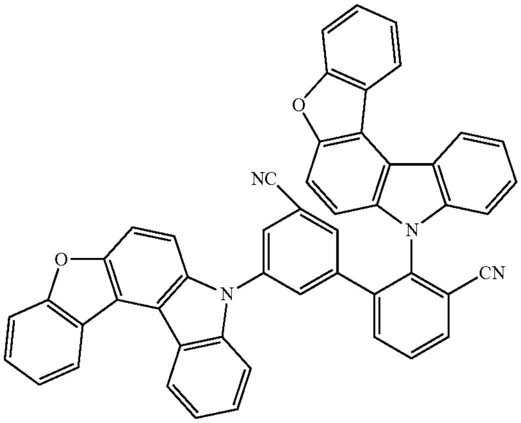
744
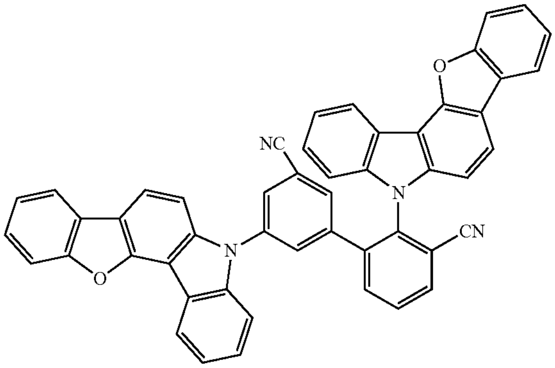
745
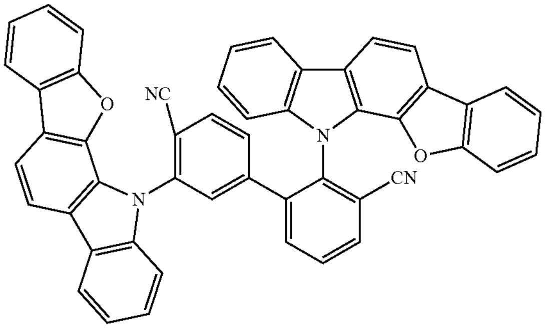
-continued
746
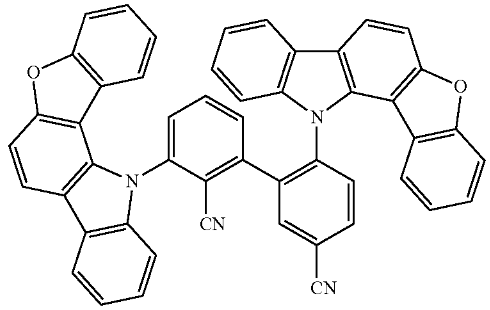
747
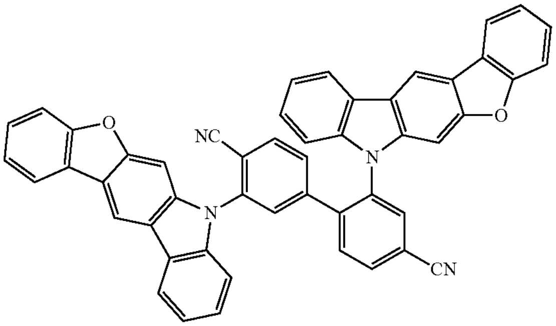
748
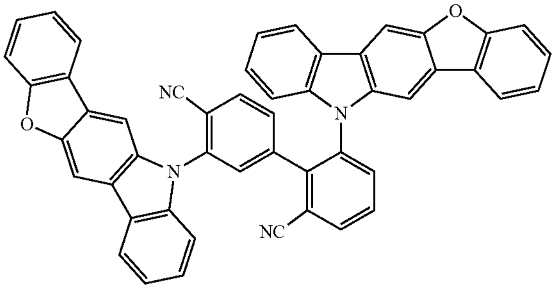
749
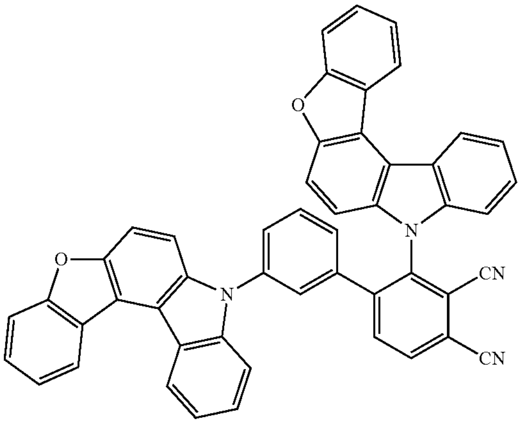

750
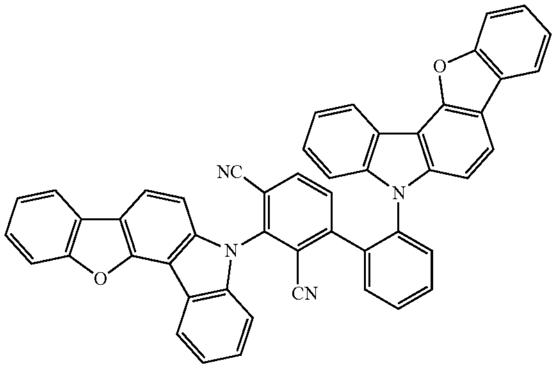
751
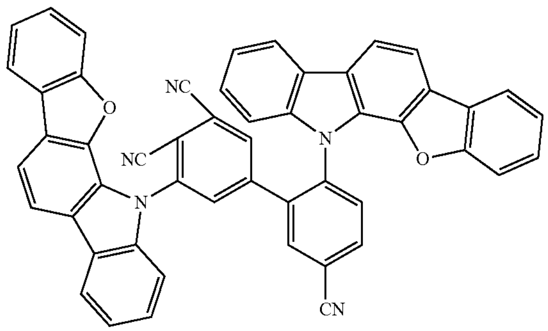
752
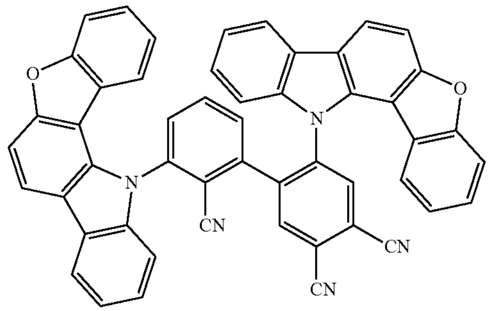
753
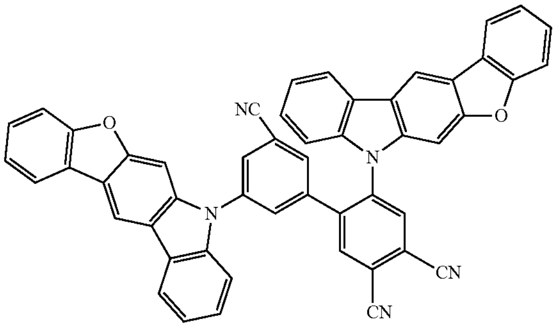
754
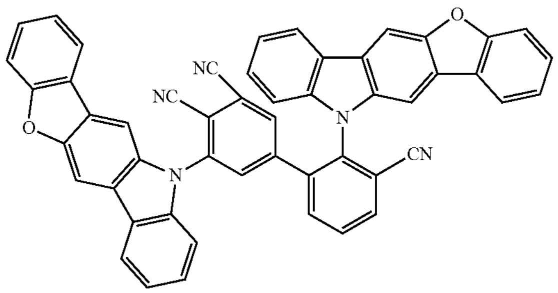
755
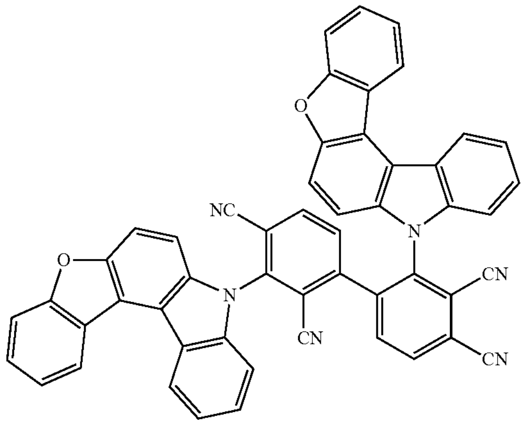
756
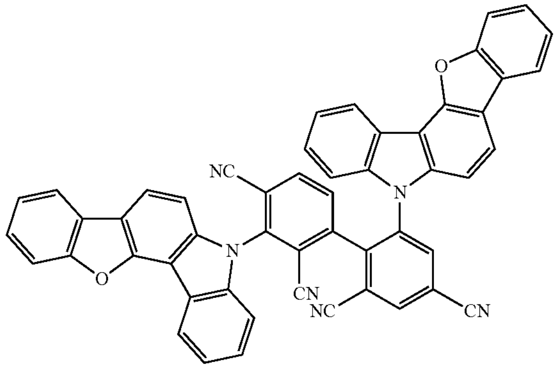
757
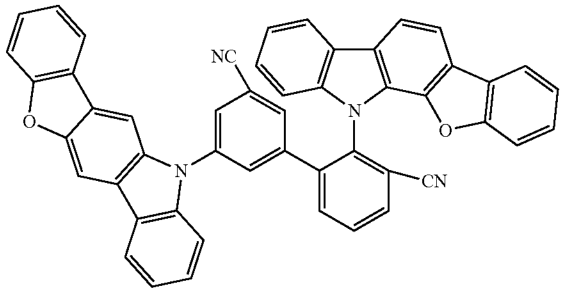

758
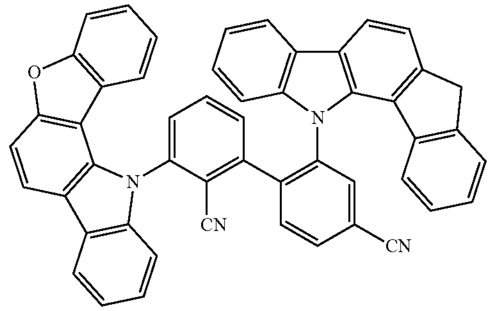
759
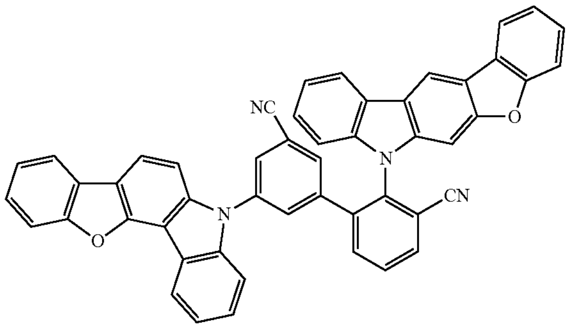
760
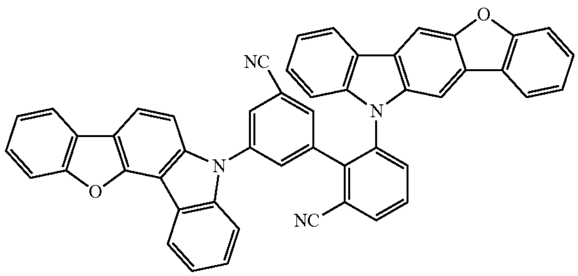
761
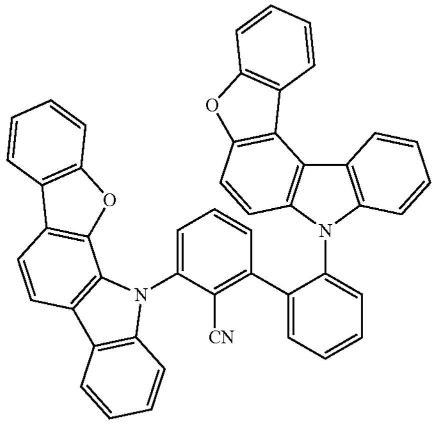
762
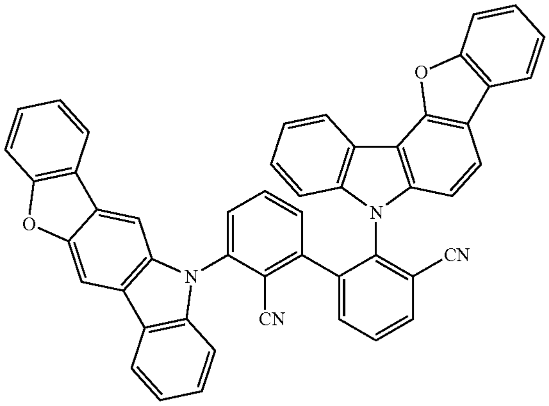
763
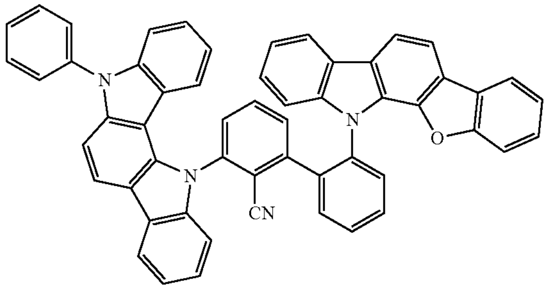
764
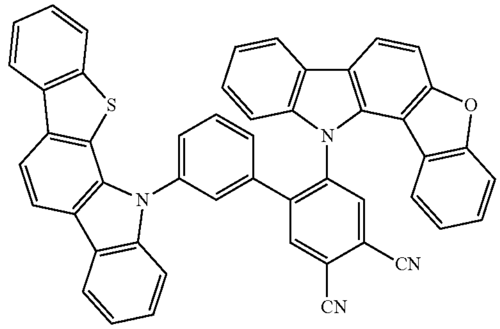
765
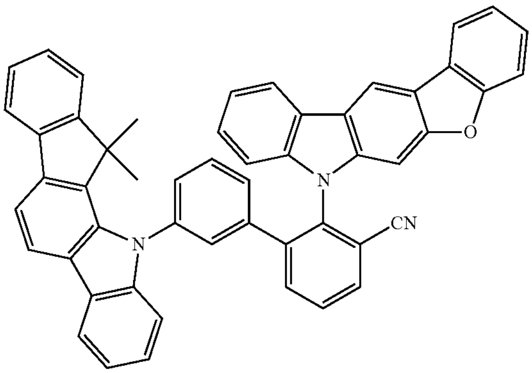

-continued
766
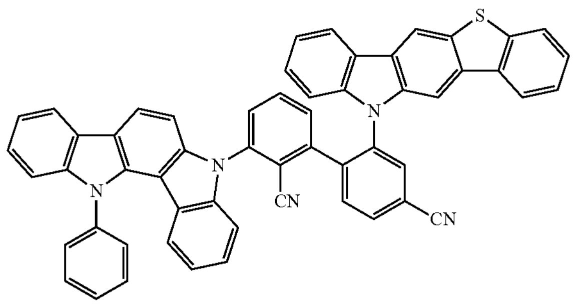
767
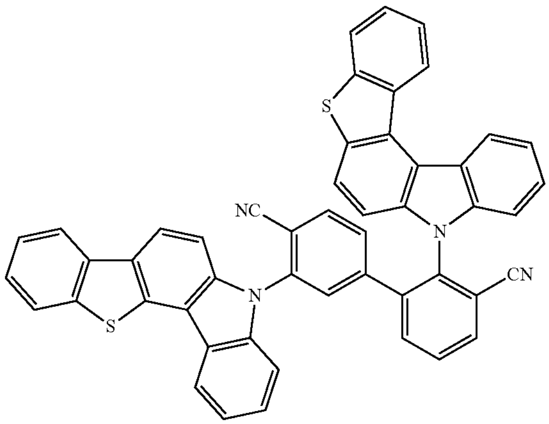
768
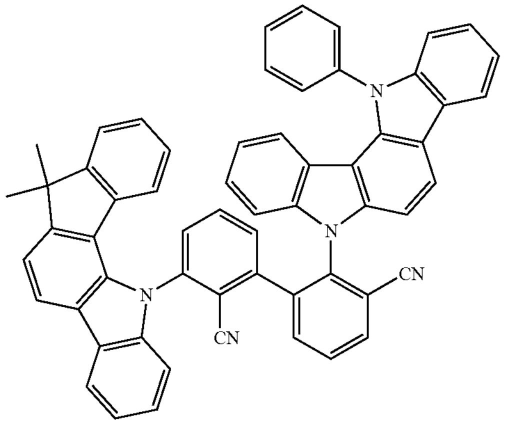
769
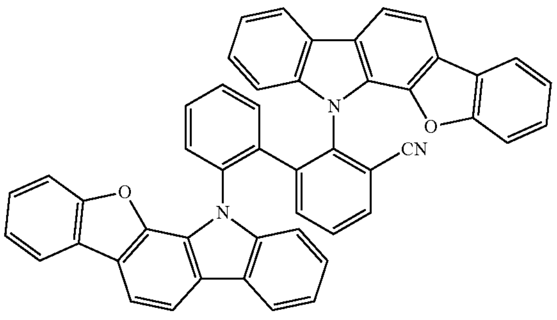
-continued
770
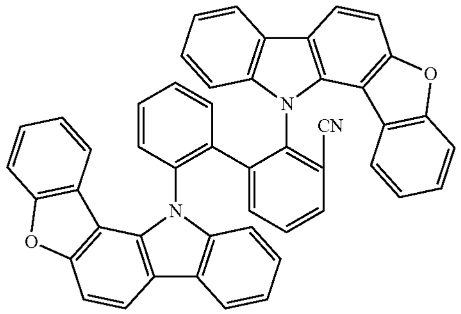
771
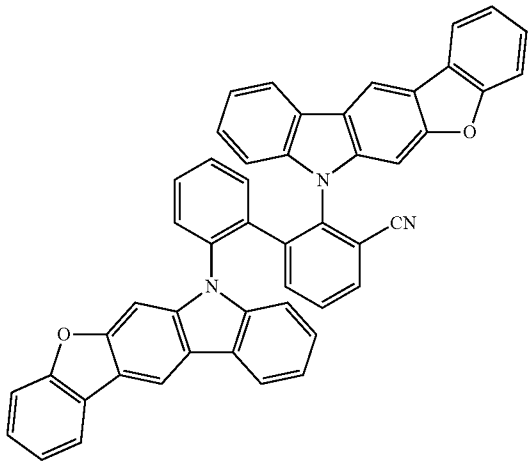
772
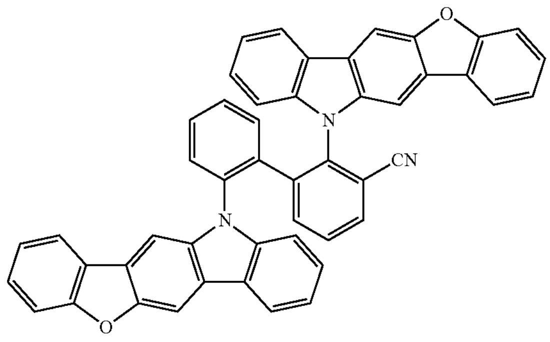
773
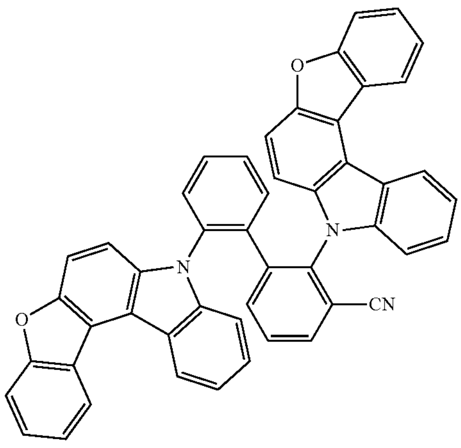

-continued
774
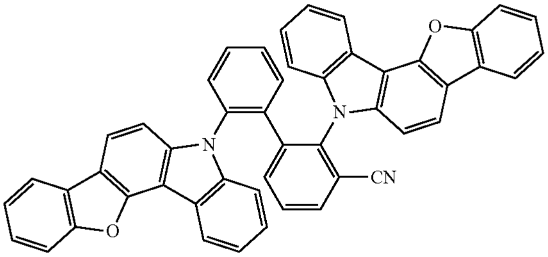
775
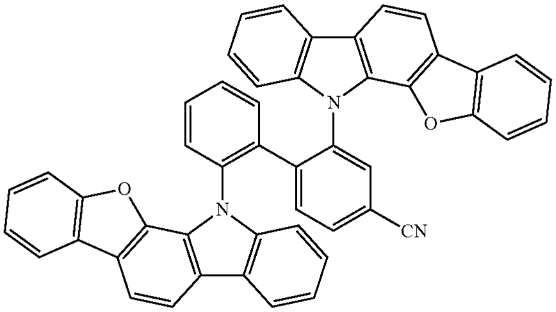
776
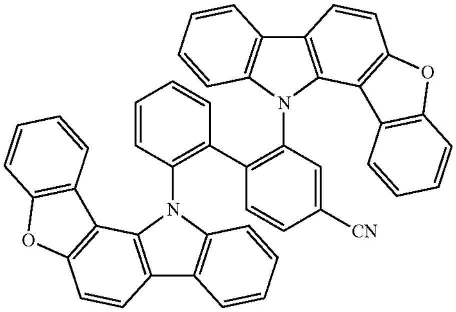
777
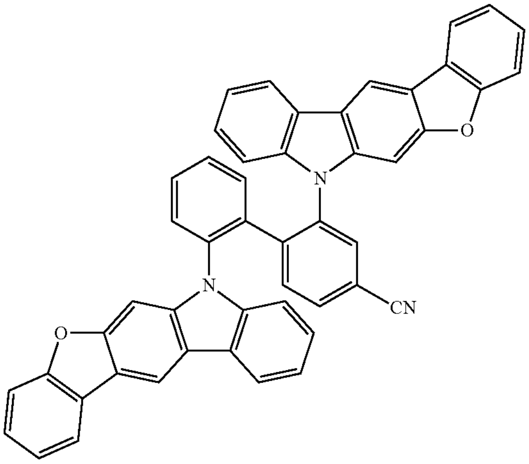
-continued
778
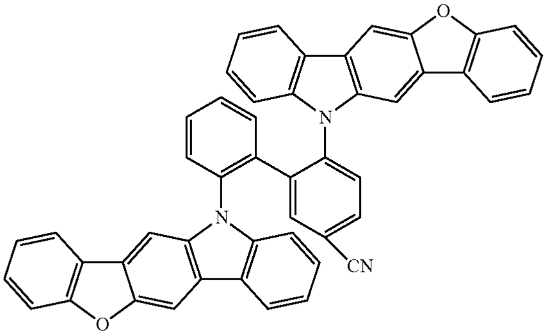
779
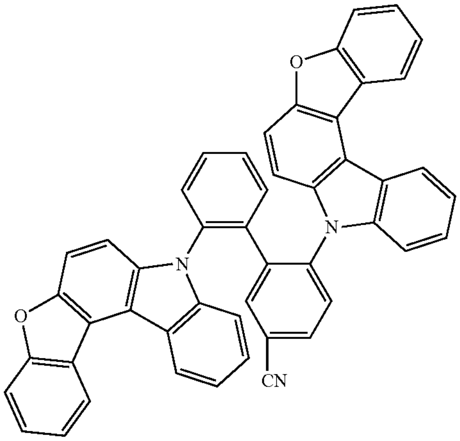
780
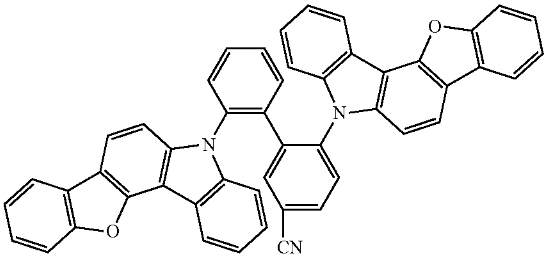
781
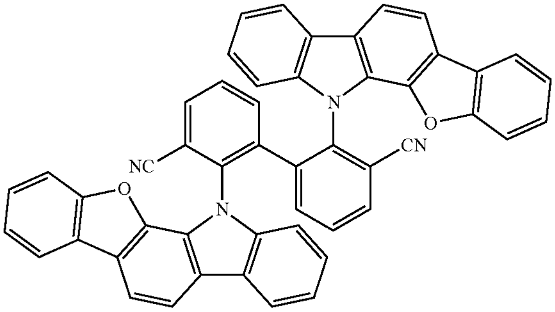

-continued
782
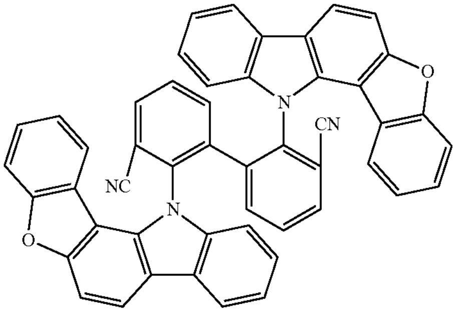
783
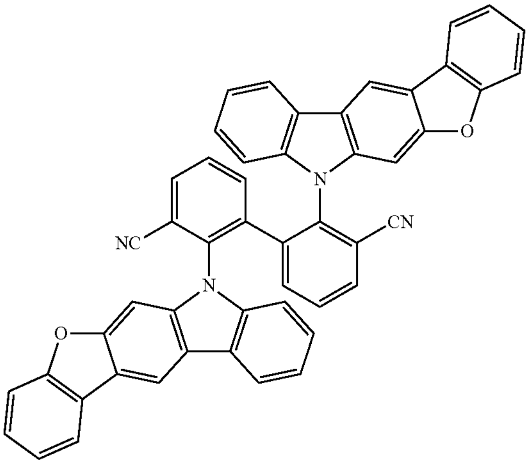
784
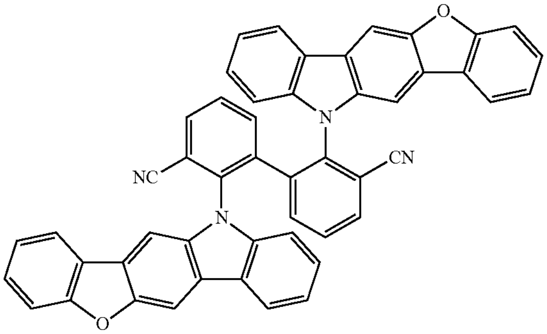
785
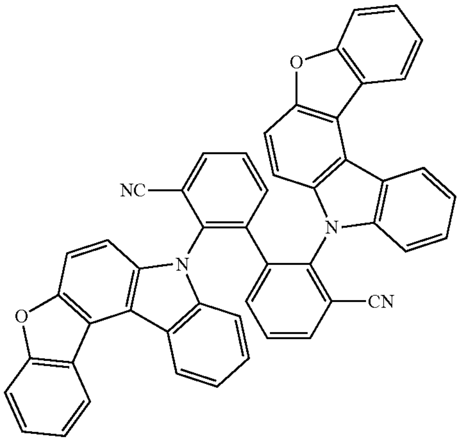
-continued
786
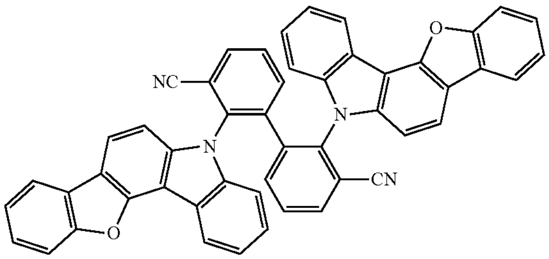
787
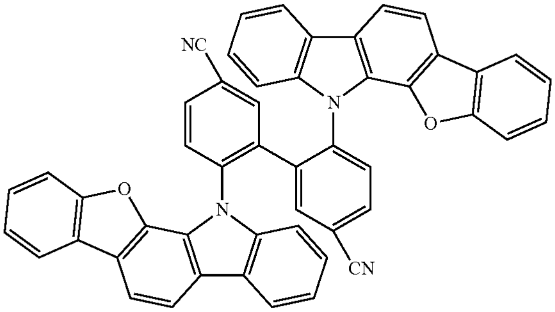
788
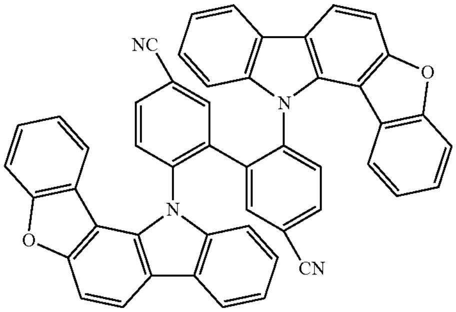
789
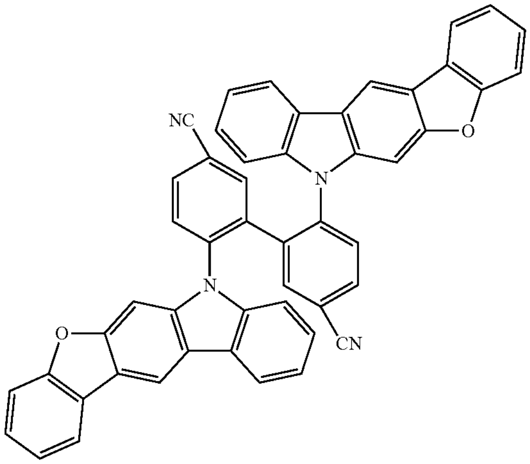

-continued
790
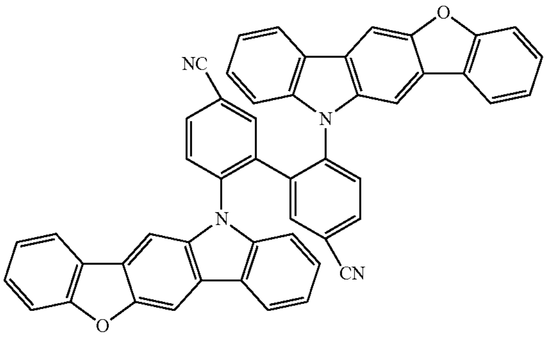
791
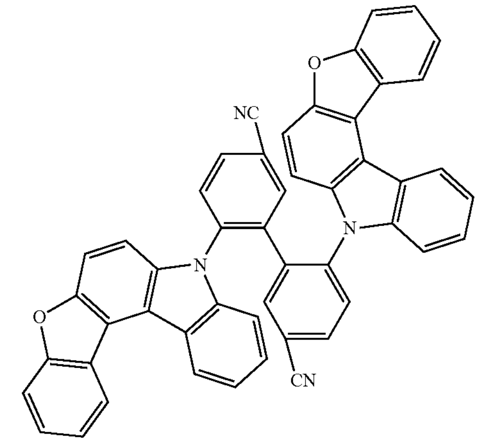
792
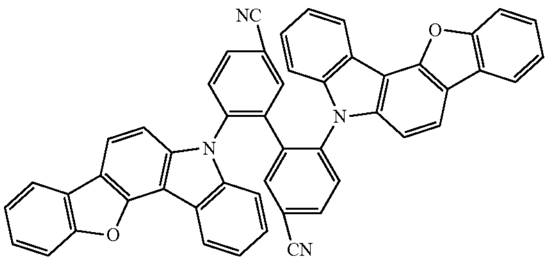
793
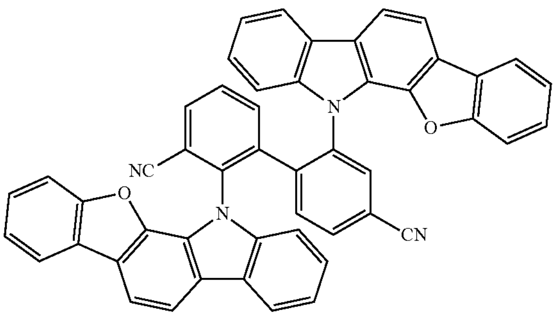
-continued
794
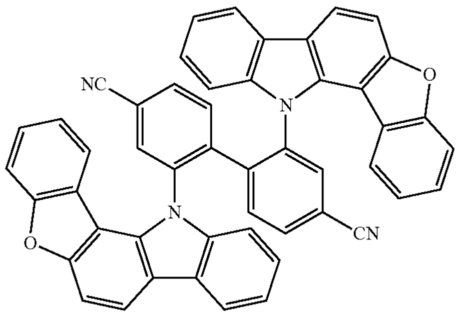
795
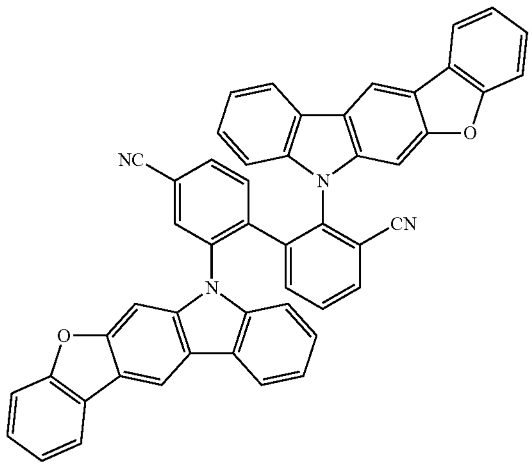
796
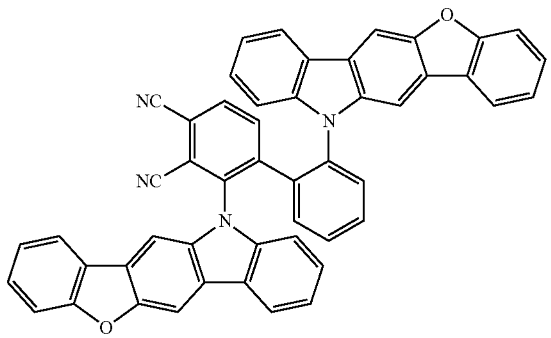
797
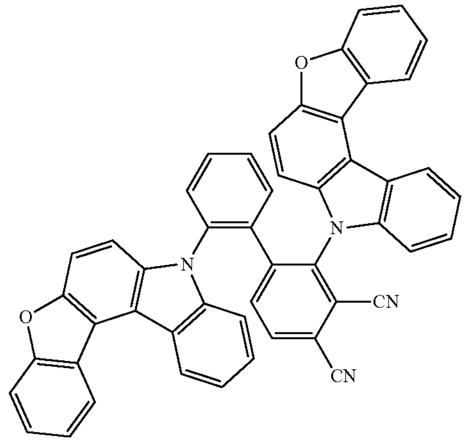

-continued
798
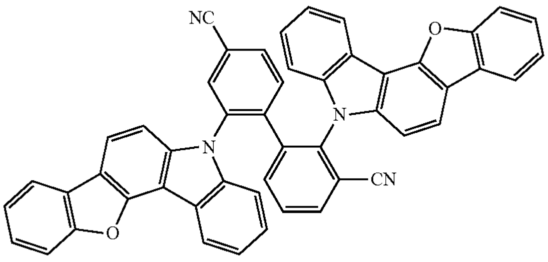
799
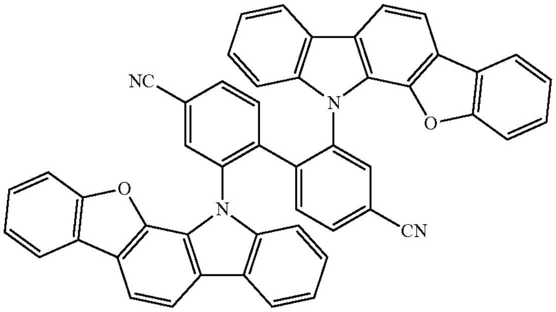
800
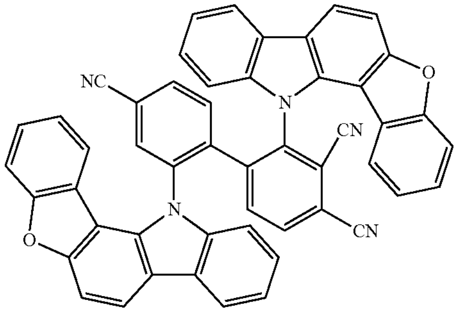
801
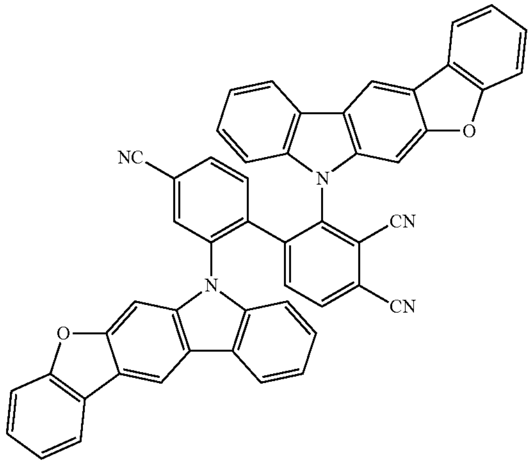
-continued
802
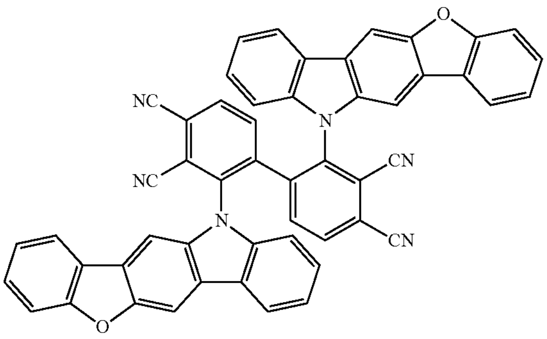
803
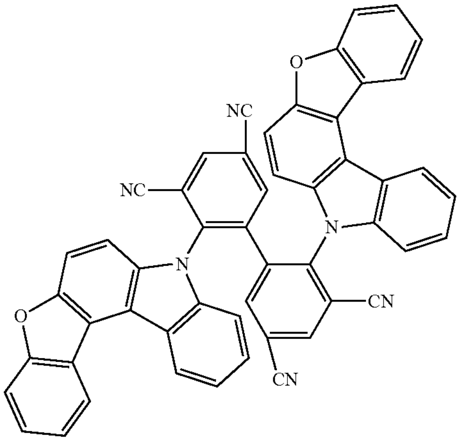
804
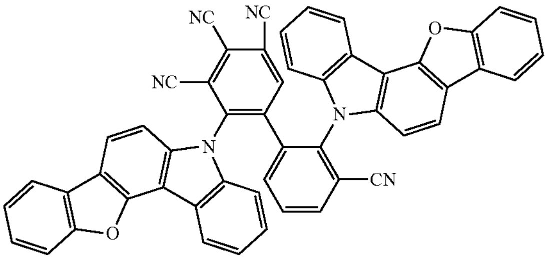
805
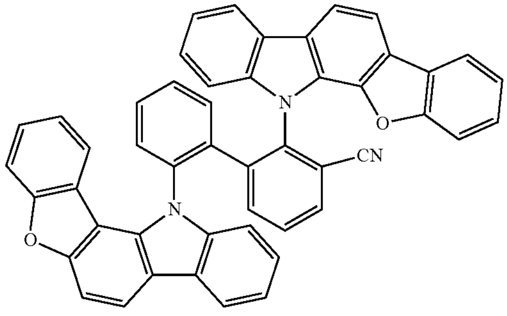

-continued
806
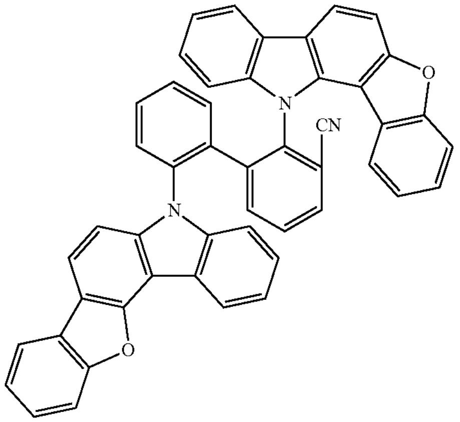
807
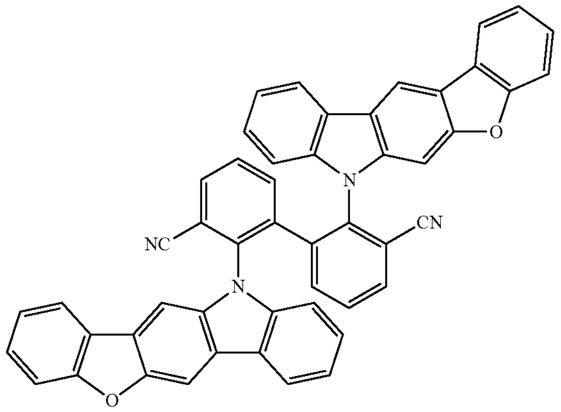
808
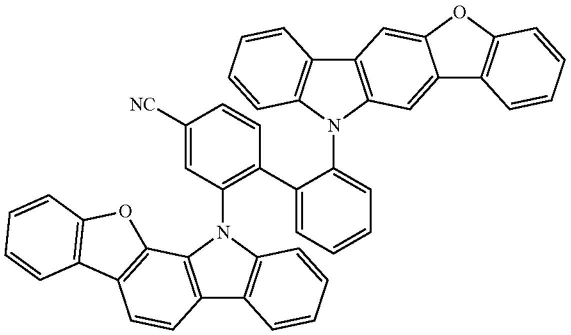
809
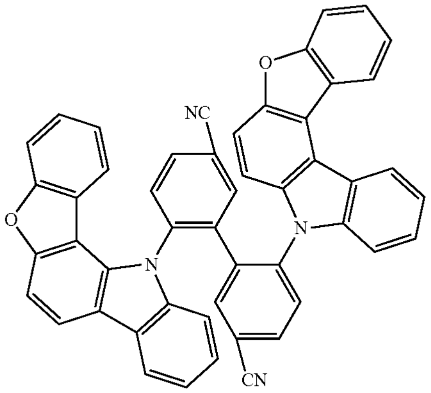
-continued
810
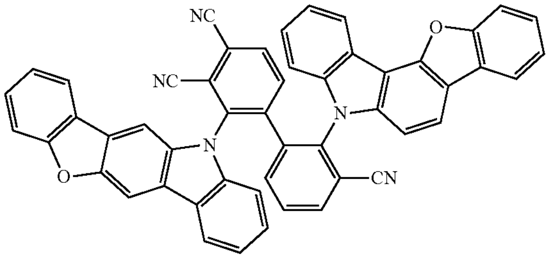
811
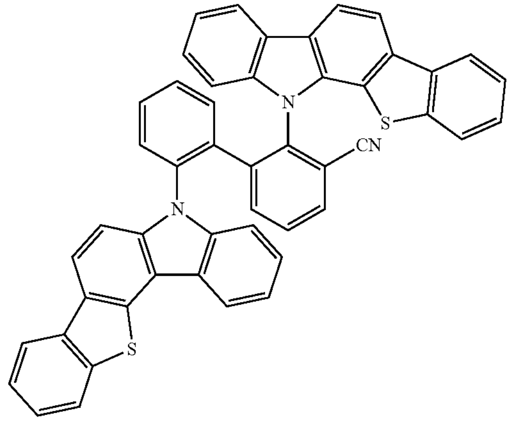
812
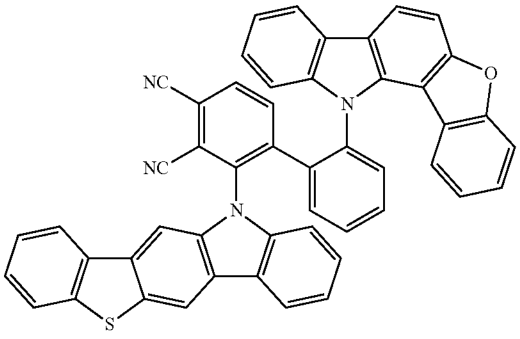
813
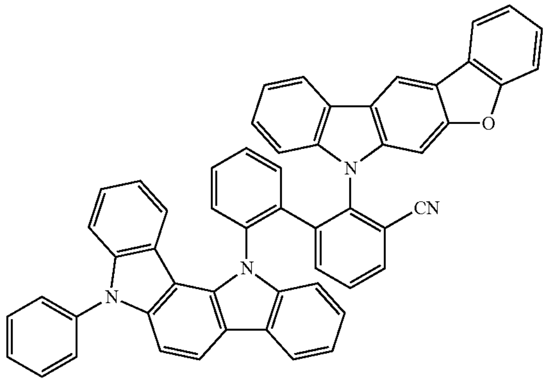

-continued
814
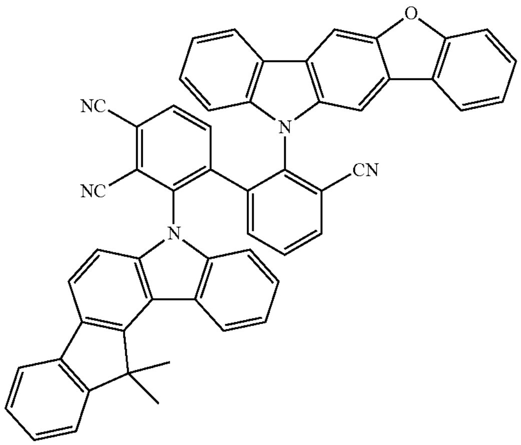
815
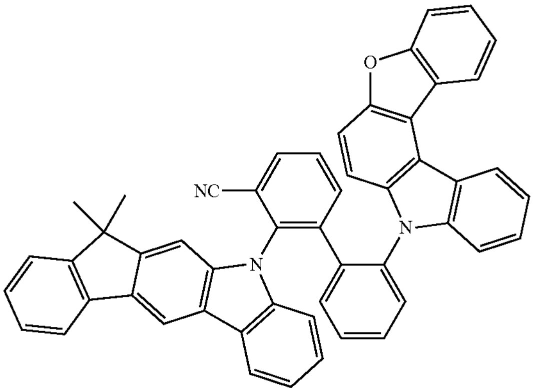
816
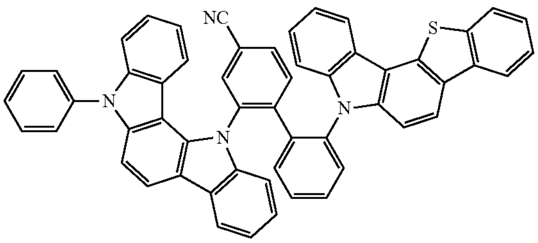
817
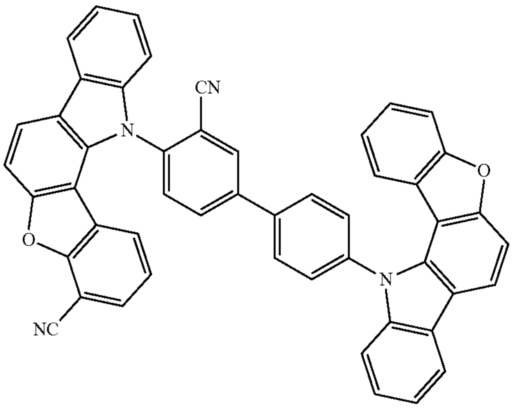
-continued
818
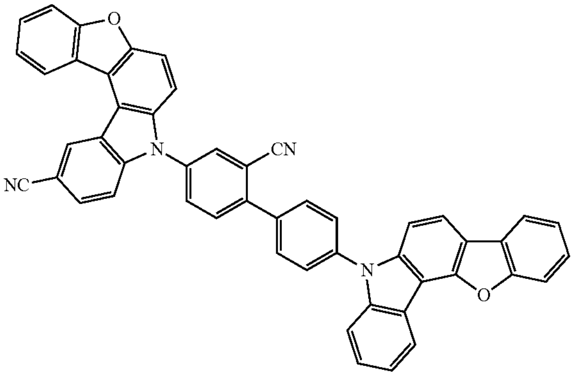
819
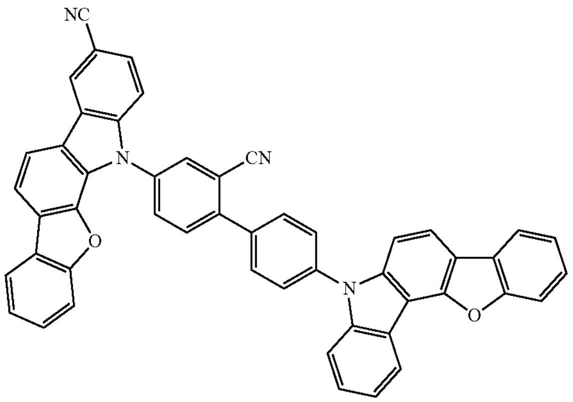
820
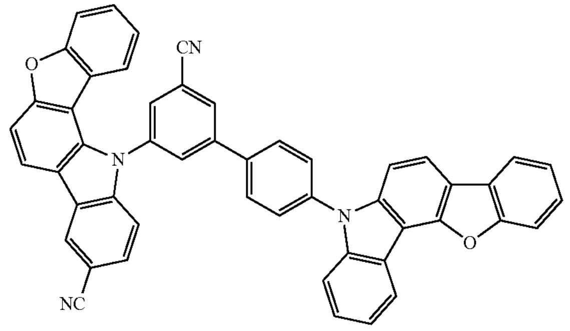
821
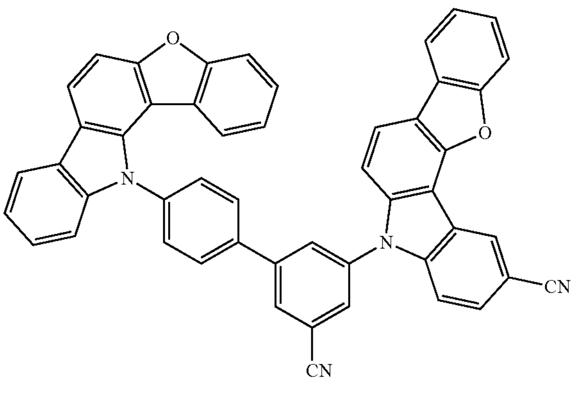

-continued
822
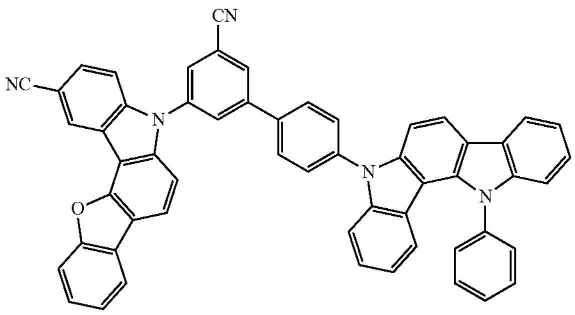
823
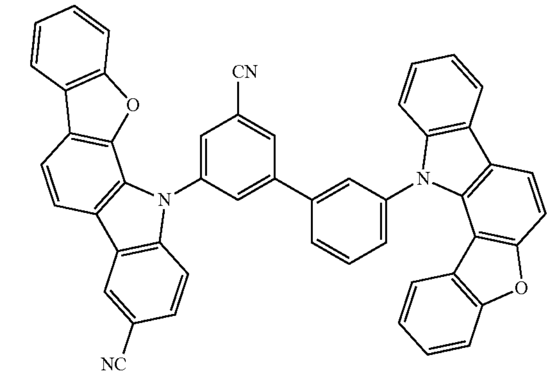
824
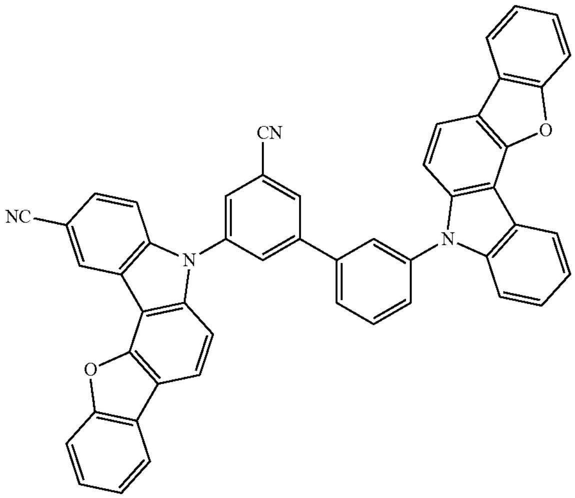
-continued
825
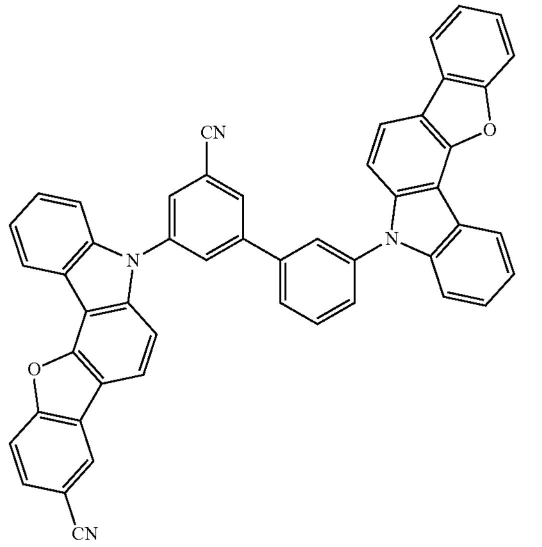
826
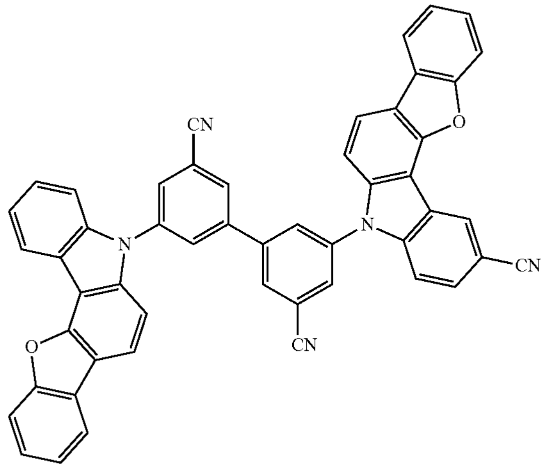
827
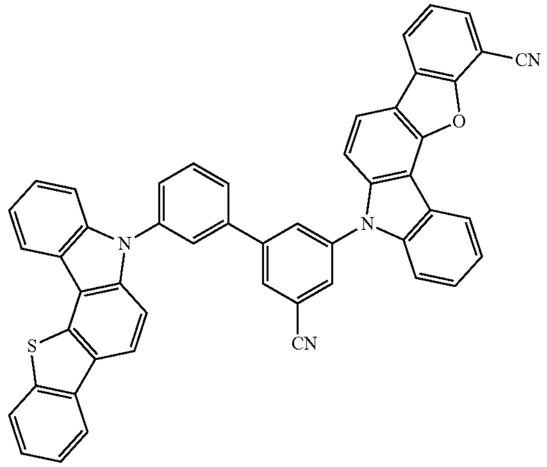

-continued
828
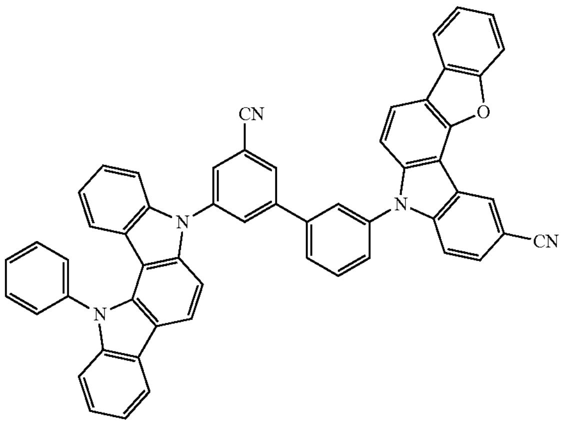
829
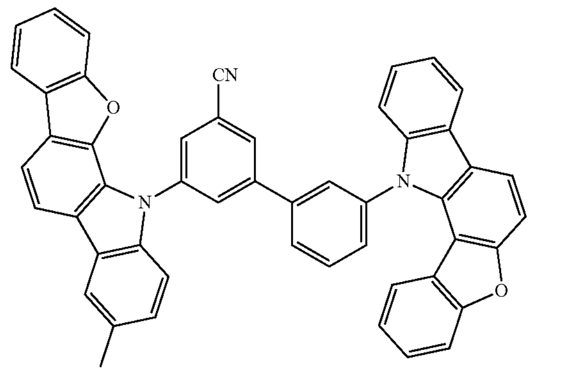
830
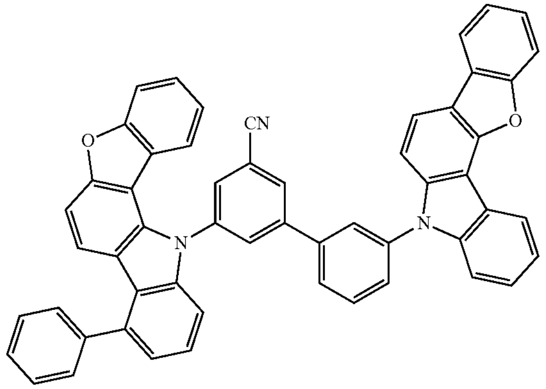
831
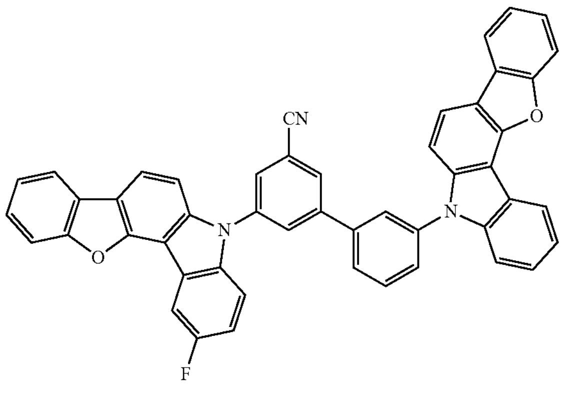
-continued
832
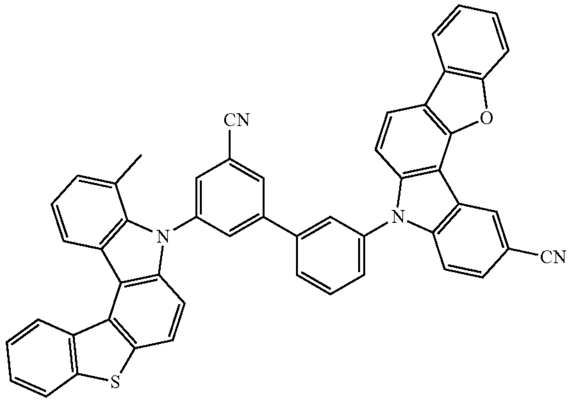
833
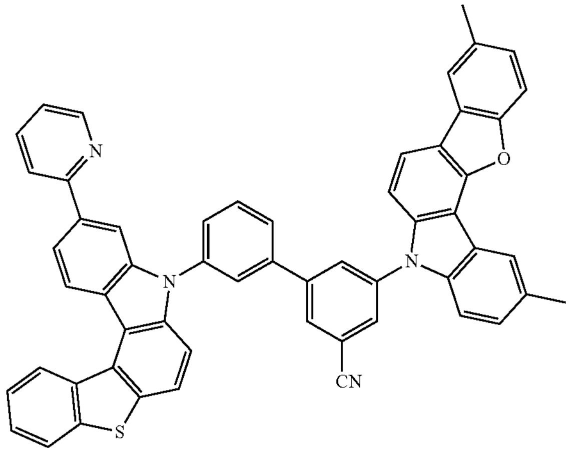
834
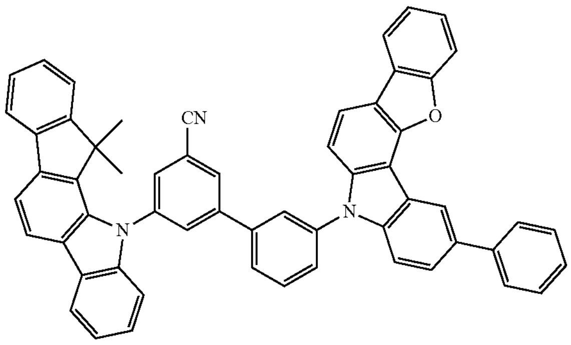
835
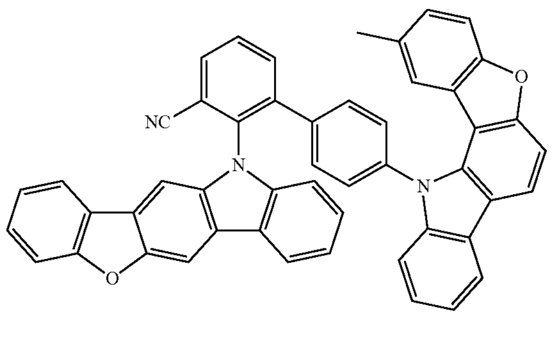

836
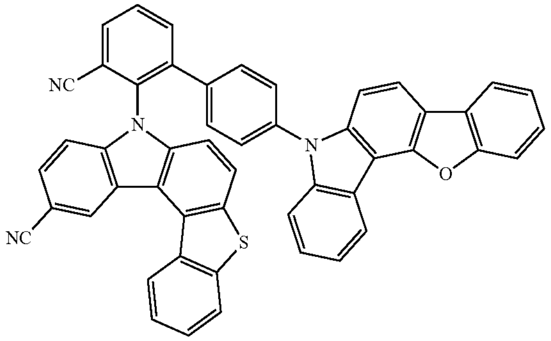
837
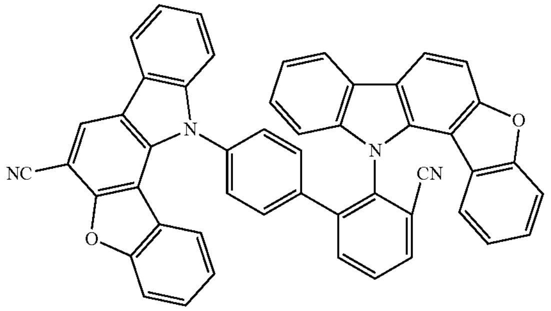
838
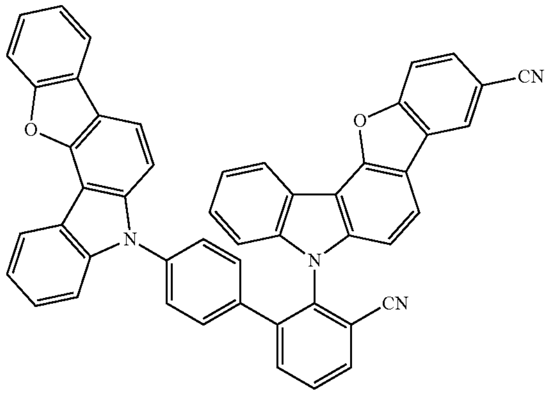
839
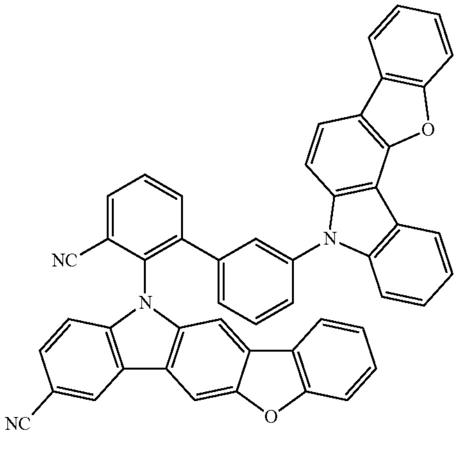
840
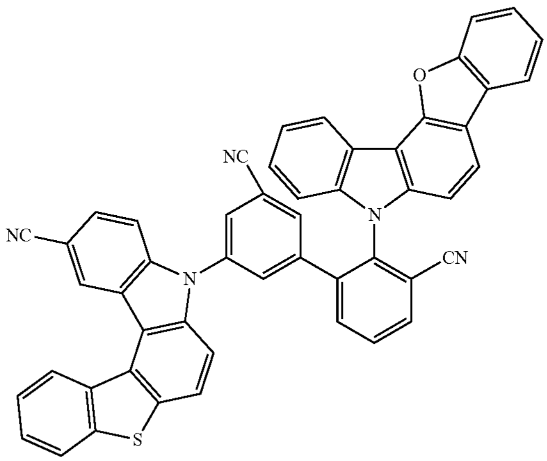
841
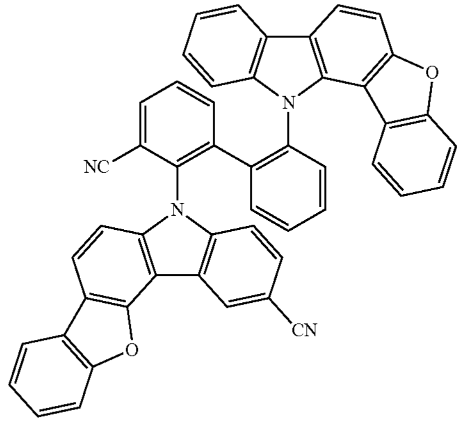
842
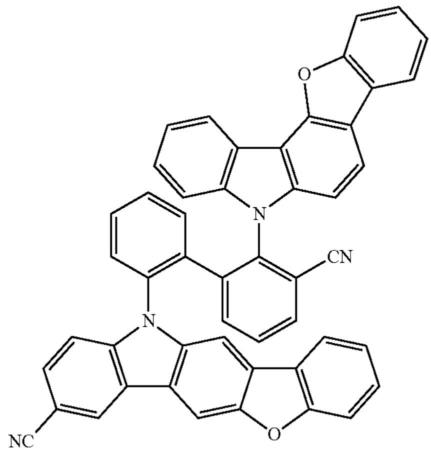

-continued
843
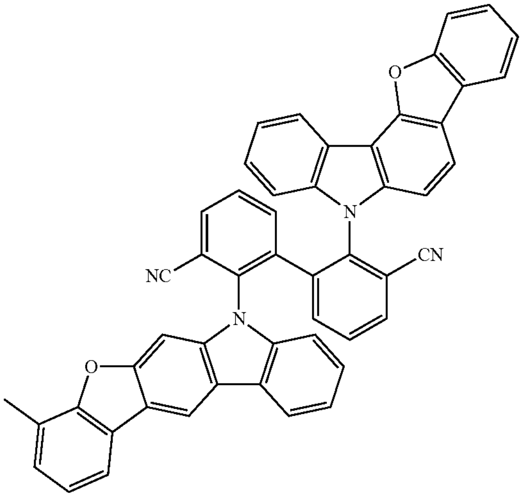
844
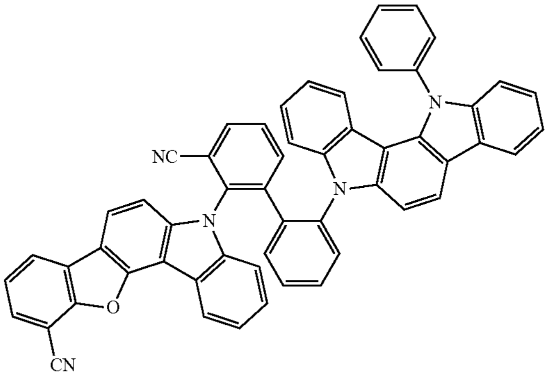
845
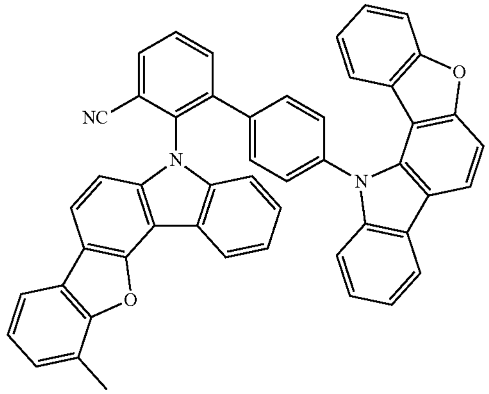
-continued
846
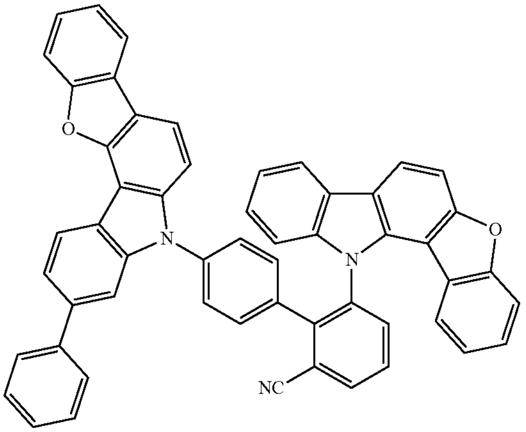
847
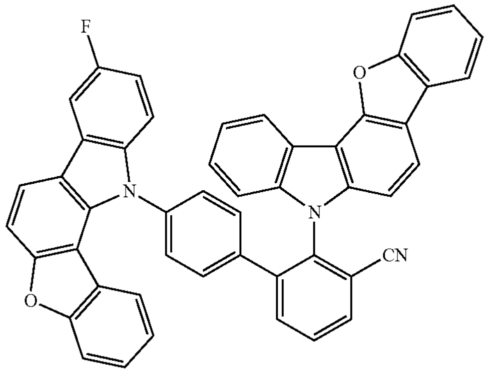
848
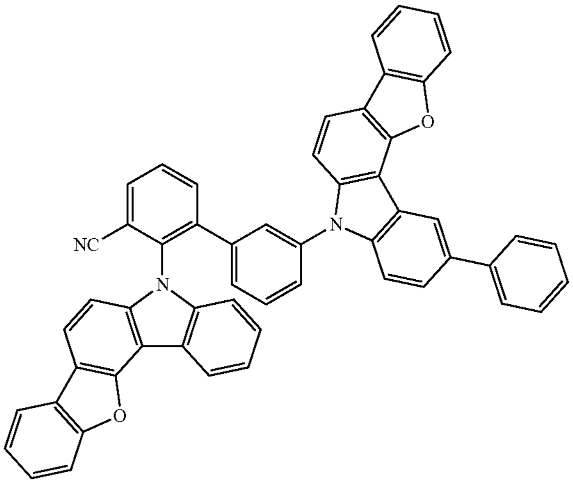

-continued
849
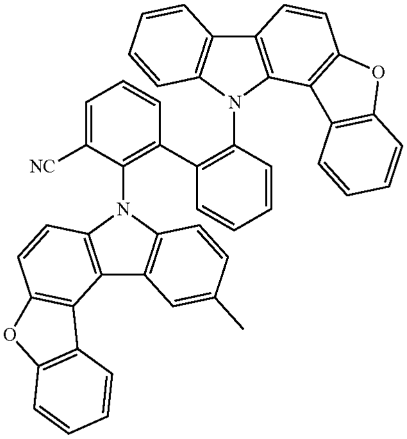
850
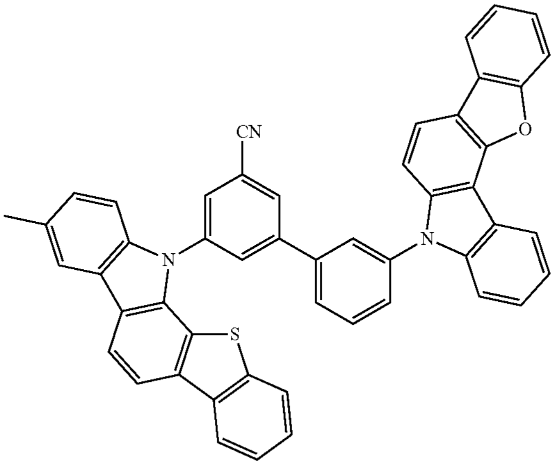
851
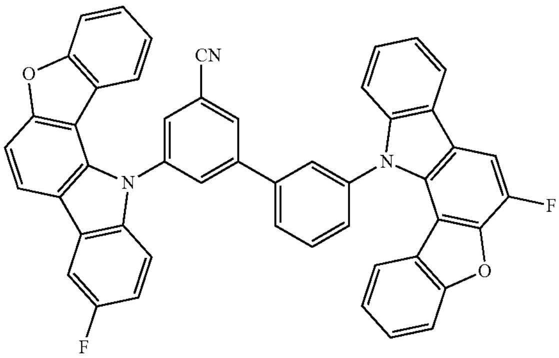
-continued
852
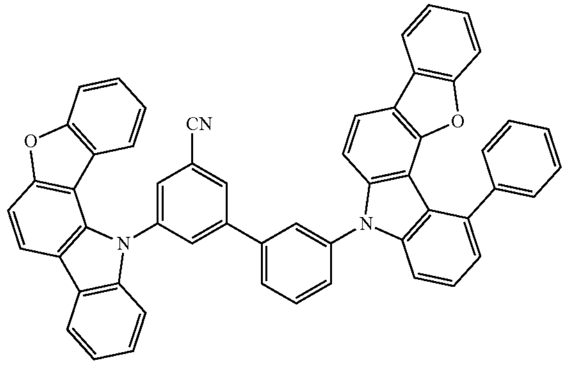
Group HE3
1
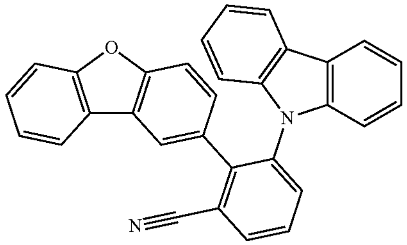
2
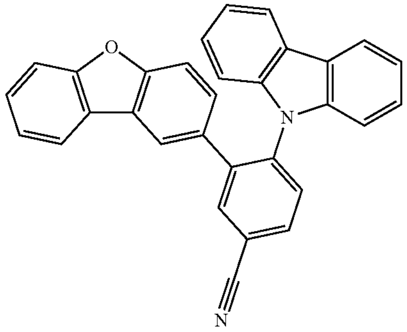
3
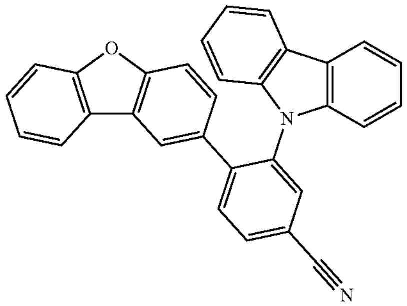

-continued
4
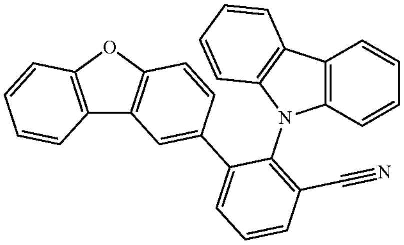
5
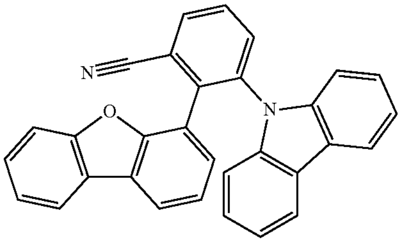
6
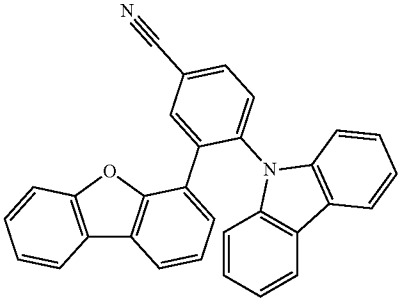
7
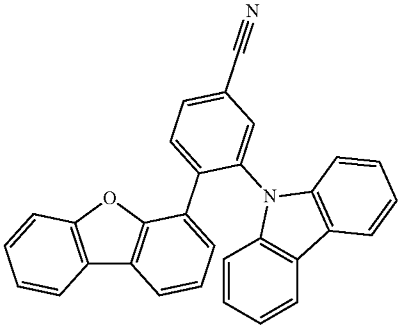
8
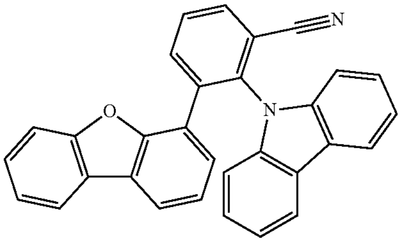
9
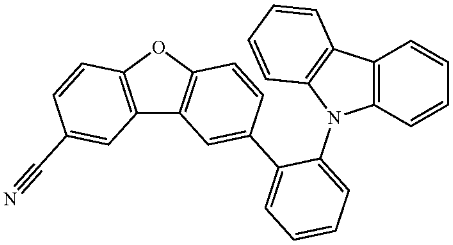
-continued
10
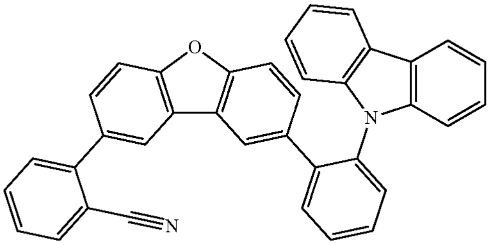
11
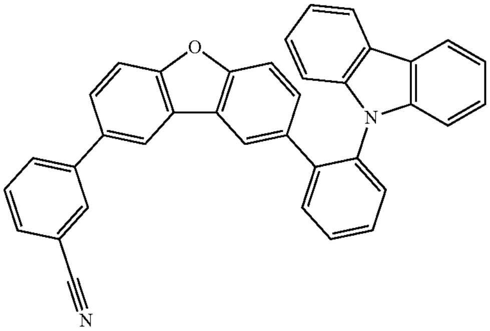
12
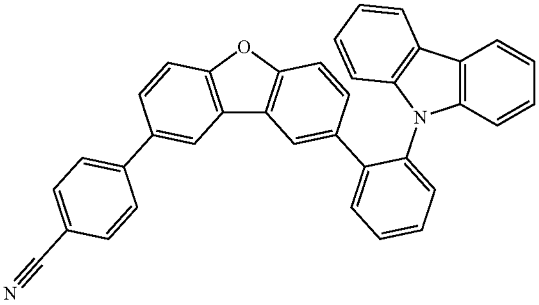
13
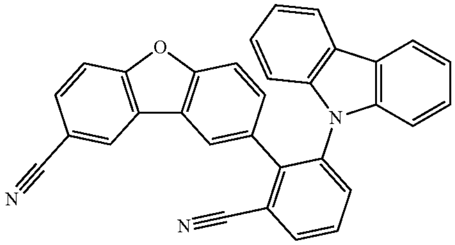
14
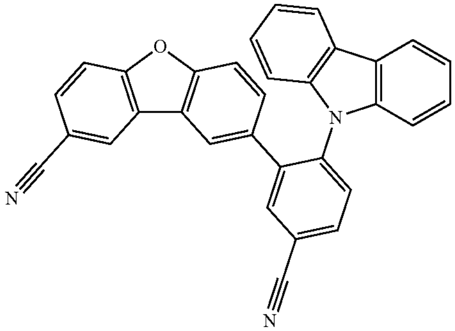

-continued
15
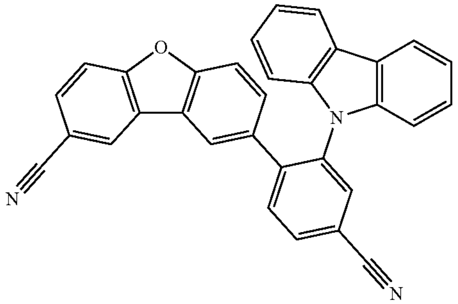
16
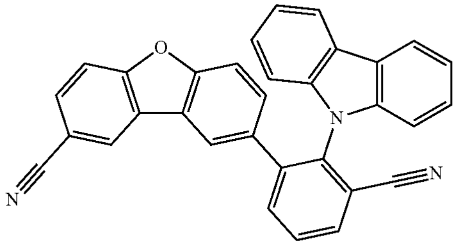
17
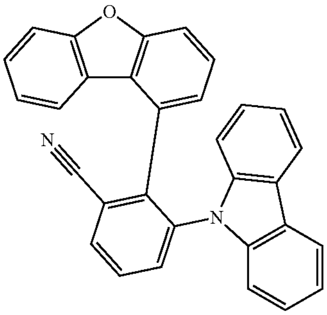
18
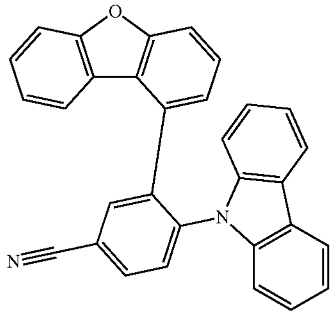
19
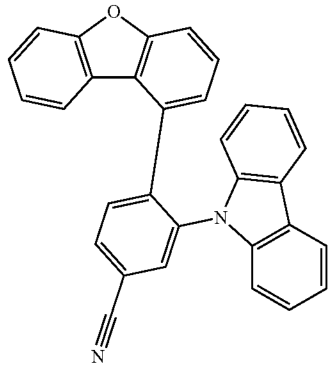
-continued
20
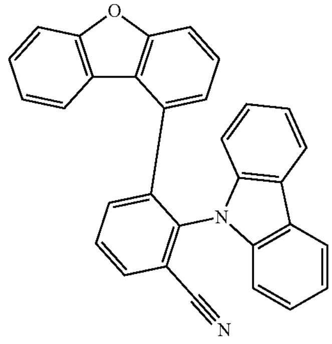
21
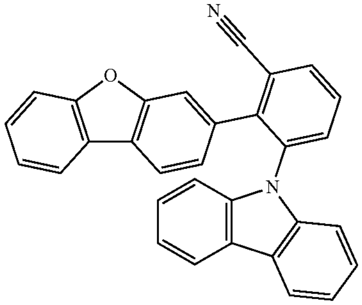
22
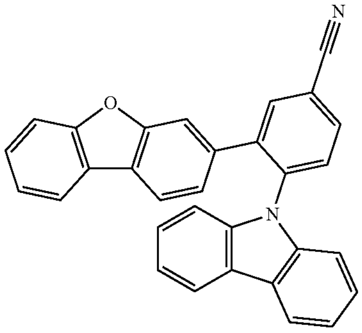
23
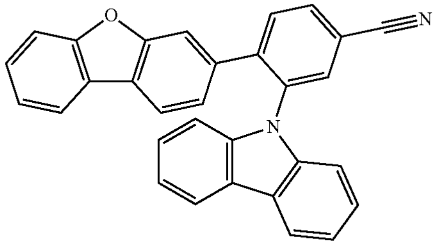
24
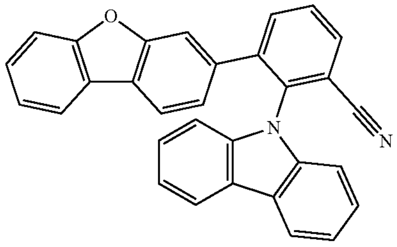

-continued
25
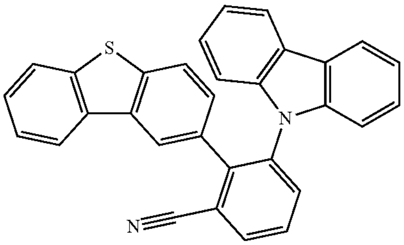
26
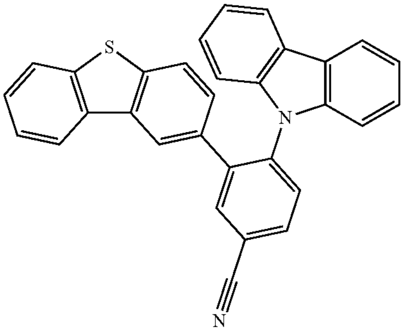
27
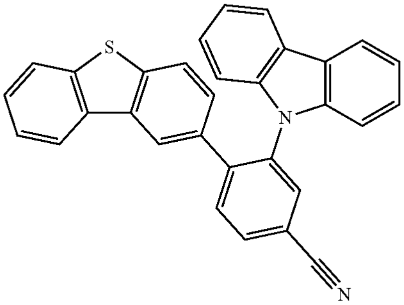
28
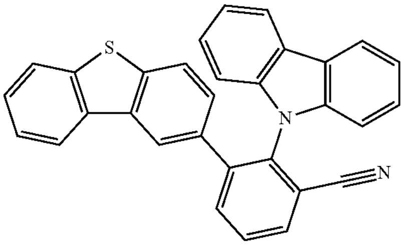
29
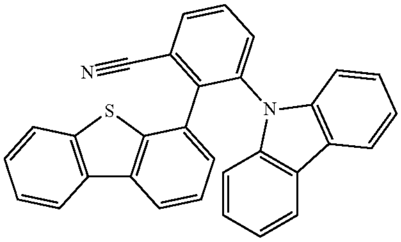
-continued
30
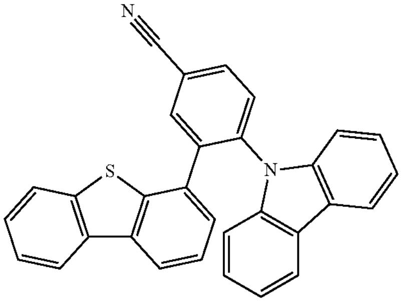
31
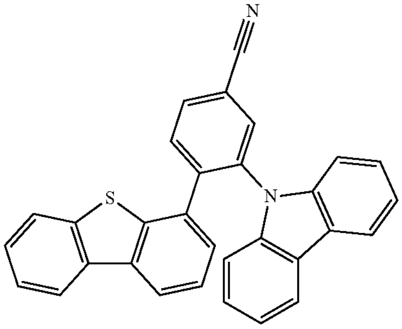
32
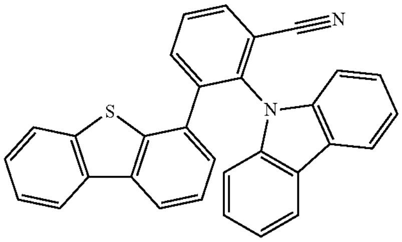
33
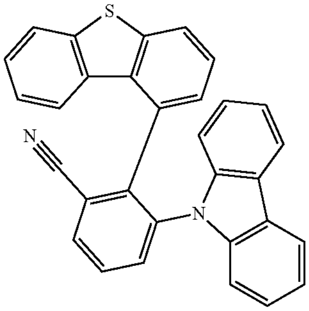
34
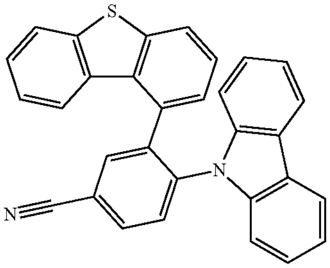

-continued
35
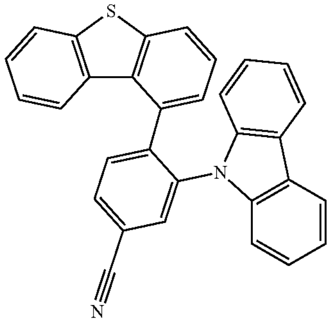
36
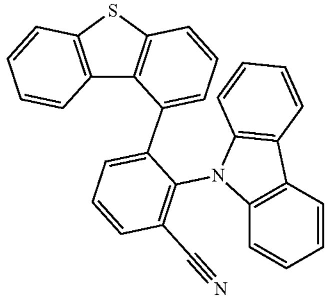
37
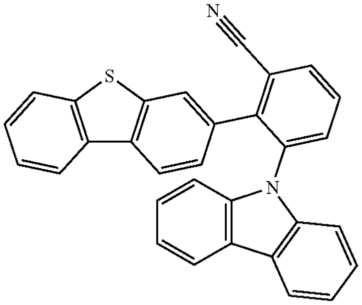
38
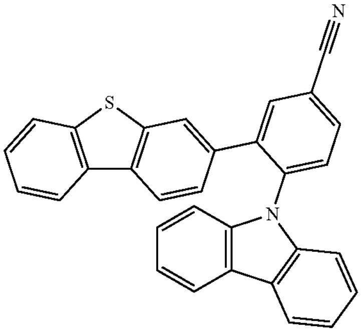
39
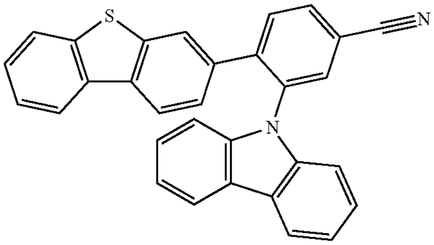
-continued
40
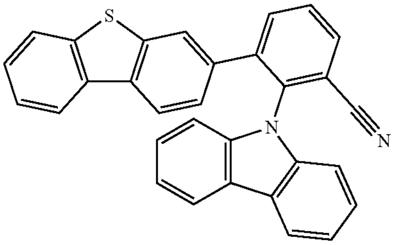
41
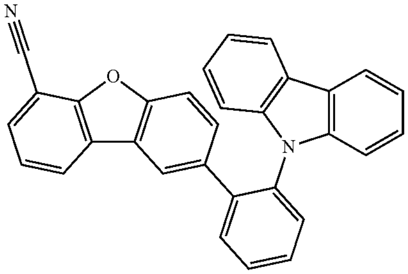
42
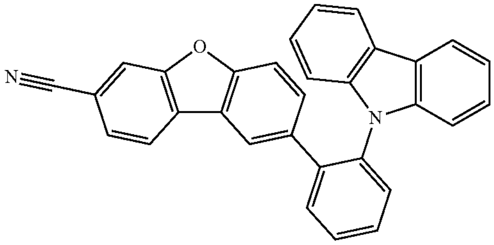
43
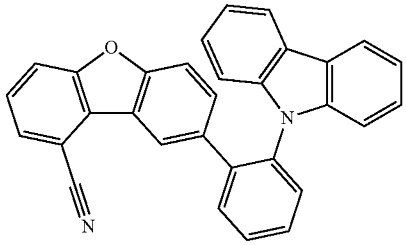
44
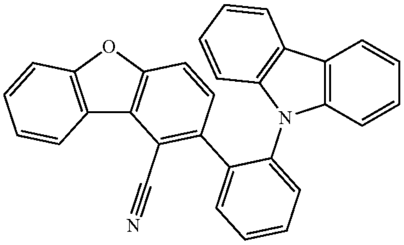

-continued
45
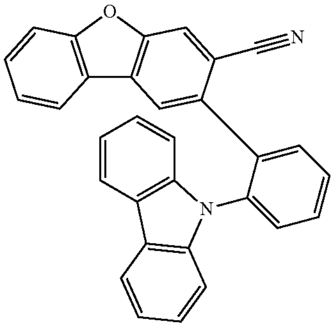
46
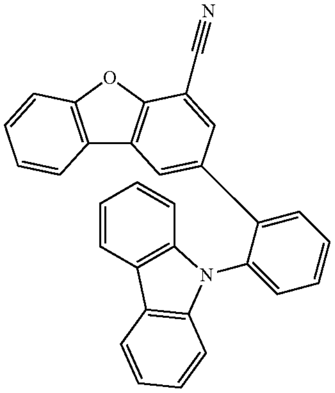
47
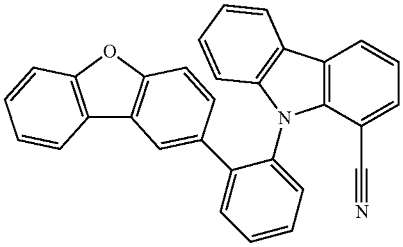
48
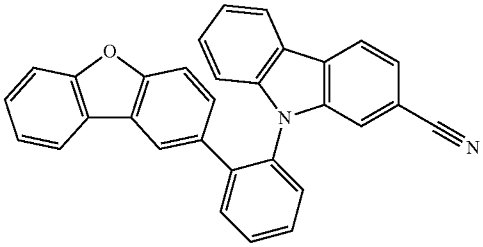
49
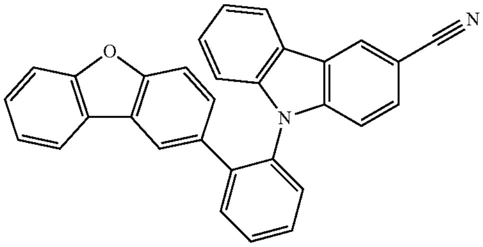
50
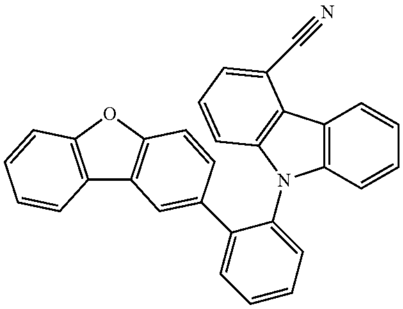
51
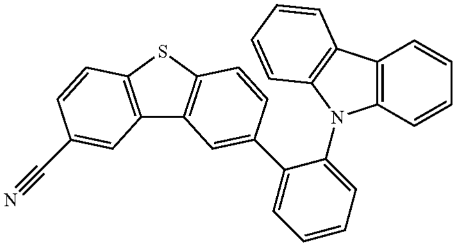
52
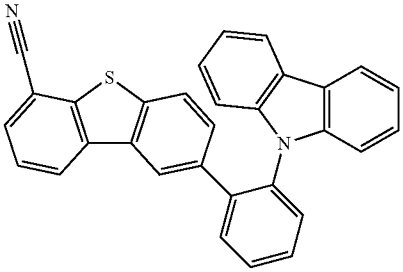
53
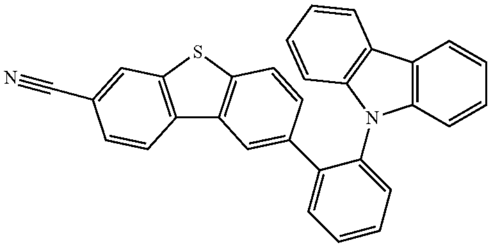
54
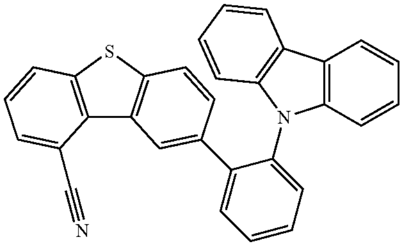
55
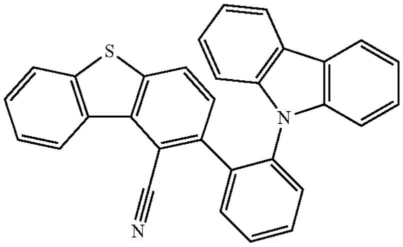

-continued
56
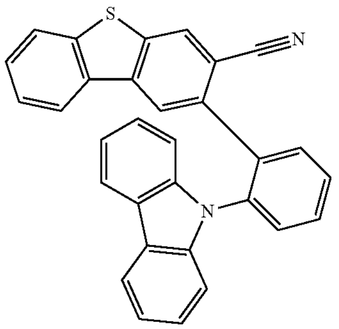
57
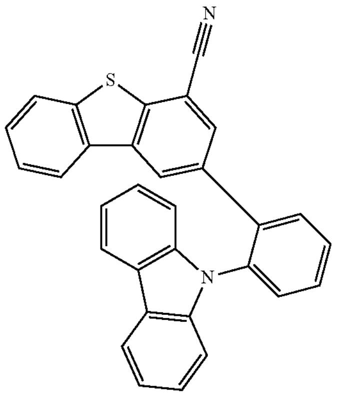
58
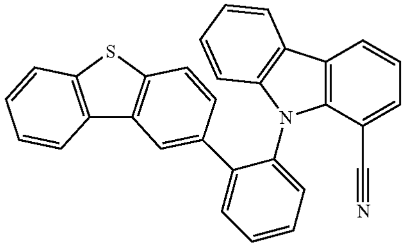
59
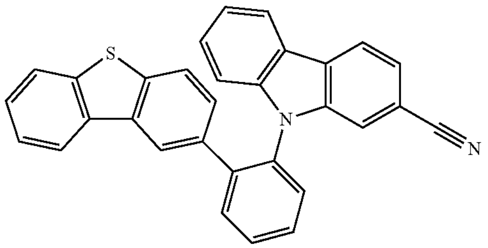
60
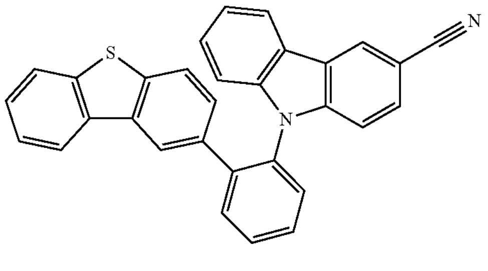
-continued
61
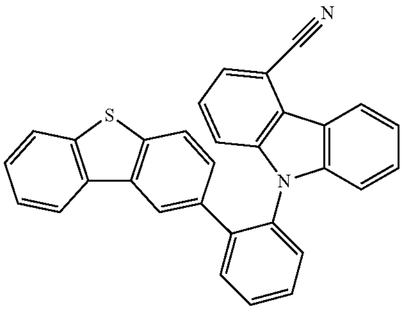
62
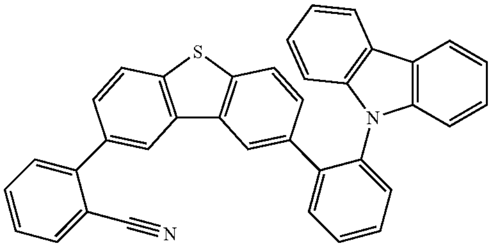
63
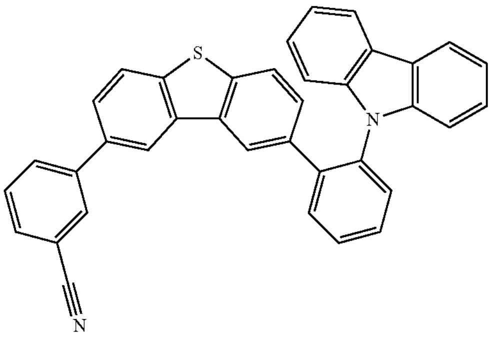
64
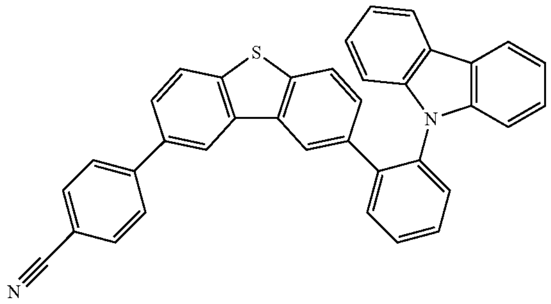
65
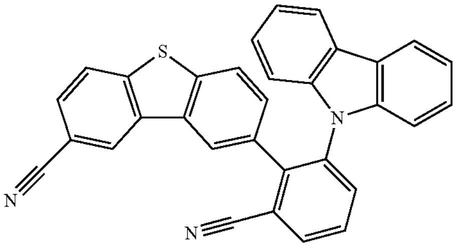

66
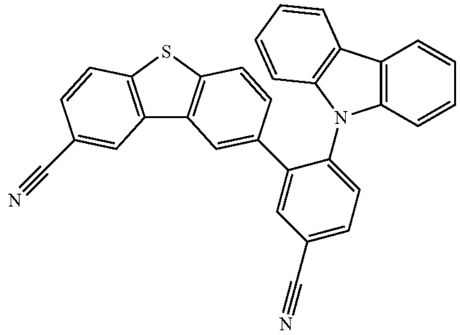
67
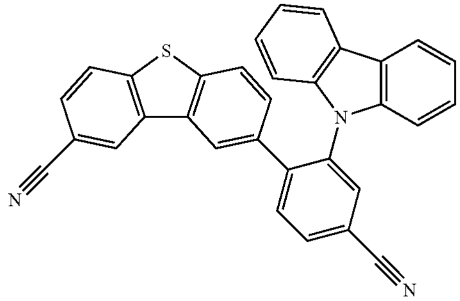
68
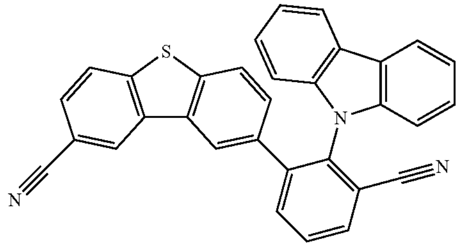
69
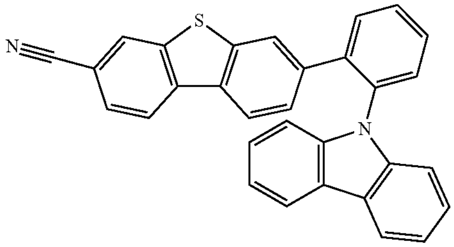
70
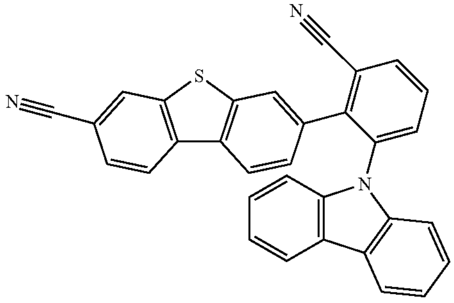
71
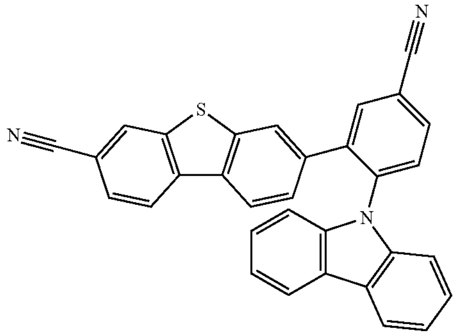
72
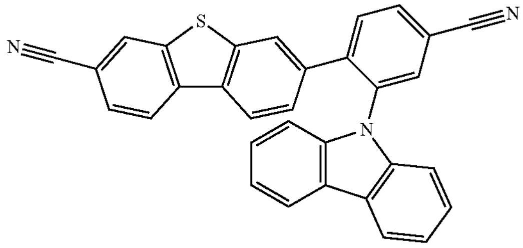
73
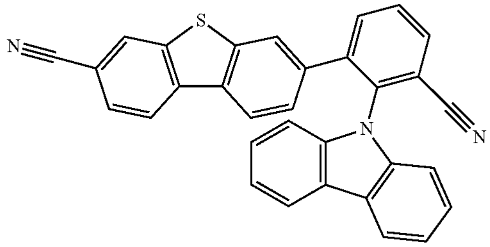
74
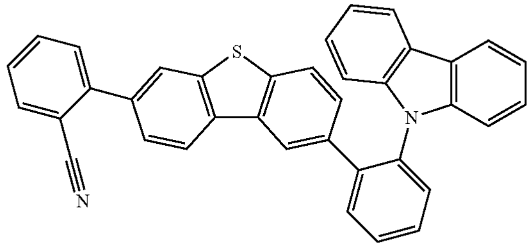
75
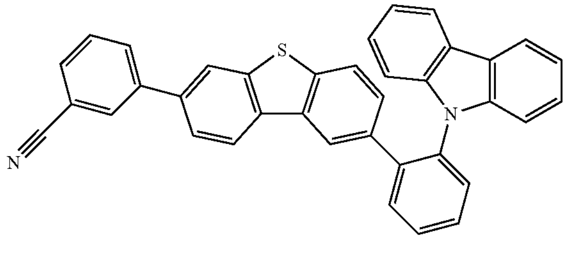

-continued
76
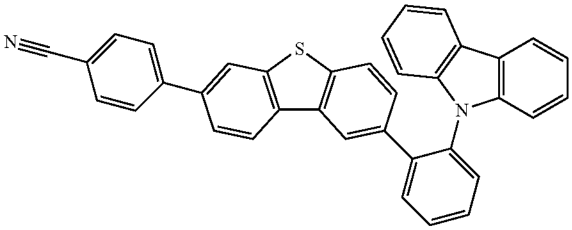
77
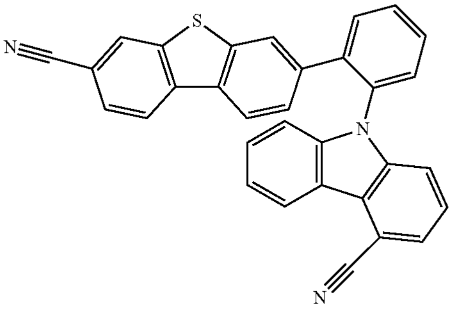
78
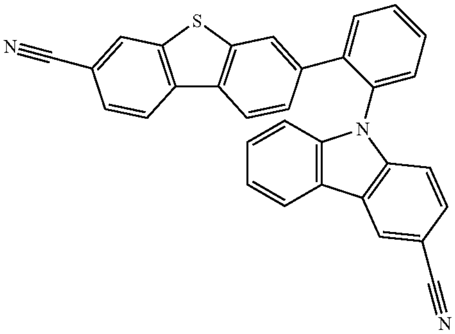
79
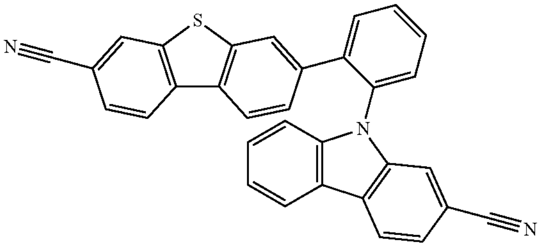
80
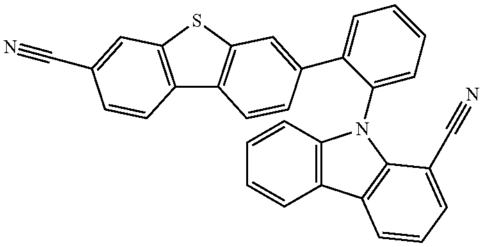
-continued
81
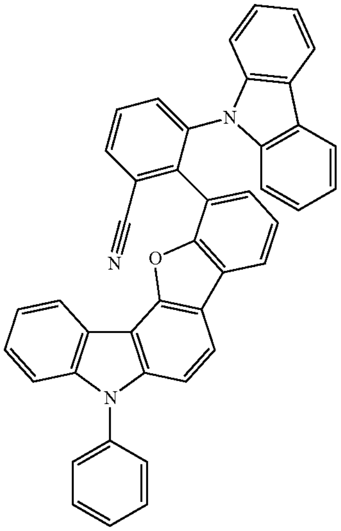
82
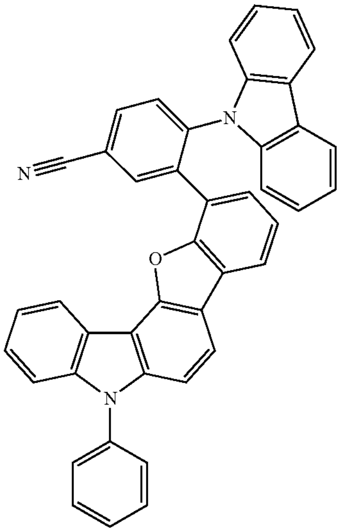
83
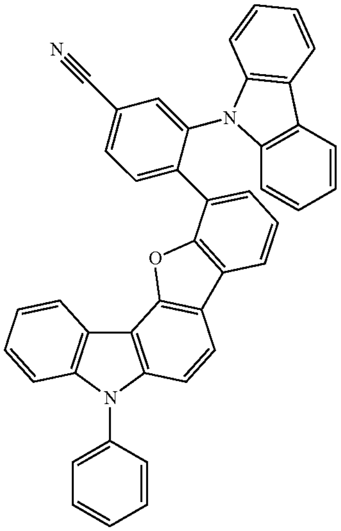

-continued
84
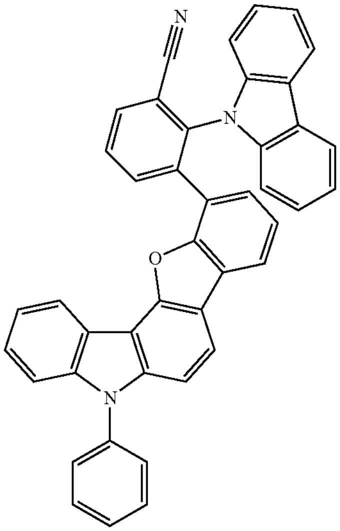
85
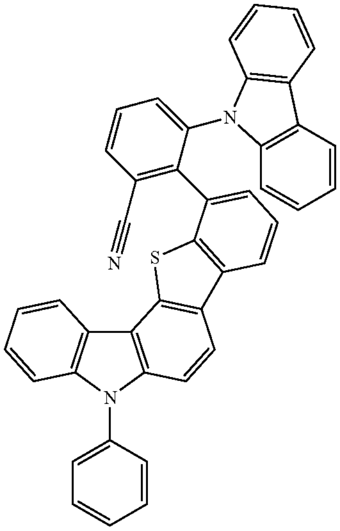
86
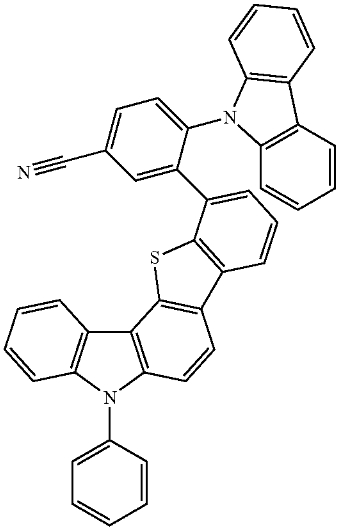
-continued
87
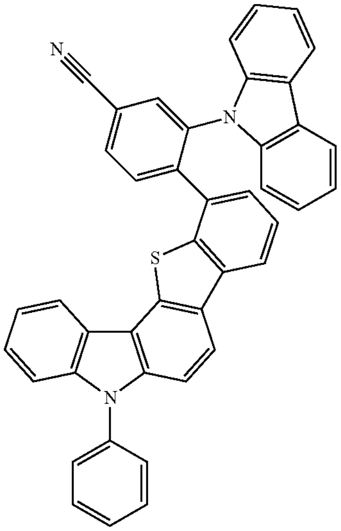
88
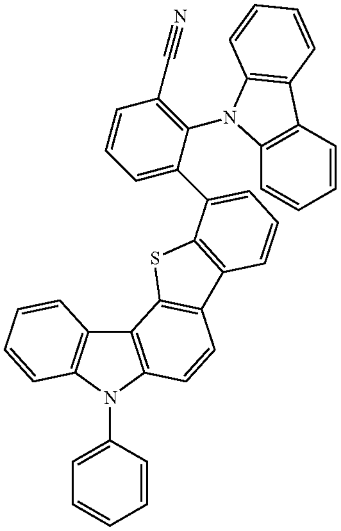

-continued
89
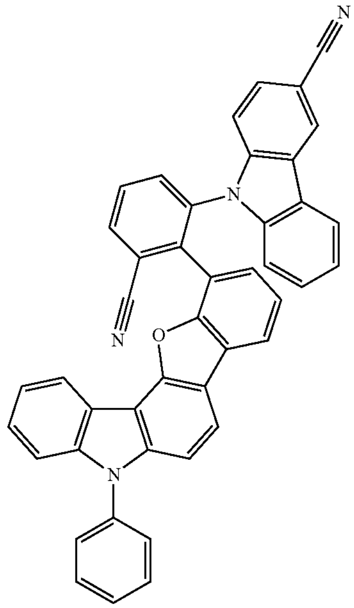
91
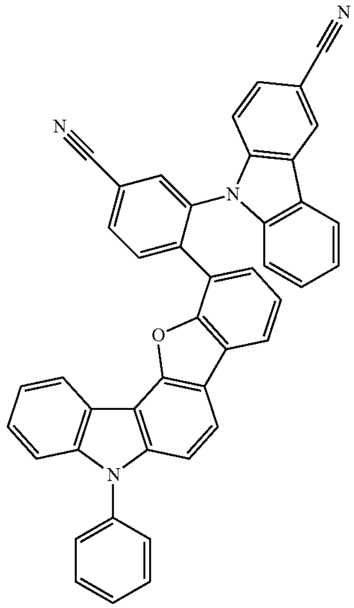
90
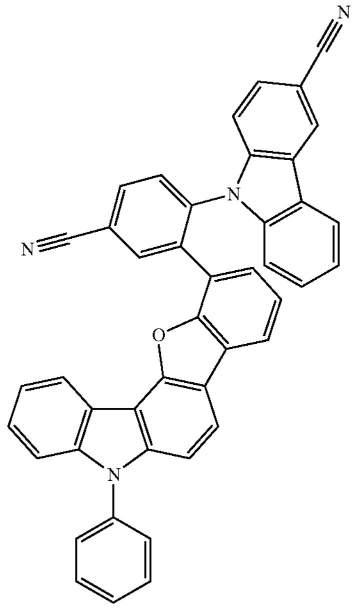
92
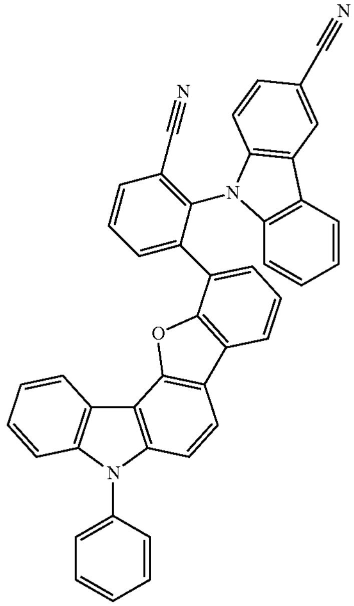

93
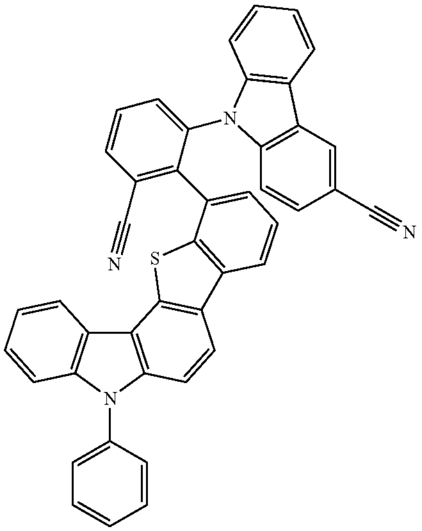
94
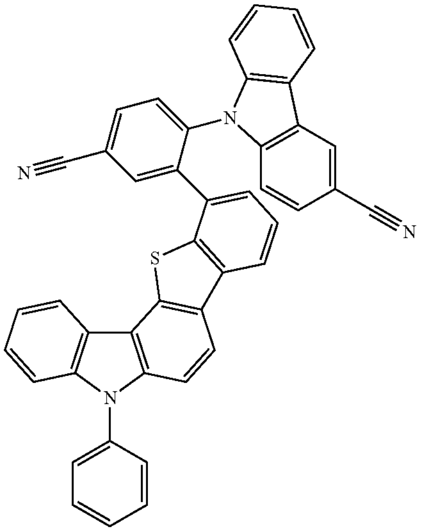
95
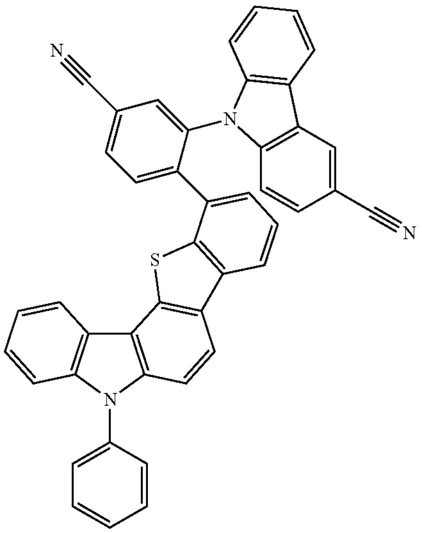
96
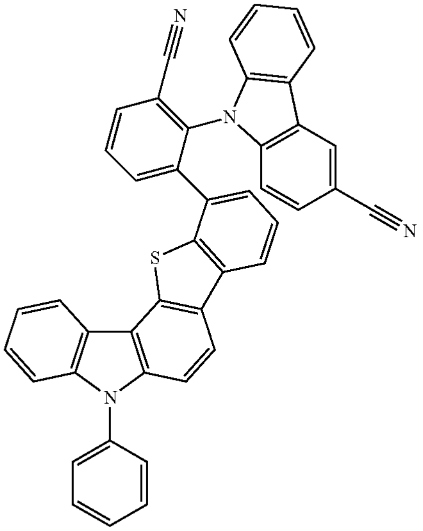
97
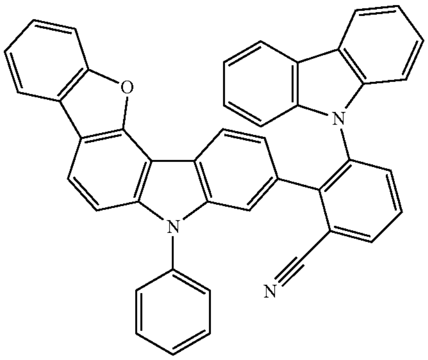
98
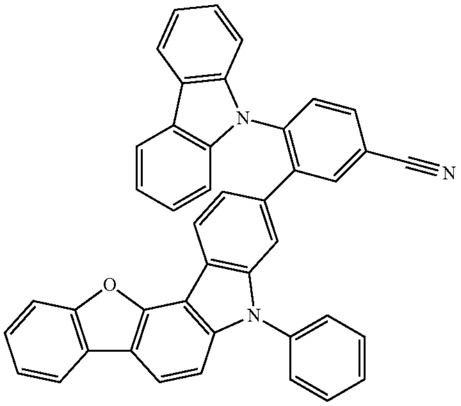

-continued
99
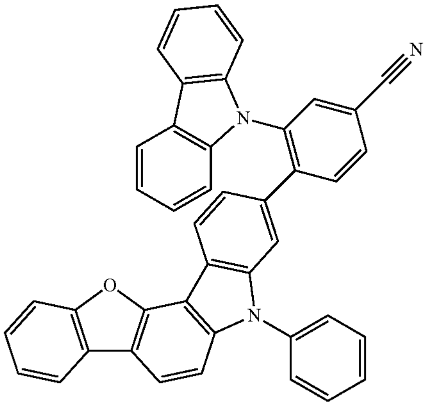
100
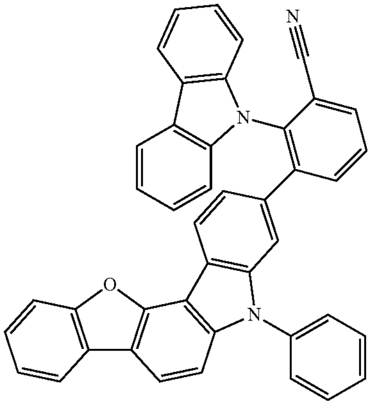
101
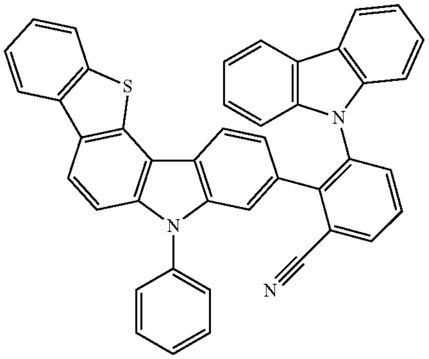
102
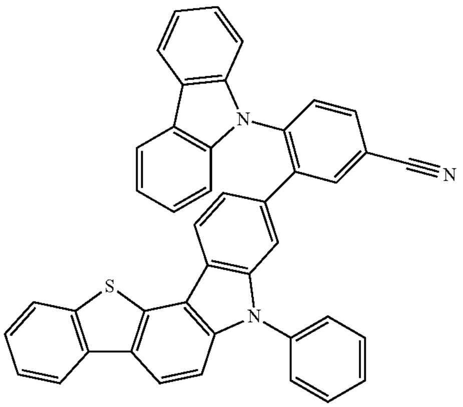
-continued
103
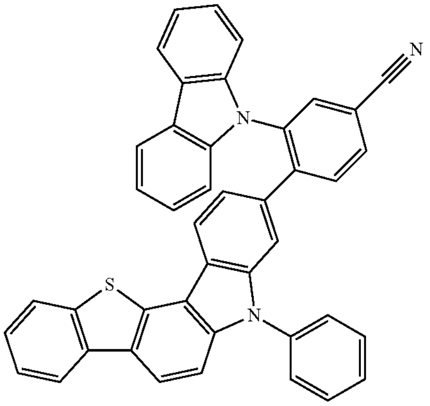
104
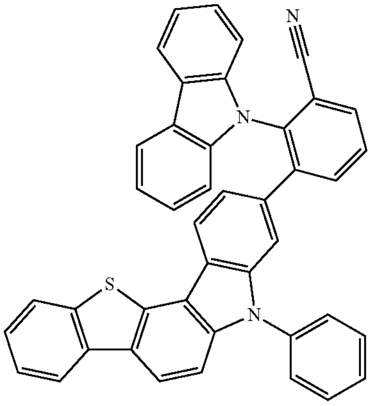
105
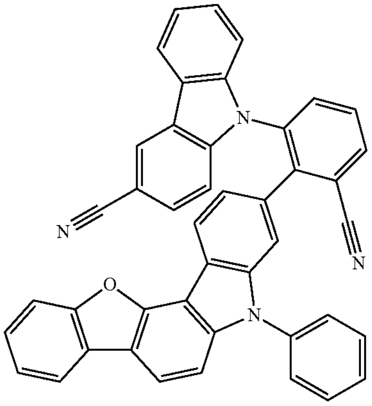
106
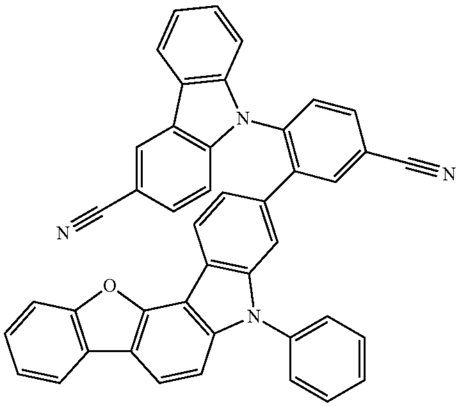

-continued
107
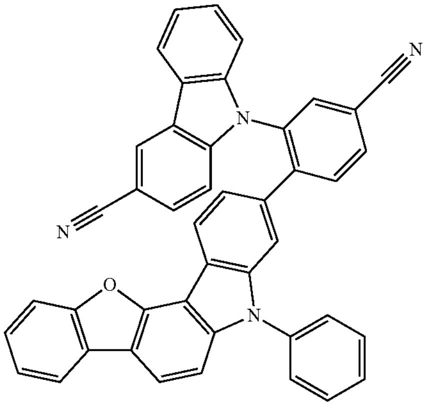
108
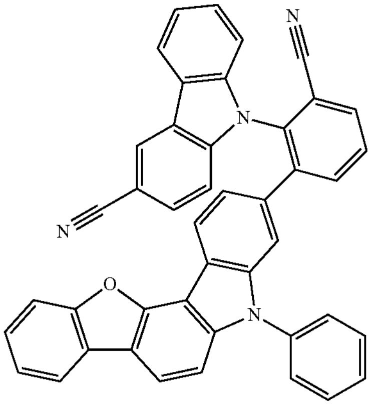
109
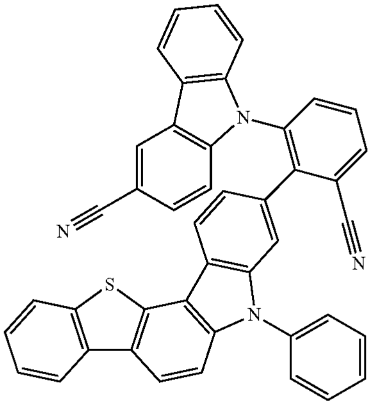
-continued
110
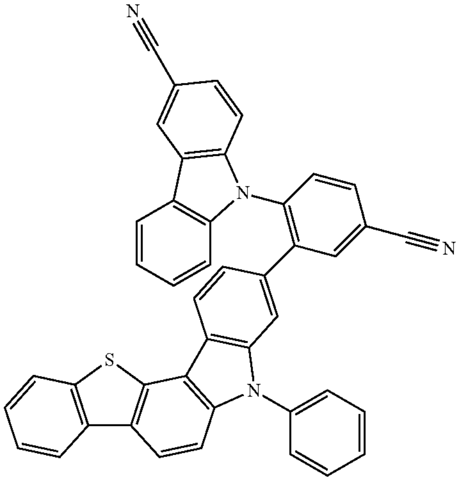
111
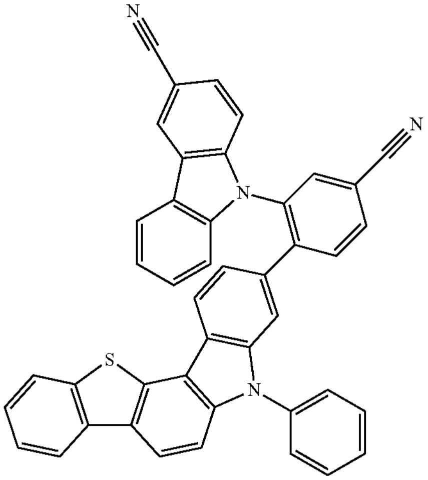
112
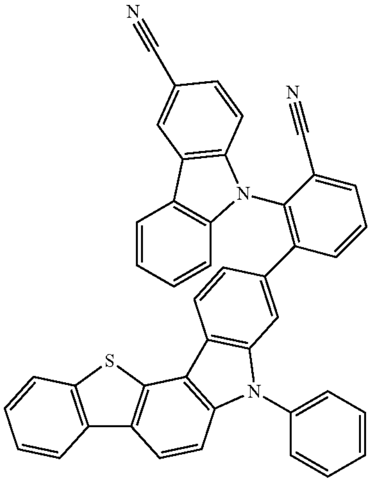

113
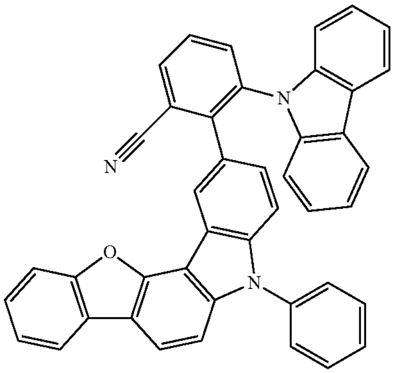
114
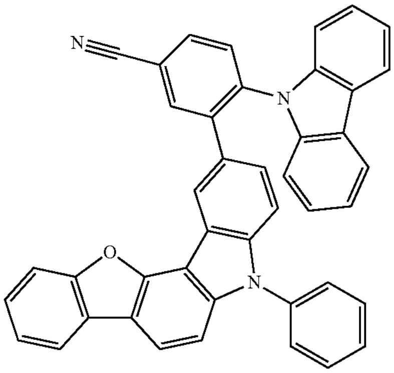
115
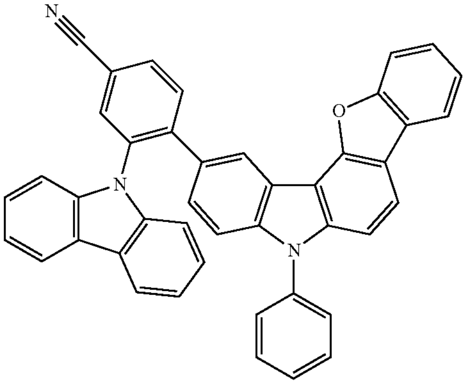
116
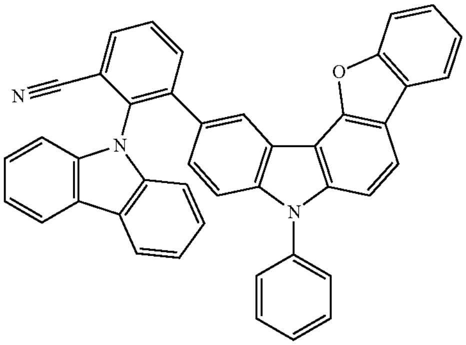
117
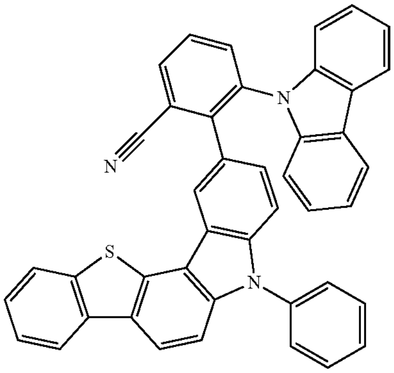
118
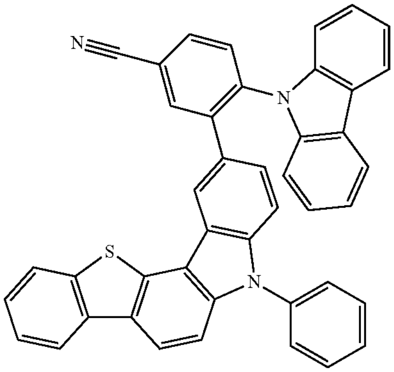
119
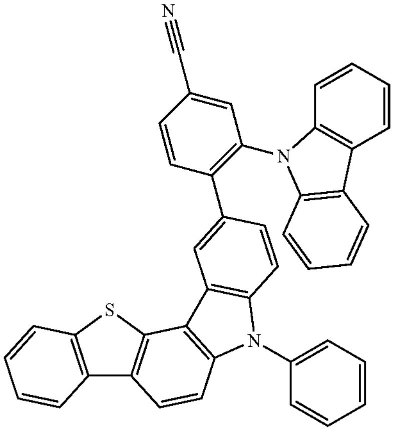
120
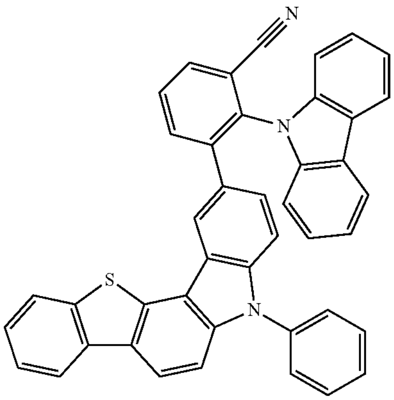

-continued
121
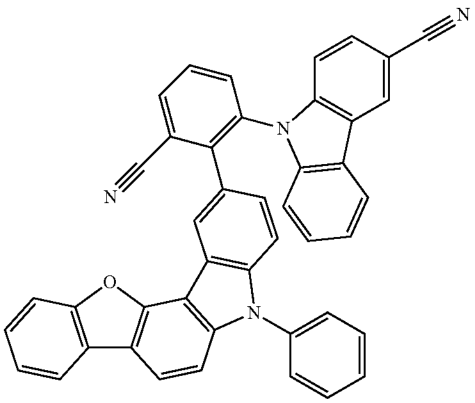
122
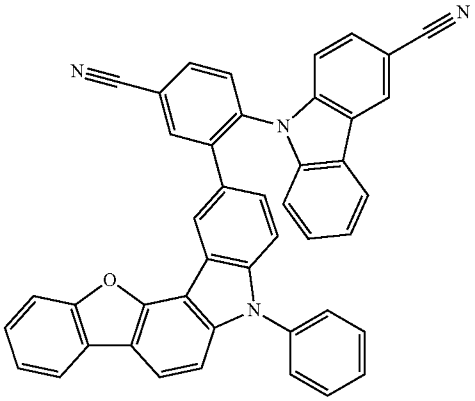
123
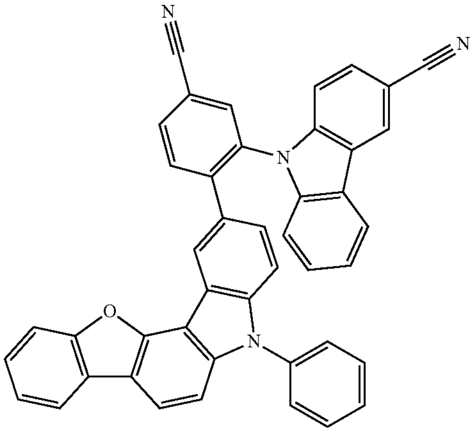
124
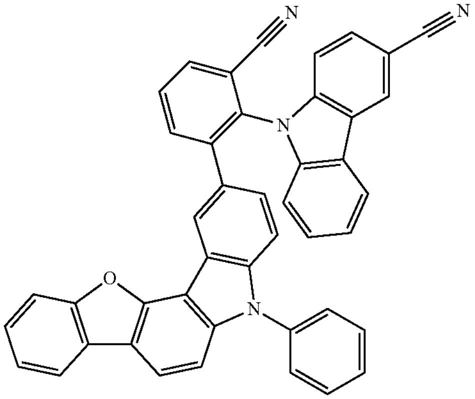
-continued
125
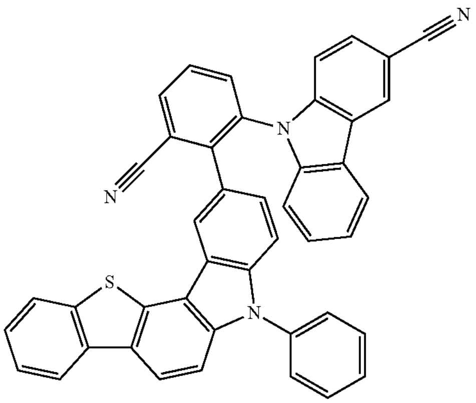
126
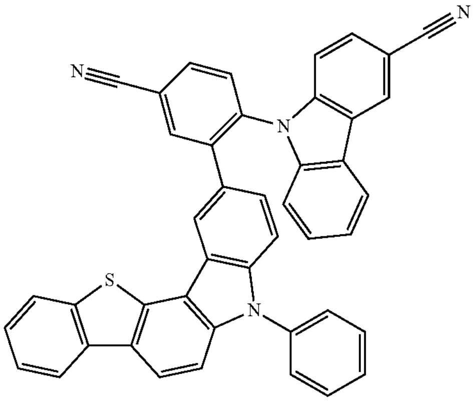
127
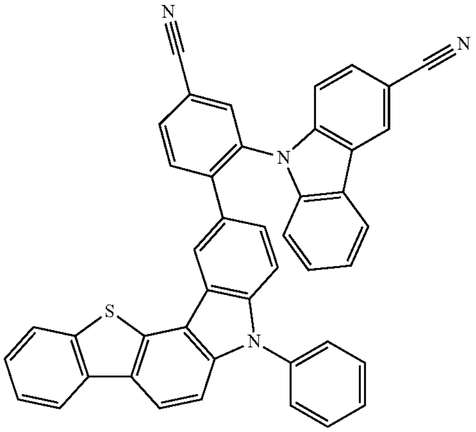
128
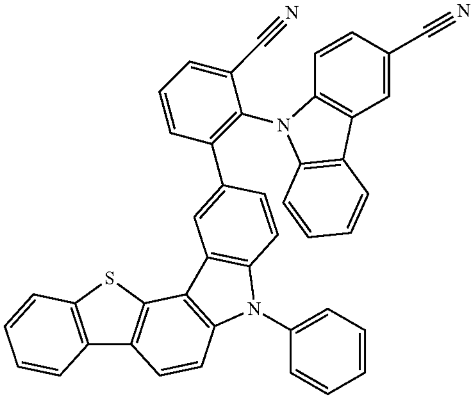

-continued
129
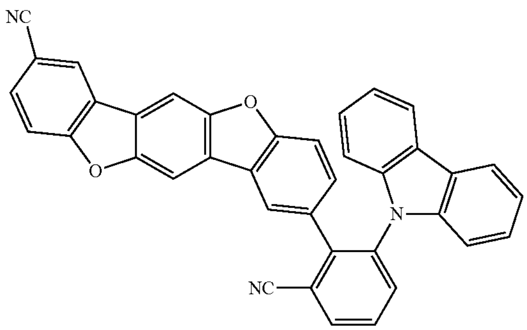
130
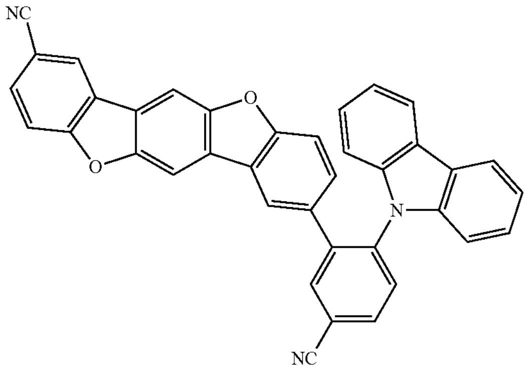
131
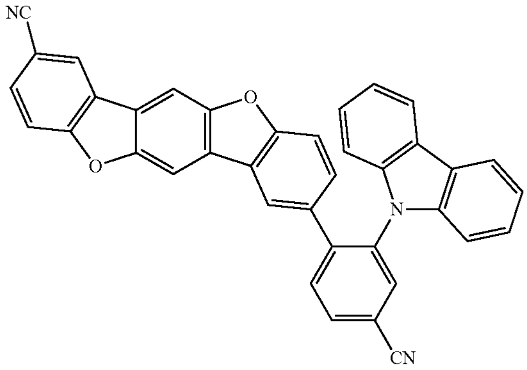
132
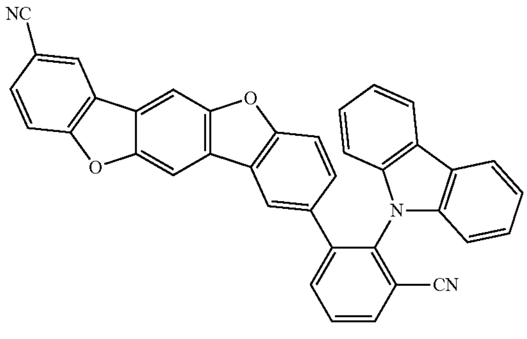
-continued
133
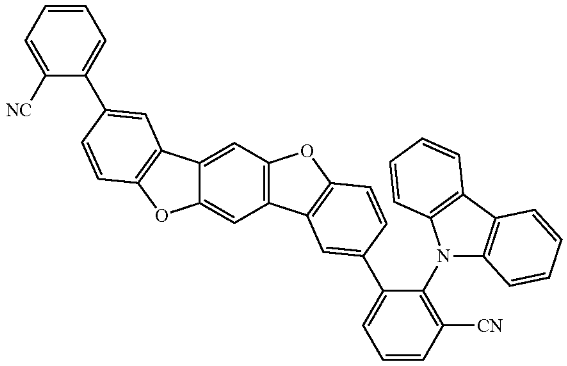
134
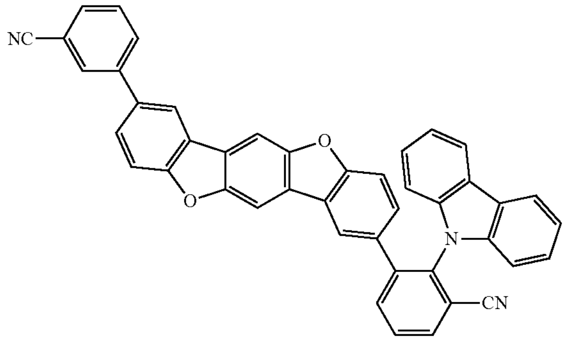
135
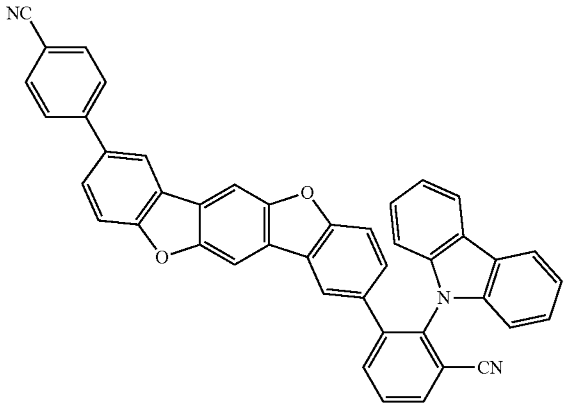
136
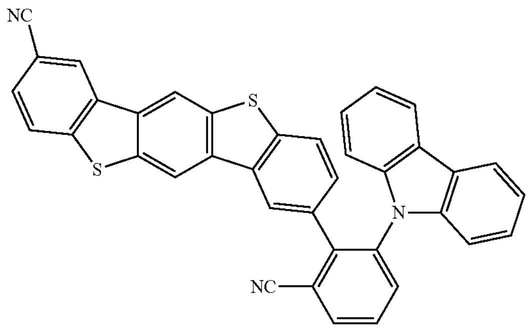

-continued
137
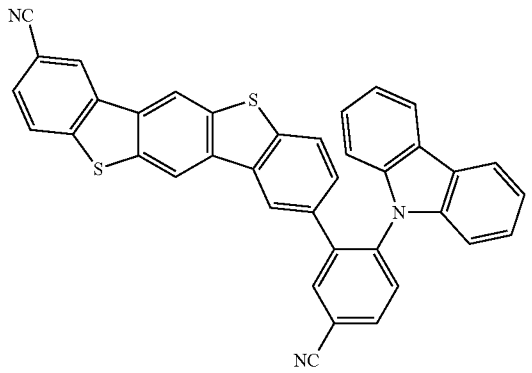
138
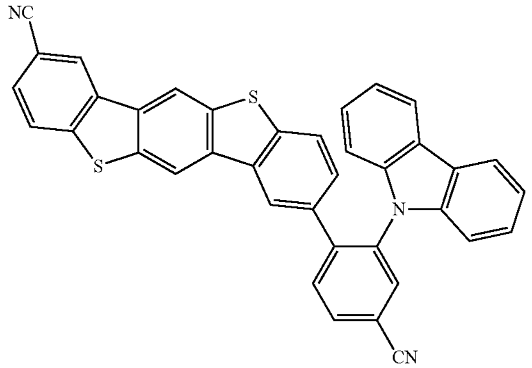
139
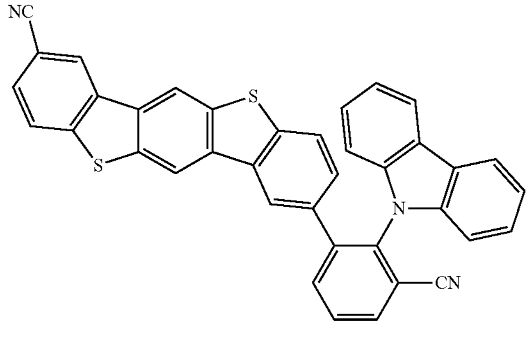
140
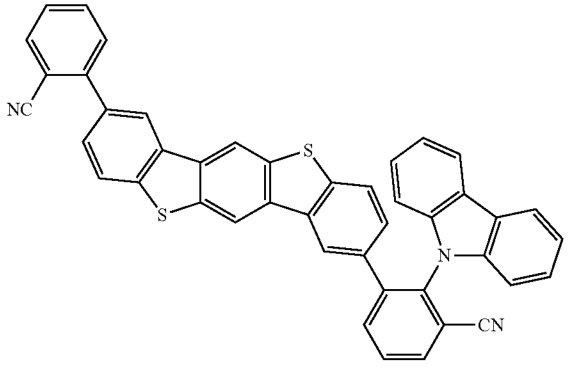
-continued
141
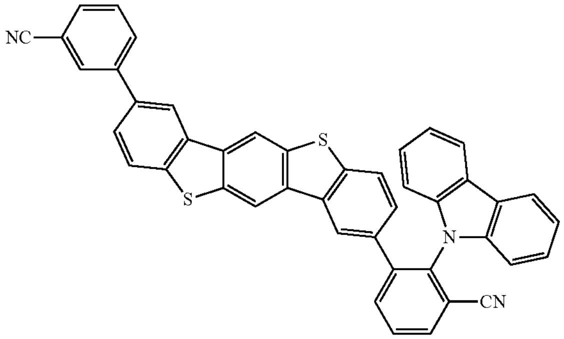
142
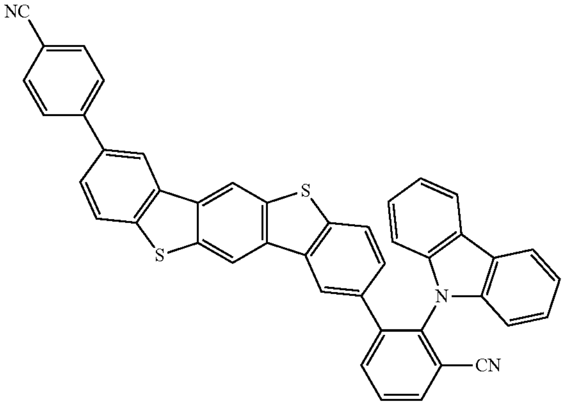
143
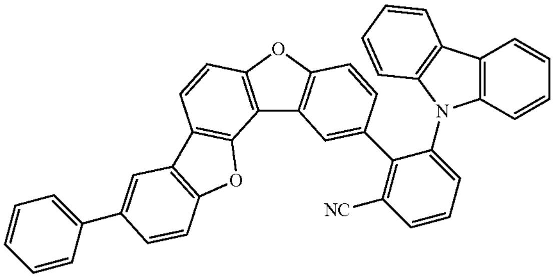
144
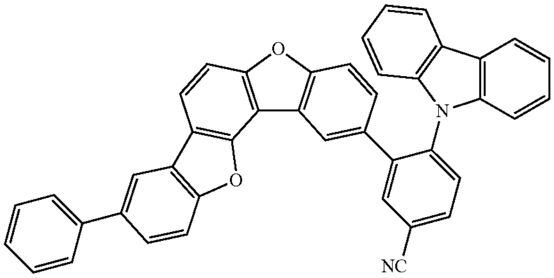

-continued
145
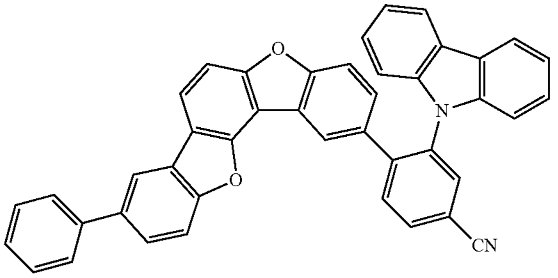
146
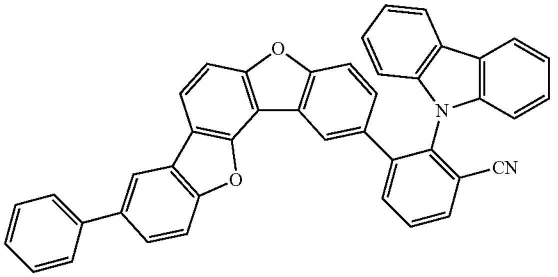
147
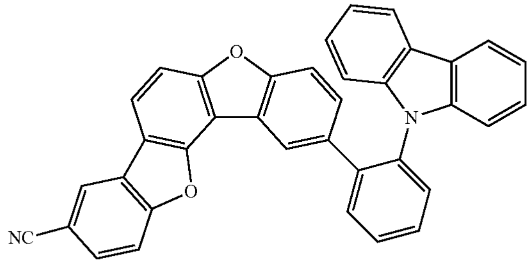
148
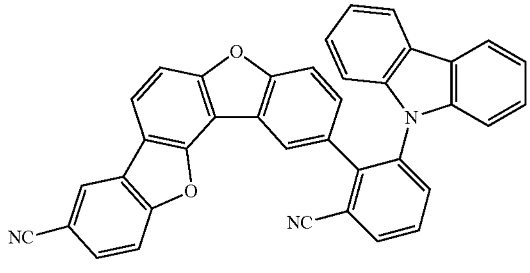
149
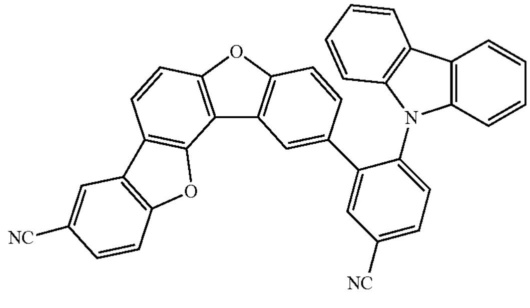
-continued
150
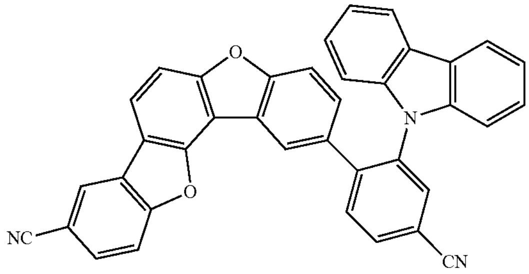
151
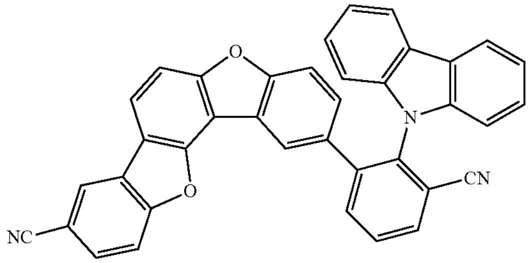
152
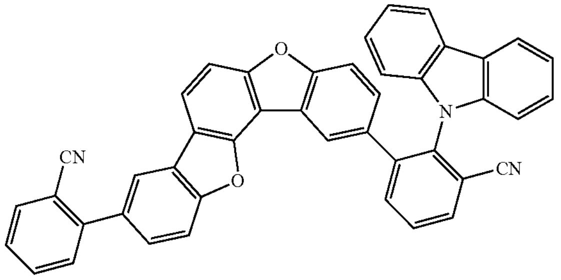
153
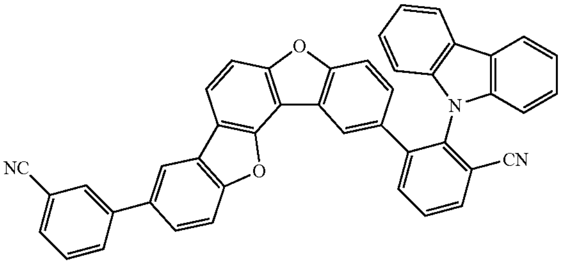
154
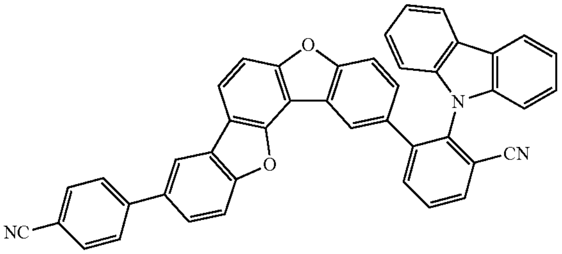

-continued
155
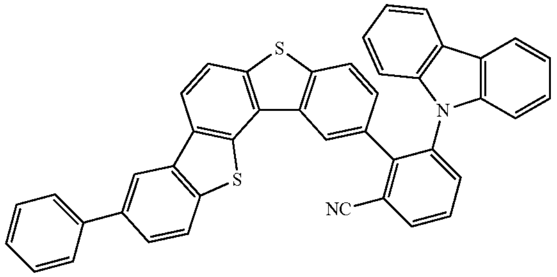
156
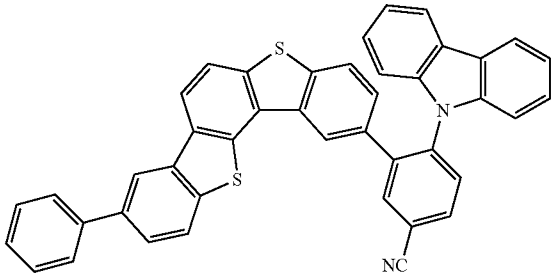
157
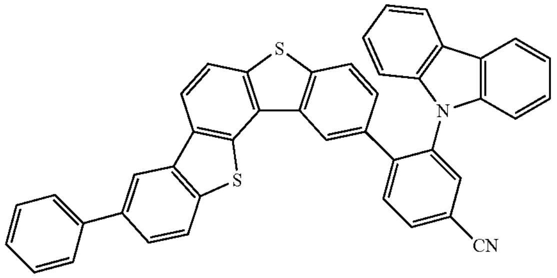
158
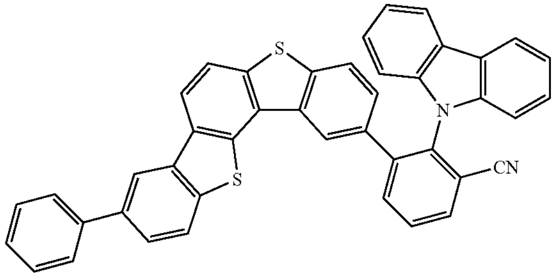
159
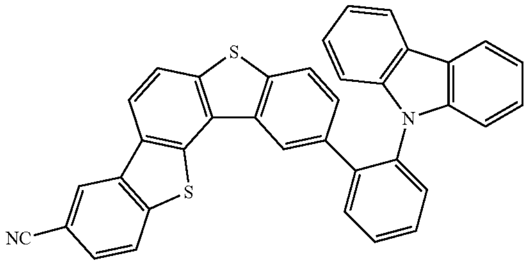
-continued
160
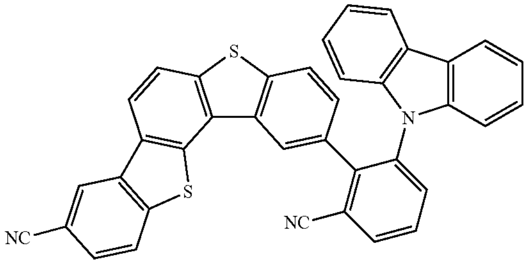
161
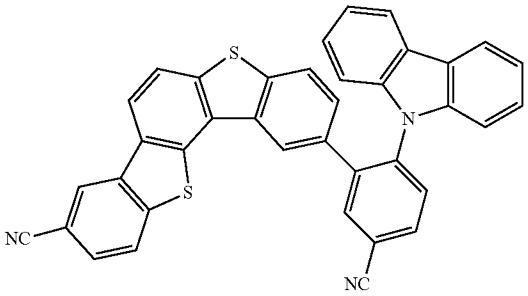
162
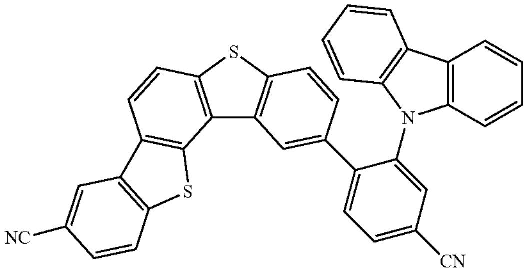
163
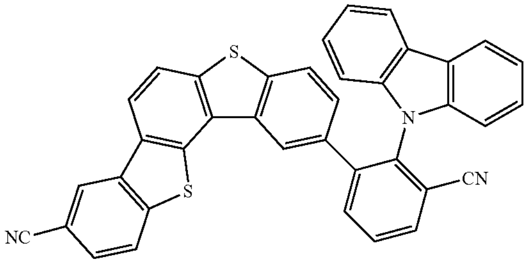
164
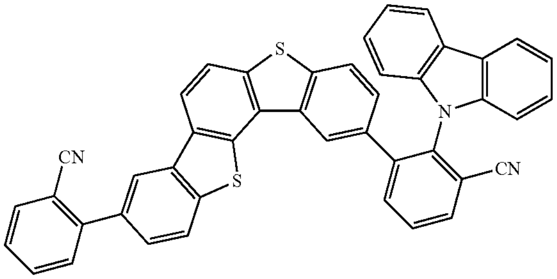

165
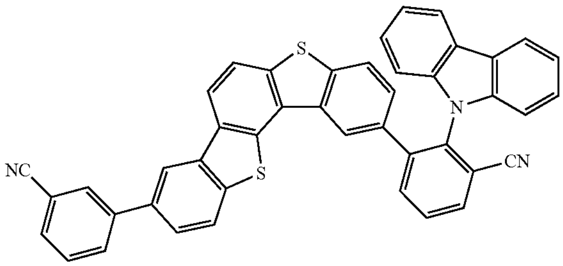
166
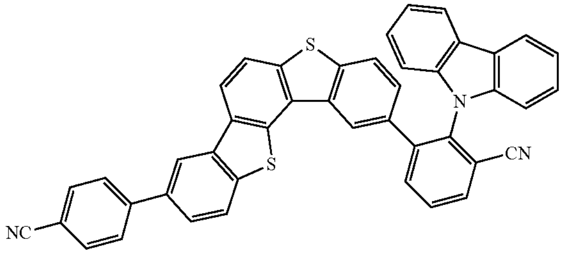
167
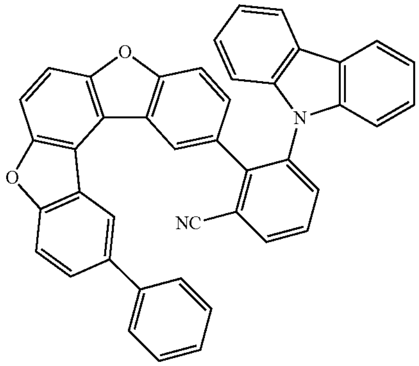
168
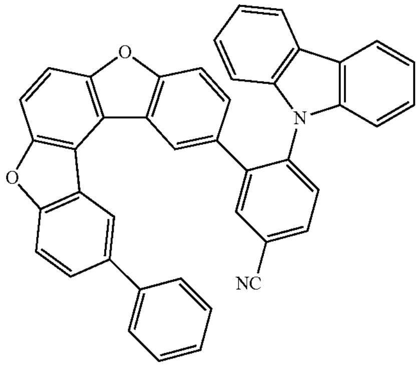
169
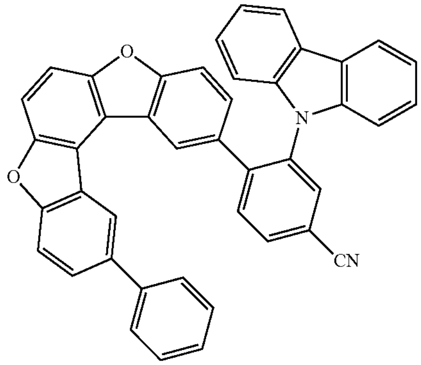
170
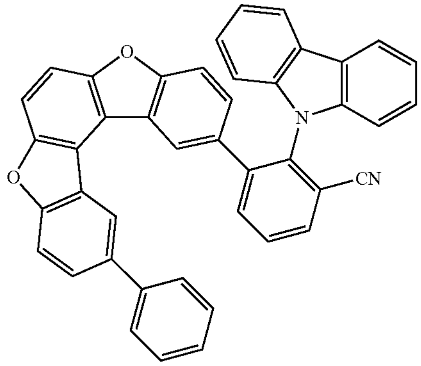
171
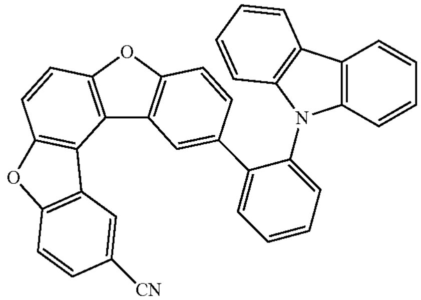
172
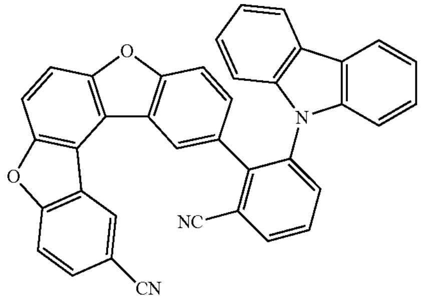

-continued
173
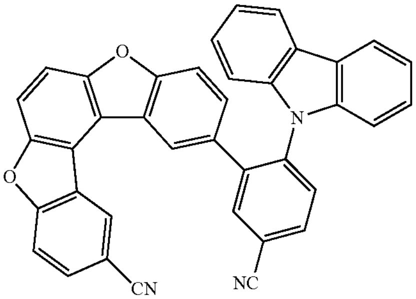
174
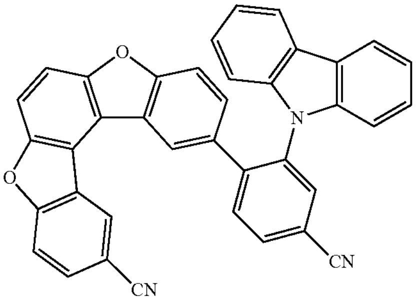
175
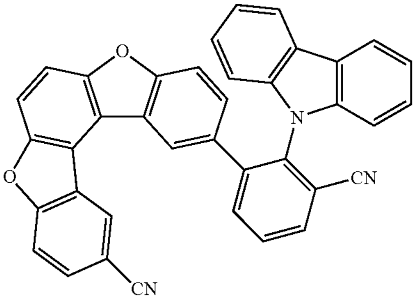
176
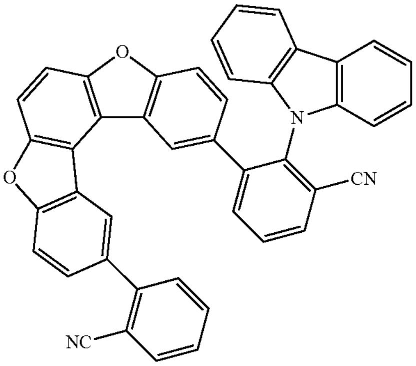
-continued
177
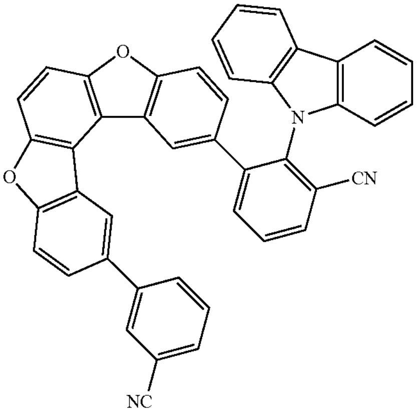
178
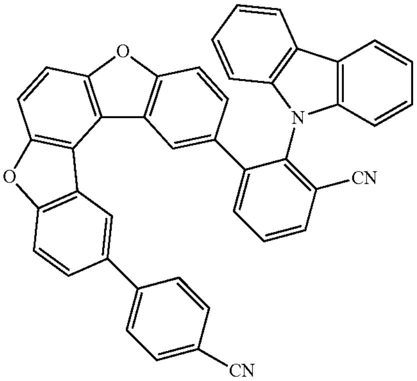
179
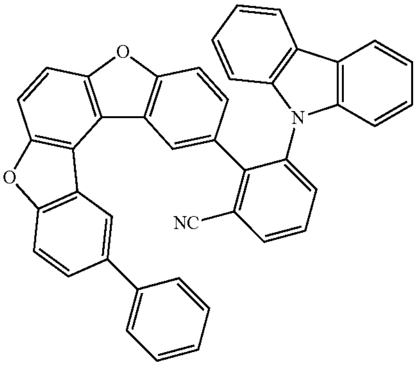
180
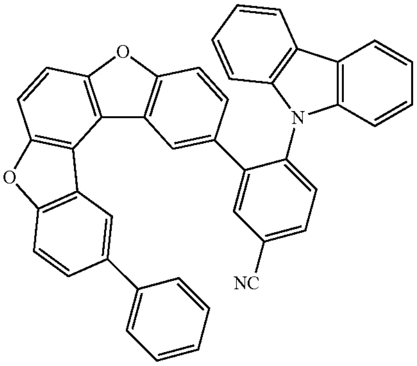

-continued
181
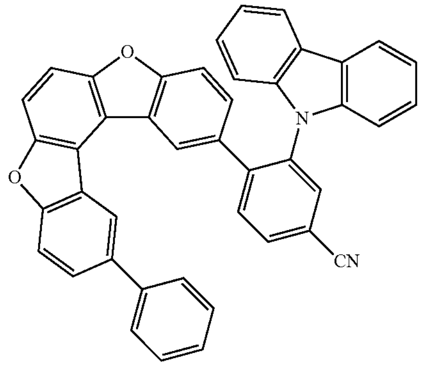
182
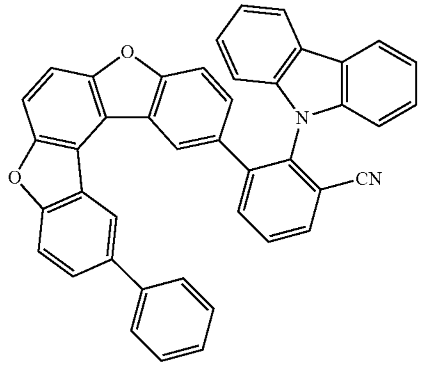
183
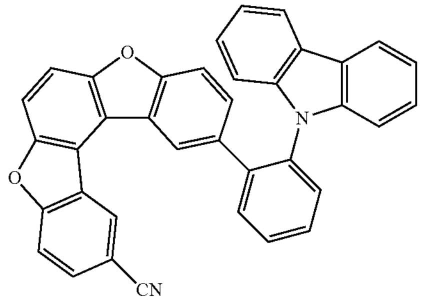
184
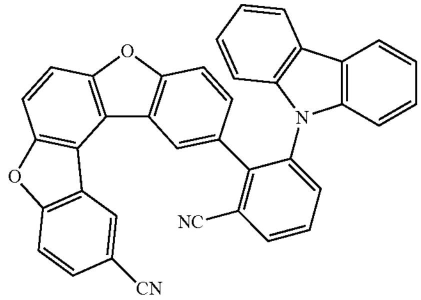
-continued
185
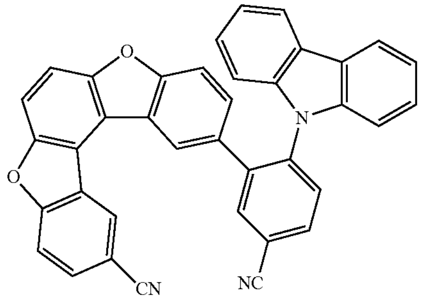
186
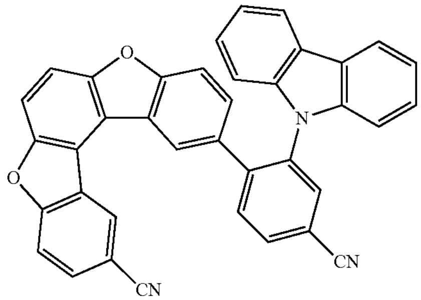
187
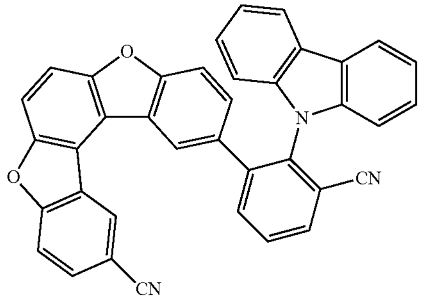
188
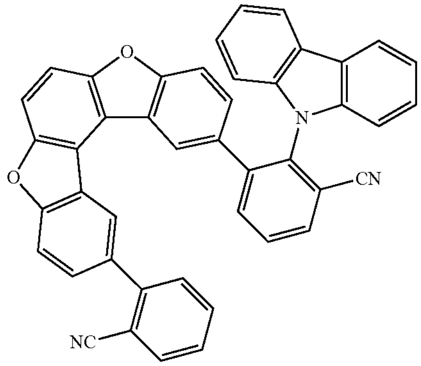

-continued
189
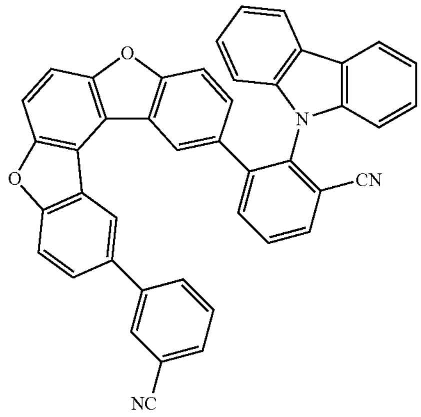
190
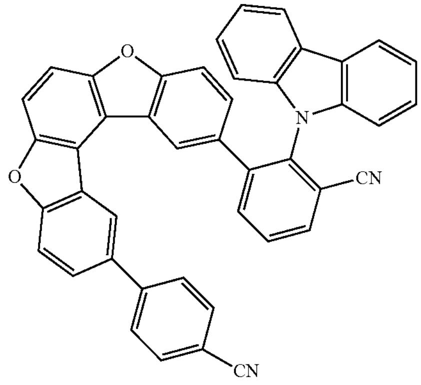
191
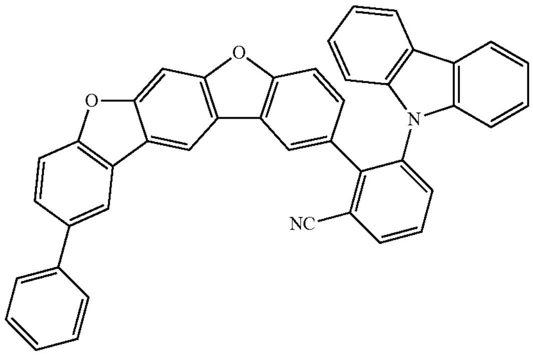
192
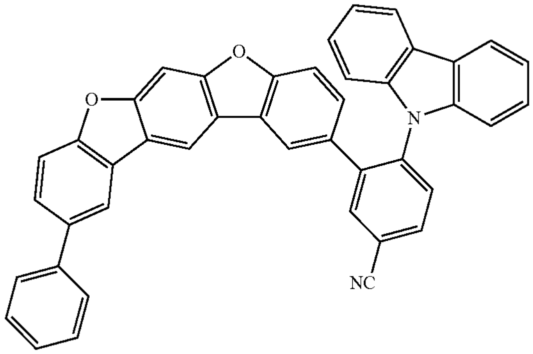
-continued
193
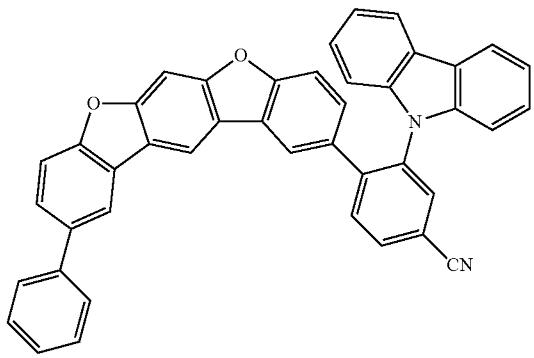
194
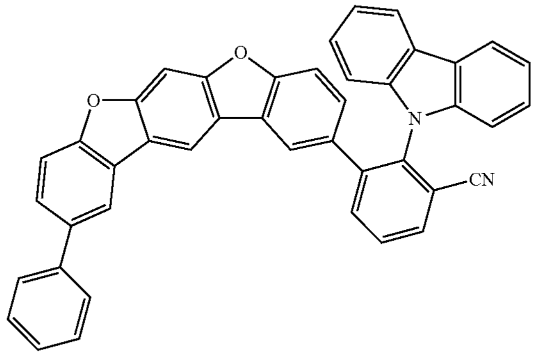
195
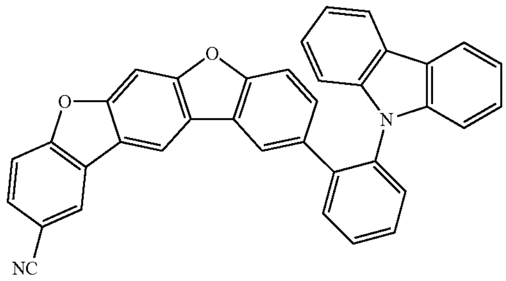
196
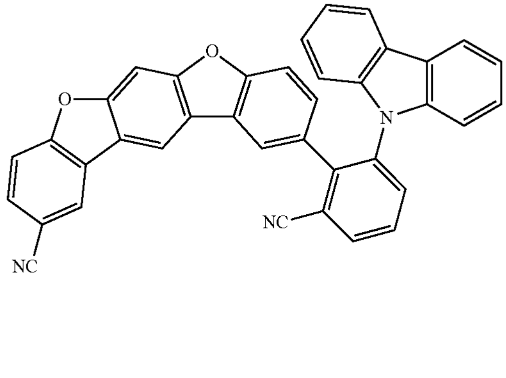

-continued
197
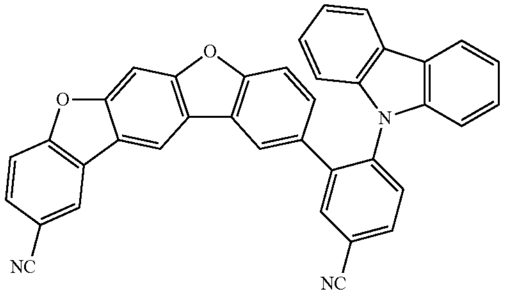
198
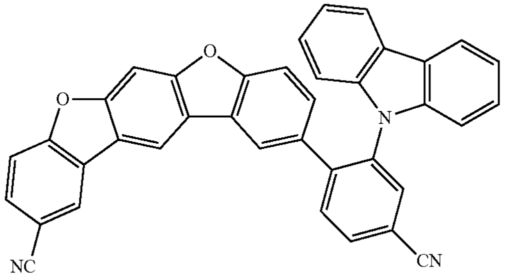
199
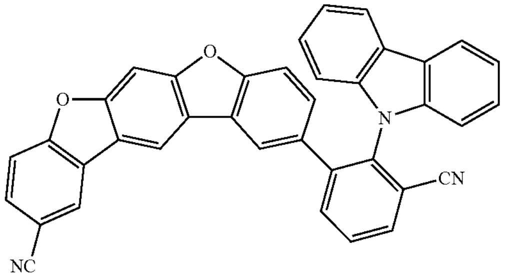
200
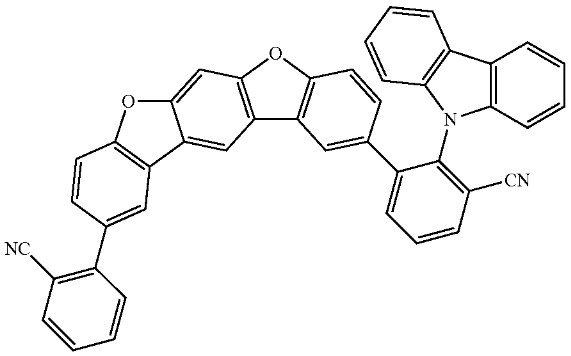
-continued
201
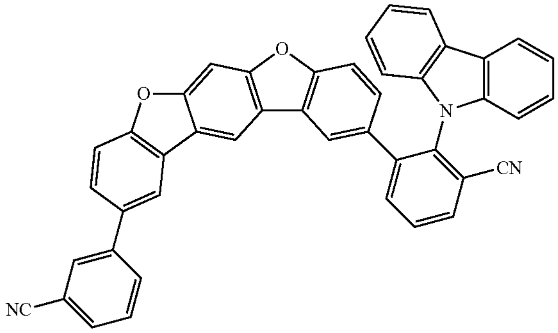
202
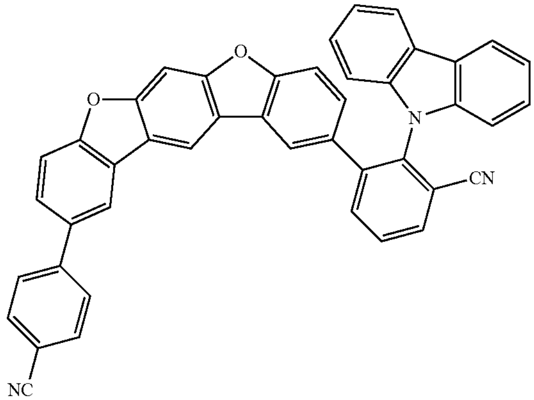
203
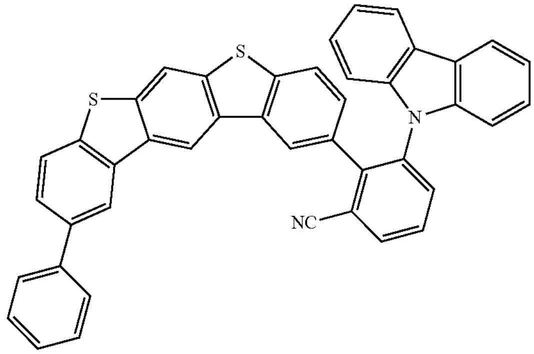
204
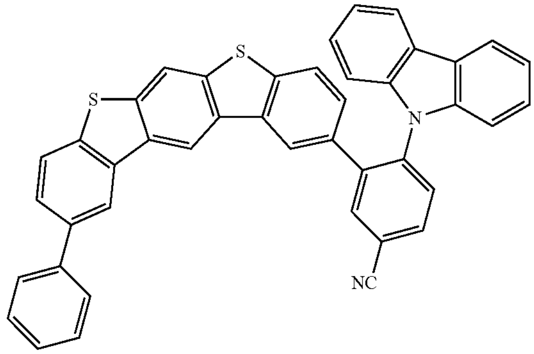

-continued
205
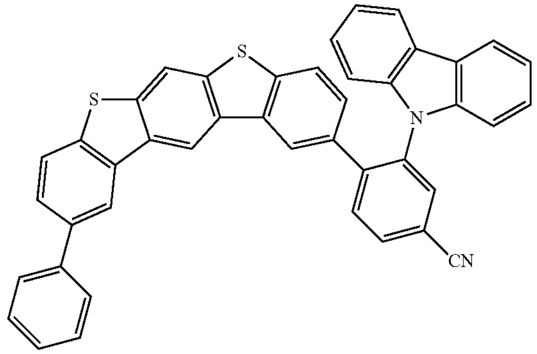
206
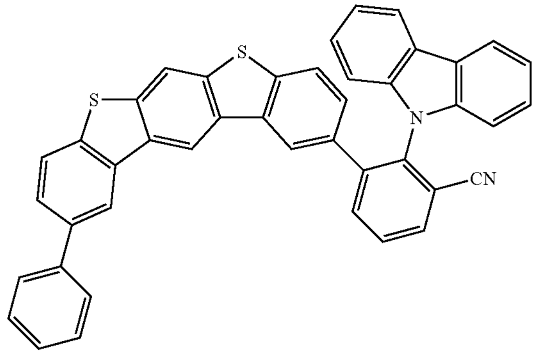
207
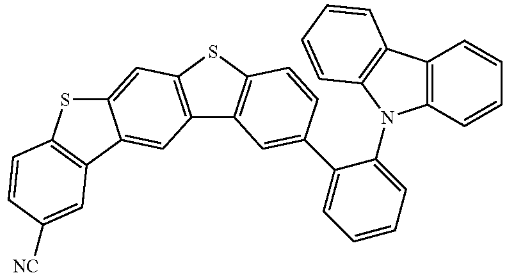
208
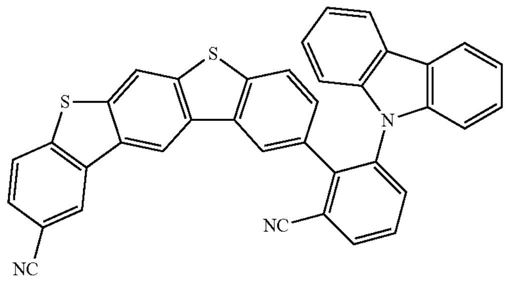
-continued
209
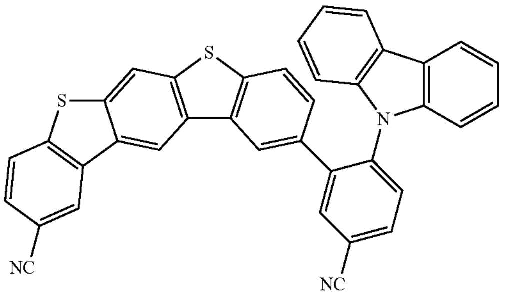
210
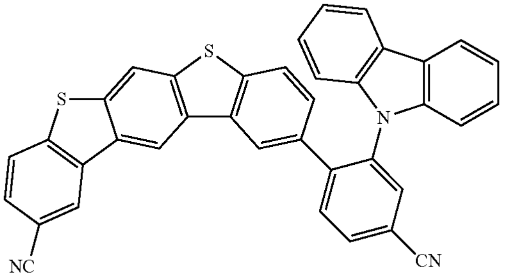
211
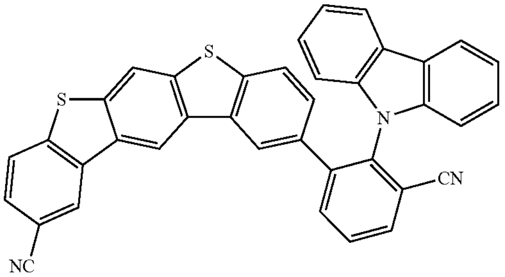
212
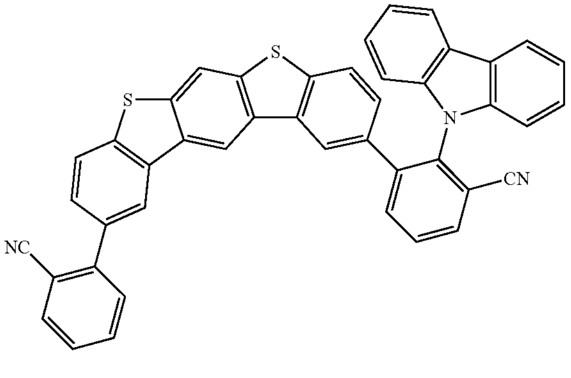

-continued
213
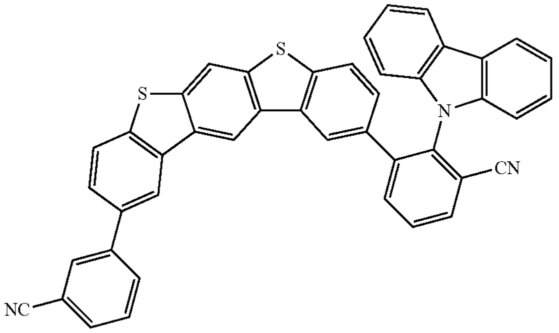
214
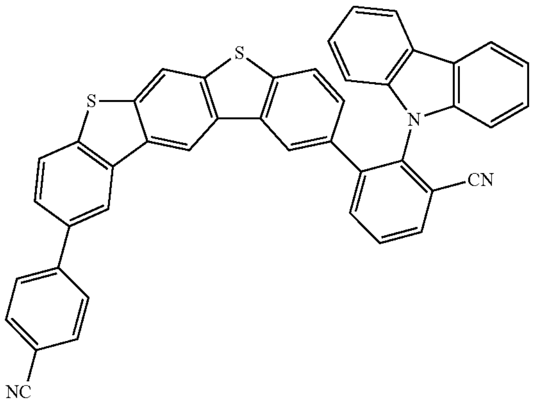
215
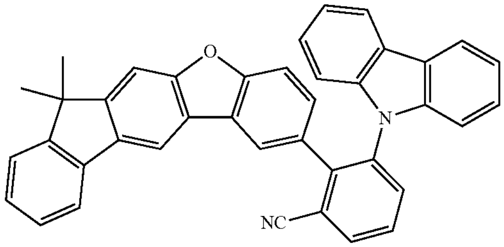
216
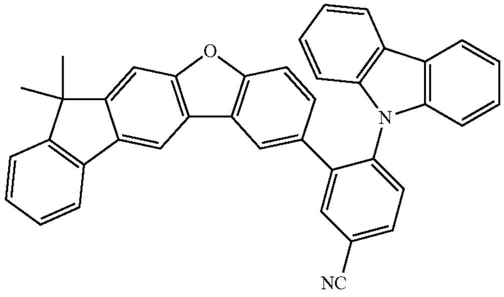
-continued
217
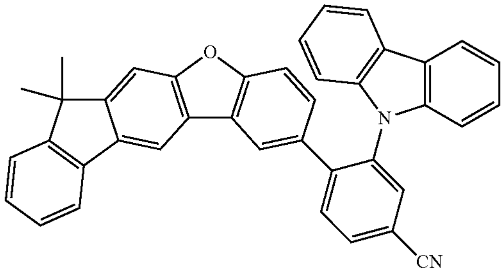
218
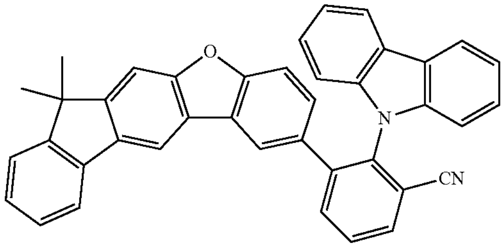
219
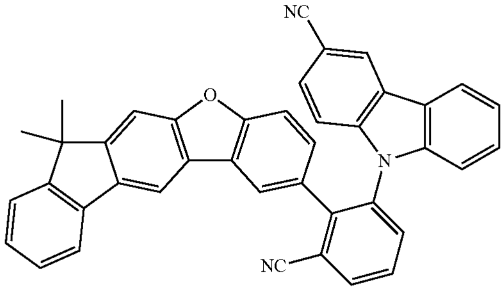
220
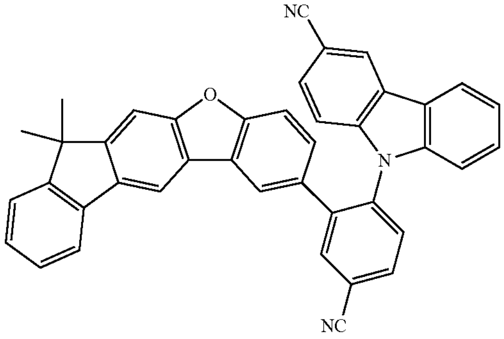
221
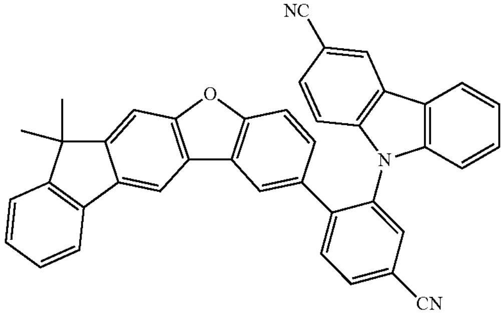

-continued
222
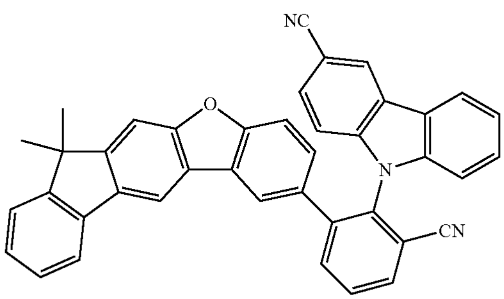
223
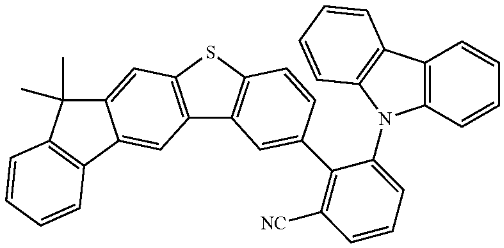
224
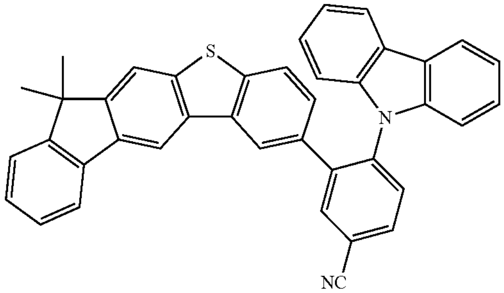
225
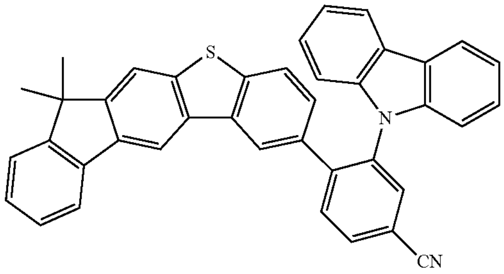
226
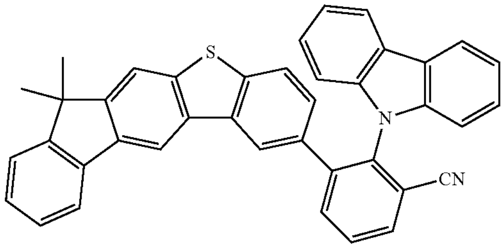
-continued
227
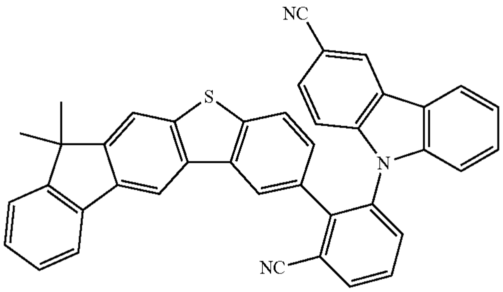
228
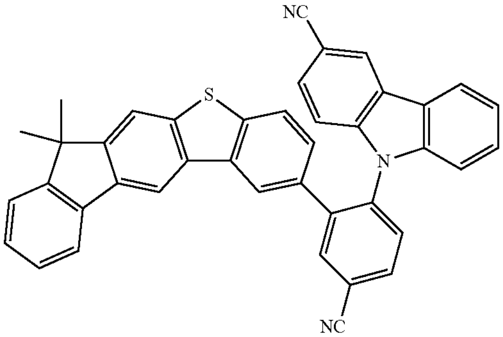
229
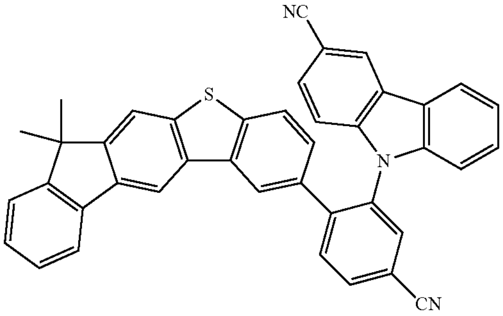
230
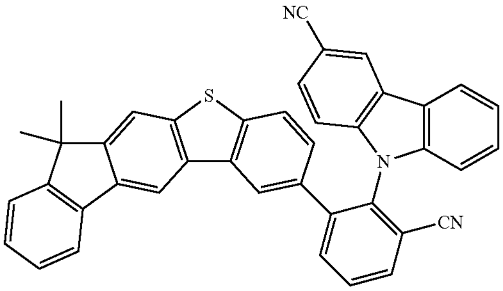
231
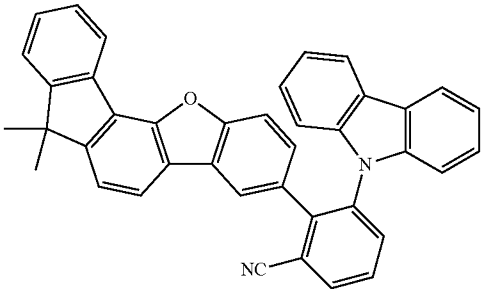

-continued
232
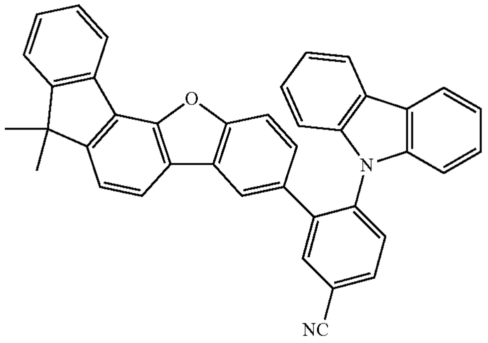
233
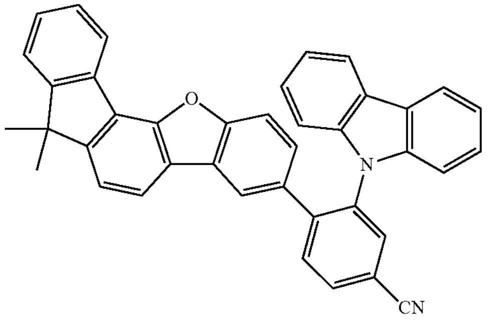
234
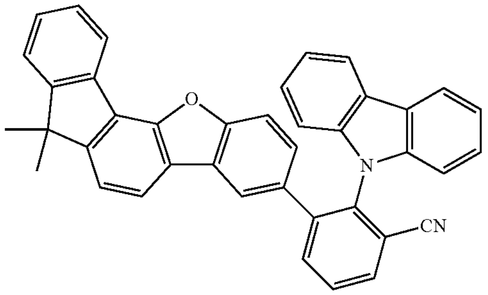
235
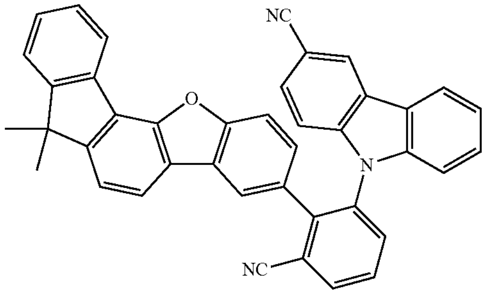
236
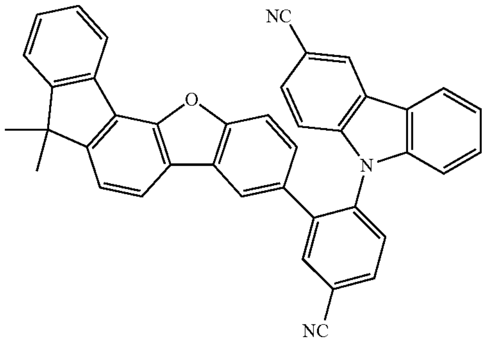
-continued
237
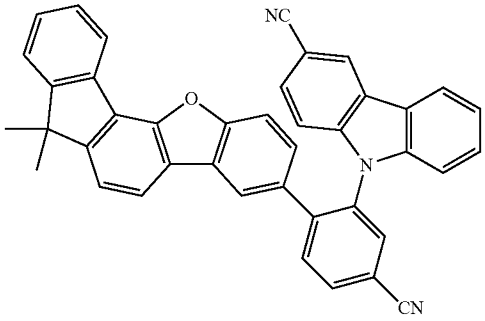
238
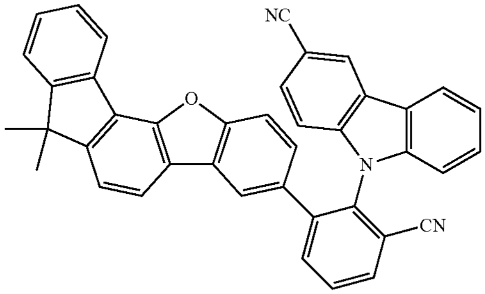
239
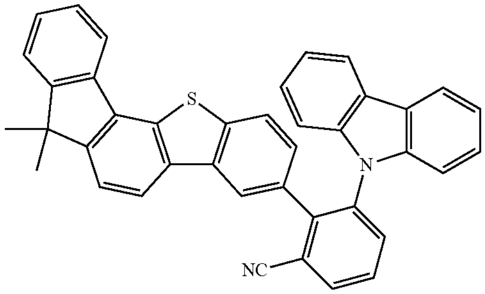
240
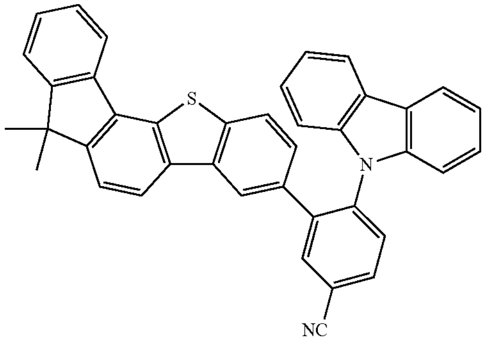
241
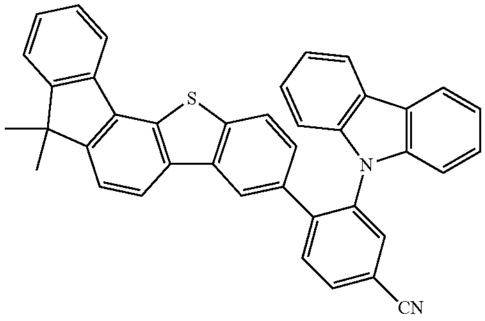

-continued
242
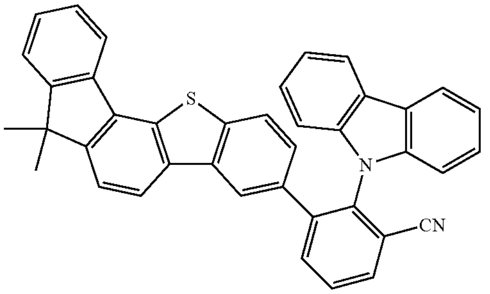
243
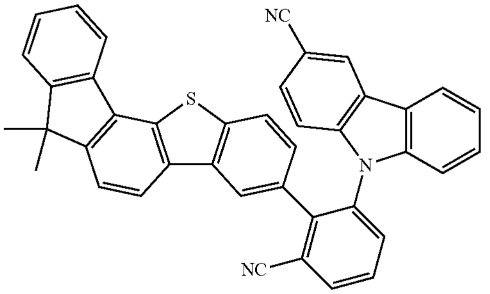
244
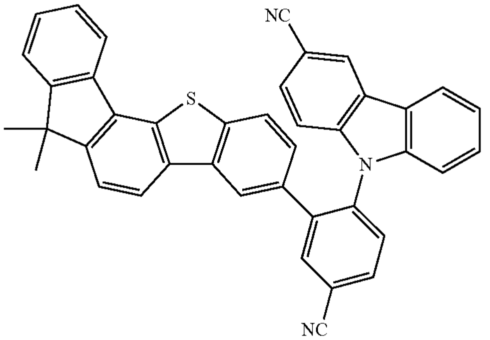
245
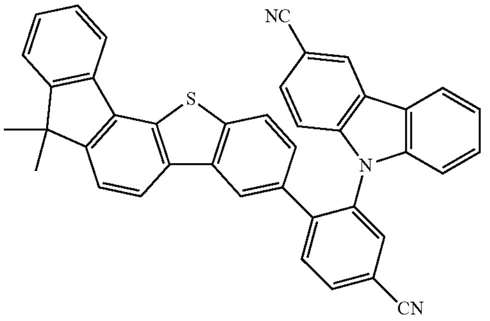
246
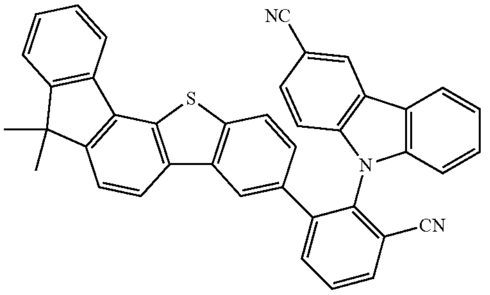
-continued
247
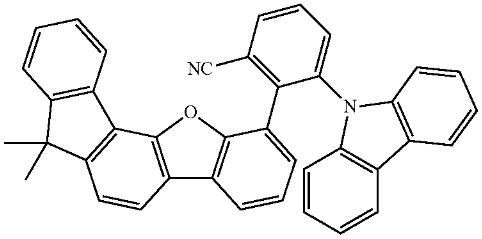
248
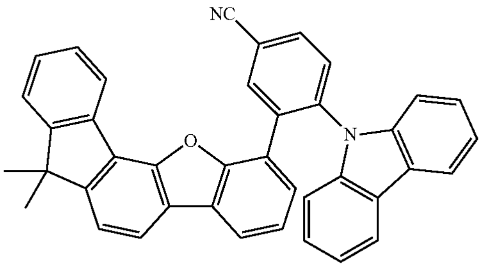
249
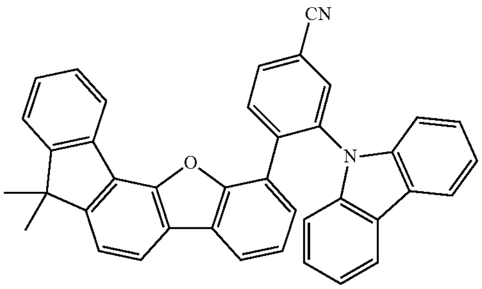
250
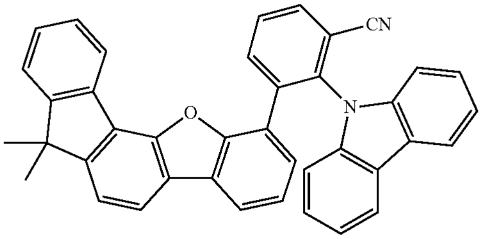
251
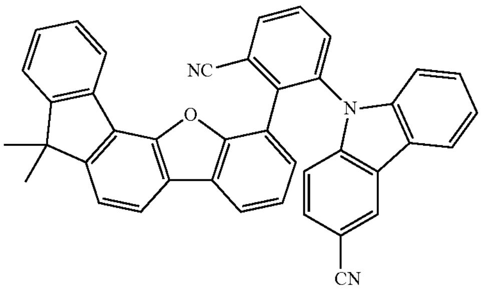

-continued
252
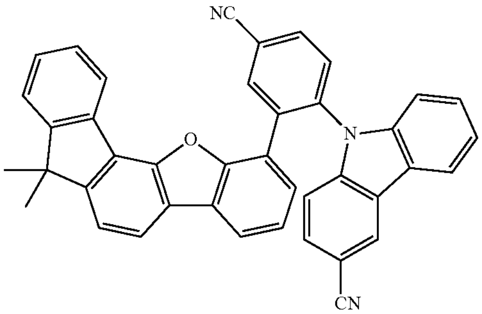
253
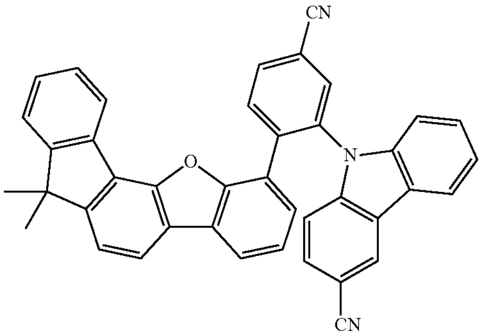
254
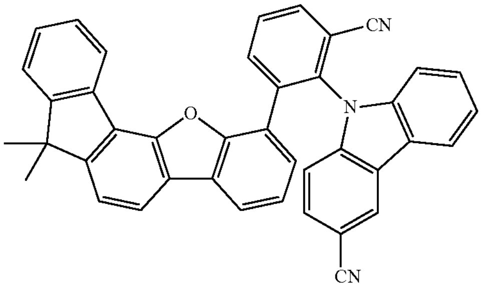
255
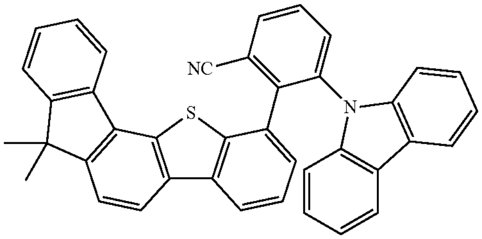
256
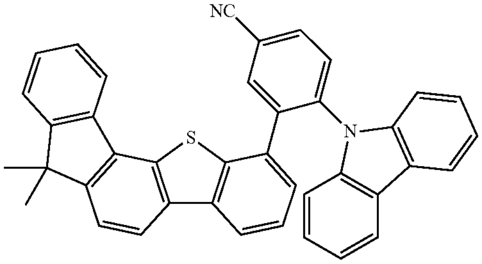
-continued
257
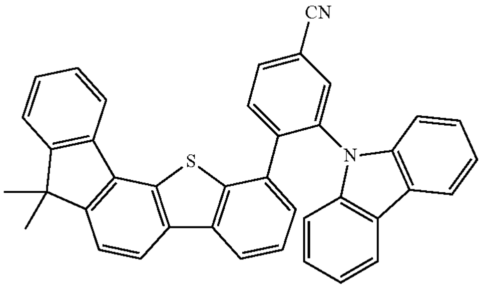
258
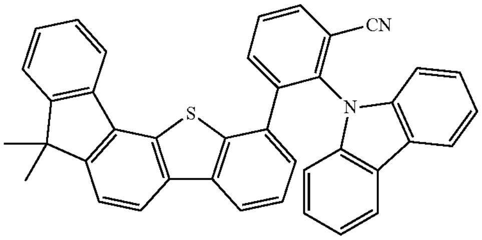
259
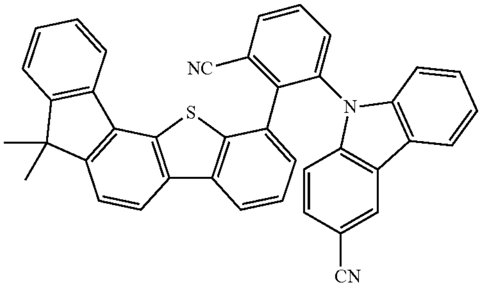
260
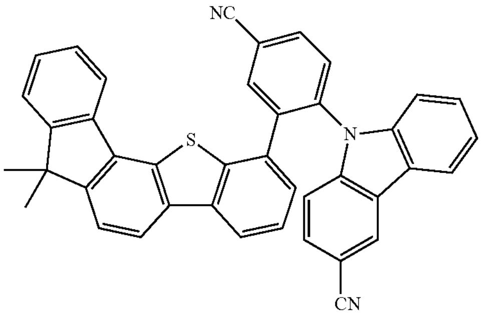
261
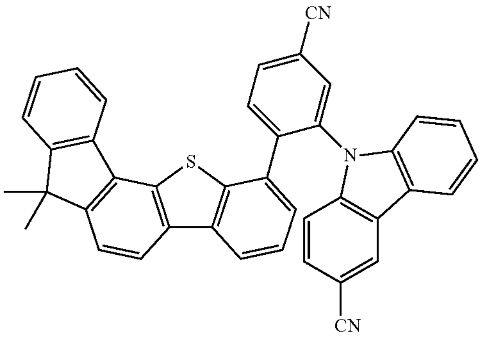

-continued
262
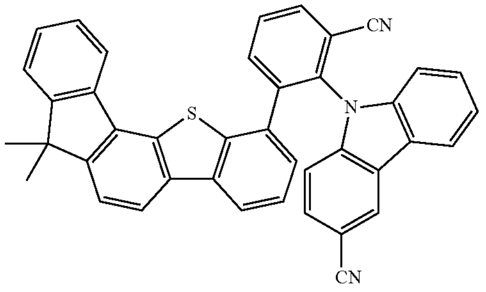
263
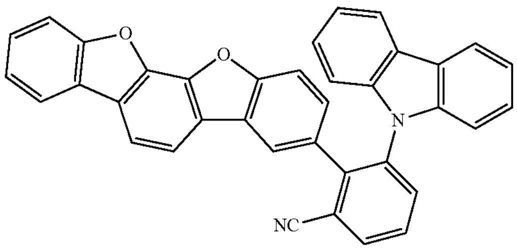
264
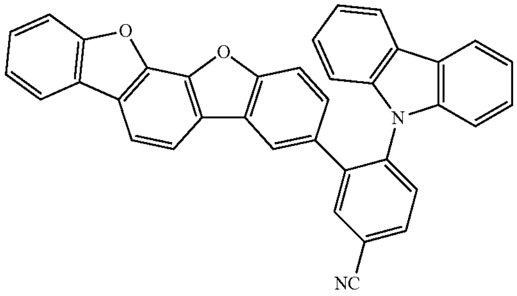
265
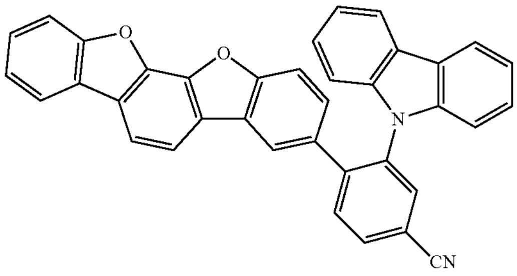
266
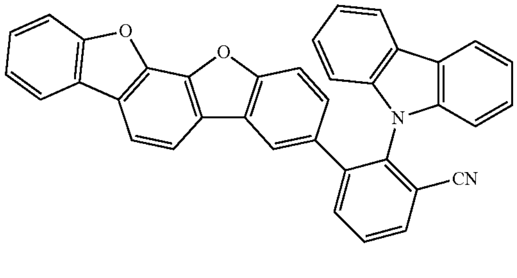
-continued
267
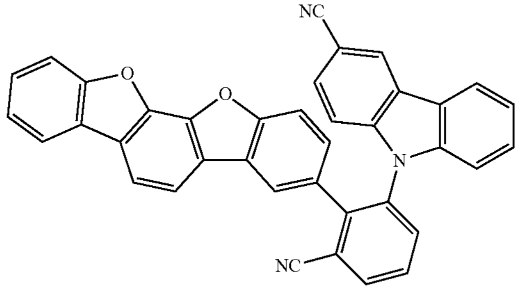
268
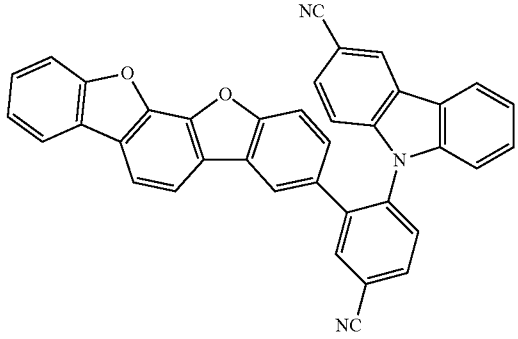
269
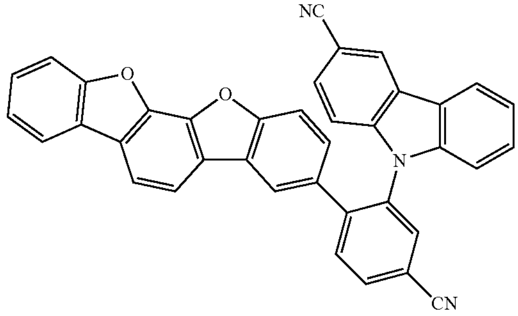
270
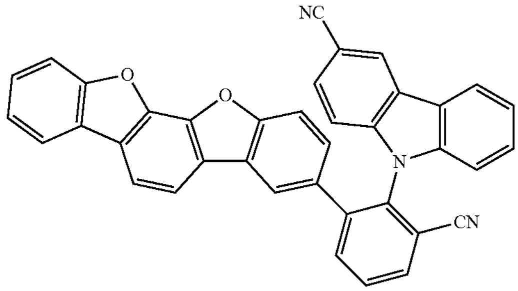
271
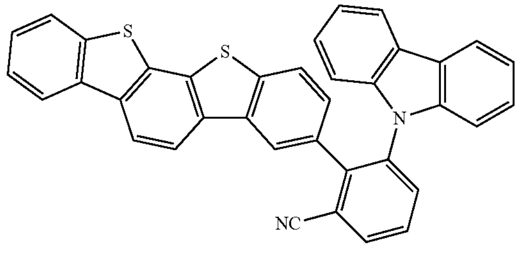

-continued
272
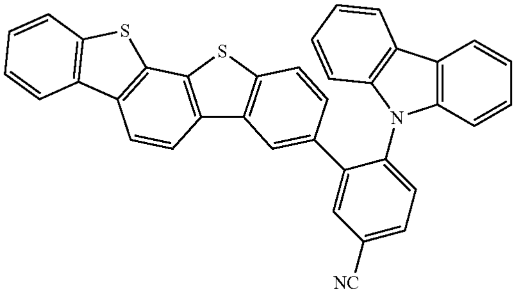
273
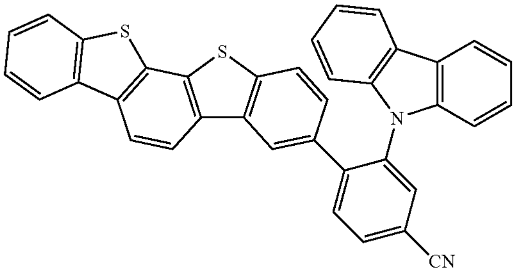
274
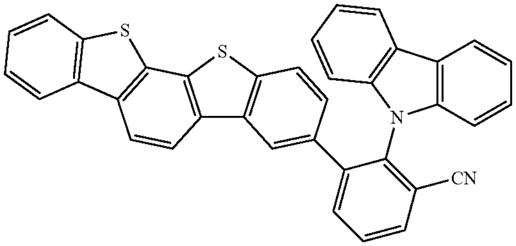
275
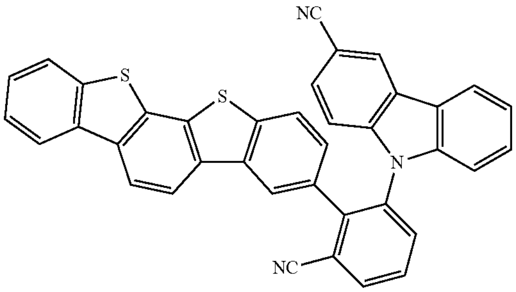
276
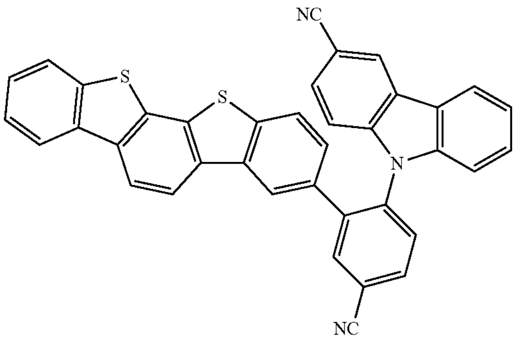
-continued
277
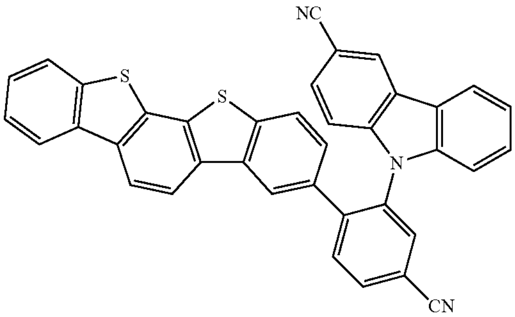
278
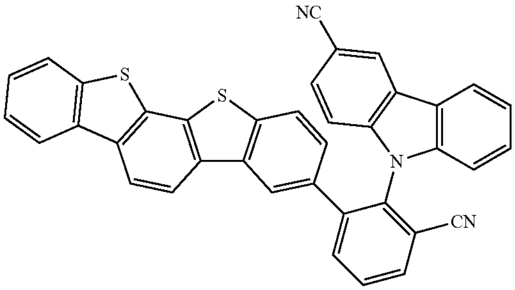
279
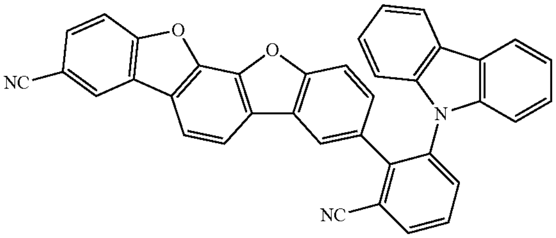
280
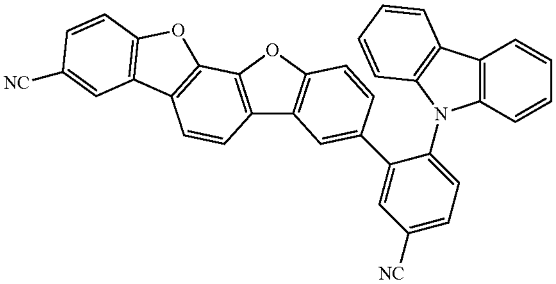
281
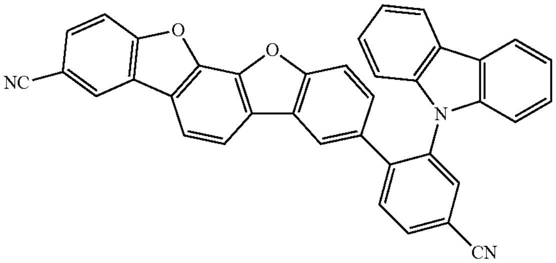

-continued
282
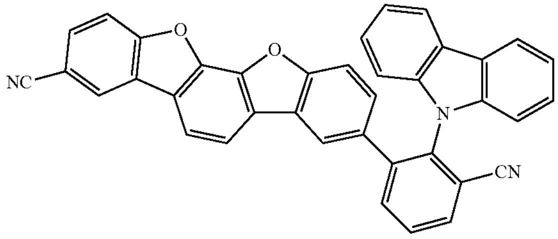
283
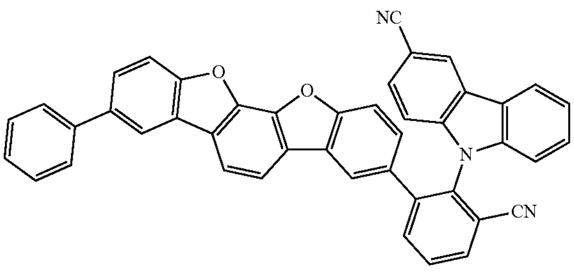
284
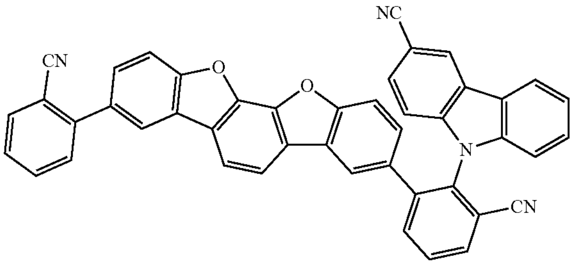
285
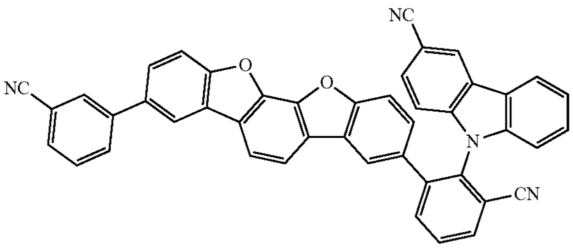
286
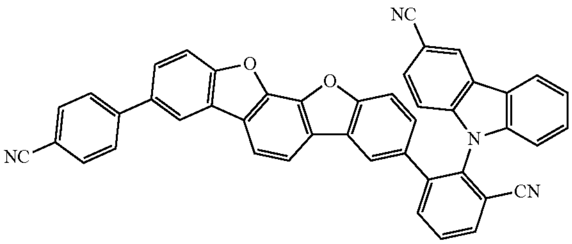
-continued
287
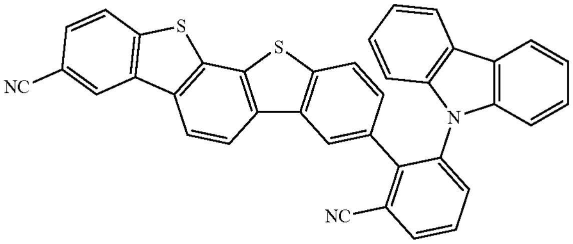
288
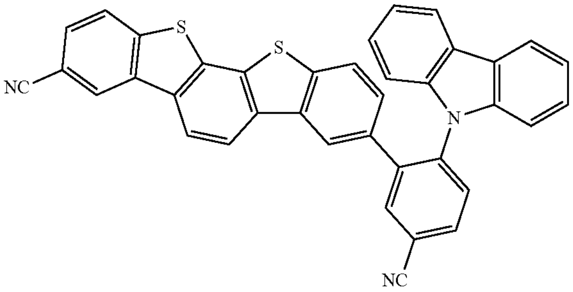
289
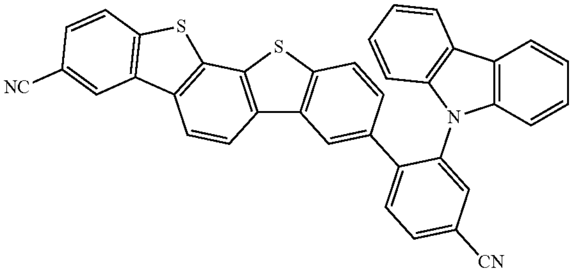
290
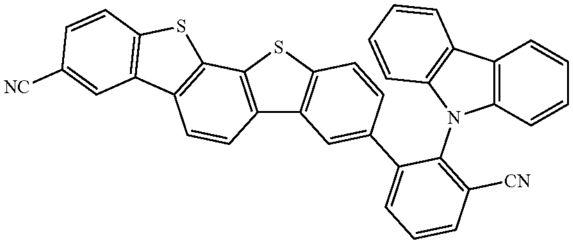
291
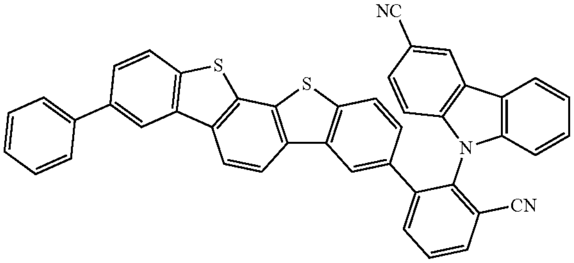

-continued
292
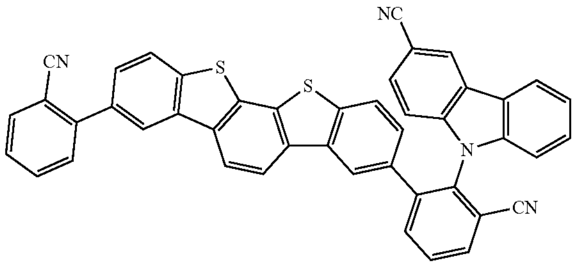
293
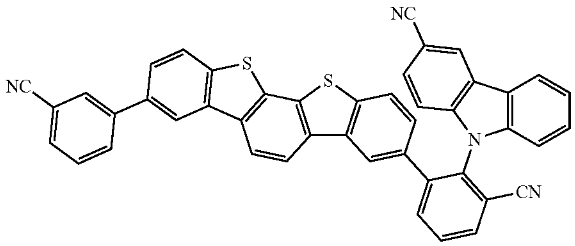
294
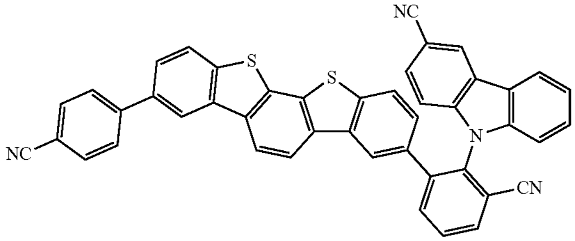
295
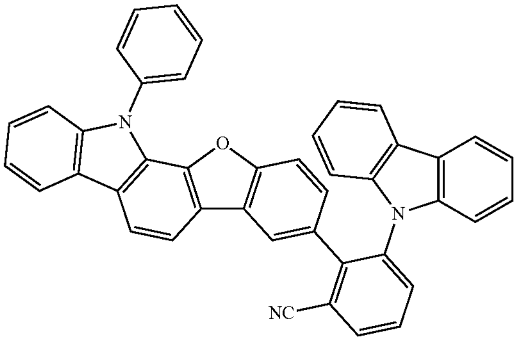
296
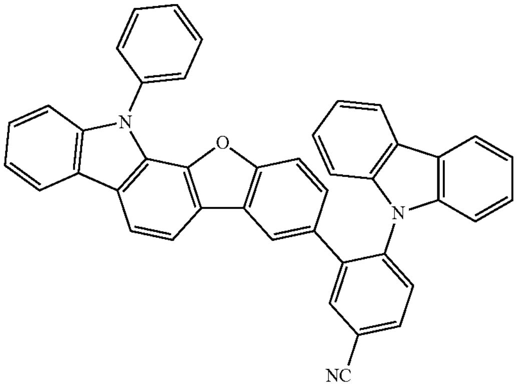
-continued
297
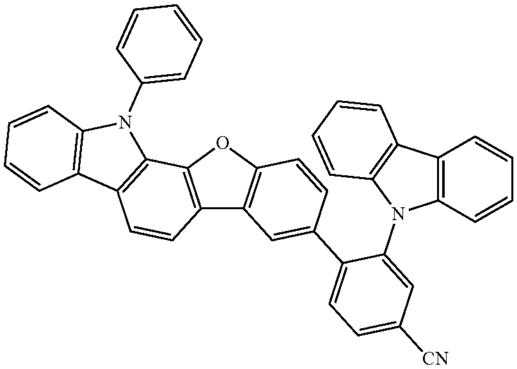
298
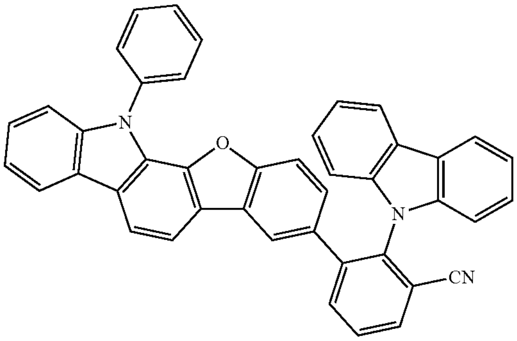
299
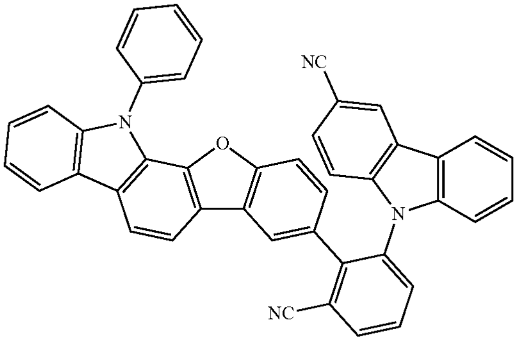
300
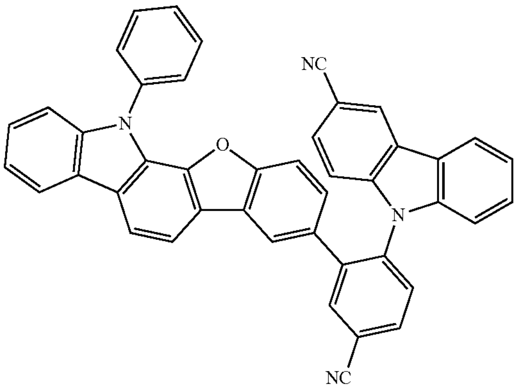

301
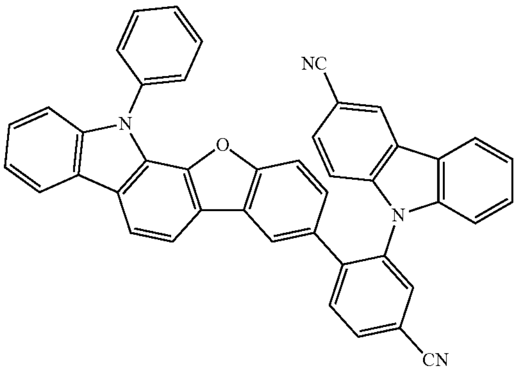
302
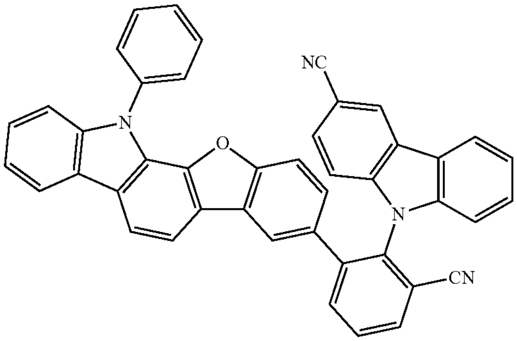
303
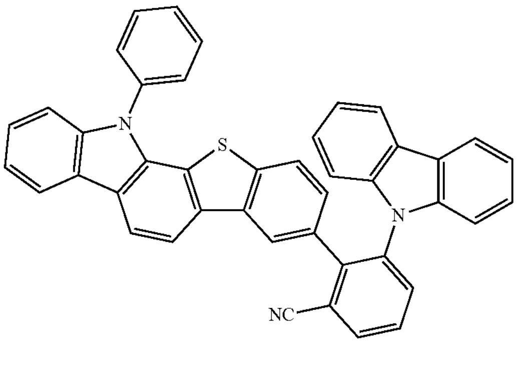
304
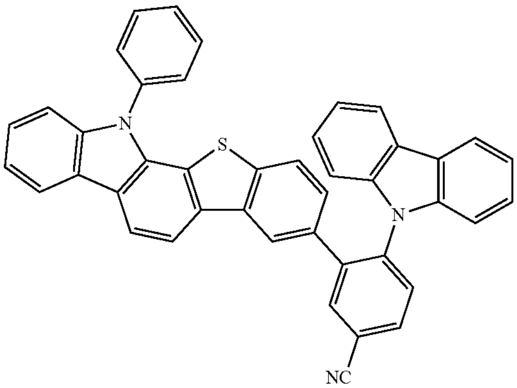
305
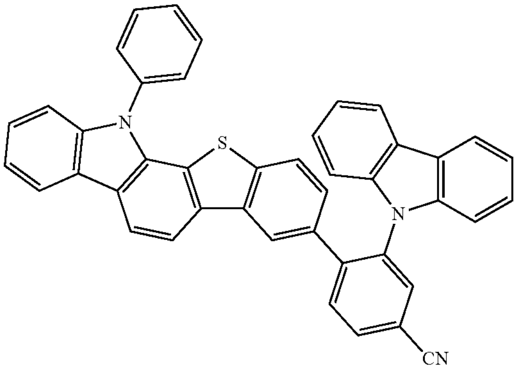
306
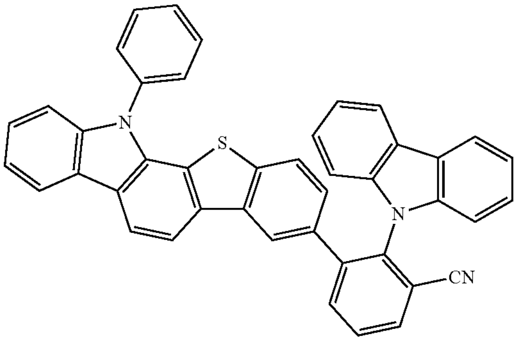
307
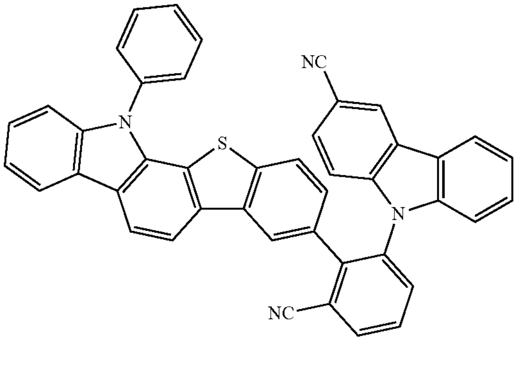
308
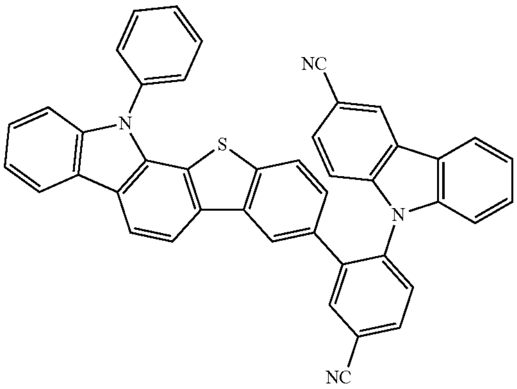

-continued
309
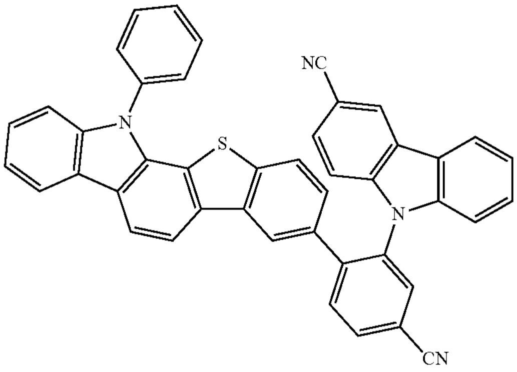
310
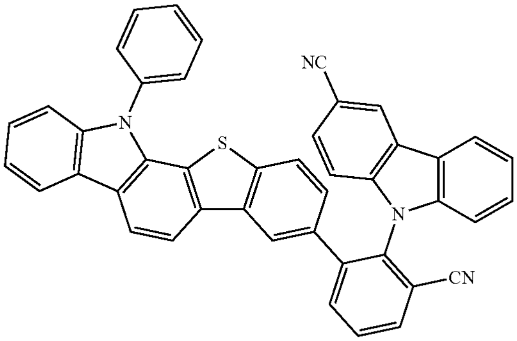
311
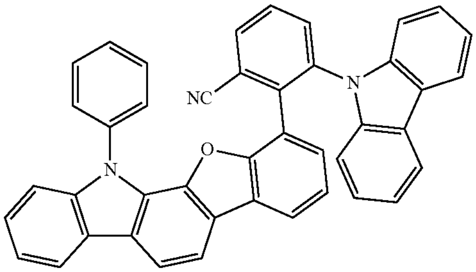
312
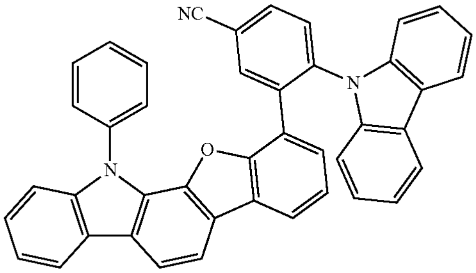
313
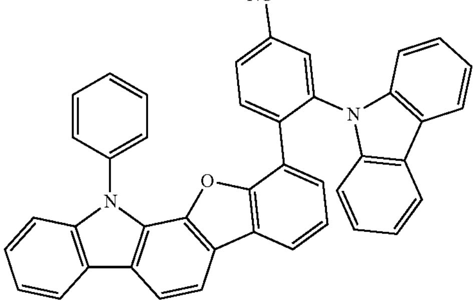
-continued
314
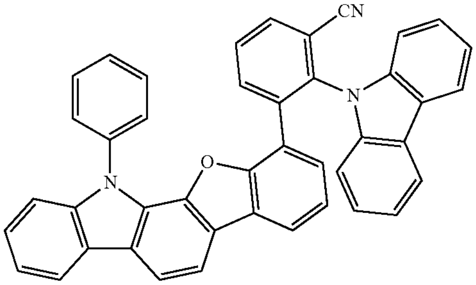
315
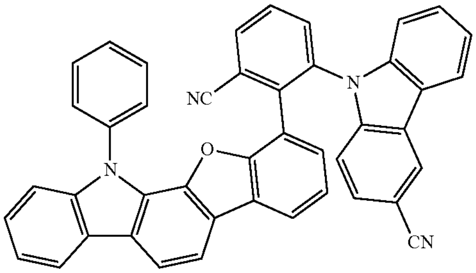
316
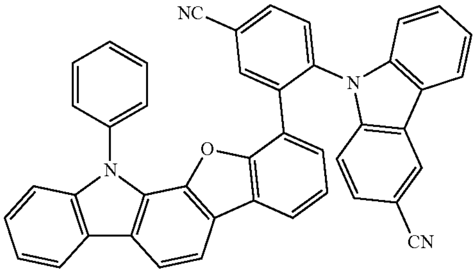
317
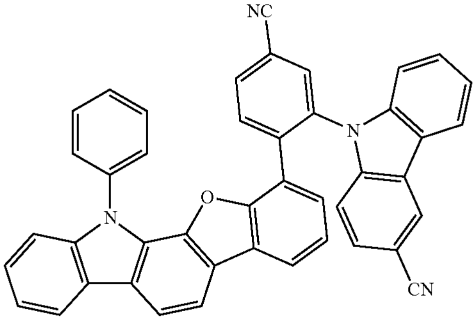
318
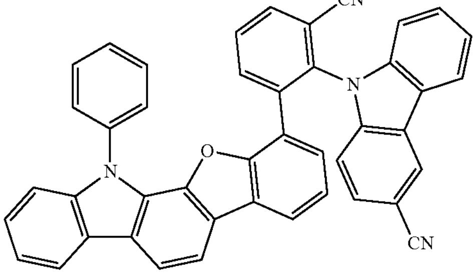

-continued
319
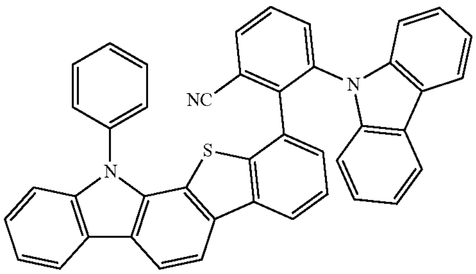
320
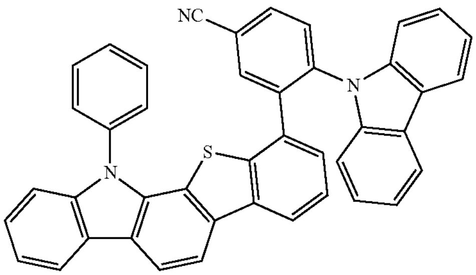
321
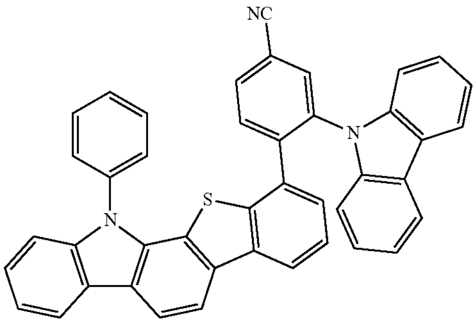
322
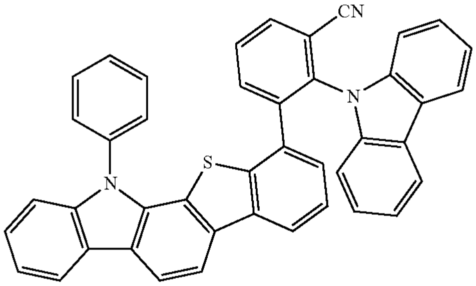
323
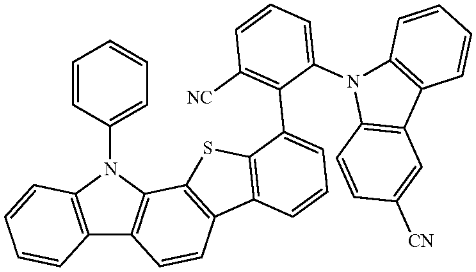
-continued
324
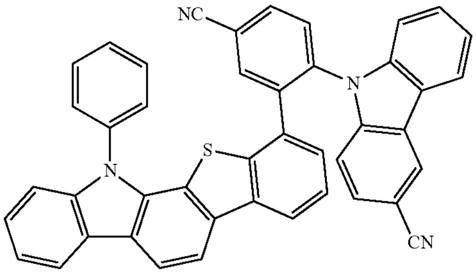
325
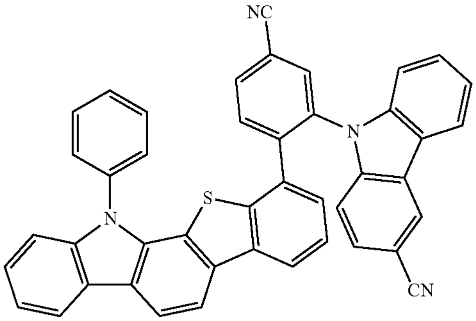
326
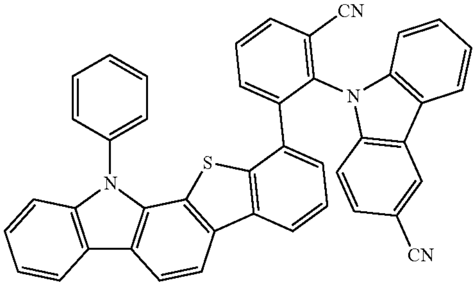
327
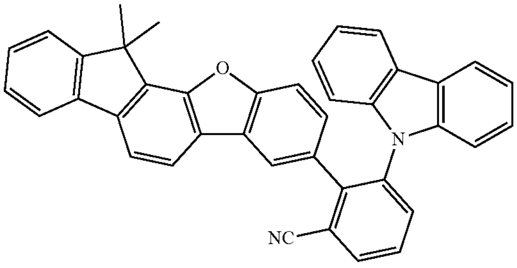
328
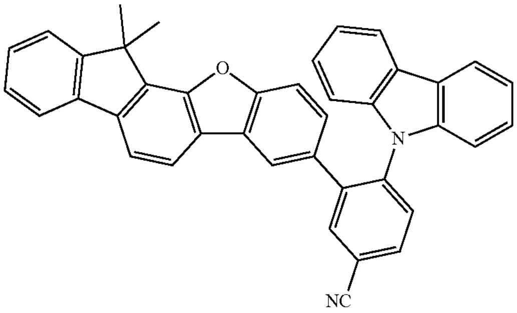

-continued
329
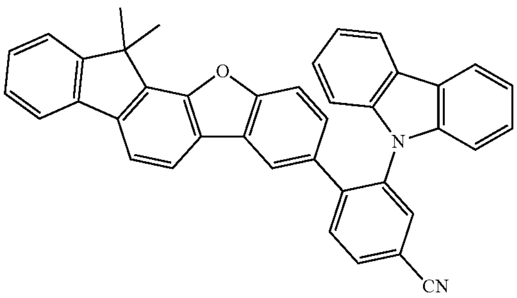
330
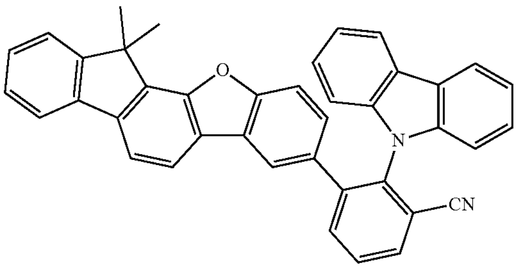
331
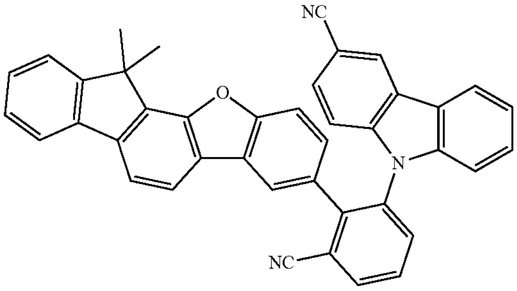
332
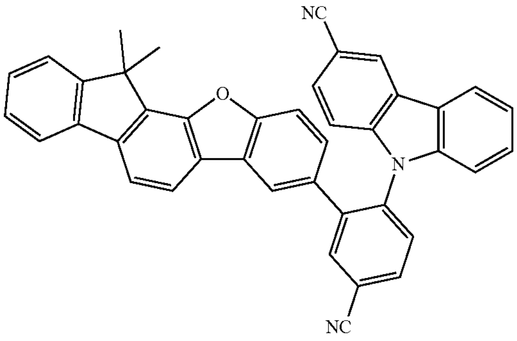
333
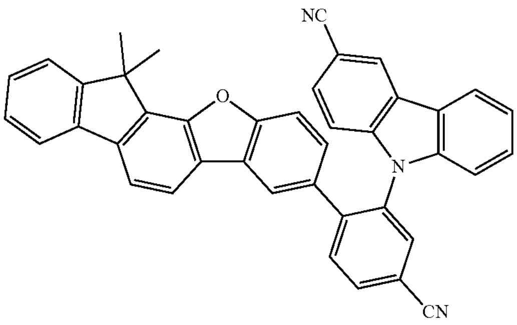
-continued
334
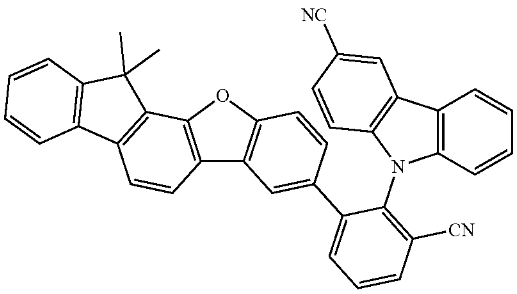
335
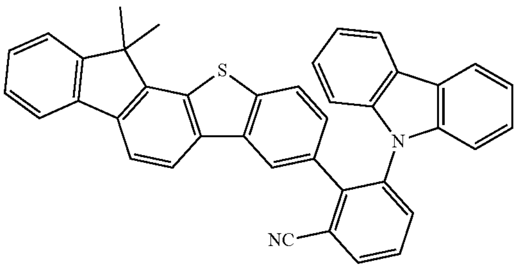
336
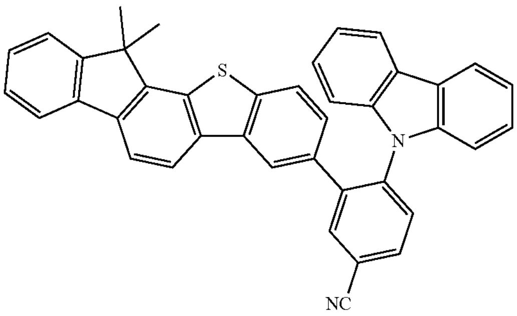
337
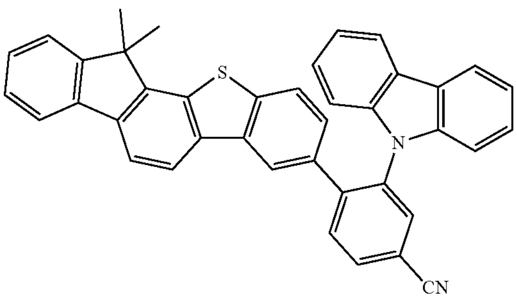
338
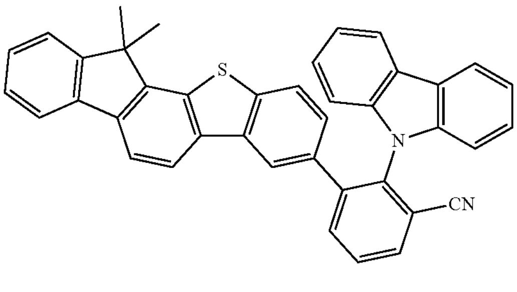

-continued
339
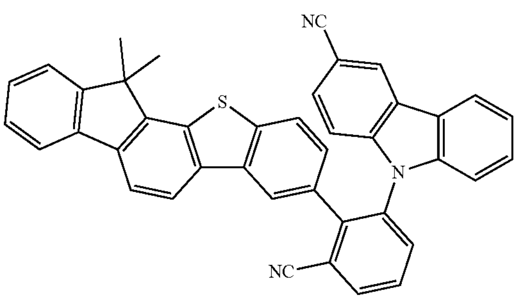
340
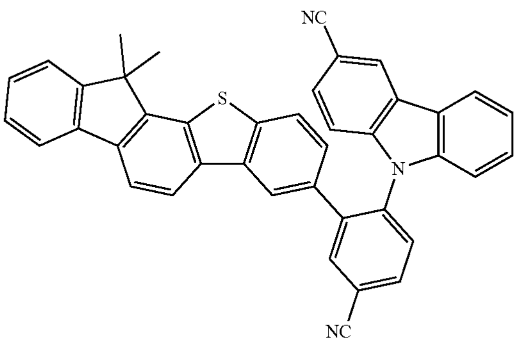
341
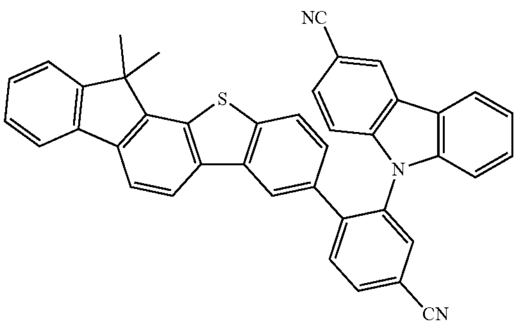
342
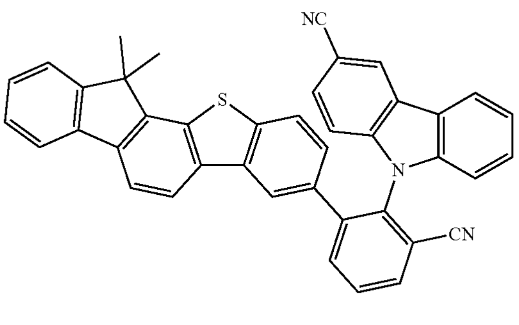
-continued
343
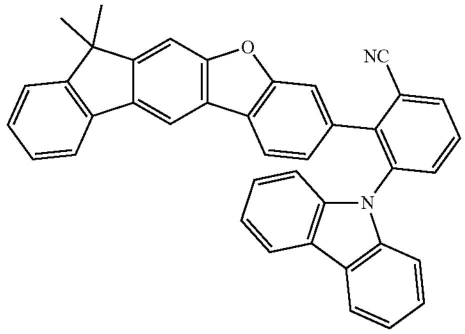
344
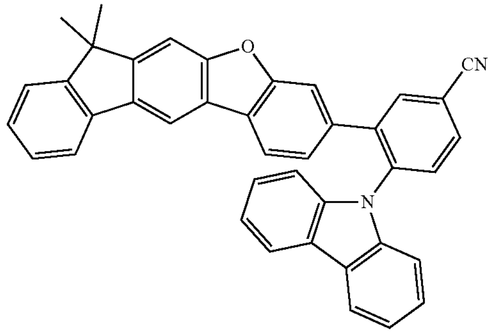
345
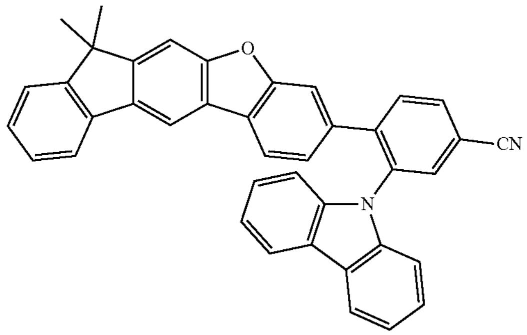
346
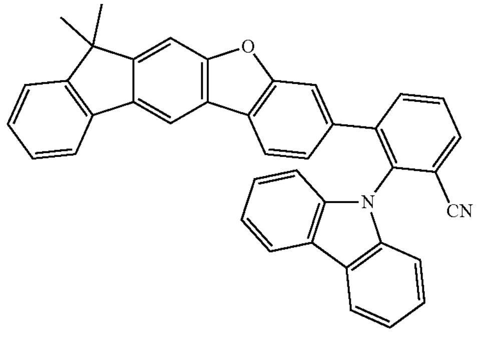

-continued
347
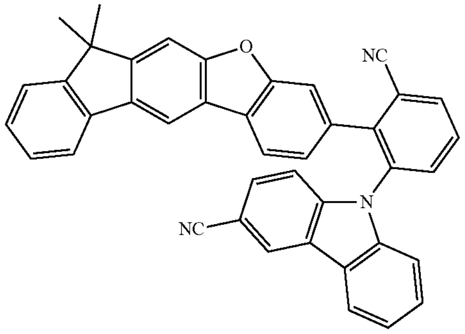
348
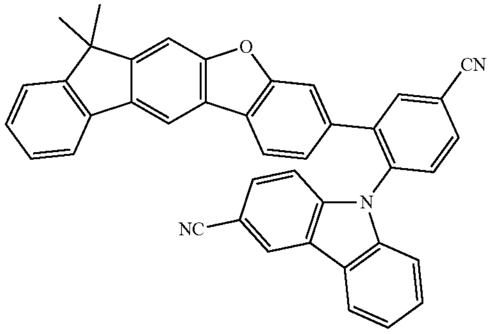
349
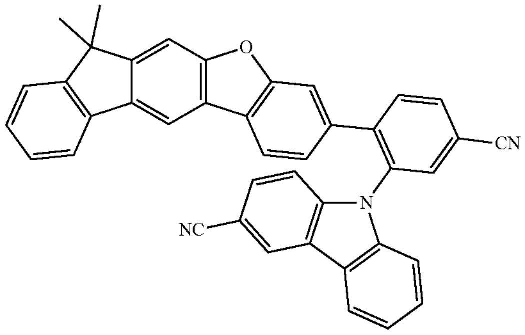
350
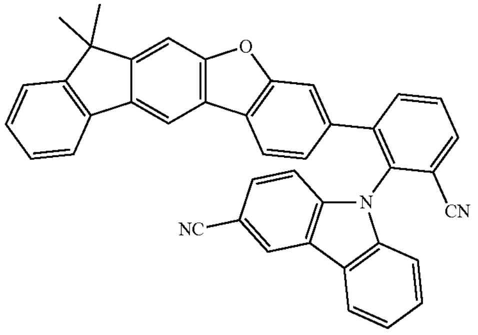
-continued
351
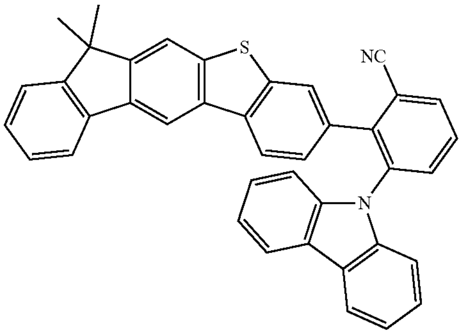
352
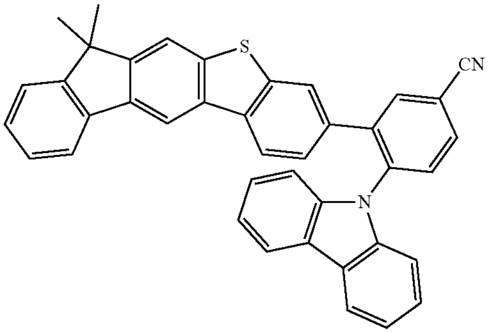
353
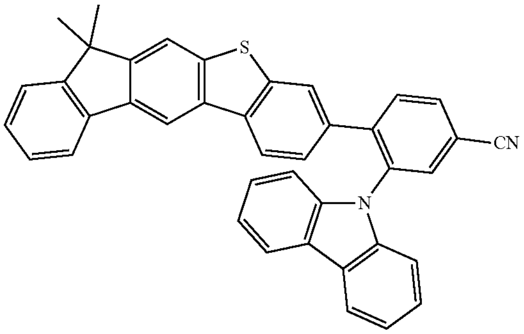
354
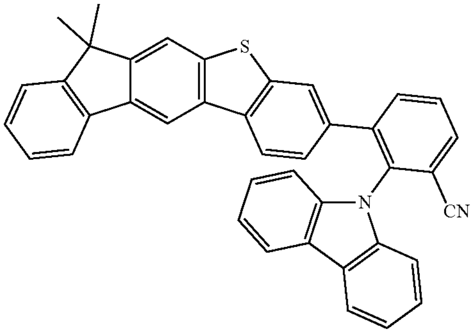

-continued
355
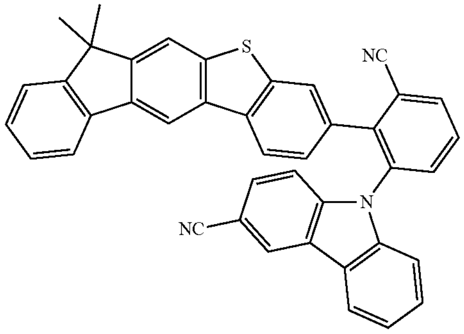
356
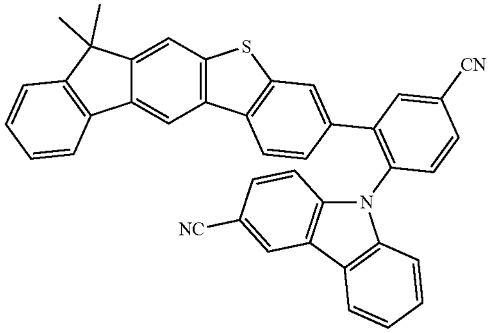
357
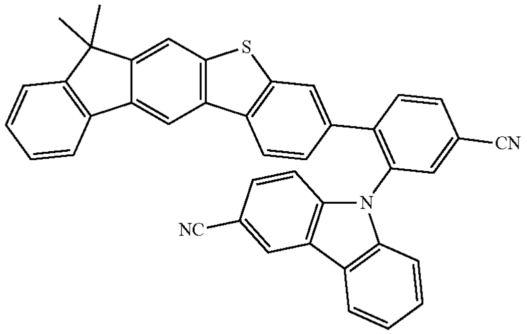
358
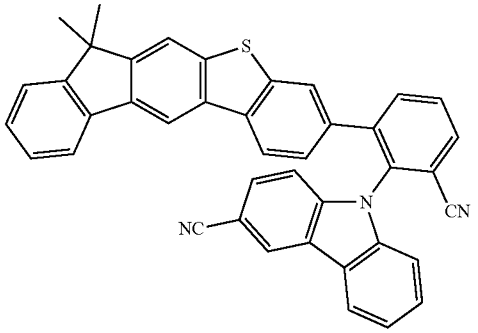
-continued
359
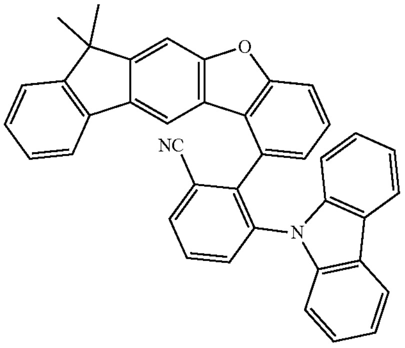
360
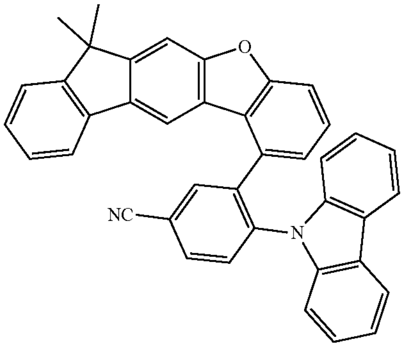
361
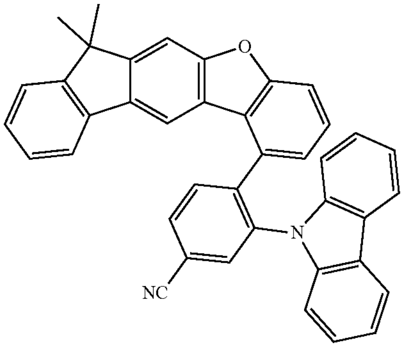
362
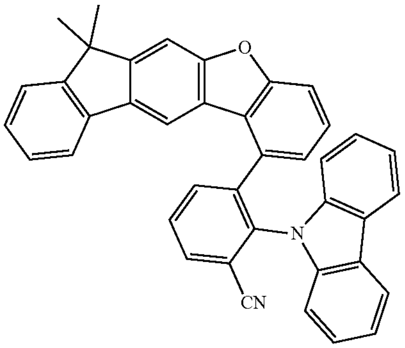

-continued
363
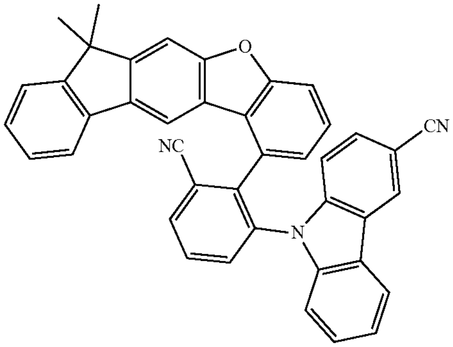
364
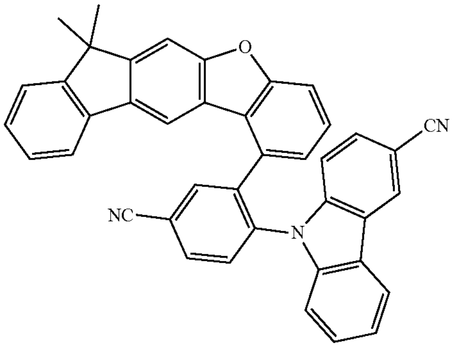
365
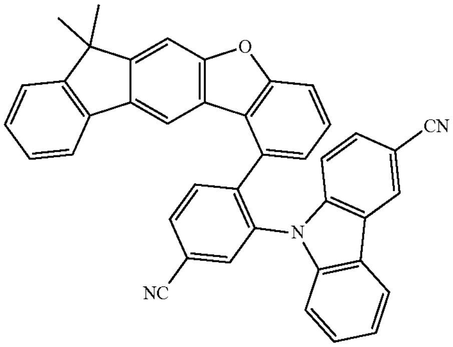
366
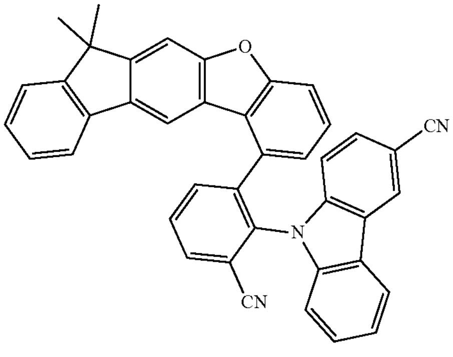
-continued
367
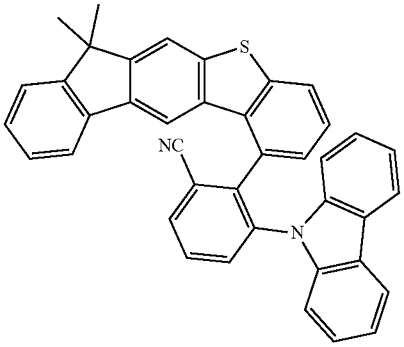
368
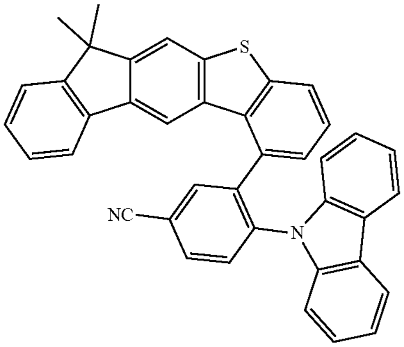
369
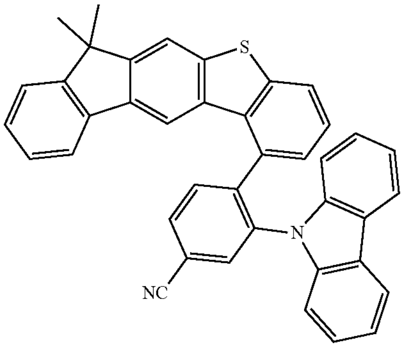
370
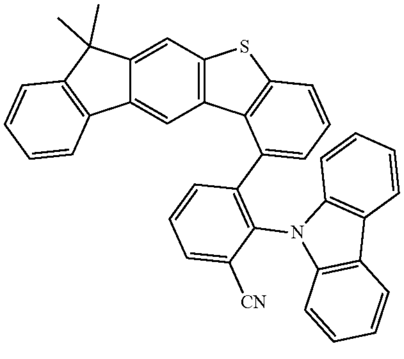

371
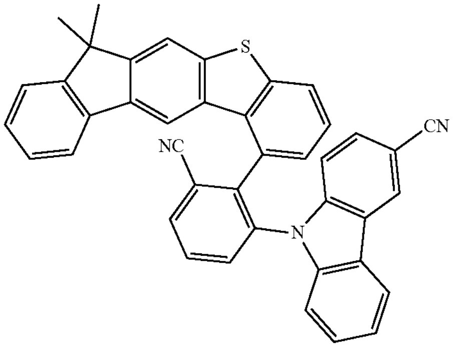
372
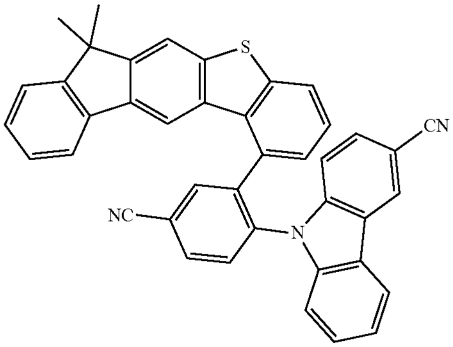
373
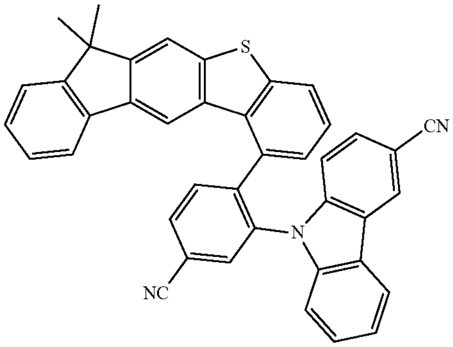
374
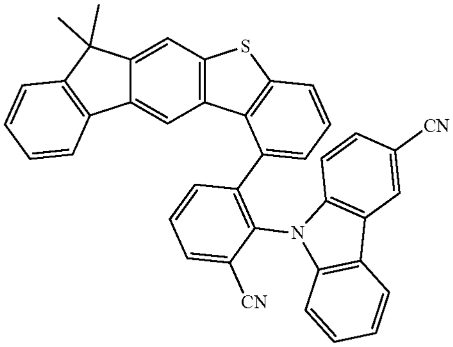
375
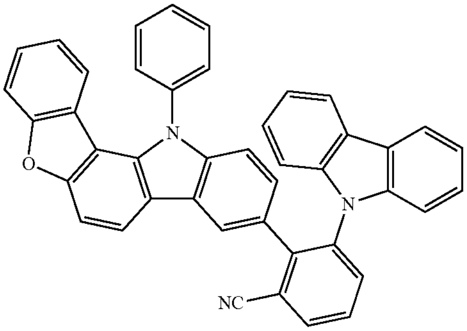
376
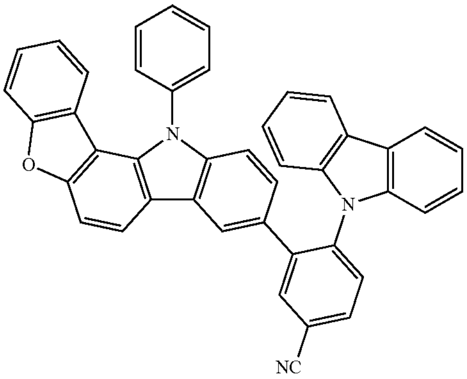
377
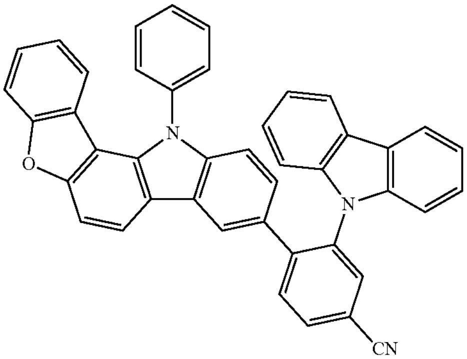
378
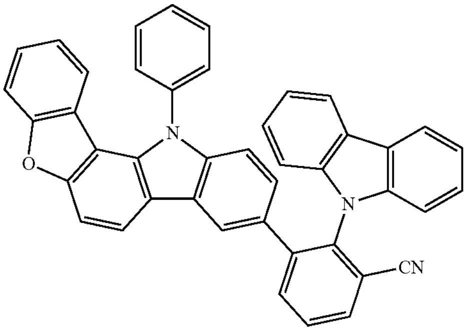

379
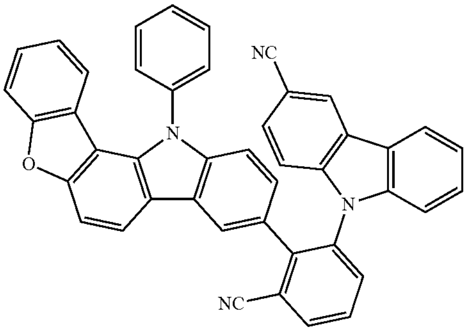
380
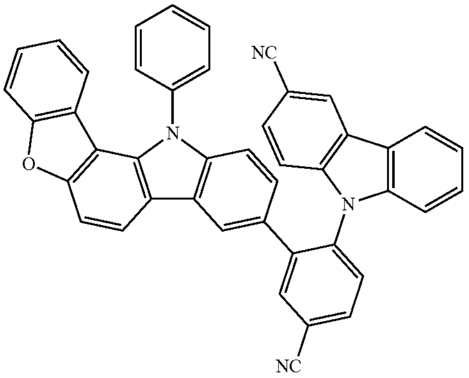
381
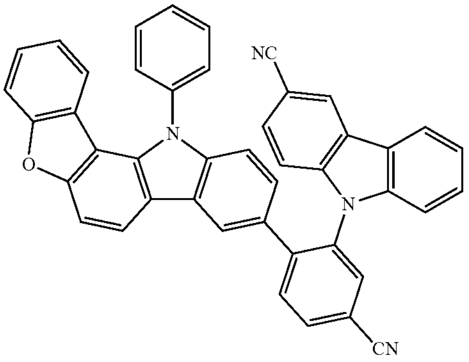
382
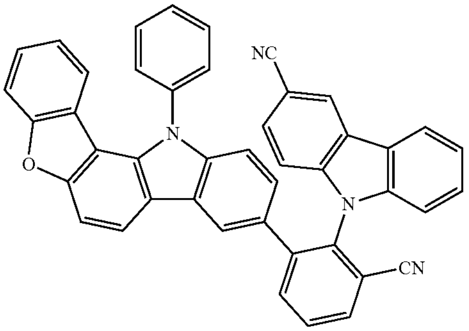
383
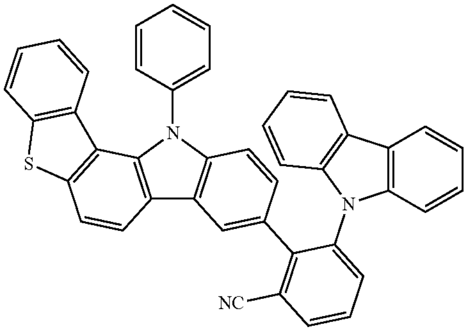
384
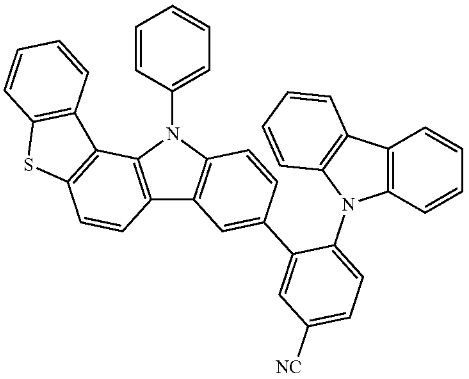
385
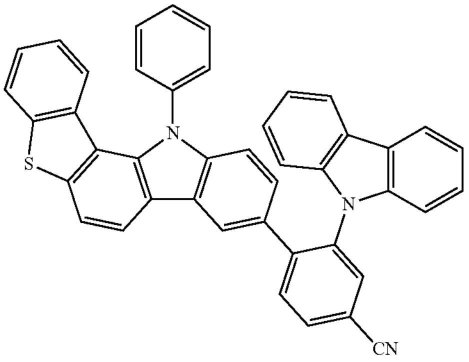
386
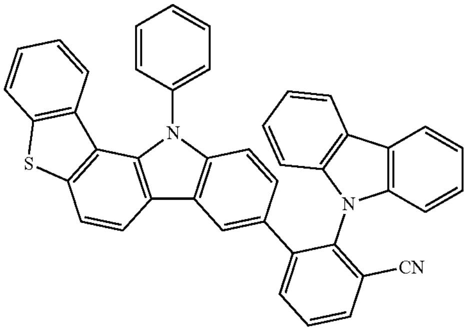

-continued
387
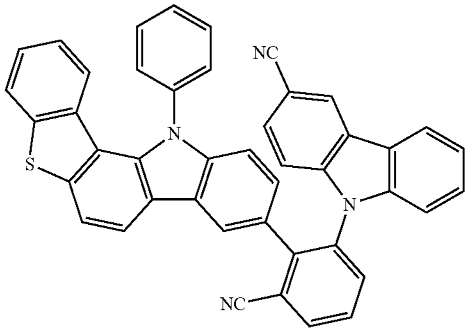
388
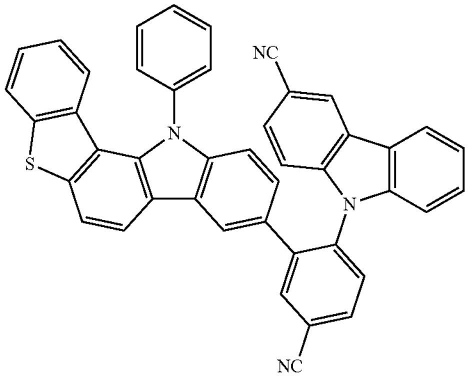
389
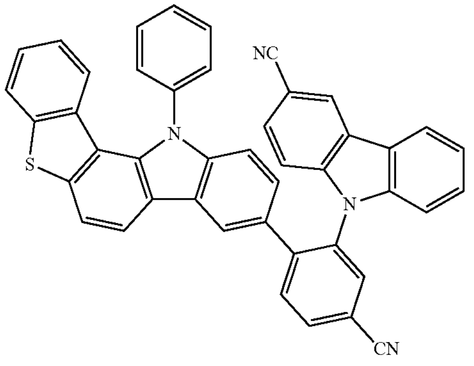
390
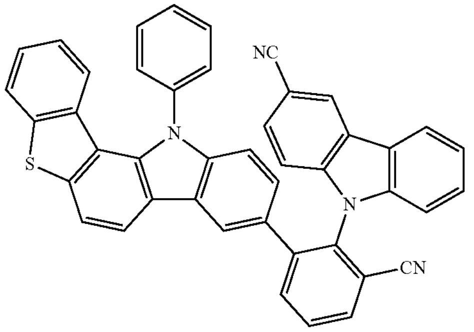
-continued
391
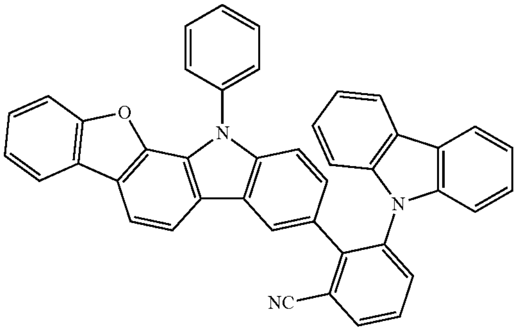
392
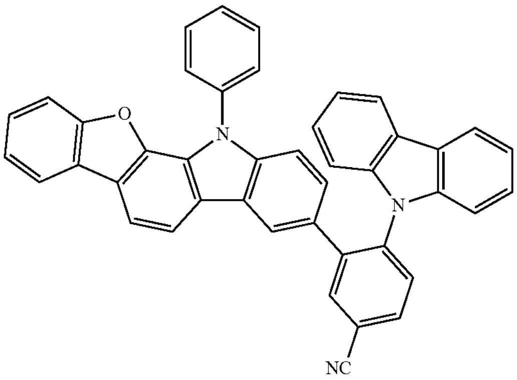
393
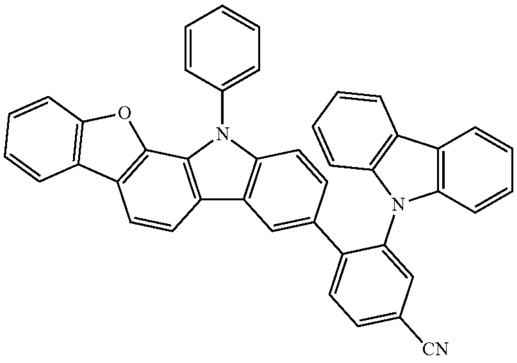
394
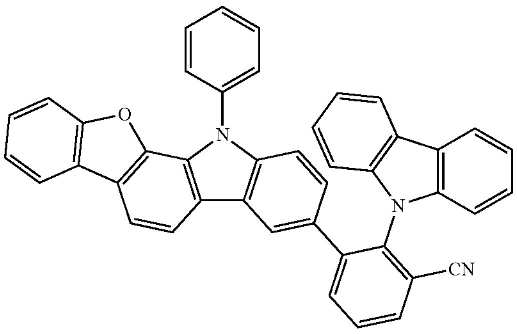

-continued
395
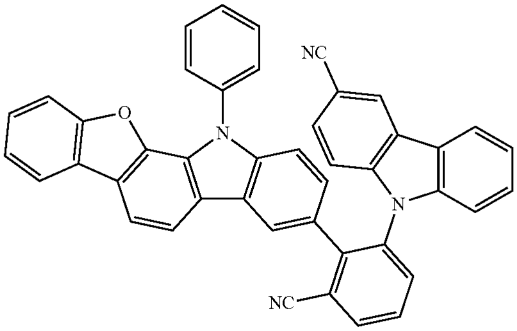
396
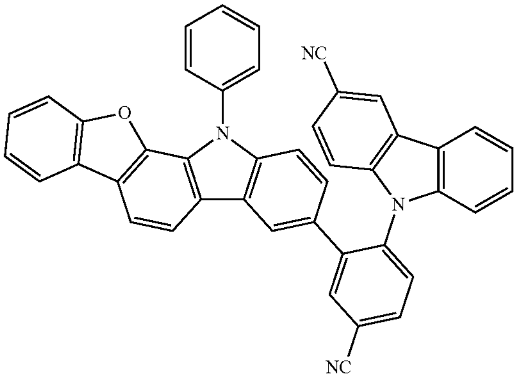
397
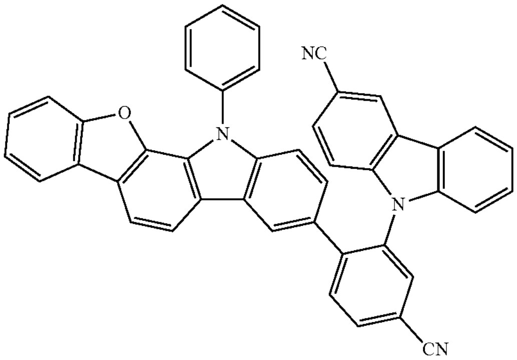
398
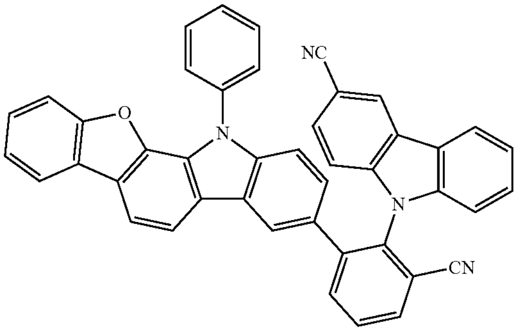
-continued
399
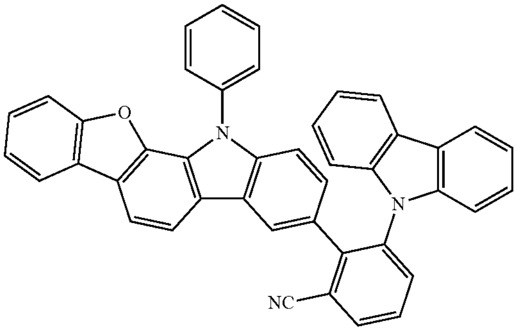
400
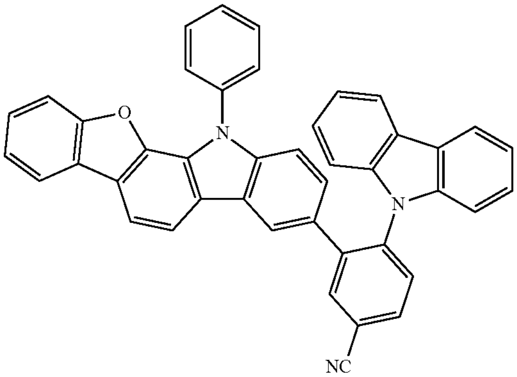
401
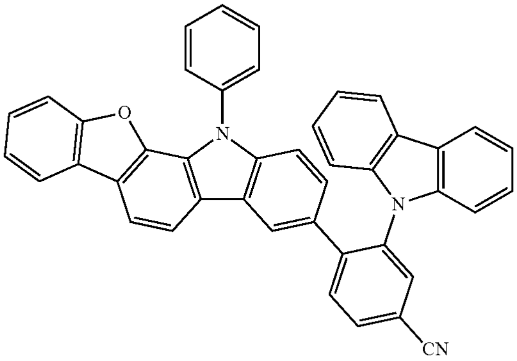
402
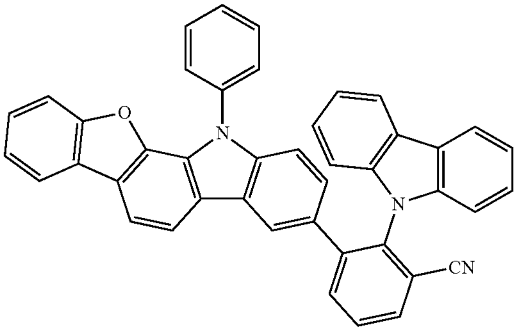

-continued
403
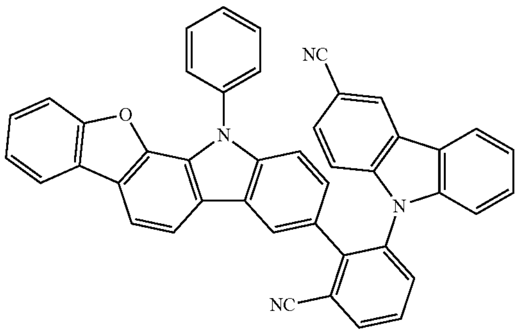
404
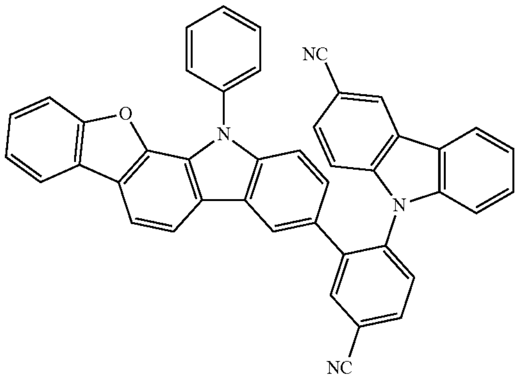
405
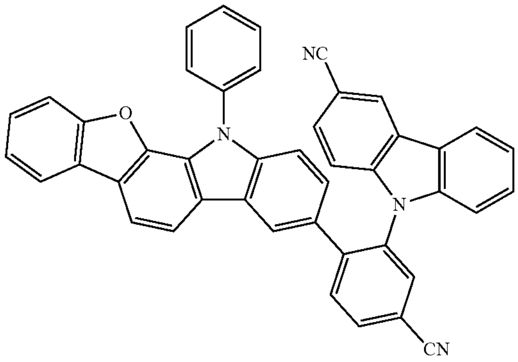
406
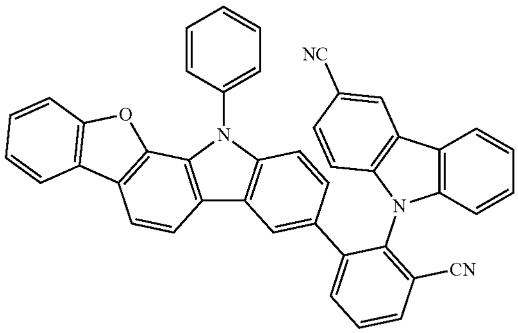
-continued
407
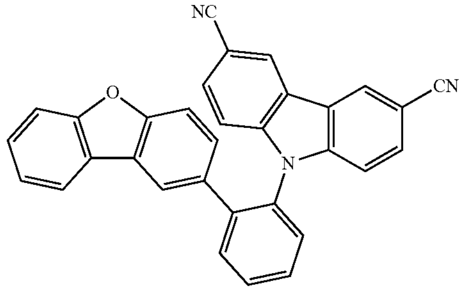
408
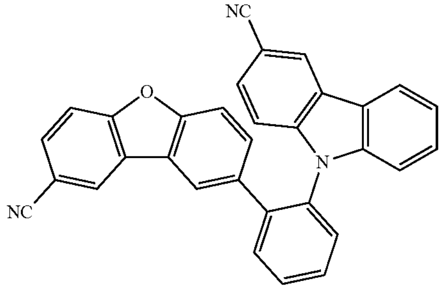
409
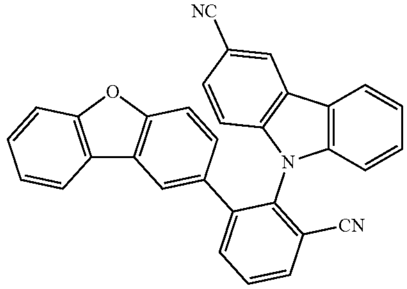
410
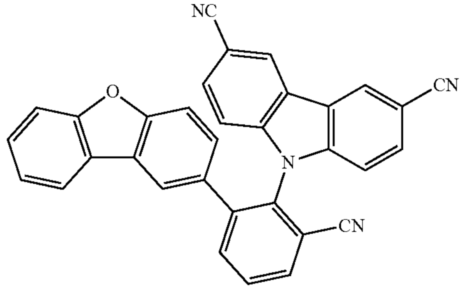
411
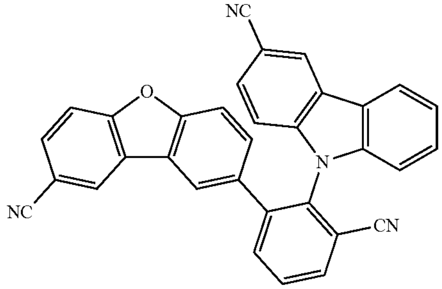

-continued
412
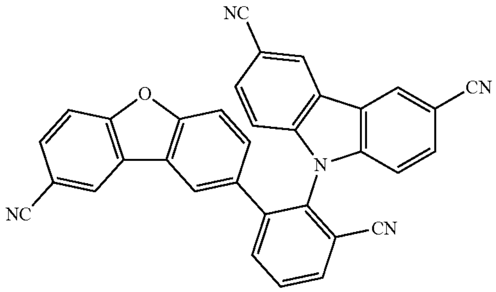
413
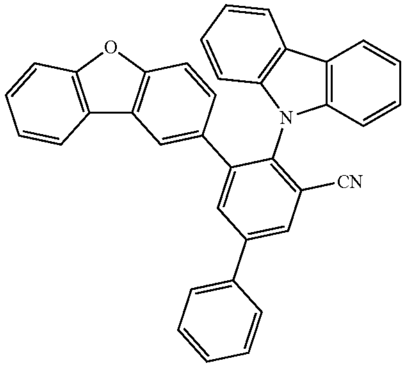
414
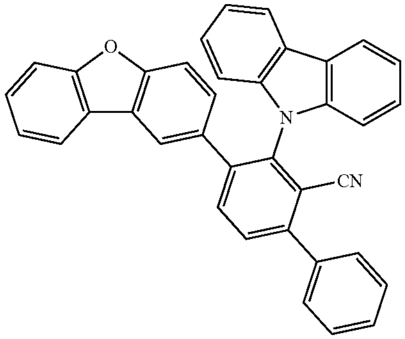
415
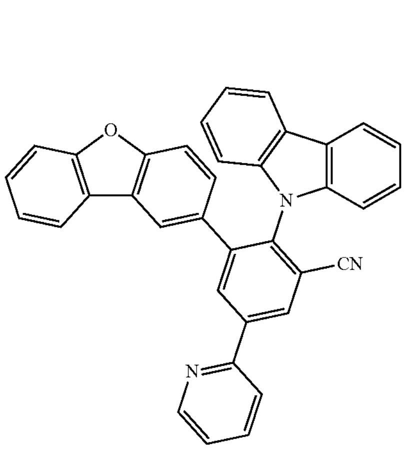
-continued
416
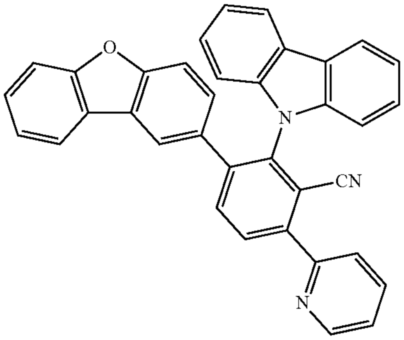
417
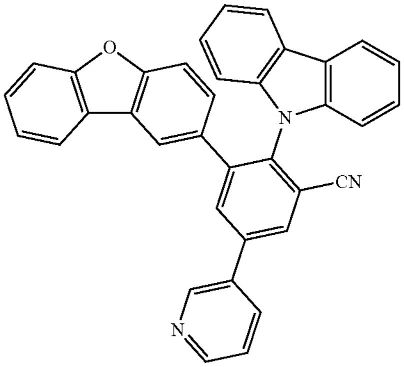
418
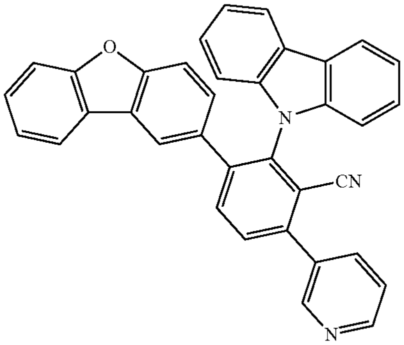
419
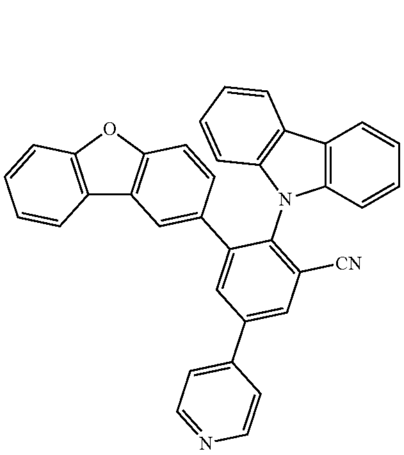

-continued
420
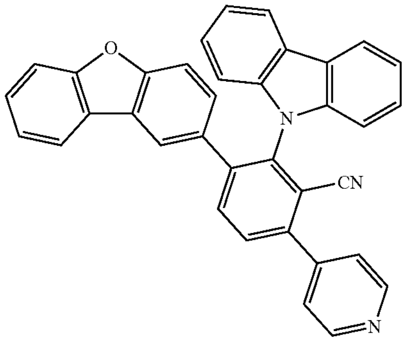
421
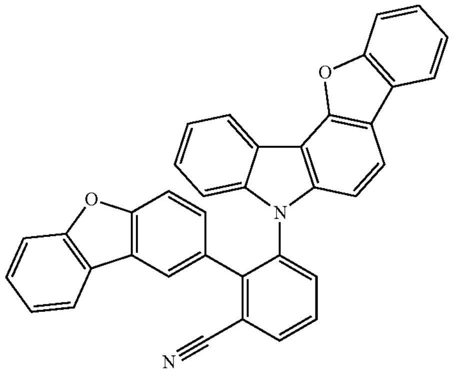
422
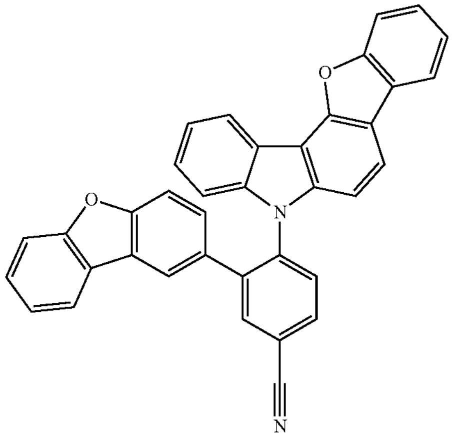
423
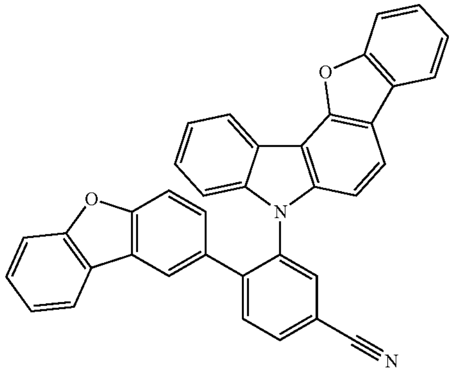
-continued
424
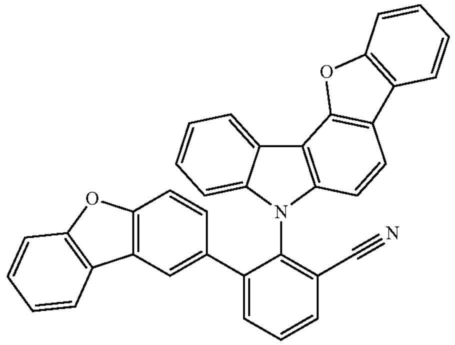
425
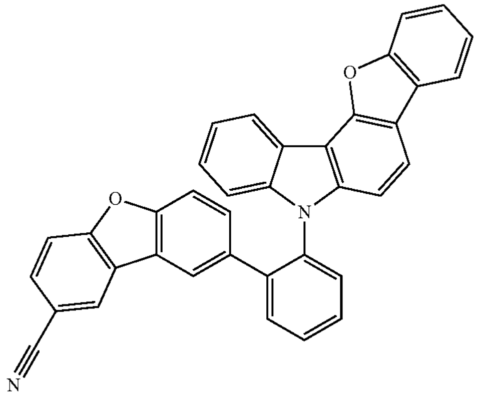
426
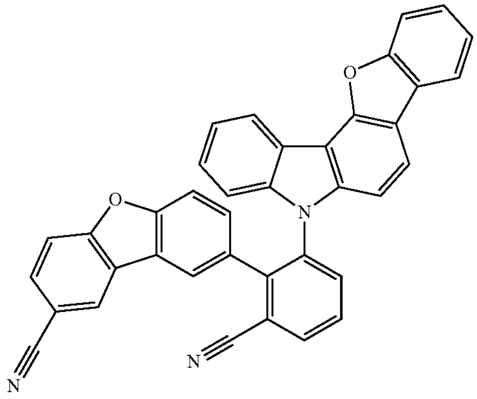
427
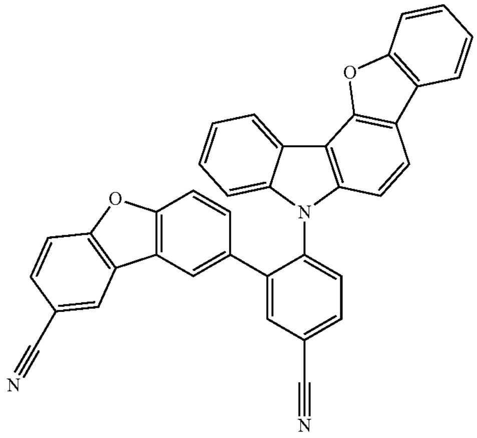

-continued
428
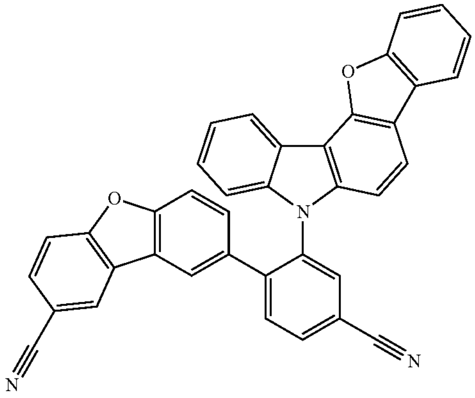
429
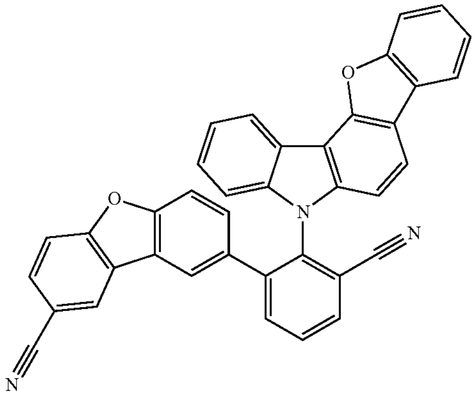
430
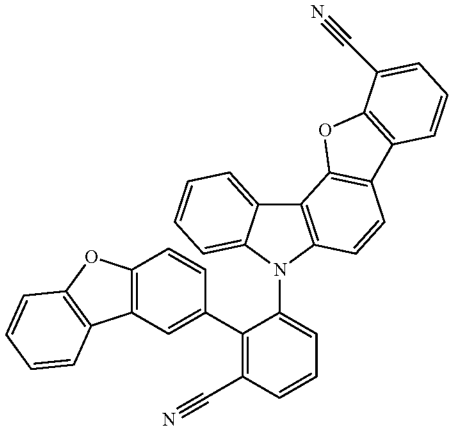
-continued
431
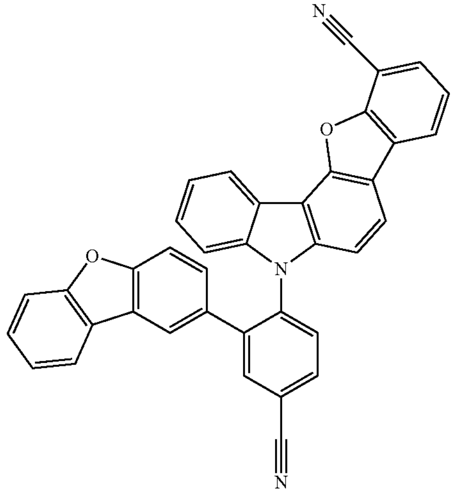
432
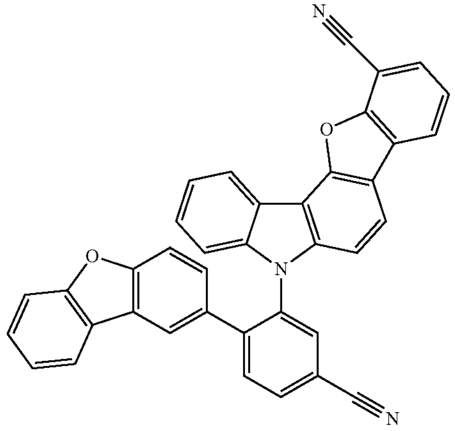
433
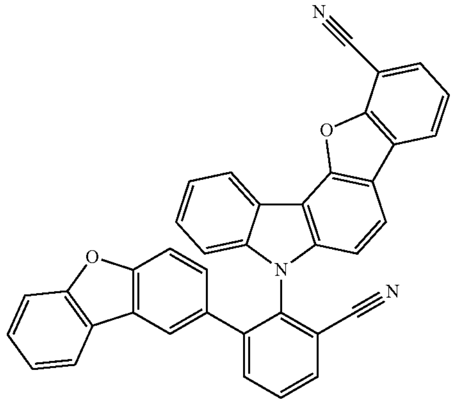

-continued
434
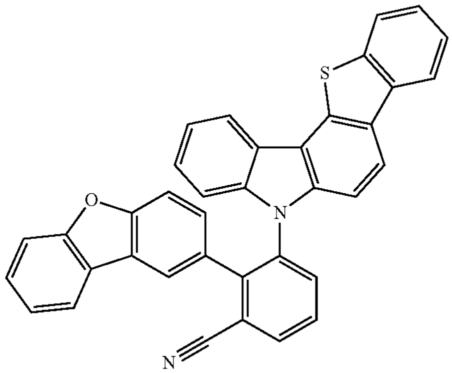
435
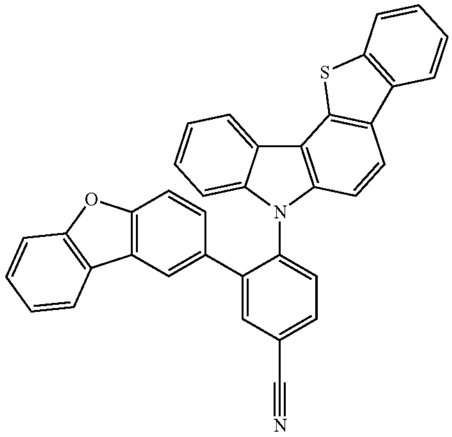
436
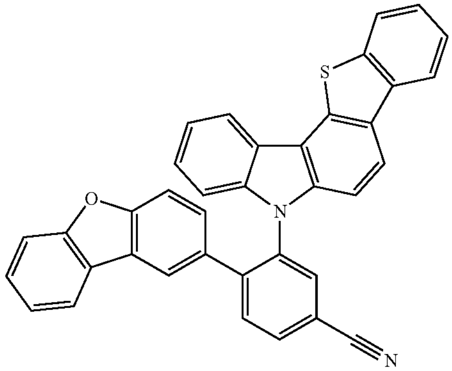
437
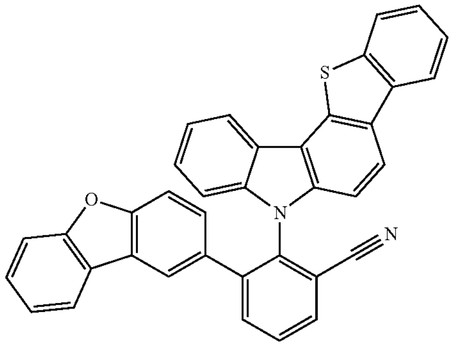
-continued
438
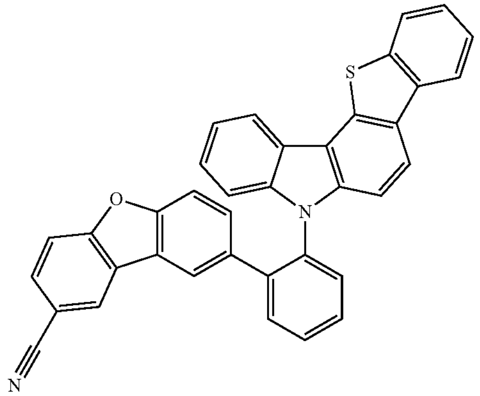
439
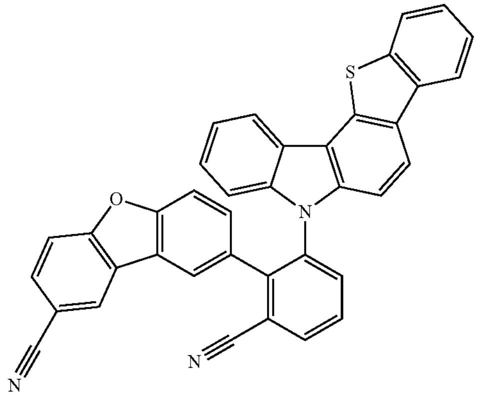
440
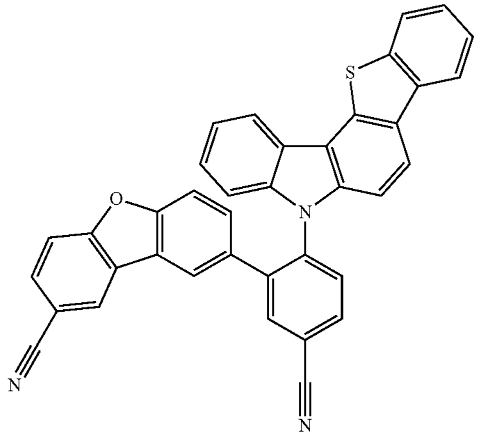
441
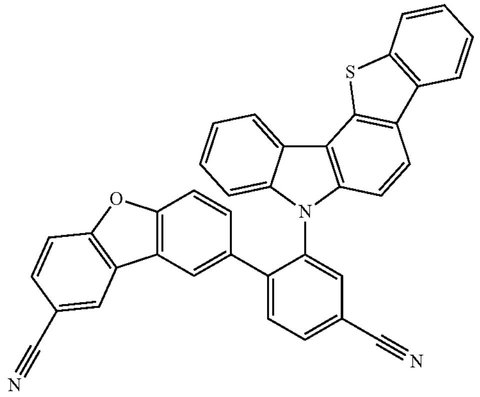

-continued
442
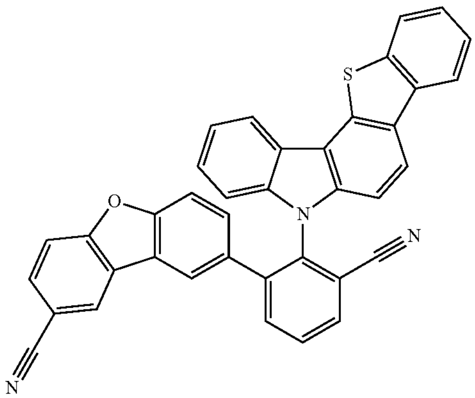
443
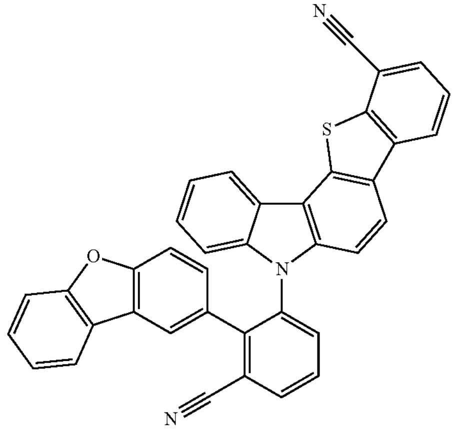
444
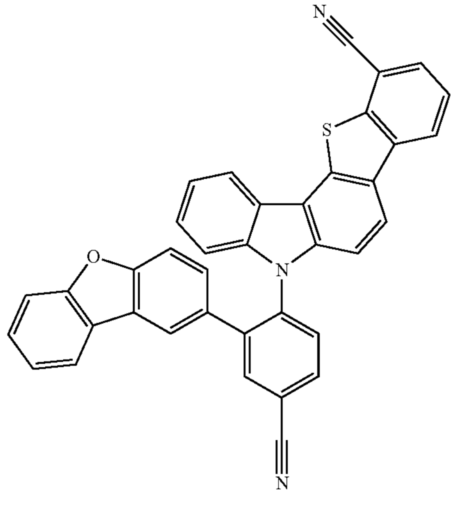
-continued
445
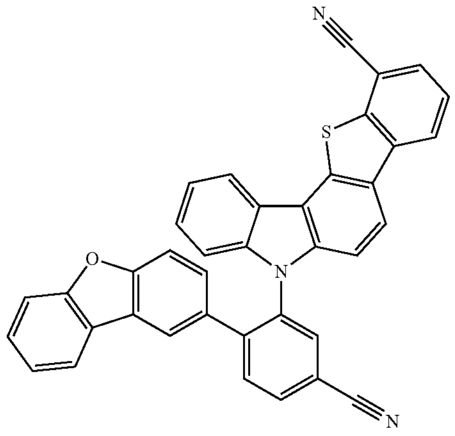
446
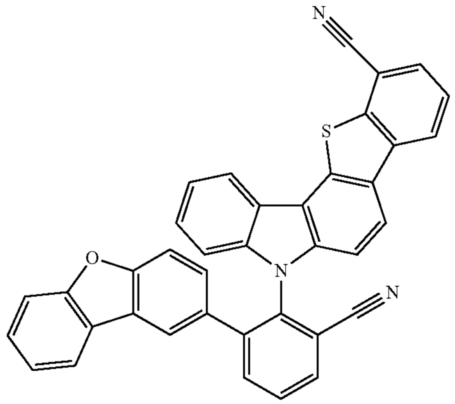
447
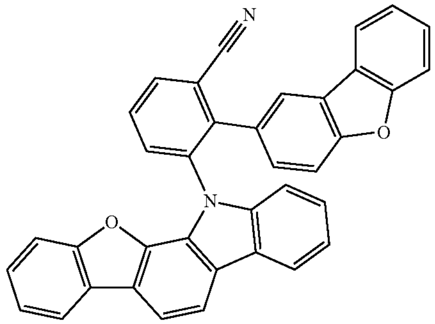
448
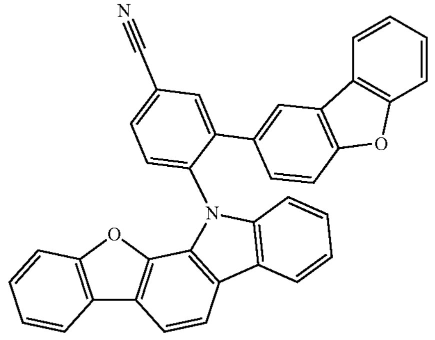

-continued
449
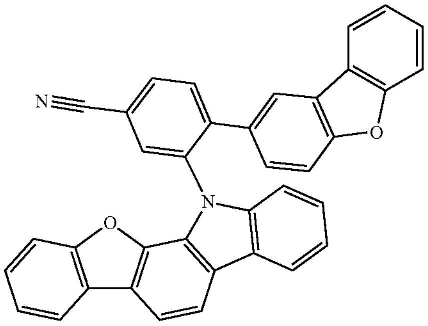
450
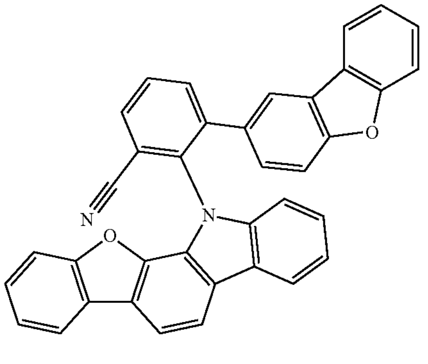
451
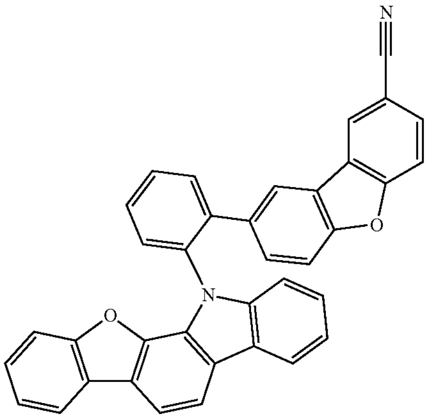
452
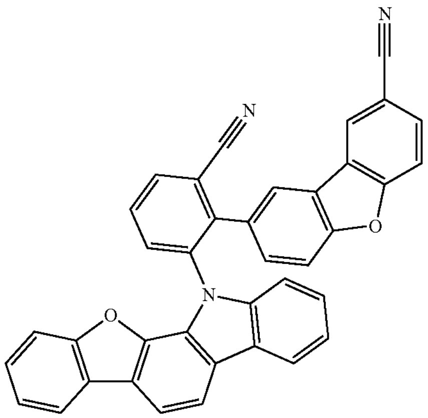
-continued
453
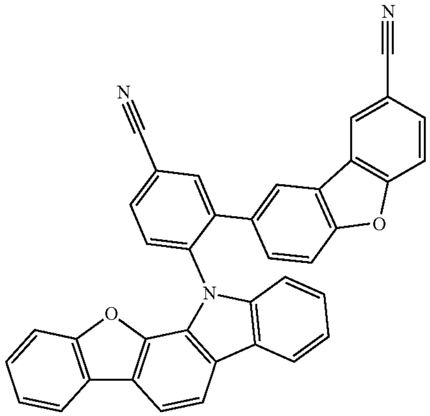
454
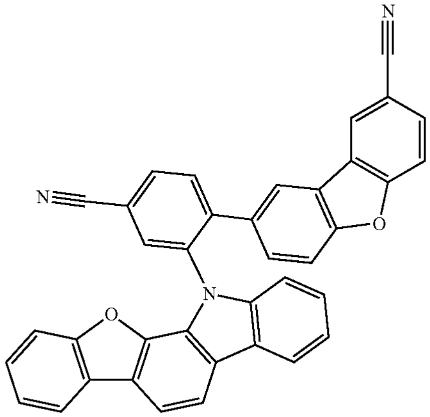
455
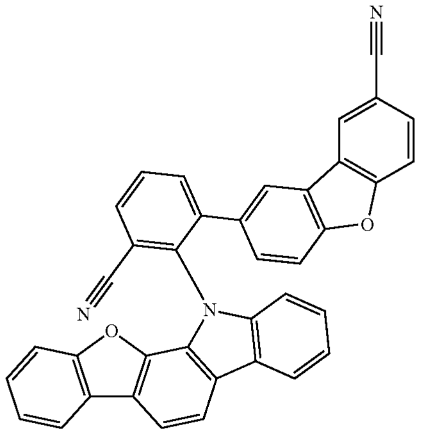
456
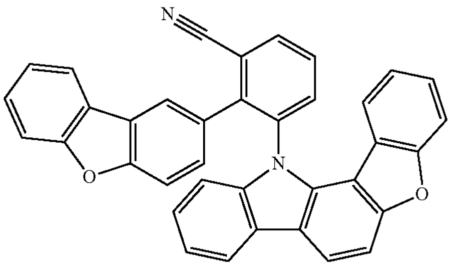

-continued
457
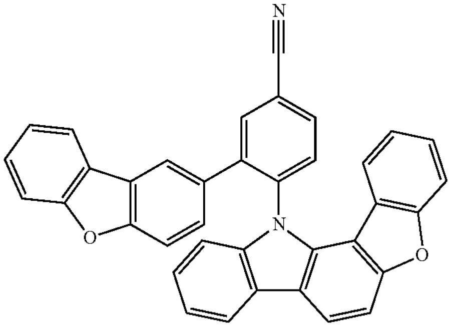
458
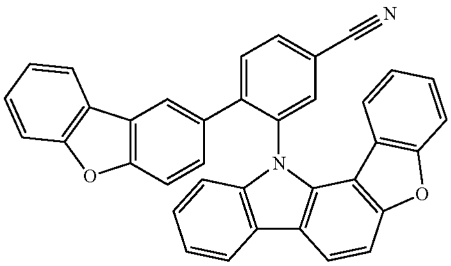
459
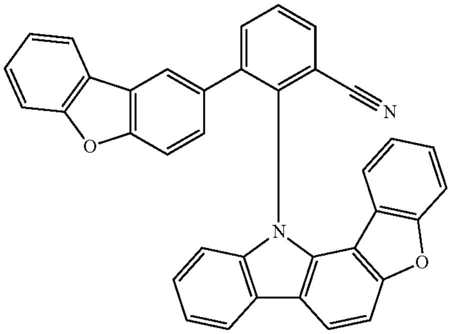
460
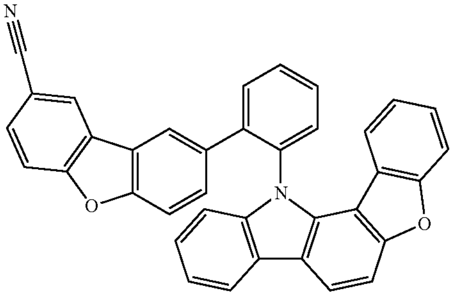
461
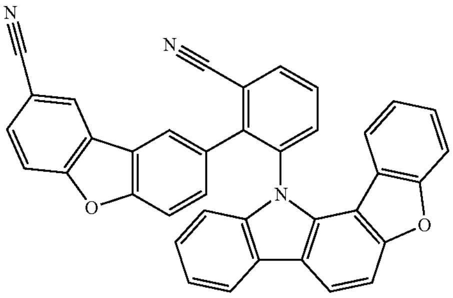
-continued
462
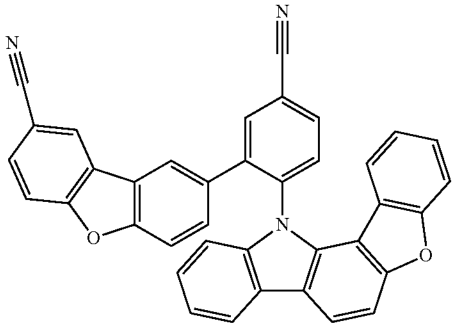
463
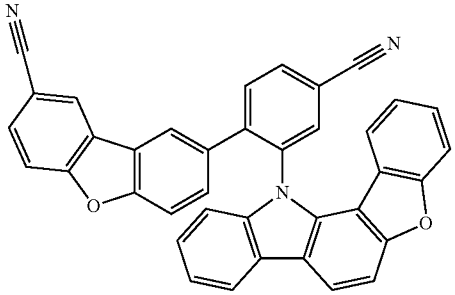
464
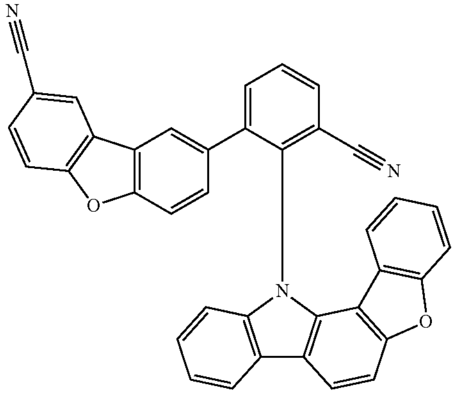
465
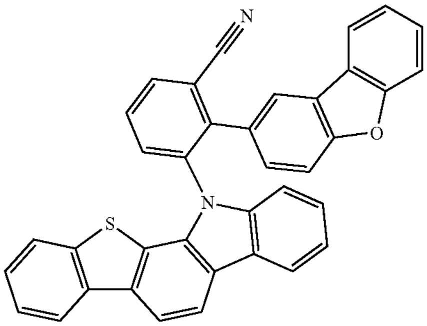

-continued
466
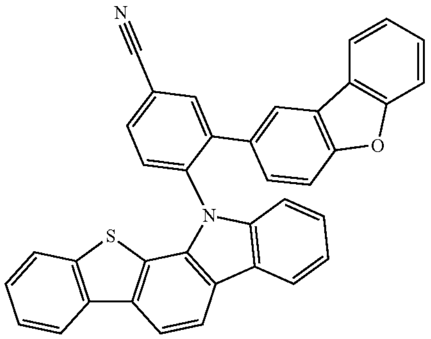
467
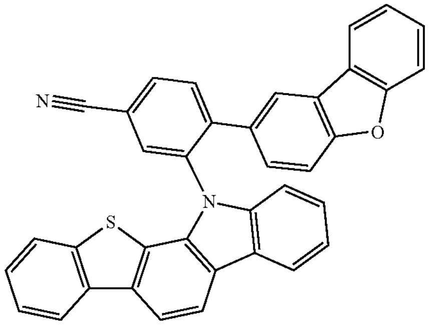
468
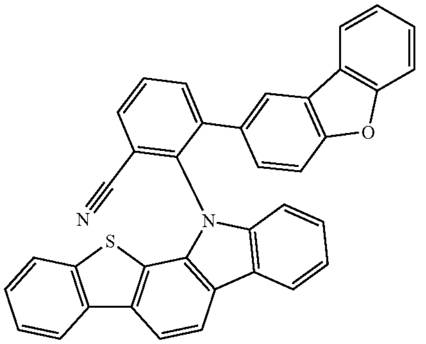
469
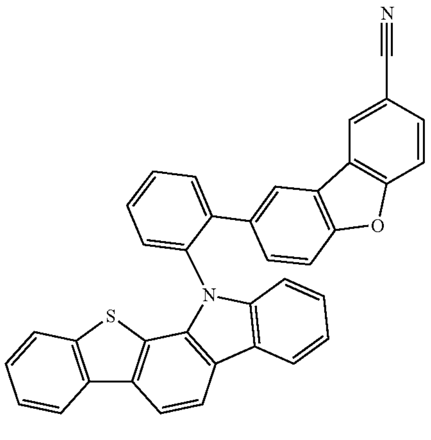
-continued
470
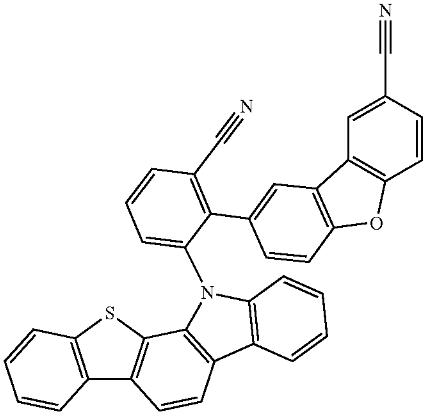
471
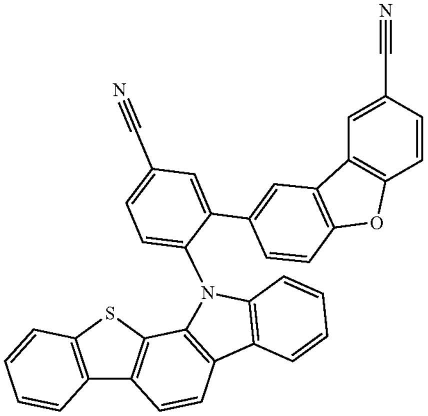
472
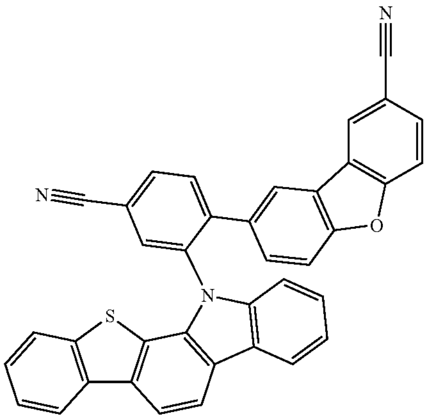

-continued
473
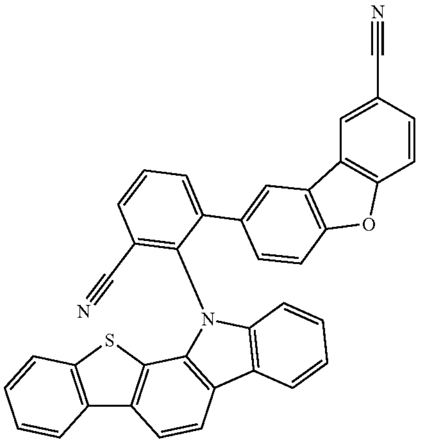
474
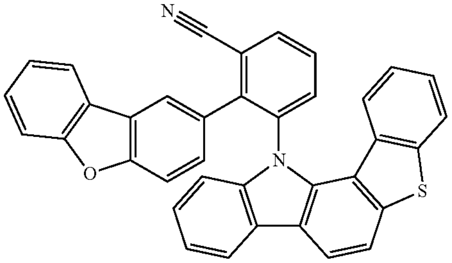
475
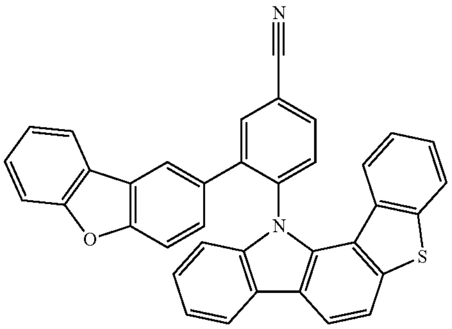
476
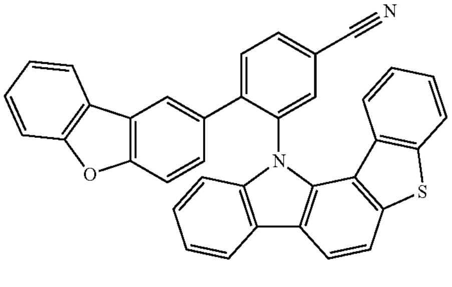
-continued
477
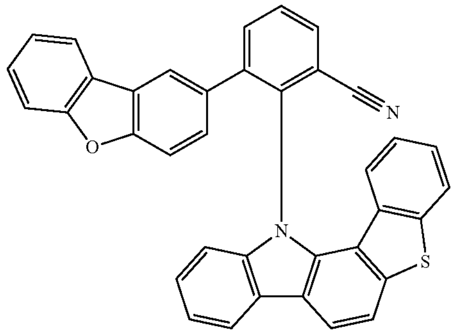
478
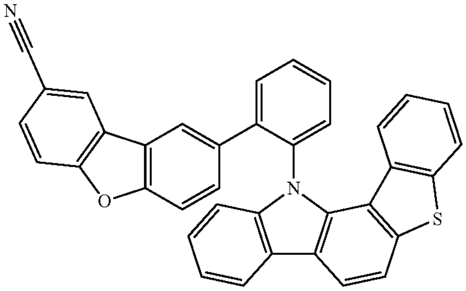
479
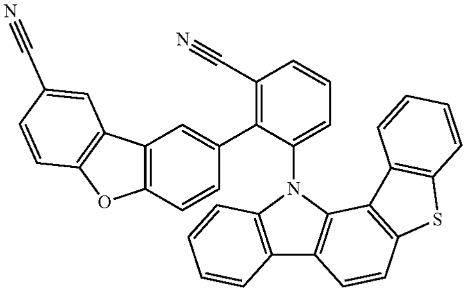
480
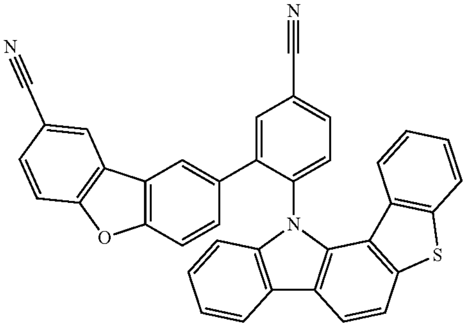
481
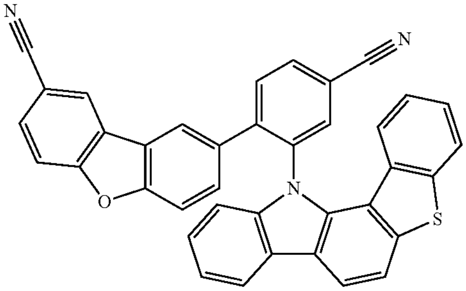

-continued
482
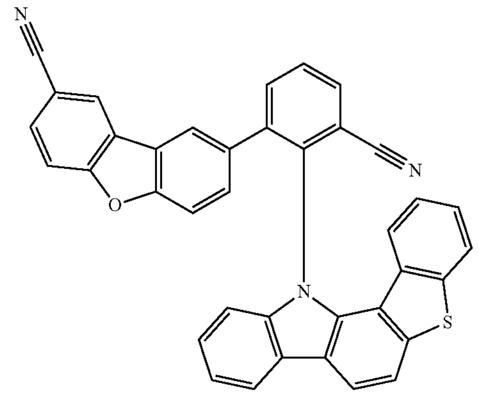
Group HE4
1
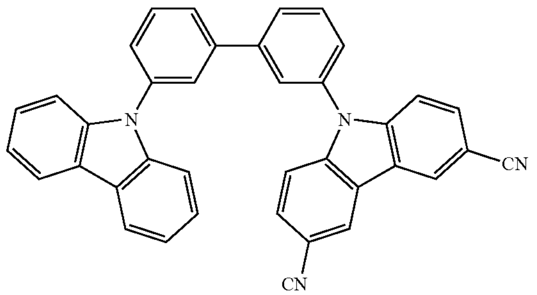
2
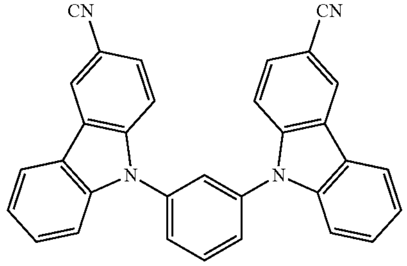
3
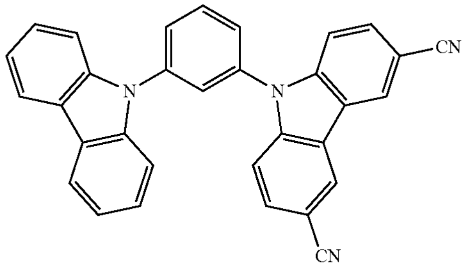
4
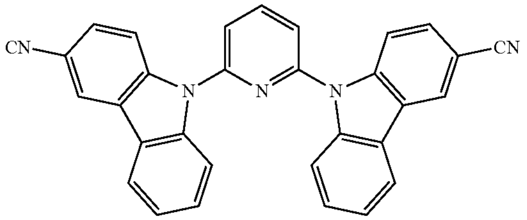
-continued
5
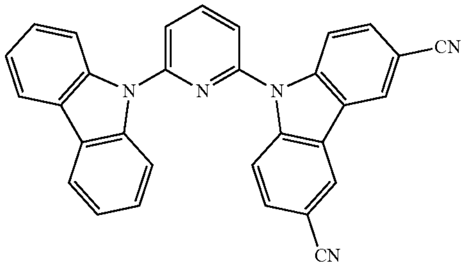
6
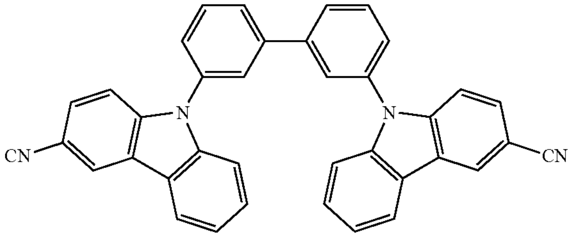
7
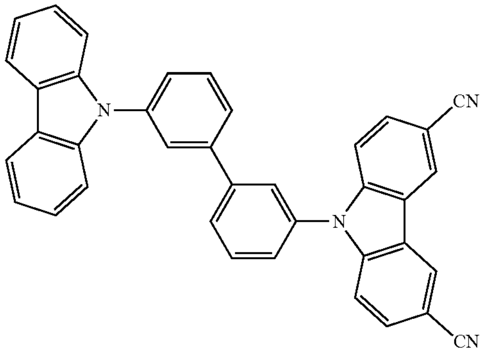
8
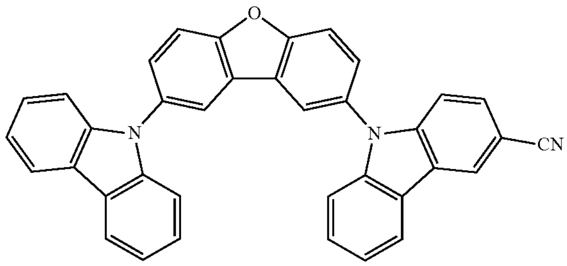
9
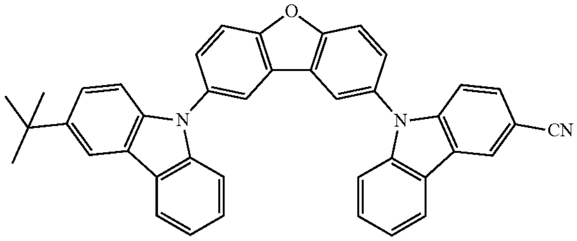

10
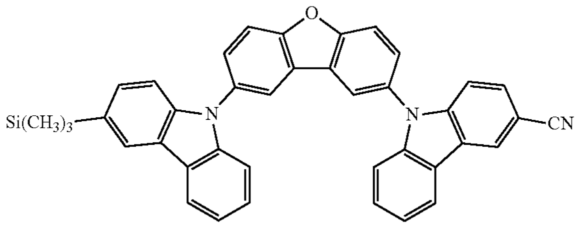
11
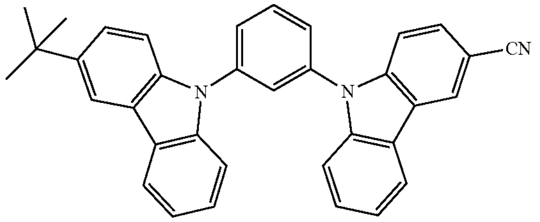
12
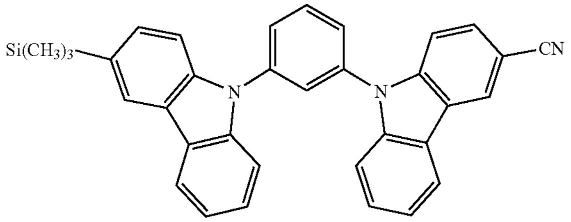
13
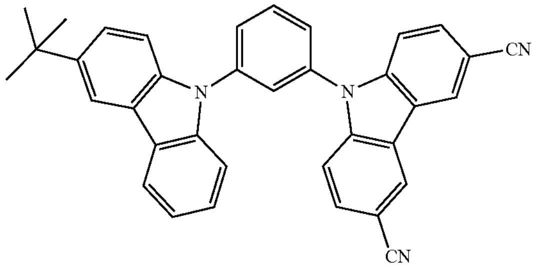
14
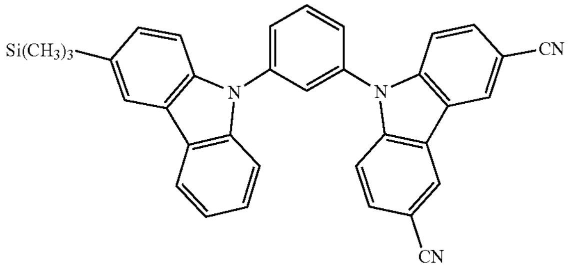
15
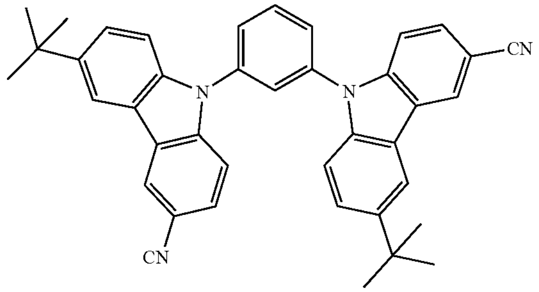
16
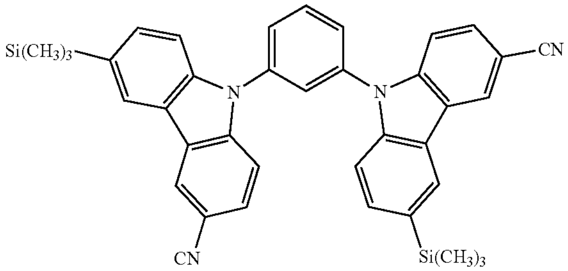
17
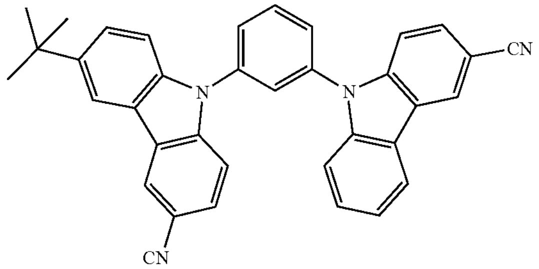
18
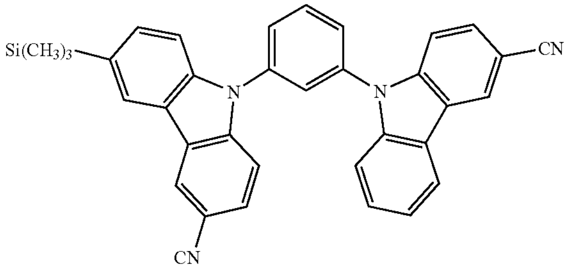
19
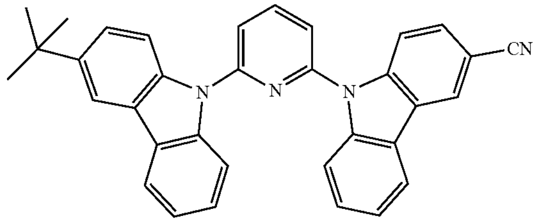

-continued
20
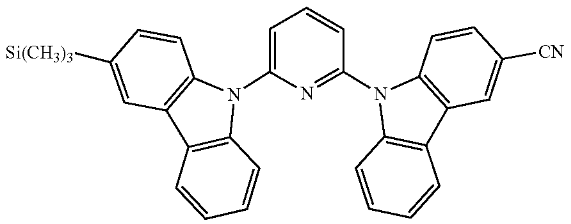
21
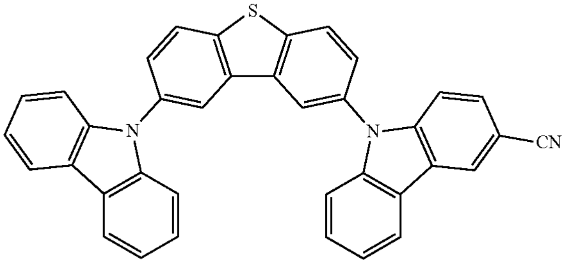
22
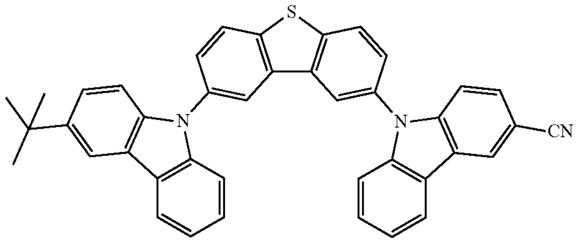
23
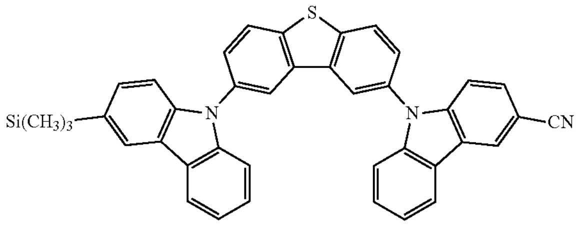
24
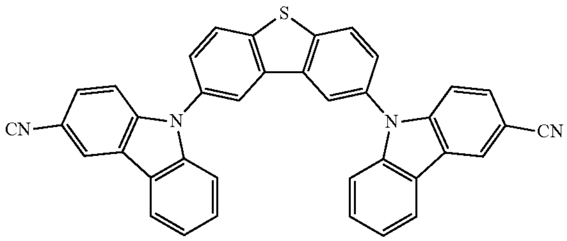
-continued
25
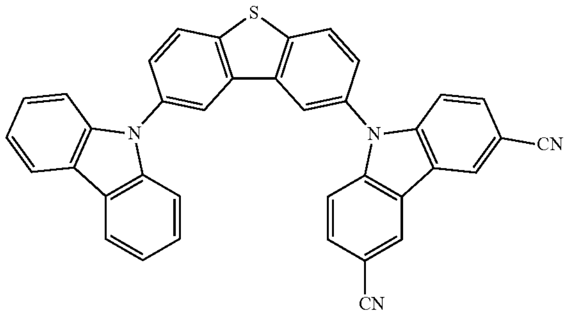
26
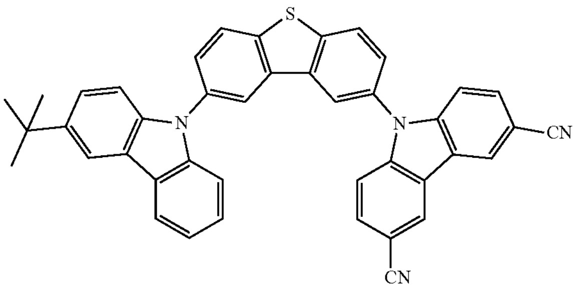
27
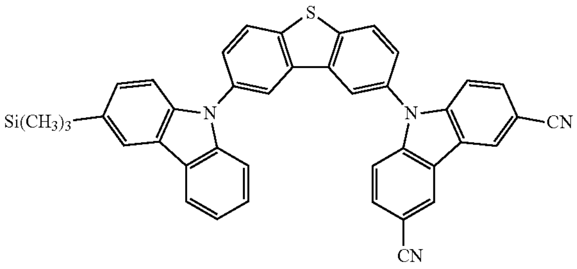
28
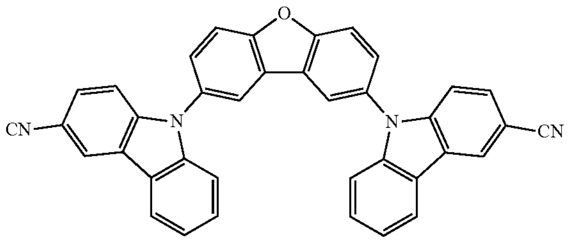
29
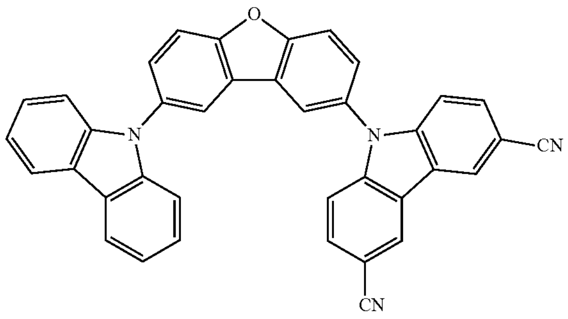

-continued
30
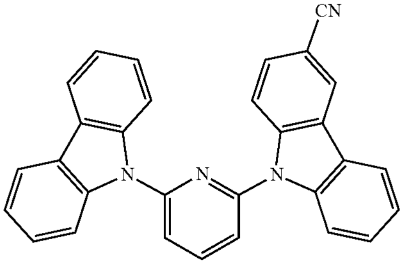
31
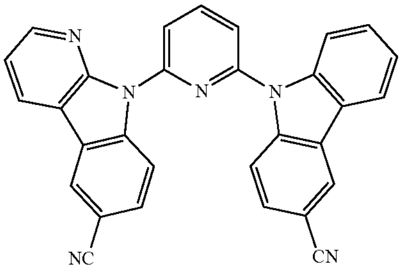
32
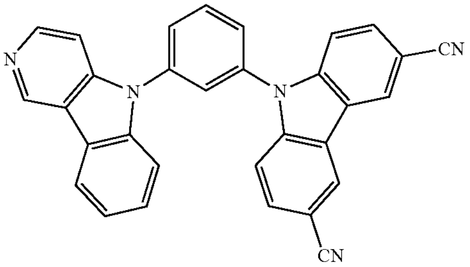
33
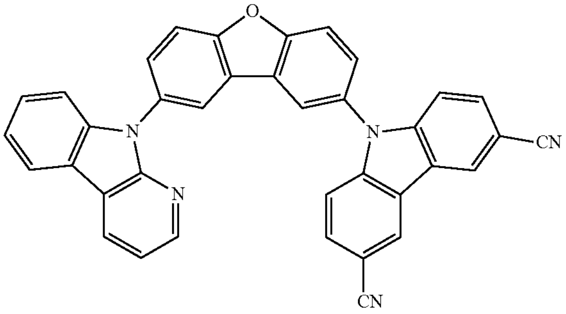
34
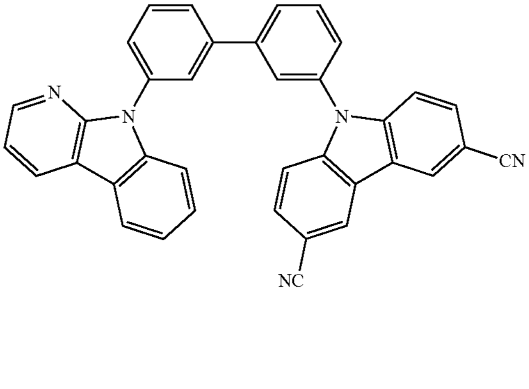
-continued
35
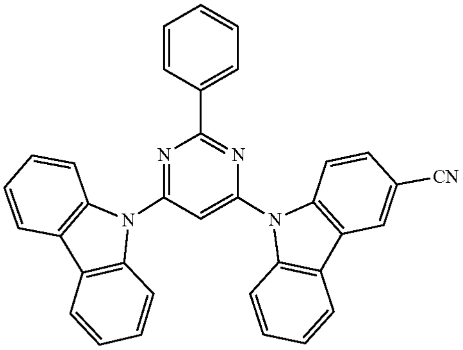
36
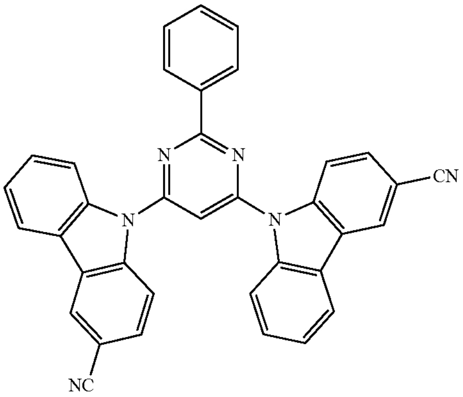
37
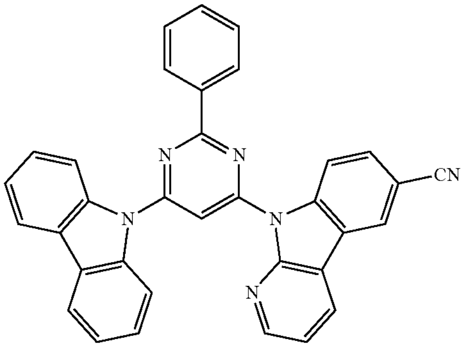
38
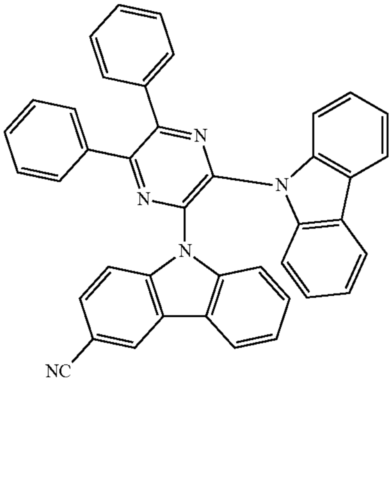

-continued
39
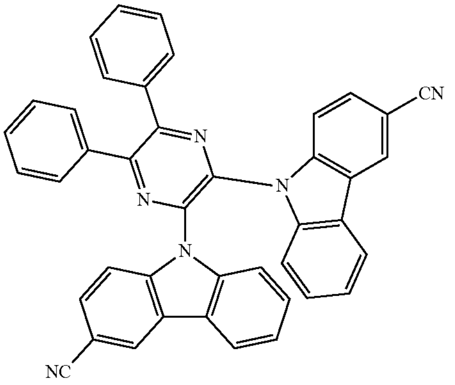
40
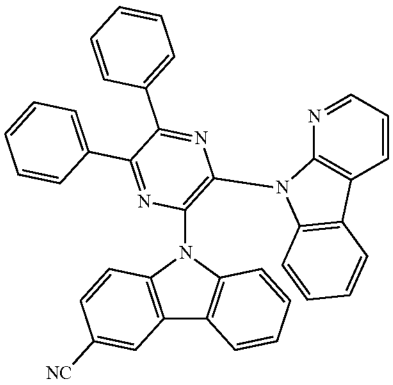
41
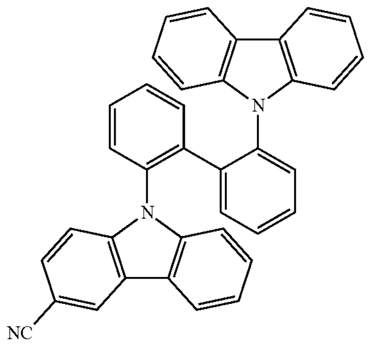
42
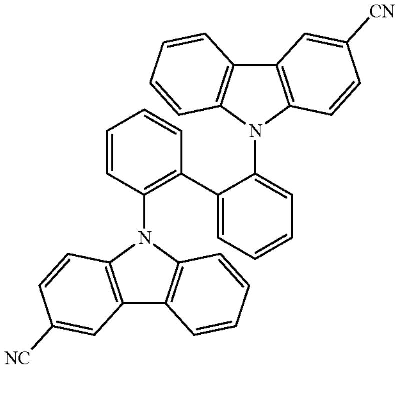
-continued
43
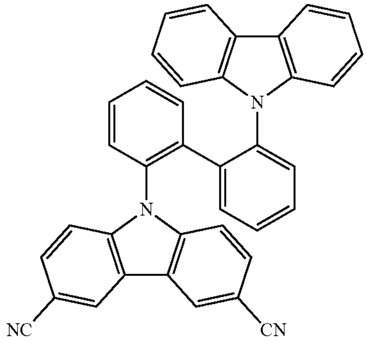
44
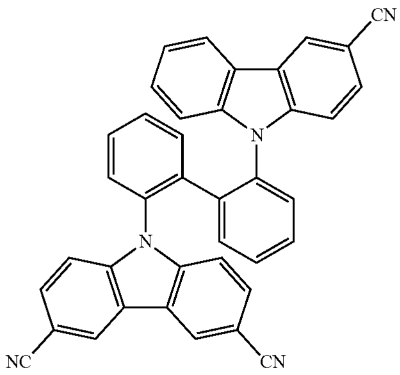
45
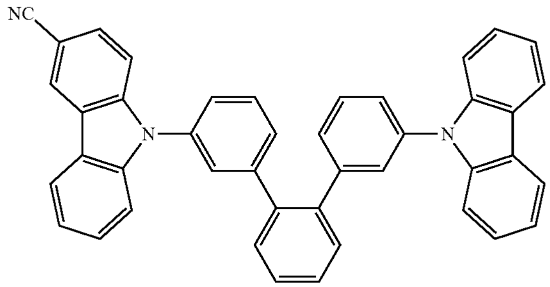
46
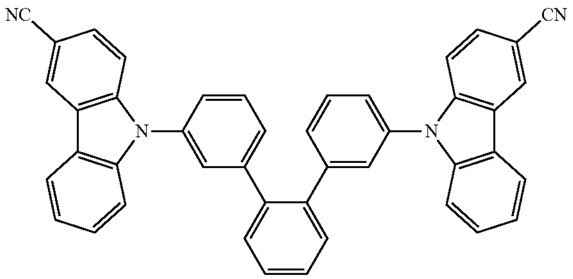
47
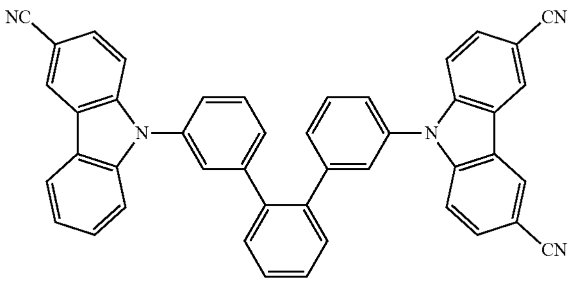

-continued
48
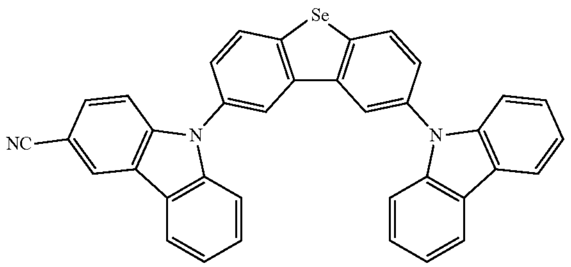
49
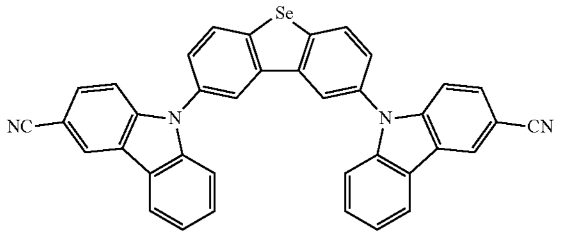
50
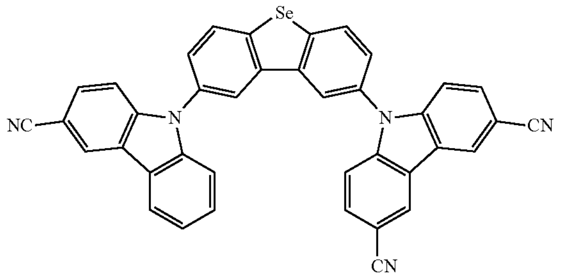
51
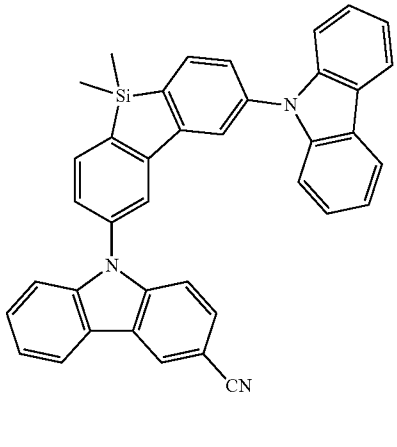
-continued
52
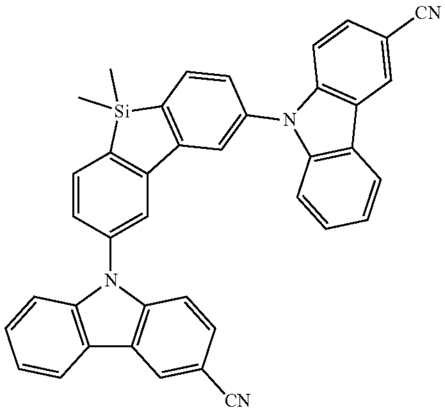
53
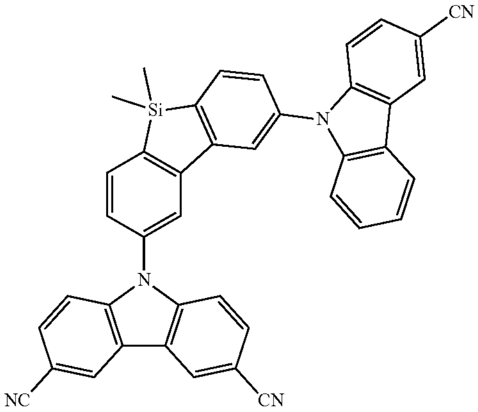
54
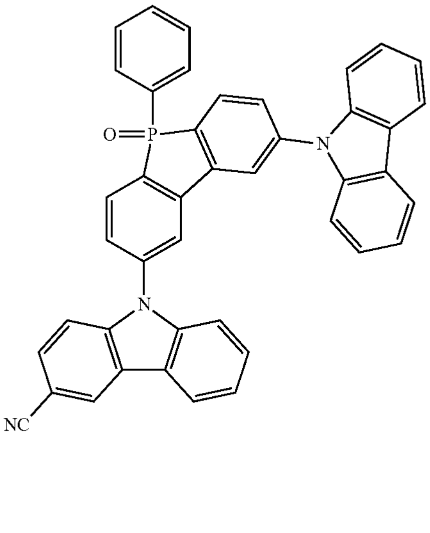

-continued
55
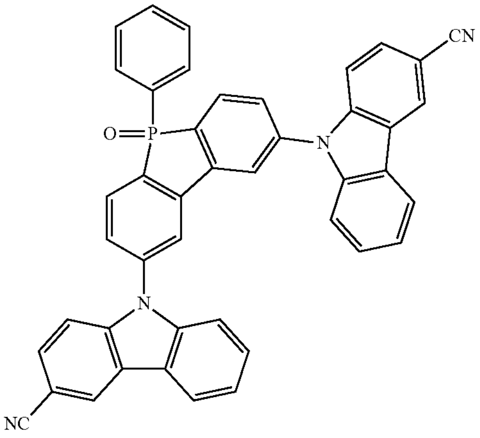
56
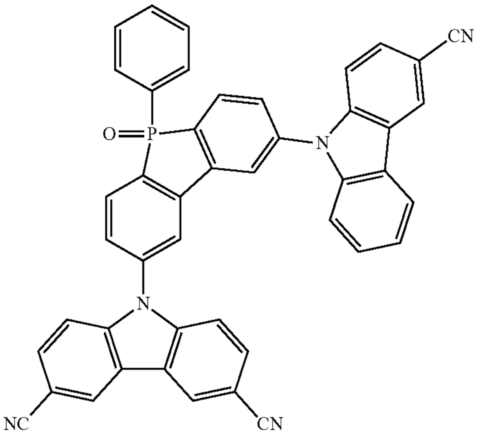
Group HE5
1
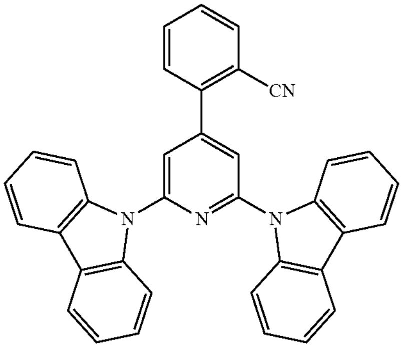
-continued
2
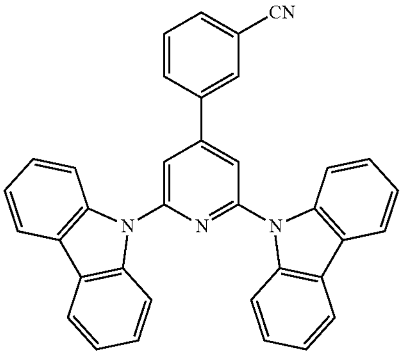
3
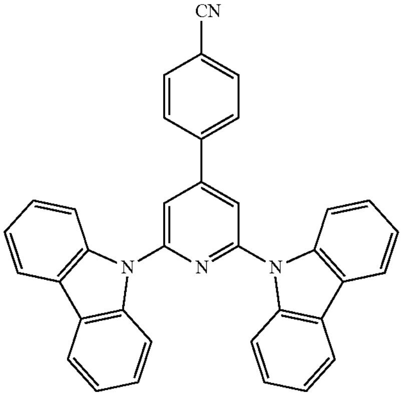
4
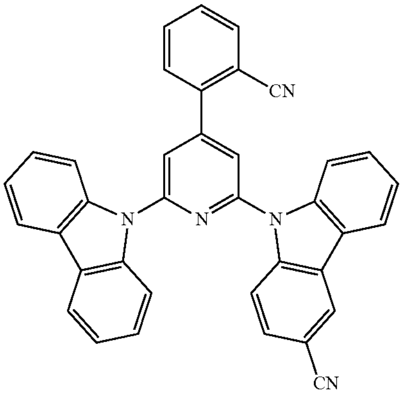
5
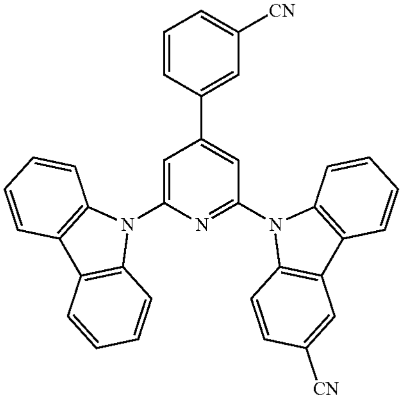

-continued
6
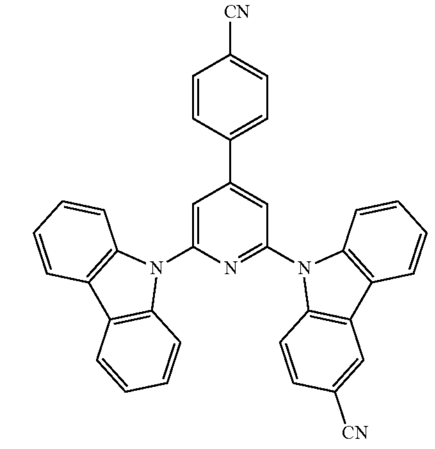
7
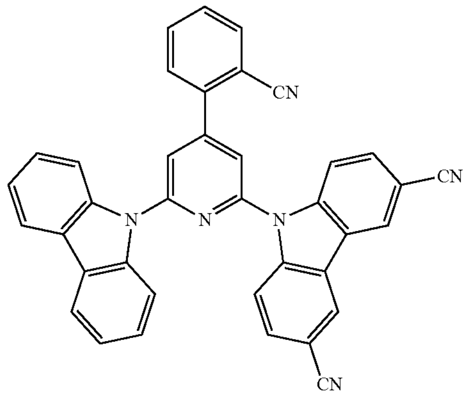
8
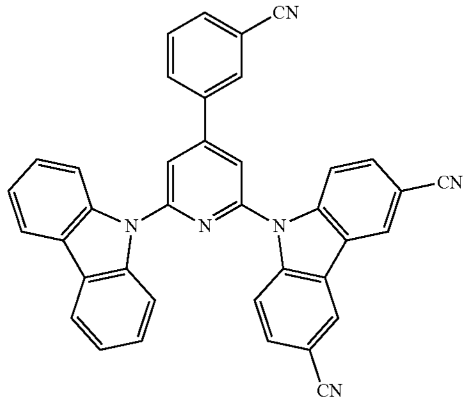
-continued
9
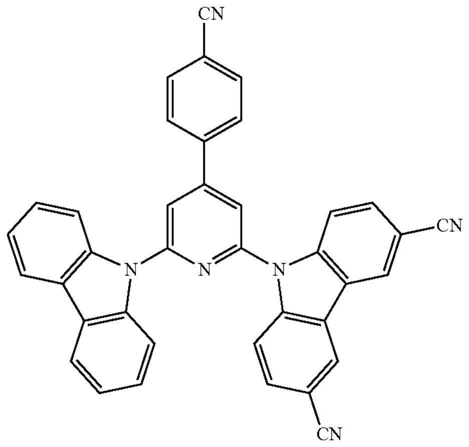
10
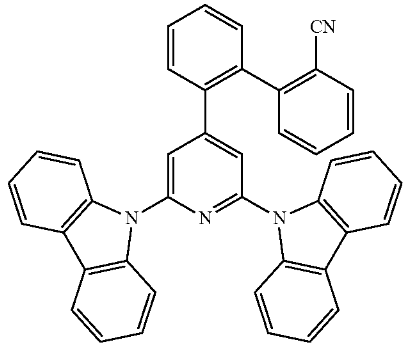
11
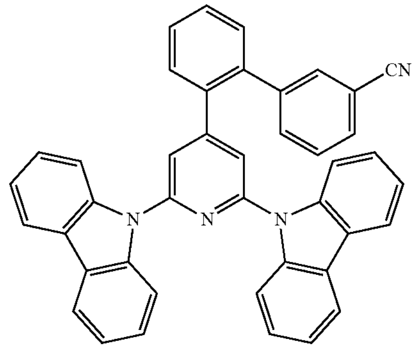
12
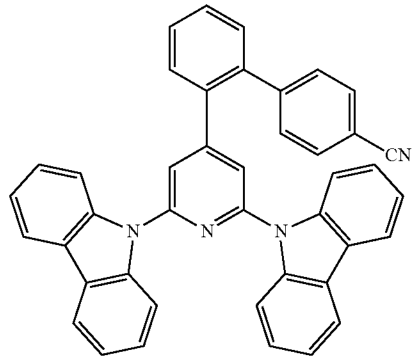

-continued
13
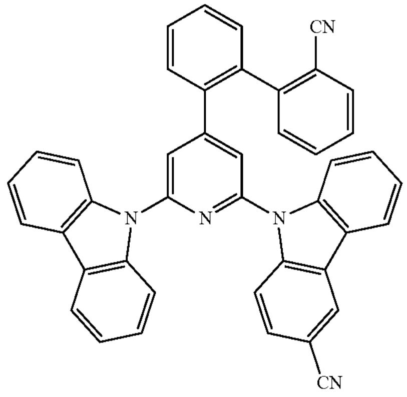
14
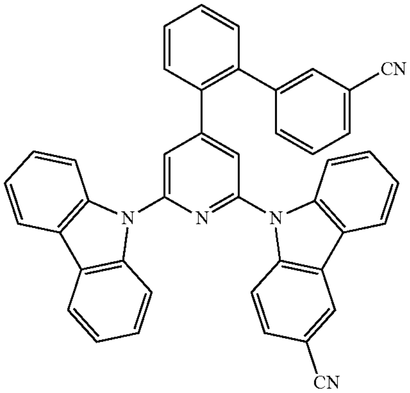
15
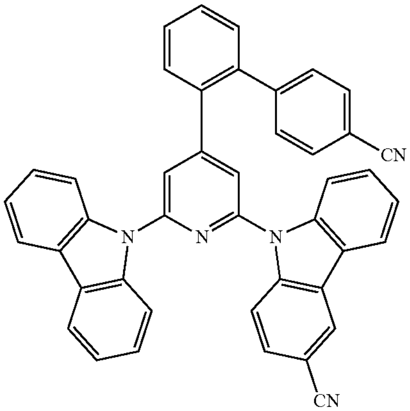
16
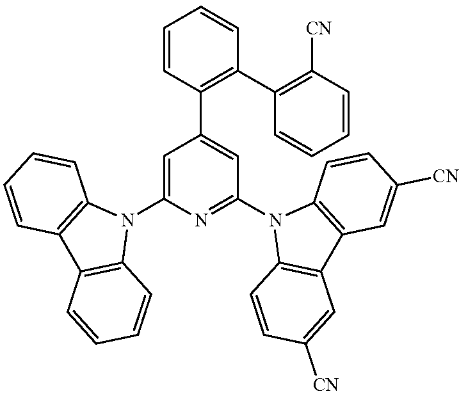
-continued
17
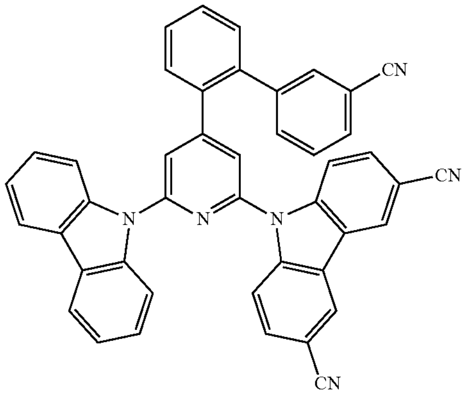
18
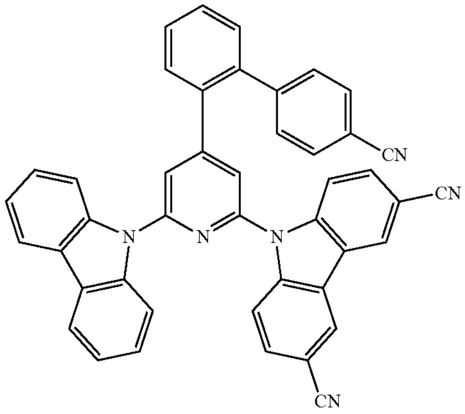
19
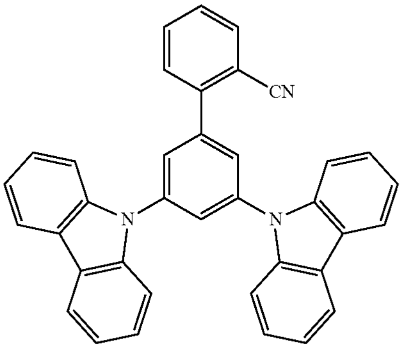
20
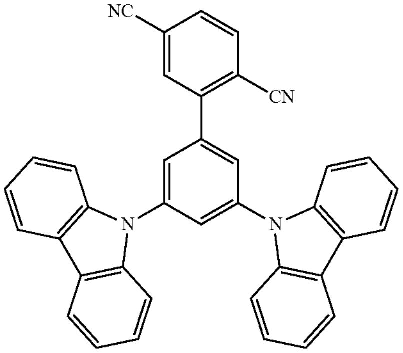

-continued
21
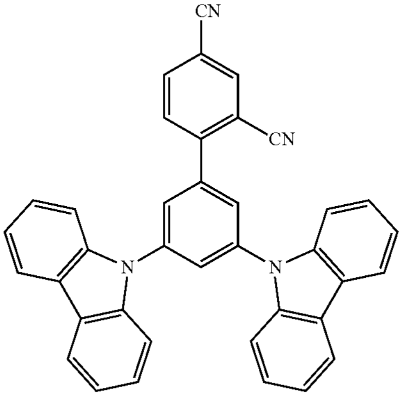
22
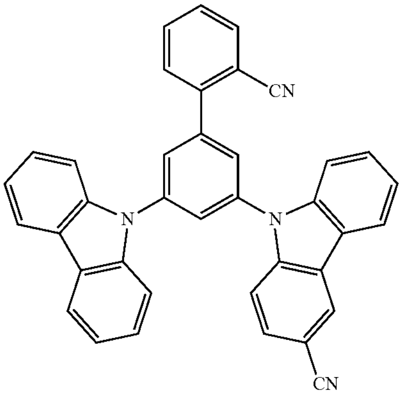
23
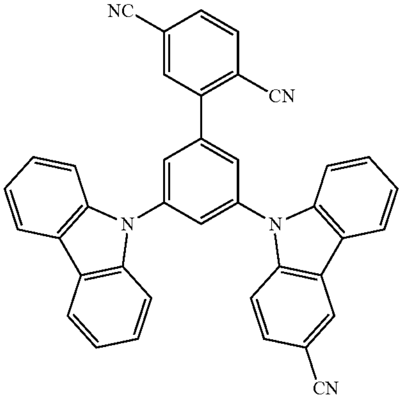
24
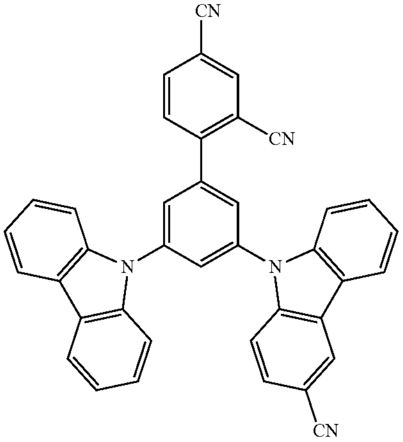
-continued
25
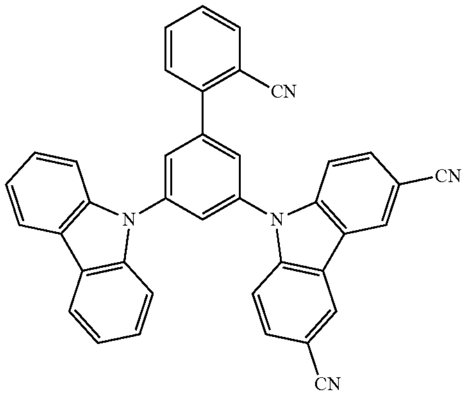
26
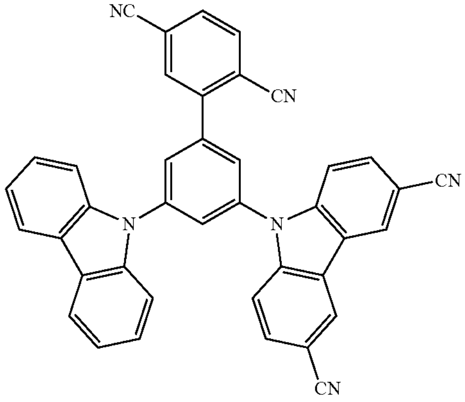
27
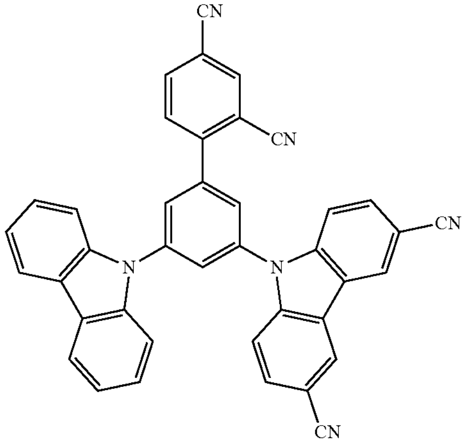
28
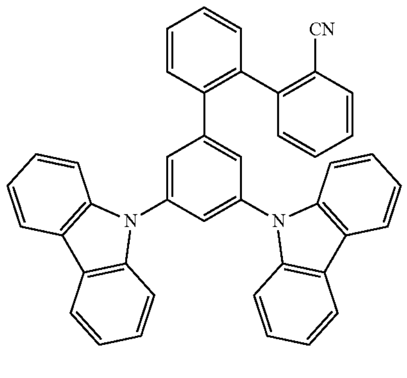

-continued
29
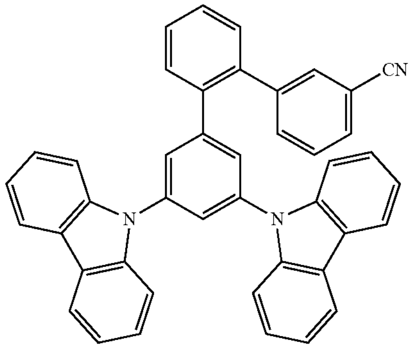
30
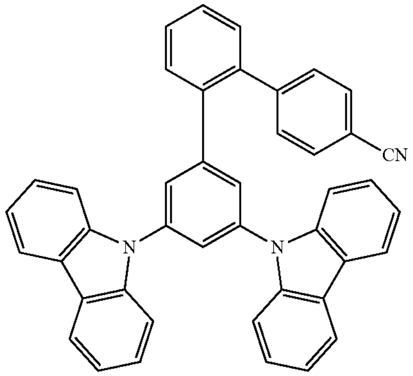
31
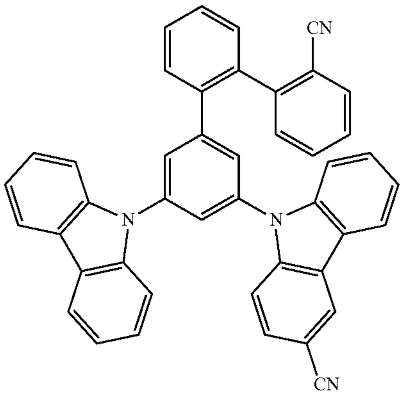
32
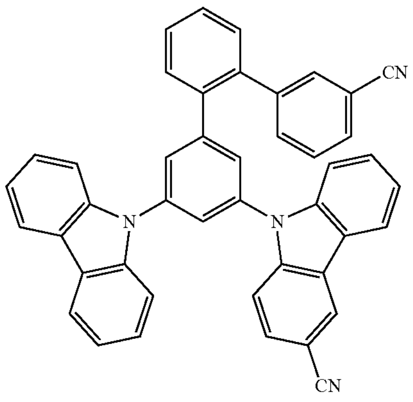
-continued
33
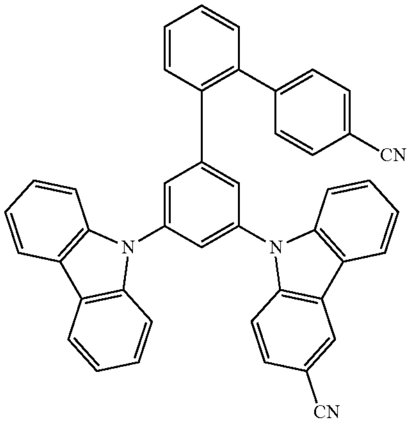
34
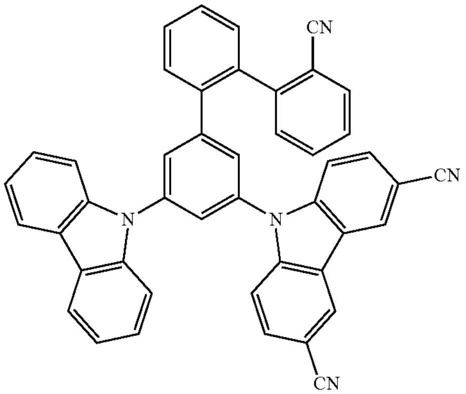
35
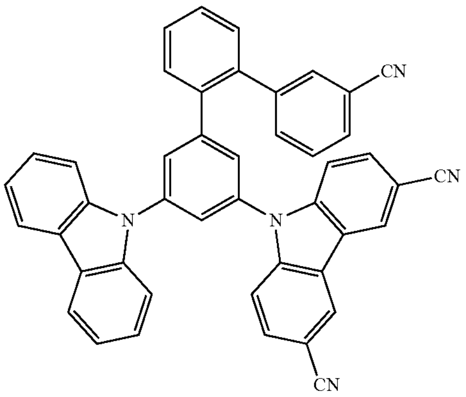
36
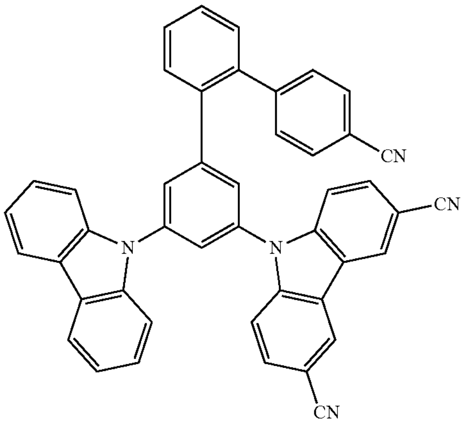

-continued
37
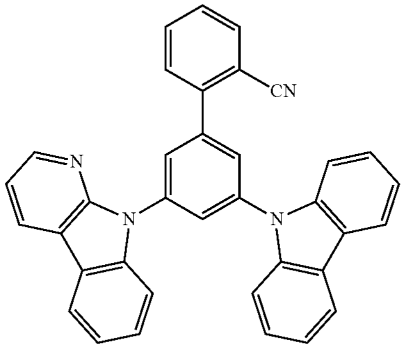
38
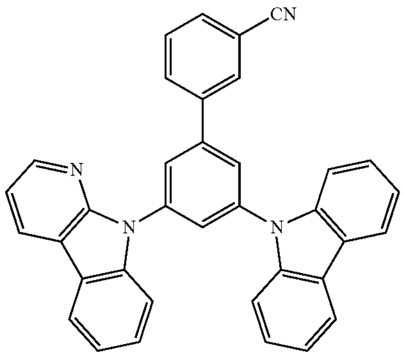
39
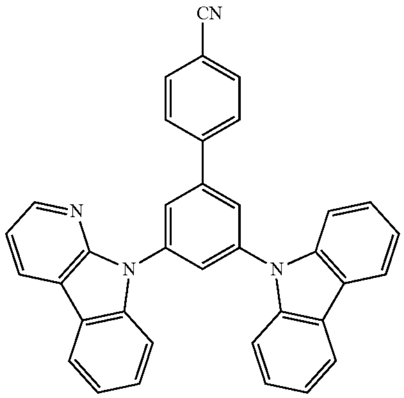
40
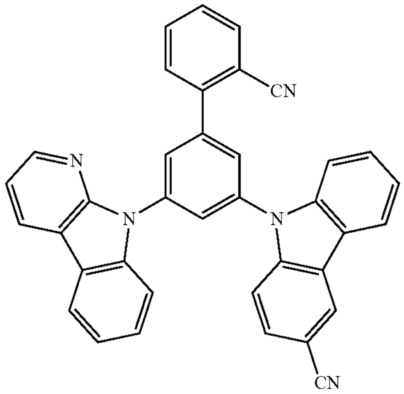
-continued
41
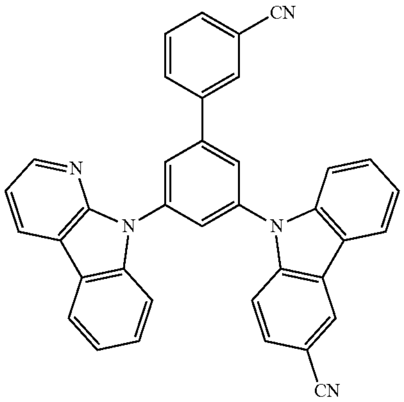
42
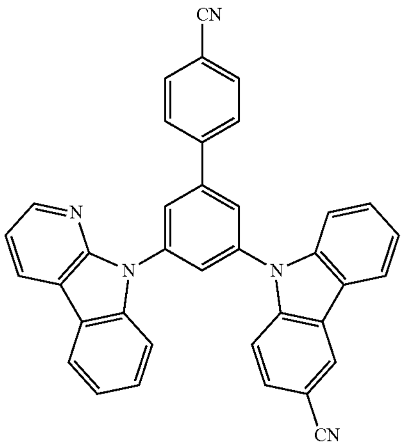
43
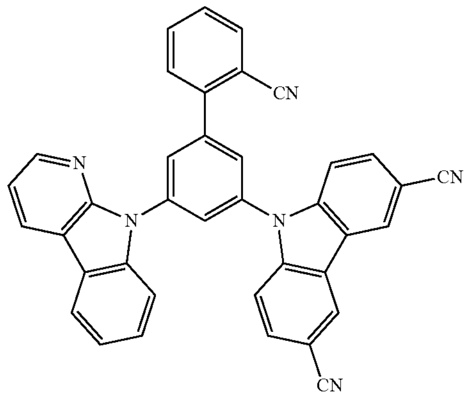
44
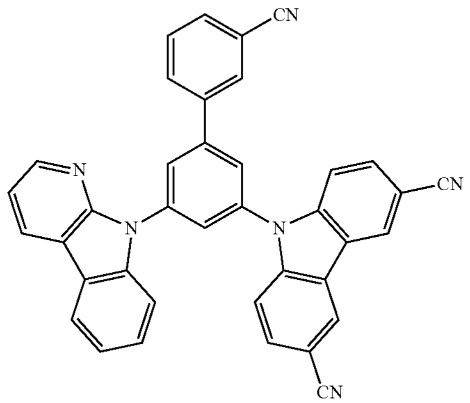

45
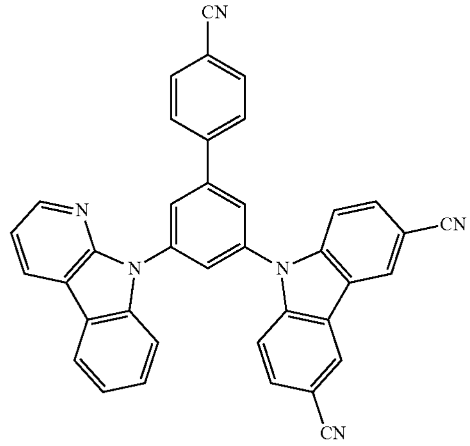
46
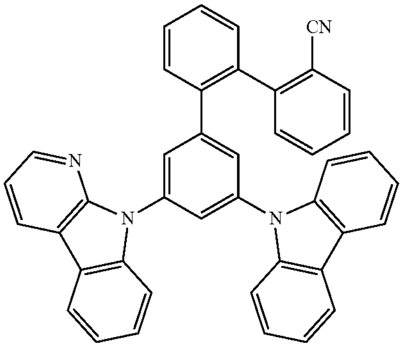
47
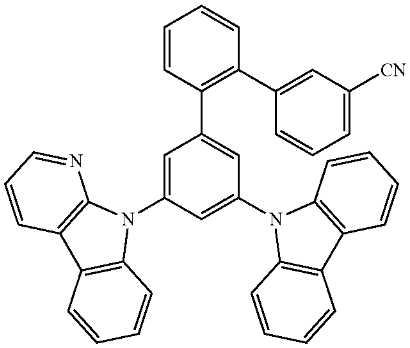
48
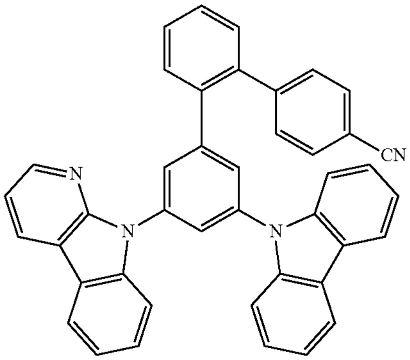
49
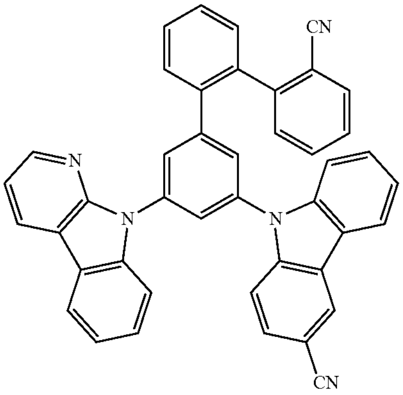
50
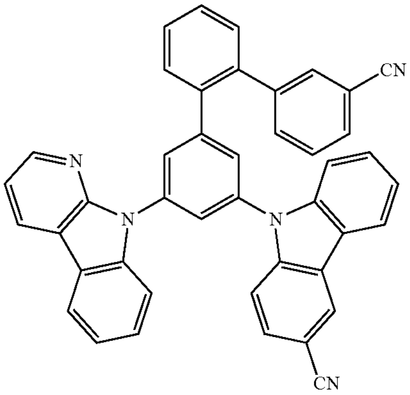
51
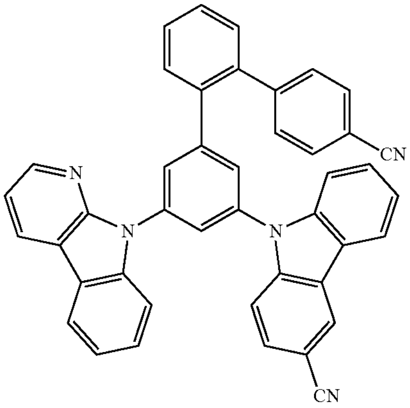
52
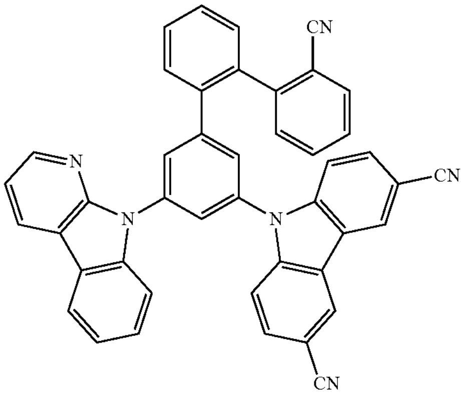

-continued
53
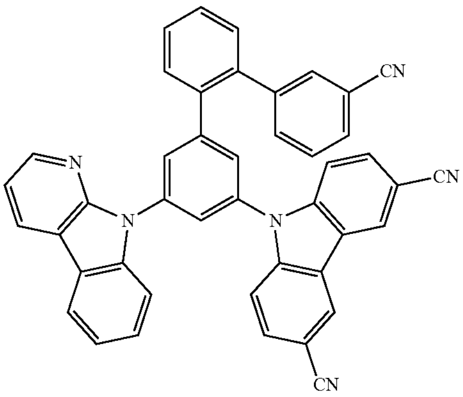
54
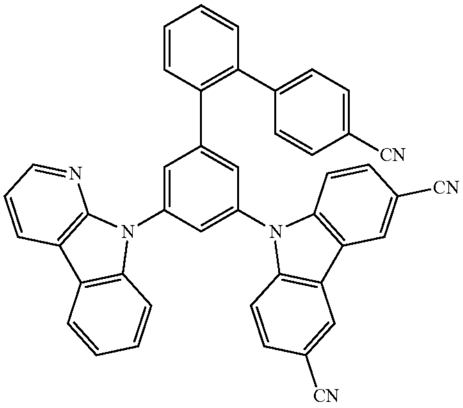
55
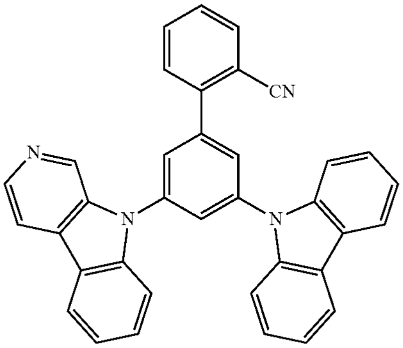
56
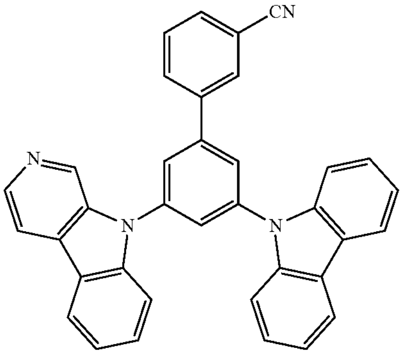
-continued
57
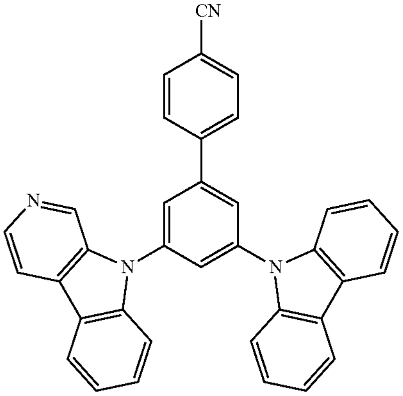
58
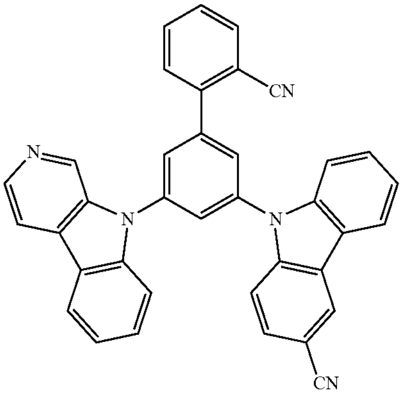
59
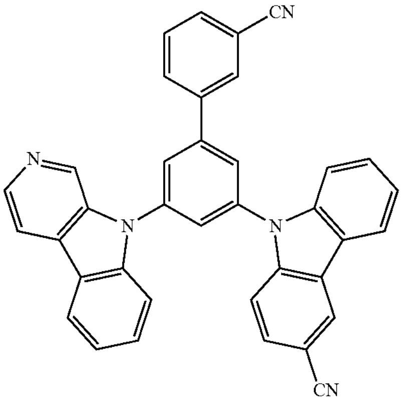
60
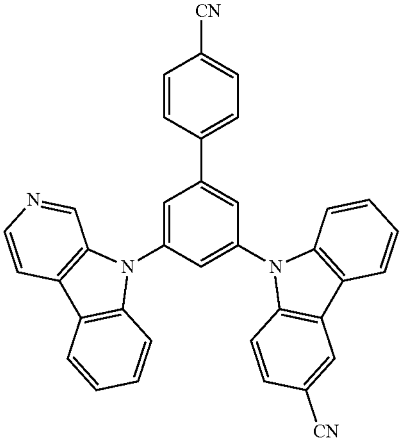

-continued
61
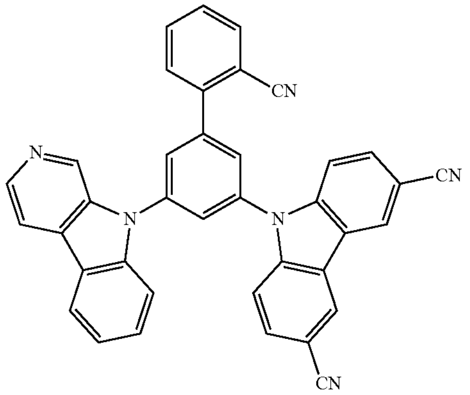
62
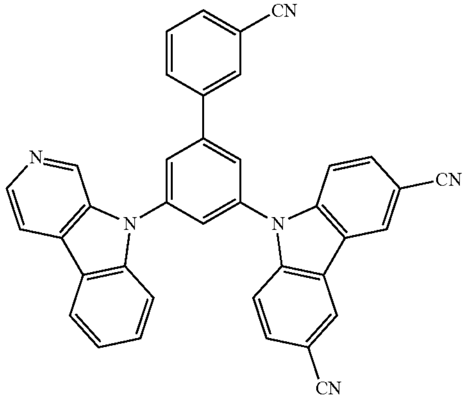
63
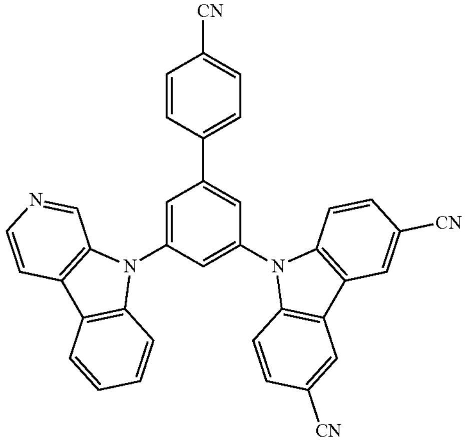
64
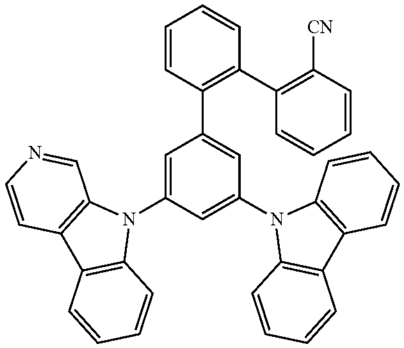
-continued
65
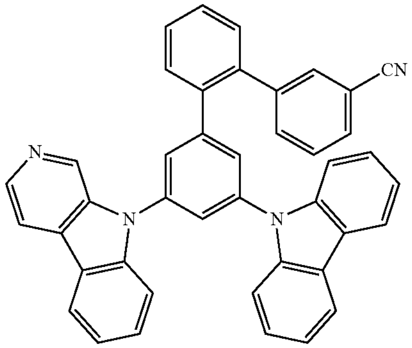
66
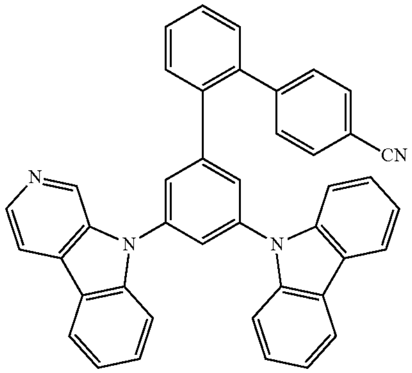
67
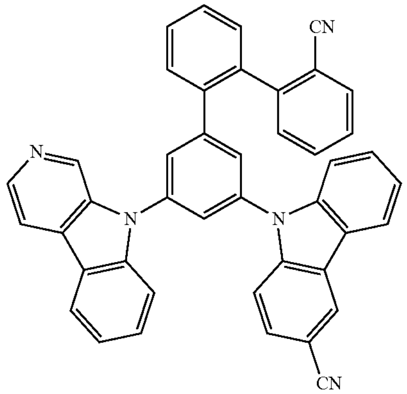
68
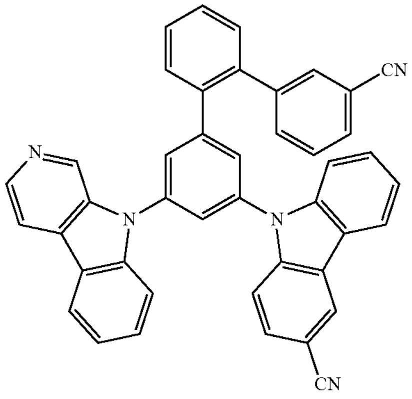

-continued
69
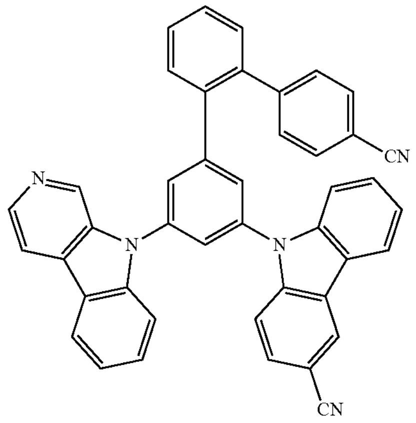
70
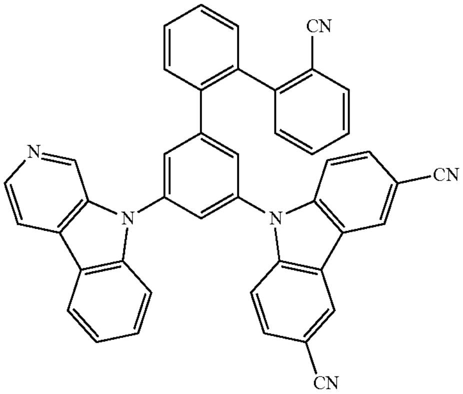
71
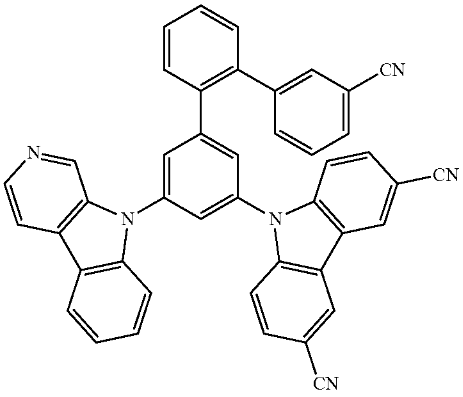
72
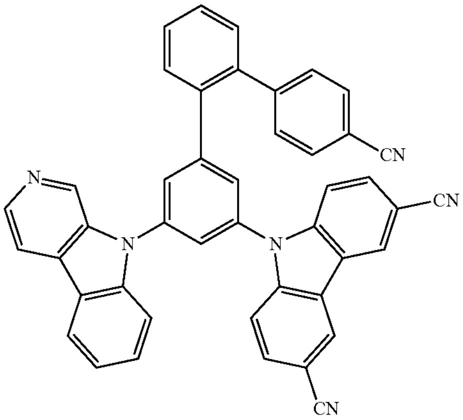
-continued
73
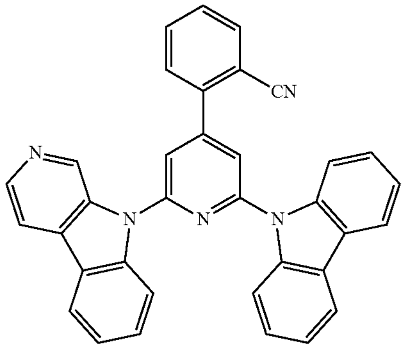
74
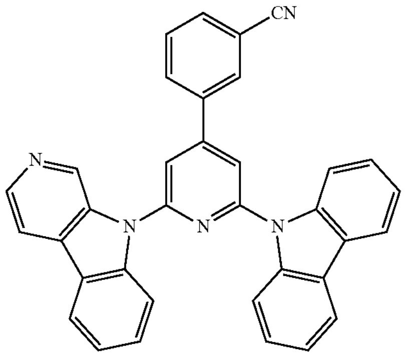
75
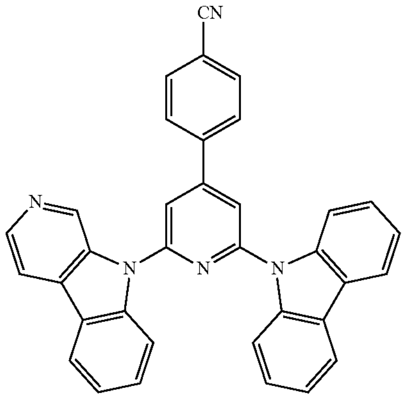
76
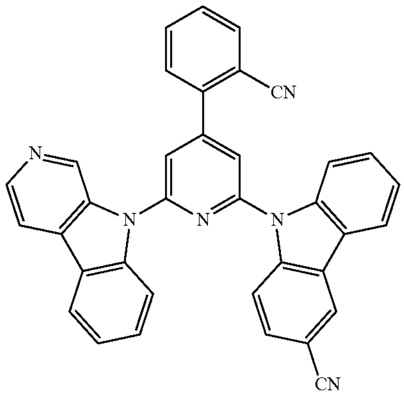

-continued
77
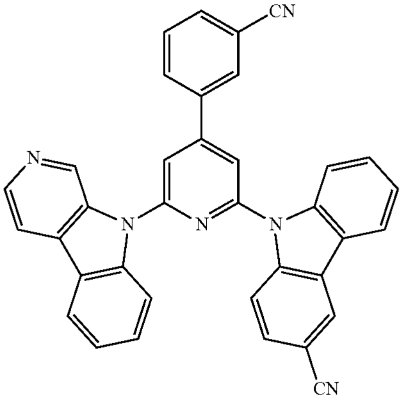
78
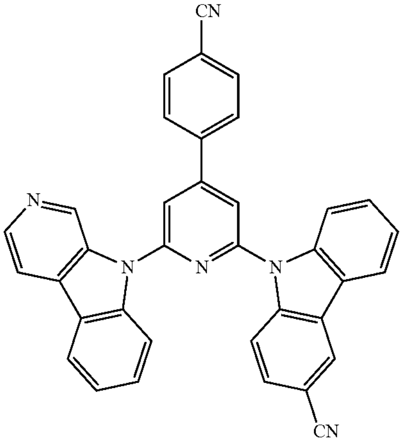
79
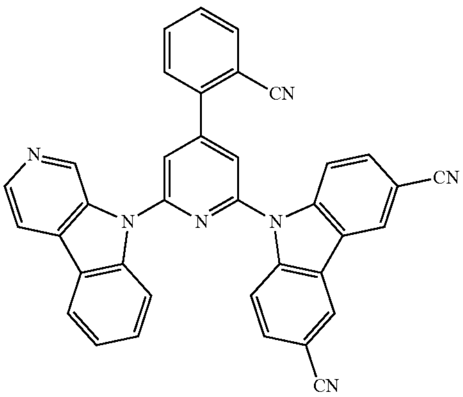
80
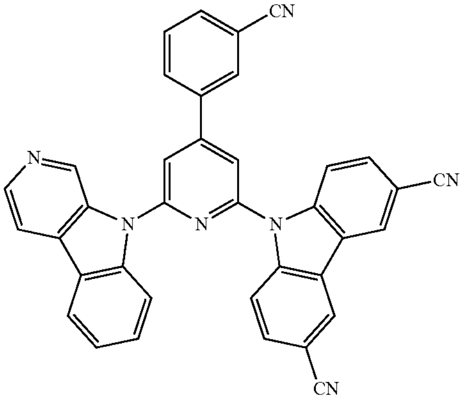
-continued
81
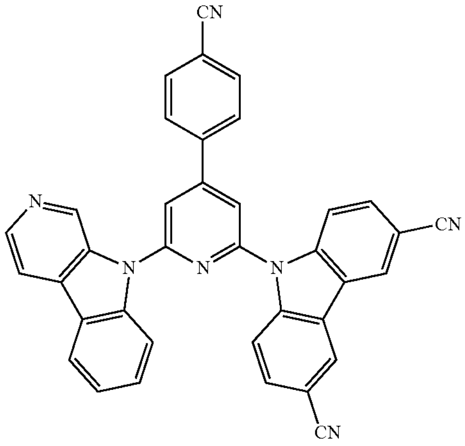
82
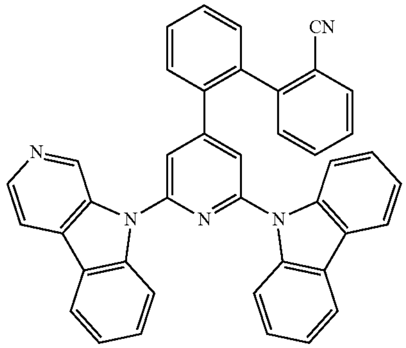
83
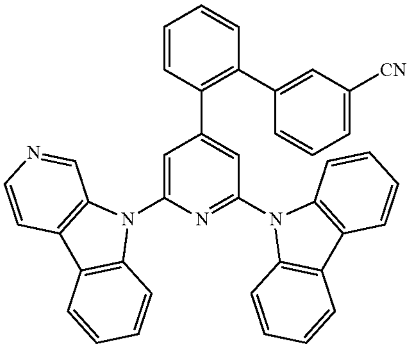
84
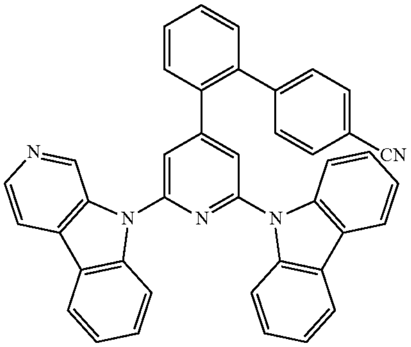

-continued
85
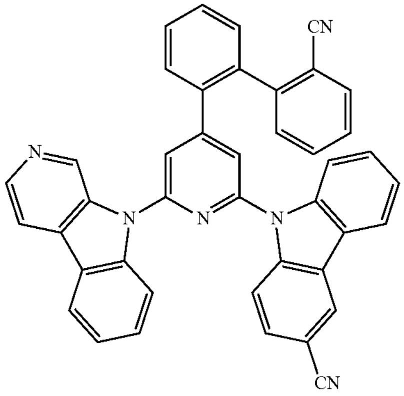
86
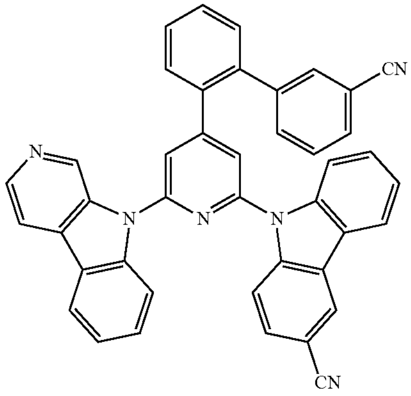
87
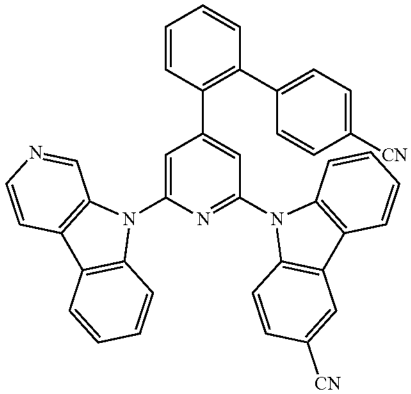
88
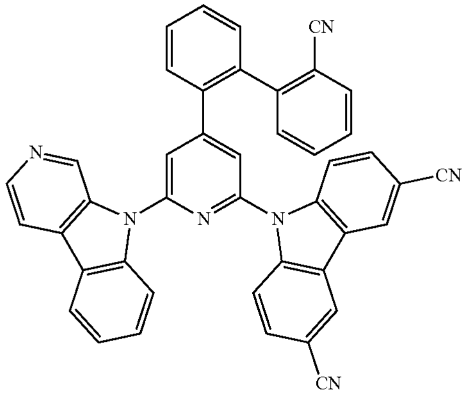
-continued
89
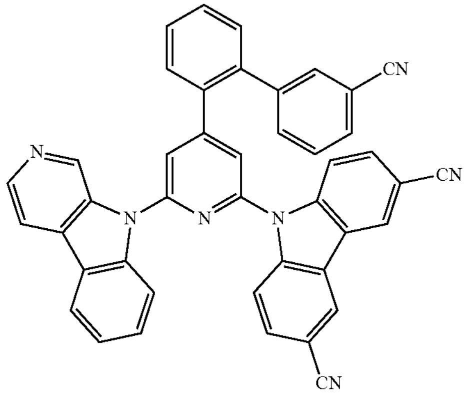
90
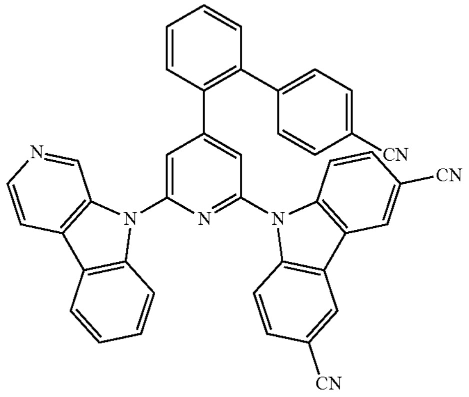
91
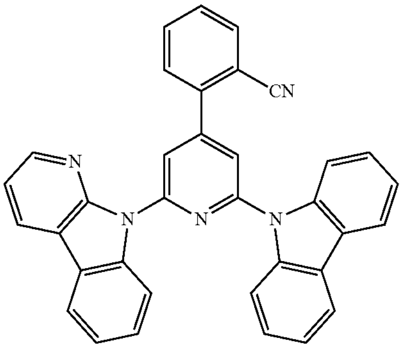
92
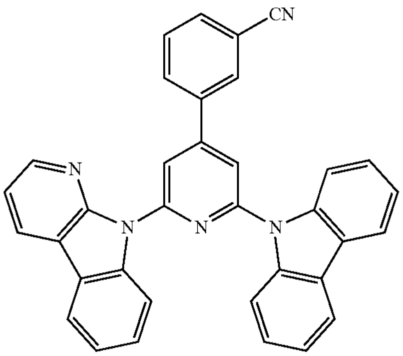

-continued
93
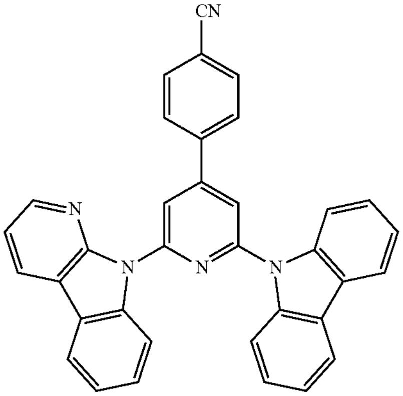
94
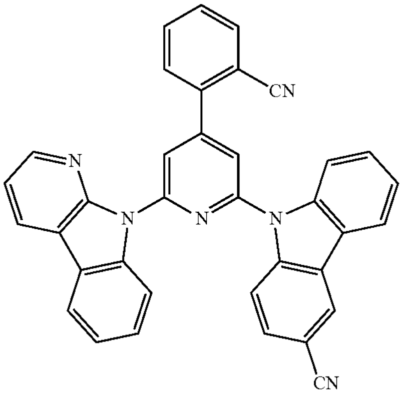
95
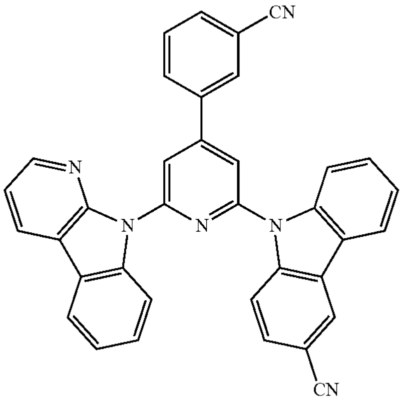
96
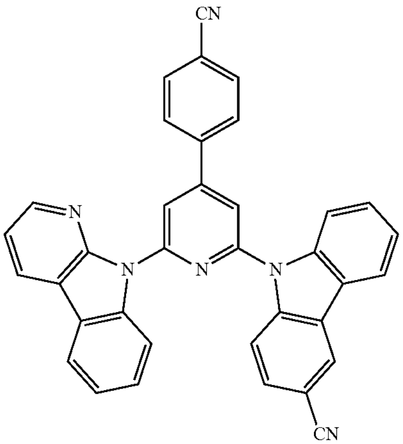
-continued
97
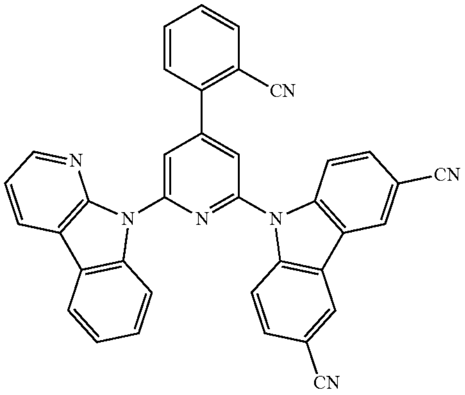
98
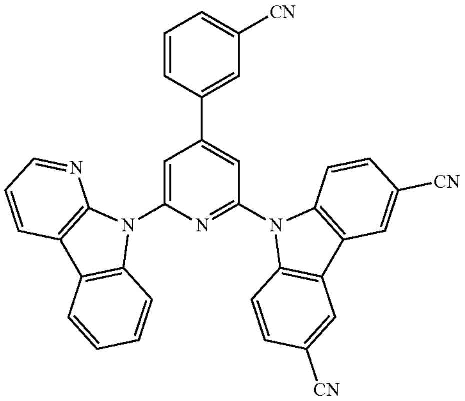
99
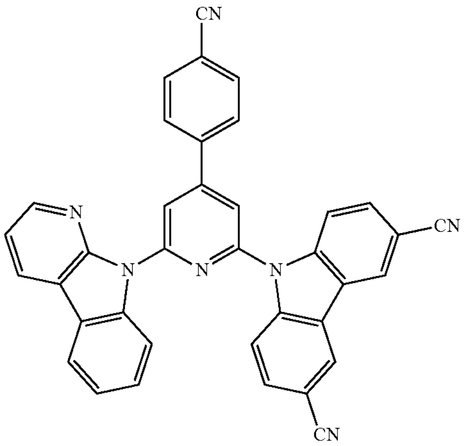
100
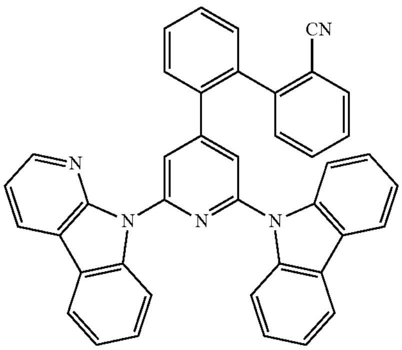

-continued
101
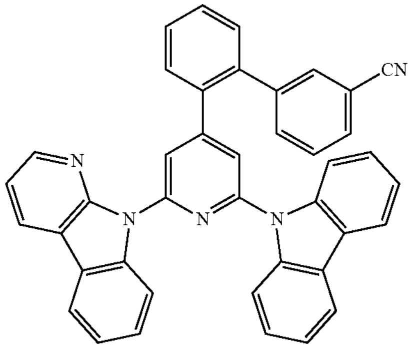
102
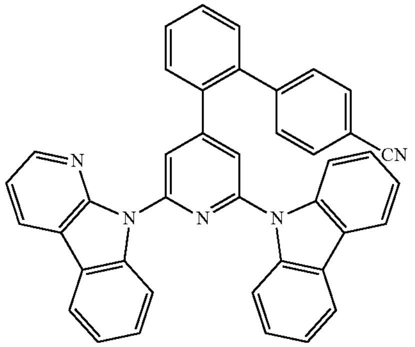
103
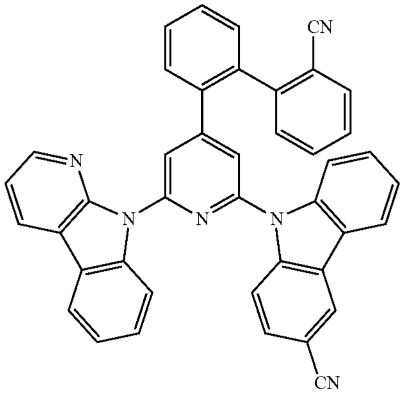
104
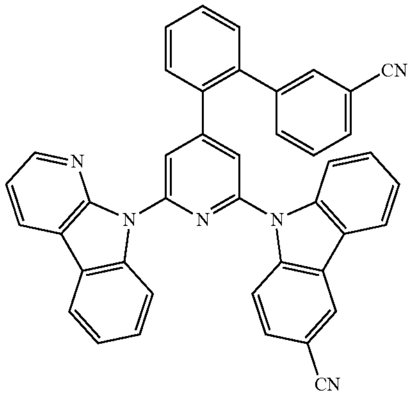
-continued
105
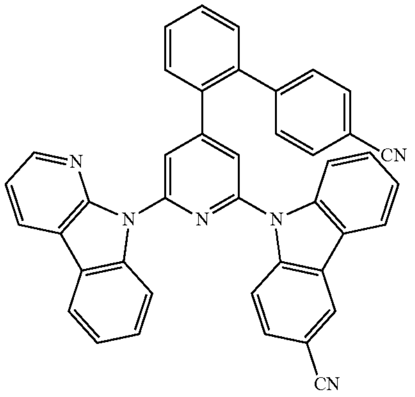
106
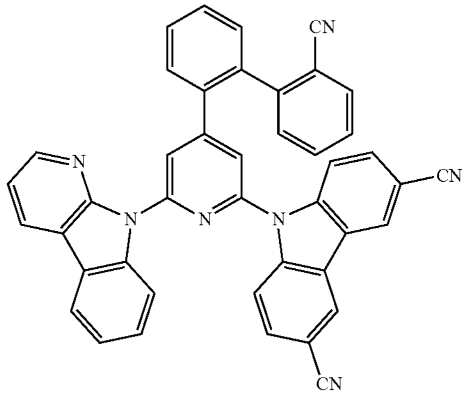
107
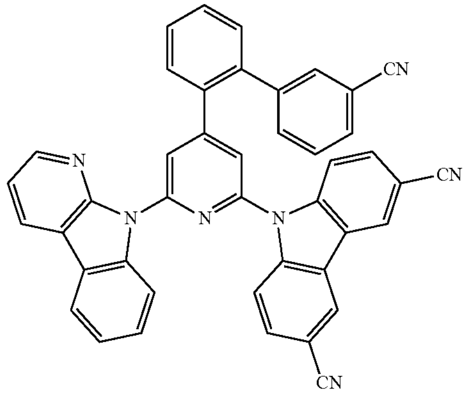
108
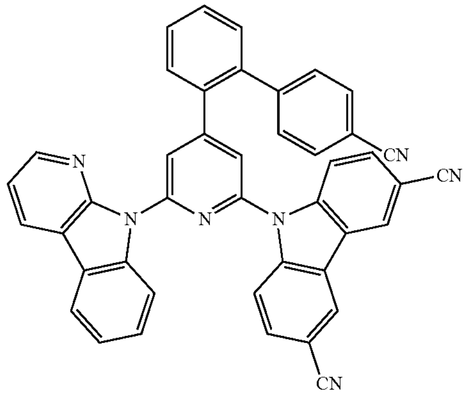

-continued
109
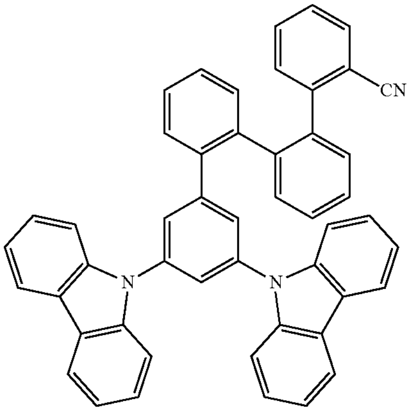
110
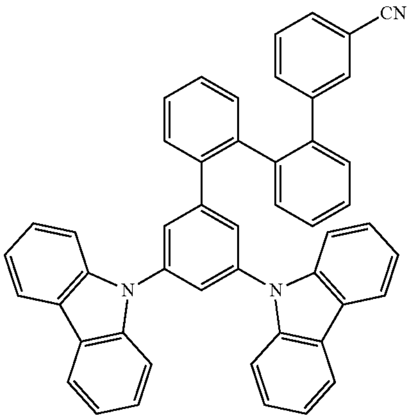
111
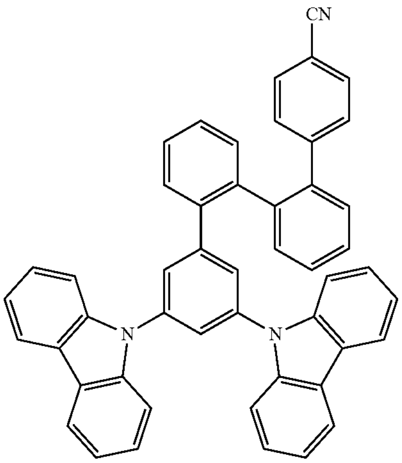
-continued
112
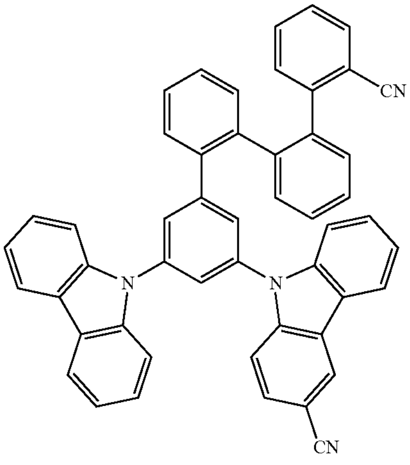
113
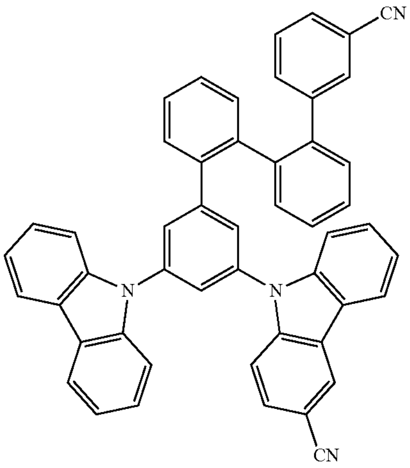
114
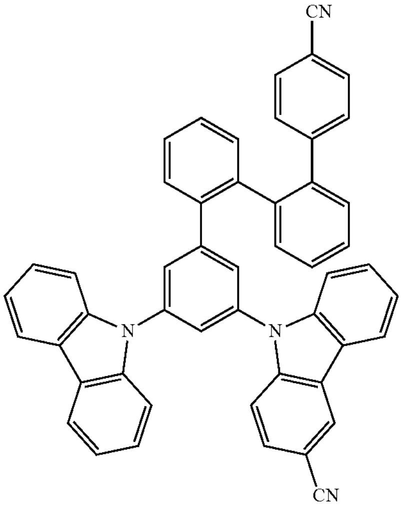

-continued
115
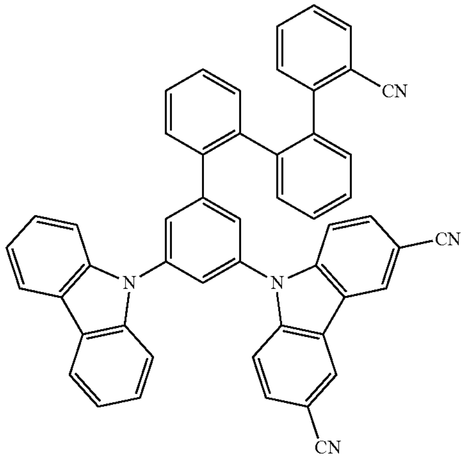
116
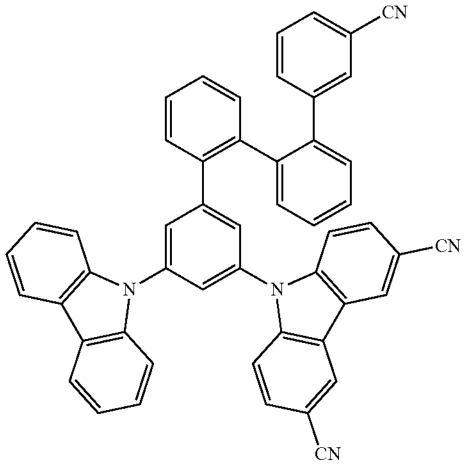
117
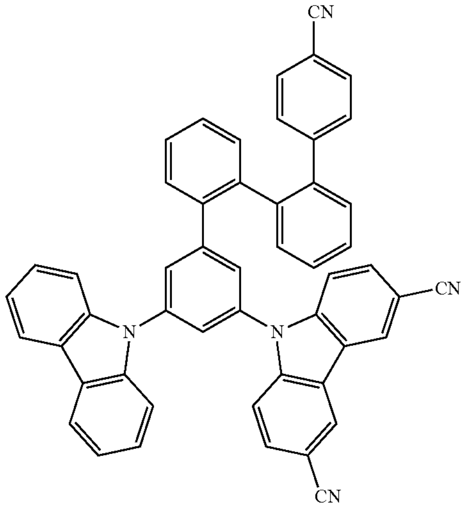
-continued
118
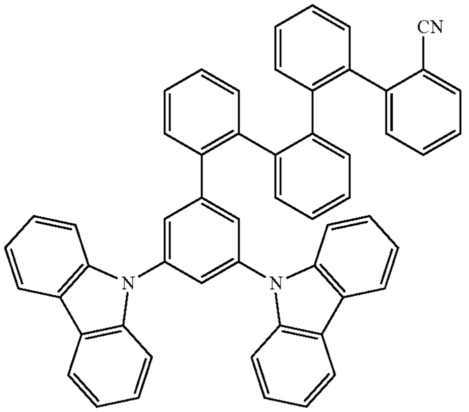
119
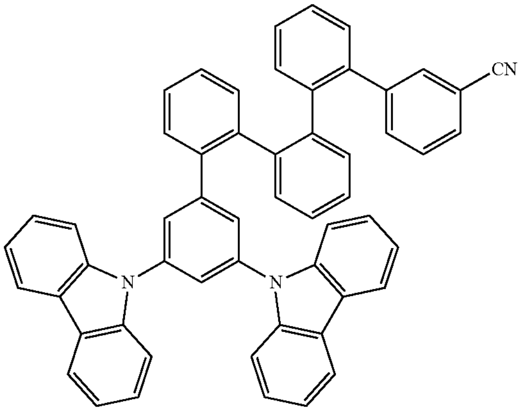
120
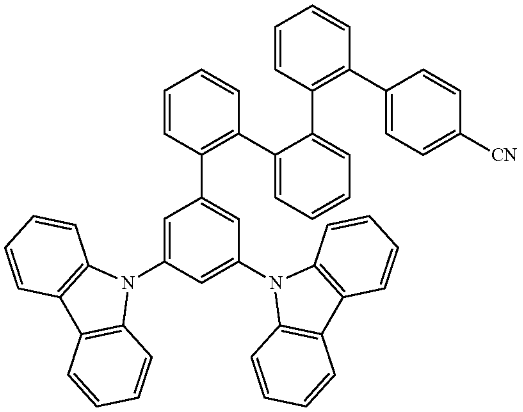

-continued
121
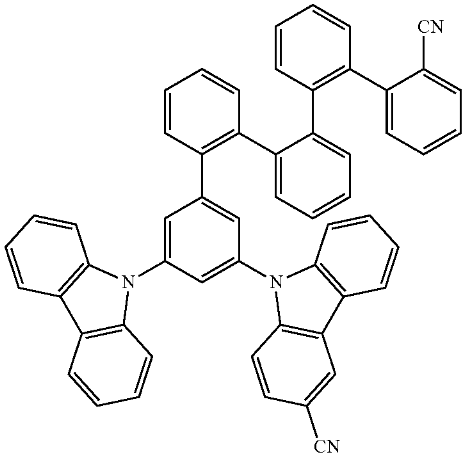
122
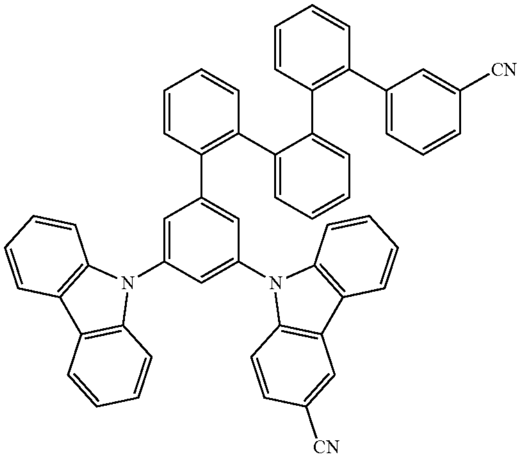
123
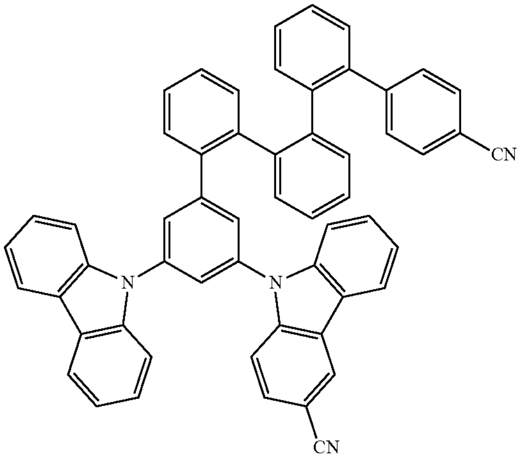
-continued
124
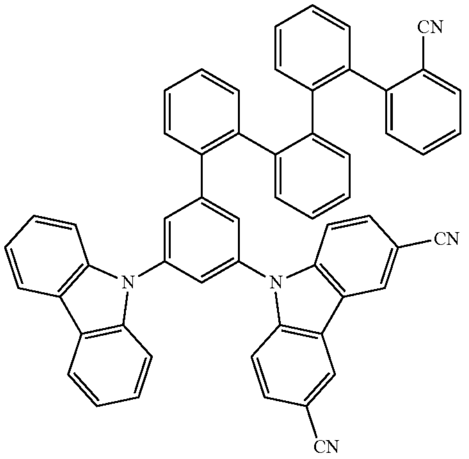
125
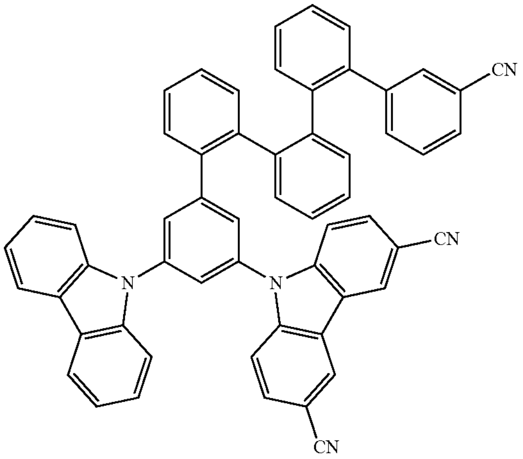
126
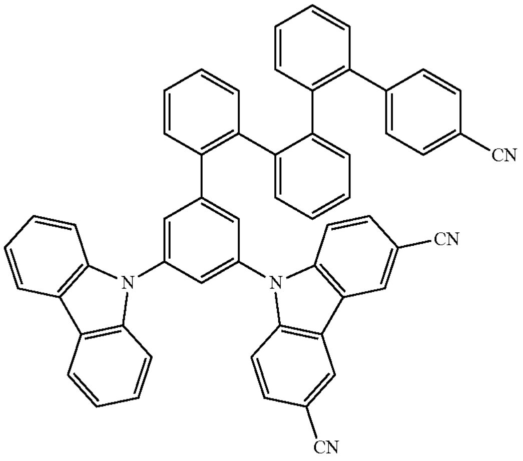

-continued
127
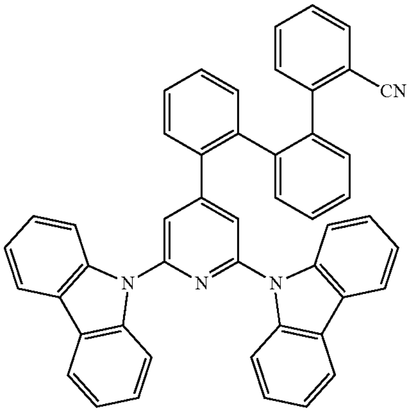
128
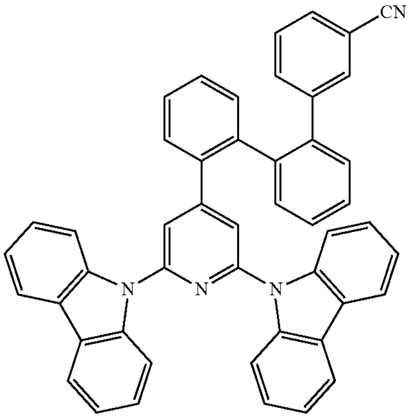
129
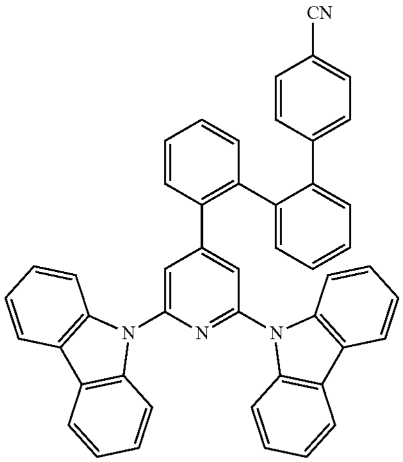
-continued
130
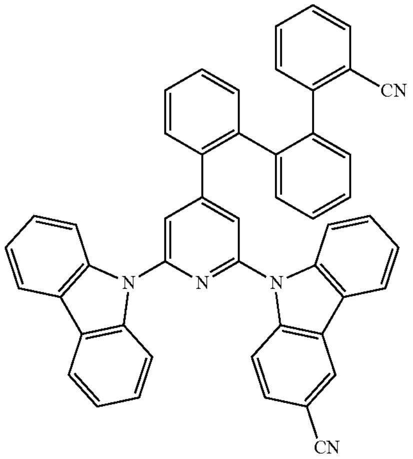
131
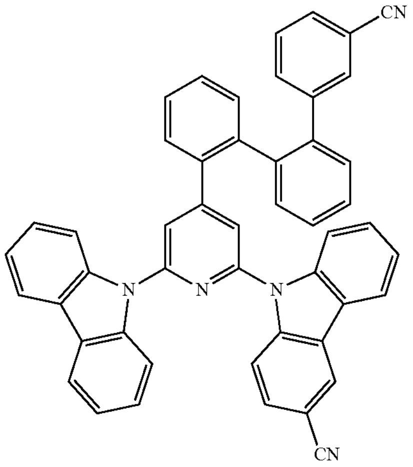
132
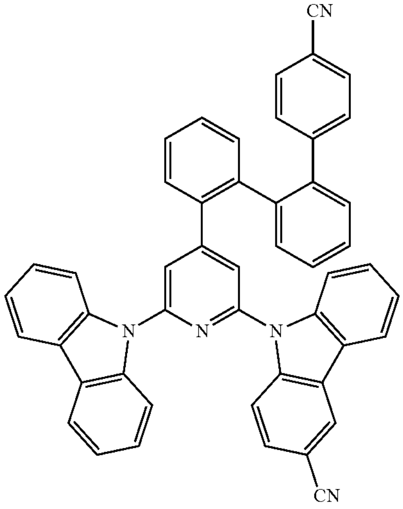

-continued
133
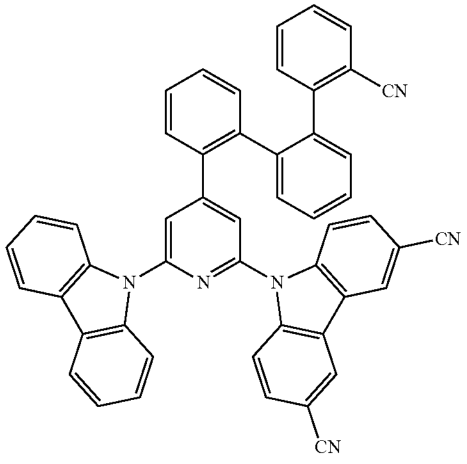
134
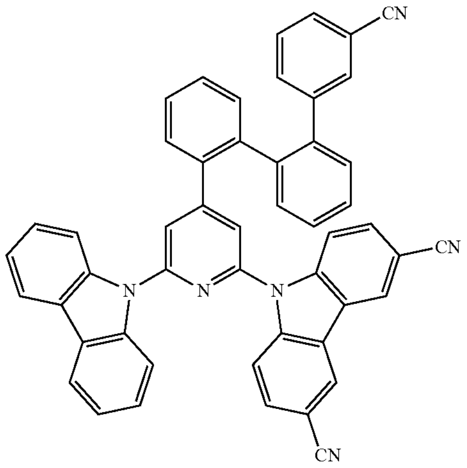
135
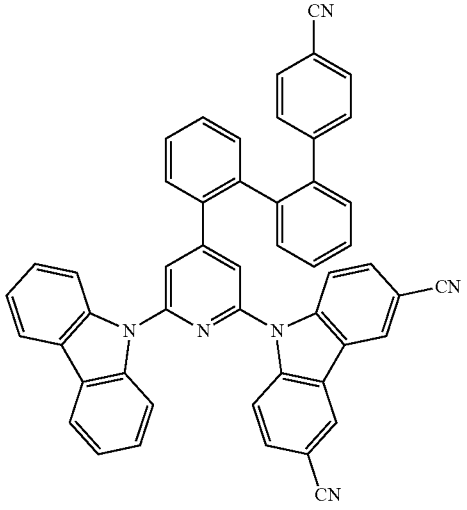
-continued
136
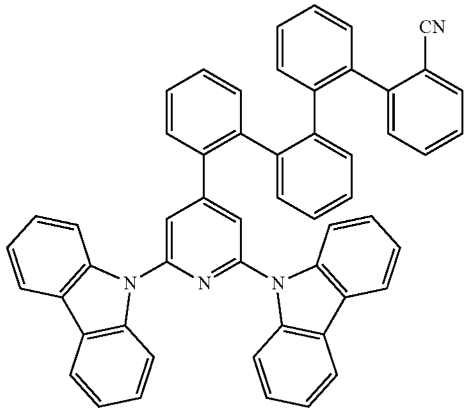
137
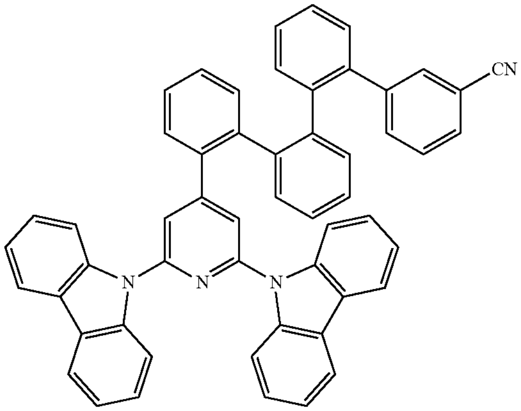
138
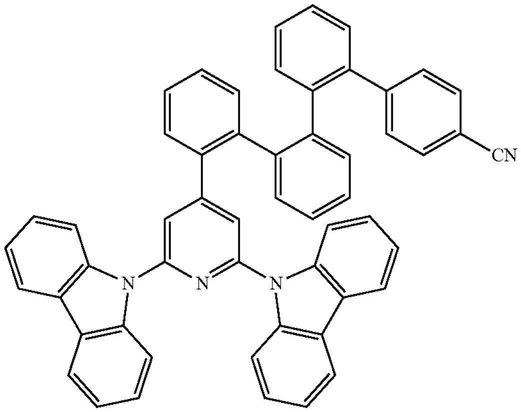

-continued
139
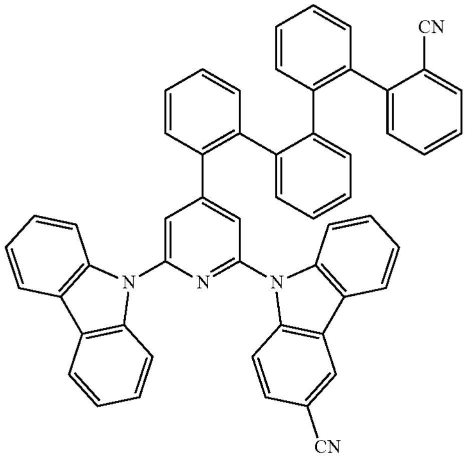
140
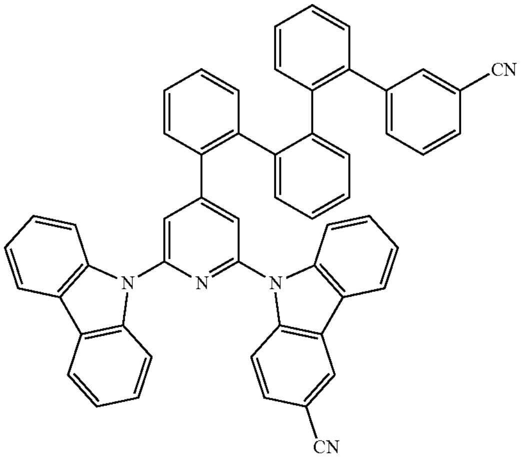
141
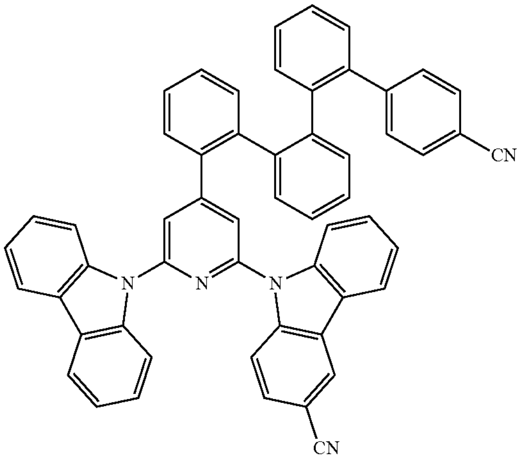
-continued
142
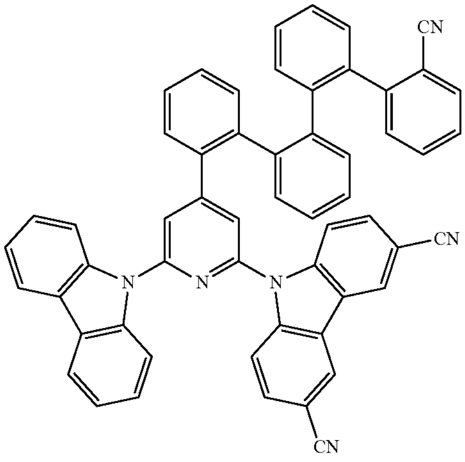
143
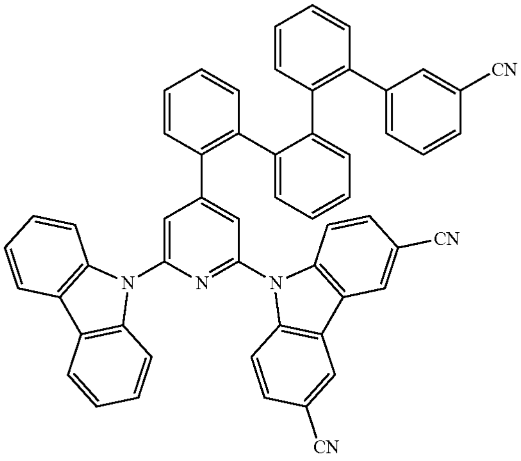
144
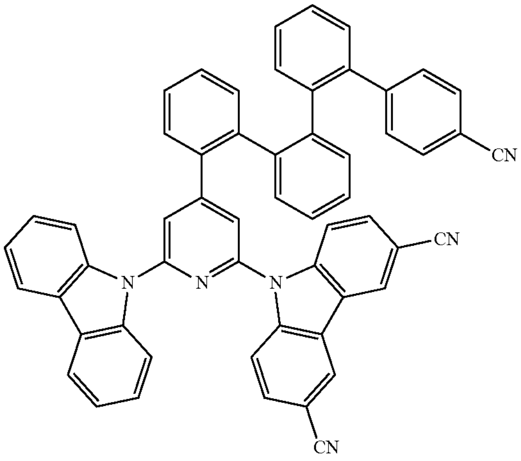

-continued
145
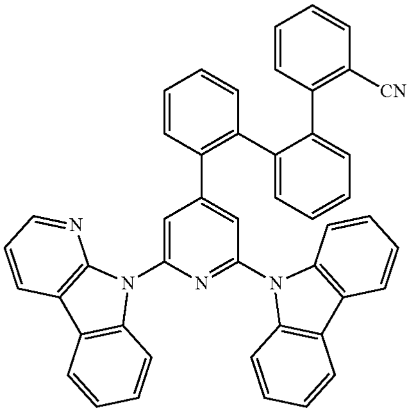
146
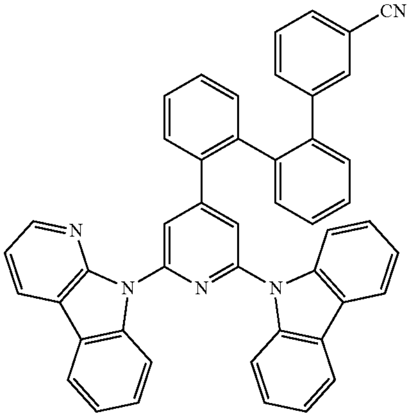
147
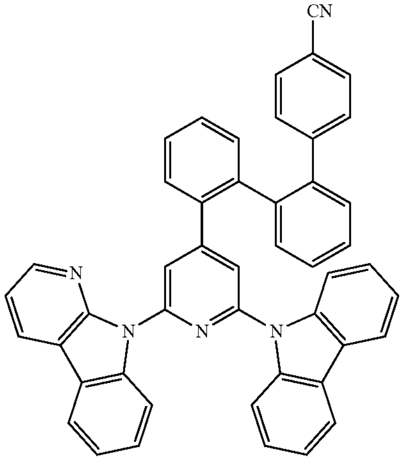
-continued
148
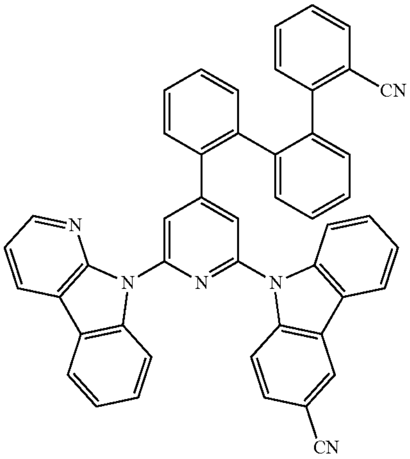
149
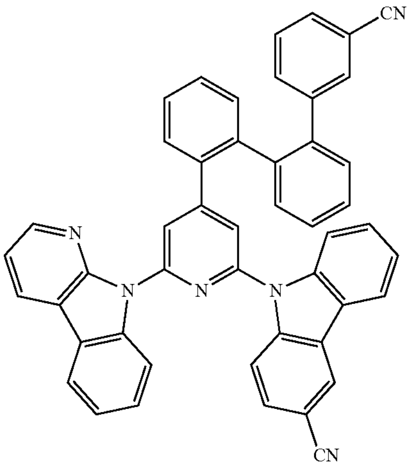
150
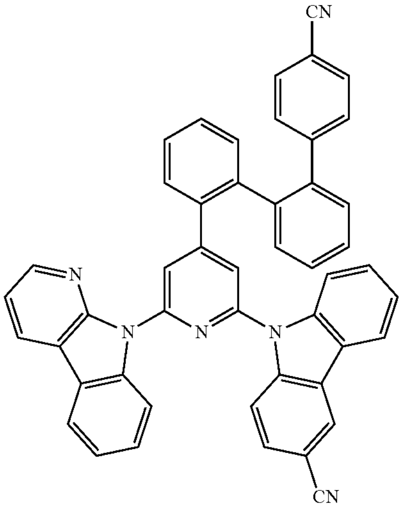

-continued
151
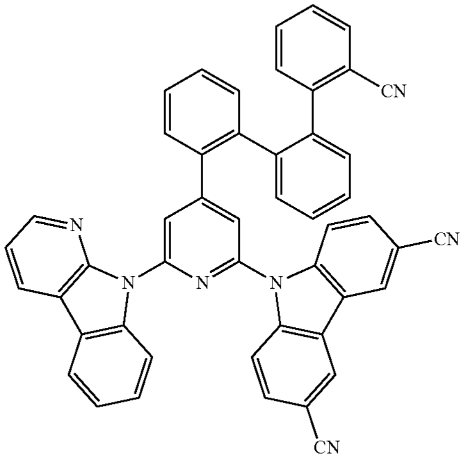
152
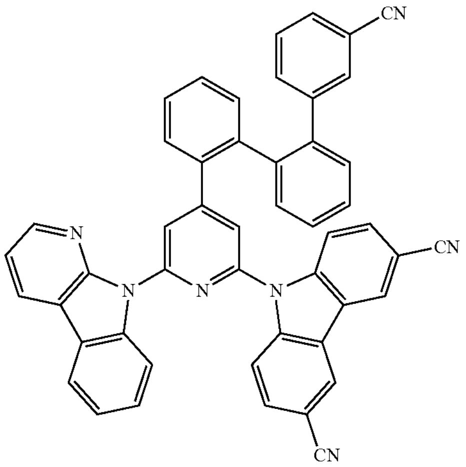
153
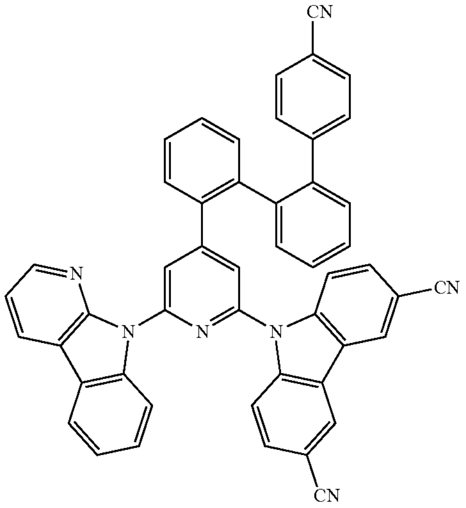
-continued
154
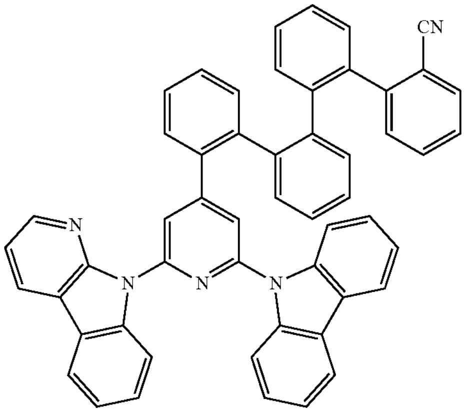
155
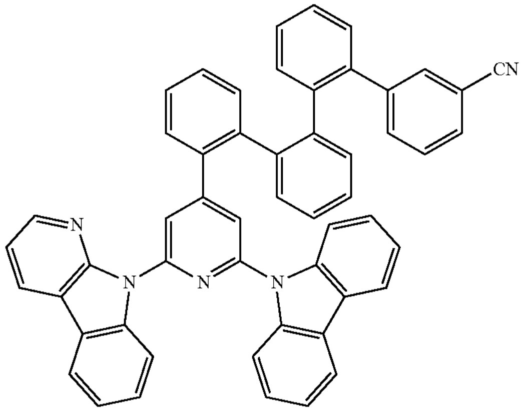
156
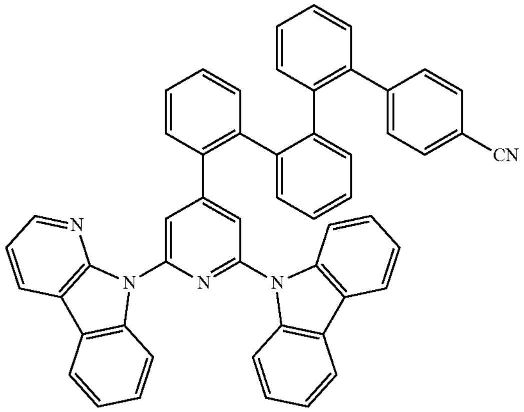

-continued
157
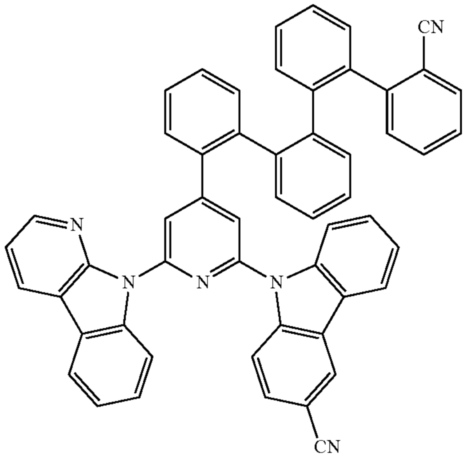
158
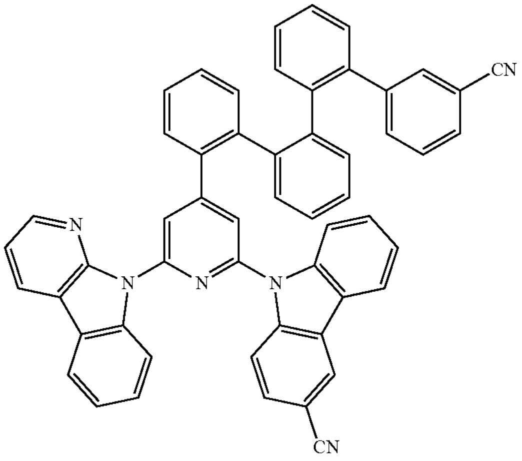
159
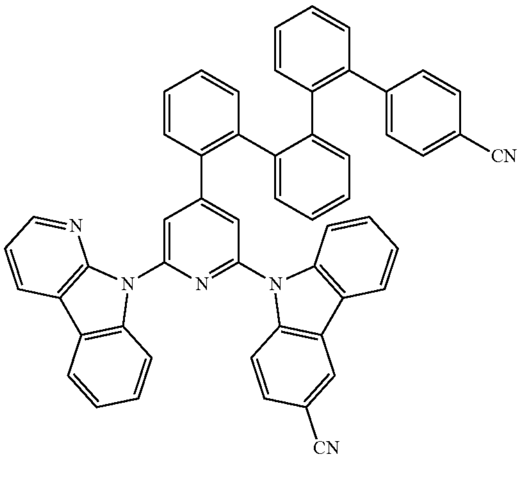
-continued
160
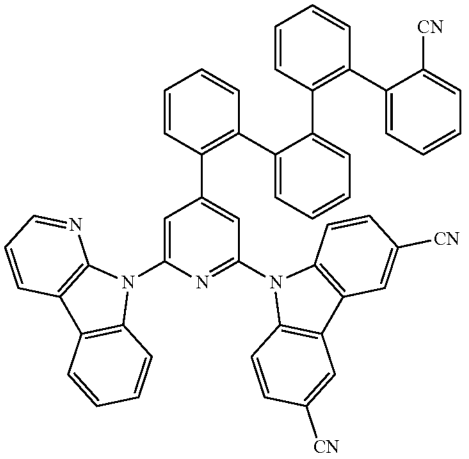
161
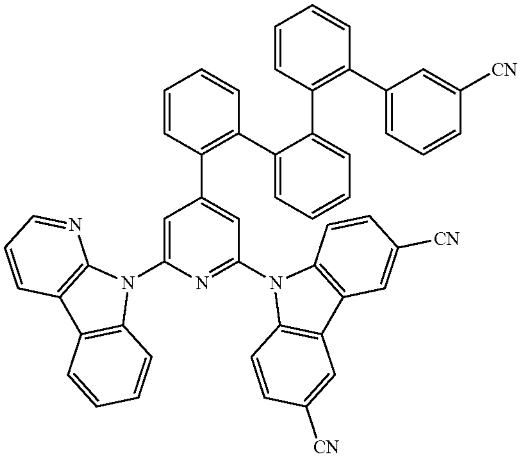
162
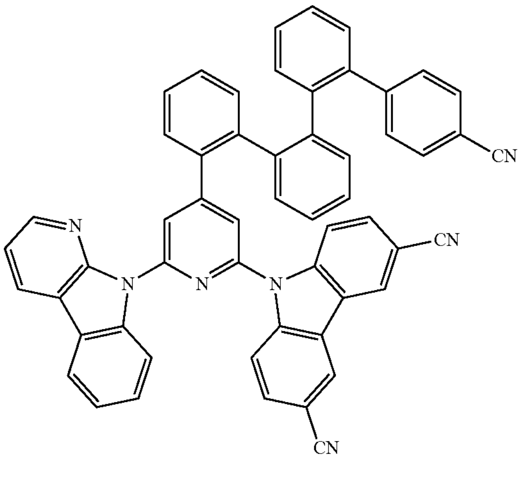

-continued
163
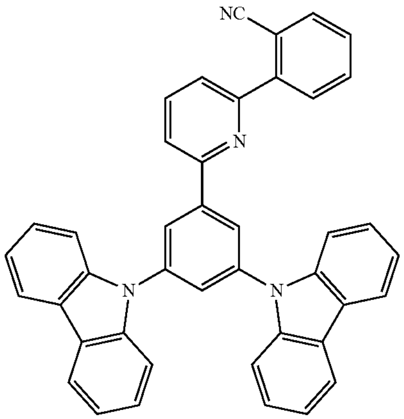
164
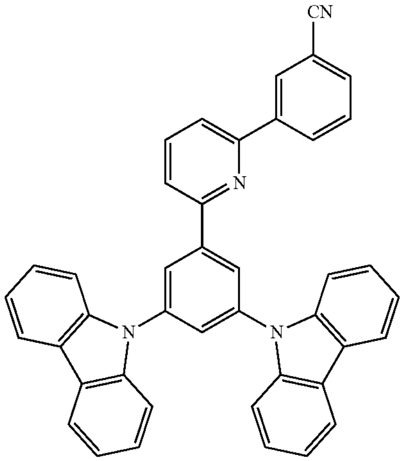
165
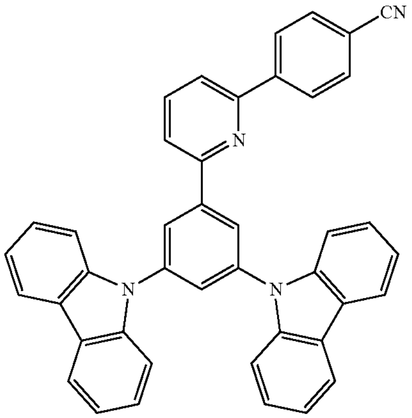
-continued
166
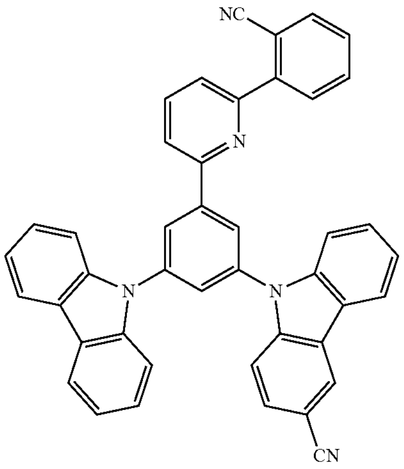
167
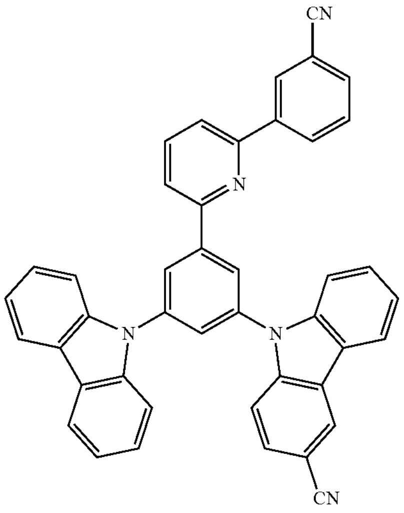
168
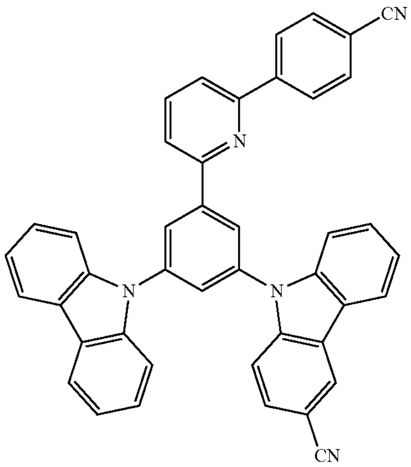

-continued
169
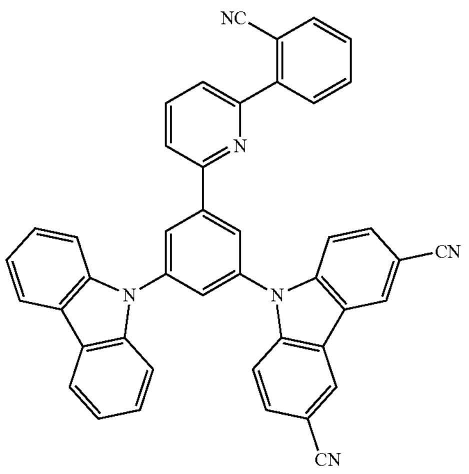
170
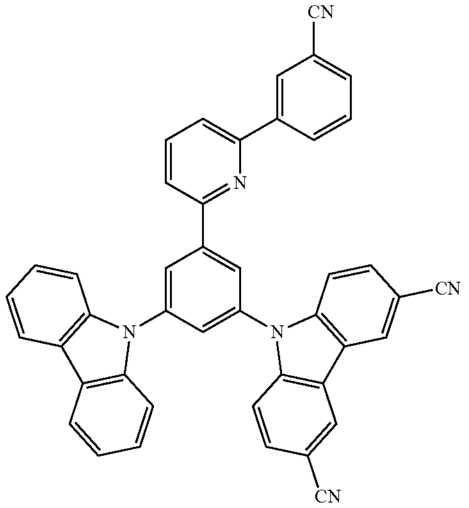
171
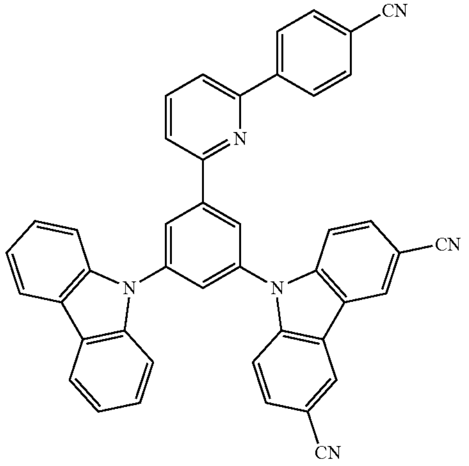
-continued
172
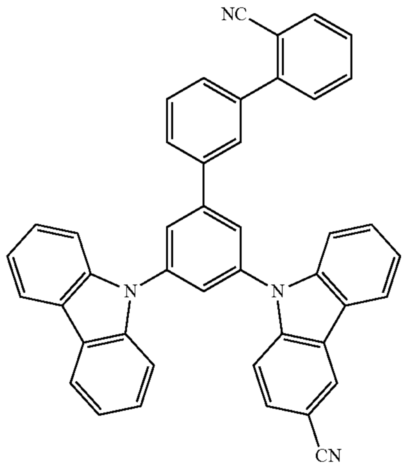
173
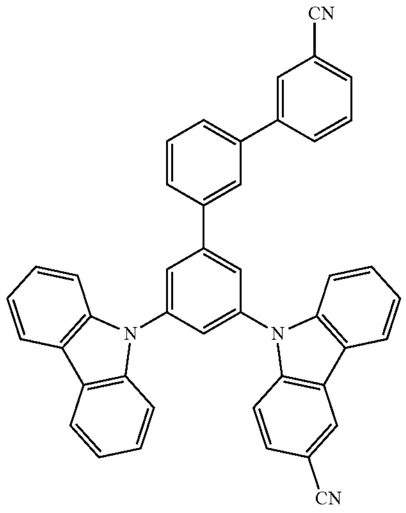
174
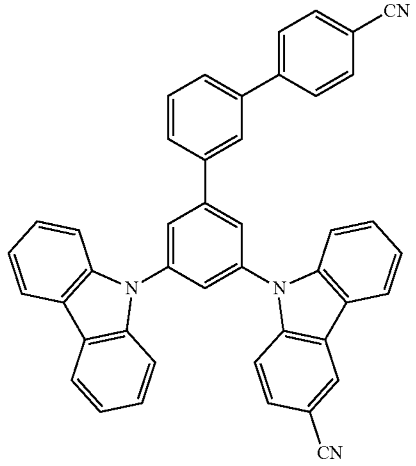

-continued
175
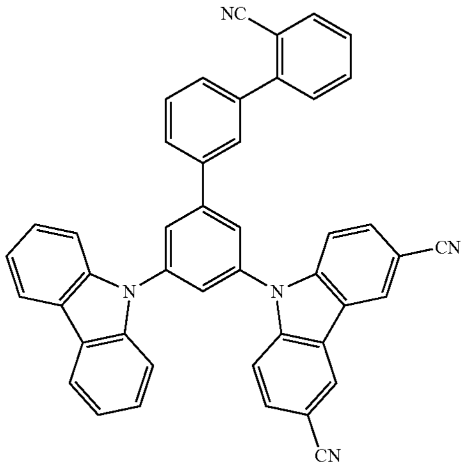
176
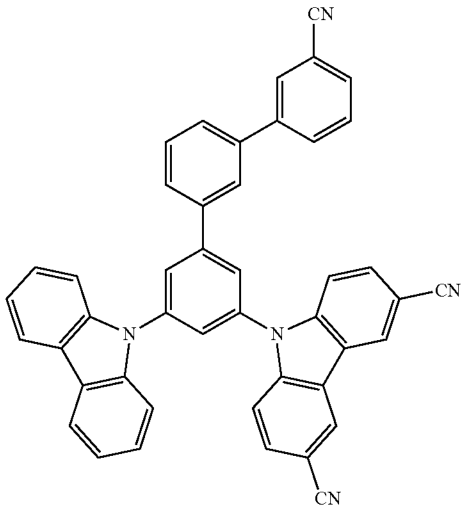
177
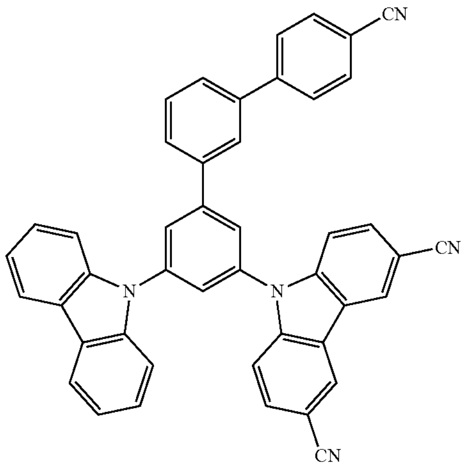
-continued
178
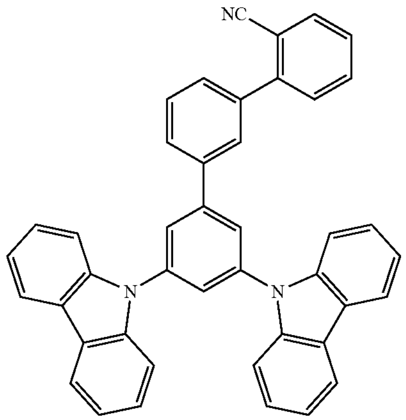
179
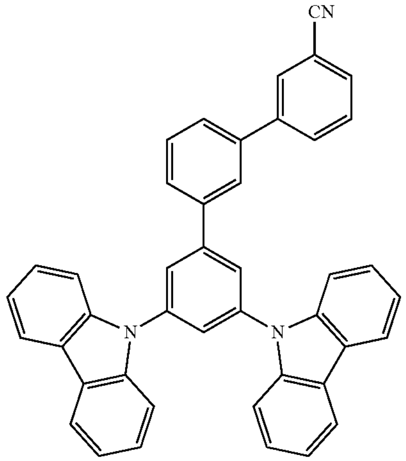
180
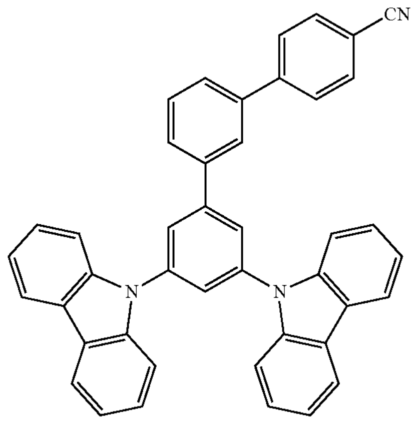

-continued
181
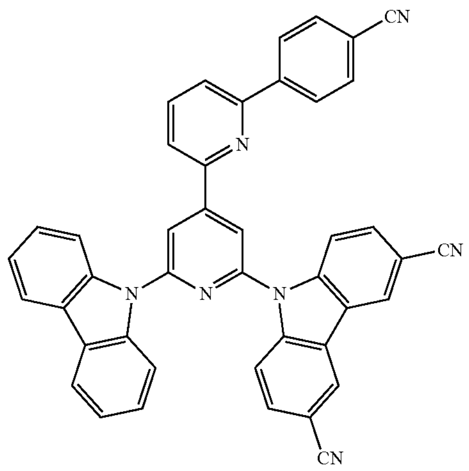
182
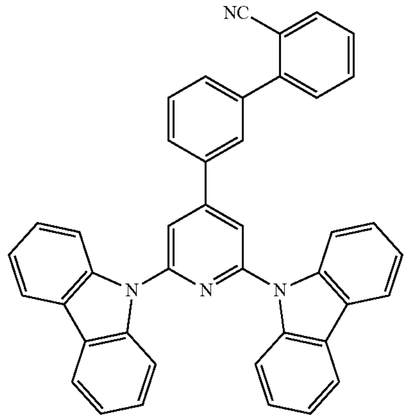
183
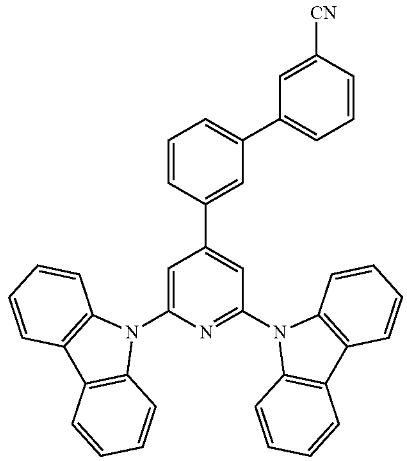
184
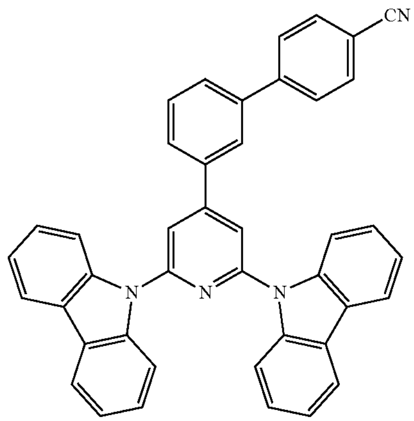
185
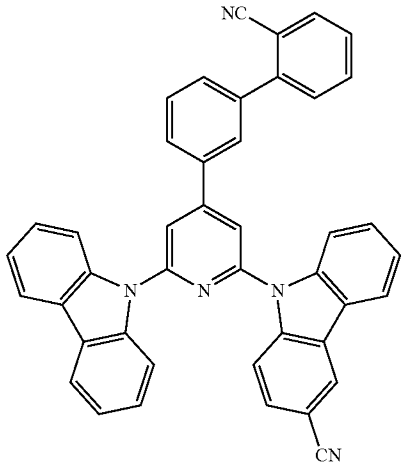
186
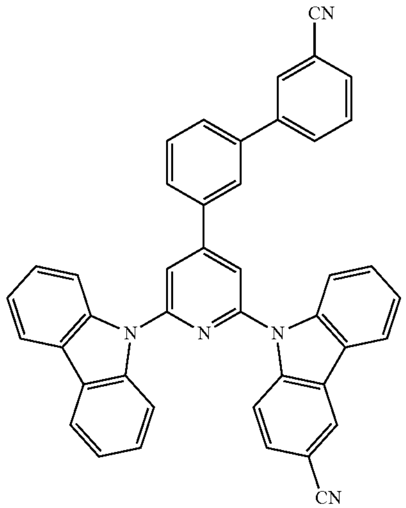

-continued
187
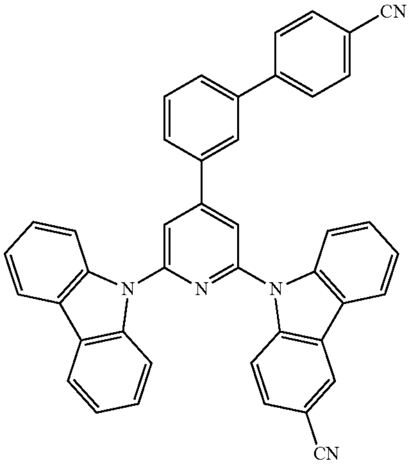
188
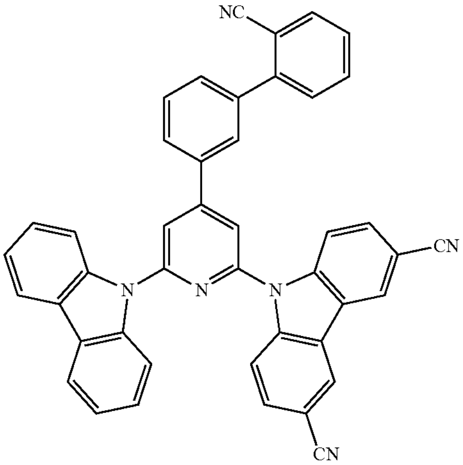
189
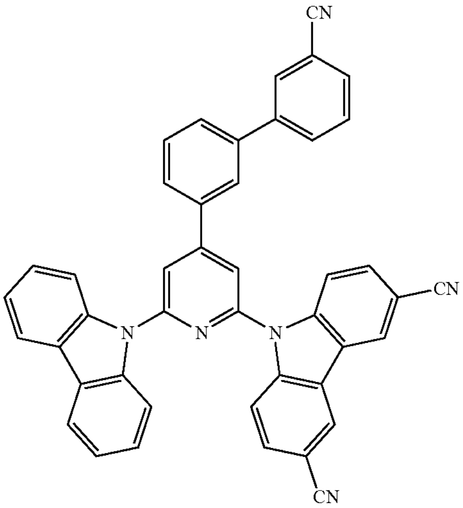
-continued
190
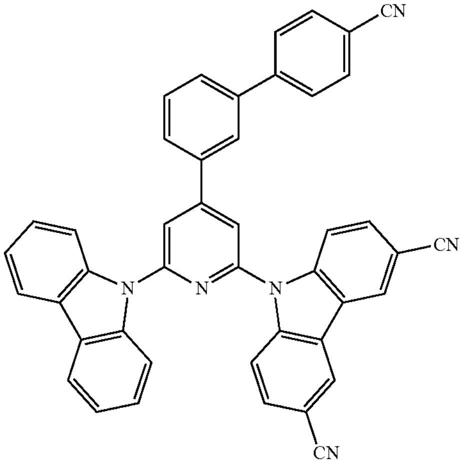
191
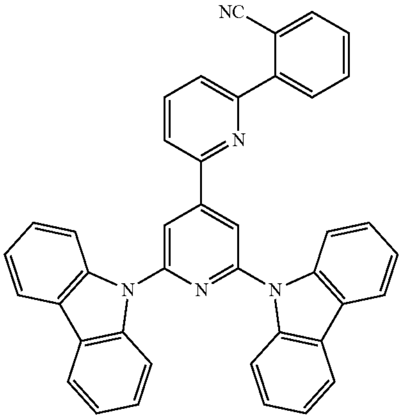
192
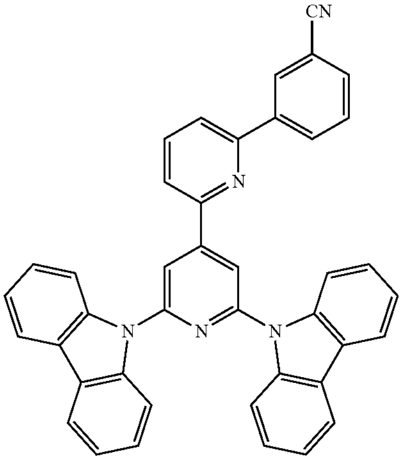

-continued
193
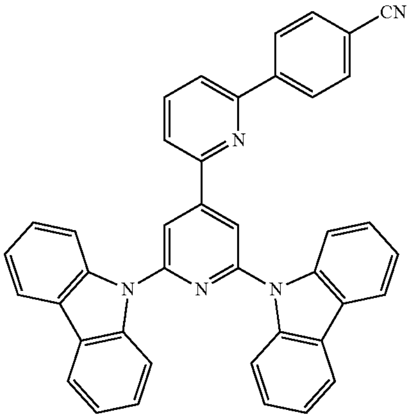
194
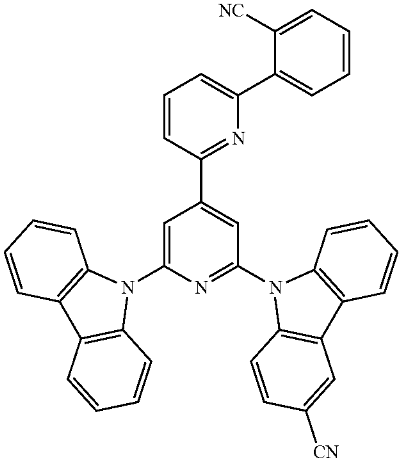
195
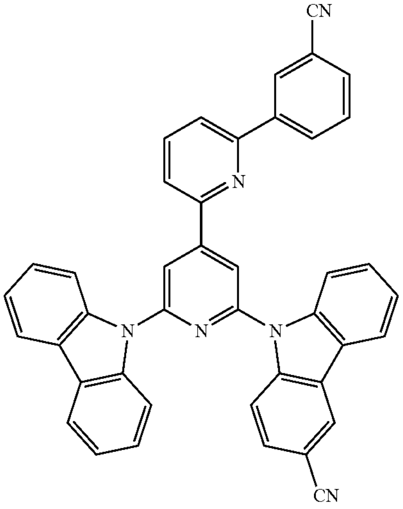
-continued
196
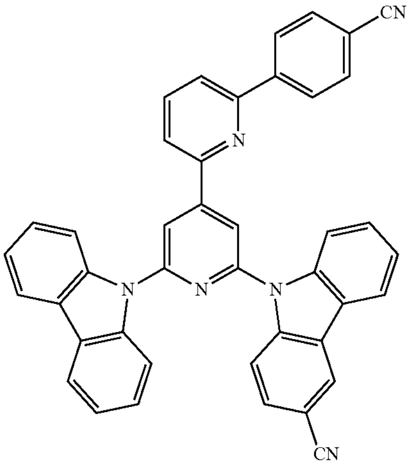
197
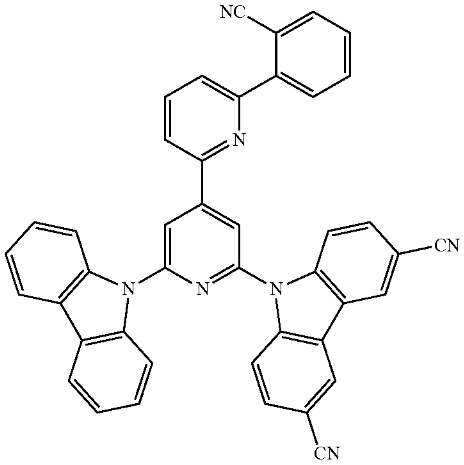
198
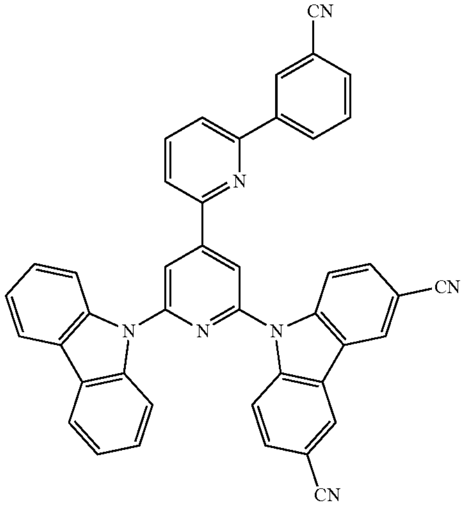

-continued
199
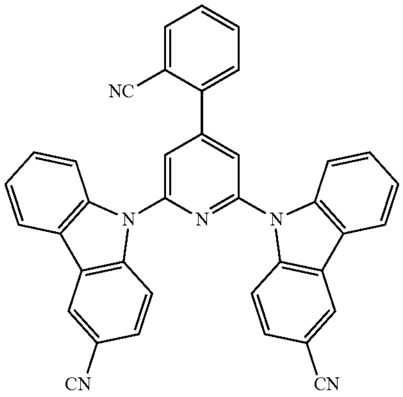
200
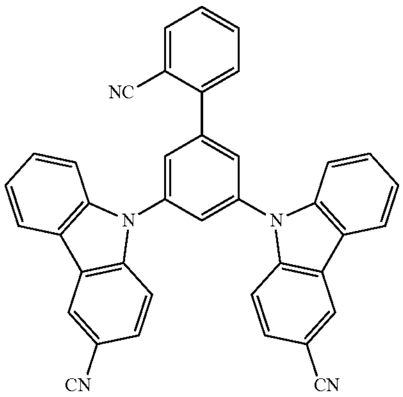
201
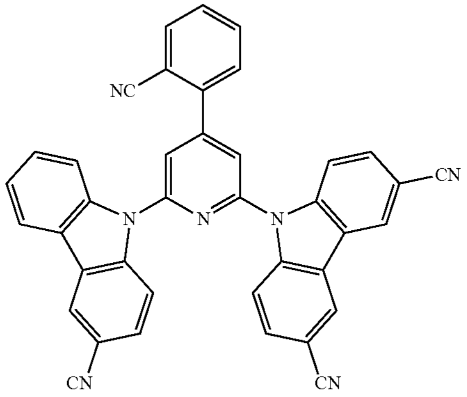
202
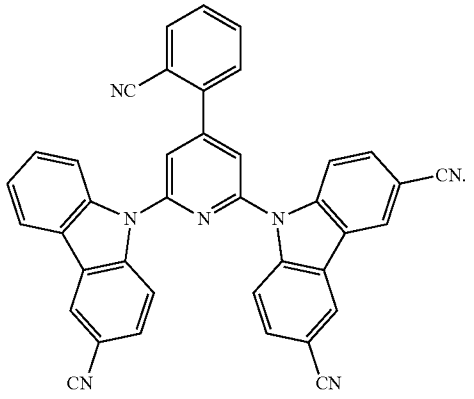
Group HE6
1
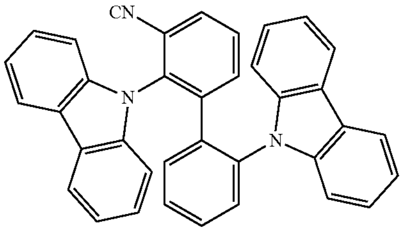
2
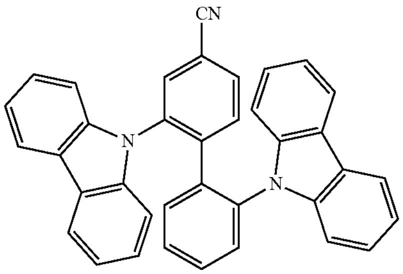
3
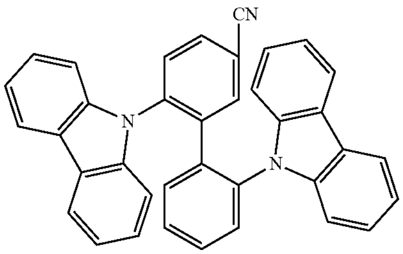
4
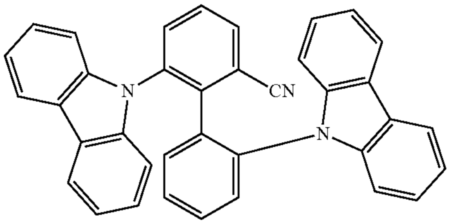
5
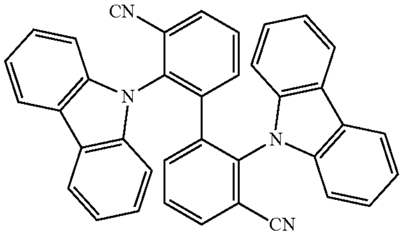
6
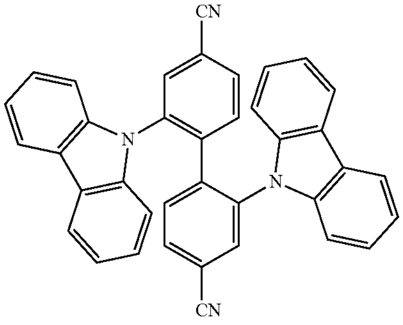

-continued
7
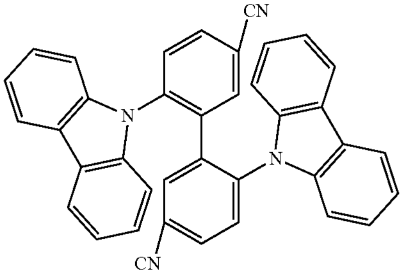
8
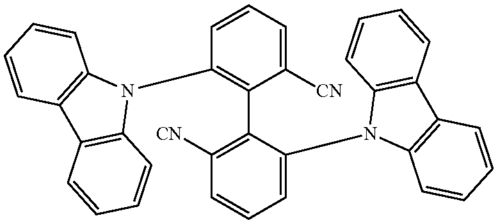
9
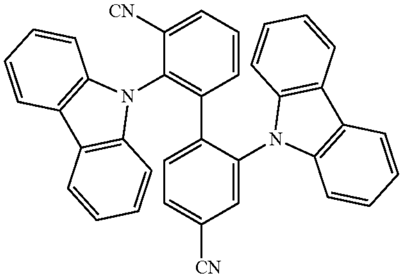
10
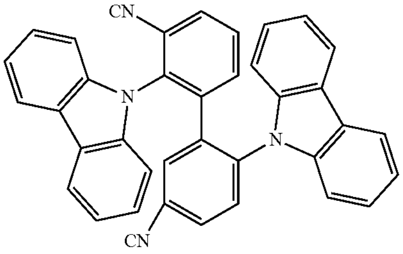
11
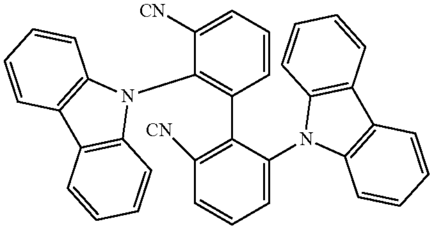
12
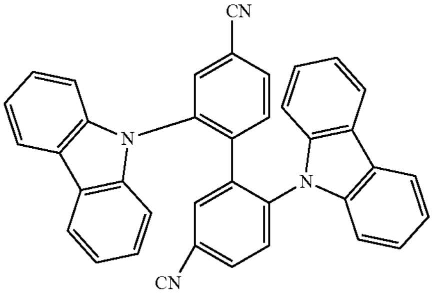
-continued
13
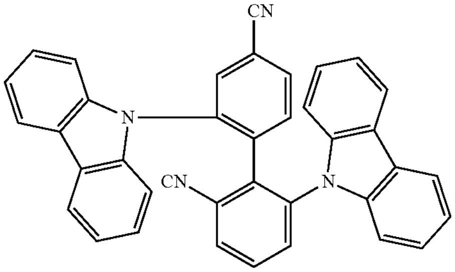
14
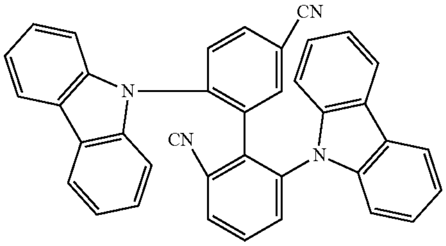
15
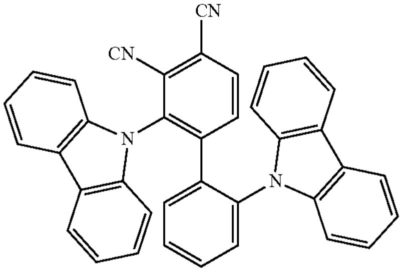
16
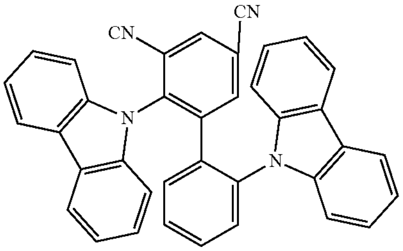
17
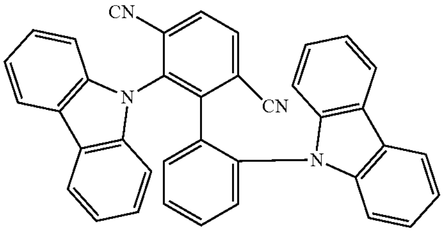
18
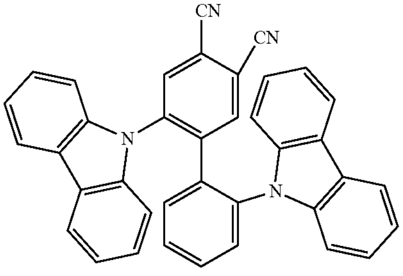

-continued
19
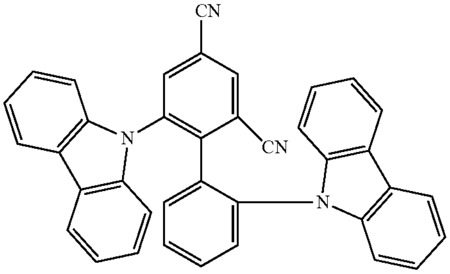
20
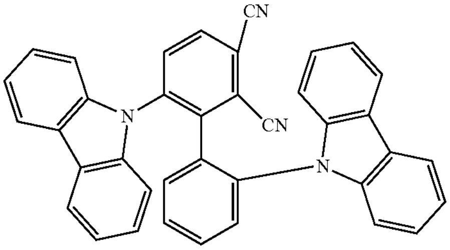
21
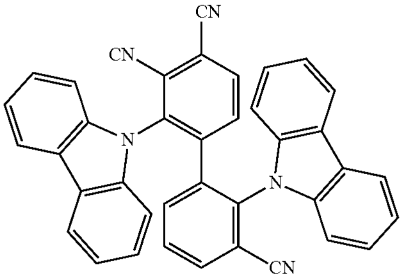
22
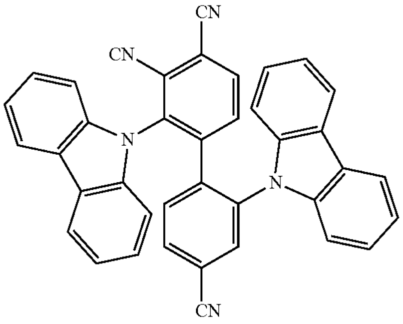
23
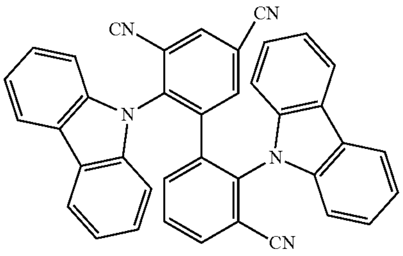
-continued
24
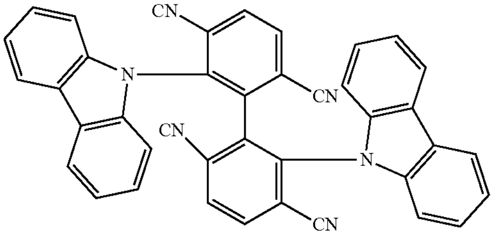
25
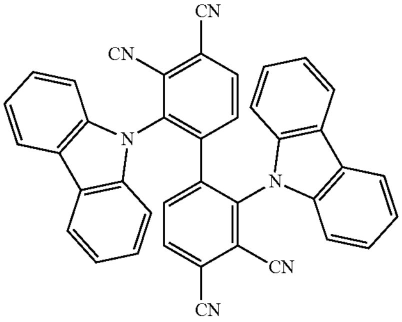
26
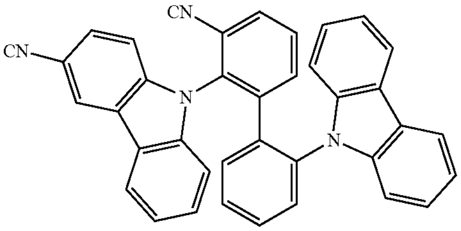
27
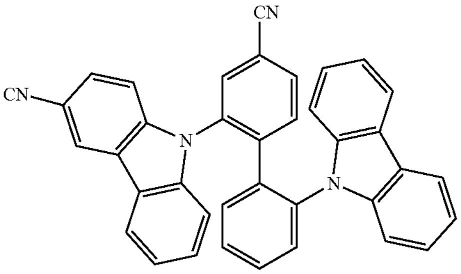
28
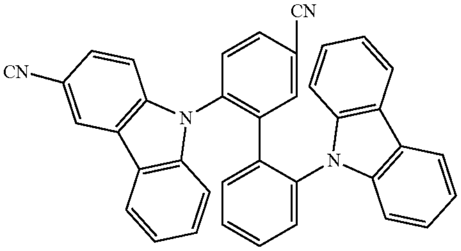
29
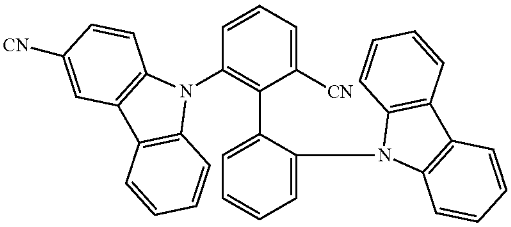

-continued
30
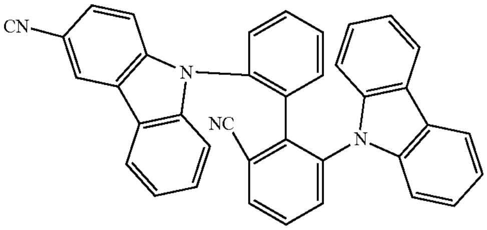
31
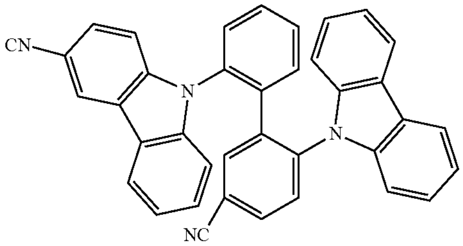
32
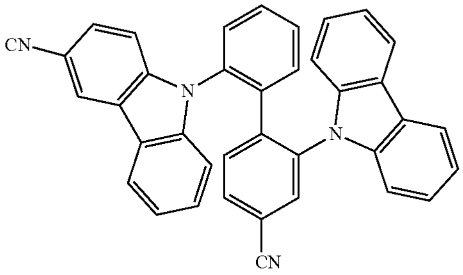
33
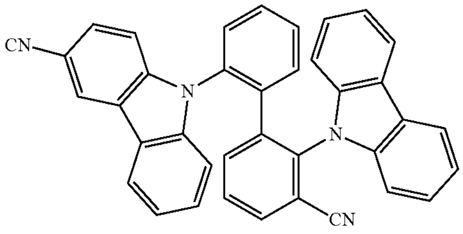
34
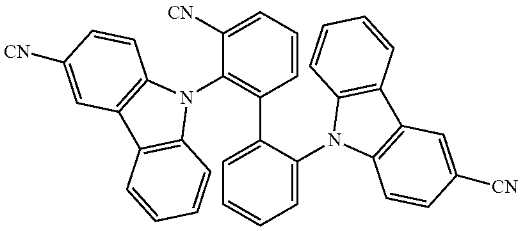
35
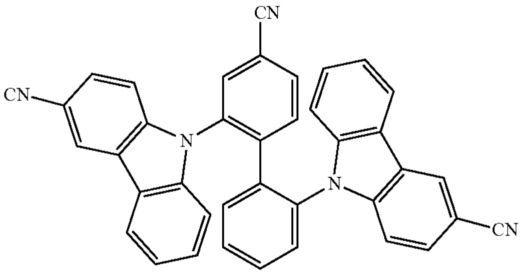
-continued
36
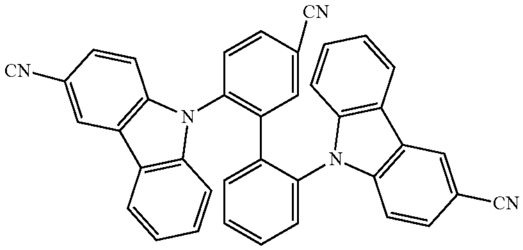
37
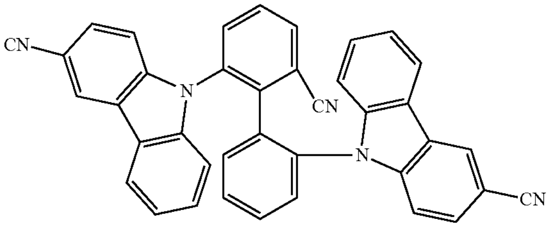
38
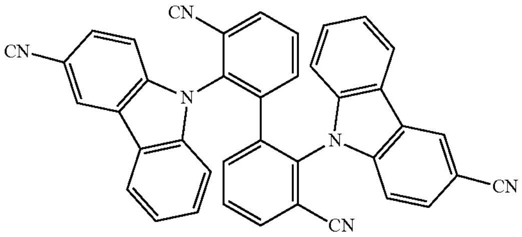
39
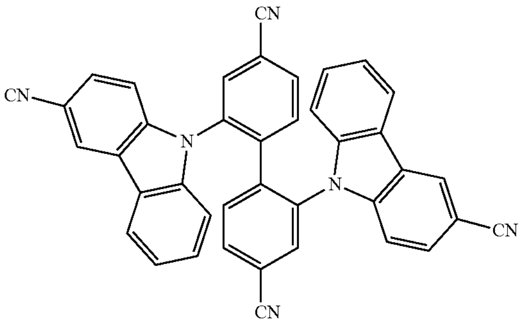
40
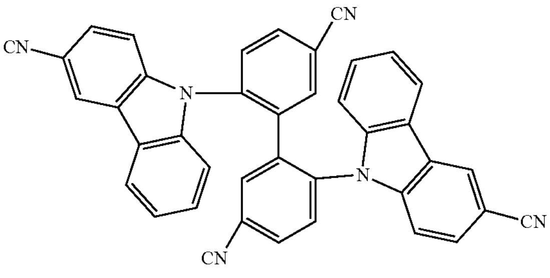

-continued
41
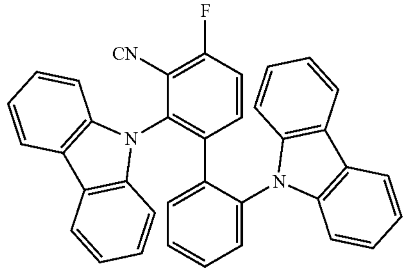
42
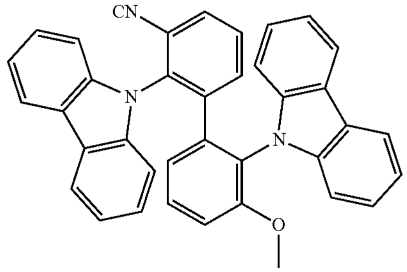
43
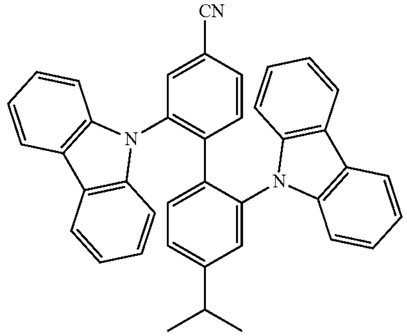
44
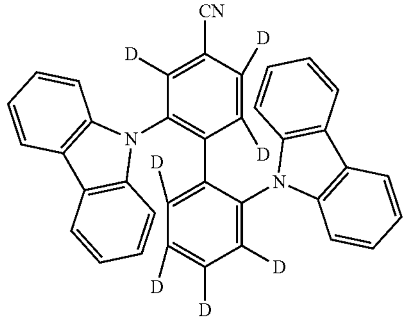
45
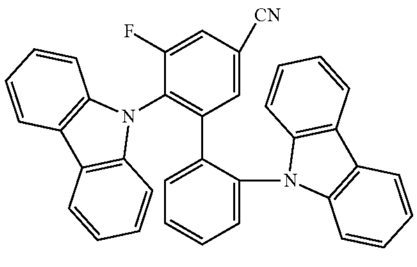
-continued
46
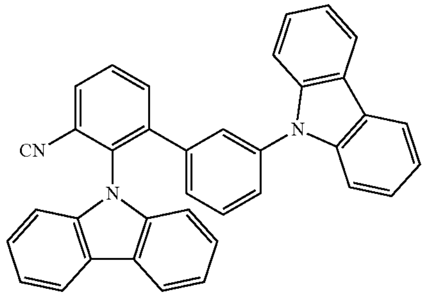
47
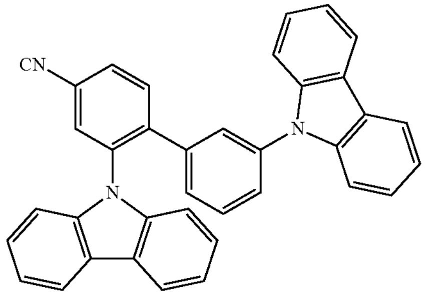
48
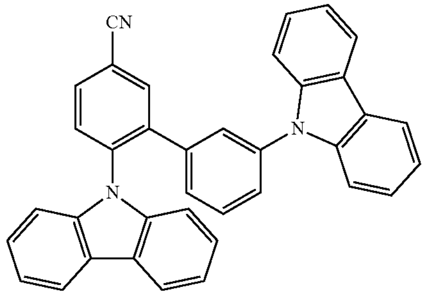
49
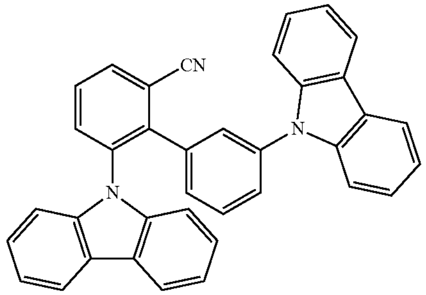
50
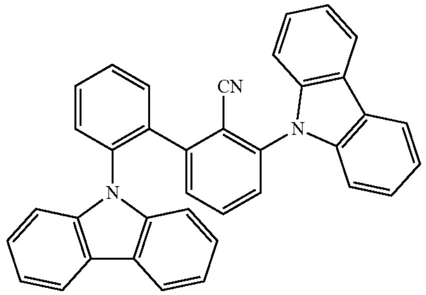

-continued
51
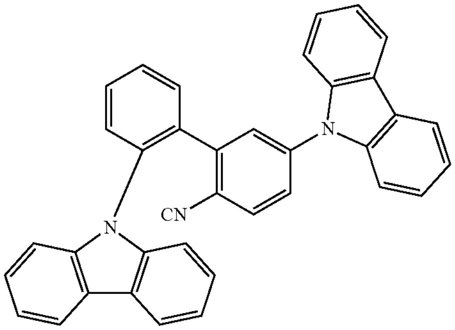
52
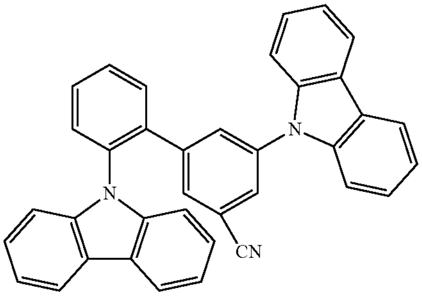
53
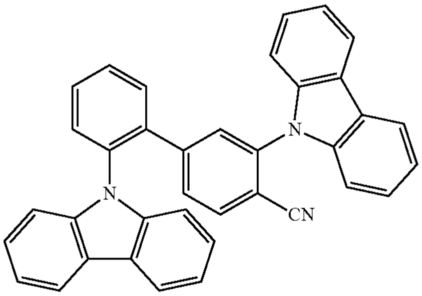
54
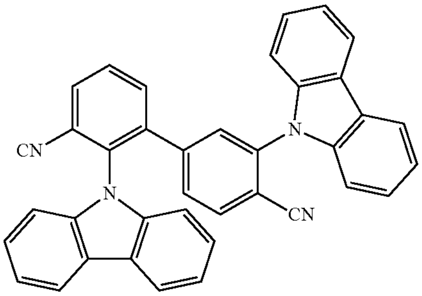
55
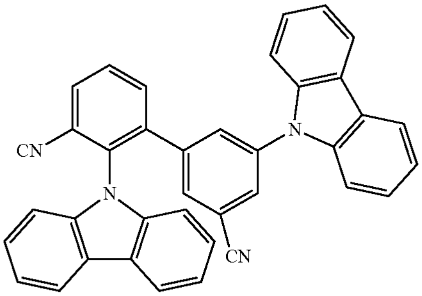
-continued
56
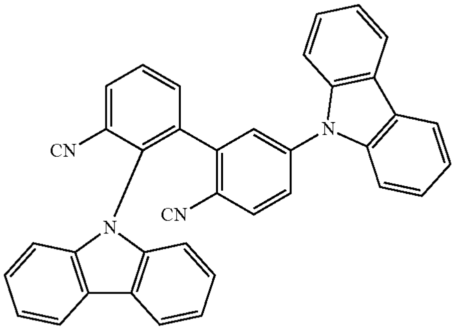
57
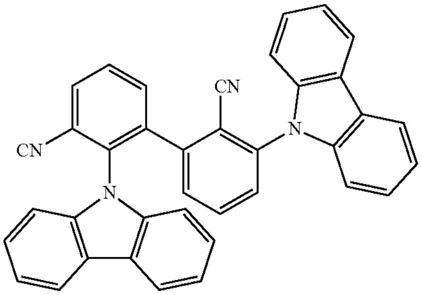
58
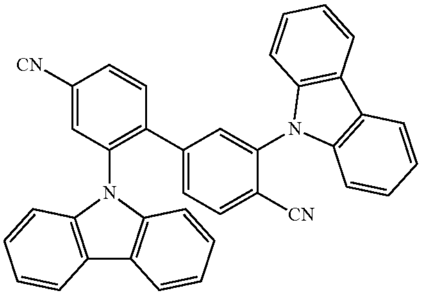
59
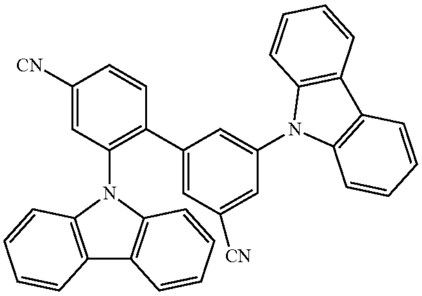
60
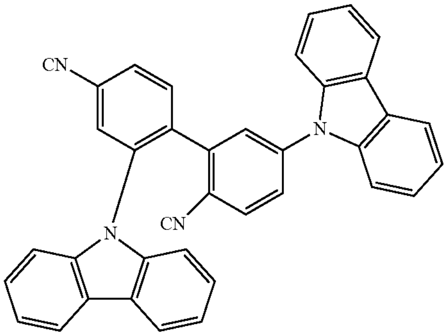

-continued
61
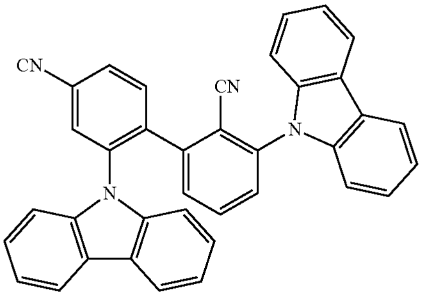
62
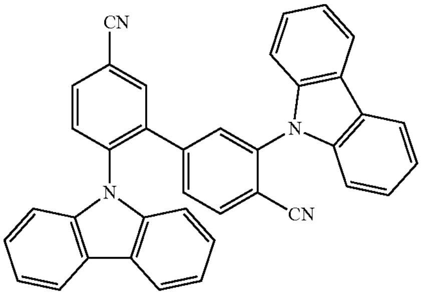
63
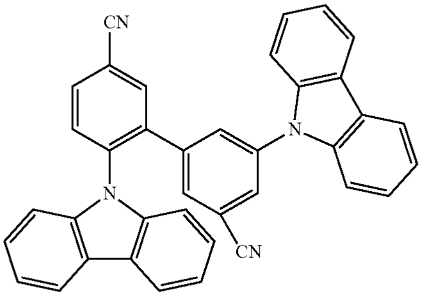
64
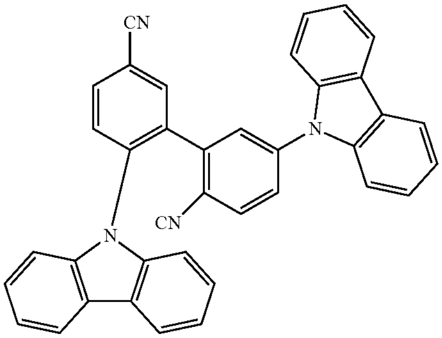
65
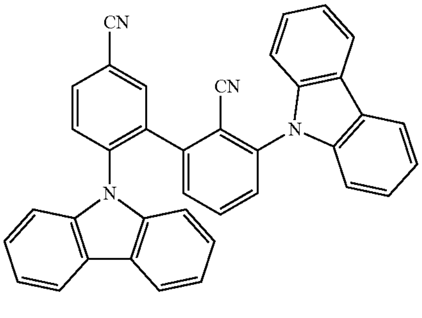
-continued
66
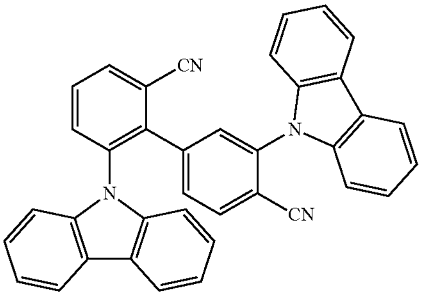
67
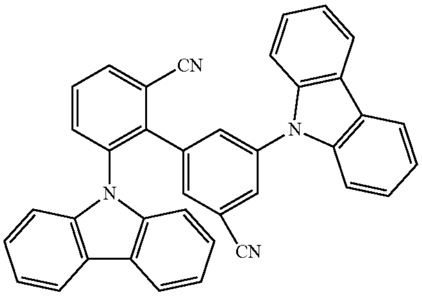
68
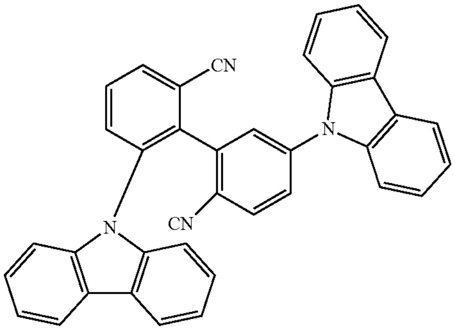
69
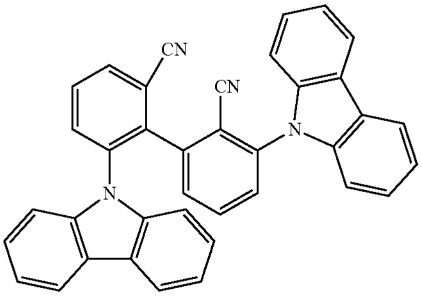
70
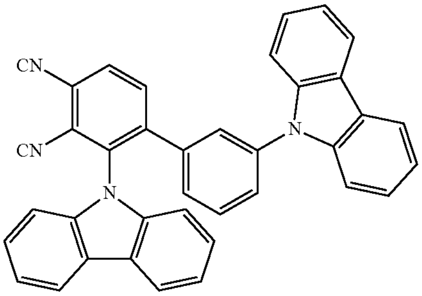

-continued
71
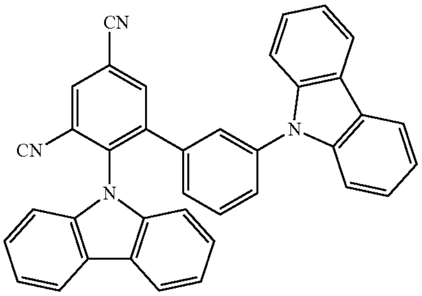
72
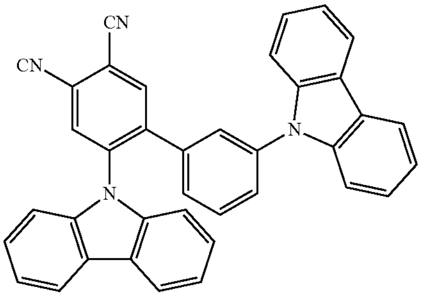
73
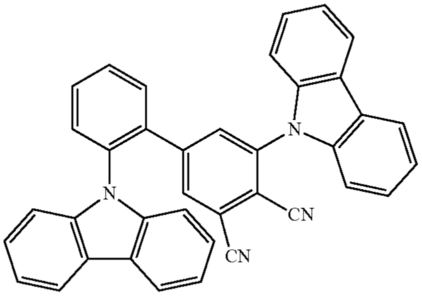
74
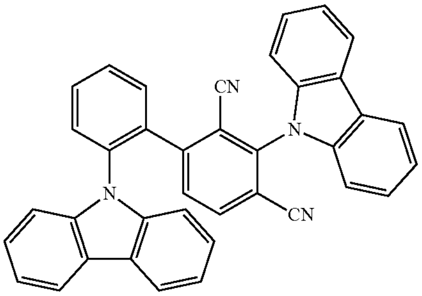
75
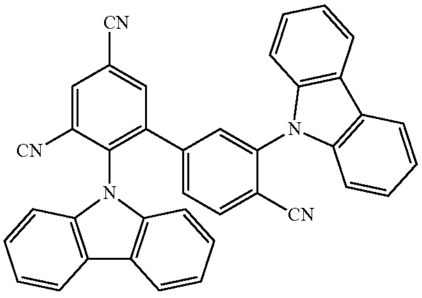
-continued
76
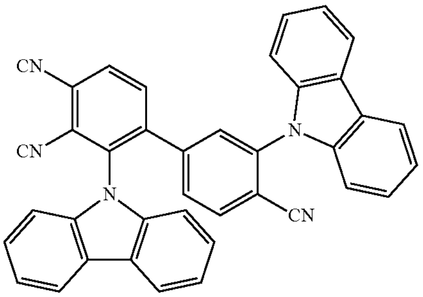
77
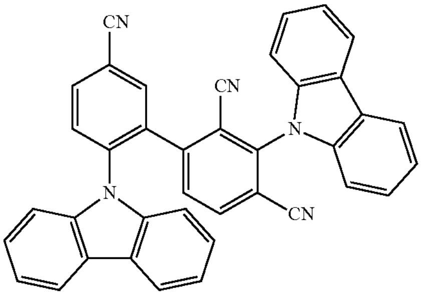
78
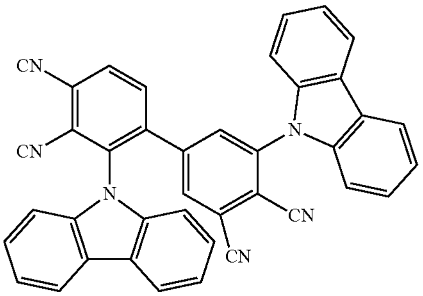
79
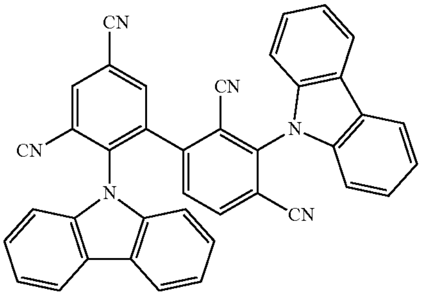
80
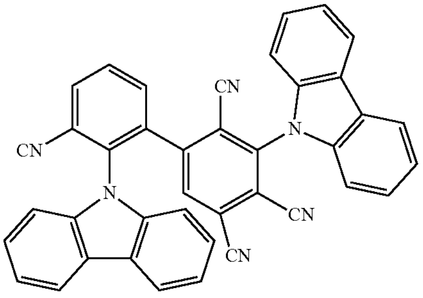

-continued
81
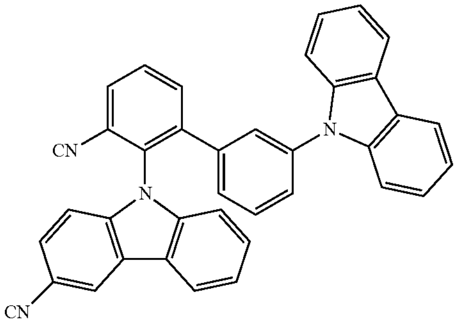
82
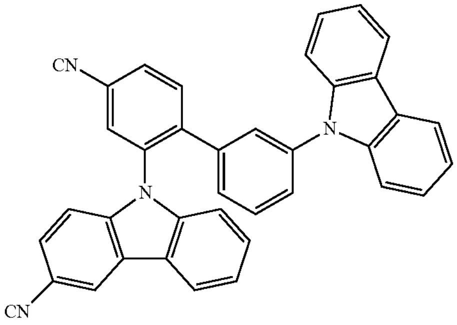
83
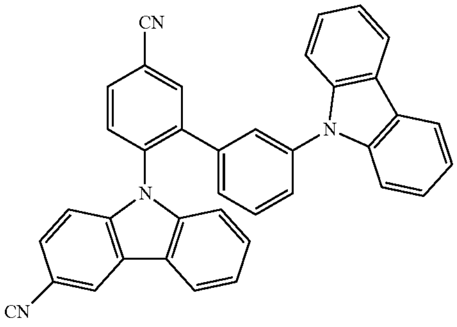
84
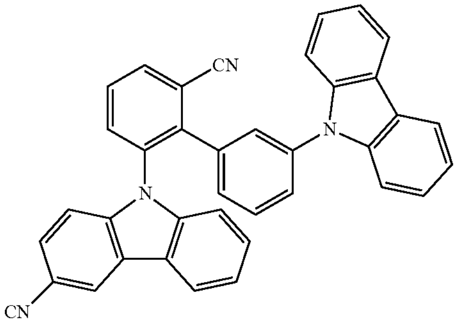
85
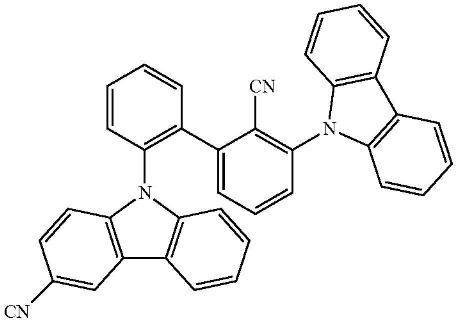
-continued
86
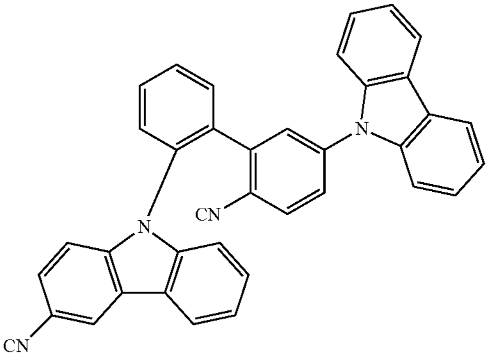
87
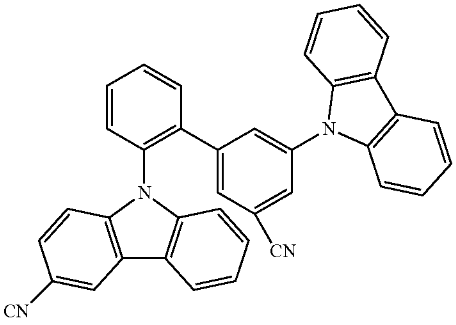
88
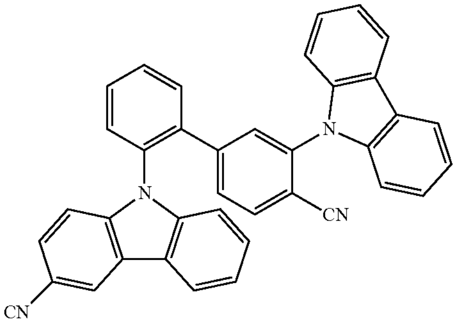
89
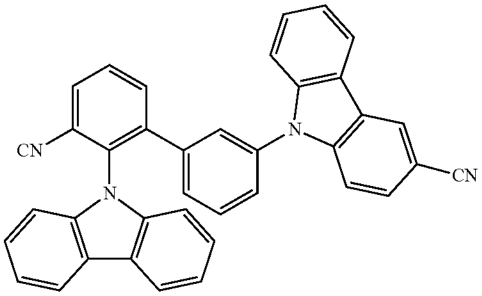
90
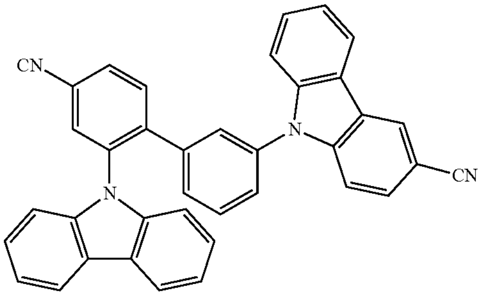

-continued
91
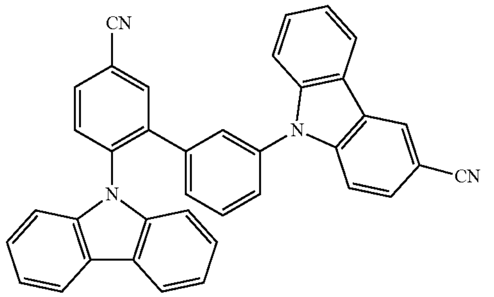
92
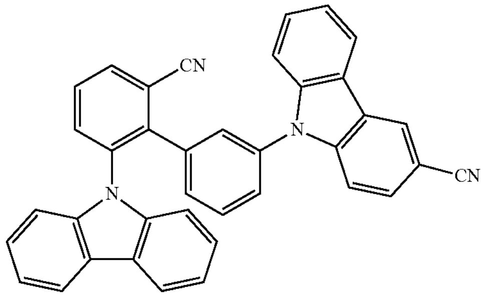
93
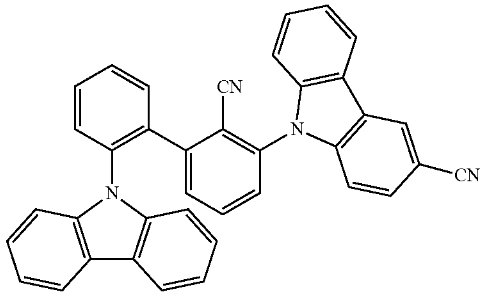
94
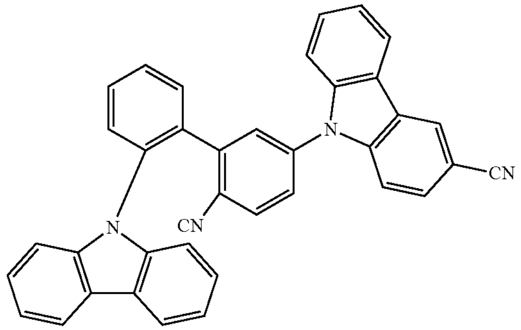
95
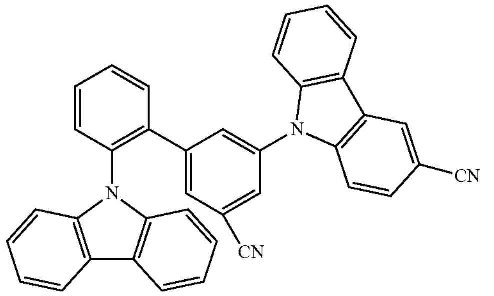
-continued
96
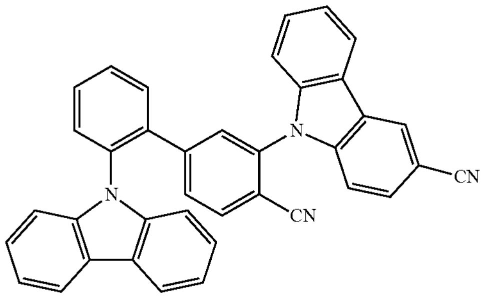
97
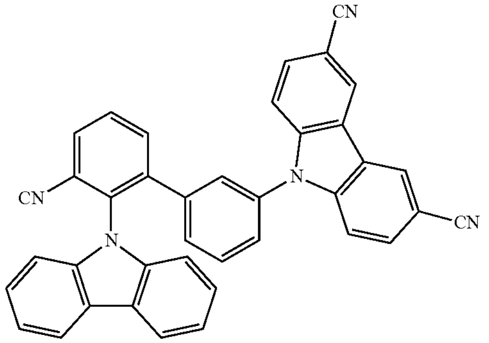
98
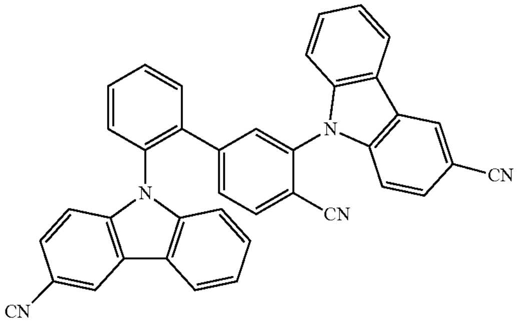
99
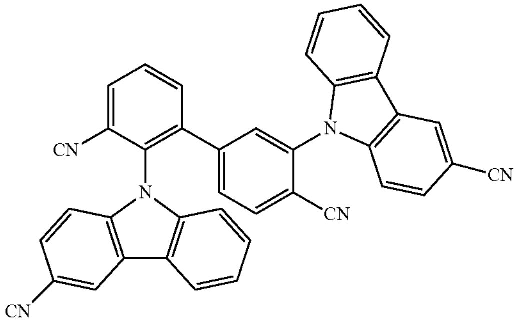

-continued
100
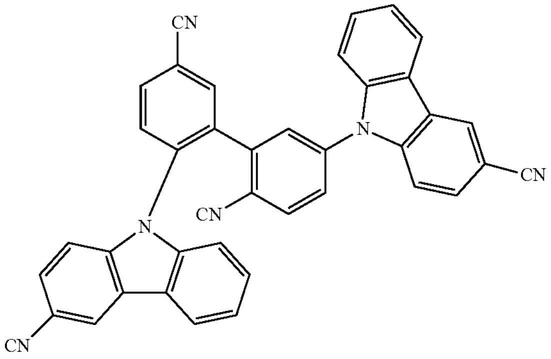
101
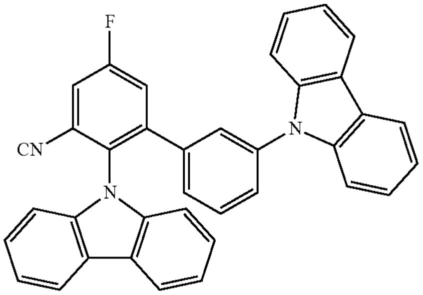
102
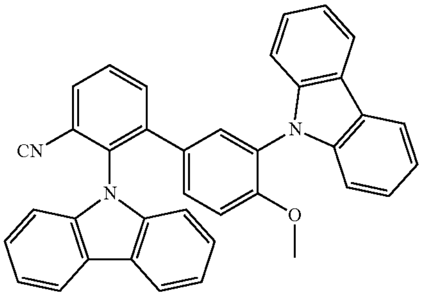
103
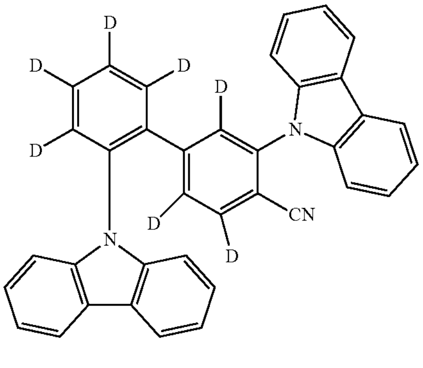
-continued
104
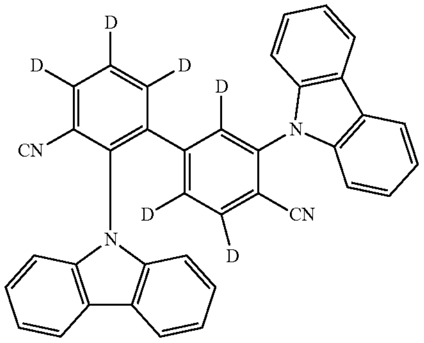
105
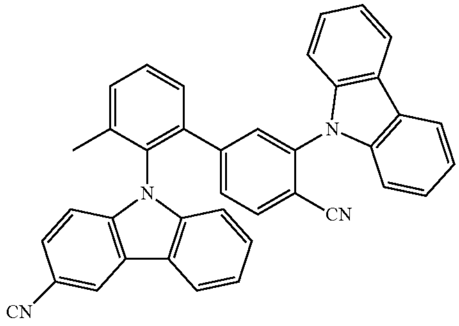
106
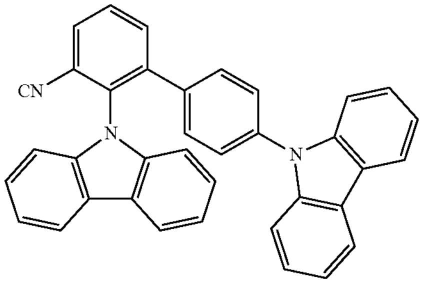
107
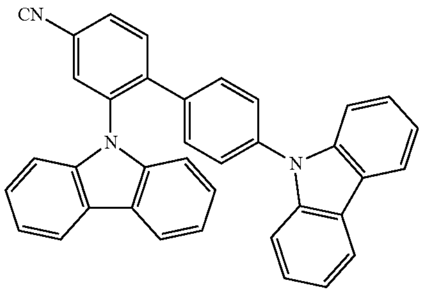
108
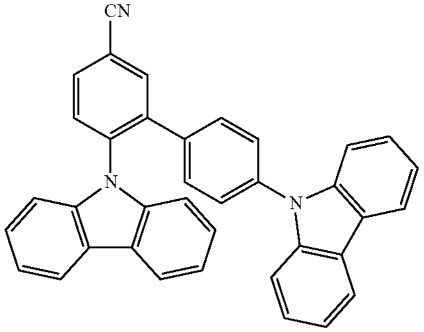

-continued
109
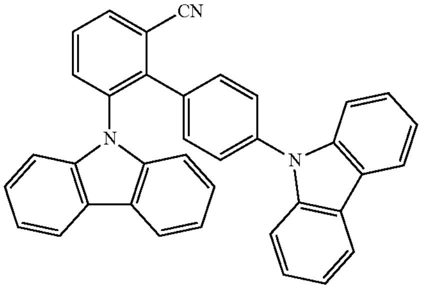
110
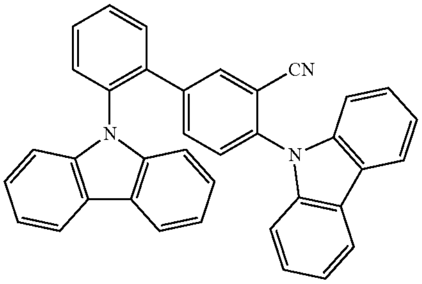
111
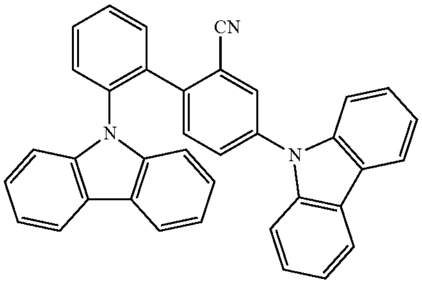
112
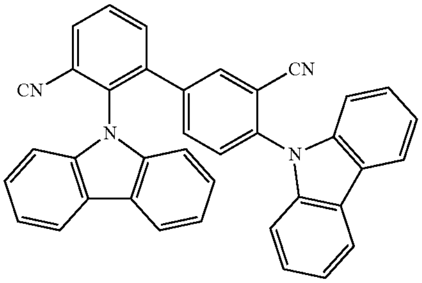
113
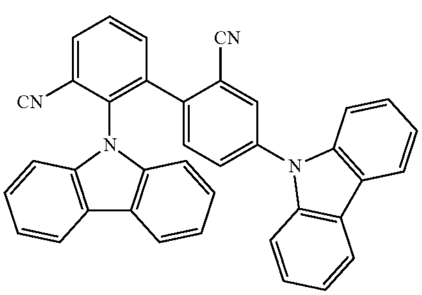
-continued
114
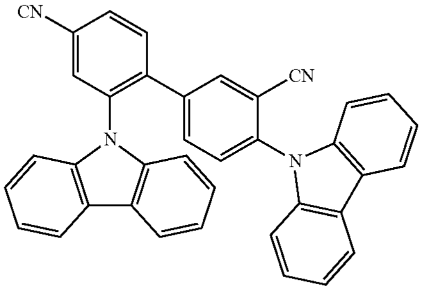
115
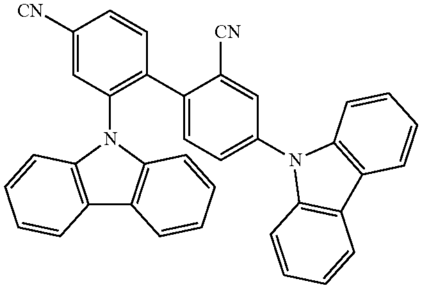
116
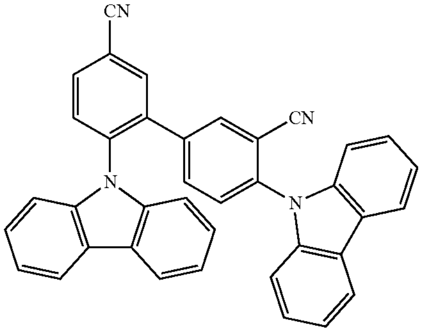
117
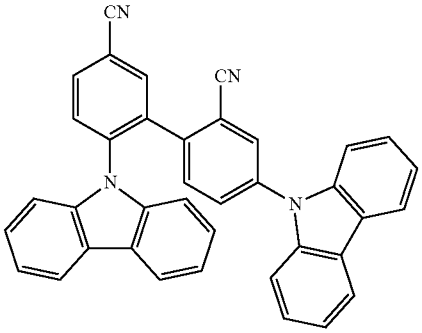
118
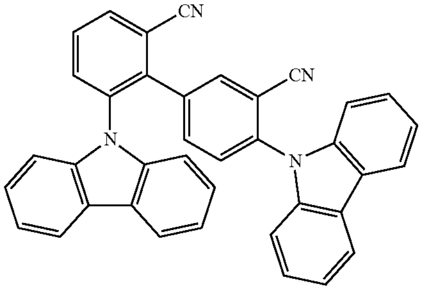

-continued
119
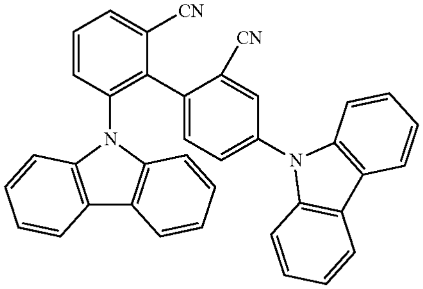
120
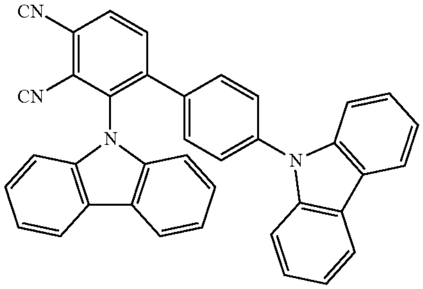
121
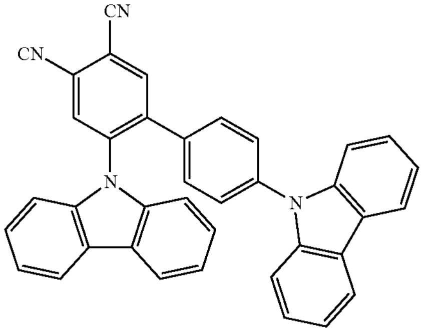
122
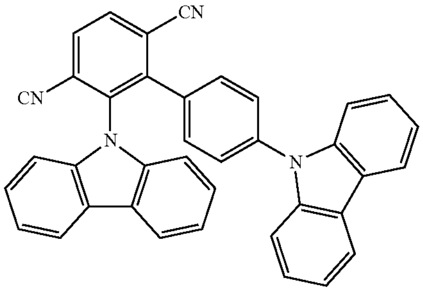
123
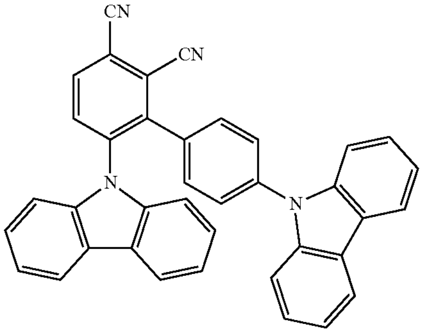
-continued
124
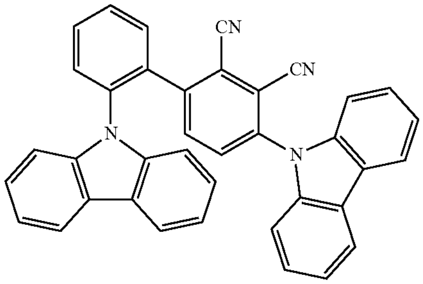
125
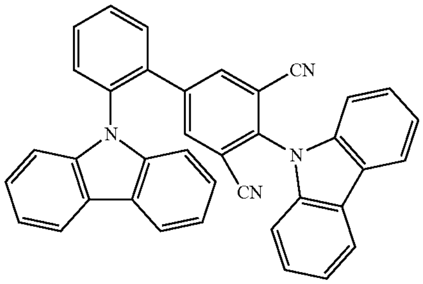
126
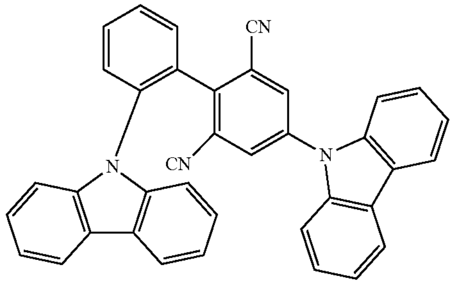
127
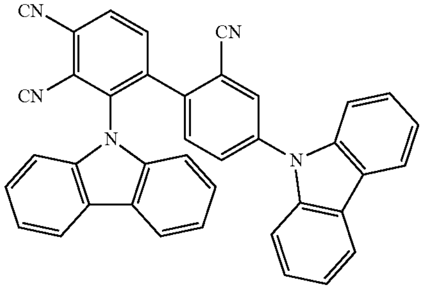
128
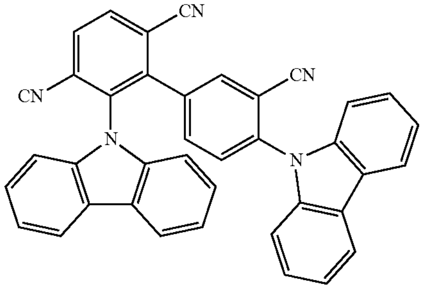

-continued
129
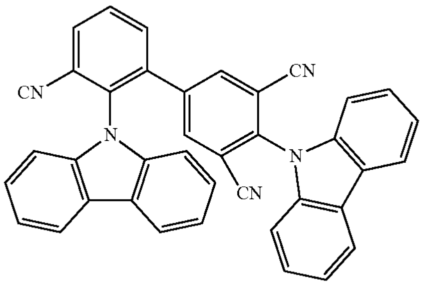
130
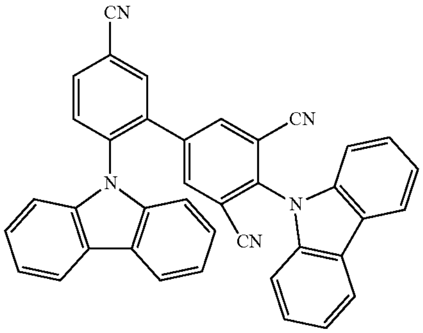
131
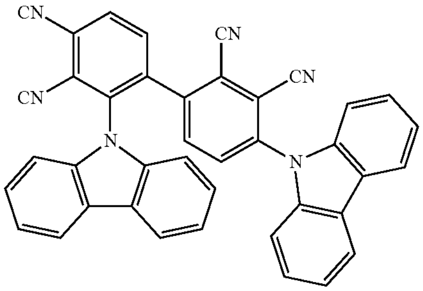
132
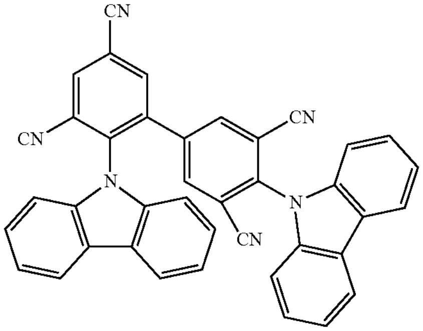
133
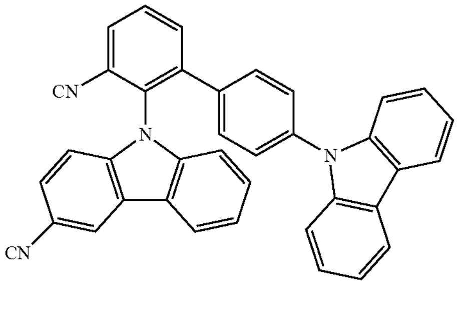
-continued
134
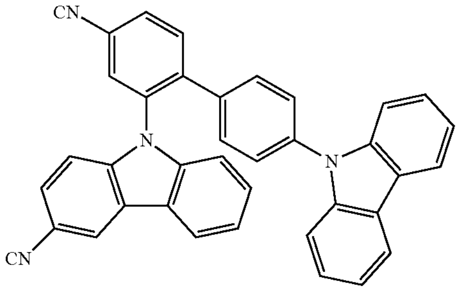
135
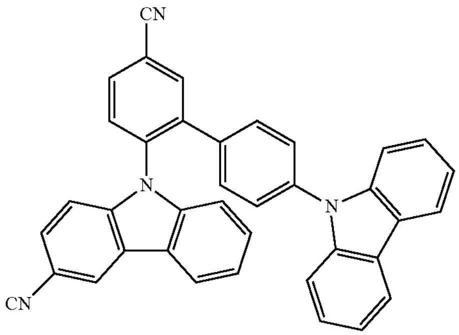
136
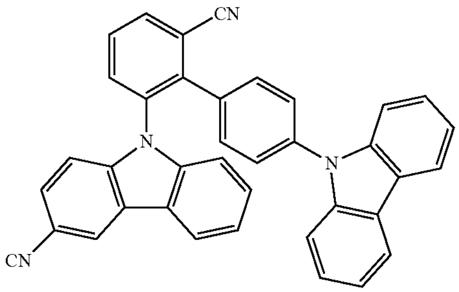
137
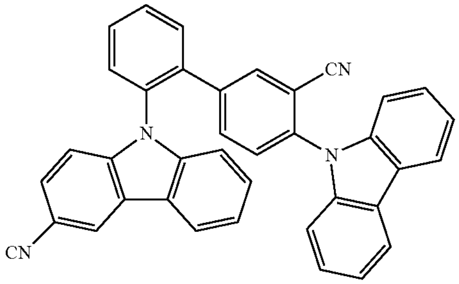
138
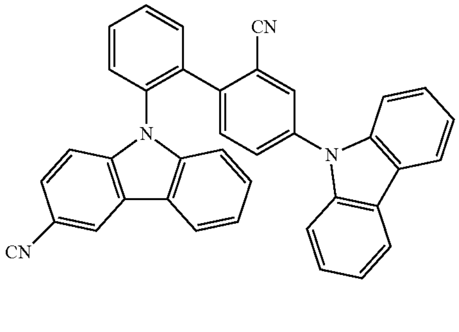

139
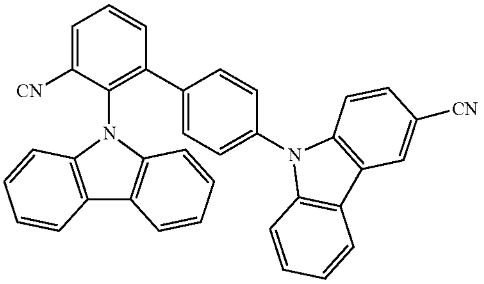
140
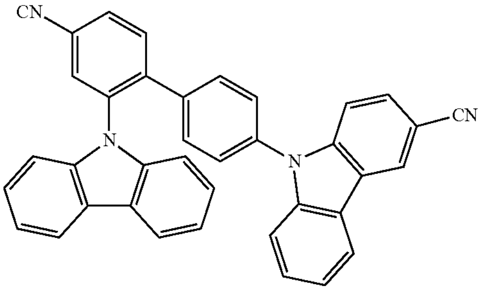
141
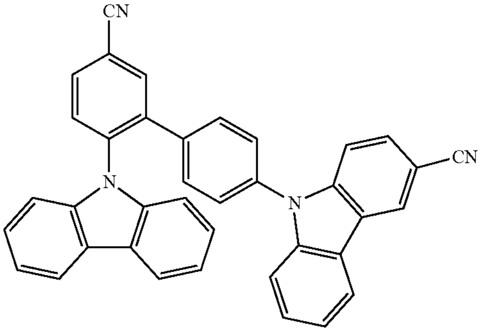
142
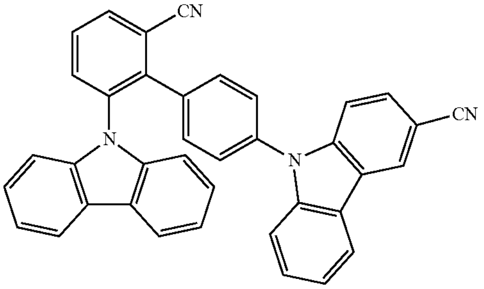
143
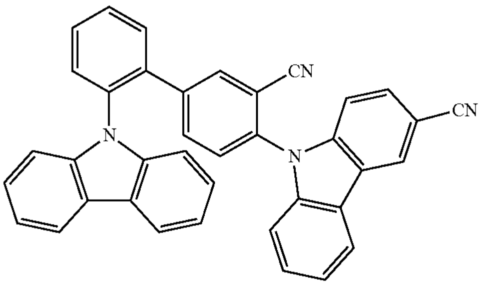
144
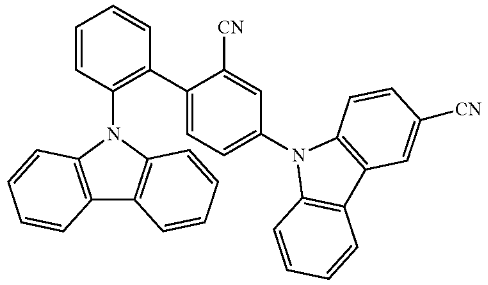
145
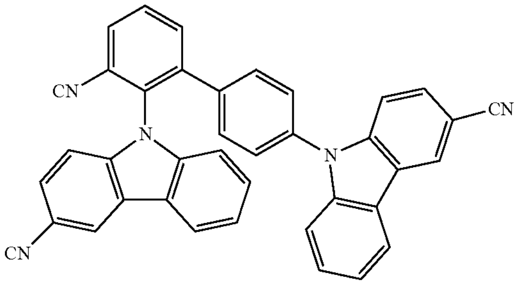
146
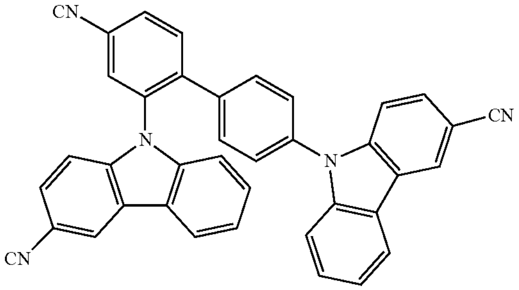
147
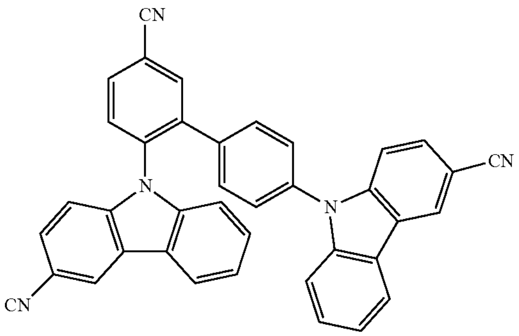
148
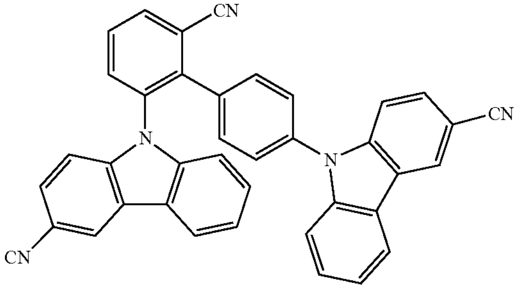

-continued
149
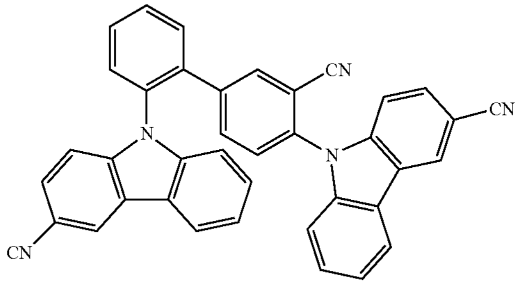
150
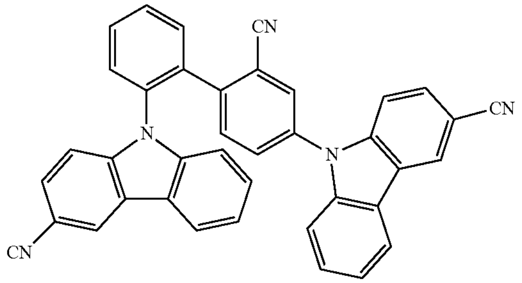
151
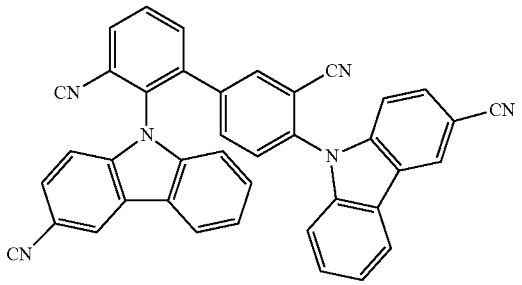
152
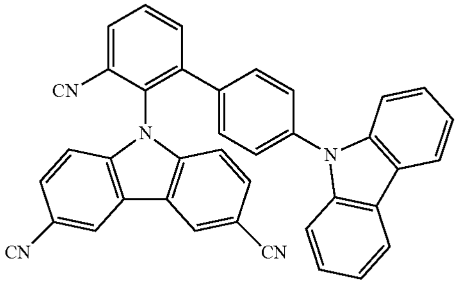
153
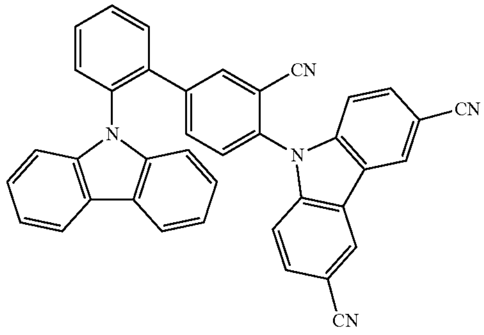
-continued
154
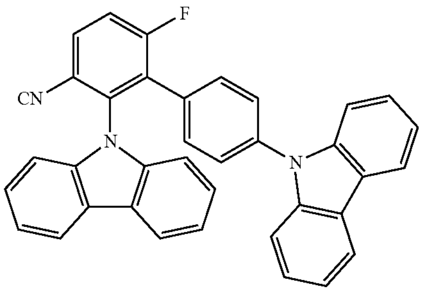
155
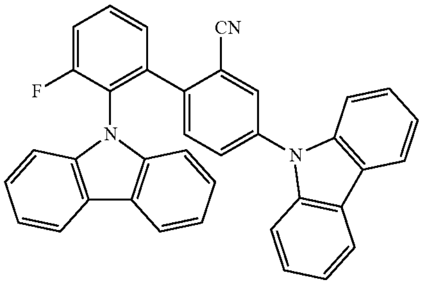
156
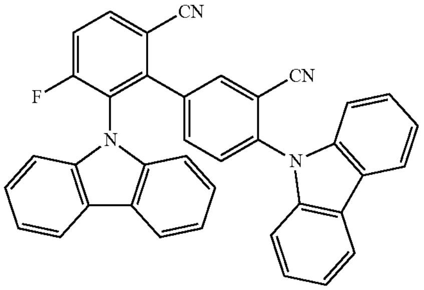
157
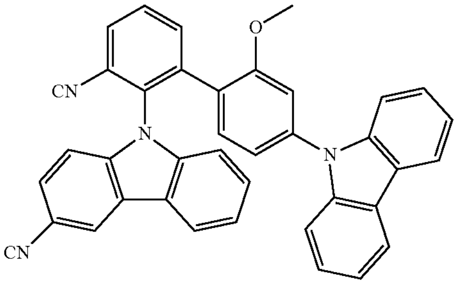
158
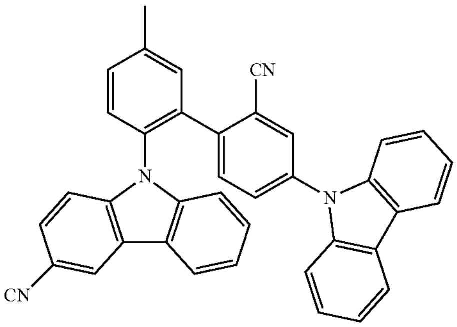

-continued
159
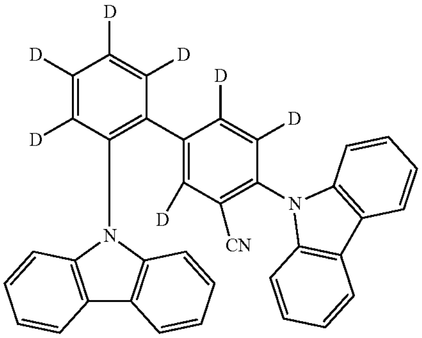
160
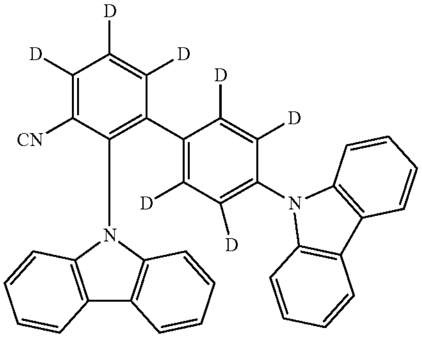
161
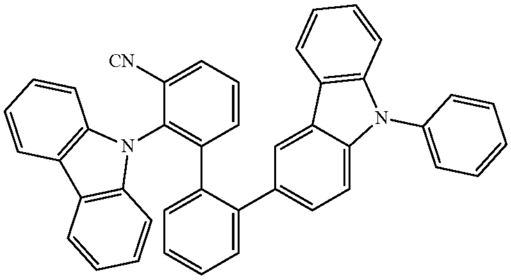
162
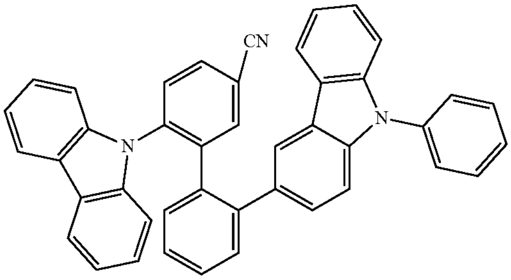
163
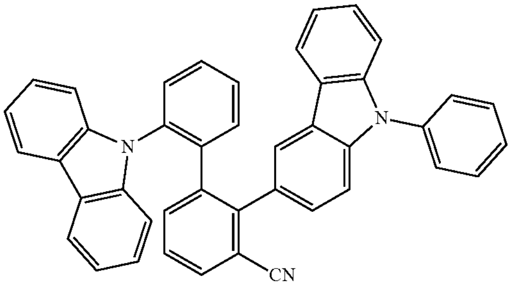
-continued
164
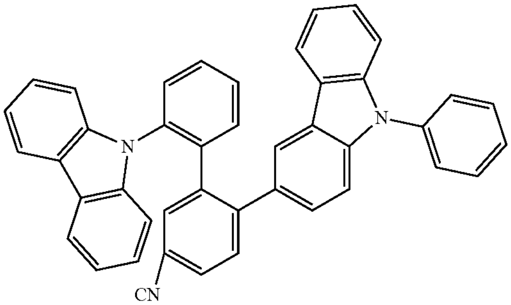
165
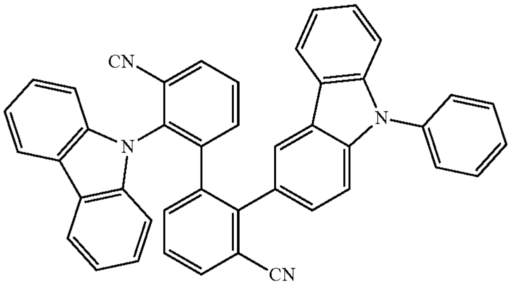
166
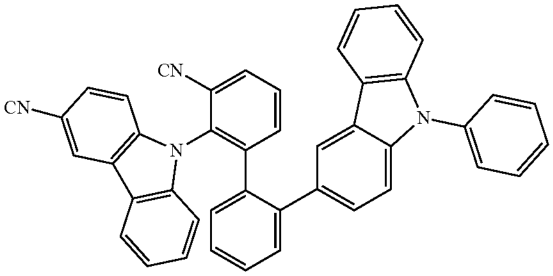
167
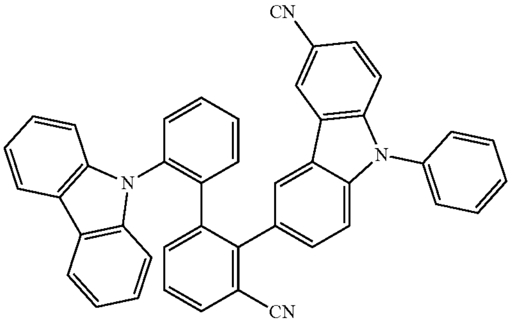
168
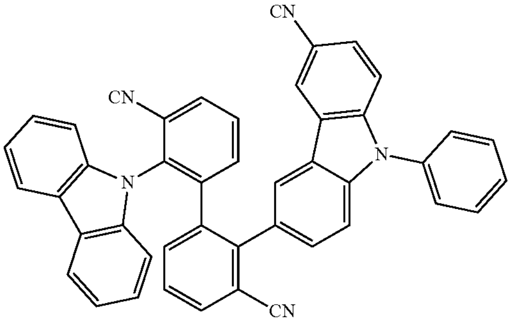

-continued
169
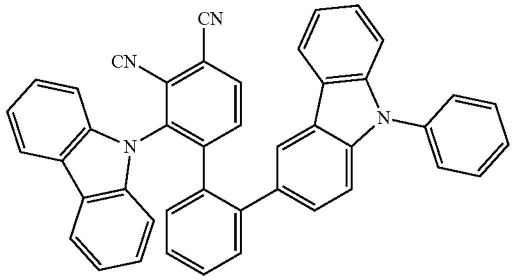
170
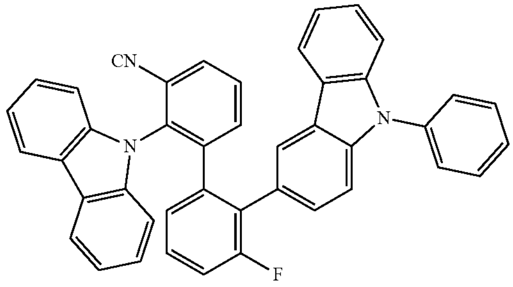
171
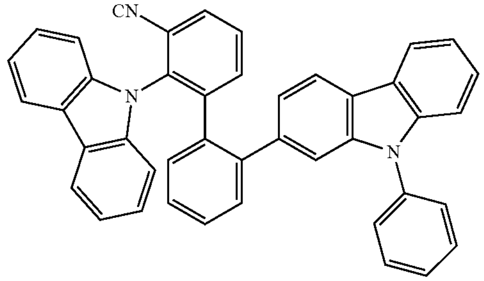
172
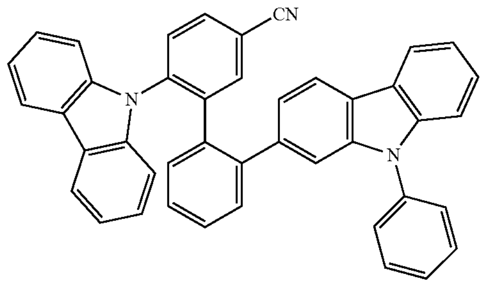
173
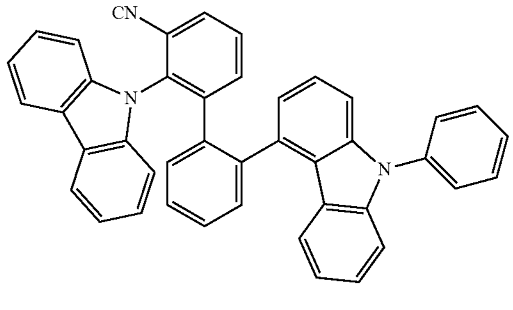
-continued
174
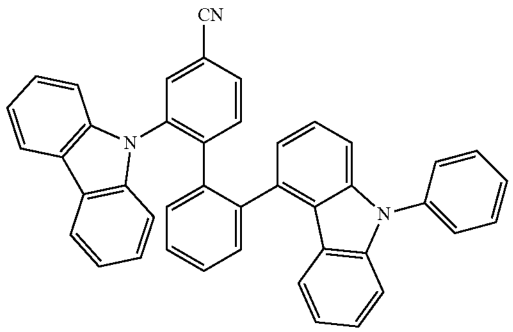
175
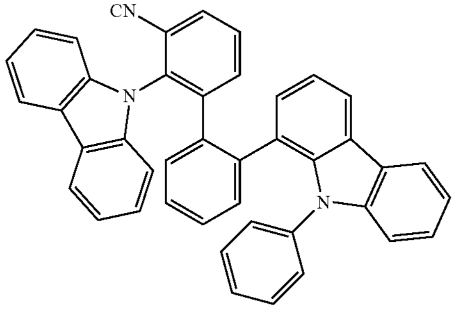
176
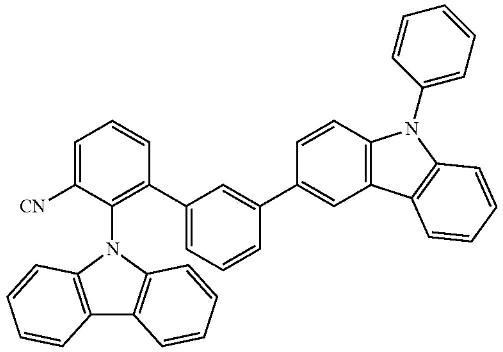
177
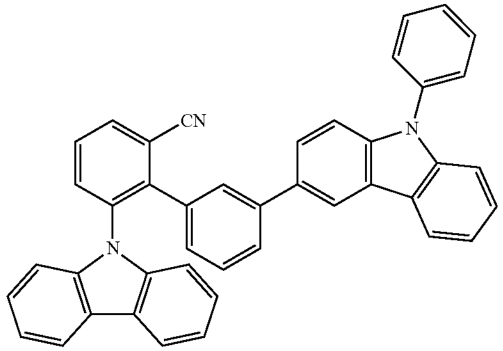

-continued
178
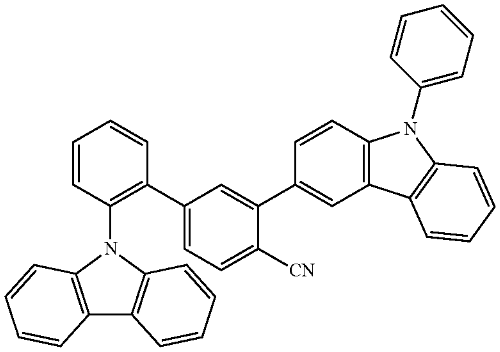
179
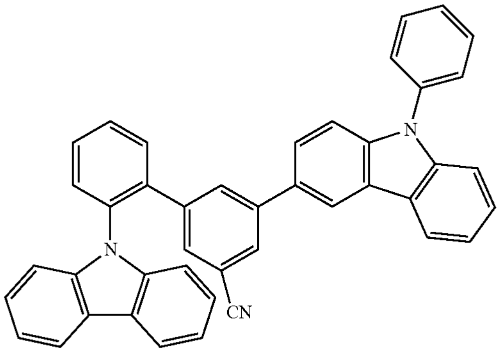
180
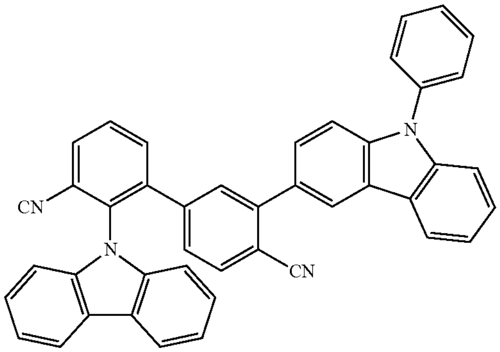
181
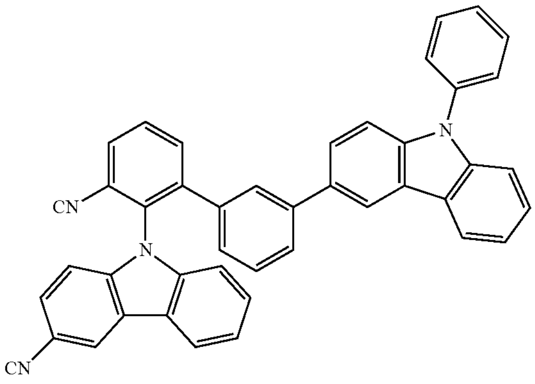
-continued
182
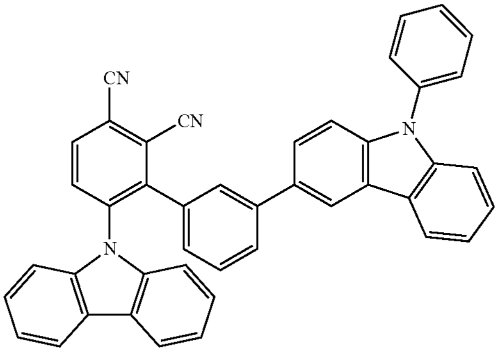
183
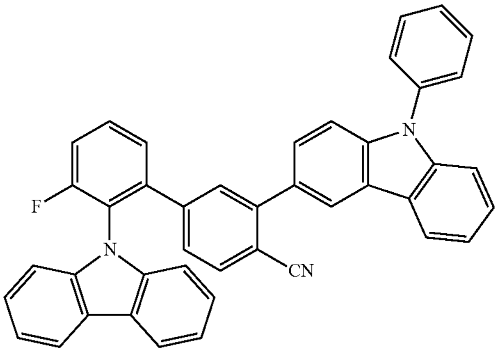
184
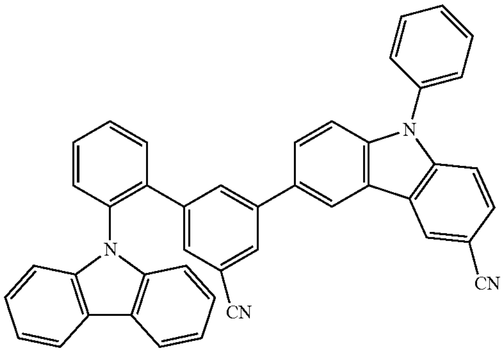
185
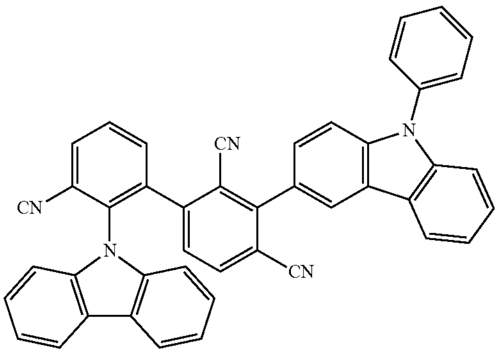

-continued
186
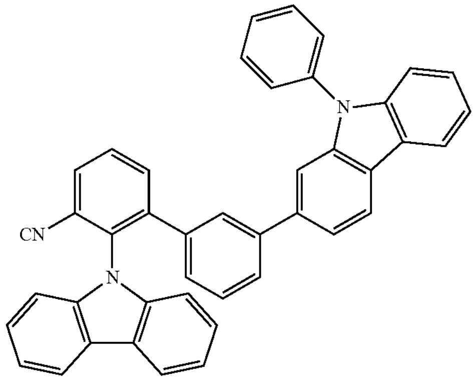
187
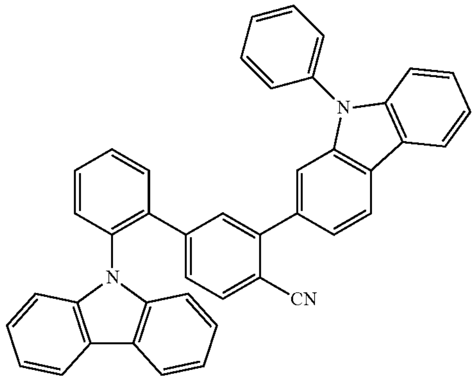
188
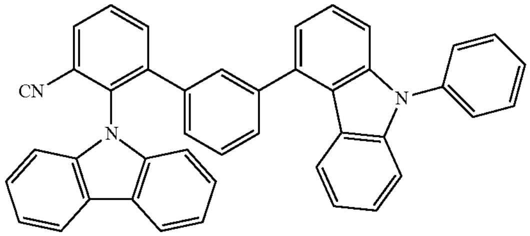
189
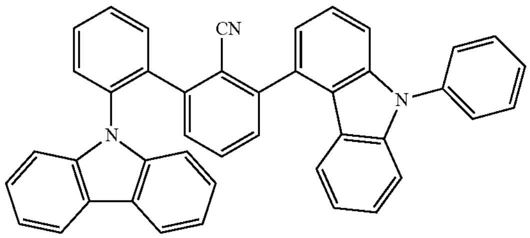
190
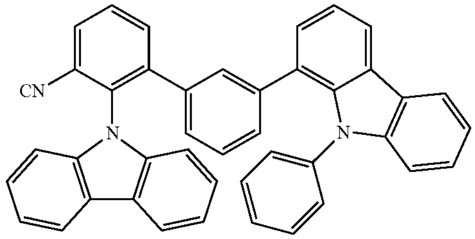
-continued
191
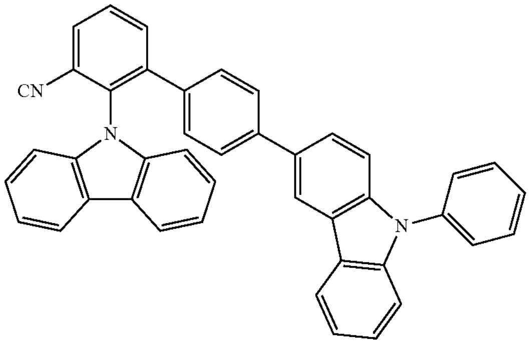
192
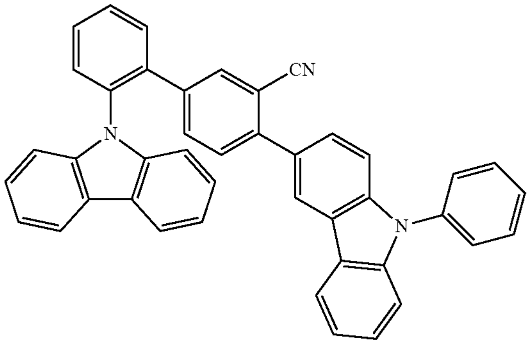
193
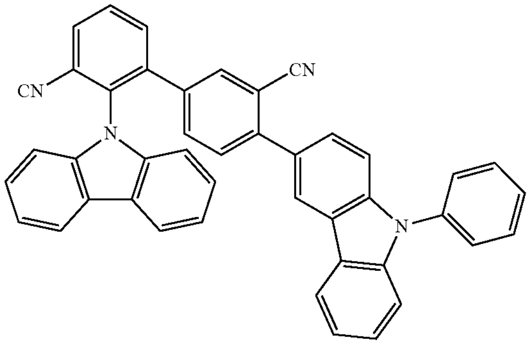
194
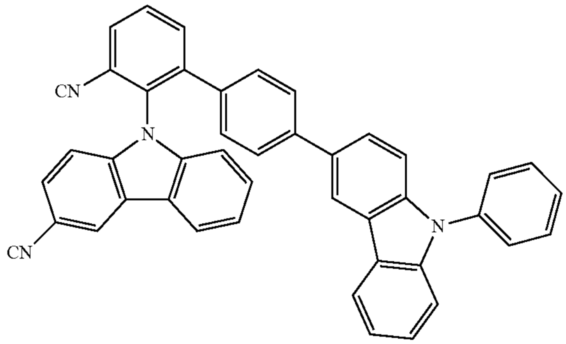

-continued
195
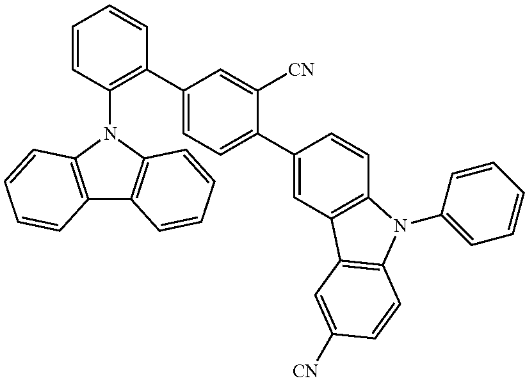
196
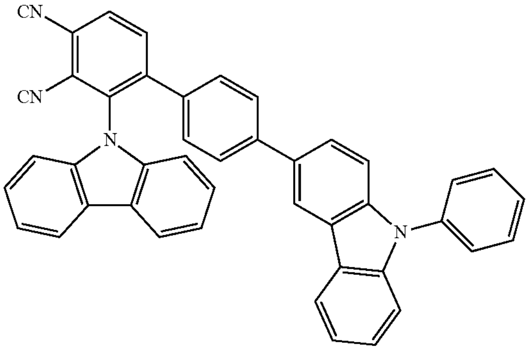
197
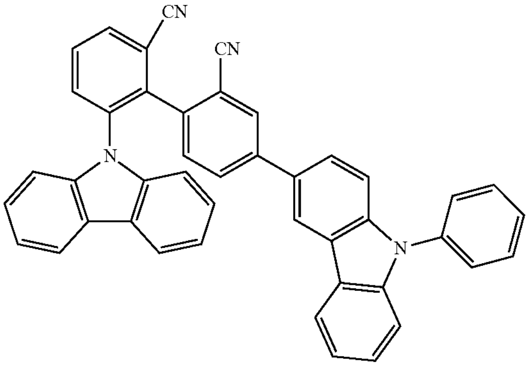
198
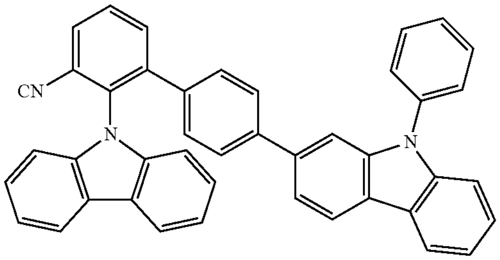
-continued
199
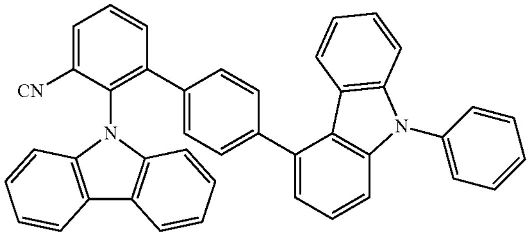
200
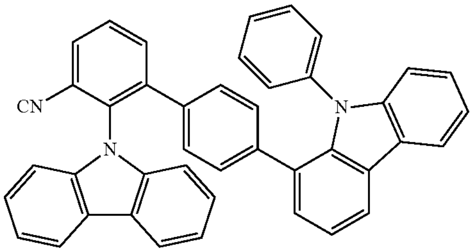
201
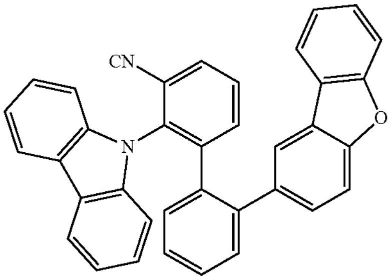
202
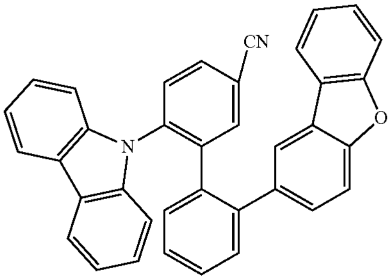
203
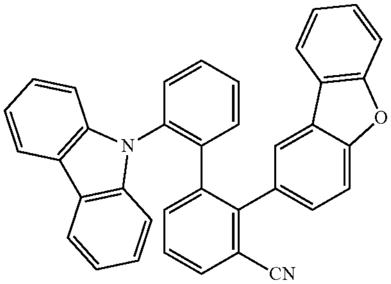

-continued
204
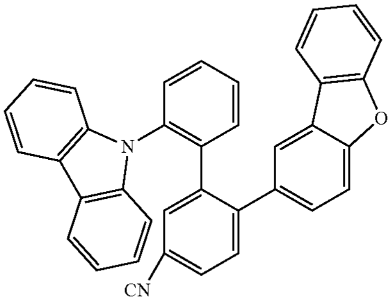
205
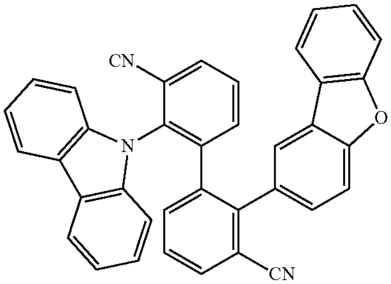
206
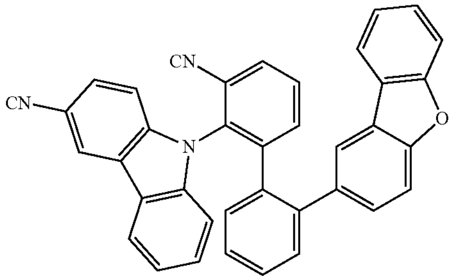
207
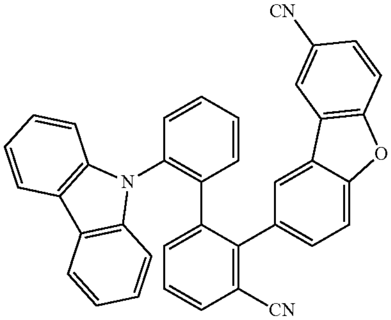
208
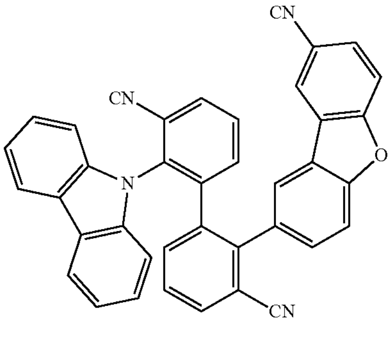
-continued
209
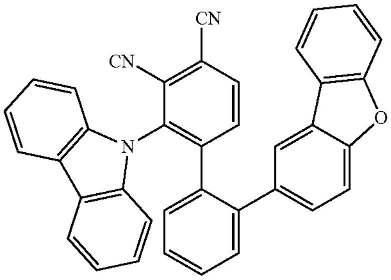
210
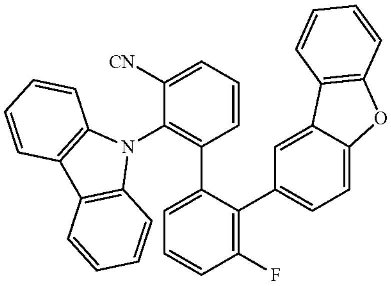
211
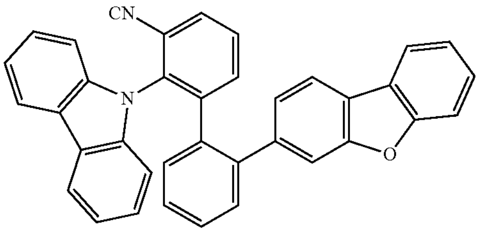
212
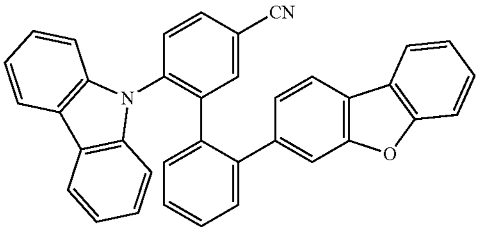
213
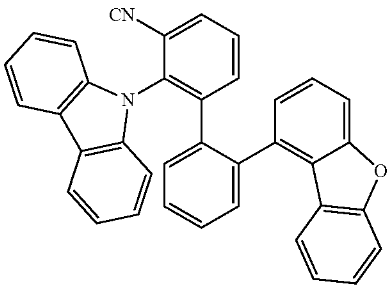

-continued
214
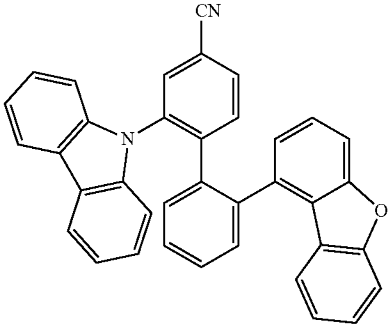
215
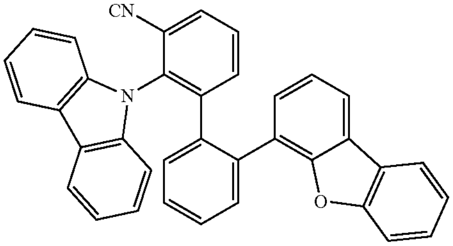
216
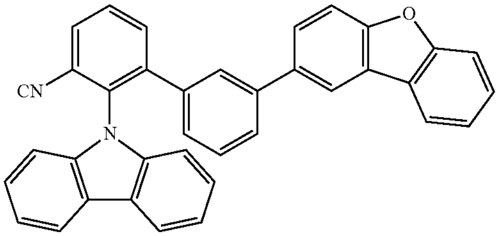
217
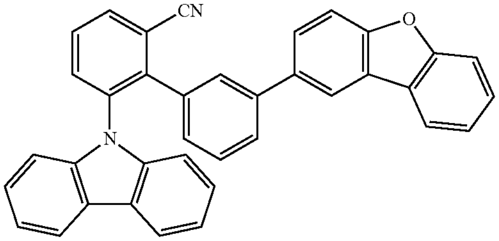
218
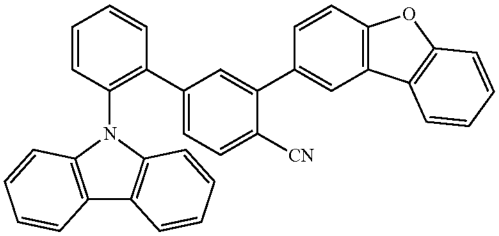
219
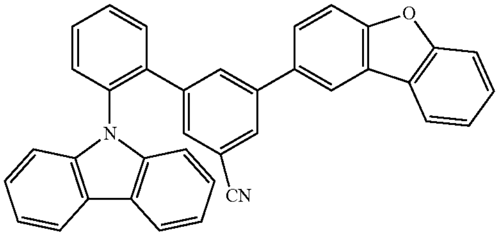
-continued
220
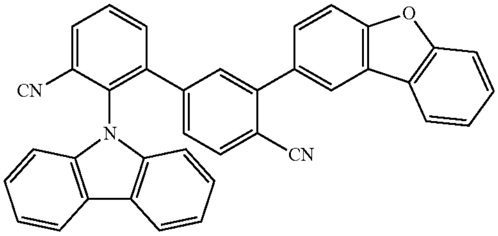
221
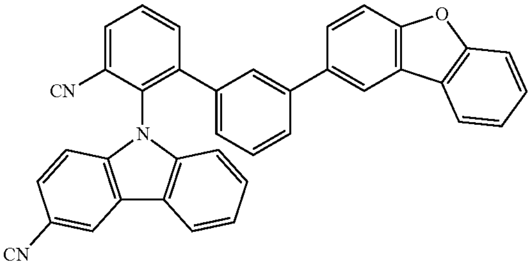
222
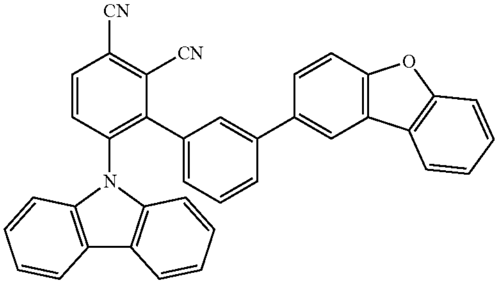
223
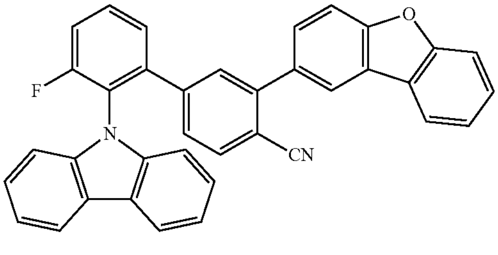
224
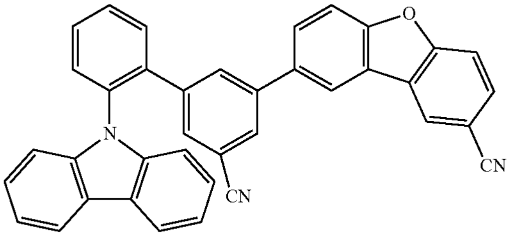
225
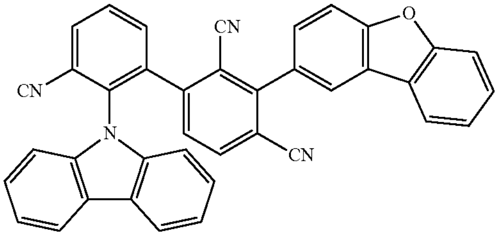

-continued
226
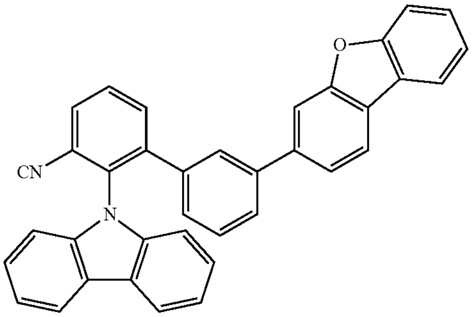
227
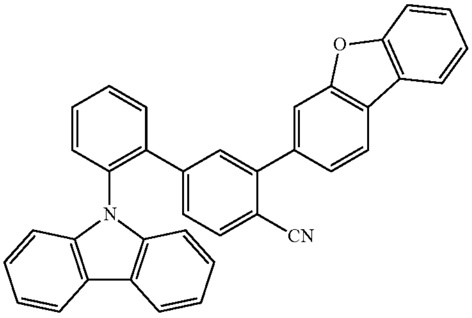
228
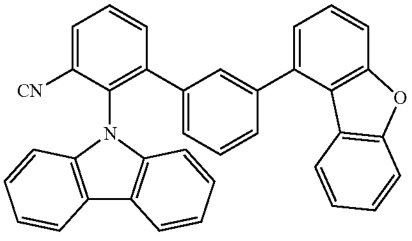
229
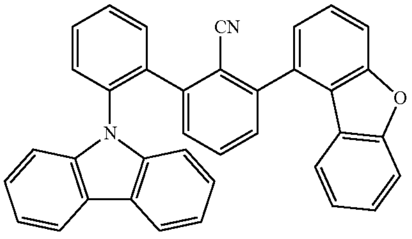
230
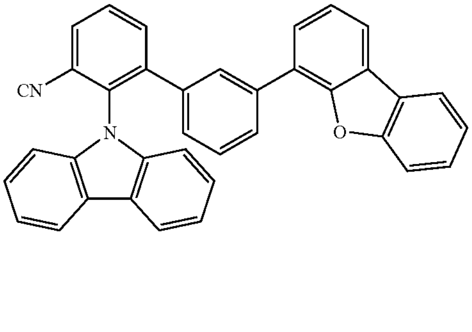
-continued
231
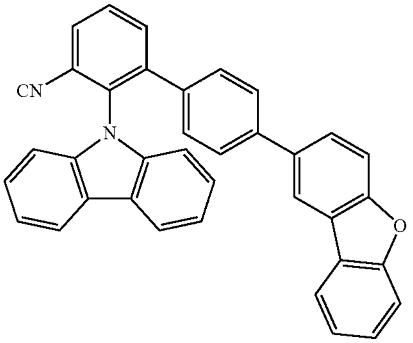
232
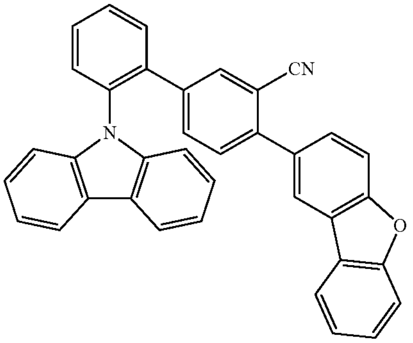
233
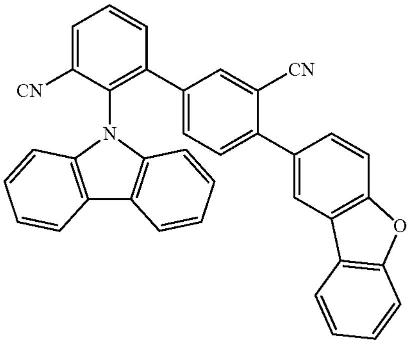
234
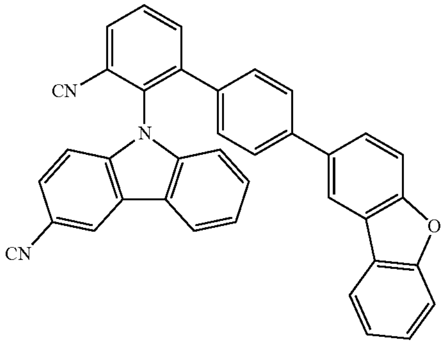

-continued
235
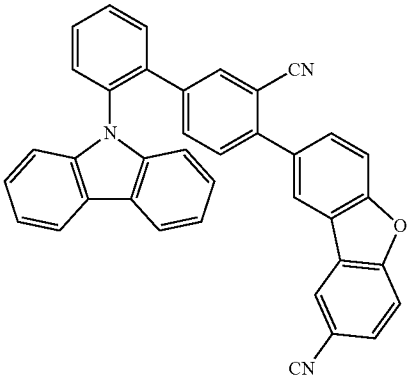
236
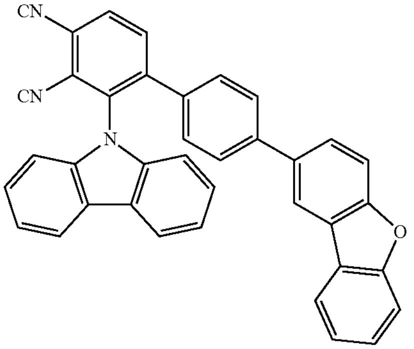
237
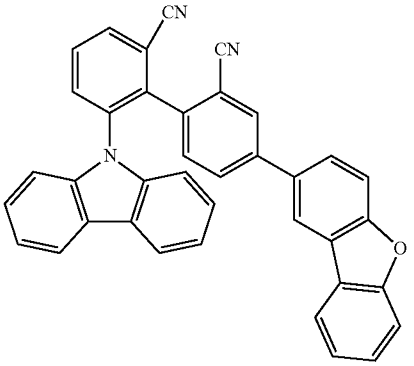
238
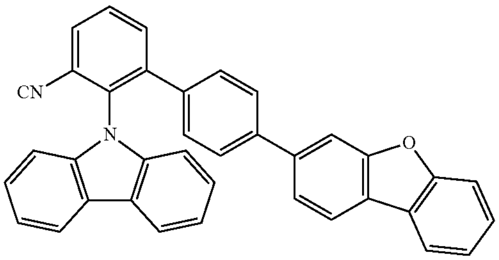
239
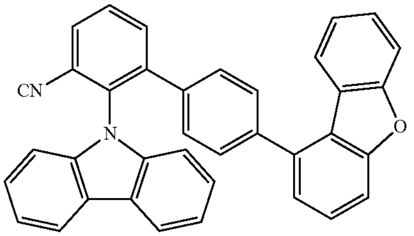
-continued
240
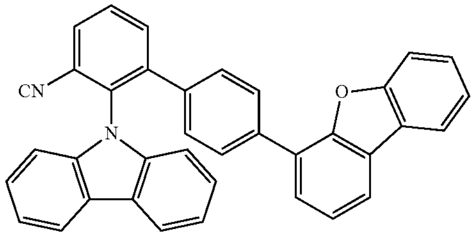
241
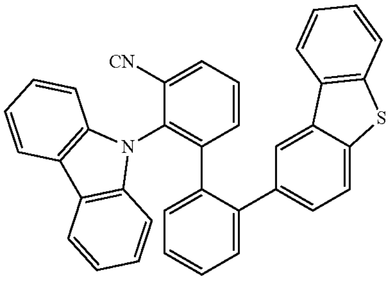
242
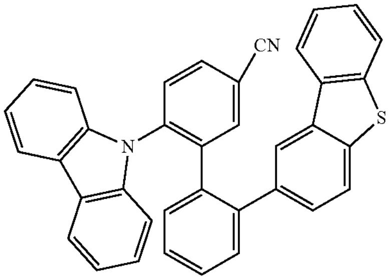
243
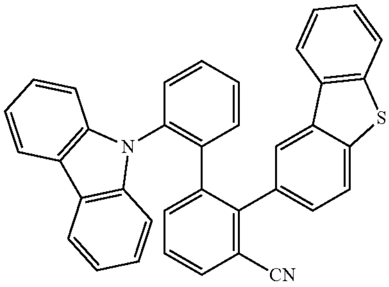
244
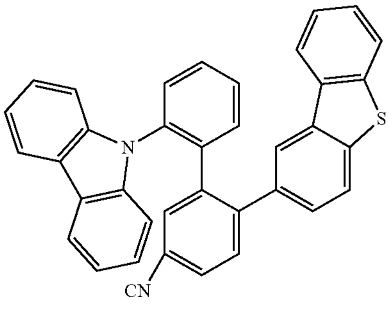

-continued
245
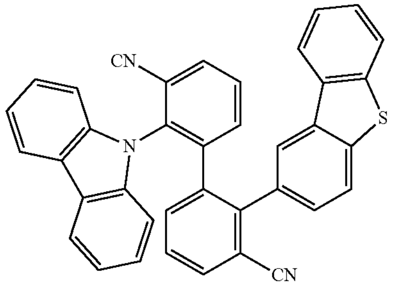
246
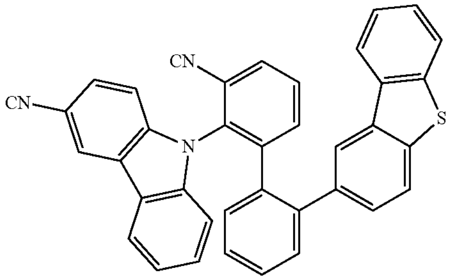
247
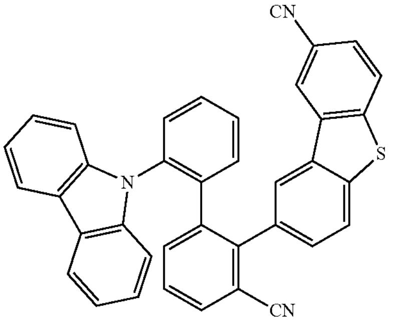
248
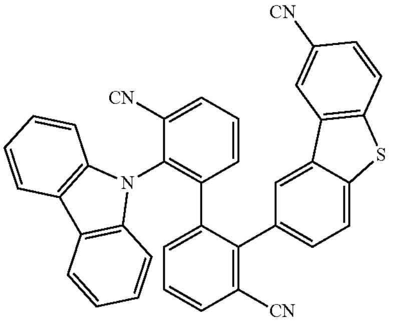
249
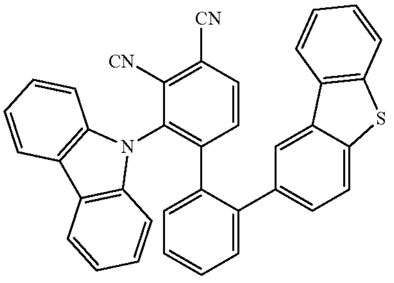
-continued
250
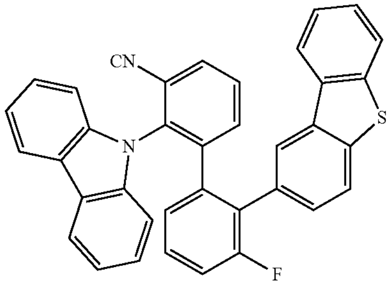
251
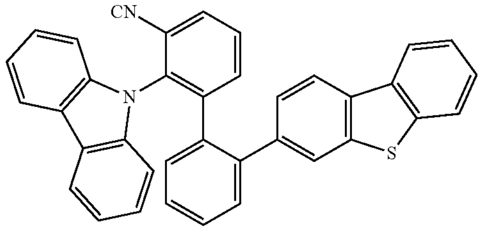
252
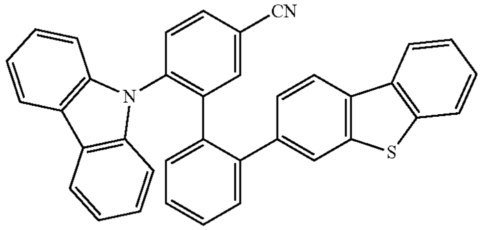
253
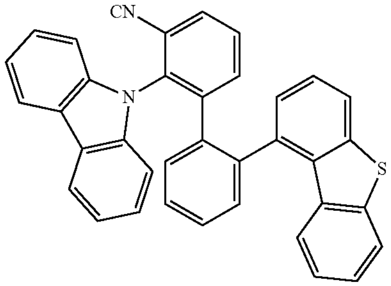
254
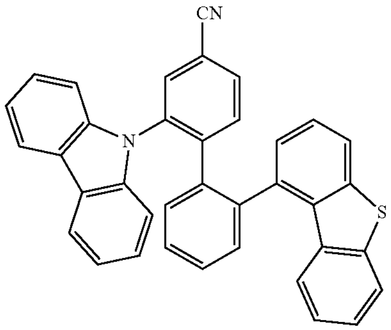
255
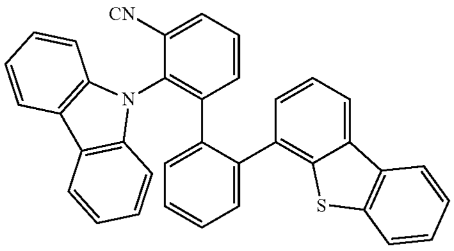

-continued
256
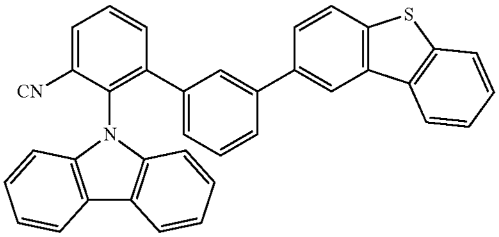
257
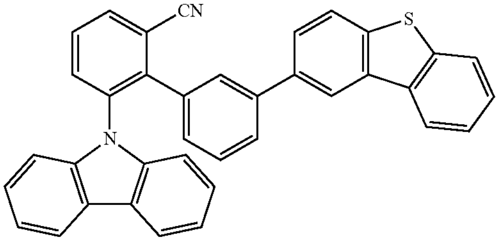
258
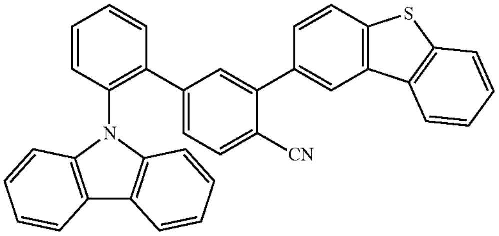
259
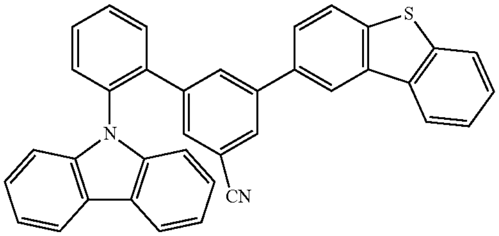
260
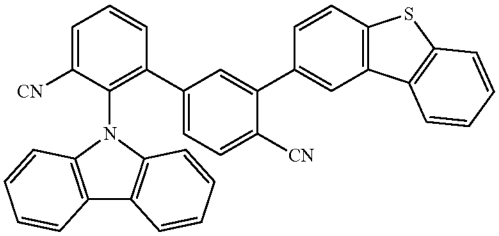
261
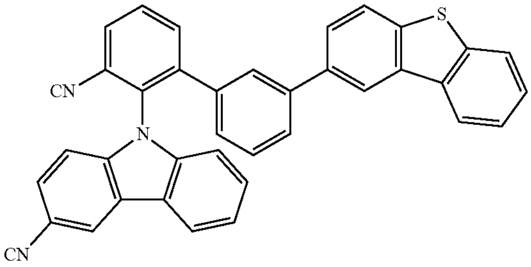
-continued
262
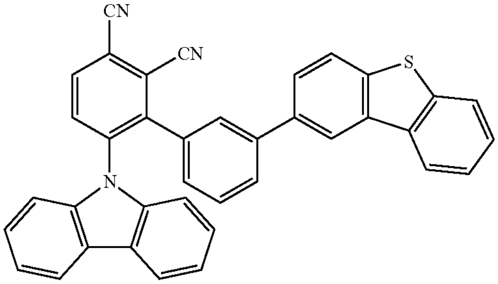
263
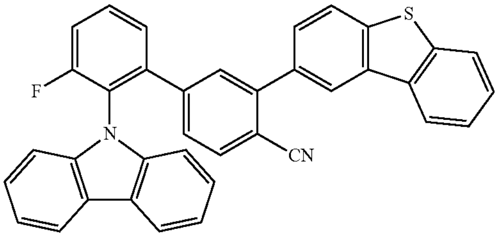
264
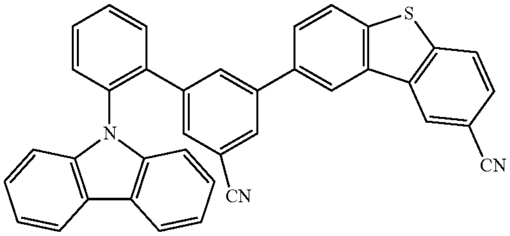
265
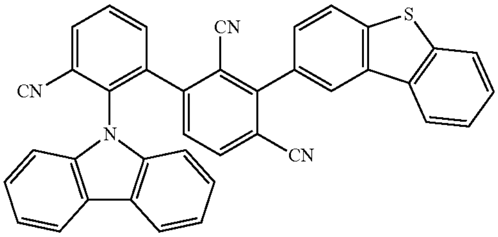
266
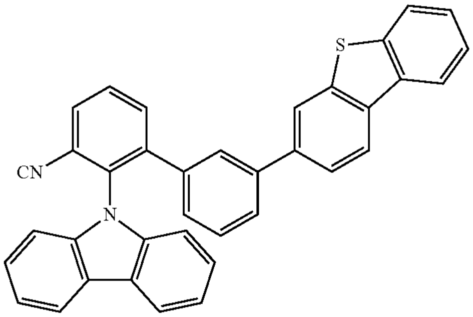

-continued
267
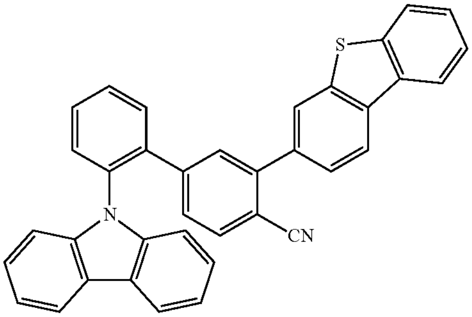
268
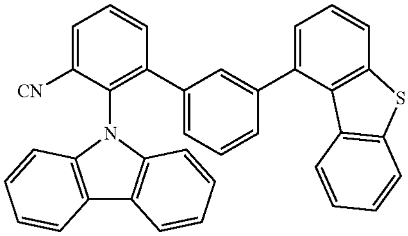
269
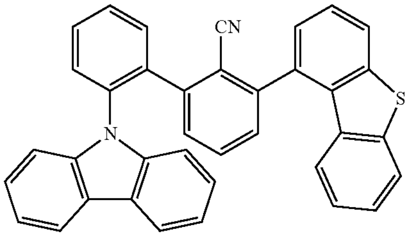
270
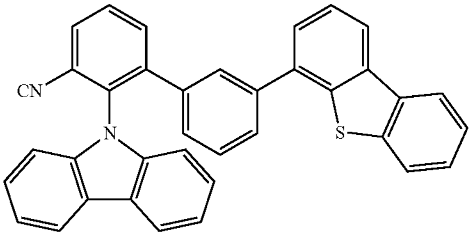
271
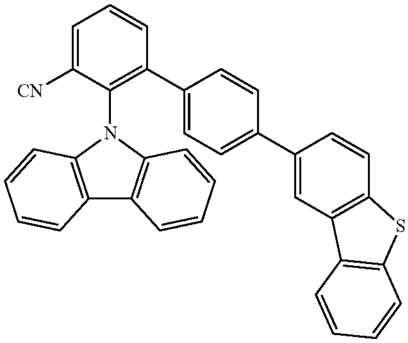
-continued
272
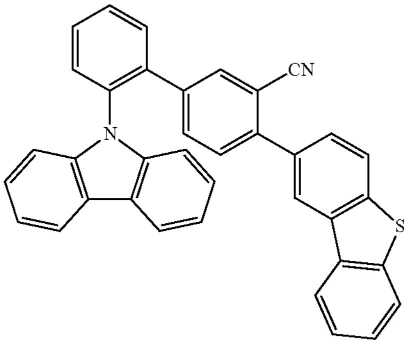
273
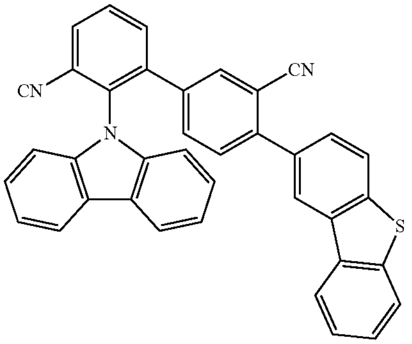
274
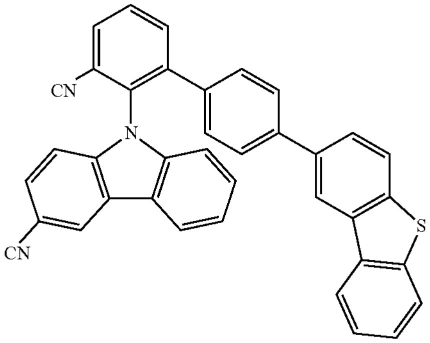
275
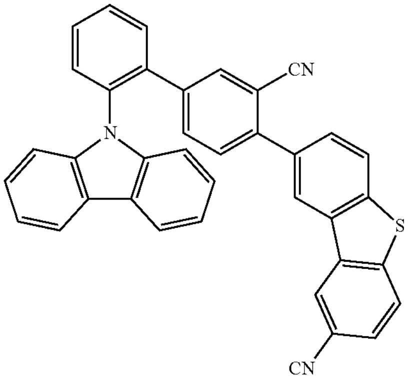

-continued
276
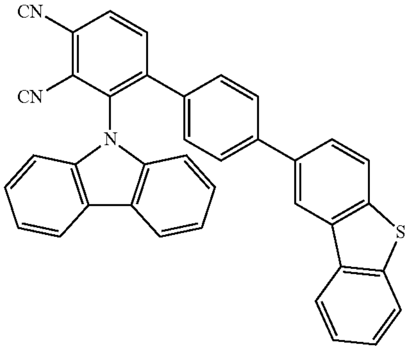
277
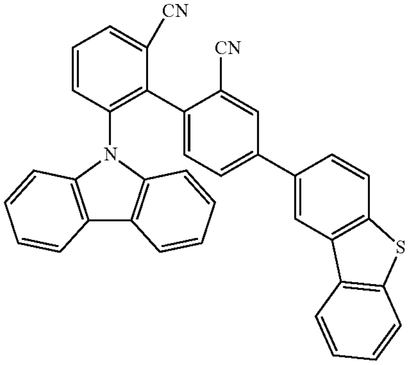
278
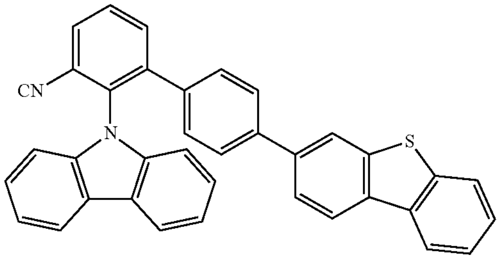
279
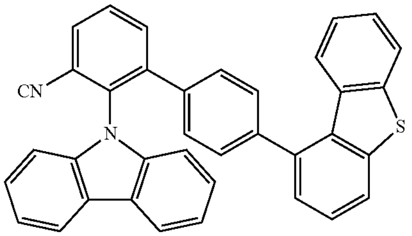
280
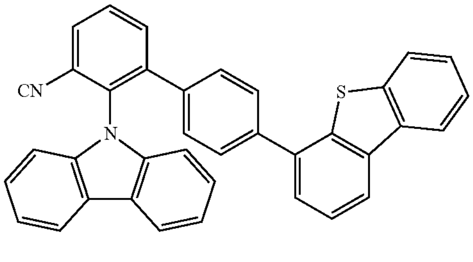
-continued
281
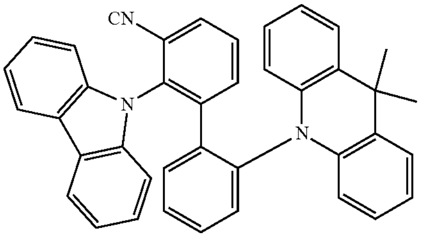
282
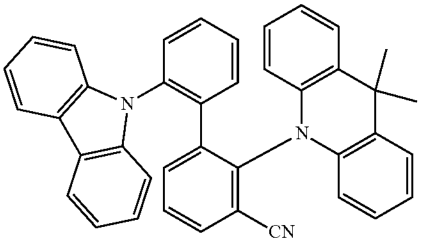
283
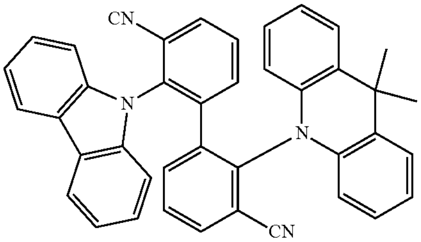
284
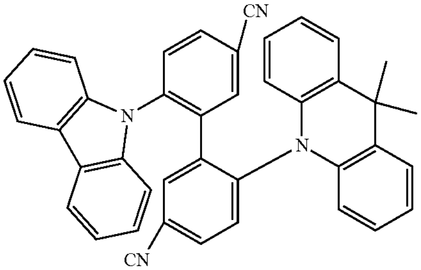
285
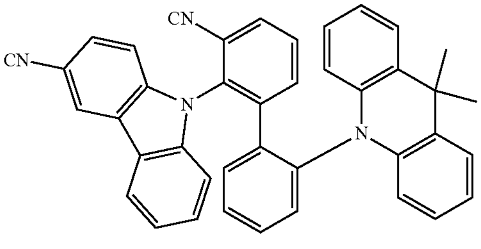
286
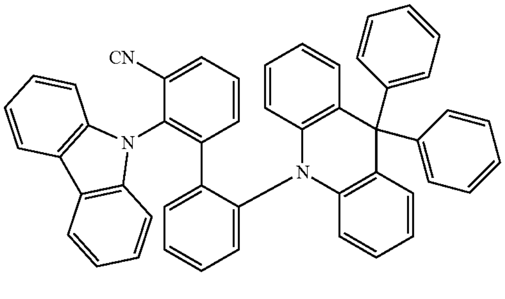

-continued
287
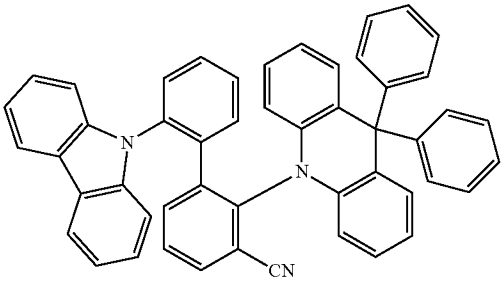
288
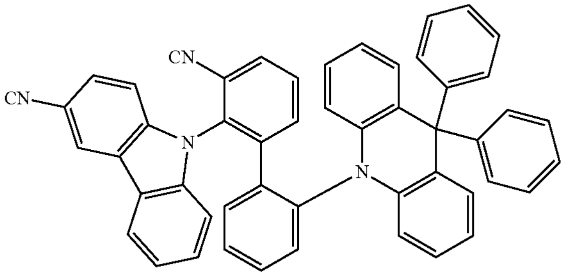
289
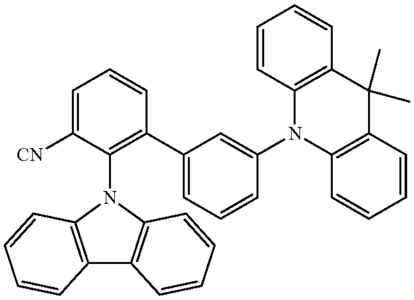
290
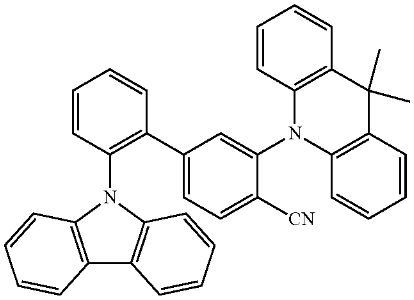
291
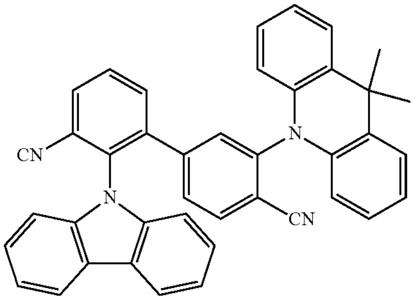
-continued
292
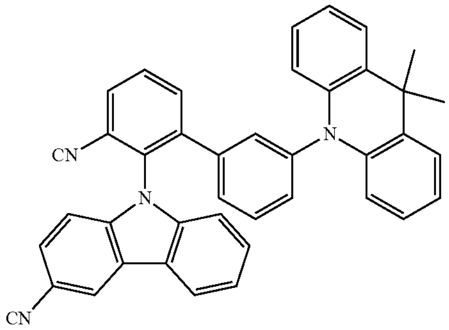
293
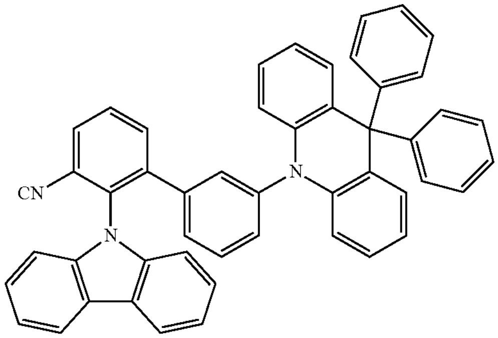
294
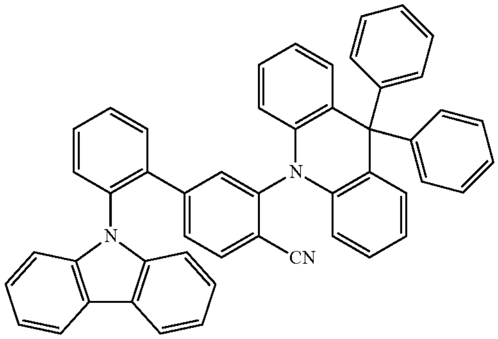
295
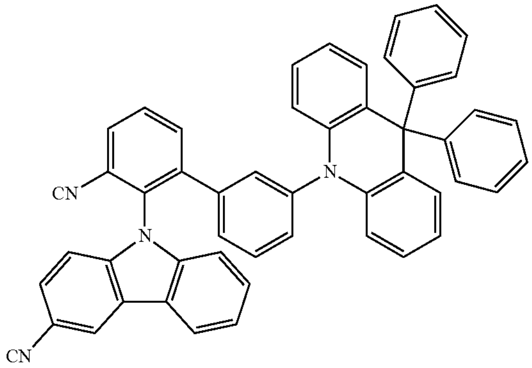

-continued
296
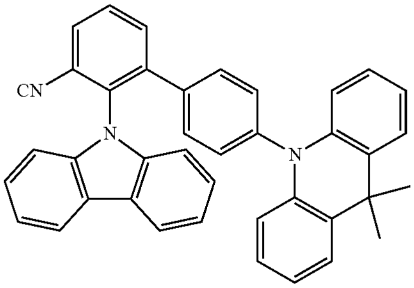
297
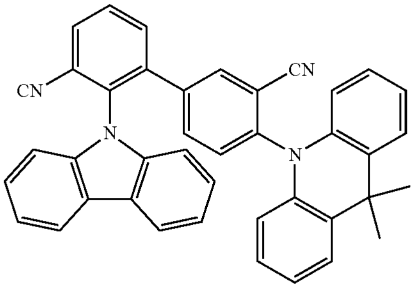
298
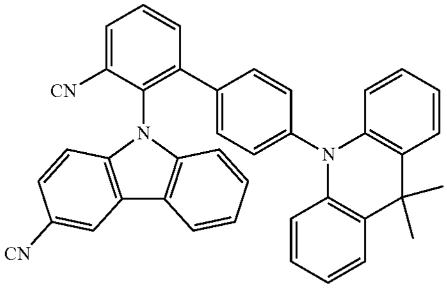
299
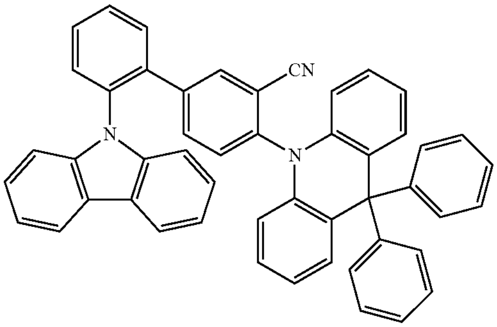
300
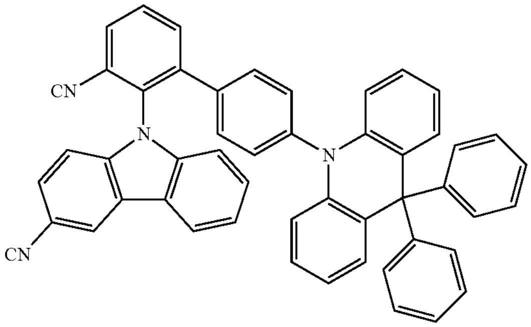
-continued
301
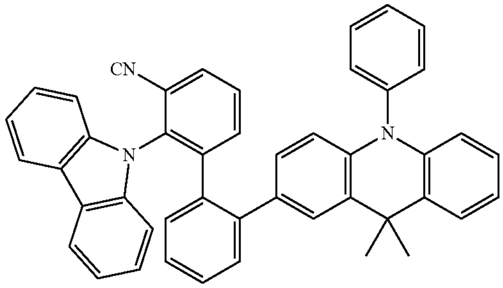
302
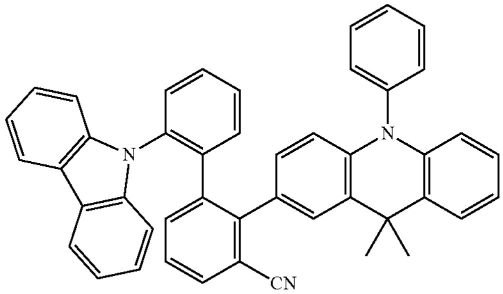
303
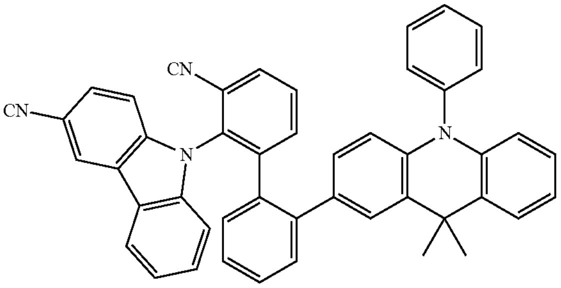
304
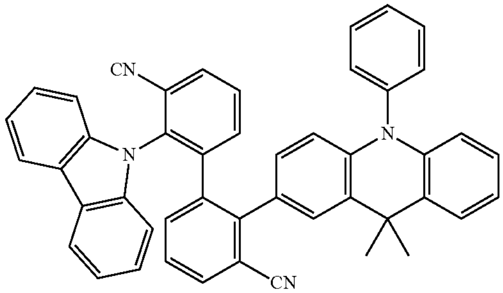
305
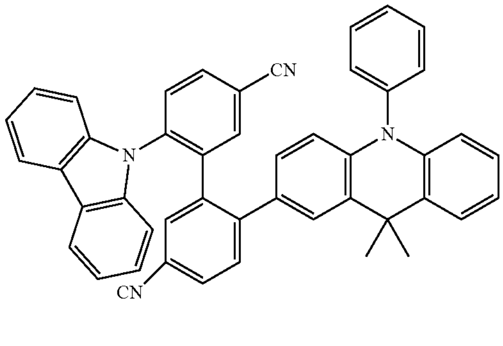

-continued
306
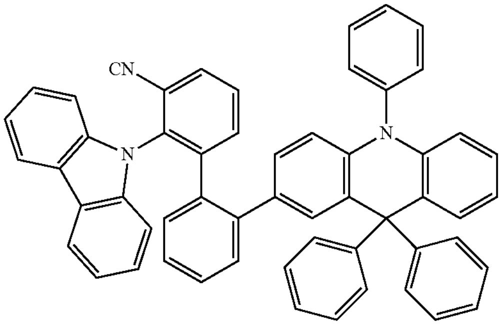
307
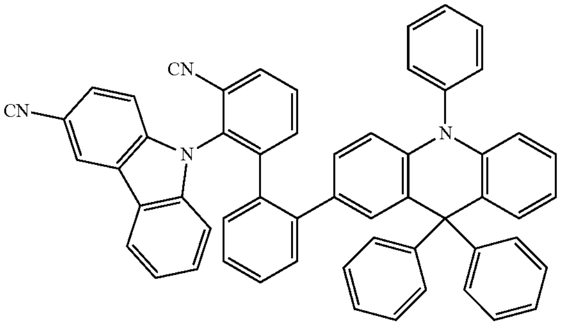
308
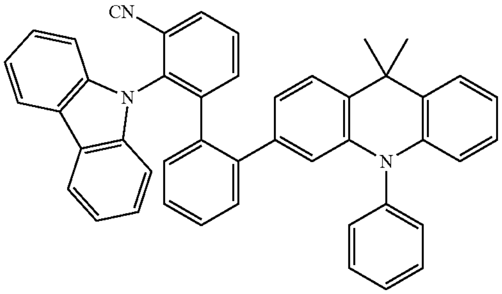
309
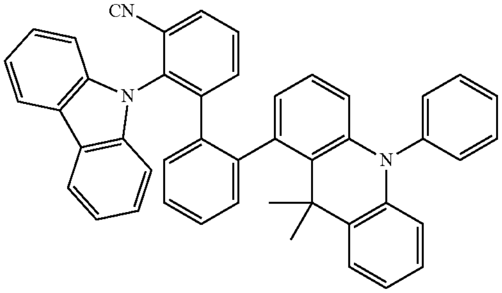
310
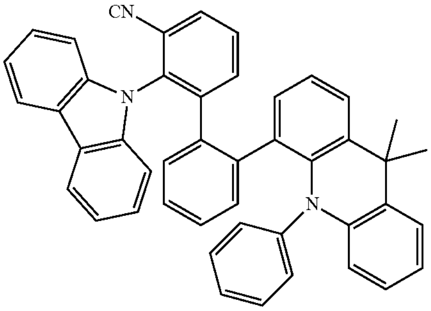
-continued
311
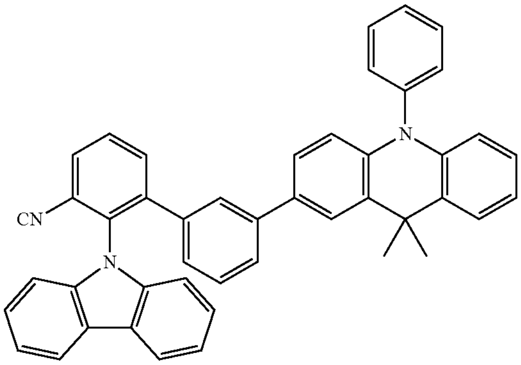
312
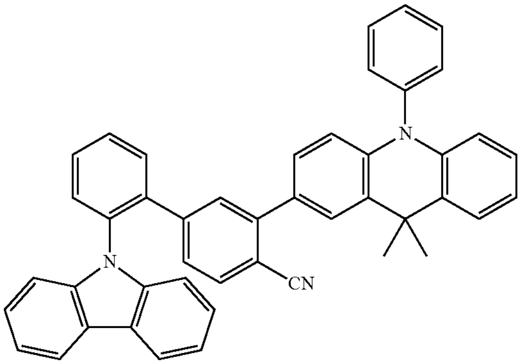
313
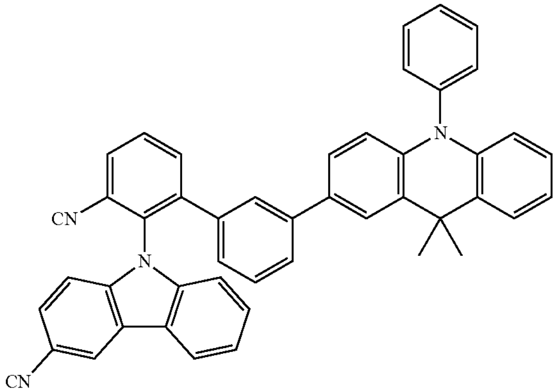
314
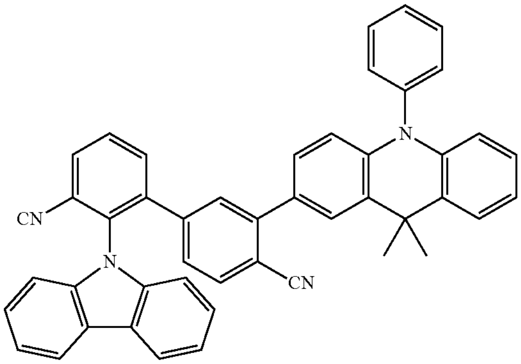

-continued
315
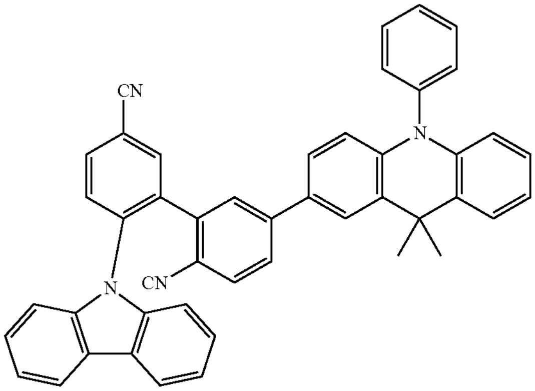
316
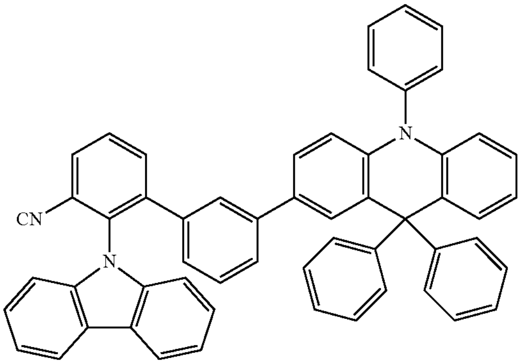
317
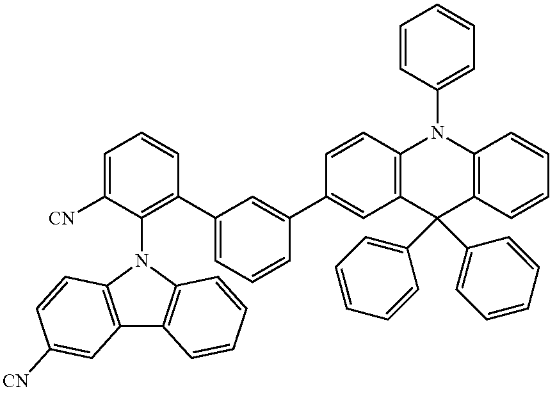
318
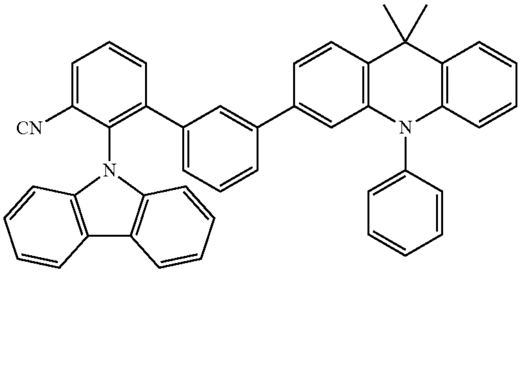
-continued
319
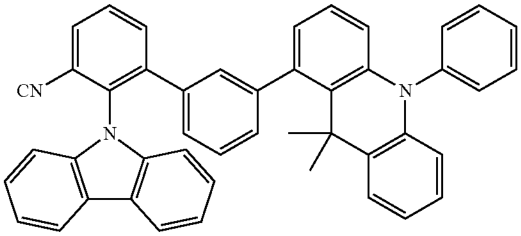
320
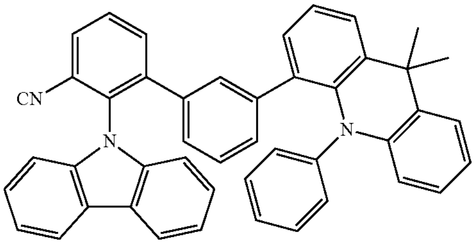
321
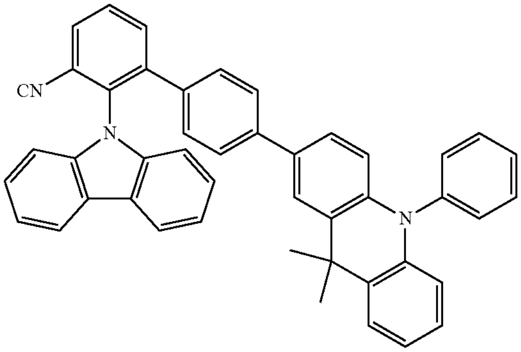
322
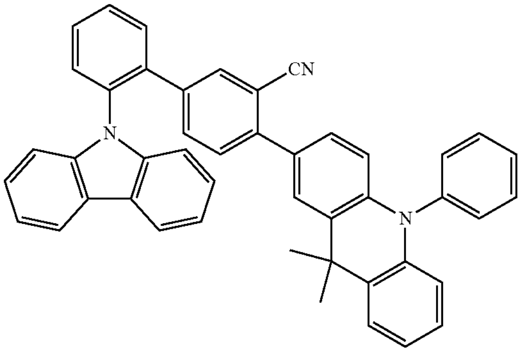
323
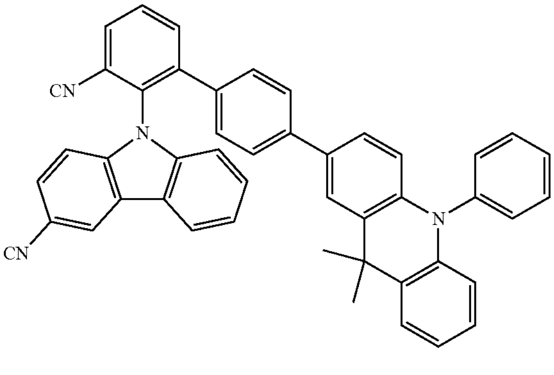

-continued
324
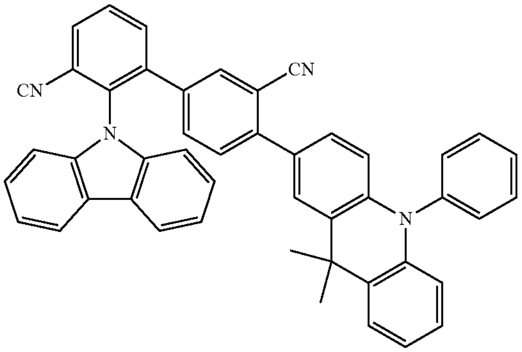
325
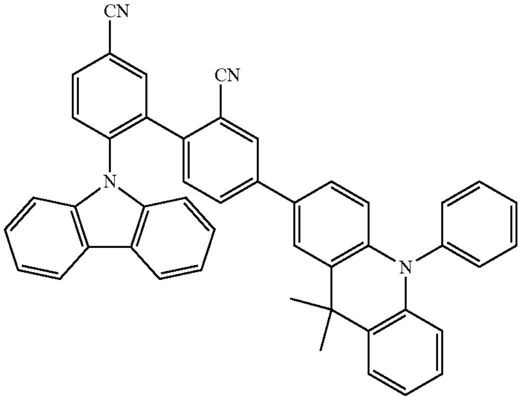
326
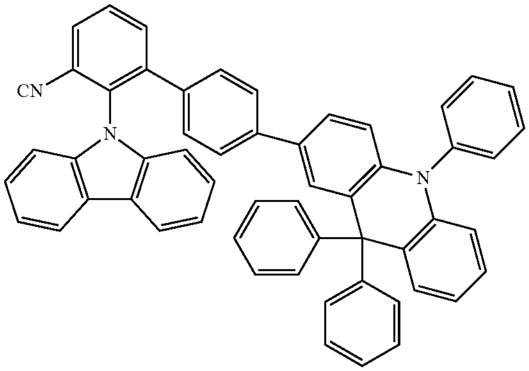
327
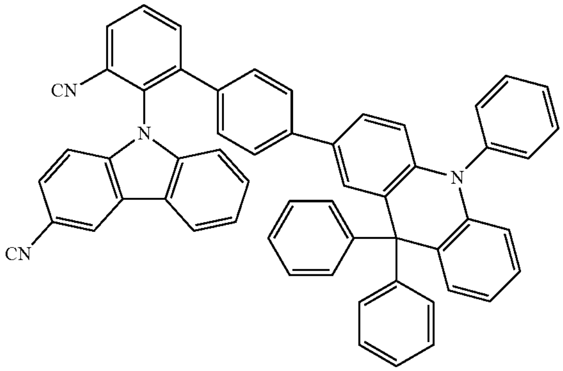
-continued
328
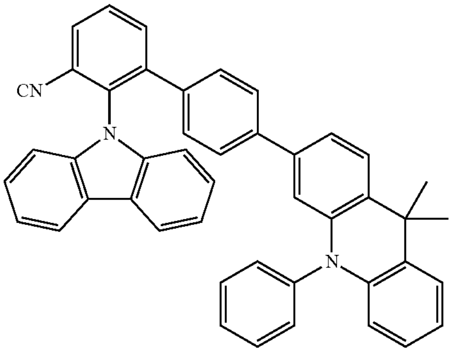
329
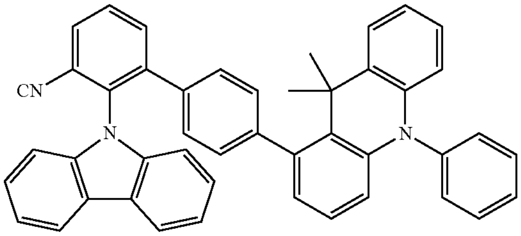
330
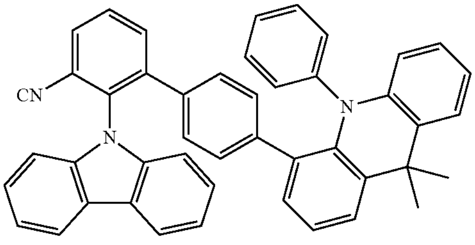
Group HE7
1
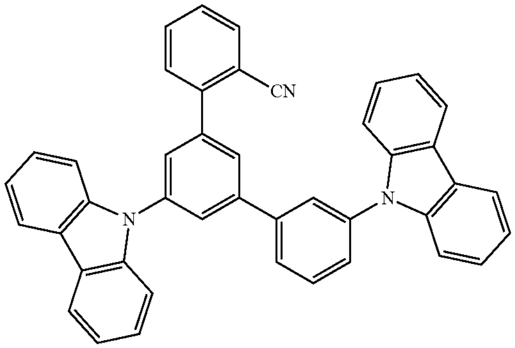

-continued
2
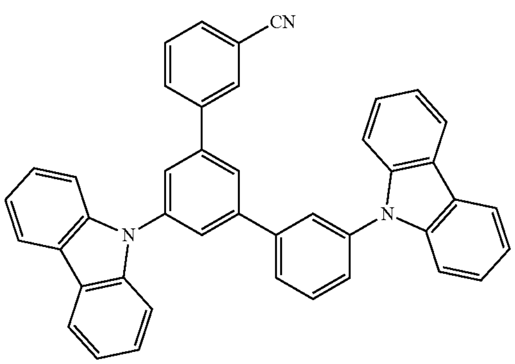
3
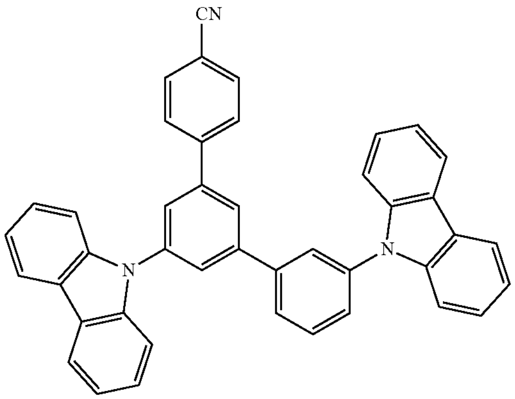
4
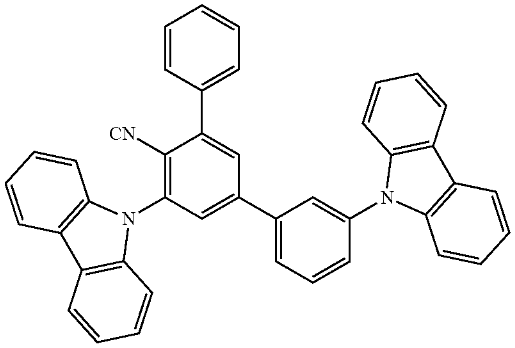
5
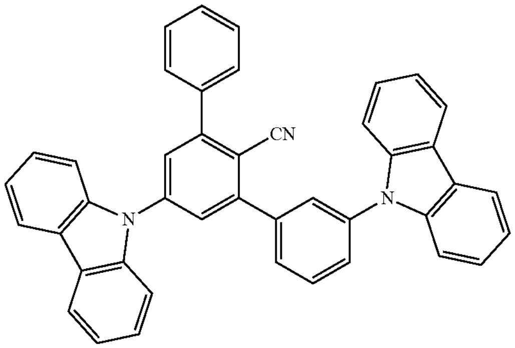
-continued
6
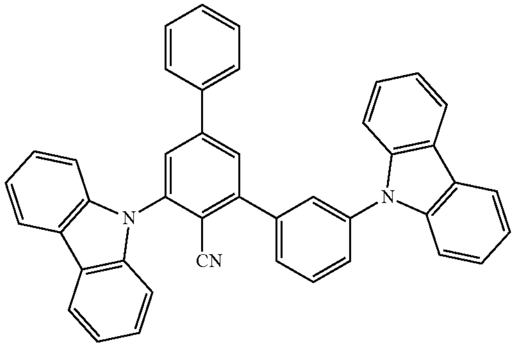
7
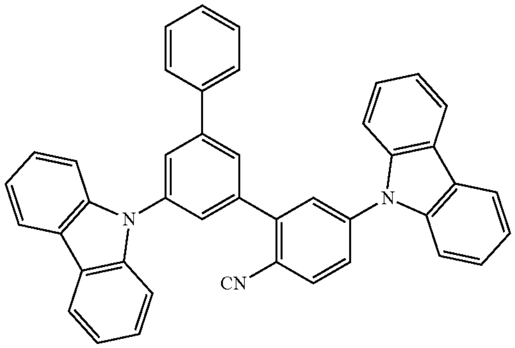
8
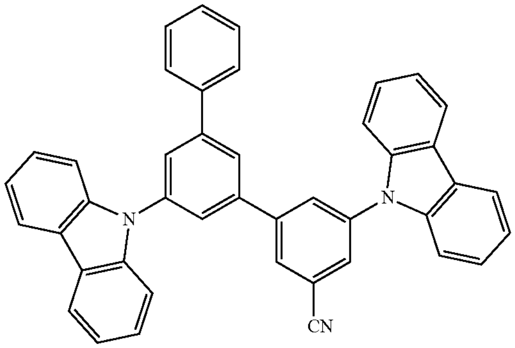
9
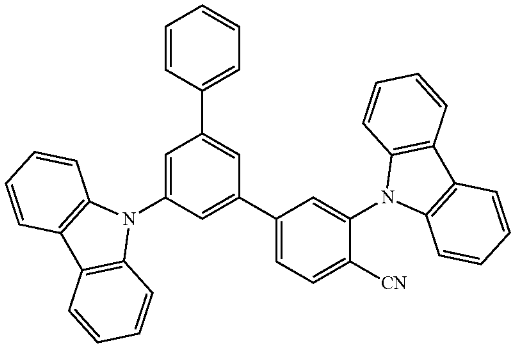

-continued
10
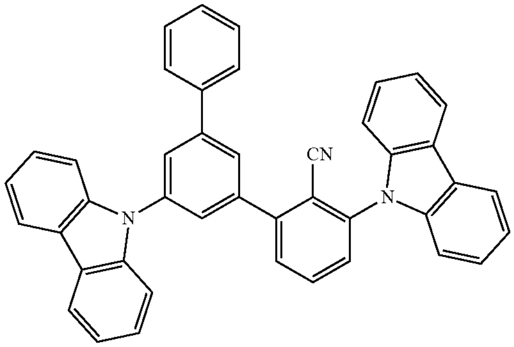
11
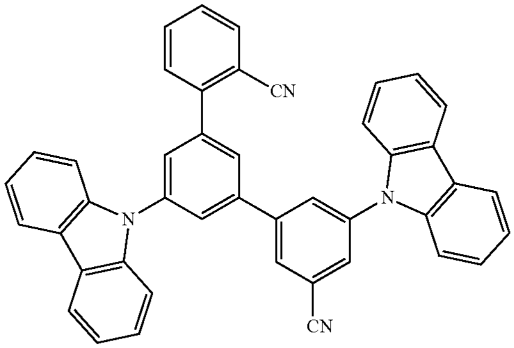
12
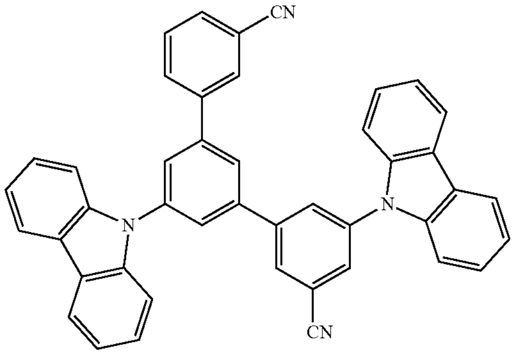
13
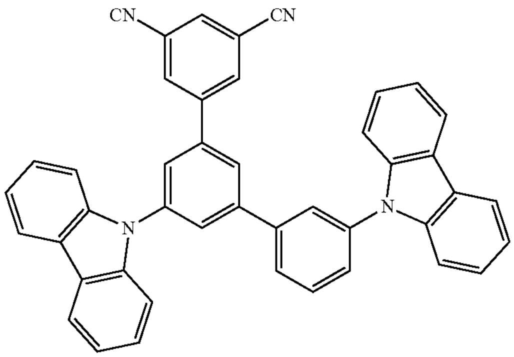
-continued
14
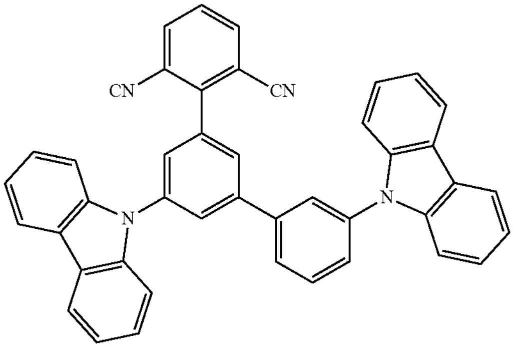
15
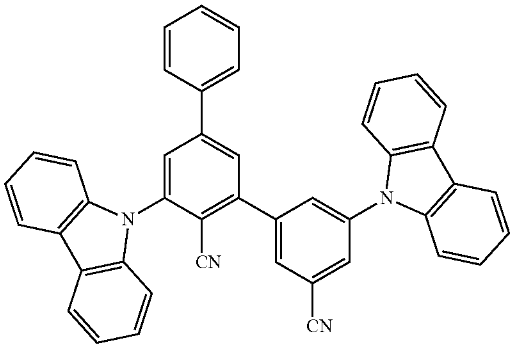
16
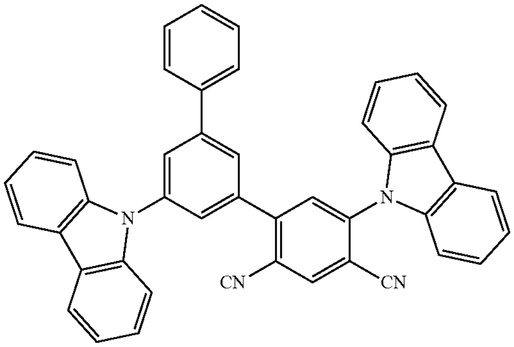
17
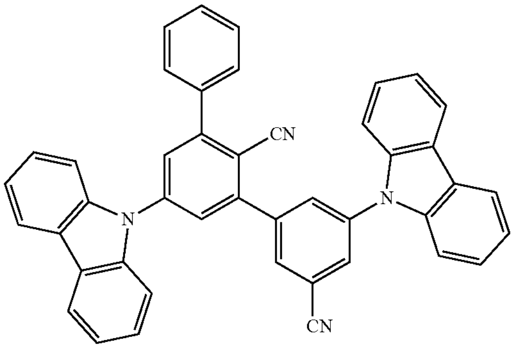

-continued
18
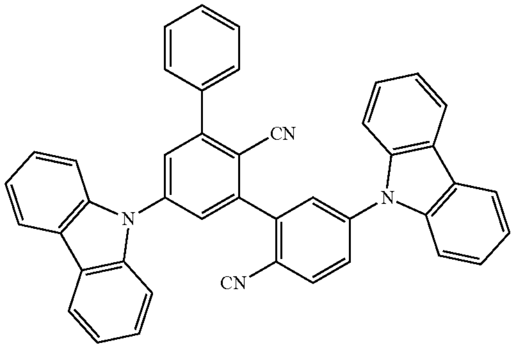
19
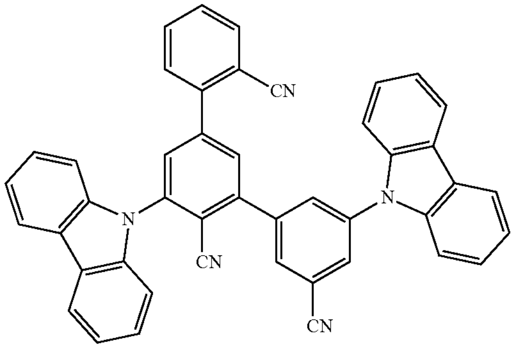
20
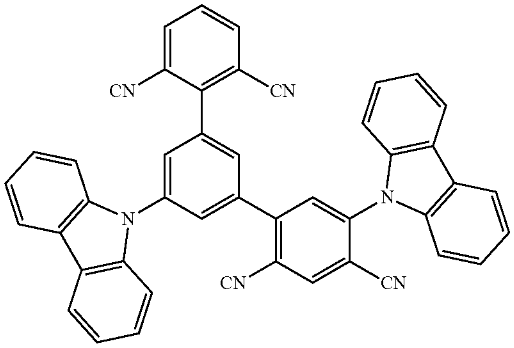
21
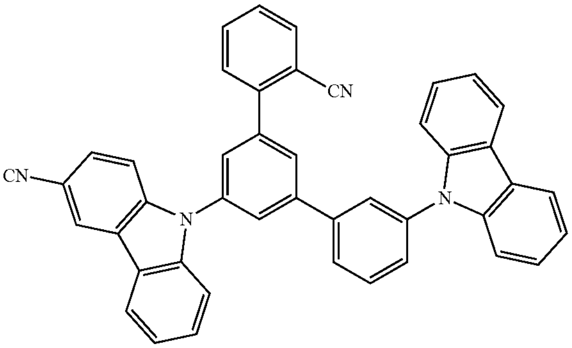
-continued
22
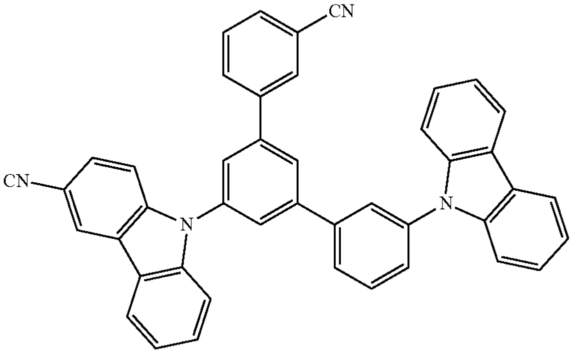
23
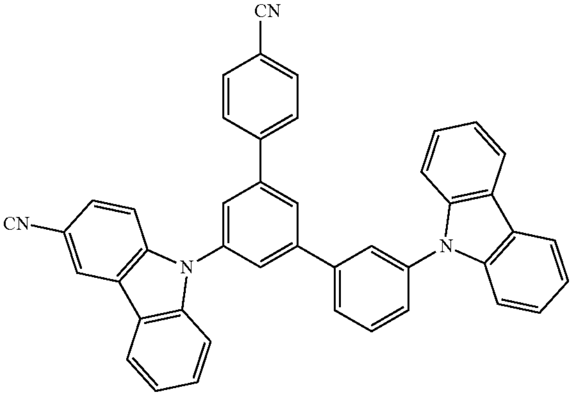
24
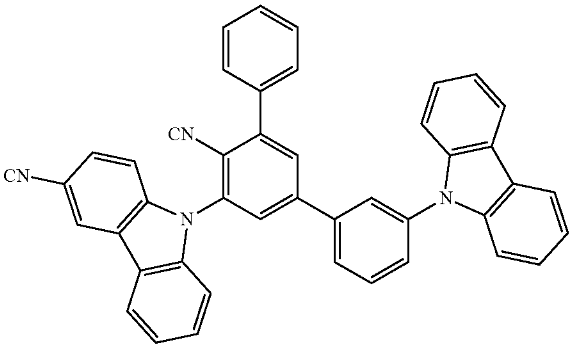
25
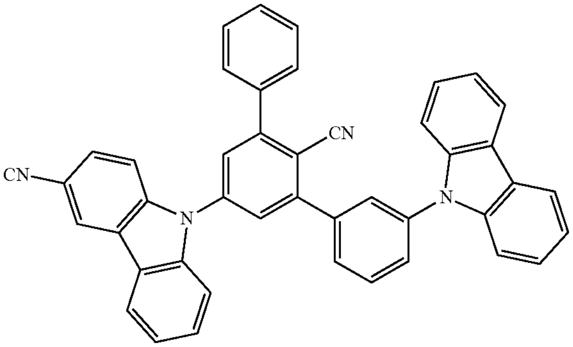

-continued
26
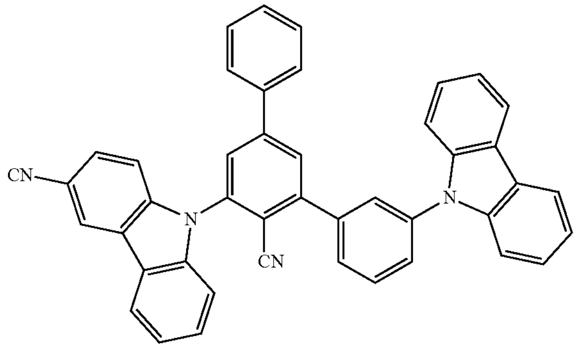
27
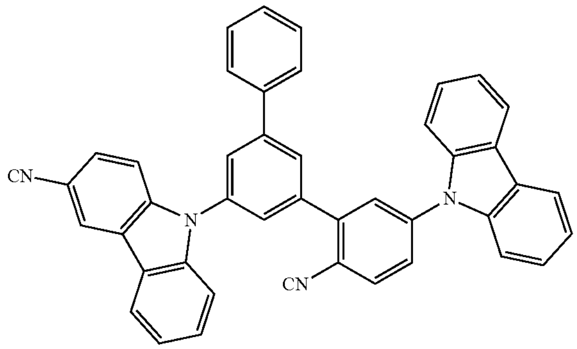
28
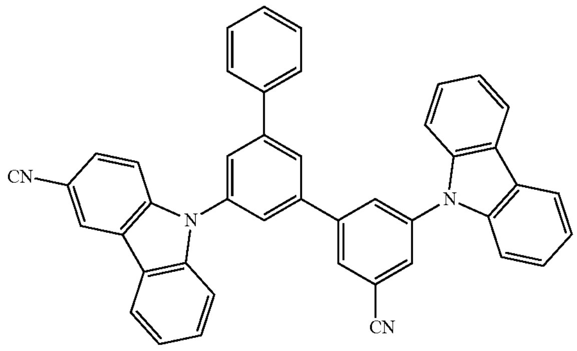
29
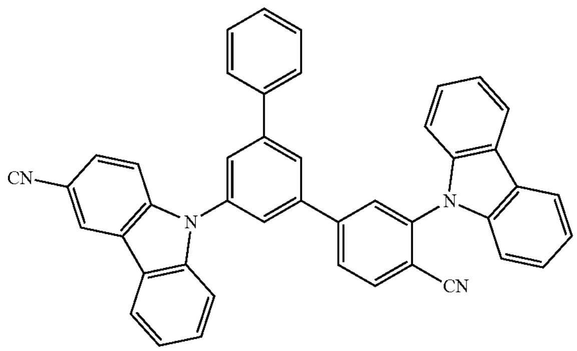
-continued
30
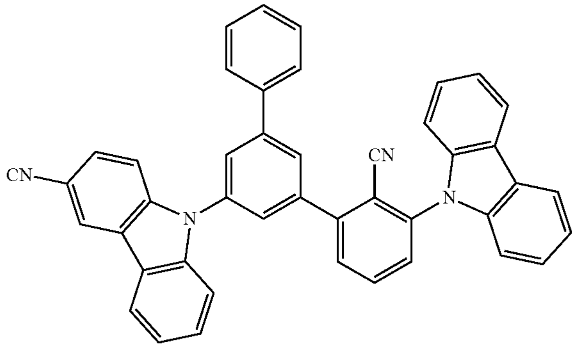
31
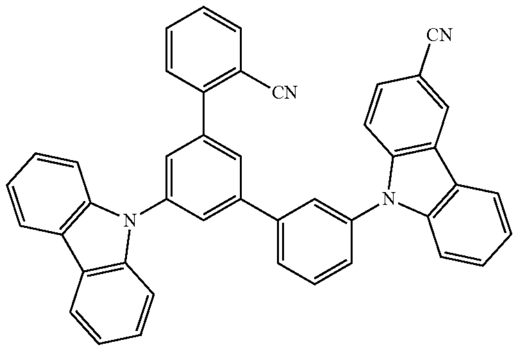
32
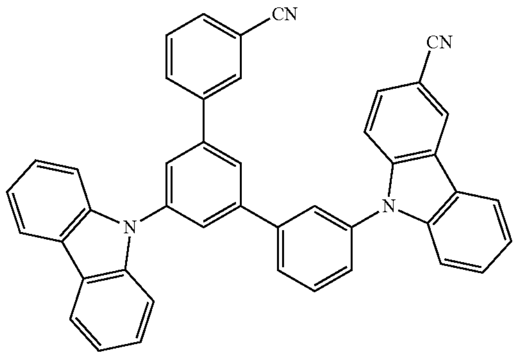
33
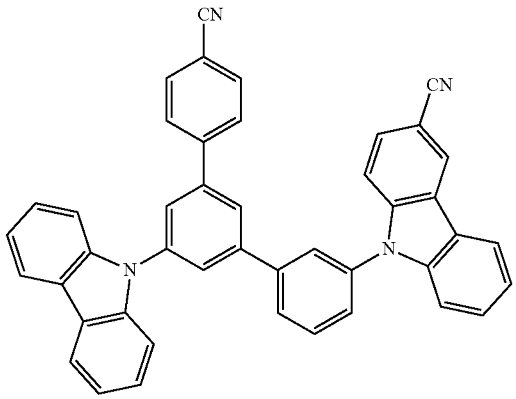

-continued
34
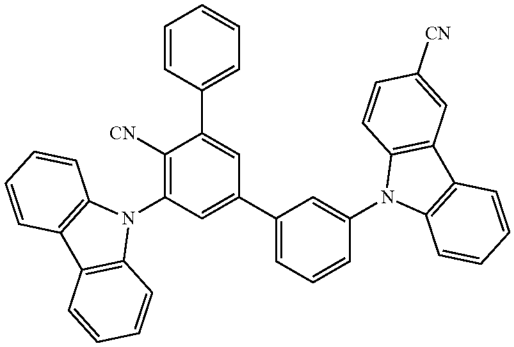
35
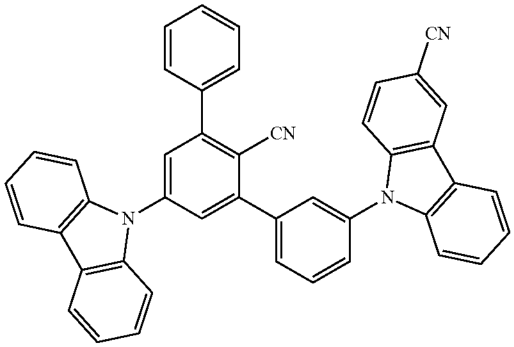
36
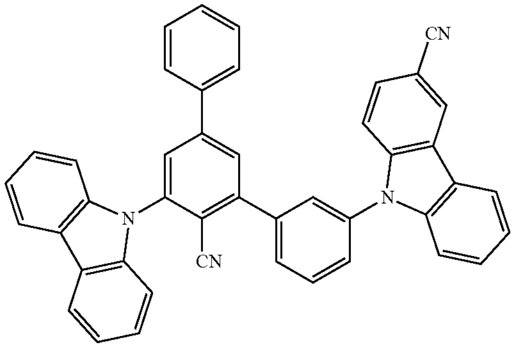
37
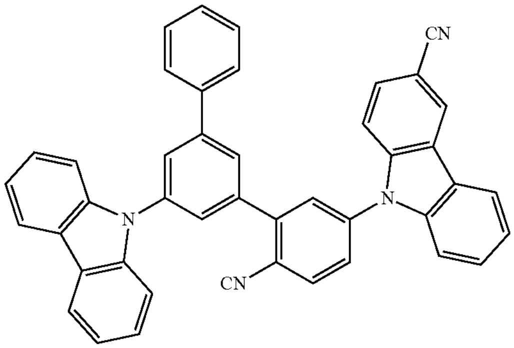
-continued
38
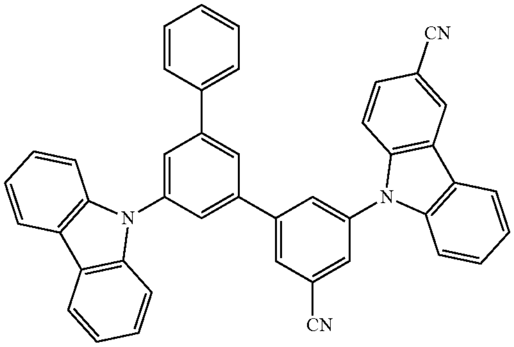
39
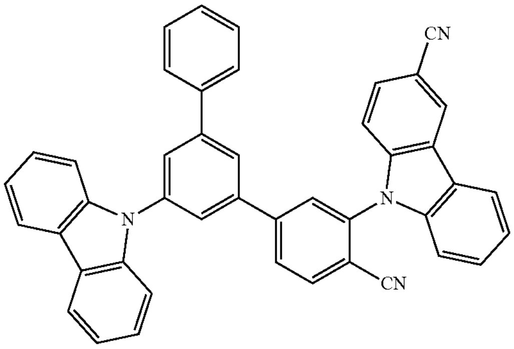
40
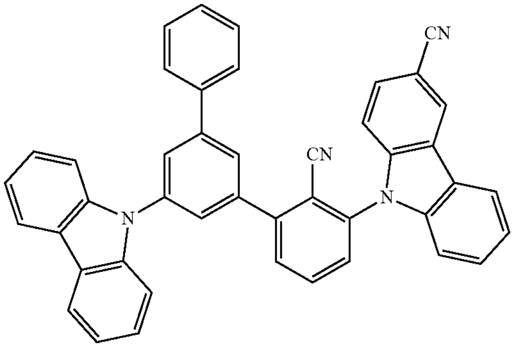
41
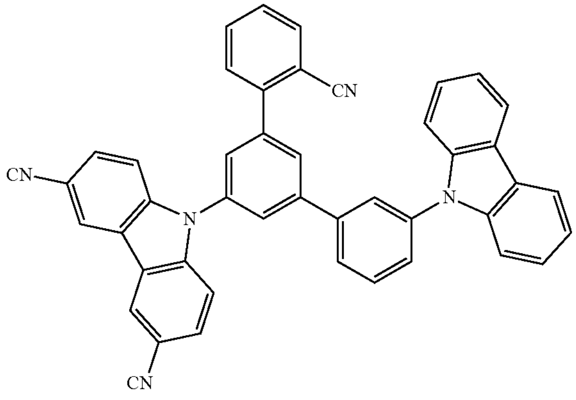

-continued
42
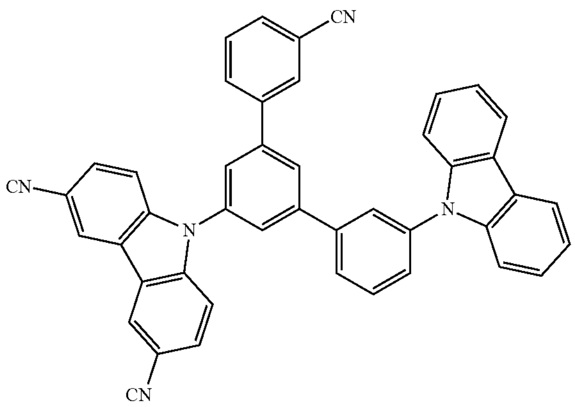
43
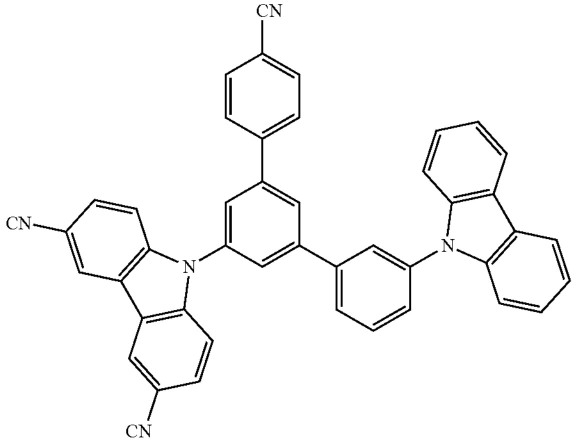
44
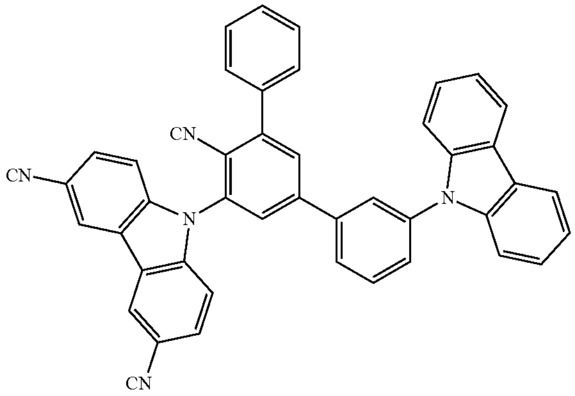
-continued
45
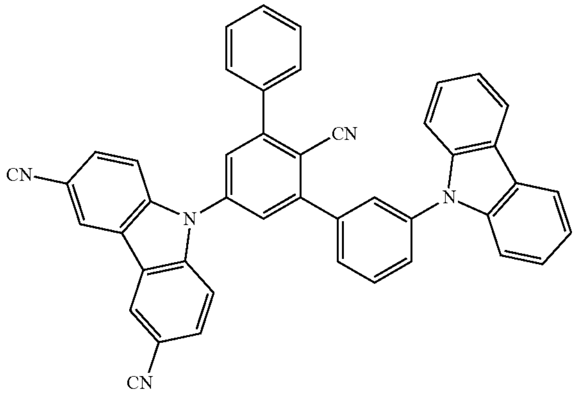
46
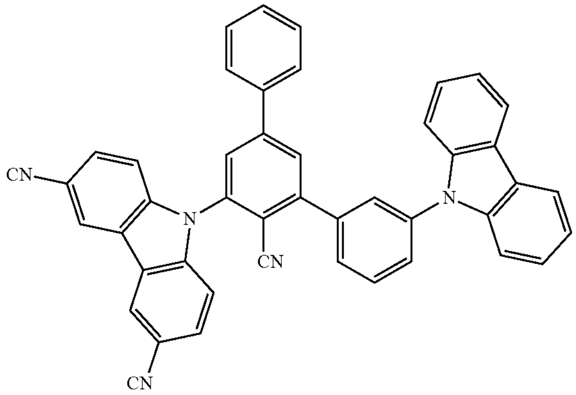
47
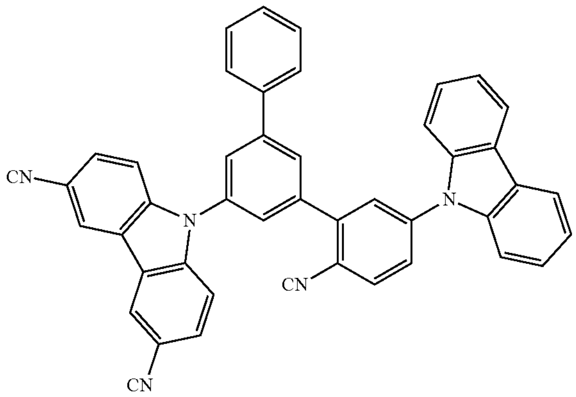

-continued
48
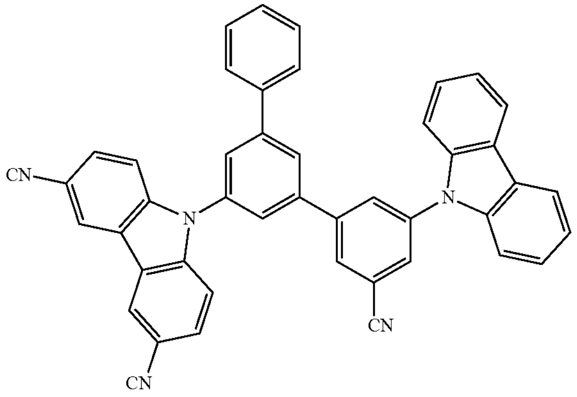
49
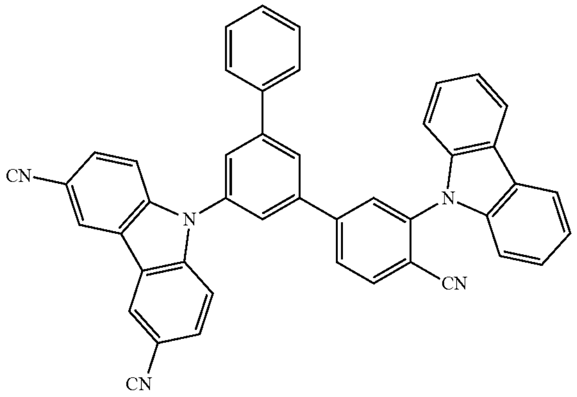
50
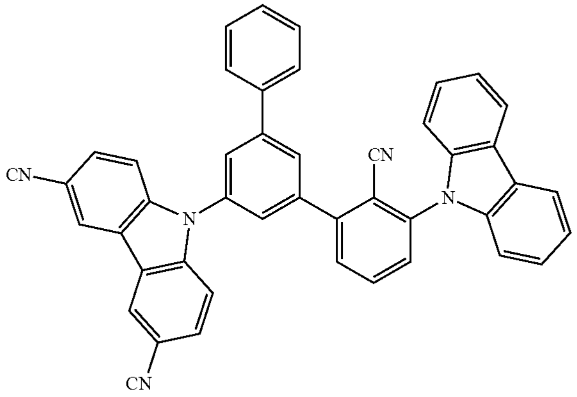
51
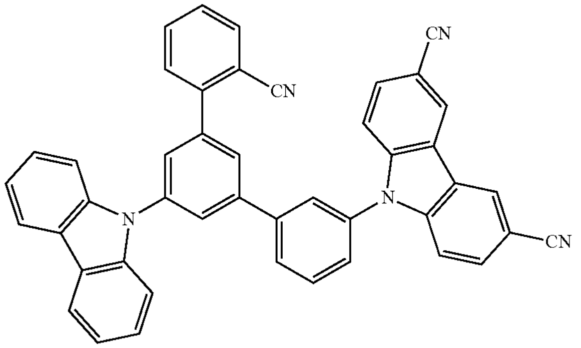
-continued
52
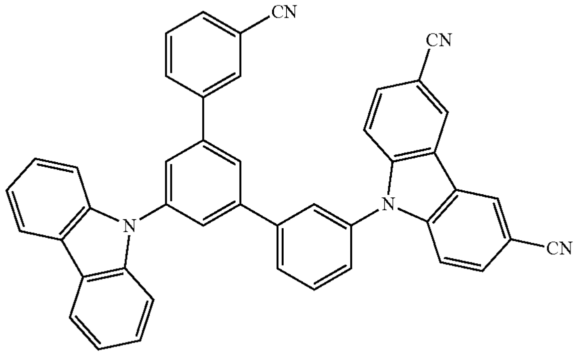
53
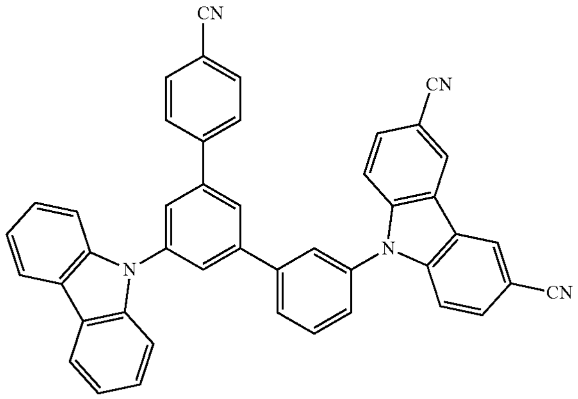
54
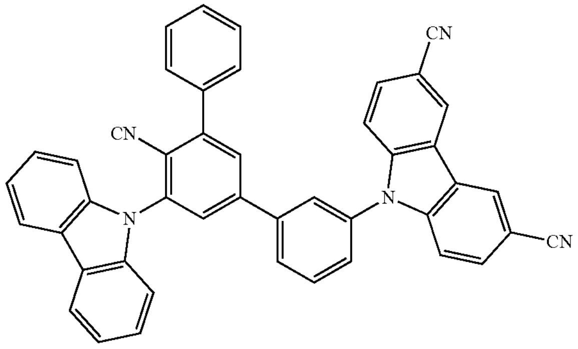
55
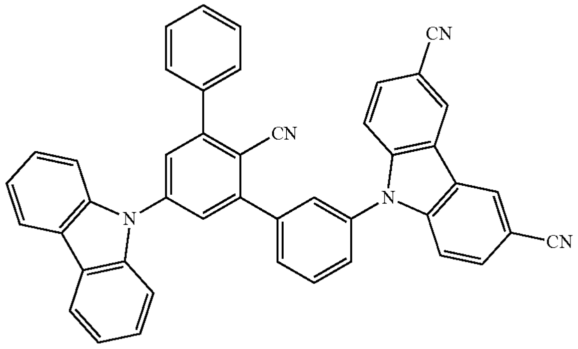

-continued
56
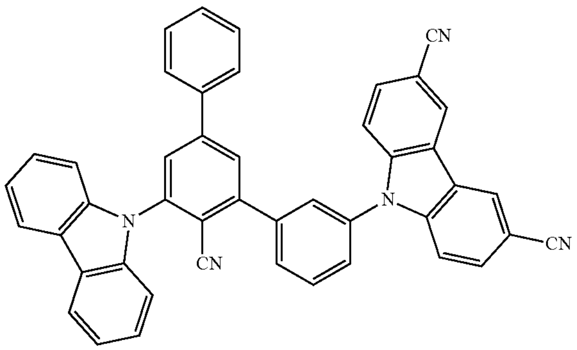
57
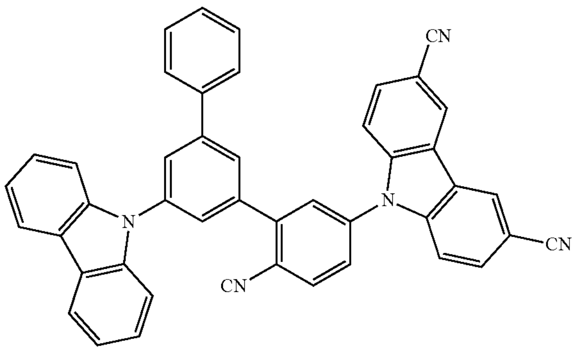
58
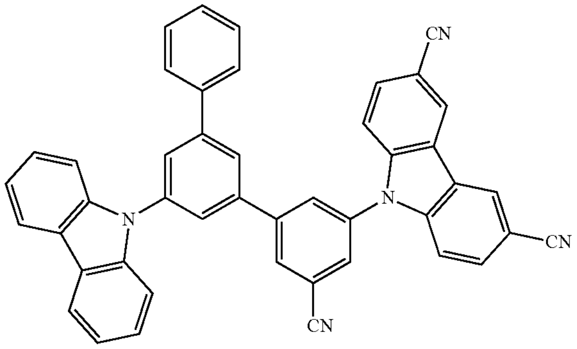
59
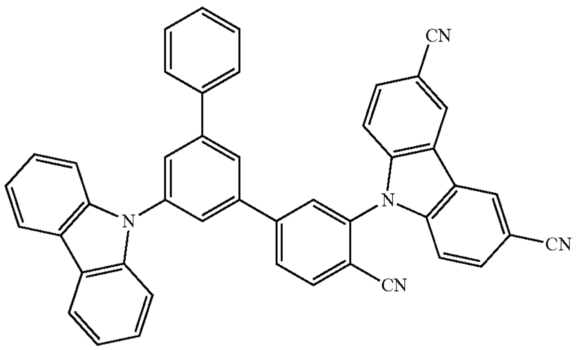
-continued
60
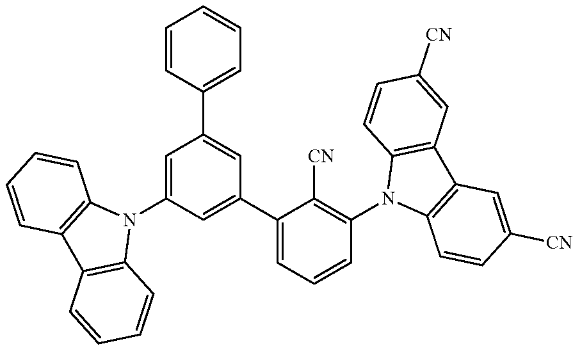
61
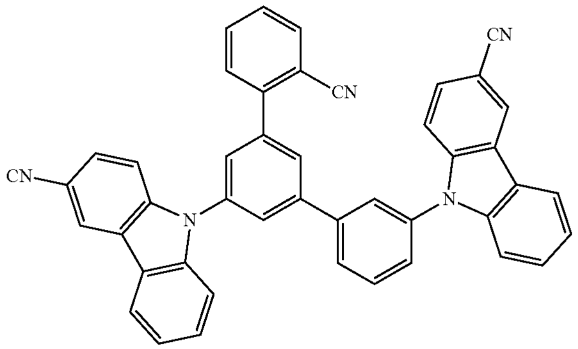
62
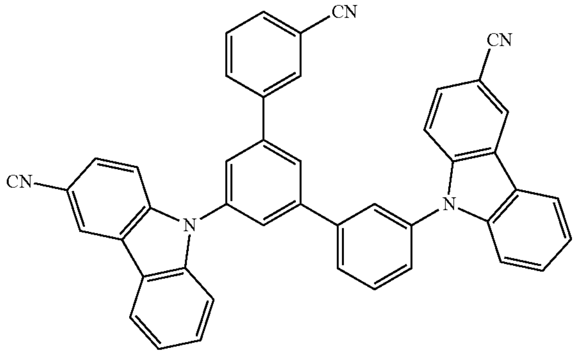
63
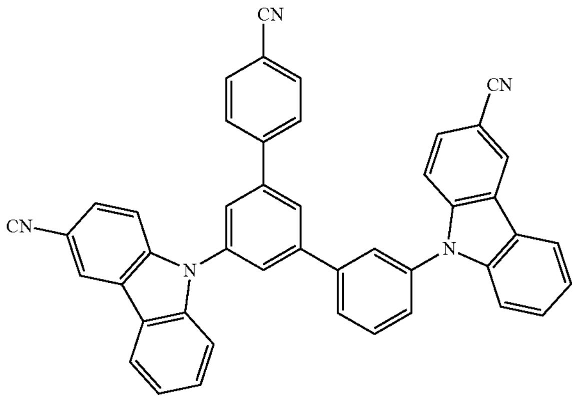

64
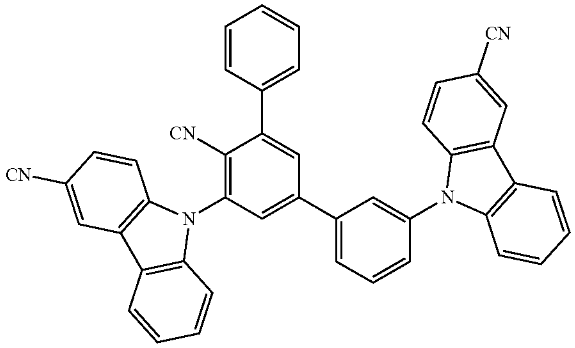
65
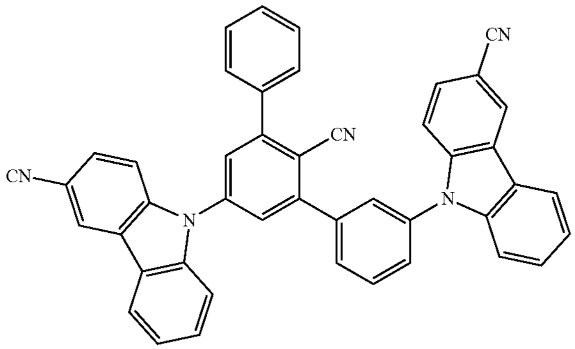
66
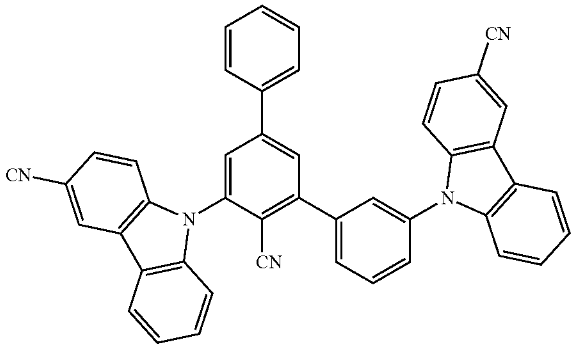
67
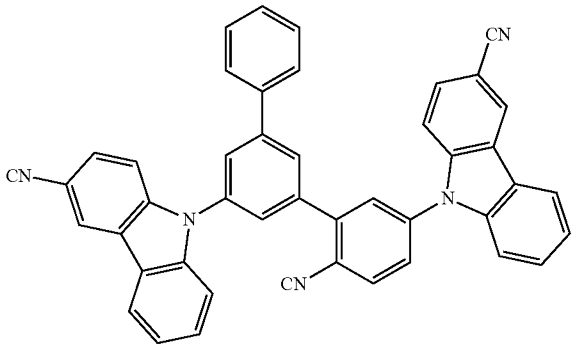
68
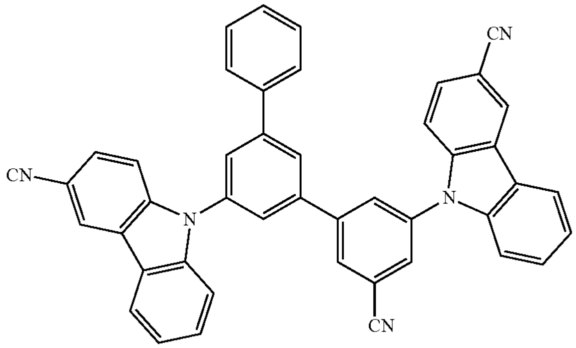
69
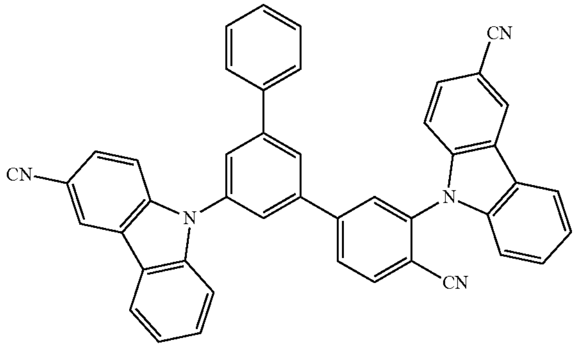
70
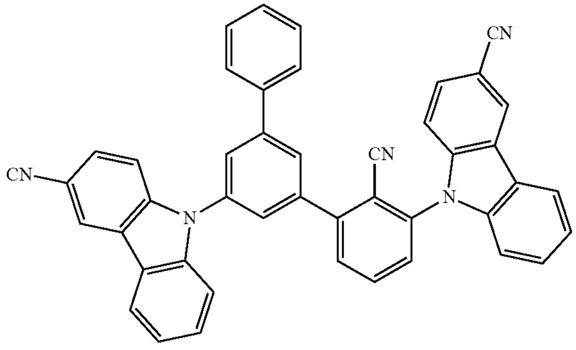
71
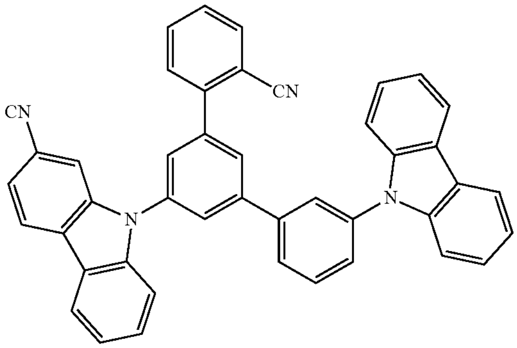

-continued
72
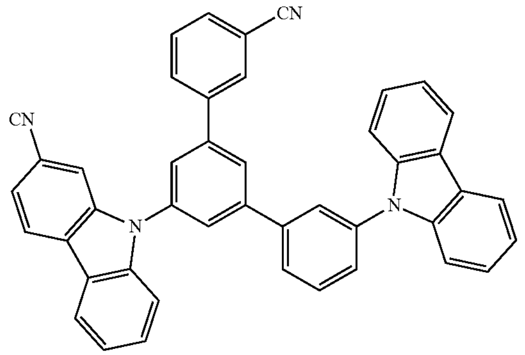
73
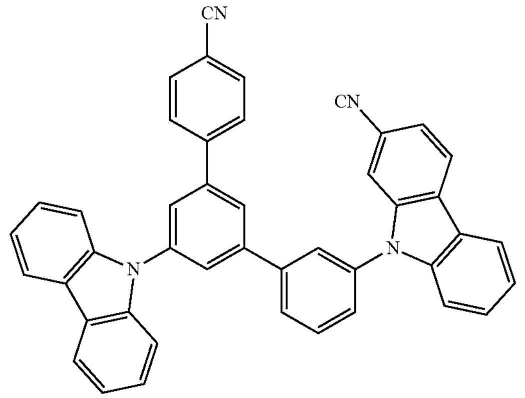
74
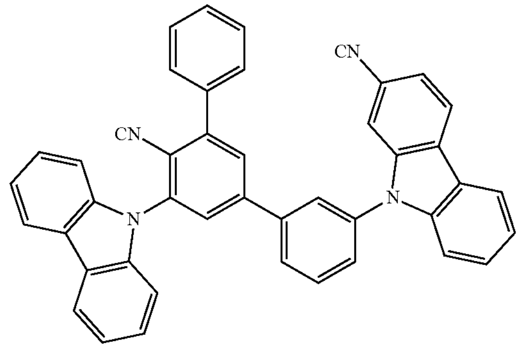
75
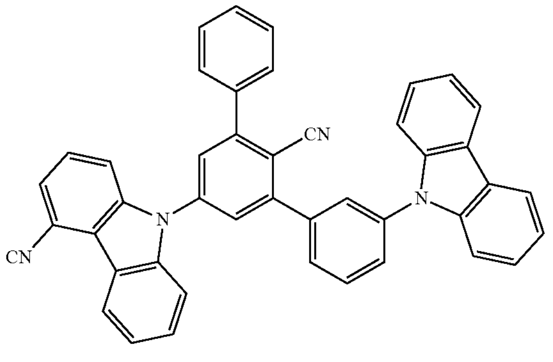
-continued
76
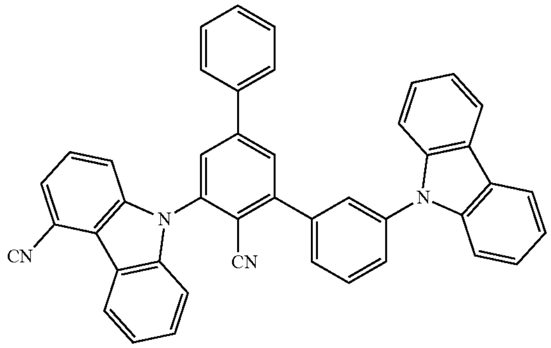
77
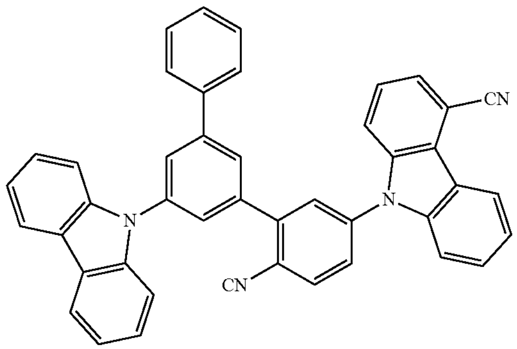
78
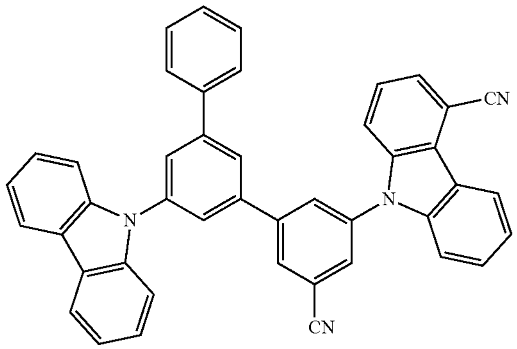
79
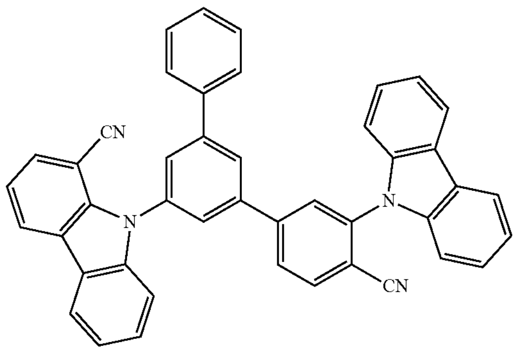

-continued
80
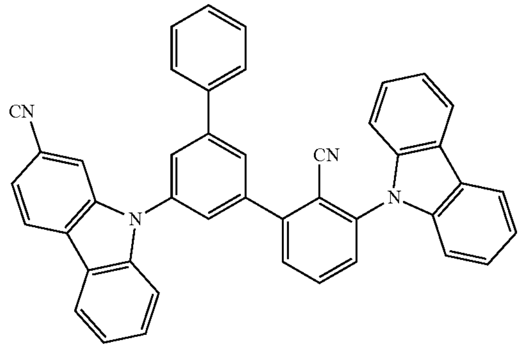
81
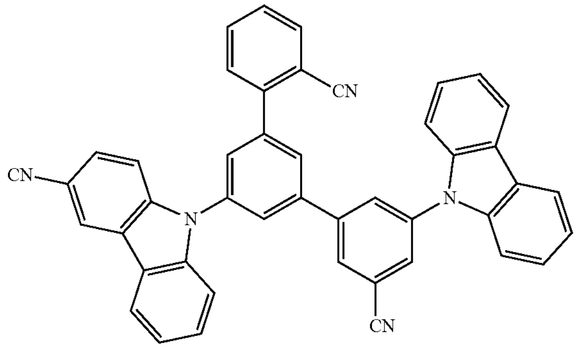
82
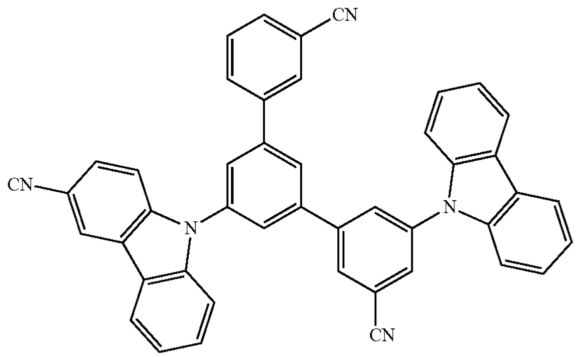
83
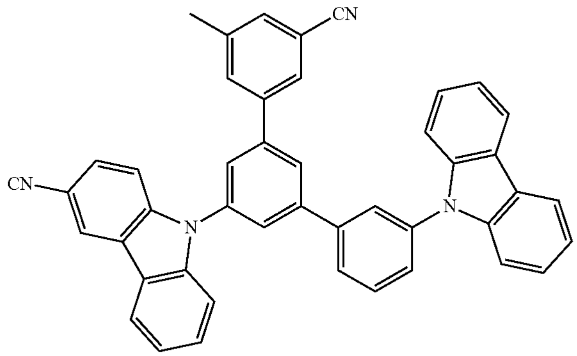
-continued
84
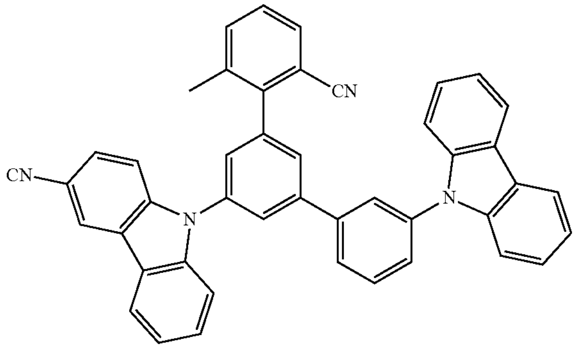
85
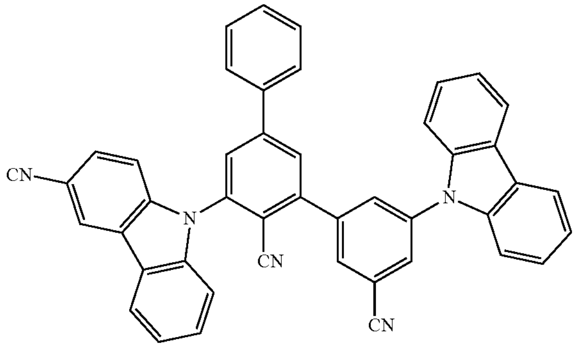
86
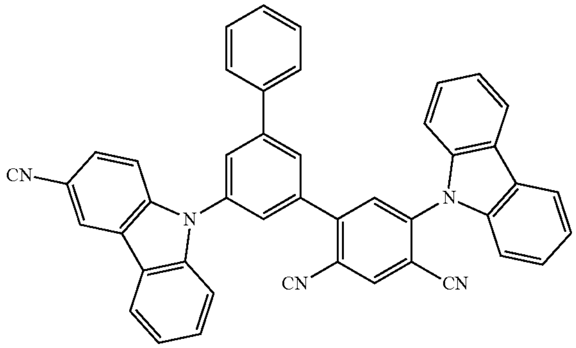
87
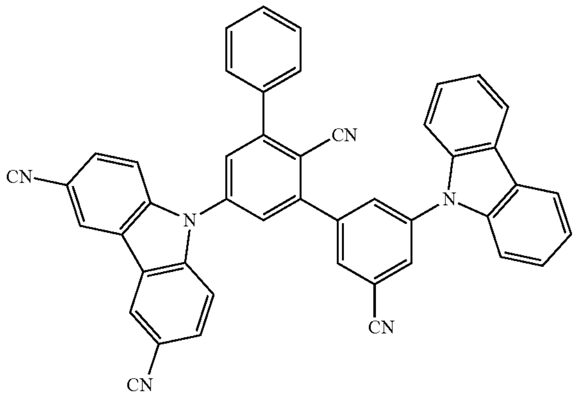

-continued
88
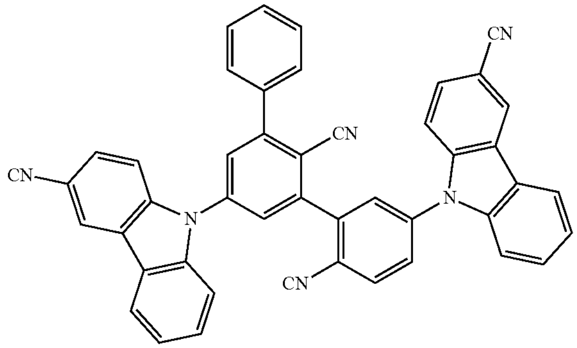
89
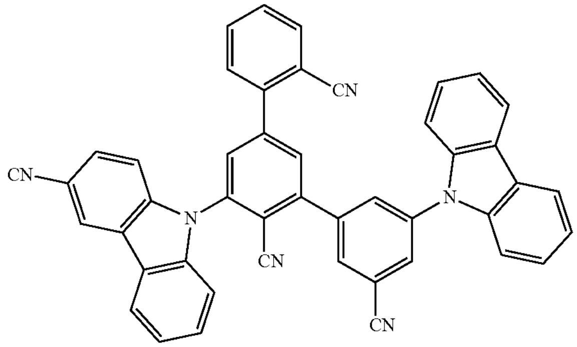
90
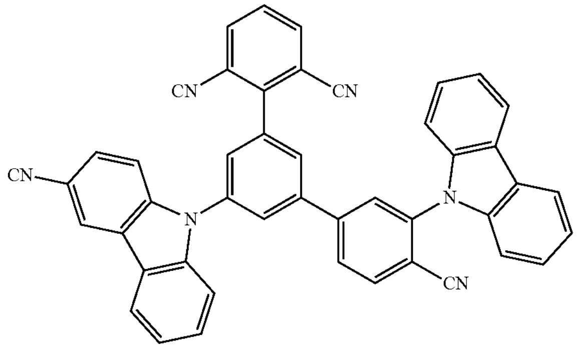
91
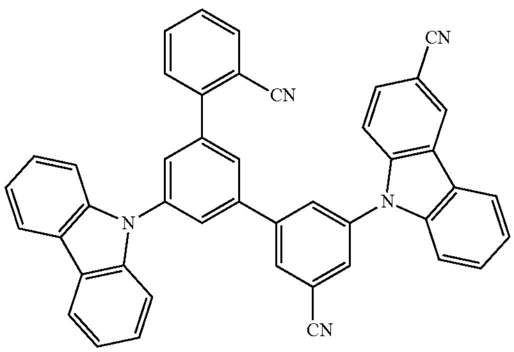
-continued
92
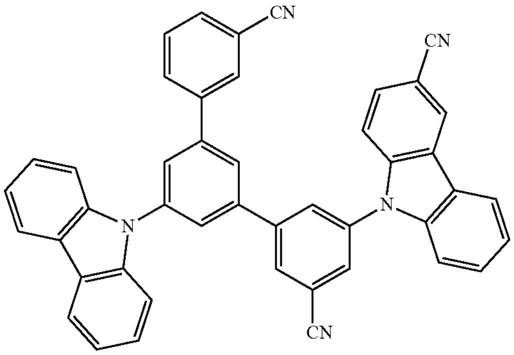
93
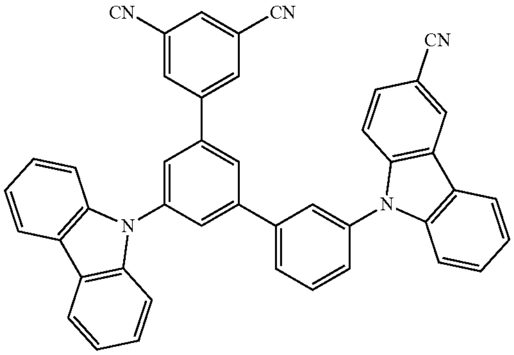
94
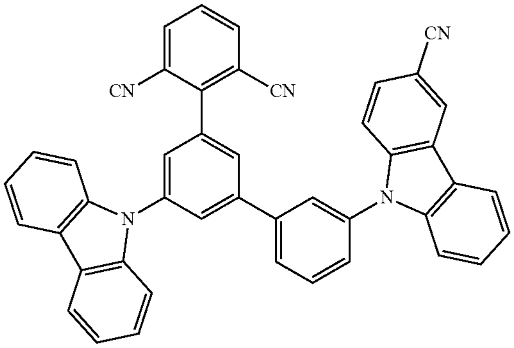
95
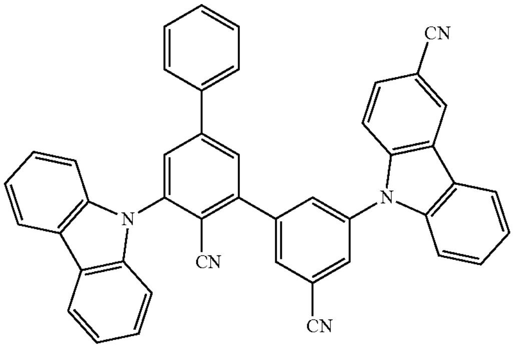

96
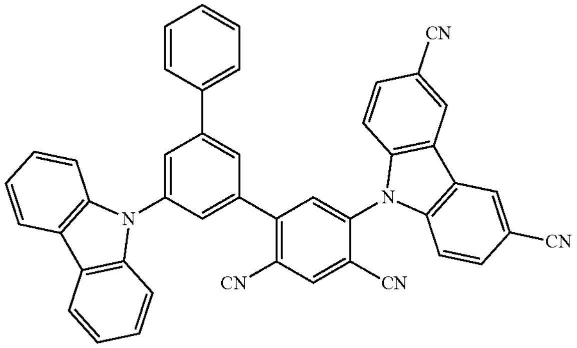
97
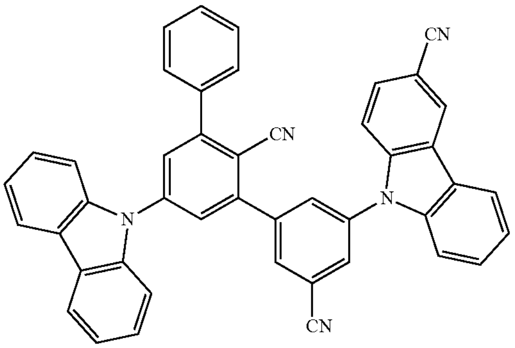
98
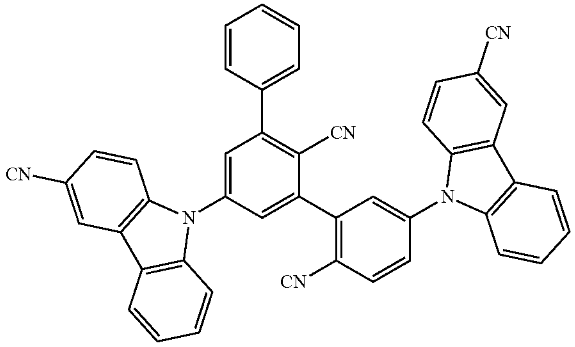
99
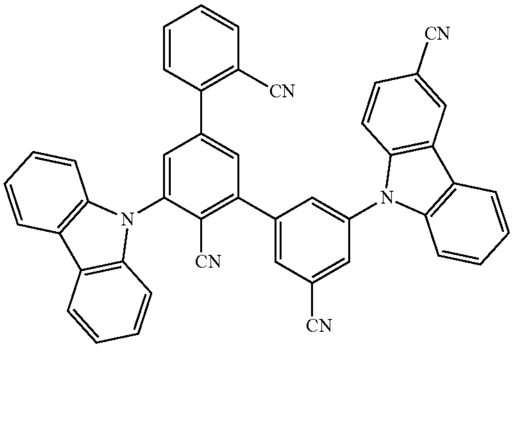
100
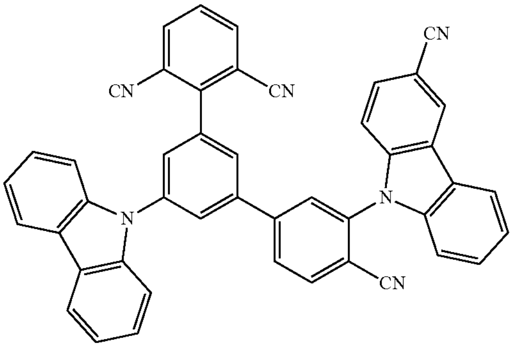
101
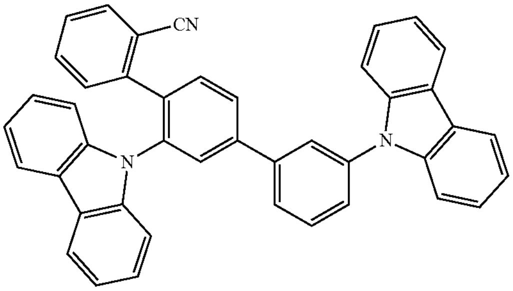
102
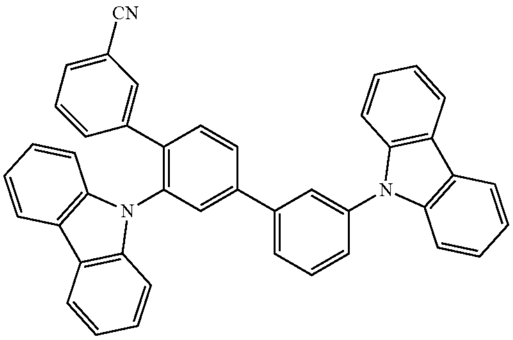
103
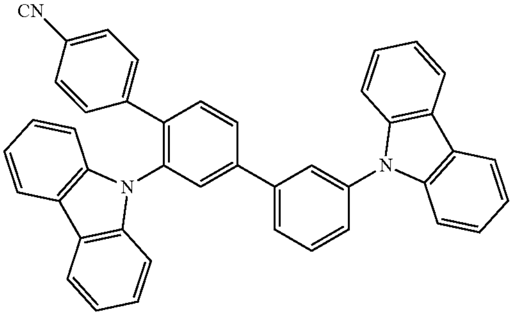

-continued
104
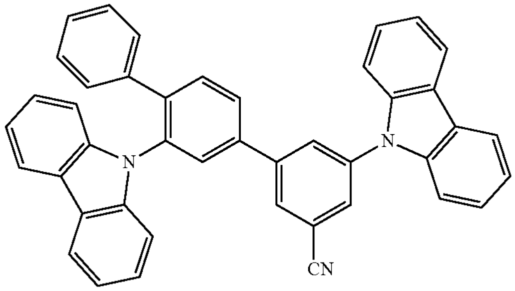
105
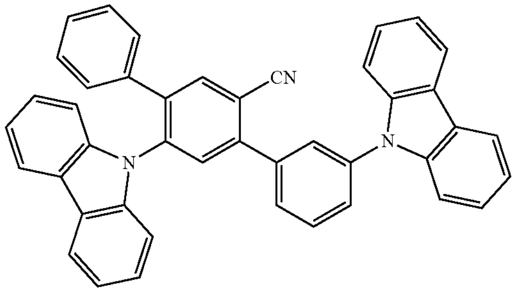
106
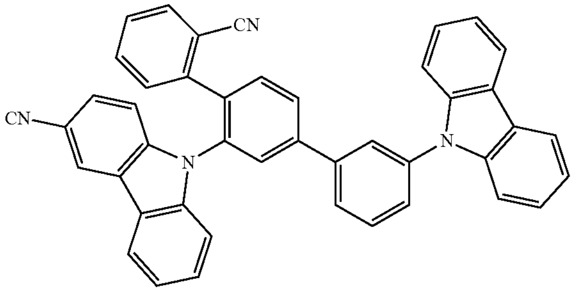
107
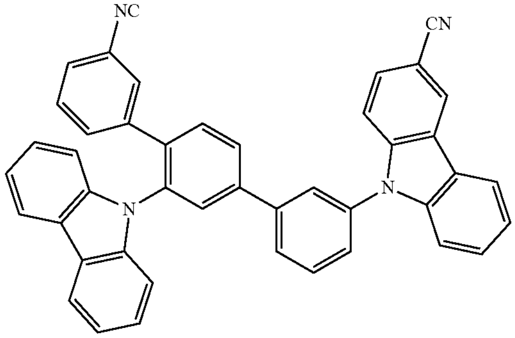
108
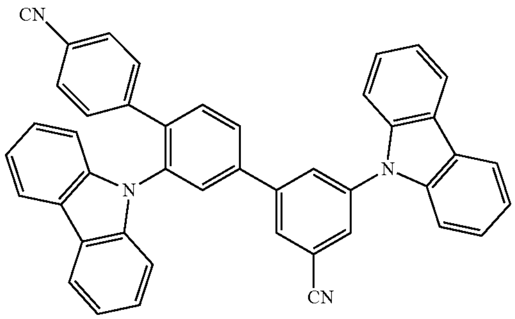
-continued
109
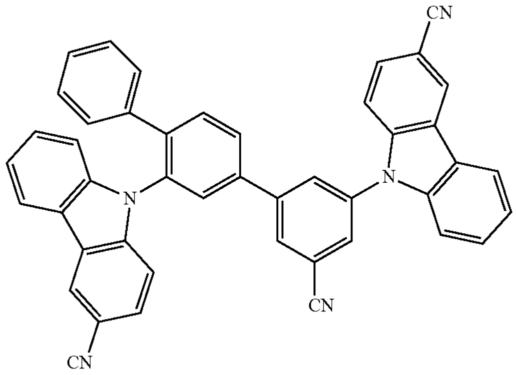
110
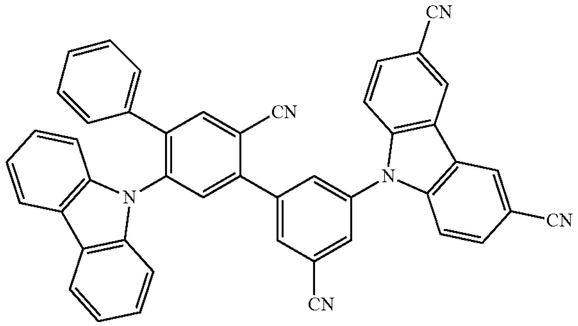
111
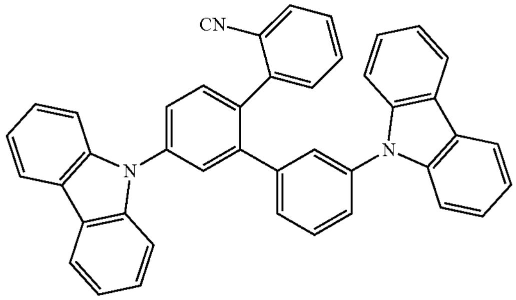
112
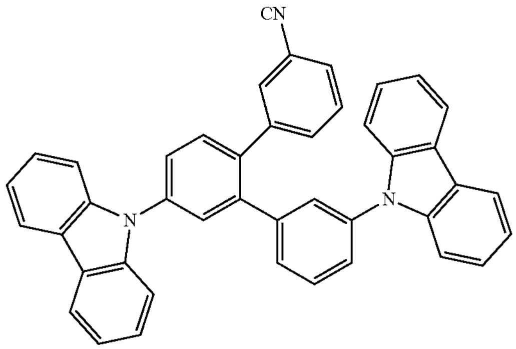

-continued
113
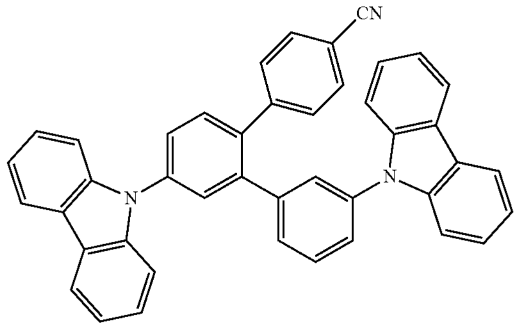
114
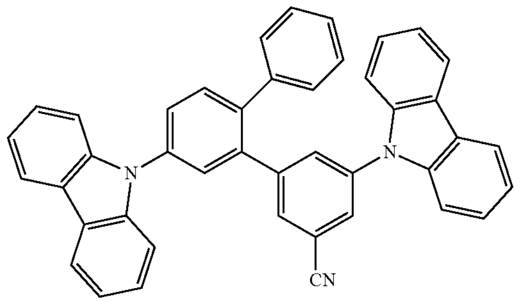
115
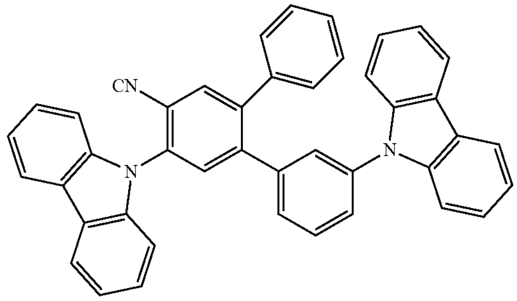
116
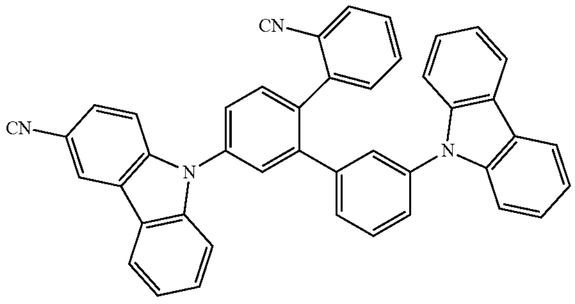
-continued
117
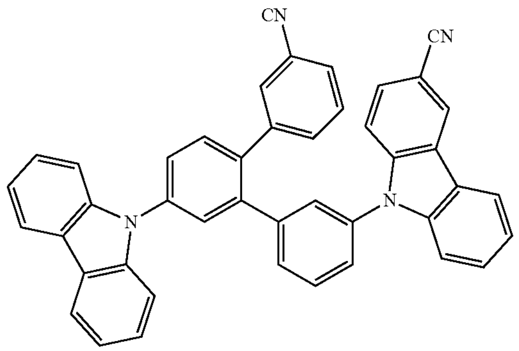
118
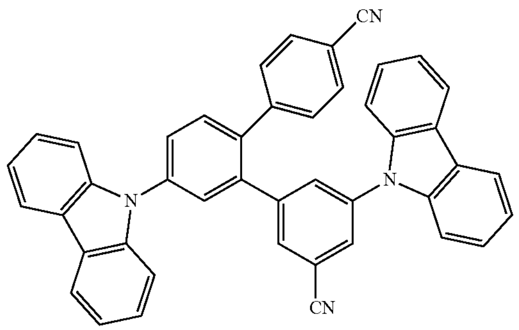
119
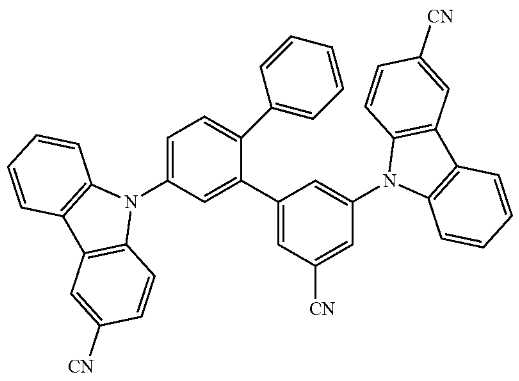
120
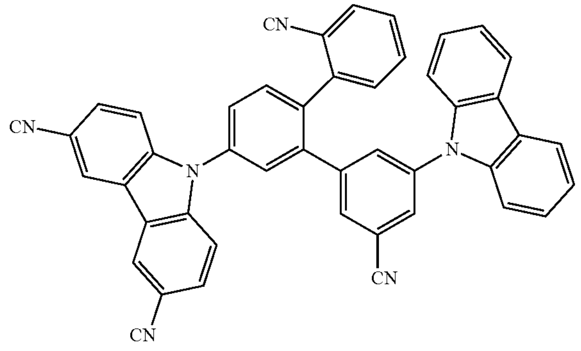

-continued
121
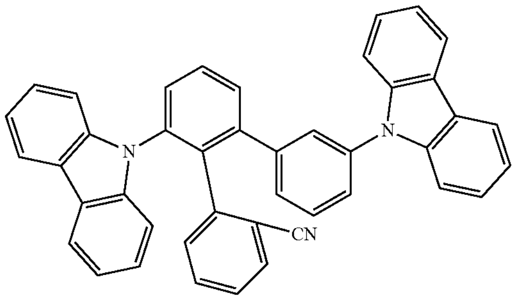
122
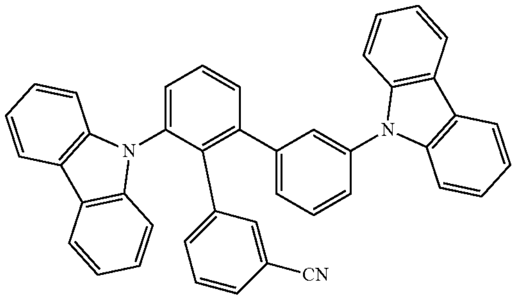
123
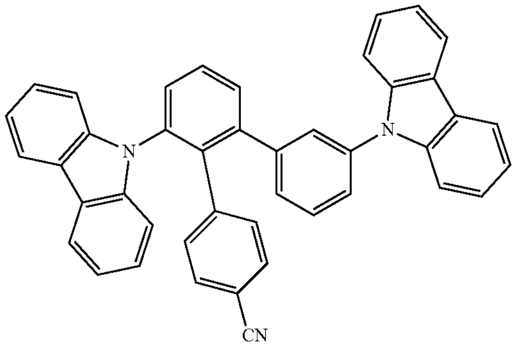
124
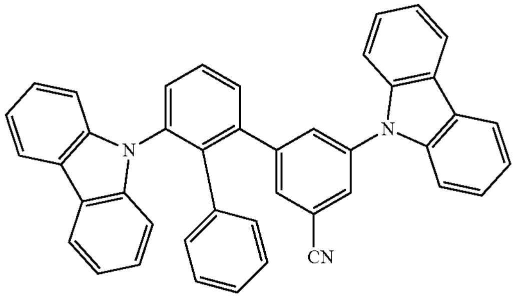
125
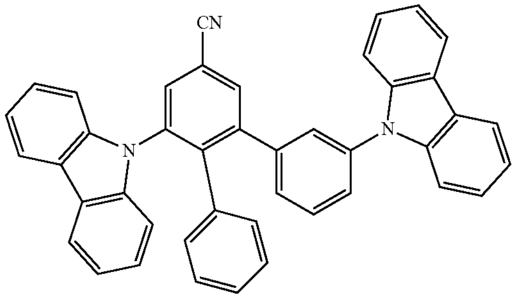
-continued
126
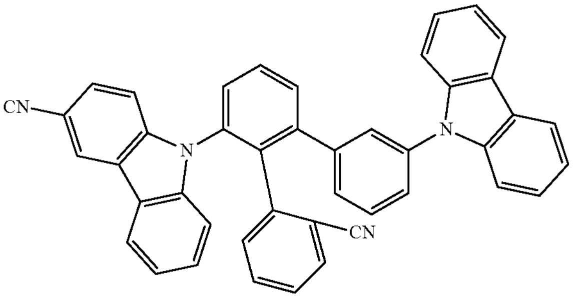
127
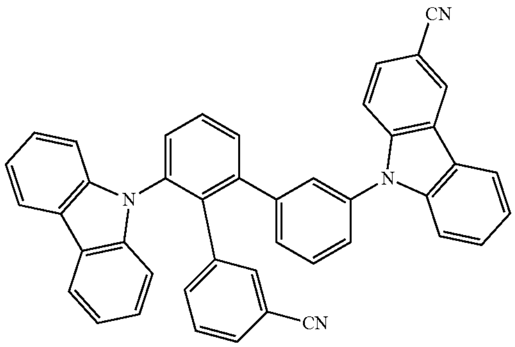
128
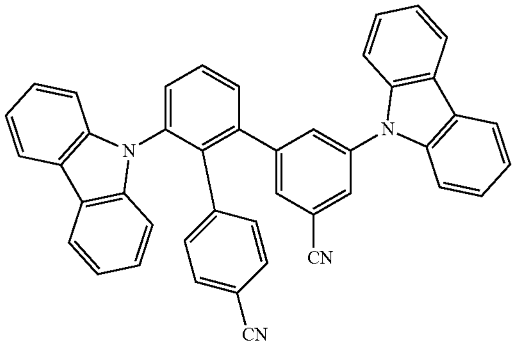
129
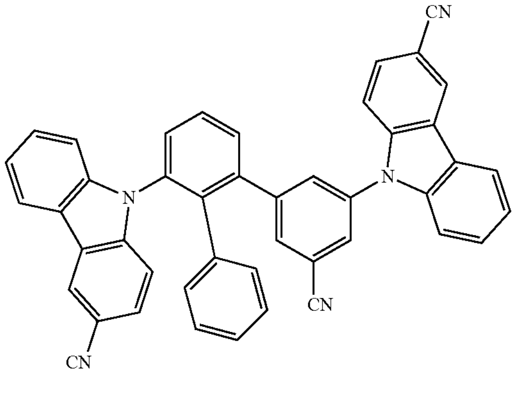

-continued
130
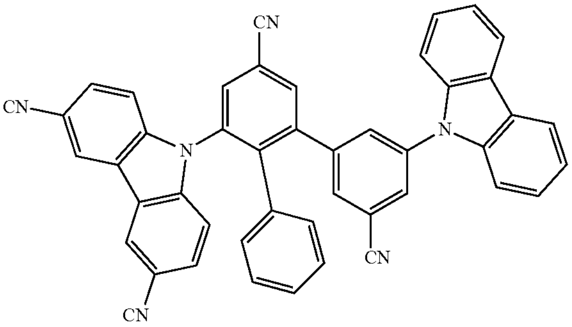
131
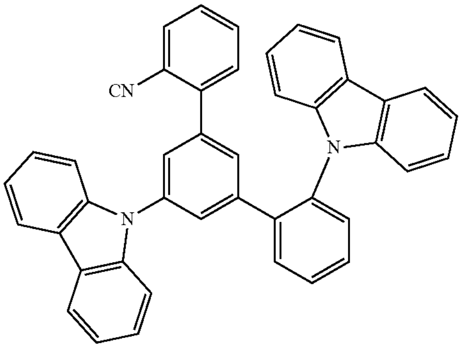
132
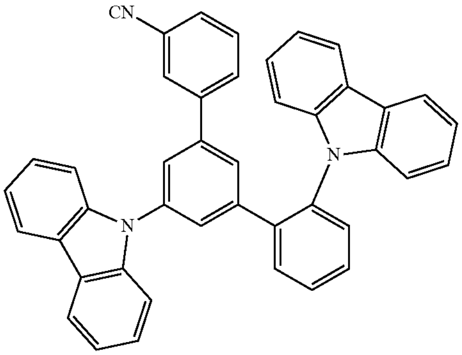
133
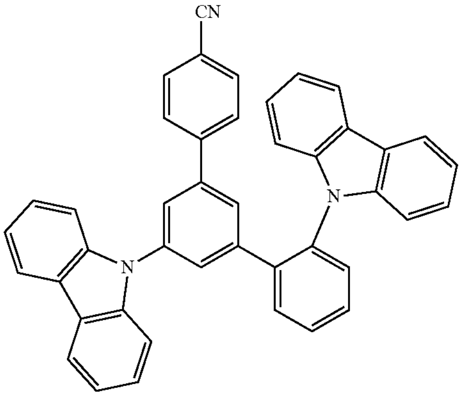
-continued
134
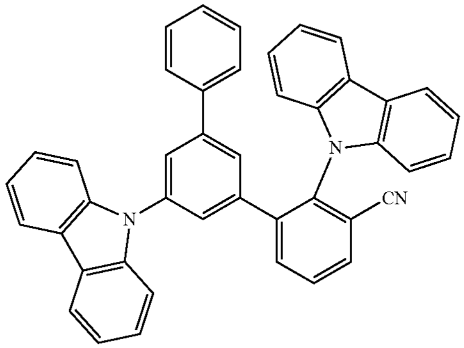
135
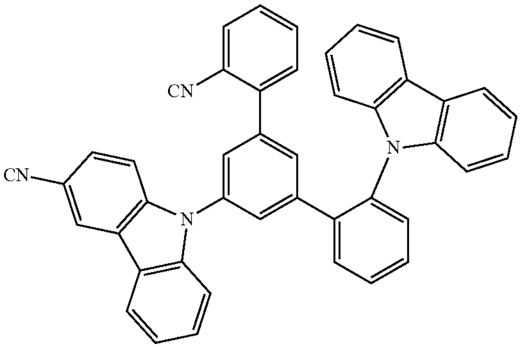
136
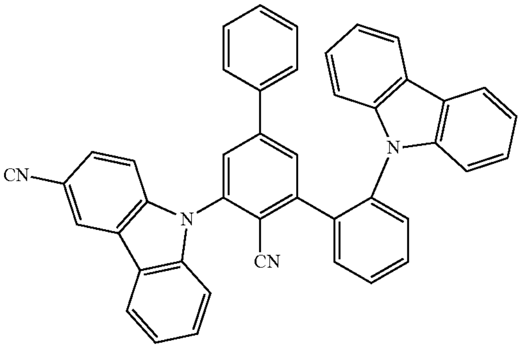
137
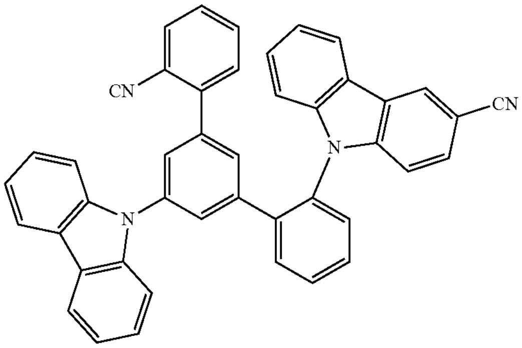

-continued
138
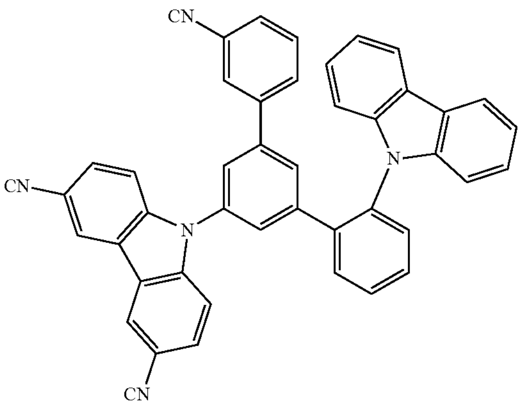
139
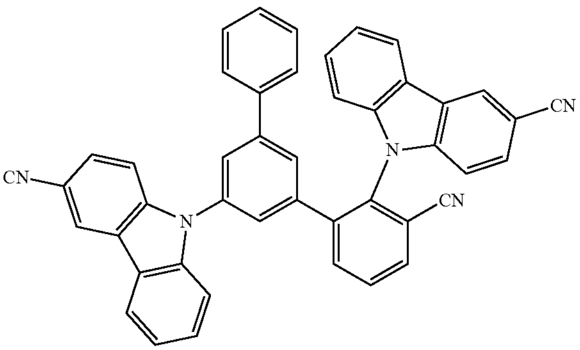
140
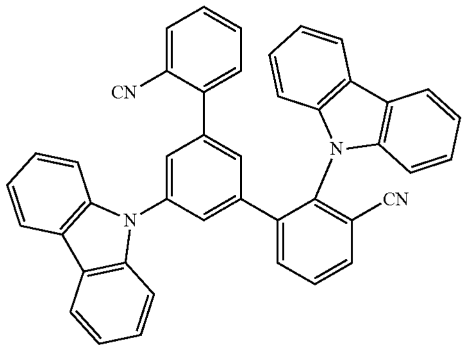
141
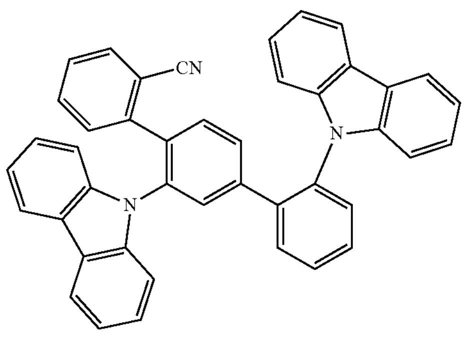
-continued
142
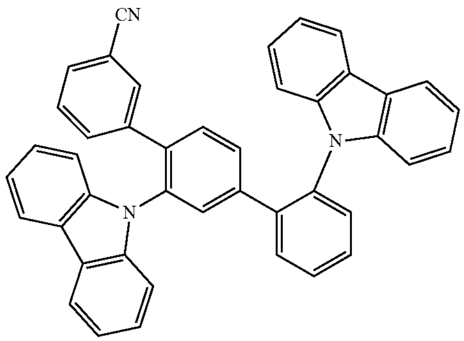
143
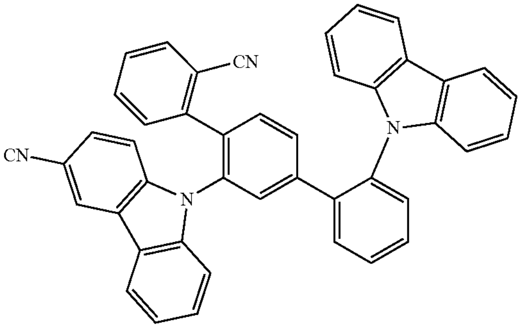
144
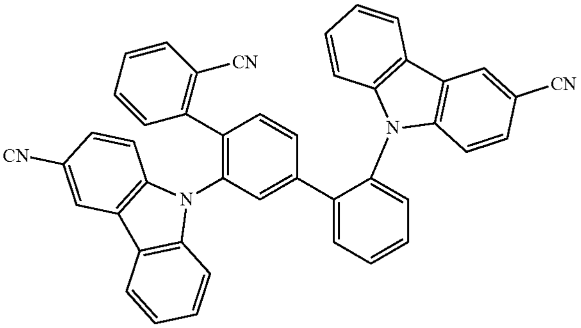
145
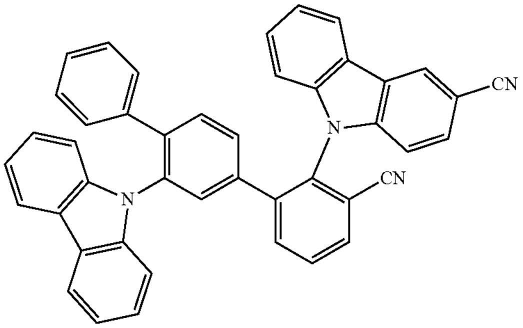

-continued
146
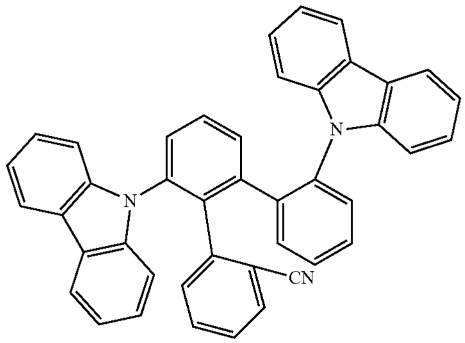
147
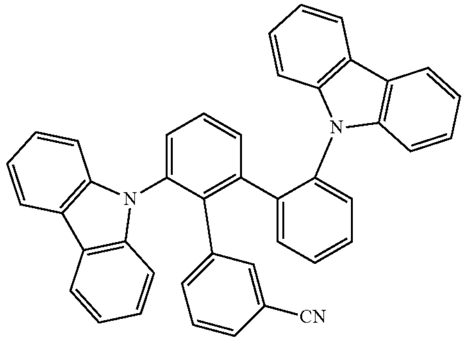
148
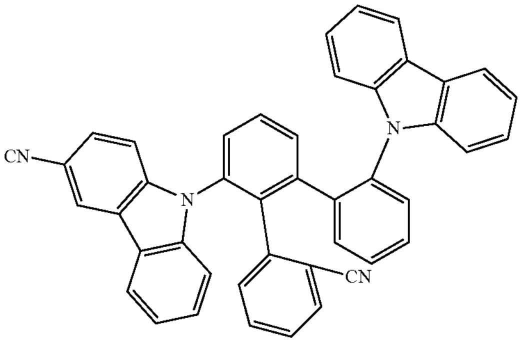
149
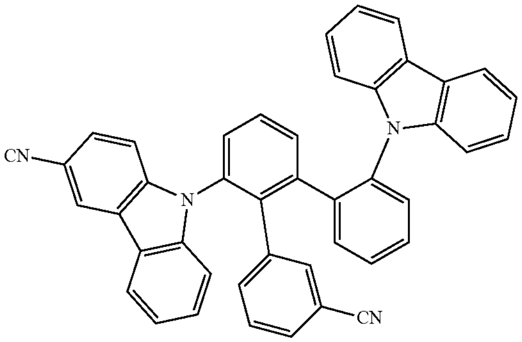
-continued
150
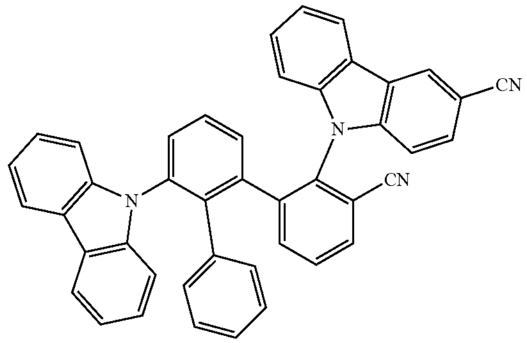
151
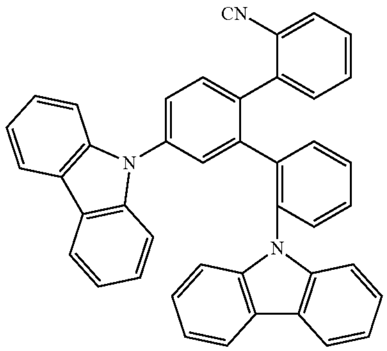
152
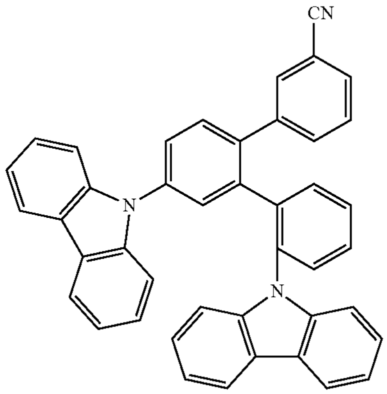
153
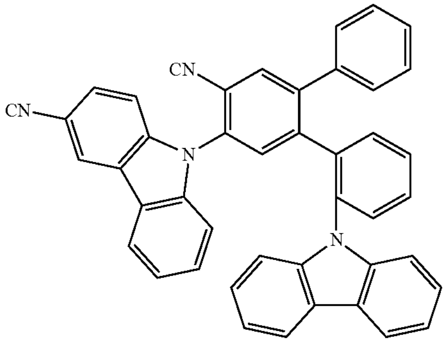

-continued
154
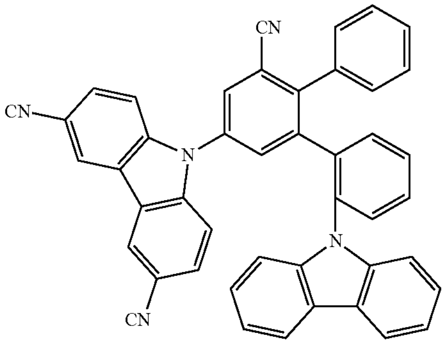
155
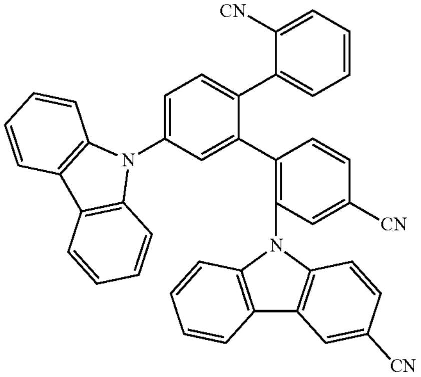
156
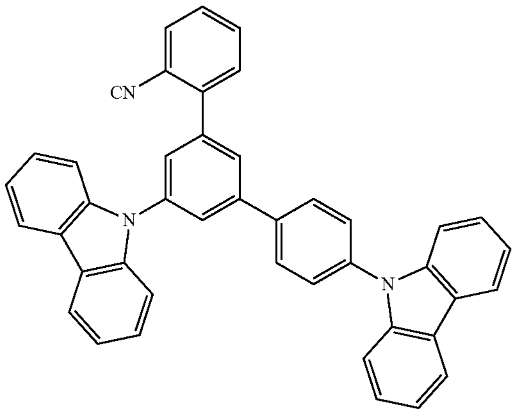
157
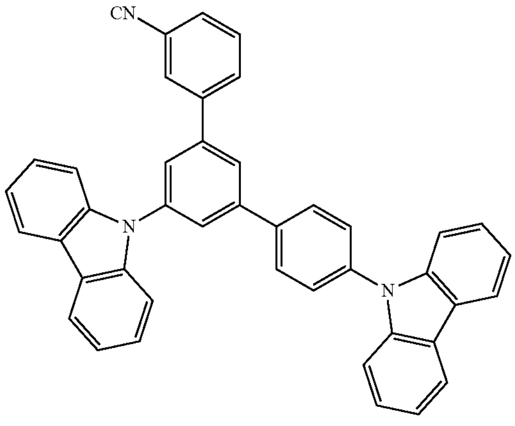
-continued
158
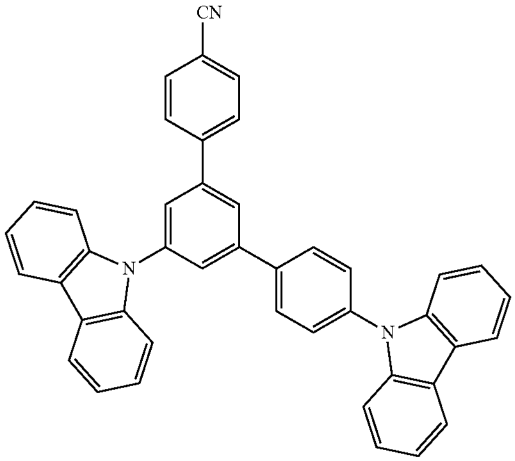
159
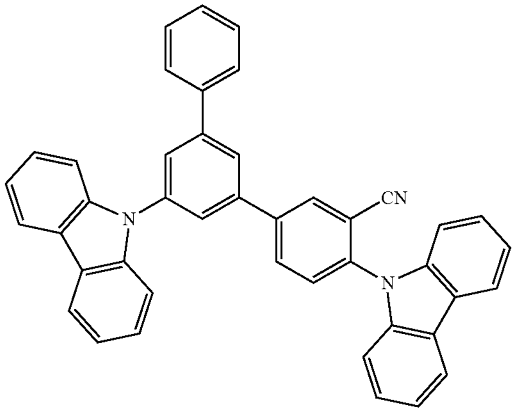
160
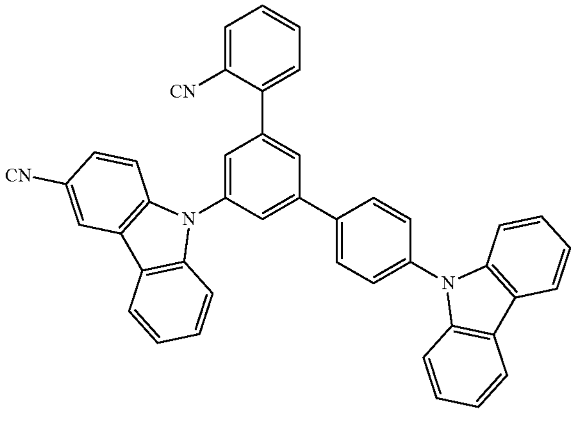

161
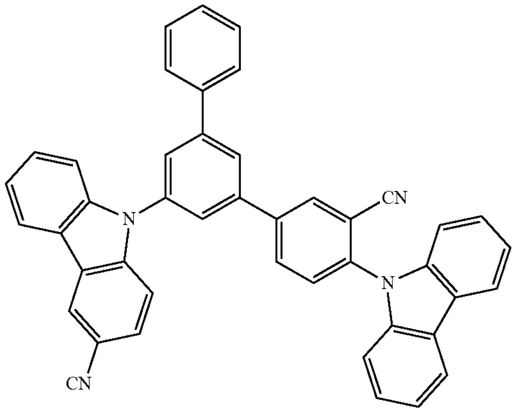
162
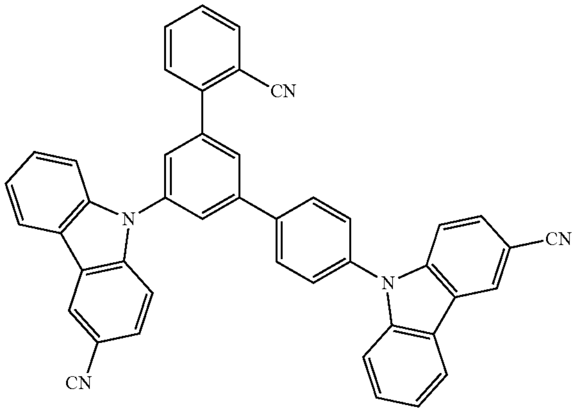
163
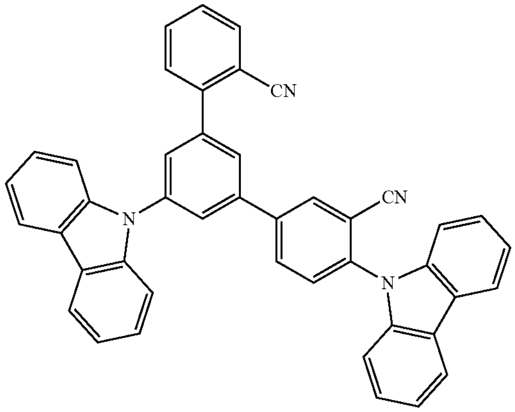
164
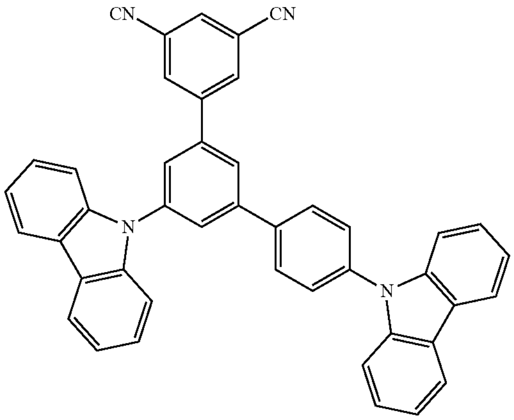
165
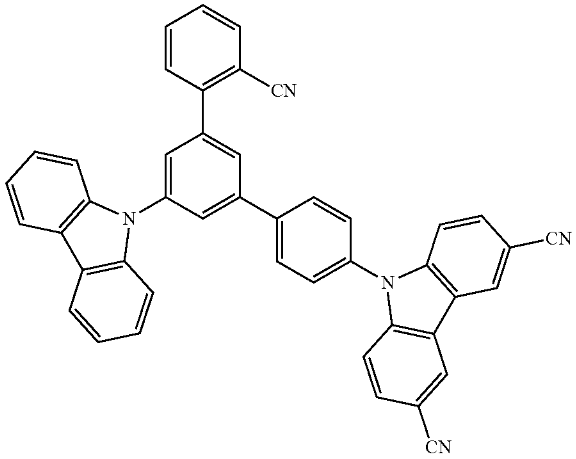
166
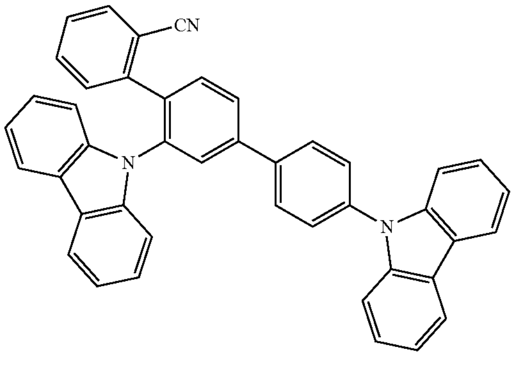

-continued
167
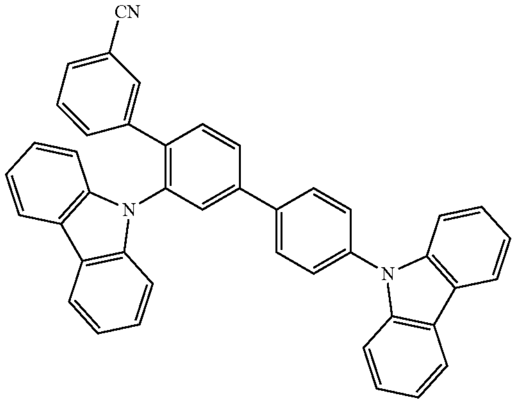
168
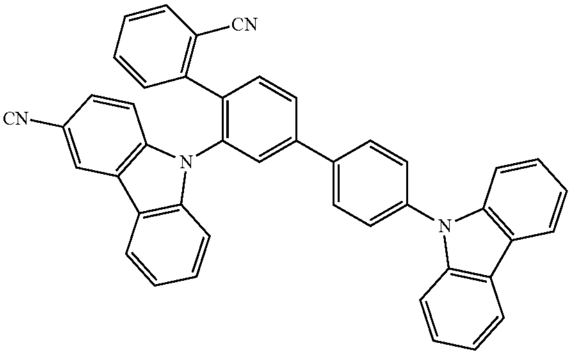
169
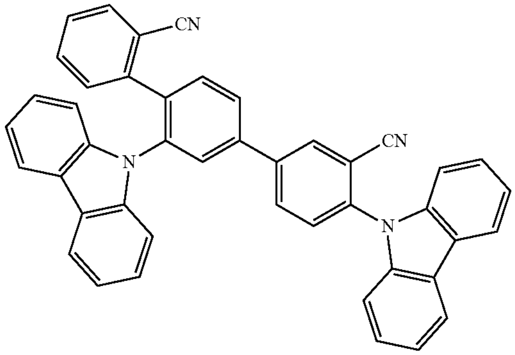
170
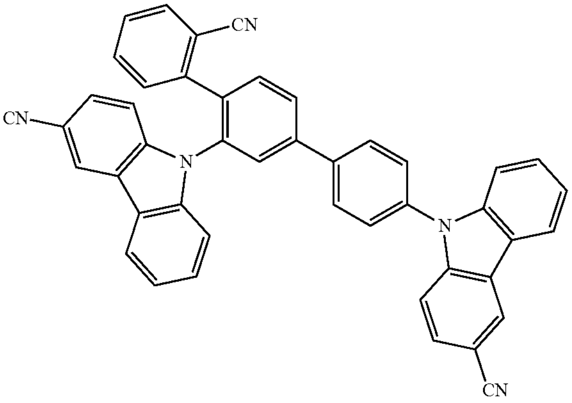
-continued
171
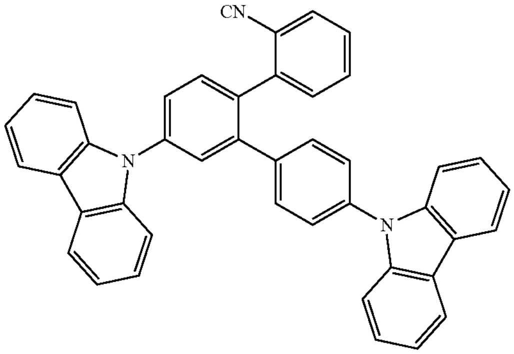
172
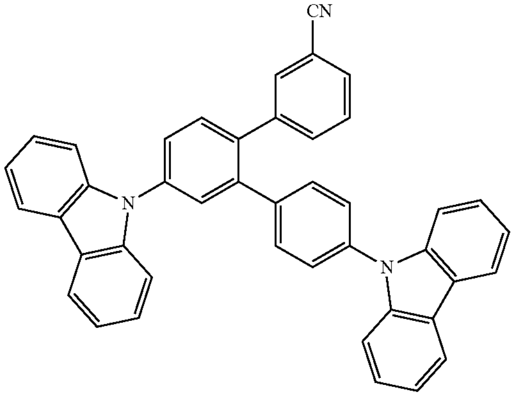
173
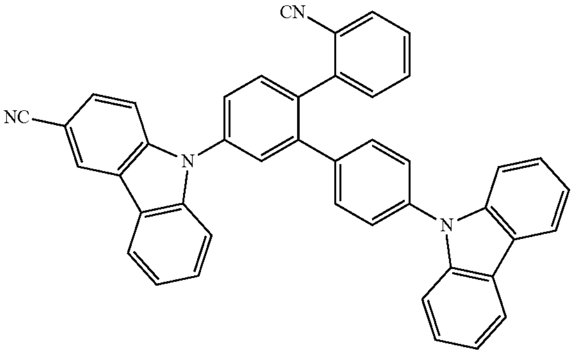
174
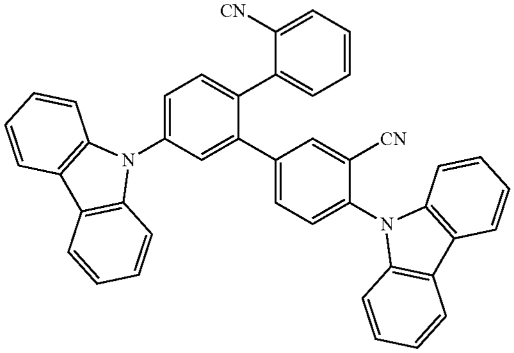

-continued
175
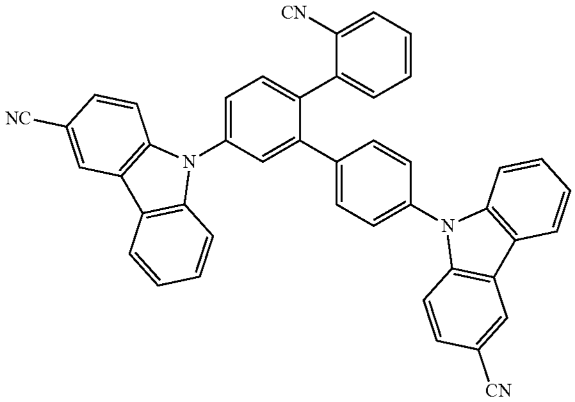
176
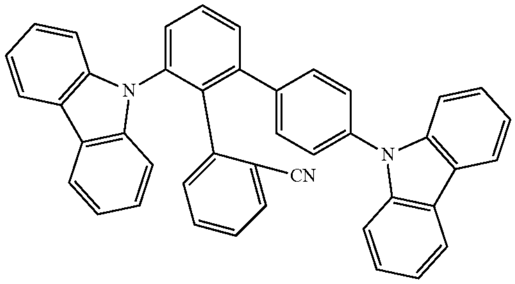
177
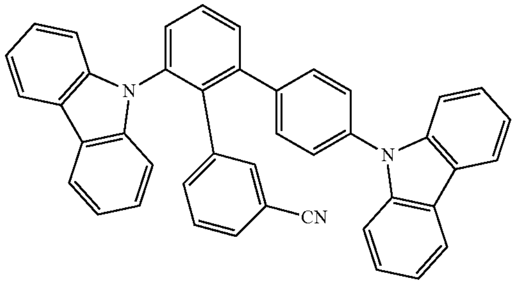
178
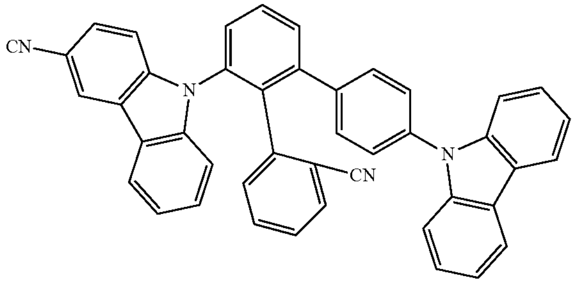
179
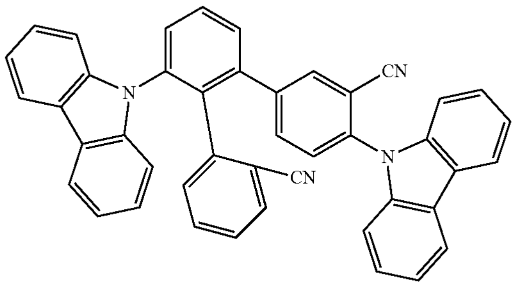
-continued
180
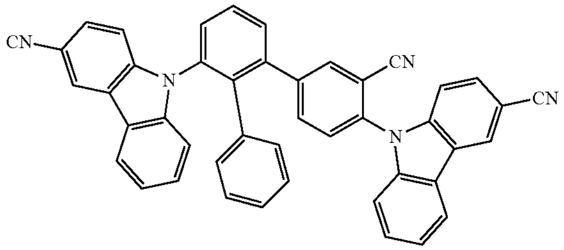
181
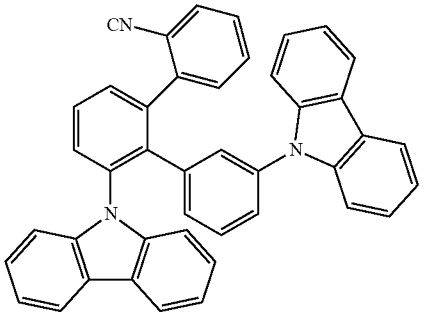
182
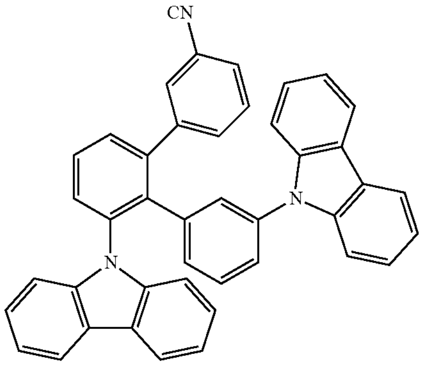
183
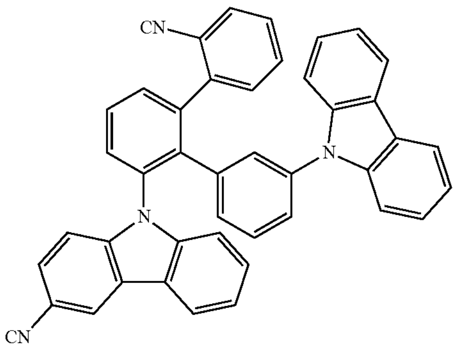

-continued
184
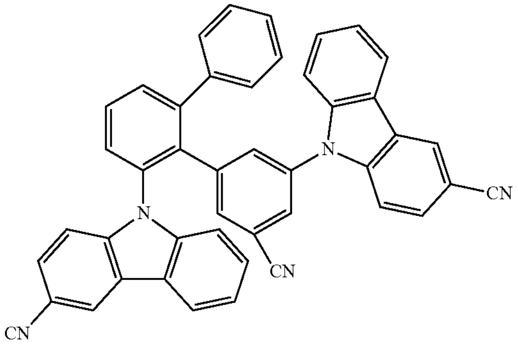
185
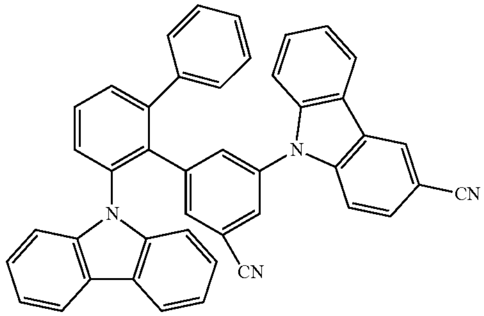
186
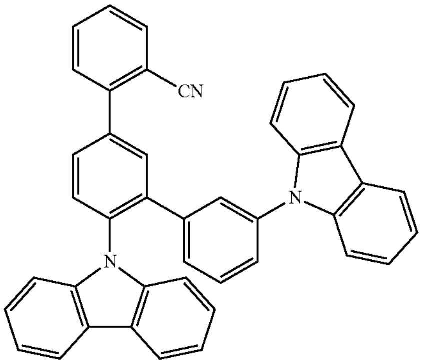
187
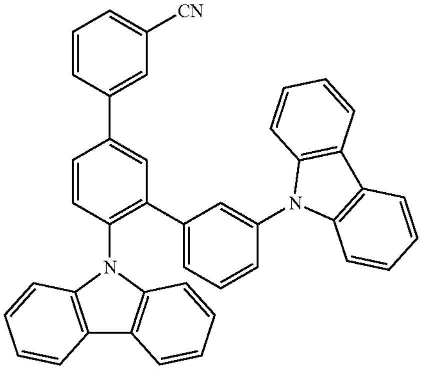
-continued
188
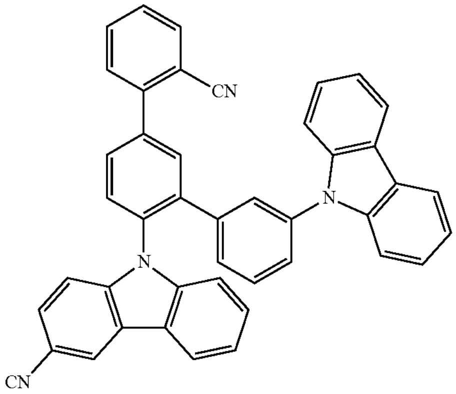
189
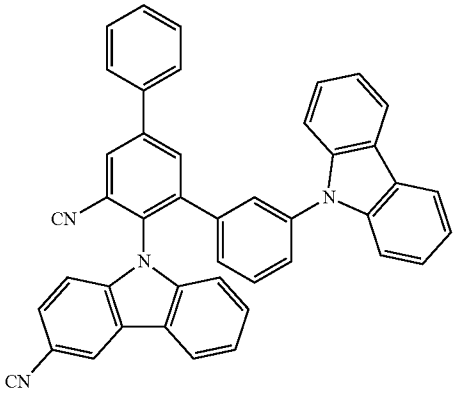
190
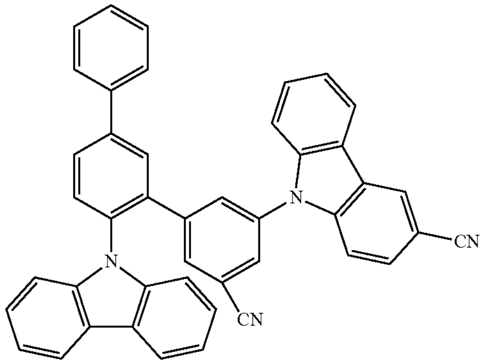
191
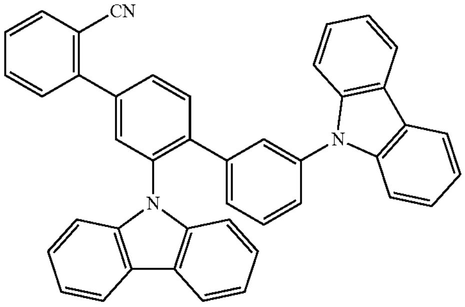

-continued
192
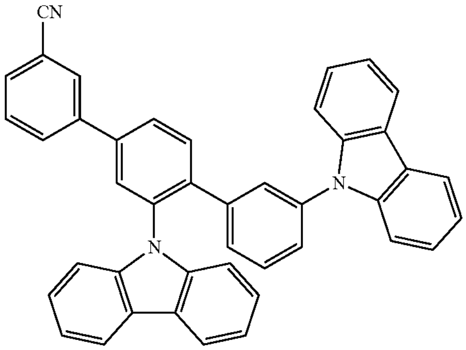
193
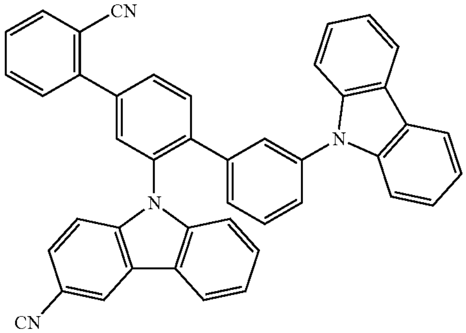
194
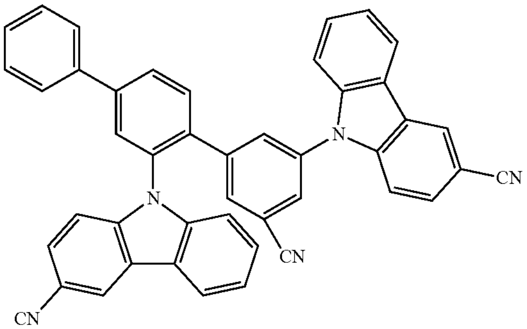
195
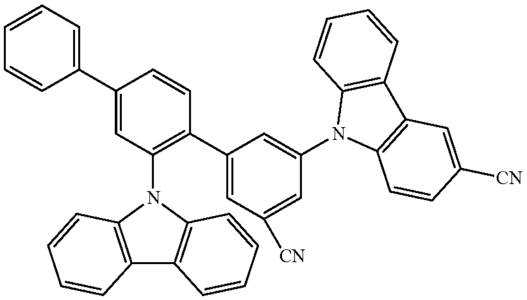
196
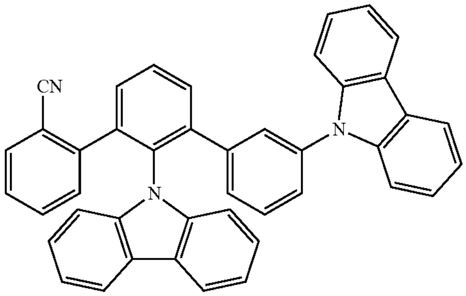
-continued
197
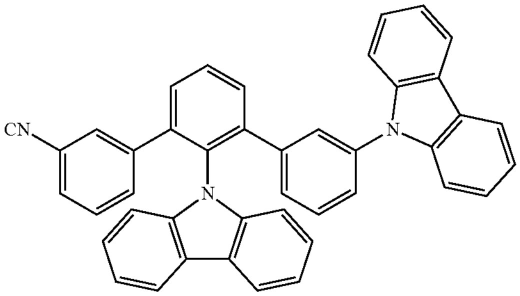
198
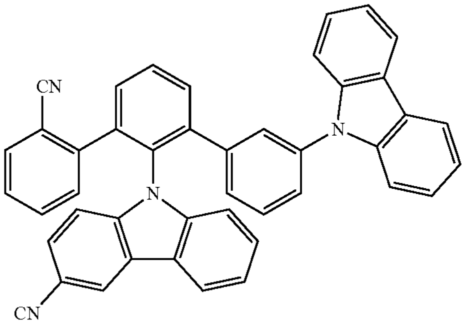
199
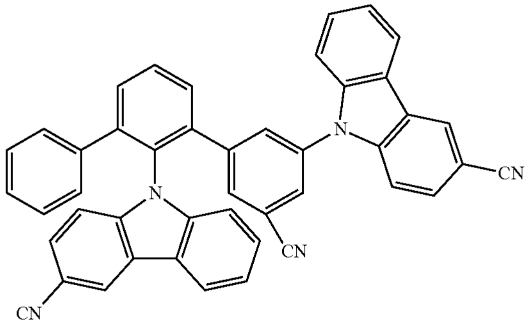
200
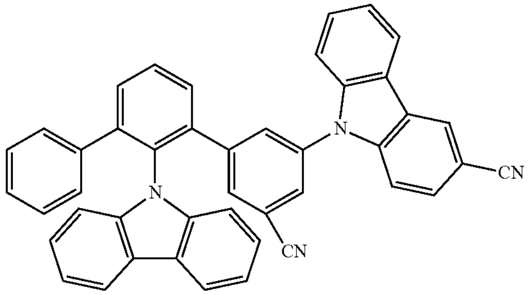
201
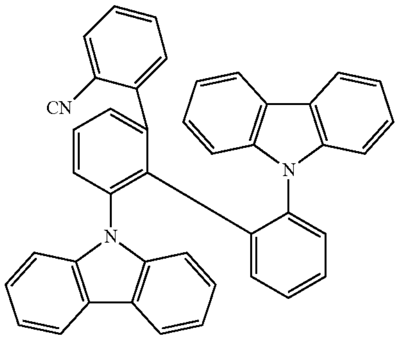

202
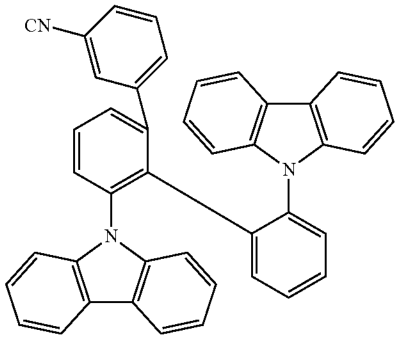
203
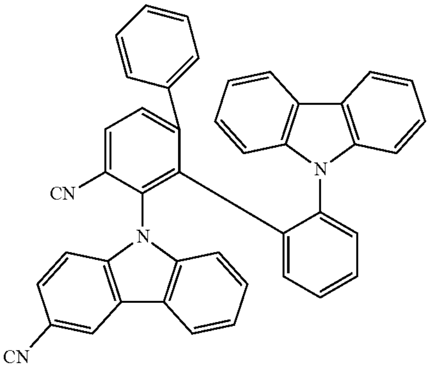
204
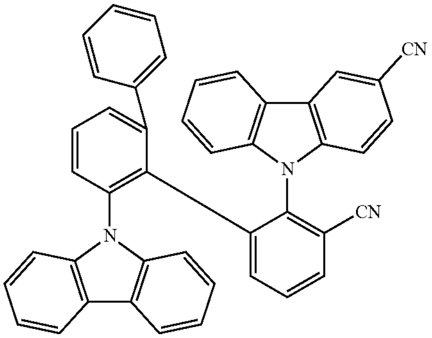
205
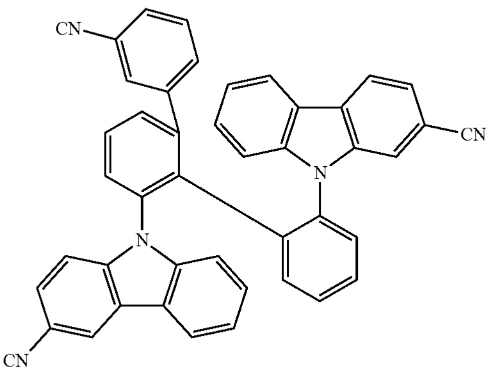
206
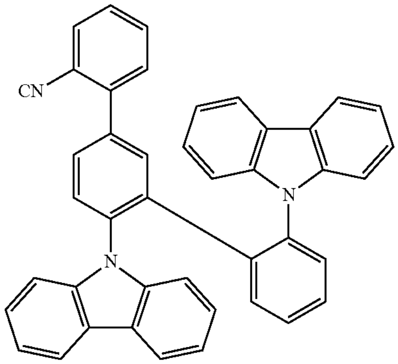
207
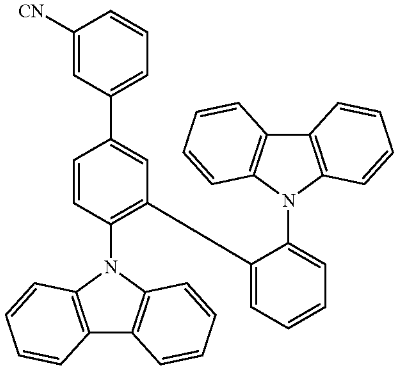
208
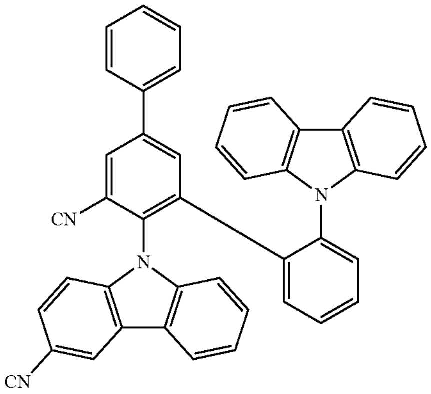
209
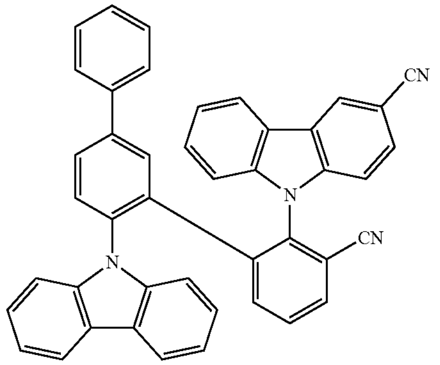

-continued
210
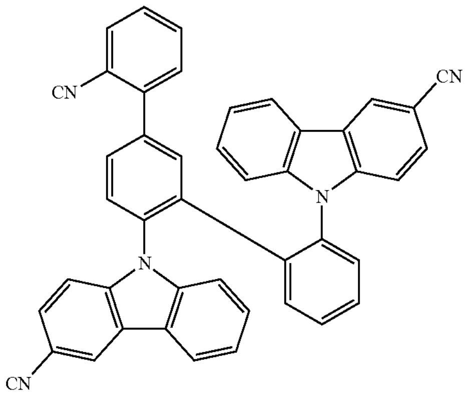
211
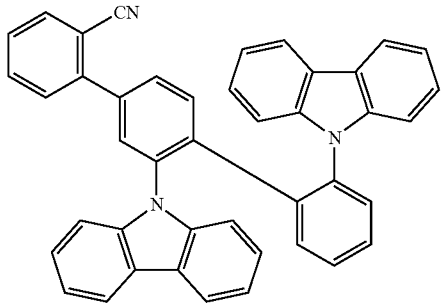
212
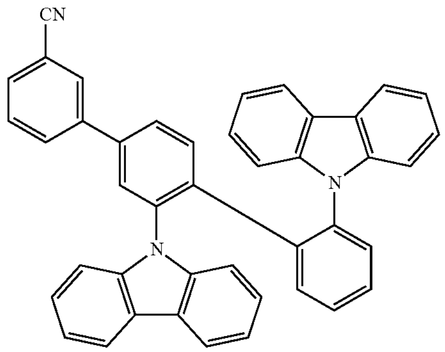
213
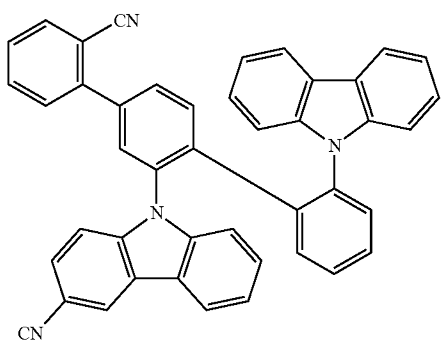
-continued
214
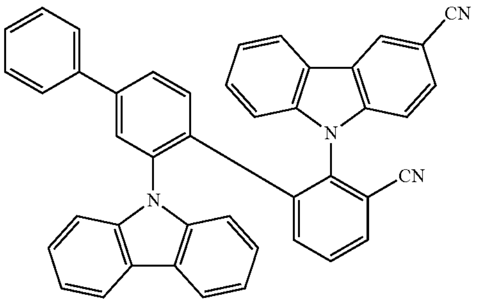
215
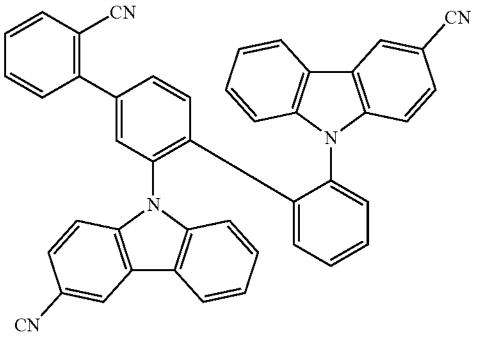
216
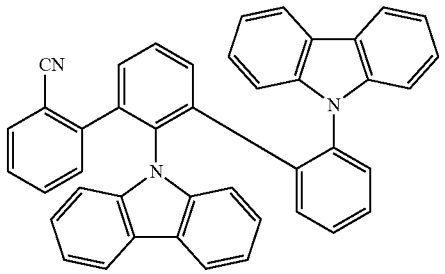
217
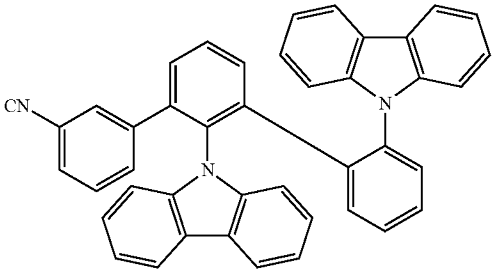
218
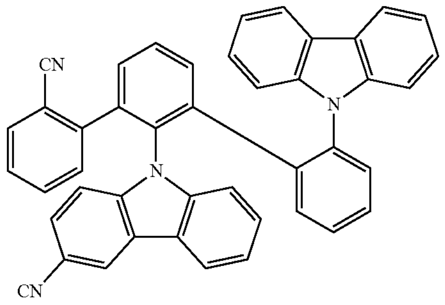

-continued
219
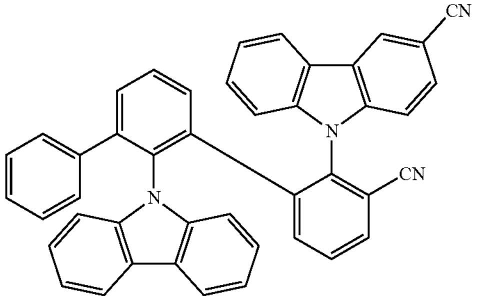
220
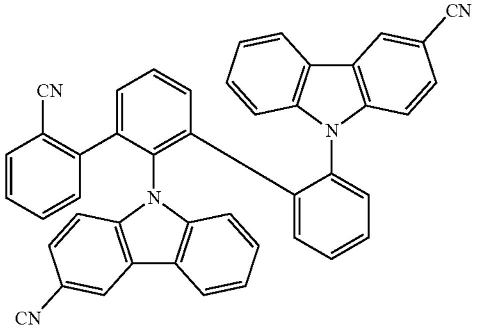
221
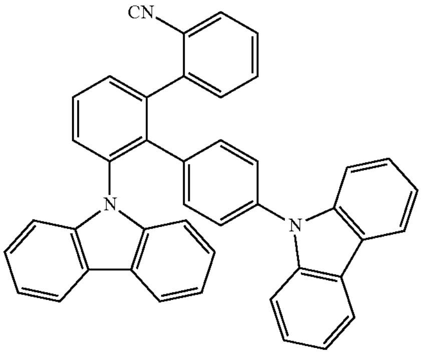
222
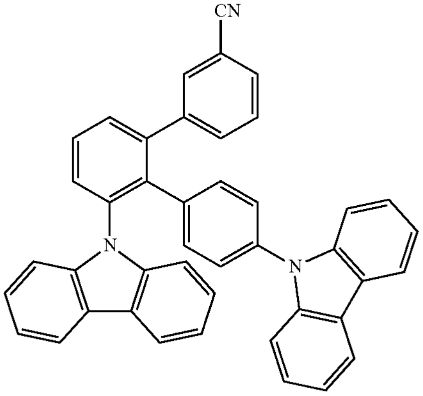
-continued
223
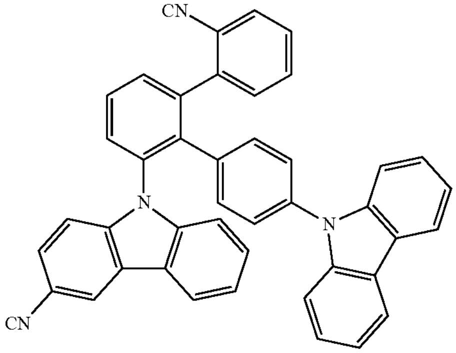
224
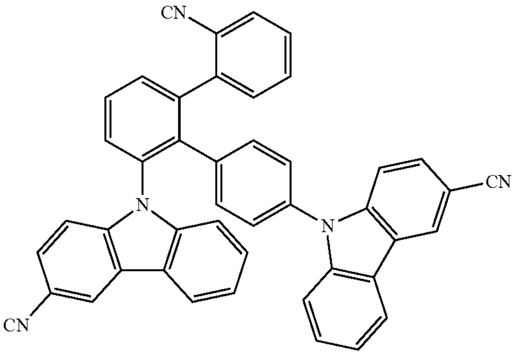
225
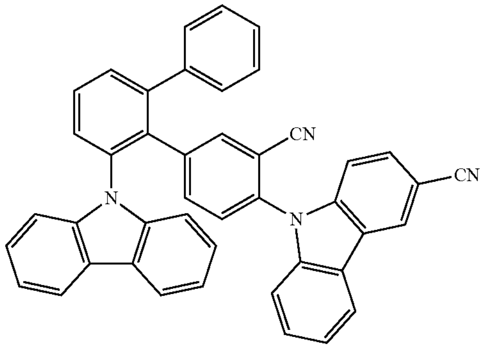
226
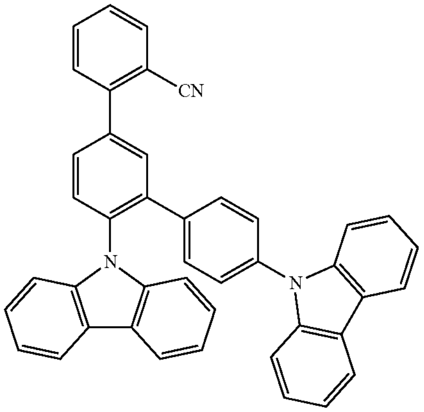

-continued
227
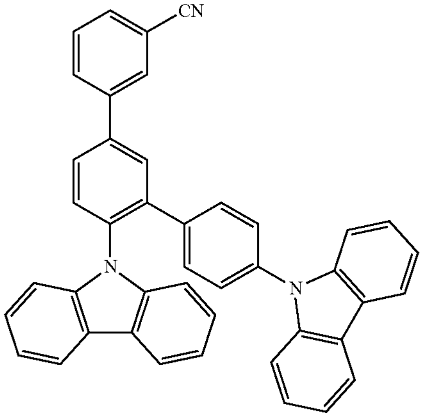
228
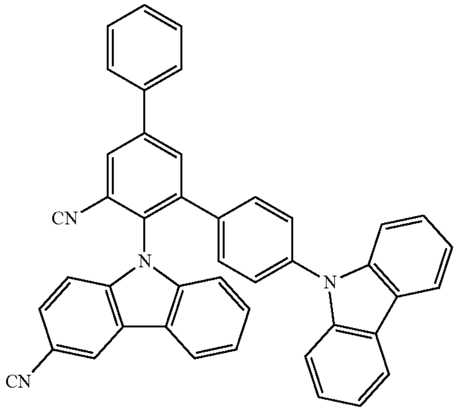
229
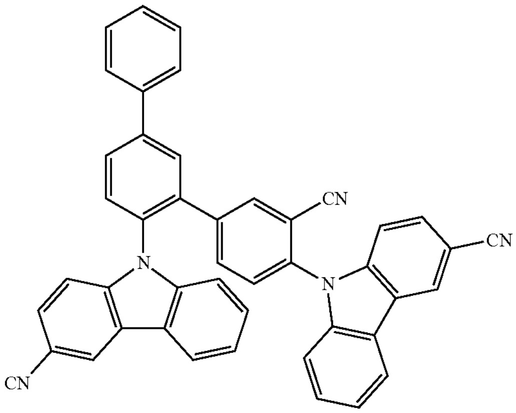
-continued
230
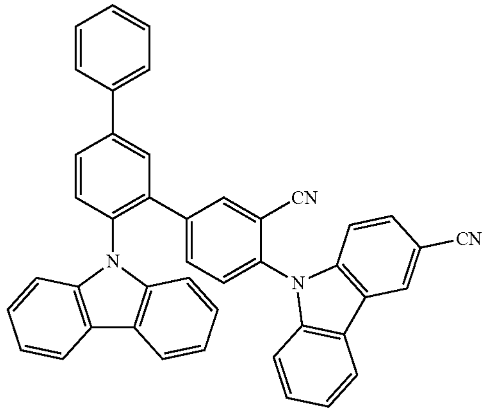
231
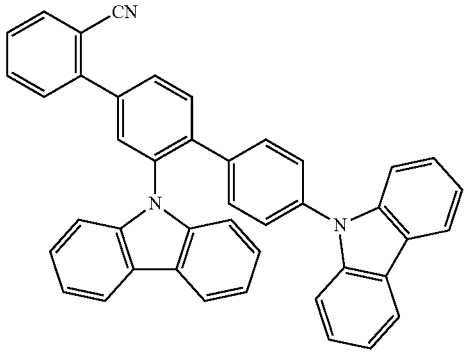
232
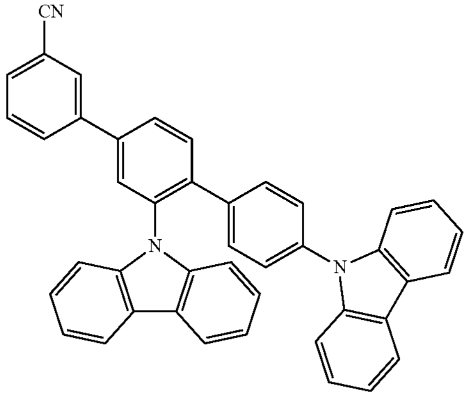
233
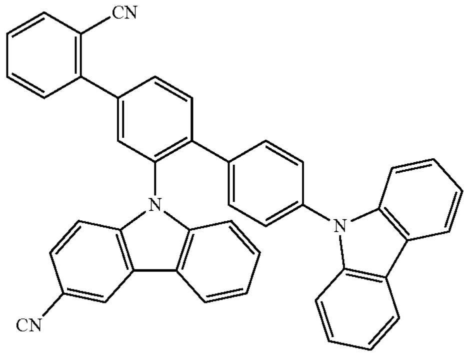

234
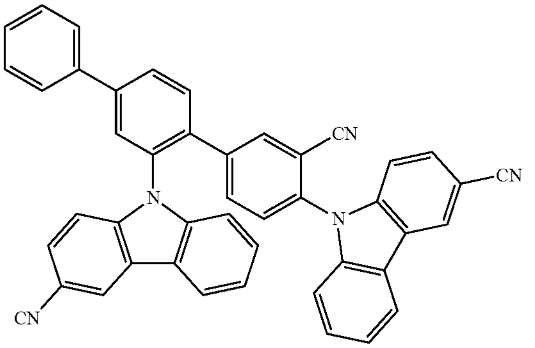
235
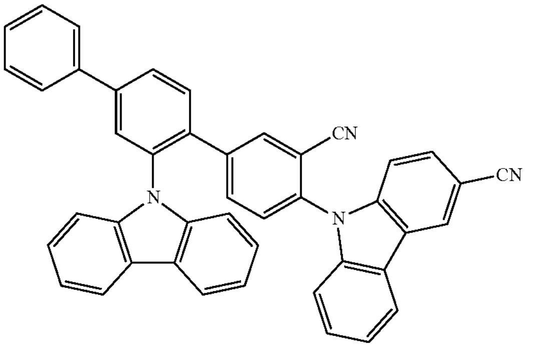
236
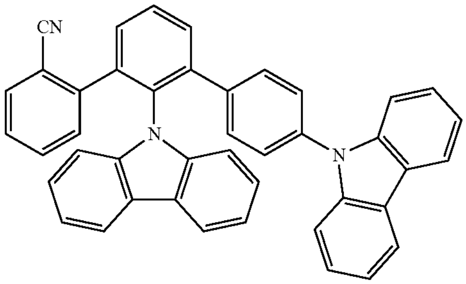
237
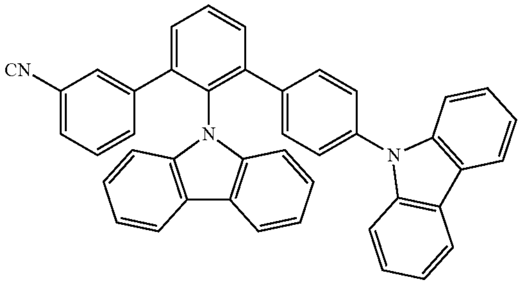
238
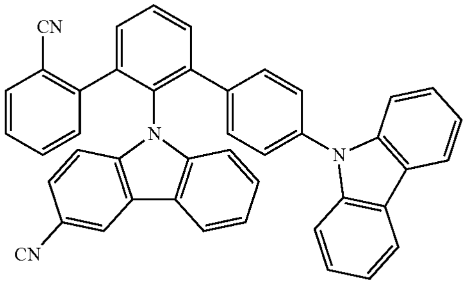
239
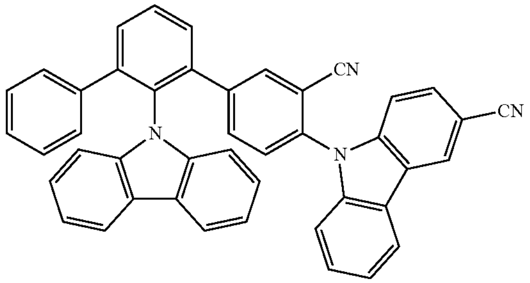
240
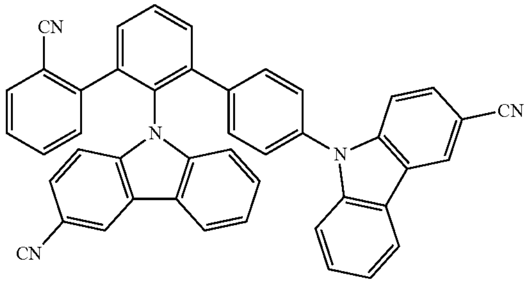
241
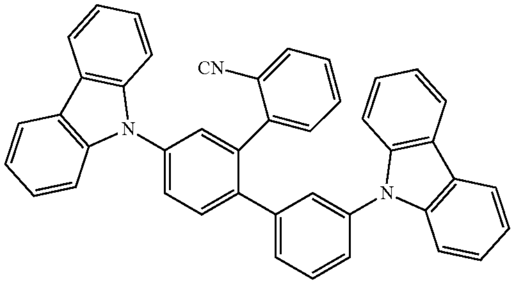
242
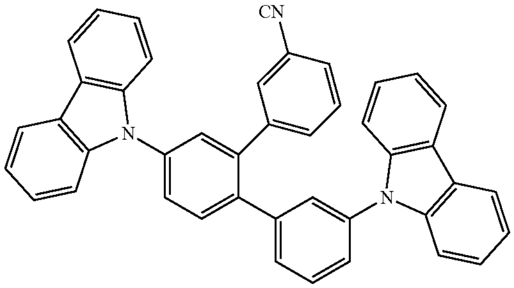
243
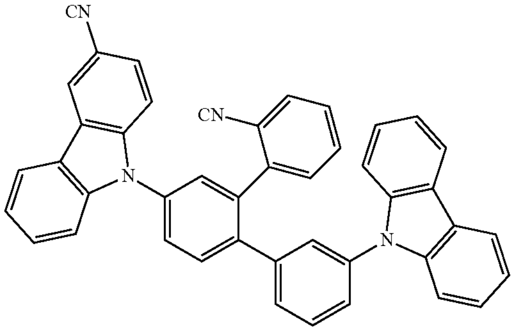

-continued
244
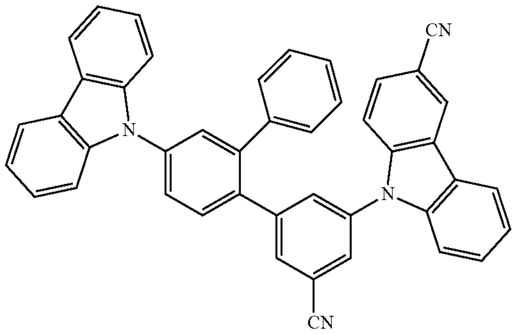
245
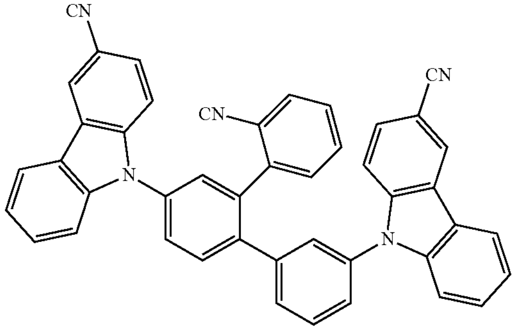
246
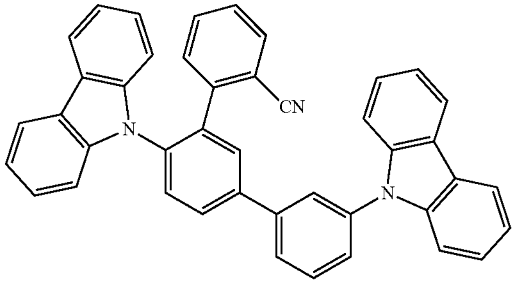
247
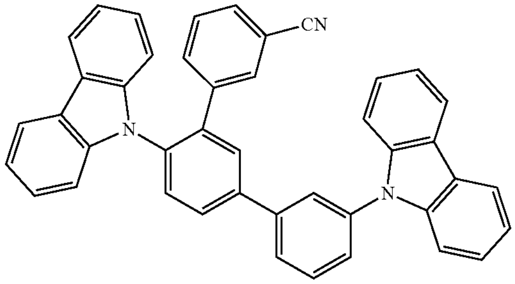
248
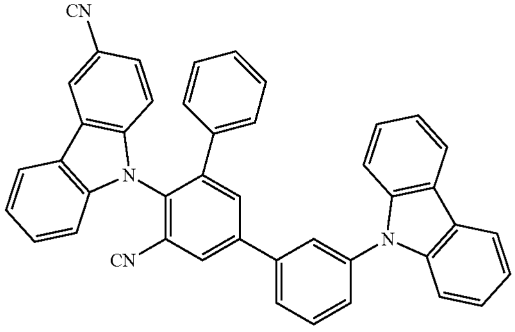
-continued
249
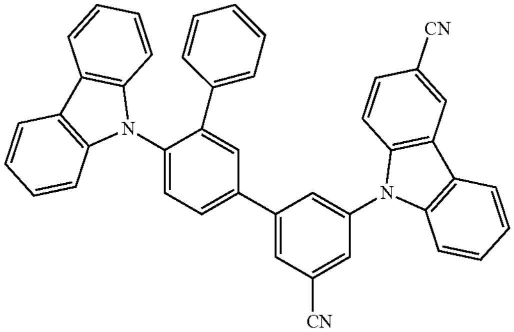
250
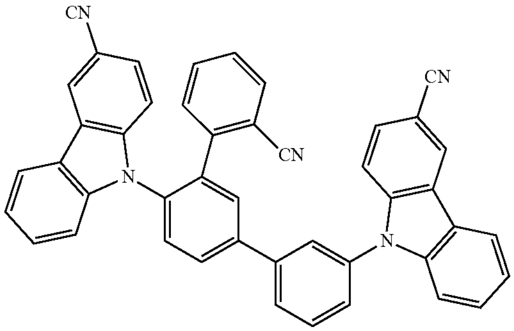
251
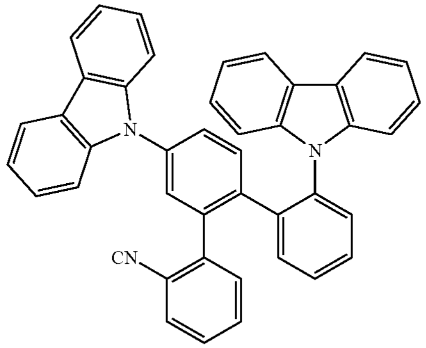
252
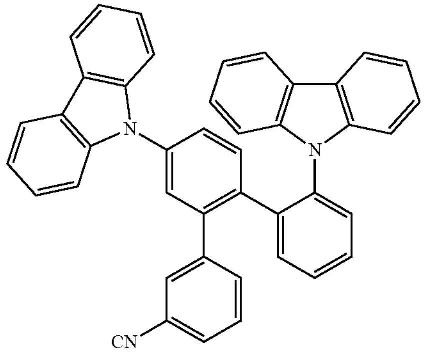

-continued
253
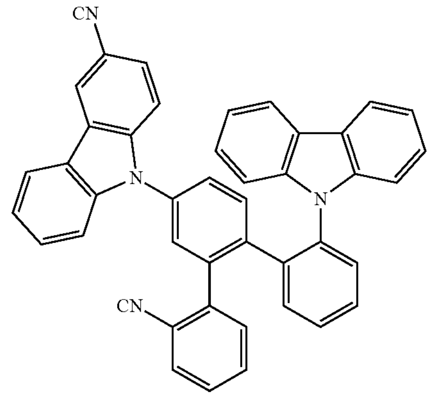
254
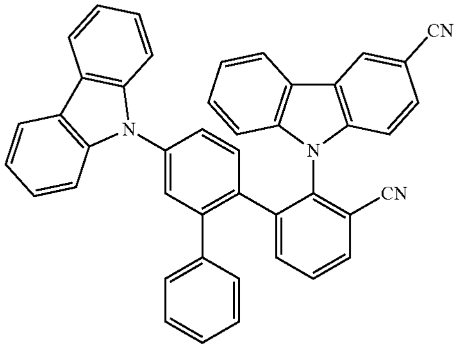
255
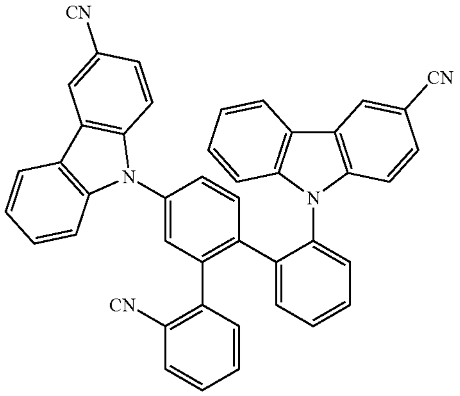
256
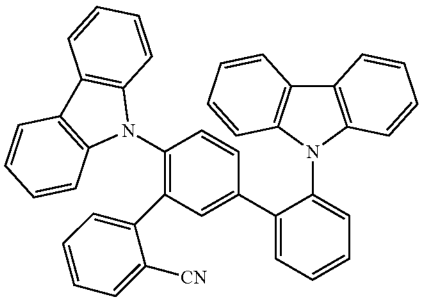
-continued
257
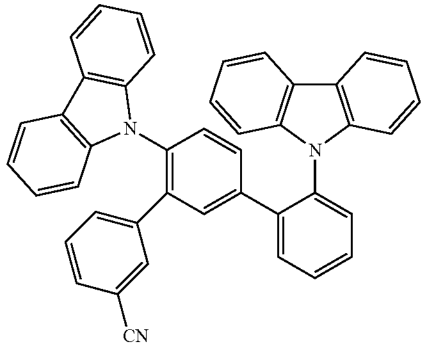
258
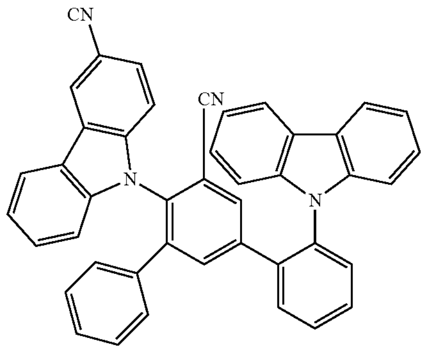
259
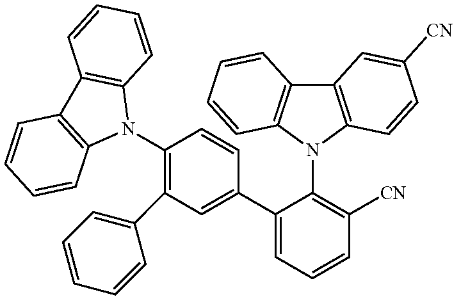
260
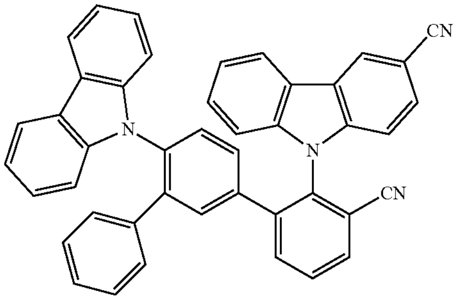
261
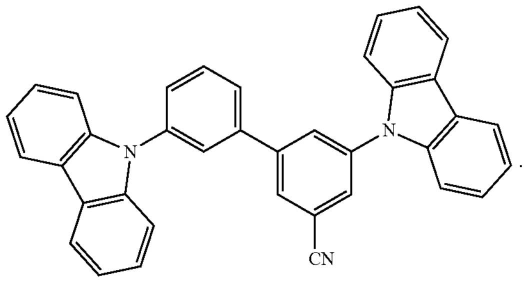

In an embodiment, the hole-transporting host may be one of Compounds H-H1 to H-H104, but embodiments of the present disclosure are not limited thereto:
H-H1
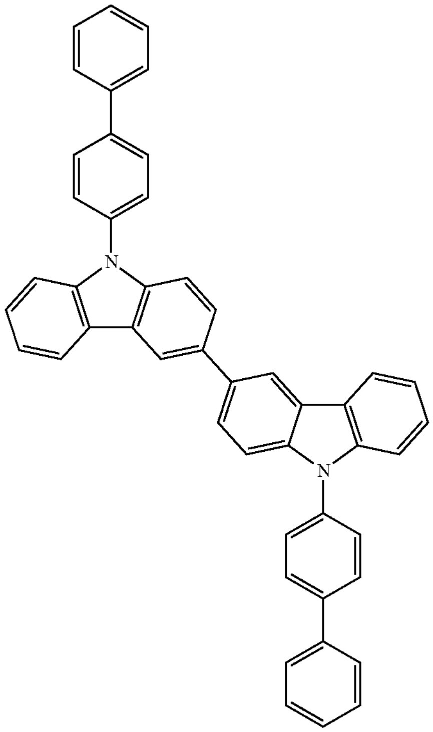
H-H2
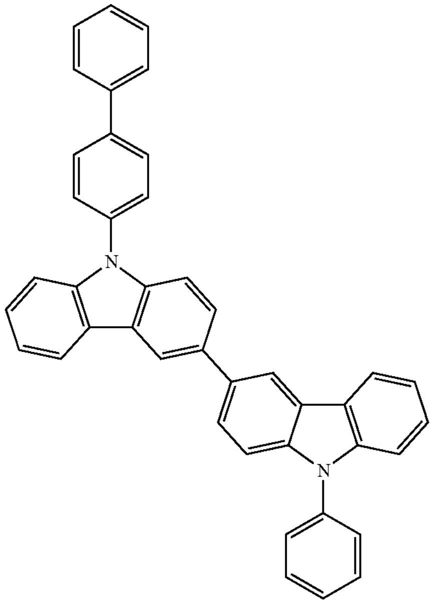
-continued
H-H3
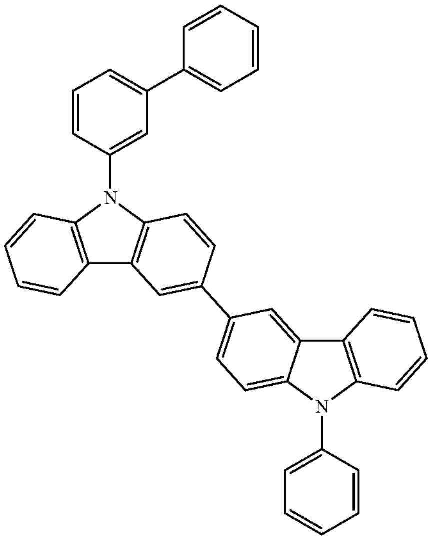
H-H4
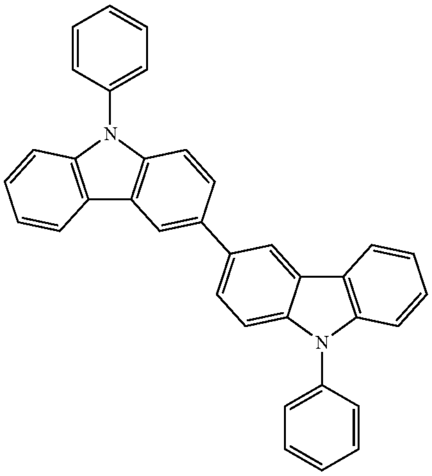
H-H5
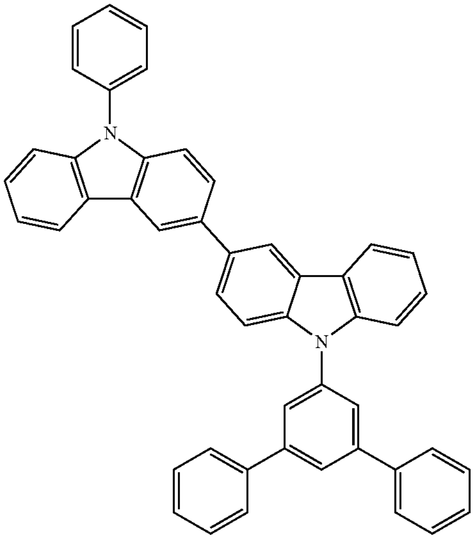

-continued
H-H6
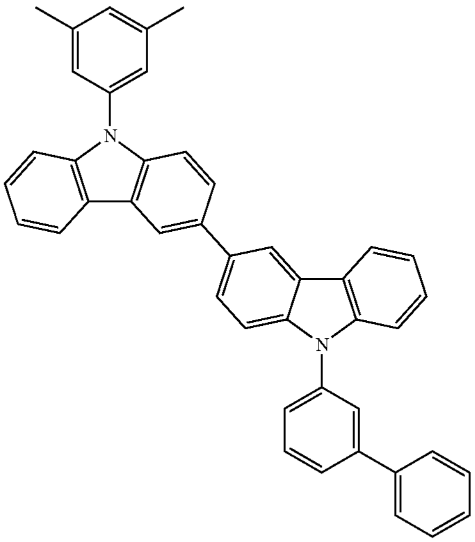
H-H7
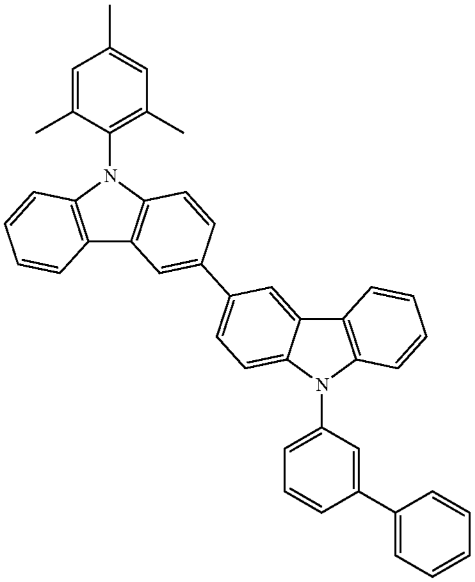
-continued
H-H8
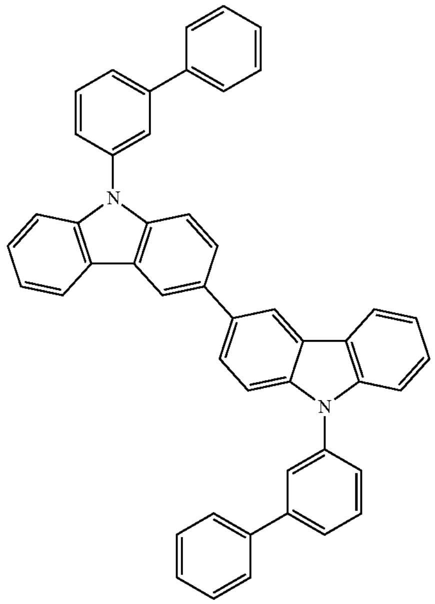
H-H9
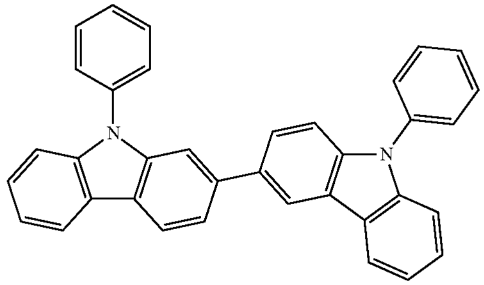
H-H10
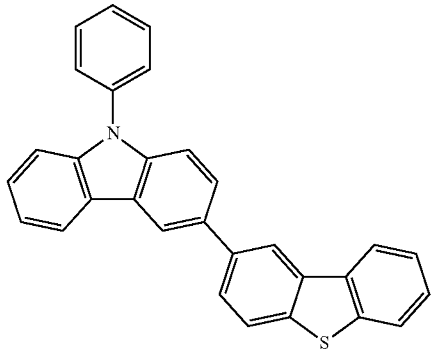
H-H11
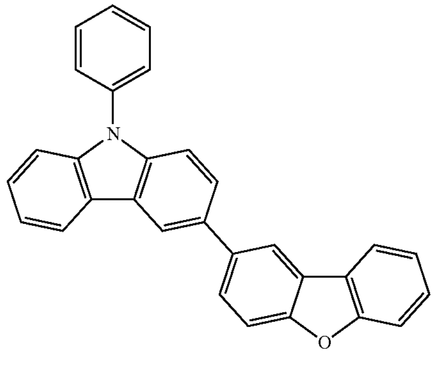

H-H12
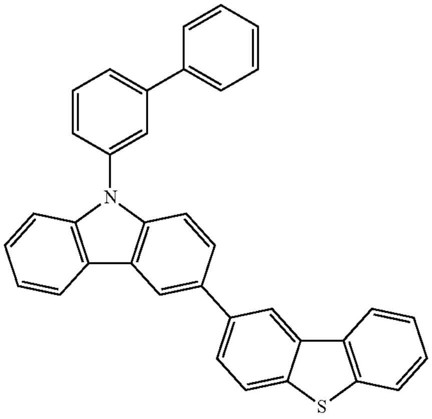
H-H13
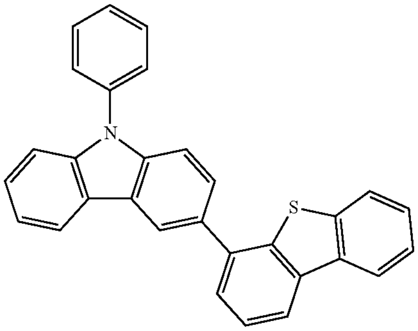
H-H14
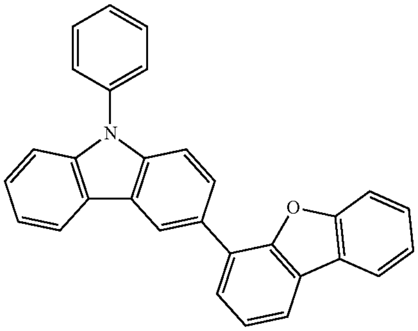
H-H15
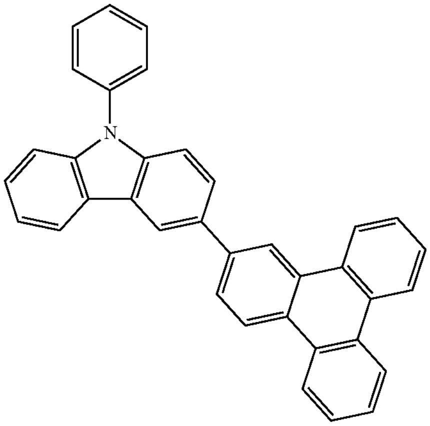
H-H16
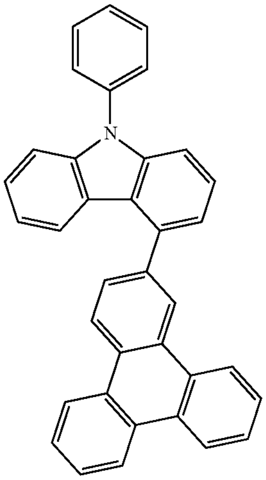
H-H17
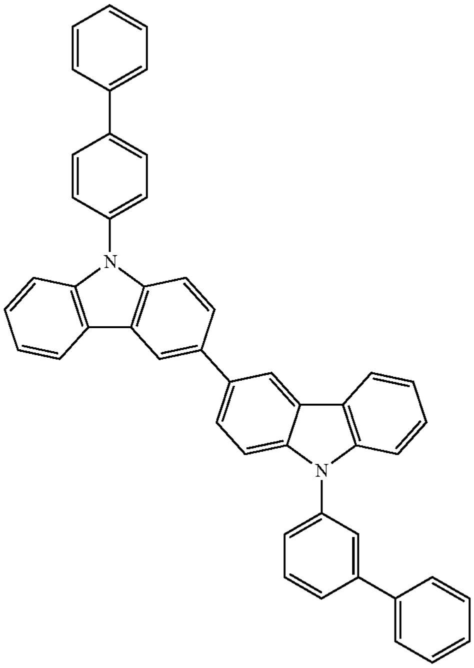
H-H18
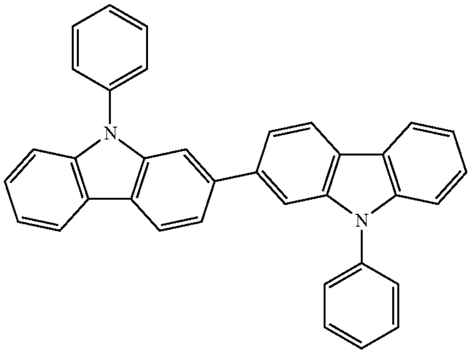

-continued
H-H19
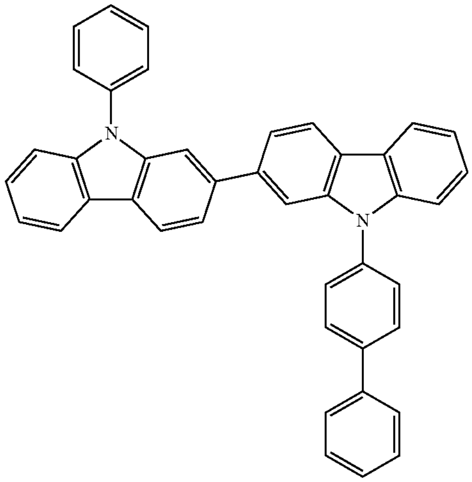
H-H20
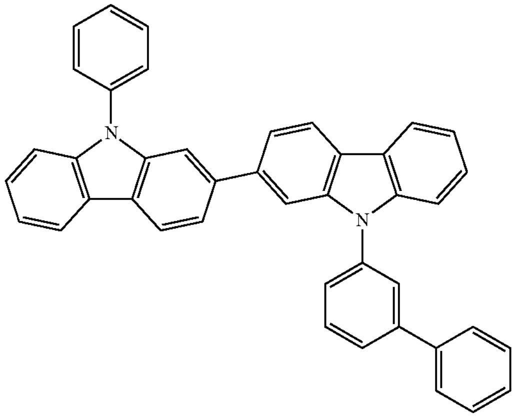
H-H21
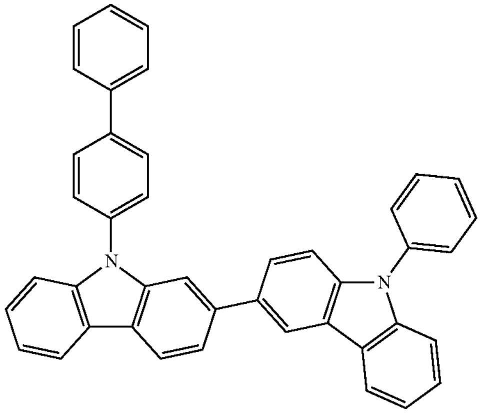
-continued
H-H22
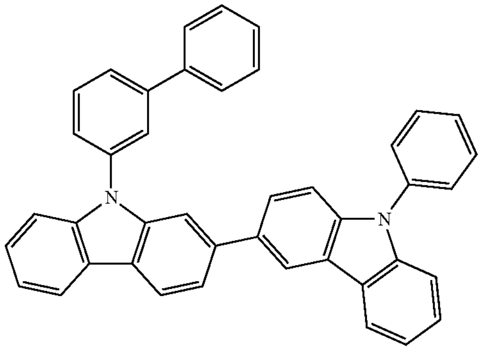
H-H23
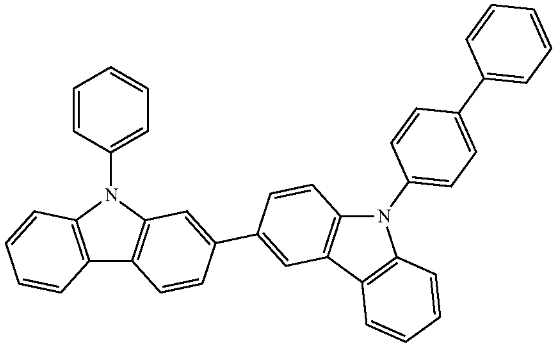
H-H24
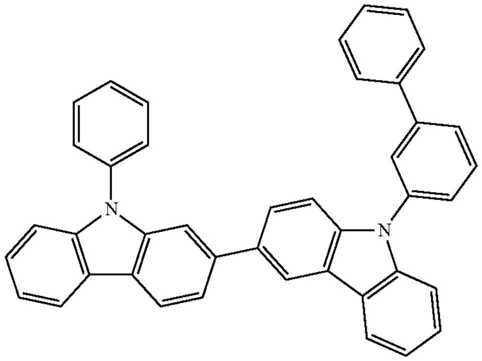
H-H25
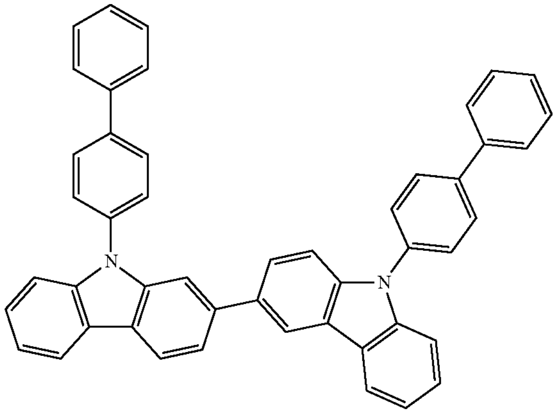

-continued
H-H26
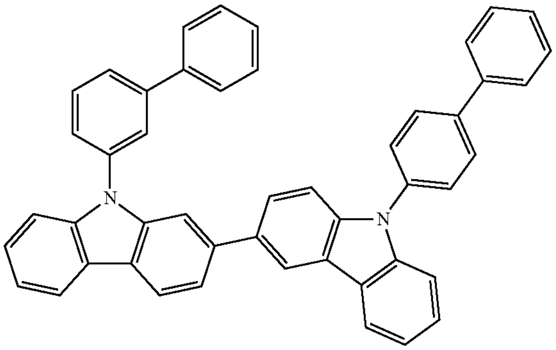
H-H27
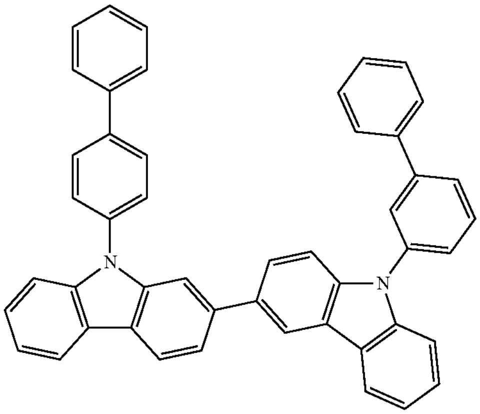
H-H28
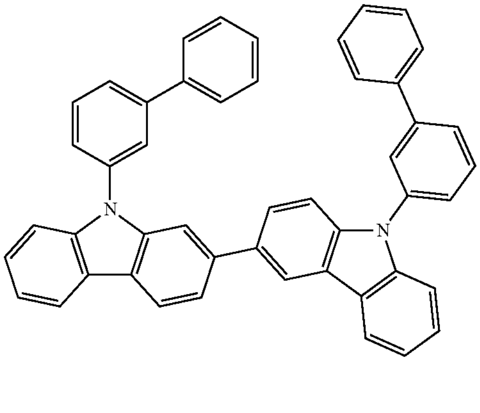
-continued
H-H29
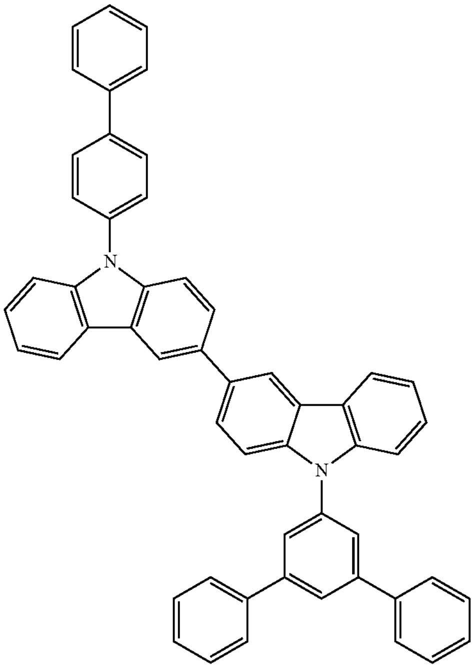
H-H30
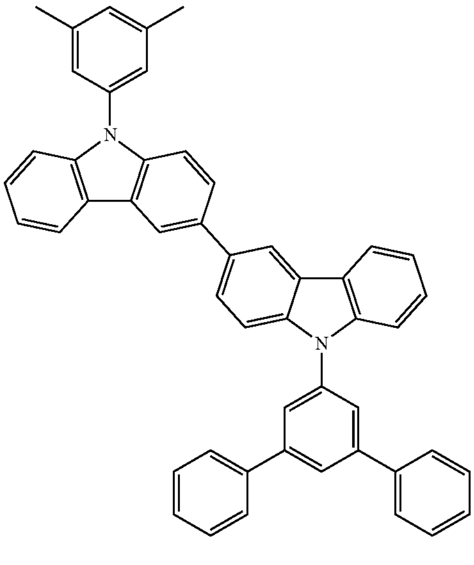

-continued
H-H31
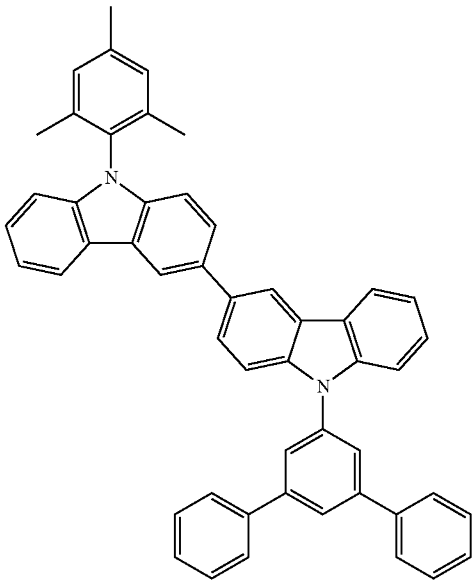
H-H32
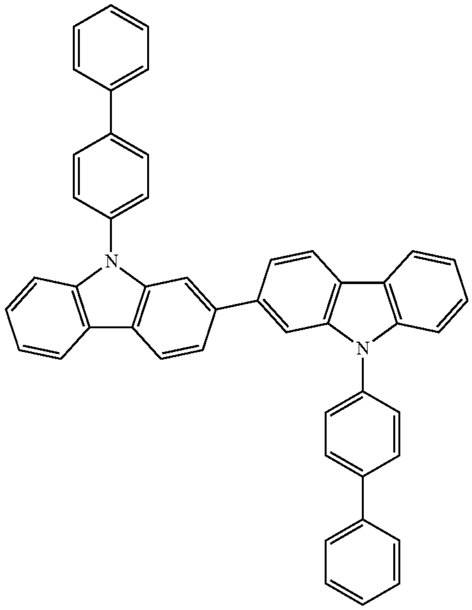
-continued
H-H33
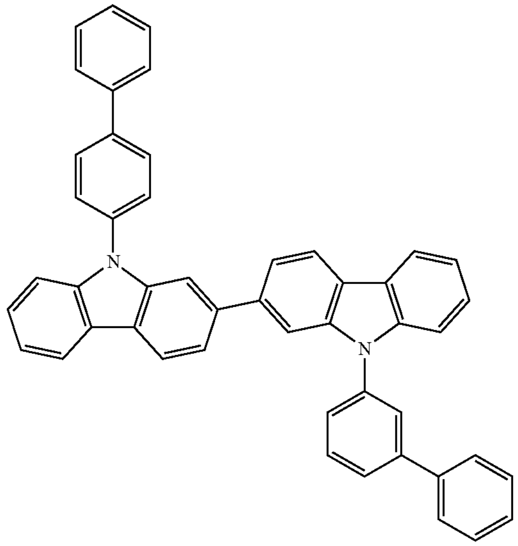
H-H34
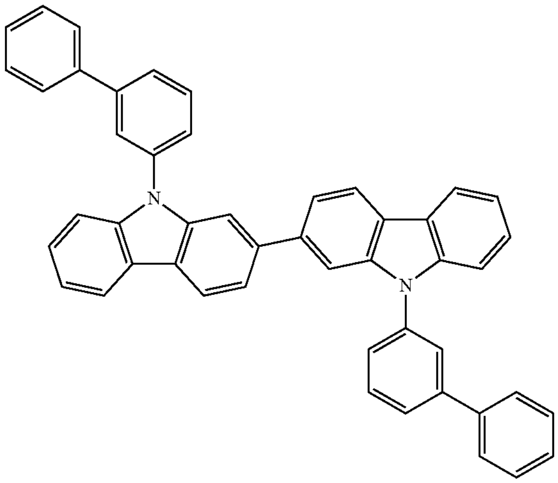
H-H35
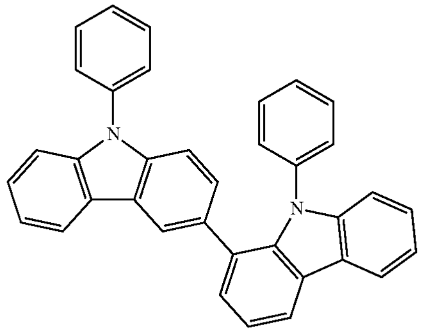

-continued
H-H36
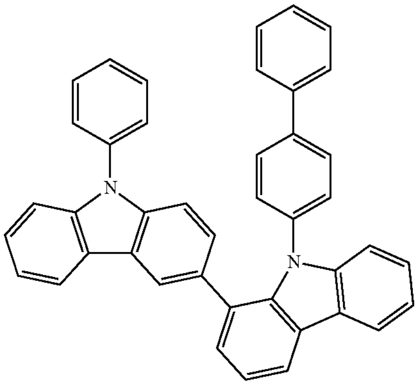
H-H37
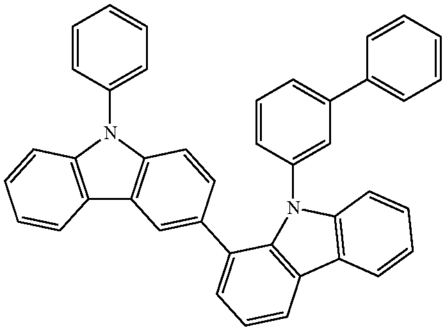
H-H38
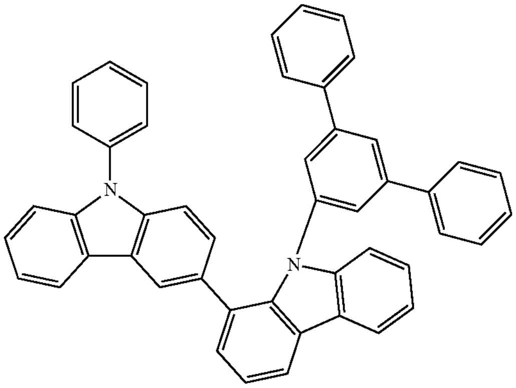
H-H39
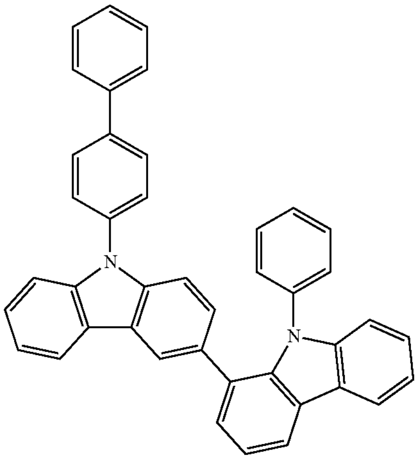
-continued
H-H40
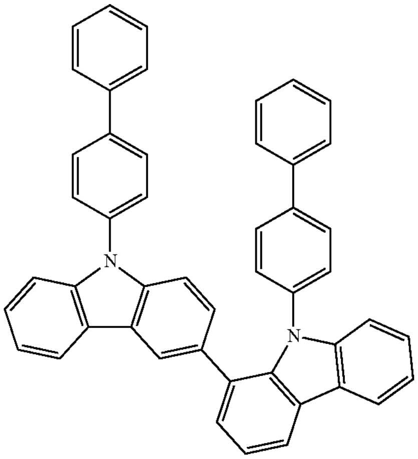
H-H41
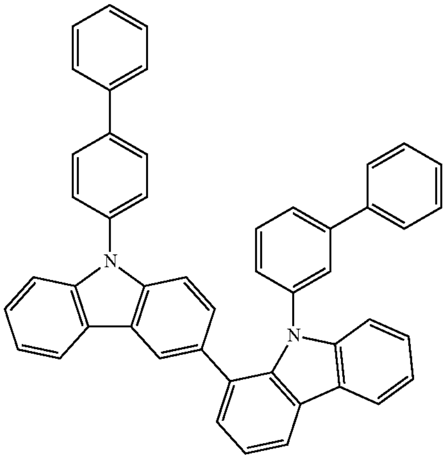
H-H42
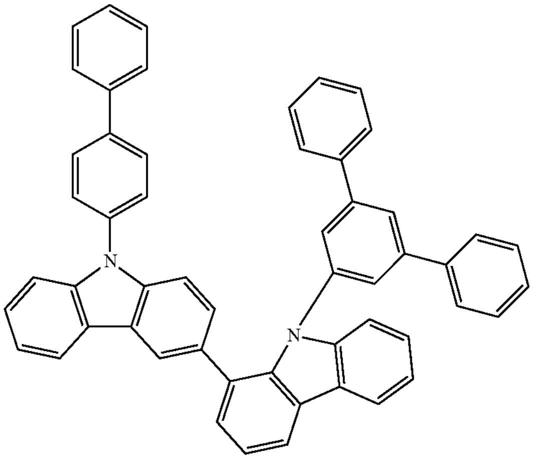

-continued
H-H43
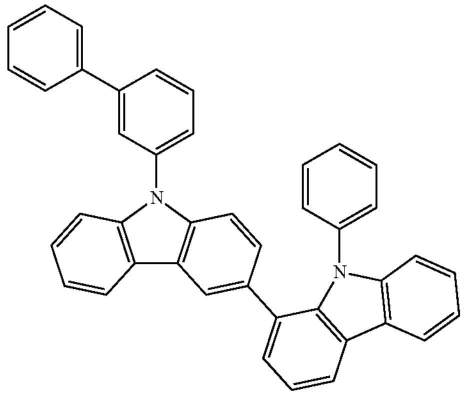
H-H44
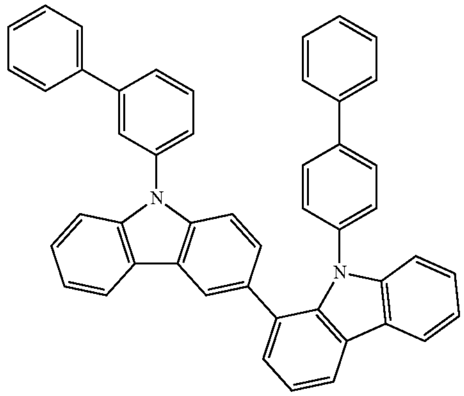
H-H45
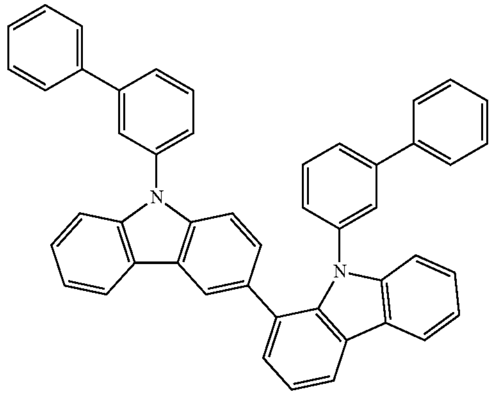
H-H46
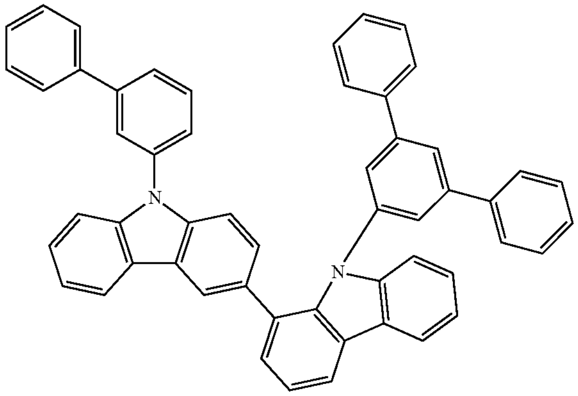
-continued
H-H47
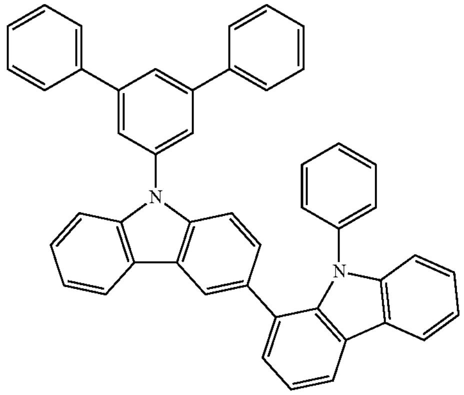
H-H48
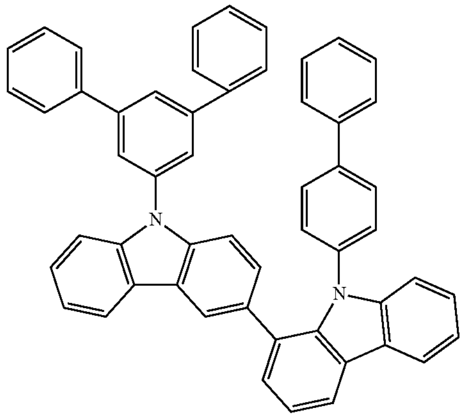
H-H49
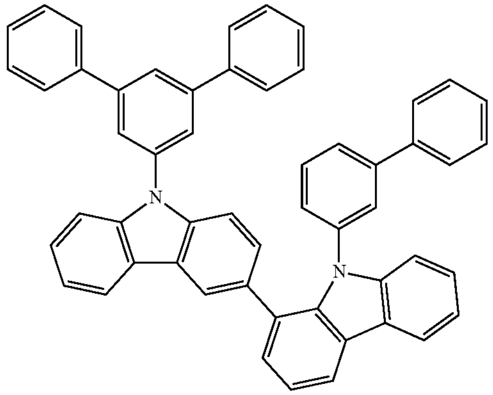

-continued
H-H50
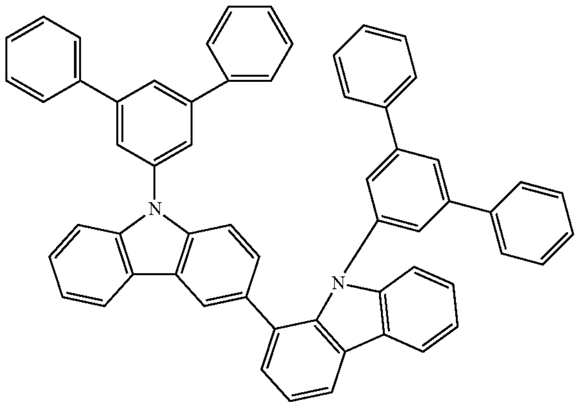
H-H51
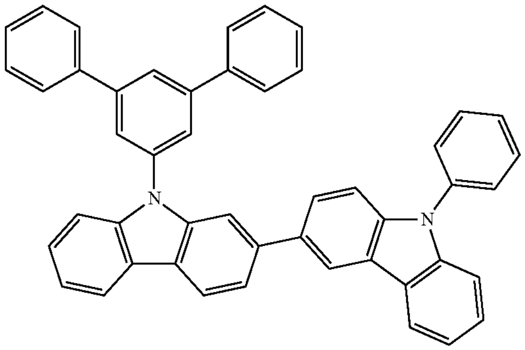
H-H52
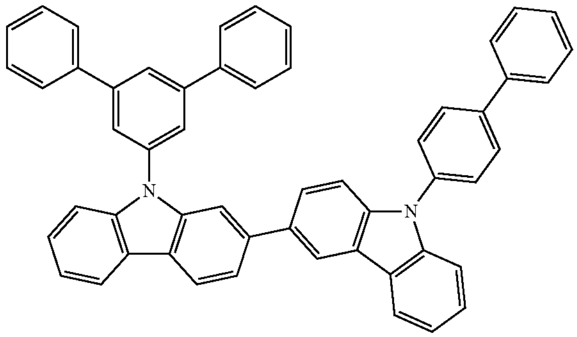
-continued
H-H53
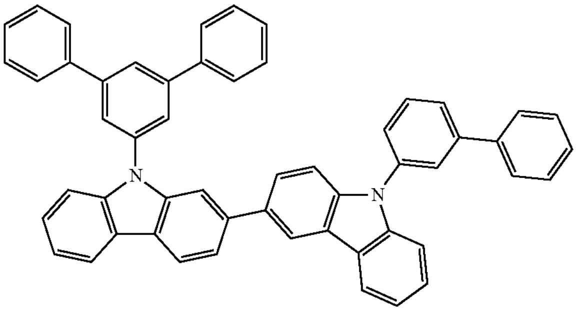
H-H54
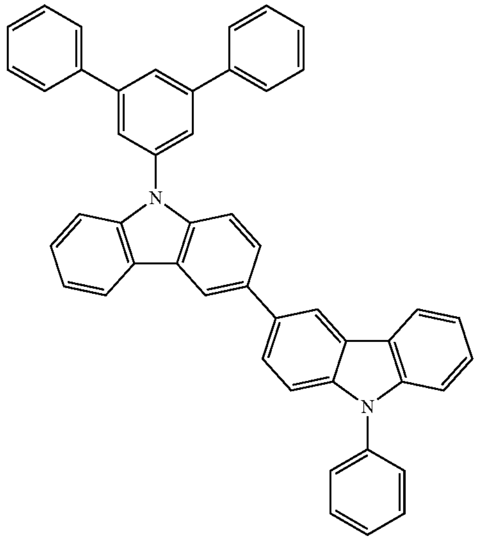
H-H55
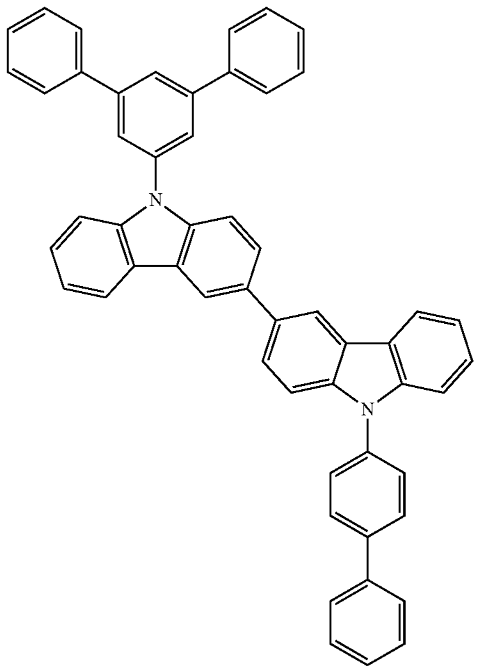

-continued
H-H56
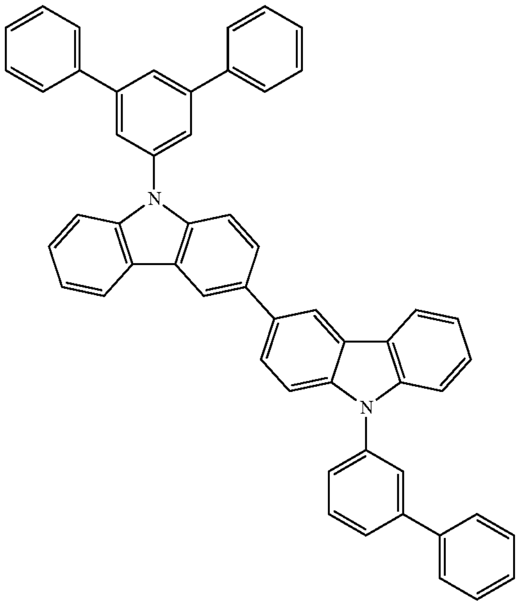
H-H57
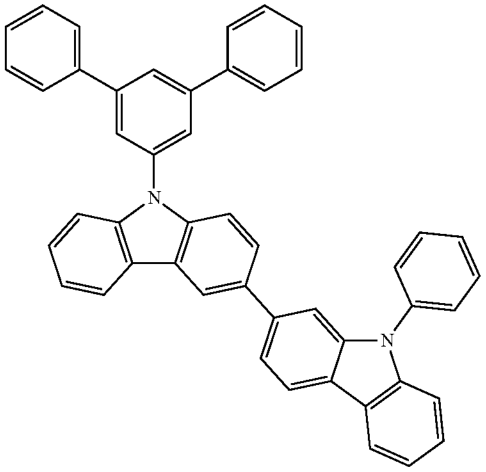
H-H58
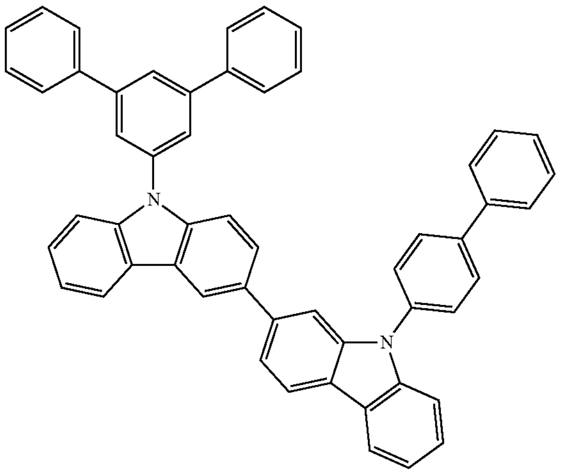
-continued
H-H59
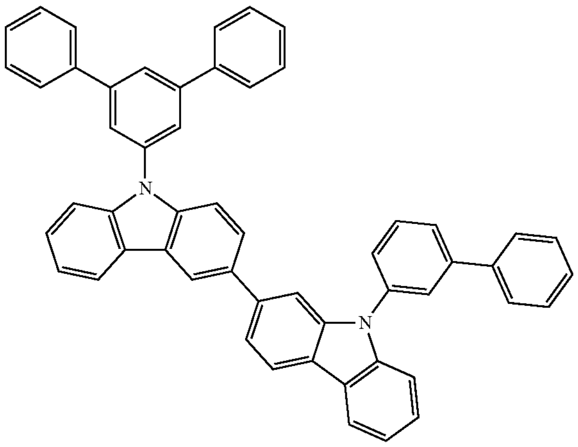
H-H60
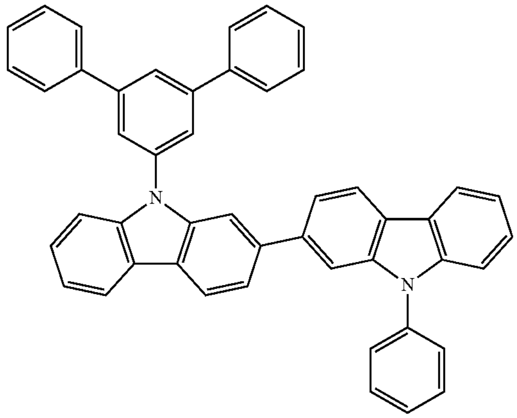
H-H61
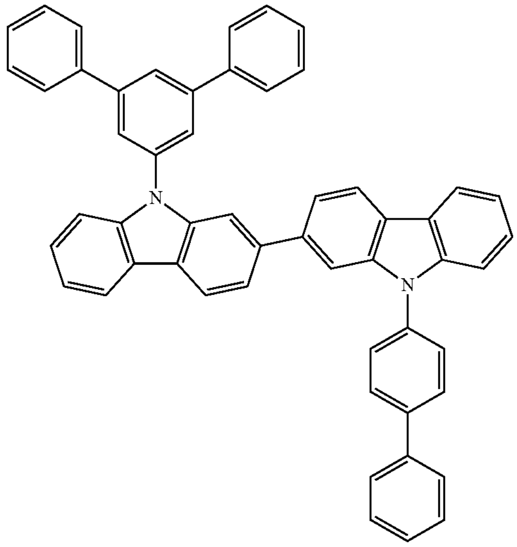

-continued
H-H62
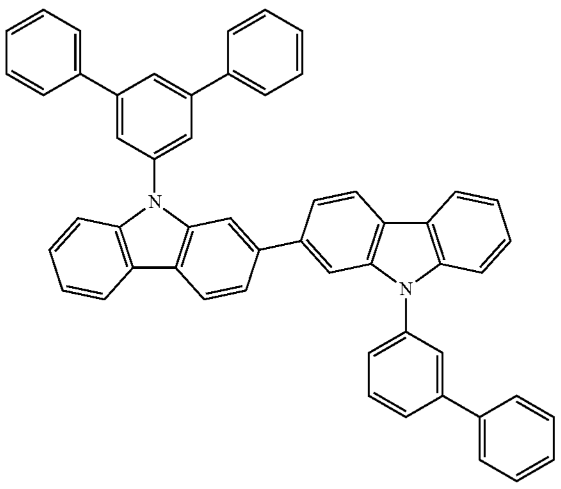
H-H63
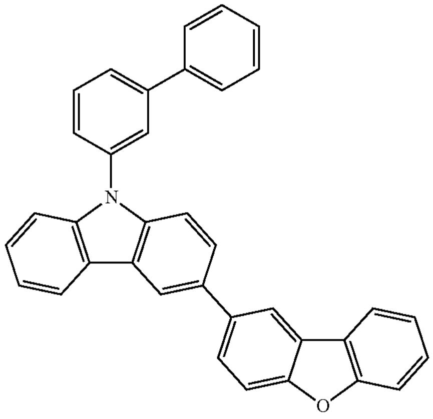
H-H64
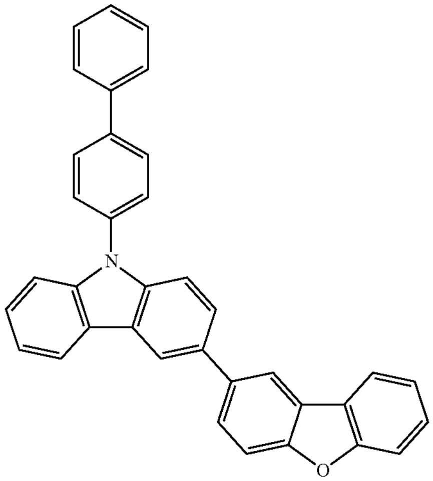
-continued
H-H65
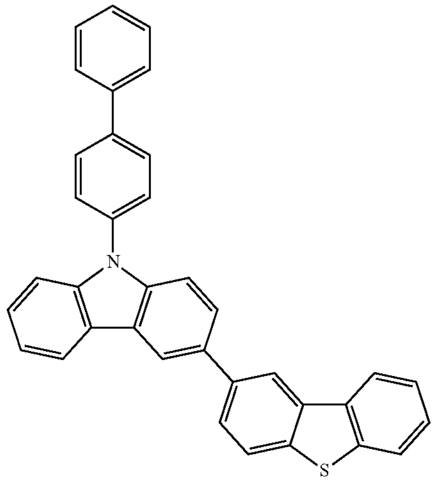
H-H66
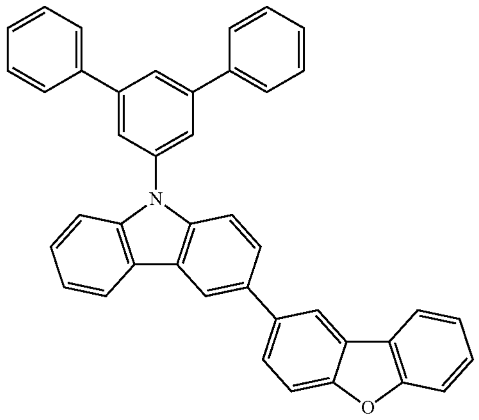
H-H67
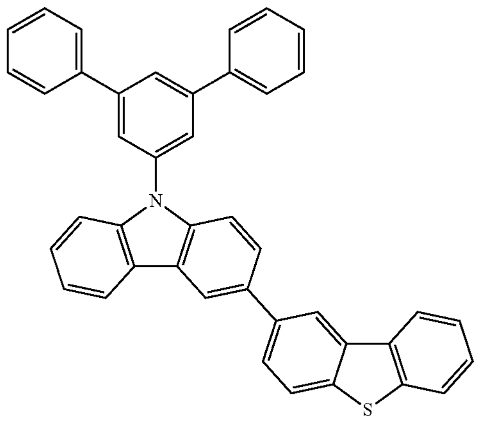

-continued
H-H68
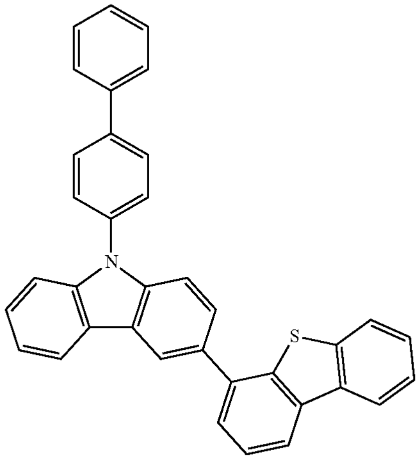
H-H69
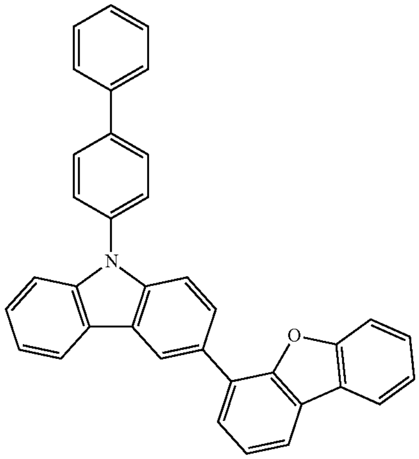
H-H70
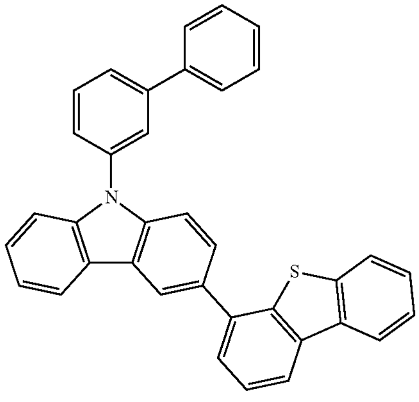
-continued
H-H71
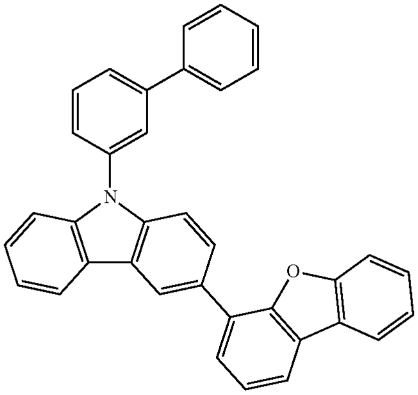
H-H72
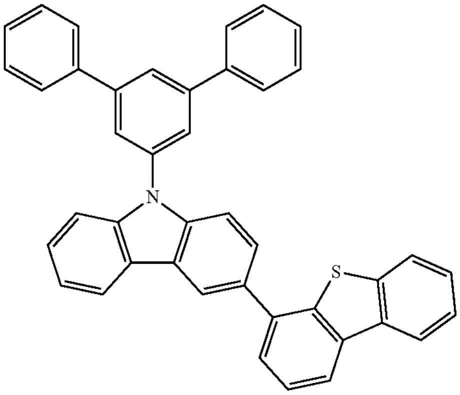
H-H73
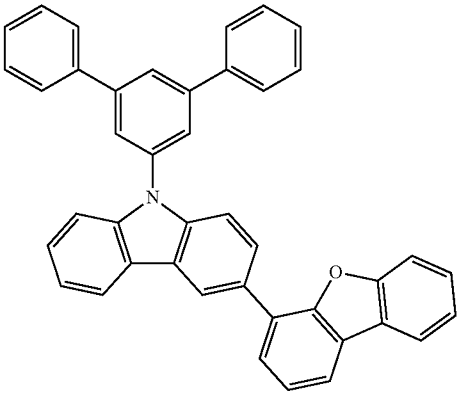
H-H74
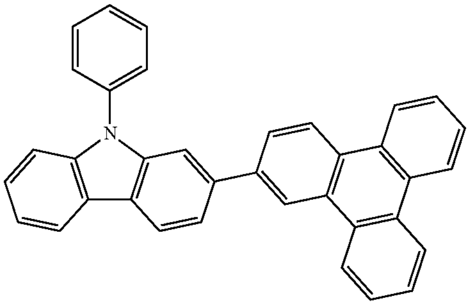

-continued
H-H75
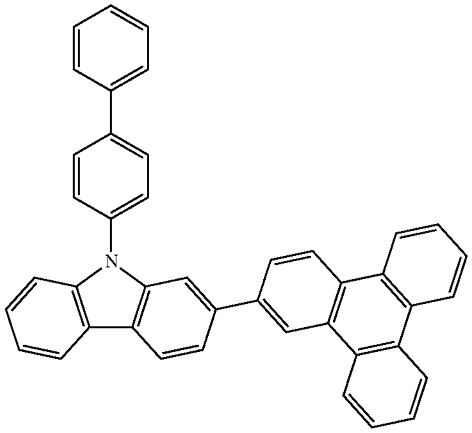
H-H76
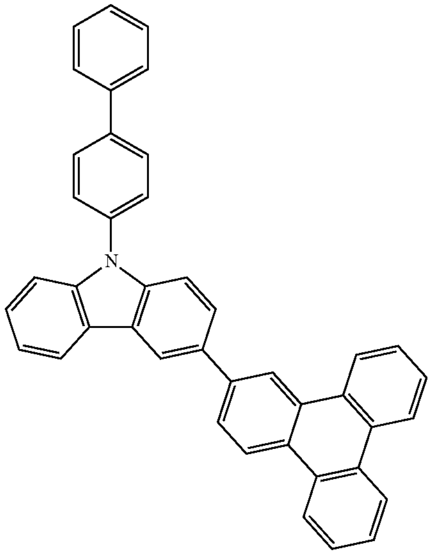
H-H77
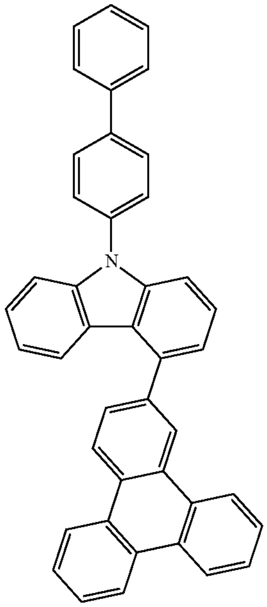
-continued
H-H78
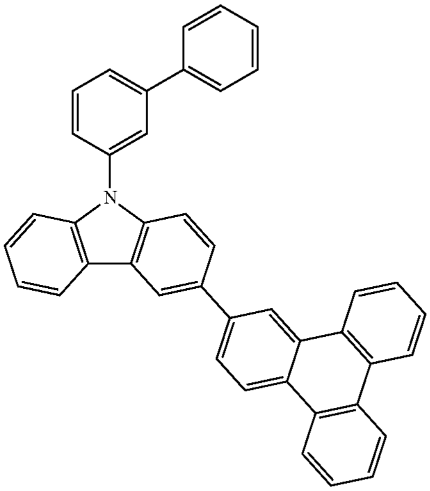
H-H79
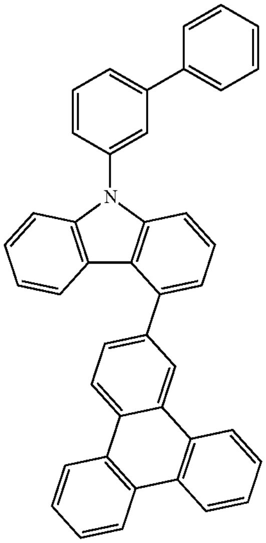
H-H80
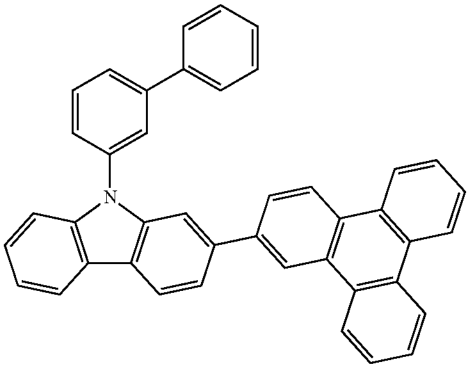

-continued
H-H81
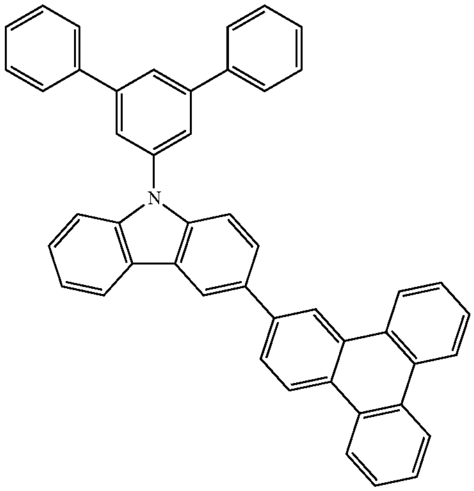
H-H82
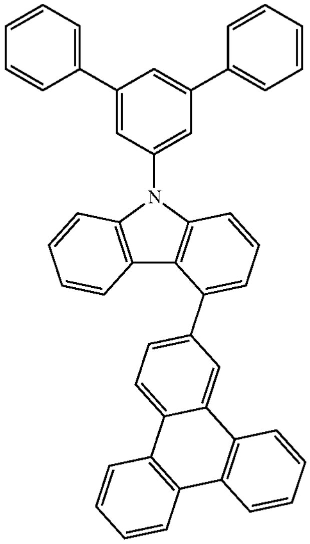
H-H83
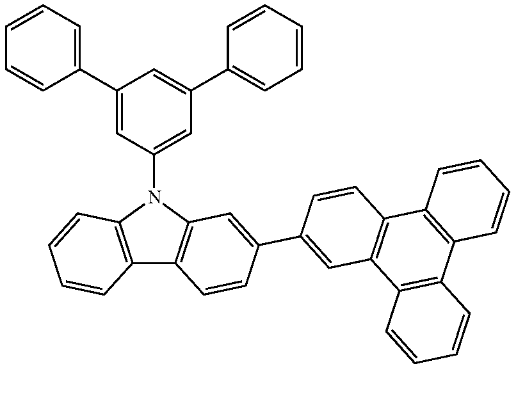
-continued
H-H84
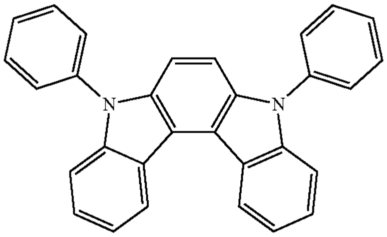
H-H85
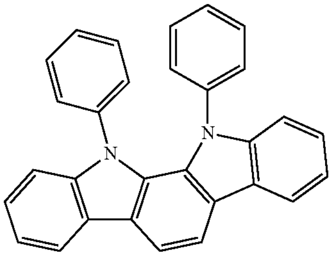
H-H86
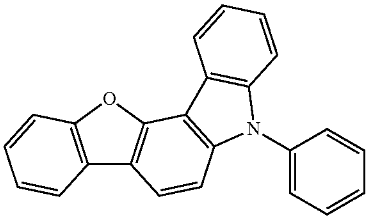
H-H87
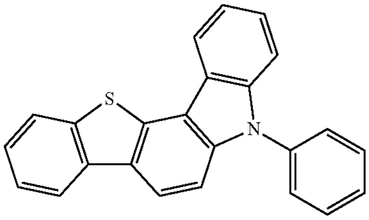
H-H88
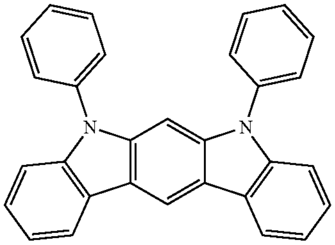
H-H89
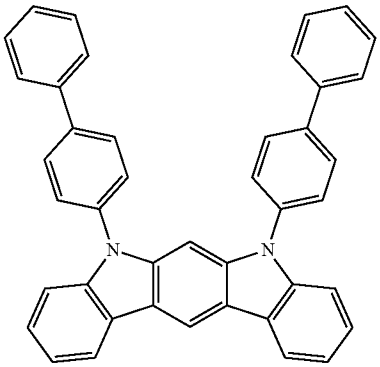

-continued
H-H90
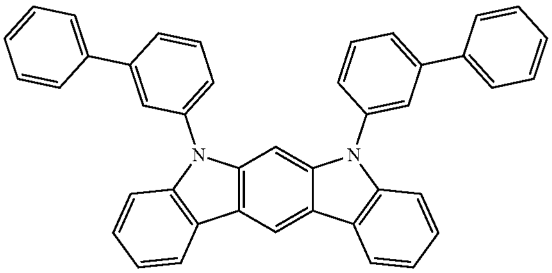
H-H91
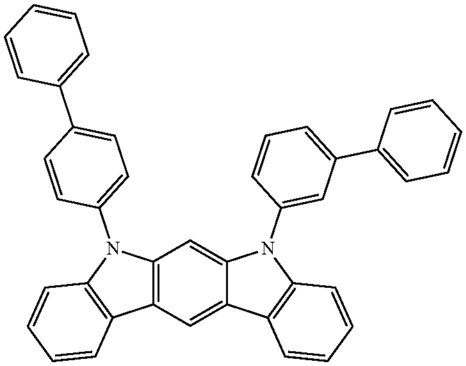
H-H92
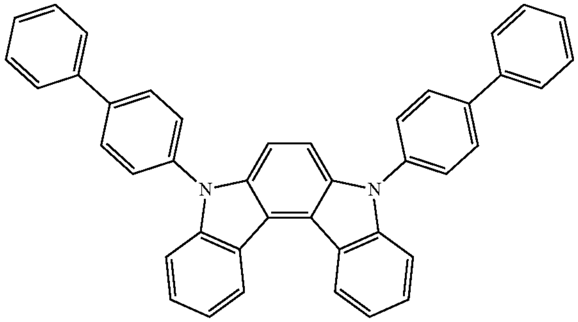
H-H93
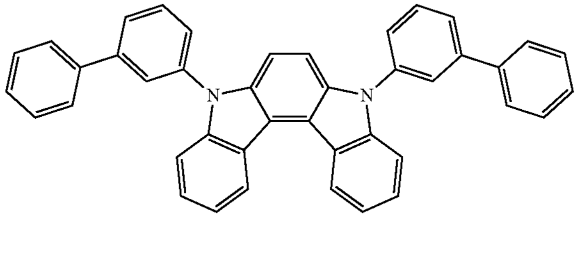
-continued
H-H94
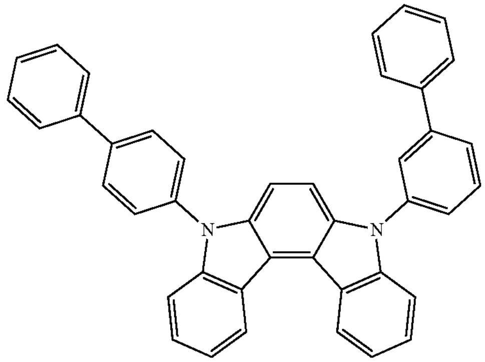
H-H95
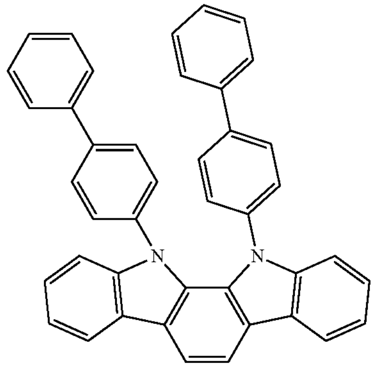
H-H96
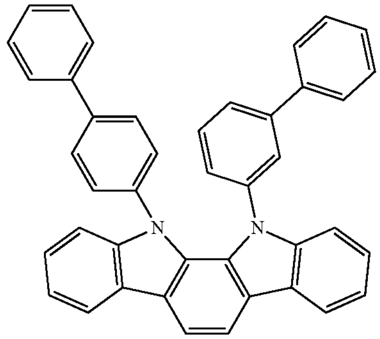
H-H97
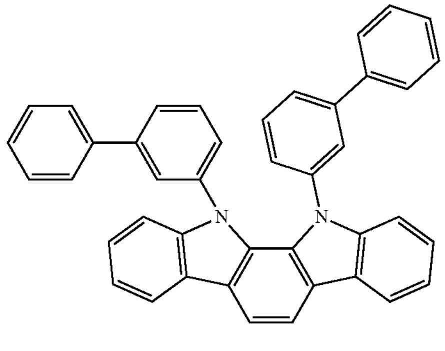

-continued
H-H98
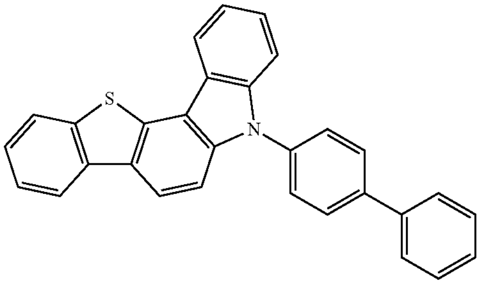
H-H99
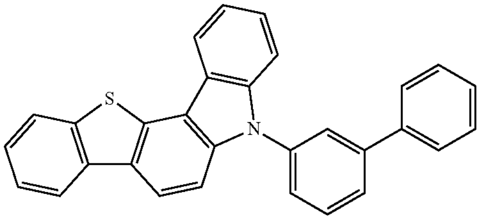
H-H100
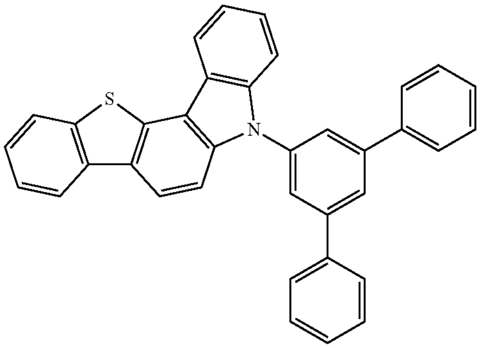
H-H101
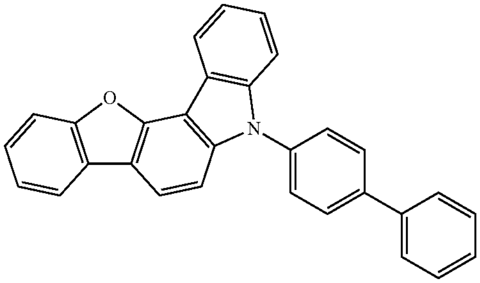
H-H102
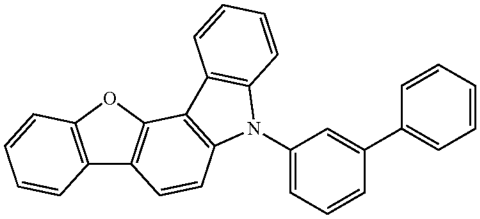
-continued
H-H103
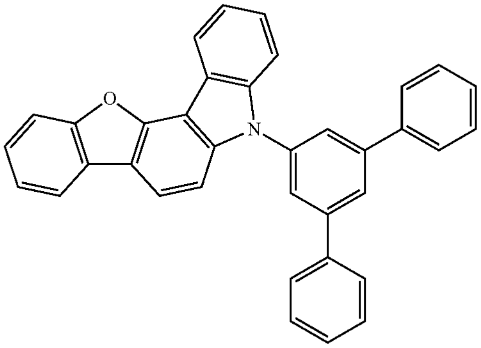
H-H104
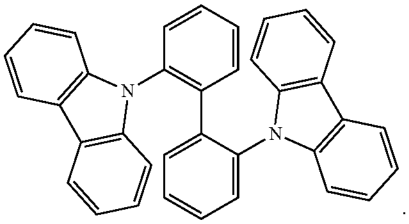
.
In an embodiment, the bipolar host may be Group HEH1, but embodiments of the present disclosure are not limited thereto:
Group HEH1
1
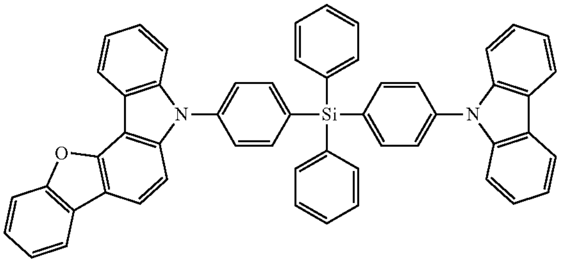
2
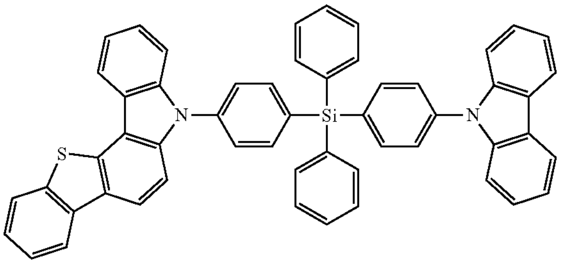

-continued
3
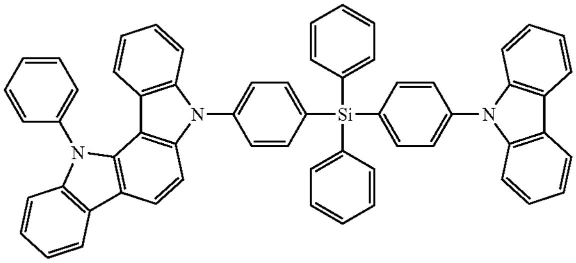
4
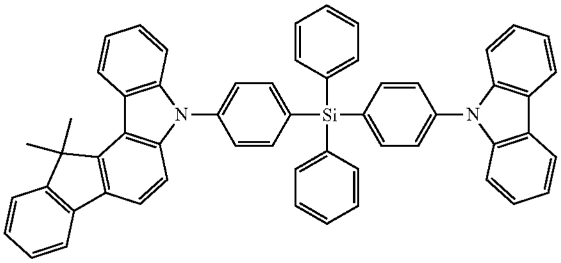
5
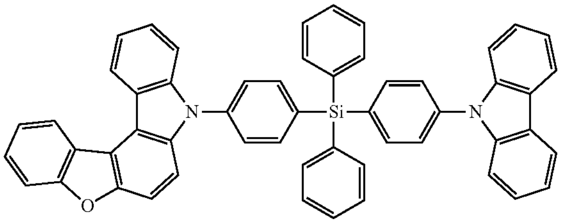
6
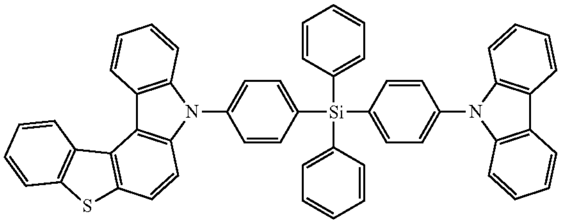
7
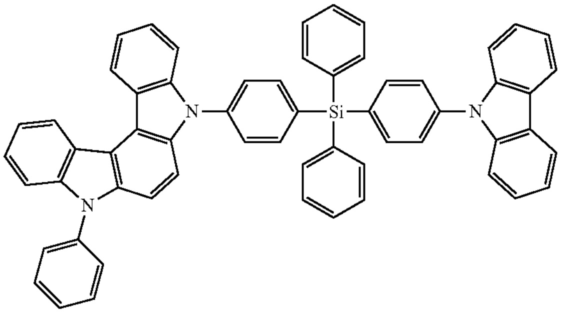
-continued
8
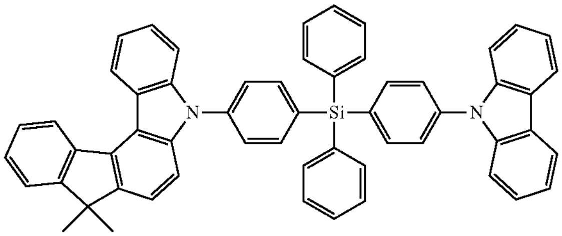
9
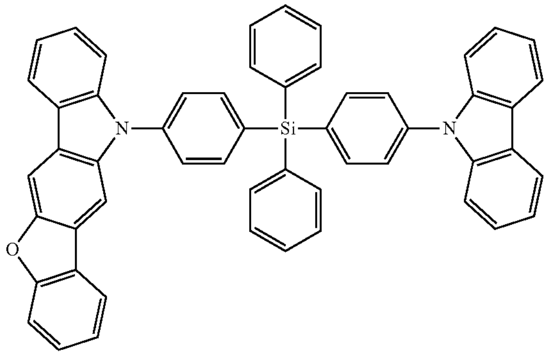
10
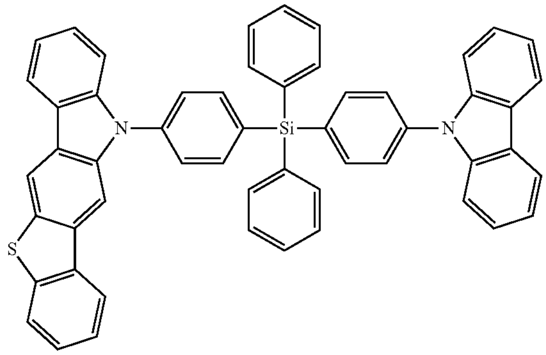
11
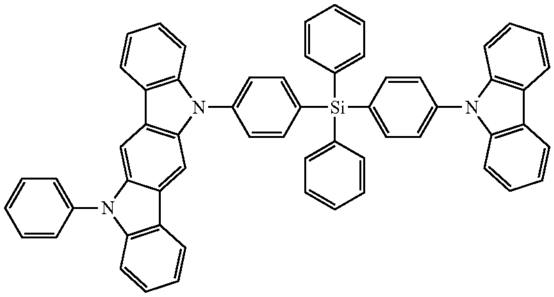

-continued
12
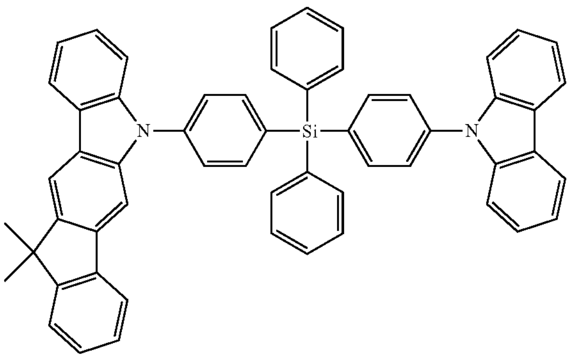
13
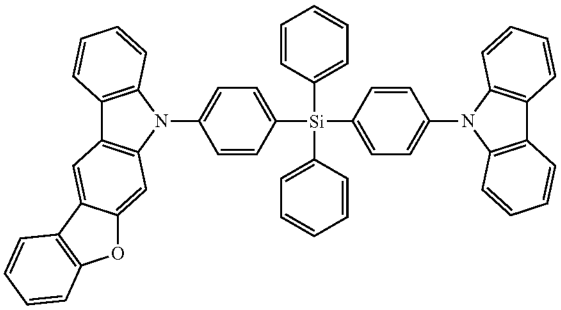
14
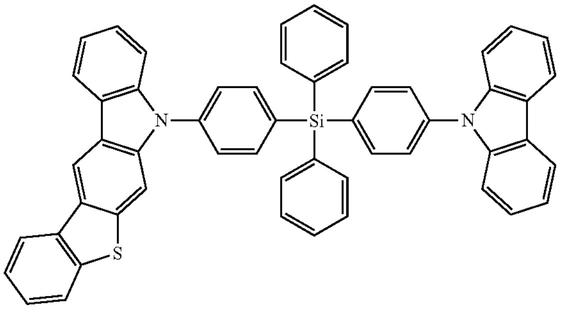
15
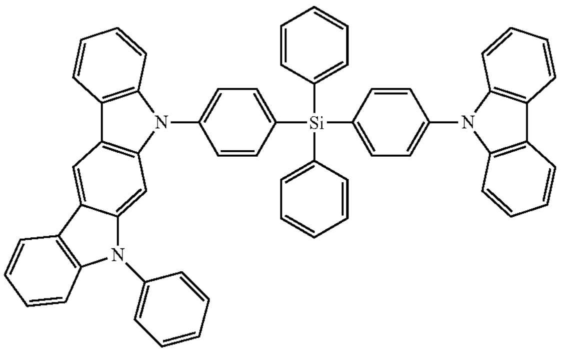
-continued
16
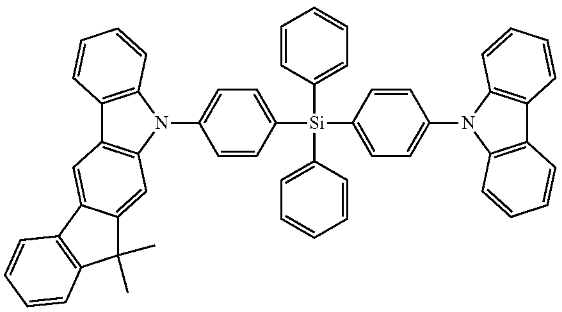
17
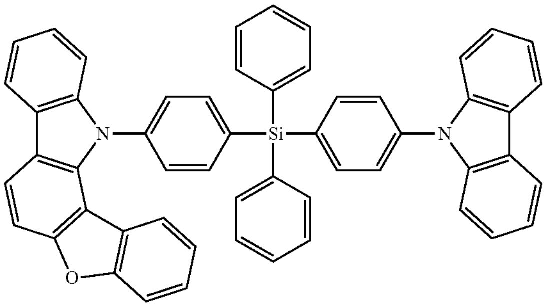
18
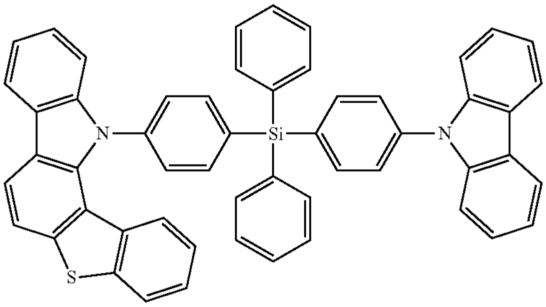
19
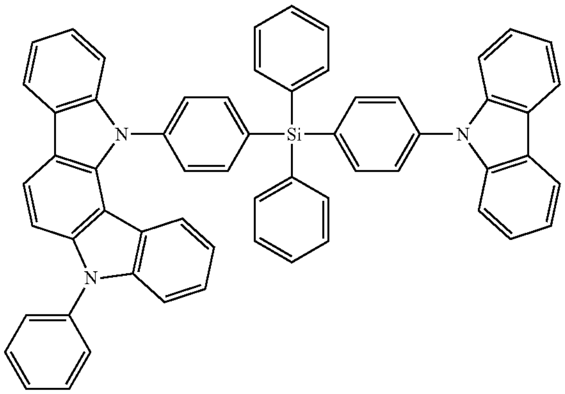

-continued
20
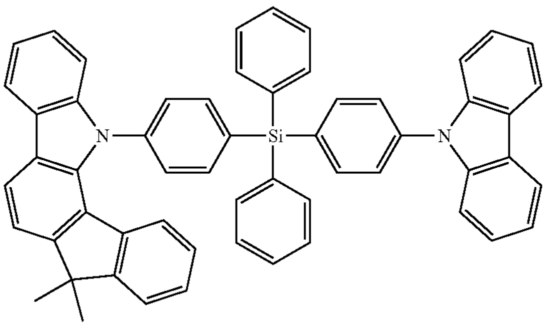
21
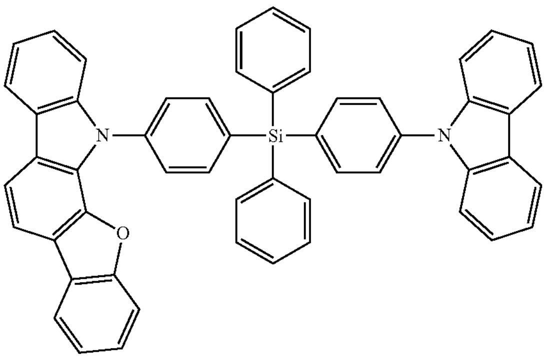
22
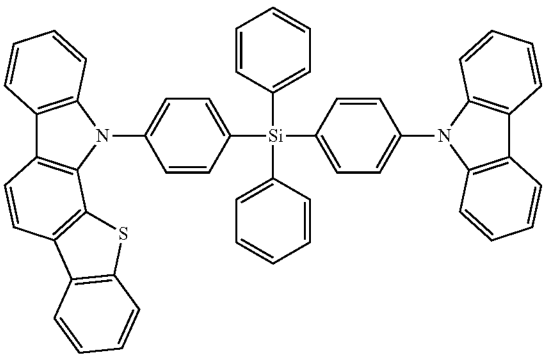
23
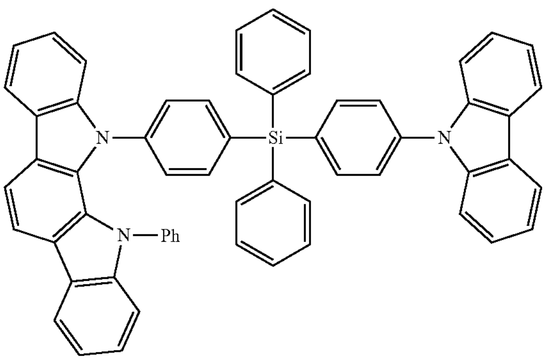
-continued
24
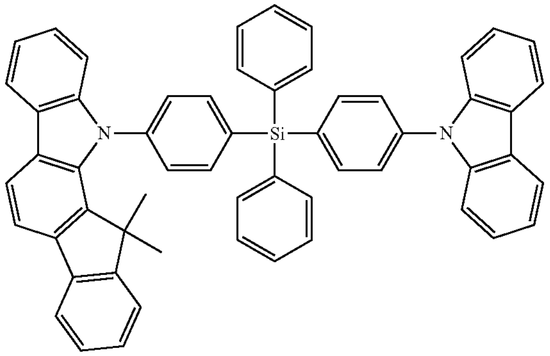
25
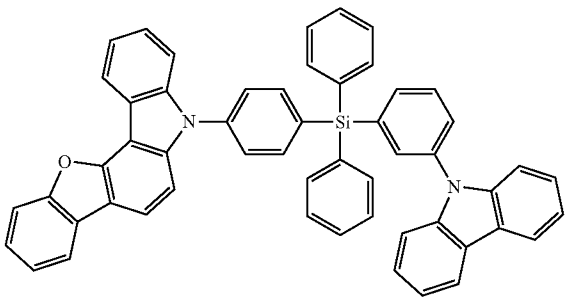
26
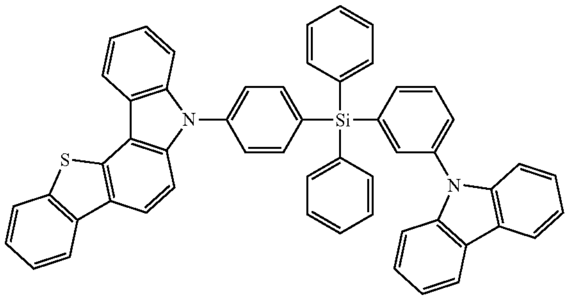
27
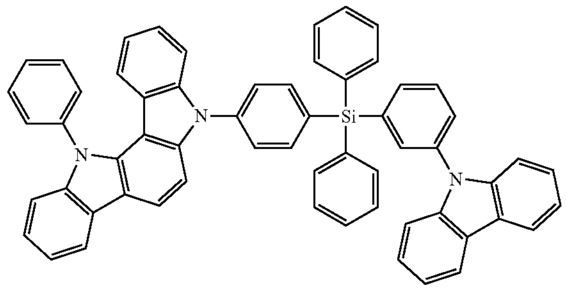

-continued
28
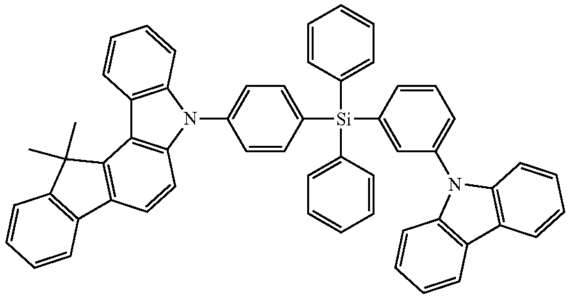
29
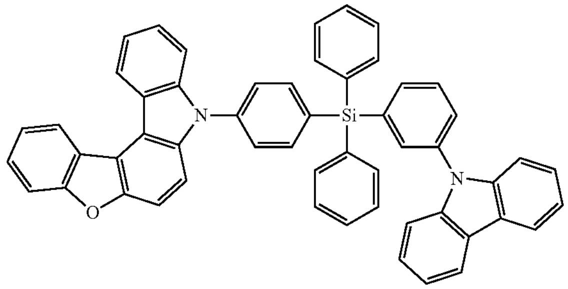
30
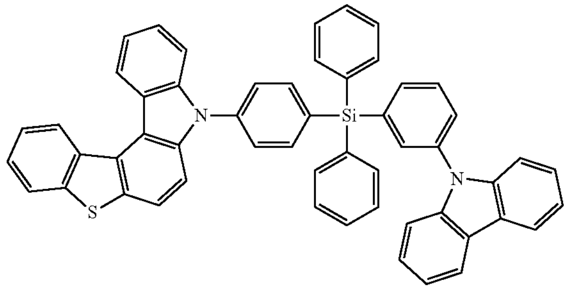
31
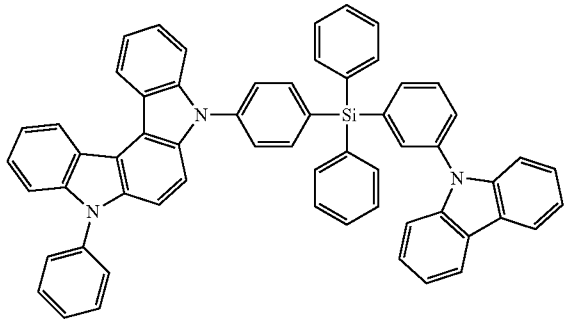
32
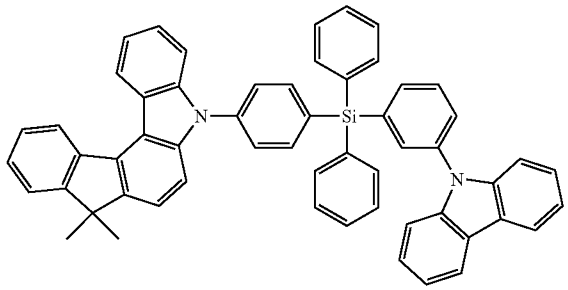
-continued
33
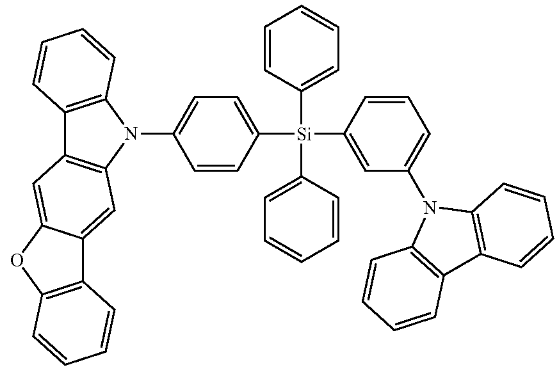
34
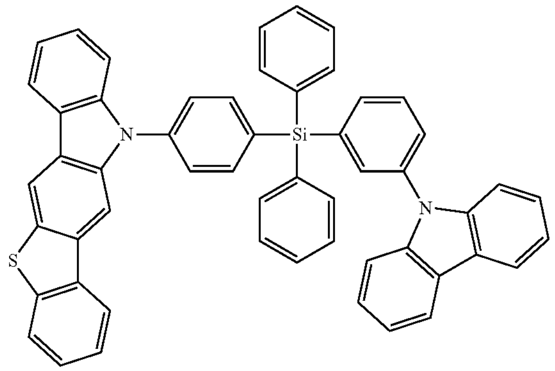
35
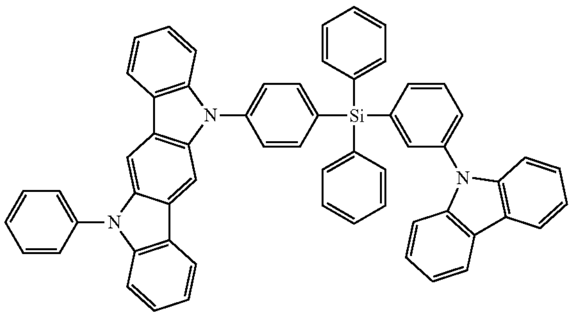
36
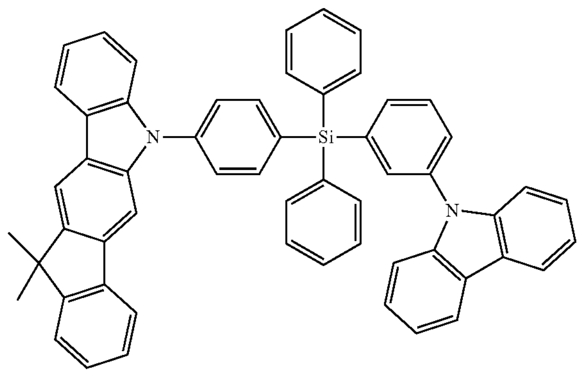

-continued
37
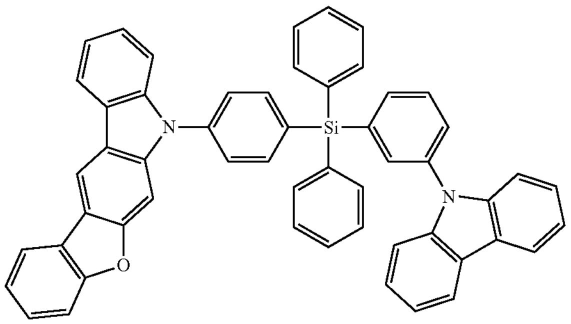
38
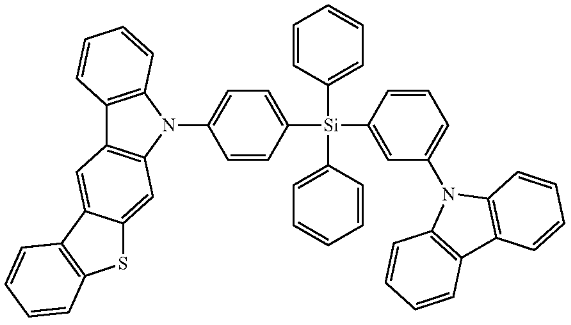
39
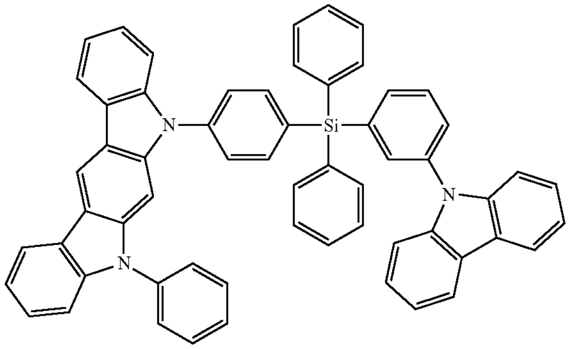
40
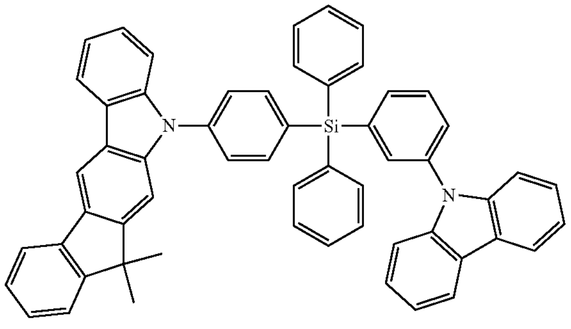
-continued
41
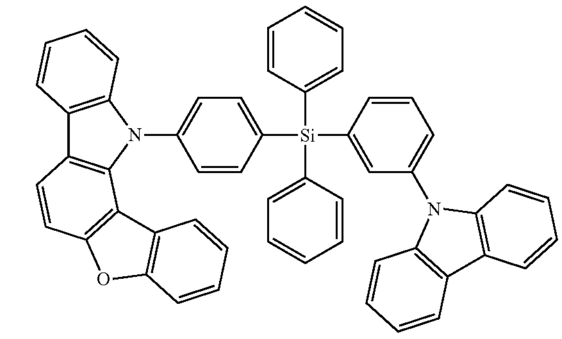
42
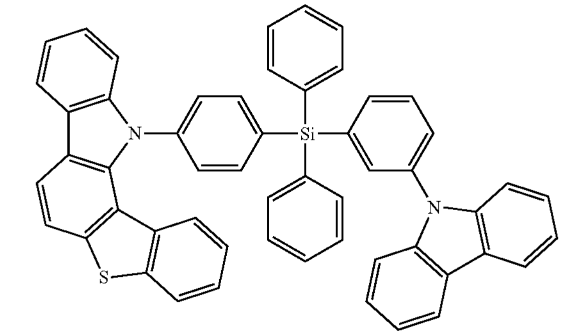
43
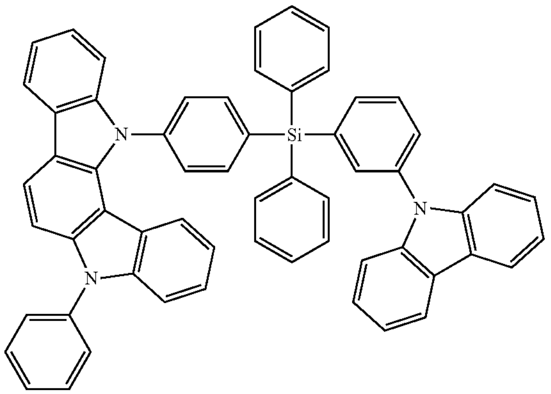
44
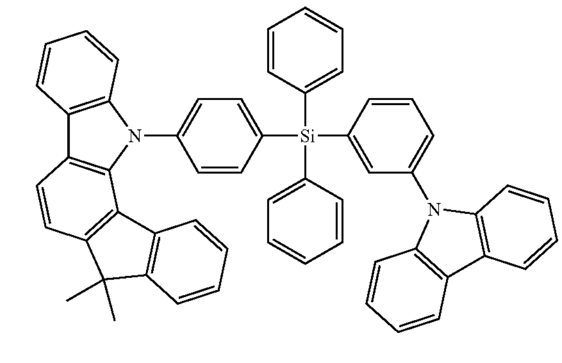

-continued
45
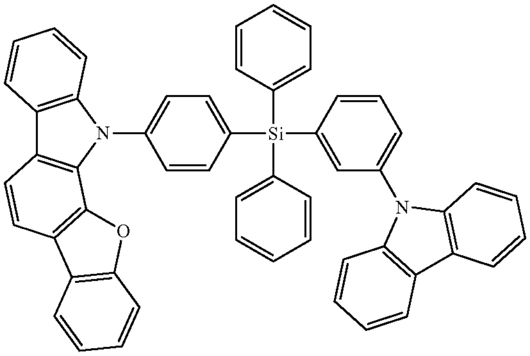
46
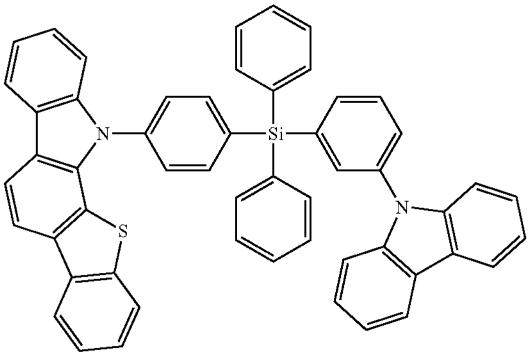
47
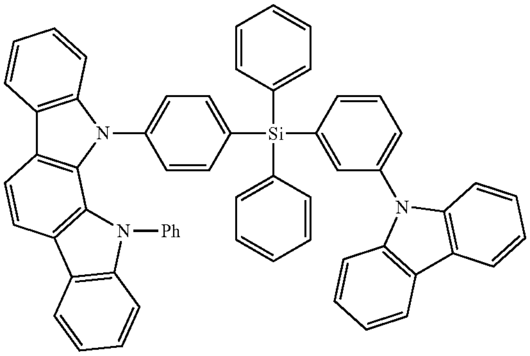
48
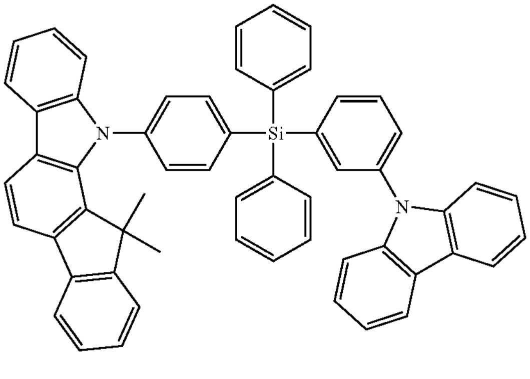
-continued
49
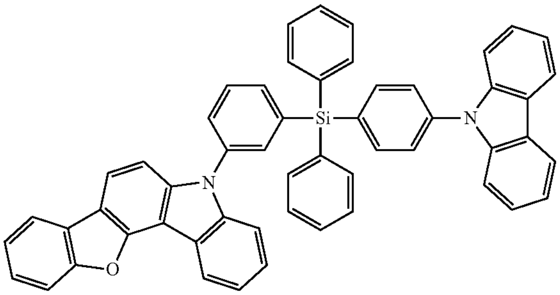
50
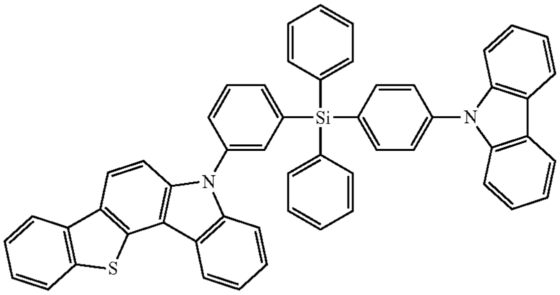
51
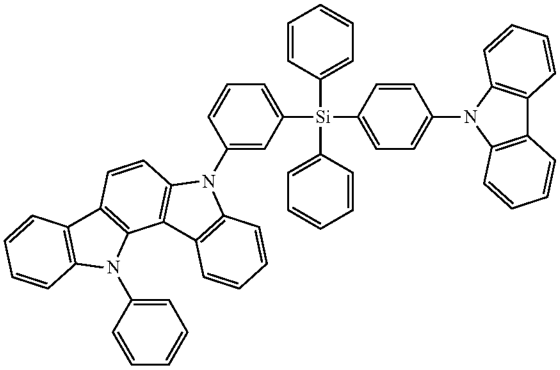
52
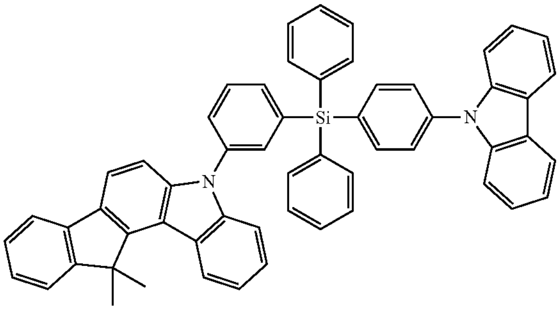

-continued
53
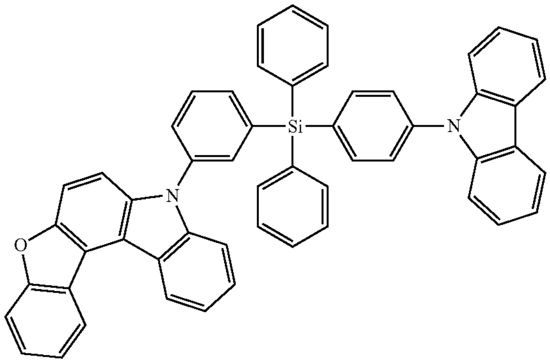
54
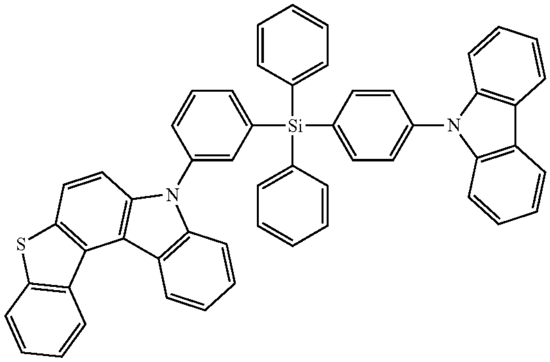
55
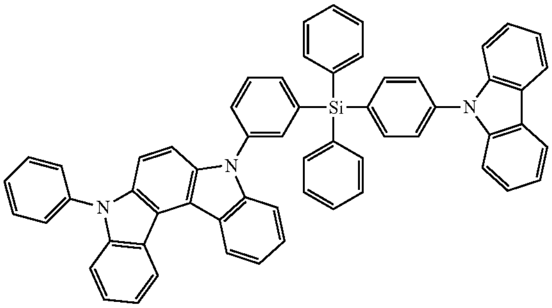
56
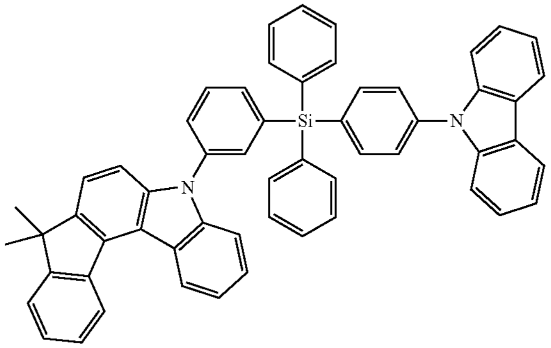
-continued
57
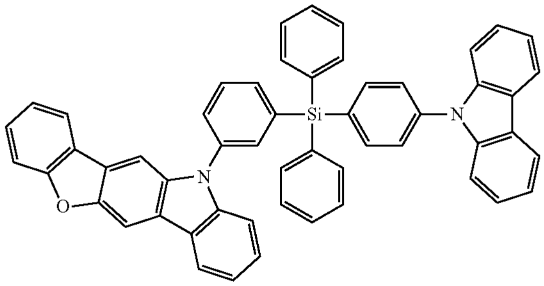
58
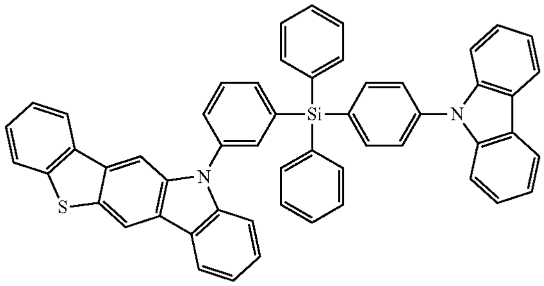
59
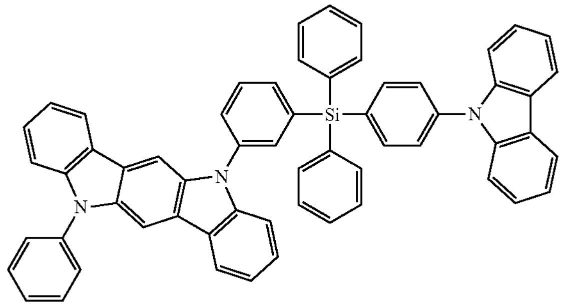
60
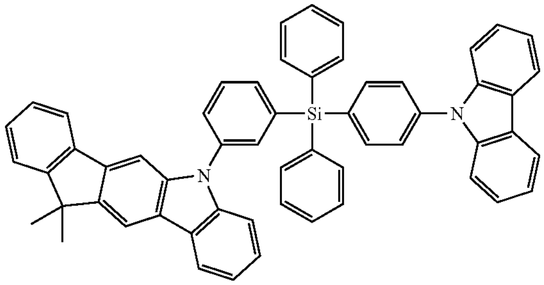
61
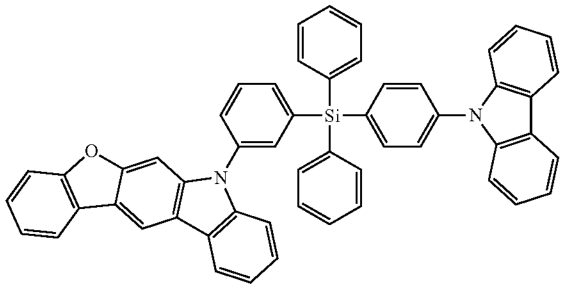

-continued
62
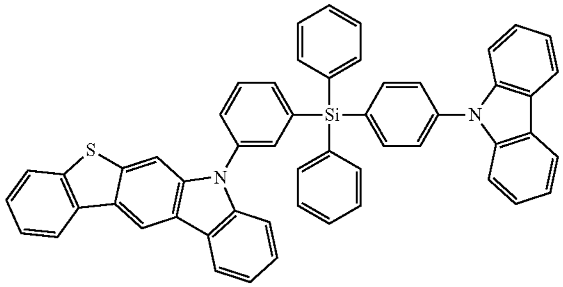
63
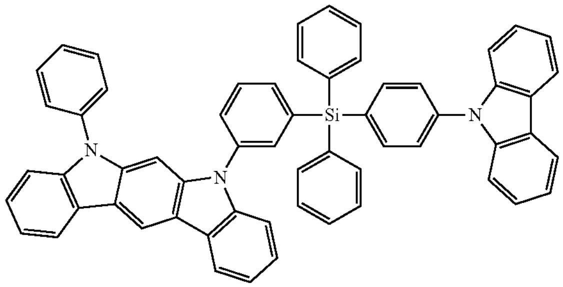
64
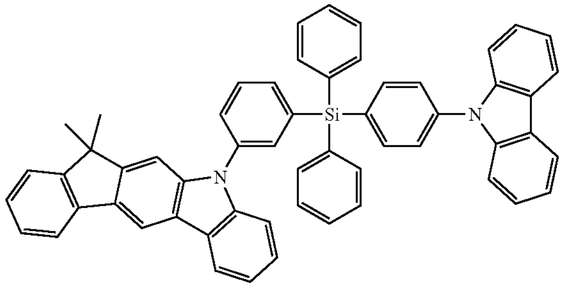
65
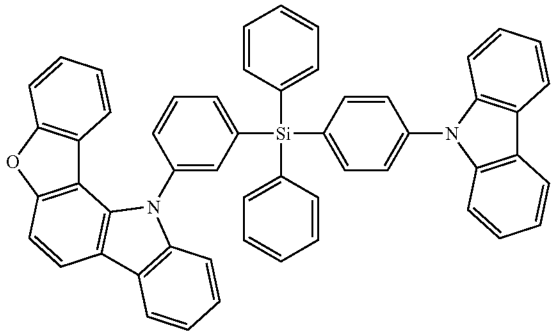
-continued
66
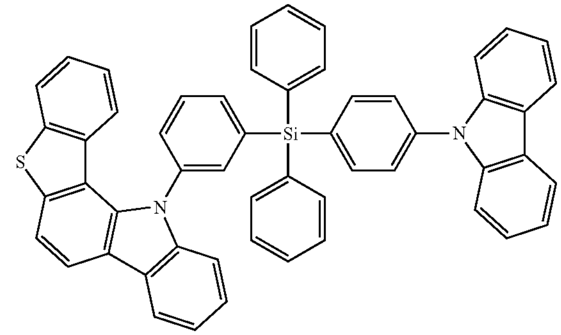
67
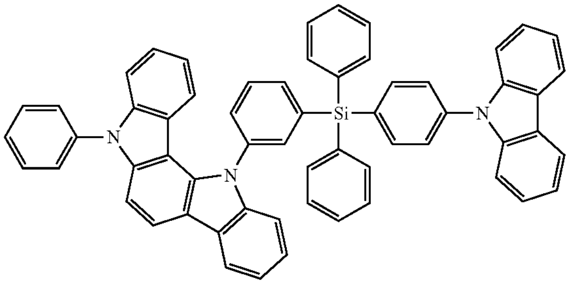
68
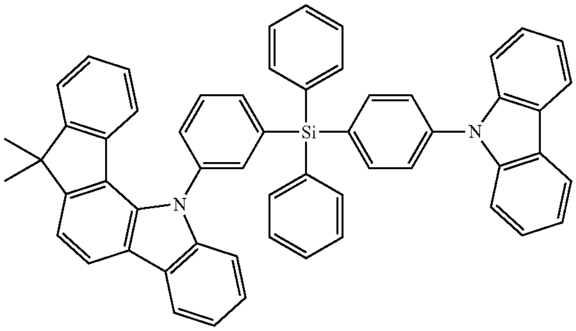
69
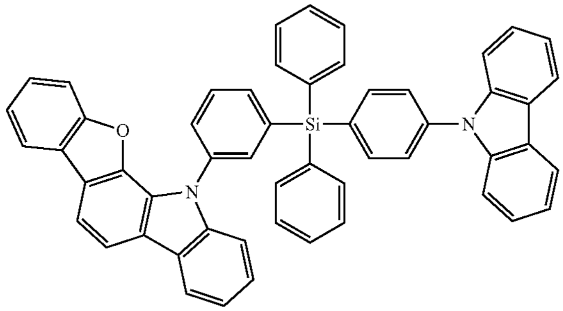

-continued
70
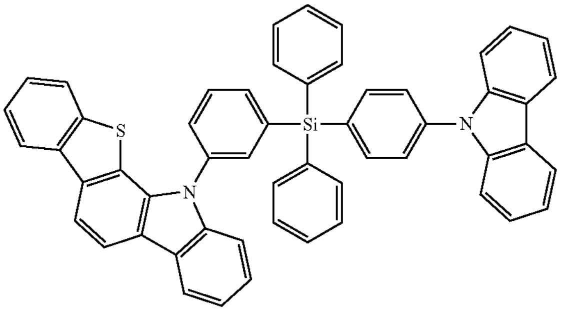
71
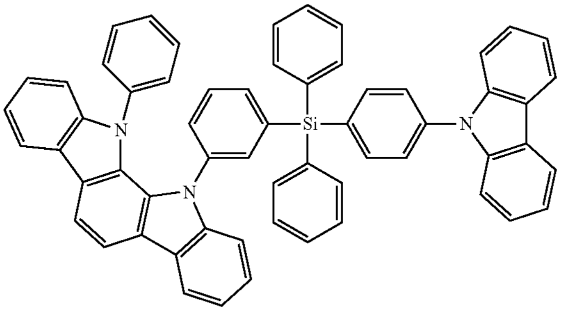
72
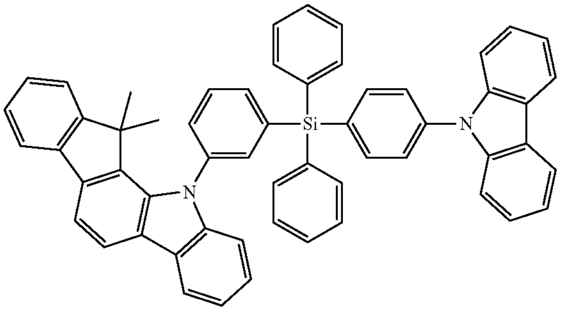
73
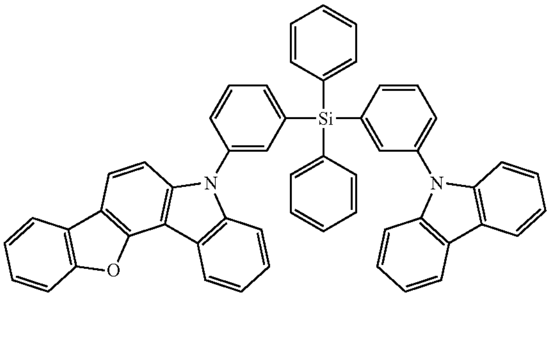
-continued
74
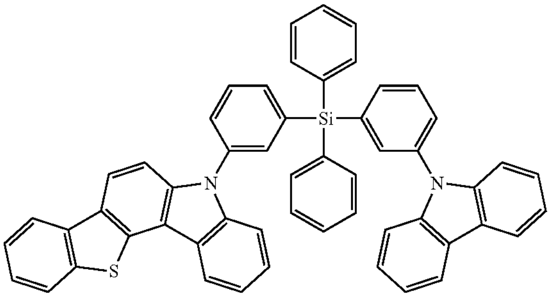
75
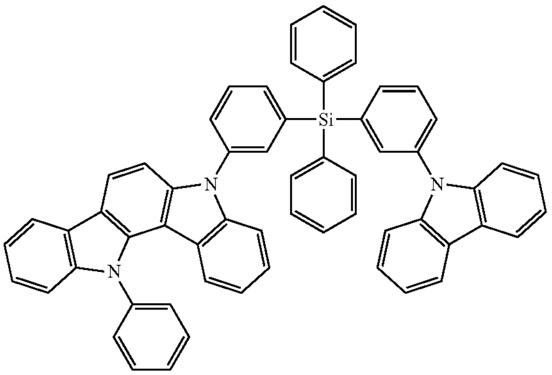
76
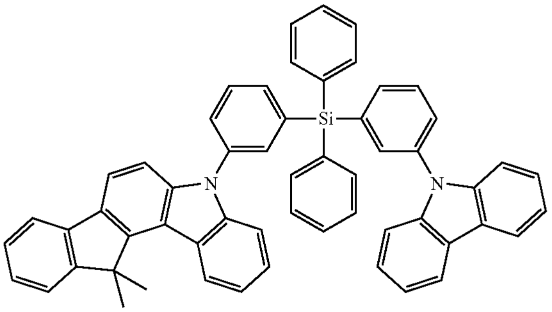
77
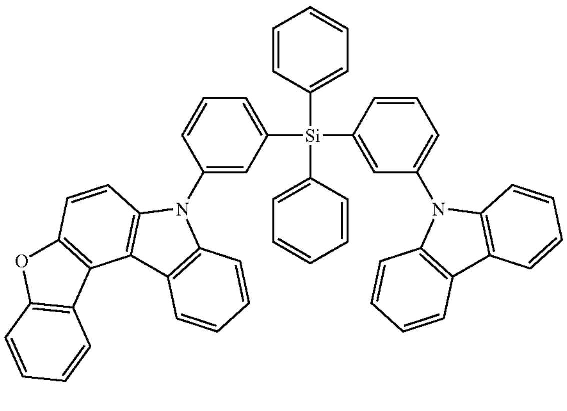

78
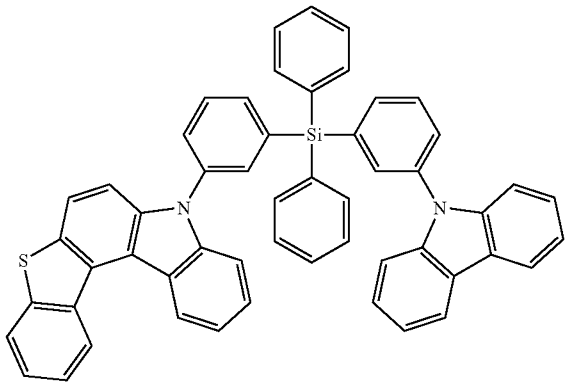
79
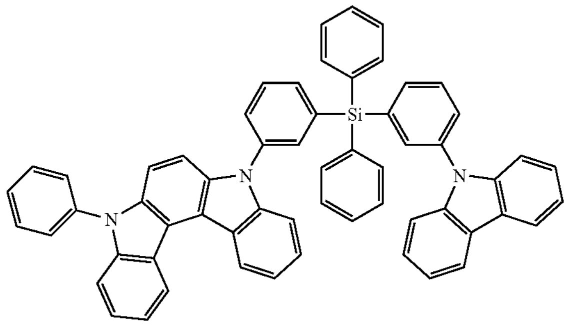
80
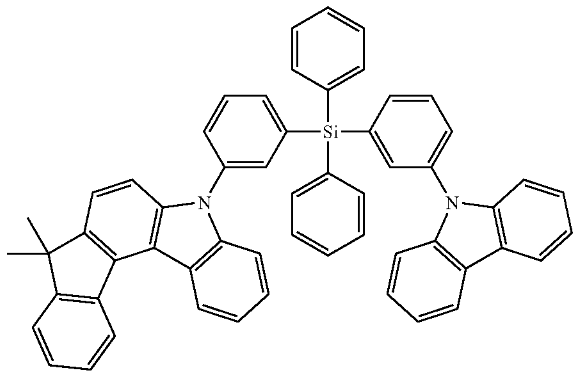
81
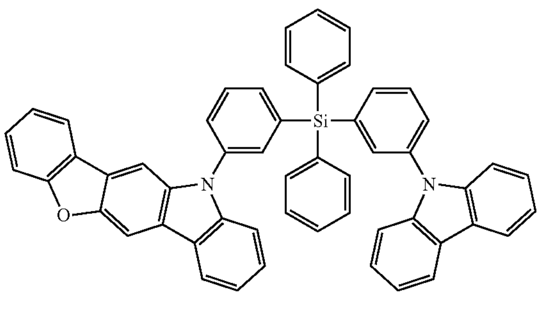
82
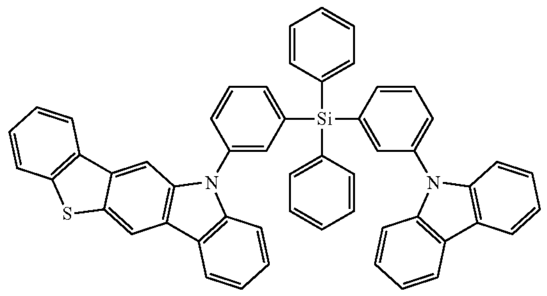
83
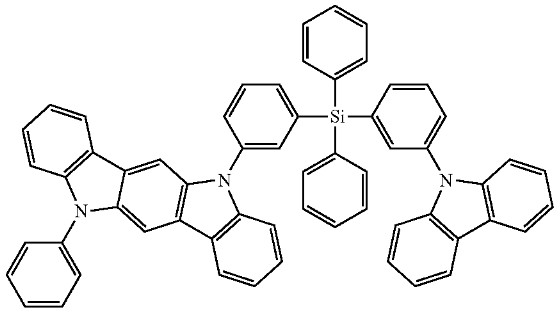
84
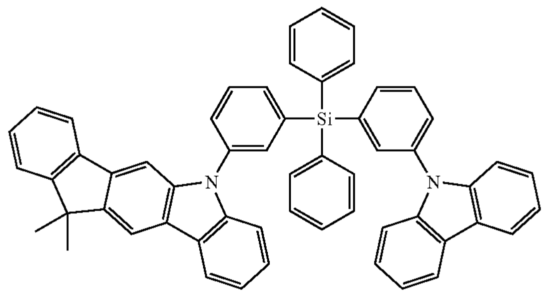
85
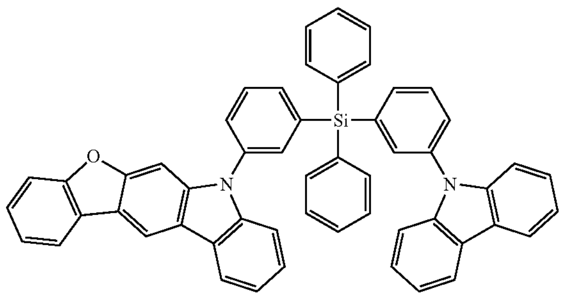
86
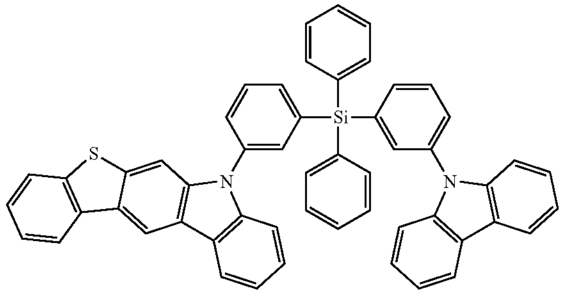

-continued
87
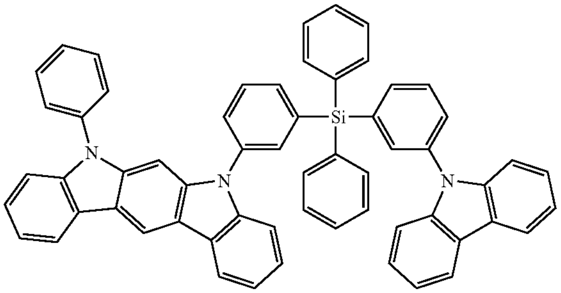
88
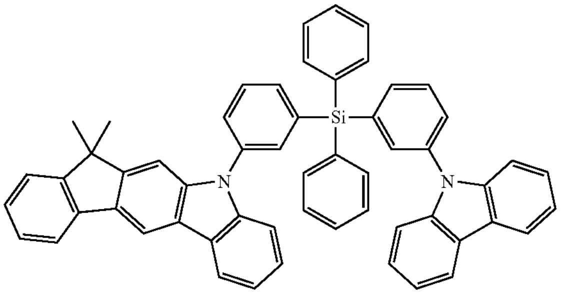
89
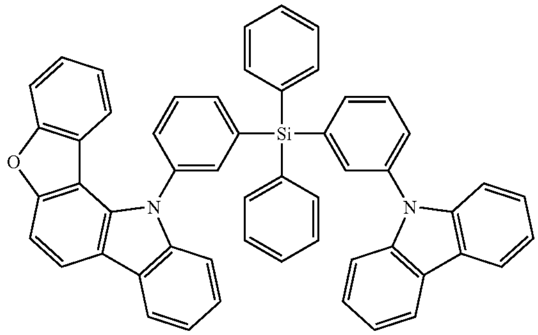
90
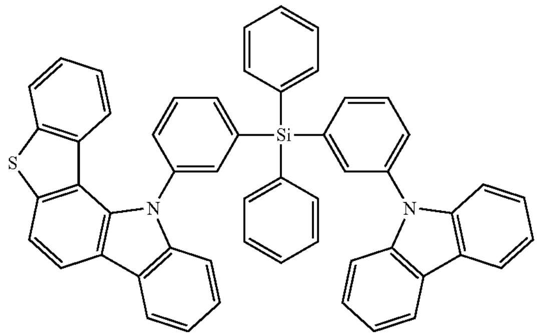
-continued
91
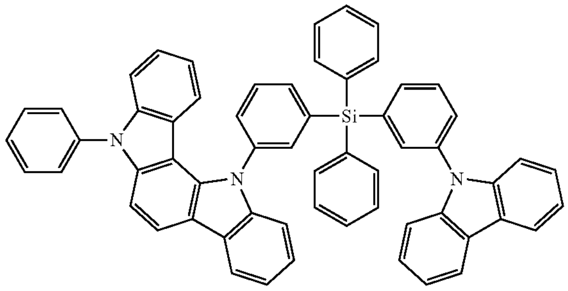
92
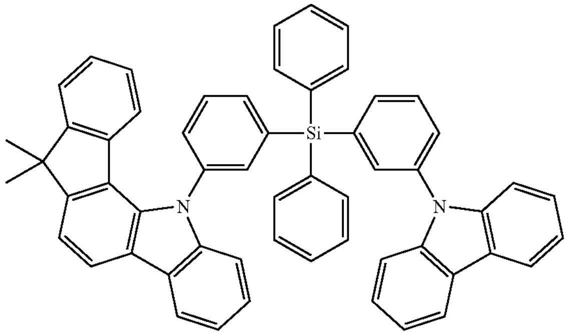
93
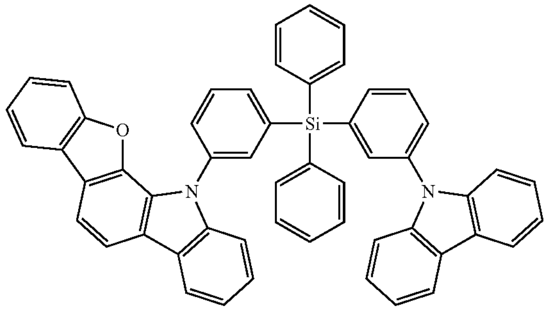
94
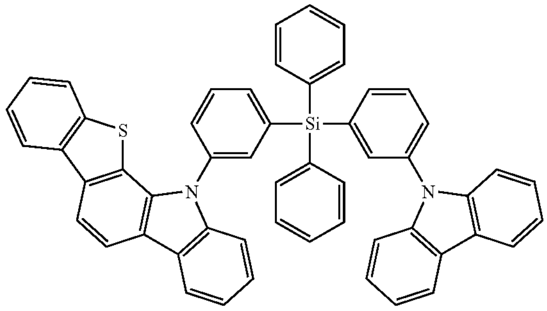

95
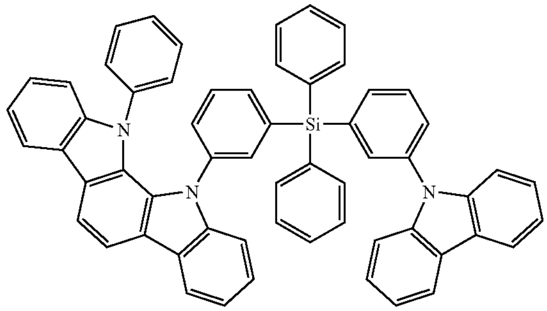
96
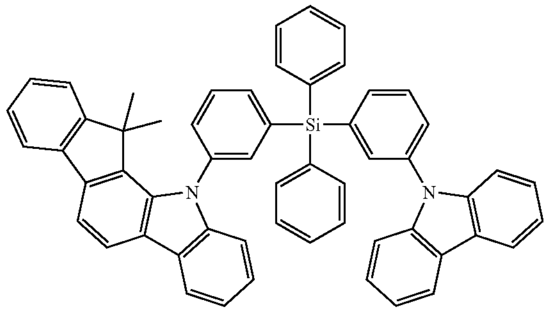
97
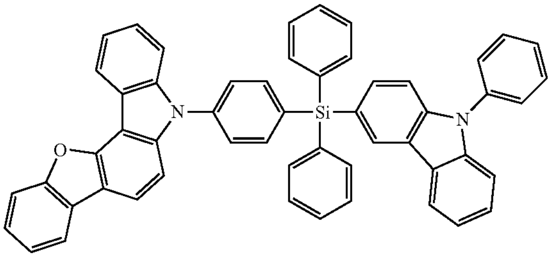
98
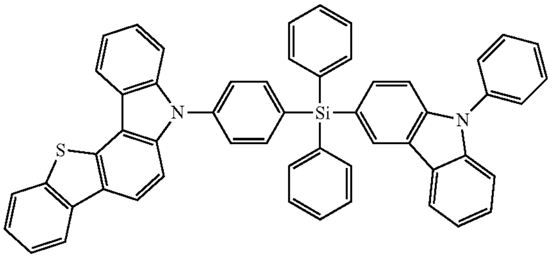
99
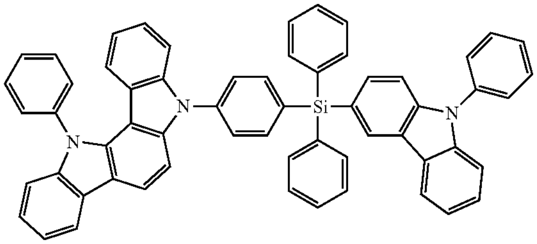
100
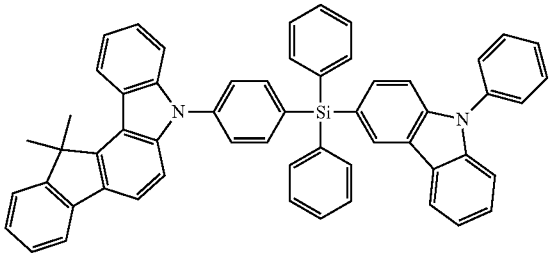
101
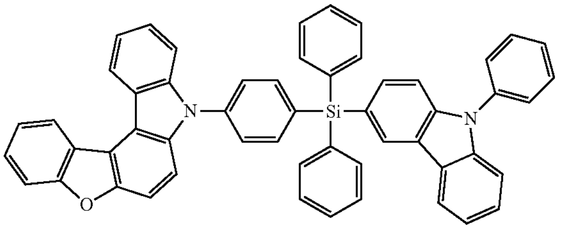
102
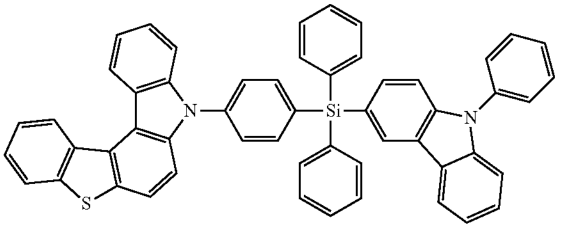
103
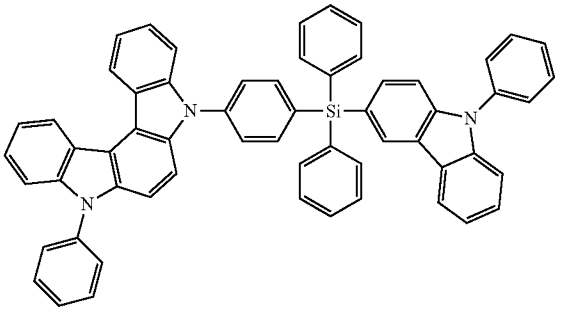
104
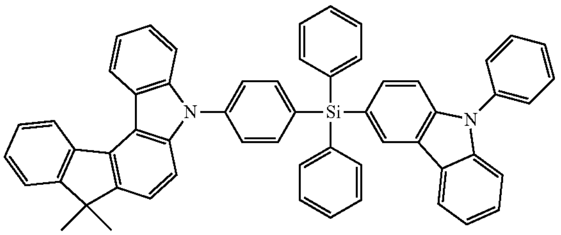

-continued
105
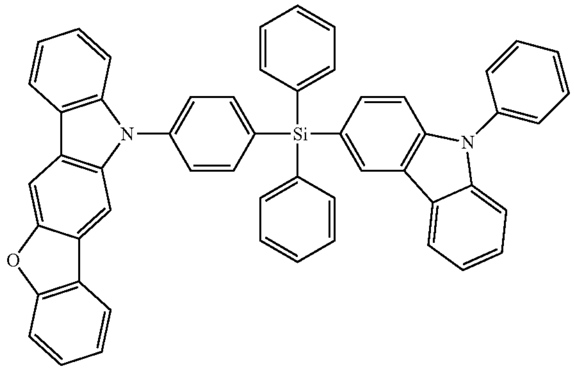
106
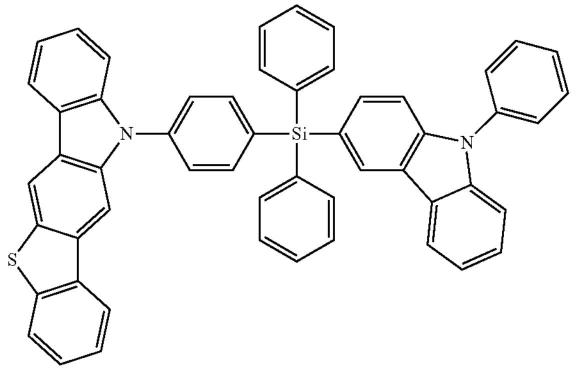
107
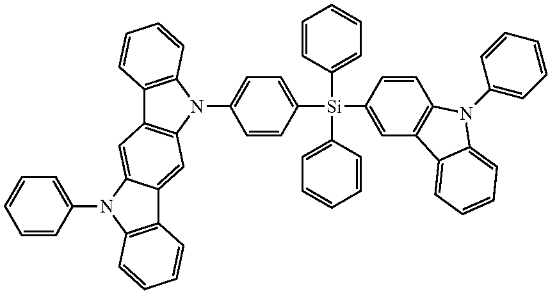
108
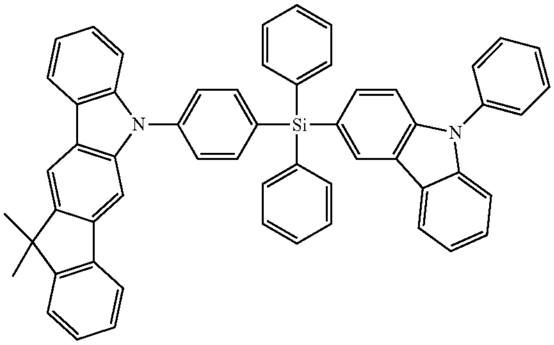
-continued
109
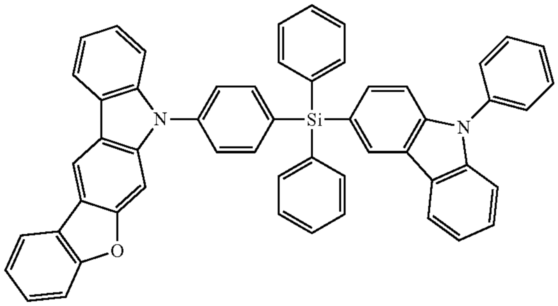
110
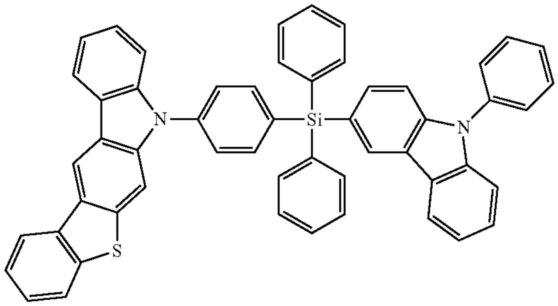
111
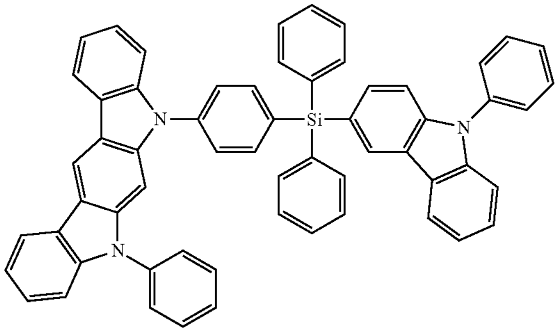
112
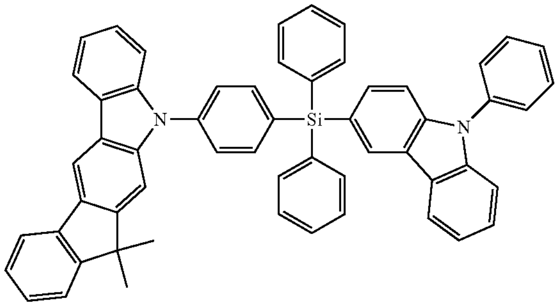

-continued
113
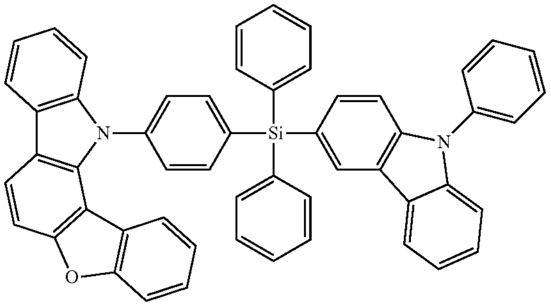
114
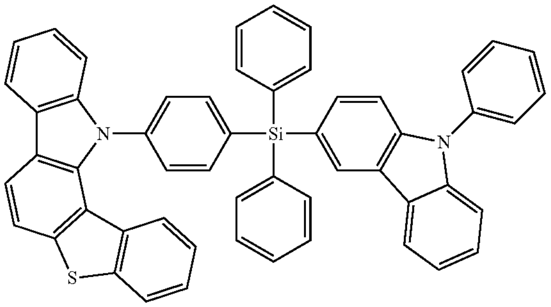
115
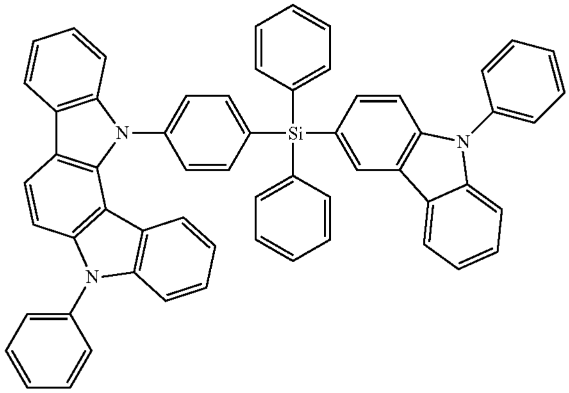
116
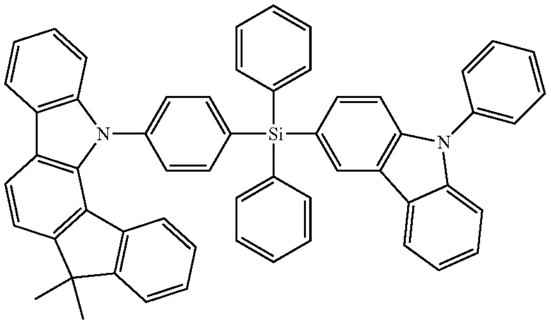
-continued
117
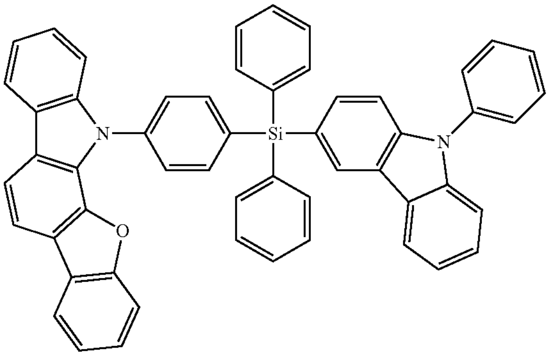
118
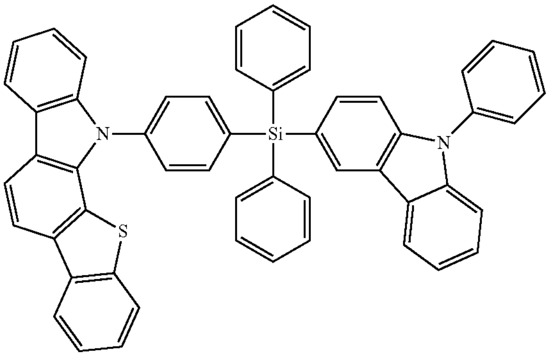
119
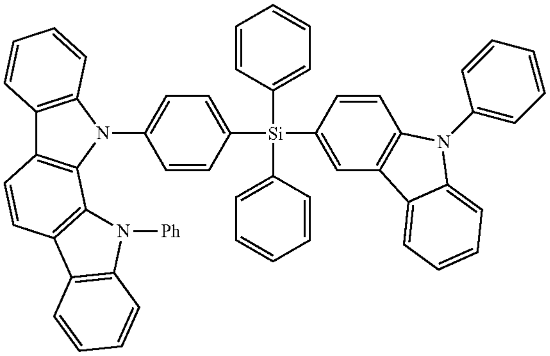
120
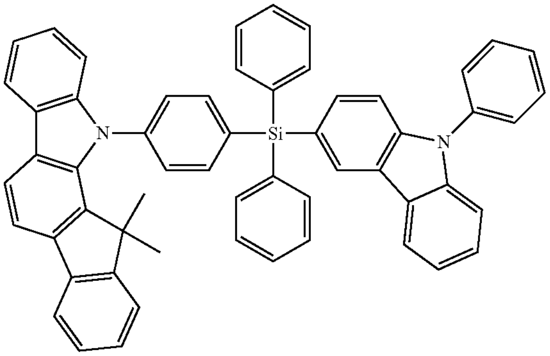

-continued
121
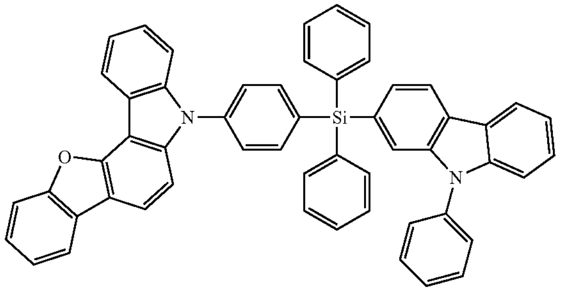
122
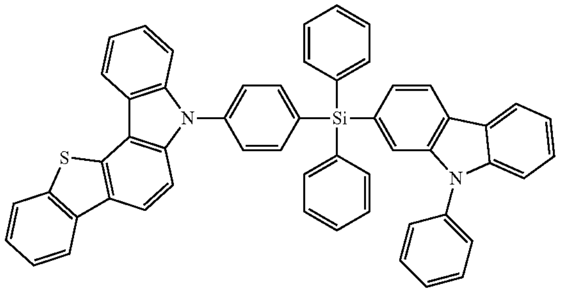
123
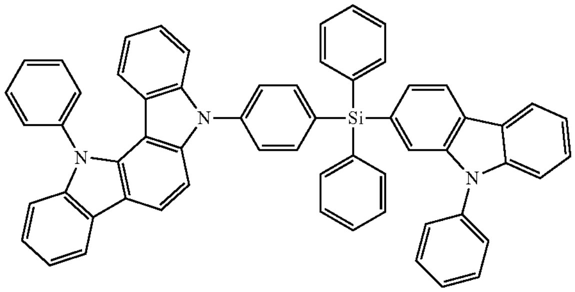
124
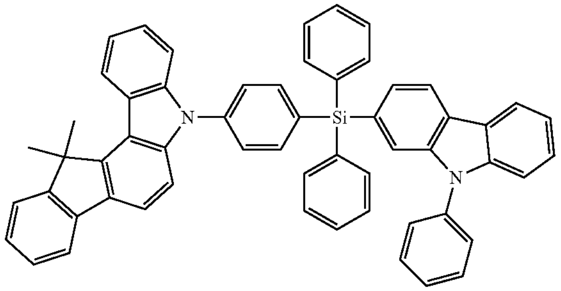
125
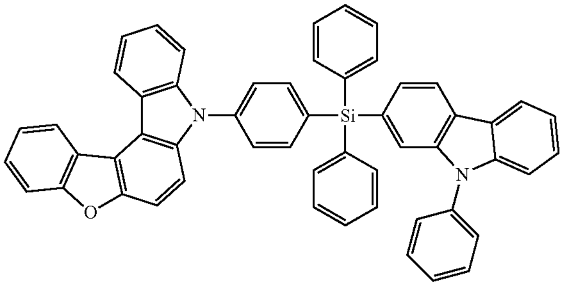
-continued
126
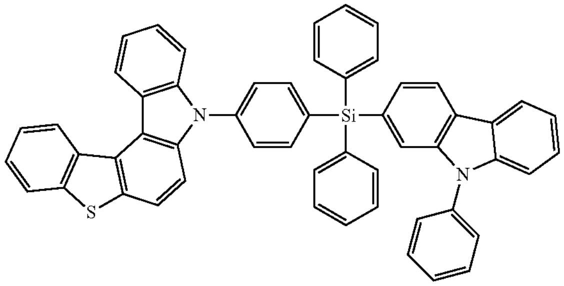
127
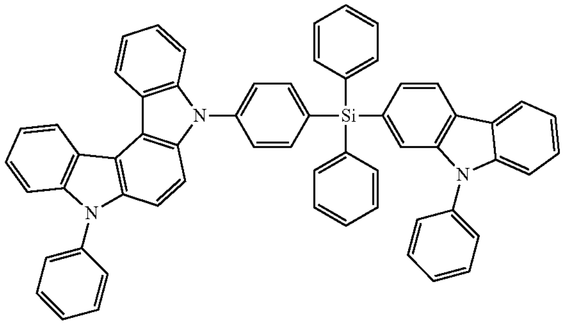
128
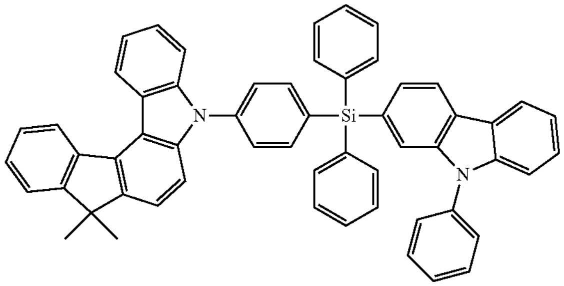
129
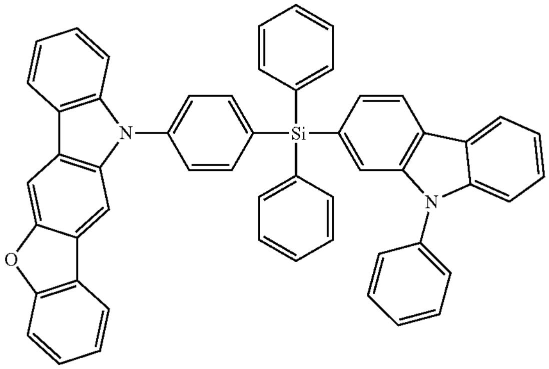

-continued
130
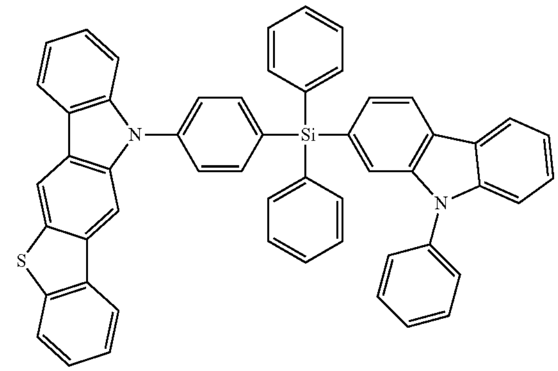
131
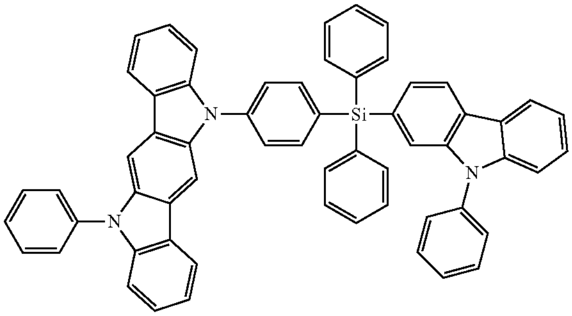
132
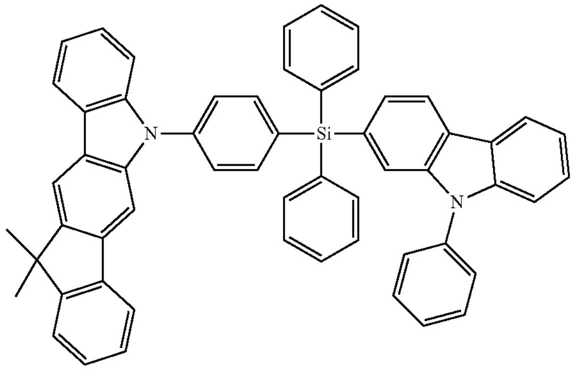
133
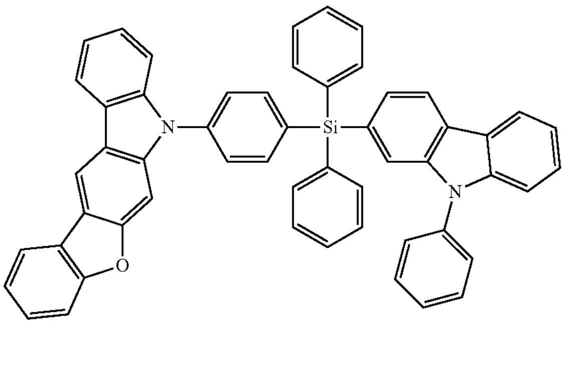
-continued
134
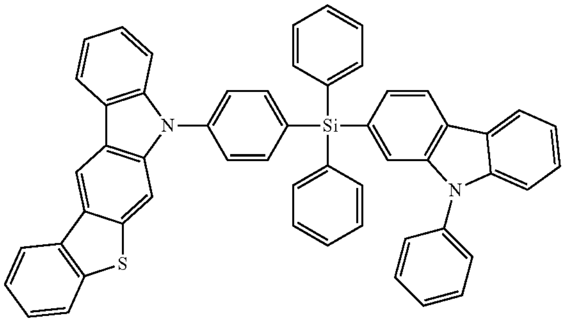
135
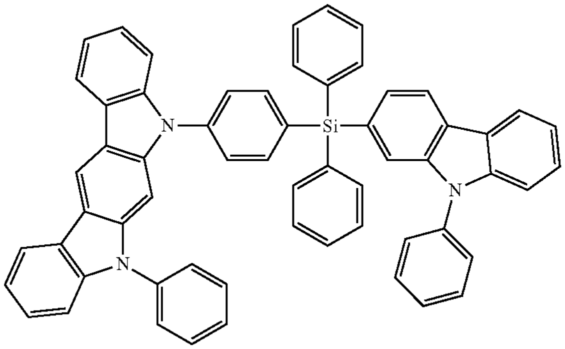
136
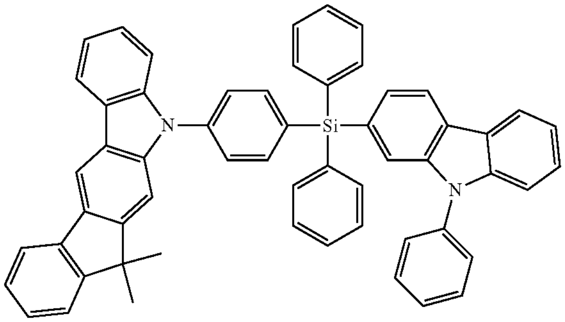
137
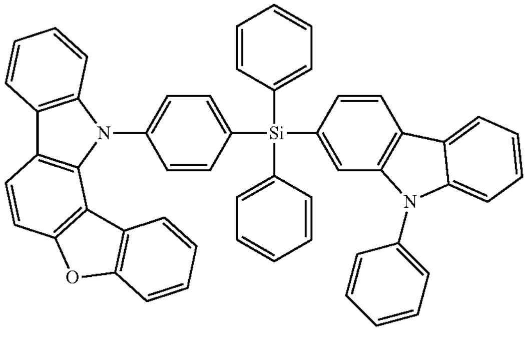

-continued
138
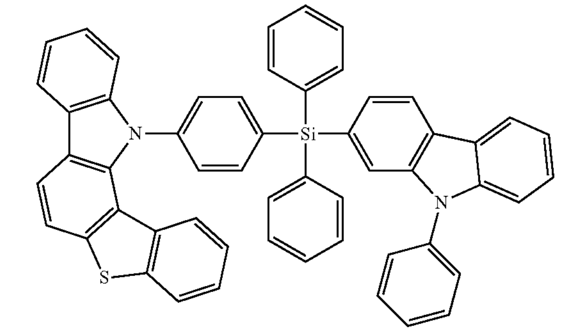
139
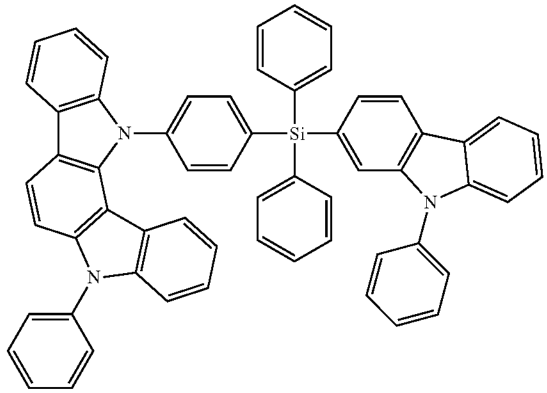
140
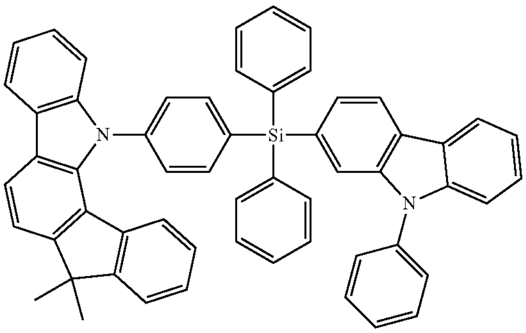
141
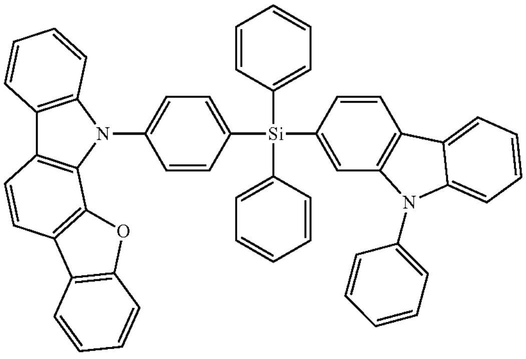
-continued
142
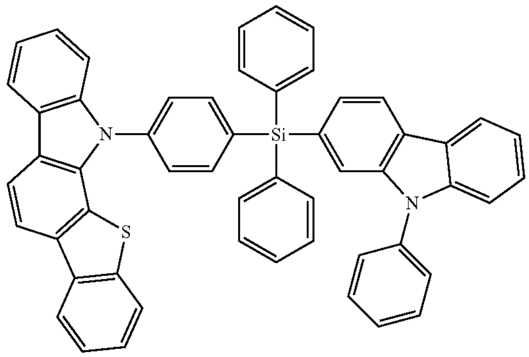
143
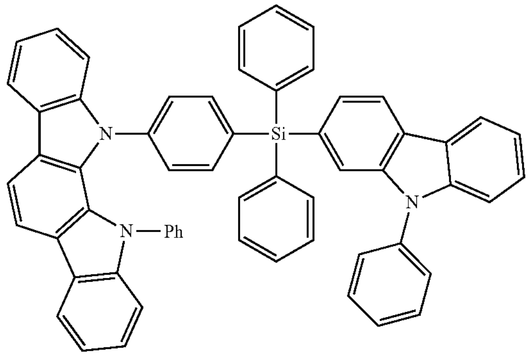
144
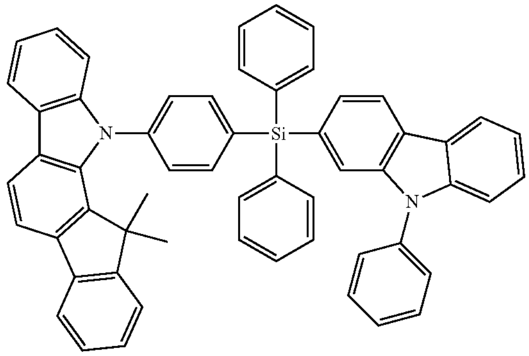
145
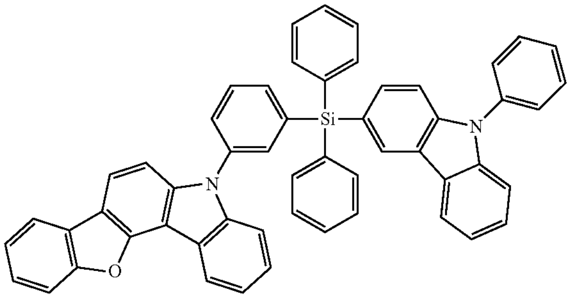

146
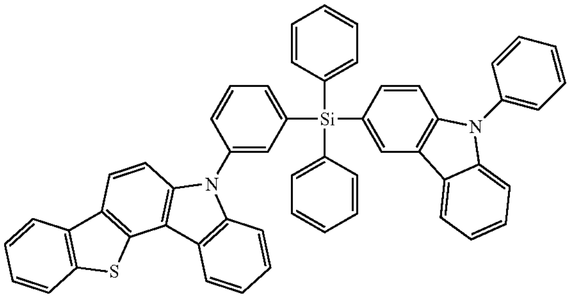
147
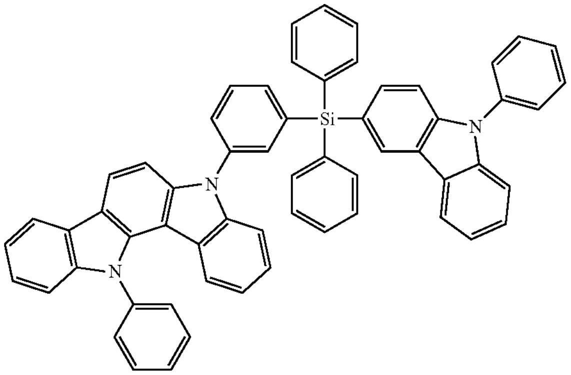
148
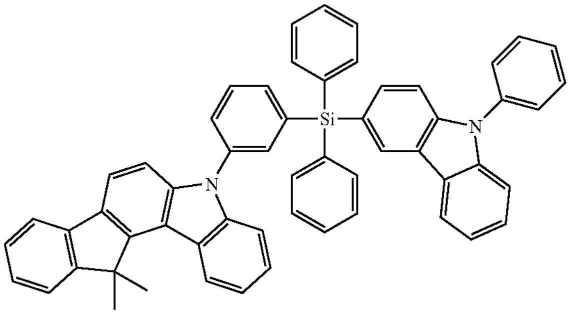
149
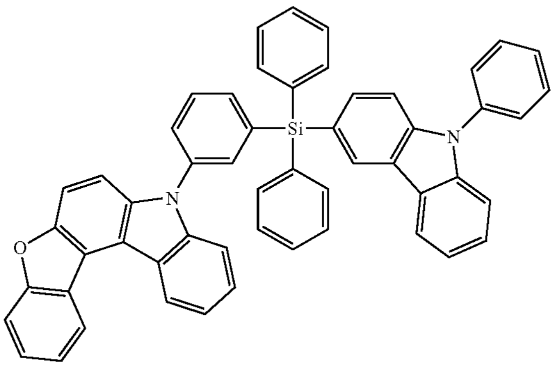
150
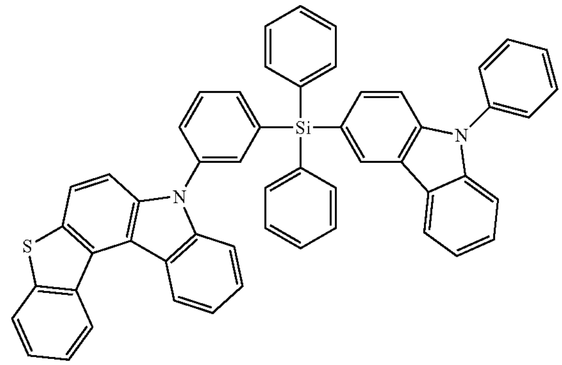
151
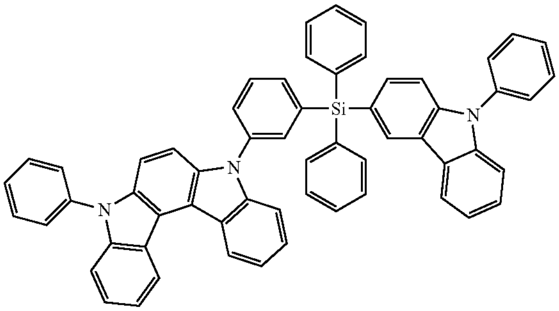
152
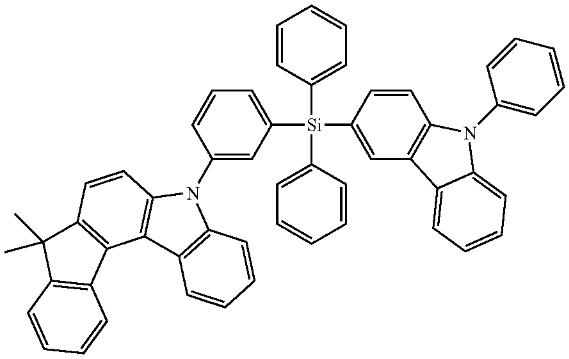
153
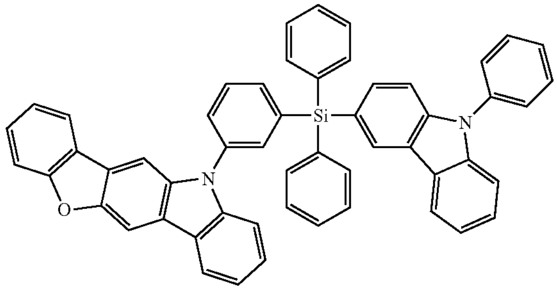

-continued
154
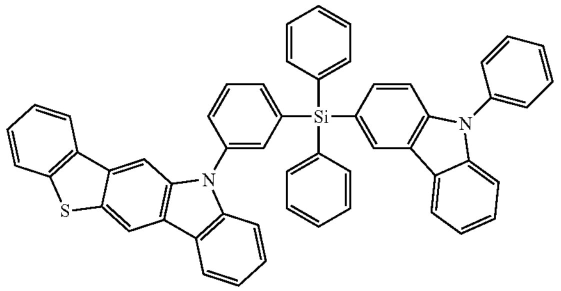
155
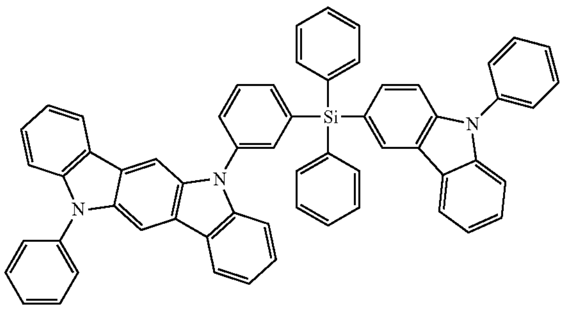
156
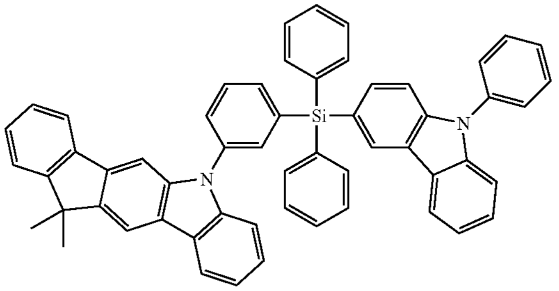
157
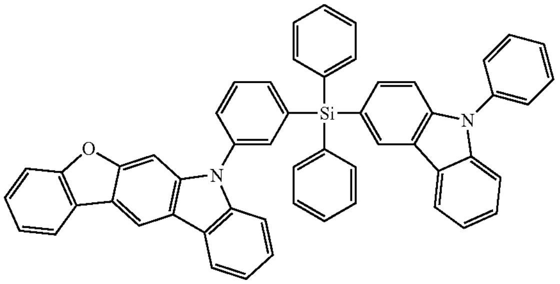
158
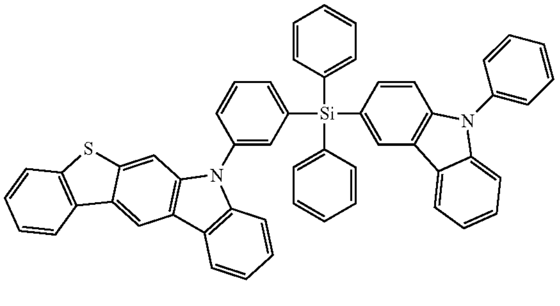
-continued
159
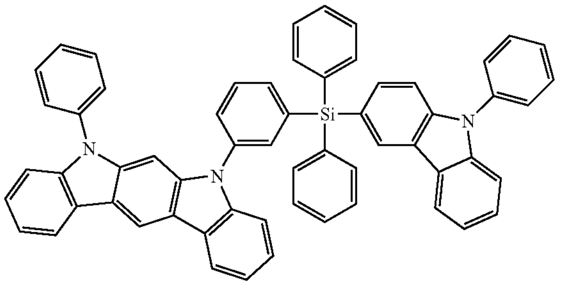
160
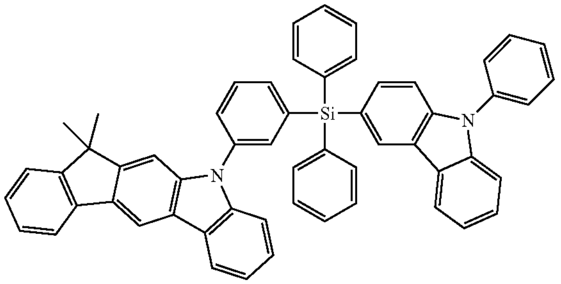
161
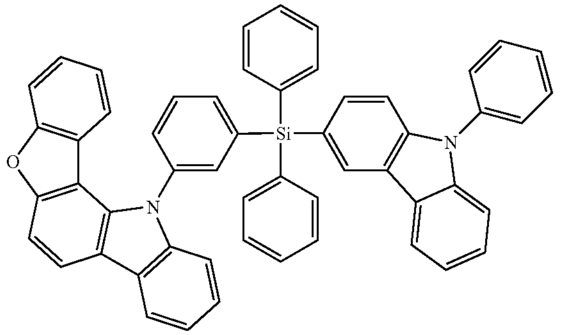
162
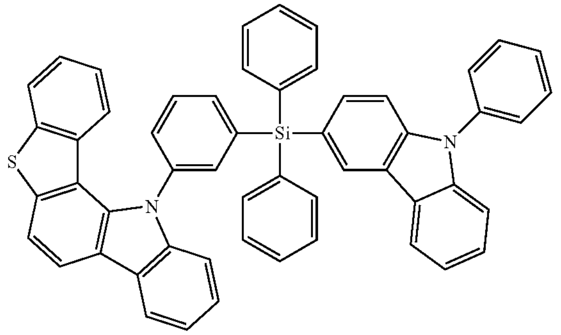
163
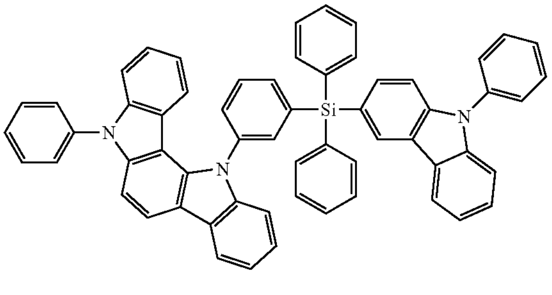

-continued
164
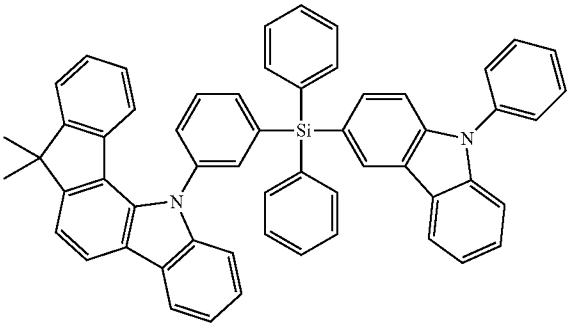
165
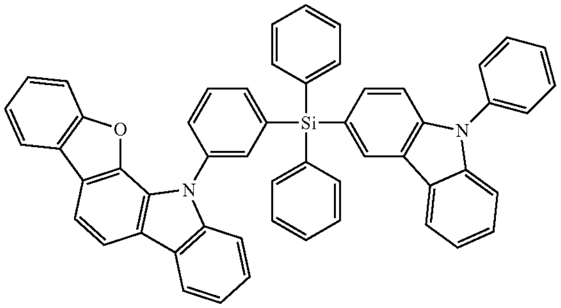
166
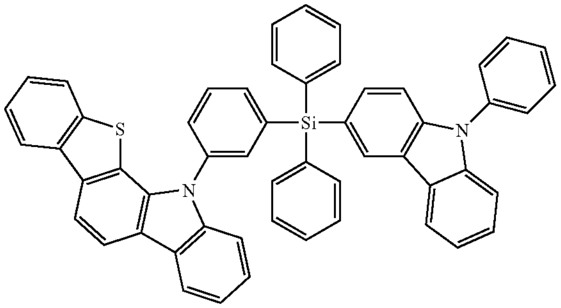
167
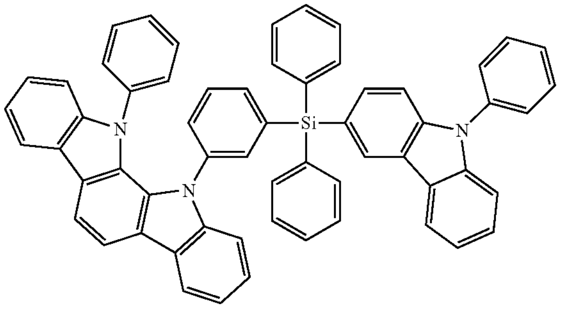
-continued
168
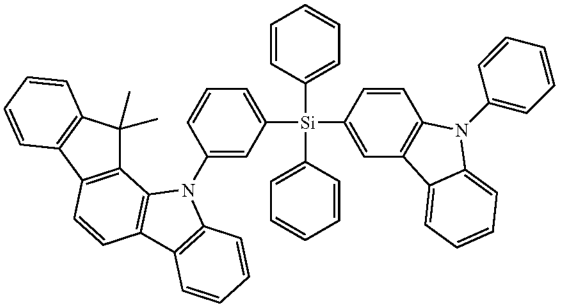
169
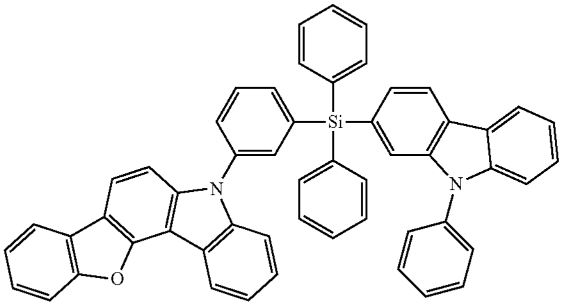
170
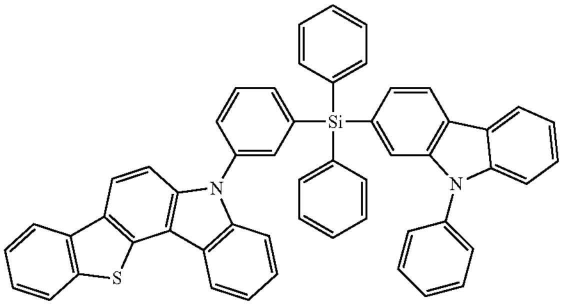
171
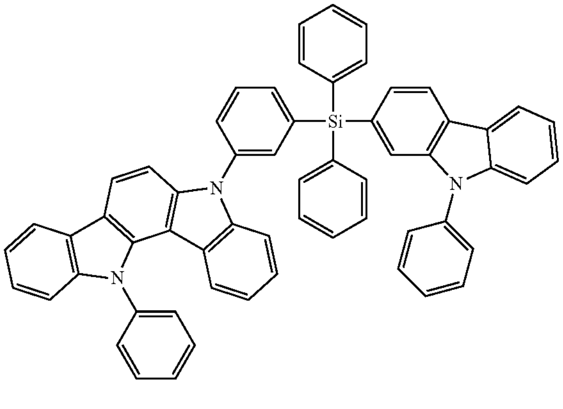

172
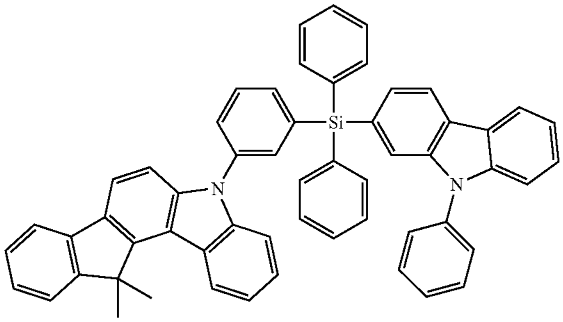
173
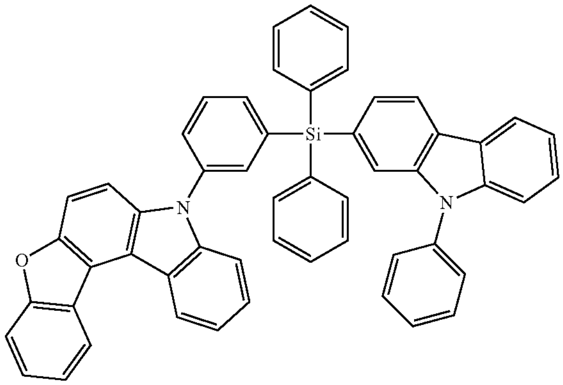
174
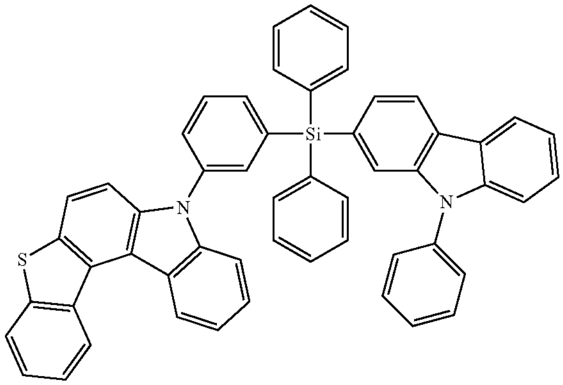
175
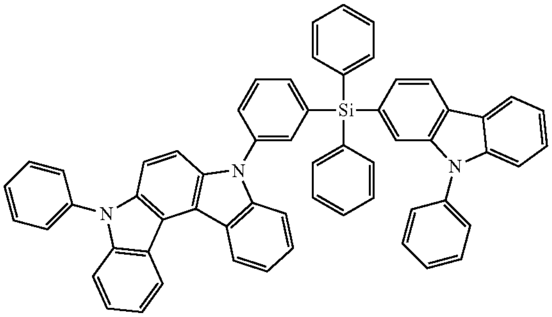
176
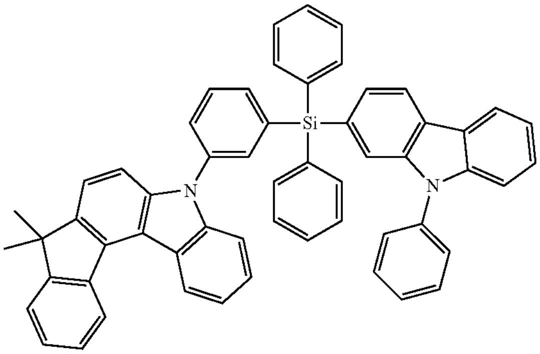
177
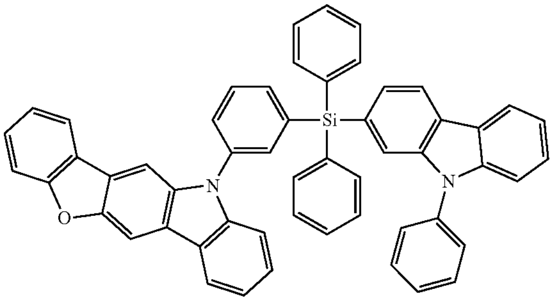
178
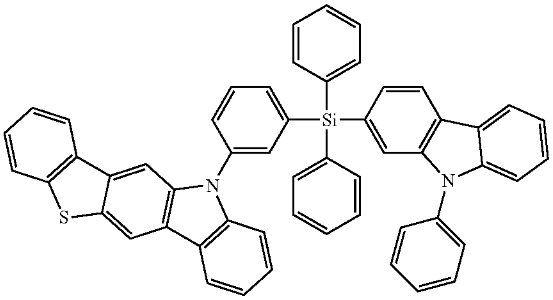
179
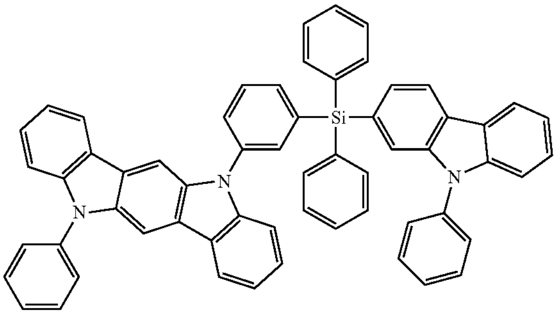

-continued
180
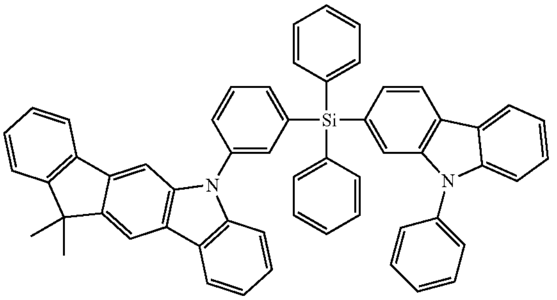
181
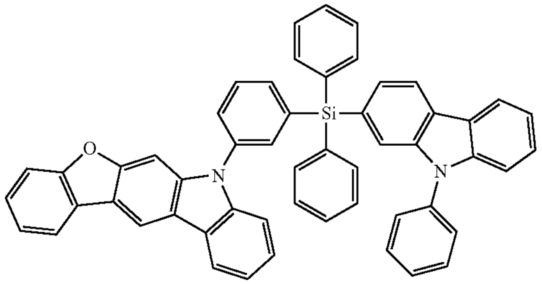
182
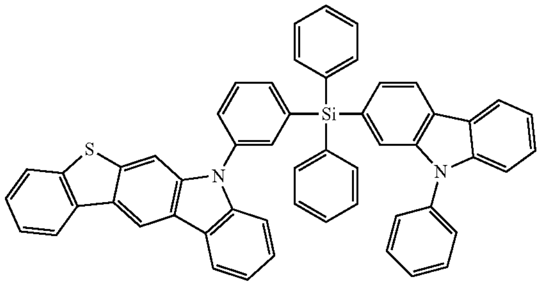
183
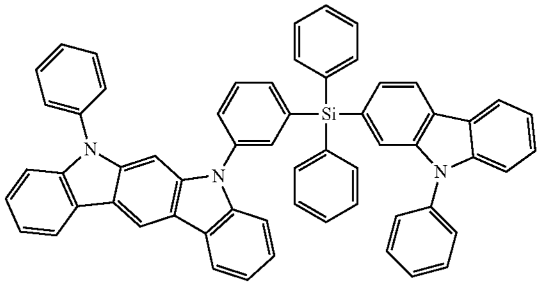
184
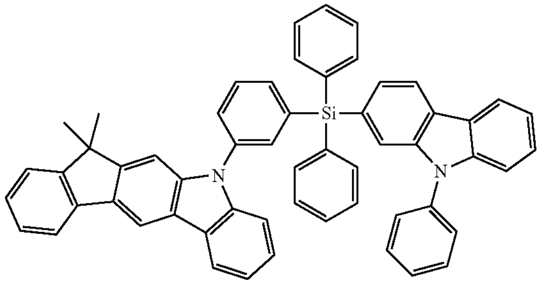
-continued
185
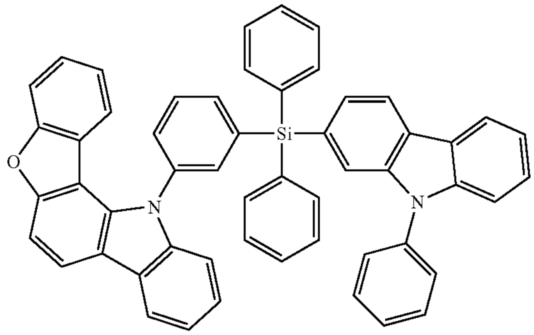
186
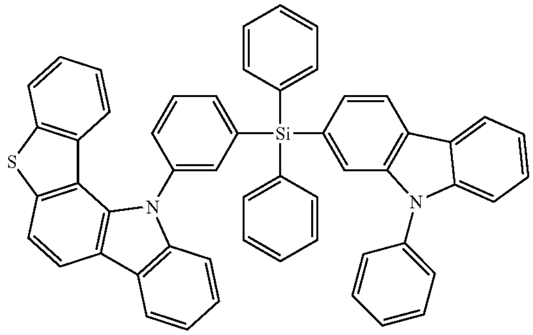
187
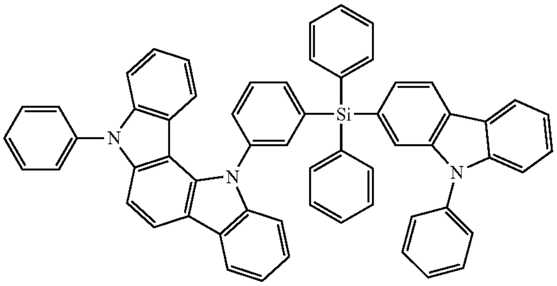
188
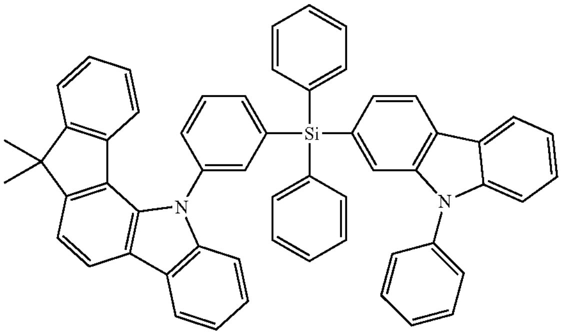

-continued
189
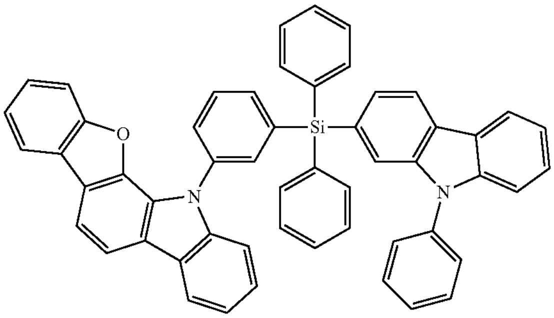
190
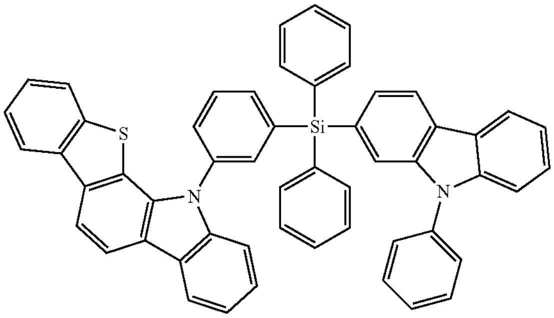
191
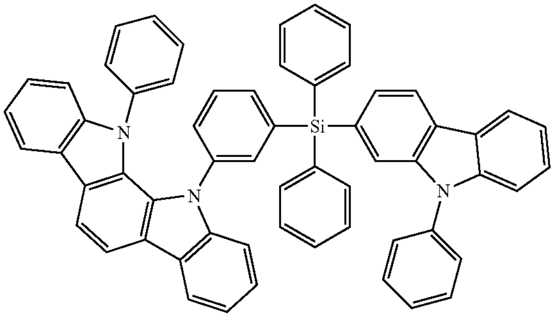
192
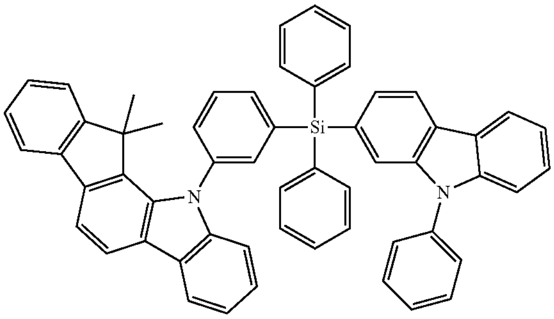
-continued
193
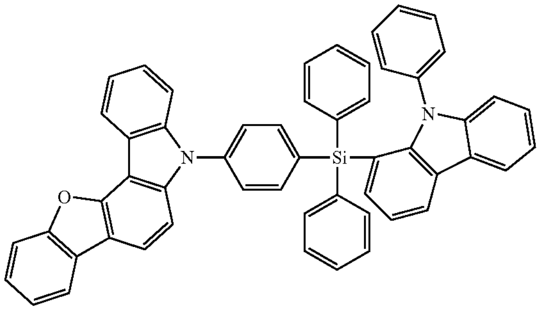
194
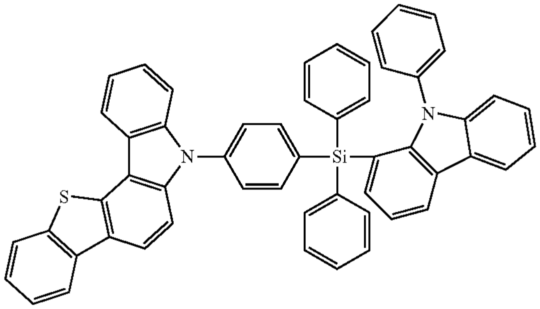
195
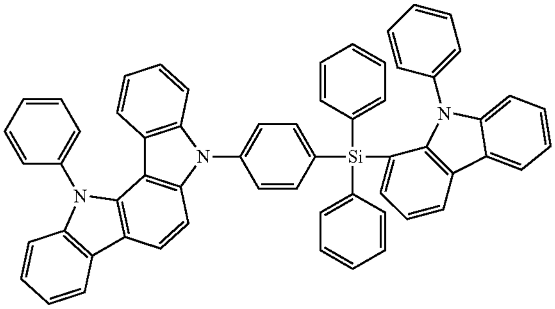
196
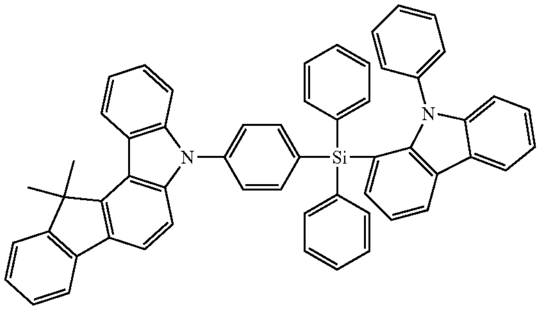
197
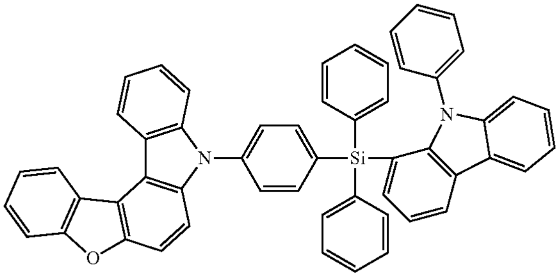

-continued
198
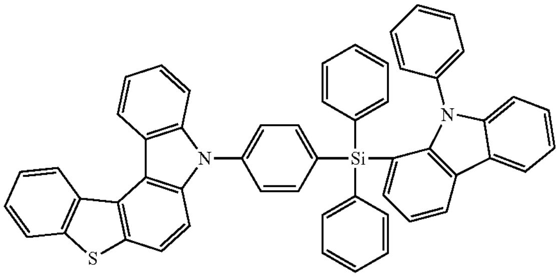
199
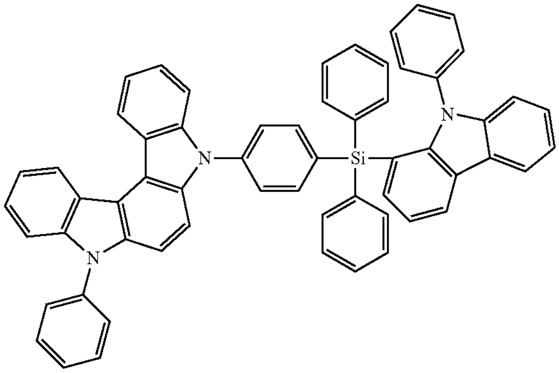
200
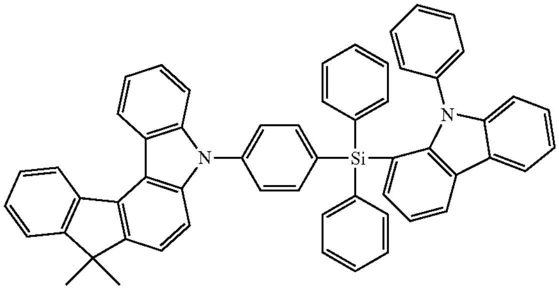
201
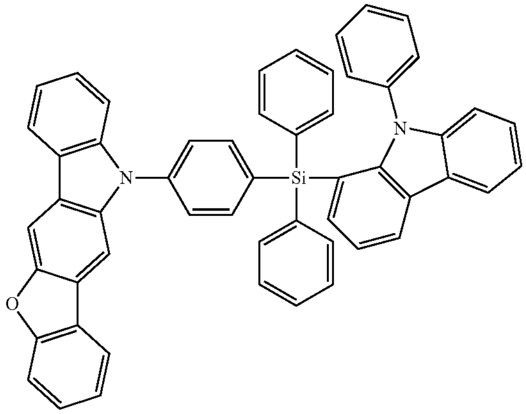
-continued
202
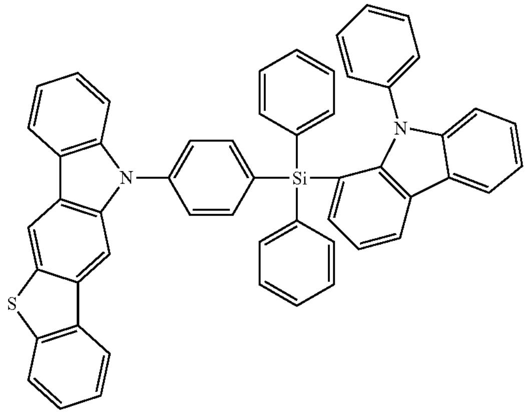
203
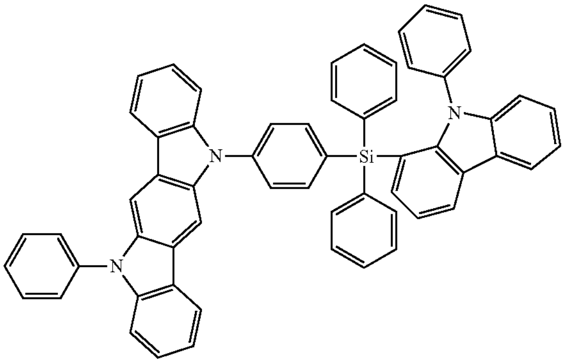
204
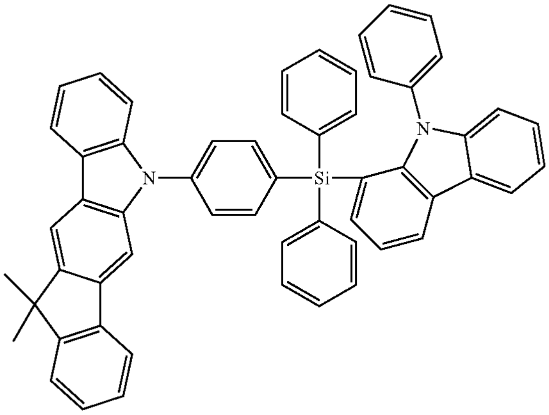

-continued
205
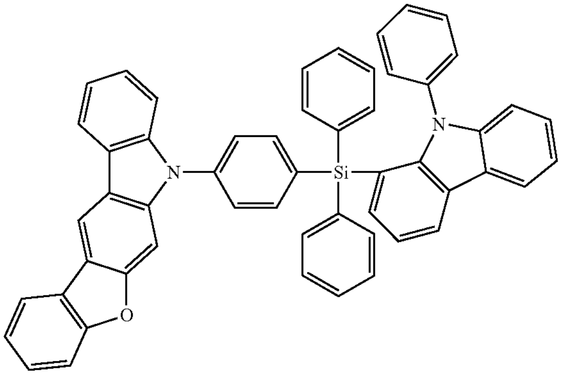
206
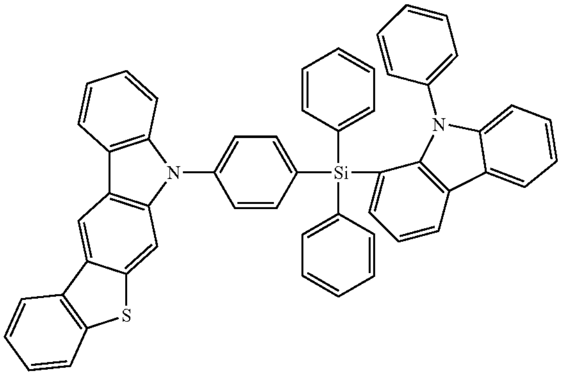
207
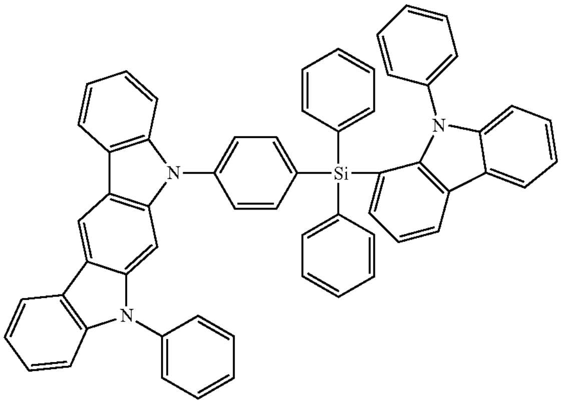
208
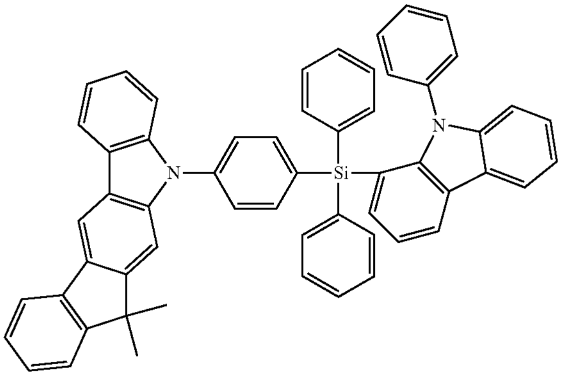
-continued
209
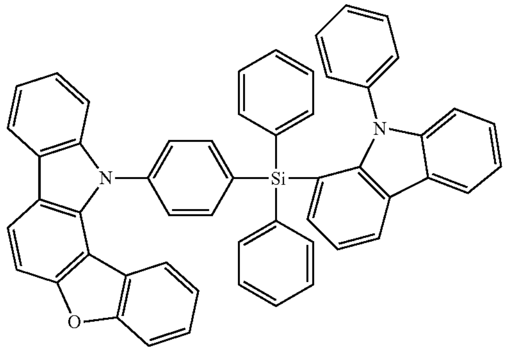
210
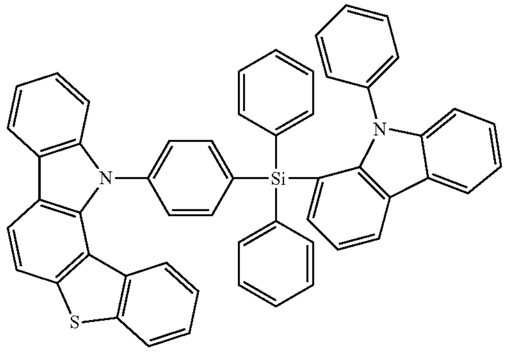
211
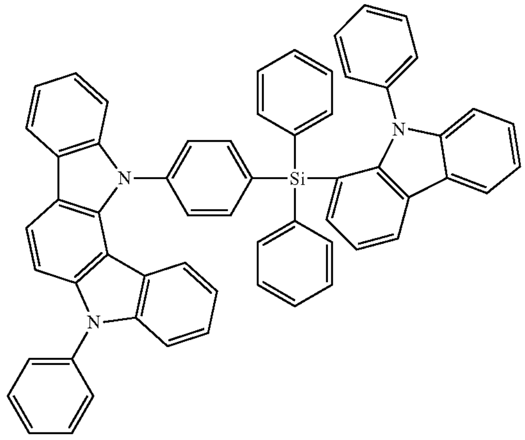
212
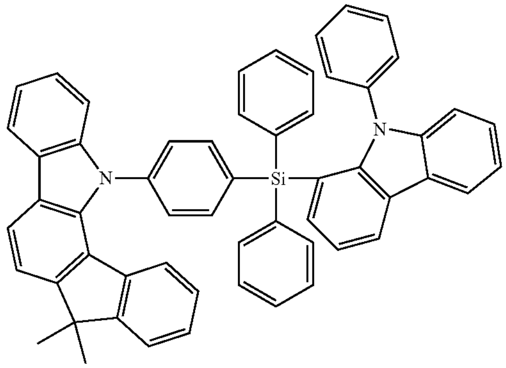

-continued
213
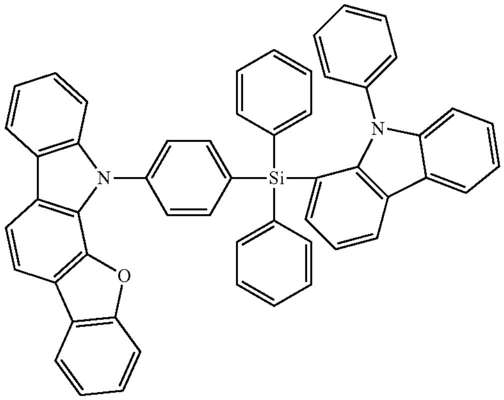
214
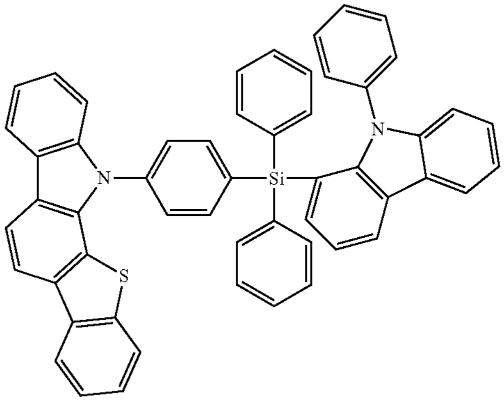
215
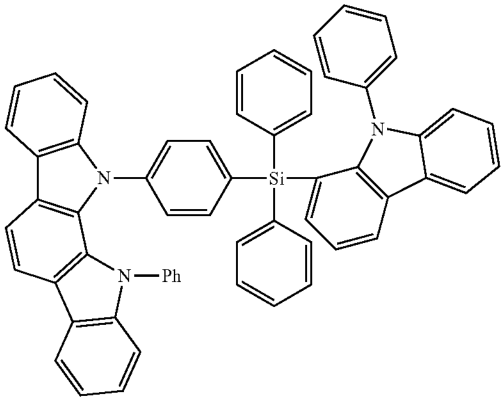
-continued
216
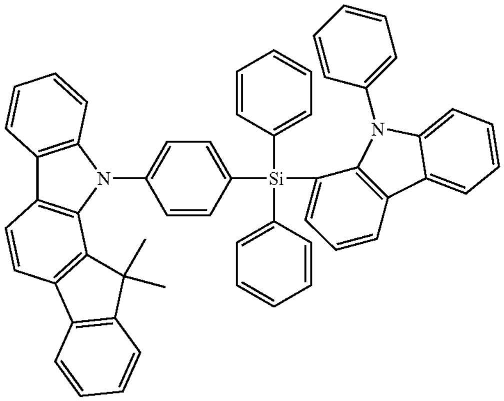
217
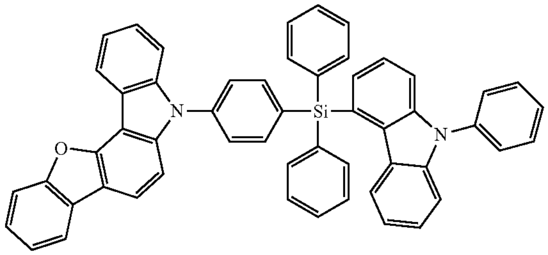
218
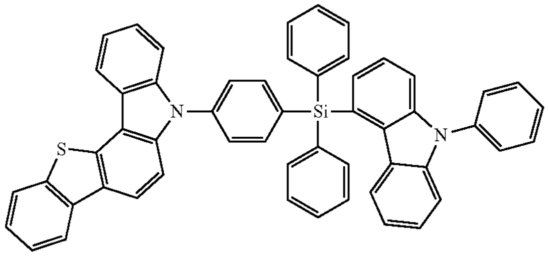
219
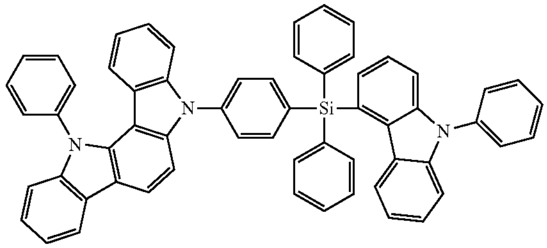
220
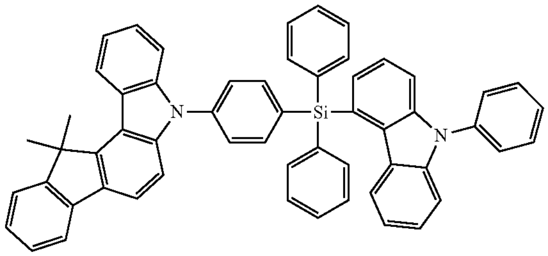

-continued
221
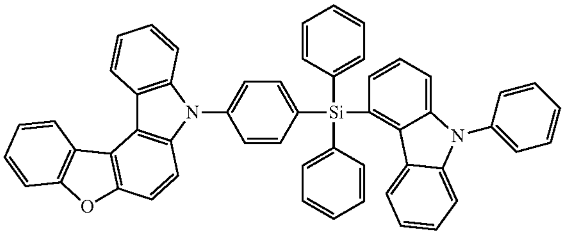
222
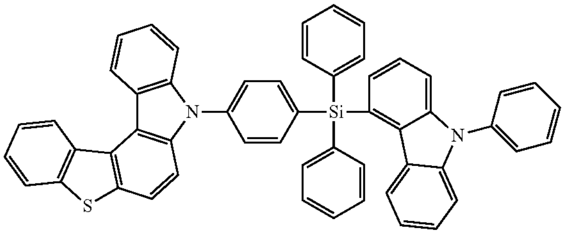
223
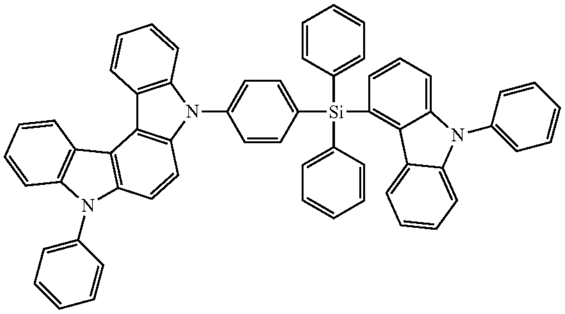
224
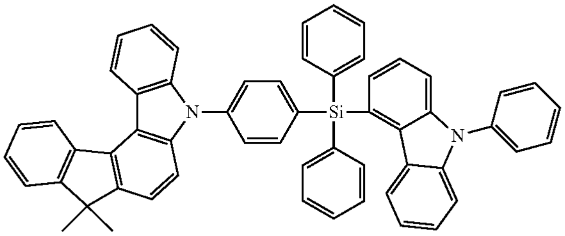
225
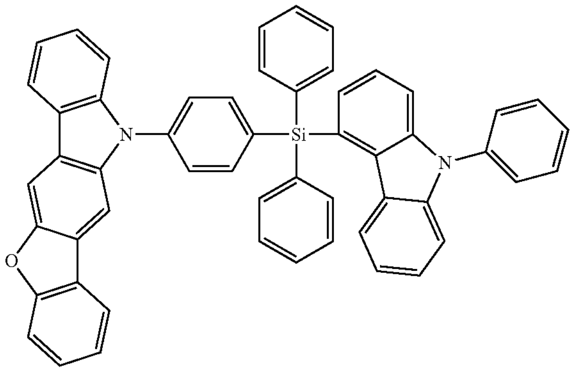
-continued
226
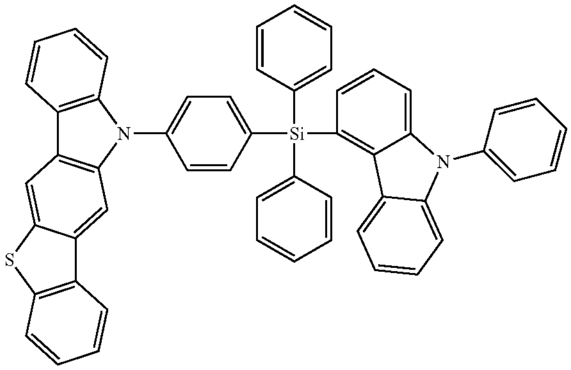
227
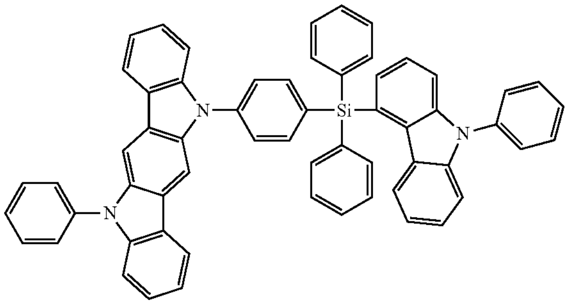
228
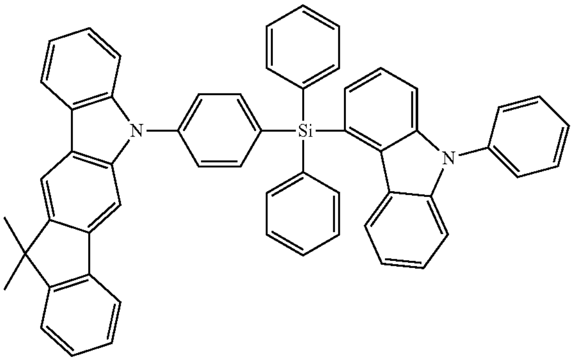
229
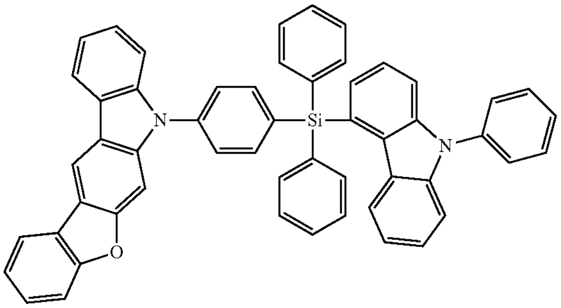

-continued
230
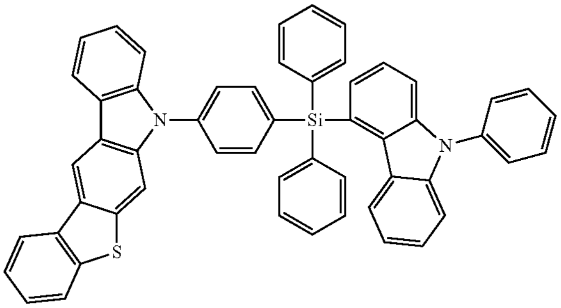
231
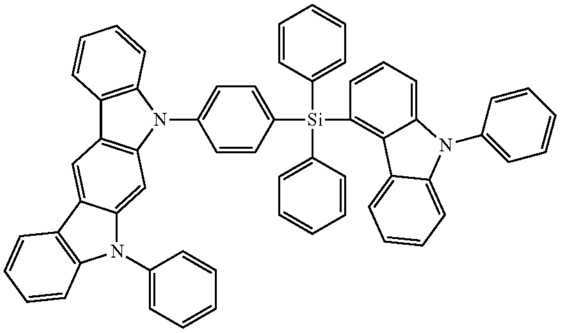
232
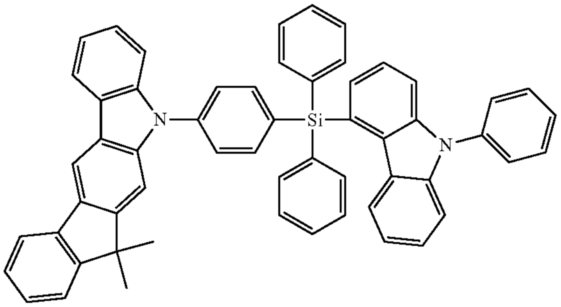
233
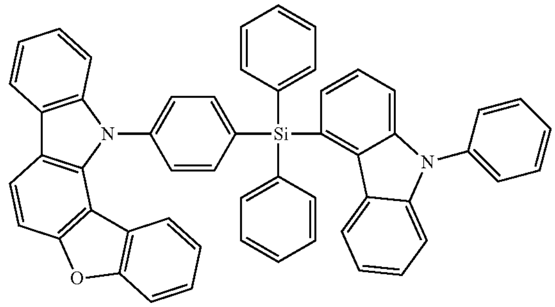
-continued
234
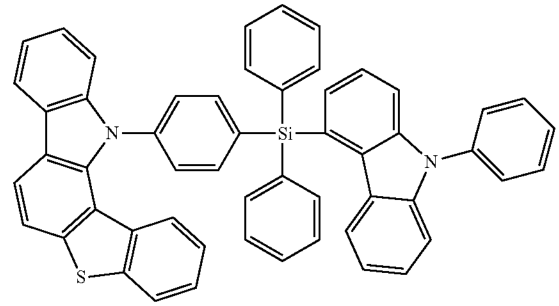
235
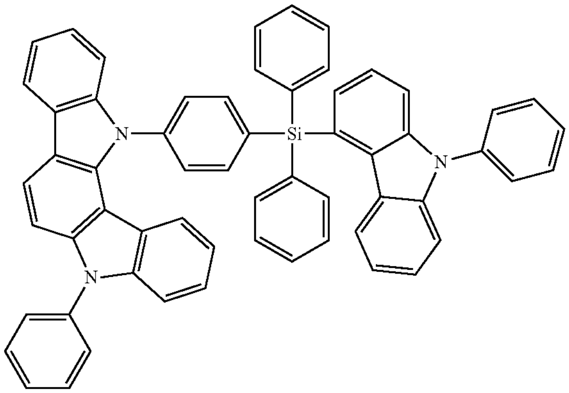
236
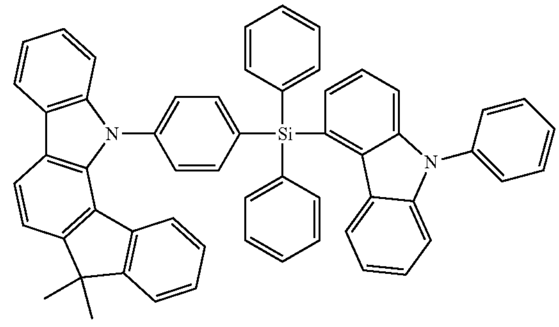

237
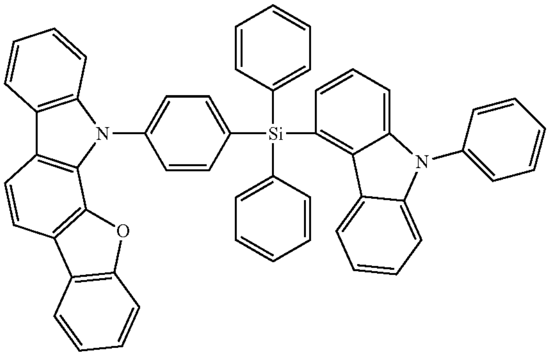
238
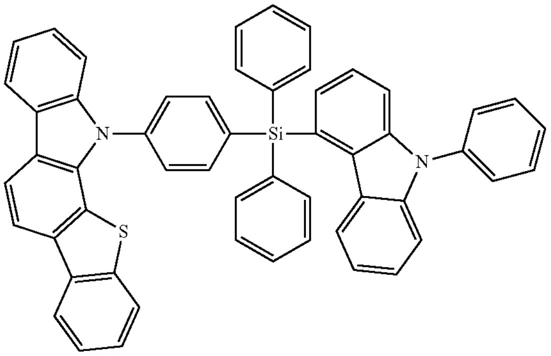
239
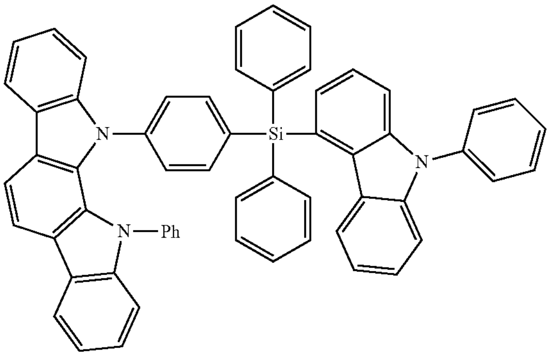
240
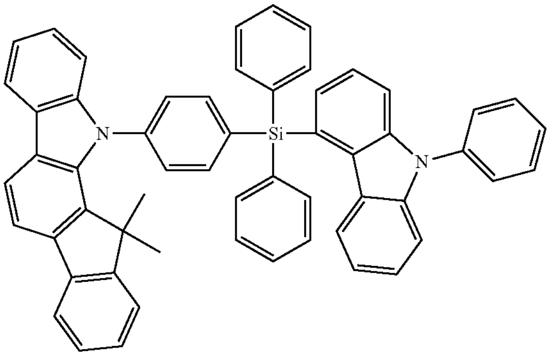
241
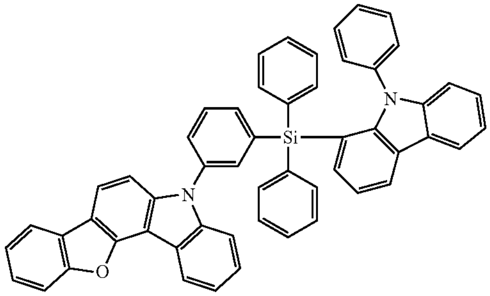
242
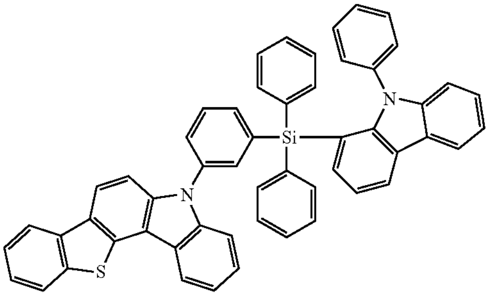
243
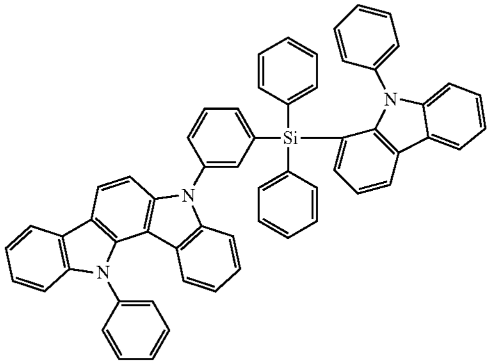
244
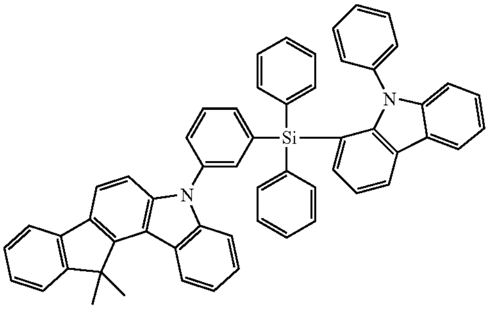

-continued
245
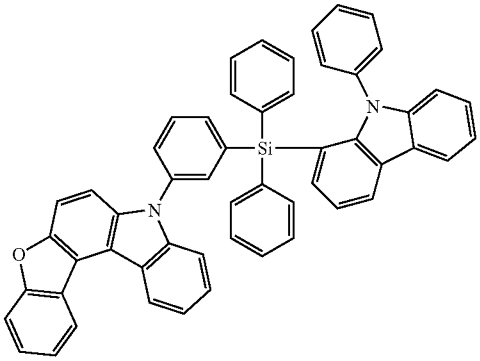
246
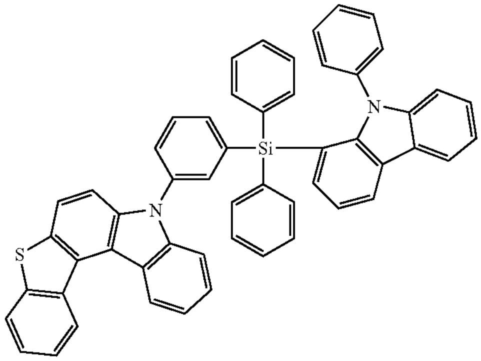
247
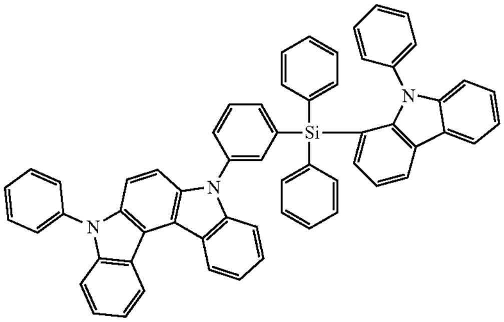
248
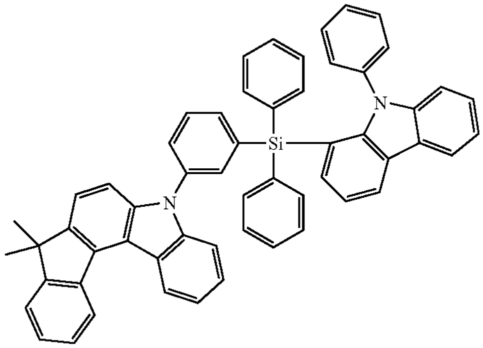
249
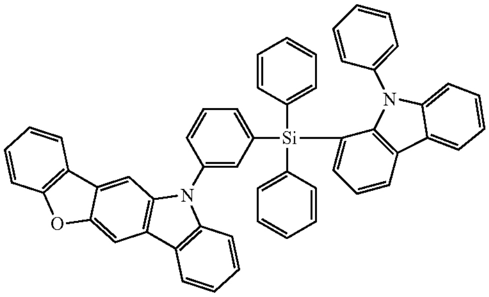
250
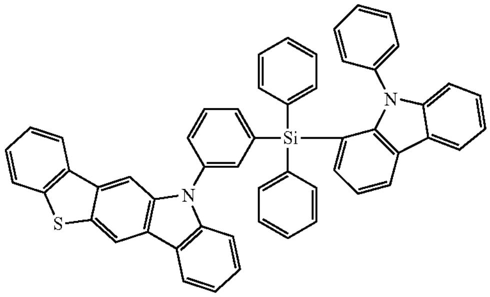
251
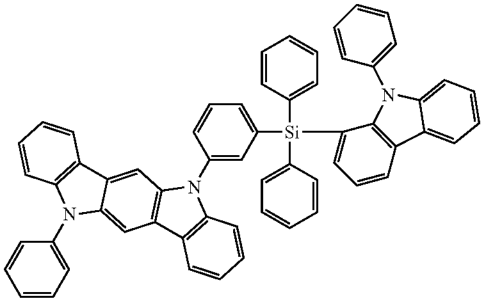
252
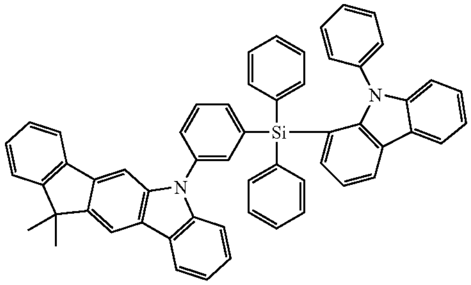
253
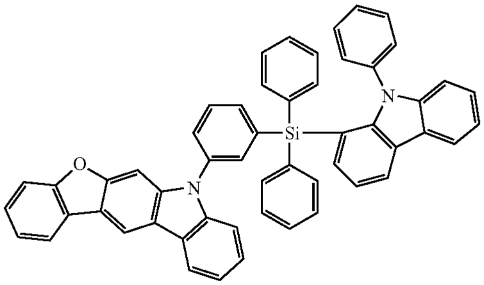
254
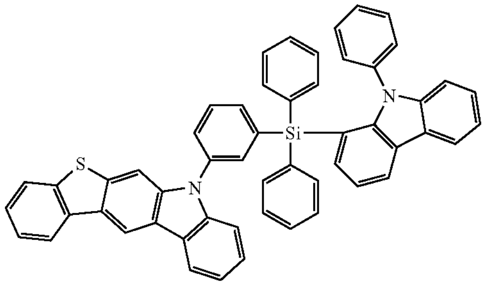

-continued
255
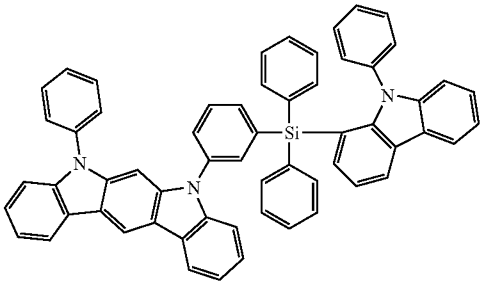
256
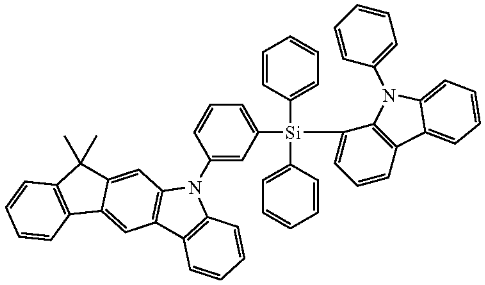
257
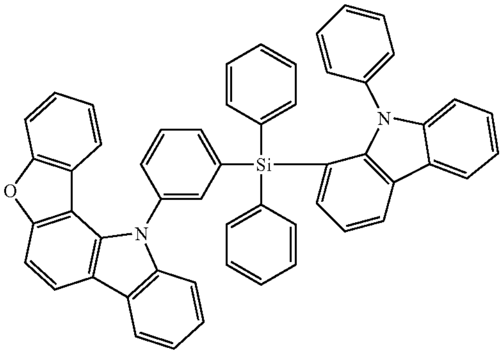
258
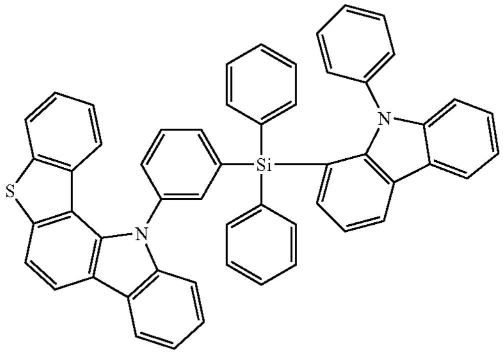
259
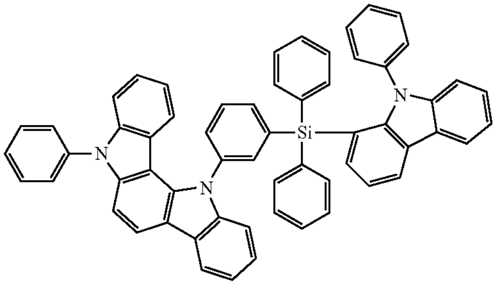
260
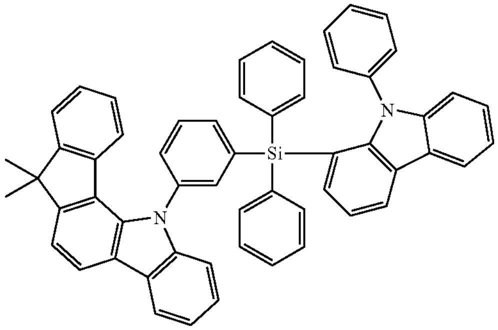
261
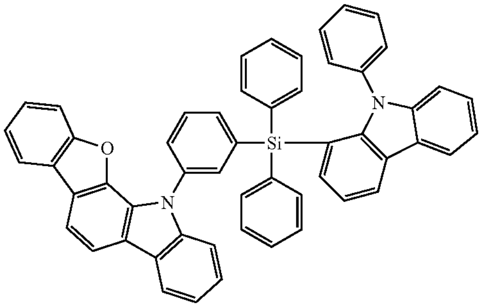
262
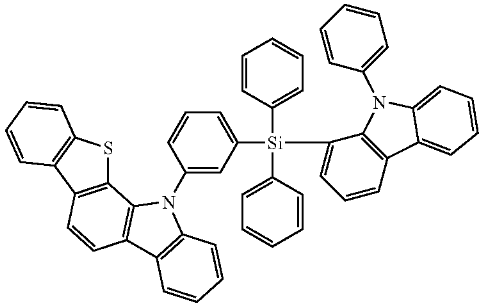
263
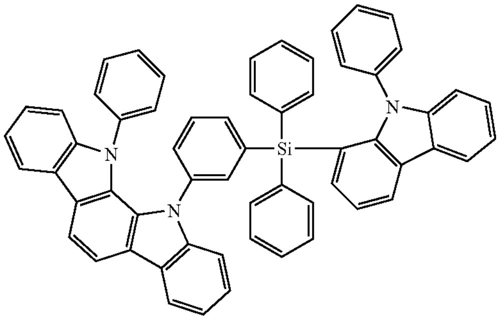
264
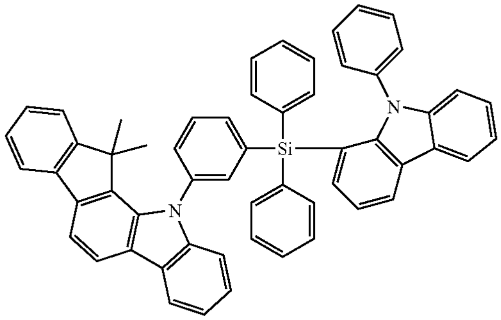

-continued
265
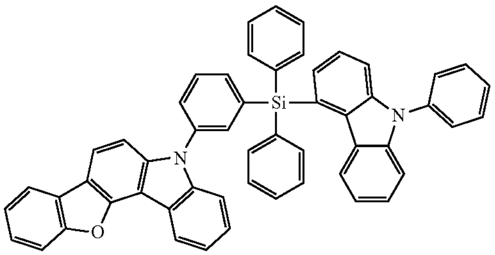
266
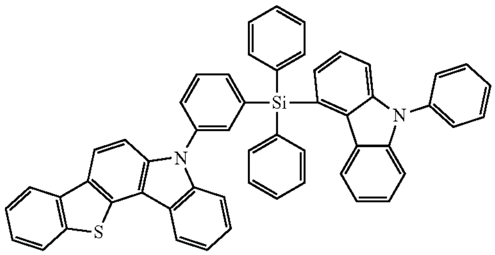
267
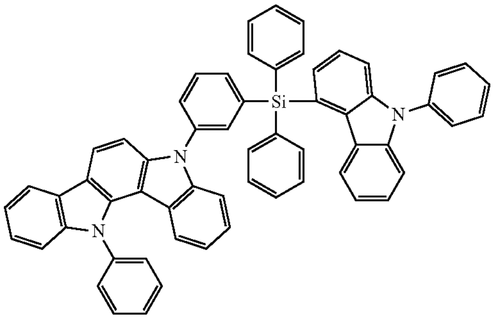
268
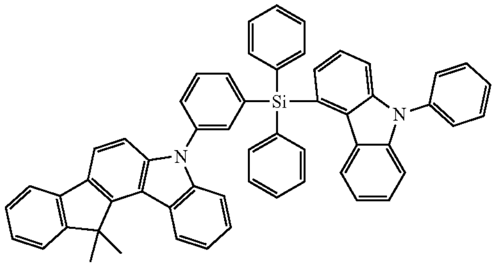
269
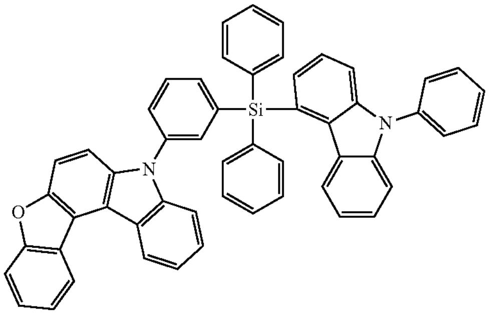
270
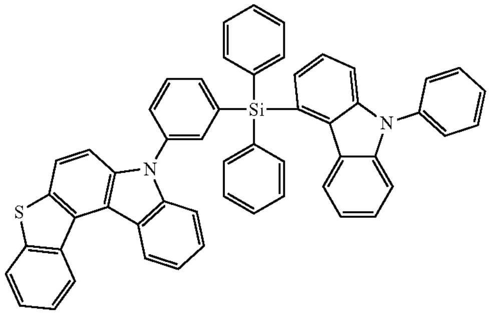
271
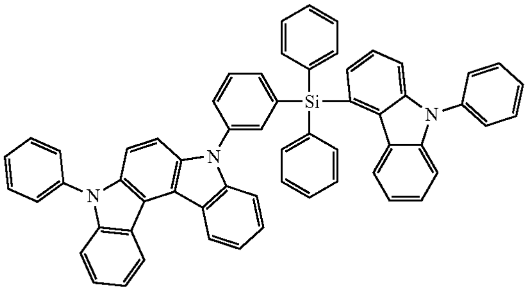
272
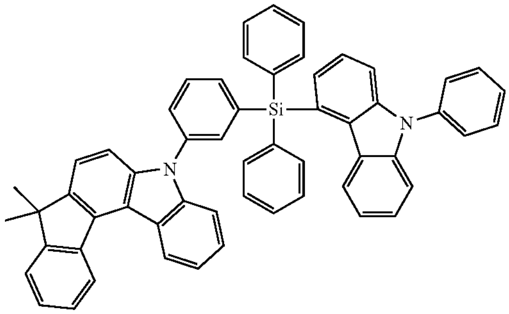
273
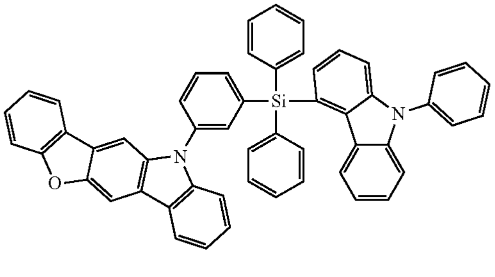
274
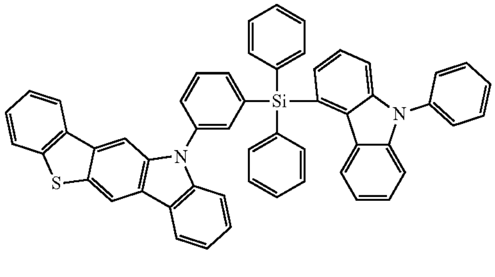

-continued
275
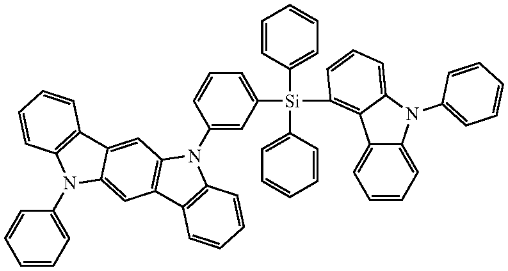
276
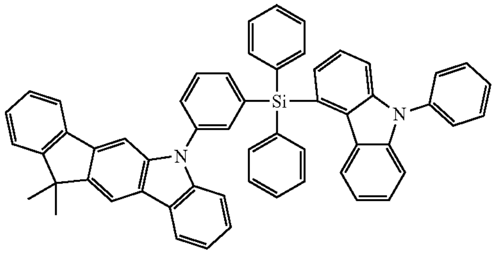
277
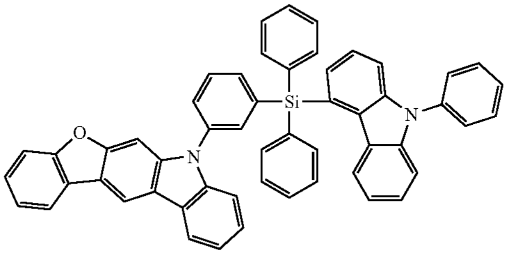
278
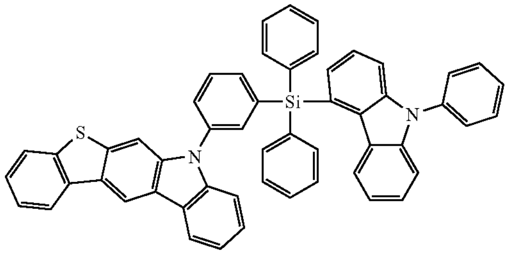
279
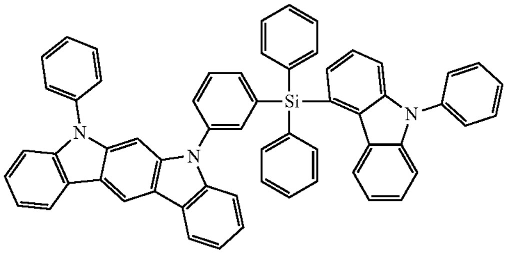
280
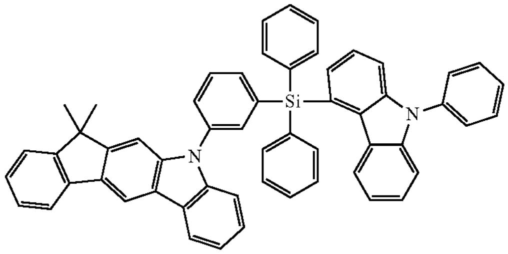
281
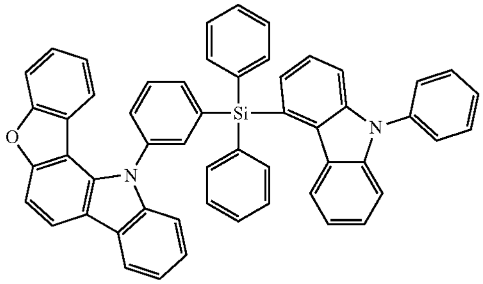
282
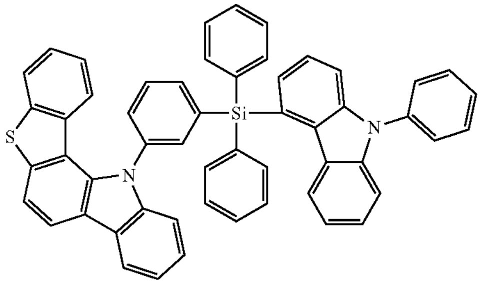
283
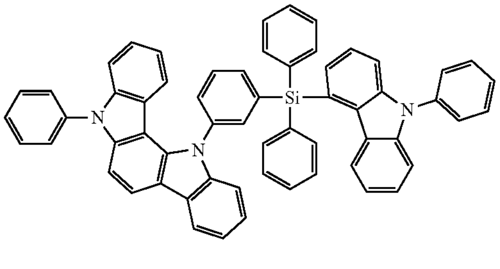
284
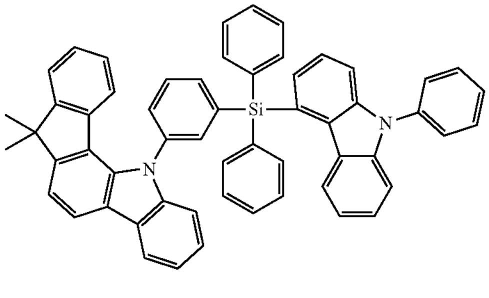

-continued
285
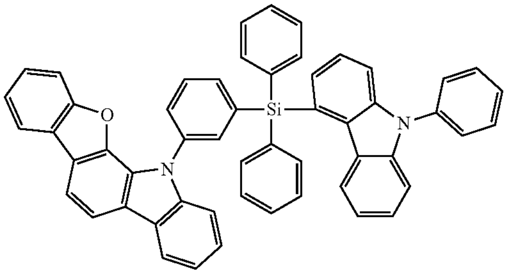
286
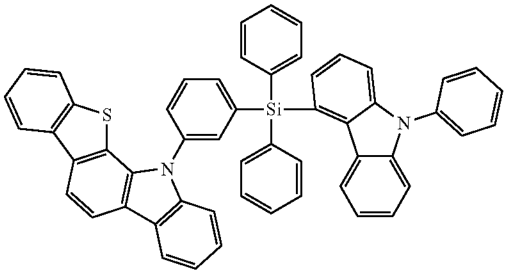
287
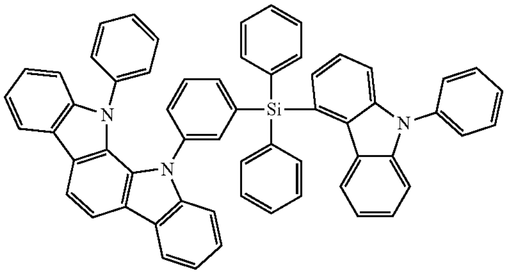
288
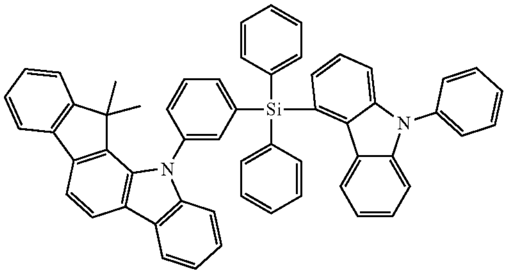
289
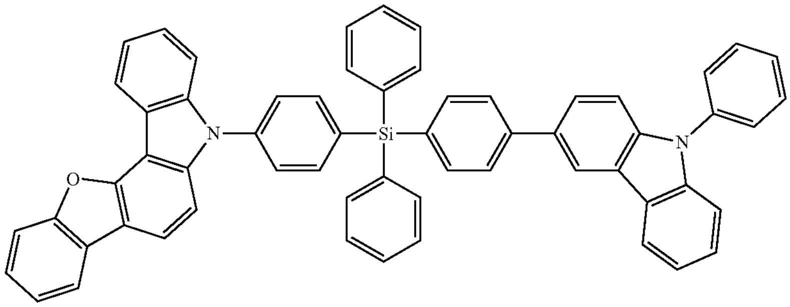
290
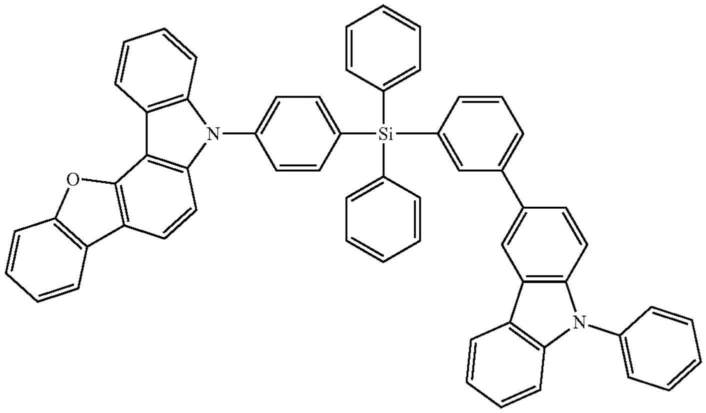
291
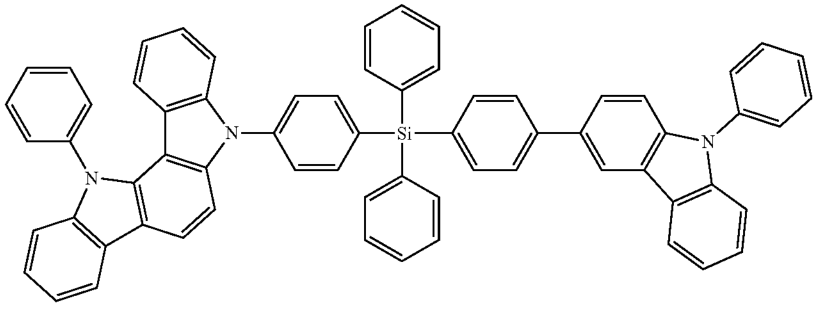

-continued
292
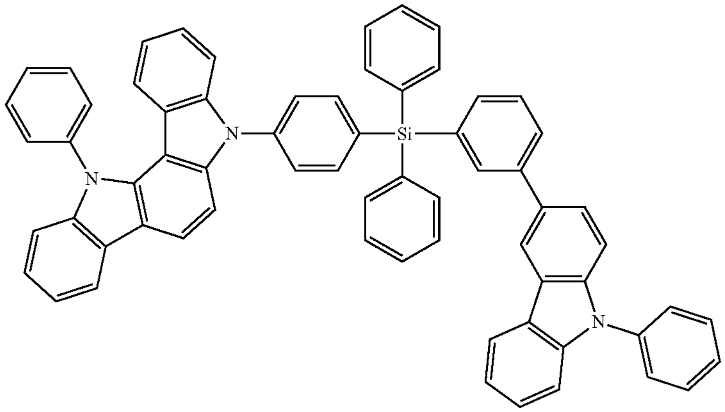
293
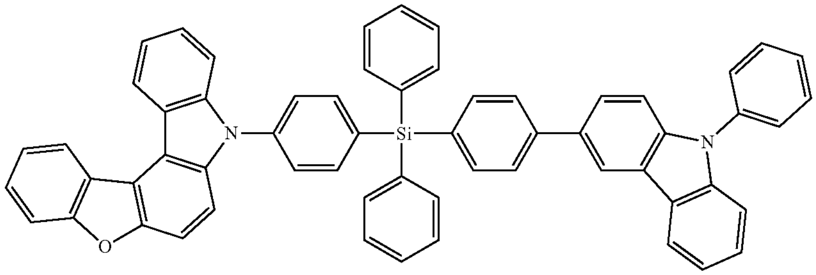
294
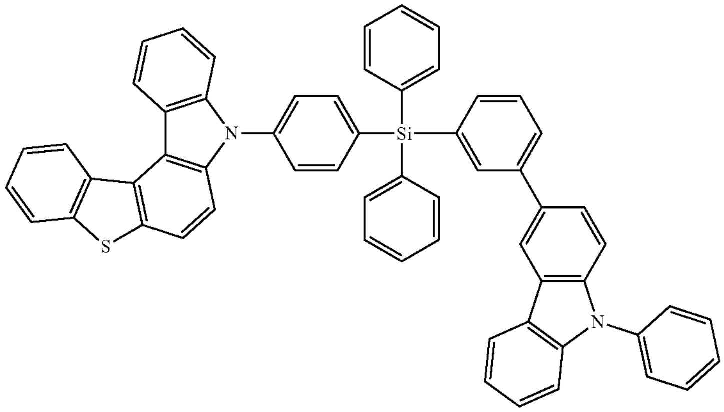
295
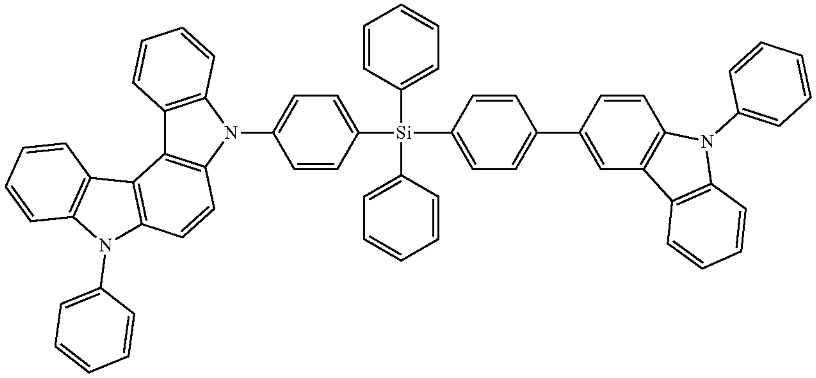

-continued
296
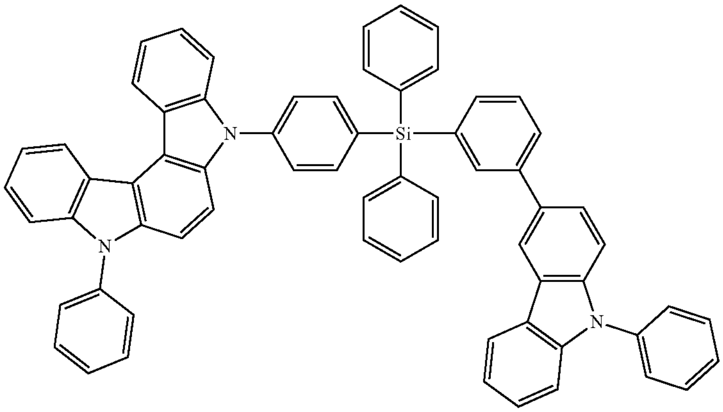
297
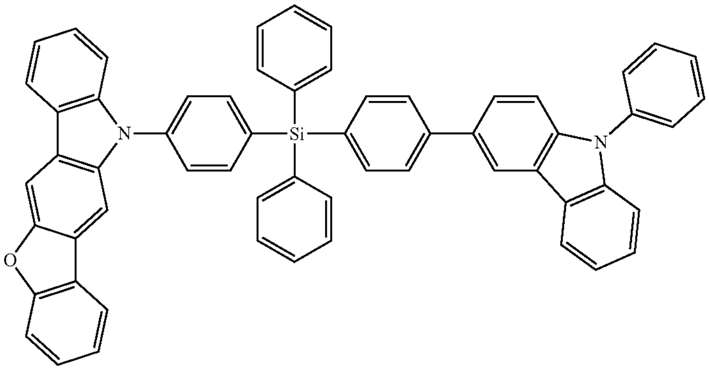
298
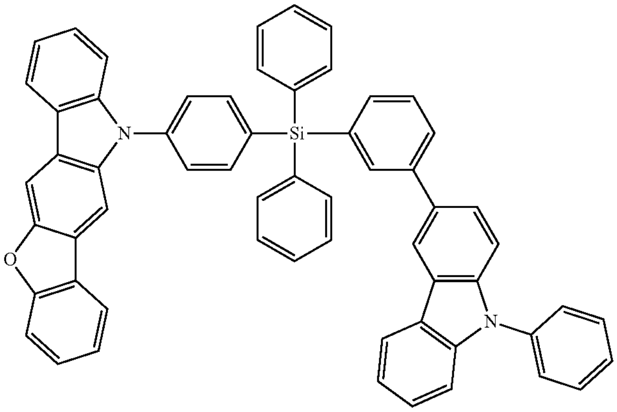
299
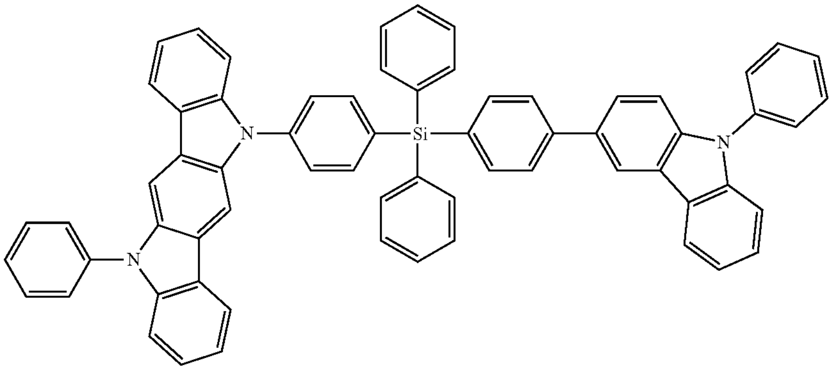

-continued
300
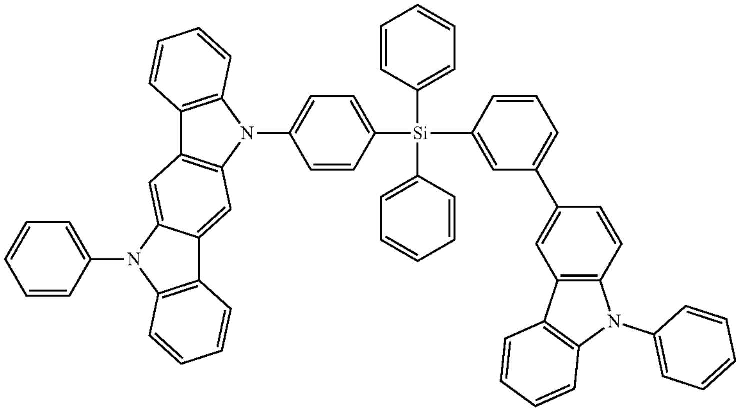
301
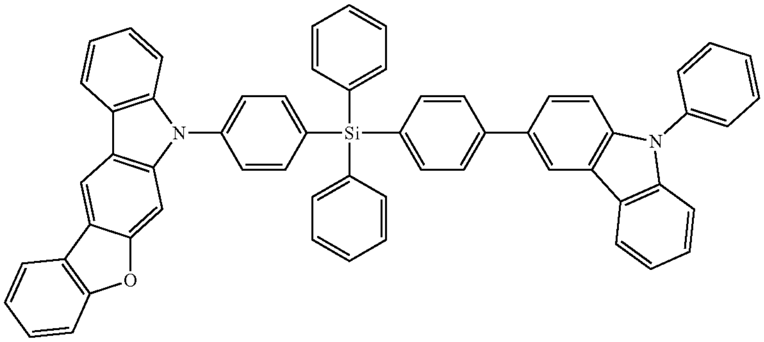
302
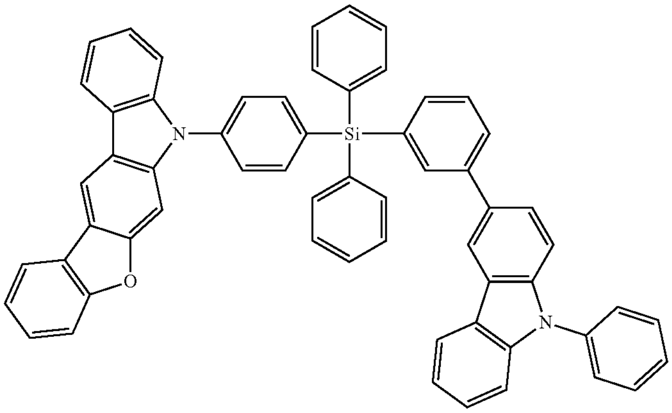
303
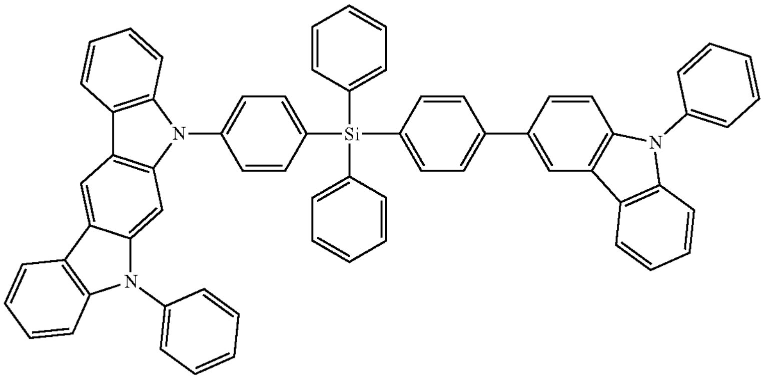

-continued
304
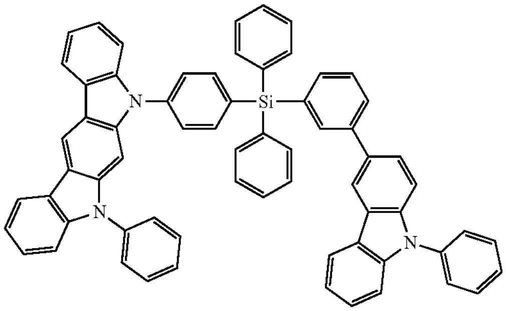
305
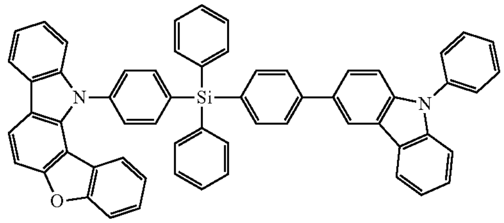
306
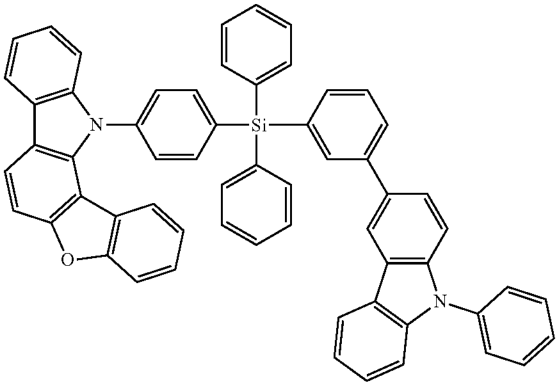
307
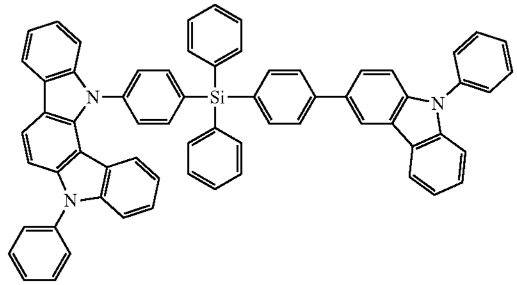
308
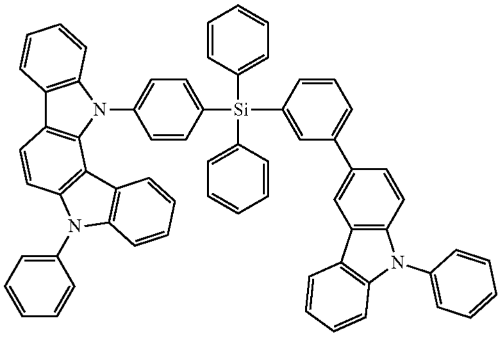
309
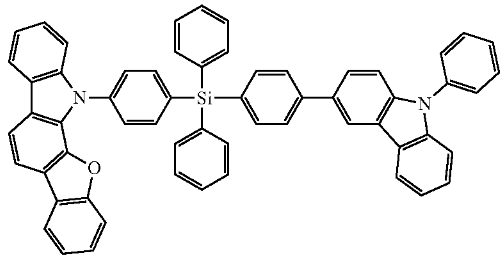
310
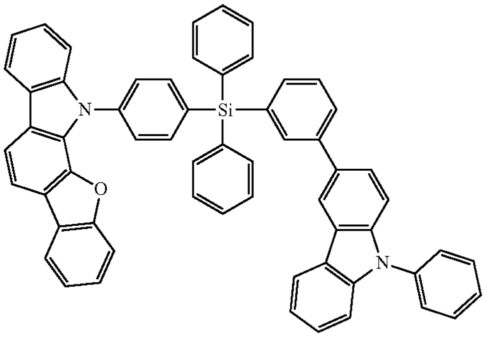
311
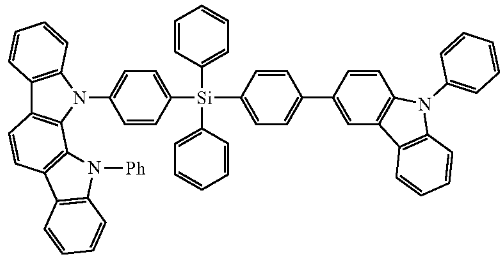

-continued
312
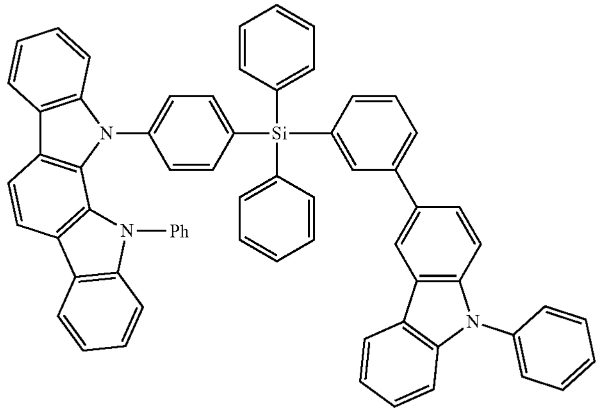
313
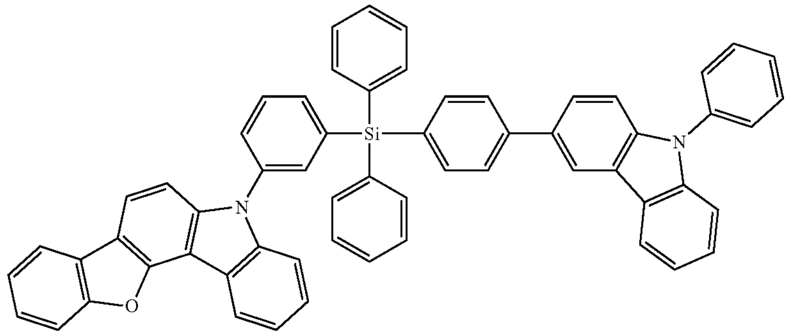
314
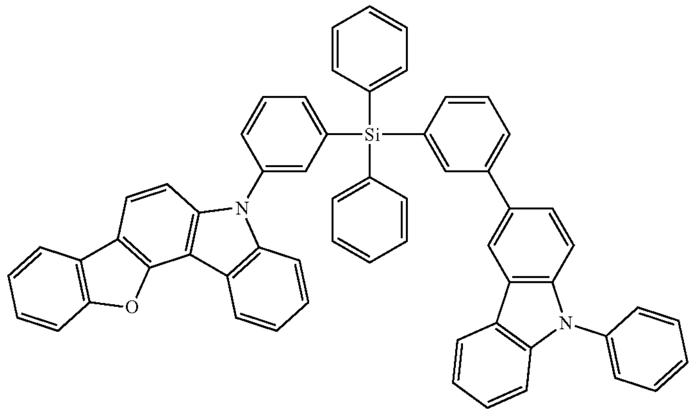
315
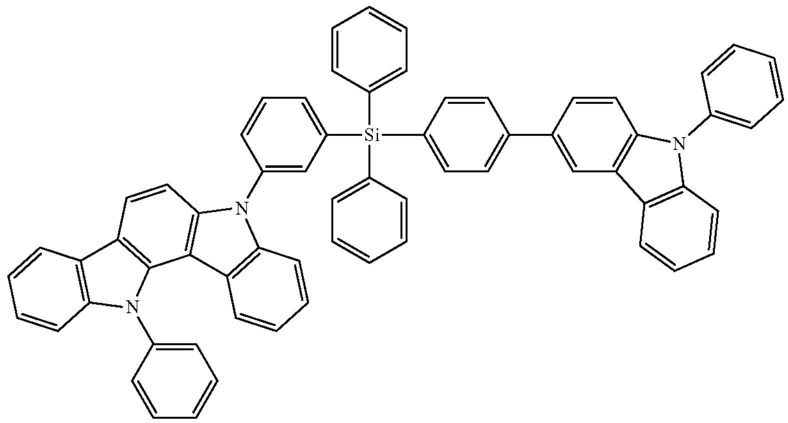

-continued
316
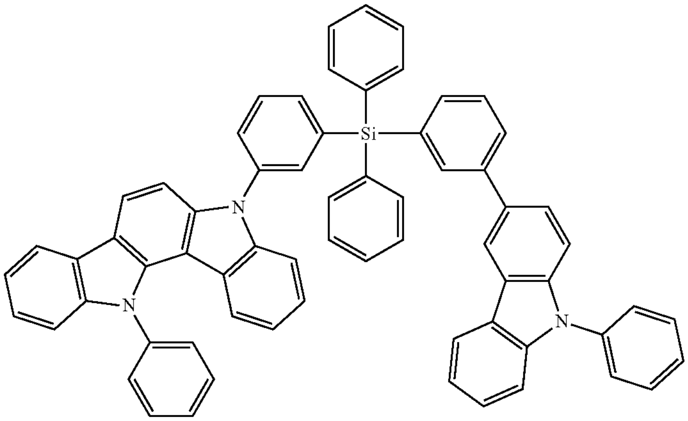
317
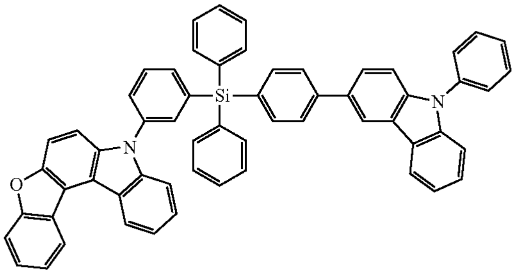
318
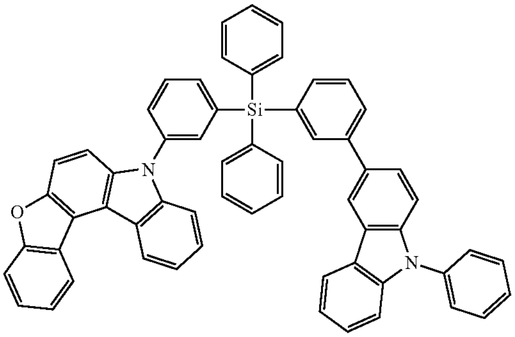
319
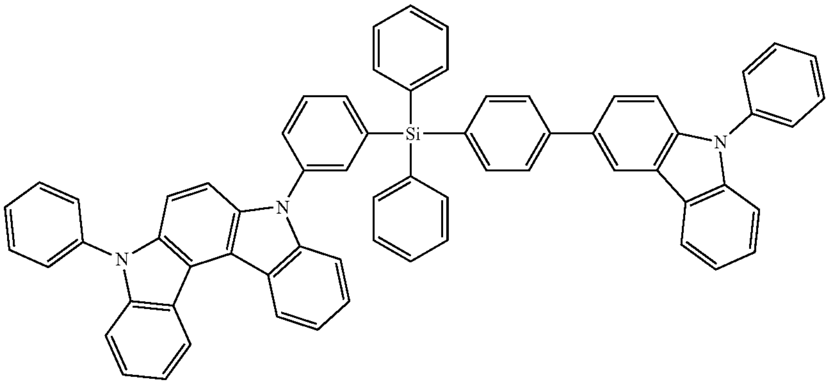
320
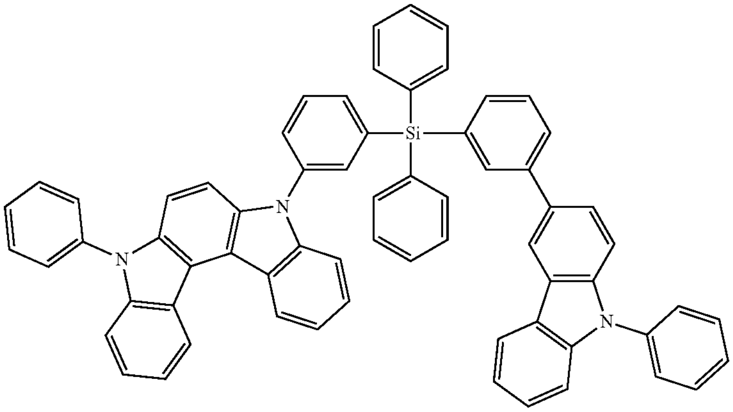

-continued
321
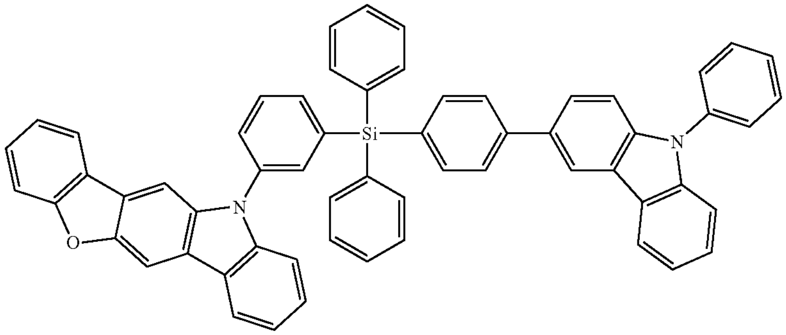
322
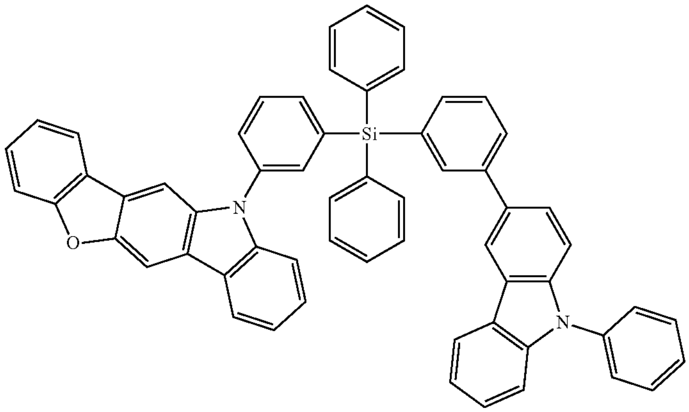
323
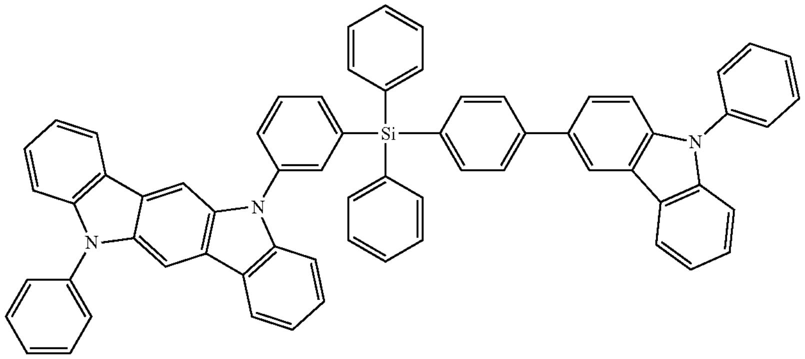
324
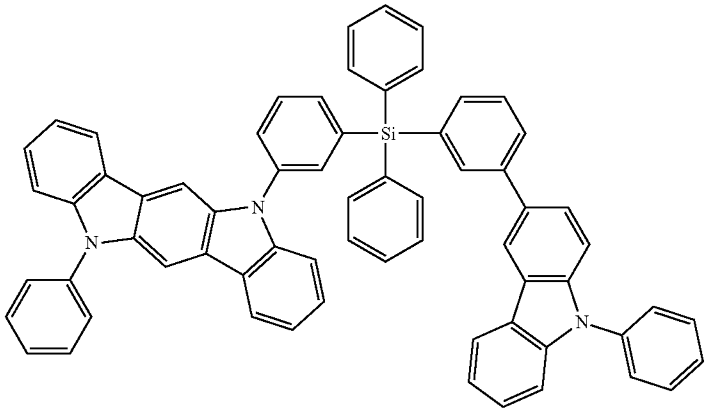

-continued
325
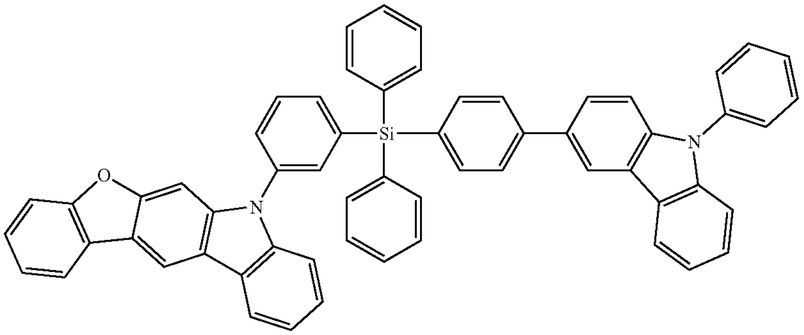
326
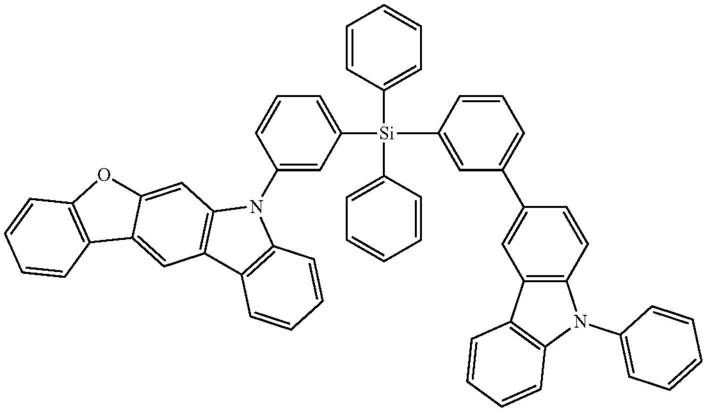
327
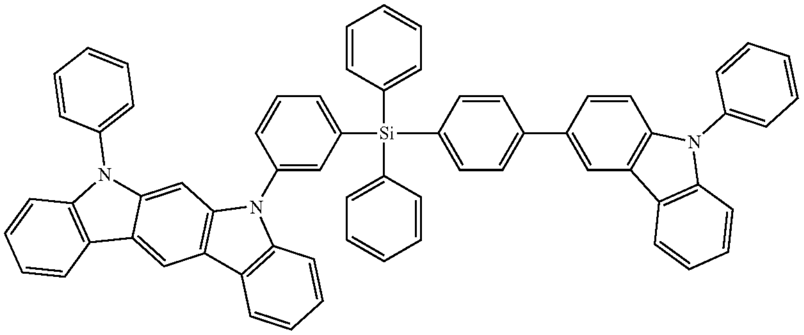
328
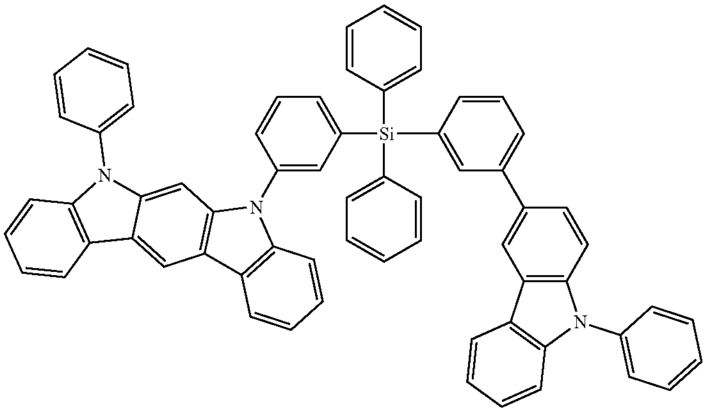

-continued
329
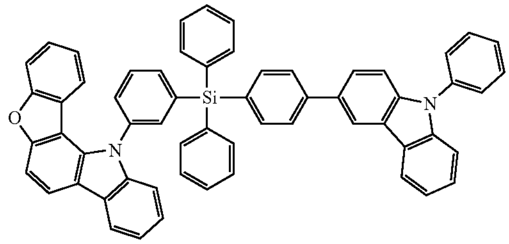
330
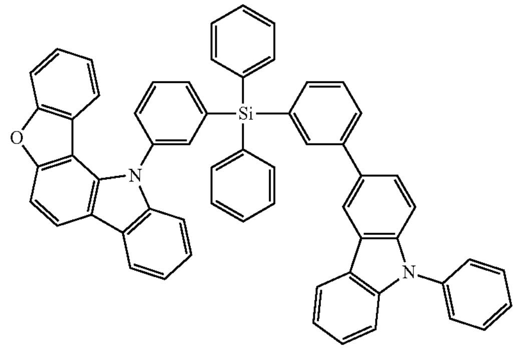
331
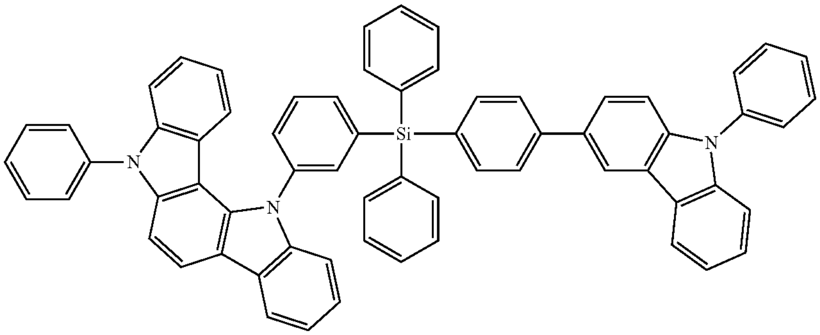
332
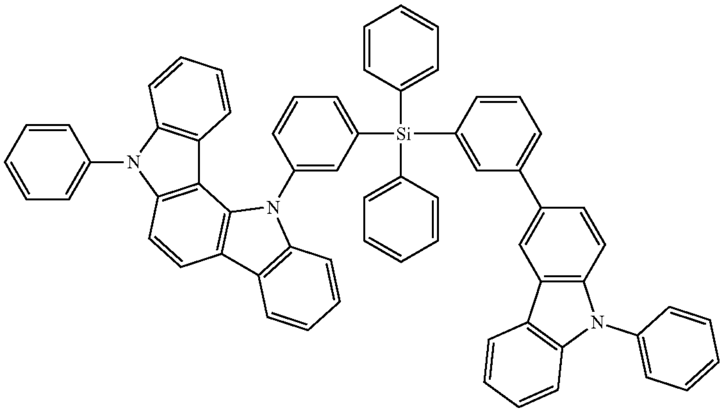
333
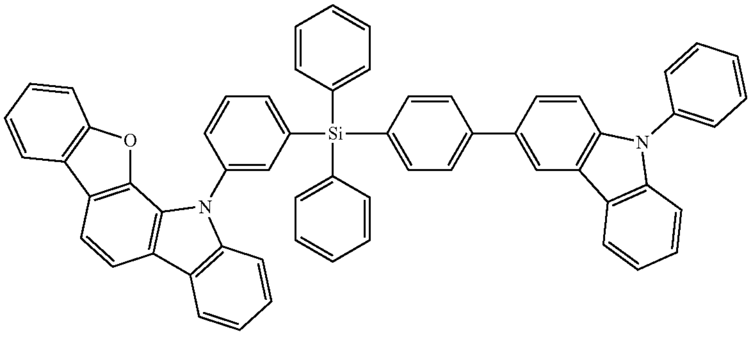

-continued
334
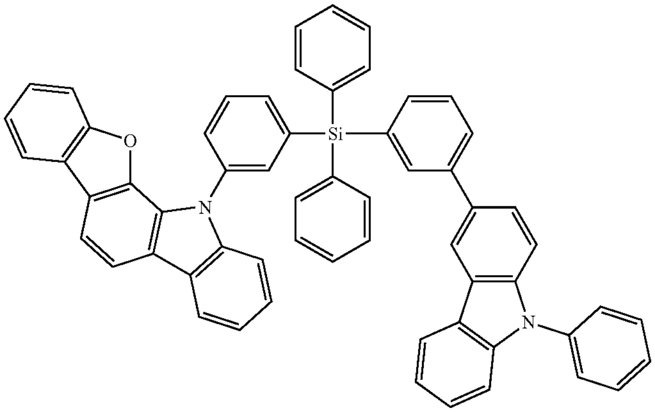
335
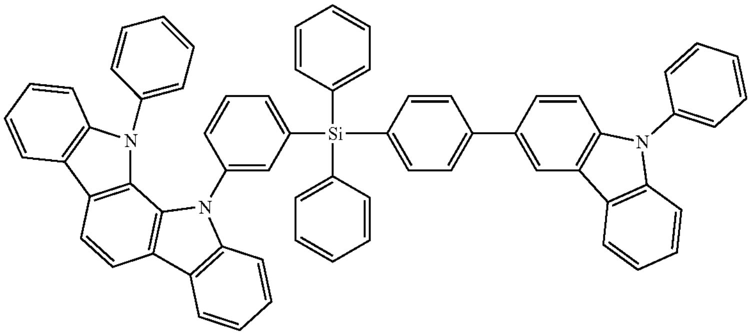
336
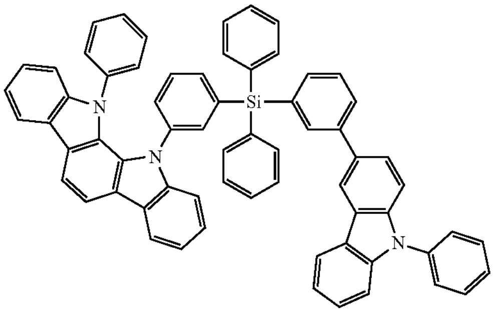
337
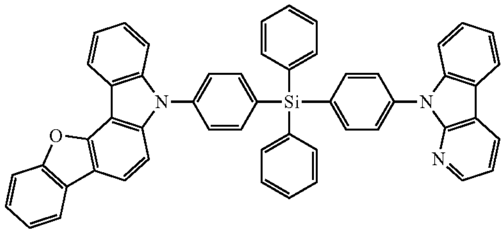
338
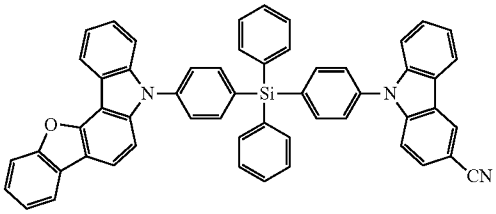
339
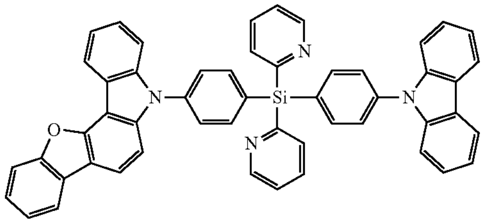
340
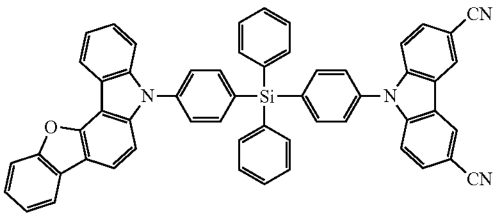
341
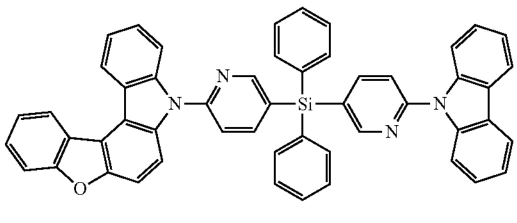

-continued
342
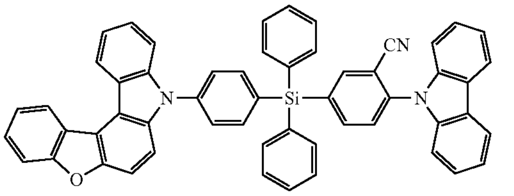
343
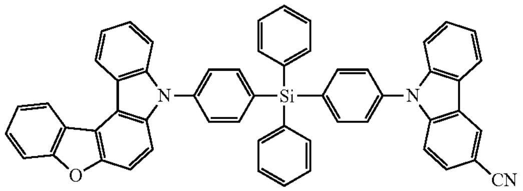
344
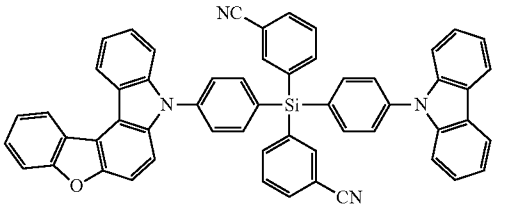
345
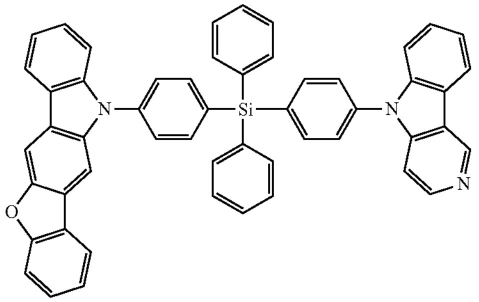
346
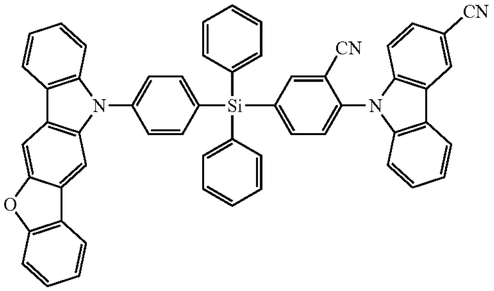
347
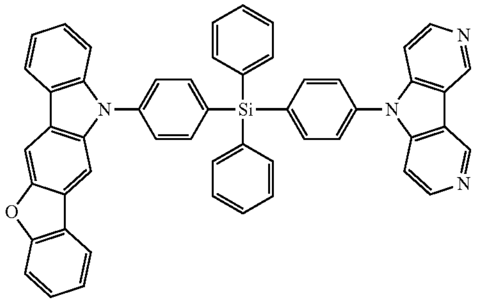
348
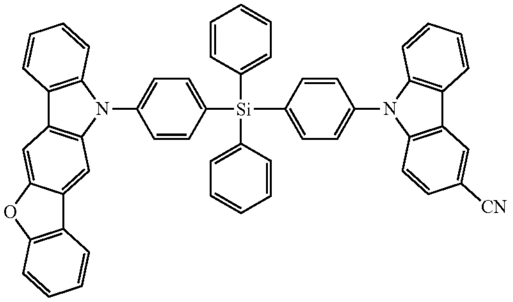
349
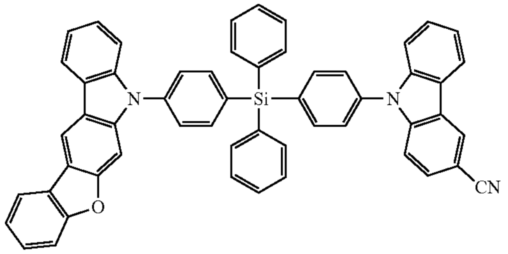
350
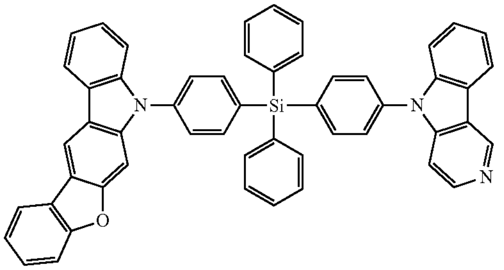
351
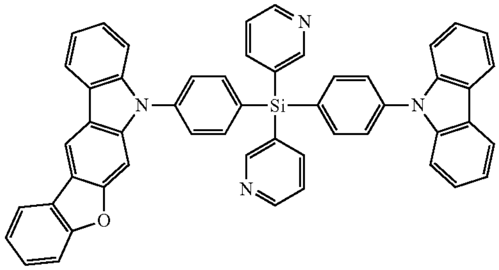

-continued
352
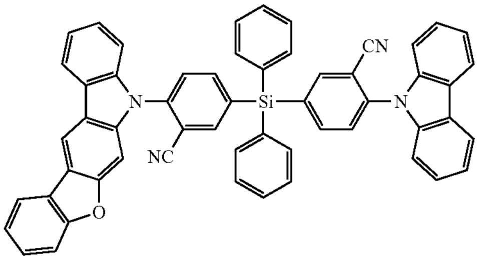
353
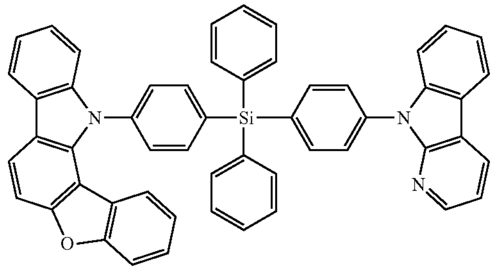
354
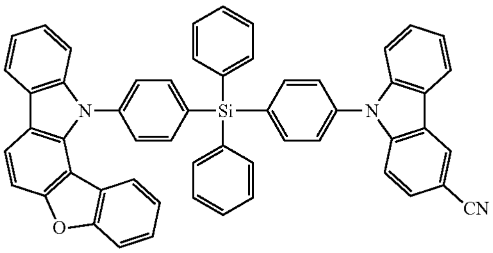
355
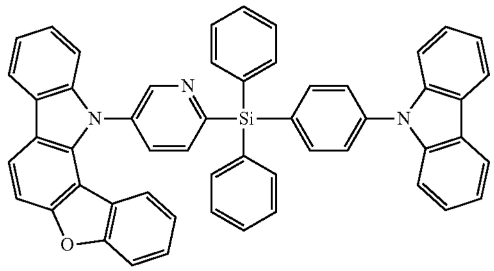
356
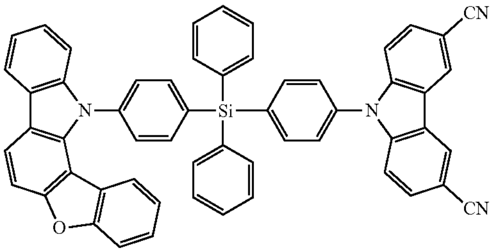
357
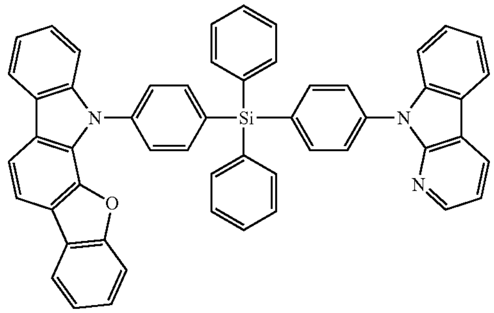
358
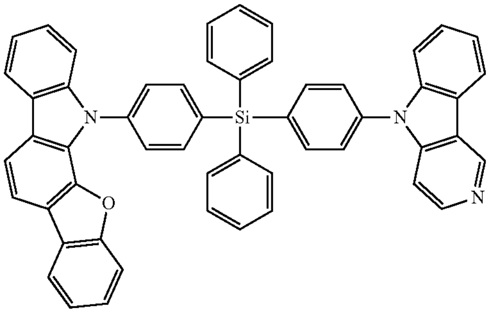
359
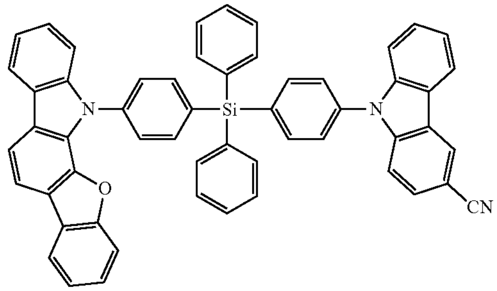
360
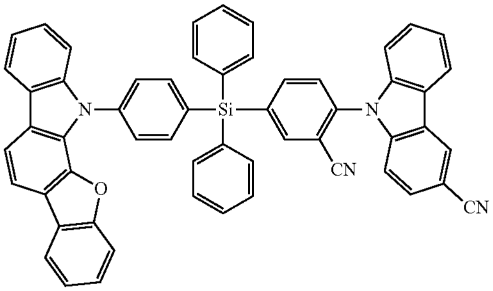
361
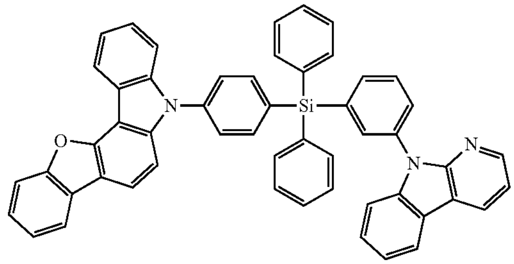

-continued
362
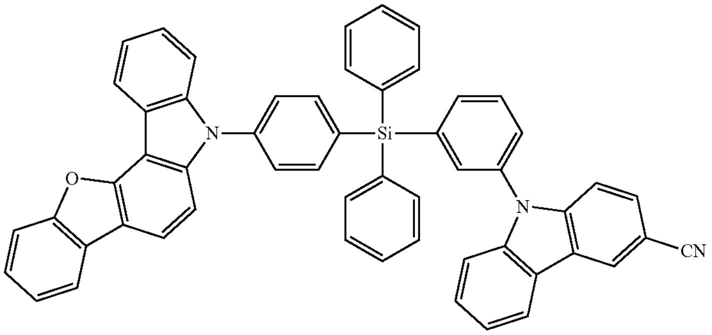
363
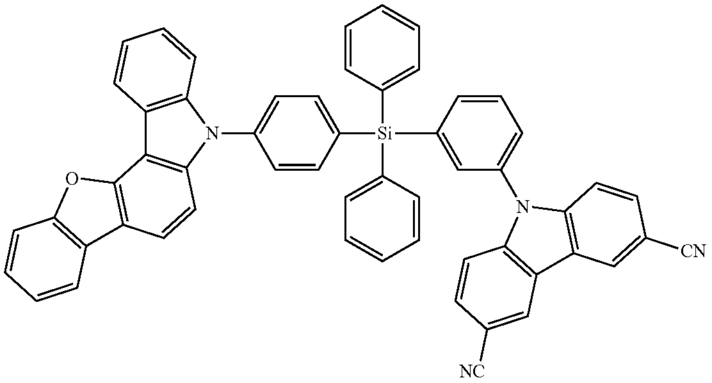
364
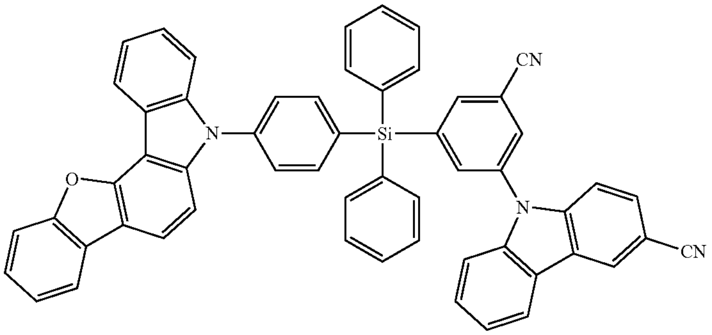
365
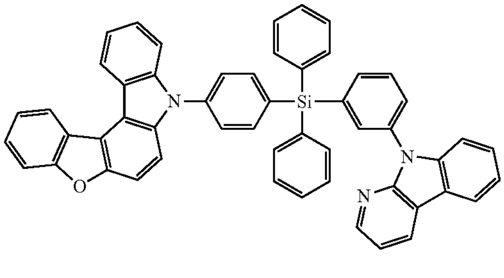
366
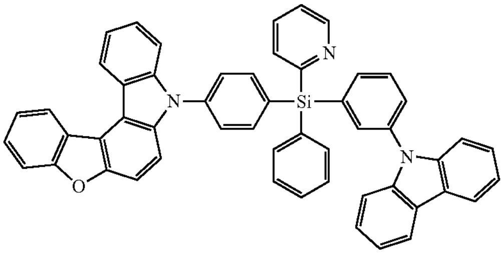

-continued
367
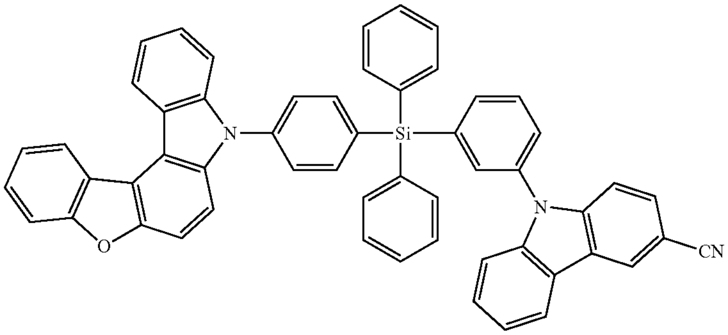
368
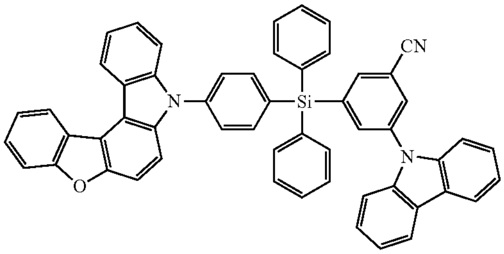
369
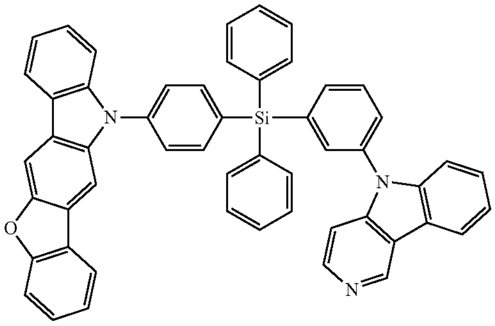
370
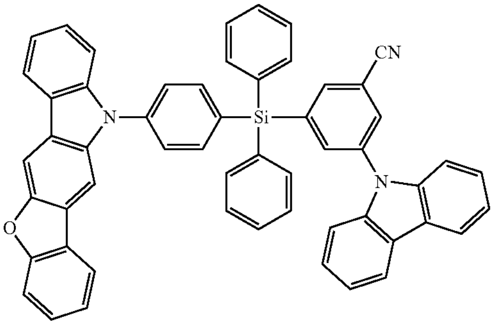
371
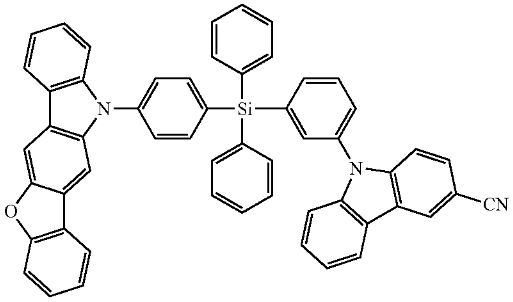
372
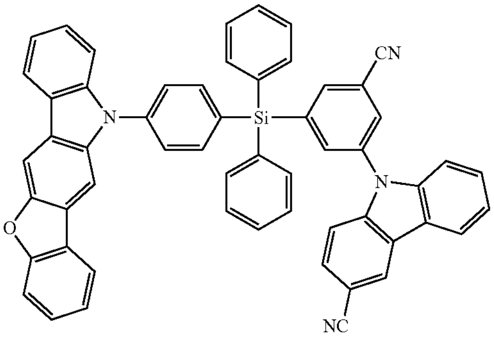
373
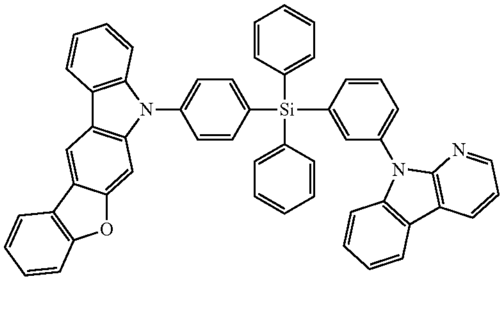
374
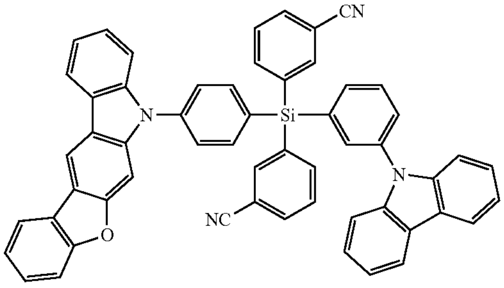
375
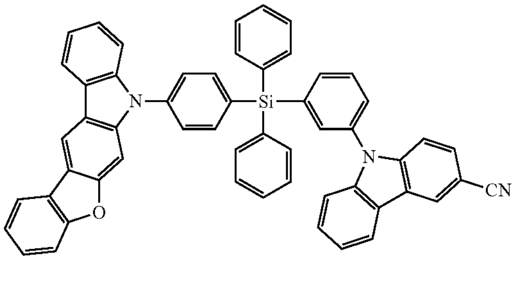

-continued
376
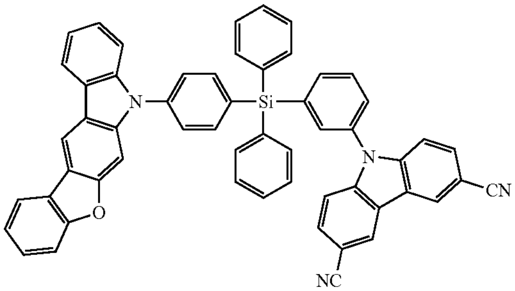
377
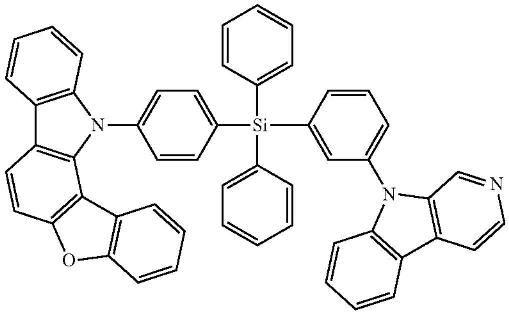
378
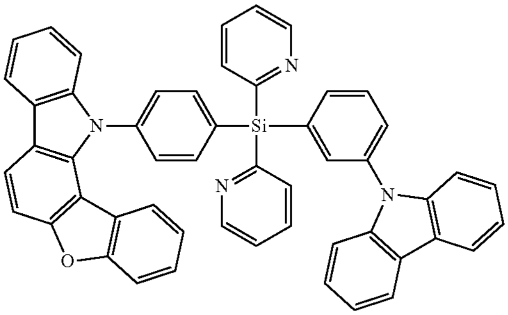
379
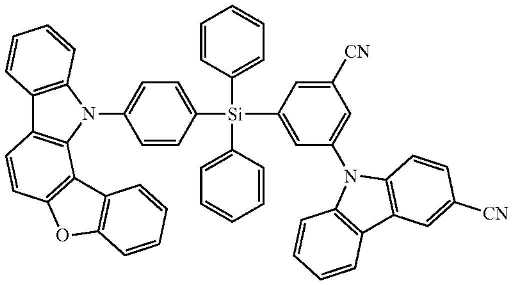
380
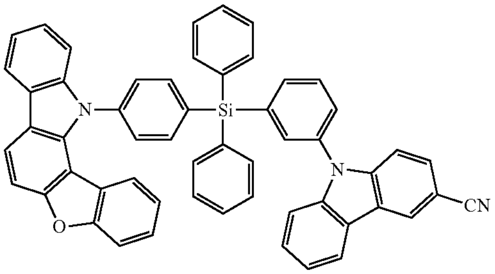
381
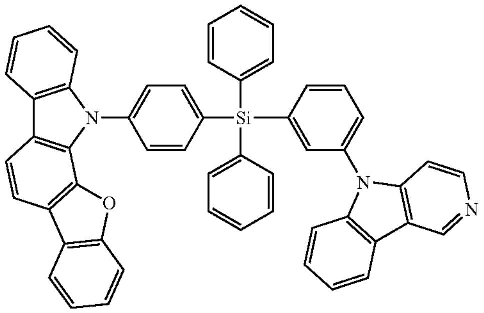
382
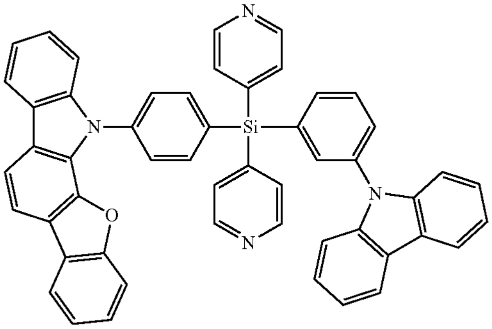
383
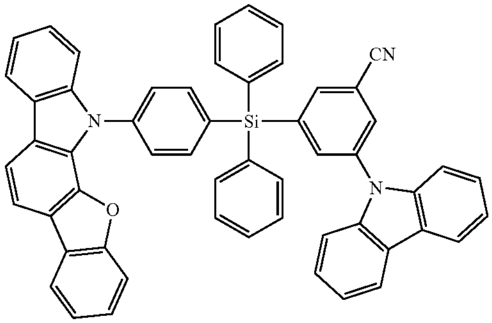
384
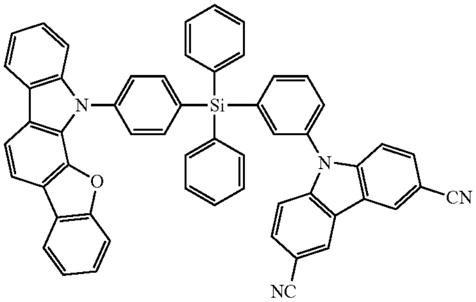
385
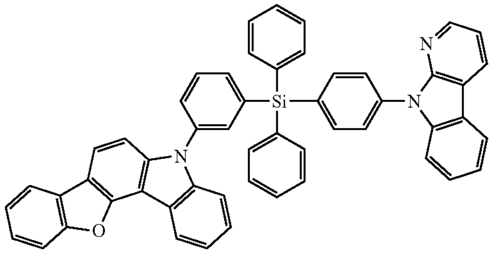

-continued
386
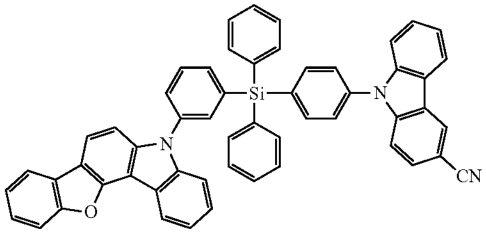
387
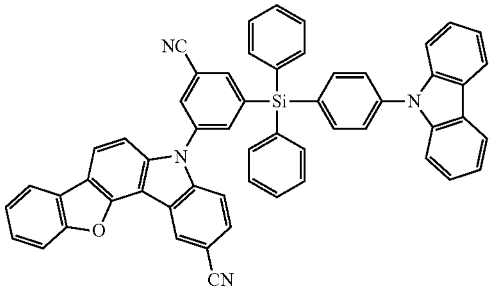
388
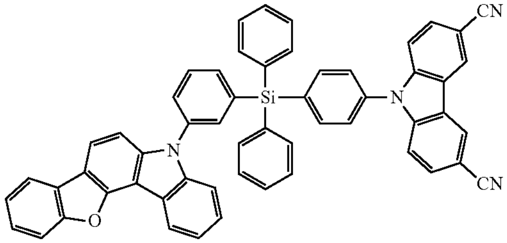
389
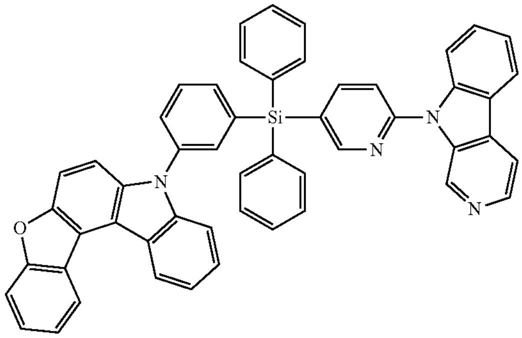
390
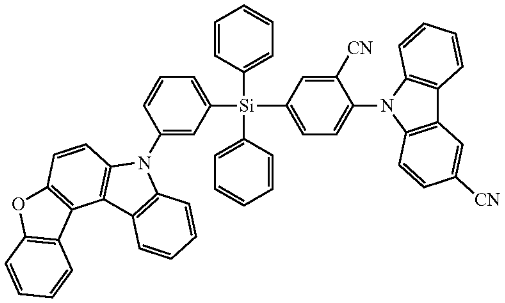
391
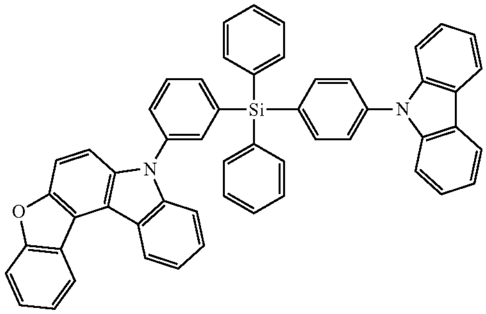
392
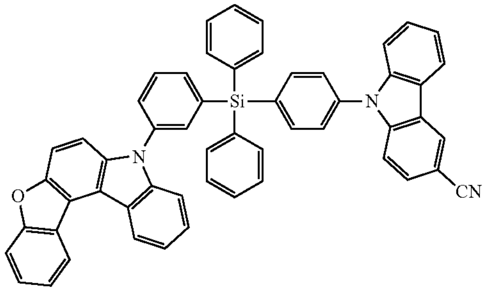
393
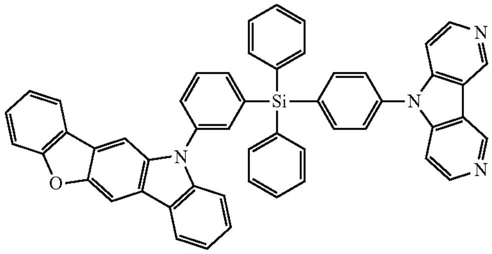
394
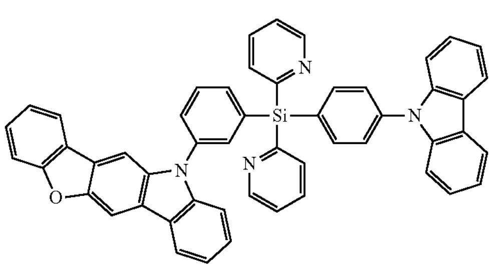
395
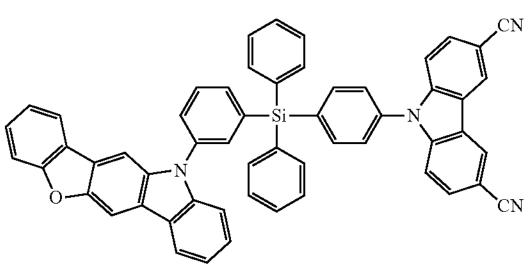

-continued
396
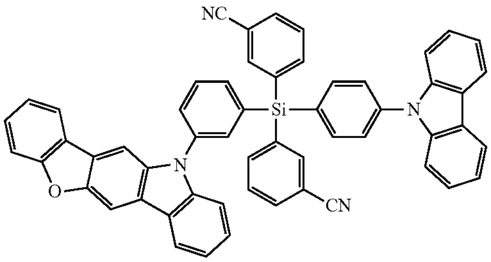
397
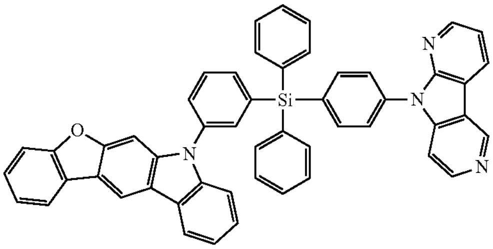
398
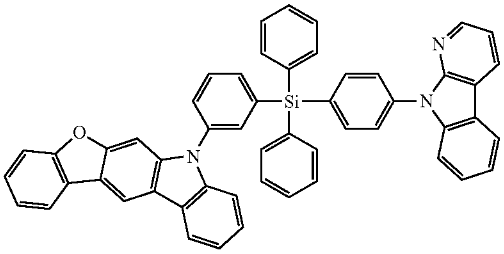
399
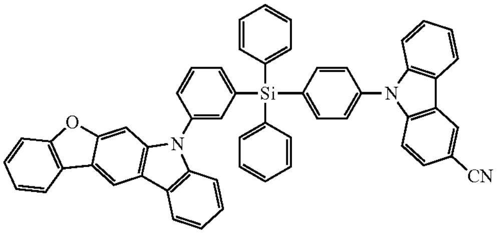
400
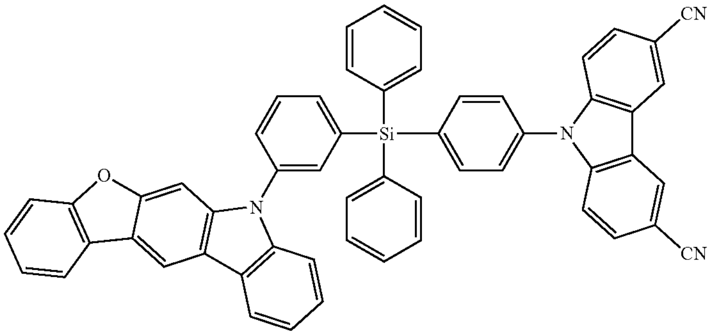
401
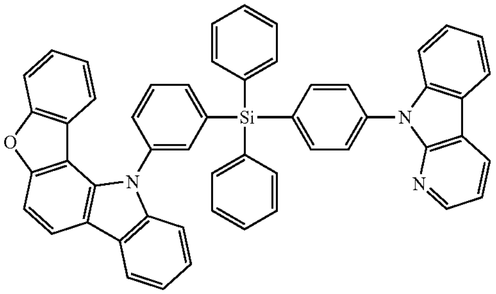
402
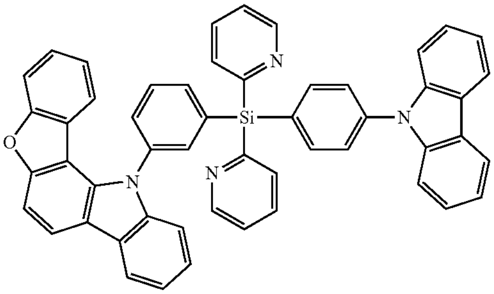
403
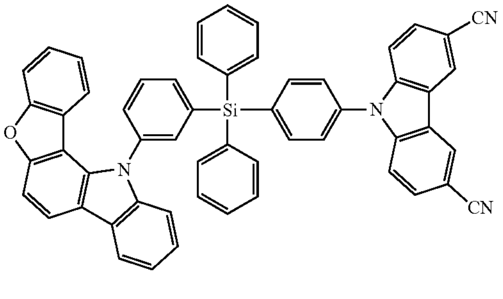
404
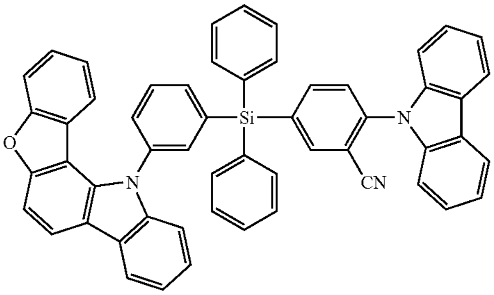

-continued
405
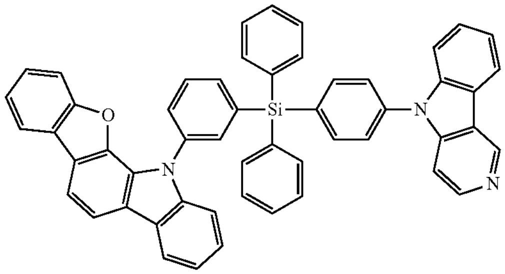
406
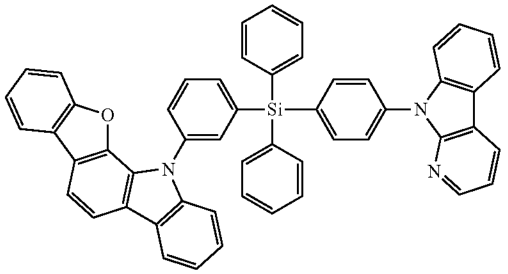
107
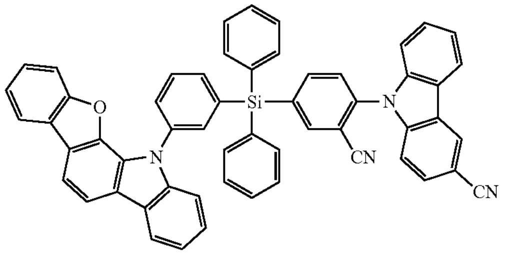
408
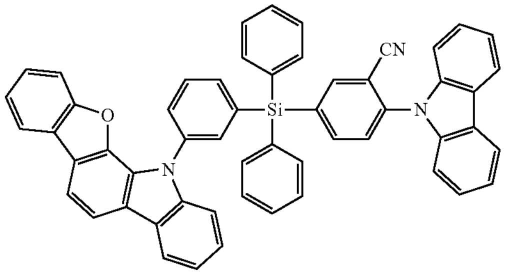
409
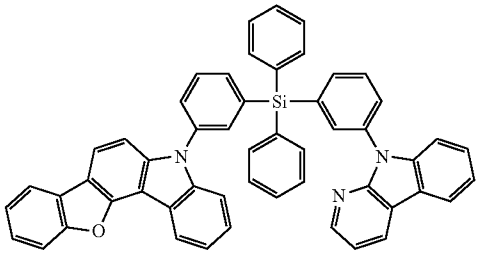
410
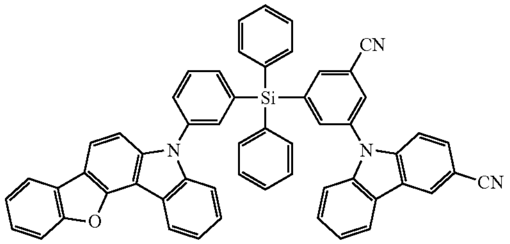
411
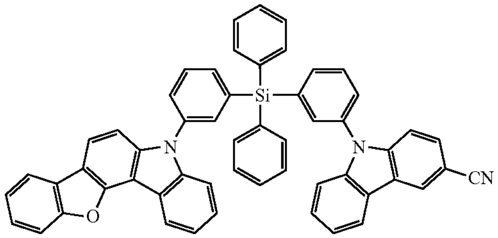
412
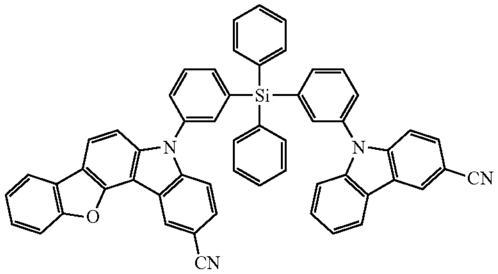
413
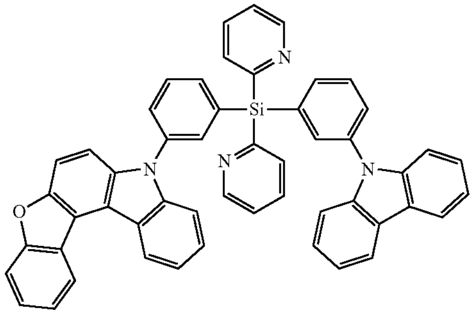
414
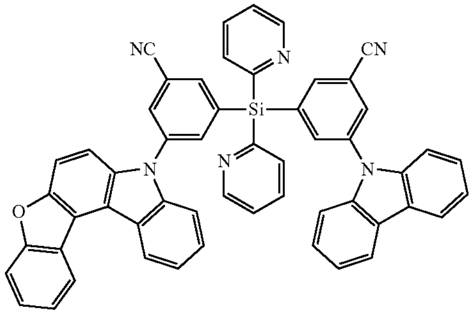

-continued
415
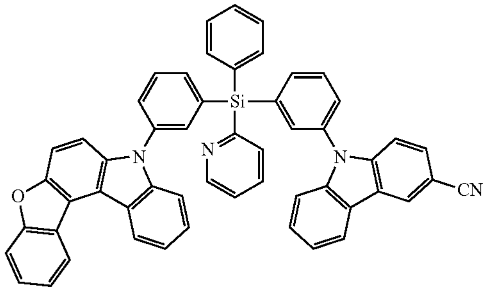
416
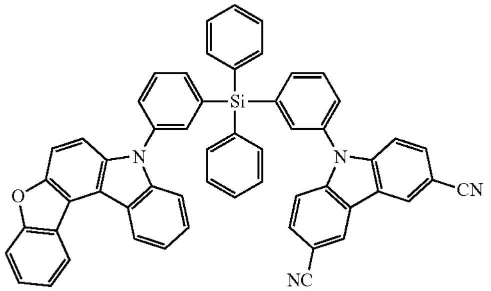
417
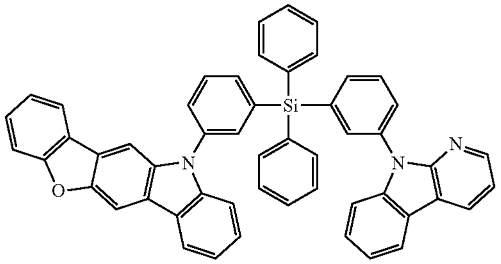
418
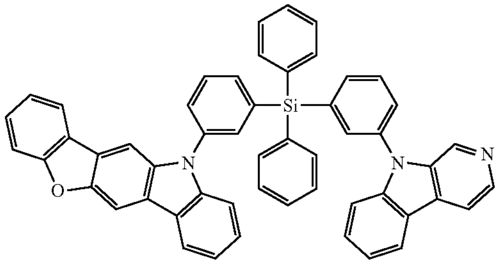
419
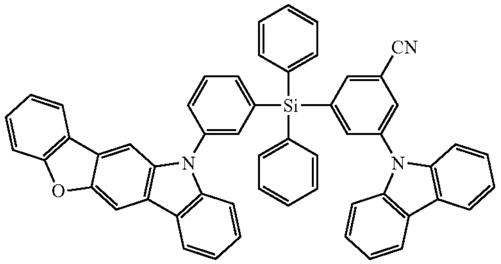
420
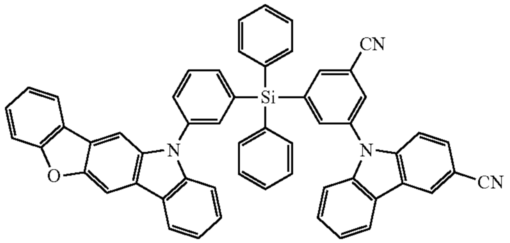
421
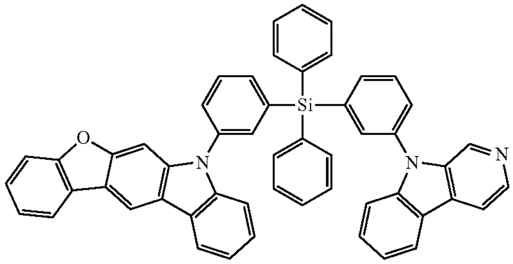
422
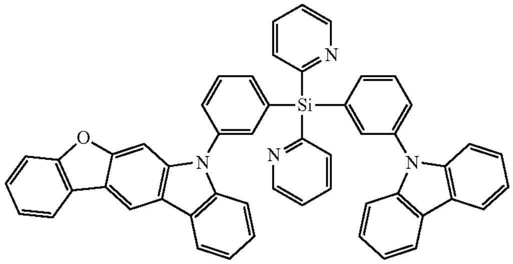
423
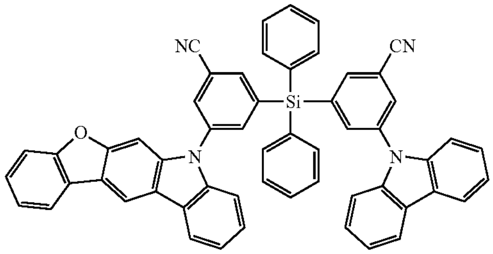
424
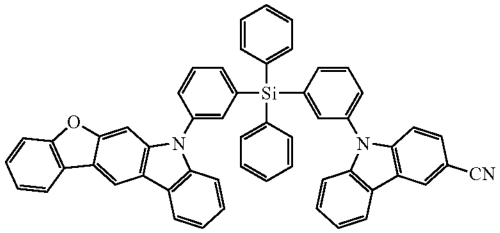

-continued

425

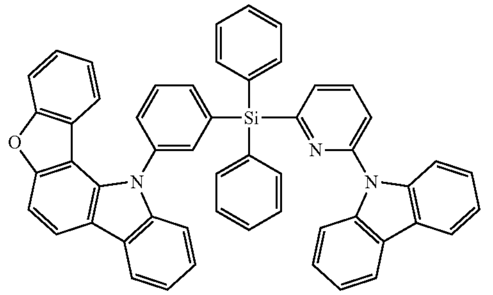

426

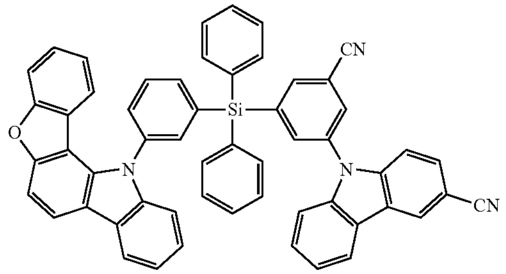

427

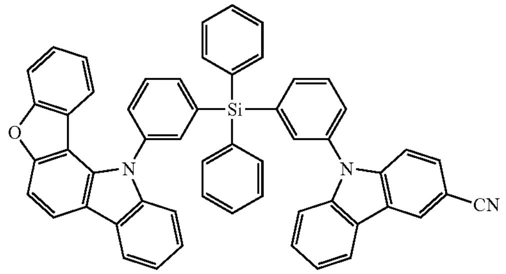

428

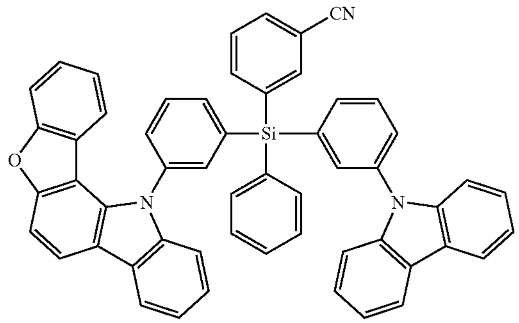

429

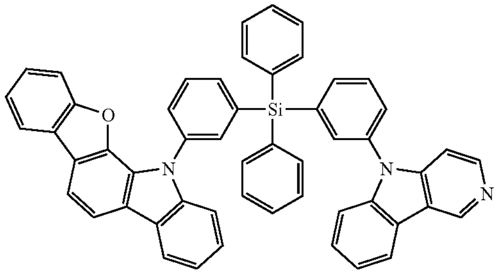

430

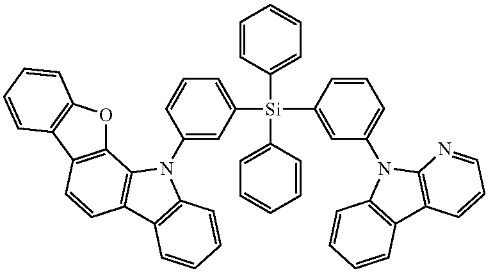

431

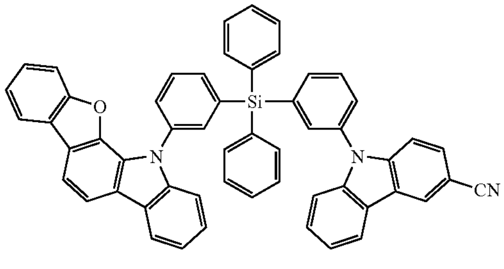

432

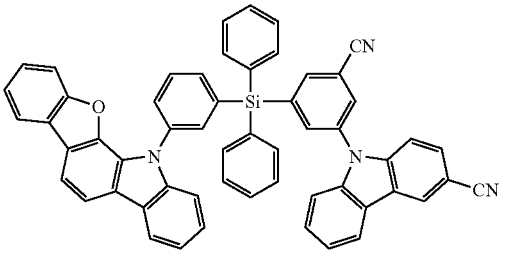

wherein, in Compounds 1 to 432,

Ph refers to a phenyl group.

When the host is a mixture of the electron-transporting host and the hole-transporting host, a weight ratio of the electron-transporting host and the hole-transporting host may be in a range of about 1:9 to 9:1, for example, about 2:8 to 8:2, for example, about 4:6 to 6:4, and for example, about 5:5. When the weight ratio of the electron transport host and the hole transport host is satisfied with these ranges, the hole-and-electron transport balance in the emission layer may be achieved.

In one or more embodiments, the host may include at least one of bis[2-(diphenylphosphino)phenyl]ether oxide (DPEPO), 3,3'-di(9H-carbazol-9-yl)-1,1'-biphenyl (Mcbp), 2,8-bis(diphenylphosphoryl)dibenzo[b,d]furan (PPF), tris(4-carbazoyl-9-ylphenyl)amine (TCTA), $Alq_3$, poly(n-vinylcarbazole) (PVK), 3-tert-butyl-9,10-di(2-naphthyl)anthracene (TBADN), (dystyryl allylene), 4,54'-bis(9-carbazolyl)-2,2'-dimethyl-biphenyl (CDBP), 2-methyl-9,10-bis(naphthalen-2-yl)anthracene (MADN), hexaphenylcyclotriphosphazene (CP1), 1,4-bis(triphenylsilyl)benzene (UGH2), (hexaphenyl)cyclotrisiloxane ($DPSiO_3$), octaphenylcyclotetrasiloxane ($DPSiO_4$), 2,8-bis(diphenylphosphoryl)dibenzofuran (PPF), TPBi, TBADN, ADN (also referred to as "DNA"), CBP, CDBP, TCP, mCP, Compounds H50 to H52, or any combination thereof:

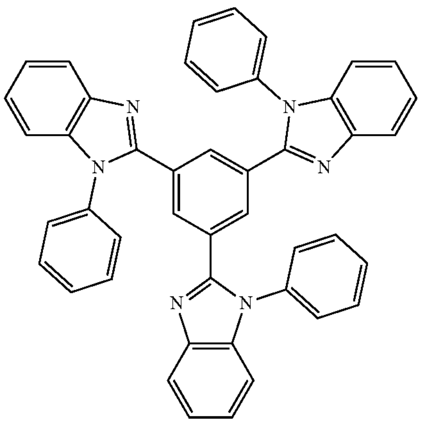
TPBi
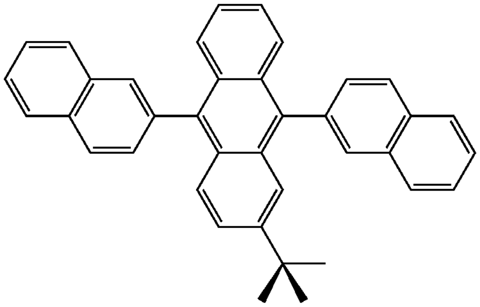
TBADN
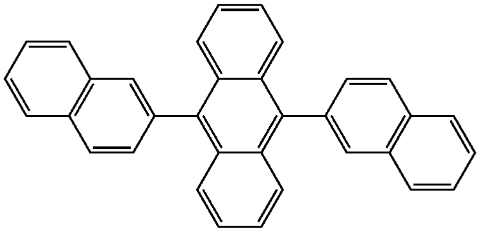
ADN
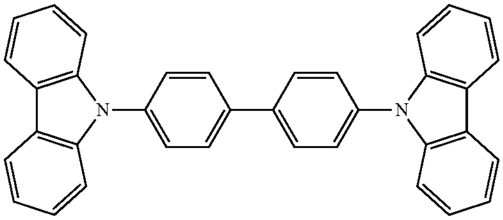
CBP
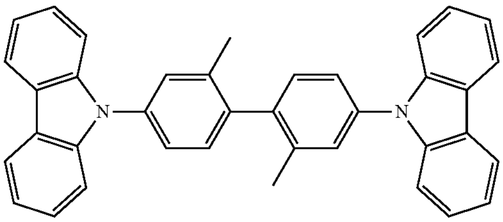
CDBP
-continued
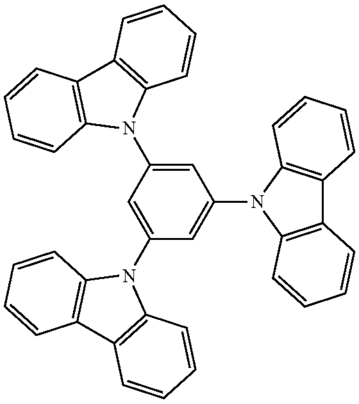
TCP
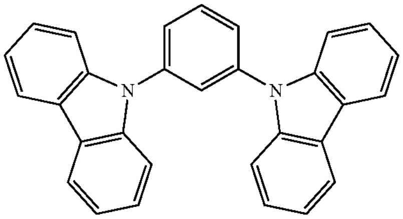
mCP
H50
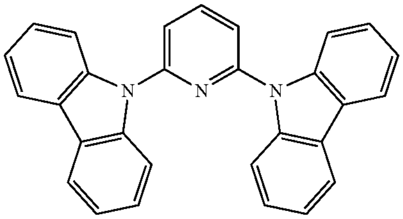
H51
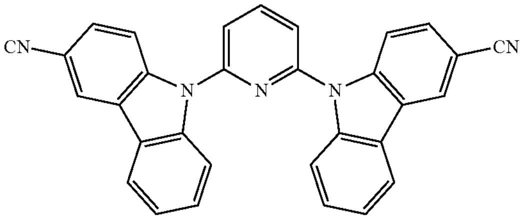
H52
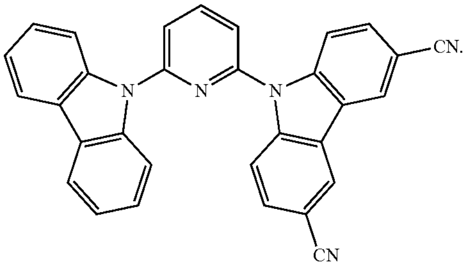

In one or more embodiments, the host may further include a compound represented by Formula 301:

Formula 301

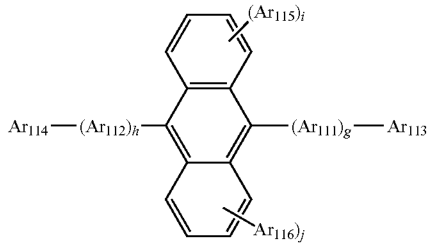

wherein, in Formula 301, $Ar_{111}$ and $Ar_{112}$ may each independently be:

a phenylene group, a naphthylene group, a phenanthrenylene group, or a pyrenylene group; or a phenylene group, a naphthylene group, a phenanthrenylene group, or a pyrenylene group, each substituted with at least one of a phenyl group, a naphthyl group, an anthracenyl group, or any combination thereof.

In Formula 301, $Ar_{113}$ to $Ar_{116}$ may each independently be:

a $C_1$-$C_{10}$ alkyl group, a phenyl group, a naphthyl group, a phenanthrenyl group, or a pyrenyl group; or a phenyl group, a naphthyl group, a phenanthrenyl group, or a pyrenyl group, each substituted with at least one of a phenyl group, a naphthyl group, an anthracenyl group, or any combination thereof.

In Formula 301, g, h, i, and j may each independently be an integer from 0 to 4, and for example, may each independently be 0, 1, or 2.

In Formula 301, $Ar_{113}$ to $Ar_{116}$ may each independently be:

a $C_1$-$C_{10}$ alkyl group substituted with at least one of a phenyl group, a naphthyl group, an anthracenyl group, or any combination thereof;

a phenyl group, a naphthyl group, an anthracenyl group, a pyrenyl, a phenanthrenyl group, or a fluorenyl group;

a phenyl group, a naphthyl group, an anthracenyl group, a pyrenyl group, a phenanthrenyl group, or a fluorenyl group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, a fluorenyl group, or any combination thereof; or

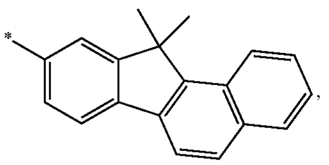 [SMILES: *c1ccc2c(c1)C(C)(C)c1c-2ccc2ccccc12], but embodiments of the present disclosure are not limited thereto.

In one or more embodiments, the host may include a compound represented by Formula 302:

Formula 302

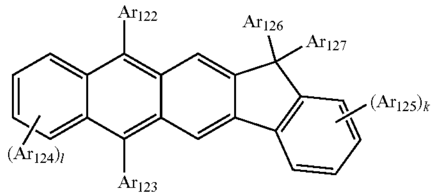

wherein, in Formula 302, $Ar_{122}$ to $Ar_{125}$ may each independently be the same as described in connection with $Ar_{113}$ in Formula 301.

In Formula 302, $Ar_{126}$ and $Ar_{127}$ may each independently be a $C_1$-$C_{10}$ alkyl group (for example, a methyl group, an ethyl group, or a propyl group).

In Formula 302, k and l may each independently be an integer from 0 to 4. For example, k and l may each independently be 0, 1, or 2.

When the organic light-emitting device 10 is a full-color organic light-emitting device, the emission layer 4 may be patterned into a red emission layer, a green emission layer, and a blue emission layer. In an embodiment, based on a stacked structure including a red emission layer, a green emission layer, and/or a blue emission layer, the emission layer 4 may emit white light, and various modifications are possible.

When the emission layer 4 includes a host and a light-emitting dopant, an amount of the light-emitting dopant may be generally in a range of about 0.01 parts by weight to about 15 parts by weight based on 100 parts by weight of the host, but embodiments of the present disclosure are not limited thereto.

A thickness of the emission layer 4 may be in a range of about 100 Å to about 1,000 Å, for example, about 200 Å to about 600 Å. When the thickness of the emission layer 4 is within these ranges, excellent luminescence characteristics may be obtained without a substantial increase in driving voltage.

In an embodiment, the light-emitting dopant may include the condensed cyclic compound represented by Formula 1.

In one or more embodiments, the light-emitting dopant may include 1,4-bis[2-(3-N-ethylcarbazolyl)-vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalene-2-yl)vinyl)phenyl)-N-phenylbenzeneamine (N-BDAVBi), 2,5,8,11-tetra-t-butylperylene (TBP), or any combination thereof.

In an embodiment, the sensitizer may include the condensed cyclic compound represented by Formula 1.

In one or more embodiments, the sensitizer may include an organic metallic compound including at least one metal of a Period 1 transition metal, Period 2 transition metal, Period 3 transition metal, or a combination thereof of the Periodic Table of Elements.

In one or more embodiments, the sensitizer may include: at least one metal ($M_{11}$) of a Period 1 transition metal, Period 2 transition metal, Period 3 transition metal, or any combination thereof of the Periodic Table of Elements; and an organic ligand ($L_1$), wherein $L_1$ and $M_{11}$ may form 1, 2, 3, or 4 cyclometallated rings.

In one or more embodiments, the sensitizer may include an organometallic compound represented by Formula 101:

$M_{11}(L_1)_{n1}(L_2)_{n2}$ Formula 101 wherein, in Formula 101, $M_{11}$ may be a Period 1 transition metal, a Period 2 transition metal, or a Period 3 transition metal of the Periodic Table of Elements, $L_1$ may be an organic ligand represented by one of Formulae 10-1 to 10-4, $L_2$ may be a monodentate ligand or a bidentate ligand, n1 may be 1, and n2 may be 0, 1, or 2, 10-1

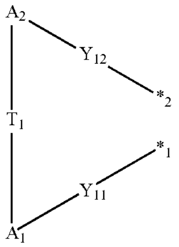

10-2

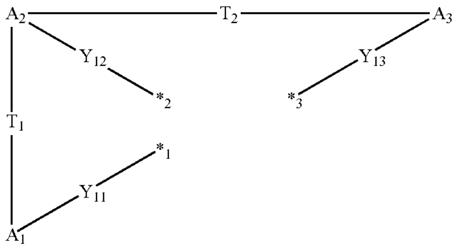

10-3

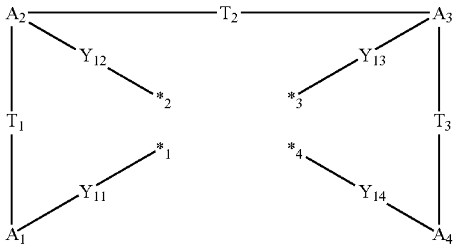

-continued 10-4

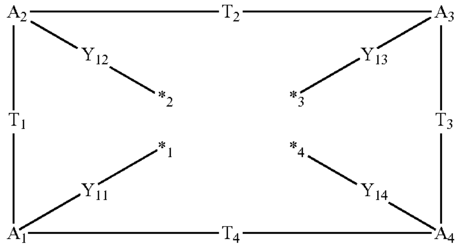

wherein, in Formulae 10-1 to 10-4, $A_1$ to $A_4$ may each independently be a substituted or unsubstituted $C_5$-$C_{30}$ carbocyclic group, a substituted or unsubstituted $C_1$-$C_{30}$ heterocyclic group, or a non-cyclic group, $Y_{11}$ to $Y_{14}$ may each independently be a chemical bond, O, S, $N(R_{91})$, $B(R_{91})$, $P(R_{91})$, or $C(R_{91})(R_{92})$, $T_1$ to $T_4$ may each independently be a single bond, a double bond, *—$N(R_{93})$—*', *—$B(R_{93})$—*', *—$P(R_{93})$—*', *—$C(R_{93})(R_{94})$—*', *—$Si(R_{93})(R_{94})$—*', *—$Ge(R_{93})(R_{94})$—*', *—S—*', *—Se—*', *—O—*', *—C(═O)—*', *—S(═O)—*', *—$S(═O)_2$—*', *—$C(R_{93})$═*', *═$C(R_{93})$—*', *—$C(R_{93})$═$C(R_{94})$—', *—C(═S)—*', or *—C≡C—*', a substituent of the substituted $C_5$-$C_{30}$ carbocyclic group, a substituent of substituted $C_1$-$C_{30}$ heterocyclic group, and $R_{91}$ to $R_{94}$ may each independently be hydrogen, deuterium, —F, —Cl, —Br, —I, —$SF_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$B(Q_1)(Q_2)$, —$N(Q_1)(Q_2)$, —$P(Q_1)(Q_2)$, —$C(═O)(Q_1)$, —$S(═O)(Q_1)$, —$S(═O)_2(Q_1)$, —$P(═O)(Q_1)(Q_2)$, or —$P(═S)(Q_1)(Q_2)$, wherein each of the substituent of the substituted $C_5$-$C_{30}$ carbocyclic group and the substituent of substituted $C_1$-$C_{30}$ heterocyclic group is not hydrogen, $*_1$, $*_2$, $*_3$, and $*_4$ each indicate a binding site to $M_{11}$, and $Q_1$ to $Q_3$ may each independently be hydrogen, deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group that is substituted with at least one deuterium, —F, a cyano group, a $C_1$-$C_{60}$ alkyl group, or a $C_6$-$C_{60}$ aryl group, or a $C_6$-$C_{60}$ aryl group that is substituted with deuterium, —F, a cyano group, a $C_1$-$C_{60}$ alkyl group, a $C_6$-$C_{60}$ aryl group, or any combination thereof.

In one or more embodiments, the sensitizer may be one of groups I to VI, but embodiments of the present disclosure are not limited thereto:

Group I

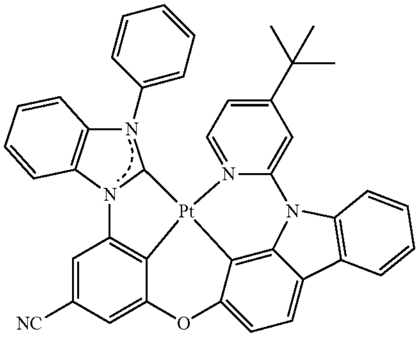

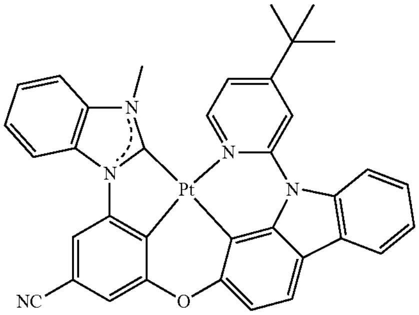

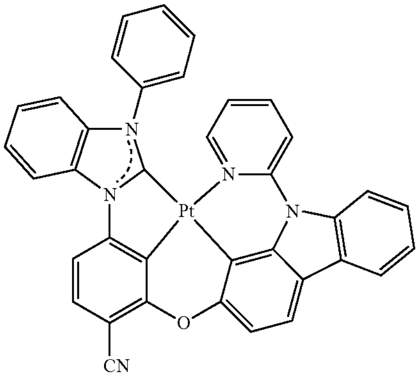

-continued

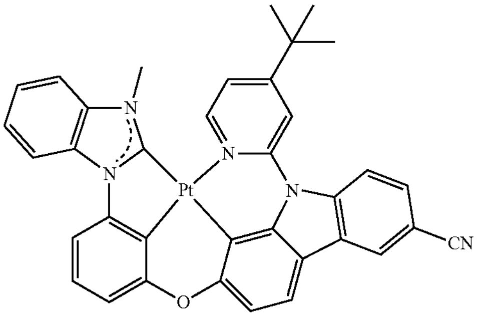

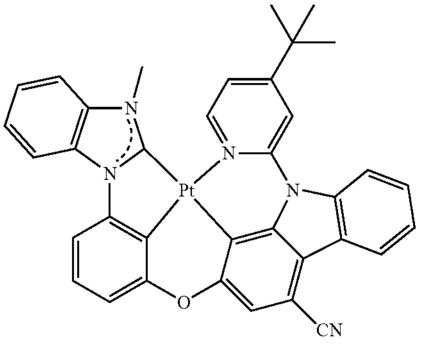

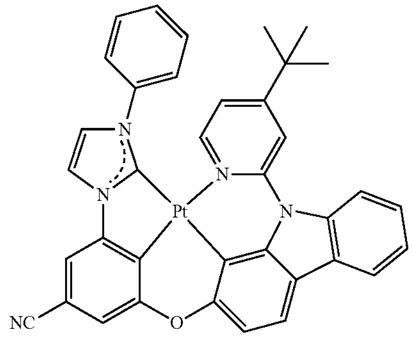

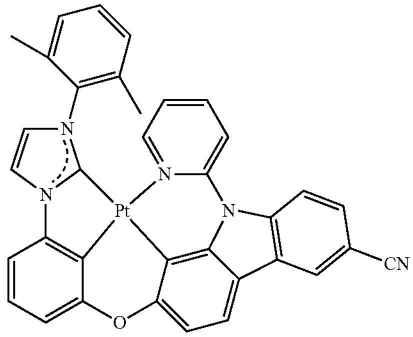

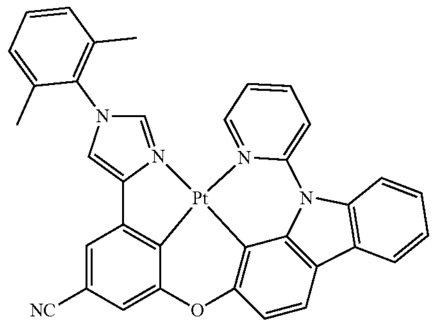

-continued
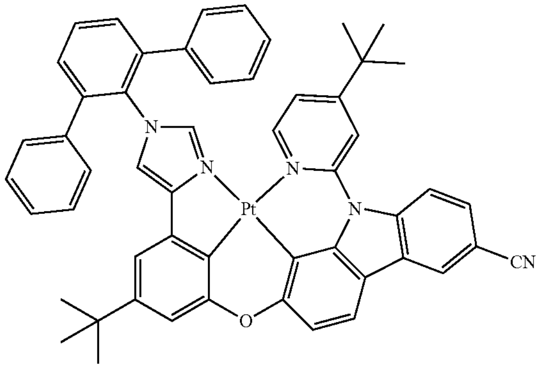
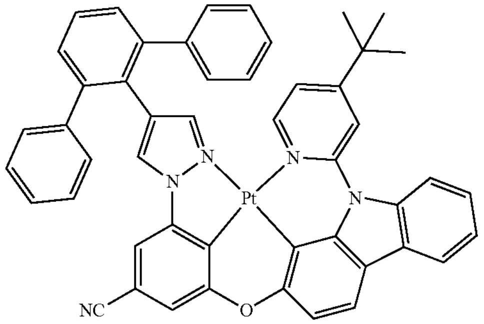
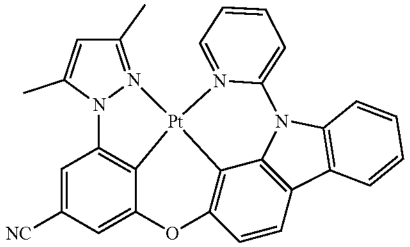
Group II
1
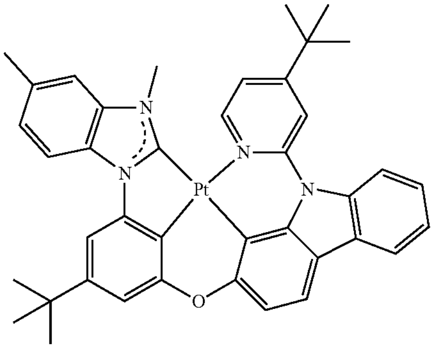
2
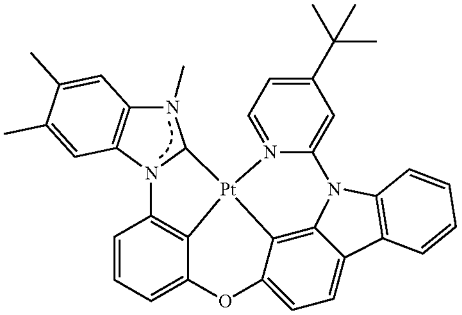
-continued
3
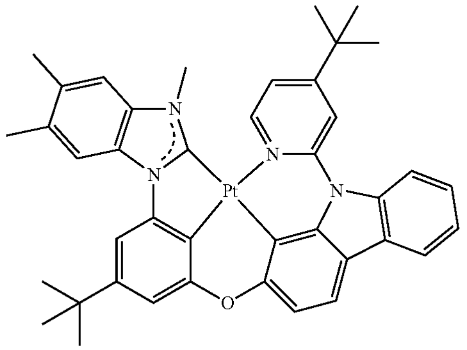
4
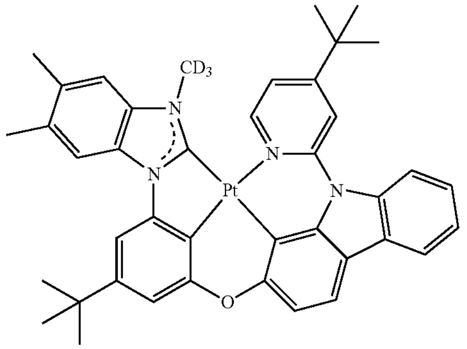
5
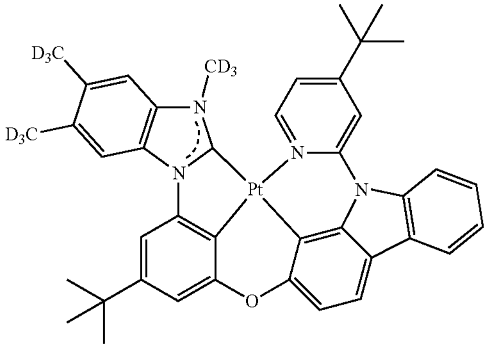
6
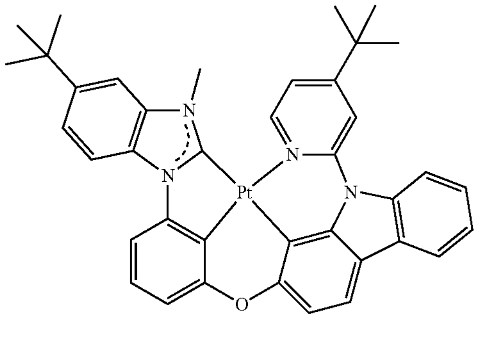

-continued
7
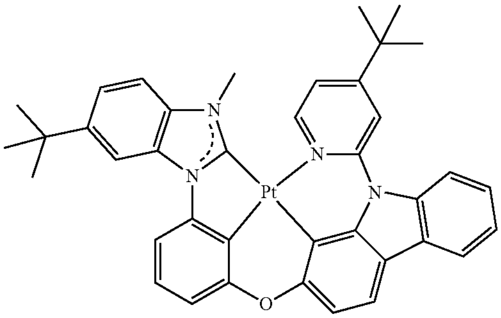
8
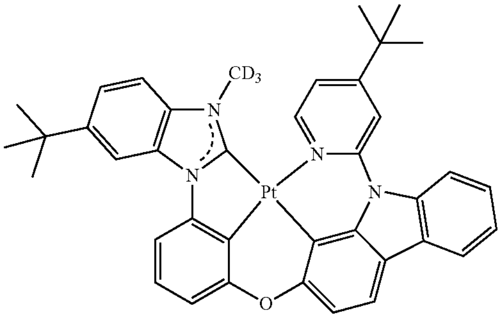
9
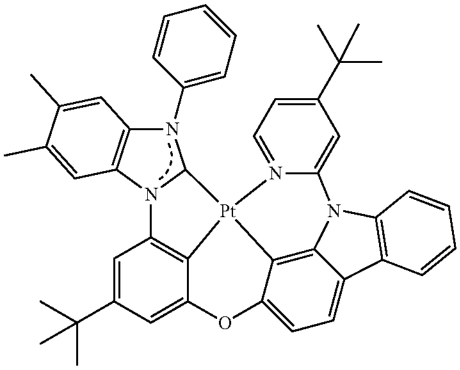
10
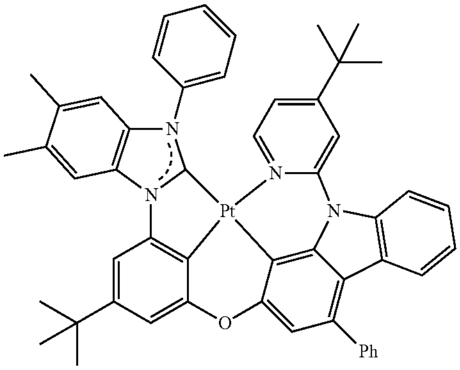
-continued
11
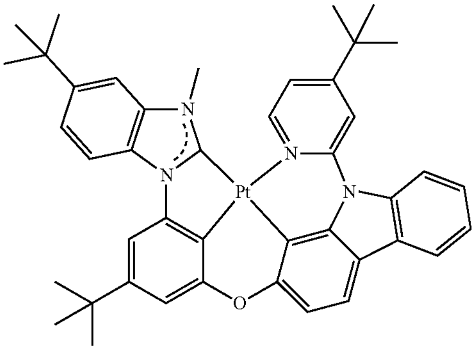
12
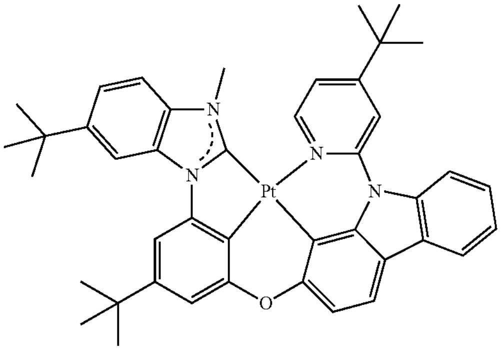
13
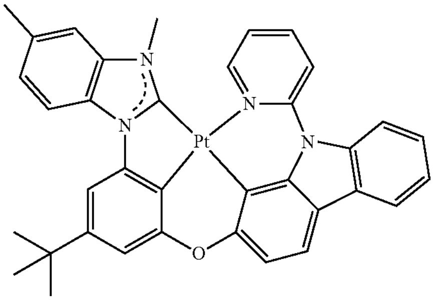
14
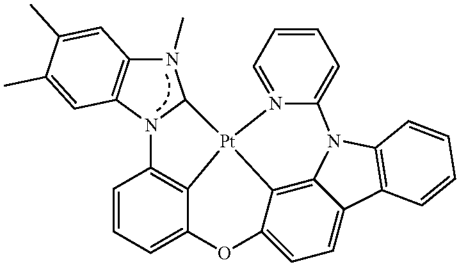
15
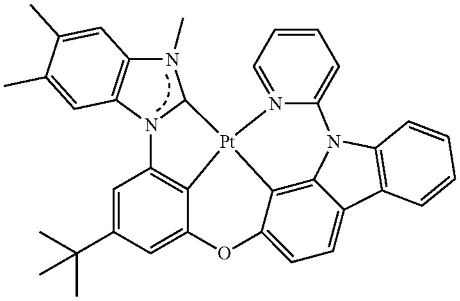

-continued
16
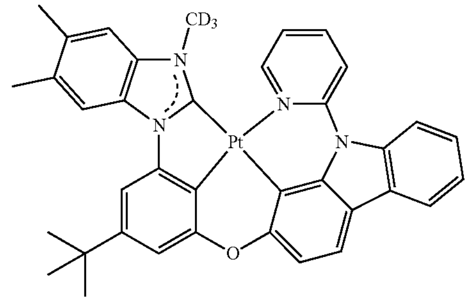
17
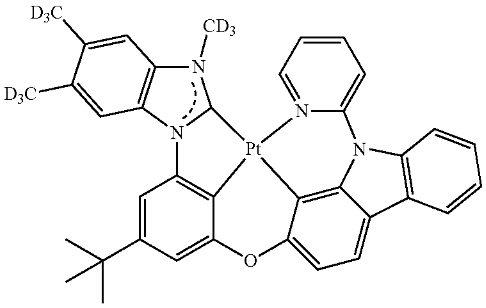
18
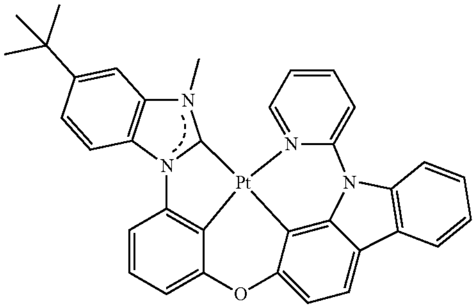
19
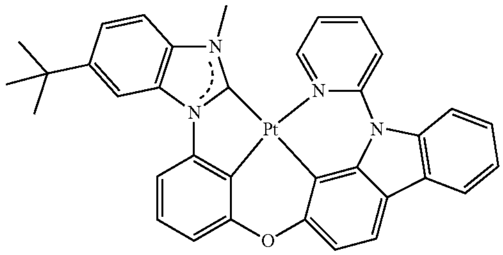
20
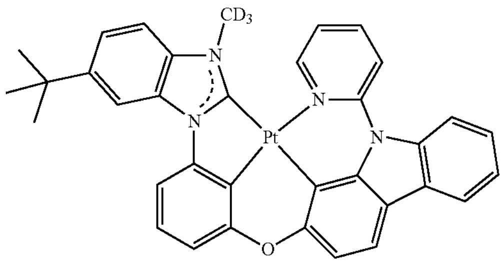
-continued
21
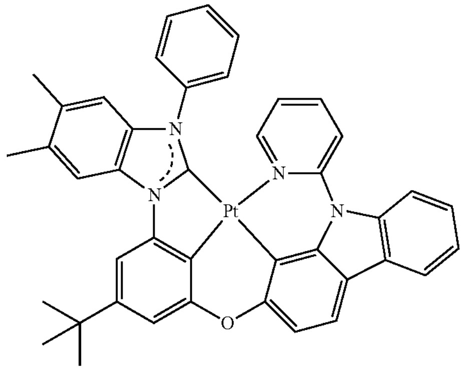
22
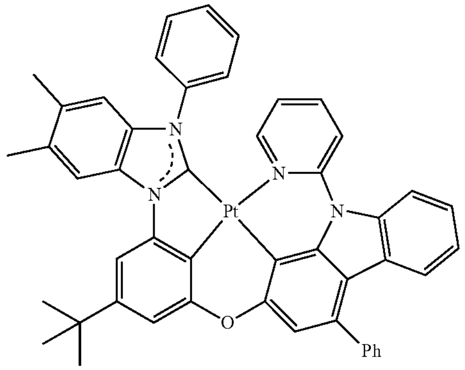
23
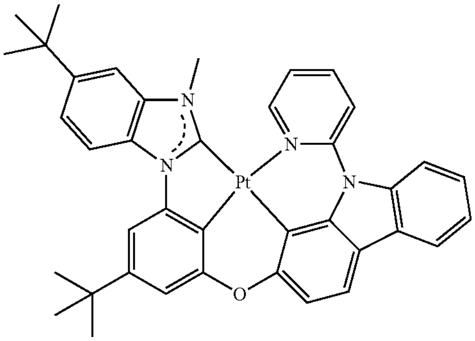
24
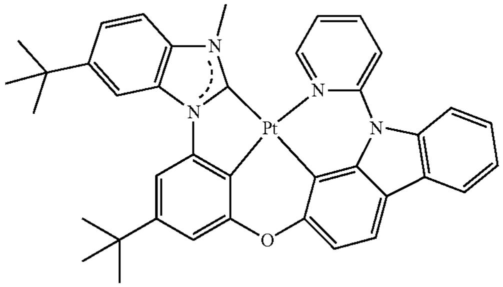

-continued
25
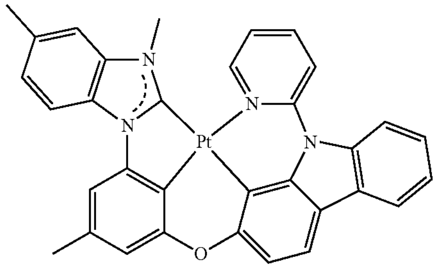
26
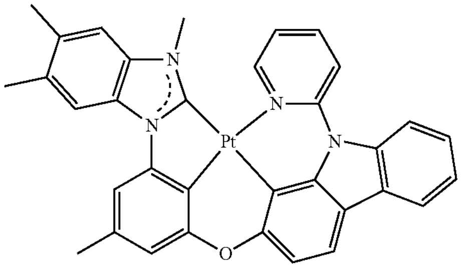
27
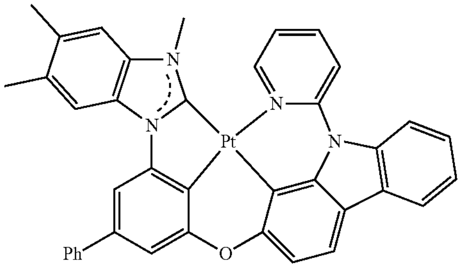
28
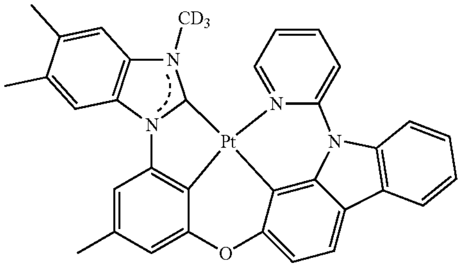
29
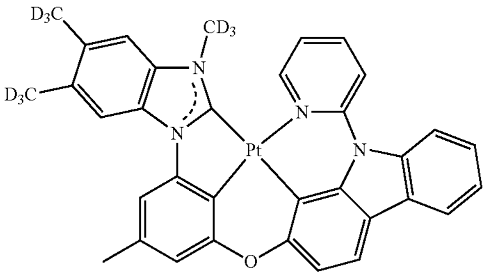
-continued
30
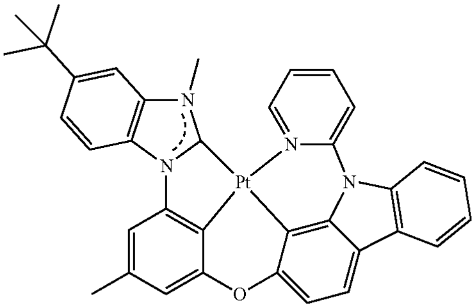
31
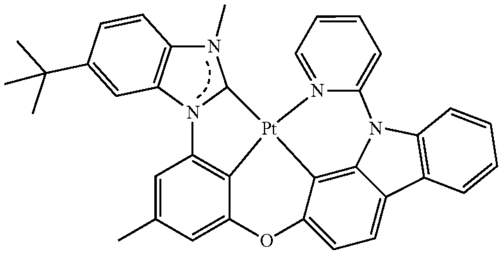
32
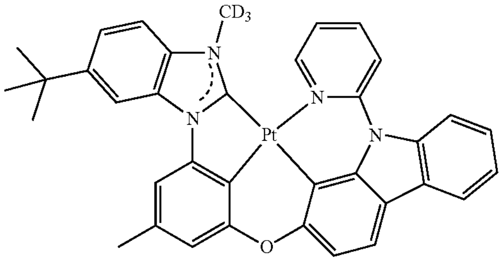
33
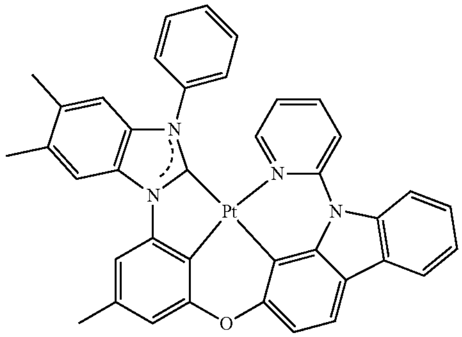
34
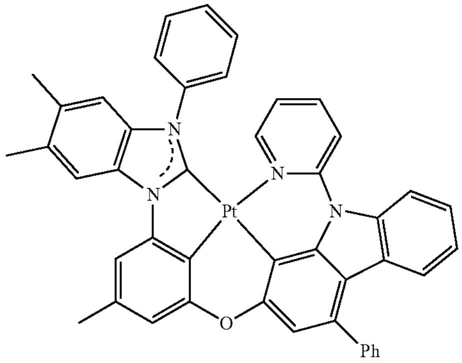

-continued
35
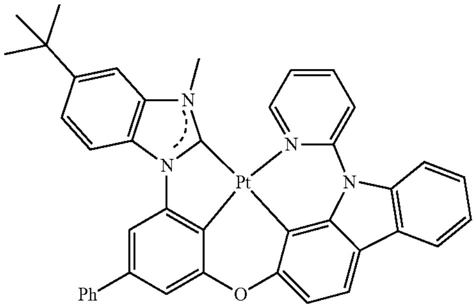
36
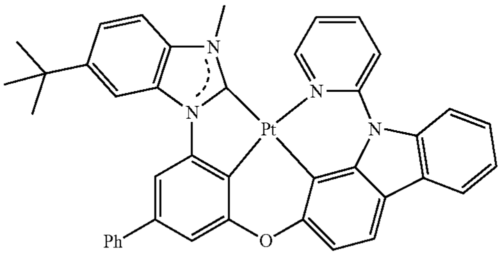
37
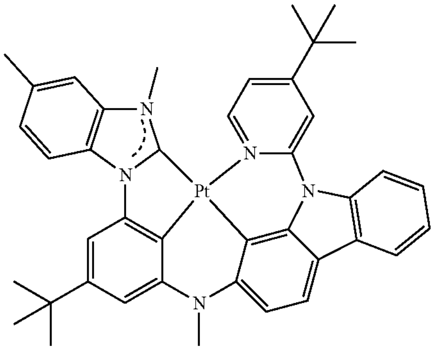
38
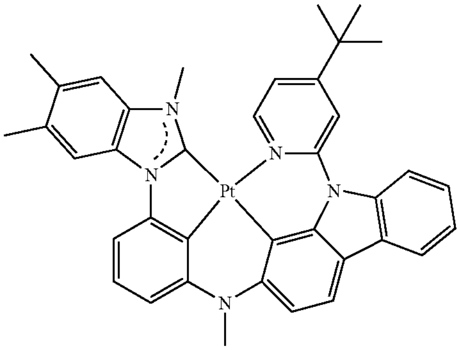
-continued
39
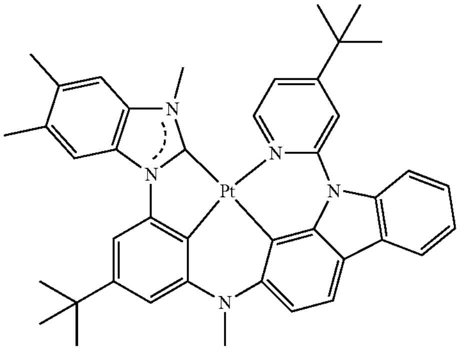
40
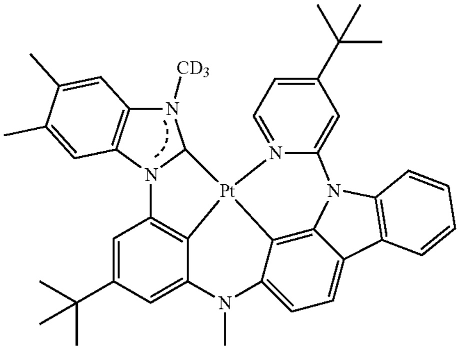
41
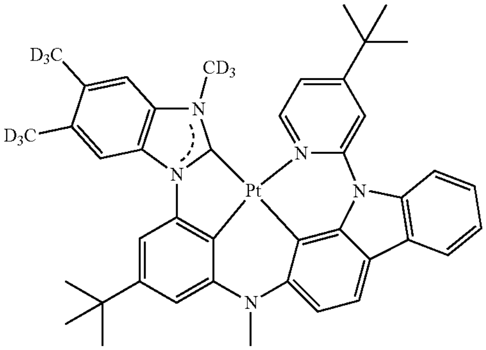
42
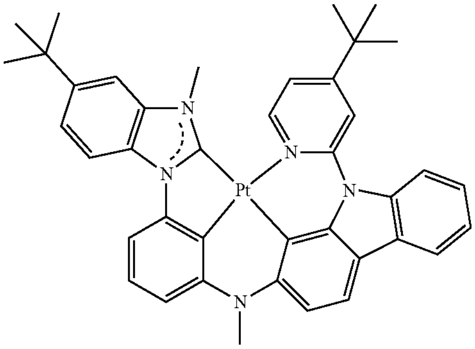

-continued
43
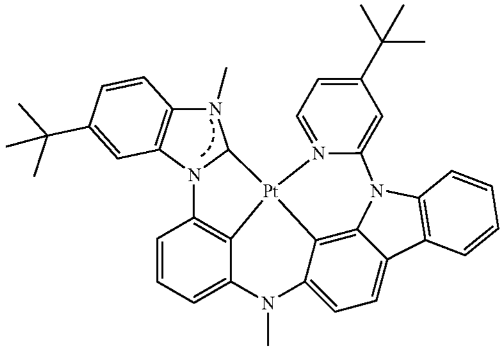
44
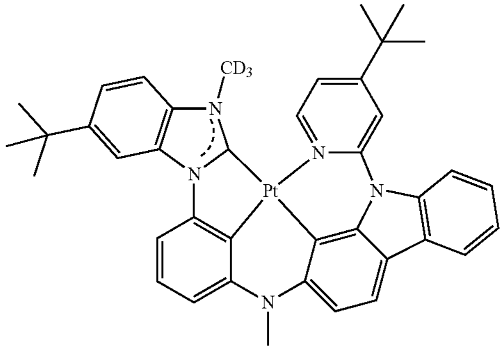
45
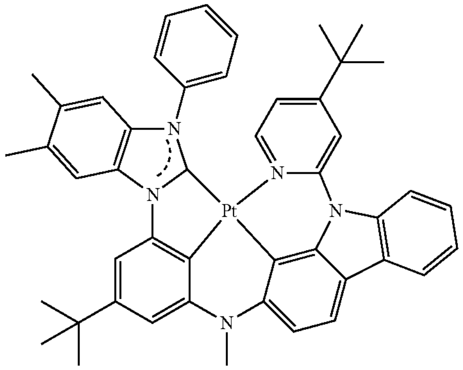
46
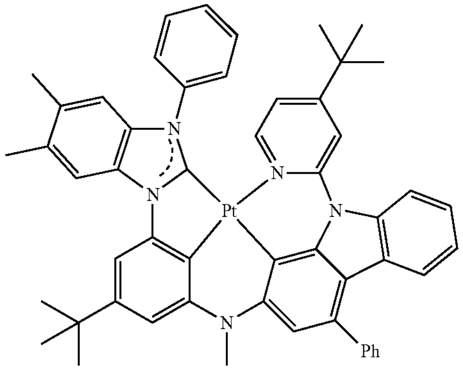
-continued
47
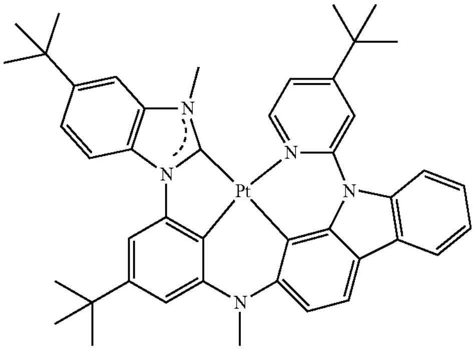
48
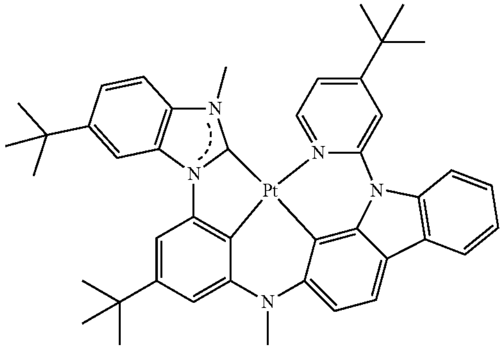
49
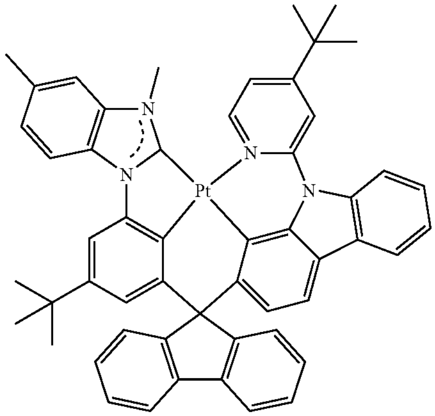
50
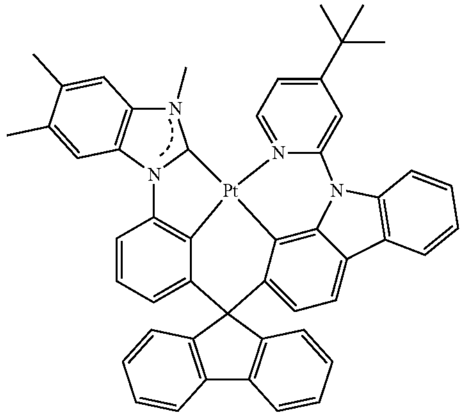

896
-continued
51
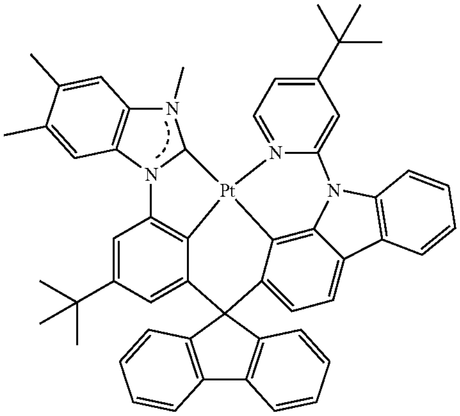
54
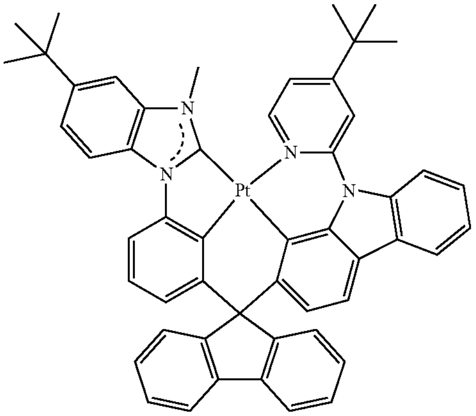
52
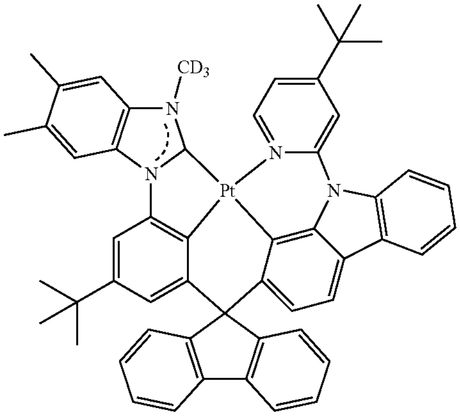
55
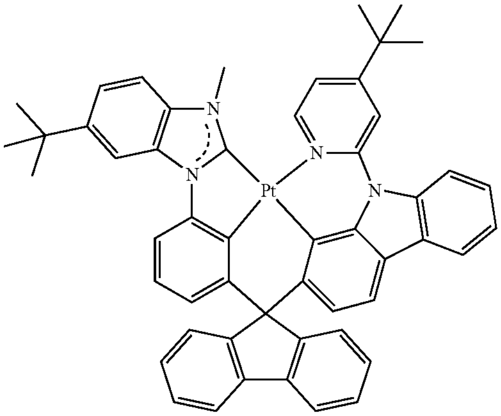
53
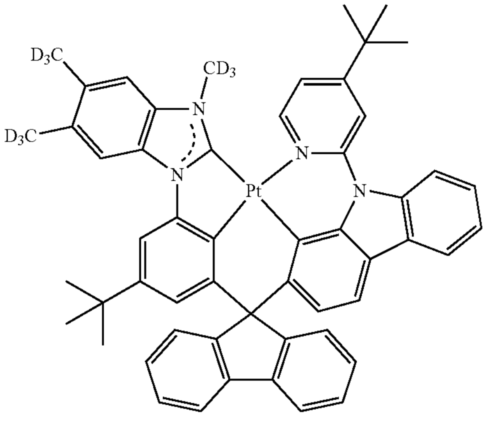
56
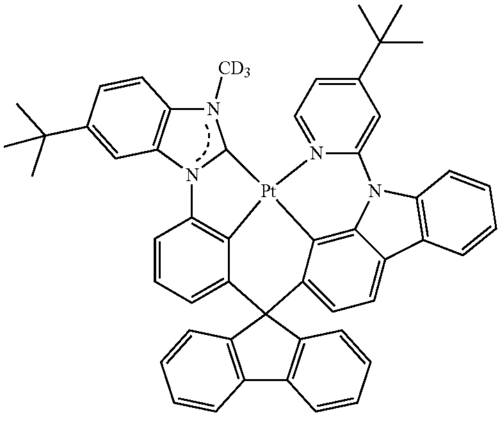

-continued
57
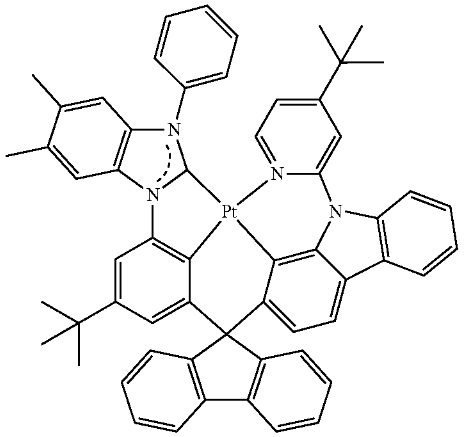
58
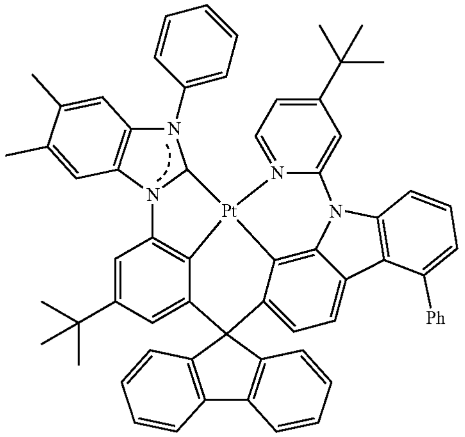
59
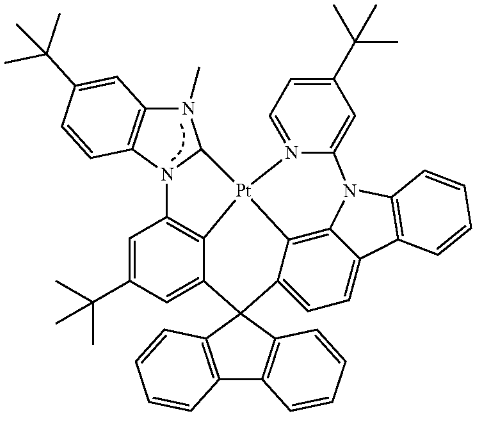
-continued
60
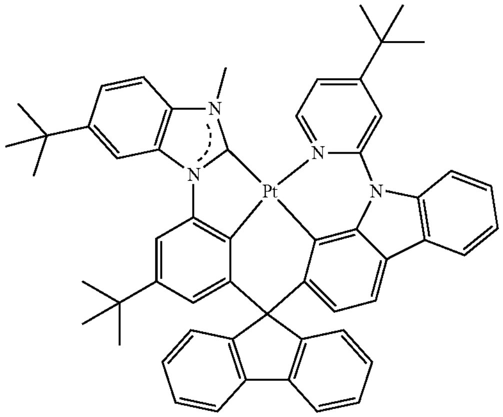
61
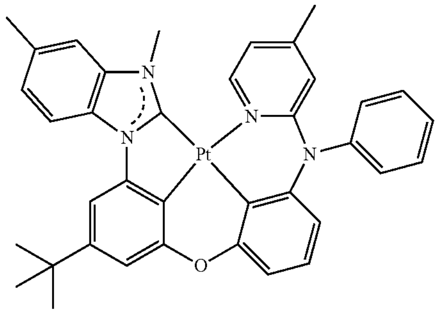
62
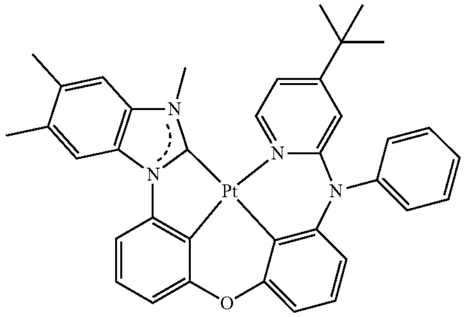
63
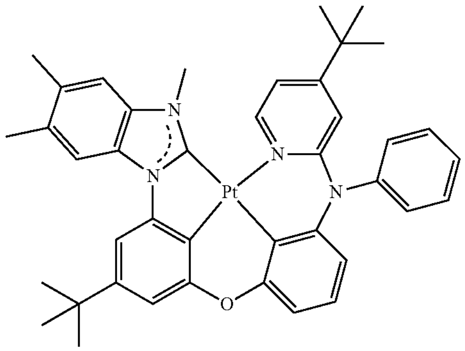

-continued
64
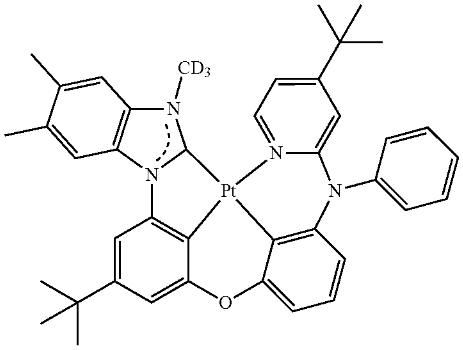
65
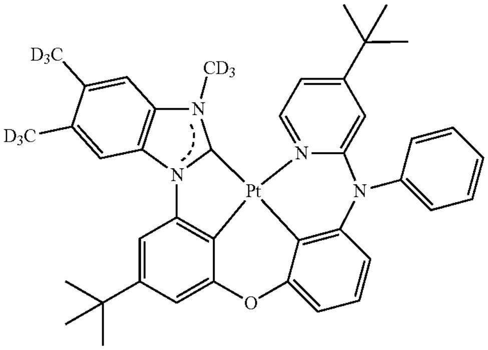
66
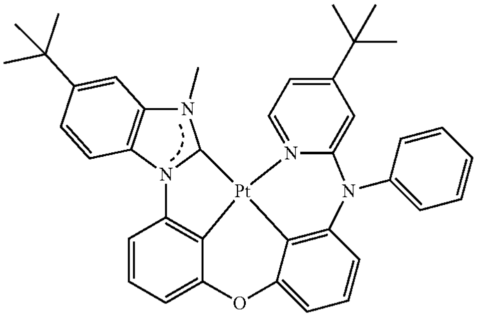
67
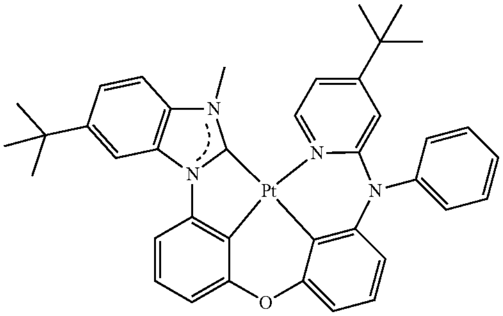
-continued
68
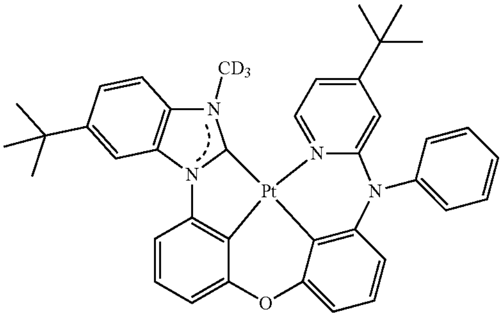
69
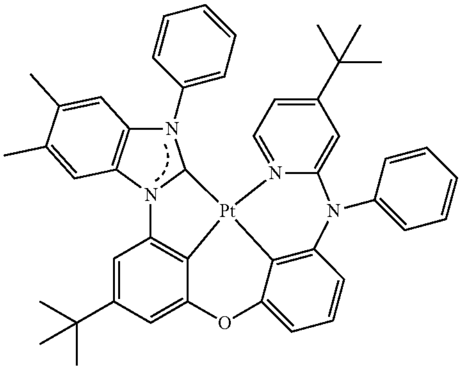
70
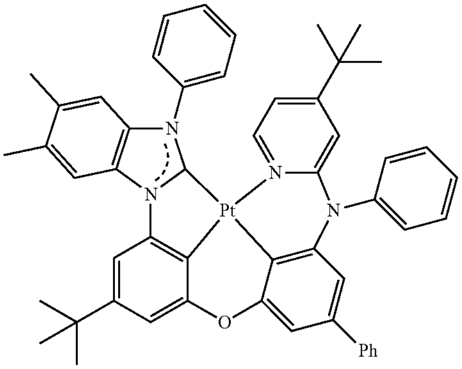
71
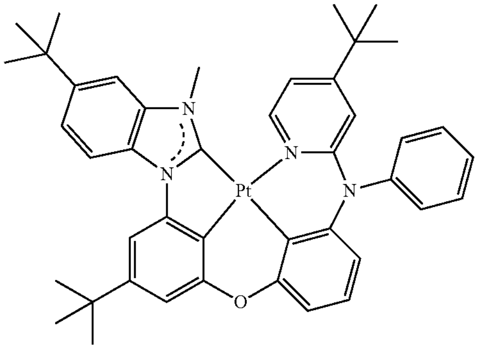

-continued
72
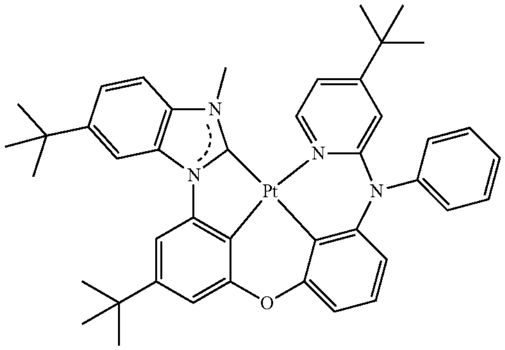
73
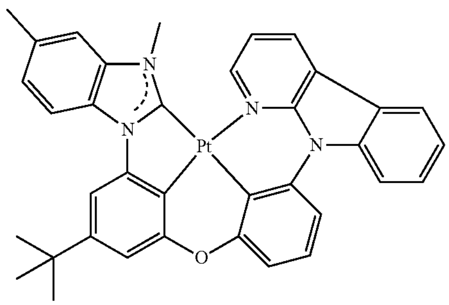
74
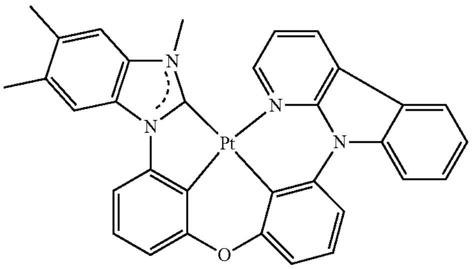
75
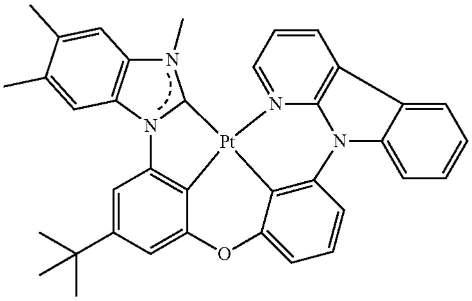
76
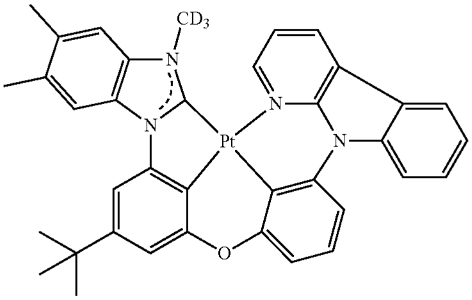
-continued
77
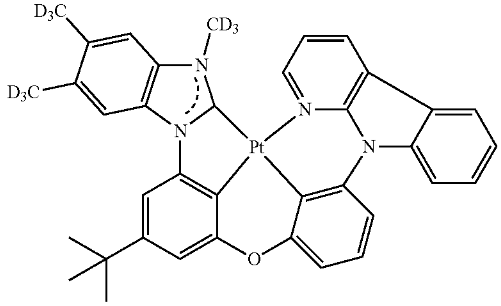
78
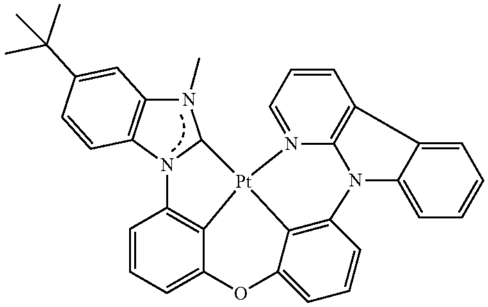
79
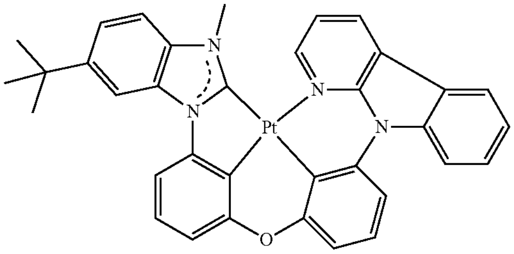
89
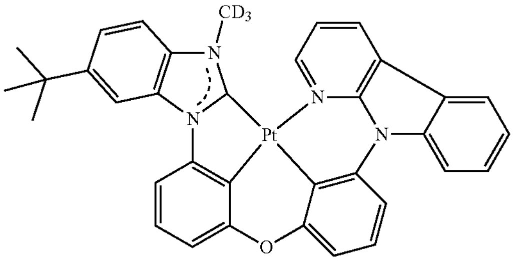
81
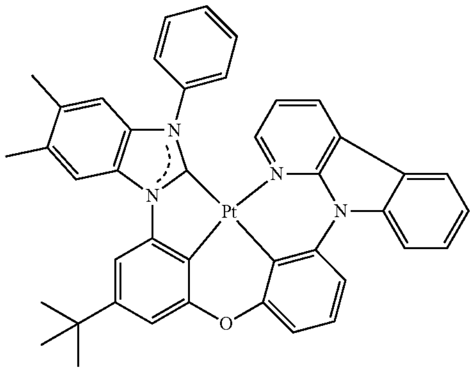

-continued
82
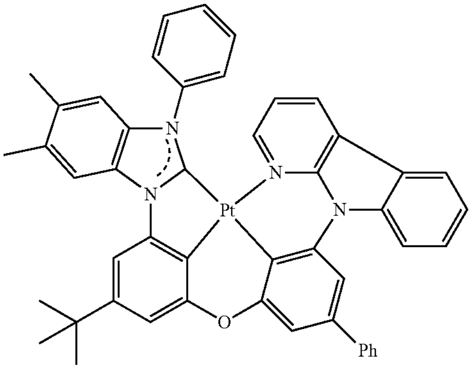
83
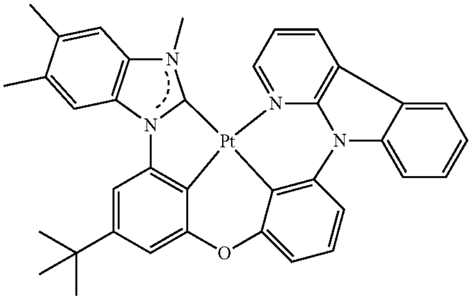
84
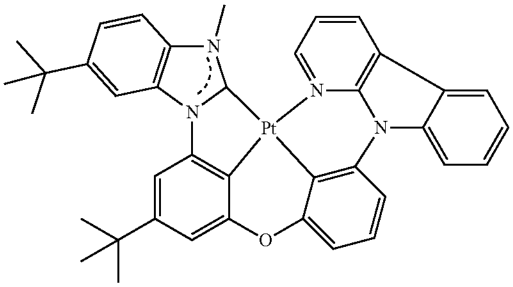
85
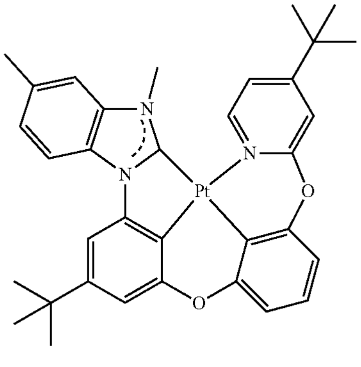
-continued
86
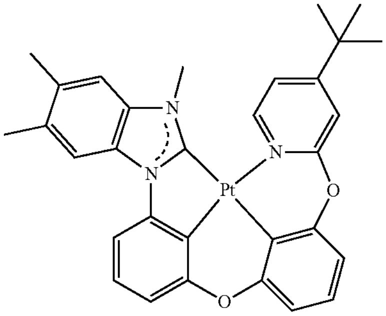
87
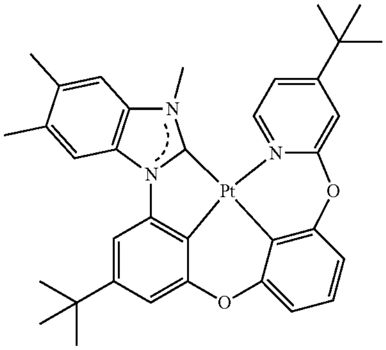
88
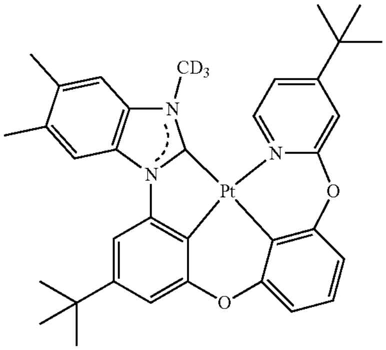
89
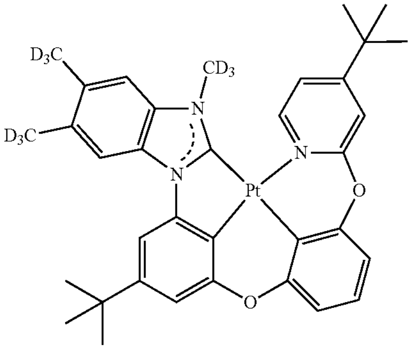

-continued
90
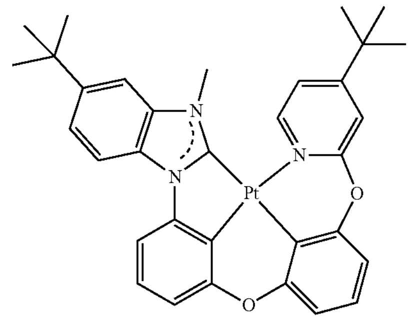
91
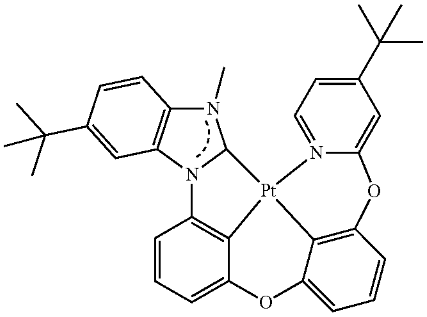
92
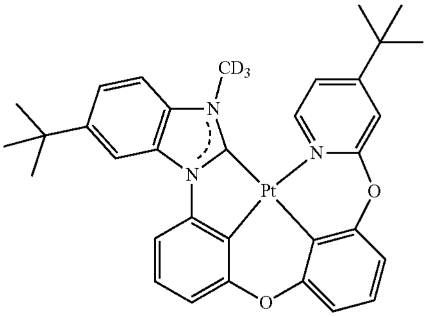
93
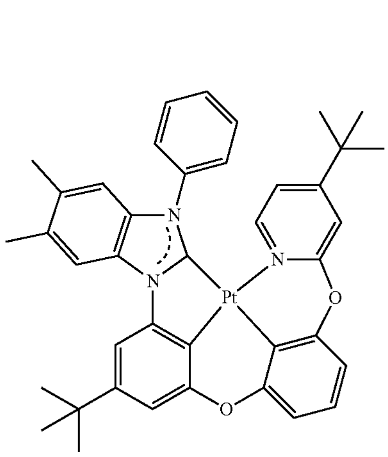
-continued
94
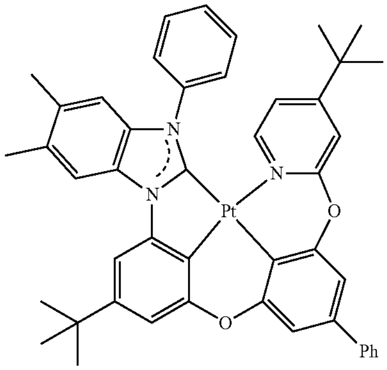
95
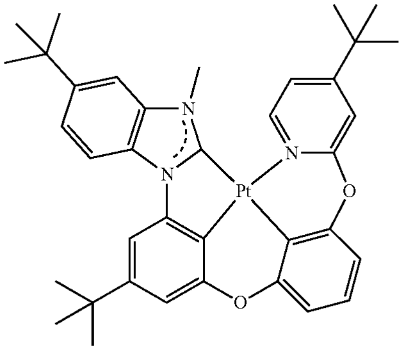
96
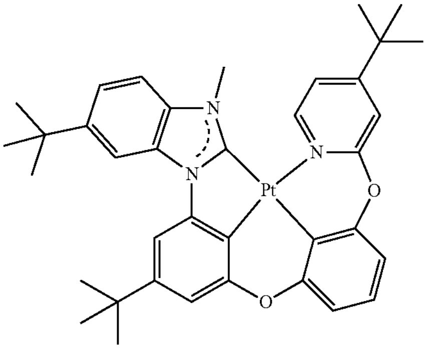
97
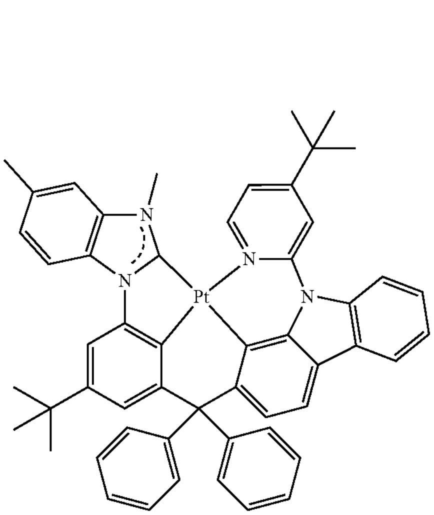

-continued
98
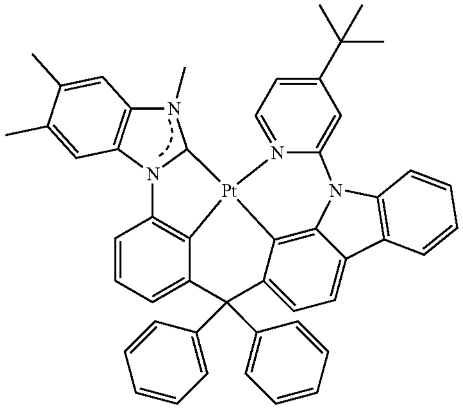
99
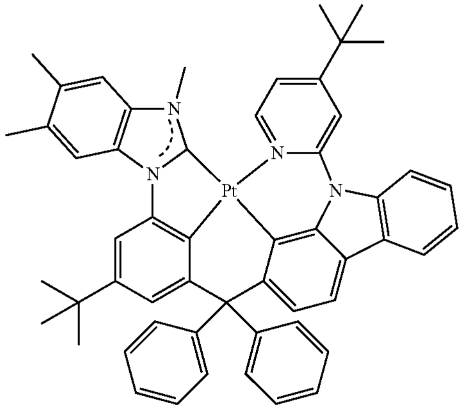
100
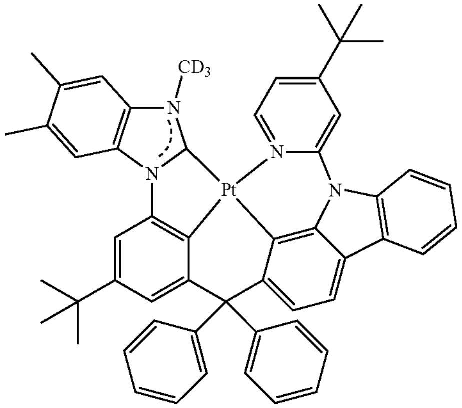
101
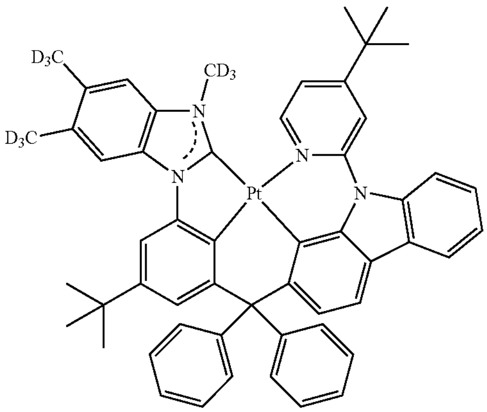
-continued
102
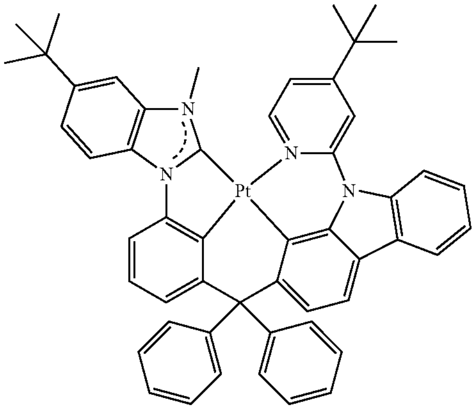
103
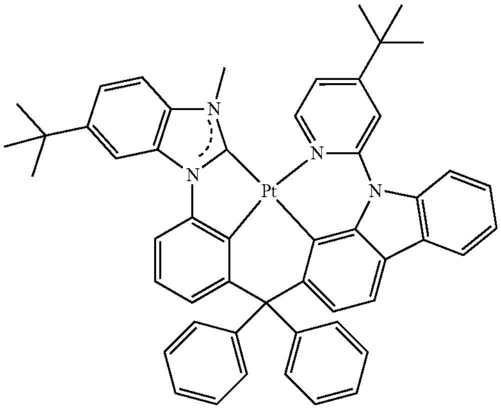
104
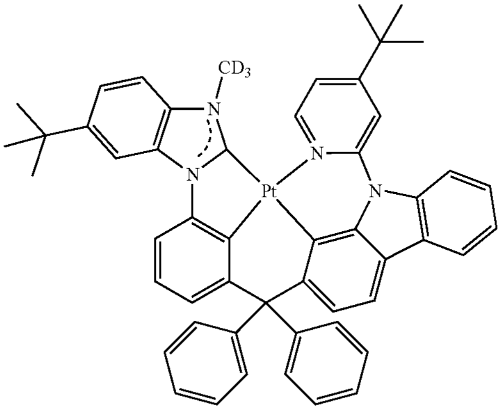

-continued
105
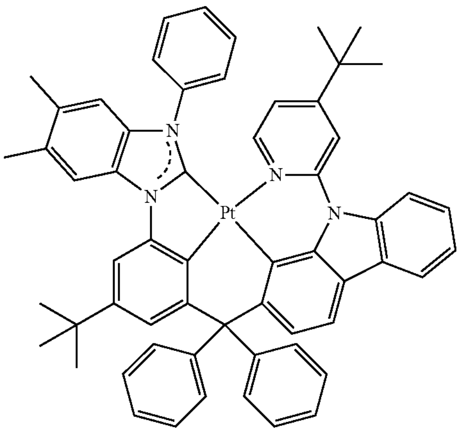
106
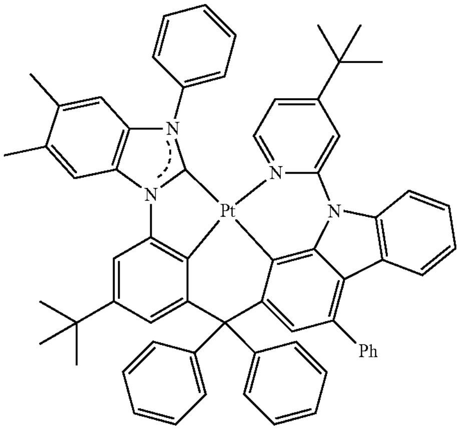
107
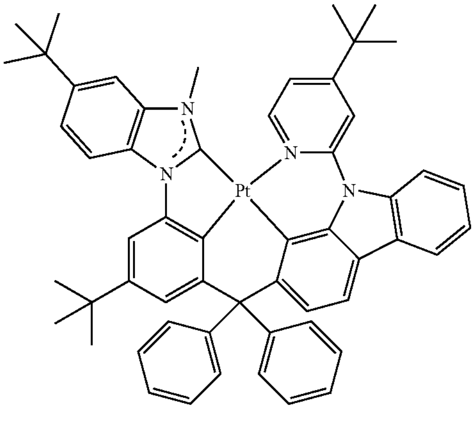
108
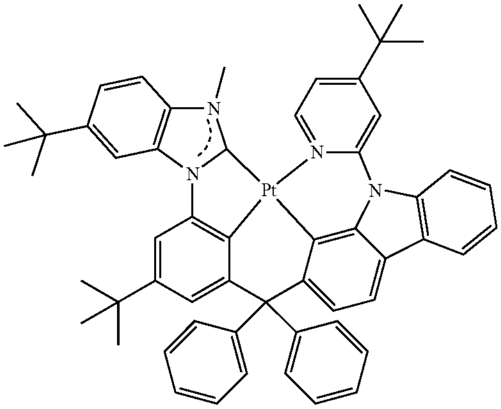
109
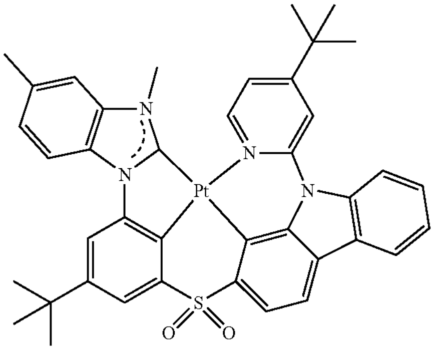
110
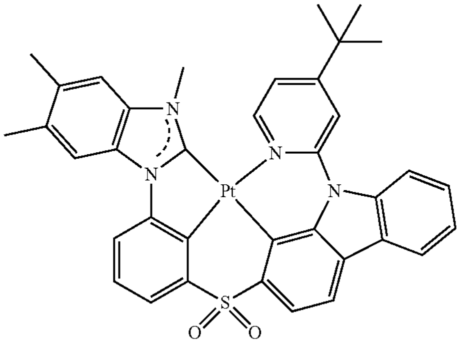
111
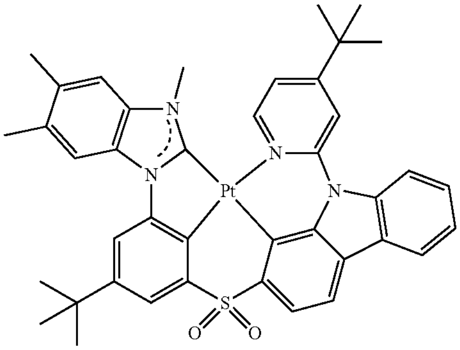

-continued
112
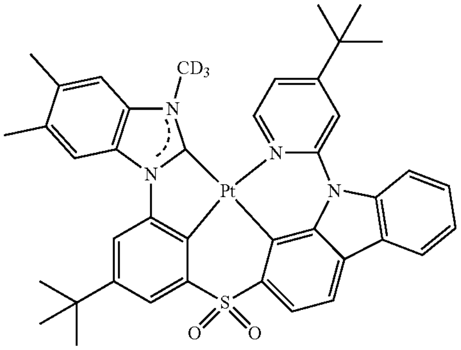
113
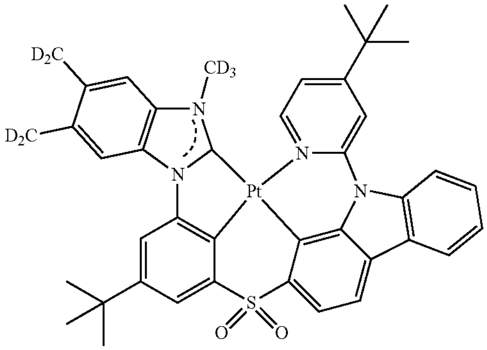
114
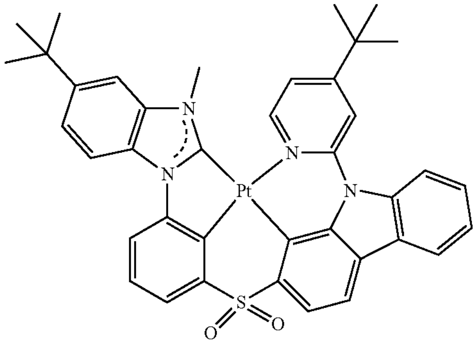
115
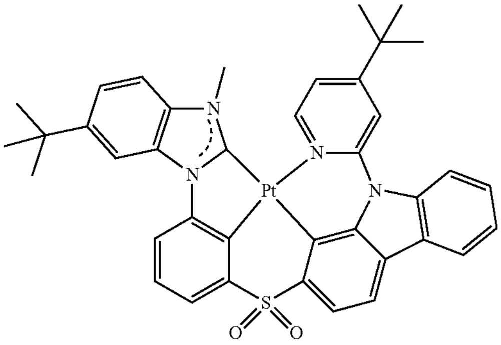
-continued
116
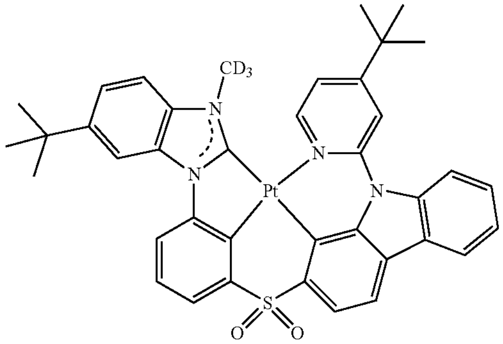
117
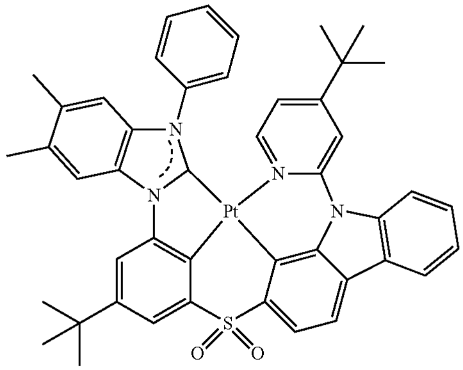
118
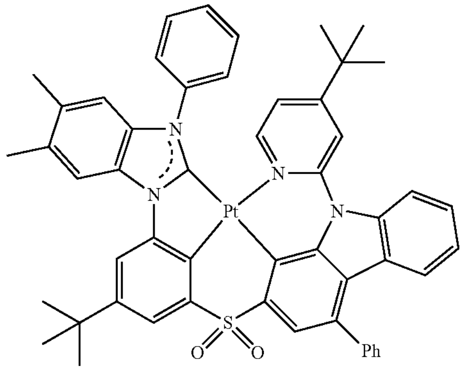
119
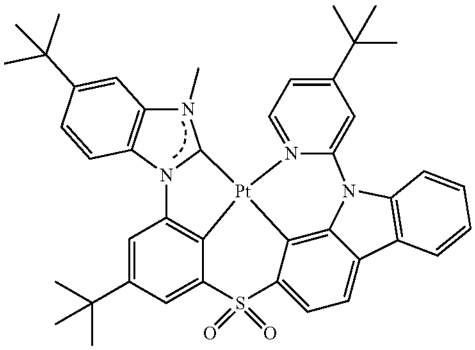

-continued
120
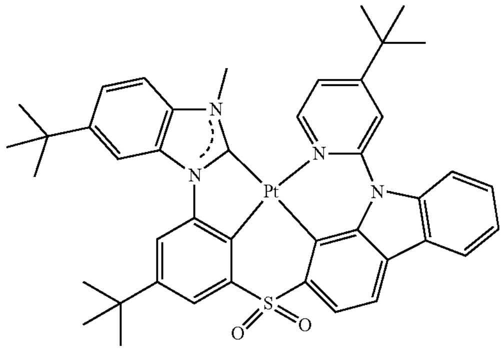
Group III
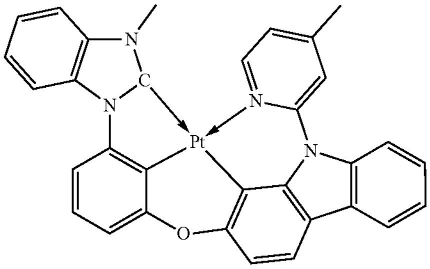
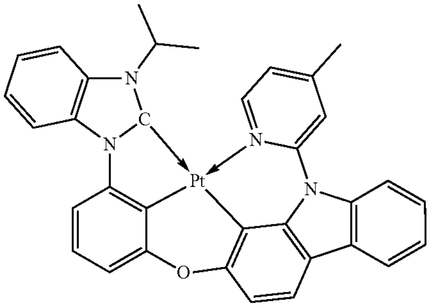
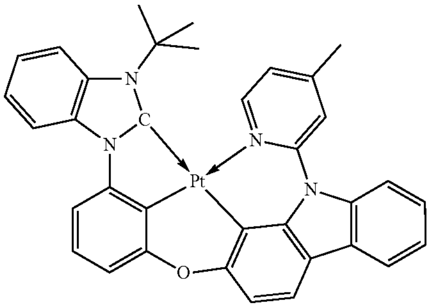
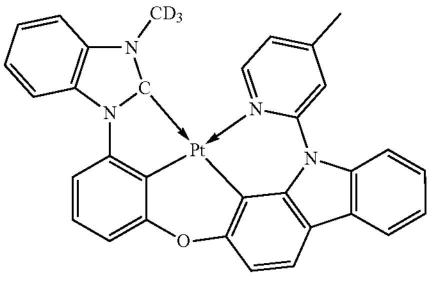
-continued
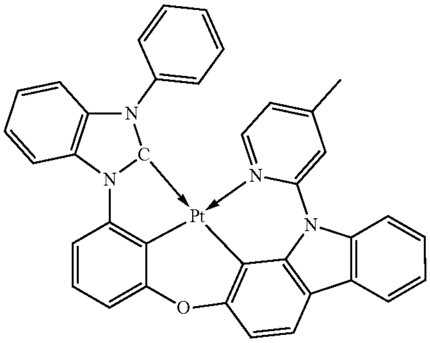
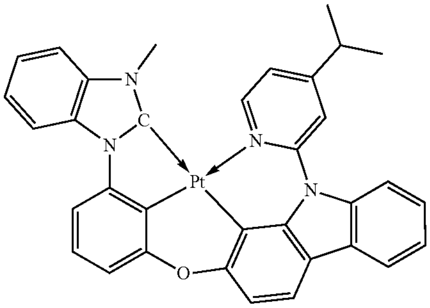
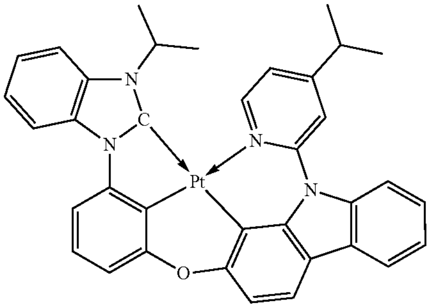
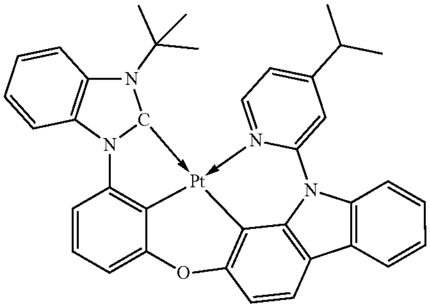
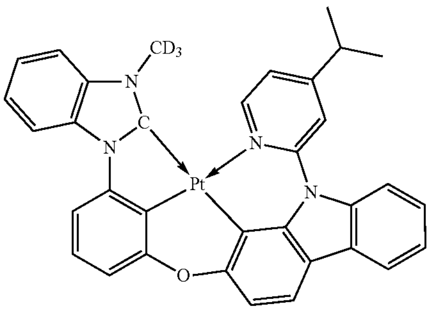

-continued
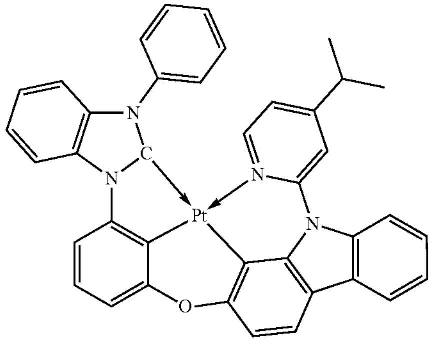
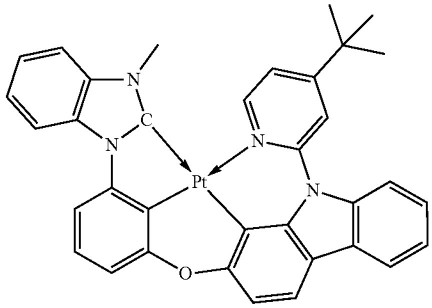
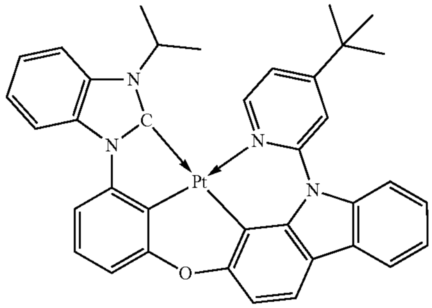
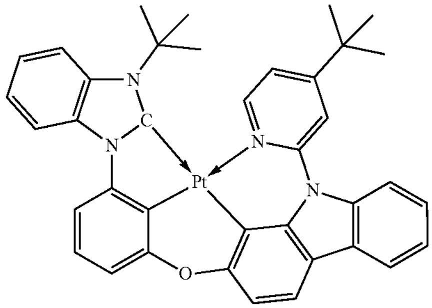
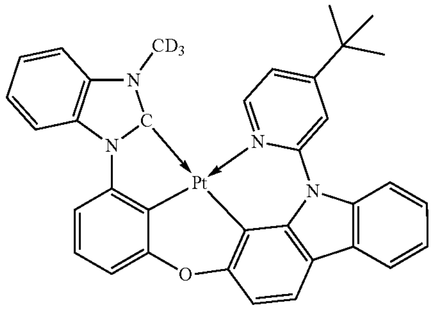
-continued
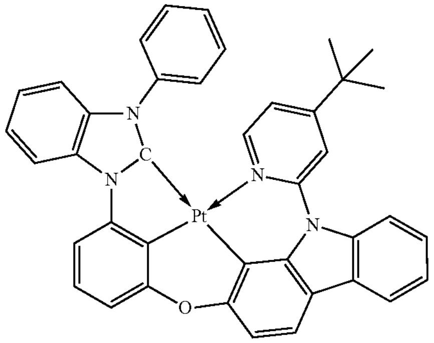
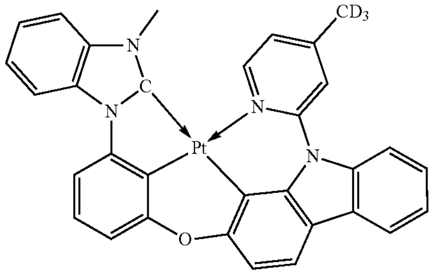
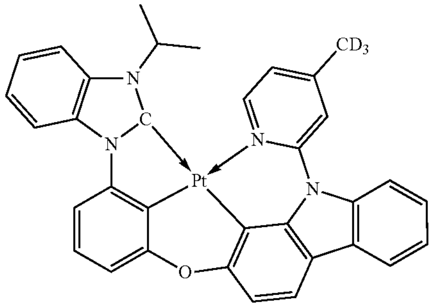
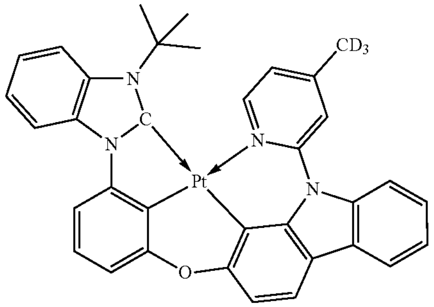
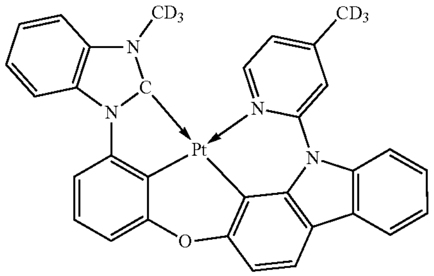

-continued
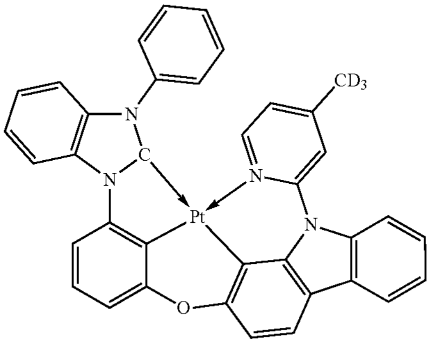
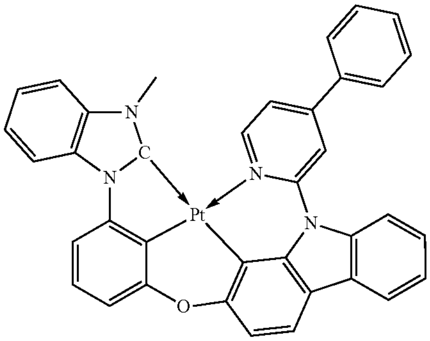
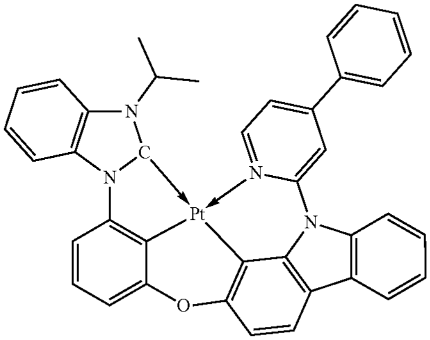
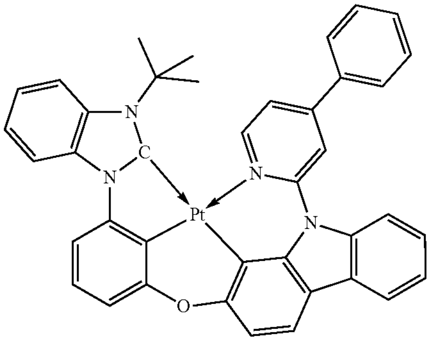
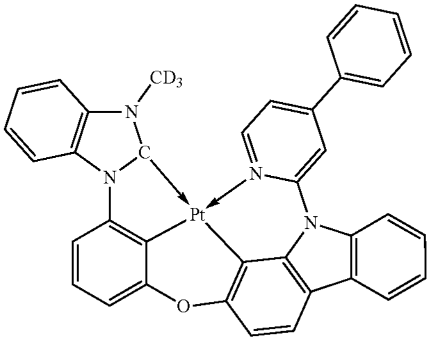
-continued
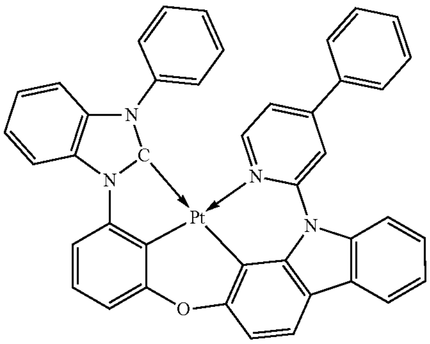
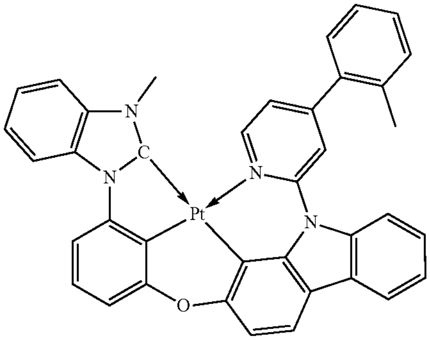
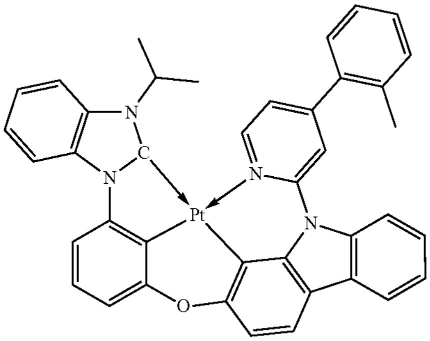
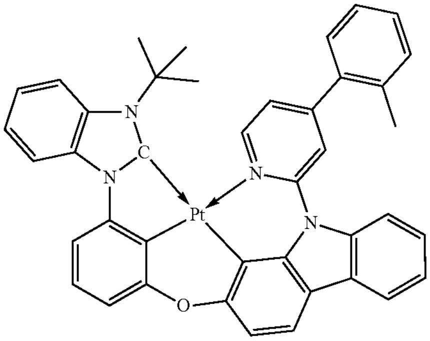
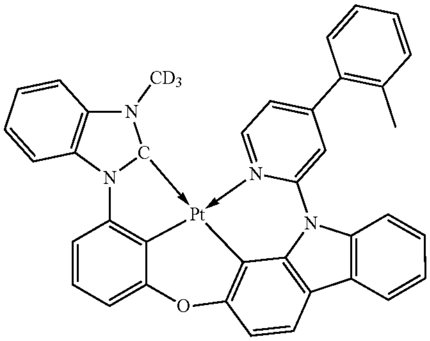

-continued
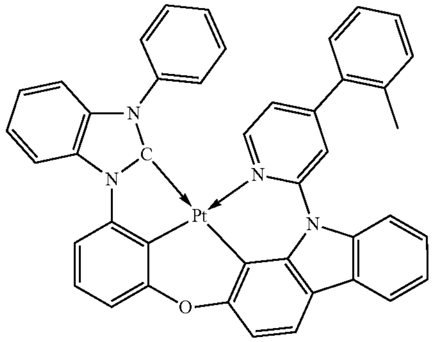
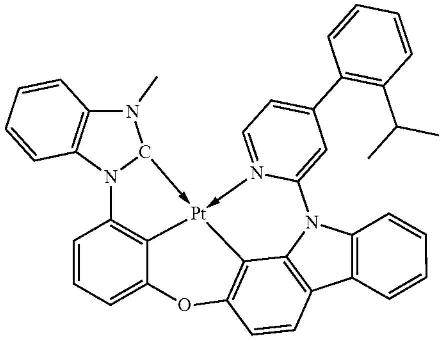
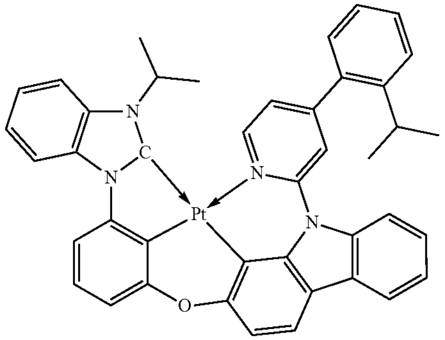
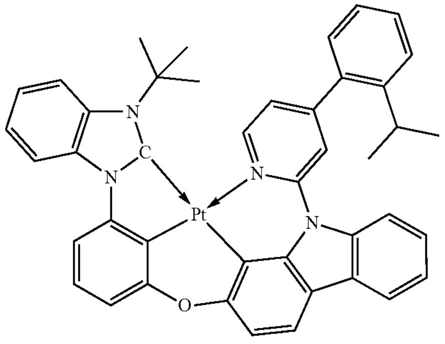
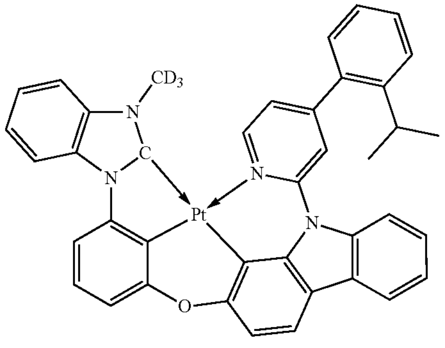
-continued
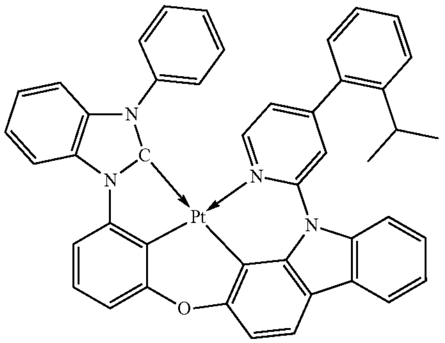
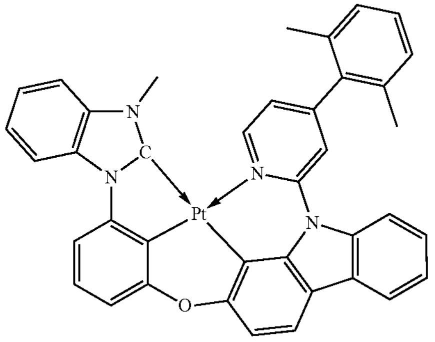
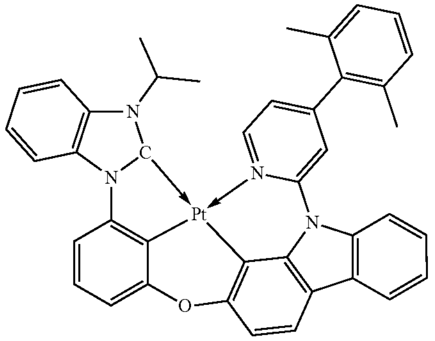
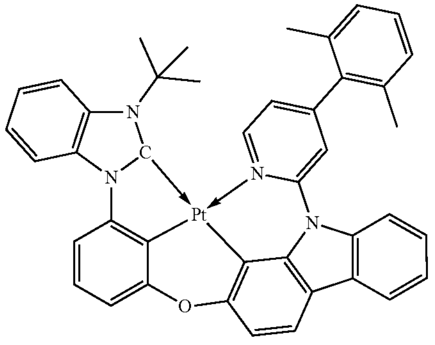
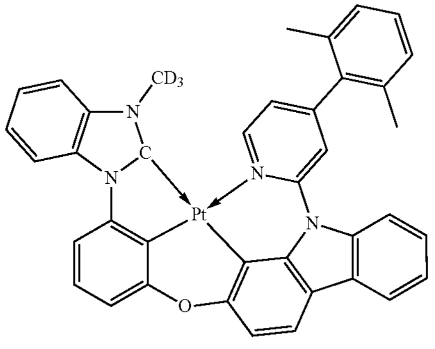

-continued
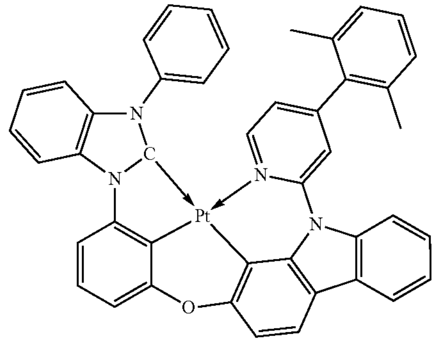
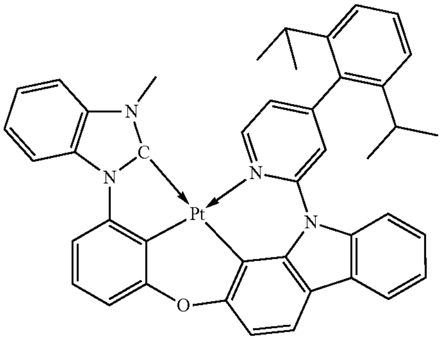
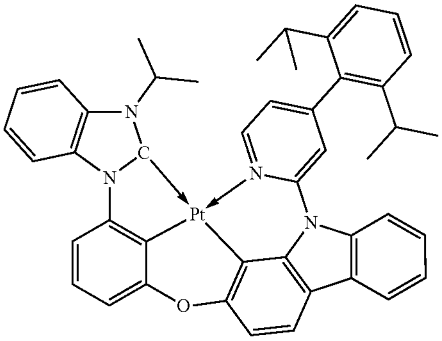
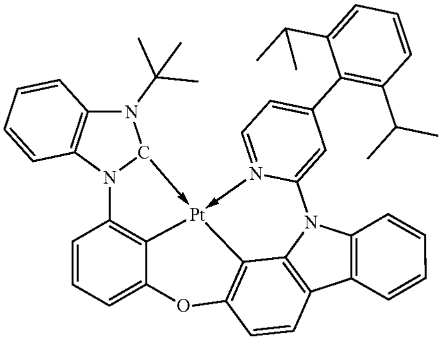
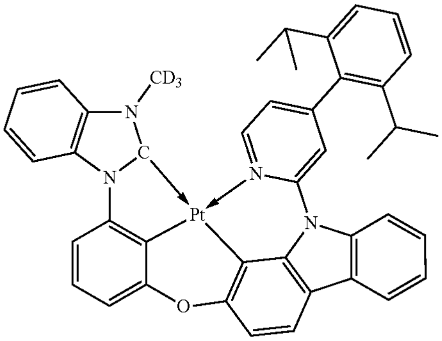
-continued
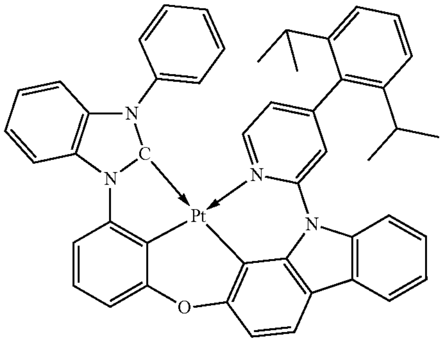
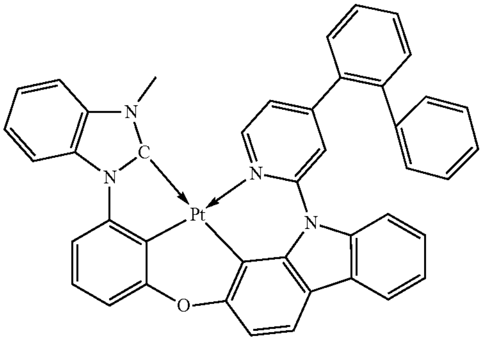
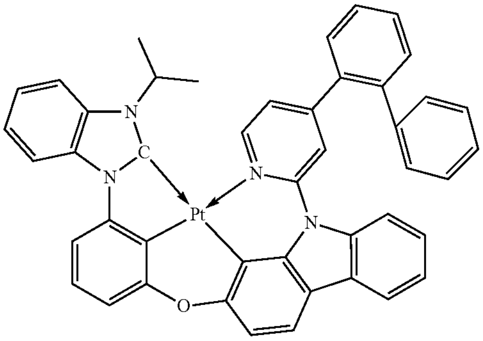
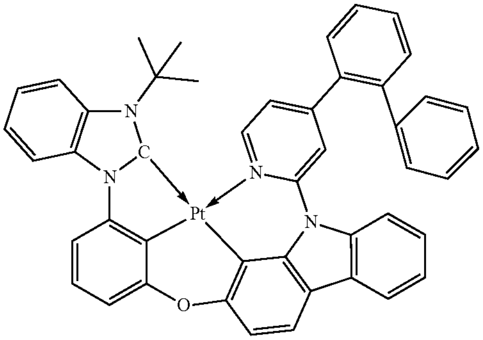
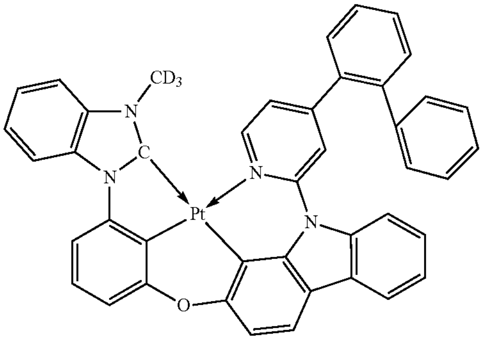

-continued
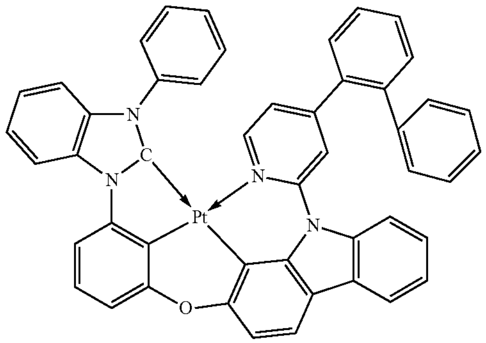
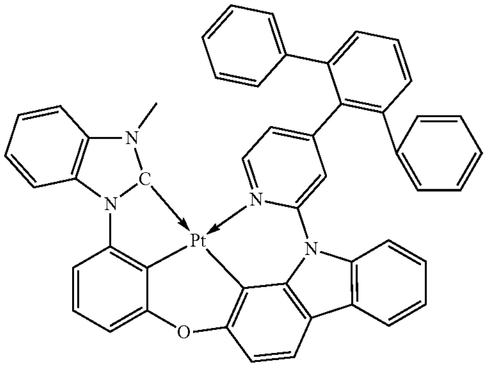
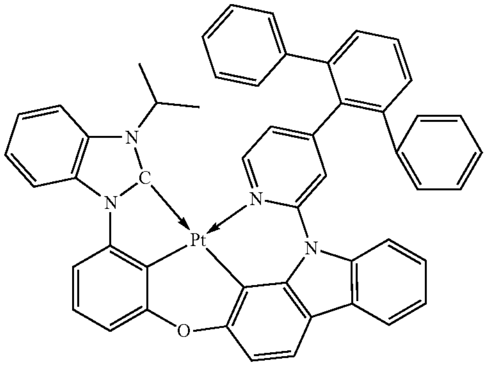
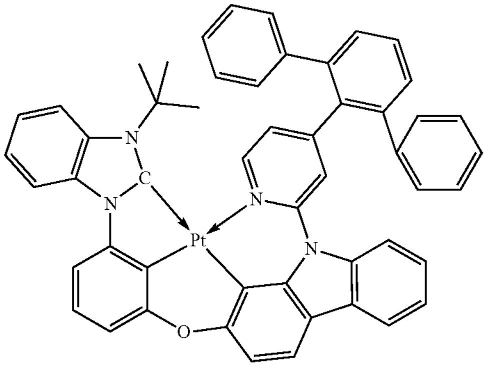
-continued
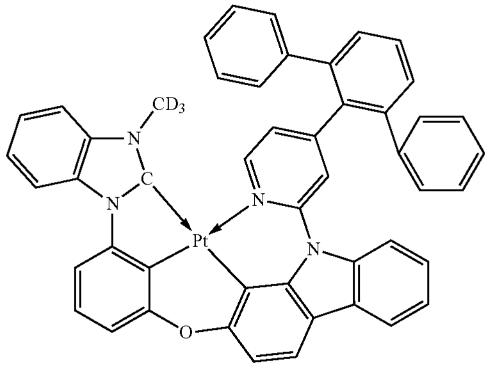
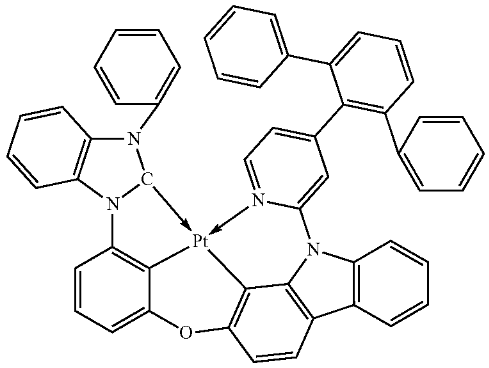
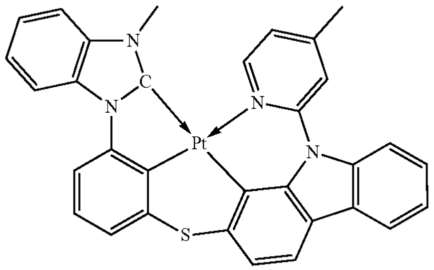
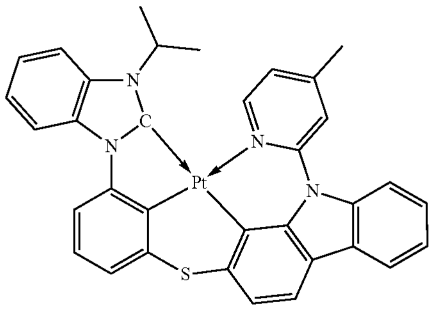
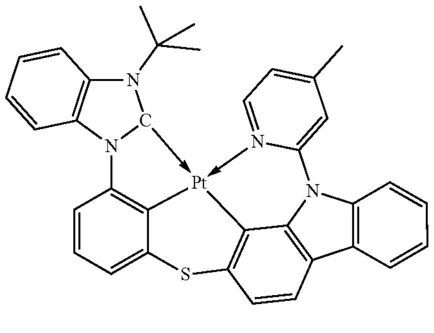

-continued
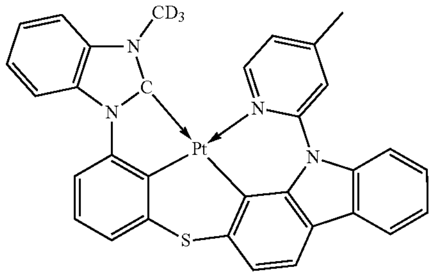
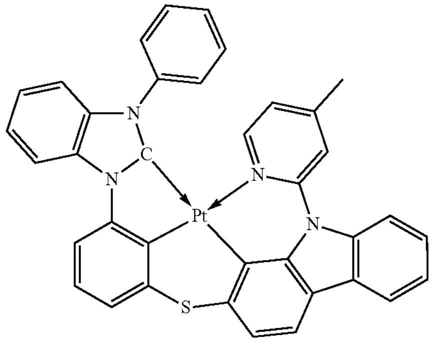
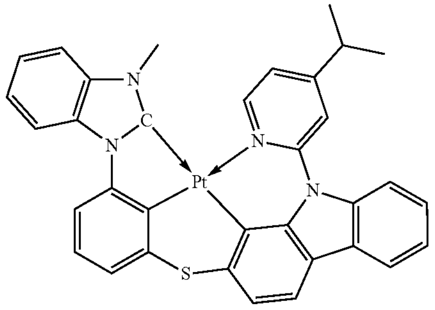
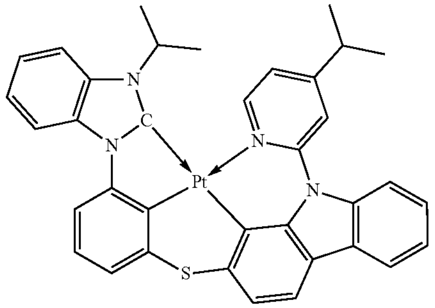
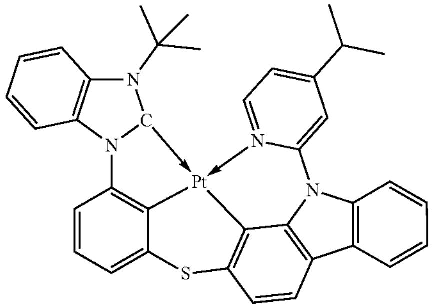
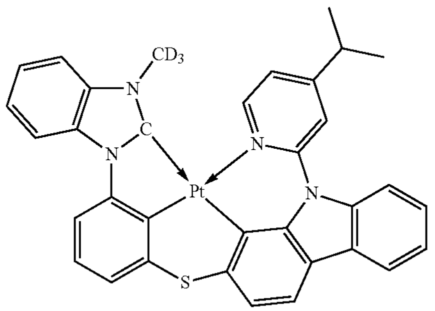
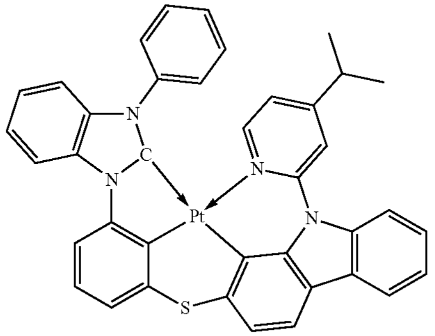
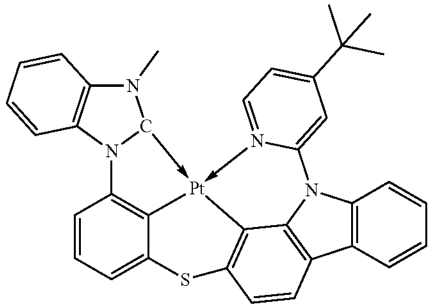
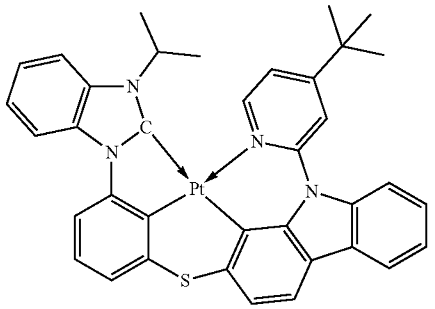
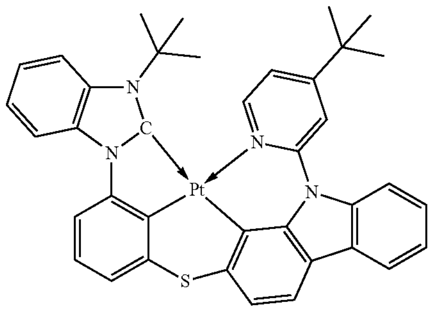

-continued
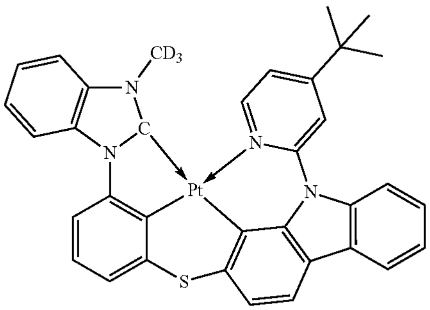
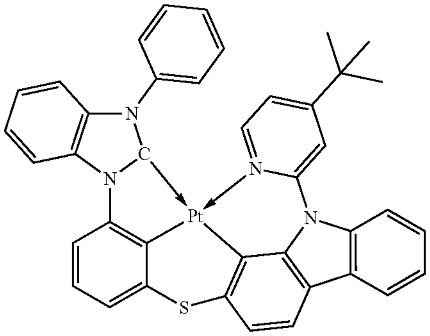
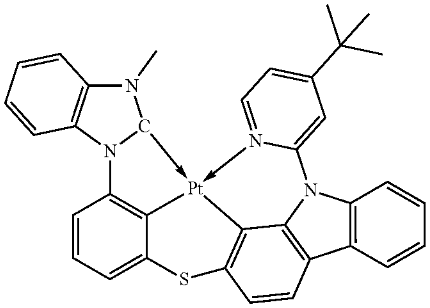
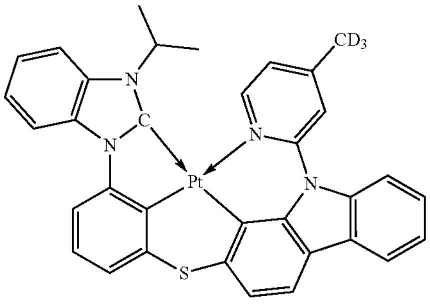
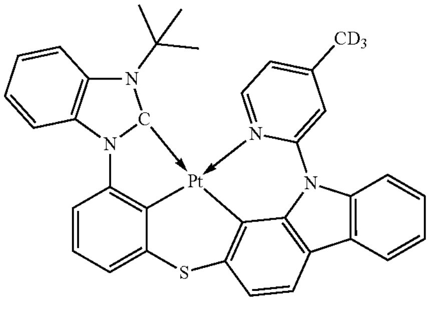
-continued
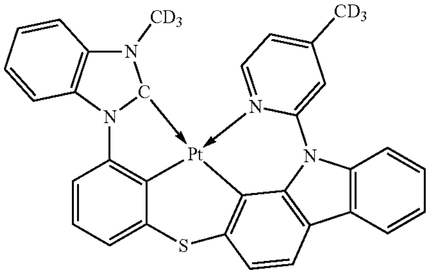
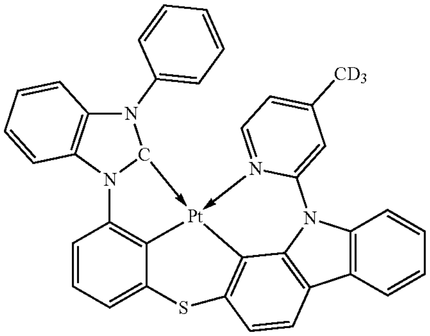
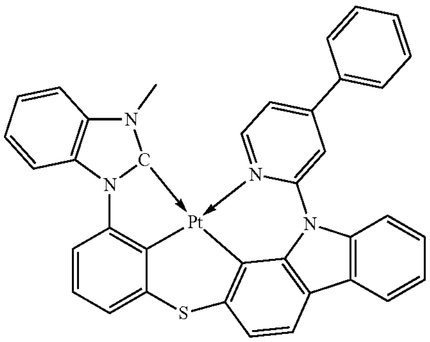
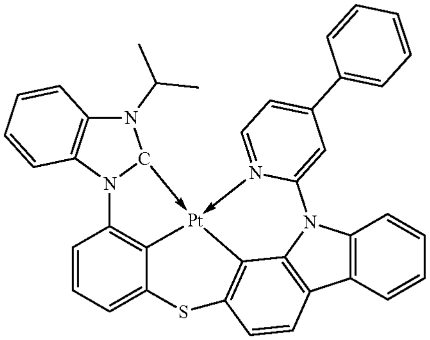
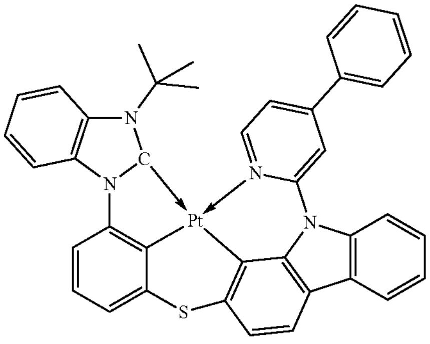

-continued
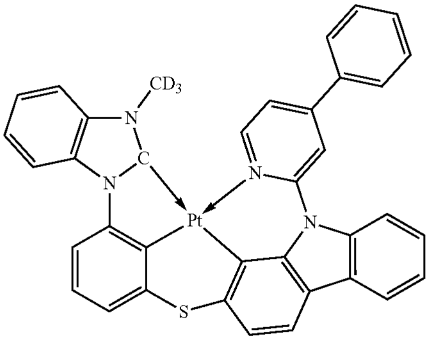
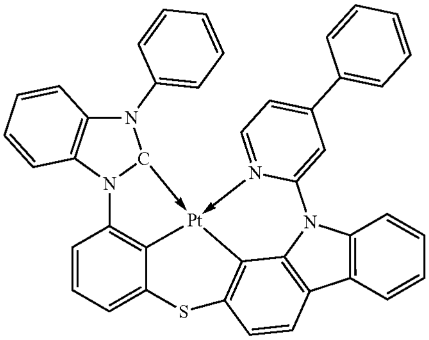
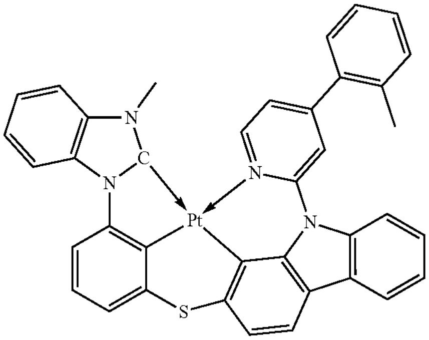
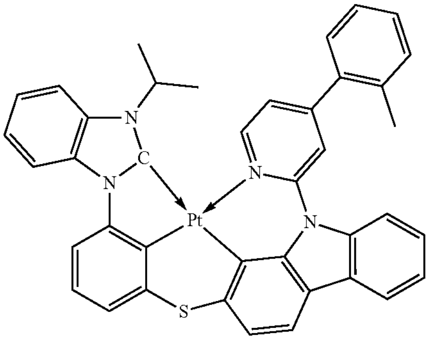
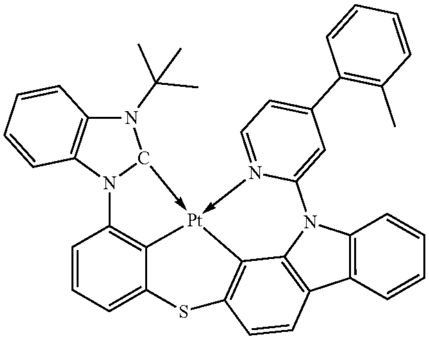
-continued
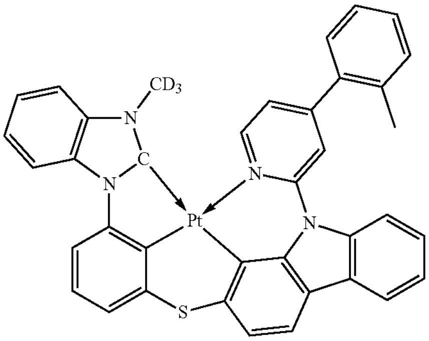
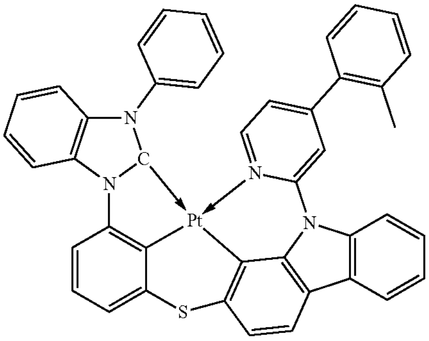
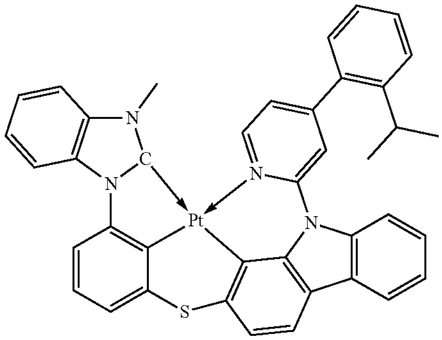
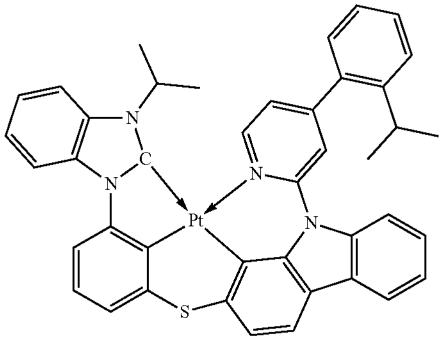
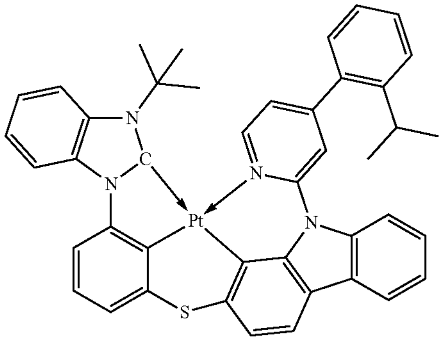

-continued
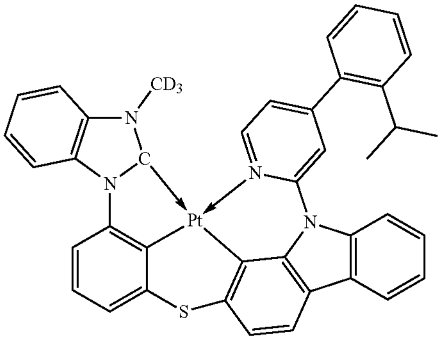
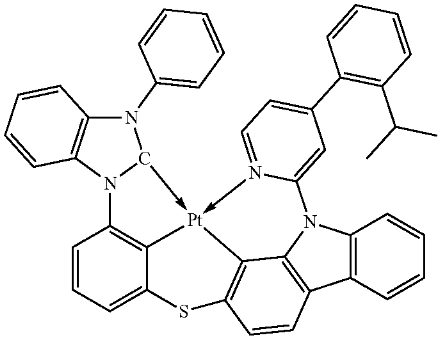
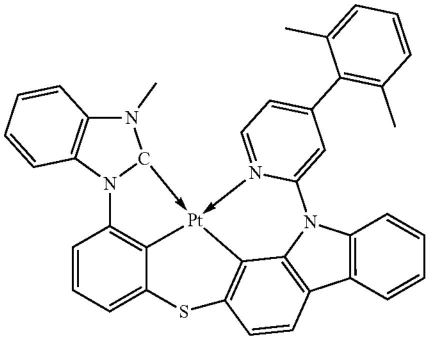
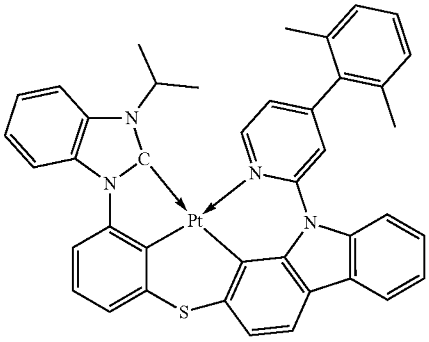
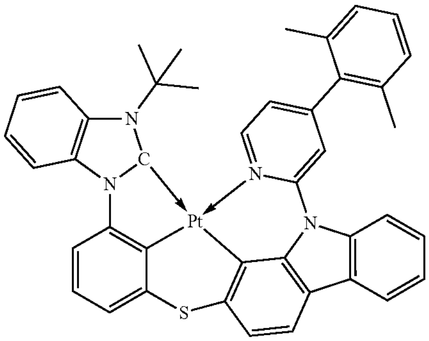
-continued
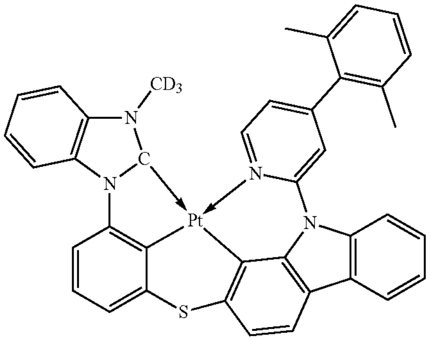
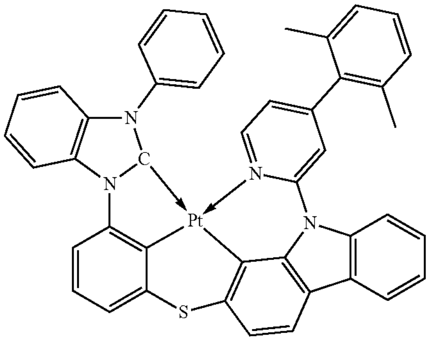
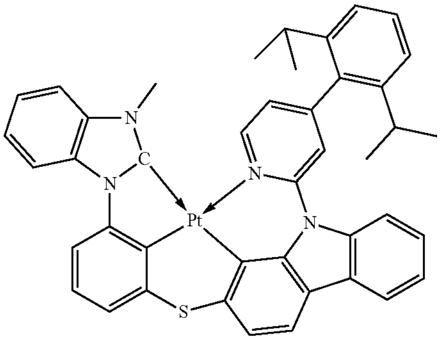
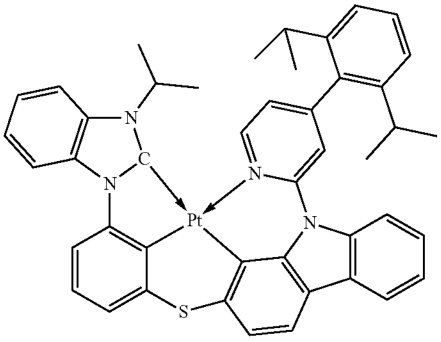
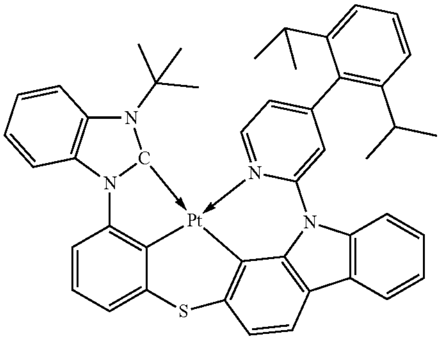

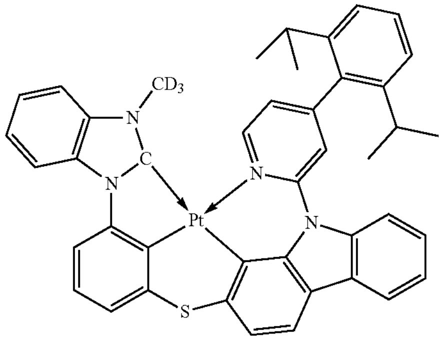
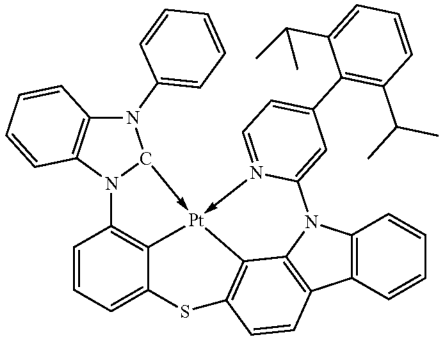
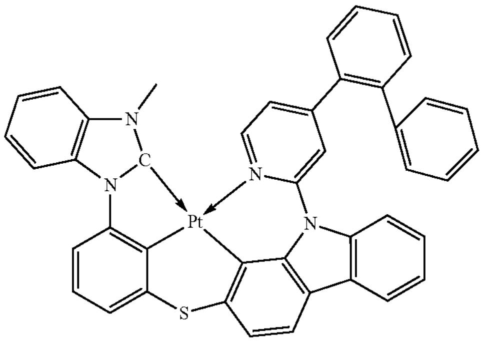
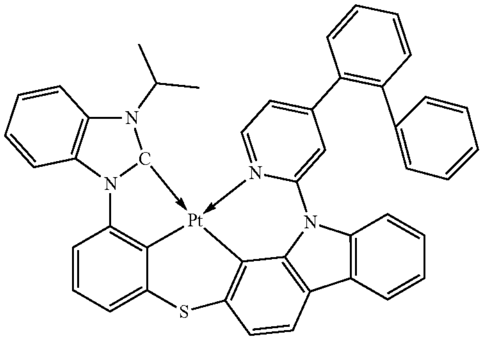
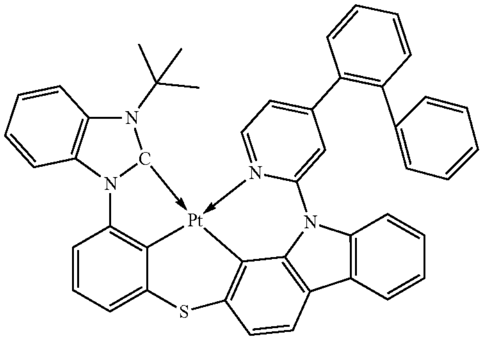
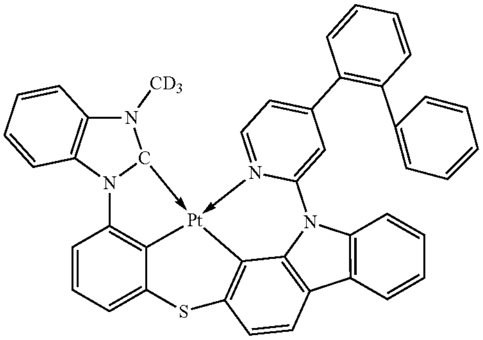
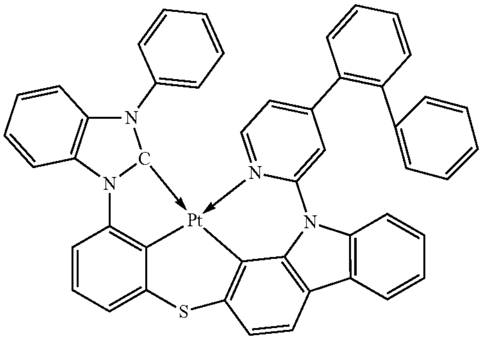
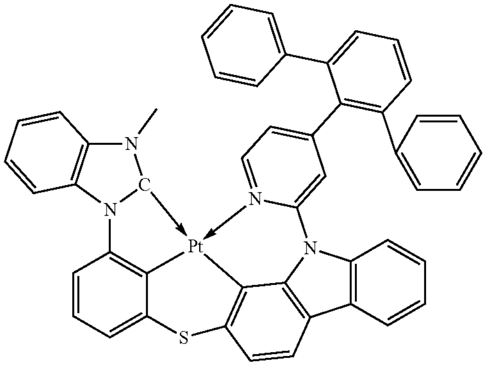
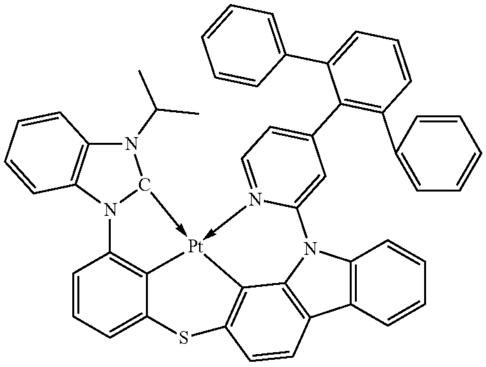

-continued
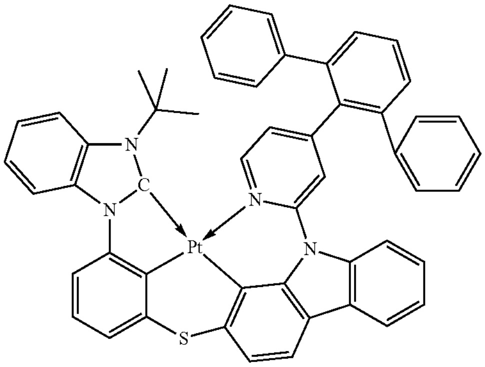
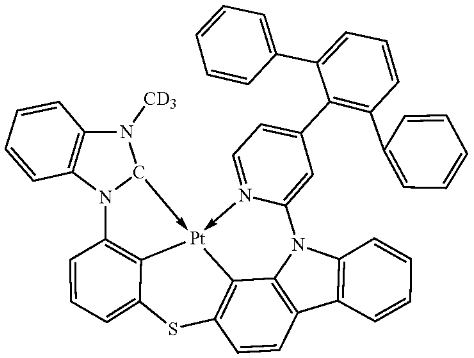
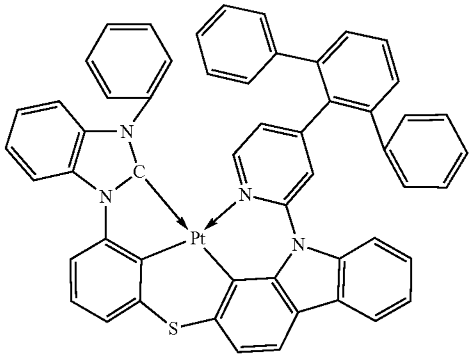
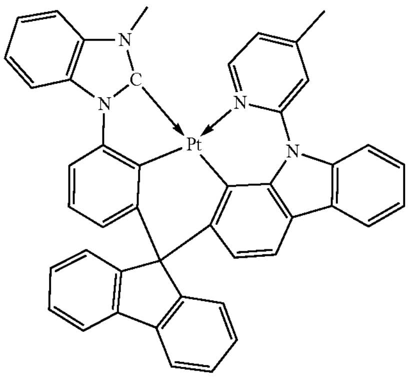
-continued
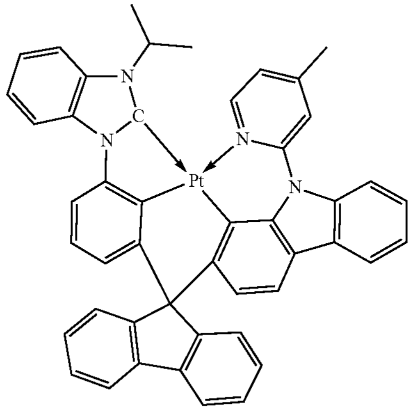
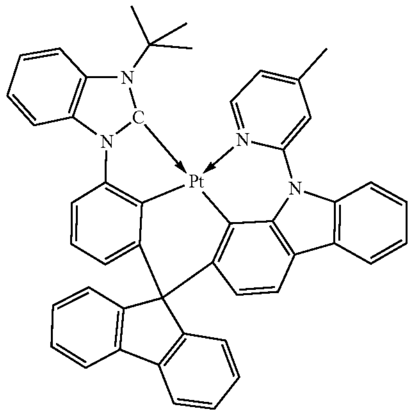
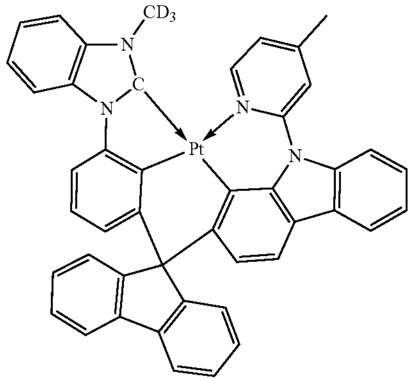
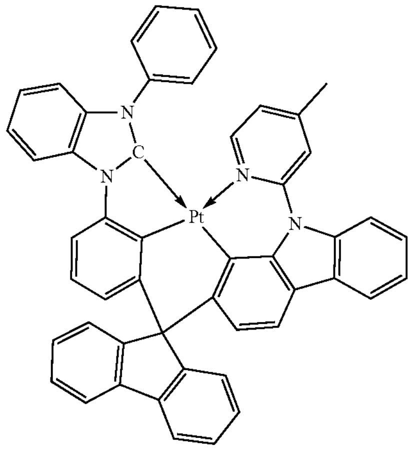

-continued
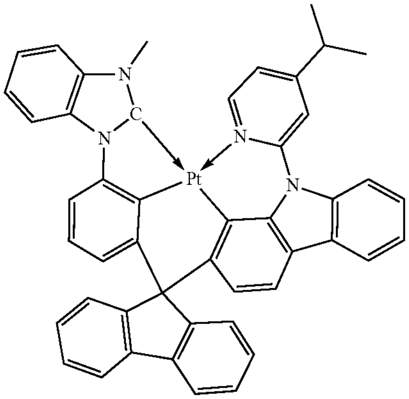
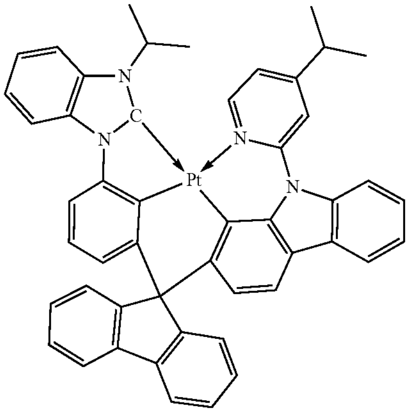
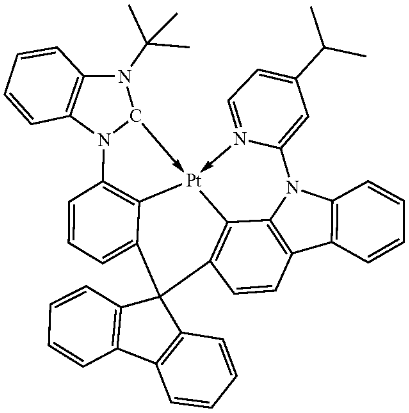
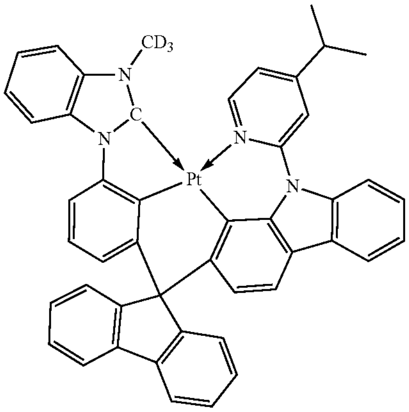
-continued
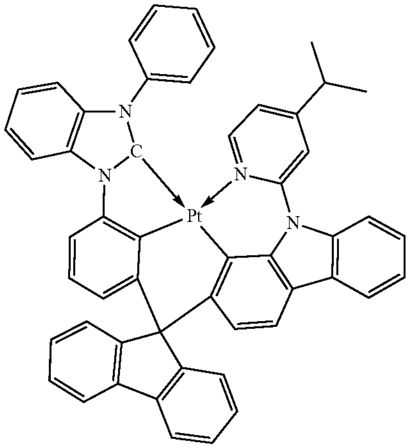
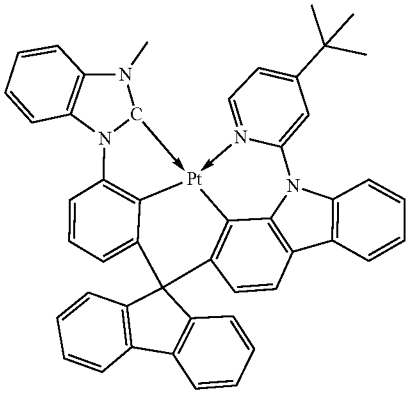
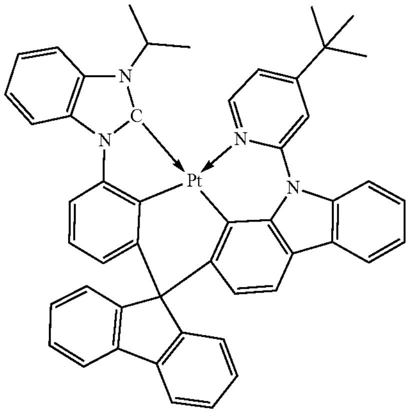
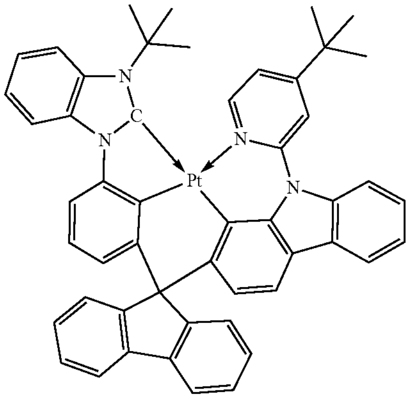

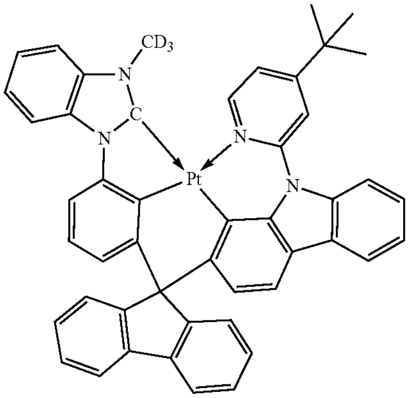
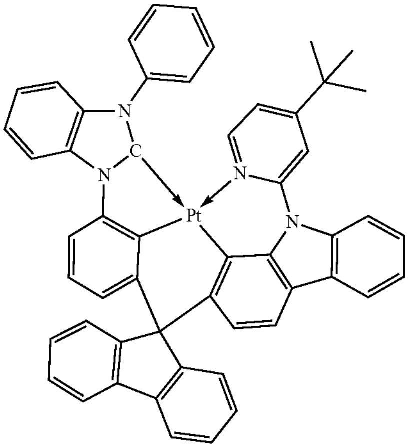
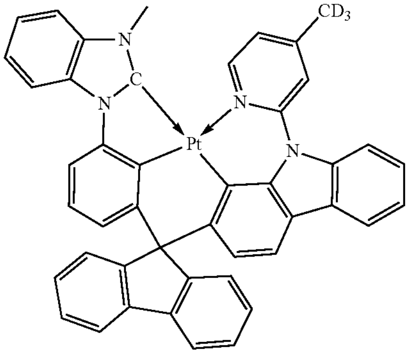
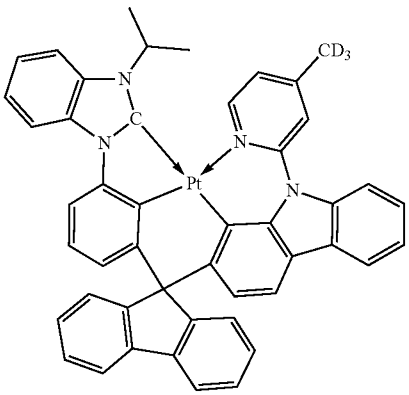
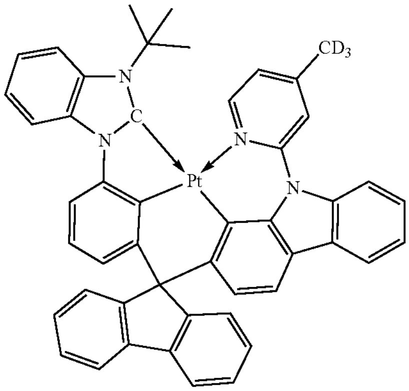
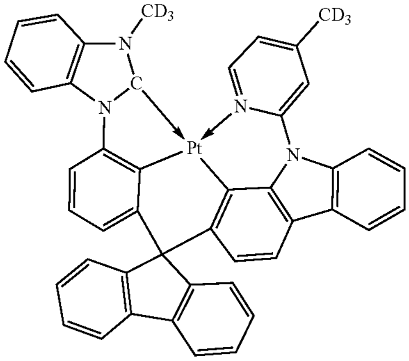
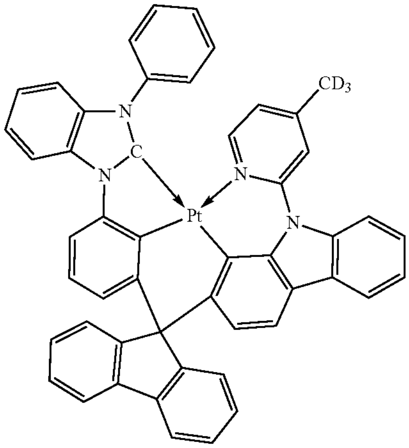
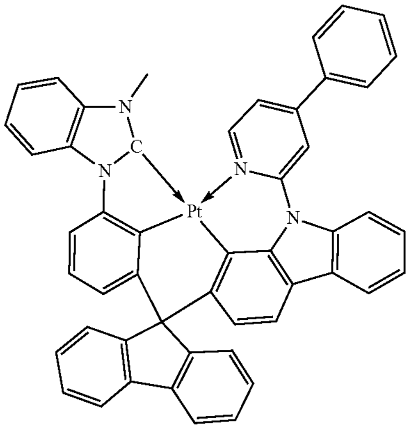

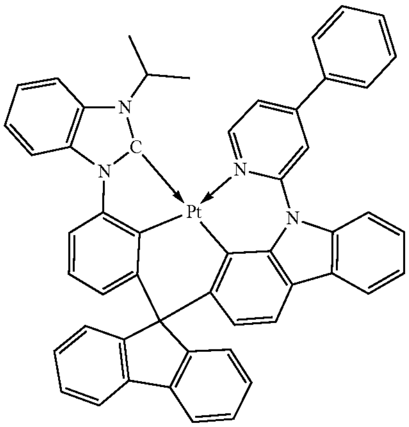
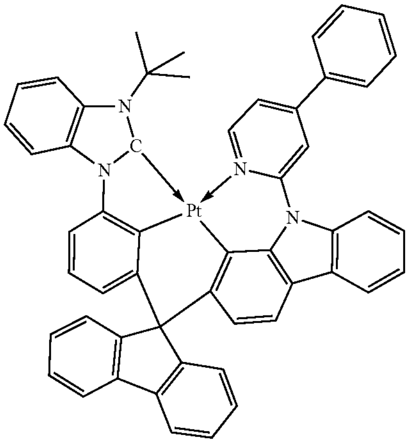
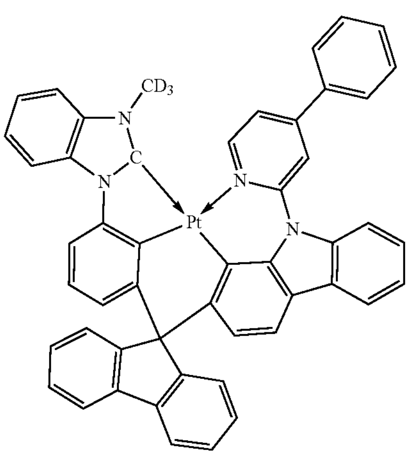
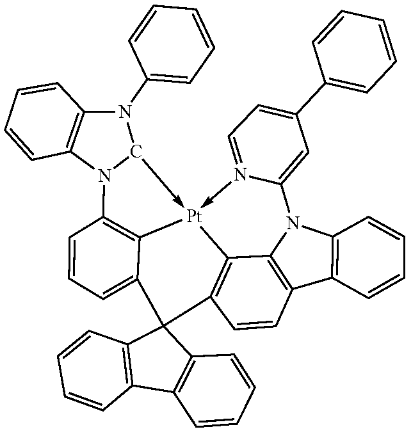
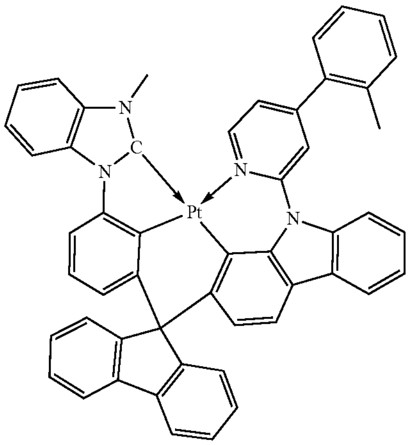
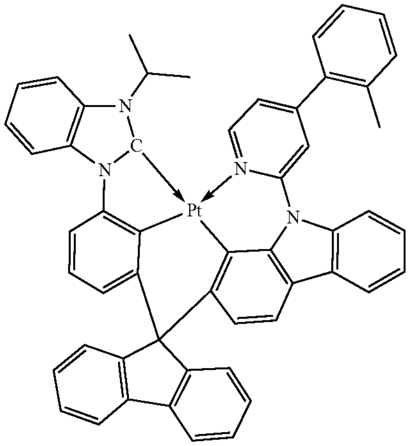

-continued
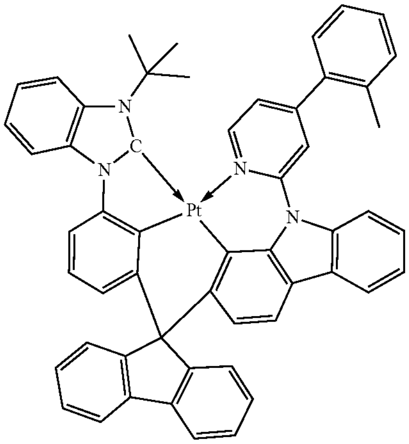
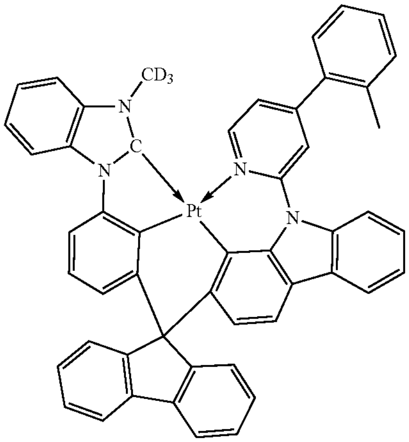
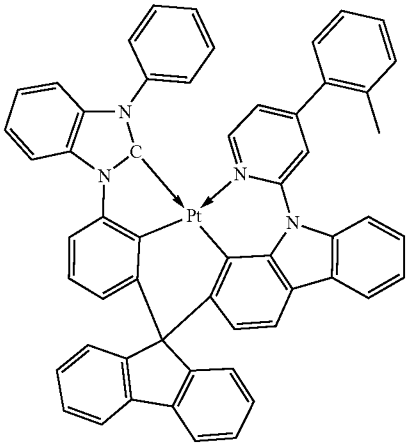
-continued
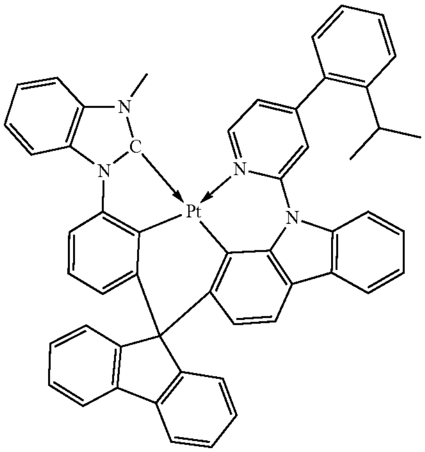
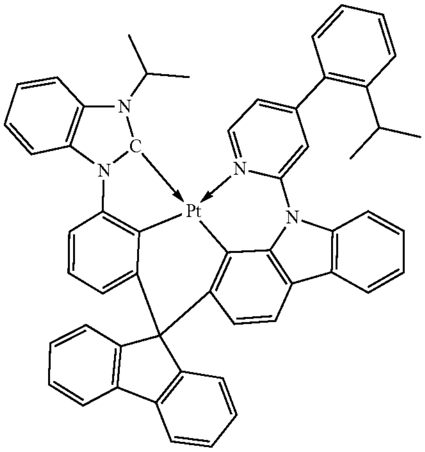
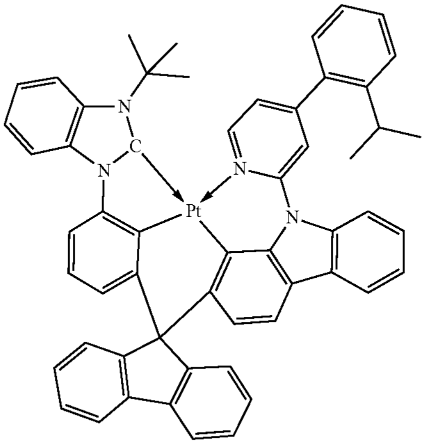

-continued
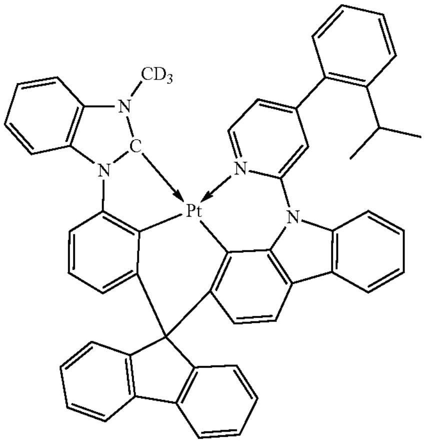
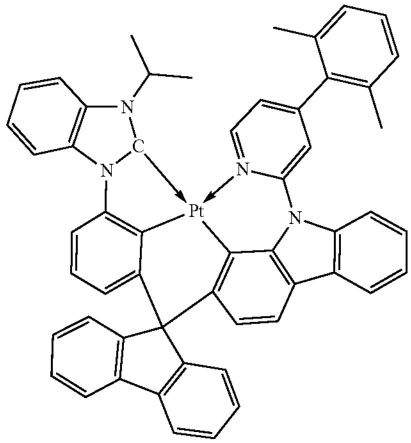
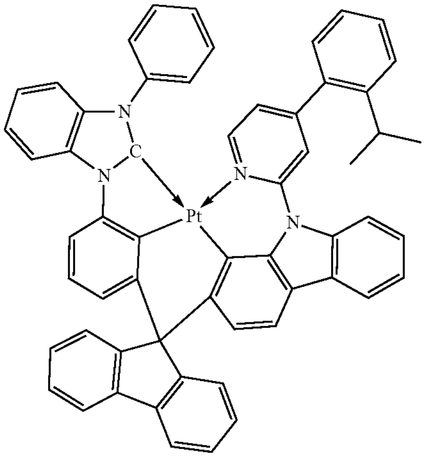
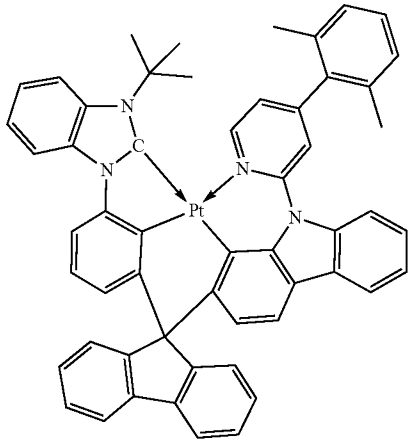
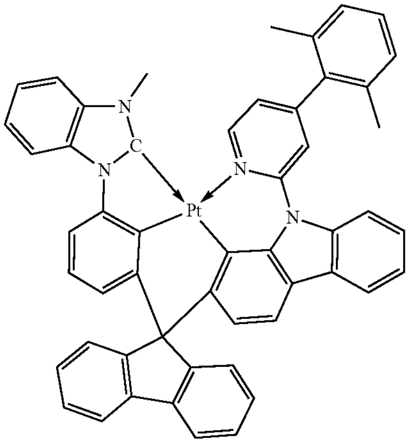
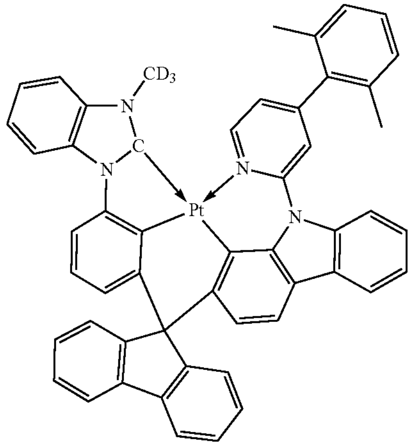
-continued -continued
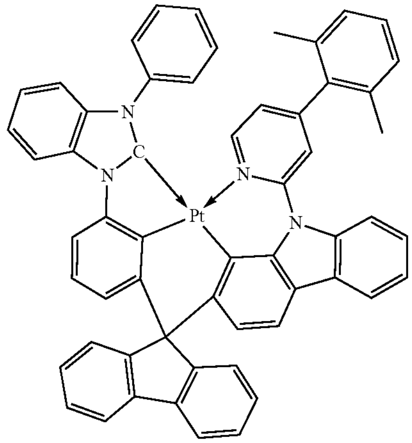
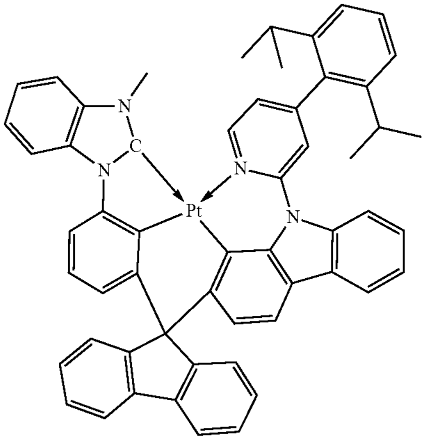
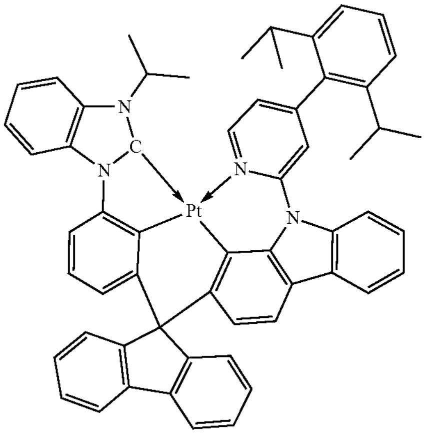
-continued
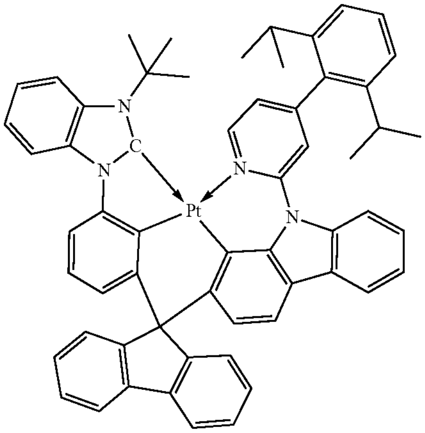
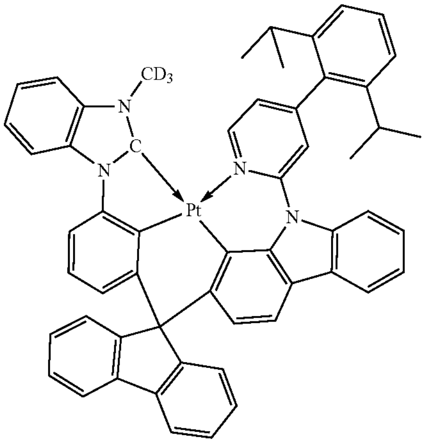
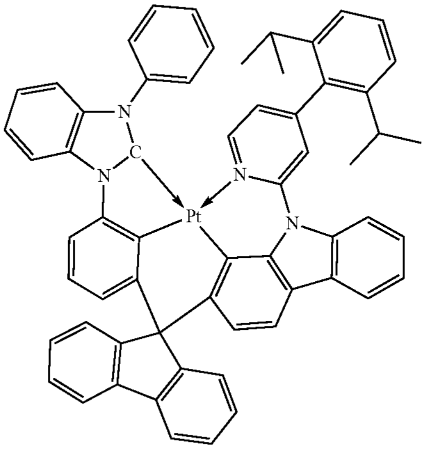

-continued
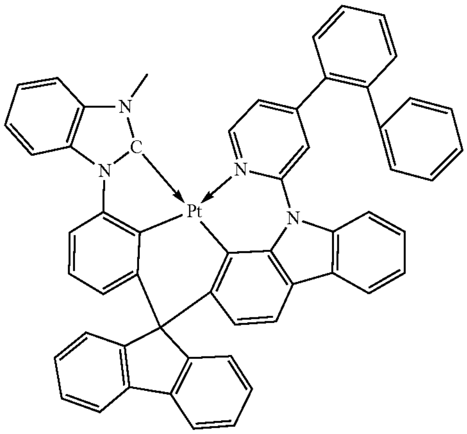
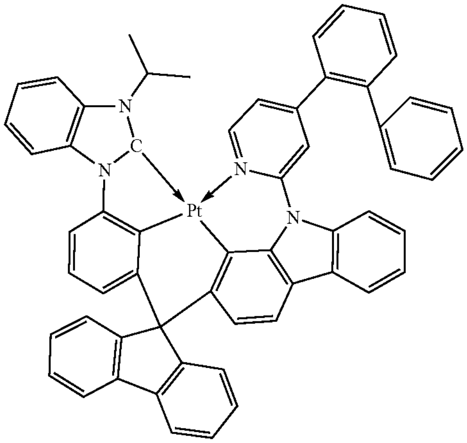
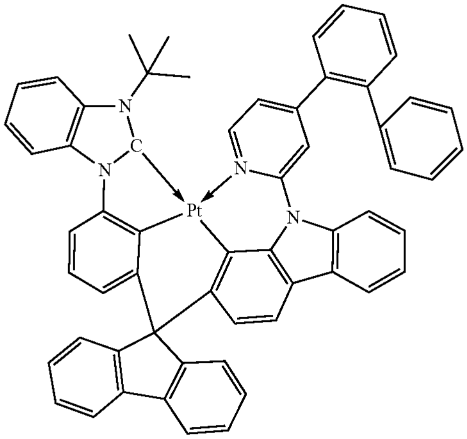
-continued
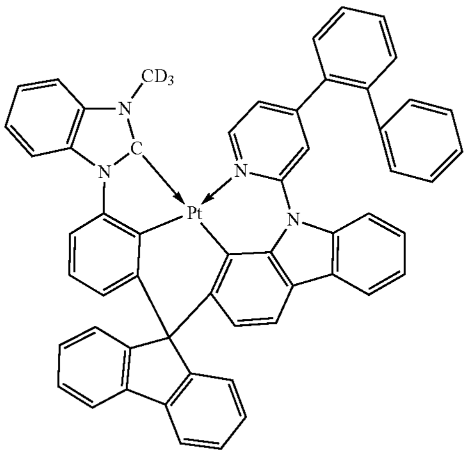
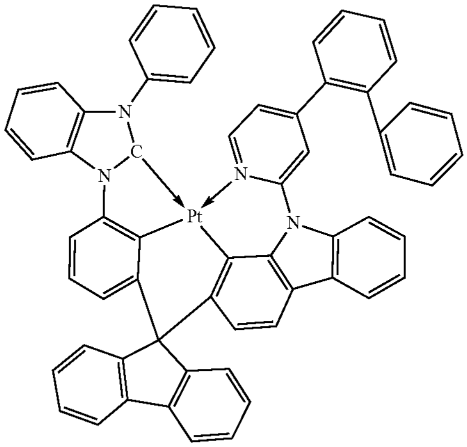
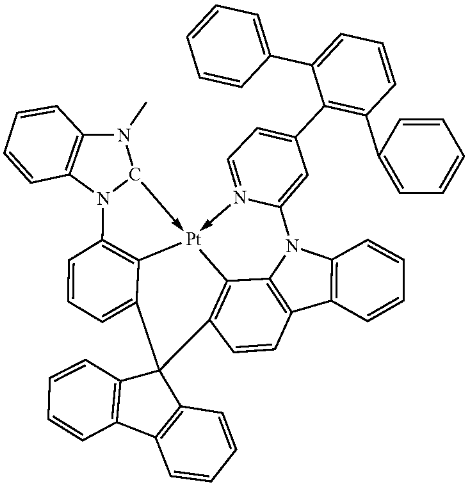

-continued
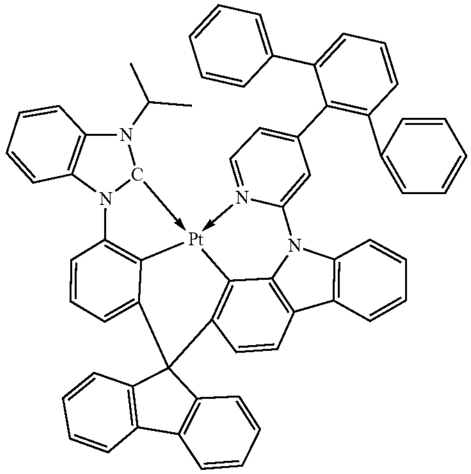
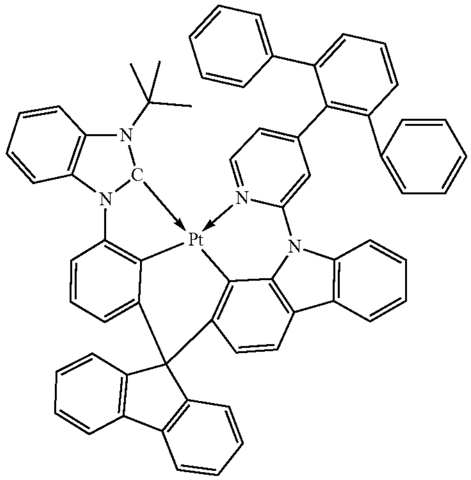
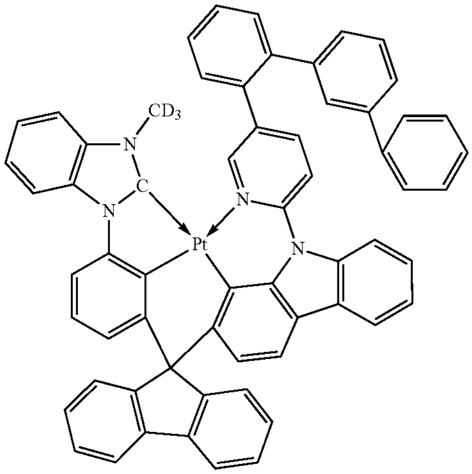
-continued
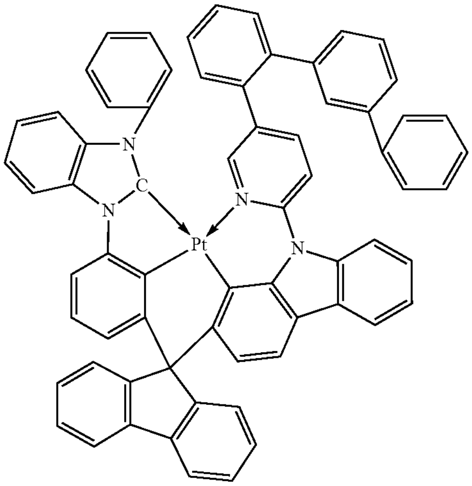
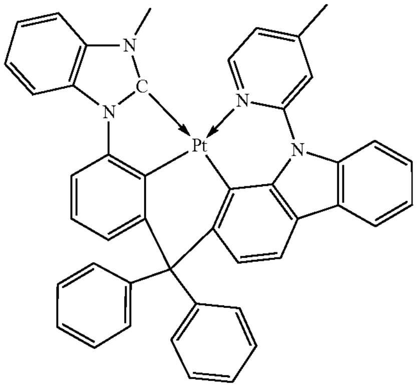
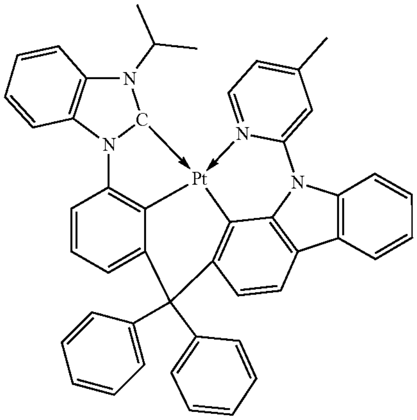
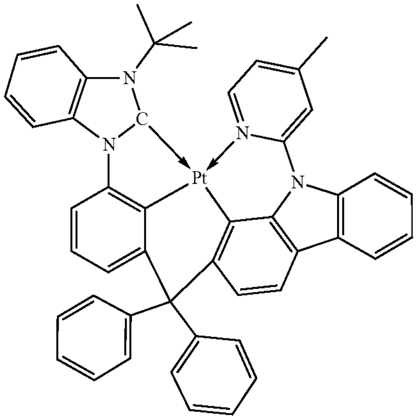

-continued
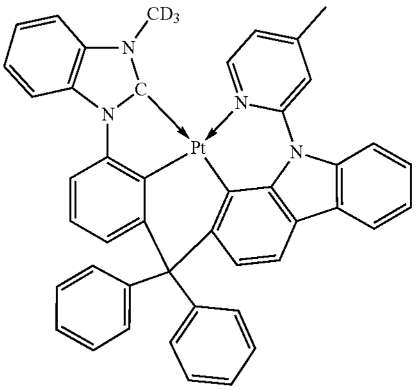
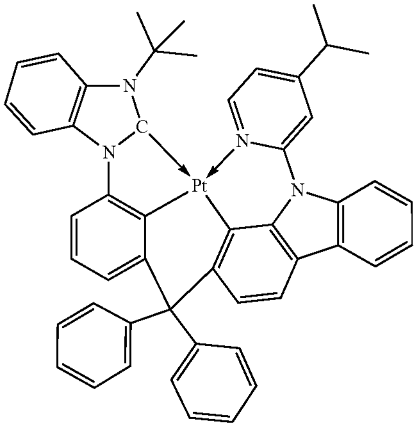
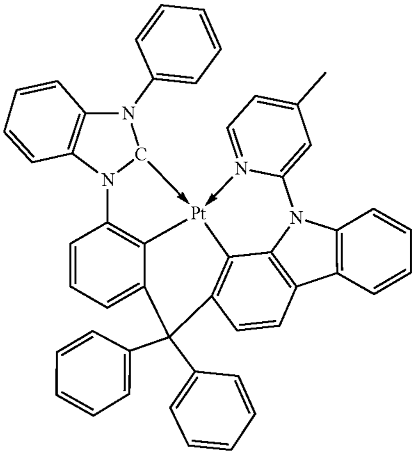
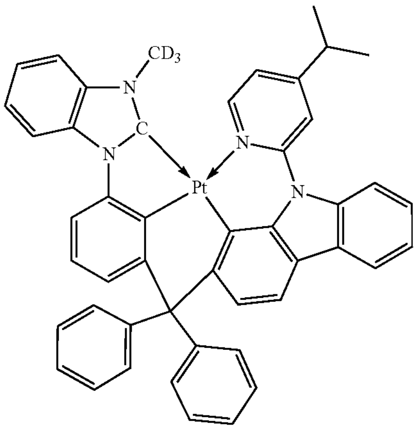
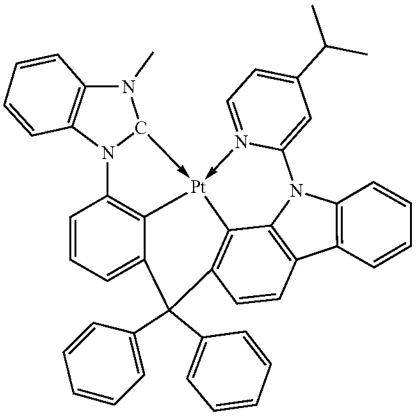
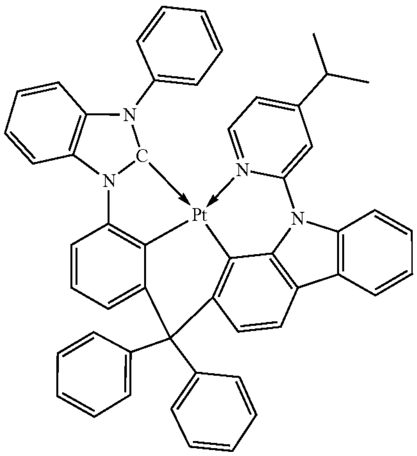
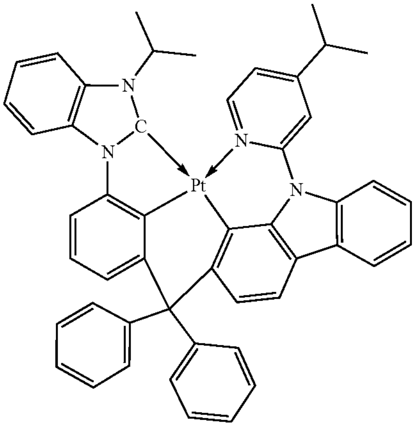
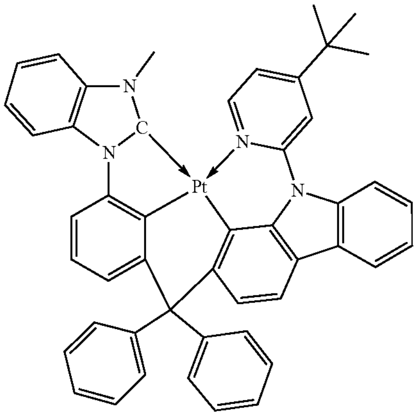
-continued -continued
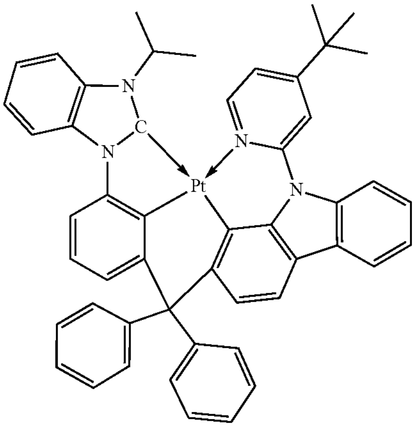
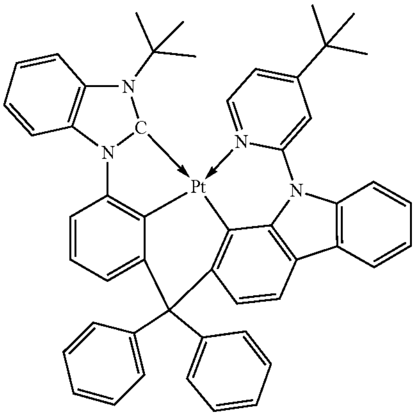
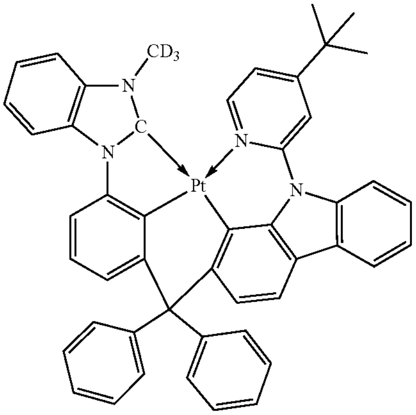
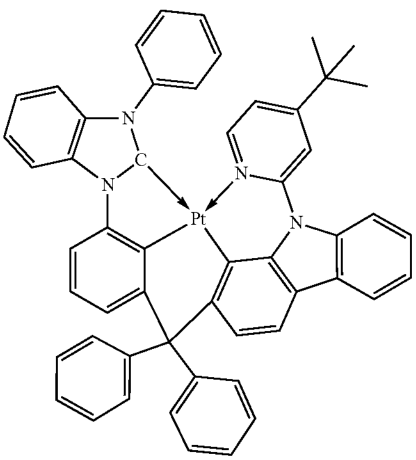
-continued
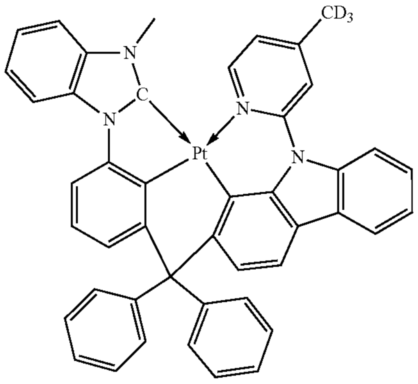
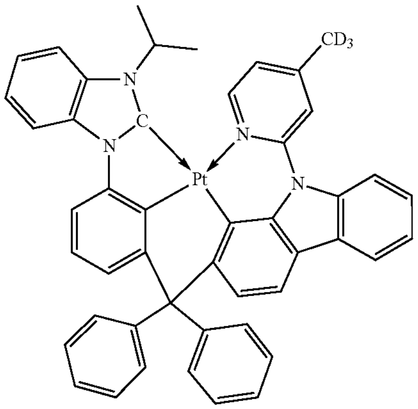
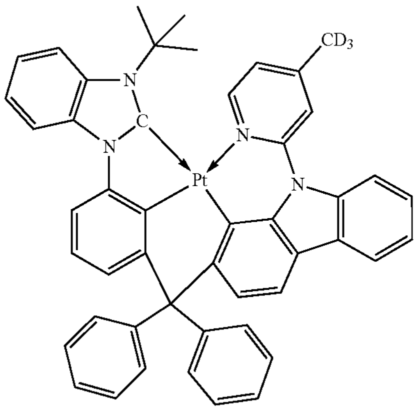
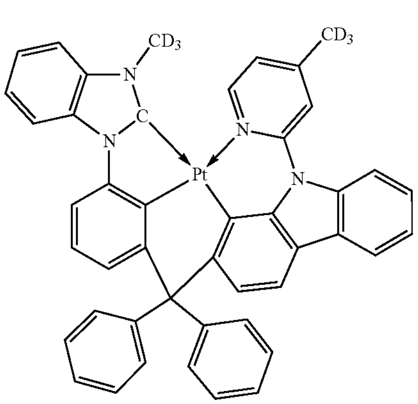

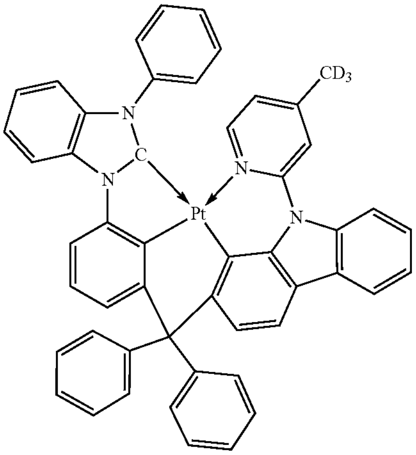
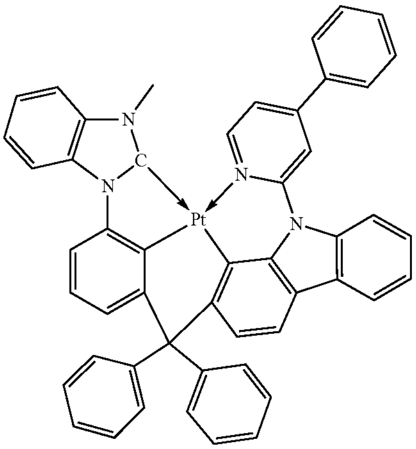
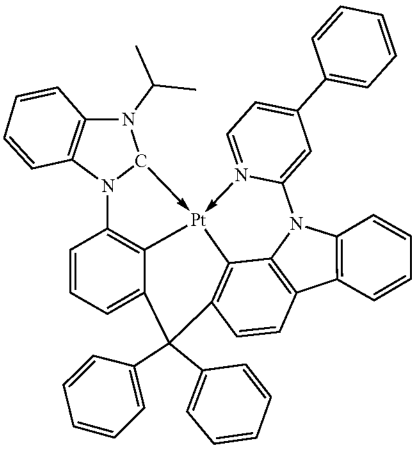
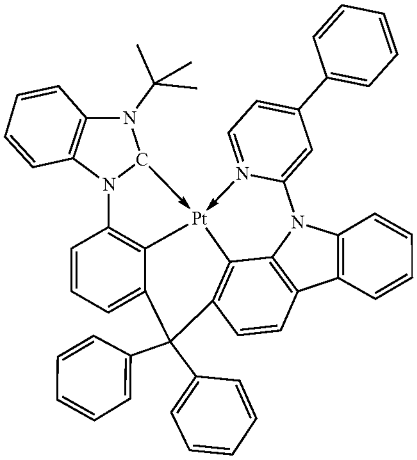
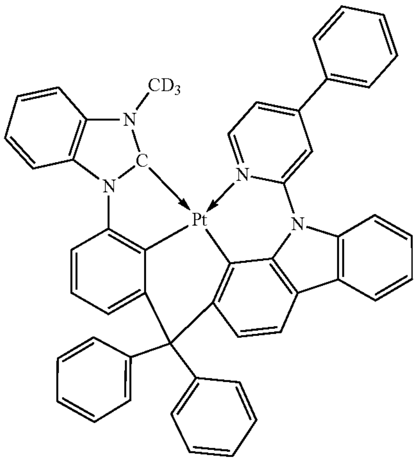
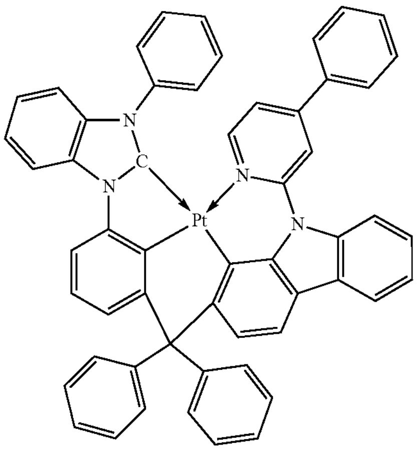

-continued
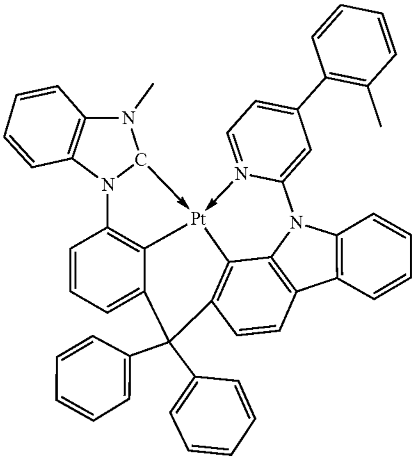
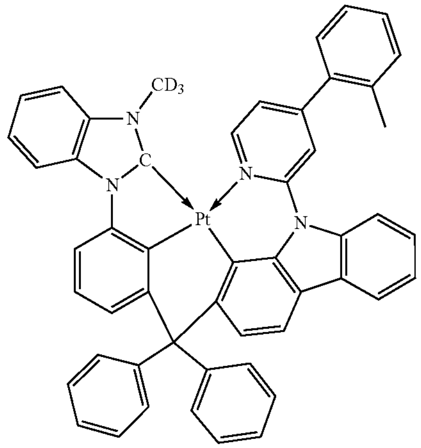
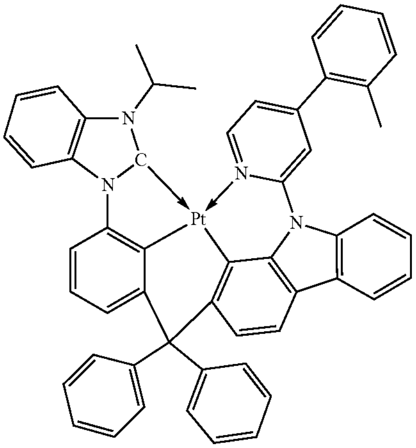
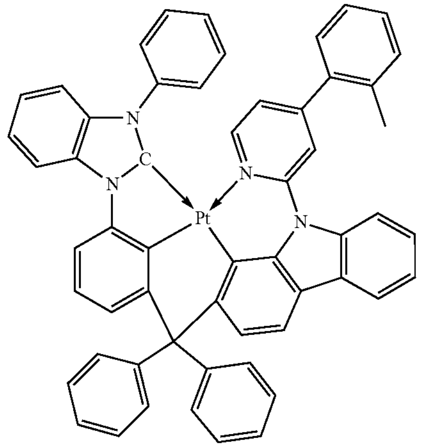
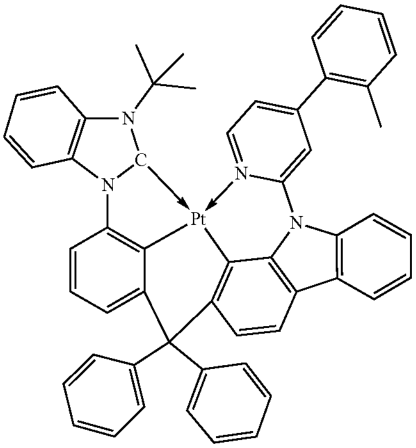
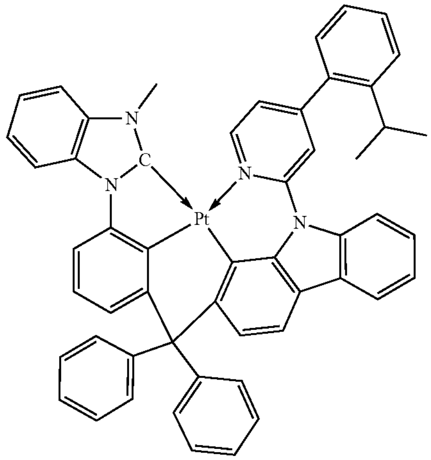
-continued

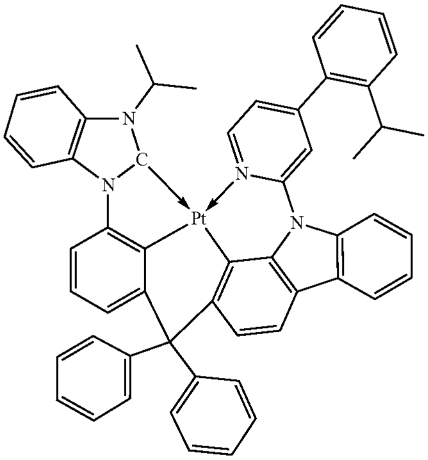
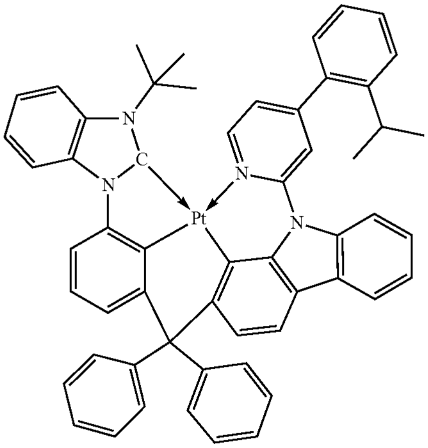
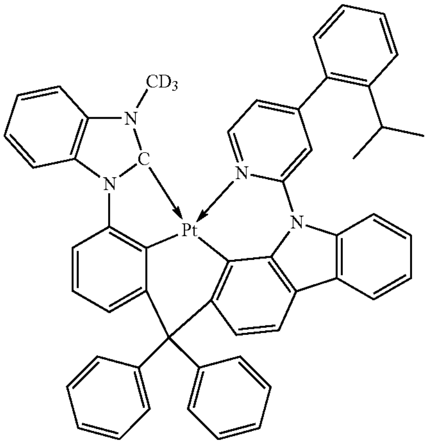
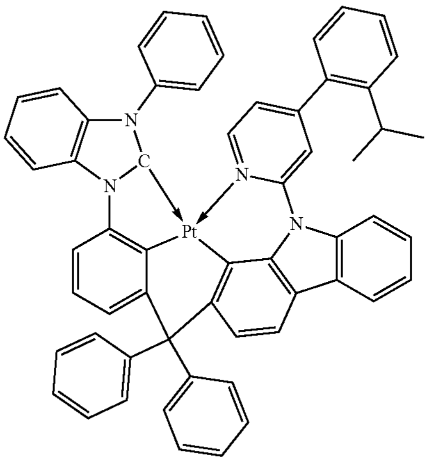
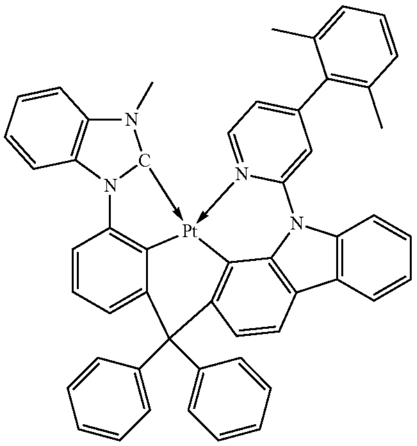
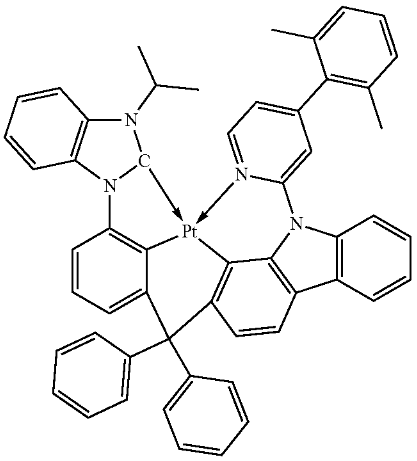

-continued
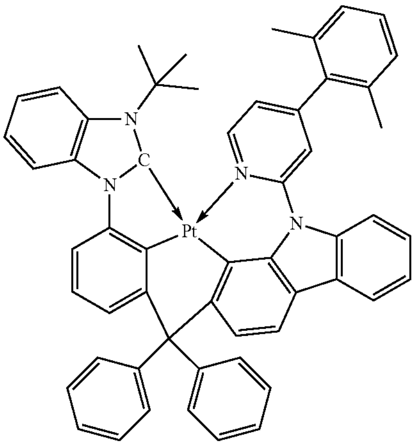
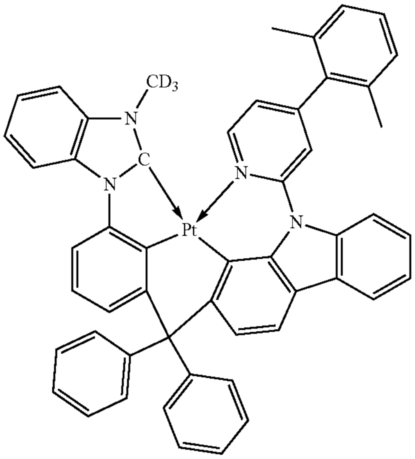
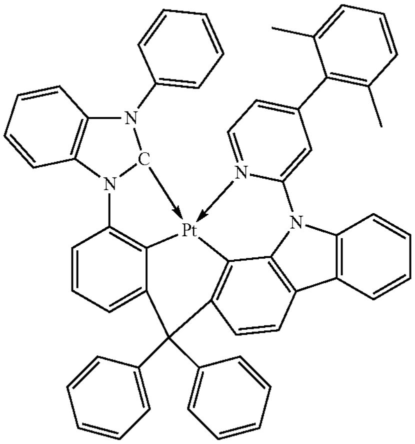
-continued
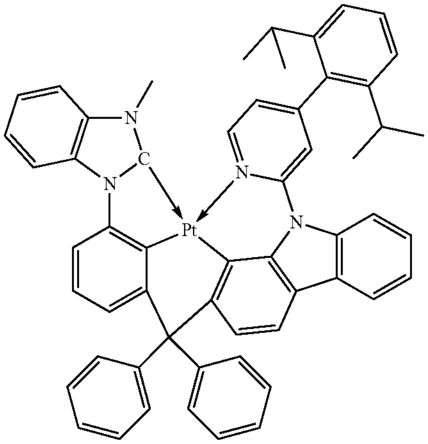
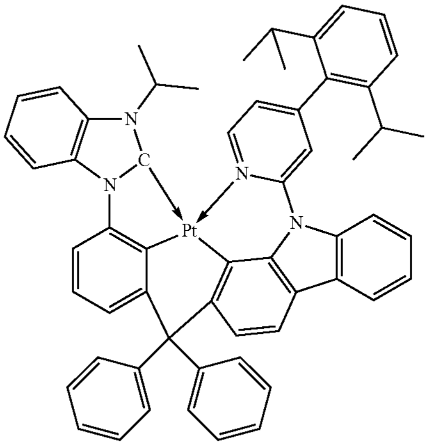
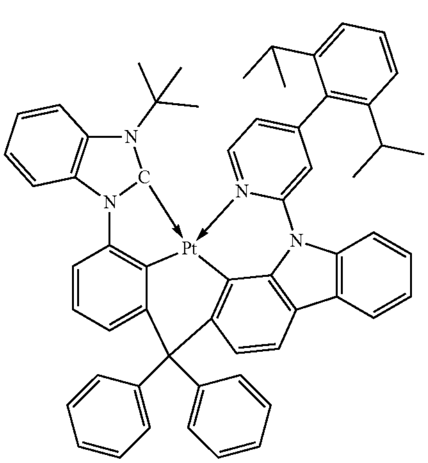

-continued
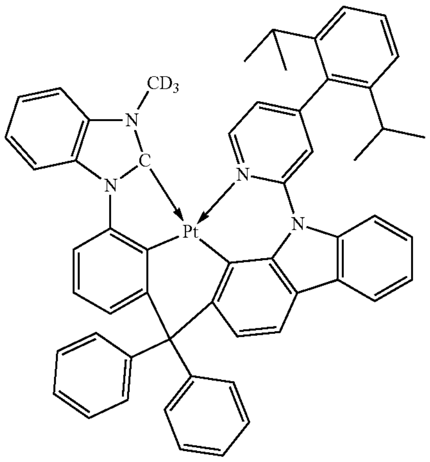
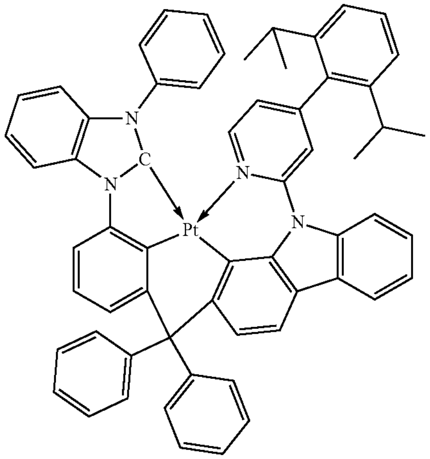
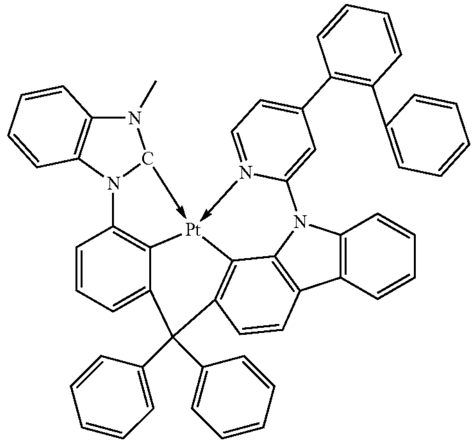
-continued
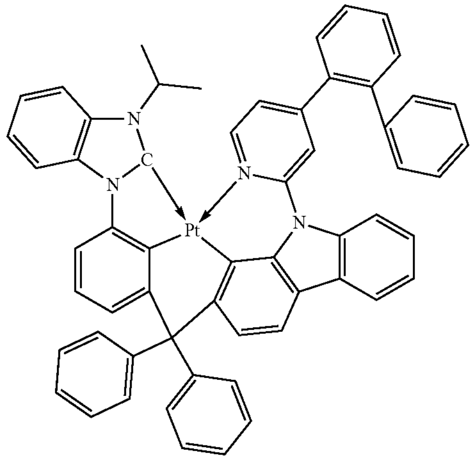
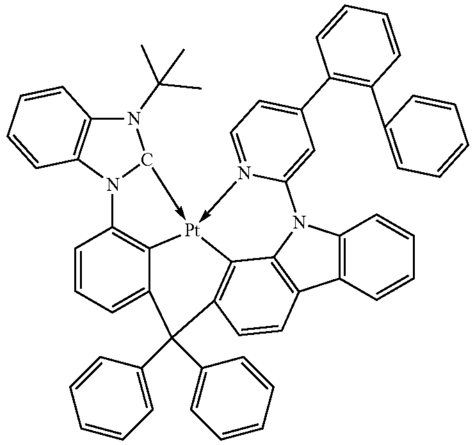
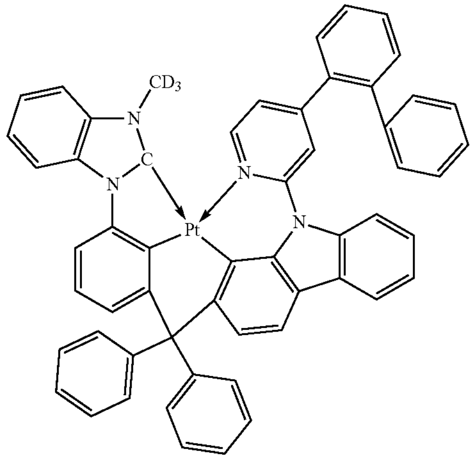

-continued
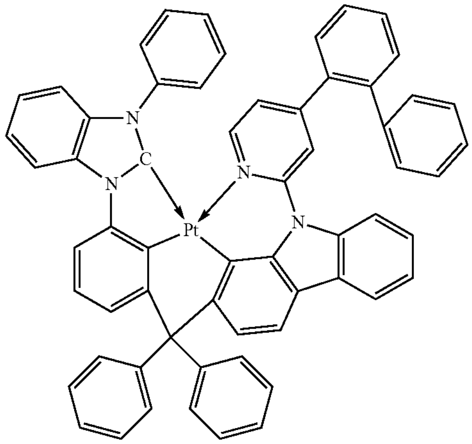
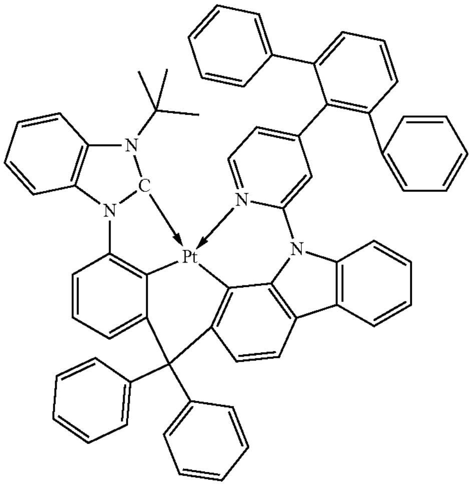
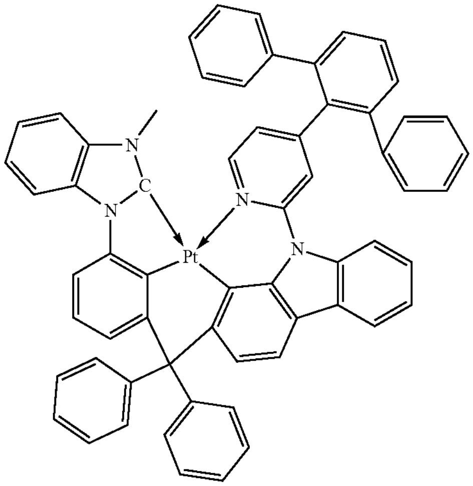
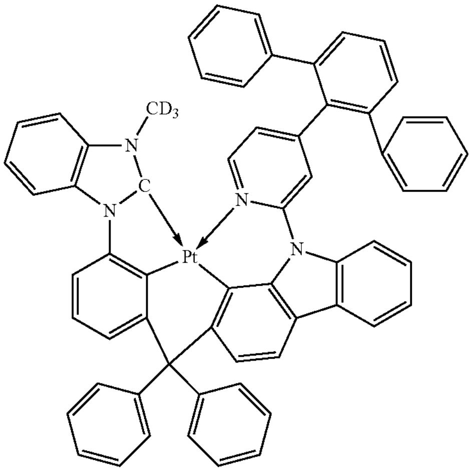
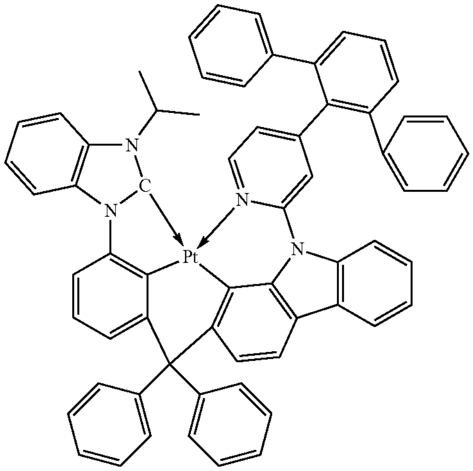
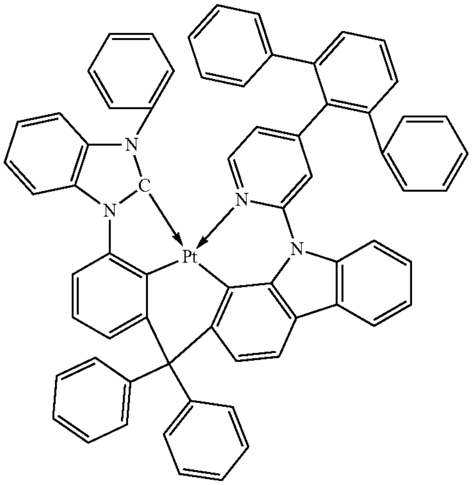
-continued -continued
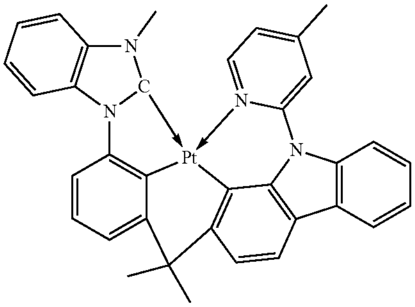
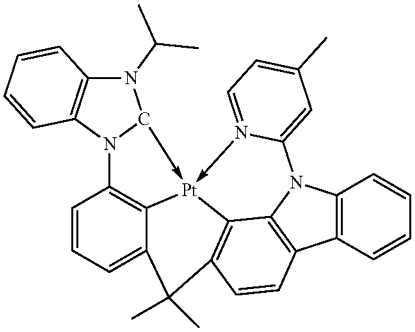
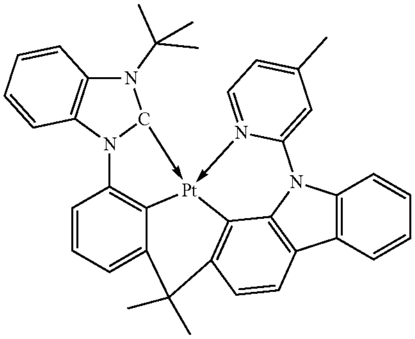
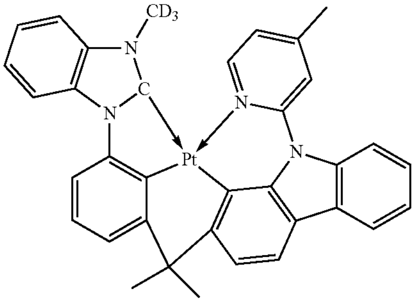
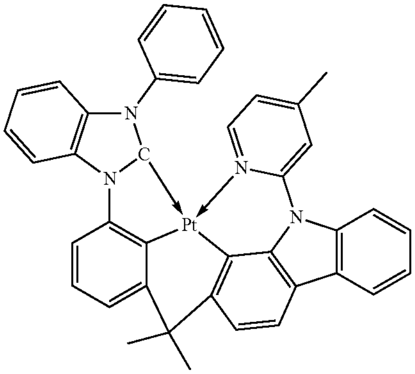
-continued
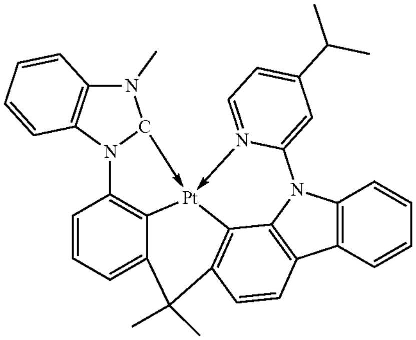
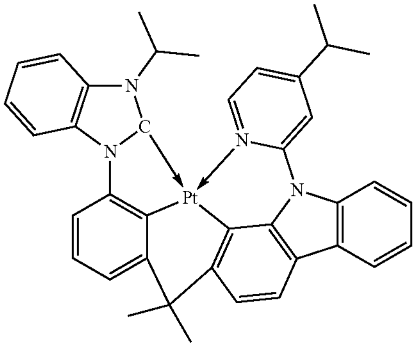
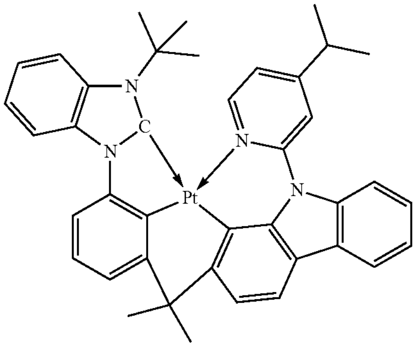
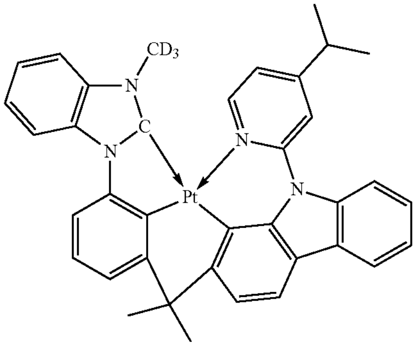

-continued
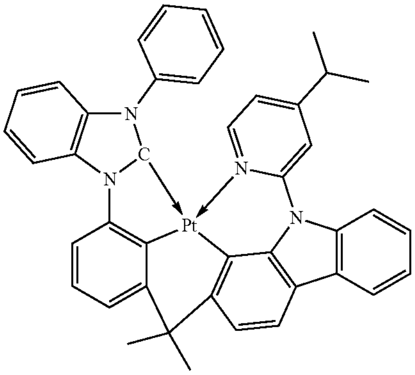
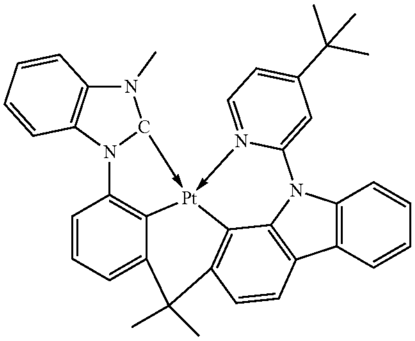
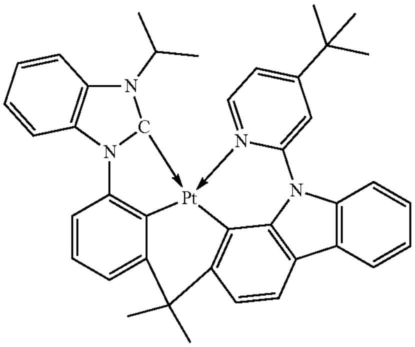
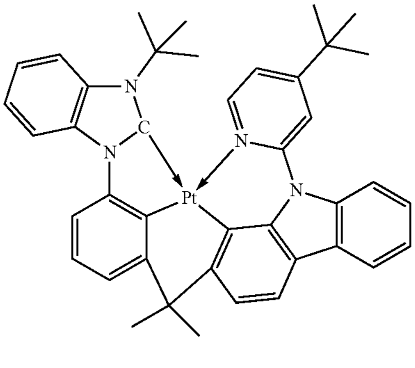
-continued
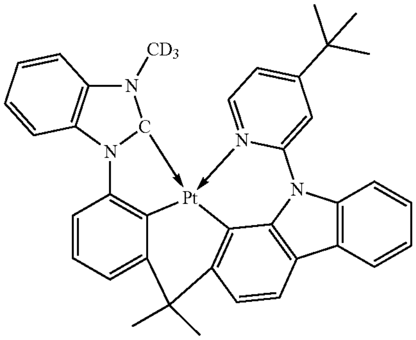
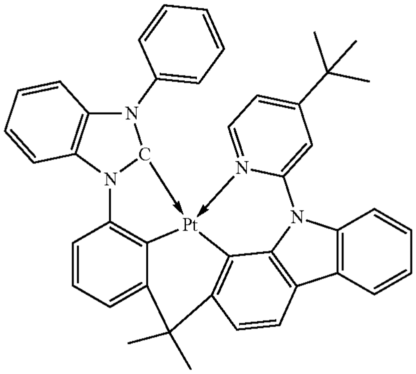
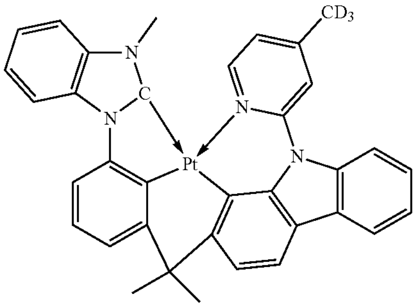
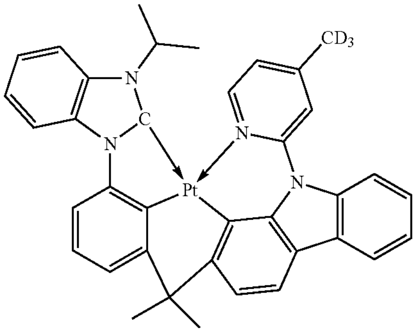
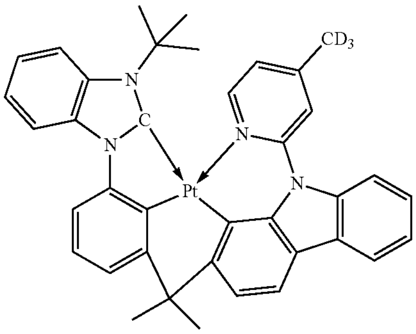

-continued
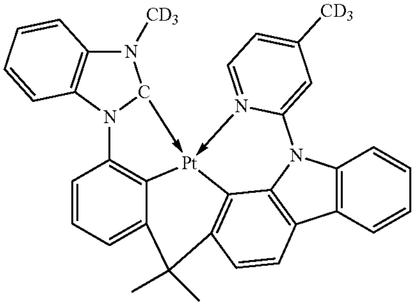
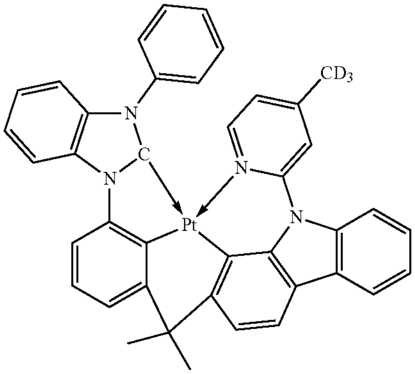
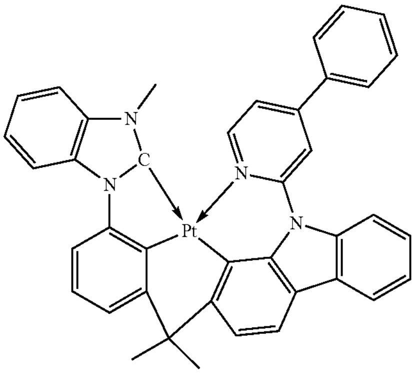
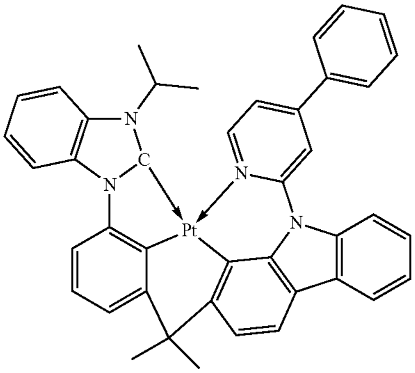
-continued
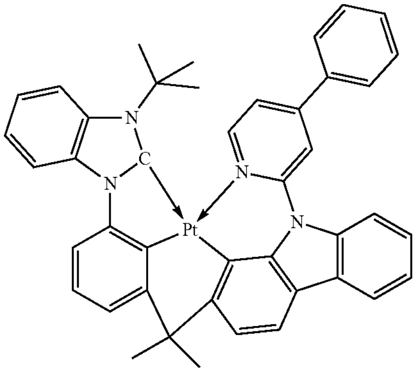
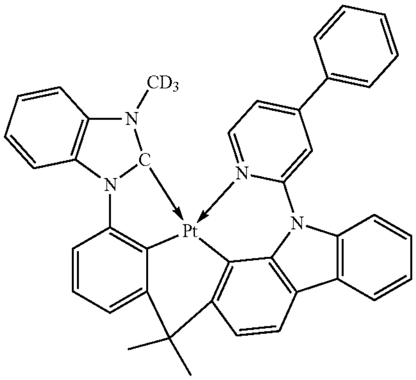
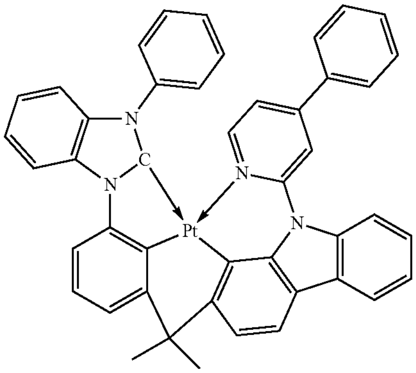
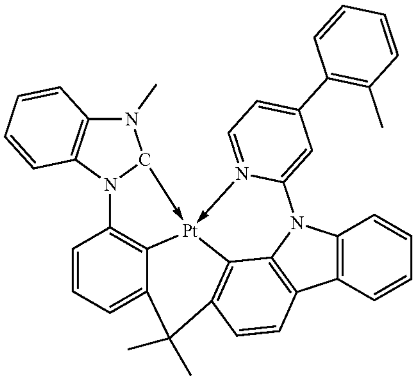

-continued
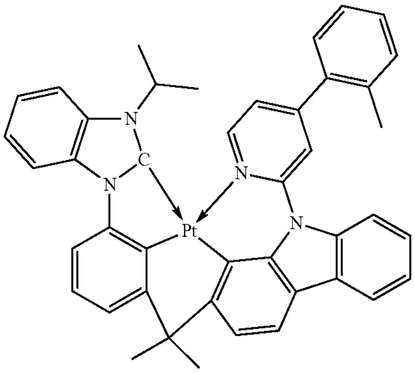
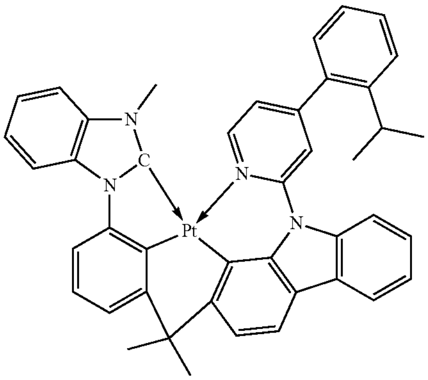
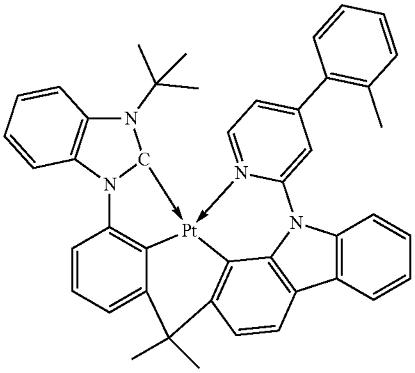
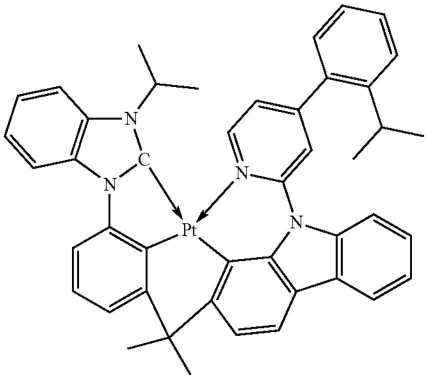
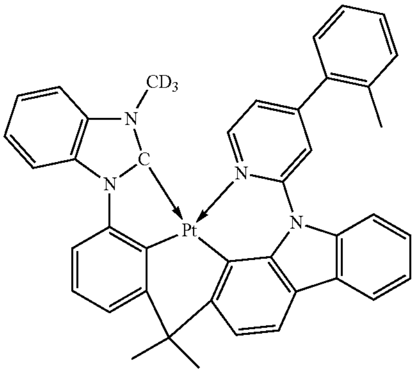
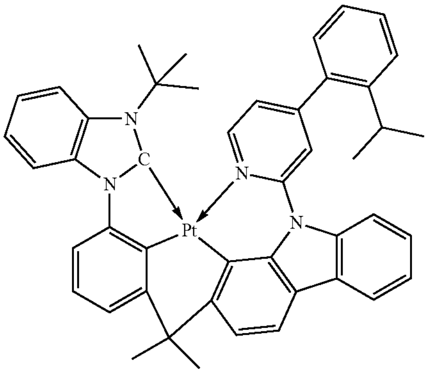
-continued
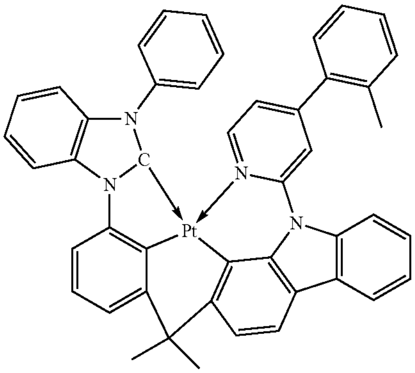
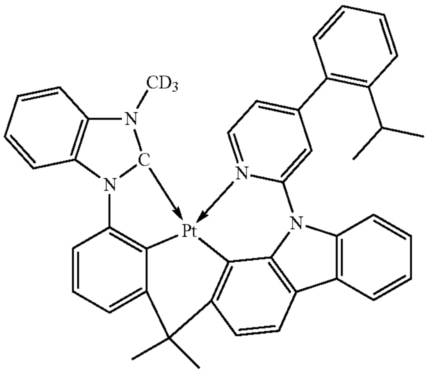

-continued
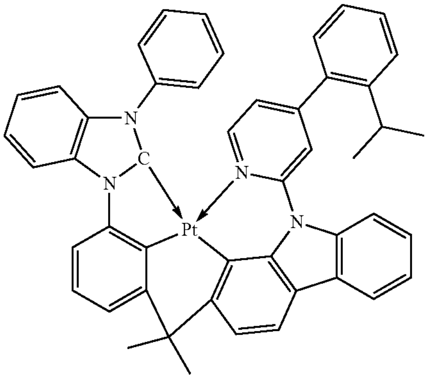
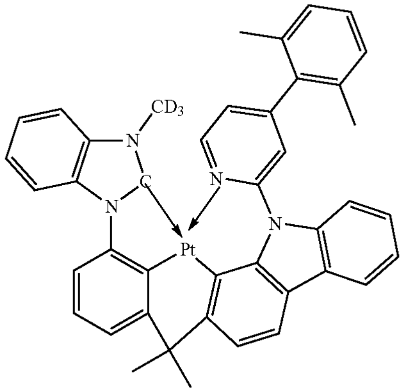
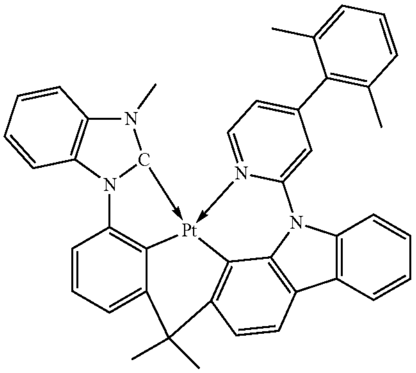
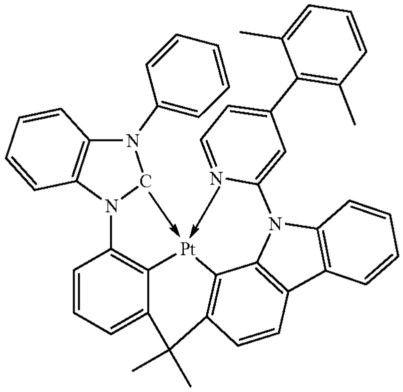
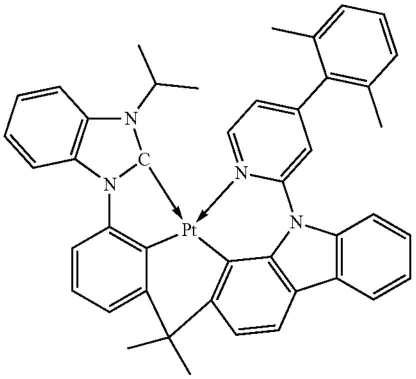
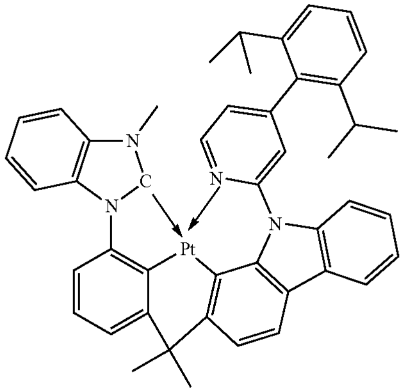
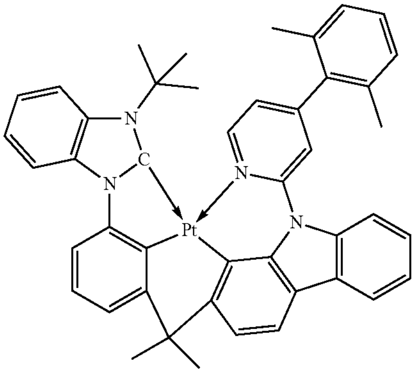
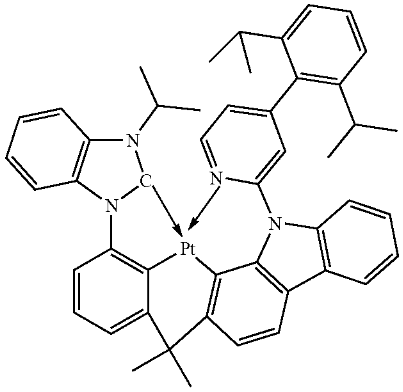

-continued
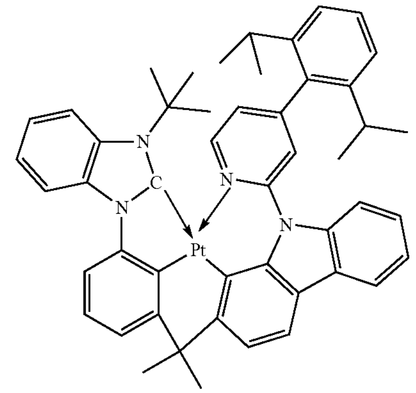
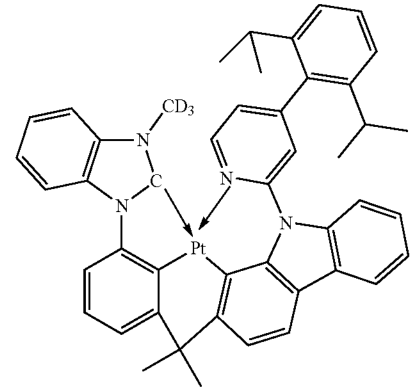
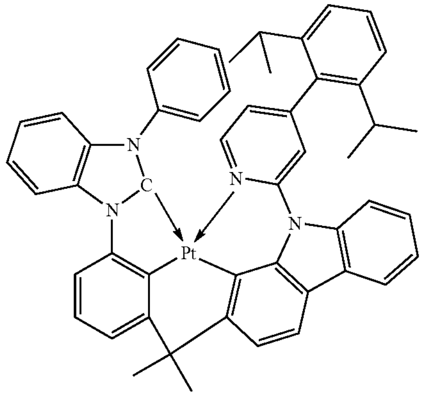
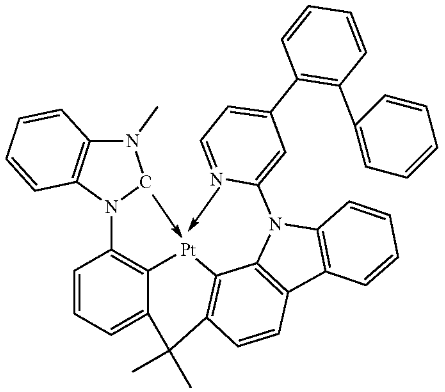
-continued
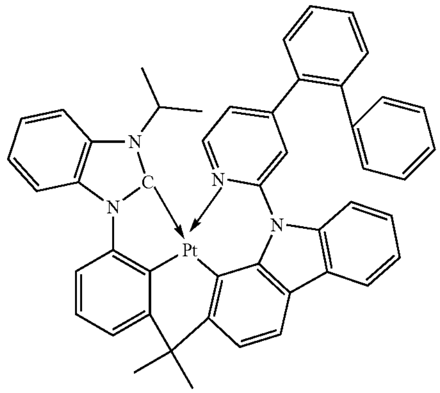
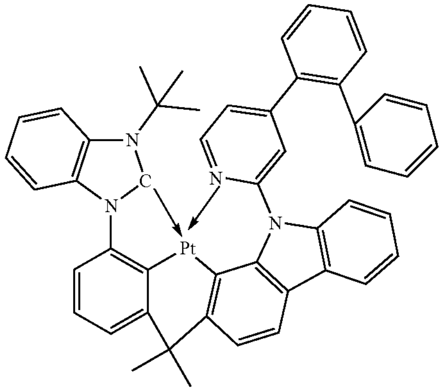
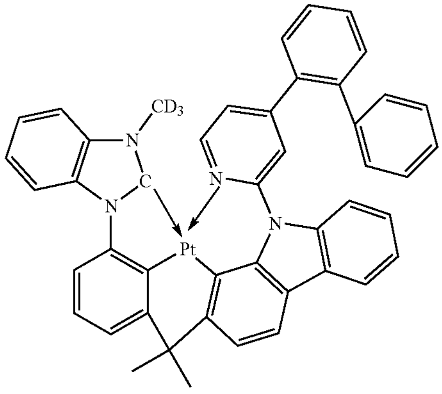
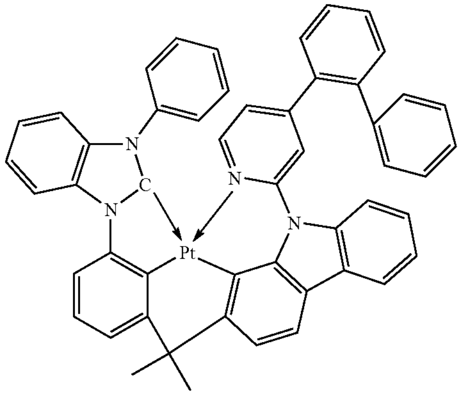

-continued
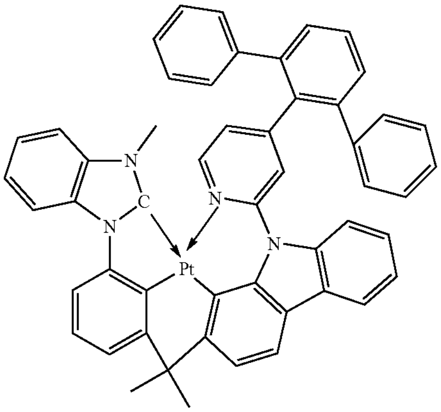
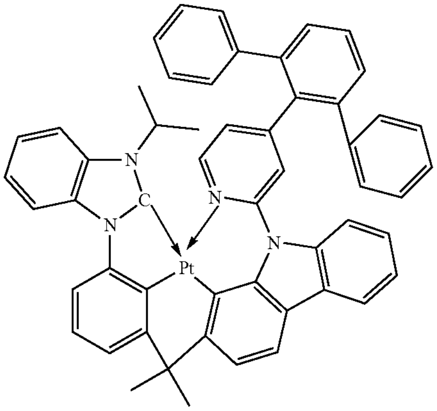
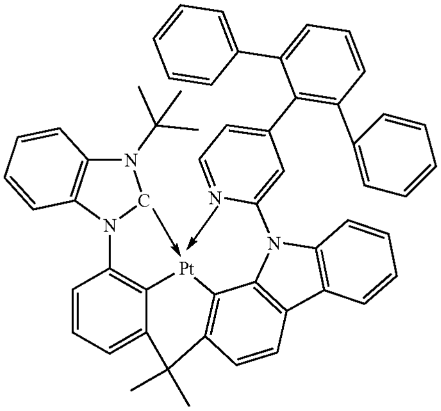
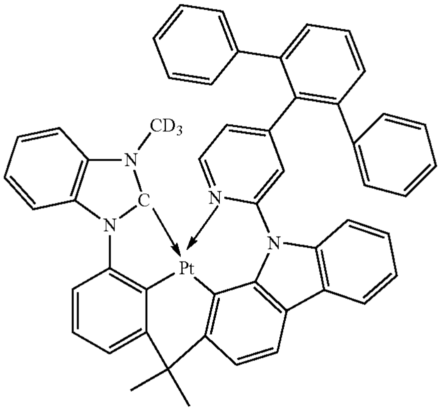
-continued
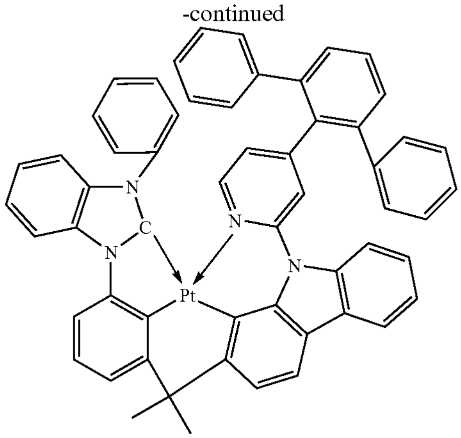
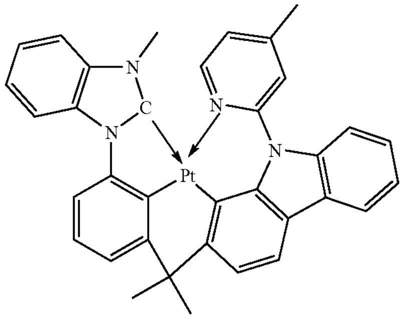
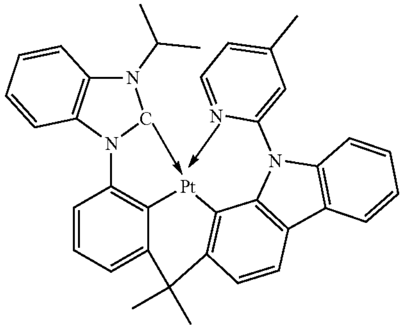
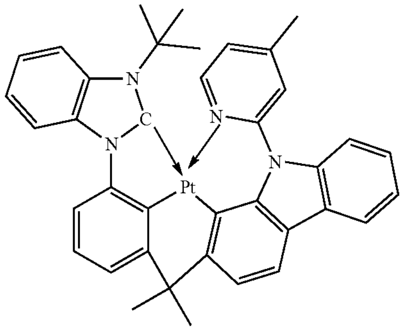
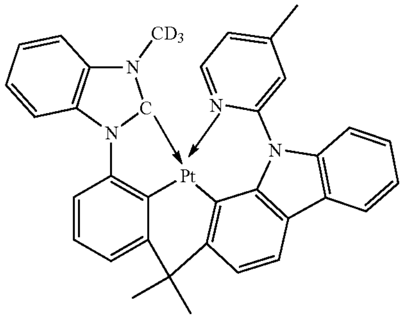

-continued
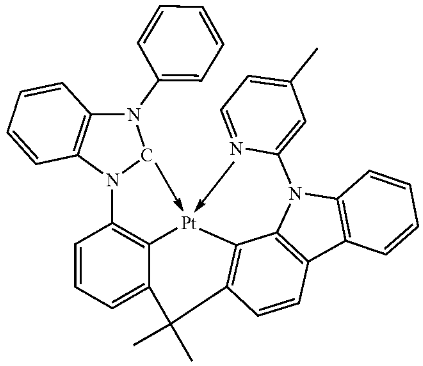
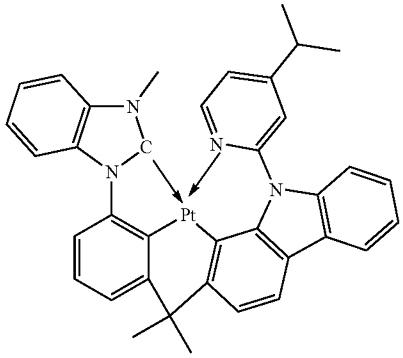
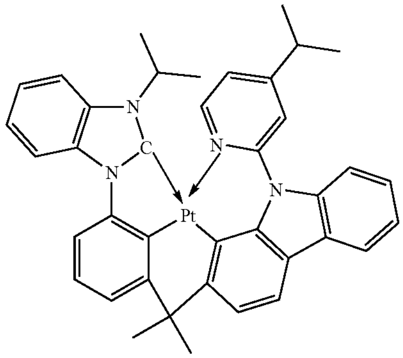
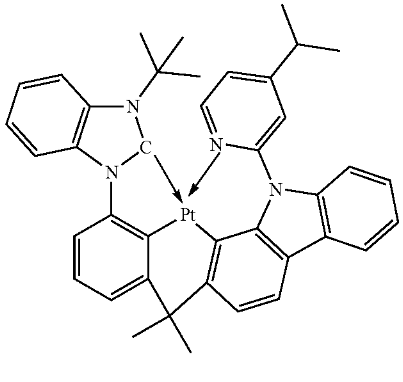
-continued
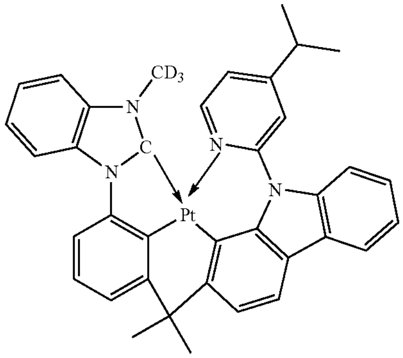
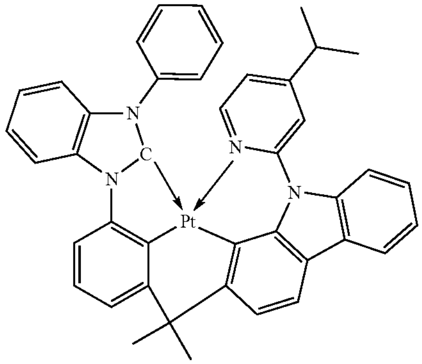
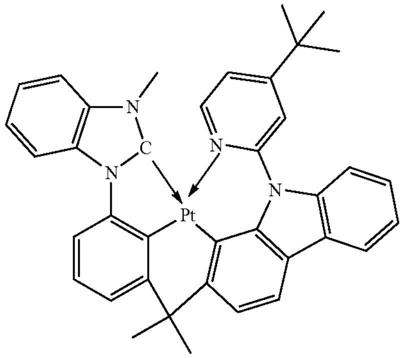
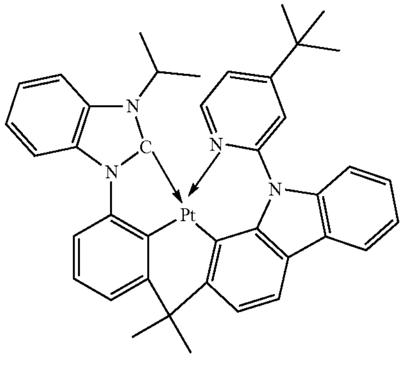

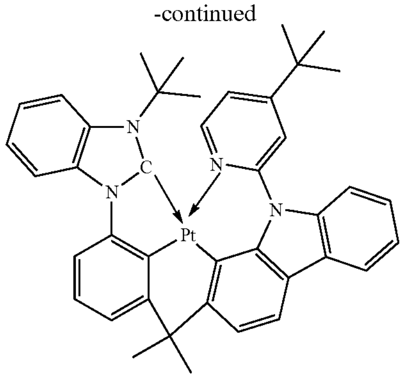
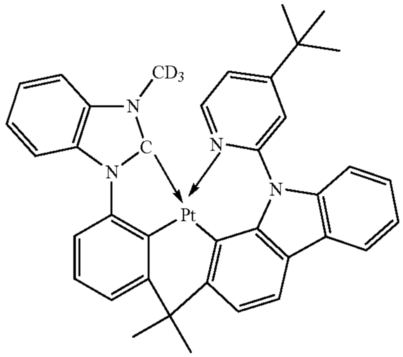
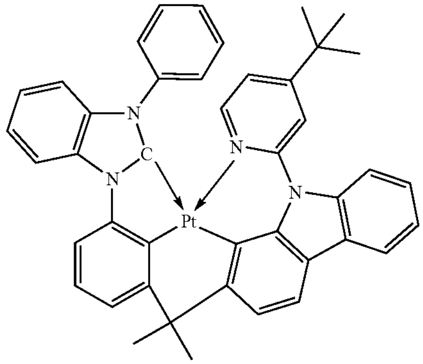
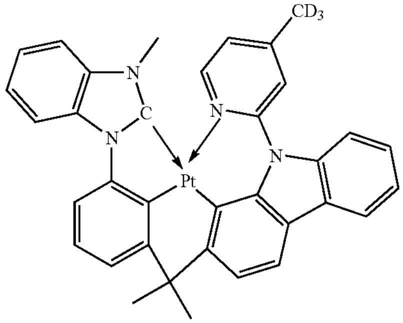
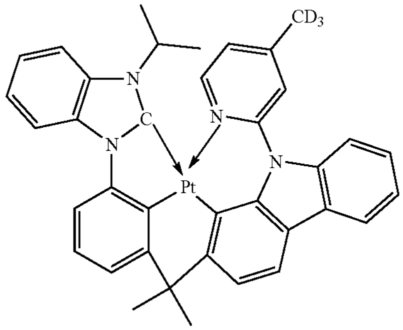
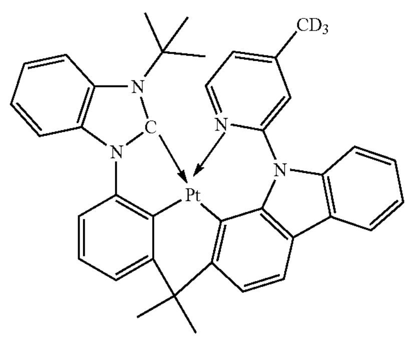
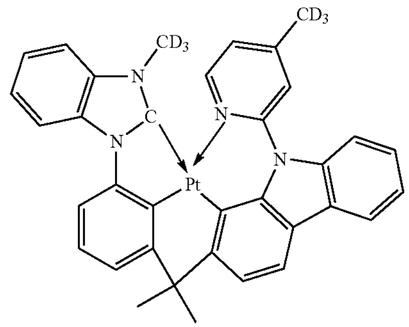
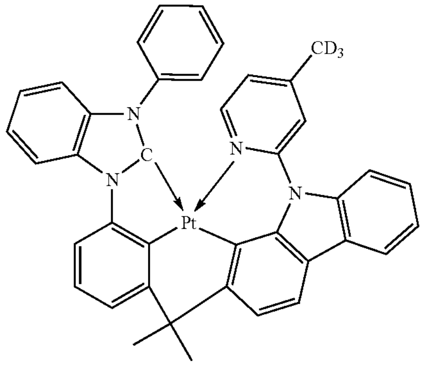
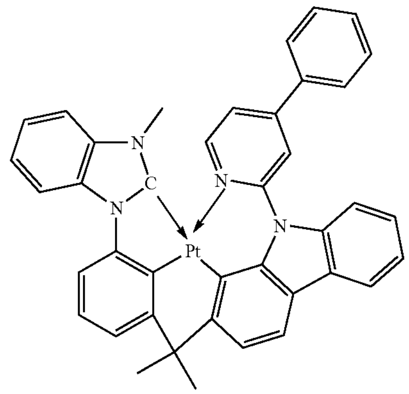

-continued
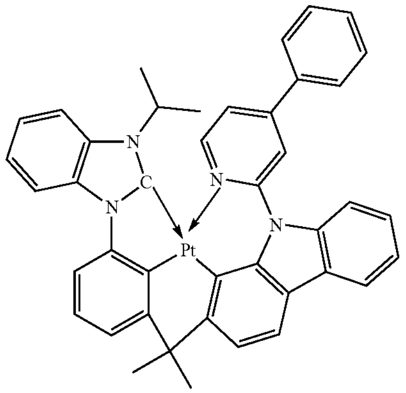
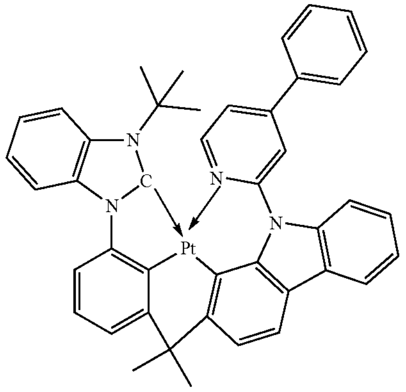
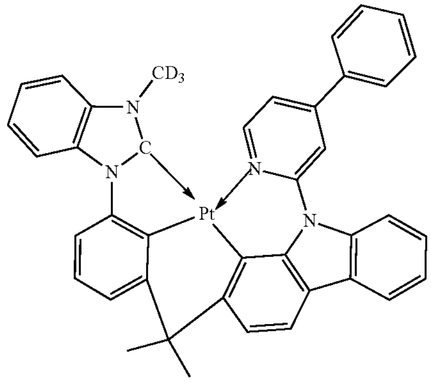
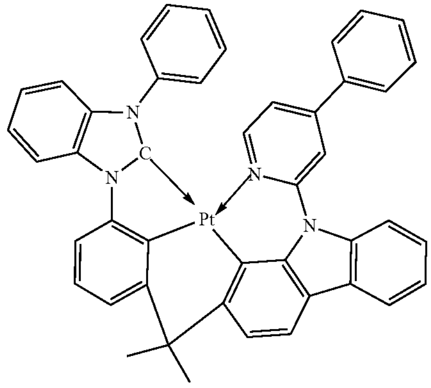
-continued
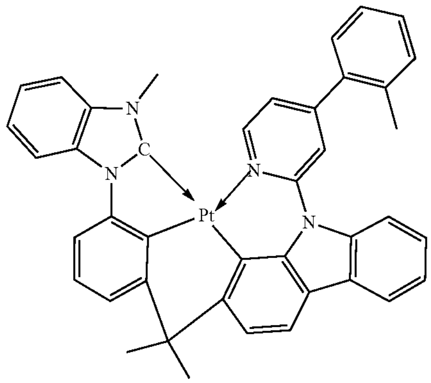
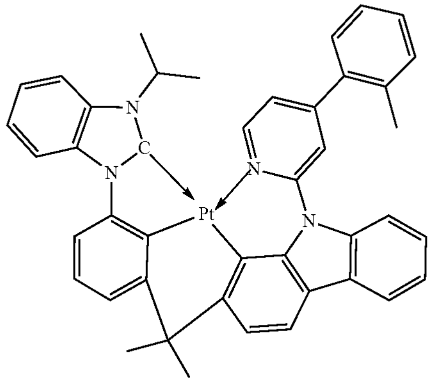
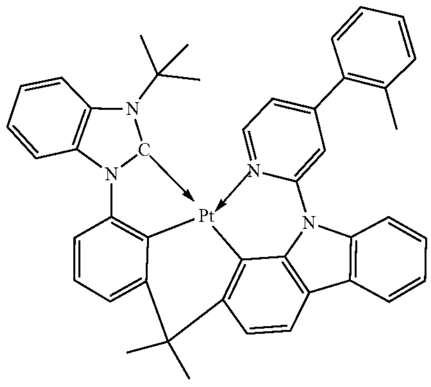
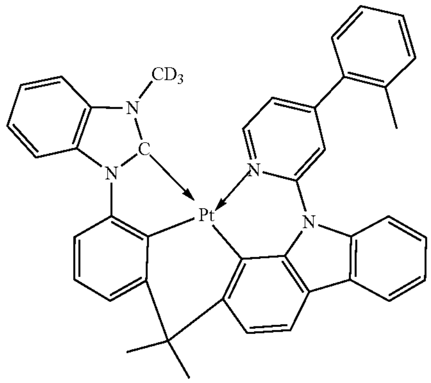

-continued
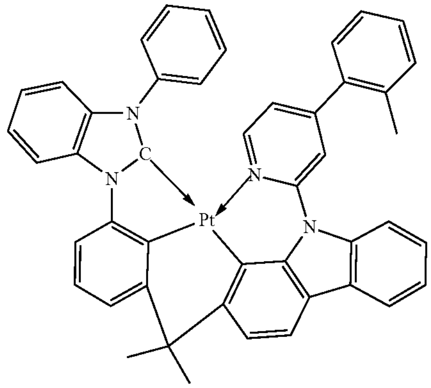
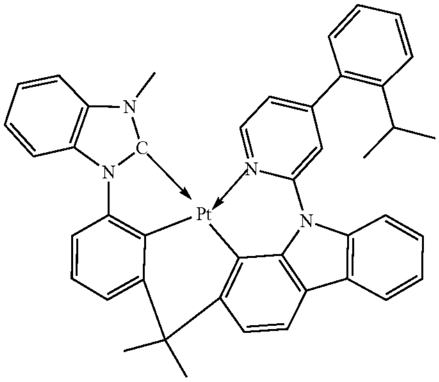
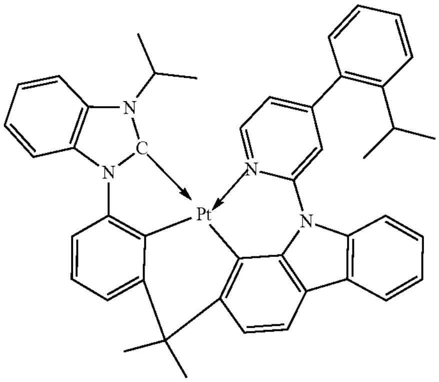
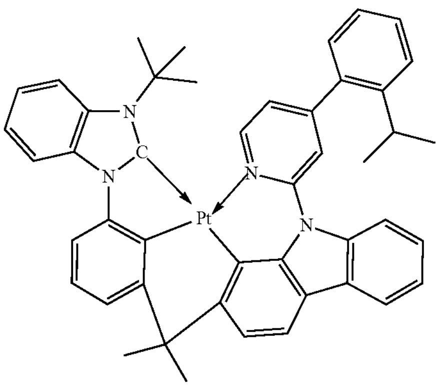
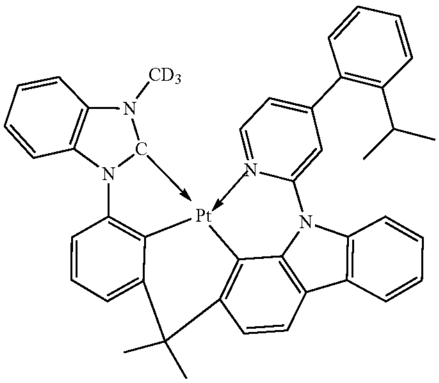
-continued
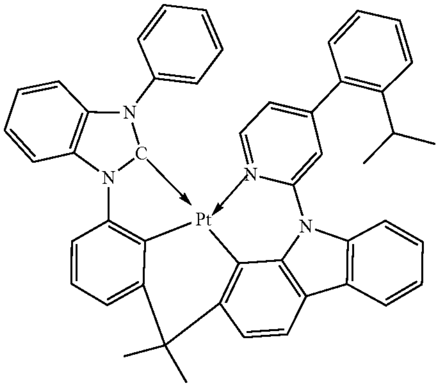
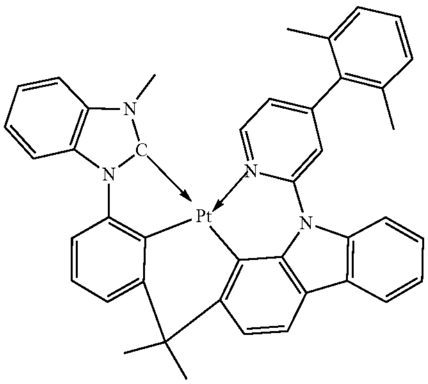
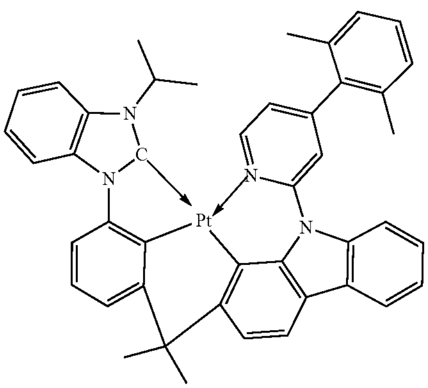

-continued
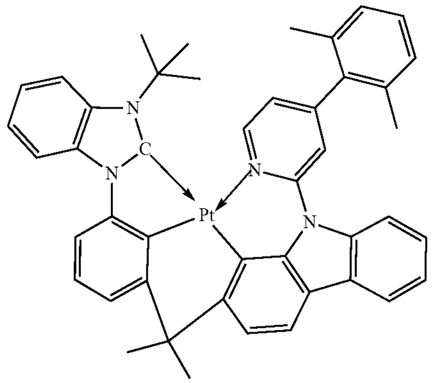
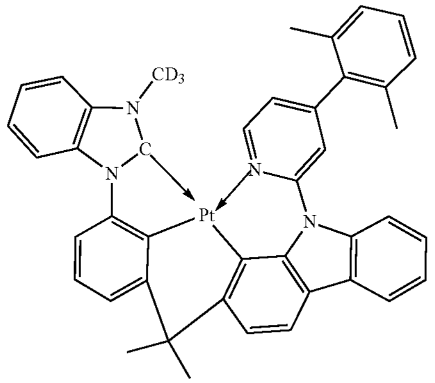
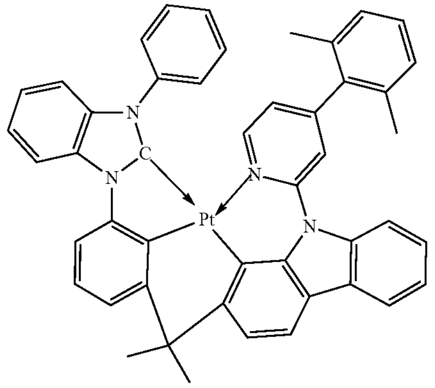
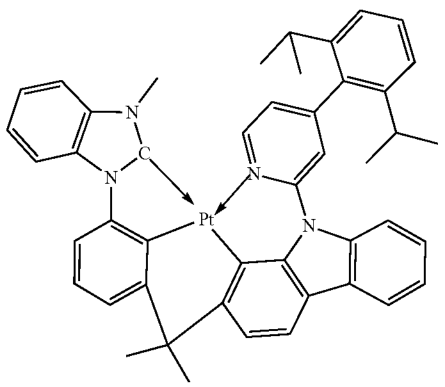
-continued
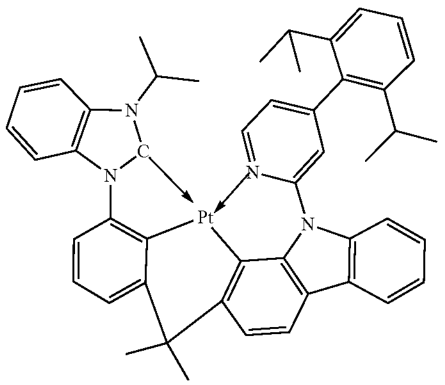
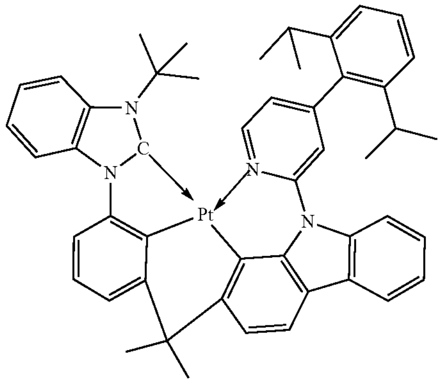
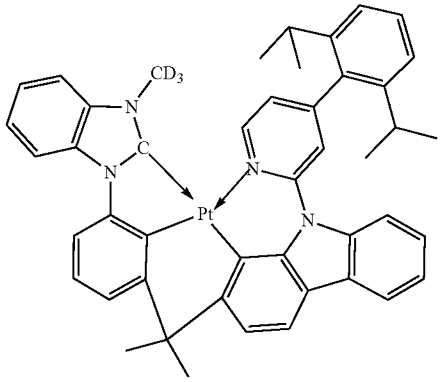
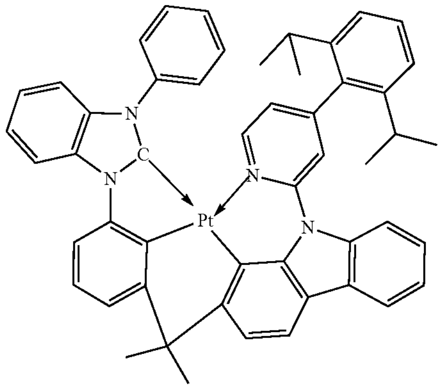

-continued
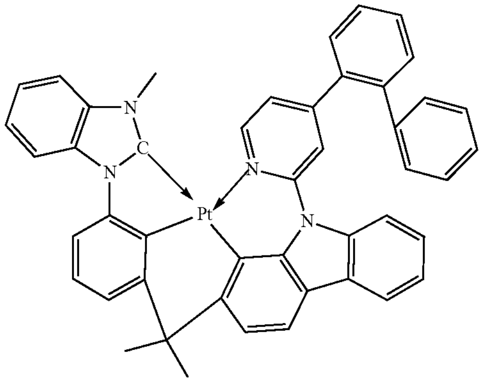
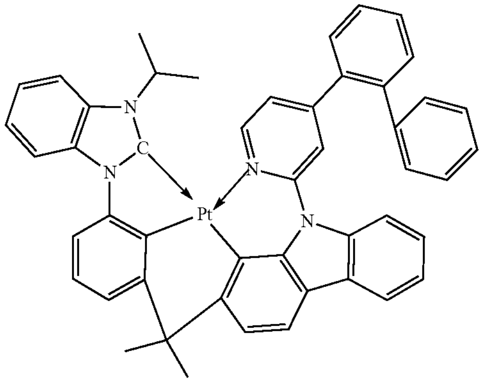
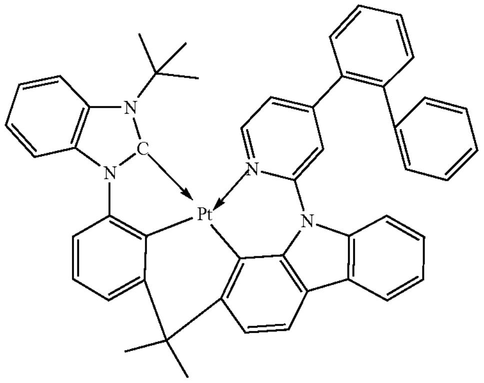
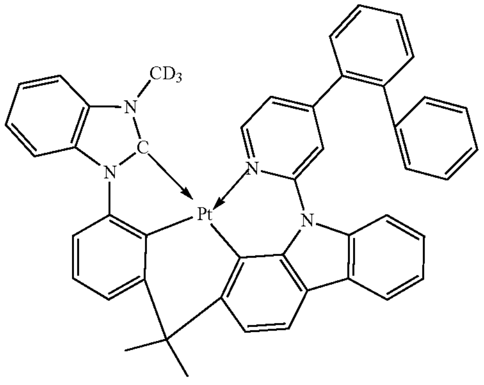
-continued
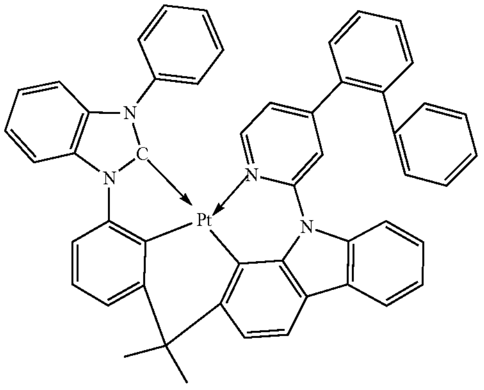
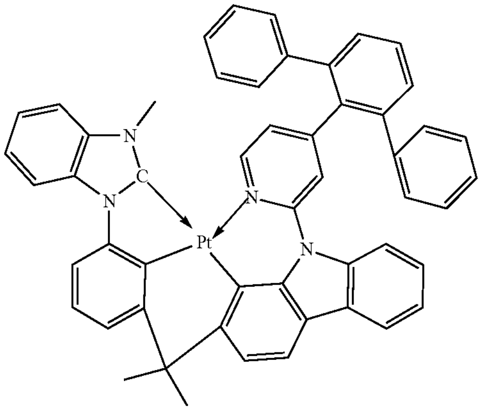
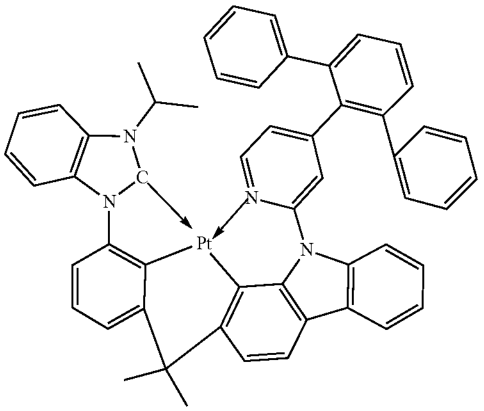
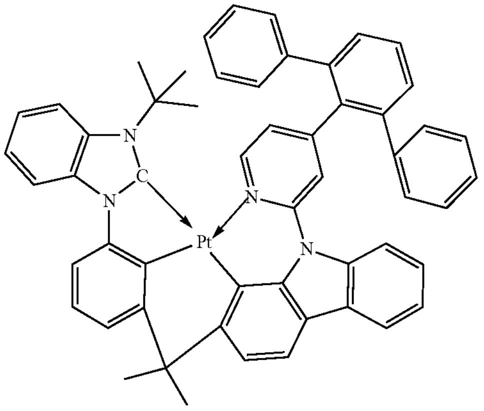

-continued
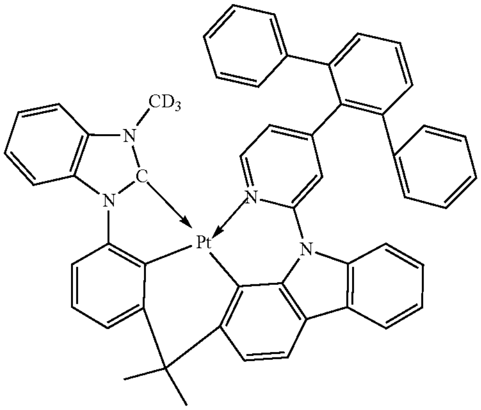
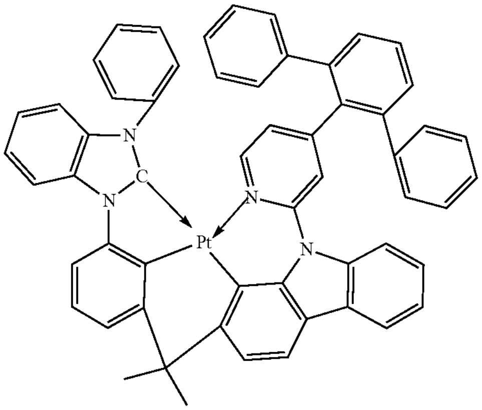
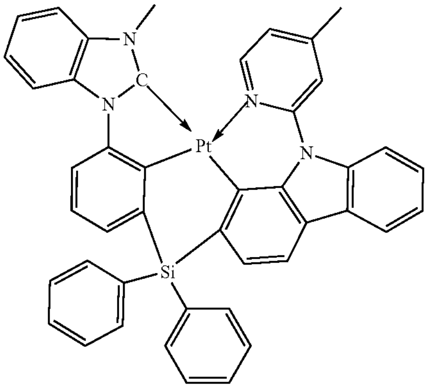
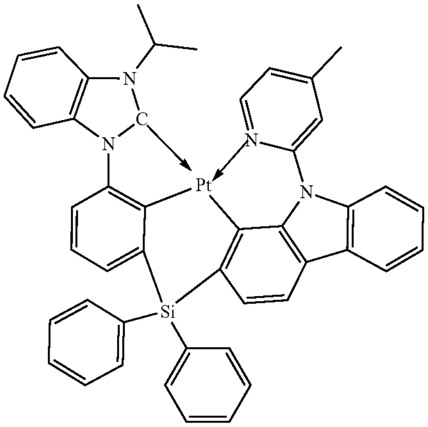
-continued
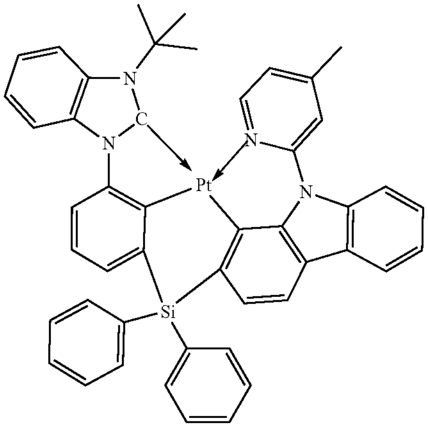
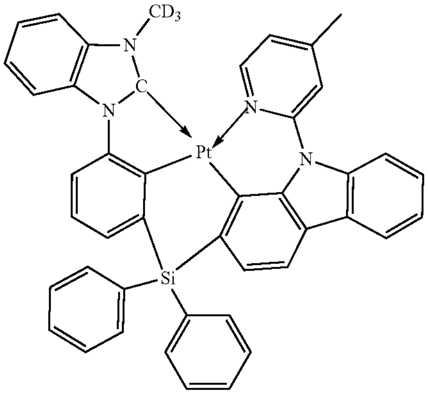
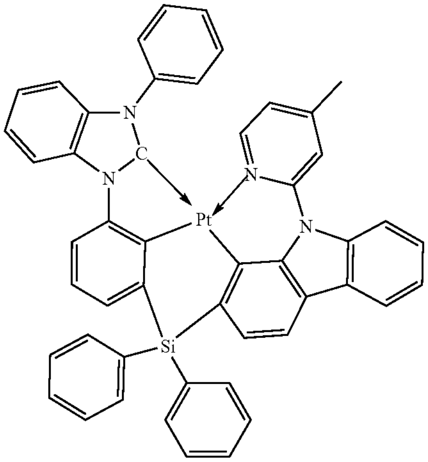
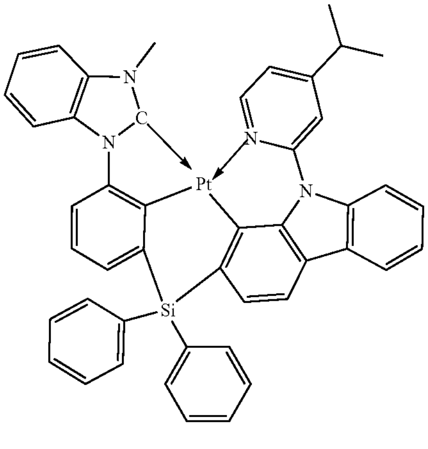

-continued
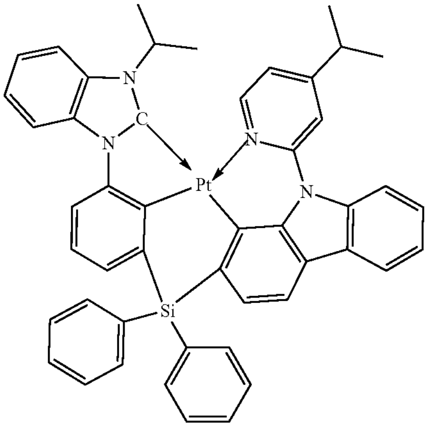
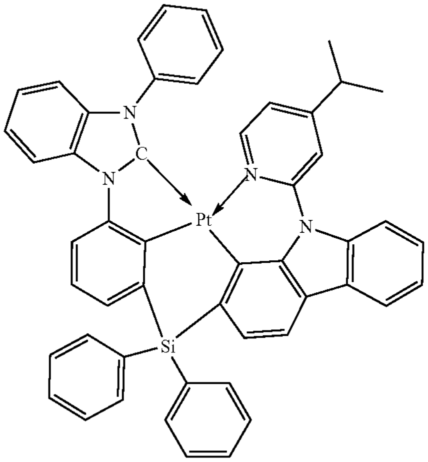
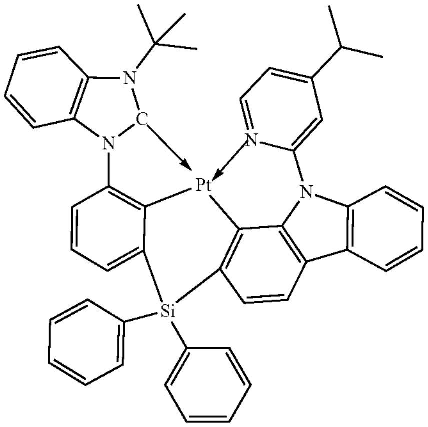
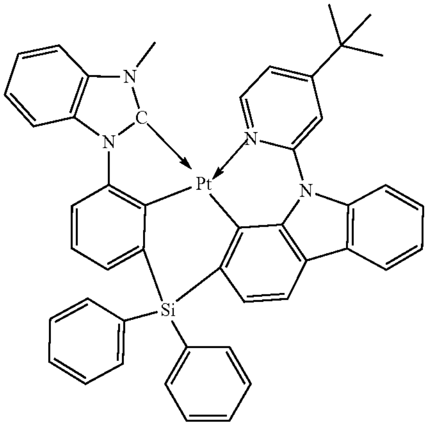
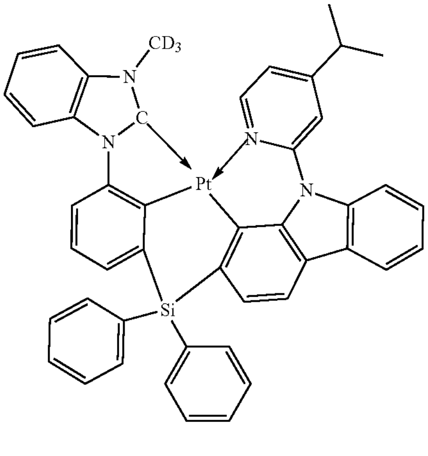
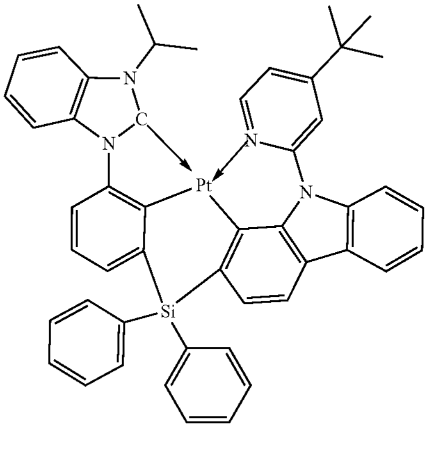

-continued
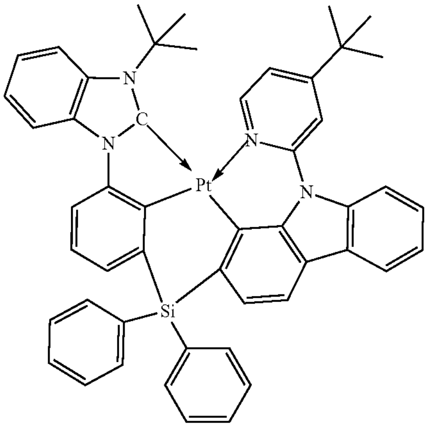
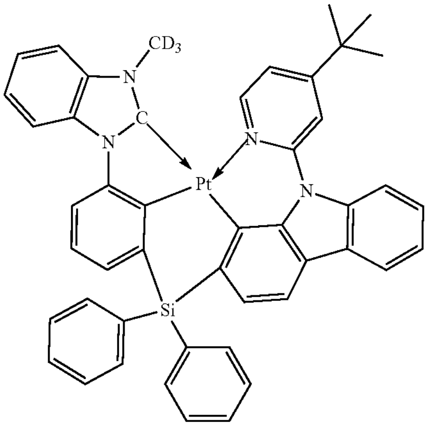
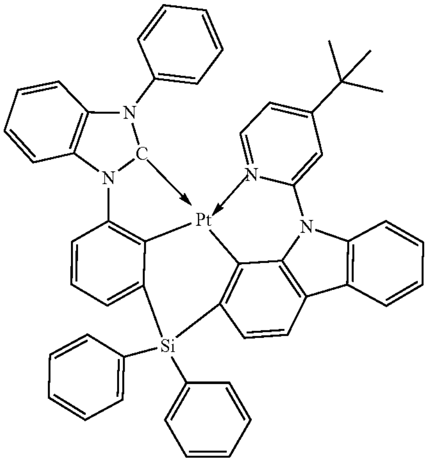
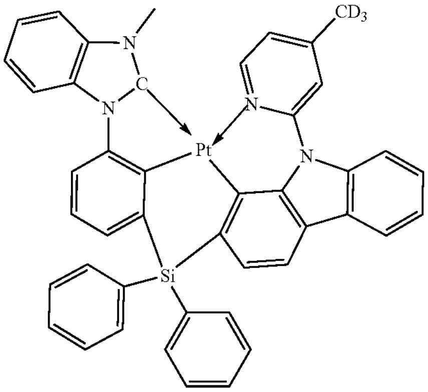
-continued
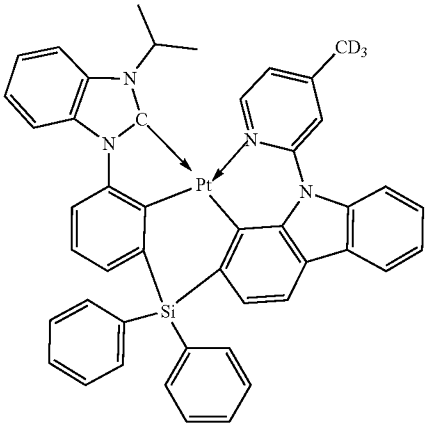
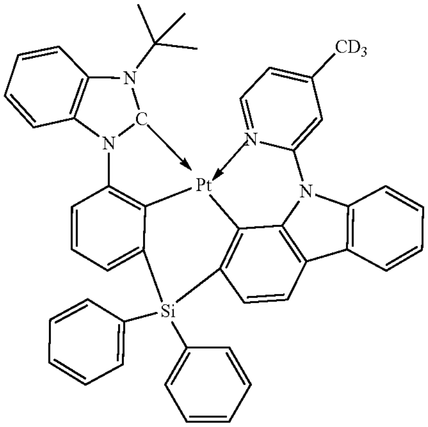
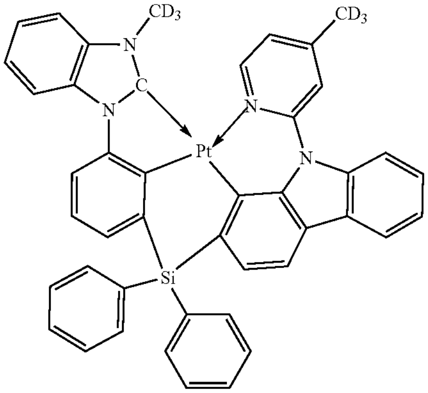
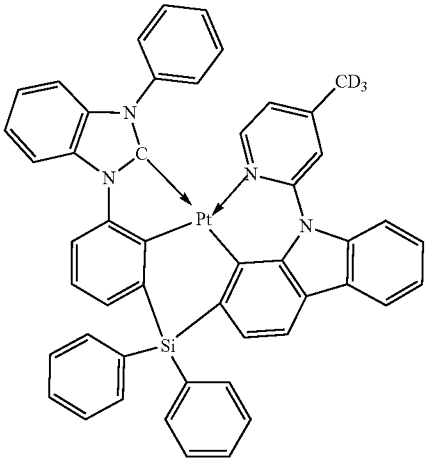

-continued
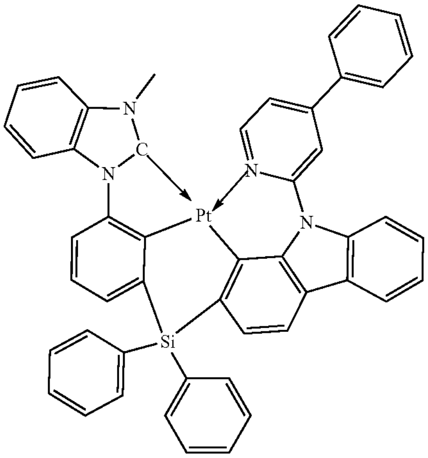
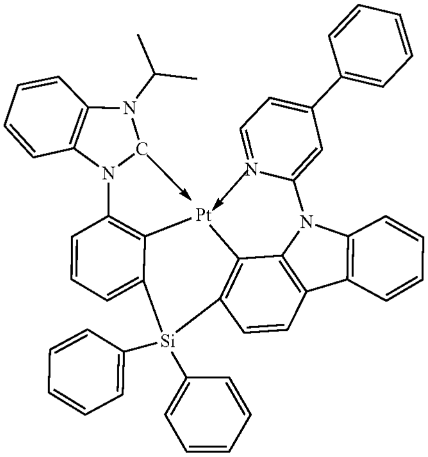
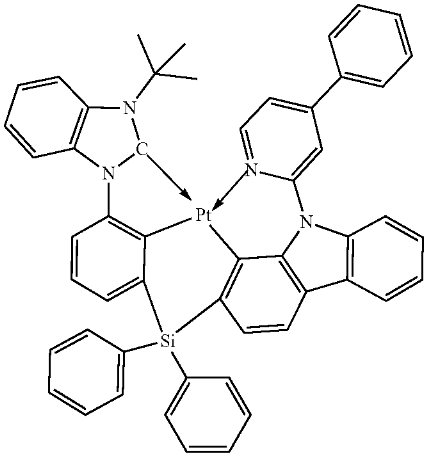
-continued
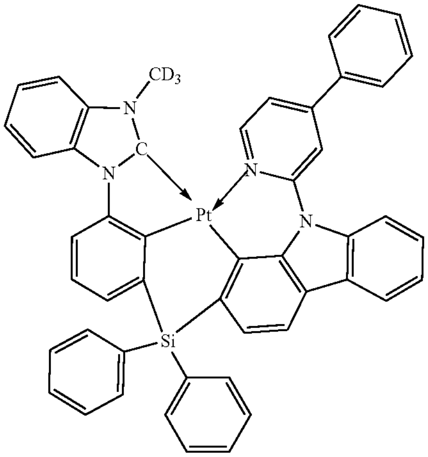
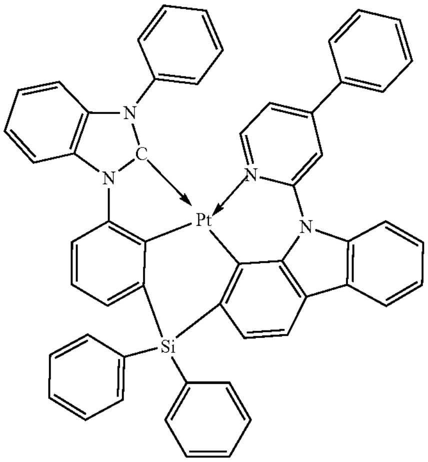
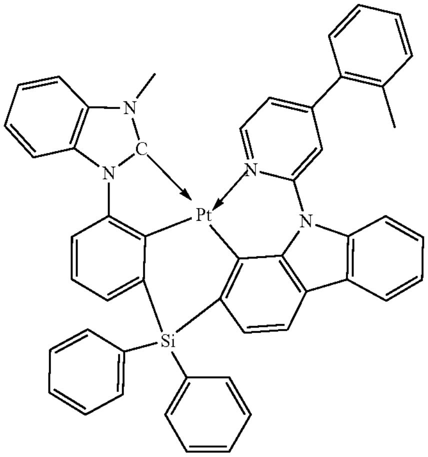

-continued
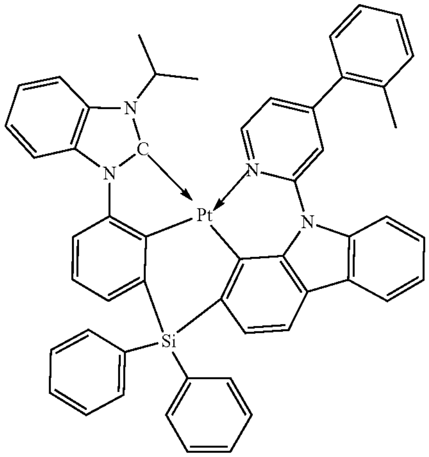
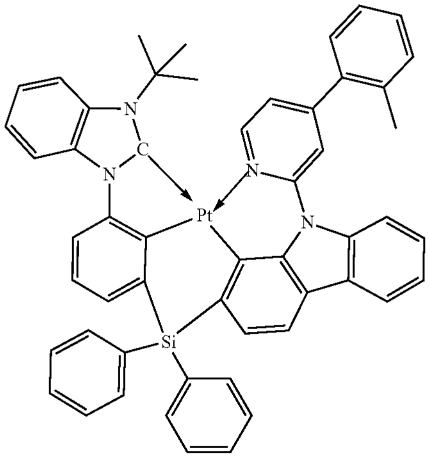
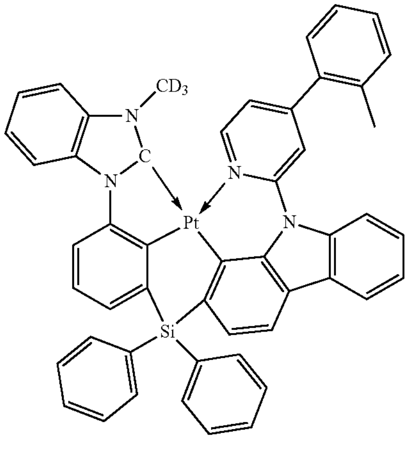
-continued
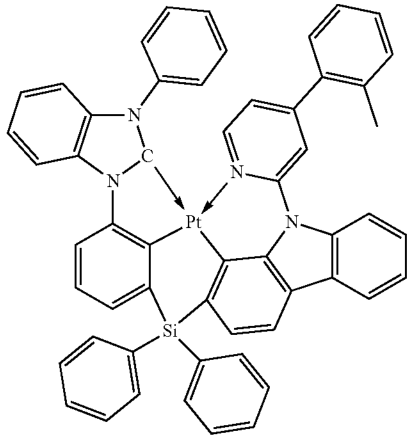
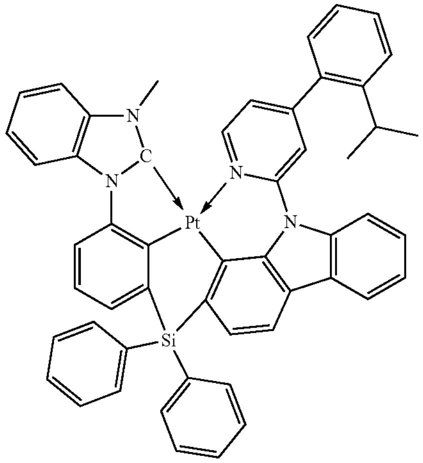
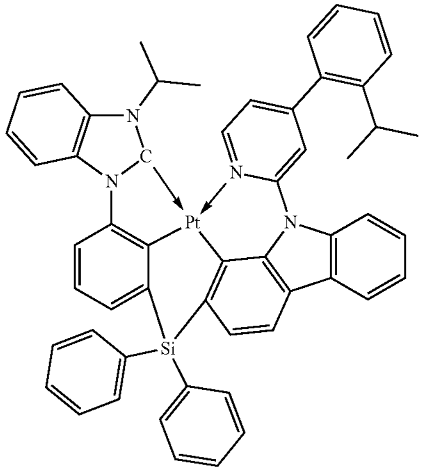

-continued
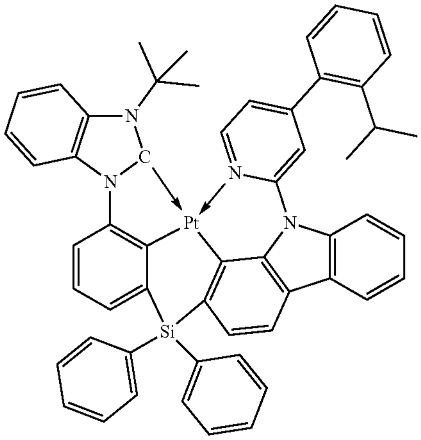
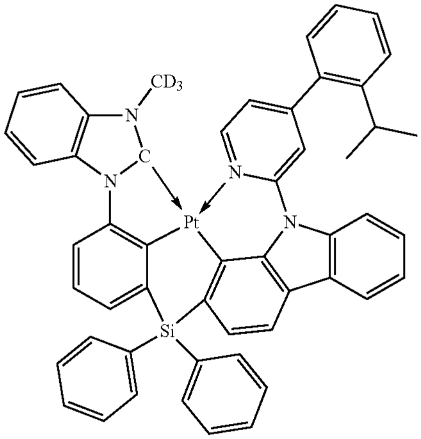
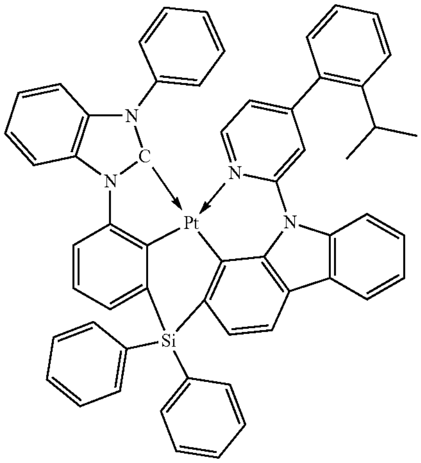
-continued
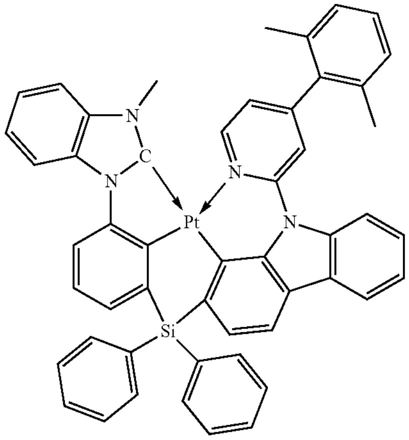
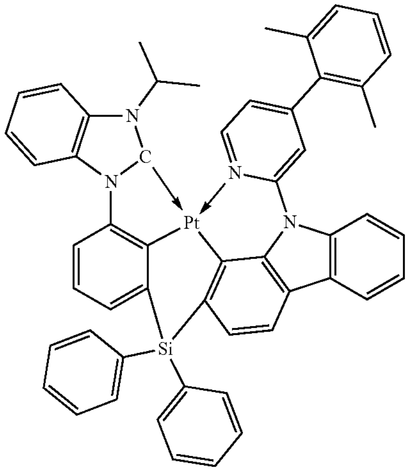
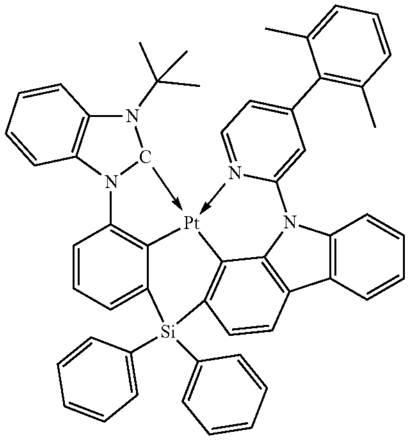

-continued
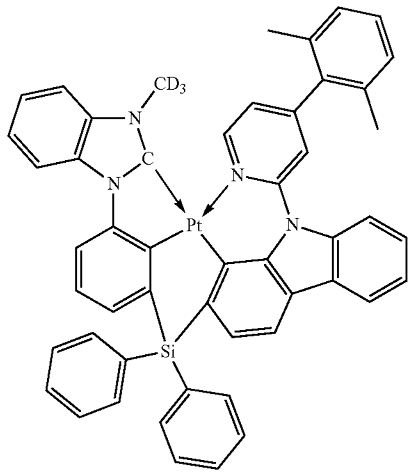
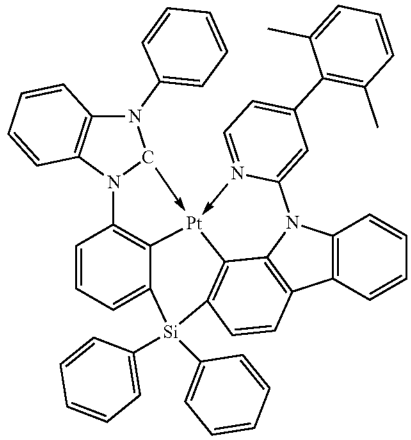
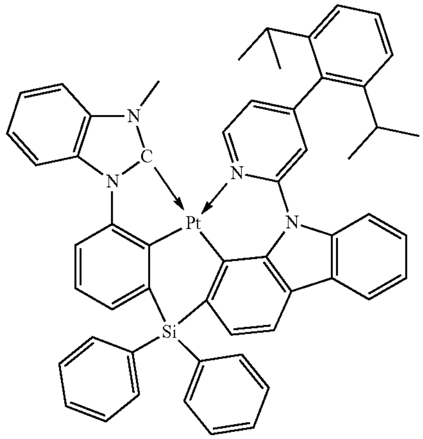
-continued
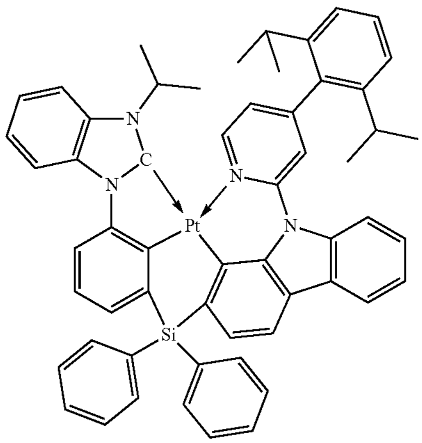
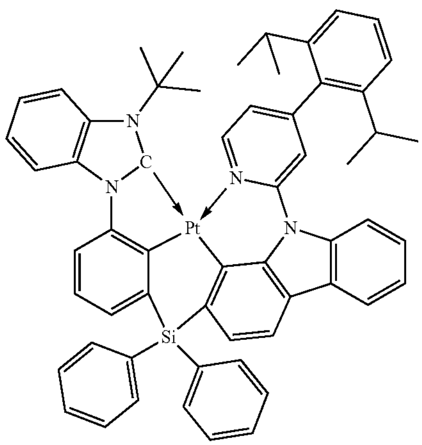
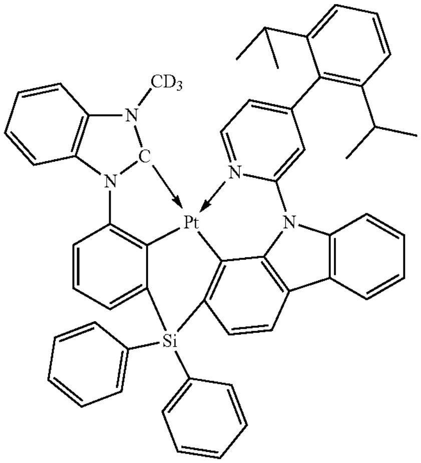

-continued
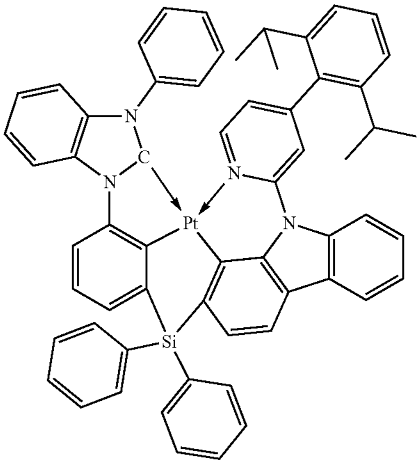
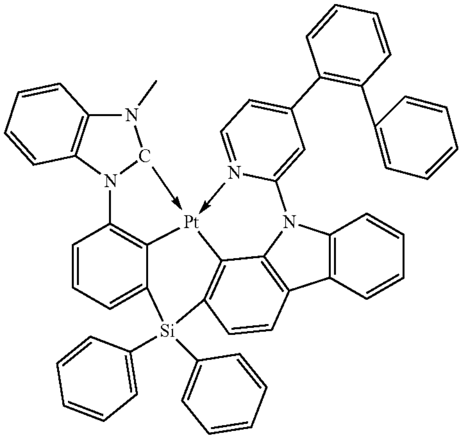
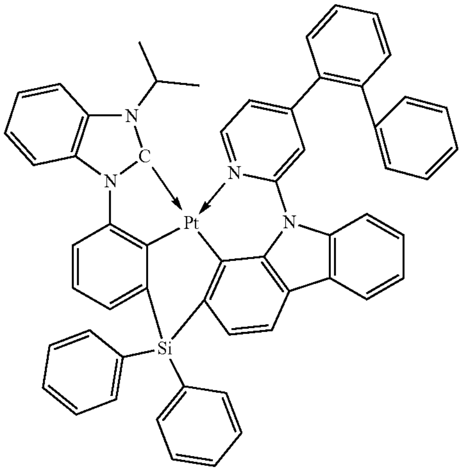
-continued
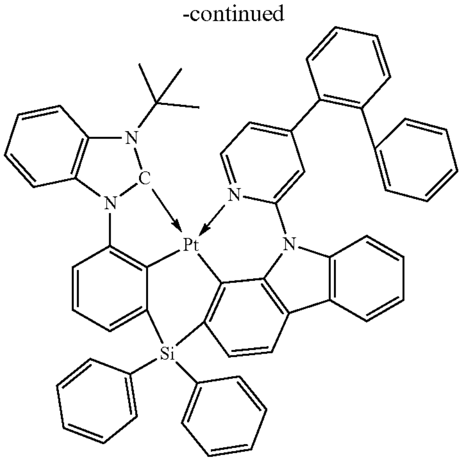
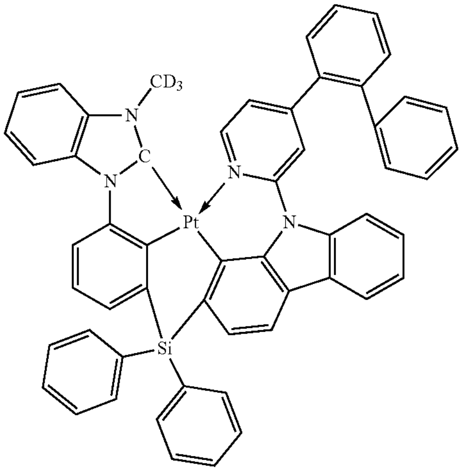
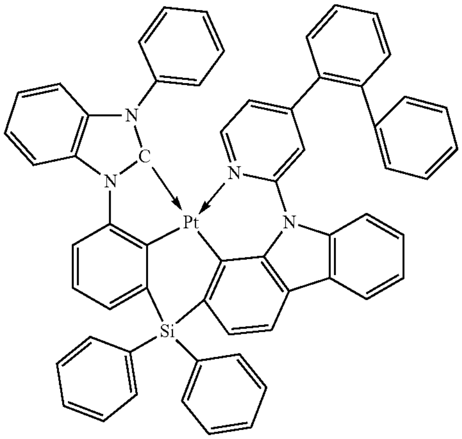

-continued
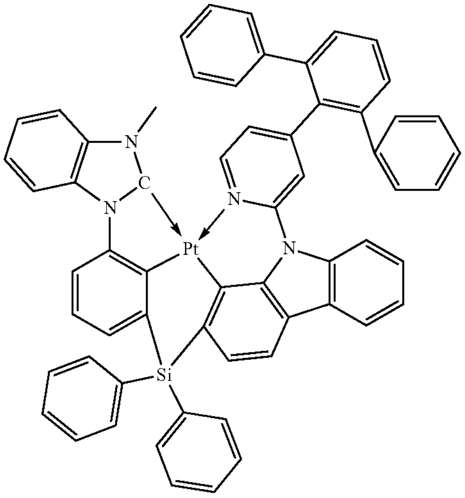
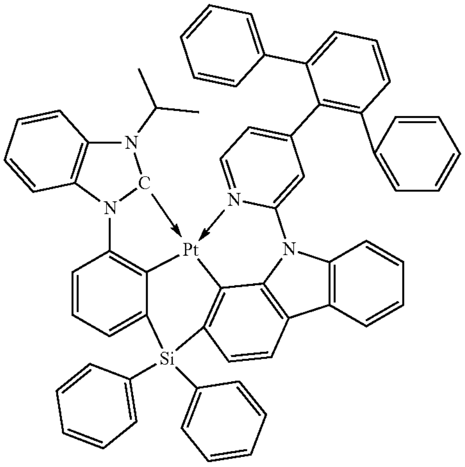
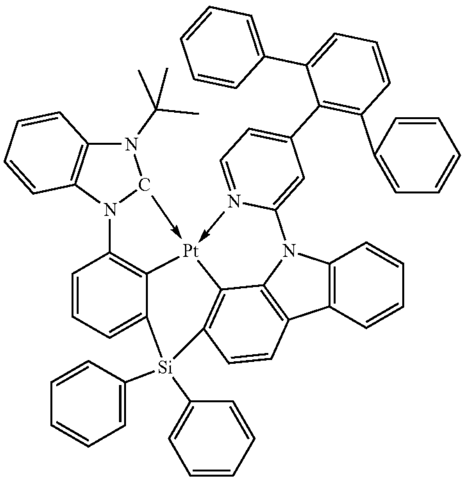
-continued
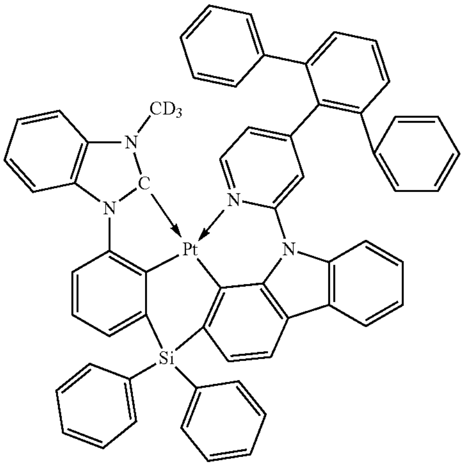
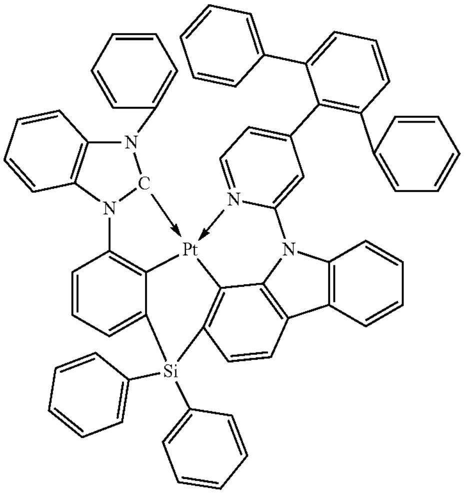
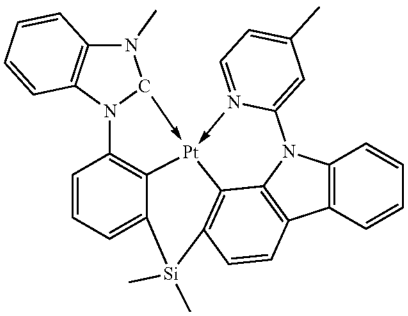
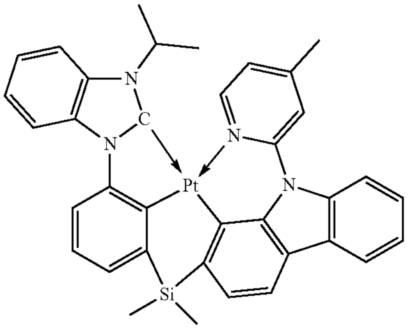

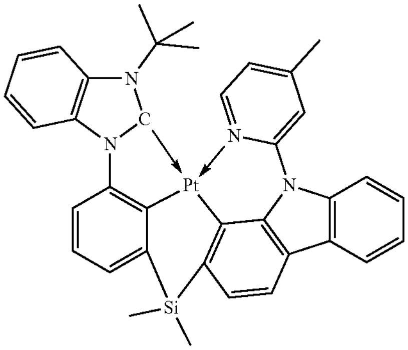
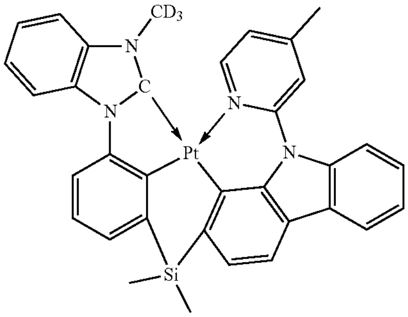
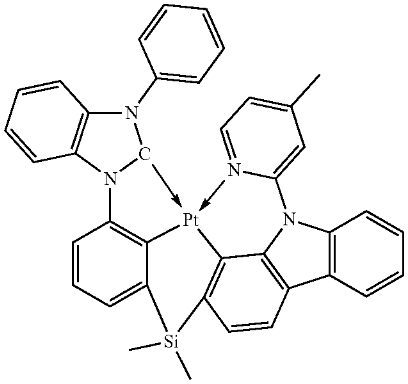
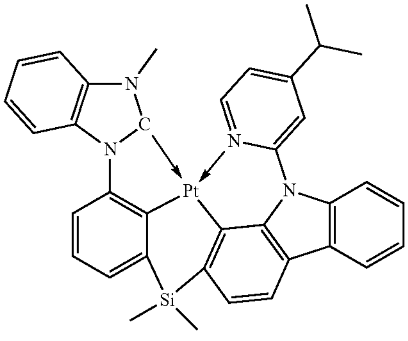
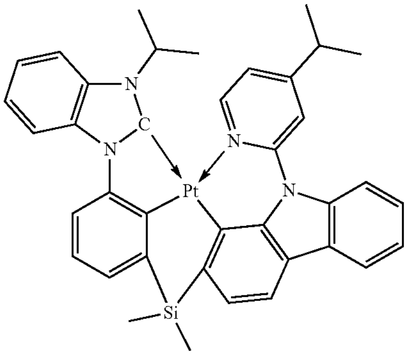
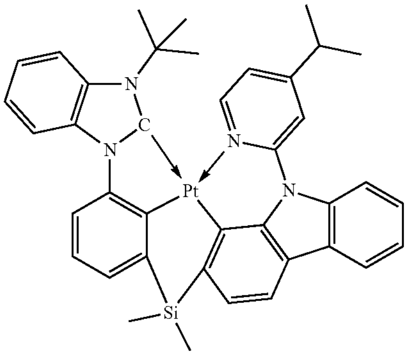
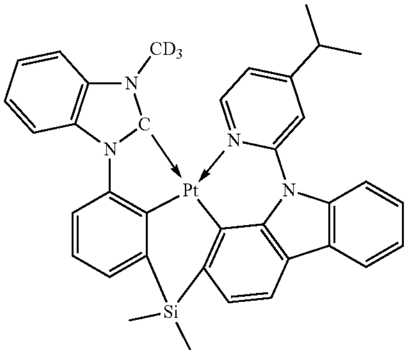
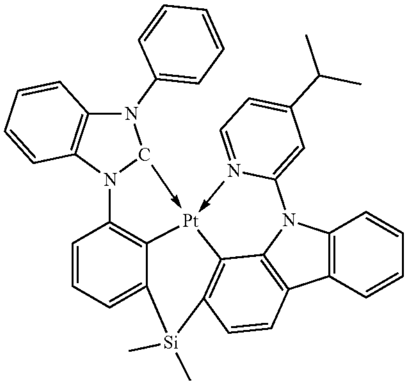

-continued
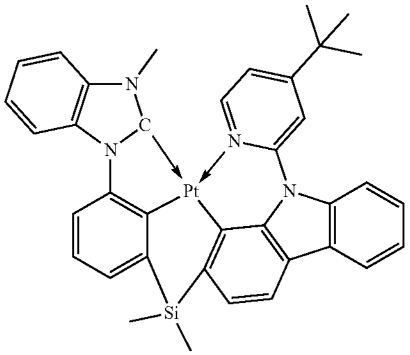
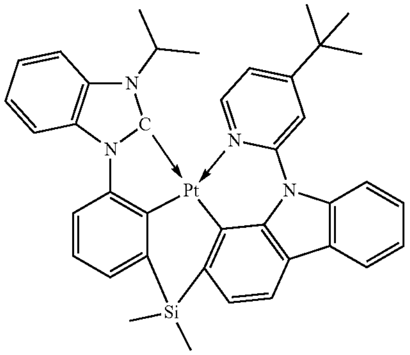
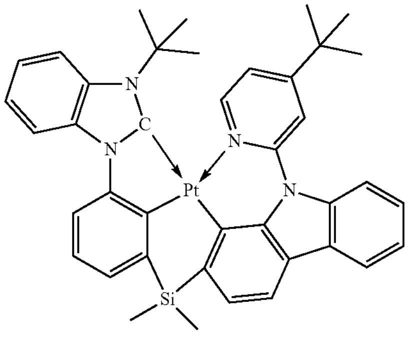
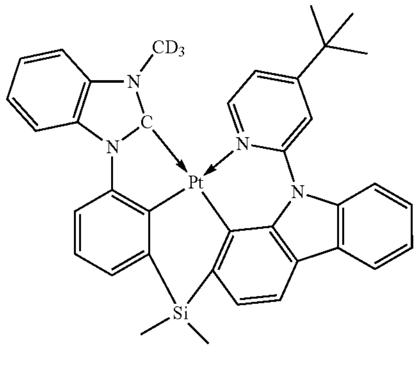
-continued
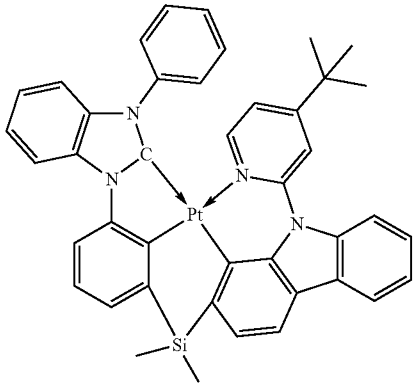
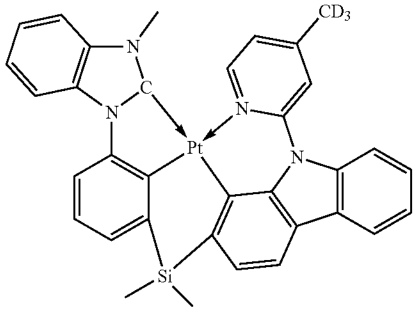
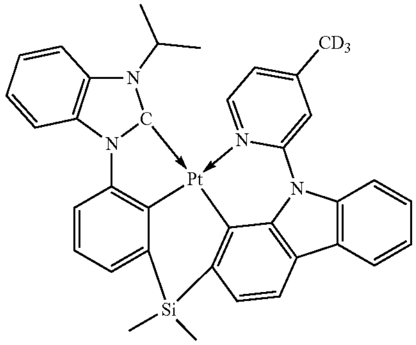
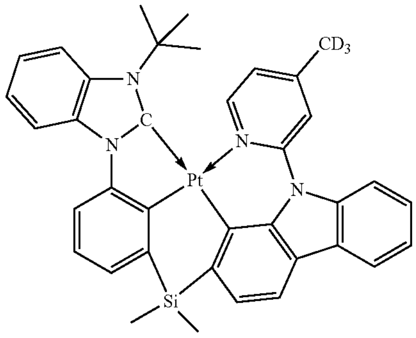
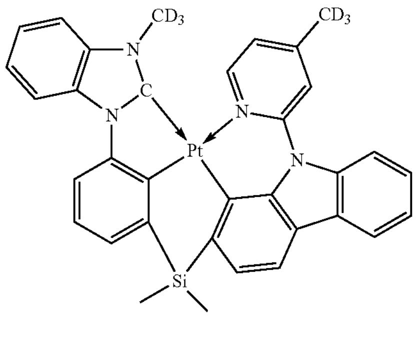

-continued
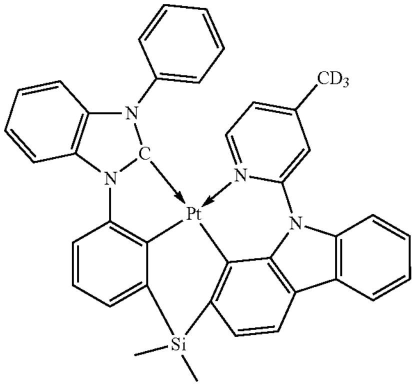
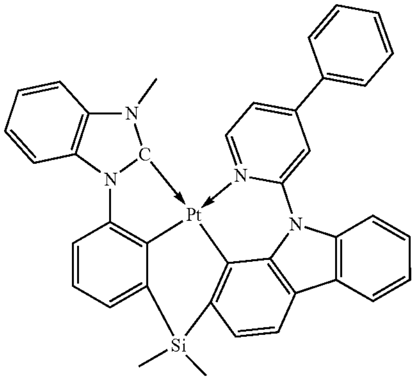
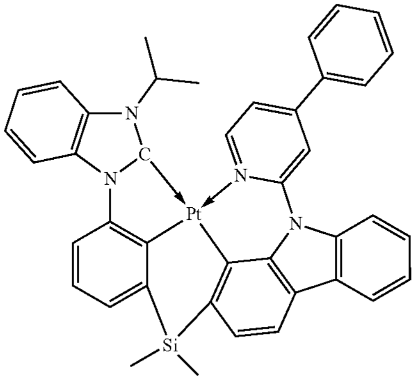
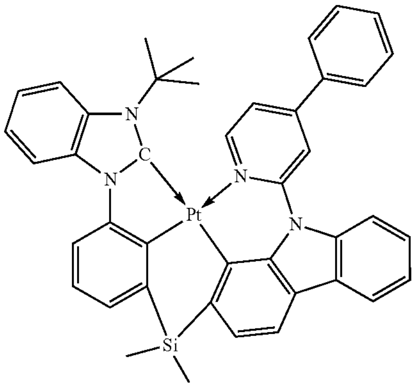
-continued
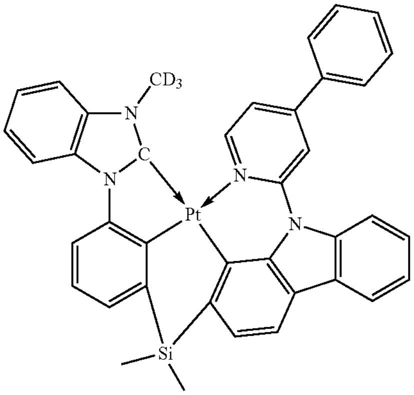
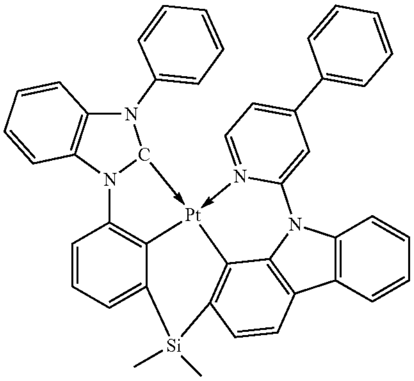
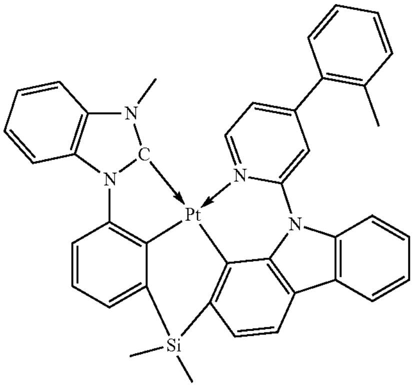
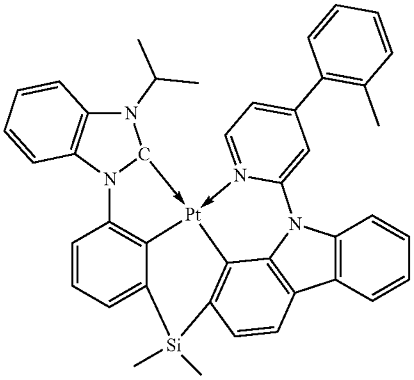

-continued
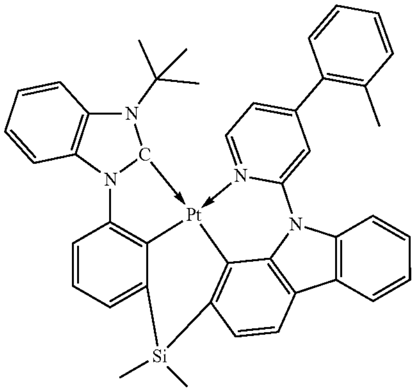
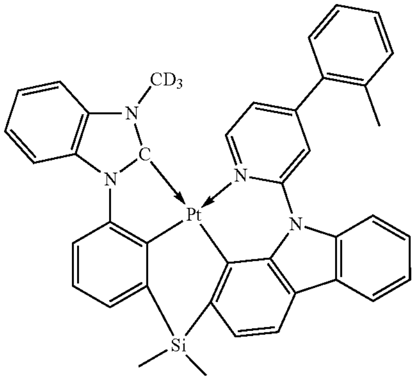
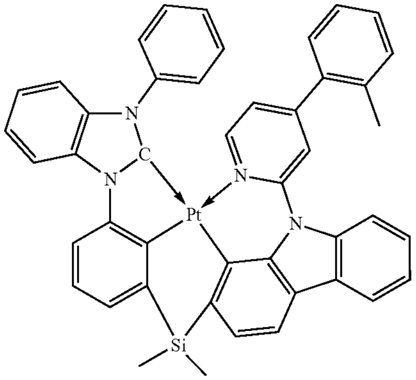
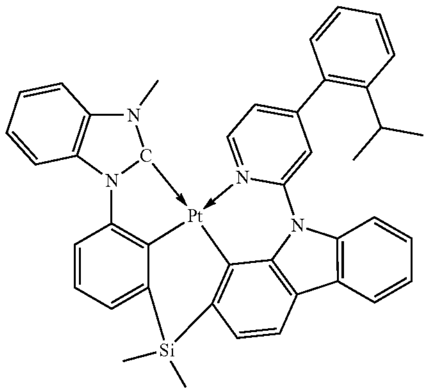
-continued
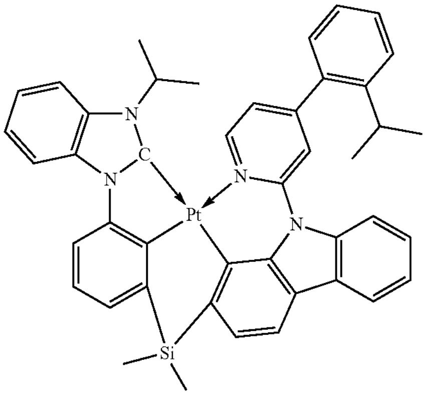
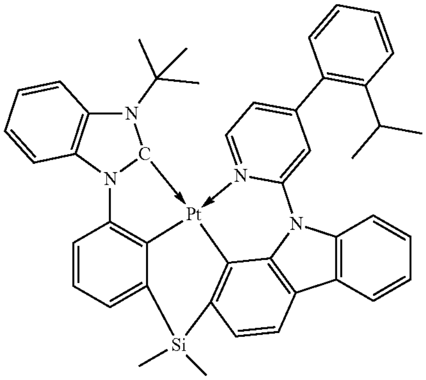
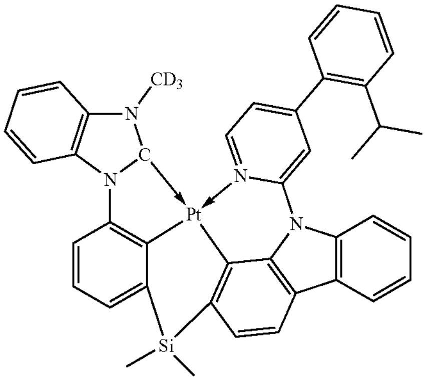
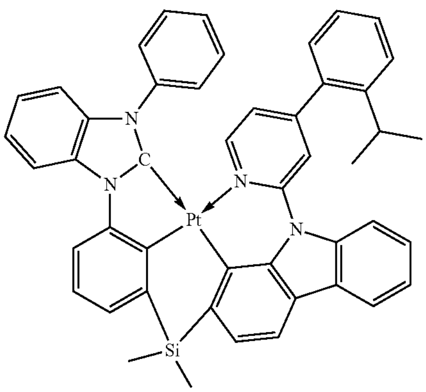

-continued
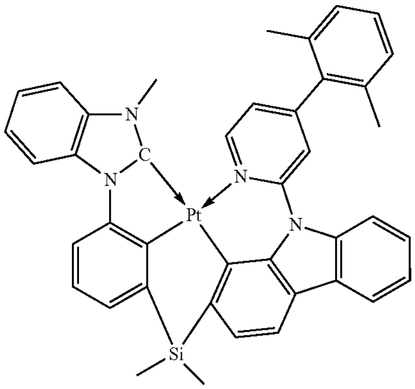
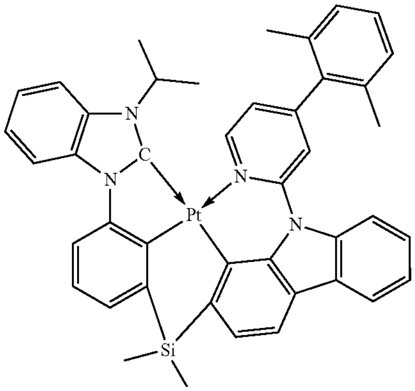
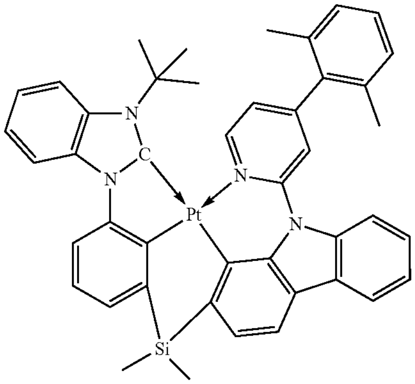
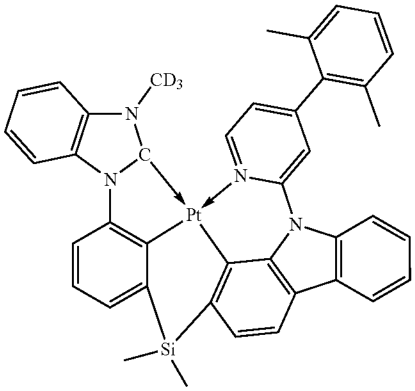
-continued
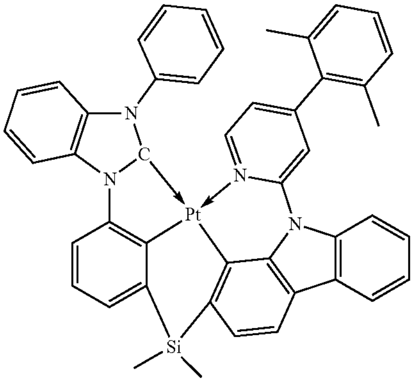
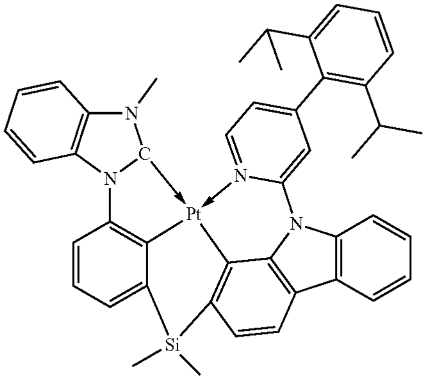
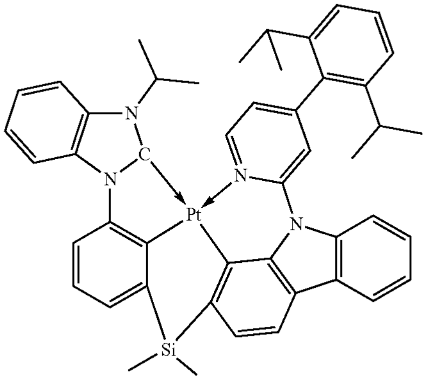
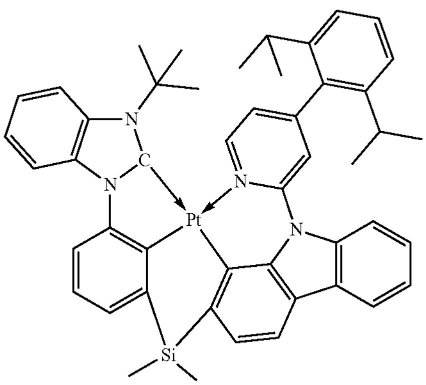

-continued
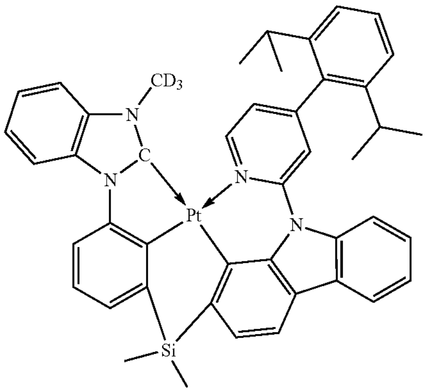
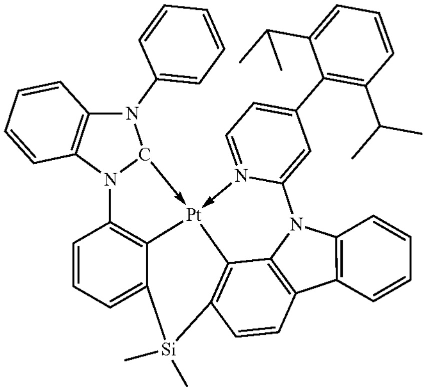
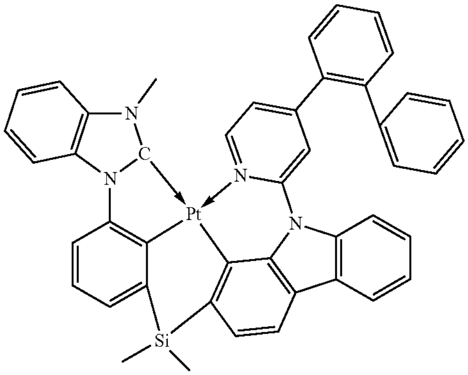
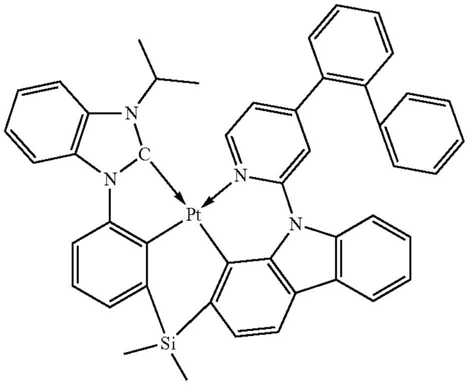
-continued
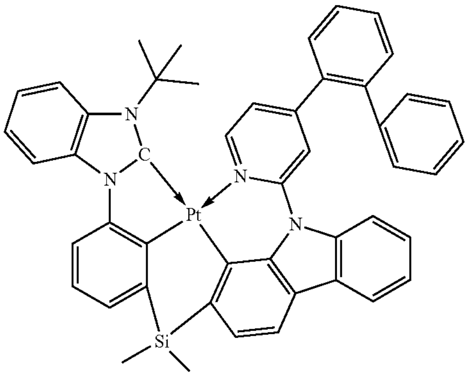
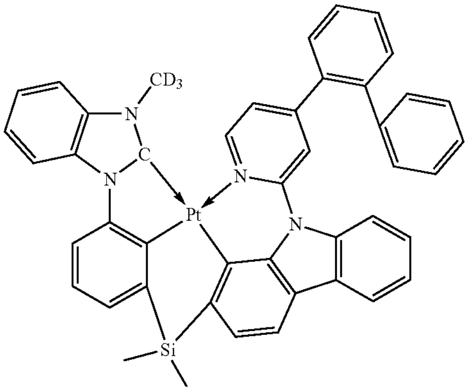
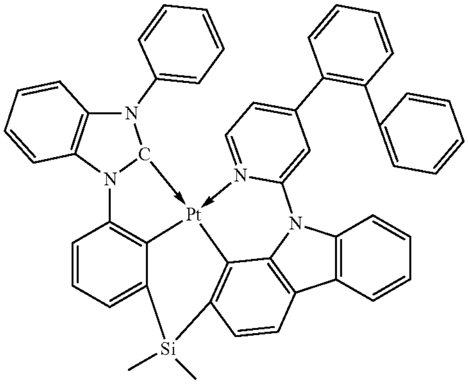
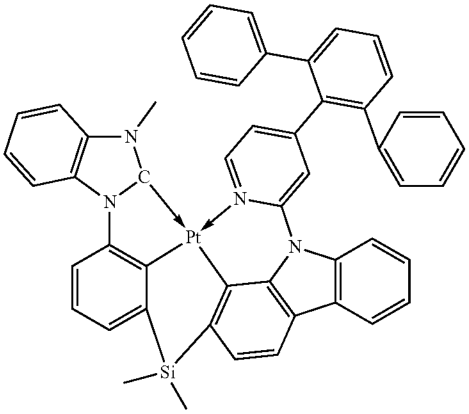

-continued
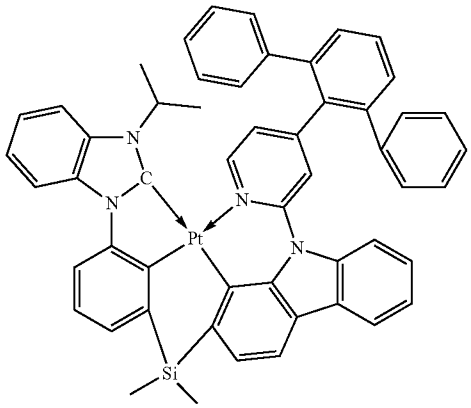
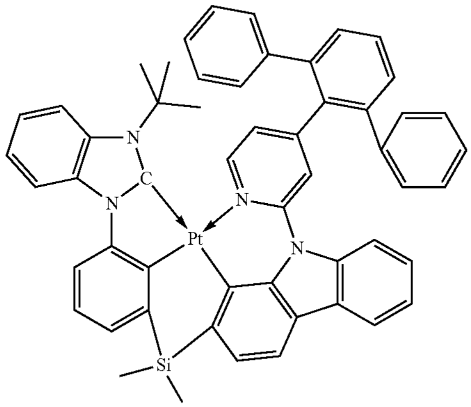
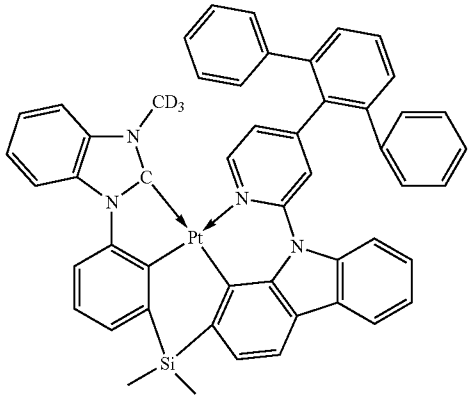
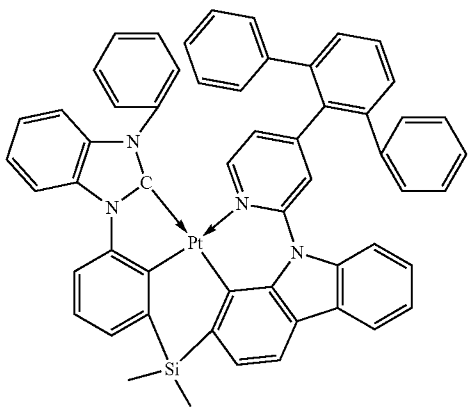
-continued
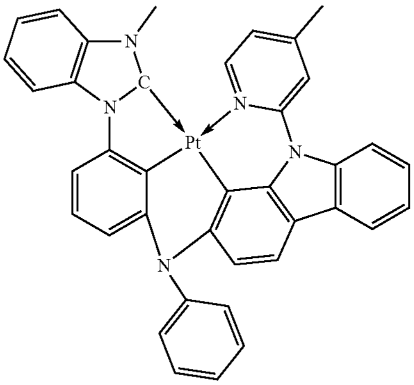
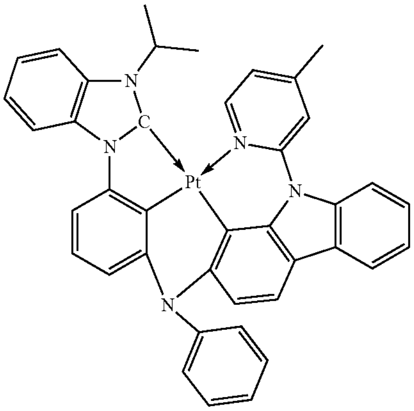
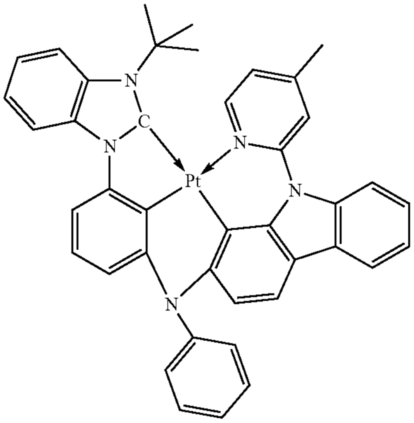
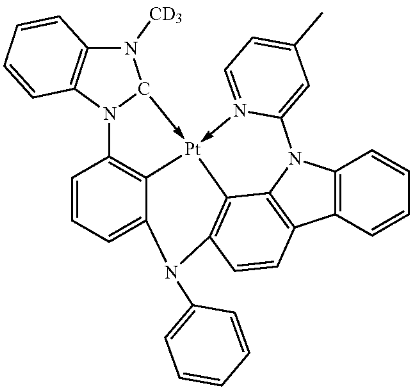

-continued
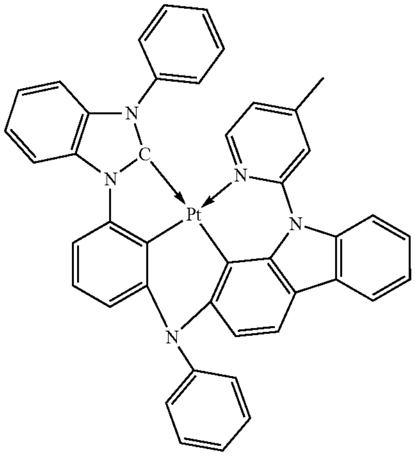
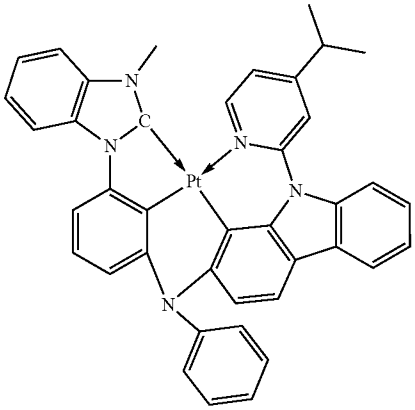
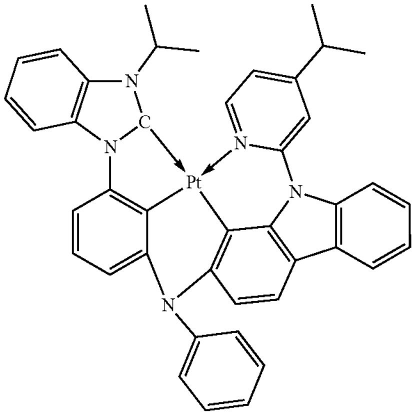
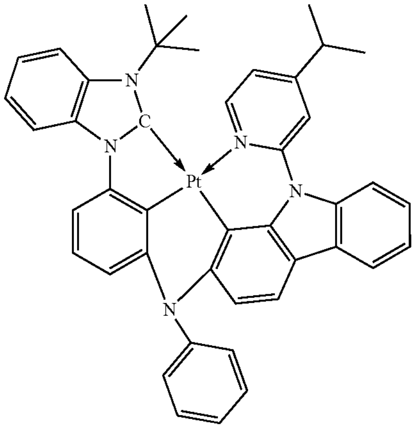
-continued
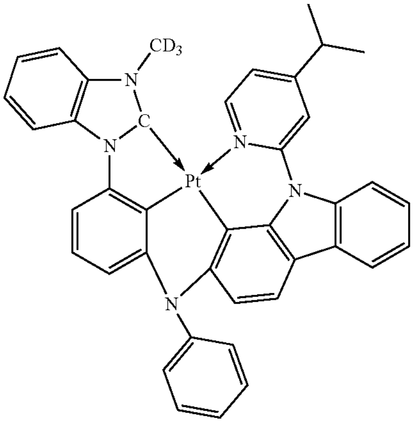
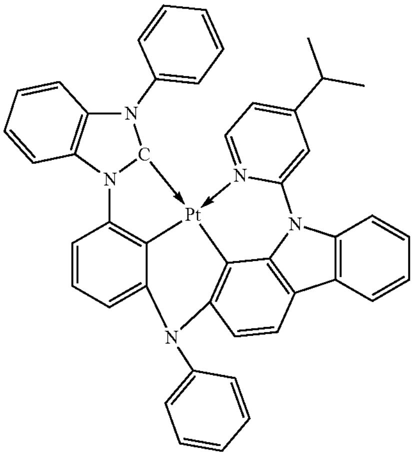
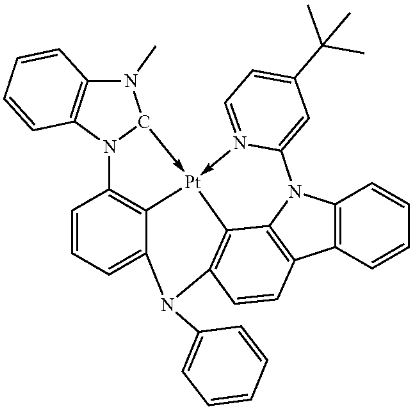
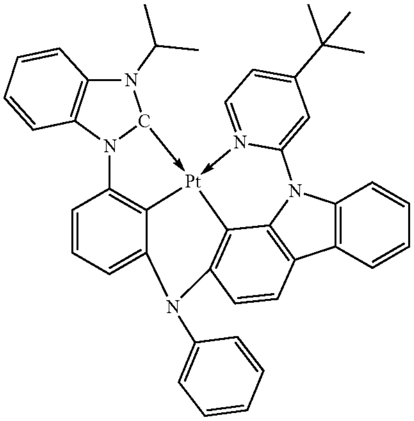

-continued
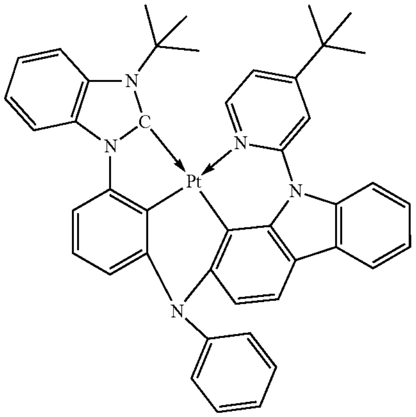
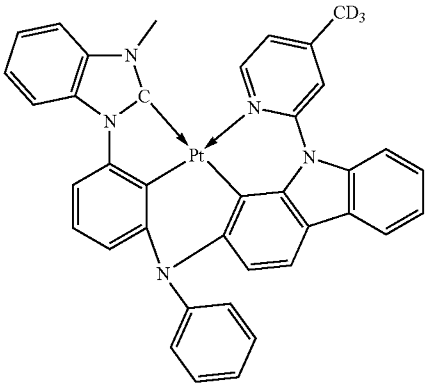
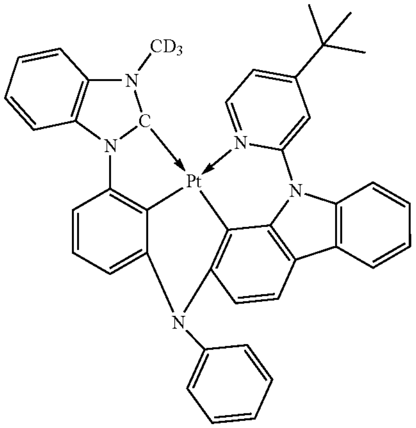
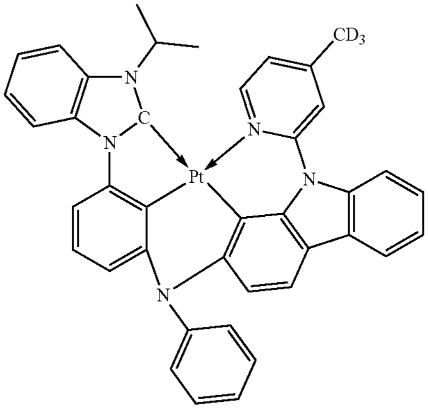
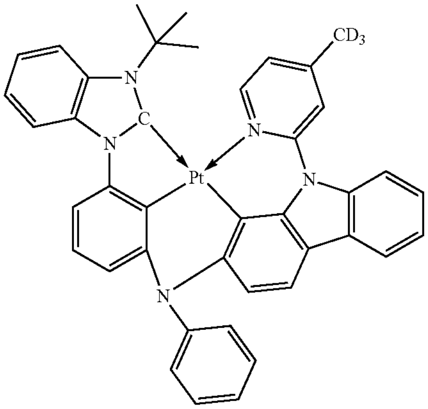
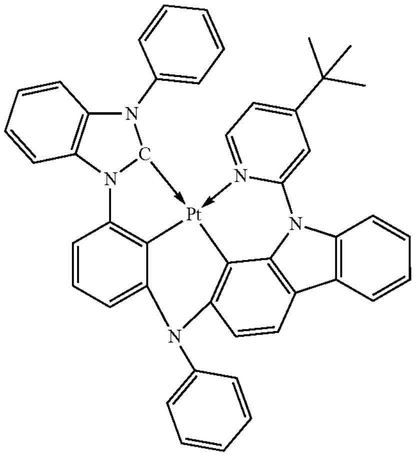
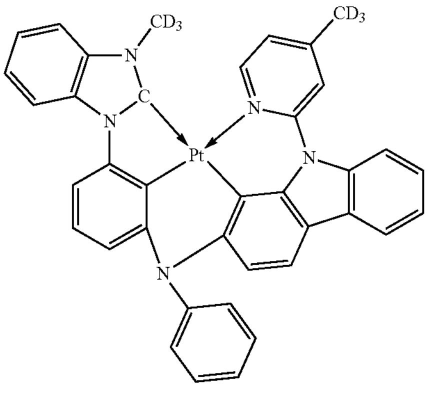

-continued
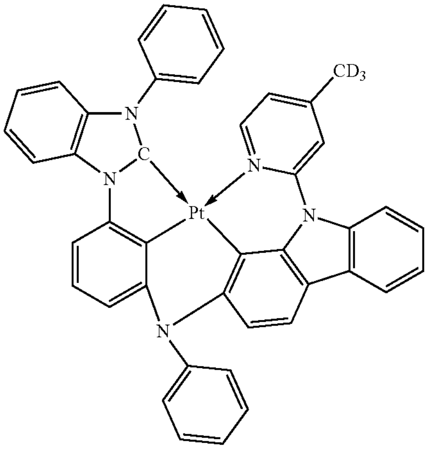
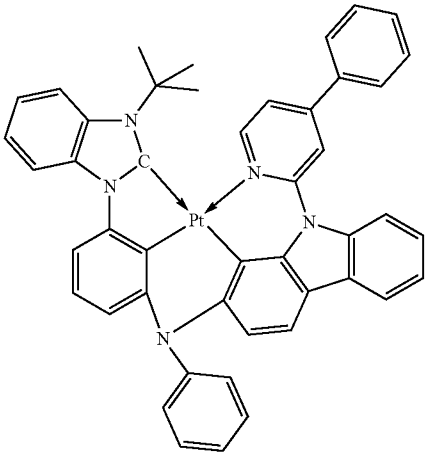
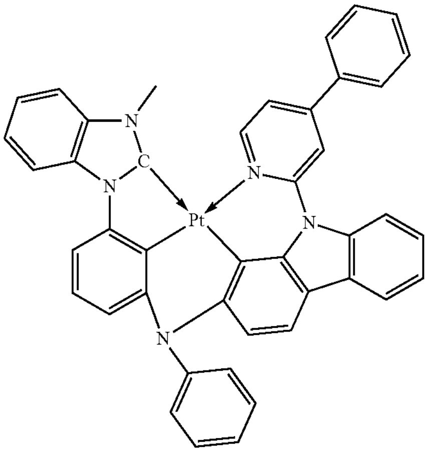
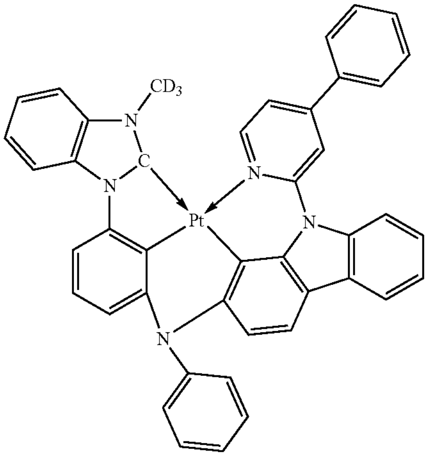
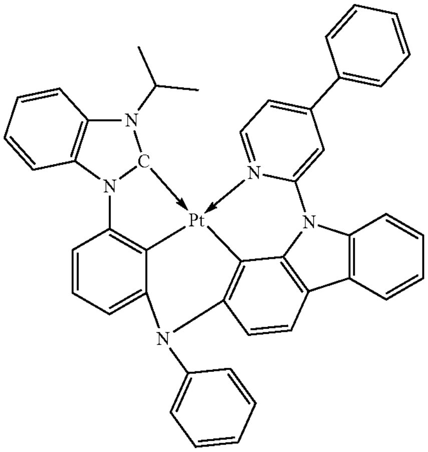
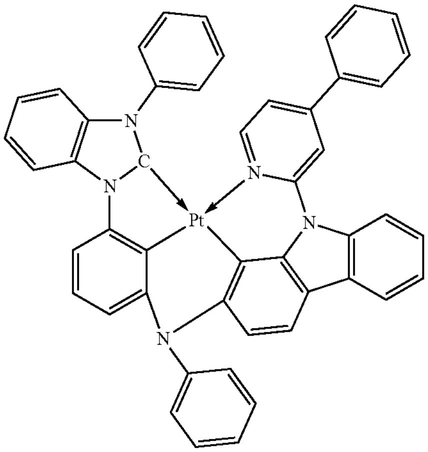

-continued
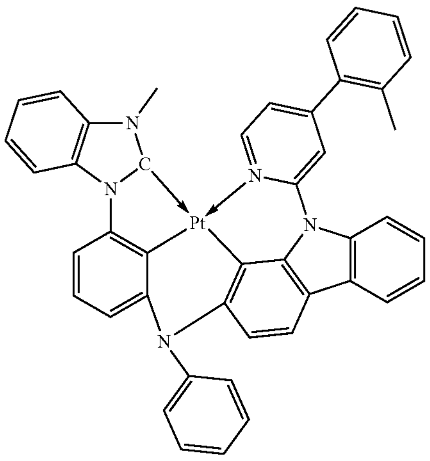
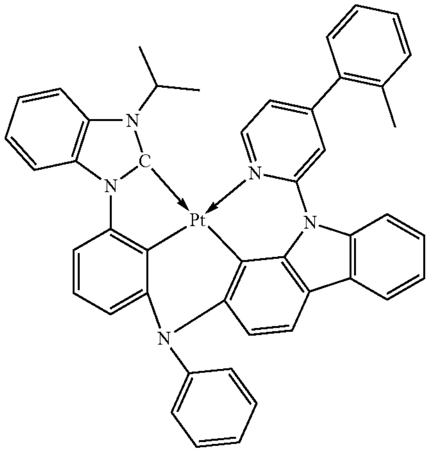
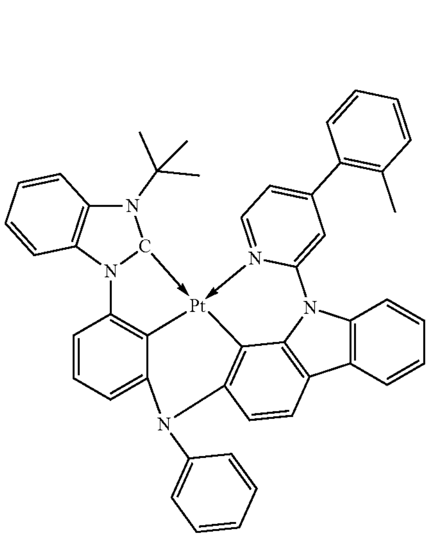
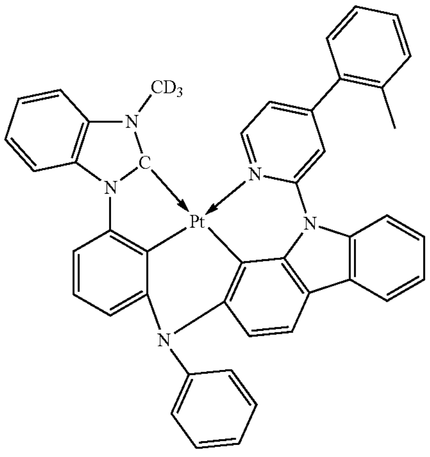
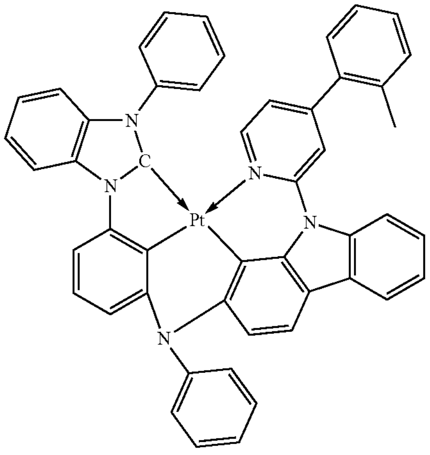
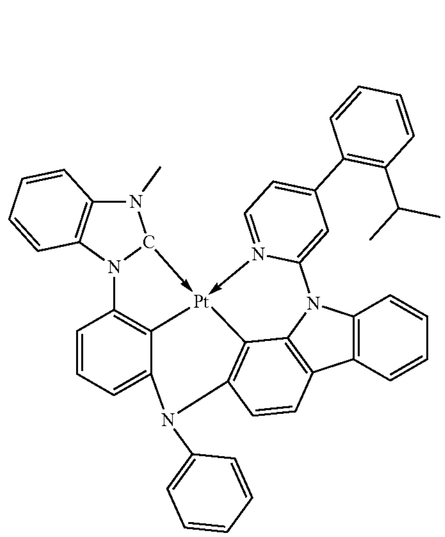

-continued
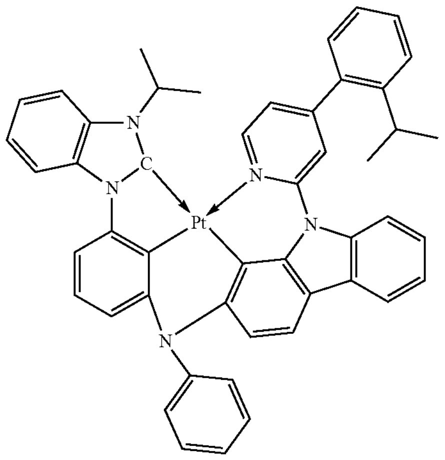
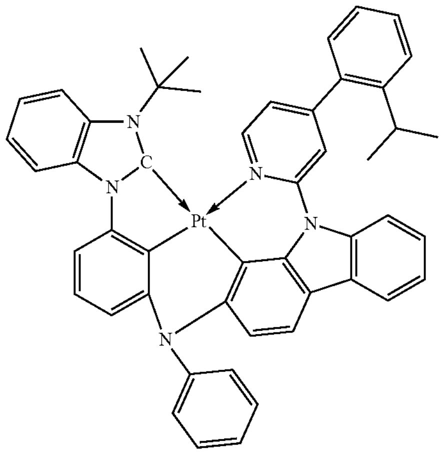
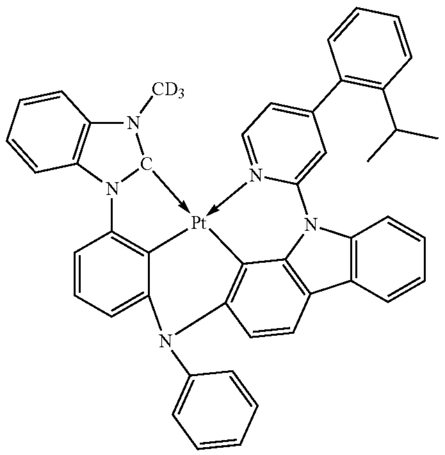
-continued
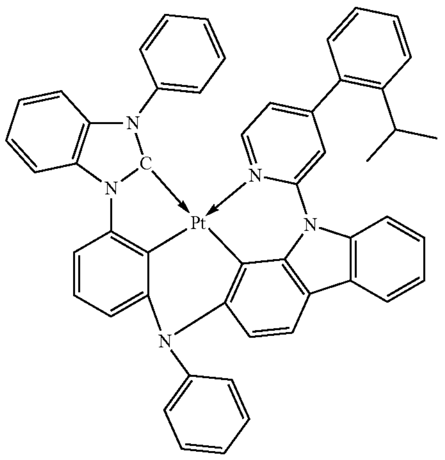
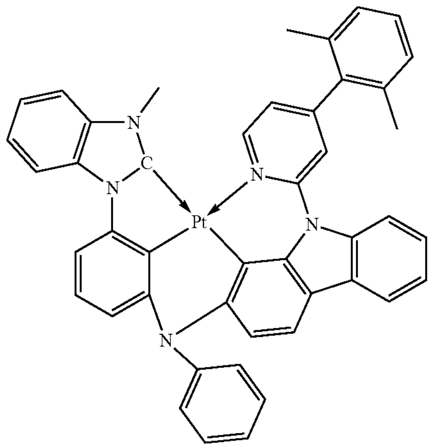
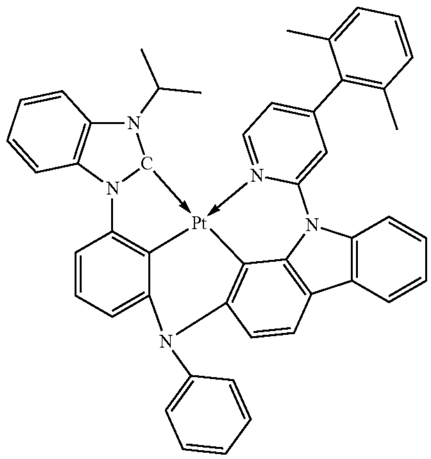

-continued
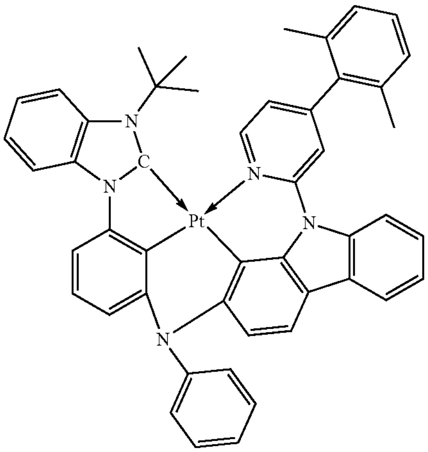
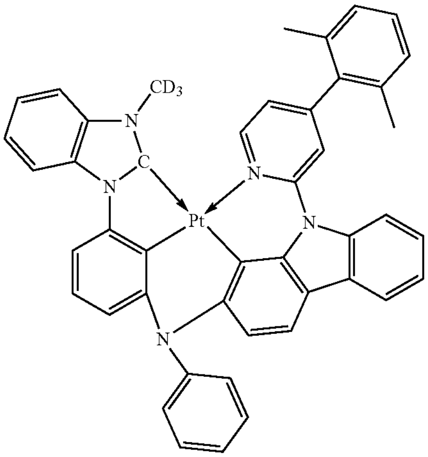
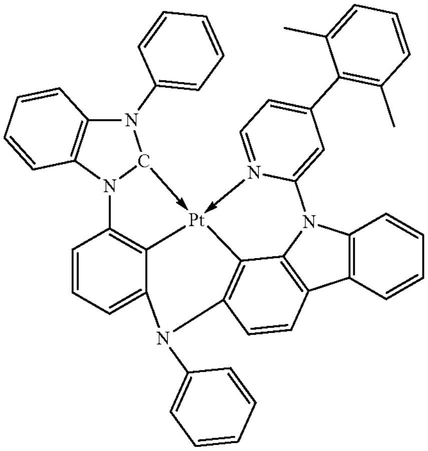
-continued
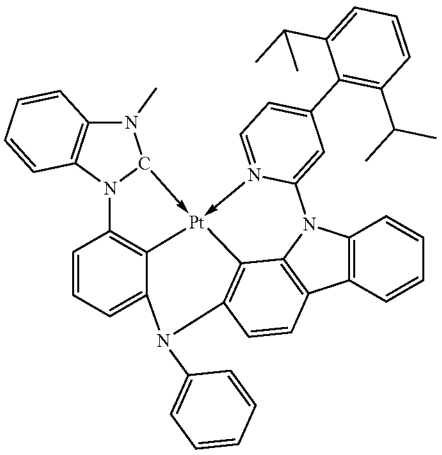
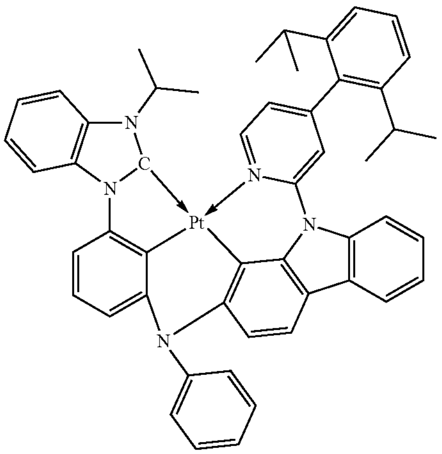
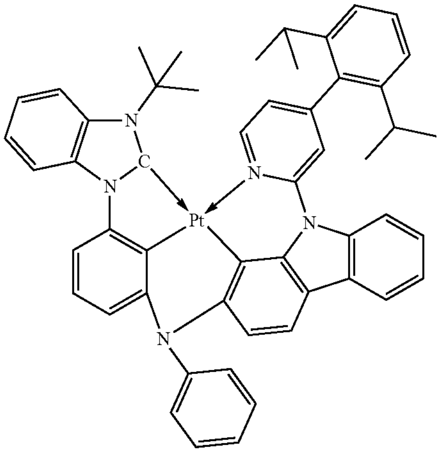

-continued
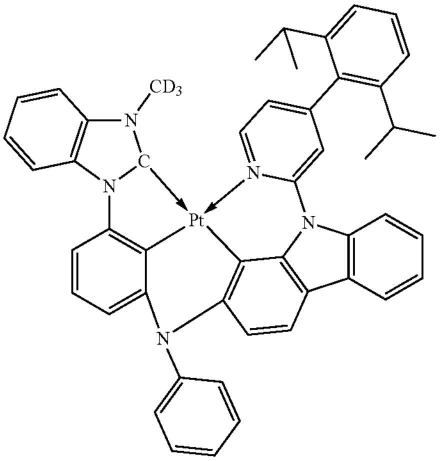
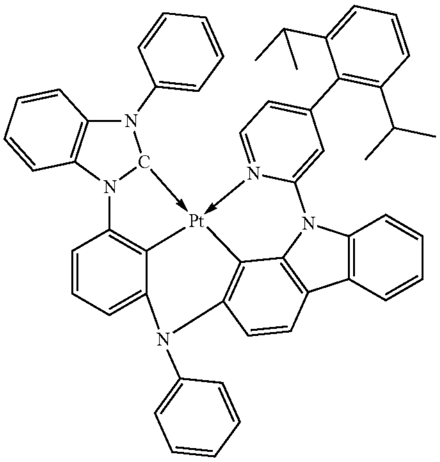
-continued
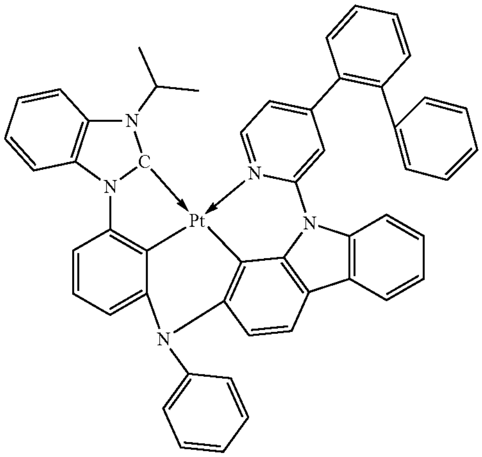
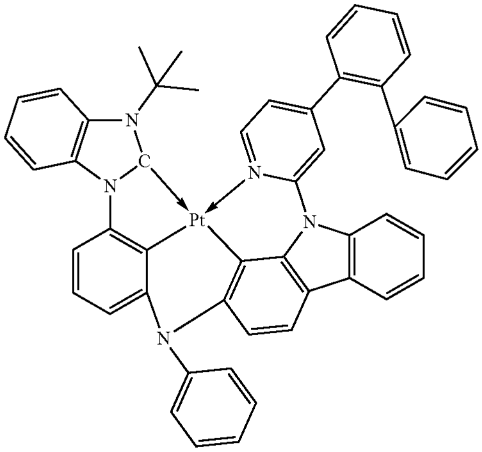
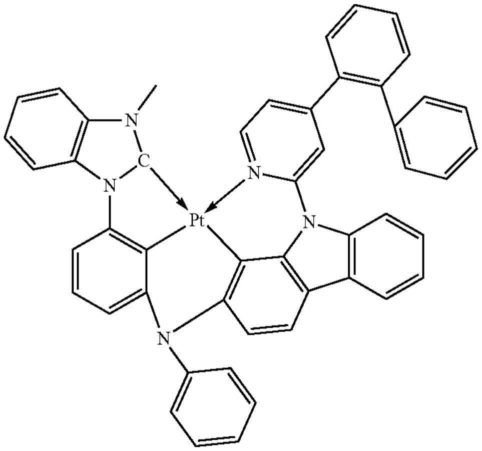
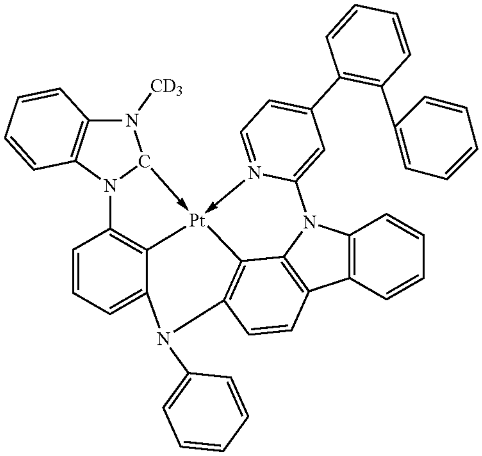

-continued
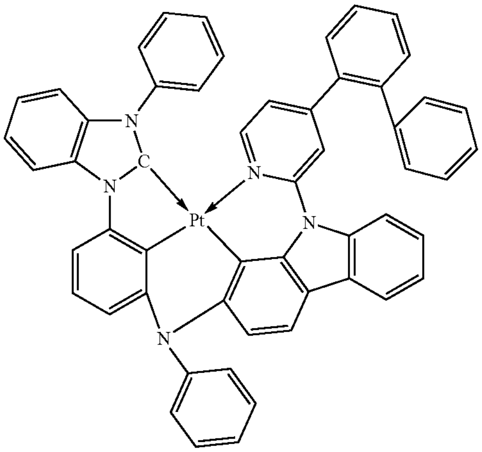
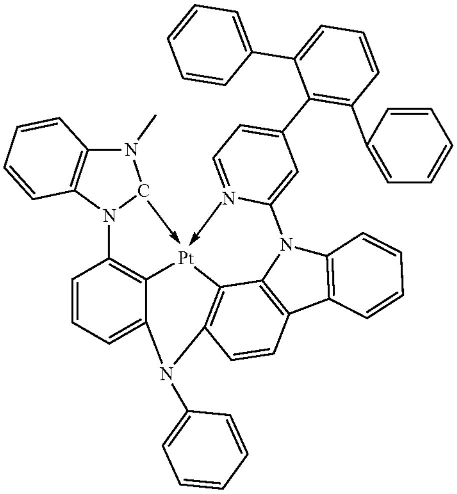
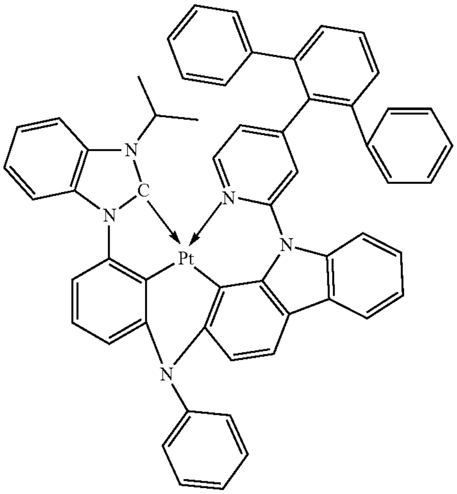
-continued
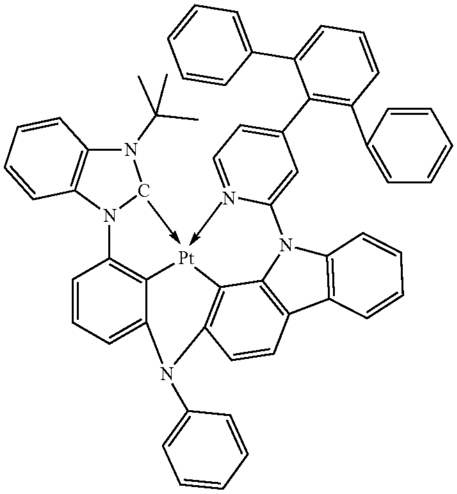
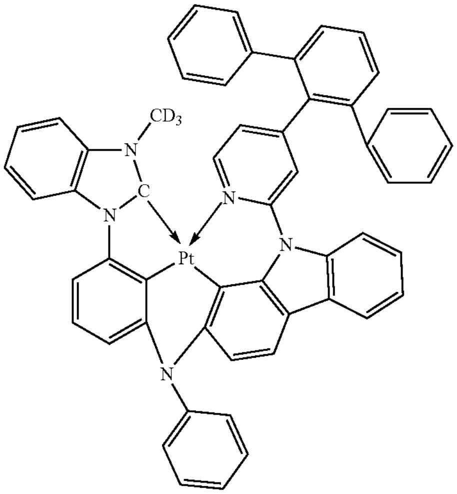
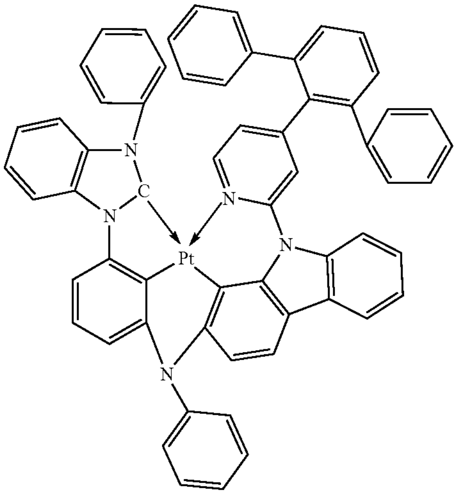

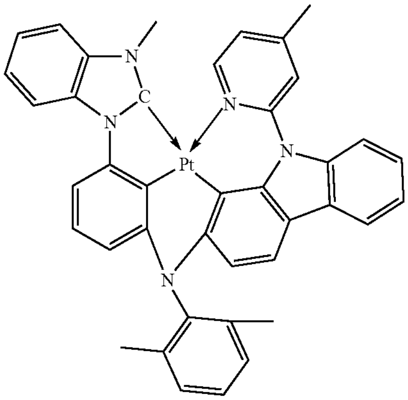
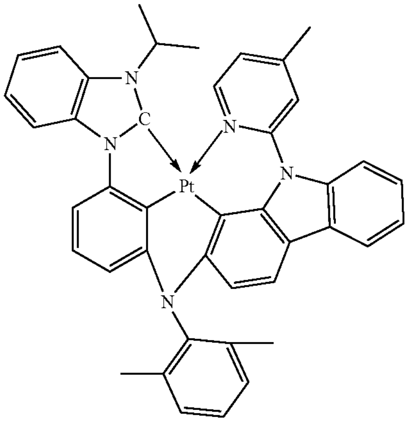
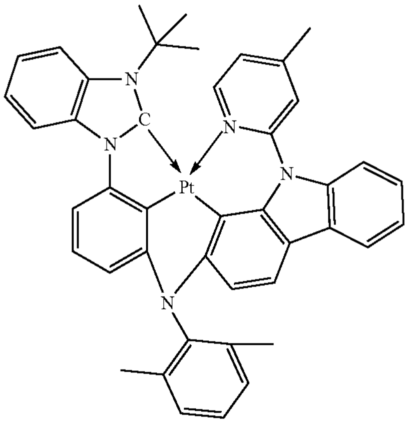
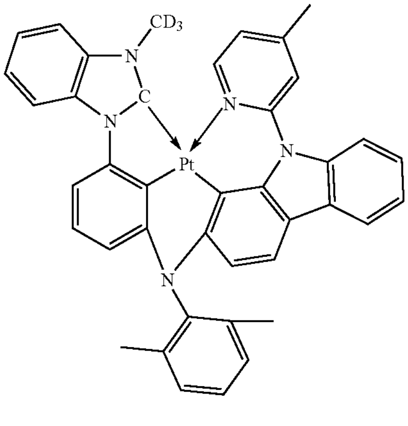
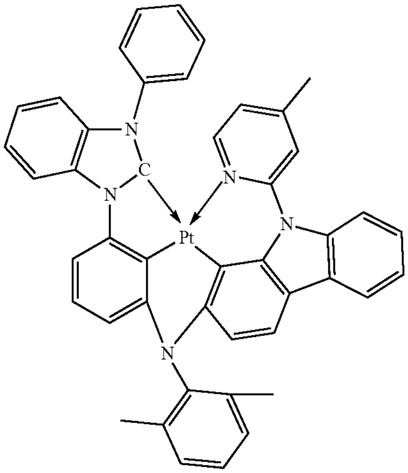
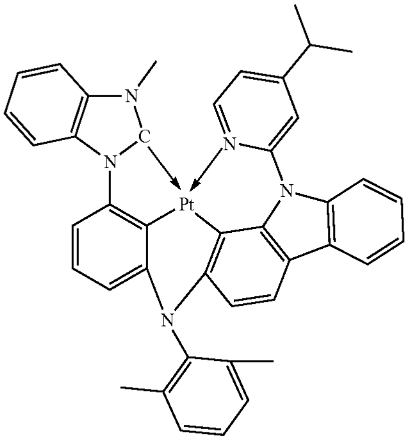
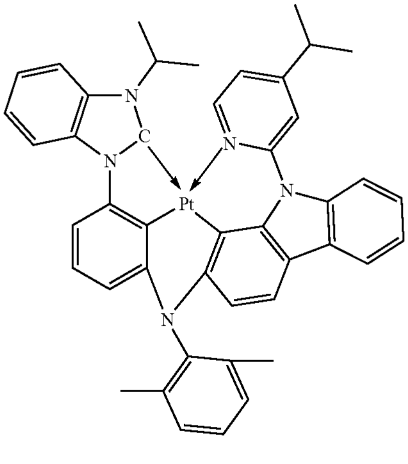

-continued
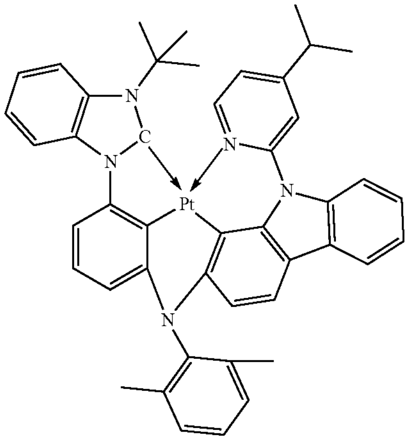
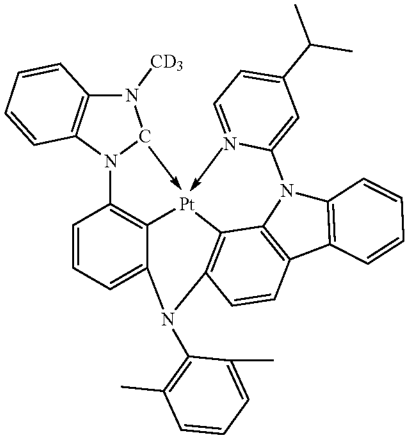
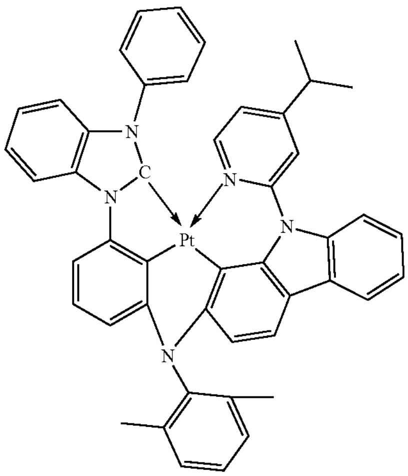
-continued
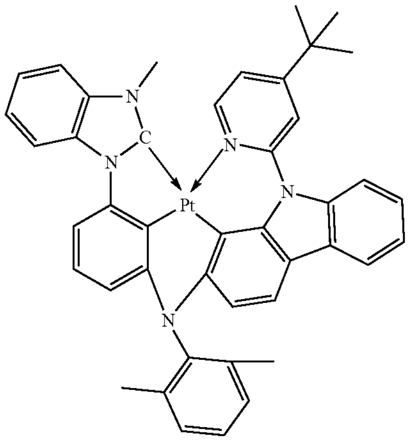
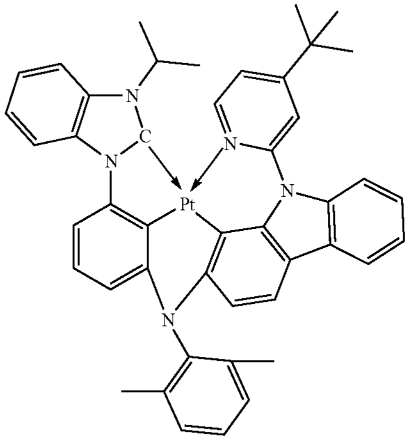
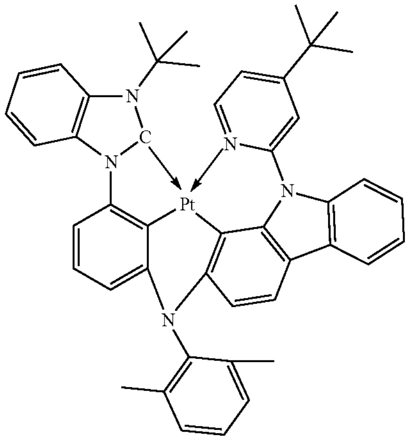

-continued
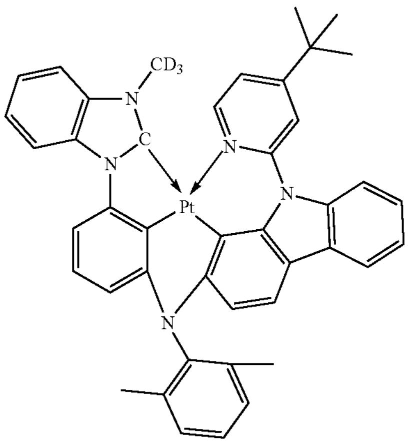
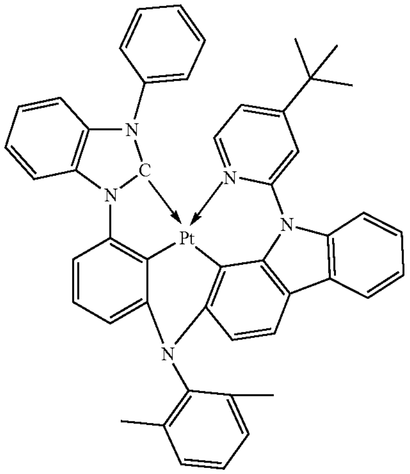
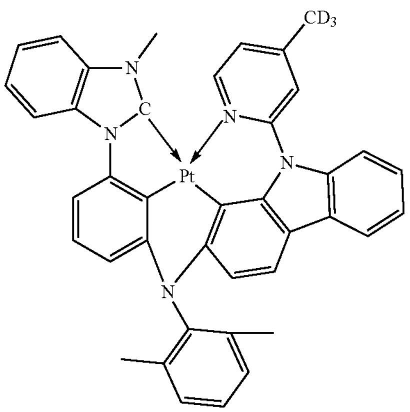
-continued
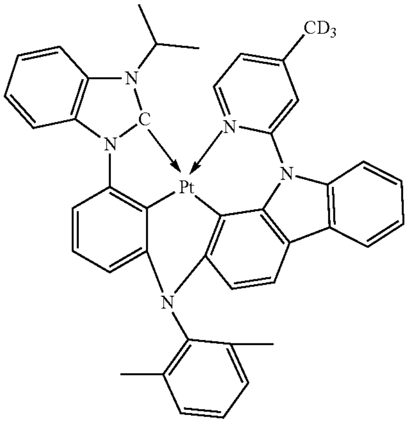
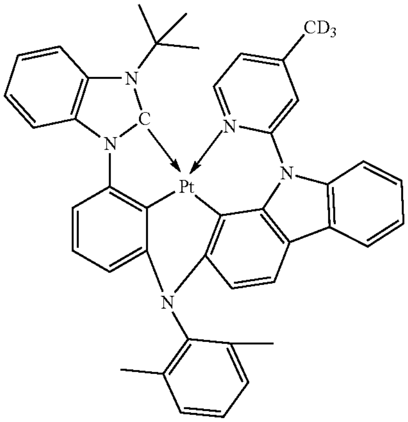
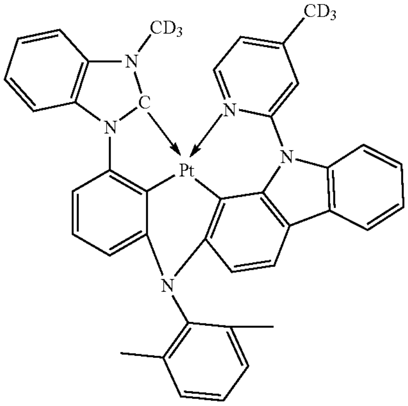
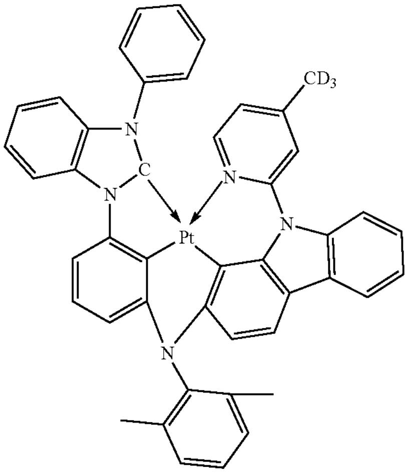

-continued
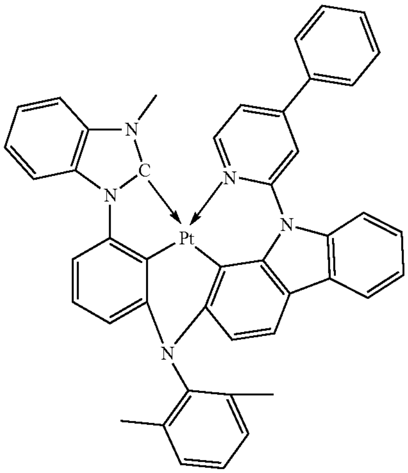
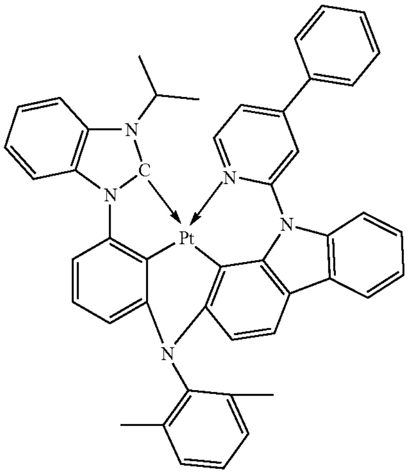
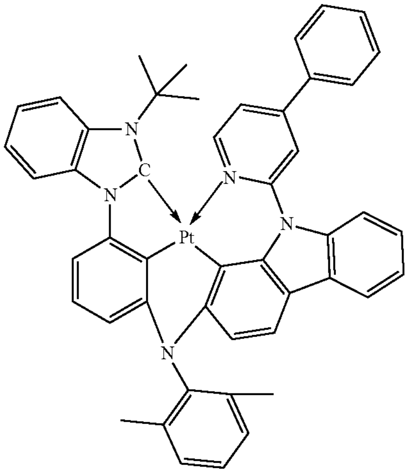
-continued
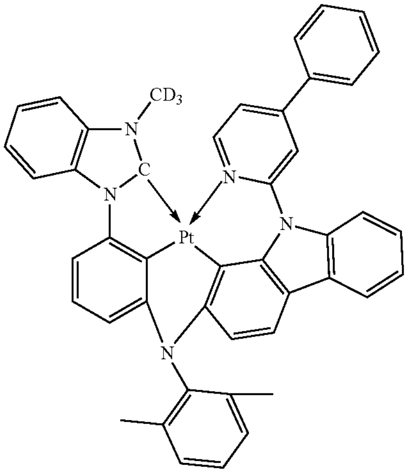
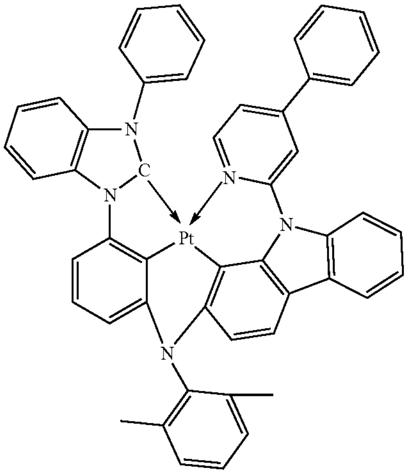
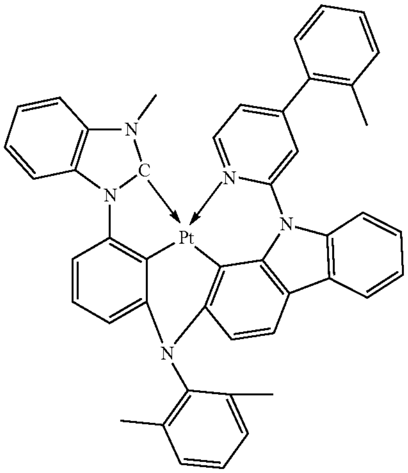

-continued
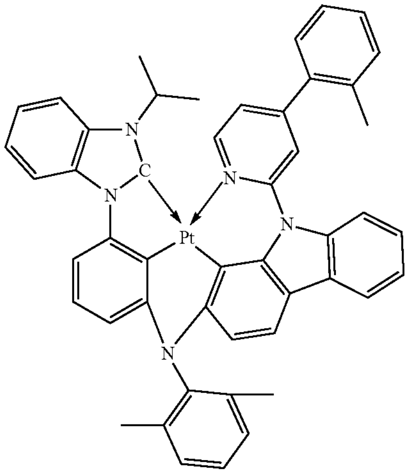
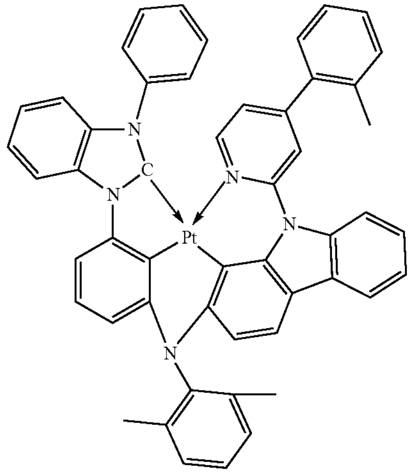
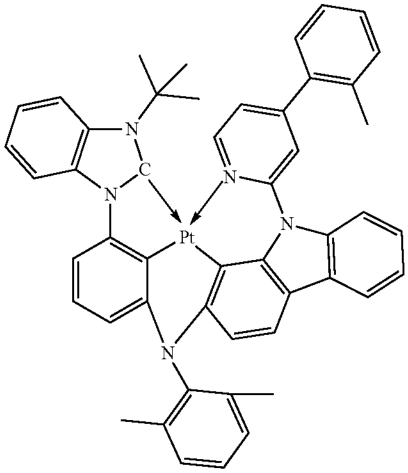
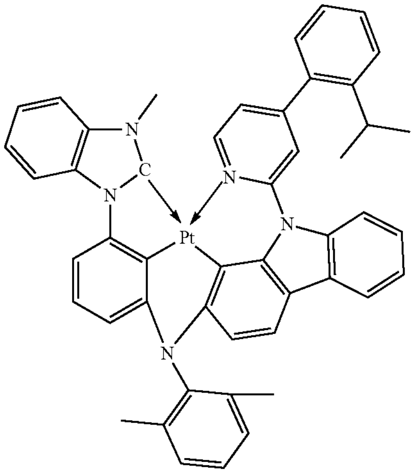
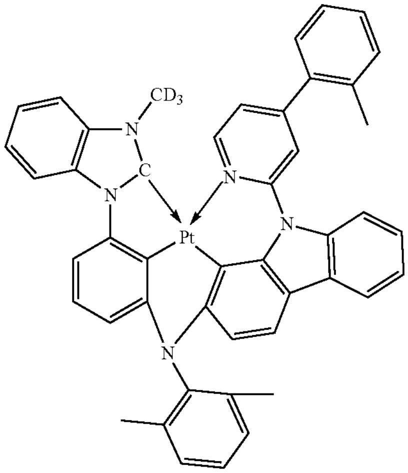
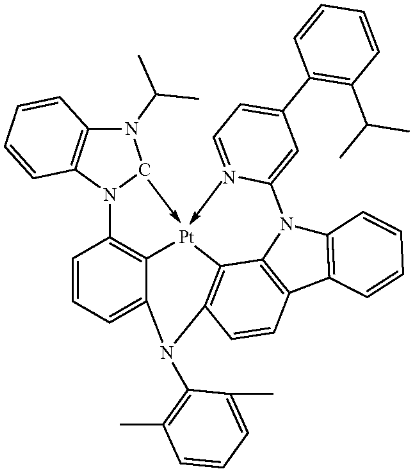
-continued -continued
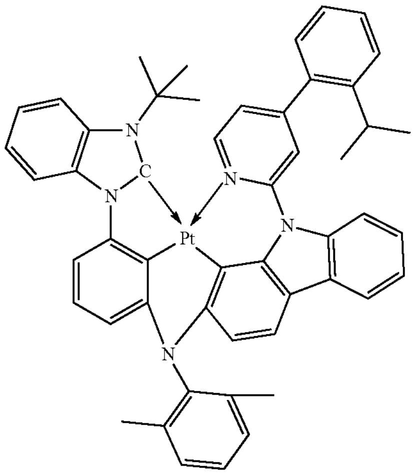
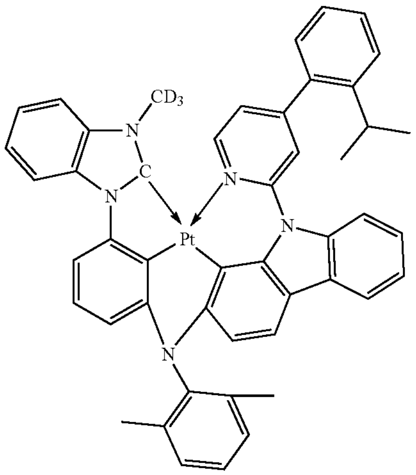
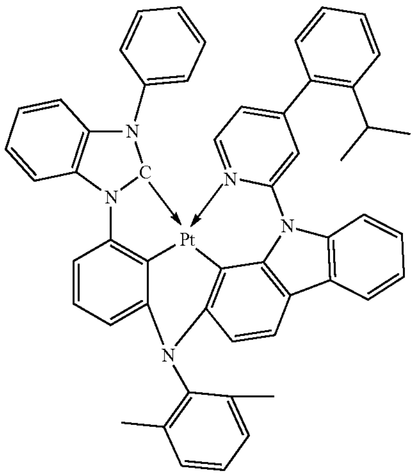
-continued
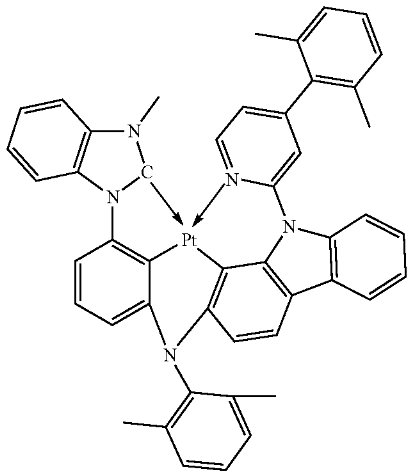
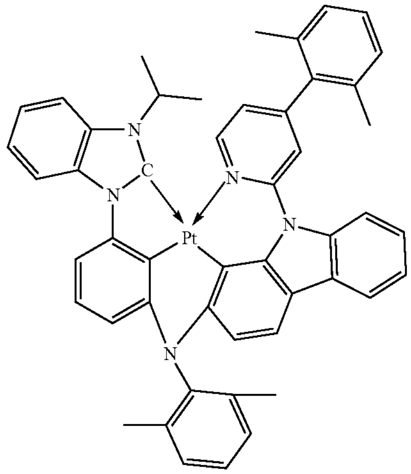
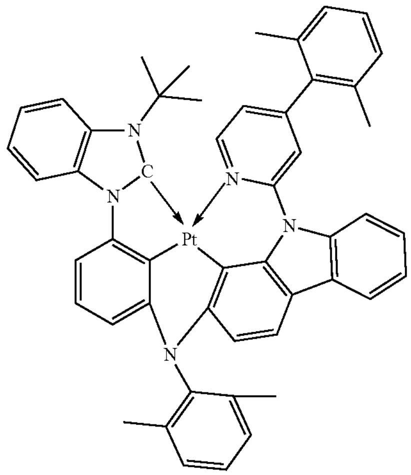

-continued
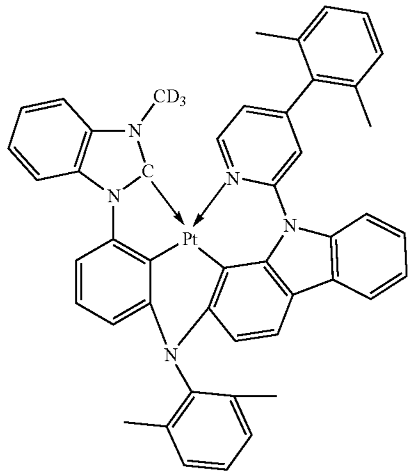
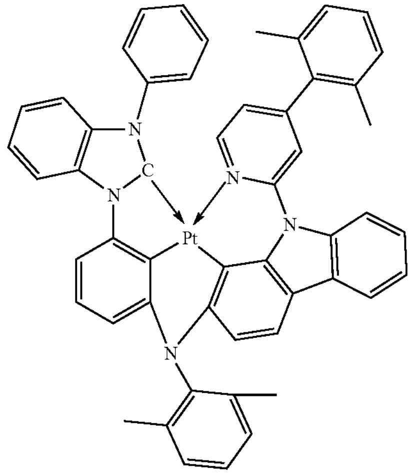
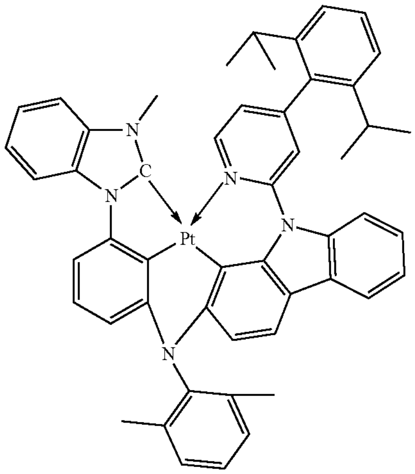
-continued
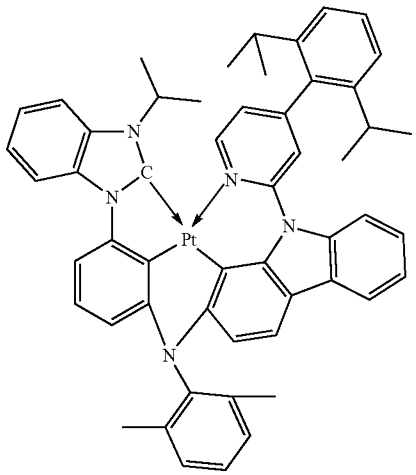
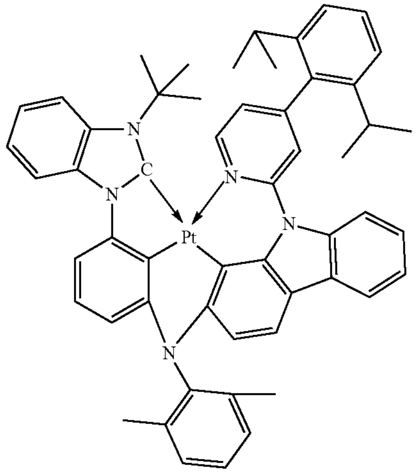
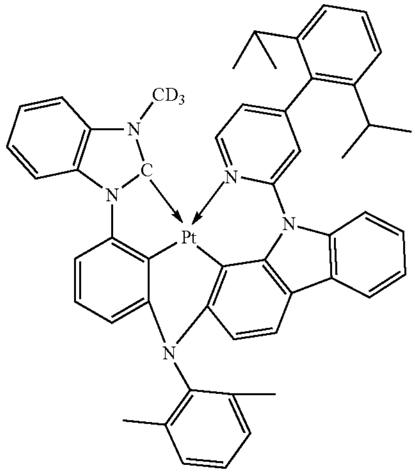

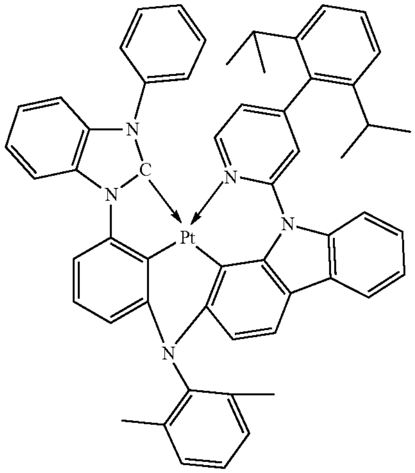
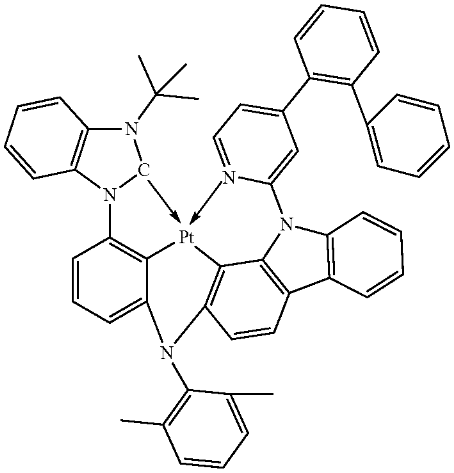
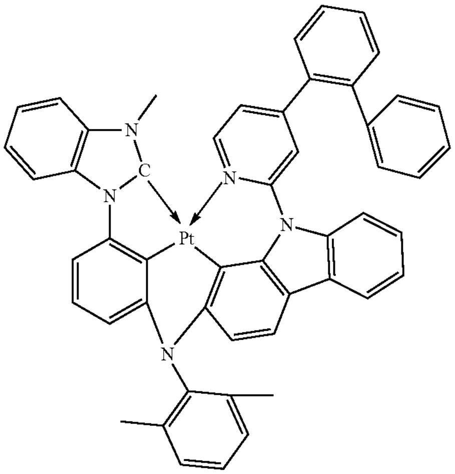
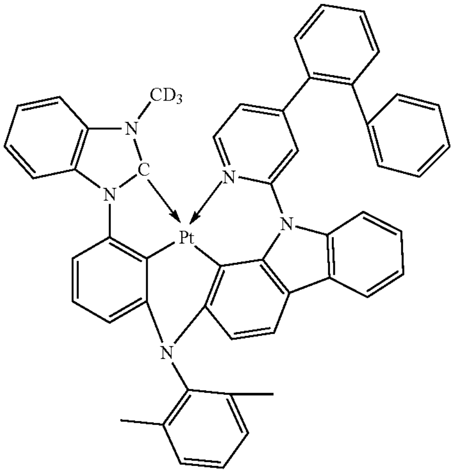
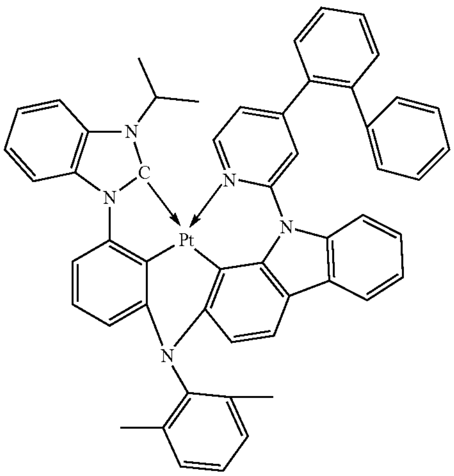
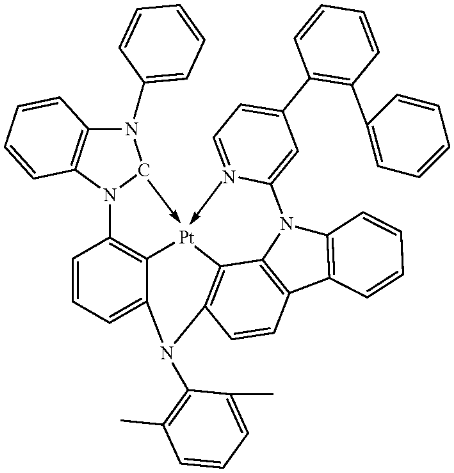

-continued
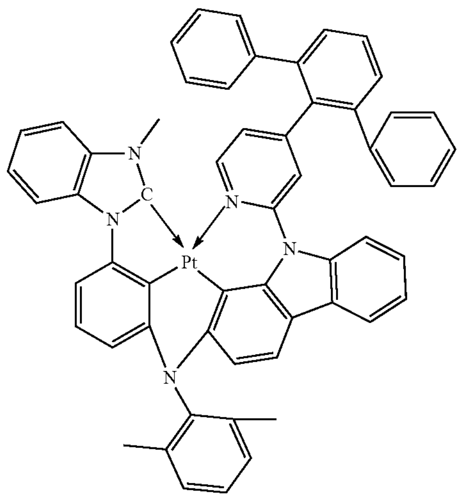
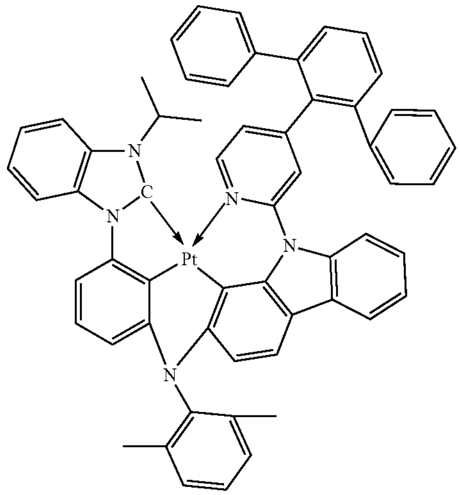
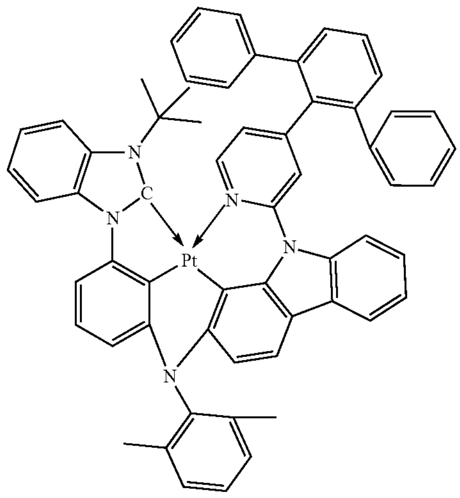
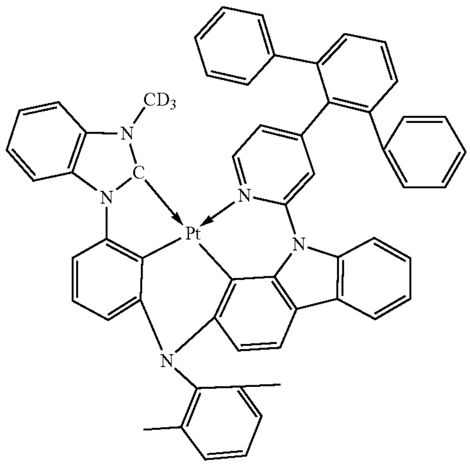
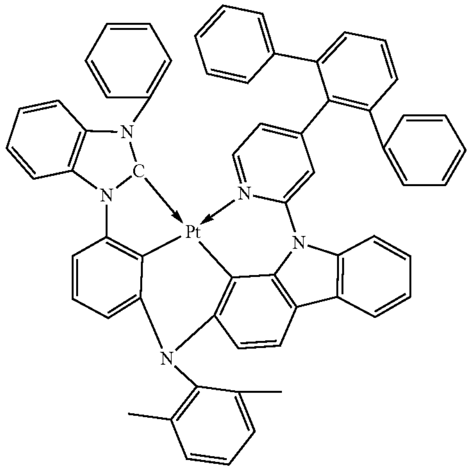
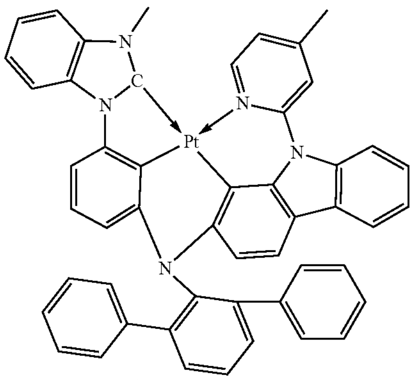
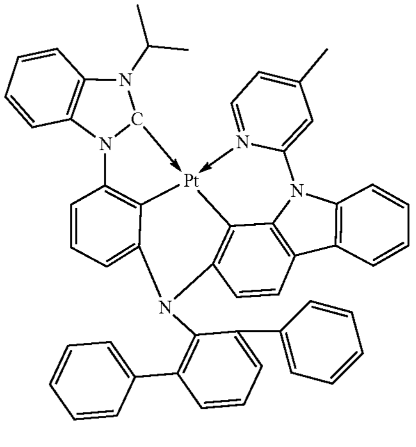

-continued
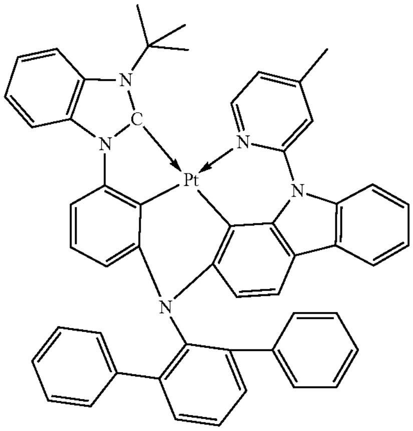
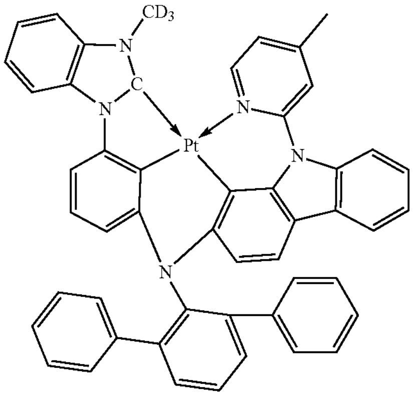
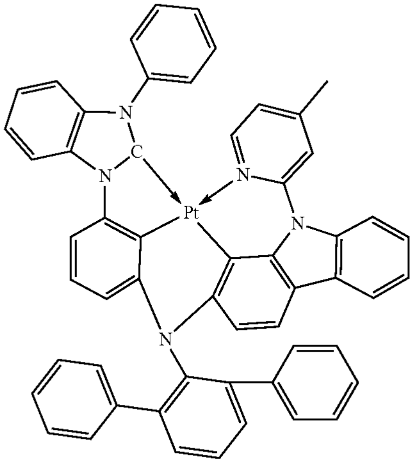
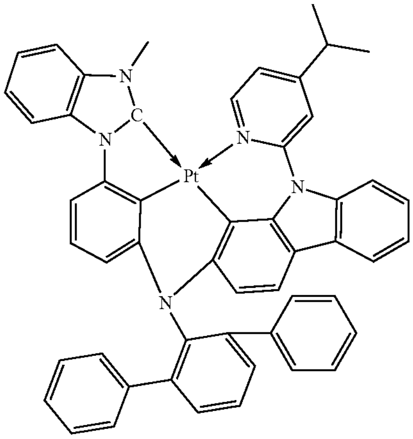
-continued
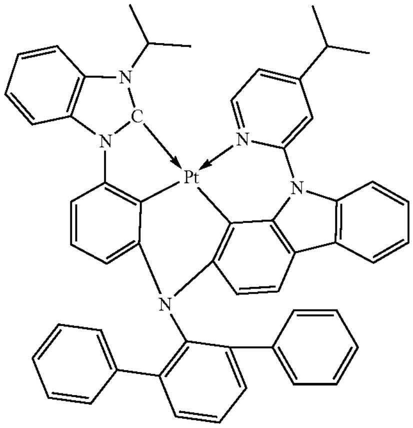
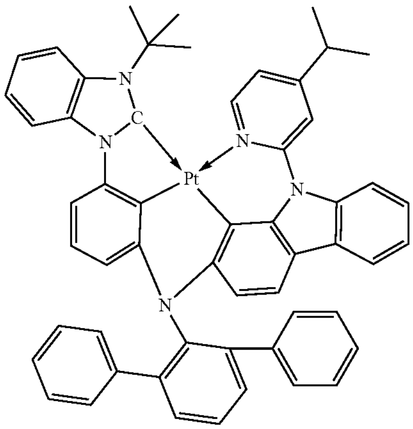
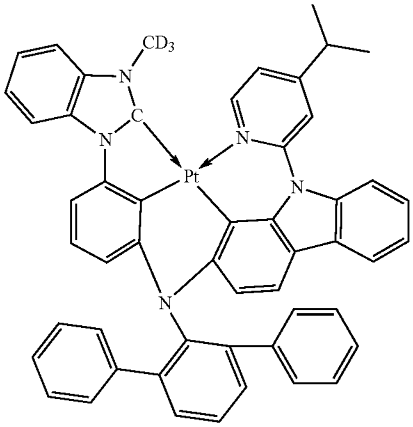

-continued
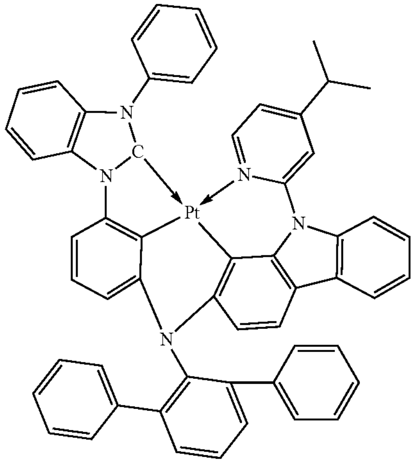
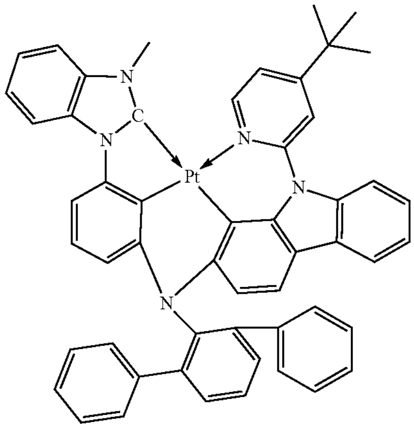
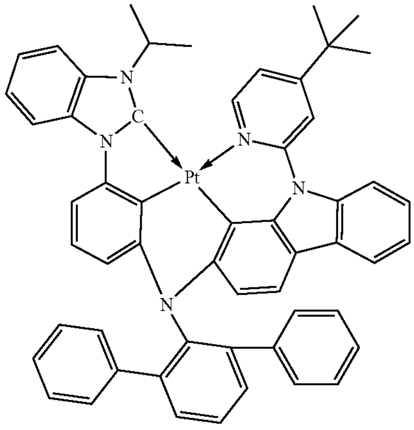
-continued
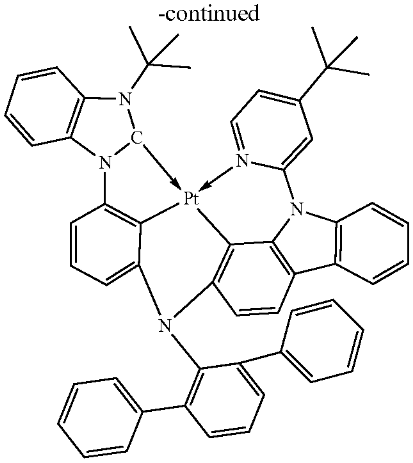
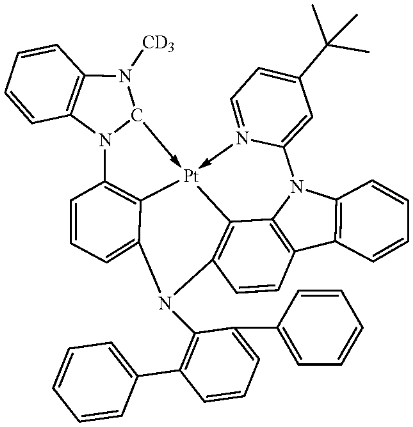
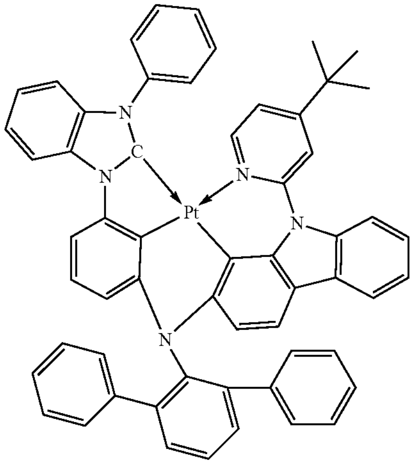
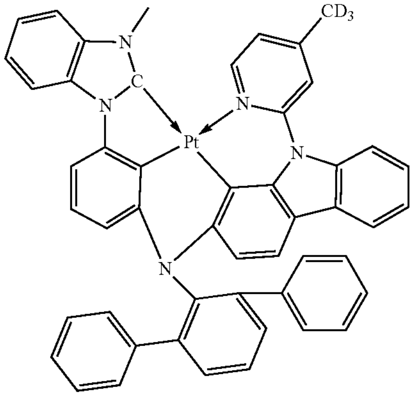

-continued
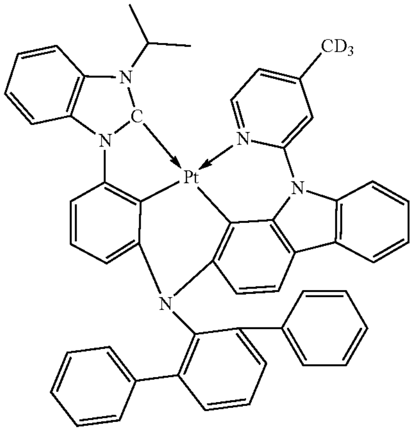
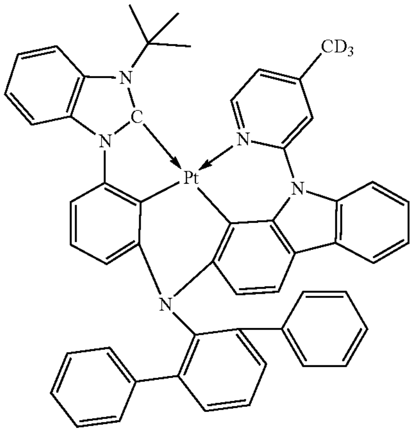
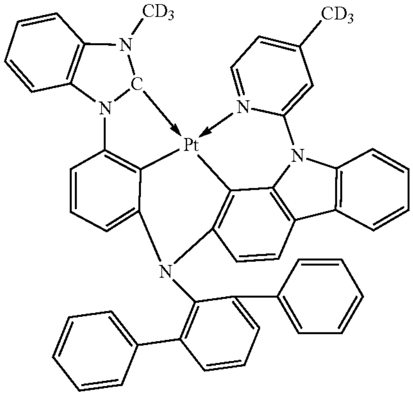
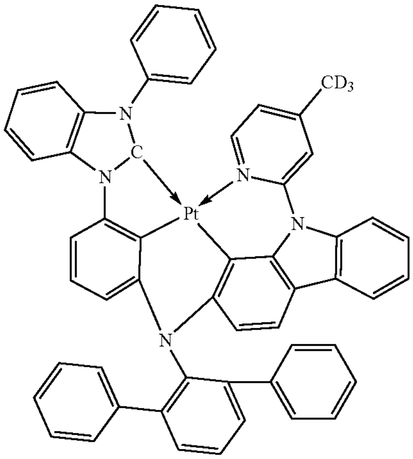
-continued
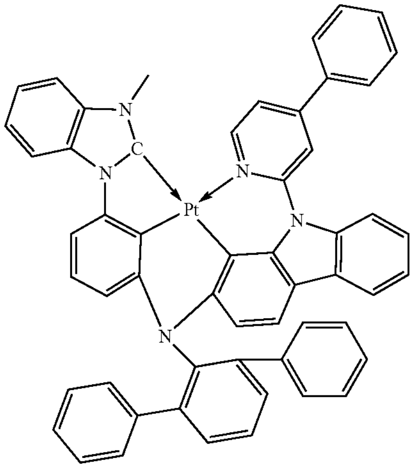
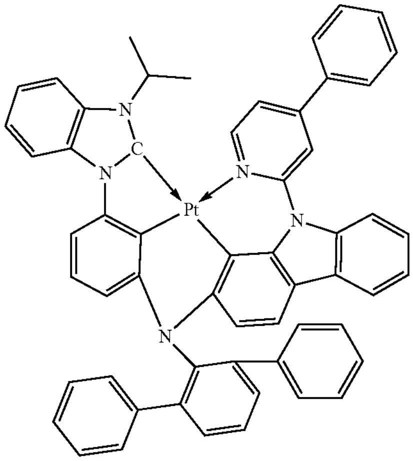
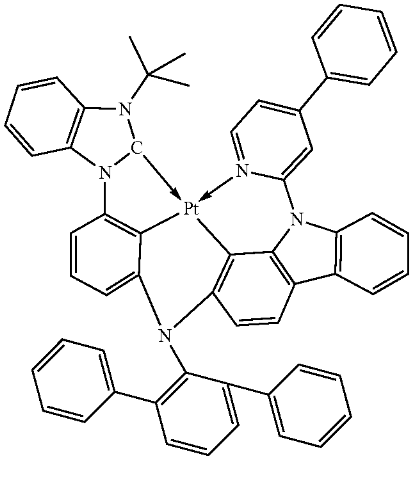

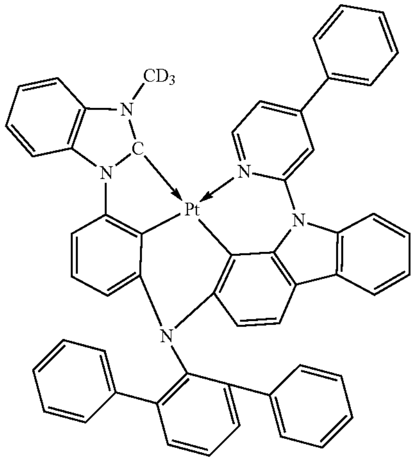
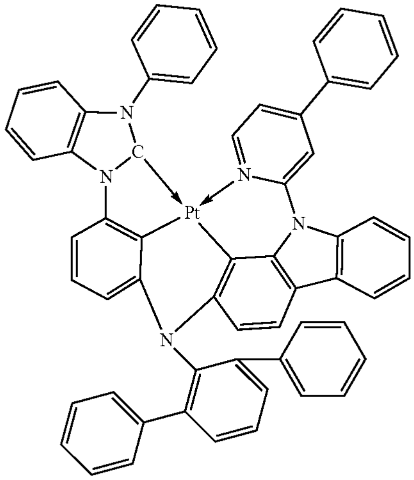
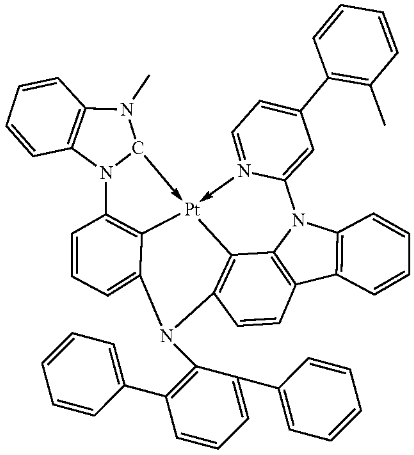
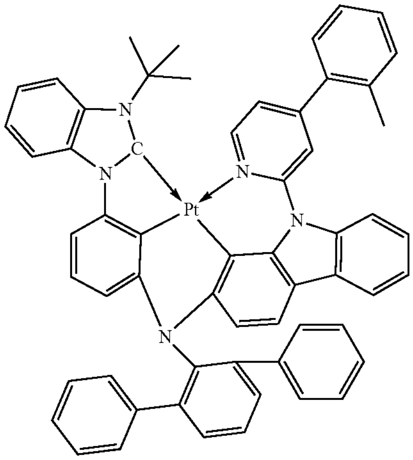
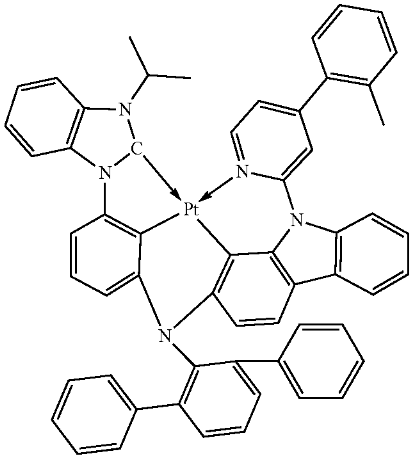
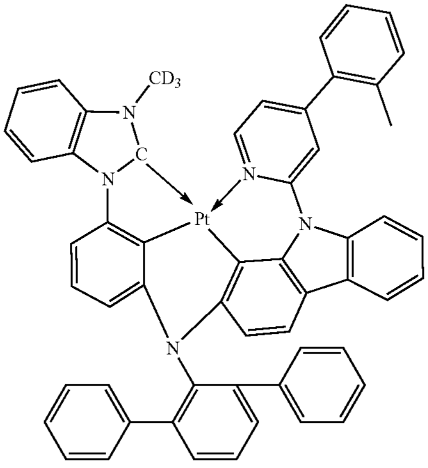

-continued
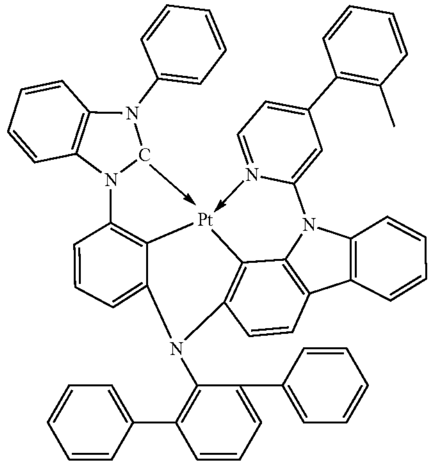
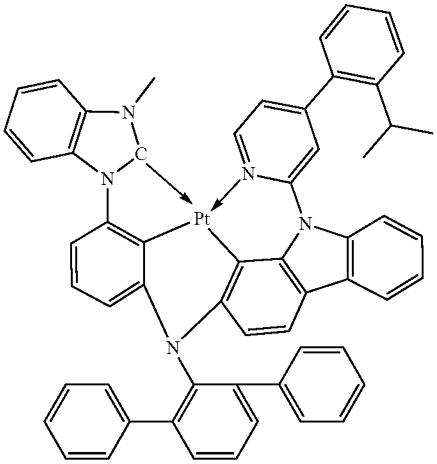
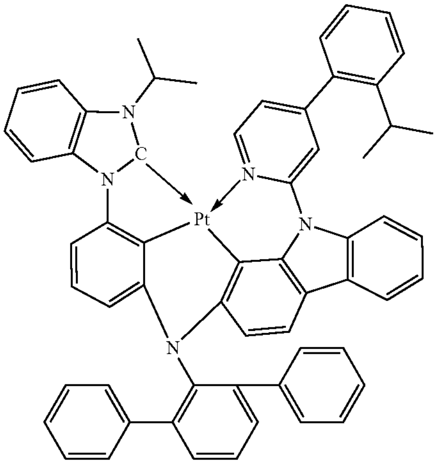
-continued
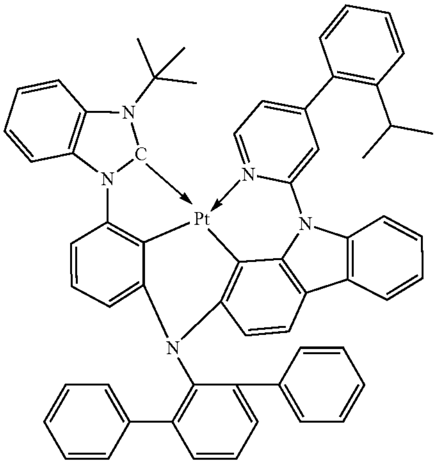
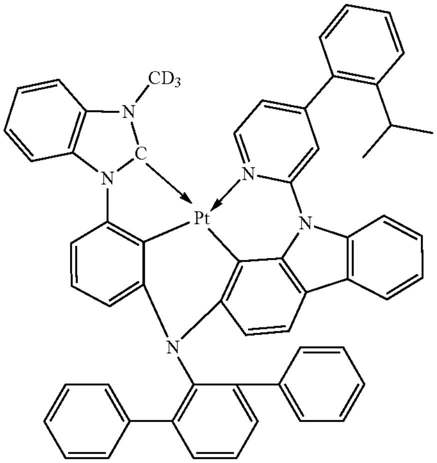
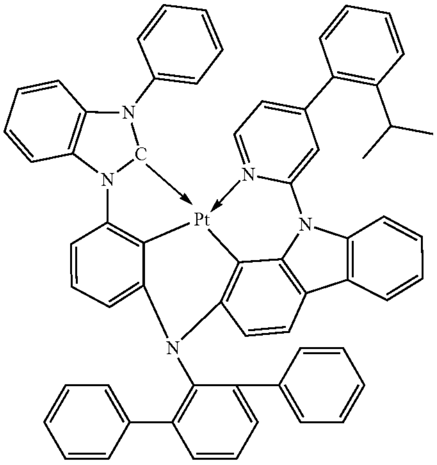

-continued
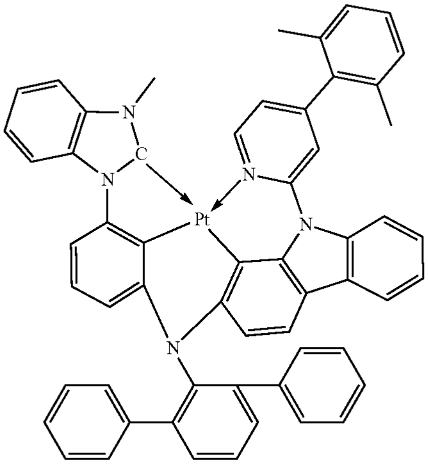
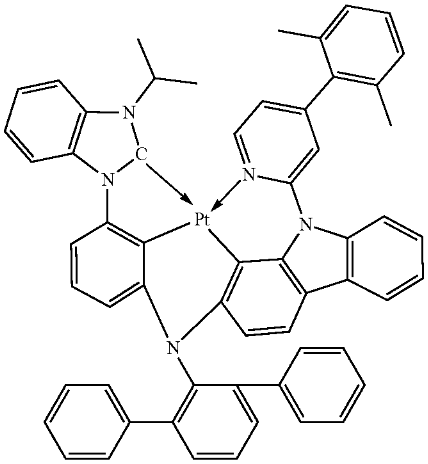
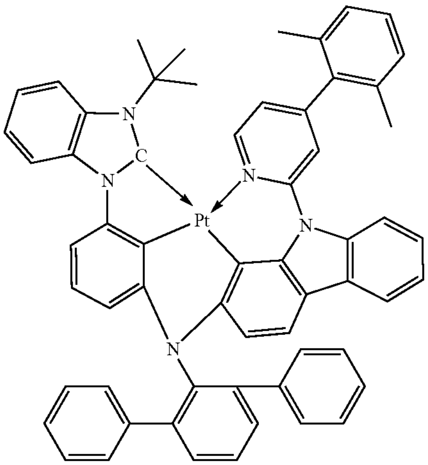
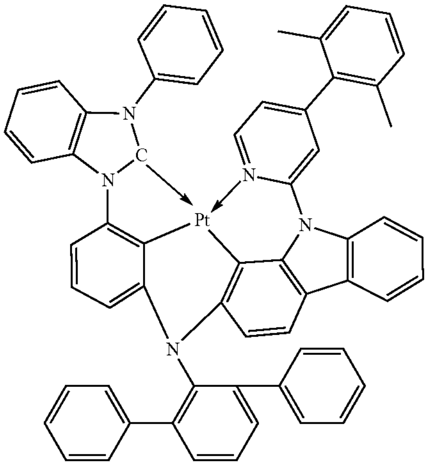
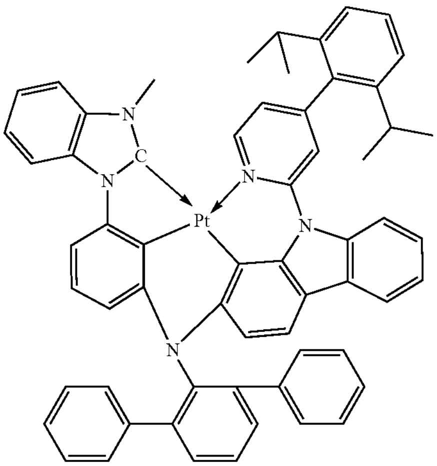
-continued
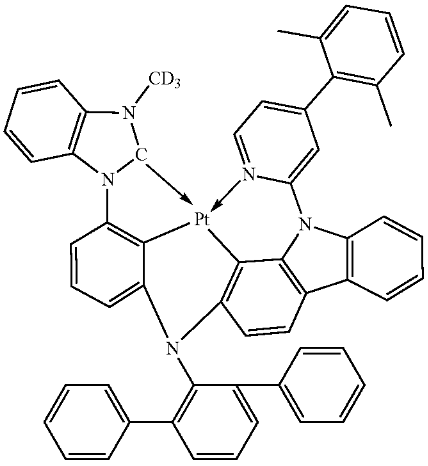

-continued
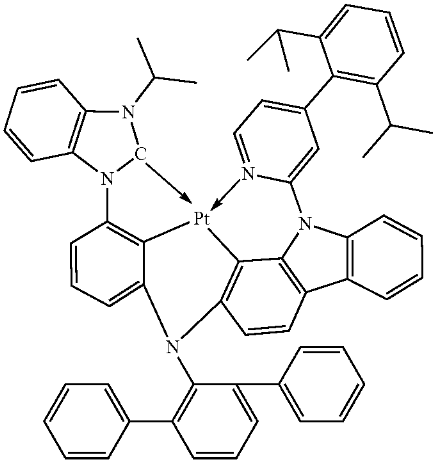
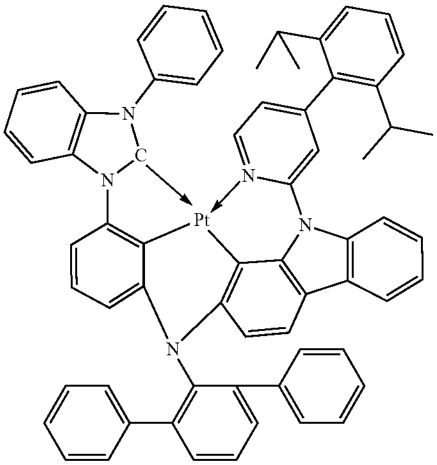
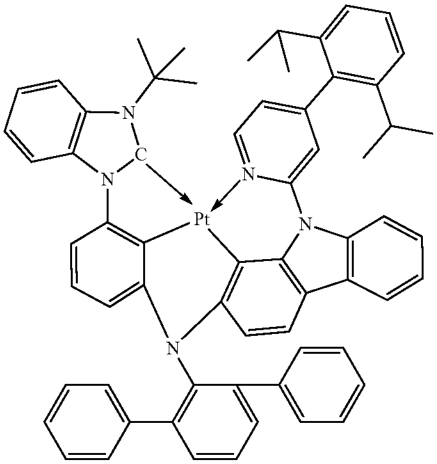
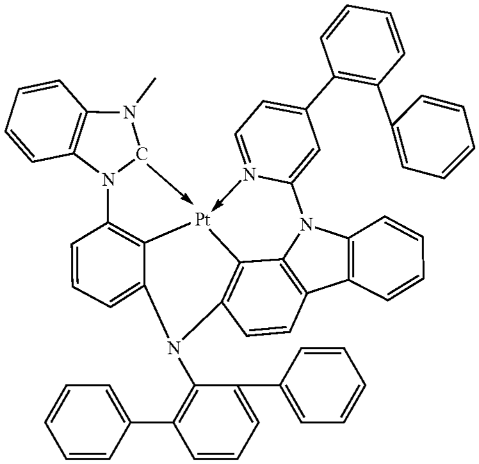
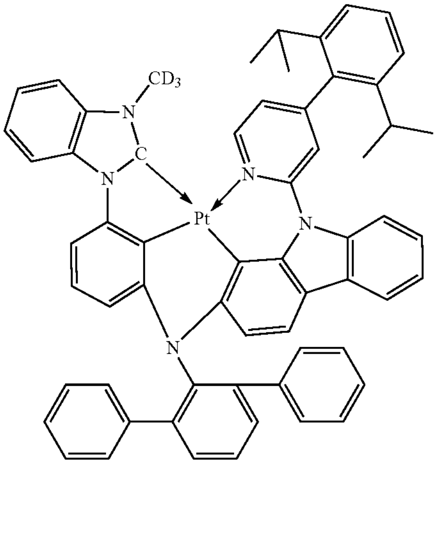
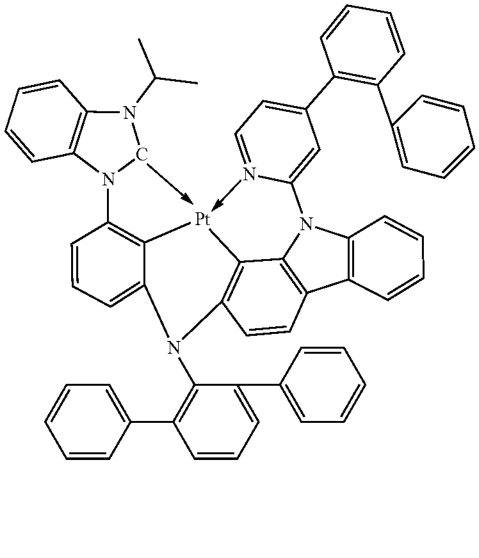

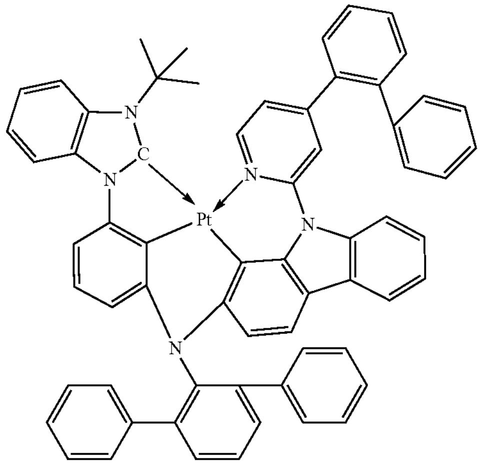
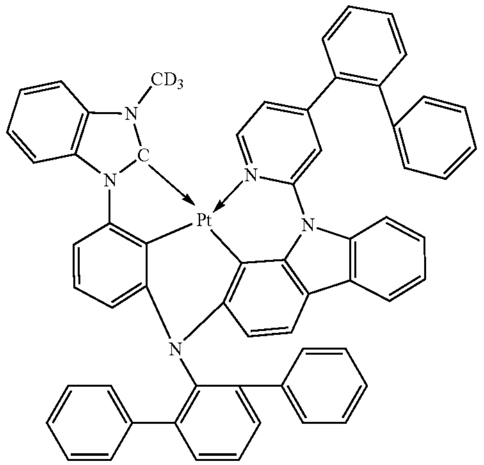
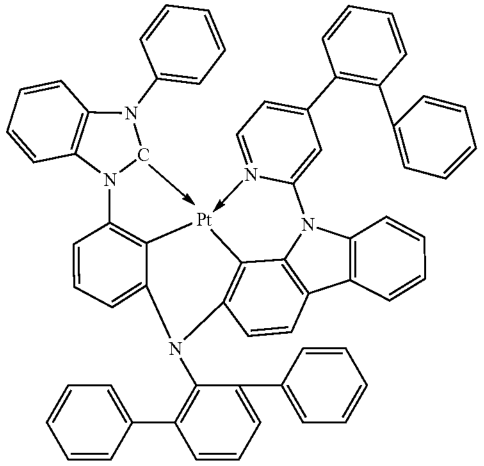
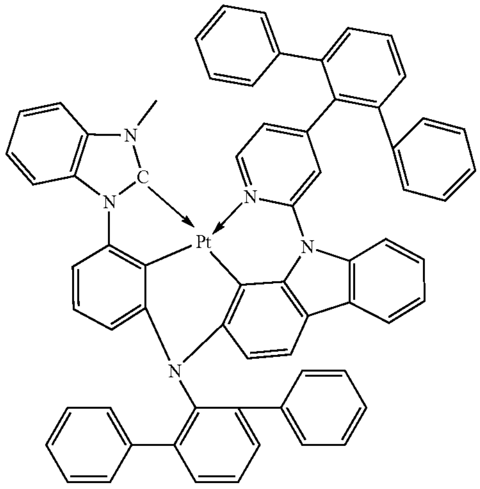
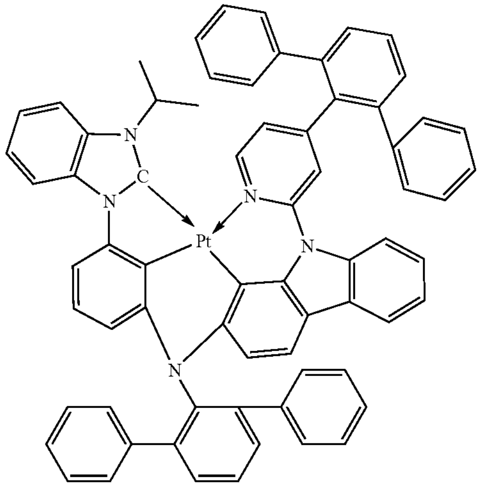
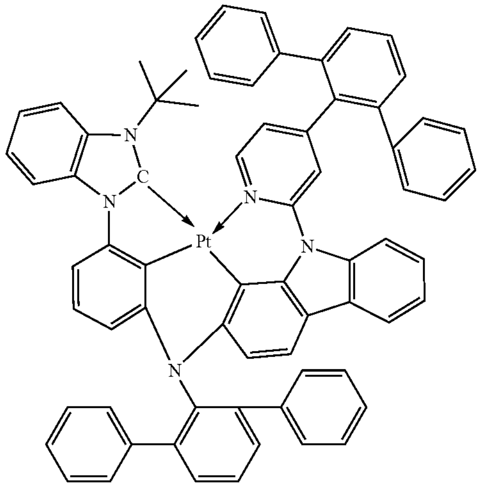

-continued
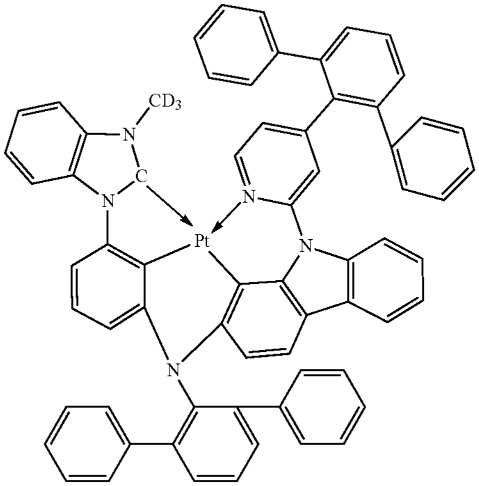
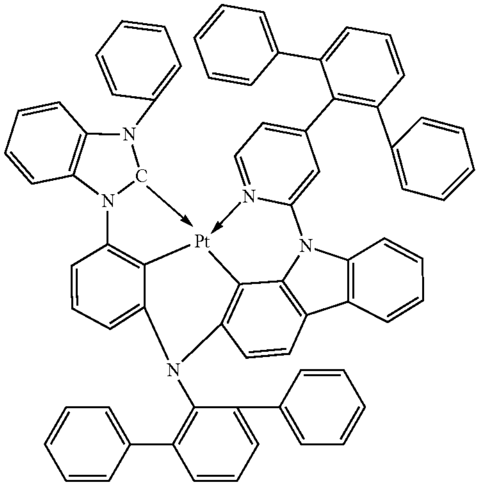
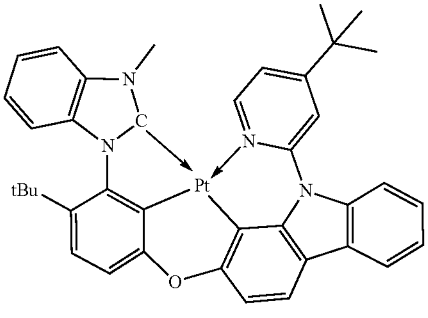
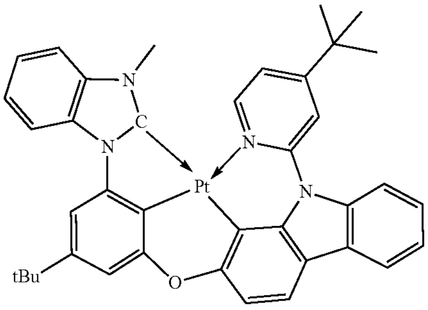
-continued
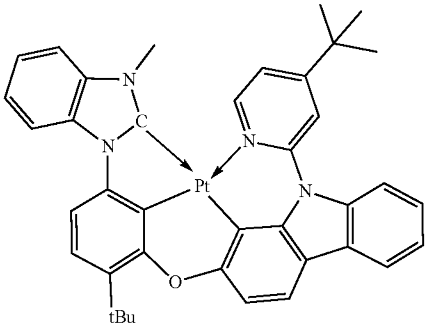
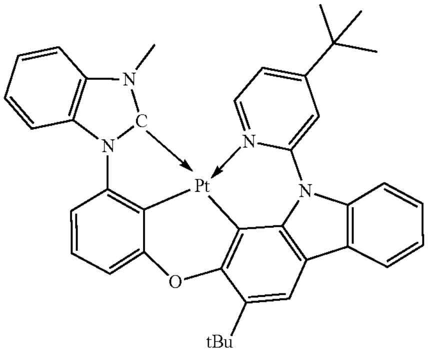
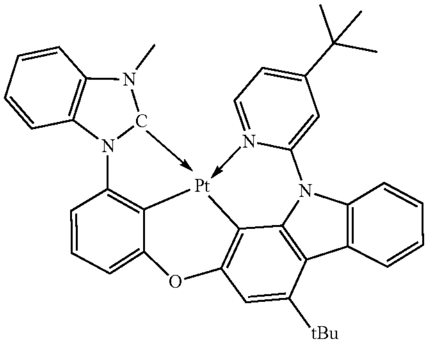
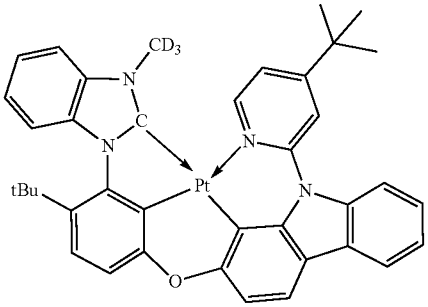
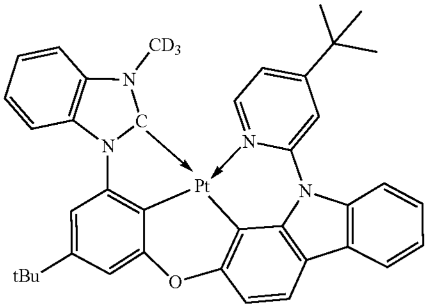

-continued
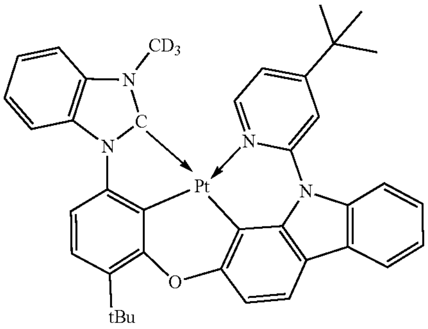
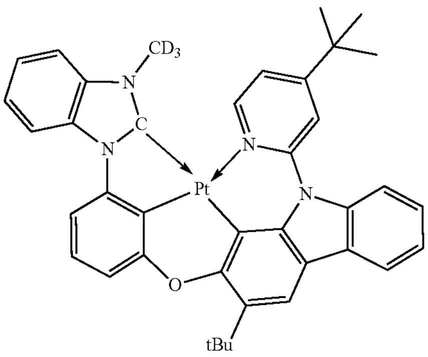
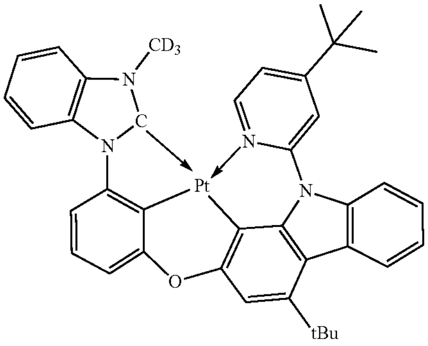
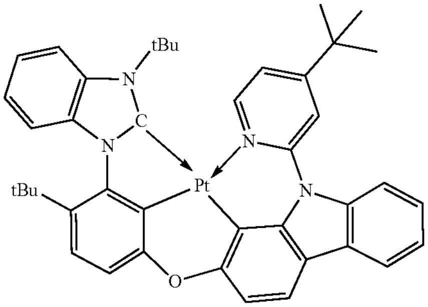
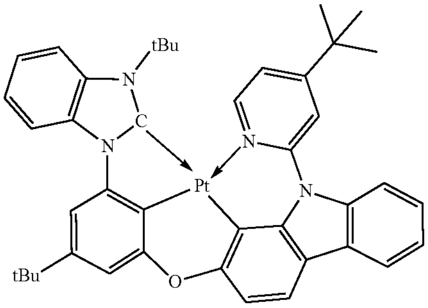
-continued
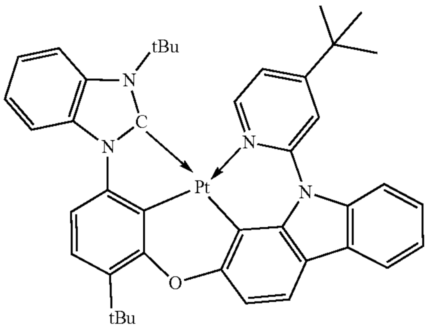
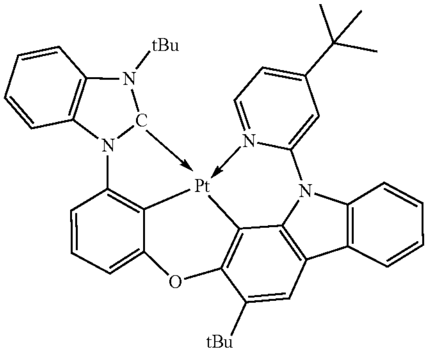
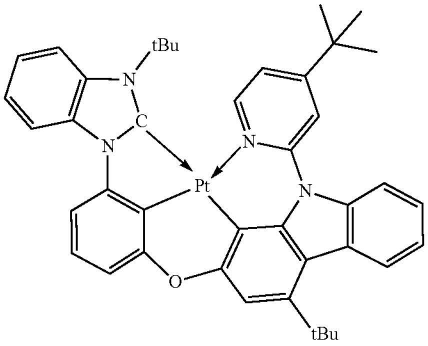
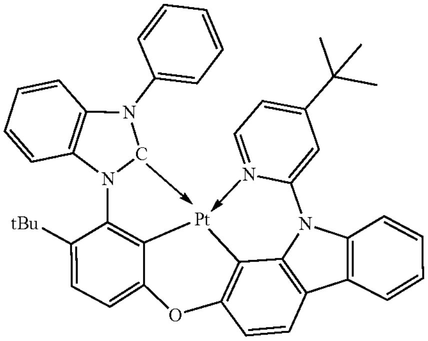
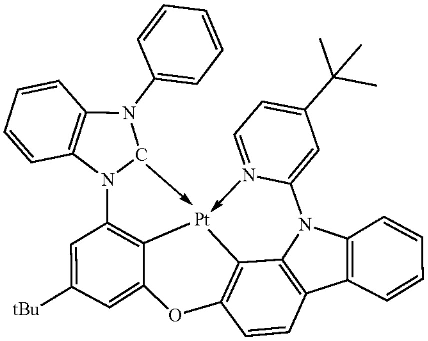

-continued
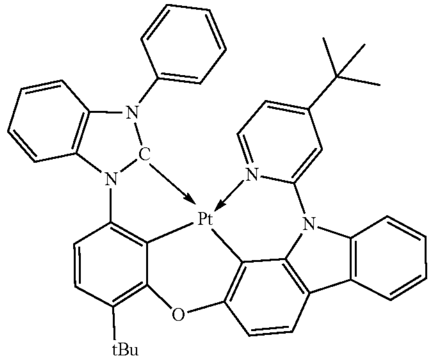
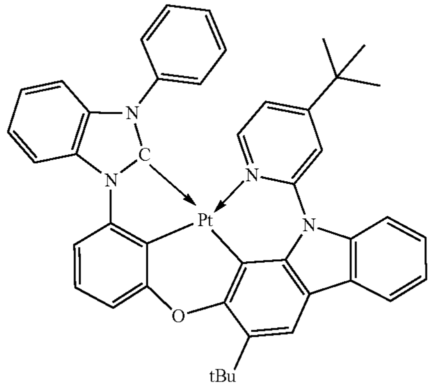
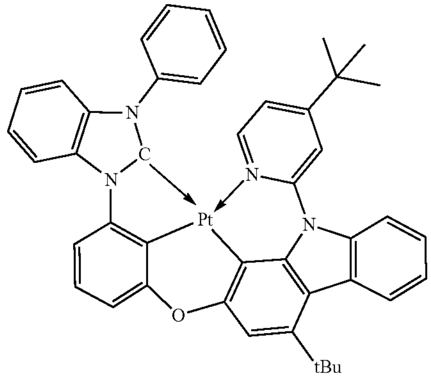
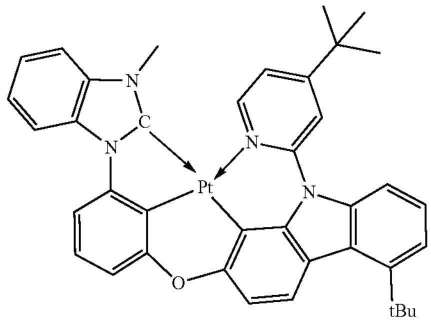
-continued
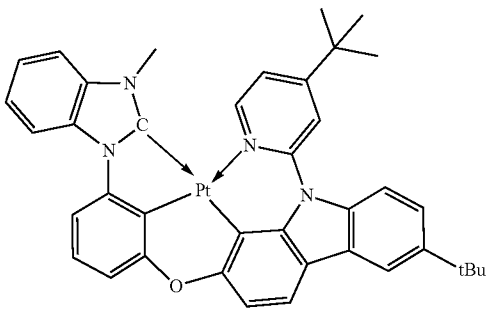
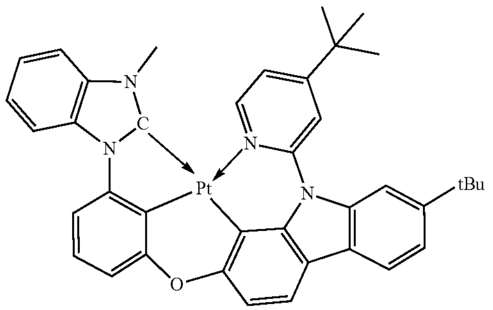
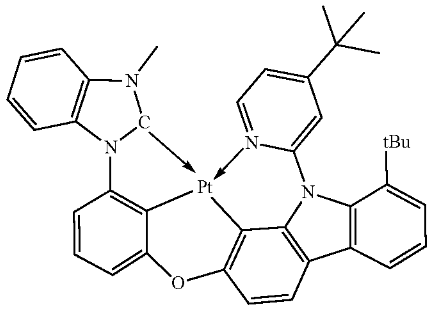
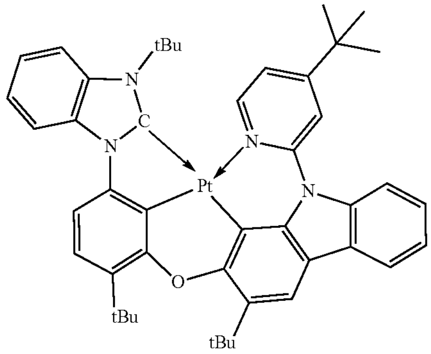
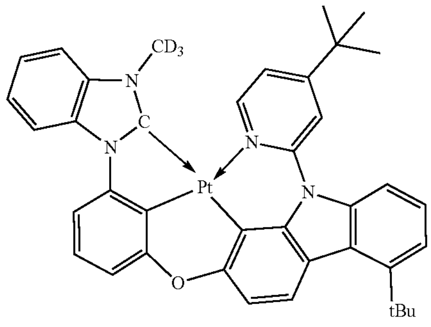

-continued
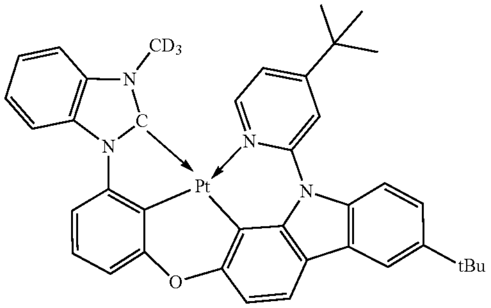
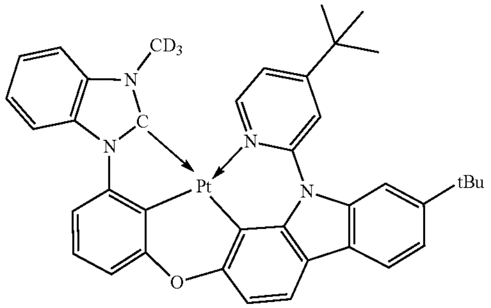
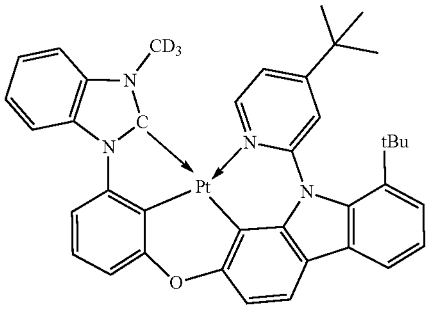
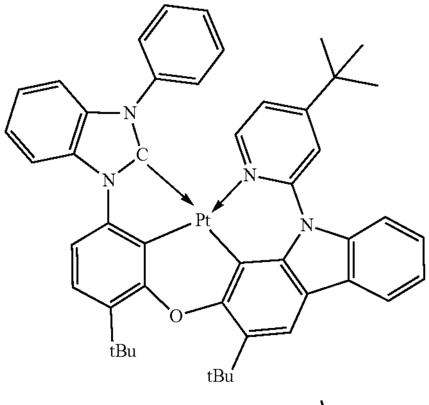
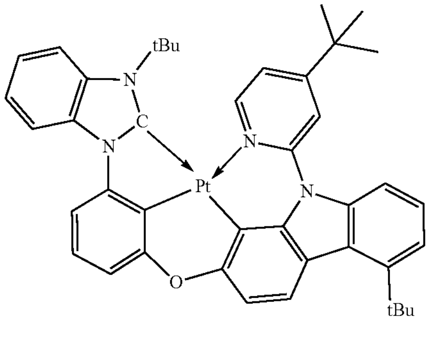
-continued
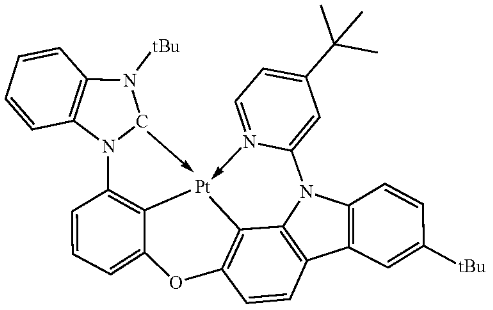
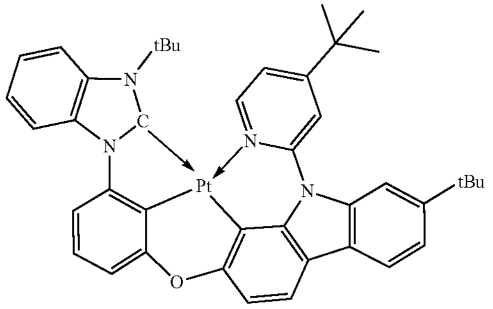
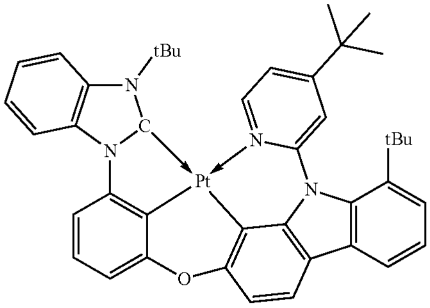
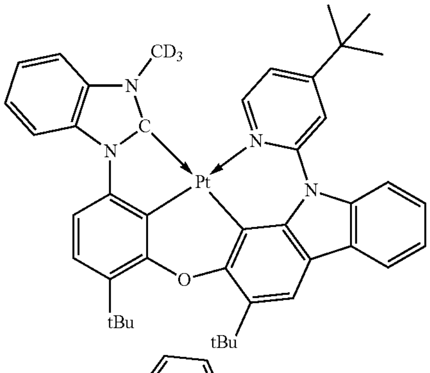
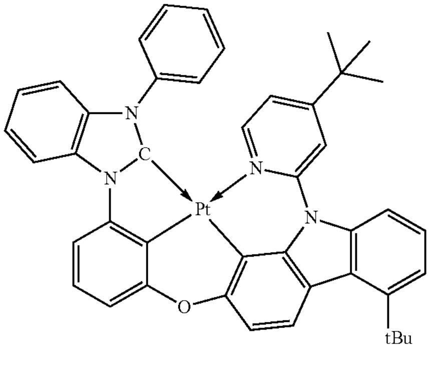

-continued
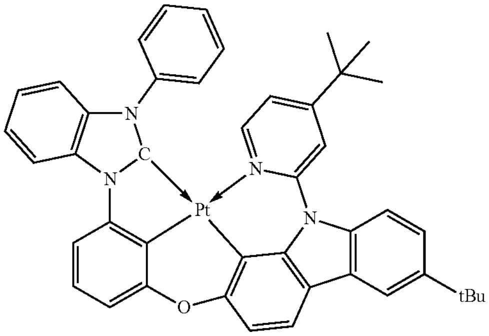
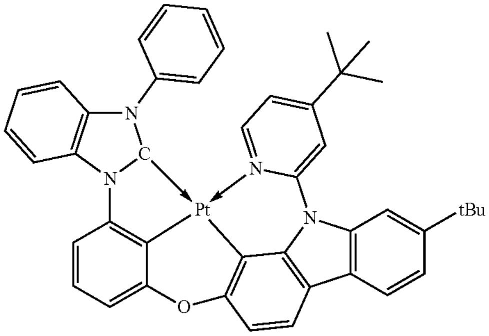
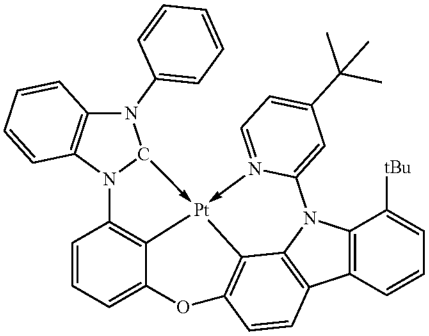
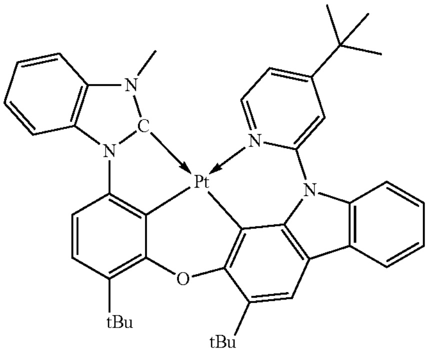
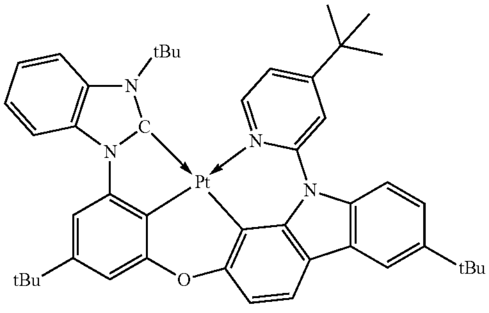
-continued
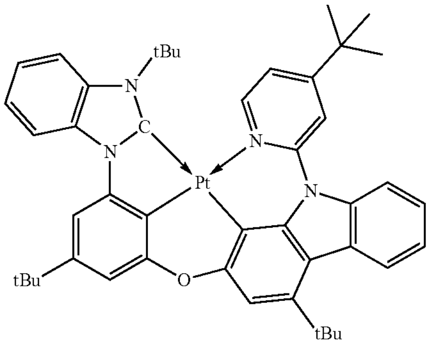
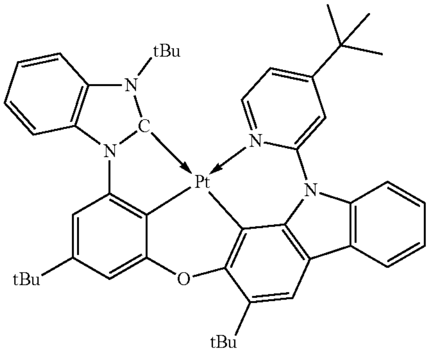
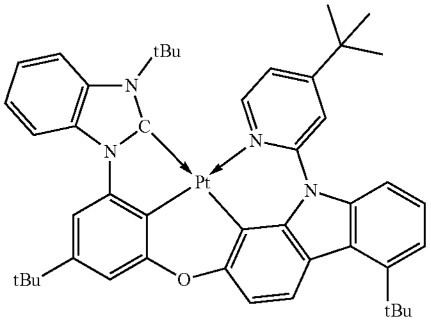
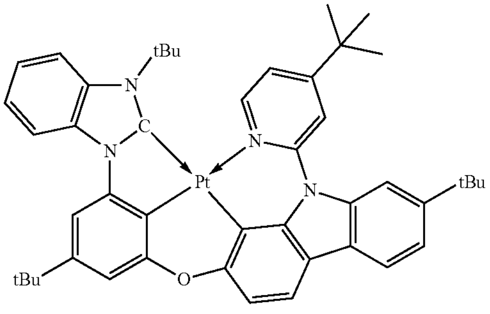
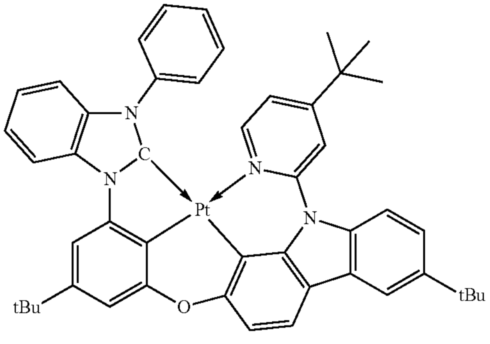

-continued
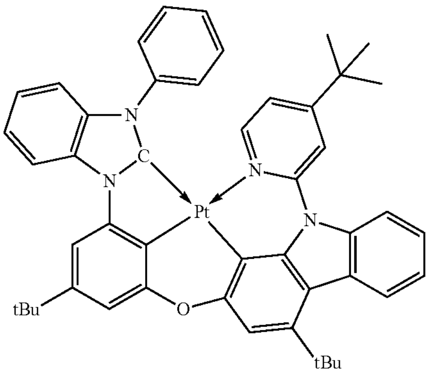
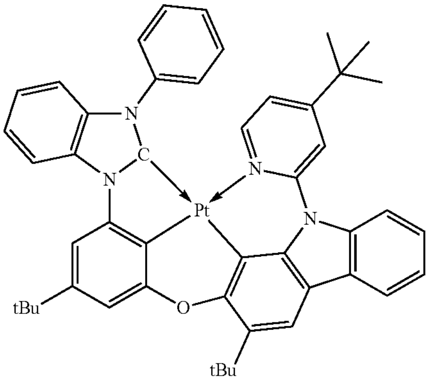
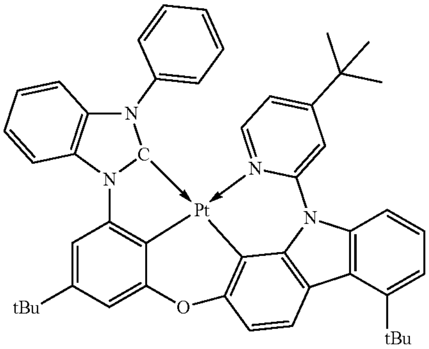
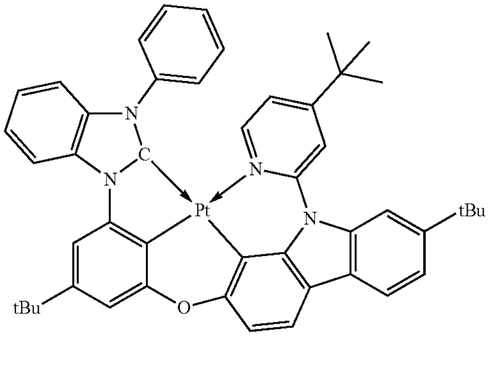
-continued
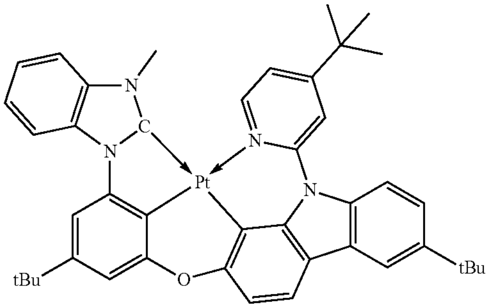
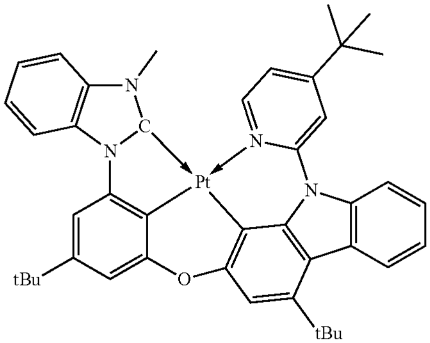
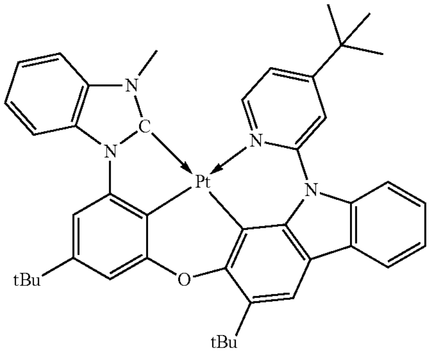
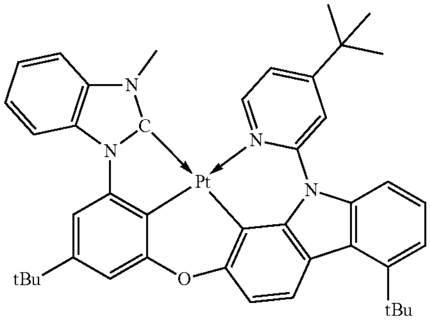
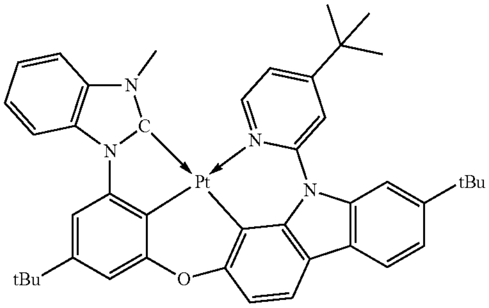

-continued
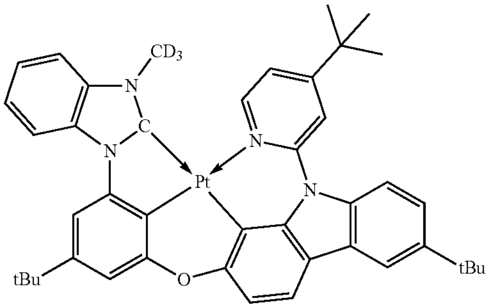
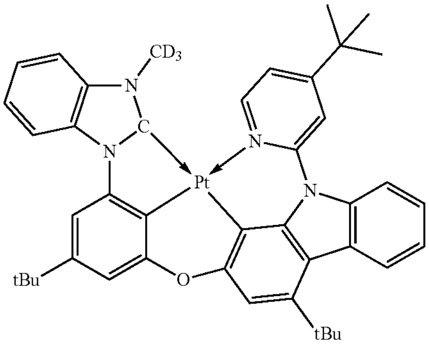
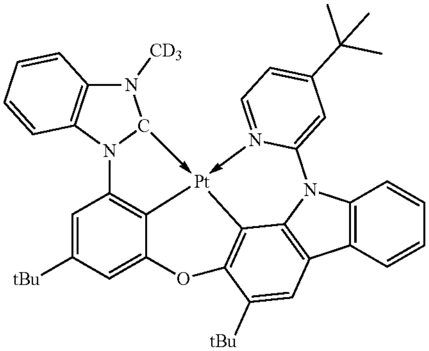
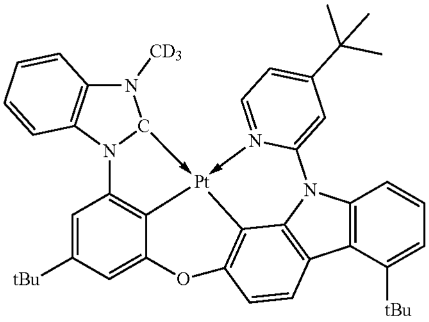
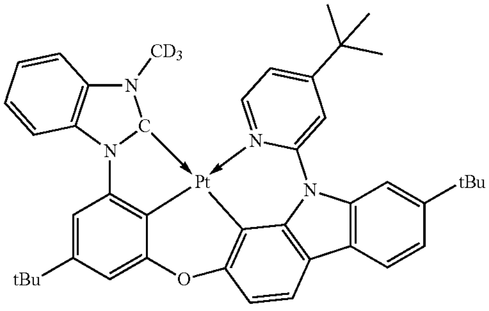
-continued
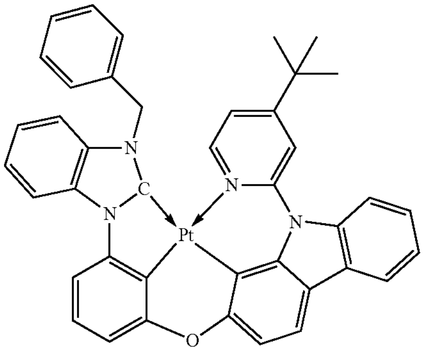
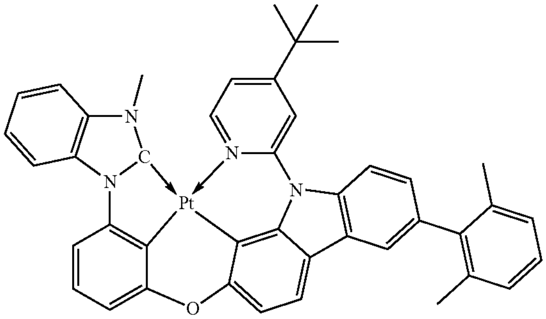
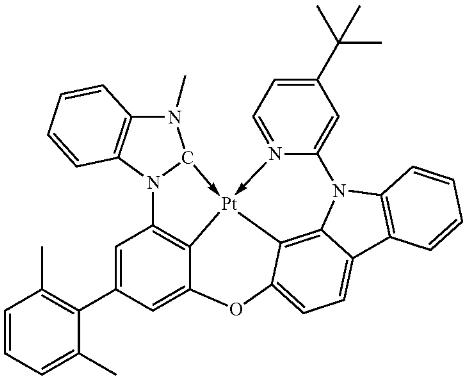
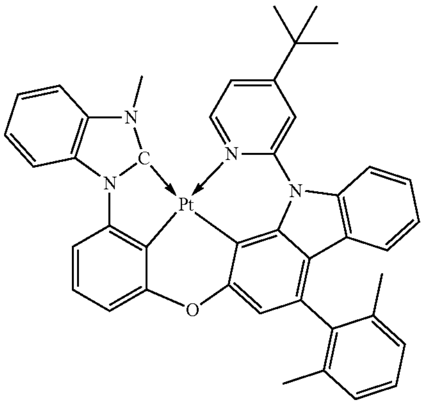

-continued
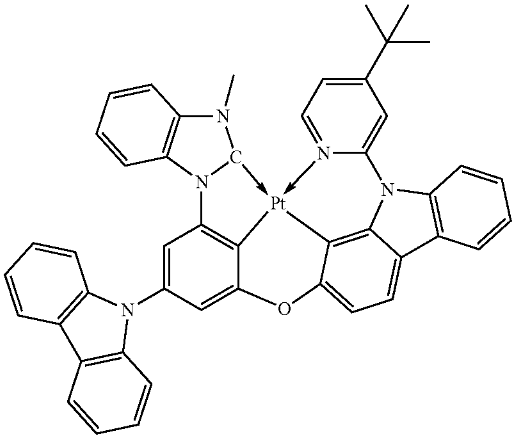
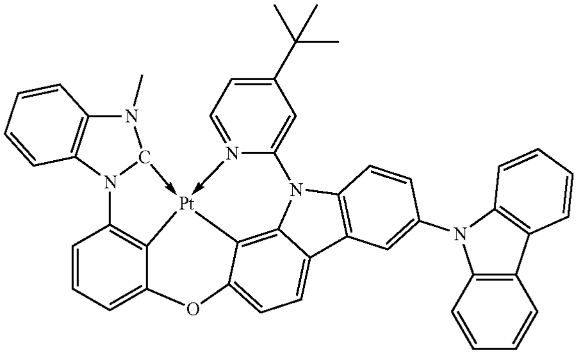
Group IV
1
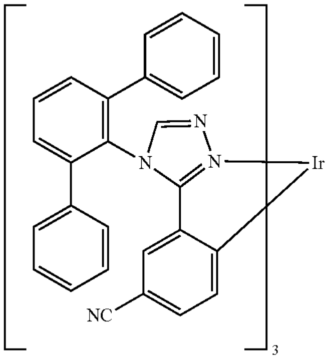
2
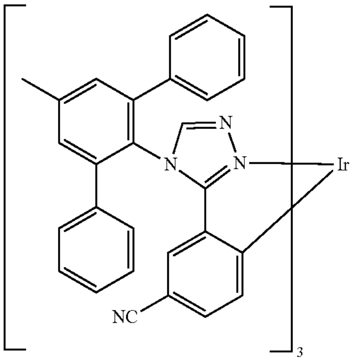
-continued
3
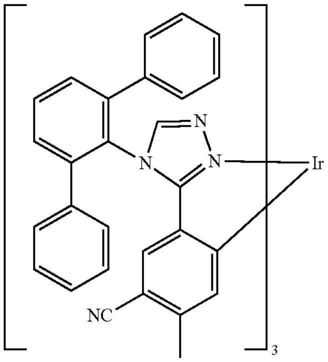
4
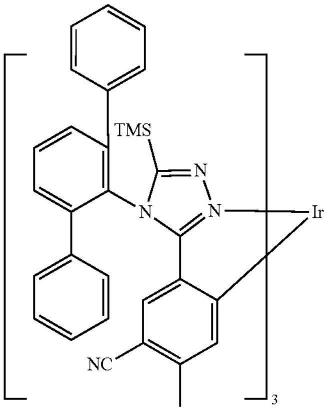
5
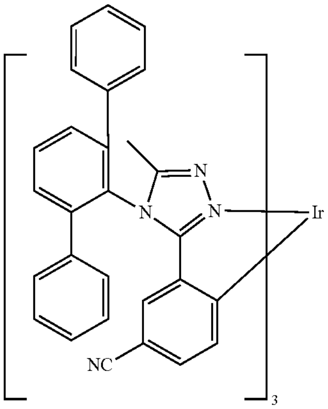
6
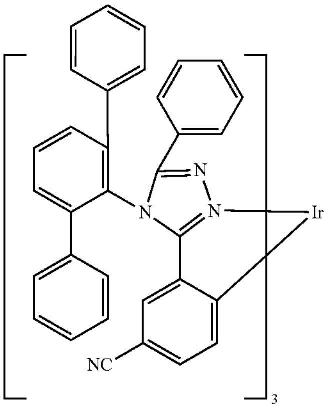

-continued

7

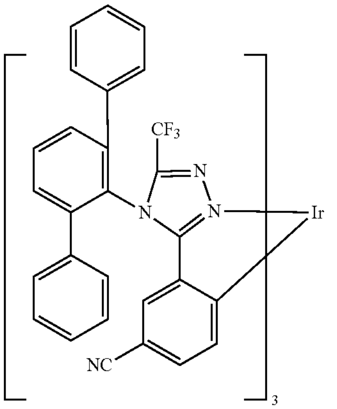

8

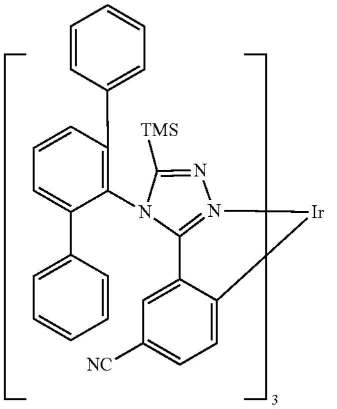

9

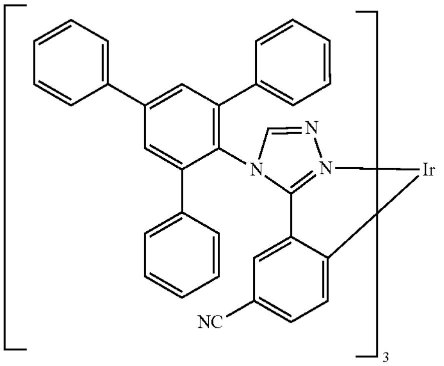

10

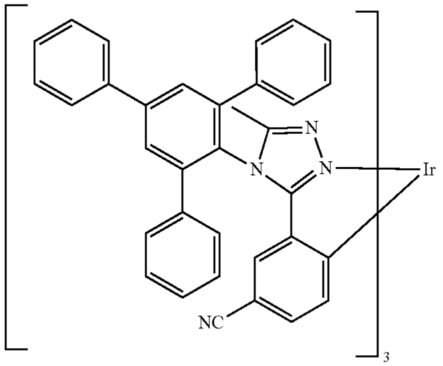

Group V a compound represented by Formula A:

$(L_{101})_{n101}\text{-}M_{101}\text{-}(L_{102})_{m101}$ Formula A wherein, in Formula A, $L_{101}$, n101, $M_{101}$, $L_{102}$, and m101 may respectively be the same as described in connection with Tables 1 to 3:

TABLE 1

| Compound name | $L_{101}$ | n101 | $M_{101}$ | $L_{102}$ | m101 |
|---|---|---|---|---|---|
| BD001 | LM1 | 3 | Ir | — | 0 |
| BD002 | LM2 | 3 | Ir | — | 0 |
| BD003 | LM3 | 3 | Ir | — | 0 |
| BD004 | LM4 | 3 | Ir | — | 0 |
| BD005 | LM5 | 3 | Ir | — | 0 |
| BD006 | LM6 | 3 | Ir | — | 0 |
| BD007 | LM7 | 3 | Ir | — | 0 |
| BD008 | LM8 | 3 | Ir | — | 0 |
| BD009 | LM9 | 3 | Ir | — | 0 |
| BD010 | LM10 | 3 | Ir | — | 0 |
| BD011 | LM11 | 3 | Ir | — | 0 |
| BD012 | LM12 | 3 | Ir | — | 0 |
| BD013 | LM13 | 3 | Ir | — | 0 |
| BD014 | LM14 | 3 | Ir | — | 0 |
| BD015 | LM15 | 3 | Ir | — | 0 |
| BD016 | LM16 | 3 | Ir | — | 0 |
| BD017 | LM17 | 3 | Ir | — | 0 |
| BD018 | LM18 | 3 | Ir | — | 0 |
| BD019 | LM19 | 3 | Ir | — | 0 |
| BD020 | LM20 | 3 | Ir | — | 0 |
| BD021 | LM21 | 3 | Ir | — | 0 |
| BD022 | LM22 | 3 | Ir | — | 0 |
| BD023 | LM23 | 3 | Ir | — | 0 |
| BD024 | LM24 | 3 | Ir | — | 0 |
| BD025 | LM25 | 3 | Ir | — | 0 |
| BD026 | LM26 | 3 | Ir | — | 0 |
| BD027 | LM27 | 3 | Ir | — | 0 |
| BD028 | LM28 | 3 | Ir | — | 0 |
| BD029 | LM29 | 3 | Ir | — | 0 |
| BD030 | LM30 | 3 | Ir | — | 0 |
| BD031 | LM31 | 3 | Ir | — | 0 |
| BD032 | LM32 | 3 | Ir | — | 0 |
| BD033 | LM33 | 3 | Ir | — | 0 |
| BD034 | LM34 | 3 | Ir | — | 0 |
| BD035 | LM35 | 3 | Ir | — | 0 |
| BD038 | LM36 | 3 | Ir | — | 0 |
| BD037 | LM37 | 3 | Ir | — | 0 |
| BD038 | LM38 | 3 | Ir | — | 0 |
| BD039 | LM39 | 3 | Ir | — | 0 |
| BD040 | LM40 | 3 | Ir | — | 0 |
| BD041 | LM41 | 3 | Ir | — | 0 |
| BD042 | LM42 | 3 | Ir | — | 0 |
| BD043 | LM43 | 3 | Ir | — | 0 |
| BD044 | LM44 | 3 | Ir | — | 0 |
| BD045 | LM45 | 3 | Ir | — | 0 |
| BD046 | LM46 | 3 | Ir | — | 0 |
| BD047 | LM47 | 3 | Ir | — | 0 |
| BD048 | LM48 | 3 | Ir | — | 0 |
| BD049 | LM49 | 3 | Ir | — | 0 |
| BD050 | LM50 | 3 | Ir | — | 0 |
| BD051 | LM51 | 3 | Ir | — | 0 |
| BD052 | LM52 | 3 | Ir | — | 0 |
| BD053 | LM53 | 3 | Ir | — | 0 |
| BD054 | LM54 | 3 | Ir | — | 0 |
| BD055 | LM55 | 3 | Ir | — | 0 |
| BD056 | LM56 | 3 | Ir | — | 0 |
| BD057 | LM57 | 3 | Ir | — | 0 |
| BD058 | LM58 | 3 | Ir | — | 0 |
| BD059 | LM59 | 3 | Ir | — | 0 |
| BD060 | LM60 | 3 | Ir | — | 0 |
| BD061 | LM61 | 3 | Ir | — | 0 |
| BD062 | LM62 | 3 | Ir | — | 0 |
| BD063 | LM63 | 3 | Ir | — | 0 |
| BD064 | LM64 | 3 | Ir | — | 0 |
| BD065 | LM65 | 3 | Ir | — | 0 |
| BD066 | LM66 | 3 | Ir | — | 0 |
| BD067 | LM67 | 3 | Ir | — | 0 |
| BD068 | LM68 | 3 | Ir | — | 0 |
| BD069 | LM69 | 3 | Ir | — | 0 |
| BD070 | LM70 | 3 | Ir | — | 0 |
| BD071 | LM71 | 3 | Ir | — | 0 |
| BD072 | LM72 | 3 | Ir | — | 0 |
| BD073 | LM73 | 3 | Ir | — | 0 |

TABLE 1-continued

| Compound name | $L_{101}$ | n101 | $M_{101}$ | $L_{102}$ | m101 |
|---|---|---|---|---|---|
| BD074 | LM74 | 3 | Ir | — | 0 |
| BD075 | LM75 | 3 | Ir | — | 0 |
| BD076 | LM76 | 3 | Ir | — | 0 |
| BD077 | LM77 | 3 | Ir | — | 0 |
| BD078 | LM78 | 3 | Ir | — | 0 |
| BD079 | LM79 | 3 | Ir | — | 0 |
| BD080 | LM80 | 3 | Ir | — | 0 |
| BD081 | LM81 | 3 | Ir | — | 0 |
| BD082 | LM82 | 3 | Ir | — | 0 |
| BD083 | LM83 | 3 | Ir | — | 0 |
| BD084 | LM84 | 3 | Ir | — | 0 |
| BD085 | LM85 | 3 | Ir | — | 0 |
| BD086 | LM86 | 3 | Ir | — | 0 |
| BD087 | LM87 | 3 | Ir | — | 0 |
| BD088 | LM88 | 3 | Ir | — | 0 |
| BD089 | LM89 | 3 | Ir | — | 0 |
| BD090 | LM90 | 3 | Ir | — | 0 |
| BD091 | LM91 | 3 | Ir | — | 0 |
| BD092 | LM92 | 3 | Ir | — | 0 |
| BD093 | LM93 | 3 | Ir | — | 0 |
| BD094 | LM94 | 3 | Ir | — | 0 |
| BD095 | LM95 | 3 | Ir | — | 0 |
| BD096 | LM96 | 3 | Ir | — | 0 |
| BD097 | LM97 | 3 | Ir | — | 0 |
| BD098 | LM98 | 3 | Ir | — | 0 |
| BD099 | LM99 | 3 | Ir | — | 0 |
| BD100 | LM100 | 3 | Ir | — | 0 |

TABLE 2

| Compound name | $L_{101}$ | n101 | $M_{101}$ | $L_{102}$ | m101 |
|---|---|---|---|---|---|
| BD101 | LM101 | 3 | Ir | — | 0 |
| BD102 | LM102 | 3 | Ir | — | 0 |
| BD103 | LM103 | 3 | Ir | — | 0 |
| BD104 | LM104 | 3 | Ir | — | 0 |
| BD105 | LM105 | 3 | Ir | — | 0 |
| BD106 | LM106 | 3 | Ir | — | 0 |
| BD107 | LM107 | 3 | Ir | — | 0 |
| BD108 | LM108 | 3 | Ir | — | 0 |
| BD109 | LM109 | 3 | Ir | — | 0 |
| BD110 | LM110 | 3 | Ir | — | 0 |
| BD111 | LM111 | 3 | Ir | — | 0 |
| BD112 | LM112 | 3 | Ir | — | 0 |
| BD113 | LM113 | 3 | Ir | — | 0 |
| BD114 | LM114 | 3 | Ir | — | 0 |
| BD115 | LM115 | 3 | Ir | — | 0 |
| BD116 | LM116 | 3 | Ir | — | 0 |
| BD117 | LM117 | 3 | Ir | — | 0 |
| BD118 | LM118 | 3 | Ir | — | 0 |
| BD119 | LM119 | 3 | Ir | — | 0 |
| BD120 | LM120 | 3 | Ir | — | 0 |
| BD121 | LM121 | 3 | Ir | — | 0 |
| BD122 | LM122 | 3 | Ir | — | 0 |
| BD123 | LM123 | 3 | Ir | — | 0 |
| BD124 | LM124 | 3 | Ir | — | 0 |
| BD125 | LM125 | 3 | Ir | — | 0 |
| BD126 | LM126 | 3 | Ir | — | 0 |
| BD127 | LM127 | 3 | Ir | — | 0 |
| BD128 | LM128 | 3 | Ir | — | 0 |
| BD129 | LM129 | 3 | Ir | — | 0 |
| BD130 | LM130 | 3 | Ir | — | 0 |
| BD131 | LM131 | 3 | Ir | — | 0 |
| BD132 | LM132 | 3 | Ir | — | 0 |
| BD133 | LM133 | 3 | Ir | — | 0 |
| BD134 | LM134 | 3 | Ir | — | 0 |
| BD135 | LM135 | 3 | Ir | — | 0 |
| BD136 | LM136 | 3 | Ir | — | 0 |
| BD137 | LM137 | 3 | Ir | — | 0 |
| BD138 | LM138 | 3 | Ir | — | 0 |
| BD139 | LM139 | 3 | Ir | — | 0 |
| BD140 | LM140 | 3 | Ir | — | 0 |
| BD141 | LM141 | 3 | Ir | — | 0 |
| BD142 | LM142 | 3 | Ir | — | 0 |
| BD143 | LM143 | 3 | Ir | — | 0 |

TABLE 2-continued

| Compound name | $L_{101}$ | n101 | $M_{101}$ | $L_{102}$ | m101 |
|---|---|---|---|---|---|
| BD144 | LM144 | 3 | Ir | — | 0 |
| BD145 | LM145 | 3 | Ir | — | 0 |
| BD146 | LM146 | 3 | Ir | — | 0 |
| BD147 | LM147 | 3 | Ir | — | 0 |
| BD148 | LM148 | 3 | Ir | — | 0 |
| BD149 | LM149 | 3 | Ir | — | 0 |
| BD150 | LM150 | 3 | Ir | — | 0 |
| BD151 | LM151 | 3 | Ir | — | 0 |
| BD152 | LM152 | 3 | Ir | — | 0 |
| BD153 | LM153 | 3 | Ir | — | 0 |
| BD154 | LM154 | 3 | Ir | — | 0 |
| BD155 | LM155 | 3 | Ir | — | 0 |
| BD156 | LM156 | 3 | Ir | — | 0 |
| BD157 | LM157 | 3 | Ir | — | 0 |
| BD158 | LM158 | 3 | Ir | — | 0 |
| BD159 | LM159 | 3 | Ir | — | 0 |
| BD160 | LM160 | 3 | Ir | — | 0 |
| BD161 | LM161 | 3 | Ir | — | 0 |
| BD162 | LM162 | 3 | Ir | — | 0 |
| BD163 | LM163 | 3 | Ir | — | 0 |
| BD164 | LM164 | 3 | Ir | — | 0 |
| BD165 | LM165 | 3 | Ir | — | 0 |
| BD166 | LM166 | 3 | Ir | — | 0 |
| BD167 | LM167 | 3 | Ir | — | 0 |
| BD168 | LM168 | 3 | Ir | — | 0 |
| BD169 | LM169 | 3 | Ir | — | 0 |
| BD170 | LM170 | 3 | Ir | — | 0 |
| BD171 | LM171 | 3 | Ir | — | 0 |
| BD172 | LM172 | 3 | Ir | — | 0 |
| BD173 | LM173 | 3 | Ir | — | 0 |
| BD174 | LM174 | 3 | Ir | — | 0 |
| BD175 | LM175 | 3 | Ir | — | 0 |
| BD176 | LM176 | 3 | Ir | — | 0 |
| BD177 | LM177 | 3 | Ir | — | 0 |
| BD178 | LM178 | 3 | Ir | — | 0 |
| BD179 | LM179 | 3 | Ir | — | 0 |
| BD180 | LM180 | 3 | Ir | — | 0 |
| BD181 | LM181 | 3 | Ir | — | 0 |
| BD182 | LM182 | 3 | Ir | — | 0 |
| BD183 | LM183 | 3 | Ir | — | 0 |
| BD184 | LM184 | 3 | Ir | — | 0 |
| BD185 | LM185 | 3 | Ir | — | 0 |
| BD186 | LM186 | 3 | Ir | — | 0 |
| BD187 | LM187 | 3 | Ir | — | 0 |
| BD188 | LM188 | 3 | Ir | — | 0 |
| BD189 | LM189 | 3 | Ir | — | 0 |
| BD190 | LM190 | 3 | Ir | — | 0 |
| BD191 | LM191 | 3 | Ir | — | 0 |
| BD192 | LM192 | 3 | Ir | — | 0 |
| BD193 | LM193 | 3 | Ir | — | 0 |
| BD194 | LM194 | 3 | Ir | — | 0 |
| BD195 | LM195 | 3 | Ir | — | 0 |
| BD196 | LM196 | 3 | Ir | — | 0 |
| BD197 | LM197 | 3 | Ir | — | 0 |
| BD198 | LM198 | 3 | Ir | — | 0 |
| BD199 | LM199 | 3 | Ir | — | 0 |
| BD200 | LM200 | 3 | Ir | — | 0 |

TABLE 3

| Compound name | $L_{101}$ | n101 | $M_{101}$ | $L_{102}$ | m101 |
|---|---|---|---|---|---|
| BD201 | LM201 | 3 | Ir | — | 0 |
| BD202 | LM202 | 3 | Ir | — | 0 |
| BD203 | LM203 | 3 | Ir | — | 0 |
| BD204 | LM204 | 3 | Ir | — | 0 |
| BD205 | LM205 | 3 | Ir | — | 0 |
| BD206 | LM206 | 3 | Ir | — | 0 |
| BD207 | LM207 | 3 | Ir | — | 0 |
| BD208 | LM208 | 3 | Ir | — | 0 |
| BD209 | LM209 | 3 | Ir | — | 0 |
| BD210 | LM210 | 3 | Ir | — | 0 |
| BD211 | LM211 | 3 | Ir | — | 0 |
| BD212 | LM212 | 3 | Ir | — | 0 |
| BD213 | LM213 | 3 | Ir | — | 0 |

TABLE 3-continued

| Compound name | $L_{101}$ | n101 | $M_{101}$ | $L_{102}$ | m101 |
|---|---|---|---|---|---|
| BD214 | LM214 | 3 | Ir | — | 0 |
| BD215 | LM215 | 3 | Ir | — | 0 |
| BD216 | LM216 | 3 | Ir | — | 0 |
| BD217 | LM217 | 3 | Ir | — | 0 |
| BD218 | LM218 | 3 | Ir | — | 0 |
| BD219 | LM219 | 3 | Ir | — | 0 |
| BD220 | LM220 | 3 | Ir | — | 0 |
| BD221 | LM221 | 3 | Ir | — | 0 |
| BD222 | LM222 | 3 | Ir | — | 0 |
| BD223 | LM223 | 3 | Ir | — | 0 |
| BD224 | LM224 | 3 | Ir | — | 0 |
| BD225 | LM225 | 3 | Ir | — | 0 |
| BD226 | LM226 | 3 | Ir | — | 0 |
| BD227 | LM227 | 3 | Ir | — | 0 |
| BD228 | LM228 | 3 | Ir | — | 0 |
| BD229 | LM229 | 3 | Ir | — | 0 |
| BD230 | LM230 | 3 | Ir | — | 0 |
| BD231 | LM231 | 3 | Ir | — | 0 |
| BD232 | LM232 | 3 | Ir | — | 0 |
| BD233 | LM233 | 3 | Ir | — | 0 |
| BD234 | LM234 | 3 | Ir | — | 0 |
| BD235 | LM235 | 3 | Ir | — | 0 |
| BD236 | LM236 | 3 | Ir | — | 0 |
| BD237 | LM237 | 3 | Ir | — | 0 |
| BD238 | LM238 | 3 | Ir | — | 0 |
| BD239 | LM239 | 3 | Ir | — | 0 |
| BD240 | LM240 | 3 | Ir | — | 0 |
| BD241 | LM241 | 3 | Ir | — | 0 |
| BD242 | LM242 | 3 | Ir | — | 0 |
| BD243 | LM243 | 3 | Ir | — | 0 |
| BD244 | LFM1 | 3 | Ir | — | 0 |
| BD245 | LFM2 | 3 | Ir | — | 0 |
| BD246 | LFM3 | 3 | Ir | — | 0 |
| BD247 | LFM4 | 3 | Ir | — | 0 |
| BD248 | LFM5 | 3 | Ir | — | 0 |
| BD249 | LFM6 | 3 | Ir | — | 0 |
| BD250 | LFM7 | 3 | Ir | — | 0 |
| BD251 | LFP1 | 3 | Ir | — | 0 |
| BD252 | LFP2 | 3 | Ir | — | 0 |
| BD253 | LFP3 | 3 | Ir | — | 0 |
| BD254 | LFP4 | 3 | Ir | — | 0 |
| BD255 | LFP5 | 3 | Ir | — | 0 |
| BD256 | LFP6 | 3 | Ir | — | 0 |
| BD257 | LFP7 | 3 | Ir | — | 0 |
| BD258 | LM47 | 2 | Ir | AN1 | 1 |
| BD259 | LM47 | 2 | Ir | AN2 | 1 |
| BD260 | LM47 | 2 | Ir | AN3 | 1 |
| BD261 | LM47 | 2 | Ir | AN4 | 1 |
| BD262 | LM47 | 2 | Ir | AN5 | 1 |
| BD263 | LM11 | 2 | Pt | — | 0 |
| BD264 | LM13 | 2 | Pt | — | 0 |
| BD265 | LM15 | 2 | Pt | — | 0 |
| BD266 | LM45 | 2 | Pt | — | 0 |
| BD267 | LM47 | 2 | Pt | — | 0 |
| BD268 | LM49 | 2 | Pt | — | 0 |
| BD269 | LM98 | 2 | Pt | — | 0 |
| BD270 | LM100 | 2 | Pt | — | 0 |
| BD271 | LM102 | 2 | Pt | — | 0 |
| BD272 | LM132 | 2 | Pt | — | 0 |
| BD273 | LM134 | 2 | Pt | — | 0 |
| BD274 | LM136 | 2 | Pt | — | 0 |
| BD275 | LM151 | 2 | Pt | — | 0 |
| BD276 | LM153 | 2 | Pt | — | 0 |
| BD277 | LM158 | 2 | Pt | — | 0 |
| BD278 | LM180 | 2 | Pt | — | 0 |
| BD279 | LM182 | 2 | Pt | — | 0 |
| BD280 | LM187 | 2 | Pt | — | 0 |
| BD281 | LM201 | 2 | Pt | — | 0 |
| BD282 | LM206 | 2 | Pt | — | 0 |
| BD283 | LM211 | 2 | Pt | — | 0 |
| BD284 | LM233 | 2 | Pt | — | 0 |
| BD285 | LM235 | 2 | Pt | — | 0 |
| BD286 | LM240 | 2 | Pt | — | 0 |
| BD287 | LFM5 | 2 | Pt | — | 0 |
| BD288 | LFM6 | 2 | Pt | — | 0 |
| BD289 | LFM7 | 2 | Pt | — | 0 |
| BD290 | LFP5 | 2 | Pt | — | 0 |
| BD291 | LFP6 | 2 | Pt | — | 0 |

TABLE 3-continued

| Compound name | $L_{101}$ | n101 | $M_{101}$ | $L_{102}$ | m101 |
|---|---|---|---|---|---|
| BD292 | LFP7 | 2 | Pt | — | 0 |
| BD293 | LM47 | 1 | Pt | AN1 | 1 |
| BD294 | LM47 | 1 | Pt | AN2 | 1 |
| BD295 | LM47 | 1 | Pt | AN3 | 1 |
| BD296 | LM47 | 1 | Pt | AN4 | 1 |
| BD297 | LM47 | 1 | Pt | AN5 | 1 |

In Tables 1 to 3, LM1 to LM243 may respectively be understood by referring to Formulae 11-1 to 11-3 and Tables 4 to 6:

11-1

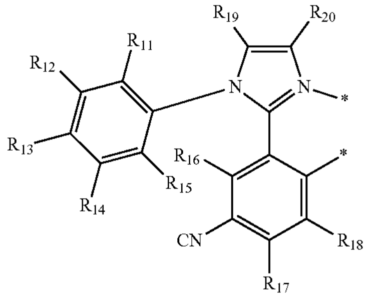

11-2

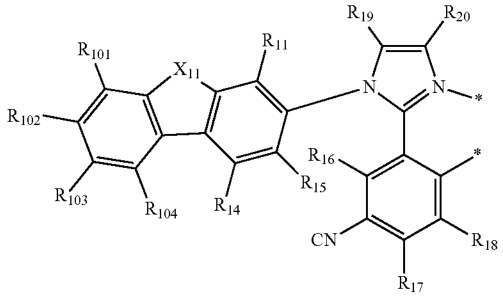

11-3

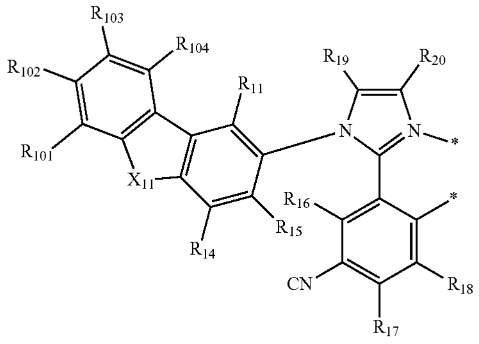

TABLE 4

| Formula 11-1 | | | | | | | | | | |
|---|---|---|---|---|---|---|---|---|---|---|
| Ligand name | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
| LM1 | X1 | H | X3 | H | X1 | H | H | H | H | D |
| LM2 | X1 | H | X3 | H | X1 | H | H | H | D | H |
| LM3 | X1 | H | X3 | H | X1 | H | H | H | D | D |
| LM4 | Y1 | H | X3 | H | Y1 | H | H | H | D | D |
| LM5 | Y2 | H | X3 | H | Y2 | H | H | H | D | D |
| LM6 | Y3 | H | X3 | H | Y3 | H | H | H | D | D |
| LM7 | Y3 | D | X3 | D | Y3 | H | H | H | D | D |
| LM8 | Y3 | D | X3 | D | Y3 | D | H | H | D | D |
| LM9 | Y3 | D | X3 | D | Y3 | D | D | H | D | D |
| LM10 | Y3 | D | X3 | D | Y3 | D | D | D | D | D |
| LM11 | Y3 | D | Y11 | D | Y3 | D | D | D | D | D |
| LM12 | Y3 | D | Y11 | D | Y3 | H | X1 | H | D | D |
| LM13 | Y3 | D | Y11 | D | Y3 | D | Y3 | D | D | D |
| LM14 | Y3 | D | Y11 | D | Y3 | H | X4 | H | D | D |
| LM15 | Y3 | D | Y11 | D | Y3 | D | Y12 | D | D | D |
| LM16 | X2 | H | X3 | H | X2 | H | H | H | H | D |
| LM17 | X2 | H | X3 | H | X2 | H | H | H | D | H |
| LM18 | X2 | H | X3 | H | X2 | H | H | H | D | D |
| LM19 | Y4 | H | X3 | H | Y4 | H | H | H | D | D |
| LM20 | Y5 | H | X3 | H | Y5 | H | H | H | D | D |
| LM21 | Y6 | H | X3 | H | Y6 | H | H | H | D | D |
| LM22 | Y7 | H | X3 | H | Y7 | H | H | H | D | D |
| LM23 | Y8 | H | X3 | H | Y8 | H | H | H | D | D |
| LM24 | Y9 | H | X3 | H | Y9 | H | H | H | D | D |
| LM25 | Y10 | H | X3 | H | Y10 | H | H | H | D | D |
| LM26 | Y10 | D | X3 | D | Y10 | H | H | H | D | D |
| LM27 | Y10 | D | X3 | D | Y10 | D | H | H | D | D |
| LM28 | Y10 | D | X3 | D | Y10 | D | D | H | D | D |
| LM29 | Y10 | D | X3 | D | Y10 | D | D | D | D | D |
| LM30 | Y10 | D | Y11 | D | Y10 | D | D | D | D | D |
| LM31 | Y10 | D | Y11 | D | Y10 | H | X1 | H | D | D |
| LM32 | Y10 | D | Y11 | D | Y10 | D | Y3 | D | D | D |
| LM33 | Y10 | D | Y11 | D | Y10 | H | X4 | H | D | D |
| LM34 | Y10 | D | Y11 | D | Y10 | D | Y12 | D | D | D |
| LM35 | X1 | H | X4 | H | X1 | H | H | H | H | D |
| LM36 | X1 | H | X4 | H | X1 | H | H | H | D | H |
| LM37 | X1 | H | X4 | H | X1 | H | H | H | D | D |
| LM38 | Y1 | H | X4 | H | Y1 | H | H | H | D | D |
| LM39 | Y2 | H | X4 | H | Y2 | H | H | H | D | D |
| LM40 | Y3 | H | X4 | H | Y3 | H | H | H | D | D |
| LM41 | Y3 | D | X4 | D | Y3 | H | H | H | D | D |
| LM42 | Y3 | D | X4 | D | Y3 | D | H | H | D | D |
| LM43 | Y3 | D | X4 | D | Y3 | D | D | H | D | D |
| LM44 | Y3 | D | X4 | D | Y3 | D | D | D | D | D |
| LM45 | Y3 | D | Y12 | D | Y3 | D | D | D | D | D |
| LM46 | Y3 | D | Y12 | D | Y3 | H | X1 | H | D | D |
| LM47 | Y3 | D | Y12 | D | Y3 | D | Y3 | D | D | D |
| LM48 | Y3 | D | Y12 | D | Y3 | H | X4 | H | D | D |
| LM49 | Y3 | D | Y12 | D | Y3 | D | Y12 | D | D | D |
| LM50 | X2 | H | X4 | H | X2 | H | H | H | H | D |
| LM51 | X2 | H | X4 | H | X2 | H | H | H | D | H |
| LM52 | X2 | H | X4 | H | X2 | H | H | H | D | D |
| LM53 | Y4 | H | X4 | H | Y4 | H | H | H | D | D |
| LM54 | Y5 | H | X4 | H | Y5 | H | H | H | D | D |
| LM55 | Y6 | H | X4 | H | Y6 | H | H | H | D | D |
| LM56 | Y7 | H | X4 | H | Y7 | H | H | H | D | D |
| LM57 | Y8 | H | X4 | H | Y8 | H | H | H | D | D |
| LM58 | Y9 | H | X4 | H | Y9 | H | H | H | D | D |
| LM59 | Y10 | H | X4 | H | Y10 | H | H | H | D | D |
| LM60 | Y10 | D | X4 | D | Y10 | H | H | H | D | D |
| LM61 | Y10 | D | X4 | D | Y10 | D | H | H | D | D |
| LM62 | Y10 | D | X4 | D | Y10 | D | D | H | D | D |
| LM63 | Y10 | D | X4 | D | Y10 | D | D | D | D | D |
| LM64 | Y10 | D | Y12 | D | Y10 | D | D | D | D | D |
| LM65 | Y10 | D | Y12 | D | Y10 | H | X1 | H | D | D |
| LM66 | Y10 | D | Y12 | D | Y10 | D | Y3 | D | D | D |
| LM67 | Y10 | D | Y12 | D | Y10 | H | X4 | H | D | D |
| LM68 | Y10 | D | Y12 | D | Y10 | D | Y12 | D | D | D |
| LM69 | X1 | H | X5 | H | X1 | H | H | H | H | D |
| LM70 | X1 | H | X5 | H | X1 | H | H | H | D | H |
| LM71 | X1 | H | X5 | H | X1 | H | H | H | D | D |
| LM72 | Y1 | H | X5 | H | Y1 | H | H | H | D | D |
| LM73 | Y2 | H | X5 | H | Y2 | H | H | H | D | D |
| LM74 | Y3 | H | X5 | H | Y3 | H | H | H | D | D |
| LM75 | Y3 | D | X5 | D | Y3 | H | H | H | D | D |
| LM76 | Y3 | D | X5 | D | Y3 | D | H | H | D | D |

TABLE 4-continued

| Ligand name | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
|---|---|---|---|---|---|---|---|---|---|---|
| Formula 11-1 | | | | | | | | | | |
| LM77 | Y3 | D | X5 | D | Y3 | D | D | H | D | D |
| LM78 | Y3 | D | X5 | D | Y3 | D | D | D | D | D |
| LM79 | Y3 | D | Y13 | D | Y3 | D | D | D | D | D |
| LM80 | Y3 | D | Y13 | D | Y3 | H | X1 | H | D | D |
| LM81 | Y3 | D | Y13 | D | Y3 | D | Y3 | D | D | D |
| LM82 | Y3 | D | Y13 | D | Y3 | H | X4 | H | D | D |
| LM83 | Y3 | D | Y13 | D | Y3 | D | Y12 | D | D | D |
| LM84 | X2 | H | X5 | H | X2 | H | H | H | H | D |
| LM85 | X2 | H | X5 | H | X2 | H | H | H | D | H |
| LM86 | X2 | H | X5 | H | X2 | H | H | H | D | D |
| LM87 | Y4 | H | X5 | H | Y4 | H | H | H | D | D |
| LM88 | Y5 | H | X5 | H | Y5 | H | H | H | D | D |
| LM89 | Y6 | H | X5 | H | Y6 | H | H | H | D | D |
| LM90 | Y7 | H | X5 | H | Y7 | H | H | H | D | D |
| LM91 | Y8 | H | X5 | H | Y8 | H | H | H | D | D |
| LM92 | Y9 | H | X5 | H | Y9 | H | H | H | D | D |
| LM93 | Y10 | H | X5 | H | Y10 | H | H | H | D | D |
| LM94 | Y10 | D | X5 | D | Y10 | H | H | H | D | D |
| LM95 | Y10 | D | X5 | D | Y10 | D | H | H | D | D |
| LM96 | Y10 | D | X5 | D | Y10 | D | D | H | D | D |
| LM97 | Y10 | D | X5 | D | Y10 | D | D | D | D | D |
| LM98 | Y10 | D | Y13 | D | Y10 | D | D | D | D | D |
| LM99 | Y10 | D | Y13 | D | Y10 | H | X1 | H | D | D |
| LM100 | Y10 | D | Y13 | D | Y10 | D | Y3 | D | D | D |
| LM101 | Y10 | D | Y13 | D | Y10 | H | X4 | H | D | D |
| LM102 | Y10 | D | Y13 | D | Y10 | D | Y12 | D | D | D |
| LM103 | X1 | H | X6 | H | X1 | H | H | H | H | D |
| LM104 | X1 | H | X6 | H | X1 | H | H | H | D | H |
| LM105 | X1 | H | X6 | H | X1 | H | H | H | D | D |
| LM106 | Y1 | H | X6 | H | Y1 | H | H | H | D | D |
| LM107 | Y2 | H | X6 | H | Y2 | H | H | H | D | D |
| LM108 | Y3 | H | X6 | H | Y3 | H | H | H | D | D |
| LM109 | Y3 | D | X6 | D | Y3 | H | H | H | D | D |
| LM110 | Y3 | D | X6 | D | Y3 | D | H | H | D | D |
| LM111 | Y3 | D | X6 | D | Y3 | D | D | H | D | D |
| LM112 | Y3 | D | X6 | D | Y3 | D | D | D | D | D |
| LM113 | Y3 | D | Y14 | D | Y3 | D | D | D | D | D |
| LM114 | Y3 | D | Y14 | D | Y3 | H | X1 | H | D | D |
| LM115 | Y3 | D | Y14 | D | Y3 | D | Y3 | D | D | D |
| LM116 | Y3 | D | Y14 | D | Y3 | H | X4 | H | D | D |
| LM117 | Y3 | D | Y14 | D | Y3 | D | Y12 | D | D | D |
| LM118 | X2 | H | X6 | H | X2 | H | H | H | H | D |
| LM119 | X2 | H | X6 | H | X2 | H | H | H | D | H |
| LM120 | X2 | H | X6 | H | X2 | H | H | H | D | D |
| LM121 | Y4 | H | X6 | H | Y4 | H | H | H | D | D |
| LM122 | Y5 | H | X6 | H | Y5 | H | H | H | D | D |
| LM123 | Y6 | H | X6 | H | Y6 | H | H | H | D | D |
| LM124 | Y7 | H | X6 | H | Y7 | H | H | H | D | D |
| LM125 | Y8 | H | X6 | H | Y8 | H | H | H | D | D |
| LM126 | Y9 | H | X6 | H | Y9 | H | H | H | D | D |
| LM127 | Y10 | H | X6 | H | Y10 | H | H | H | D | D |
| LM128 | Y10 | D | X6 | D | Y10 | H | H | H | D | D |
| LM129 | Y10 | D | X6 | D | Y10 | D | H | H | D | D |
| LM130 | Y10 | D | X6 | D | Y10 | D | D | H | D | D |
| LM131 | Y10 | D | X6 | D | Y10 | D | D | D | D | D |
| LM132 | Y10 | D | Y14 | D | Y10 | D | D | D | D | D |
| LM133 | Y10 | D | Y14 | D | Y10 | H | X1 | H | D | D |
| LM134 | Y10 | D | Y14 | D | Y10 | D | Y3 | D | D | D |
| LM135 | Y10 | D | Y14 | D | Y10 | H | X4 | H | D | D |
| LM136 | Y10 | D | Y14 | D | Y10 | D | Y12 | D | D | D |
| LM137 | X1 | H | X7 | H | X1 | H | H | H | H | D |
| LM138 | X1 | H | X7 | H | X1 | H | H | H | D | H |
| LM139 | X1 | H | X7 | H | X1 | H | H | H | D | D |
| LM140 | Y1 | H | X7 | H | Y1 | H | H | H | D | D |
| LM141 | Y2 | H | X7 | H | Y2 | H | H | H | D | D |
| LM142 | Y3 | H | X7 | H | Y3 | H | H | H | D | D |
| LM143 | Y3 | D | X7 | D | Y3 | H | H | H | D | D |
| LM144 | Y3 | D | X7 | D | Y3 | D | H | H | D | D |
| LM145 | Y3 | D | X7 | D | Y3 | D | D | H | D | D |
| LM146 | Y3 | D | X7 | D | Y3 | D | D | D | D | D |
| LM147 | Y3 | D | X8 | D | Y3 | D | D | D | D | D |
| LM148 | Y3 | D | Y16 | D | Y3 | D | D | D | D | D |
| LM149 | Y3 | D | Y17 | D | Y3 | D | D | D | D | D |
| LM150 | Y3 | D | Y18 | D | Y3 | D | D | D | D | D |
| LM151 | Y3 | D | Y15 | D | Y3 | D | D | D | D | D |
| LM152 | Y3 | D | Y15 | D | Y3 | H | X1 | H | D | D |

TABLE 4-continued

| Formula 11-1 | | | | | | | | | | |
|---|---|---|---|---|---|---|---|---|---|---|
| Ligand name | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
| LM153 | Y3 | D | Y15 | D | Y3 | D | Y3 | D | D | D |
| LM154 | Y3 | D | Y16 | D | Y3 | D | Y3 | D | D | D |
| LM155 | Y3 | D | Y17 | D | Y3 | D | Y3 | D | D | D |
| LM156 | Y3 | D | Y18 | D | Y3 | D | Y3 | D | D | D |
| LM157 | Y3 | D | Y15 | D | Y3 | H | X4 | H | D | D |
| LM158 | Y3 | D | Y15 | D | Y3 | D | Y12 | D | D | D |
| LM159 | Y3 | D | Y16 | D | Y3 | D | Y12 | D | D | D |
| LM160 | Y3 | D | Y17 | D | Y3 | D | Y12 | D | D | D |
| LM161 | Y3 | D | Y18 | D | Y3 | D | Y12 | D | D | D |
| LM162 | X2 | H | X7 | H | X2 | H | H | H | H | D |
| LM163 | X2 | H | X7 | H | X2 | H | H | H | D | H |
| LM164 | X2 | H | X7 | H | X2 | H | H | H | D | D |
| LM165 | Y4 | H | X7 | H | Y4 | H | H | H | D | D |
| LM166 | Y5 | H | X7 | H | Y5 | H | H | H | D | D |
| LM167 | Y6 | H | X7 | H | Y6 | H | H | H | D | D |
| LM168 | Y7 | H | X7 | H | Y7 | H | H | H | D | D |
| LM169 | Y8 | H | X7 | H | Y8 | H | H | H | D | D |
| LM170 | Y9 | H | X7 | H | Y9 | H | H | H | D | D |
| LM171 | Y10 | H | X7 | H | Y10 | H | H | H | D | D |
| LM172 | Y10 | D | X7 | D | Y10 | H | H | H | D | D |
| LM173 | Y10 | D | X7 | D | Y10 | D | H | H | D | D |
| LM174 | Y10 | D | X7 | D | Y10 | D | D | H | D | D |
| LM175 | Y10 | D | X7 | D | Y10 | D | D | D | D | D |
| LM176 | Y10 | D | X8 | D | Y10 | D | D | D | D | D |
| LM177 | Y10 | D | Y16 | D | Y10 | D | D | D | D | D |
| LM178 | Y10 | D | Y17 | D | Y10 | D | D | D | D | D |
| LM179 | Y10 | D | Y18 | D | Y10 | D | D | D | D | D |
| LM180 | Y10 | D | Y15 | D | Y10 | D | D | D | D | D |
| LM181 | Y10 | D | Y15 | D | Y10 | H | X1 | H | D | D |
| LM182 | Y10 | D | Y15 | D | Y10 | D | Y3 | D | D | D |
| LM183 | Y10 | D | Y16 | D | Y10 | D | Y3 | D | D | D |
| LM184 | Y10 | D | Y17 | D | Y10 | D | Y3 | D | D | D |
| LM185 | Y10 | D | Y18 | D | Y10 | D | Y3 | D | D | D |
| LM186 | Y10 | D | Y15 | D | Y10 | H | X4 | H | D | D |
| LM187 | Y10 | D | Y15 | D | Y10 | D | Y12 | D | D | D |
| LM188 | Y10 | D | Y16 | D | Y10 | D | Y12 | D | D | D |
| LM189 | Y10 | D | Y17 | D | Y10 | D | Y12 | D | D | D |
| LM190 | Y10 | D | Y18 | D | Y10 | D | Y12 | D | D | D |
| LM191 | X1 | X7 | H | H | X1 | H | H | H | H | D |
| LM192 | X1 | X7 | H | H | X1 | H | H | H | D | H |
| LM193 | X1 | X7 | H | H | X1 | H | H | H | D | D |
| LM194 | Y1 | X7 | H | H | Y1 | H | H | H | D | D |
| LM195 | Y2 | X7 | H | H | Y2 | H | H | H | D | D |
| LM196 | Y3 | X7 | H | H | Y3 | H | H | H | D | D |
| LM197 | Y3 | X7 | D | D | Y3 | H | H | H | D | D |
| LM198 | Y3 | X7 | D | D | Y3 | D | H | H | D | D |
| LM199 | Y3 | X7 | D | D | Y3 | D | D | H | D | D |
| LM200 | Y3 | X7 | D | D | Y3 | D | D | D | D | D |
| LM201 | Y3 | Y15 | D | D | Y3 | D | D | D | D | D |
| LM202 | Y3 | Y16 | D | D | Y3 | D | D | D | D | D |
| LM203 | Y3 | Y17 | D | D | Y3 | D | D | D | D | D |
| LM204 | Y3 | Y18 | D | D | Y3 | D | D | D | D | D |
| LM205 | Y3 | Y15 | D | D | Y3 | H | X1 | H | D | D |
| LM206 | Y3 | Y15 | D | D | Y3 | D | Y3 | D | D | D |
| LM207 | Y3 | Y16 | D | D | Y3 | D | Y3 | D | D | D |
| LM208 | Y3 | Y17 | D | D | Y3 | D | Y3 | D | D | D |
| LM209 | Y3 | Y18 | D | D | Y3 | D | Y3 | D | D | D |
| LM210 | Y3 | Y15 | D | D | Y3 | H | X4 | H | D | D |
| LM211 | Y3 | Y15 | D | D | Y3 | D | Y12 | D | D | D |
| LM212 | Y3 | Y16 | D | D | Y3 | D | Y12 | D | D | D |
| LM213 | Y3 | Y17 | D | D | Y3 | D | Y12 | D | D | D |
| LM214 | Y3 | Y18 | D | D | Y3 | D | Y12 | D | D | D |
| LM215 | X2 | X7 | H | H | X2 | H | H | H | H | D |
| LM216 | X2 | X7 | H | H | X2 | H | H | H | D | H |
| LM217 | X2 | X7 | H | H | X2 | H | H | H | D | D |
| LM218 | Y4 | X7 | H | H | Y4 | H | H | H | D | D |
| LM219 | Y5 | X7 | H | H | Y5 | H | H | H | D | D |
| LM220 | Y6 | X7 | H | H | Y6 | H | H | H | D | D |
| LM221 | Y7 | X7 | H | H | Y7 | H | H | H | D | D |
| LM222 | Y8 | X7 | H | H | Y8 | H | H | H | D | D |
| LM223 | Y9 | X7 | H | H | Y9 | H | H | H | D | D |
| LM224 | Y10 | X7 | H | H | Y10 | H | H | H | D | D |
| LM225 | Y10 | X7 | D | D | Y10 | H | H | H | D | D |
| LM226 | Y10 | X7 | D | D | Y10 | D | H | H | D | D |
| LM227 | Y10 | X7 | D | D | Y10 | D | D | H | D | D |
| LM228 | Y10 | X7 | D | D | Y10 | D | D | D | D | D |

TABLE 4-continued

| Formula 11-1 | | | | | | | | | | |
|---|---|---|---|---|---|---|---|---|---|---|
| Ligand name | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
| LM229 | Y10 | X8 | D | D | Y10 | D | D | D | D | D |
| LM230 | Y10 | Y16 | D | D | Y10 | D | D | D | D | D |
| LM231 | Y10 | Y17 | D | D | Y10 | D | D | D | D | D |
| LM232 | Y10 | Y18 | D | D | Y10 | D | D | D | D | D |
| LM233 | Y10 | Y15 | D | D | Y10 | D | D | D | D | D |
| LM234 | Y10 | Y15 | D | D | Y10 | H | X1 | H | D | D |
| LM235 | Y10 | Y15 | D | D | Y10 | D | Y3 | D | D | D |
| LM236 | Y10 | Y16 | D | D | Y10 | D | Y3 | D | D | D |
| LM237 | Y10 | Y17 | D | D | Y10 | D | Y3 | D | D | D |
| LM238 | Y10 | Y18 | D | D | Y10 | D | Y3 | D | D | D |
| LM239 | Y10 | Y15 | D | D | Y10 | H | X4 | H | D | D |
| LM240 | Y10 | Y15 | D | D | Y10 | D | Y12 | D | D | D |
| LM241 | Y10 | Y16 | D | D | Y10 | D | Y12 | D | D | D |
| LM242 | Y10 | Y17 | D | D | Y10 | D | Y12 | D | D | D |
| LM243 | Y10 | Y18 | D | D | Y10 | D | Y12 | D | D | D |

TABLE 5

| Formula 11-2 | | | | | | | | | | | | |
|---|---|---|---|---|---|---|---|---|---|---|---|---|
| Ligand name | $R_{11}$ | $X_{11}$ | $R_{101}$ | $R_{102}$ | $R_{103}$ | $R_{104}$ | $R_{14}$ | $R_{15}$ | $R_{16}$ | $R_{17}$ | $R_{18}$ | $R_{19}$ | $R_{20}$ |
| LFM1 | Y10 | N—Ph | D | D | D | D | D | Y10 | D | D | D | D | D |
| LFM2 | Y10 | S | D | D | D | D | D | Y10 | D | D | D | D | D |
| LFM3 | Y10 | O | D | D | D | D | D | Y10 | D | D | D | D | D |
| LFM4 | Y3 | O | D | D | D | D | D | Y3 | D | D | D | D | D |
| LFM5 | Y10 | O | D | D | D | D | D | Y10 | D | D | D | D | D |
| LFM6 | Y10 | O | D | D | D | D | D | Y10 | D | Y3 | D | D | D |
| LFM7 | Y10 | O | D | D | D | D | D | Y10 | D | Y12 | D | D | D |

TABLE 6

| Formula 11-3 | | | | | | | | | | | | | |
|---|---|---|---|---|---|---|---|---|---|---|---|---|---|
| Ligand name | $R_{11}$ | $X_{11}$ | $R_{101}$ | $R_{102}$ | $R_{103}$ | $R_{104}$ | $R_{14}$ | $R_{15}$ | $R_{16}$ | $R_{17}$ | $R_{18}$ | $R_{19}$ | $R_{20}$ |
| LFP1 | Y10 | N—Ph | D | D | D | D | D | Y10 | D | D | D | D | D |
| LFP2 | Y10 | S | D | D | D | D | D | Y10 | D | D | D | D | D |
| LFP3 | Y10 | O | D | D | D | D | D | Y10 | D | D | D | D | D |
| LFP4 | Y3 | O | D | D | D | D | D | Y3 | D | D | D | D | D |
| LFP5 | Y10 | O | D | D | D | D | D | Y10 | D | D | D | D | D |
| LFP6 | Y10 | O | D | D | D | D | D | Y10 | D | Y3 | D | D | D |
| LFP7 | Y10 | O | D | D | D | D | D | Y10 | D | Y12 | D | D | D |

In Tables 4 to 6, X1 to X10 and Y1 to Y18 may respectively be the same as described herein, and Ph in the tables refers to a phenyl group:

X1

*—$CH_3$

X2

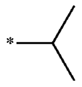

X3

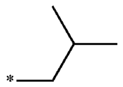

-continued

X4

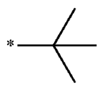

X5

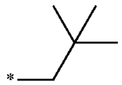

X6

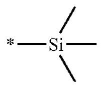

-continued
X7
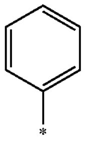
X8
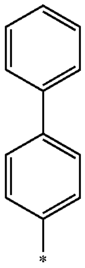
X9
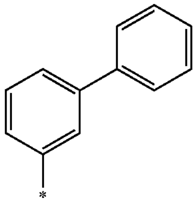
X10
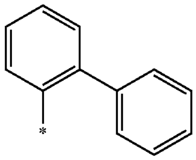
Y1
*—$CH_2D$
Y2
*—$CHD_2$
Y3
*—$CD_3$
Y4
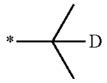
Y5
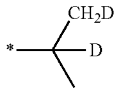
Y6
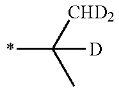
Y7
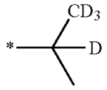
Y8
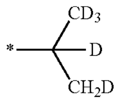
Y9
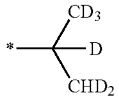
-continued
Y10
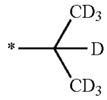
Y11
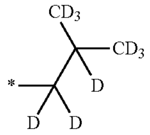
Y12
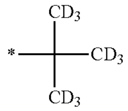
Y13
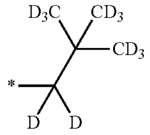
Y14
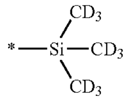
Y15
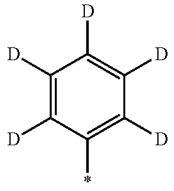
Y16
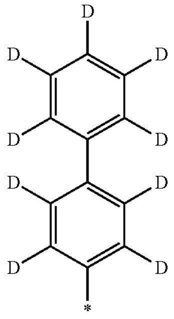
Y17
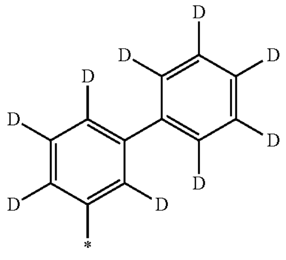

-continued

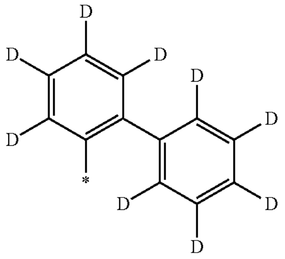

Group VI

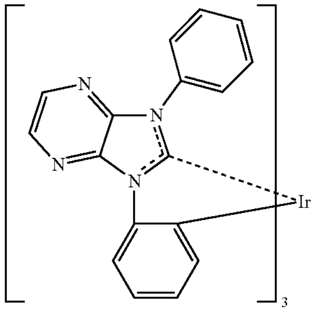

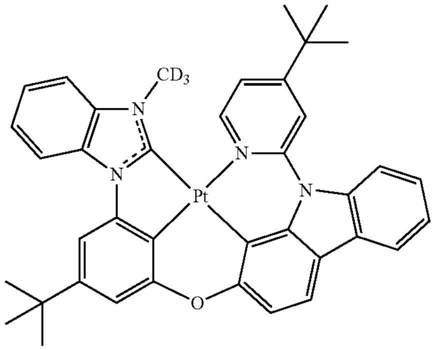

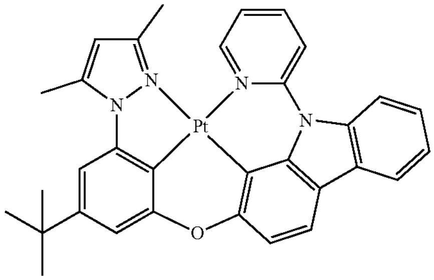

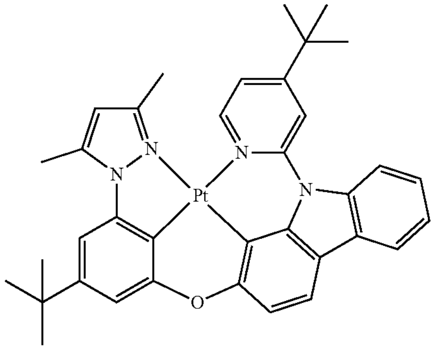

-continued

Y18

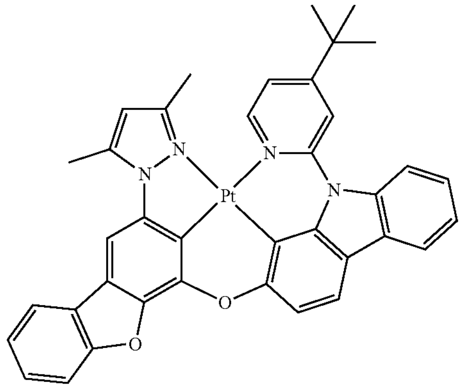

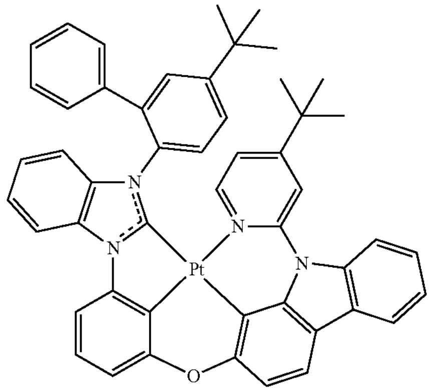

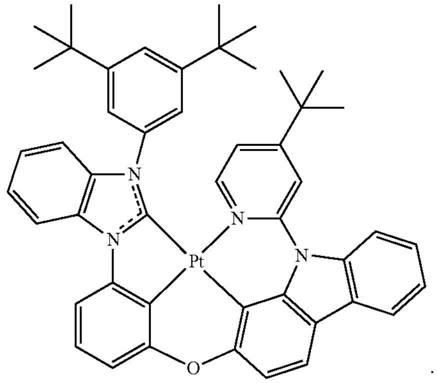

In one or more embodiments, the sensitizer may be a TADF emitter that satisfies Condition 7:

$$\Delta E_{ST} \leq 0.3 \text{ eV} \quad \text{Condition 7}$$

wherein, in Condition 7, $\Delta E_{ST}$ is the difference between a excitation singlet energy level and a excitation triplet energy level of the sensitizer.

In one or more embodiments, the sensitizer may include a TADF emitter represented by Formula 401 or 402:

Formula 401

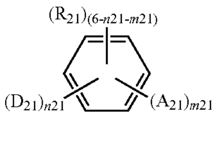

-continued

Formula 402

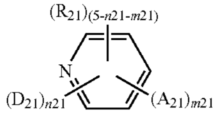

wherein, in Formulae 401 and 402, $A_{21}$ may be an acceptor group, $D_{21}$ may be a donor group, m21 may be 1, 2, or 3, and n21 may be 1, 2, or 3, the sum of n21 and m21 in Formula 401 may be 6 or less, and the sum of n21 and m21 in Formula 402 may be 5 or less, $R_{21}$ may be hydrogen, deuterium, —F, —Cl, —Br, —I, $SF_5$, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ alkylheteroaryl group, a substituted or unsubstituted $C_2$-$C_{60}$ heteroaryl alkyl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(═O)($Q_1$), —S(═O)($Q_1$), —S(═O)$_2$($Q_1$), —P(═O)($Q_1$)($Q_2$), or —P(═S)($Q_1$)($Q_2$), wherein a plurality of $R_{21}$(s) may optionally be linked together to form a substituted or unsubstituted $C_5$-$C_{30}$ carbocyclic group or a substituted or unsubstituted $C_1$-$C_{30}$ heterocyclic group, and $Q_1$ to $Q_3$ may each independently be hydrogen, deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group that is substituted with at least one deuterium, —F, a cyano group, a $C_1$-$C_{60}$ alkyl group, a $C_6$-$C_{60}$ aryl group, or any combination thereof, or a $C_6$-$C_{60}$ aryl group that is substituted with at least one deuterium, —F, a cyano group, a $C_1$-$C_{60}$ alkyl group, a $C_6$-$C_{60}$ aryl group, or a combination thereof.

For example, $A_{21}$ in Formulae 401 and 402 may be a substituted or unsubstituted π electron-deficient nitrogen-free cyclic group.

In an embodiment, the π electron-deficient nitrogen-free cyclic group may be: a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coprogen group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a triindolobenzene group; or a condensed cyclic group in which two or more π electron-deficient nitrogen-free cyclic a group are condensed with each other, but embodiments of the present disclosure are not limited thereto.

For example, $D_{21}$ in Formulae 401 and 402 may be: —F, a cyano group, or an π-electron deficient nitrogen-containing cyclic group;

a $C_1$-$C_{60}$ alkyl group, an π-electron deficient nitrogen-containing cyclic group, or an π electron-deficient nitrogen-free cyclic group, each substituted with at least one —F, a cyano group, or any combination thereof; or an π-electron deficient nitrogen-containing cyclic group, each substituted with at least one deuterium, a $C_1$-$C_{60}$ alkyl group, an π-electron deficient nitrogen-containing cyclic group, an π electron-deficient nitrogen-free cyclic group, or any combination thereof.

In detail, the π electron-deficient nitrogen-free cyclic group may be the same as described herein.

The term "π electron-deficient nitrogen-containing cyclic group" as used herein refers to a cyclic group having at least one *—N═*' moiety, and, for example, may be: an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, and a benzimidazolobenzimidazole group; or a condensed cyclic group in which two or more π electron-efficient nitrogen-containing cyclic a group are condensed with each other.

In one or more embodiments, the sensitizer may be A group VII to XI, but embodiments of the present disclosure are not limited thereto:
Group VII
1
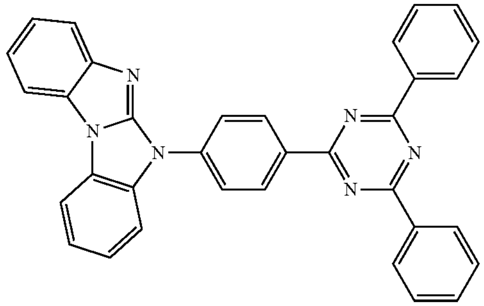
2
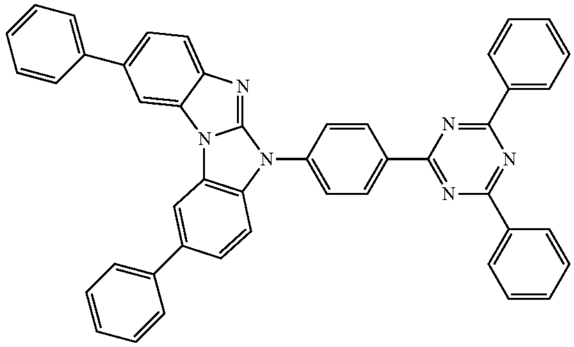
3
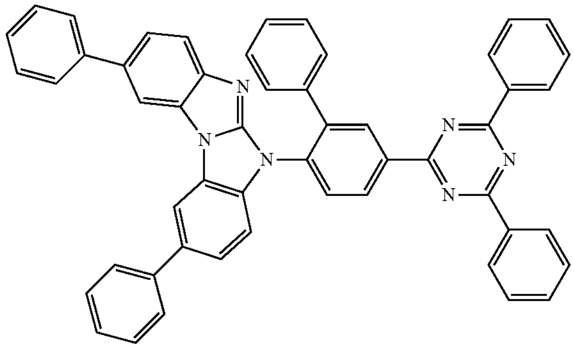
4
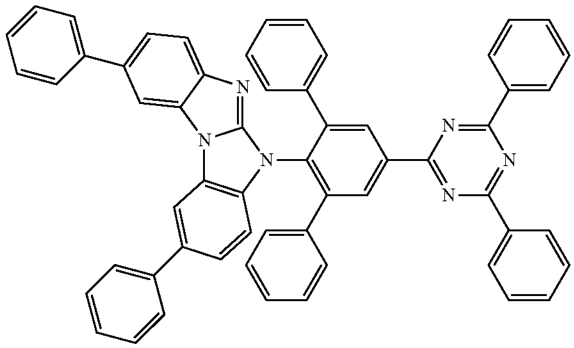
-continued
5
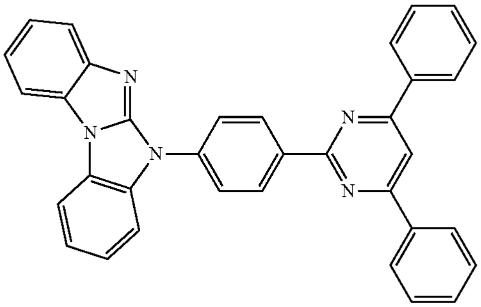
6
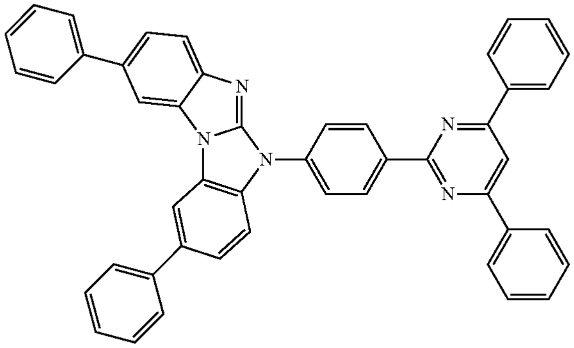
7
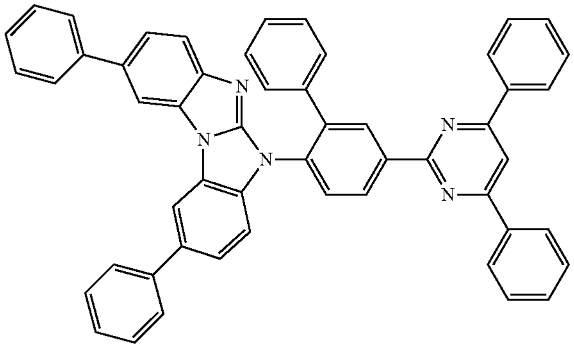
8
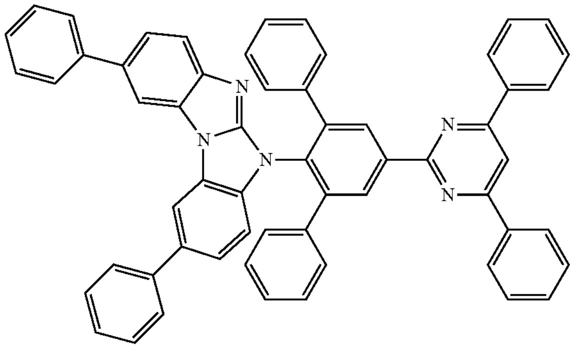

9
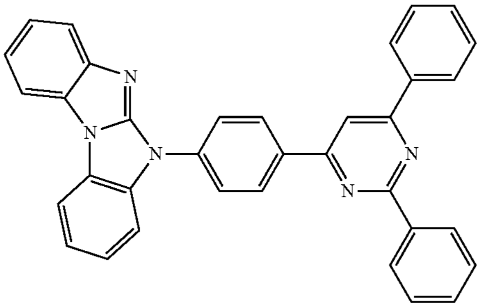
10
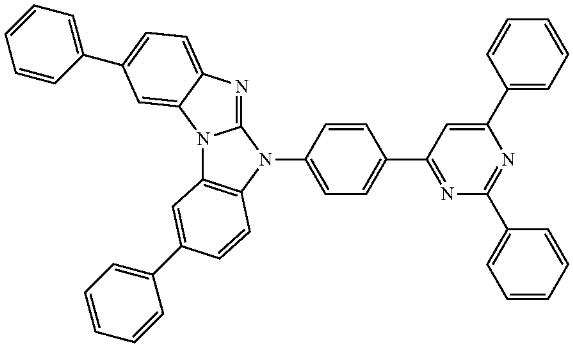
11
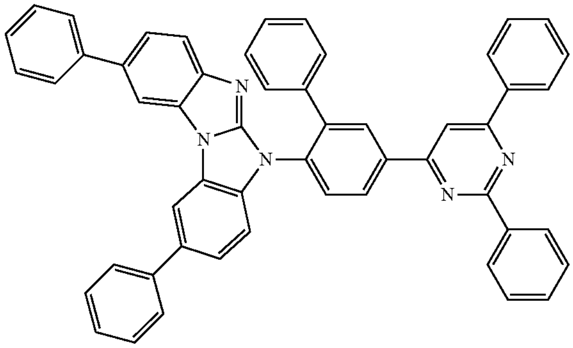
12
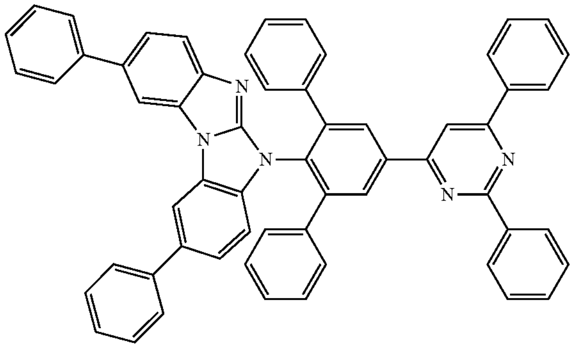
13
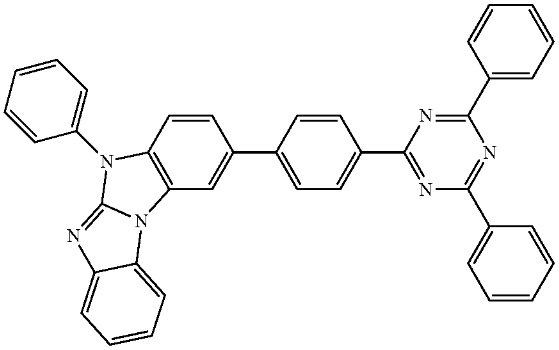
14
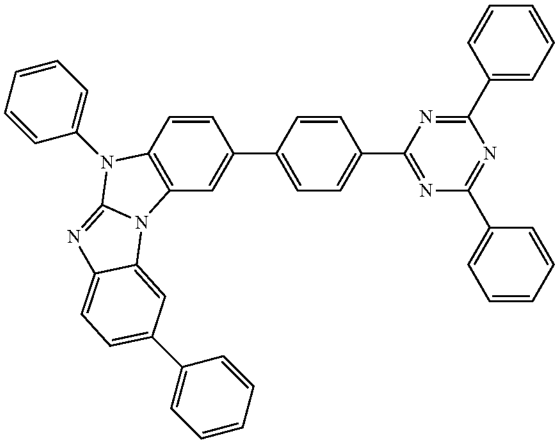
15
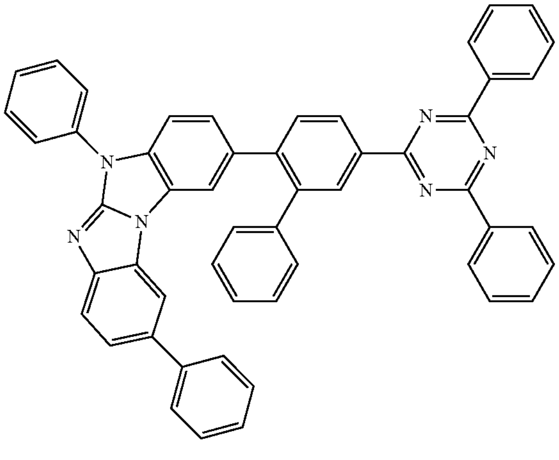

-continued
16
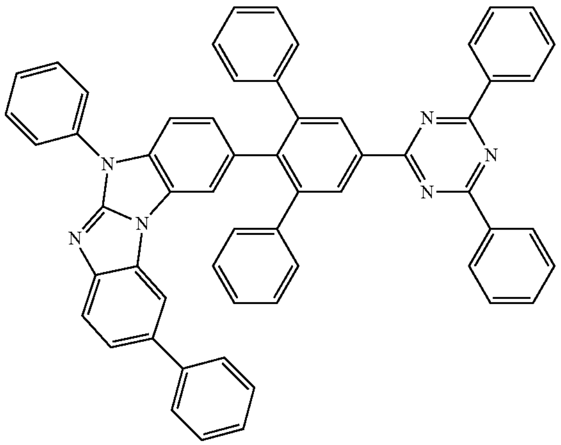
17
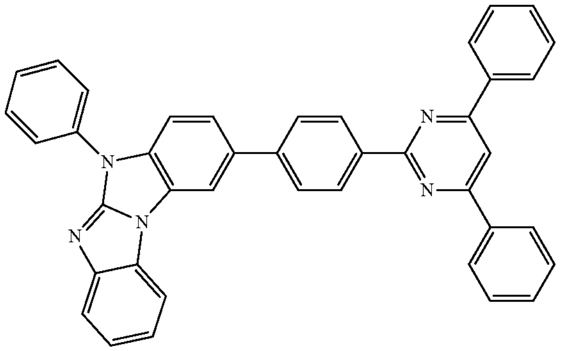
18
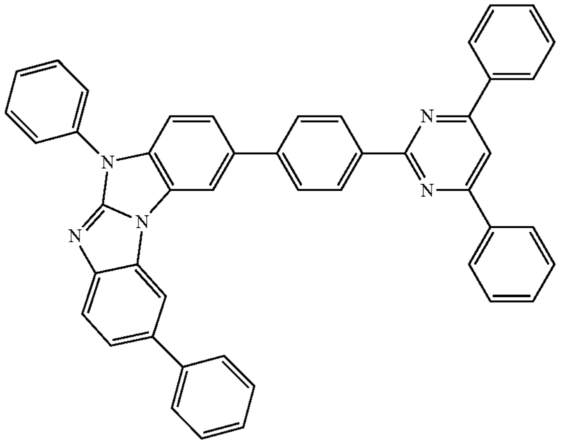
-continued
19
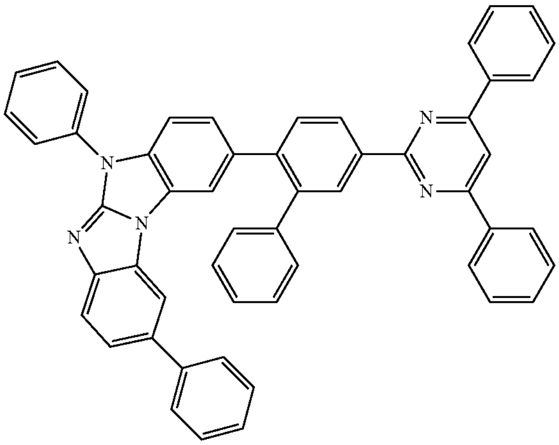
20
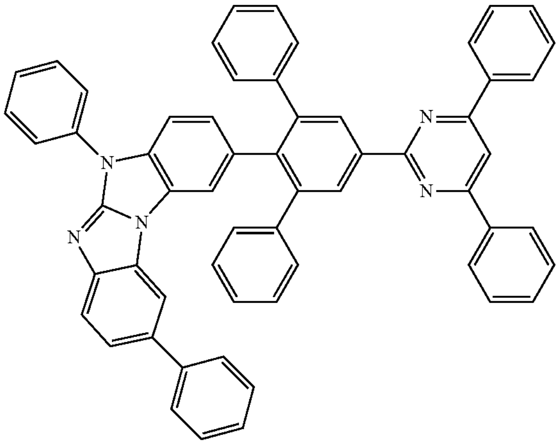
21
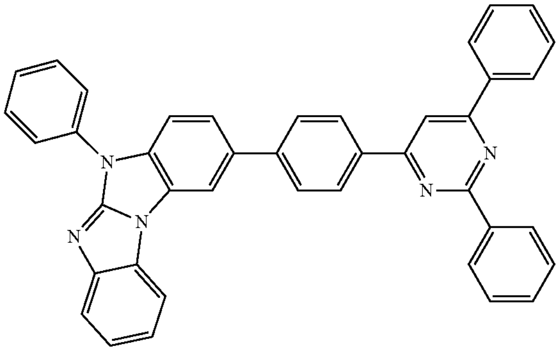

22
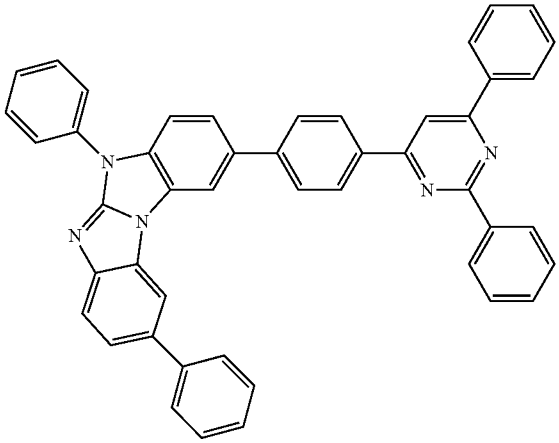
23
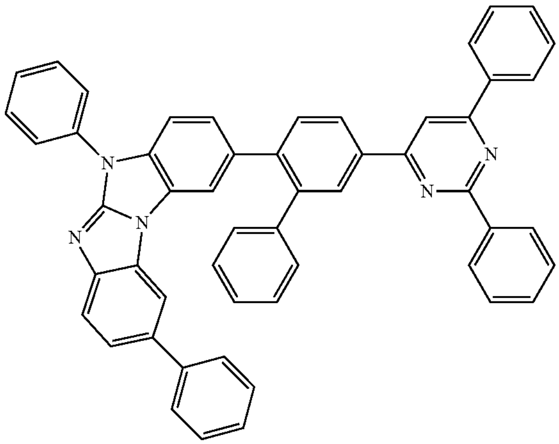
24
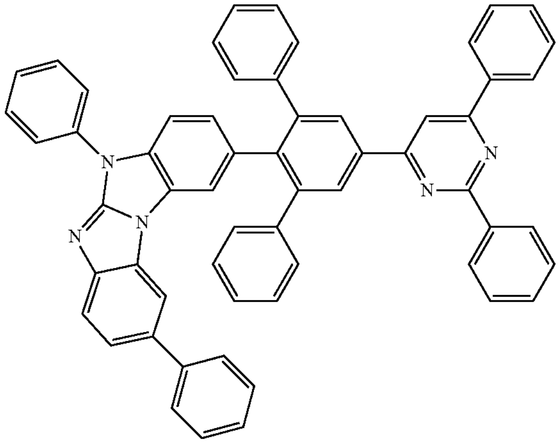
25
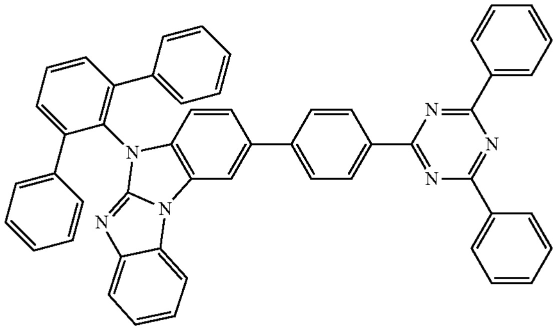
26
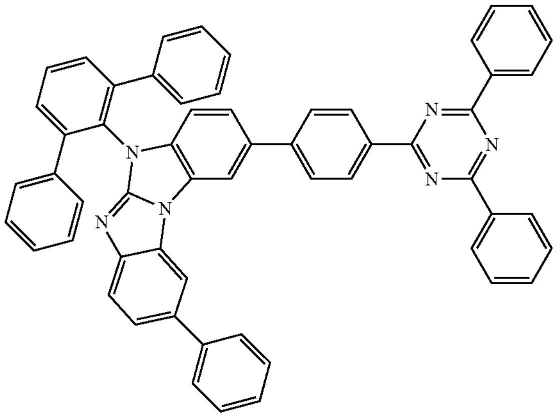
27
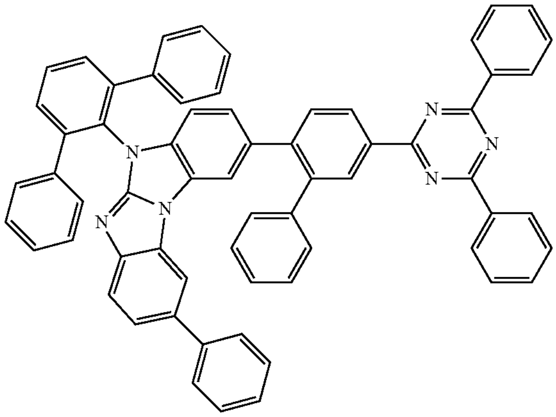

-continued
28
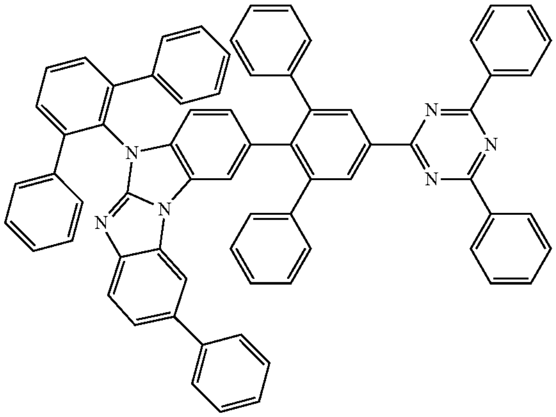
29
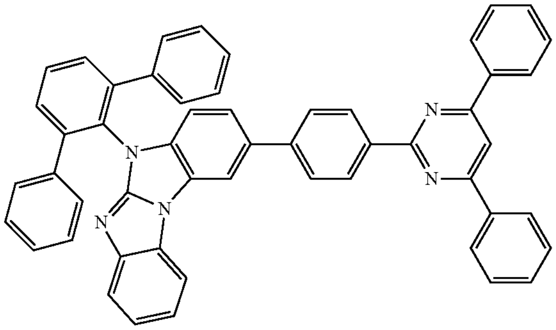
30
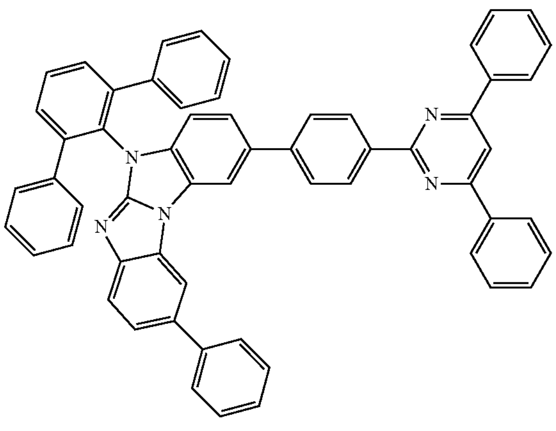
-continued
31
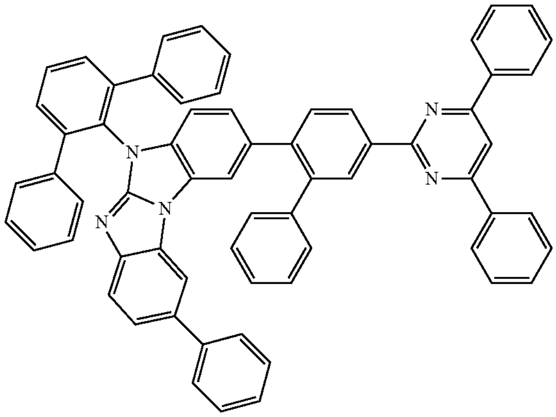
32
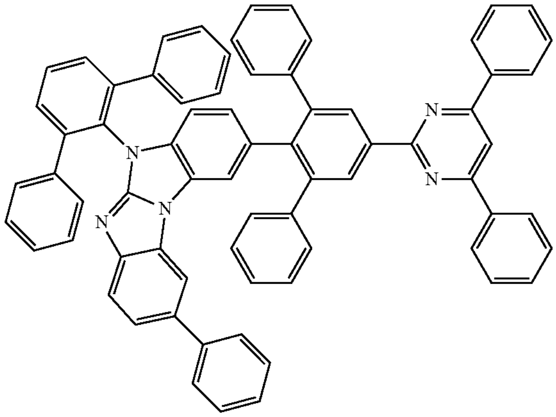
33
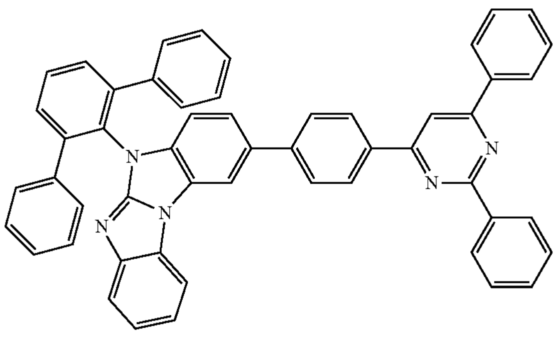

-continued
34
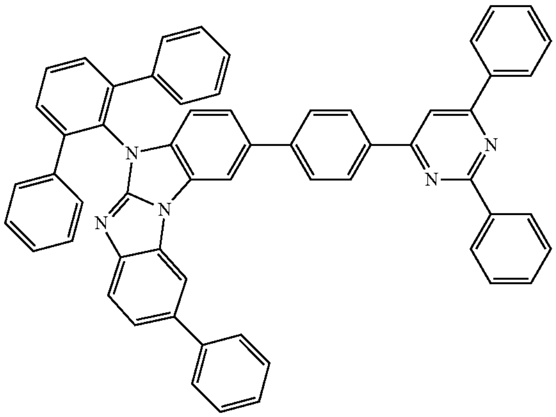
35
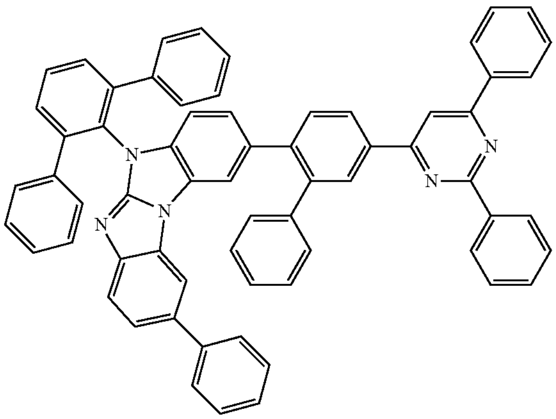
36
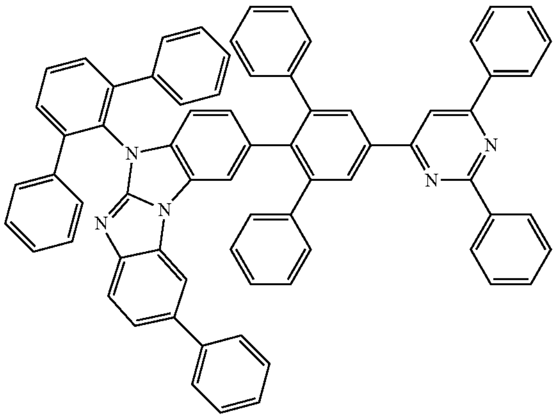
-continued
37
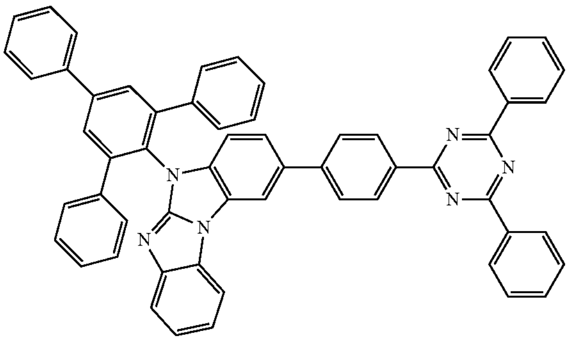
38
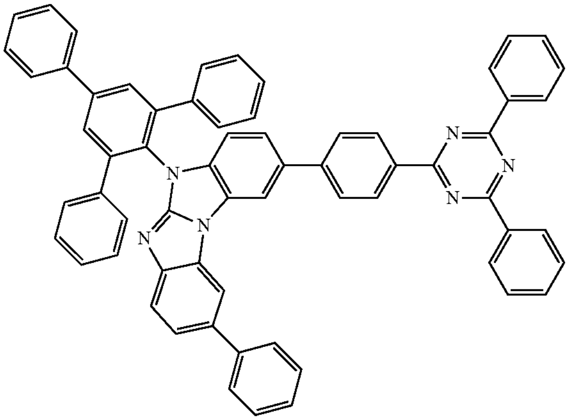
39
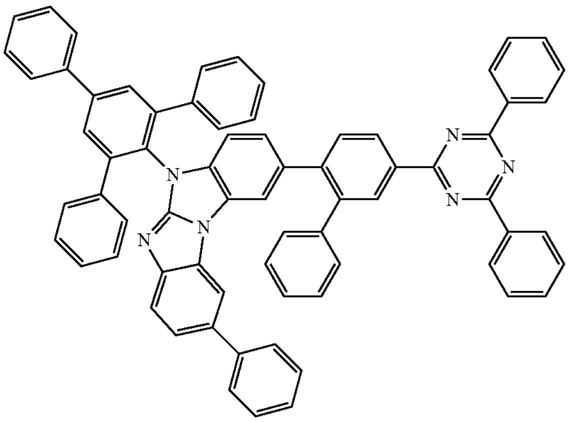

-continued
40
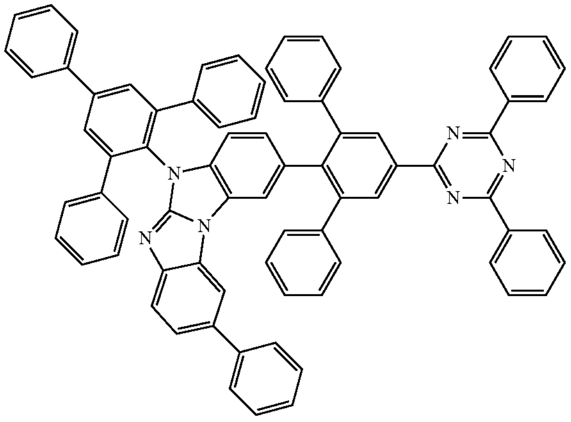
41
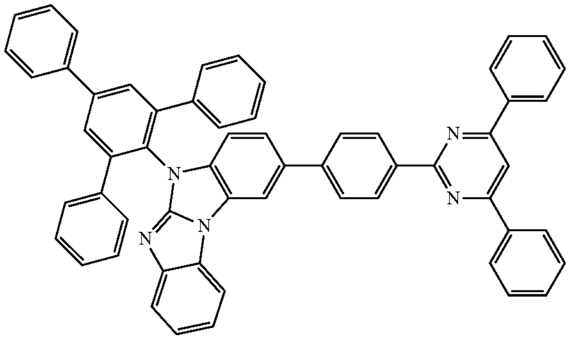
42
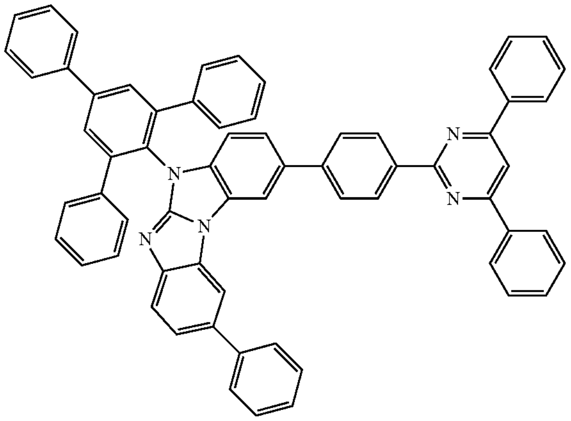
-continued
43
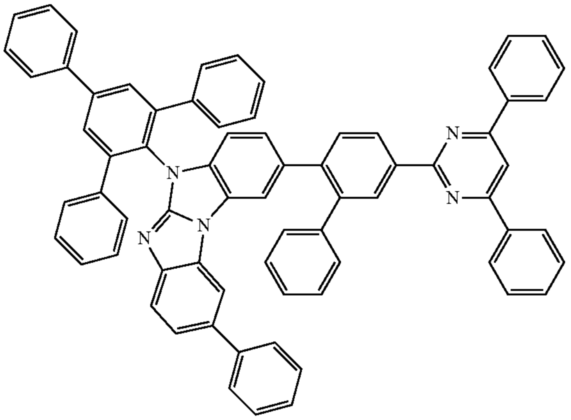
44
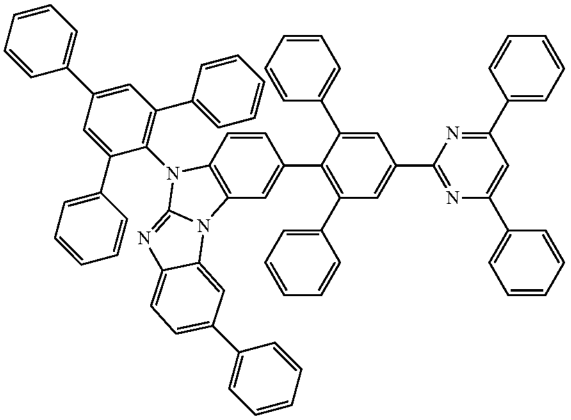
45
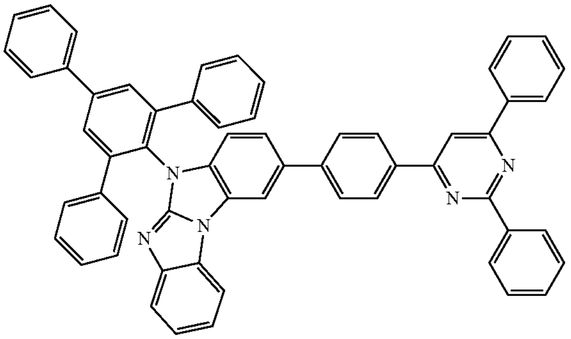

-continued
46
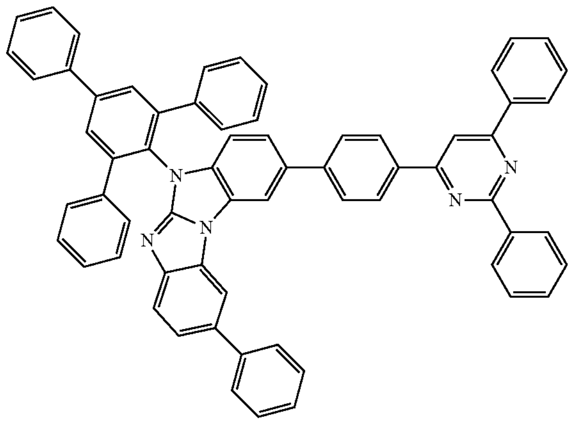
47
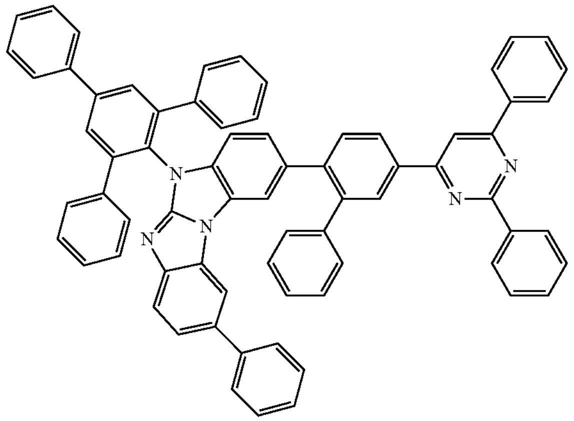
48
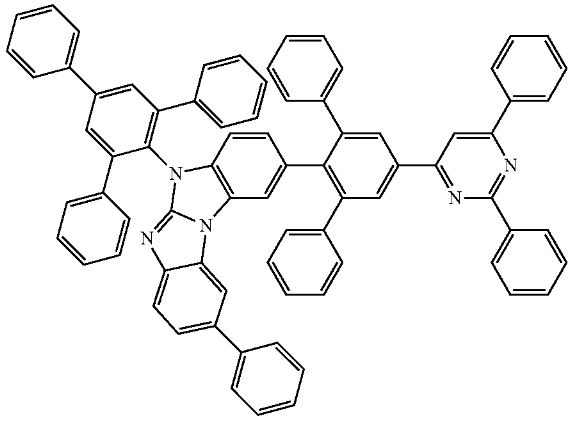
-continued
49
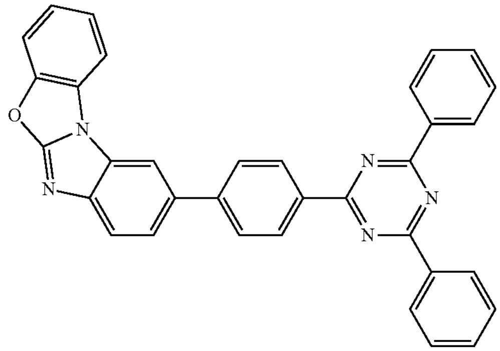
50
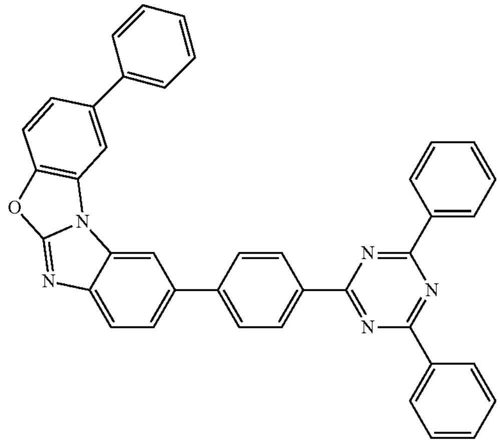
51
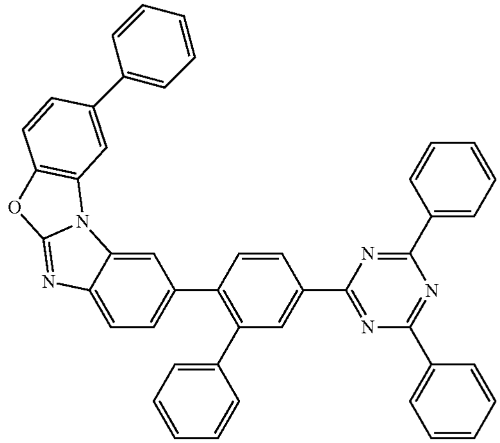

-continued
52
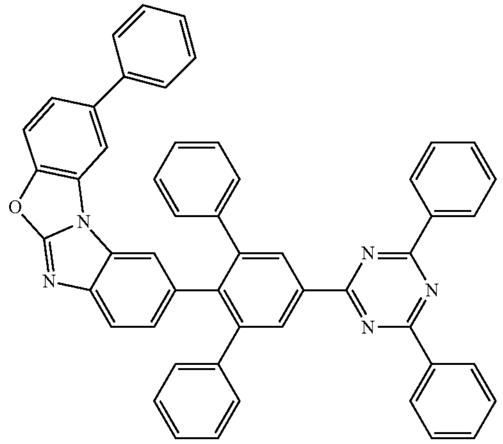
53
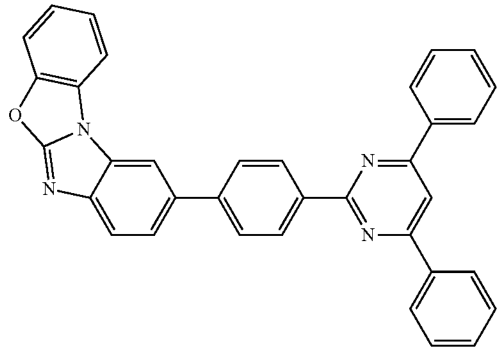
54
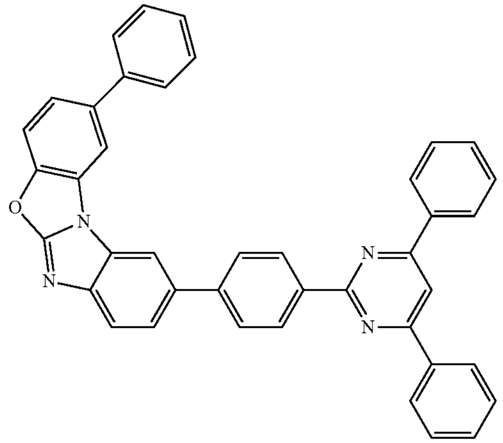
-continued
55
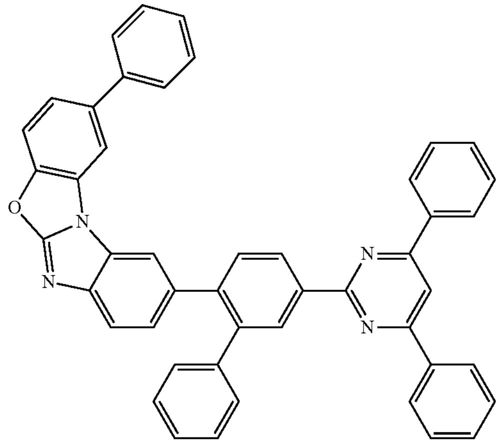
56
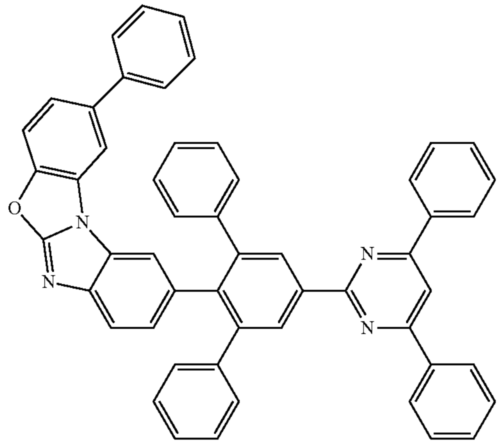
57
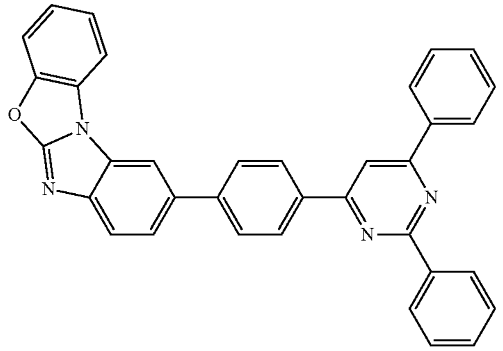

-continued
58
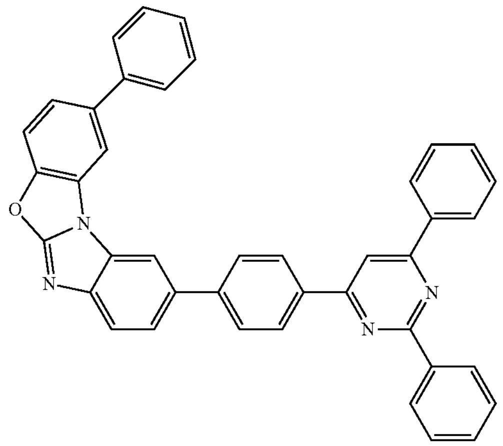
59
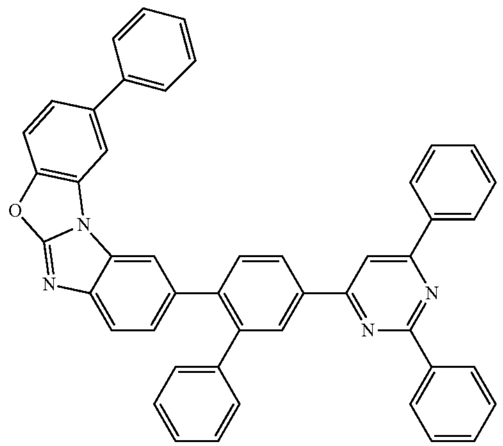
60
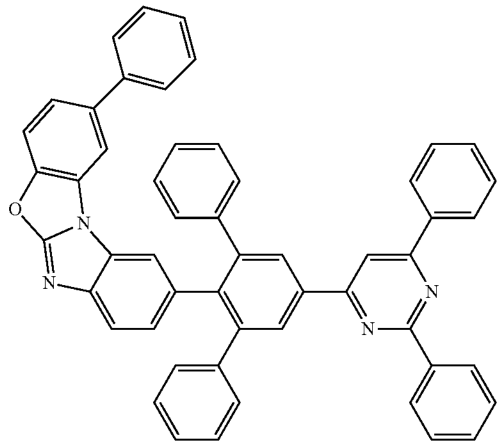
-continued
61
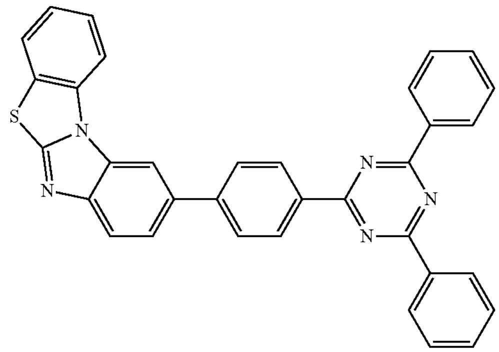
62
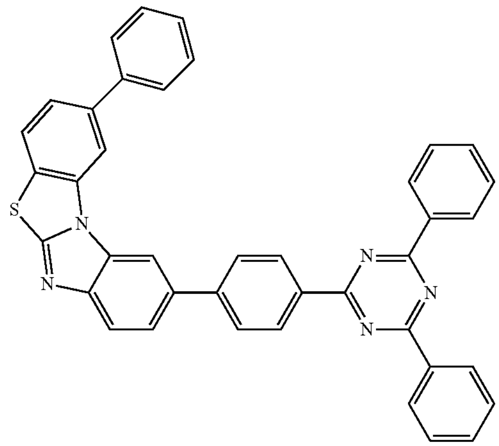
63
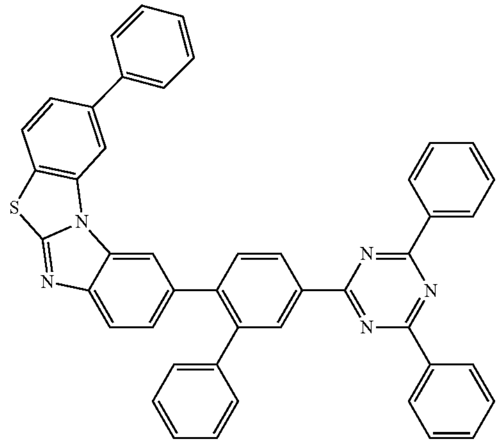

-continued
64
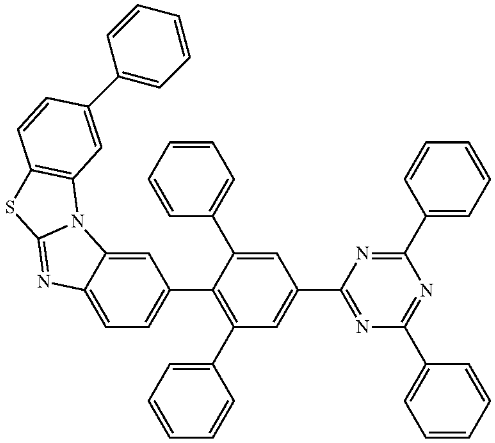
65
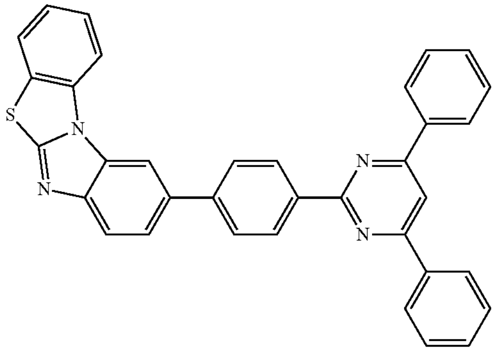
66
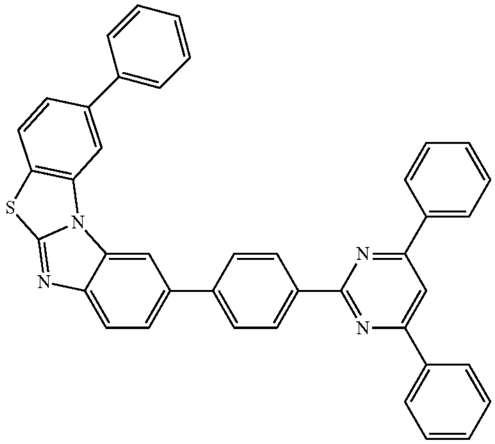
-continued
67
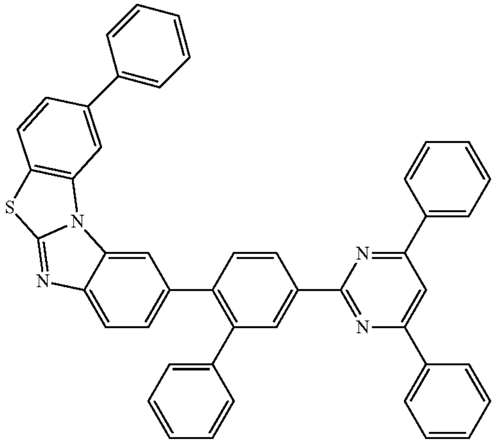
68
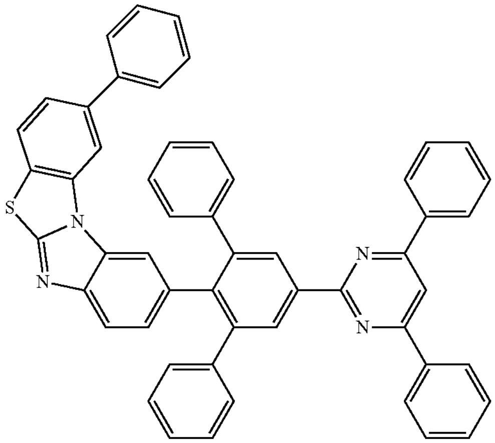
69
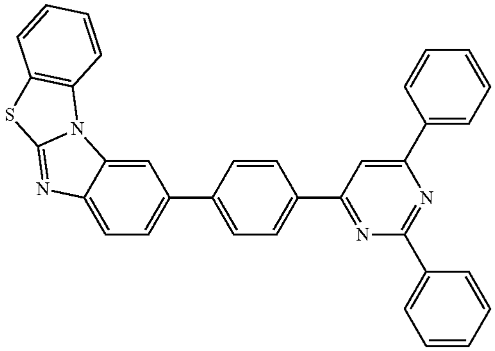

-continued
70
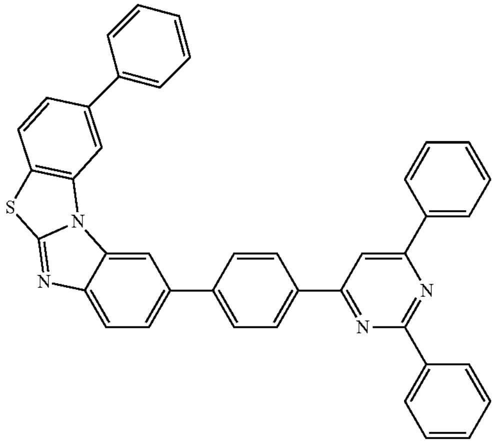
71
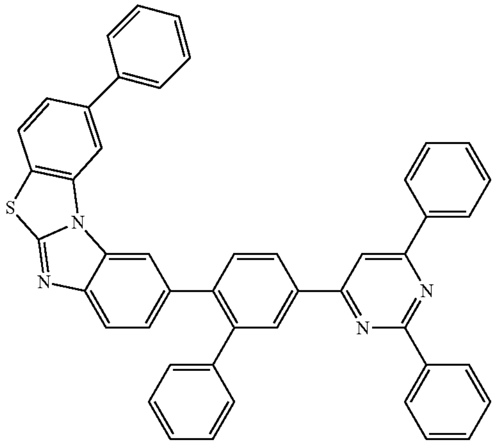
72
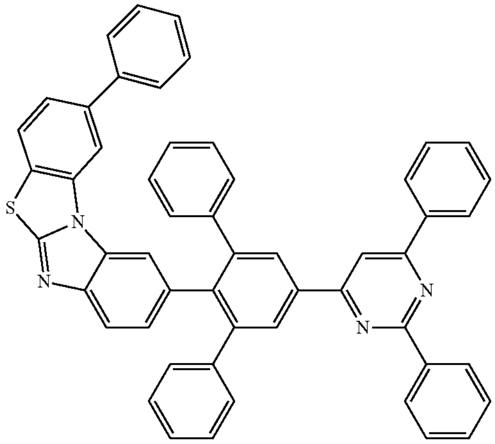
-continued
73
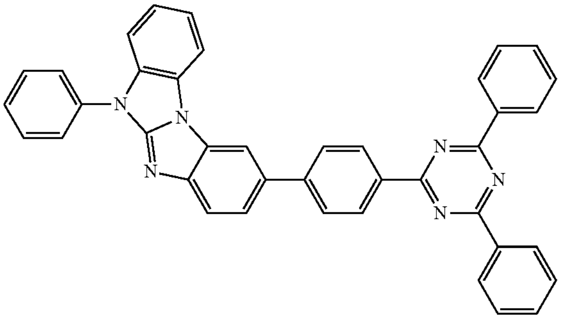
74
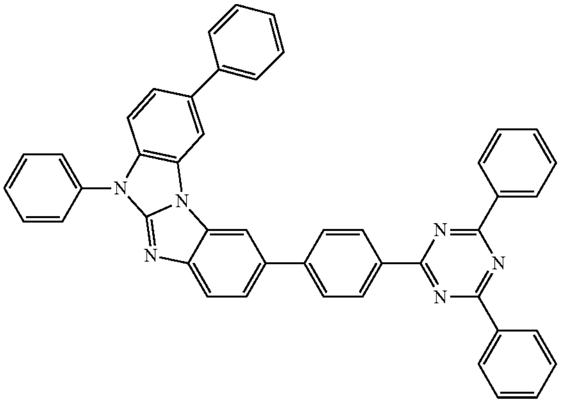
75
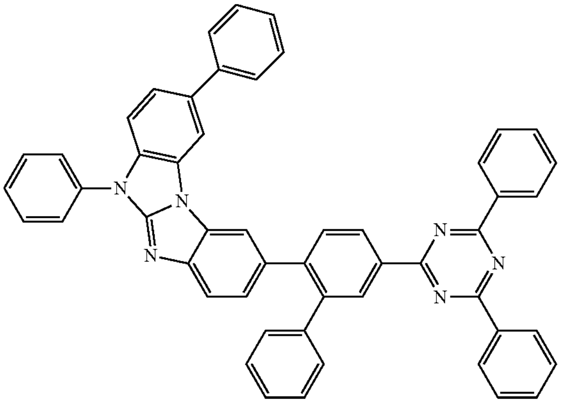
76
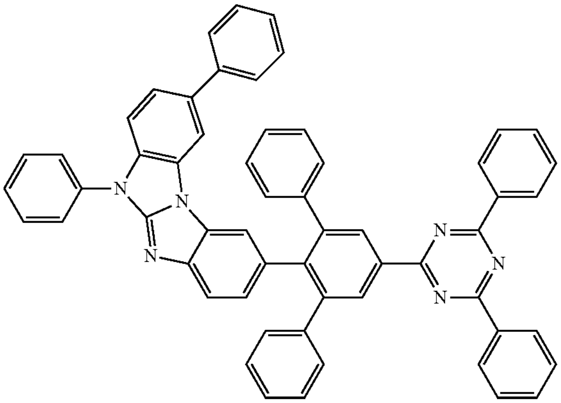

-continued
77
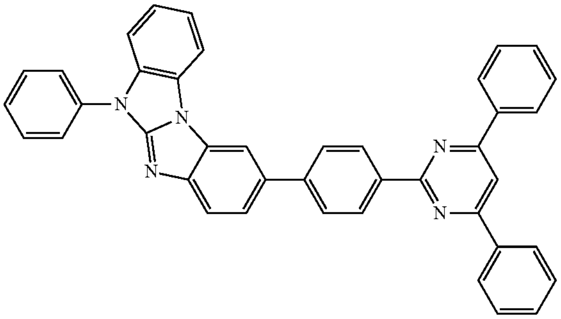
78
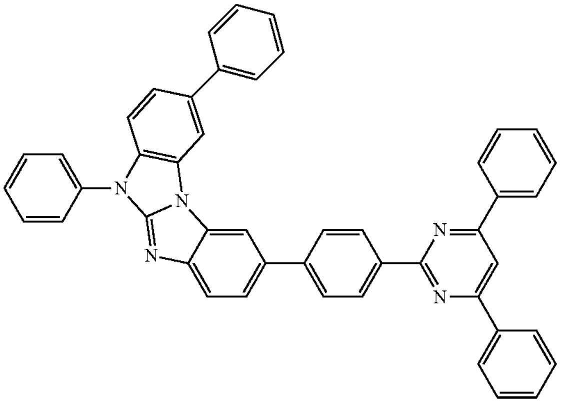
79
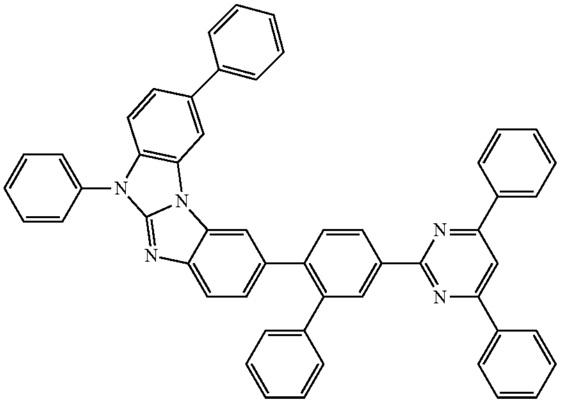
80
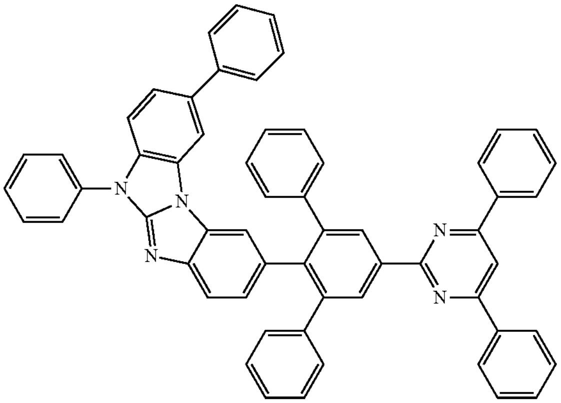
-continued
81
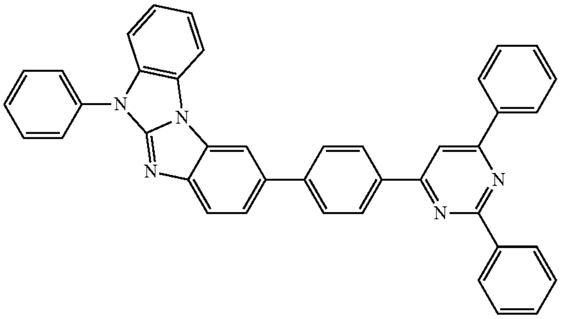
82
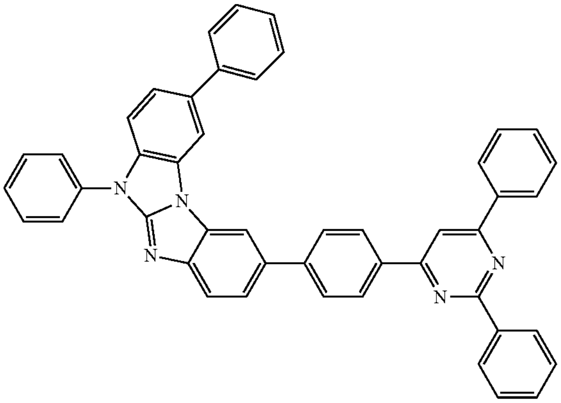
83
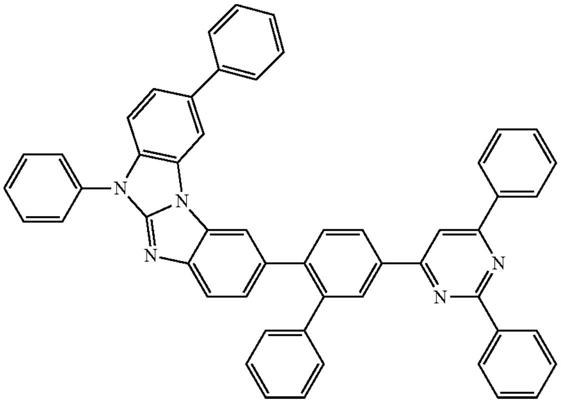
84
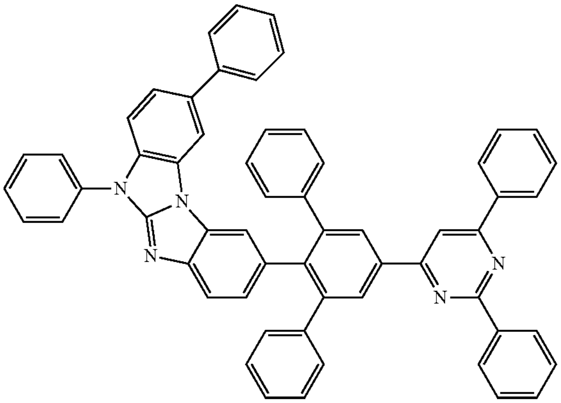

-continued
85
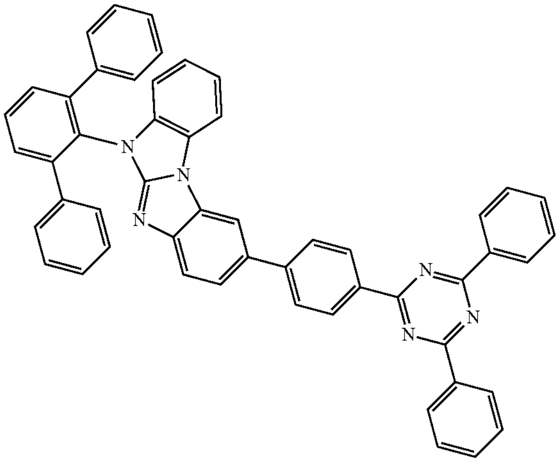
86
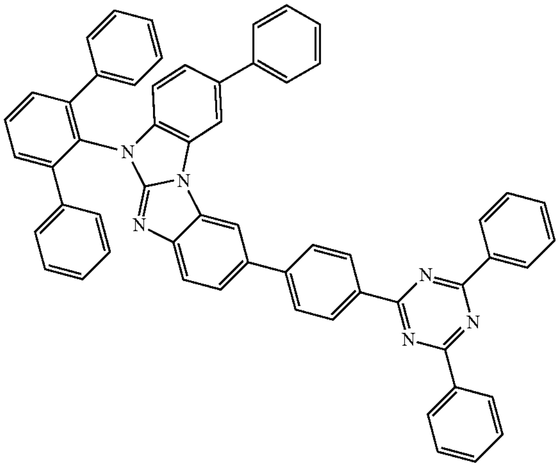
87
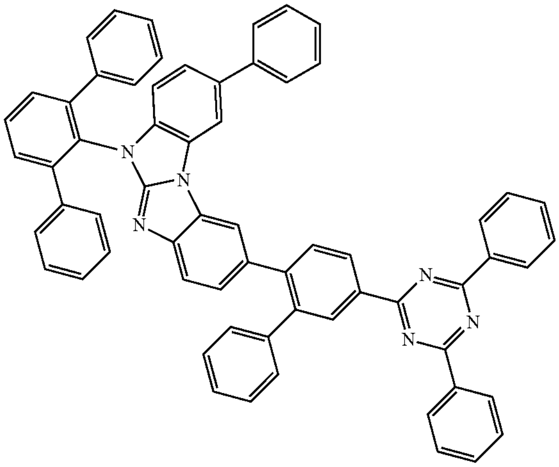
-continued
88
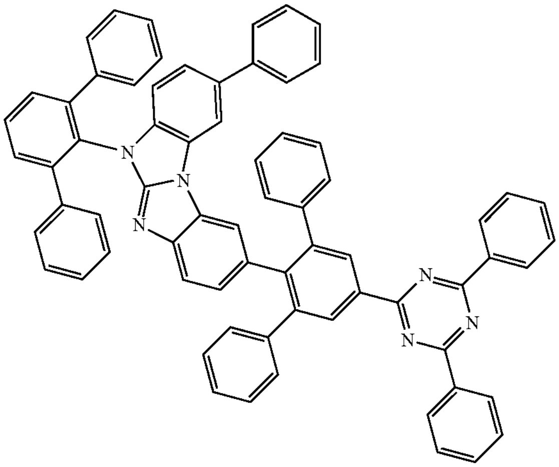
89
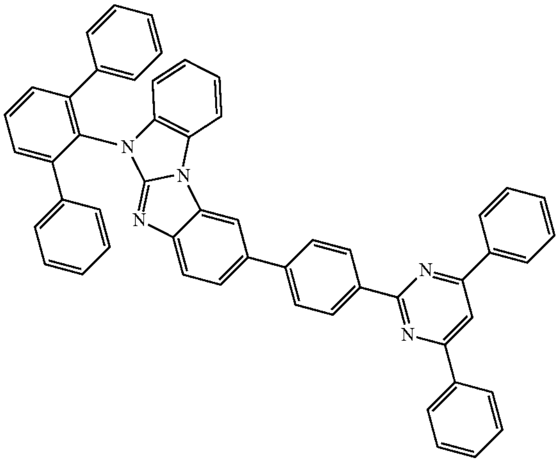
90
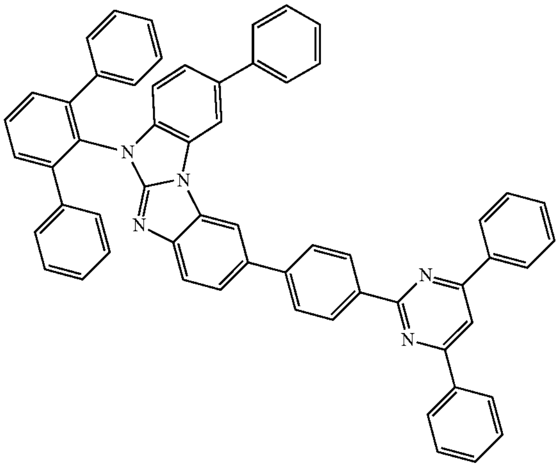

-continued
91
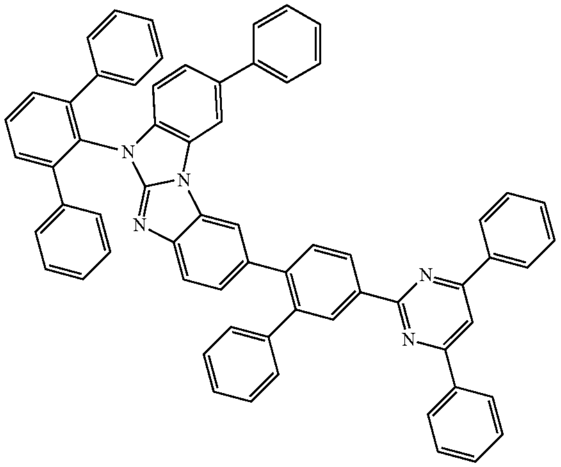
92
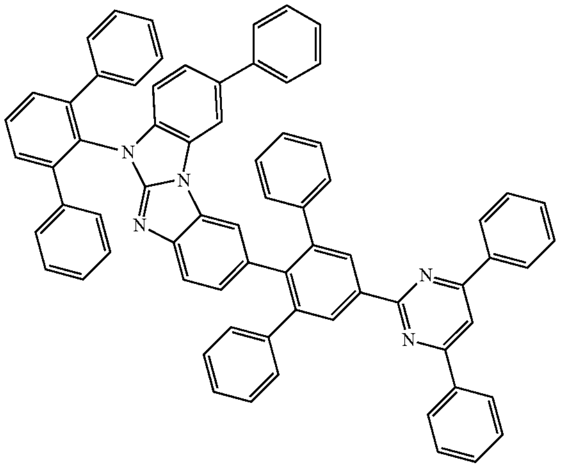
93
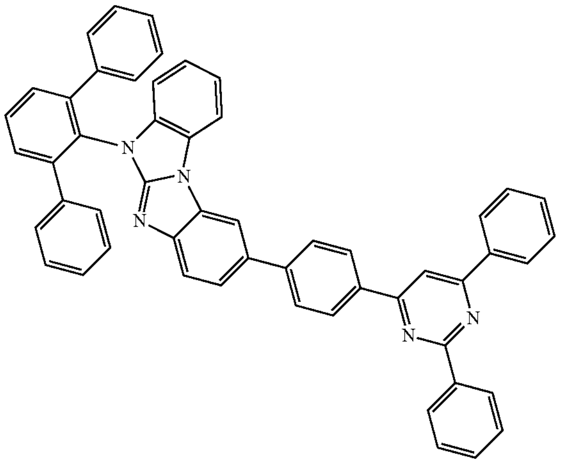
-continued
94
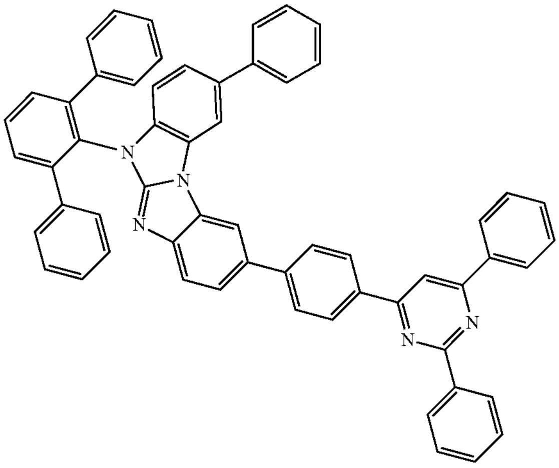
95
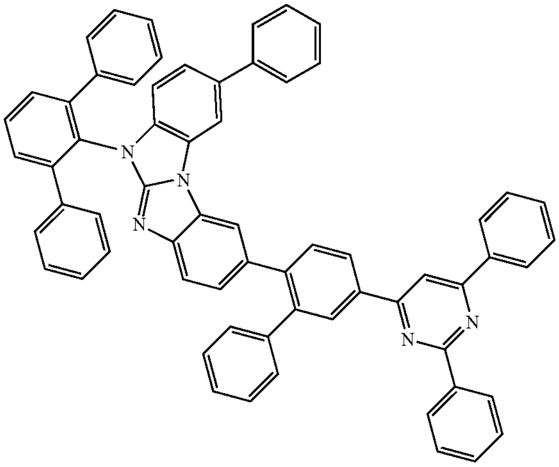
96
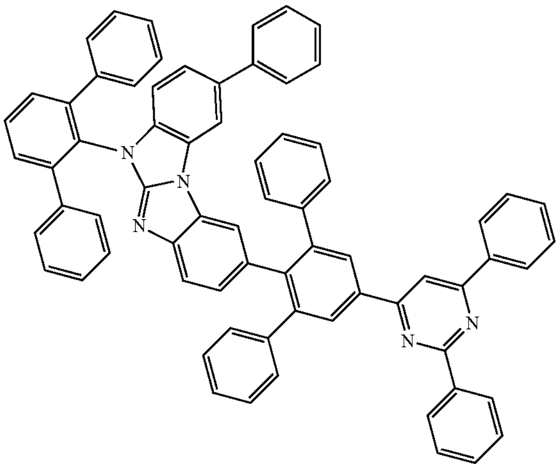

-continued
97
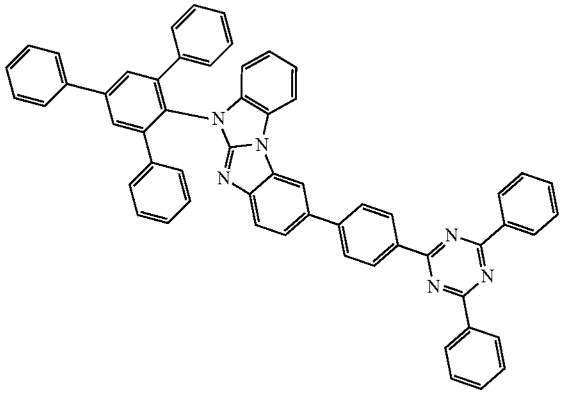
98
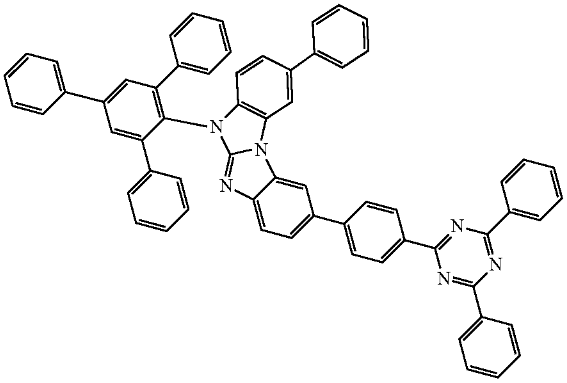
99
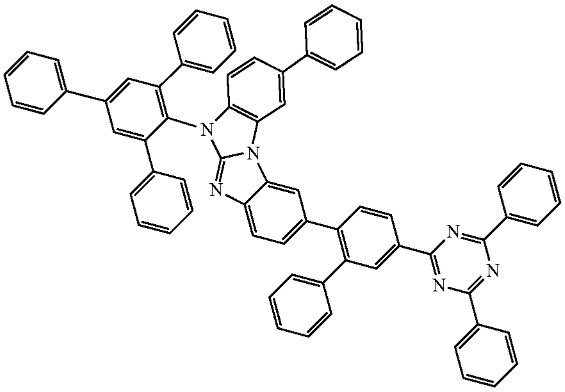
-continued
100
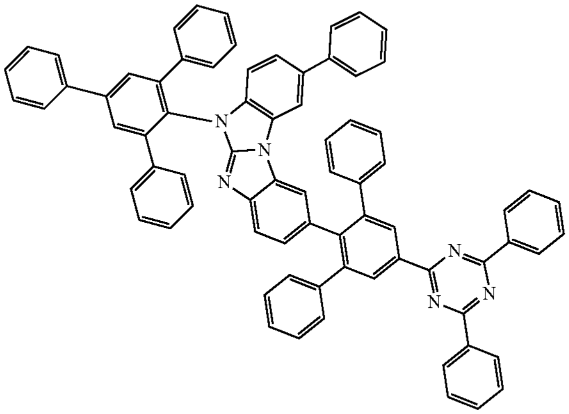
101
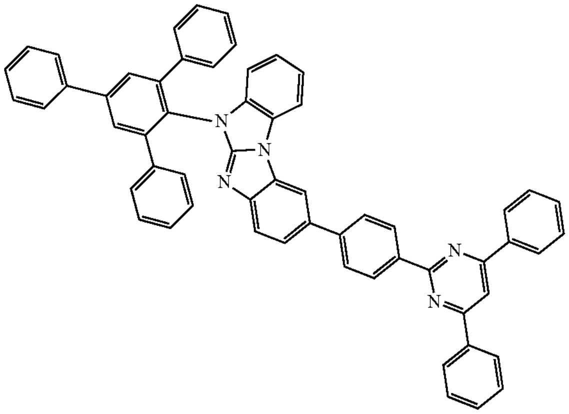
102
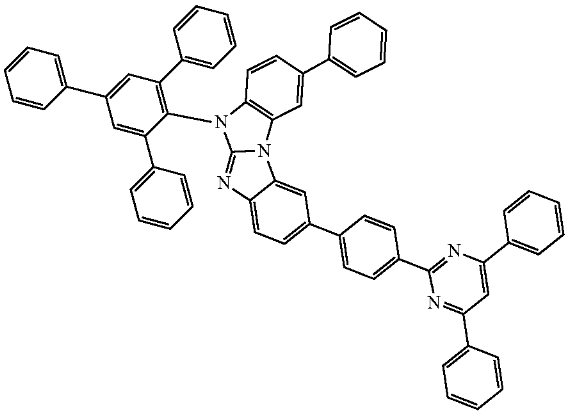

-continued
103
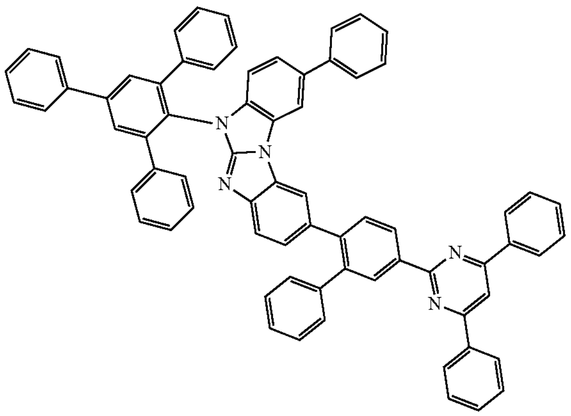
104
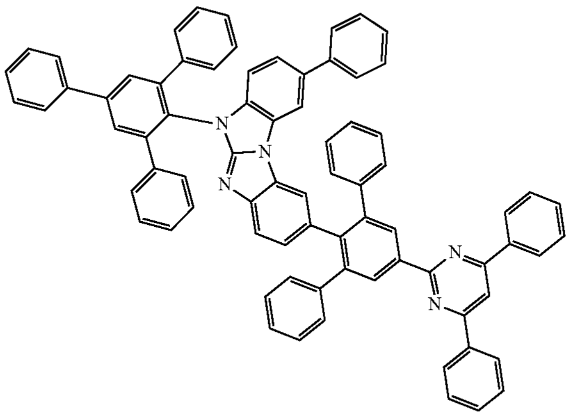
105
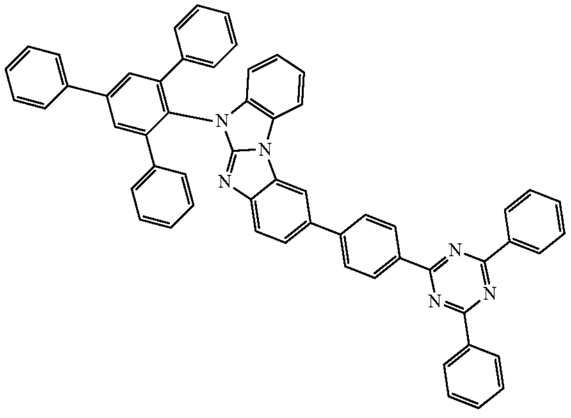
-continued
106
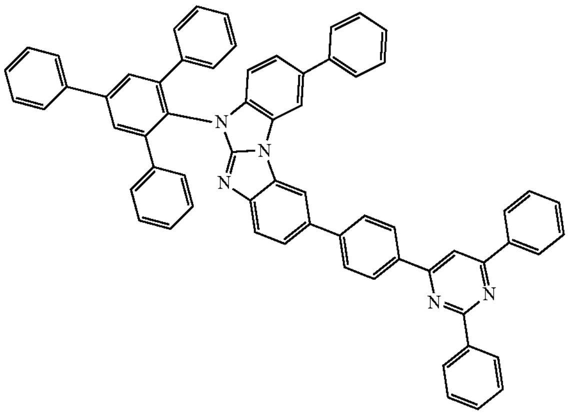
107
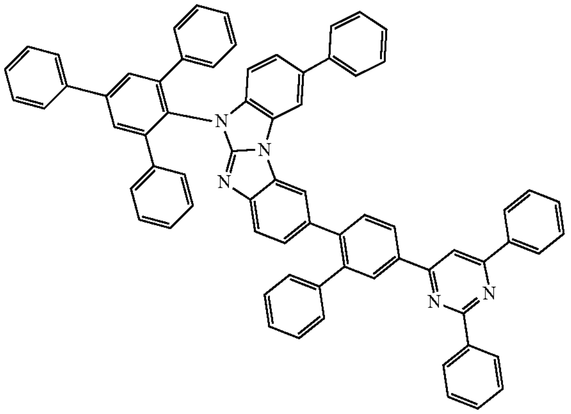
108
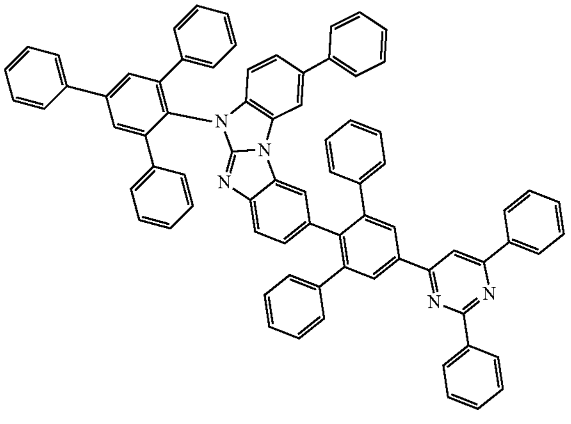

109
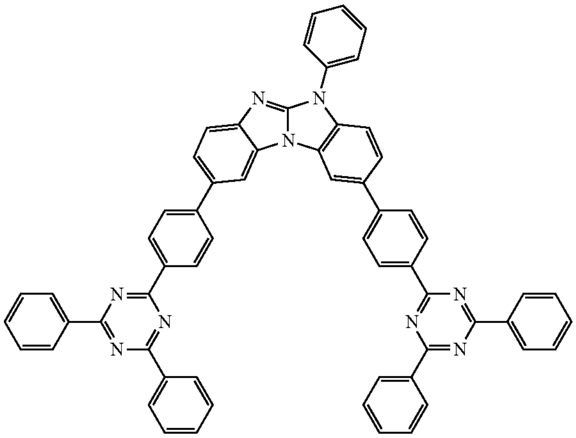
110
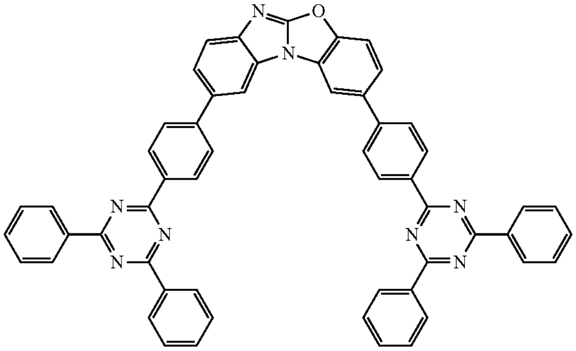
111
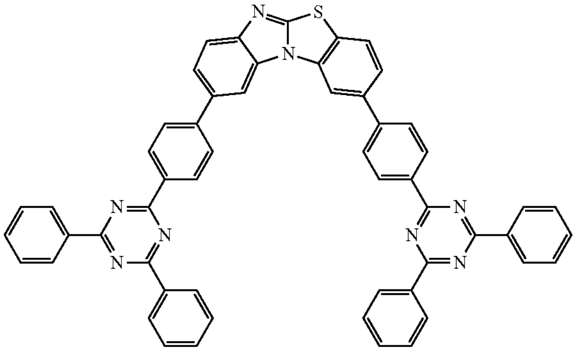
112
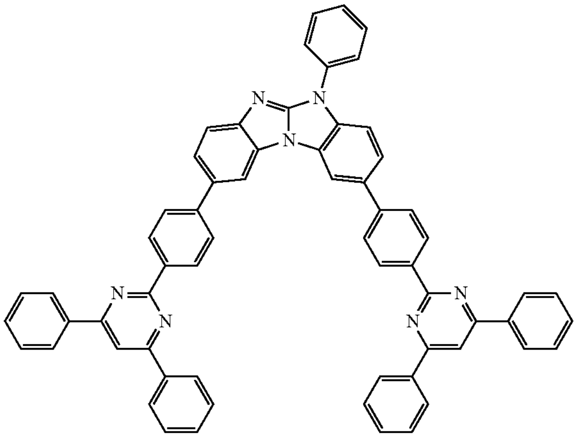
113
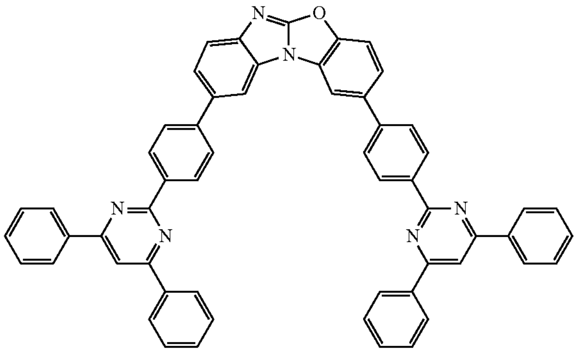
114
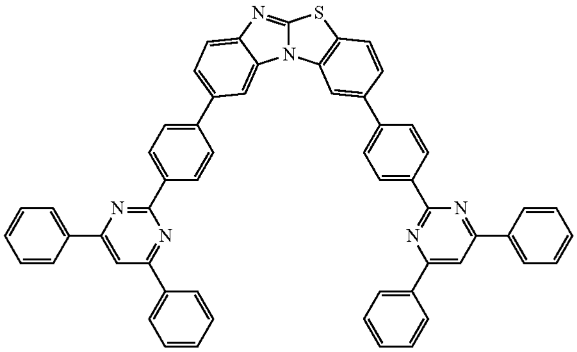

-continued
115
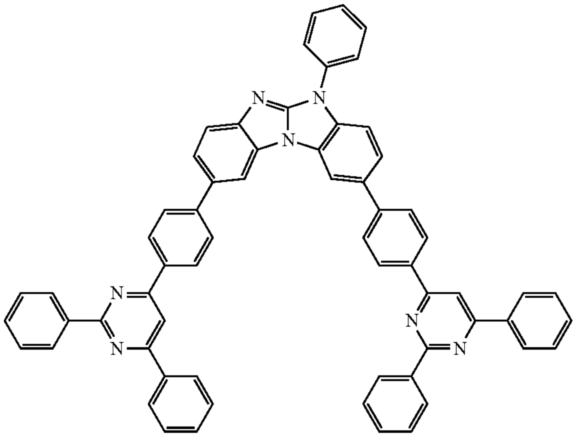
116
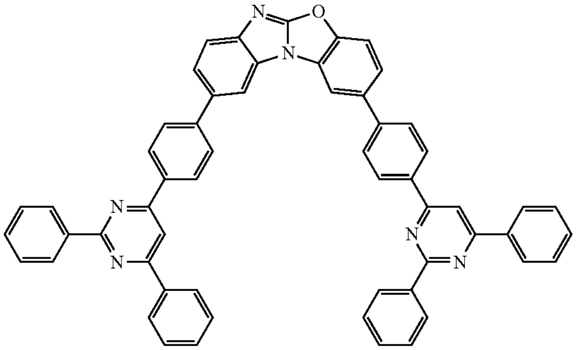
117
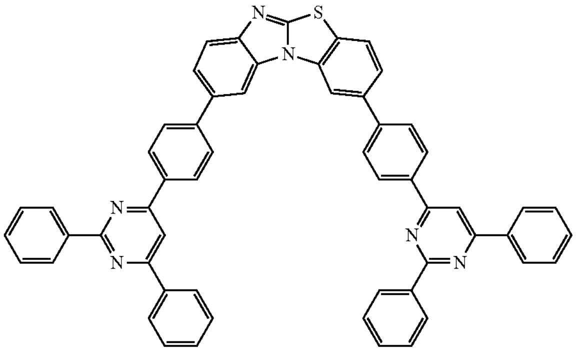
Group VIII
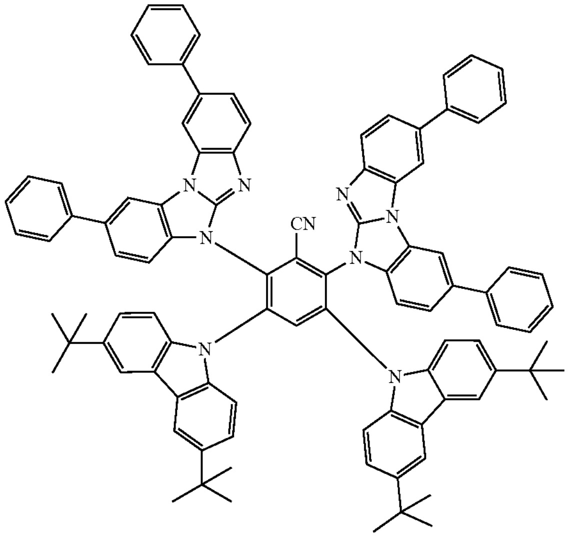
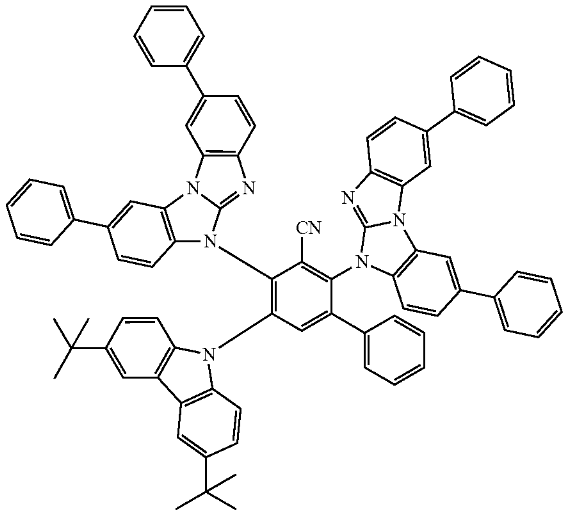
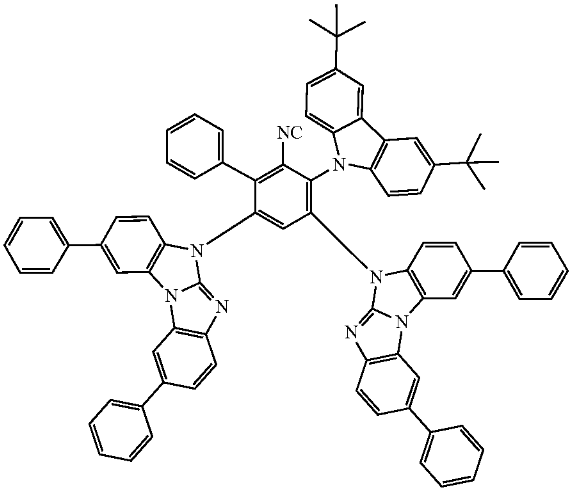

-continued
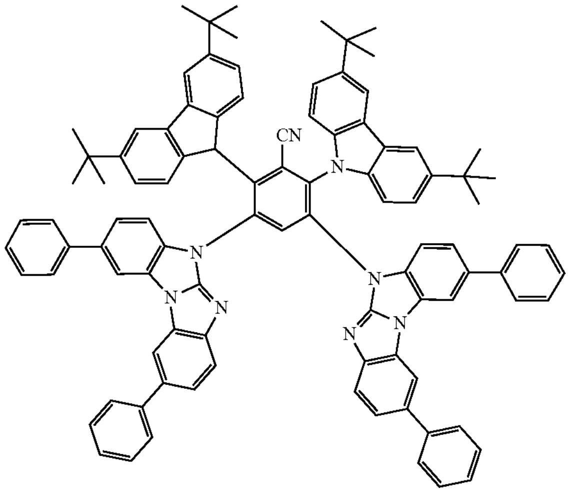
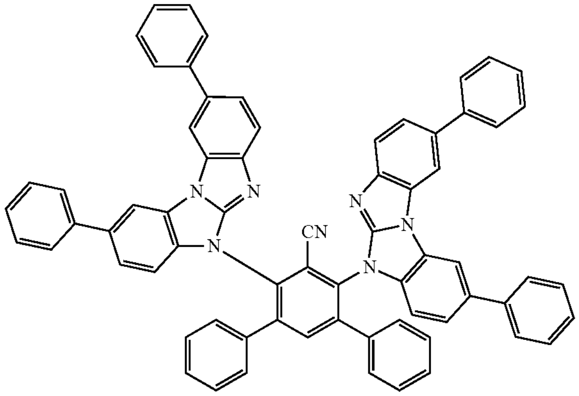
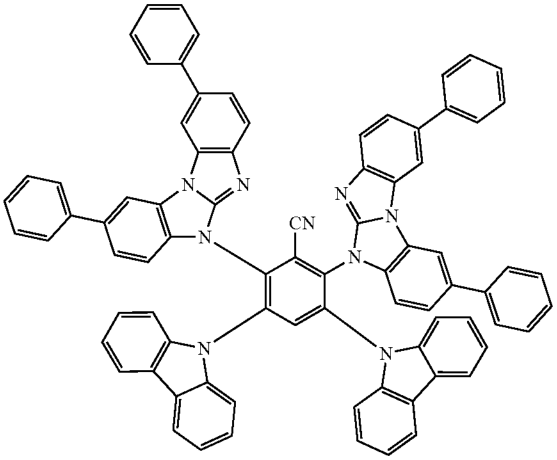
-continued
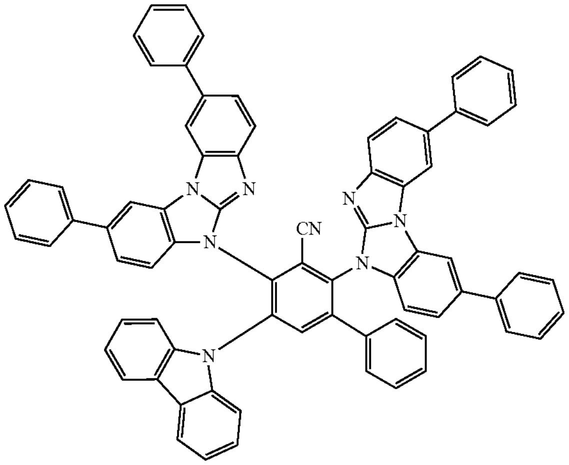
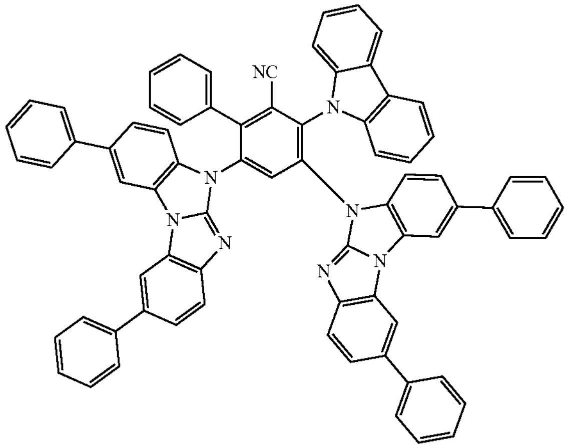
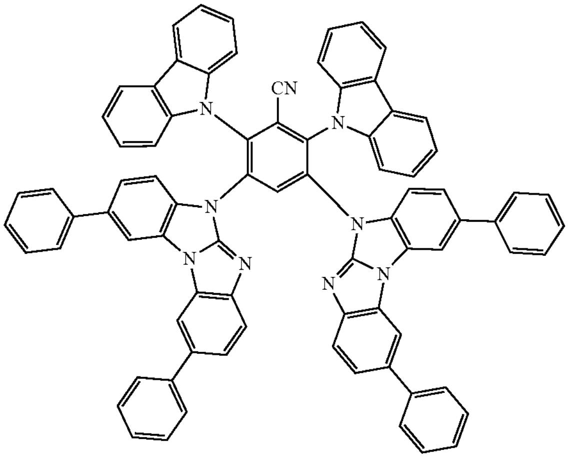

-continued
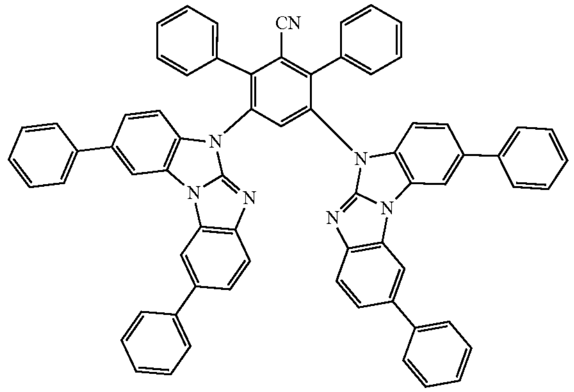
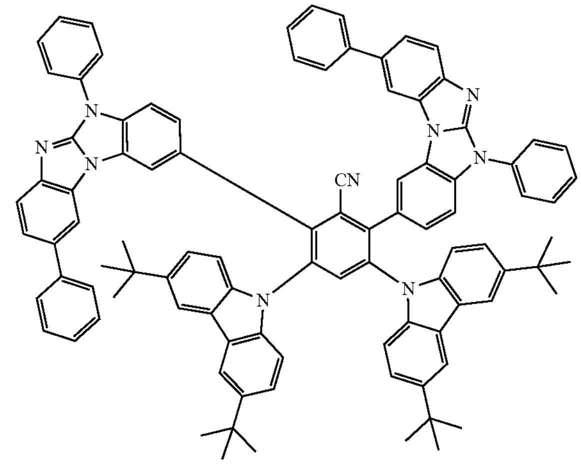
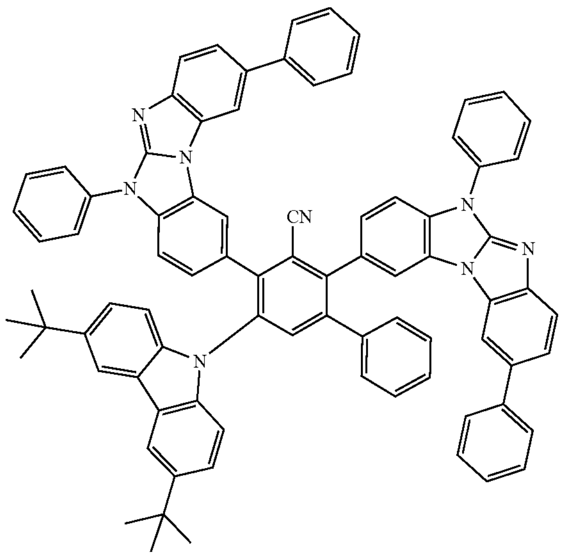
-continued
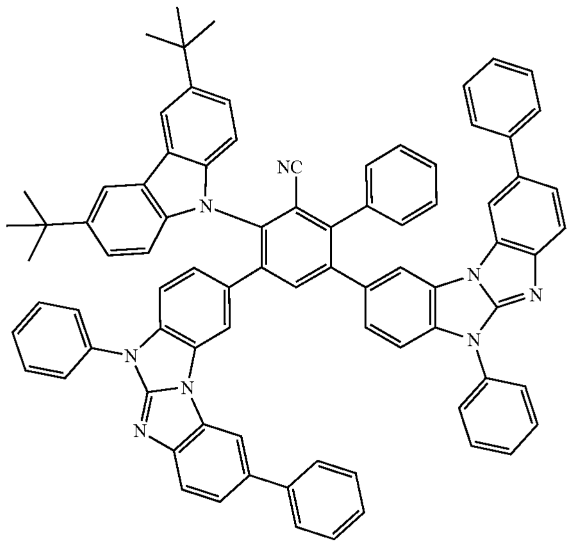
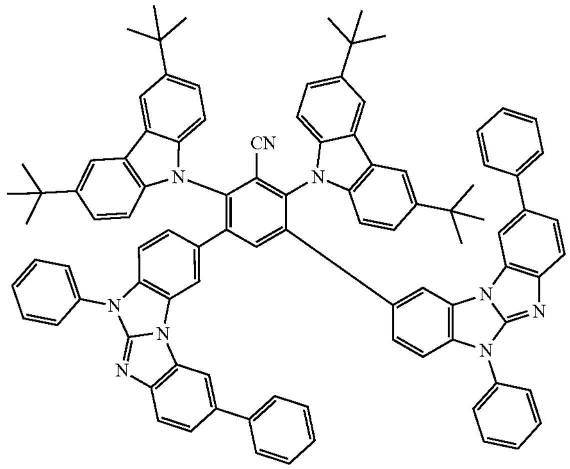
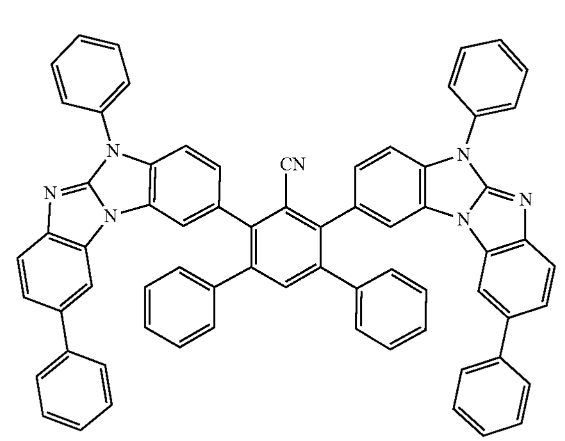

-continued
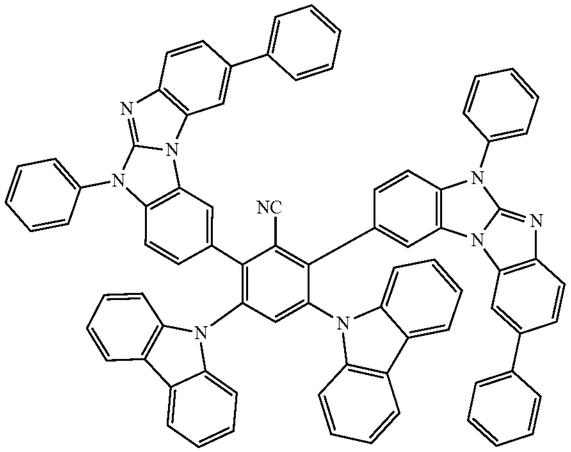
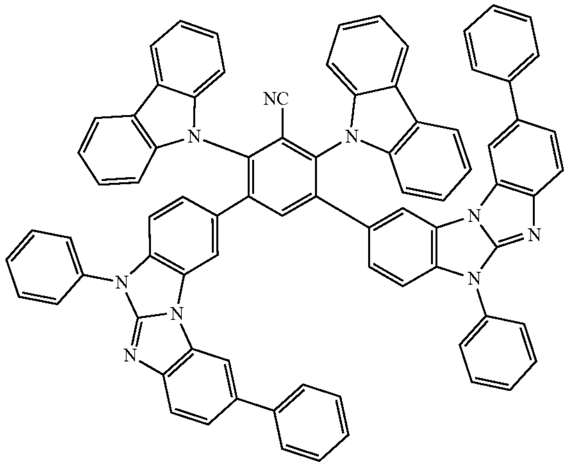
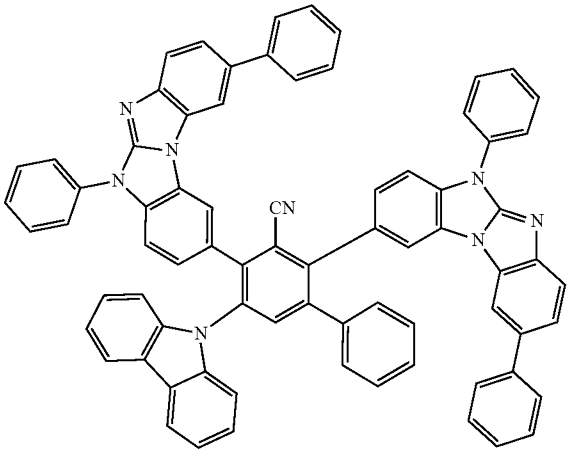
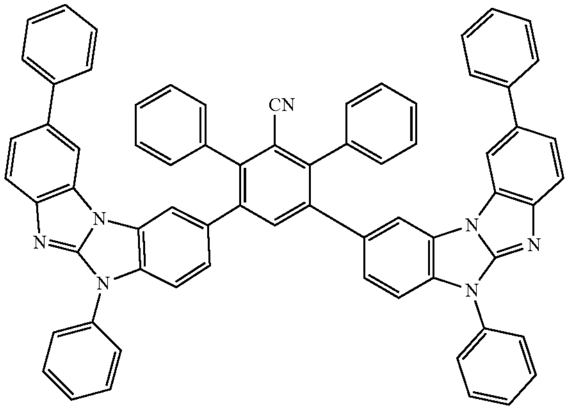
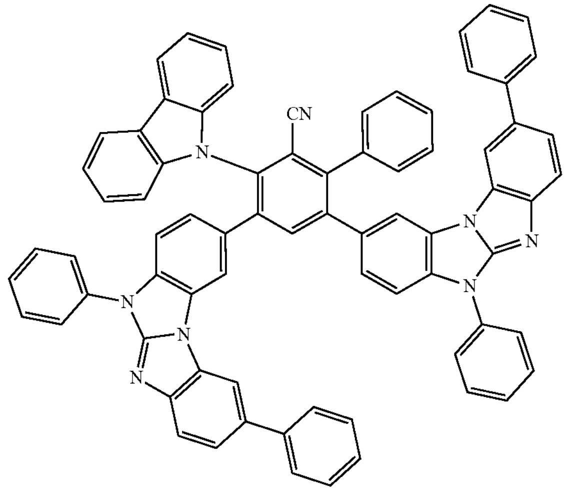
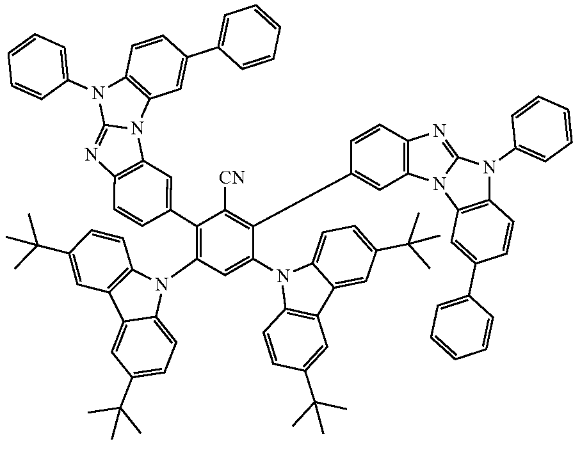
-continued

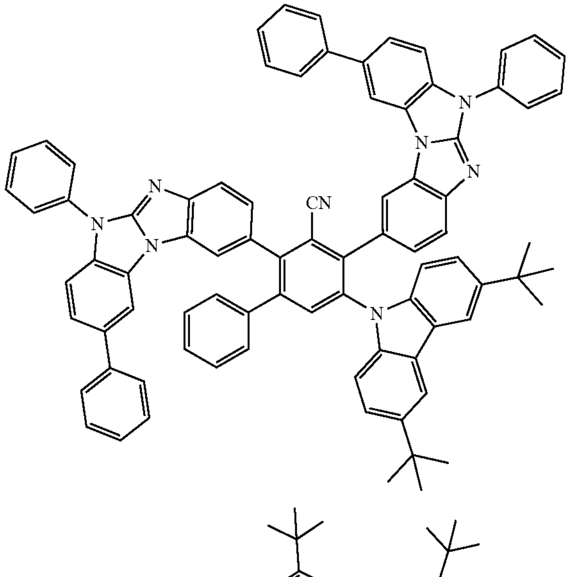
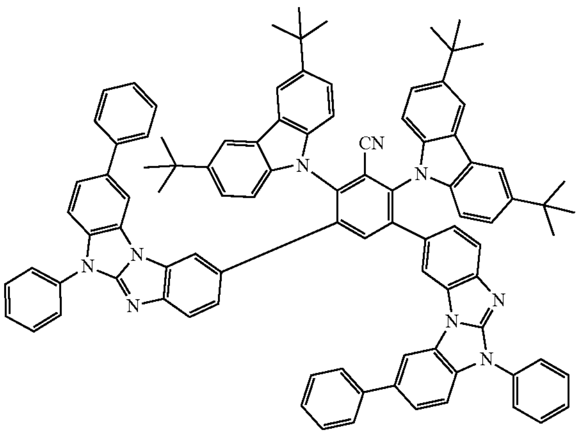
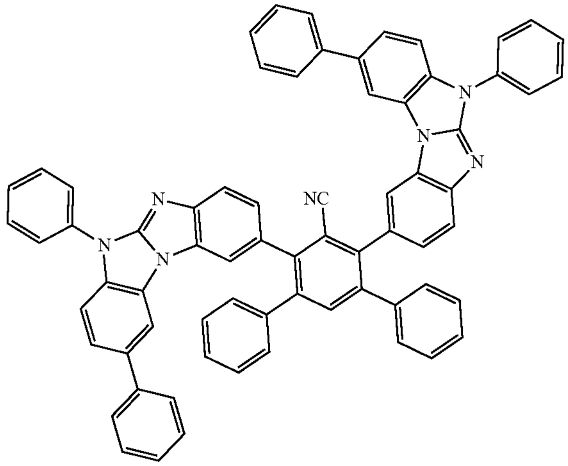
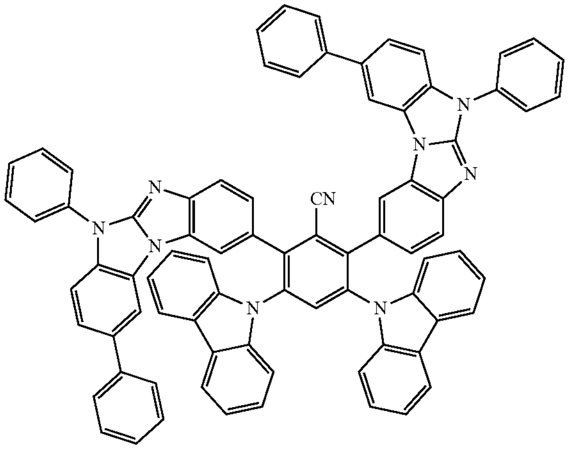
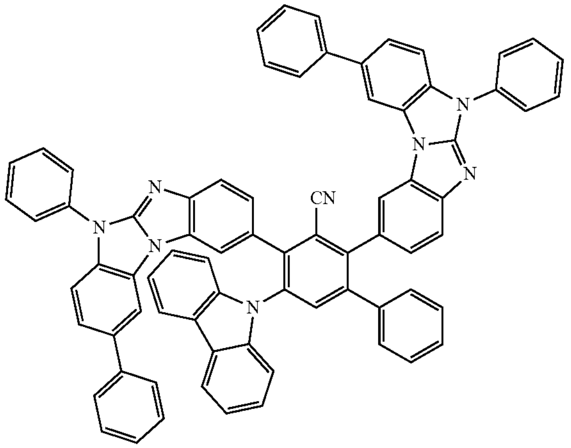
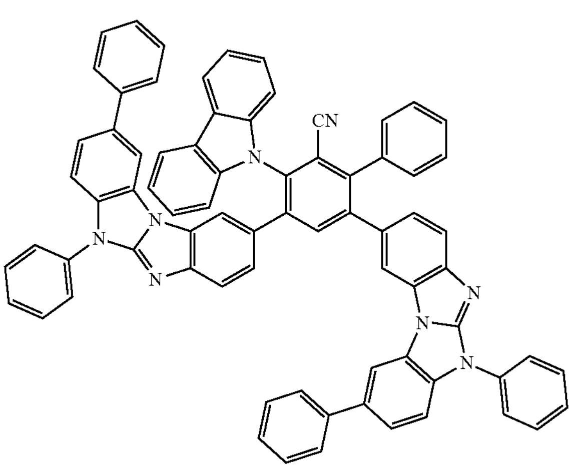

-continued
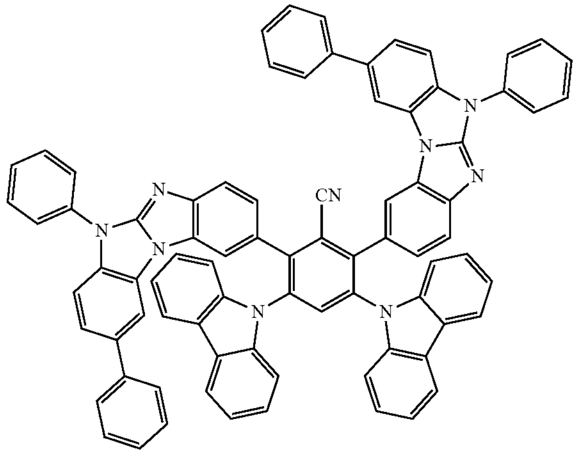
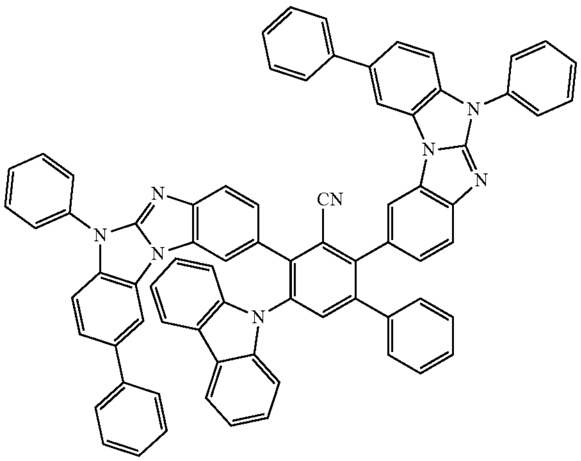
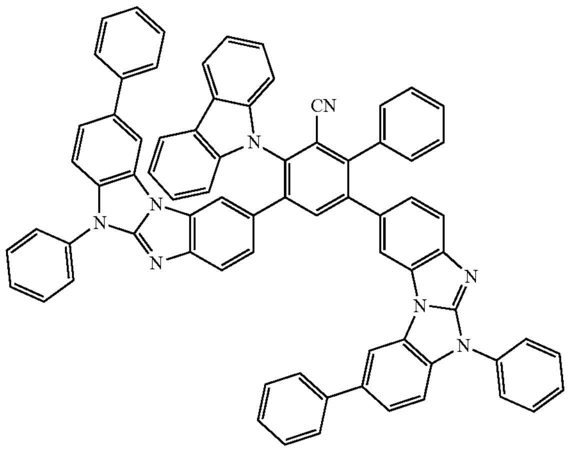
-continued
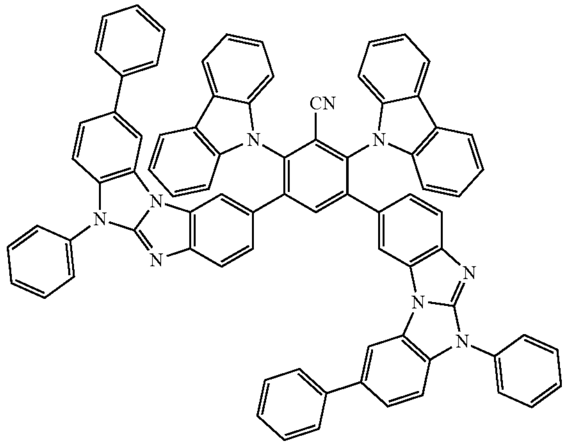
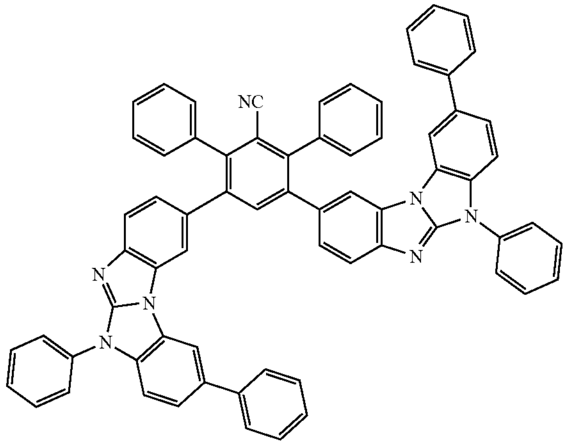
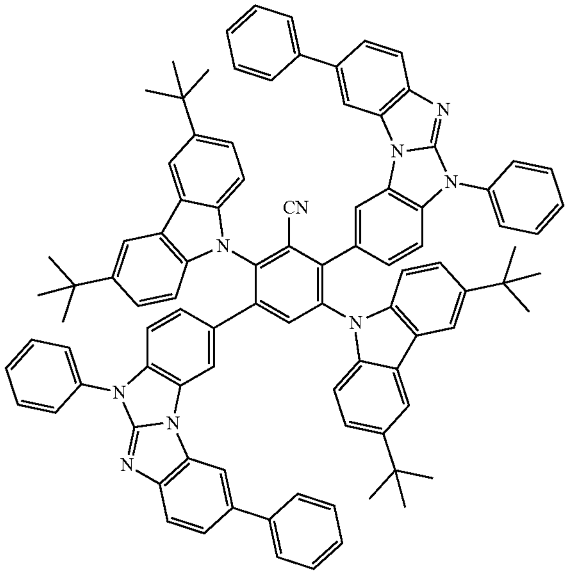

-continued
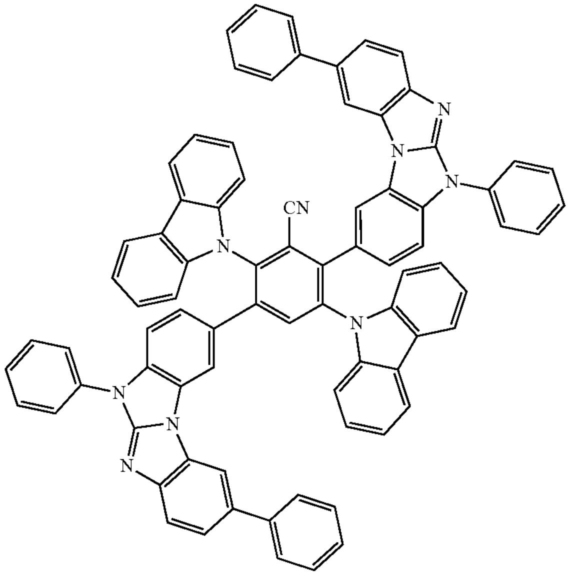
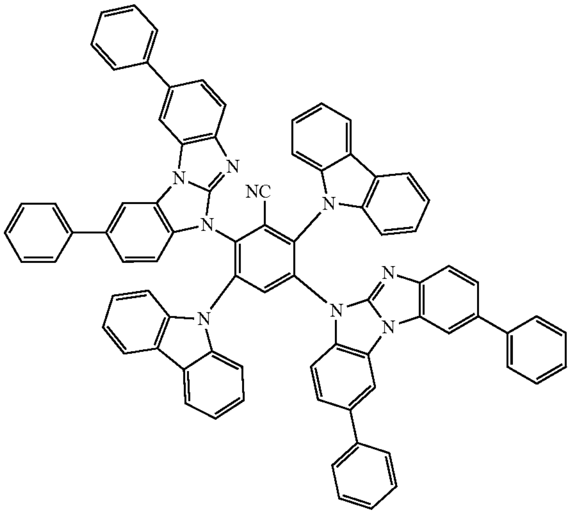
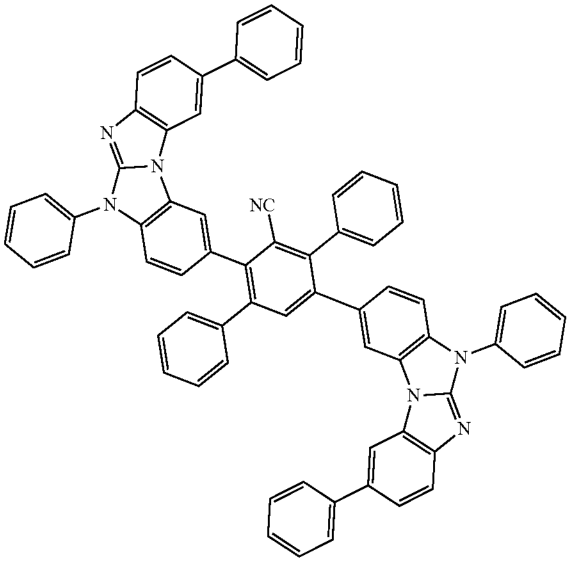
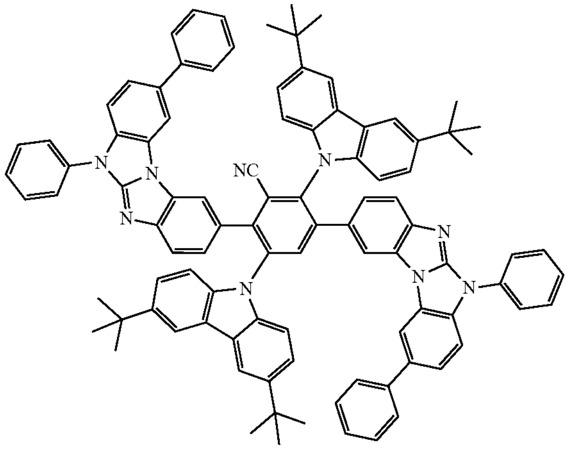
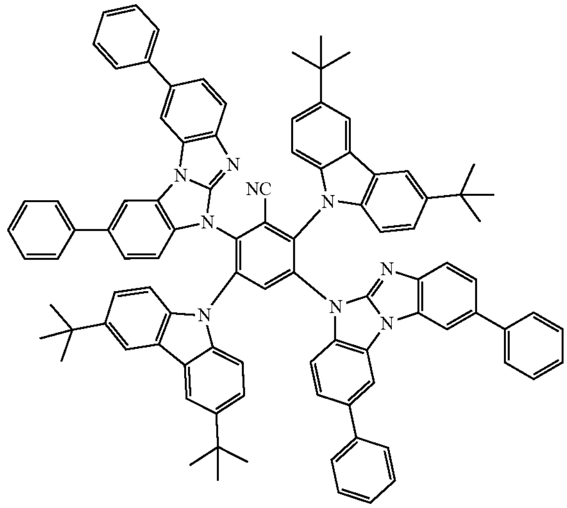
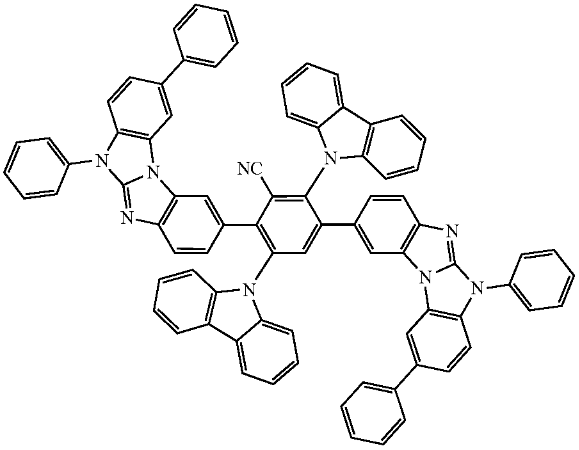
-continued -continued
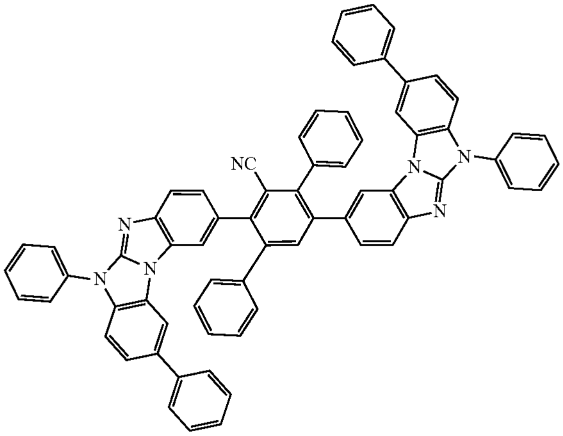
Group IX
1
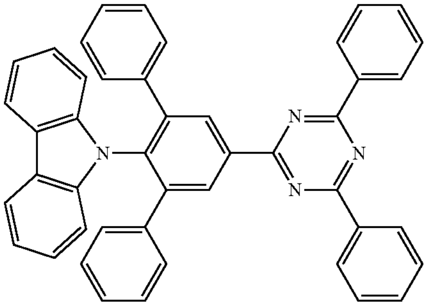
2
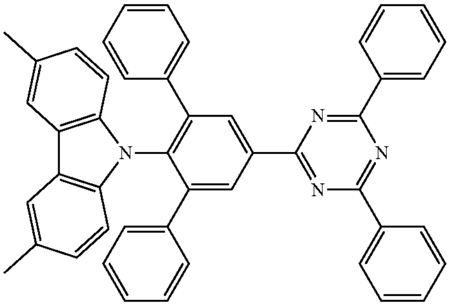
3
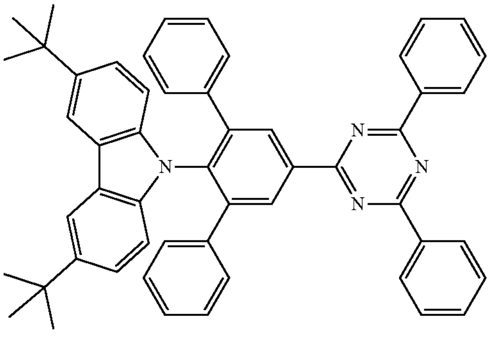
-continued
4
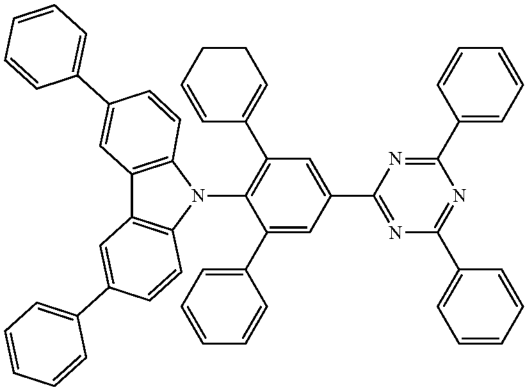
5
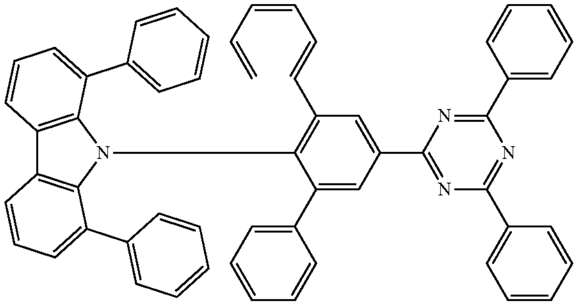
6
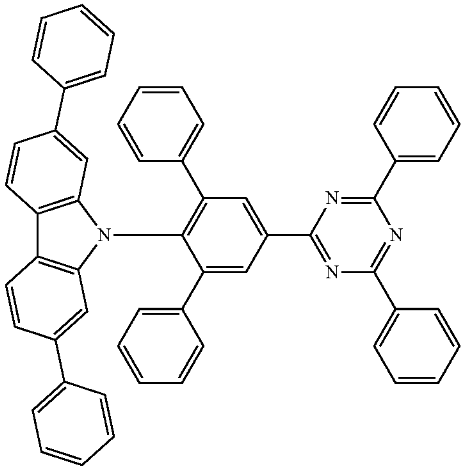
7
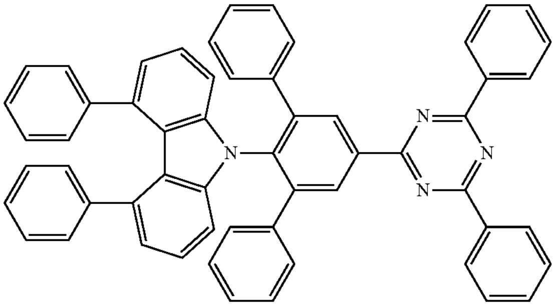

-continued
8
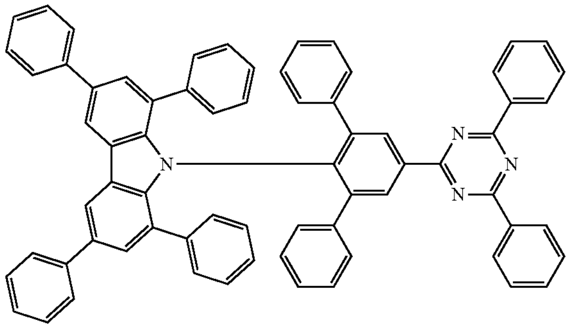
9
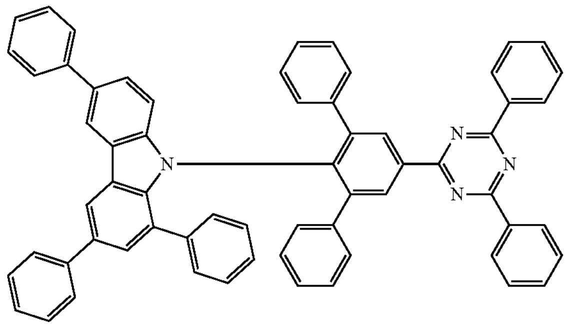
10
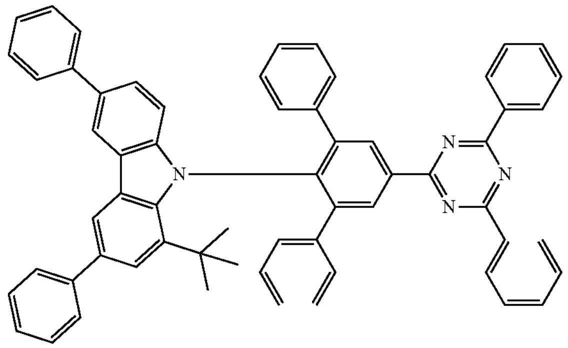
11
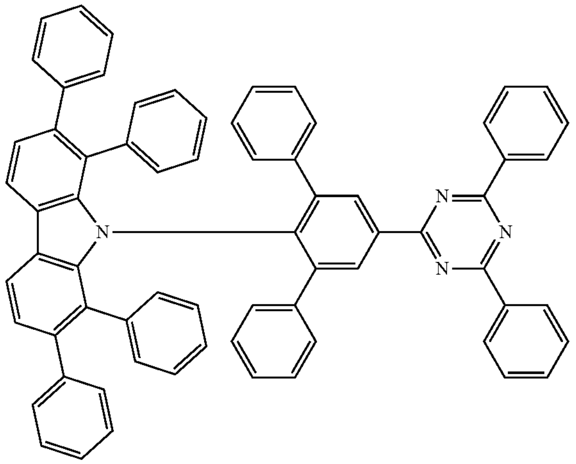
-continued
12
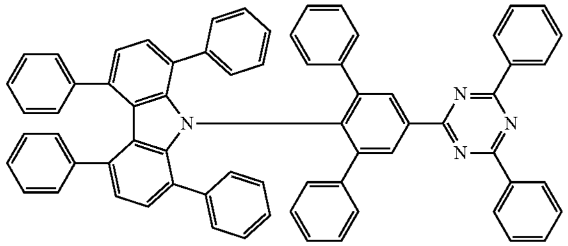
13
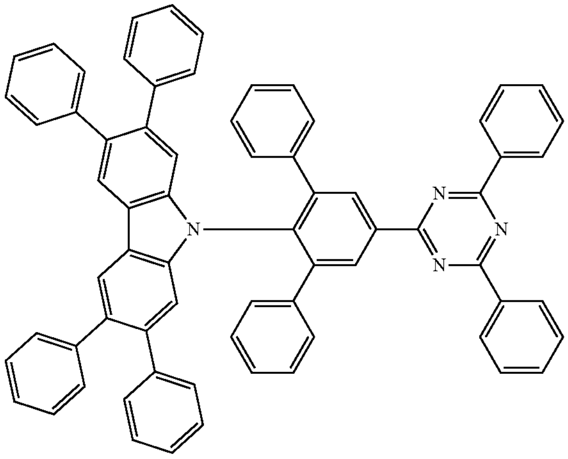
14
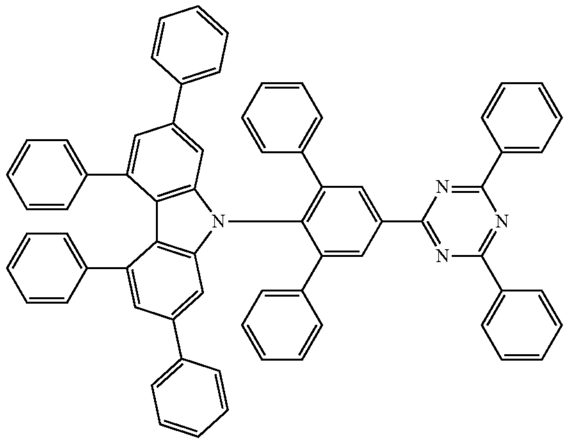
15
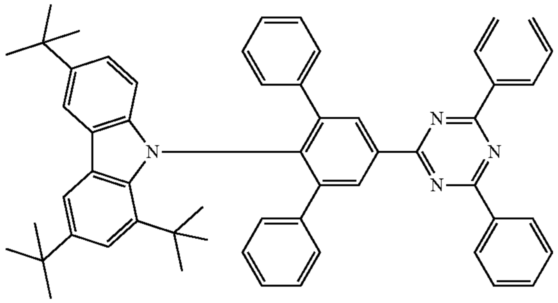

-continued
16
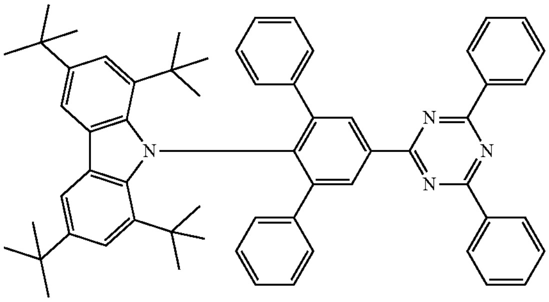
17
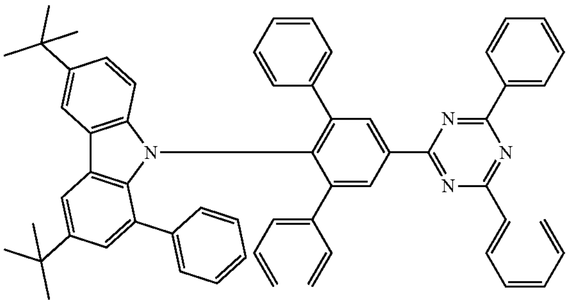
18
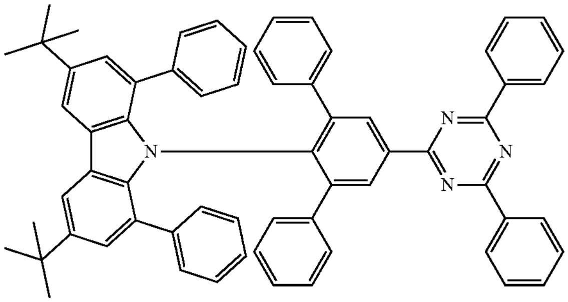
19
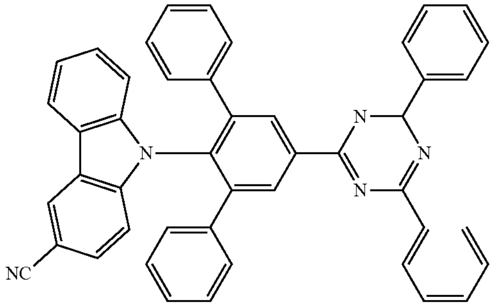
20
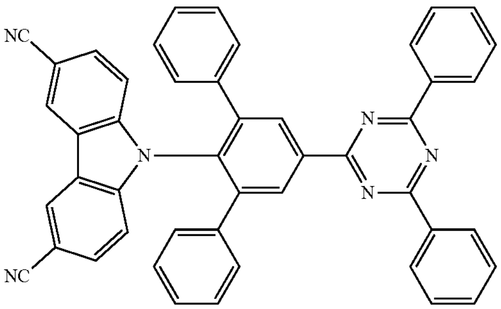
-continued
21
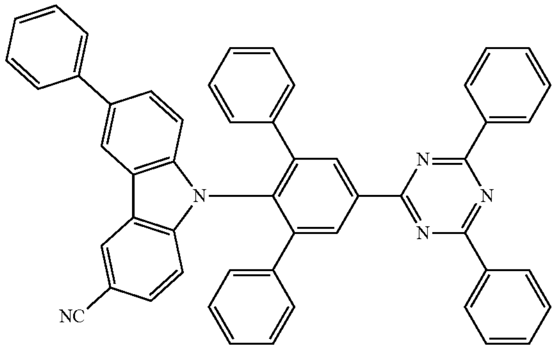
22
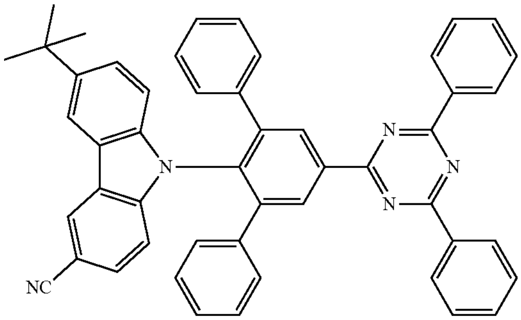
23
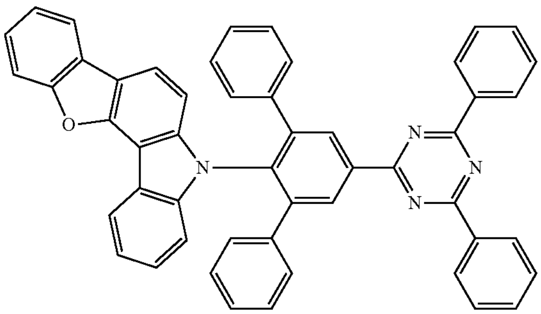
24
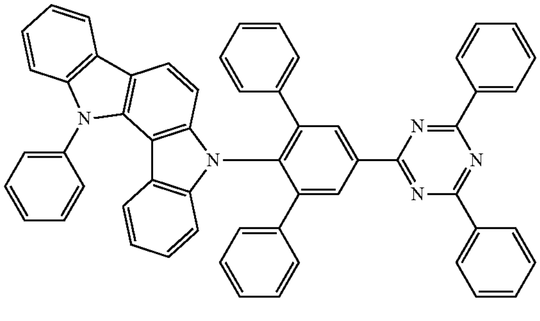

-continued
25
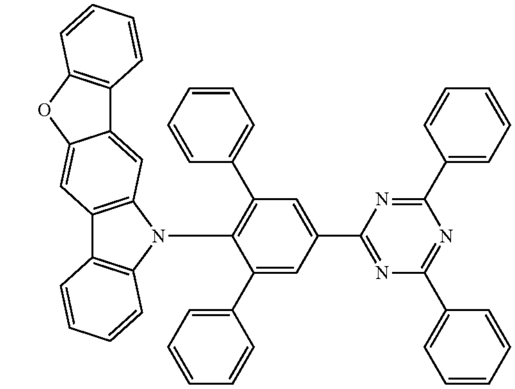
26
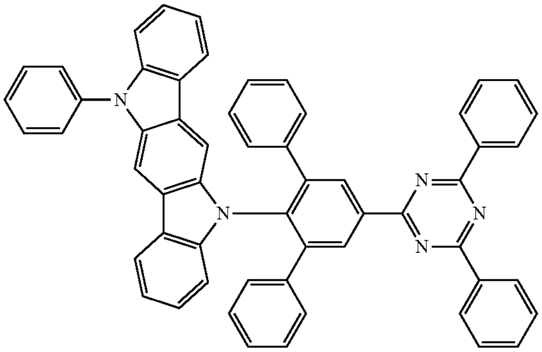
27
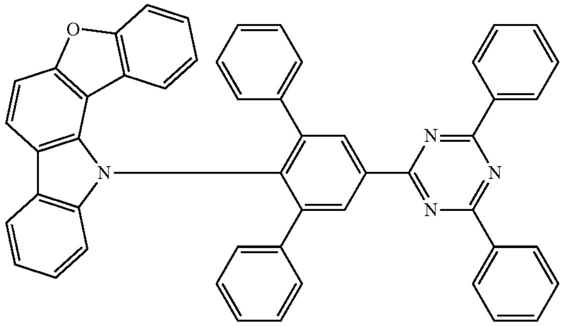
28
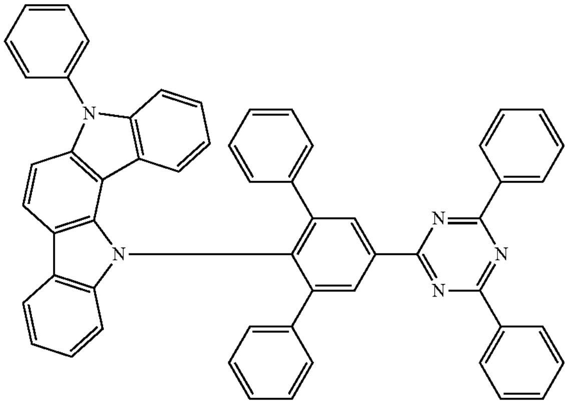
-continued
29
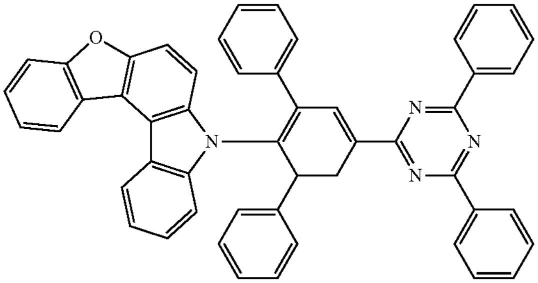
30
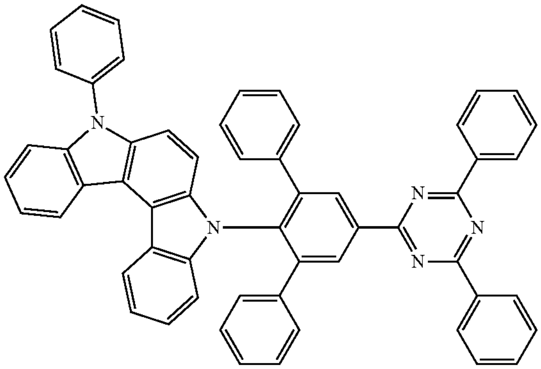
31
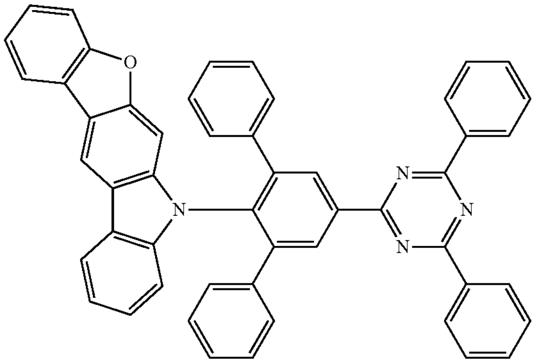
32
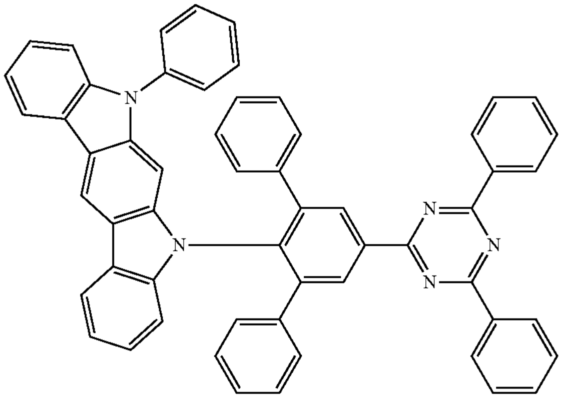

33
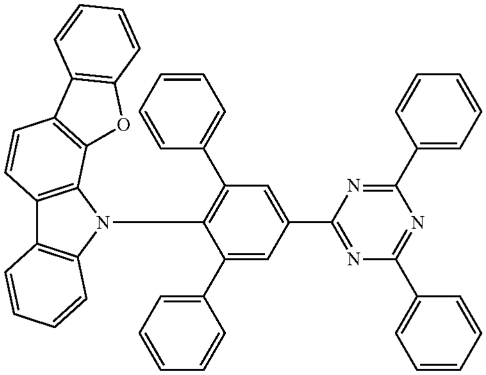
34
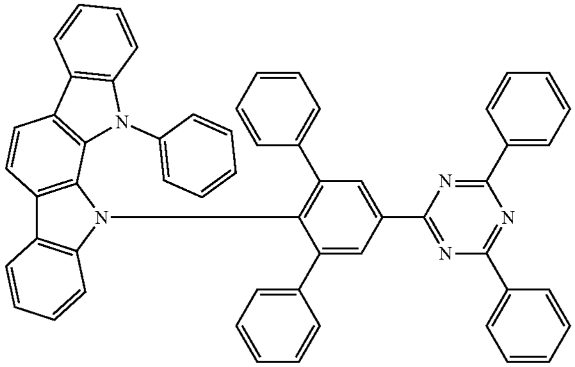
35
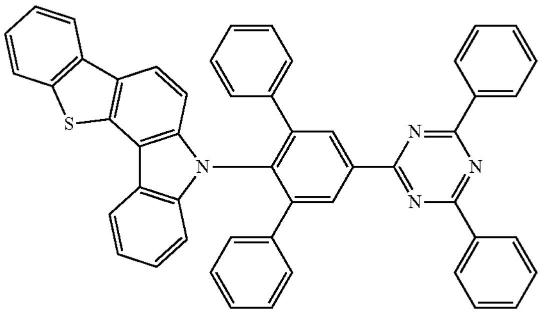
36
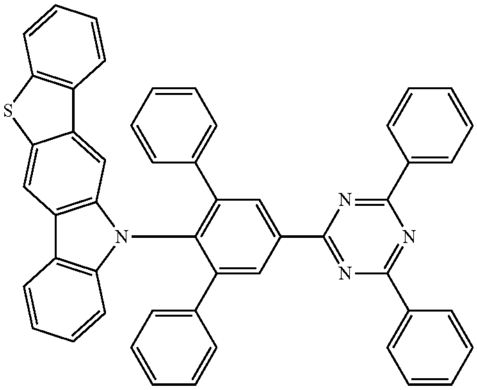
37
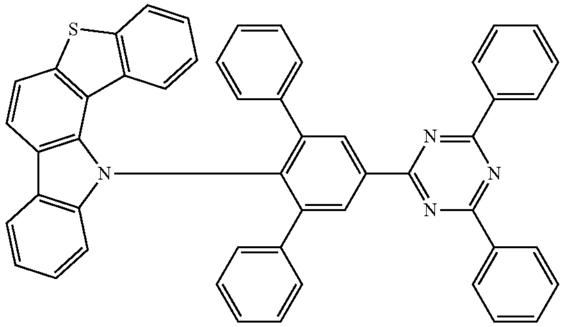
38
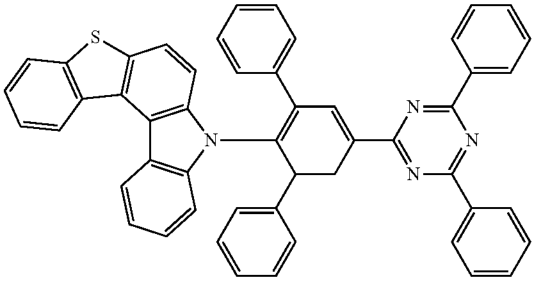
39
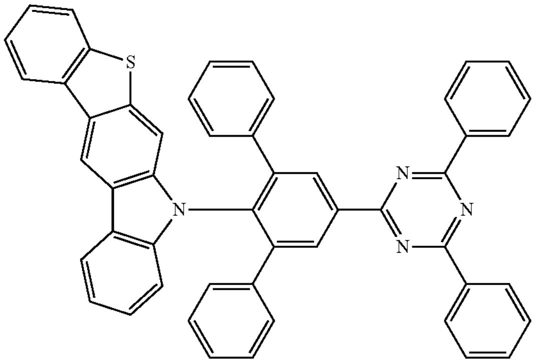
40
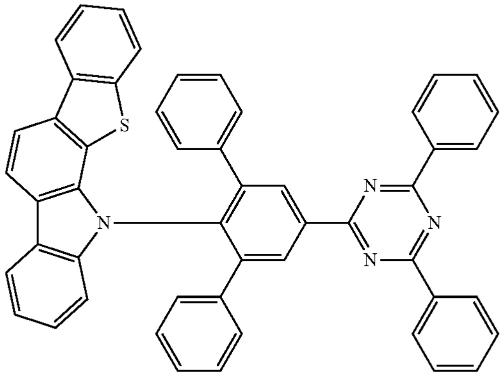

-continued
41
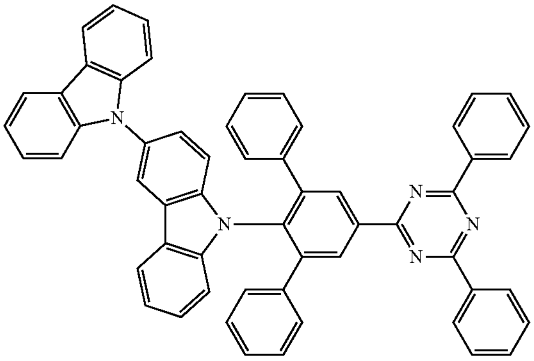
42
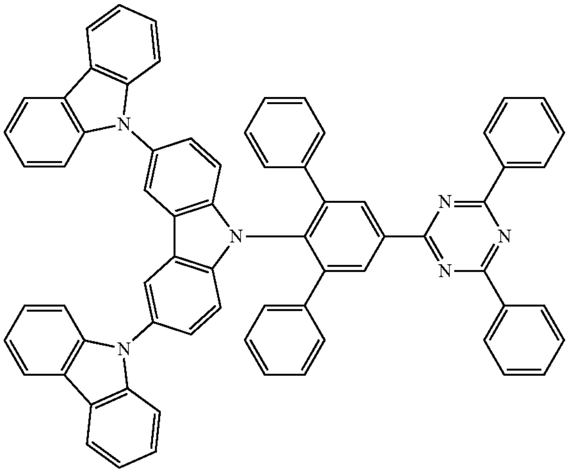
43
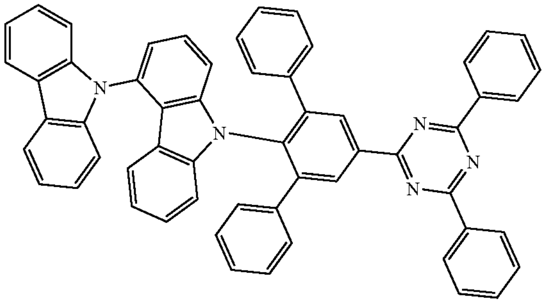
44
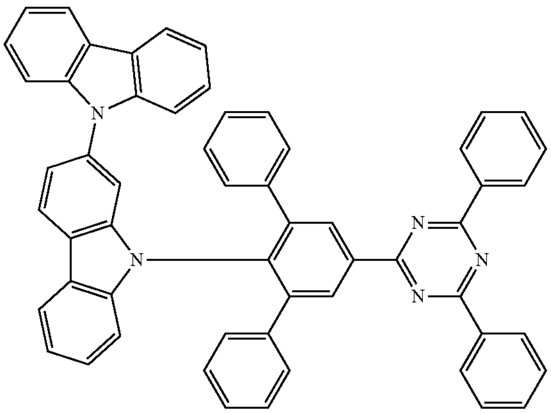
-continued
45
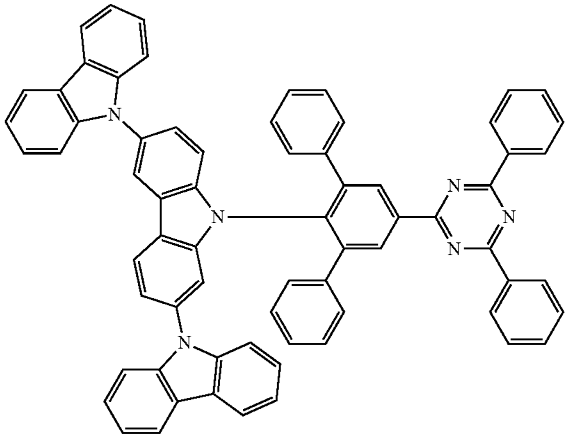
46
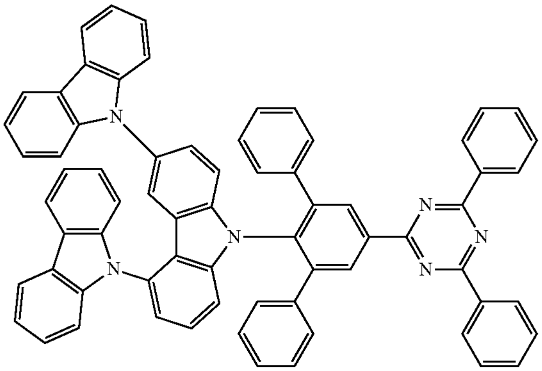
47
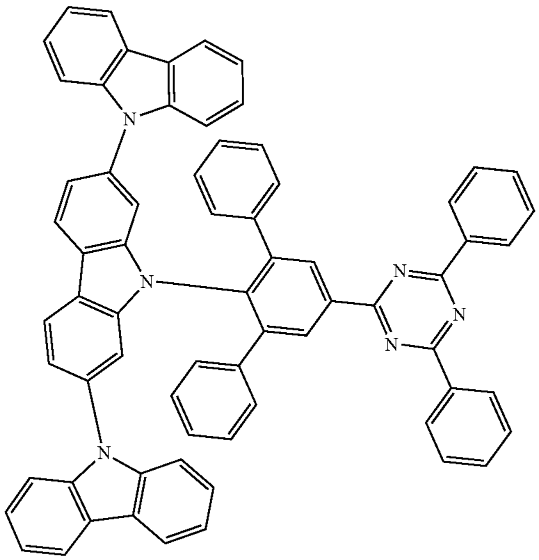

-continued
48
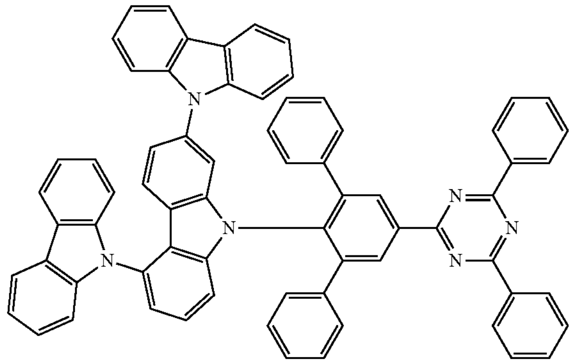
49
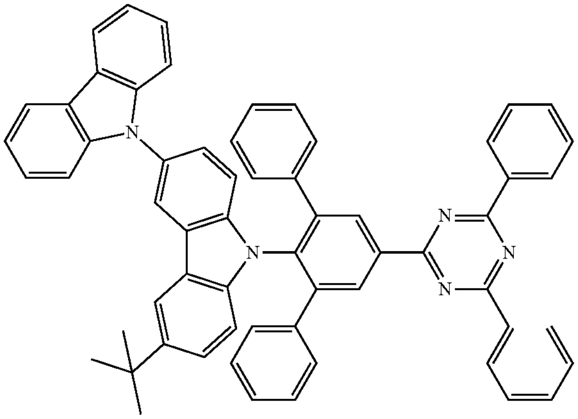
50
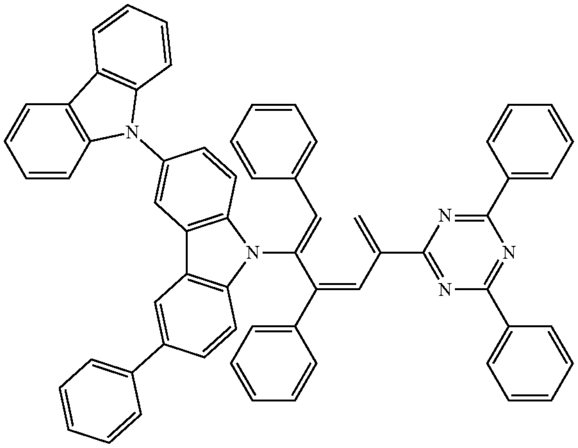
-continued
51
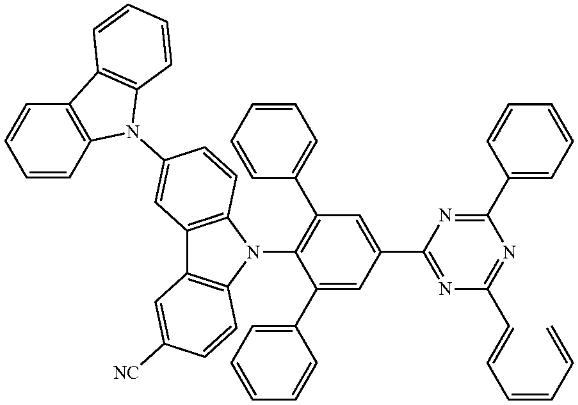
52
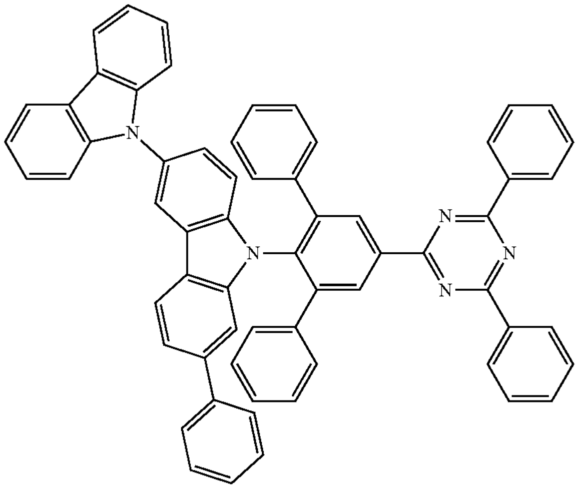
53
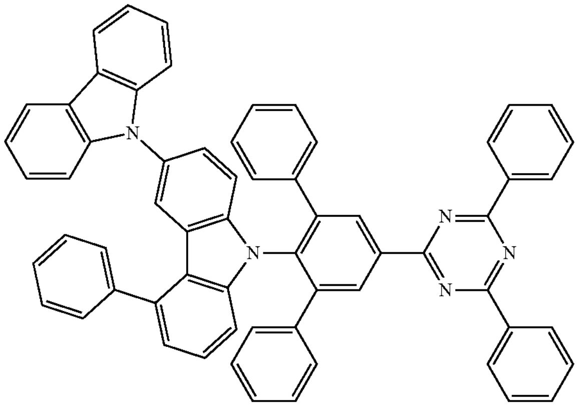

-continued
54
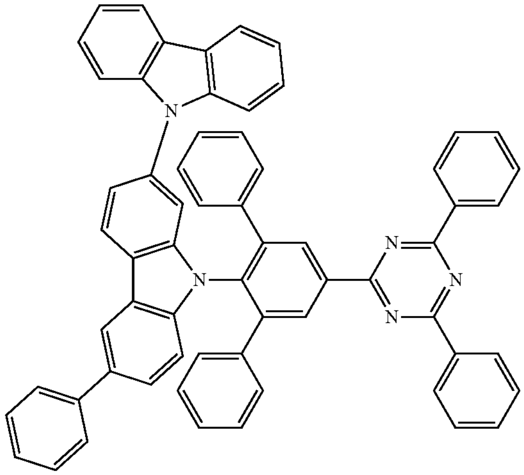
55
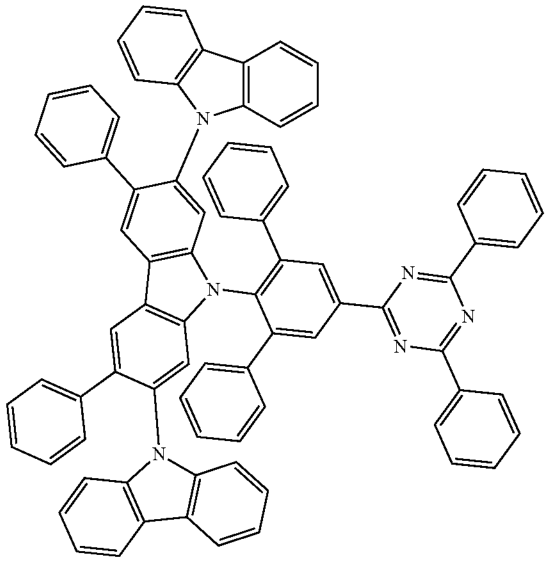
56
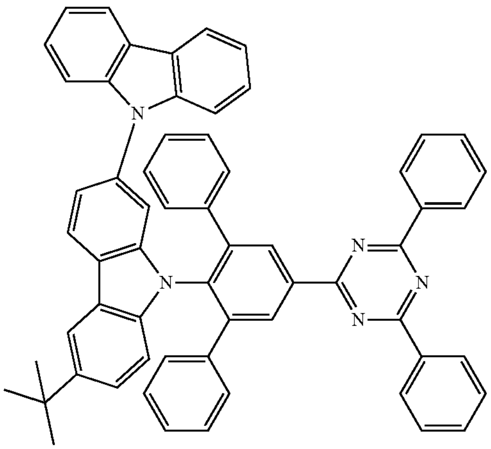
-continued
57
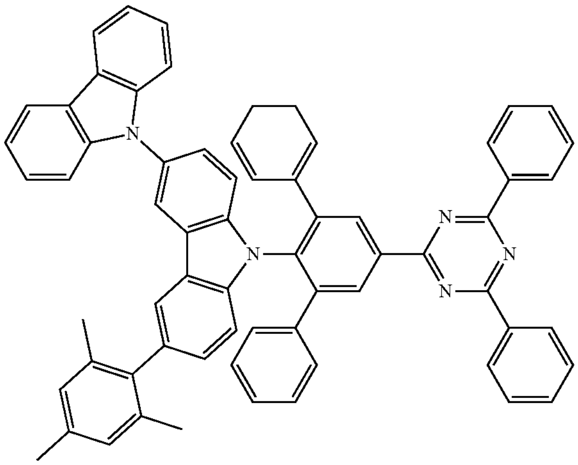
58
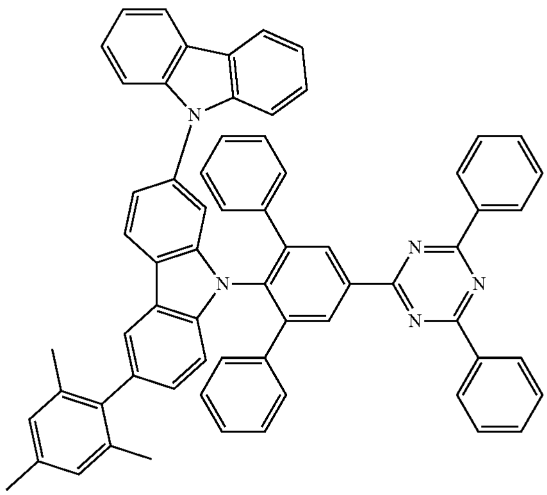
59
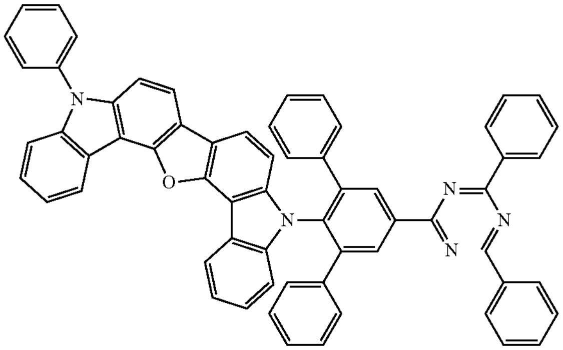

-continued
60
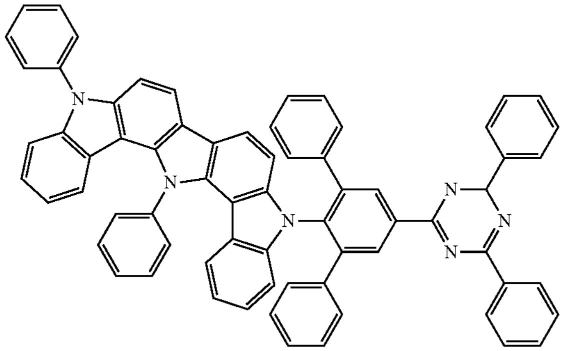
61
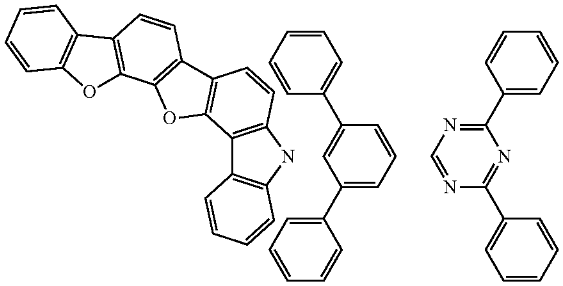
62
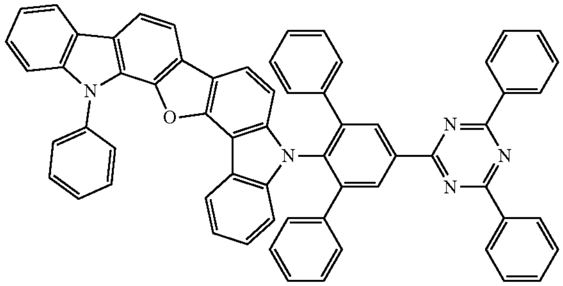
63
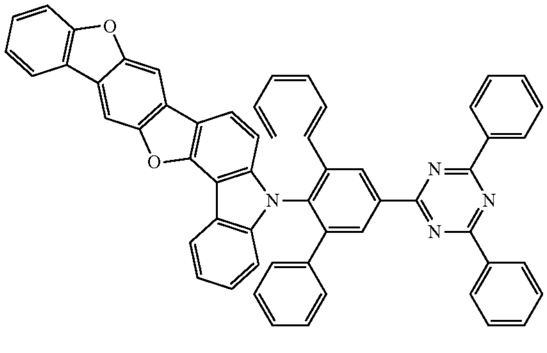
-continued
64
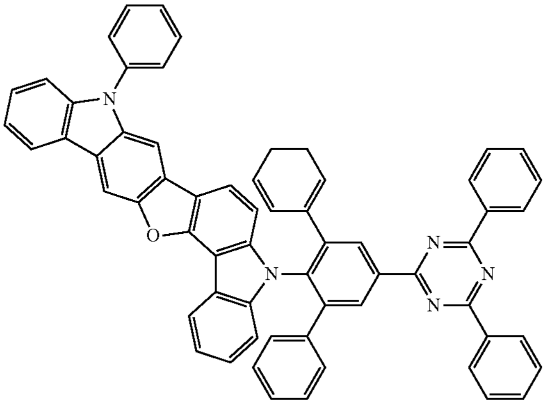
65
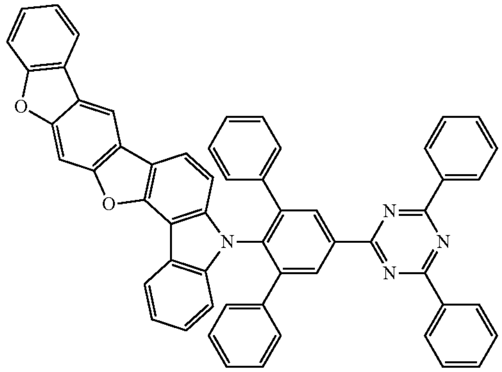
66
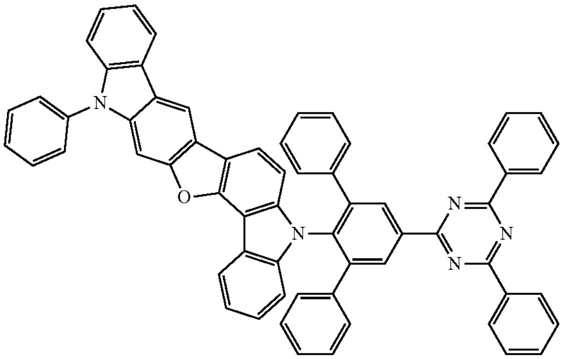
67
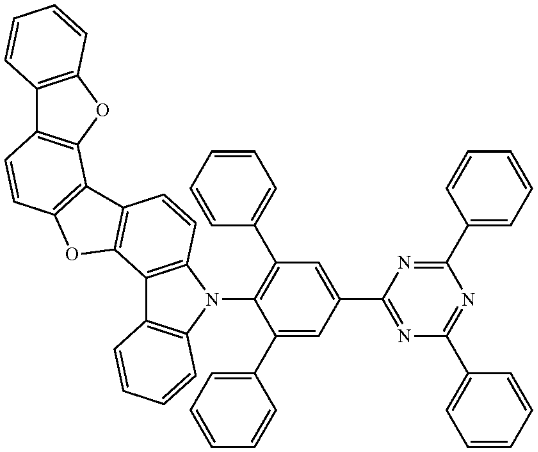

-continued
68
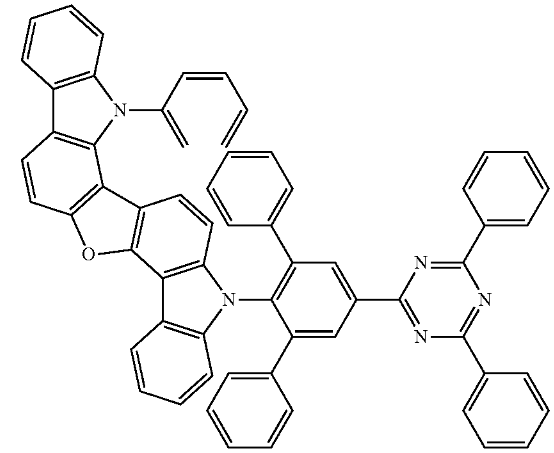
69
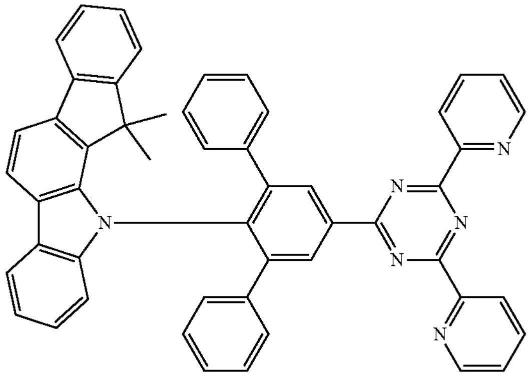
70
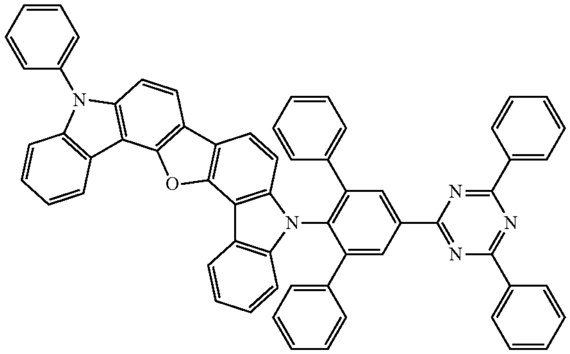
71
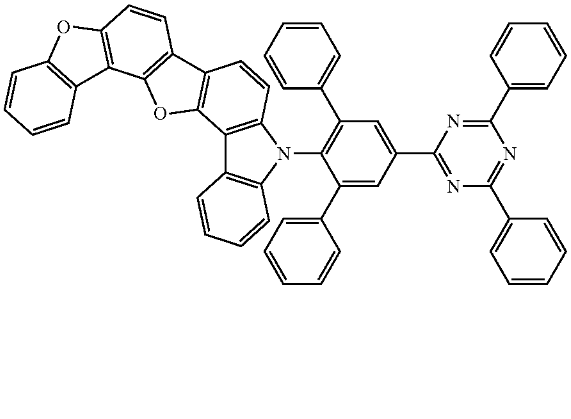
-continued
72
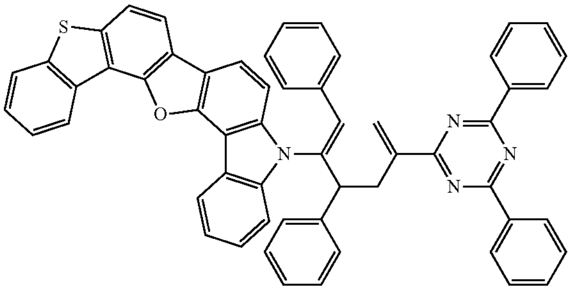
73
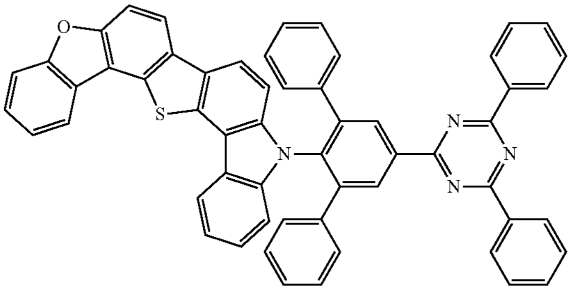
74
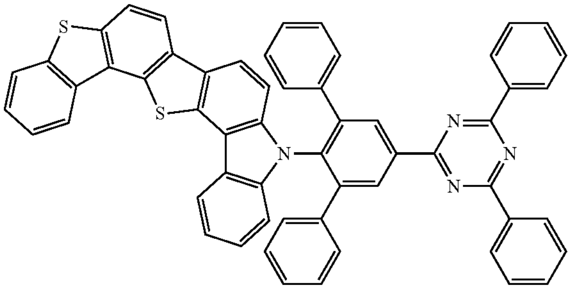
75
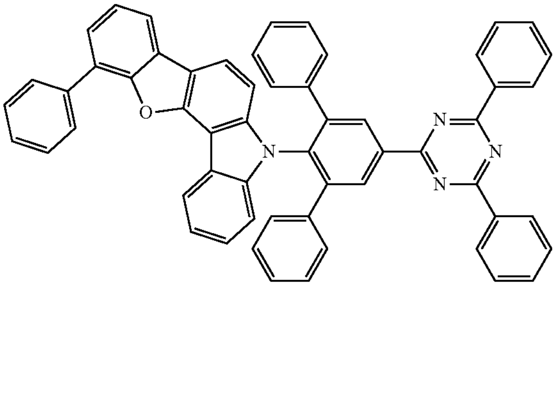

-continued
76
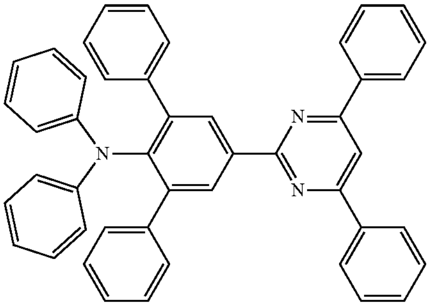
77
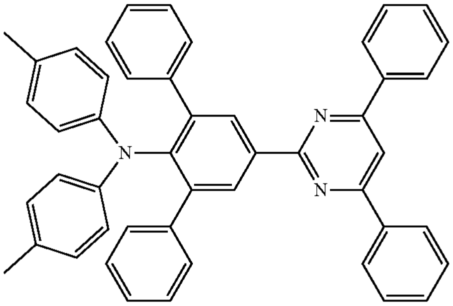
78
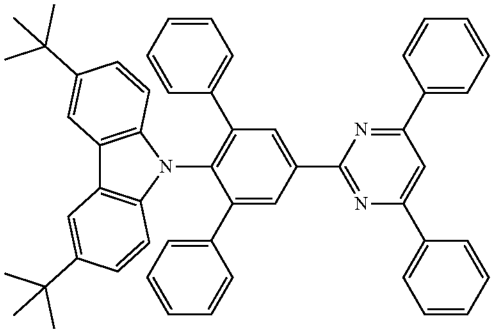
79
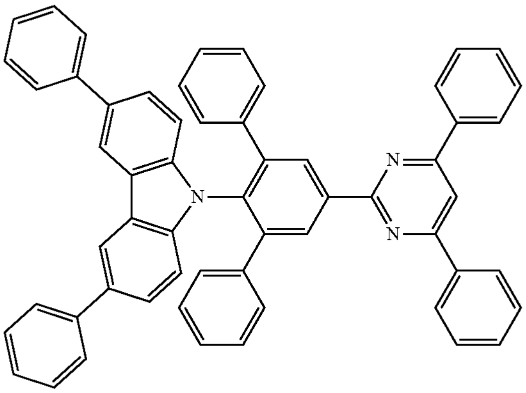
-continued
80
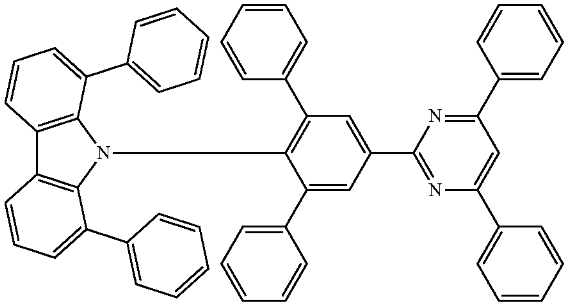
81
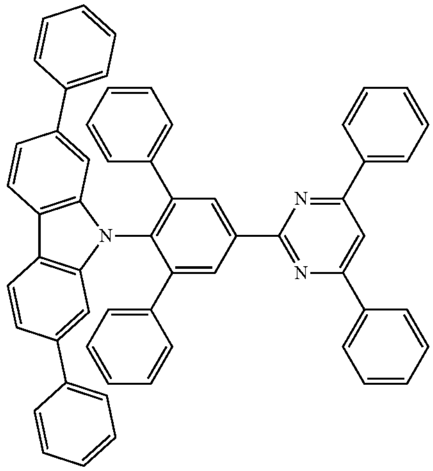
82
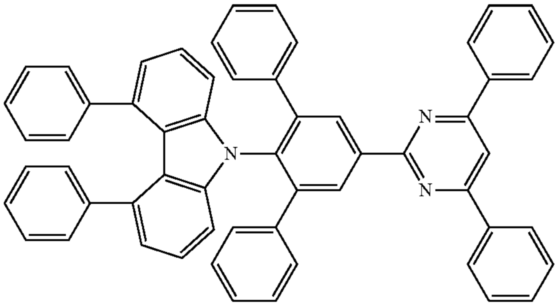
83
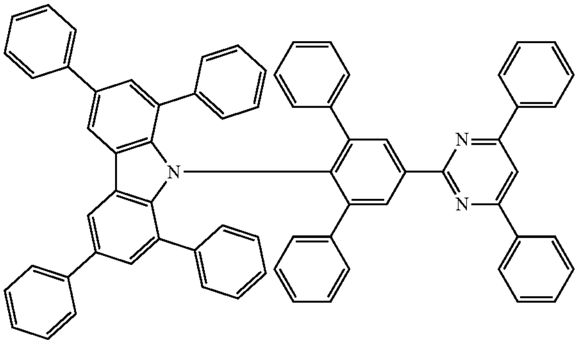

84
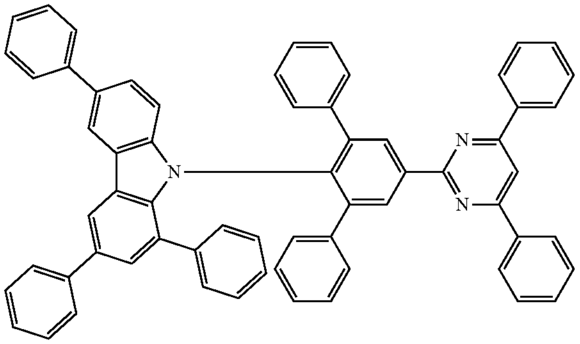
85
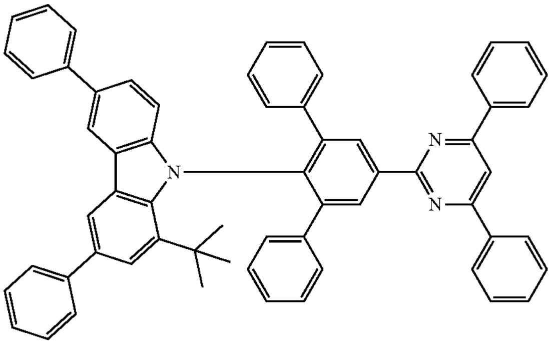
86
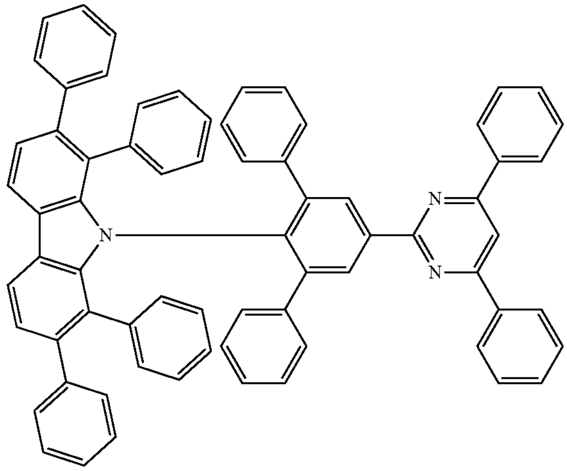
87
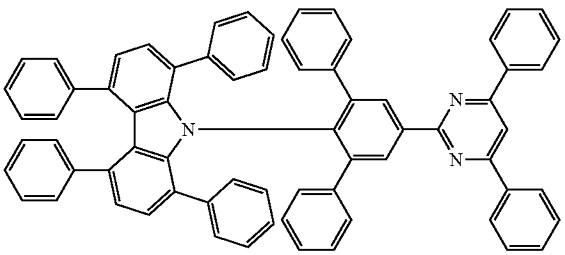
88
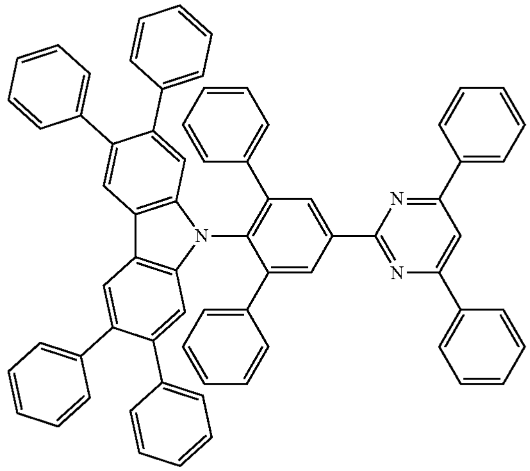
89
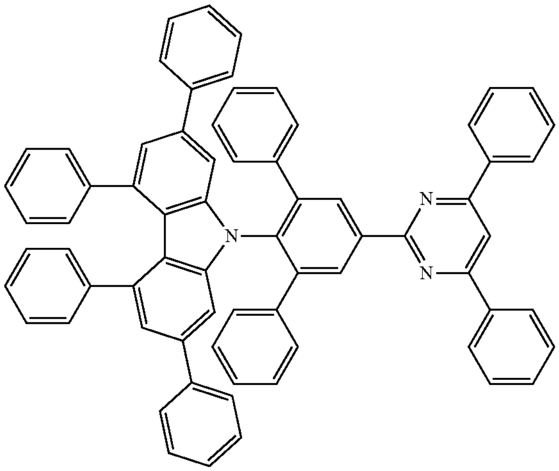
90
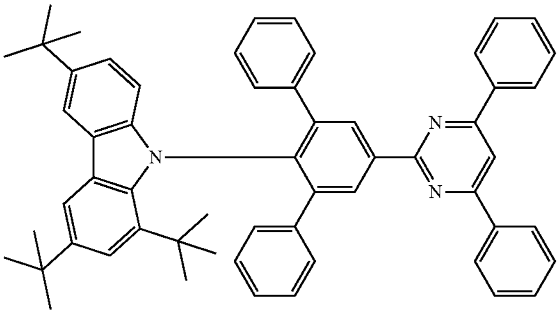
91
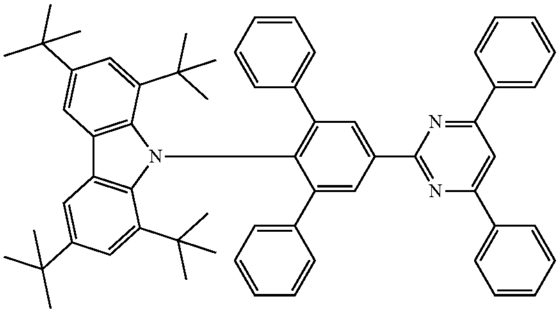

-continued
92
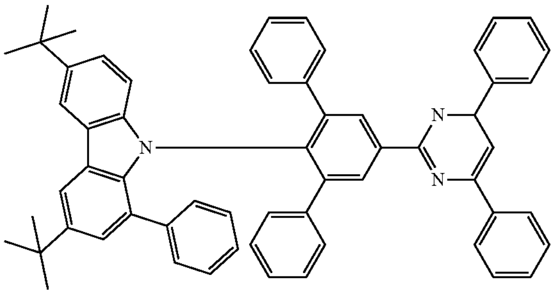
93
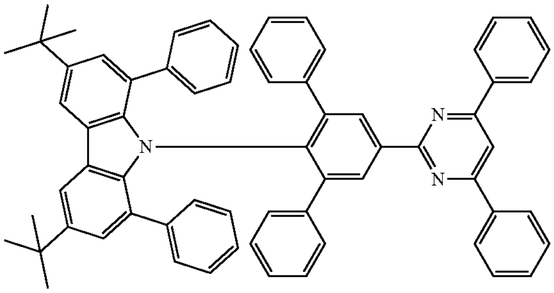
94
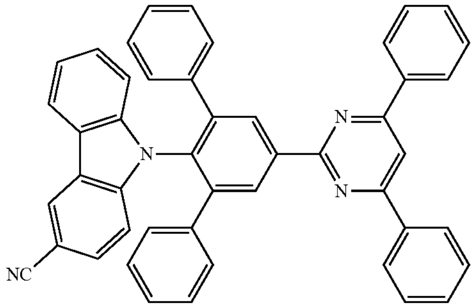
95
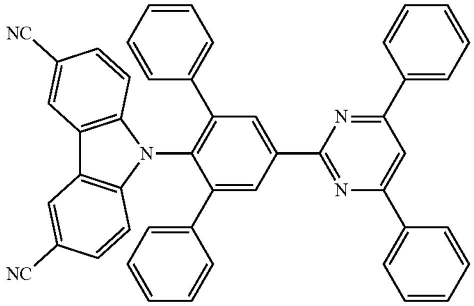
96
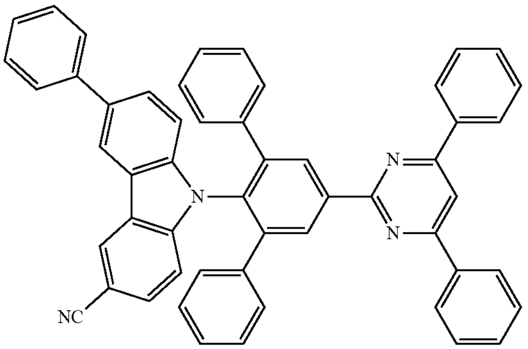
-continued
97
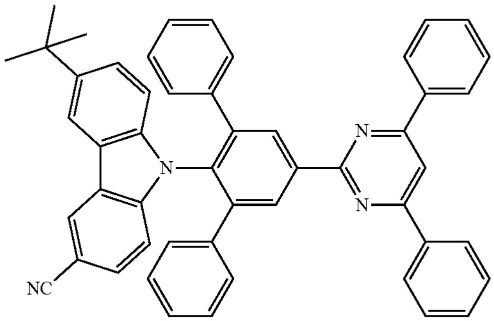
98
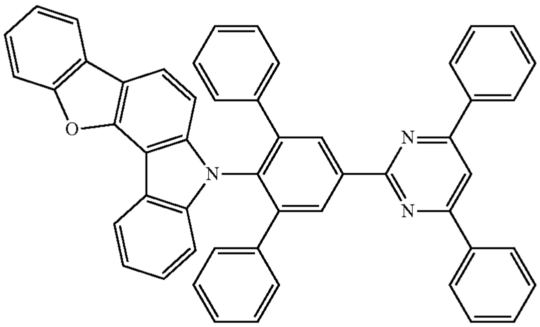
99
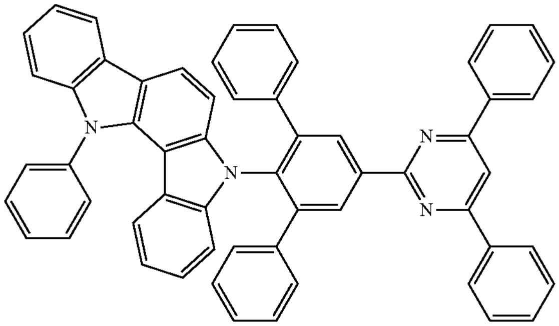
100
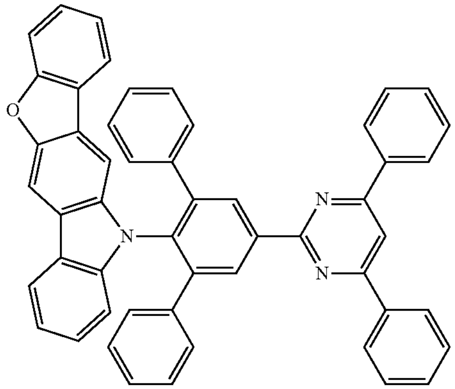

-continued
101
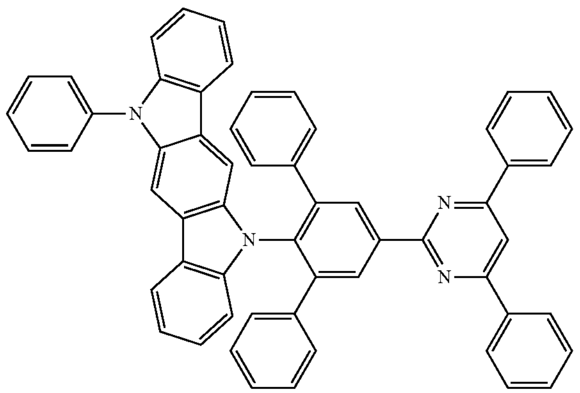
102
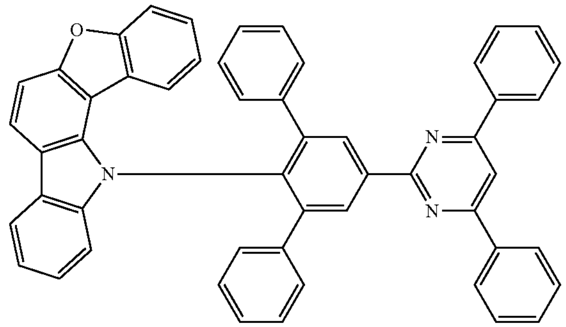
103
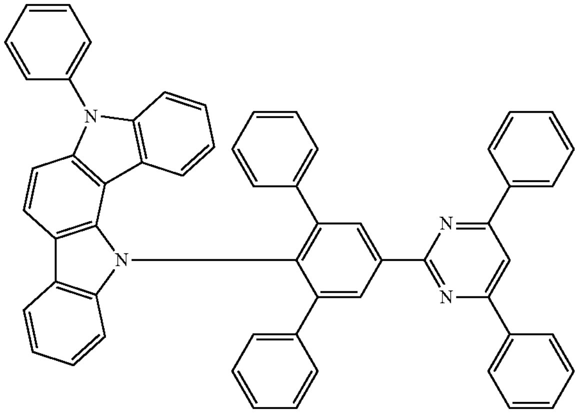
104
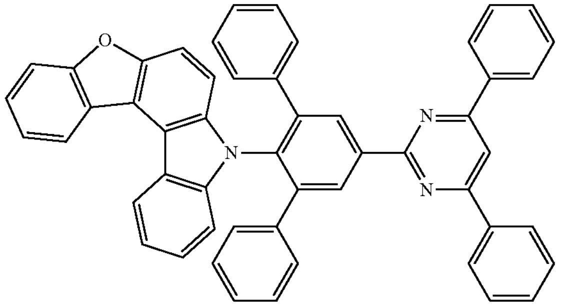
-continued
105
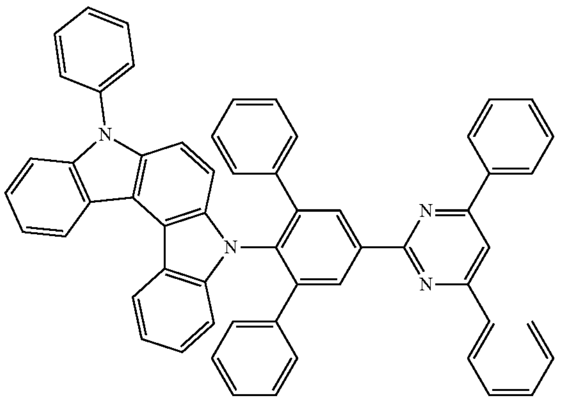
106
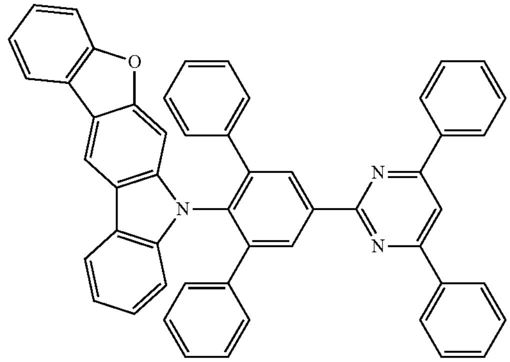
107
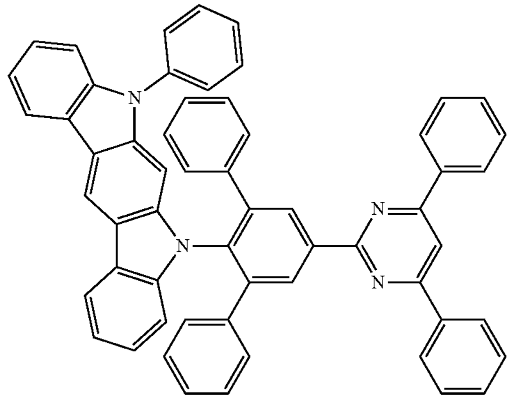
108
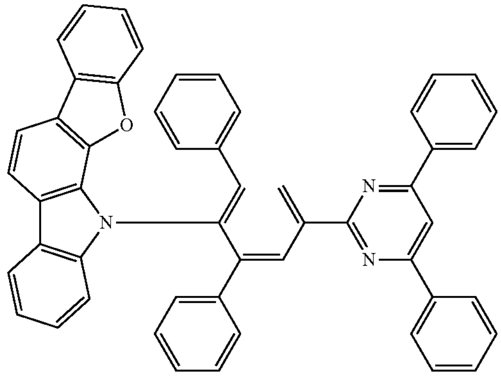

-continued
109
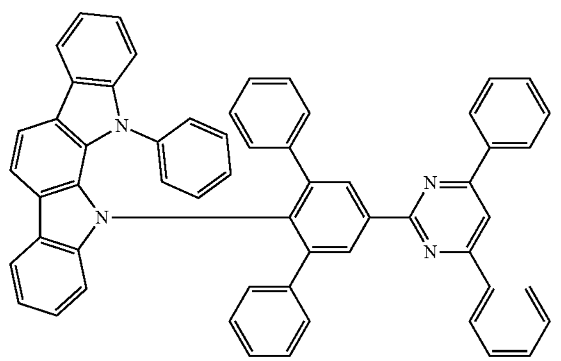
110
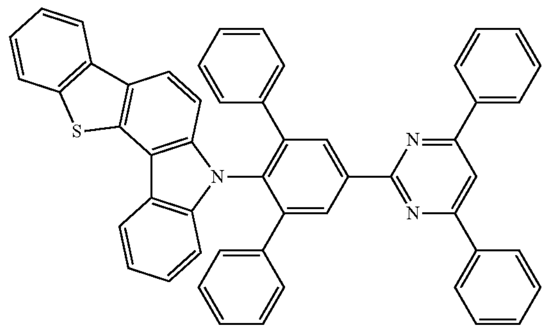
111
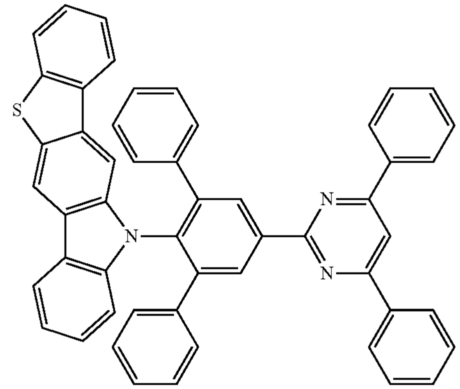
112
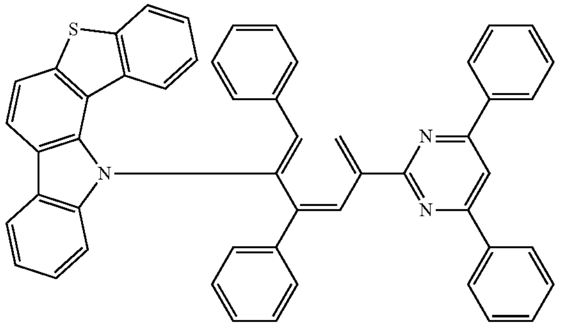
-continued
113
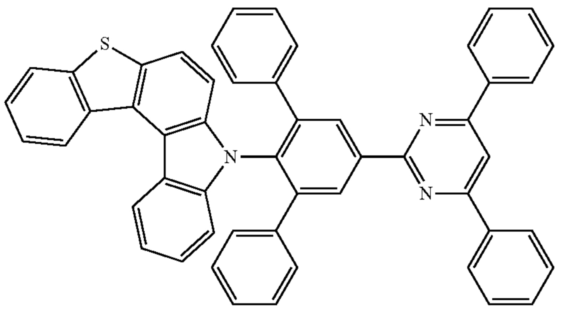
114
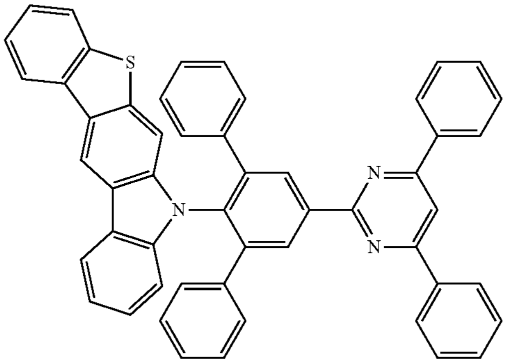
115
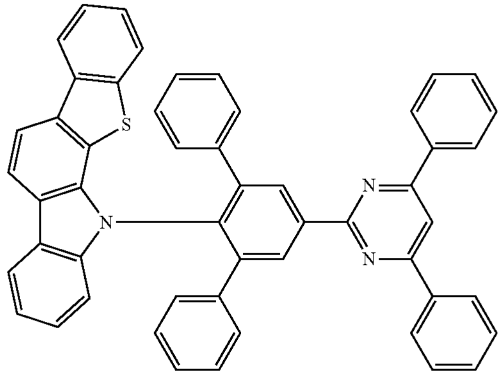
116
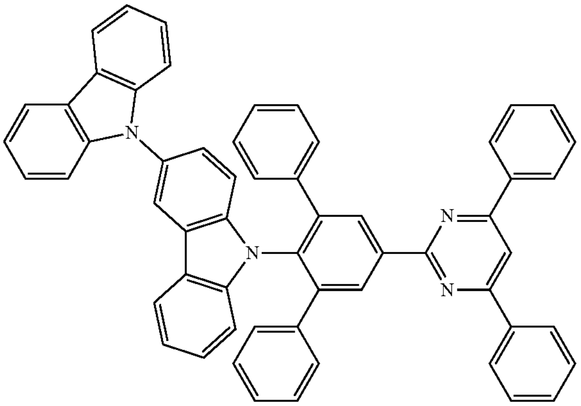

-continued
117
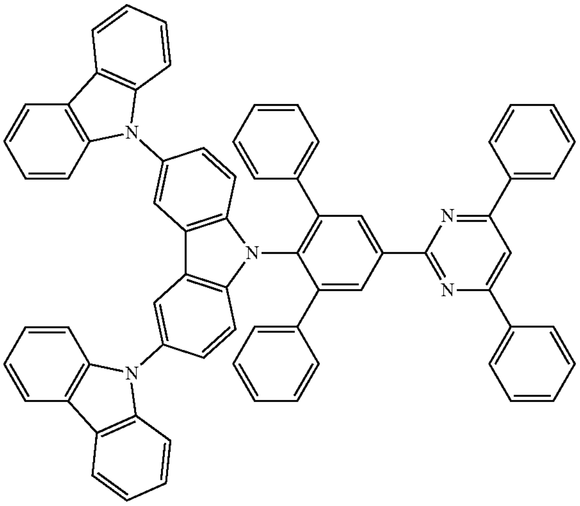
118
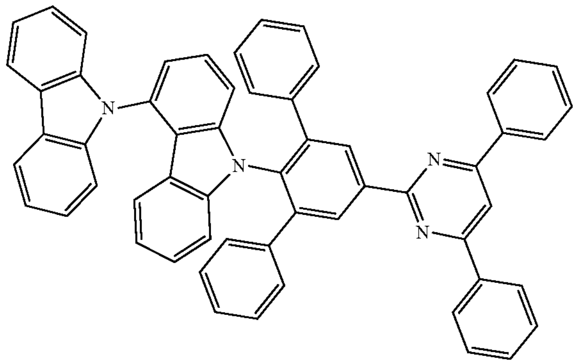
119
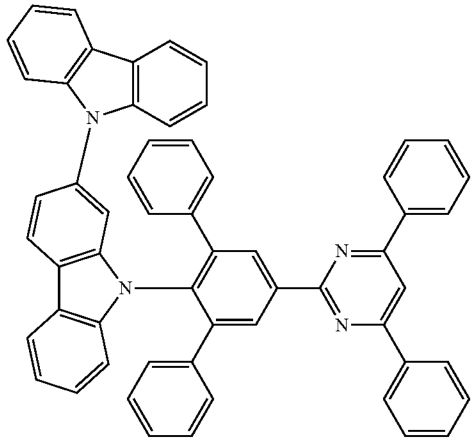
-continued
120
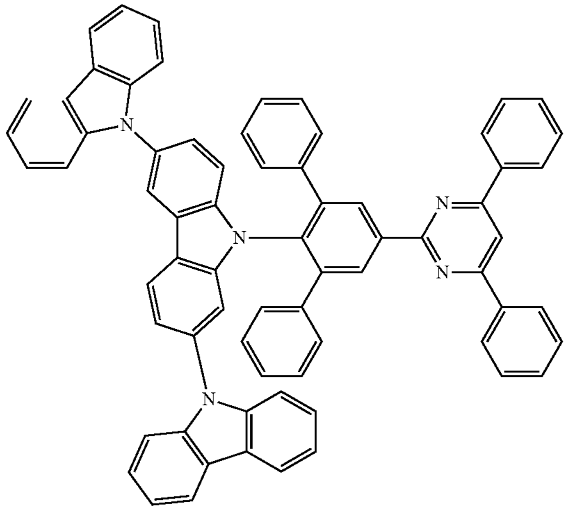
121
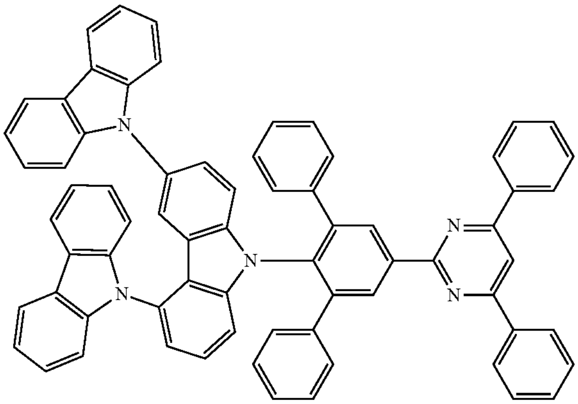
122
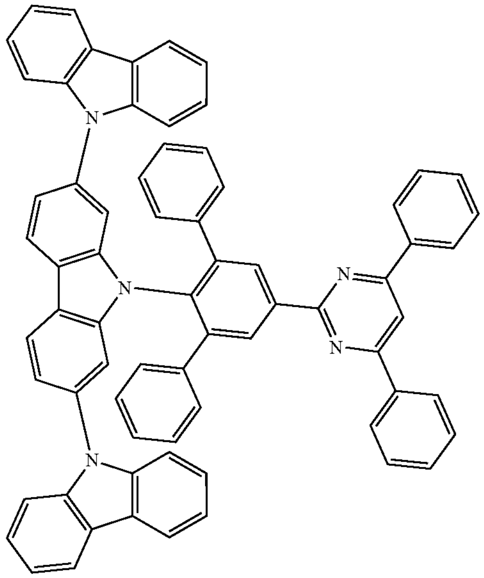

-continued
123
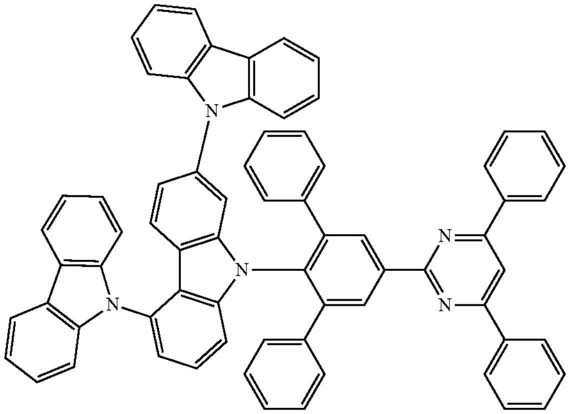
124
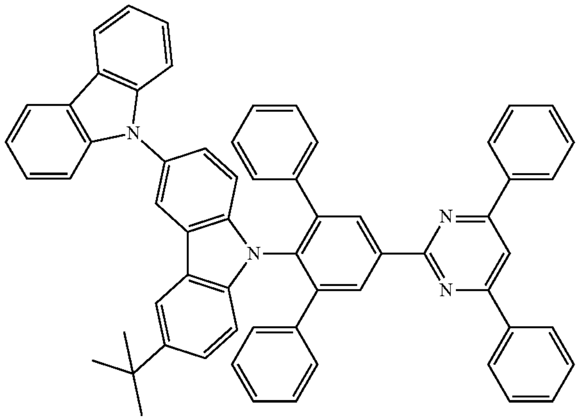
125
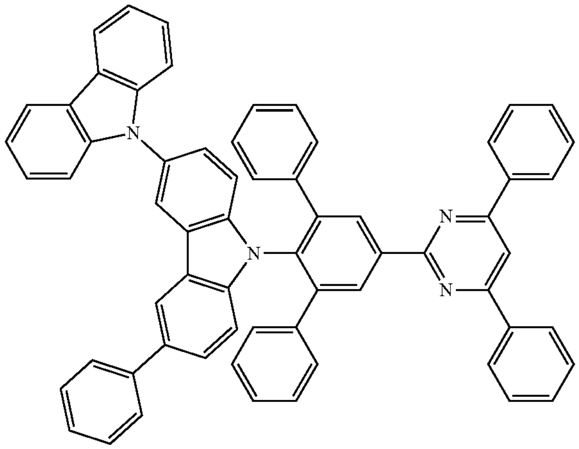
-continued
126
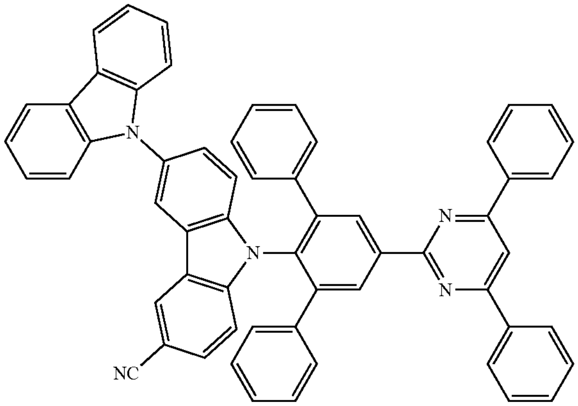
127
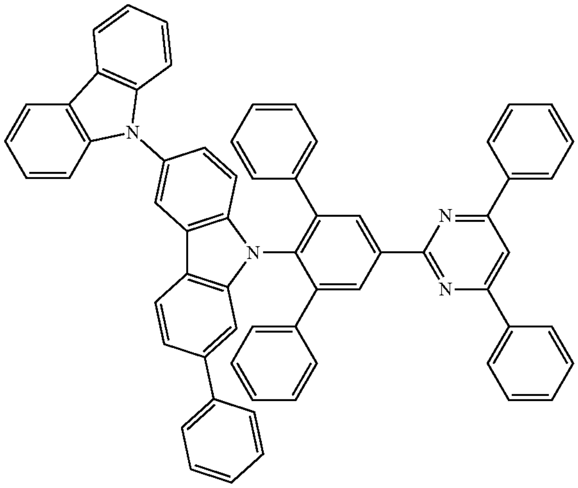
128
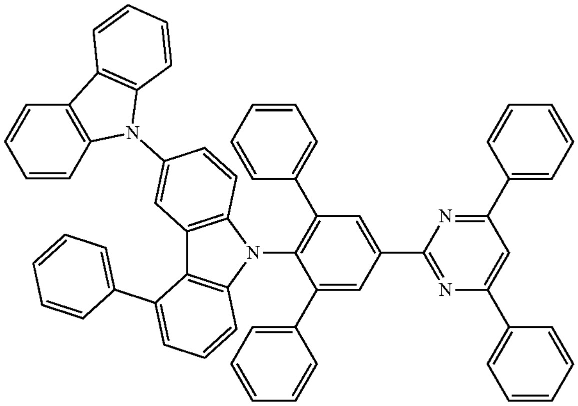

129
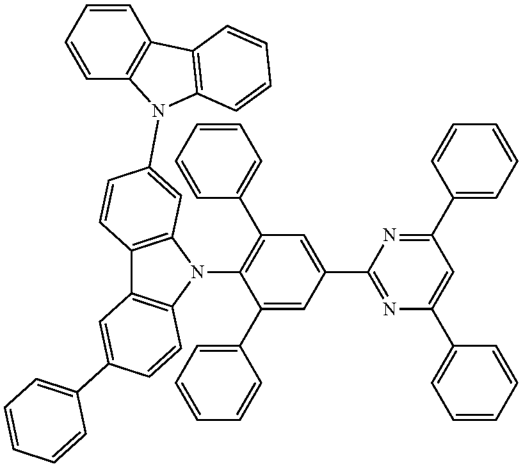
130
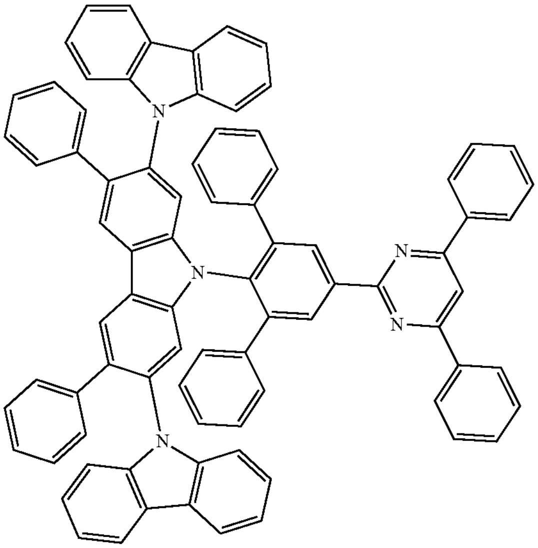
131
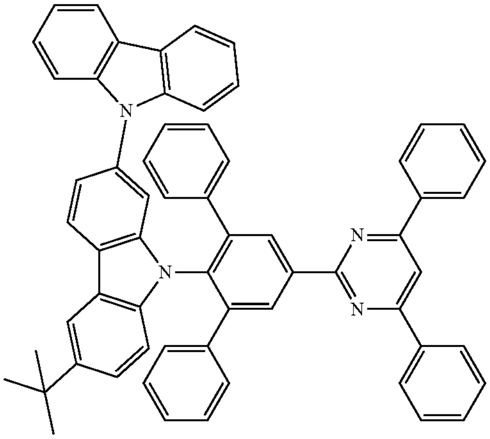
132
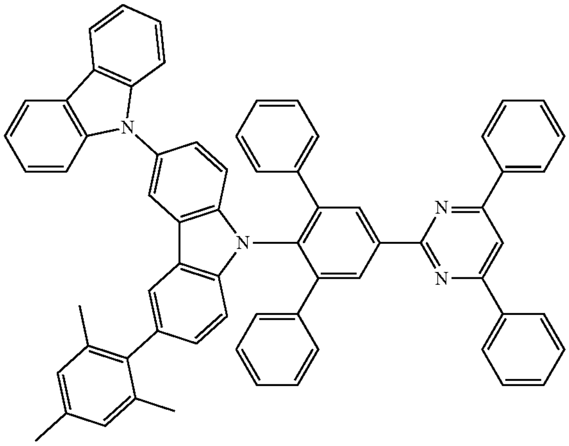
133
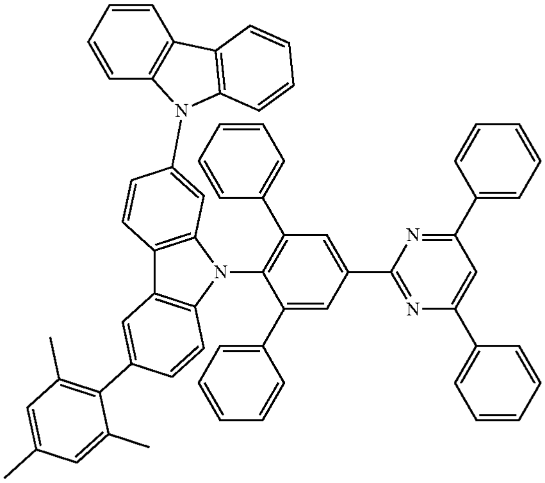
134
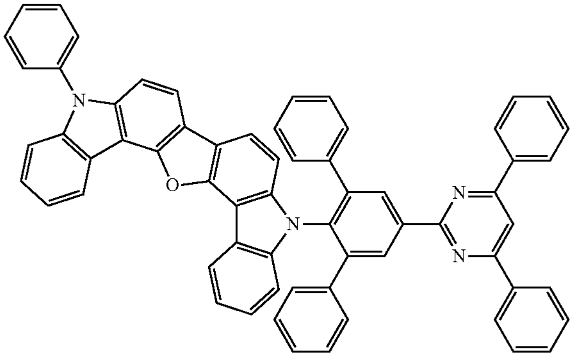

135
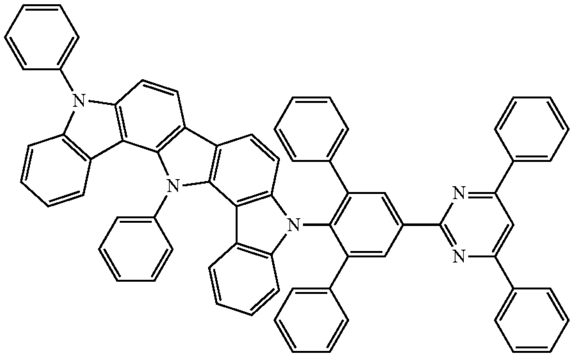
136
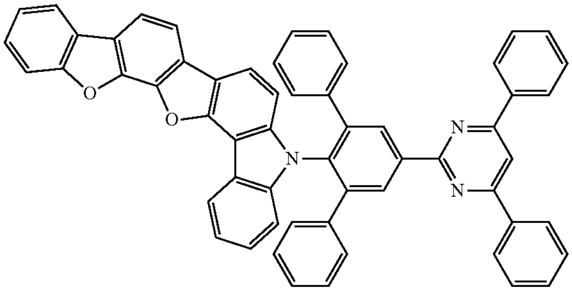
137
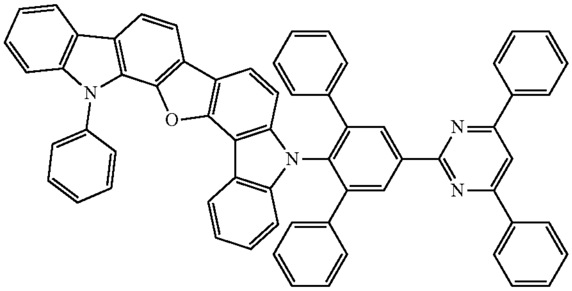
138
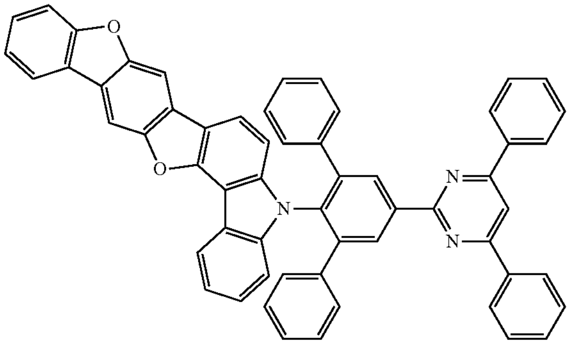
139
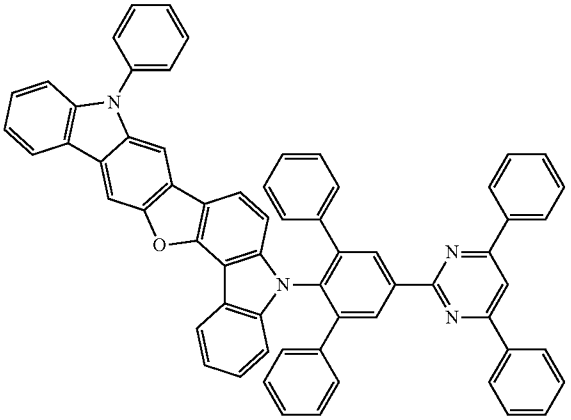
140
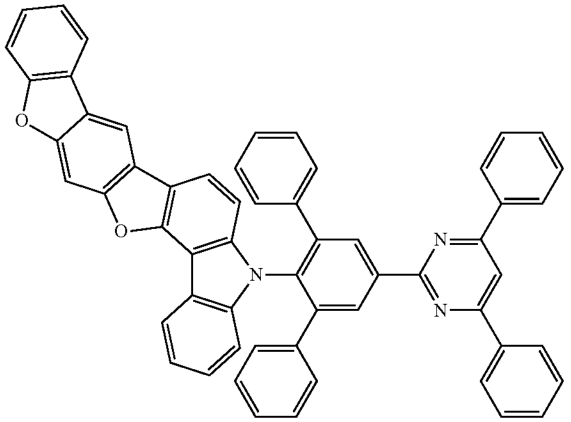
141
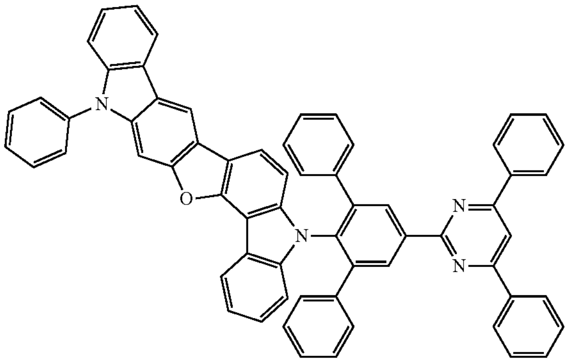

-continued
142
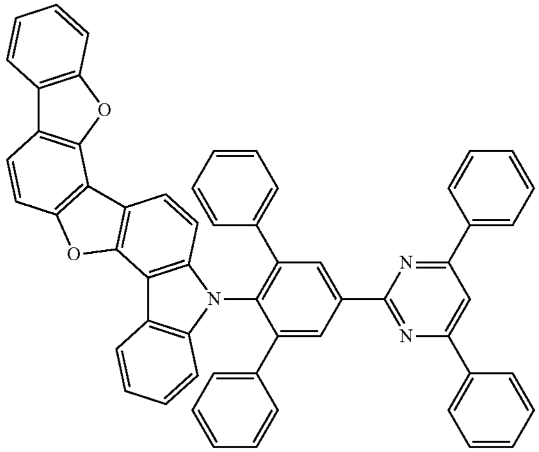
143
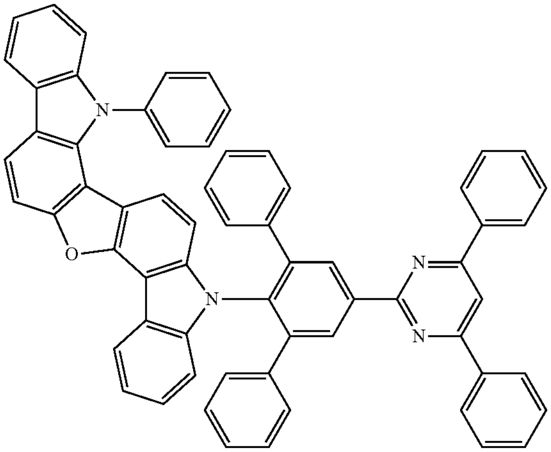
144
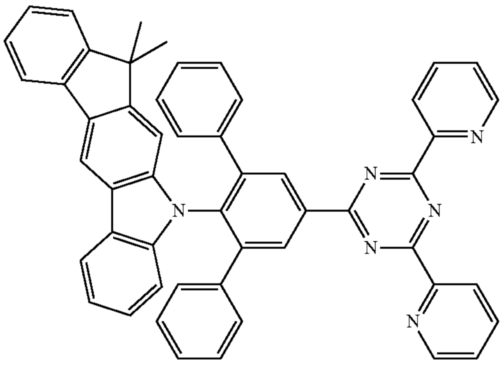
-continued
145
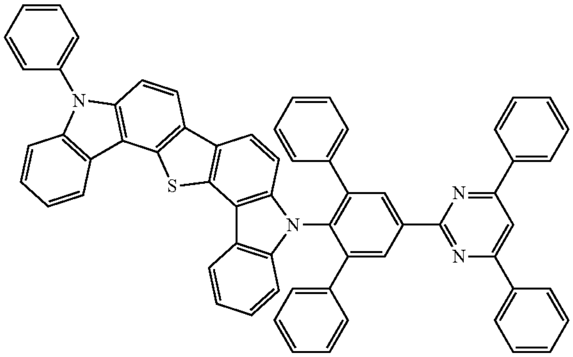
146
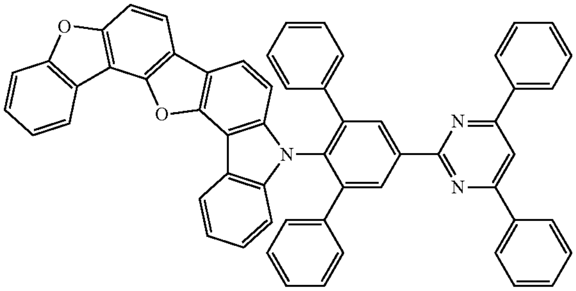
147
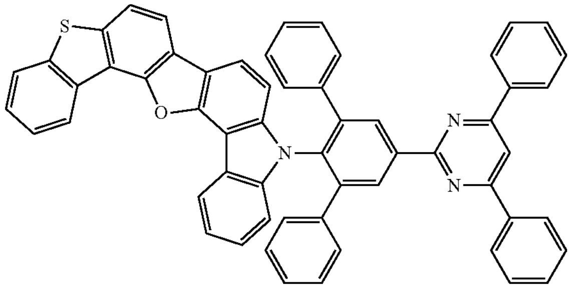
148
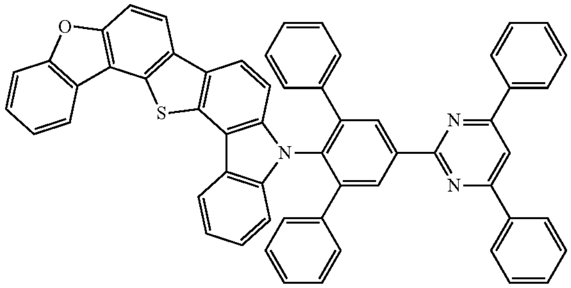
149
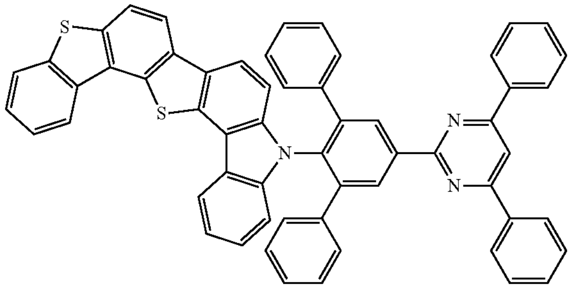

150
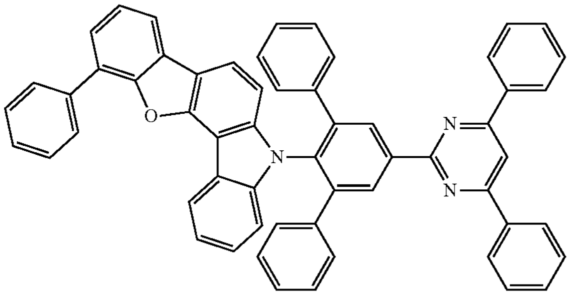
151
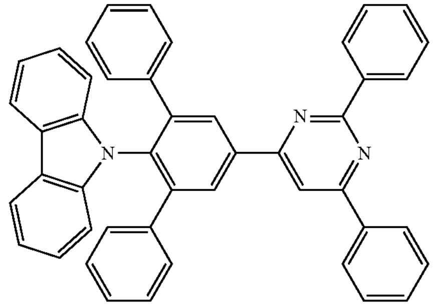
152
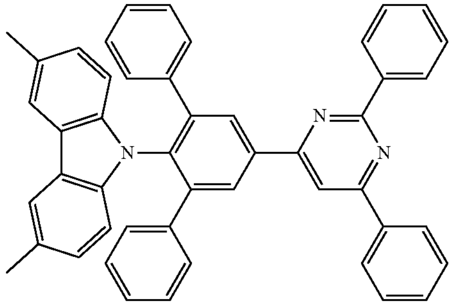
153
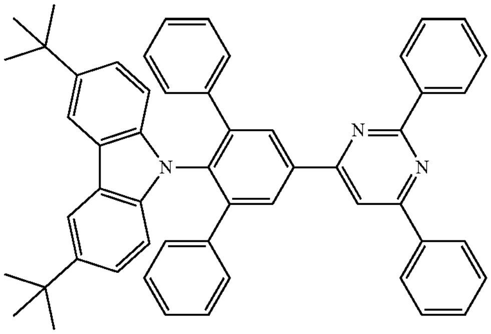
154
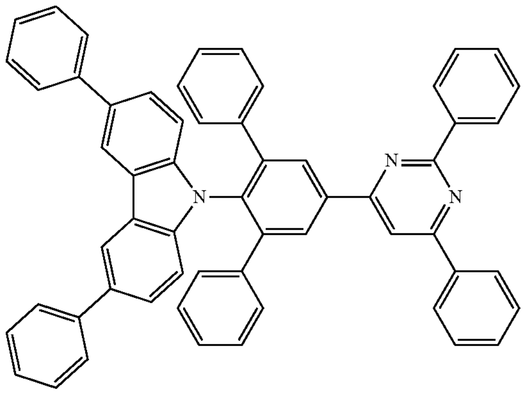
155
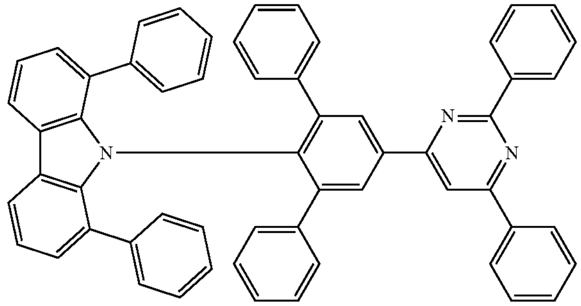
156
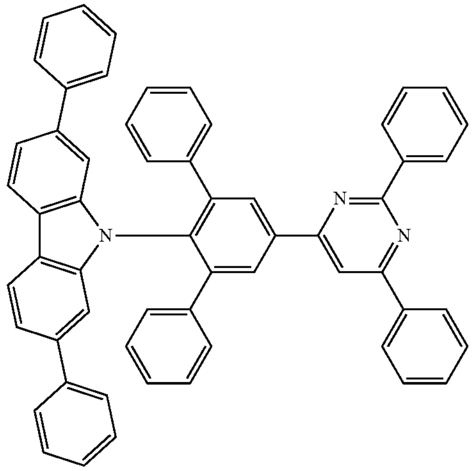
157
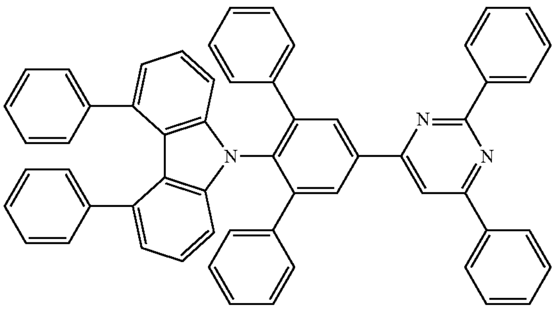

158
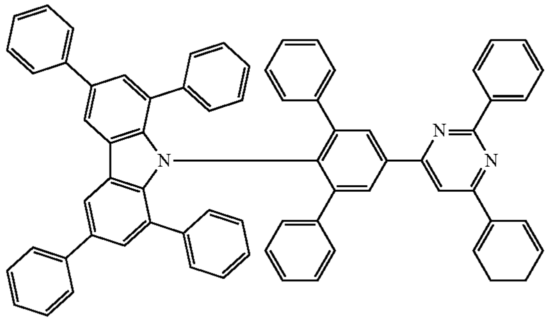
159
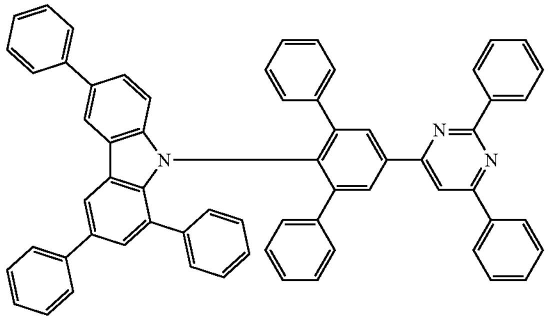
160
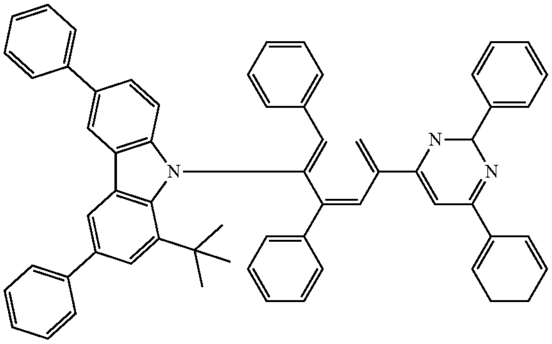
161
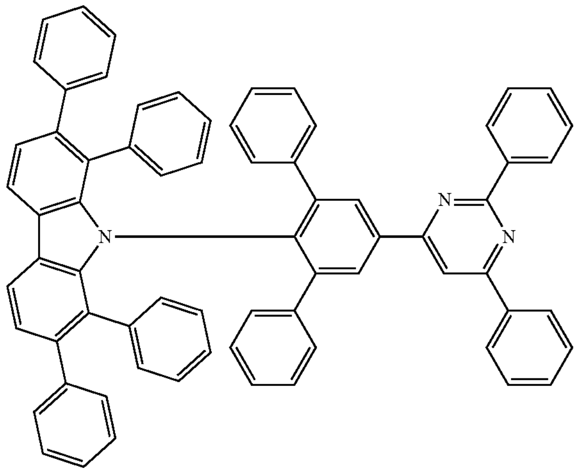
162
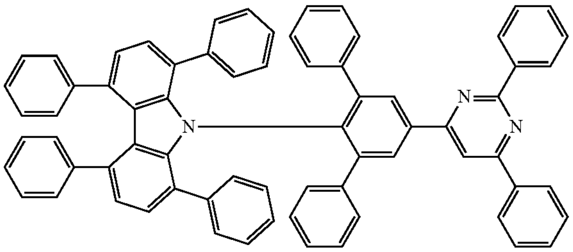
163
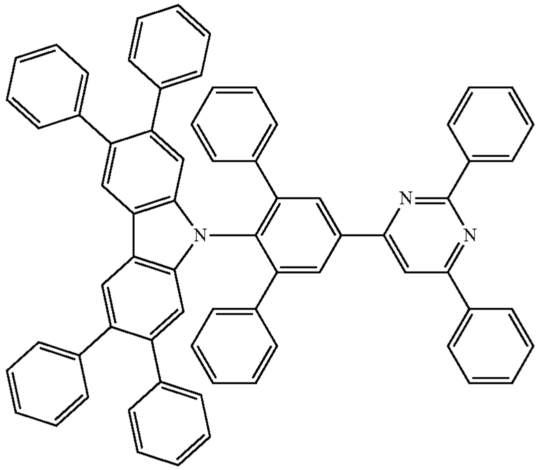
164
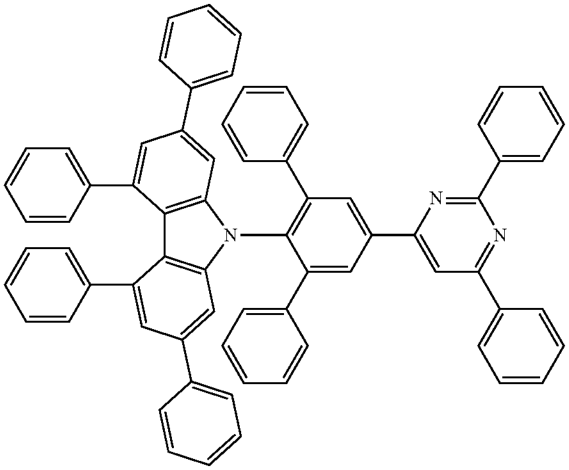
165
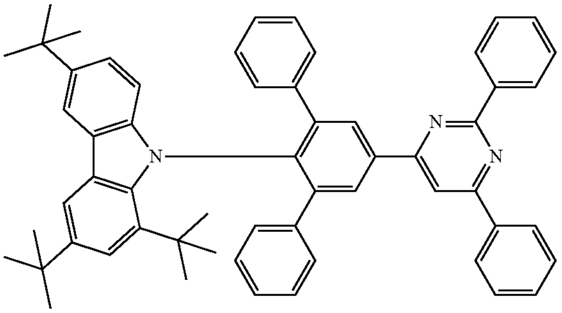

-continued
166
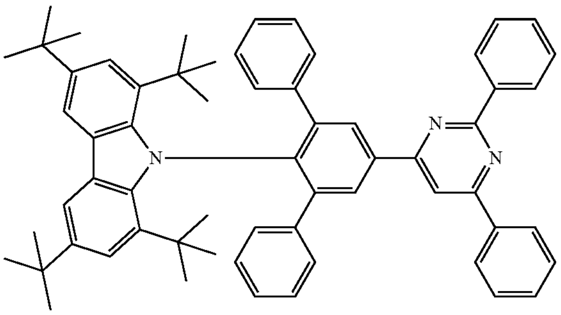
167
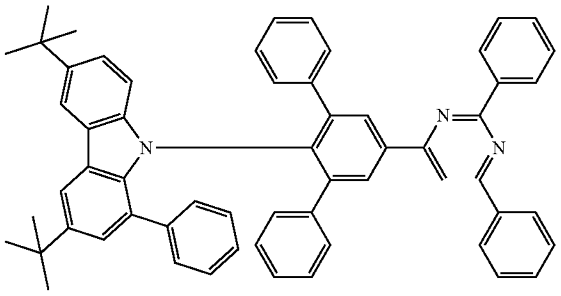
168
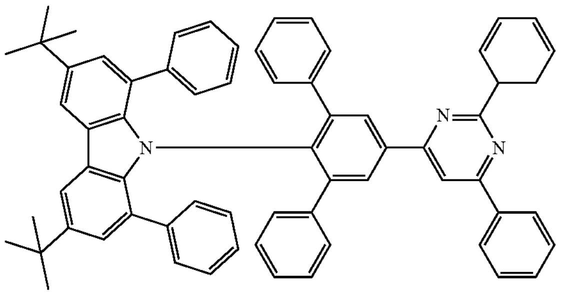
169
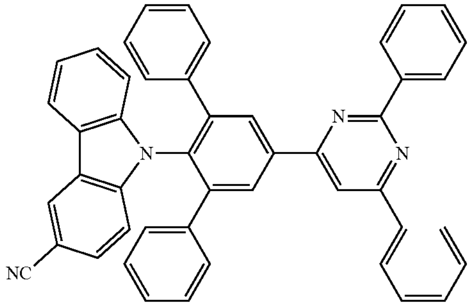
170
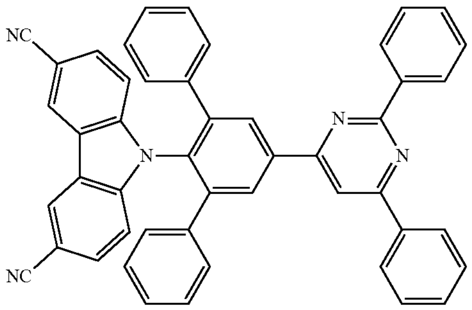
-continued
171
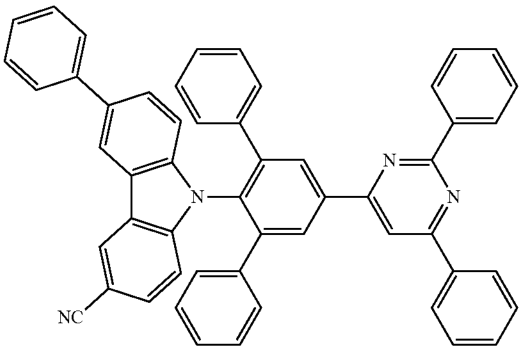
172
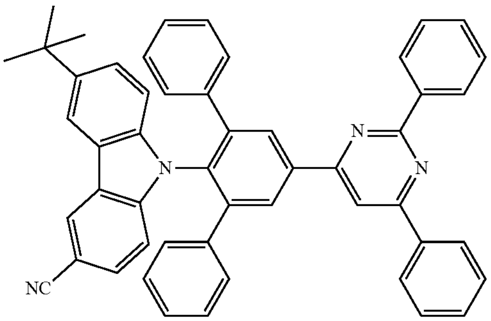
173
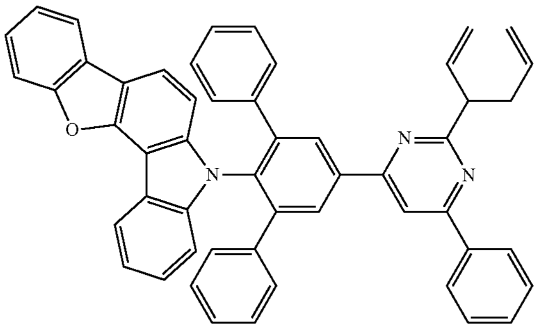
174
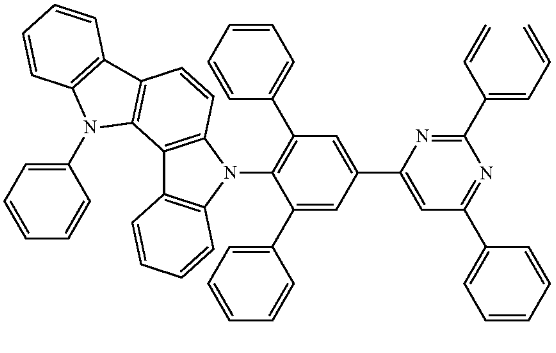

-continued
175
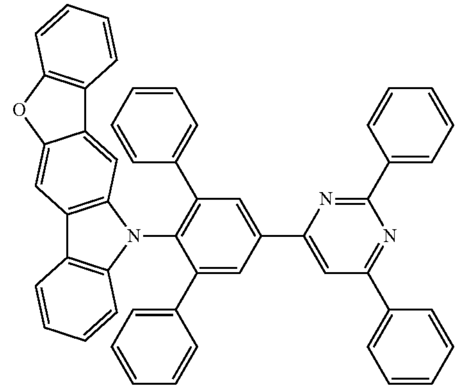
176
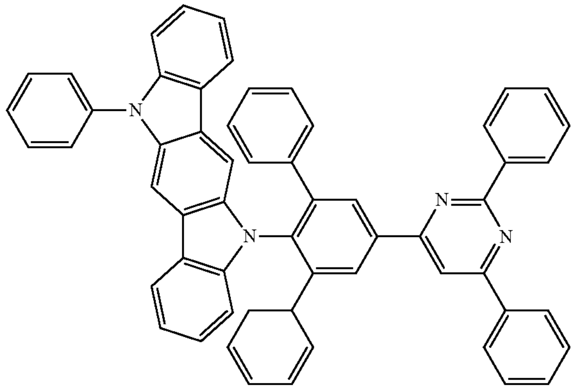
177
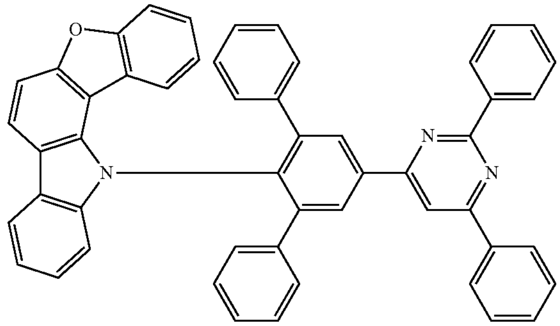
178
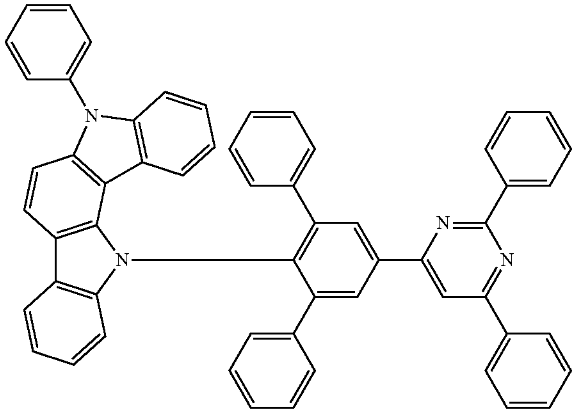
-continued
179
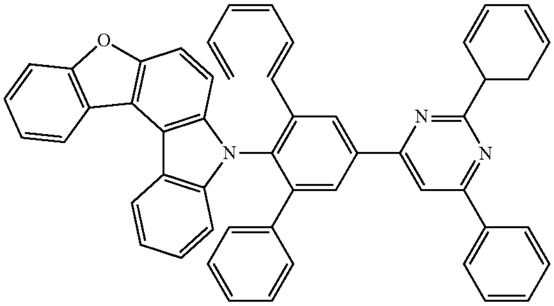
180
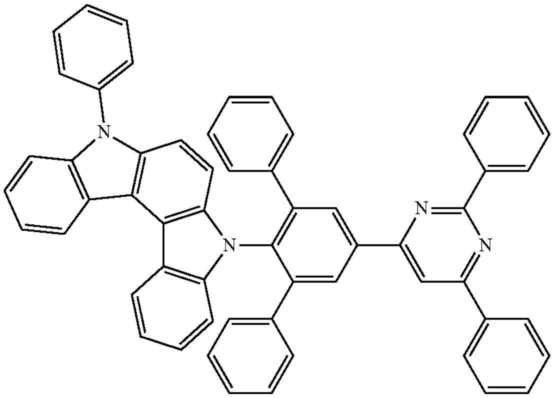
181
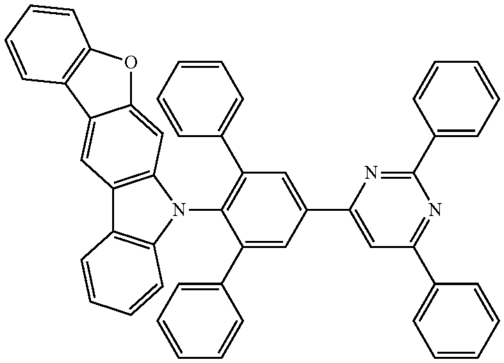
182
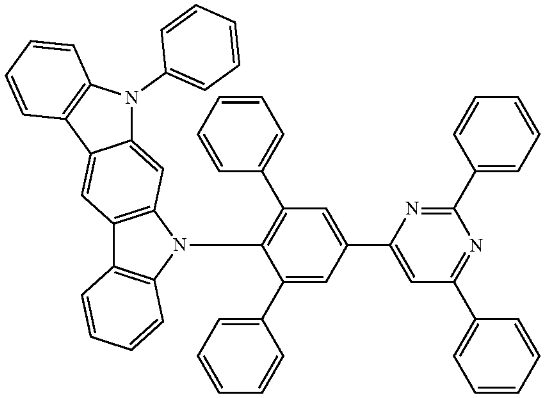

183
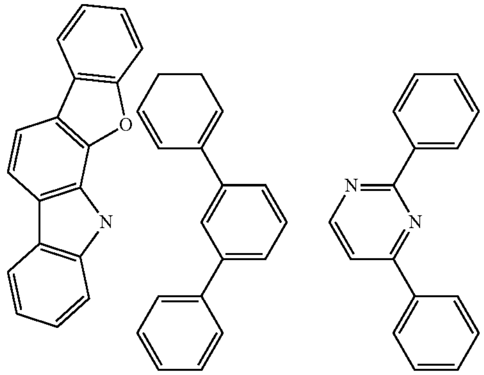
184
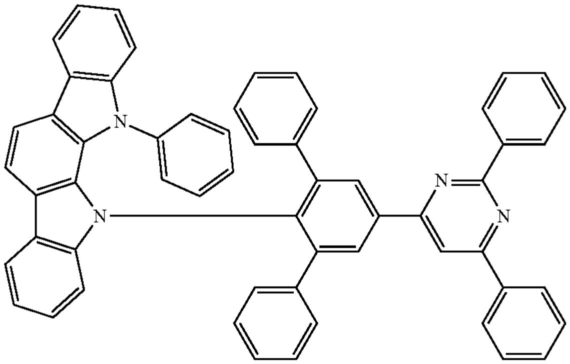
185
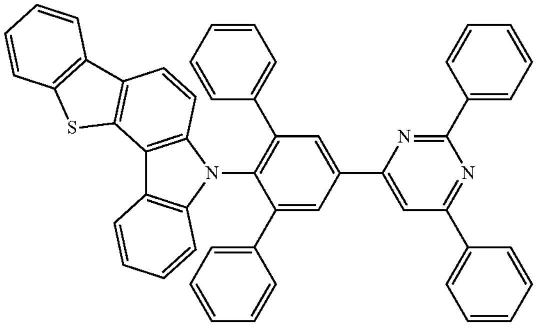
186
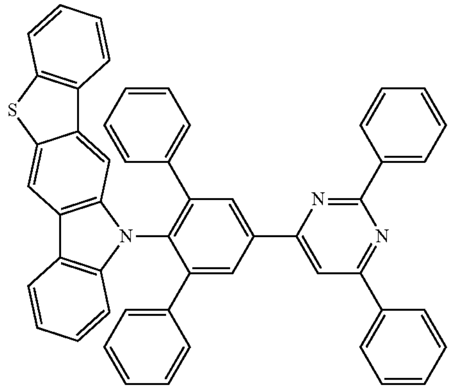
187
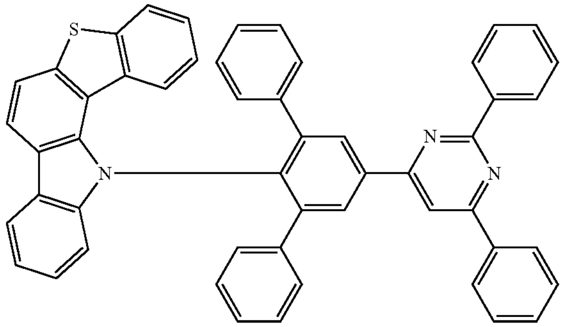
188
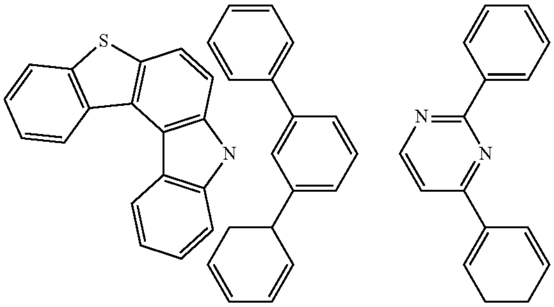
189
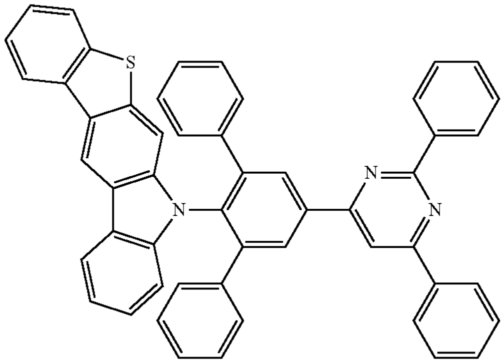
190
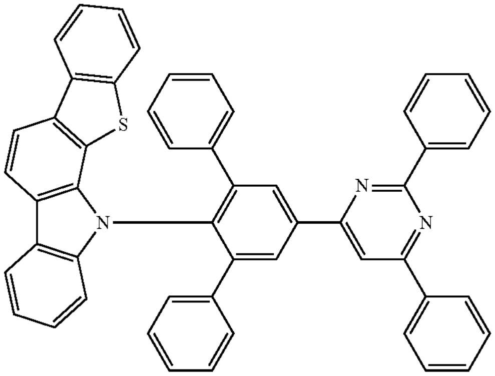

-continued
191
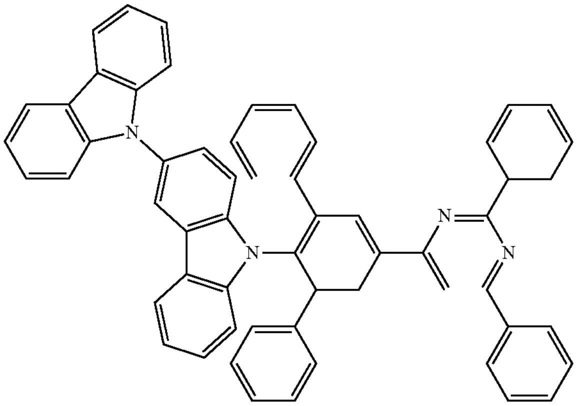
192
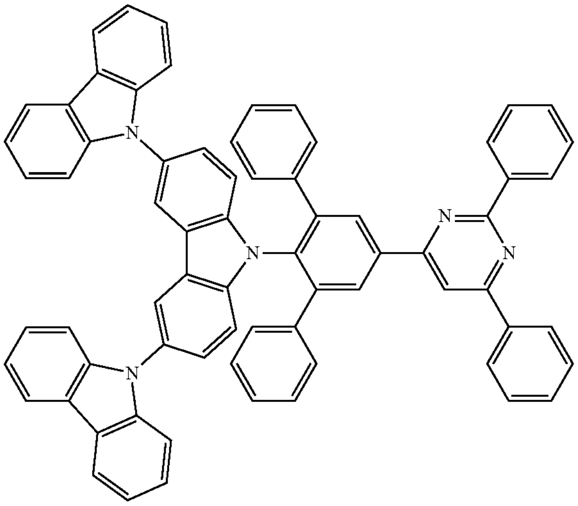
193
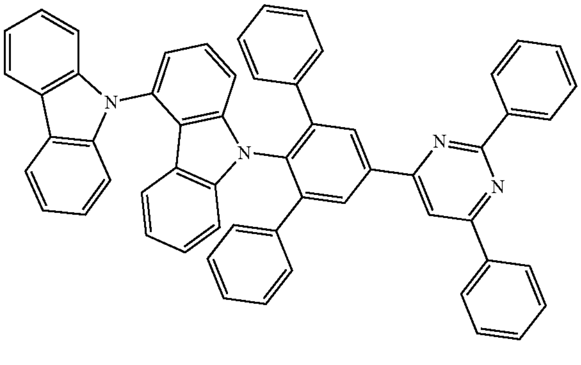
-continued
194
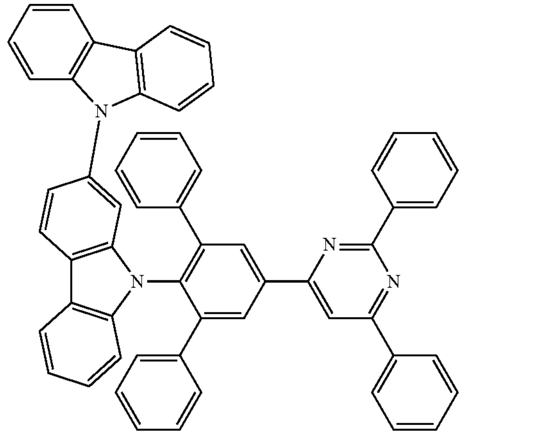
195
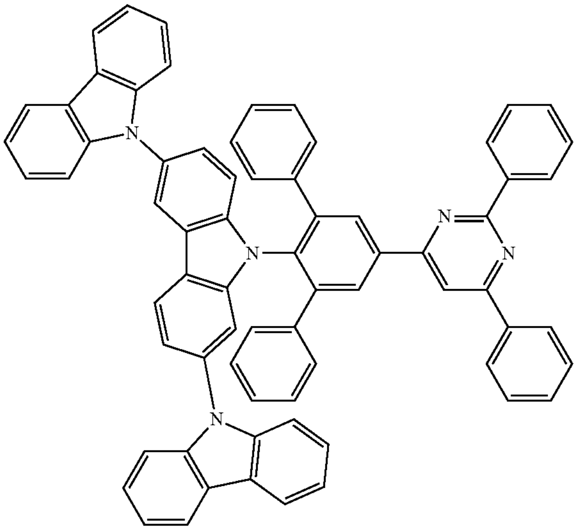
196
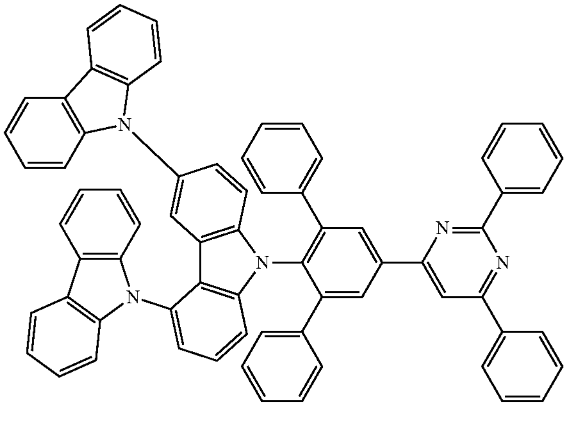

-continued
197
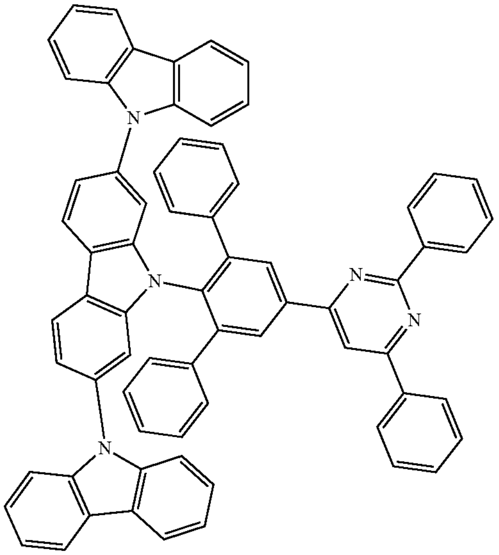
198
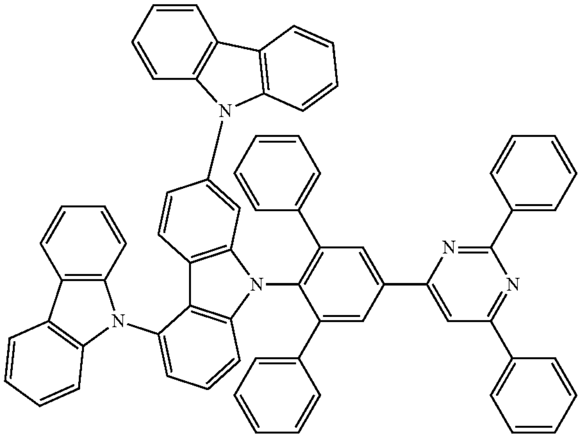
199
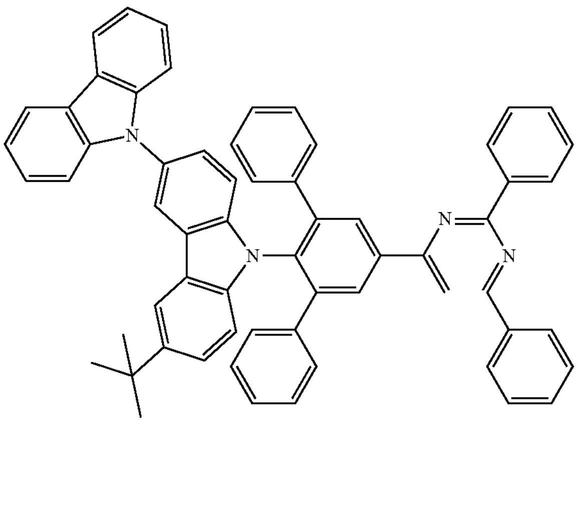
-continued
200
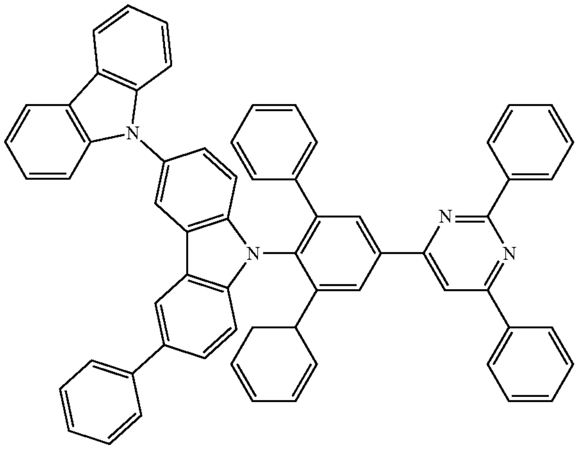
201
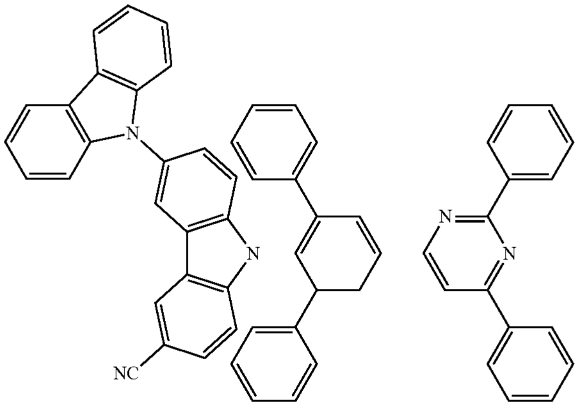
202
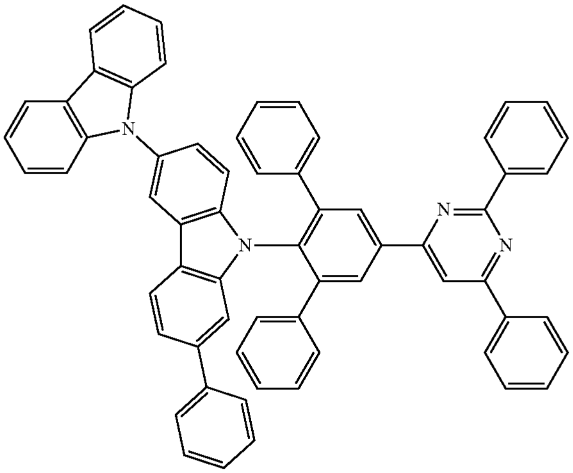

203
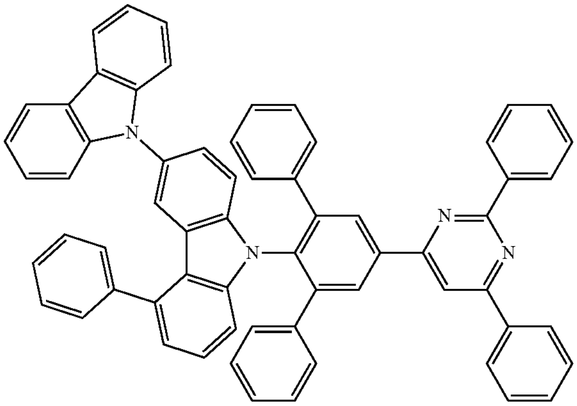
204
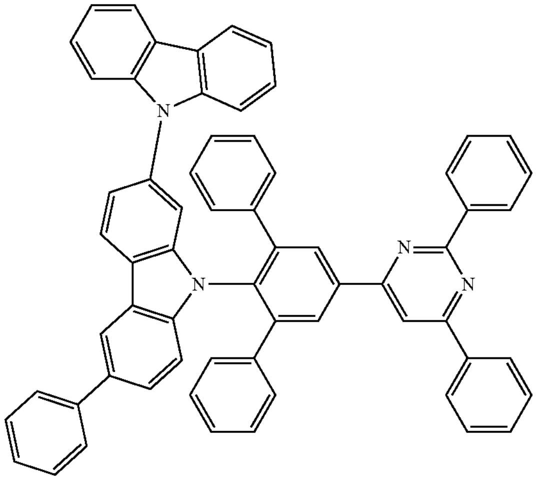
205
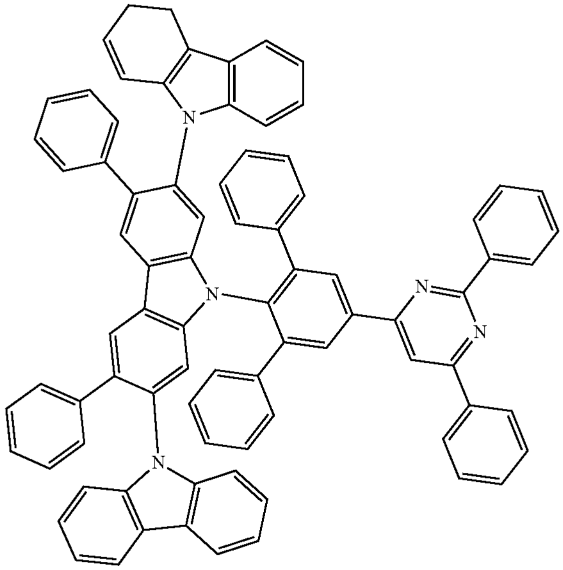
206
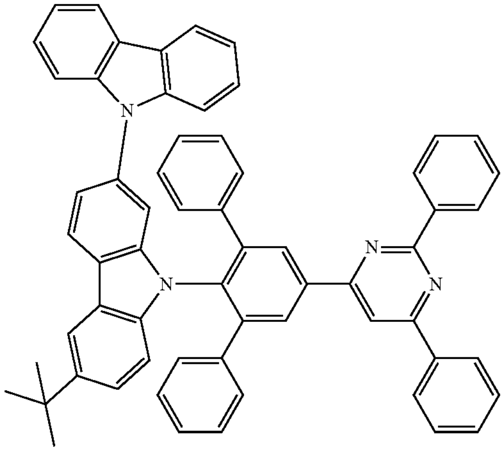
207
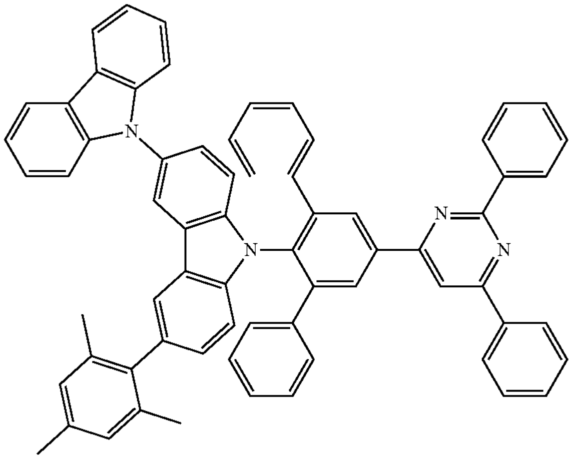
208
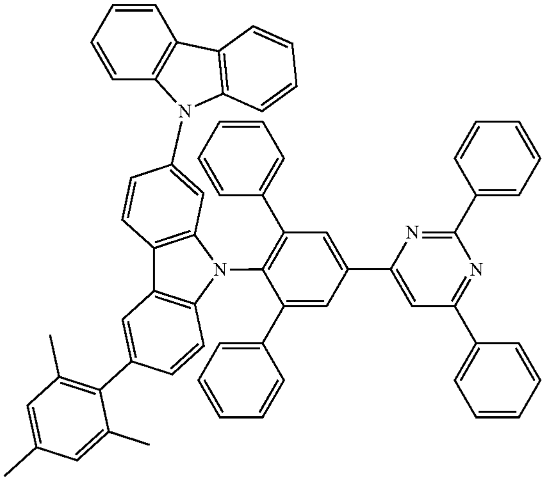

-continued
209
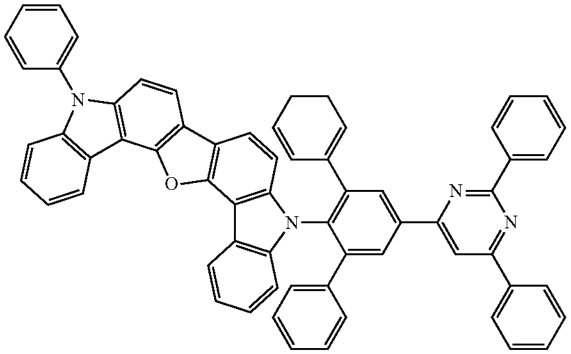
210
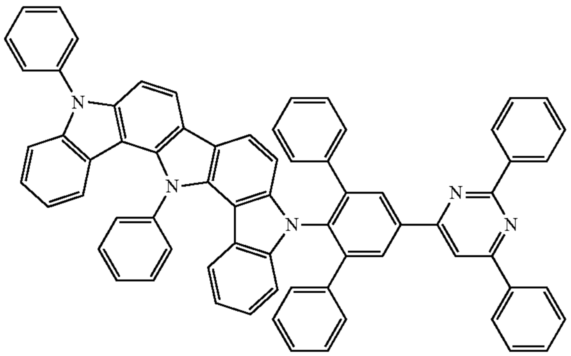
211
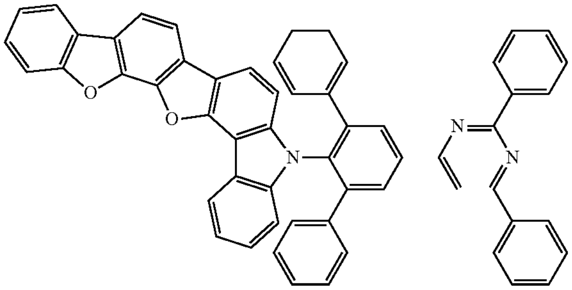
212
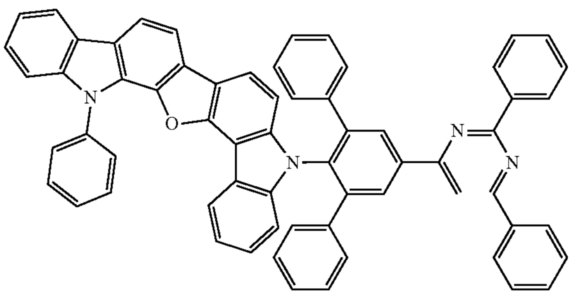
-continued
213
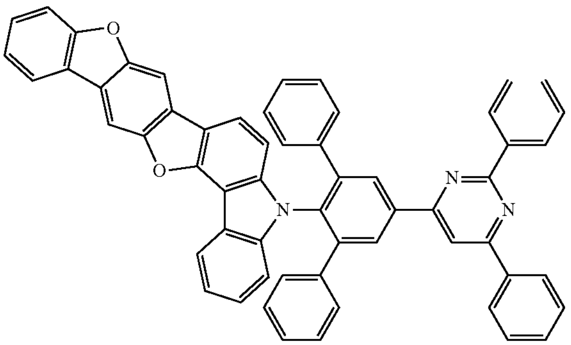
214
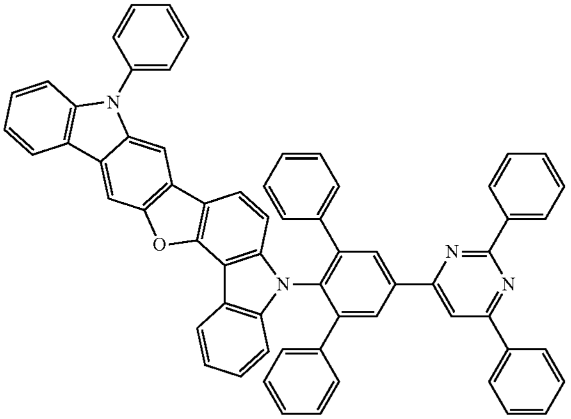
215
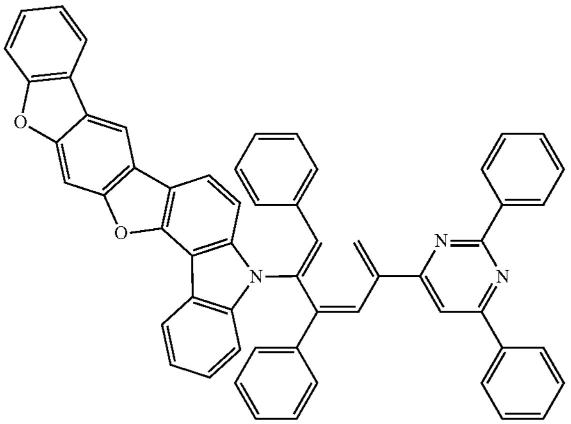
216
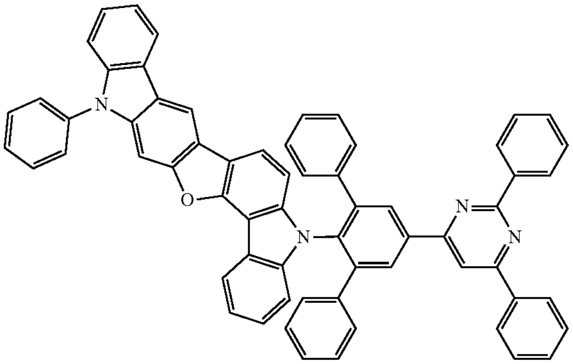

-continued
217
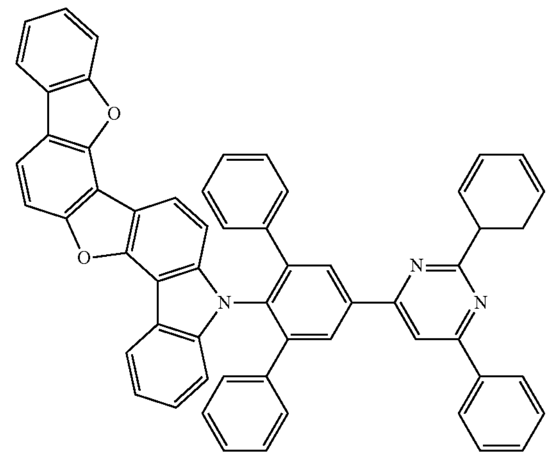
218
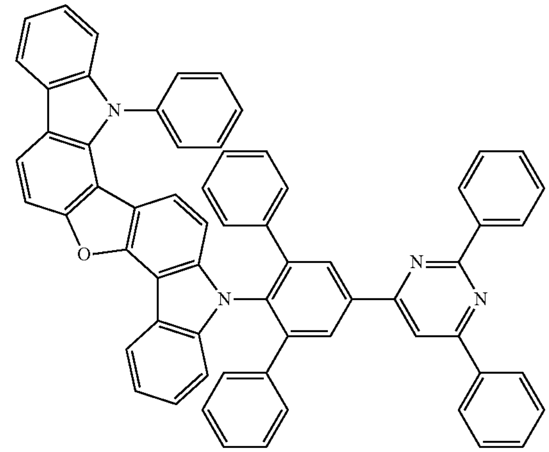
219
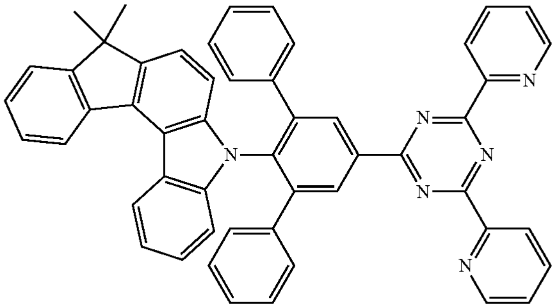
220
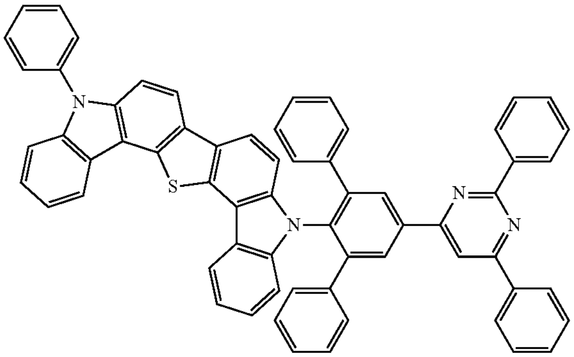
-continued
221
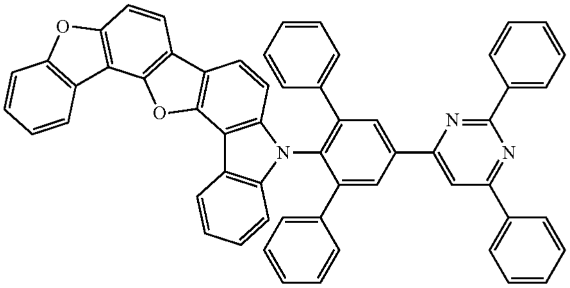
222
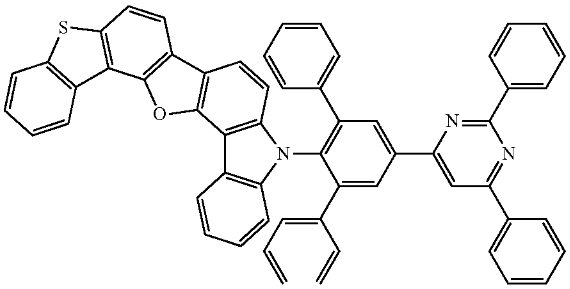
223
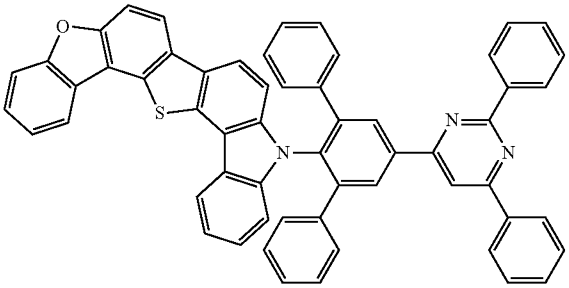
224
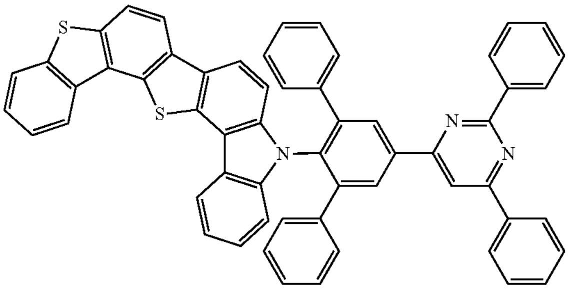
225
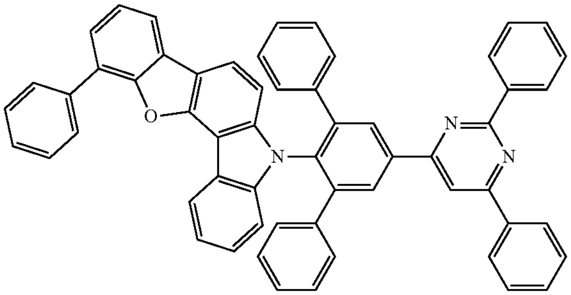

-continued
226
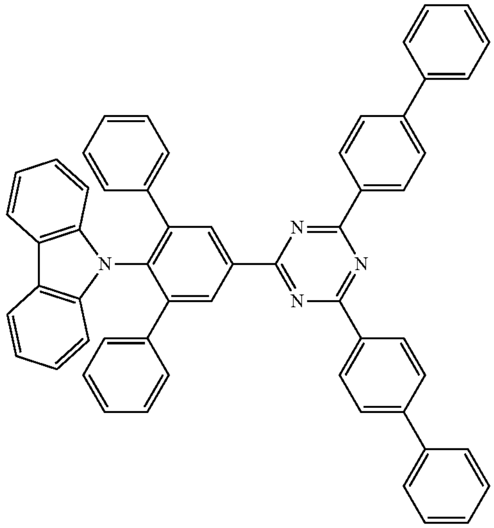
227
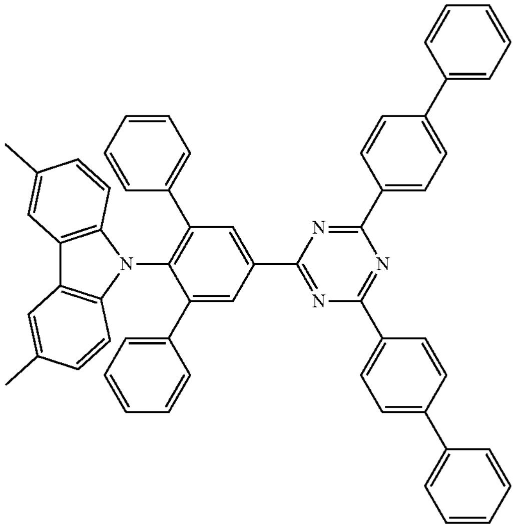
228
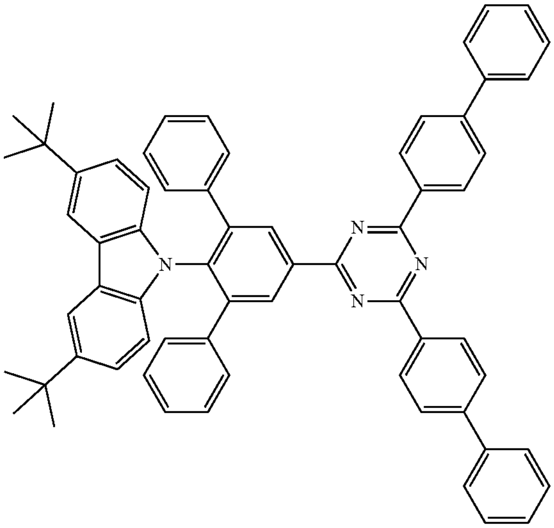
-continued
229
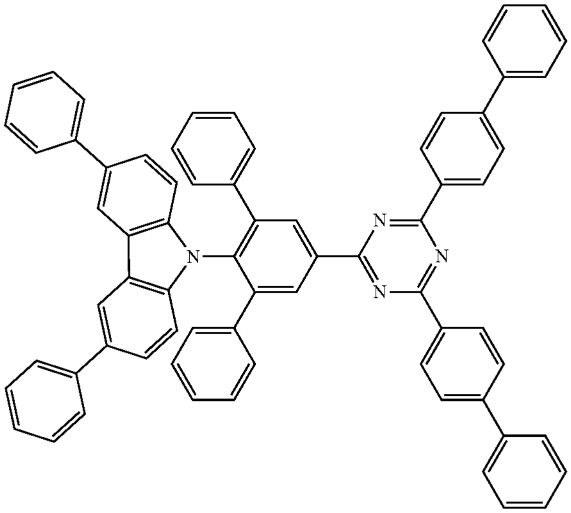
230
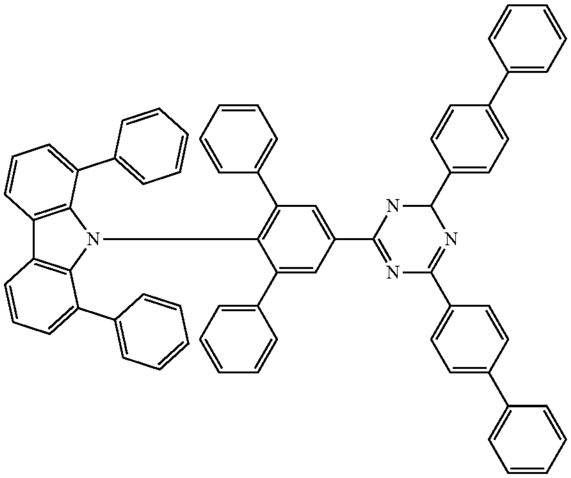
231
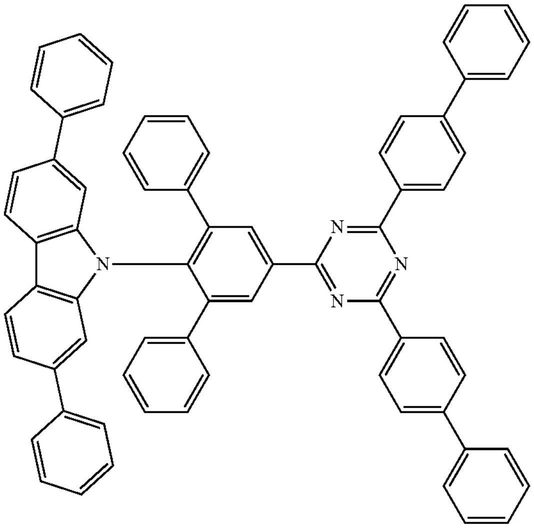

-continued
232
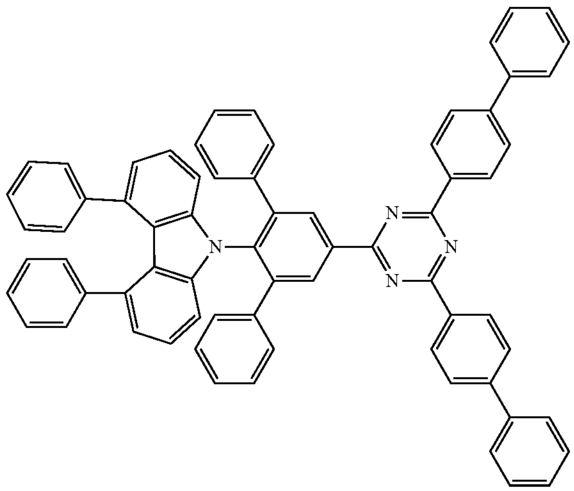
233
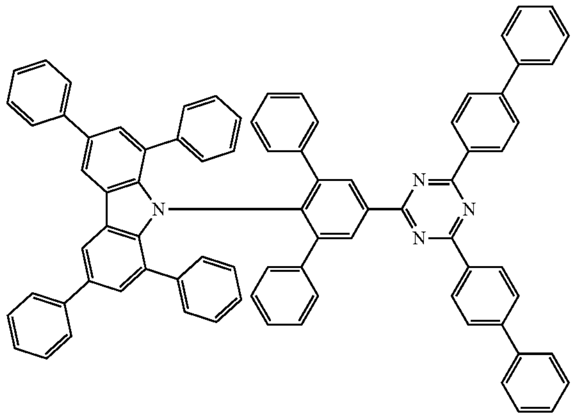
234
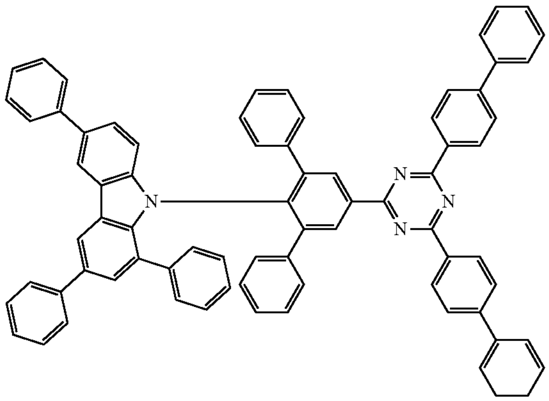
-continued
235
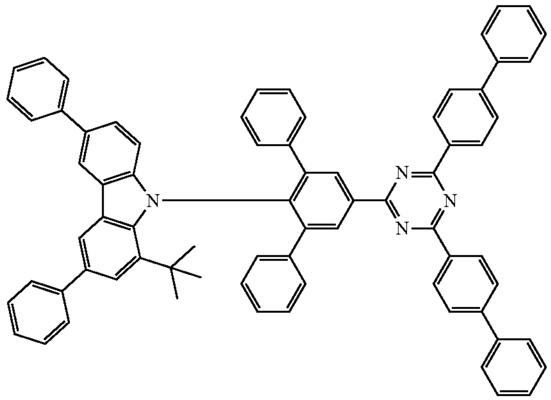
236
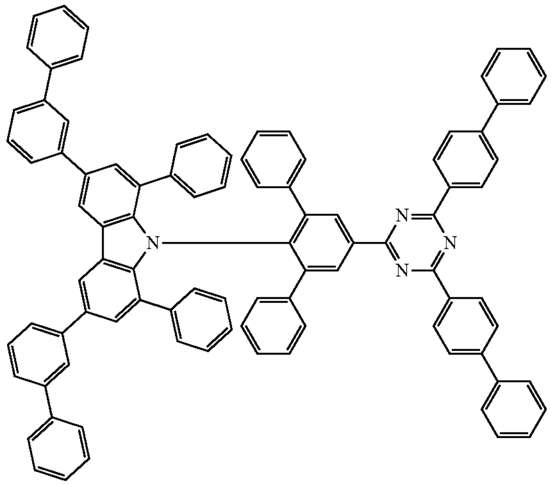
237
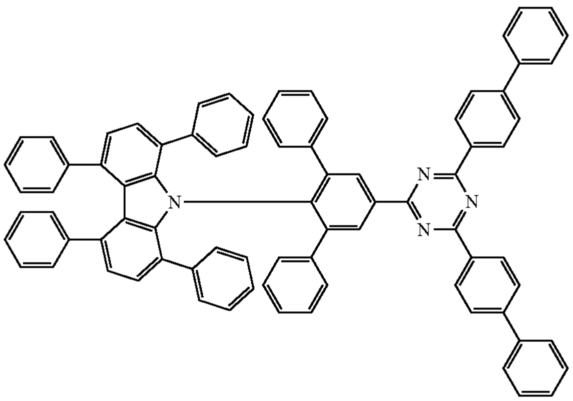

238
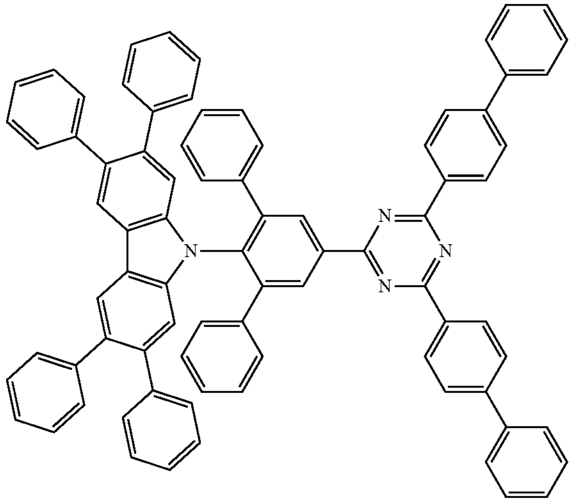
239
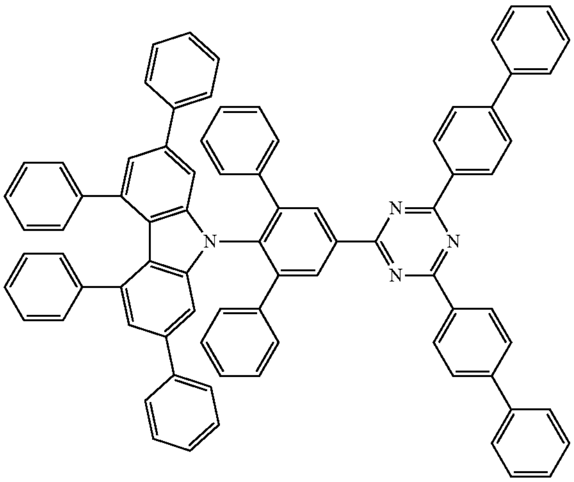
240
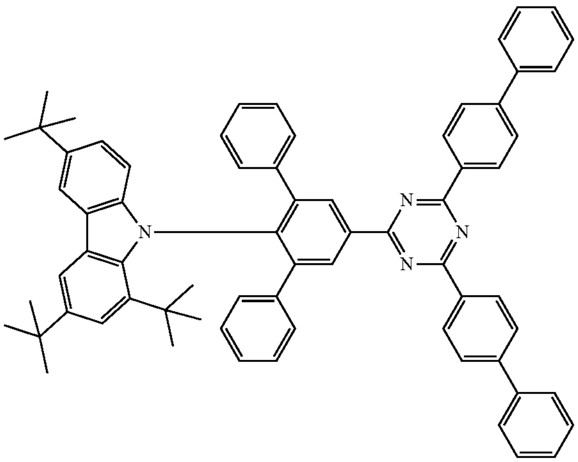
-continued
241
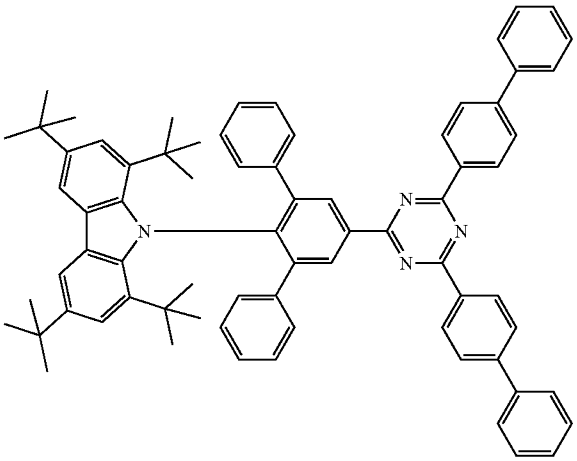
242
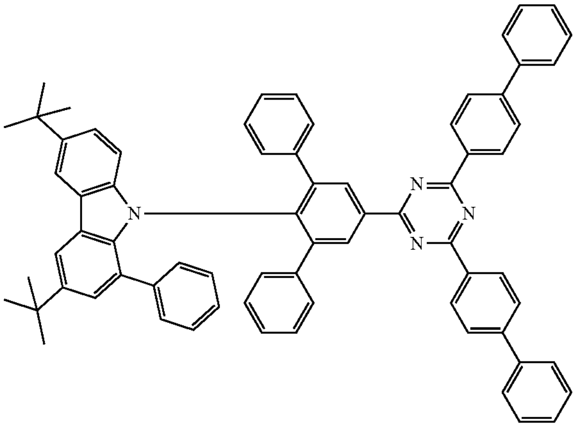
243
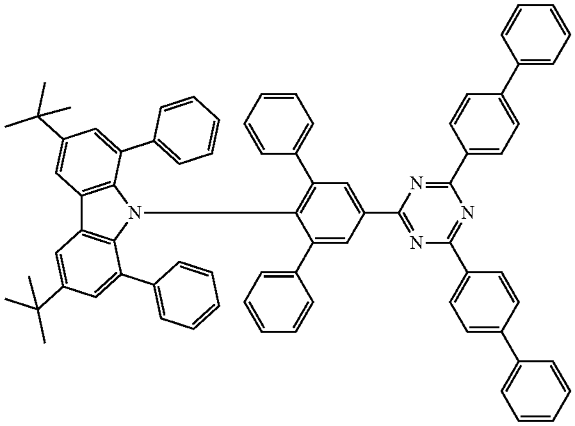

-continued
244
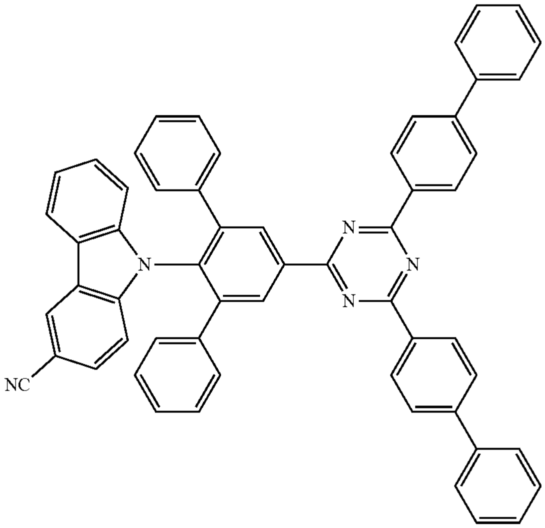
245
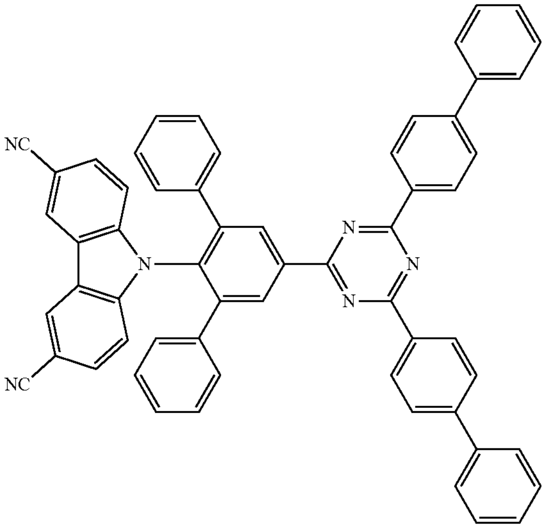
246
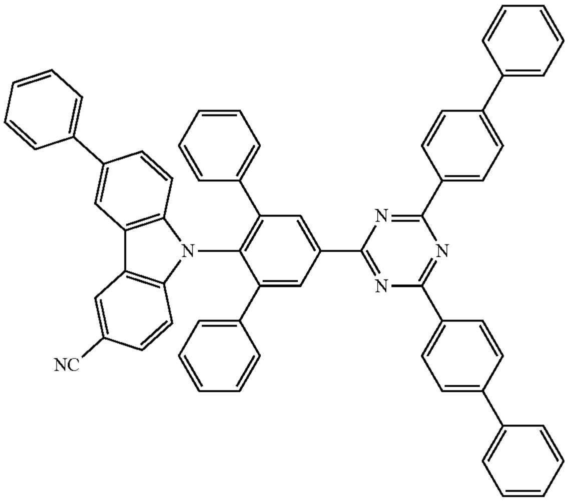
-continued
247
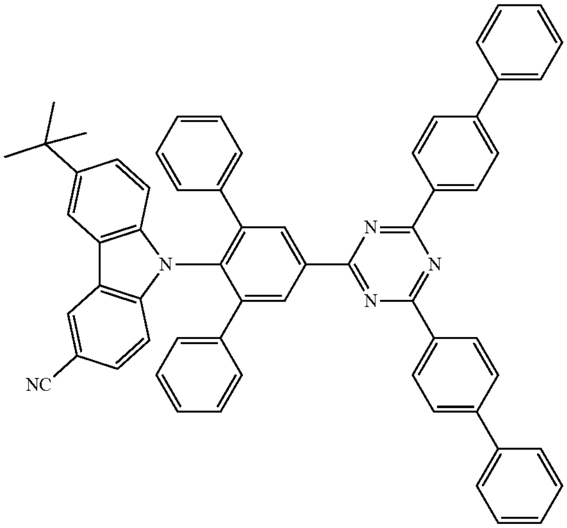
248
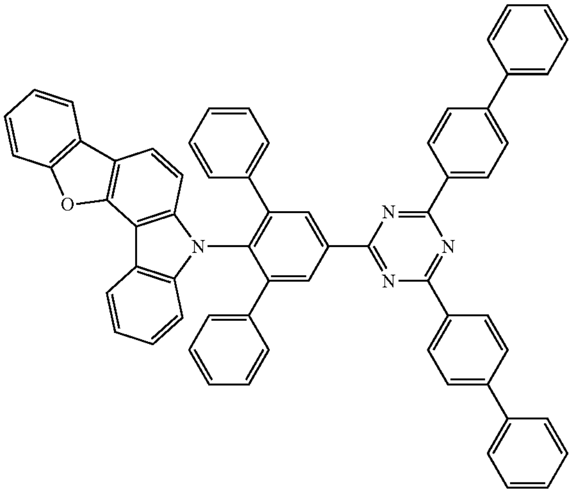
249
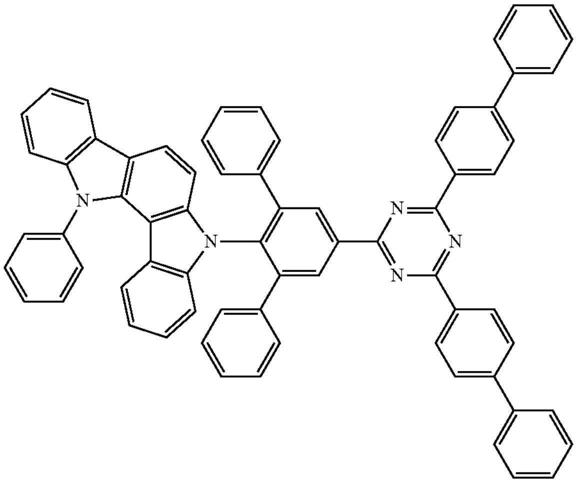

-continued
250
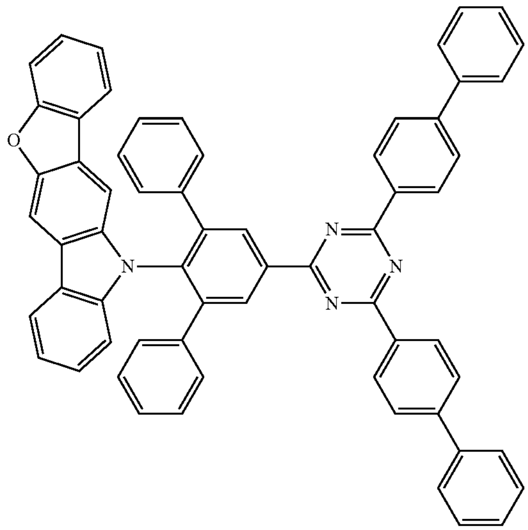
251
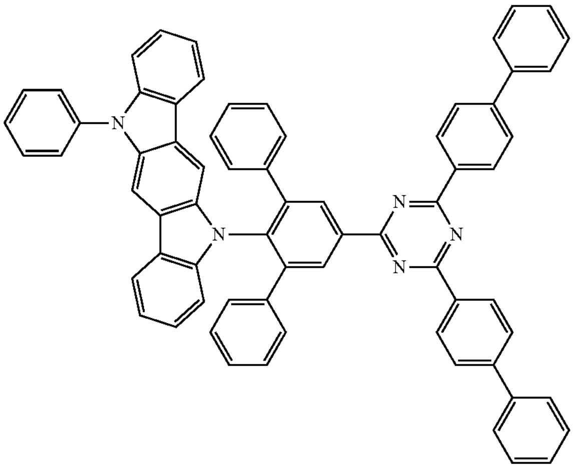
252
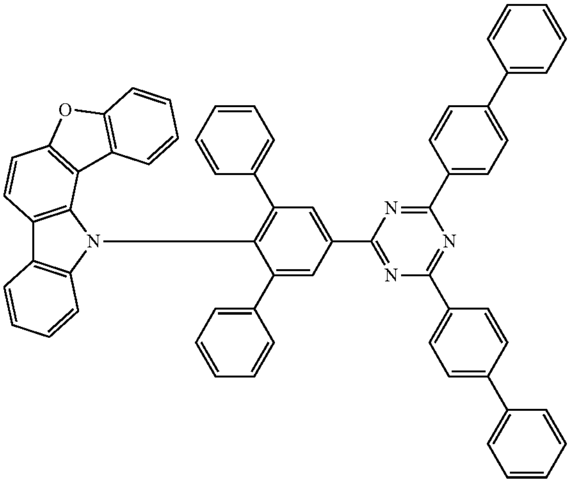
-continued
253
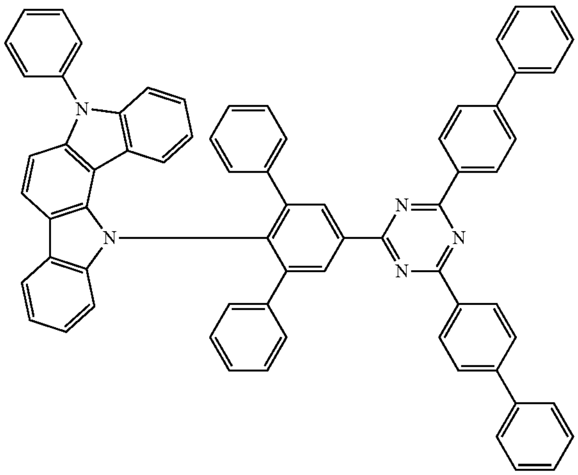
254
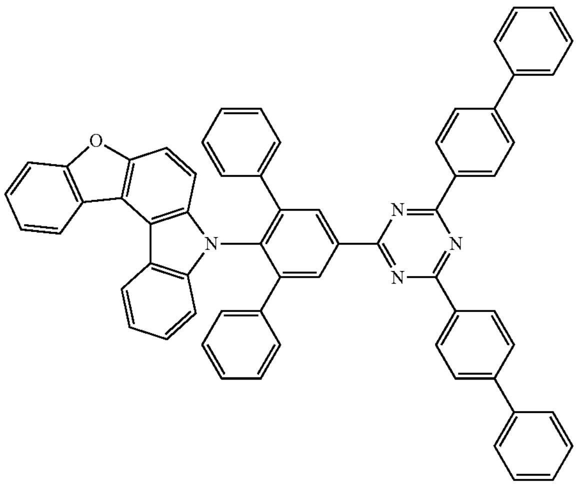
255
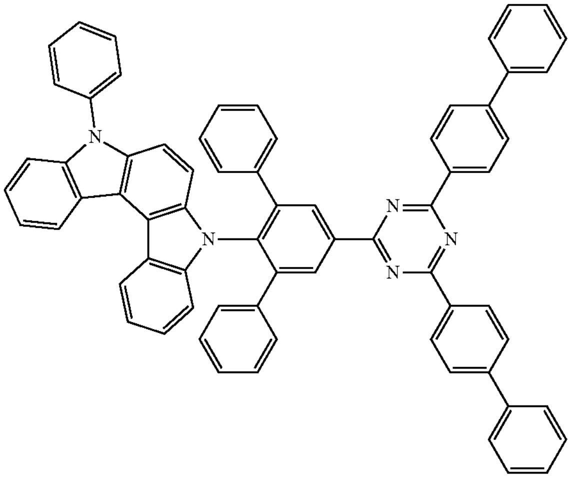

-continued
256
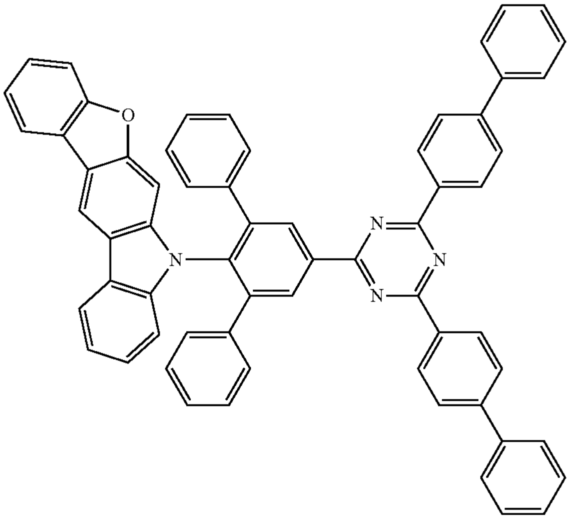
257
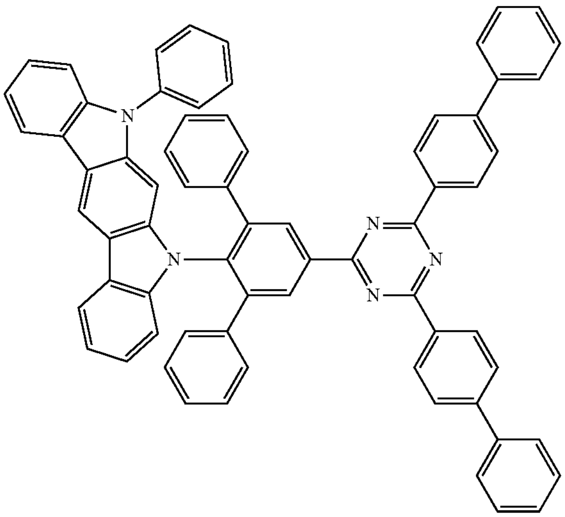
258
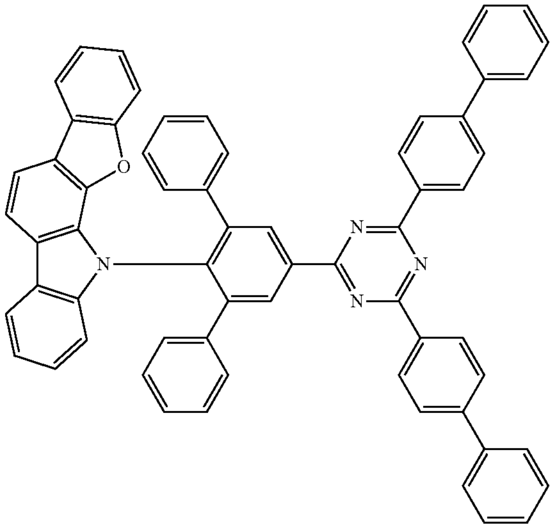
-continued
259
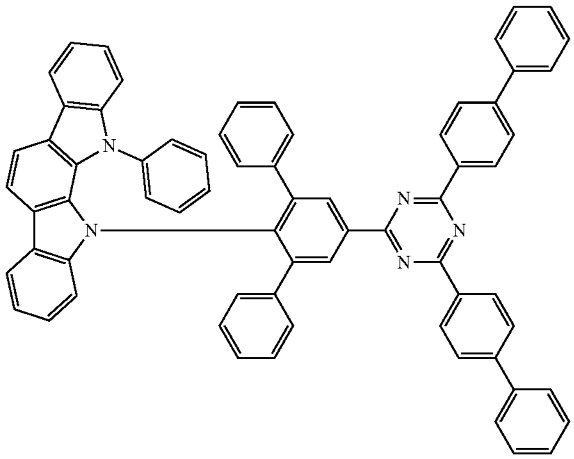
260
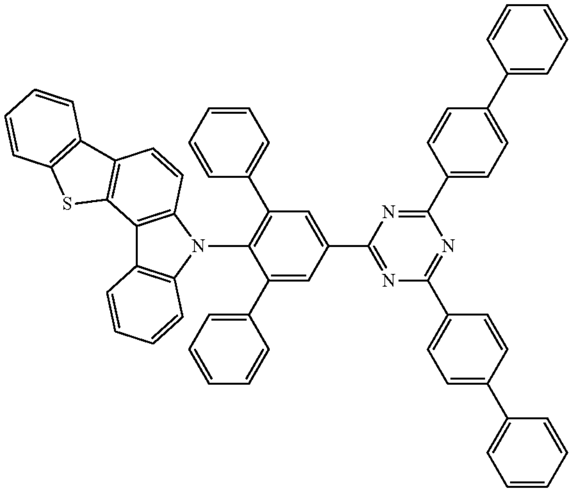
261
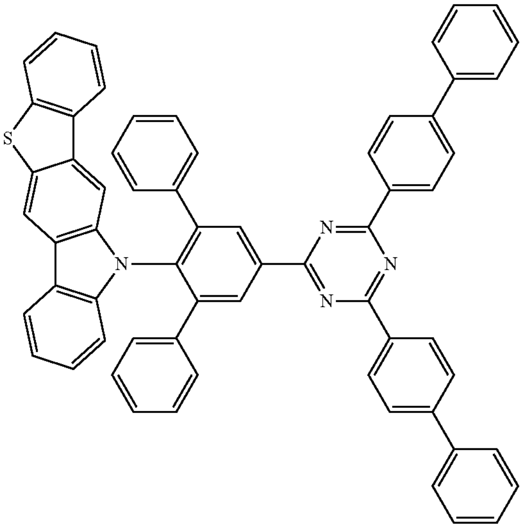

-continued
262
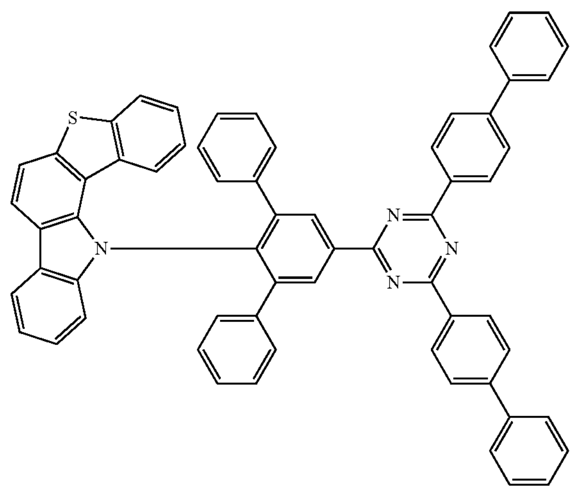
263
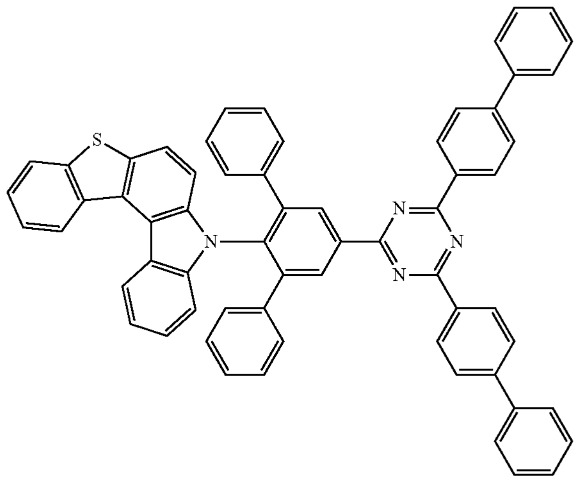
264
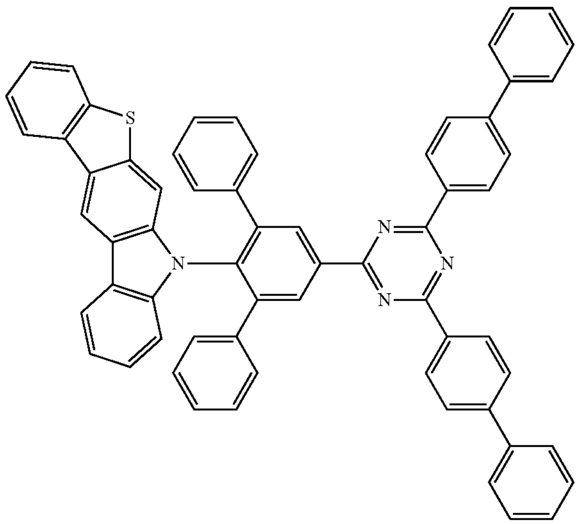
-continued
265
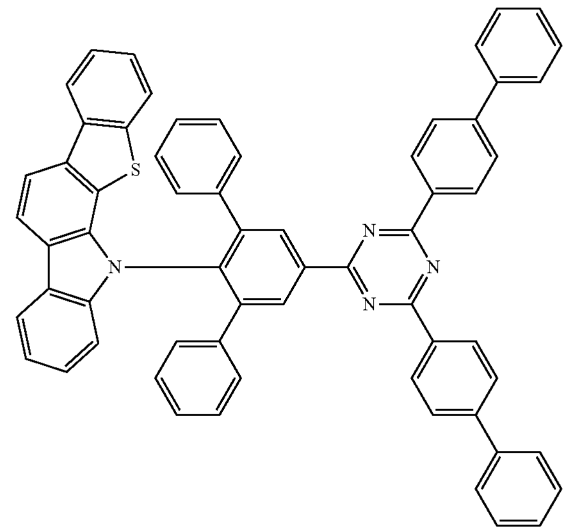
266
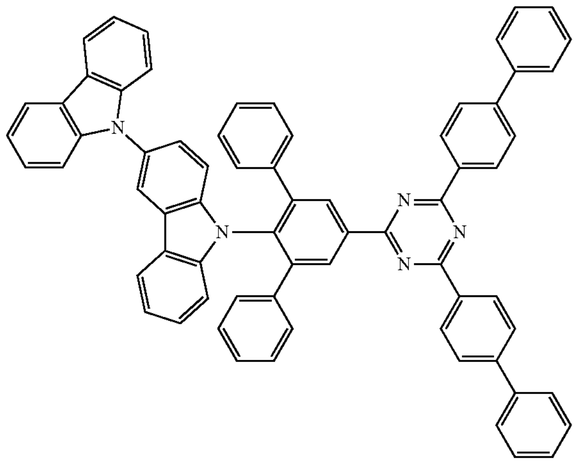
267
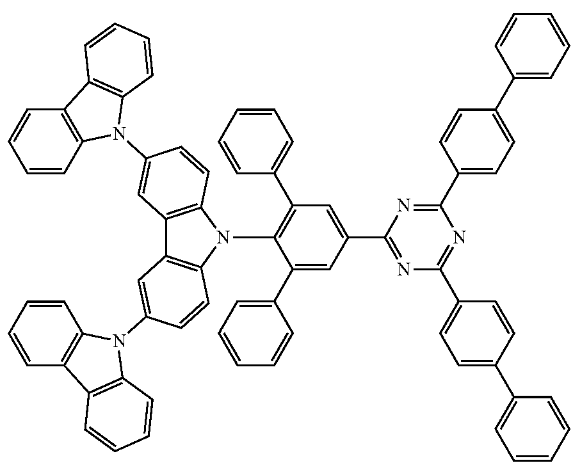

-continued
268
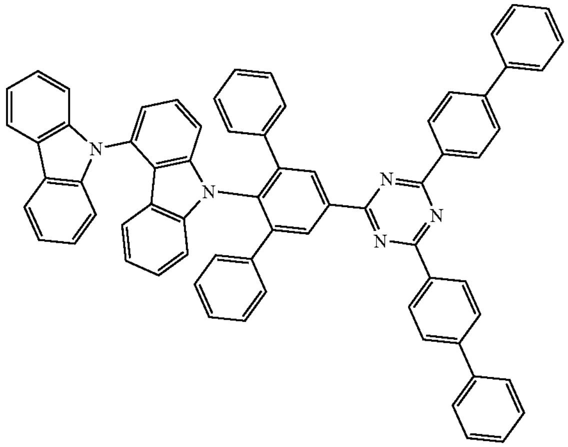
269
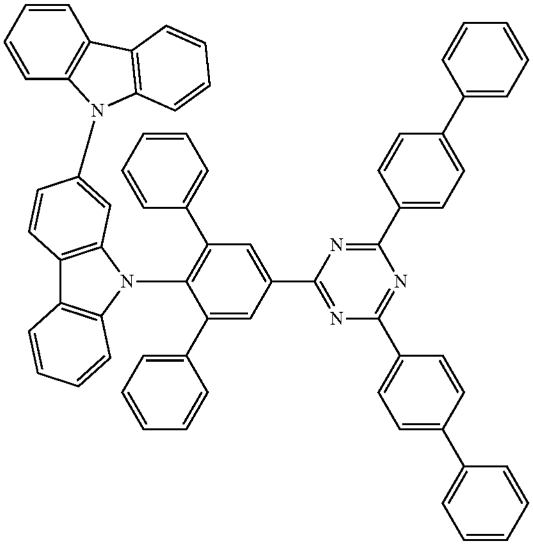
270
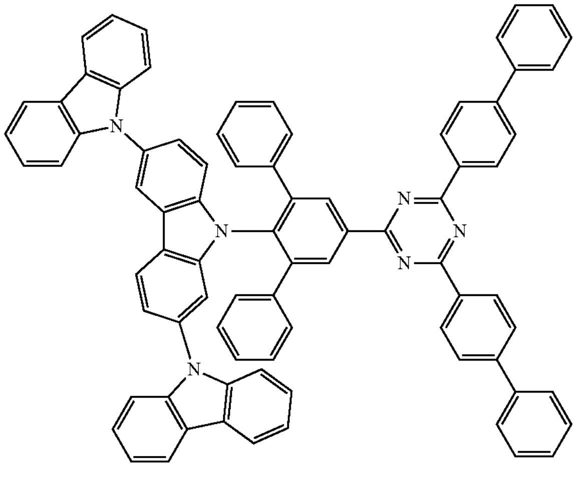
-continued
271
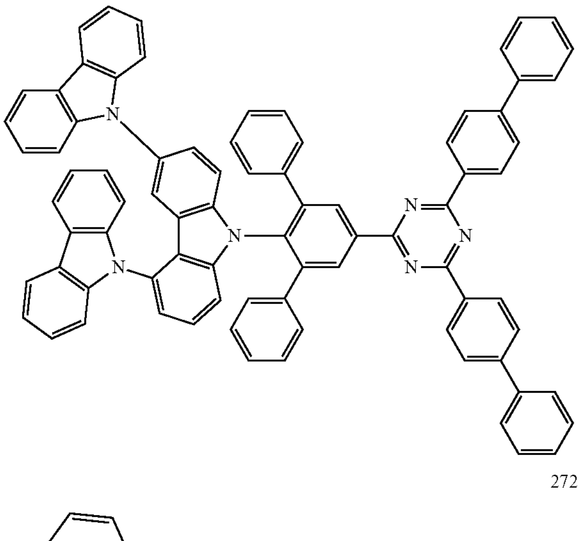
272
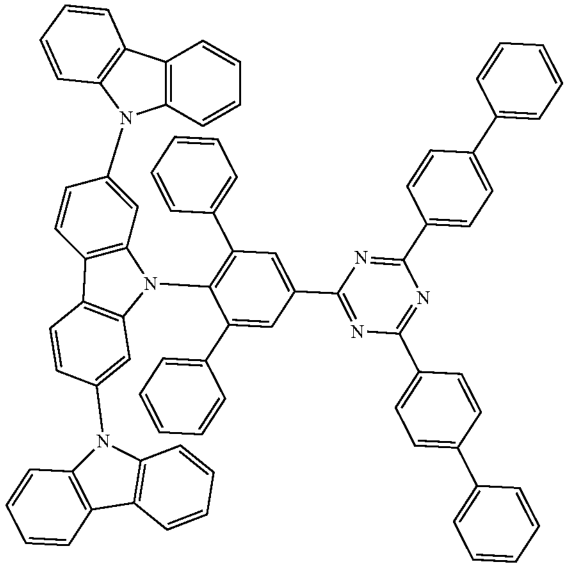
273
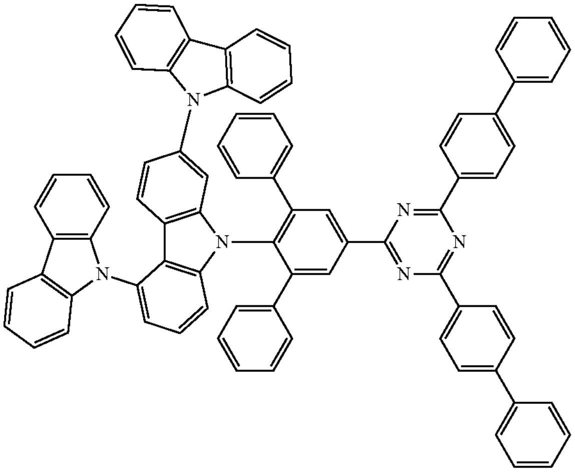

-continued
274
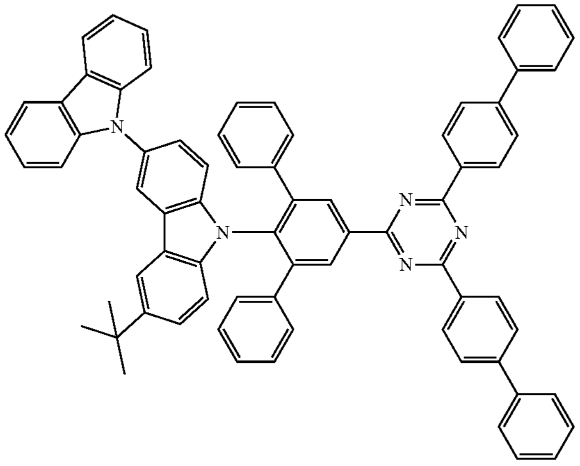
277
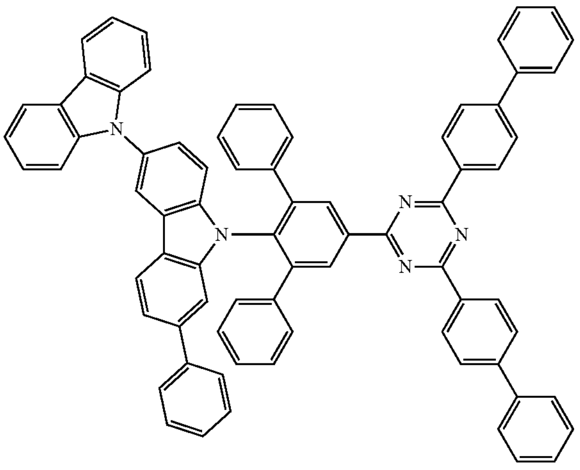
275
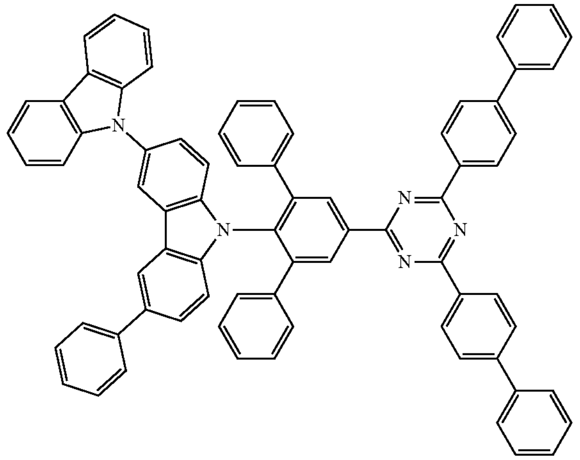
278
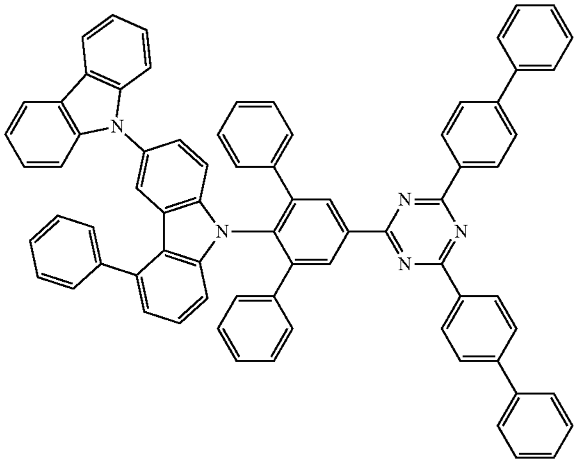
276
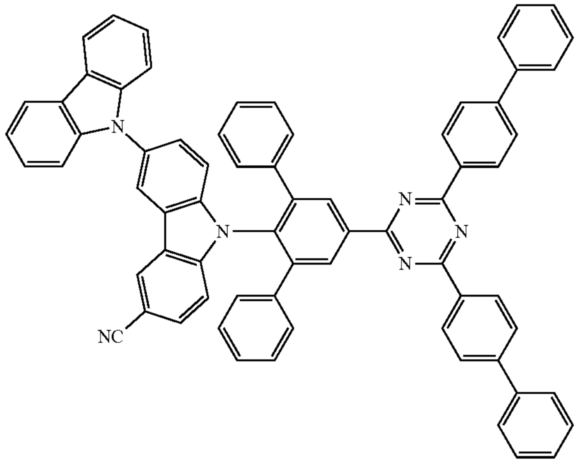
279
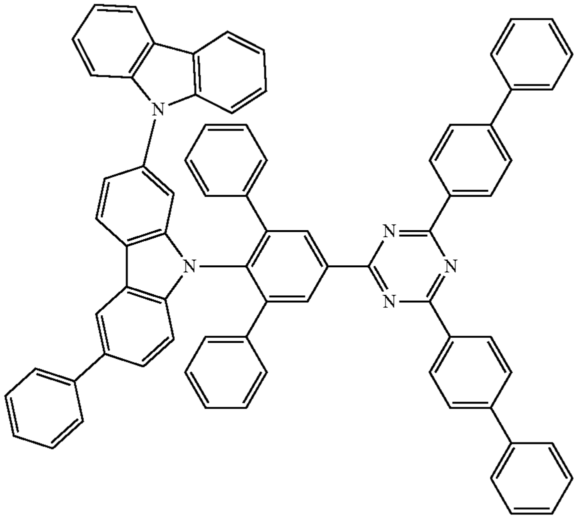

-continued
280
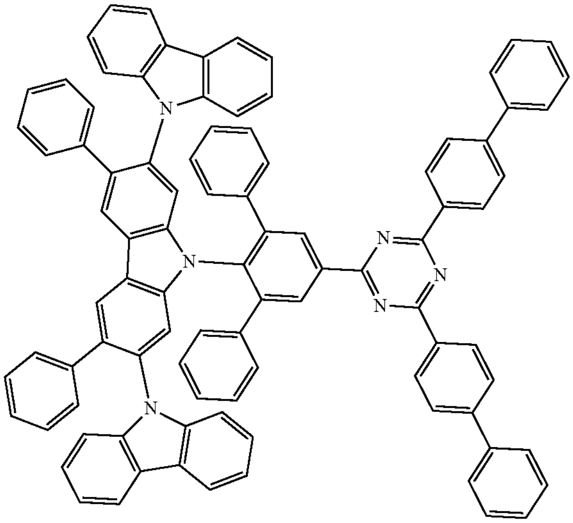
281
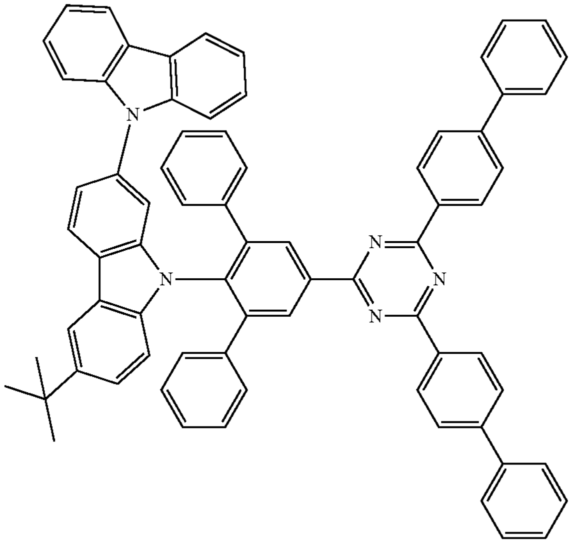
282
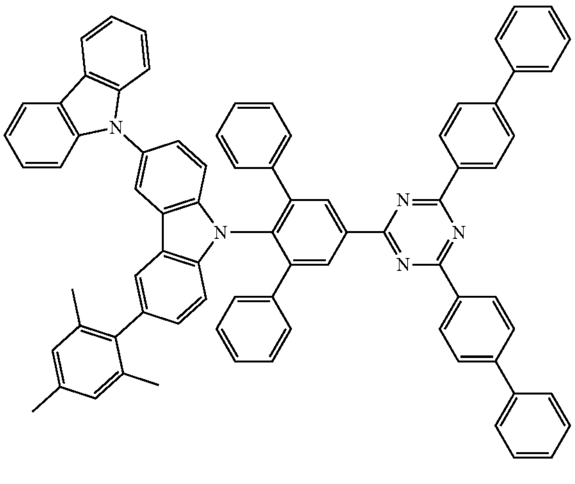
-continued
283
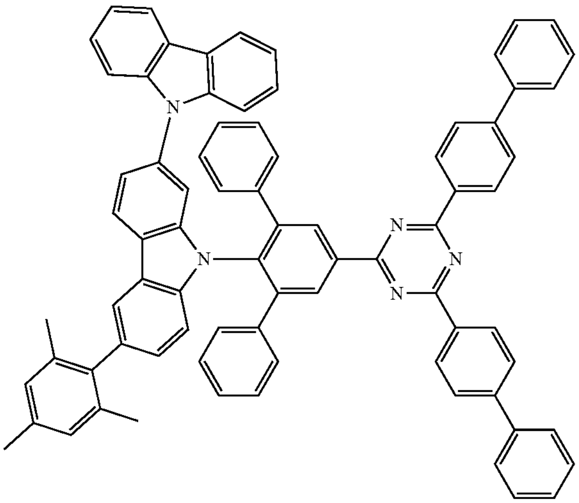
284
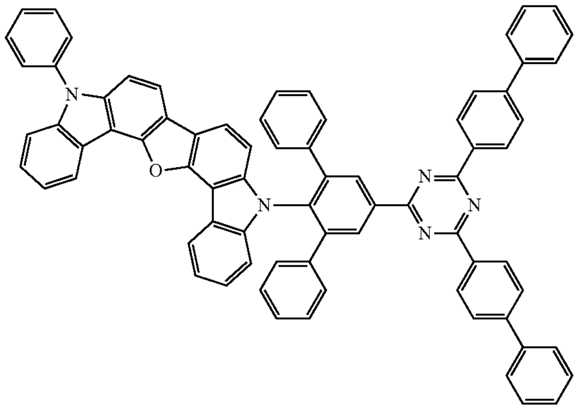
285
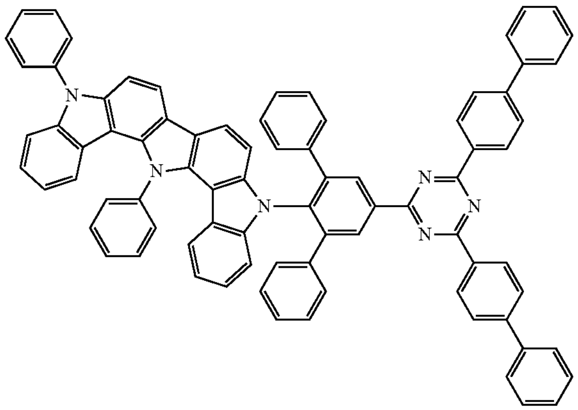

286
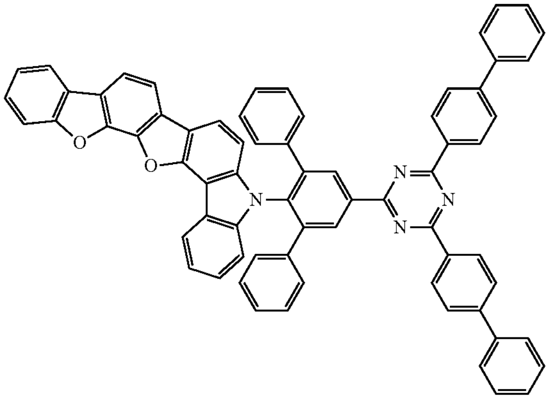
287
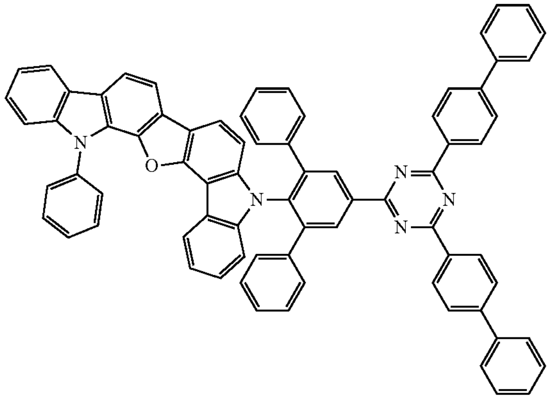
288
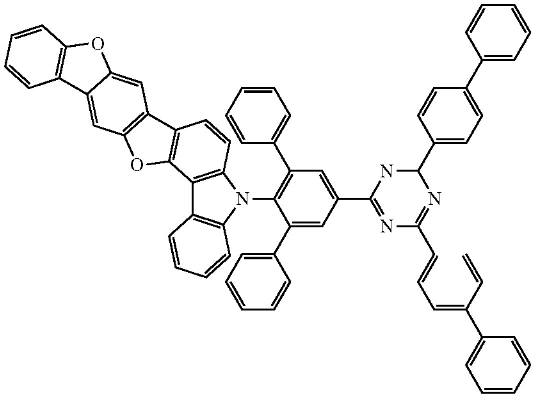
289
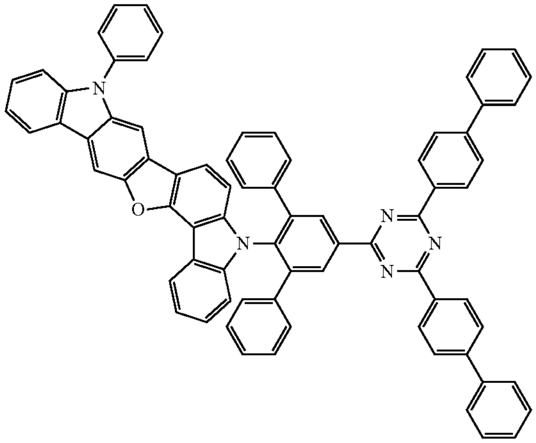
290
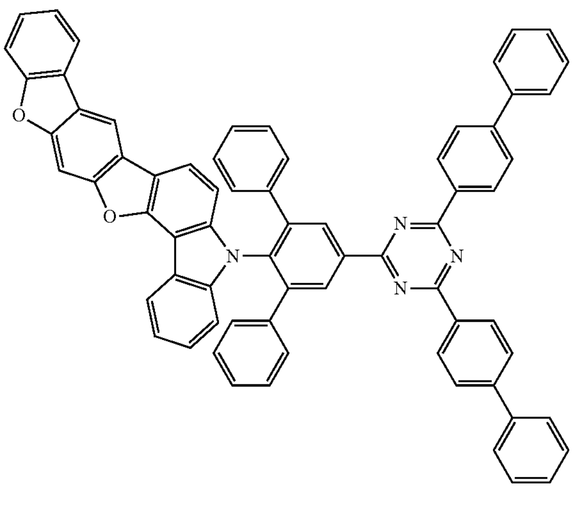
291
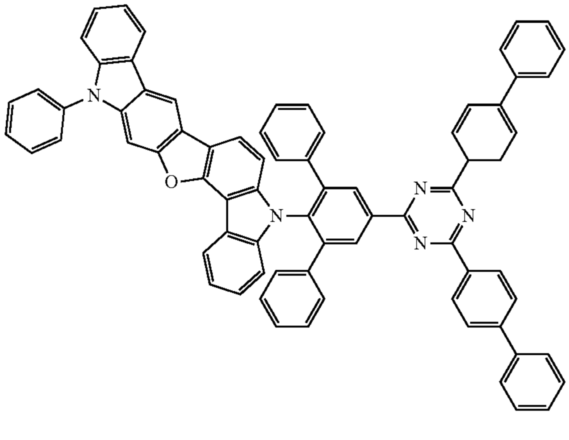

-continued
292
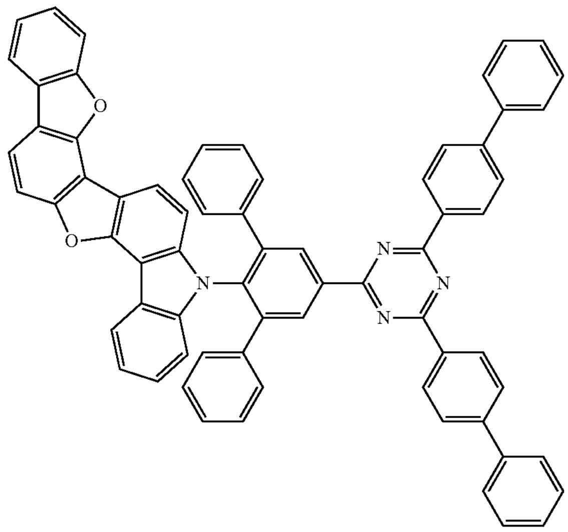
293
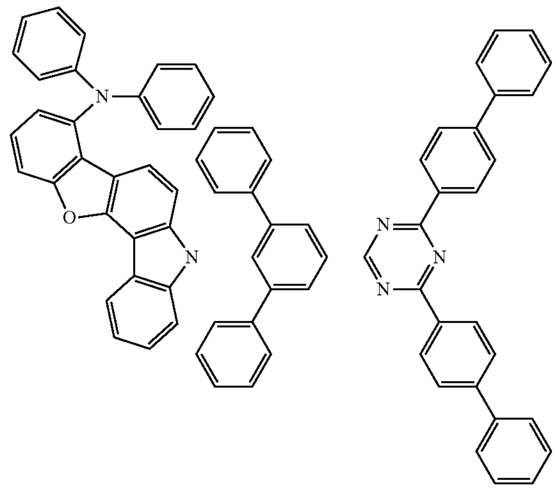
294
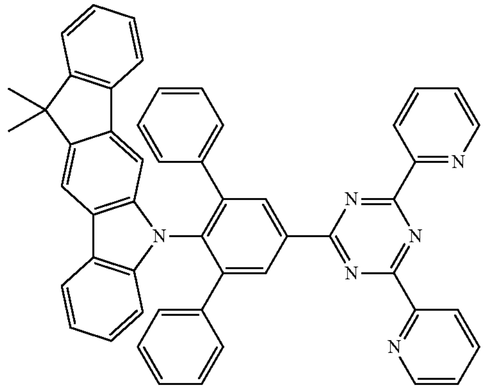
295
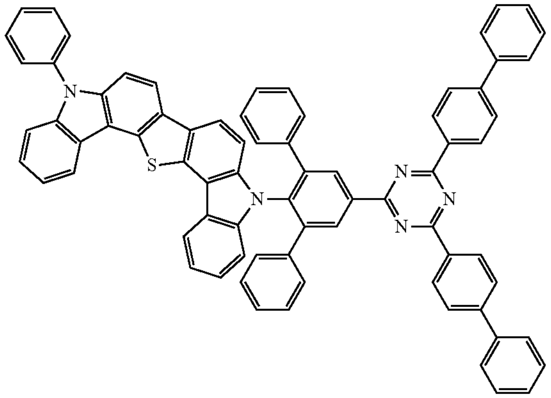
296
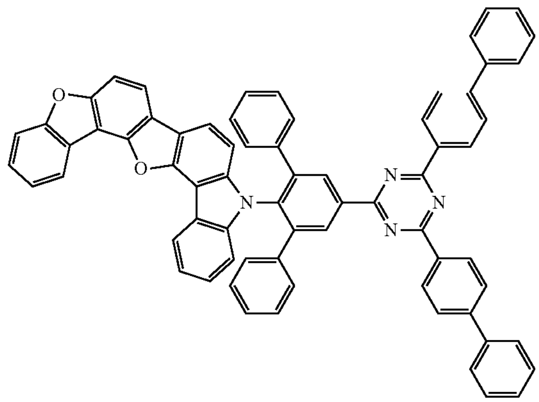
297
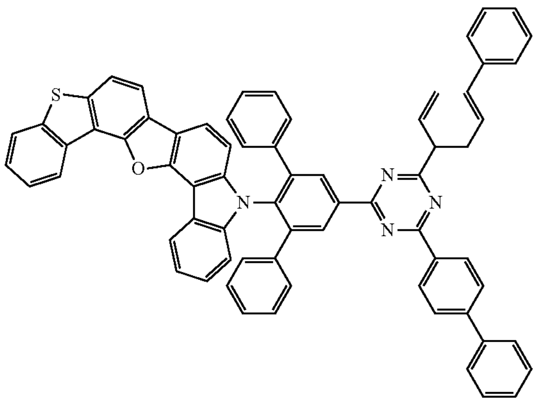

-continued
298
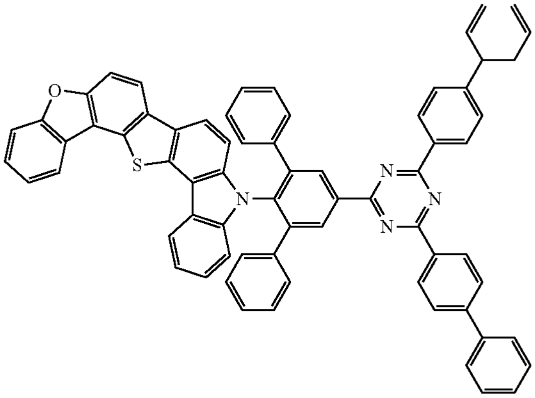
299
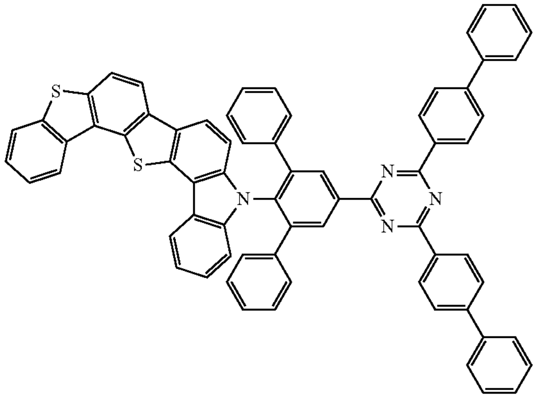
300
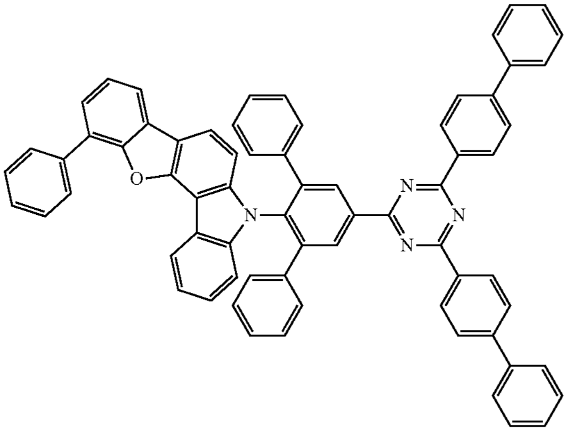
301
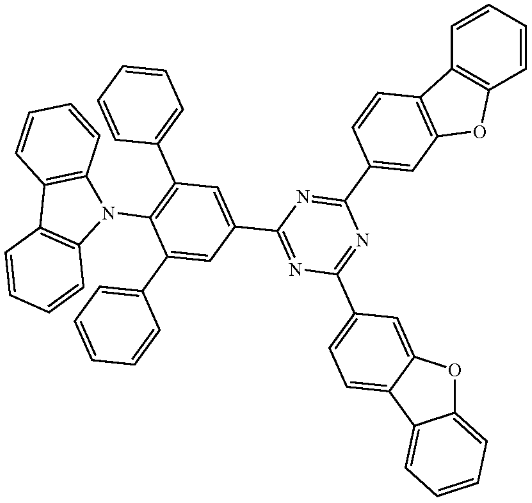
302
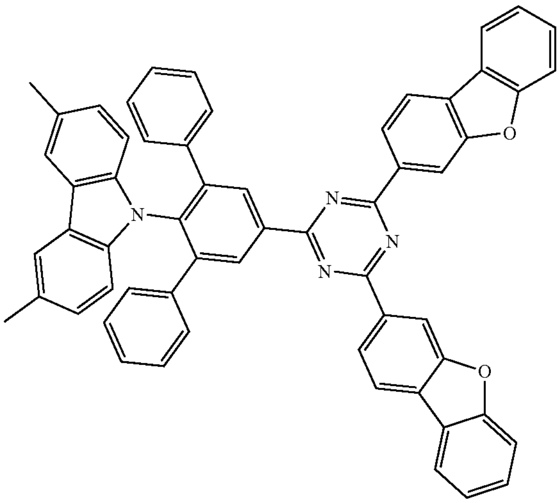
303
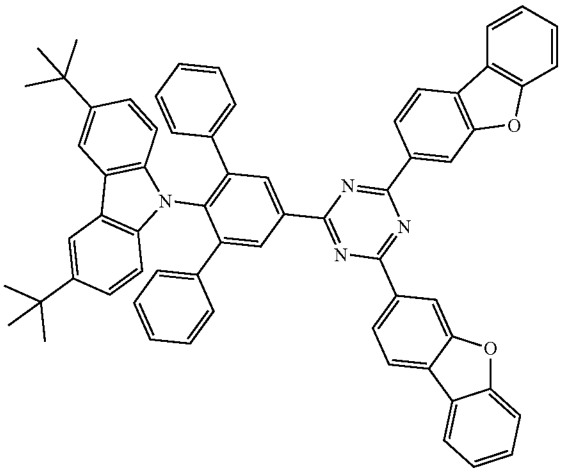

-continued
304
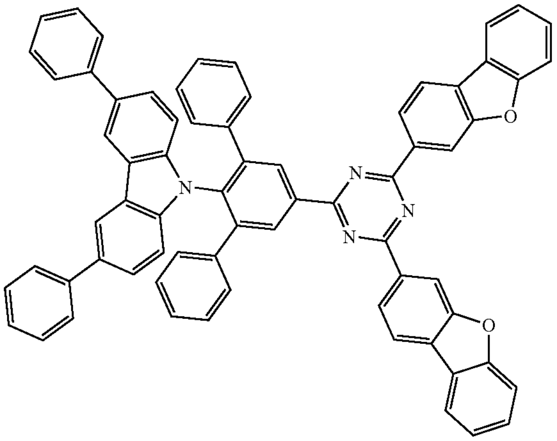
305
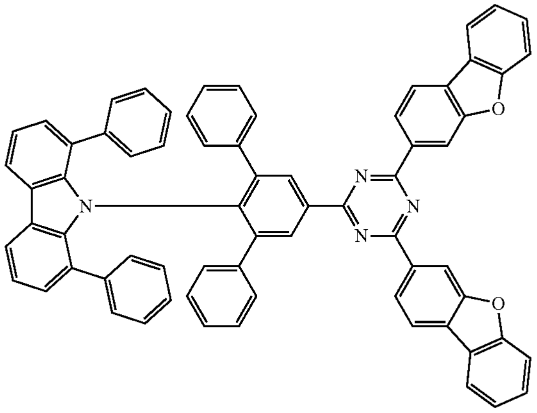
306
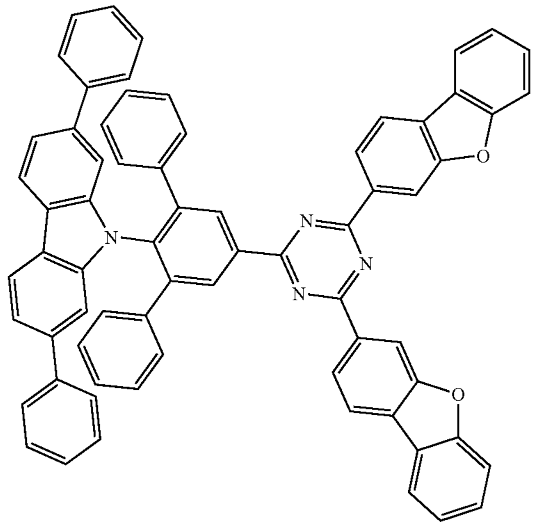
307
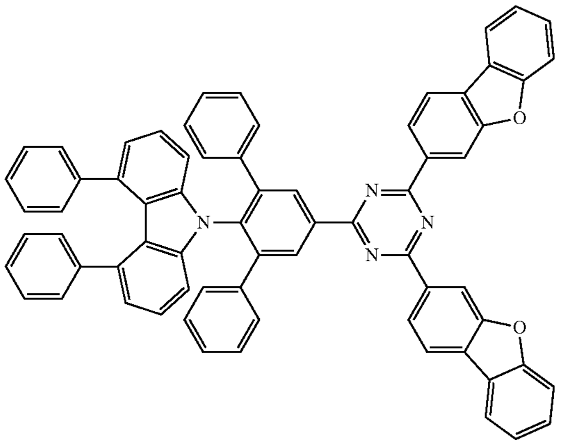
308
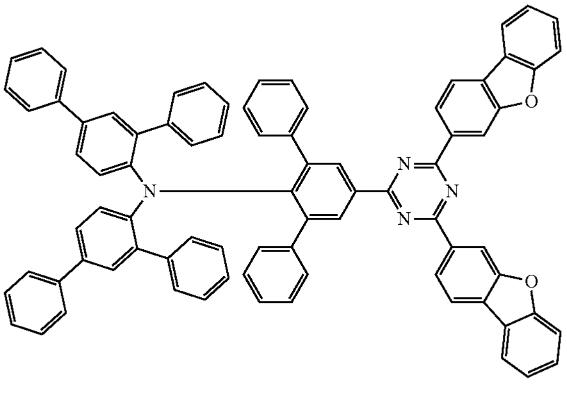
309
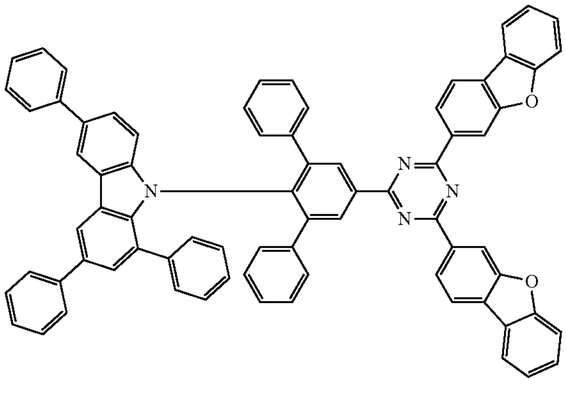

-continued
310
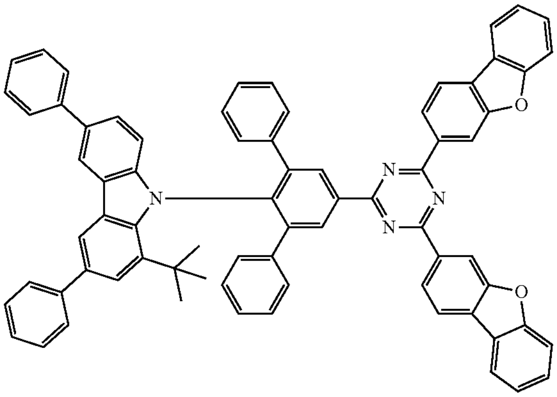
311
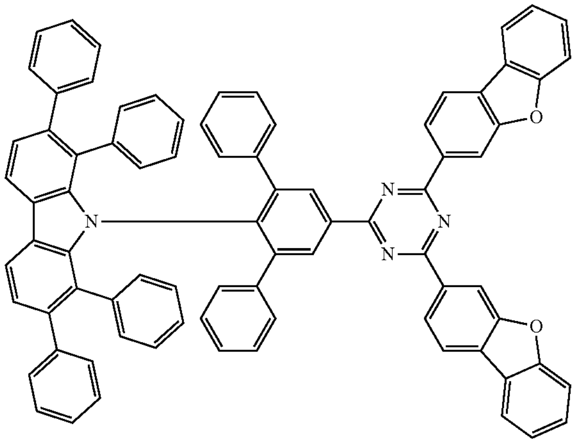
312
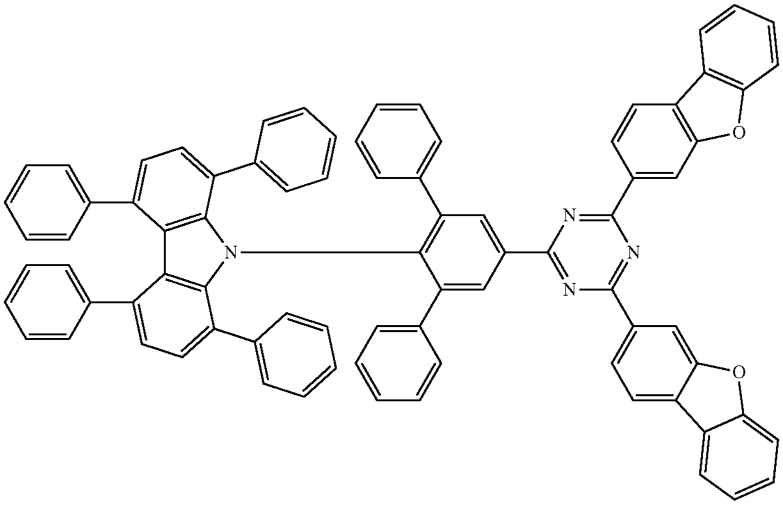
313
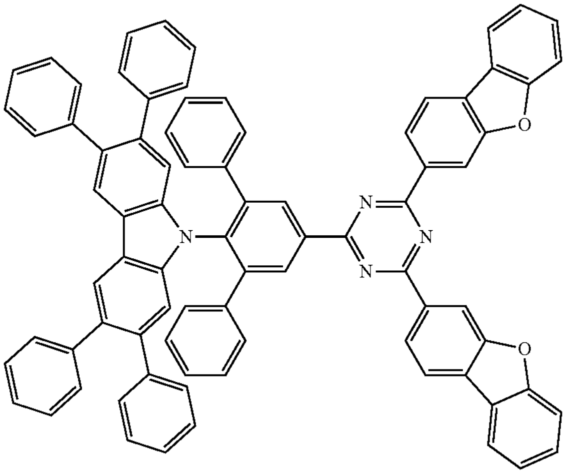
314
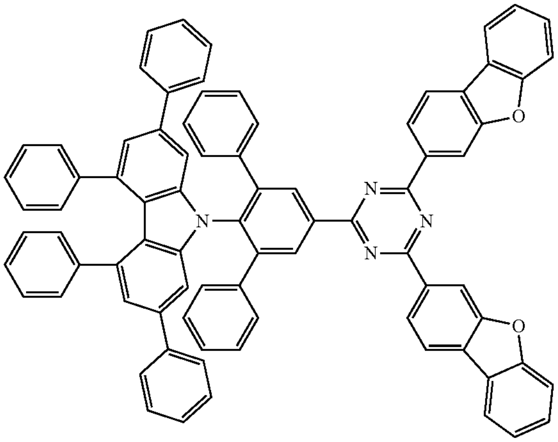

315
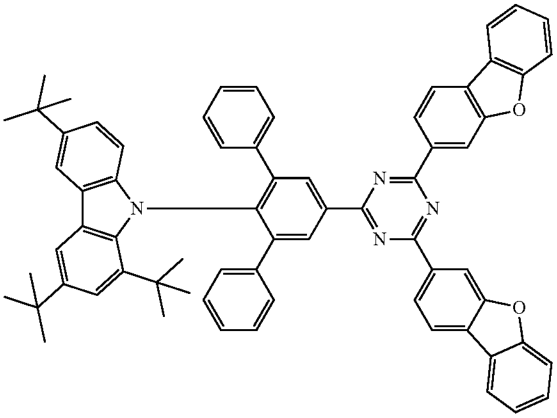
316
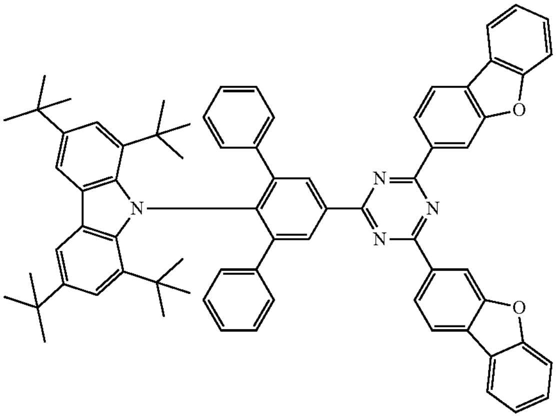
317
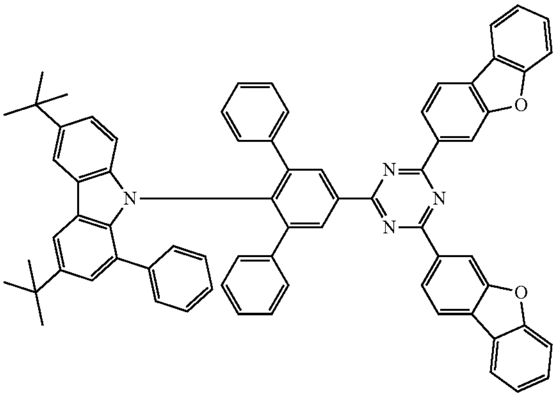
-continued
318
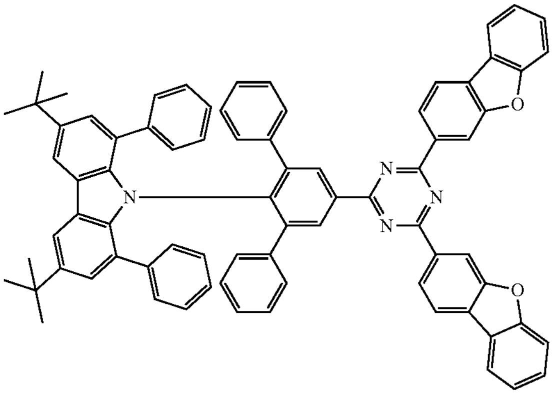
319
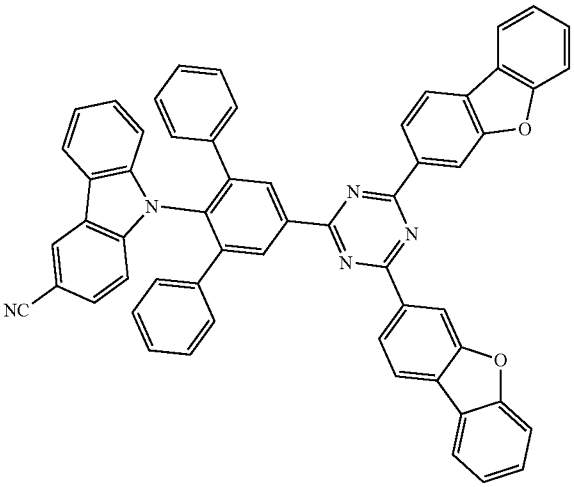
320
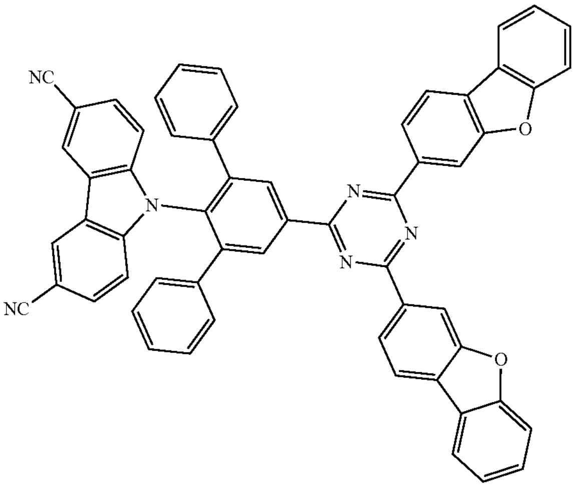

-continued
321
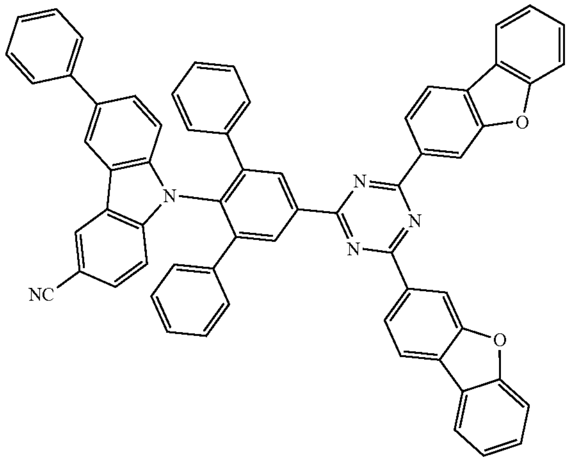
322
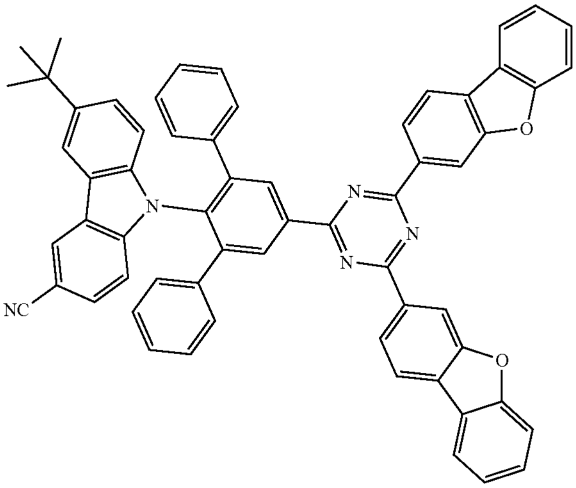
323
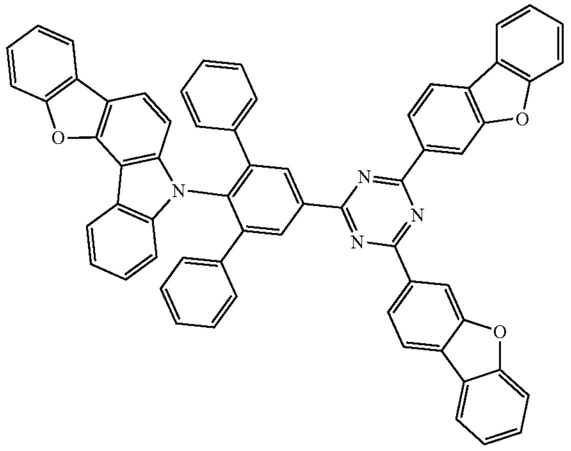
-continued
324
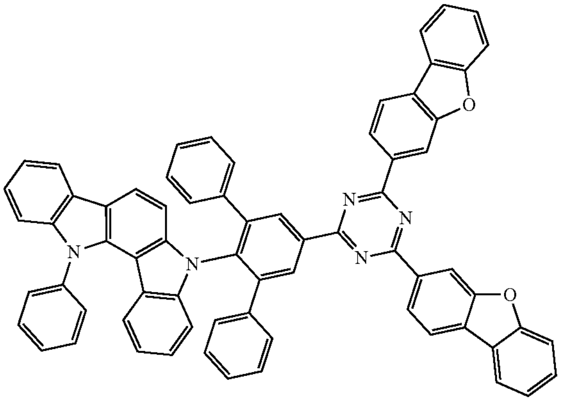
325
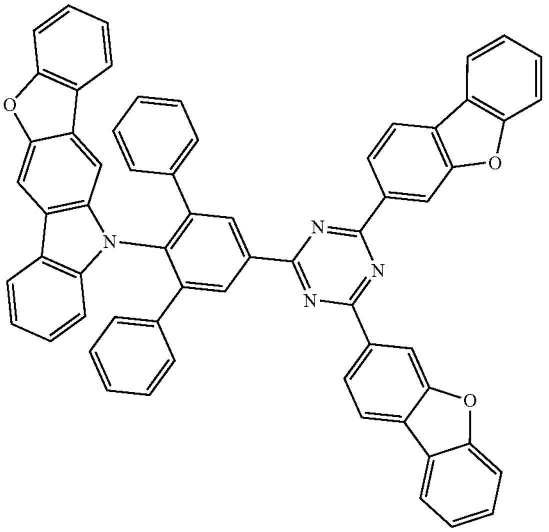
326
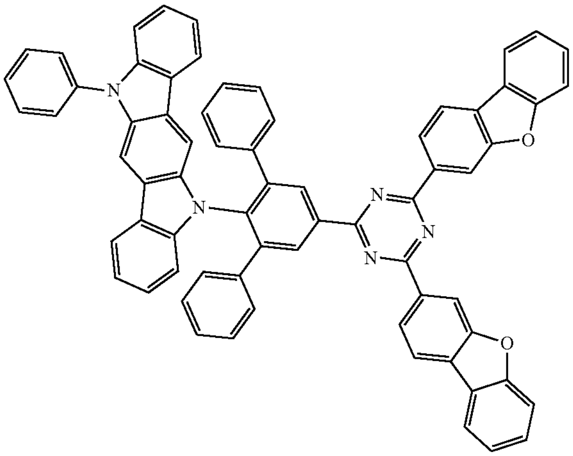

-continued
327
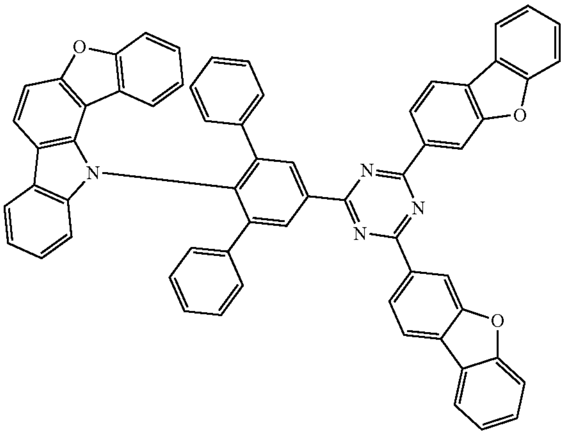
328
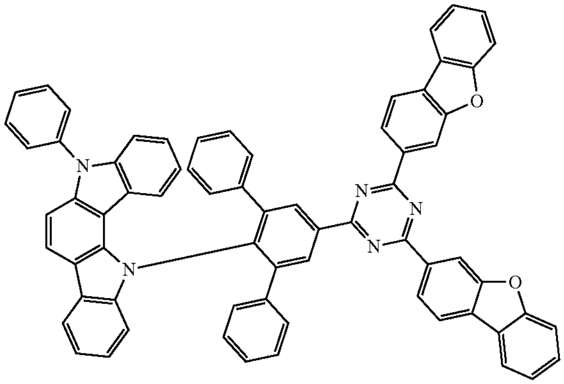
329
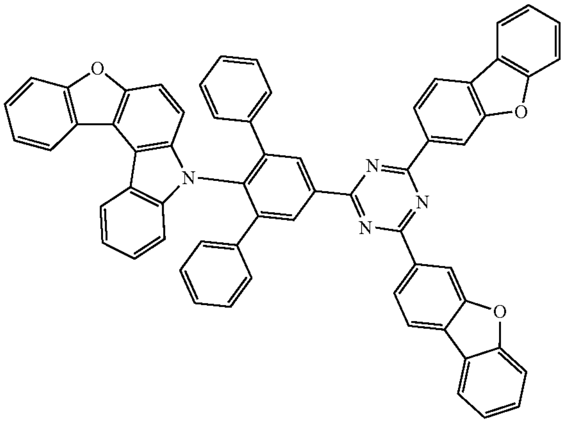
-continued
330
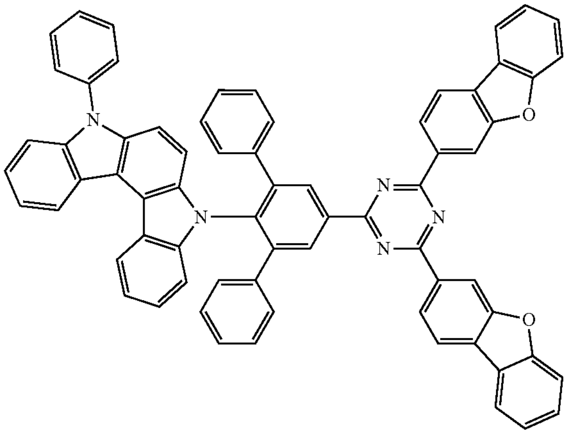
331
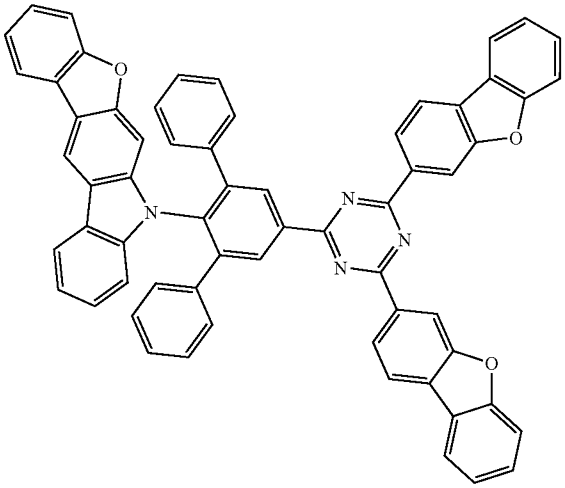
332
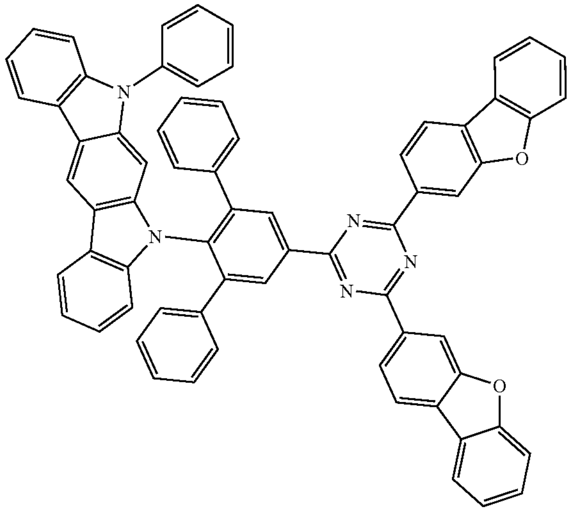

-continued
333
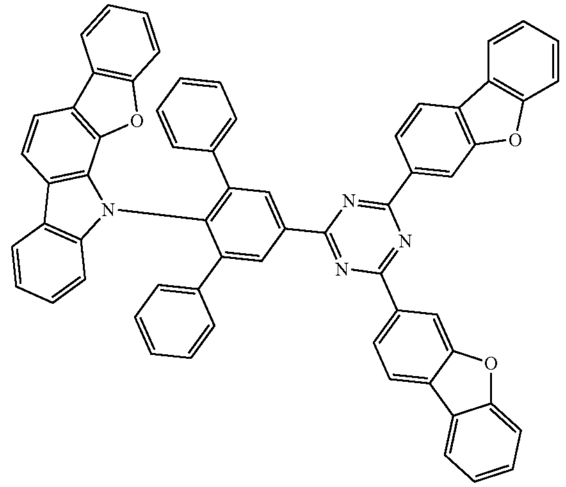
334
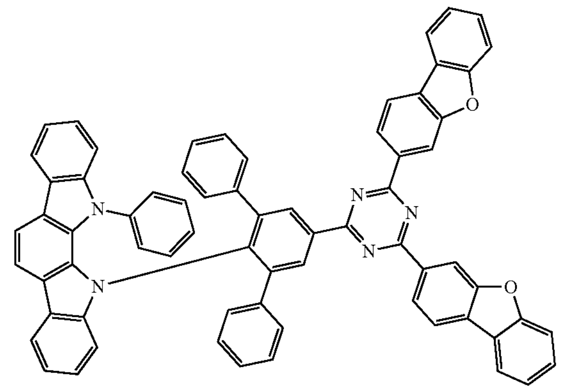
335
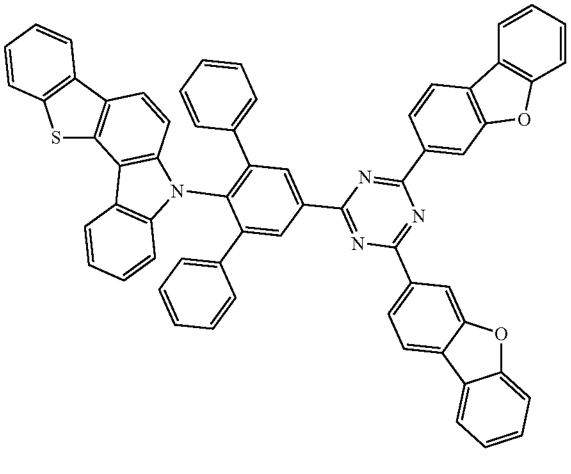
-continued
336
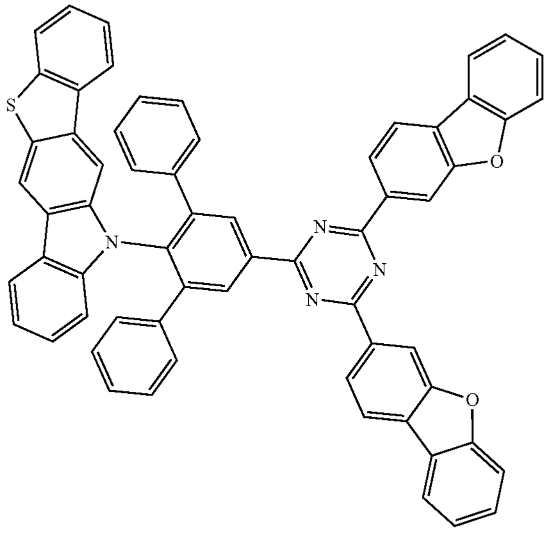
337
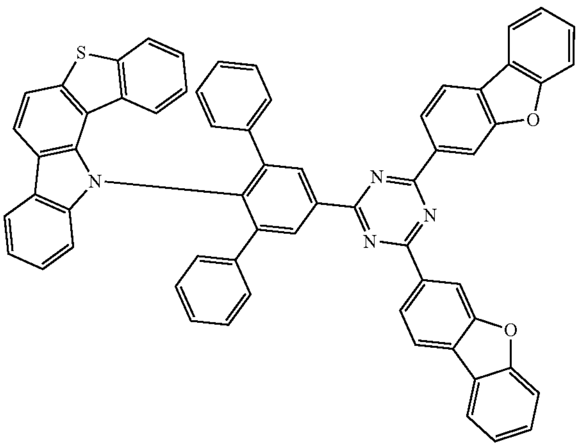
338
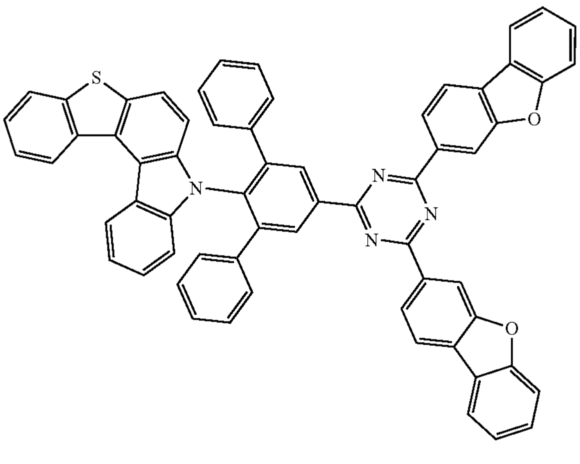

-continued
339
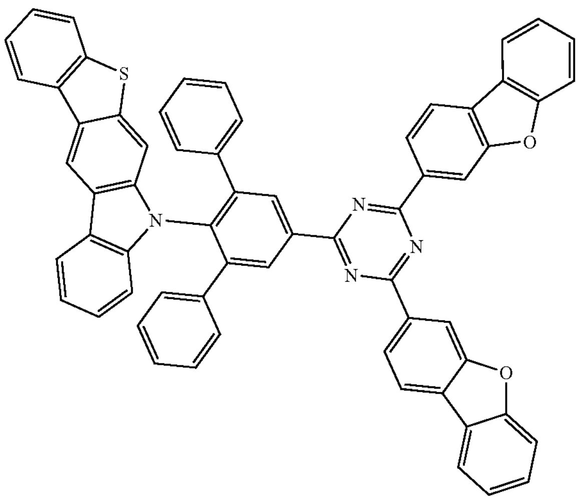
340
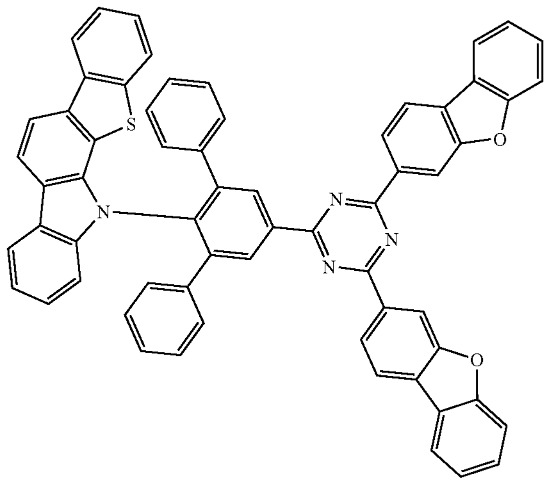
341
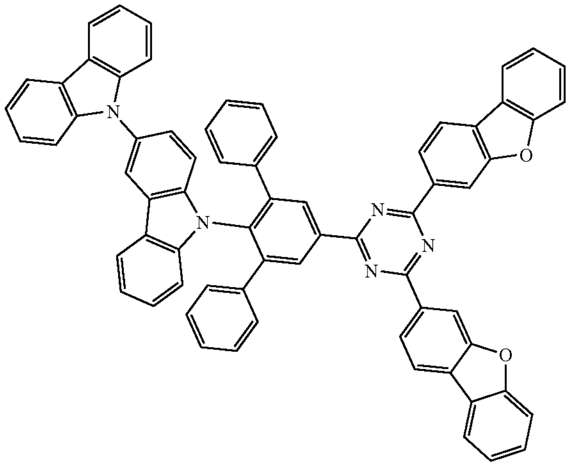
-continued
342
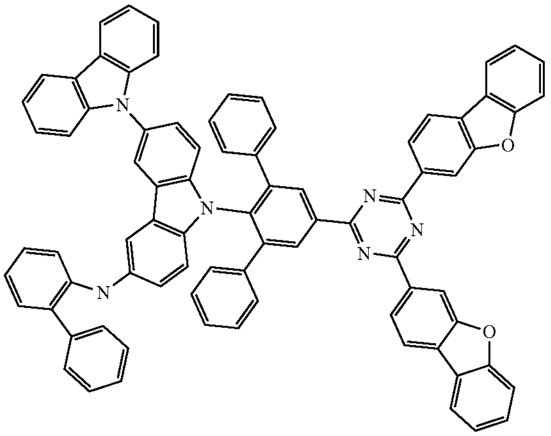
343
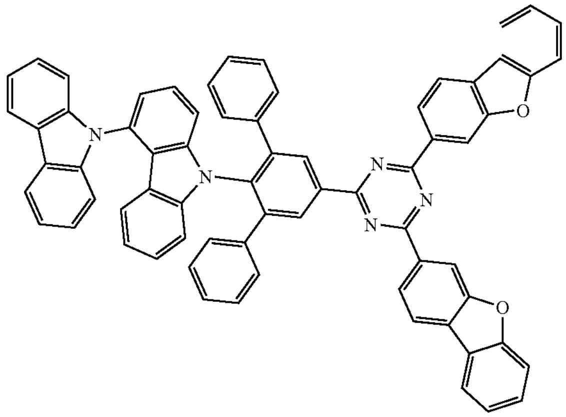
344
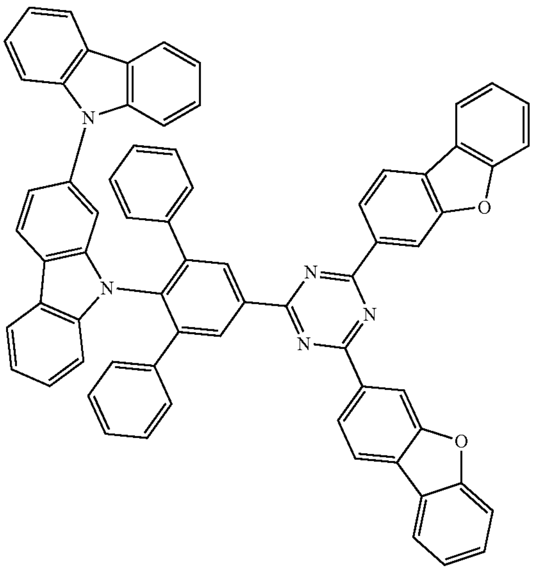

-continued
345
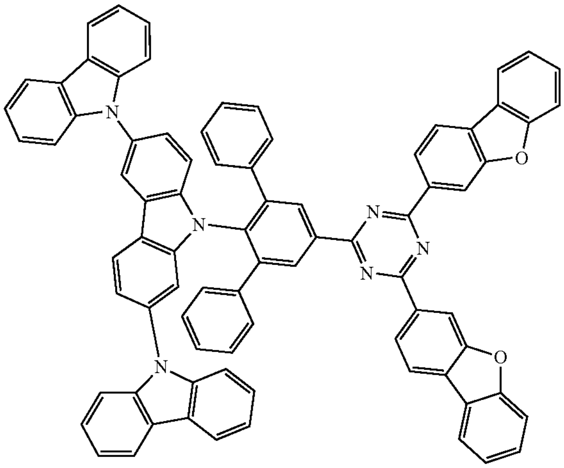
346
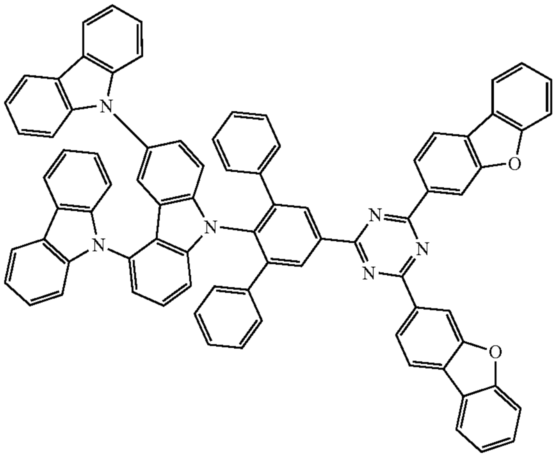
347
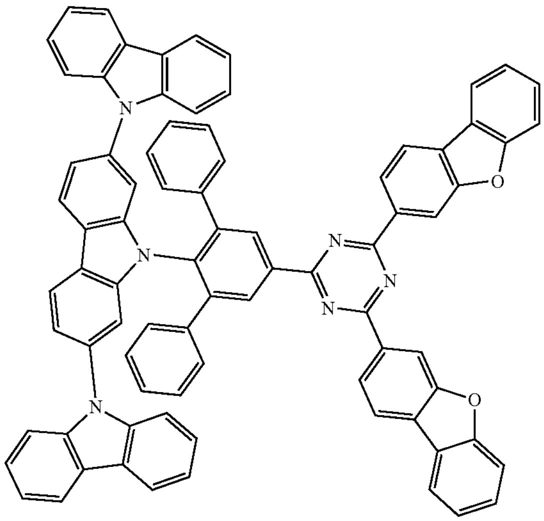
-continued
348
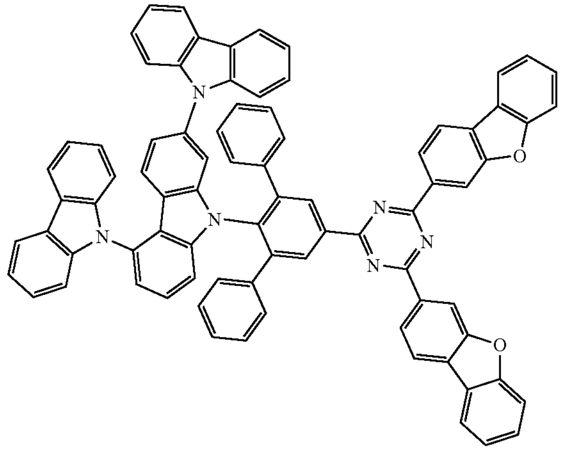
349
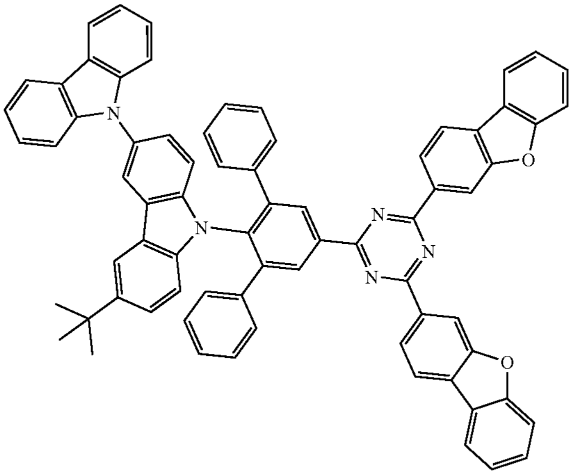
350
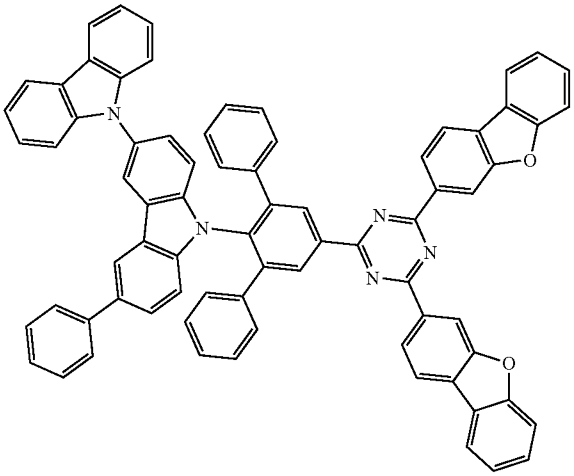

-continued
351
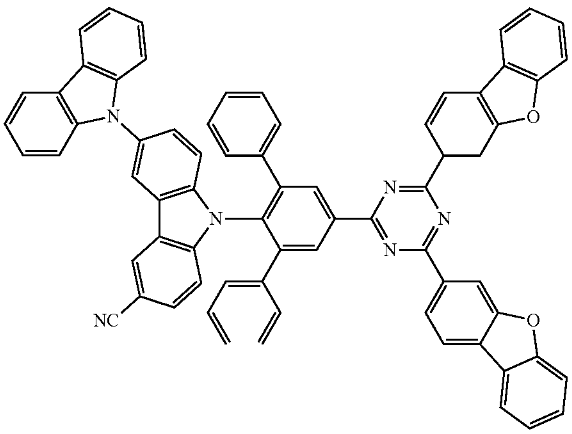
352
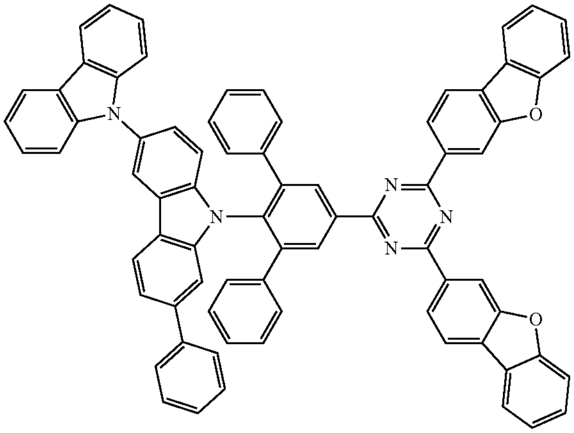
-continued
353
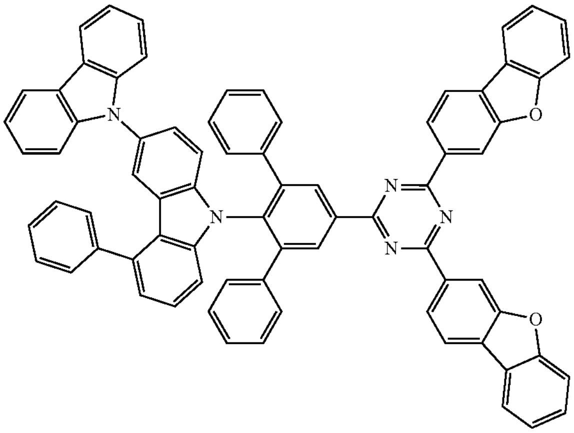
354
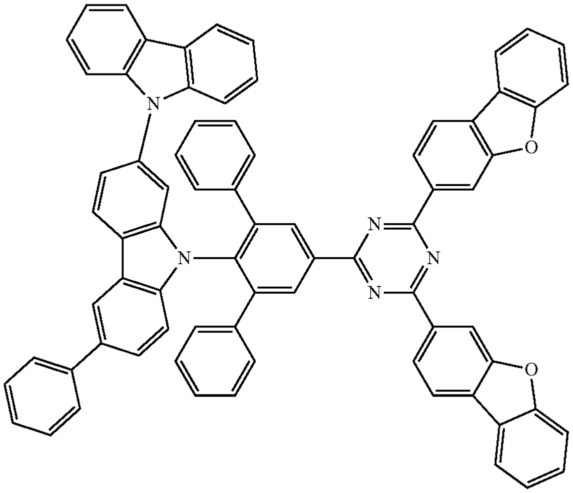
355
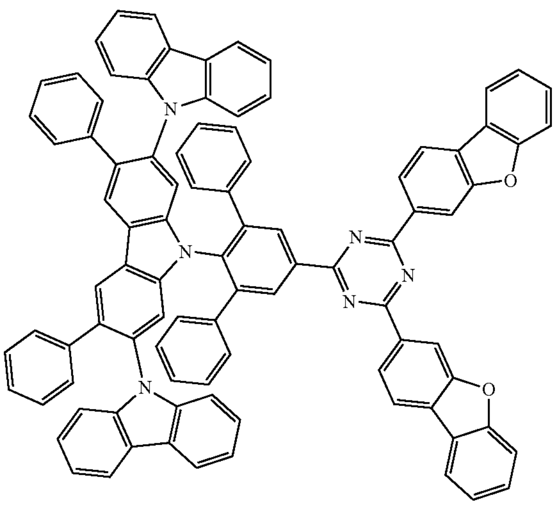
356
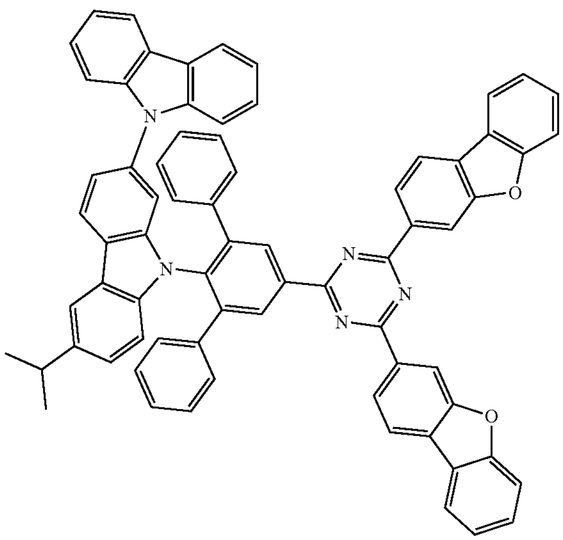

-continued
357
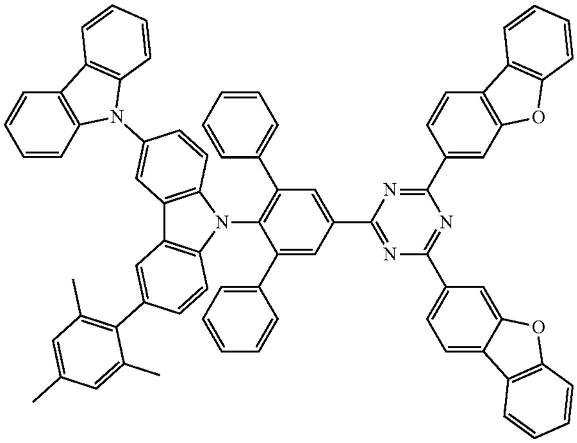
358
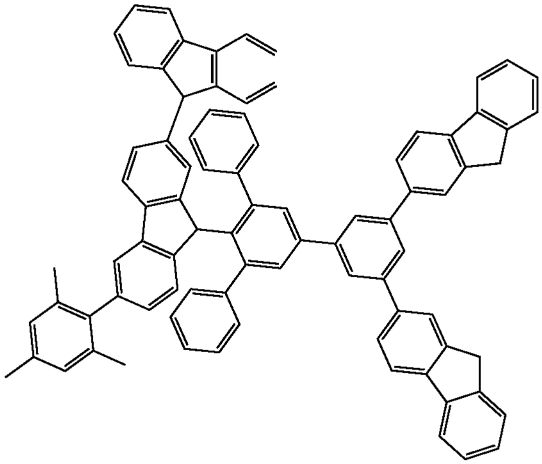
359
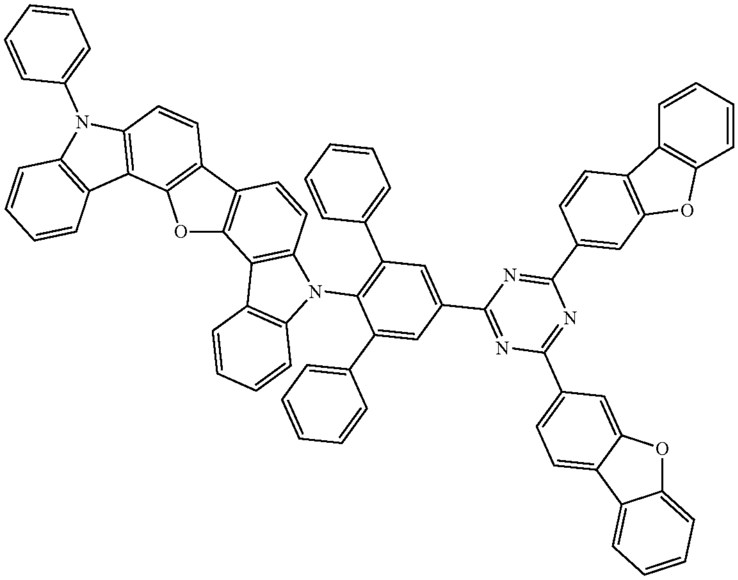
360
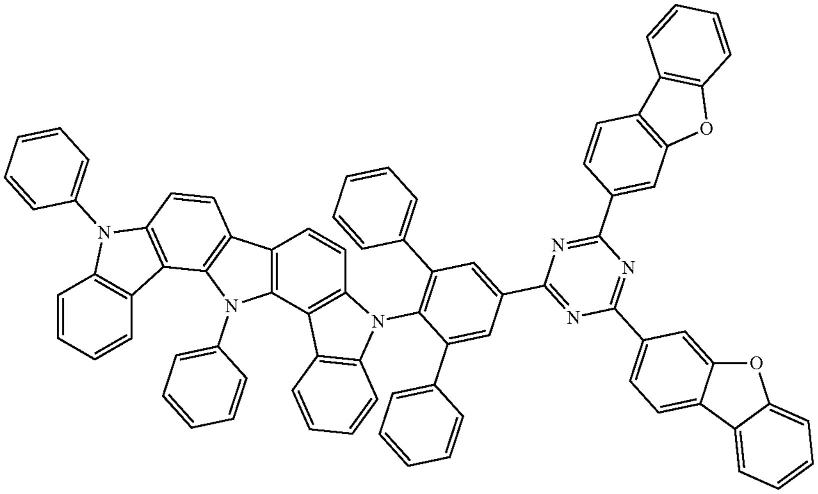

-continued
361
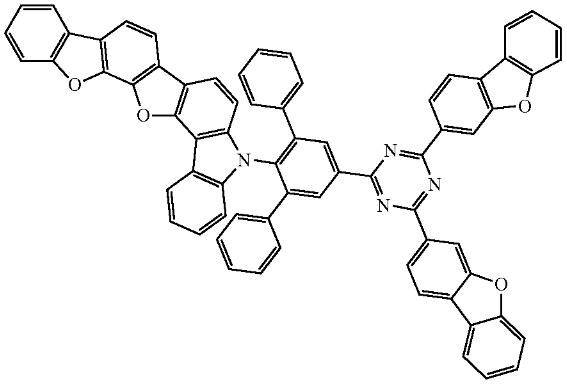
362
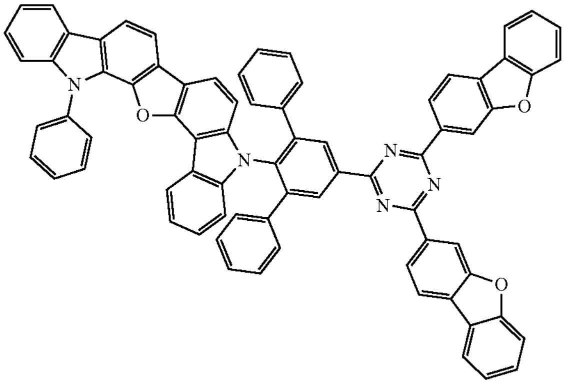
363
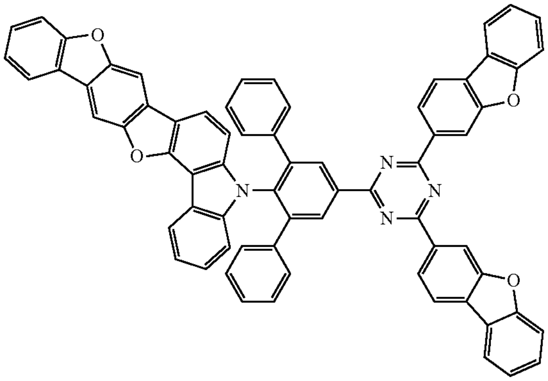
364
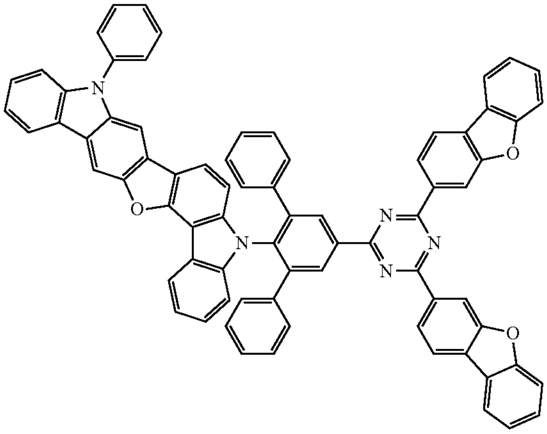
365
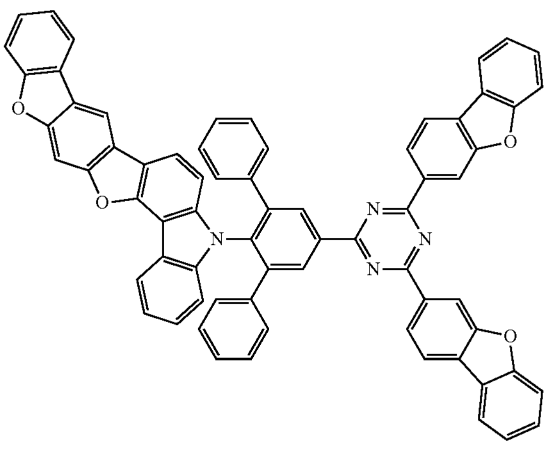
366
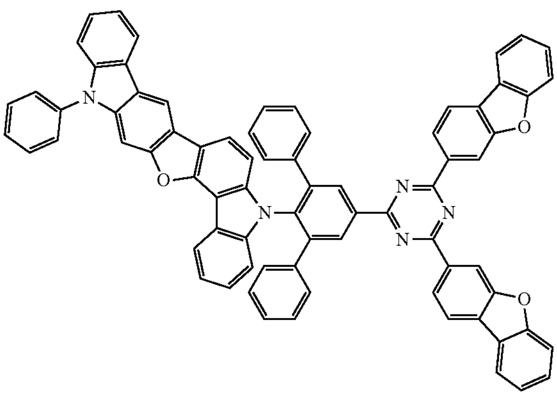

-continued
367
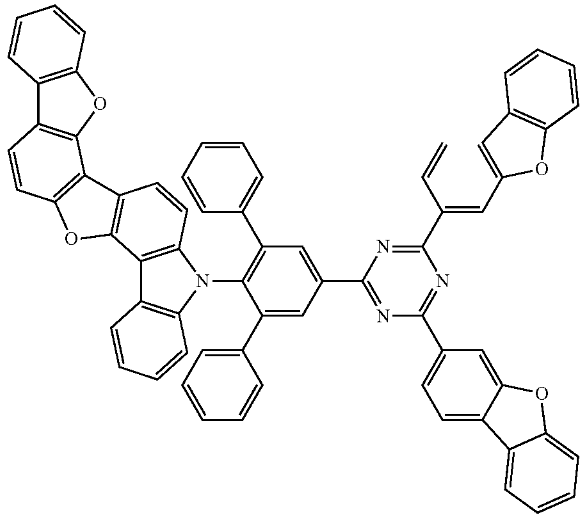
368
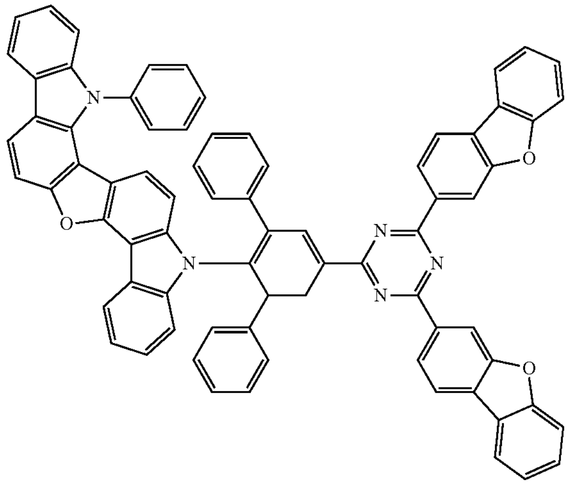
369
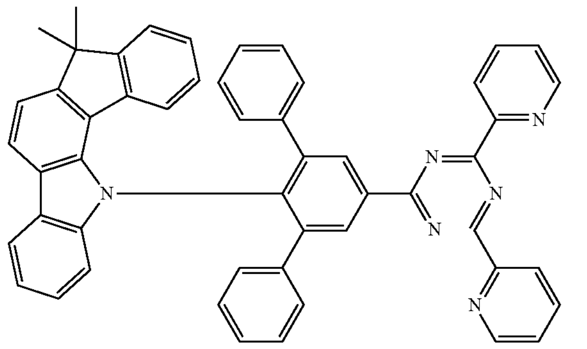
370
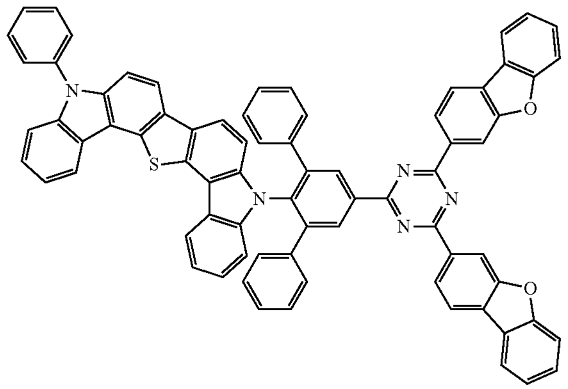
371
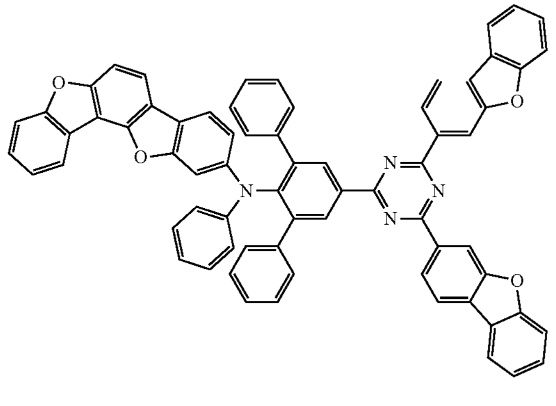
372
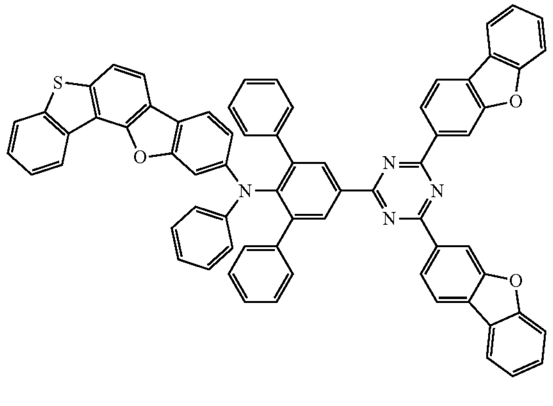

-continued
373
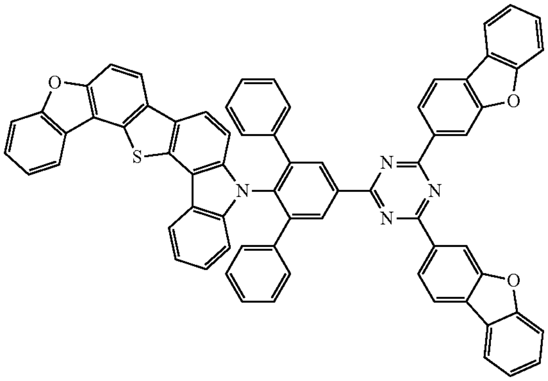
374
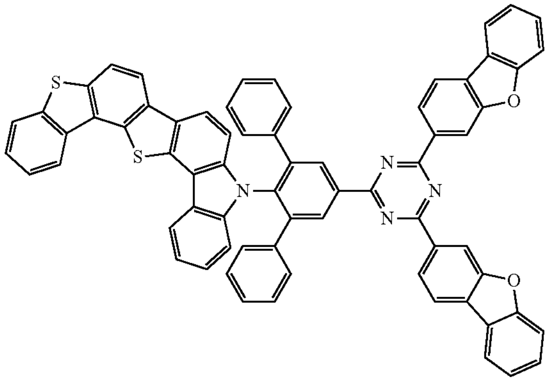
375
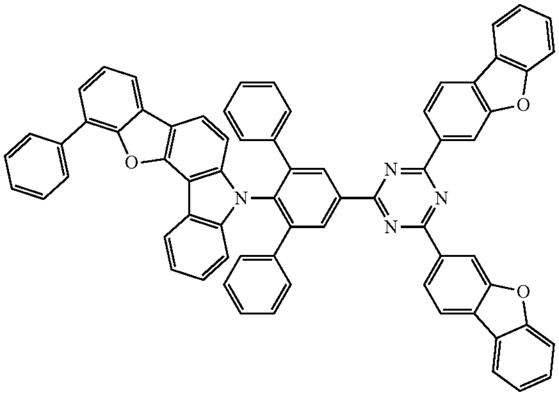
376
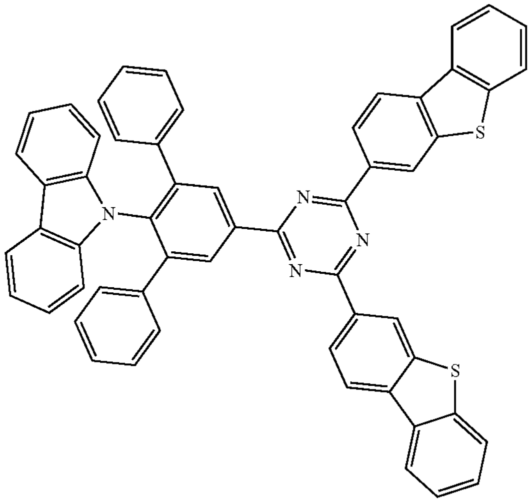
377
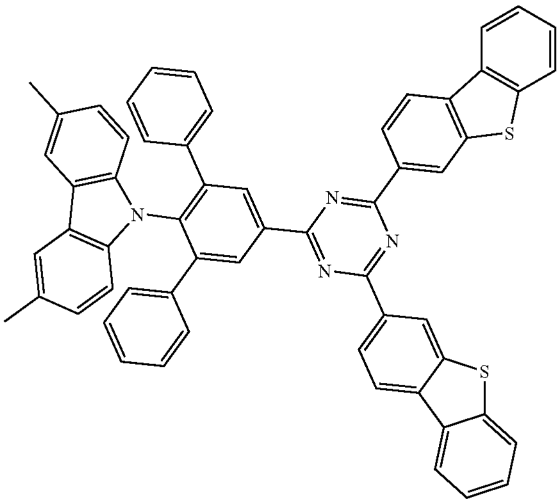
378
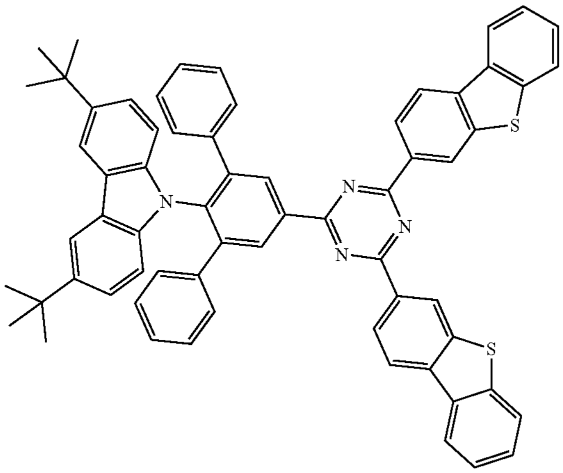

-continued
379
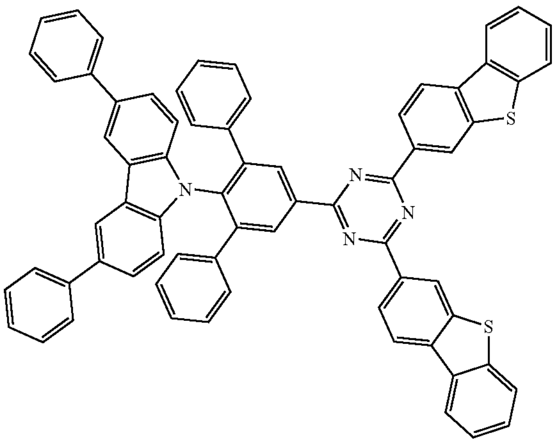
380
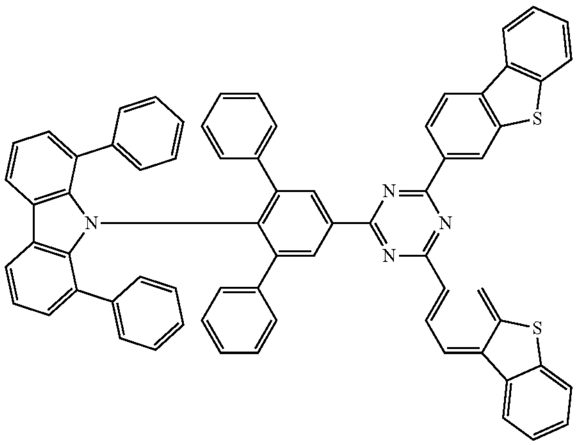
381
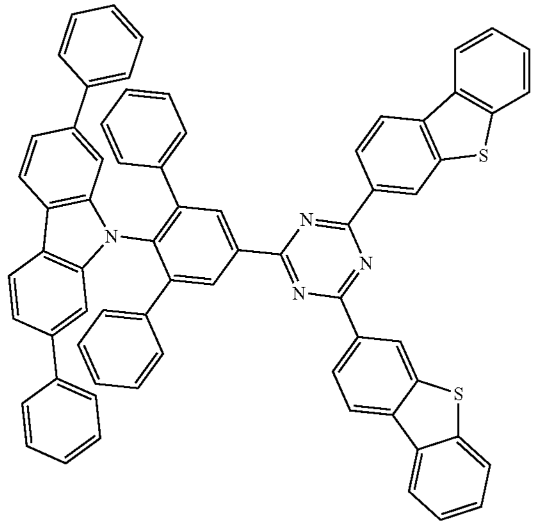
382
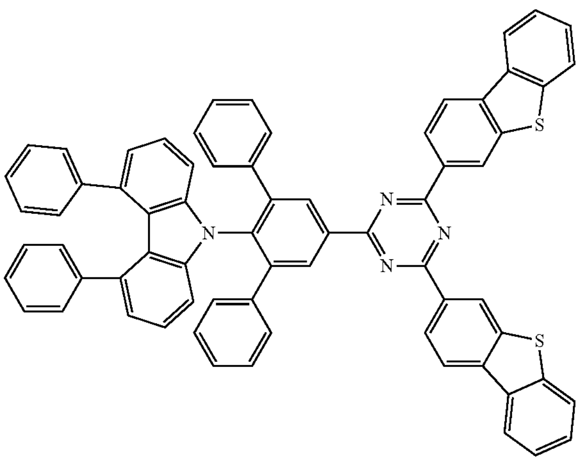
383
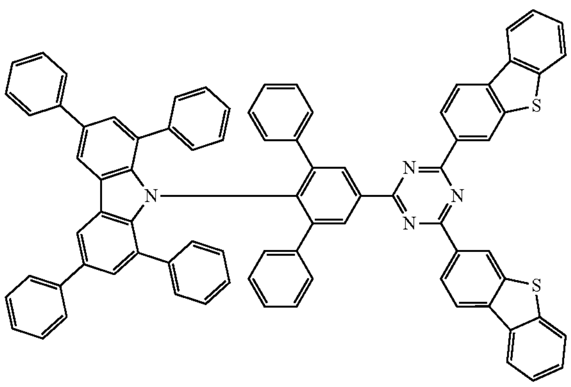

-continued
384
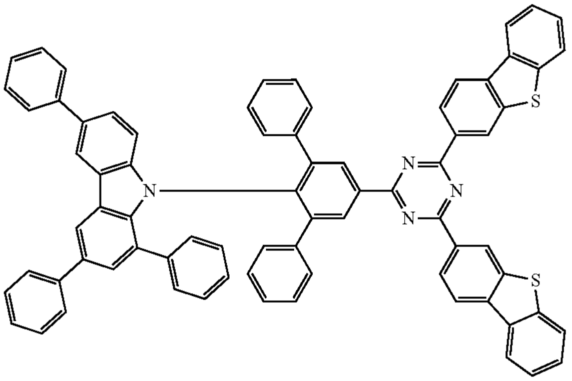
385
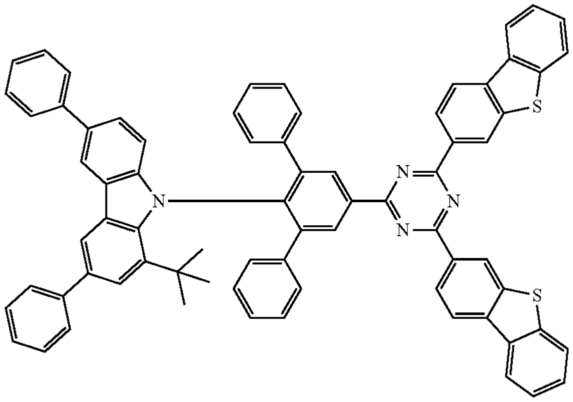
386
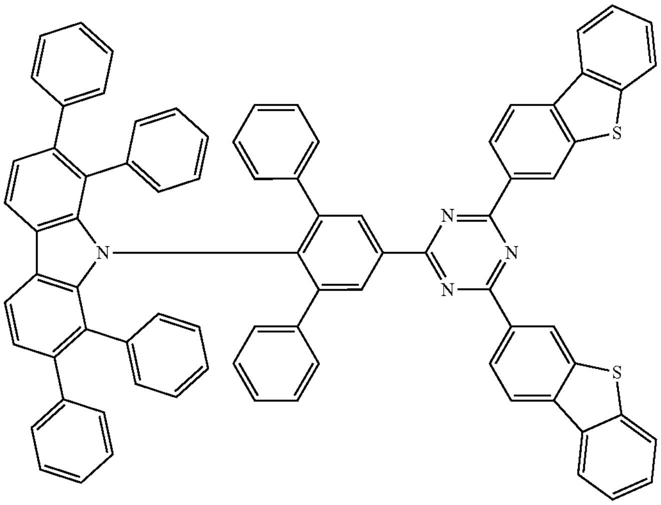
387
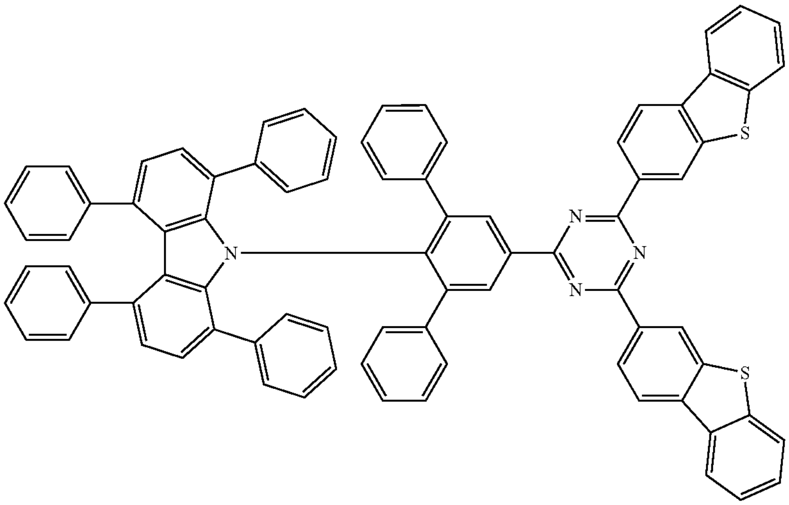

-continued
388
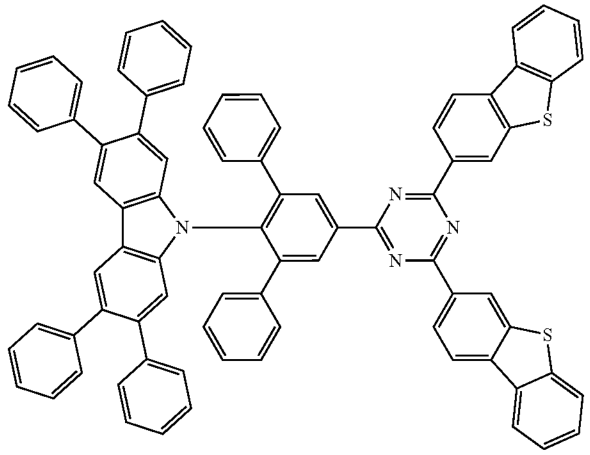
389
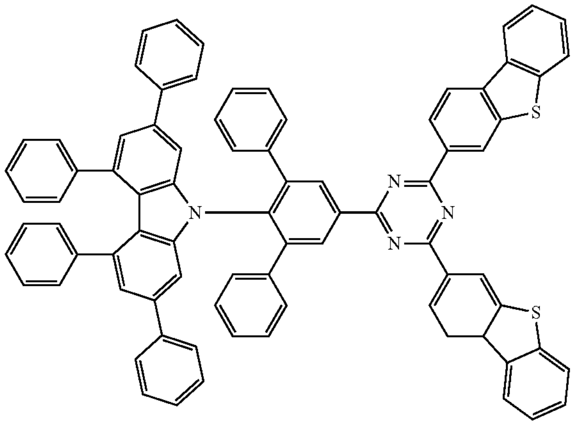
390
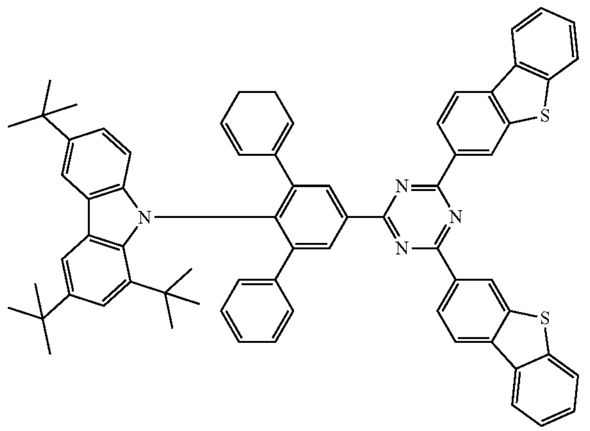
391
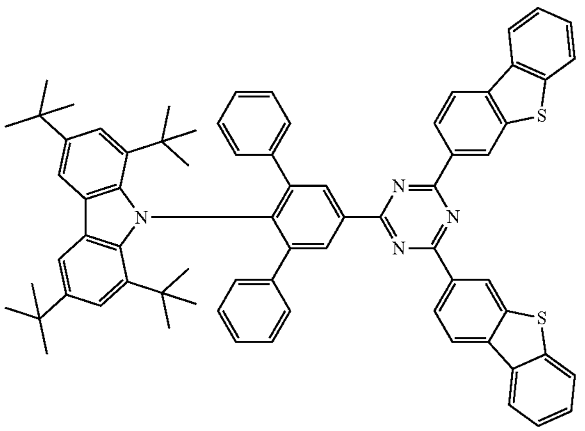
392
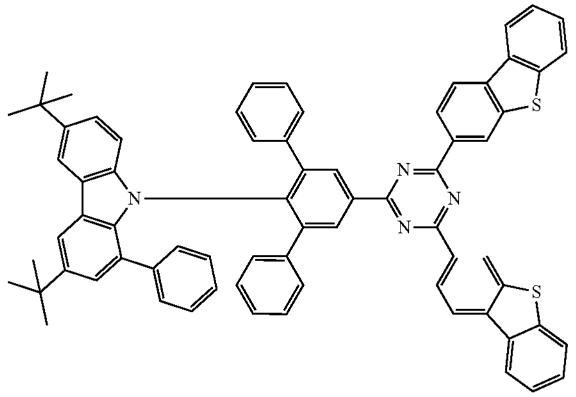
393
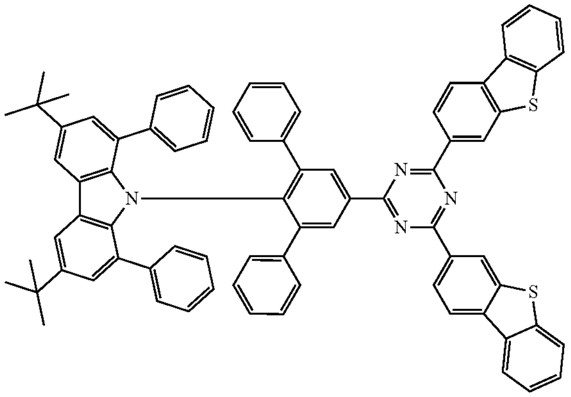

-continued
394
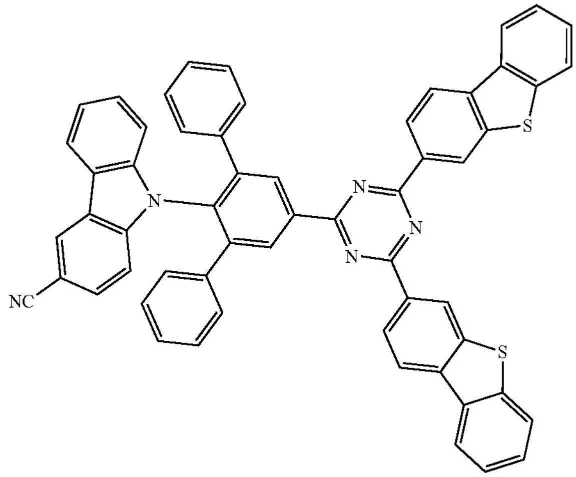
395
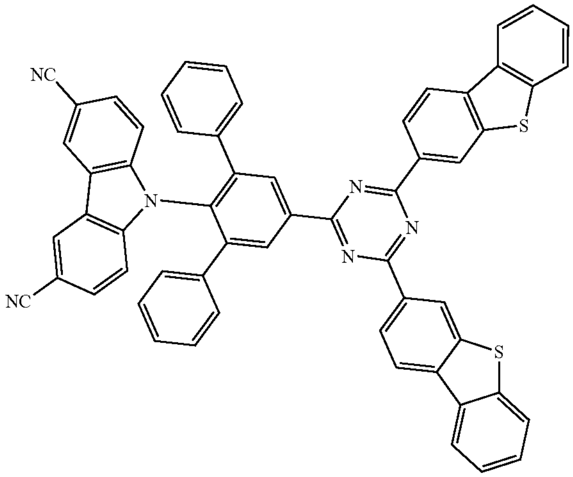
396
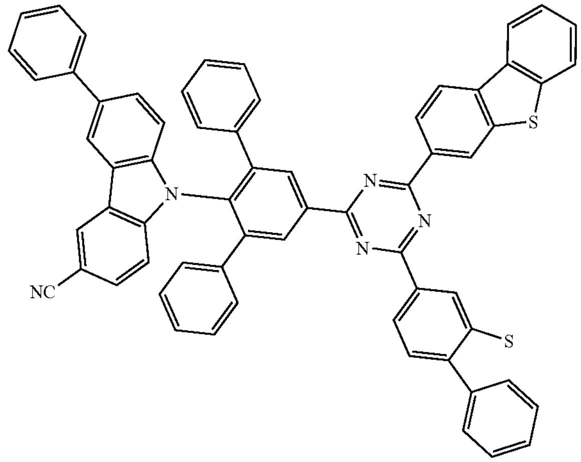
397
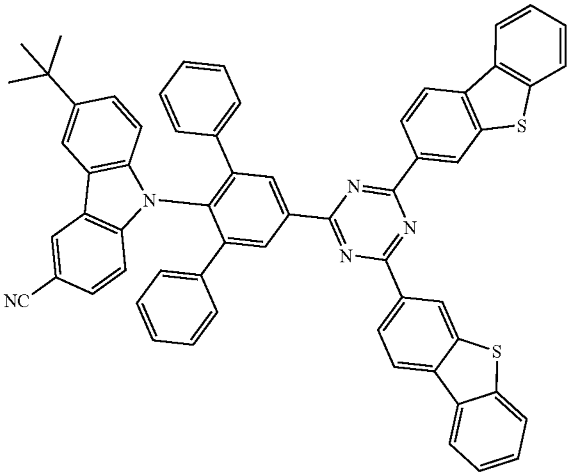
398
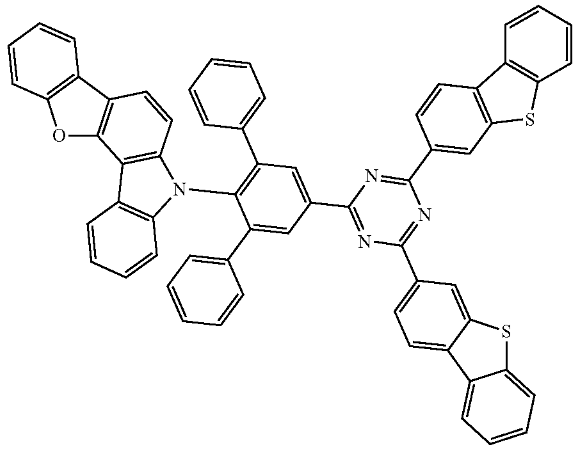
399
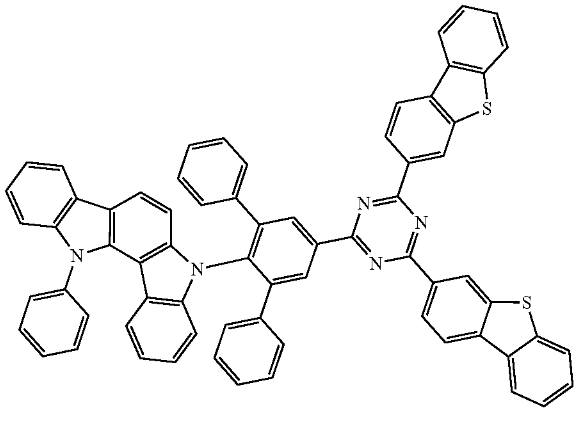

-continued
400
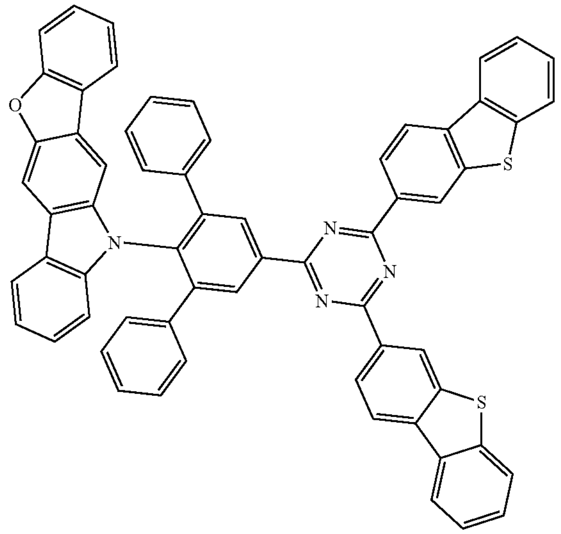
401
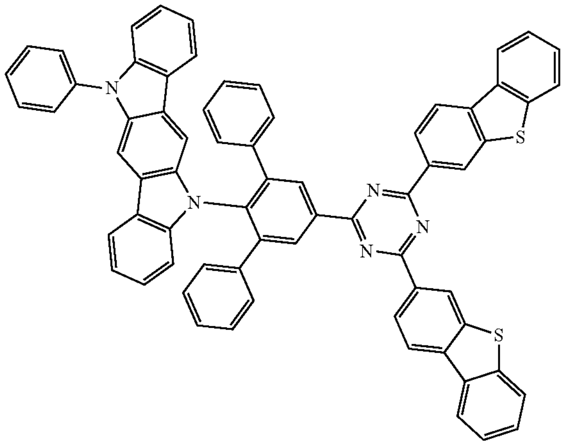
402
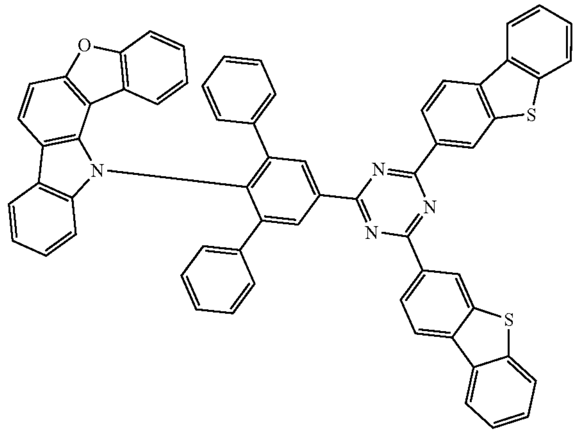
403
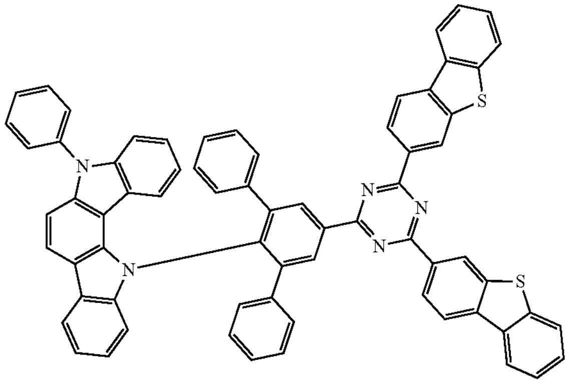
404
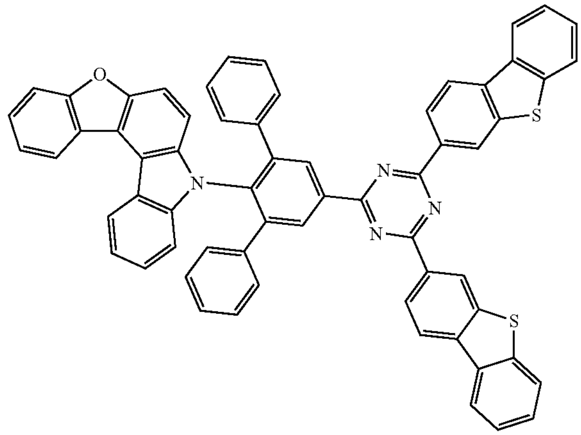
405
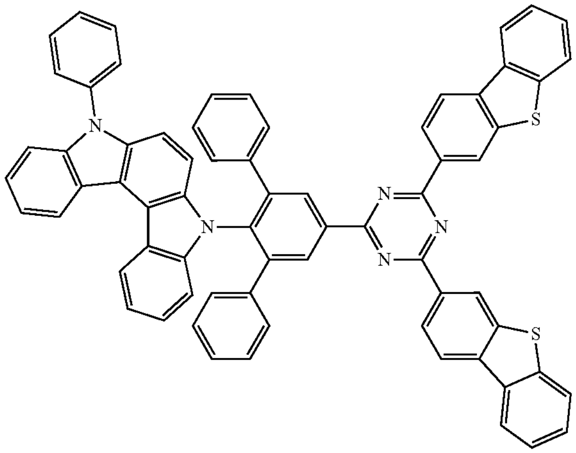

-continued
406
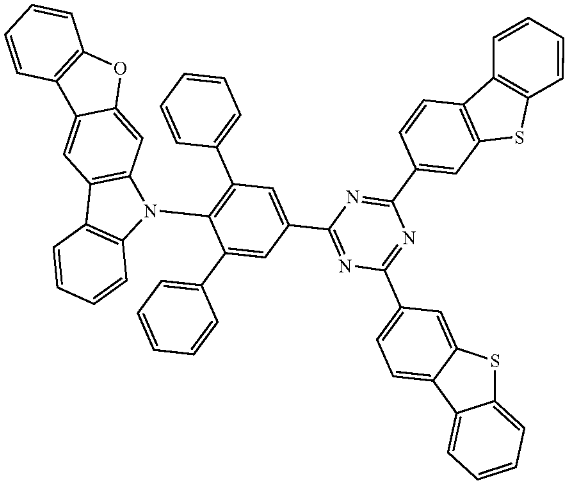
407
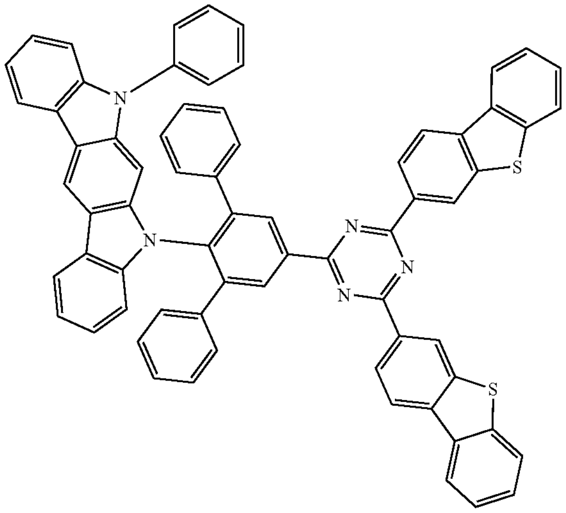
408
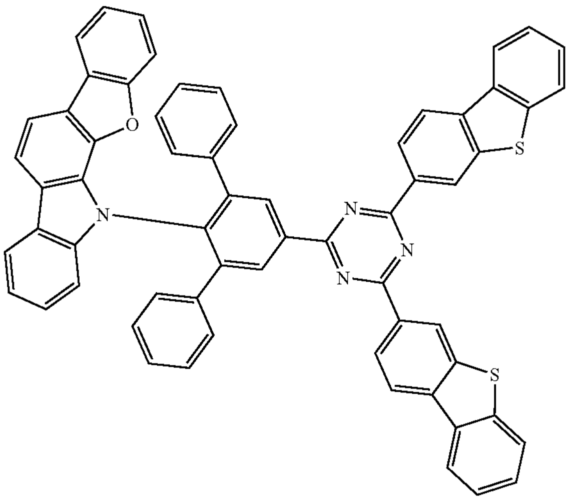
409
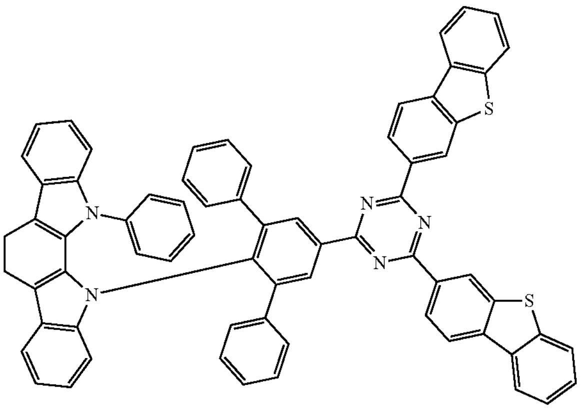
410
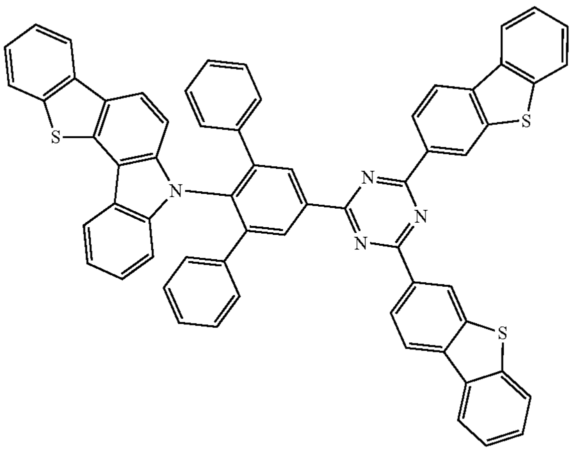
411
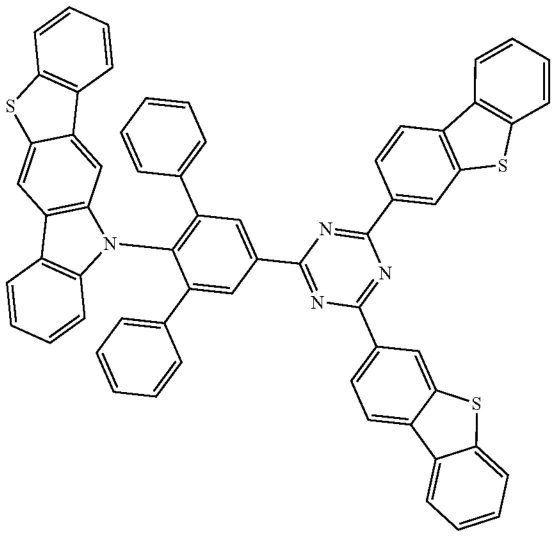

-continued
412
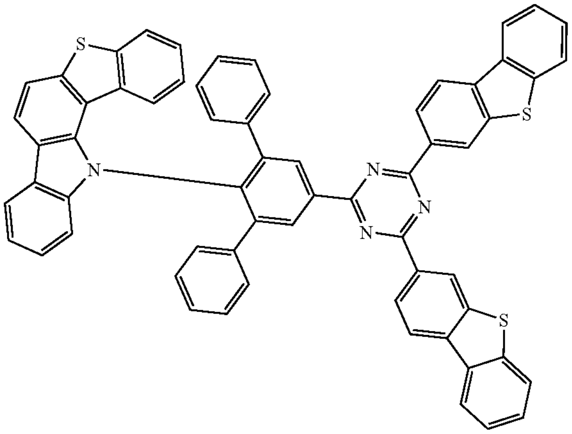
413
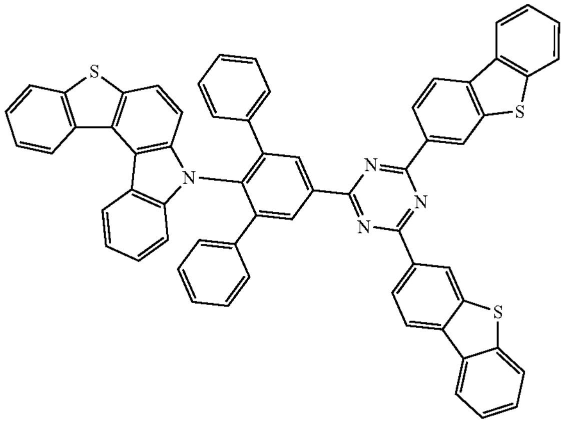
414
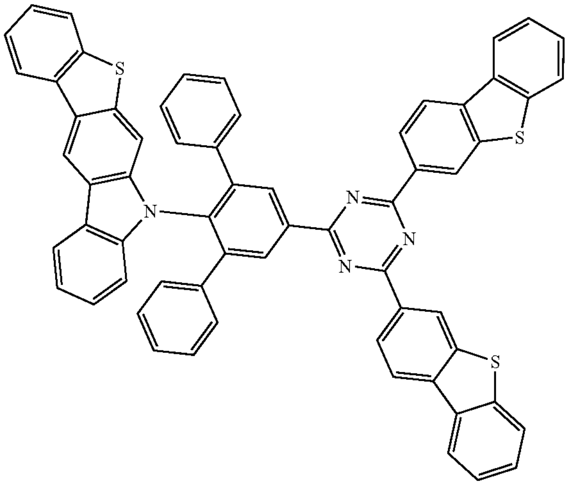
415
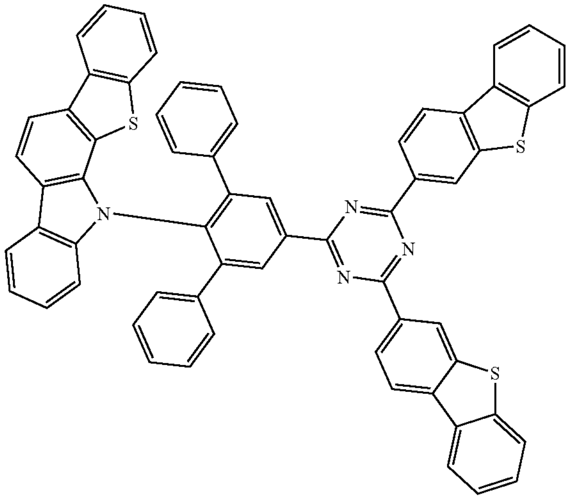
416
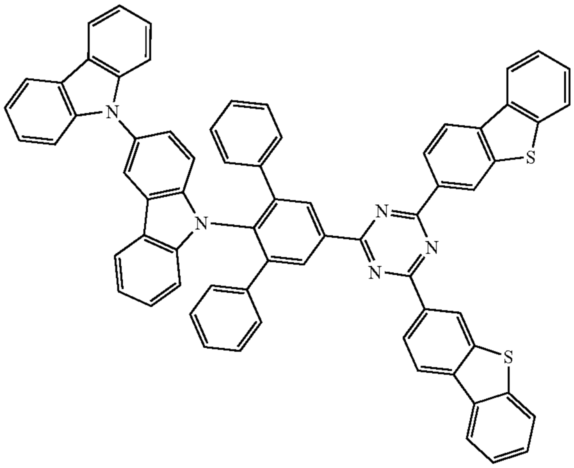
417
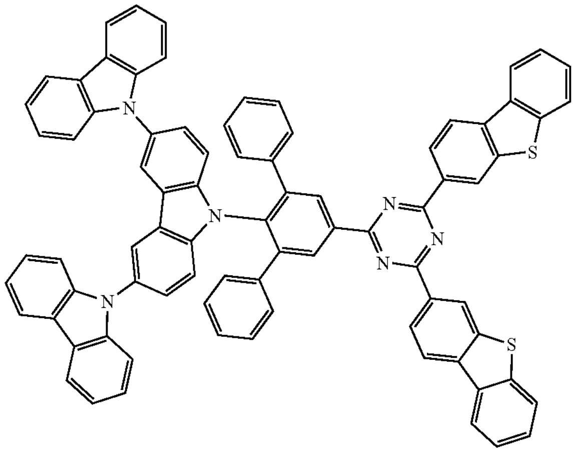

-continued
418
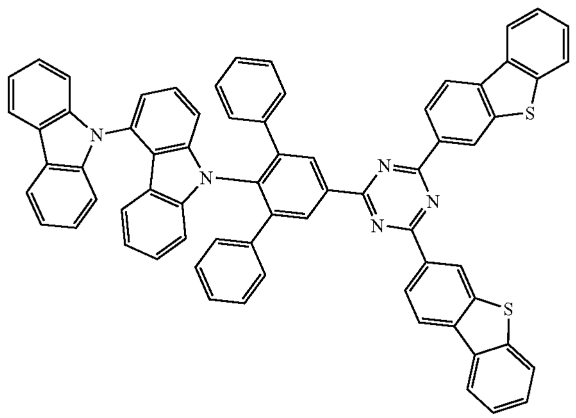
419
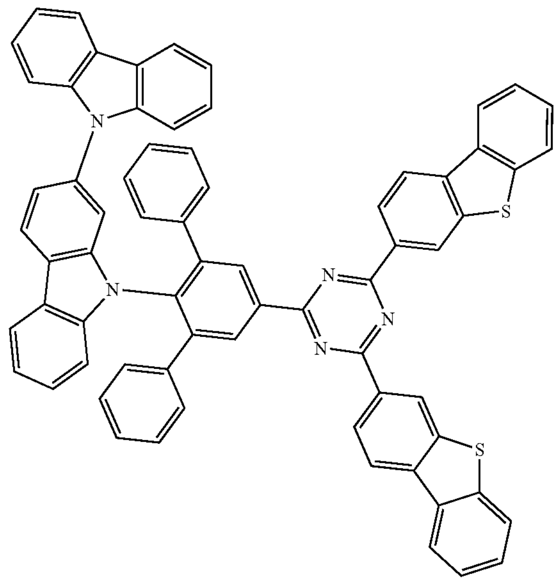
420
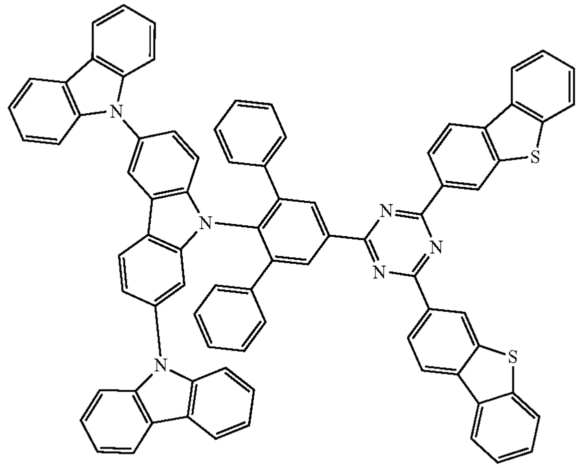
421
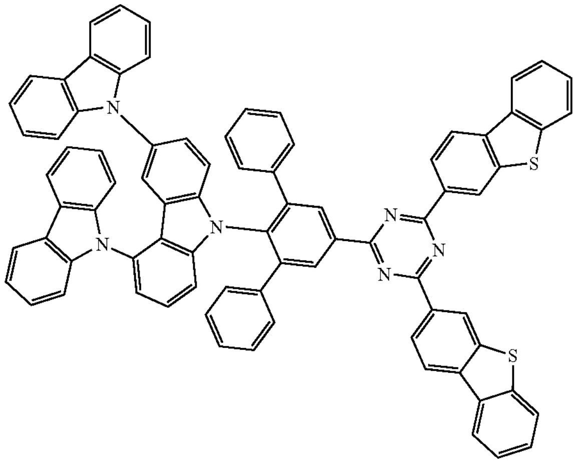
422
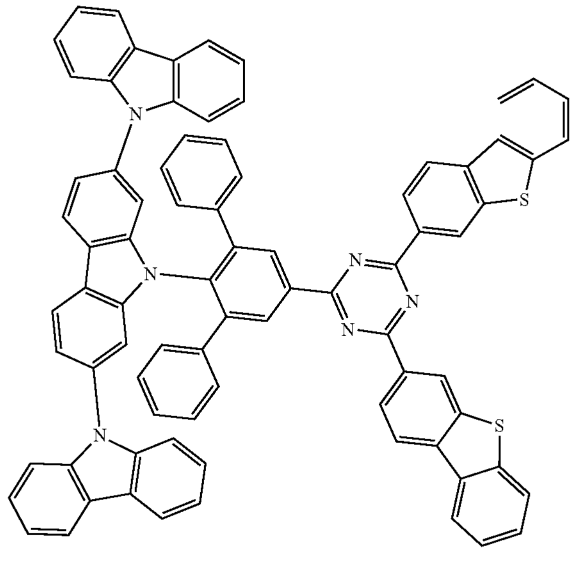
423
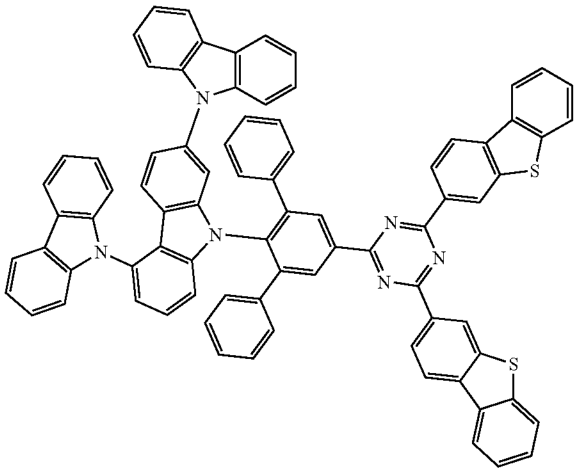

-continued
424
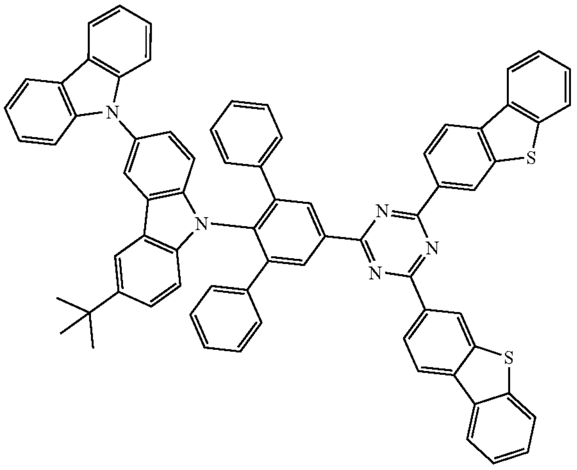
425
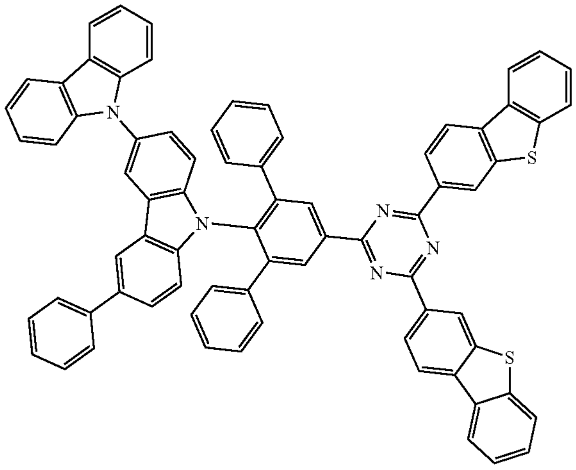
426
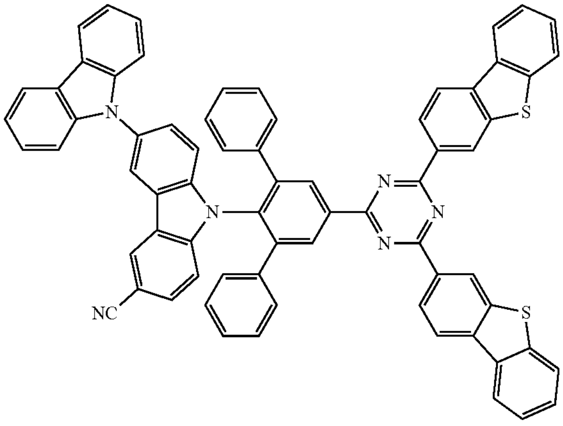
427
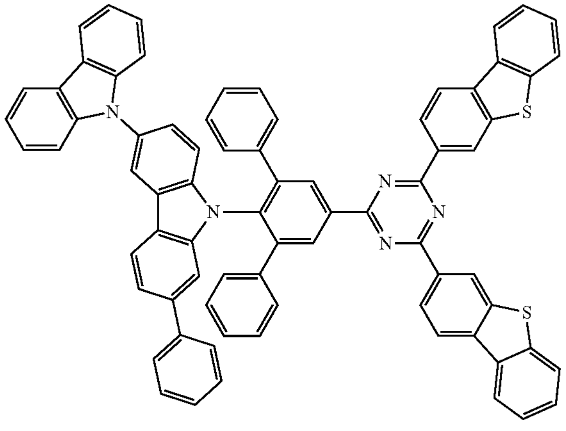
428
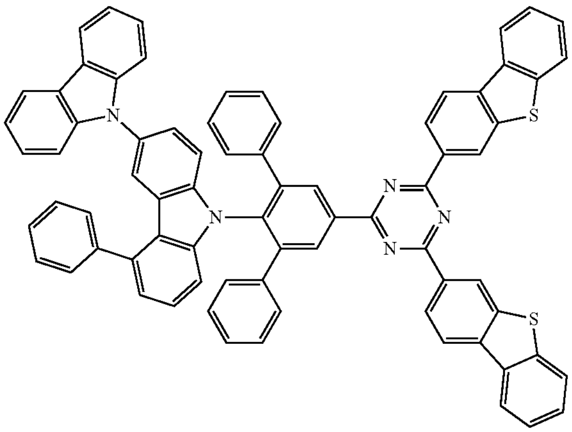
429
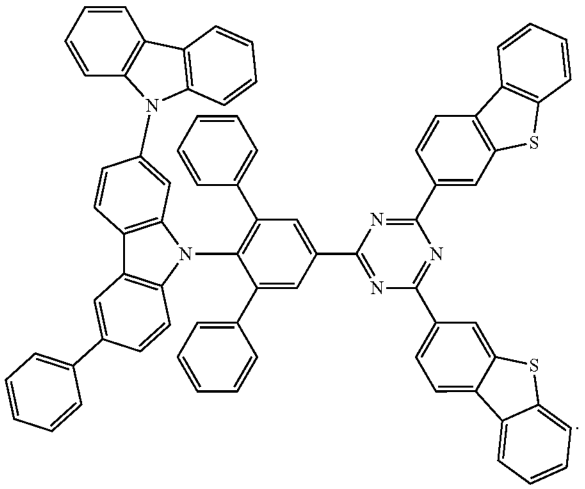

430
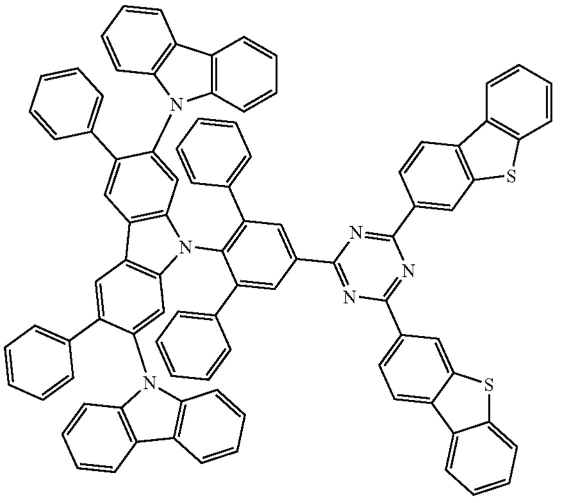
431
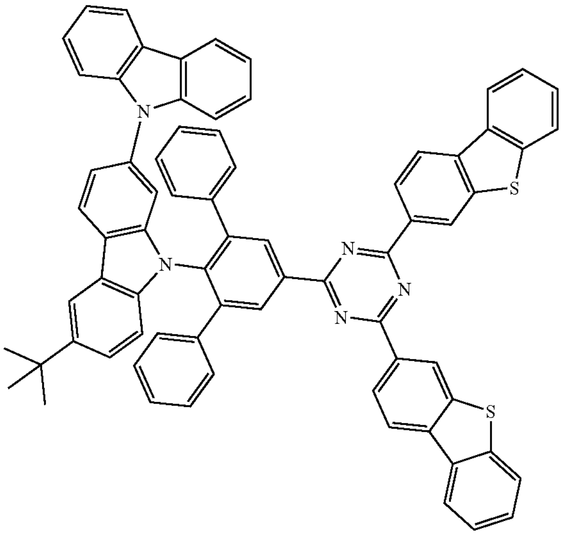
432
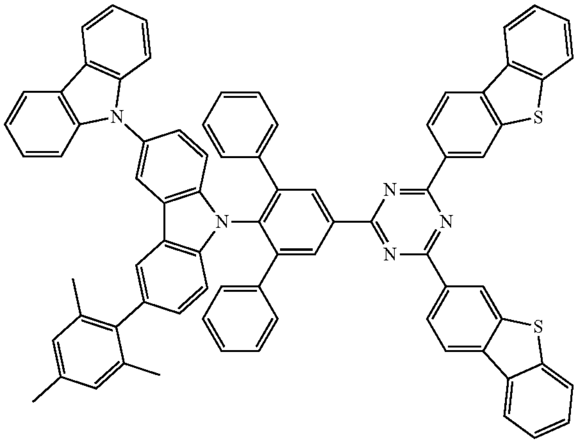
433
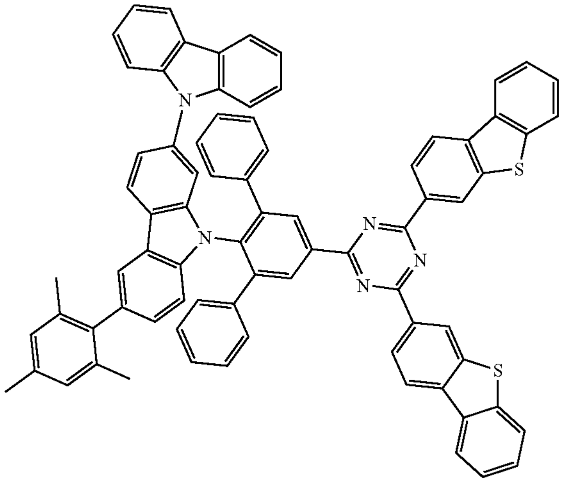
434
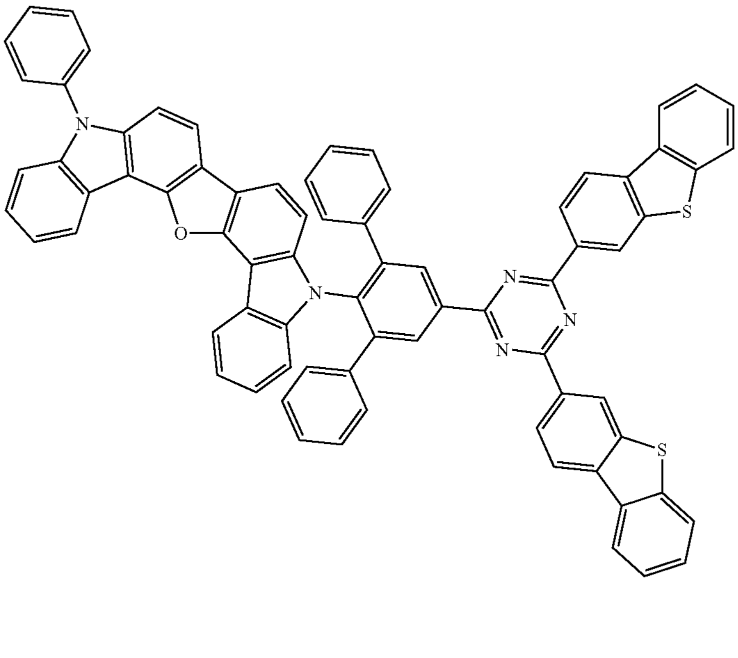

-continued
435
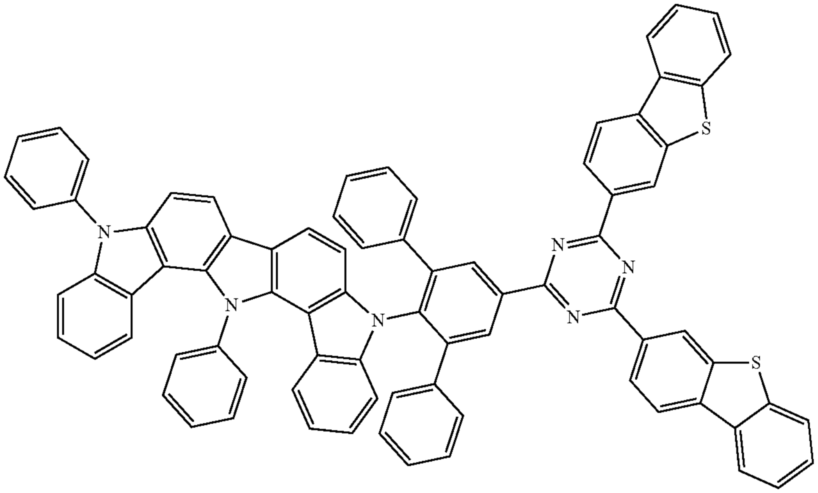
436
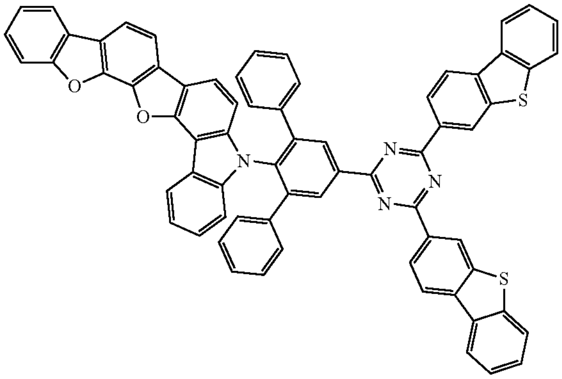
437
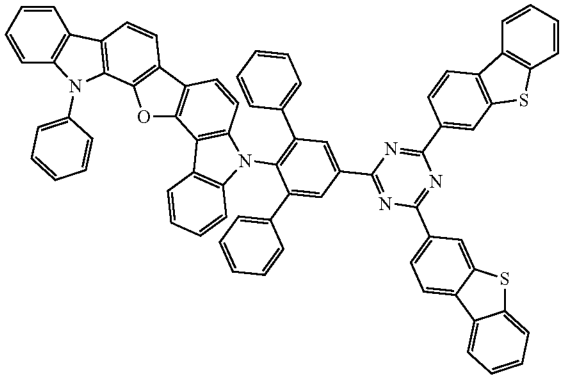
438
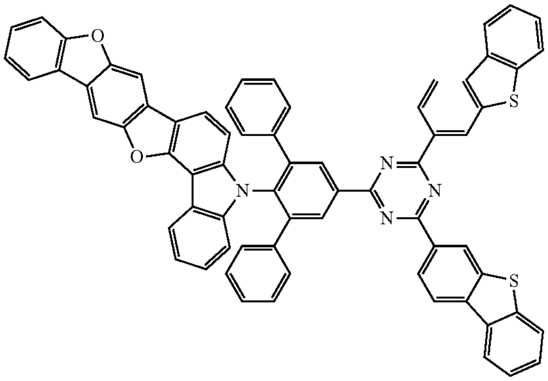
439
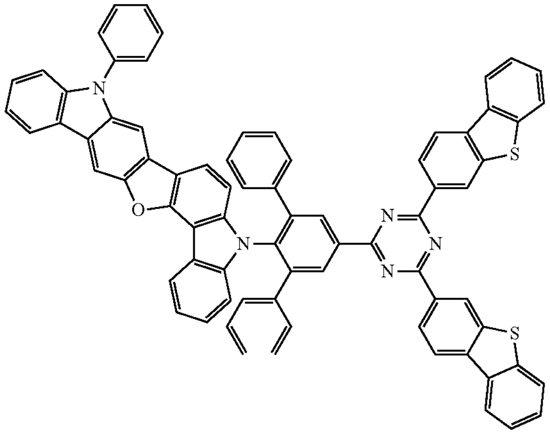

-continued
440
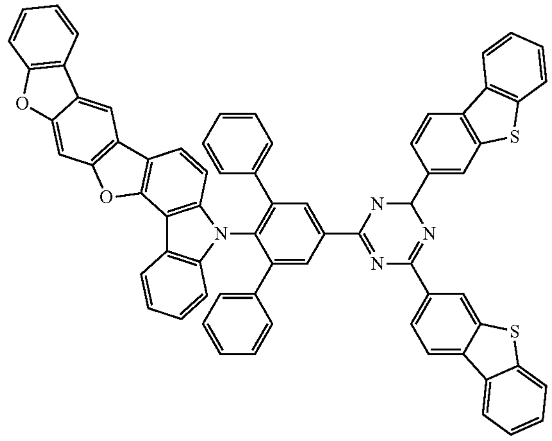
441
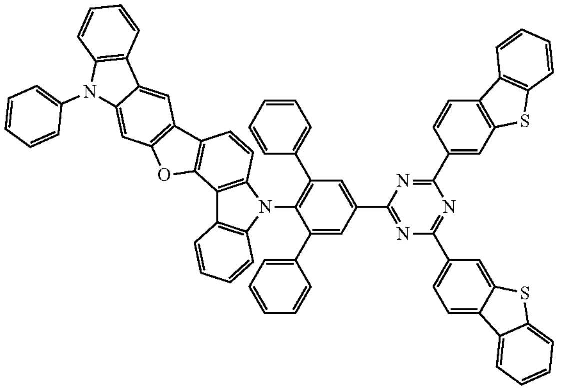
442
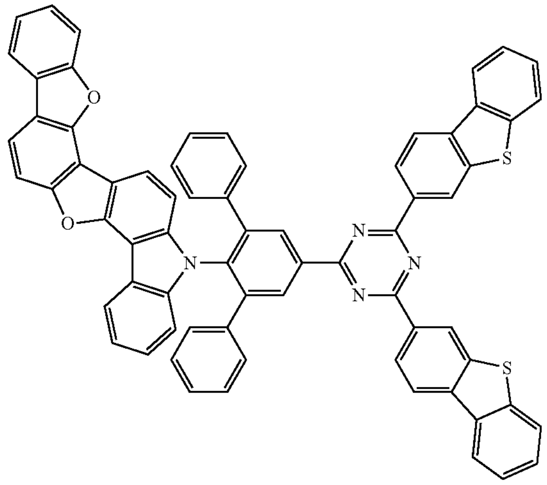
443
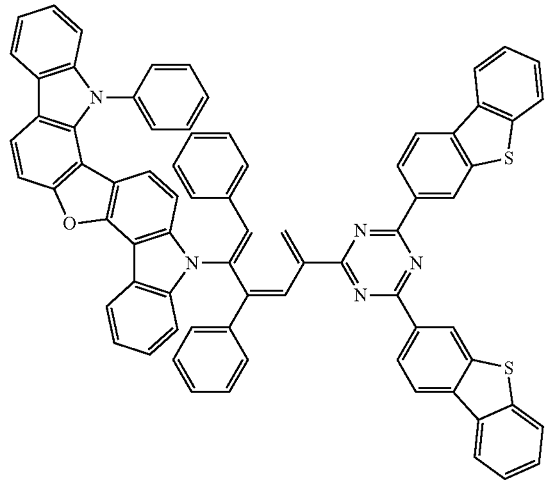
444
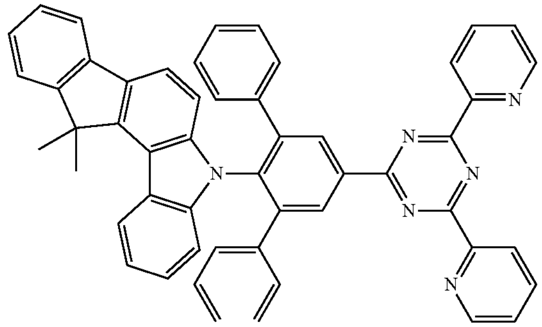
445
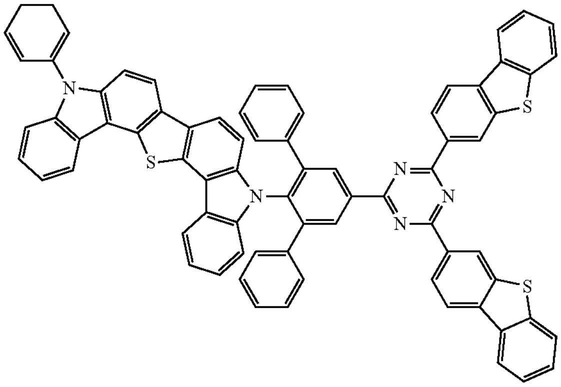

-continued
446
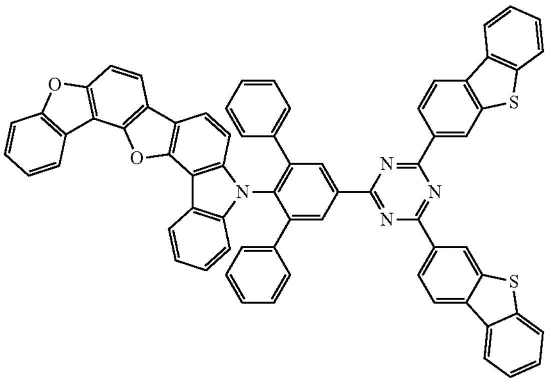
447
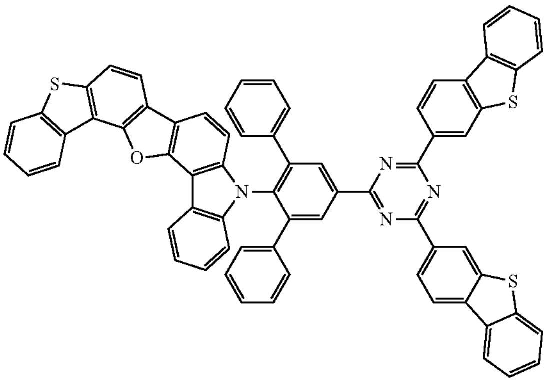
448
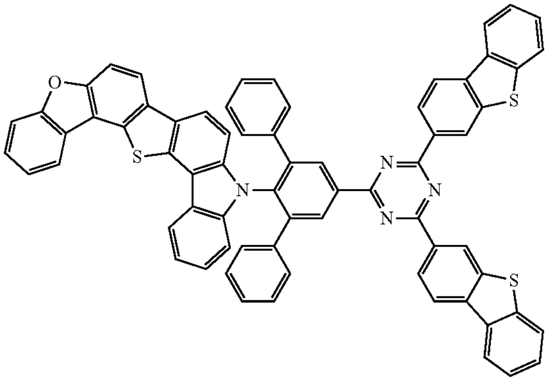
449
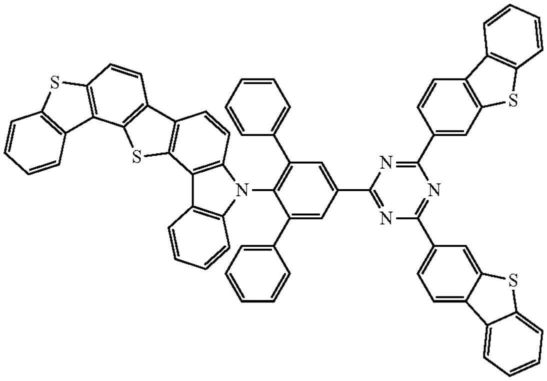
450
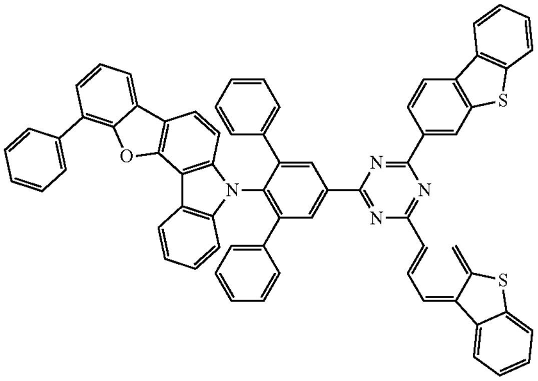
451
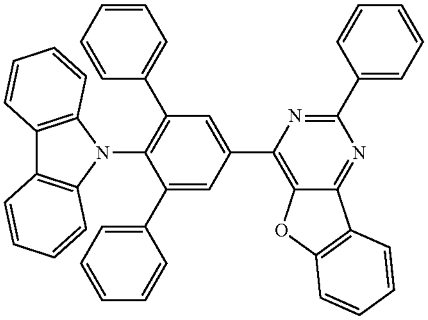
452
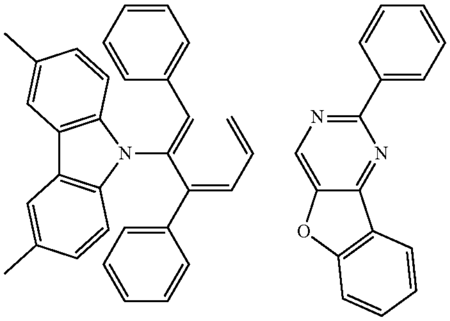
453
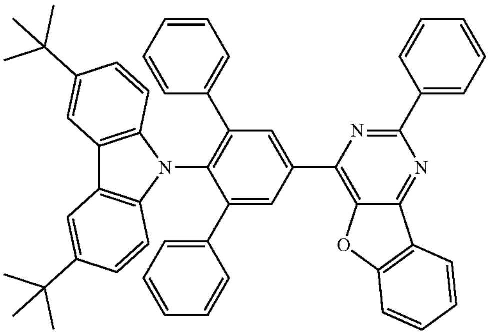

-continued
454
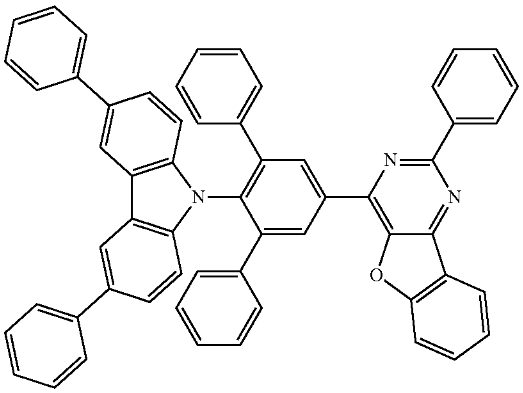
455
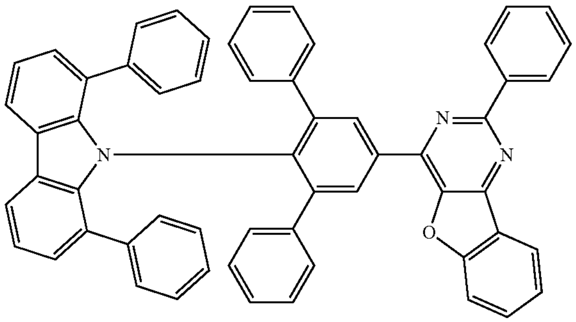
456
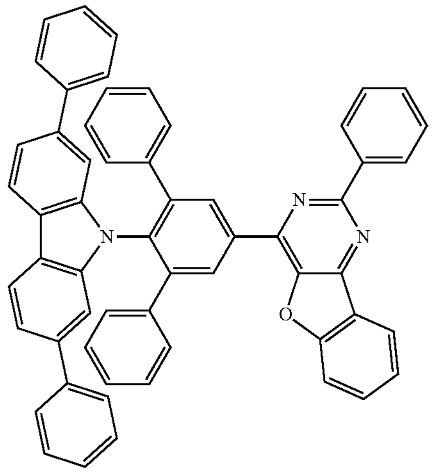
457
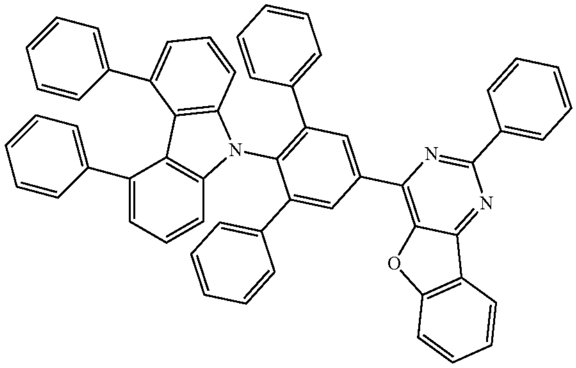
458
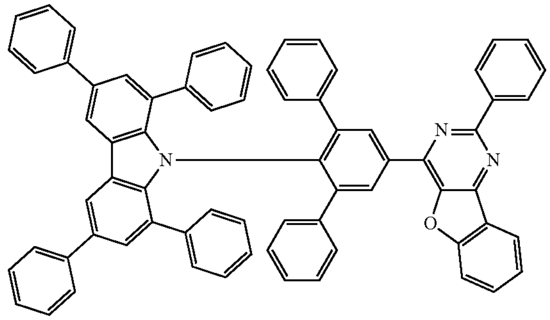
459
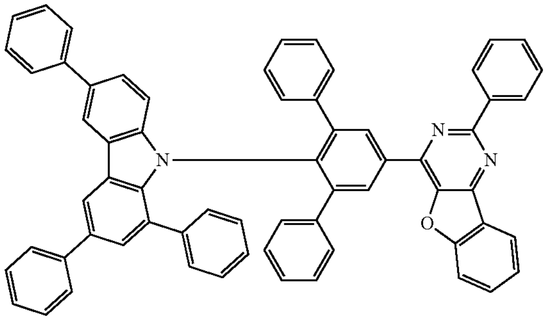
460
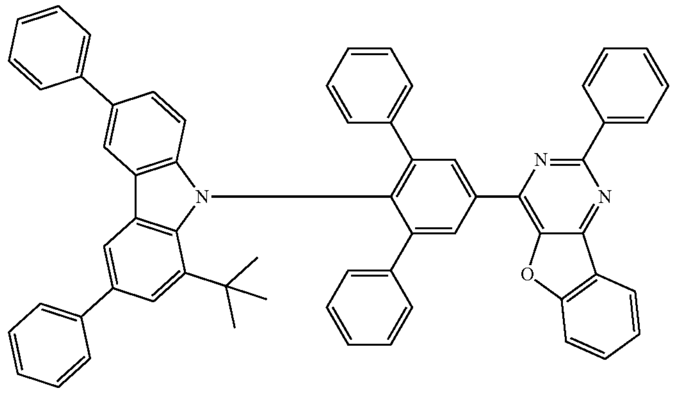

-continued
461
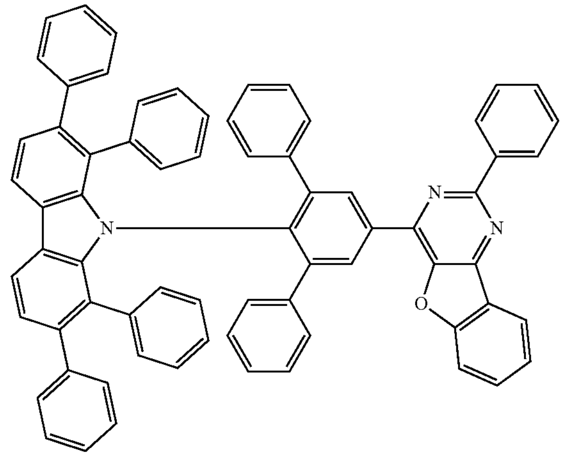
462
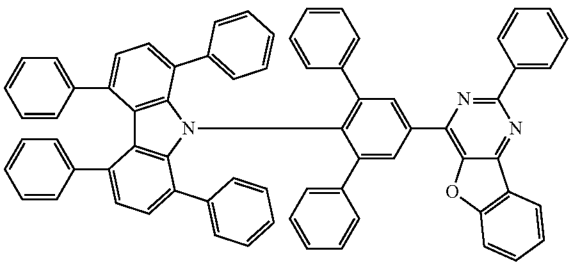
463
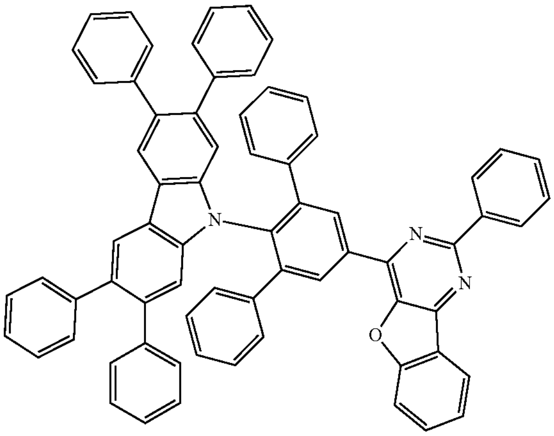
464
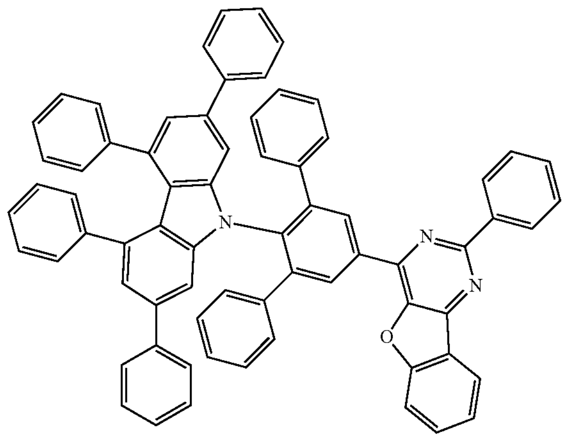
465
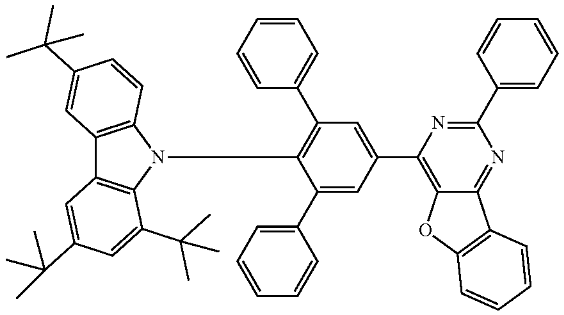
466
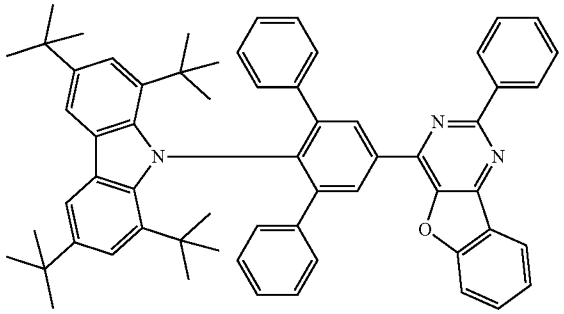
467
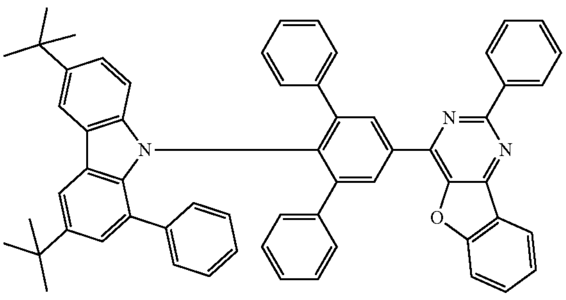

468
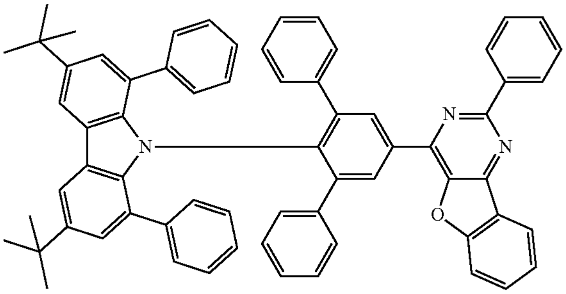
469
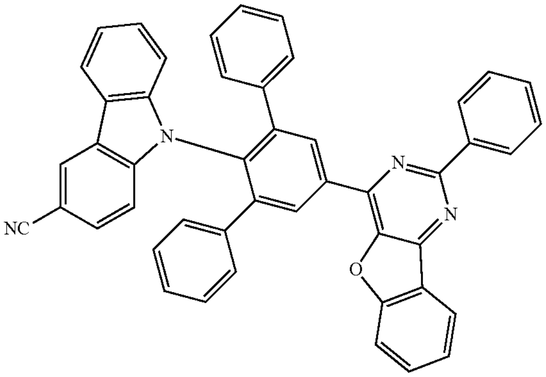
470
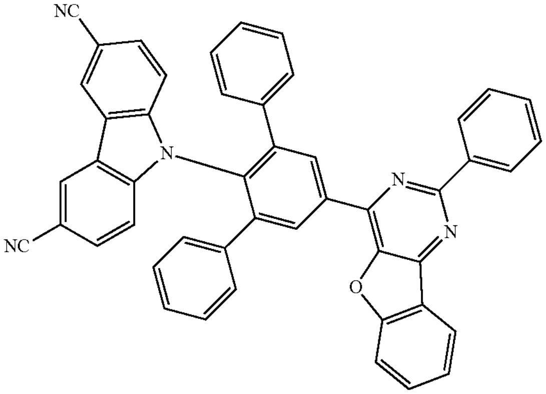
471
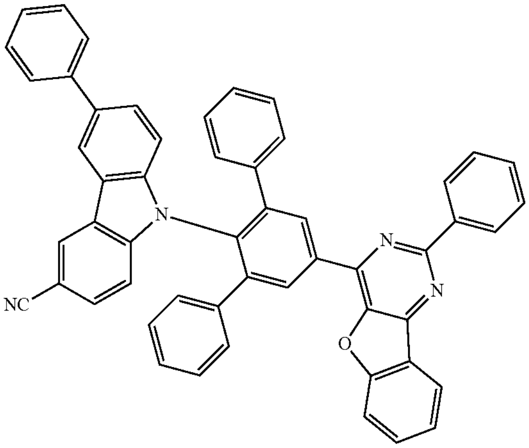
472
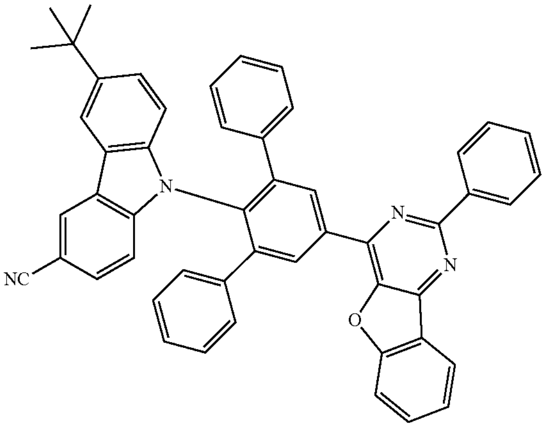
473
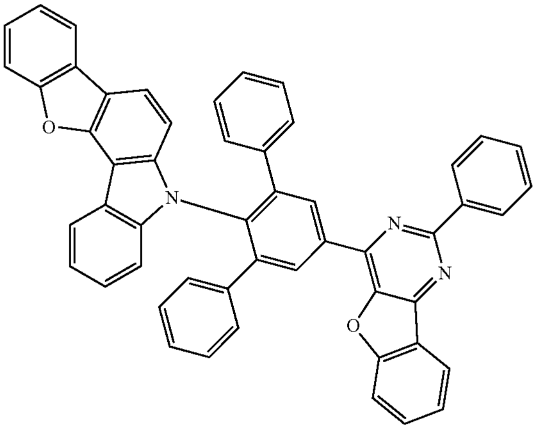
474
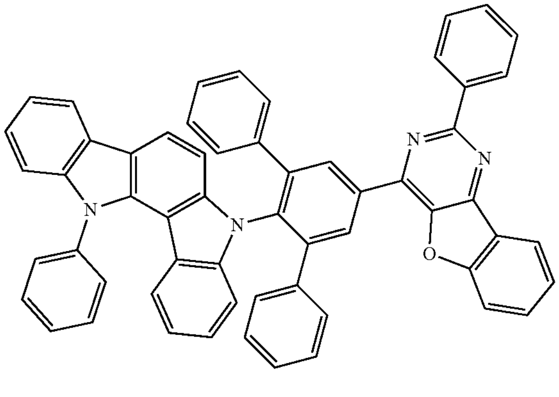

-continued
475
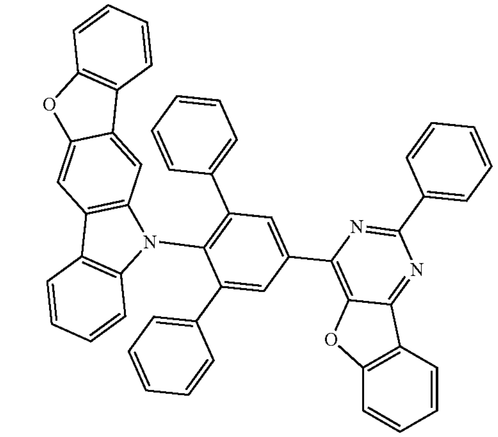
476
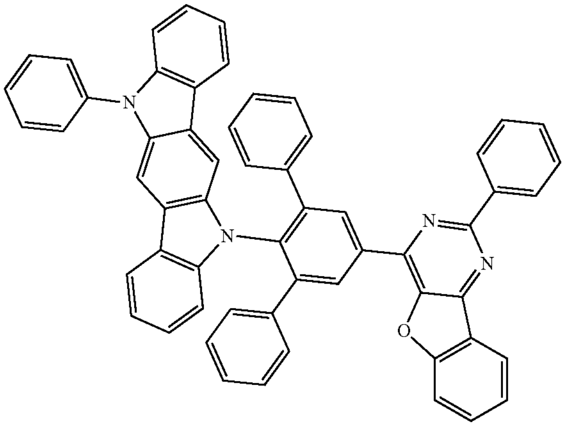
477
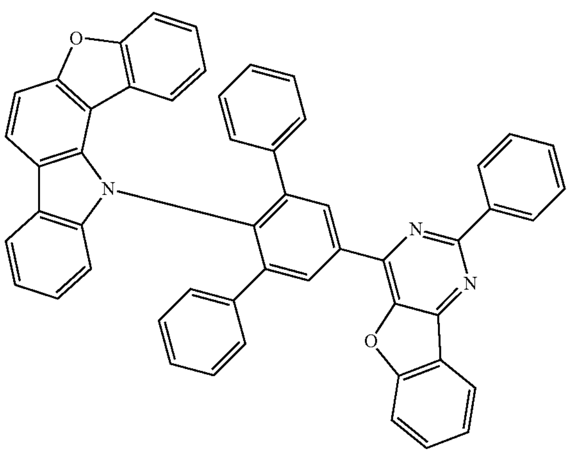
-continued
478
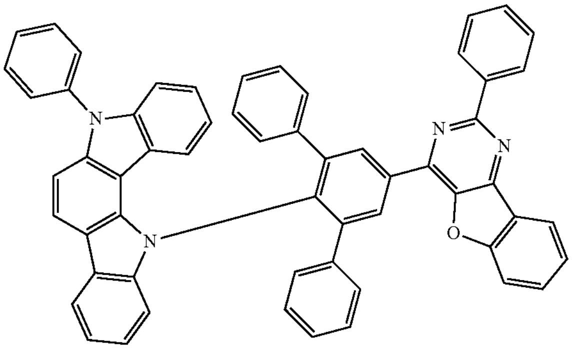
479
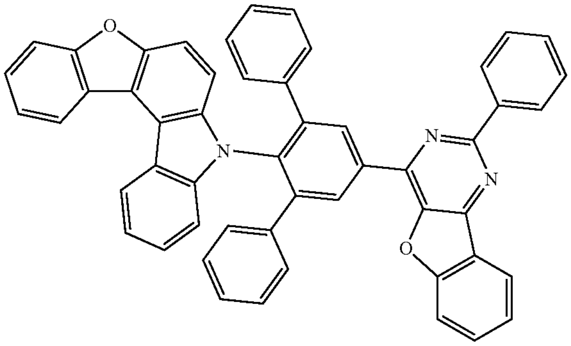
480
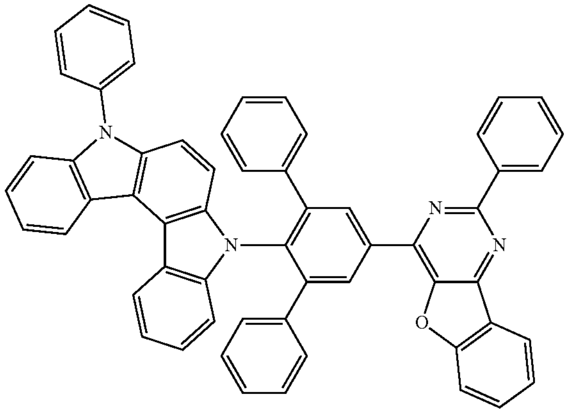
481
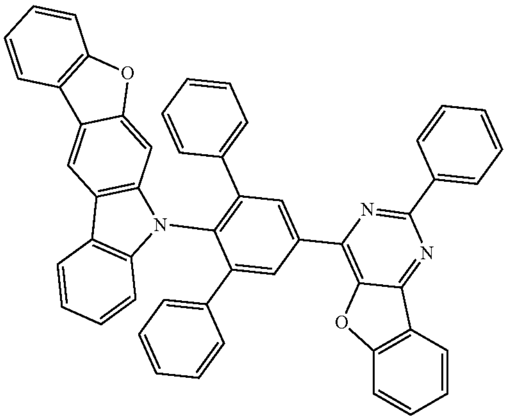

482
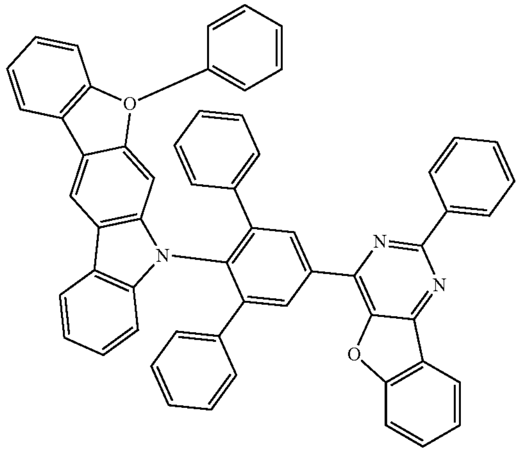
483
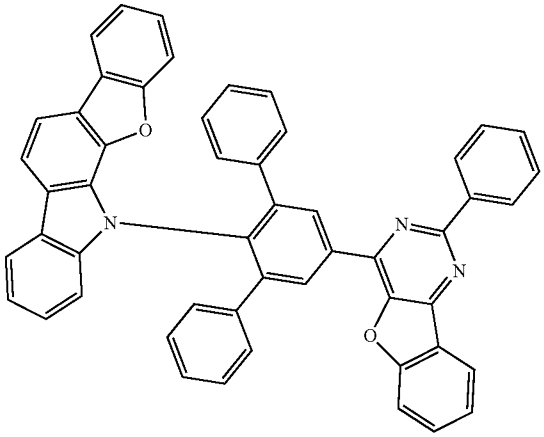
484
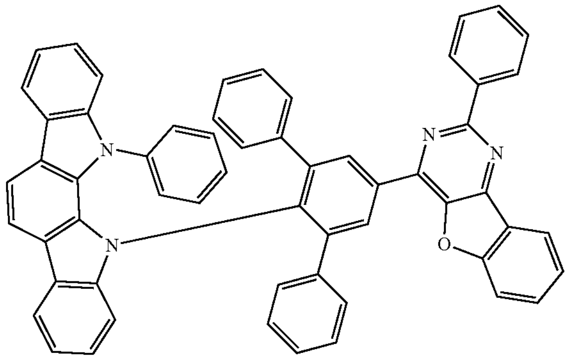
485
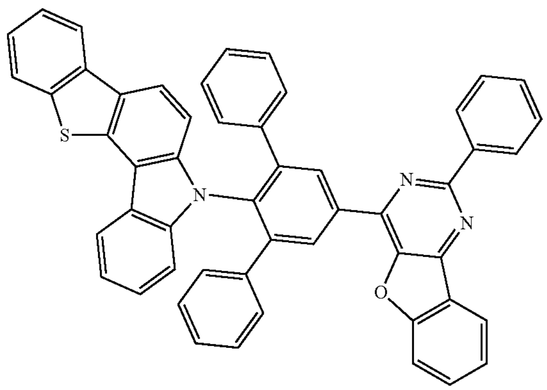
486
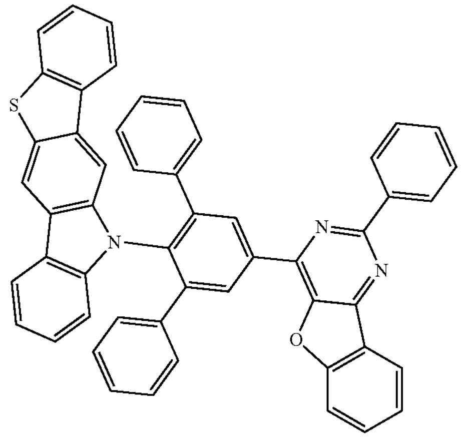
487
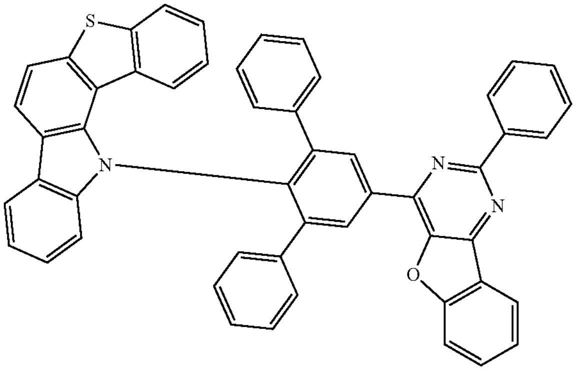
488
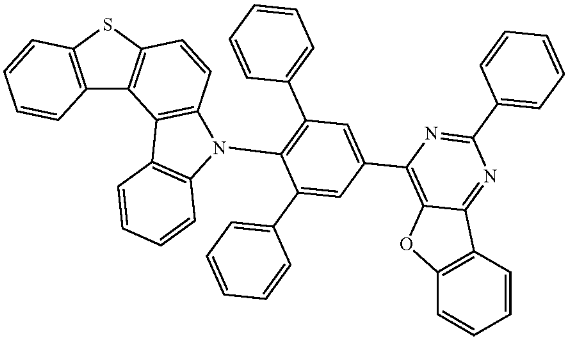

-continued
489
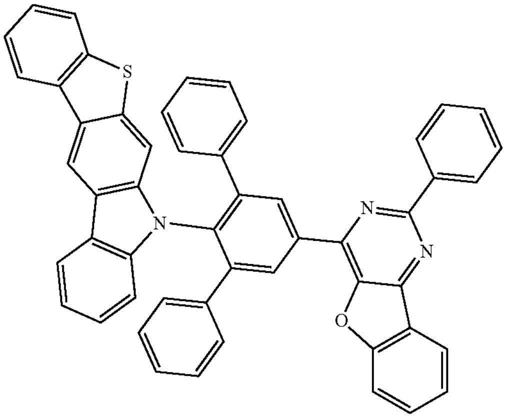
490
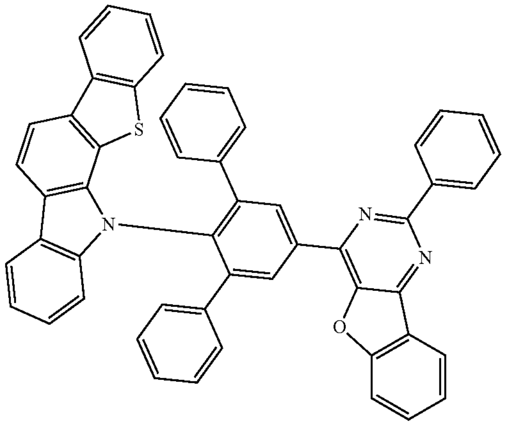
491
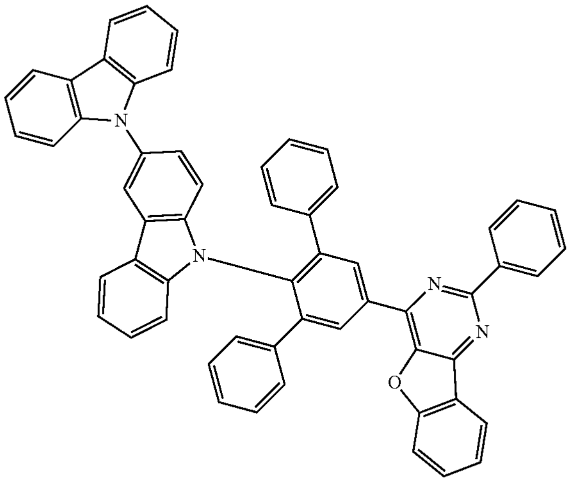
-continued
492
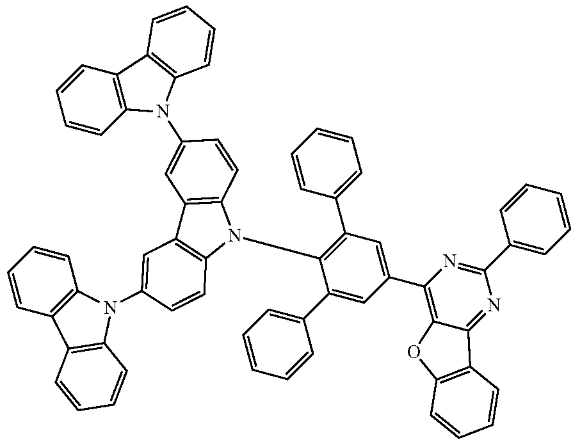
493
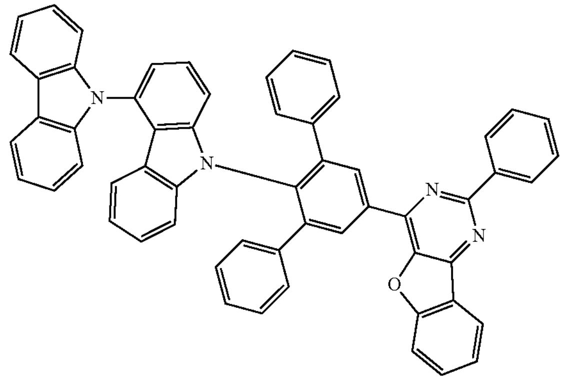
494
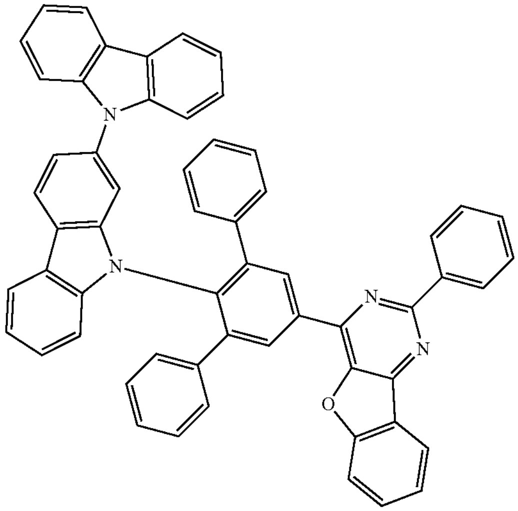

-continued
495
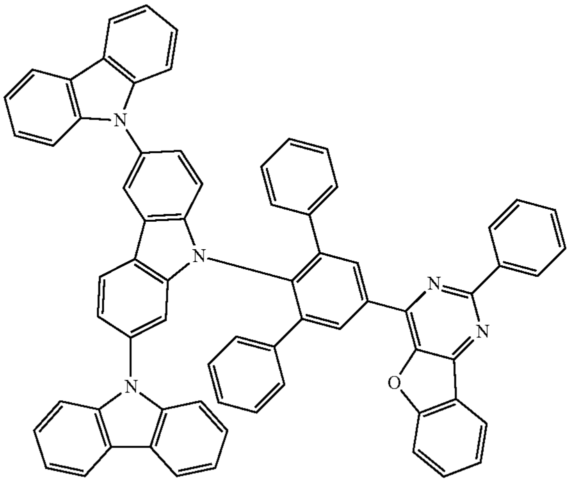
496
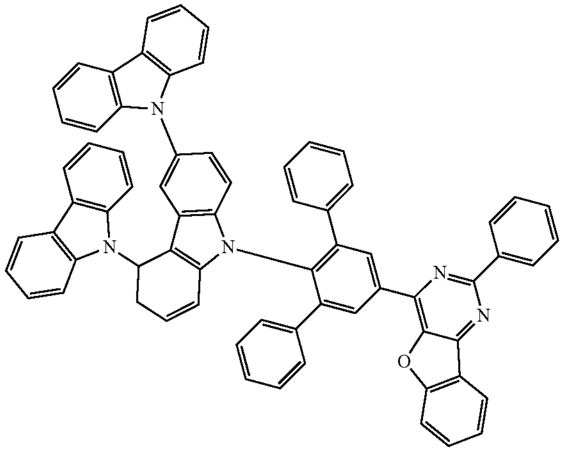
497
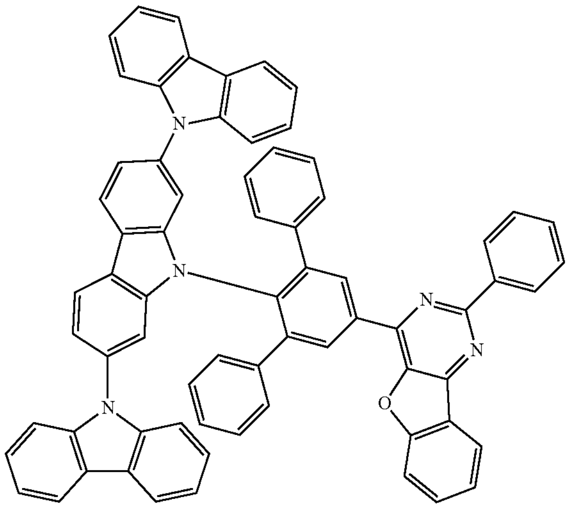
-continued
498
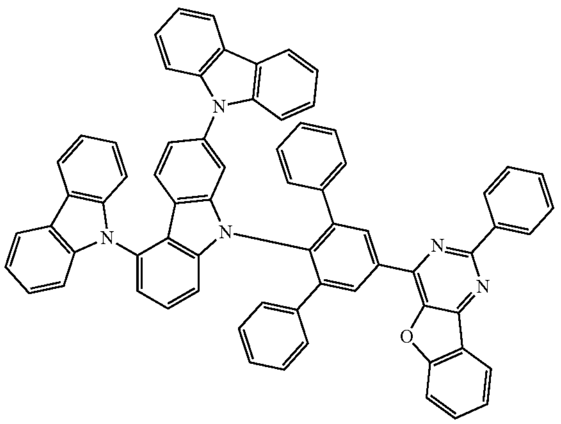
499
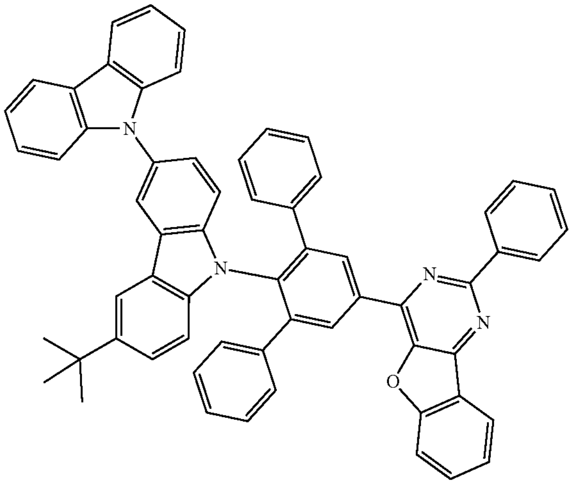
500
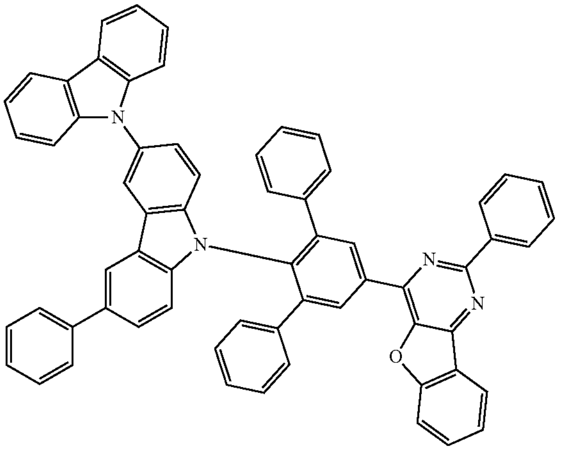

501
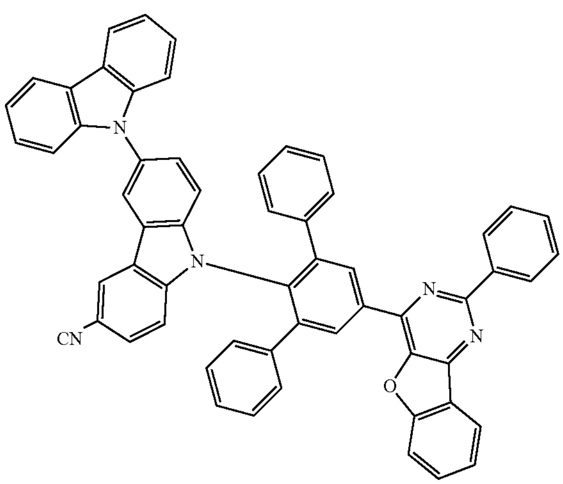
502
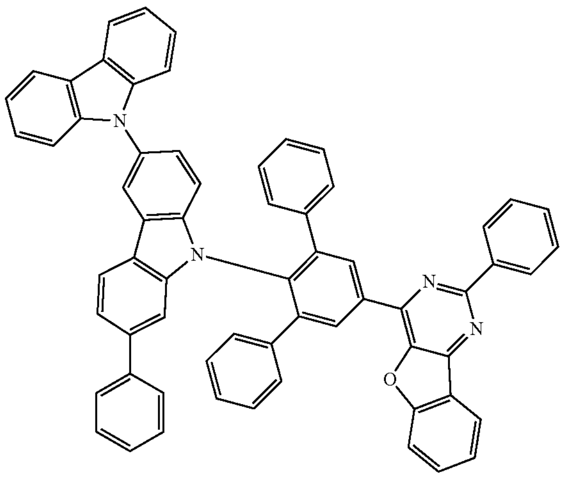
503
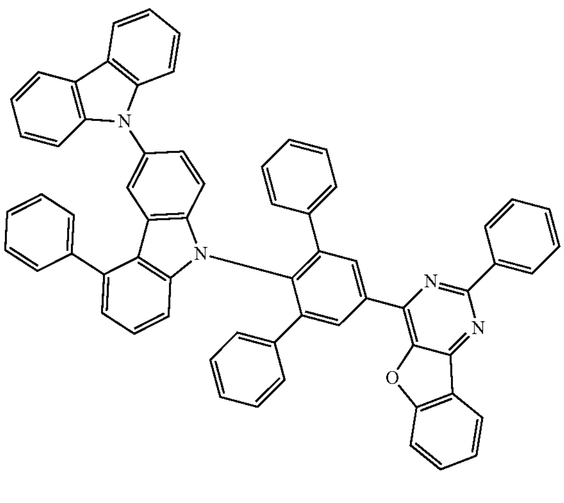
-continued
504
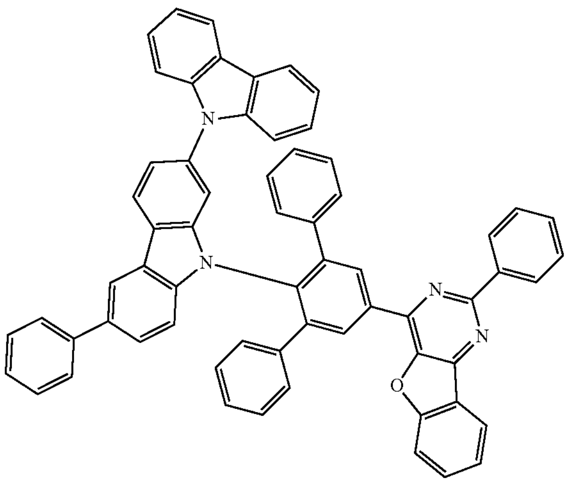
505
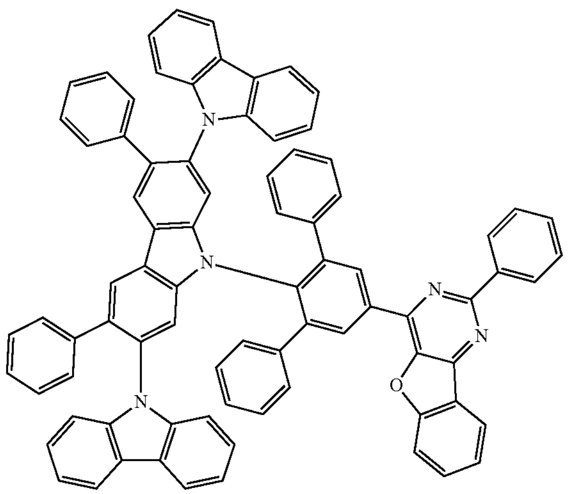
506
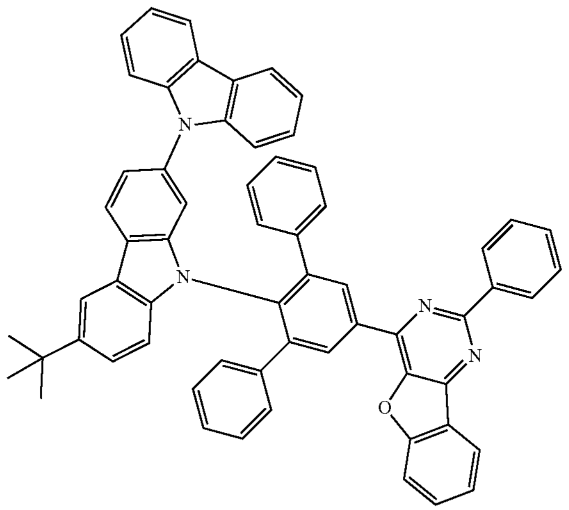

-continued
507
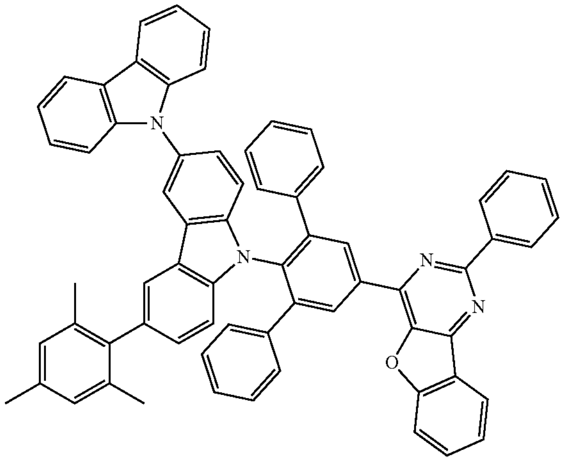
508
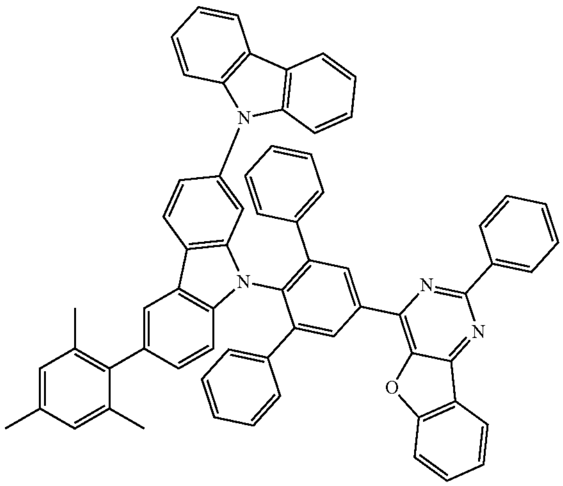
509
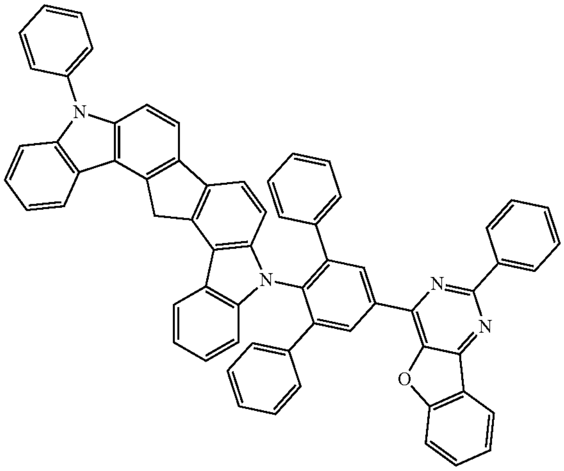
510
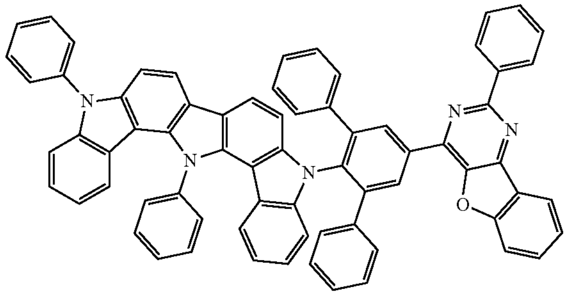
511
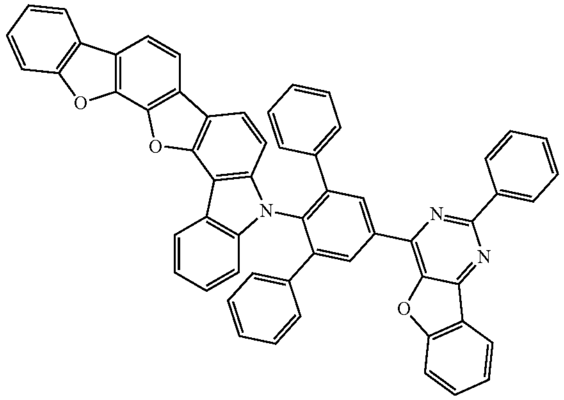
512
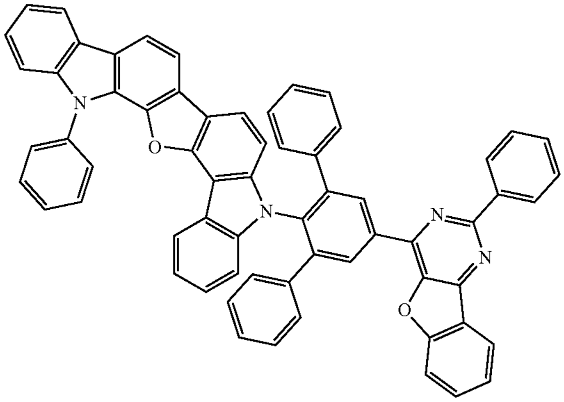
513
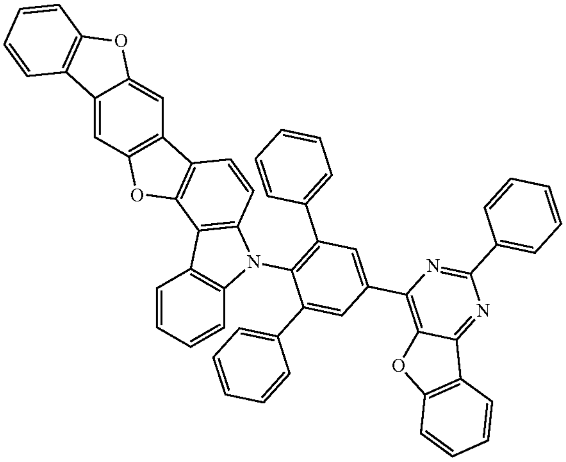

-continued
514
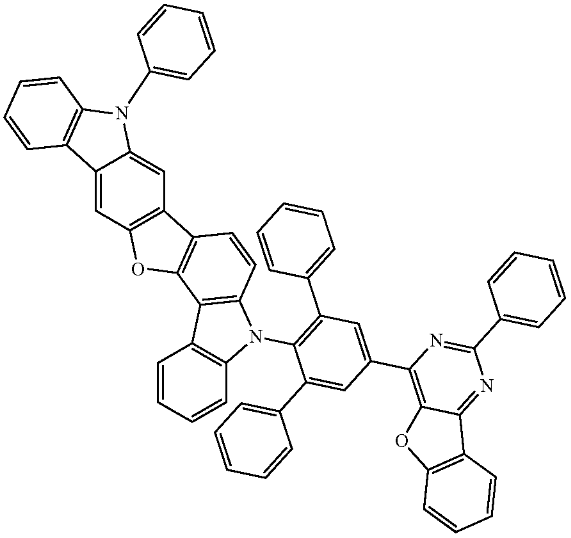
515
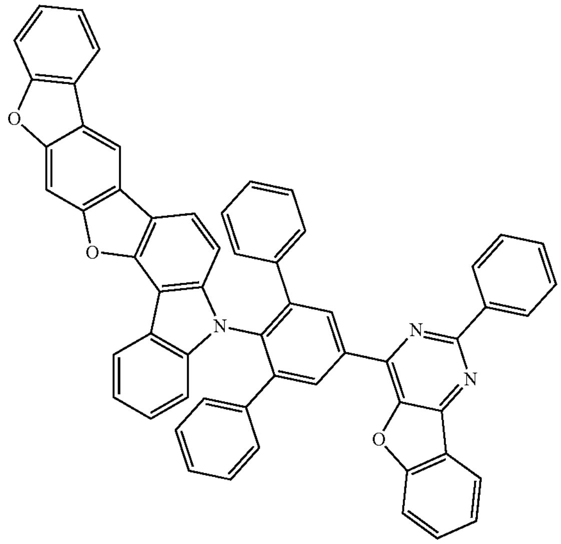
516
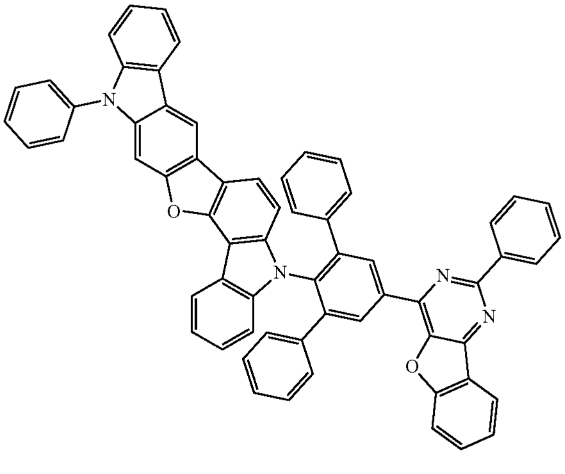
-continued
517
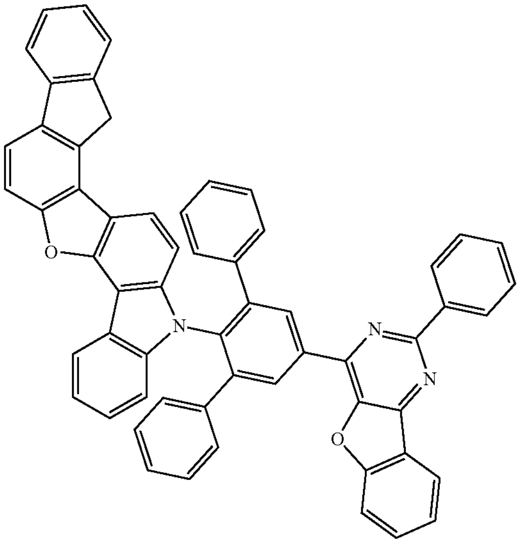
518
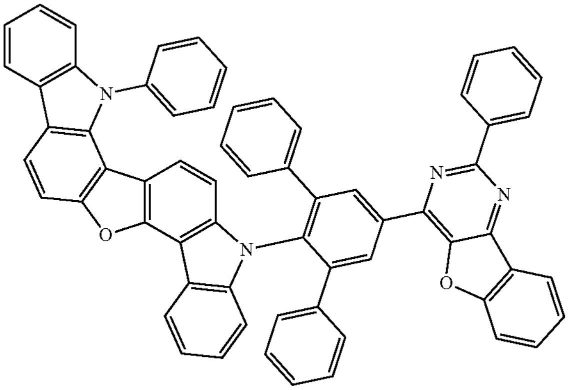
519
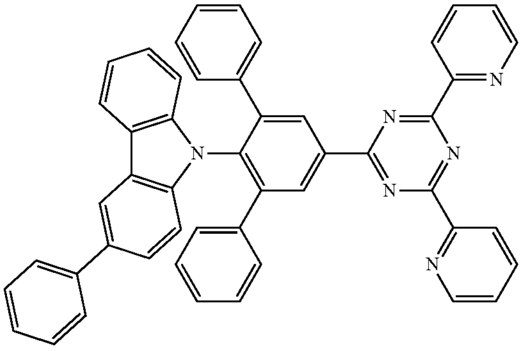

-continued
520
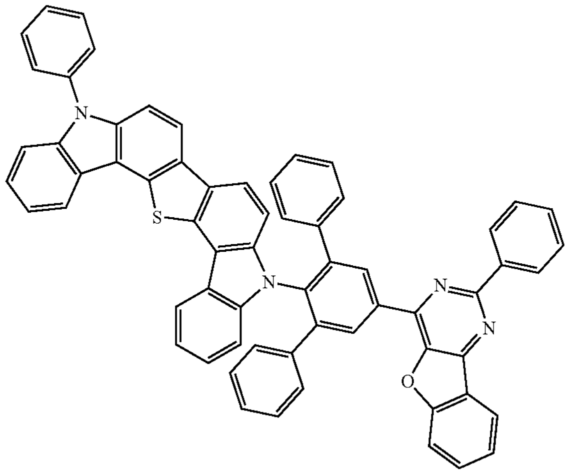
521
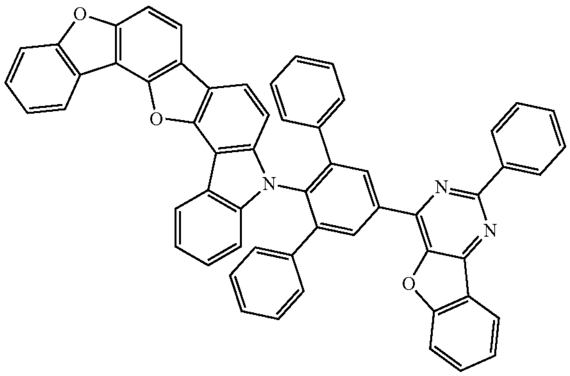
522
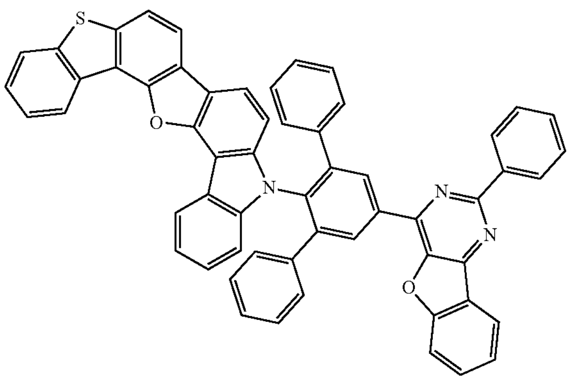
-continued
523
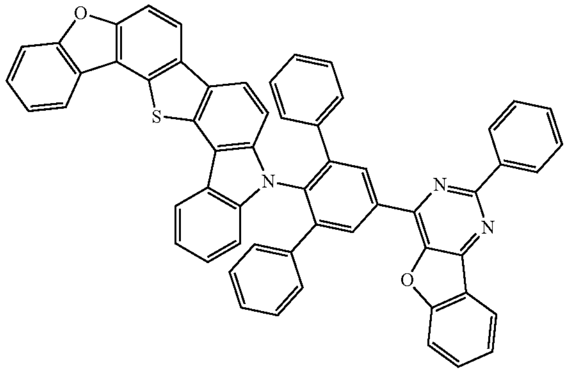
524
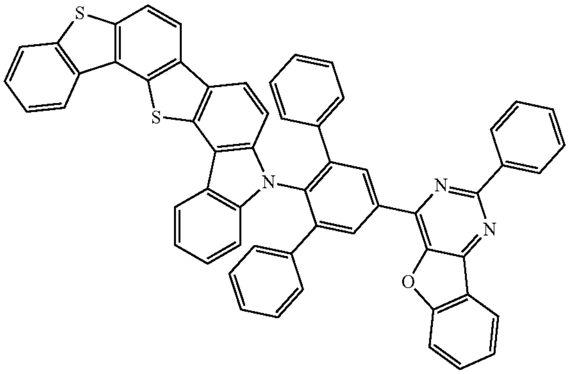
525
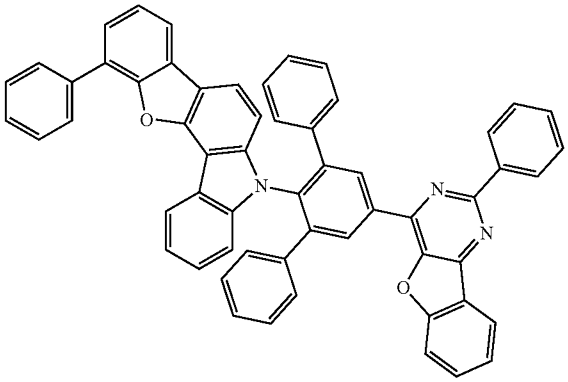
526
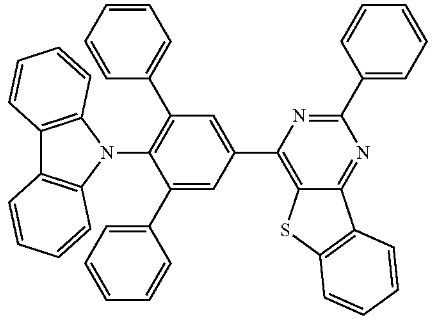

-continued
527
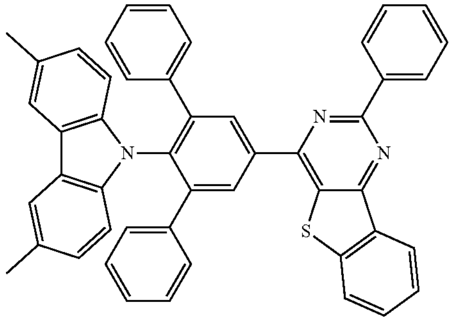
528
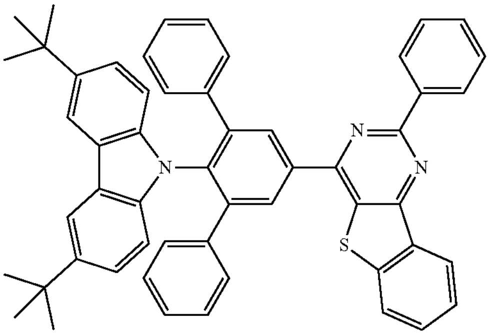
529
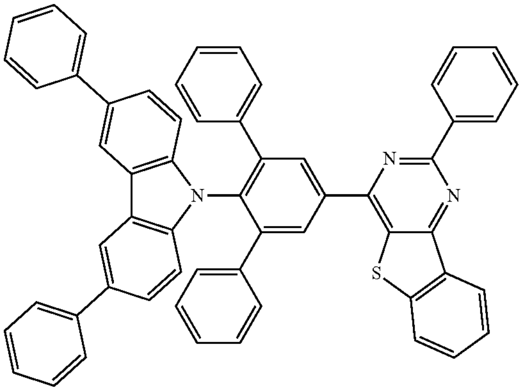
530
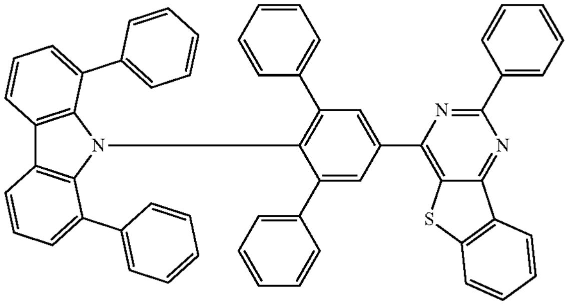
-continued
531
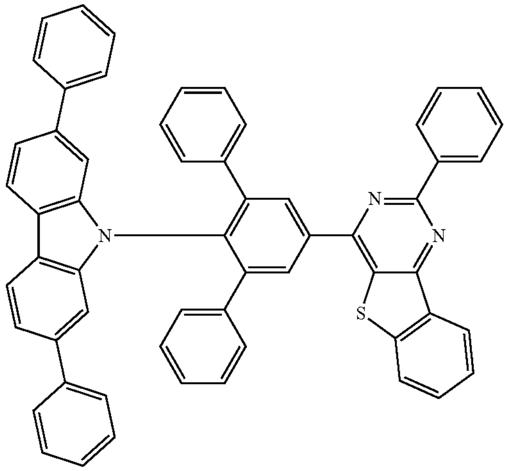
532
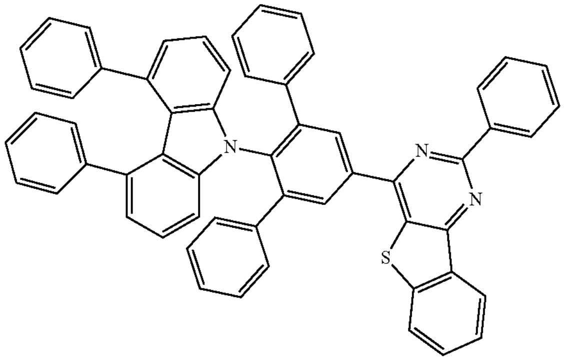
533
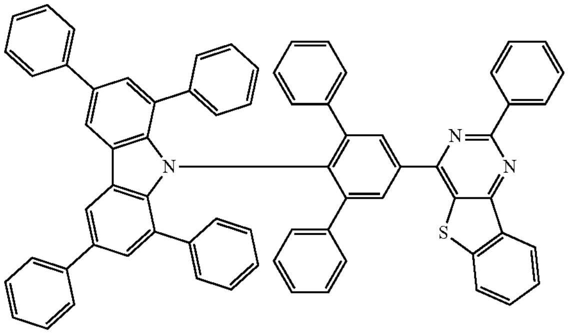
534
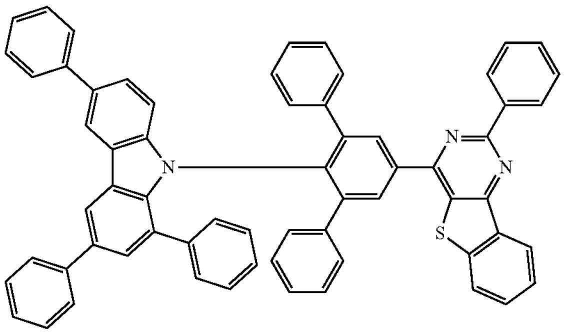

-continued
535
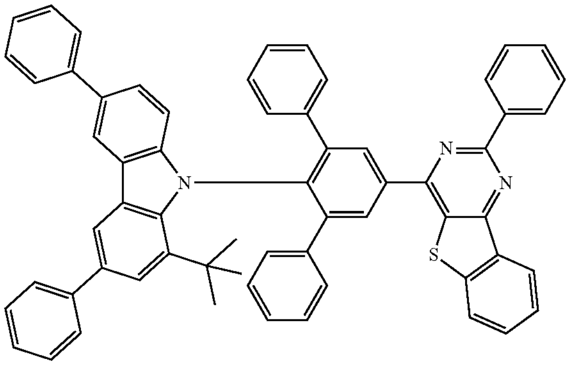
536
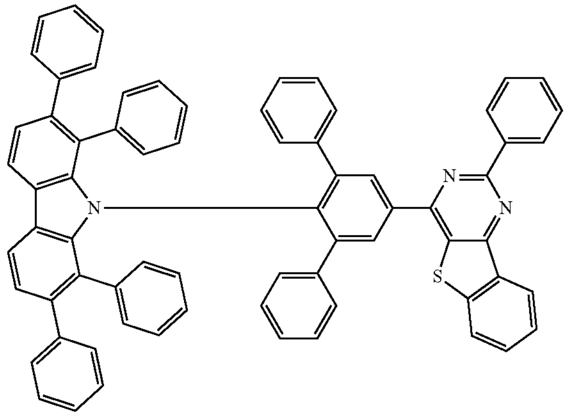
537
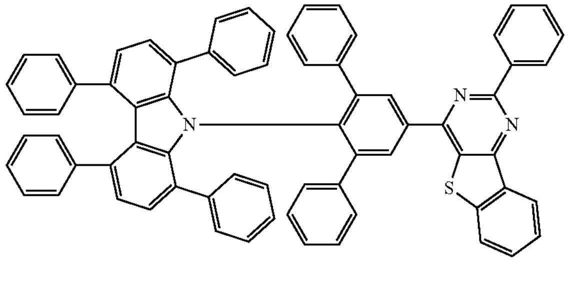
538
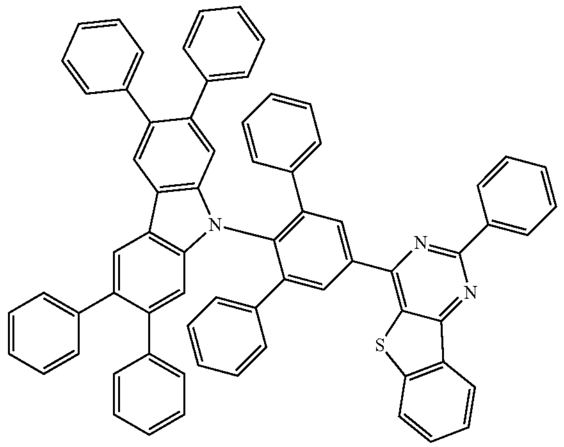
539
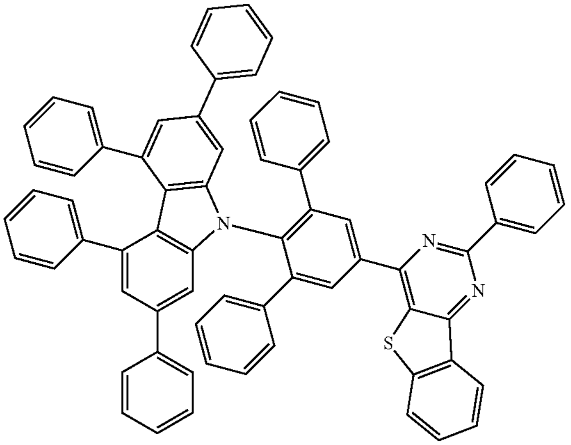
540
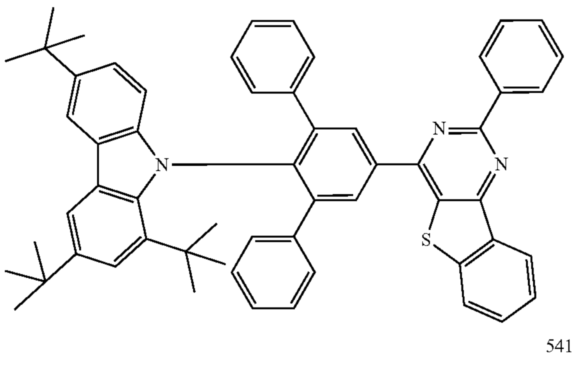
541
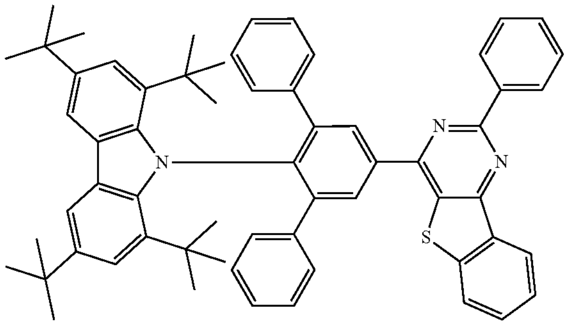

-continued
542
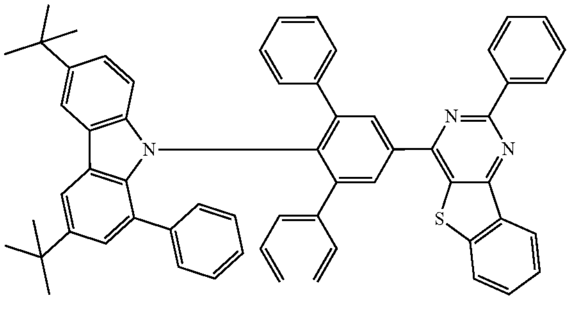
543
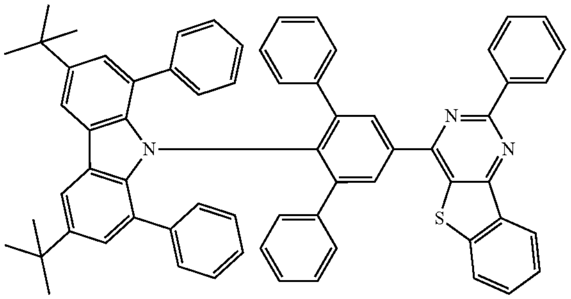
544
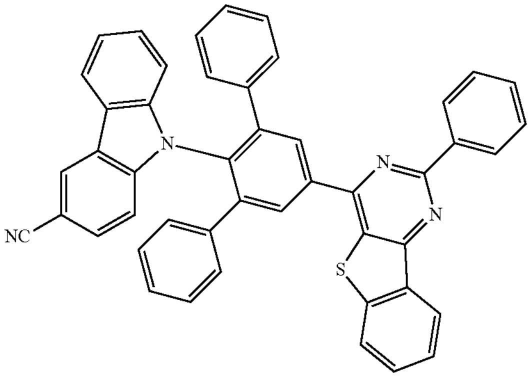
545
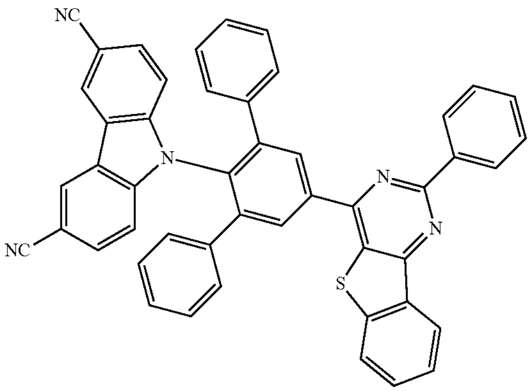
-continued
546
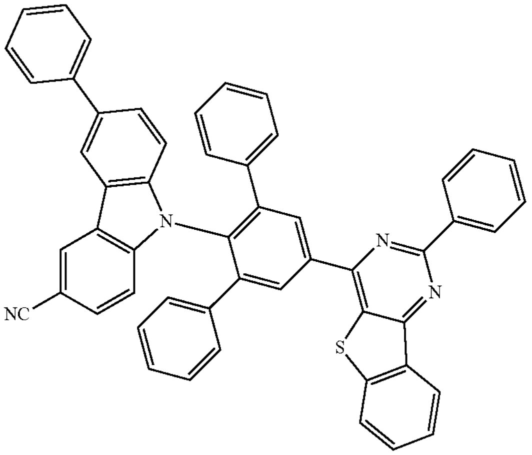
547
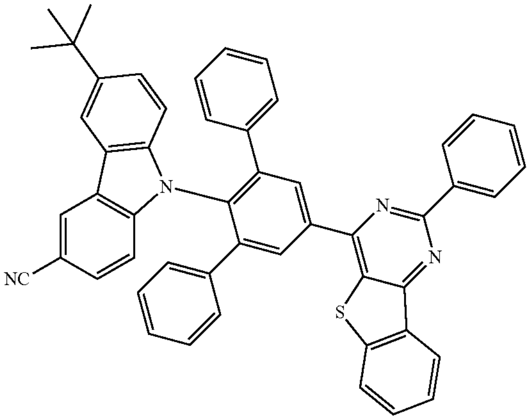
548
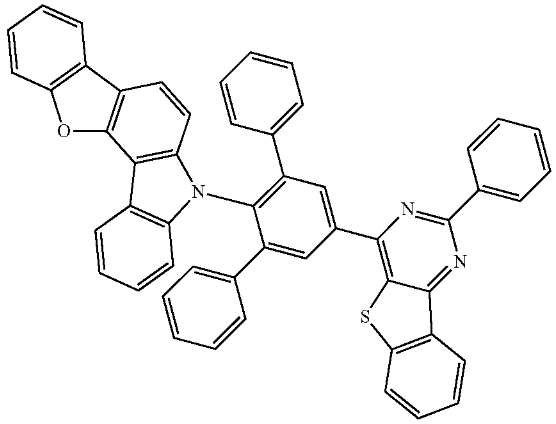

-continued
549
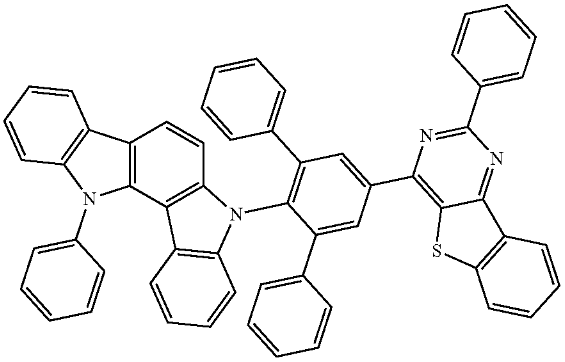
550
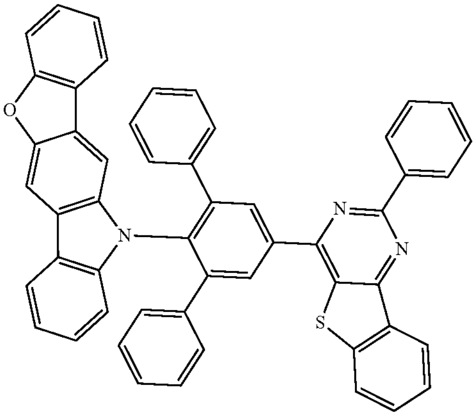
551
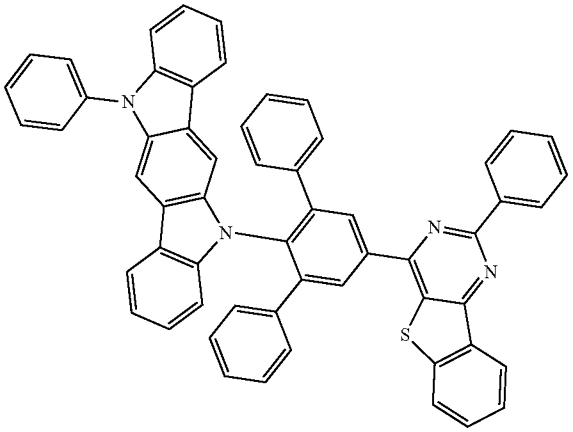
552
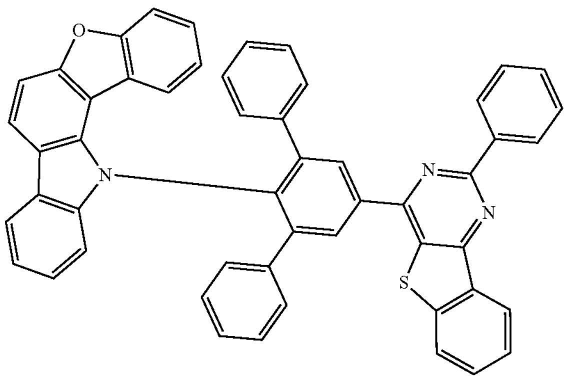
-continued
553
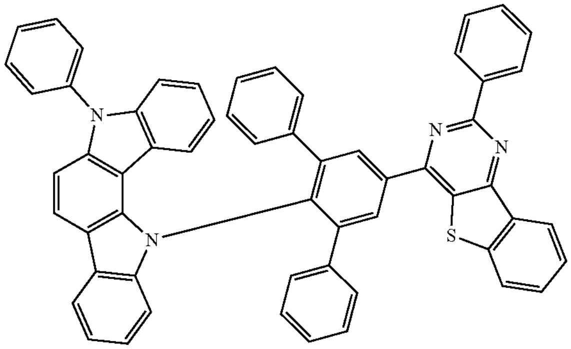
554
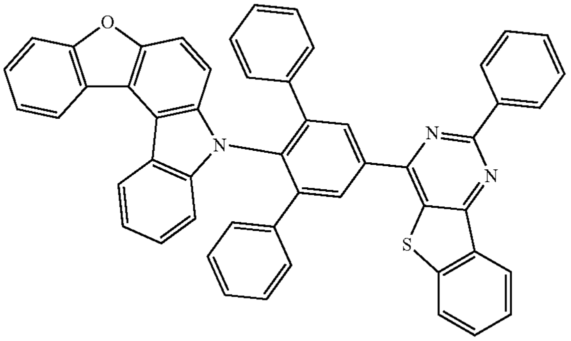
555
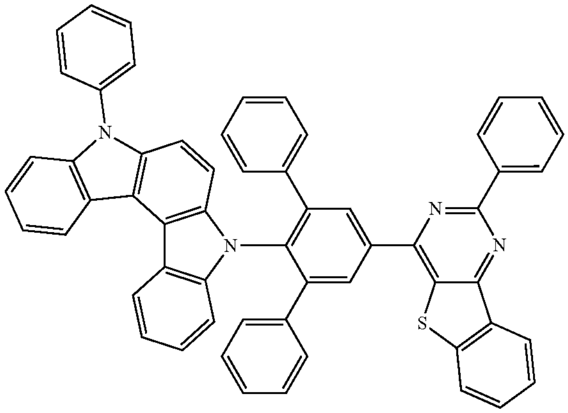
556
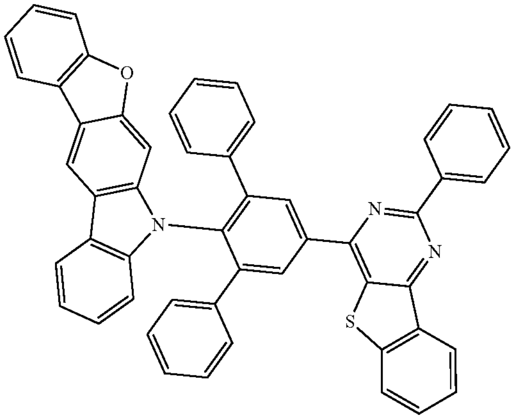

-continued
557
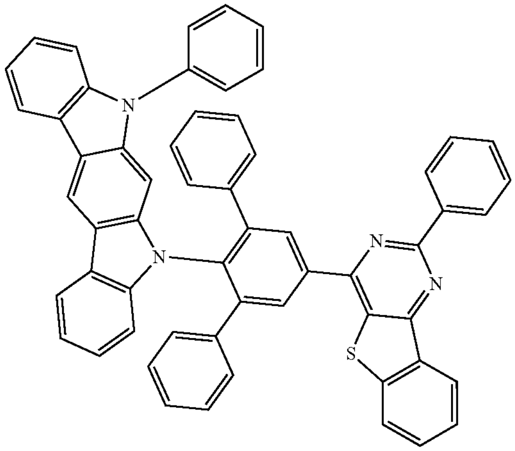
558
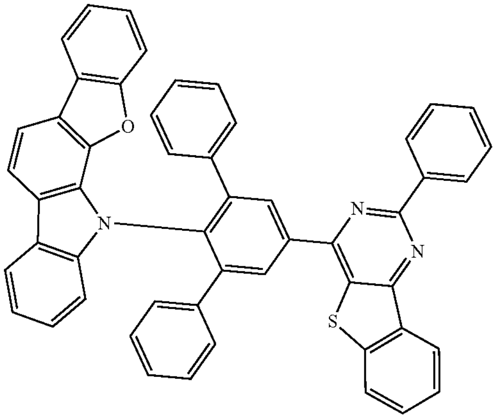
559
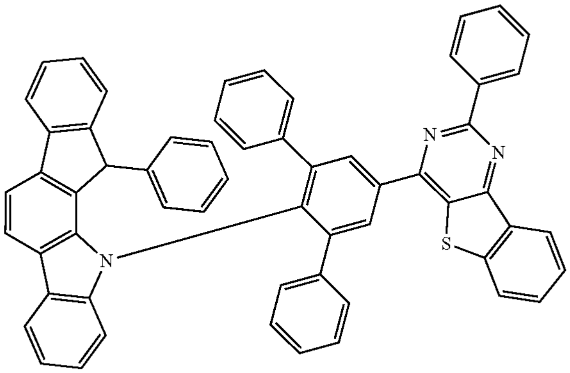
-continued
560
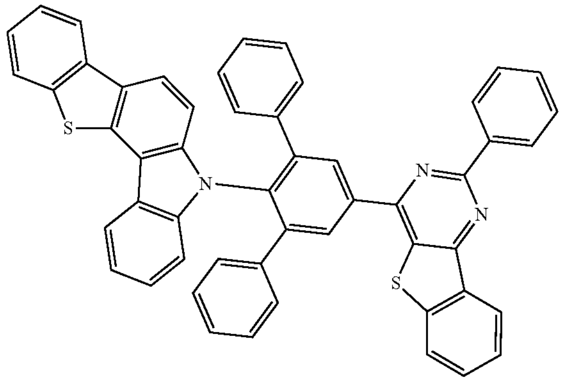
561
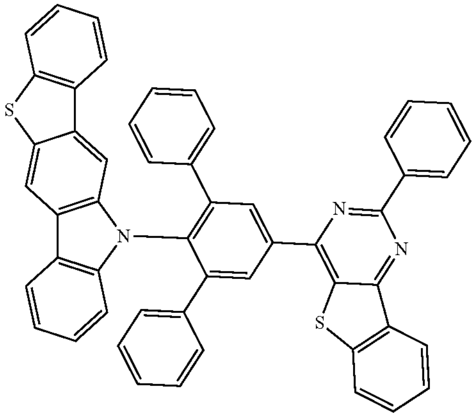
562
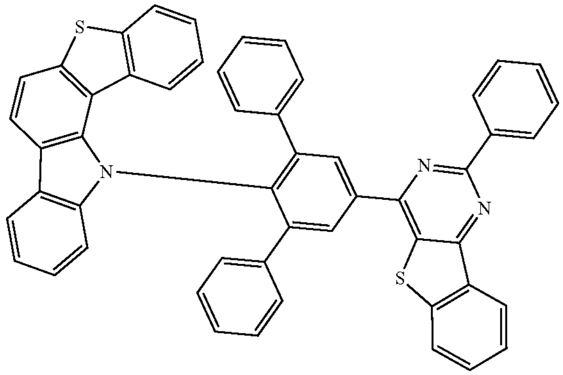
563
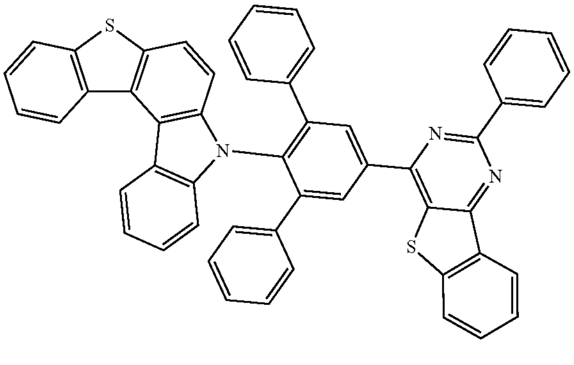

-continued
564
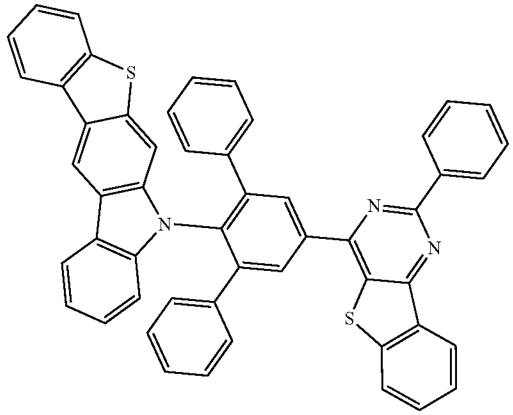
565
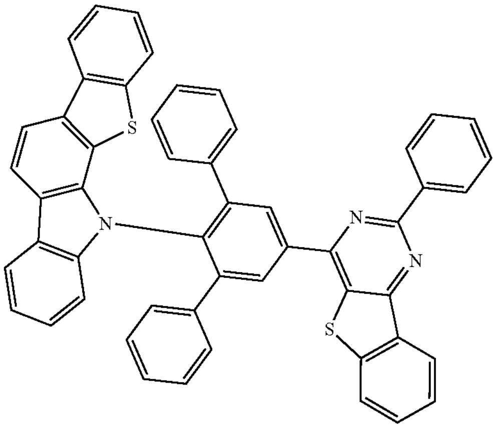
566
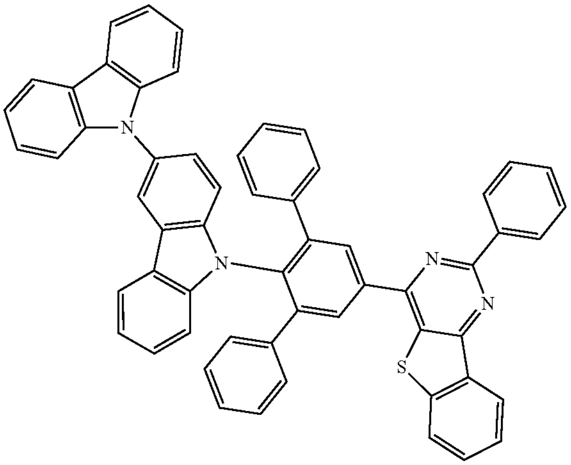
-continued
567
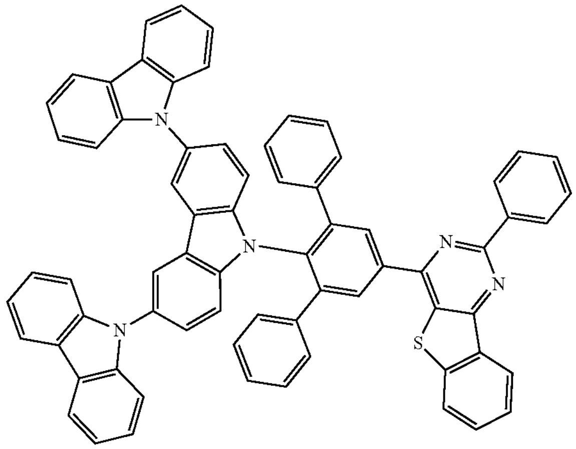
568
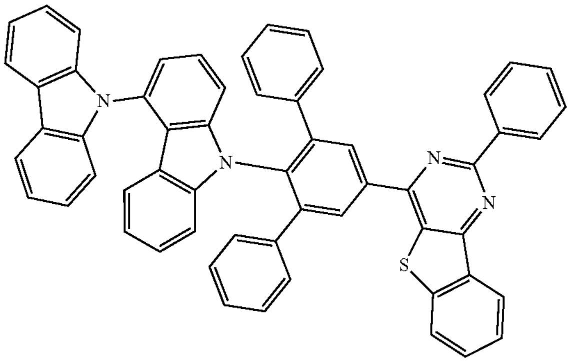
569
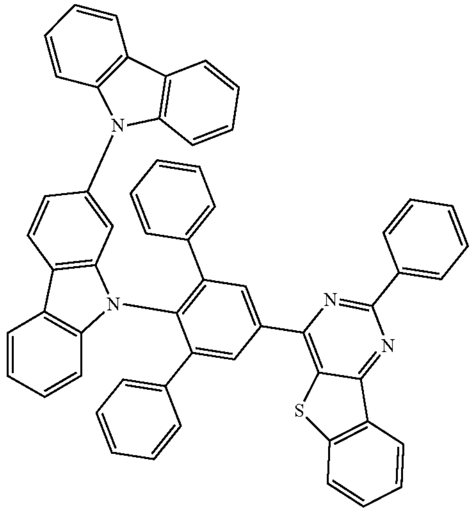

-continued
570
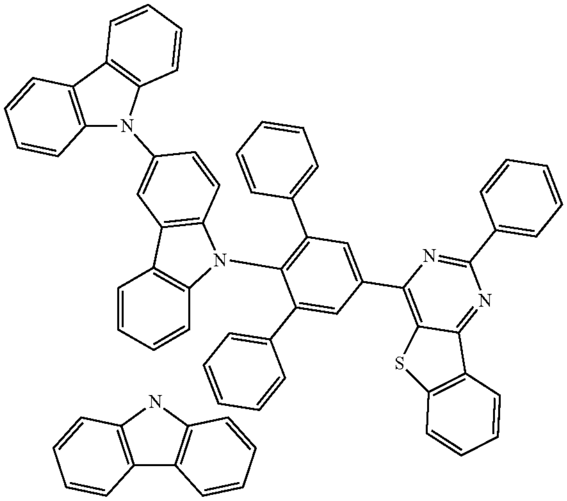
571
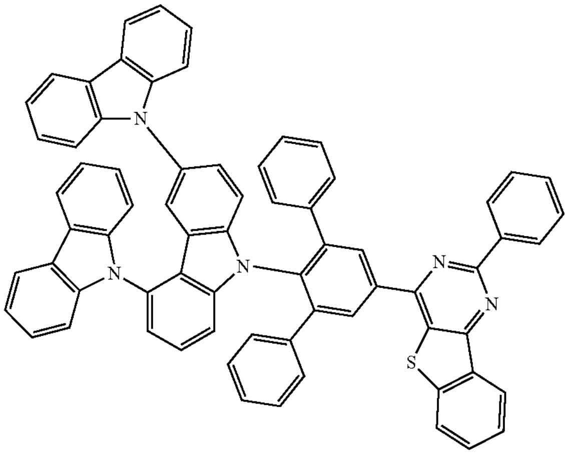
572
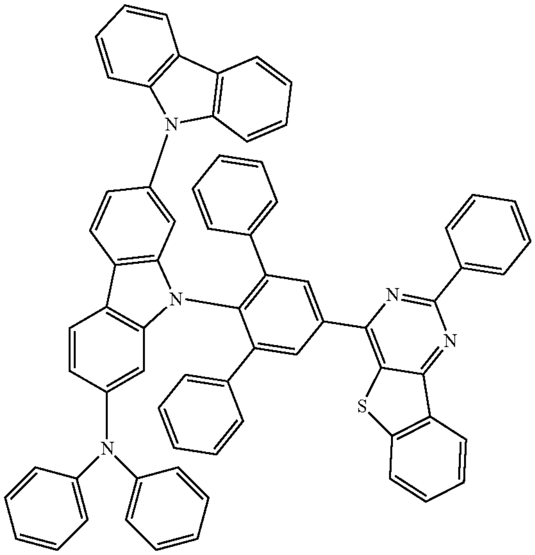
-continued
573
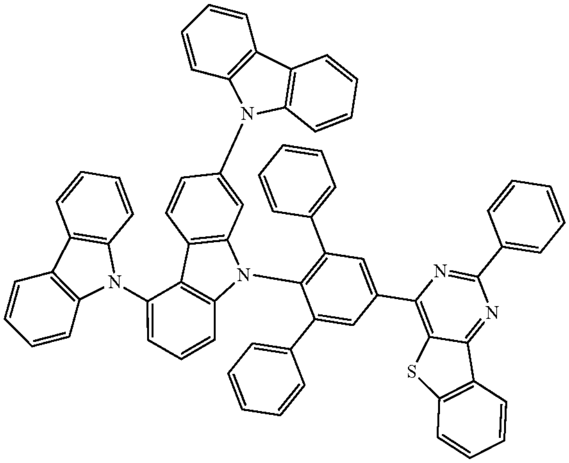
574
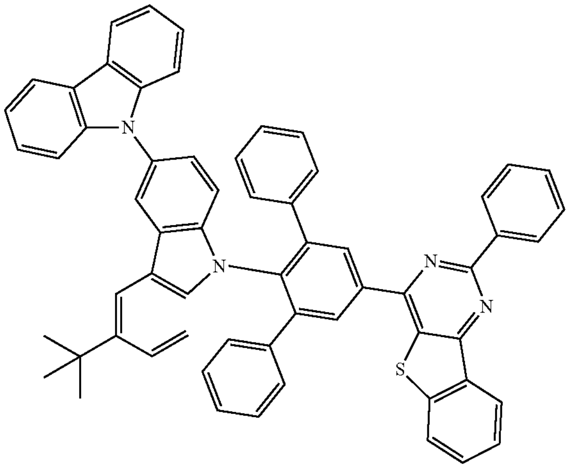
575
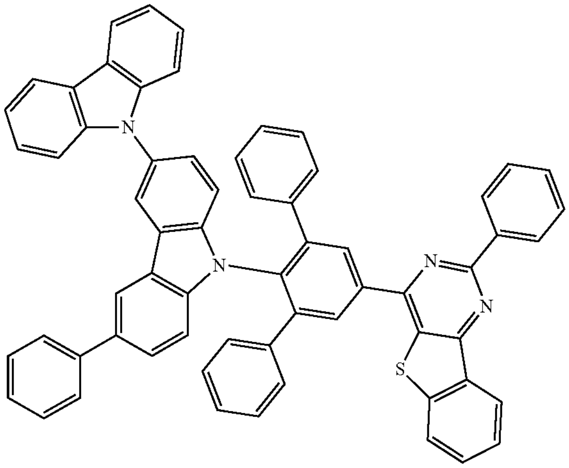

-continued
576
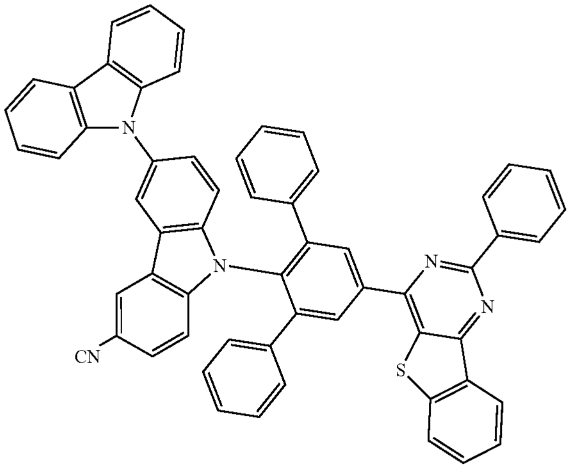
577
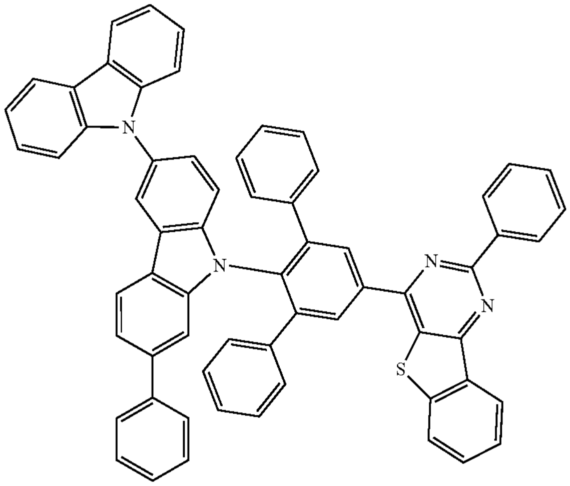
578
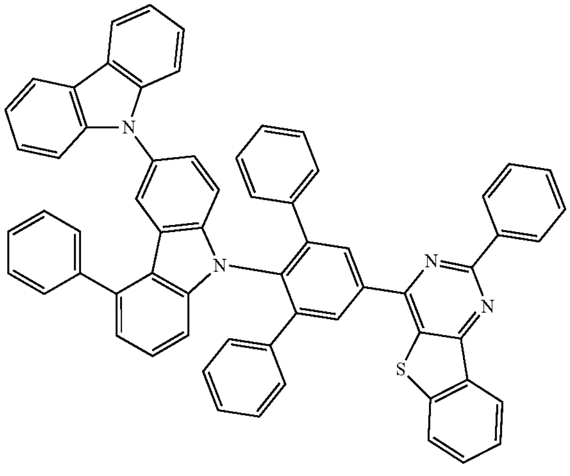
-continued
579
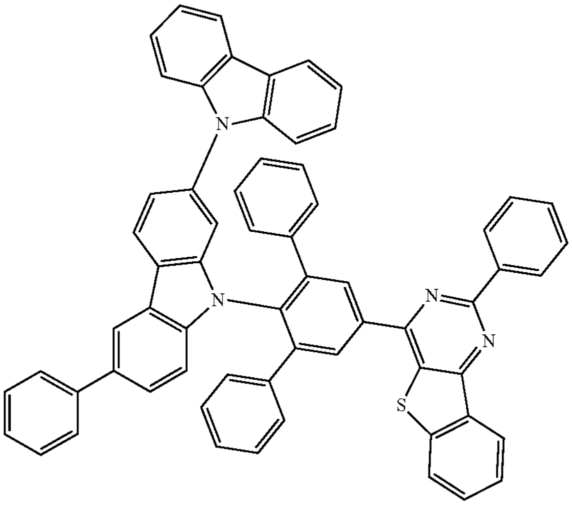
580
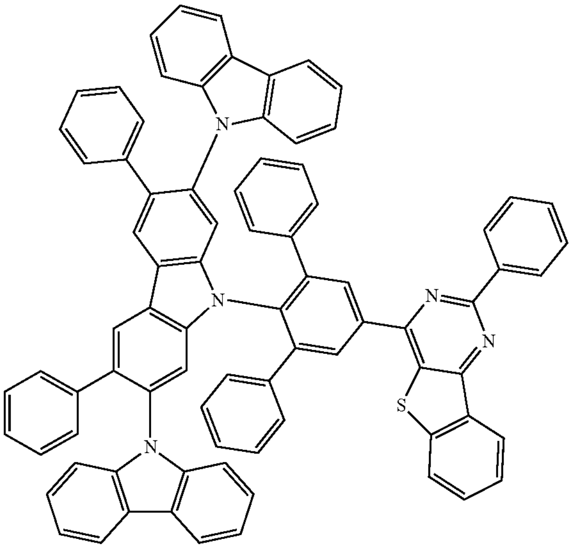
581
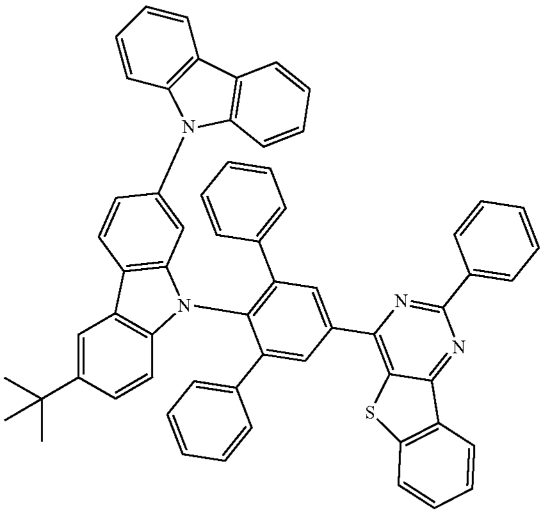

-continued
582
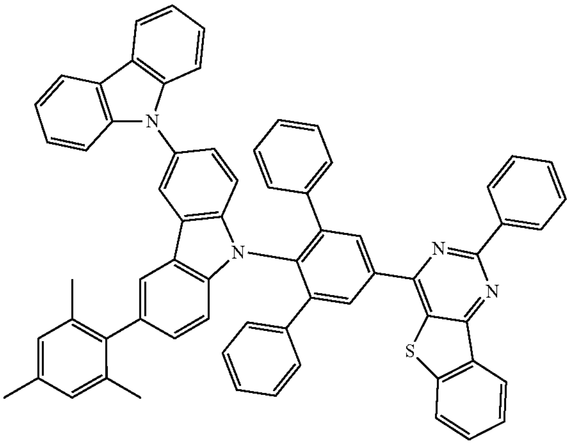
583
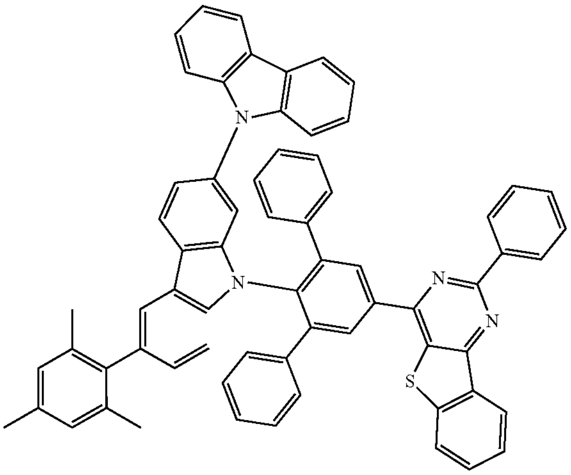
584
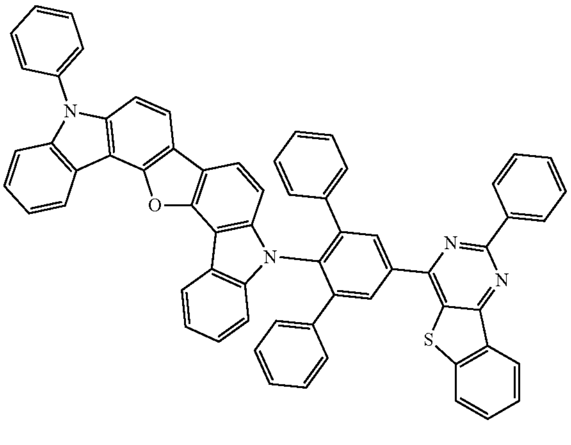
-continued
585
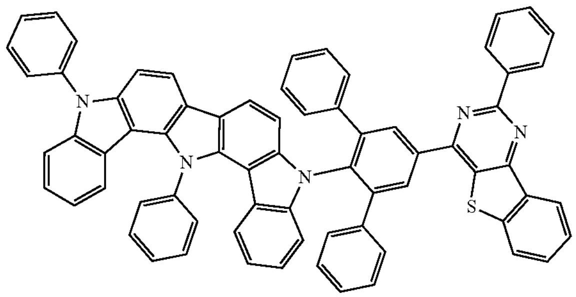
586
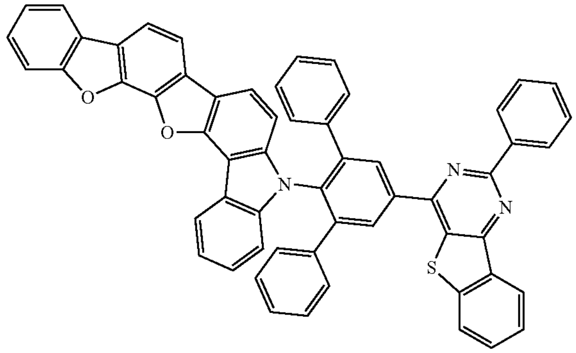
587
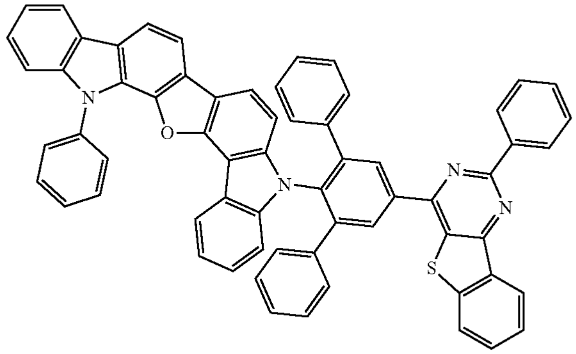
588
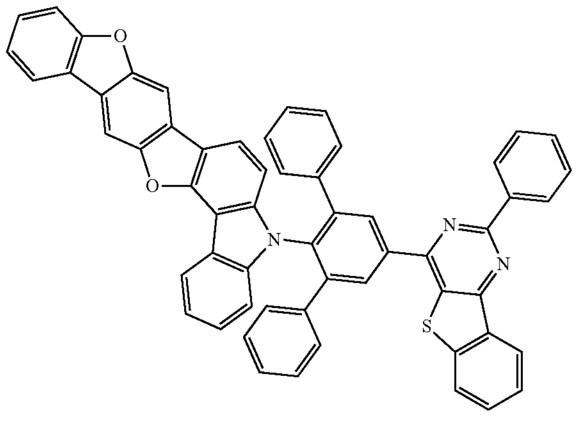

-continued
589
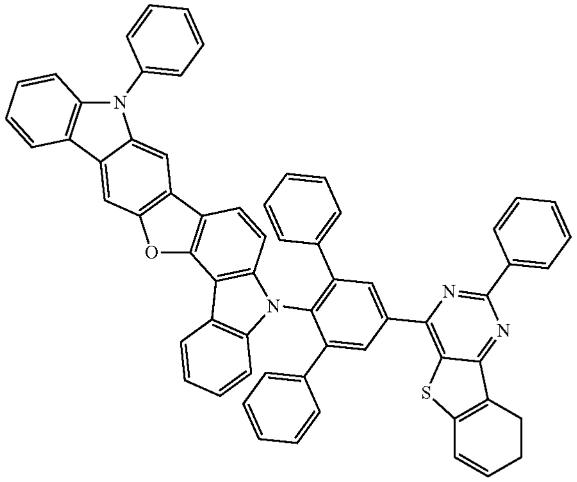
590
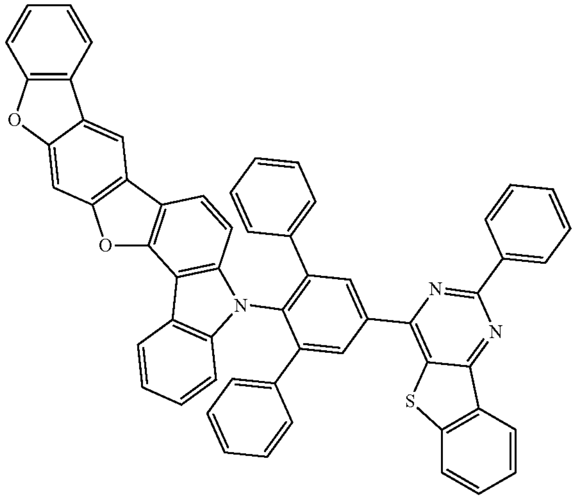
591
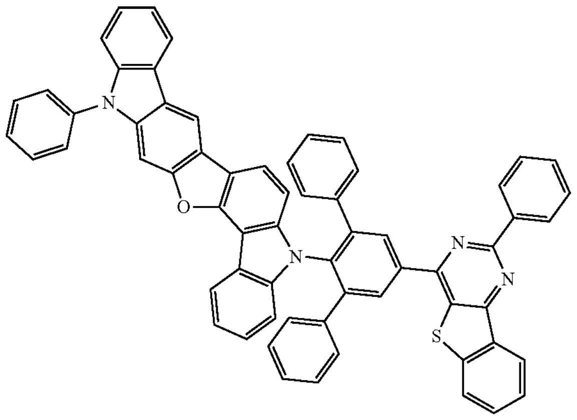
-continued
592
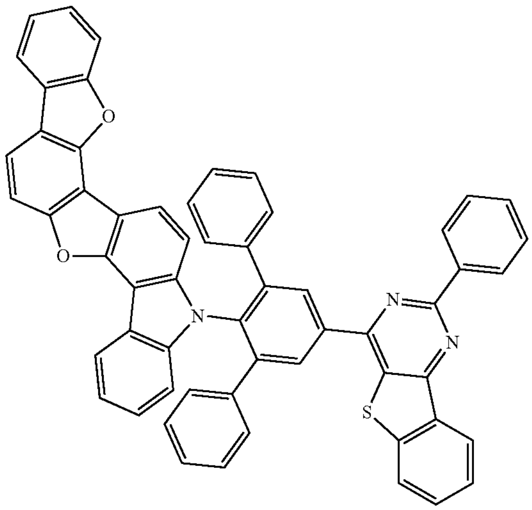
593
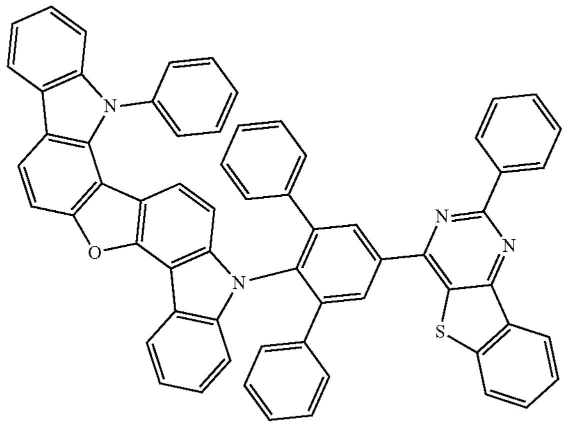
594
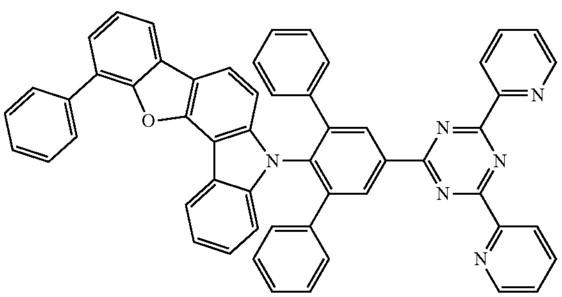

595
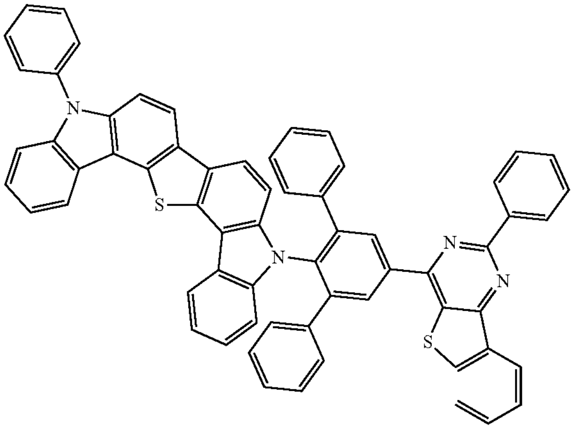
596
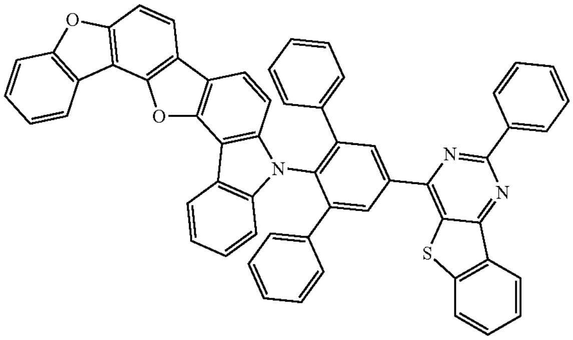
597
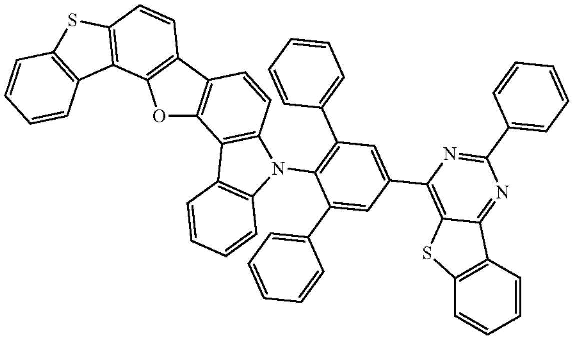
598
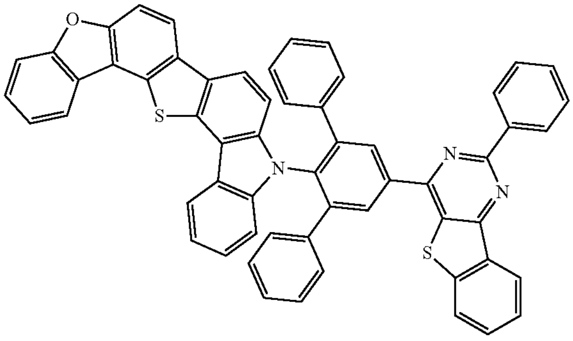
599
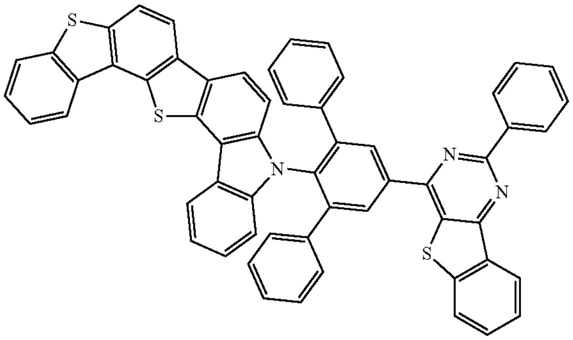
600
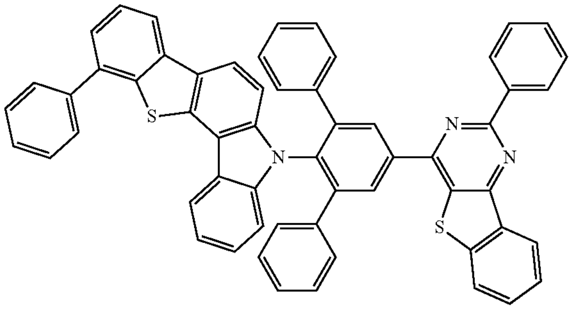
601
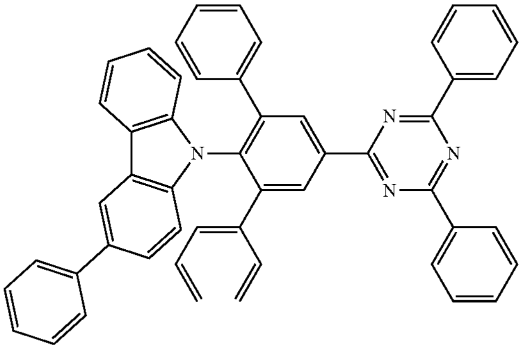
602
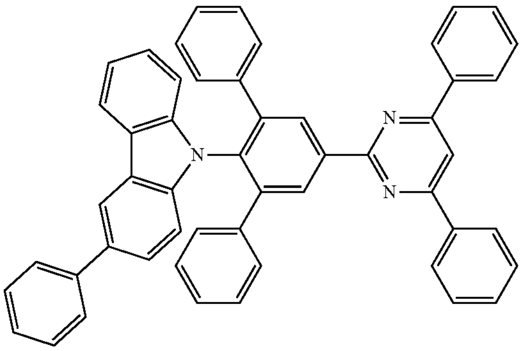

-continued
603
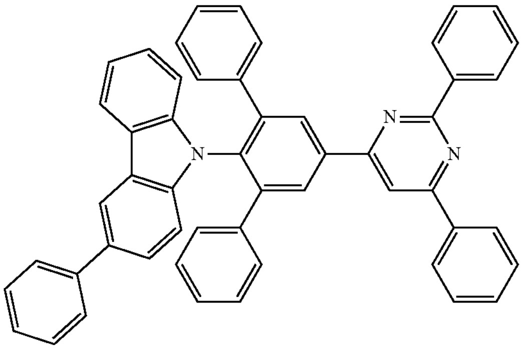
604
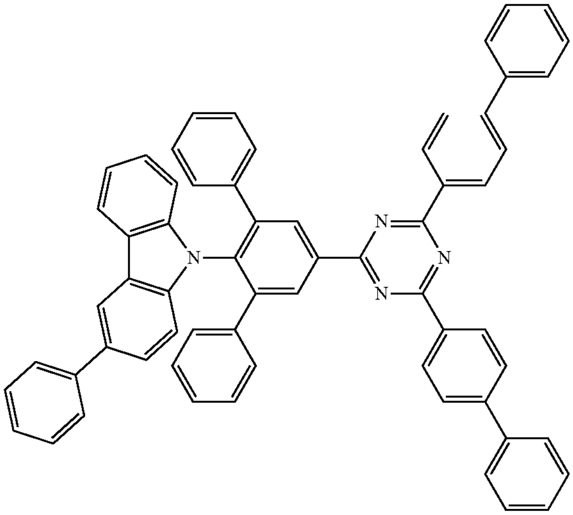
605
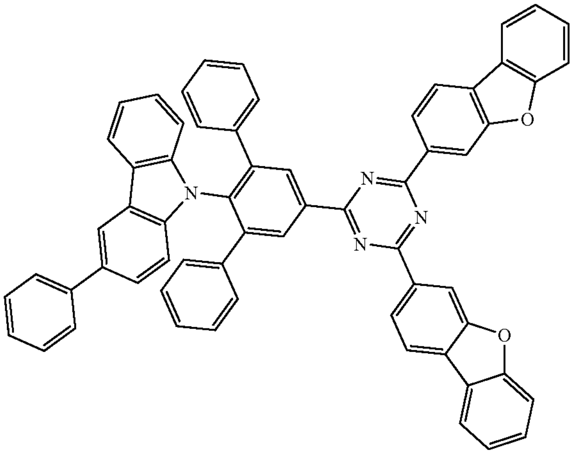
-continued
606
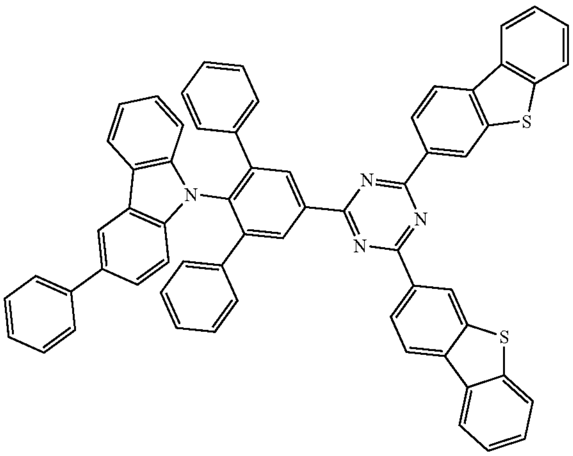
607
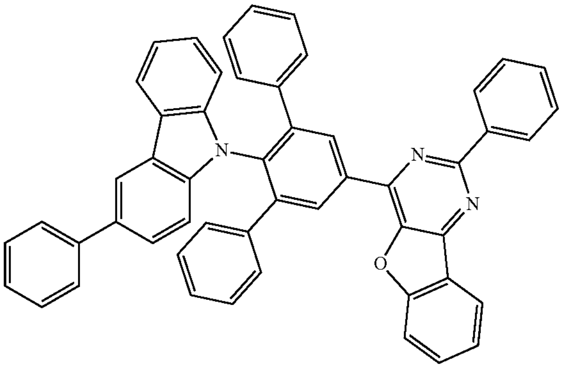
608
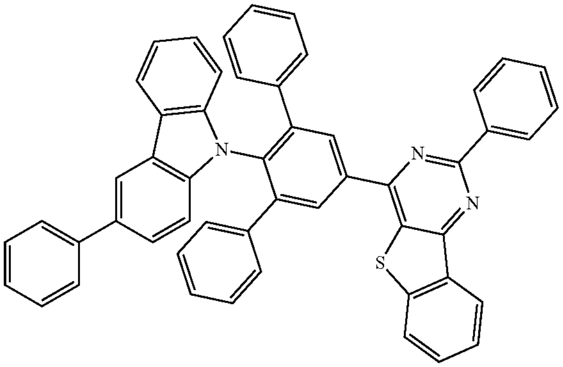

-continued
609
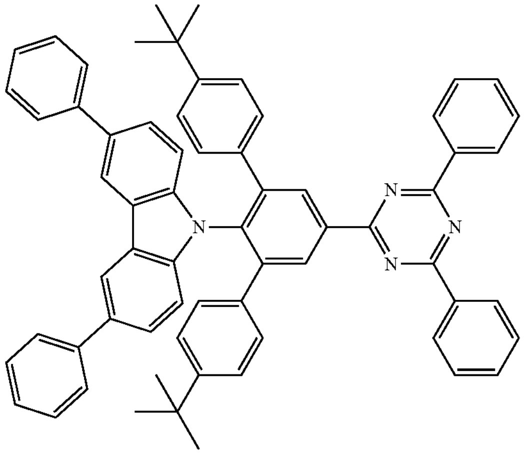
610
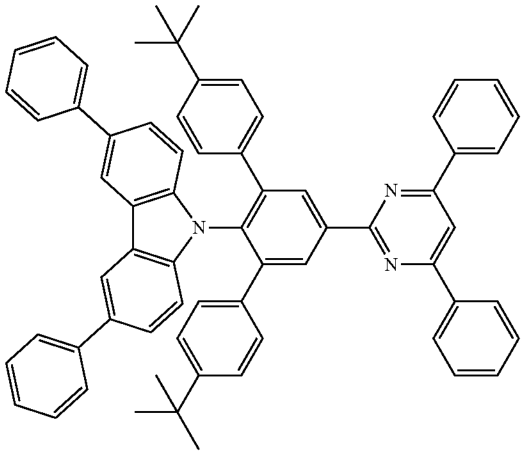
611
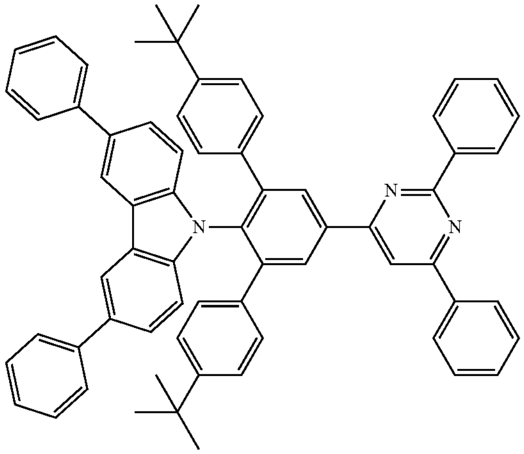
-continued
612
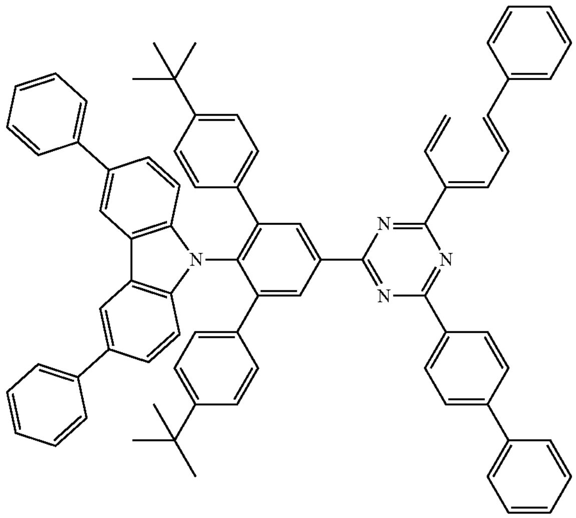
613
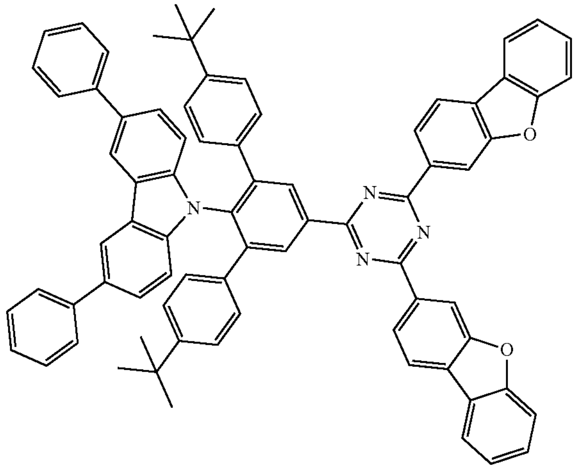
614
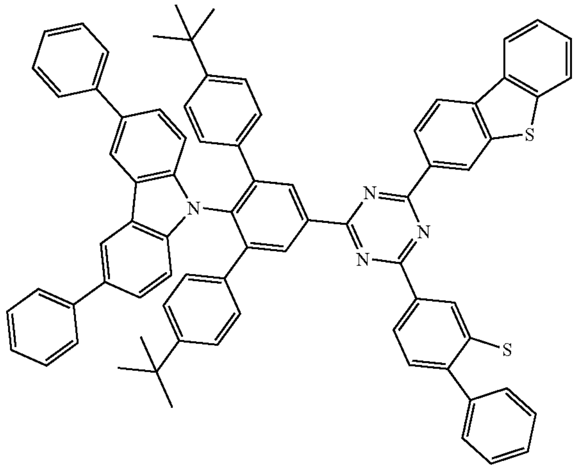

-continued
615
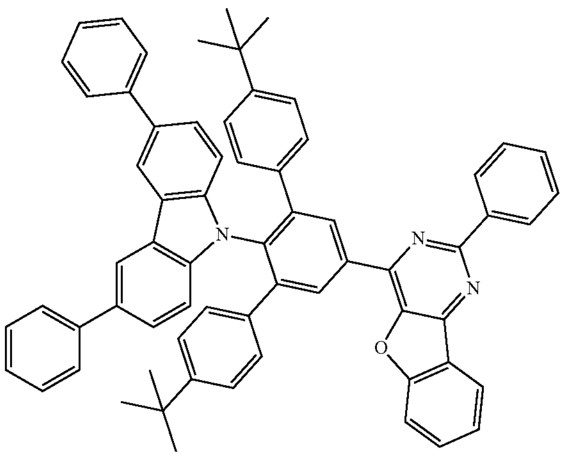
616
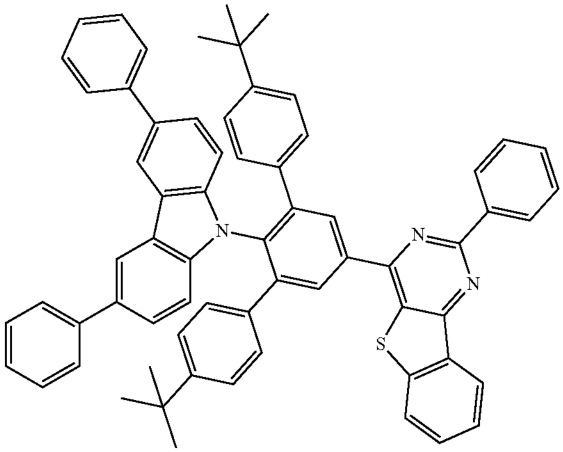
617
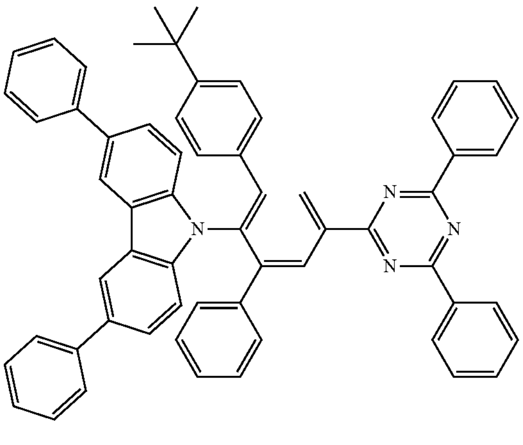
-continued
618
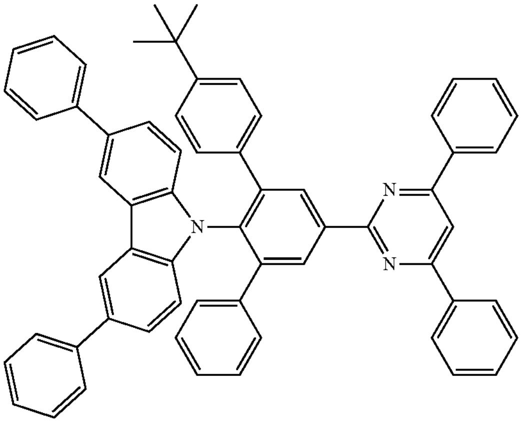
619
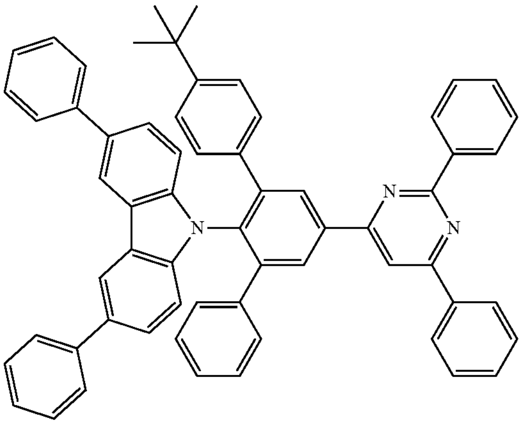
620
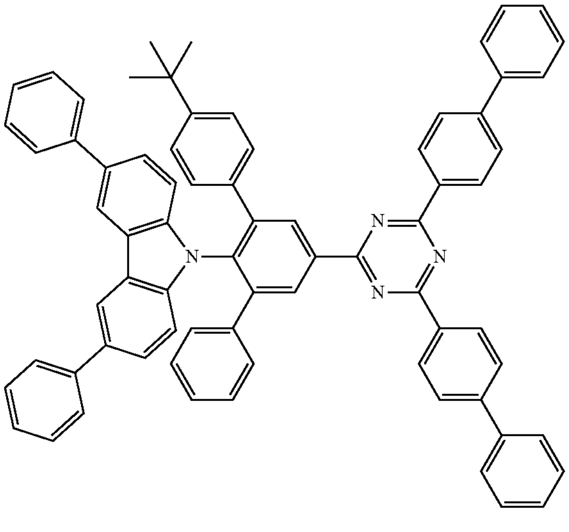

-continued
621
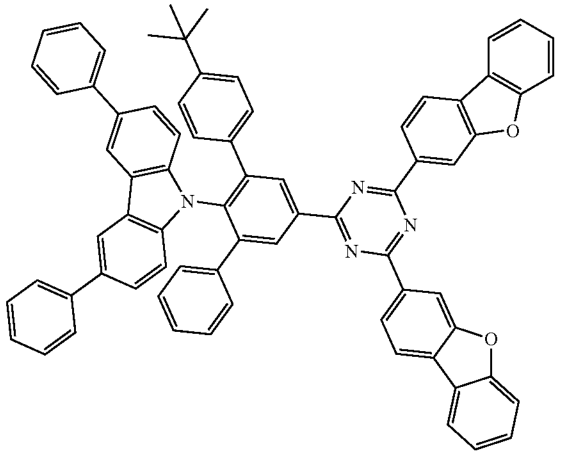
622
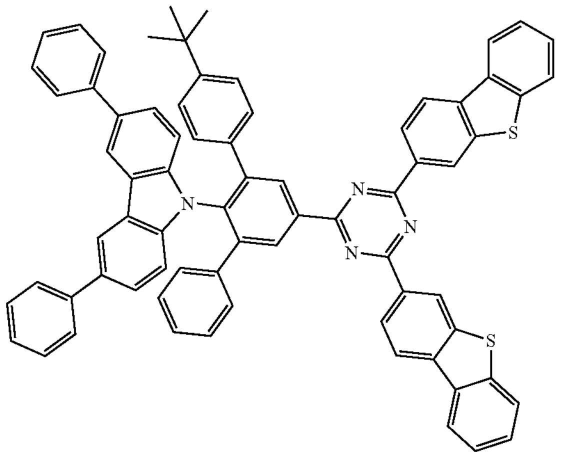
623
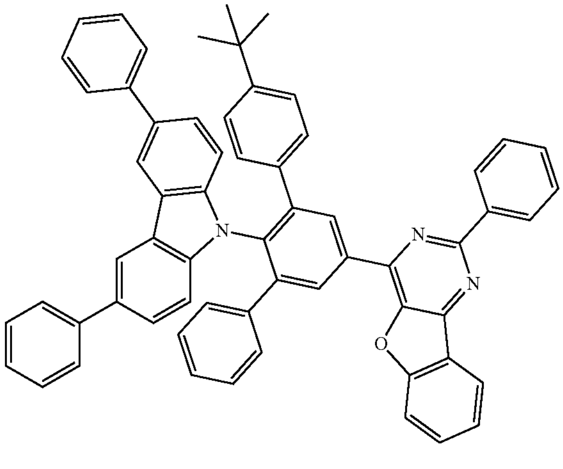
-continued
624
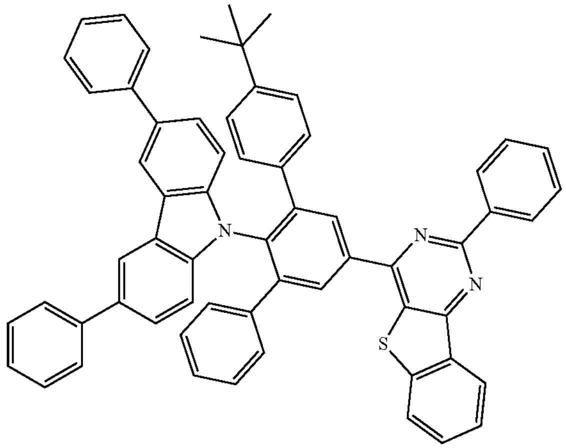
625
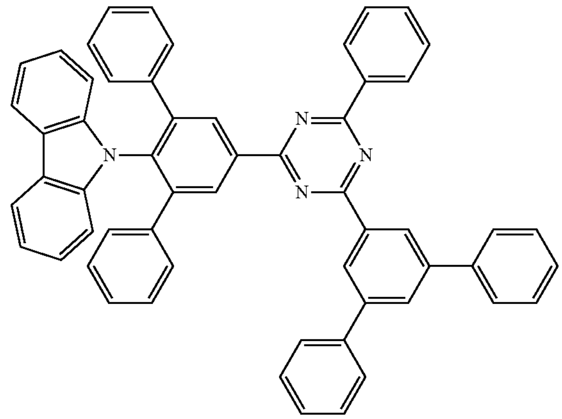
626
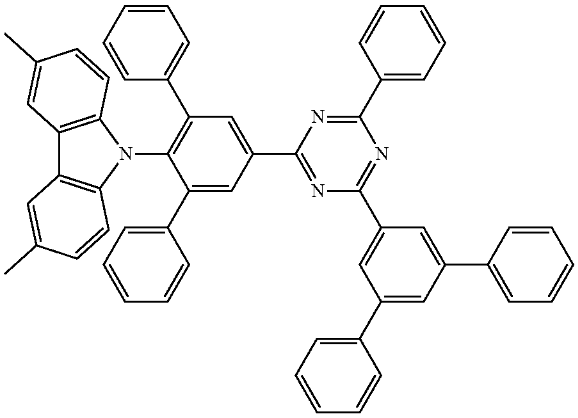

-continued
627
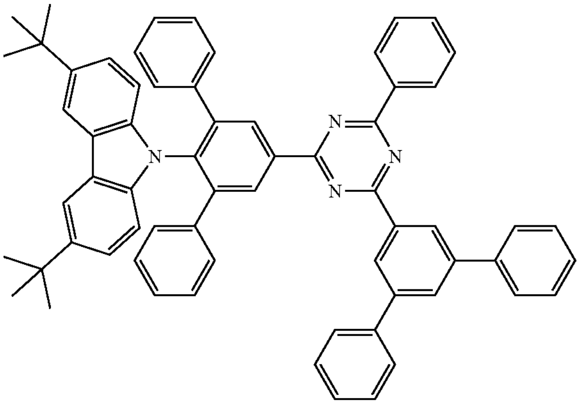
628
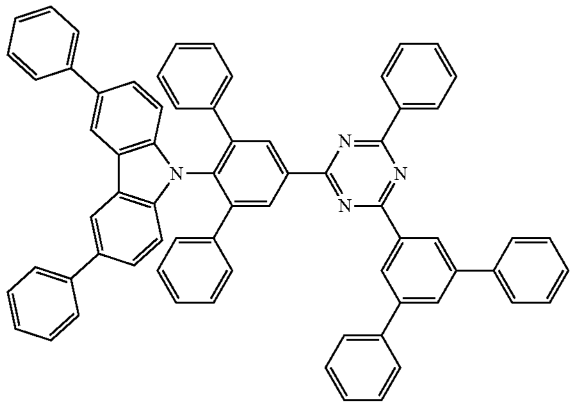
629
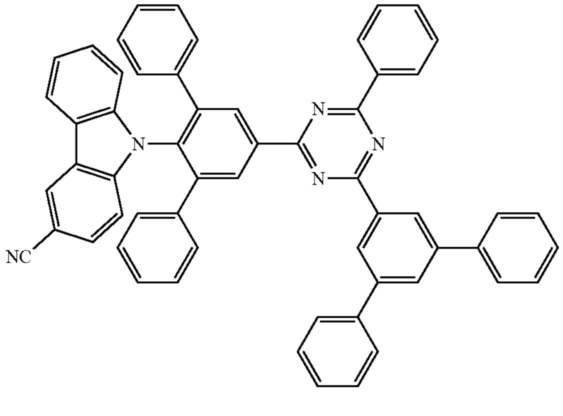
-continued
630
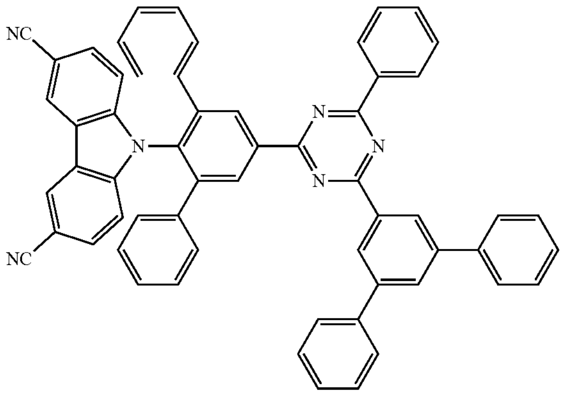
631
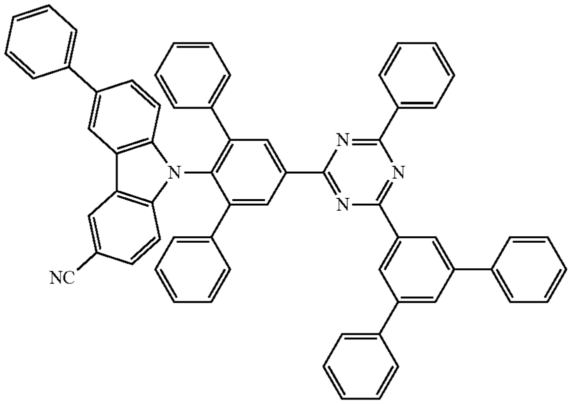
632
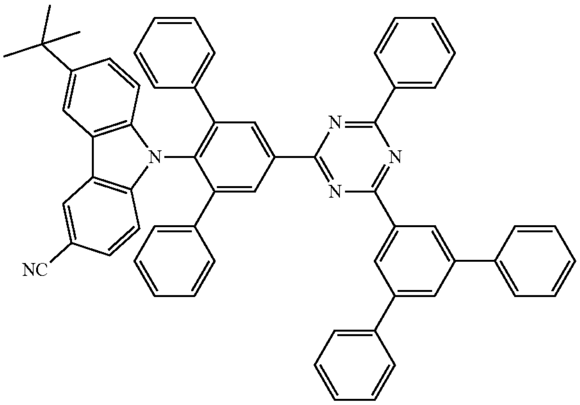
633
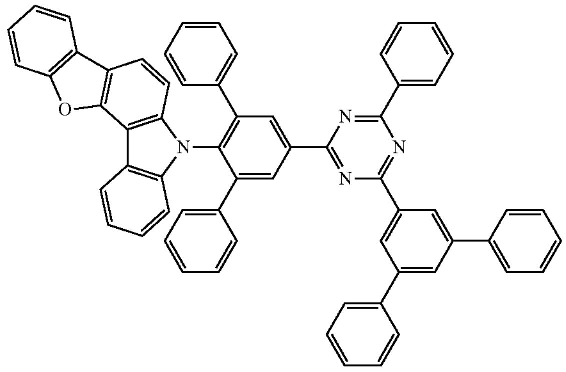

-continued
634
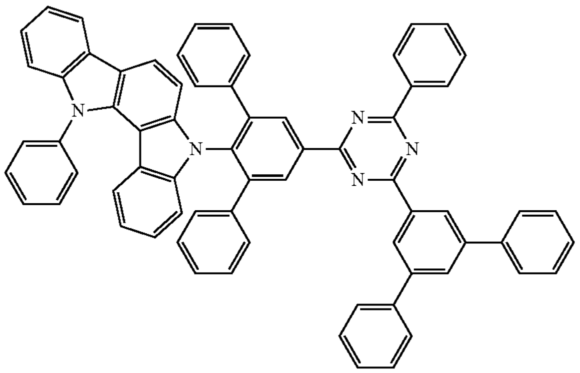
635
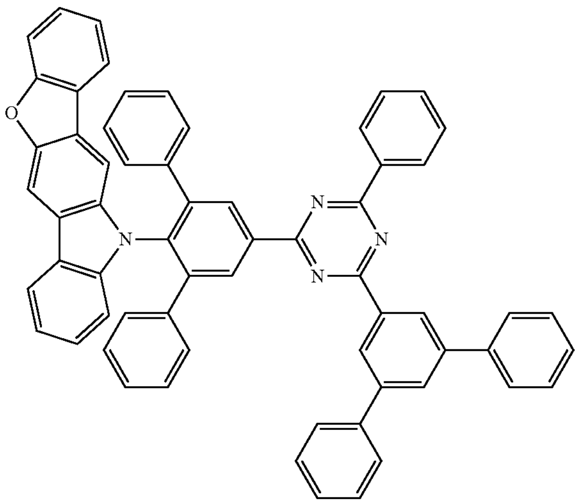
636
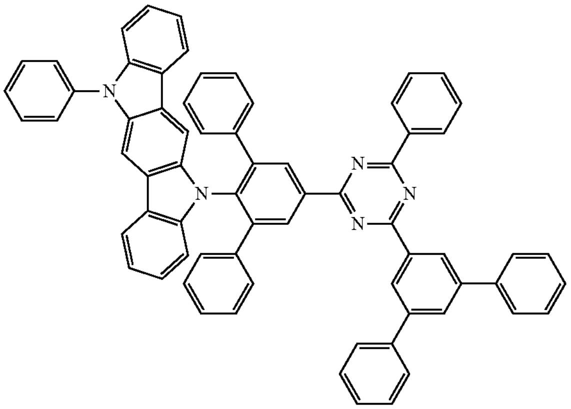
-continued
637
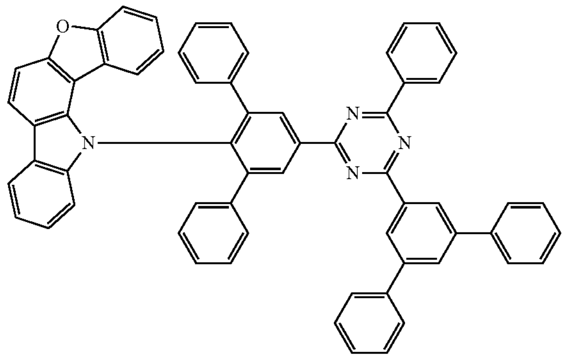
638
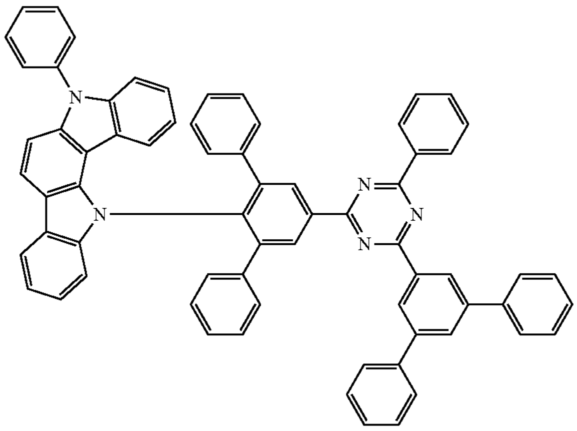
639
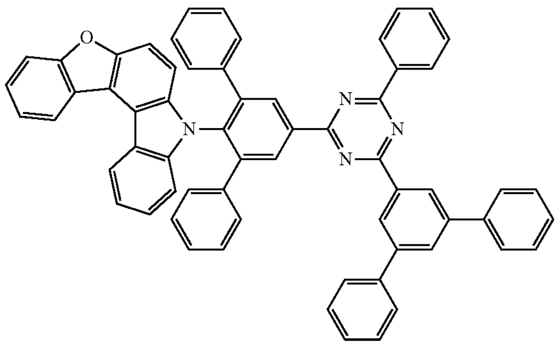
640
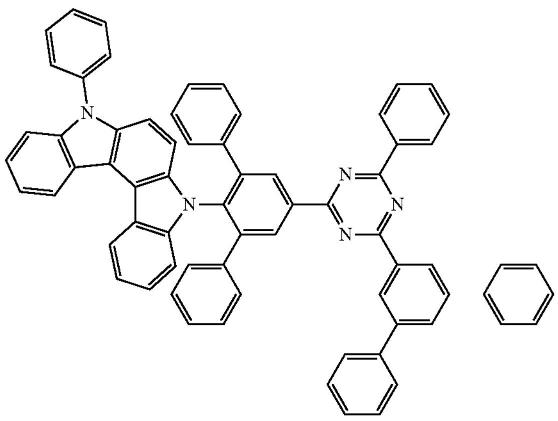

-continued
641
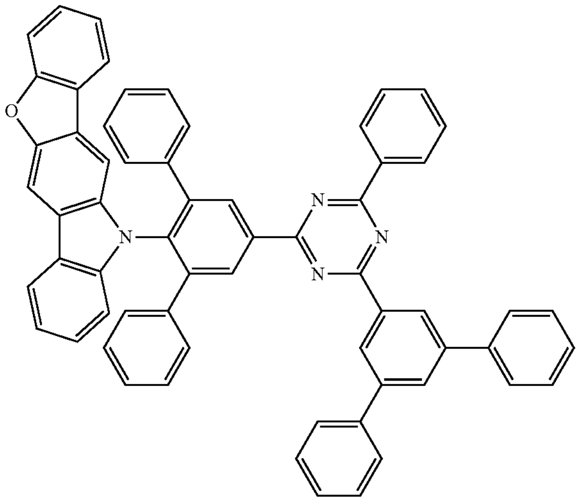
642
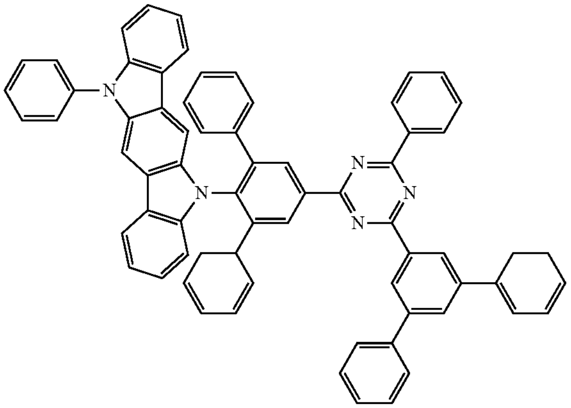
643
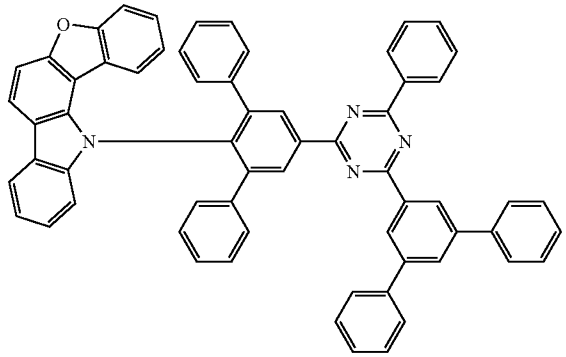
-continued
644
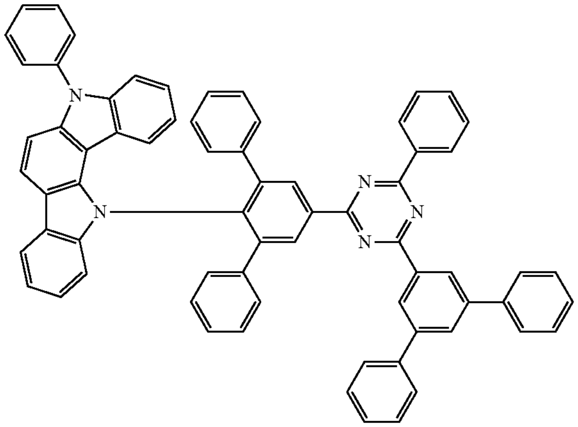
645
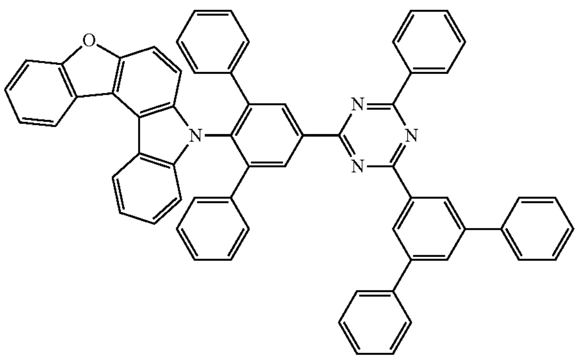
646
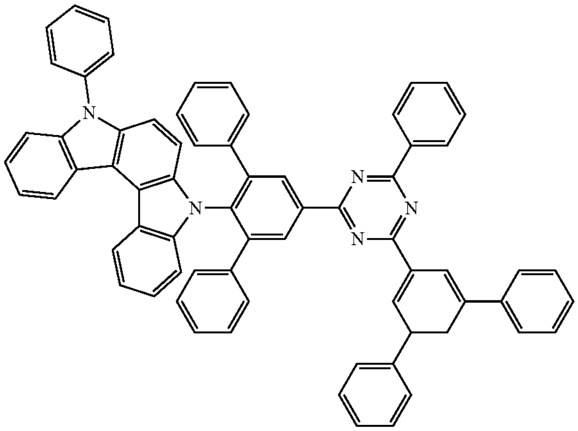

-continued
647
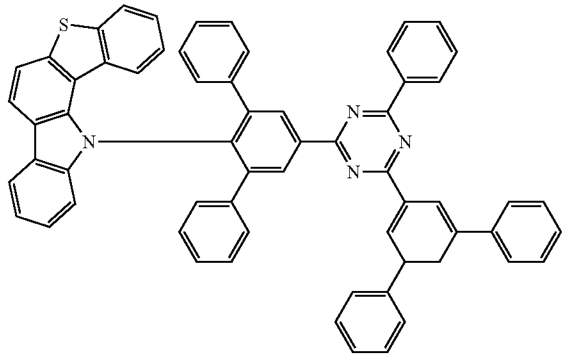
648
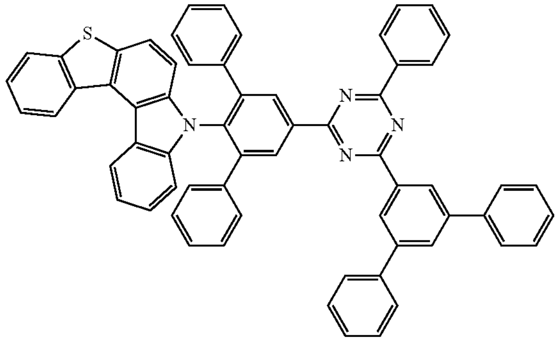
649
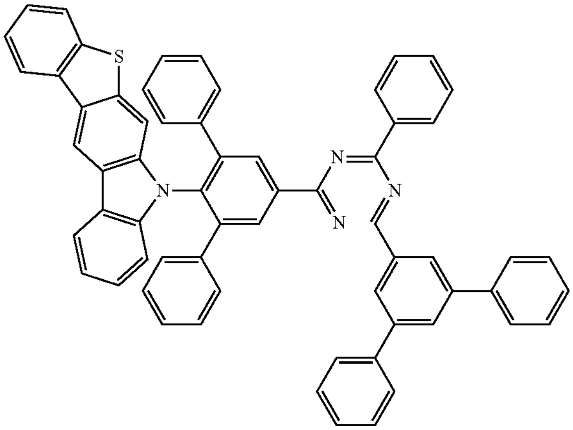
650
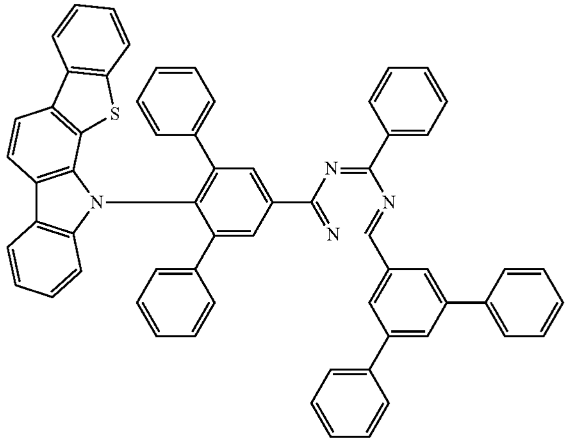
-continued
651
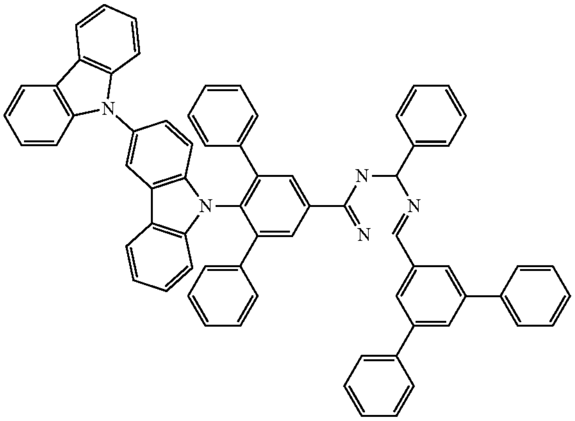
652
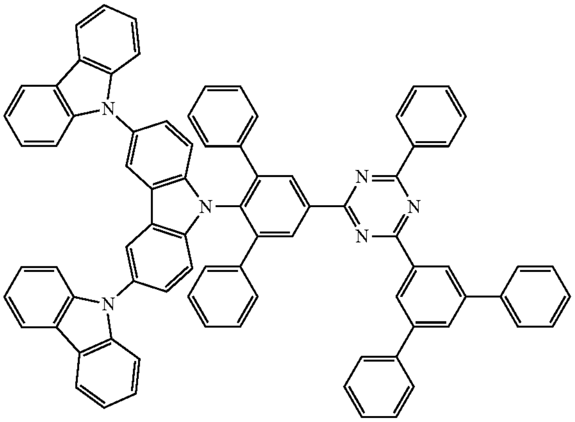
653
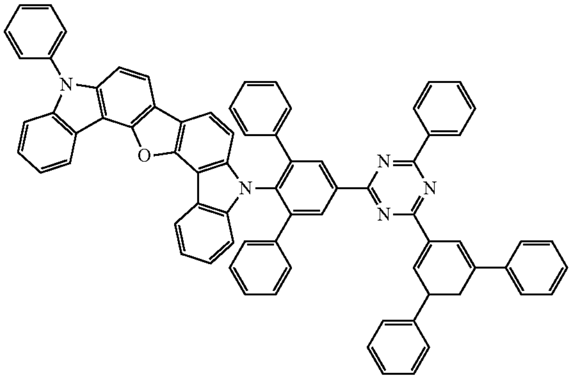

-continued
654
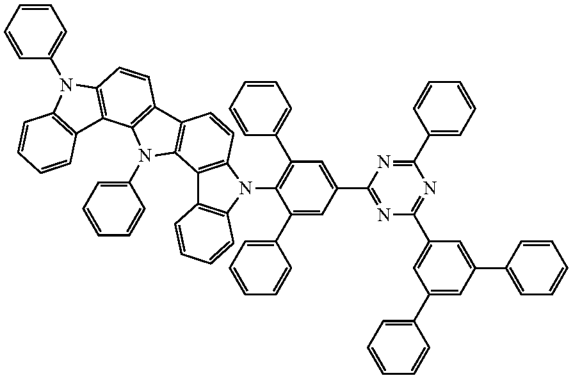
655
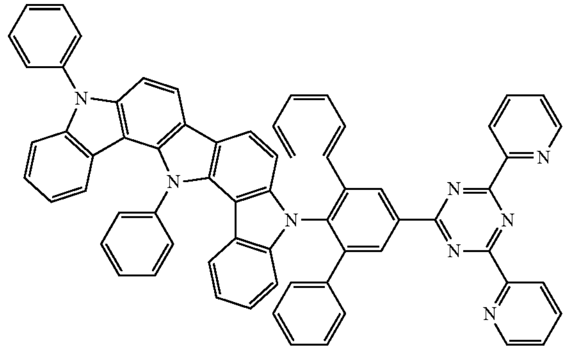
656
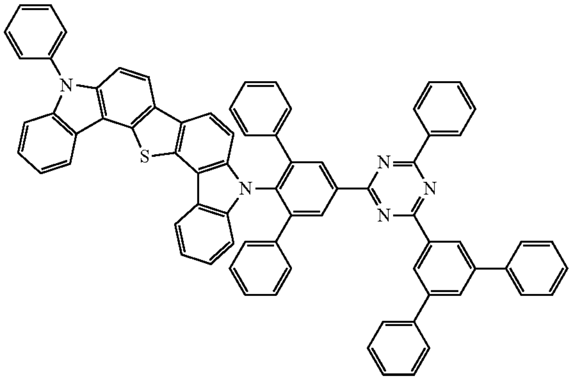
657
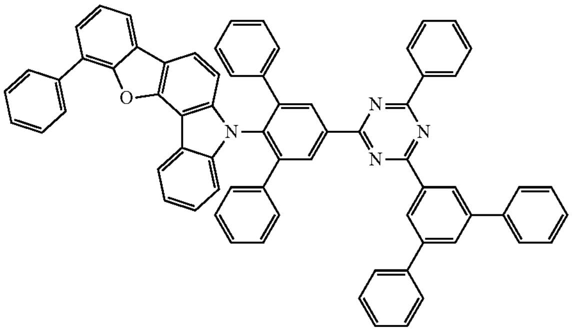
-continued
658
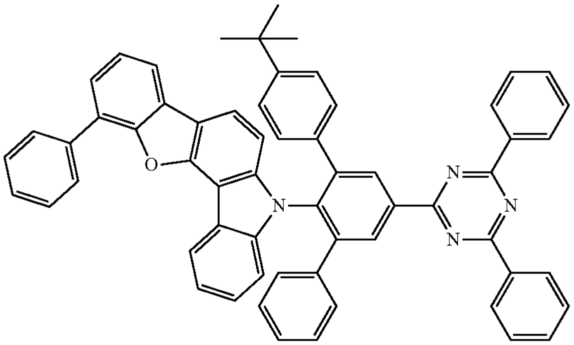
659
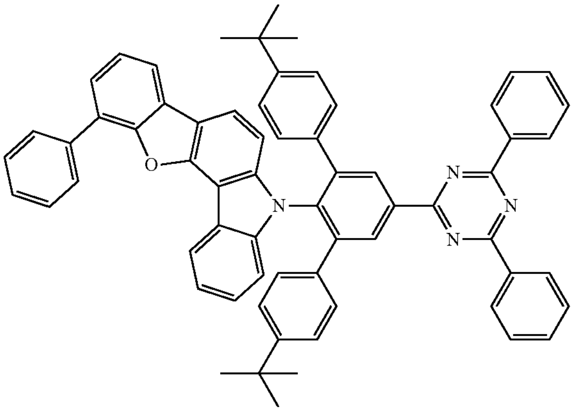
660
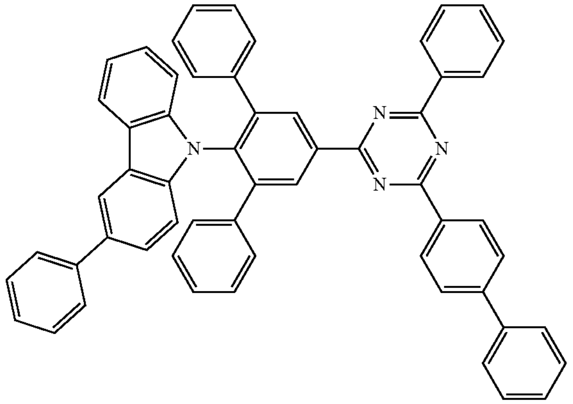
661
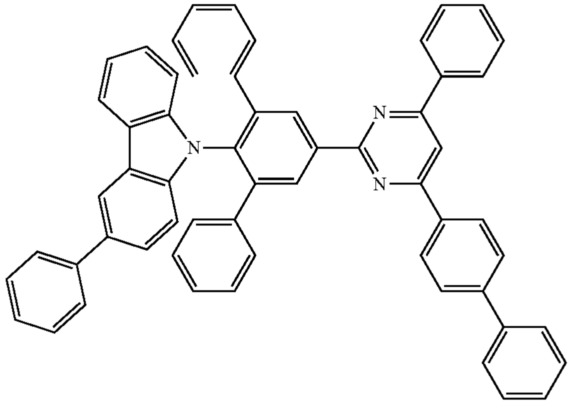

-continued
662
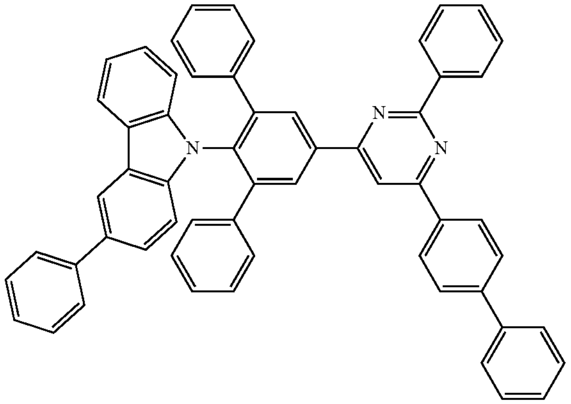
663
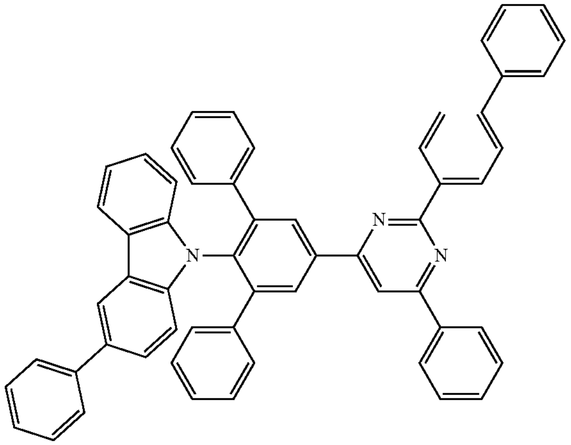
664
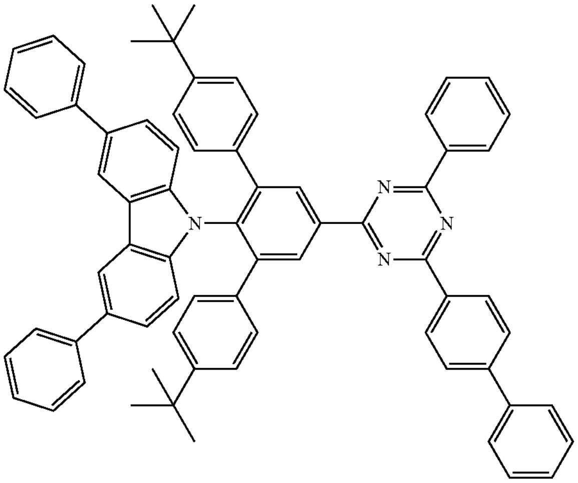
-continued
665
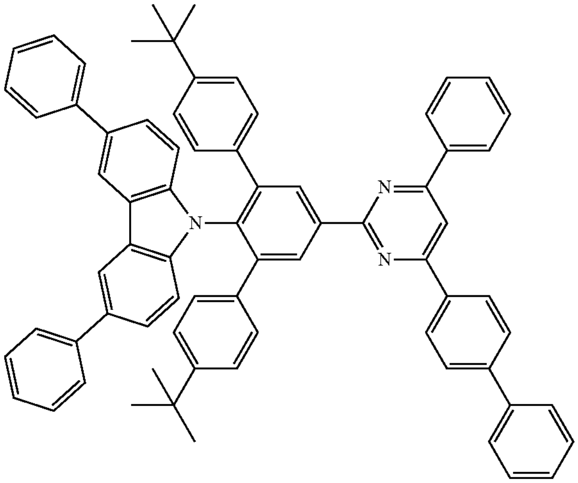
666
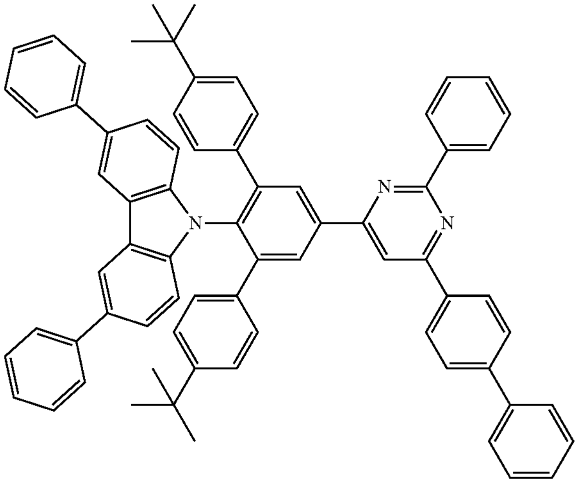
667
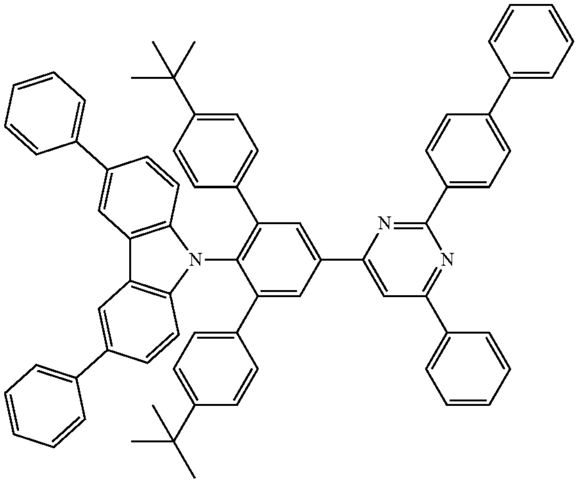

-continued
668
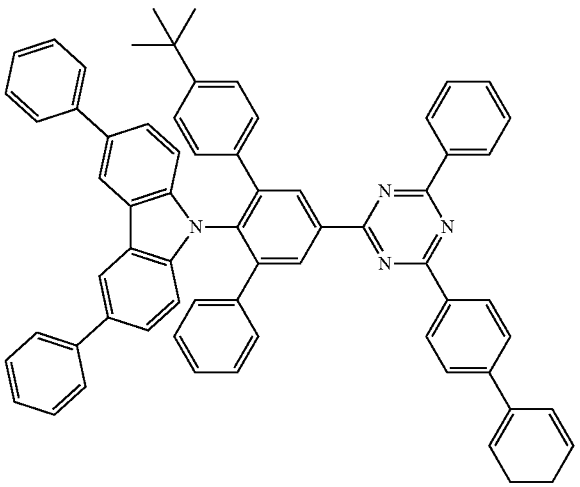
669
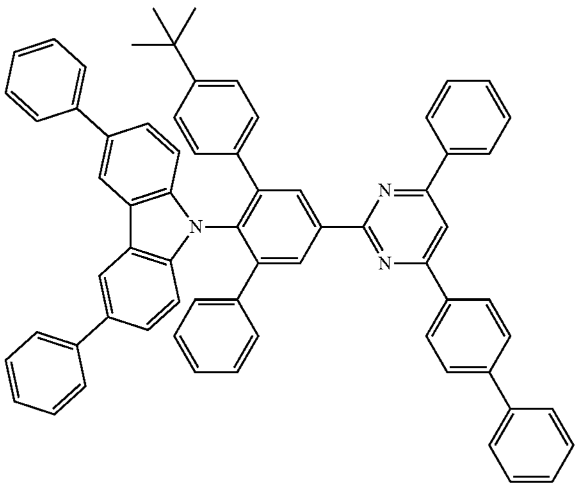
670
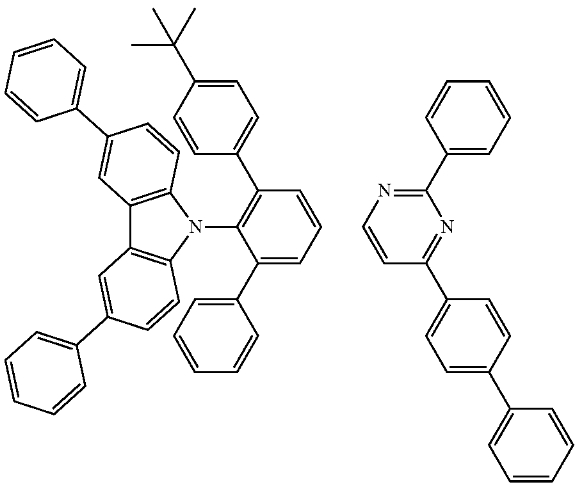
-continued
671
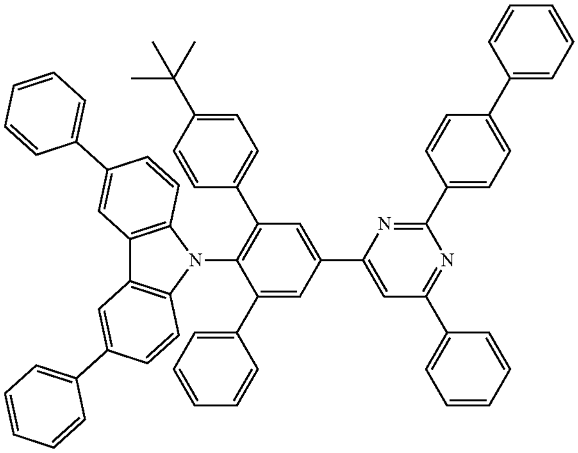
672
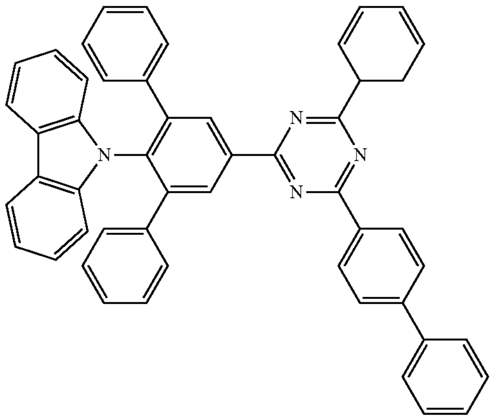
673
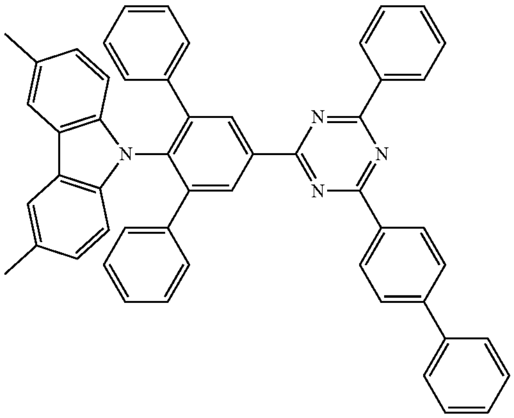

-continued
674
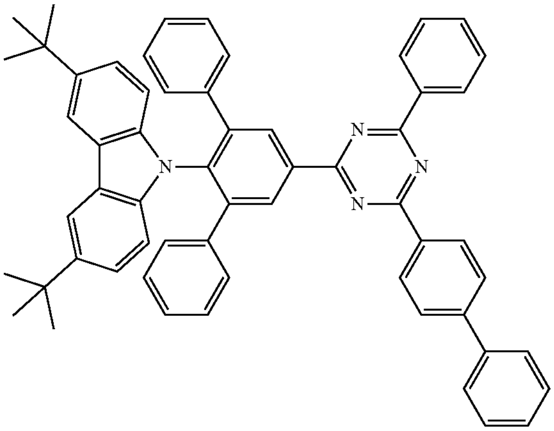
675
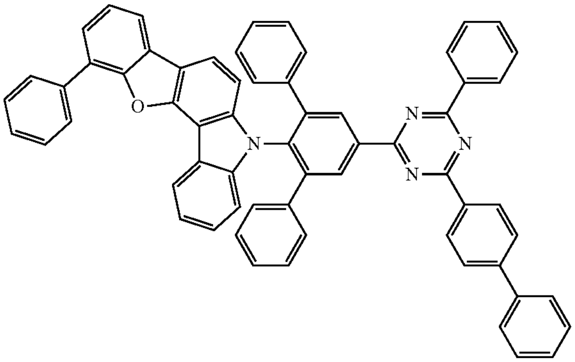
676
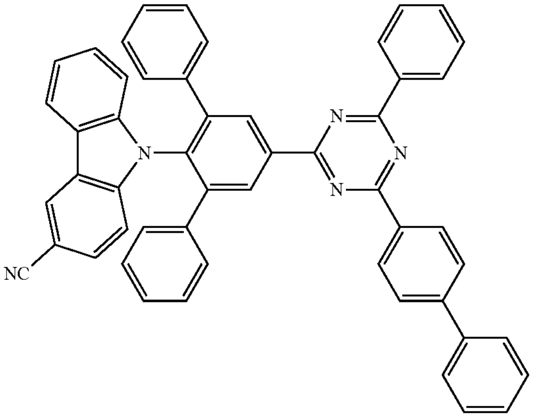
-continued
677
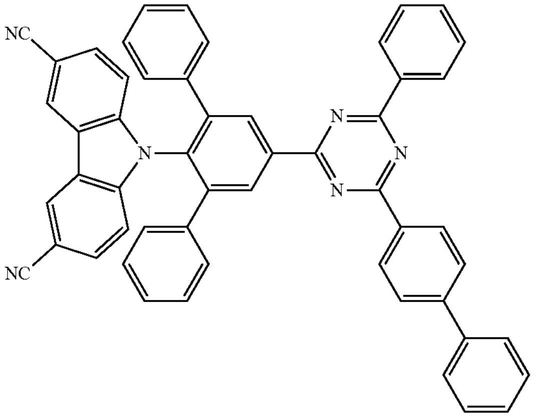
678
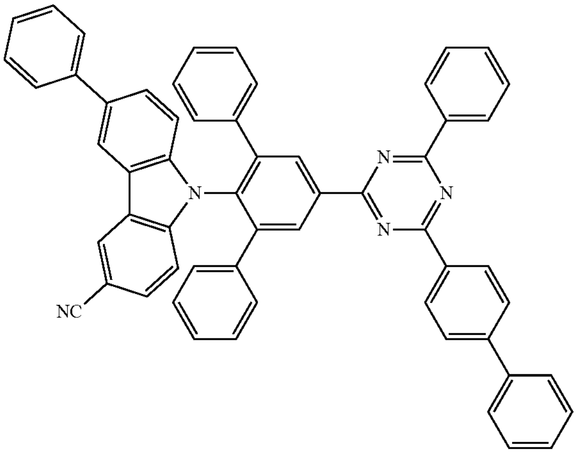
679
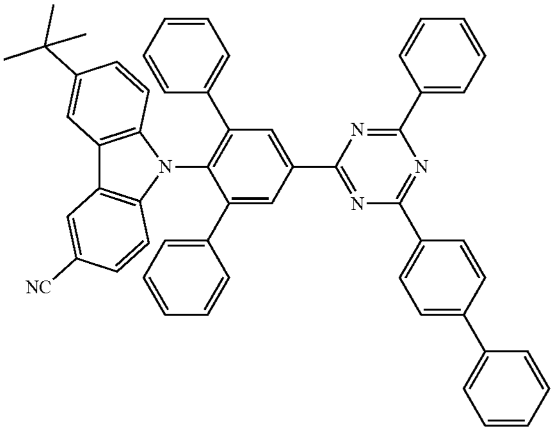

-continued
680
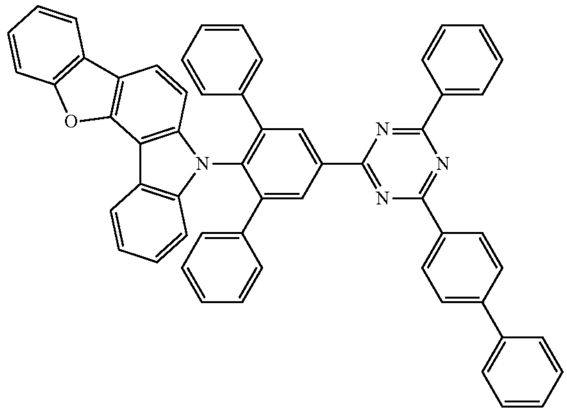
681
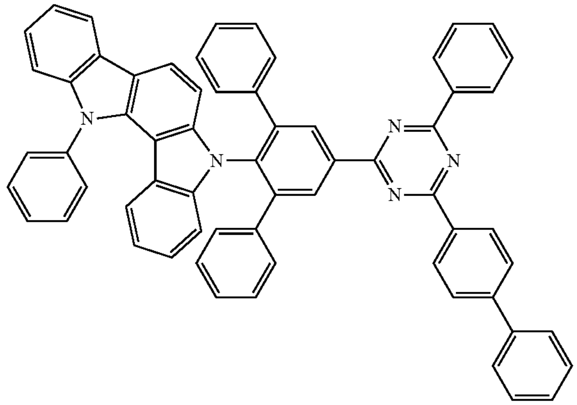
682
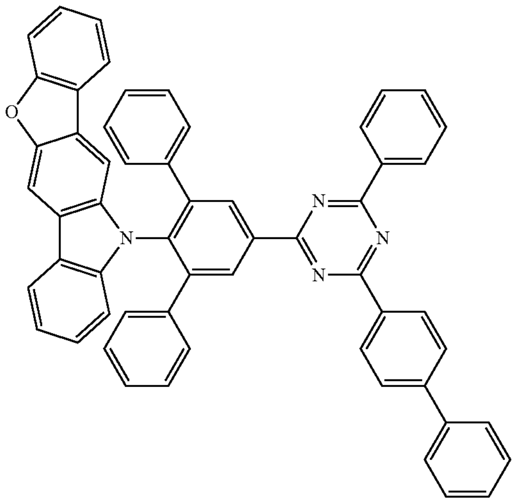
-continued
683
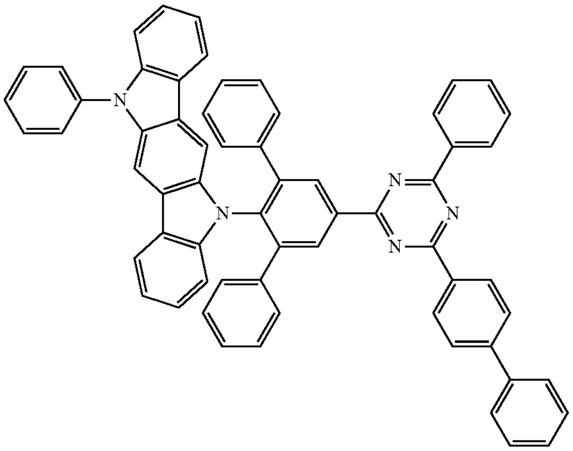
684
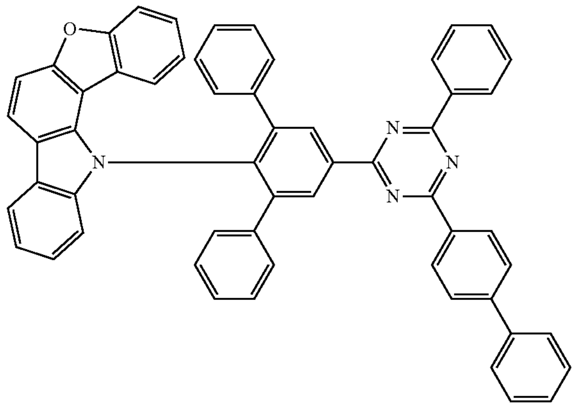
685
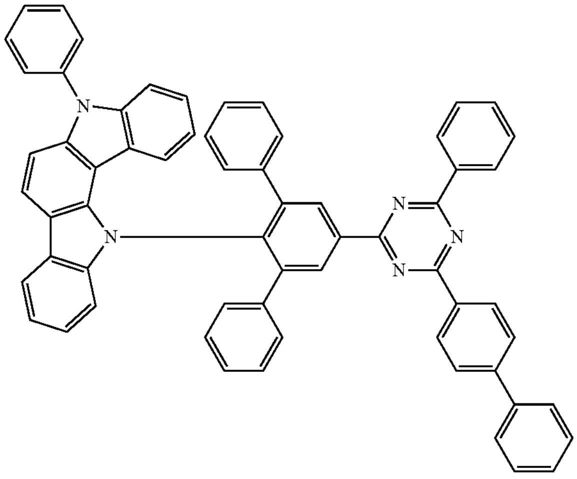

-continued
686
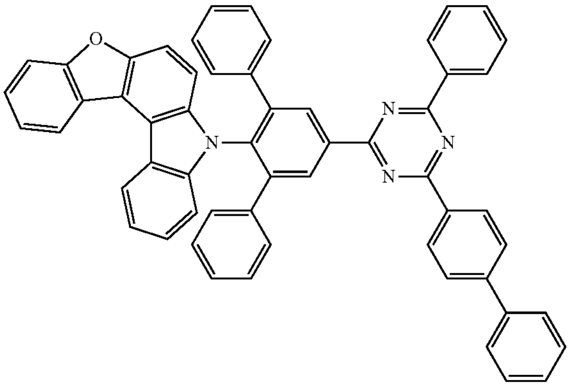
687
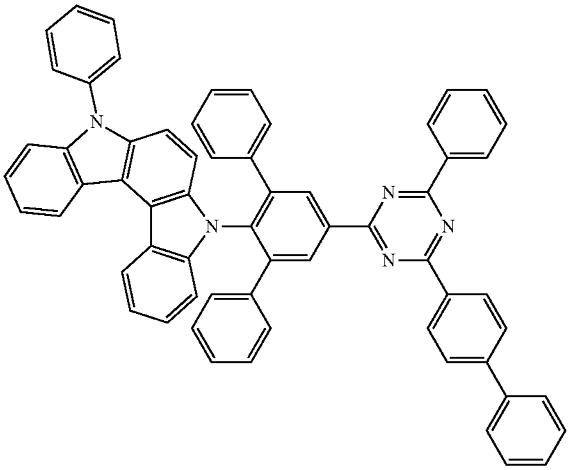
688
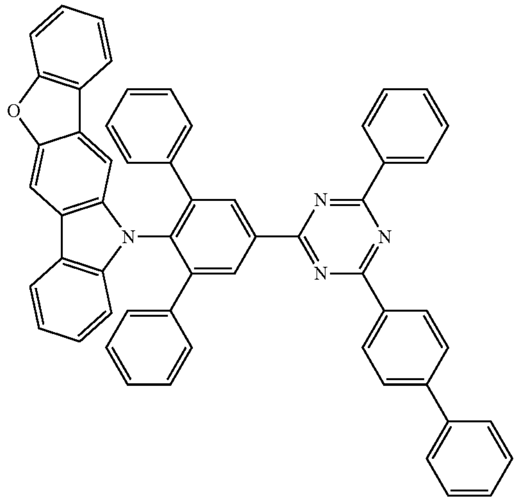
-continued
689
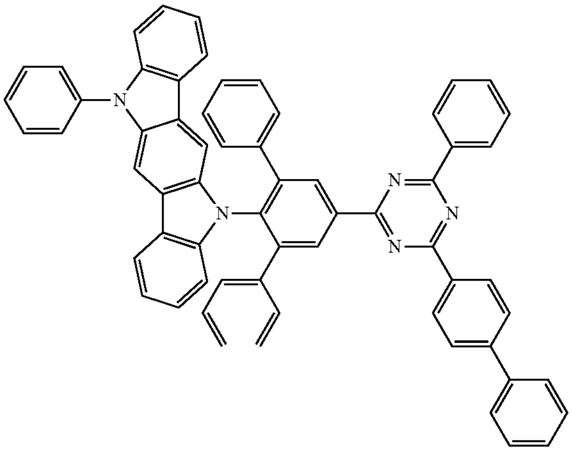
690
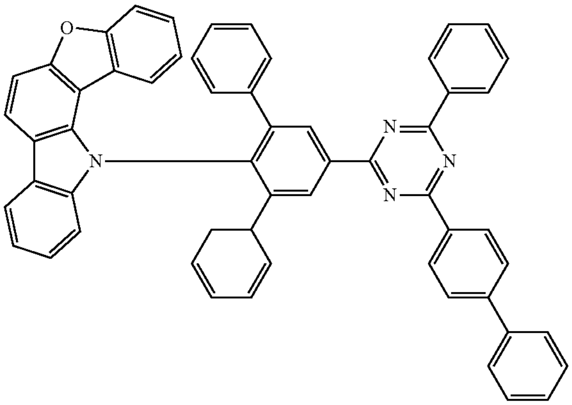
691
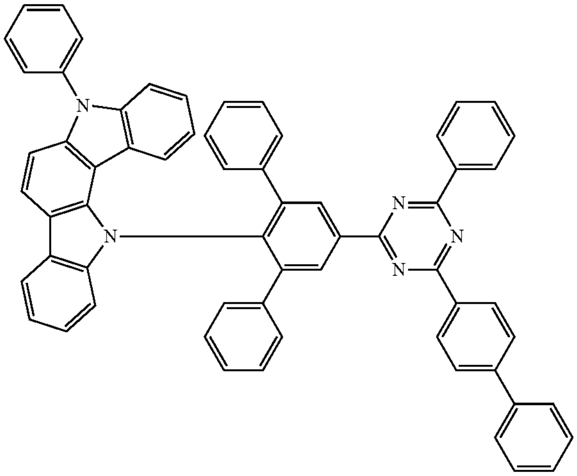

-continued
692
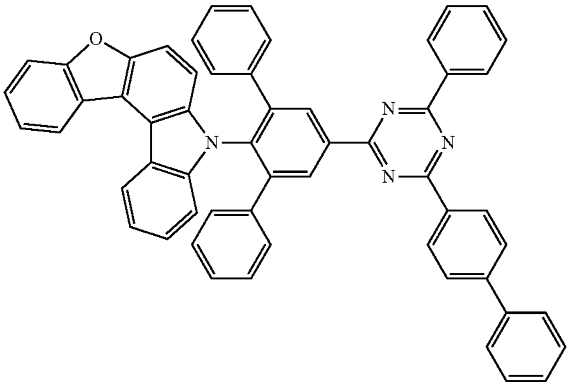
693
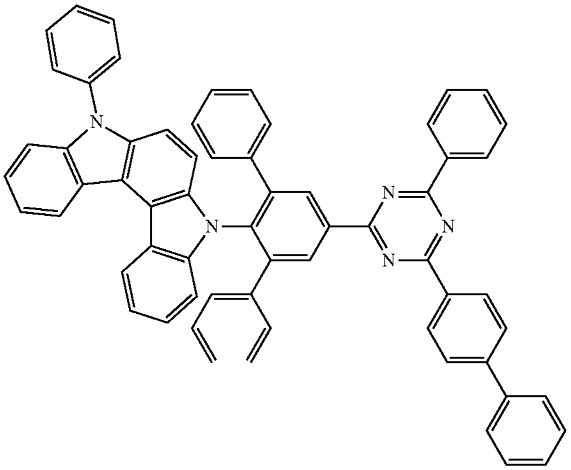
694
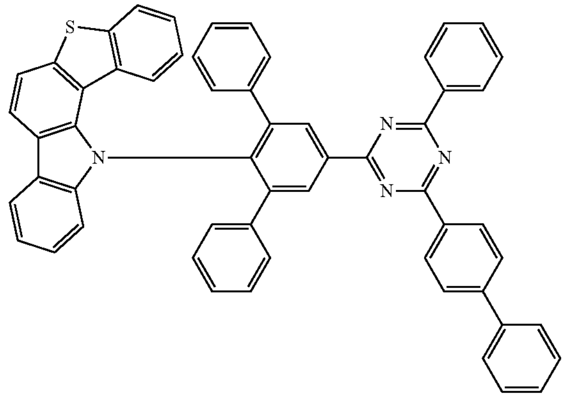
-continued
695
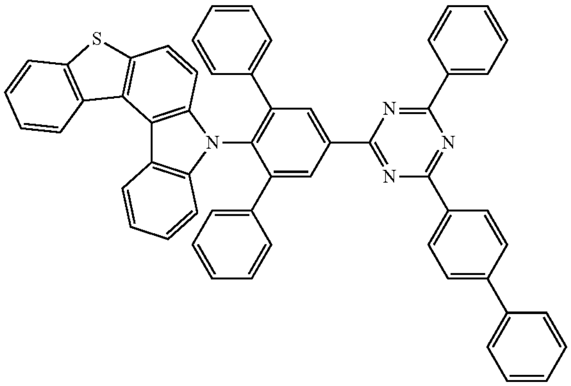
696
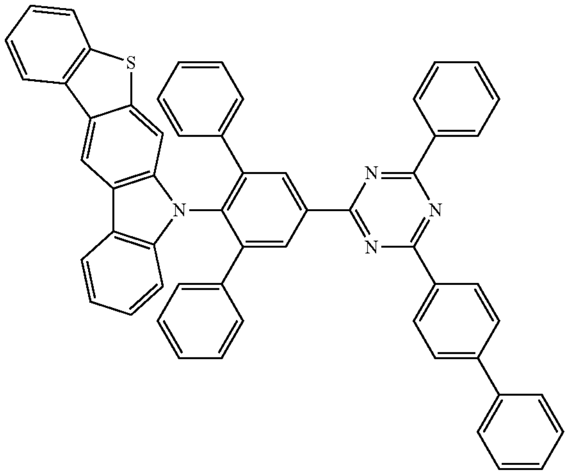
697
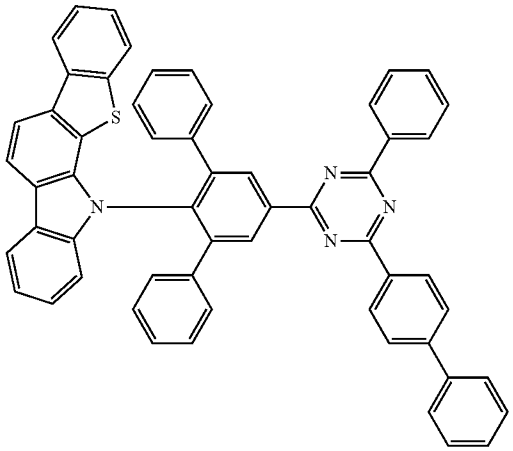

698
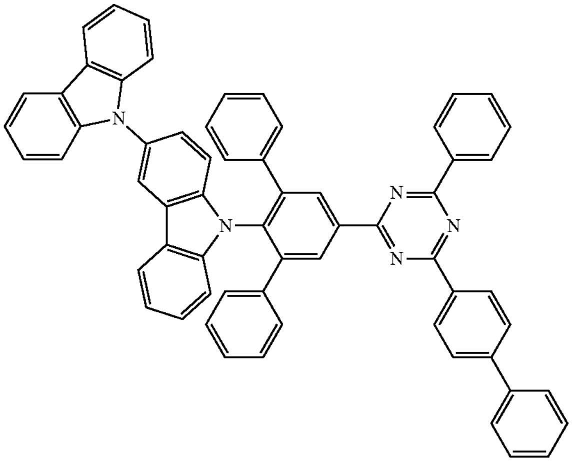
699
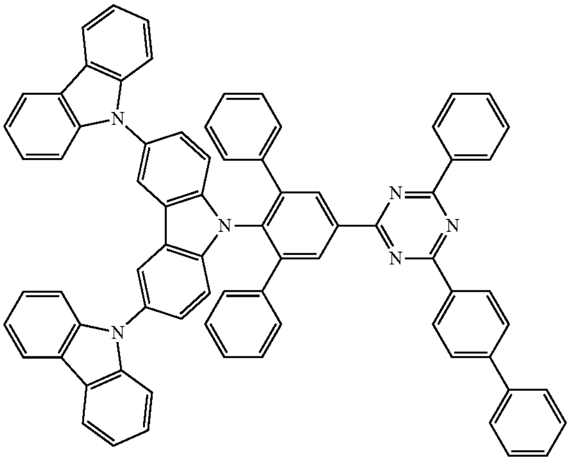
700
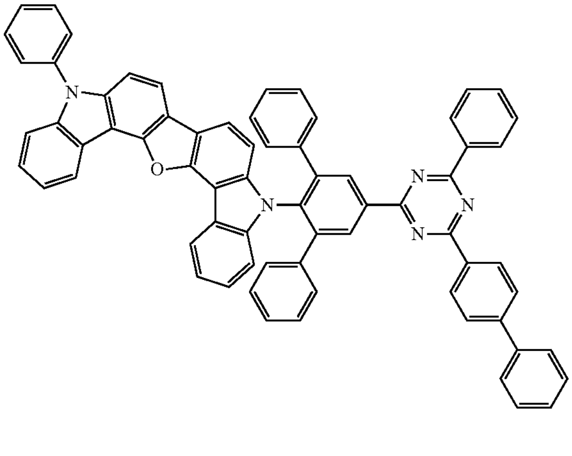
701
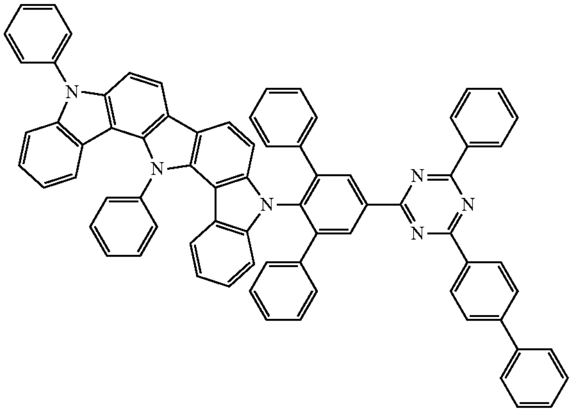
702
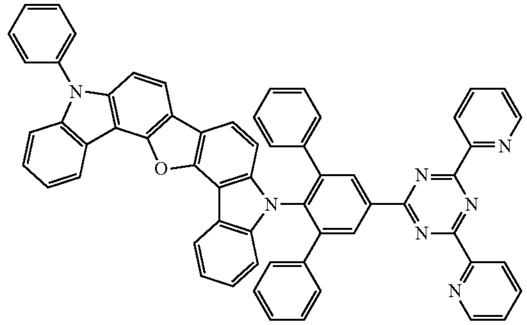
703
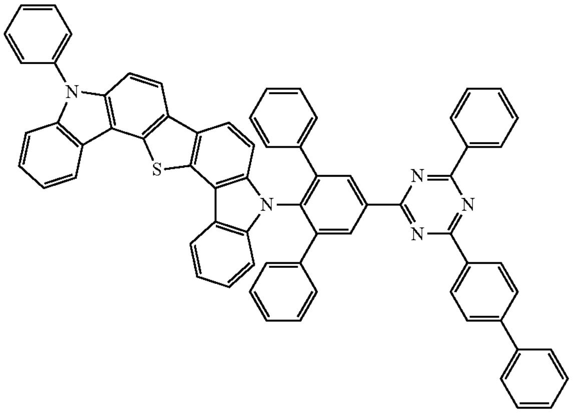
704
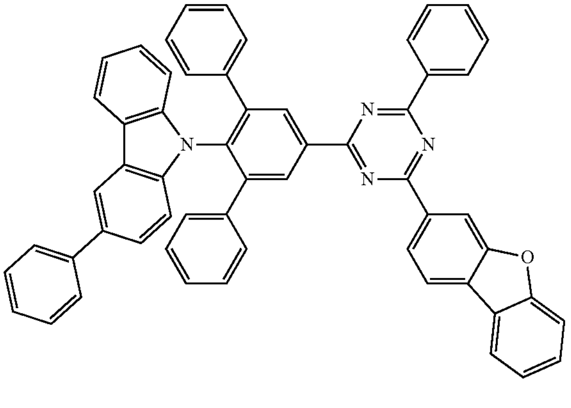

-continued
705
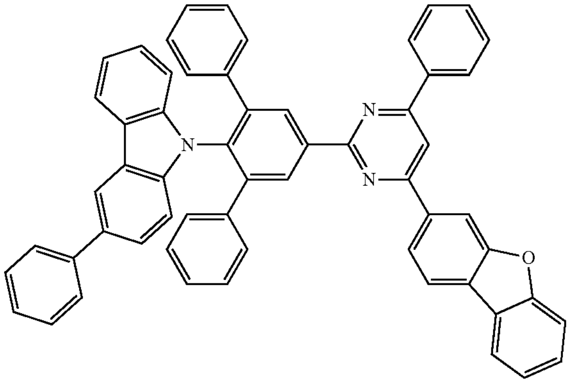
706
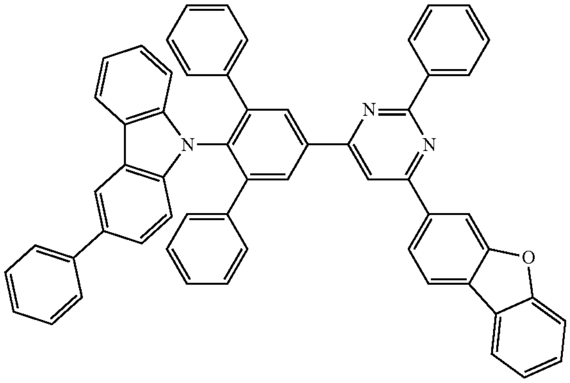
707
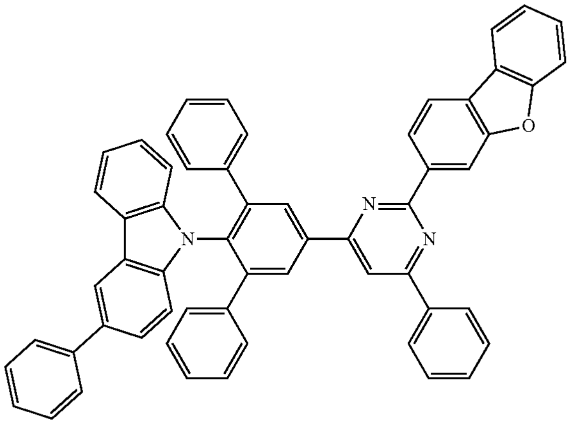
-continued
708
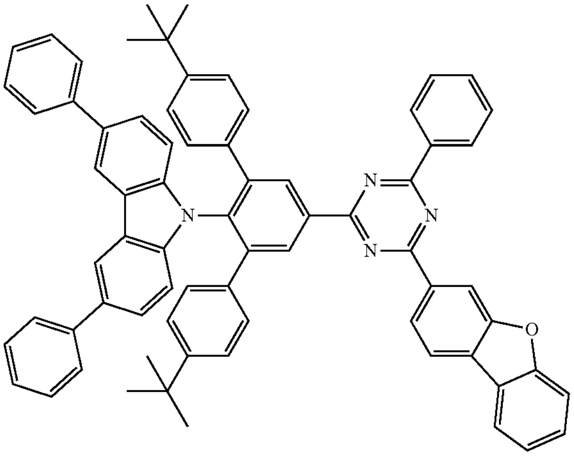
709
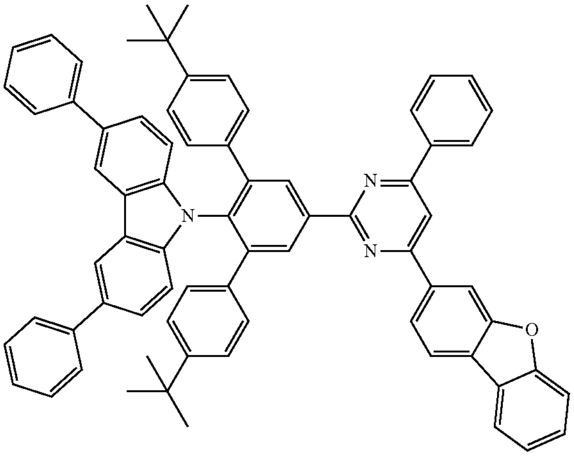
710
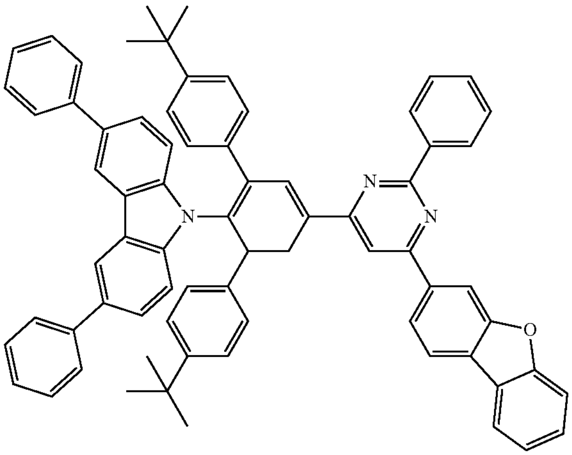

-continued
711
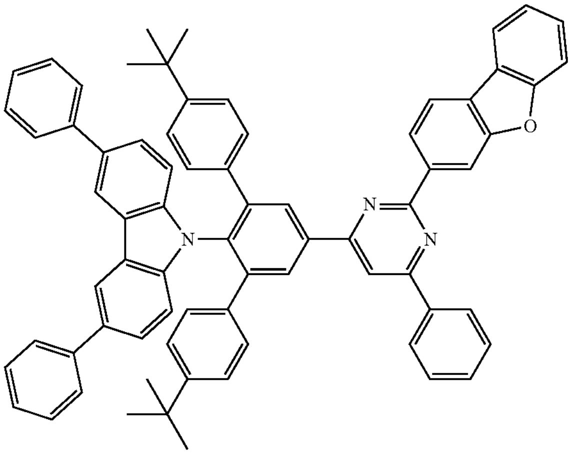
712
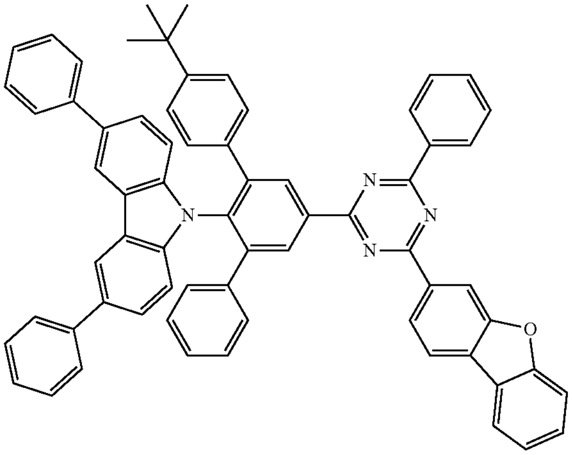
713
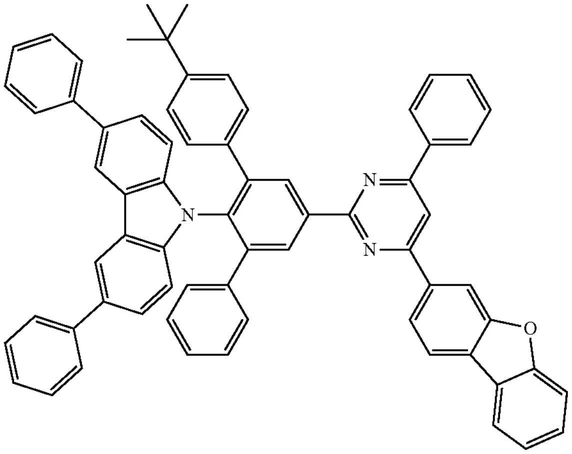
-continued
714
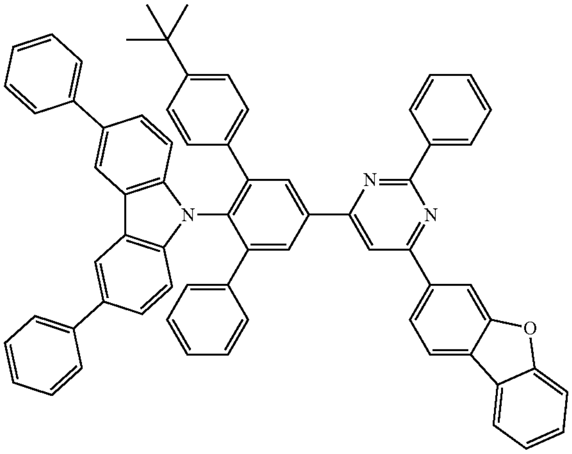
715
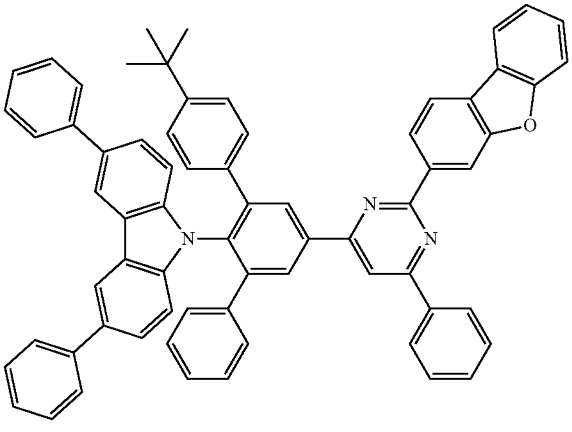
716
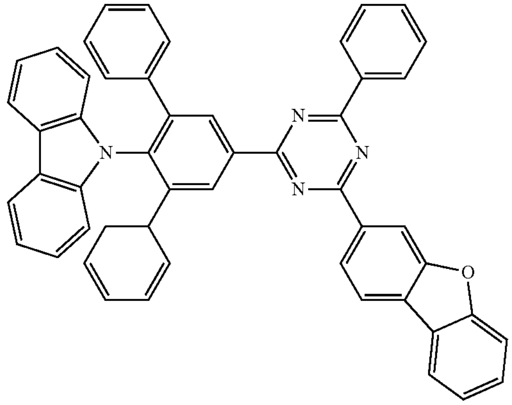

-continued
717
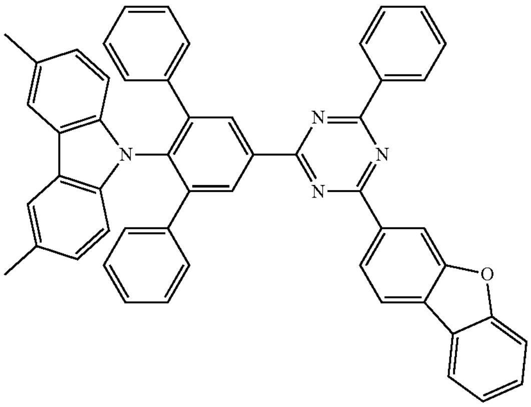
718
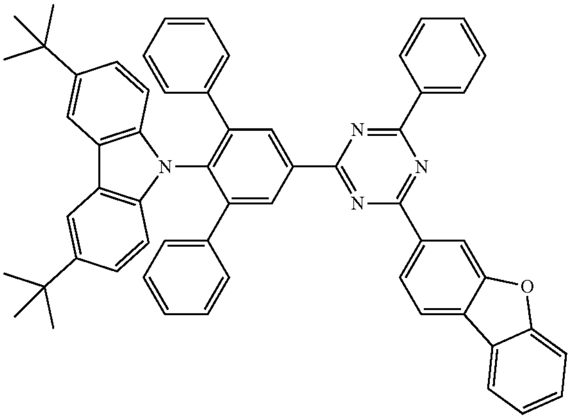
719
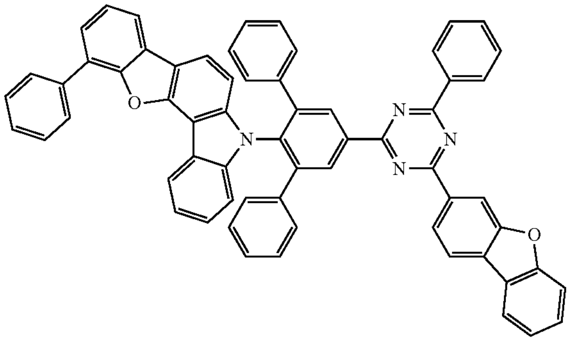
-continued
720
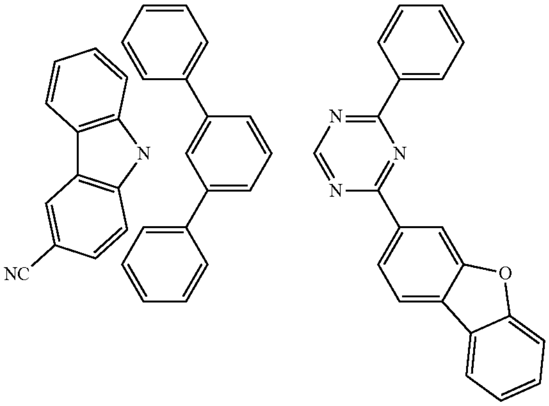
721
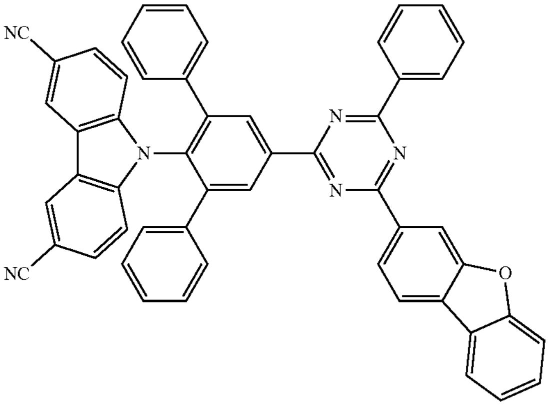
722
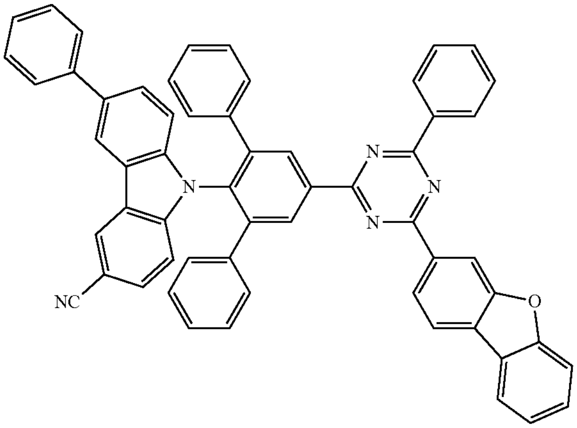

723
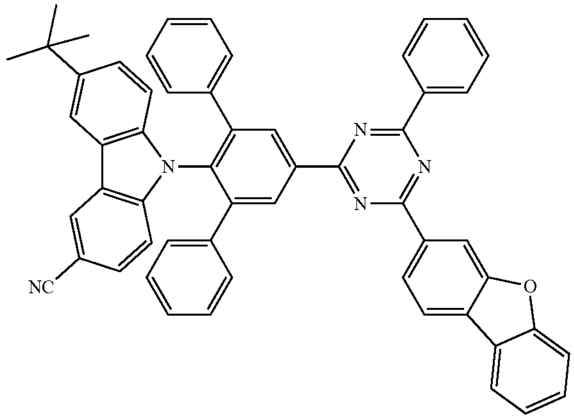
724
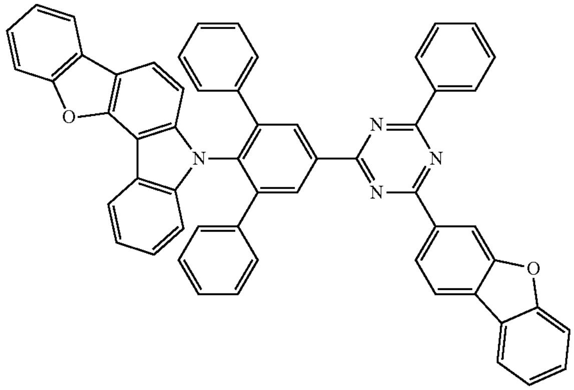
725
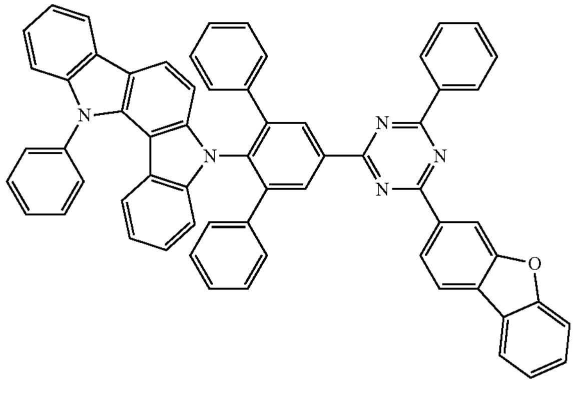
726
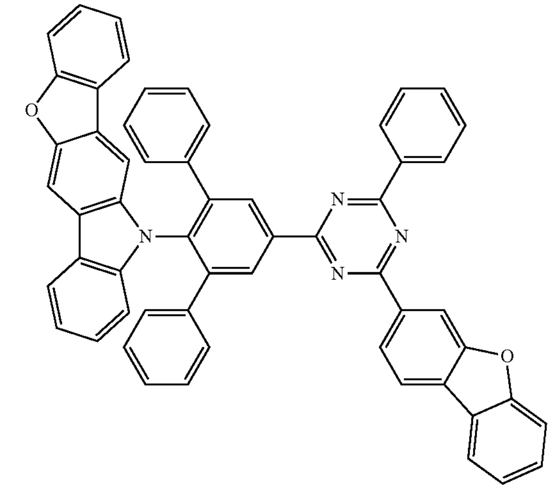
727
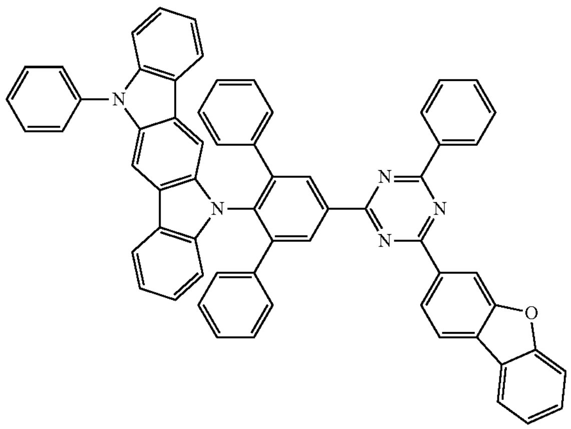
728
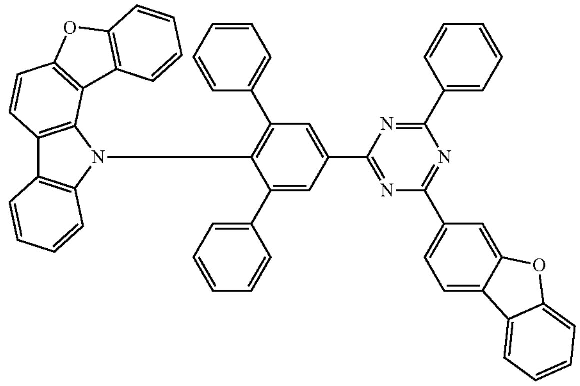

-continued
729
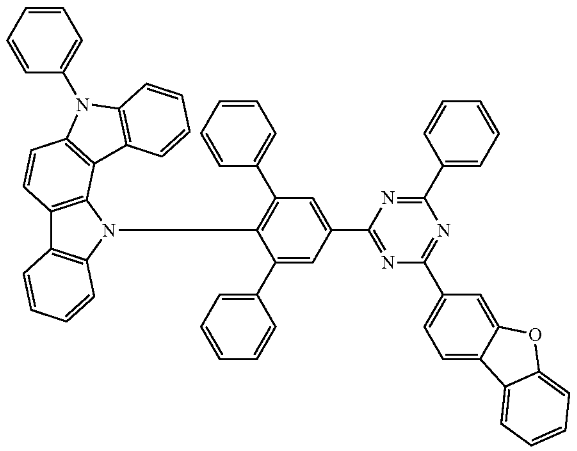
730
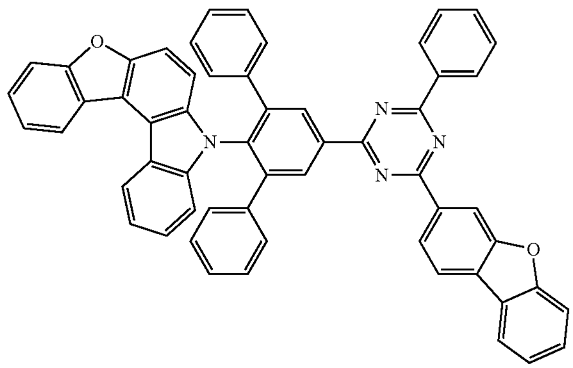
731
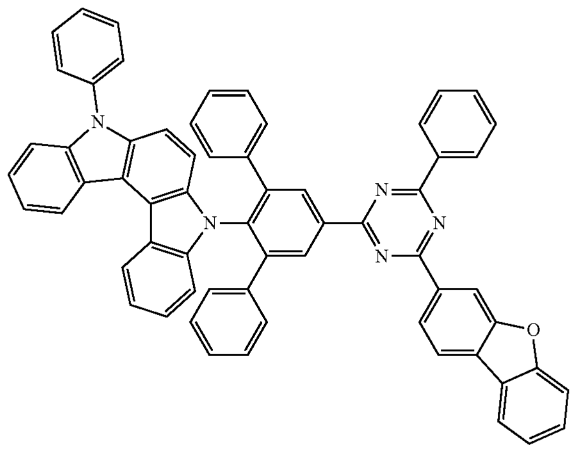
-continued
732
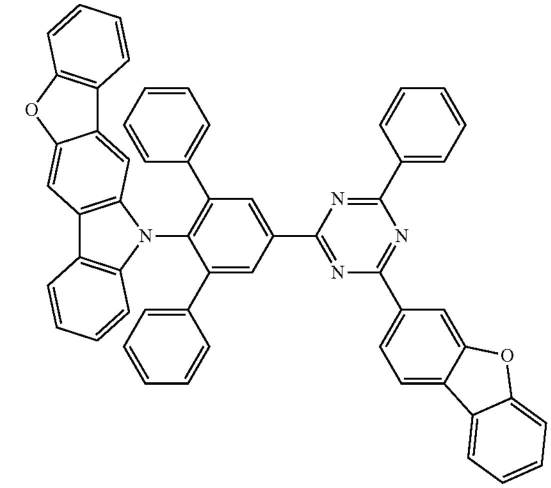
733
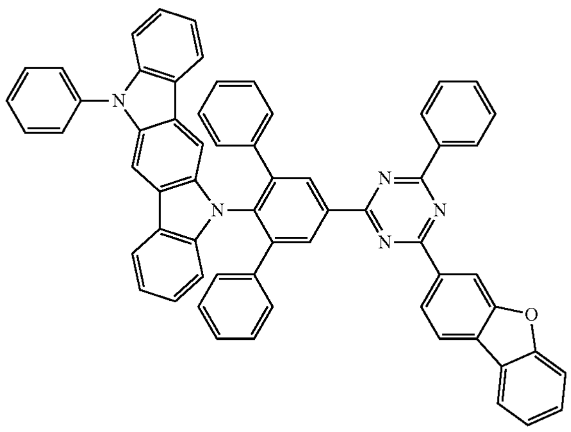
734
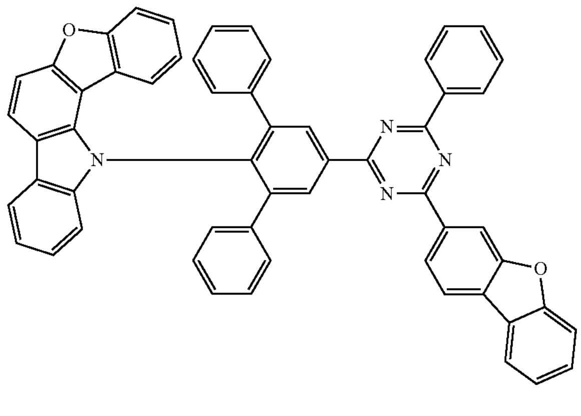

-continued
735
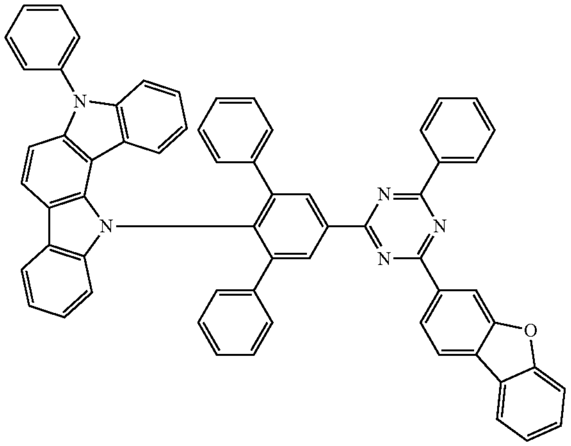
736
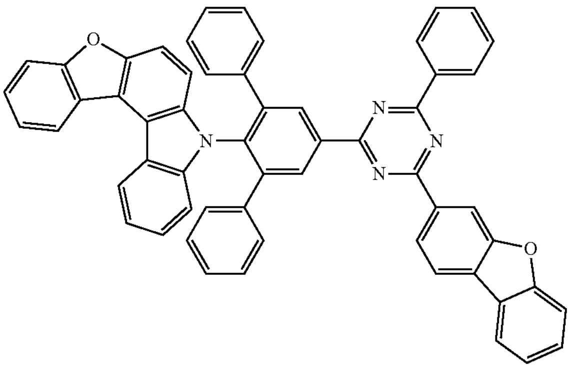
737
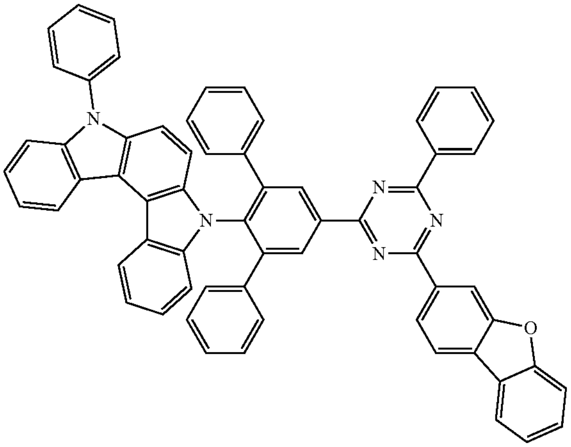
738
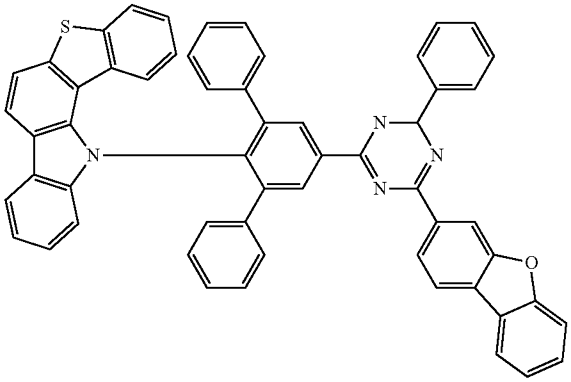
739
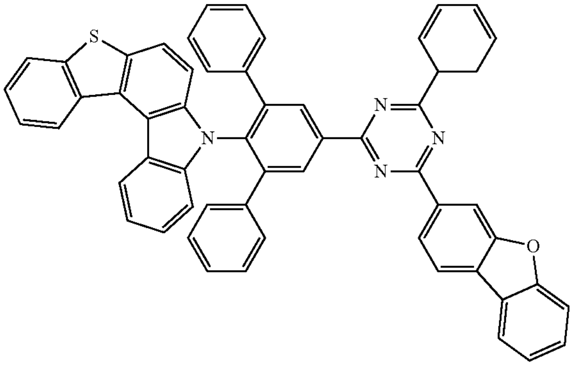

-continued
740
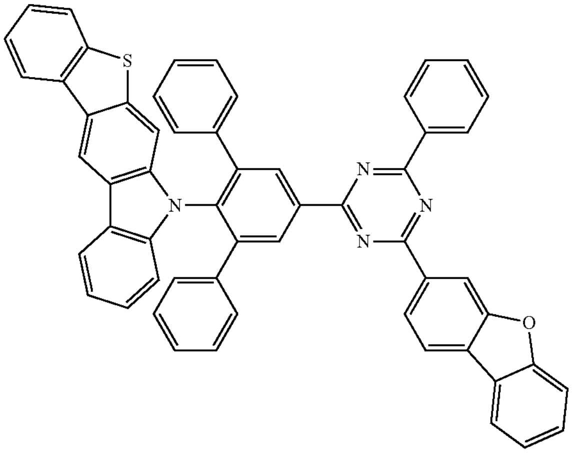
741
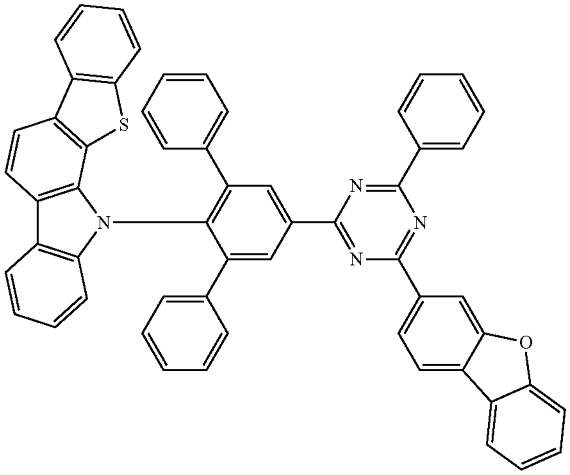
-continued
742
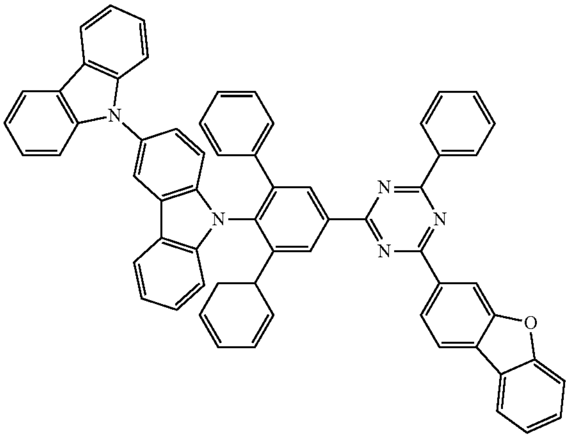
743
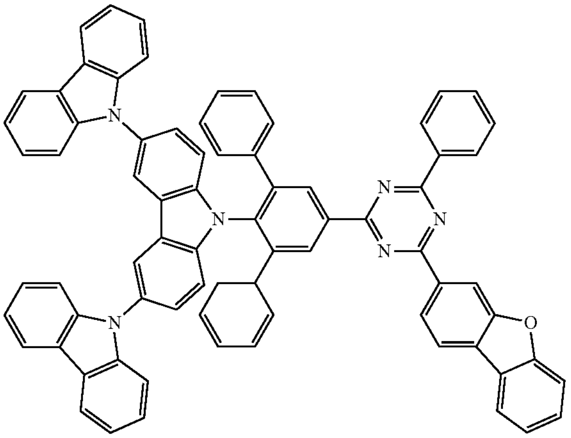
744
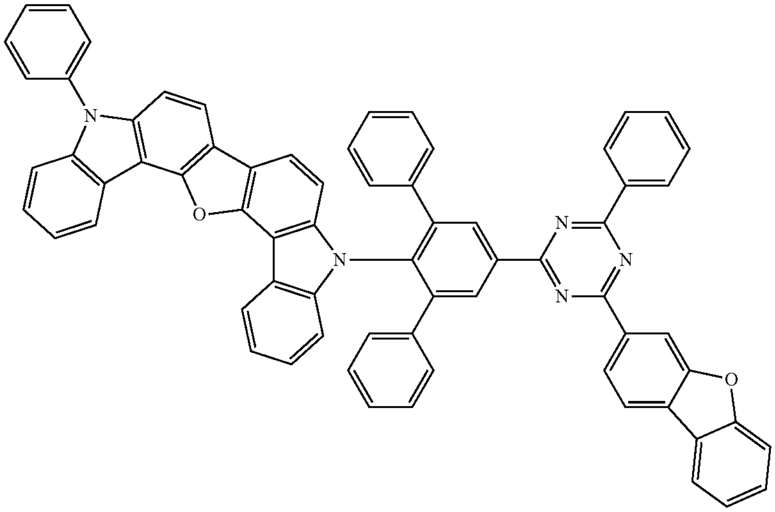

-continued
745
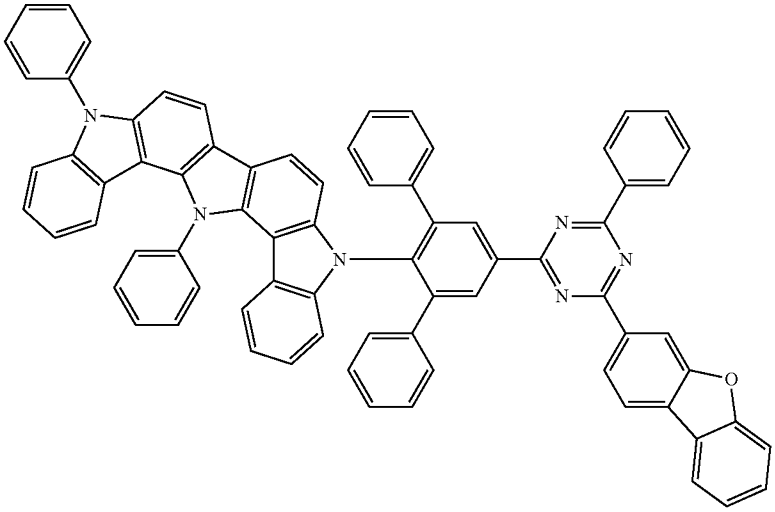
746
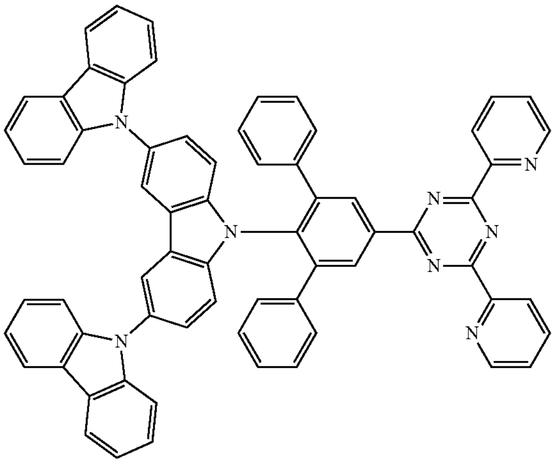
747
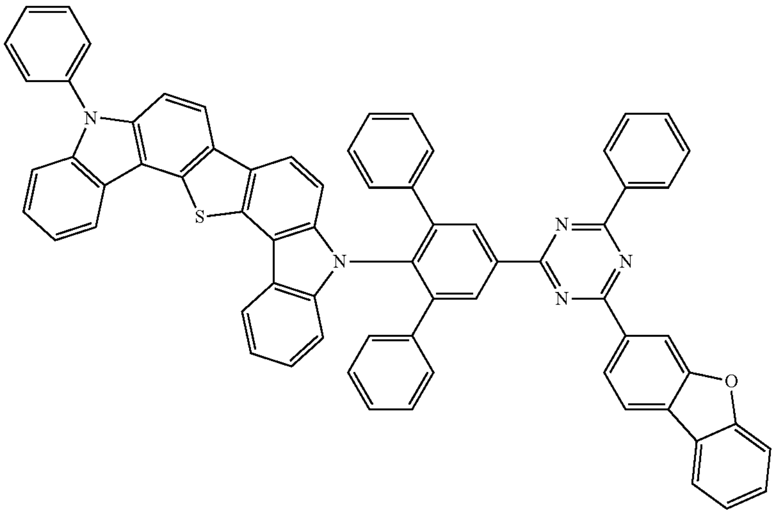

-continued
748
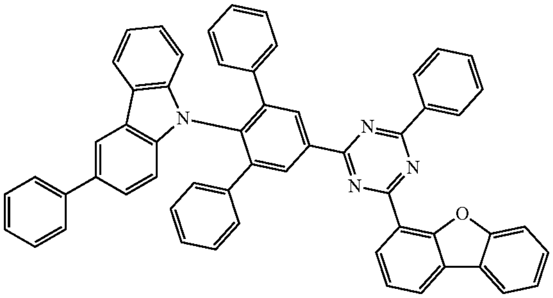
749
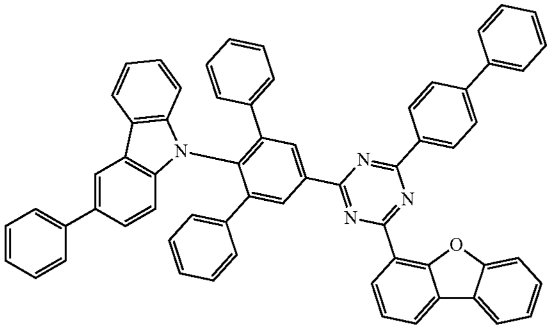
750
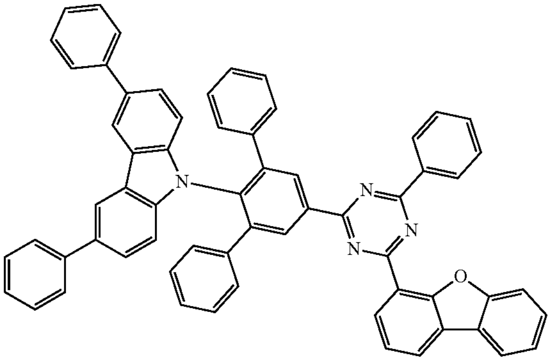
751
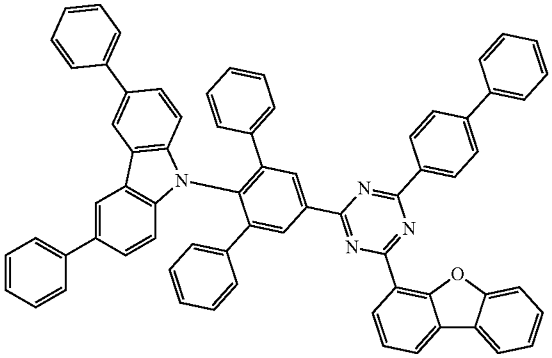
752
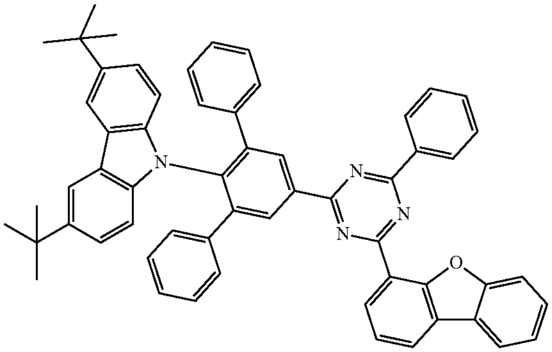
753
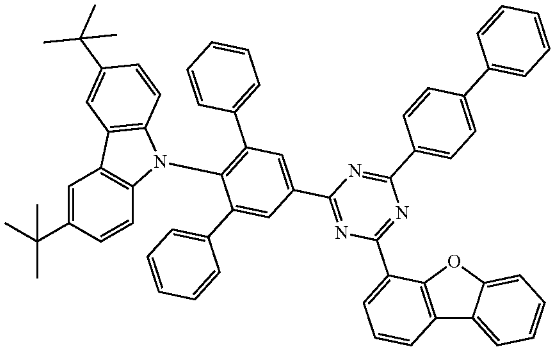
754
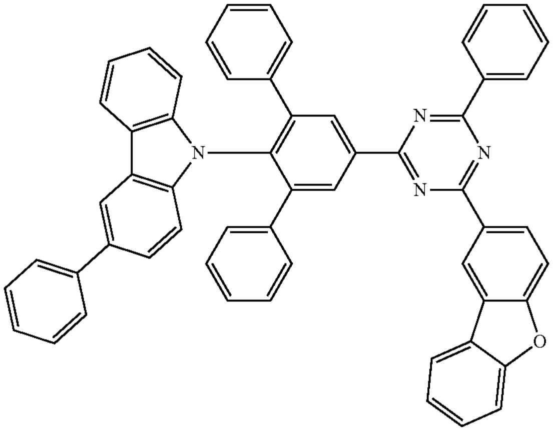
755
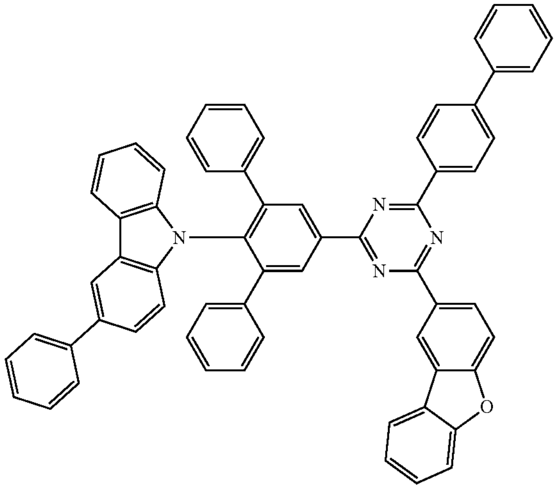

-continued
756
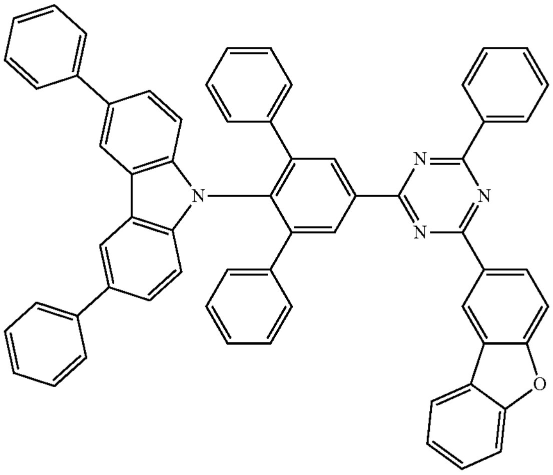
757
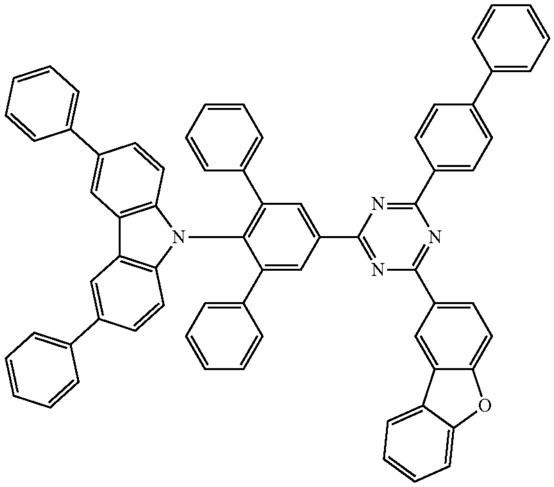
758
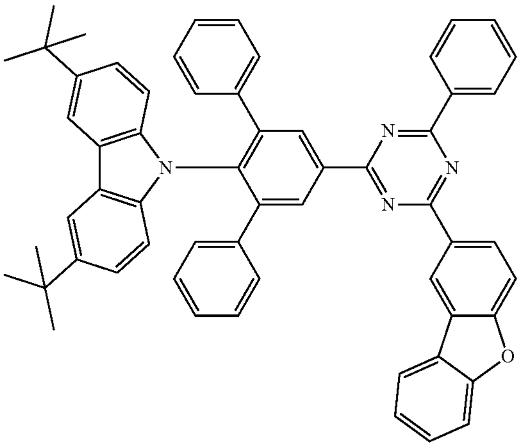
759
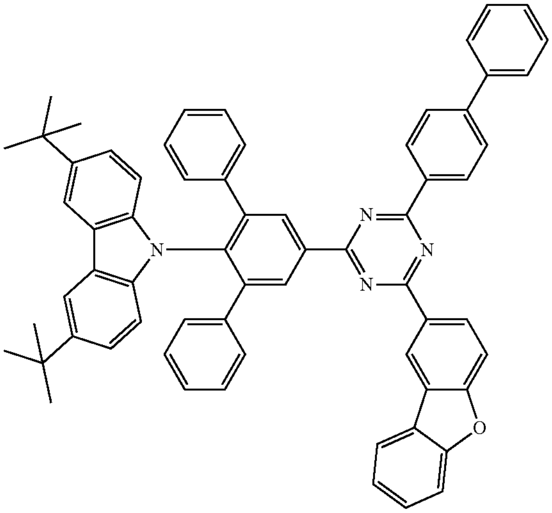
760
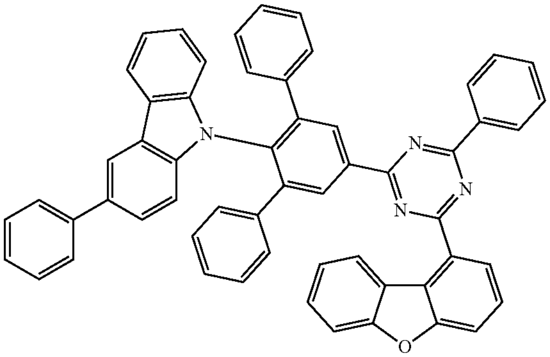
761
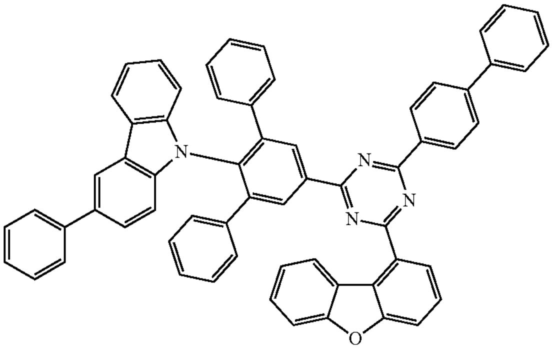

-continued
762
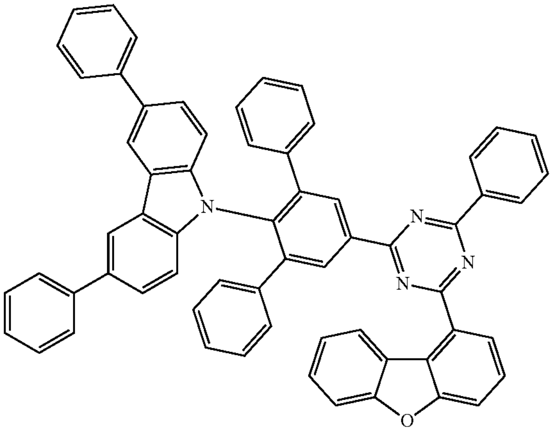
763
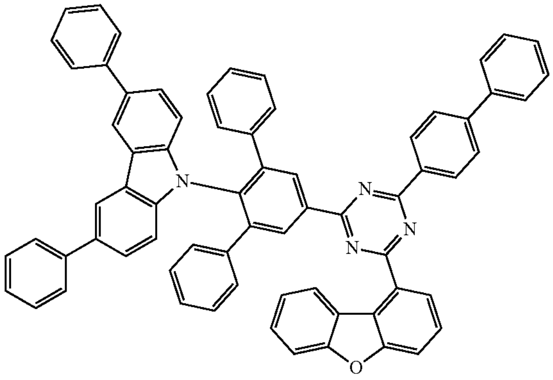
764
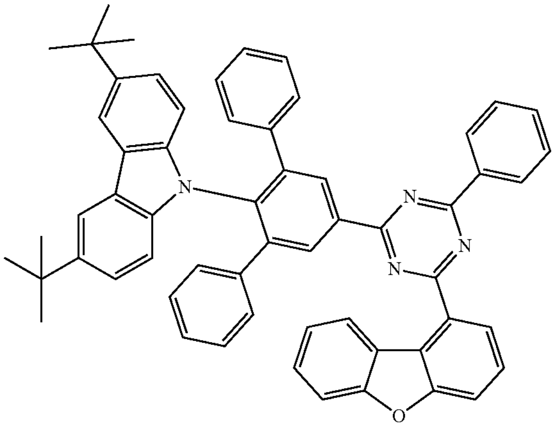
765
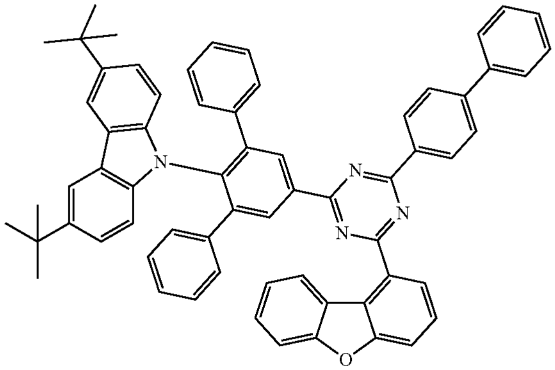
766
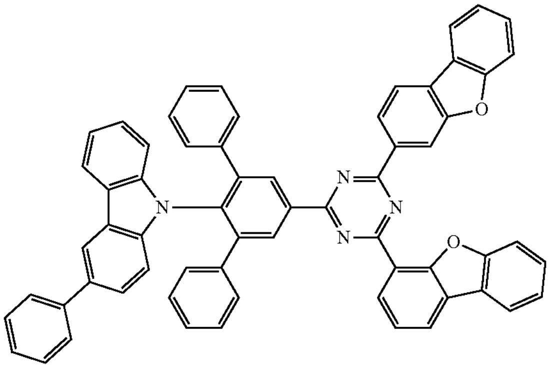
767
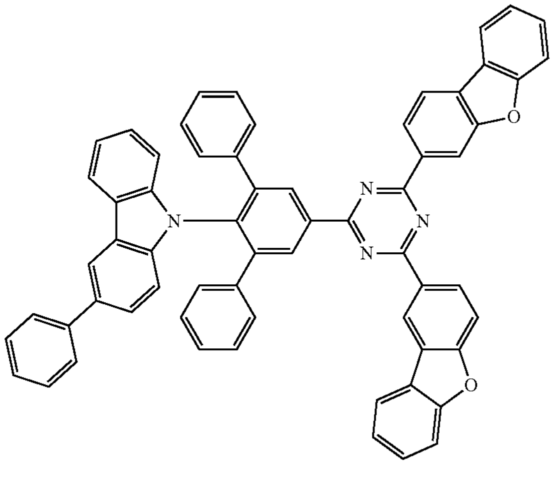

-continued
768
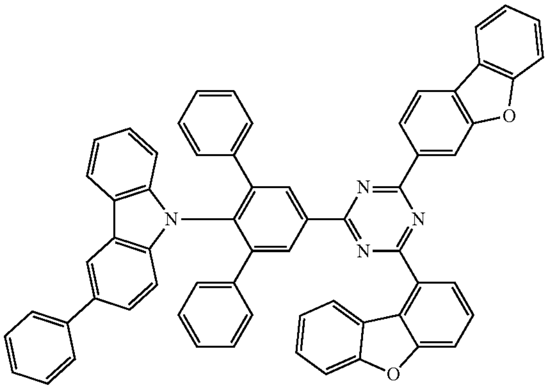
769
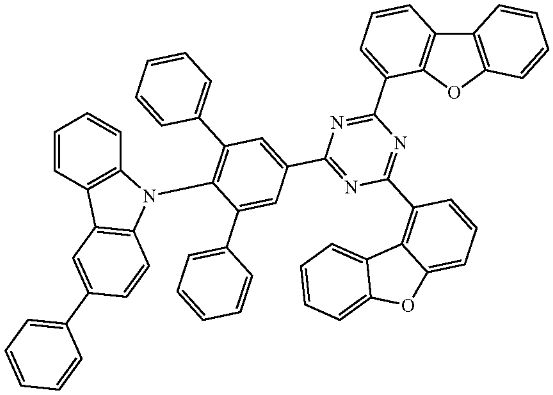
770
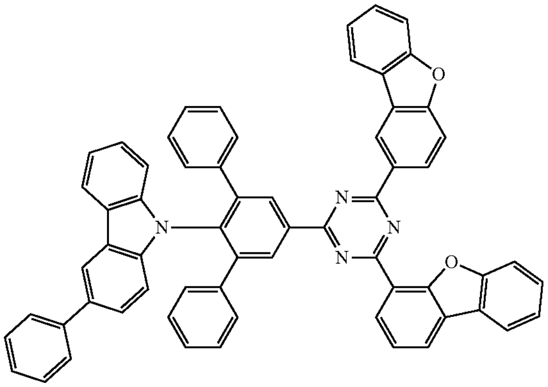
771
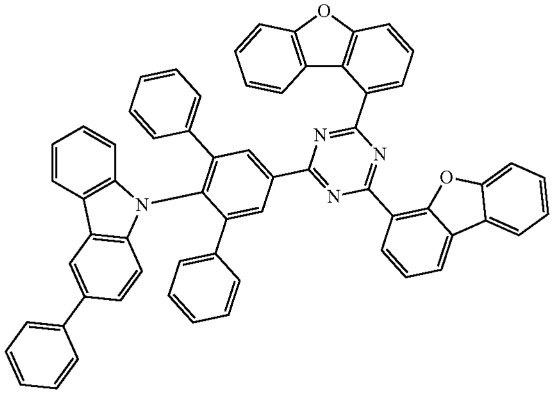
772
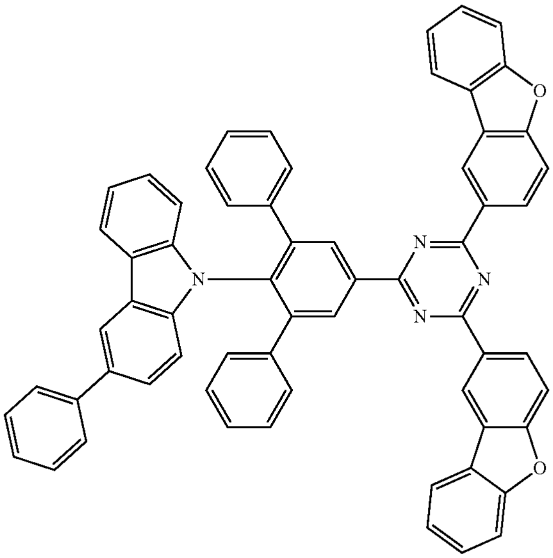
773
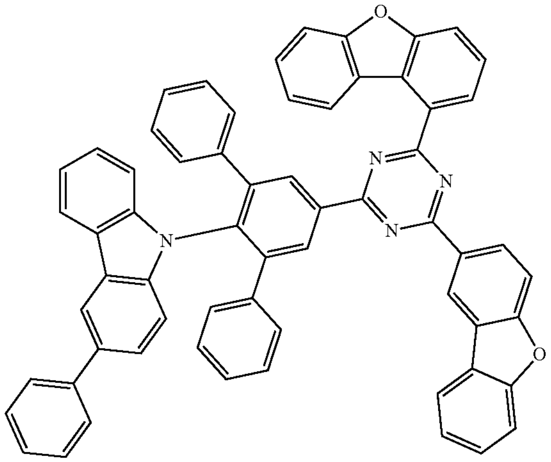

-continued
774
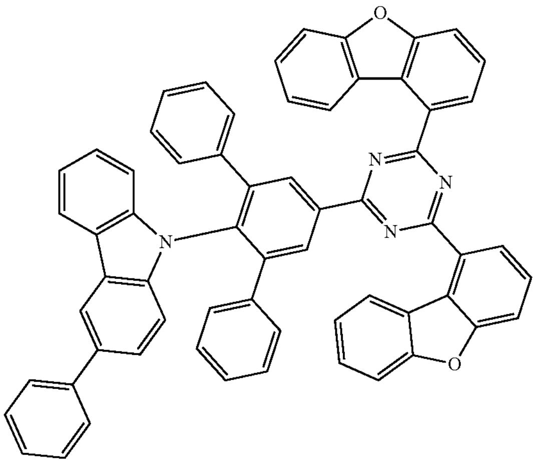
776
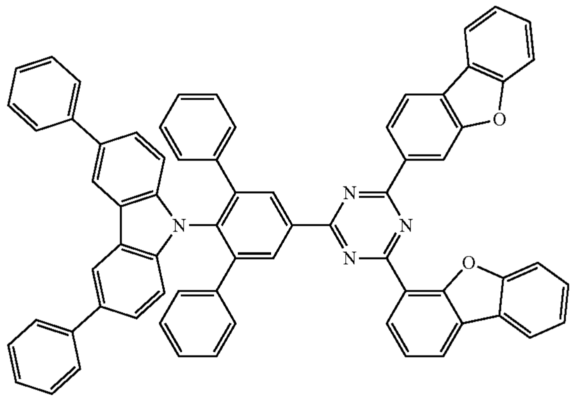
777
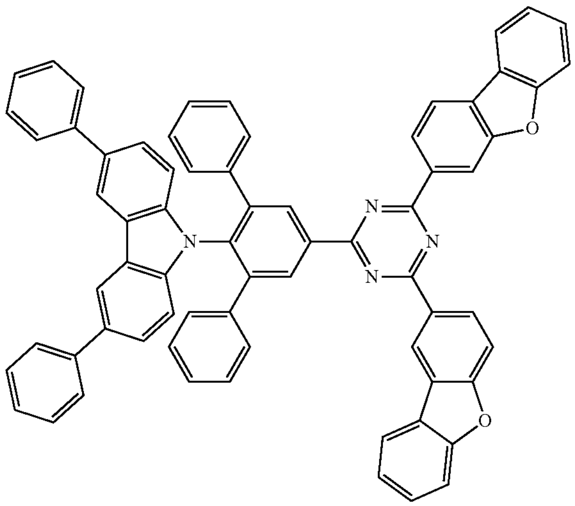
775
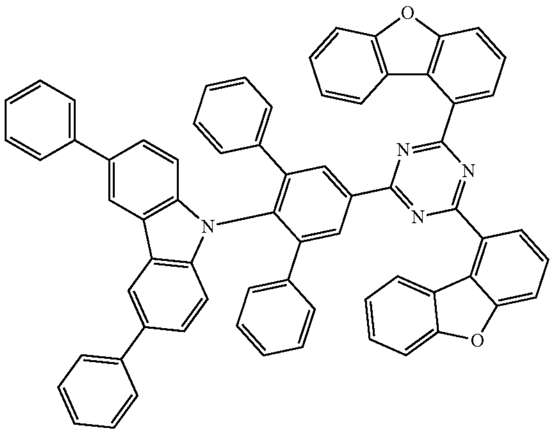
-continued
778
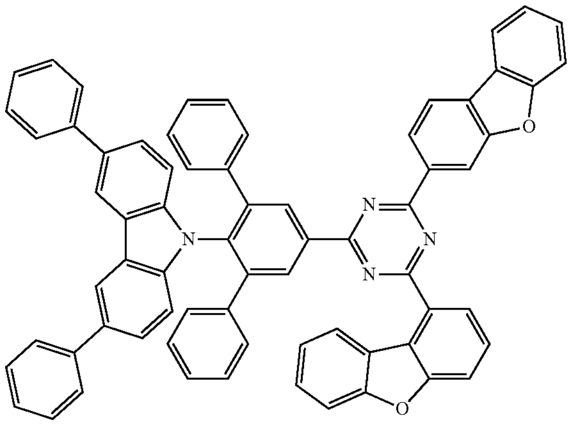
779
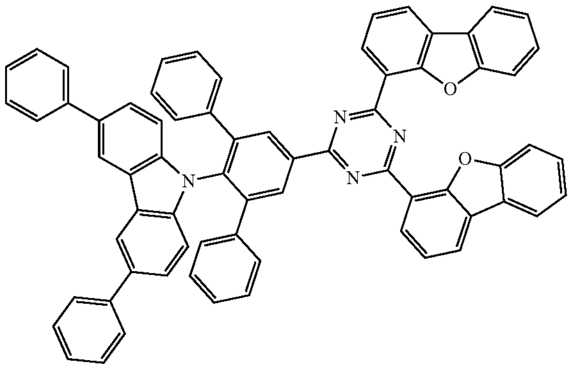

780
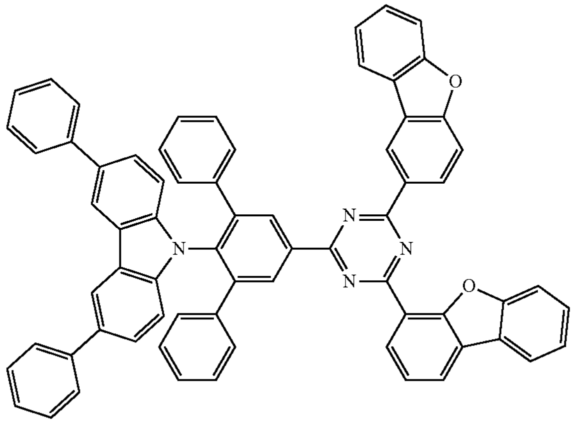
781
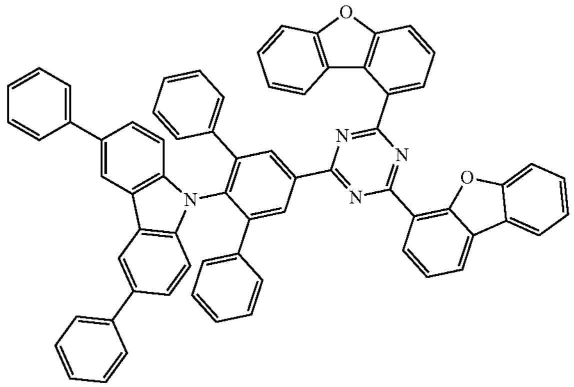
782
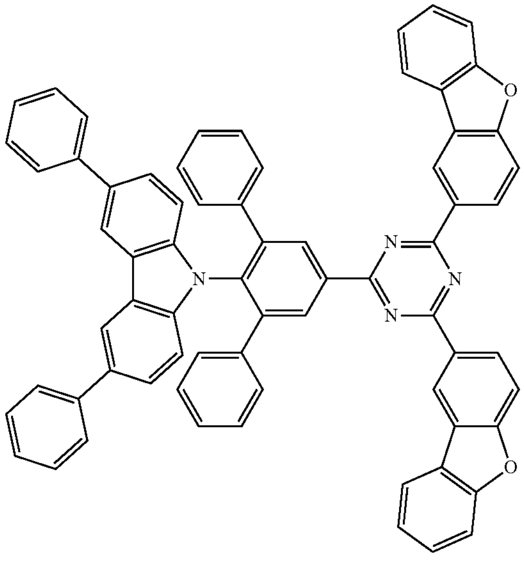
783
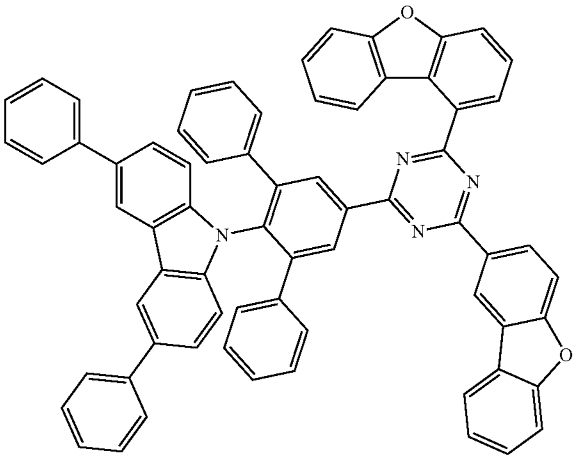
784
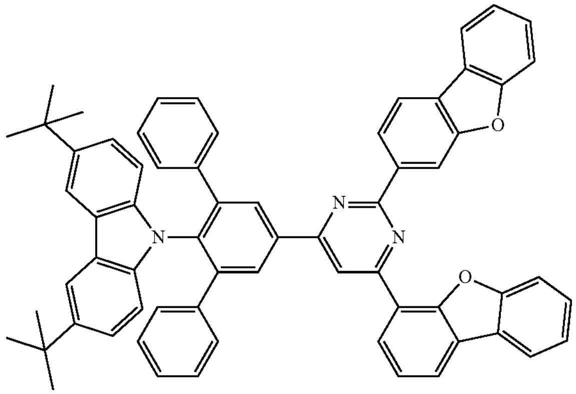
785
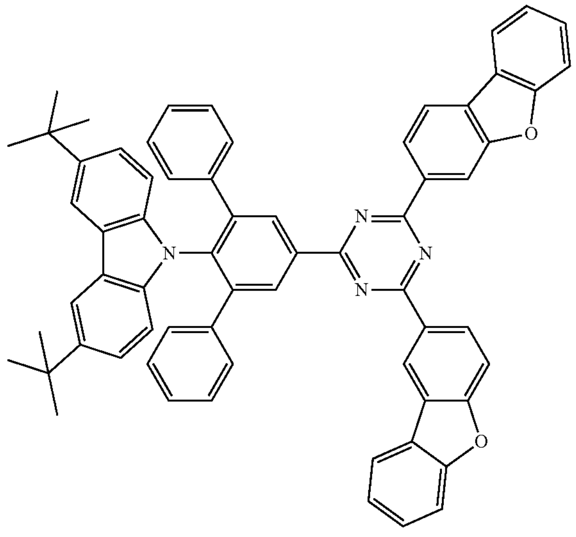

786
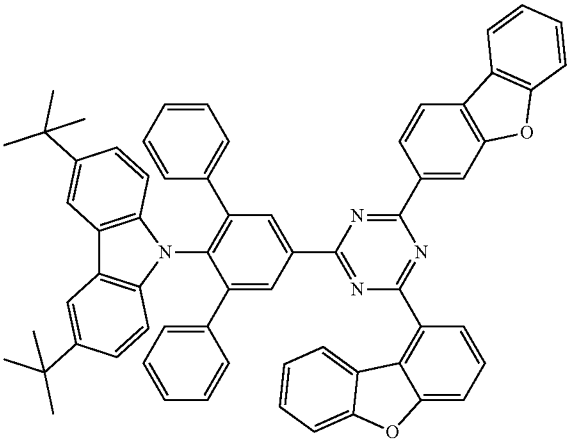
787
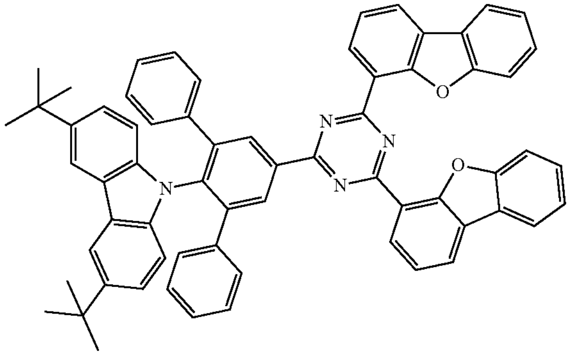
788
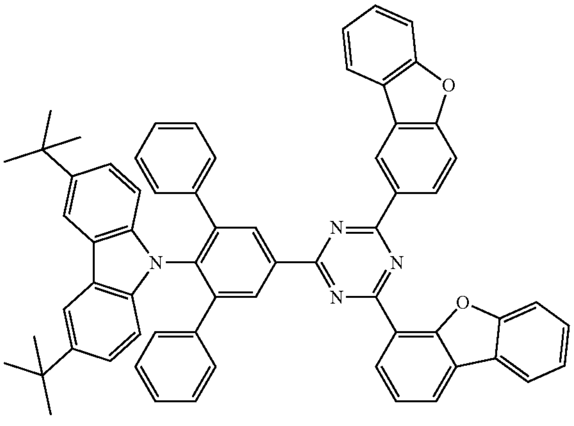
789
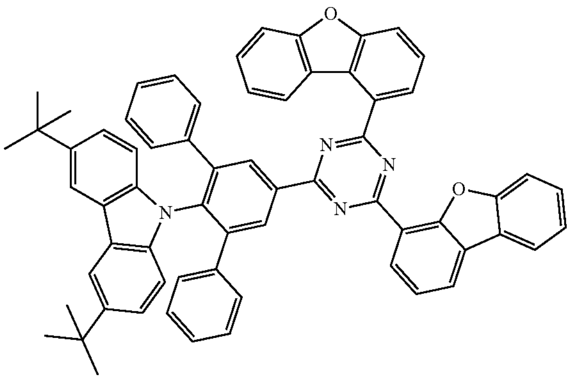
790
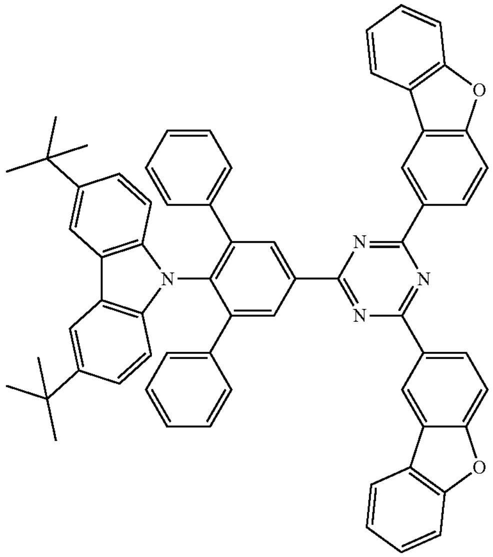
791
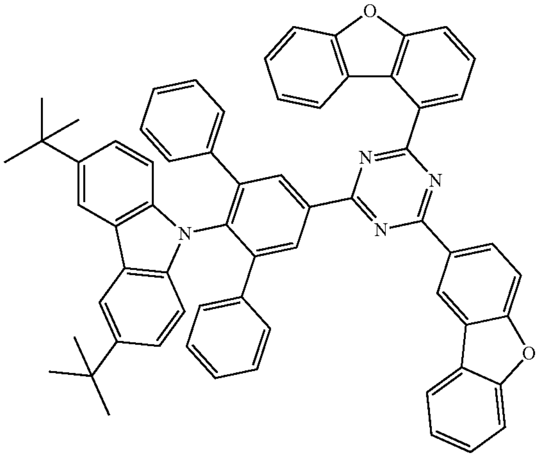

-continued
792
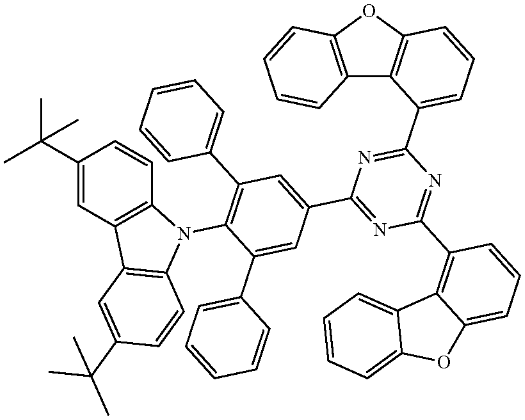
793
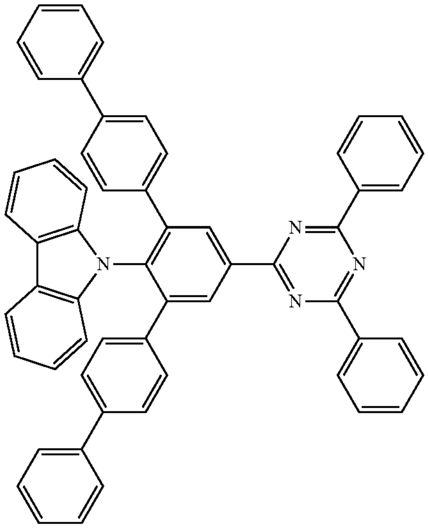
794
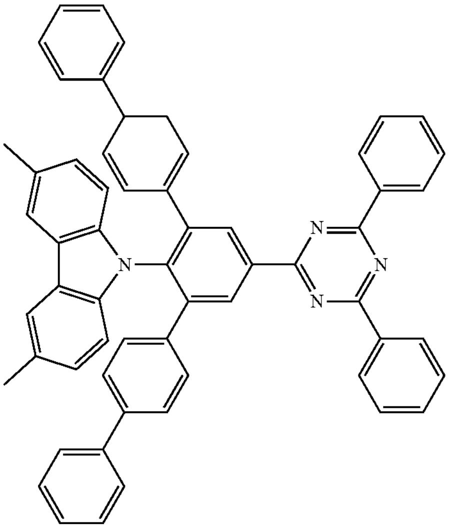
-continued
795
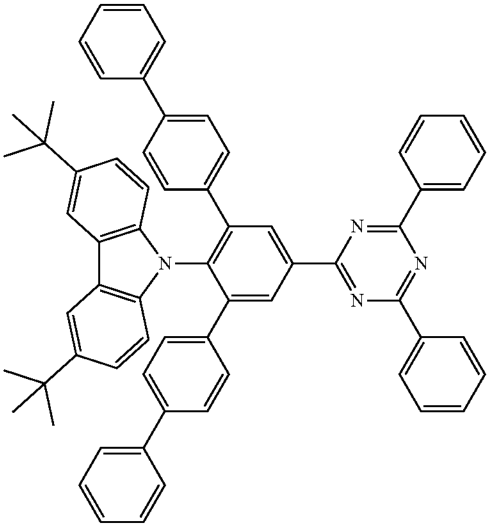
796
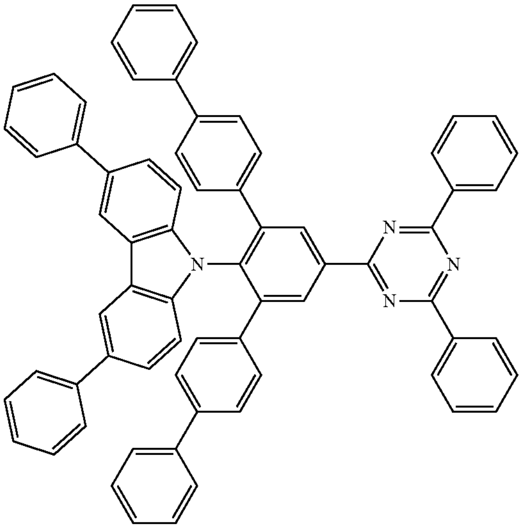
797
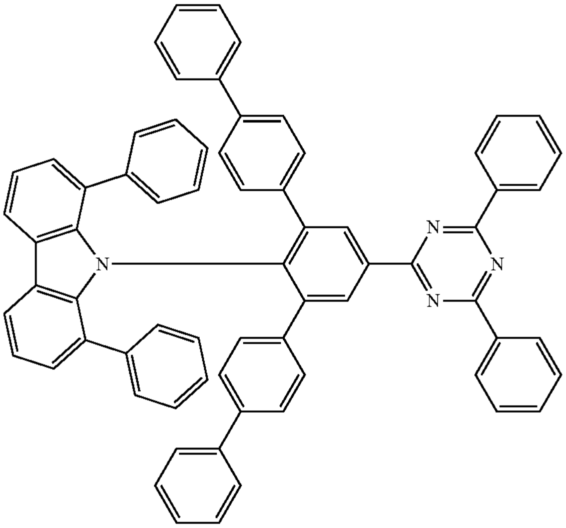

-continued
798
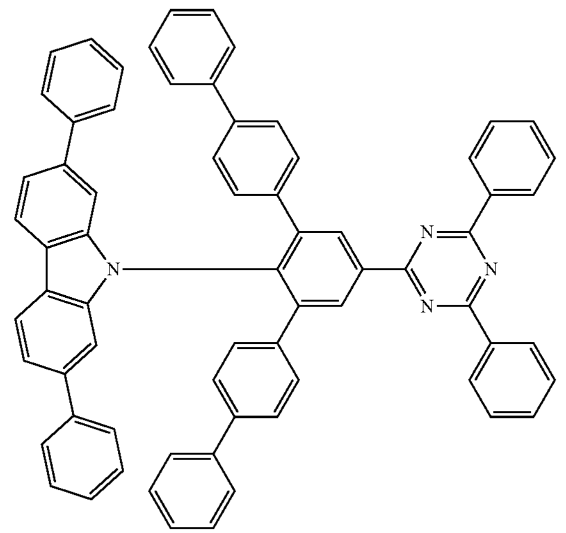
799
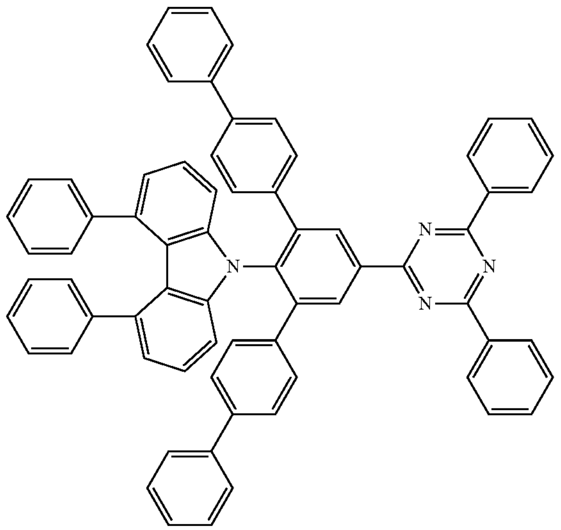
800
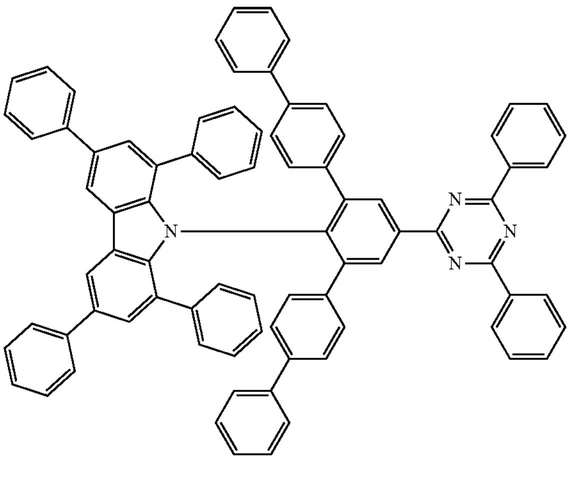
-continued
801
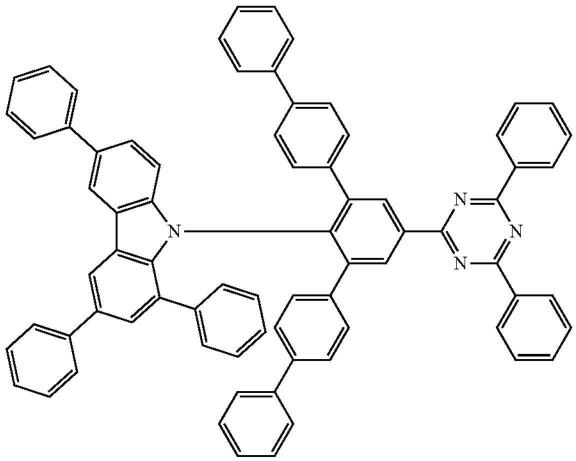
802
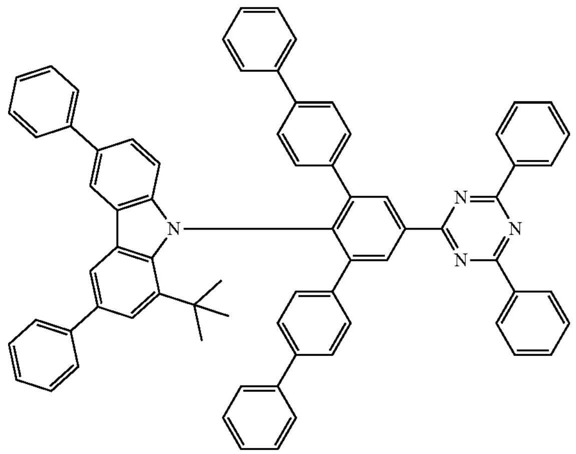
803
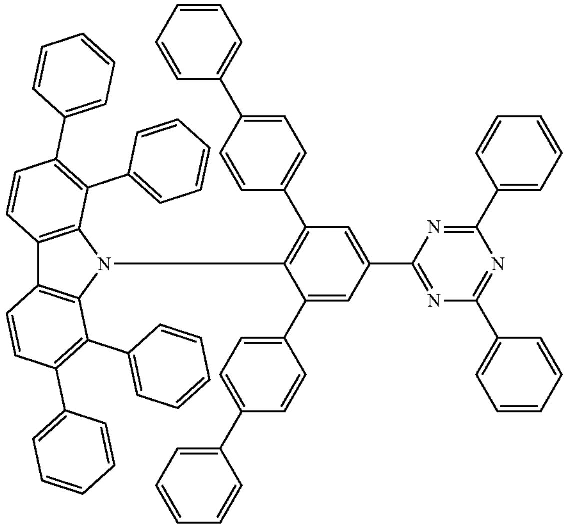

804
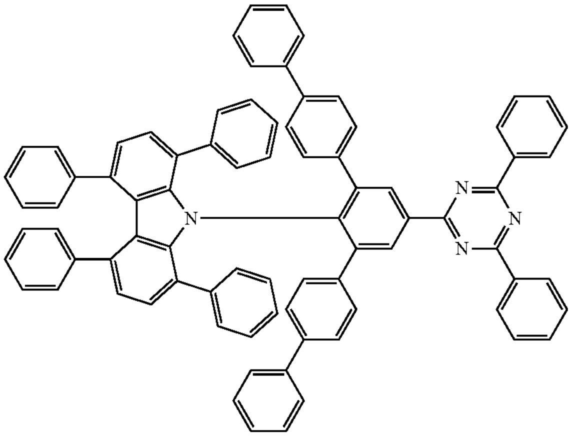
805
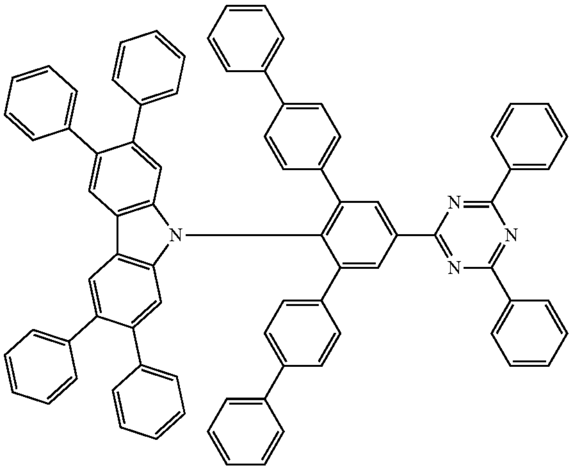
806
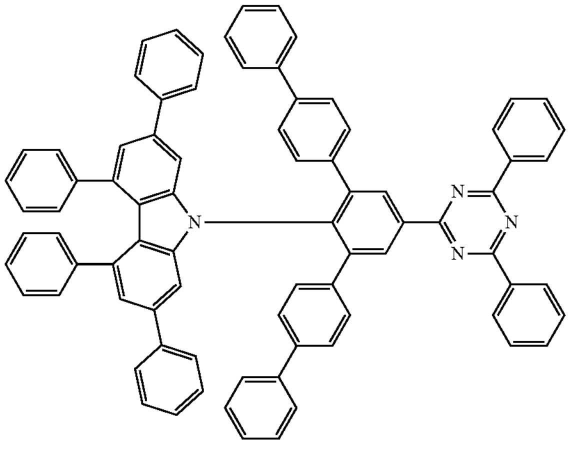
807
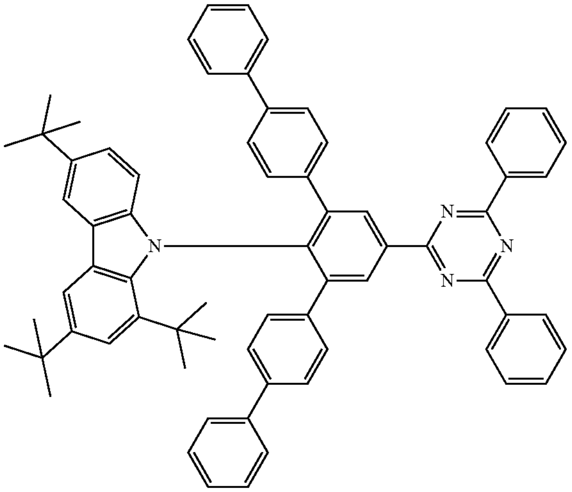
808
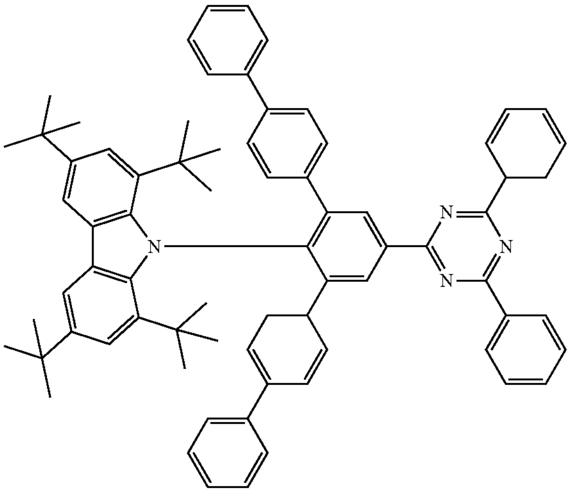
809
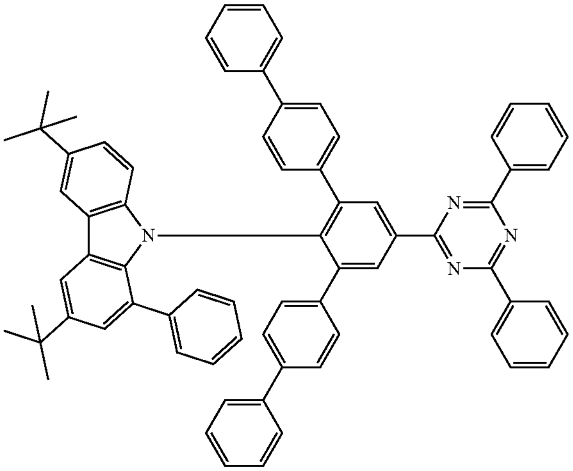

-continued
810
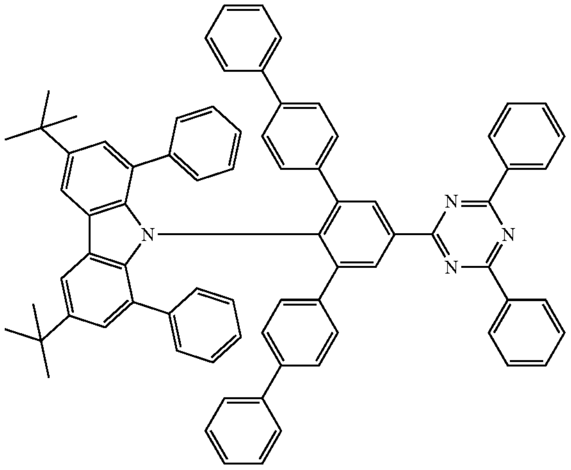
811
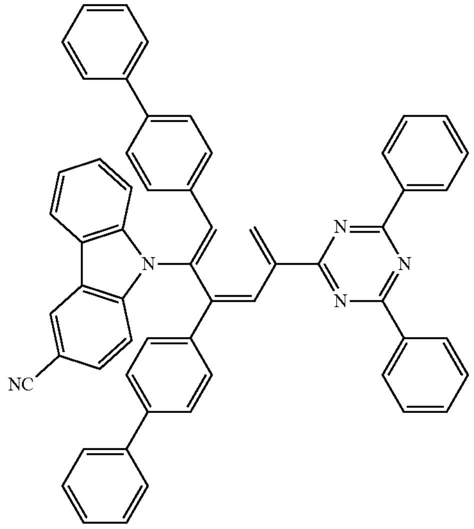
812
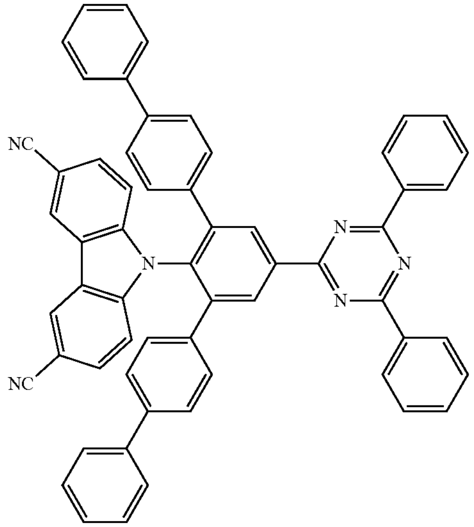
-continued
813
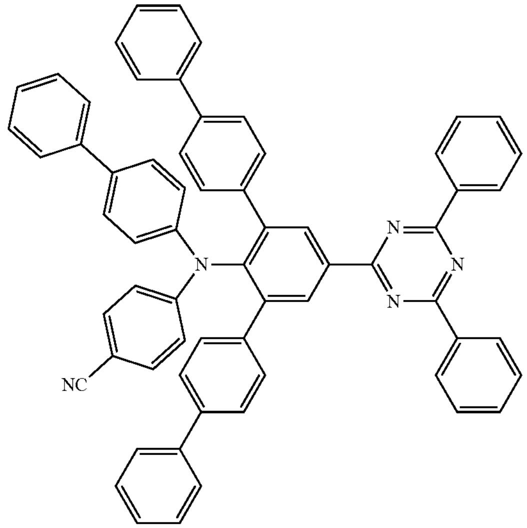
814
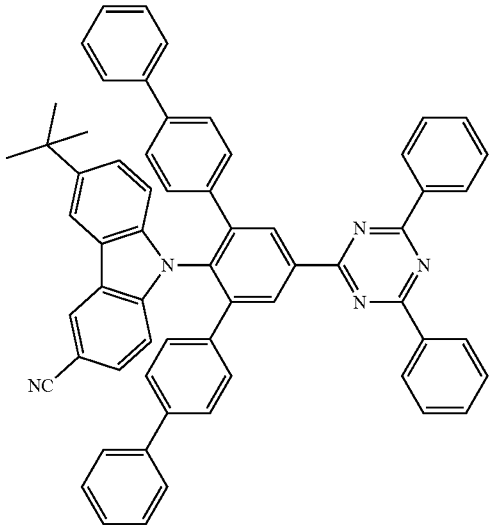
815
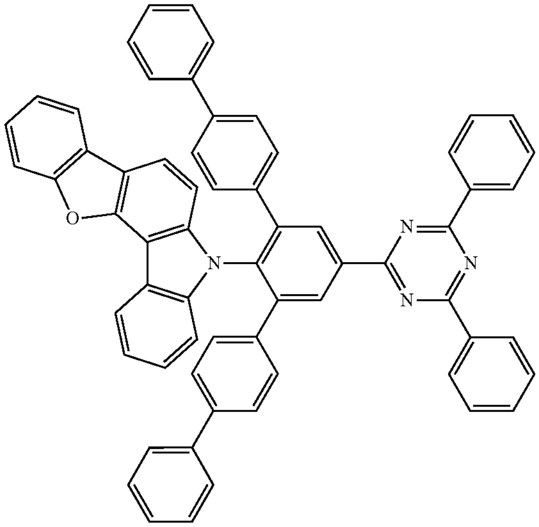

-continued
816
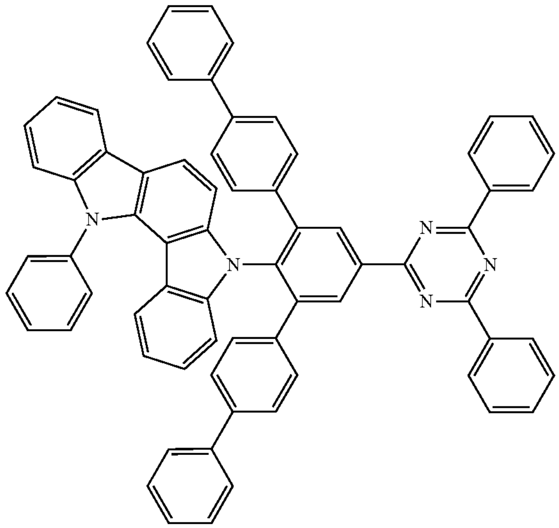
817
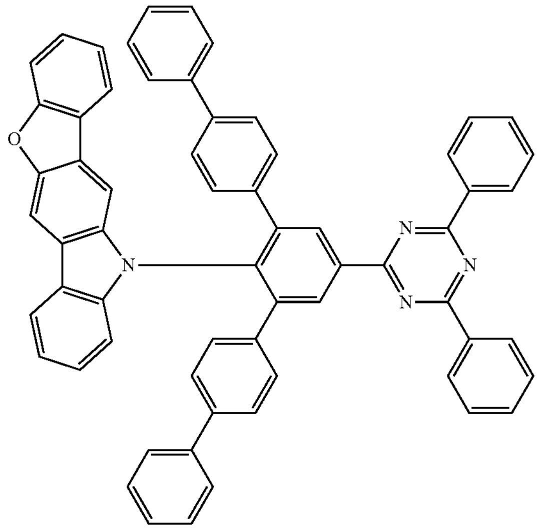
818
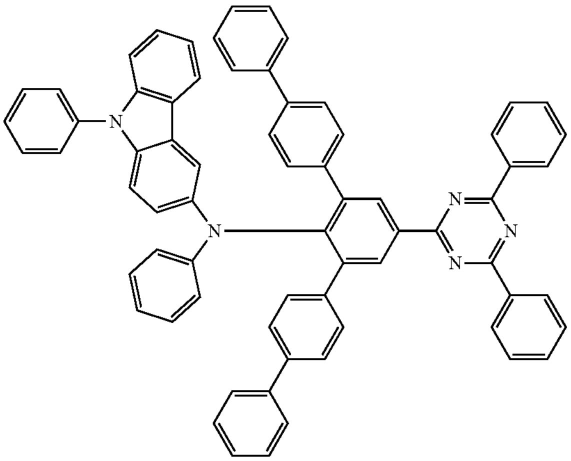
-continued
819
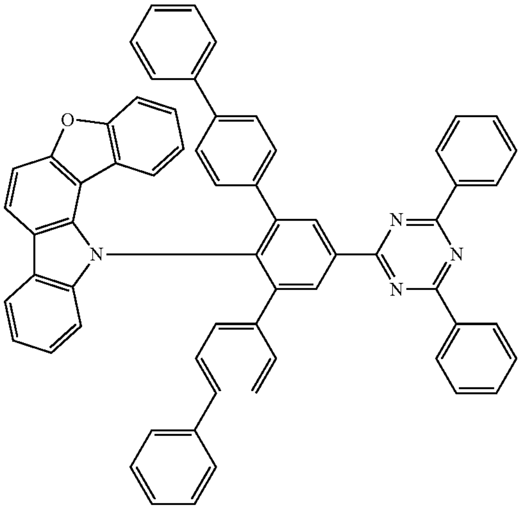
820
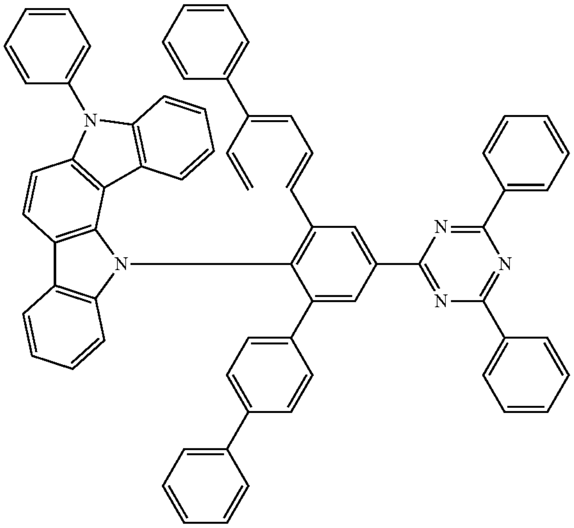
821
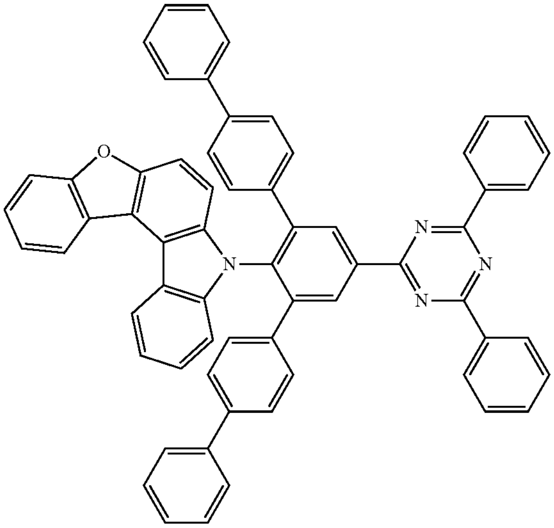

-continued
822
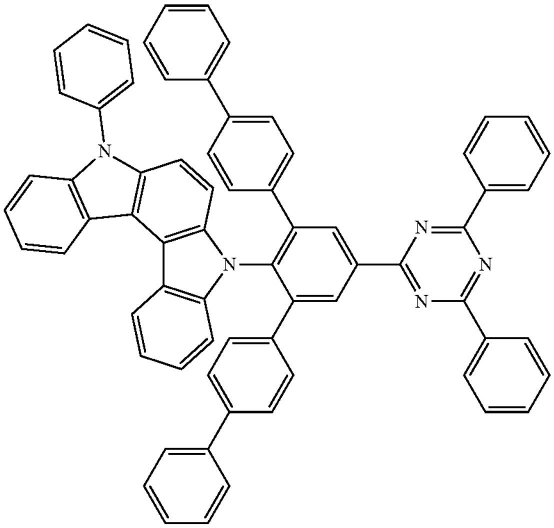
823
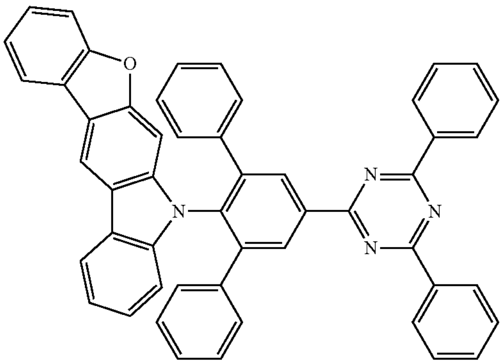
824
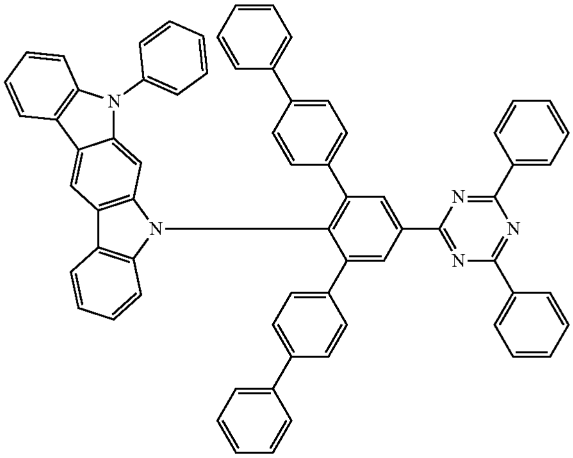
-continued
825
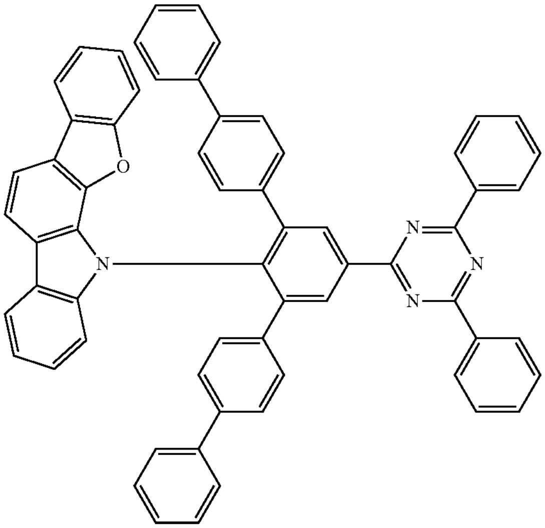
826
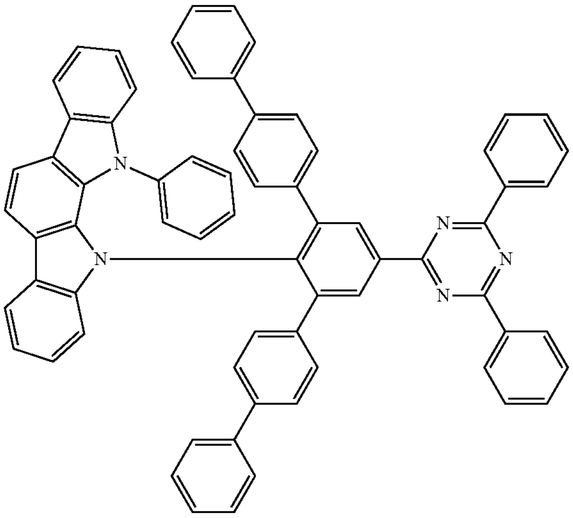
827
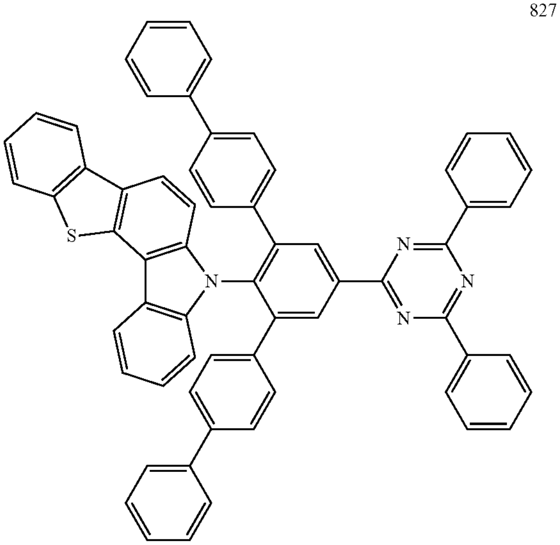

828
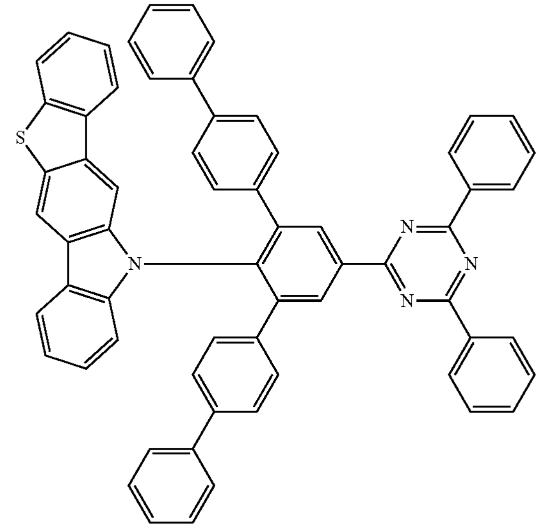
829
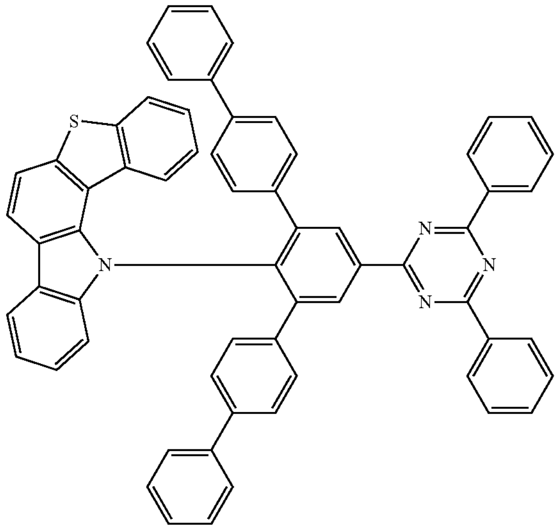
830
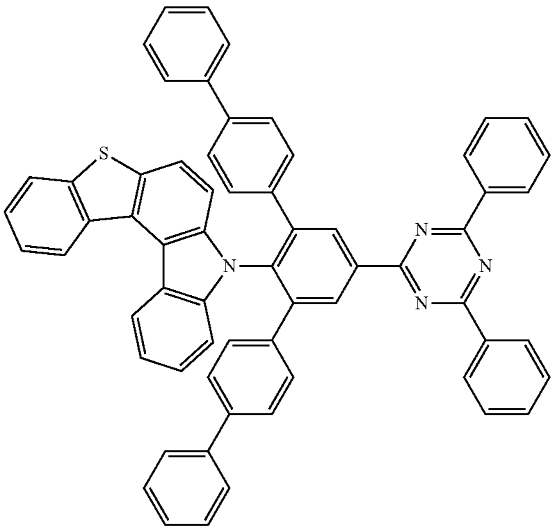
831
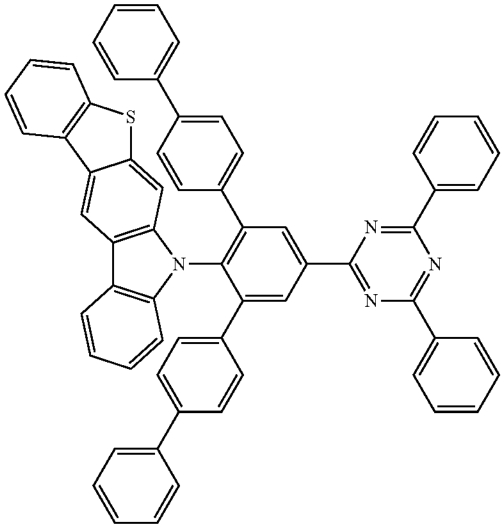
832
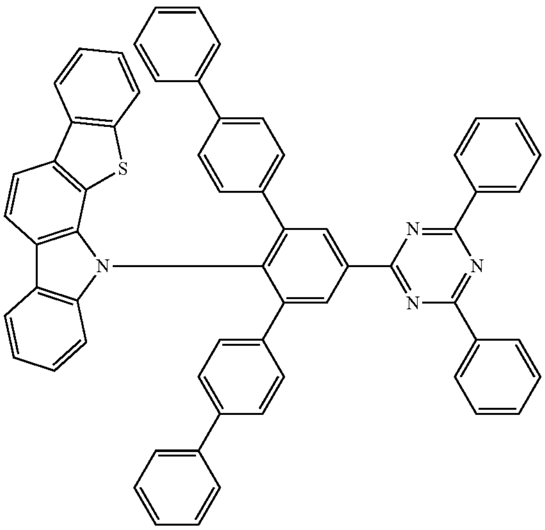
833
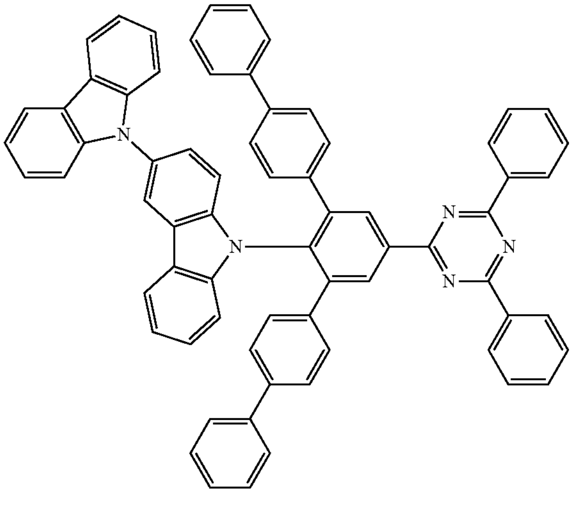

-continued
834
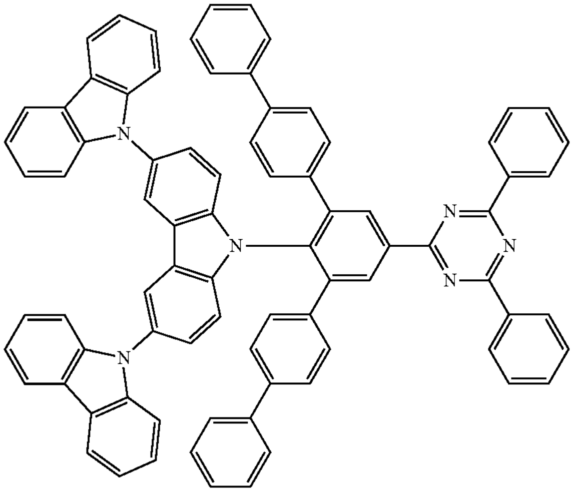
835
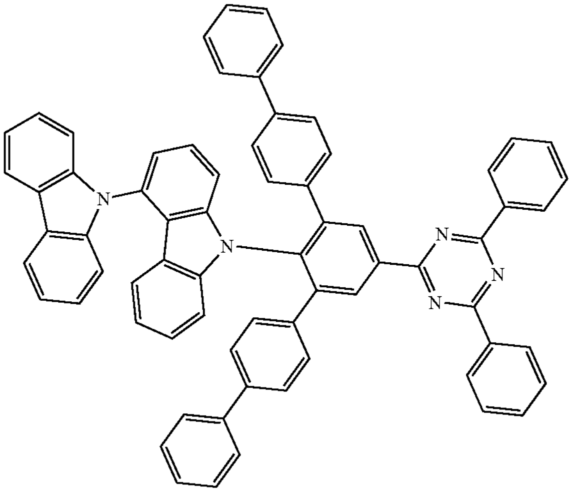
836
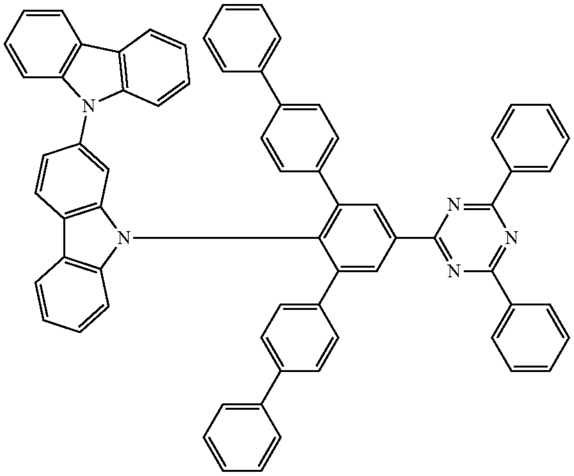
-continued
837
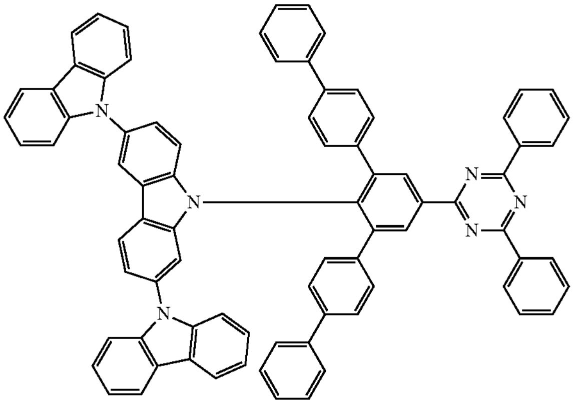
838
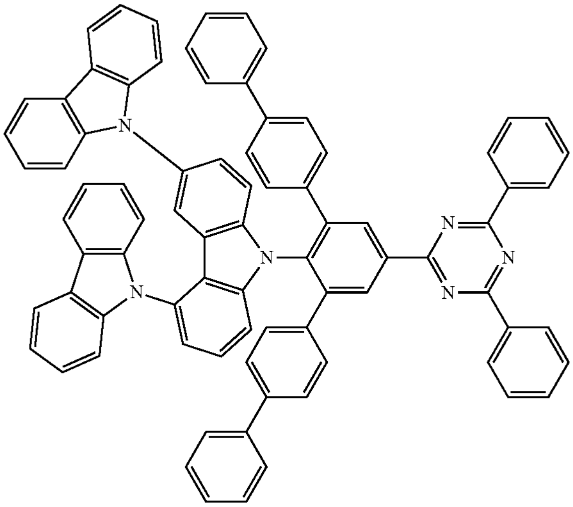
839
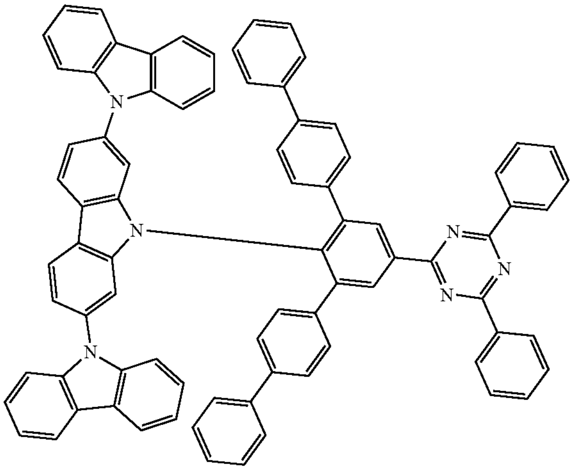

-continued
840
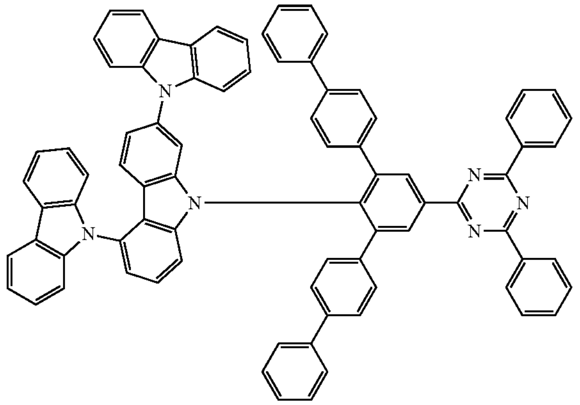
841
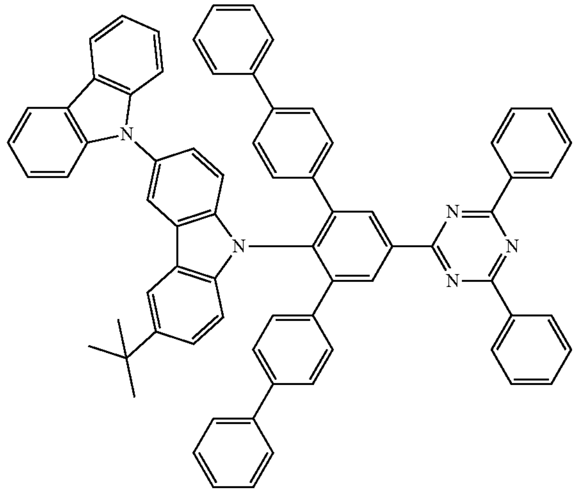
842
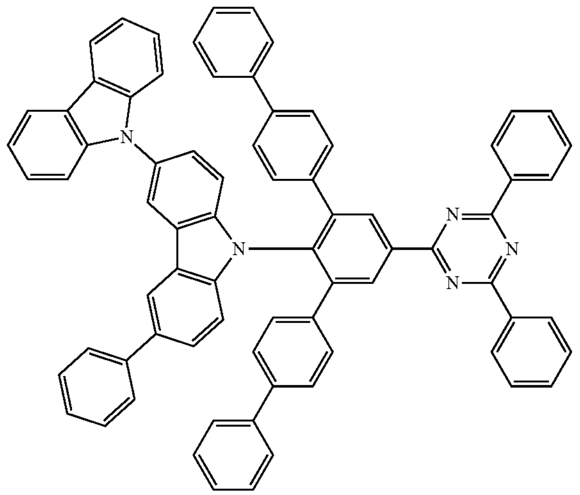
-continued
843
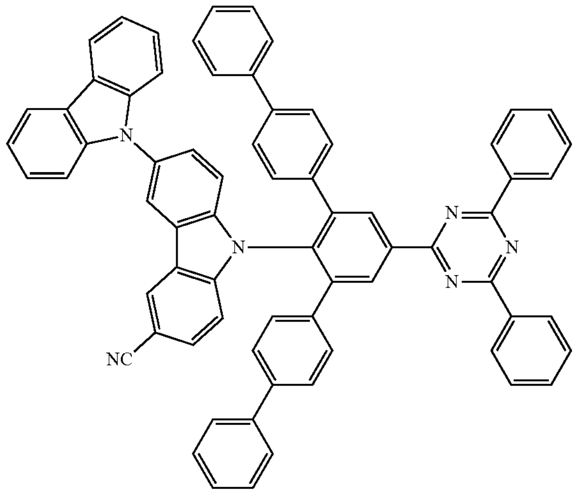
844
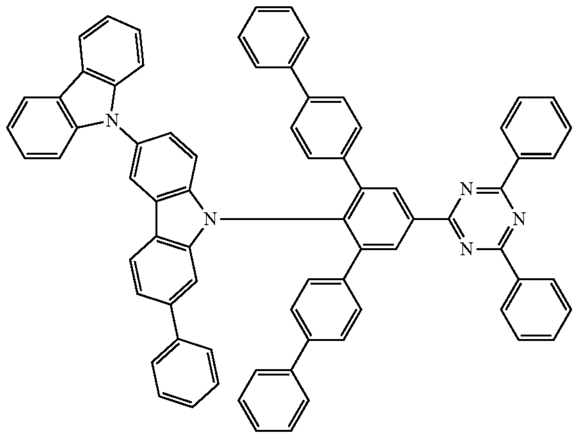
845
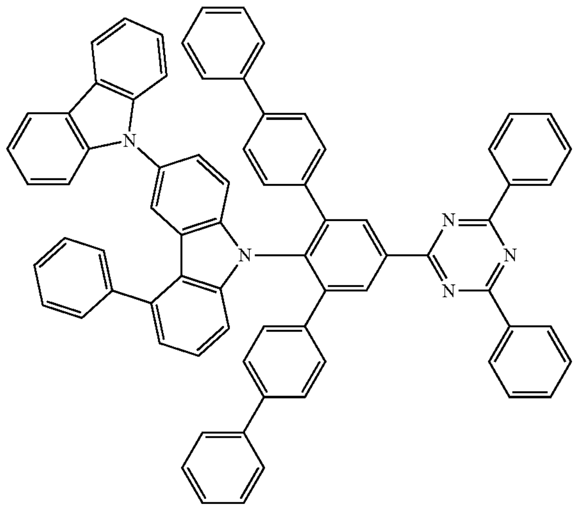

-continued
846
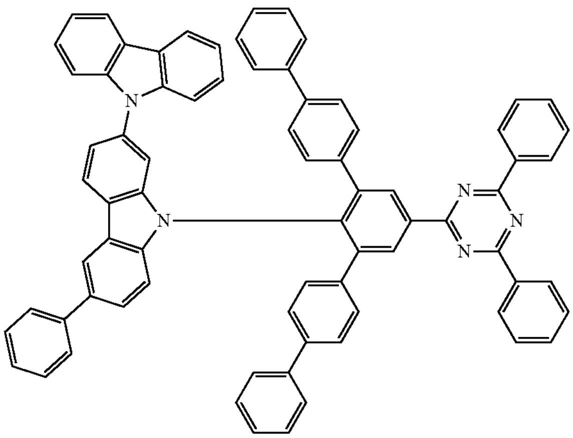
847
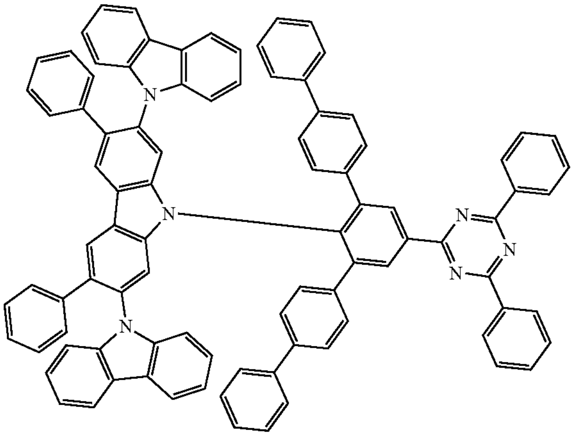
848
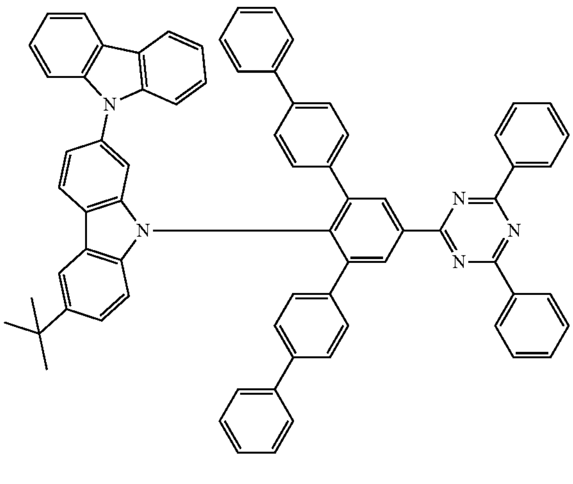
-continued
849
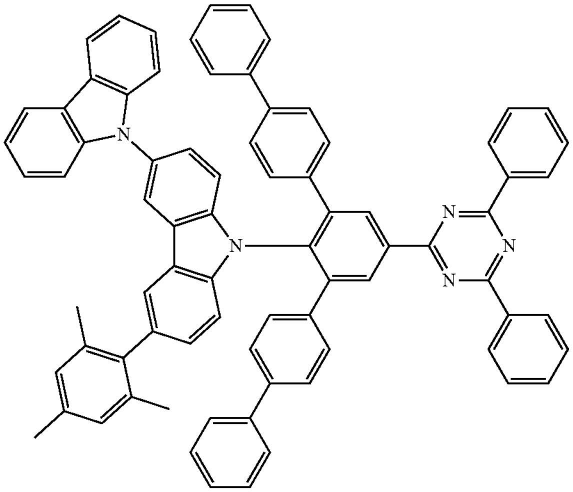
850
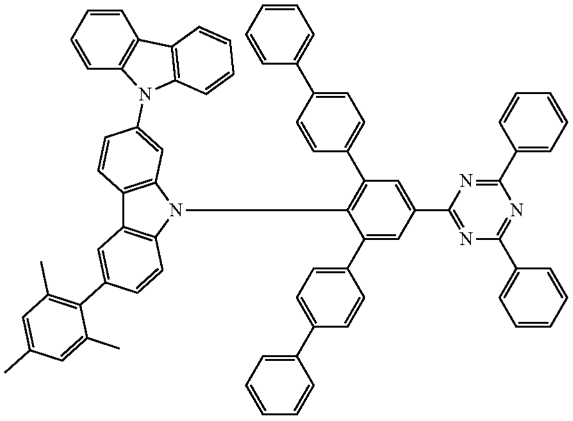
851
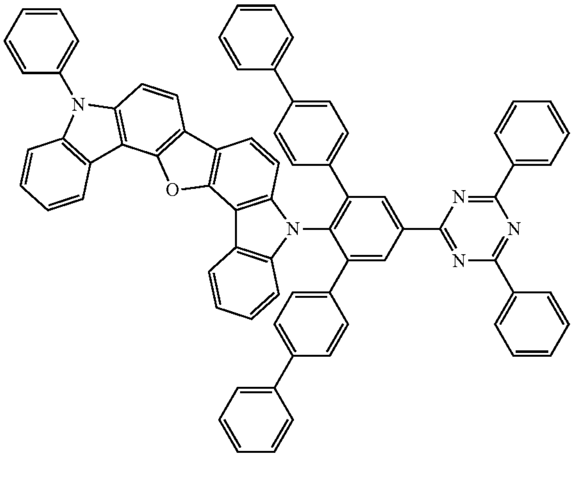

-continued
852
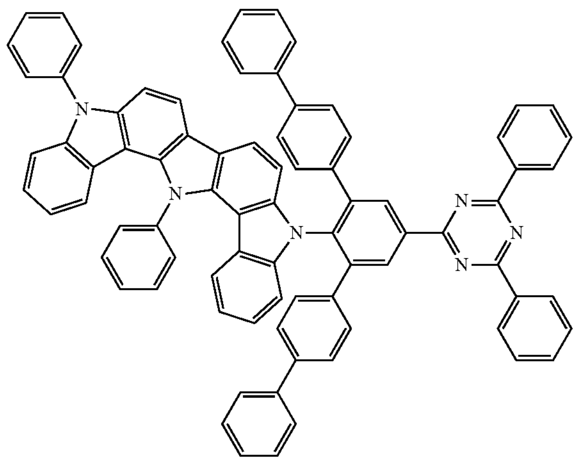
853
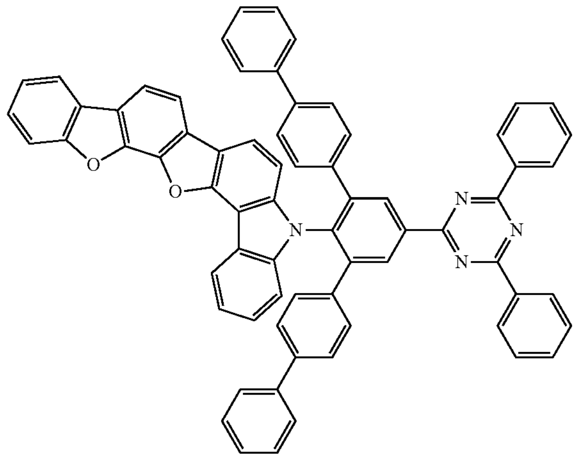
854
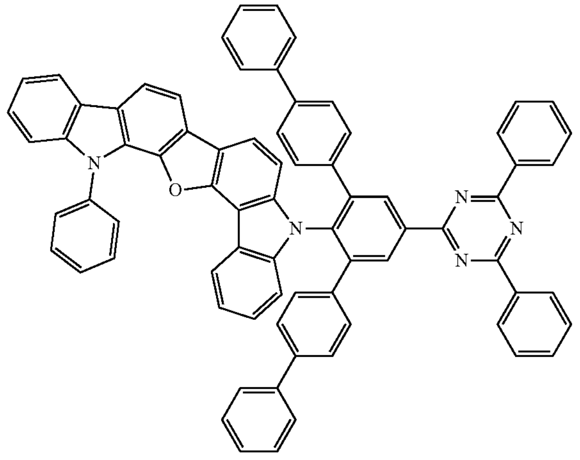
855
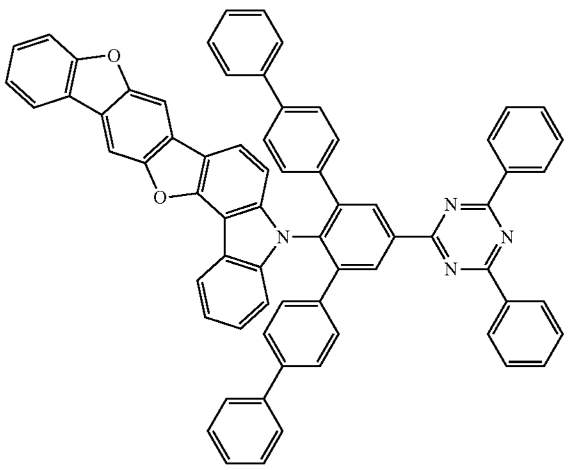
856
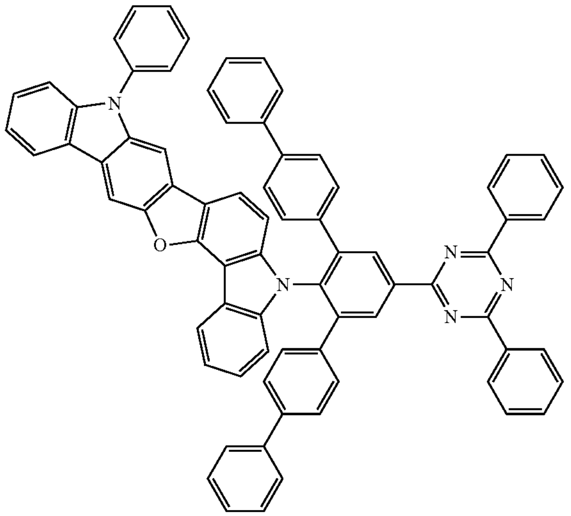
857
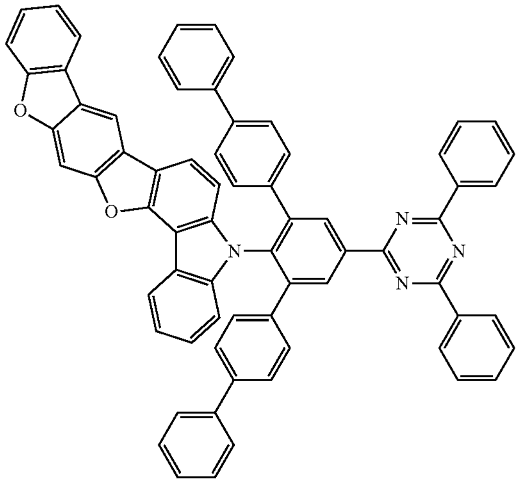

-continued
858
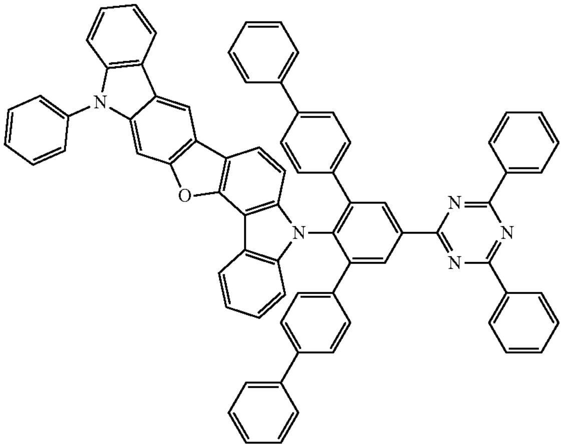
859
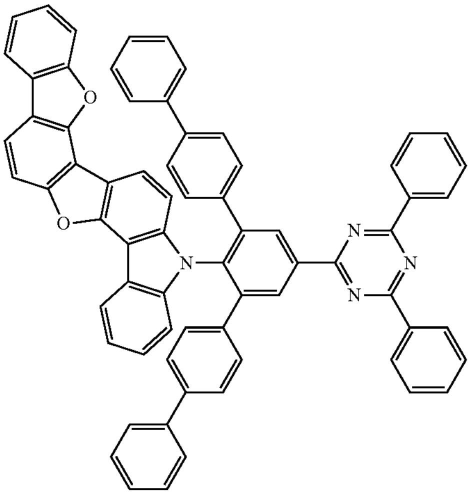
860
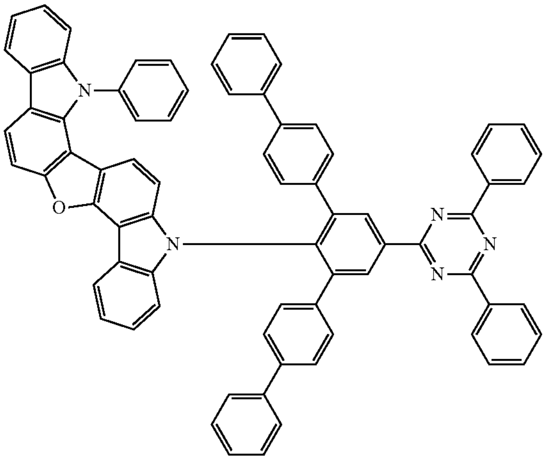
-continued
861
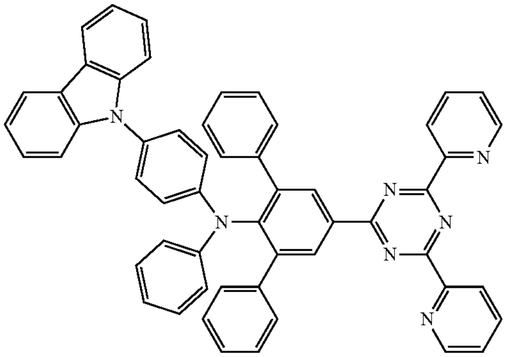
862
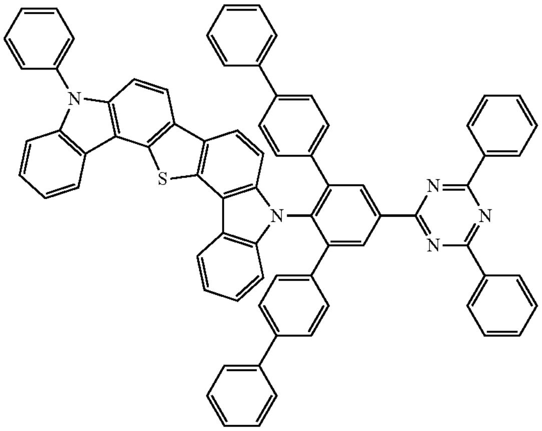
863
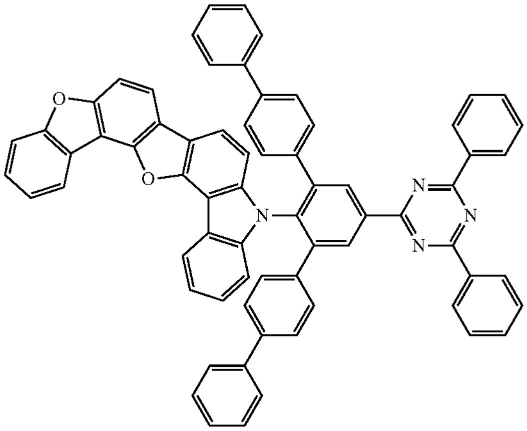

864
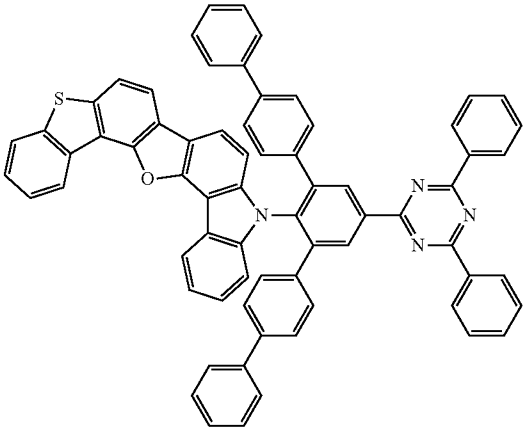
865
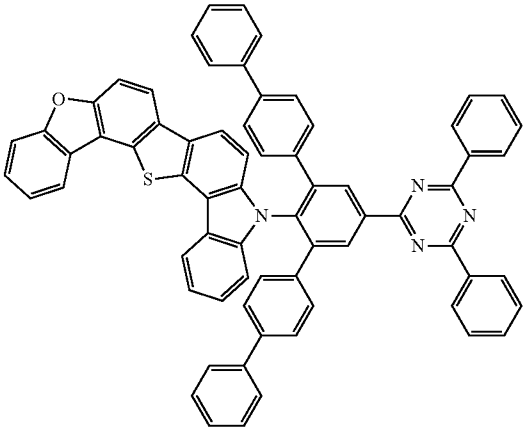
866
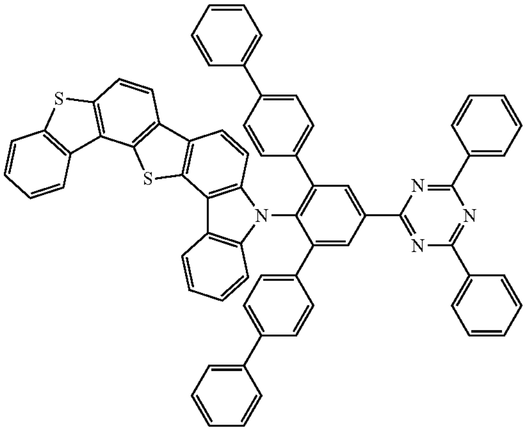
867
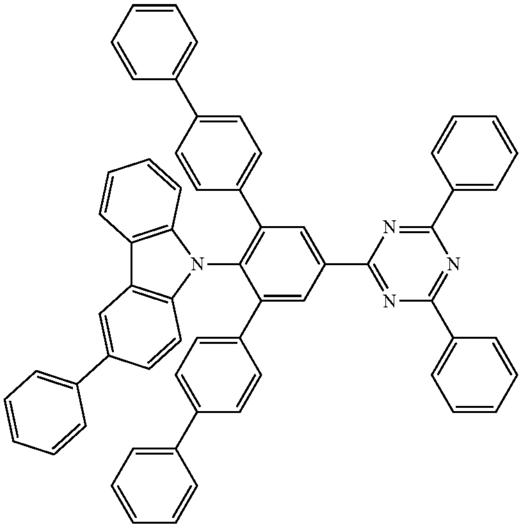
868
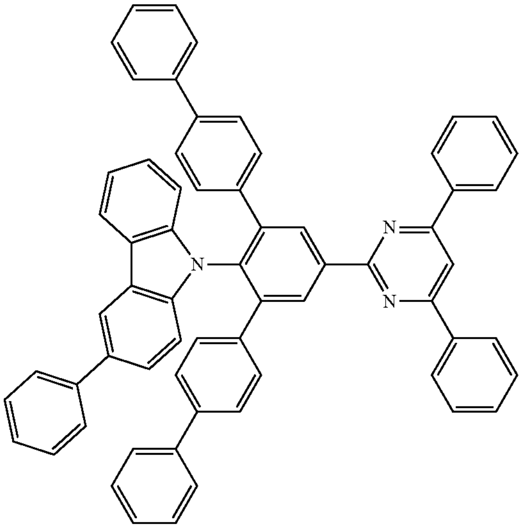
869
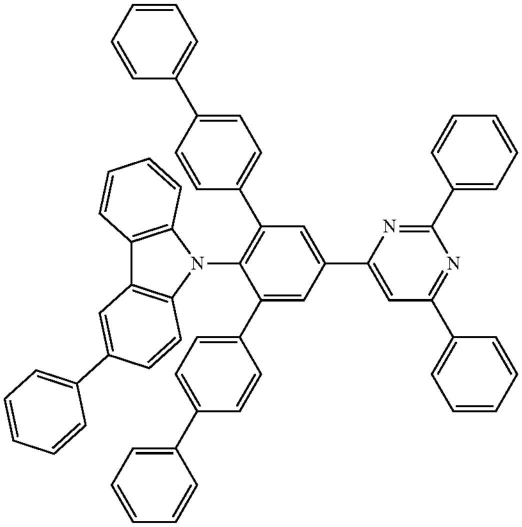

-continued
870
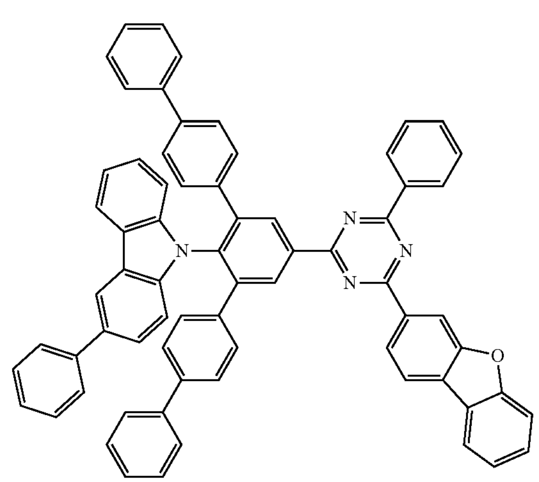
871
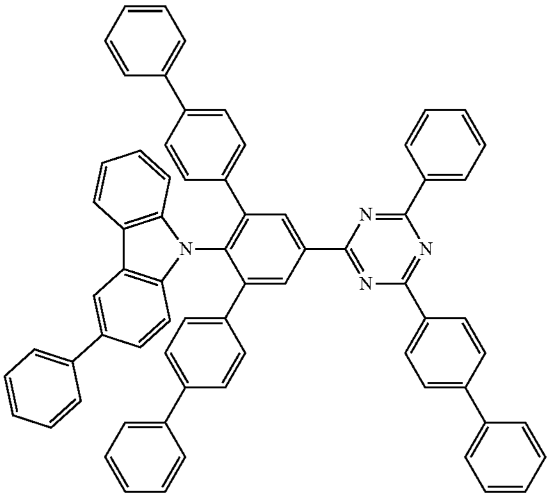
872
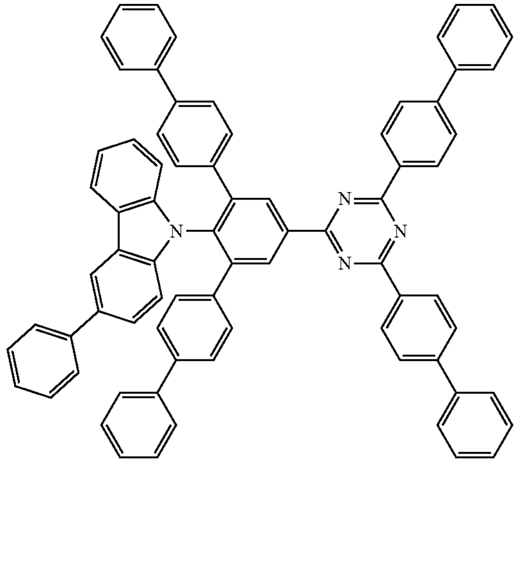
-continued
873
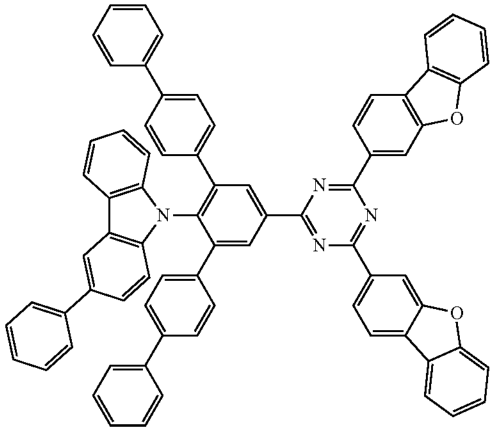
874
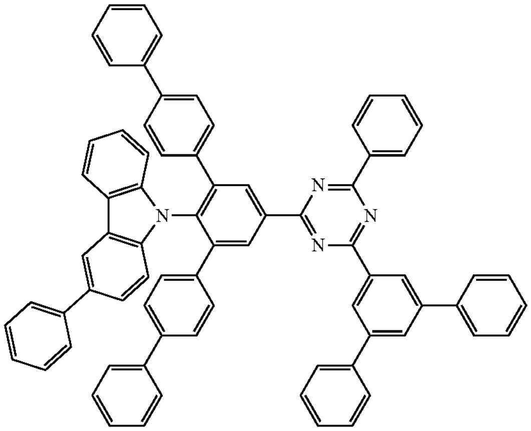
875
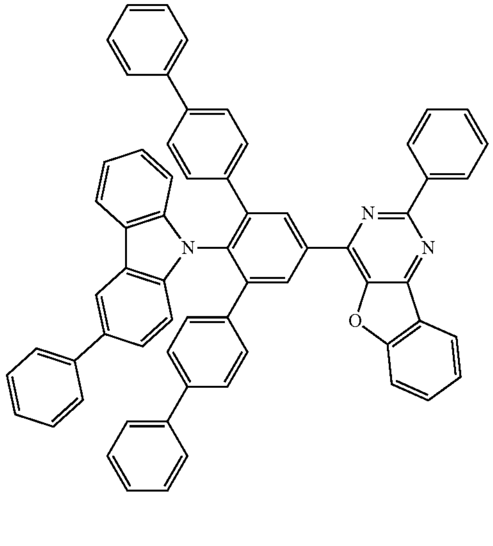

-continued
876
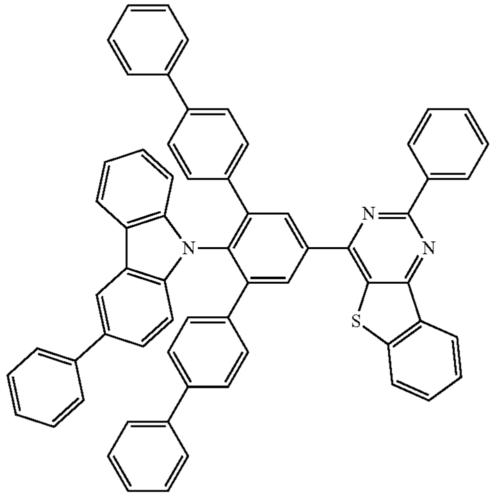
877
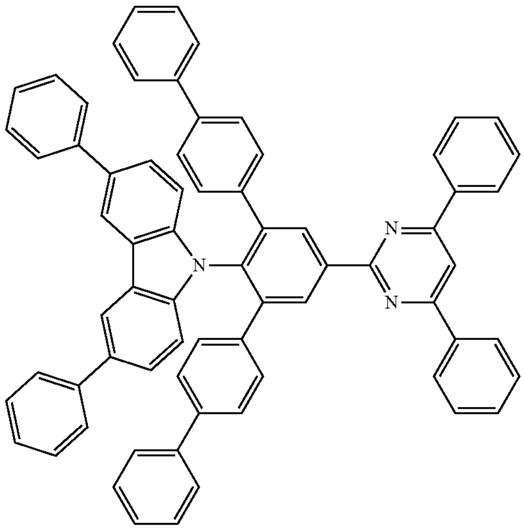
878
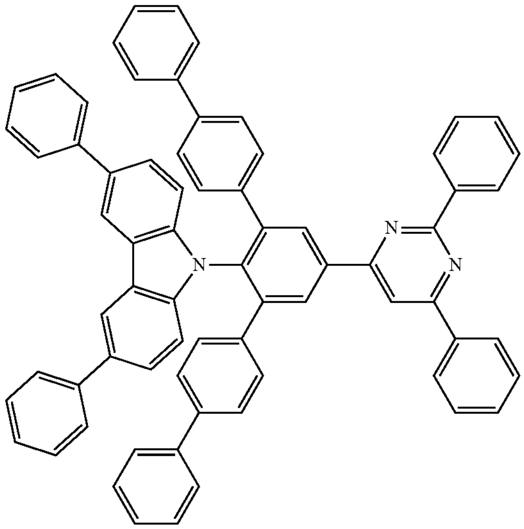
-continued
879
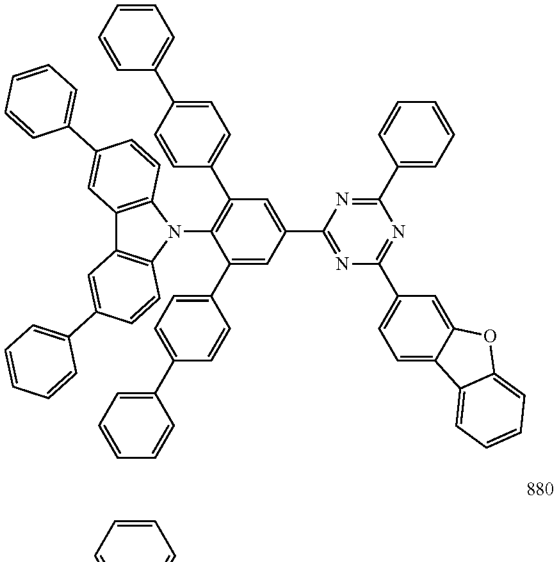
880
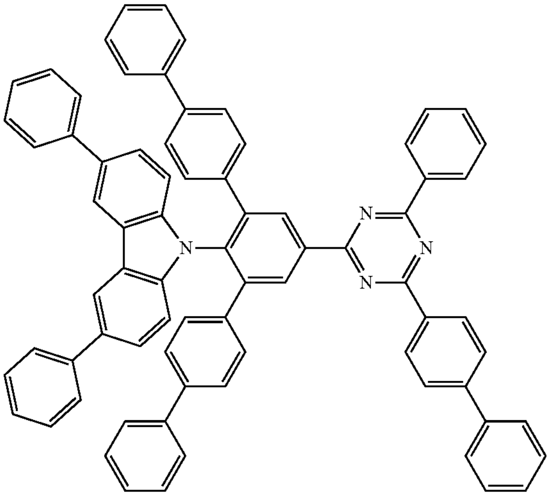
881
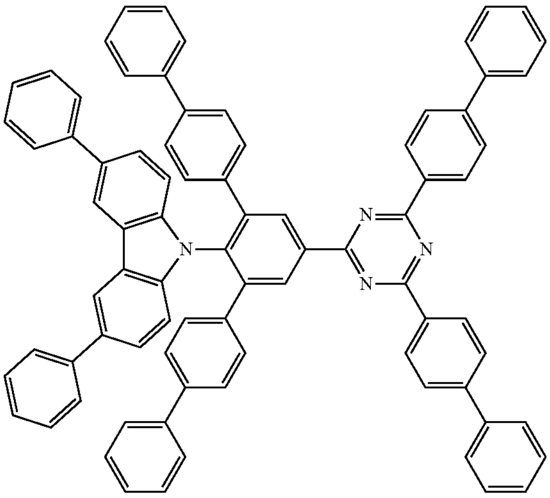

-continued
882
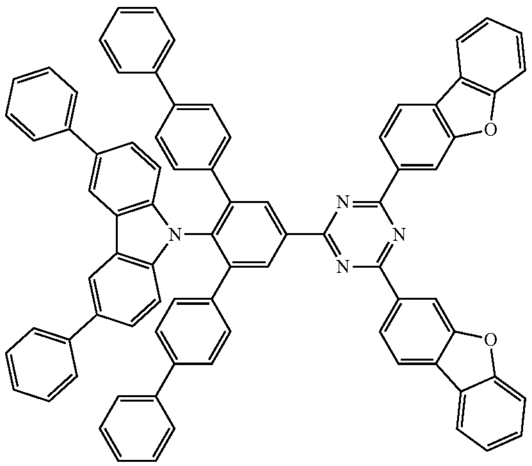
883
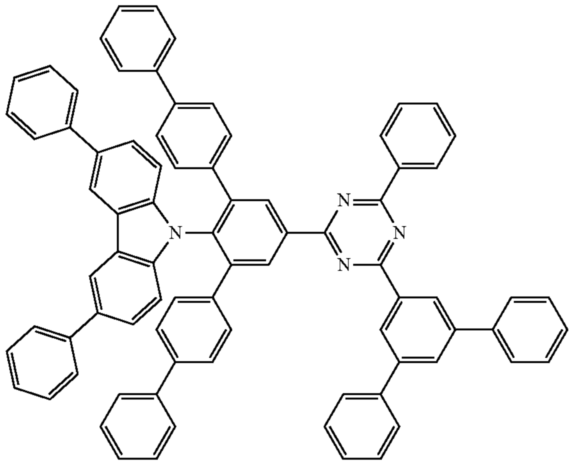
884
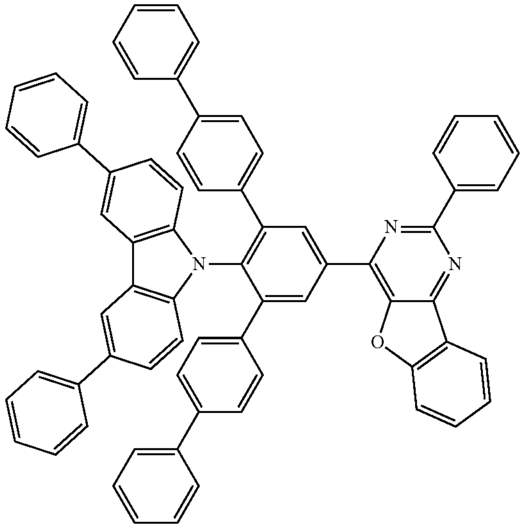
-continued
885
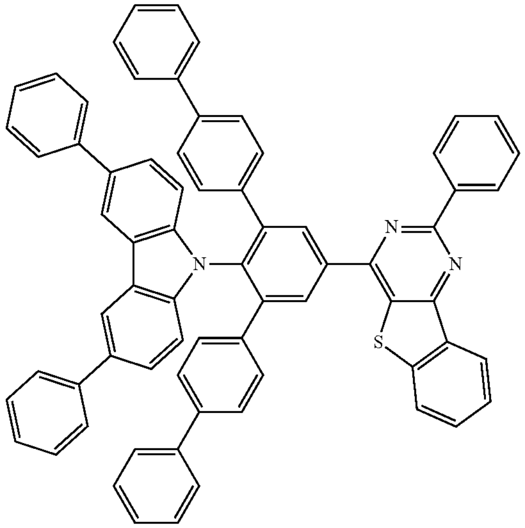
886
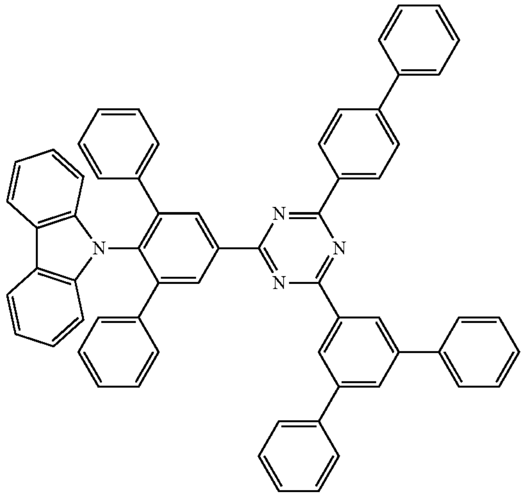
887
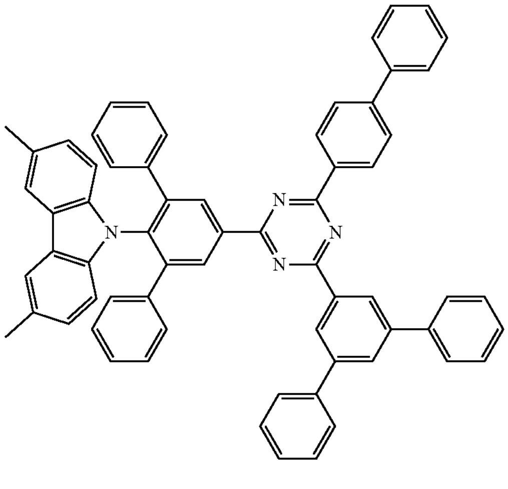

-continued
888
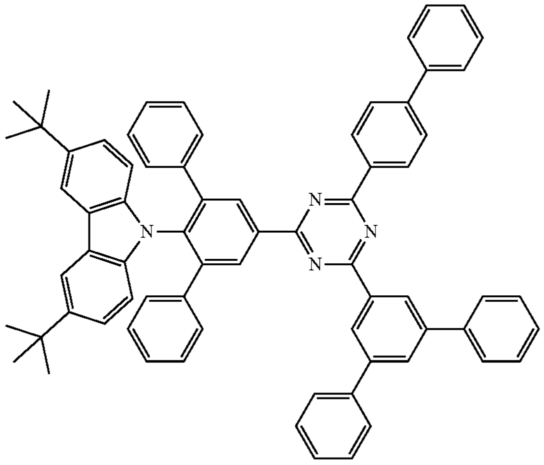
889
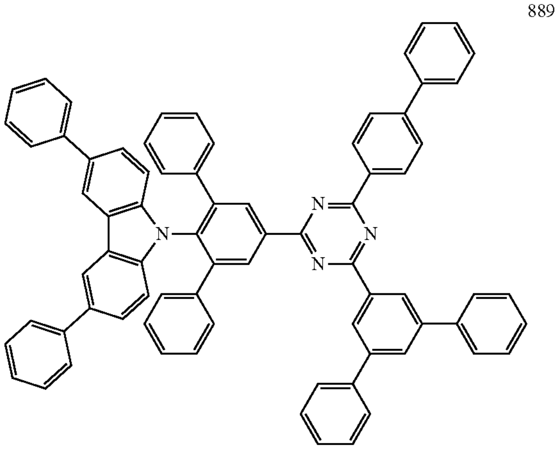
890
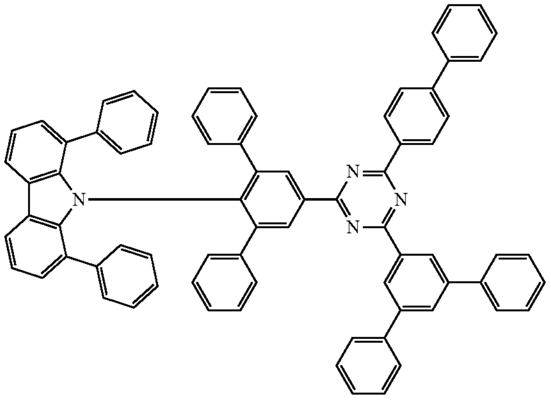
-continued
891
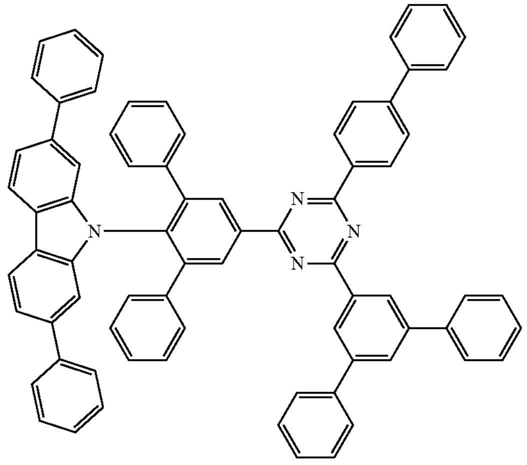
892
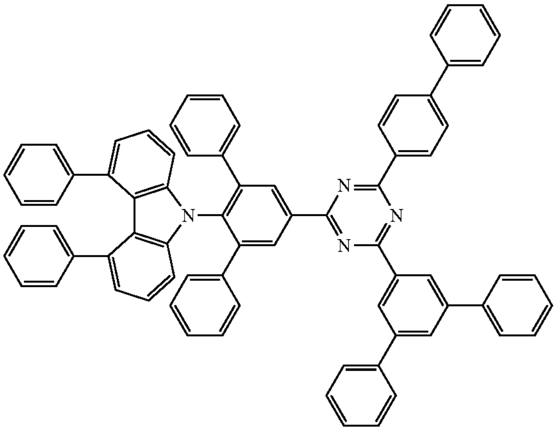
893
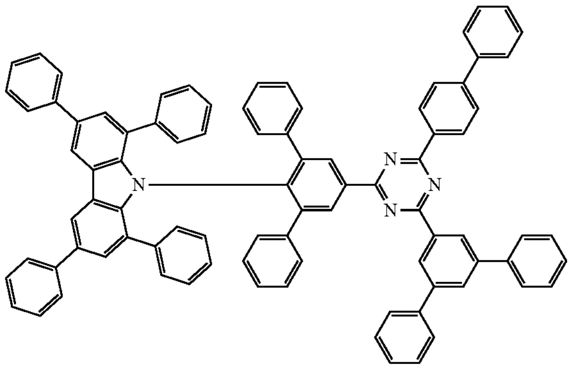

-continued
894
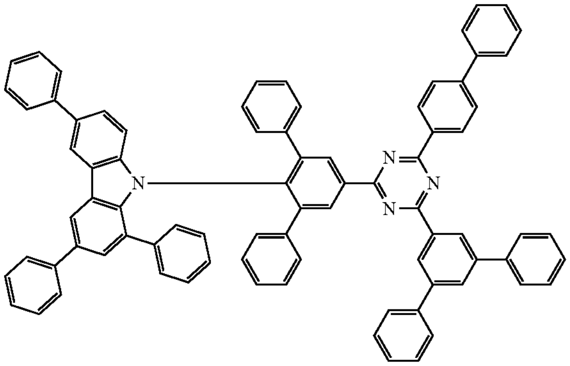
895
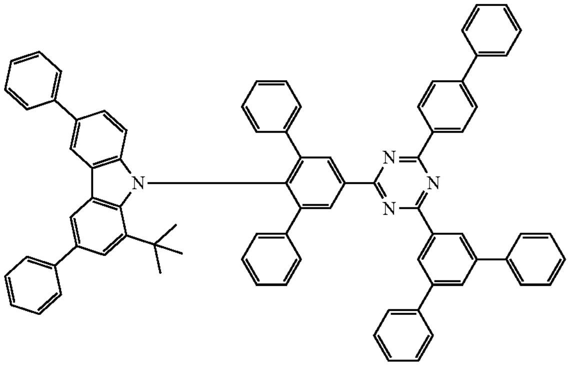
896
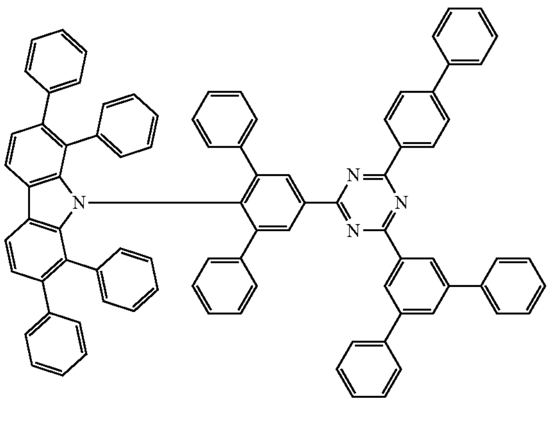
-continued
897
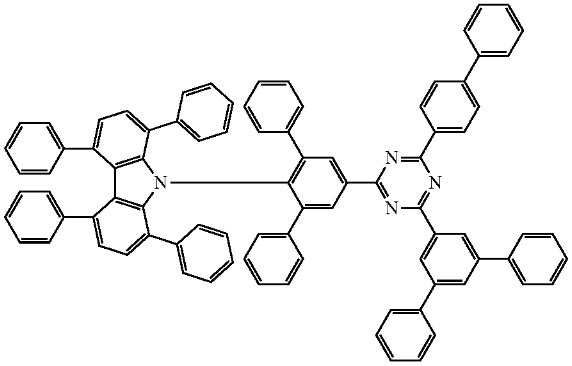
898
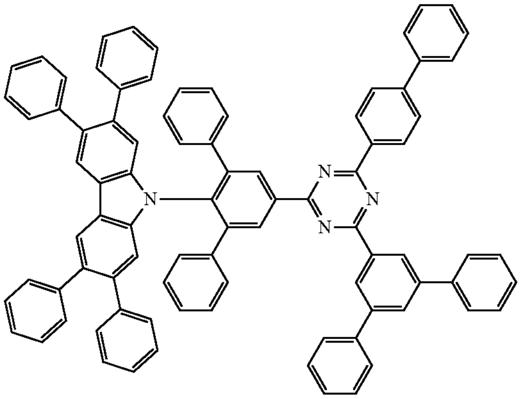
899
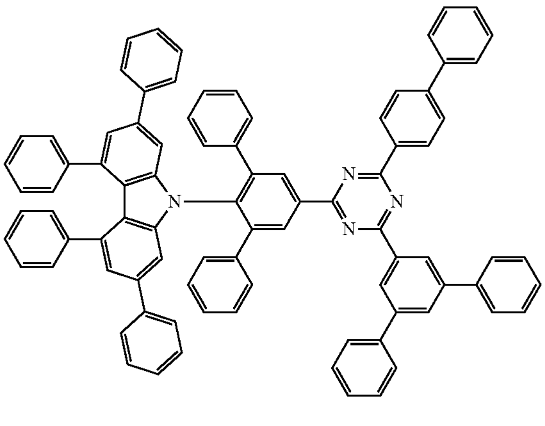

900
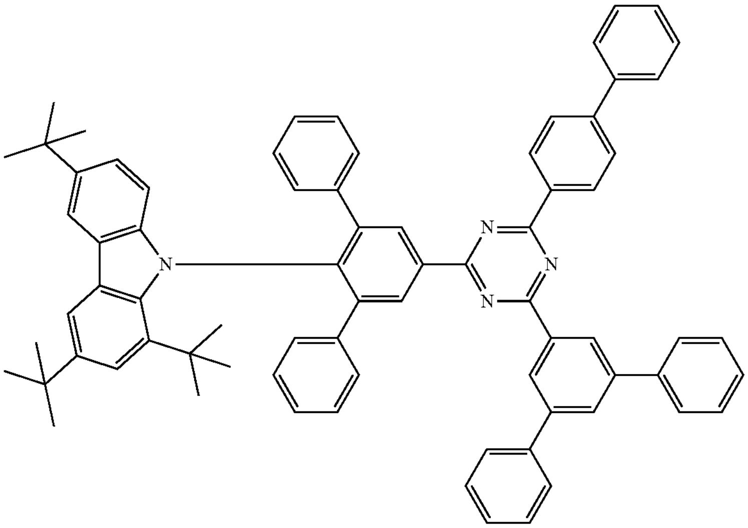
901
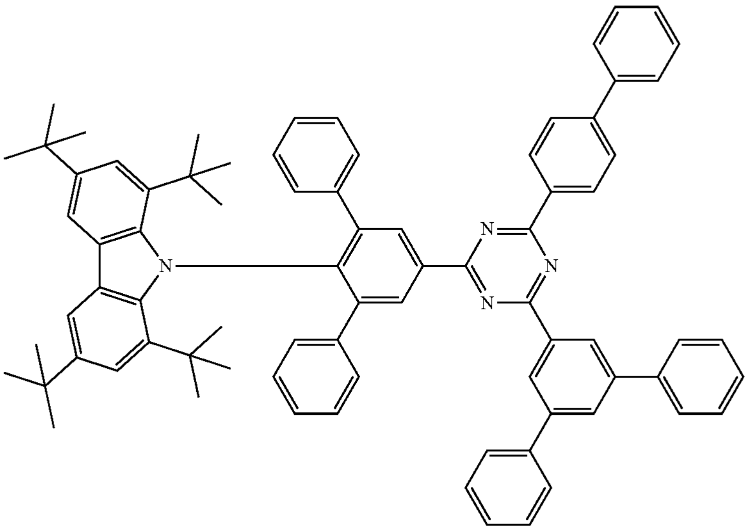
902
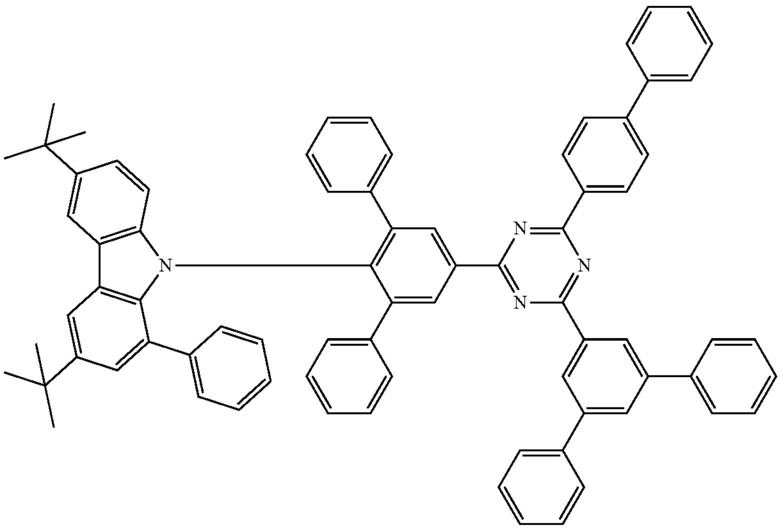

-continued
903
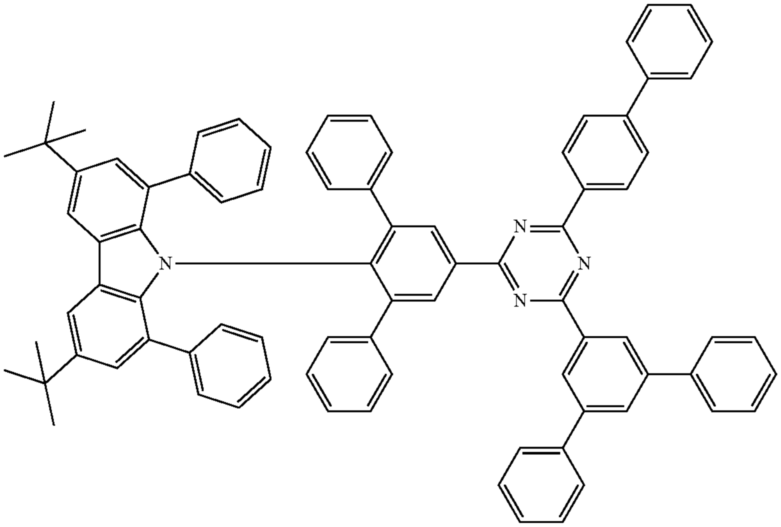
904
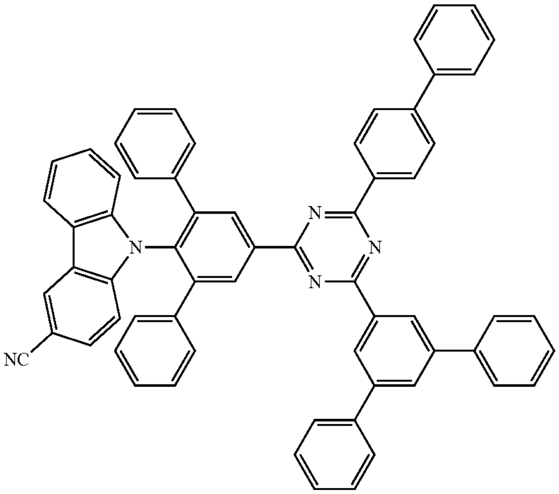
905
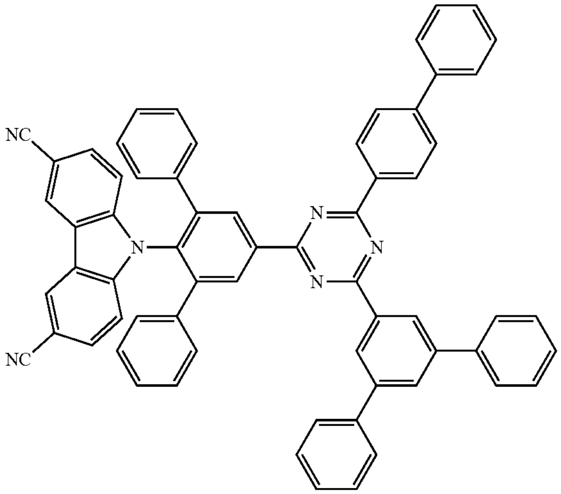
906
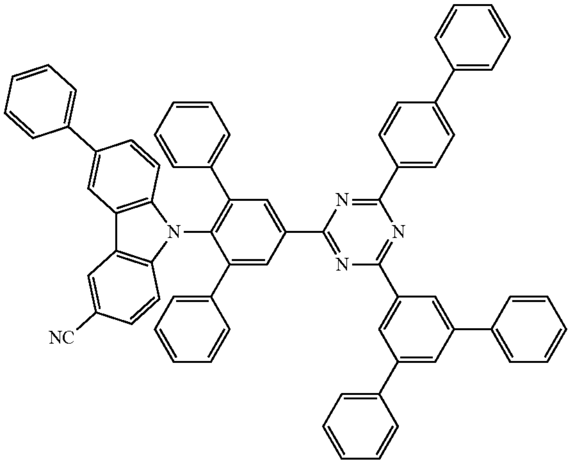
907
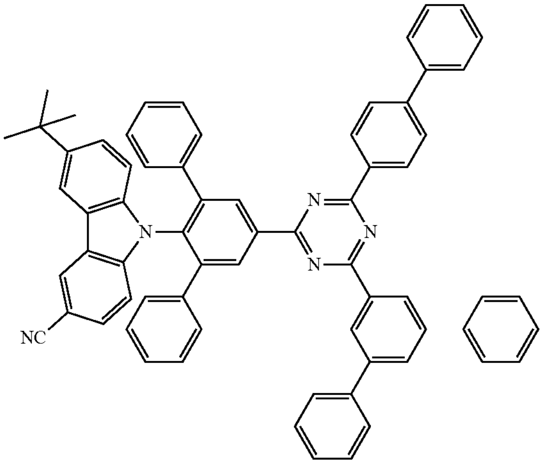

-continued
908
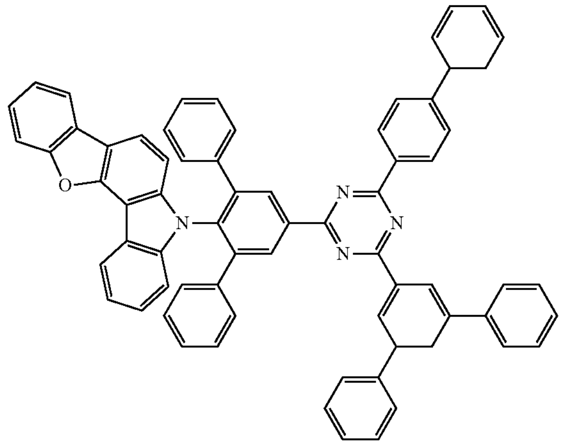
909
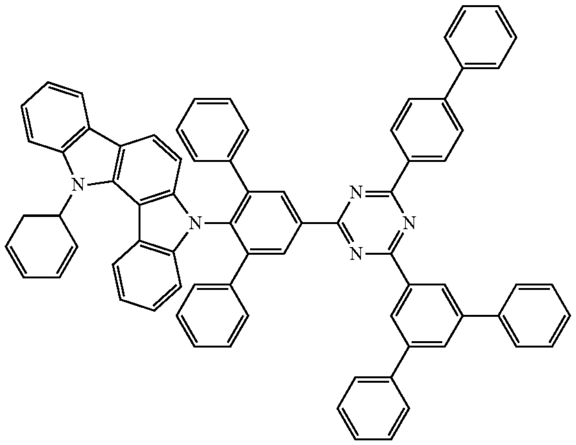
910
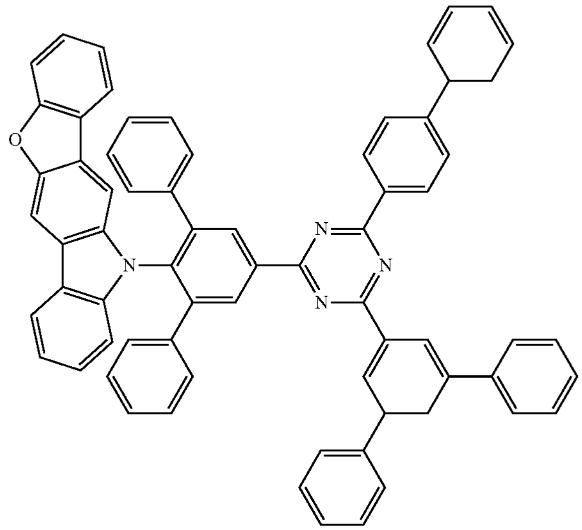
911
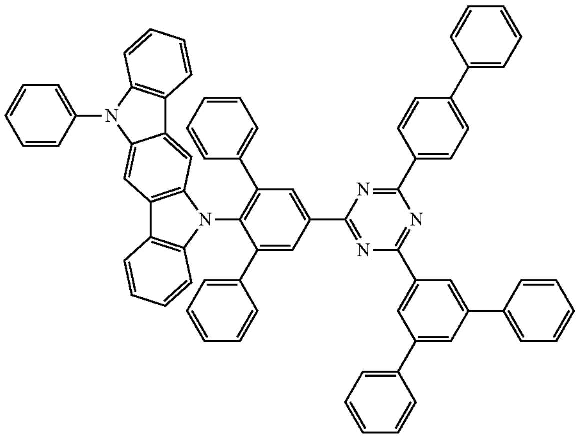
912
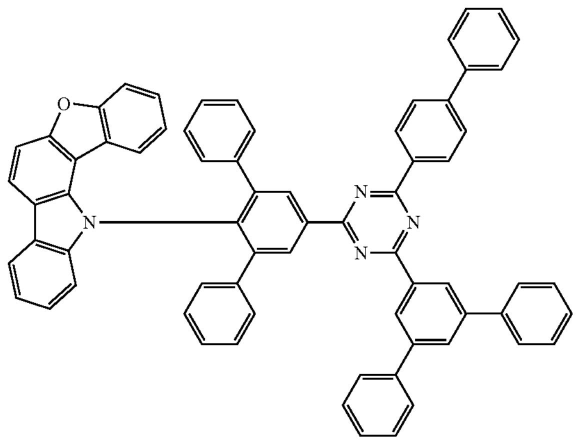
913
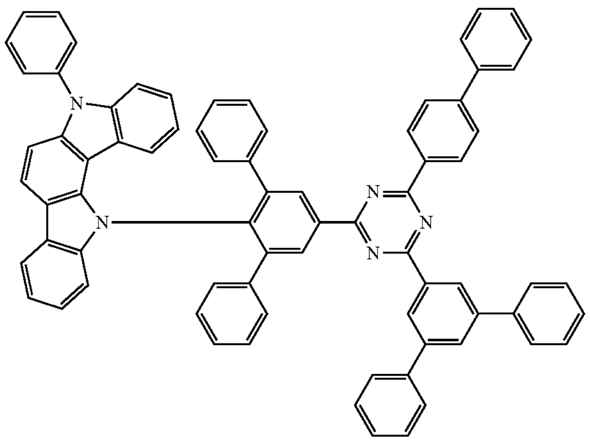

-continued
914
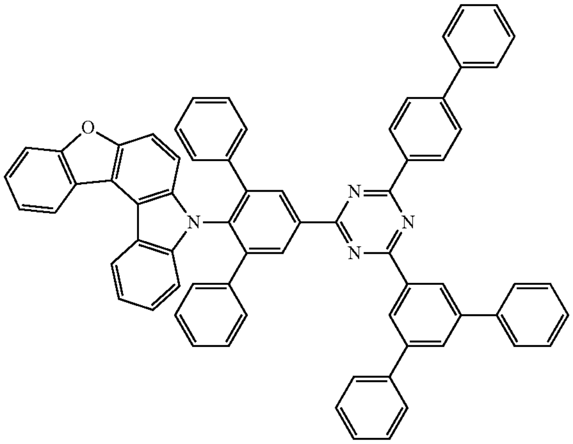
915
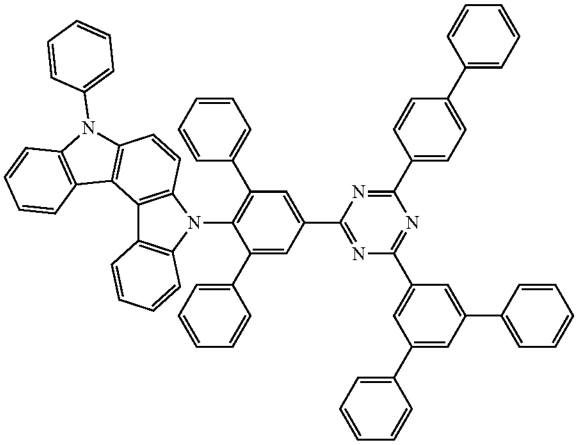
916
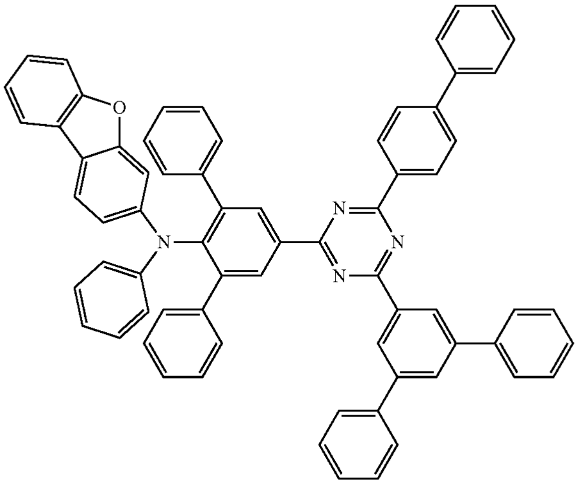
917
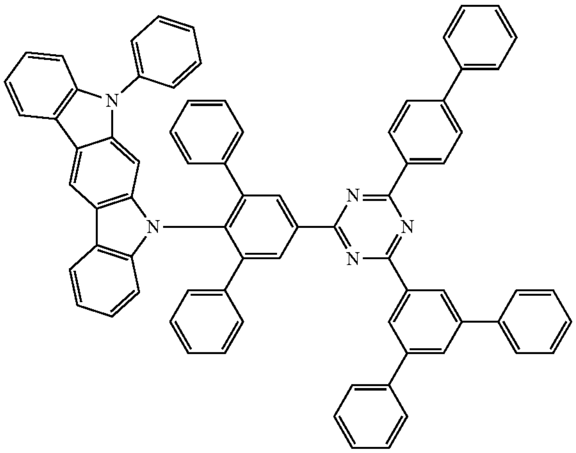
918
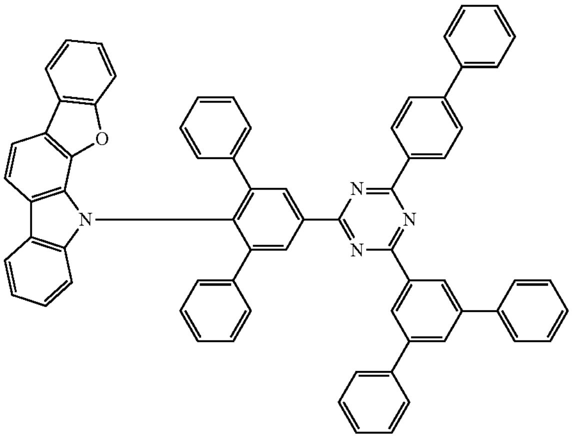
919
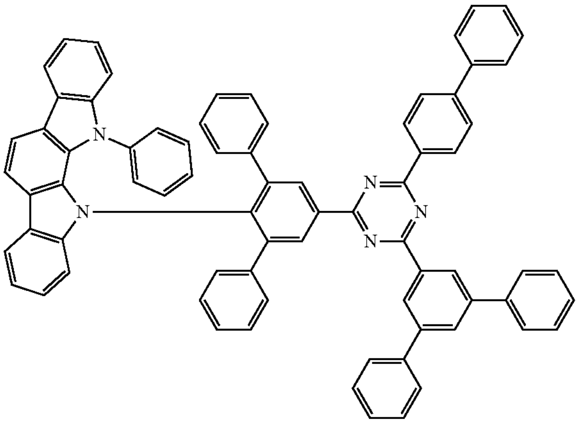

-continued
920
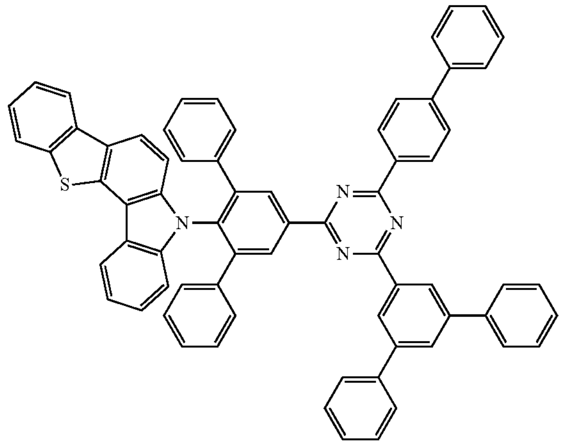
921
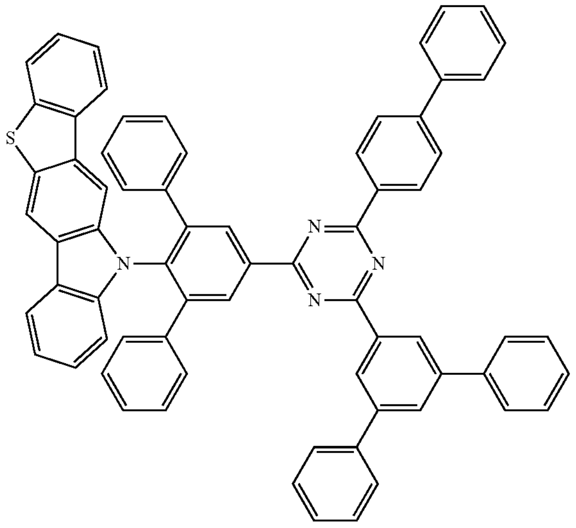
922
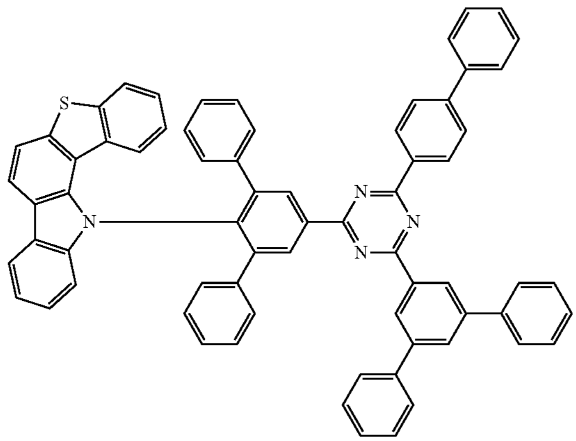
923
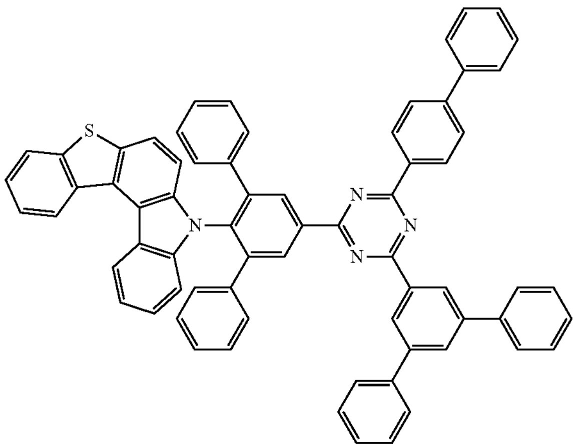
924
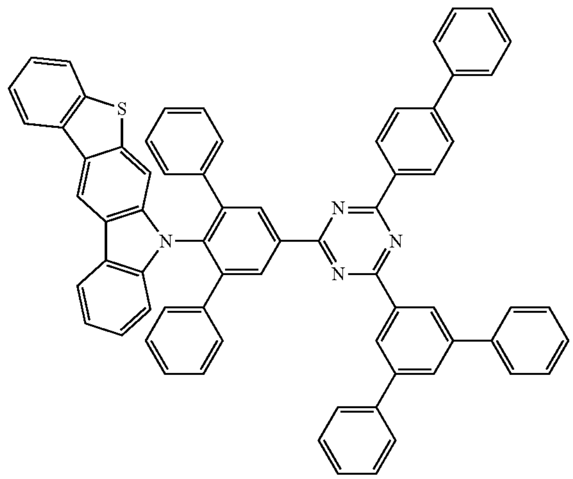
925
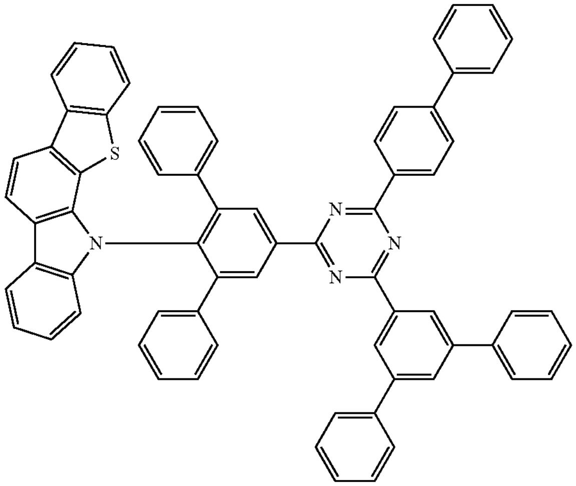

-continued
926
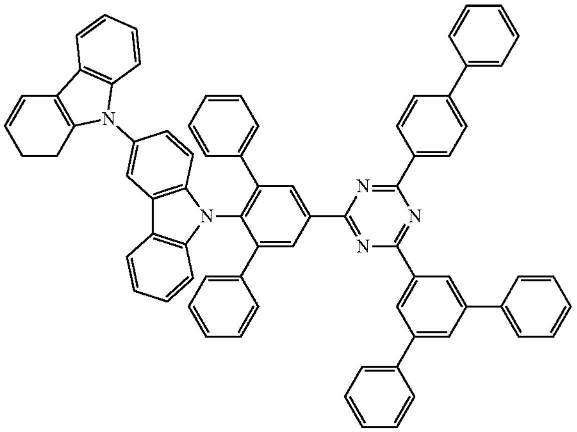
927
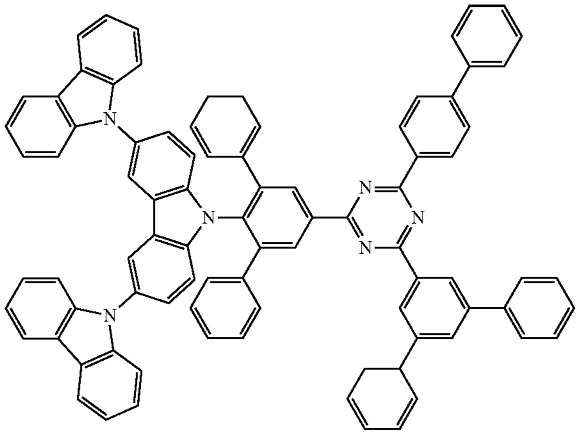
928
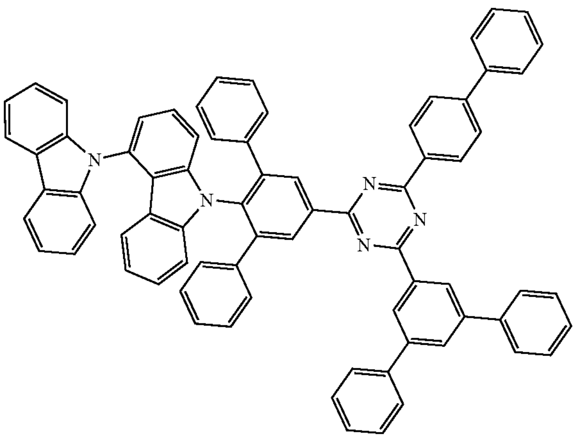
929
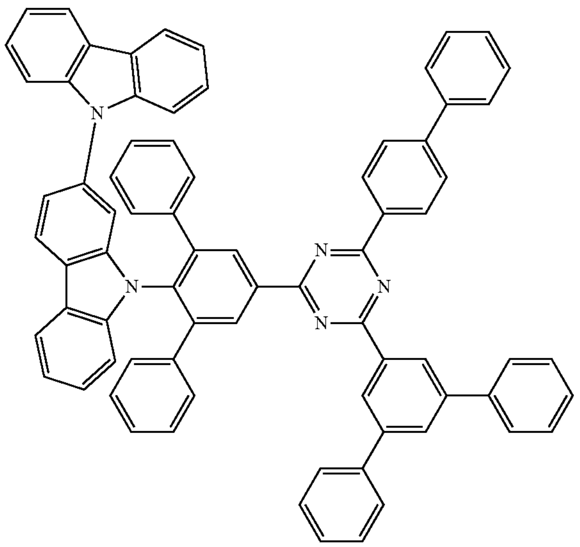
930
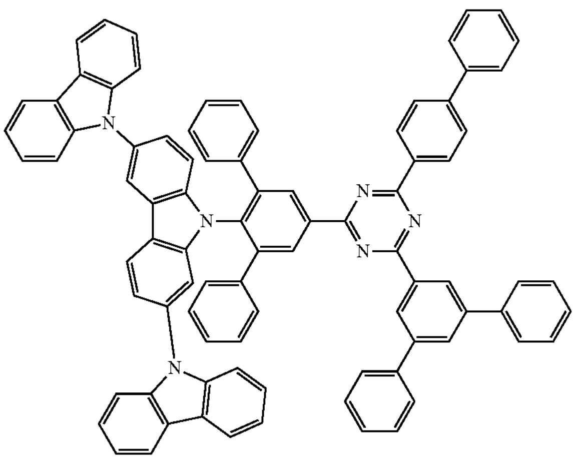
931
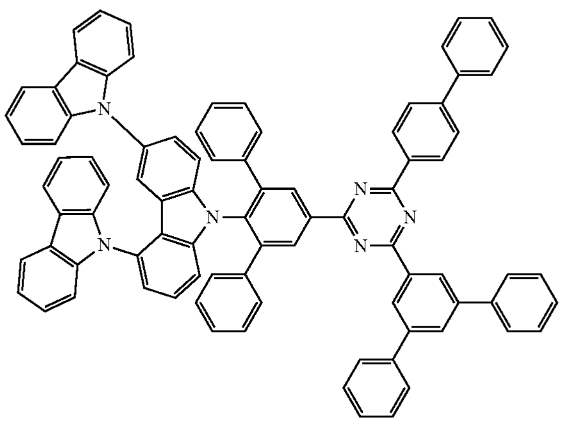

-continued
932
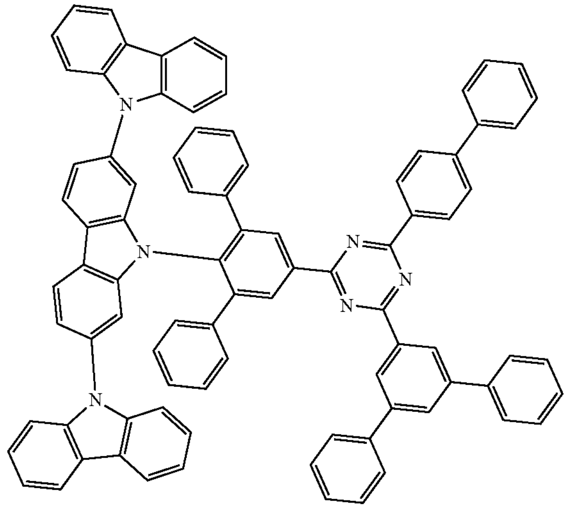
933
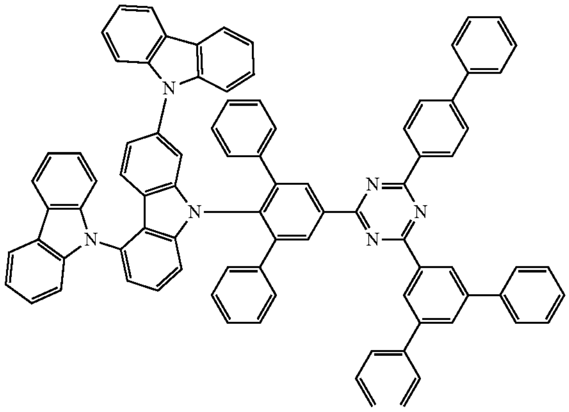
934
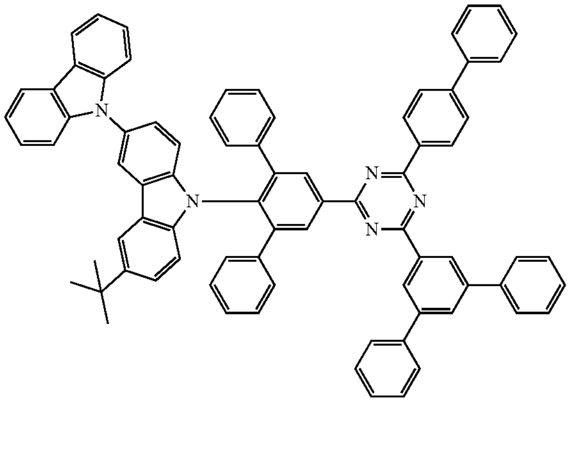
935
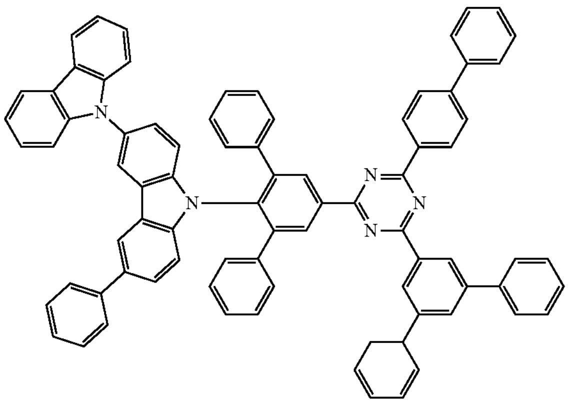
936
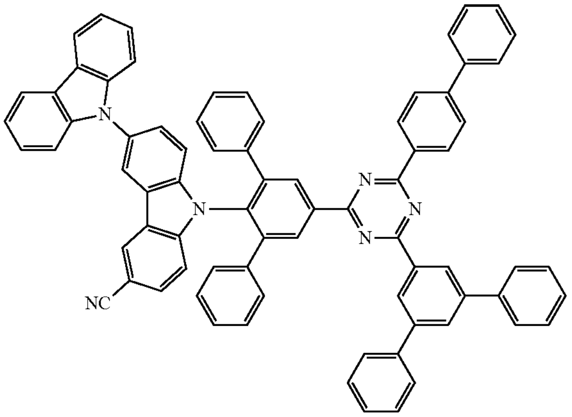
937
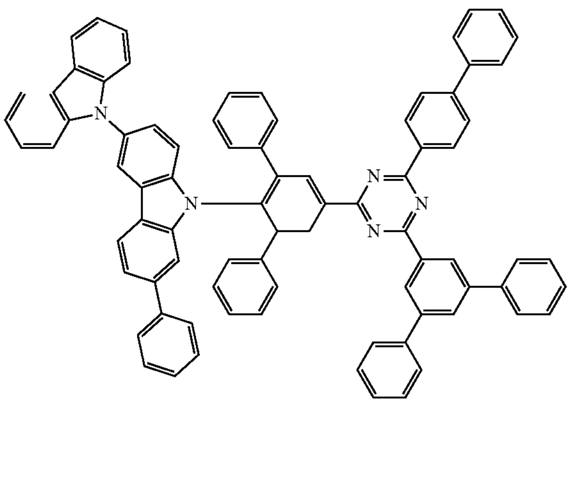

-continued
938
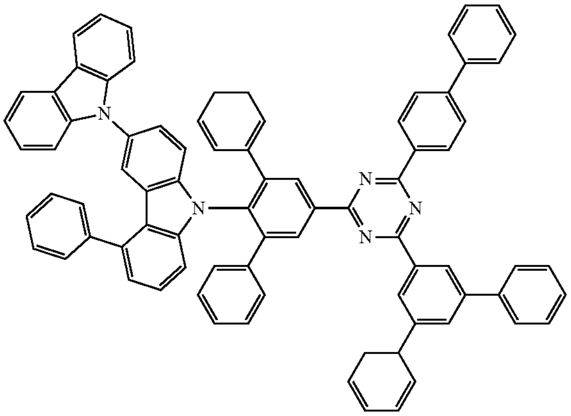
939
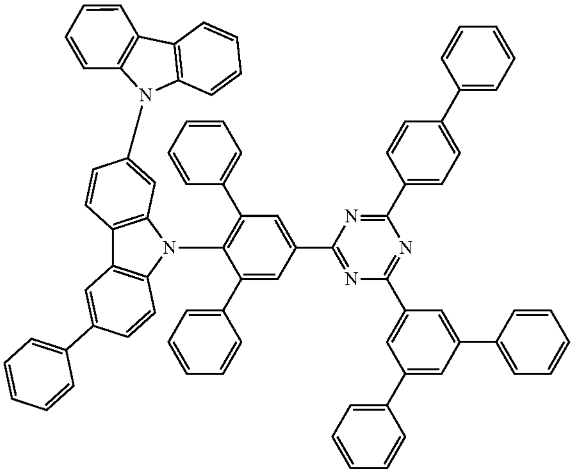
940
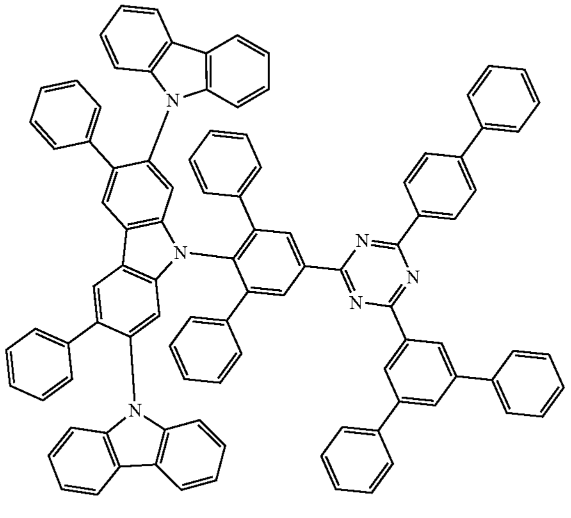
-continued
941
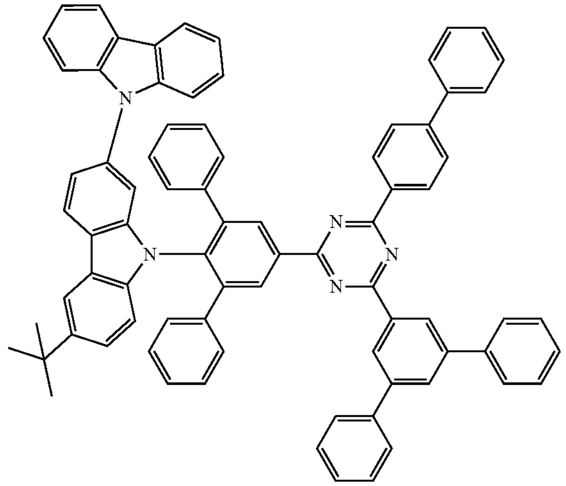
942
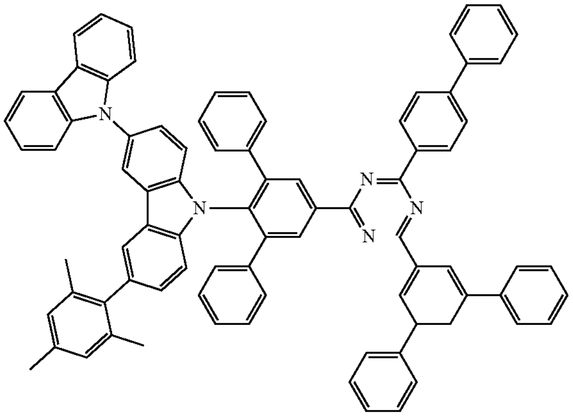
943
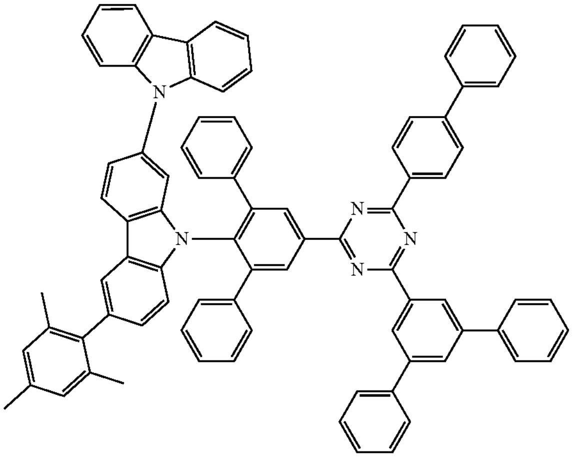

-continued
944
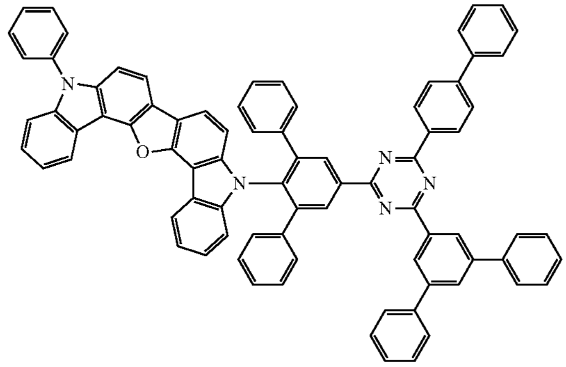
945
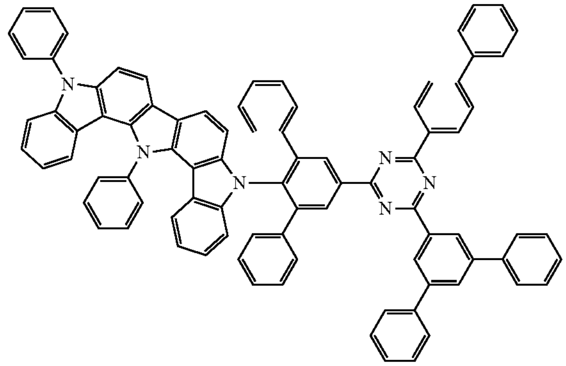
946
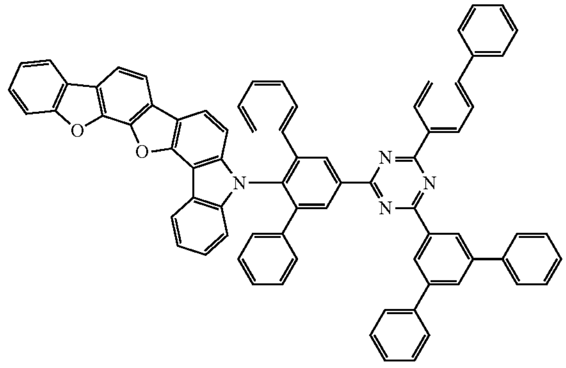
947
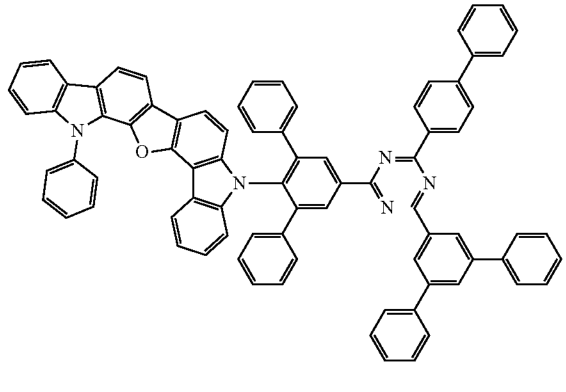
-continued
948
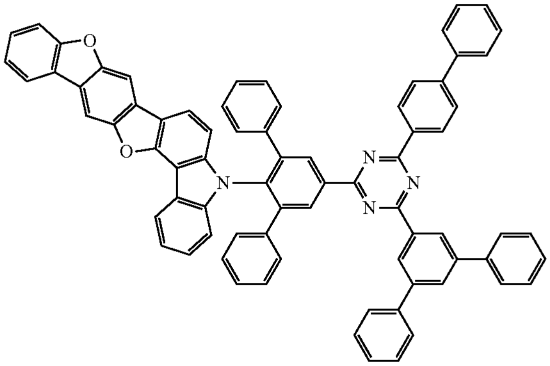
949
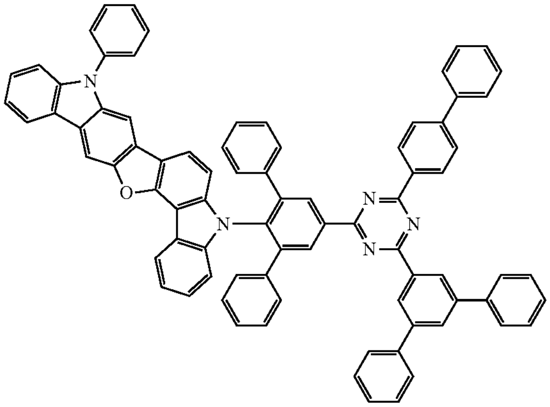
950
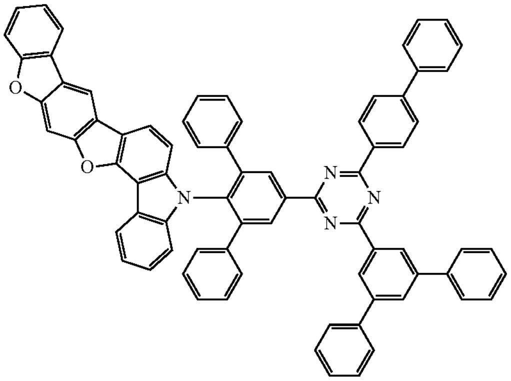
951
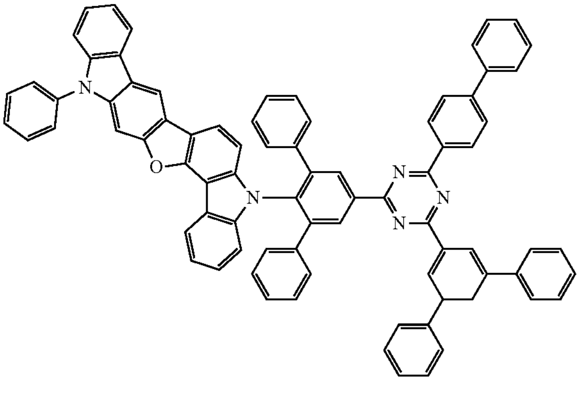

-continued
952
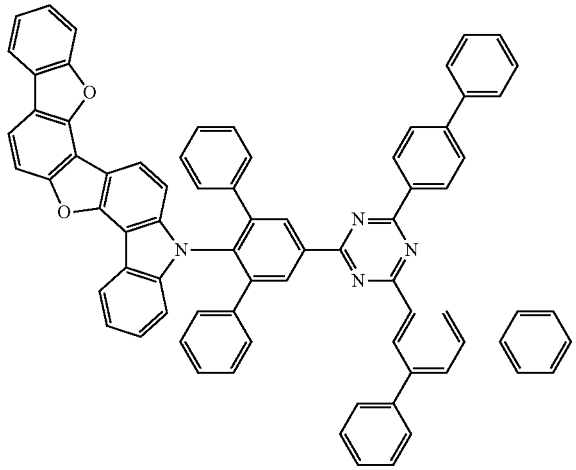
953
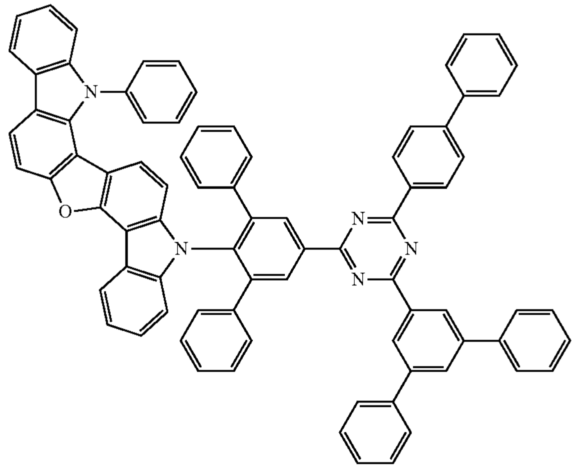
954
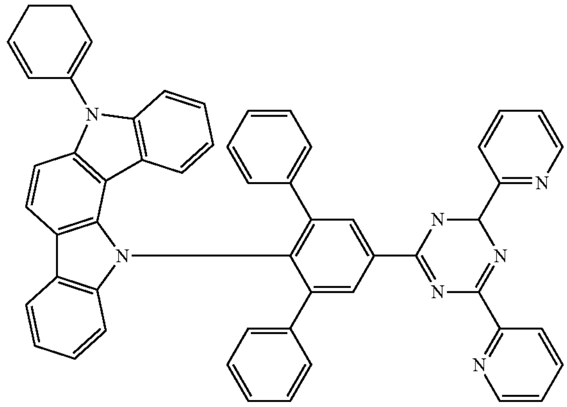
-continued
955
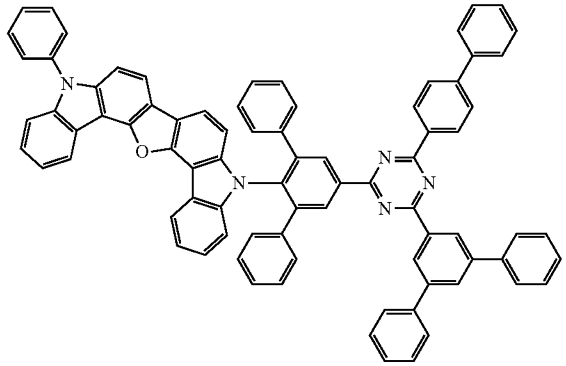
956
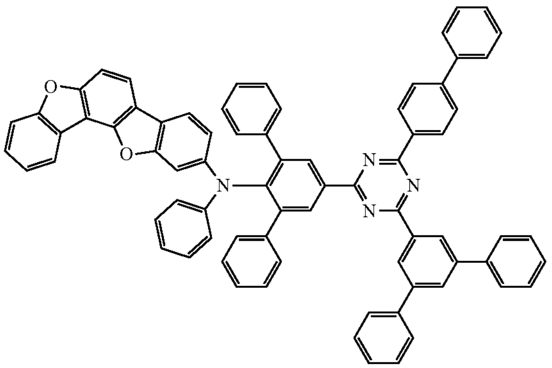
957
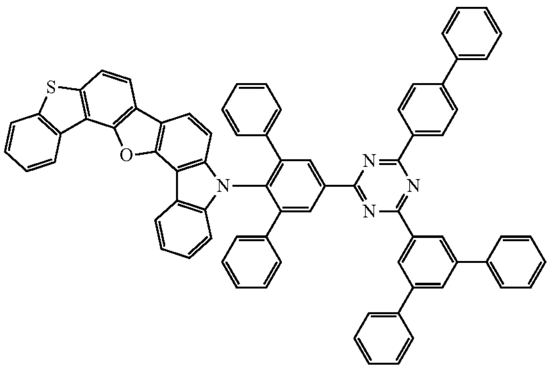
958
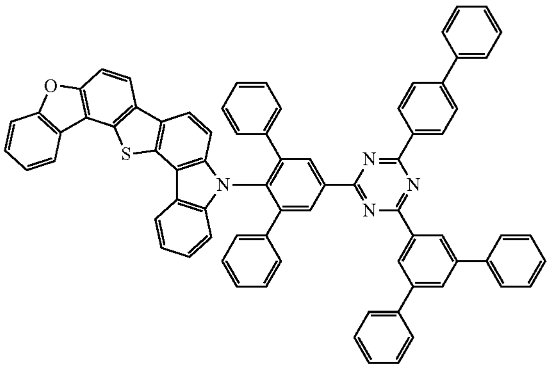

-continued
959
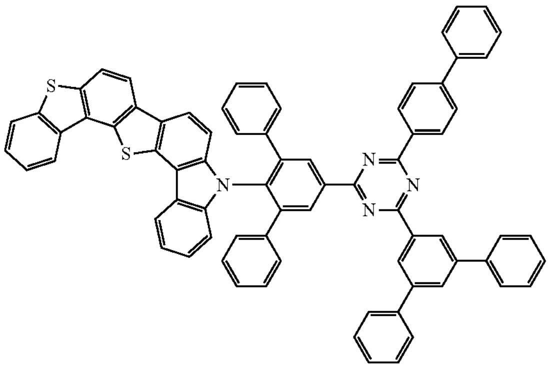
960
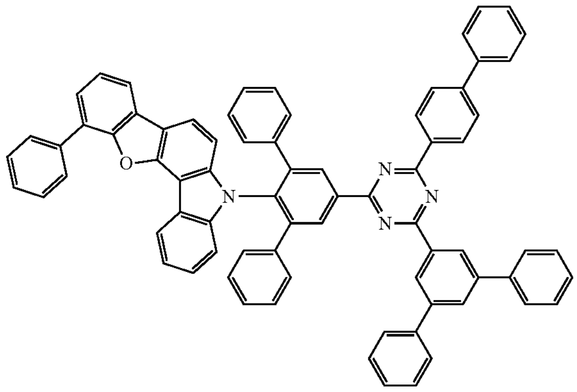
961
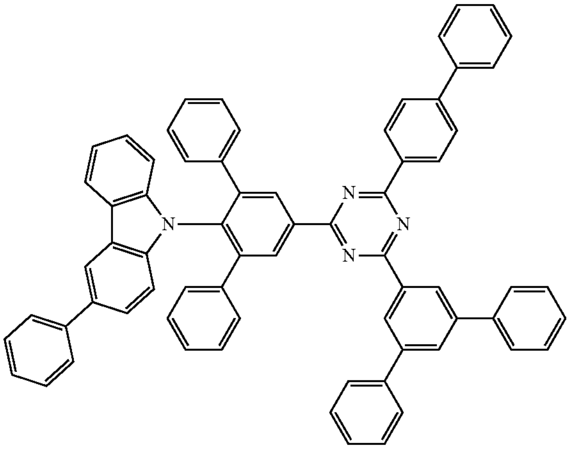
962
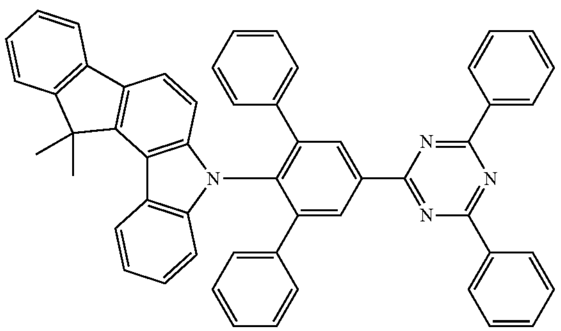
-continued
963
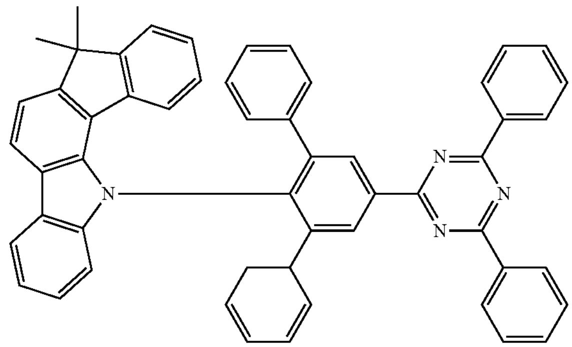
964
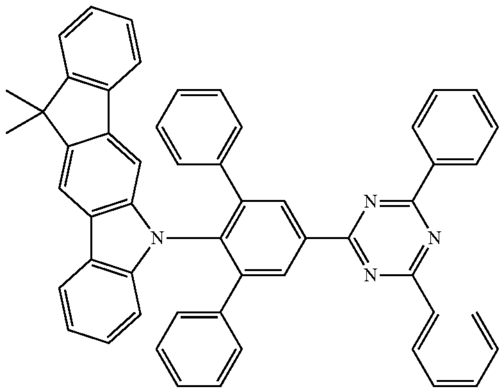
965
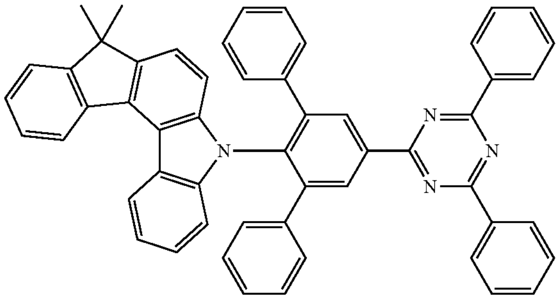
966
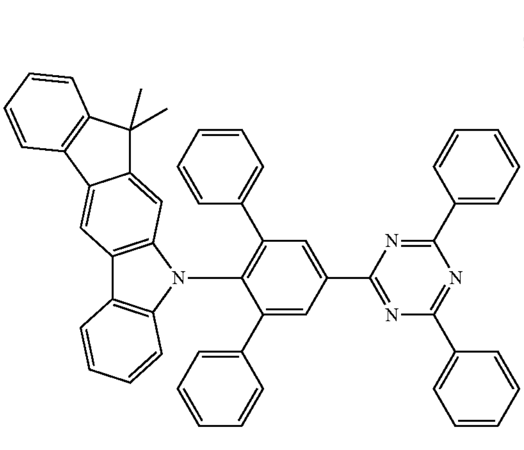

-continued
967
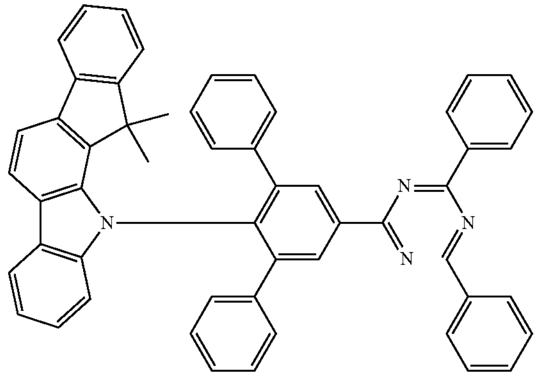
968
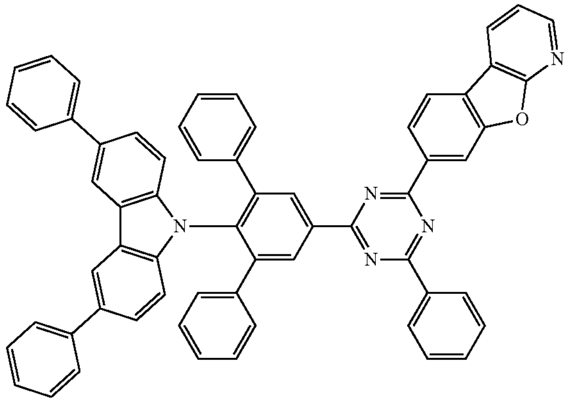
969
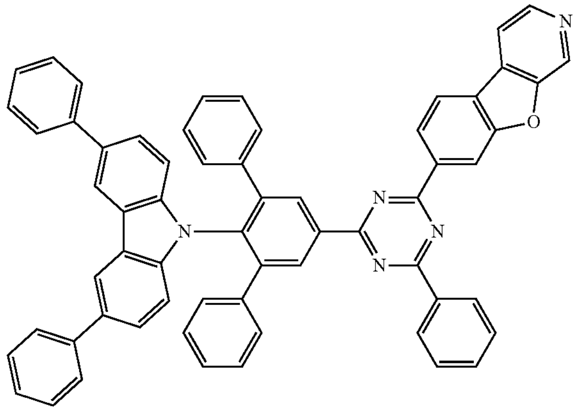
-continued
970
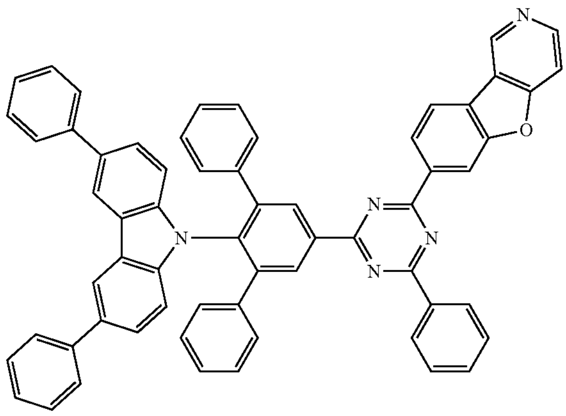
971
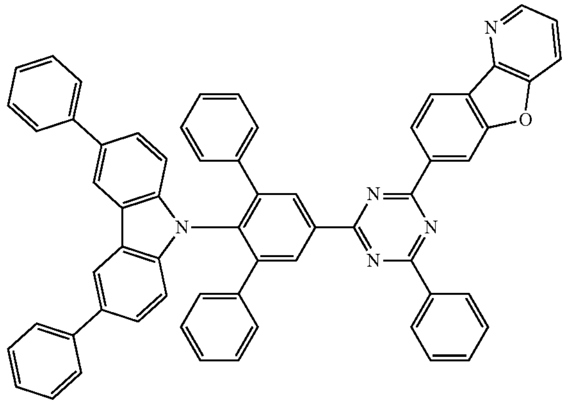
972
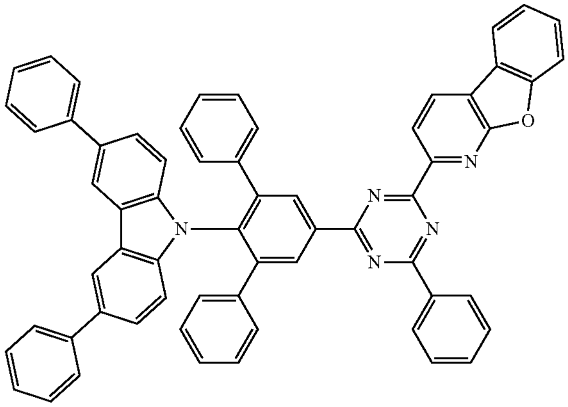

-continued
973
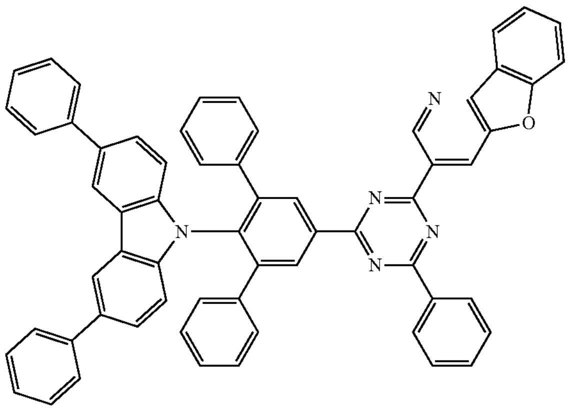
974
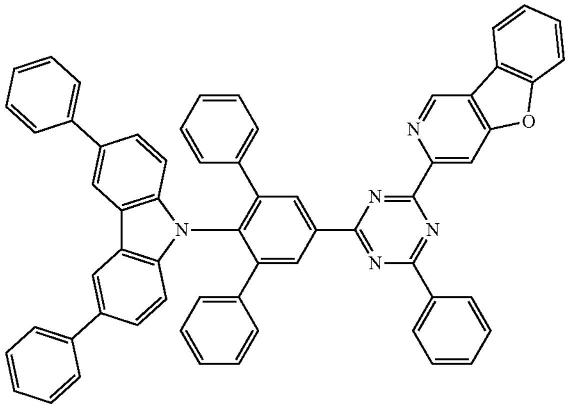
975
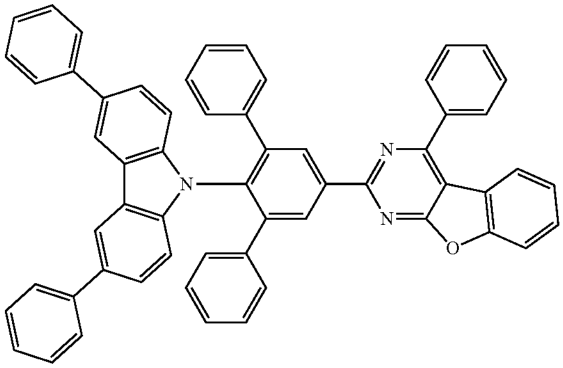
976
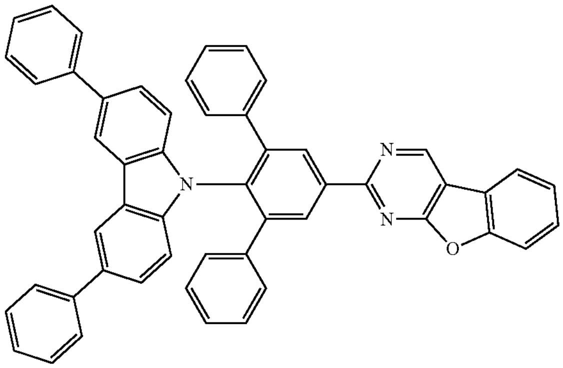
-continued
977
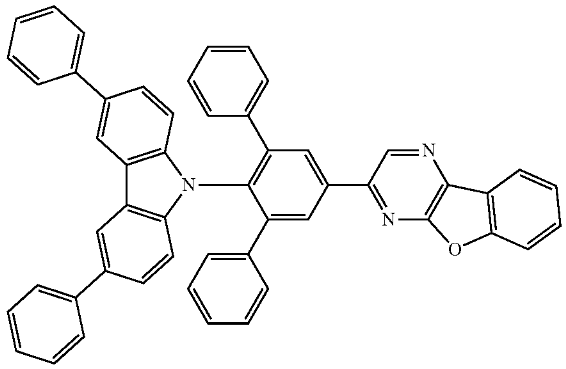
978
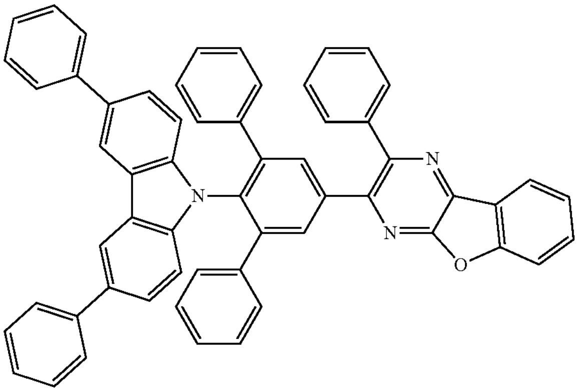
979
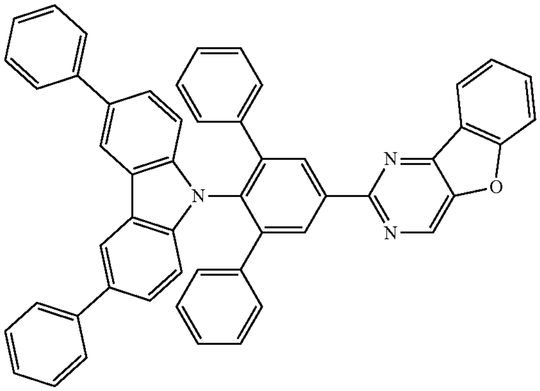

-continued
980
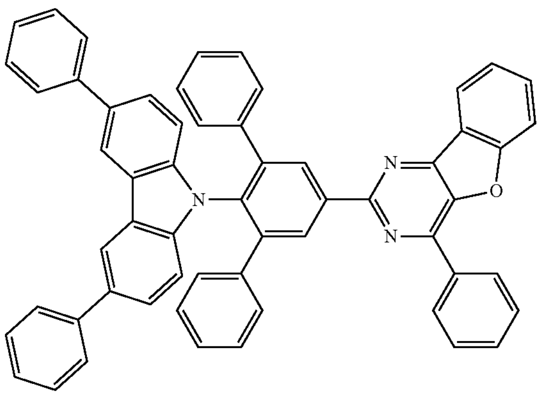
981
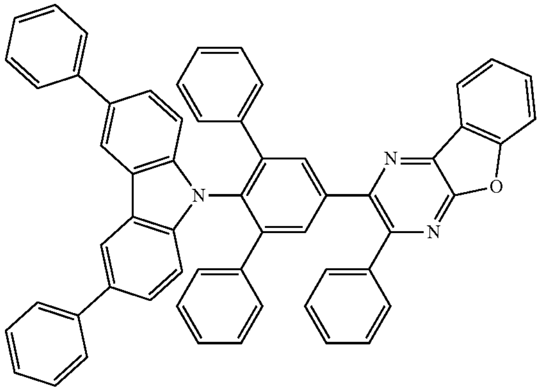
982
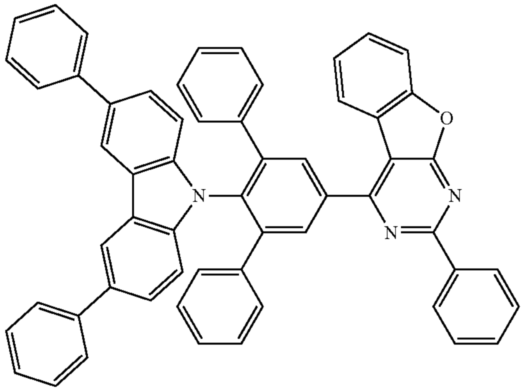
983
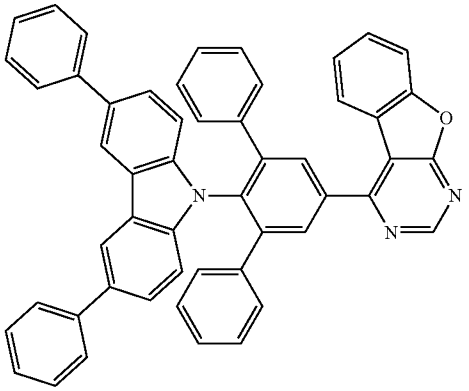
-continued
984
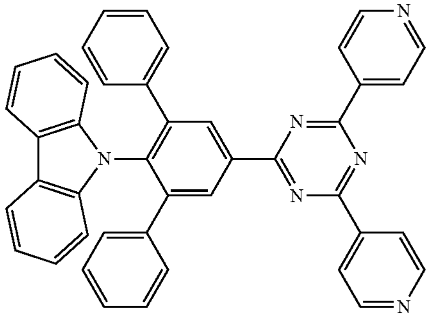
985
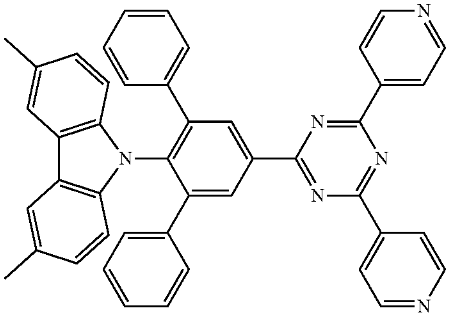
986
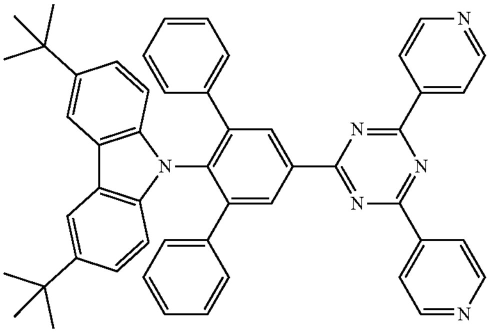
987
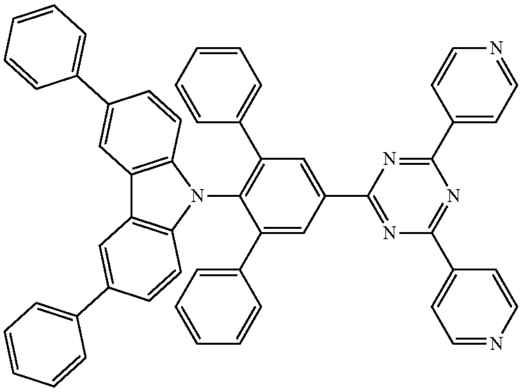

-continued
988
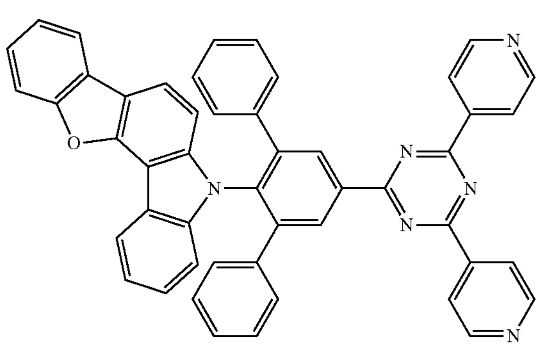
989
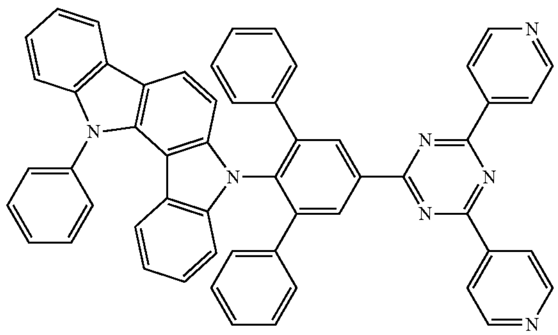
990
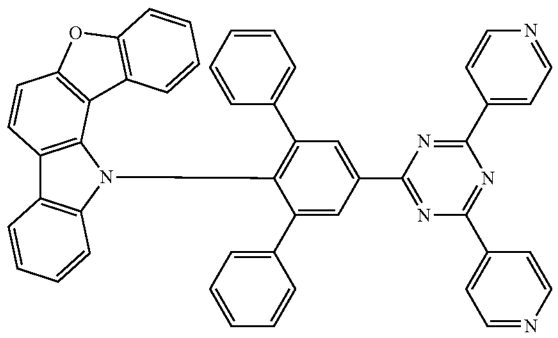
991
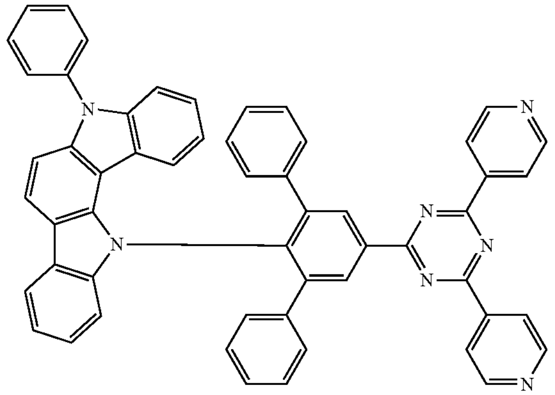
-continued
992
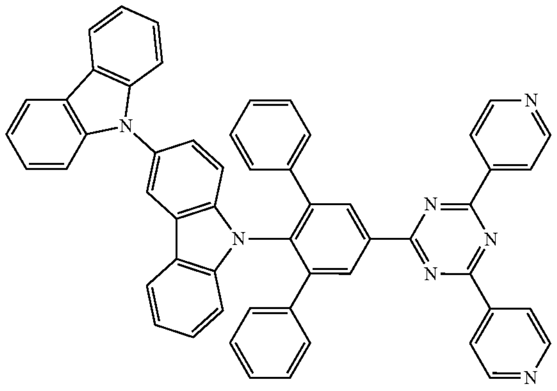
993
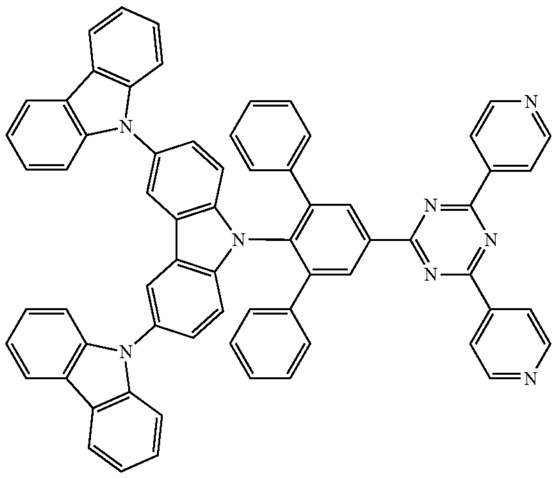
994
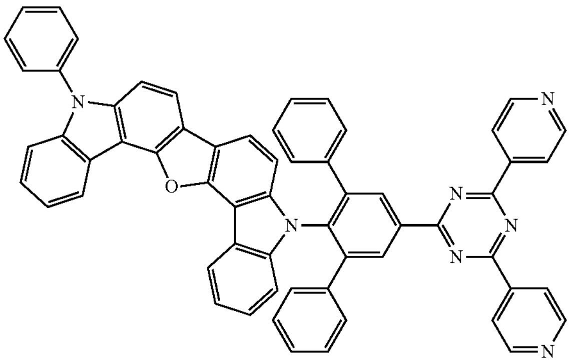

-continued
995
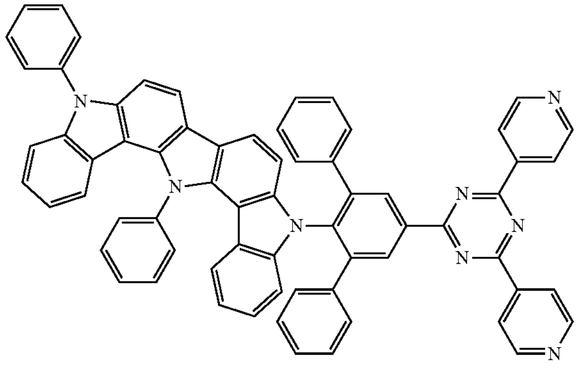
996
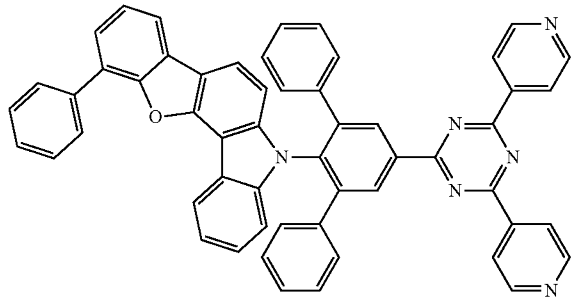
997
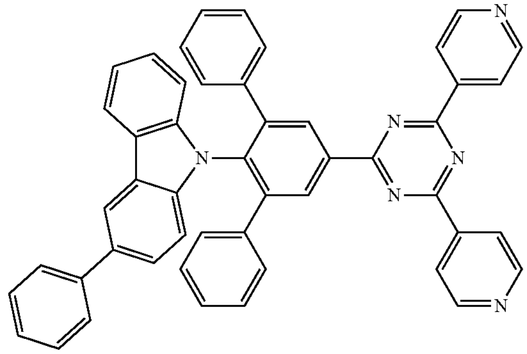
998
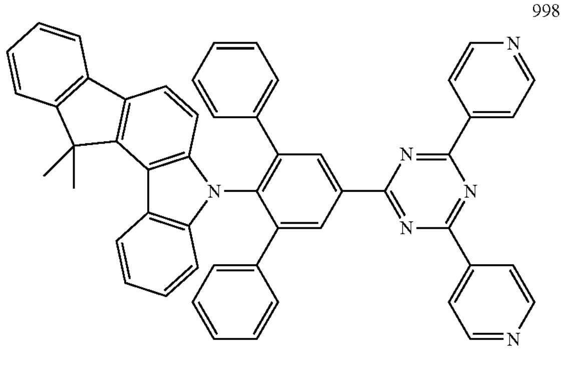
-continued
999
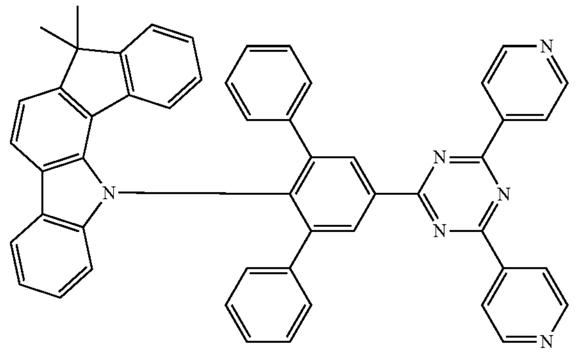
1000
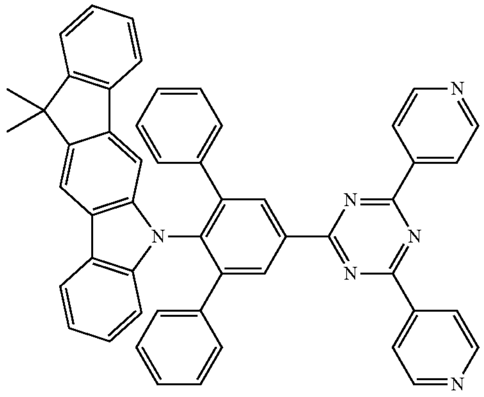
1001
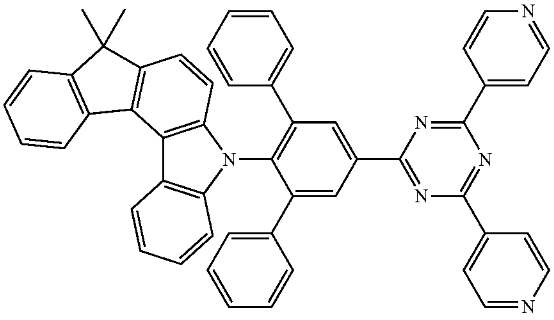
1002
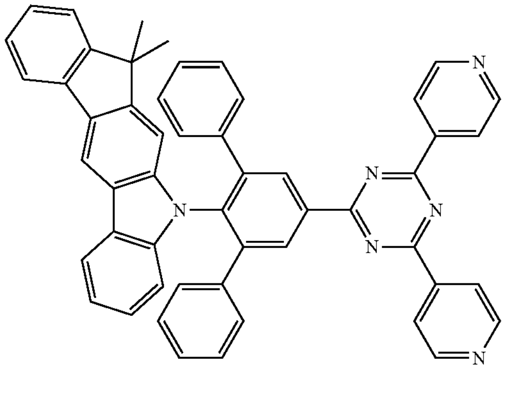

-continued
1003
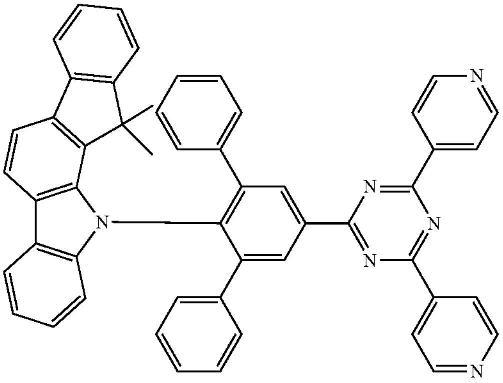
1004
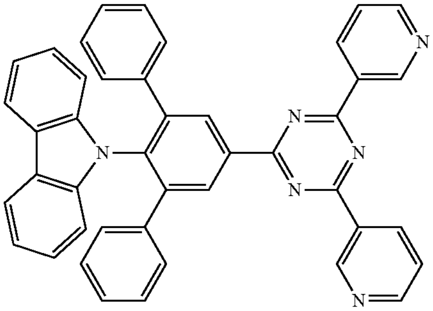
1005
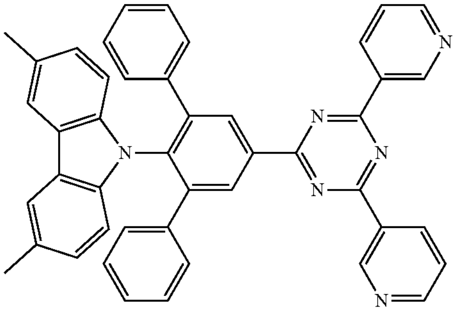
1006
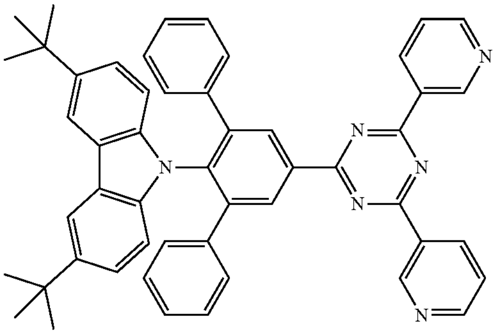
-continued
1007
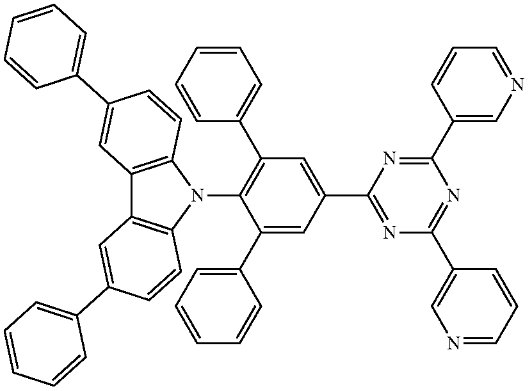
1008
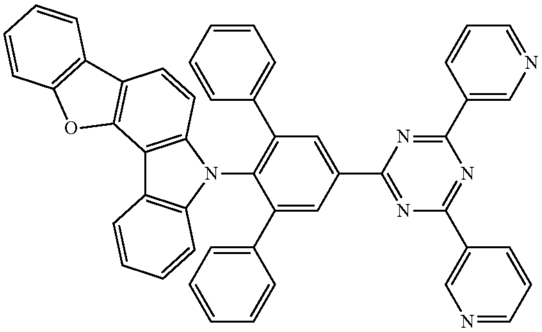
1009
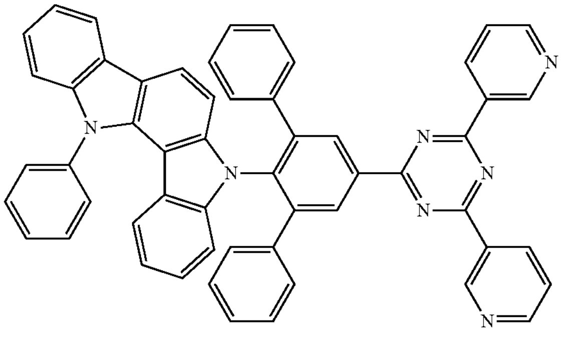
1010
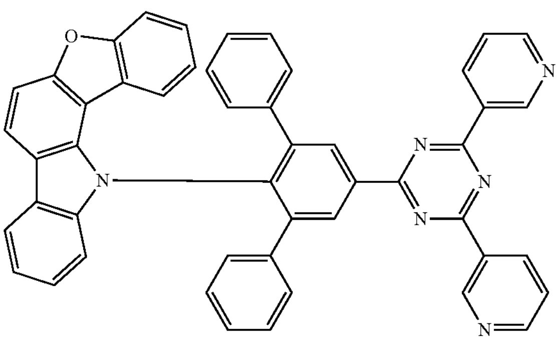

-continued
1011
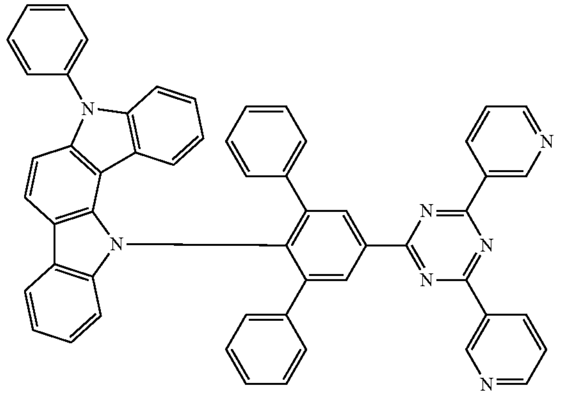
1012
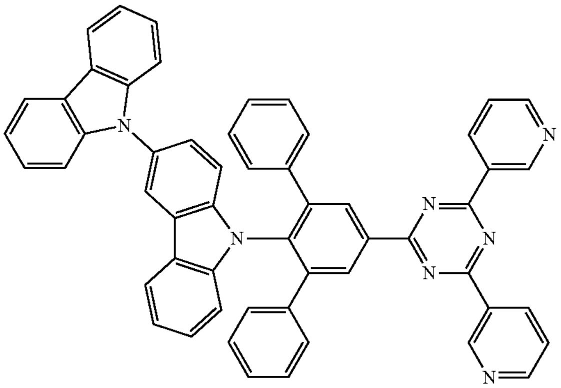
1013
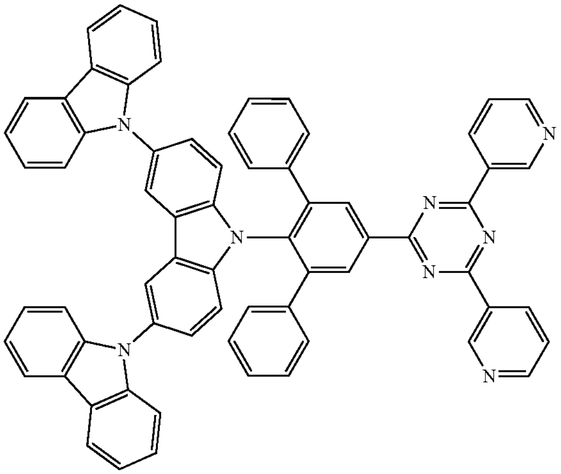
-continued
1014
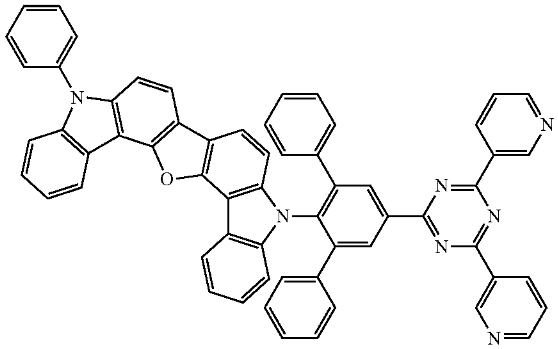
1015
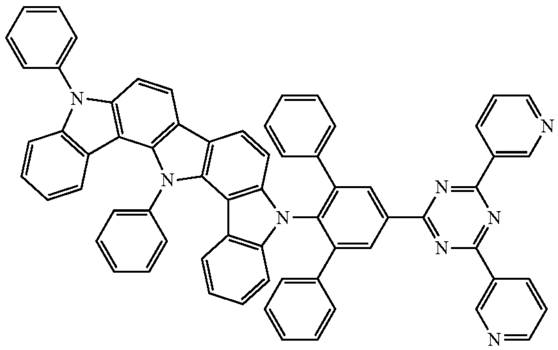
1016
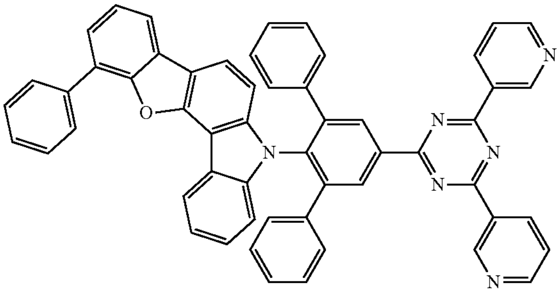
1017
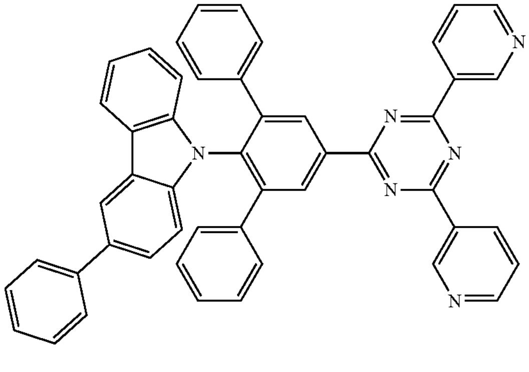

1018
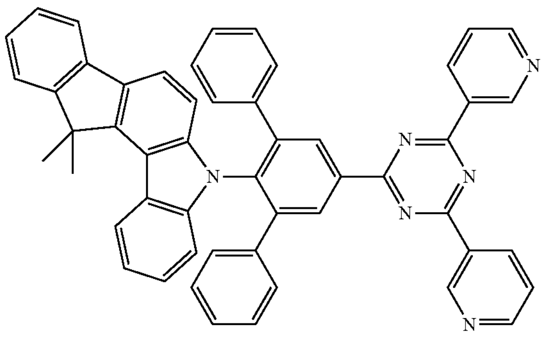
1019
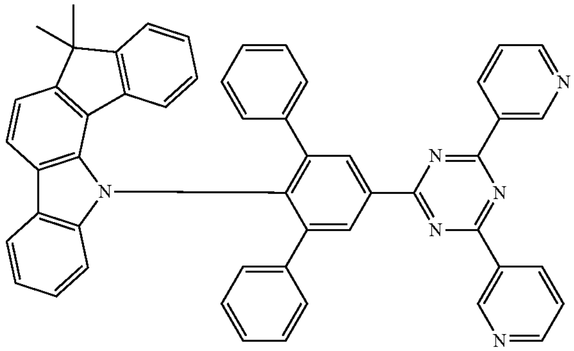
1020
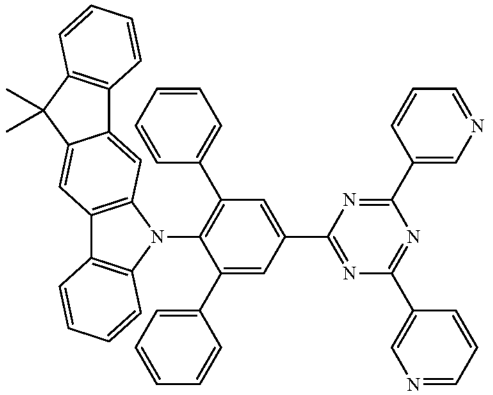
1021
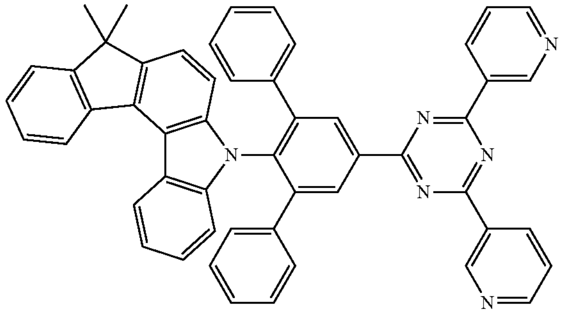
1022
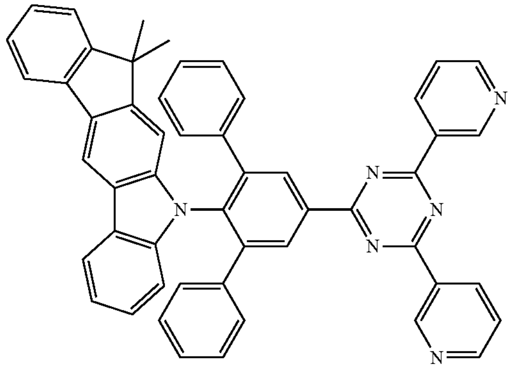
1023
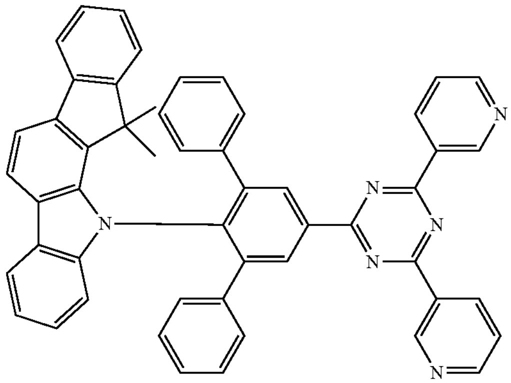
1024
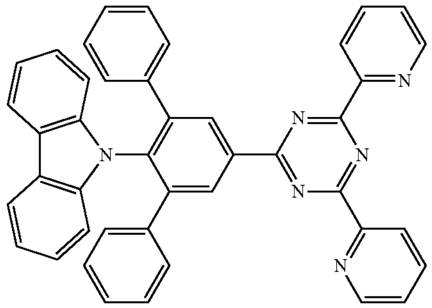
1025
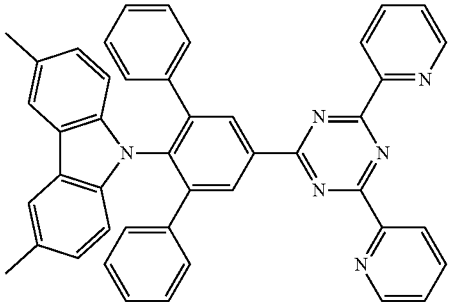

1026
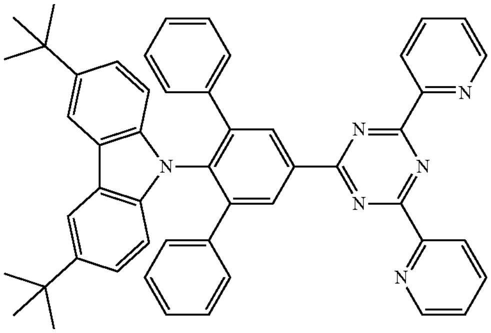
1027
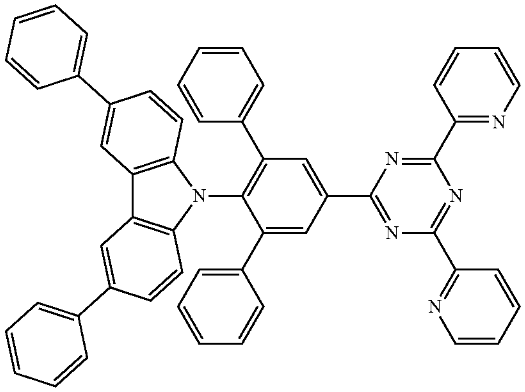
1028
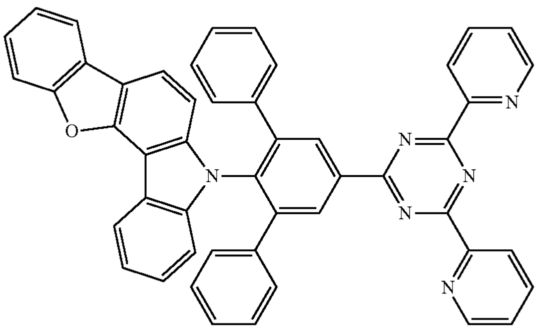
1029
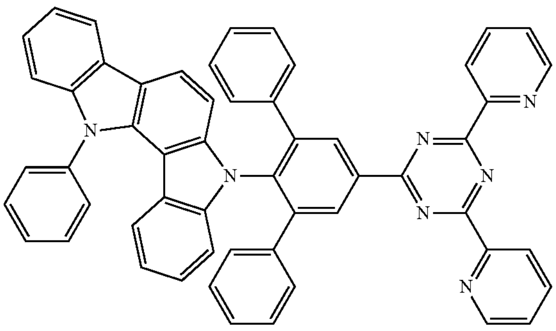
-continued
1030
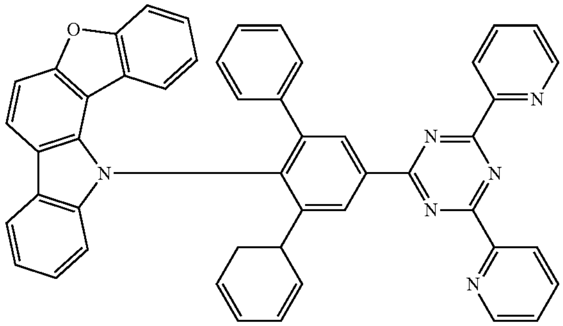
Group X
1
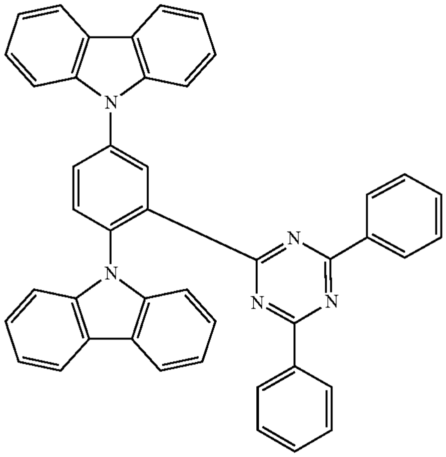
2
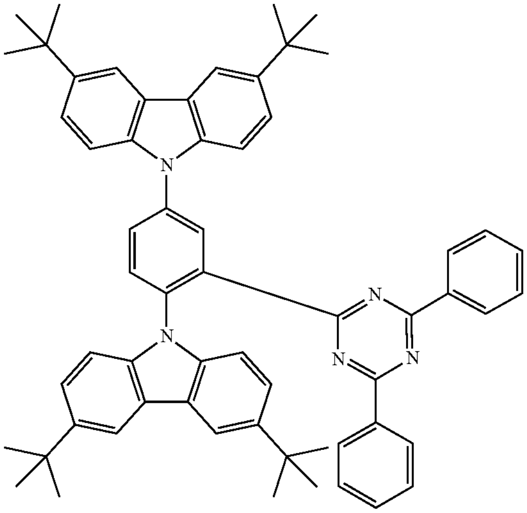

-continued
3
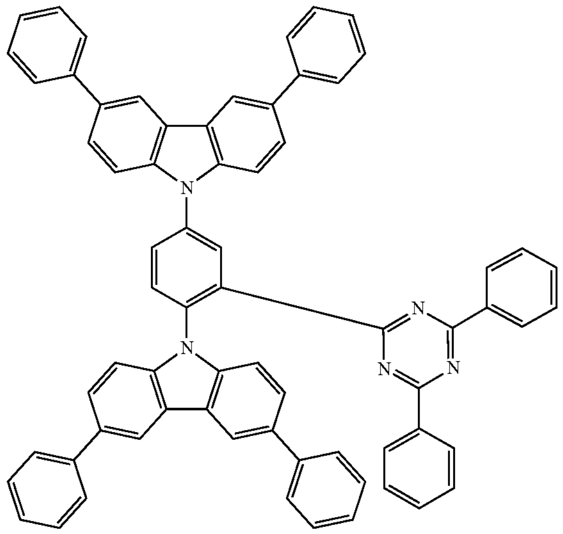
4
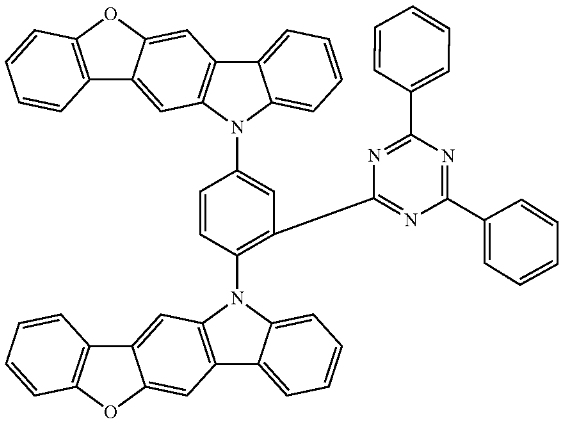
5
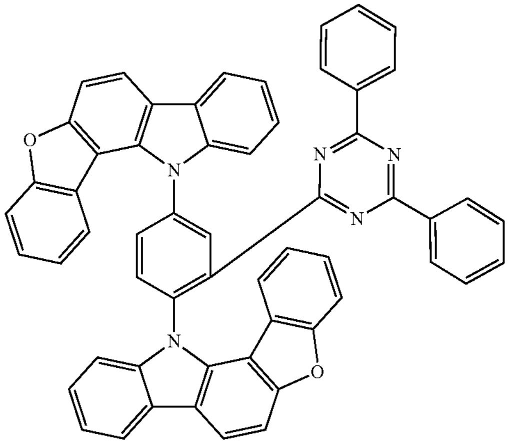
-continued
6
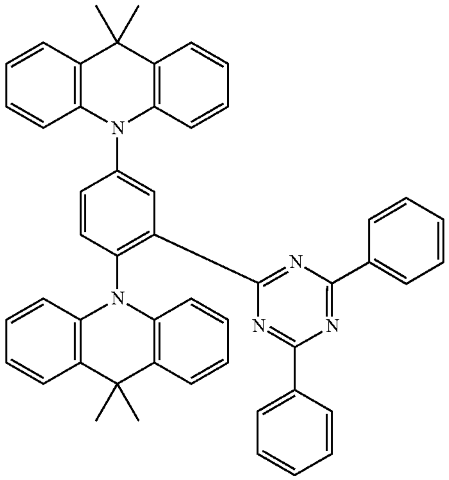
7
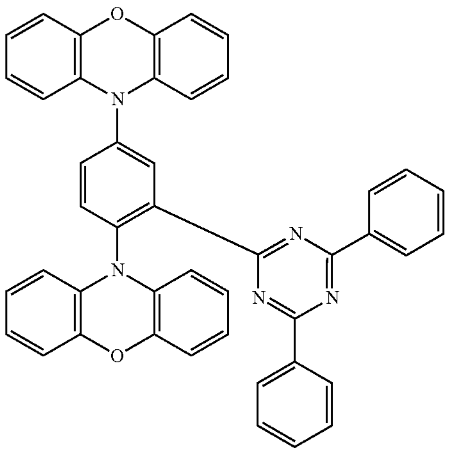
8
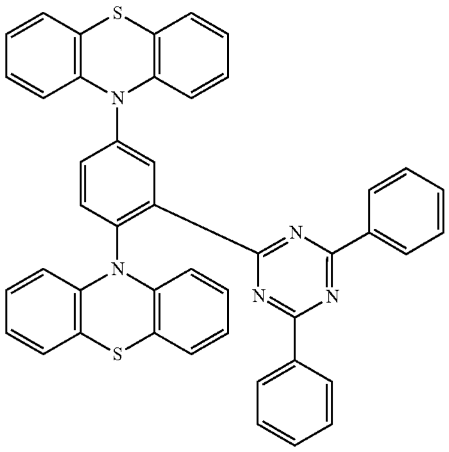

-continued
9
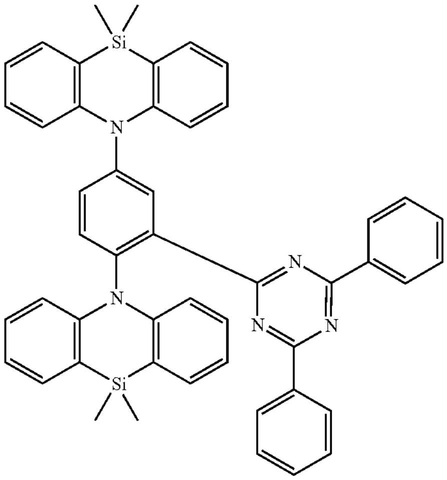
10
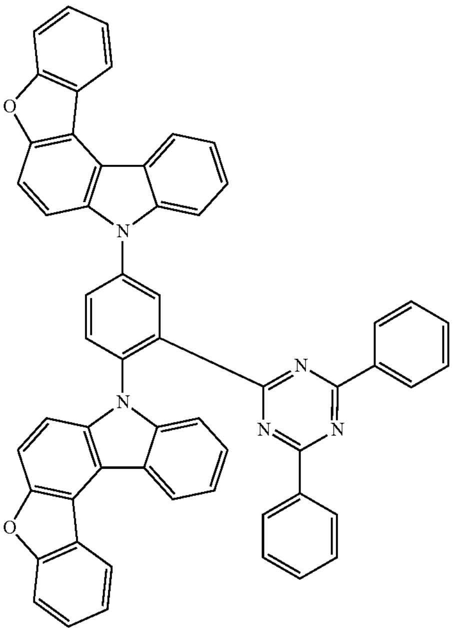
11
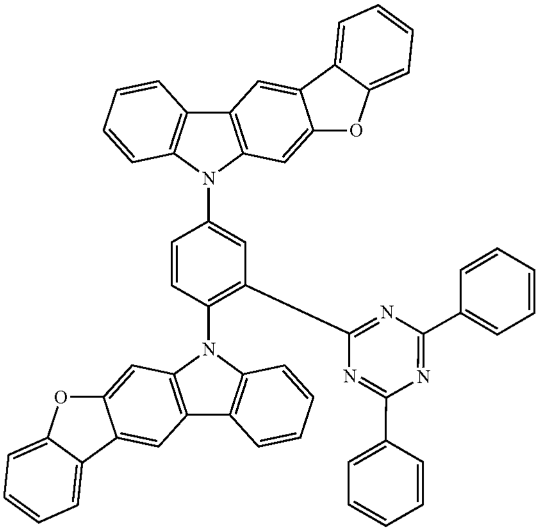
-continued
12
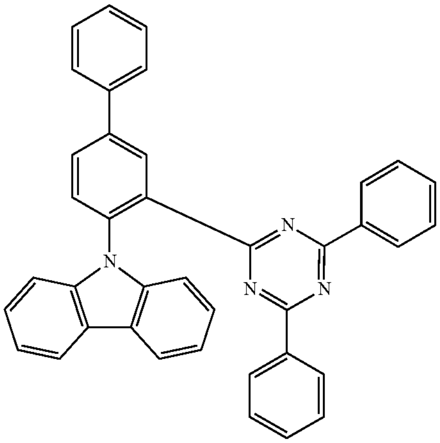
13
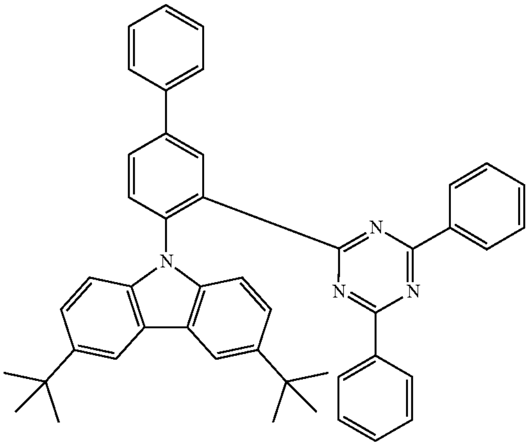
14
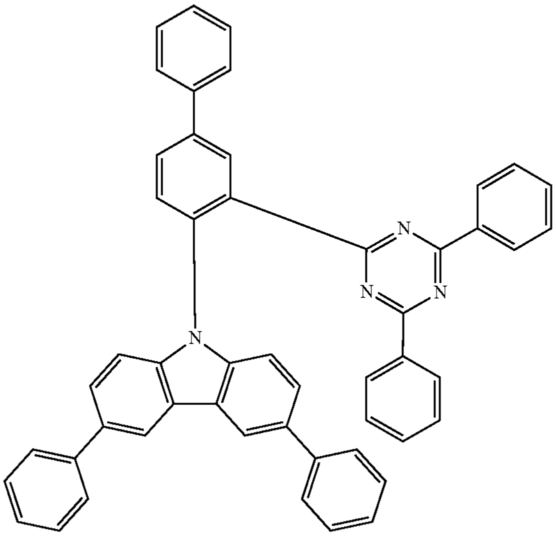

-continued
15
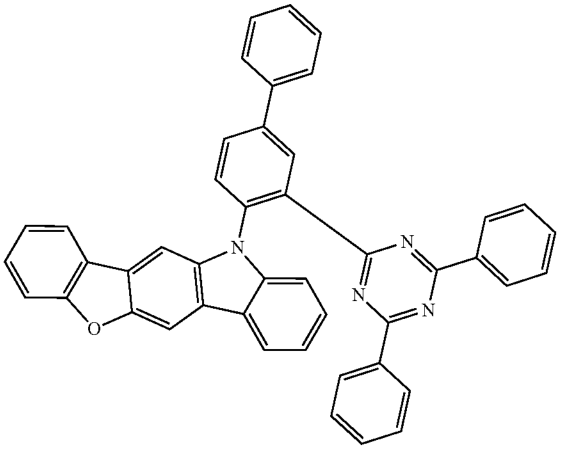
16
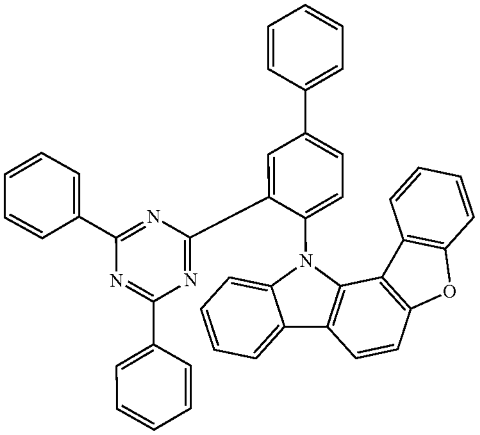
17
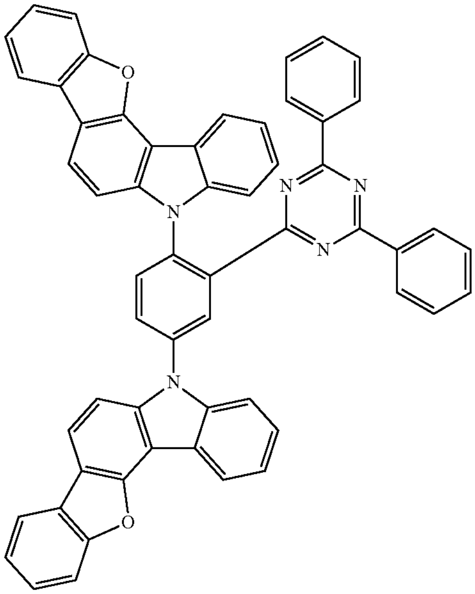
-continued
18
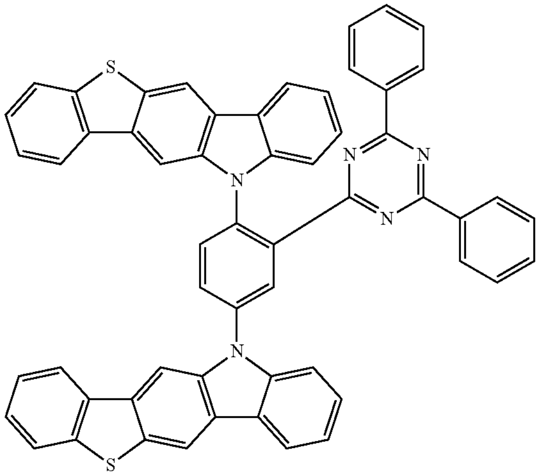
19
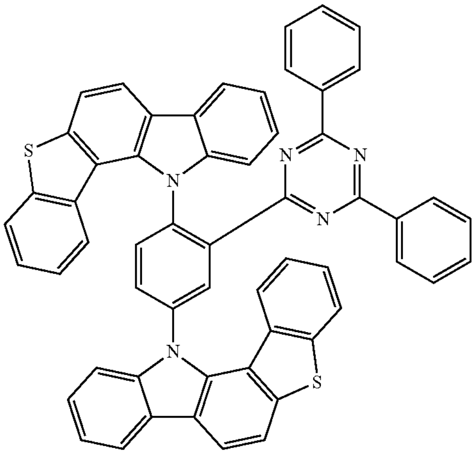
20
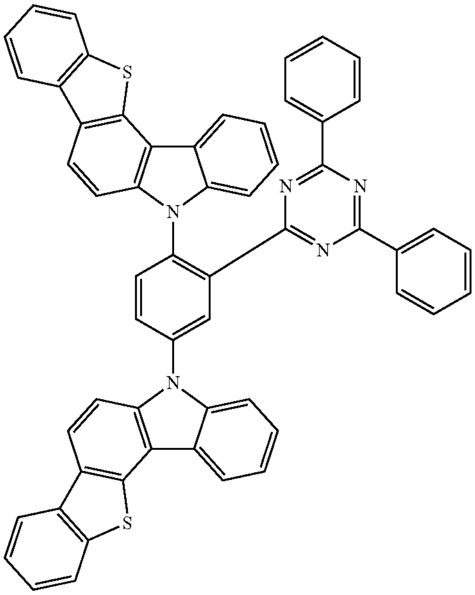

-continued
21
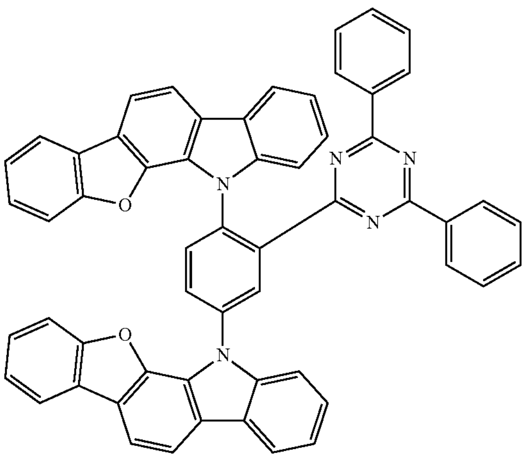
22
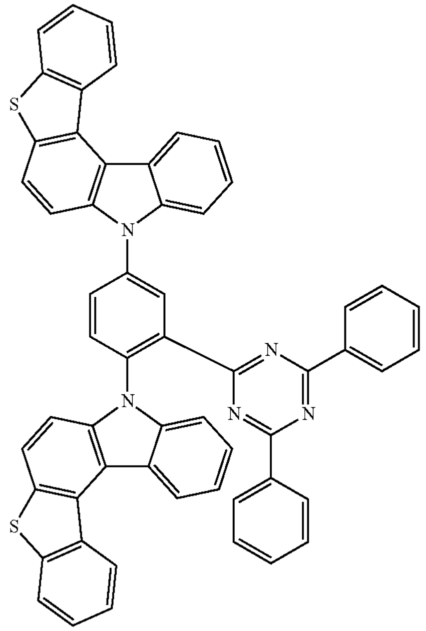
23
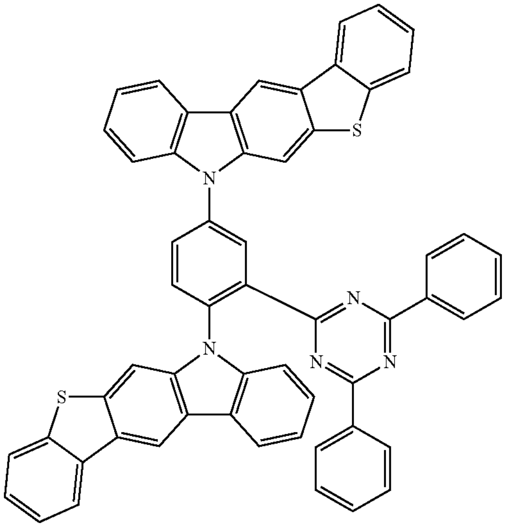
-continued
24
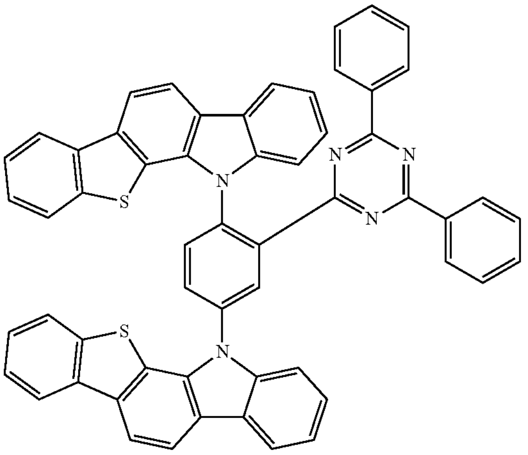
25
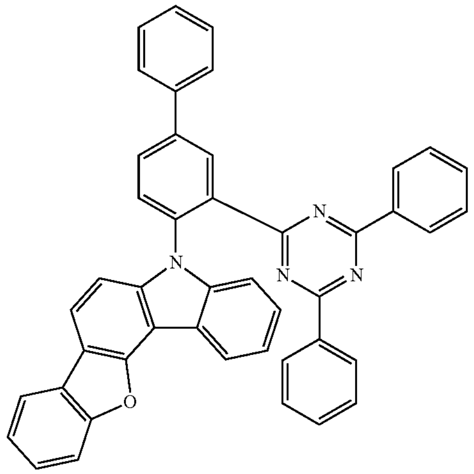
26
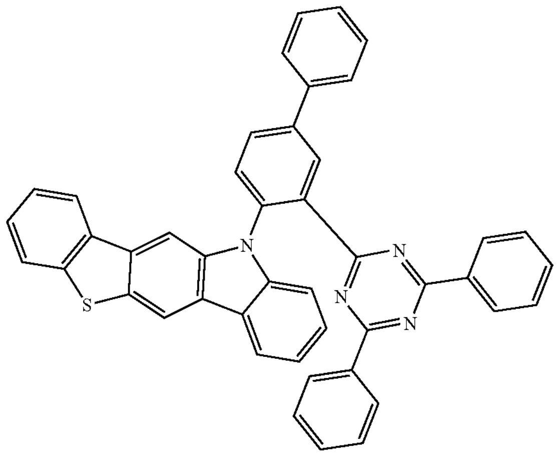

27
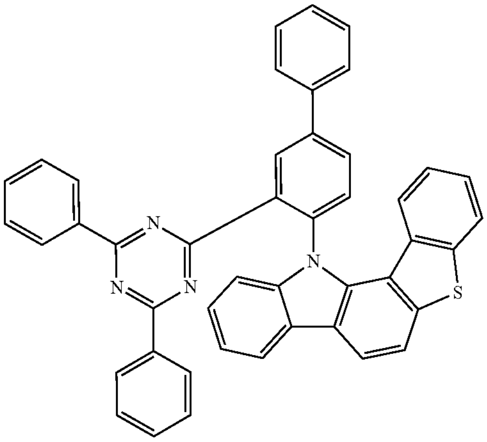
28
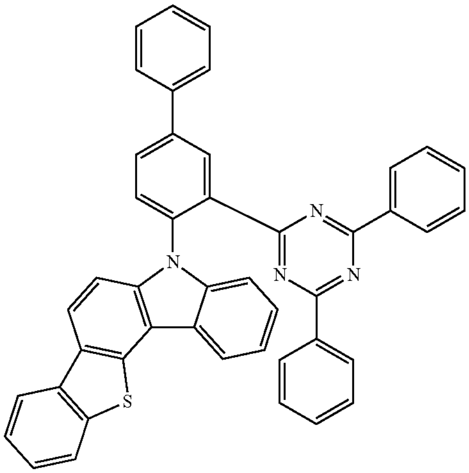
29
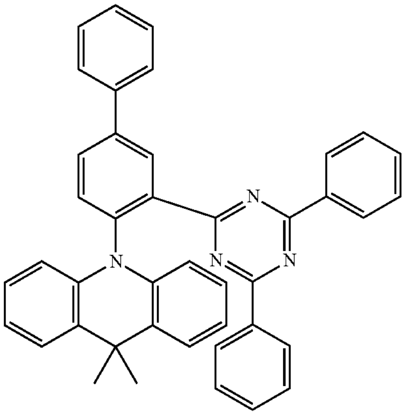
30
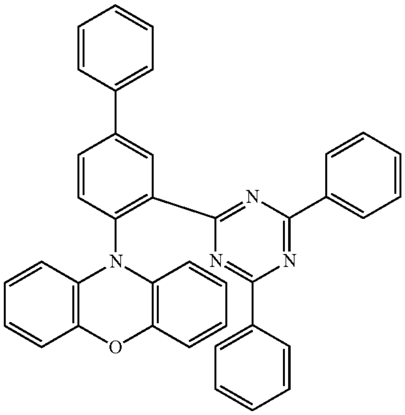
31
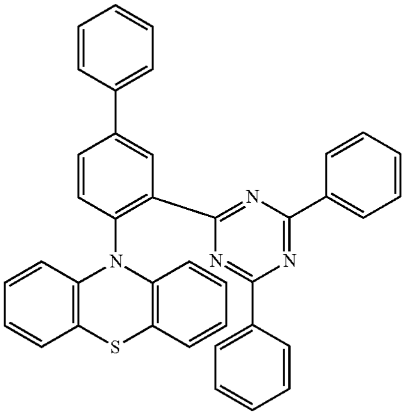
32
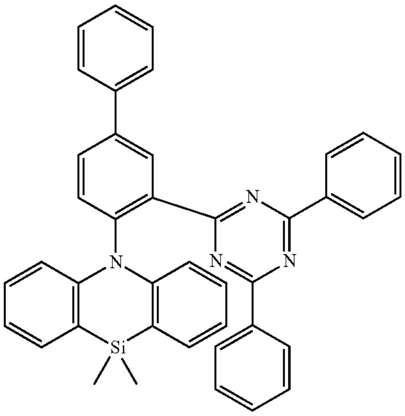

-continued
33
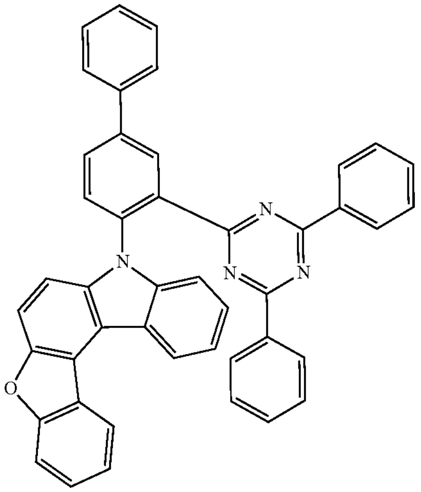
34
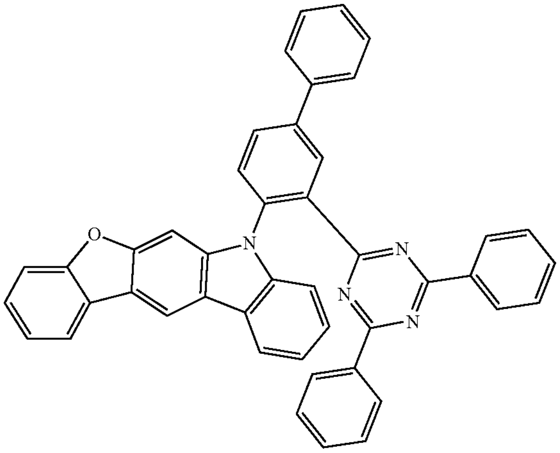
35
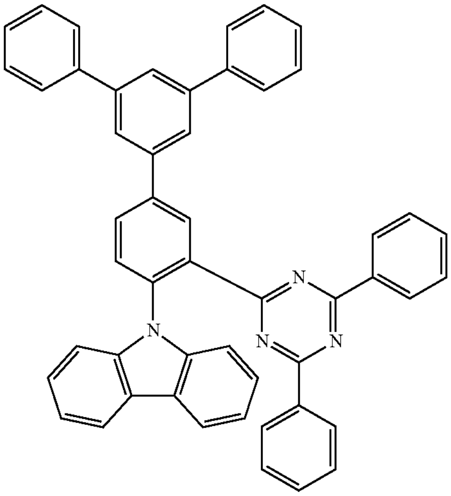
-continued
36
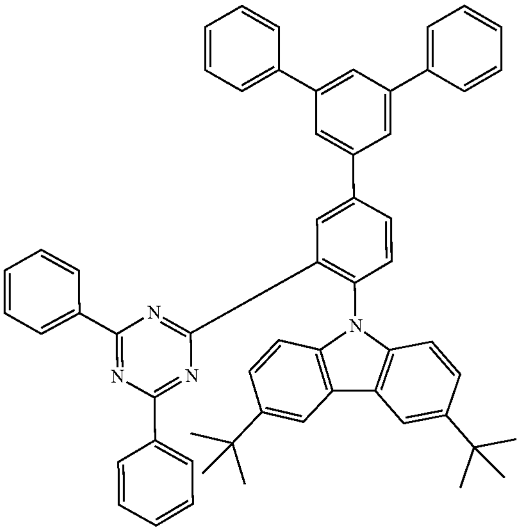
37
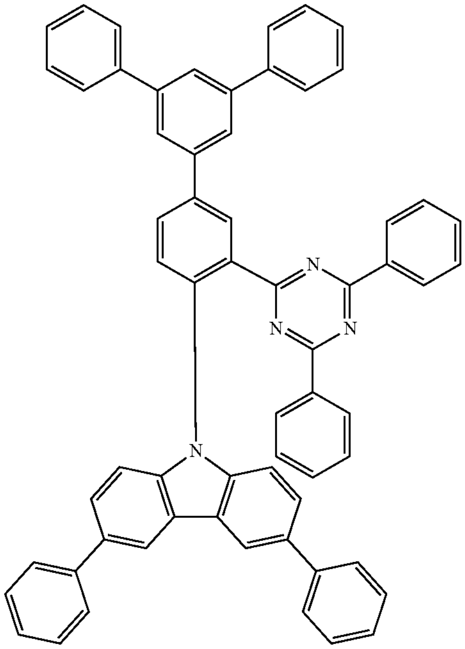

-continued
38
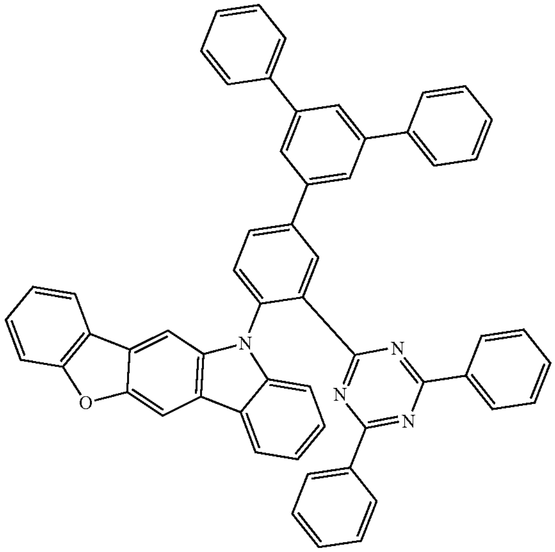
39
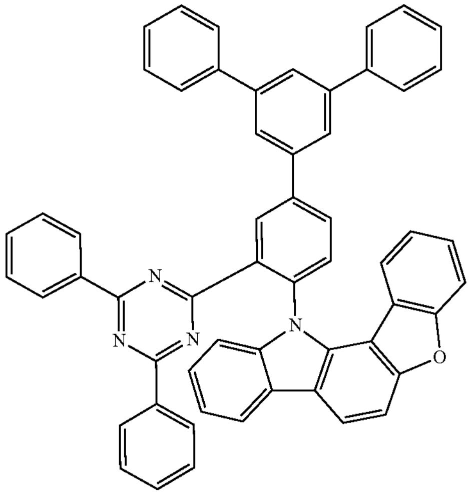
40
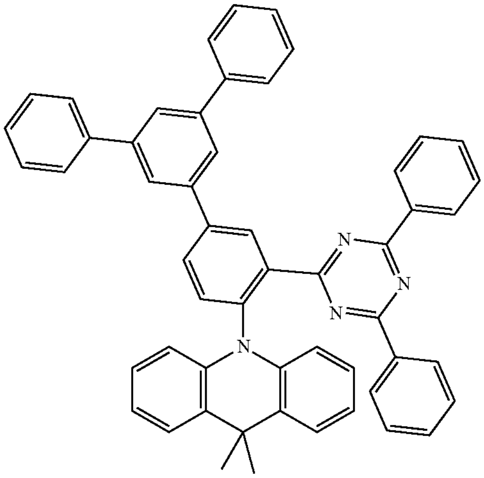
-continued
41
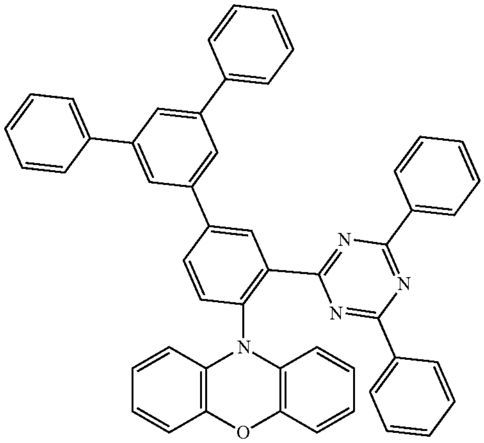
42
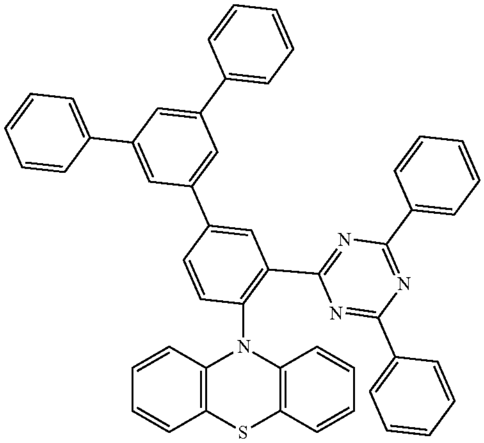
43
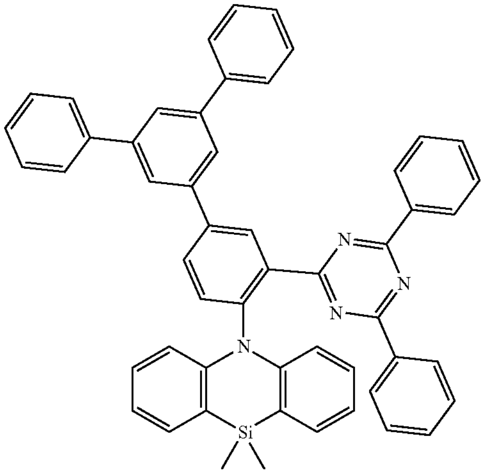

-continued
44
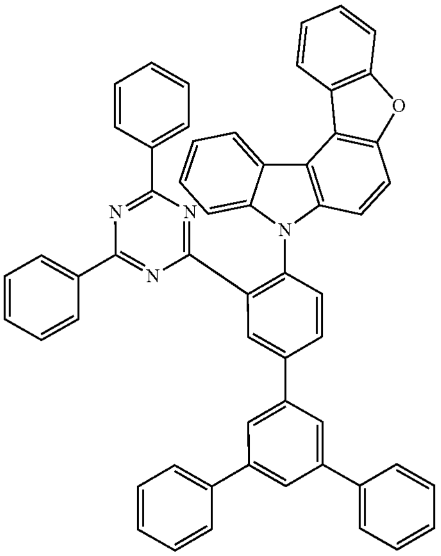
45
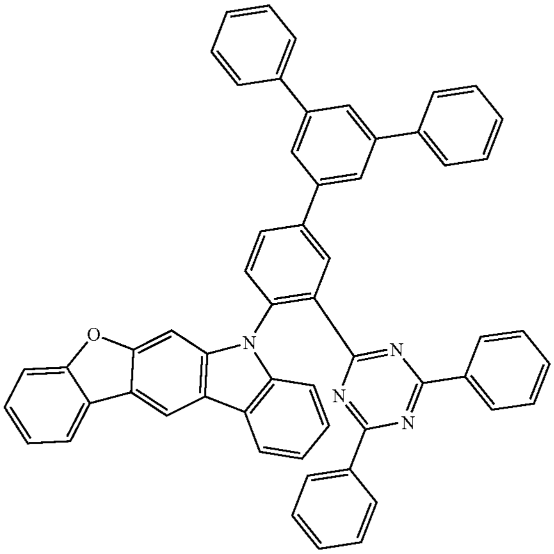
46
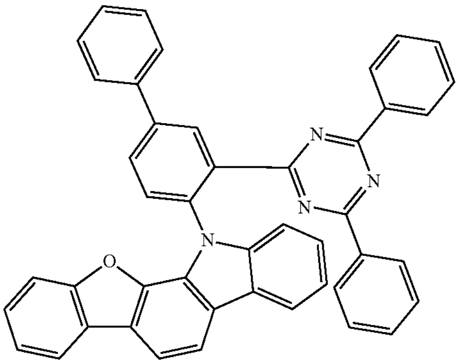
-continued
47
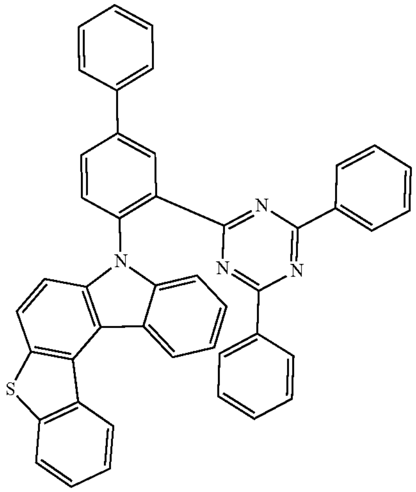
48
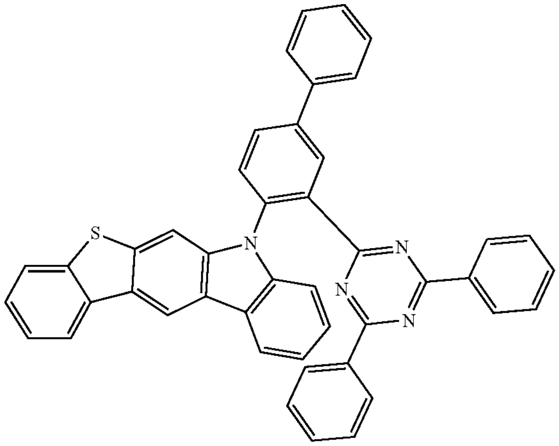
49
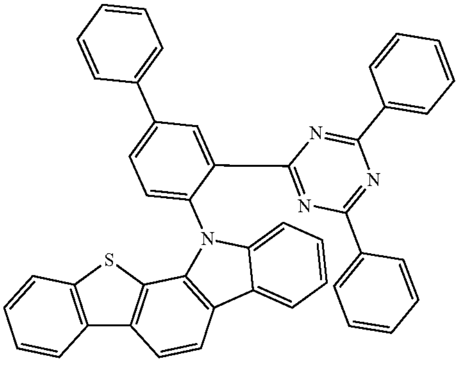

-continued
50
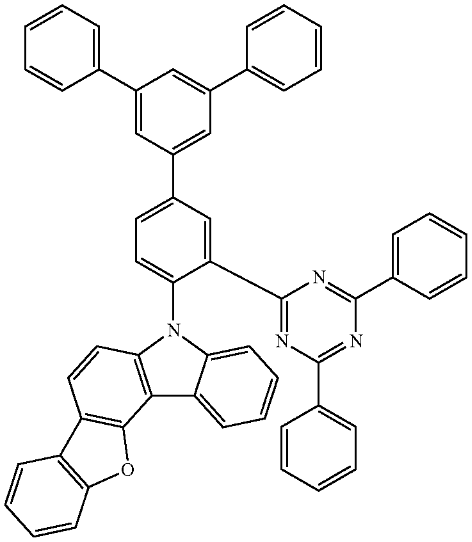
51
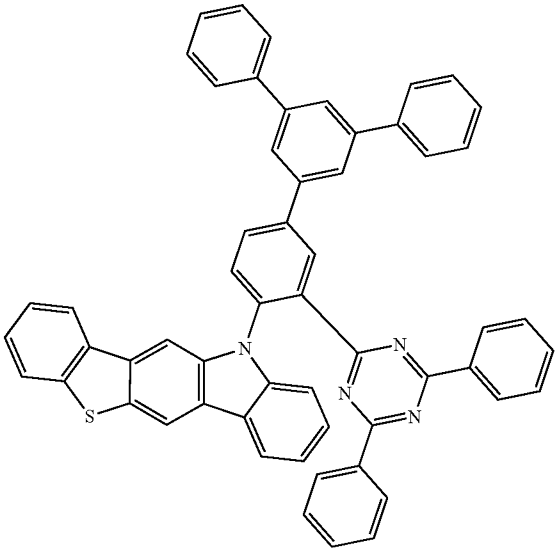
52
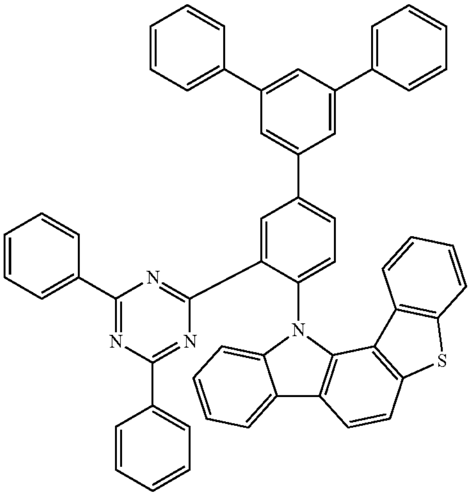
-continued
53
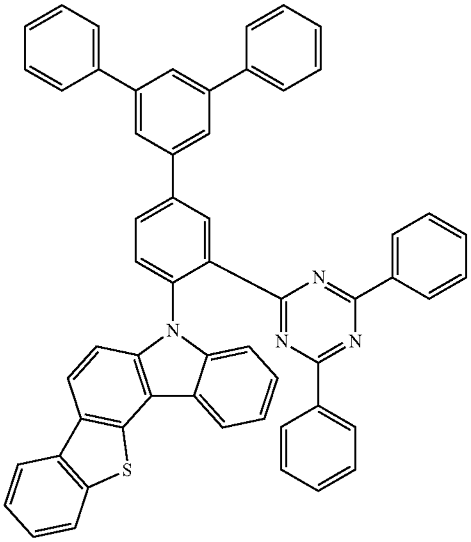
54
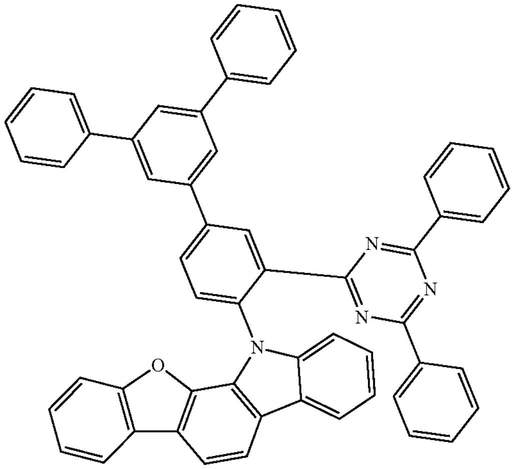
55
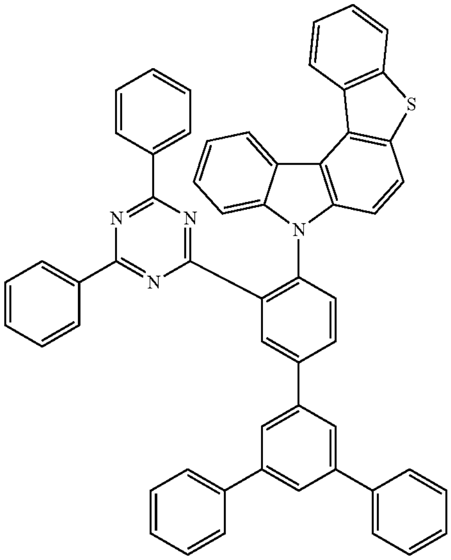

-continued
56
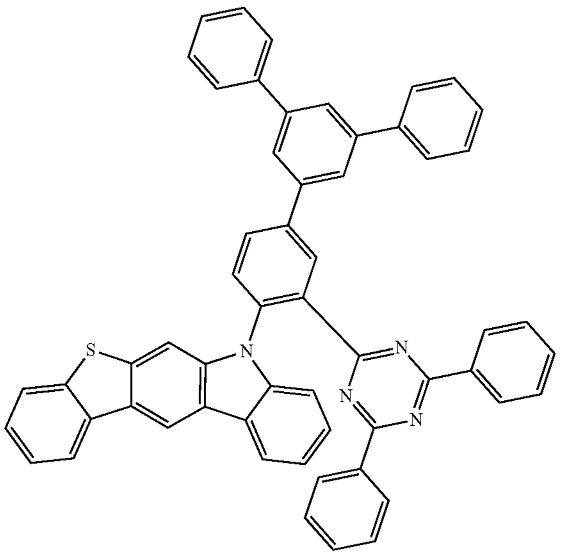
57
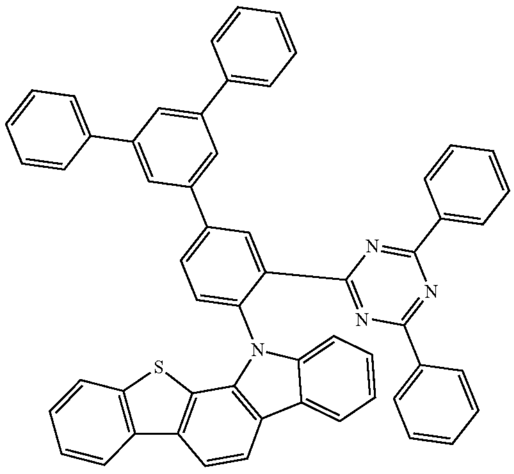
58
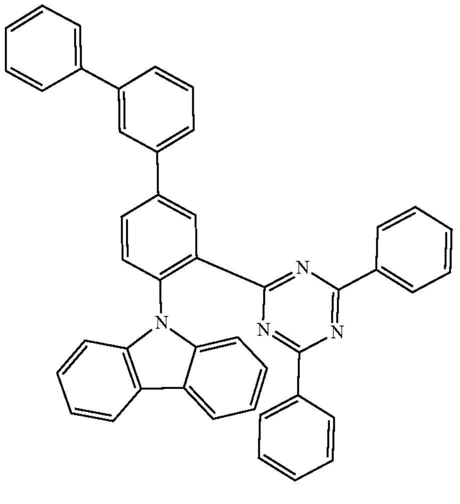
-continued
59
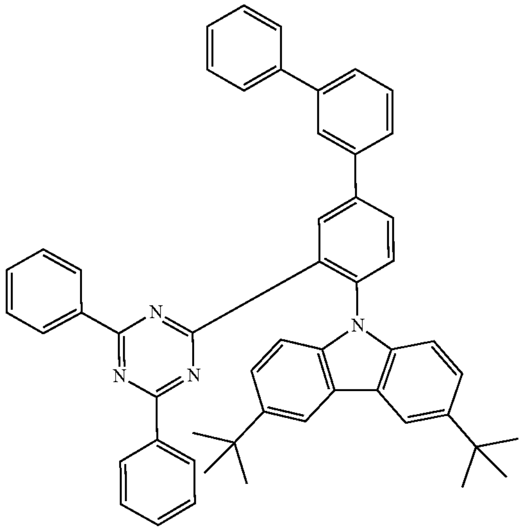
60
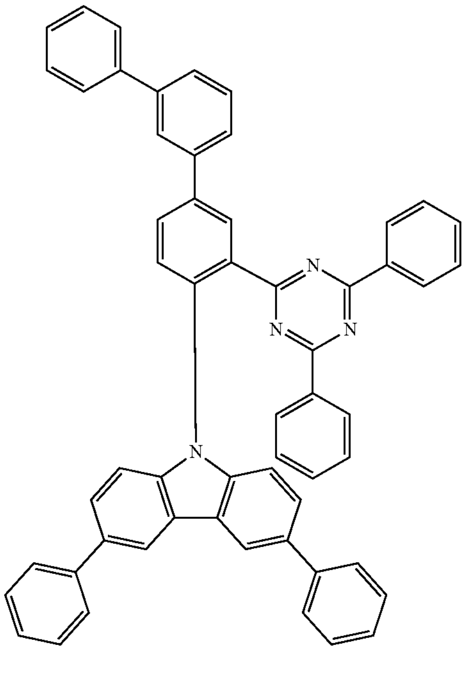

61
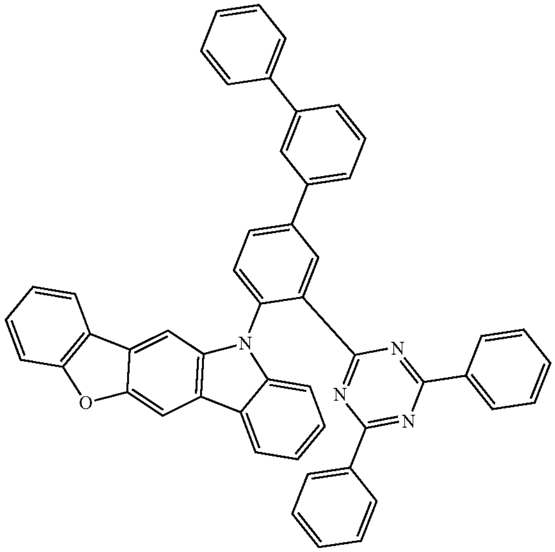
62
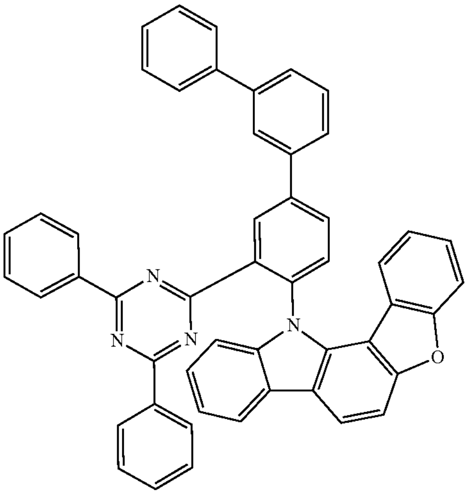
63
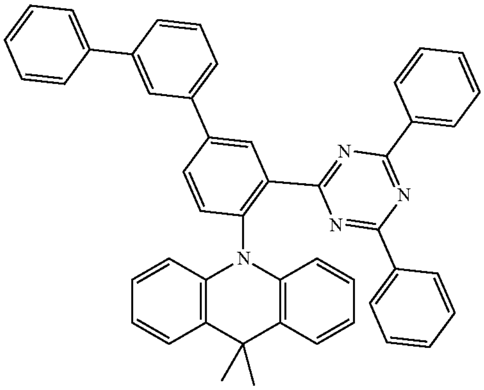
64
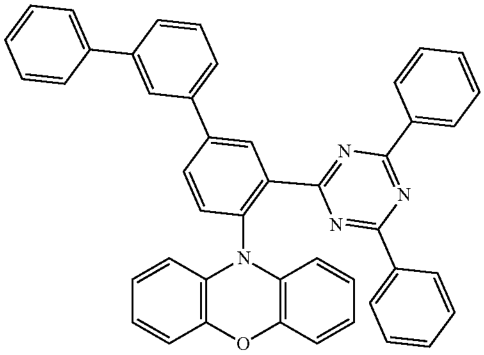
65
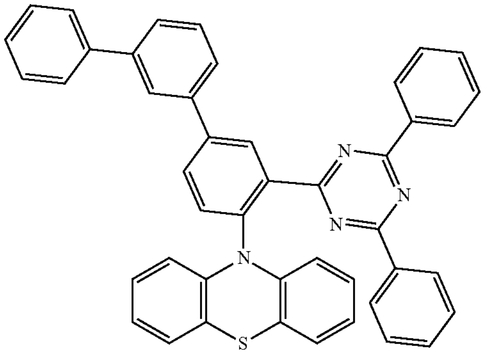
66
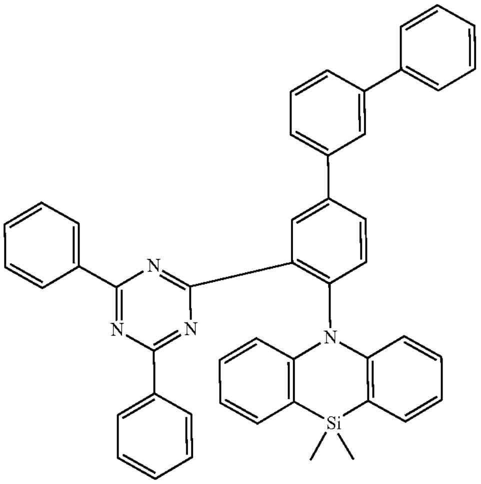

-continued
67
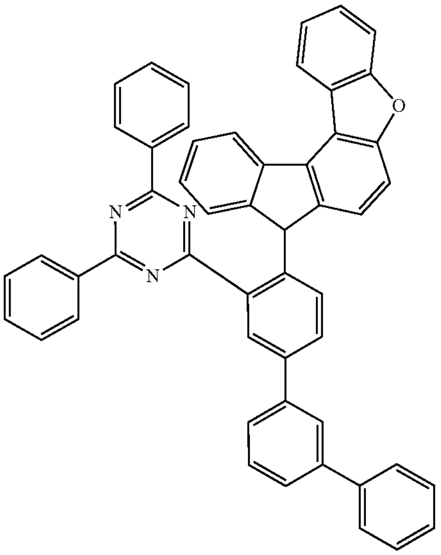
68
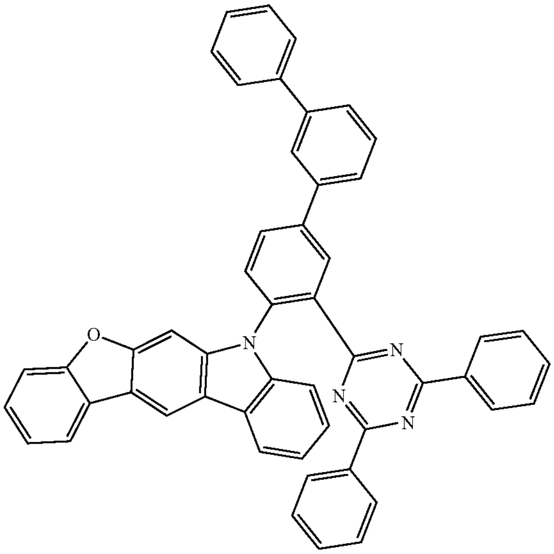
69
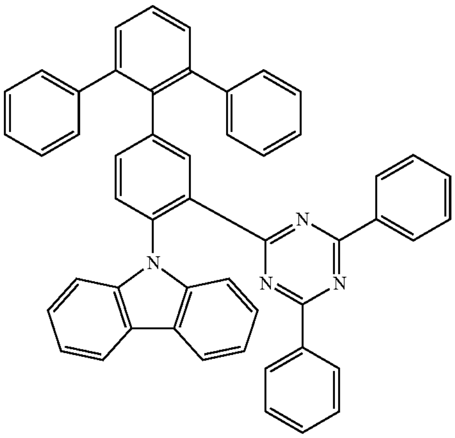
-continued
70
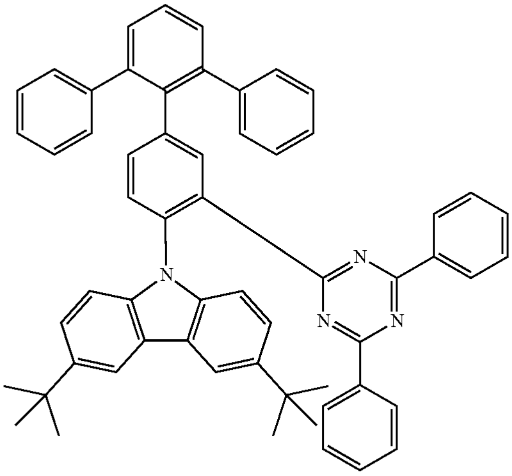
71
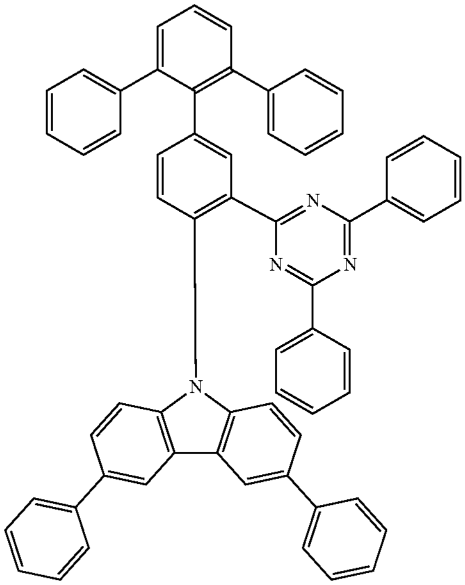
72
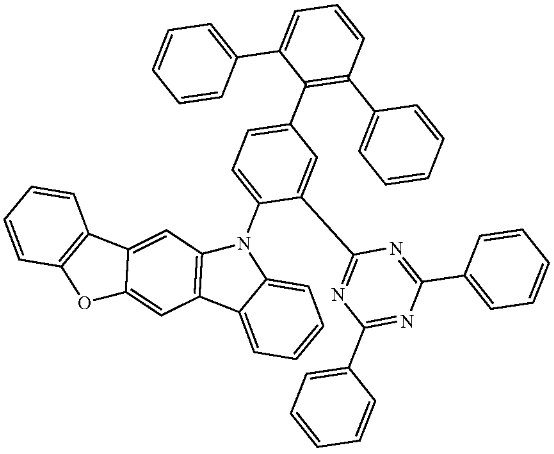

-continued
73
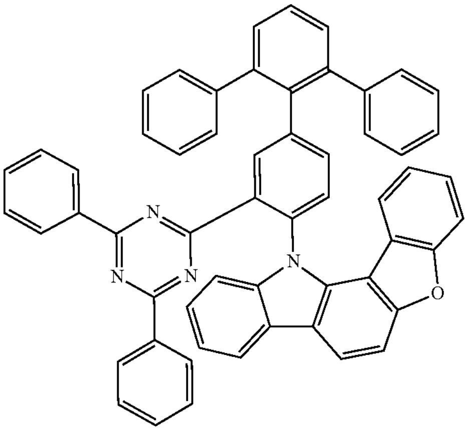
74
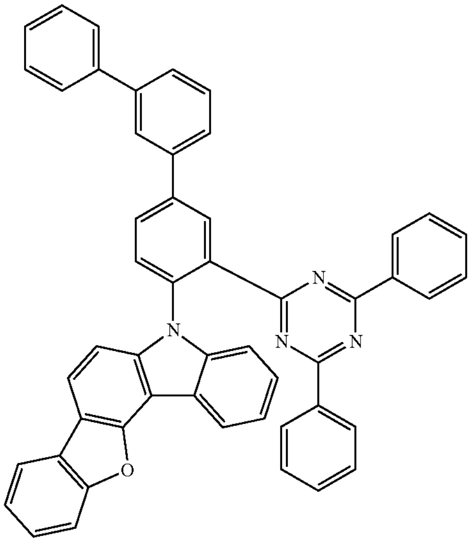
75
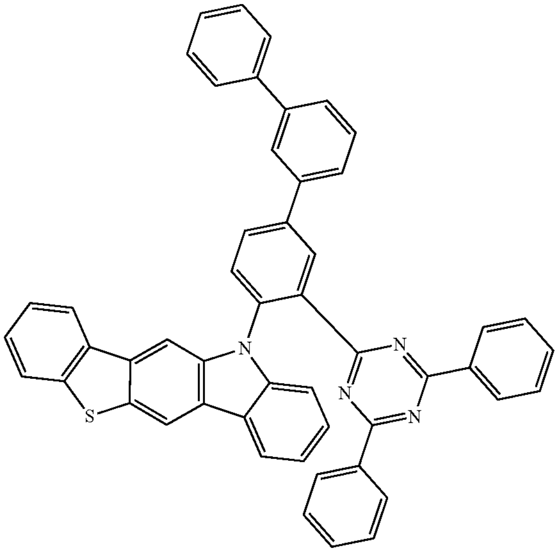
-continued
76
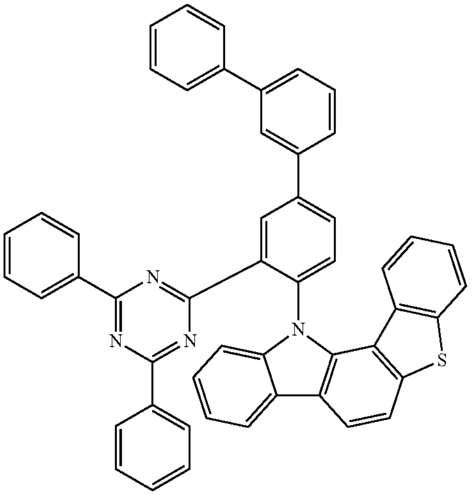
77
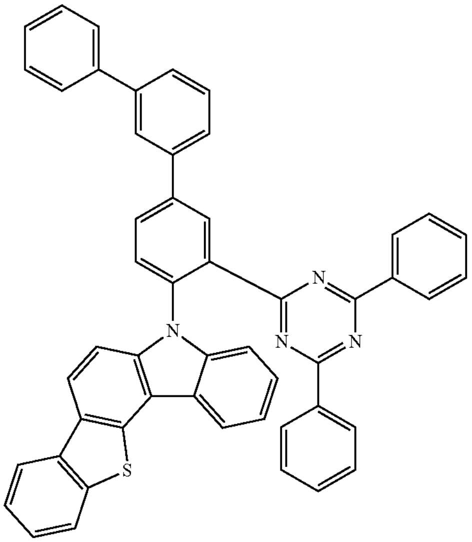
78
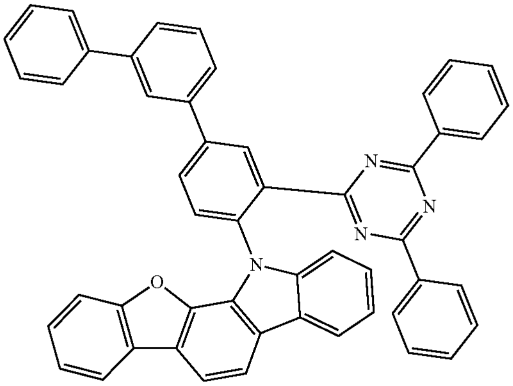

-continued
79
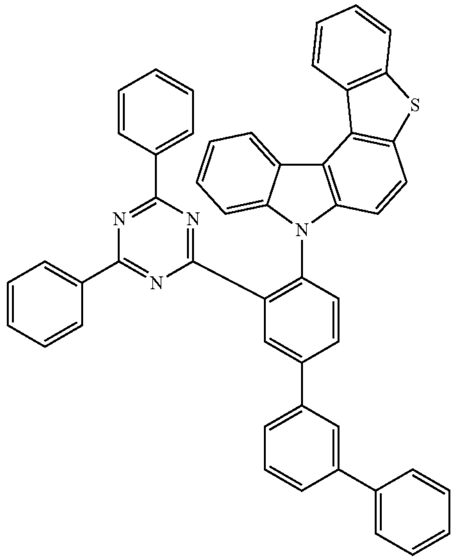
80
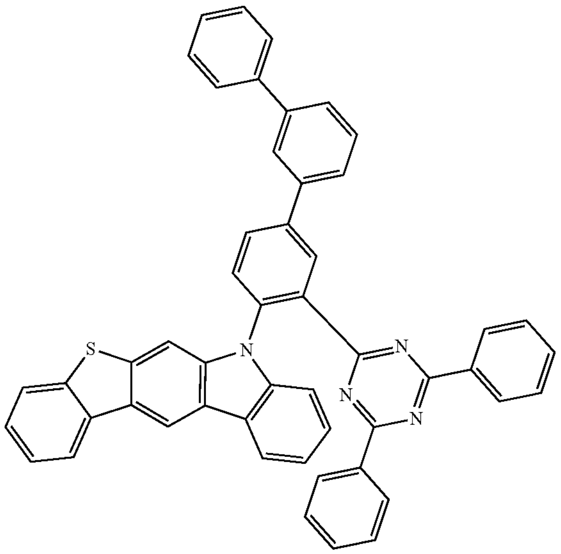
81
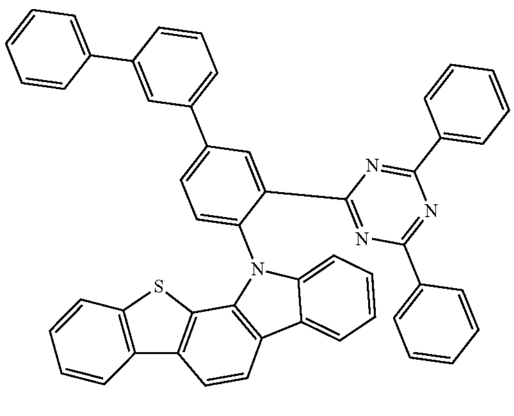
-continued
82
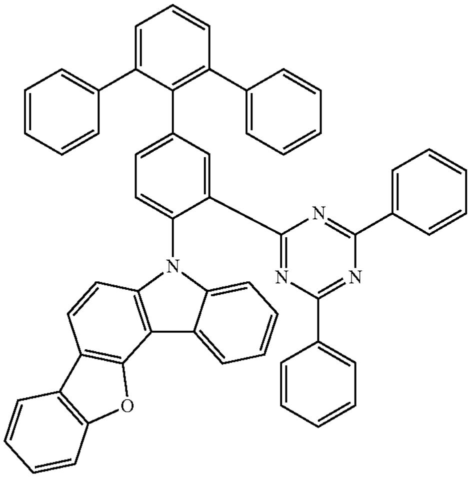
83
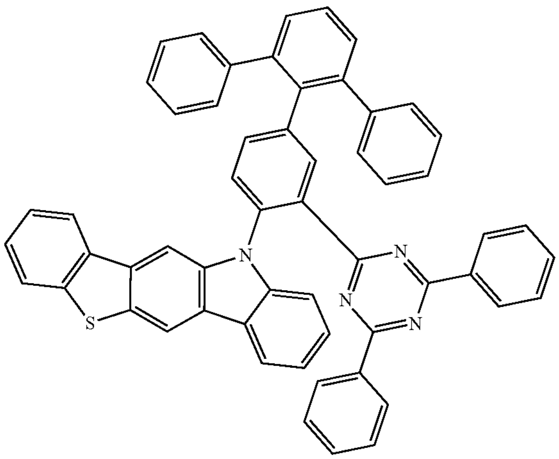
84
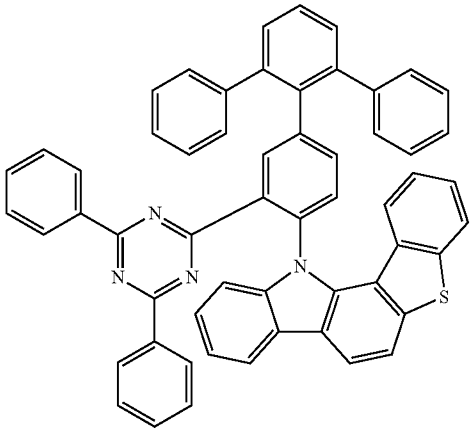

-continued
85
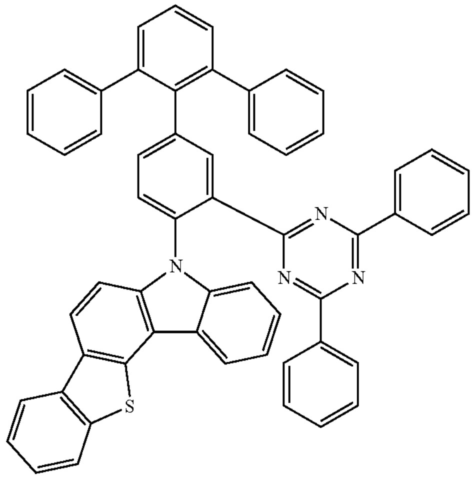
86
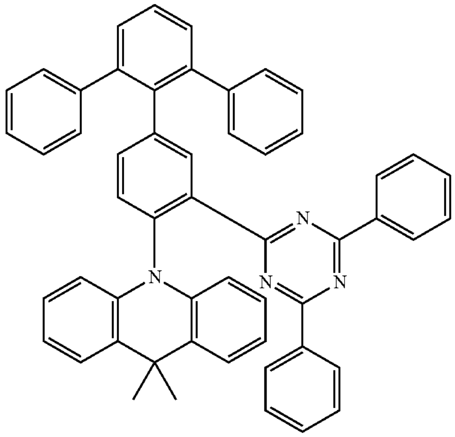
87
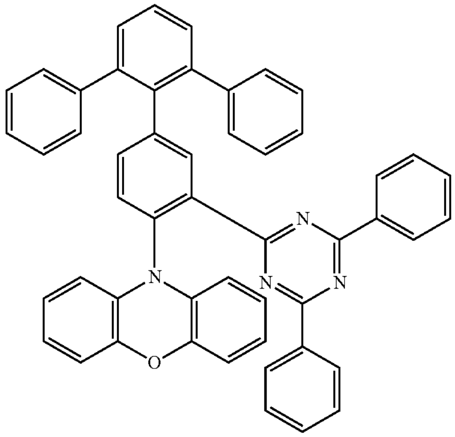
-continued
88
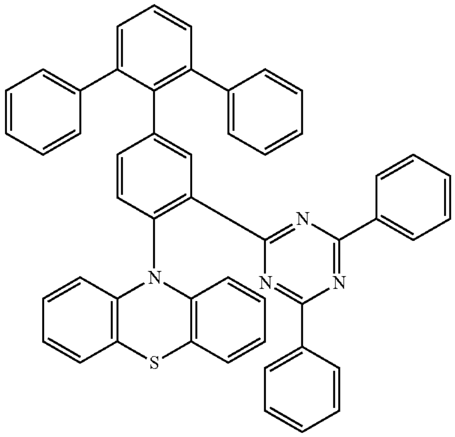
89
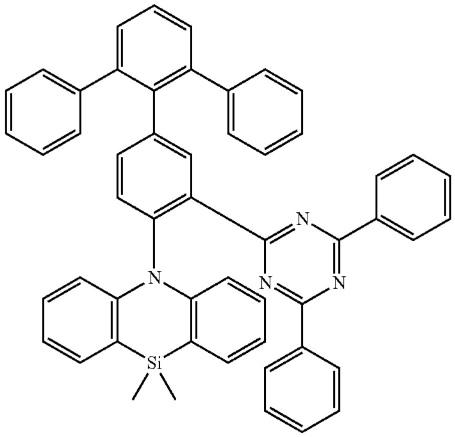
90
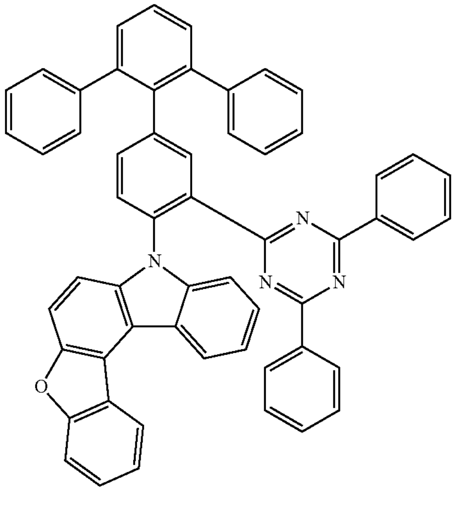

-continued
91
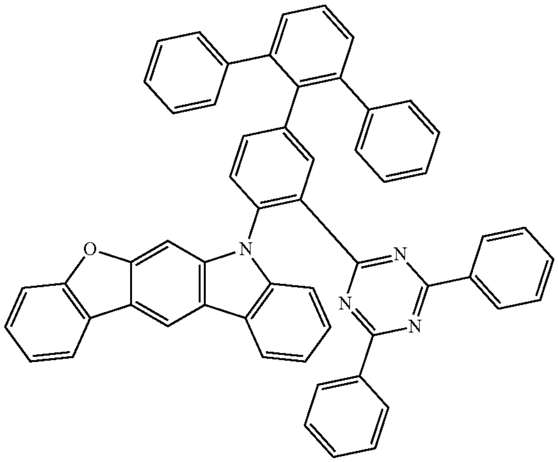
92
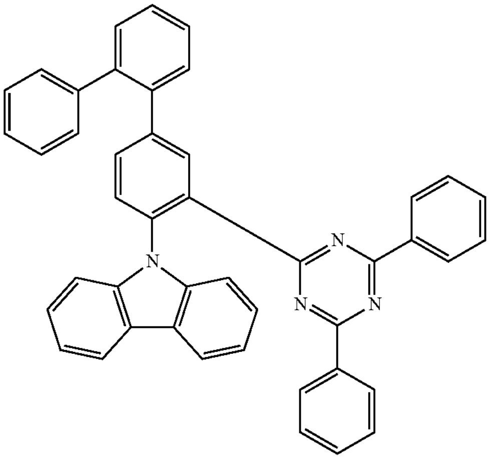
93
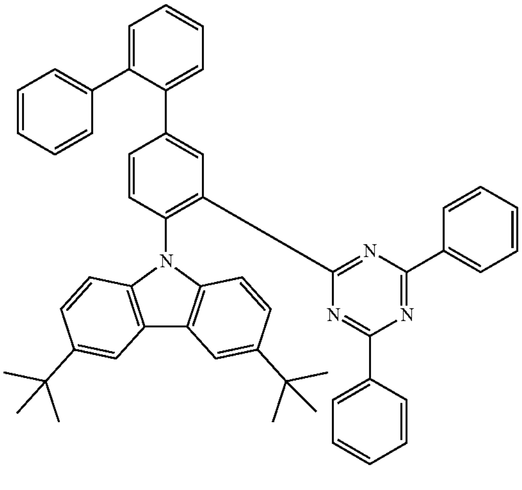
-continued
94
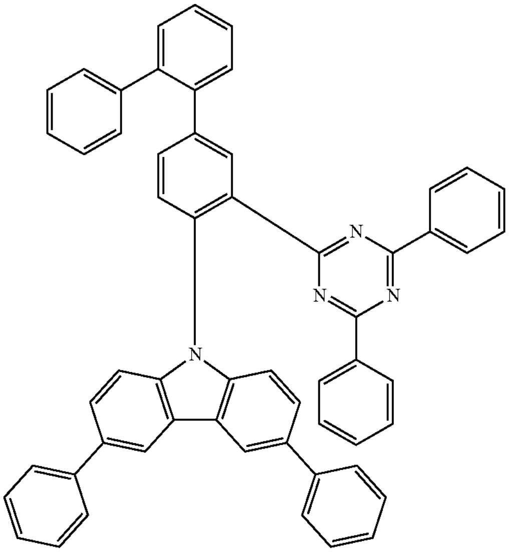
95
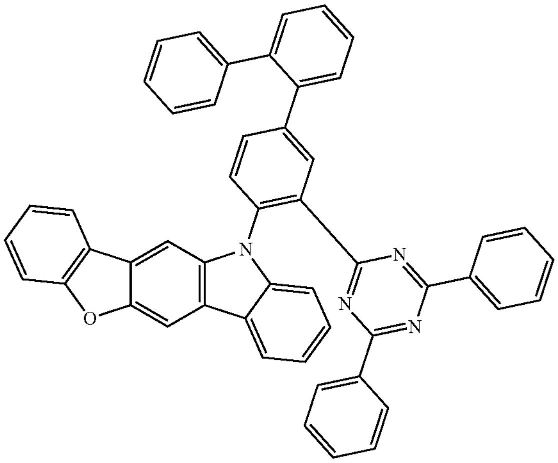
96
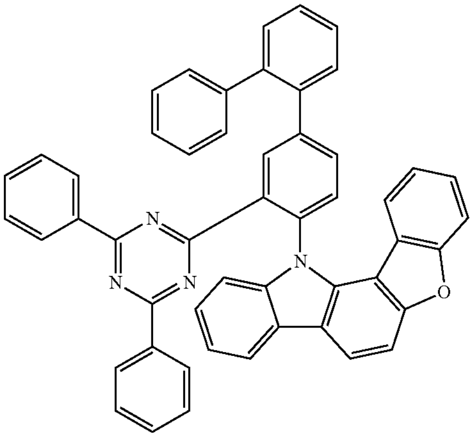

-continued
97
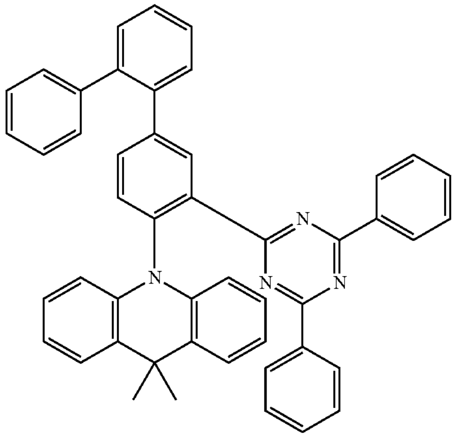
98
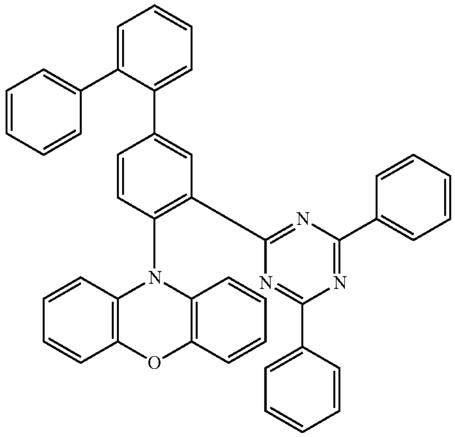
99
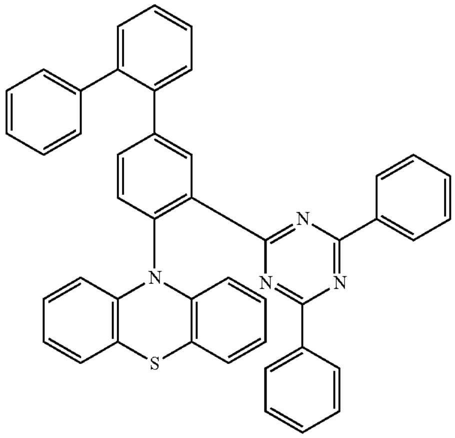
-continued
100
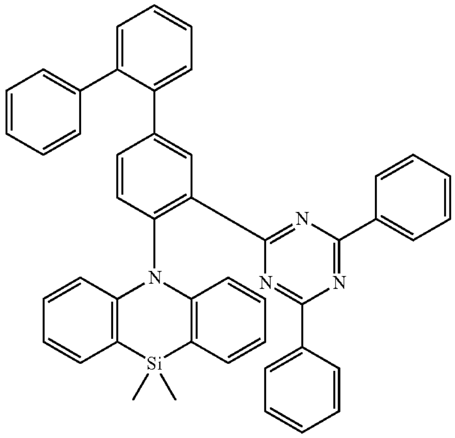
101
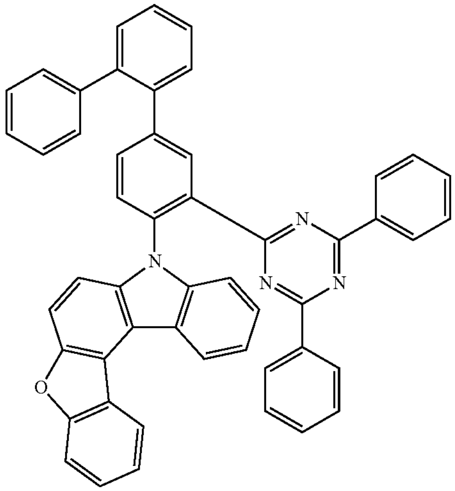
102
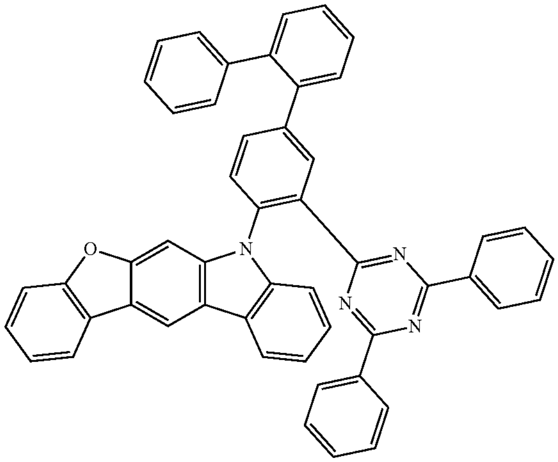

-continued
103
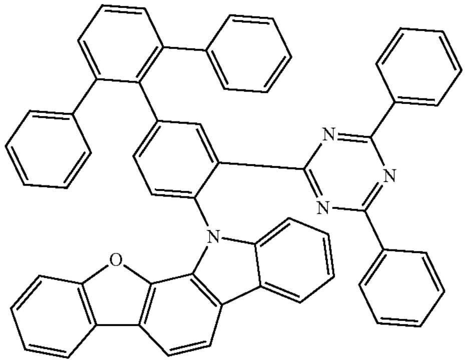
104
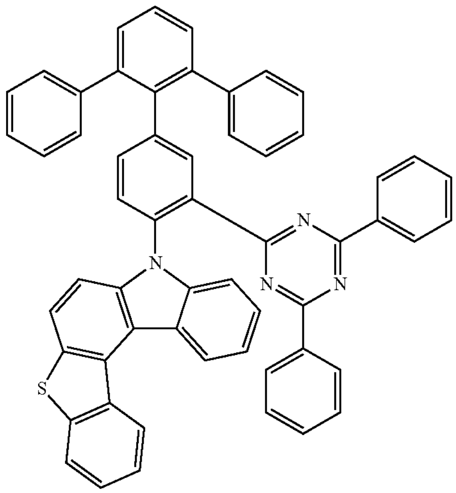
105
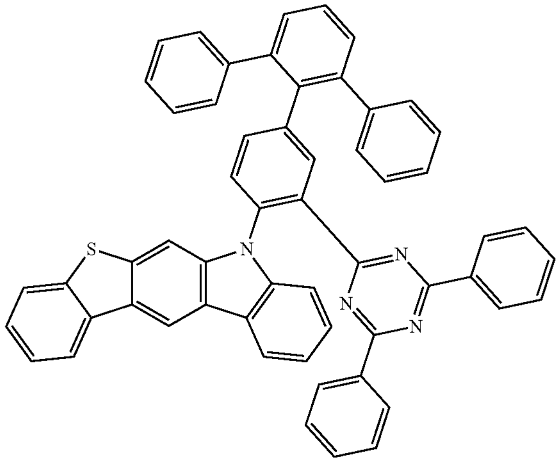
-continued
106
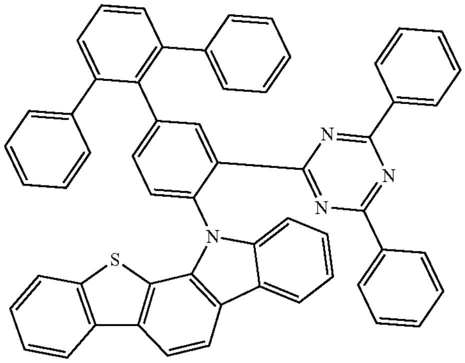
107
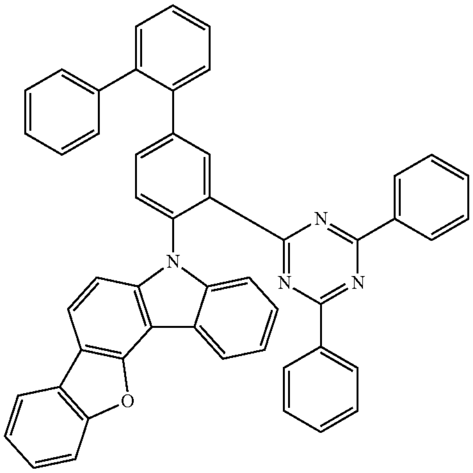
108
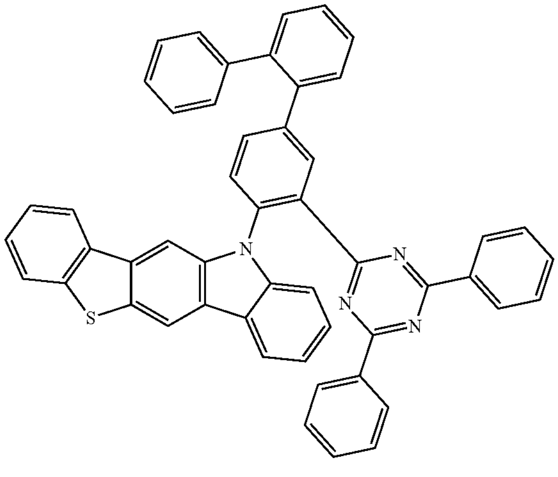

-continued
109
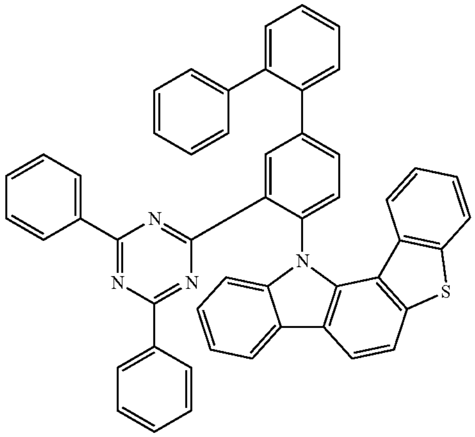
110
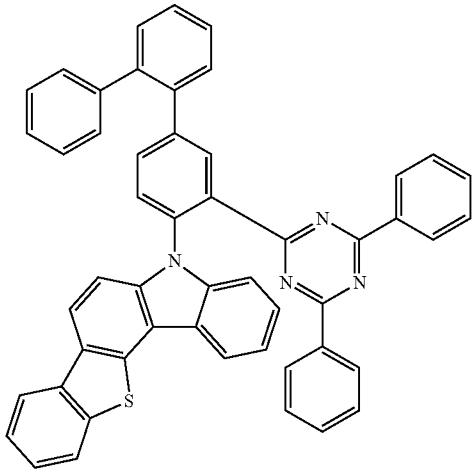
111
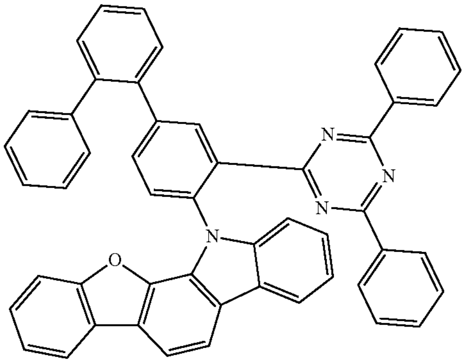
-continued
112
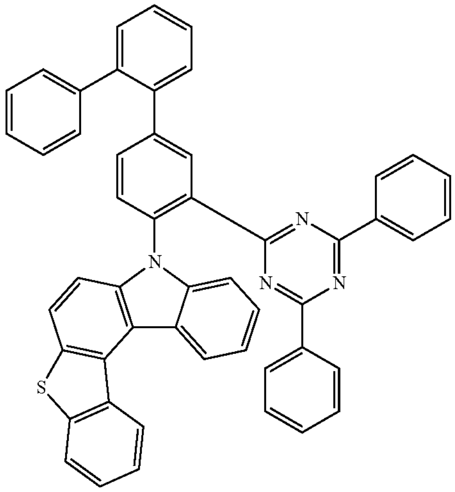
113
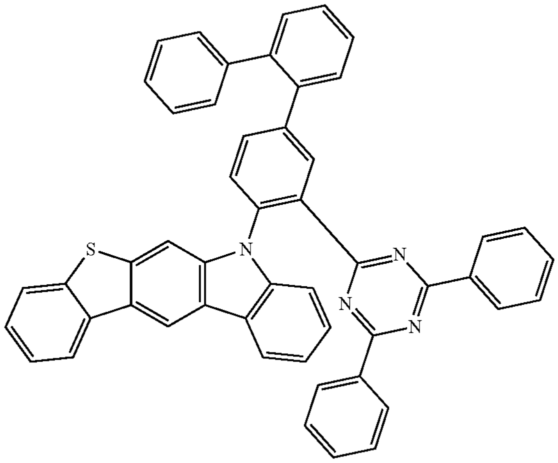
114
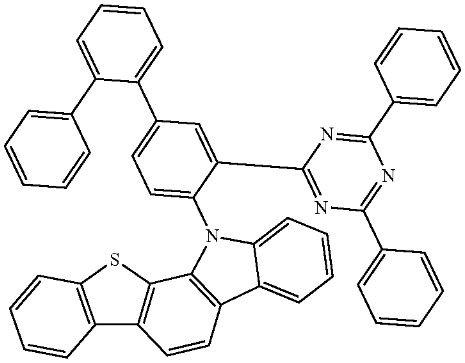

-continued
115
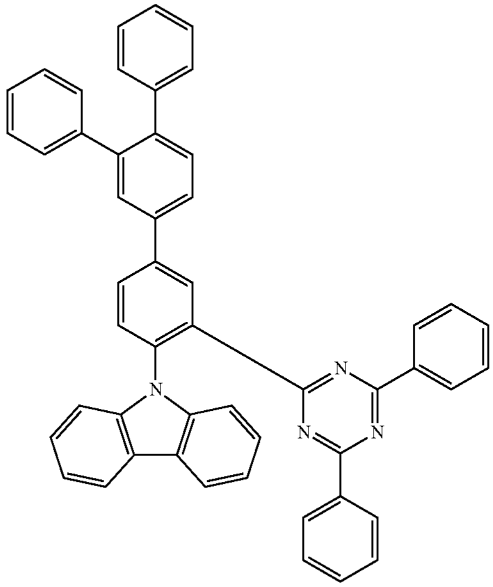
116
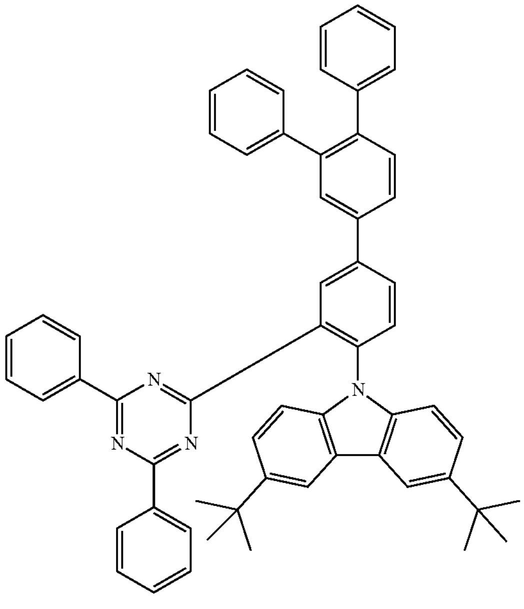
-continued
117
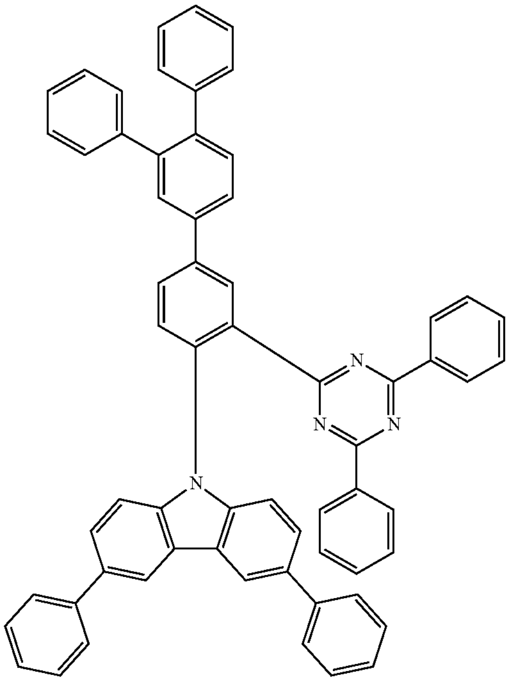
118
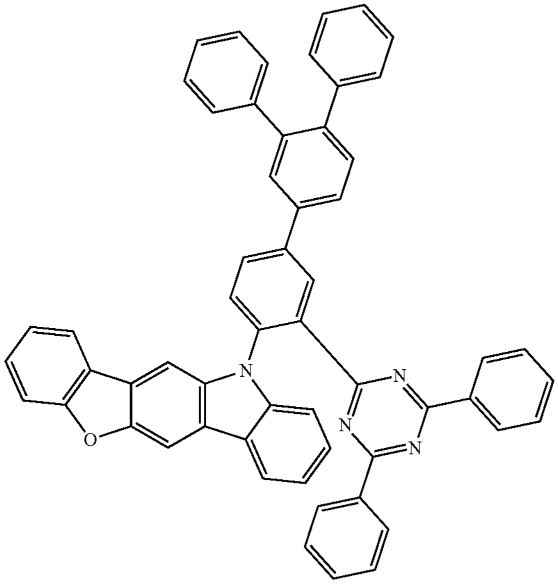

-continued
119
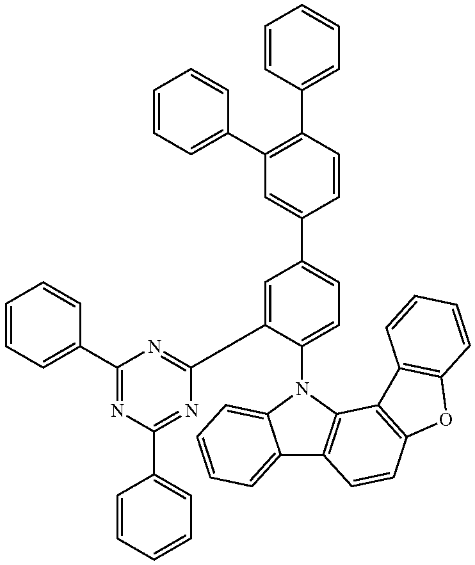
120
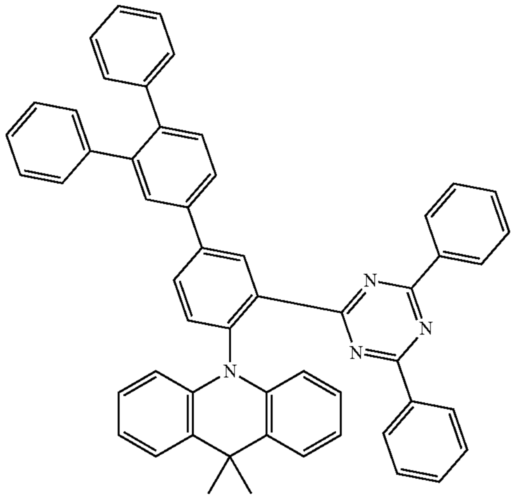
121
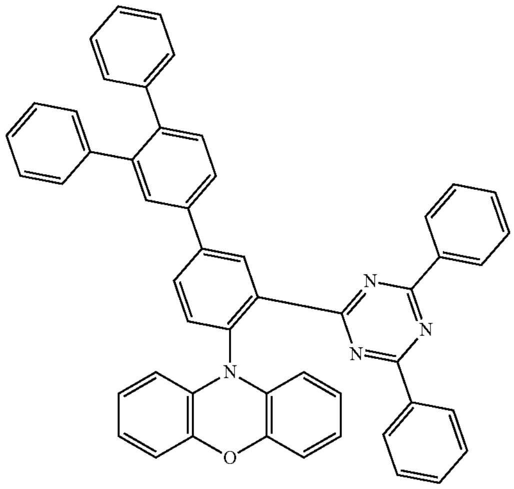
-continued
122
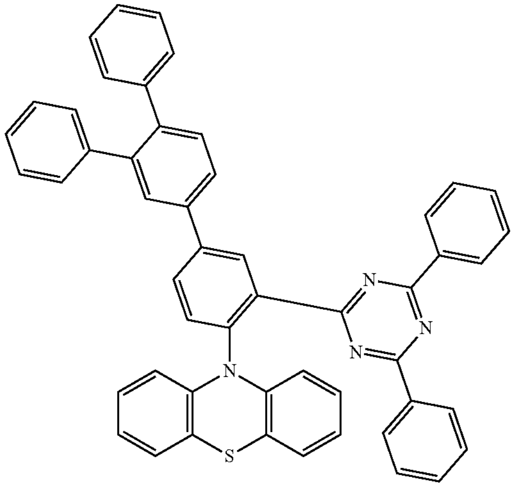
123
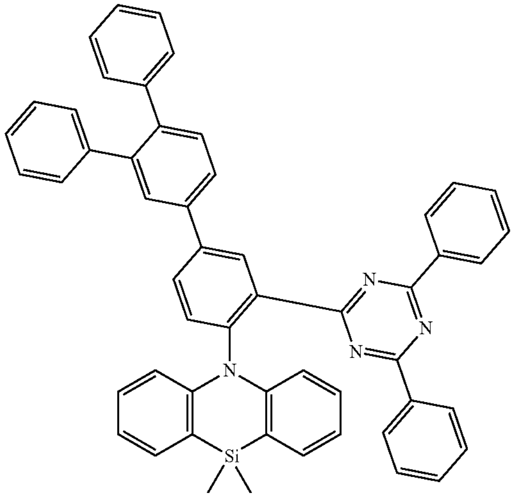
124
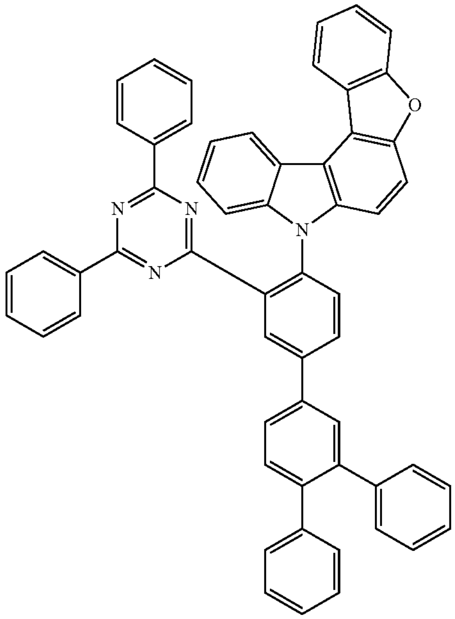

-continued
125
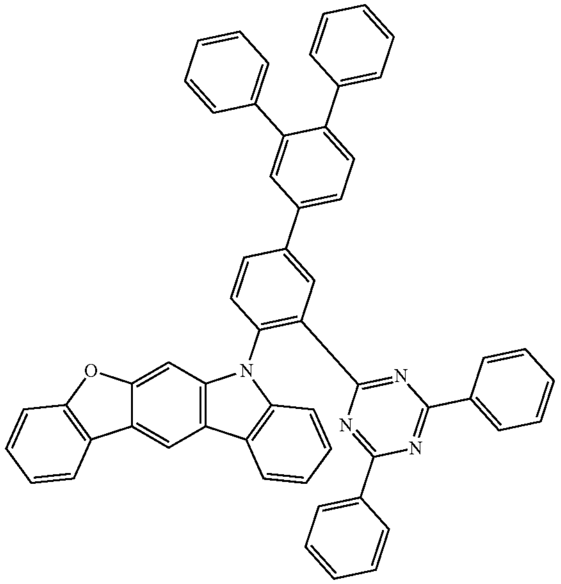
126
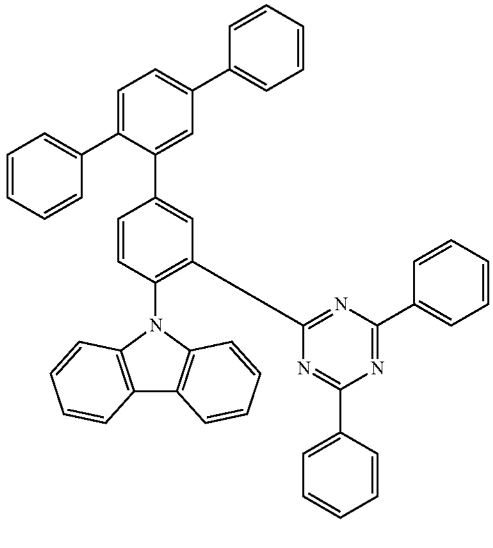
-continued
127
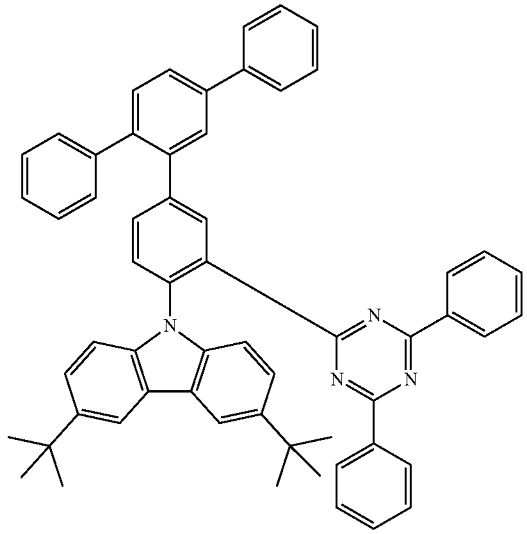
128
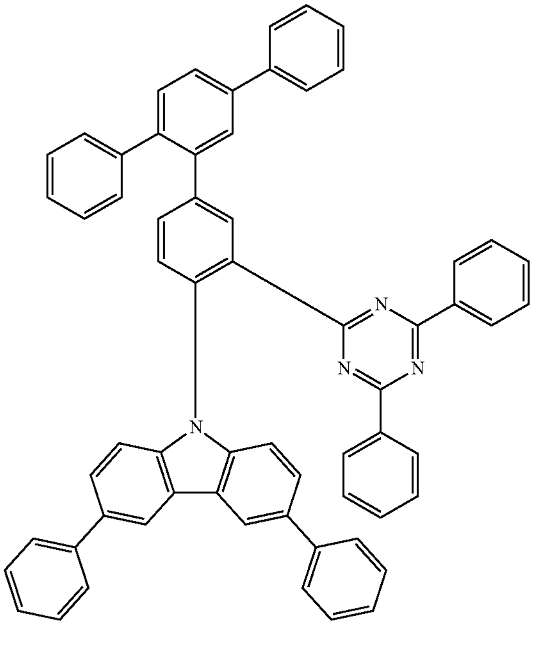

-continued
129
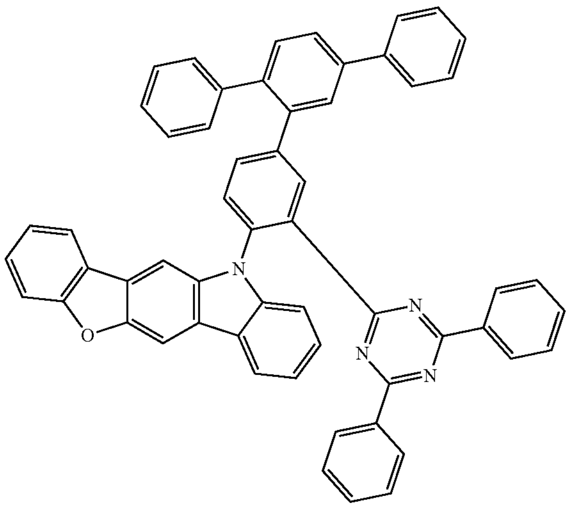
130
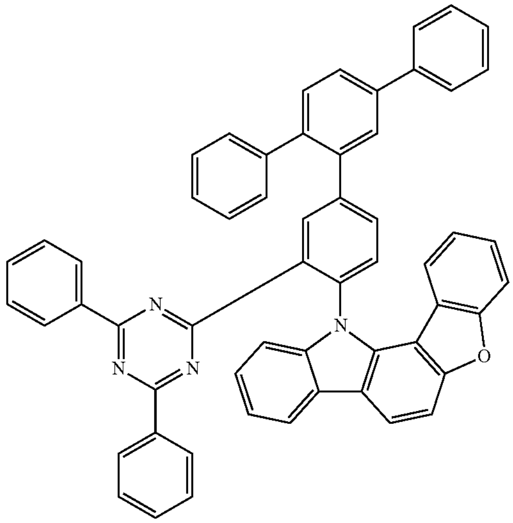
131
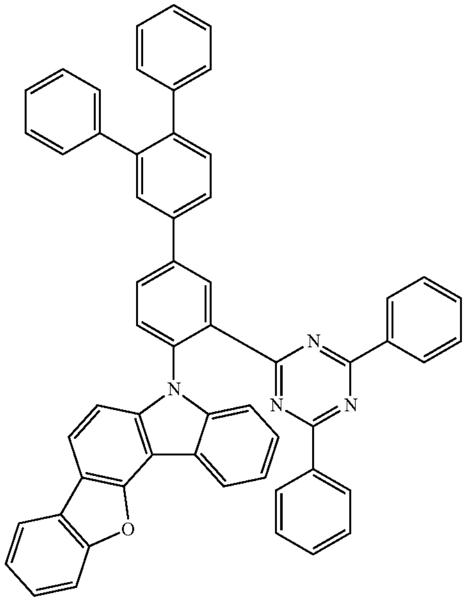
-continued
132
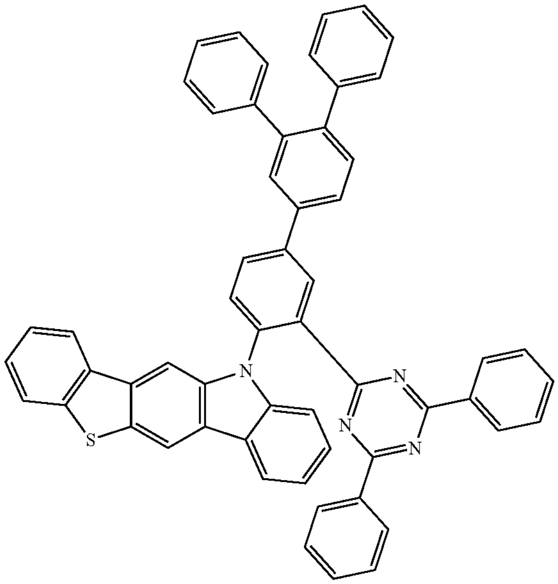
133
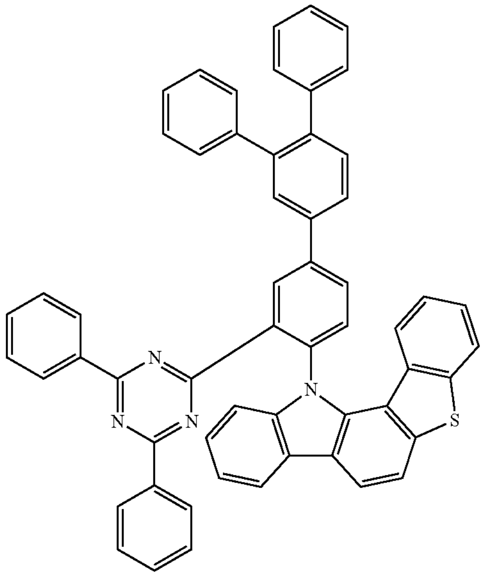

-continued
134
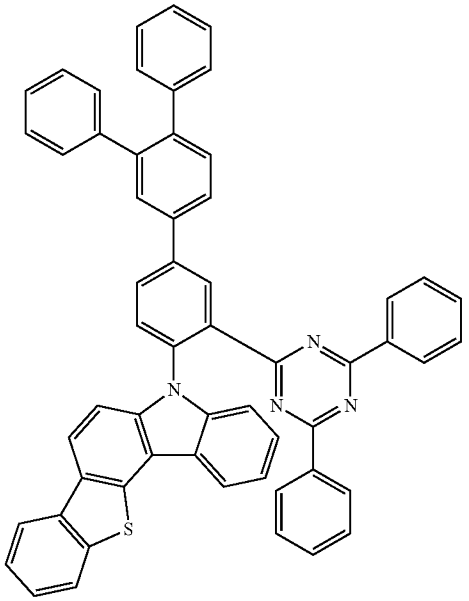
135
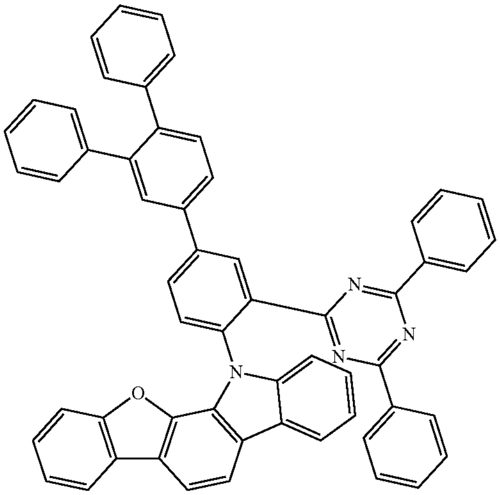
-continued
136
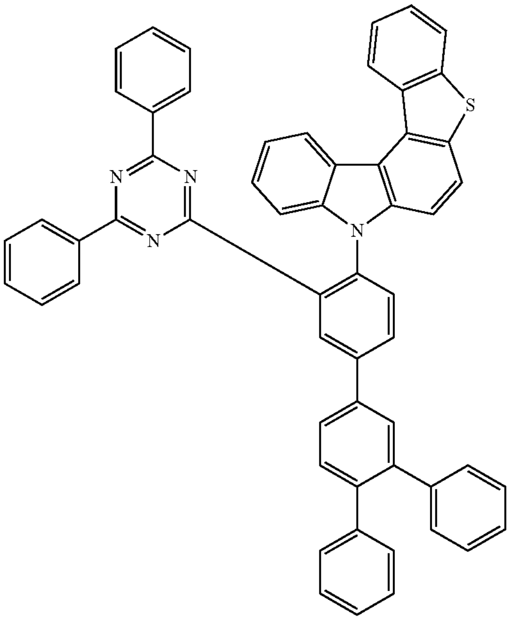
137
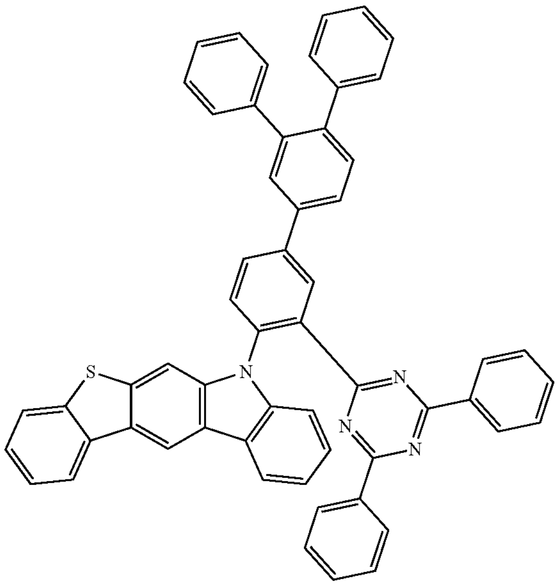

-continued
138
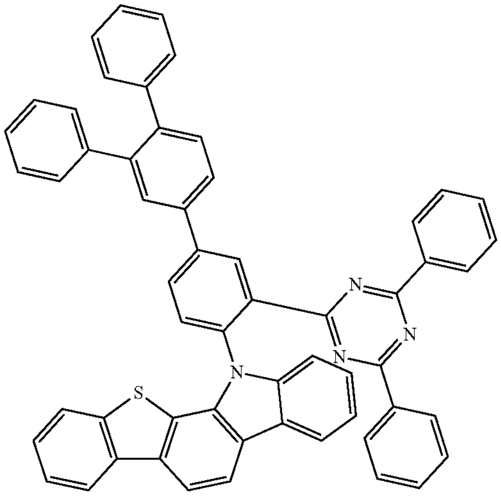
139
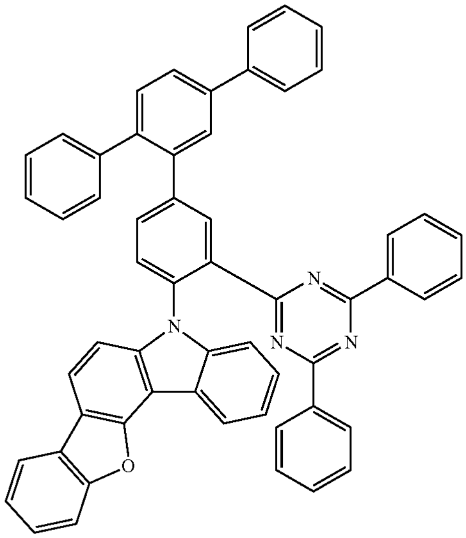
140
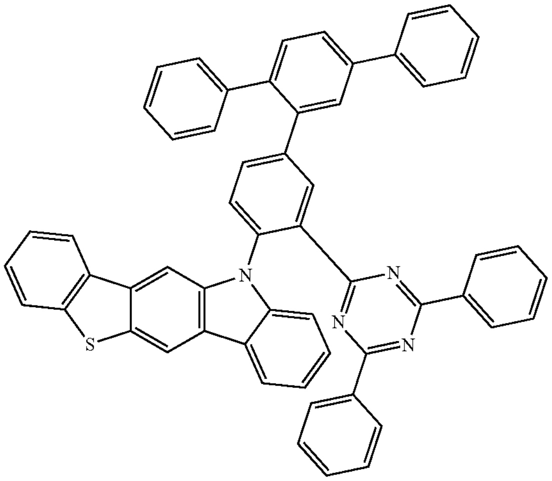
-continued
141
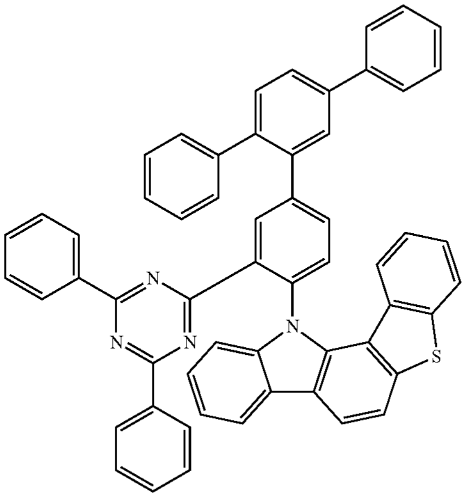
142
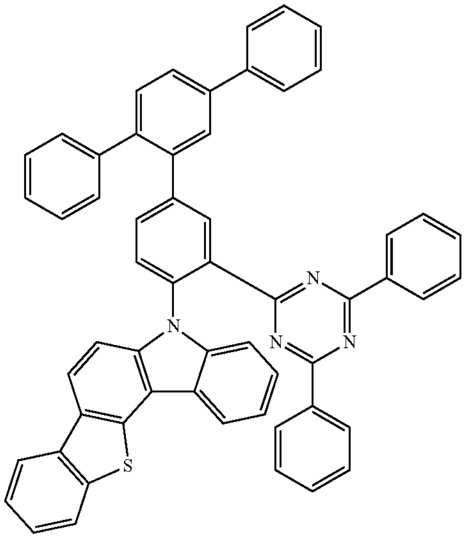
143
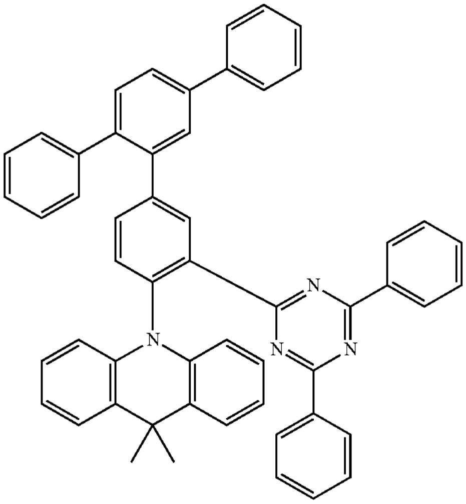

144
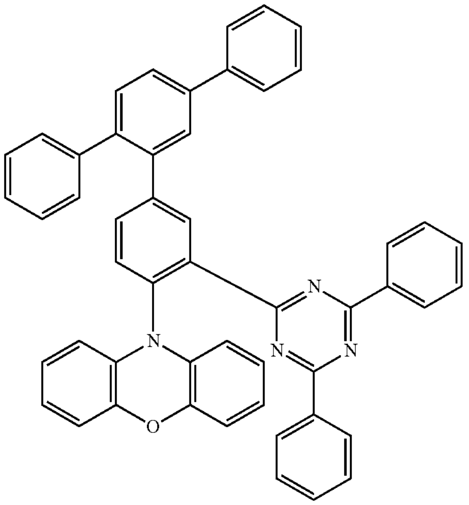
145
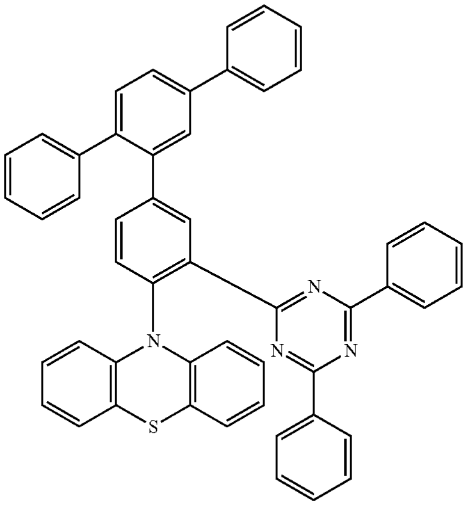
146
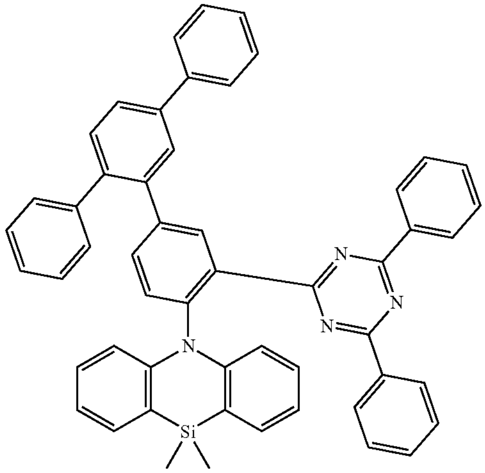
147
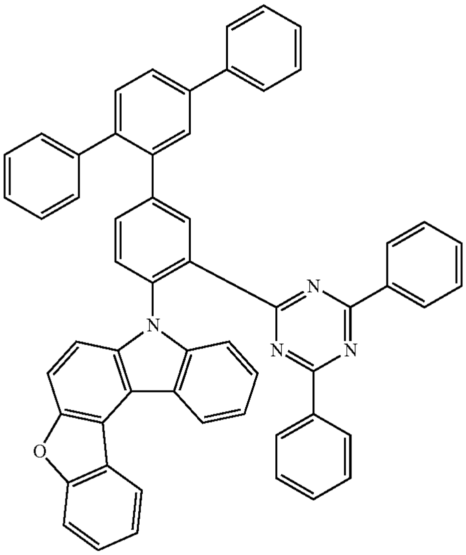
148
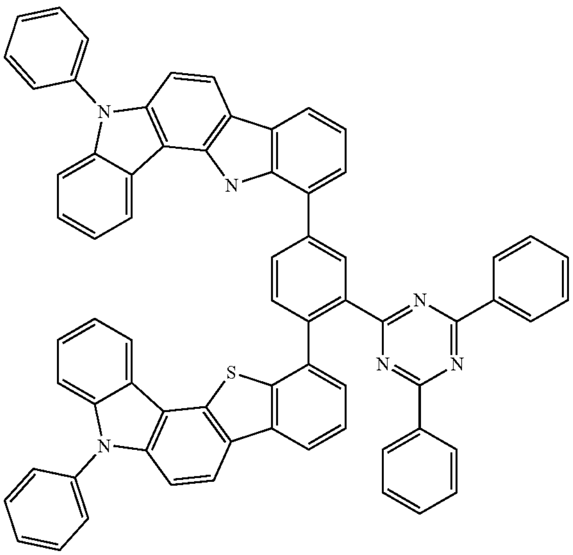

149
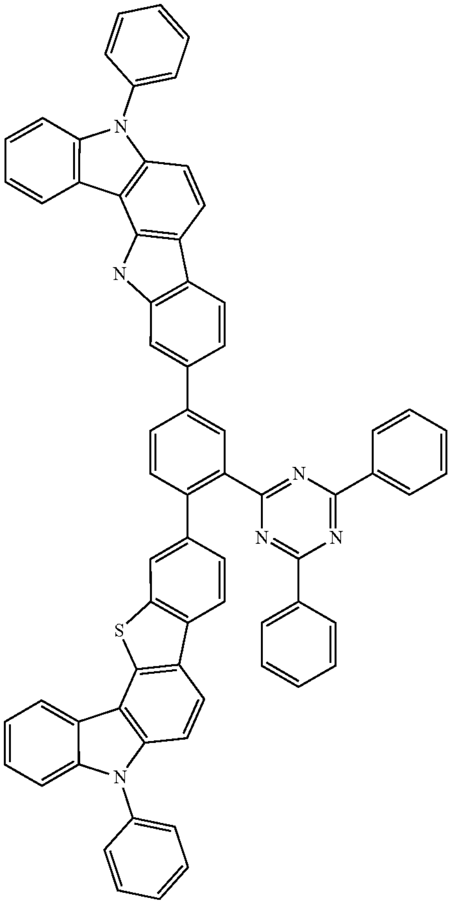
150
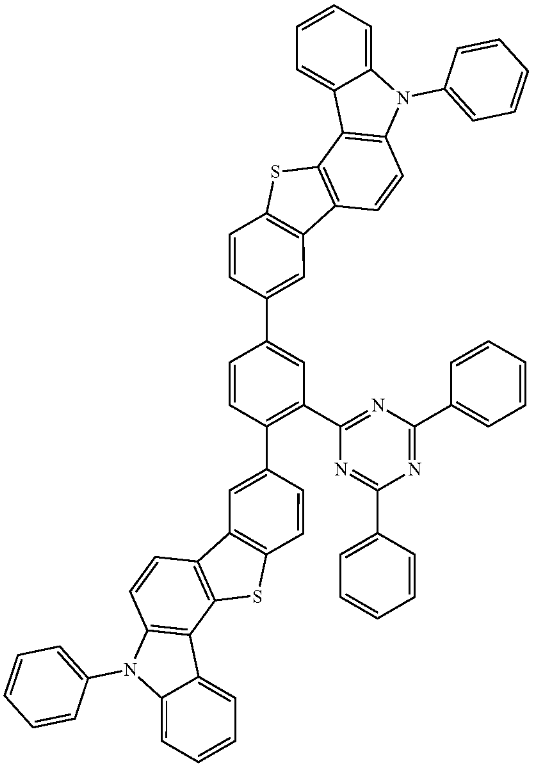
151
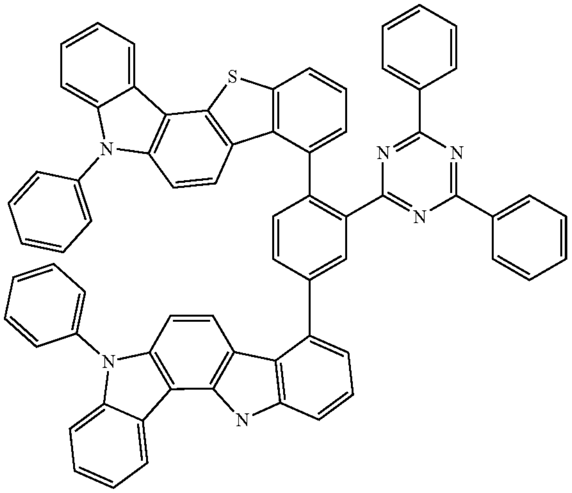
152
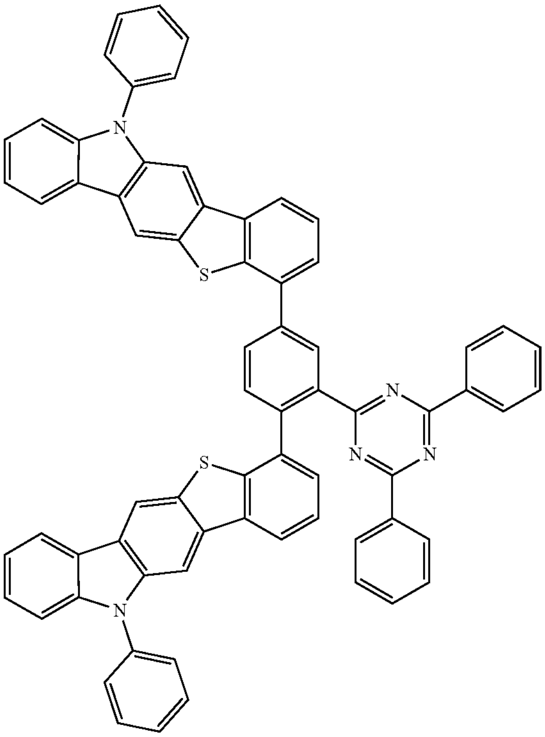

-continued
153
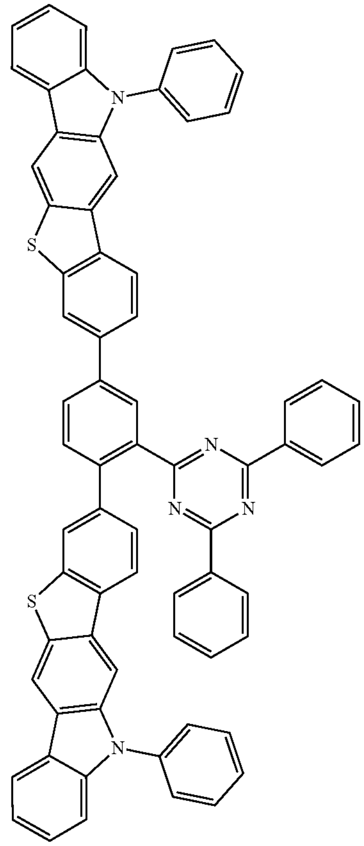
154
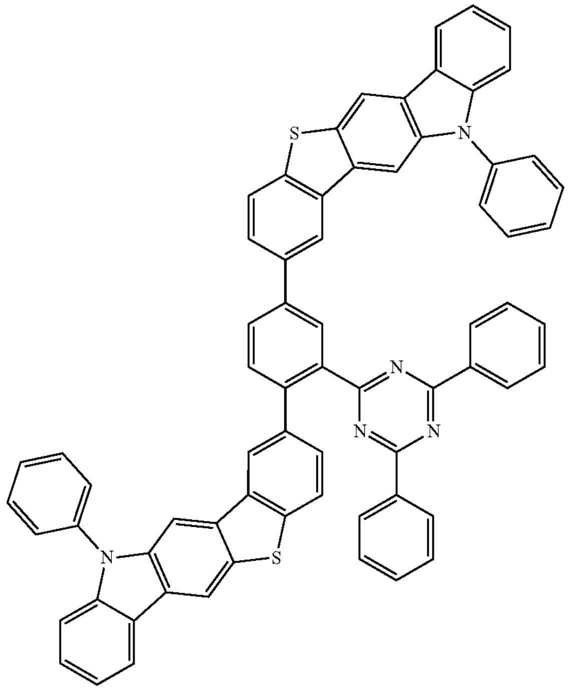
-continued
155
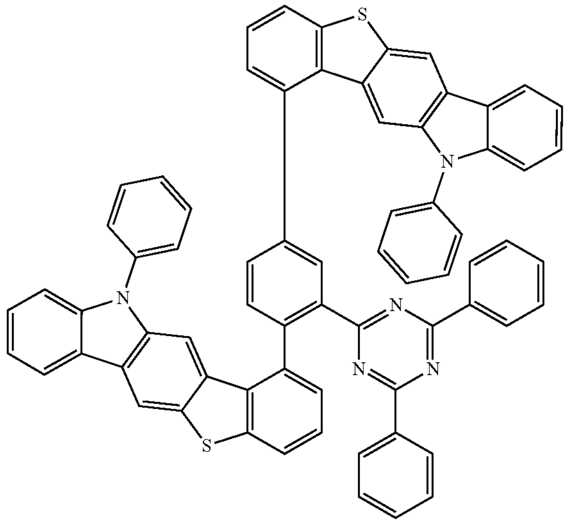
156
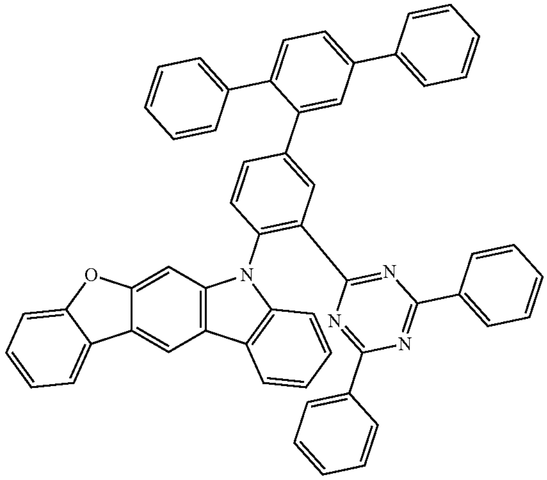
157
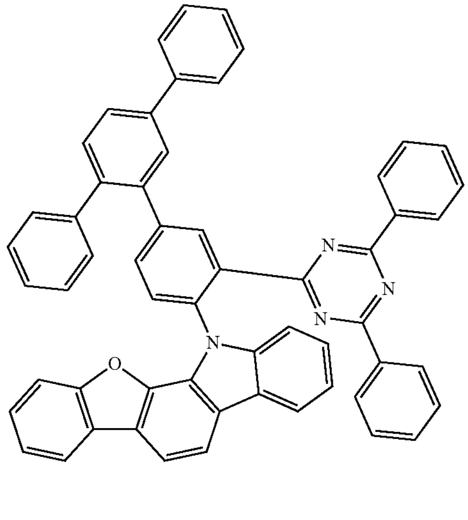

-continued
158
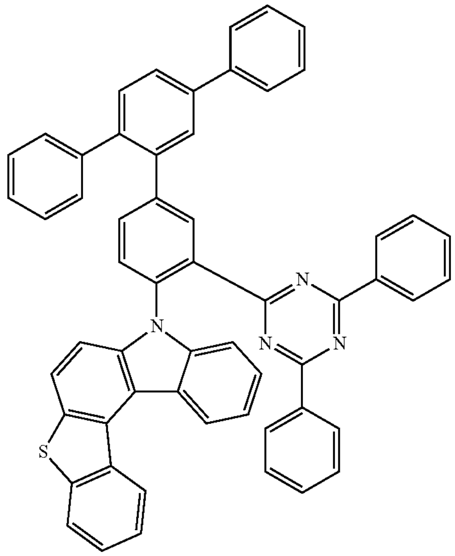
159
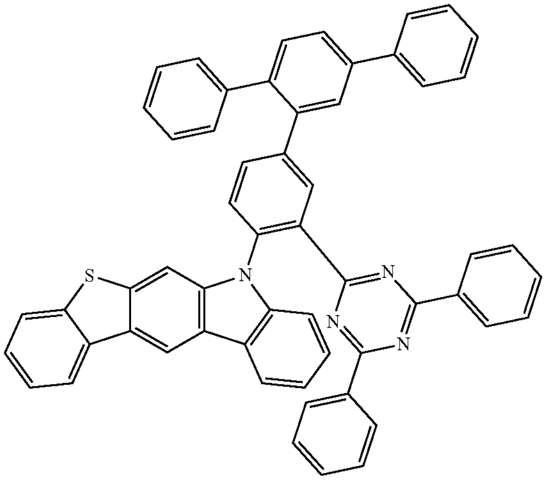
160
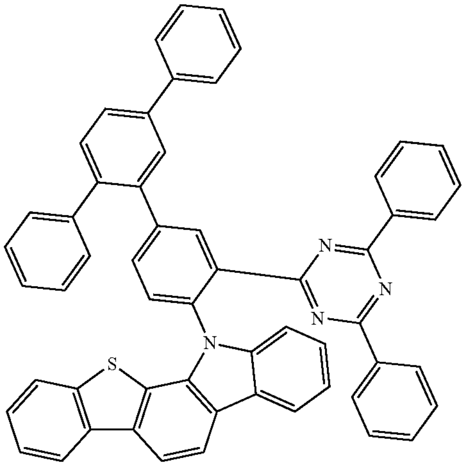
-continued
161
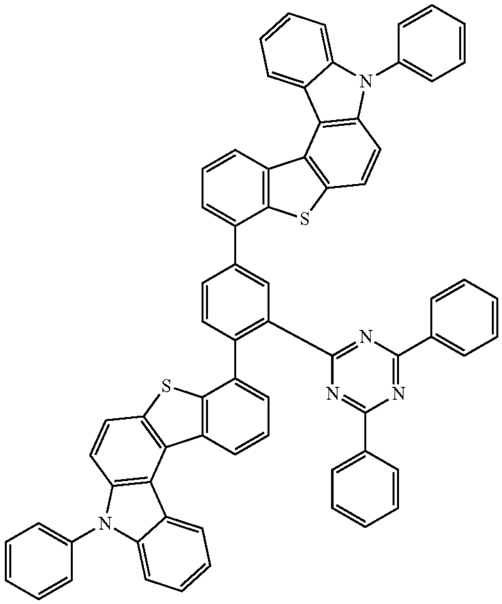
162
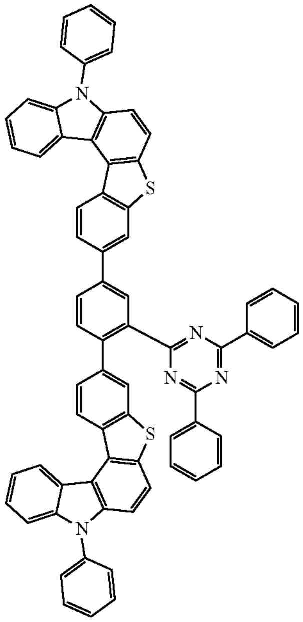

-continued
163
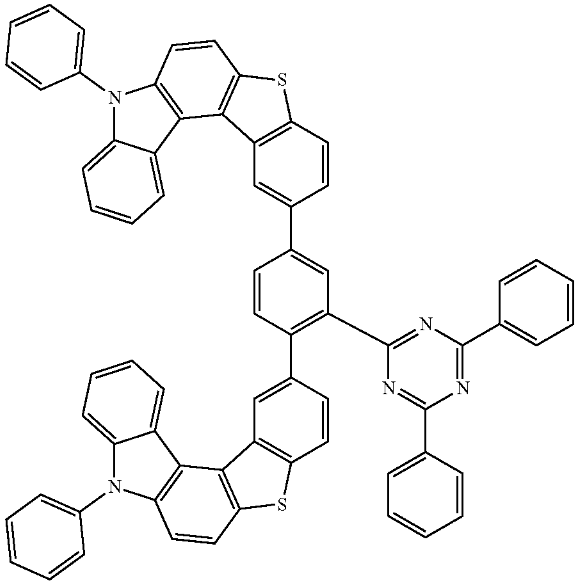
164
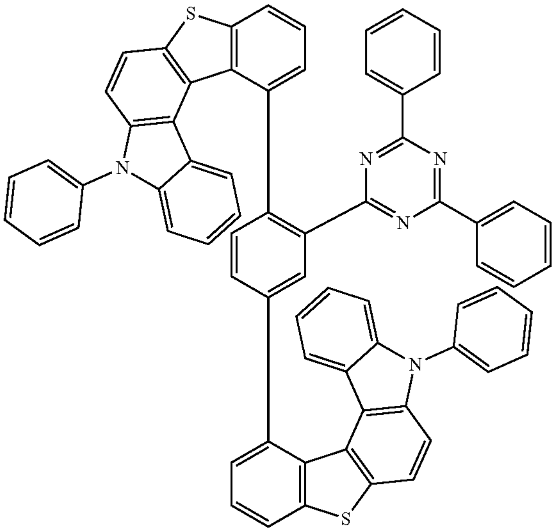
-continued
165
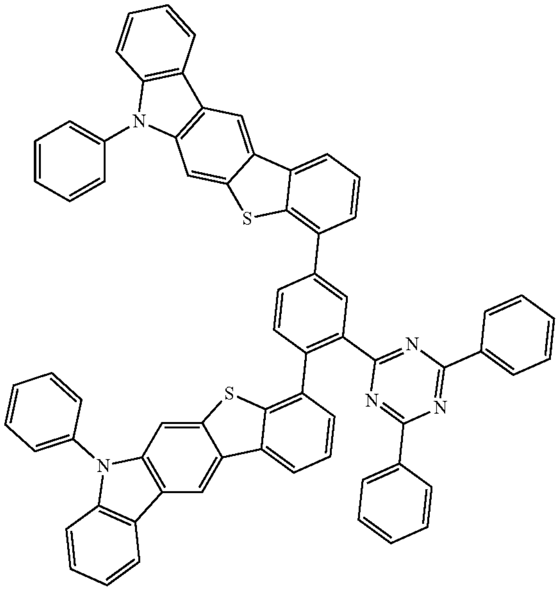
166
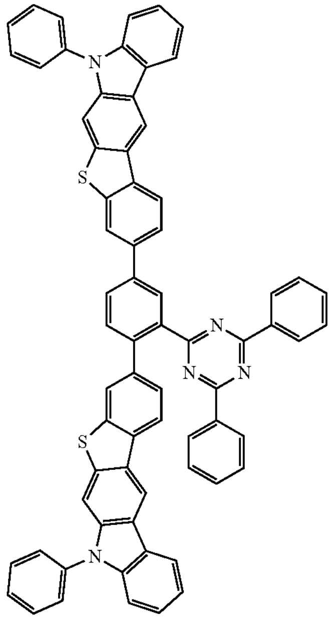

-continued
167
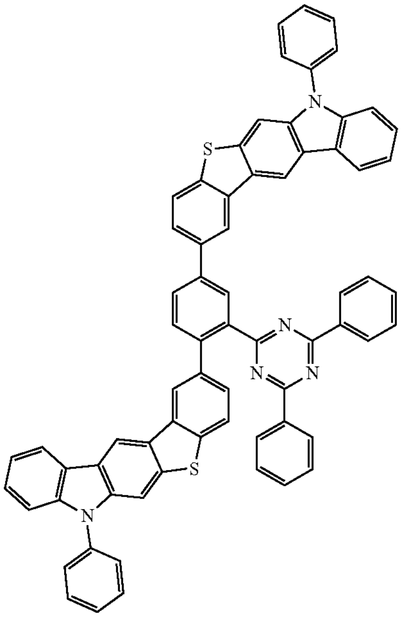
168
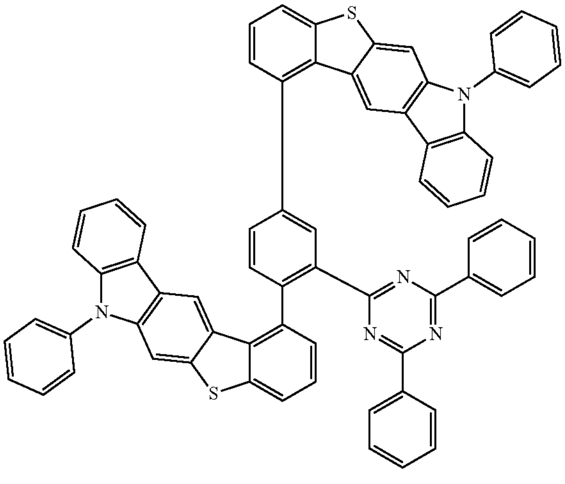
-continued
169
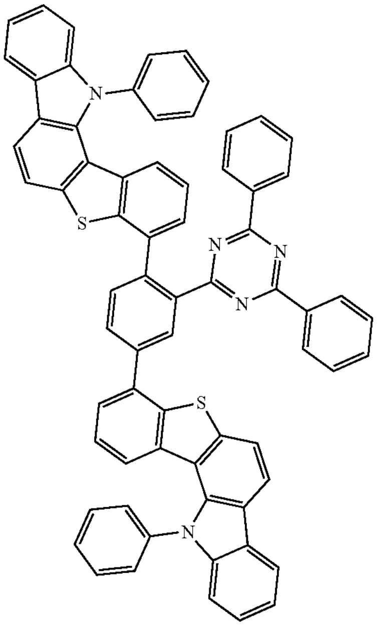
170
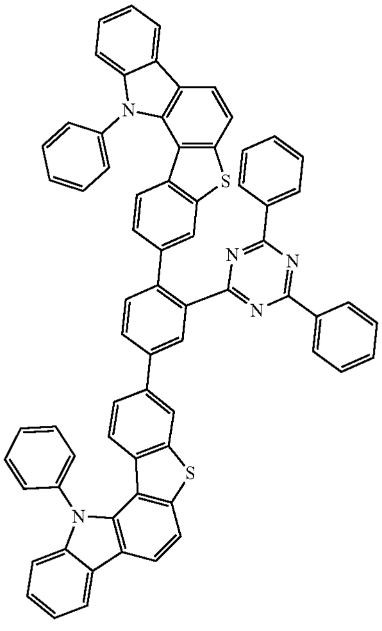

-continued
171
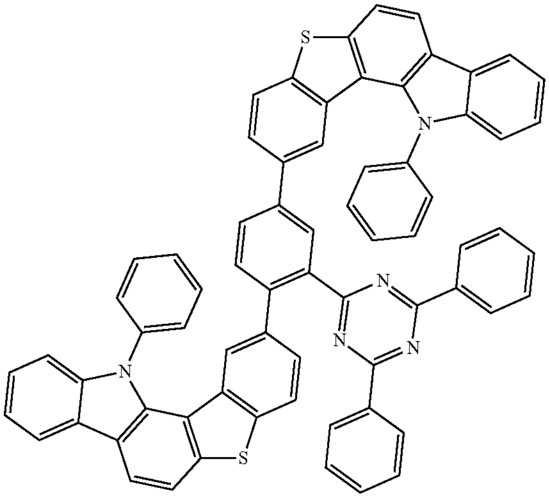
172
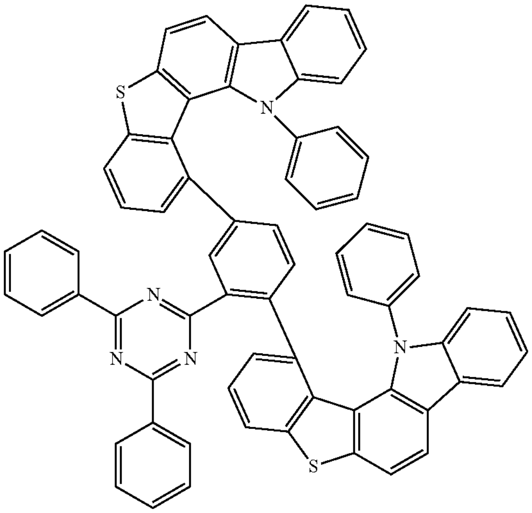
173
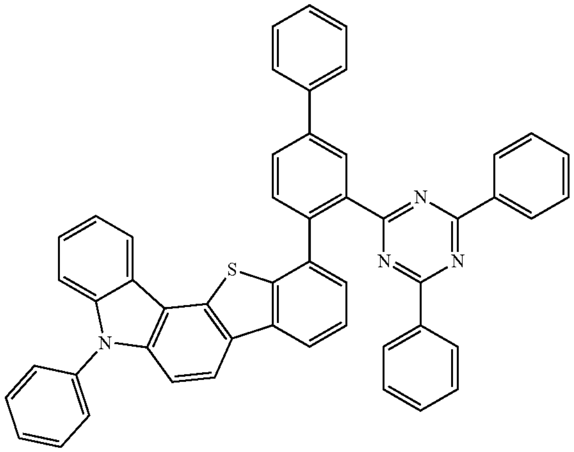
-continued
174
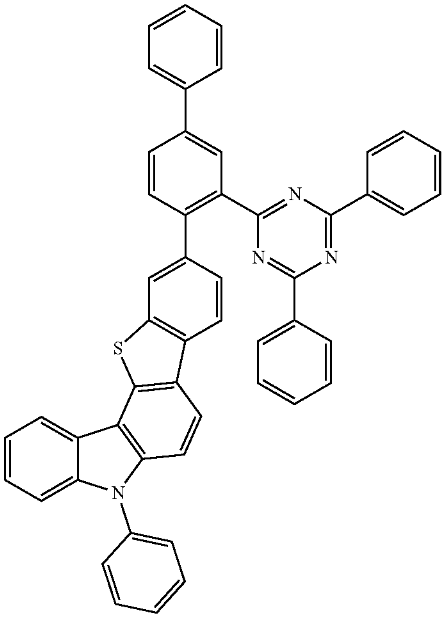
175
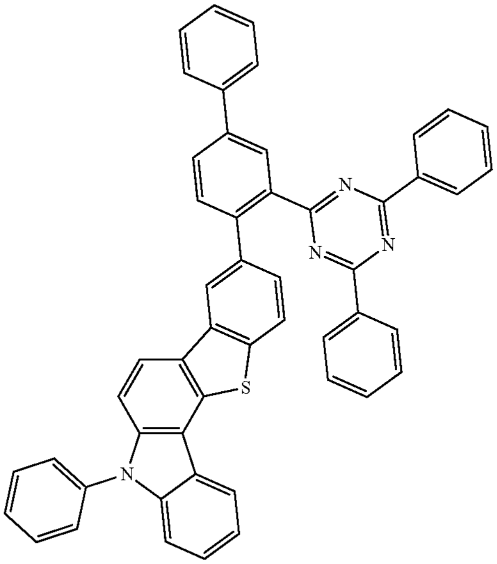
176
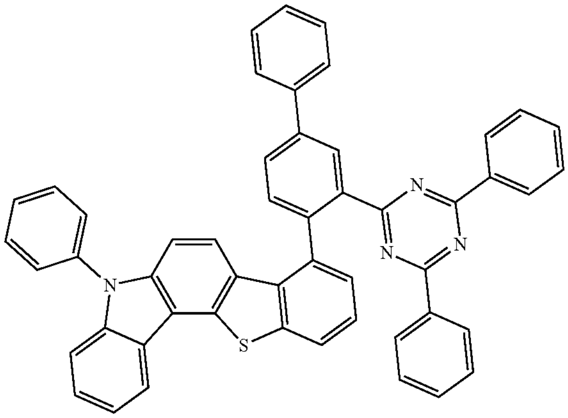

-continued
177
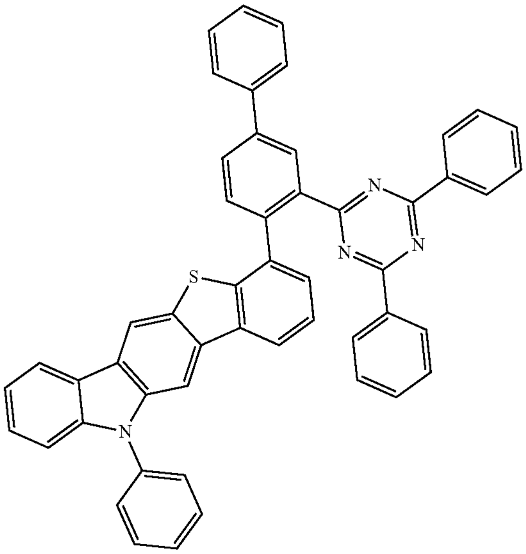
178
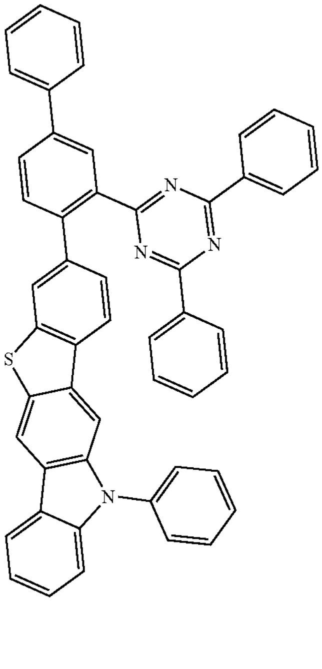
-continued
179
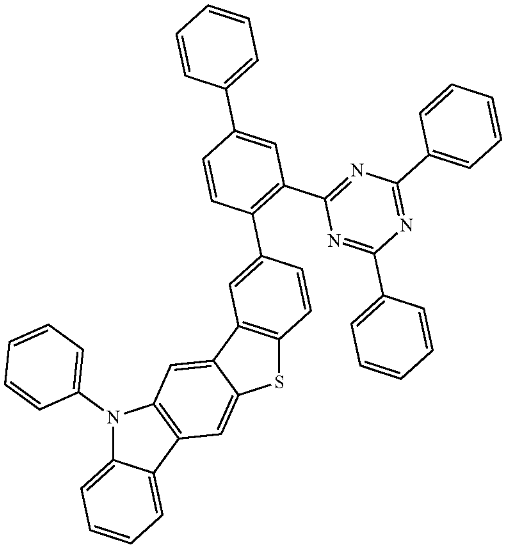
180
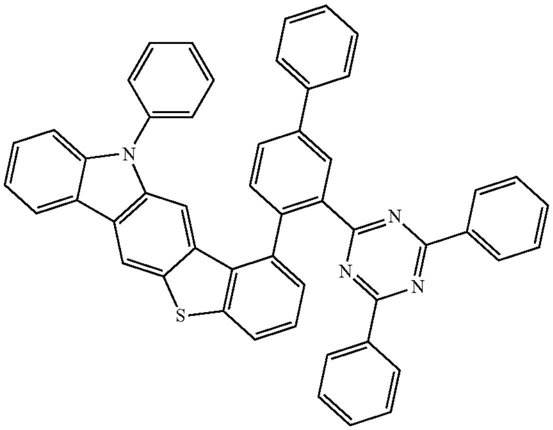
181
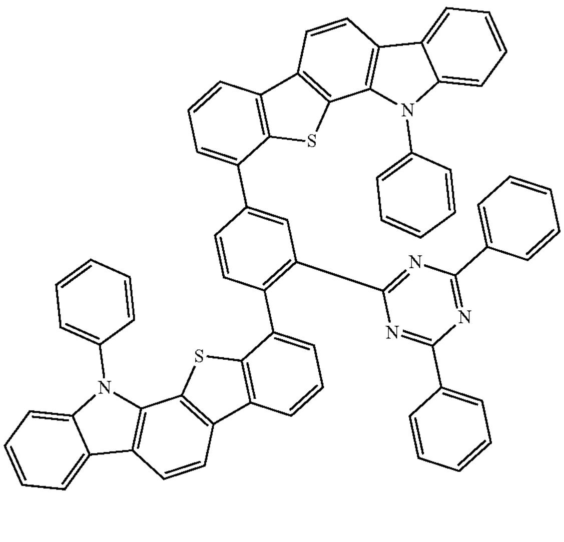

-continued
182
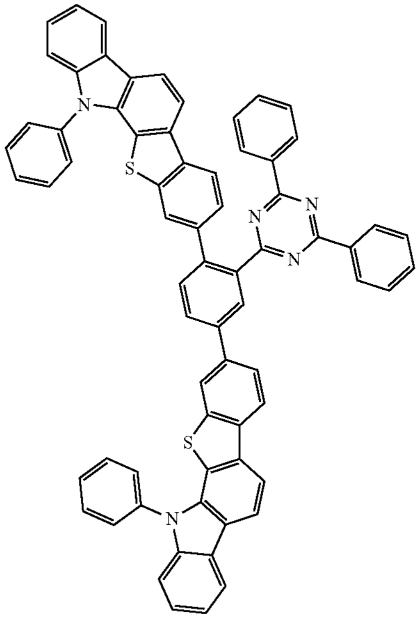
183
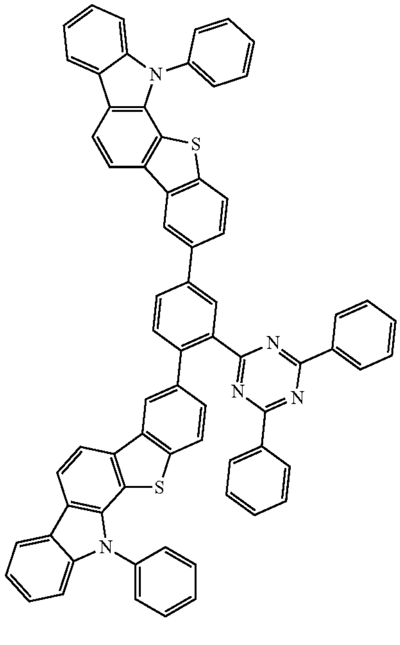
-continued
184
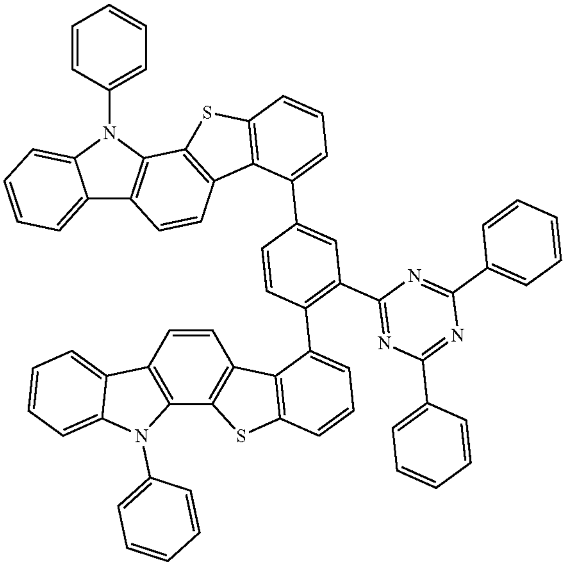
185
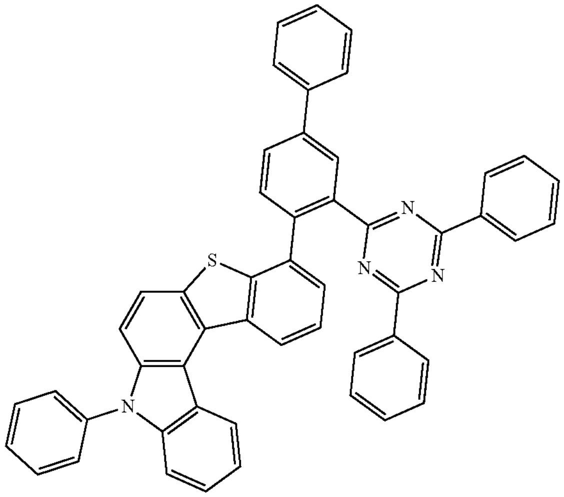

-continued
186
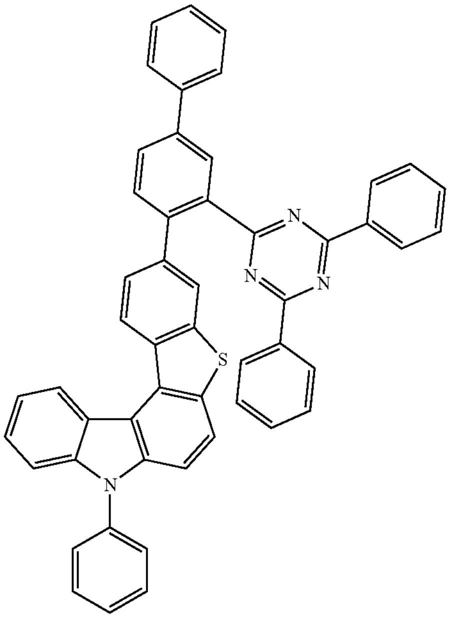
187
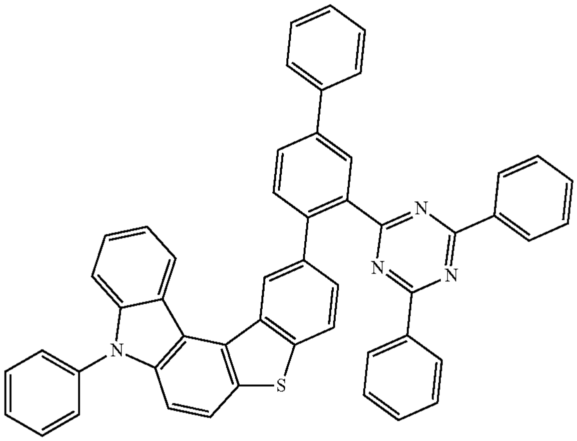
188
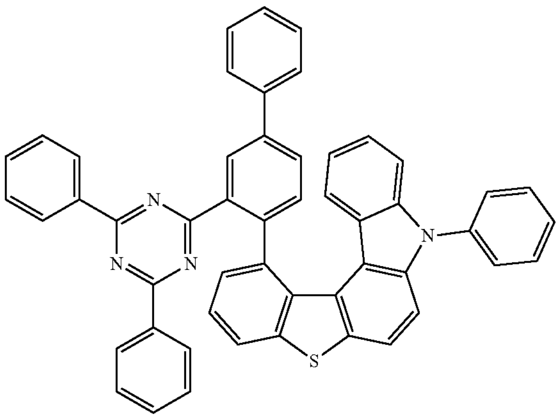
-continued
189
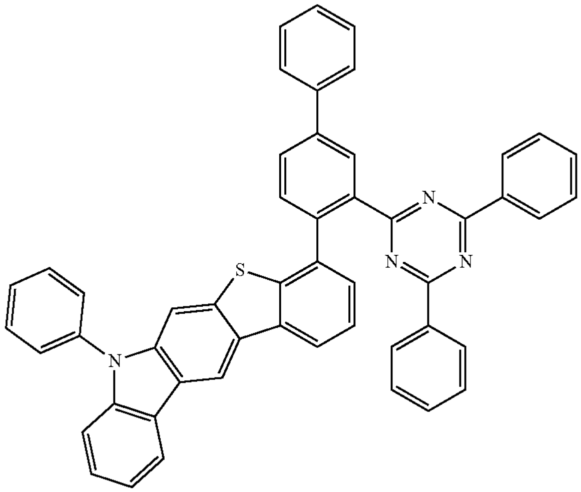
190
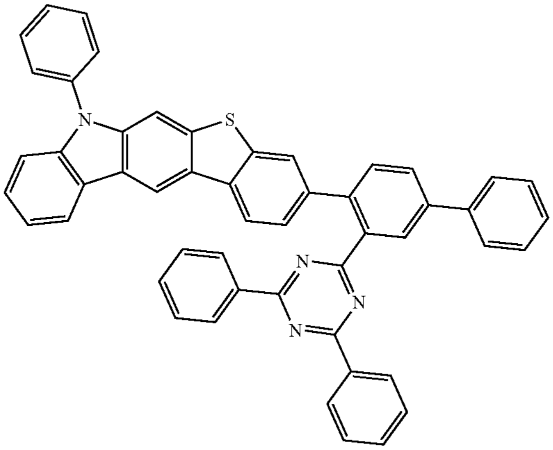
191
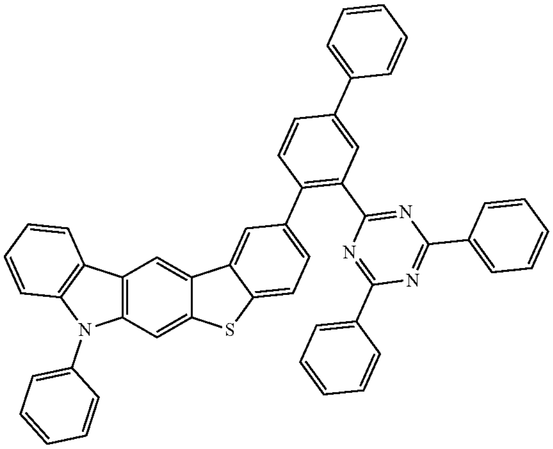

-continued
192
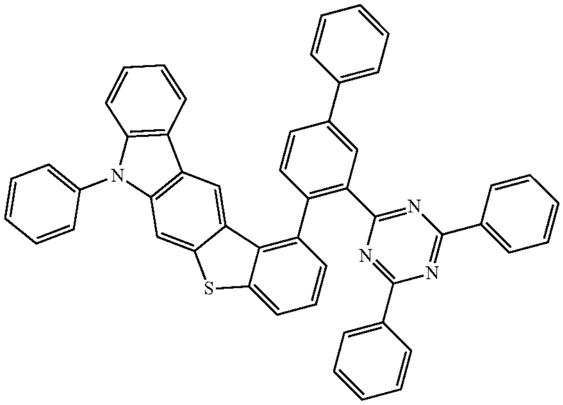
193
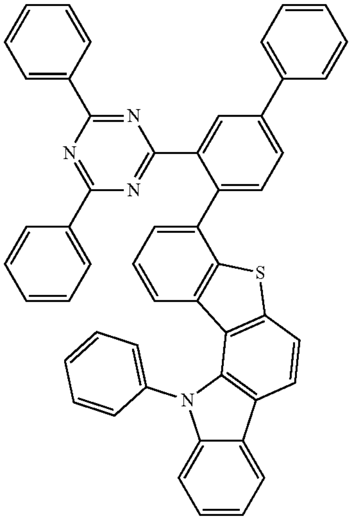
194
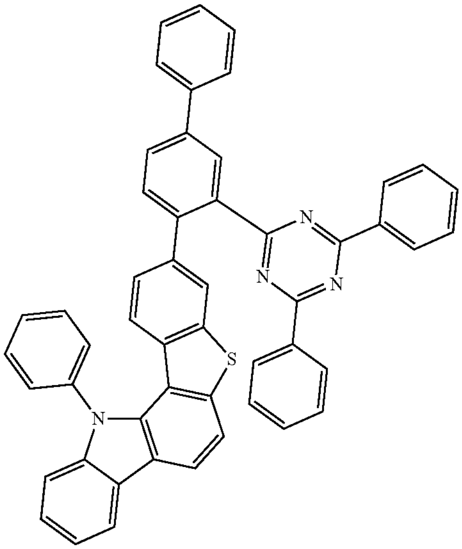
-continued
195
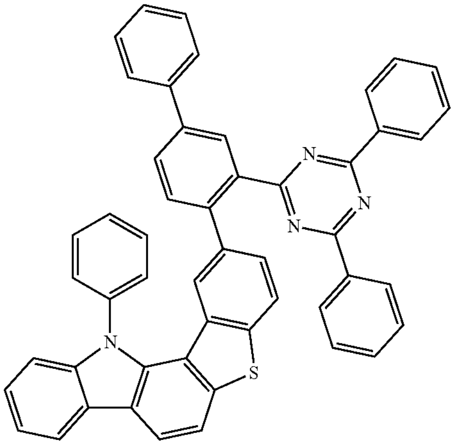
196
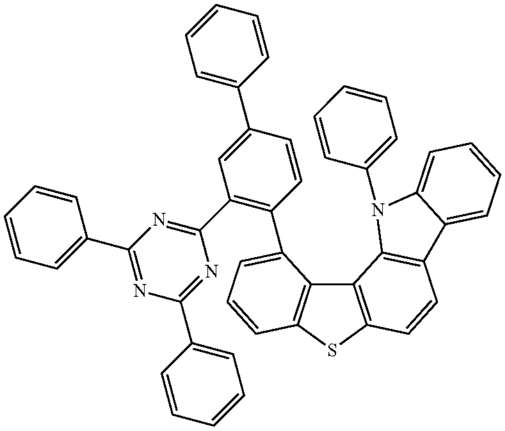
197
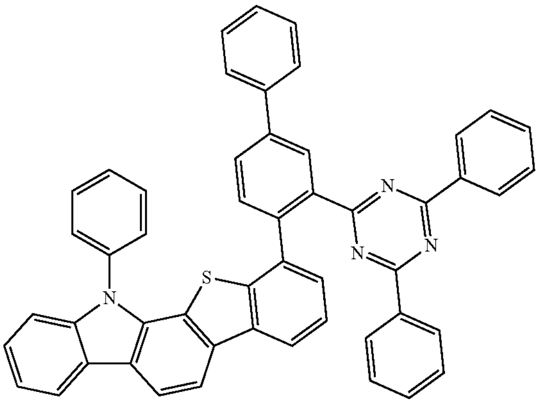

198
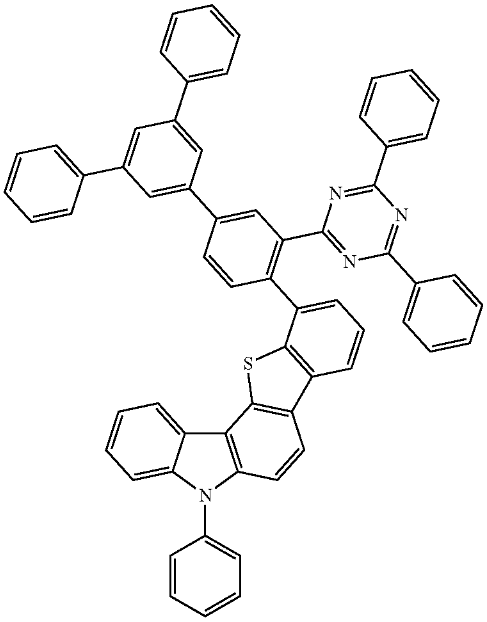
199
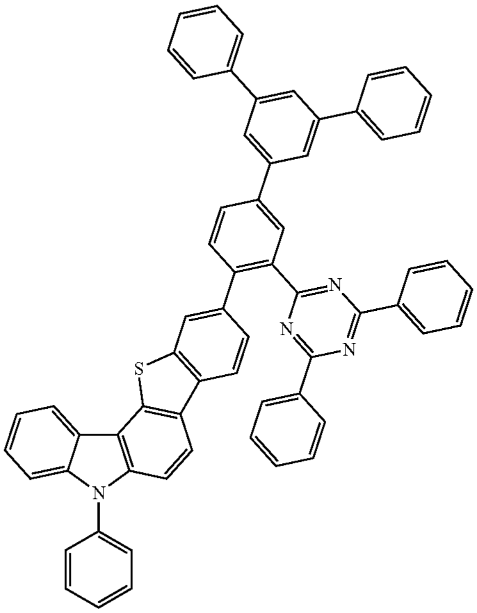
200
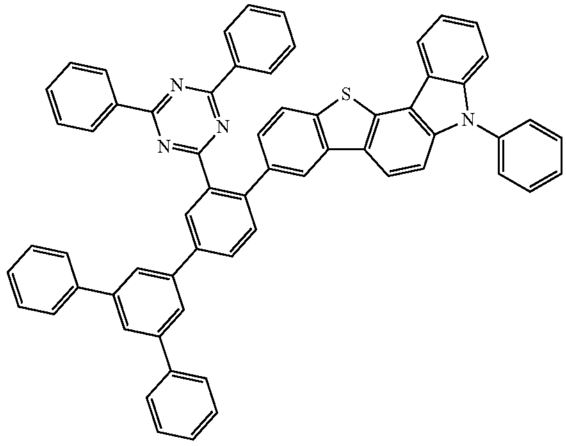
201
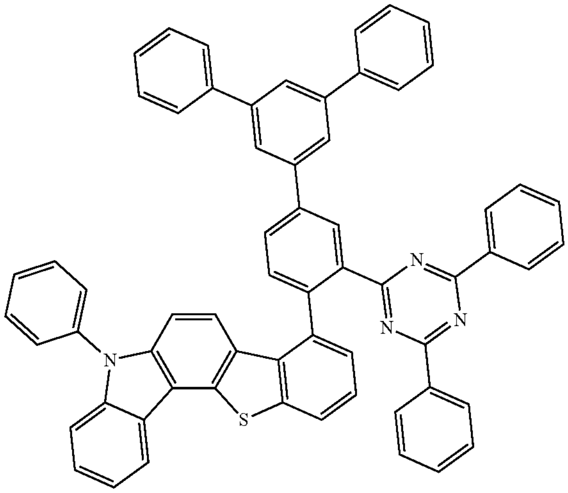
202
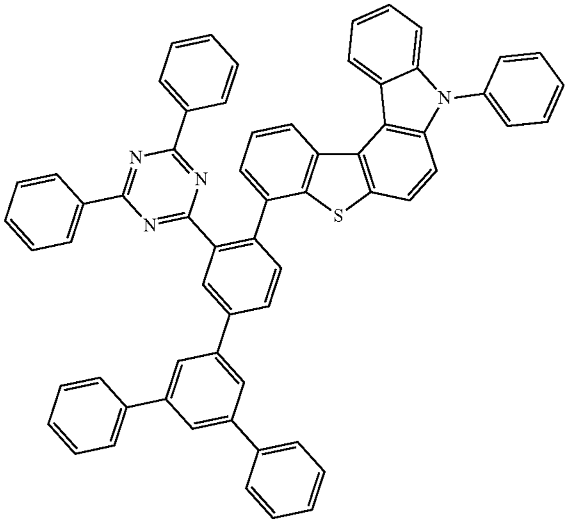

-continued
203
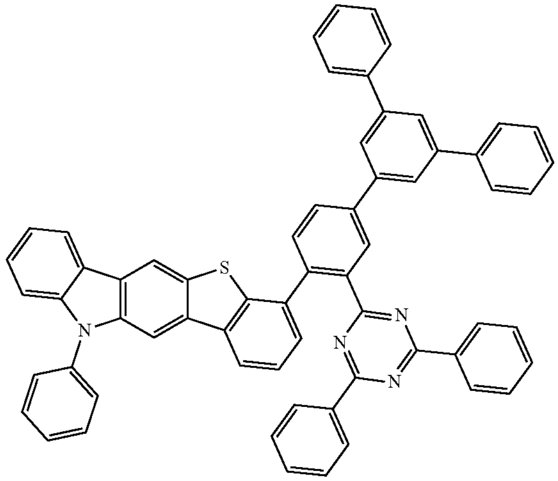
204
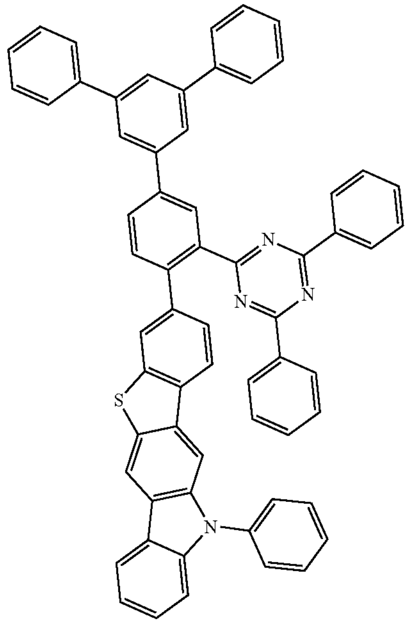
-continued
205
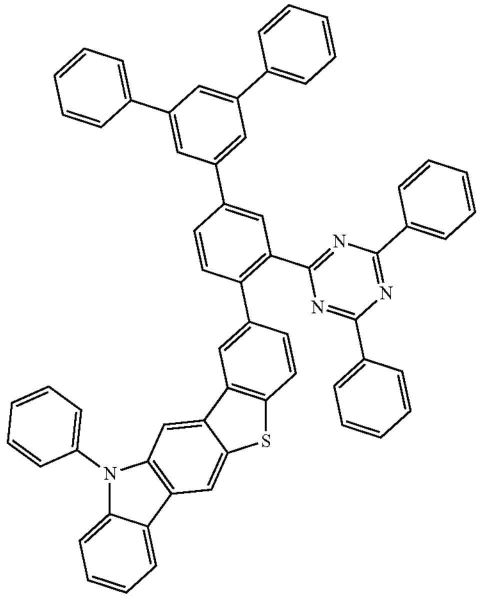
206
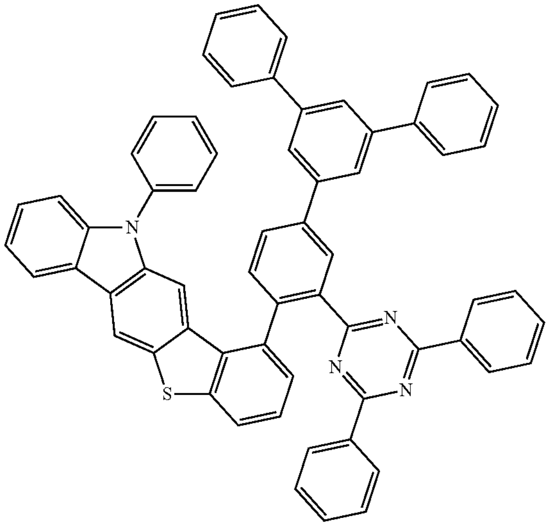

-continued
207
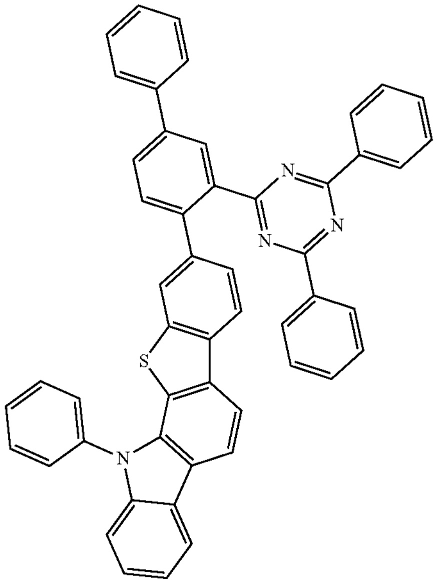
208
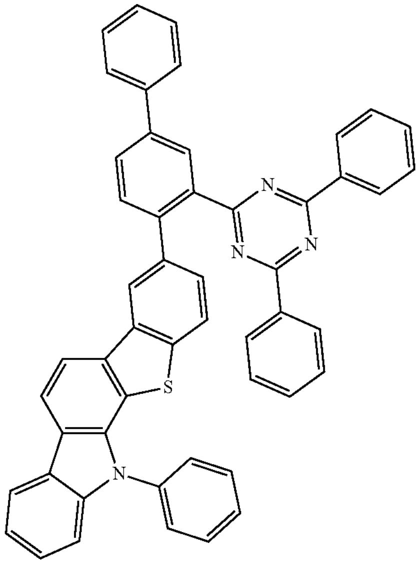
209
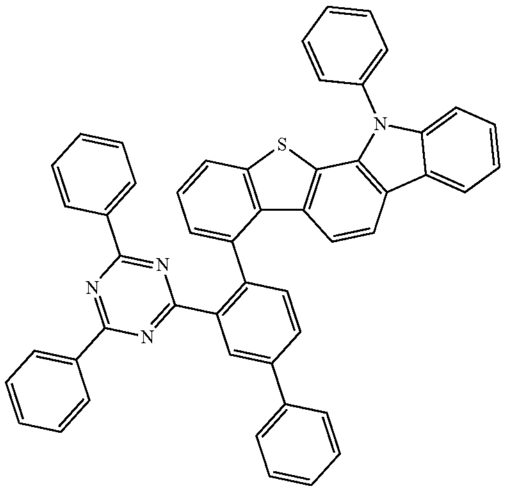
-continued
210
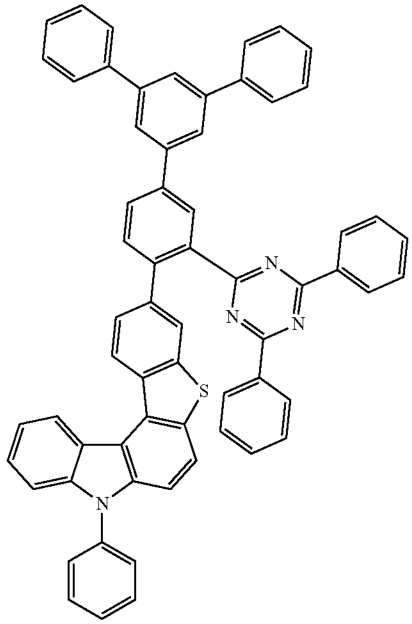
211
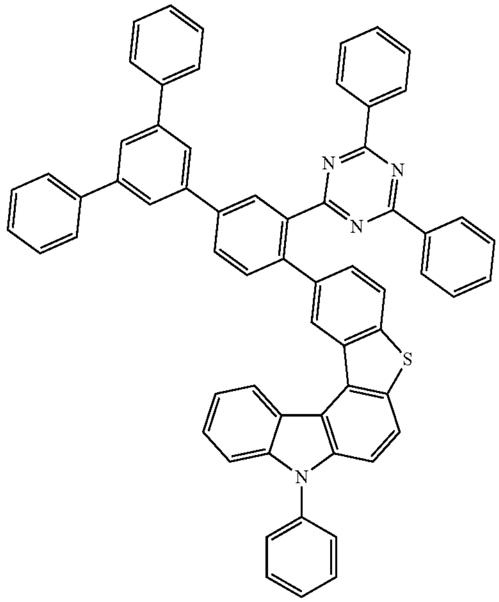

-continued
212
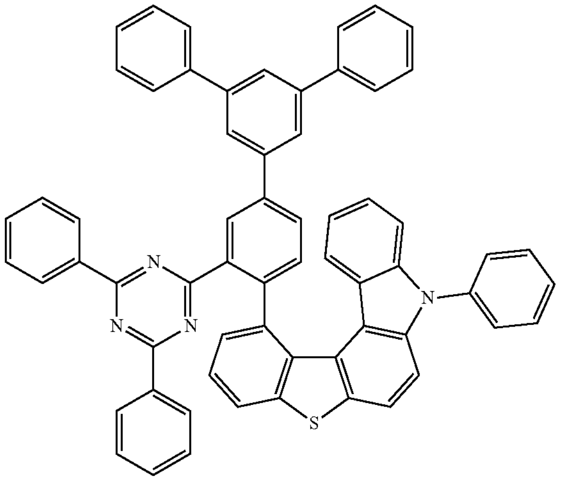
213
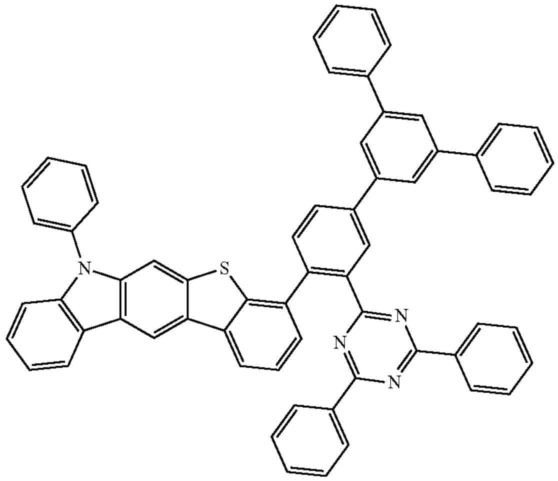
214
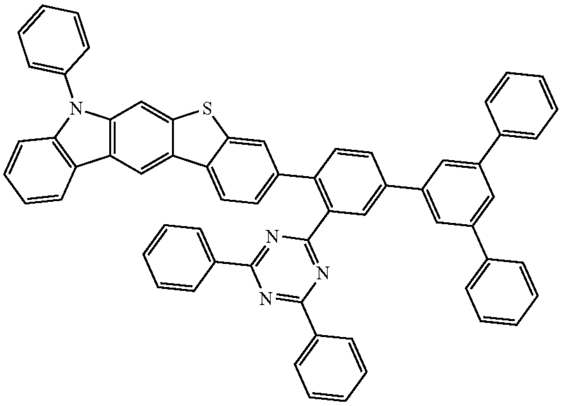
-continued
215
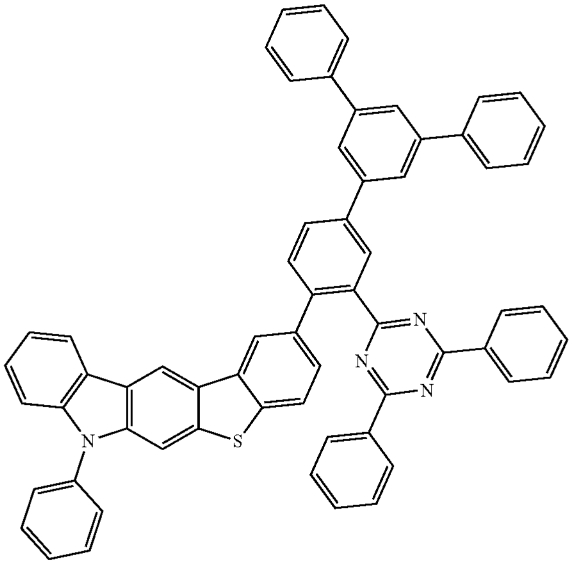
216
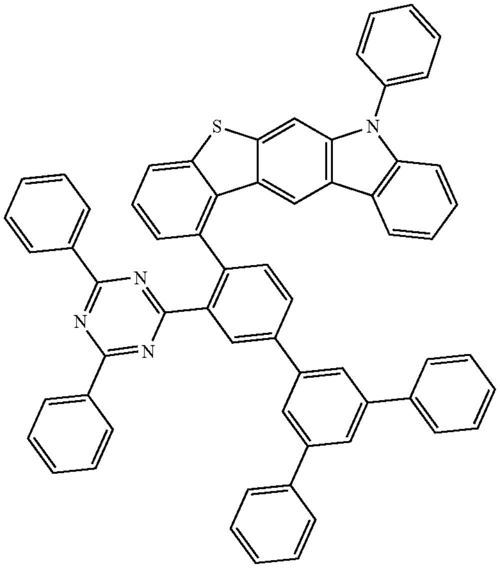

-continued
217
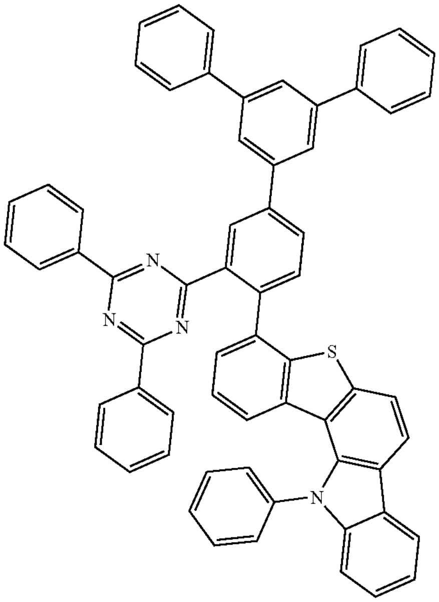
218
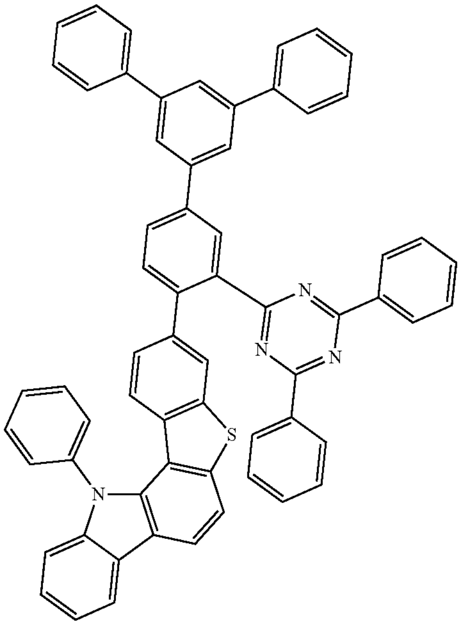
-continued
219
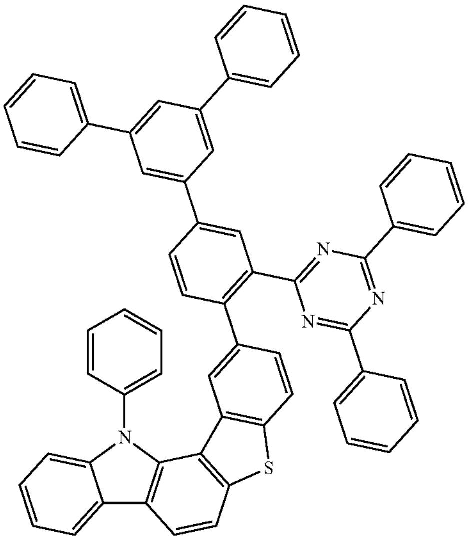
220
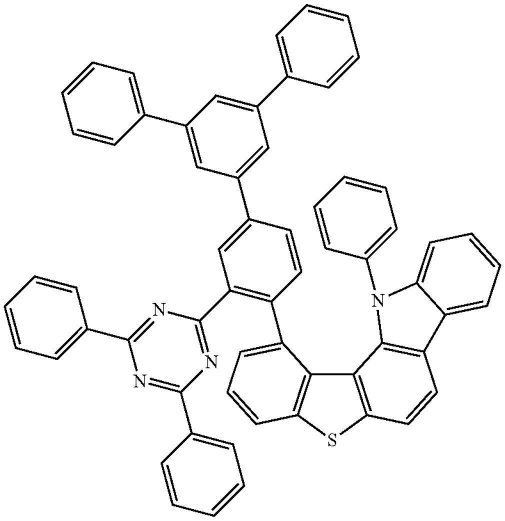

-continued
221
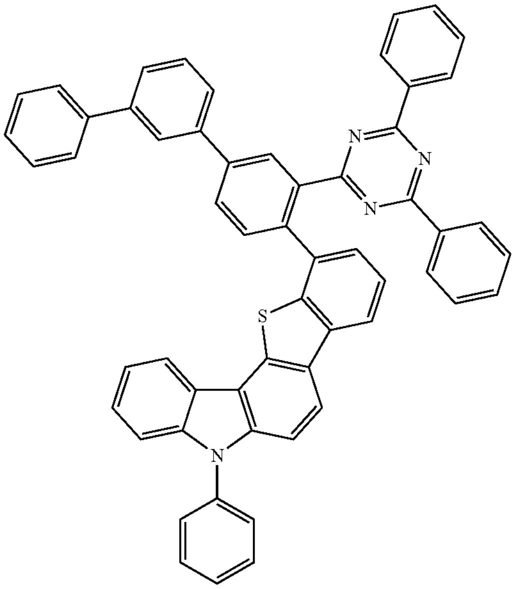
222
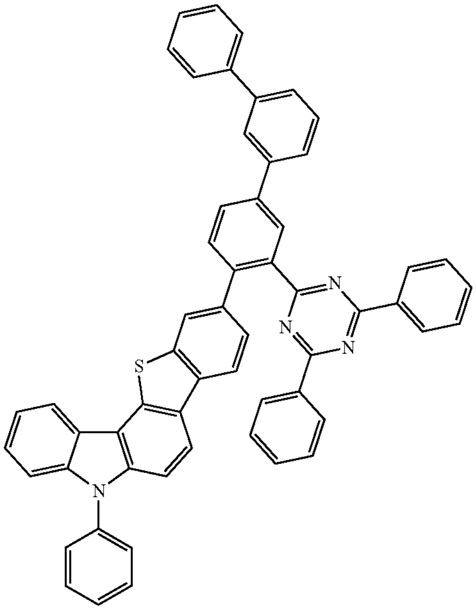
-continued
223
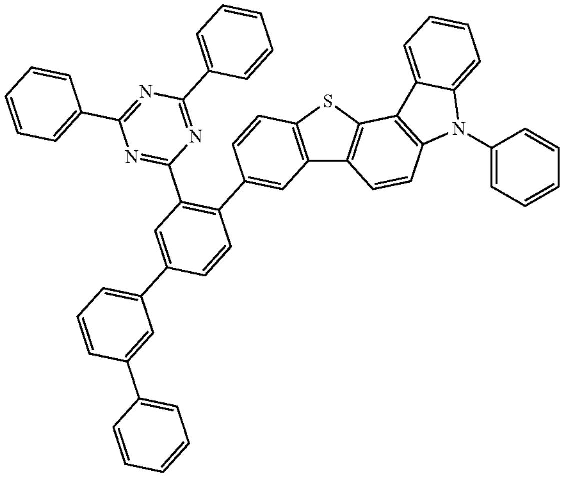
224
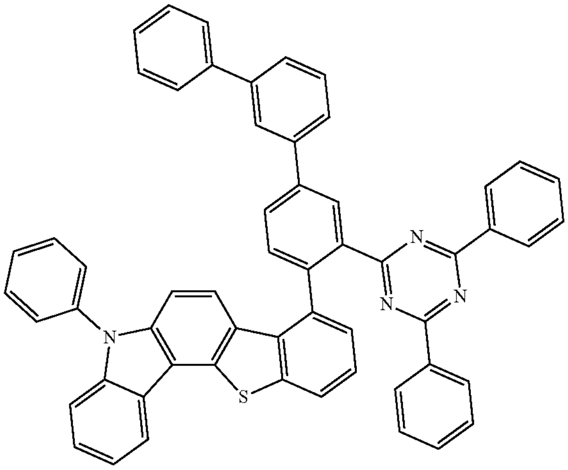
225
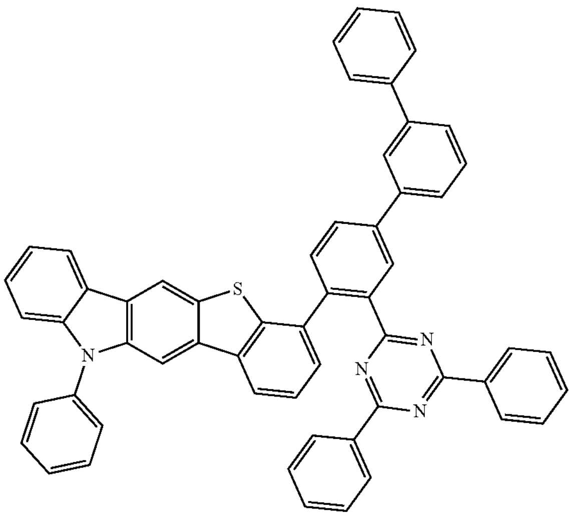

-continued
226
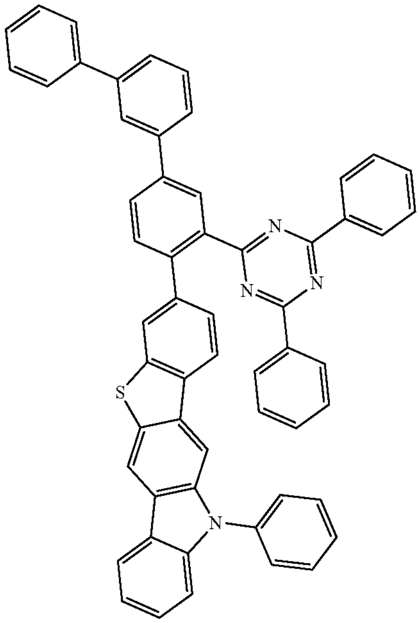
227
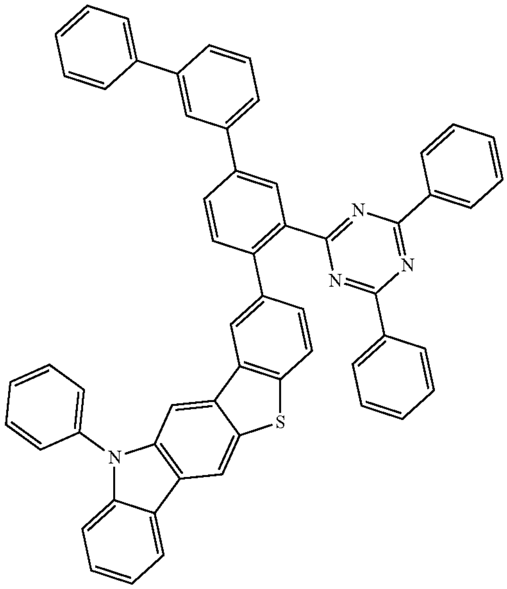
-continued
228
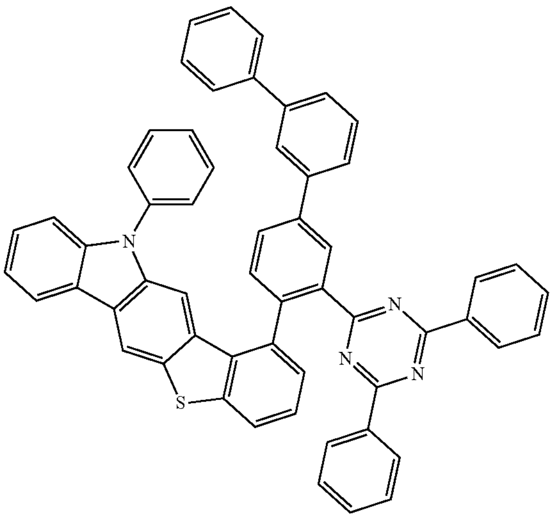
229
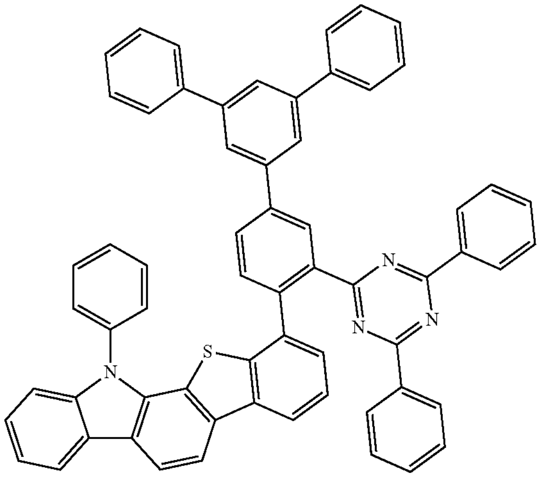
230
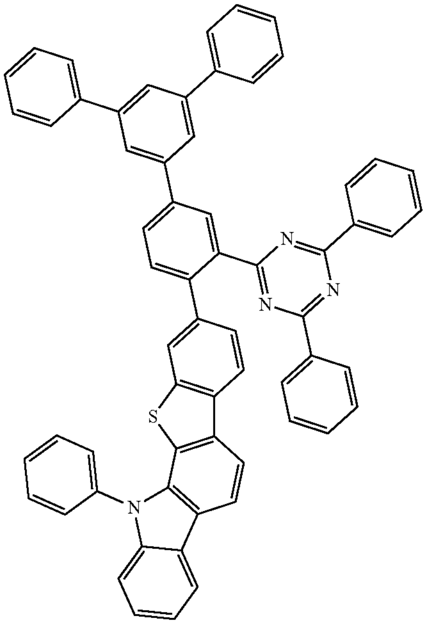

-continued
231
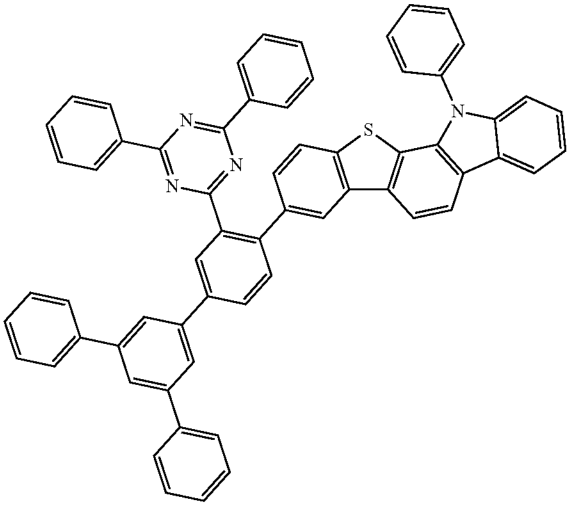
232
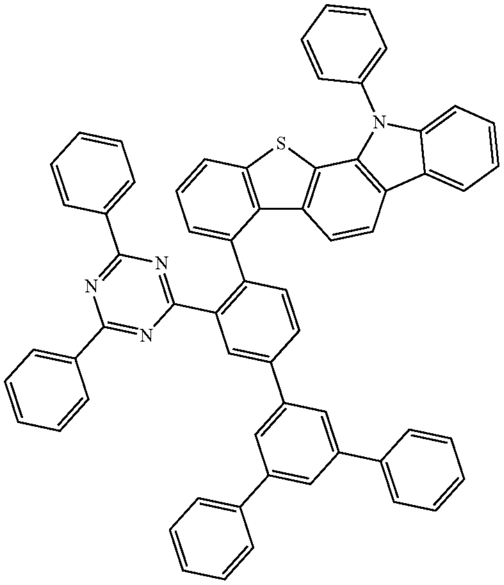
-continued
233
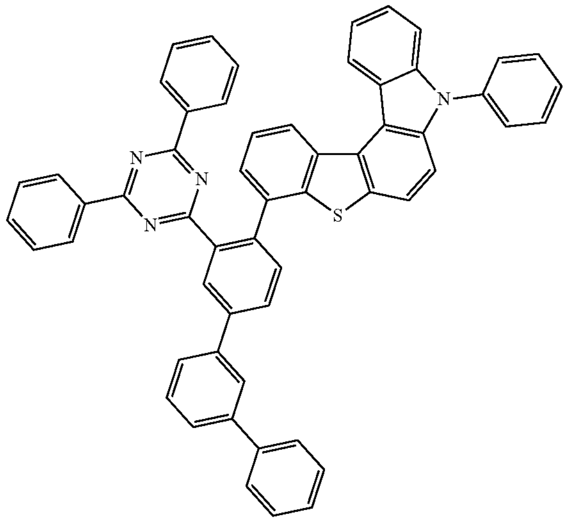
234
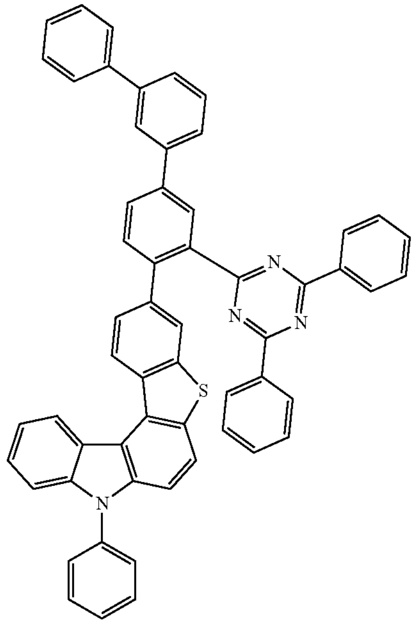

-continued
235
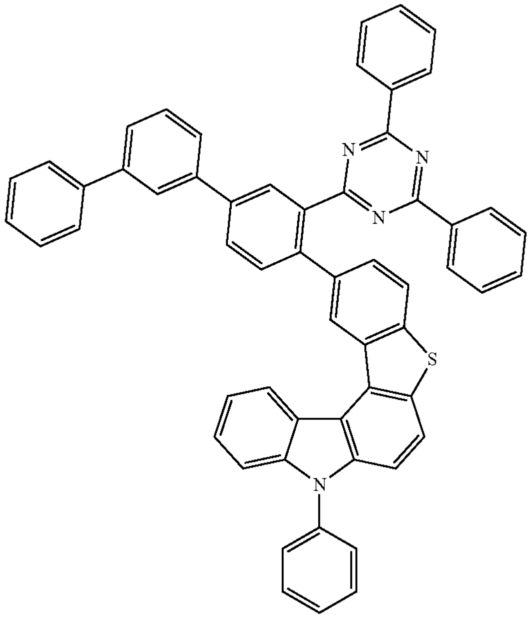
236
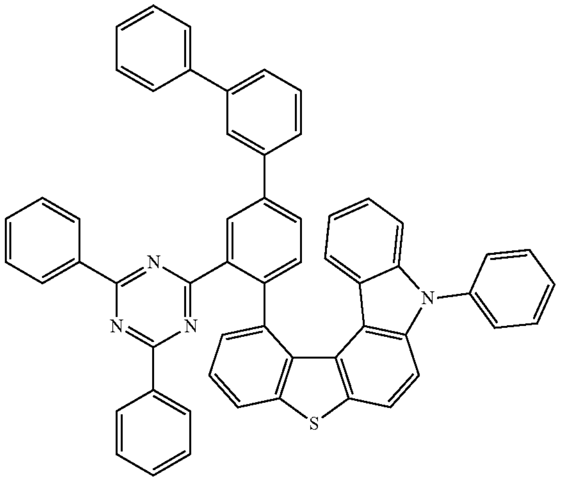
-continued
237
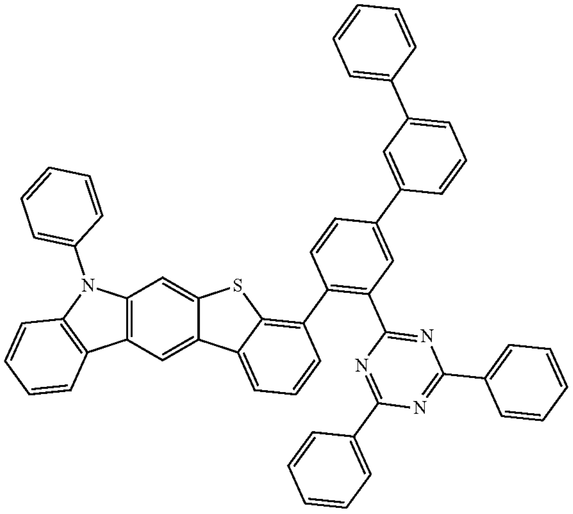
238
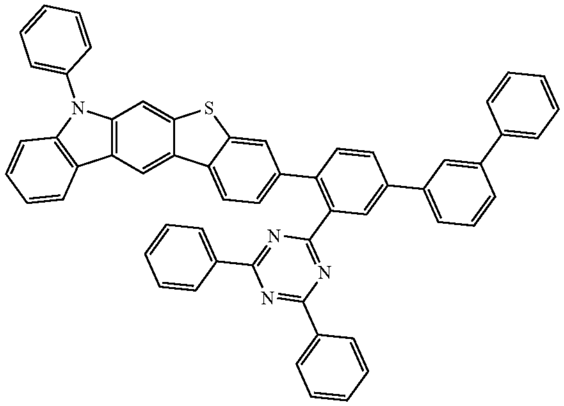
239
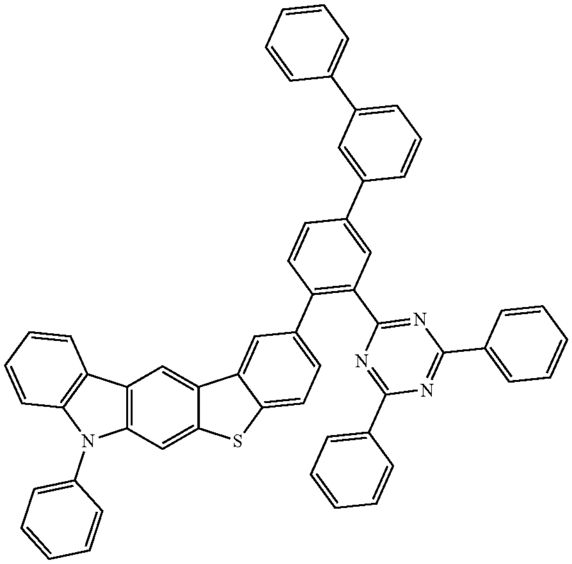

-continued
240
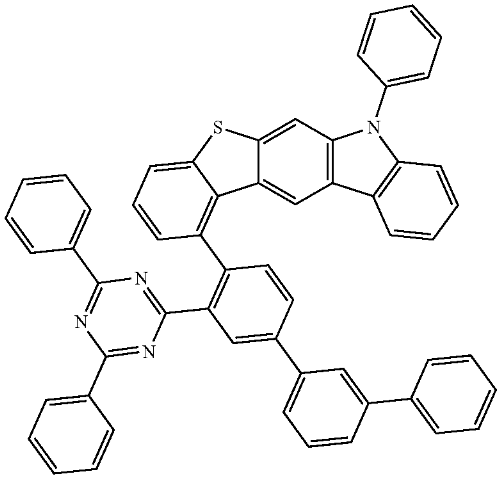
241
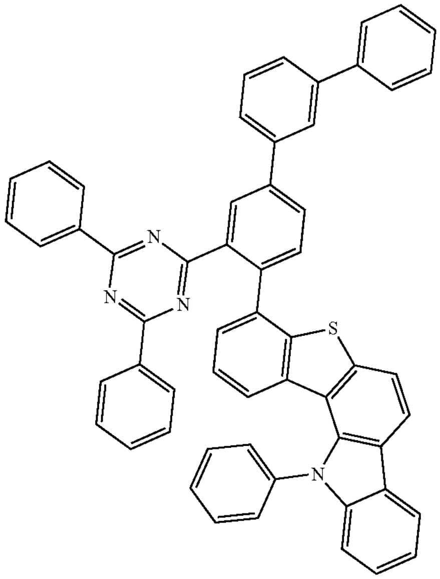
-continued
242
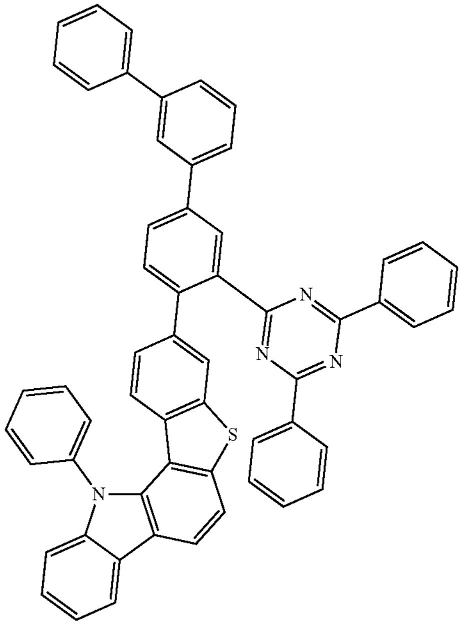
243
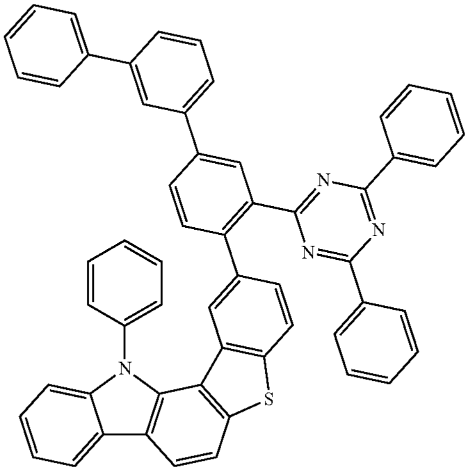
244
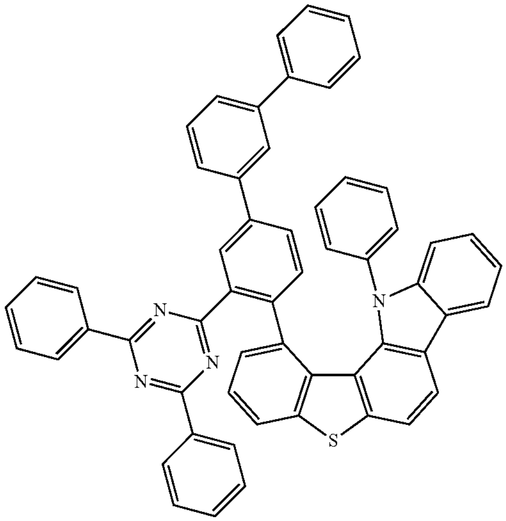

-continued
245
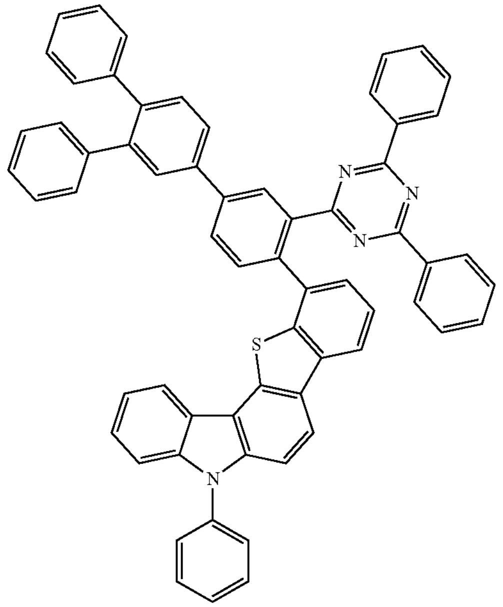
246
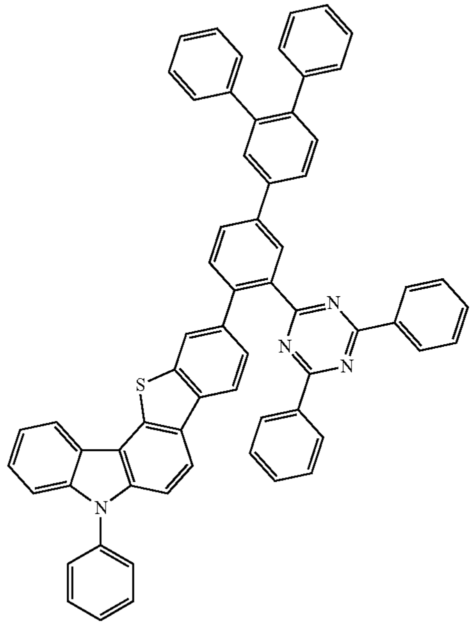
-continued
247
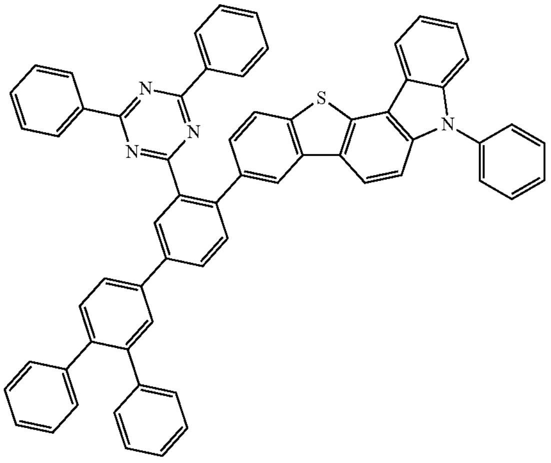
248
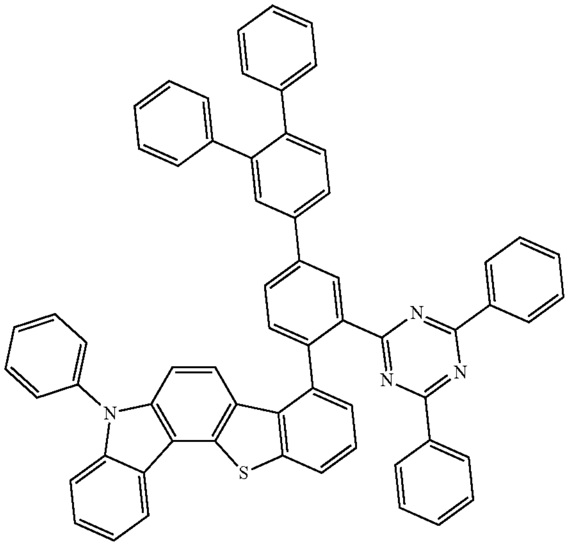
249
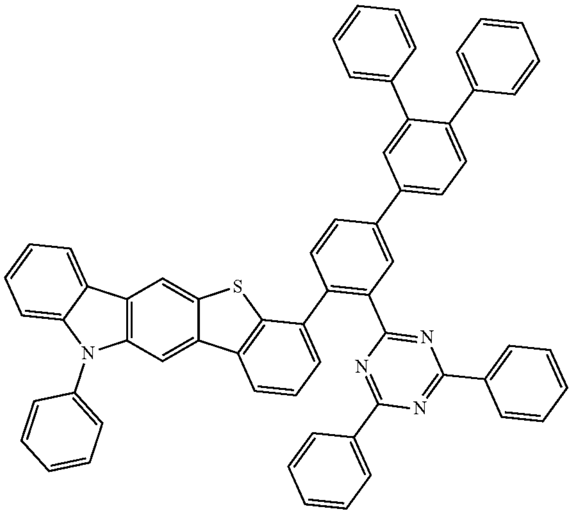

250
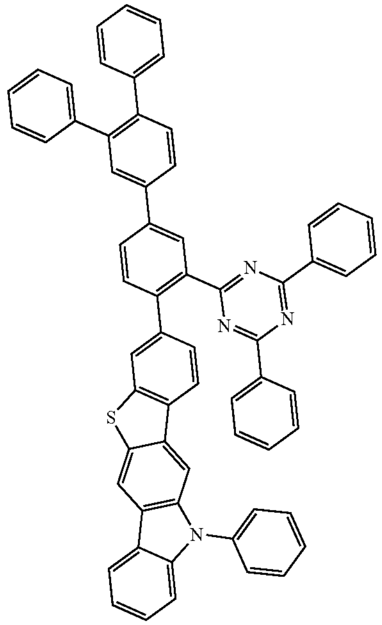
251
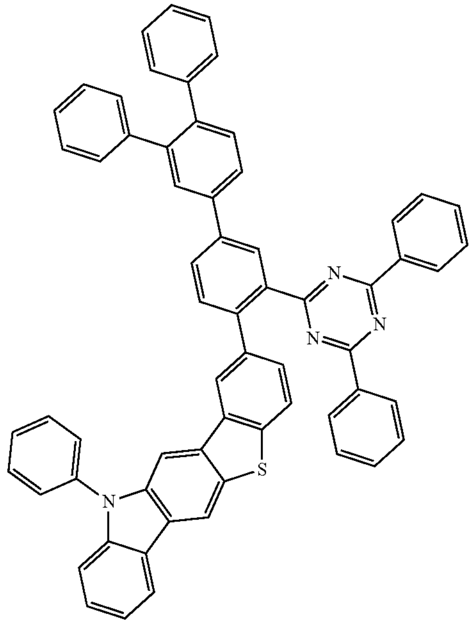
252
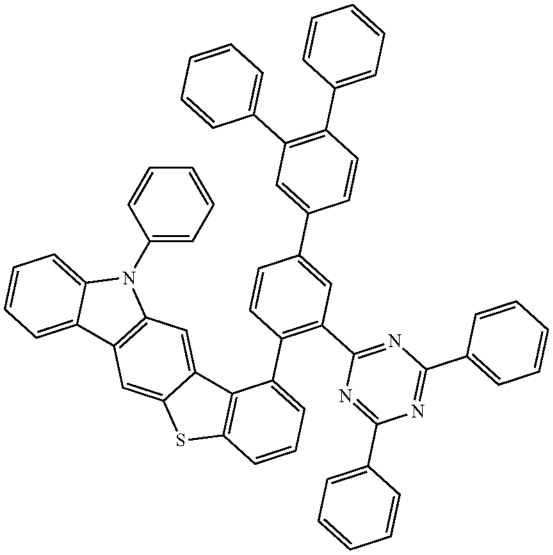
253
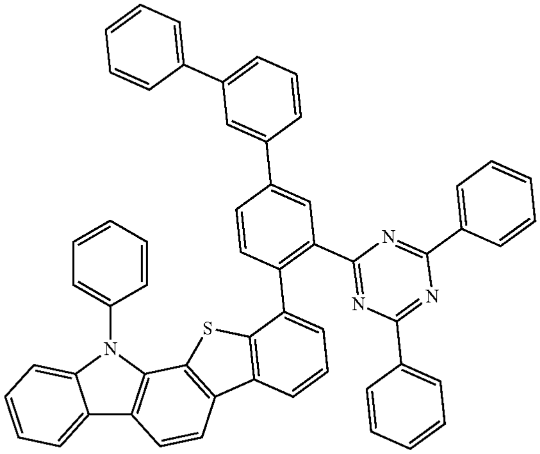

-continued
254
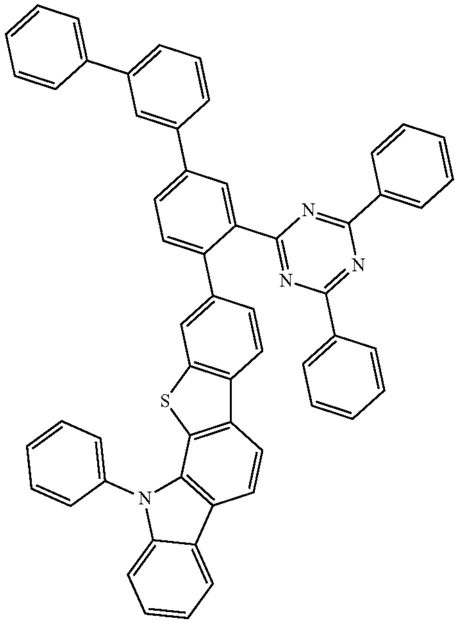
255
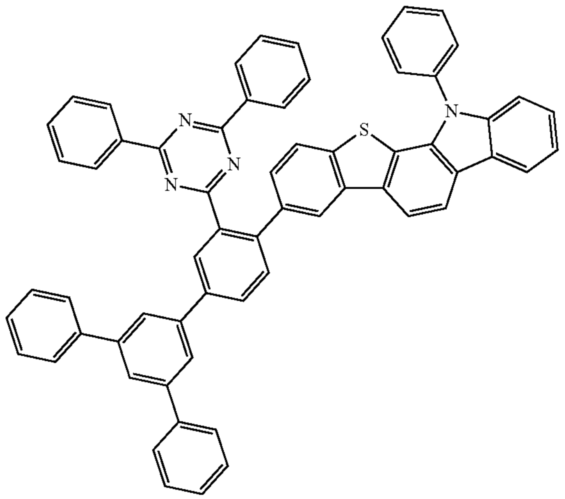
-continued
256
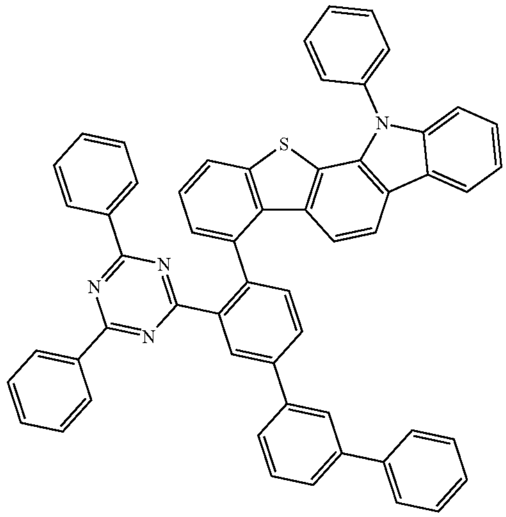
257
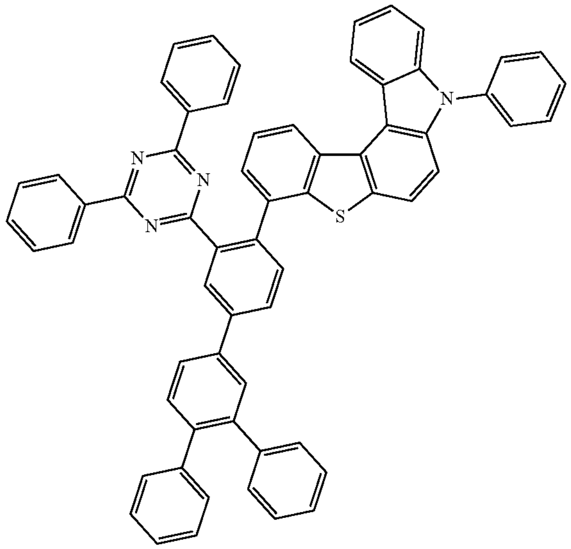

-continued
258
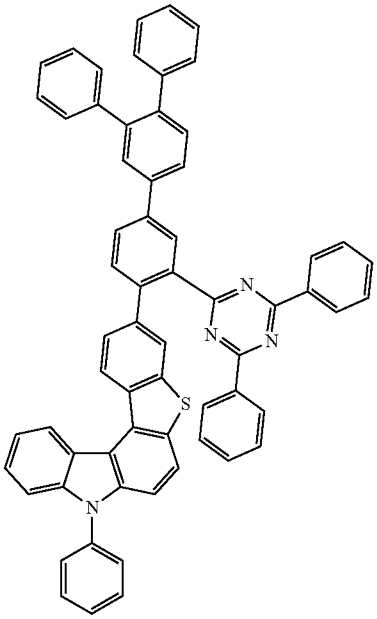
259
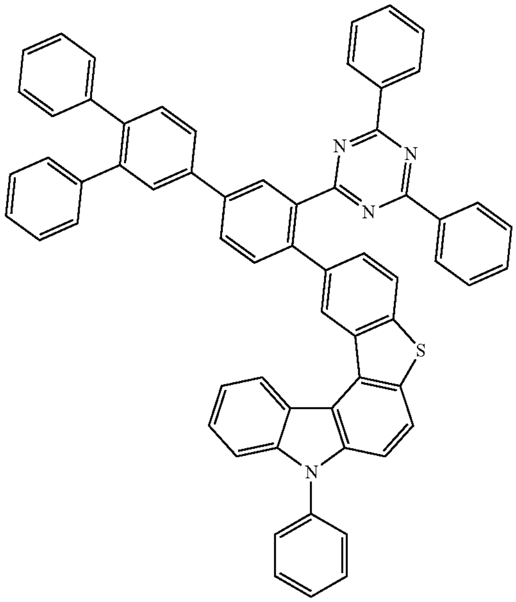
-continued
260
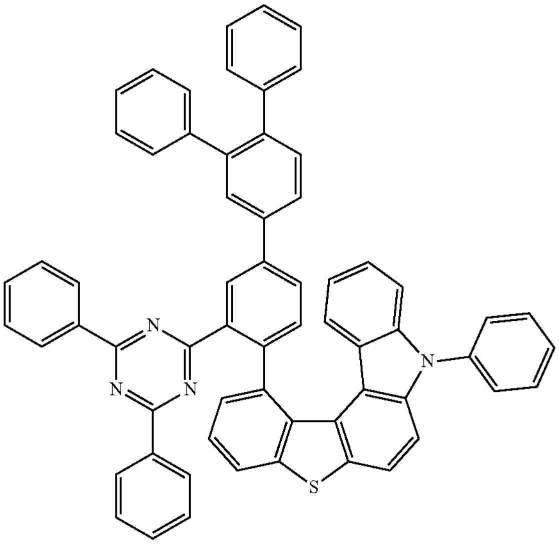
261
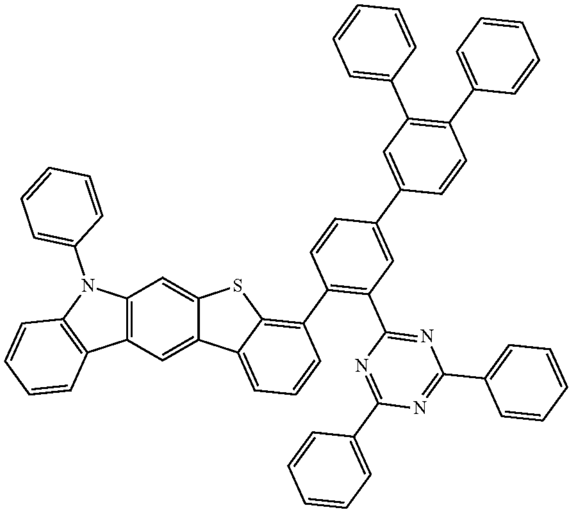
262
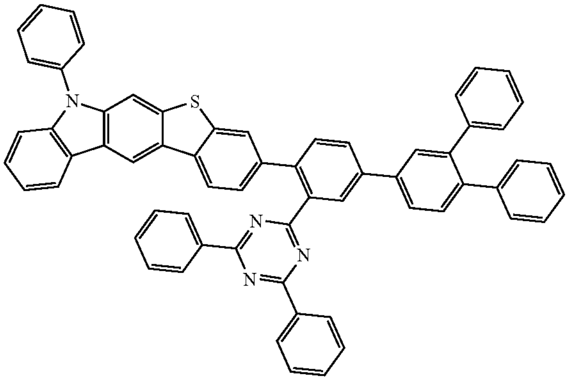

-continued
263
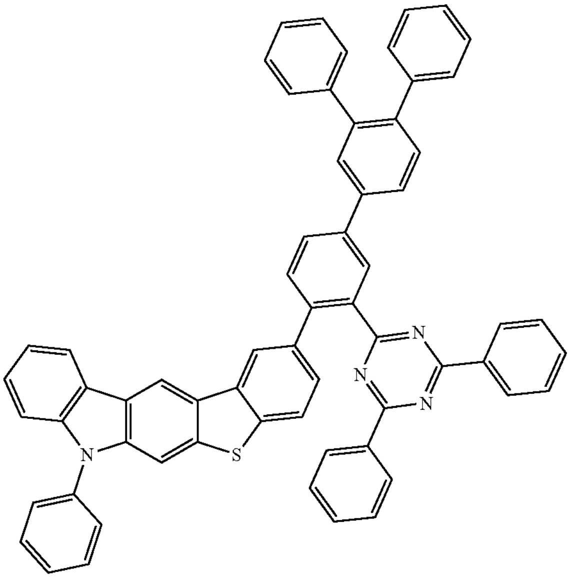
264
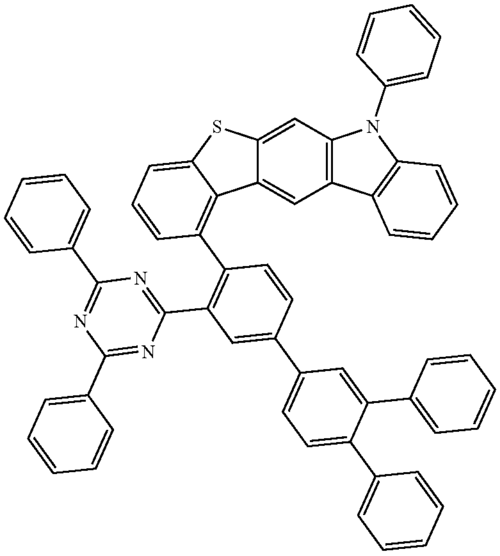
-continued
265
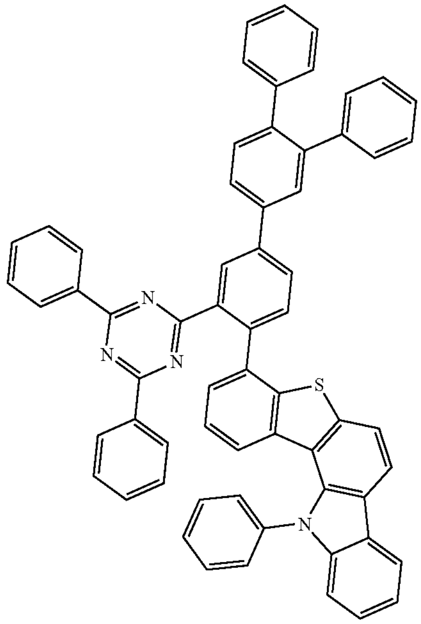
266
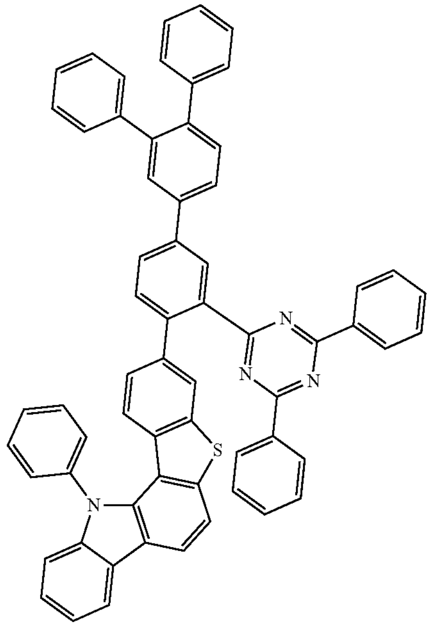

-continued
267
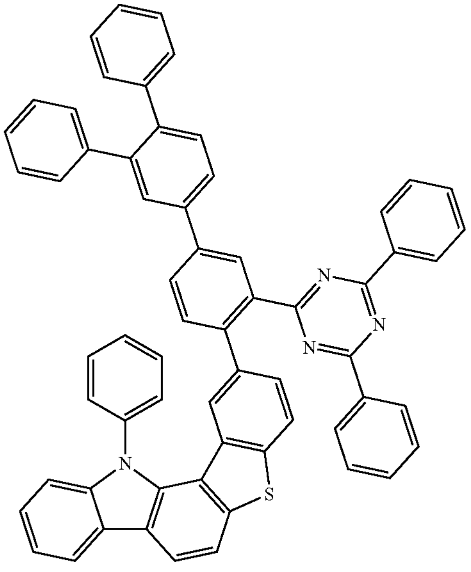
268
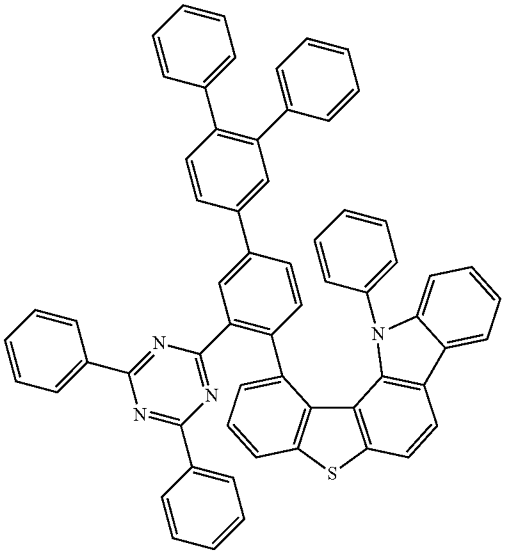
-continued
269
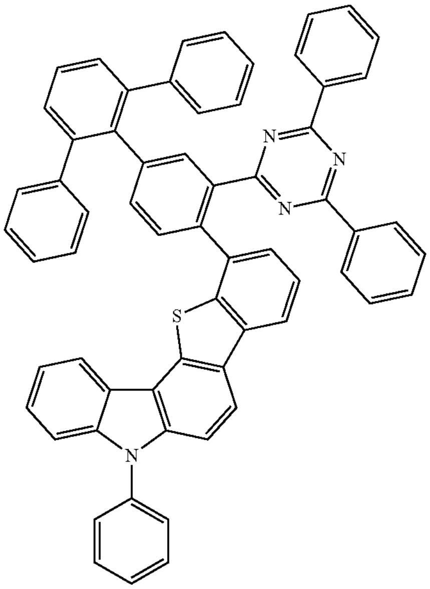
270
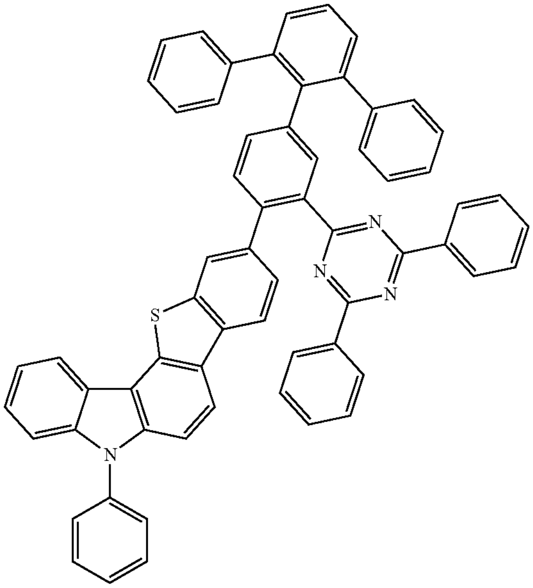
271
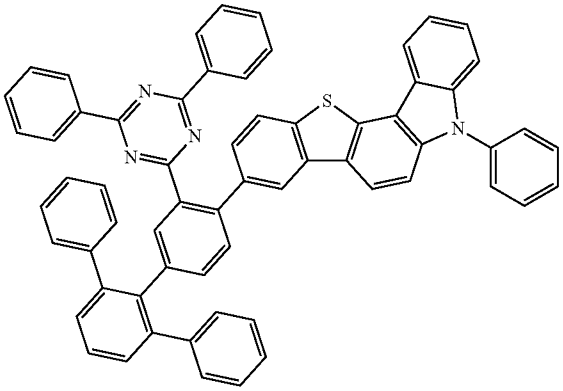

-continued
272
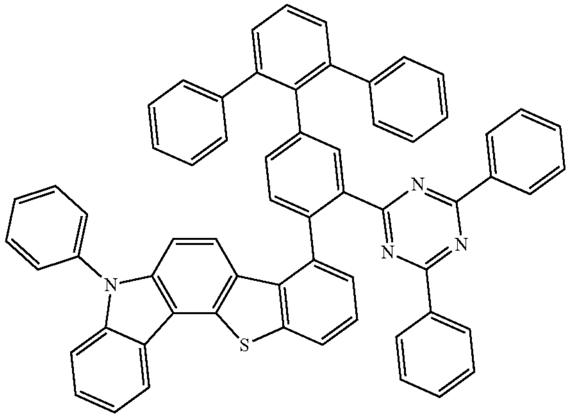
273
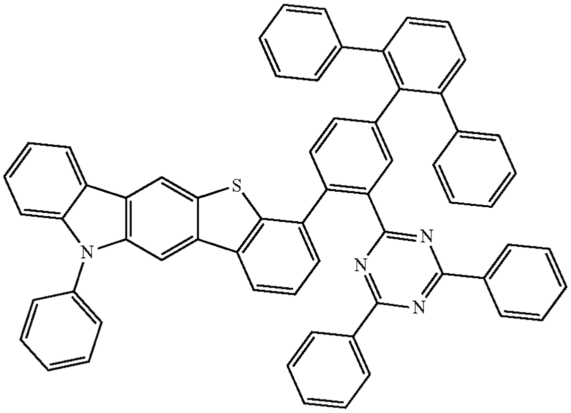
274
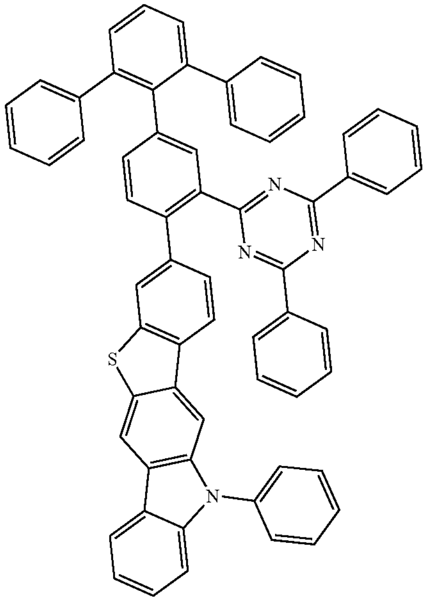
-continued
275
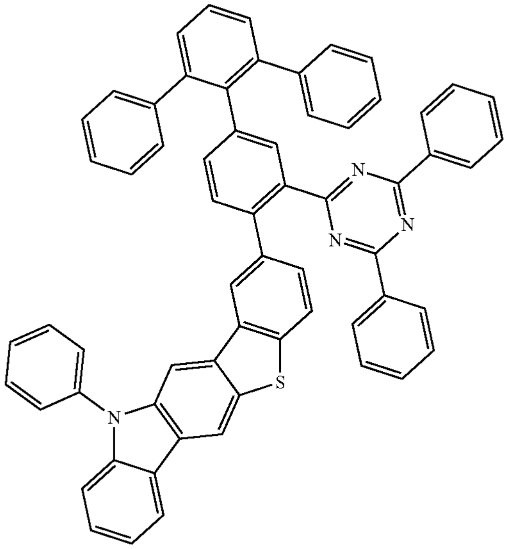
276
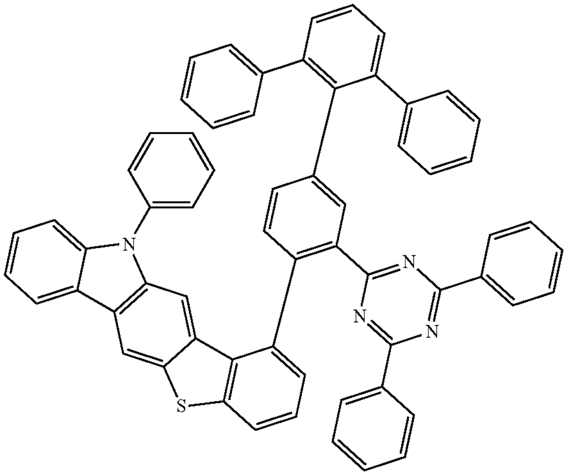

-continued
277
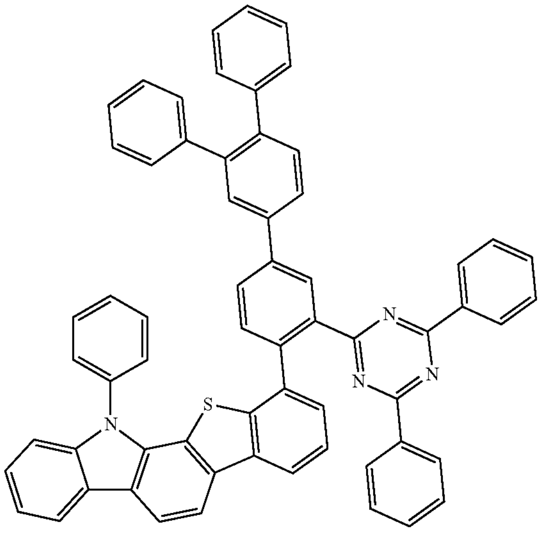
278
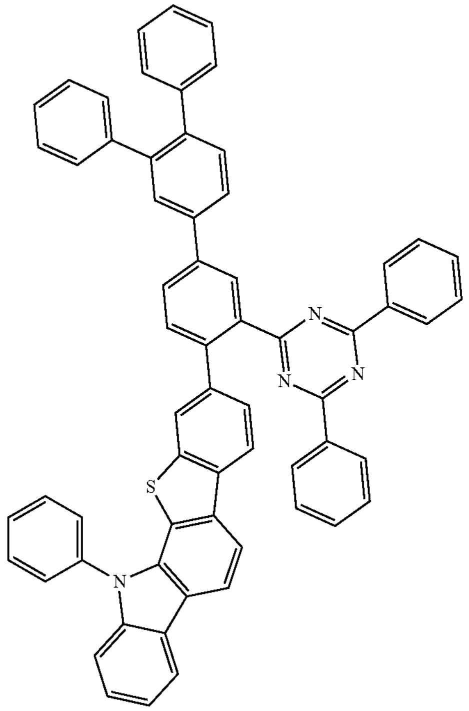
279
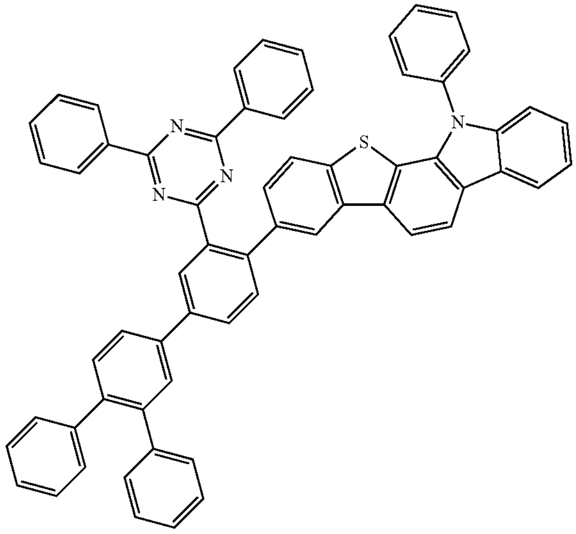
280
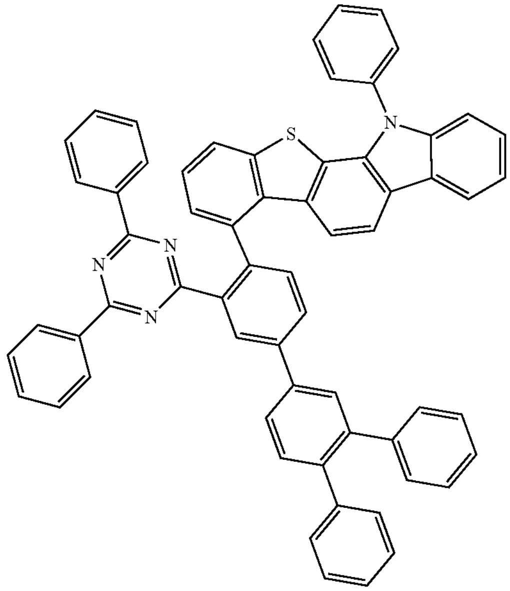
281
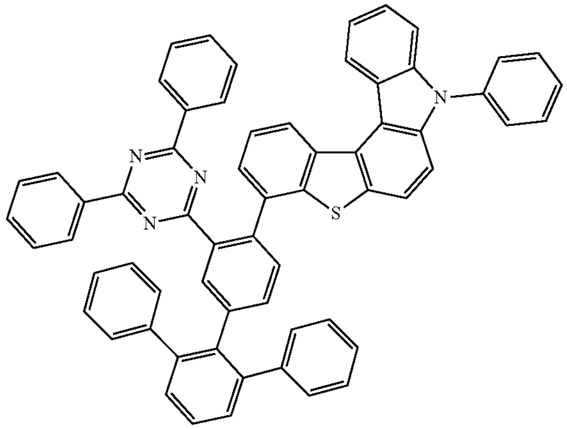

-continued
282
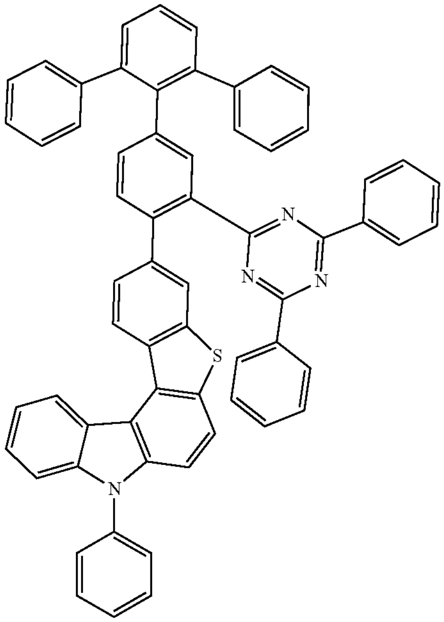
283
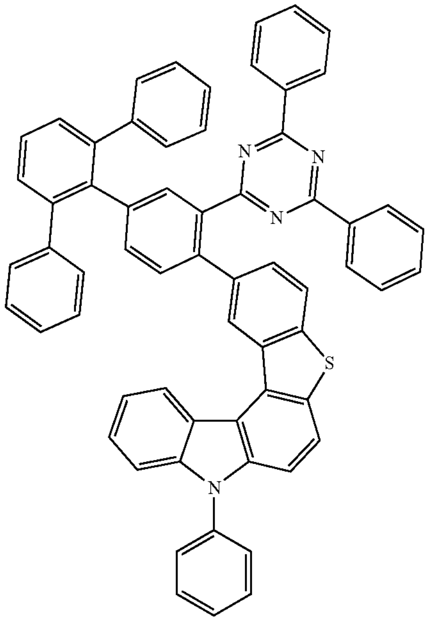
-continued
284
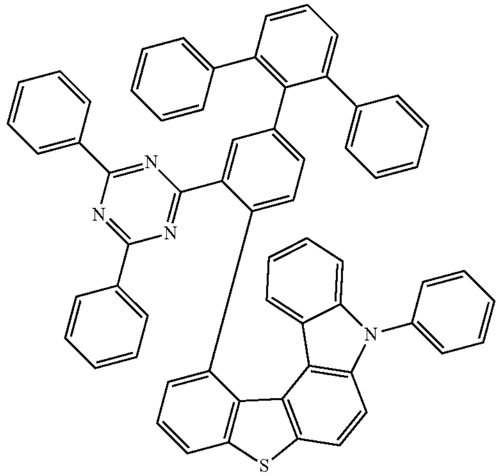
285
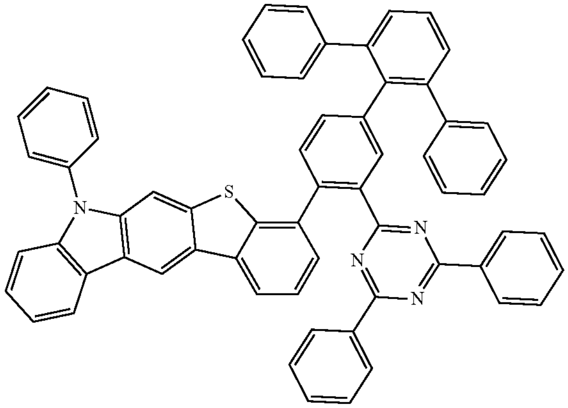
286
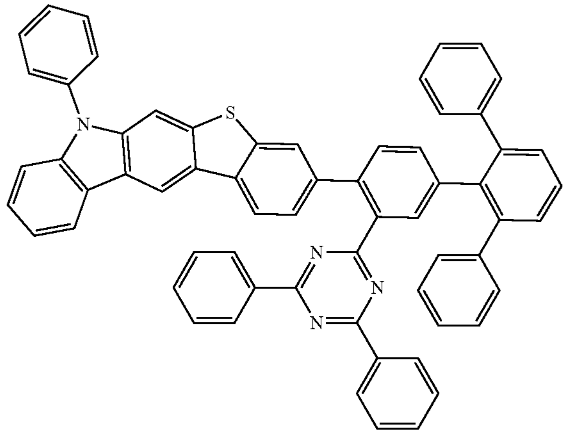

-continued
287
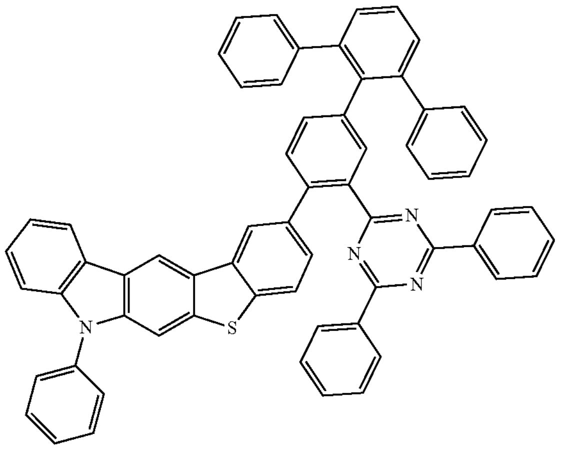
288
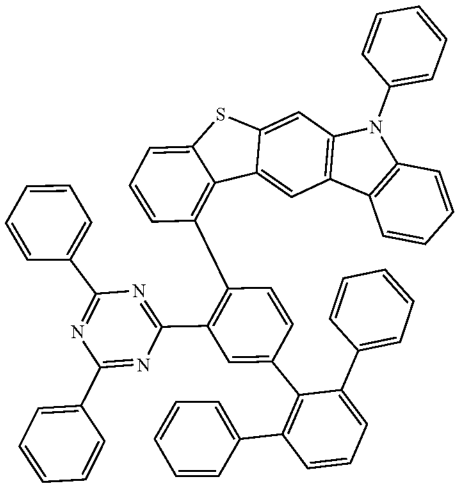
289
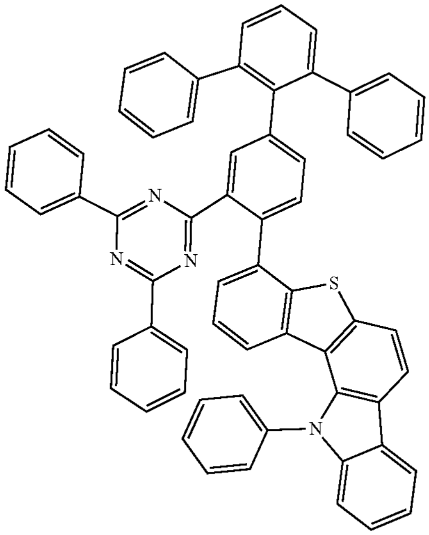
-continued
290
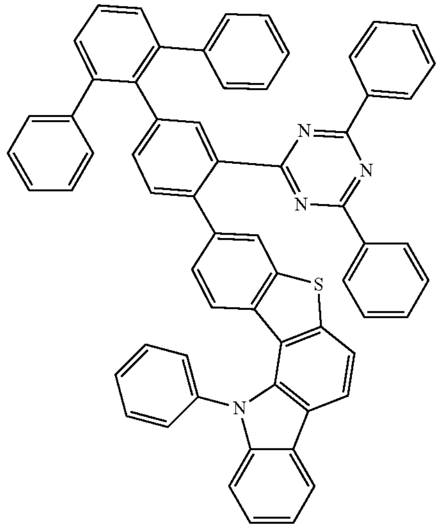
291
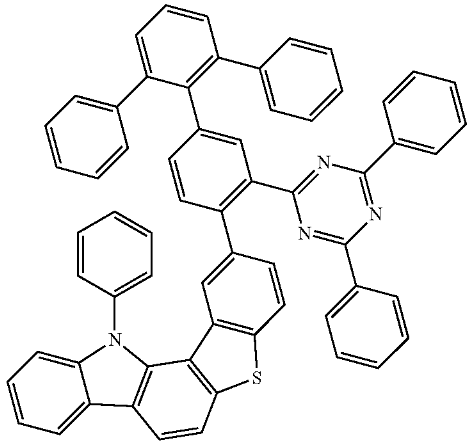
292
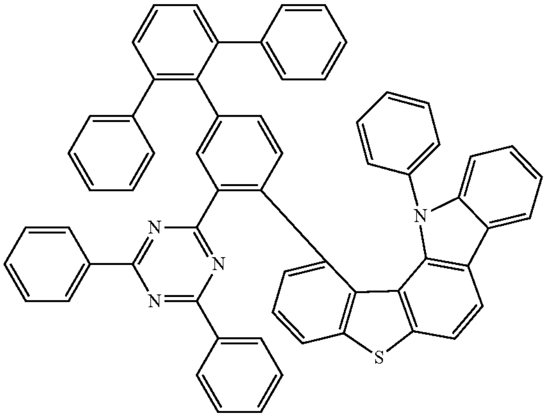

-continued
293
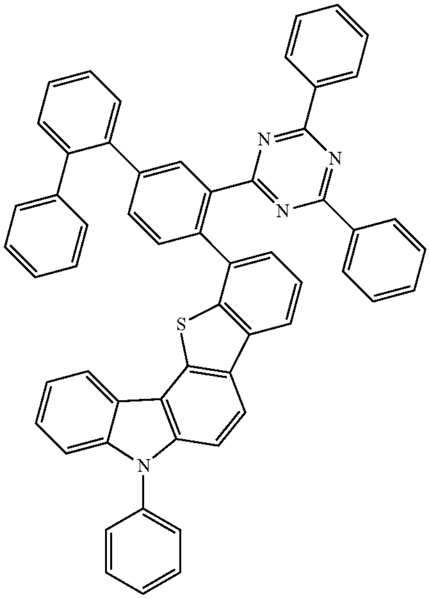
294
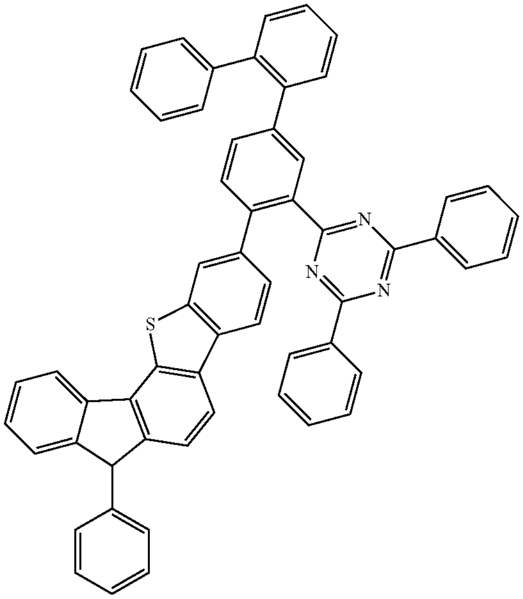
295
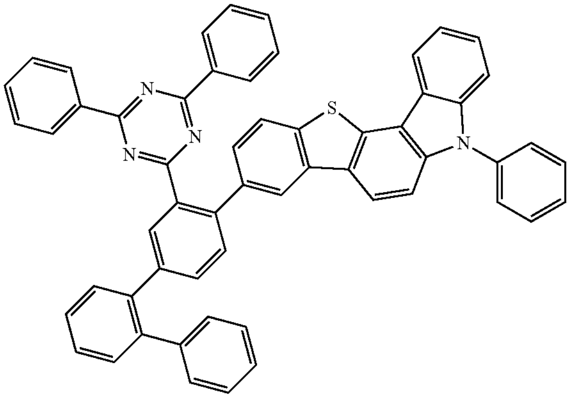
-continued
296
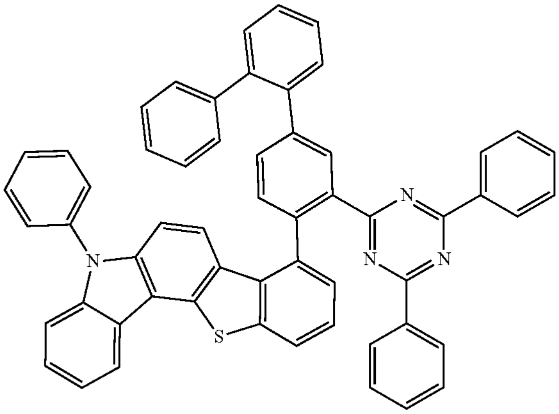
297
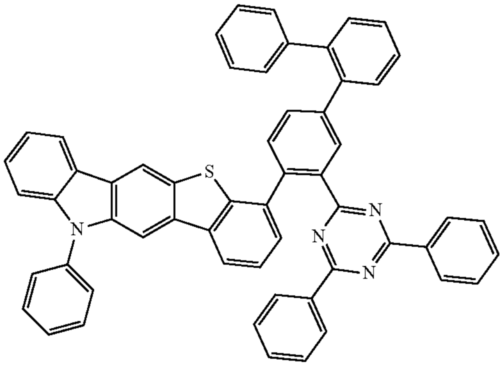
298
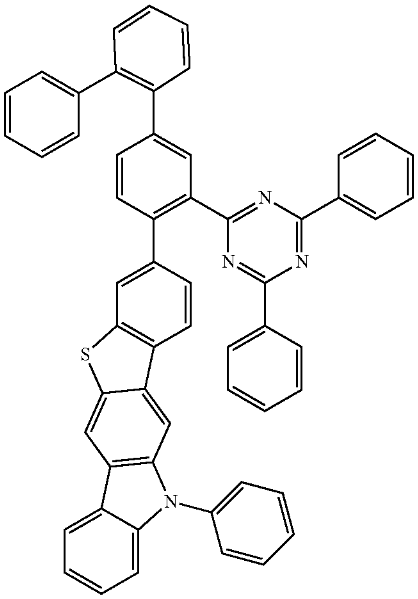

-continued
299
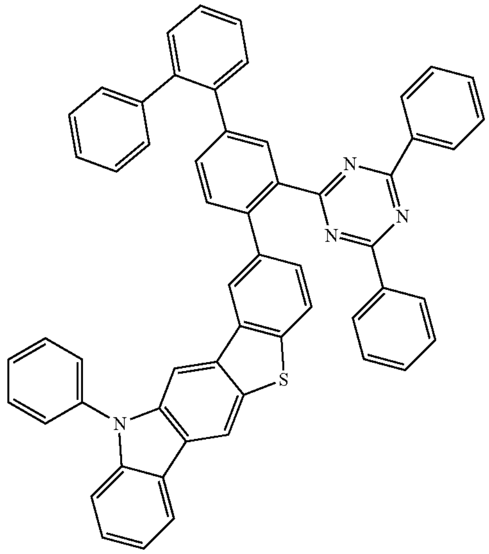
300
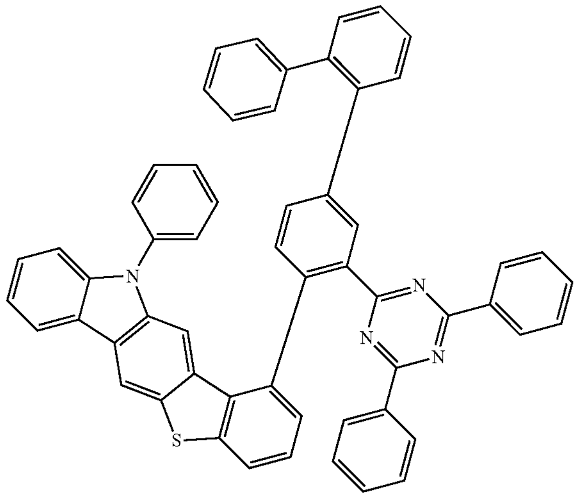
301
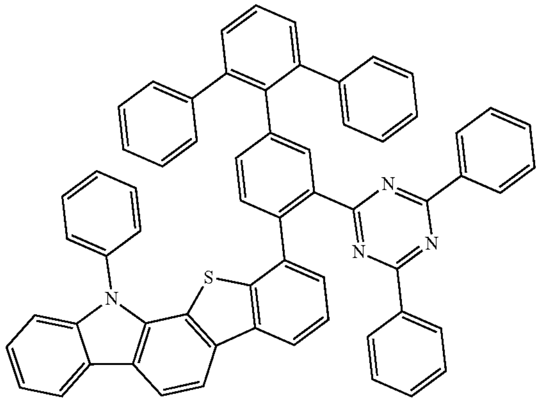
-continued
302
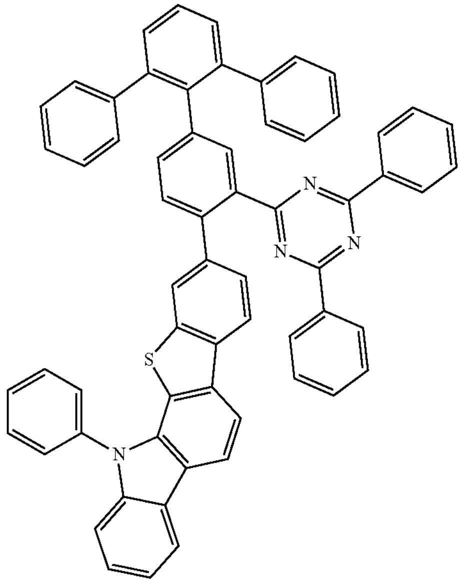
303
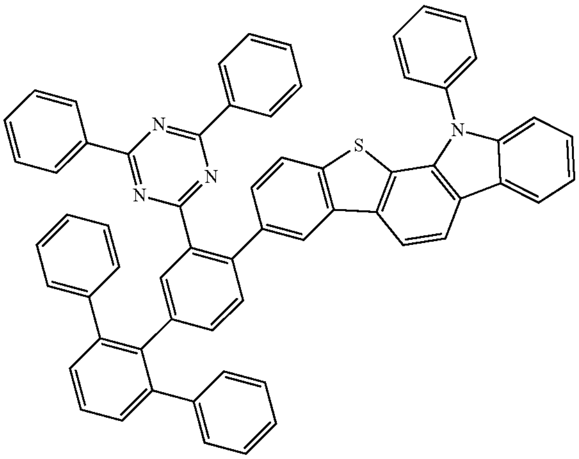
304
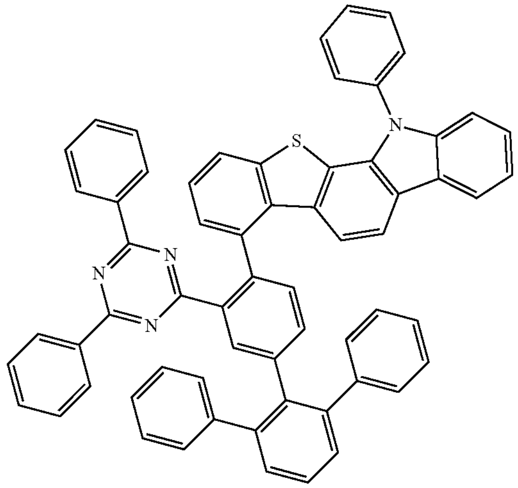

305
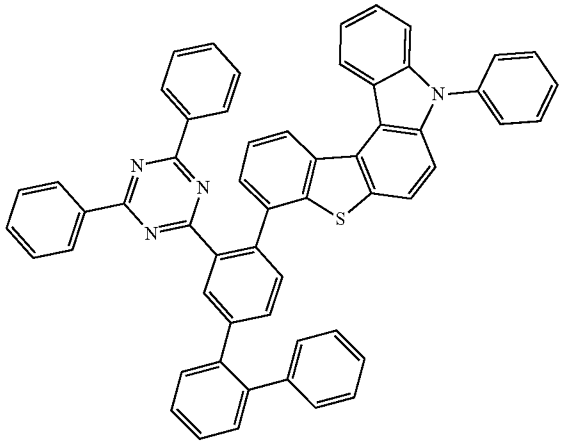
306
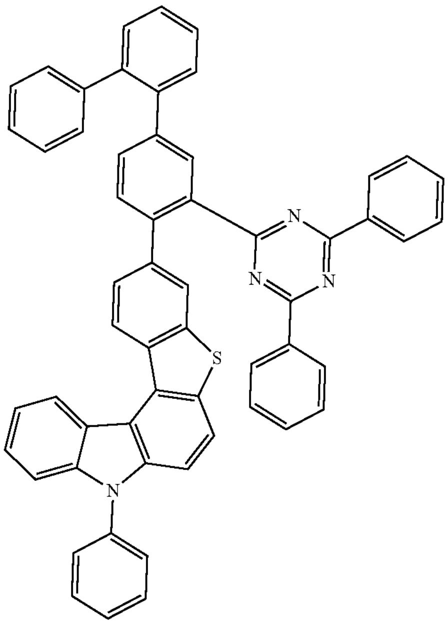
307
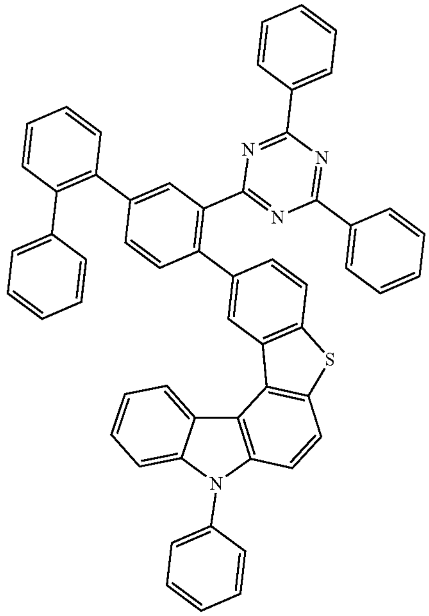
308
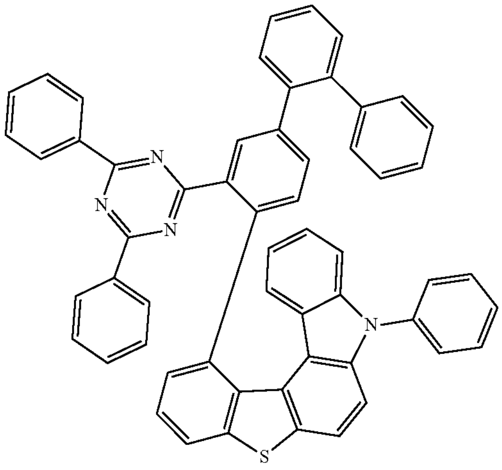
309
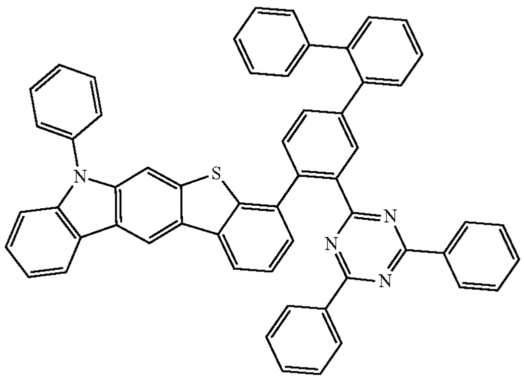

-continued
310
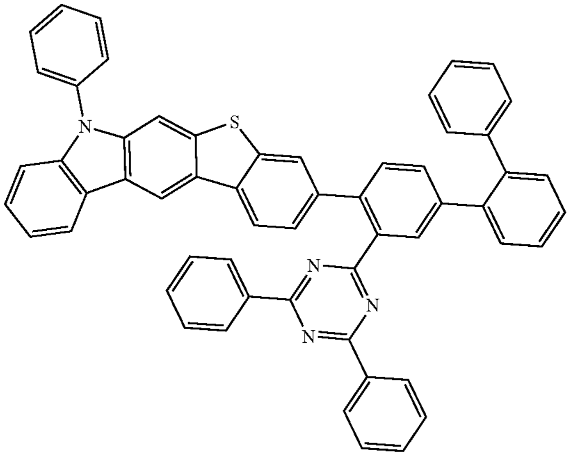
311
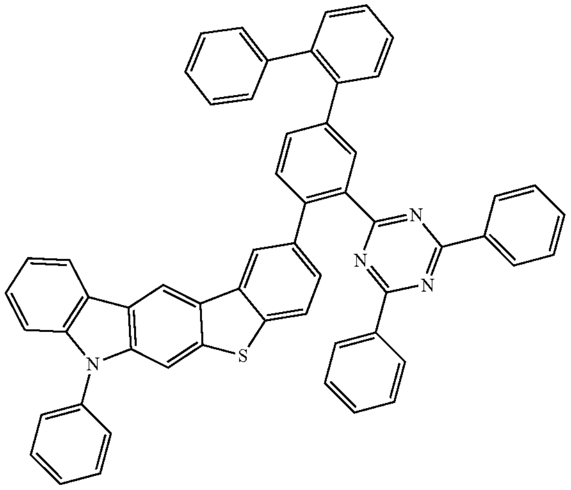
312
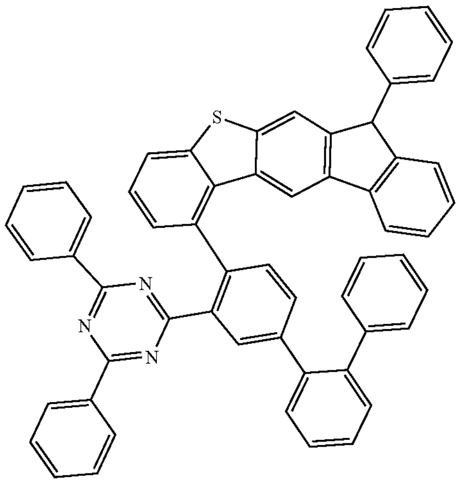
-continued
313
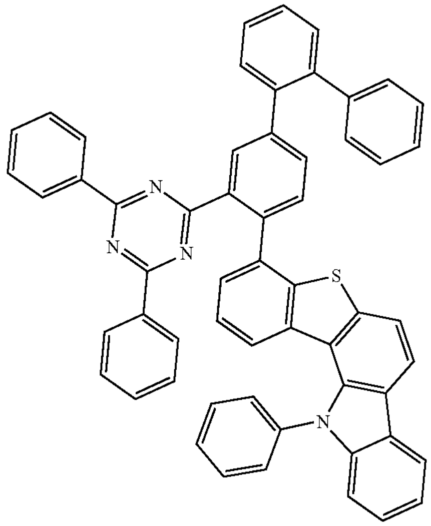
314
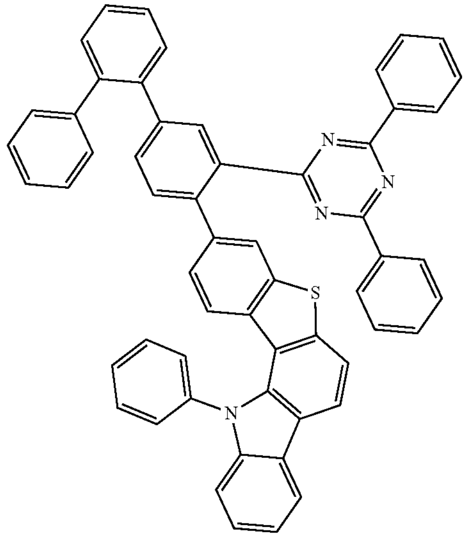
315
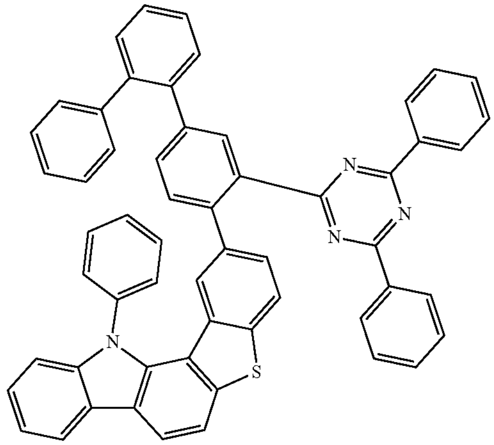

-continued
316
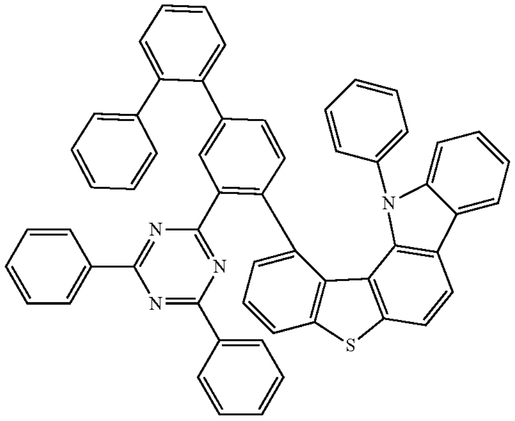
317
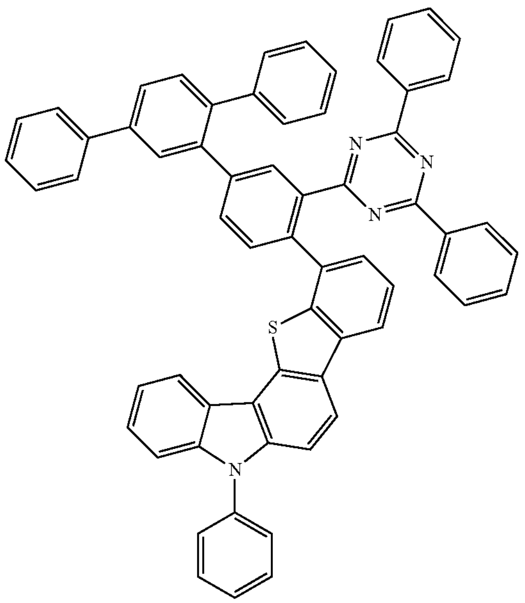
-continued
318
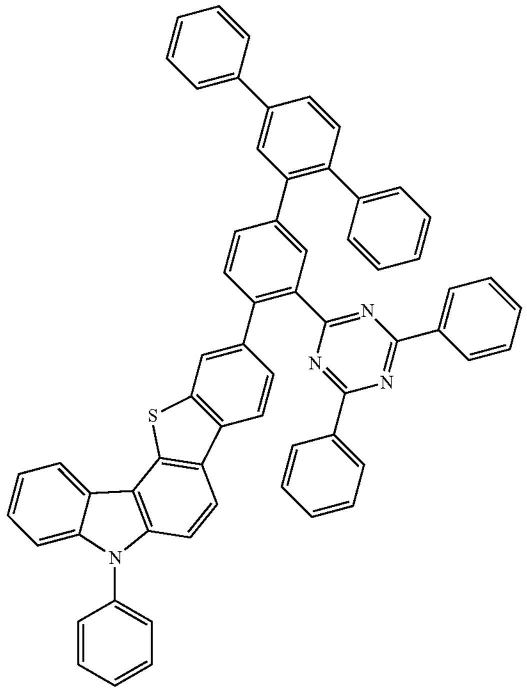
319
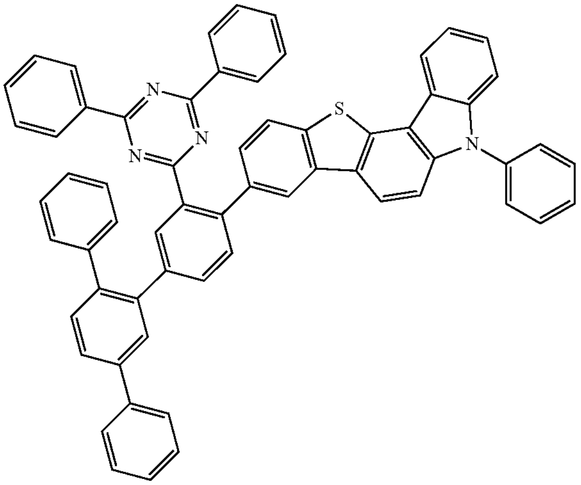

320
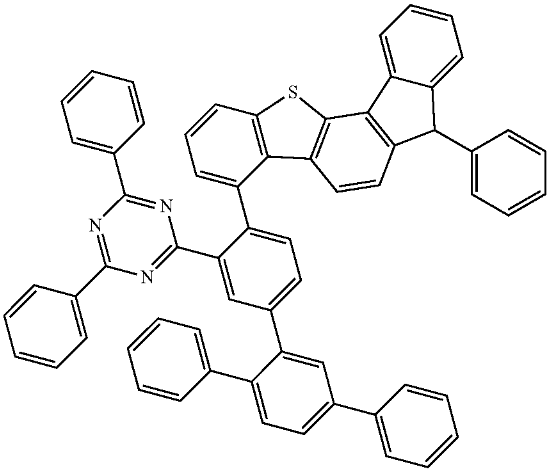
321
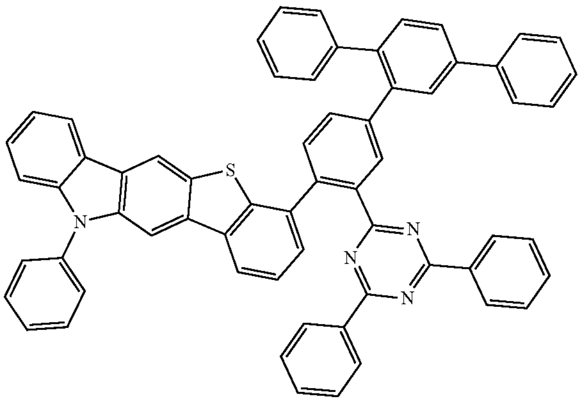
322
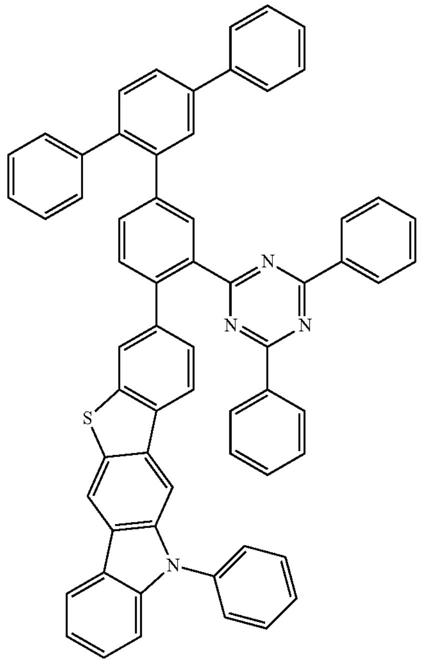
323
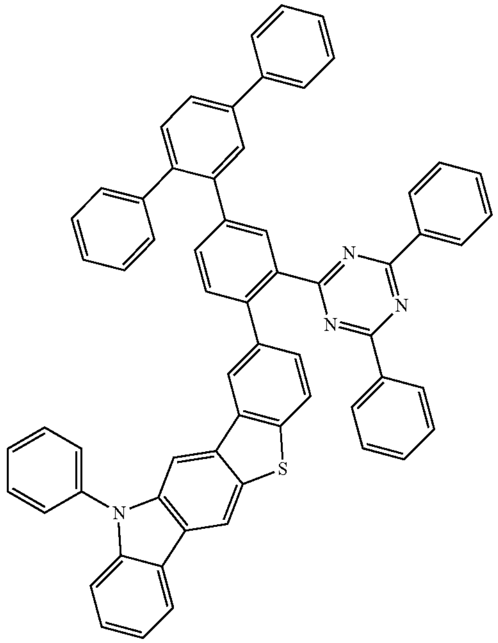
324
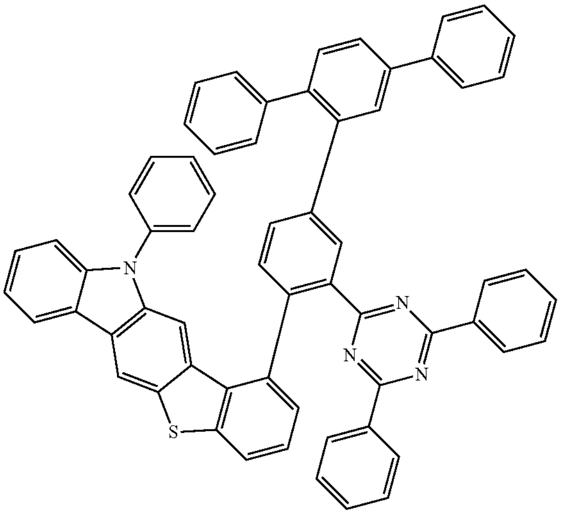
325
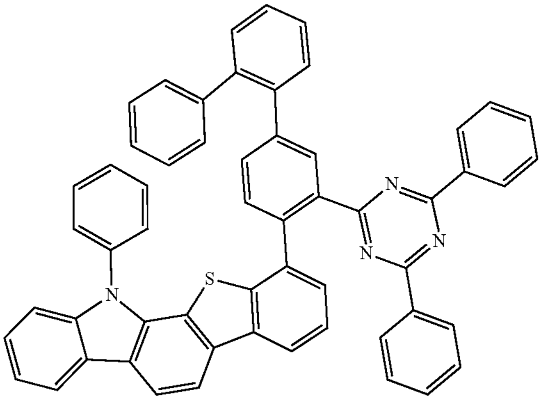

326
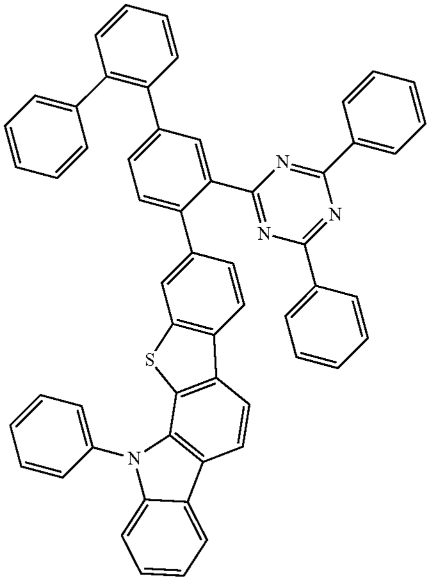
327
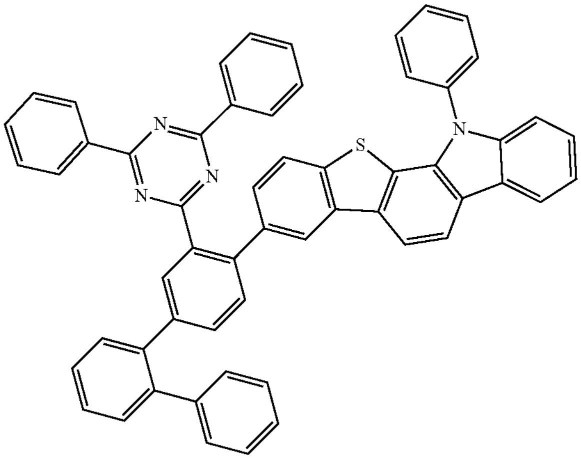
328
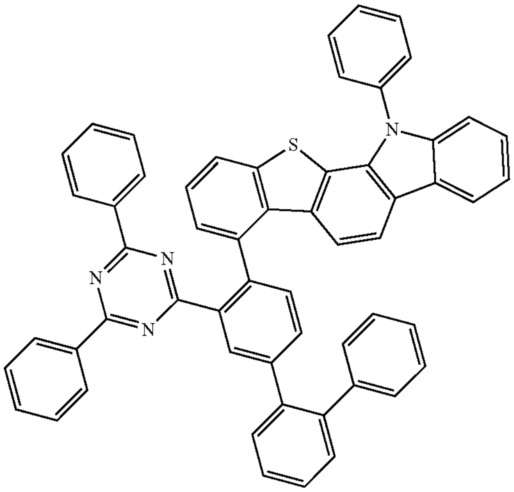
329
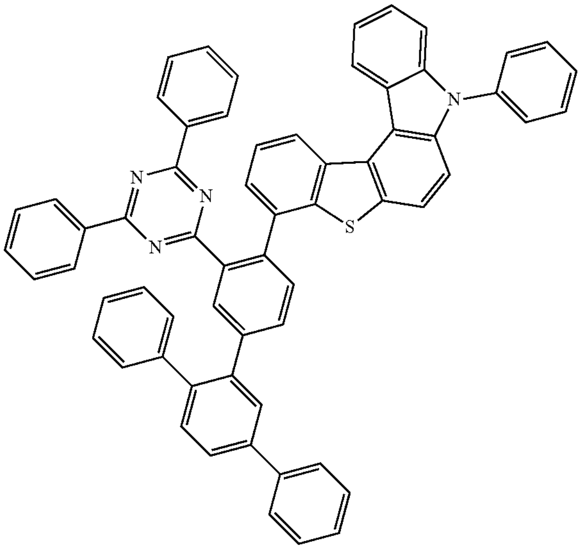
330
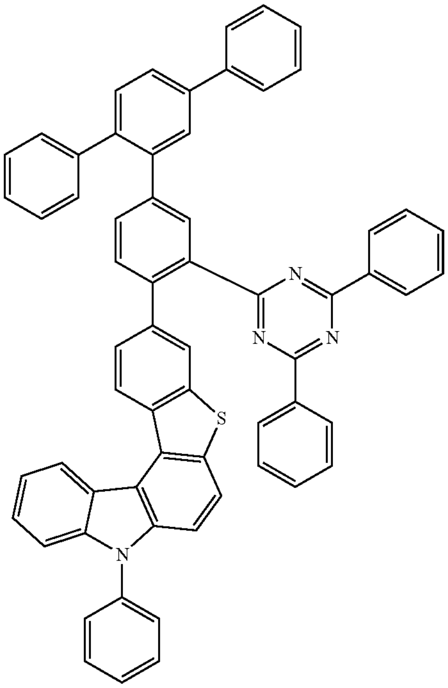

-continued
331
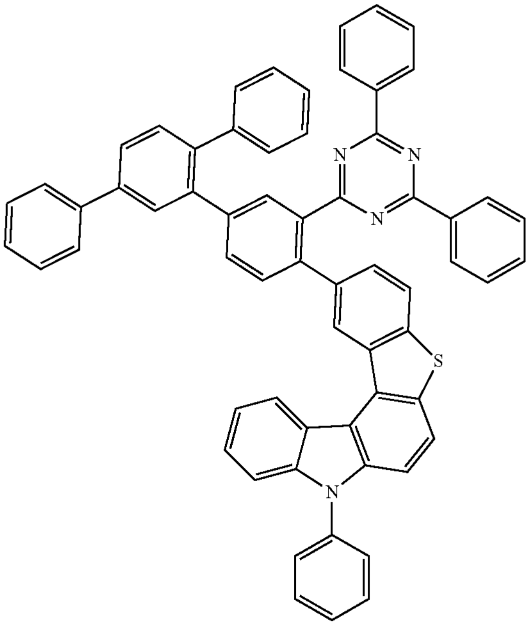
332
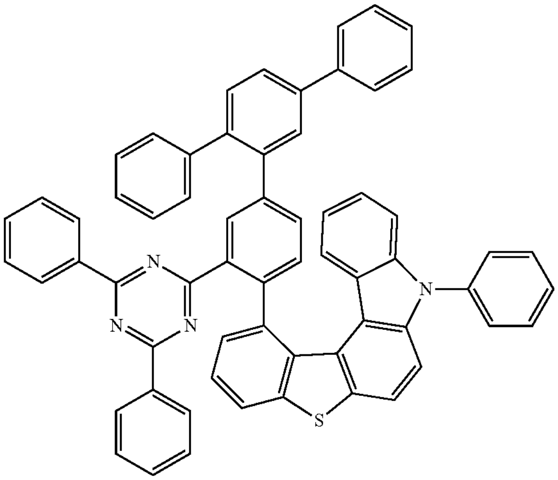
333
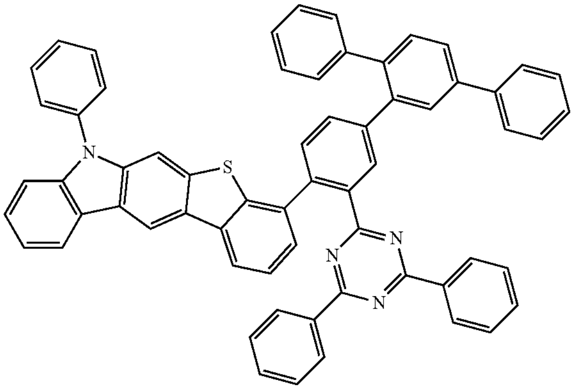
-continued
334
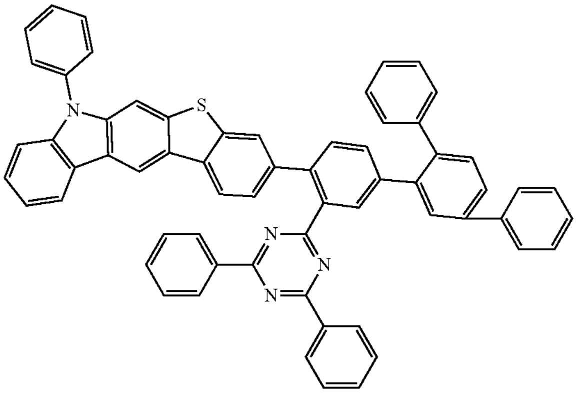
335
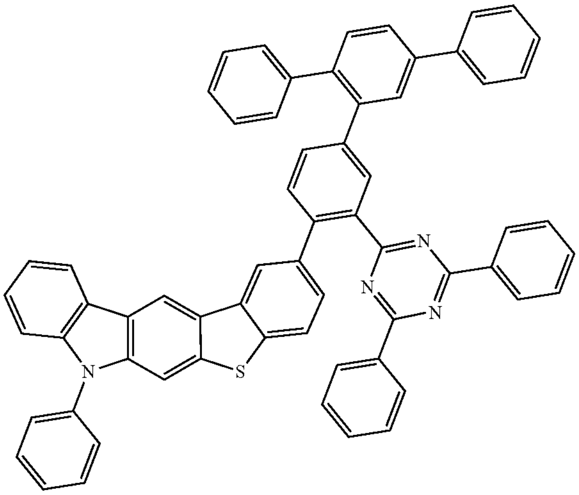
336
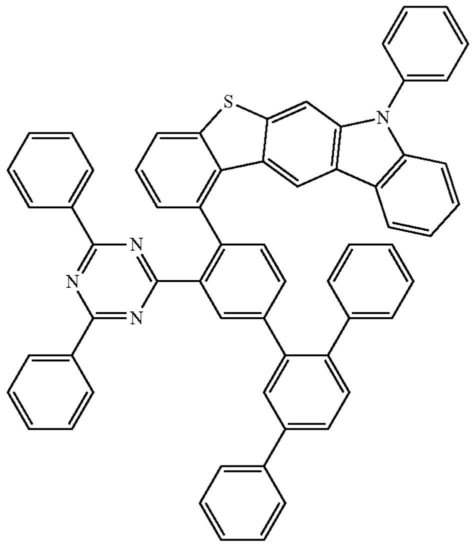

-continued
337
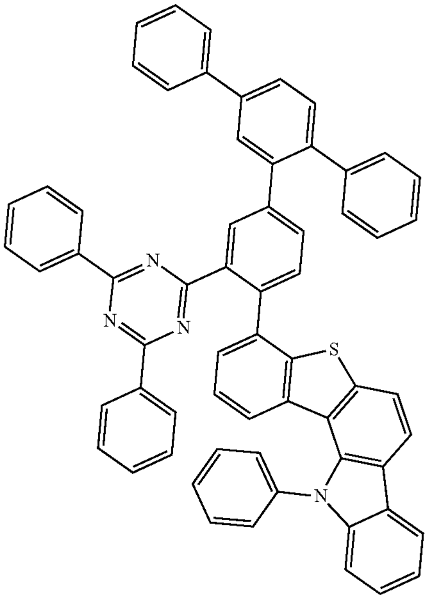
338
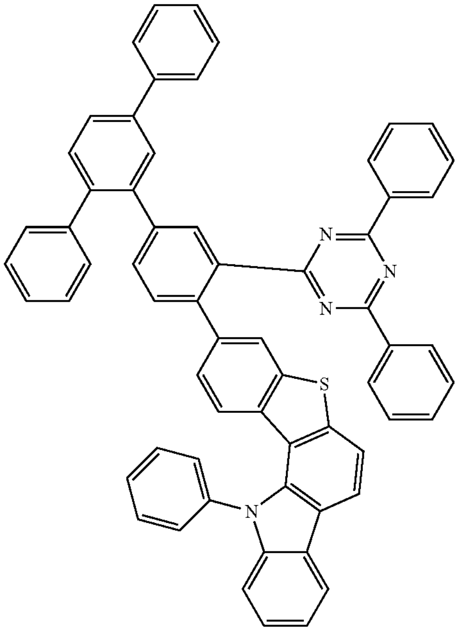
-continued
339
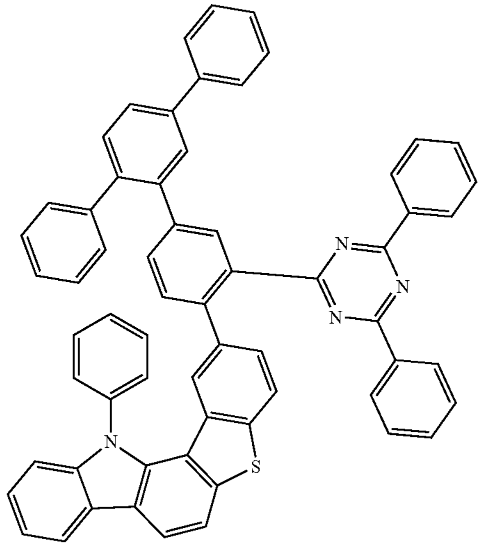
340
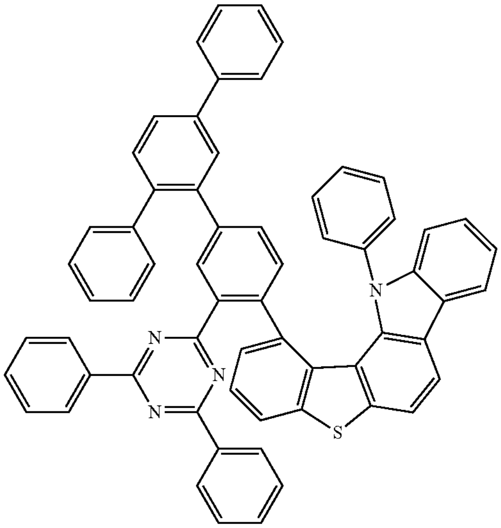
341
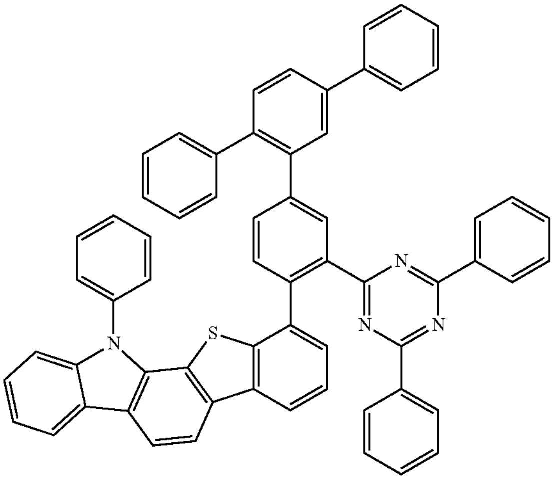

-continued
342
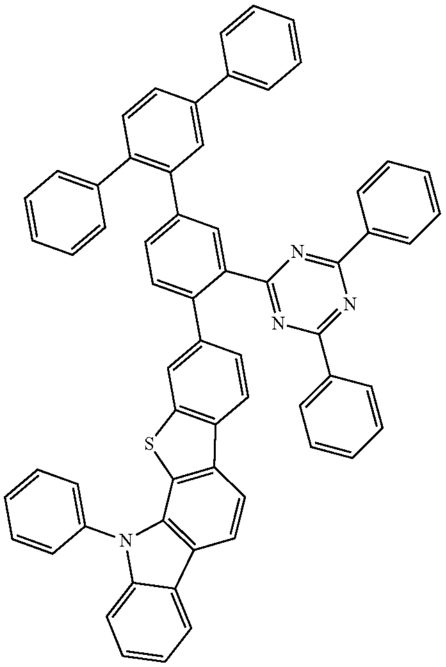
343
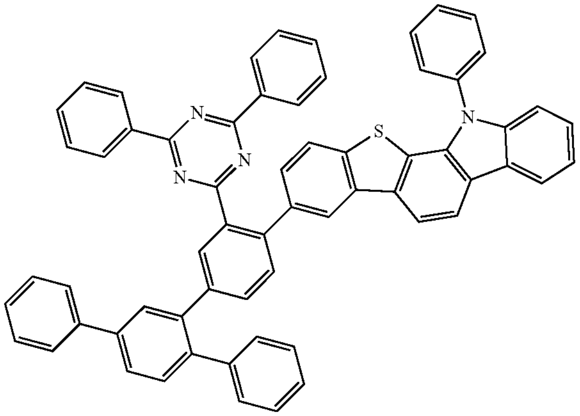
-continued
344
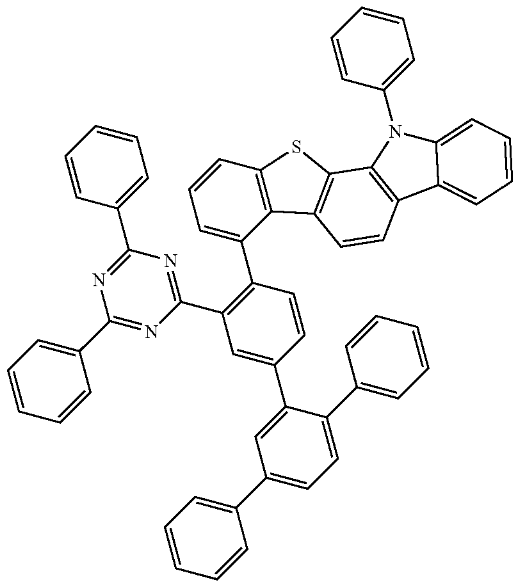
345
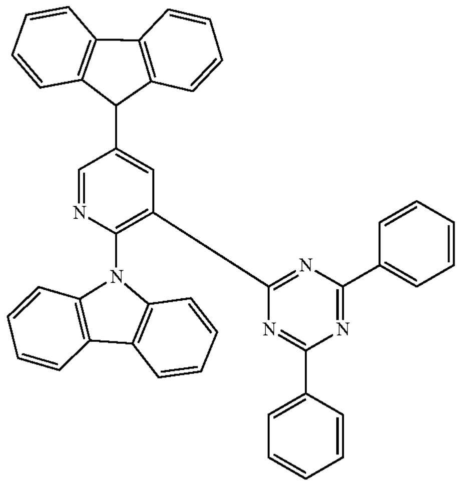
346
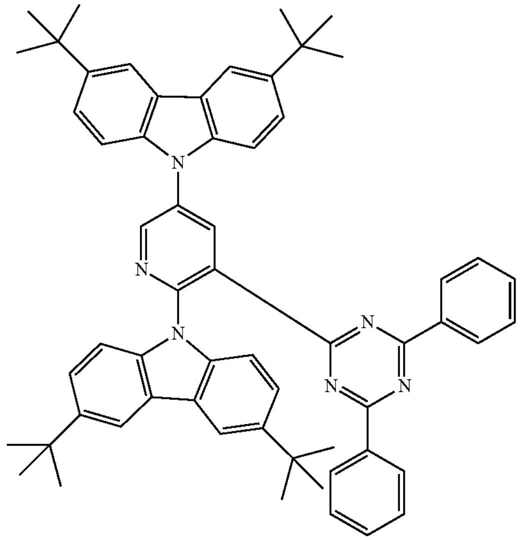

-continued
347
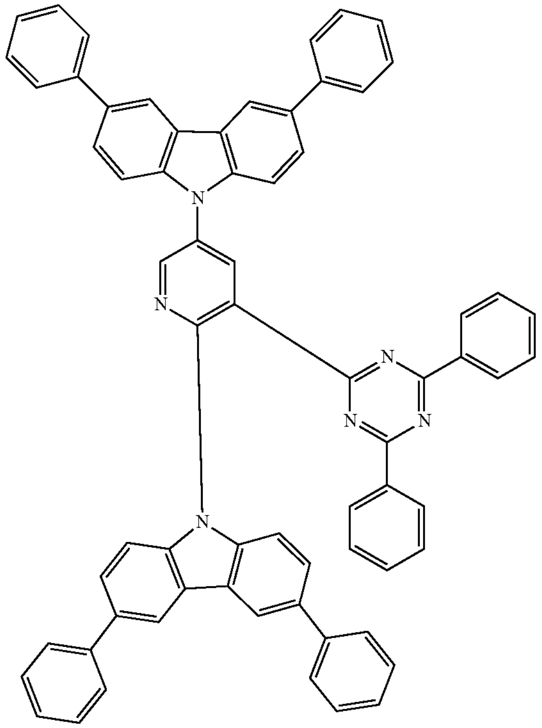
348
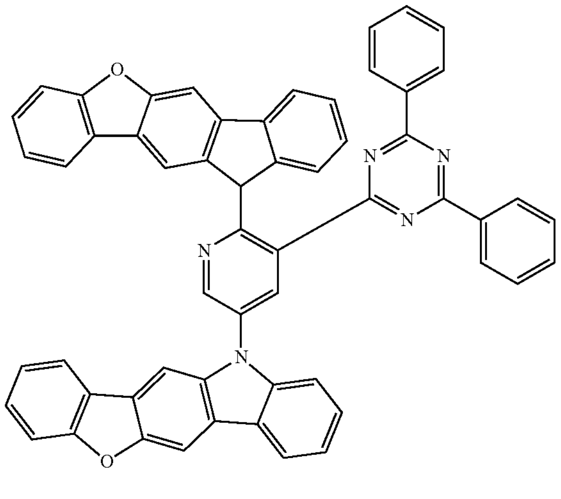
-continued
349
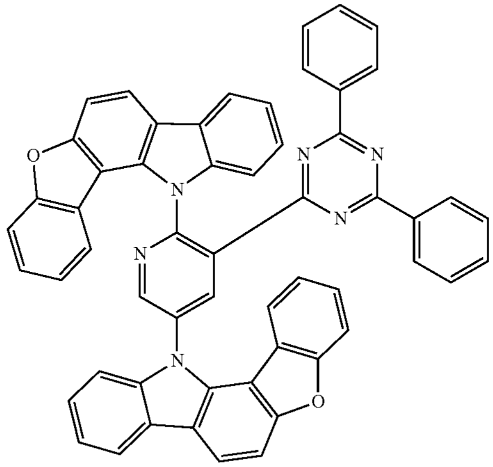
350
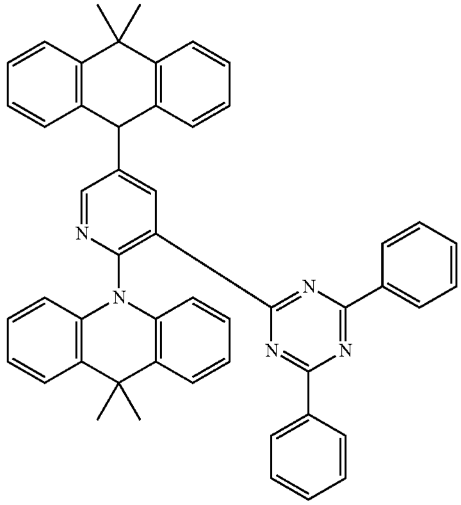
351
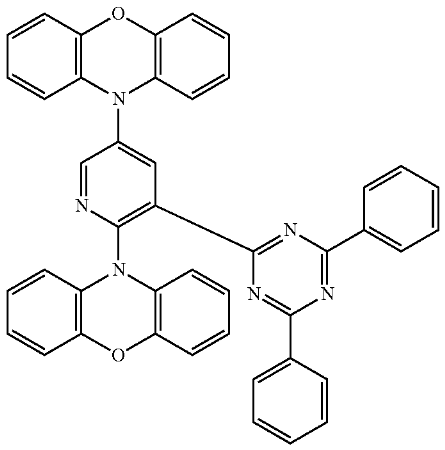

352
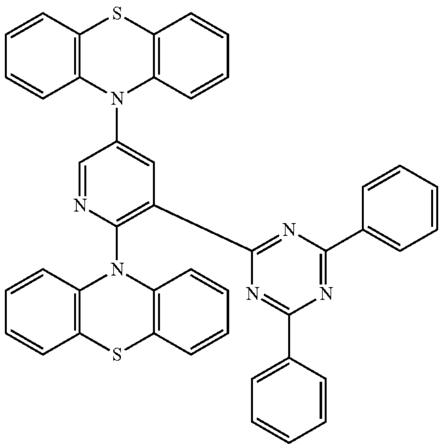
353
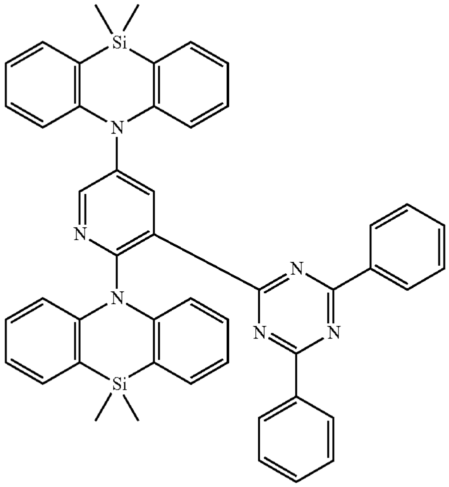
354
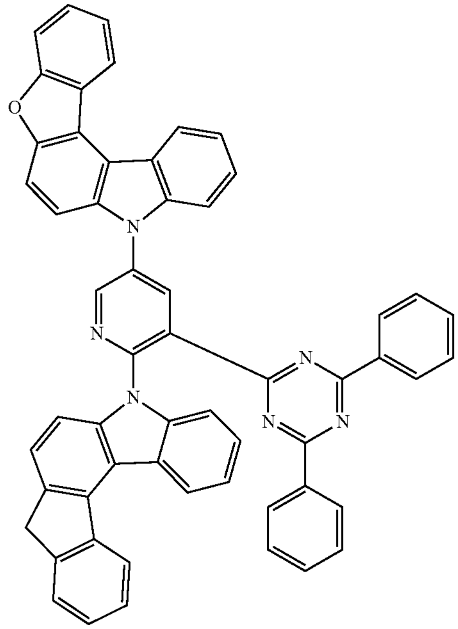
355
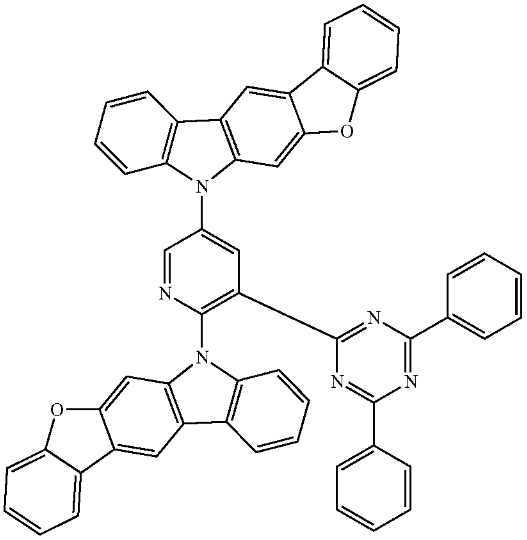
356
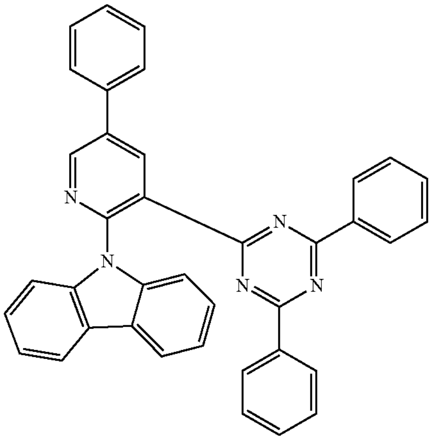
357
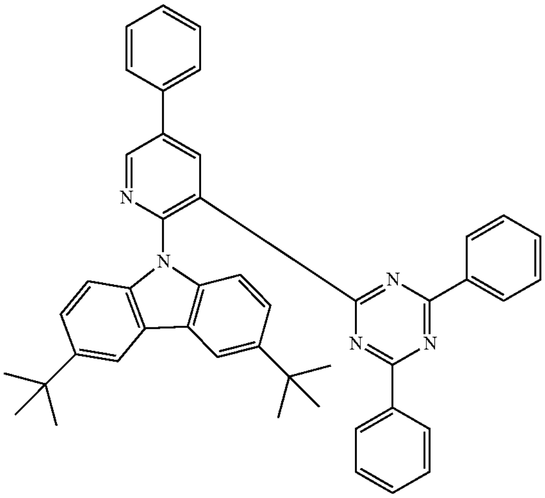

-continued
358
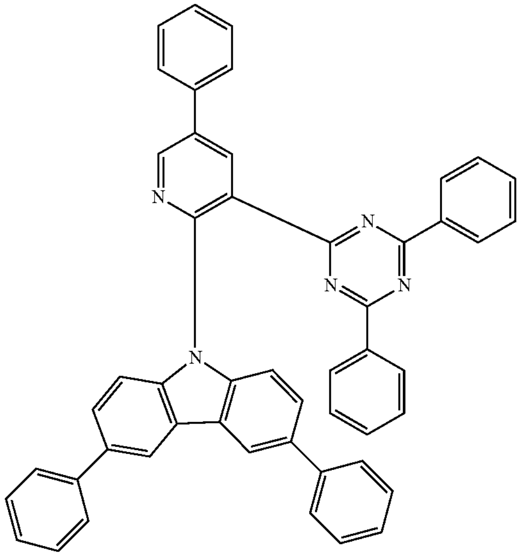
359
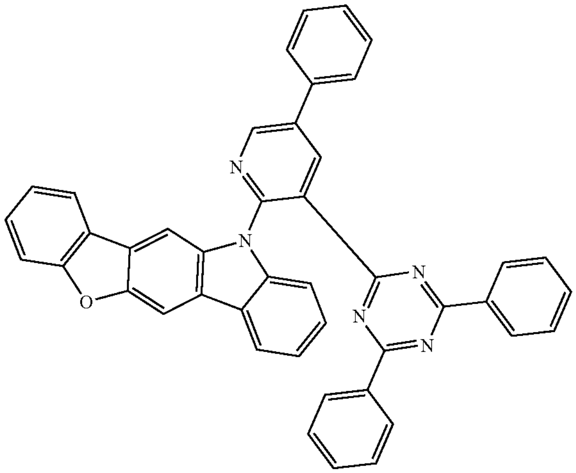
360
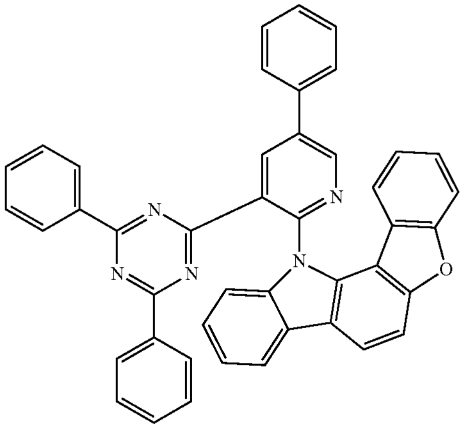
361
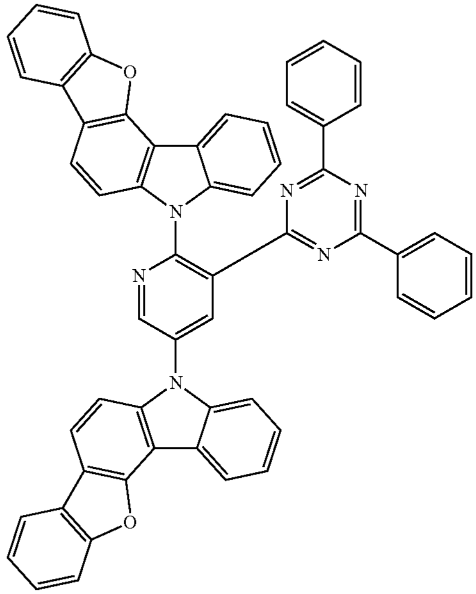
362
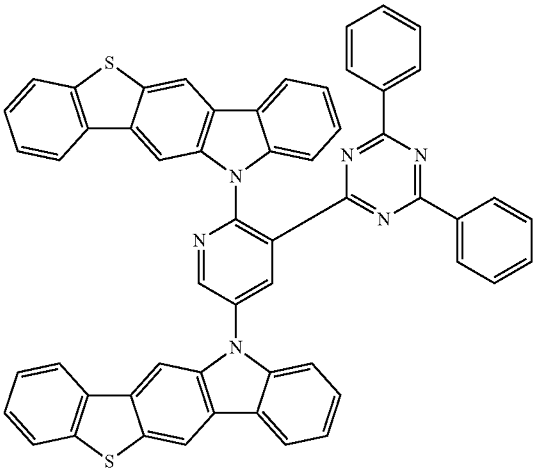
363
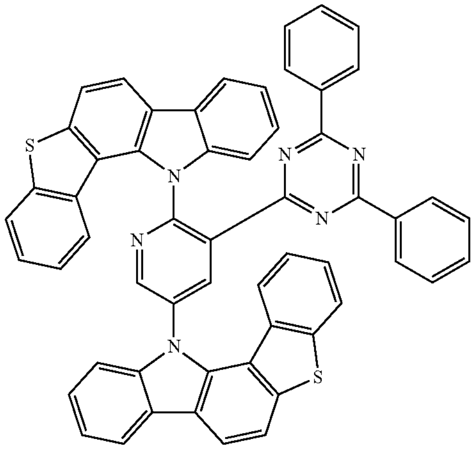

-continued
364
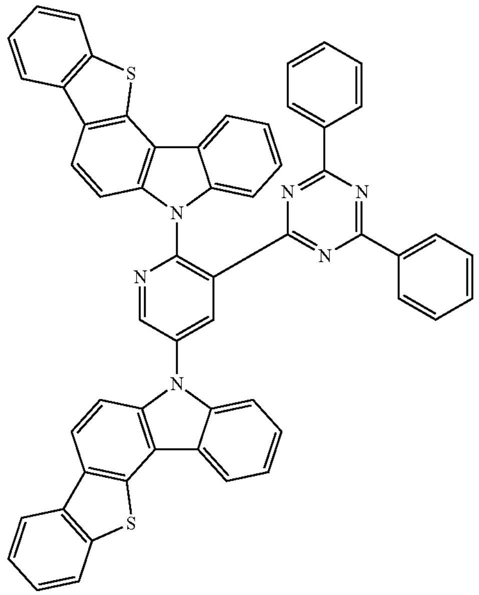
365
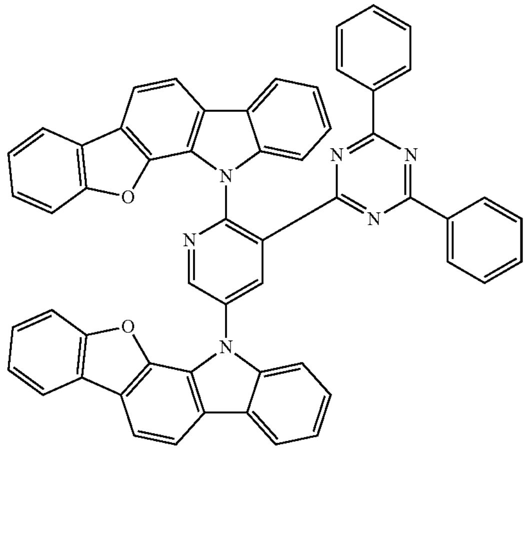
-continued
366
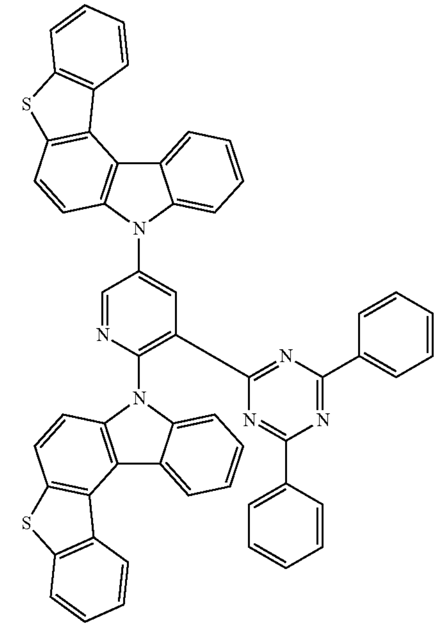
367
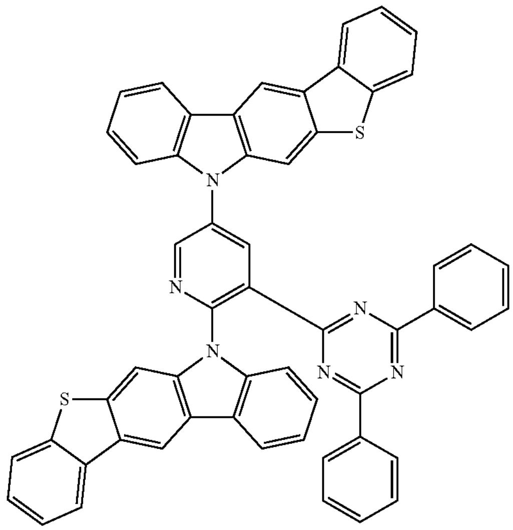
368
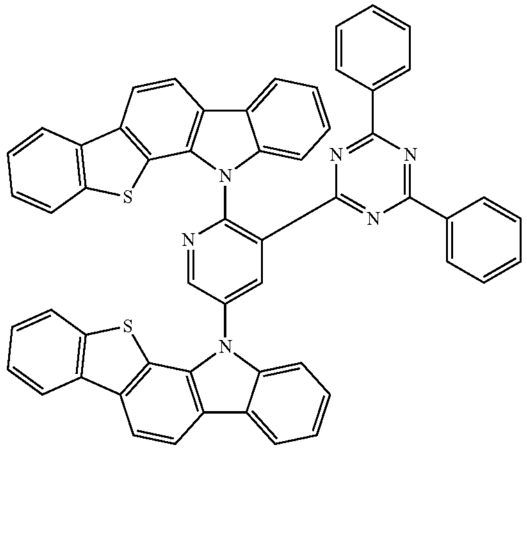

-continued
369
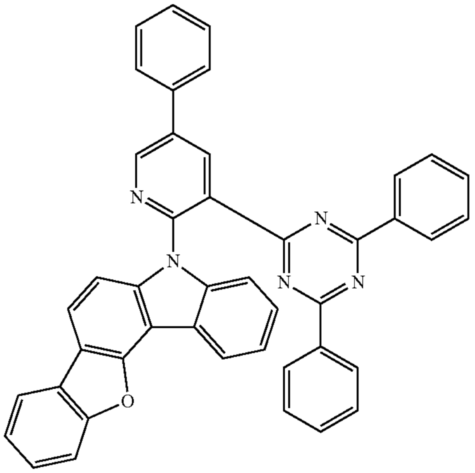
370
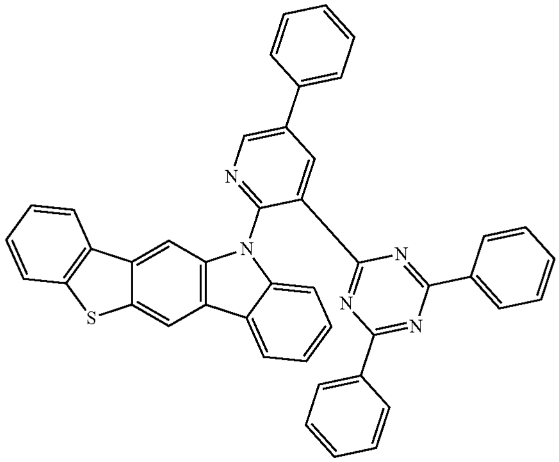
371
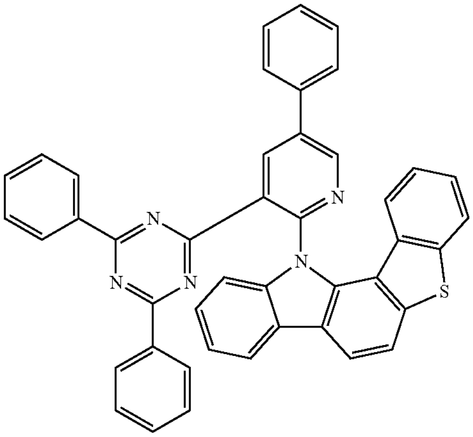
-continued
372
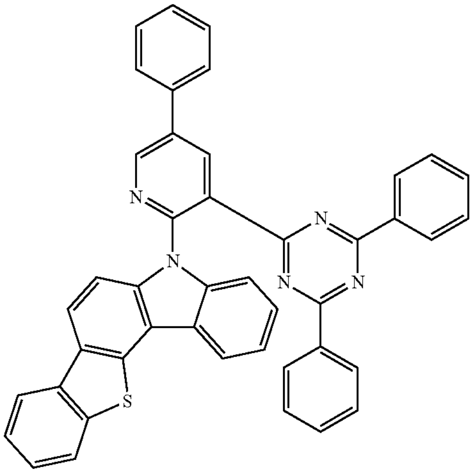
373
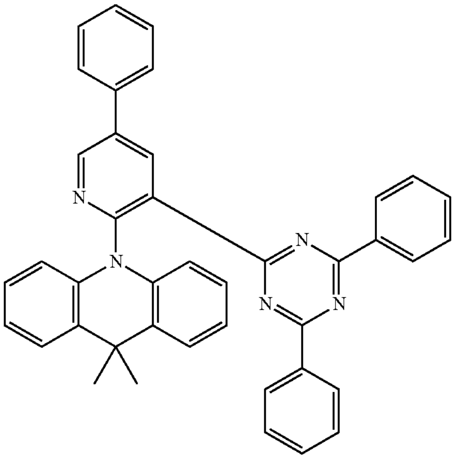
374
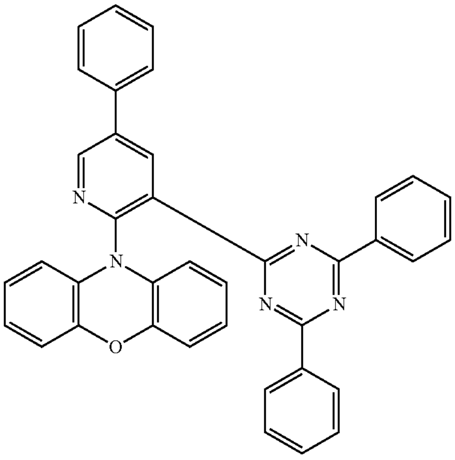

-continued
375
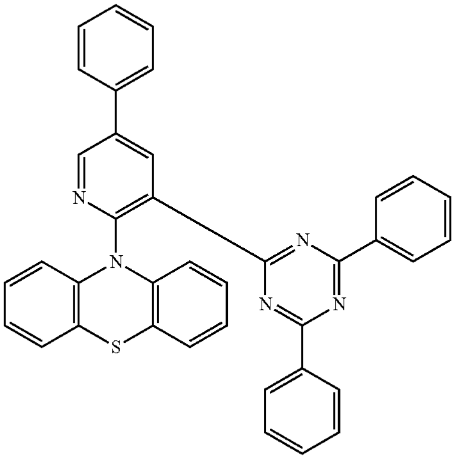
376
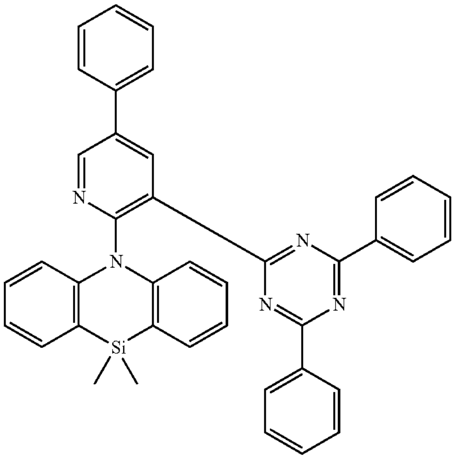
377
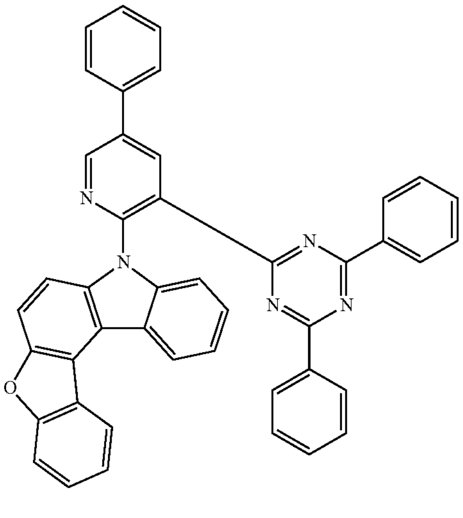
-continued
378
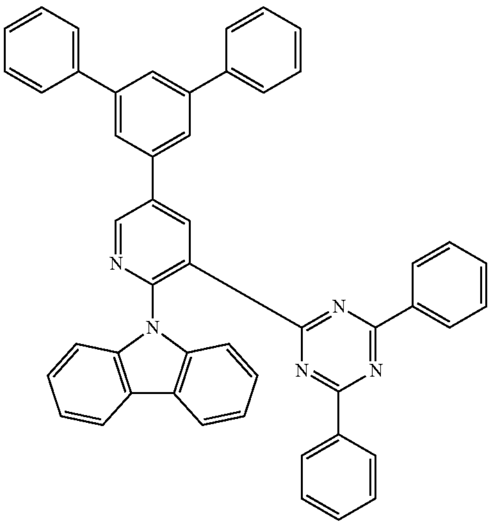
379
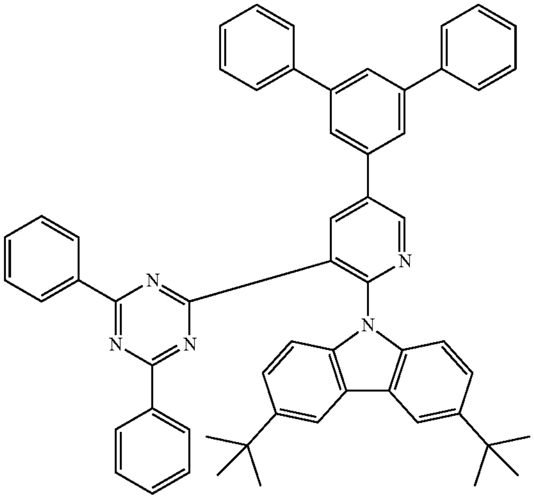
380
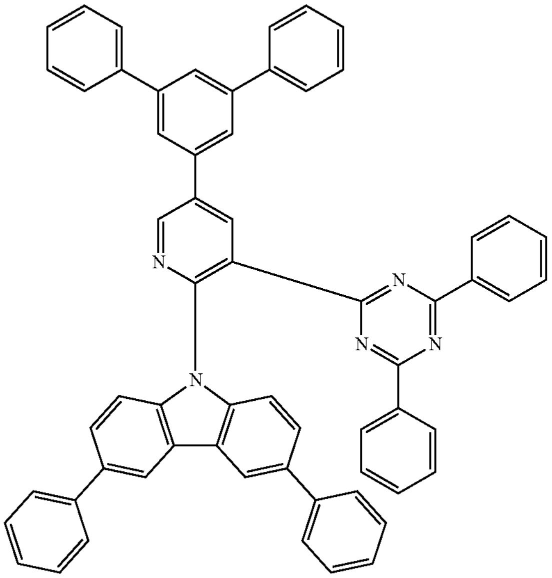

-continued
381
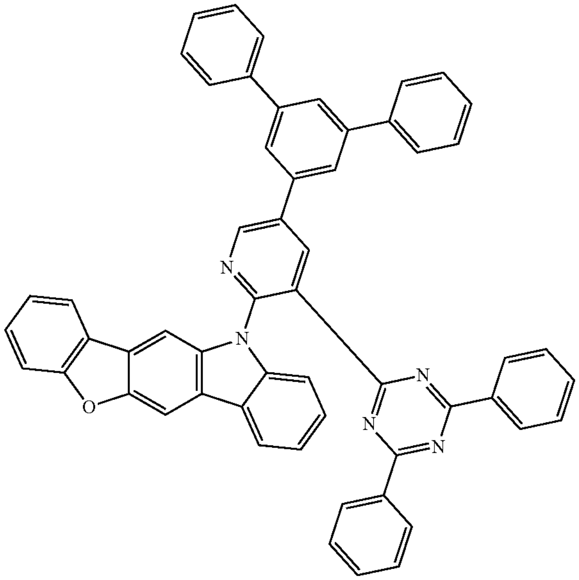
382
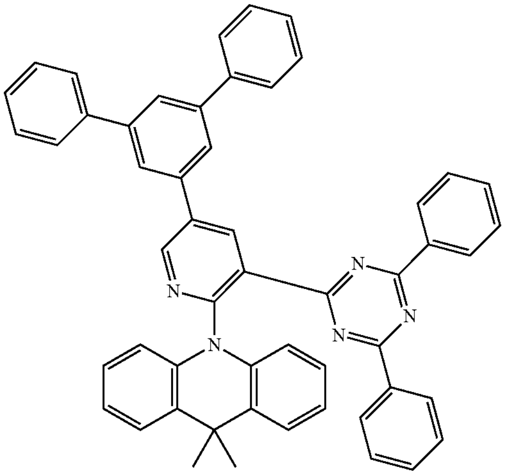
383
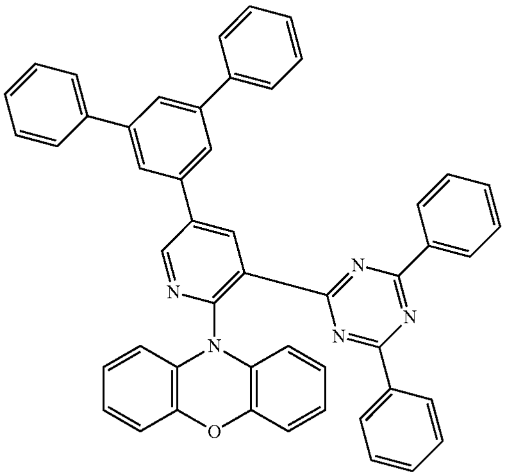
-continued
384
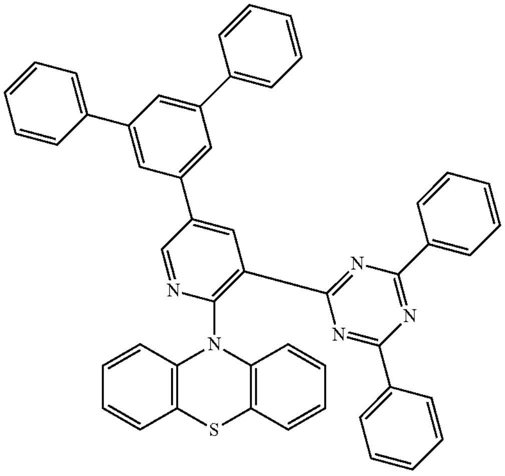
385
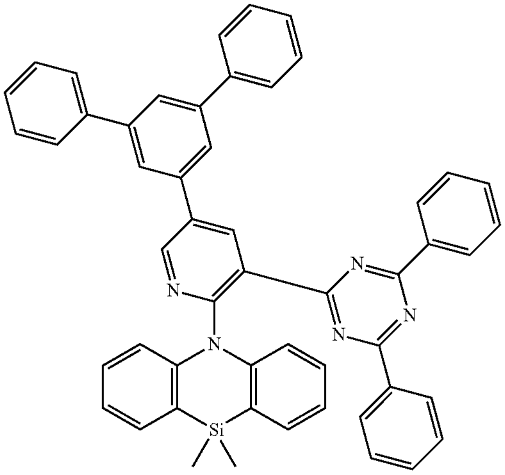
386
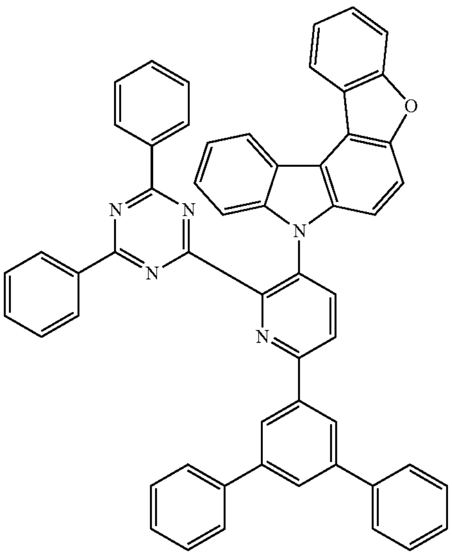

-continued
387
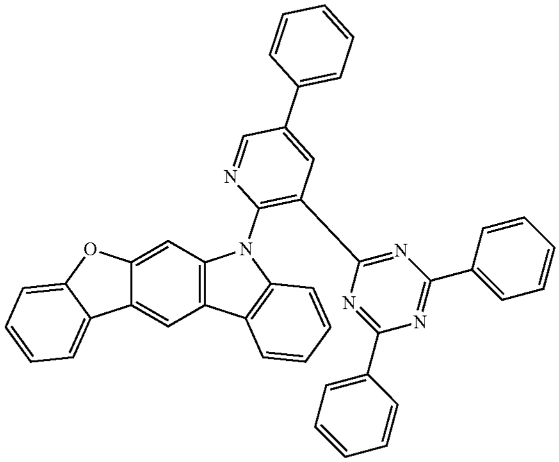
388
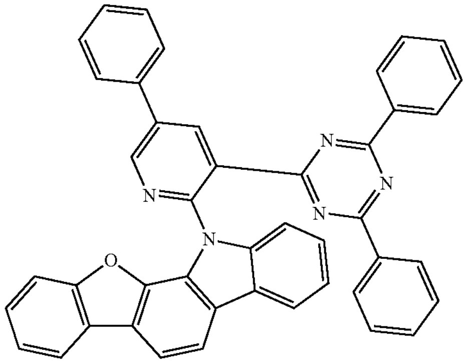
389
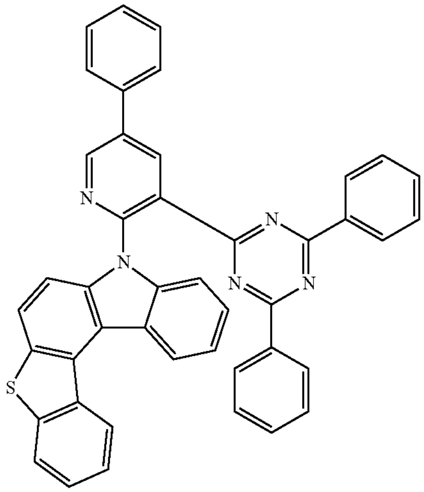
-continued
390
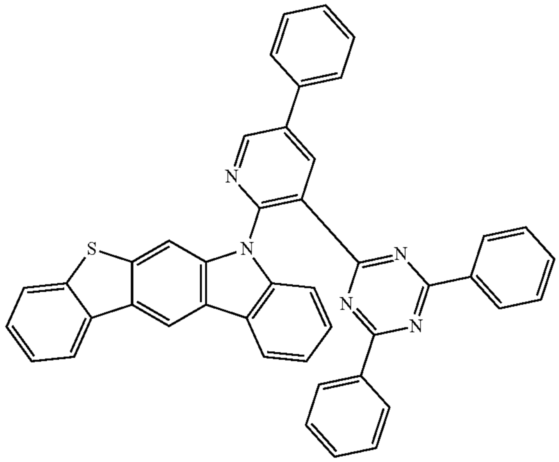
391
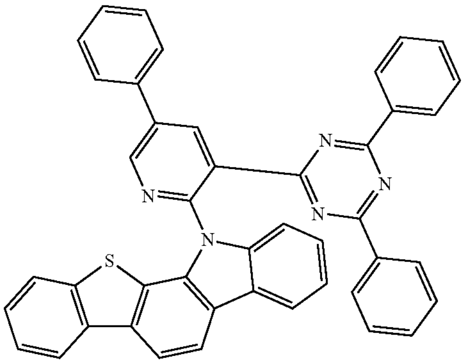
392
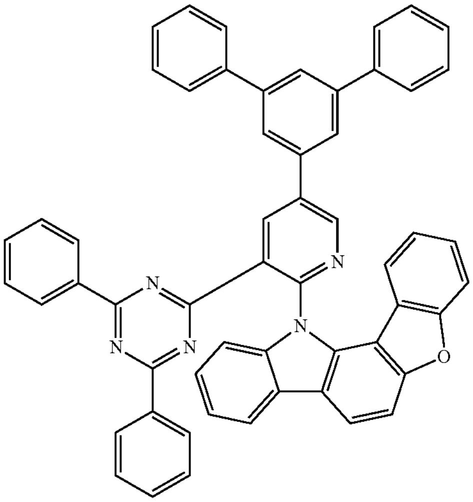

-continued
393
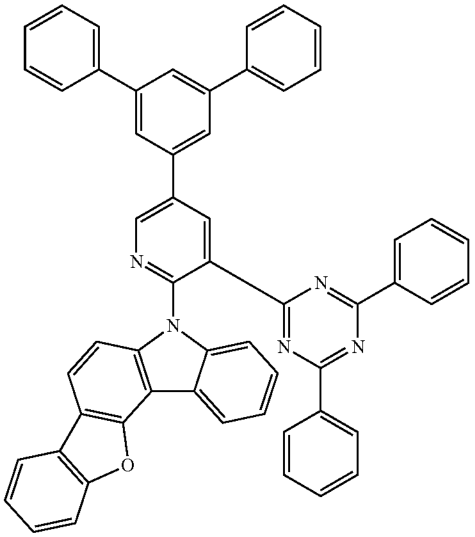
394
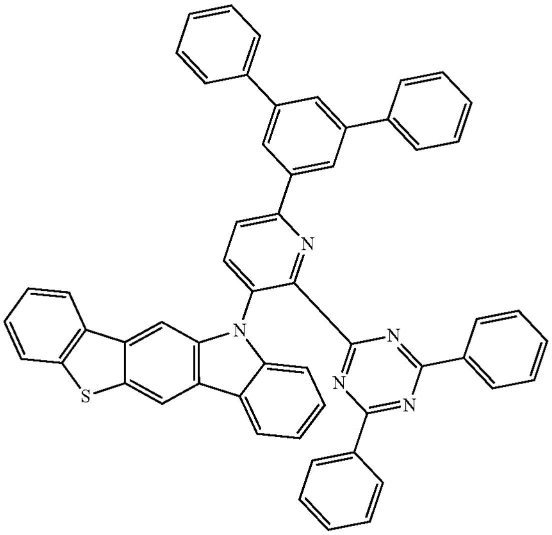
395
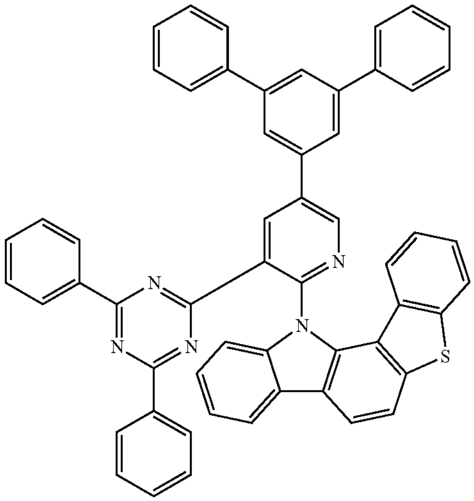
-continued
396
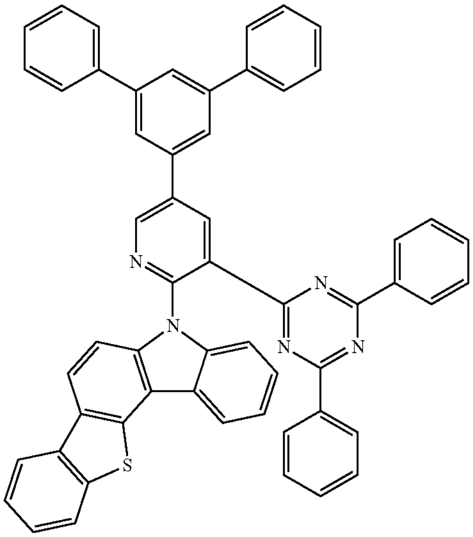
397
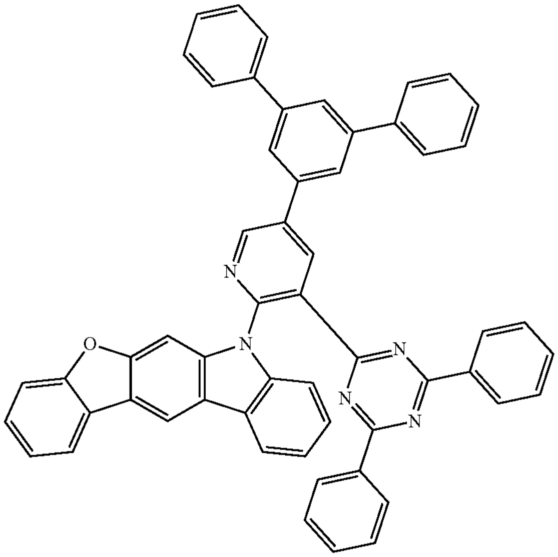
398
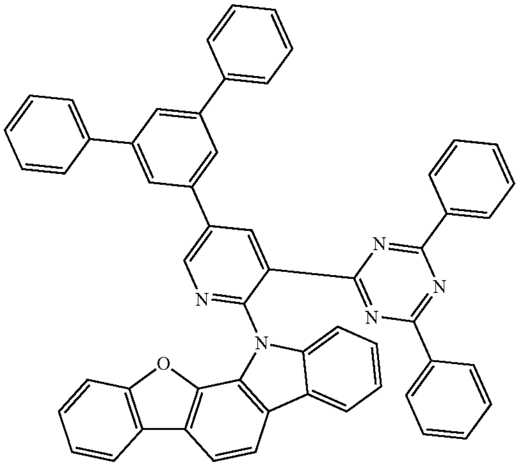

-continued
399
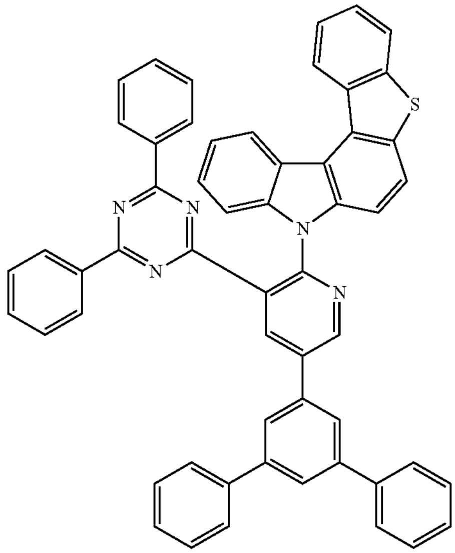
400
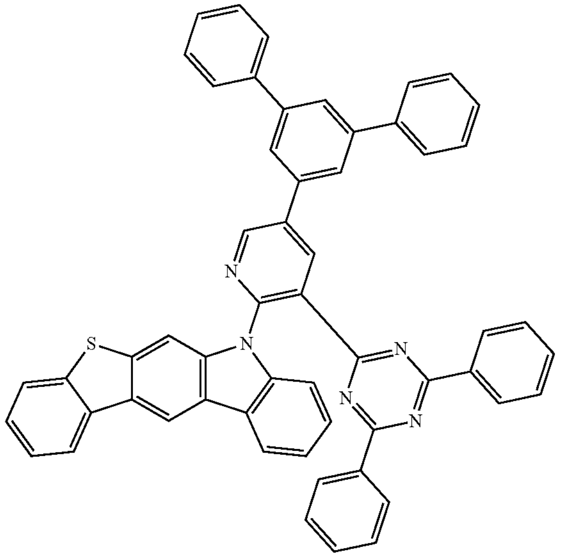
401
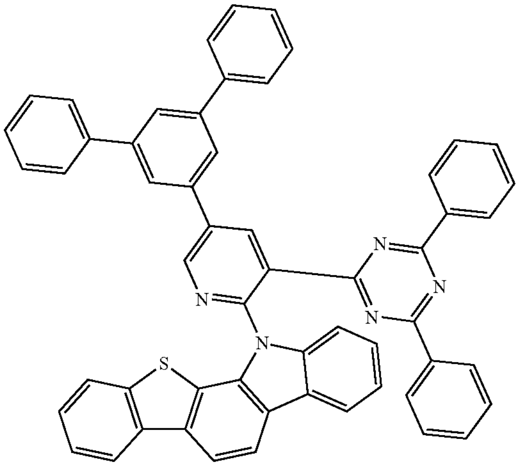
-continued
402
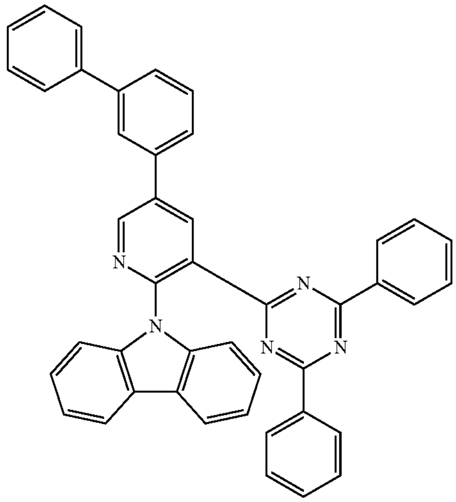
403
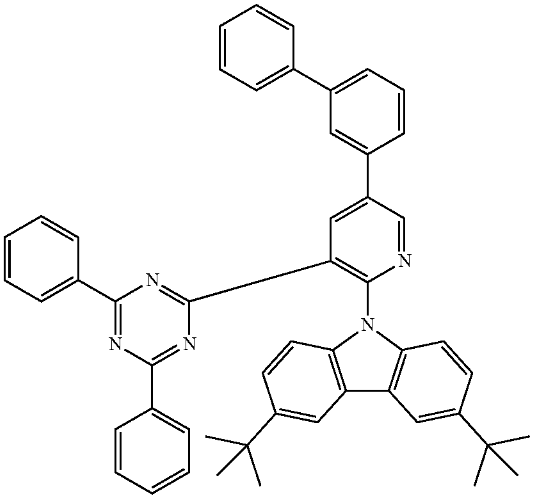
404
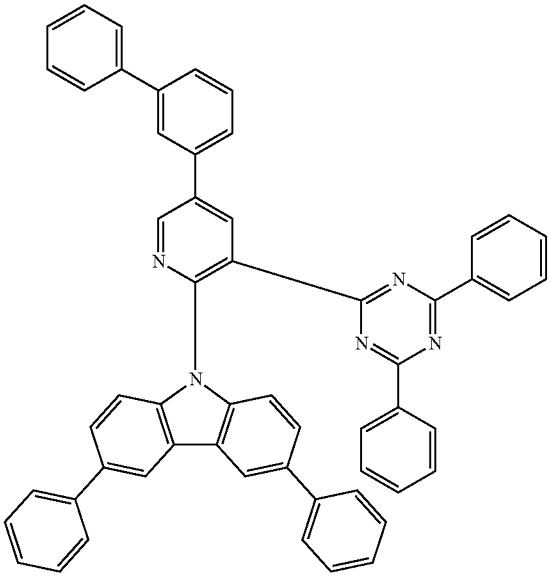

-continued
405
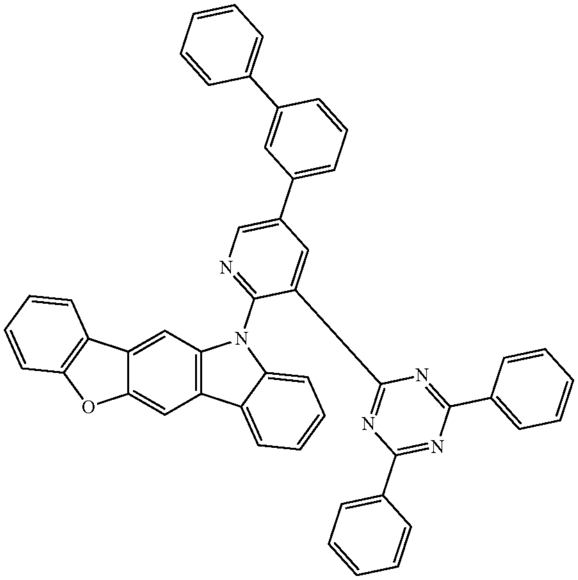
406
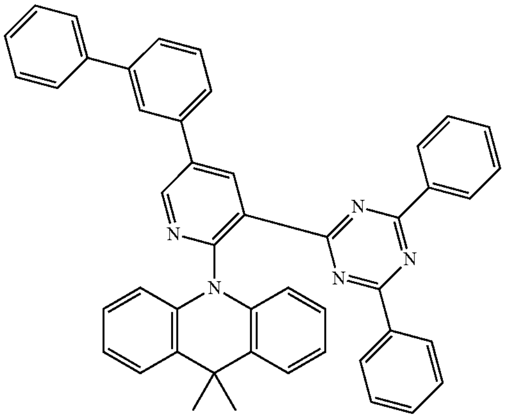
407
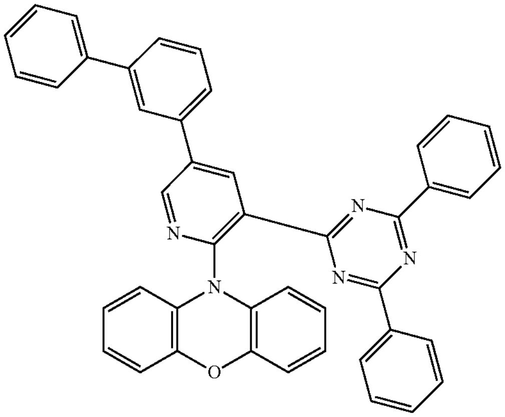
-continued
408
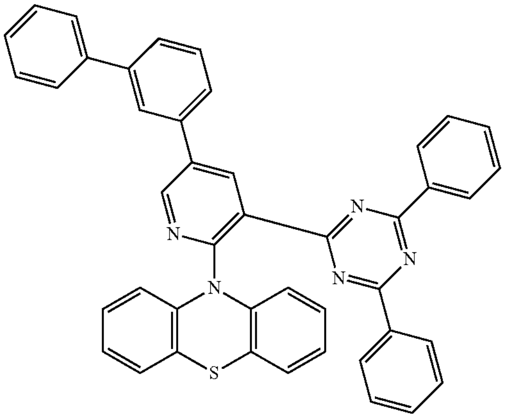
409
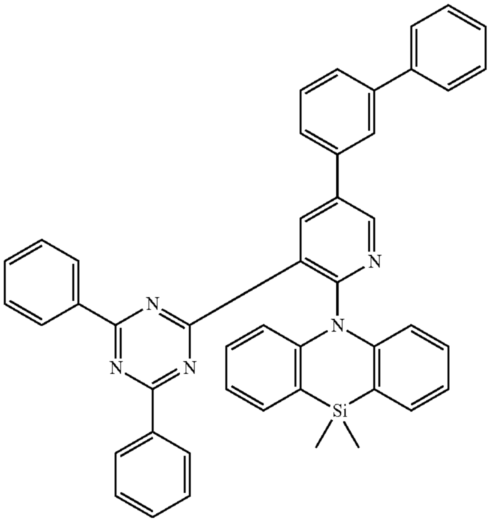
410
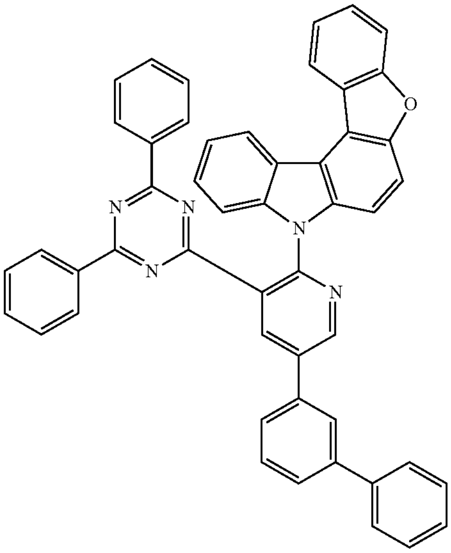

-continued
411
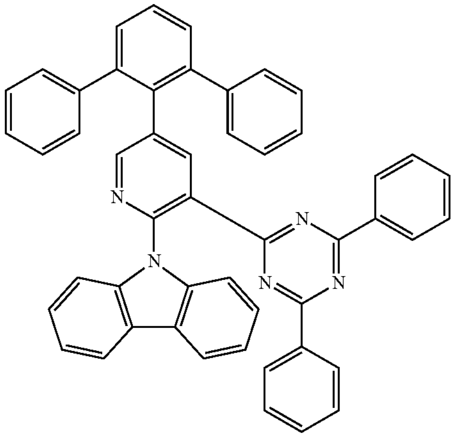
412
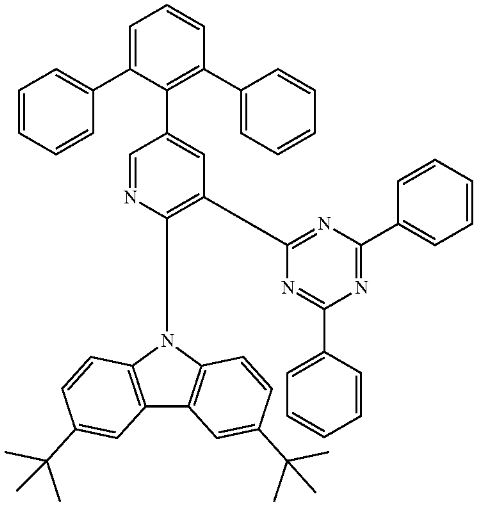
413
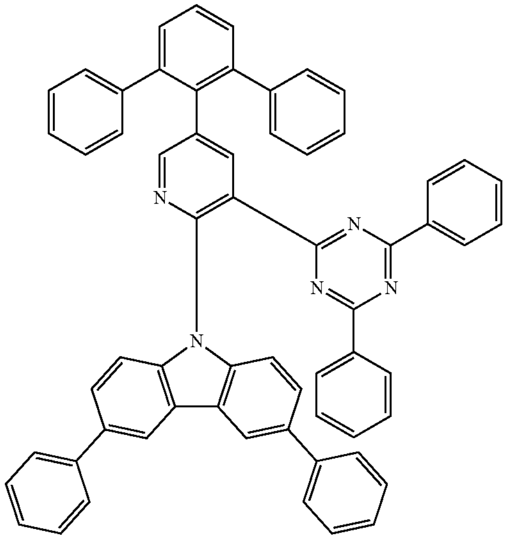
-continued
414
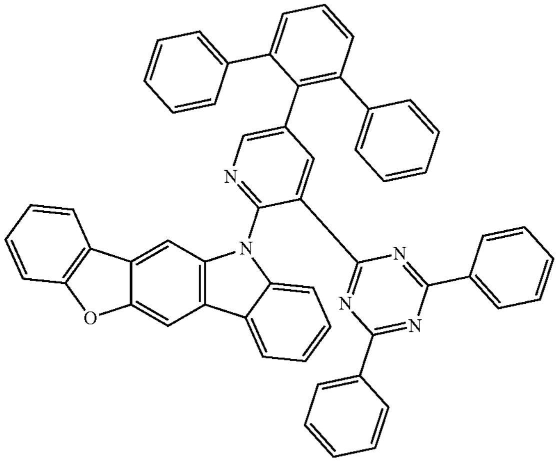
415
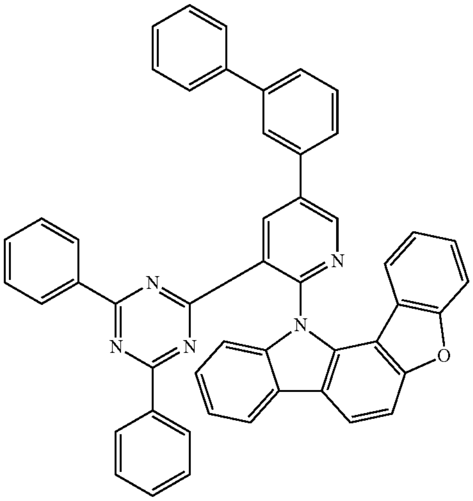
416
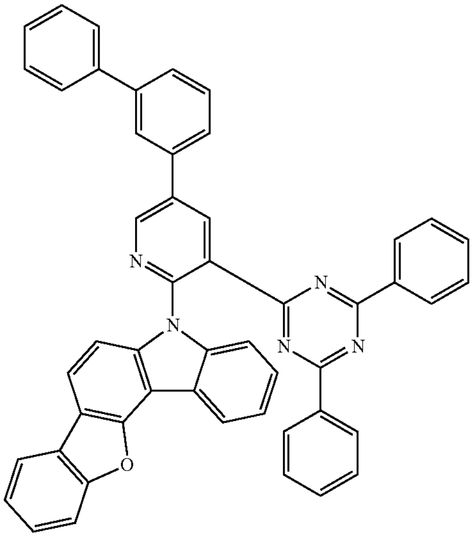

-continued
417
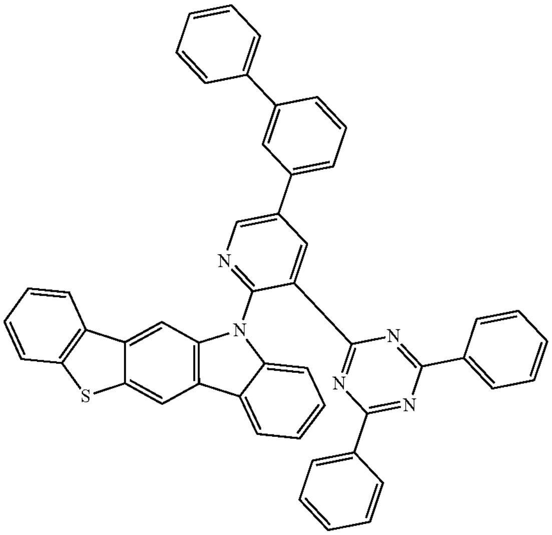
418
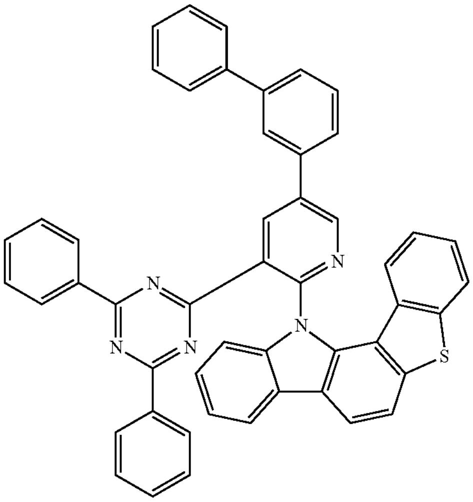
419
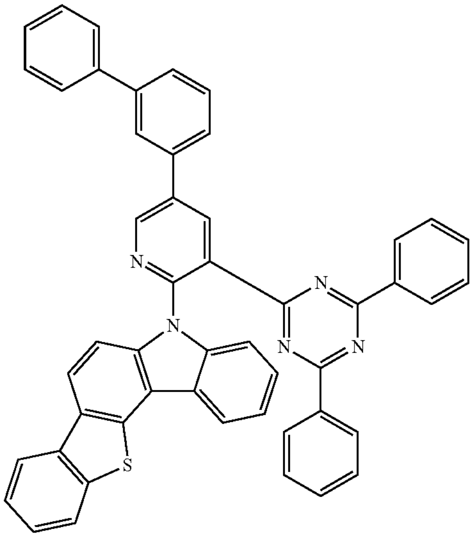
-continued
420
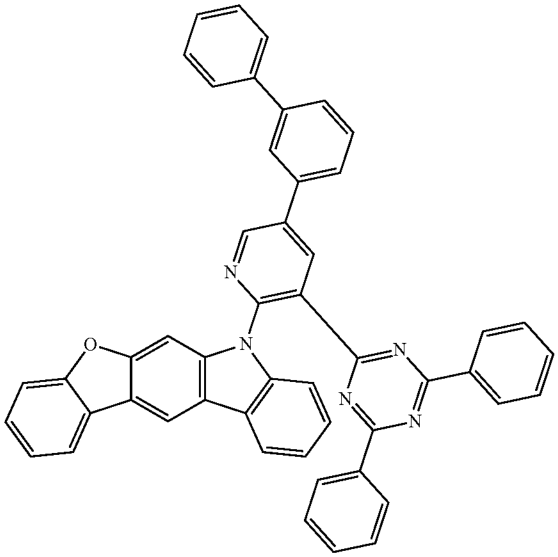
421
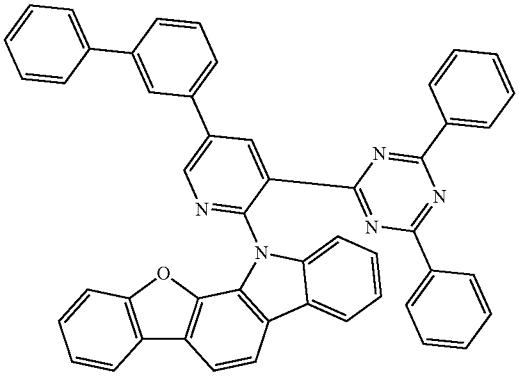
423
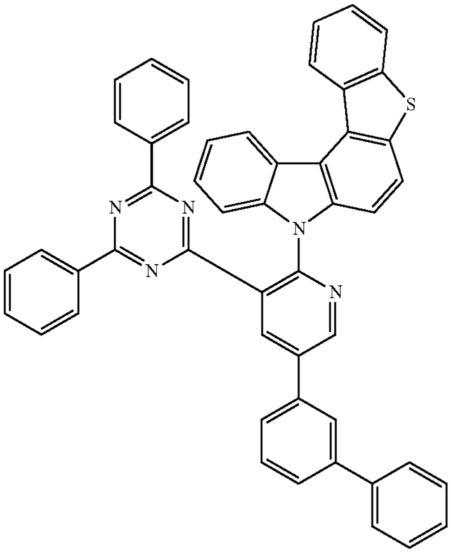

-continued
424
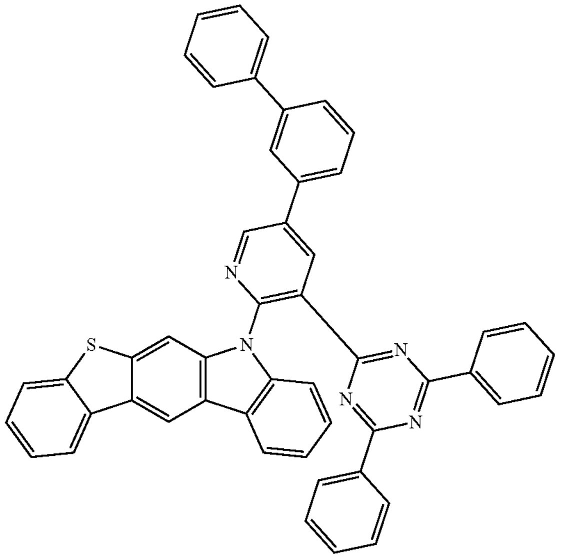
425
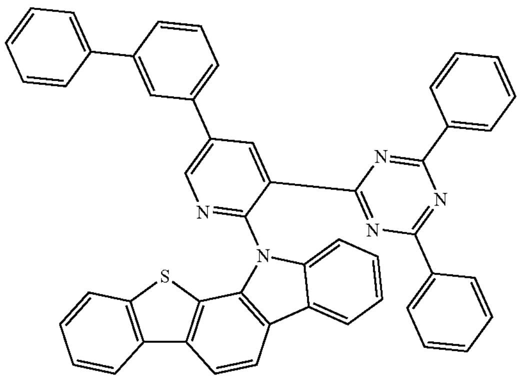
426
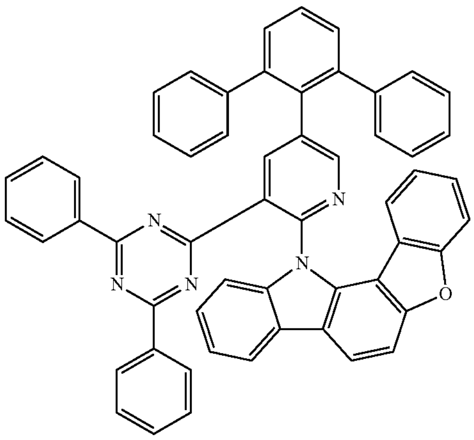
-continued
427
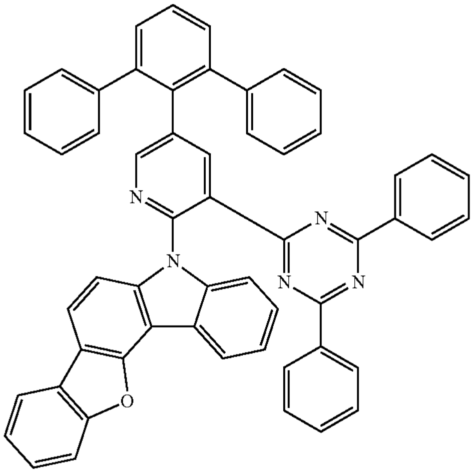
428
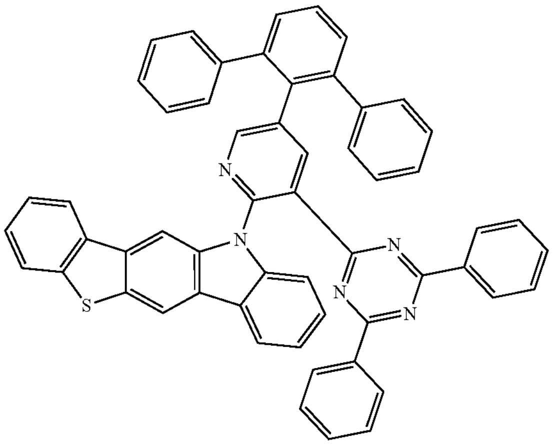
429
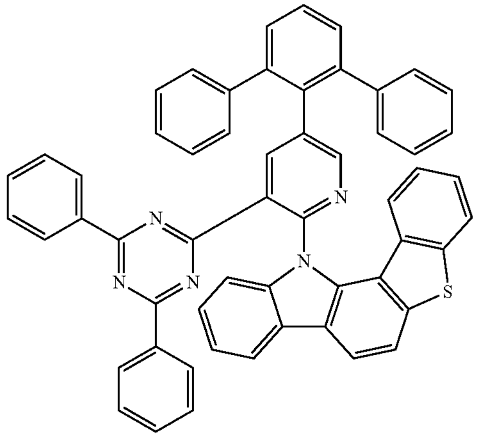

430
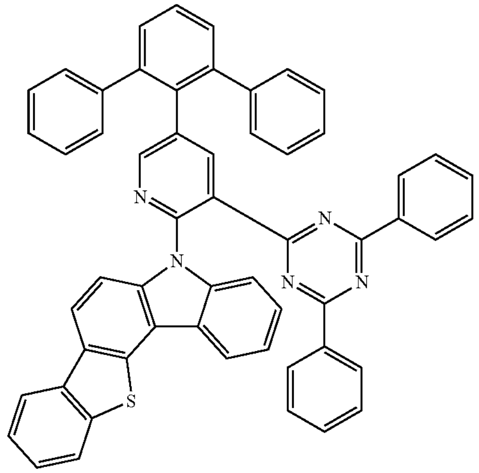
431
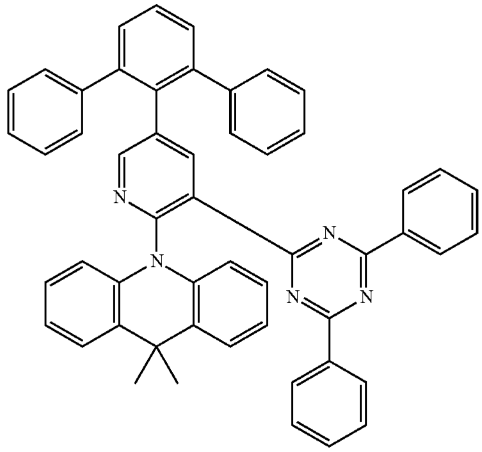
432
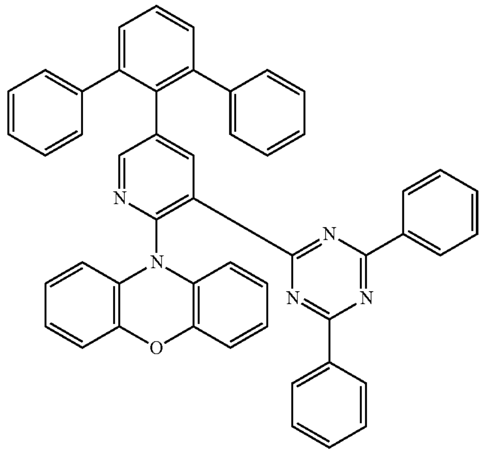
433
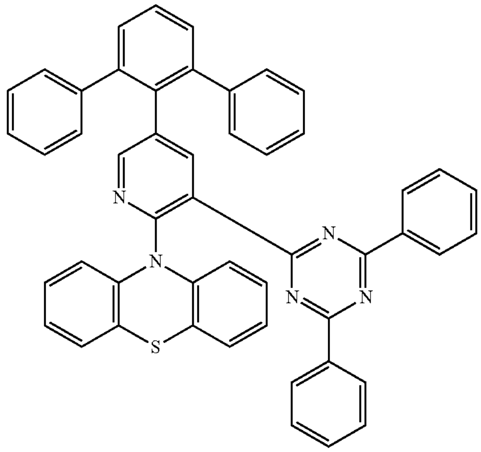
434
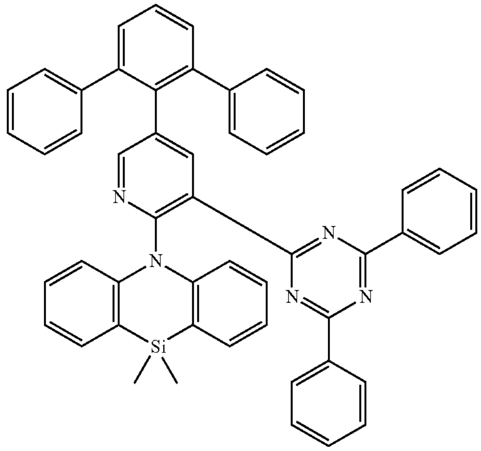
435
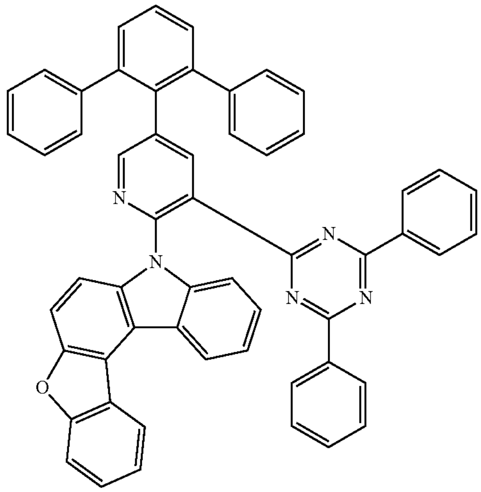

-continued
436
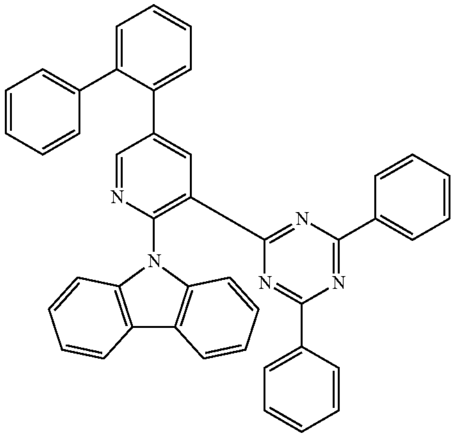
437
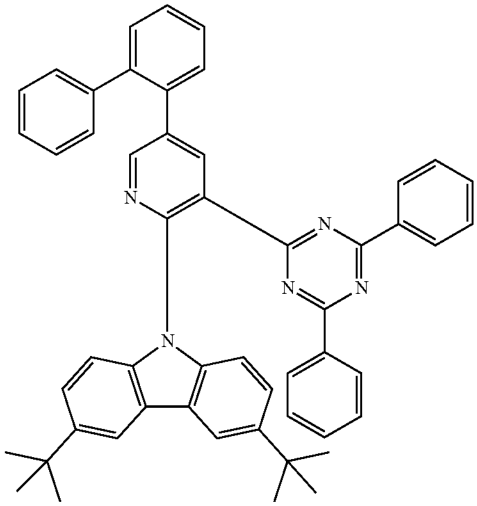
438
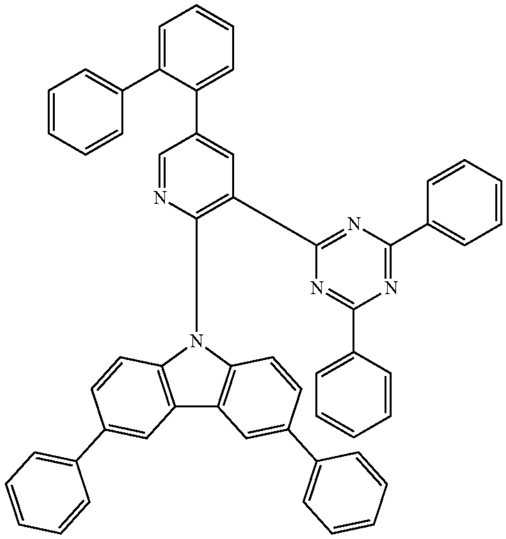
-continued
439
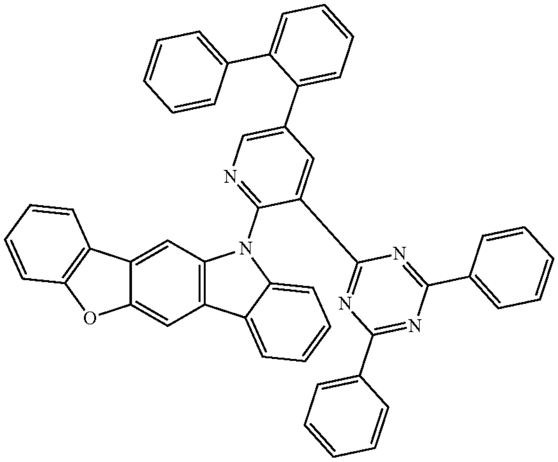
440
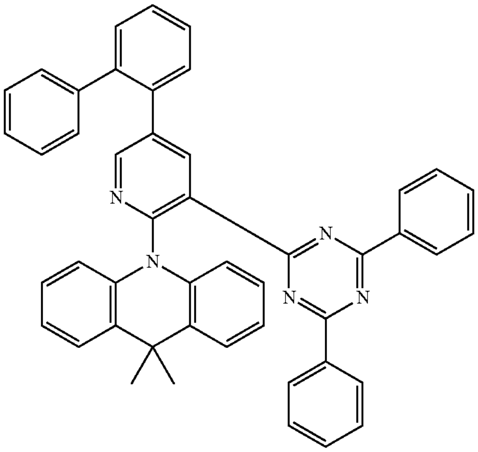
441
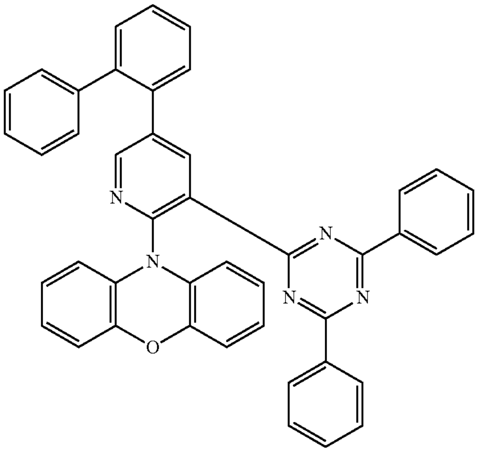

-continued
442
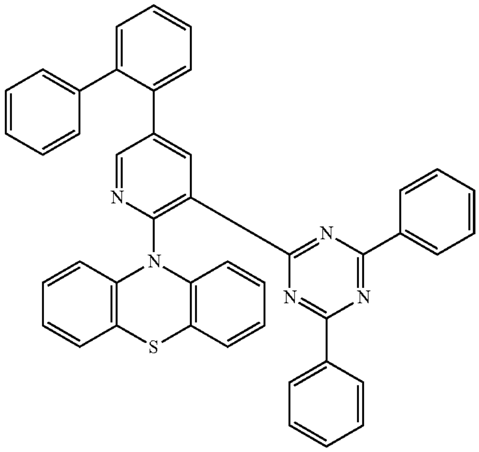
443
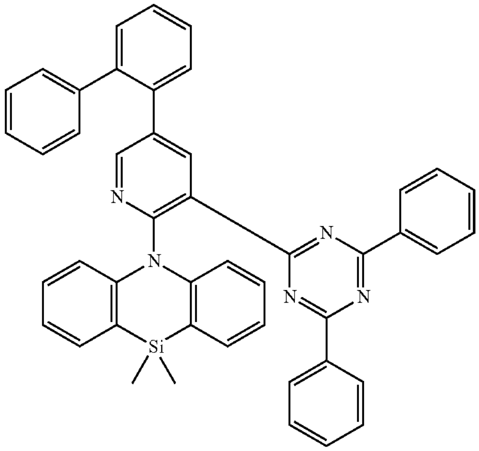
444
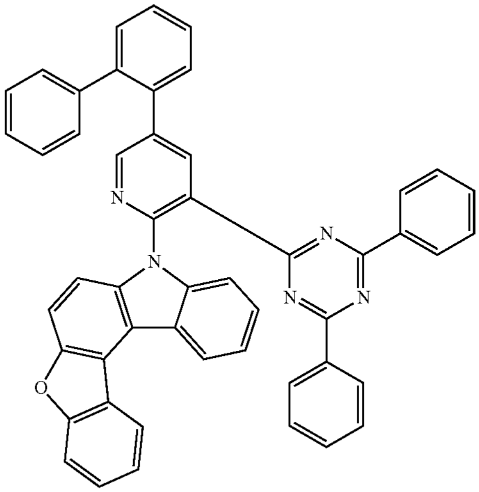
-continued
445
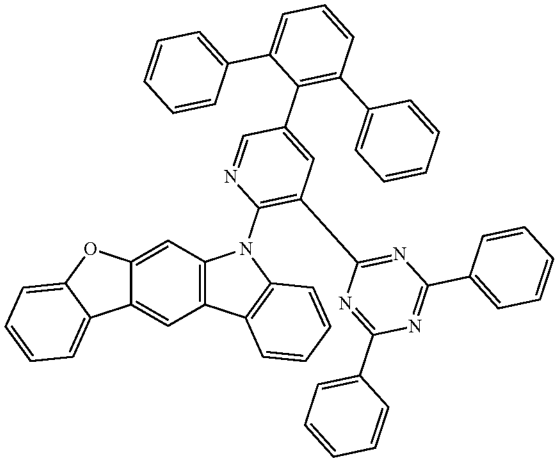
446
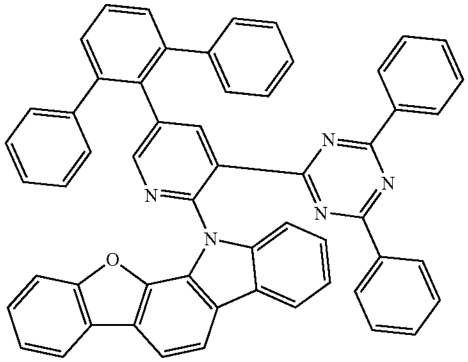
447
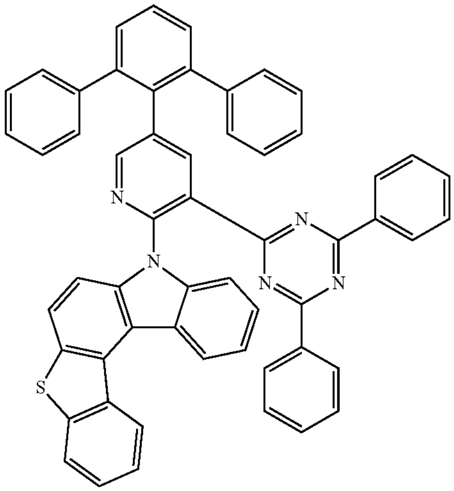

-continued
448
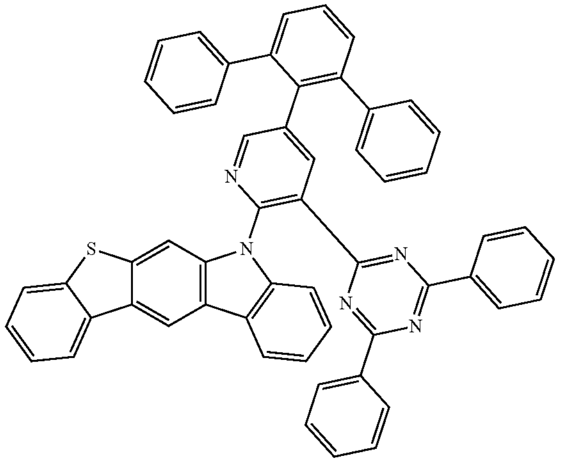
449
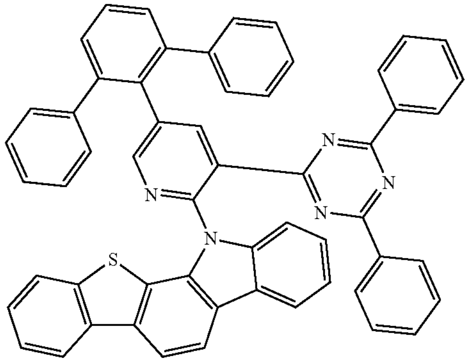
450
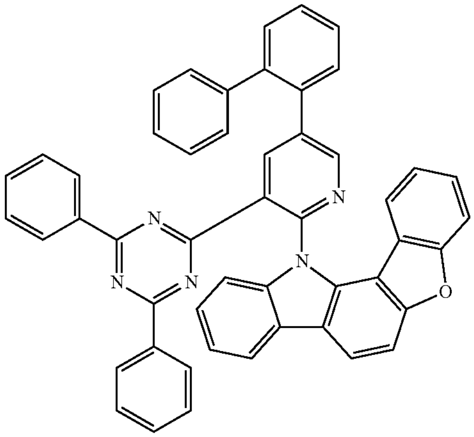
-continued
451
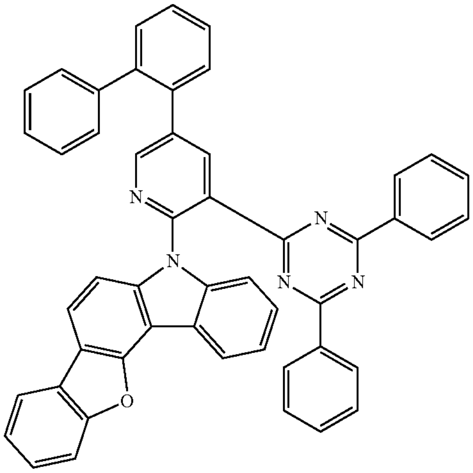
452
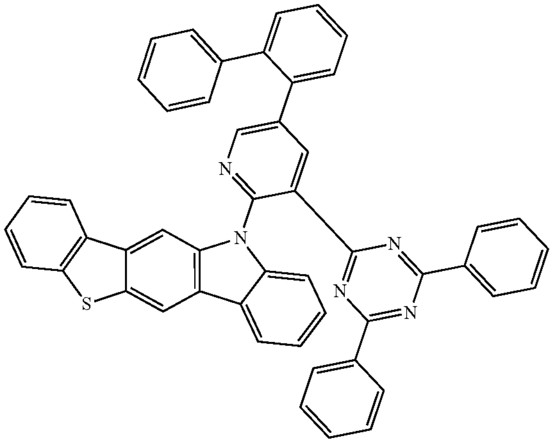
453
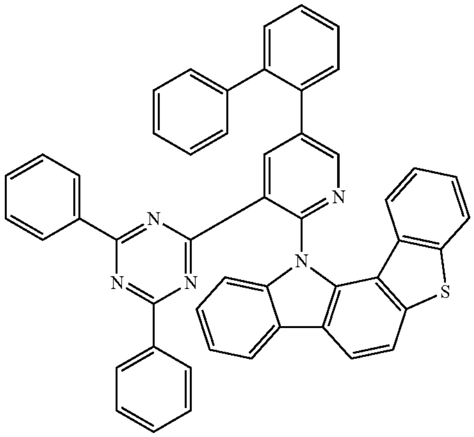

-continued
454
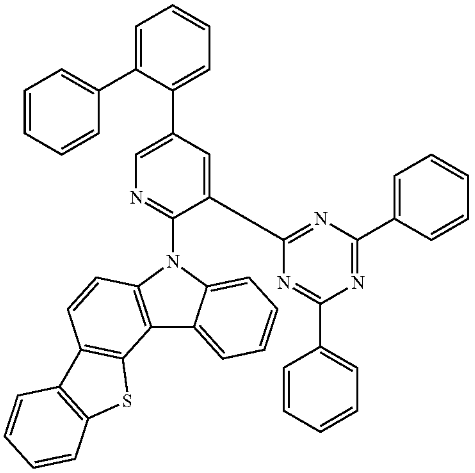
455
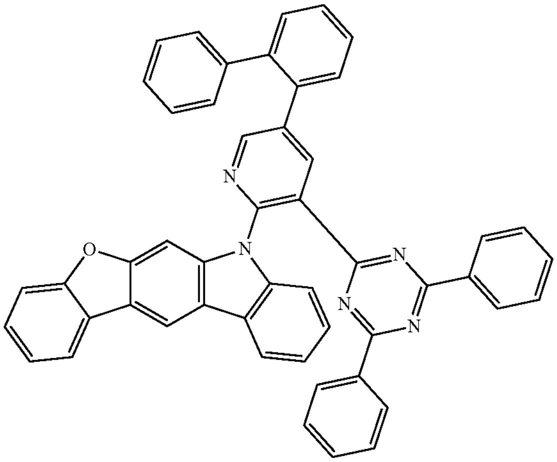
456
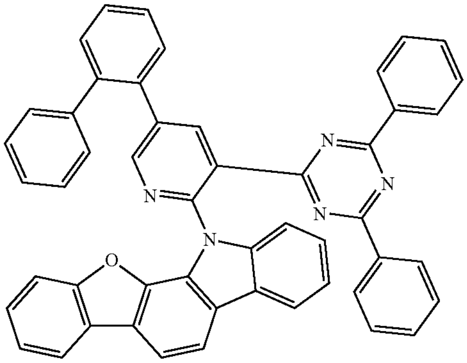
-continued
457
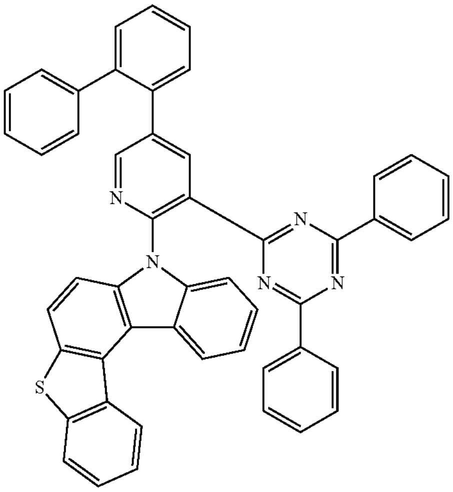
458
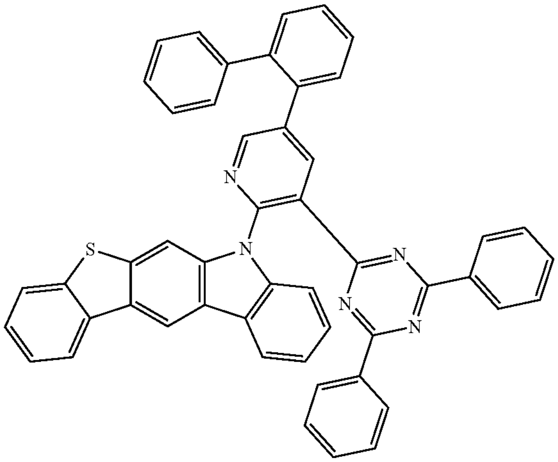
459
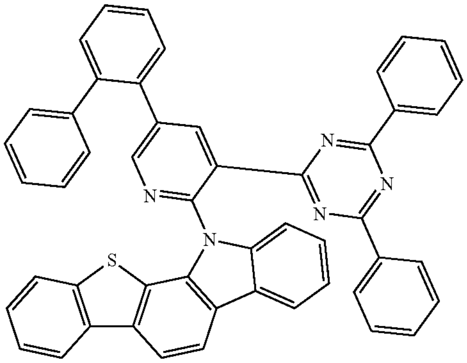

-continued
460
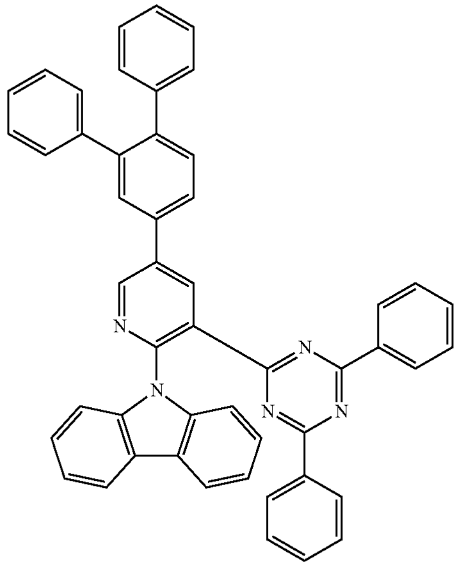
462
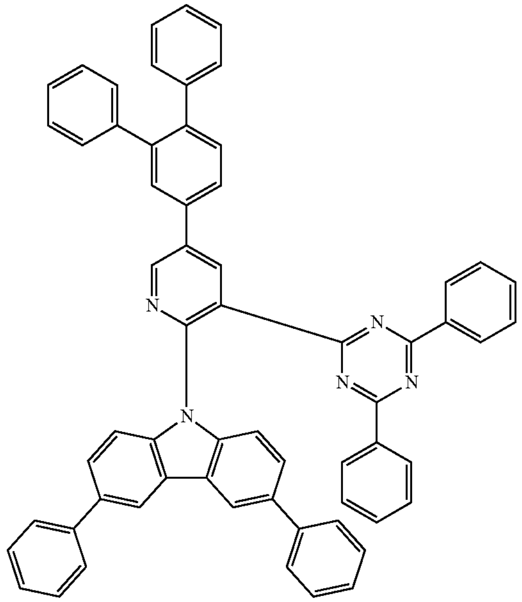
461
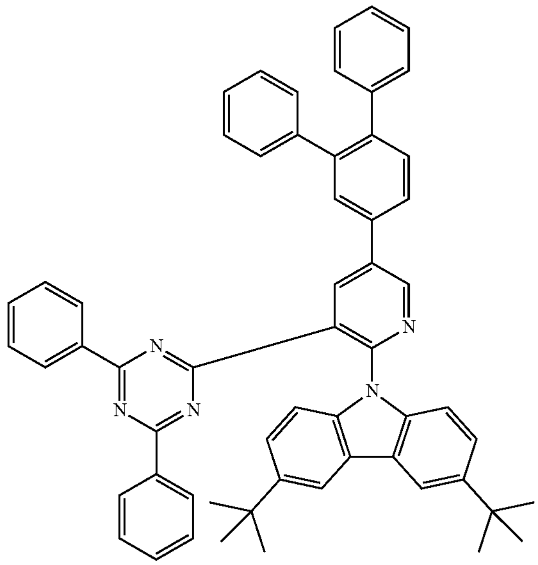
463
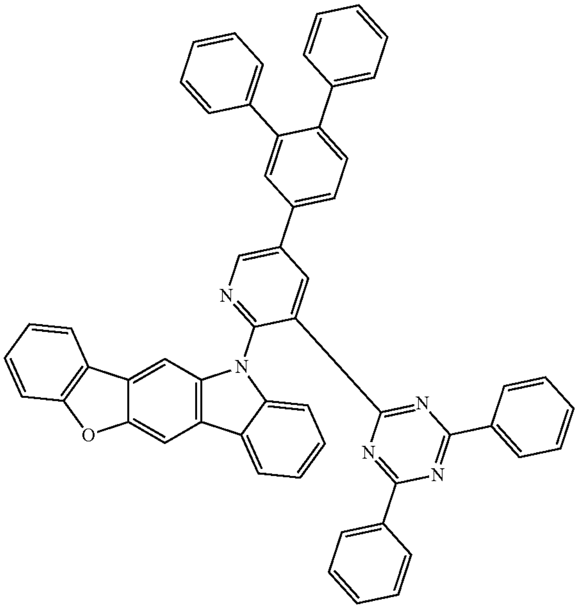

-continued
464
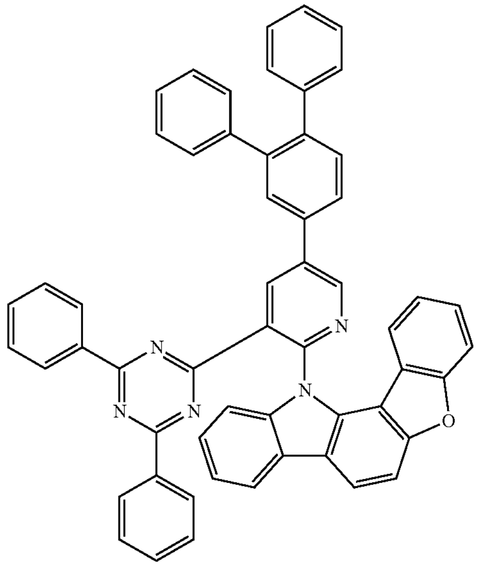
465
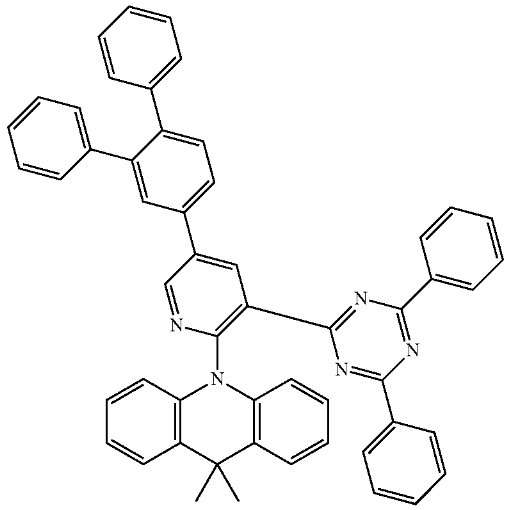
466
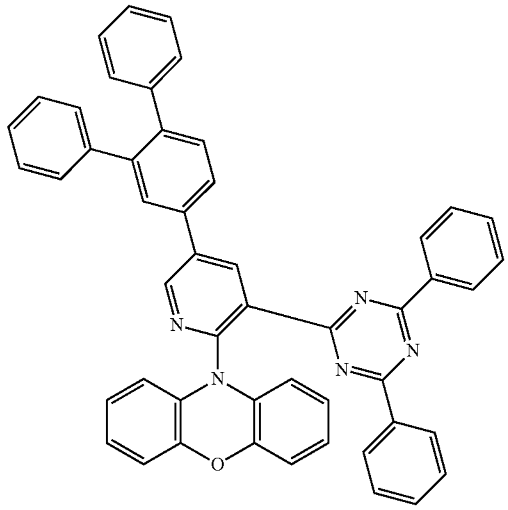
-continued
467
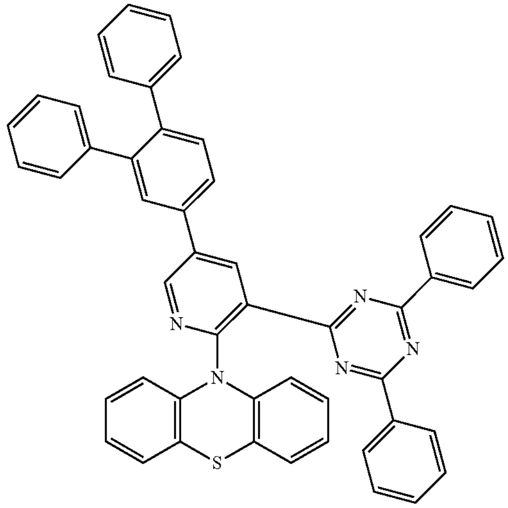
468
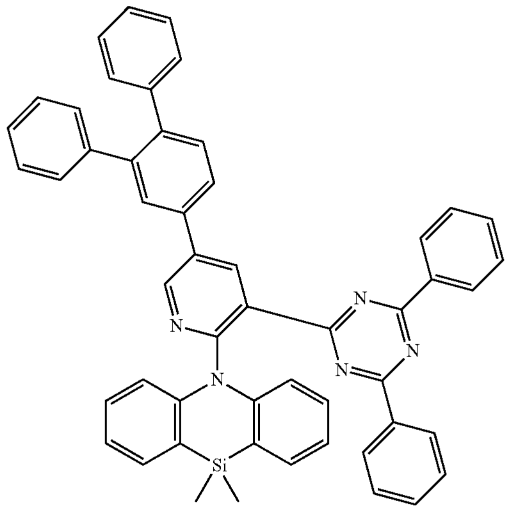

-continued
469
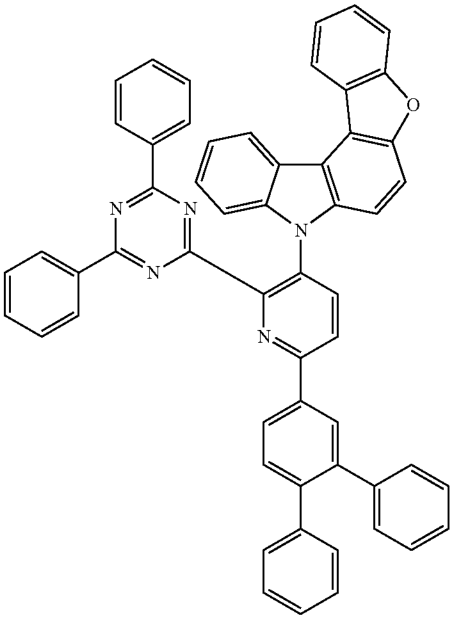
470
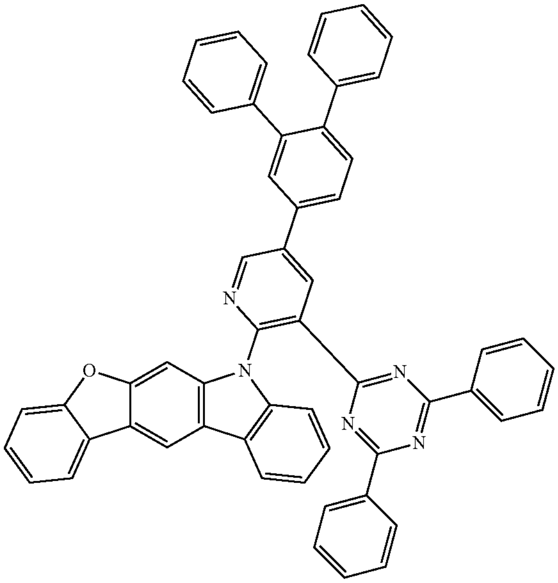
-continued
471
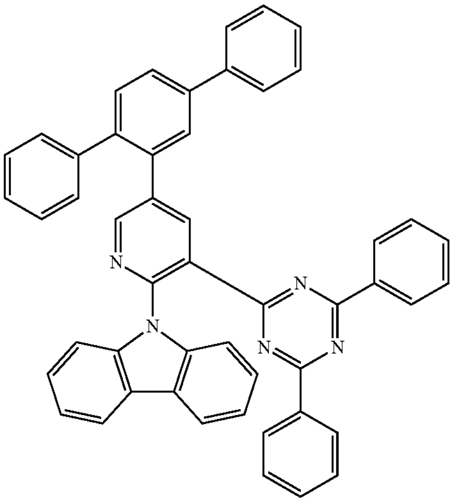
472
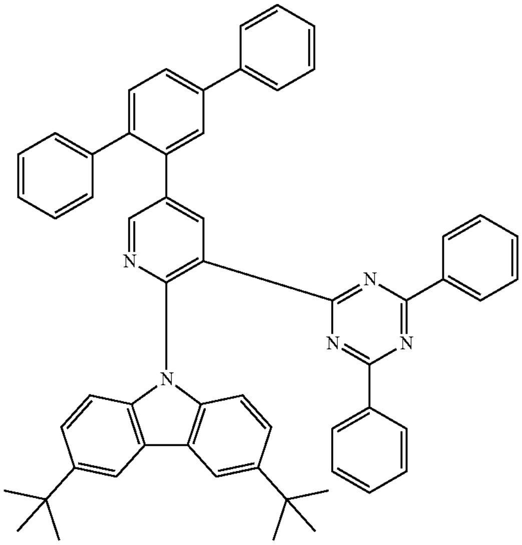
473
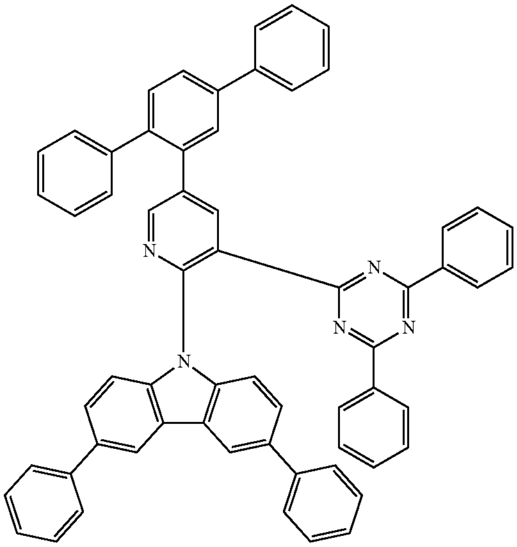

-continued
474
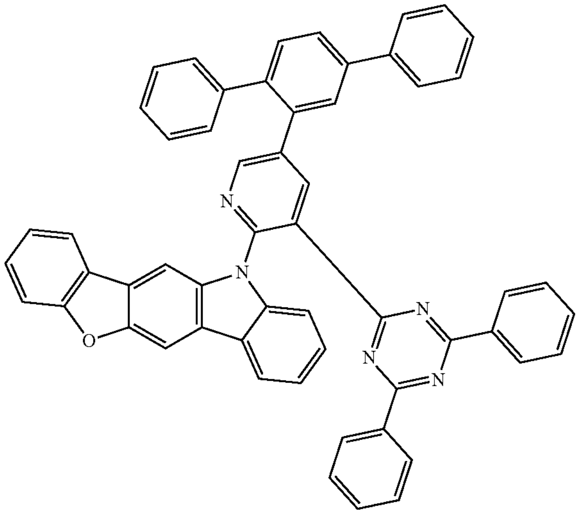
475
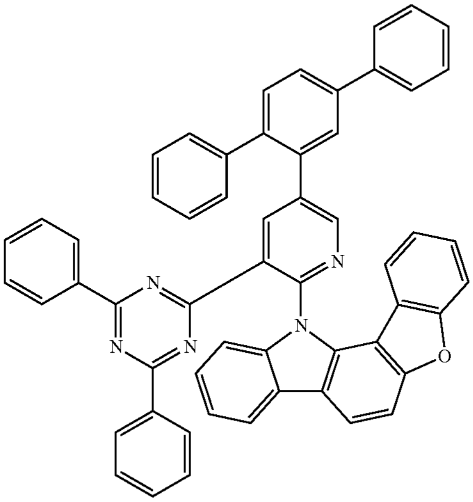
476
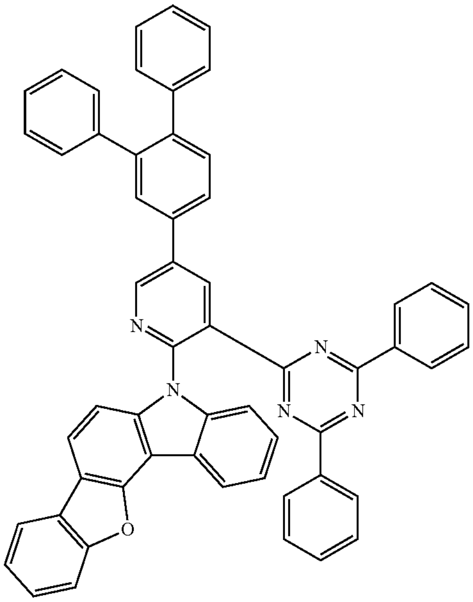
-continued
477
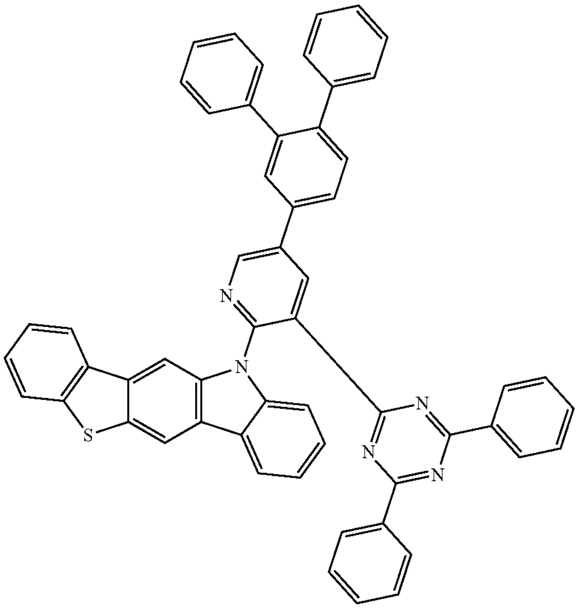
478
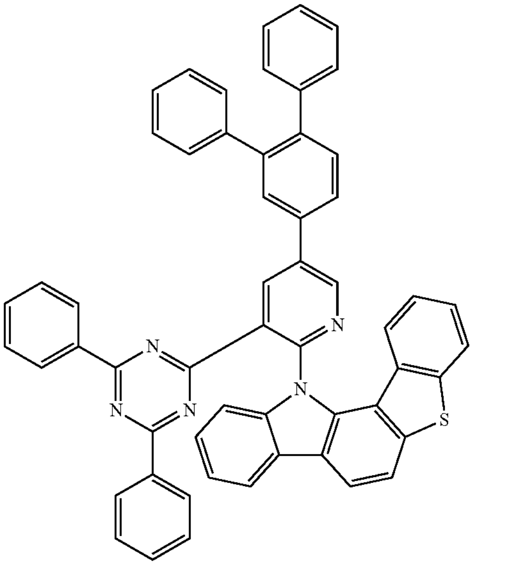

479
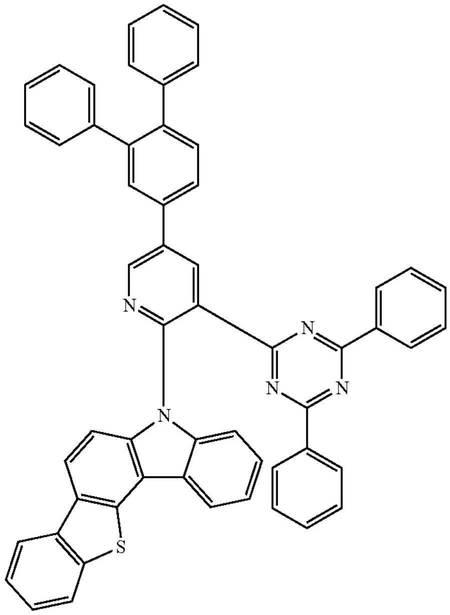
480
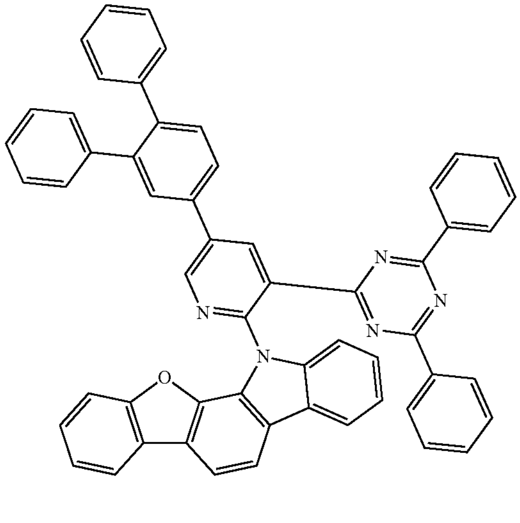
481
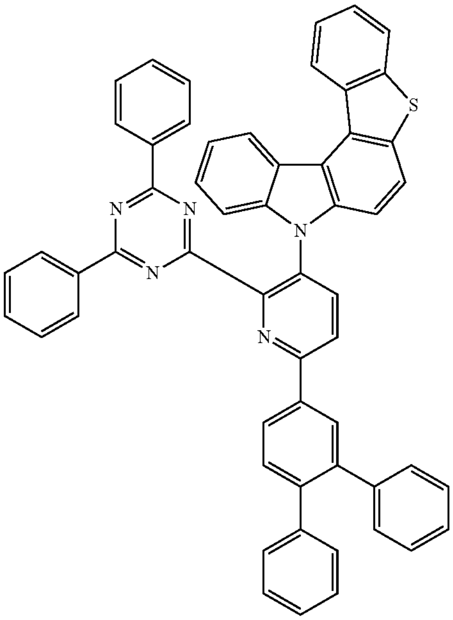
482
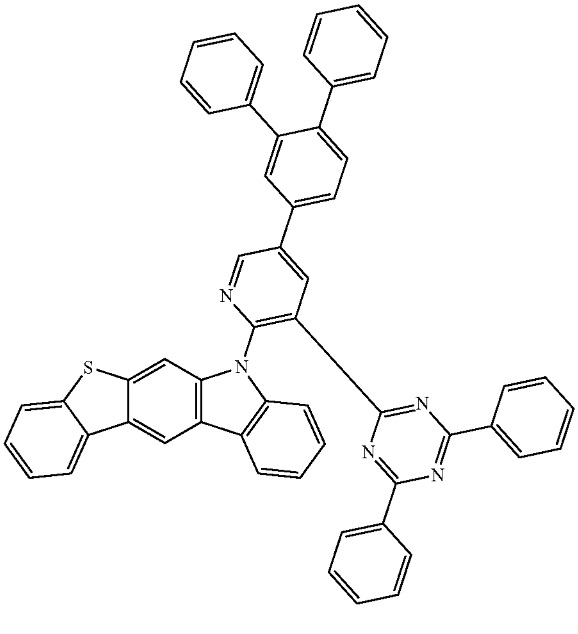

-continued
483
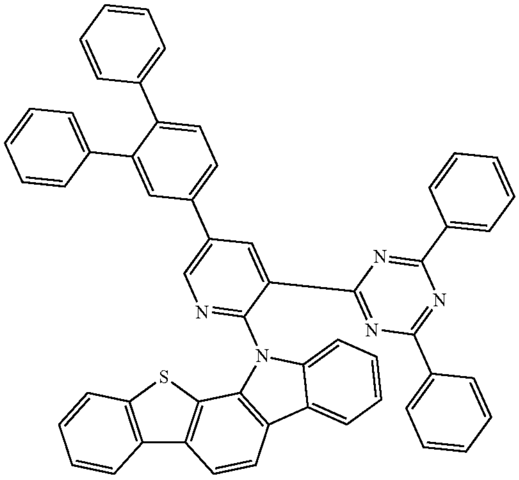
484
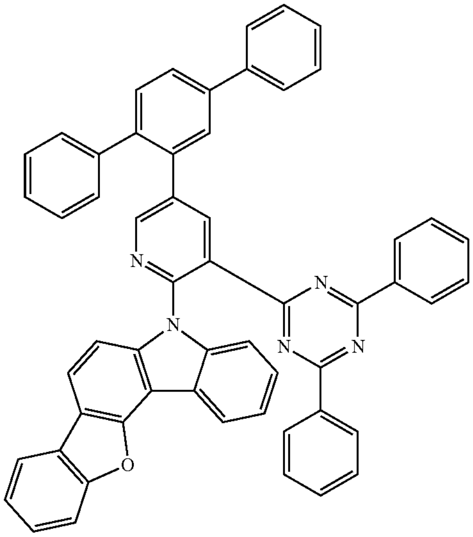
485
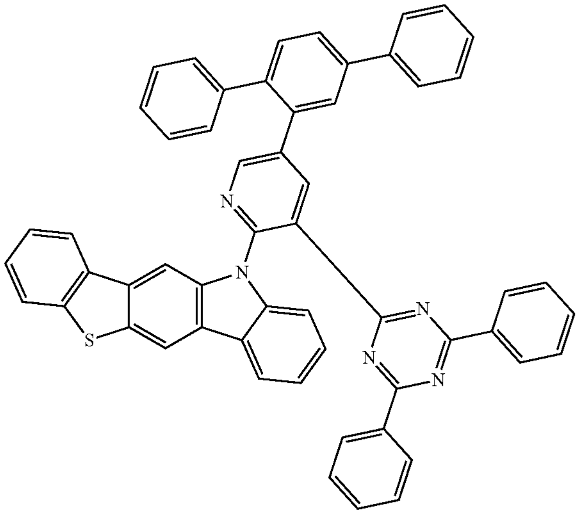
-continued
486
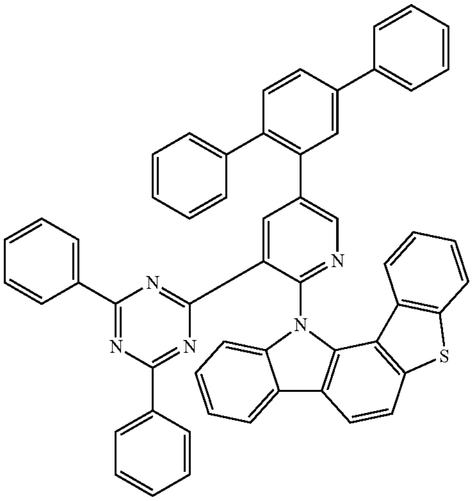
487
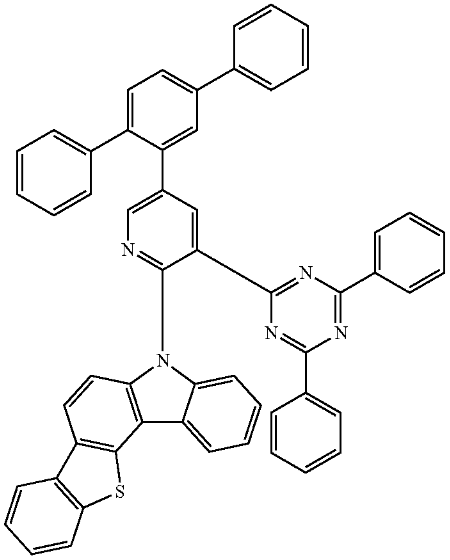
488
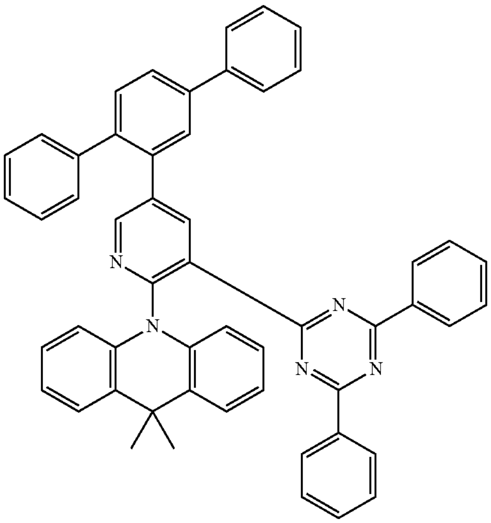

-continued
489
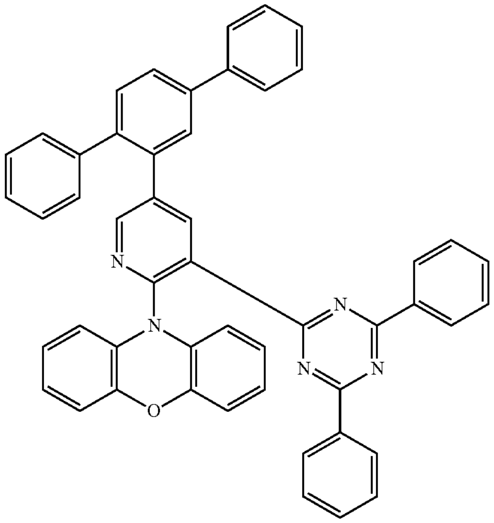
490
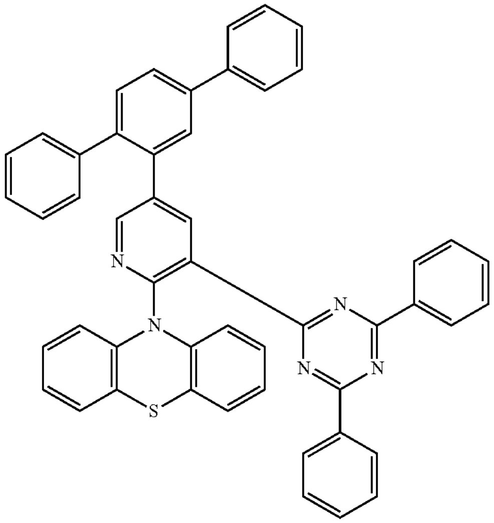
491
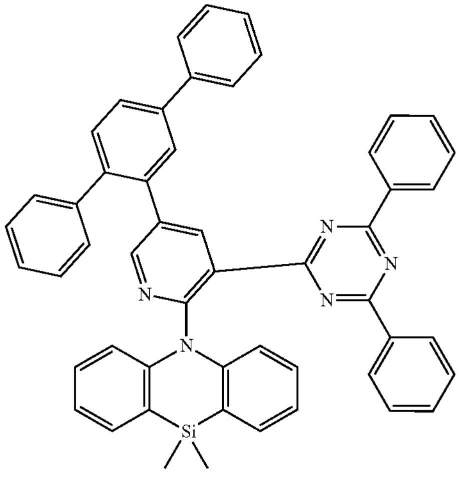
-continued
492
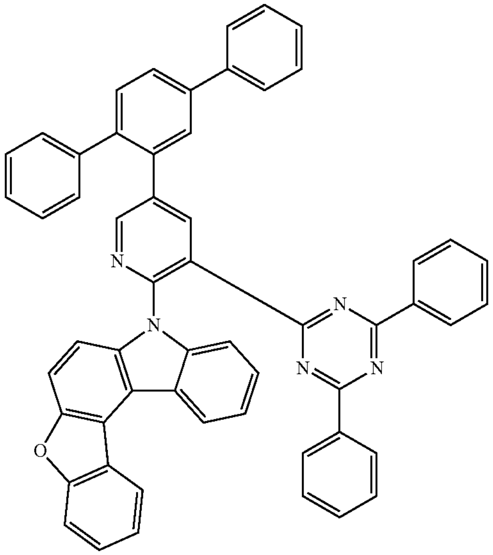
493
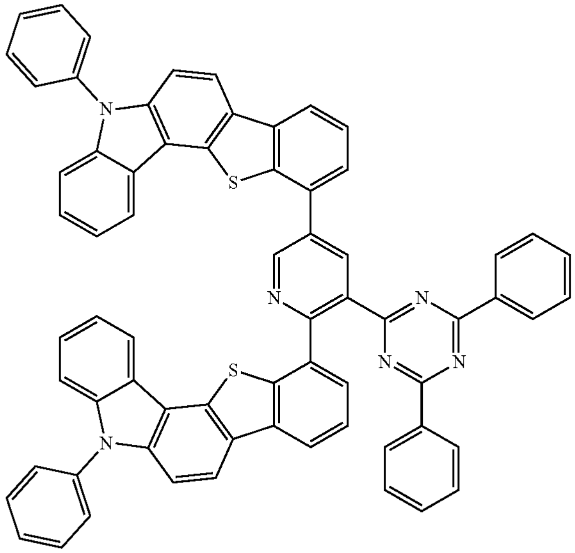

-continued
494
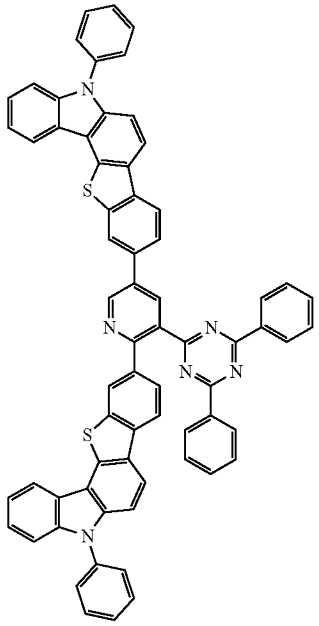
495
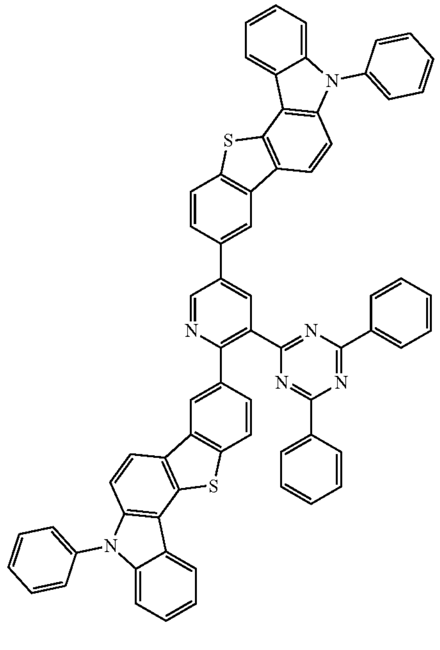
-continued
496
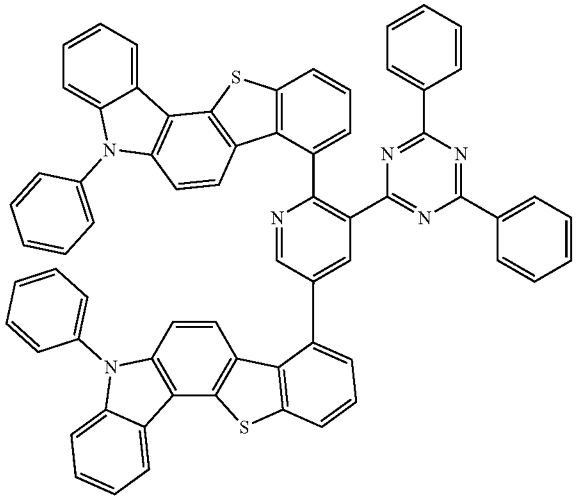
497
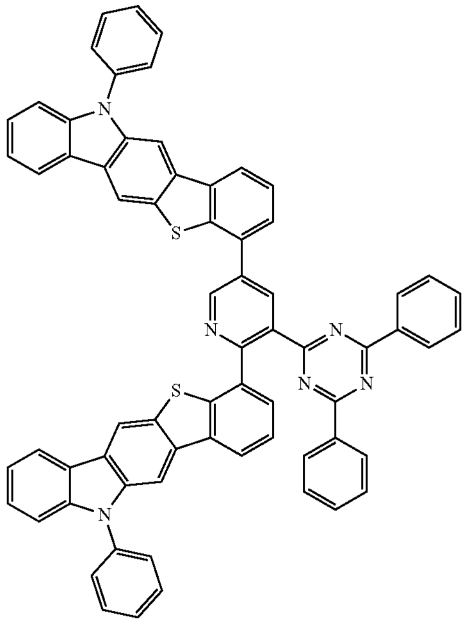

-continued
498
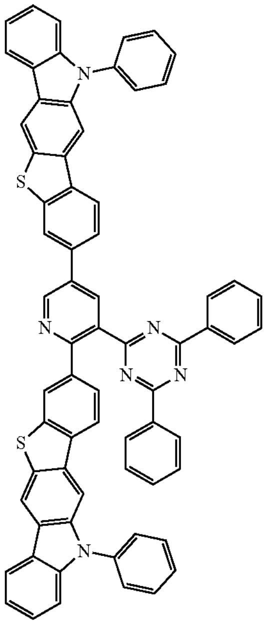
499
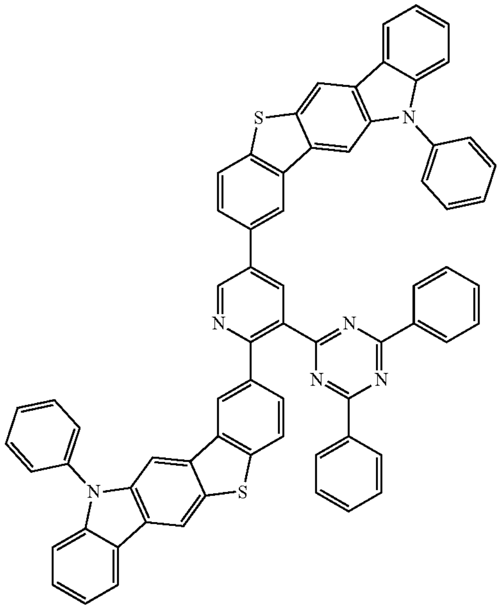
-continued
500
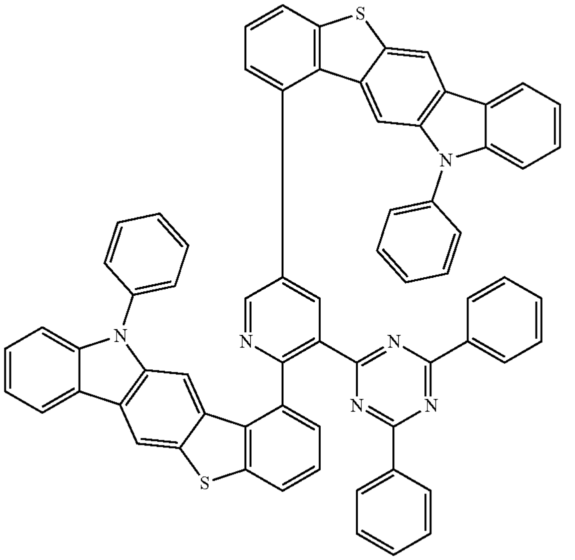
501
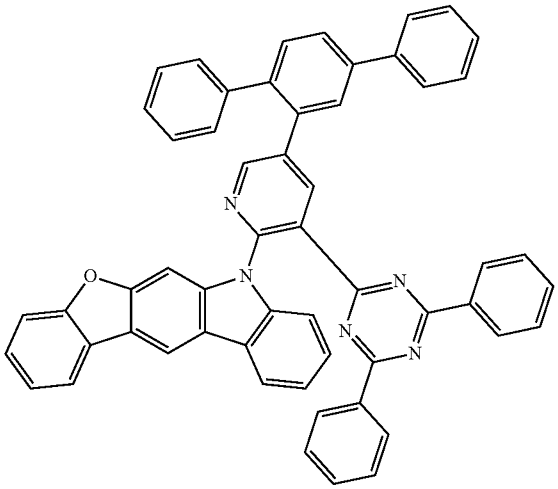
502
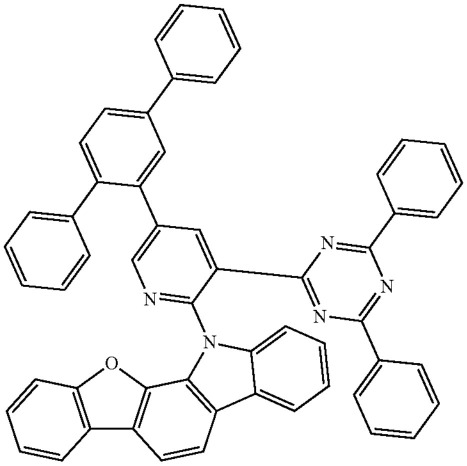

-continued
503
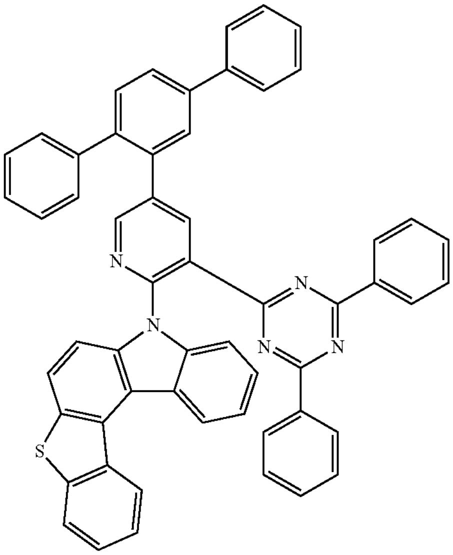
504
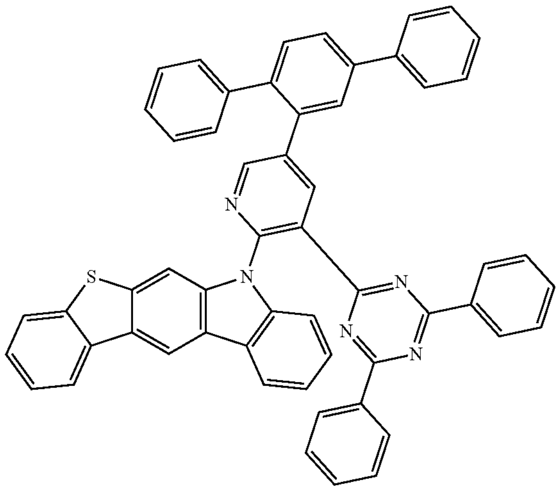
505
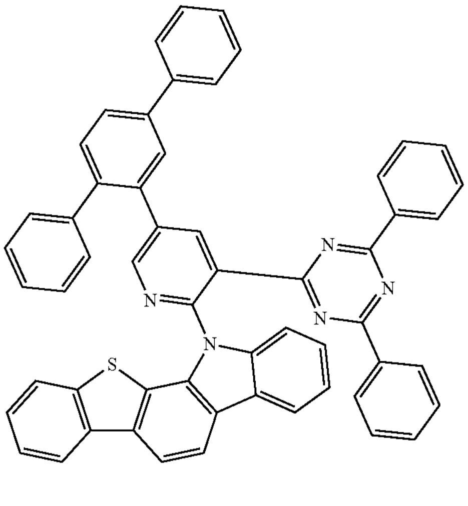
-continued
506
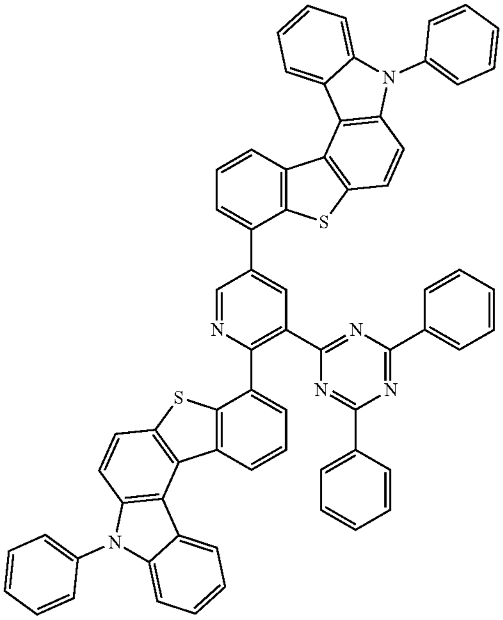
507
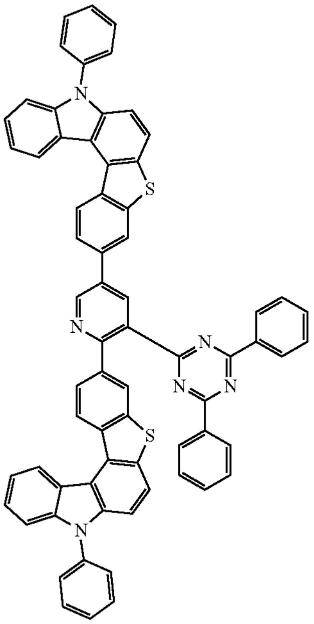

-continued
508
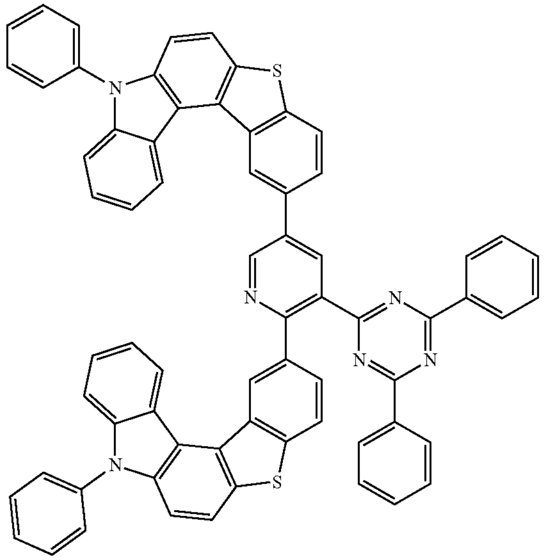
510
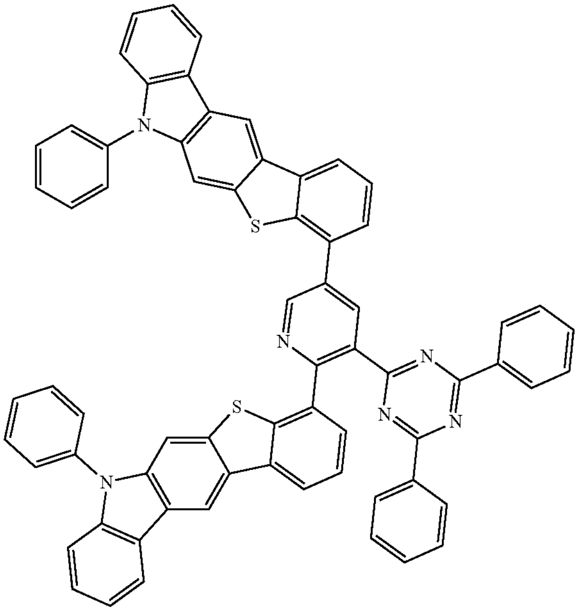
509
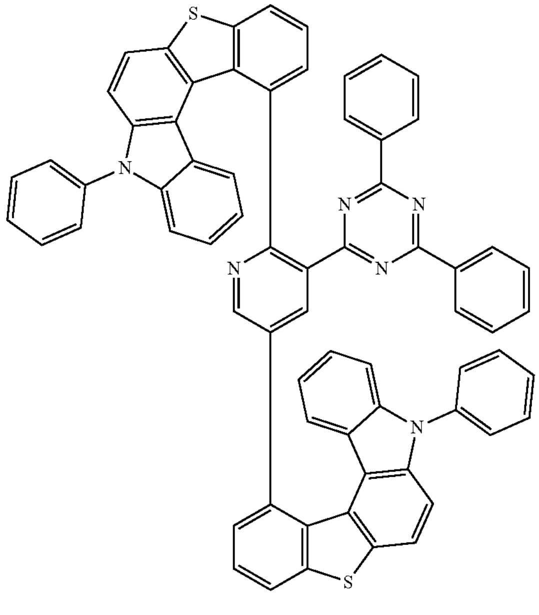
511
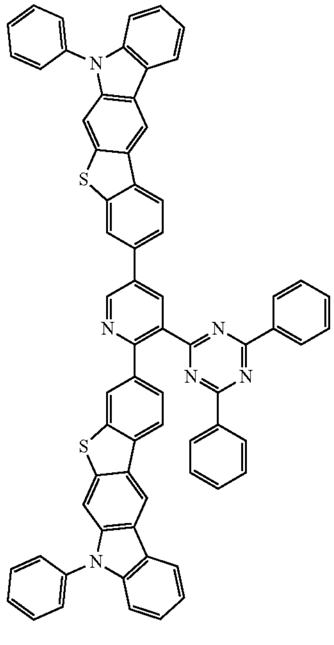

-continued
512
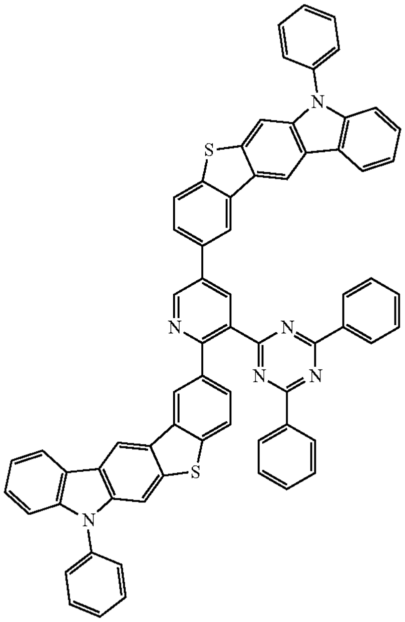
513
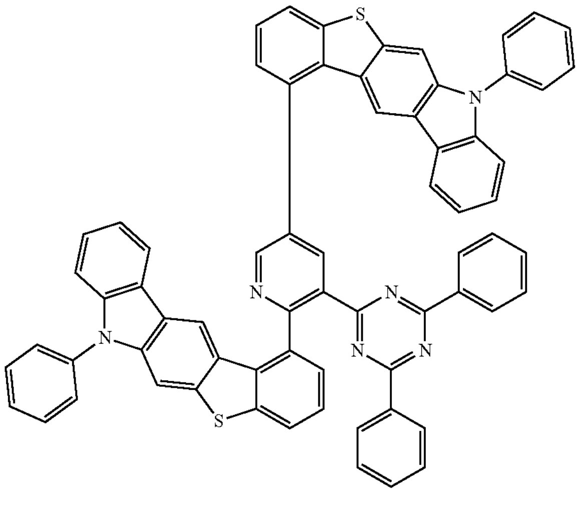
-continued
514
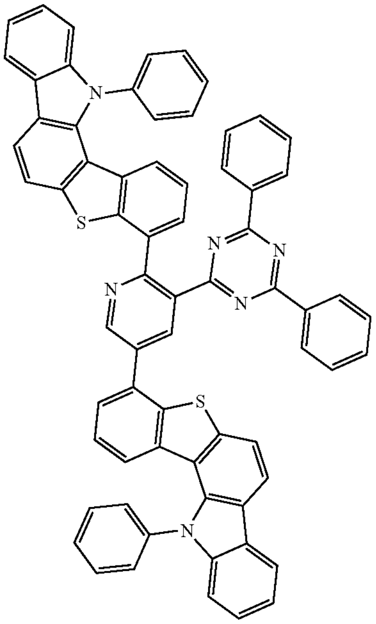
515
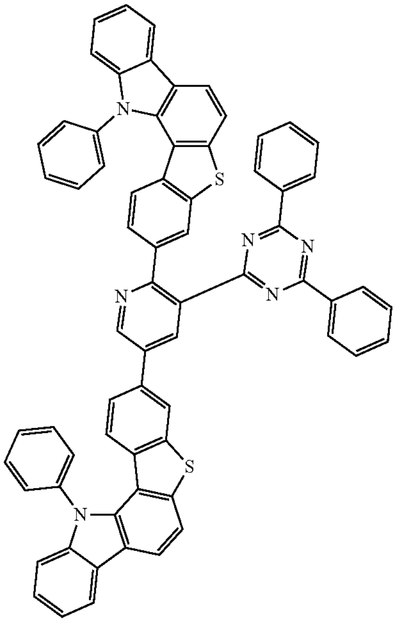

-continued
516
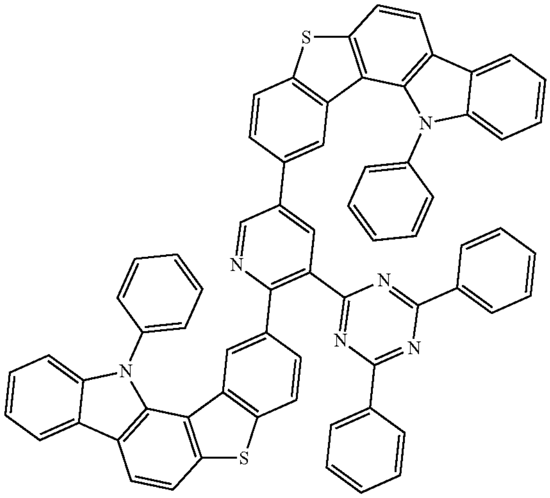
517
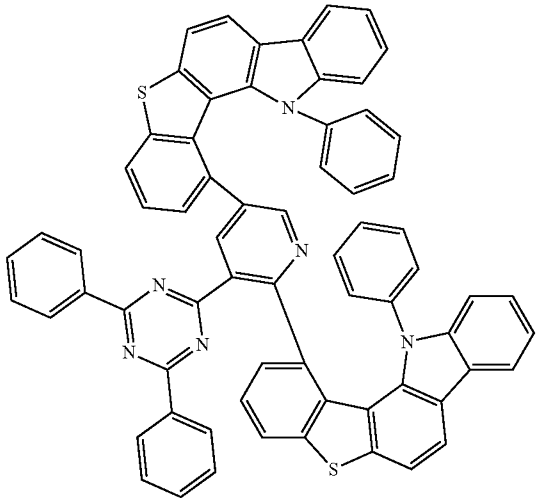
518
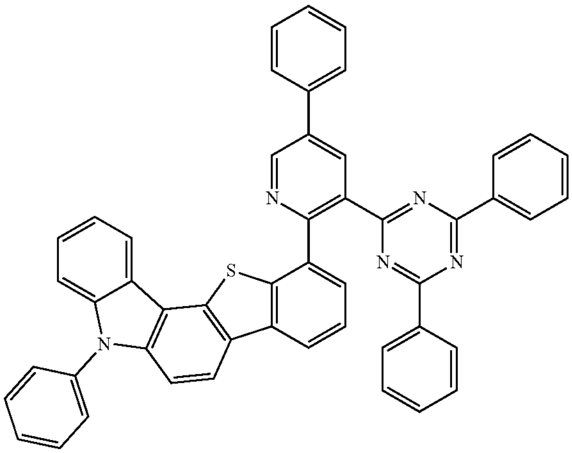
-continued
519
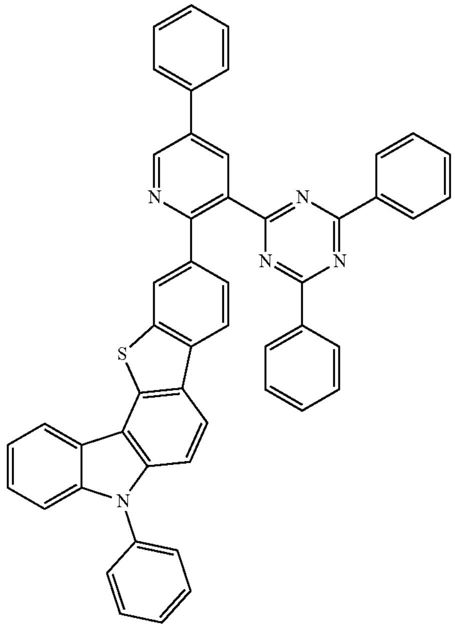
520
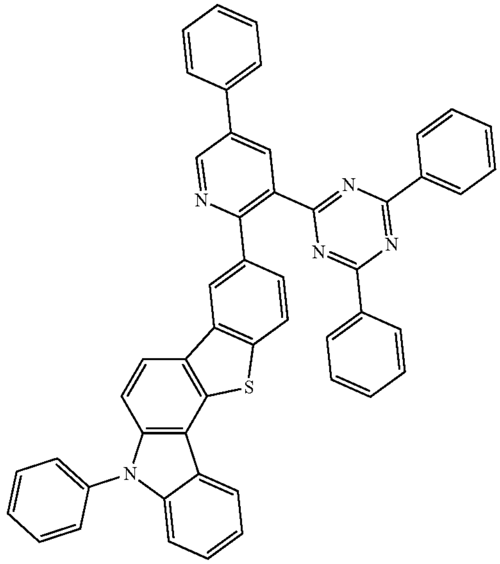
521
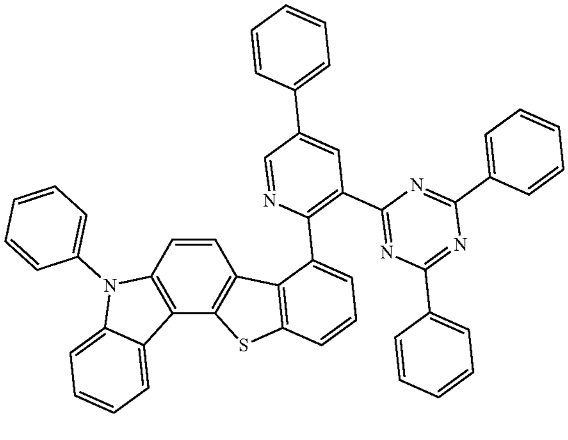

-continued
522
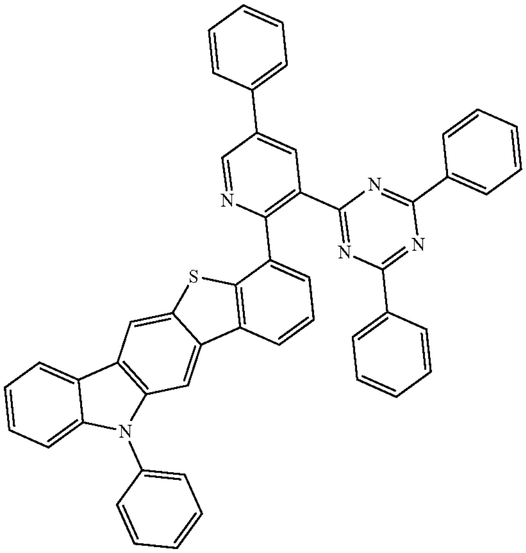
523
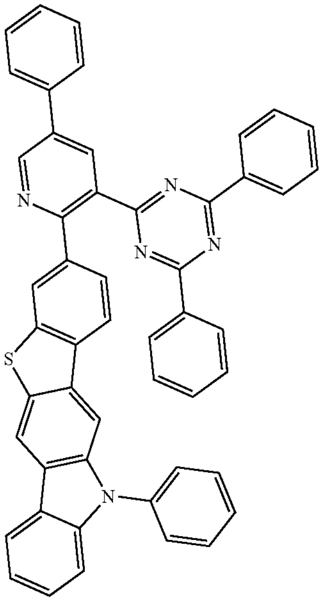
-continued
524
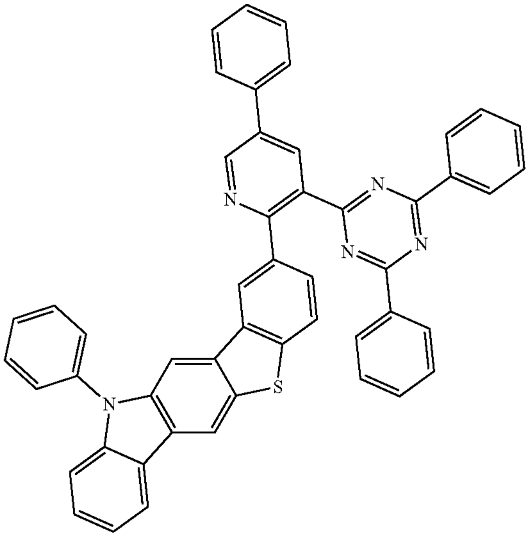
525
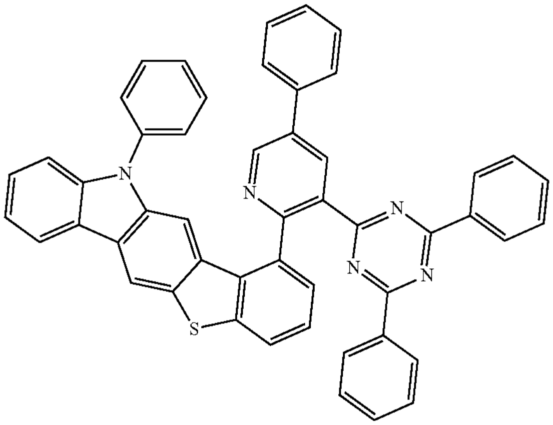
526
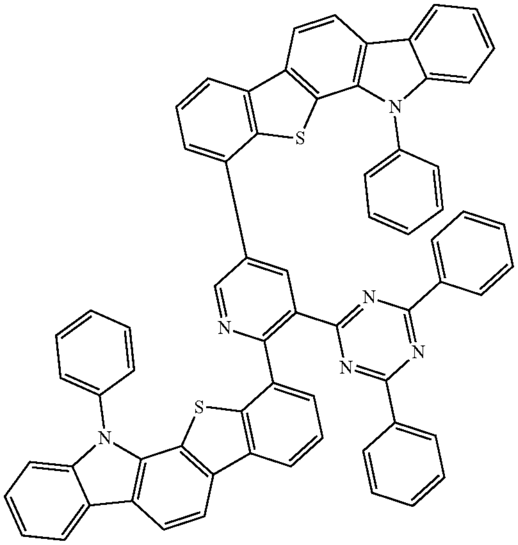

-continued
527
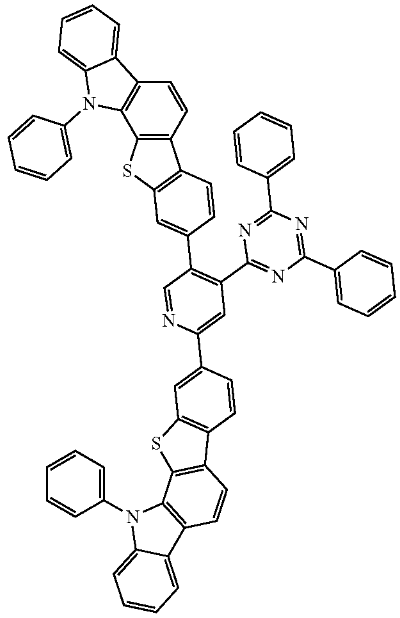
528
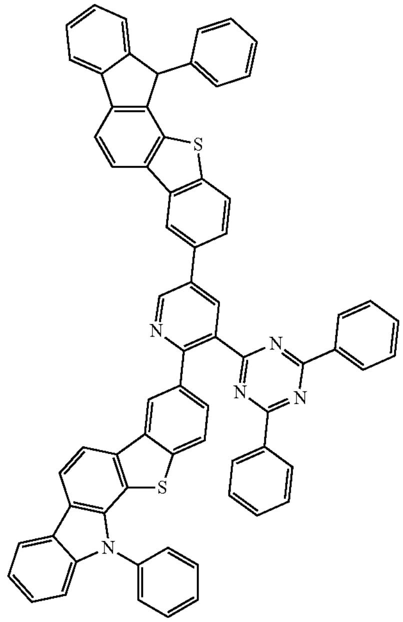
-continued
529
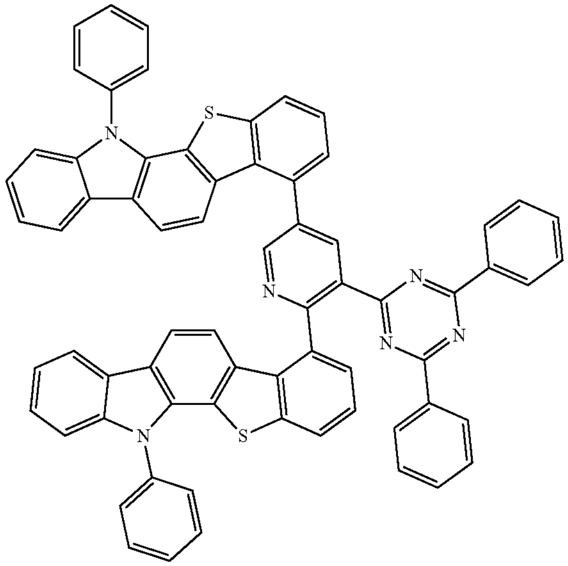
530
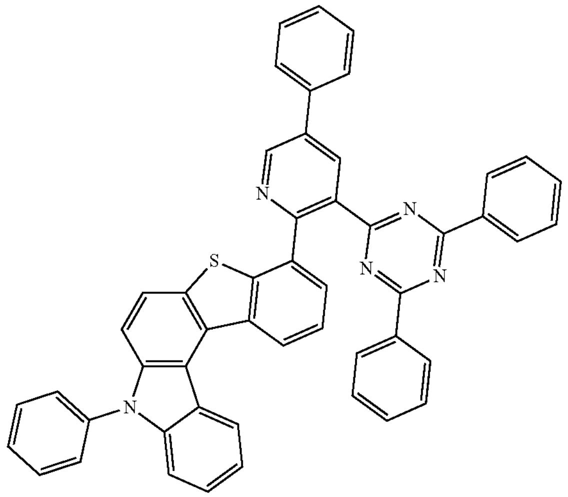

-continued
531
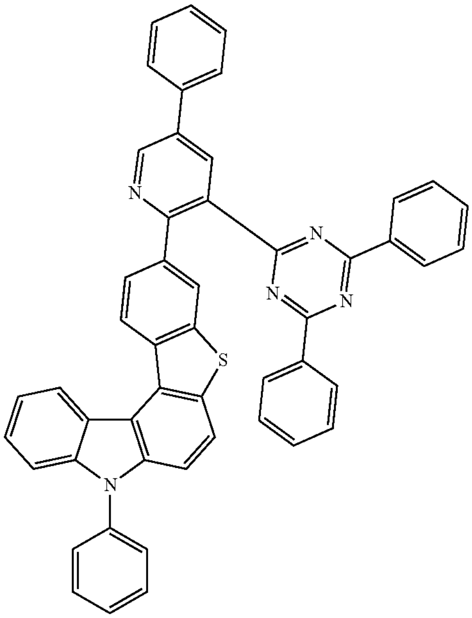
532
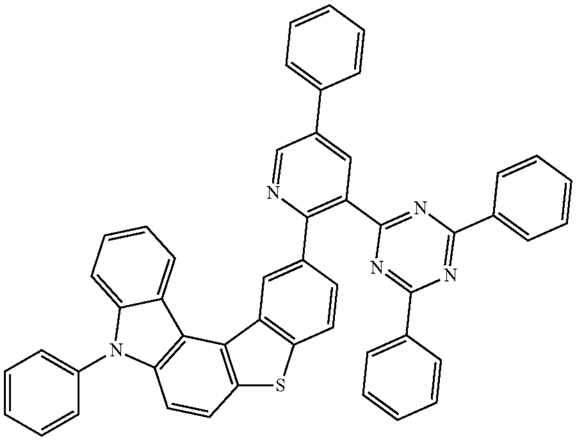
533
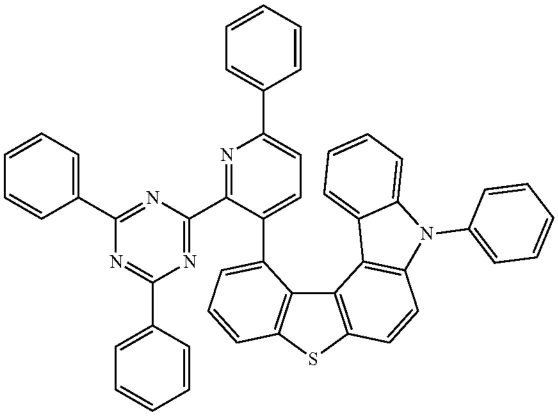
-continued
534
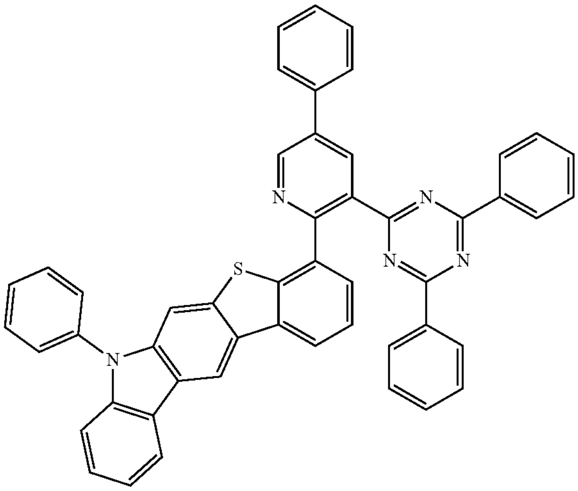
535
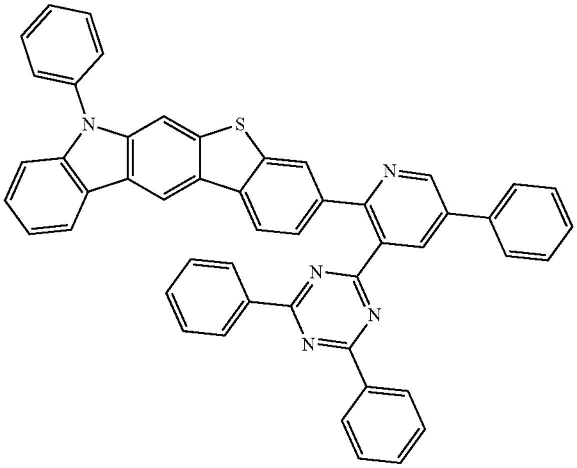
536
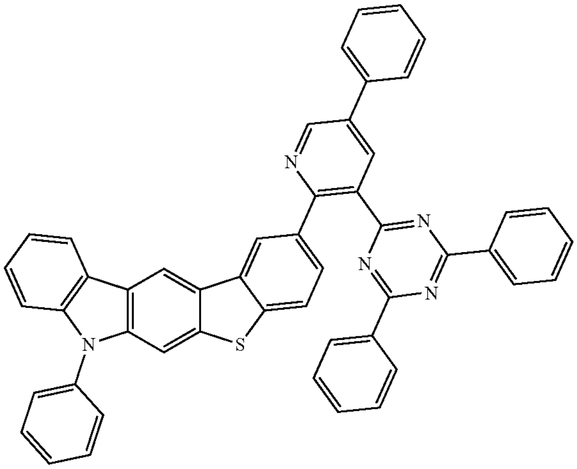

537
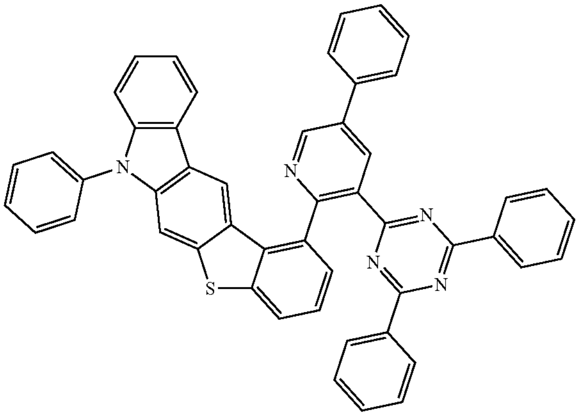
538
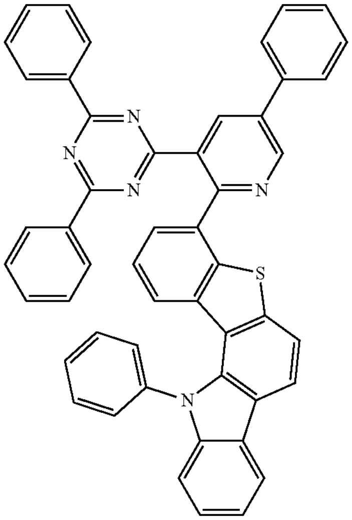
539
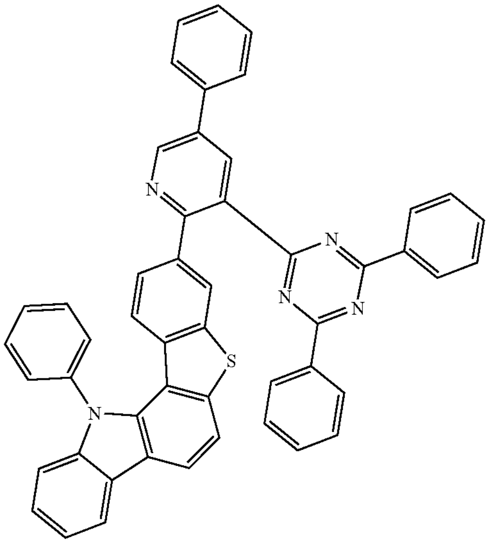
540
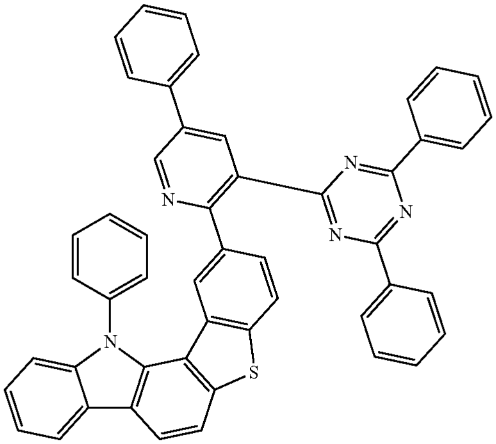
541
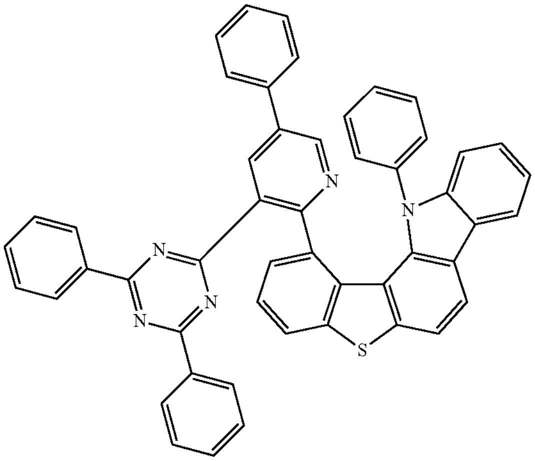
542
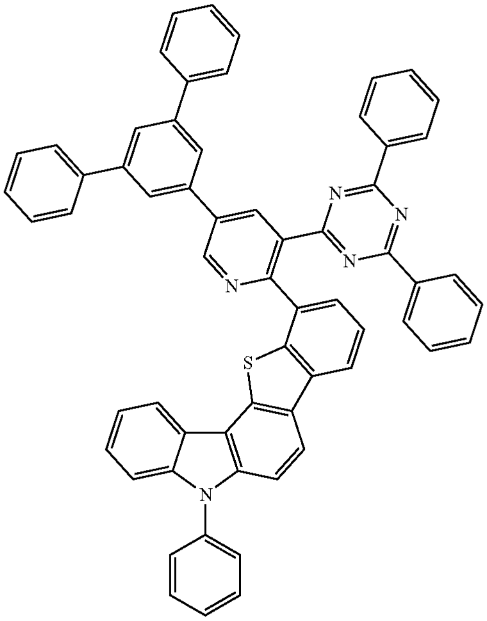

-continued
543
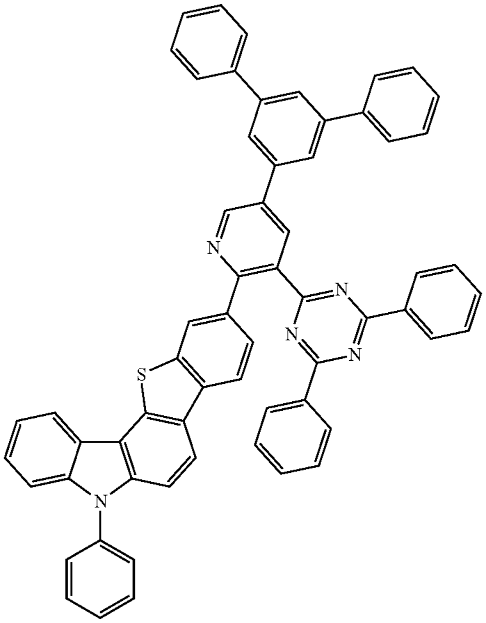
544
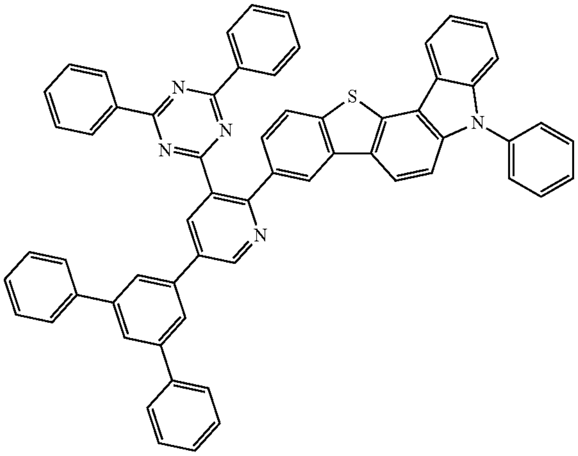
545
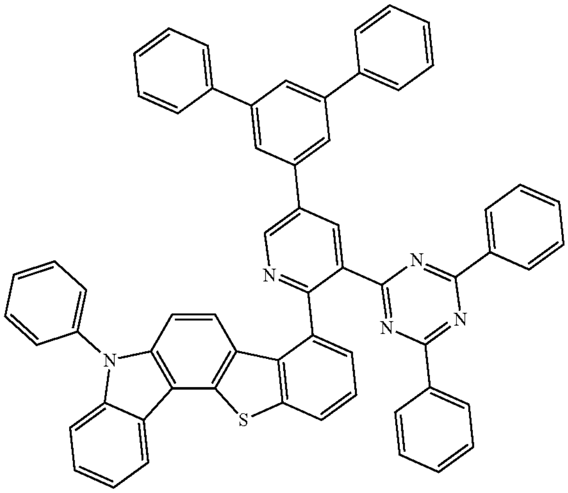
-continued
546
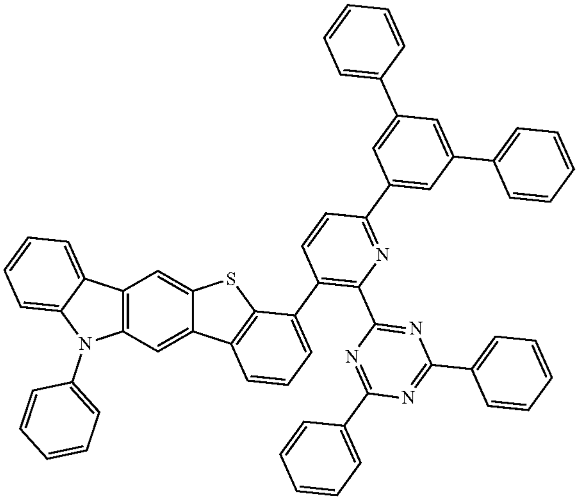
547
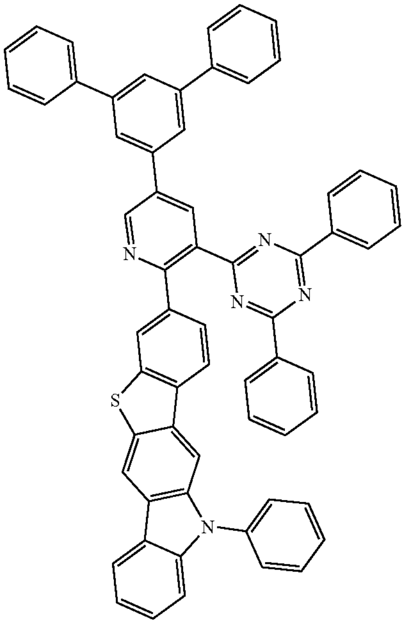

-continued
548
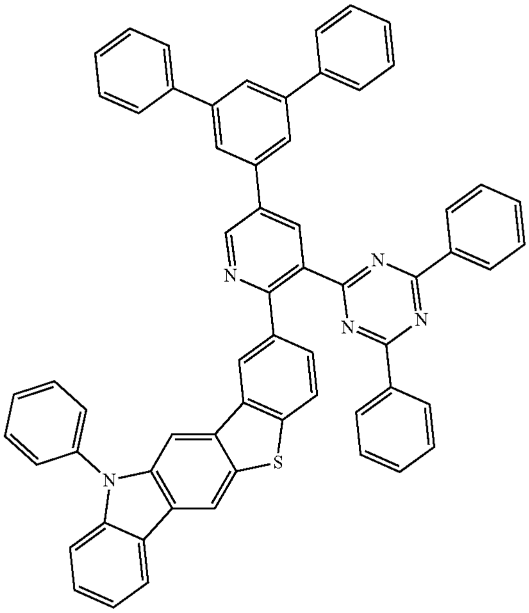
549
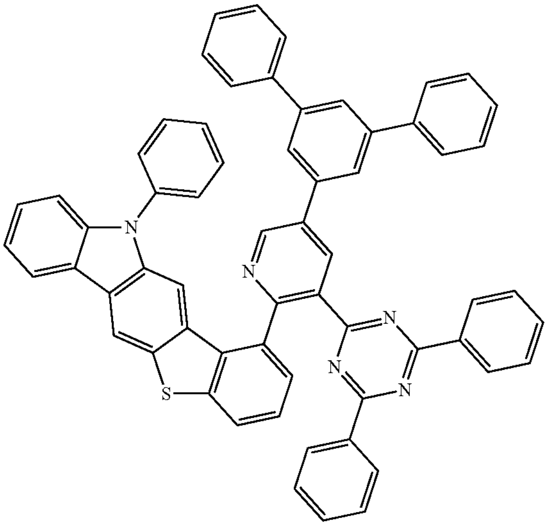
550
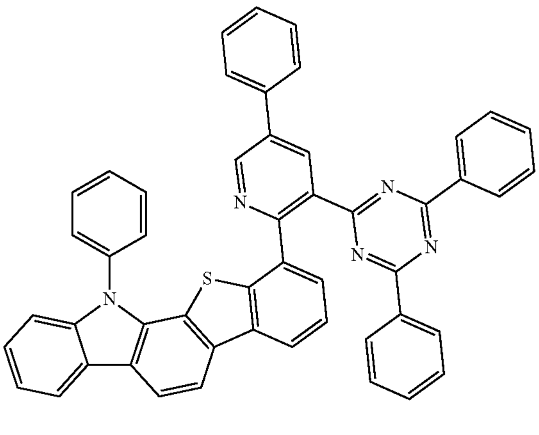
-continued
551
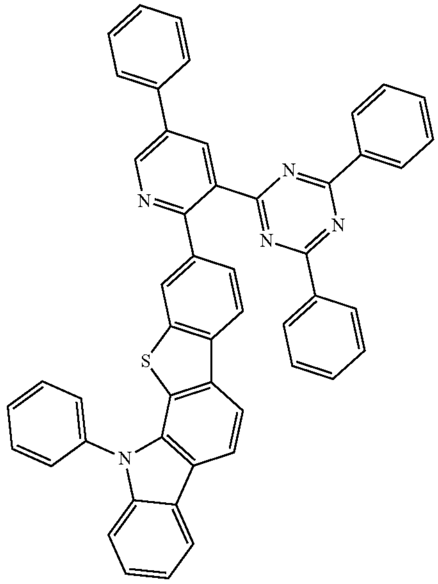
552
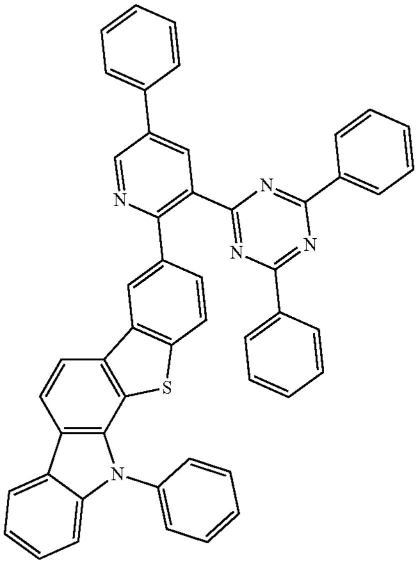
553
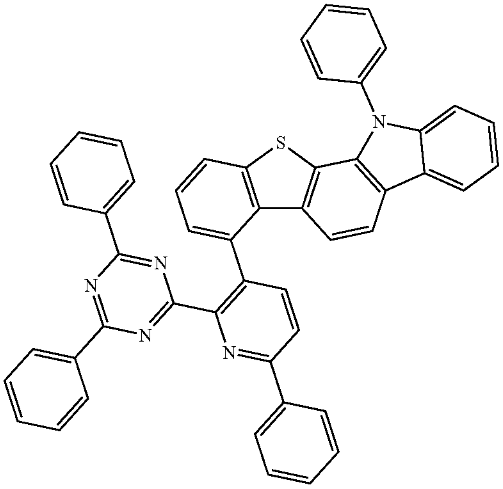

-continued
554
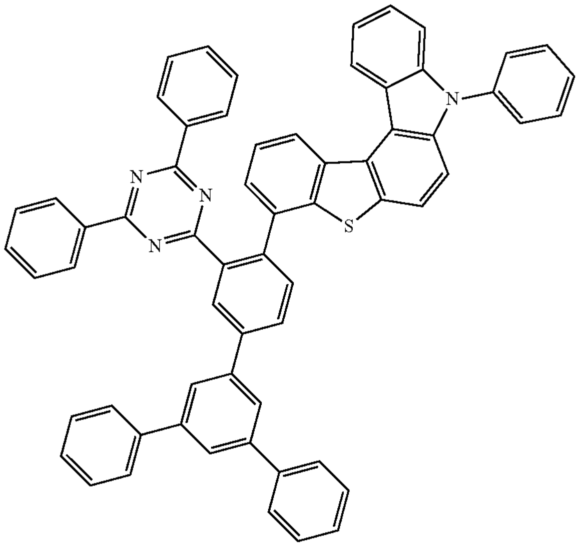
555
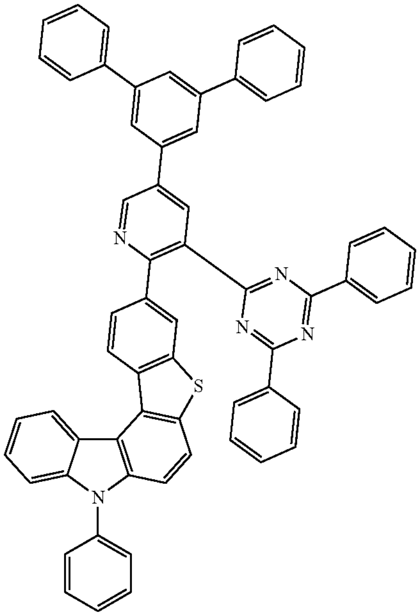
-continued
556
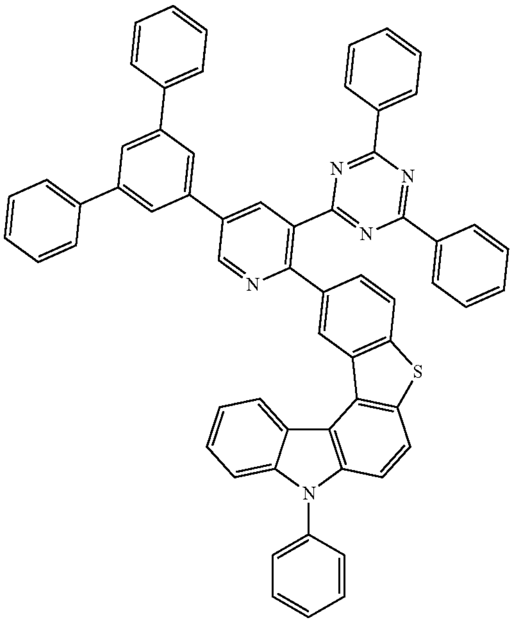
557
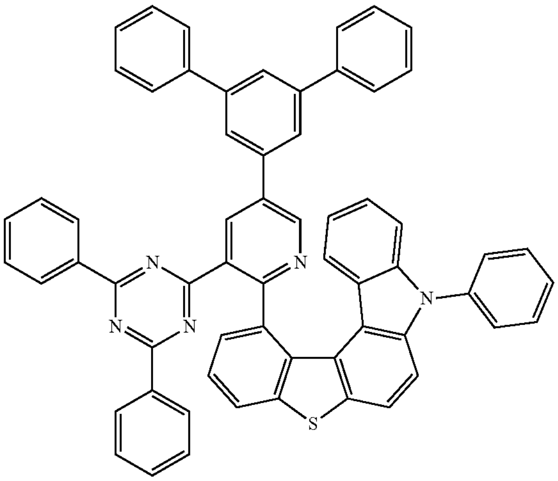
558
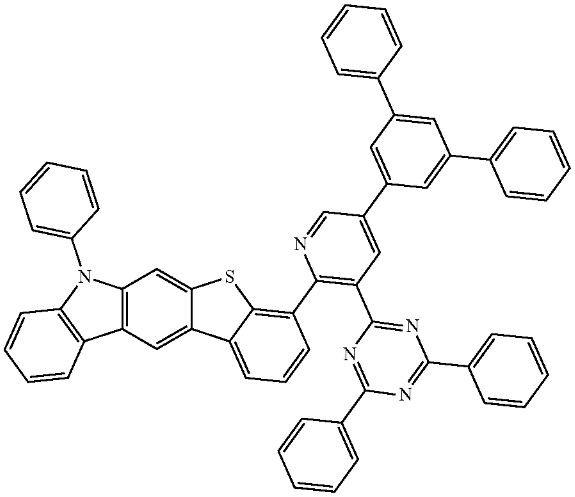

-continued
559
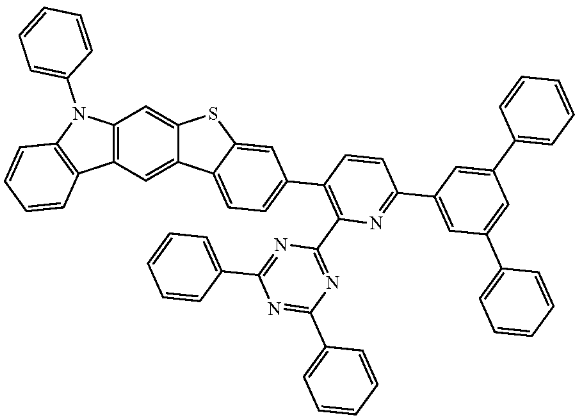
560
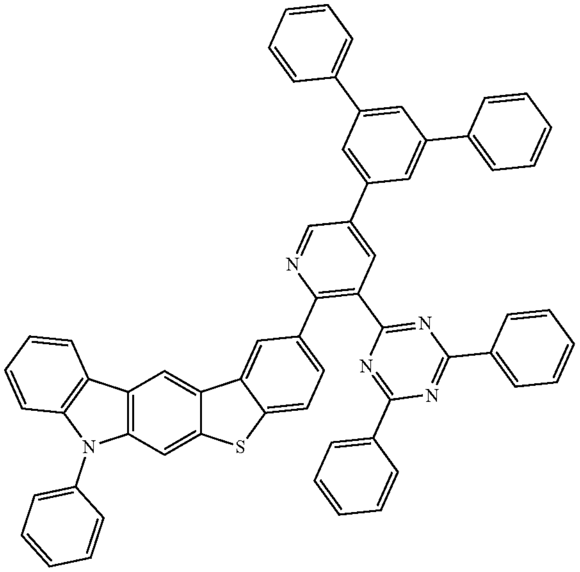
561
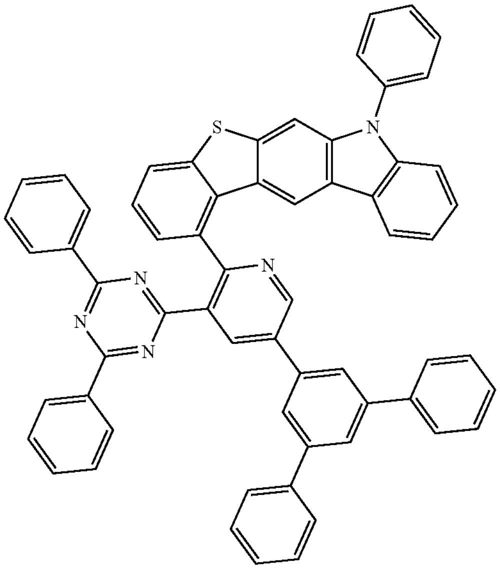
-continued
562
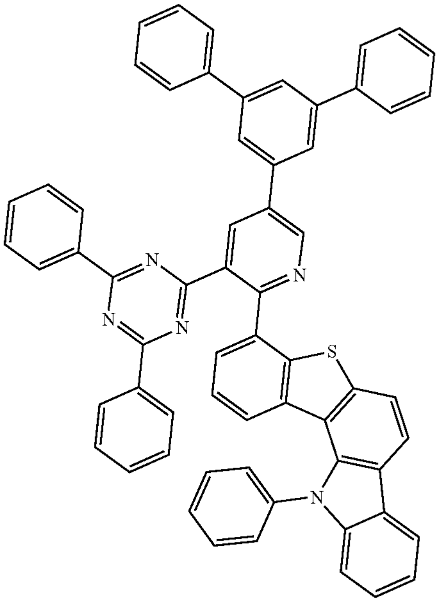
563
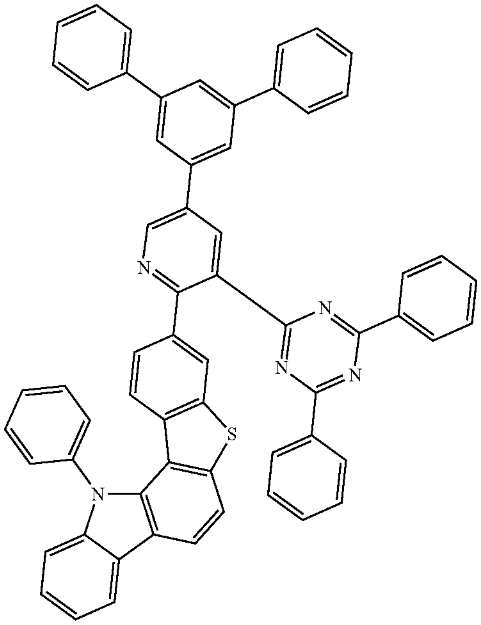

-continued
564
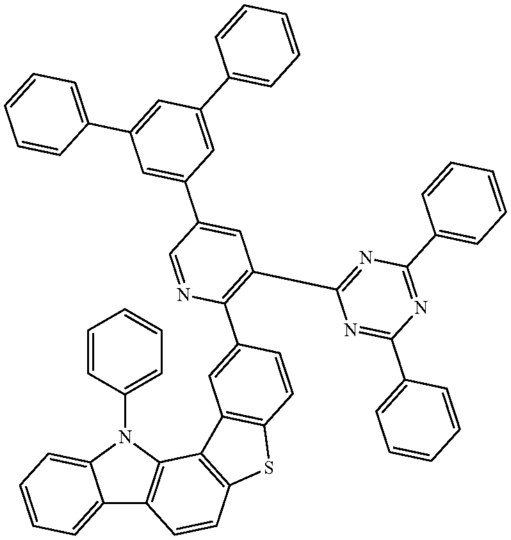
565
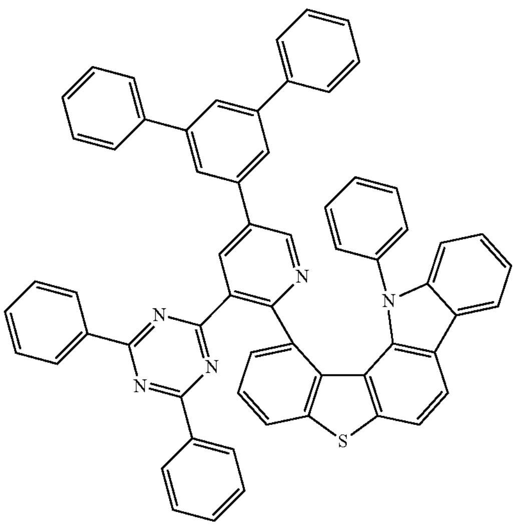
-continued
566
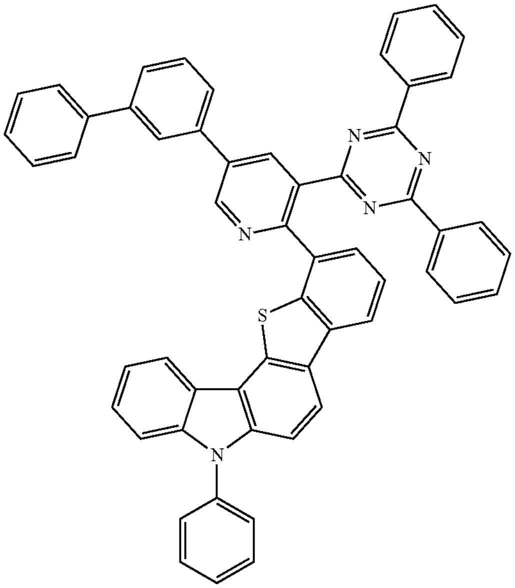
567
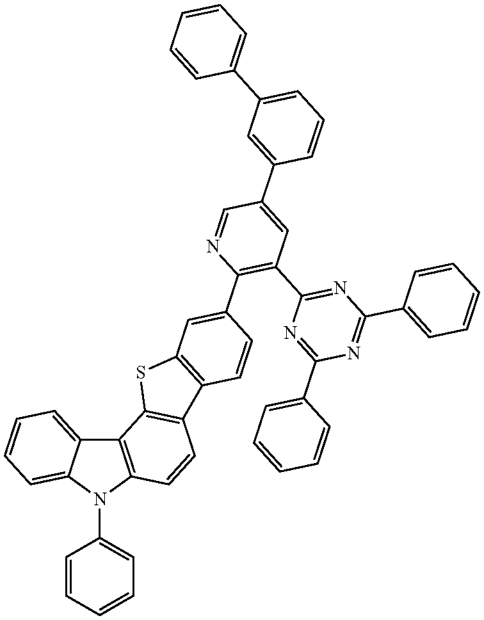

-continued
568
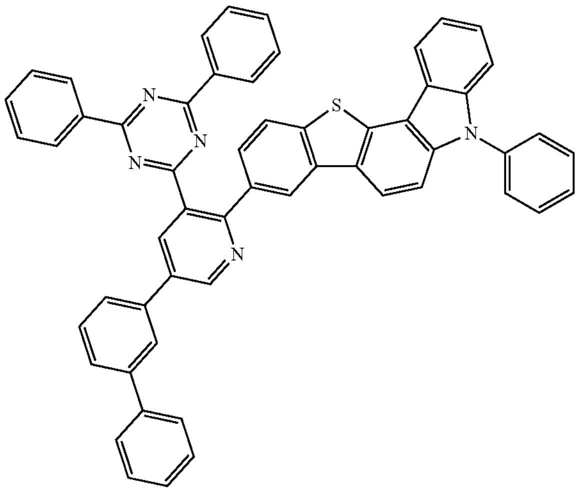
569
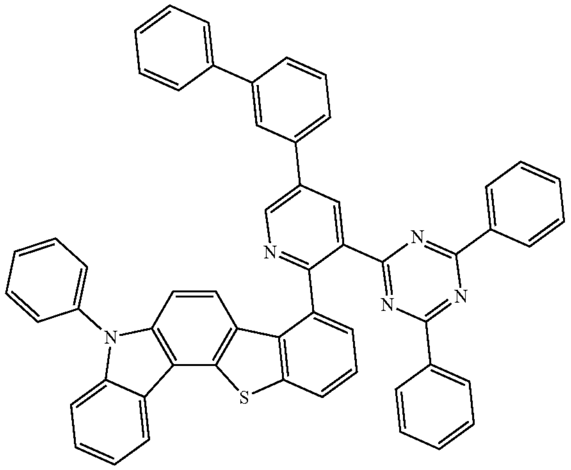
570
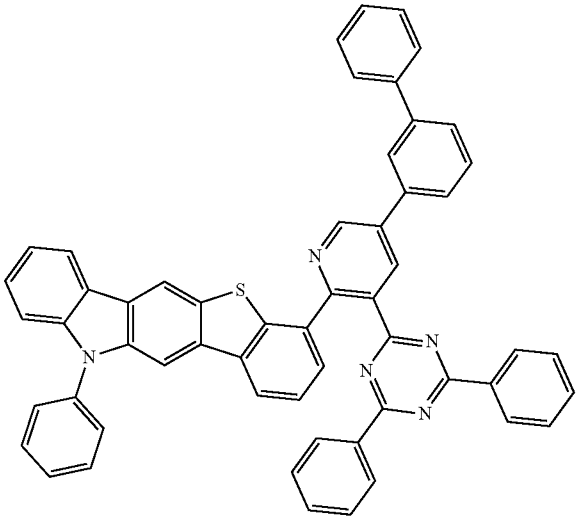
-continued
571
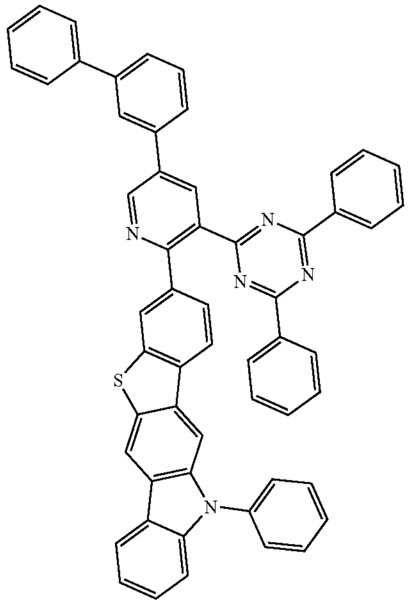
572
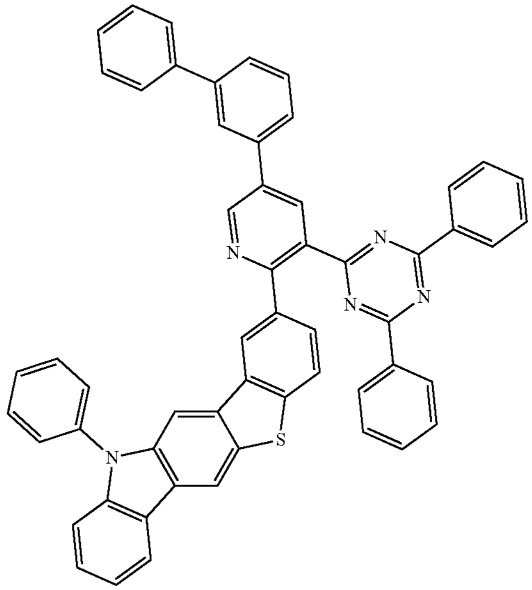

573
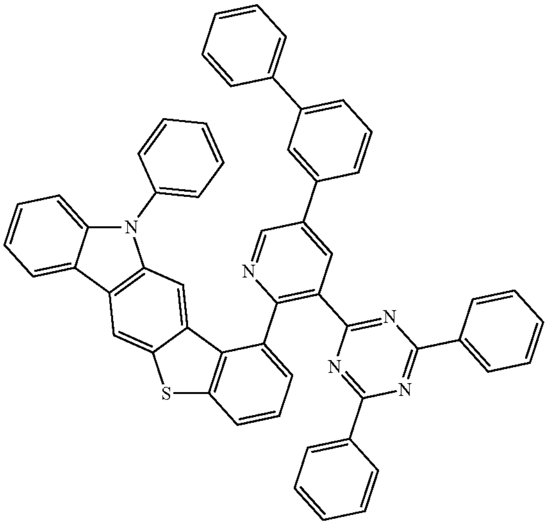
574
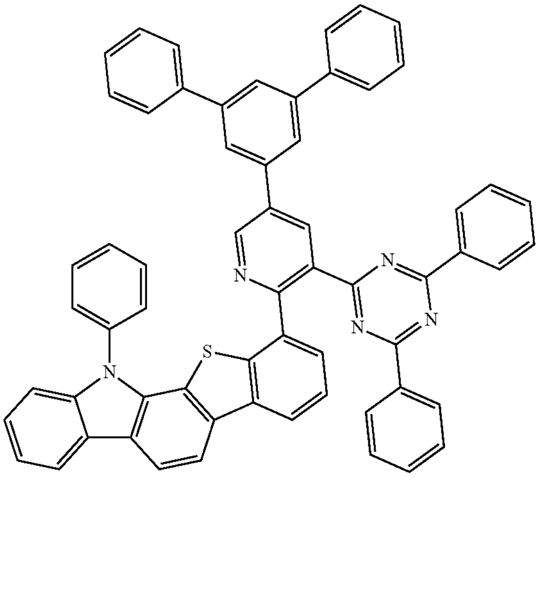
575
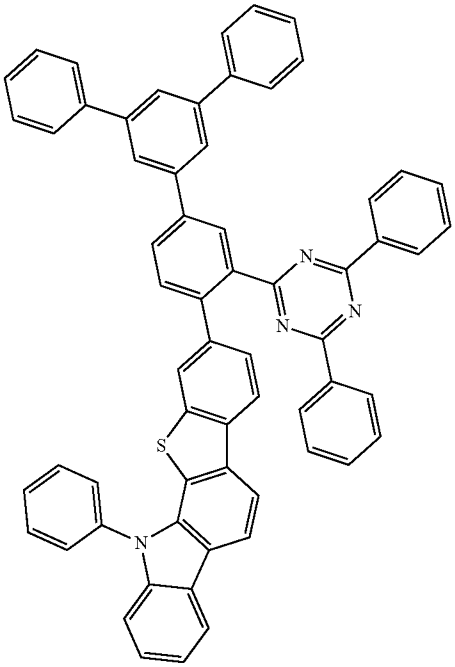
576
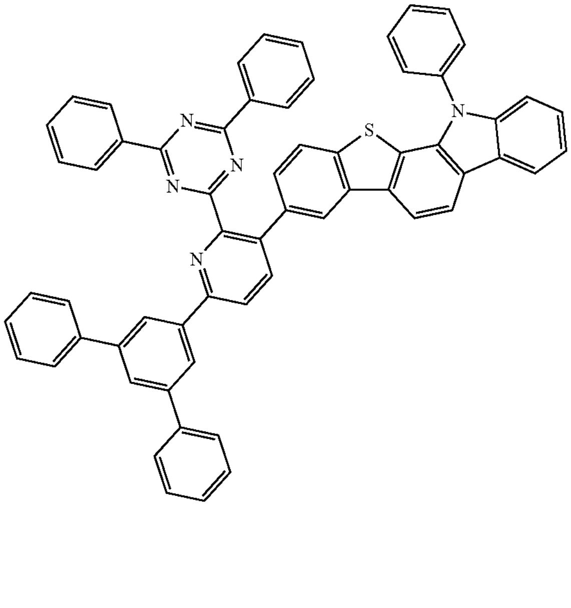

-continued
577
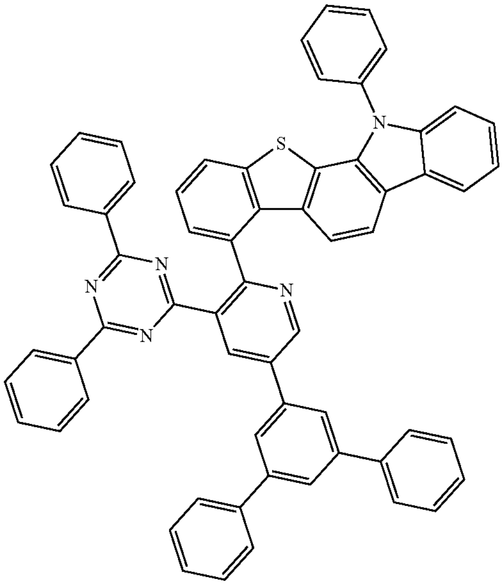
578
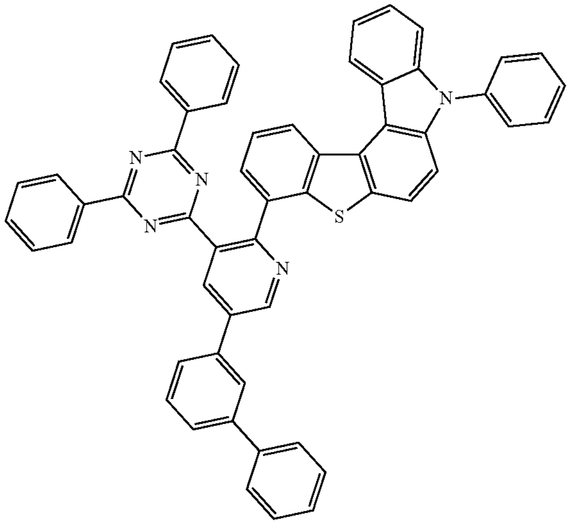
-continued
579
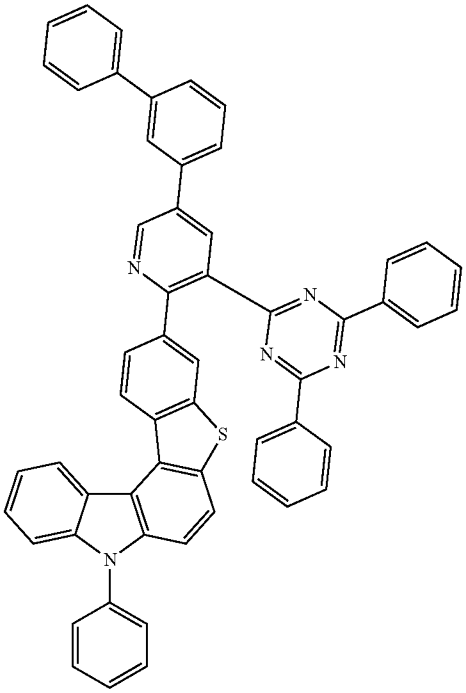
580
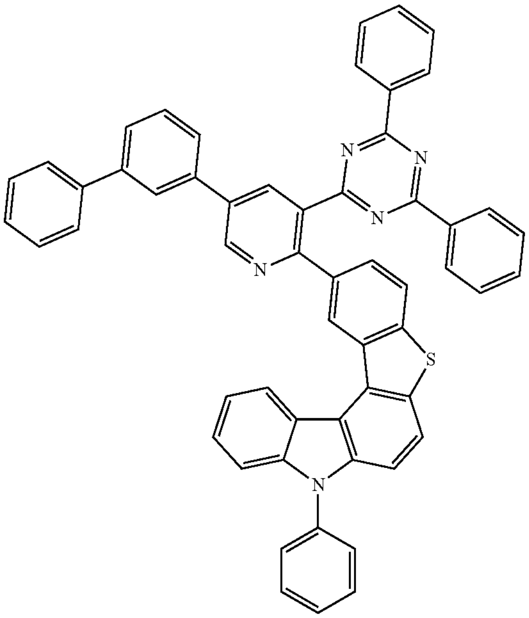

581
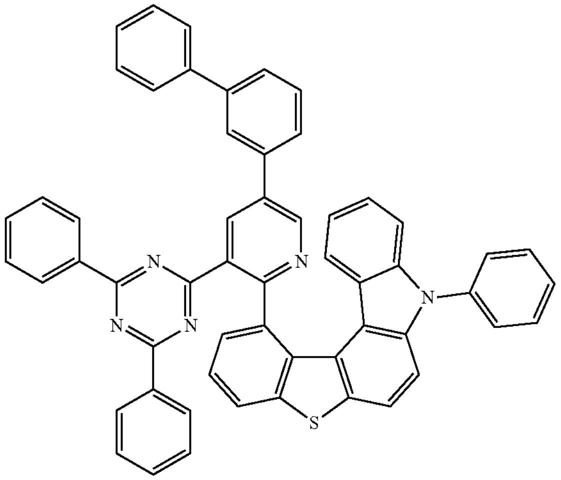
582
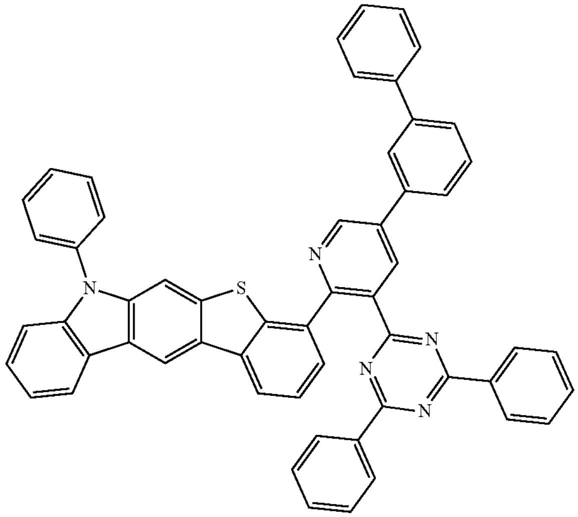
583
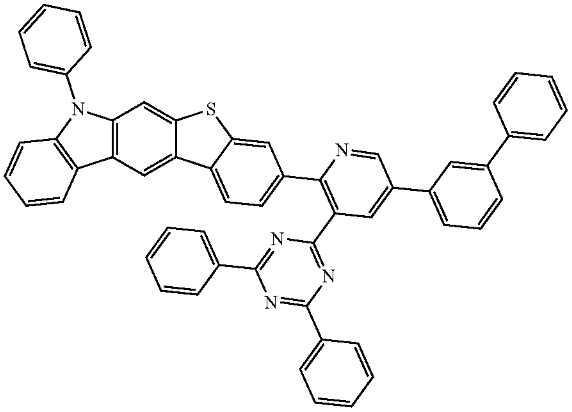
584
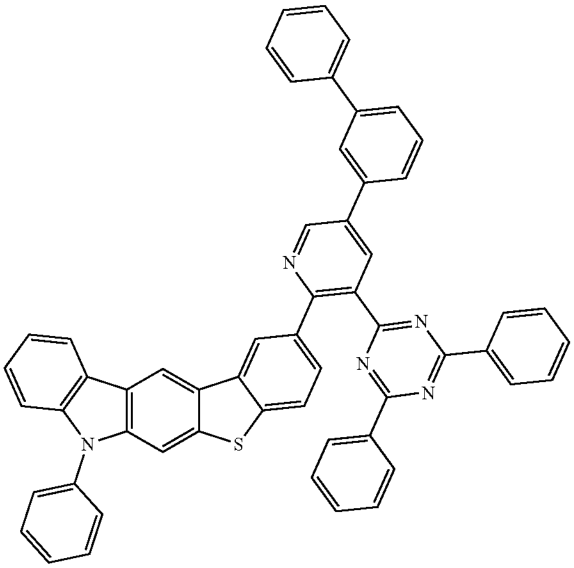
585
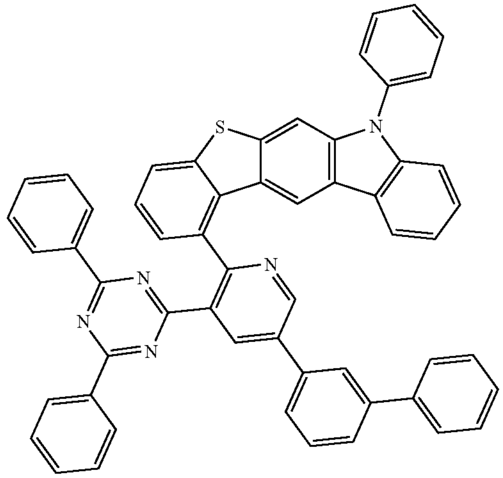
586
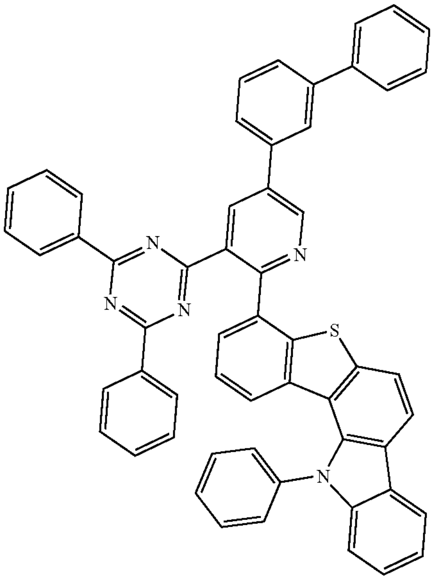

587
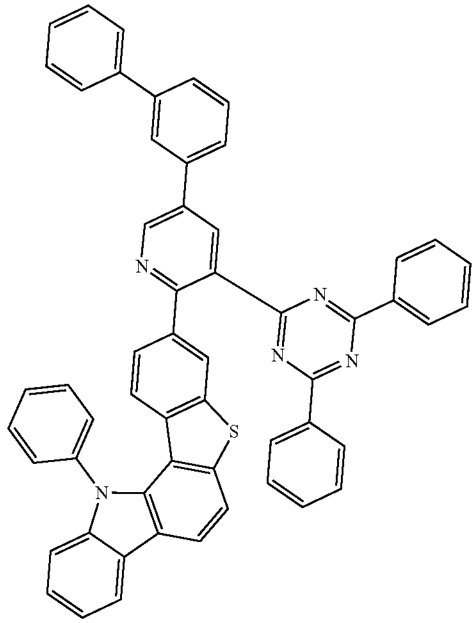
588
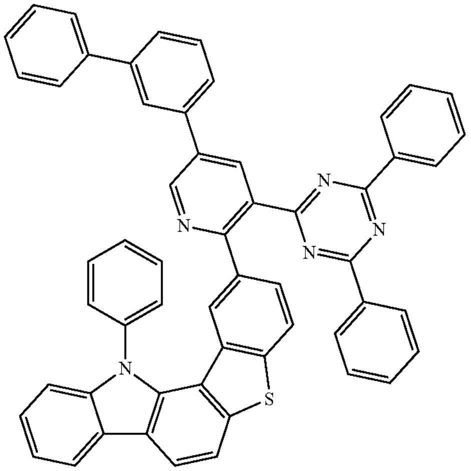
589
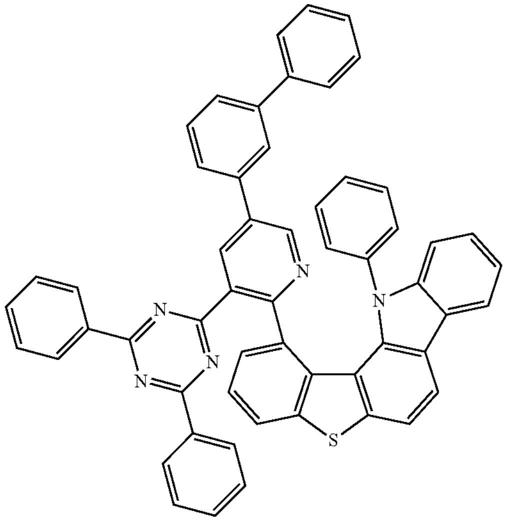
590
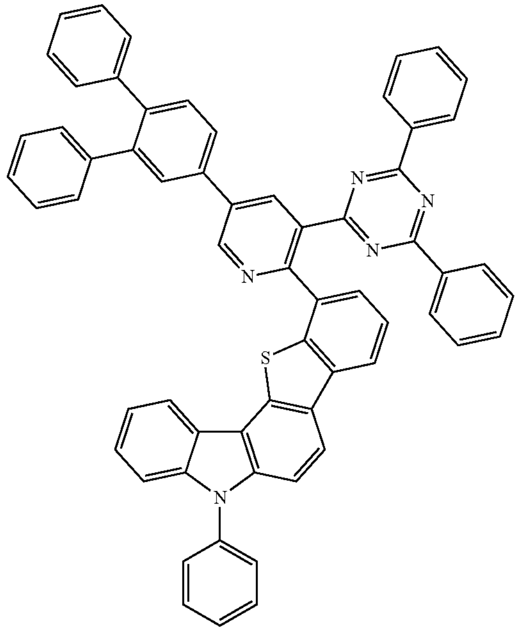
591
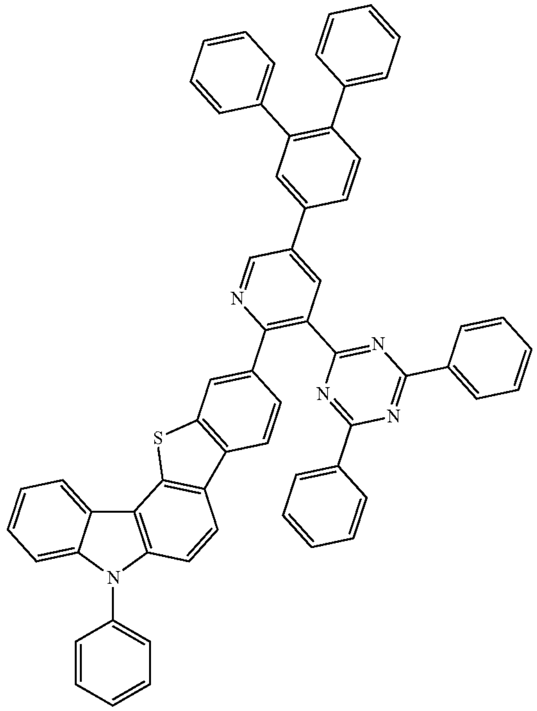

-continued
592
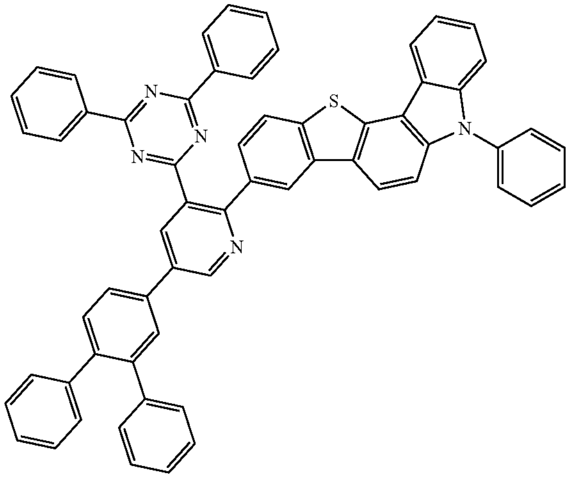
593
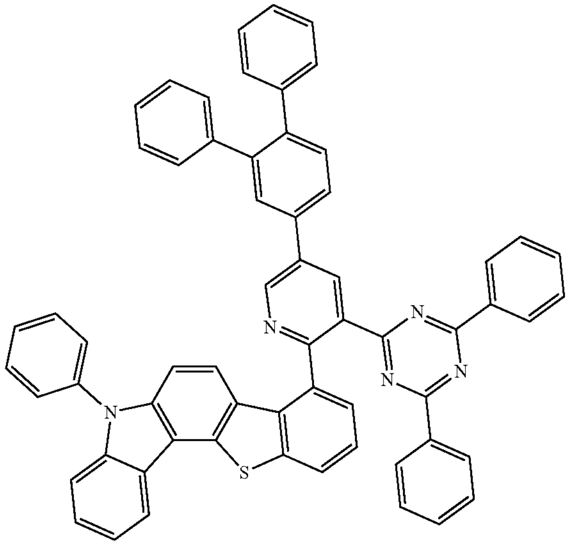
594
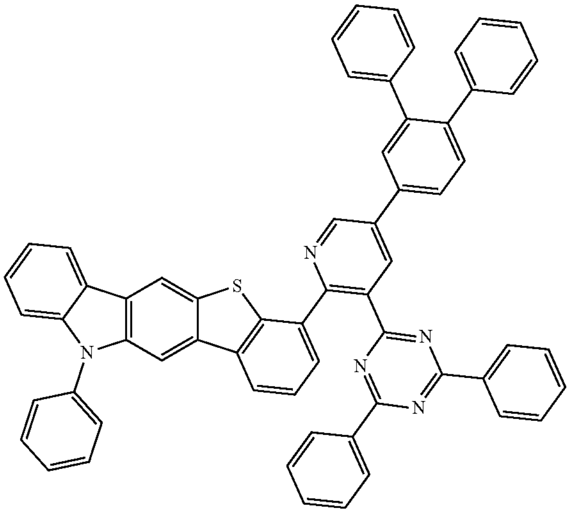
-continued
595
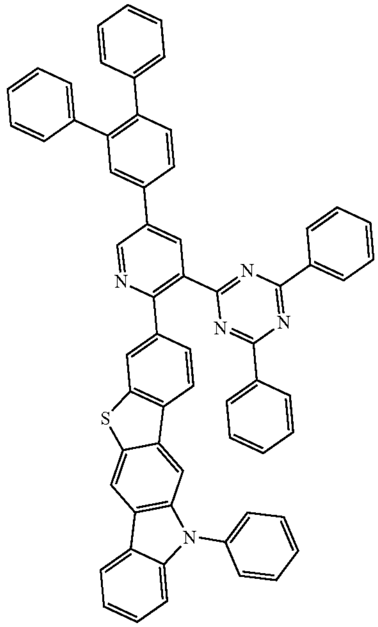
596
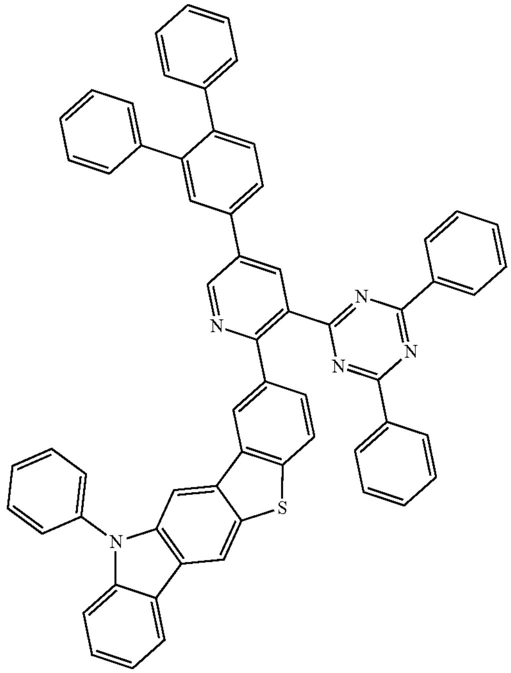

597
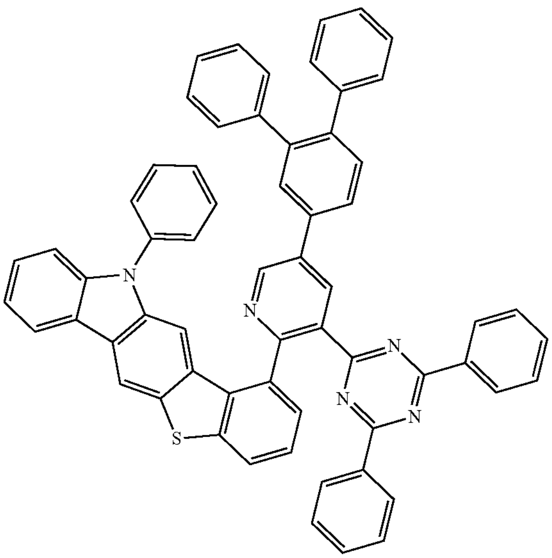
598
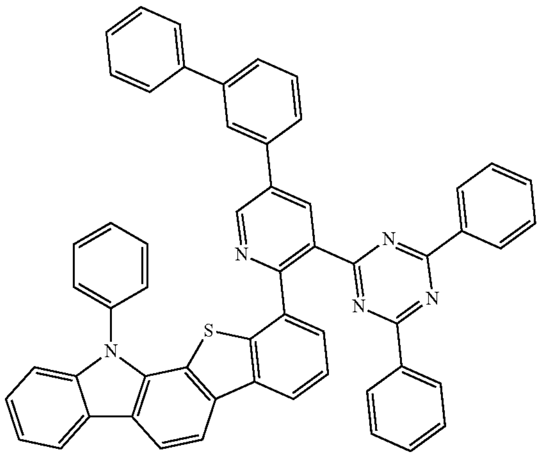
599
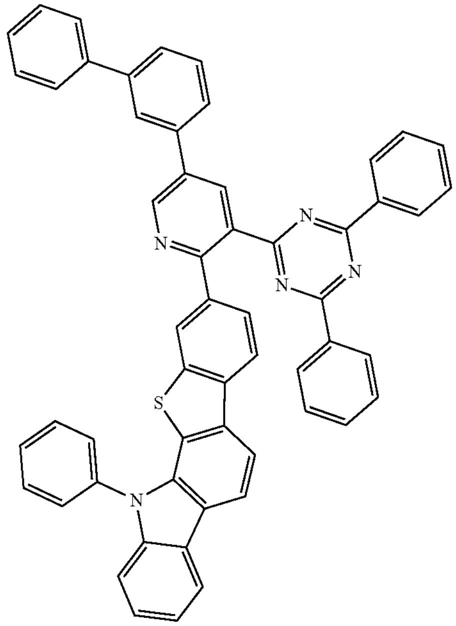
600
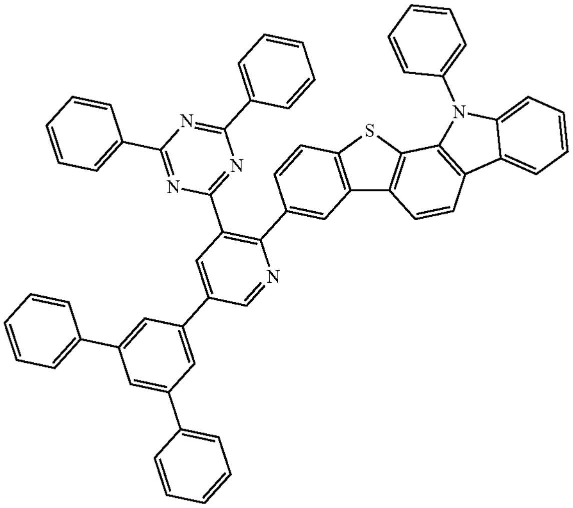
601
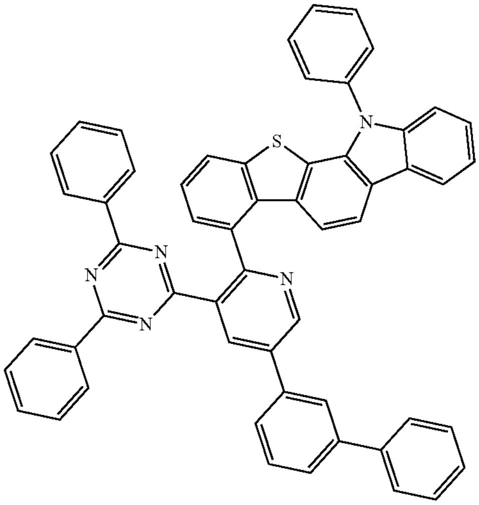

-continued
602
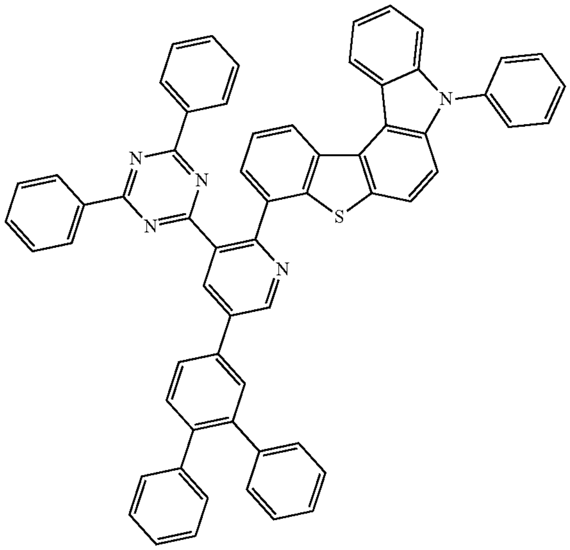
603
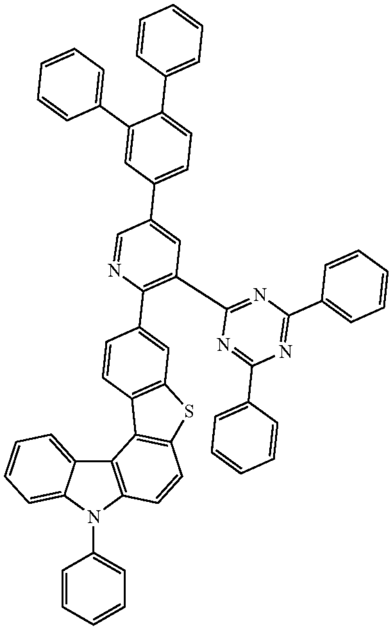
-continued
604
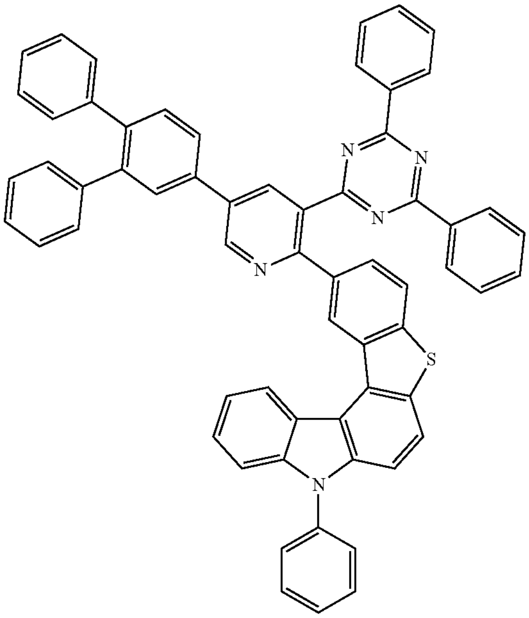
605
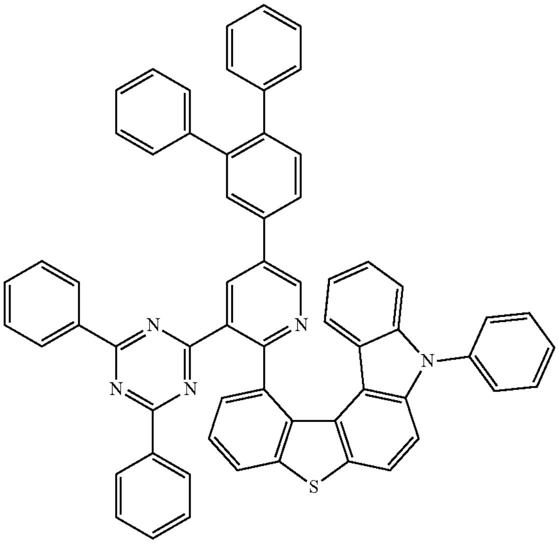

-continued
606
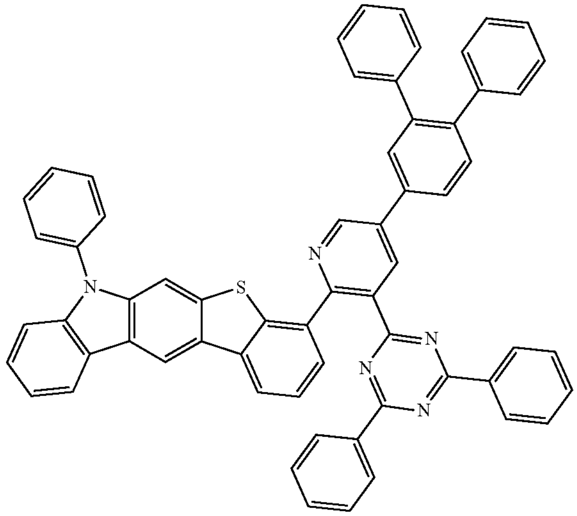
607
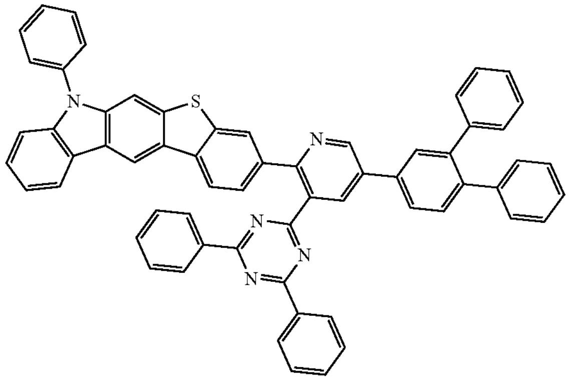
608
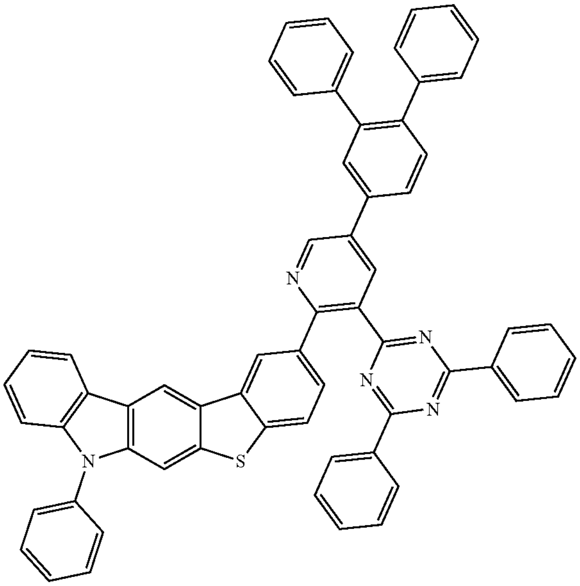
-continued
609
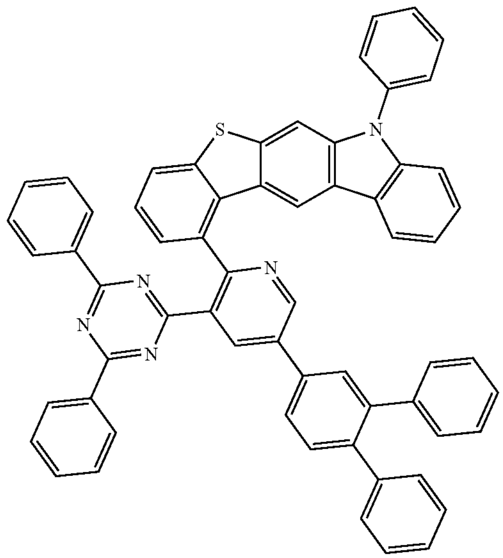
610
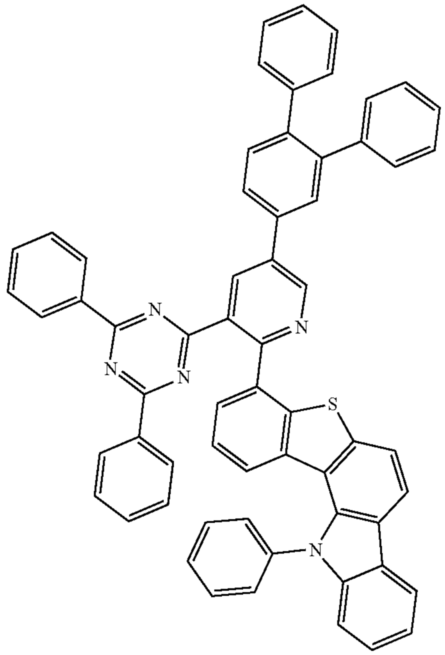

611
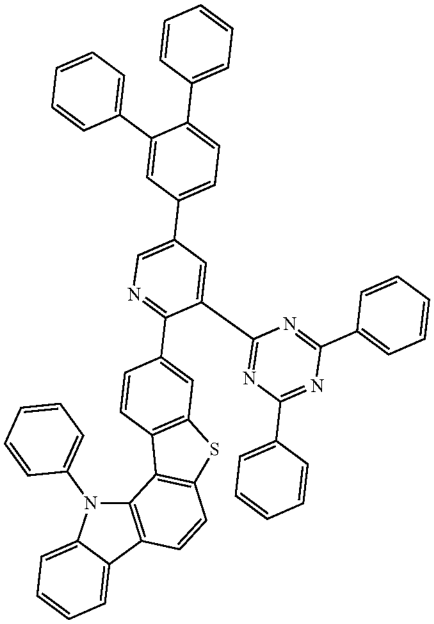
612
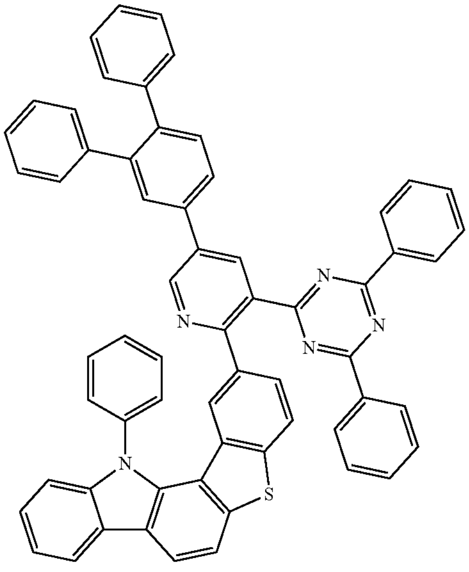
613
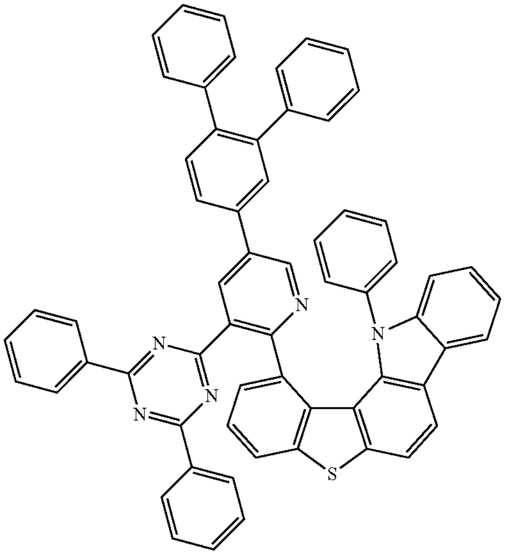
614
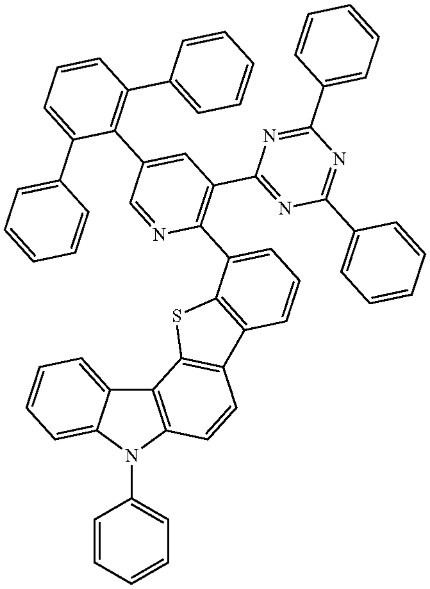

-continued
615
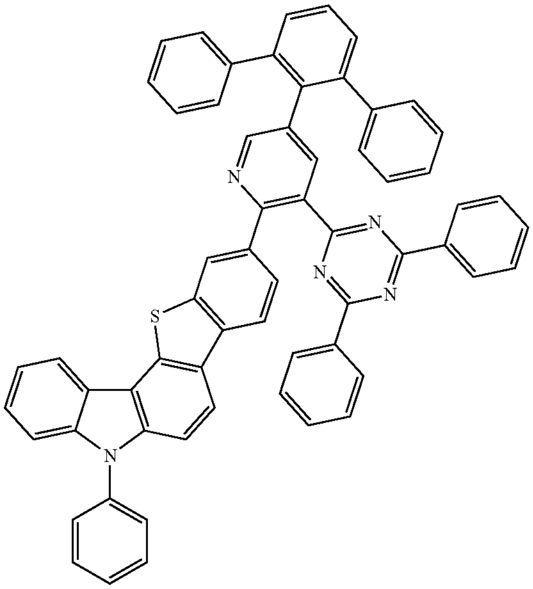
616
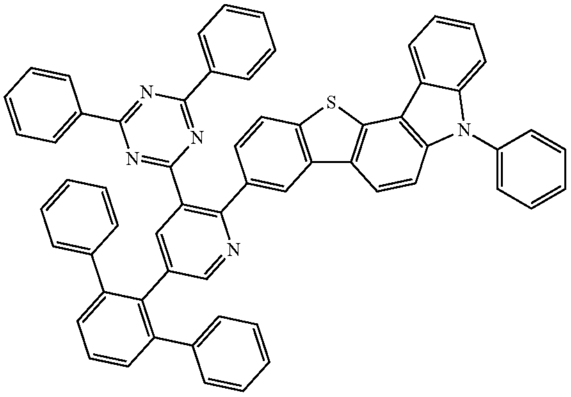
617
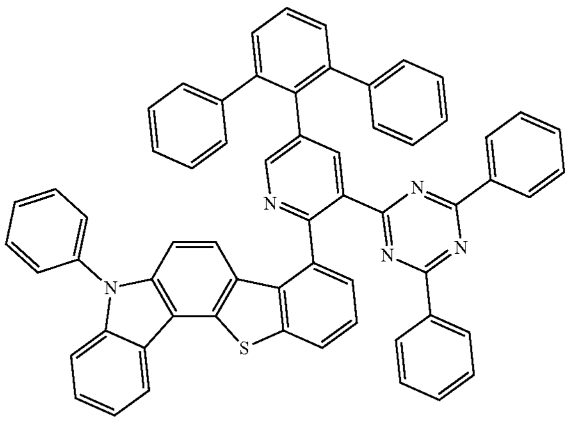
-continued
618
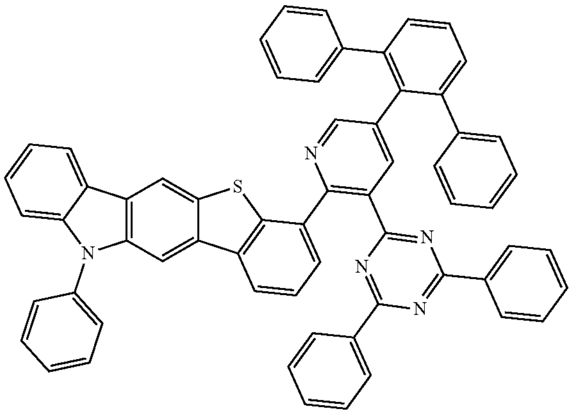
619
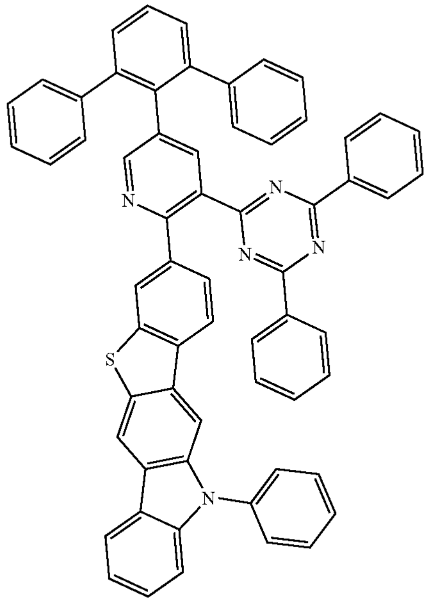
620
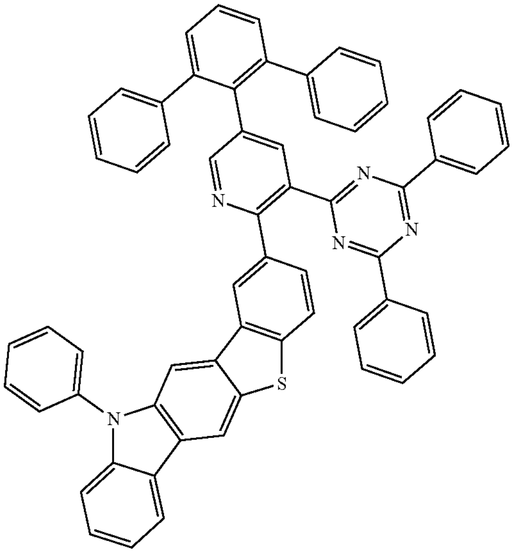

-continued
621
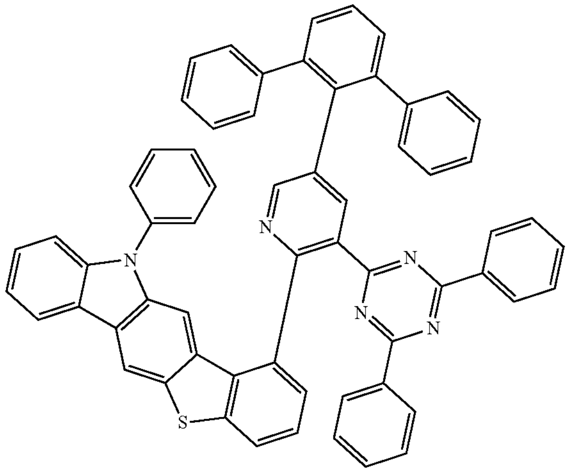
622
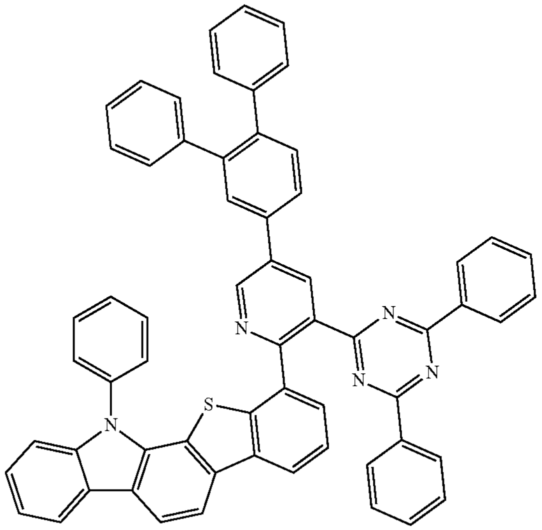
623
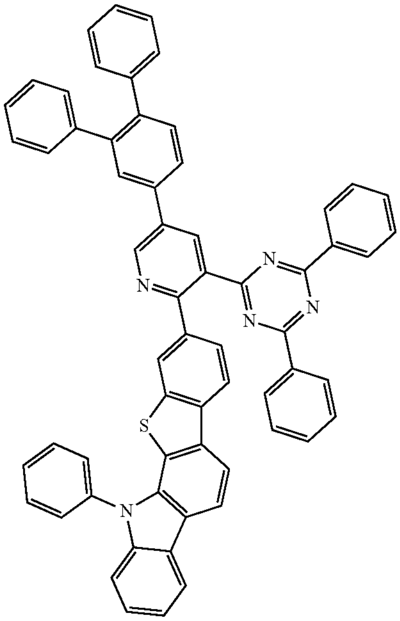
-continued
624
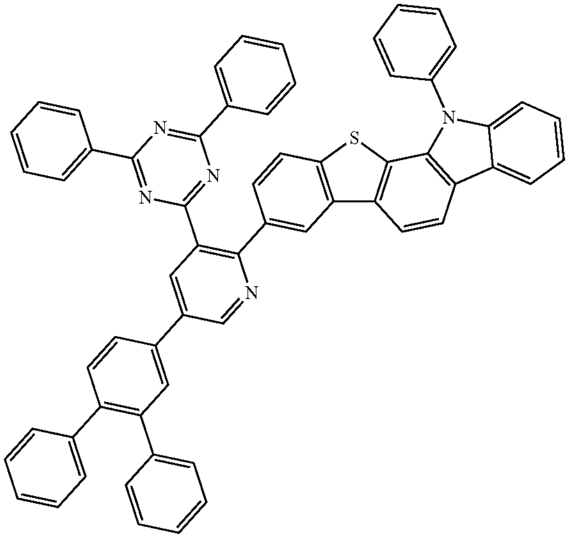
625
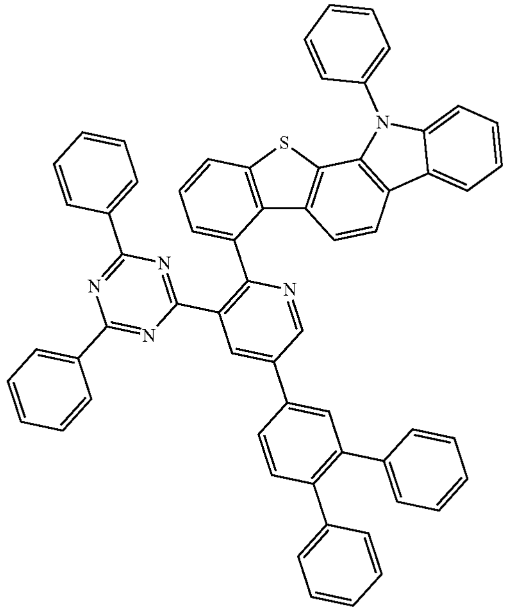
626
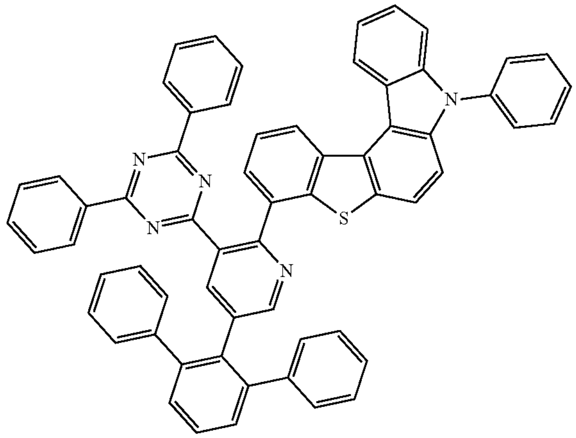

-continued
627
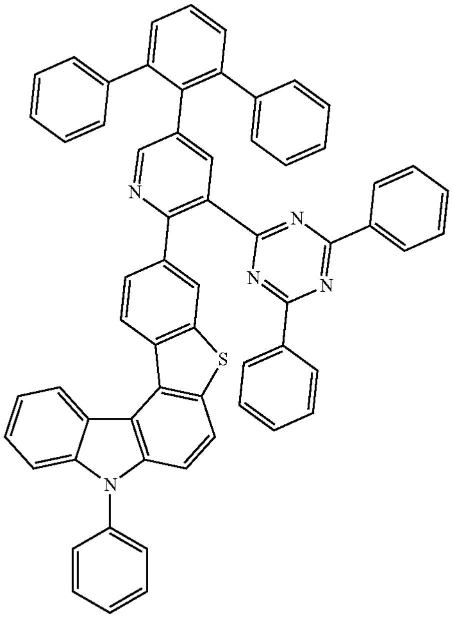
628
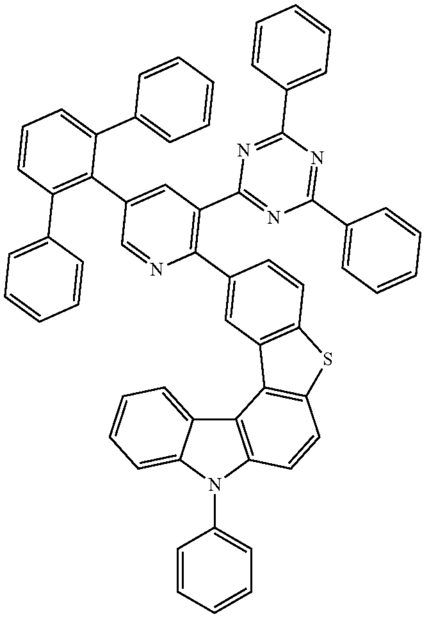
-continued
629
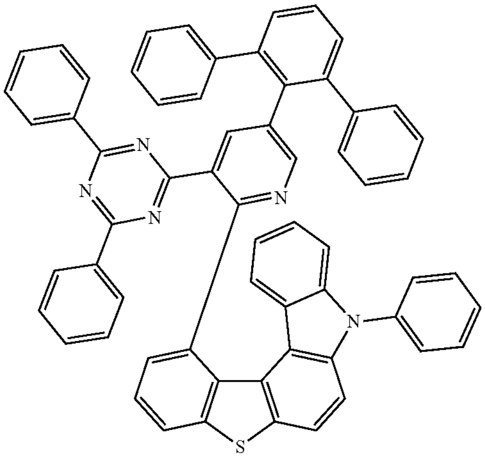
630
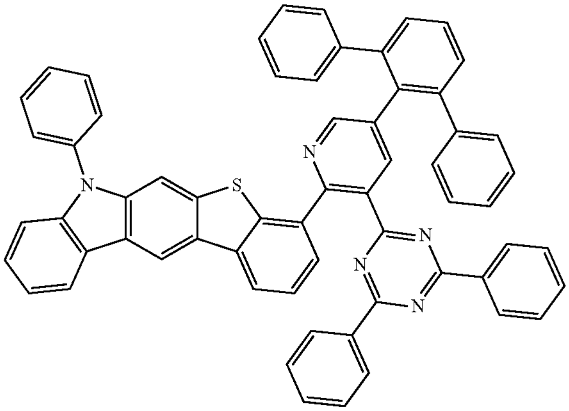
631
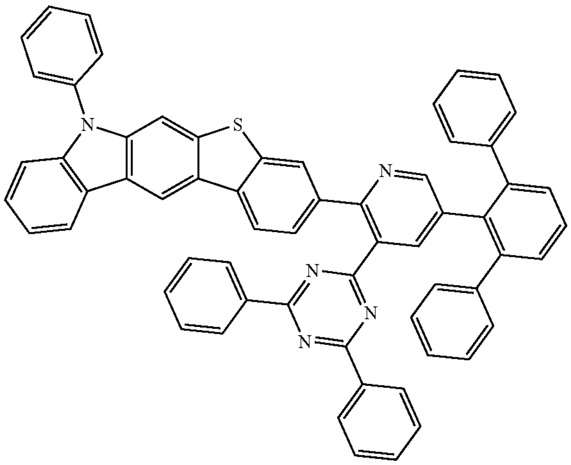

-continued
632
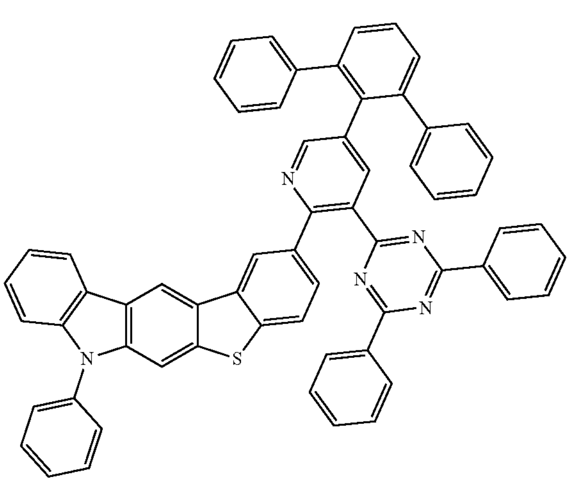
633
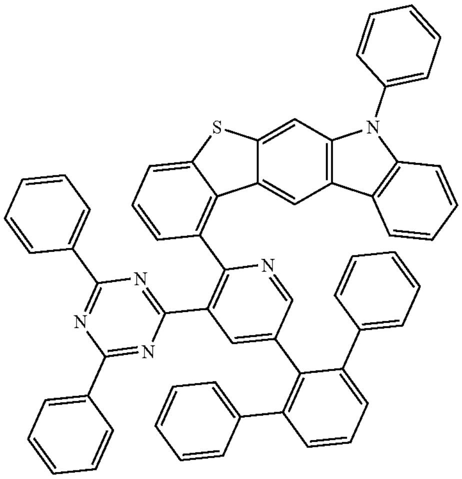
634
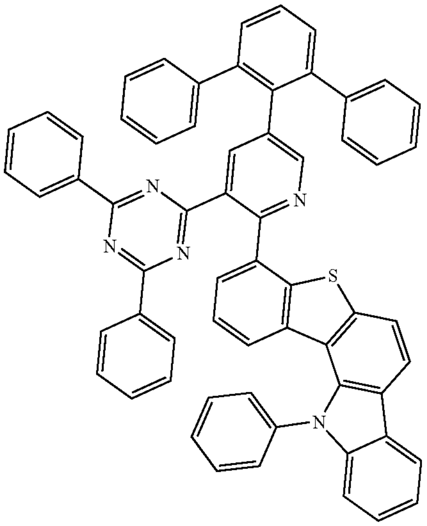
635
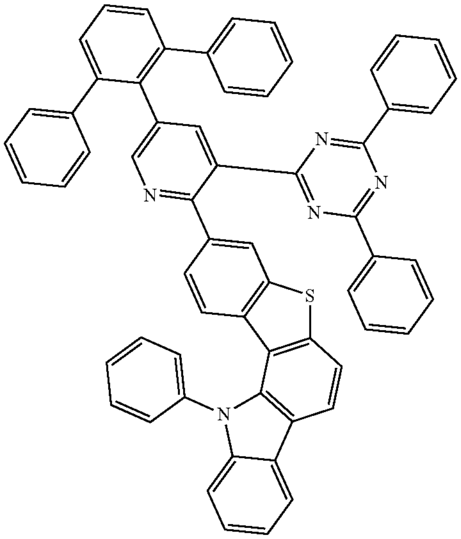
636
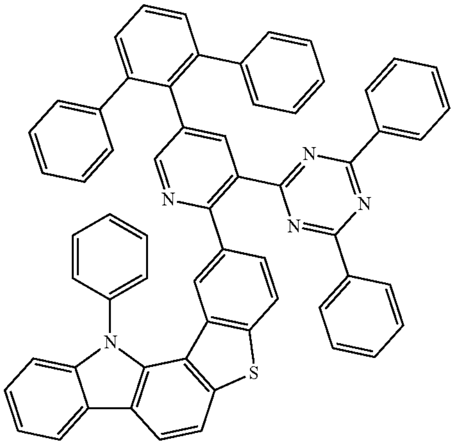
637
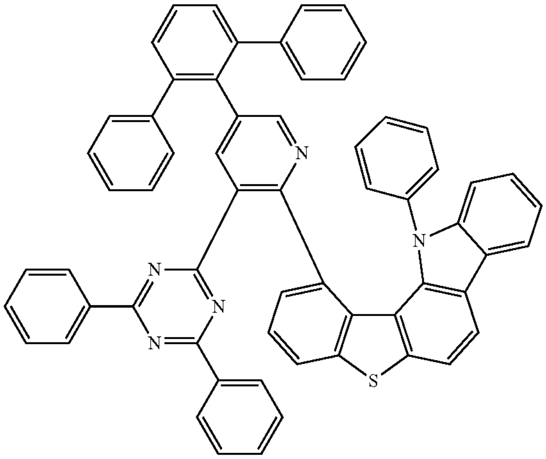

-continued
638
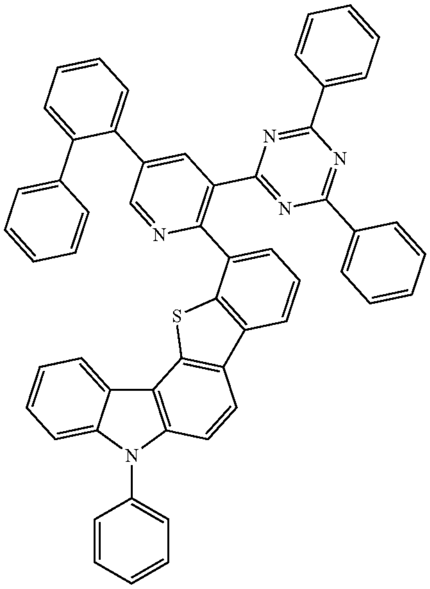
639
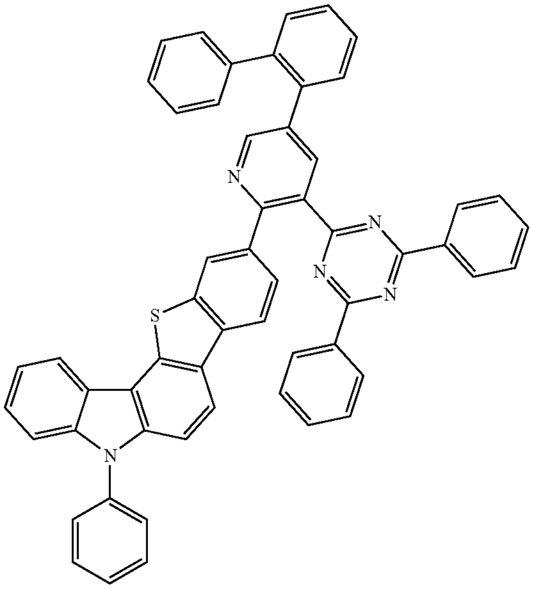
640
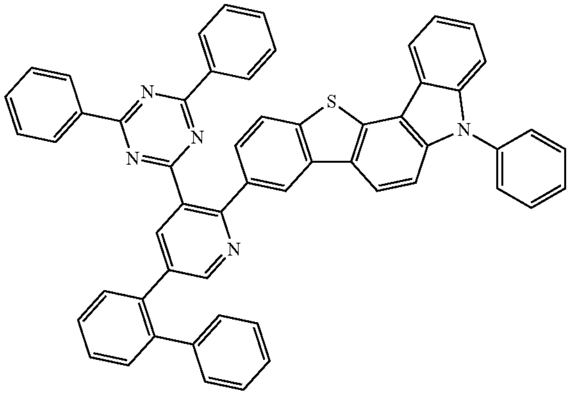
-continued
641
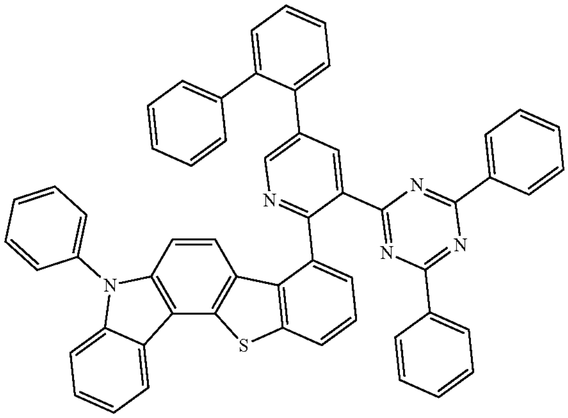
642
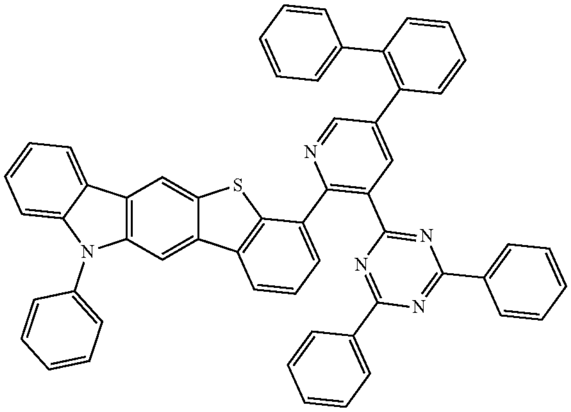
643
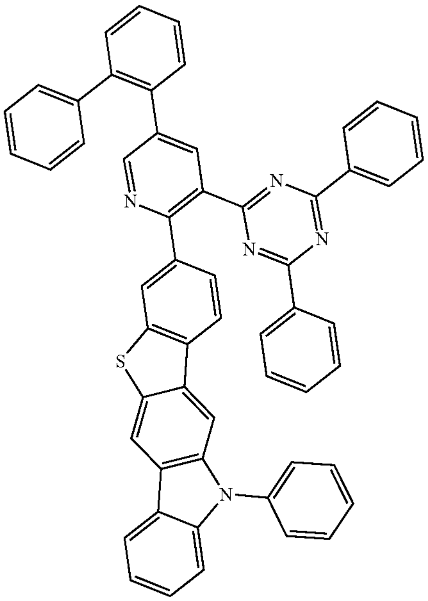

644
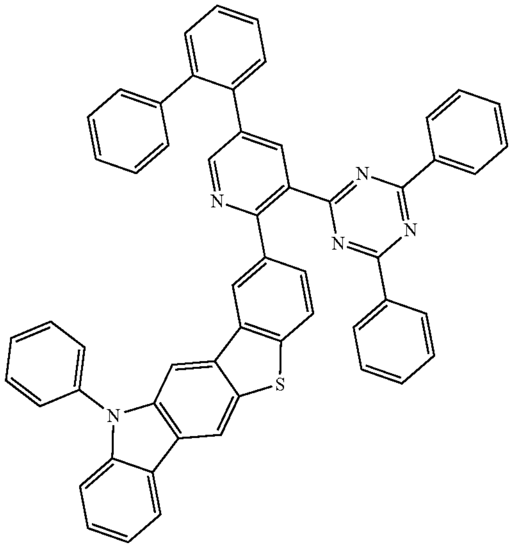
645
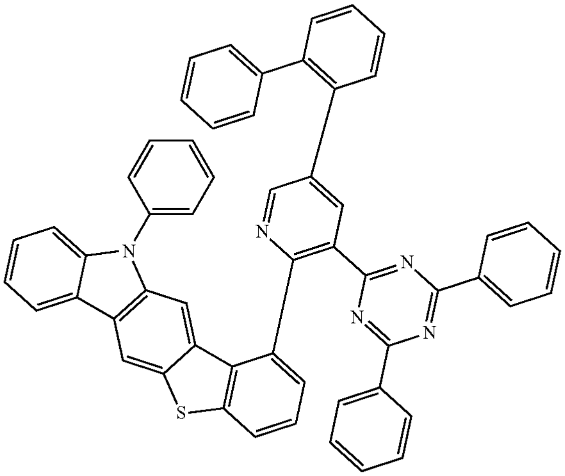
646
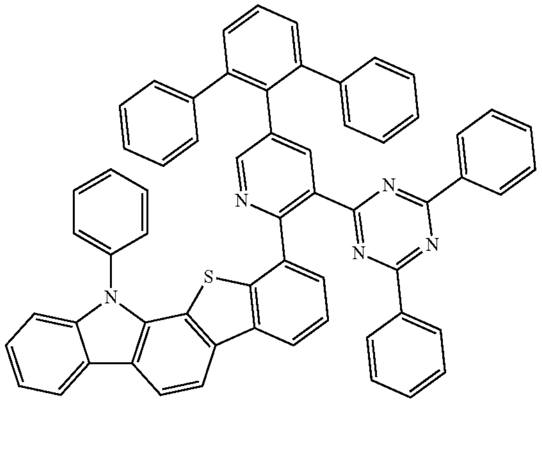
647
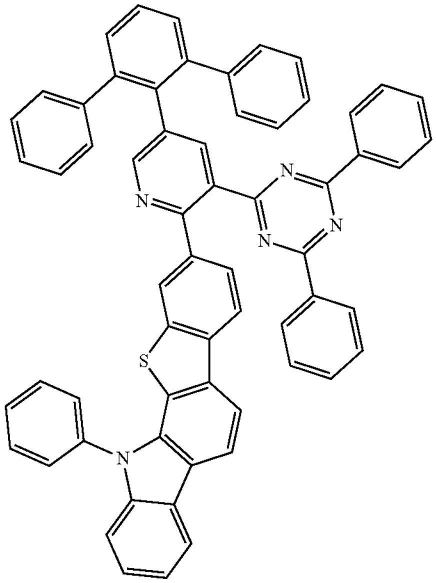
648
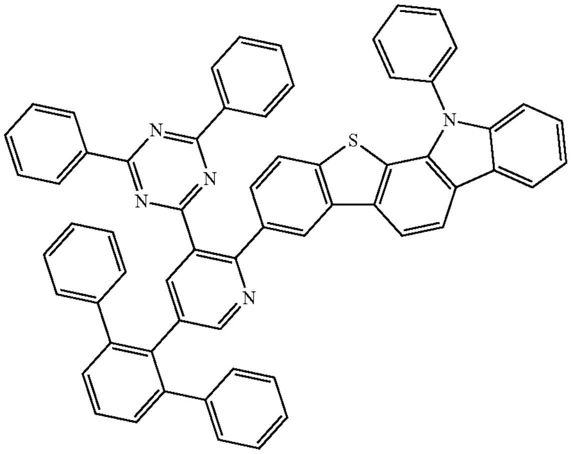
649
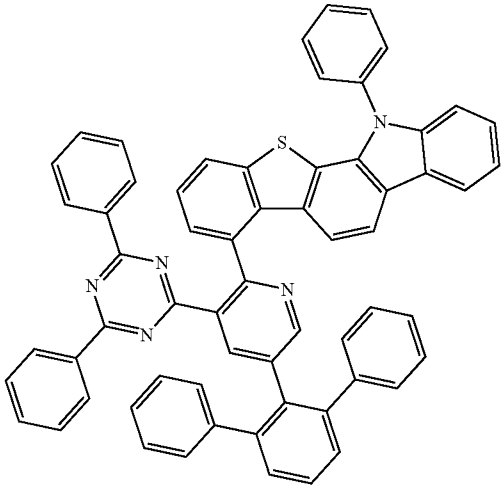

-continued
650
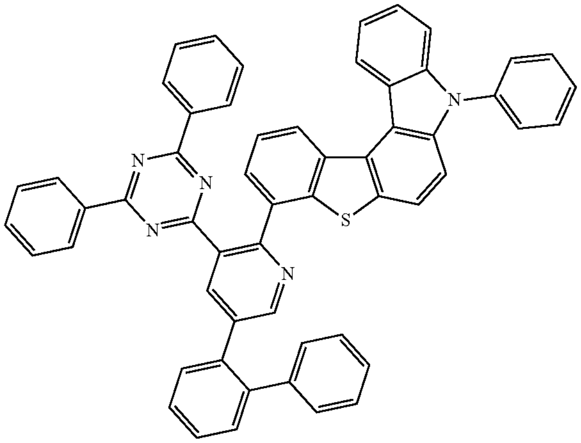
651
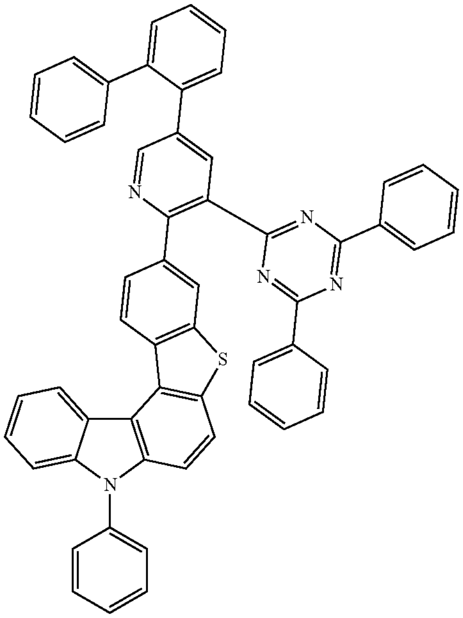
-continued
652
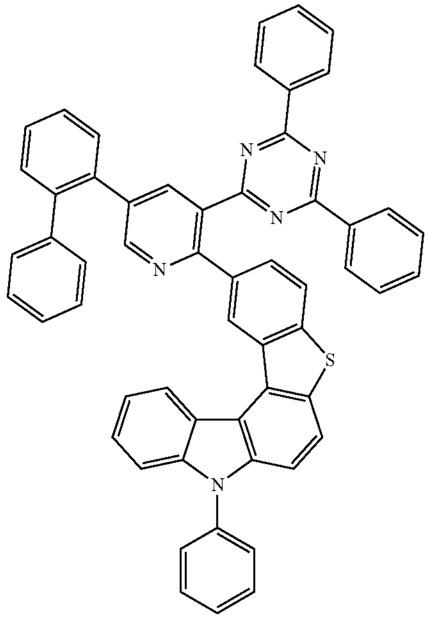
653
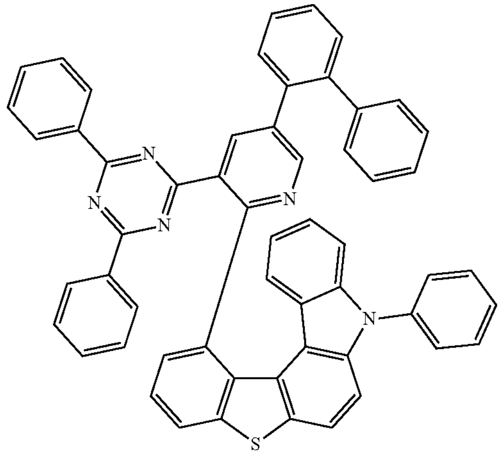
654
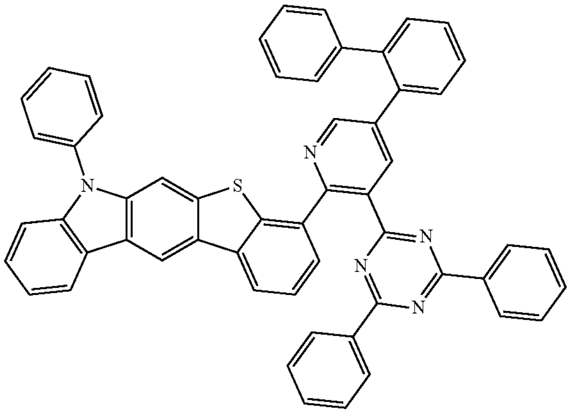

655
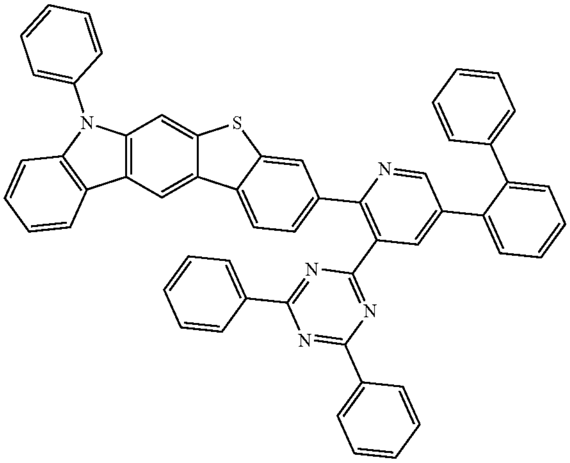
656
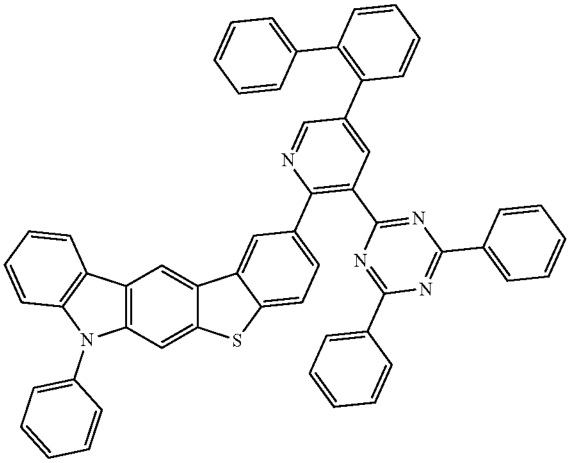
657
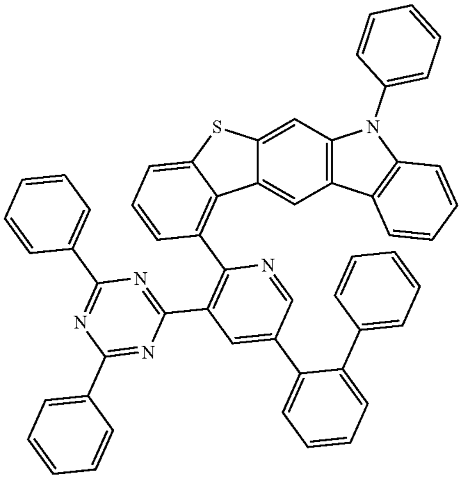
658
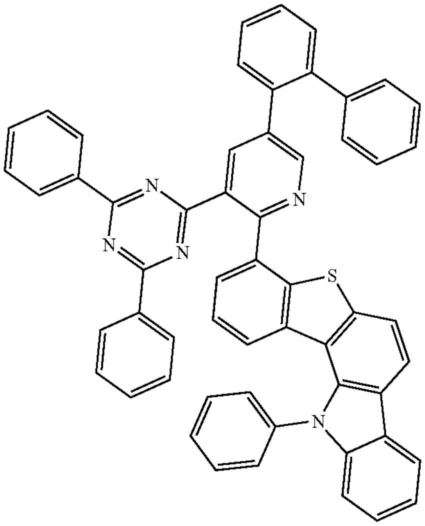
659
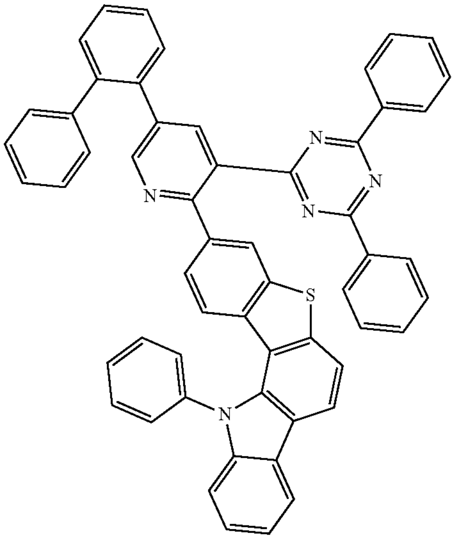
660
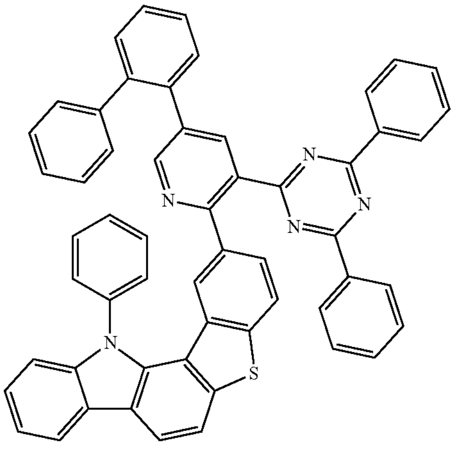

-continued
661
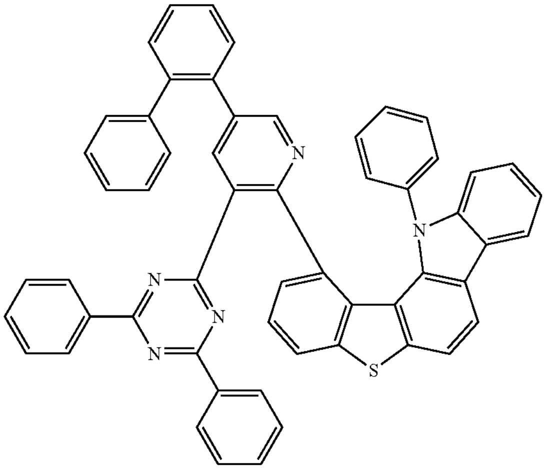
662
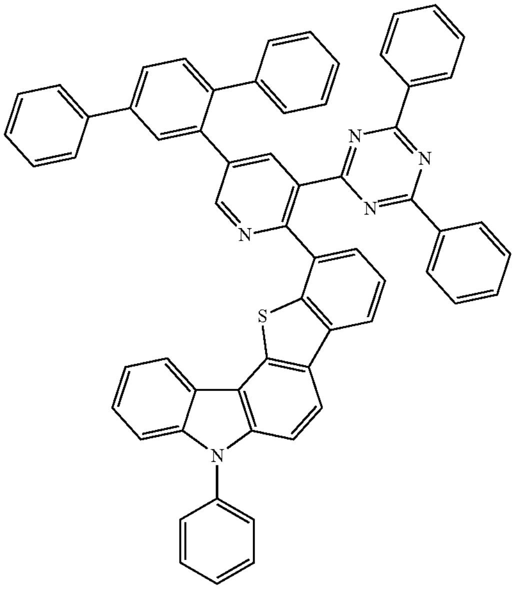
-continued
663
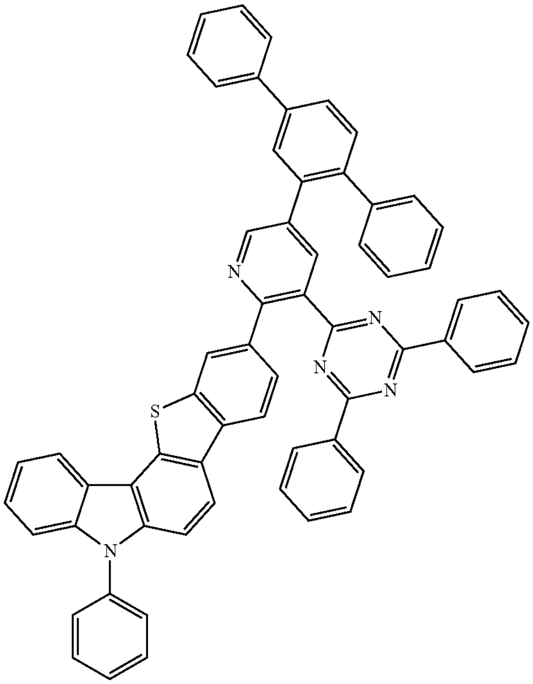
664
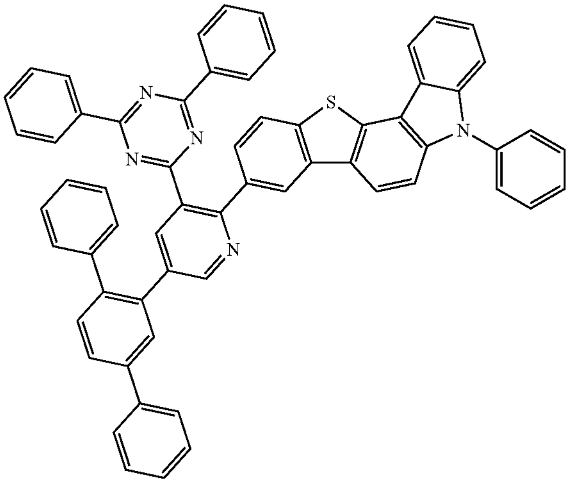

665
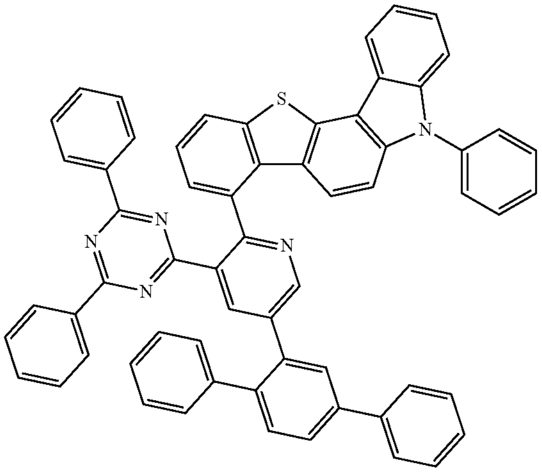
666
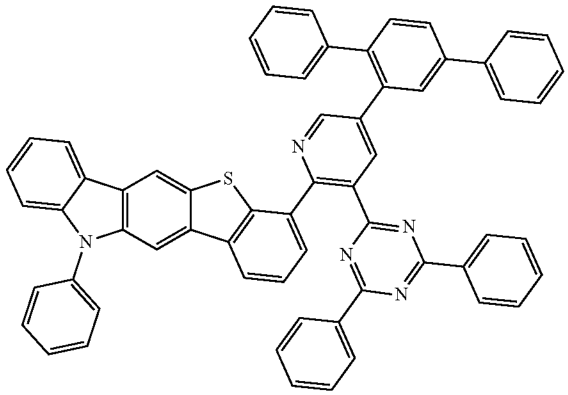
667
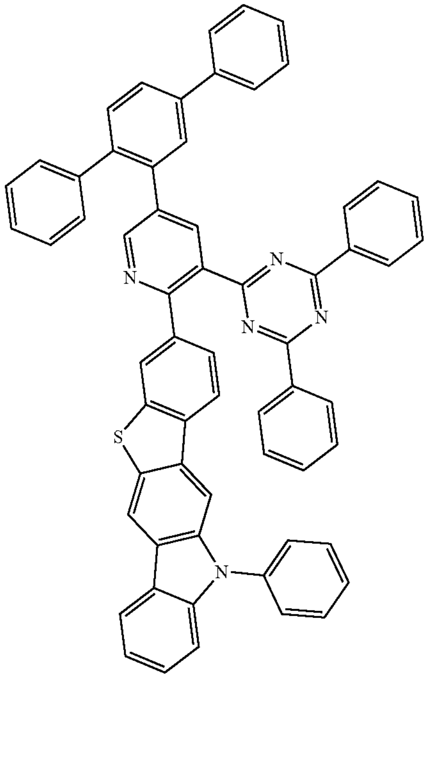
668
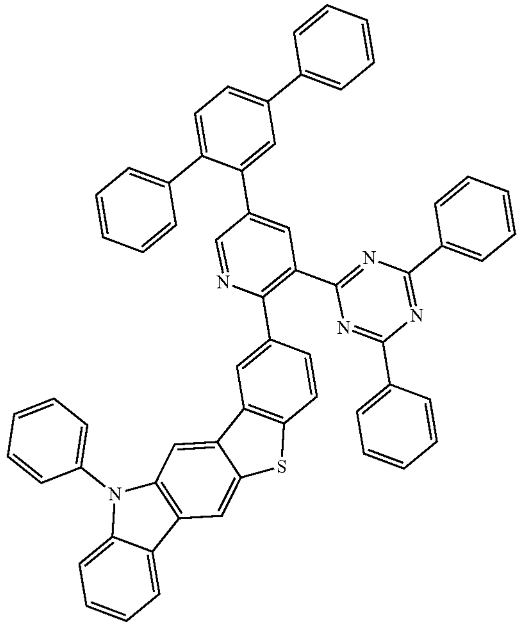
669
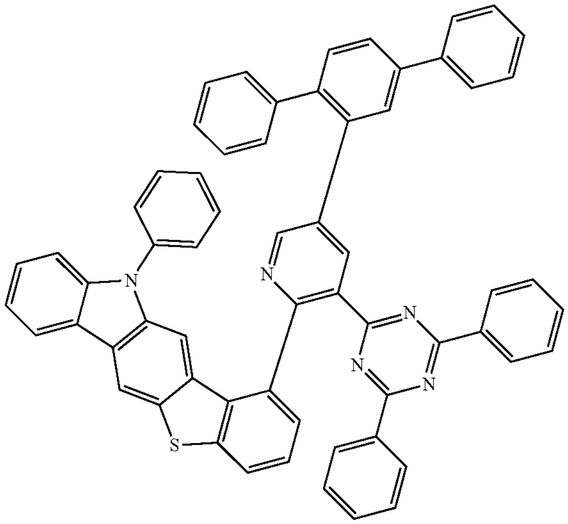
670
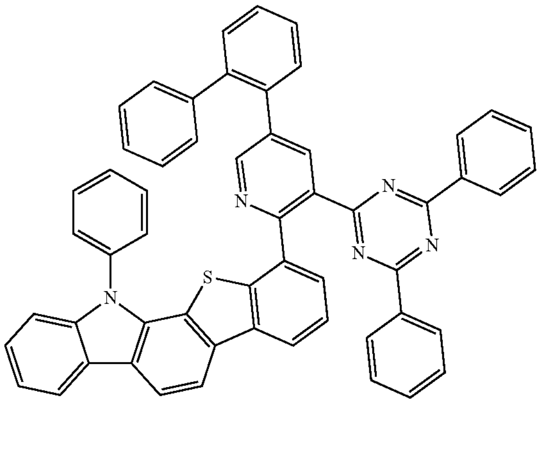

671
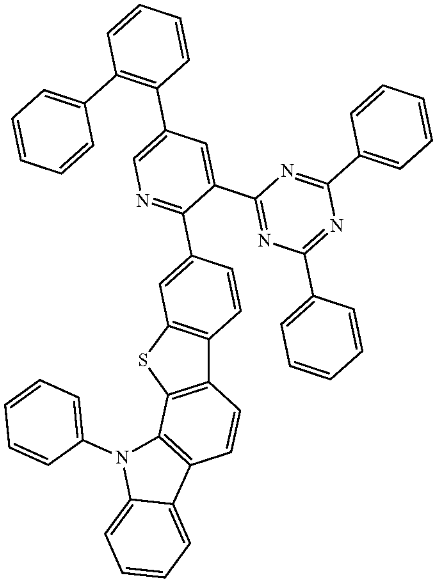
672
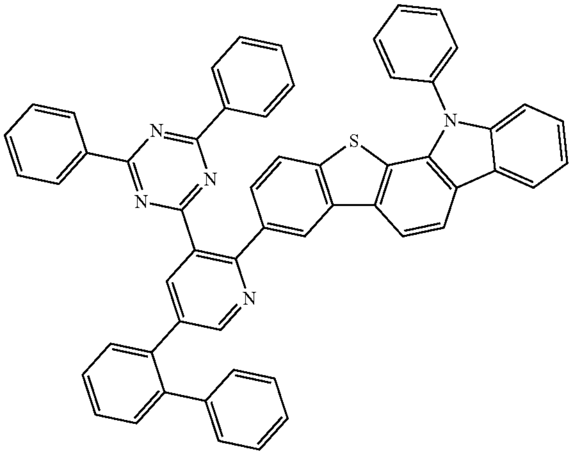
673
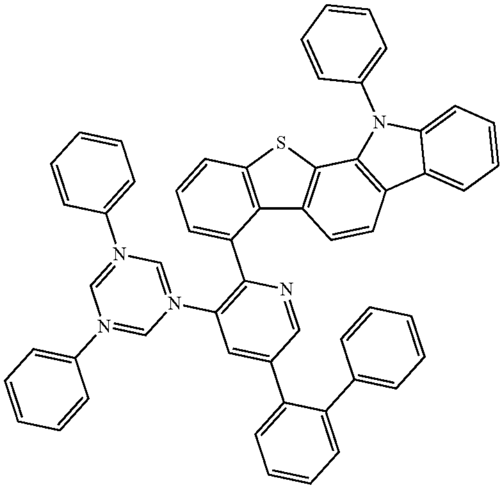
674
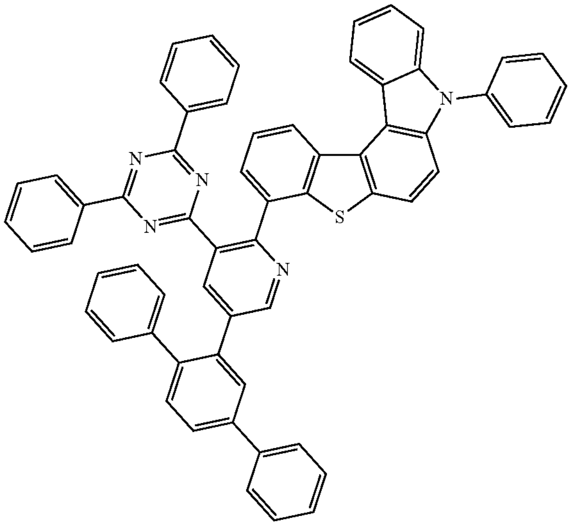
675
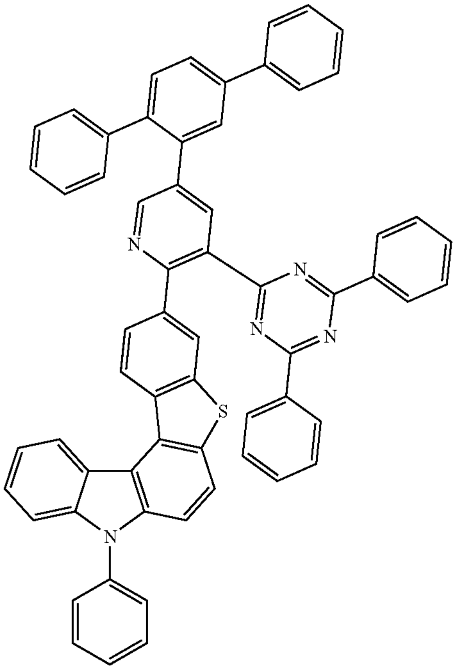

676
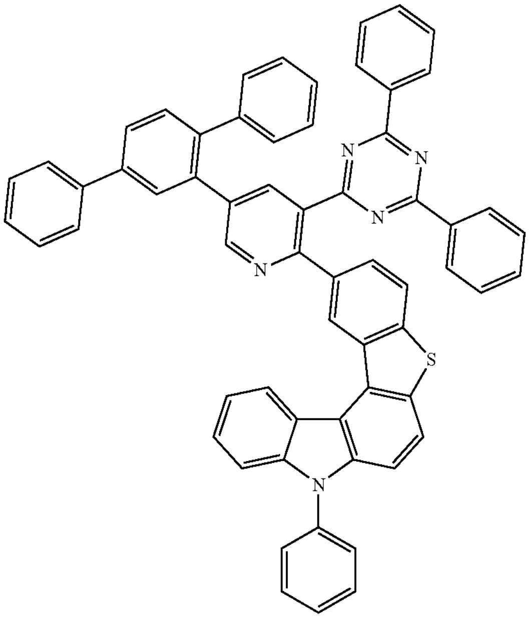
677
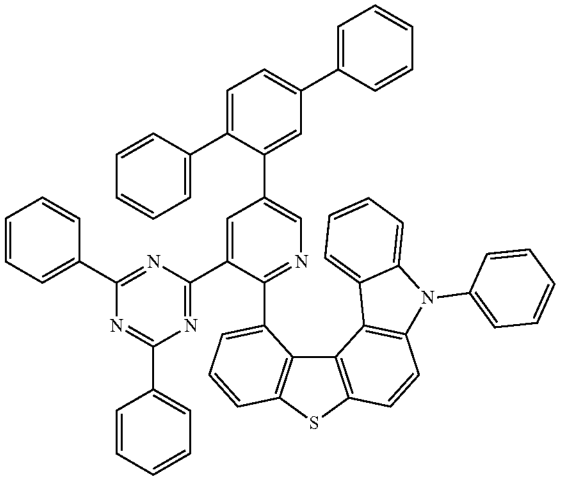
678
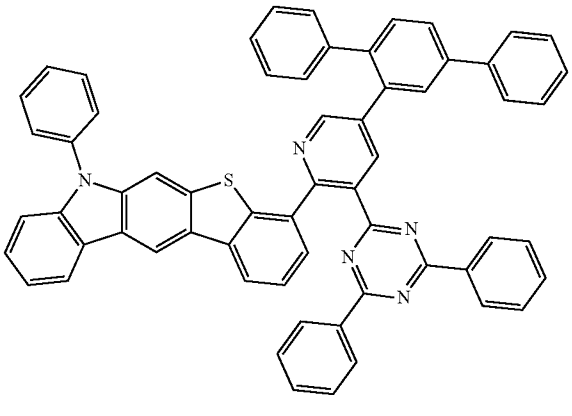
679
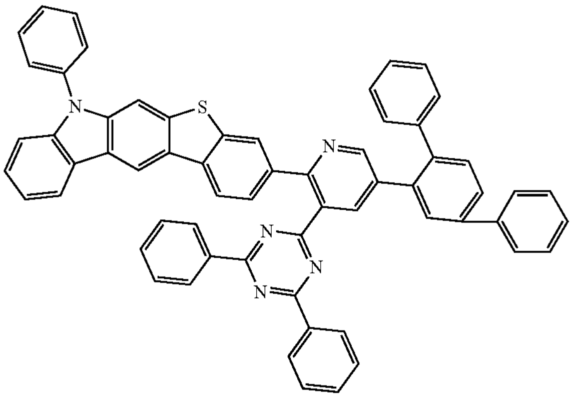
680
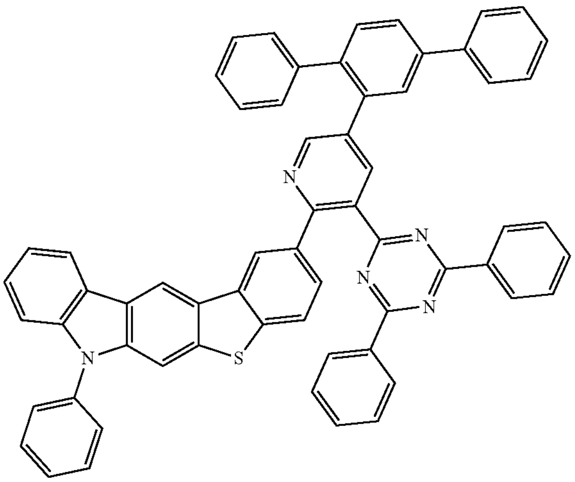
681
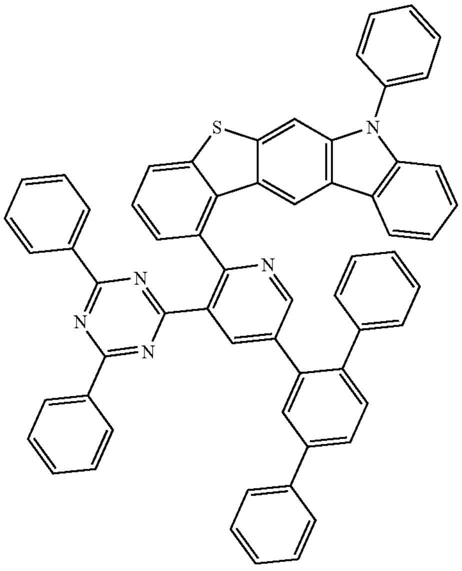

-continued
682
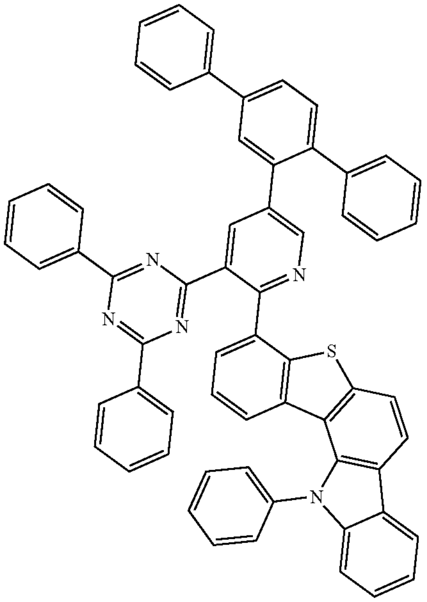
683
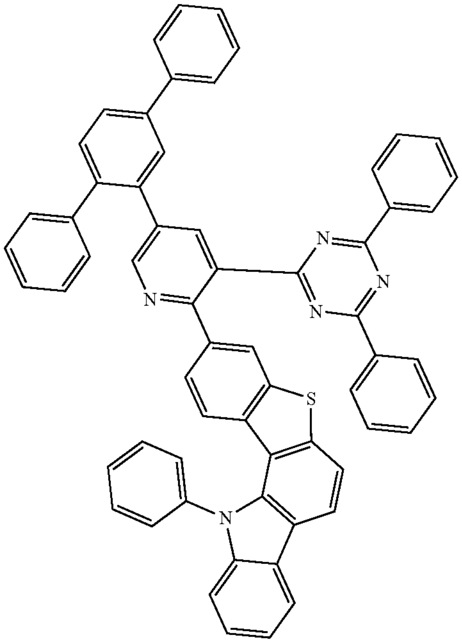
-continued
684
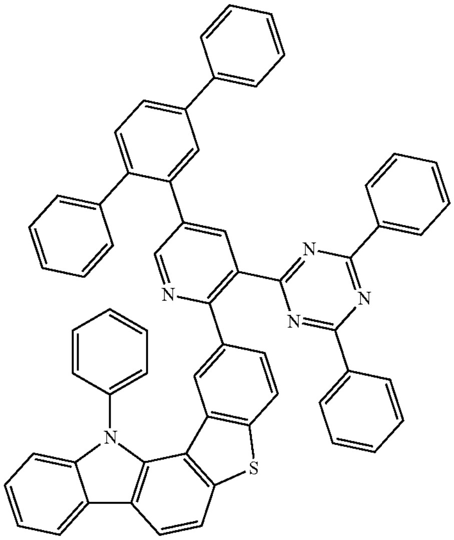
685
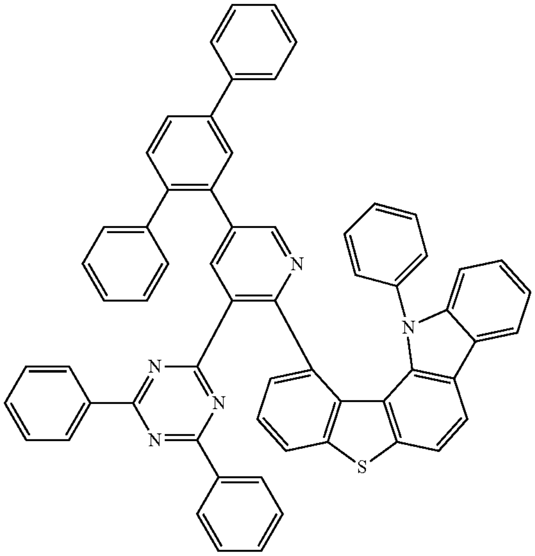
686
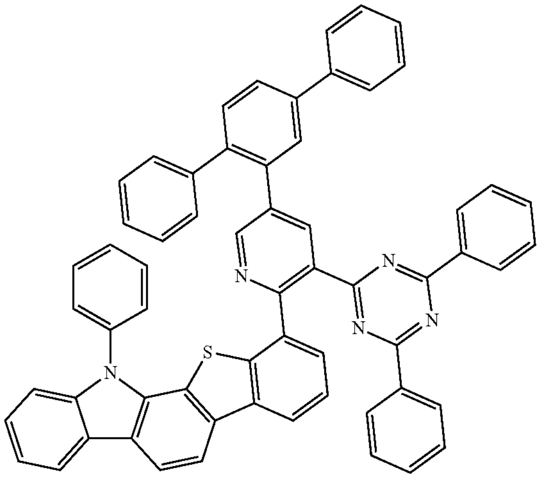

687
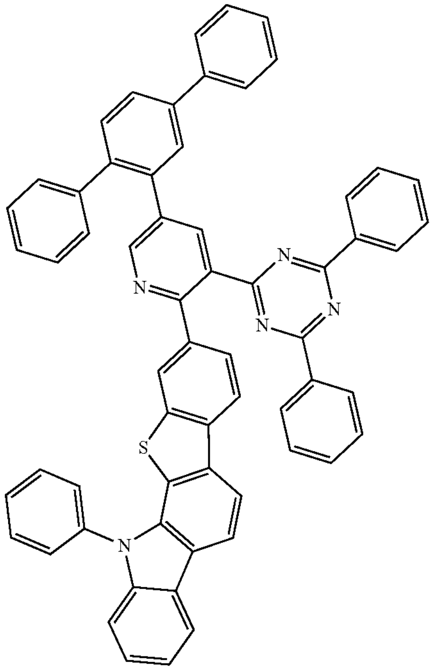
688
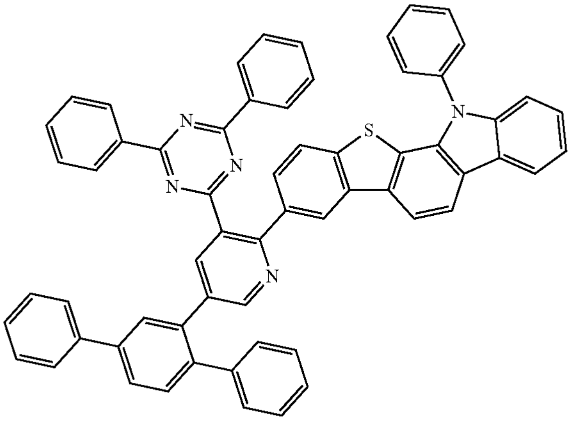
689
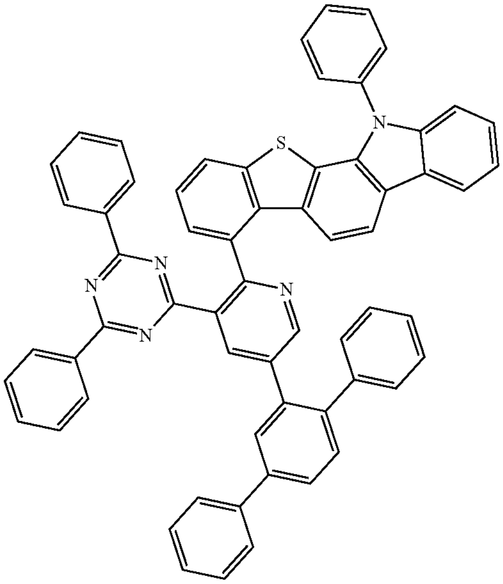
690
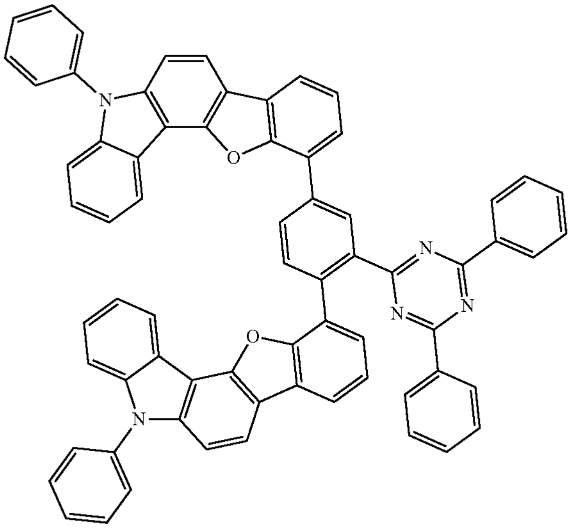

691
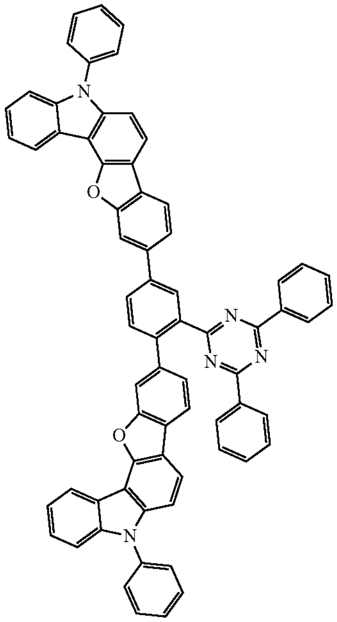
692
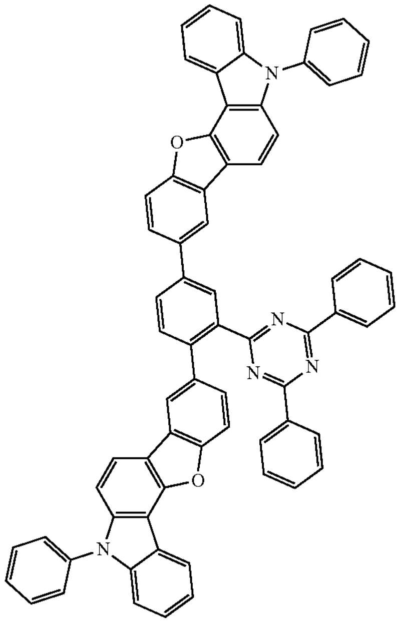
693
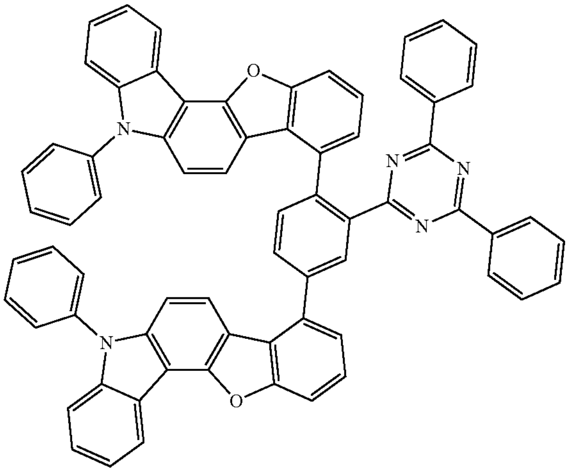
694
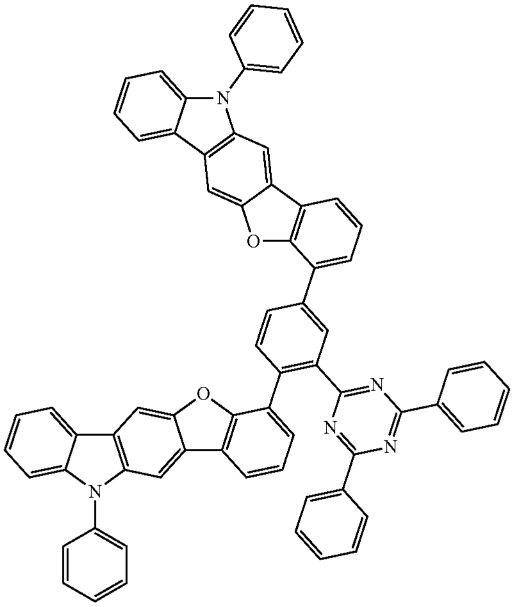

-continued
695
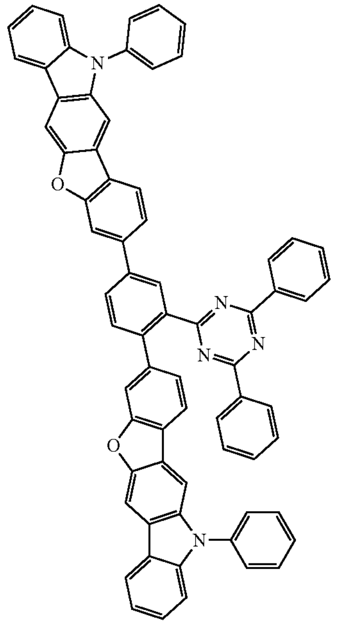
696
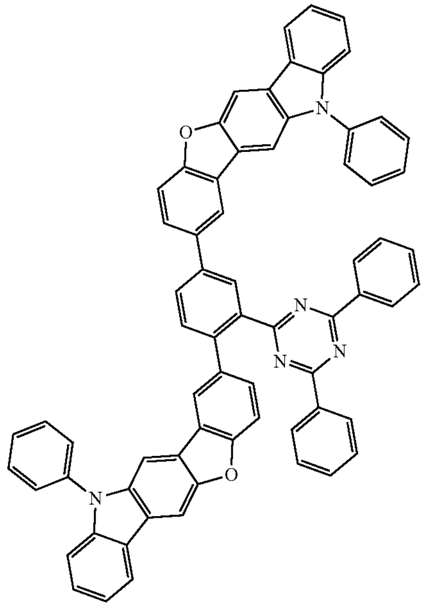
-continued
697
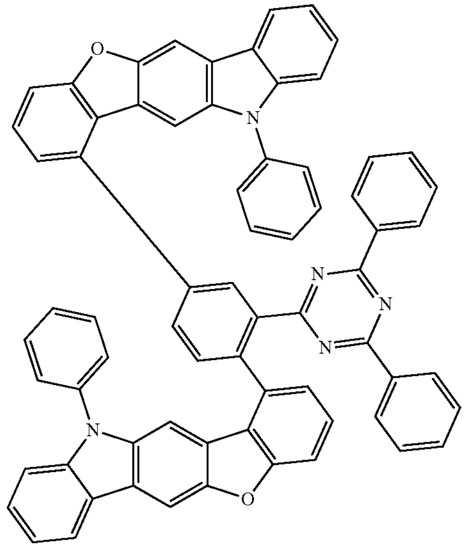
698
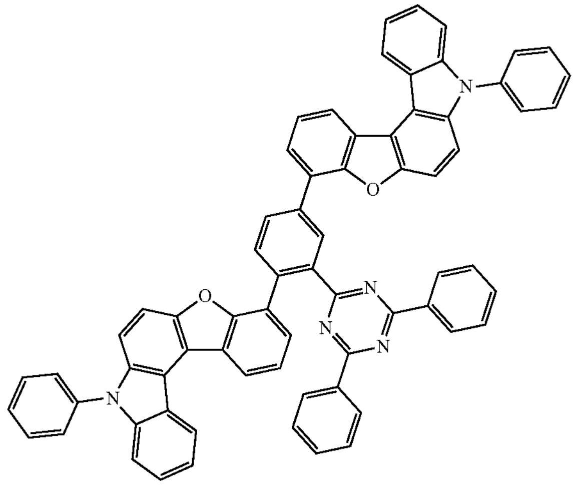

-continued
699
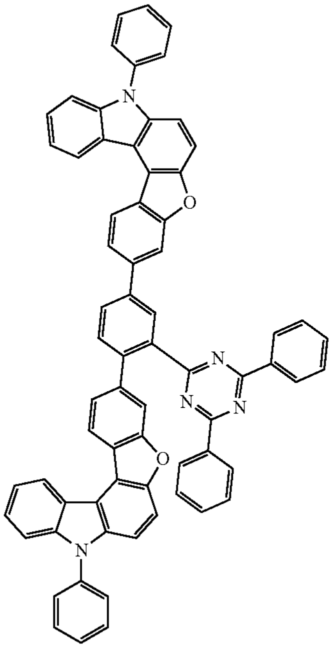
700
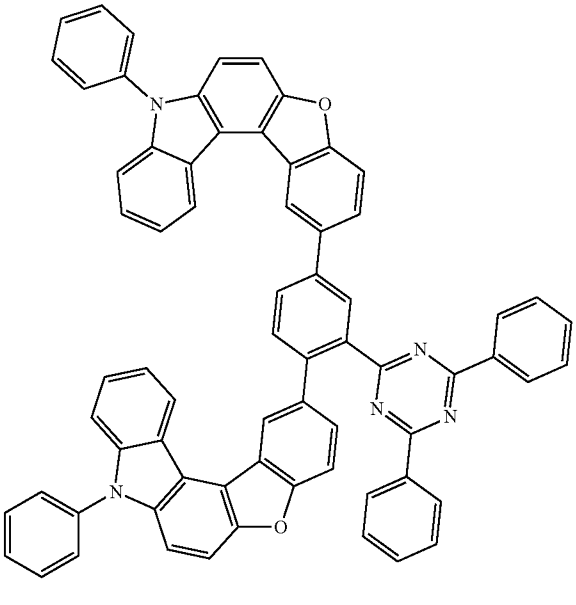
-continued
701
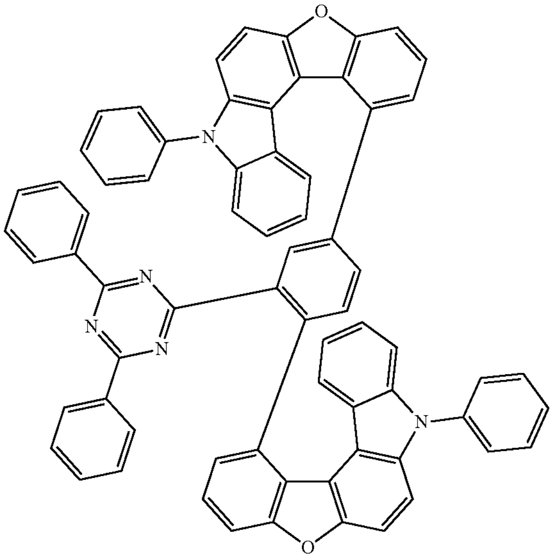
702
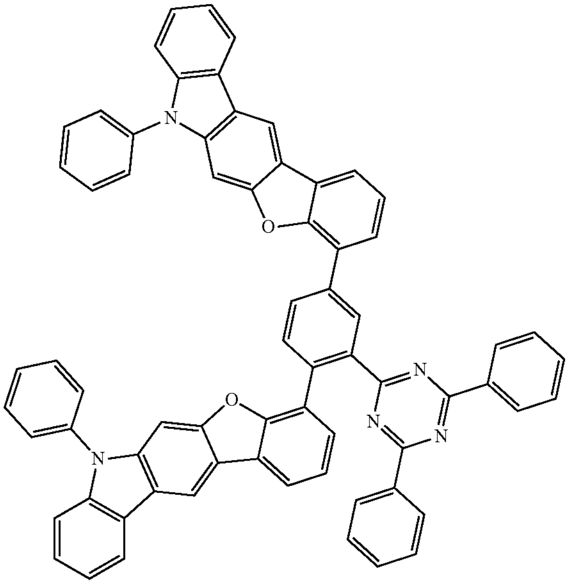

-continued
703
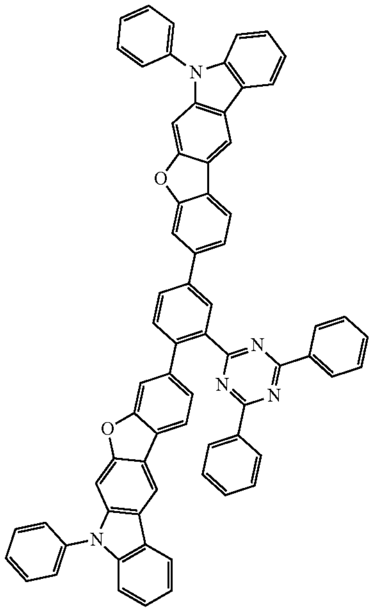
704
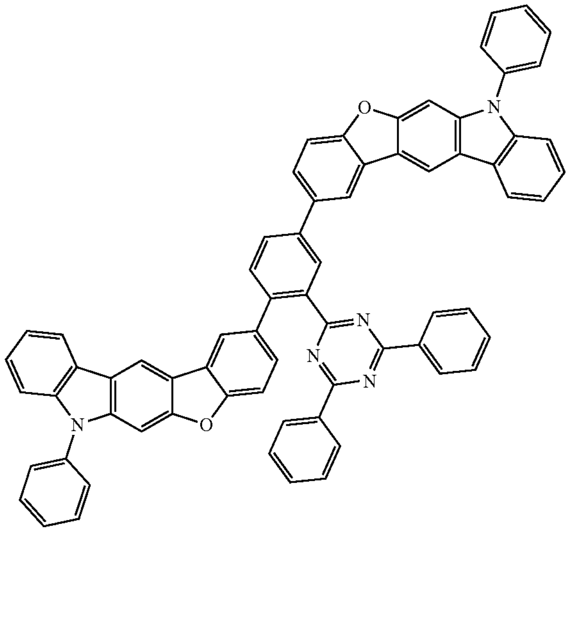
-continued
705
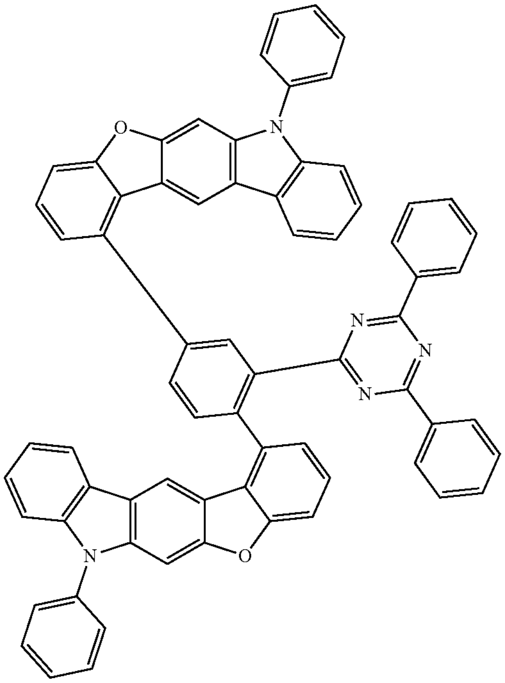
706
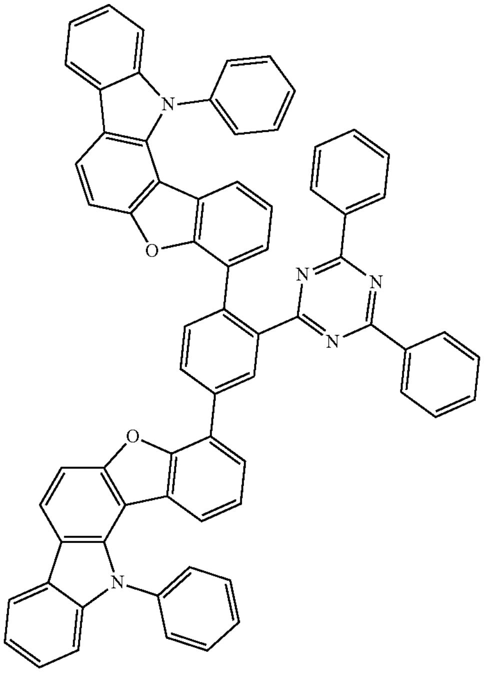

-continued
707
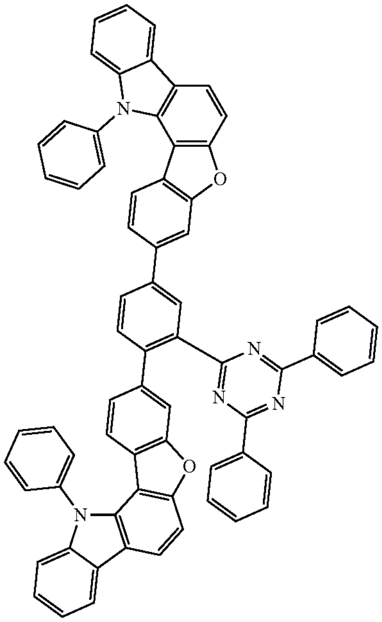
708
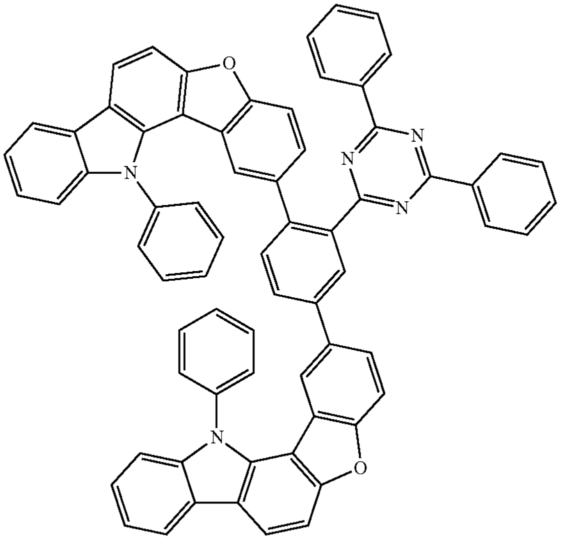
709
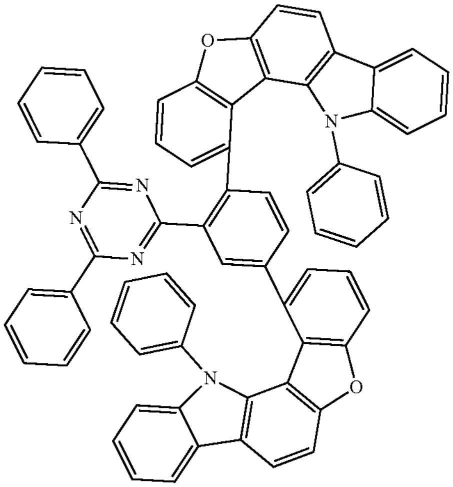
-continued
710
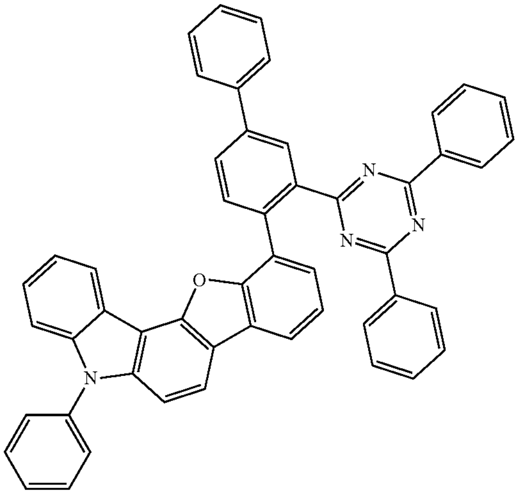
711
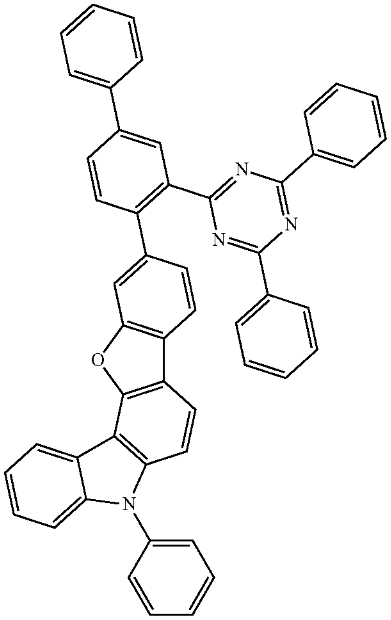

-continued
712
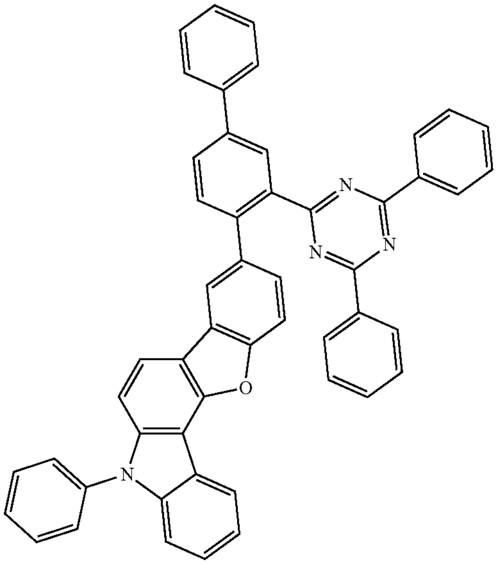
713
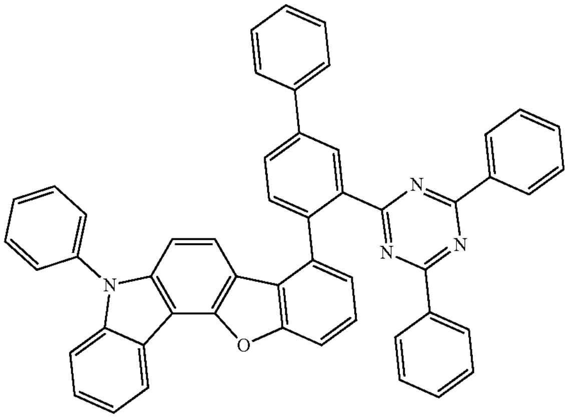
714
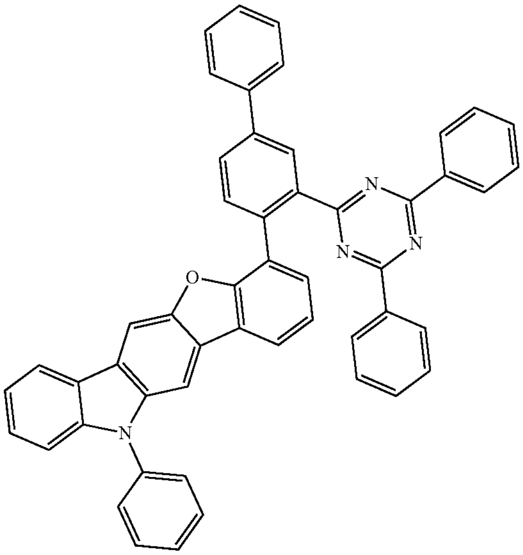
-continued
715
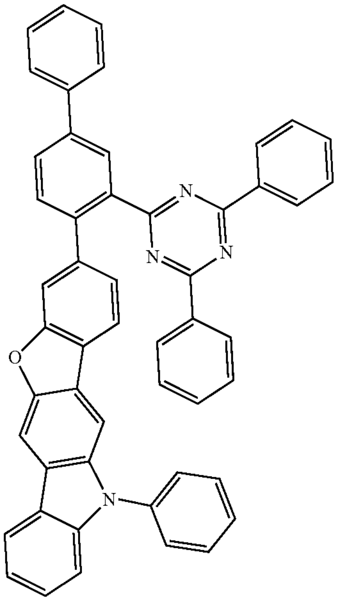
716
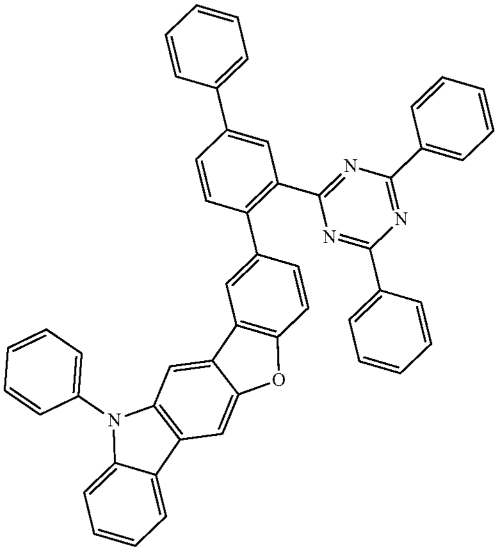
717
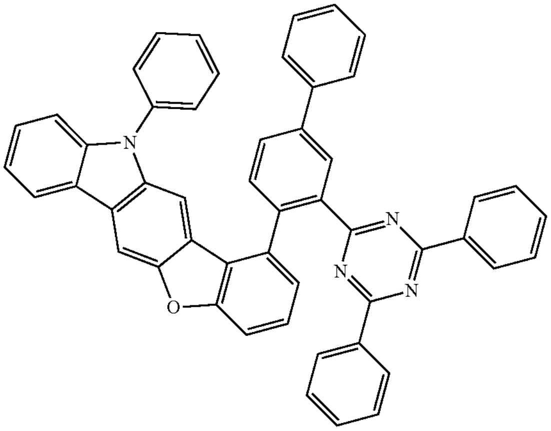

-continued
718
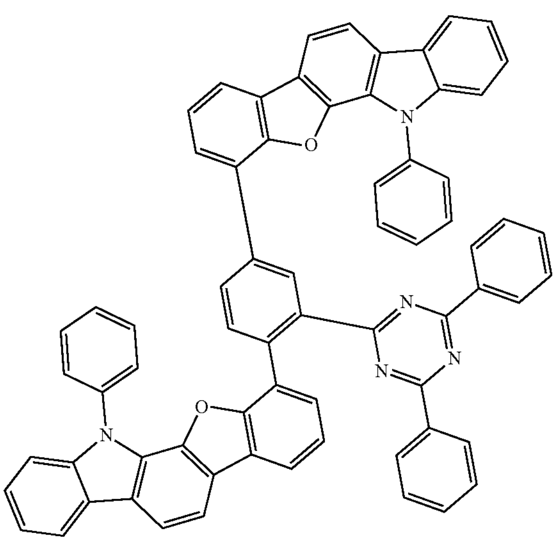
719
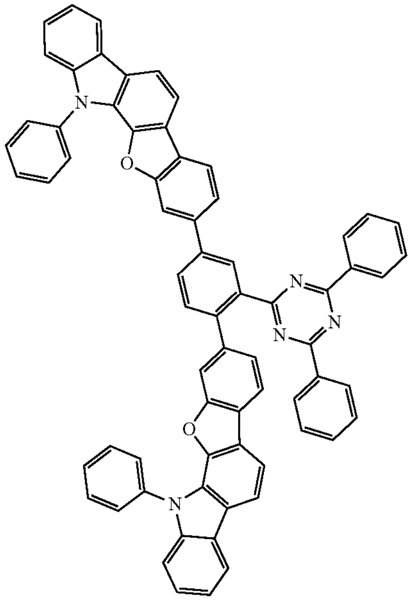
-continued
720
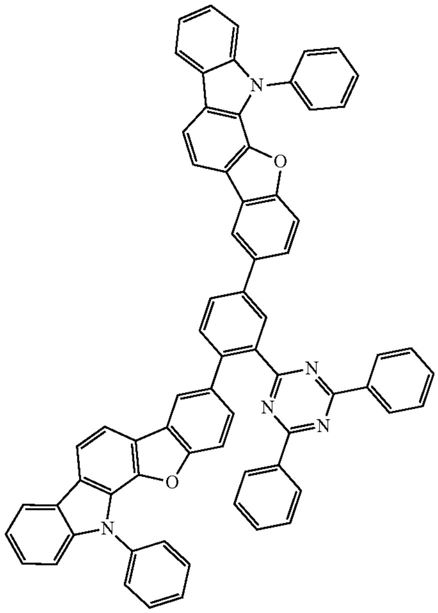
721
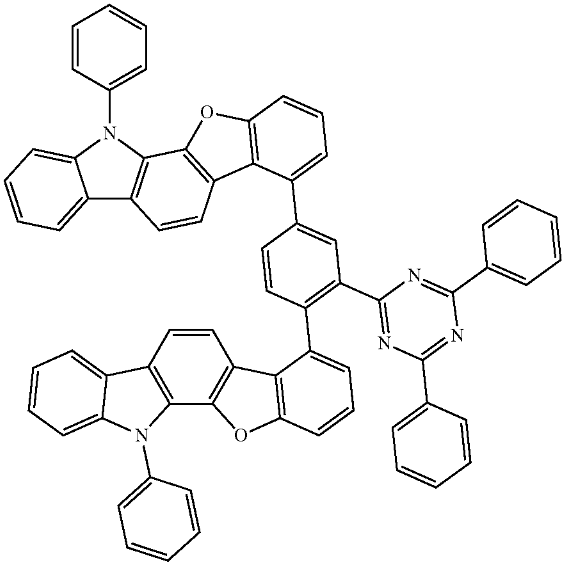

-continued
722
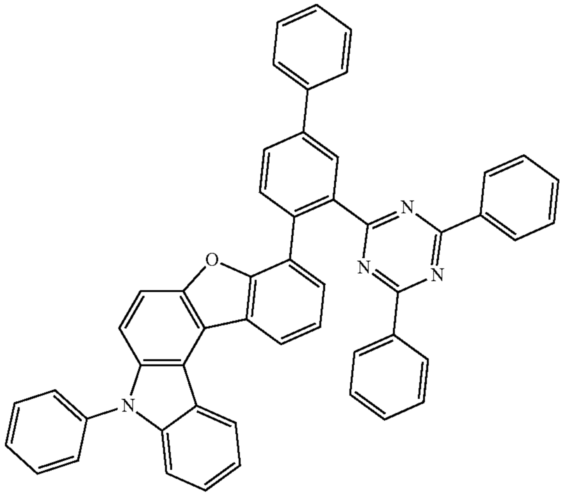
723
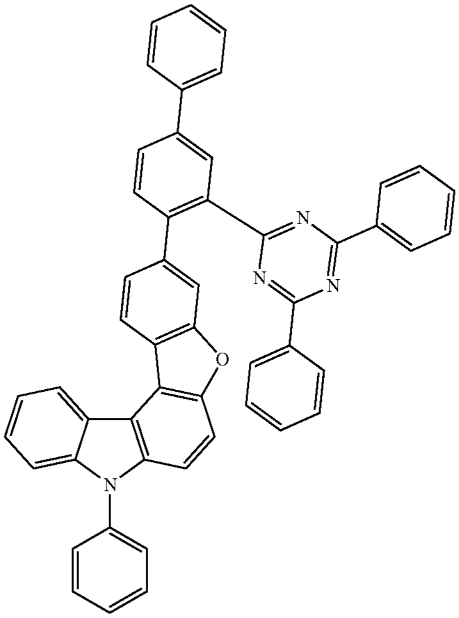
724
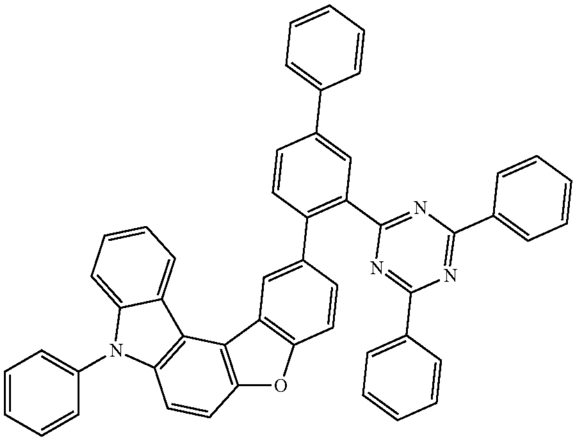
-continued
725
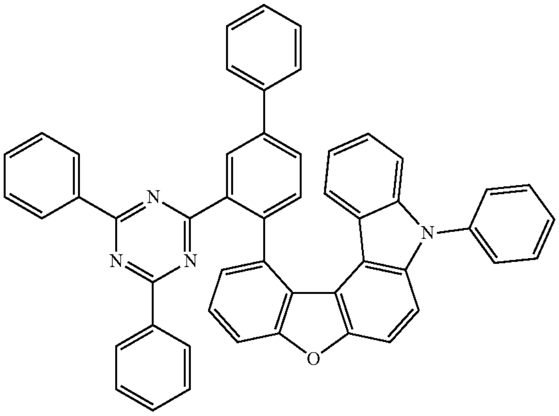
726
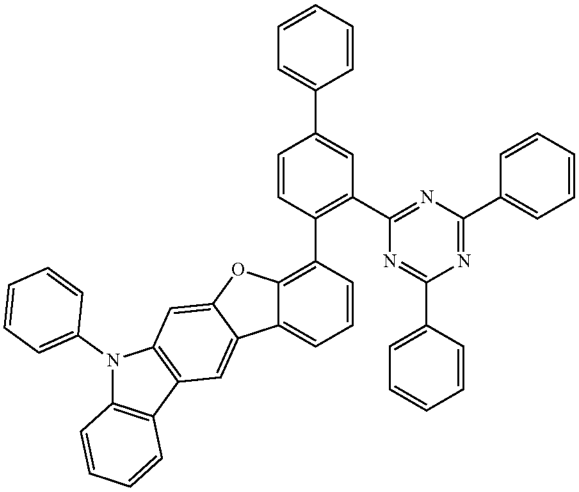
727
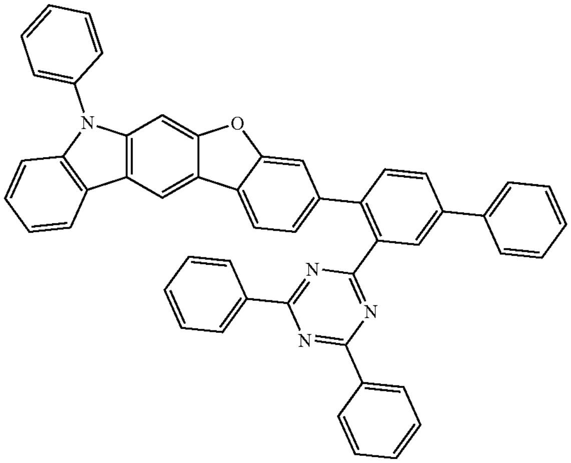

-continued
728
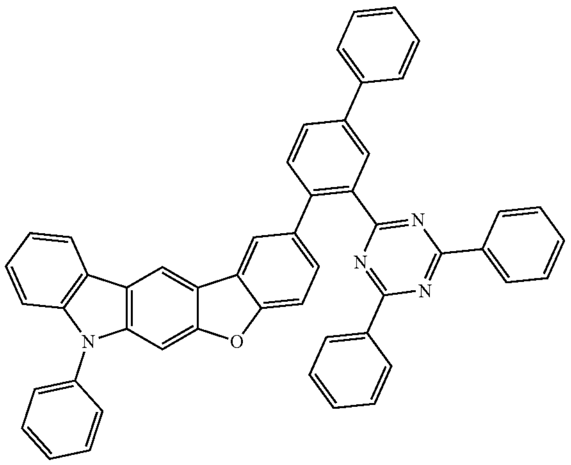
729
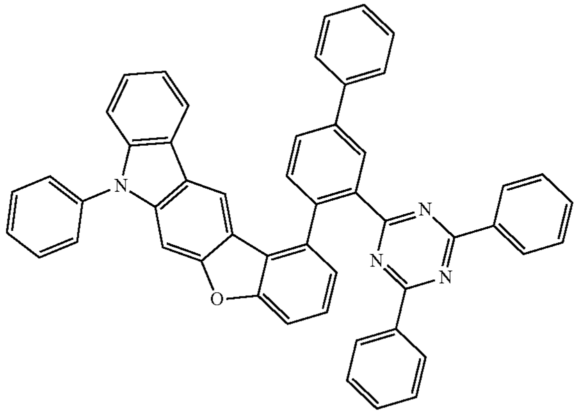
730
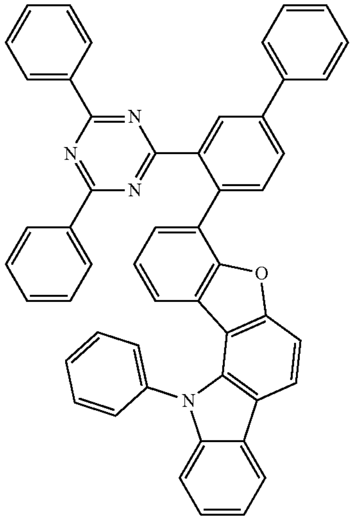
-continued
731
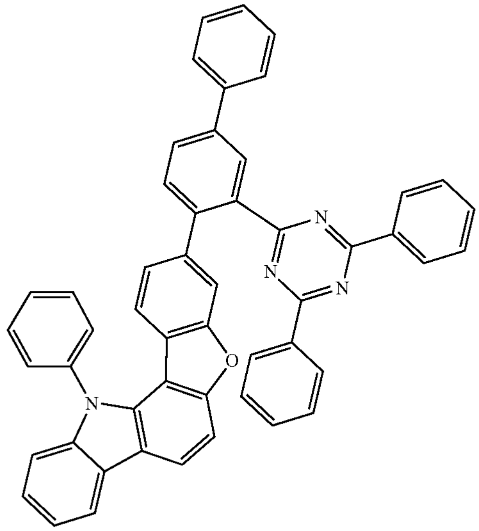
732
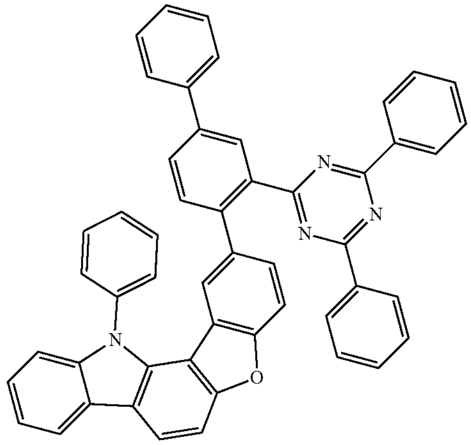
733
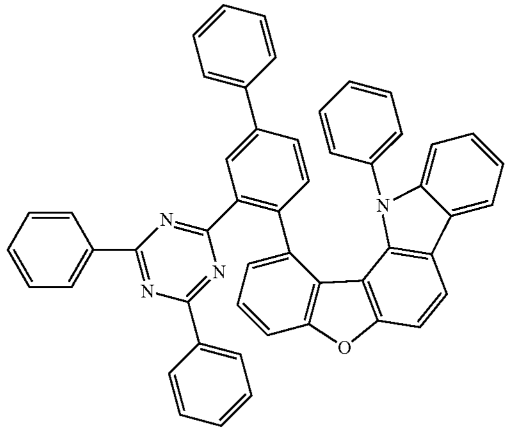

-continued
734
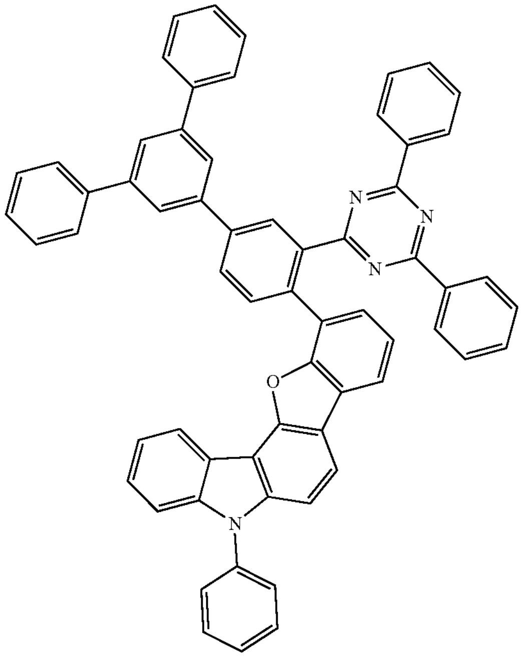
735
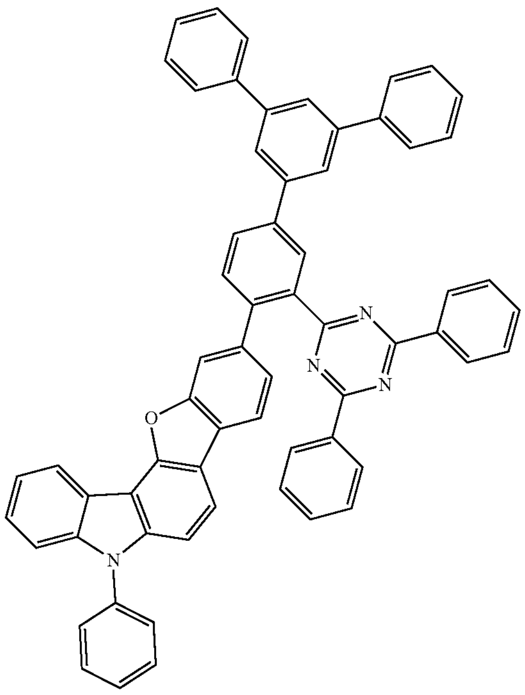
-continued
736
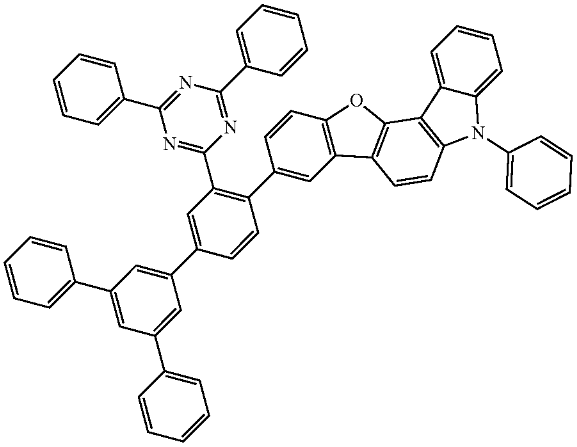
737
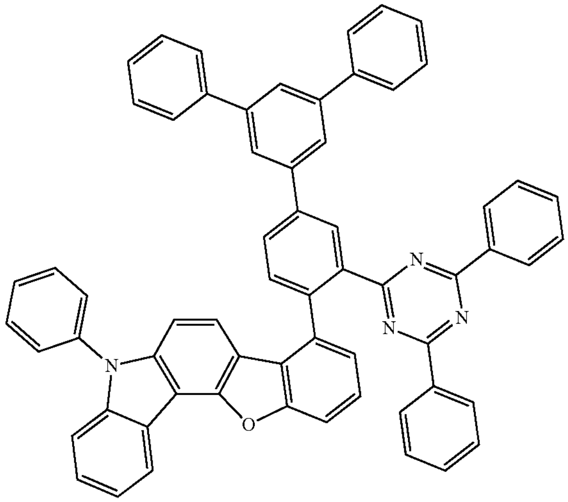
738
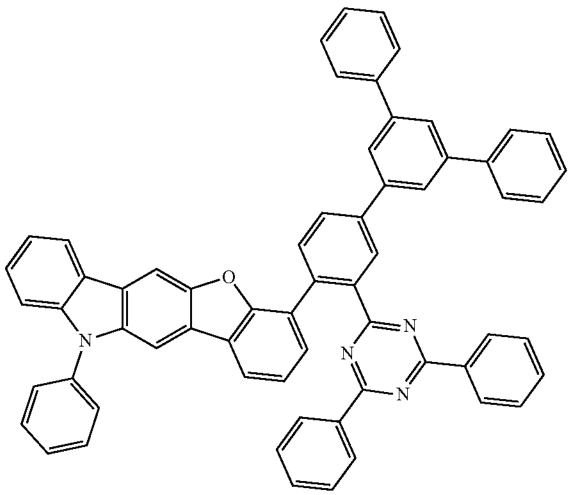

739
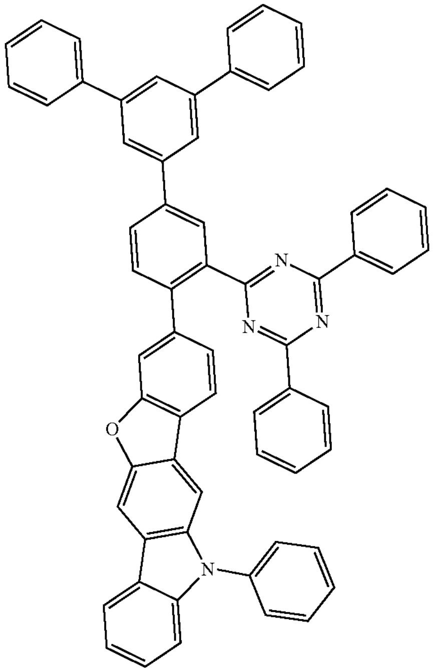
740
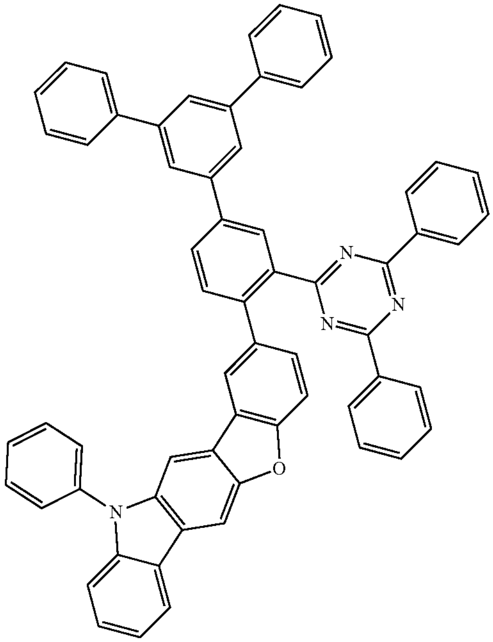
741
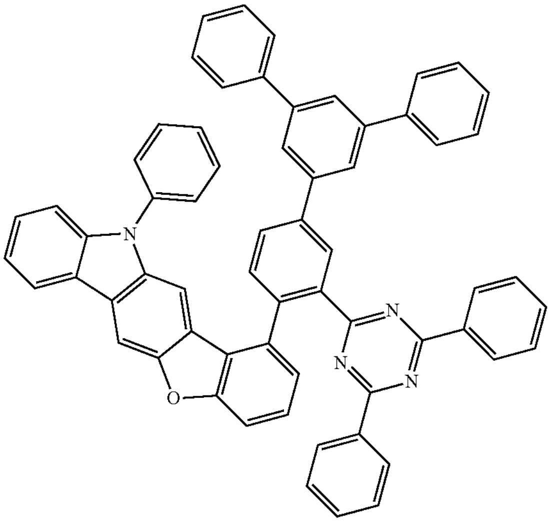
742
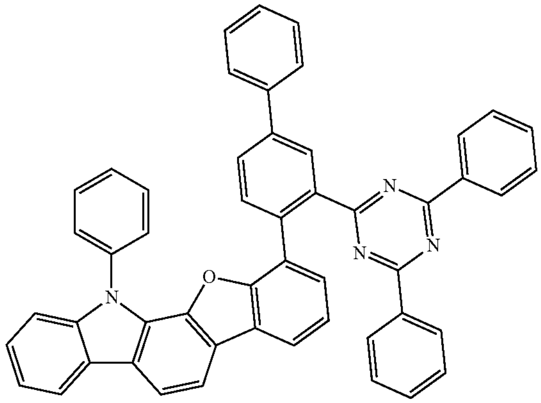
743
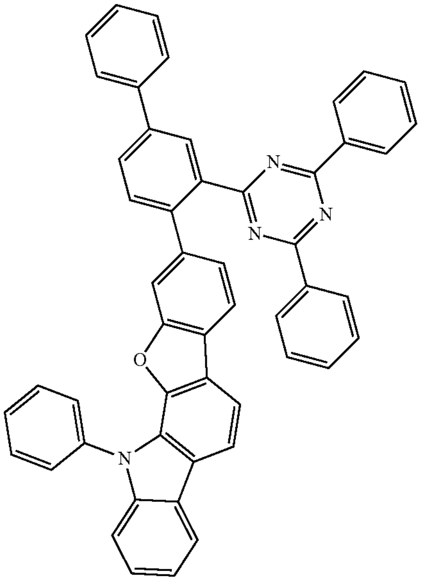

-continued
744
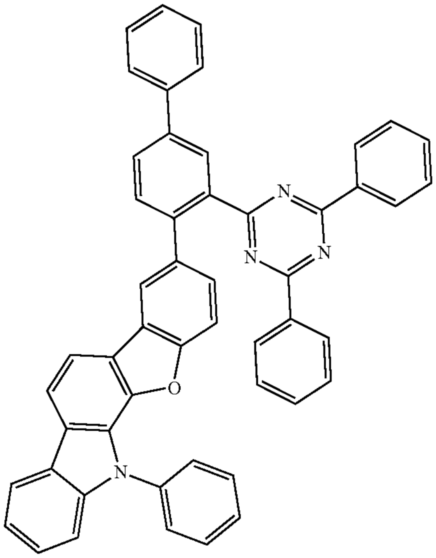
745
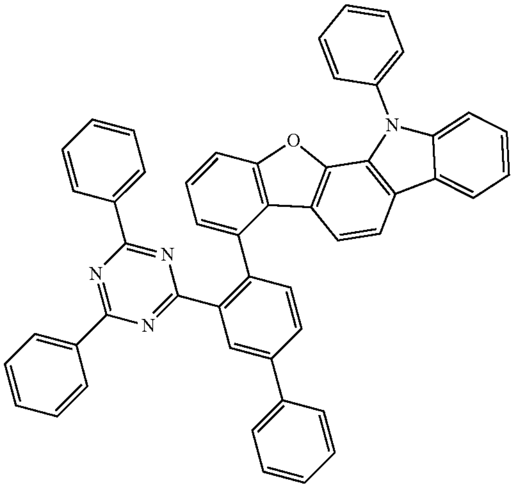
746
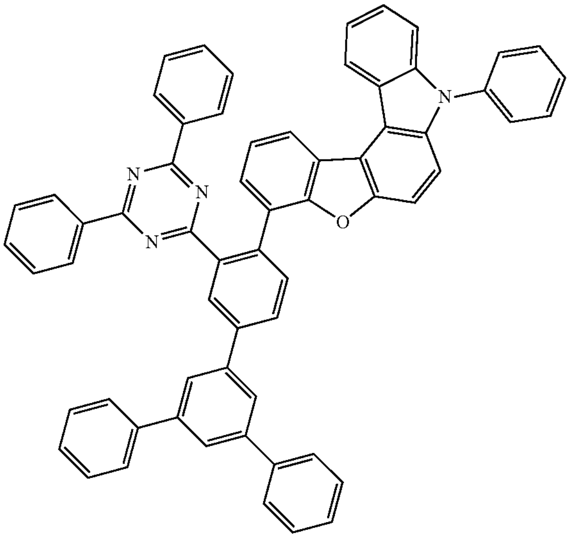
-continued
747
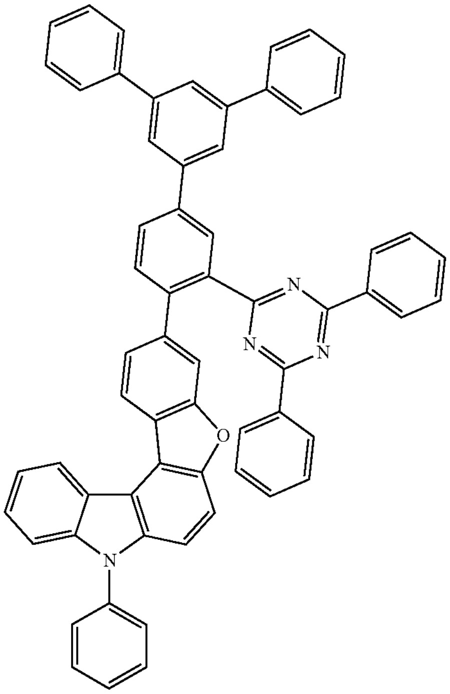
748
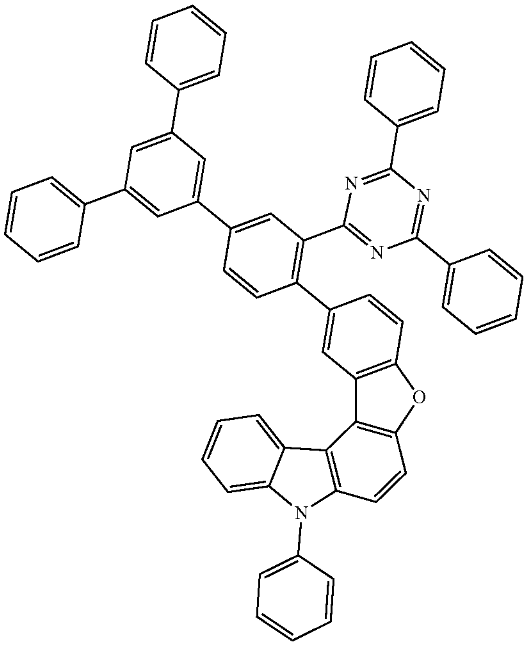

-continued
749
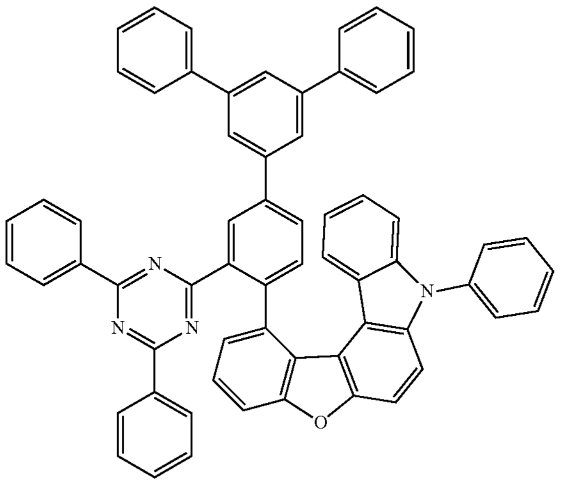
750
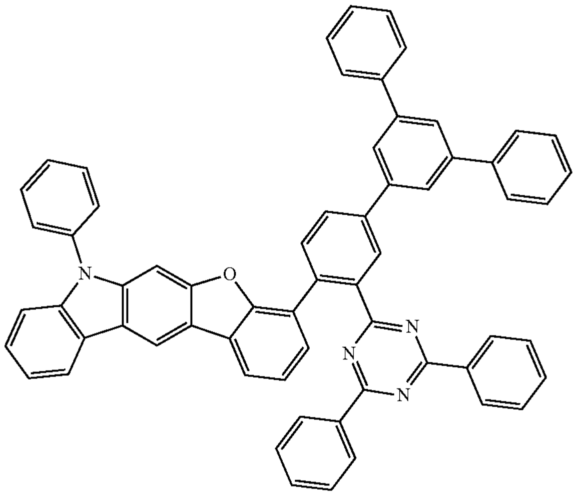
751
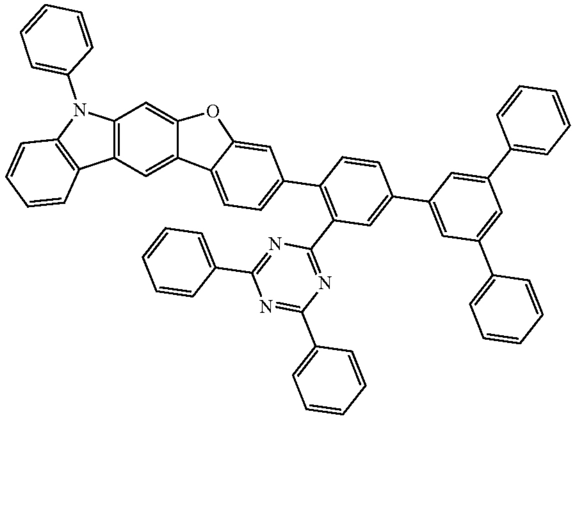
-continued
752
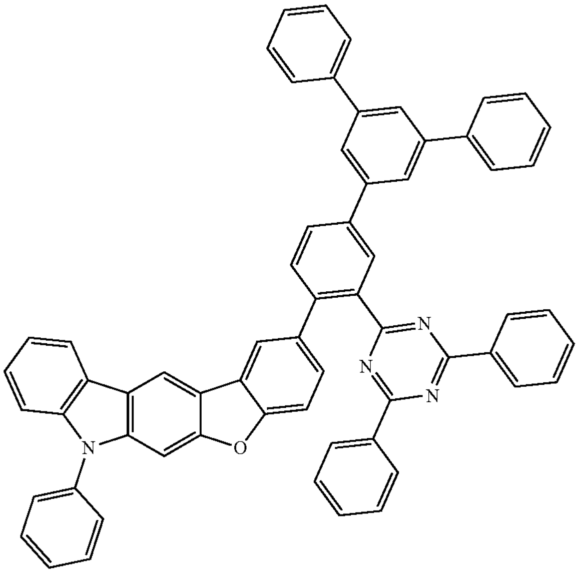
753
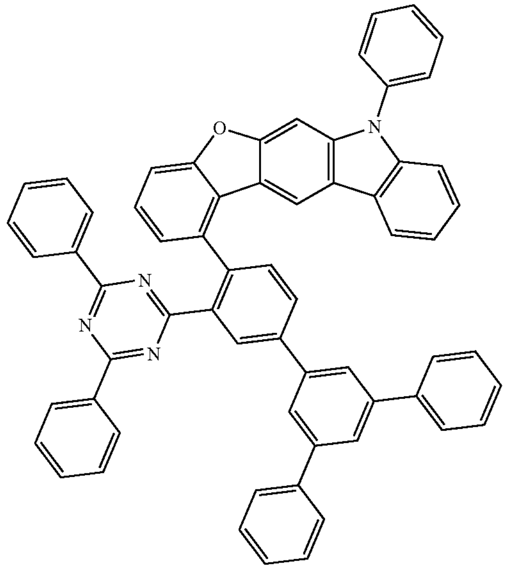

-continued
754
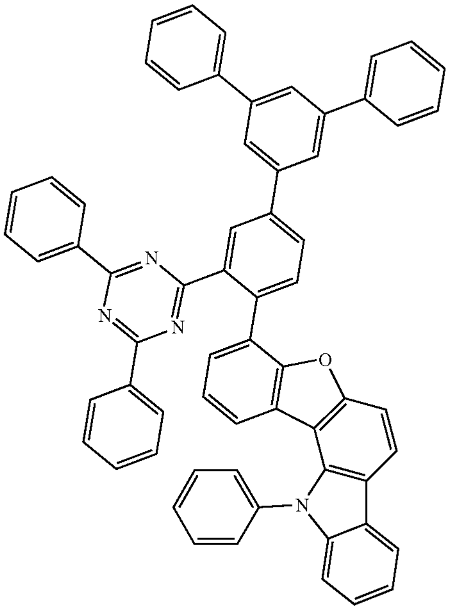
755
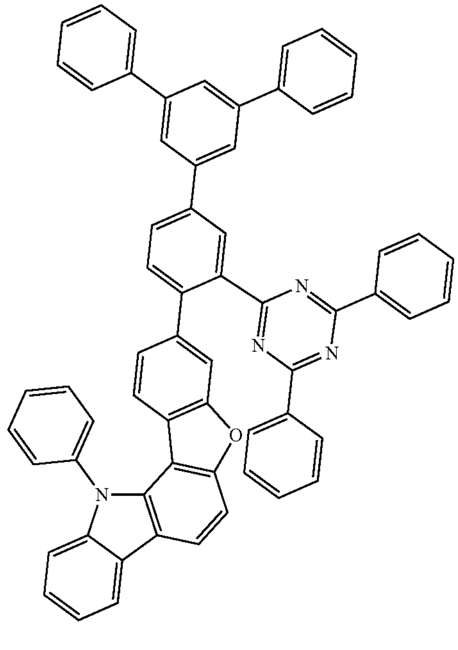
-continued
756
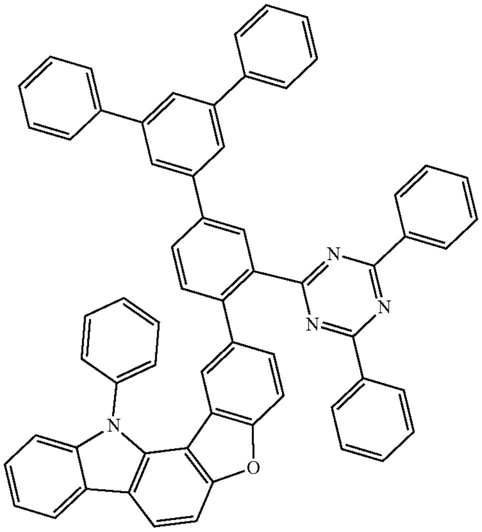
757
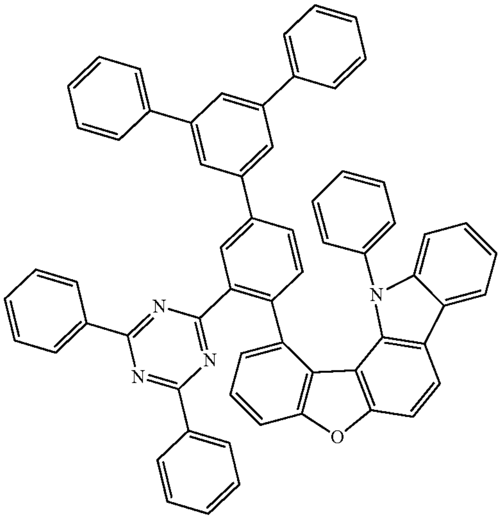
758
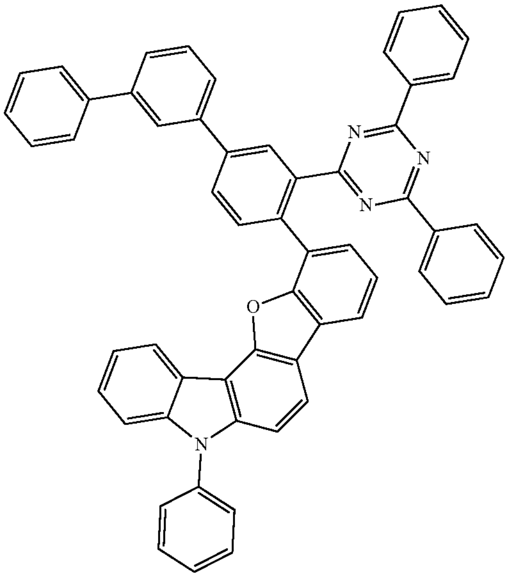

-continued
759
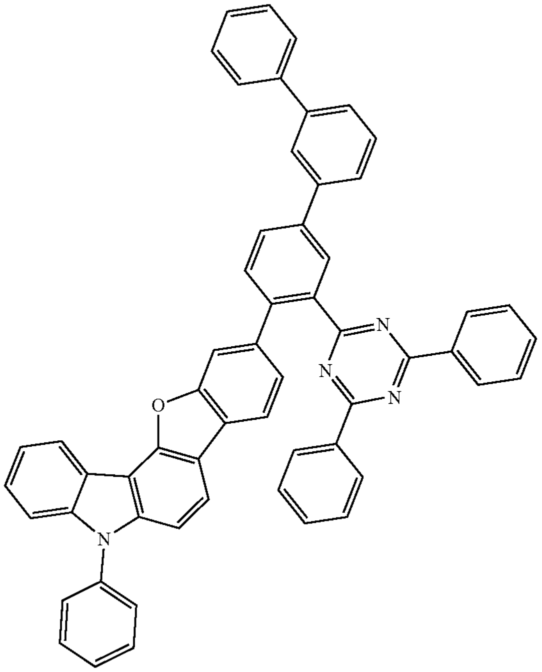
760
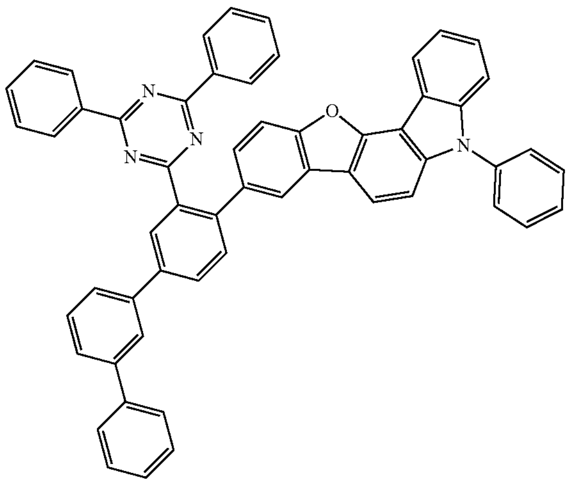
-continued
761
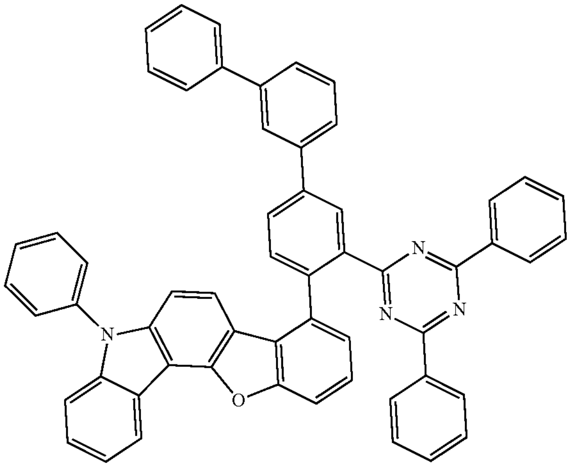
762
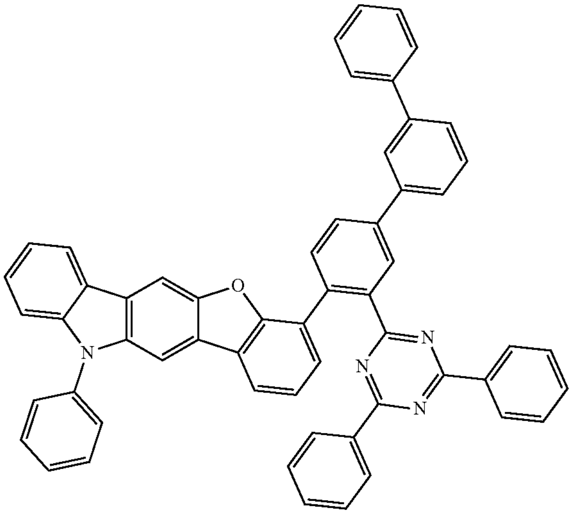
763
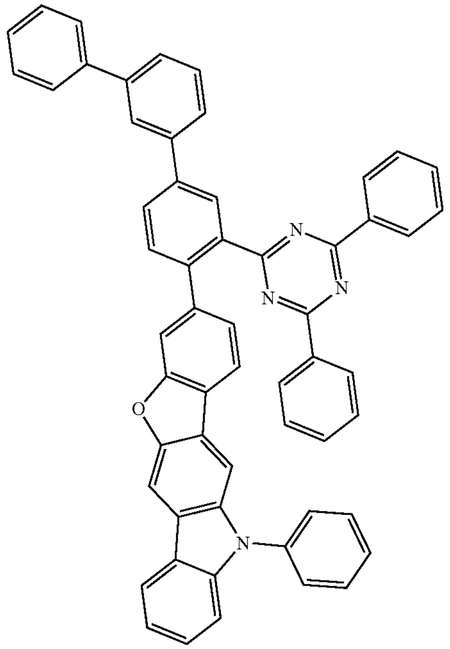

-continued
764
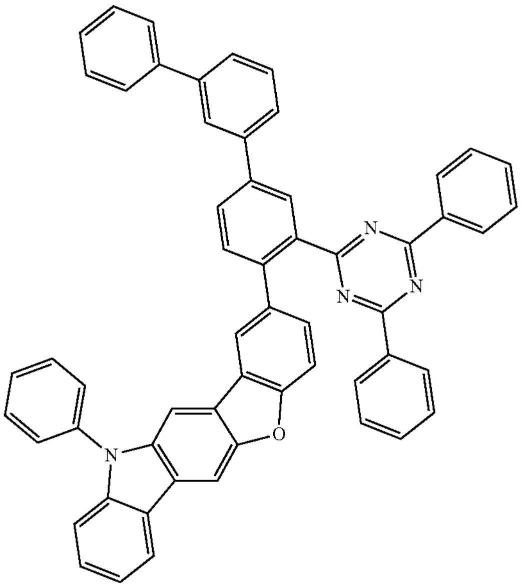
765
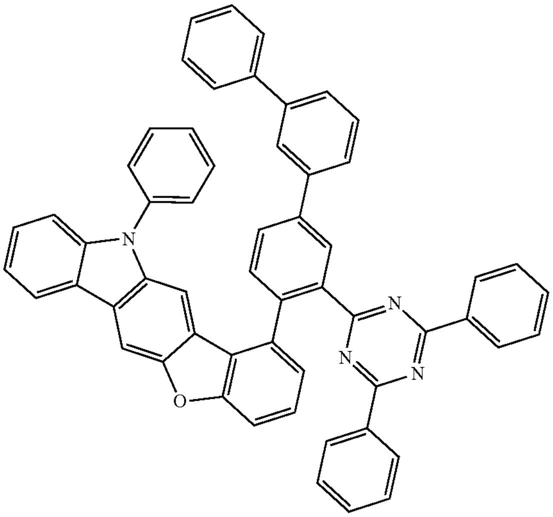
766
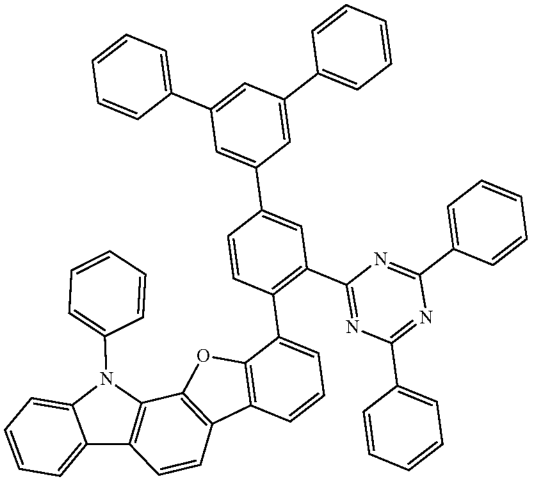
-continued
767
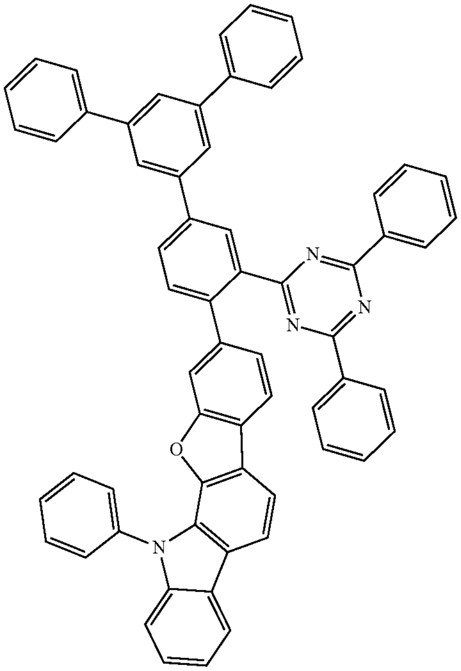
768
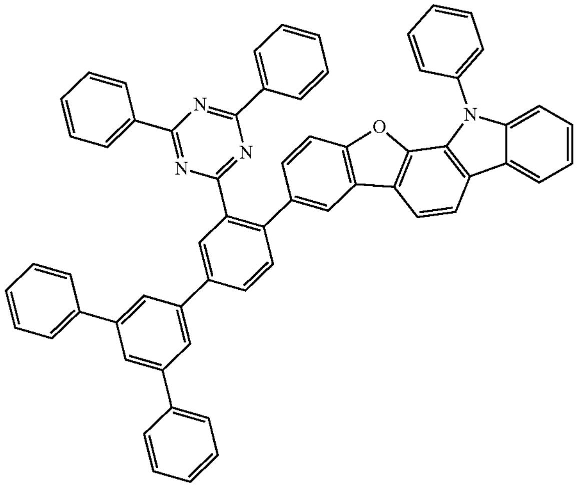

769
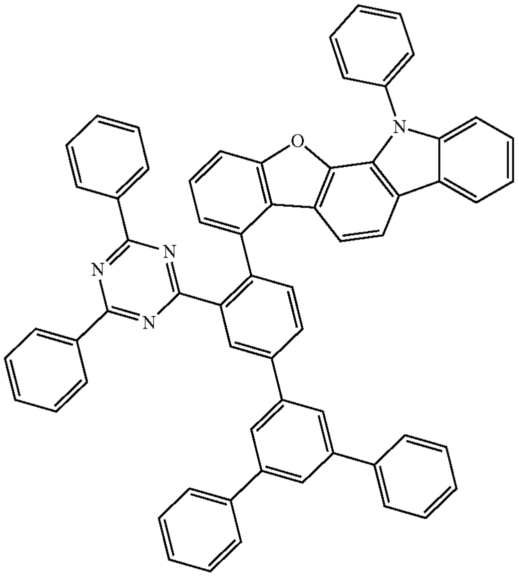
770
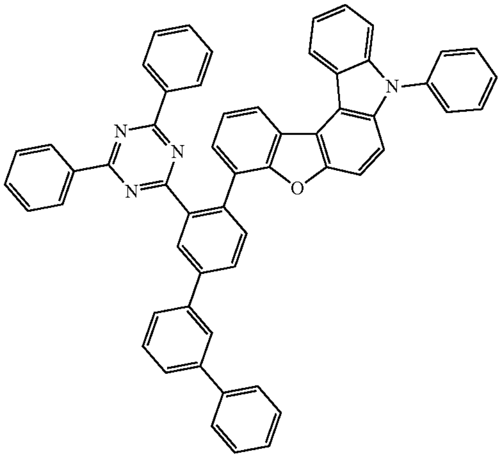
771
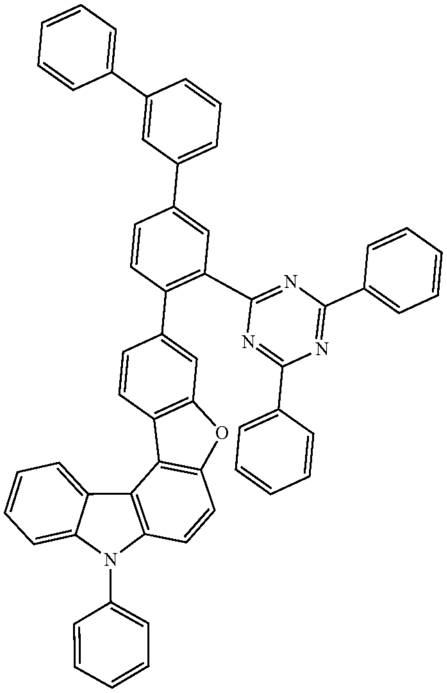
772
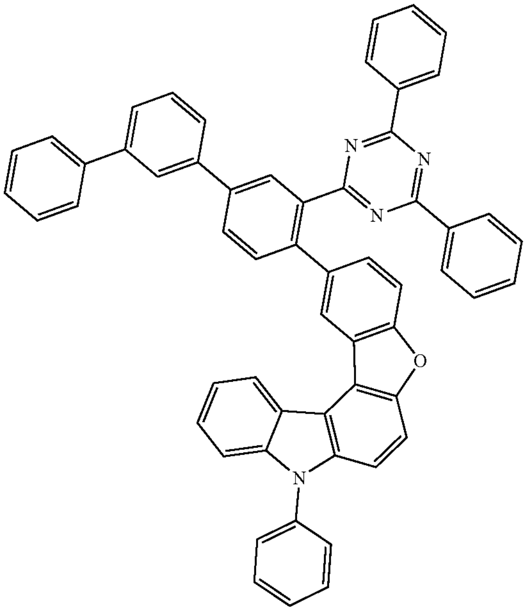

773
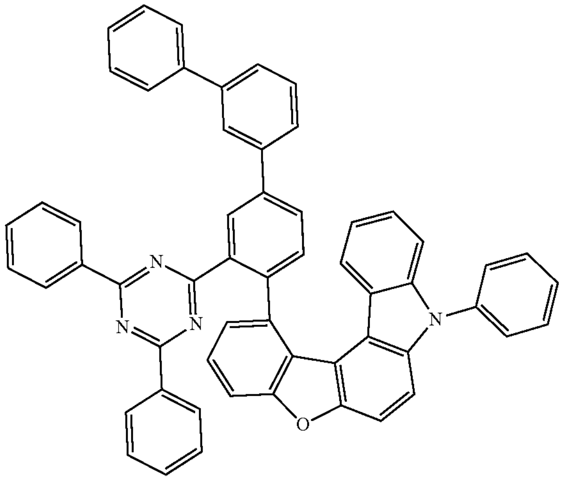
774
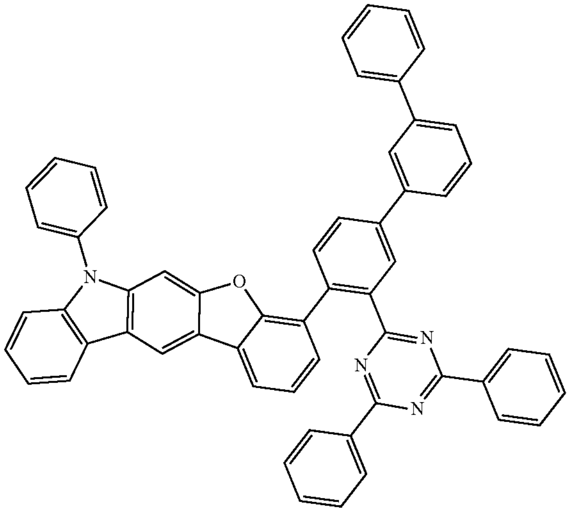
775
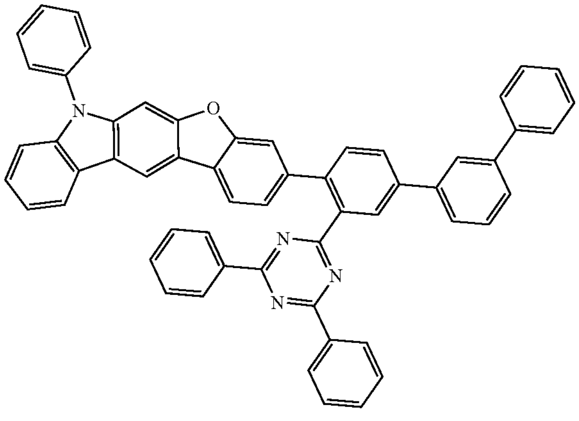
776
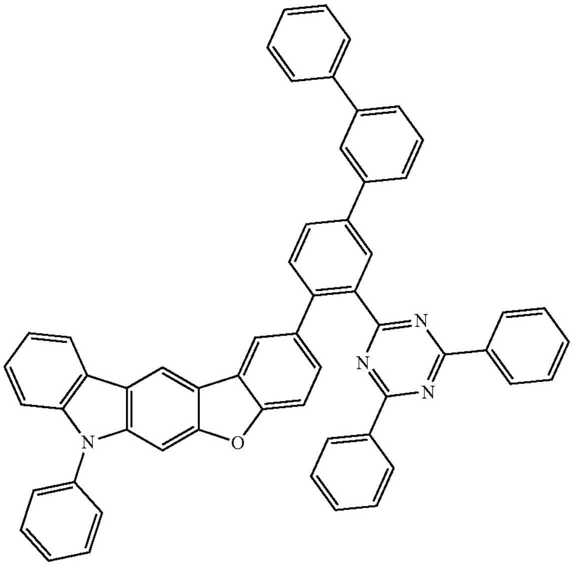
777
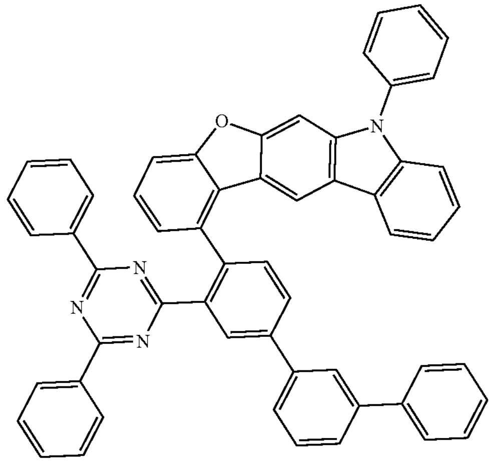
778
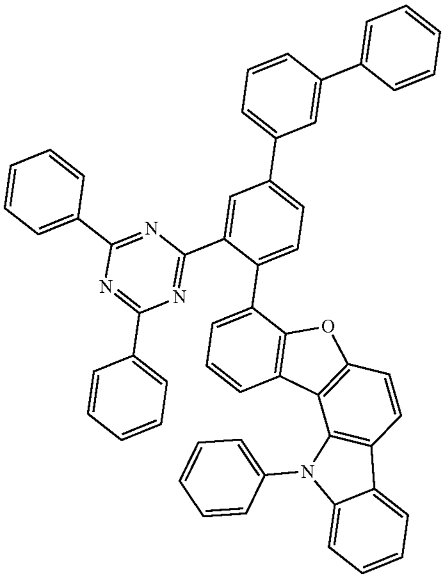

-continued
779
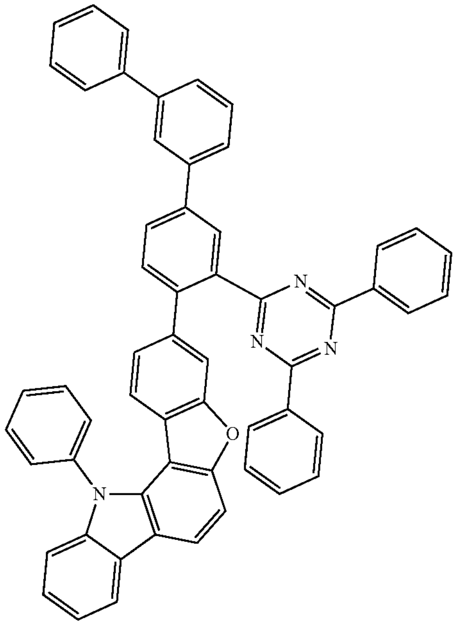
780
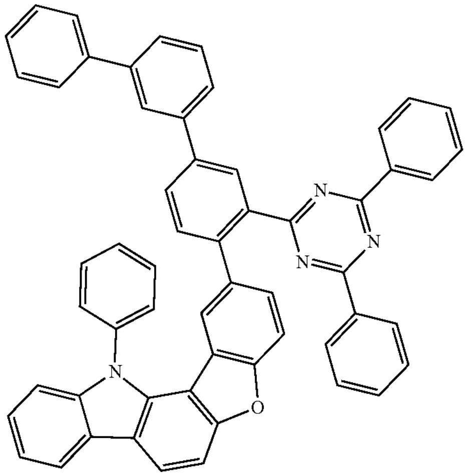
781
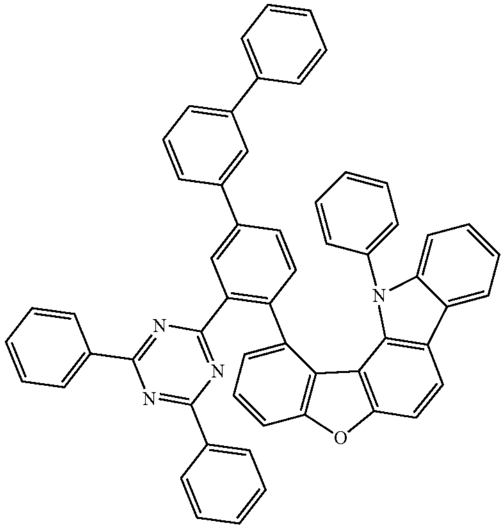
-continued
782
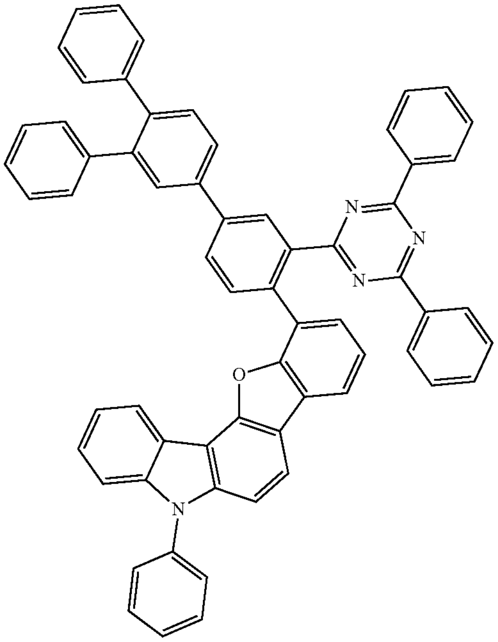
783
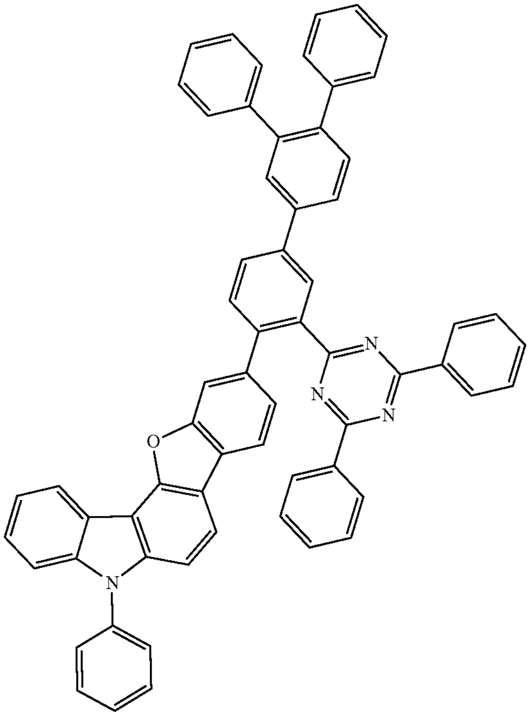

-continued
784
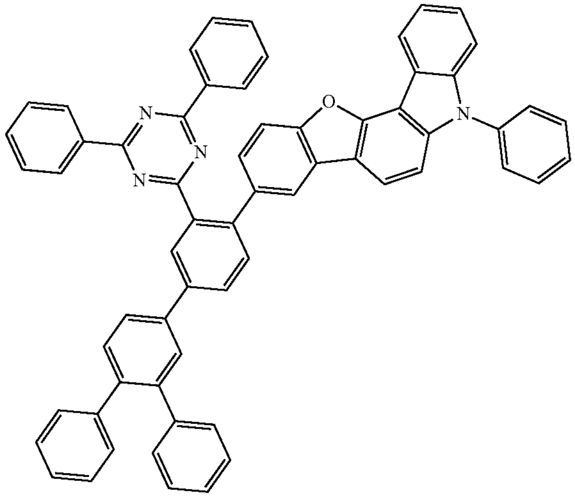
785
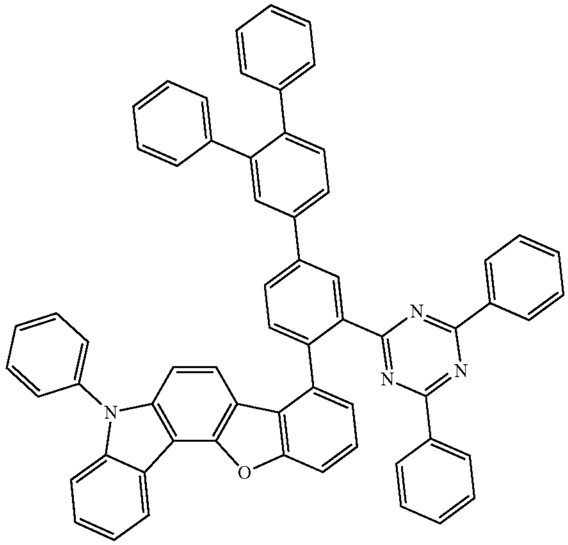
786
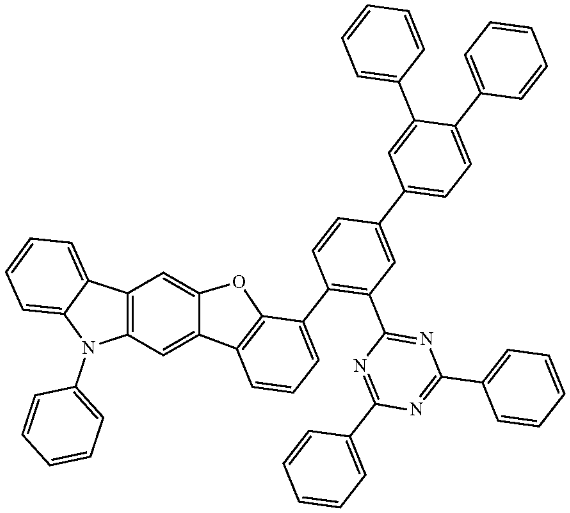
-continued
787
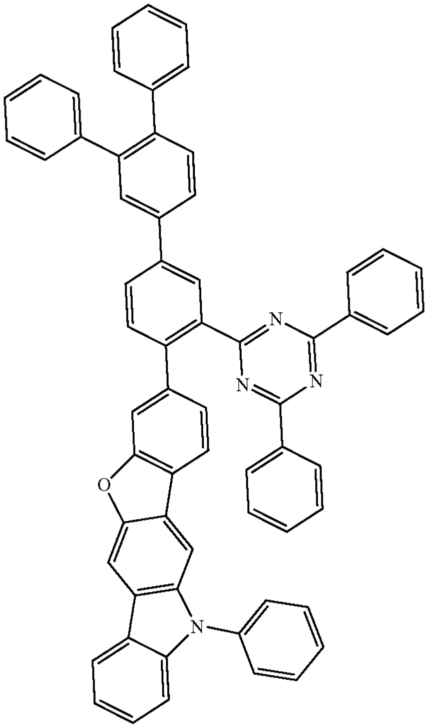
788
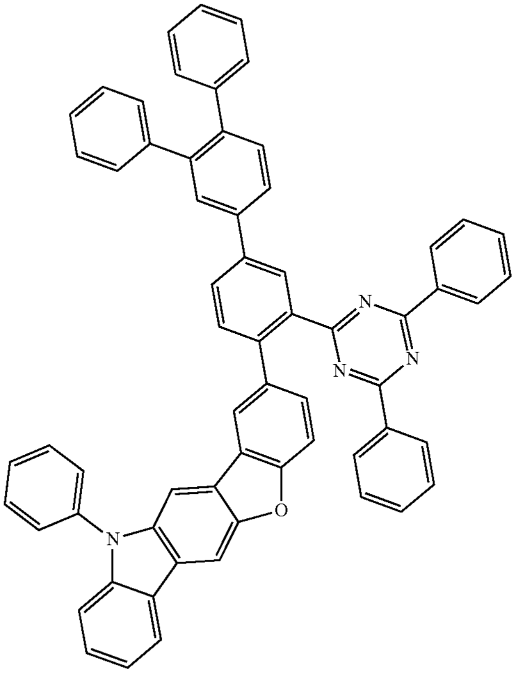

-continued
789
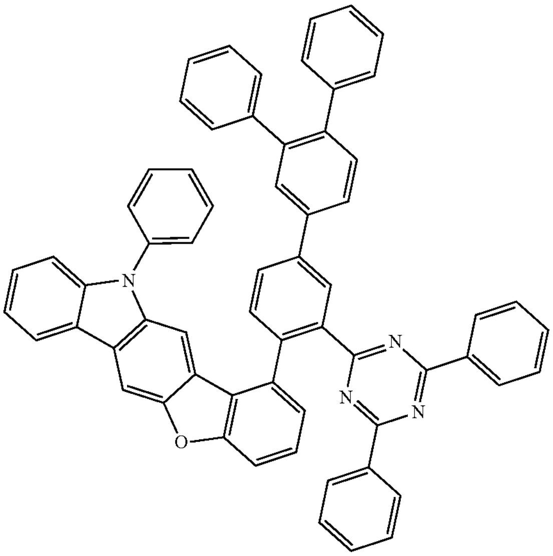
790
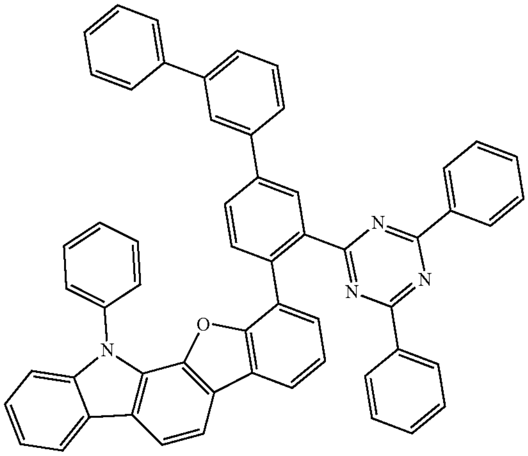
-continued
791
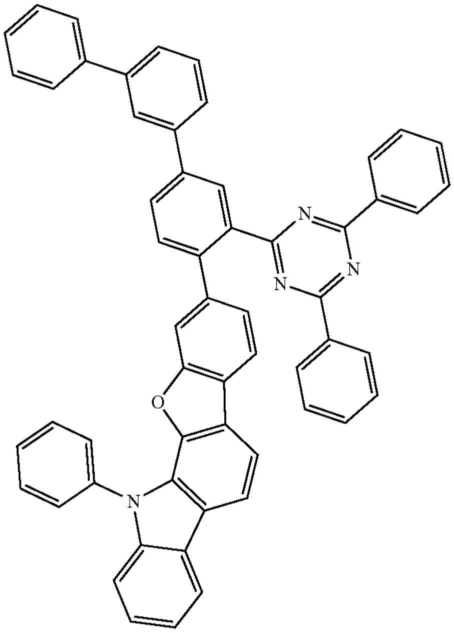
792
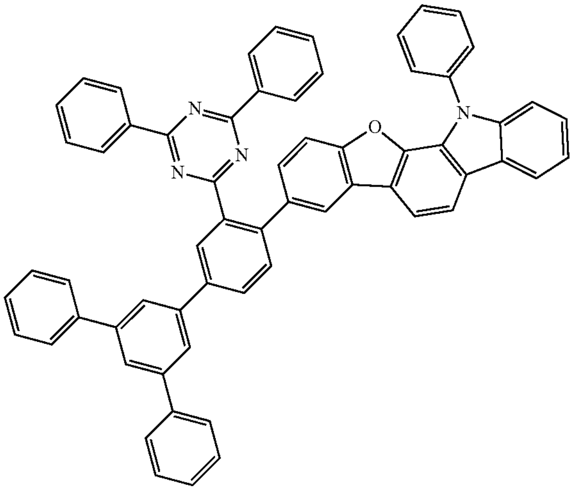

793
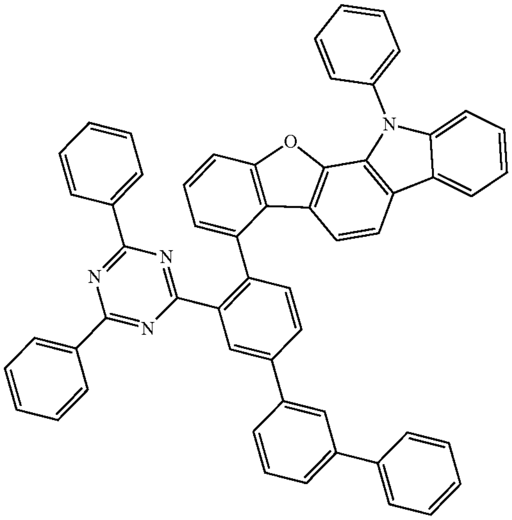
794
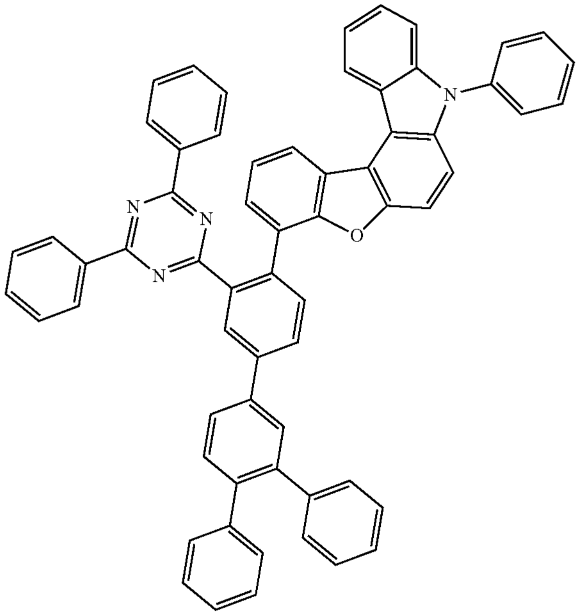
795
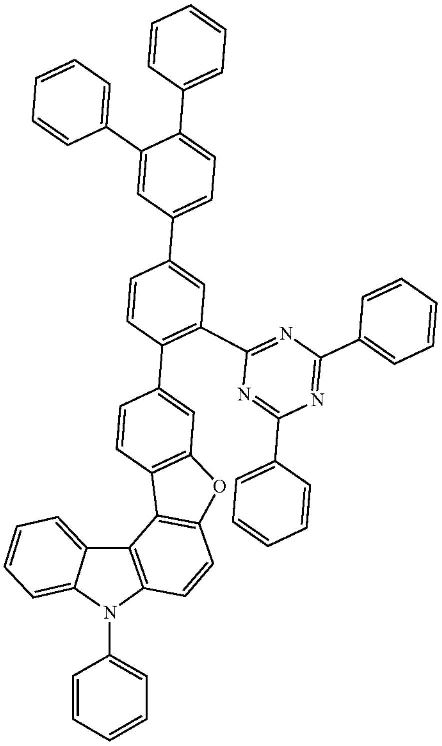
796
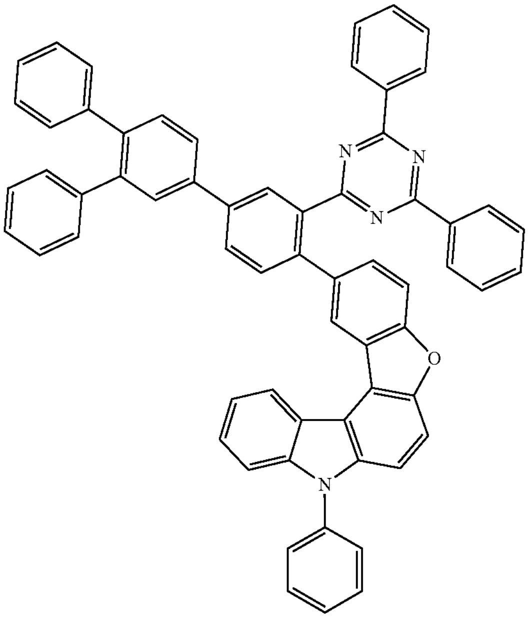

-continued
797
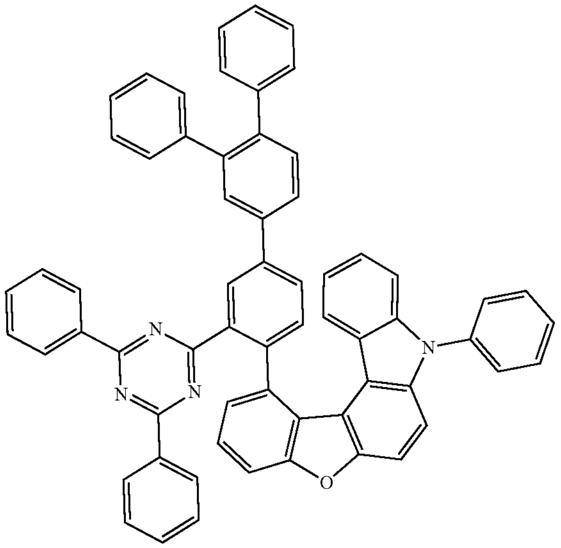
798
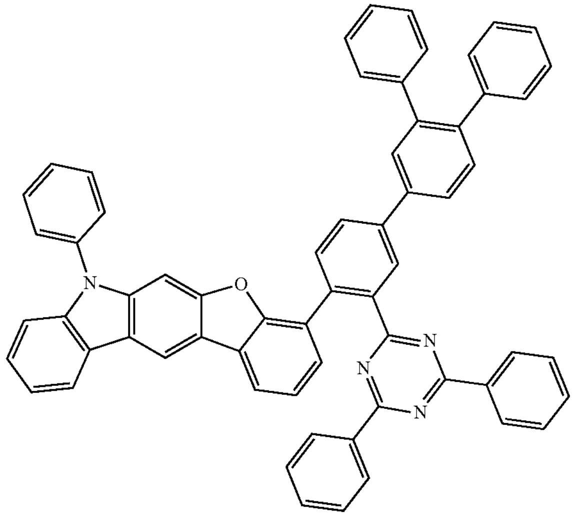
799
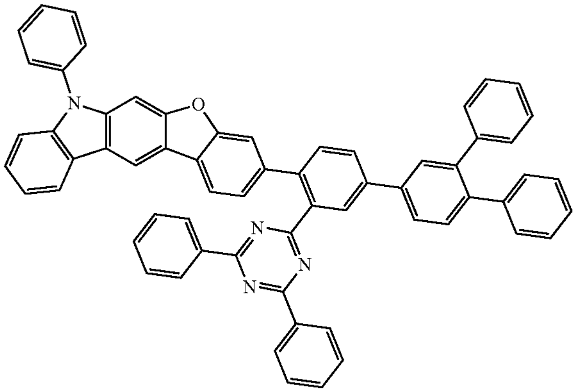
-continued
800
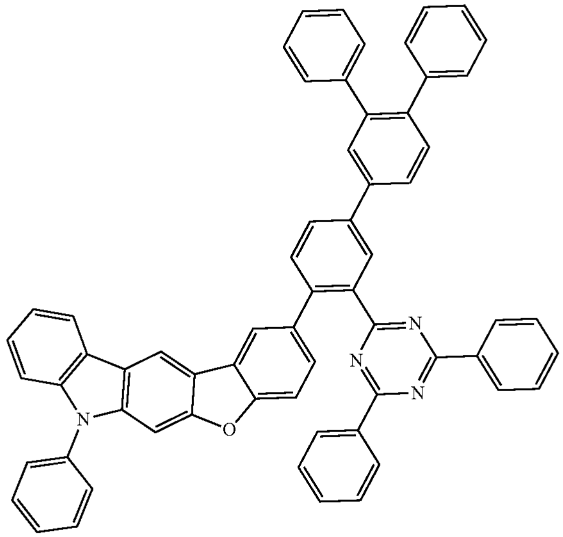
801
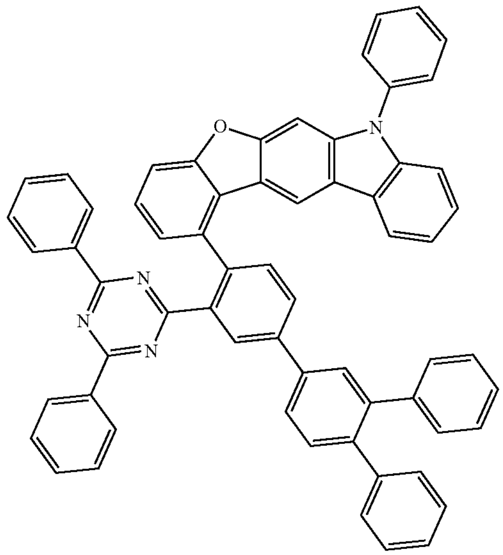

802
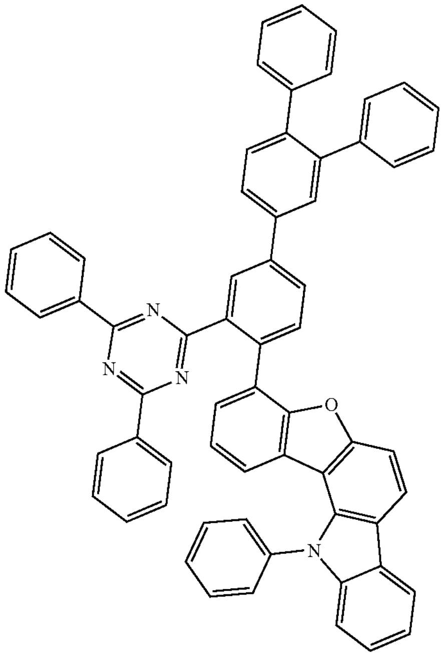
803
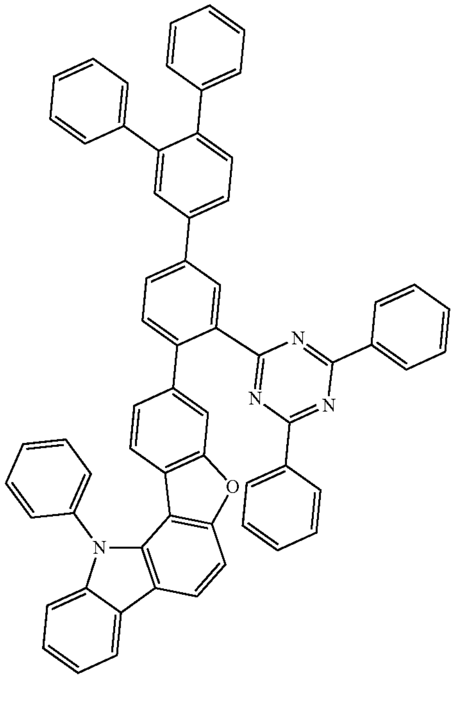
804
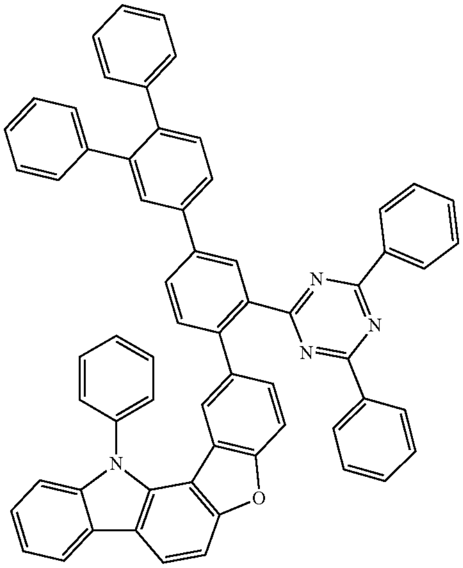
805
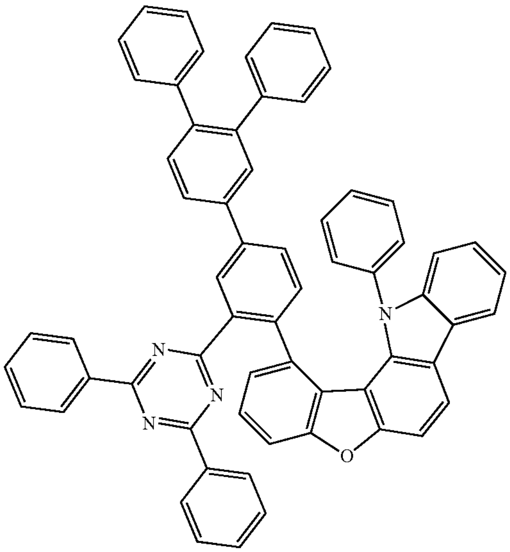

-continued
806
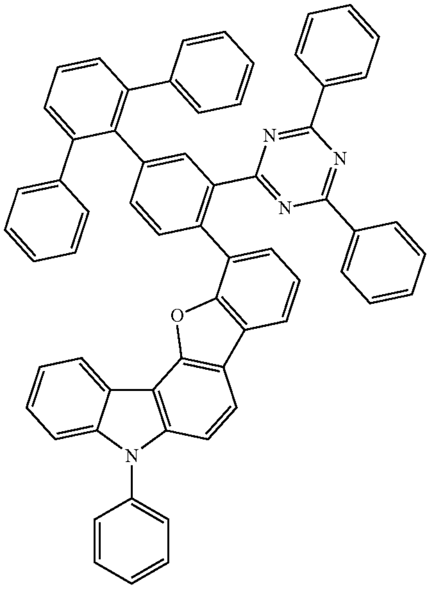
807
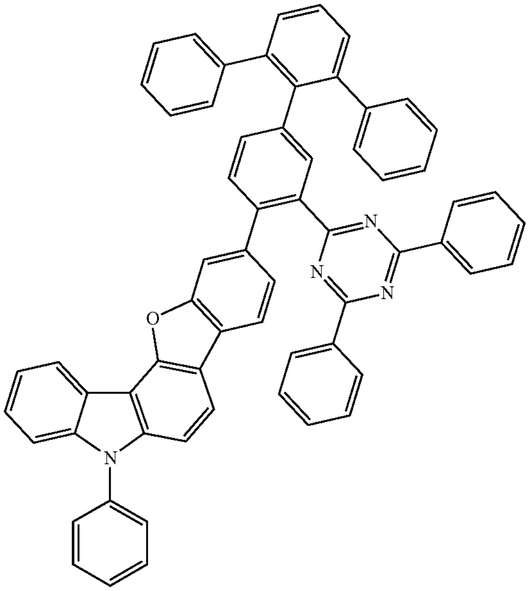
808
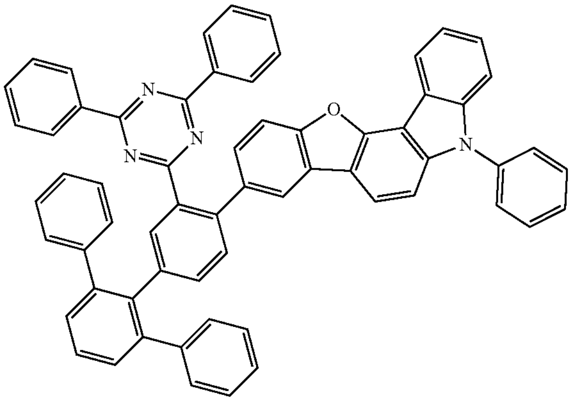
-continued
809
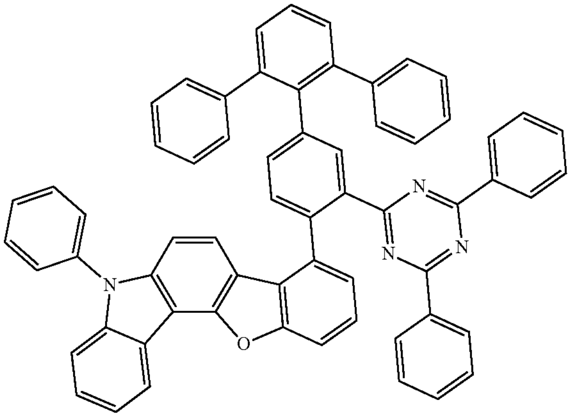
810
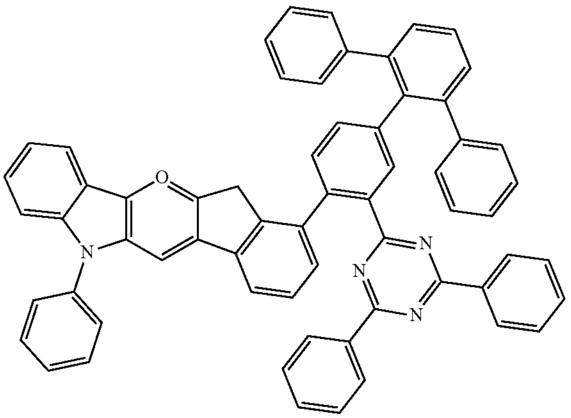
811
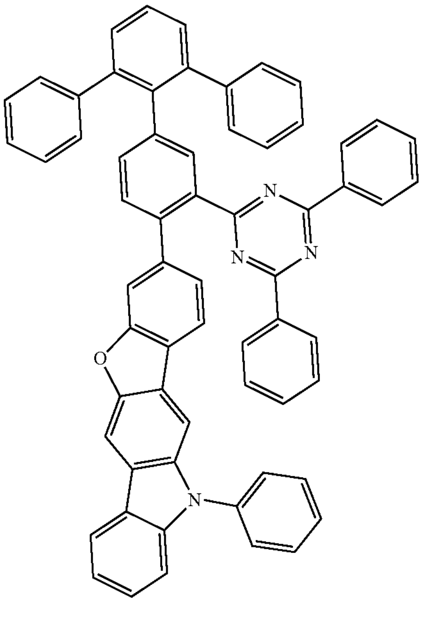

812
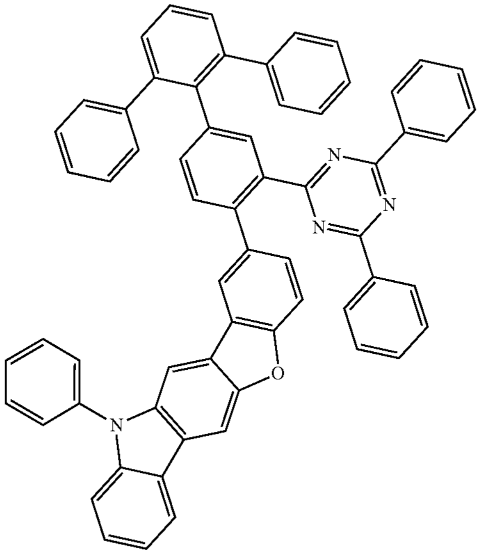
813
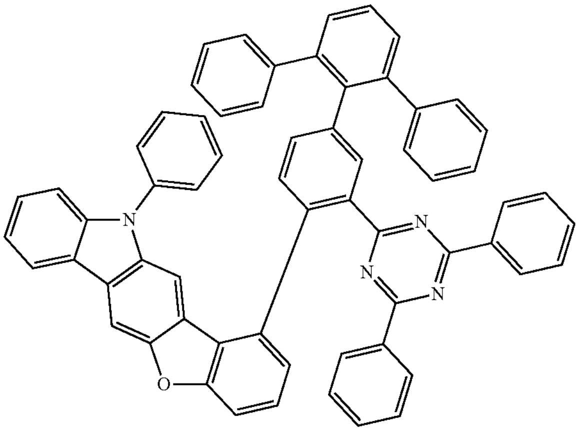
814
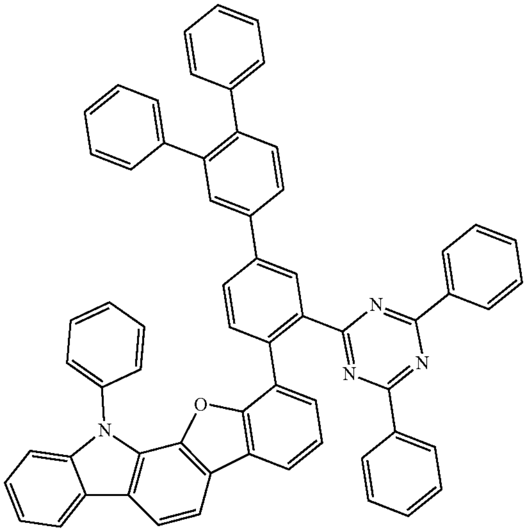
815
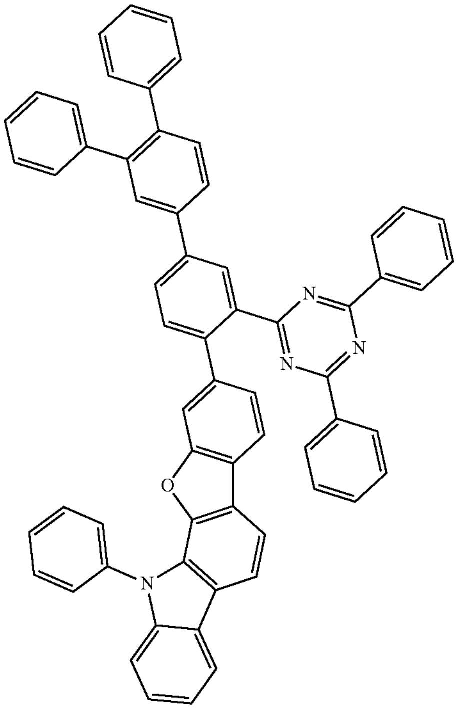
816
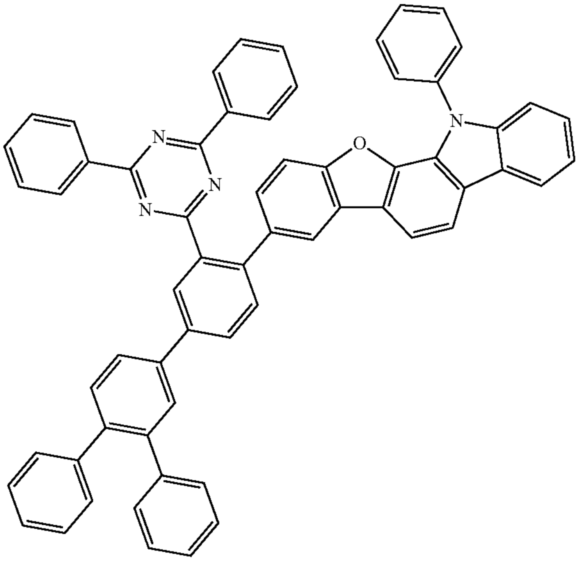

-continued
817
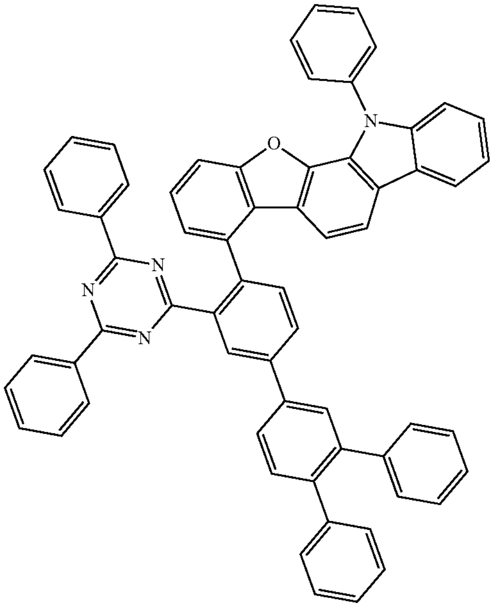
818
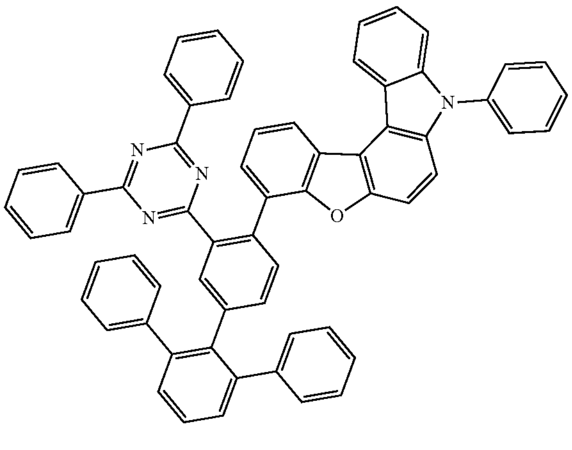
-continued
819
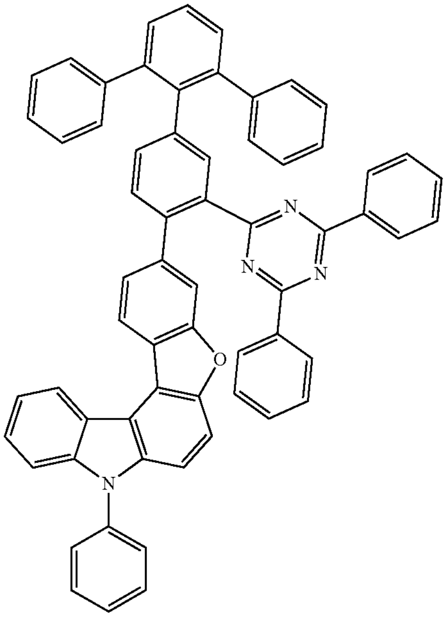
820
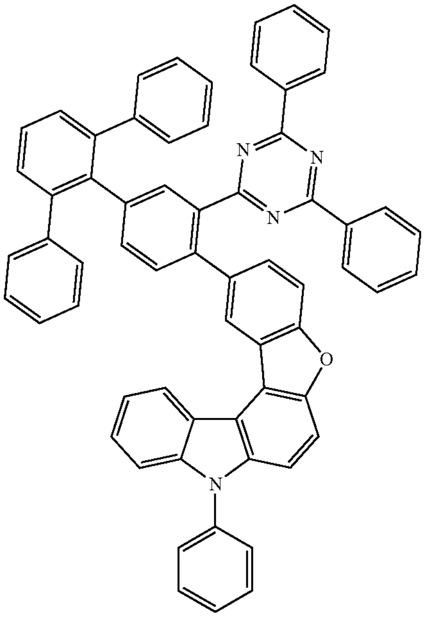

-continued
821
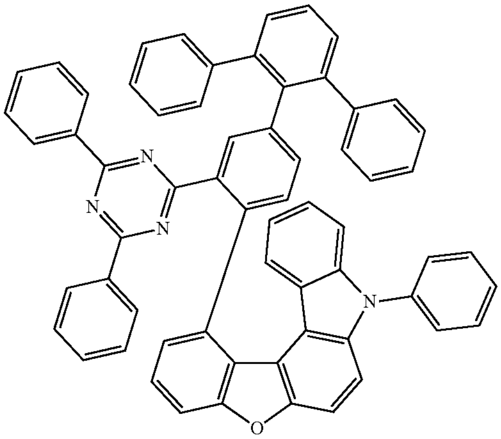
822
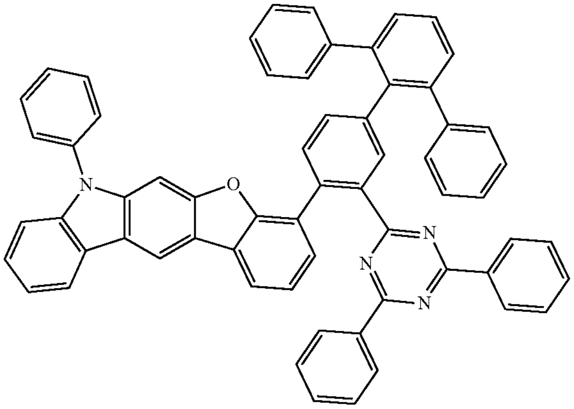
823
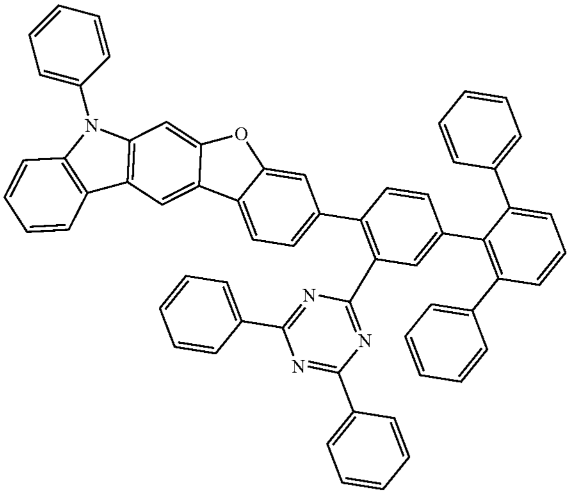
-continued
824
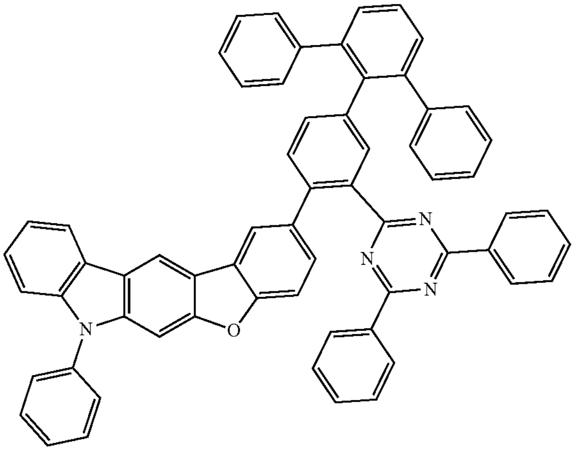
825
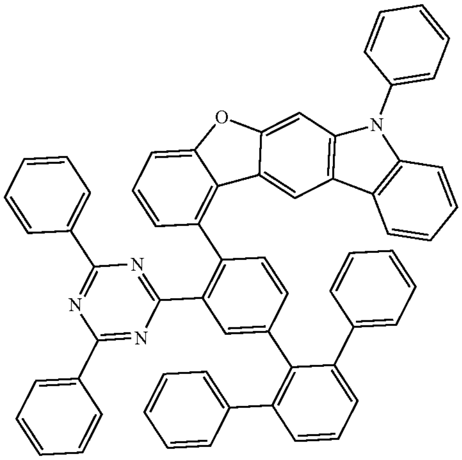
826
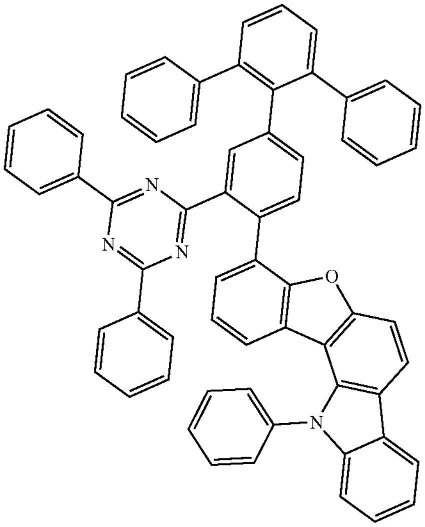

-continued
827
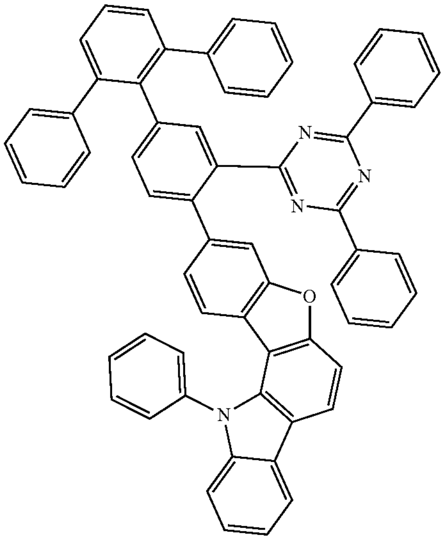
828
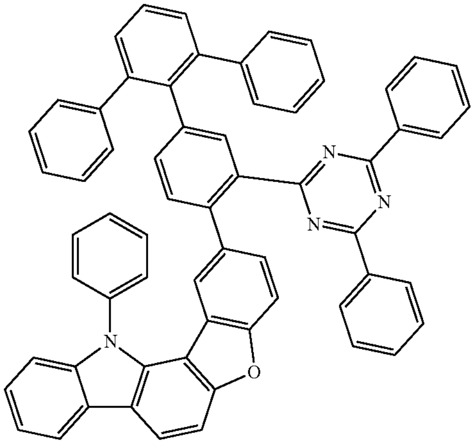
829
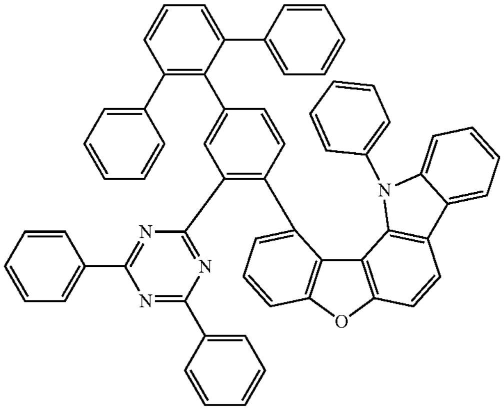
-continued
830
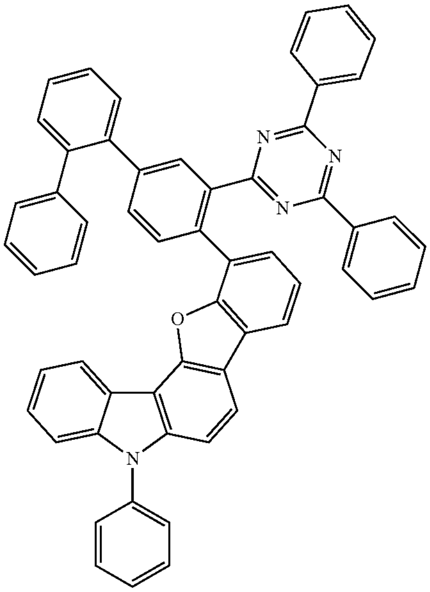
831
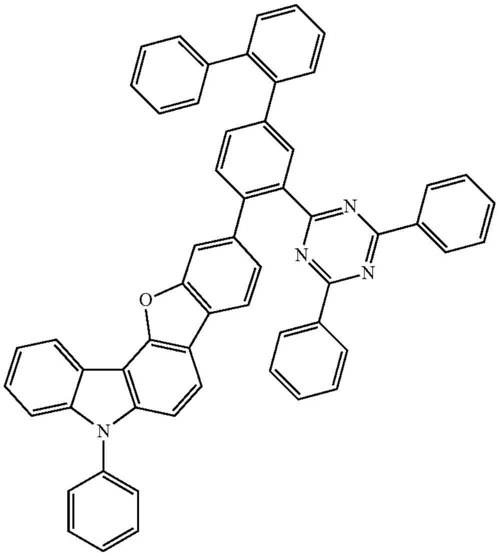
832
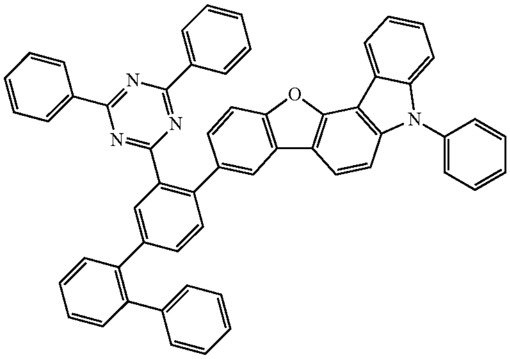

-continued
833
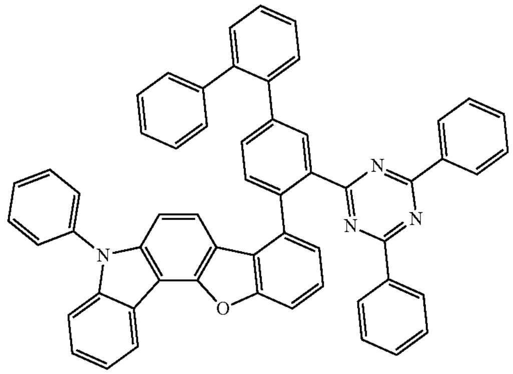
834
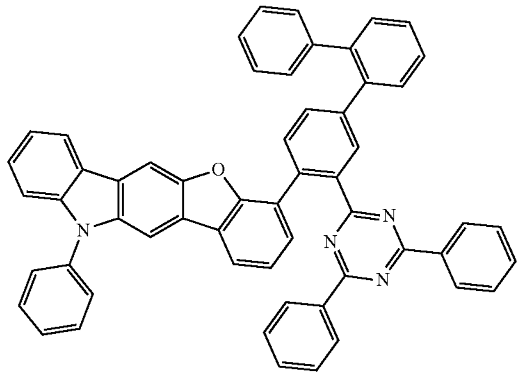
835
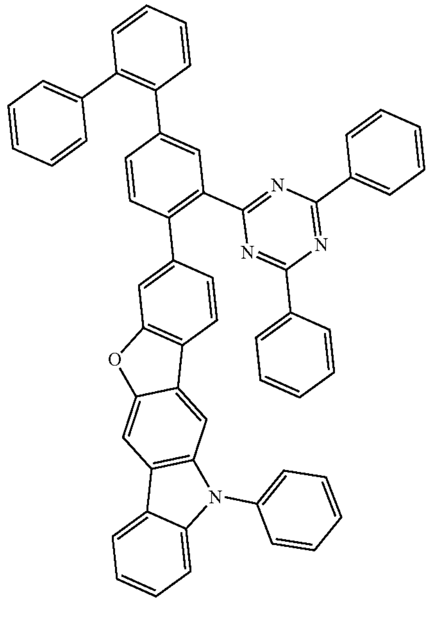
-continued
836
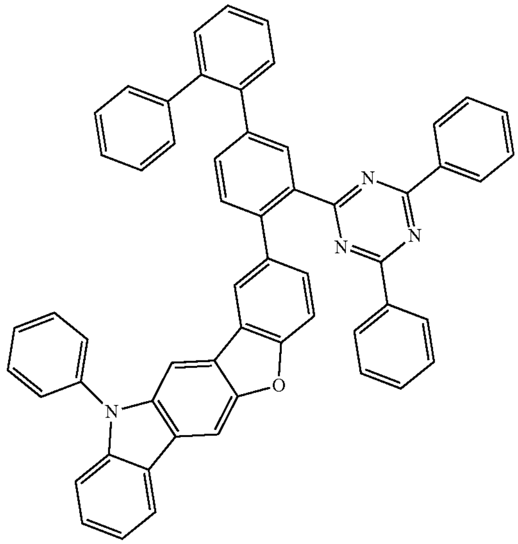
837
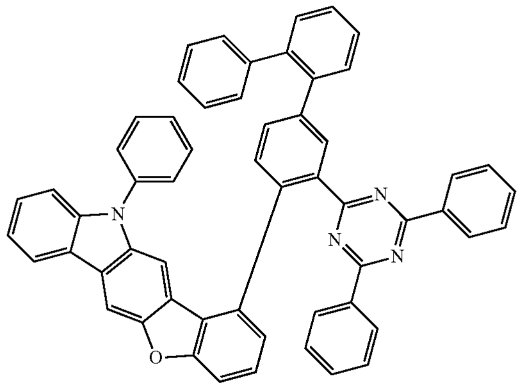
838
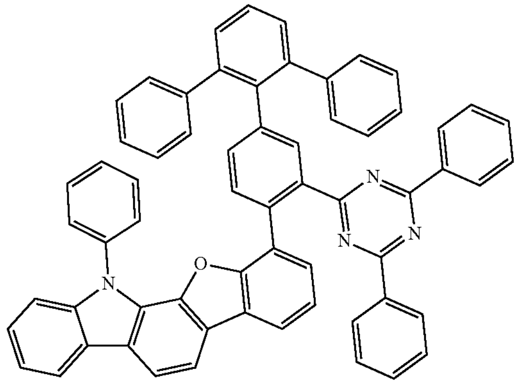

-continued
839
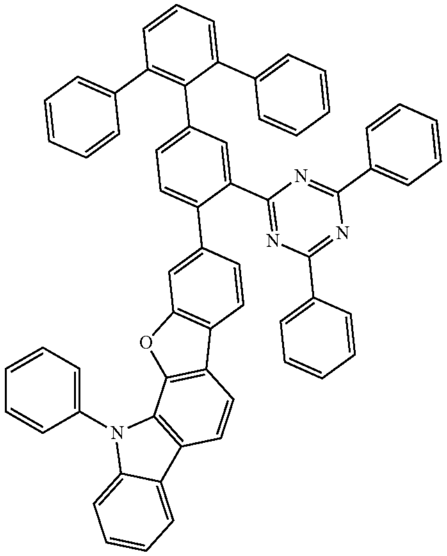
840
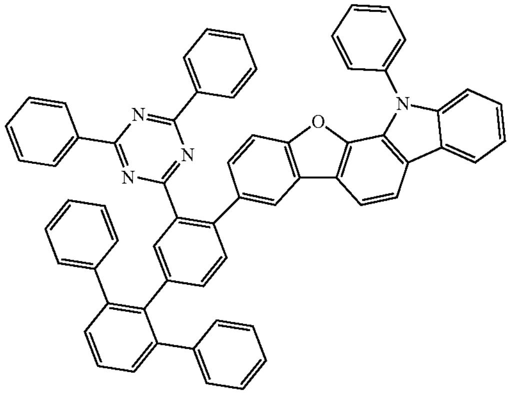
841
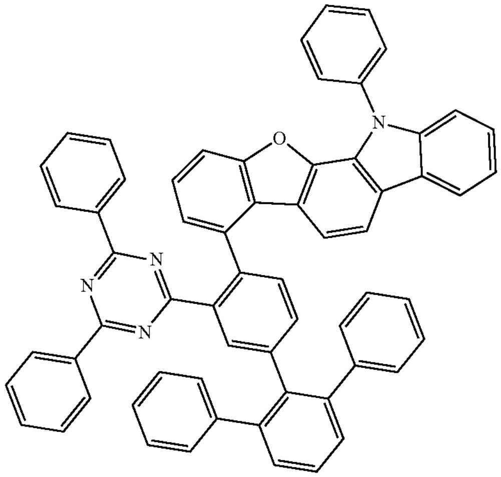
-continued
842
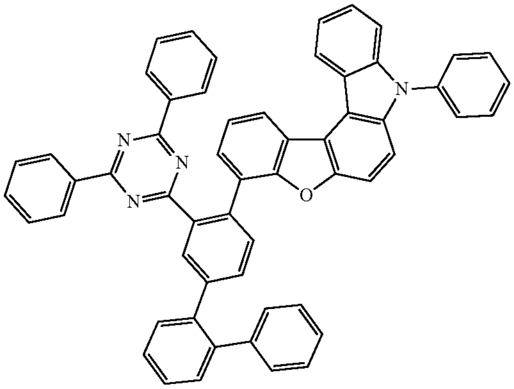
843
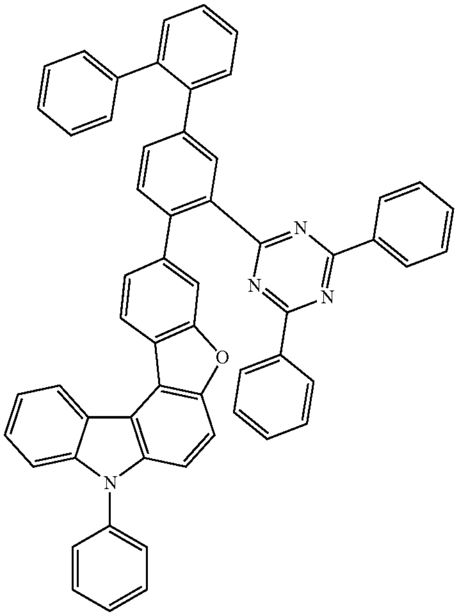
844
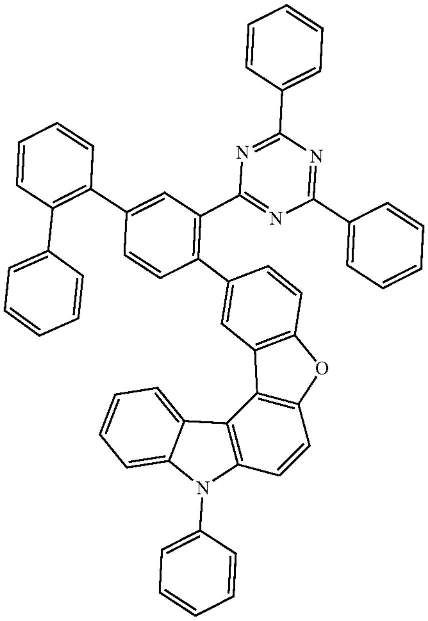

-continued
845
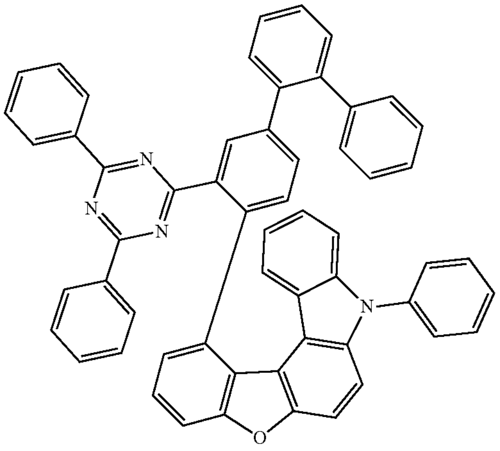
846
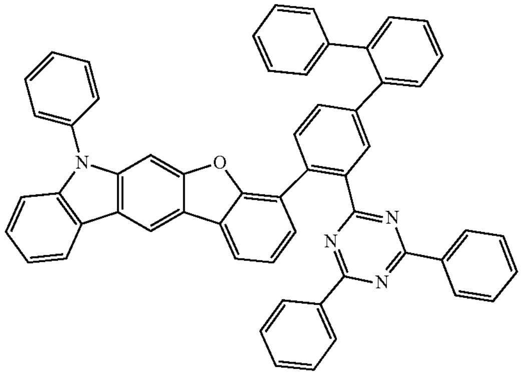
847
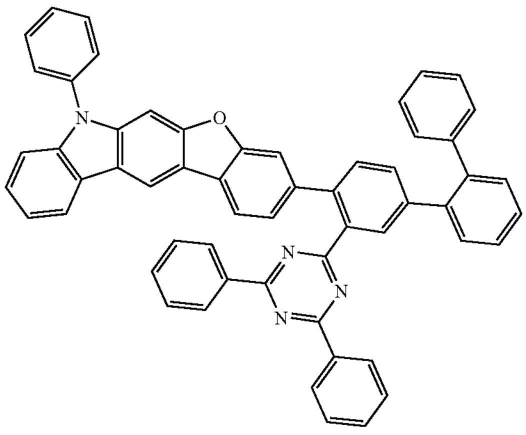
-continued
848
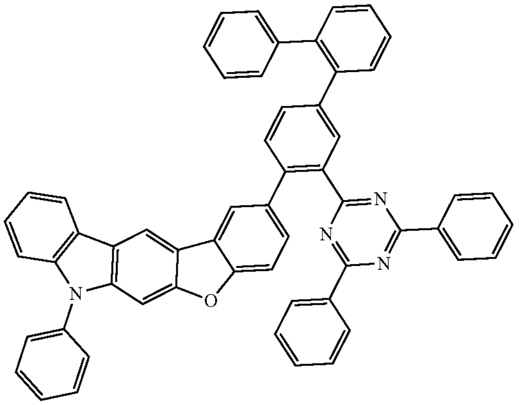
849
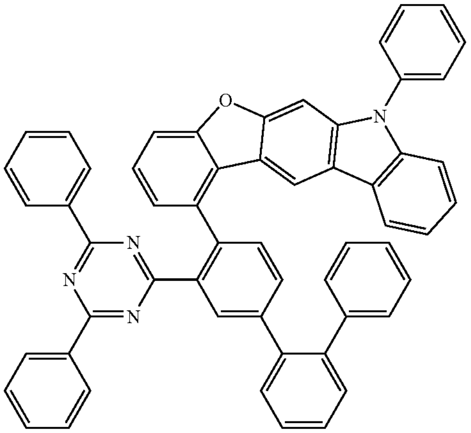
850
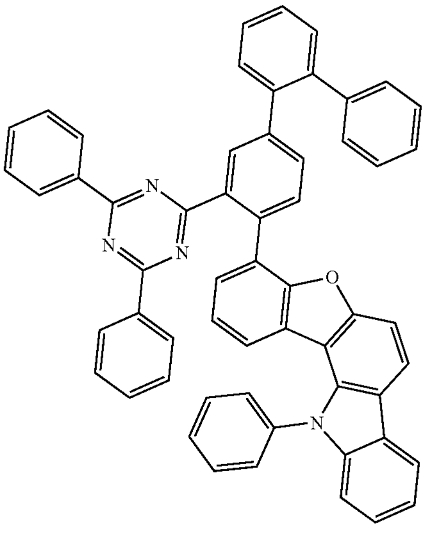

-continued
851
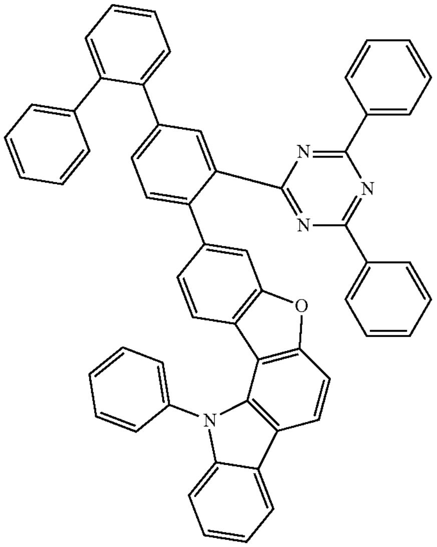
852
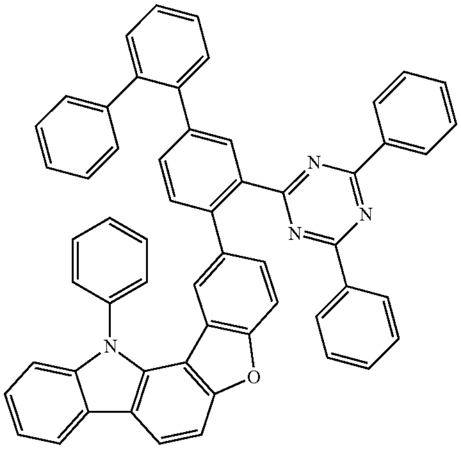
853
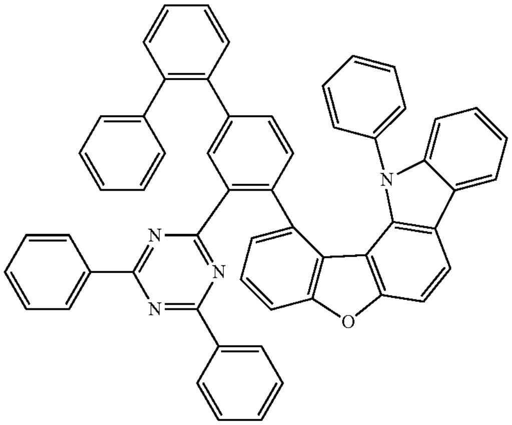
-continued
854
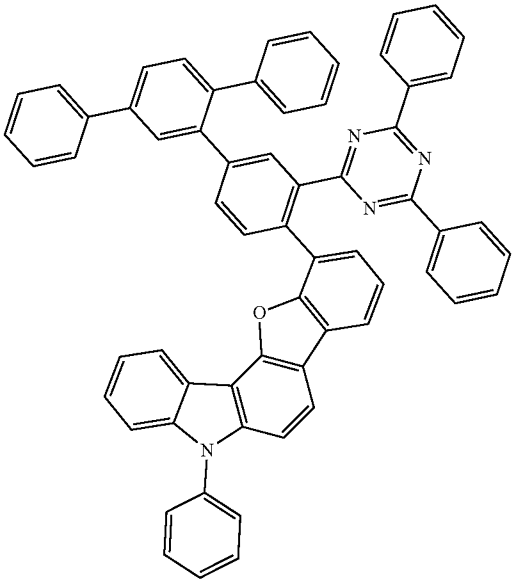
855
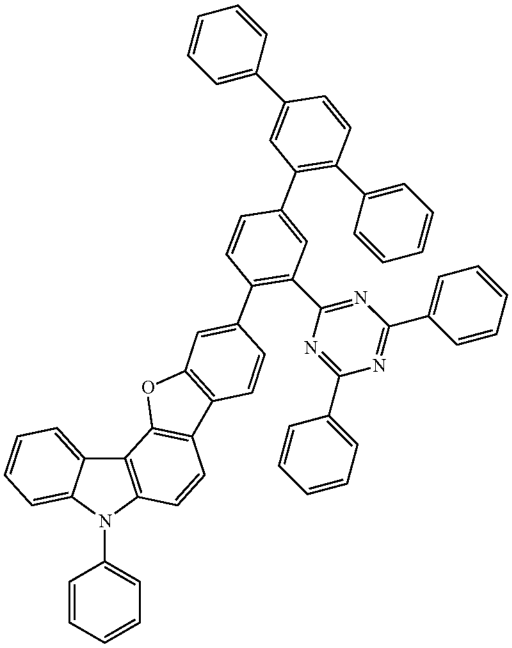

-continued
856
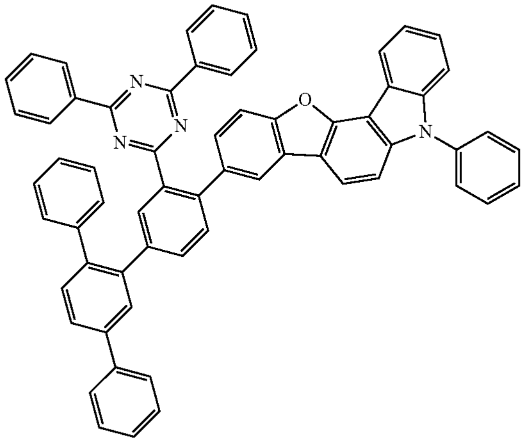
857
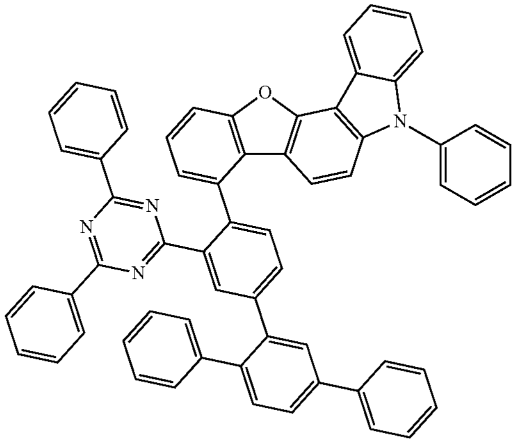
858
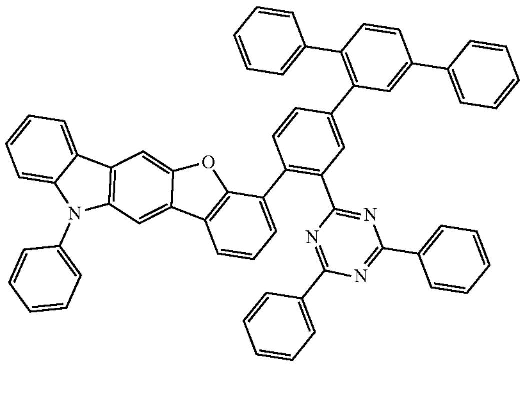
-continued
859
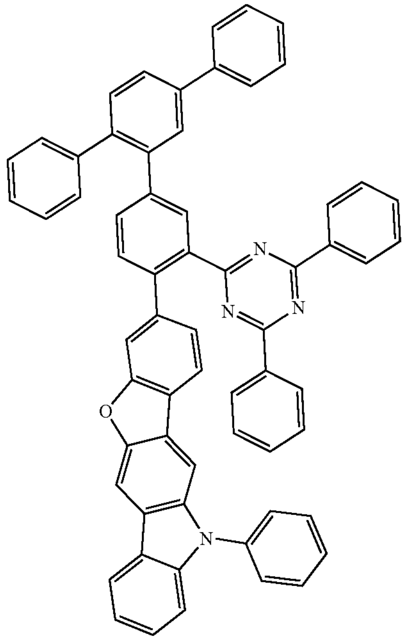
860
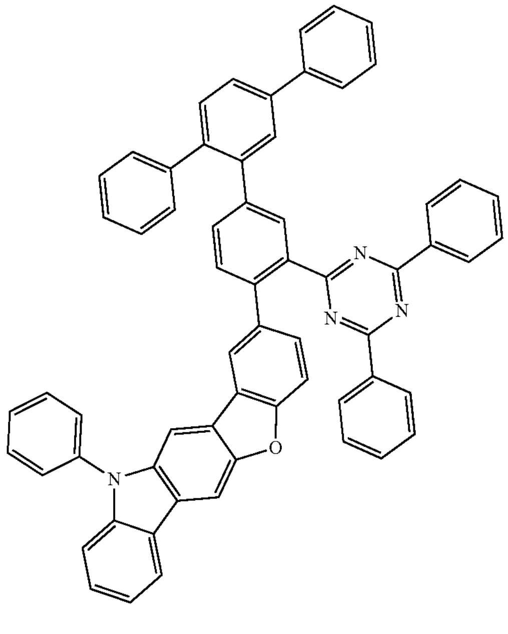

-continued
861
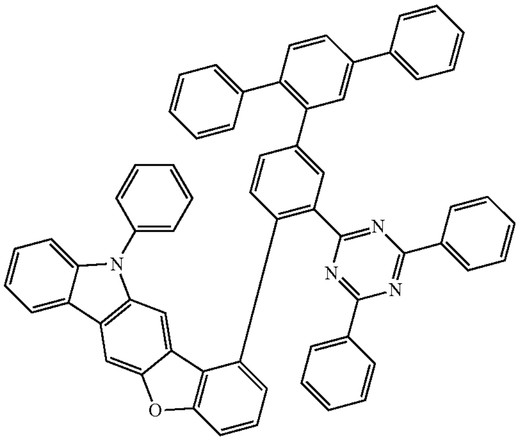
862
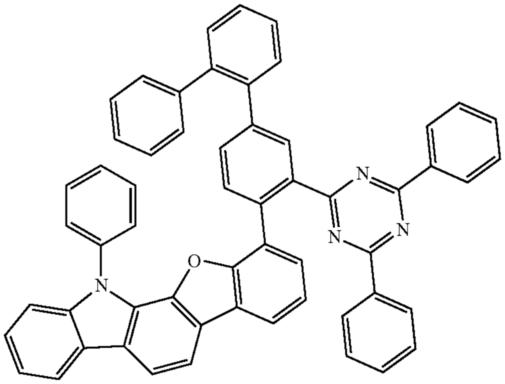
863
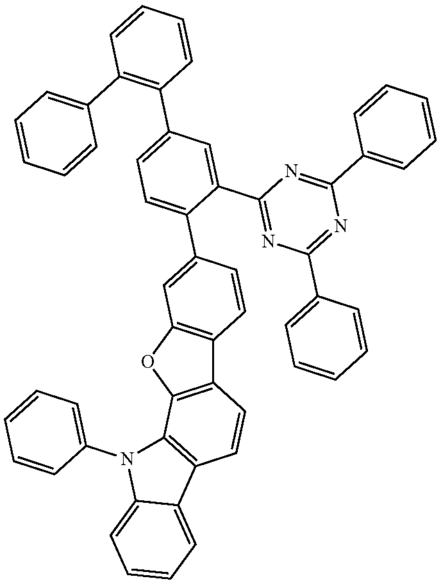
-continued
864
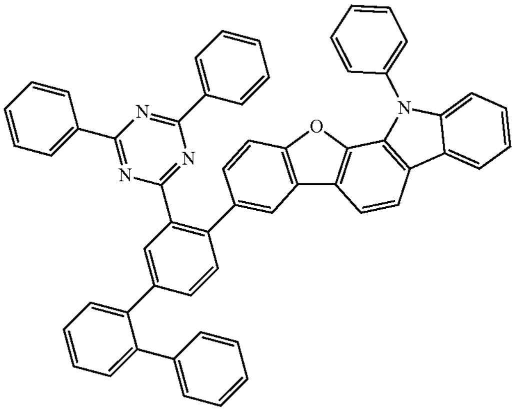
865
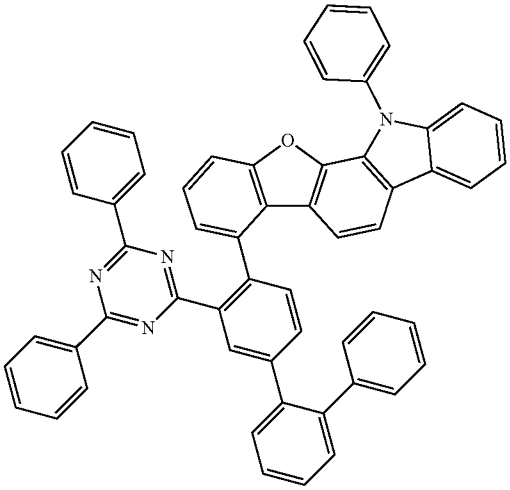
866
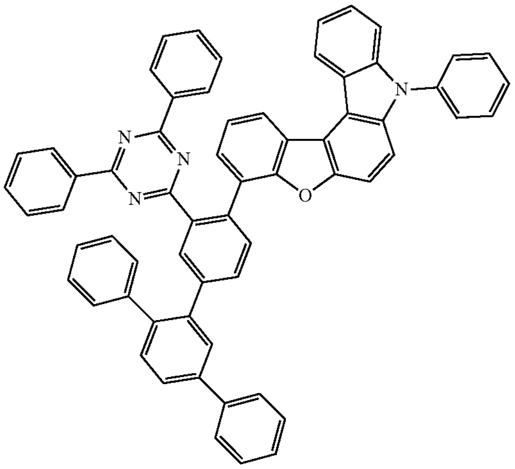

-continued
867
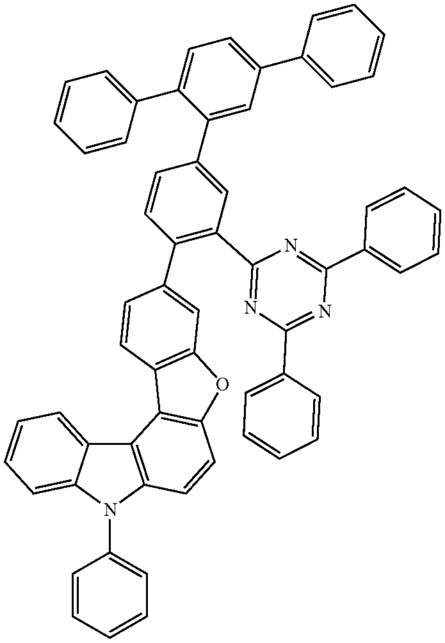
868
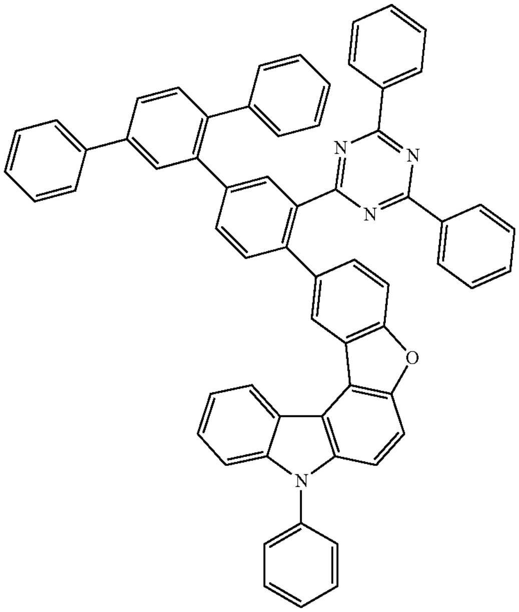
-continued
869
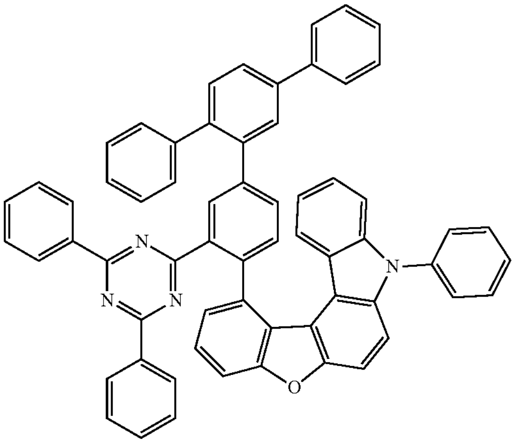
870
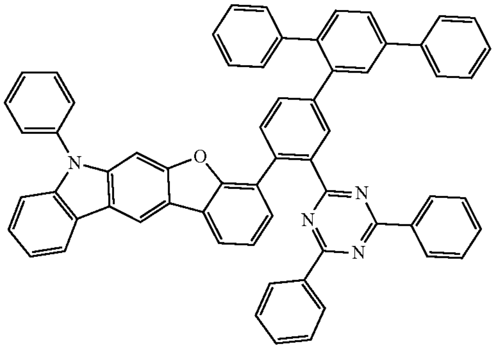
871
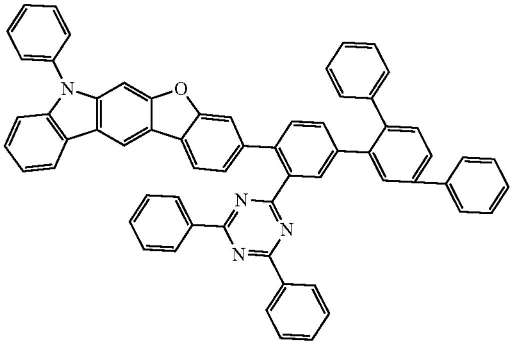

-continued
872
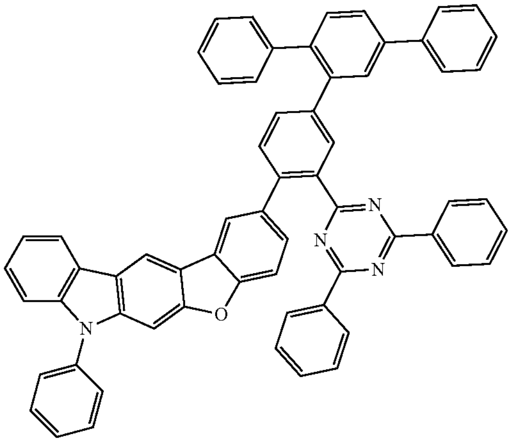
873
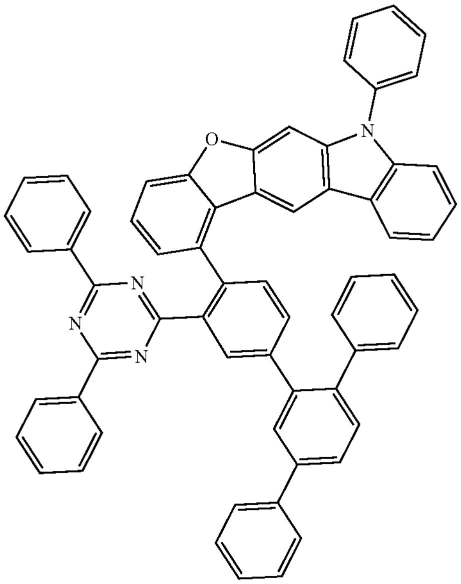
874
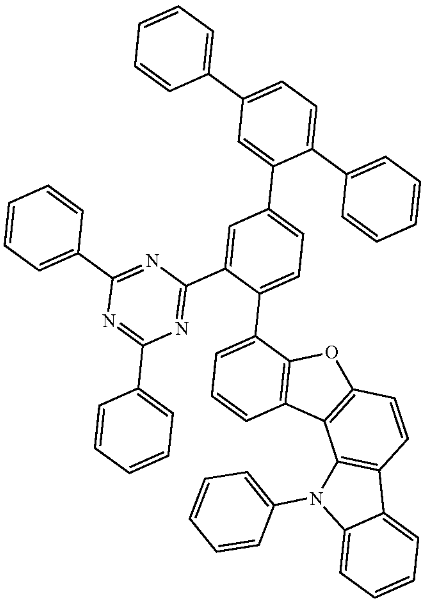
-continued
875
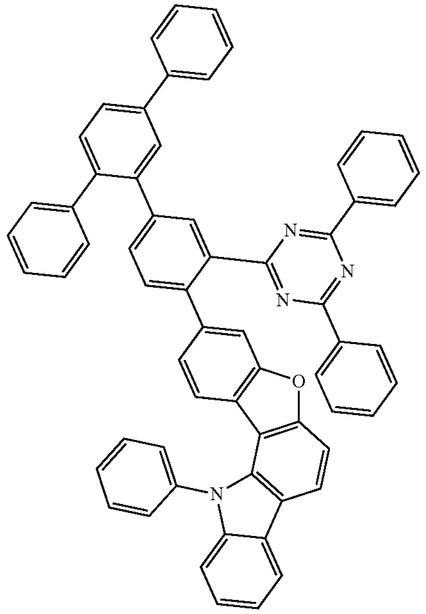
876
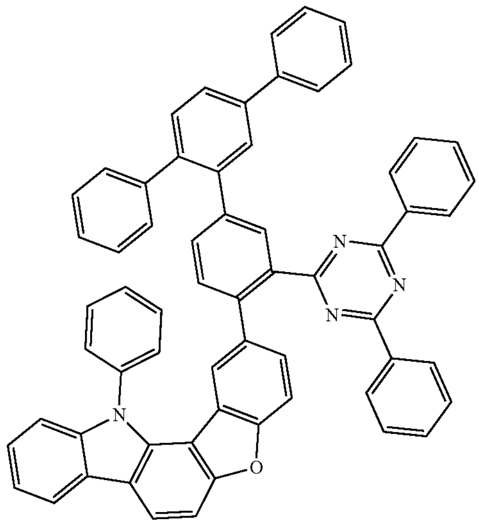

-continued
877
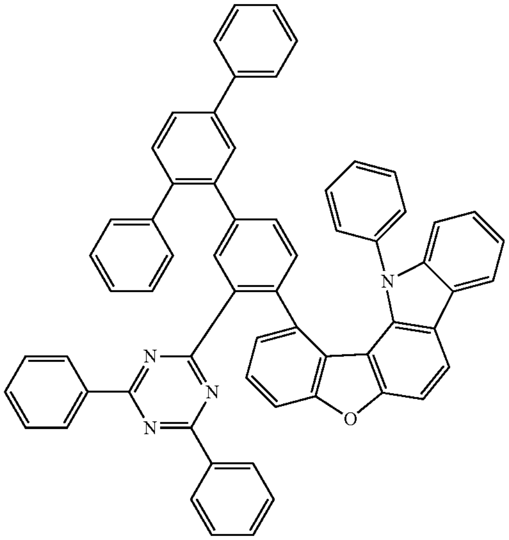
878
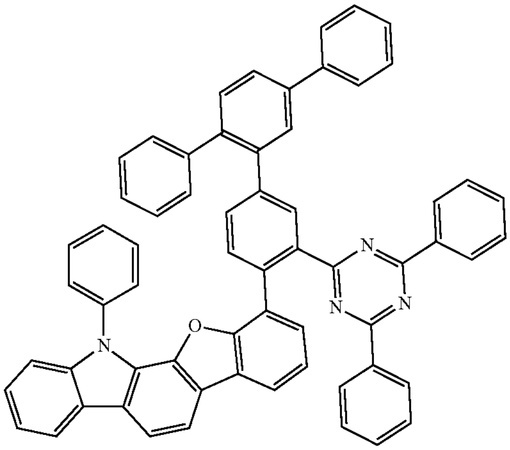
-continued
879
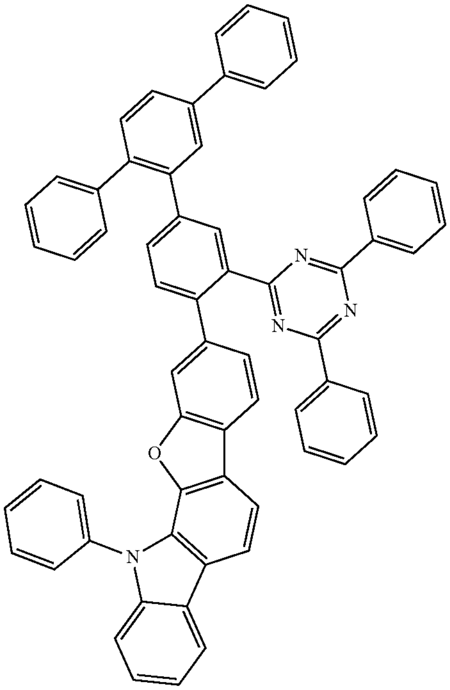
880
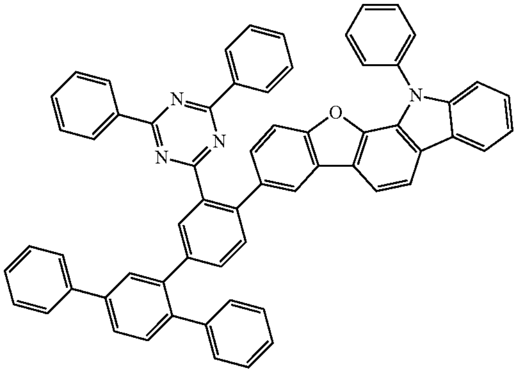

-continued
881
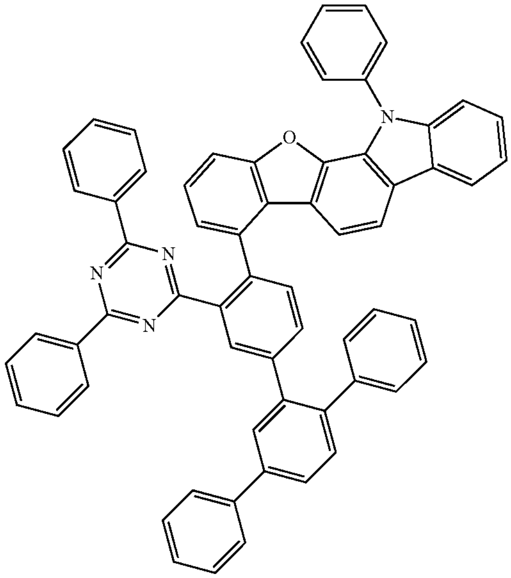
882
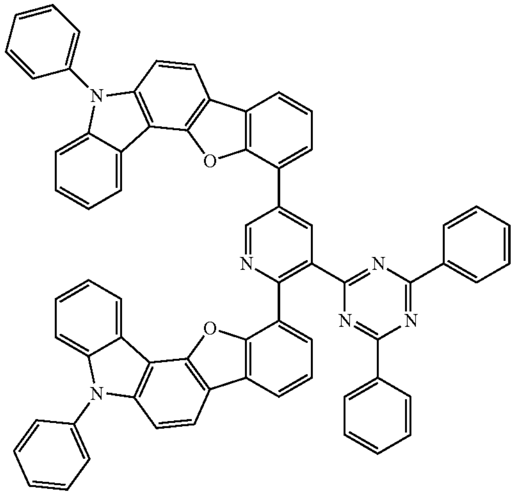
-continued
883
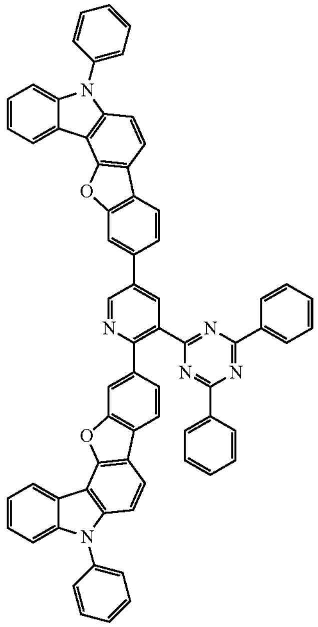
884
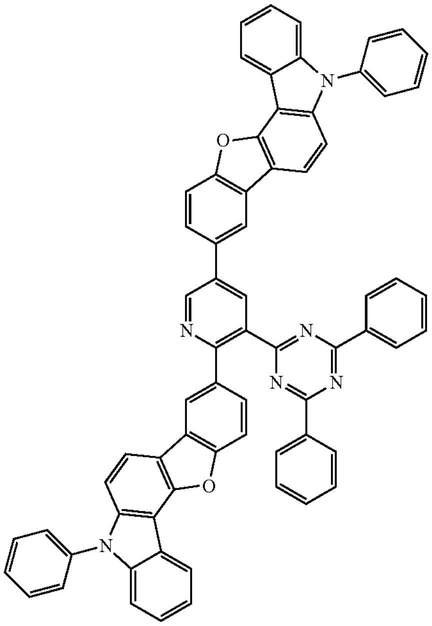

-continued
885
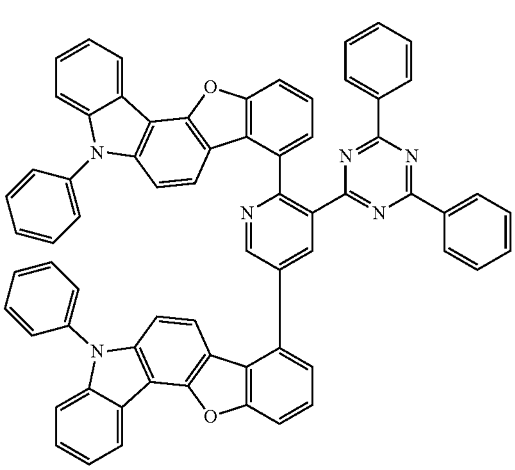
886
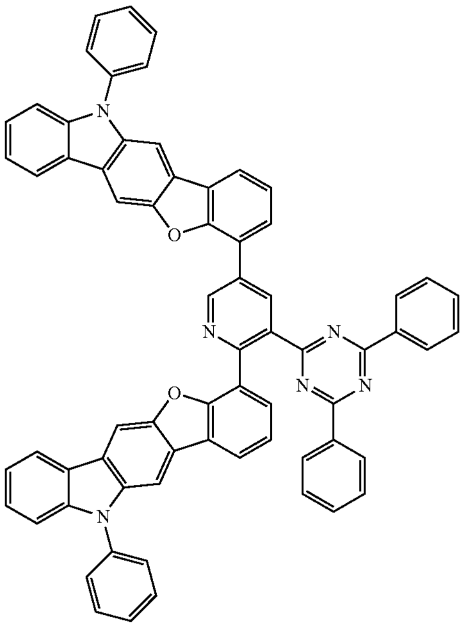
-continued
887
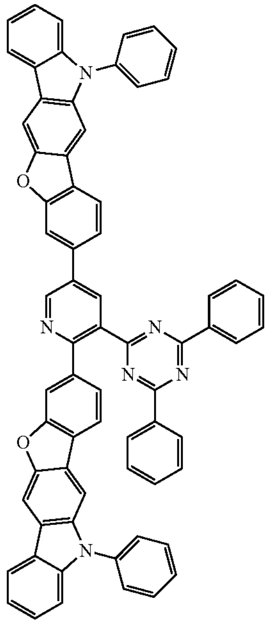
888
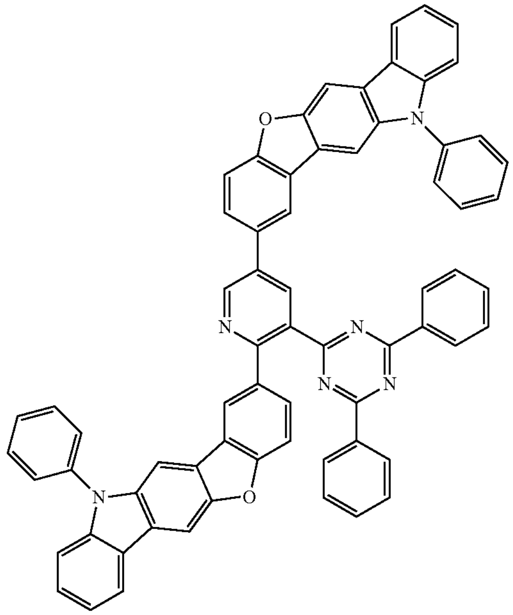

-continued
889
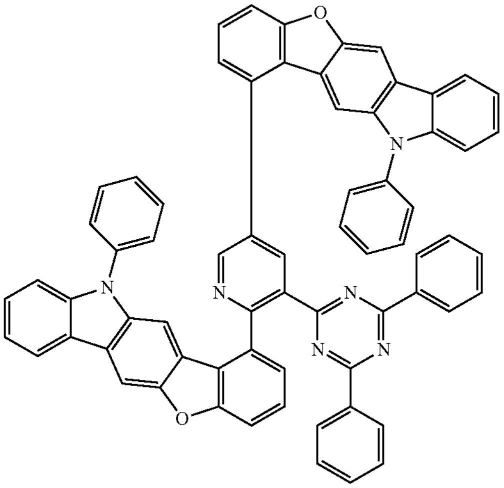
890
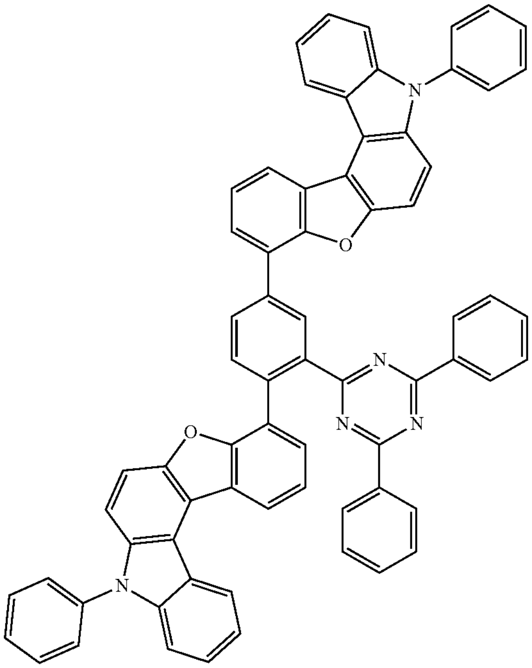

-continued
891
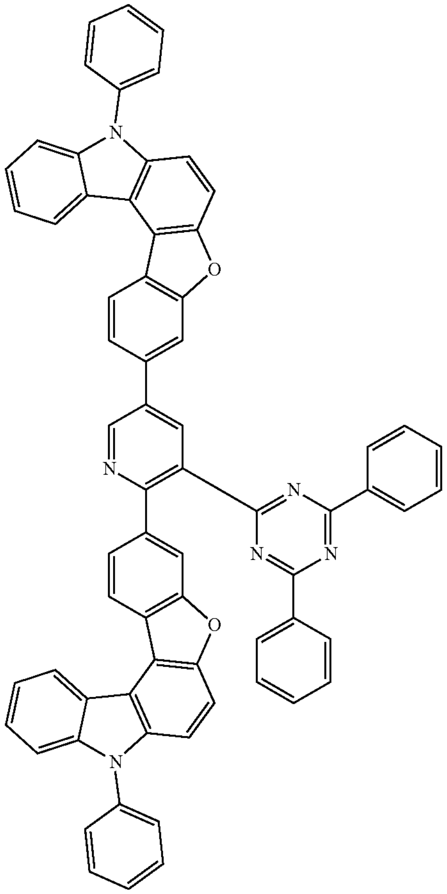
892
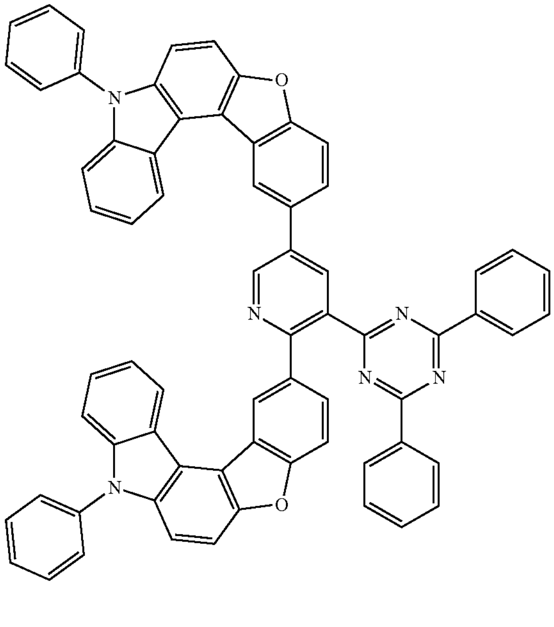

-continued
893
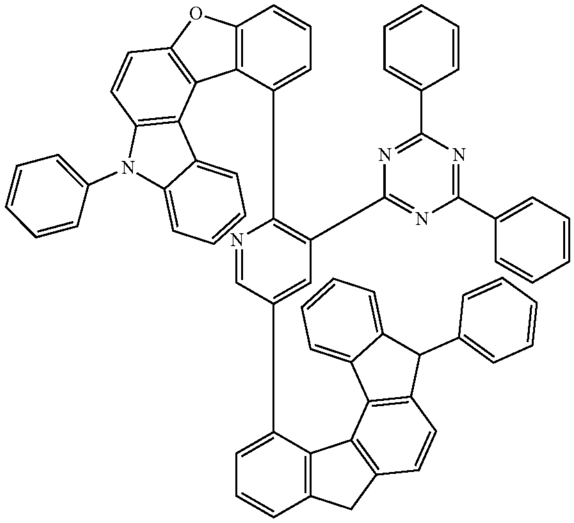
894
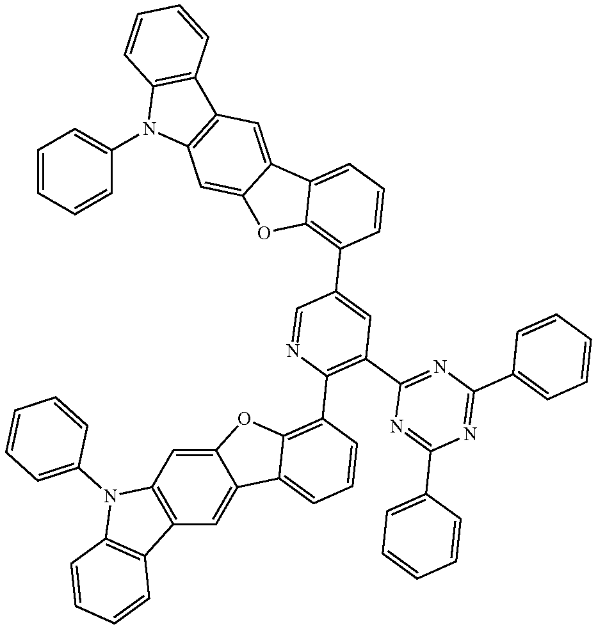

-continued
895
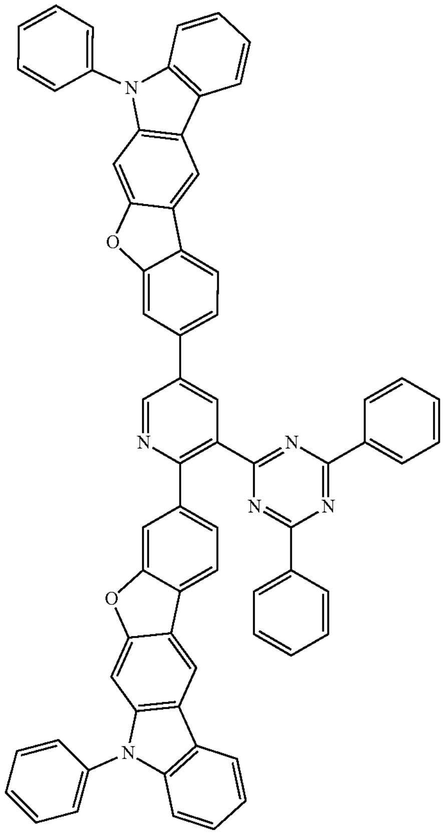
896
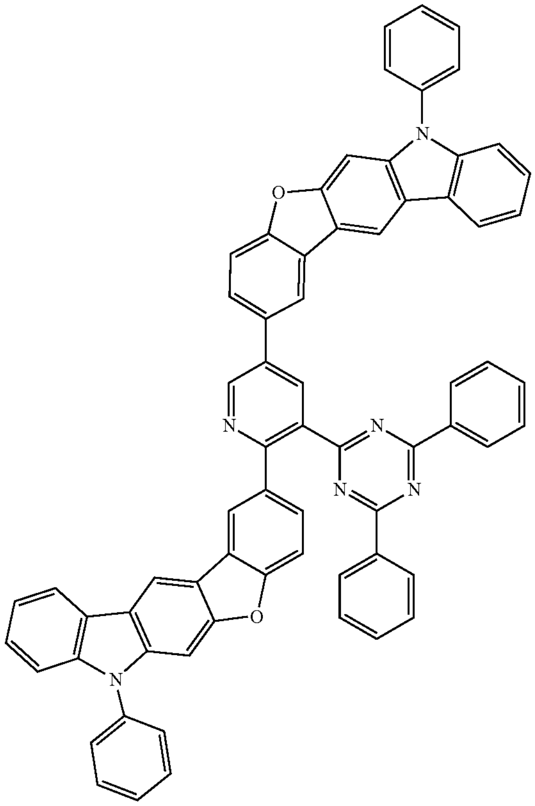

-continued
897
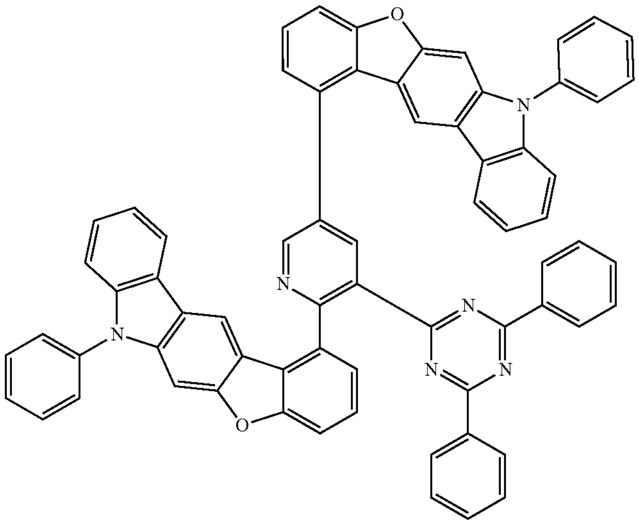
898
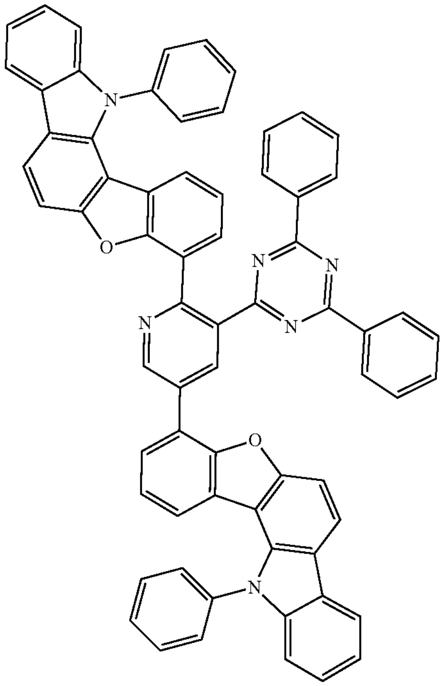

-continued
899
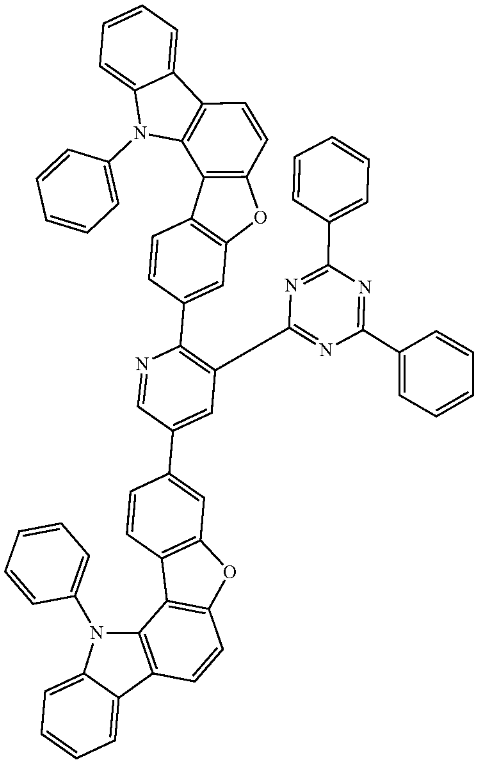
900
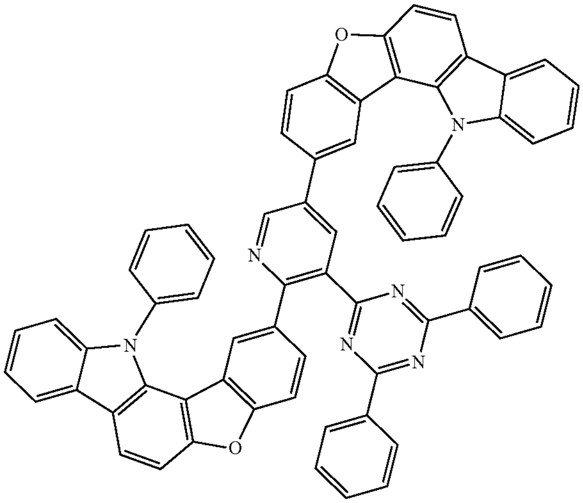

-continued
901
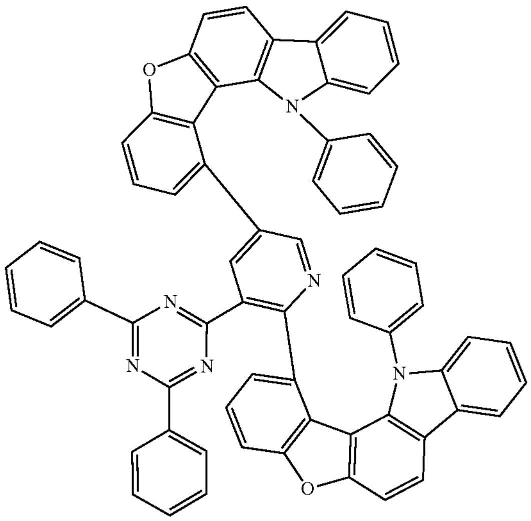
902
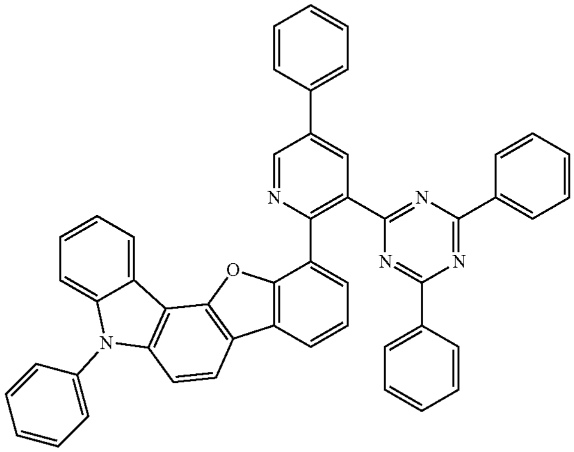
903
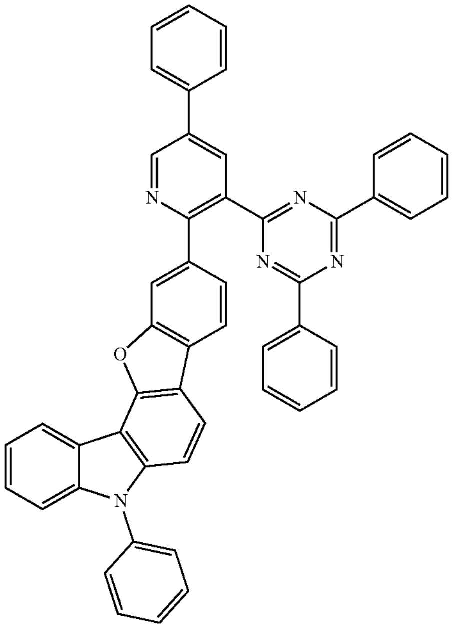

-continued
904
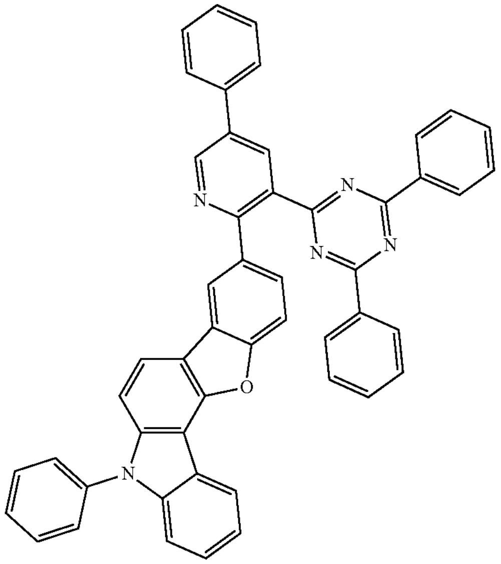
905
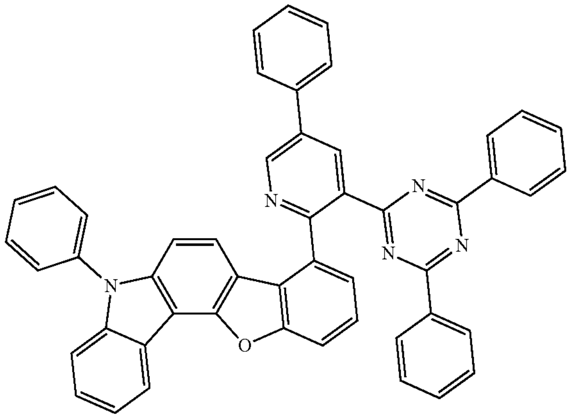
906
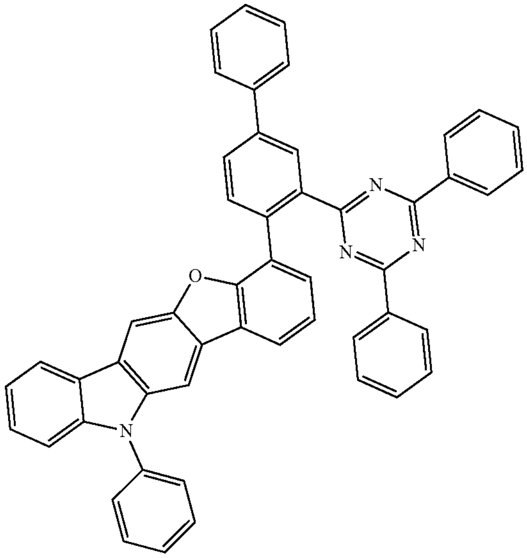

-continued
907
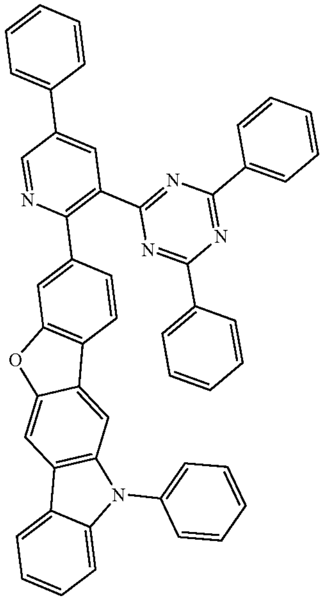
908
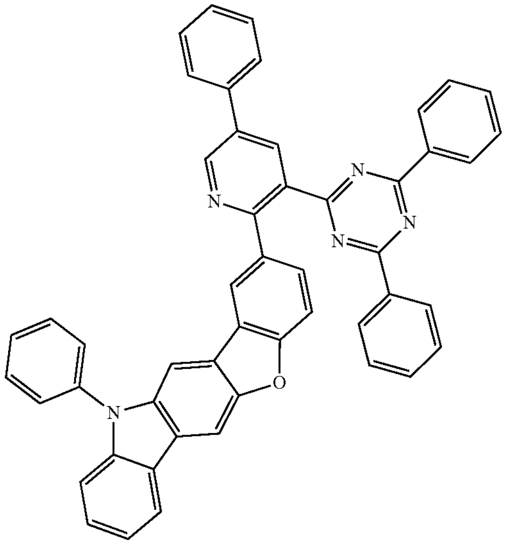
909
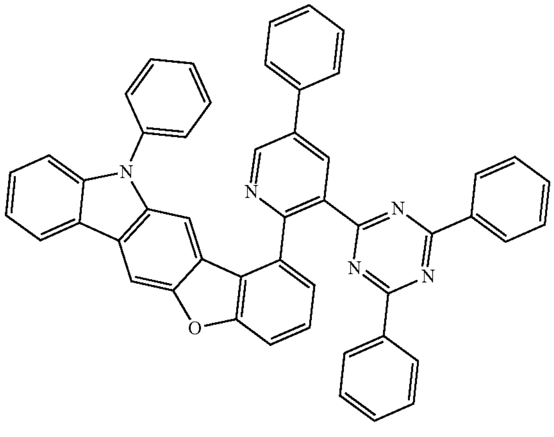

-continued
910
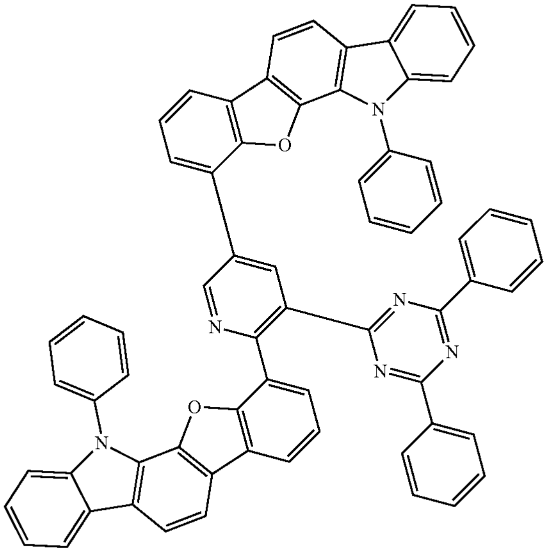
911
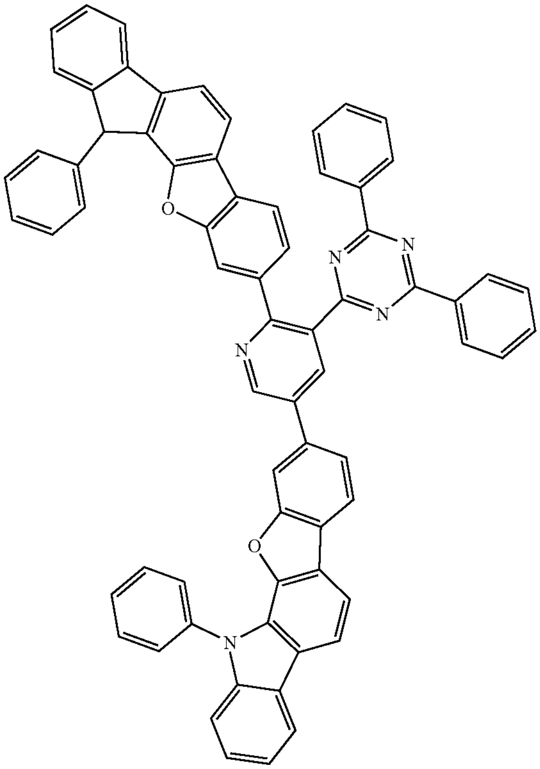

-continued
912
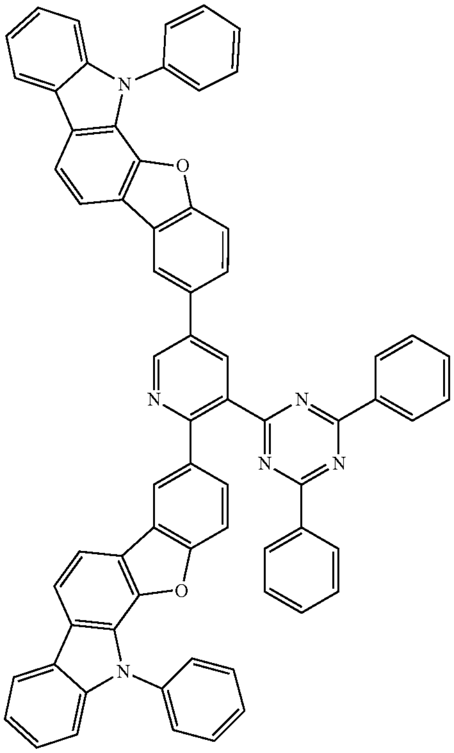
913
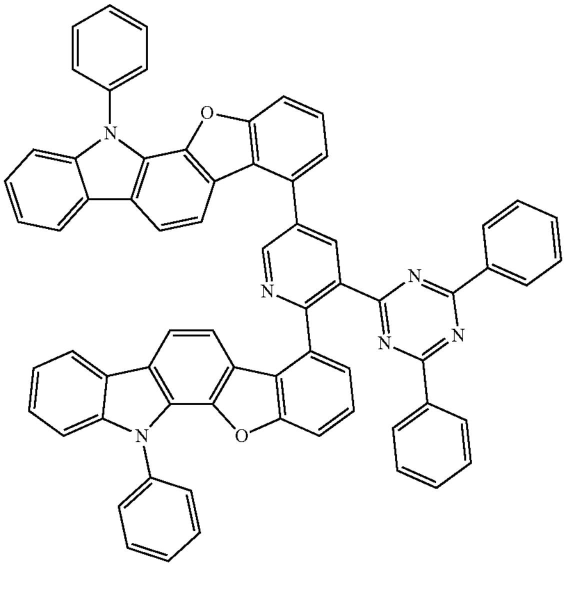

-continued
914
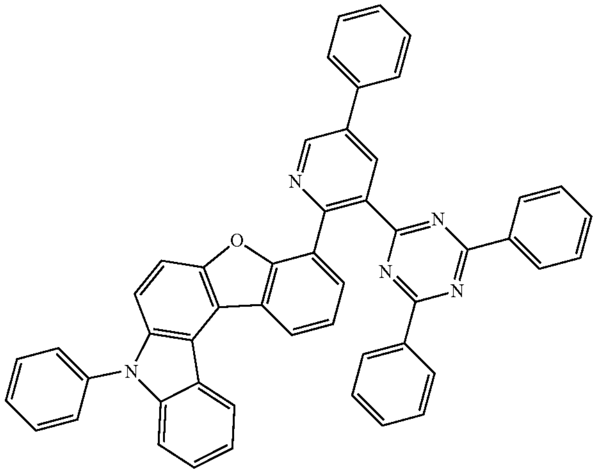
915
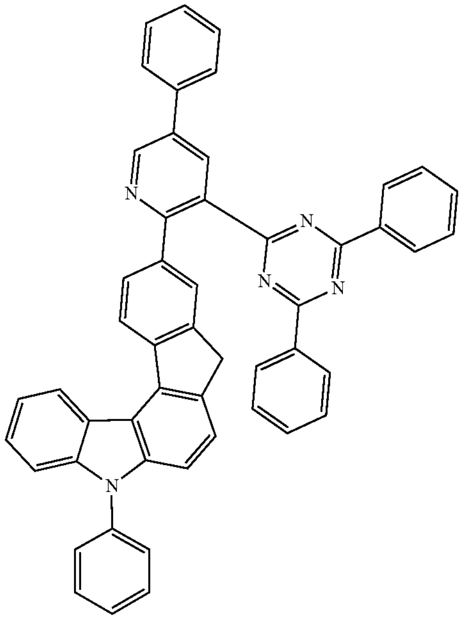
916
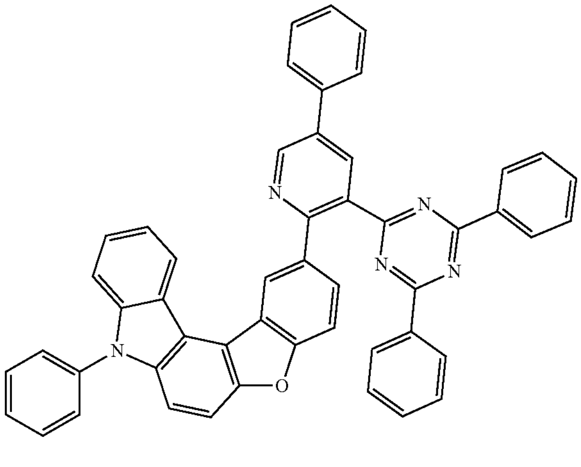

-continued
917
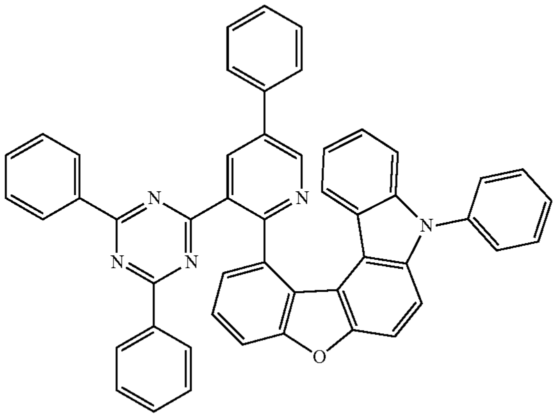
918
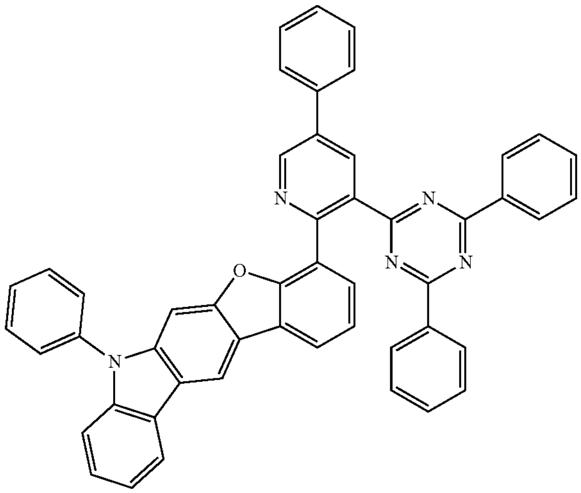
919
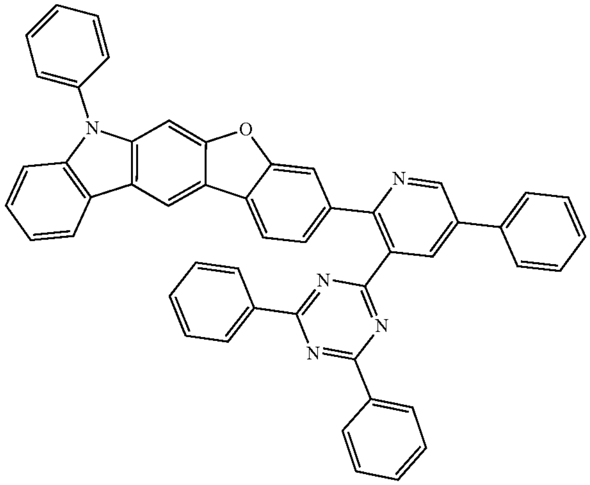

-continued
920
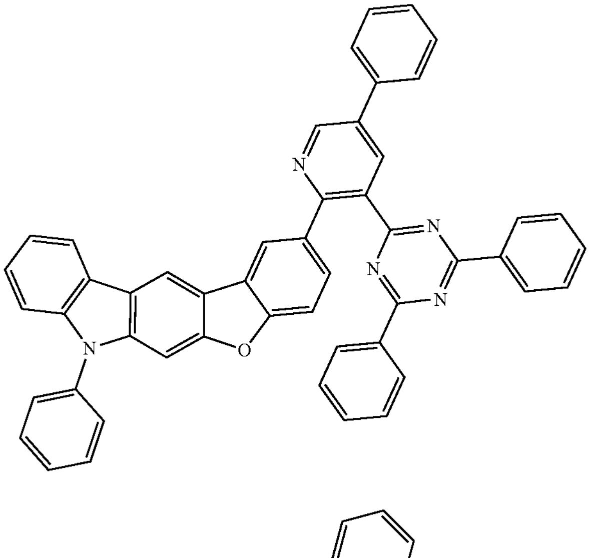
921
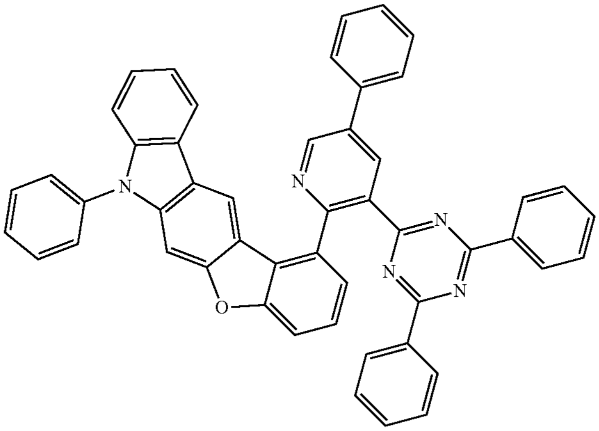
922
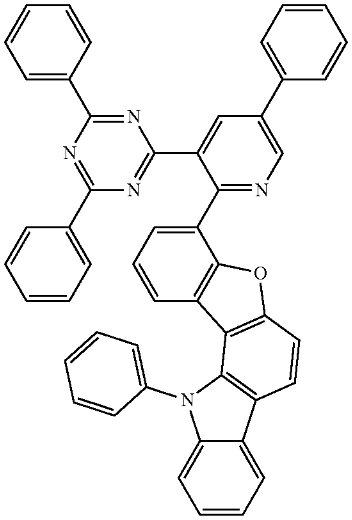

-continued
923
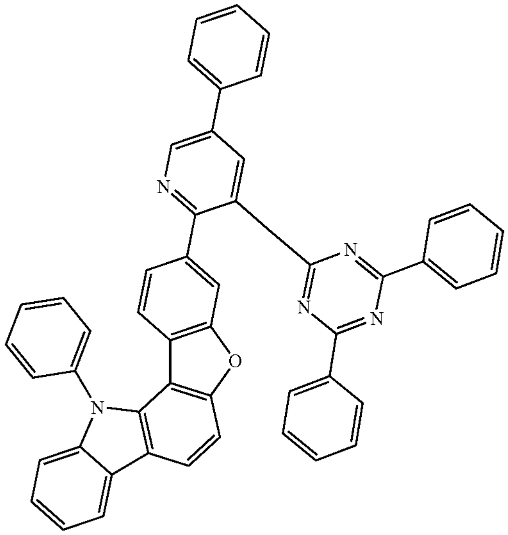
924
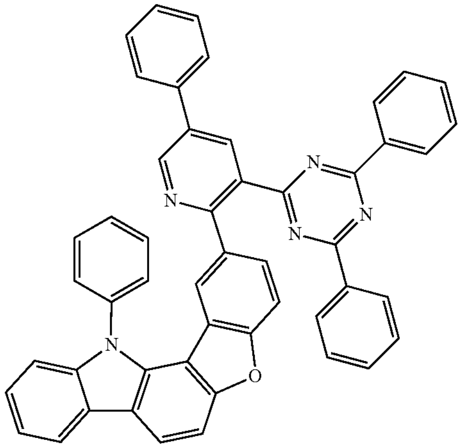
925
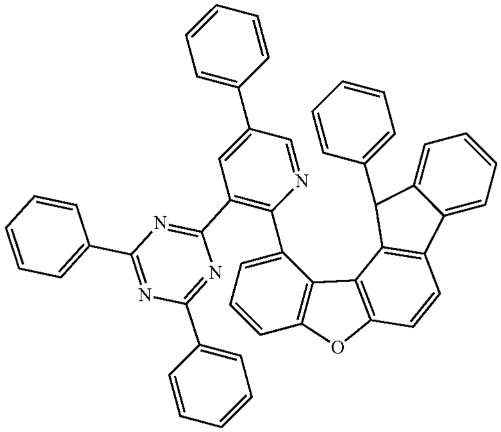

-continued
926
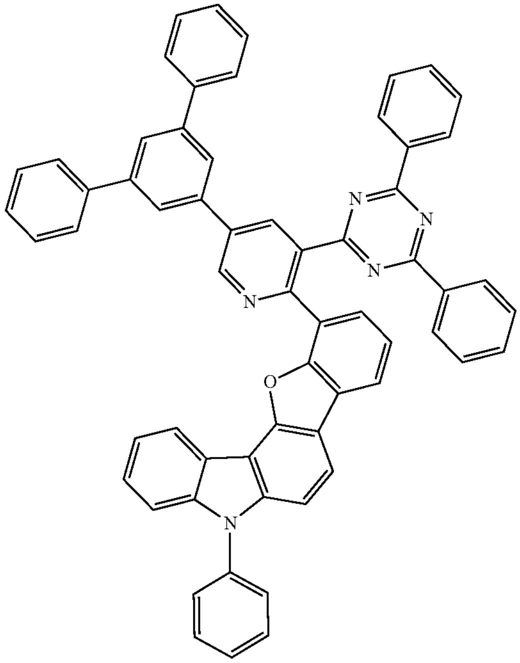
927
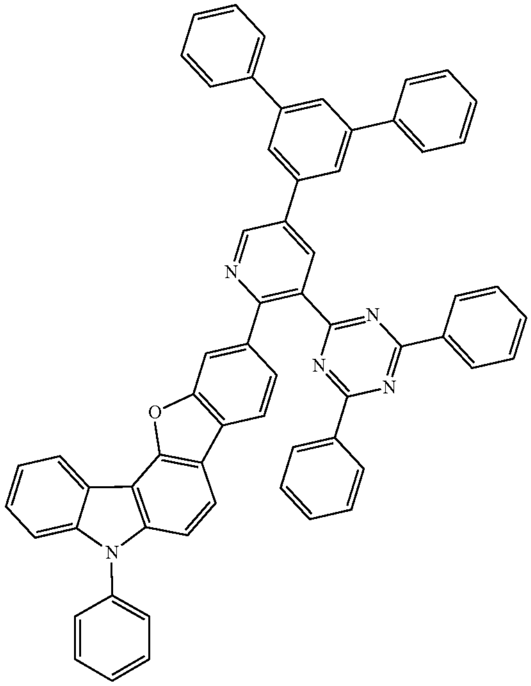

-continued
928
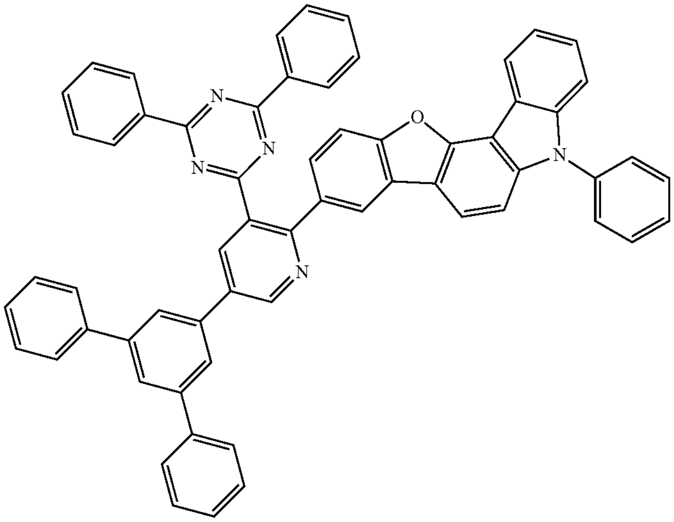
929
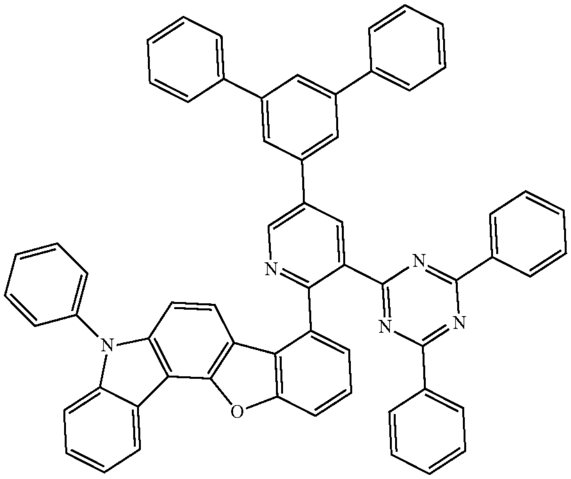
930
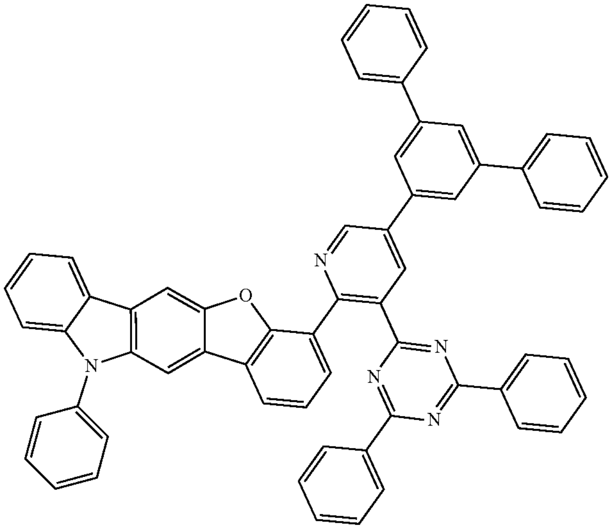

-continued
931
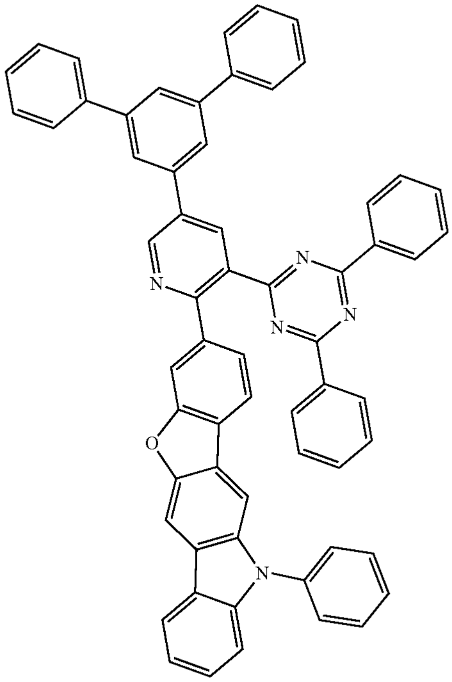
932
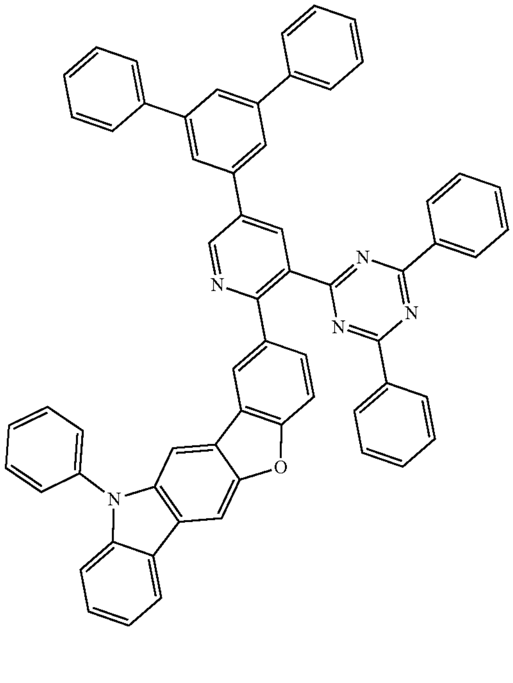

-continued
933
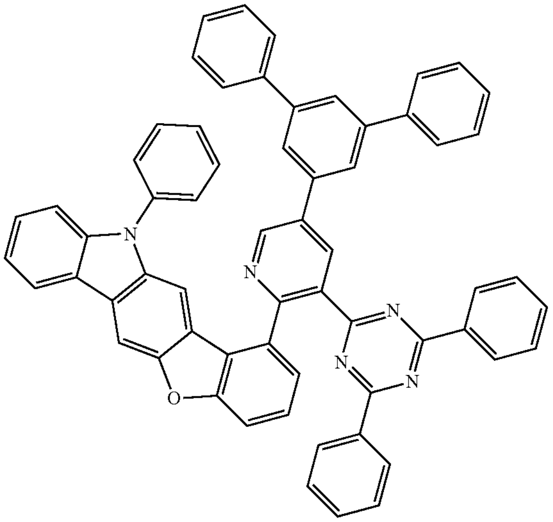
934
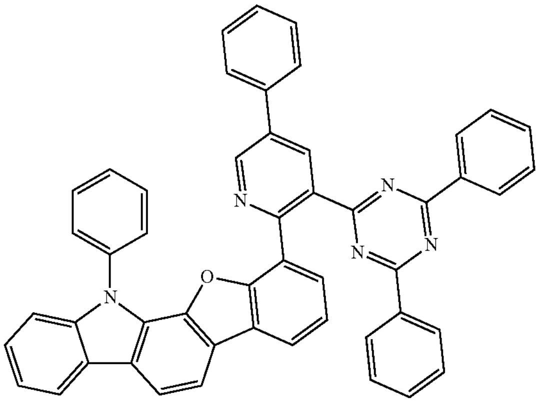
935
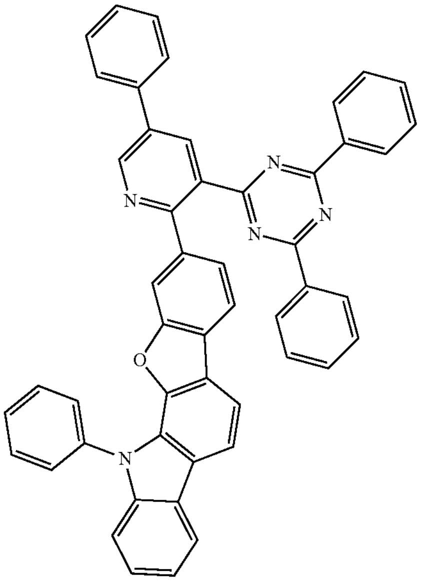

-continued
936
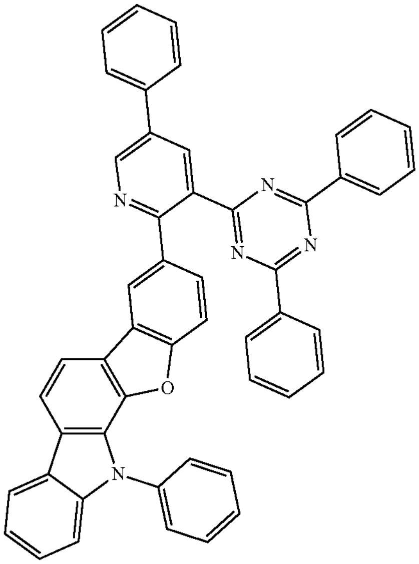
937
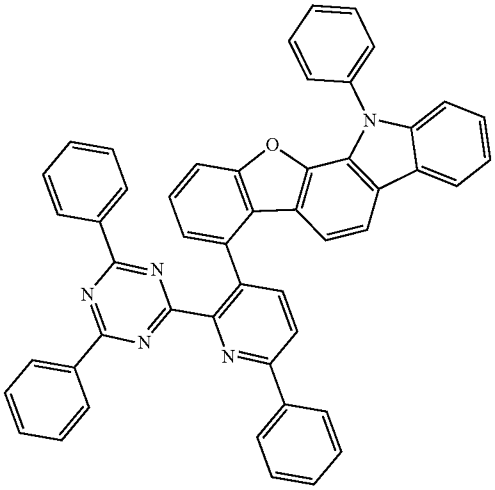
938
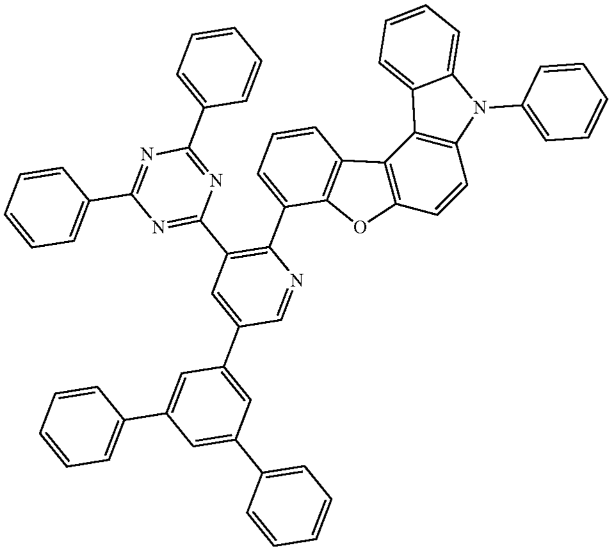

-continued
939
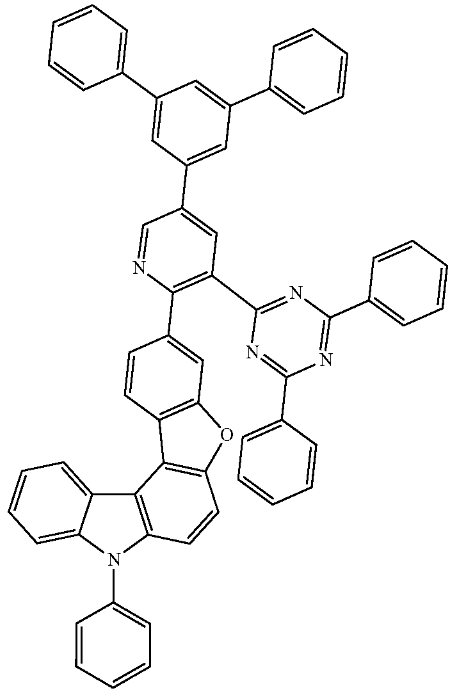
940
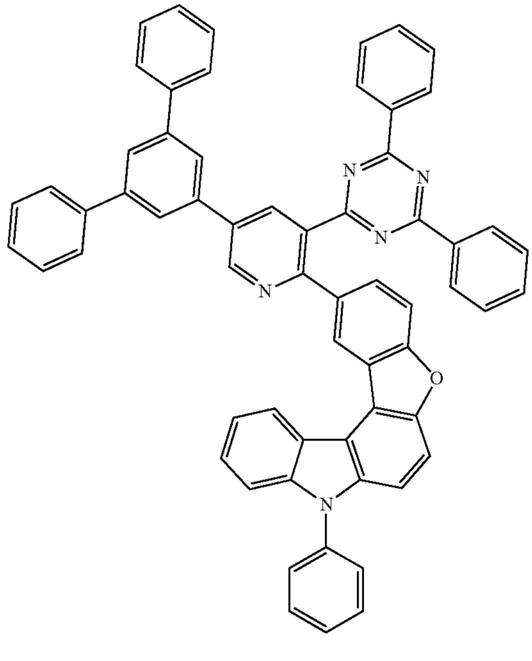

-continued
941
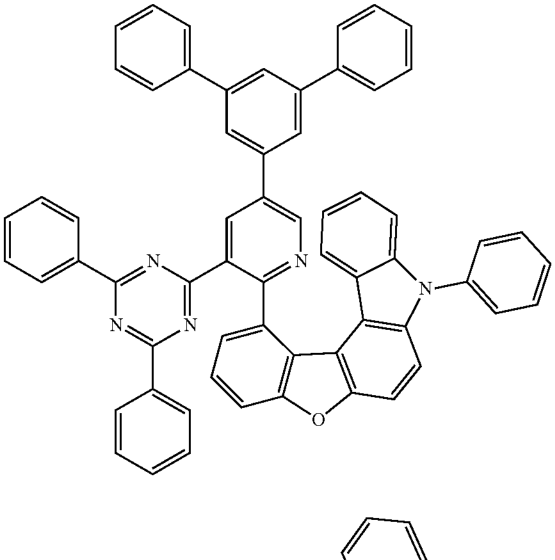
942
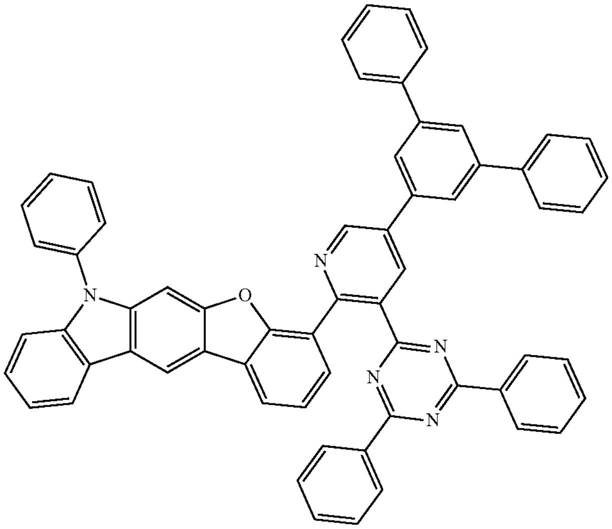
943
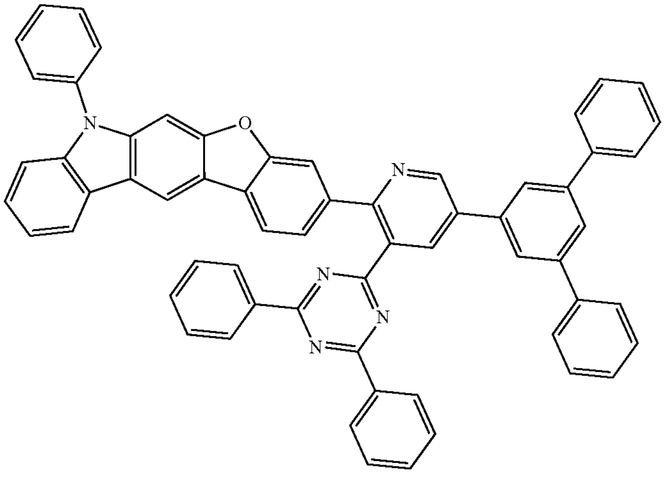

-continued
944
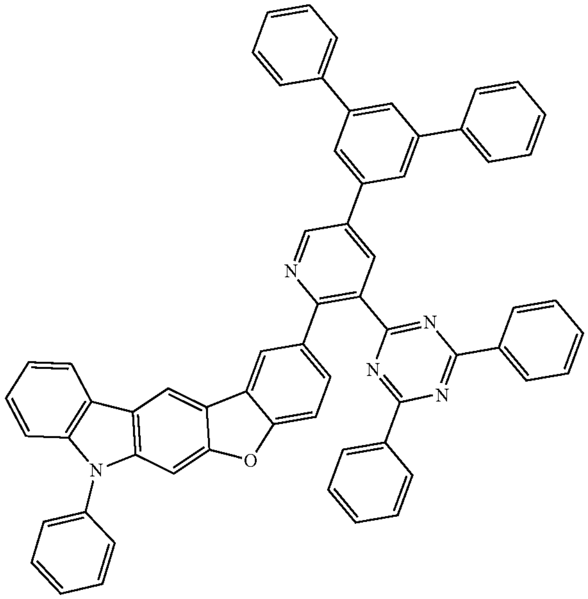
945
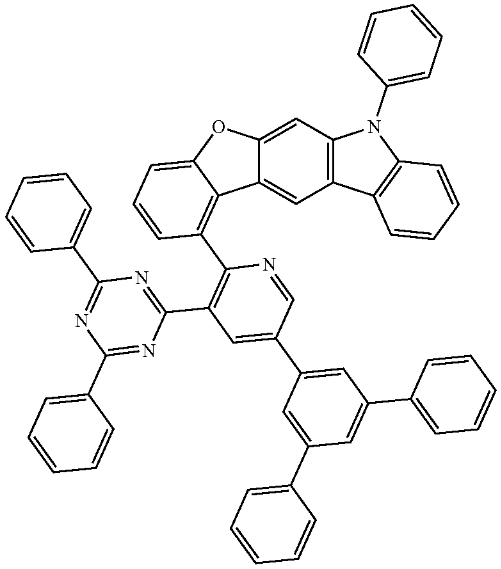

-continued
946
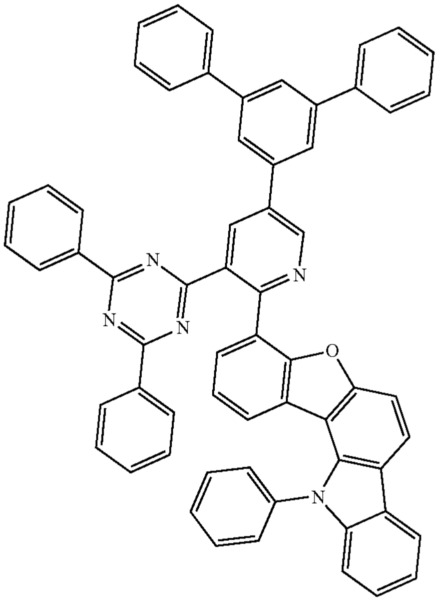
947
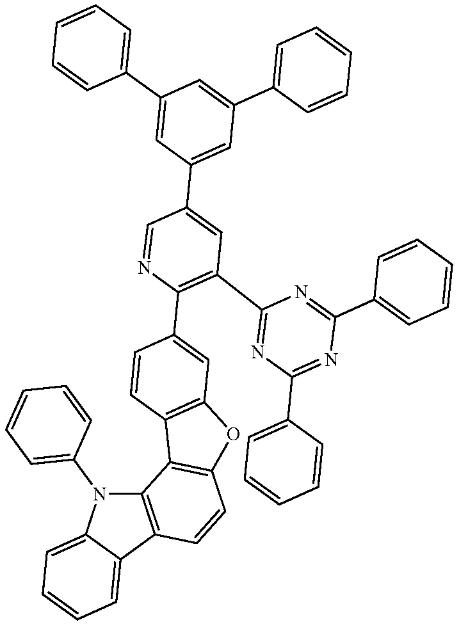

-continued
948
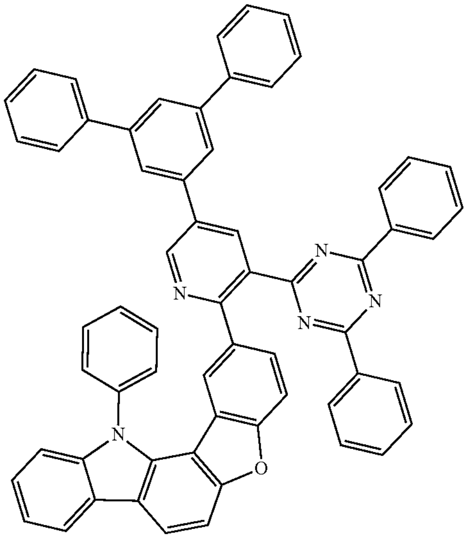
949
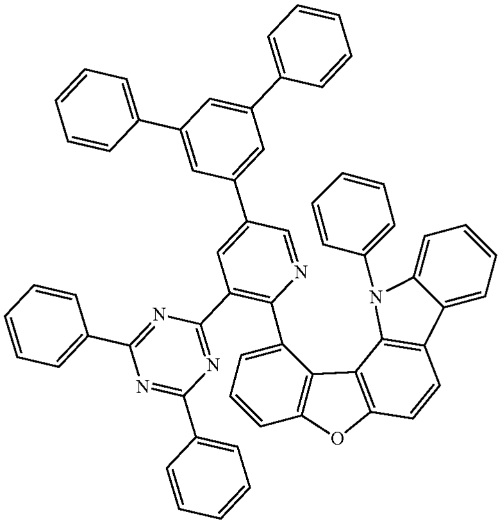
950
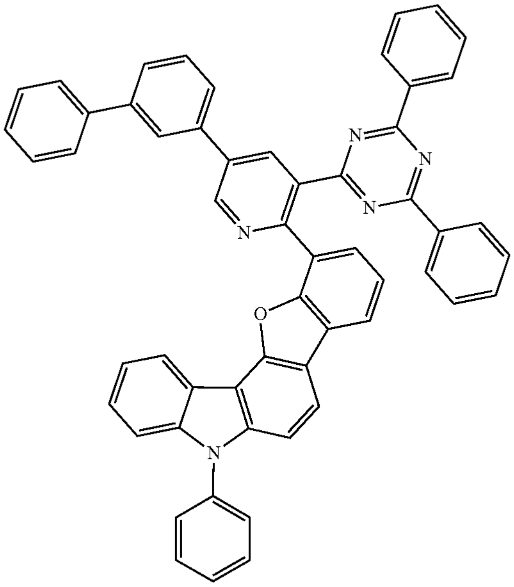

-continued
951
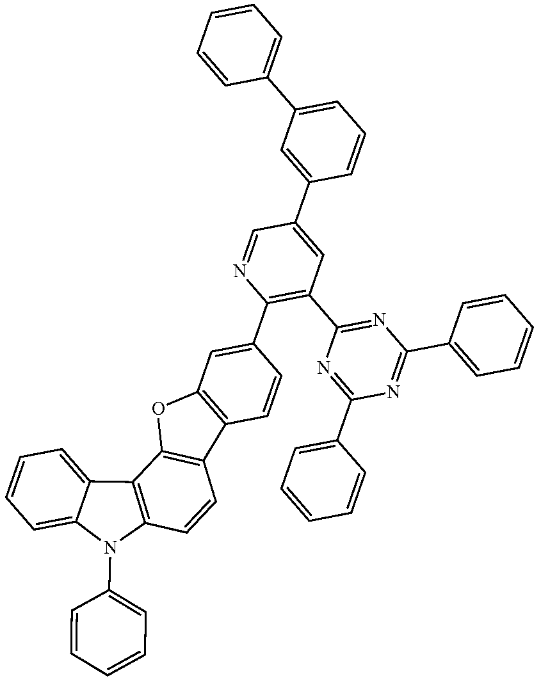
952
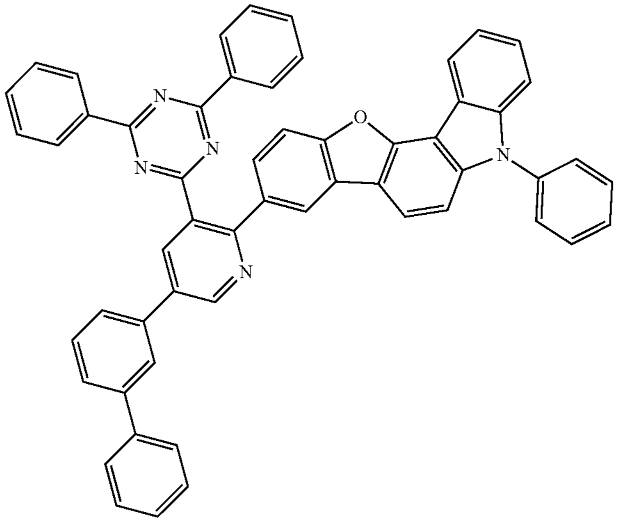
953
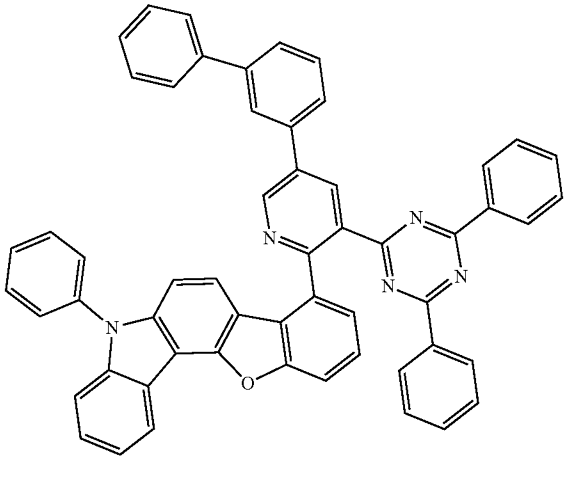

-continued
954
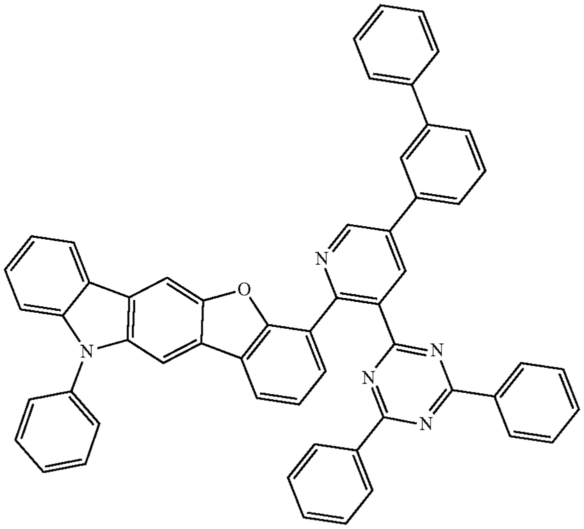
955
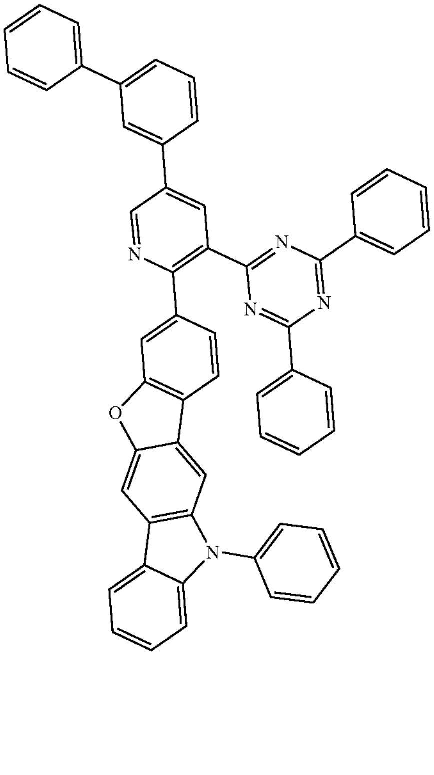

-continued
956
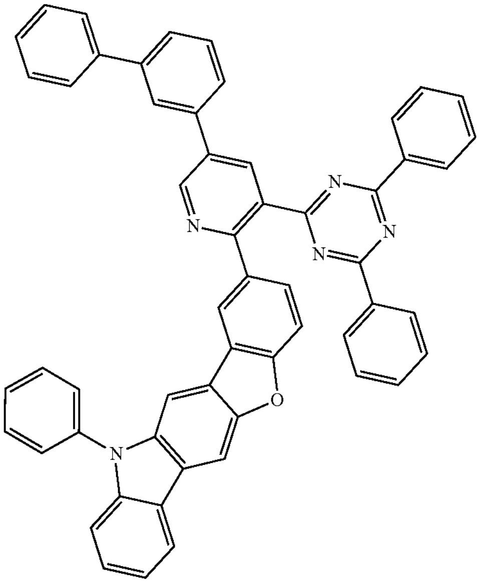
957
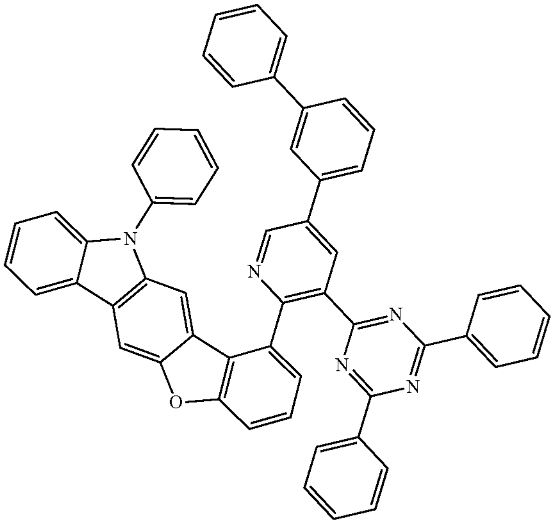
958
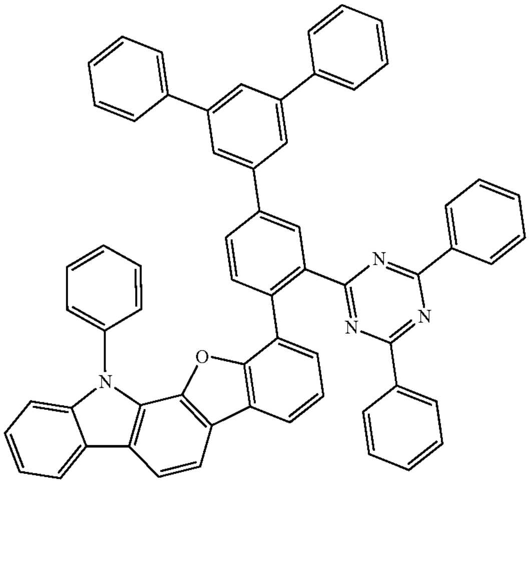

-continued
959
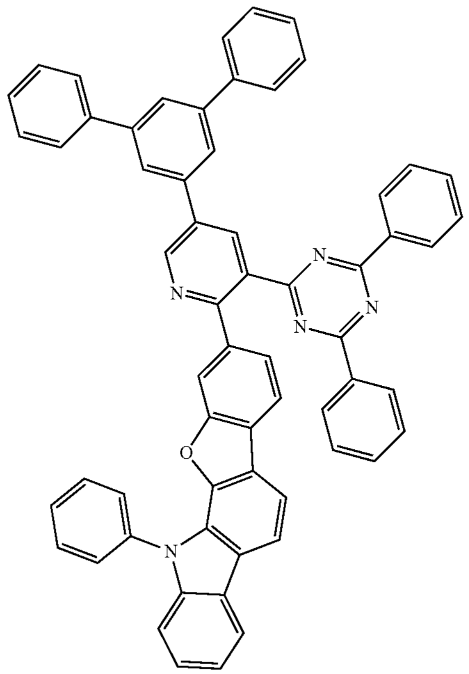
960
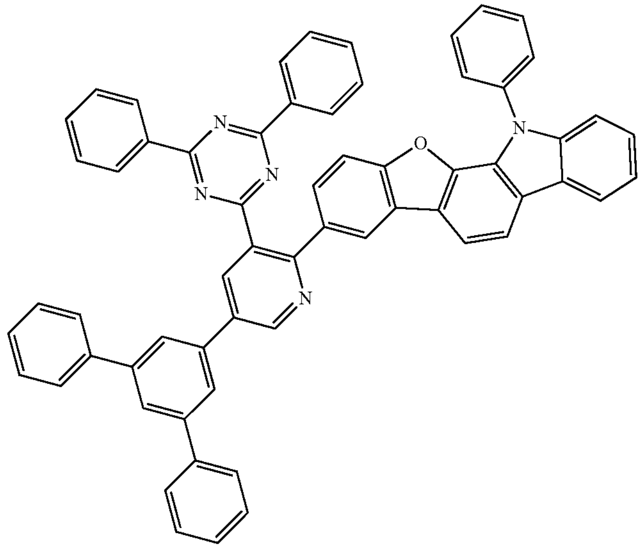

-continued
961
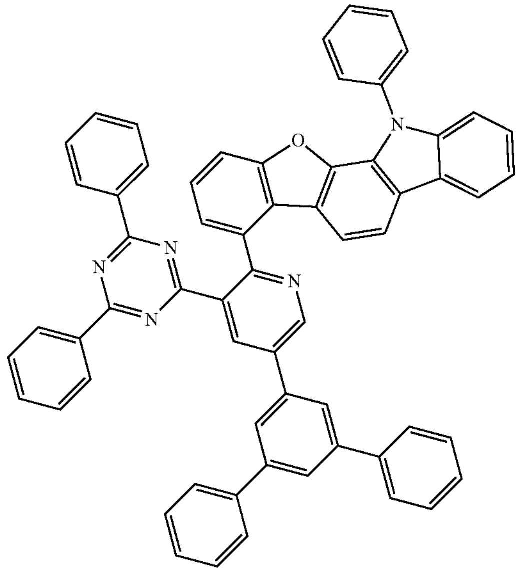
962
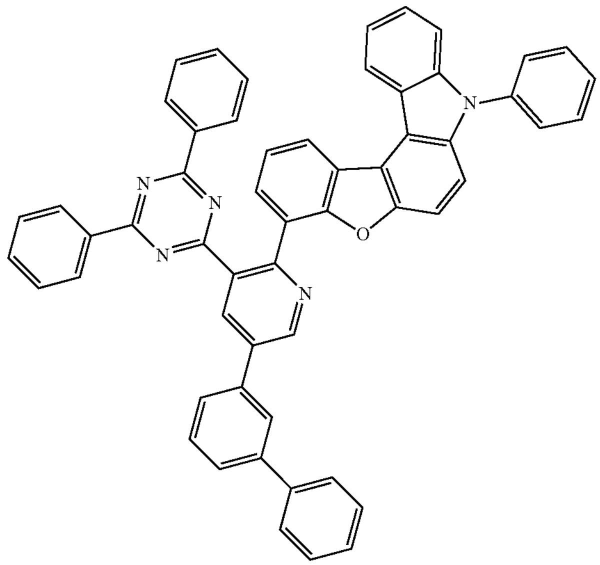

-continued
963
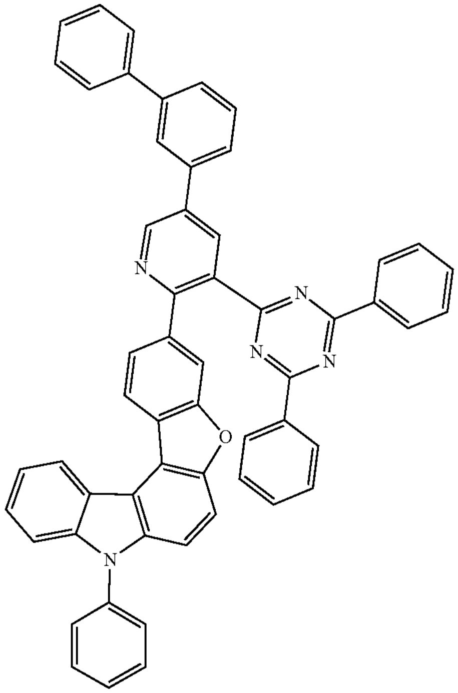
964
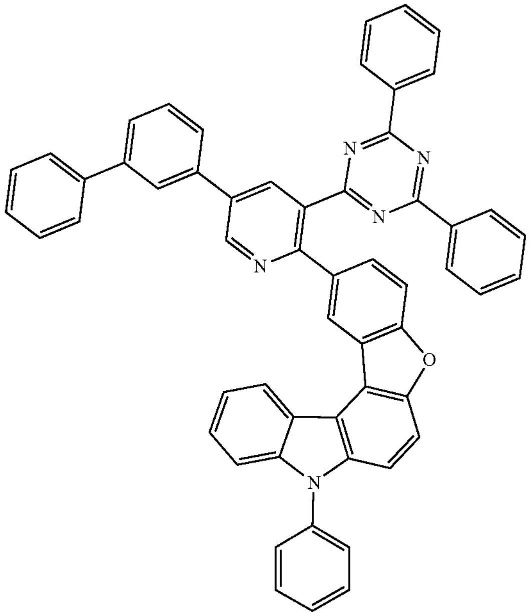

-continued
965
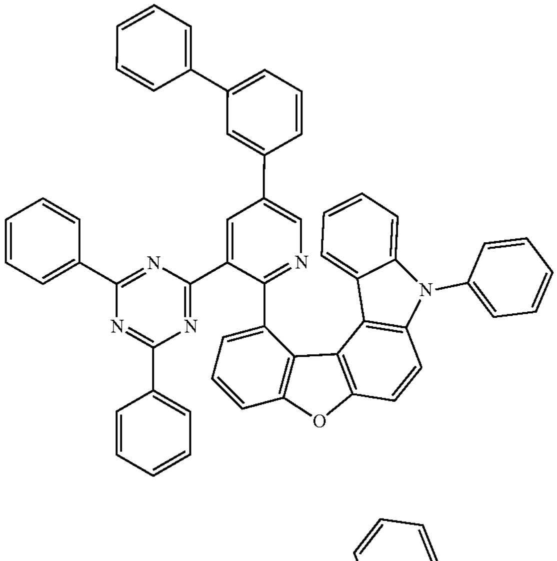
966
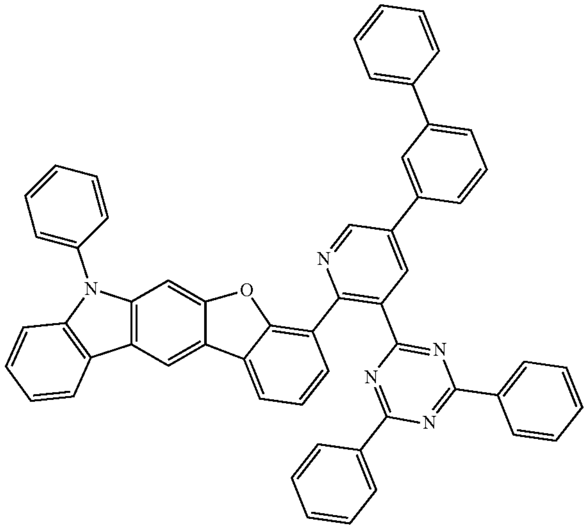
967
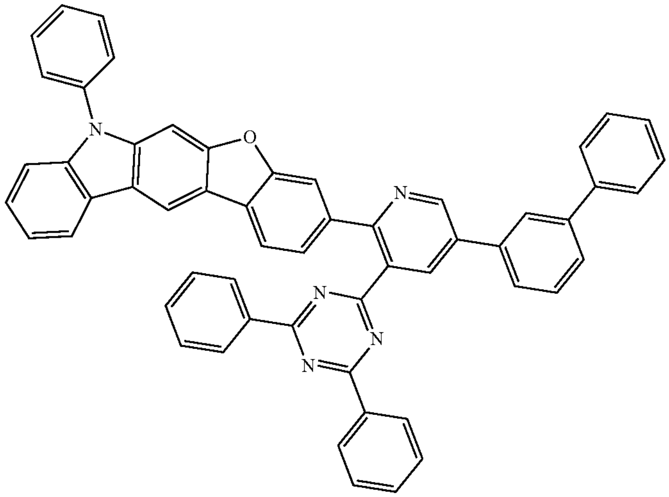

-continued
968
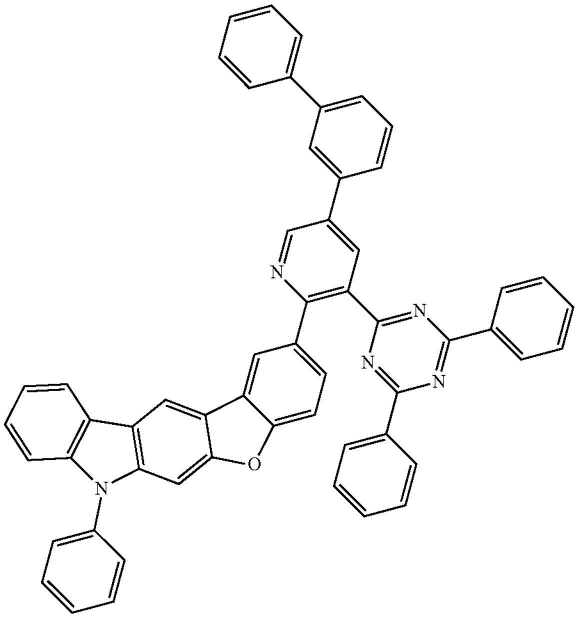
969
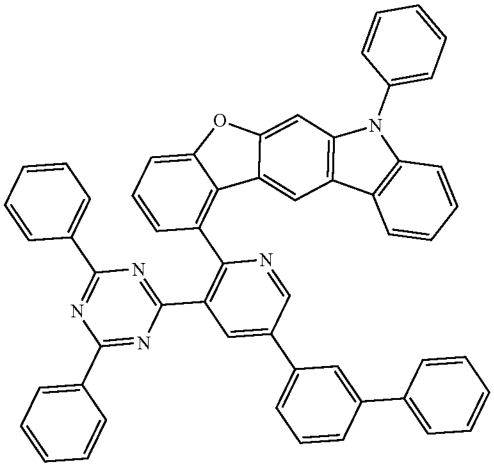
970
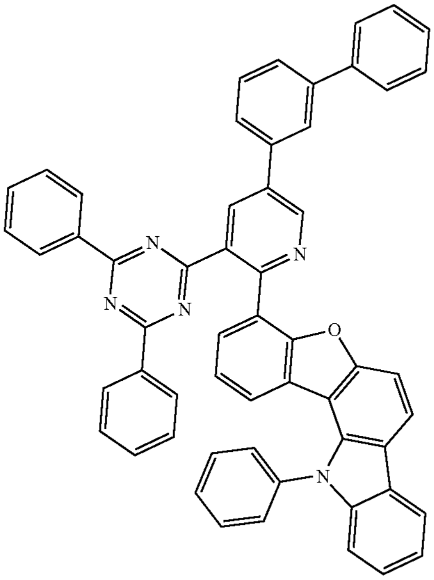

-continued
971
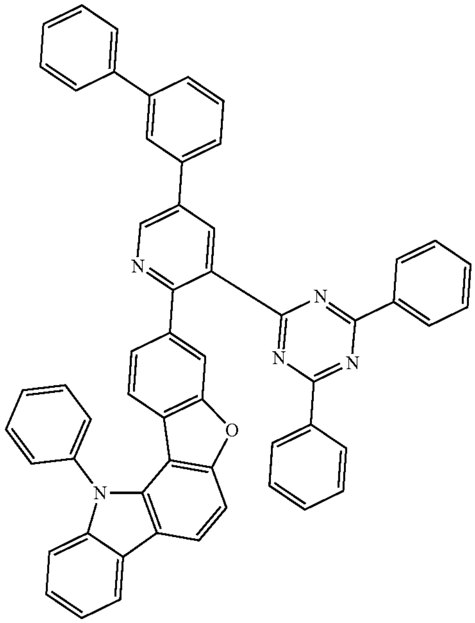
972
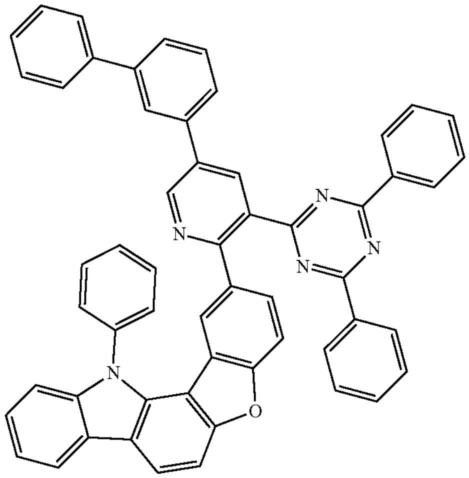
973
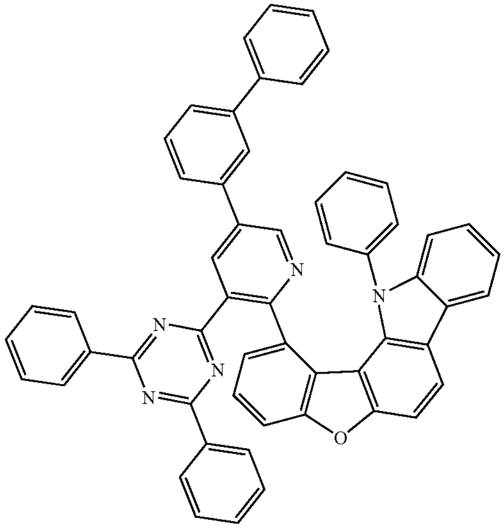

-continued
974
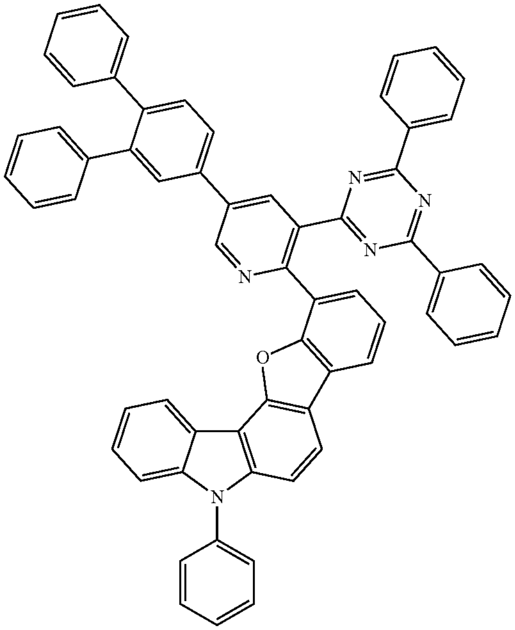
975
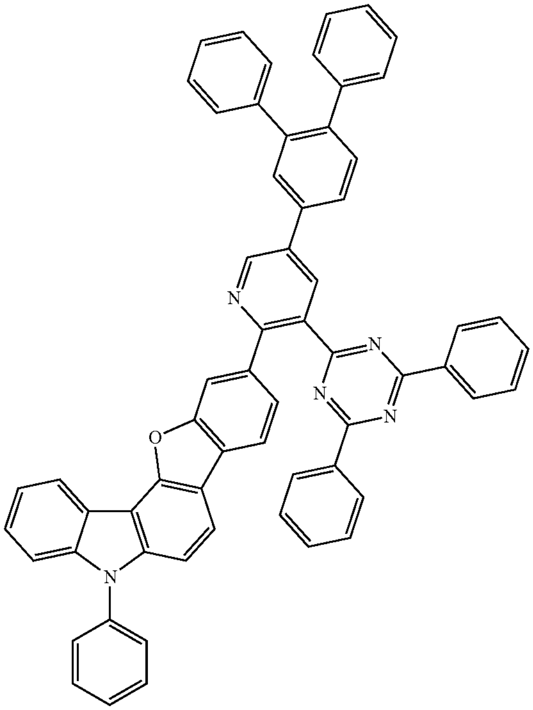

-continued
976
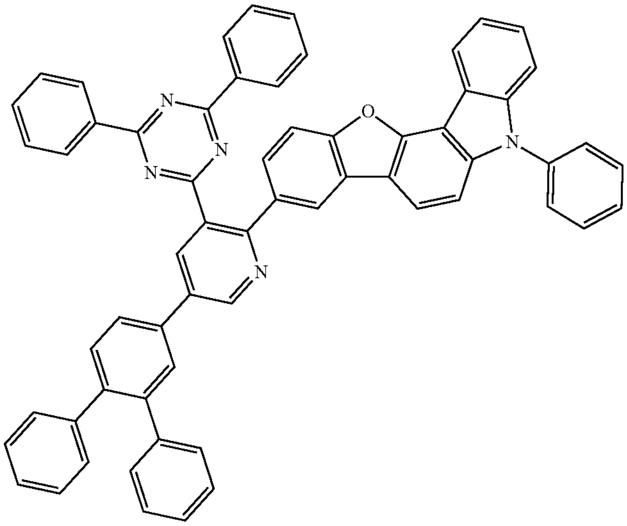
977
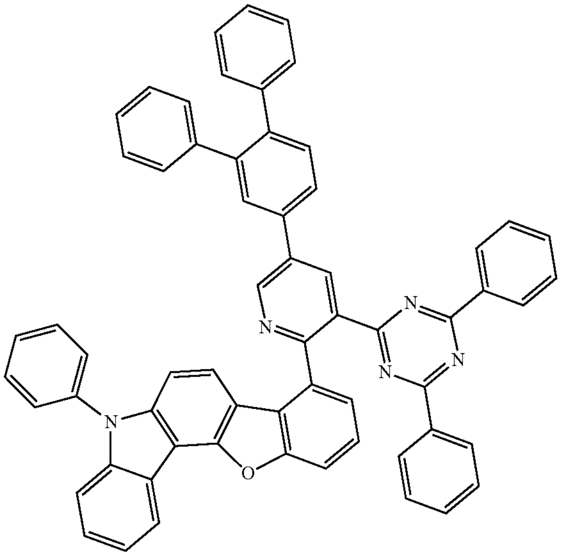
978
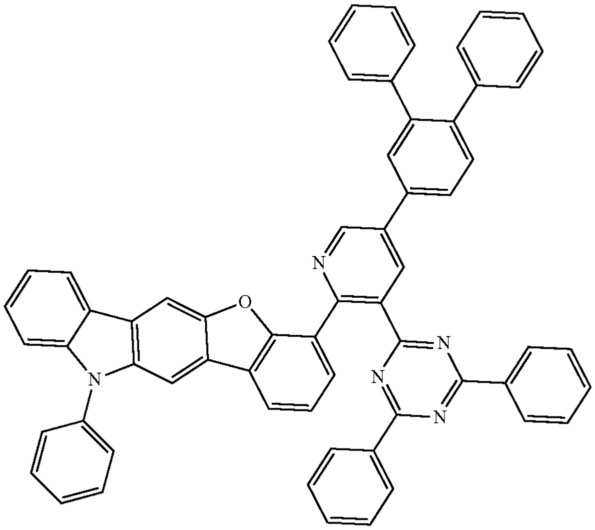

-continued
979
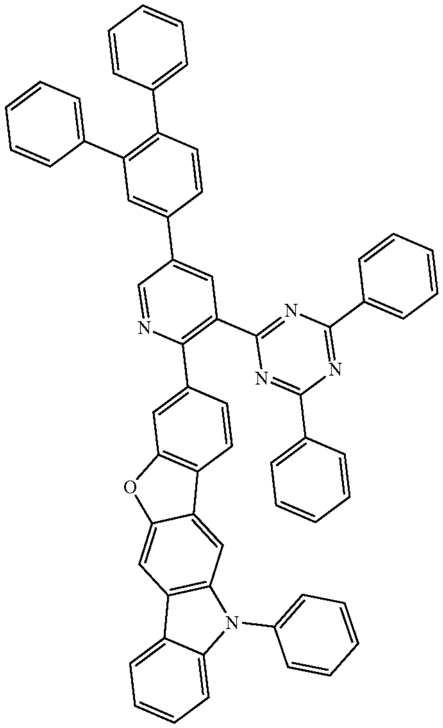
980
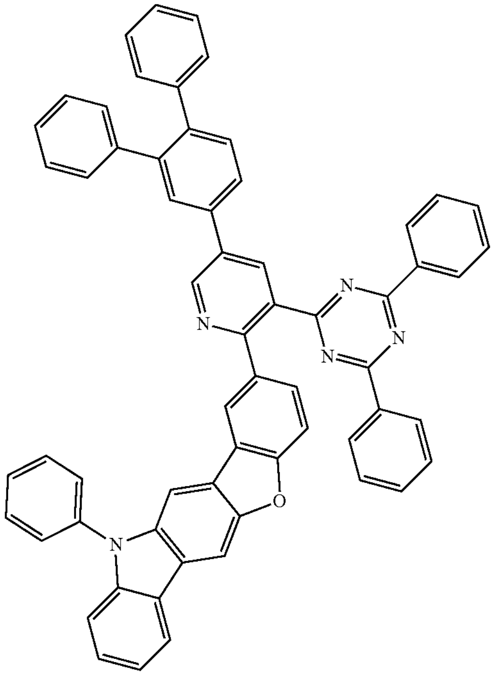

-continued
981
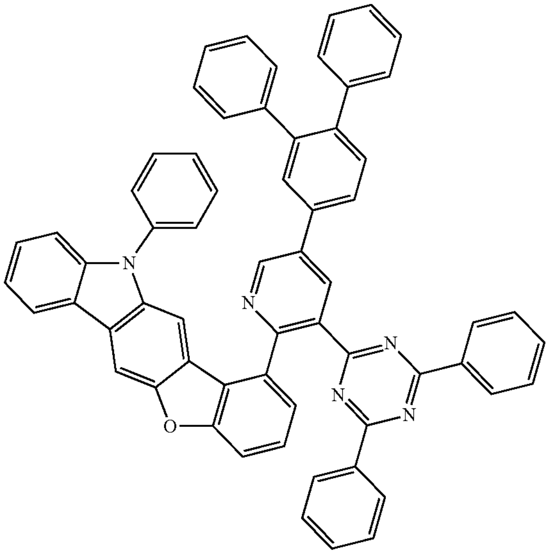
982
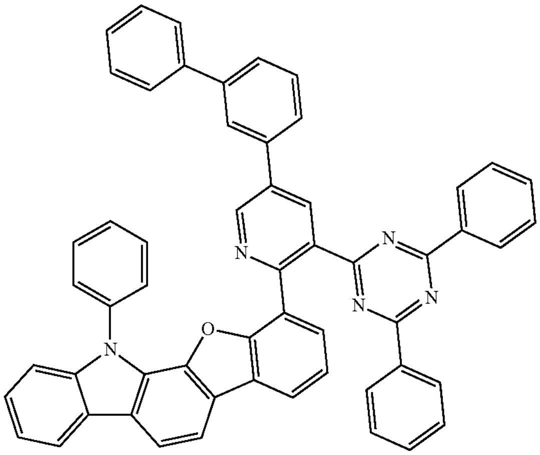
983
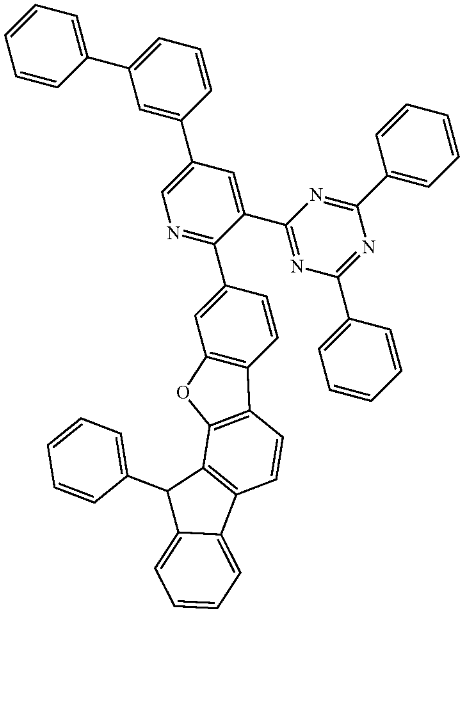

-continued
984
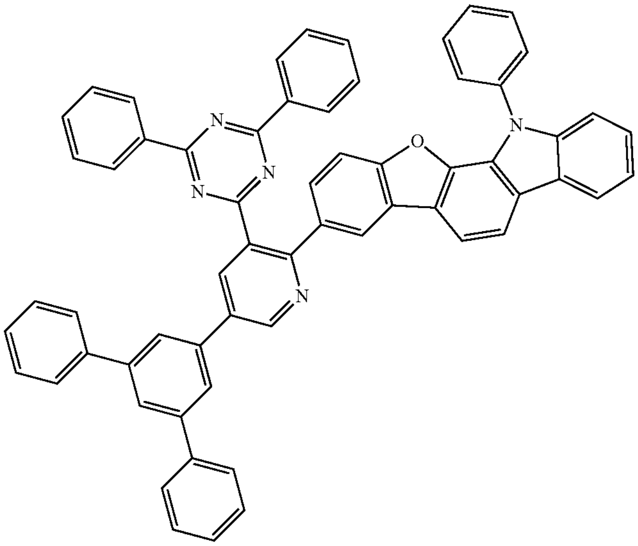
985
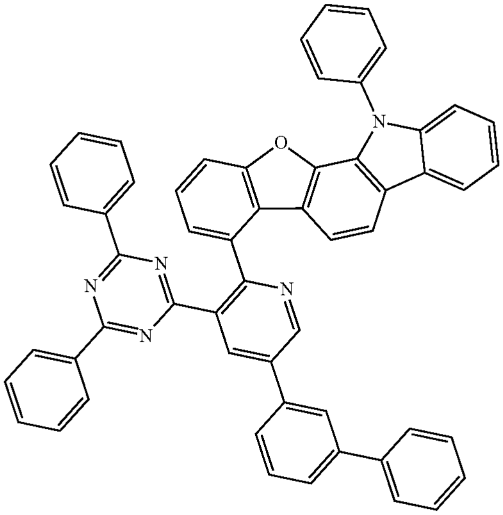
986
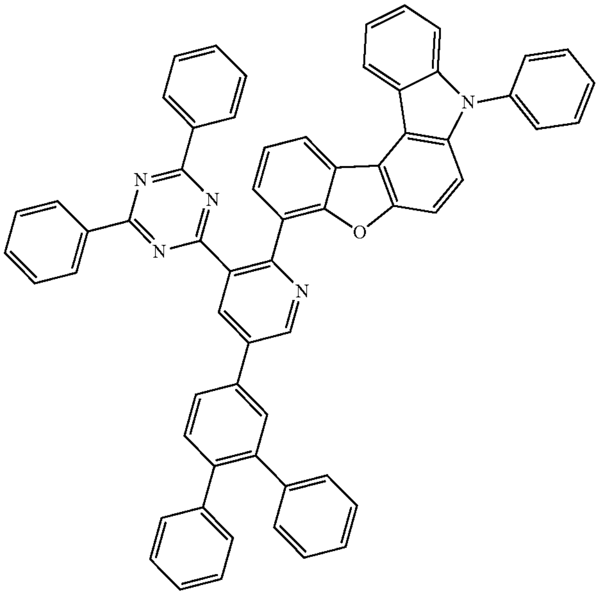

-continued
987
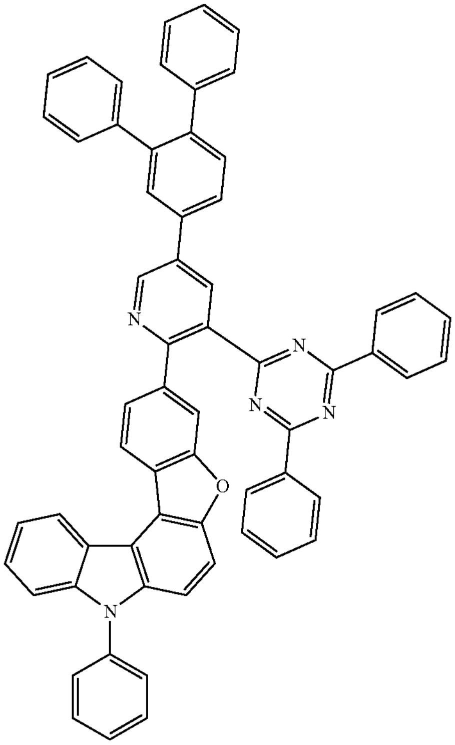
988
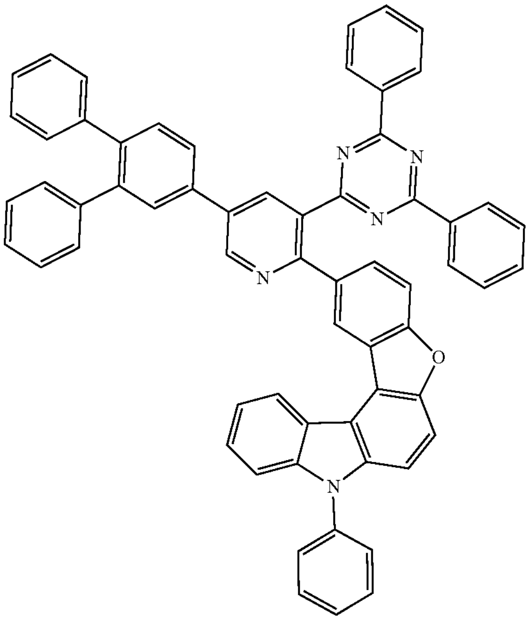

-continued
989
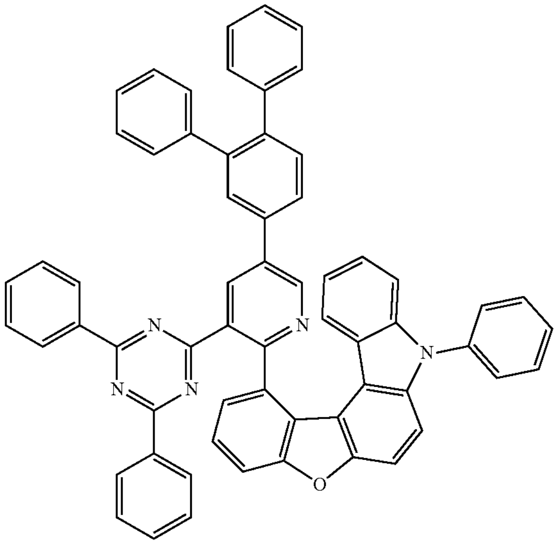
990
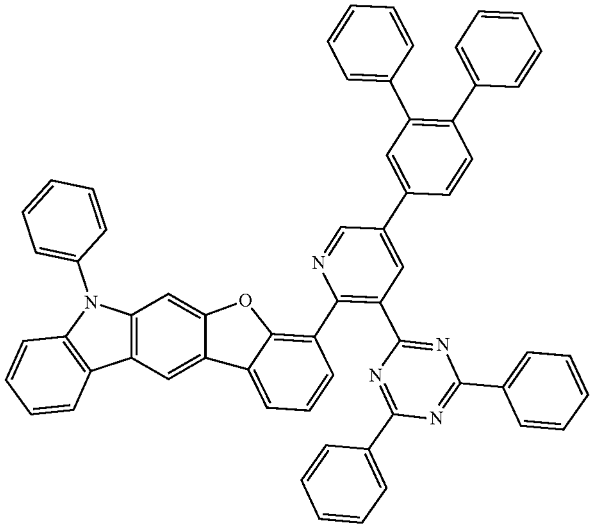
991
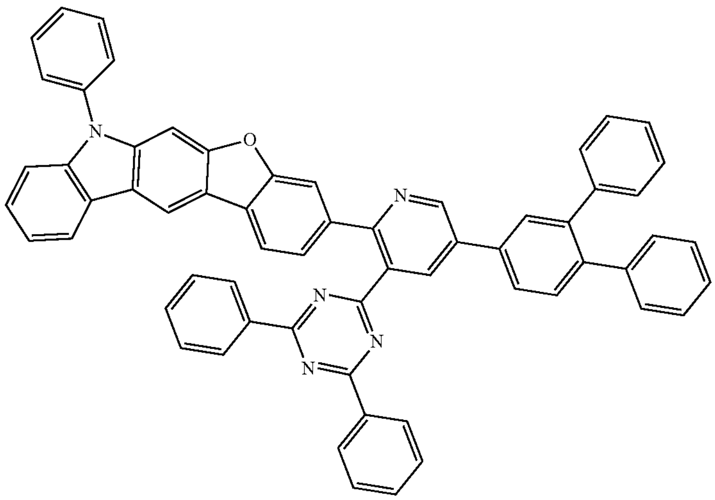

-continued
992
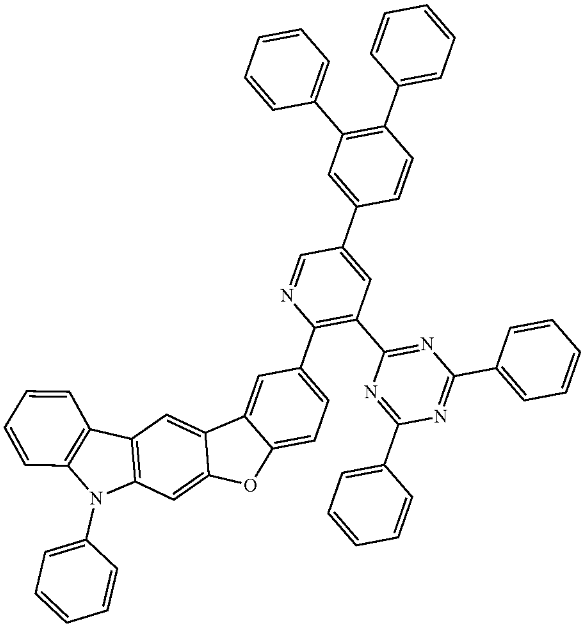
993
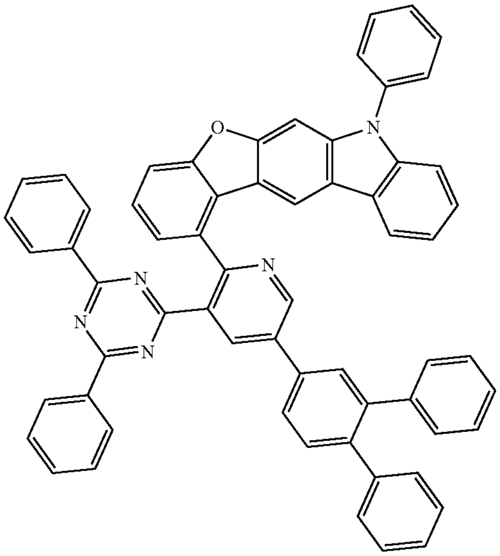

-continued
994
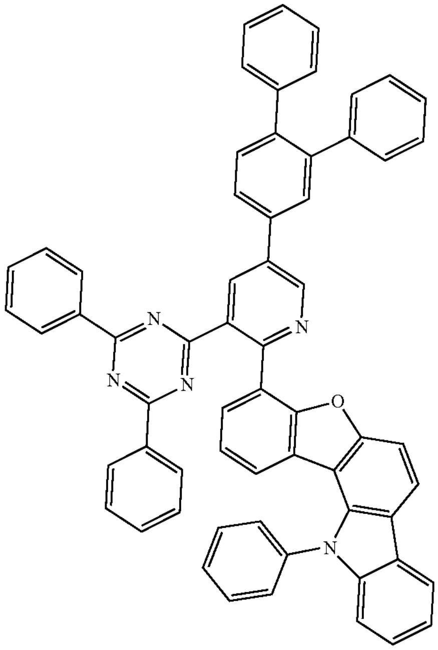
995
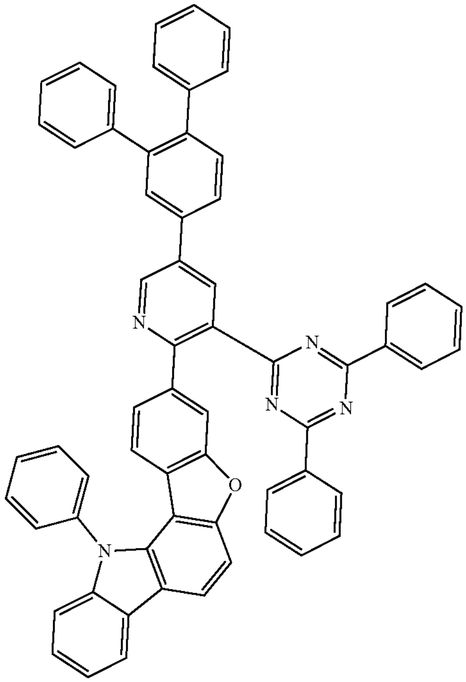

-continued
996
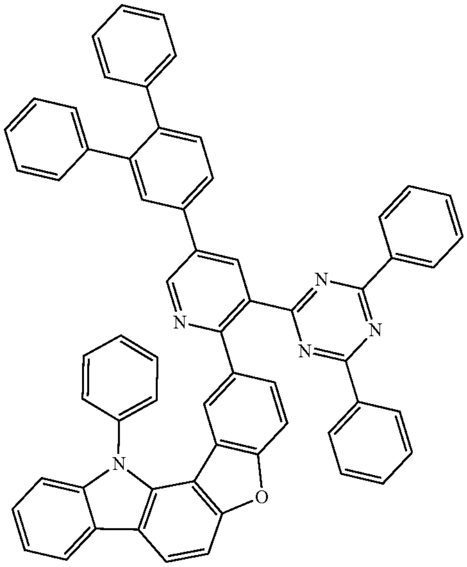
997
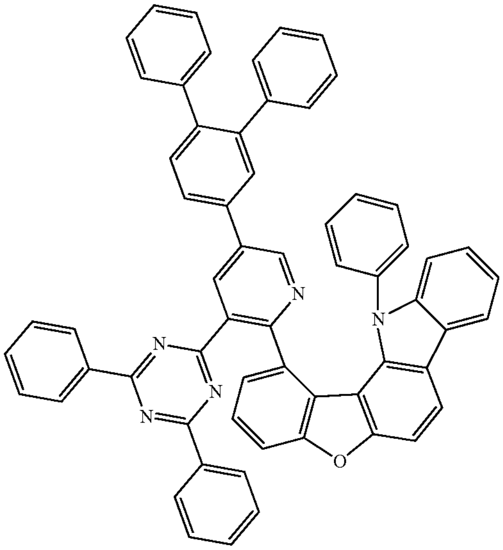

-continued
998
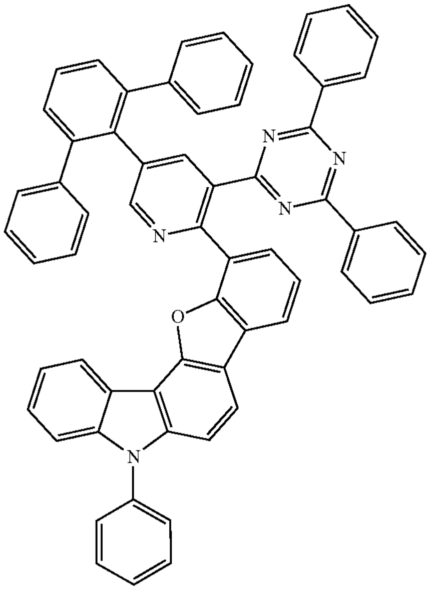
999
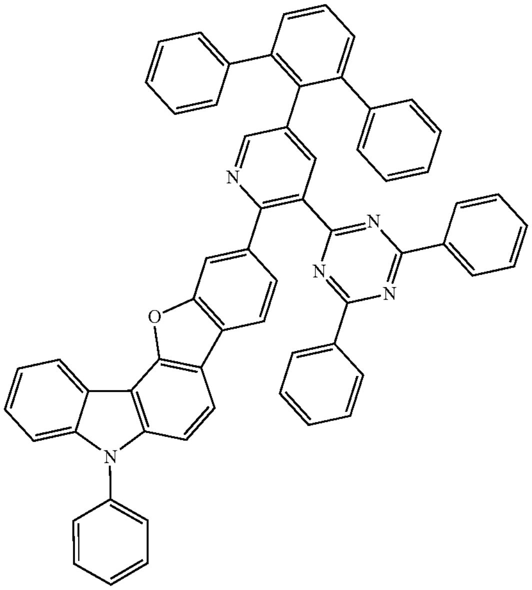
1000
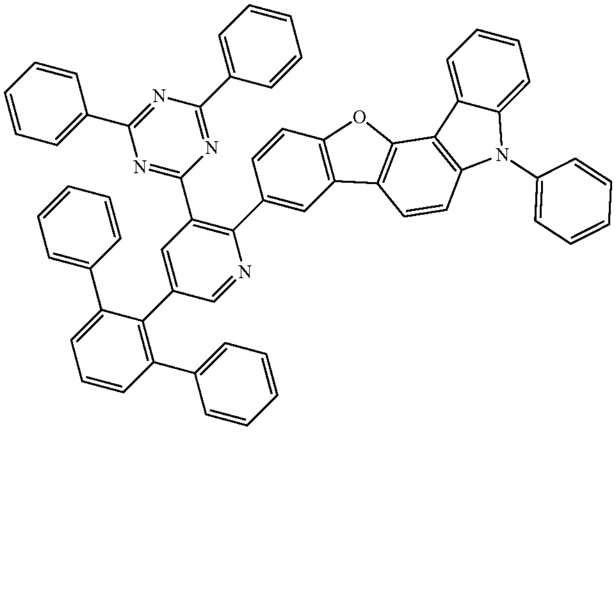

-continued
1001
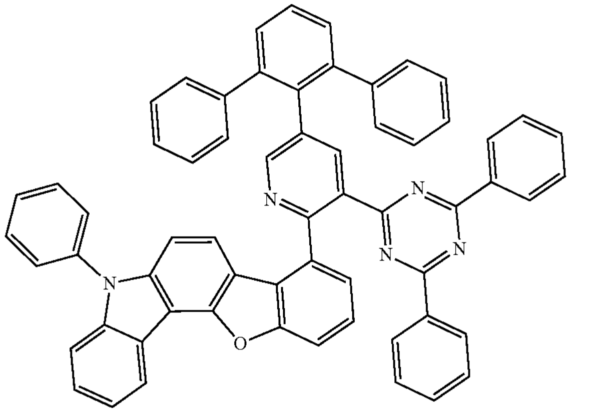
1002
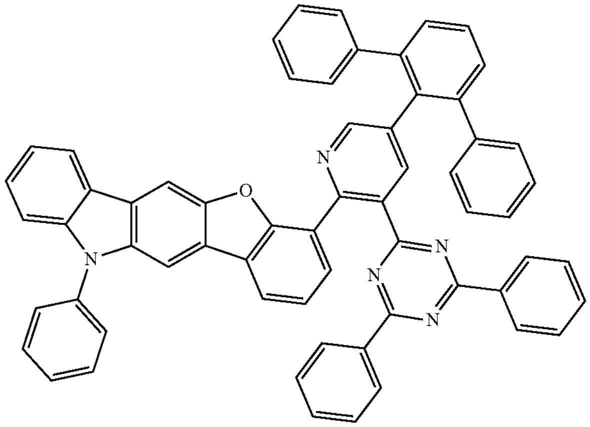
1003
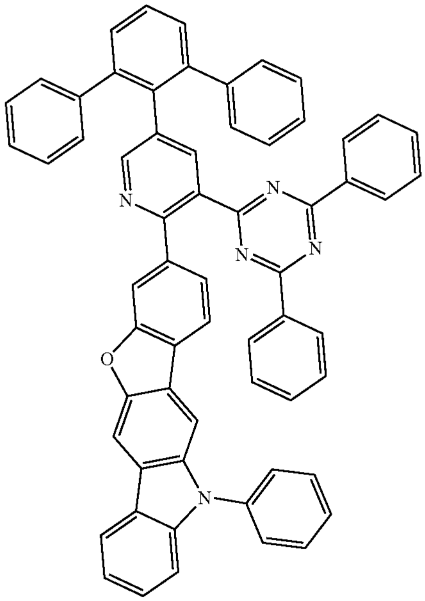

-continued
1004
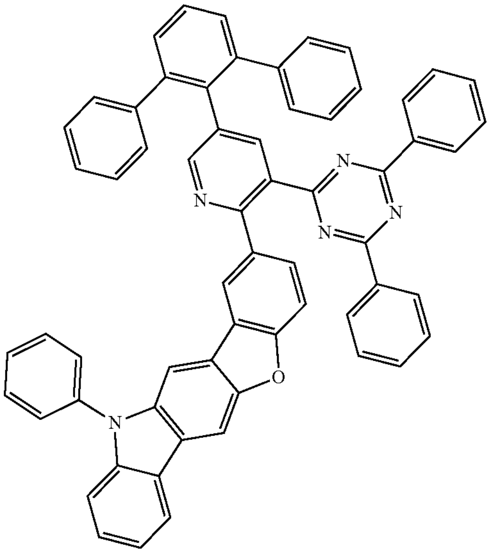
1005
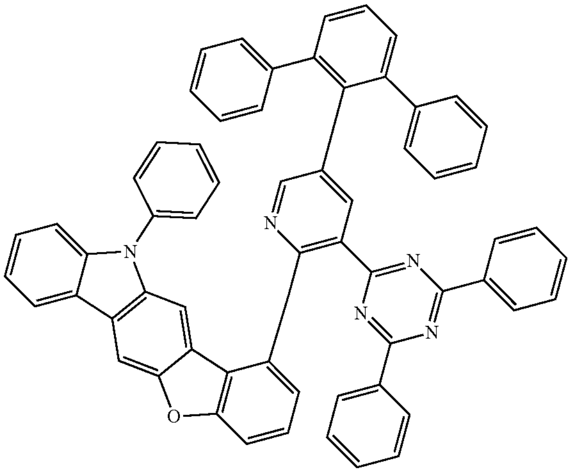
1006
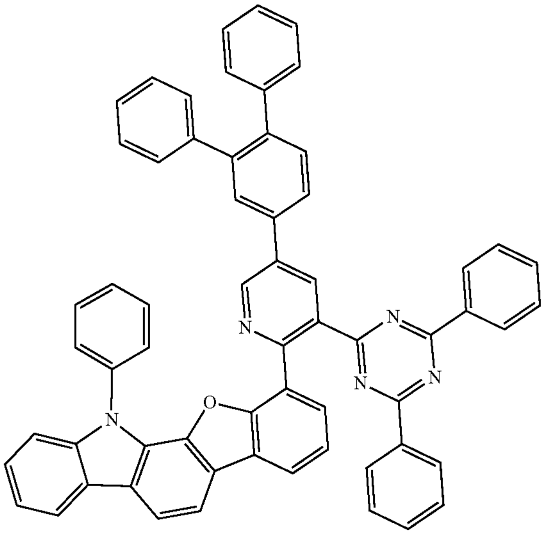

-continued
1007
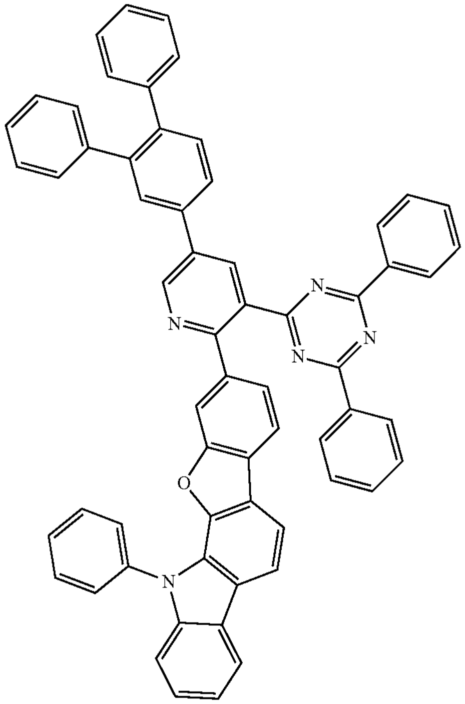
1008
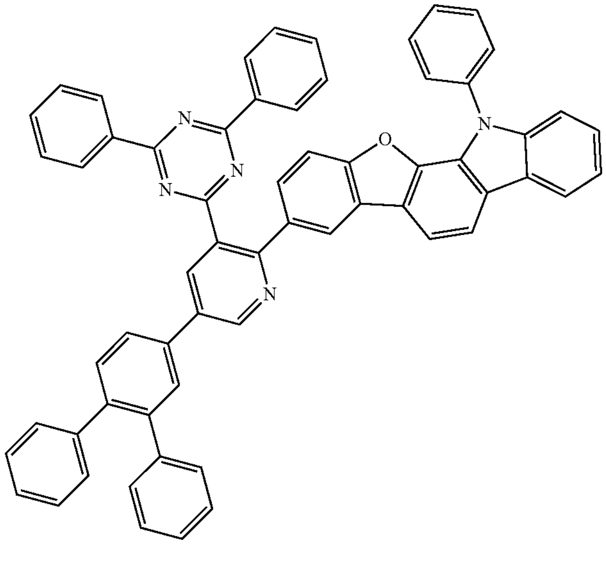

-continued
1009
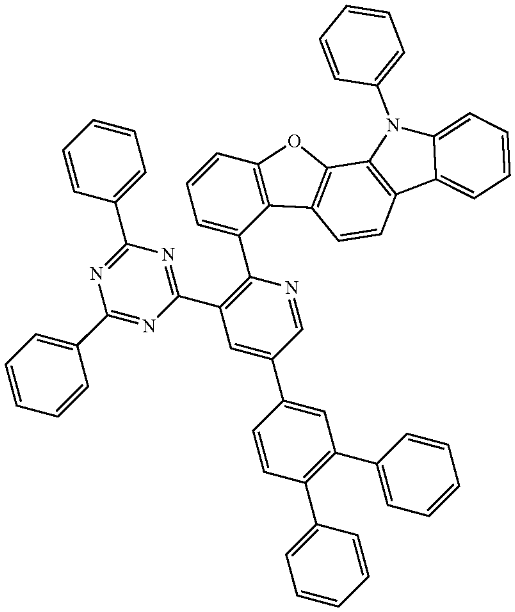
1010
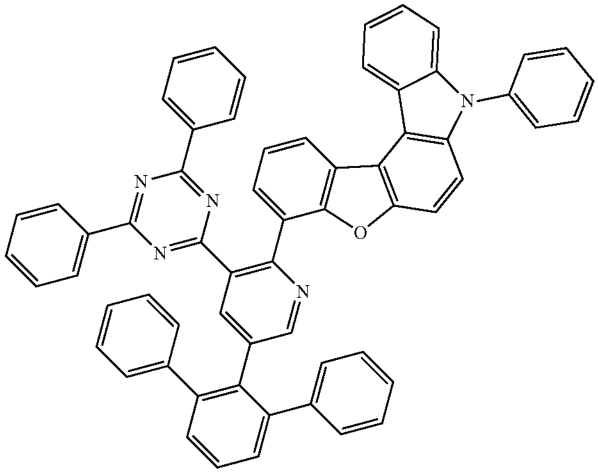

-continued
1011
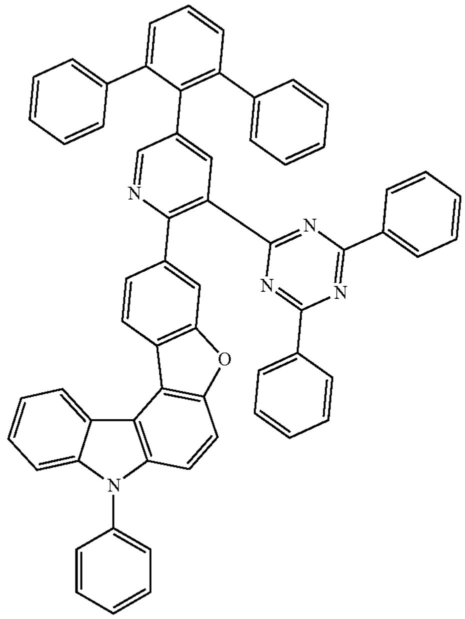
1012
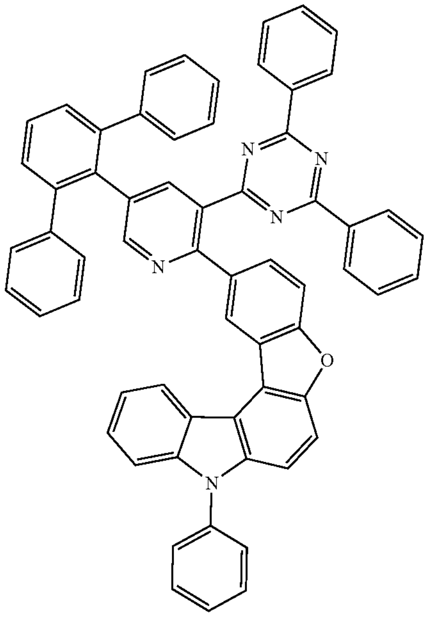

-continued
1013
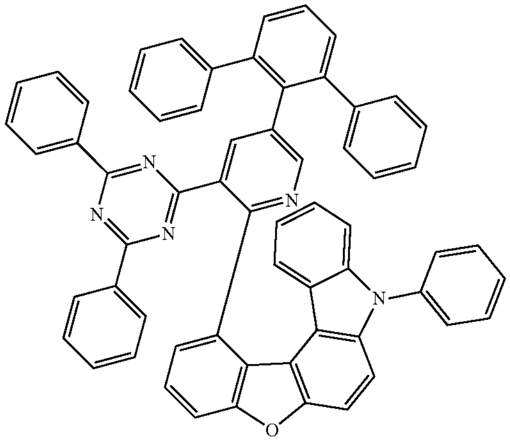
1014
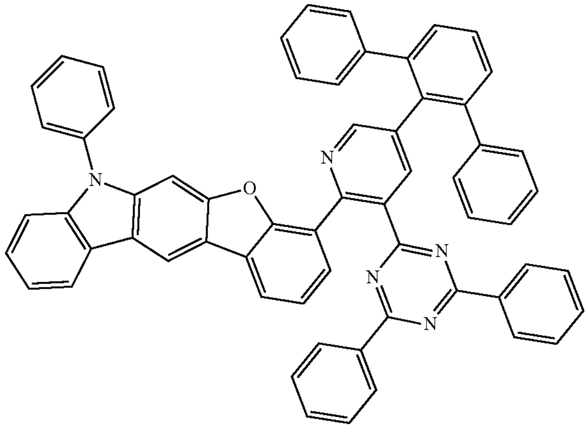
1015
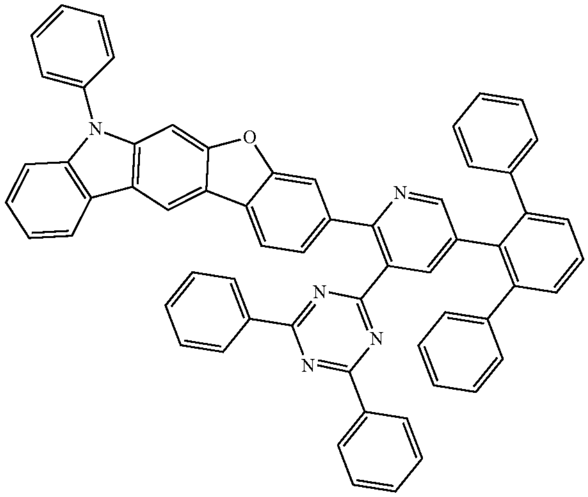

-continued
1016
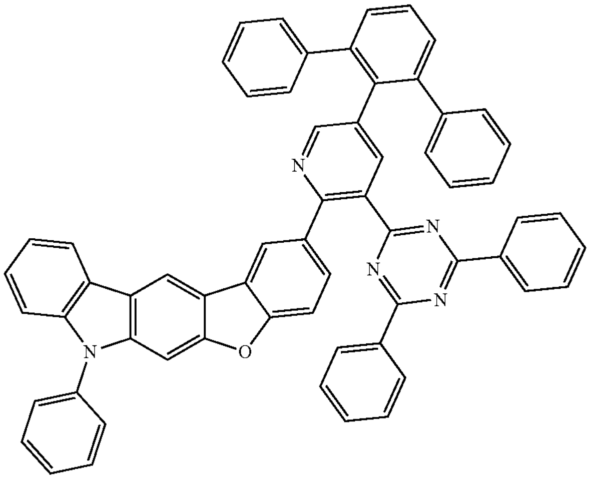
1017
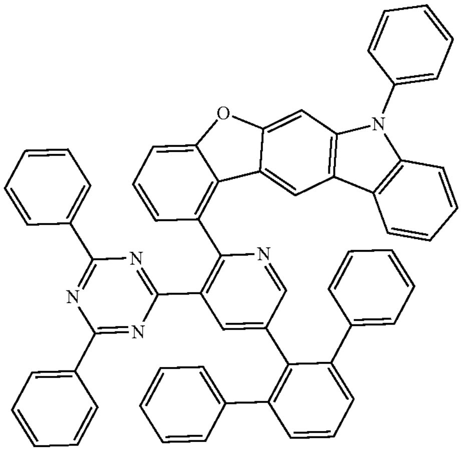
1018
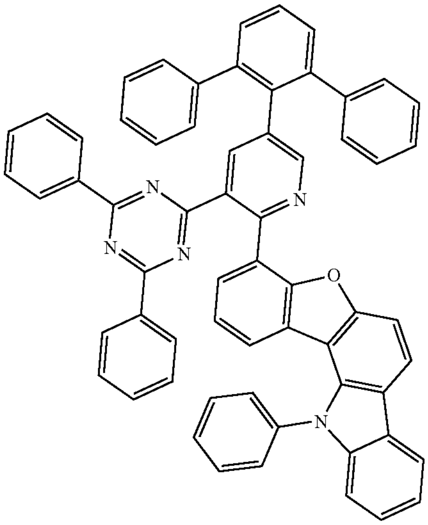
-continued
1019
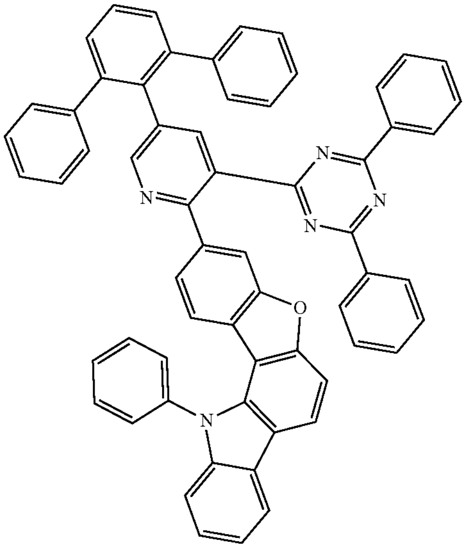

-continued
1020
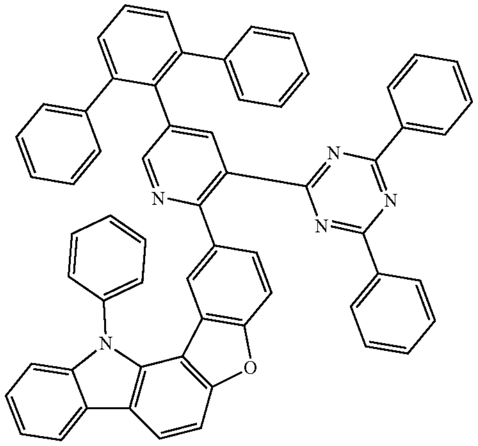
1021
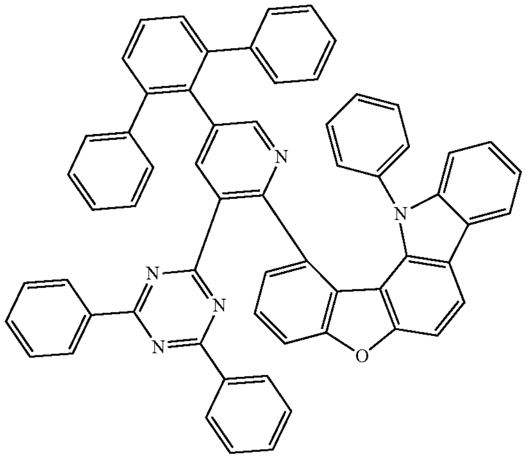
1022
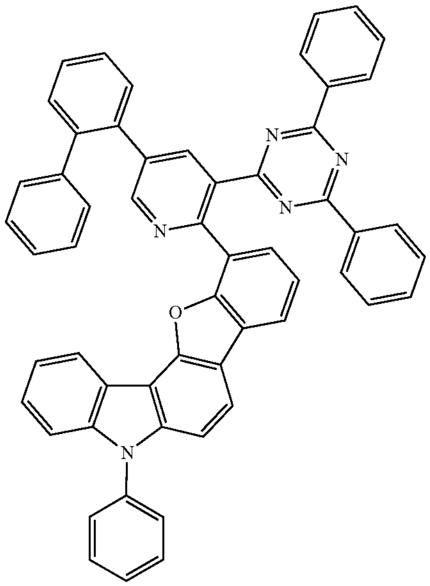
-continued
1023
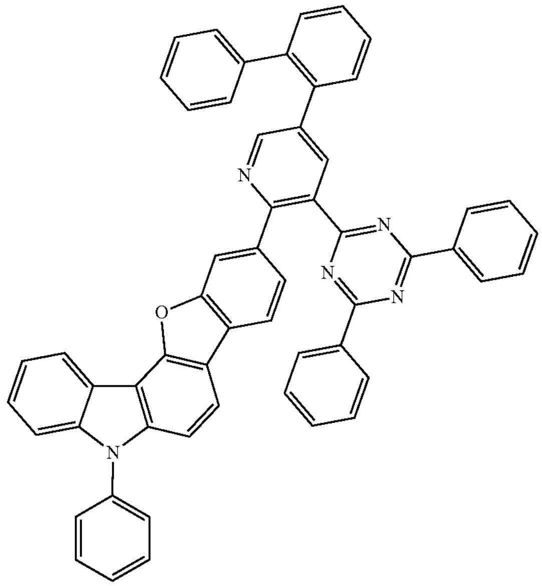
1024
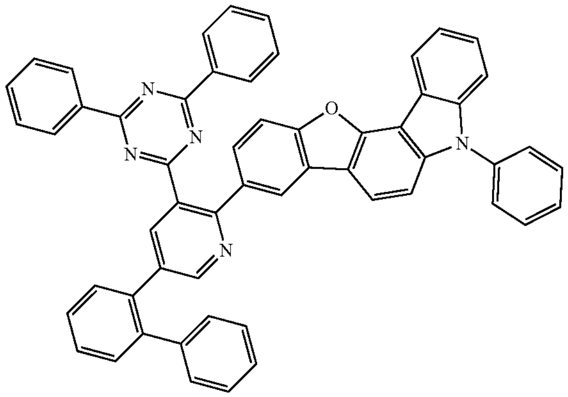
1025
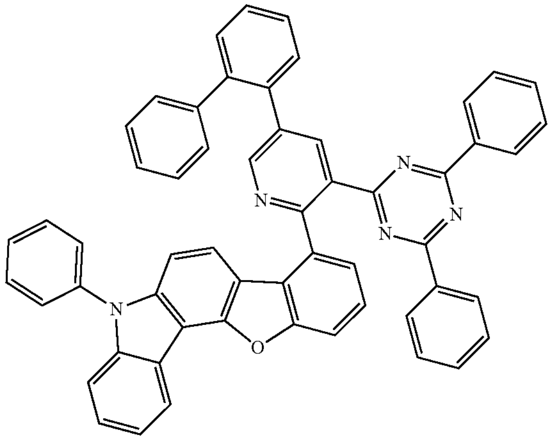

-continued
1026
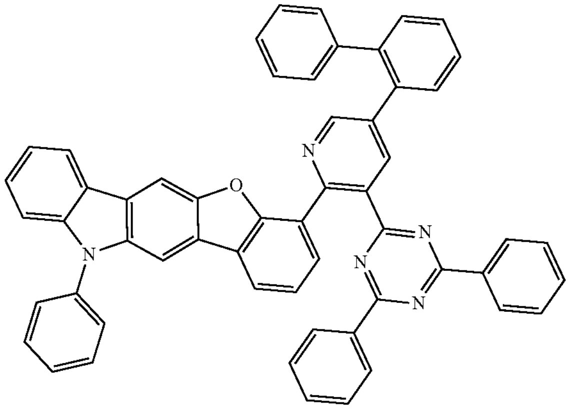
1027
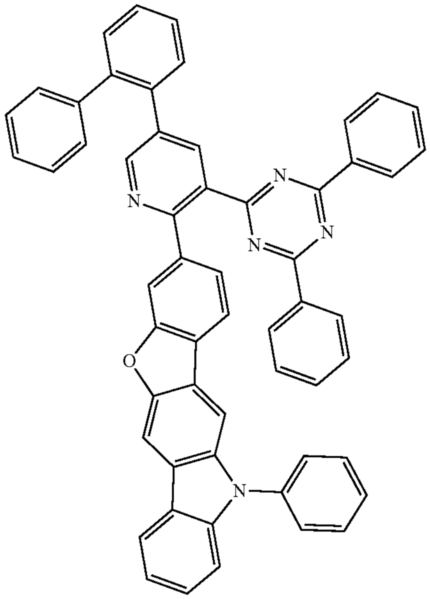
1028
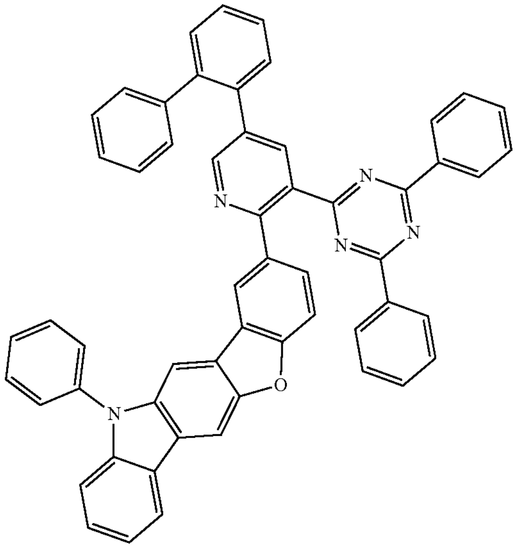
-continued
1029
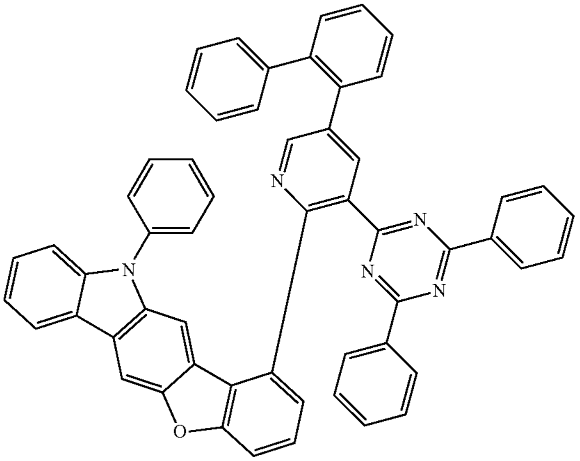
1030
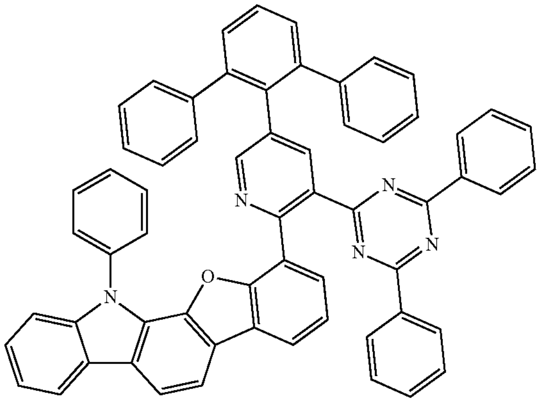
1031
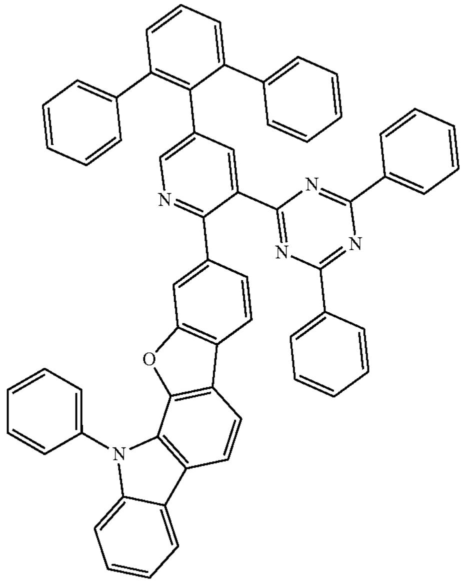

-continued
1032
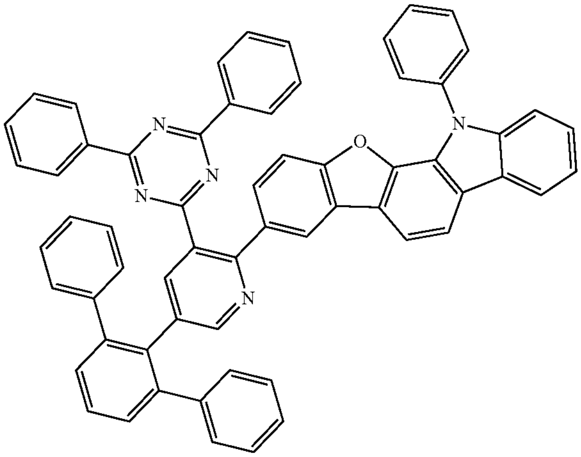
1033
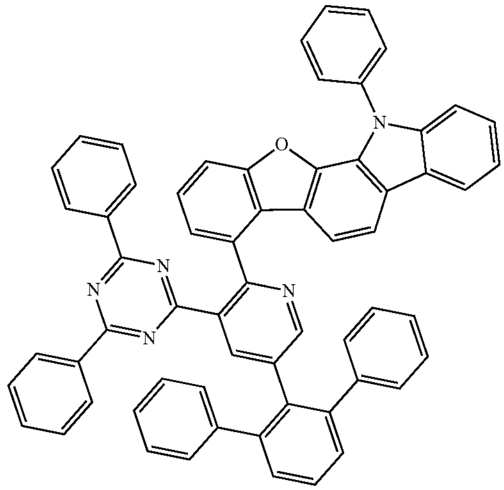
1034
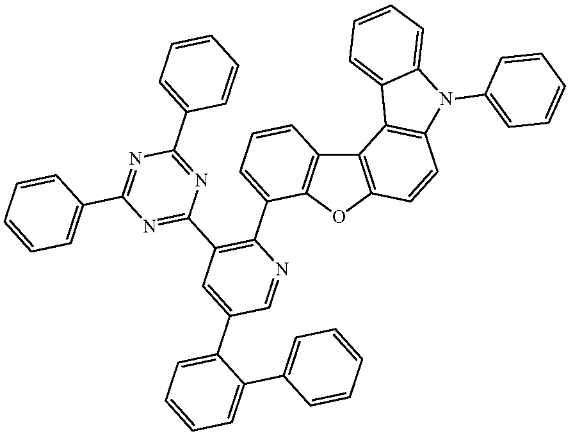
-continued
1035
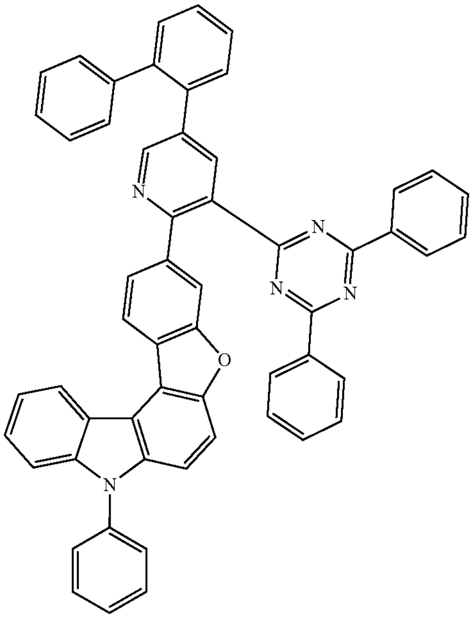
1036
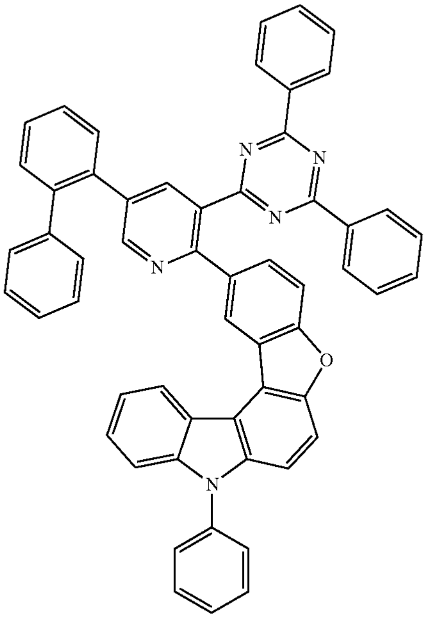

1037
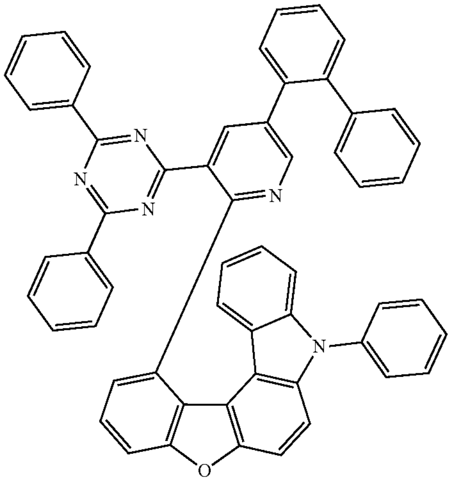
1038
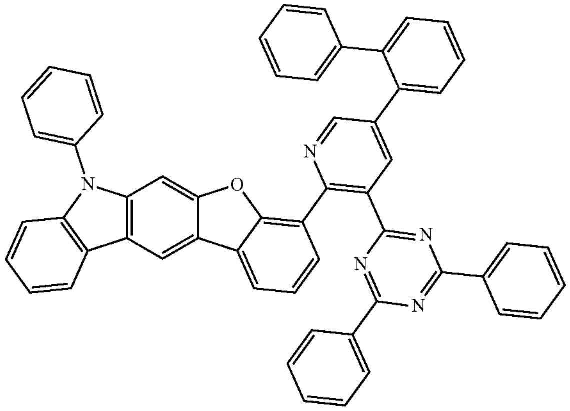
1039
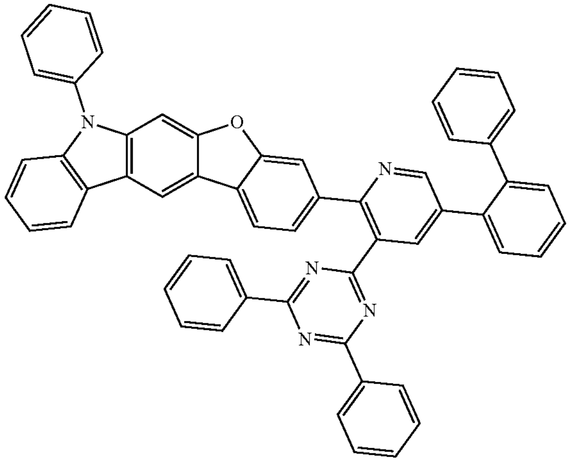
1040
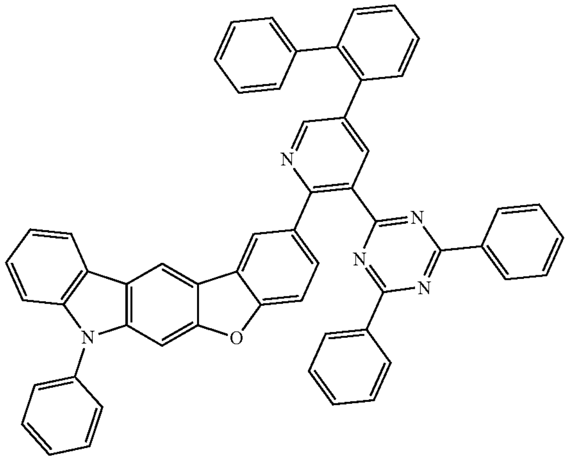
1041
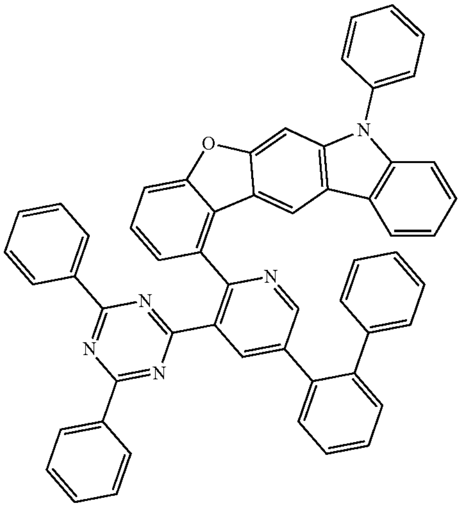
1042
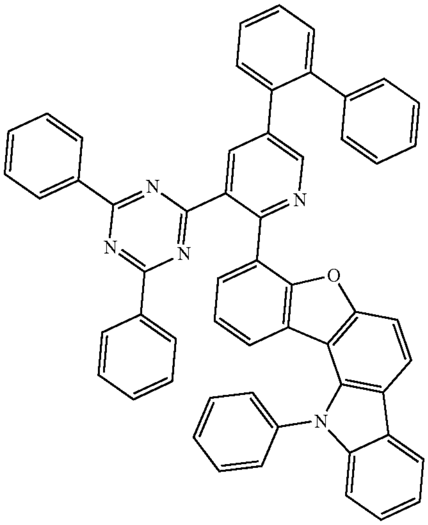

1043
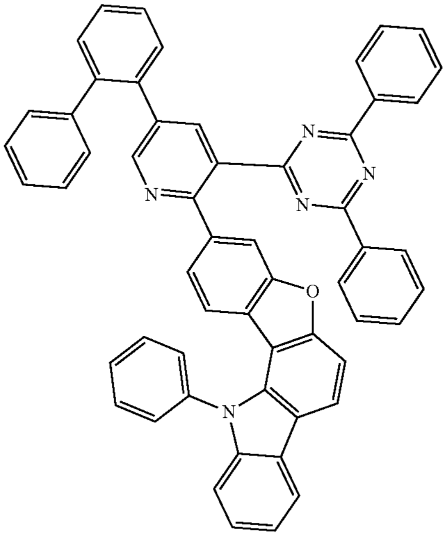
1044
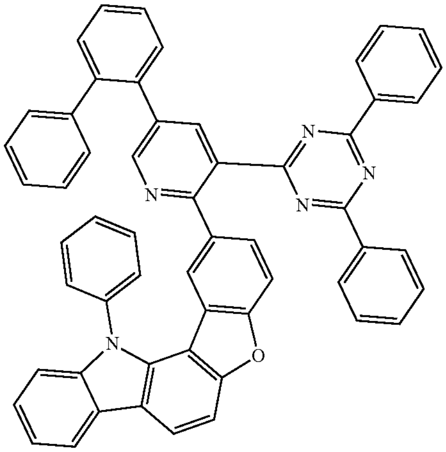
1045
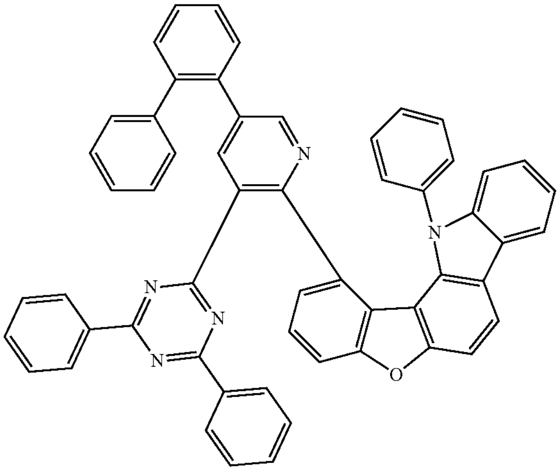
1046
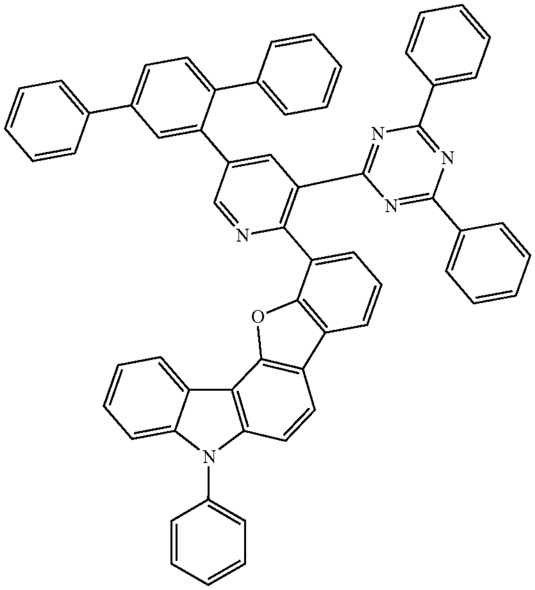
1047
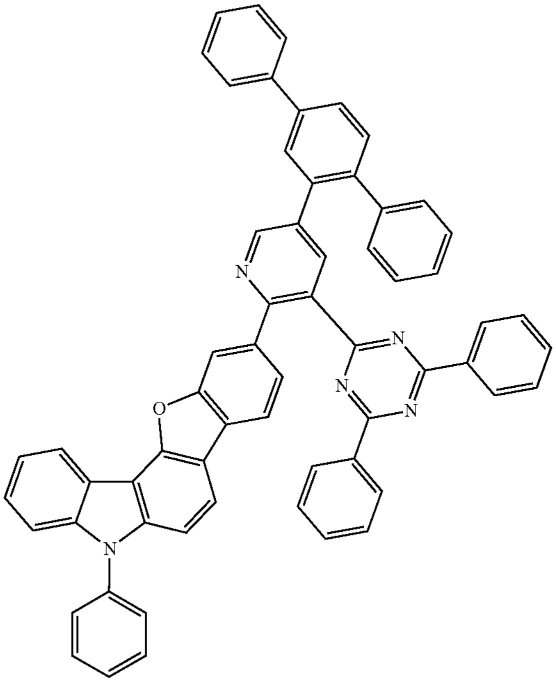

-continued
1048
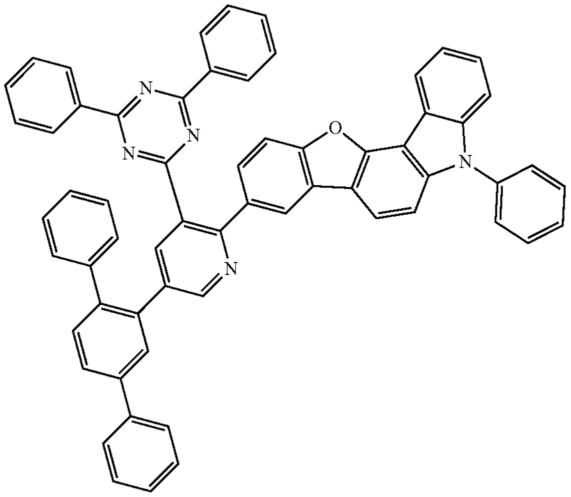
1049
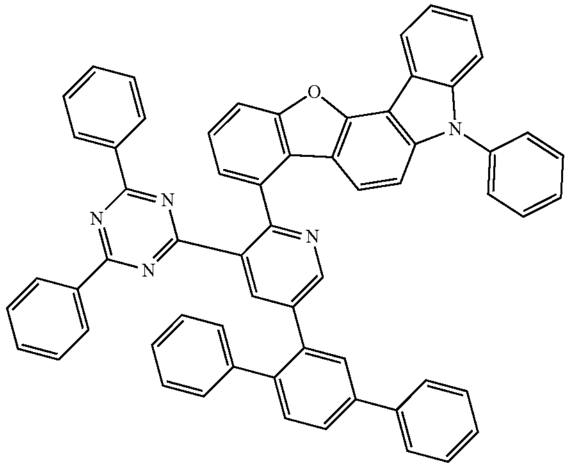
1050
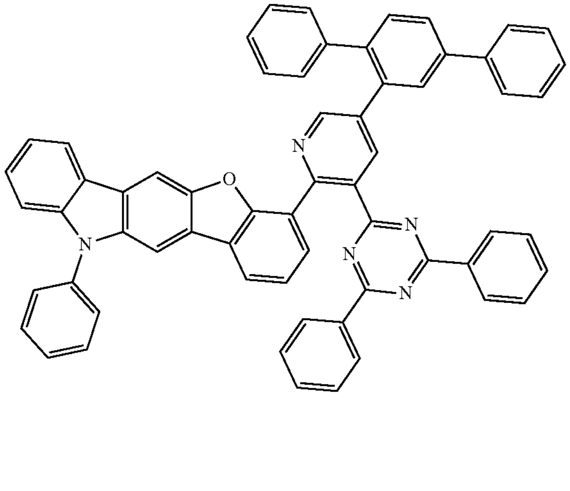
-continued
1051
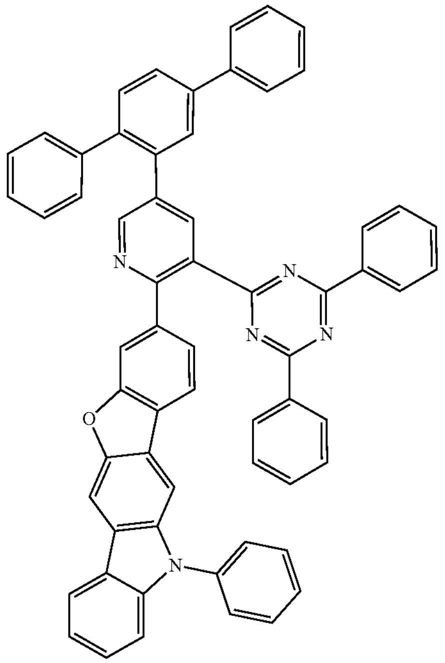
1052
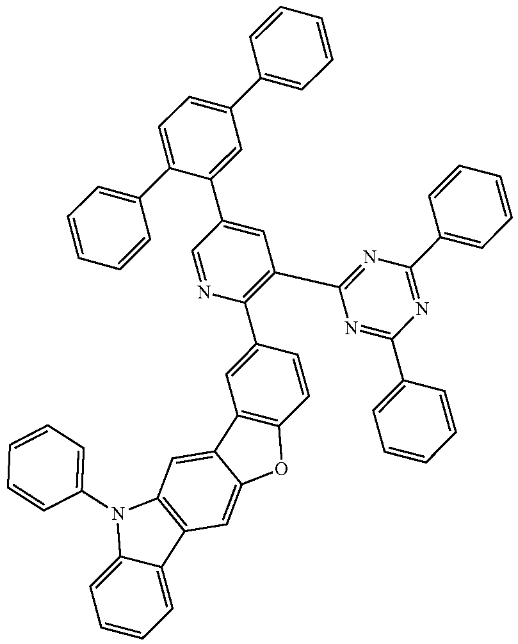

-continued
1053
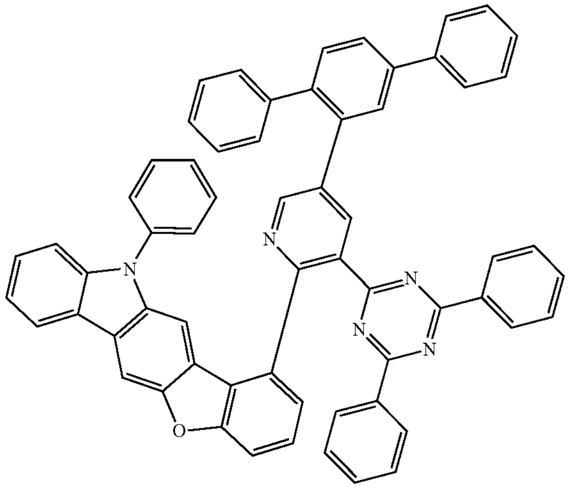
1054
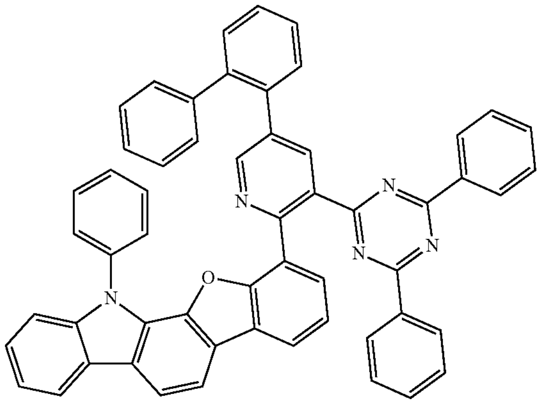
1055
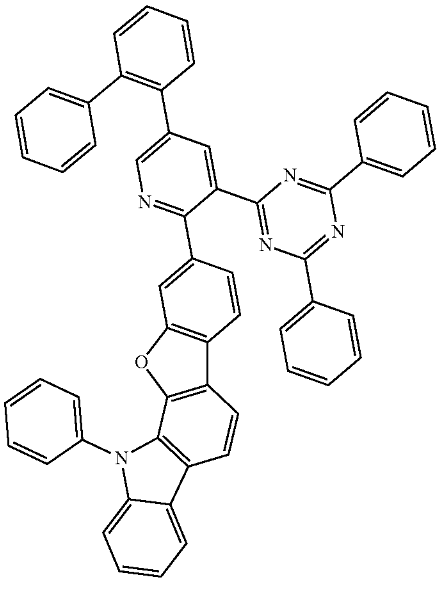
-continued
1056
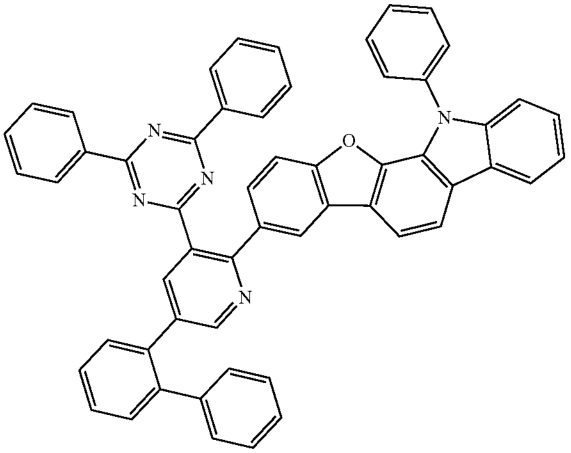
1057
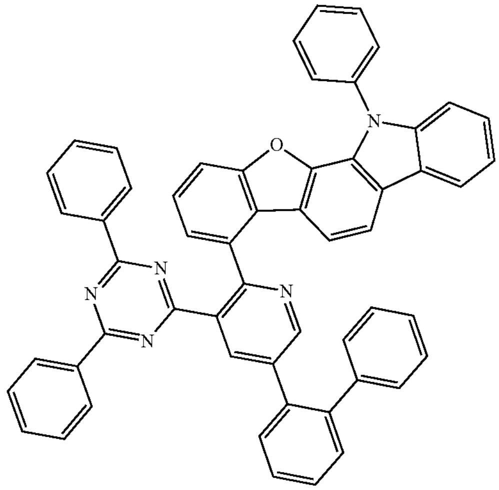
1058
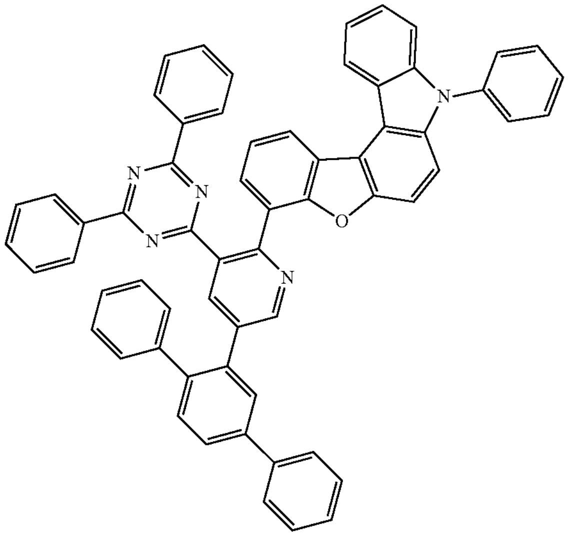

-continued
1059
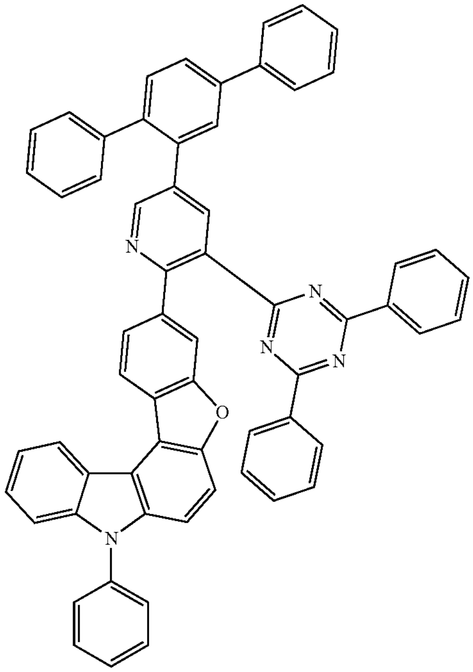
1060
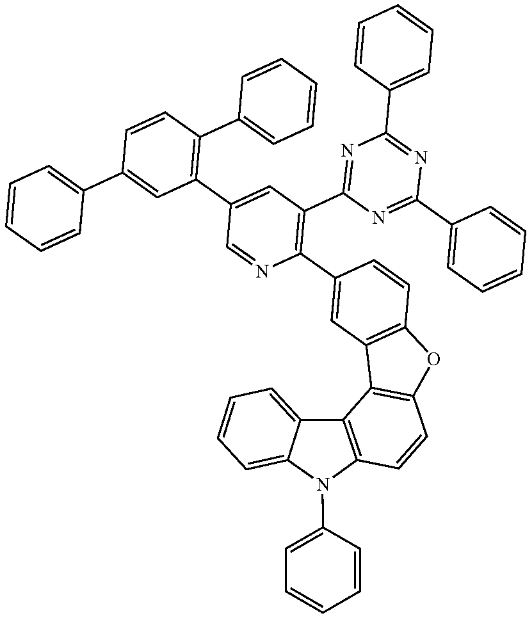
-continued
1061
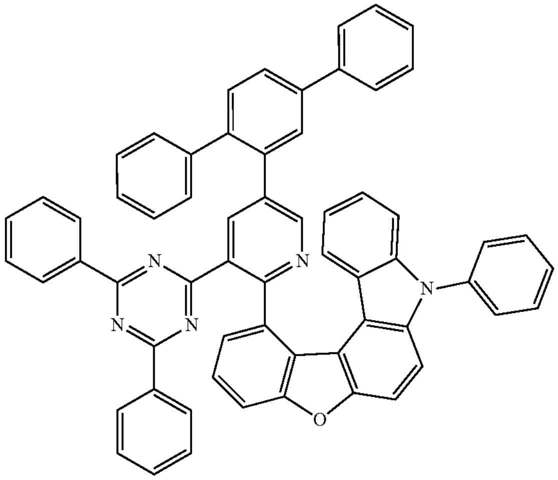
1062
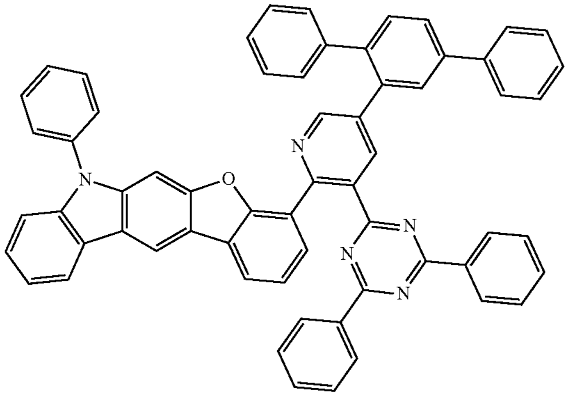
1063
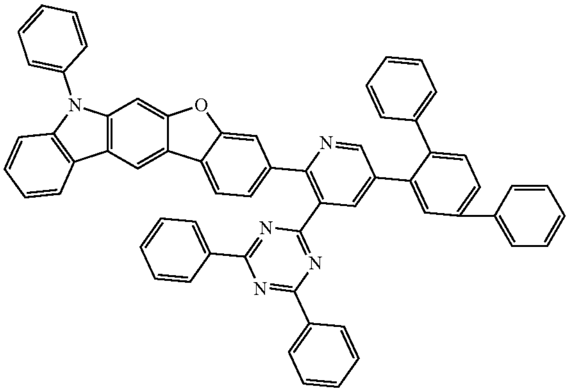

1064
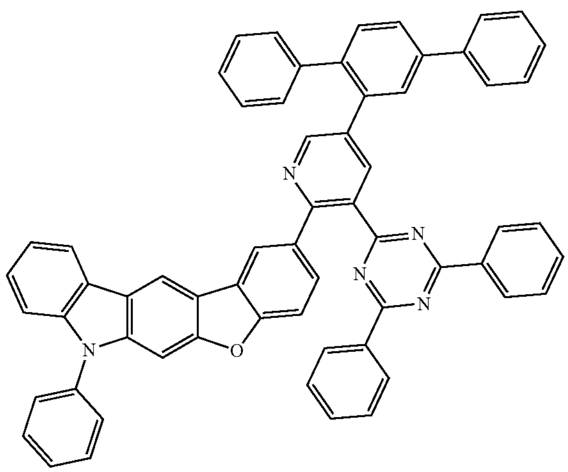
1065
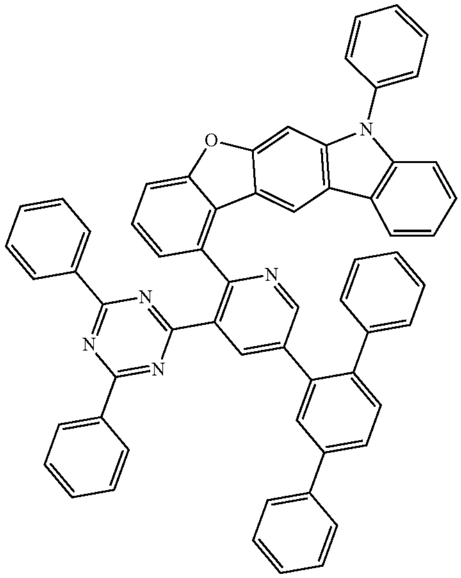
1066
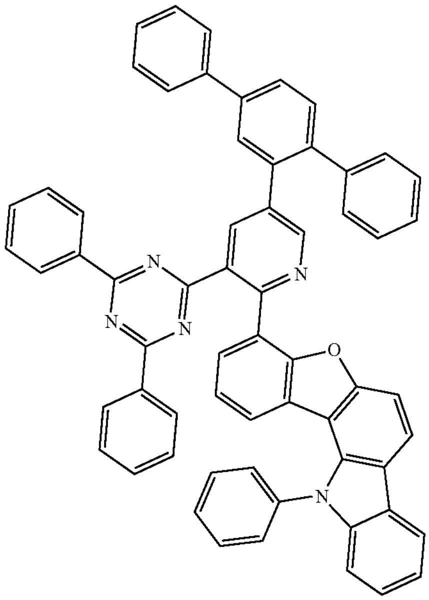
1067
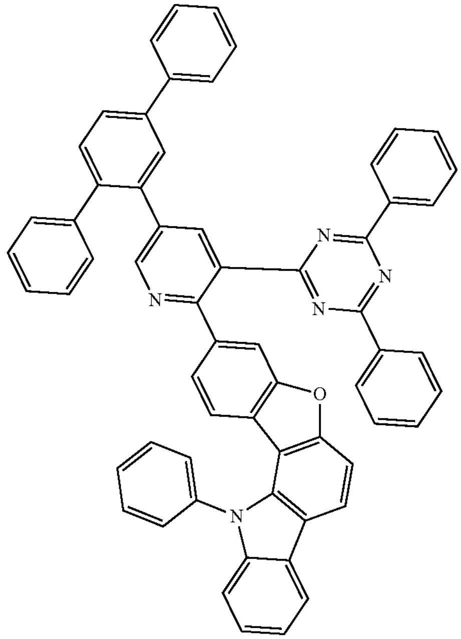
1068
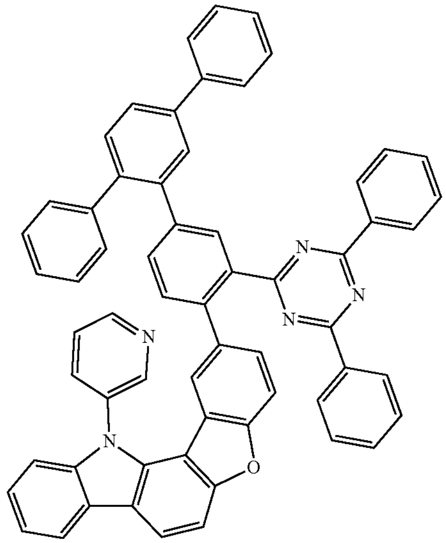

1069
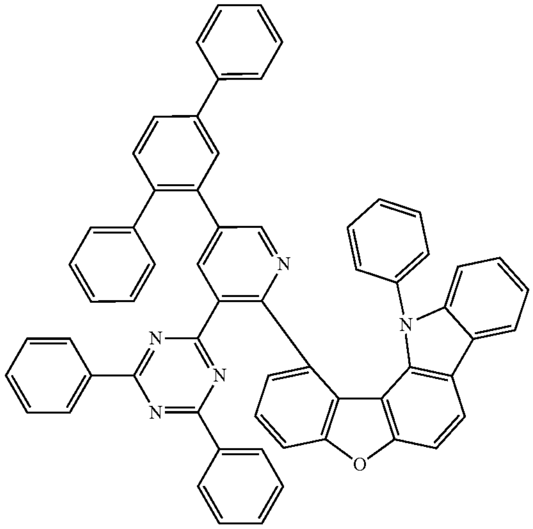
1070
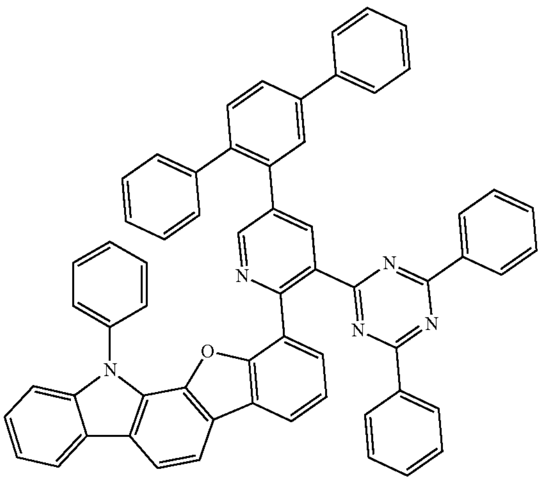
1071
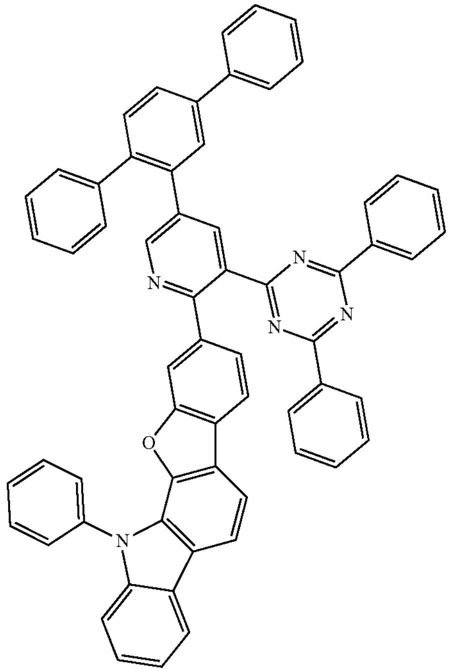
1072
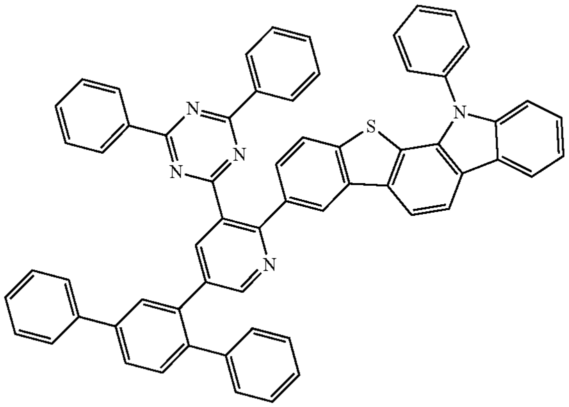

-continued
1073
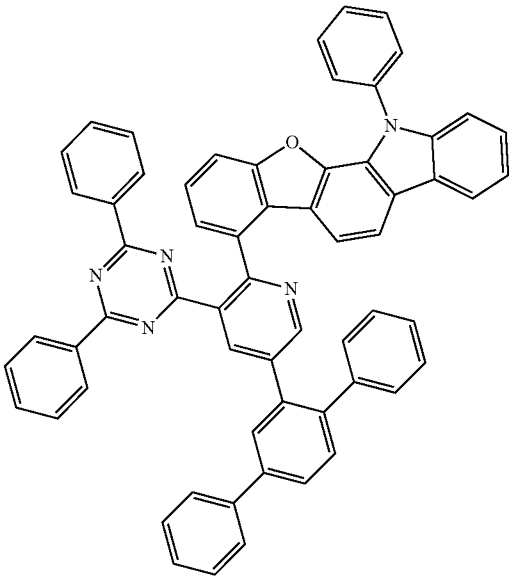
1074
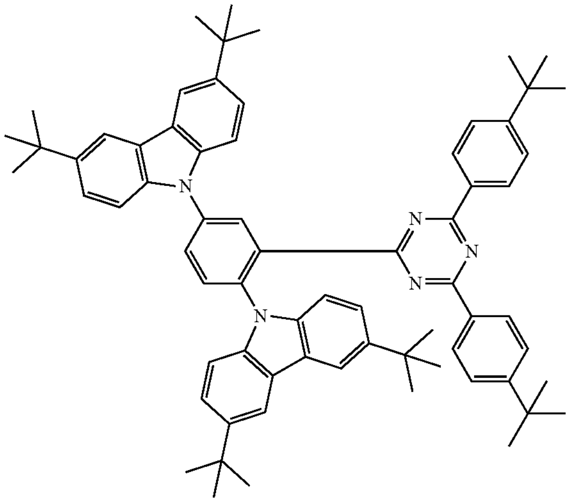
1075
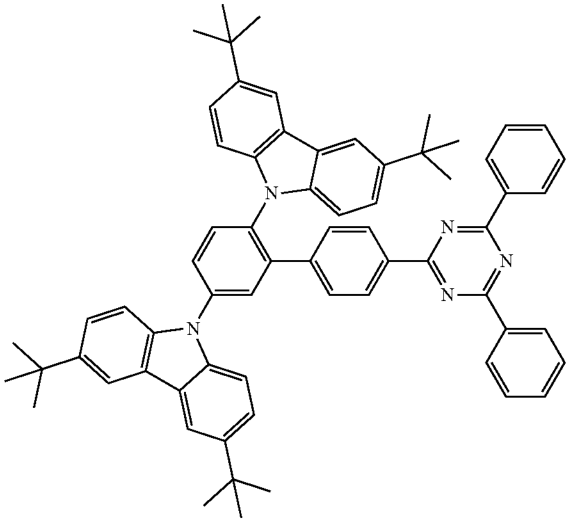
-continued
1076
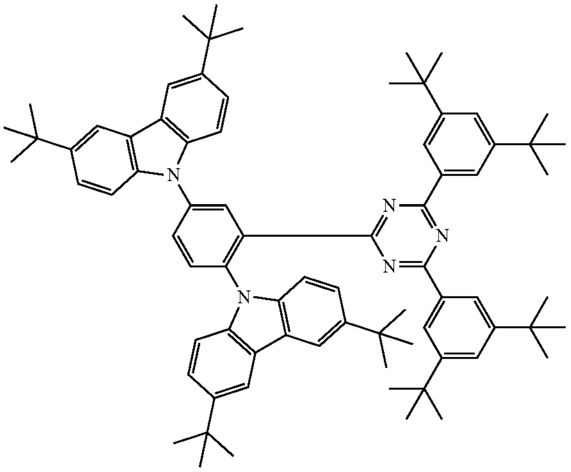
1077
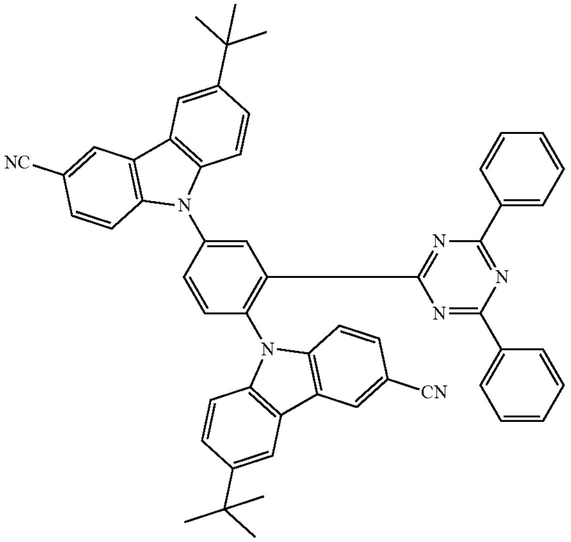
1078
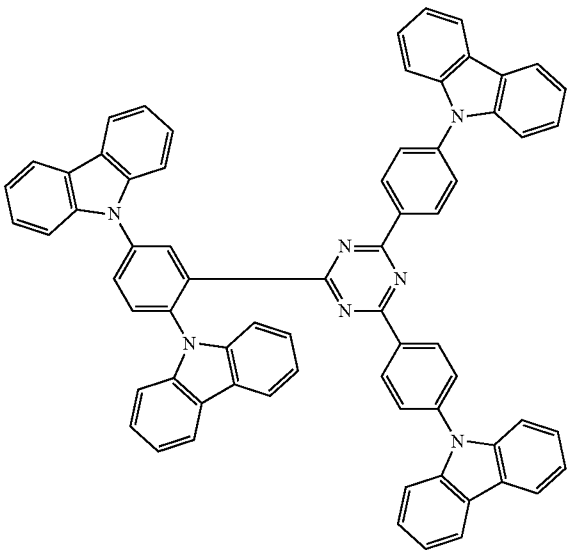

Group XI

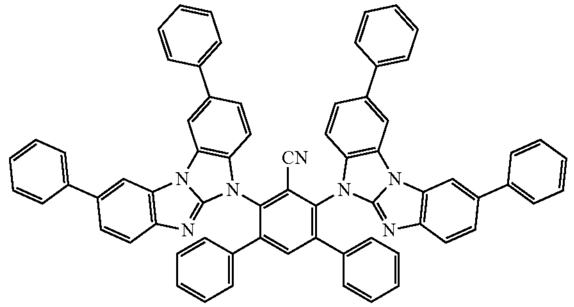

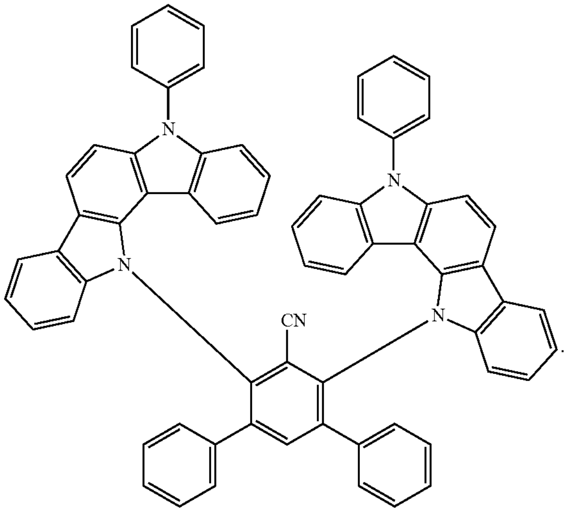

.

Electron Transport Region 5

Next, the electron transport region 5 is arranged on the emission layer 4.

In the organic light-emitting device 10, the electron transport region 5 may be arranged between the emission layer 4 and the second electrode 6.

The electron transport region 5 may have a single-layered structure or a multi-layered structure.

For example, the electron transport region 5 may consist of an electron transport layer, or may have an electron transport layer/electron injection layer structure, a buffer layer/electron transport layer structure, a hole blocking layer/electron transport layer structure, a buffer layer/electron transport layer/electron injection layer structure, or a hole blocking layer/electron transport layer/electron injection layer structure, but embodiments of the present disclosure are not limited thereto. The electron transport region 5 may further include an electron control layer.

The electron transport region 5 may include an electron-transporting material known in the art.

The electron transport region 5 (for example, a buffer layer, a hole blocking layer, an electron control layer, or an electron transport layer in the electron transport region) may include a metal-free compound containing at least one π electron-deficient nitrogen-containing $C_1$-$C_{60}$ cyclic group. The π electron-deficient nitrogen-containing $C_1$-$C_{60}$ cyclic group may be the same as described herein.

In an embodiment, the electron transport region 5 may include a compound represented by Formula 601:

$$[Ar_{601}]_{xe11}\text{-}[(L_{601})_{xe1}\text{-}R_{601}]_{xe21} \qquad \text{Formula 601}$$

wherein, in Formula 601, $Ar_{601}$ and $L_{601}$ may each independently be a substituted or unsubstituted $C_5$-$C_{60}$ carbocyclic group unsubstituted or substituted with at least one $R_{601a}$ or a $C_1$-$C_{60}$ heterocyclic group unsubstituted or substituted with at least one $R_{601a}$, xe11 may be 1, 2, or 3, xe1 may be an integer from 0 to 5, $R_{601a}$ and $R_{601}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(═O)($Q_{601}$), —S(═O)$_2$($Q_{601}$), or —P(═O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In an embodiment, at least one of $Ar_{601}$(s) in the number of xe11 and $R_{601}$(s) in the number of xe21 may include the π electron-deficient nitrogen-containing $C_1$-$C_{60}$ cyclic group.

In an embodiment, $Ar_{601}$ and $L_{601}$ in Formula 601 may each independently be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(═O)$_2$($Q_{31}$), —P(═O)($Q_{31}$)($Q_{32}$), or any combination thereof, and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

When xe11 in Formula 601 is 2 or more, two or more of $Ar_{601}$(s) may be linked to each other via a single bond.

In one or more embodiments, $Ar_{601}$ in Formula 601 may be an anthracene group.

In an embodiment, the compound represented by Formula 601 may be represented by Formula 601-1:

Formula 601-1

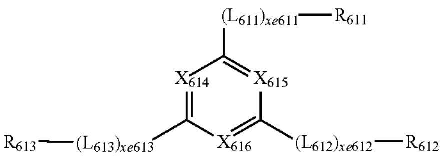

wherein, in Formula 601-1, $X_{614}$ may be N or $C(R_{614})$, $X_{615}$ may be N or $C(R_{615})$, $X_{616}$ may be N or $C(R_{616})$, and at least one of $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, or a naphthyl group.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formulae 601 and 601-1 may each independently be: a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, or an azacarbazolyl group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, or any combination thereof; or $-S(=O)_2(Q_{601})$ or $-P(=O)(Q_{601})(Q_{602})$, and $Q_{601}$ and $Q_{602}$ may respectively be the same as described herein.

In an embodiment, the electron transport region 5 may include at least one compound of Compounds ET1 to ET36 and HE6-203, but embodiments of the present disclosure are not limited thereto:

ET1

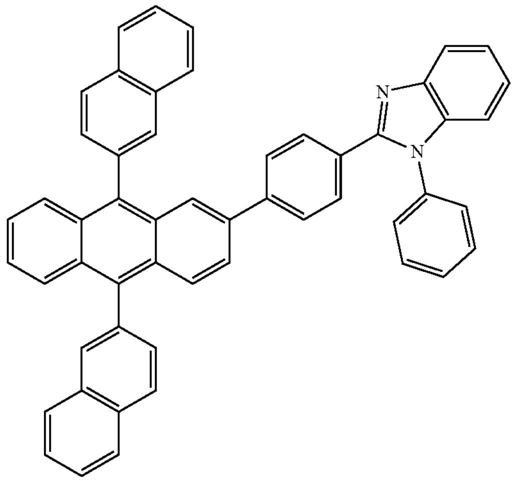

ET2
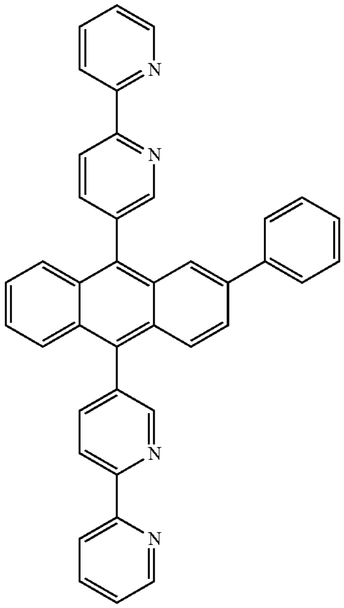
ET3
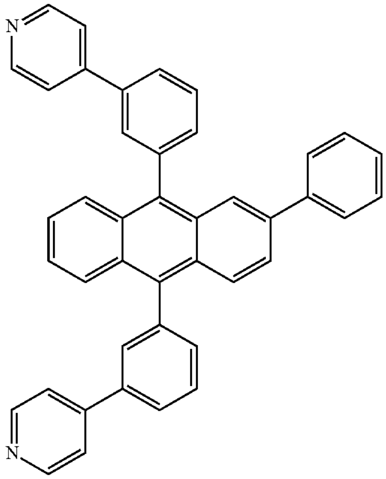
ET4
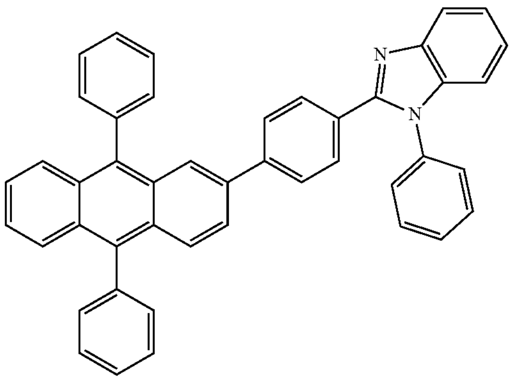
ET5
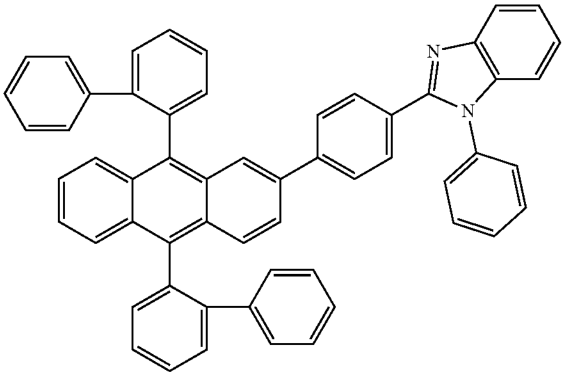
ET6
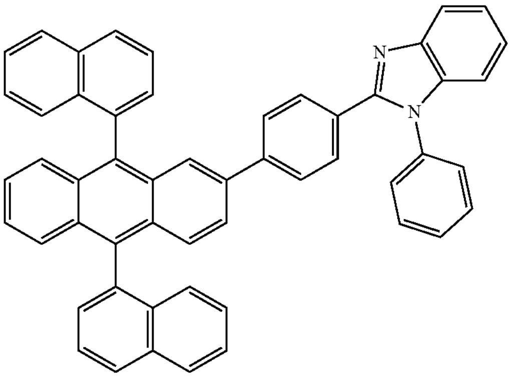
ET7
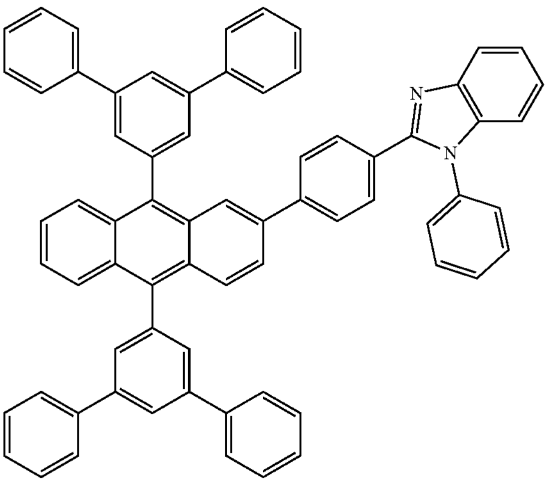

-continued
ET8
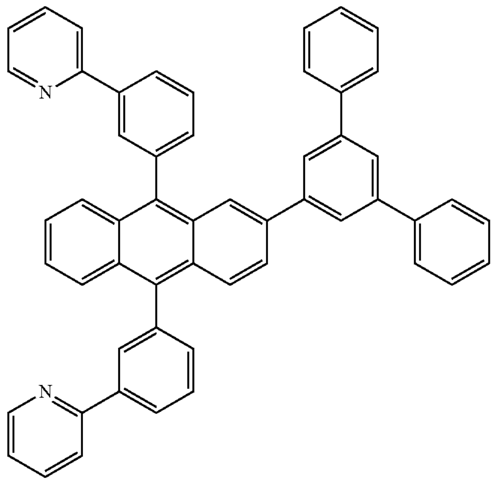
ET9
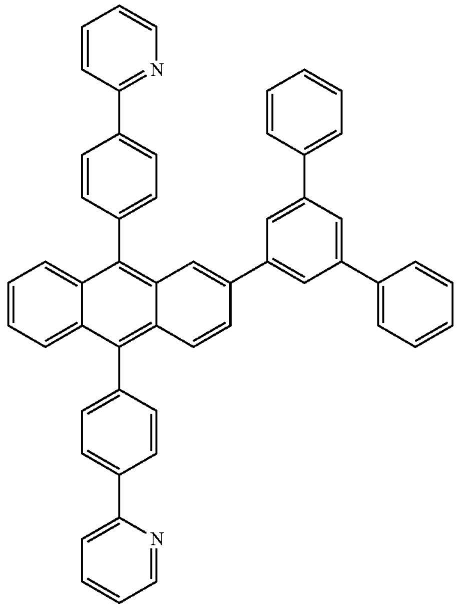
-continued
ET10
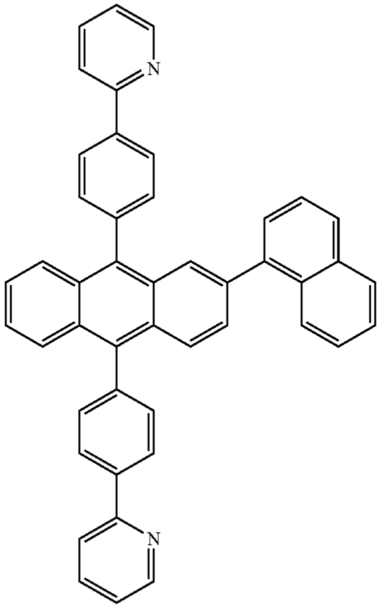
ET11
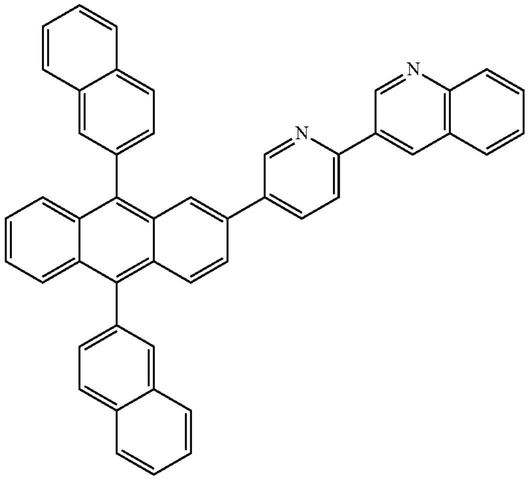
ET12
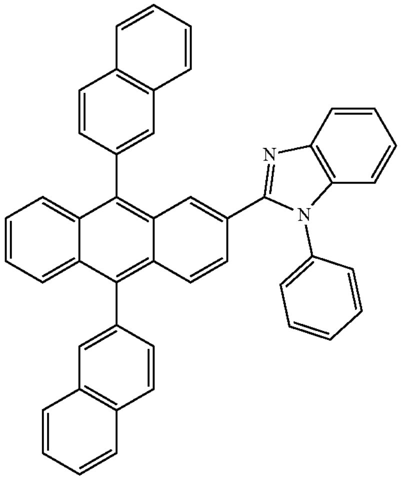

-continued
ET13
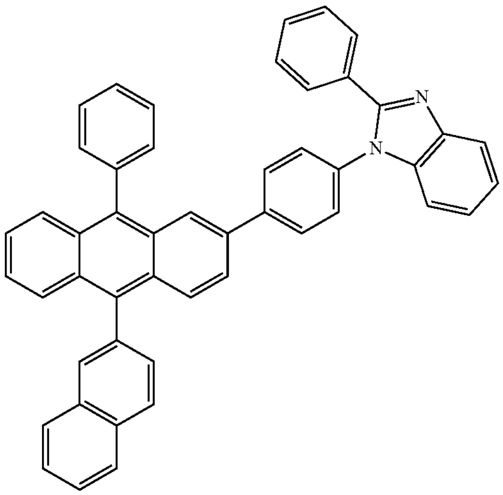
ET14
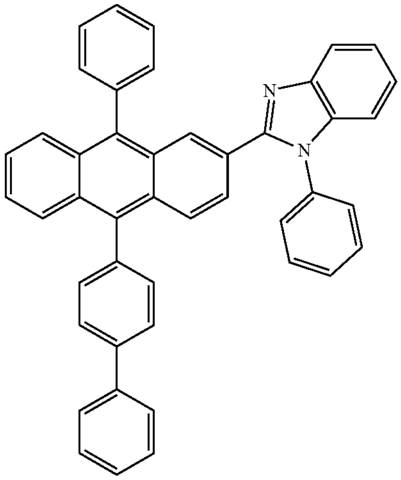
ET15
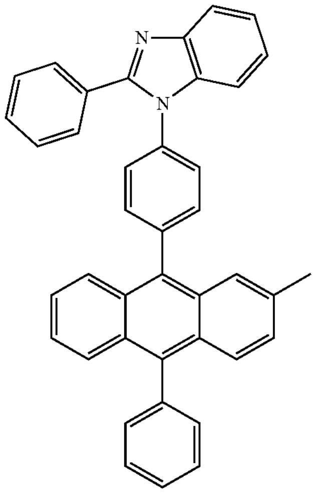
-continued
ET16
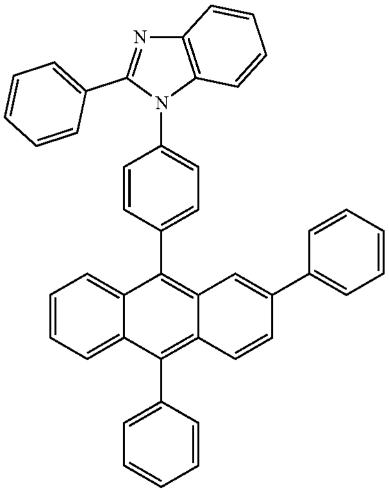
ET17
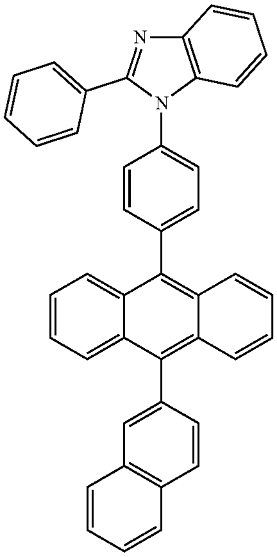
ET18
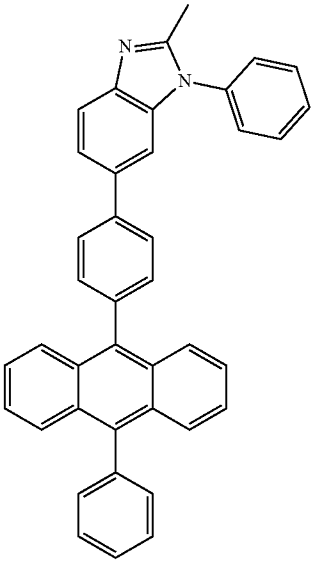

ET19
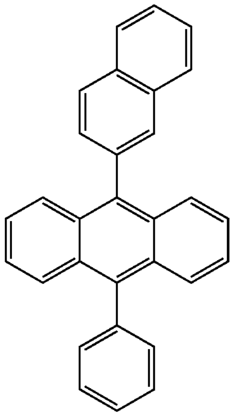
ET20
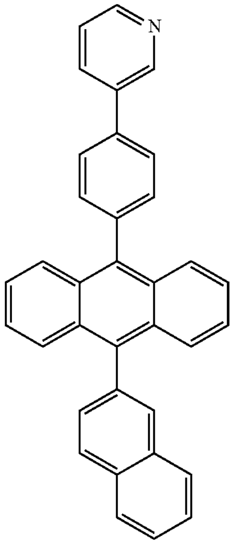
ET21
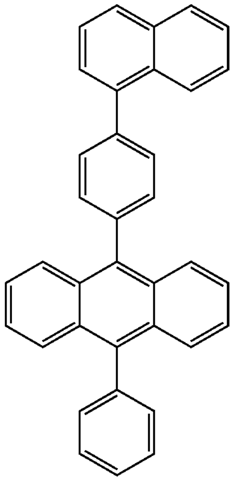
ET22
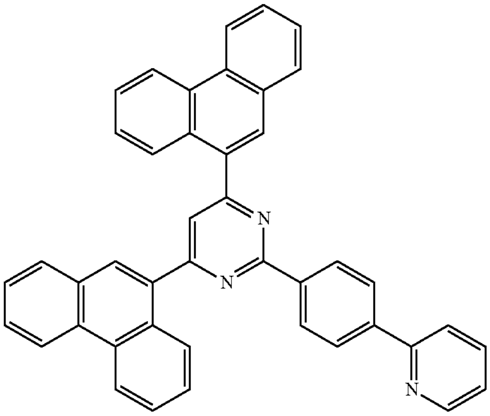
ET23
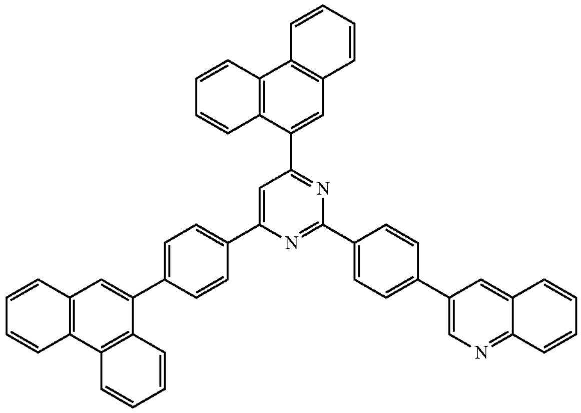
ET24
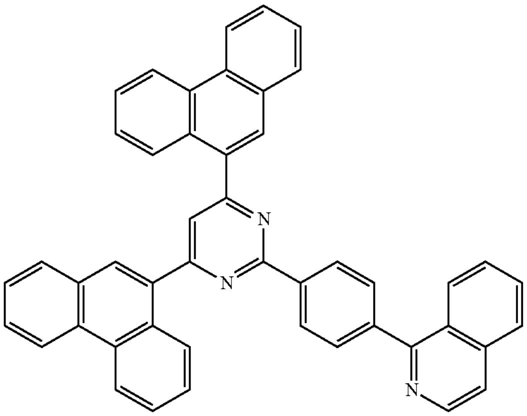

-continued
ET25
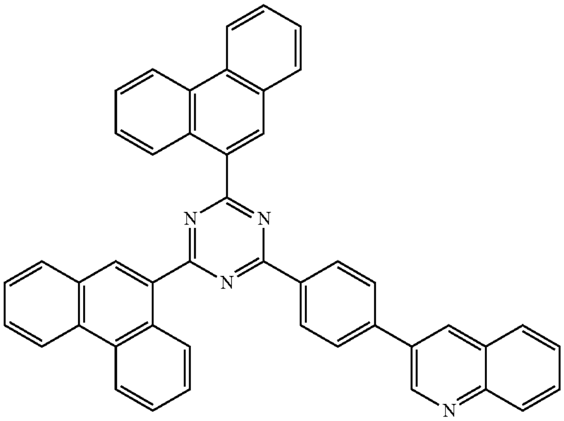
ET26
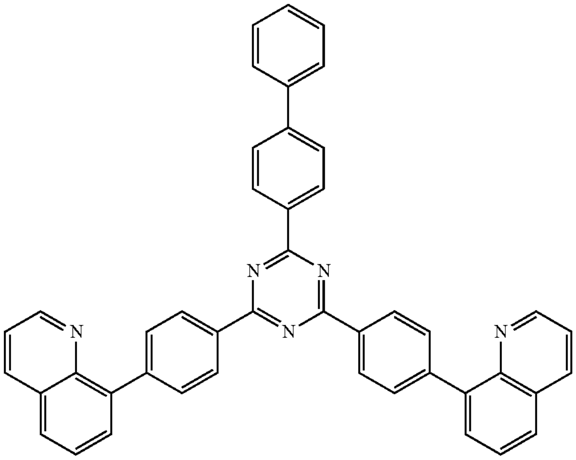
ET27
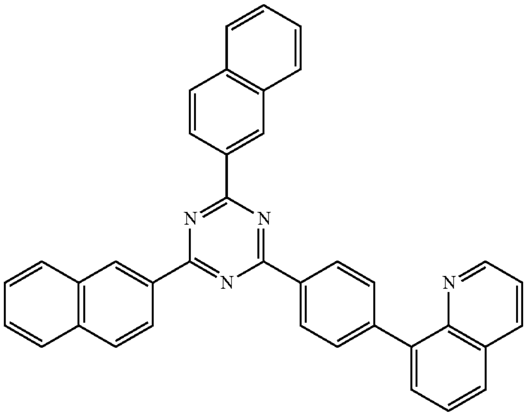
-continued
ET28
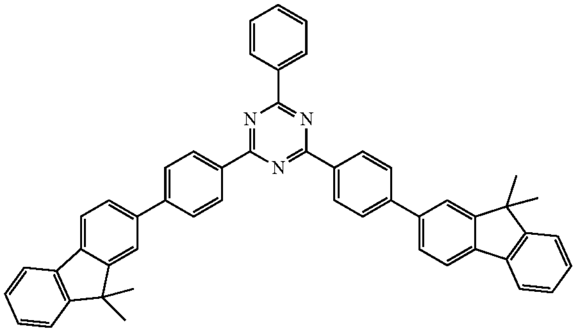
ET29
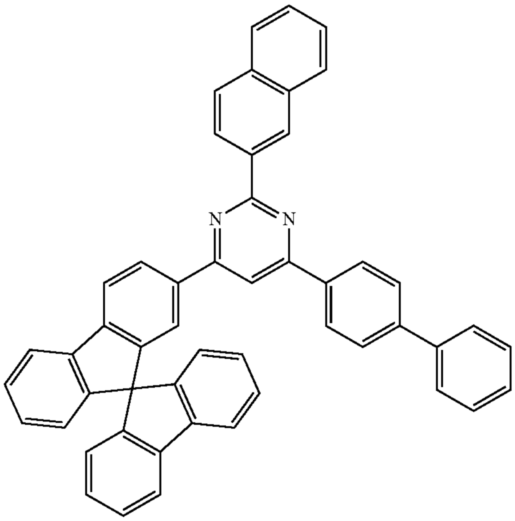
ET30
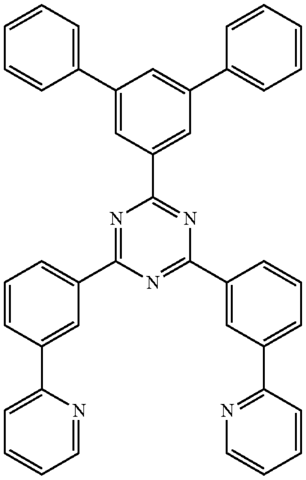

-continued
ET31
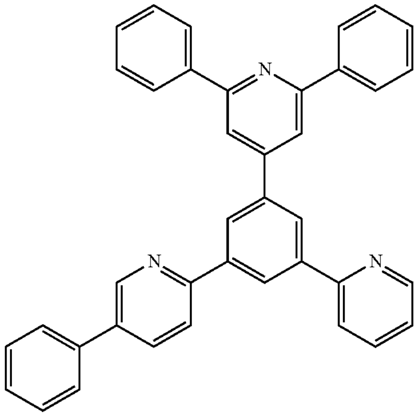
ET32
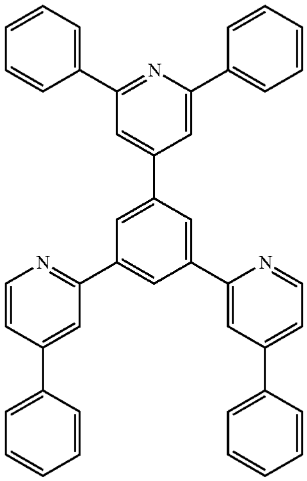
ET33
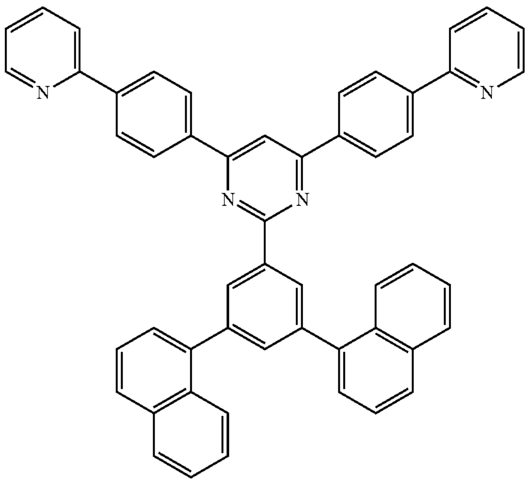
-continued
ET34
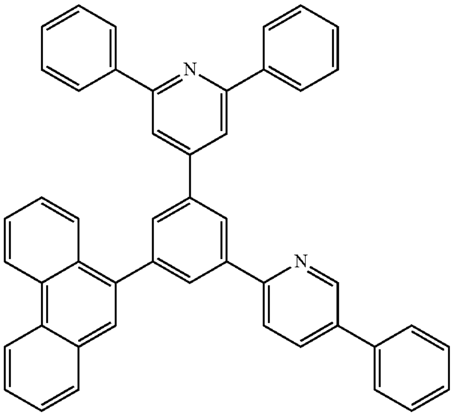
ET35
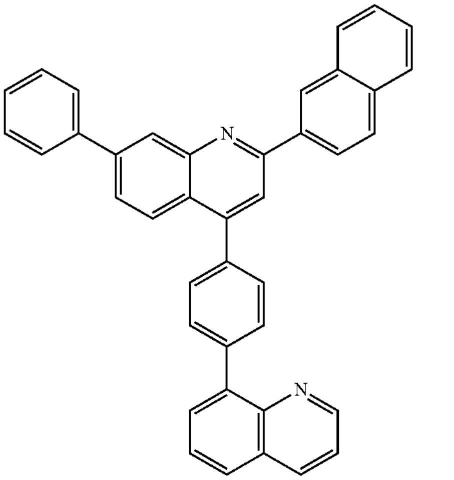
ET36
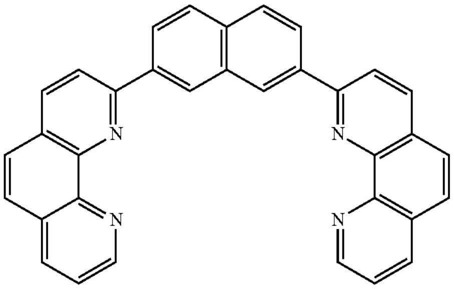
HE6-203
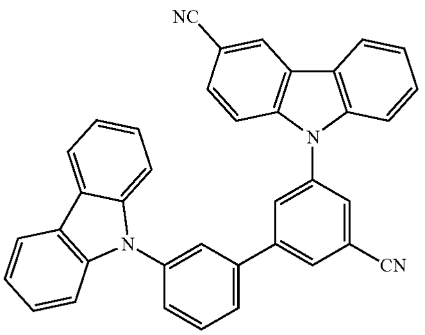
In one or more embodiments, the electron transport region 5 may include at least one of 2,9-dimethyl-4,7-diphenyl-1,10-phenanthroline (BCP), 4,7-diphenyl-1,10-phenanthroline (Bphen), $Alq_3$, BAlq, 3-(biphenyl-4-yl)-5-(4-tert-butylphenyl)-4-phenyl-4H-1,2,4-triazole (TAZ), NTAZ, or any combination thereof:

$Alq_3$

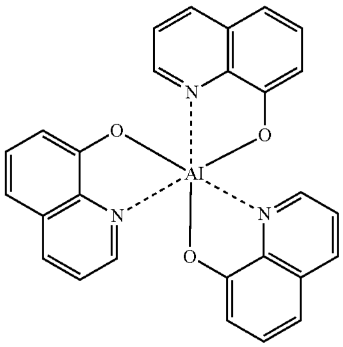

BAlq

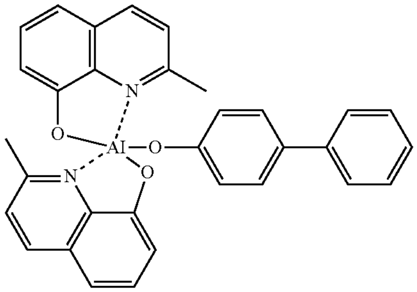

TAZ

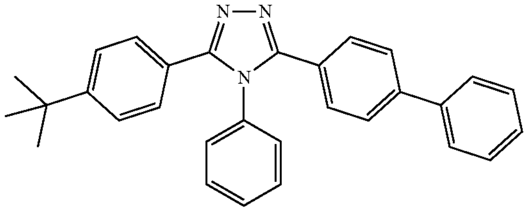

NTAZ

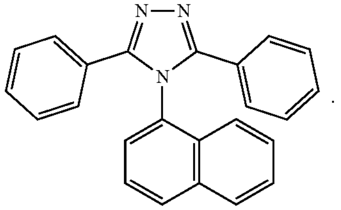

A thicknesses of each of the buffer layer, the hole blocking layer, and the electron control layer may each independently be in a range of about 20 Å to about 1,000 Å, for example, about 30 Å to about 300 Å. When the thickness of the buffer layer, the hole blocking layer, or the electron control layer is within these ranges, excellent hole blocking characteristics or excellent electron control characteristics may be obtained without a substantial increase in driving voltage.

A thickness of the electron transport layer may be in a range of about 100 Å to about 1,000 Å, for example, about 150 Å to about 500 Å. When the thickness of the electron transport layer is within these ranges, satisfactory electron transporting characteristics may be obtained without a substantial increase in driving voltage.

In one or more embodiments, the electron transport region 5 (for example, the electron transport layer in the electron transport region) may further include, in addition to the materials described above, a metal-containing material.

The metal-containing material may include at least one of an alkali metal complex, an alkaline earth-metal complex, or a combination thereof. The alkali metal complex may include a Li ion, a Na ion, a K ion, a Rb ion, a Cs ion, or any combination thereof, and the alkaline earth-metal complex may include a Be ion, a Mg ion, a Ca ion, a Sr ion, a Ba ion, or any combination thereof. A ligand coordinated with the metal ion of the alkali metal complex or the alkaline earth-metal complex may be a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, or a cyclopentadiene, but embodiments of the present disclosure are not limited thereto.

For example, the metal-containing material may include a Li complex. The Li complex may include, for example, Compound ET-D1 (LiQ) or ET-D2:

ET-D1

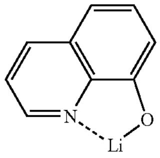

ET-D2

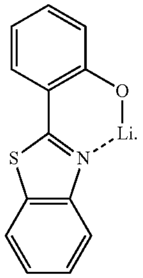

The electron transport region 5 may include an electron injection layer that facilitates the injection of electrons from the second electrode 6. The electron injection layer may directly contact the second electrode 6.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth metal complex, a rare earth metal complex, or any combination thereof.

The alkali metal may be Li, Na, K, Rb, or Cs. In an embodiment, the alkali metal may be Li, Na, or Cs. In one or more embodiments, the alkali metal may be Li or Cs, but embodiments of the present disclosure are not limited thereto.

The alkaline earth metal may be Mg, Ca, Sr, or Ba.

The rare earth metal may be Sc, Y, Ce, Tb, Yb, or Gd.

The alkali metal compound, the alkaline earth-metal compound, and the rare earth metal compound may be an oxide or a halide (for example, fluorides, chlorides, bromides, or iodides) of the alkali metal, the alkaline earth-metal, or the rare earth metal.

The alkali metal compound may be an alkali metal oxide, such as $Li_2O$, $Cs_2O$, or $K_2O$, or an alkali metal halide, such as LiF, NaF, CsF, KF, LiI, NaI, CsI, or KI. In an embodiment, the alkali metal compound may be LiF, $Li_2O$, NaF, LiI, NaI, CsI, or KI, but embodiments of the present disclosure are not limited thereto.

The alkaline earth metal compound may be an alkaline earth metal oxide, such as BaO, SrO, CaO, $Ba_xSr_{1-x}O$ ($0<x<1$), or $Ba_xCa_{1-x}O$ ($0<x<1$). In an embodiment, the alkaline earth metal compound may be BaO, SrO, and CaO, but embodiments of the present disclosure are not limited thereto.

The rare earth metal compound may be $YbF_3$, $ScF_3$, $ScO_3$, $Y_2O_3$, $Ce_2O_3$, $GdF_3$, or $TbF_3$. In an embodiment, the rare earth metal compound may be $YbF_3$, $ScF_3$, $TbF_3$, $YbI_3$, $ScI_3$, or $TbI_3$, but embodiments of the present disclosure are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be hydroxy quinoline, hydroxy isoquinoline, hydroxy benzoquinoline, hydroxy acridine, hydroxy phenanthridine, hydroxy phenyloxazole, hydroxy, phenylthiazole, hydroxy diphenyloxadiazole, hydroxy diphenylthiadiazole, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may consist of an alkali metal, an alkaline earth metal, a rare earth metal, an alkali metal compound, an alkaline earth metal compound, a rare earth metal compound, an alkali metal complex, an alkaline earth metal complex, a rare earth metal complex, or any combination thereof, as described above. In one or more embodiments, the electron injection layer may further include an organic material. When the electron injection layer further includes an organic material, an alkali metal, an alkaline earth metal, a rare earth metal, an alkali metal compound, an alkaline earth metal compound, a rare earth metal compound, an alkali metal complex, an alkaline earth-metal complex, a rare earth metal complex, or any combination thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within these ranges, satisfactory electron injection characteristics may be obtained without a substantial increase in driving voltage.

Second Electrode 6

The second electrode 6 may be arranged on the electron transport region 5. The second electrode 6 may be a cathode which is an electron injection electrode, and in this regard, a material for forming the second electrode 6 may be a metal, an alloy, an electrically conductive compound, and a combination thereof, each having a relatively low work function.

The second electrode 6 may include at least one of lithium (Li), silver (Ag), magnesium (Mg), aluminum (Al), aluminum-lithium (Al—Li), calcium (Ca), magnesium-indium (Mg—In), magnesium-silver (Mg—Ag), ITO, IZO, or any combination thereof, but embodiments of the present disclosure are not limited thereto. The second electrode 6 may be a transmissive electrode, a semi-transmissive electrode, or a reflective electrode.

The second electrode 6 may have a single-layered structure having a single layer or a multi-layered structure including a plurality of layers.

A thickness of the second electrode 6 may be about 100 Å or more and about 10,000 Å or less, but embodiments of the present disclosure are not limited thereto.

In addition, a sealing layer may be further arranged on the second electrode 6. The sealing layer is not particularly limited, and for example, may include α-NPD, NPB, TPD, m-MTDATA, $Alq_3$, CuPc, N4, N4, N4', N4'-tetra(phenyl-4-yl)biphenyl-4,4'-diamine (TPD15), 4,4',4"-tris(carbazol-9-yl)-triphenylamine (TCTA), N,N'-bis(naphthalene-1-yl), or any combination thereof.

Hereinbefore, the organic light-emitting device has been described with reference to FIG. 1, but embodiments of the present disclosure are not limited thereto.

Diagnostic Composition

Another aspect of the present disclosure provides a diagnostic composition including at least one condensed cyclic compound represented by Formula 1.

Since the condensed cyclic compound represented by Formula 1 provides high luminescence efficiency, the diagnostic composition including the at least one condensed cyclic compound may have high diagnostic efficiency.

The diagnostic composition may be used in various applications including a diagnosis kit, a diagnosis reagent, a biosensor, and a biomarker.

Electronic Apparatus

Another aspect of the present disclosure provides an electronic apparatus including the organic light-emitting device.

In an embodiment, the electronic device may further include a thin-film transistor, and the thin-film transistor may include a source electrode and a drain electrode, wherein the first electrode of the organic light-emitting device may be electrically connected to at least one of the source electrode and the drain electrode of the thin-film transistor.

In an embodiment, the electronic device may be applied in various fields such as, a diagnostic kit, a biosensor, a biomarker, a display, and a lighting device.

Figure 2:
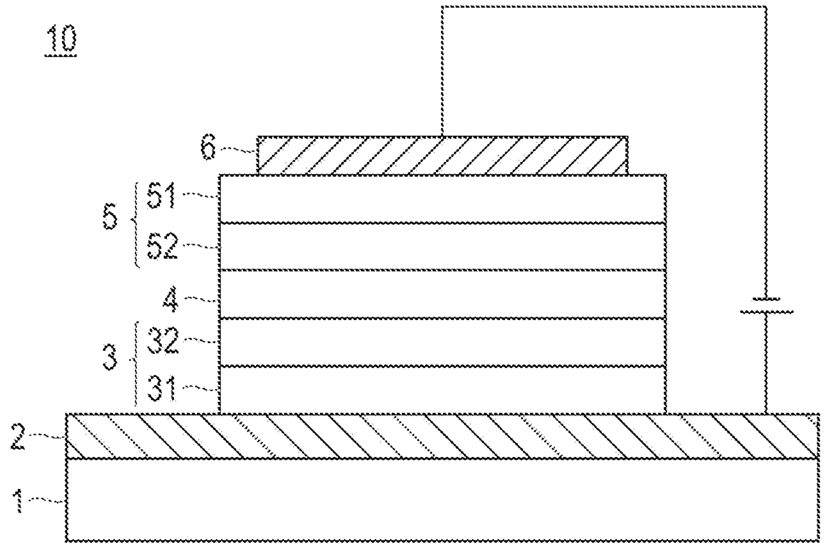
Figure 3:
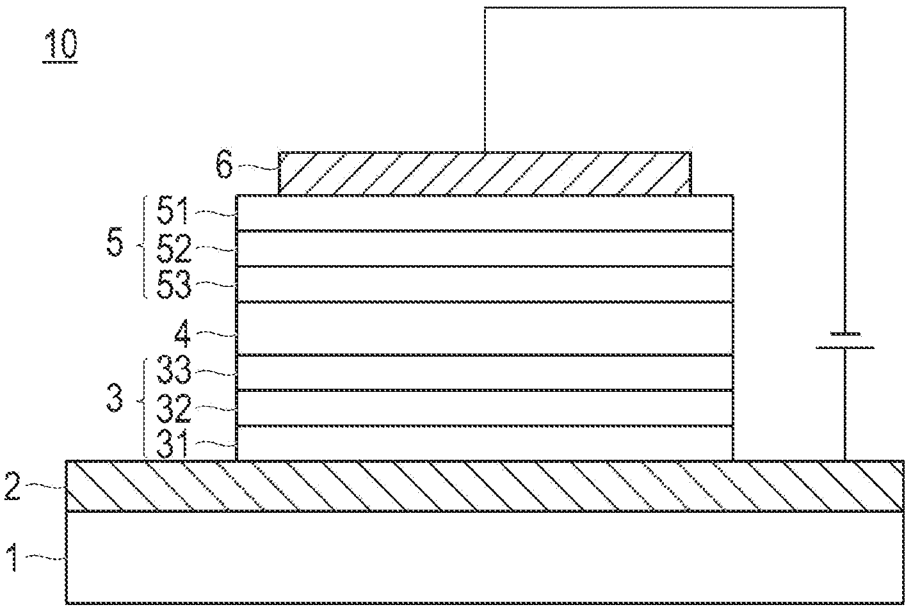
Figure 4:
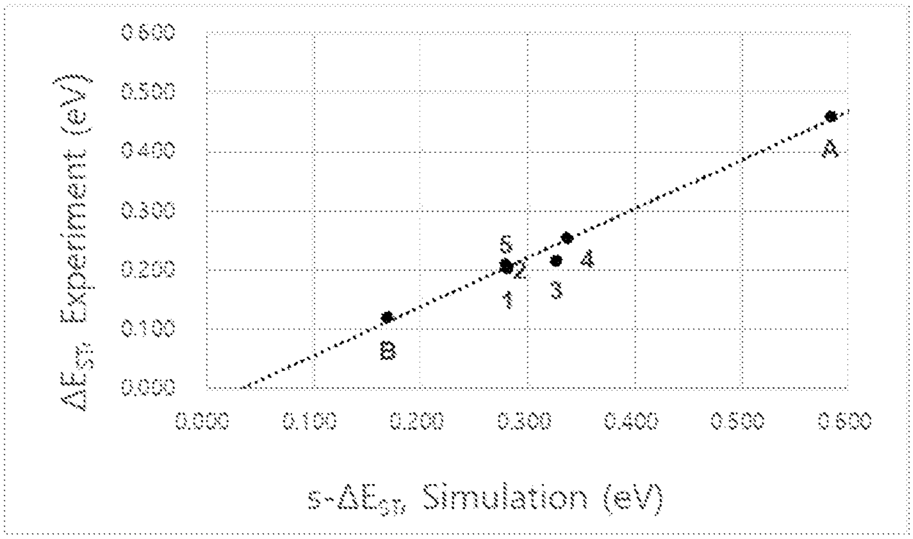
FIG. 4 is a graph showing the correlation of $\Delta E_{ST}$ simulation data (s-$\Delta E_{ST}$) and $\Delta E_{ST}$.

Descriptions of FIGS. 2 and 3

FIG. 2 is a schematic cross-sectional view of the organic light-emitting device 10 according to another exemplary embodiment of the present disclosure. In the organic light emitting device 10, the substrate 1, the first electrode 2, the hole transport region 3, the emission layer 4, the electron transport region 5, and the second electrode 6 are sequentially stacked, and the hole transport region 3 has a structure in which a hole injection layer 31 and a hole transport layer 32 are sequentially stacked. In addition, the electron transport region 5 has a structure in which an electron transport layer 52 and an electron injection layer 51 are sequentially stacked.

FIG. 3 is a schematic cross-sectional view of the organic light-emitting device 10 according to another exemplary embodiment of the present disclosure. In the organic light emitting device 10, the substrate 1, the first electrode 2, the hole transport region 3, the emission layer 4, the electron transport region 5, and the second electrode 6 are sequentially stacked, and the hole transport region 3 has a structure in which a hole injection layer 31 and a hole transport layer 32 are sequentially stacked. In addition, the electron transport region 5 has a structure in which a hole blocking layer 53, an electron transport layer 52 and an electron injection layer 51 are sequentially stacked.

Definitions of Terms

The term "$C_1$-$C_{60}$ alkyl group" as used herein refers to a linear or branched saturated aliphatic hydrocarbon monovalent group having 1 to 60 carbon atoms, and examples thereof are a methyl group, an ethyl group, a propyl group, an isobutyl group, a sec-butyl group, a tert-butyl group, a pentyl group, an isoamyl group, a hexyl group, and the like. The term "$C_1$-$C_{60}$ alkylene group" as used herein refers to a divalent group having the same structure as the $C_1$-$C_{60}$ alkyl group.

The term "$C_1$-$C_{60}$ alkoxy group" used herein refers to a monovalent group represented by —$OA_{101}$ (wherein $A_{101}$ is the $C_1$-$C_{60}$ alkyl group), and examples thereof are a methoxy group, an ethoxy group, an isopropyloxy group, and the like.

The term "$C_2$-$C_{60}$ alkenyl group" as used herein refers to a hydrocarbon group formed by substituting at least one carbon-carbon double bond in the middle or at the terminus of the $C_2$-$C_{60}$ alkyl group, and examples thereof are an ethenyl group, a propenyl group, a butenyl group, and the like. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by substituting at least one carbon-carbon triple bond in the middle or at the terminus of the $C_2$-$C_{60}$ alkyl group, and examples thereof are an ethynyl group, a propynyl group, and the like. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and examples thereof are a cyclopropyl group, a cyclobutyl group, a cyclopentyl group, a cyclohexyl group, a cycloheptyl group, and the like. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom of N, O, P, Si, B, Se, Ge, Te, S, or a combination thereof as a ring-forming atom and 1 to 10 carbon atoms, and examples thereof are a tetrahydrofuranyl group, a tetrahydrothiophenyl group, and the like. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and examples thereof are a cyclopentenyl group, a cyclohexenyl group, a cycloheptenyl group, and the like. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom N, O, P, Si, B, Se, Ge, Te, S, or a combination thereof as a ring-forming atom, 1 to 10 carbon atoms, and at least one carbon-carbon double bond in its ring. Examples of the $C_1$-$C_{10}$ heterocycloalkenyl group are a 2,3-dihydrofuranyl group, a 2,3-dihydrothiophenyl group, and the like. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, a chrysenyl group, and the like. When the $C_6$-$C_{60}$ aryl group and the $C_6$-$C_{60}$ arylene group each include two or more rings, the two or more rings may be fused to each other.

The term "$C_1$-$C_{60}$ heteroaryl group" as used herein refers to a monovalent group having a carbocyclic aromatic system that has at least one heteroatom of N, O, P, Si, B, Se, Ge, Te, S, or a combination thereof as a ring-forming atom, and 1 to 60 carbon atoms. The term "$C_1$-$C_{60}$ heteroarylene group" as used herein refers to a divalent group having a carbocyclic aromatic system that has at least one heteroatom of N, O, P, B, Se, Ge, Te, S, or a combination thereof as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, an isoquinolinyl group, and the like. When the $C_6$-$C_{60}$ heteroaryl group and the $C_6$-$C_{60}$ heteroarylene group each include two or more rings, the two or more rings may be fused to each other.

The term "$C_6$-$C_{60}$ aryloxy group" as used herein refers to —$OA_{102}$ (where $A_{102}$ is the $C_6$-$C_{60}$ aryl group), the term "$C_6$-$C_{60}$ arylthio group" as used herein refers to —$SA_{103}$ (where $A_{103}$ is the $C_6$-$C_{60}$ aryl group), and the term "$C_6$-$C_{60}$ arylalkyl group" as used herein refers to —$(CR_2)_nA_{104}$ (where $A_{104}$ is the $C_6$-$C_{60}$ aryl group, R is H or a $C_1$-$C_{10}$ alkyl group, and n is an integer from 1 to 10).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group are a fluorenyl group and the like. The term "divalent non-aromatic condensed polycyclic group" as used herein refers to a divalent group having the same structure as the monovalent non-aromatic condensed polycyclic group described above.

The term "monovalent non-aromatic condensed heteropolycyclic group" as used herein refers to a monovalent group (for example, having 2 to 60 carbon atoms) having two or more rings condensed with each other, a heteroatom N, O, P, Si, and S, other than carbon atoms, as a ring-forming atom, and no aromaticity in its entire molecular structure. Examples of the monovalent non-aromatic condensed heteropolycyclic group are a carbazolyl group and the like. The term "divalent non-aromatic condensed heteropolycyclic group" as used herein refers to a divalent group having the same structure as the monovalent non-aromatic condensed heteropolycyclic group described above.

The term "$C_5$-$C_{30}$ carbocyclic group" as used herein refers to a saturated or unsaturated cyclic group having, as a ring-forming atom, 5 to 30 carbon atoms only. The $C_5$-$C_{30}$ carbocyclic group may be a monocyclic group or a polycyclic group. When the $C_5$-$C_{30}$ carbocyclic group is an unsaturated cyclic group, the unsaturated cyclic group can be aromatic or non-aromatic.

The term "$C_1$-$C_{30}$ heterocyclic group" as used herein refers to a saturated or unsaturated cyclic group having, as a ring-forming atom, at least one of heteroatom N, O, Si, P, B, Se, Ge, Te, S, or a combination thereof other than 1 to 30 carbon atoms. The $C_1$-$C_{30}$ heterocyclic group may be a monocyclic group or a polycyclic group. When the $C_1$-$C_{30}$ heterocyclic group is an unsaturated cyclic group, the unsaturated cyclic group can be aromatic or non-aromatic.

In an embodiment, the π electron-deficient nitrogen-containing $C_1$-$C_{60}$ cyclic group may be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, a benzoisoxazole group, a triazole group, a tetrazole group, an oxadiazole group, a triazine group, a thiadiazole group, an imidazopyridine group, an imidazopyrimidine group, an azacarbazole group, an azadibenzofuran group, an azadibenzothiophene group, an azadibenzosilole group, an acridine group, or a pyridopyrazine group.

For example, the π electron-rich $C_3$-$C_{60}$ cyclic group may be a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a pyrrolophenanthrene group, a furanophenanthrene group, a thienophenanthrene group, a benzonaphthofuran group, a benzonaphthothiophene group, an (indolo)phenanthrene group, a (benzofuran)phenanthrene group, or a (benzothieno)phenanthrene group.

For example, the $C_5$-$C_{60}$ cyclic group may be a cyclopentane group, a cyclohexane group, a cyclohexene group, a benzene group, a naphthalene group, an anthracene group, a phenanthrene group, a triphenylene group, a pyrene group, a chrysene group, a 1,2,3,4-tetrahydronaphthalene group, a cyclopentadiene group, an indene group, a fluorene group, a 5,6,7,8-tetrahydroisoquinoline group, a 5,6,7,8-tetrahydroquinoline group, an adamantane group, a norbornane group, or a norbornene group.

For example, the $C_1$-$C_{60}$ heterocyclic group may be a thiophene group, a furan group, a pyrrole group, a cyclopentadiene group, a silole group, a borole group, phosphole group, a selenophene group, a germole group, a benzothiophene group, a benzofuran group, an indole group, an indene group, a benzosilole group, a benzoborole group, a benzophosphole group, a benzoselenophene group, a benzogermole group, a dibenzothiophene group, a dibenzofuran group, a carbazole group, a dibenzosilole group, a dibenzoborole group, a dibenzophosphole group, a dibenzoselenophene group, a dibenzogermole group, a dibenzothiophene 5-oxide group, a 9H-fluoren-9-one group, a dibenzothiophene 5,5-dioxide group, an azabenzothiophene group, an azabenzofuran group, an azaindole group, an azaindene group, an azabenzosilole group, an azabenzoborole group, an azabenzophosphole group, an azabenzoselenophene group, an azabenzogermole group, an azadibenzothiophene group, an azadibenzofuran group, an azacarbazole group, an azafluorene group, an azadibenzosilole group, an azadibenzoborole group, an azadibenzophosphole group, an azadibenzoselenophene group, an azadibenzogermole group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, or a benzothiadiazole group.

The term "a π electron-deficient nitrogen-containing $C_1$-$C_{60}$ cyclic group, a π electron-rich $C_3$-$C_{60}$ cyclic group, a $C_5$-$C_{60}$ cyclic group, and a $C_1$-$C_{60}$ heterocyclic group" may be part of a condensed cycle or may be a monovalent, a divalent, a trivalent, a tetravalent, a pentavalent, or a hexavalent group, depending on the formula structure.

At least one substituent of the substituted π electron-deficient nitrogen-containing $C_1$-$C_{60}$ cyclic group, the substituted π electron-rich $C_3$-$C_{60}$ cyclic group, the substituted $C_5$-$C_{30}$ carbocyclic group, the substituted $C_2$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_6$-$C_{60}$ aryl alkyl group, the substituted $C_1$-$C_{60}$ heteroaryl group, the substituted monovalent non-aromatic condensed polycyclic group, and the substituted monovalent non-aromatic condensed heteropolycyclic group may be:

deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group, a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_6$-$C_{60}$ aryl alkyl group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, —$P(=O)(Q_{18})(Q_{19})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_6$-$C_{60}$ aryl alkyl group, a $C_1$-$C_{60}$ heteroaryl group, a monovalent non-aromatic condensed polycyclic group, or a monovalent non-aromatic condensed heteropolycyclic group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_6$-$C_{60}$ aryl alkyl group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, —$P(=O)(Q_{28})(Q_{29})$, or any combination thereof; or —$N(Q_{31})(Q_{32})$, —$Si(Q_{33})(Q_{34})(Q_{35})$, —$B(Q_{36})(Q_{37})$, or —$P(=O)(Q_{38})(Q_{39})$, and $Q_1$ to $Q_9$, $Q_{11}$ to $Q_{19}$, $Q_{21}$ to $Q_{29}$, and $Q_{31}$ to $Q_{39}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_6$-$C_{60}$ aryl alkyl group, a $C_1$-$C_{60}$ heteroaryl group, a monovalent non-aromatic condensed polycyclic group, or a monovalent non-aromatic condensed heteropolycyclic group.

For example, $Q_1$ to $Q_9$, $Q_{11}$ to $Q_{19}$, $Q_{21}$ to $Q_{29}$, and $Q_{31}$ to $Q_{39}$ as used herein may each independently be:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$; or an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, a $C_1$-$C_{10}$ alkyl group, a phenyl group, or any combination thereof.

As used herein, the number of carbons in each group that is substituted (e.g., $C_1$-$C_{60}$) excludes the number of carbons in the substituent. For example, a $C_1$-$C_{60}$ alkyl group can be substituted with a $C_1$-$C_{60}$ alkyl group. The total number of carbons included in the $C_1$-$C_{60}$ alkyl group substituted with the $C_1$-$C_{60}$ alkyl group is not limited to 60 carbons. In addition, more than one $C_1$-$C_{60}$ alkyl substituent may be present on the $C_1$-$C_{60}$ alkyl group. This definition is not limited to the $C_1$-$C_{60}$ alkyl group and applies to all substituted groups that recite a carbon range.

The term "room temperature" as used herein refers to a temperature of about 25° C.

The terms "a biphenyl group, a terphenyl group, and a tetraphenyl group" as used herein respectively refer to monovalent a group in which two, three, or four phenyl a group which are linked together via a single bond.

The terms "a cyano-containing phenyl group, a cyano-containing biphenyl group, a cyano-containing terphenyl group, and a cyano-containing tetraphenyl group" as used herein respectively refer to a phenyl group, a biphenyl group, a terphenyl group, and a tetraphenyl group, each of which is substituted with at least one cyano group. In "a cyano-containing phenyl group, a cyano-containing biphenyl group, a cyano-containing terphenyl group, and a cyano-containing tetraphenyl group", a cyano group may be substituted to any position of the corresponding group, and "the cyano-containing phenyl group, the cyano-containing biphenyl group, the cyano-containing terphenyl group, and the cyano-containing tetraphenyl group" may further include substituents other than a cyano group. For example, a phenyl group substituted with a cyano group and a phenyl group substituted with a cyano group and a methyl group may all belong to "a cyano-containing phenyl group".

The term "$R_{10a}$" as used herein may be:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, a $C_2$-$C_{60}$ heteroarylalkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$.

In the present specification, $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group, a $C_1$-$C_{60}$ heterocyclic group, a $C_7$-$C_{60}$ aryl alkyl group, or a $C_2$-$C_{60}$ heteroaryl alkyl group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

In the present specification, * and *', unless defined otherwise, each refer to a binding site to a neighboring atom in a corresponding formula or moiety.

Hereinafter, a compound and an organic light-emitting device according to embodiments are described in detail with reference to Synthesis Examples and Examples. However, the organic light-emitting device is not limited thereto. The wording "'B' was used instead of 'A'" as used in describing Synthesis Examples means that an amount of 'A' used was identical to an amount of 'B' used, in terms of a molar equivalent.

EXAMPLES

Synthesis Example 1: Synthesis of Compound 1

1) Synthesis of Intermediate 1-1

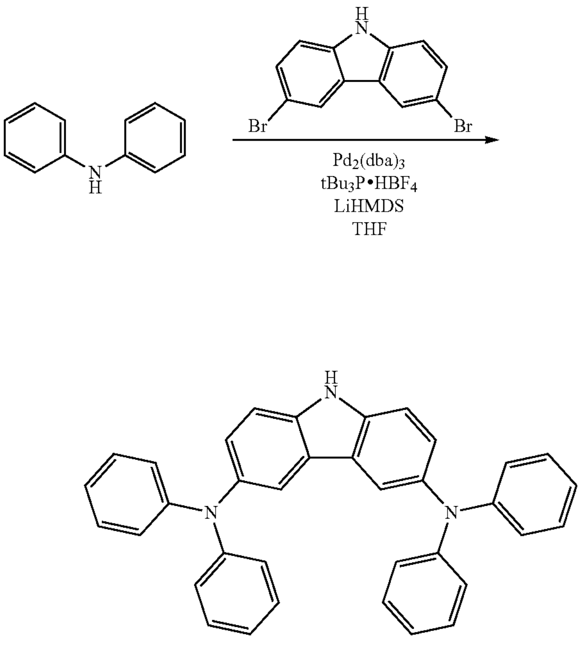

1-1

In a three-neck flask under argon atmosphere, 3,6-dibromocarbazole (1 eq. 61.5 mmol, 20 g), diphenylamine (2.2 eq. 135.4 mmol, 22.9 g), tris(dibenzylideneacetone)dipalladium (1.23 mmol, 1.1 g), tri-tert-butylphosphonium-tetrafluoroborate (6.15 mmol, 1.79 g), and THF (125 ml) were added and stirred. Then, lithium bis(trimethylsilyl)amide (1 M tetrahydrofuran solution, 203 mmol, 203 ml) was added to the resultant mixture and stirred at 65° C. for 6 hours. The temperature of the reaction solution was lowered to room temperature, and $H_2O$ (about 500 ml) was added thereto and stirred. The resultant reaction solution was filtered, and the solid thus obtained was purified by silica gel column chromatography, so as to obtain Intermediate 1-1.

2) Synthesis of Intermediate 1-2

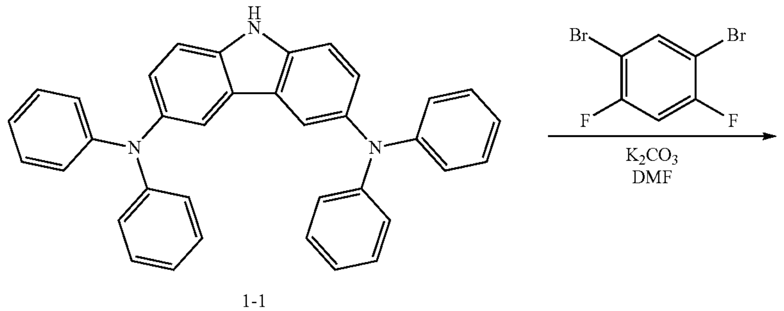

1-1

-continued

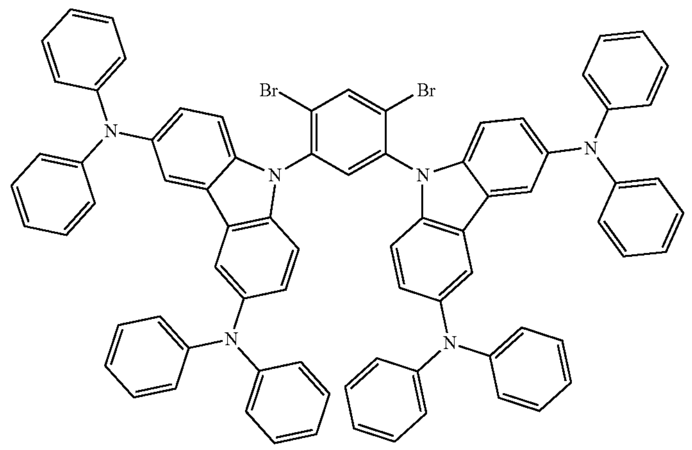

1-2

In a three-neck flask under argon atmosphere, Intermediate 1-1 (2.05 eq. 19.83 mmol, 9.95 g), 1, 5-dibromo-2, 4-difluorobenzene (1 eq. 9.67 mmol, 2.63 g), $K_2CO_3$ (2.4 eq. 23.22 mmol, 3.21 g), and N—N-dimethylformamide (50 ml) were added and stirred at 120° C. for 8 hours. After completion of the reaction, the reaction solution was cooled to room temperature, and $H_2O$ (100 ml) and methanol (MeOH) (100 ml) were added thereto and stirred. The solid obtained by filtering the resultant reaction solution was purified by silica gel column chromatography and then subjected to recrystallization using toluene and hexane, so as to obtain Intermediate 1-2.

3) Synthesis of Compound 1

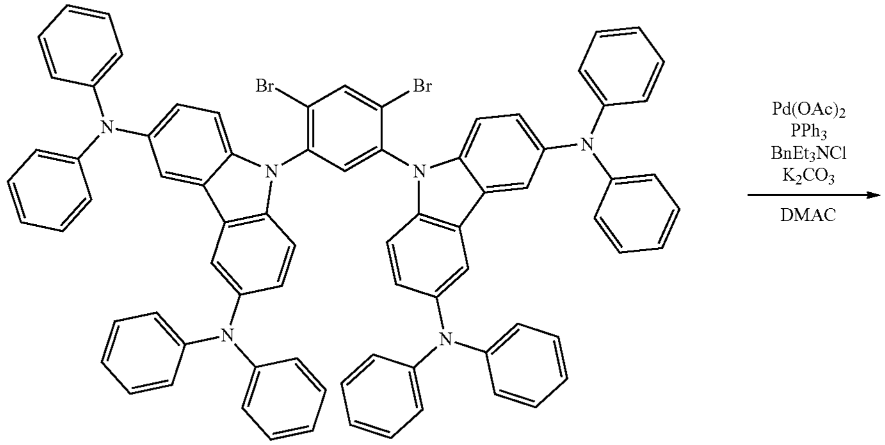

1-2

-continued

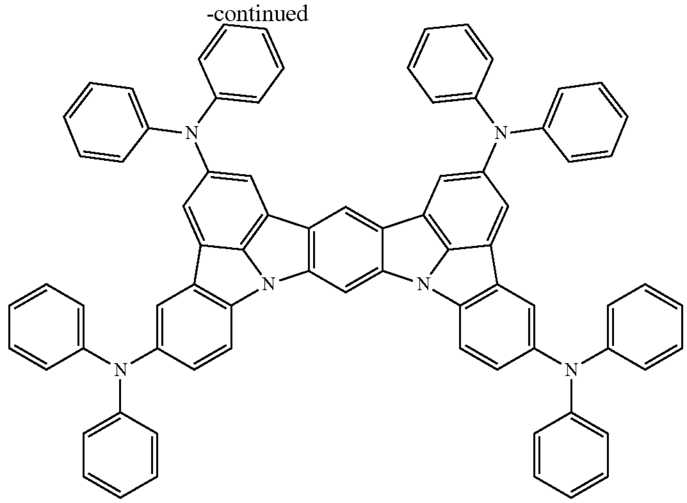

1

In a three-neck flask under argon atmosphere, Intermediate 1-2 (1 eq. 6.23 mmol, 7.69 g), palladium acetate (30 mol %, 1.87 mmol, 0.42 g), triphenylphosphine (0.7 eq. 4.36 mmol, 1.14 g), $K_2CO_3$ (10 eq. 62.3 mmol, 8.604 g), benzyltriethylammonium chloride (2 eq. 12.45 mmol, 2.836 g), and N, N-dimethylacetamide (500 ml) were added and stirred at 160° C. for 8 hours. After completion of the reaction, the reaction solution was cooled to room temperature, and $H_2O$ (200 ml) and methanol (MeOH) (200 ml) were added thereto and stirred. The solid obtained by filtering the resultant reaction solution was purified by silica gel column chromatography and then subjected to recrystallization using toluene and hexane, so as to obtain Compound 1.

Compound 1 was dissolved in tetrahydrofuran at a concentration of 0.1 wt %, and mass spectrometry was performed thereon by using a LC-MS measurement apparatus 1260 Infinity-4 Quadrupole 6100MS (manufactured by Agilent technologies, Inc.). Results thereof were as follows.

LC-MS: 1074 ($[M+H]^+$).

Synthesis Example 2: Synthesis of Compound 2

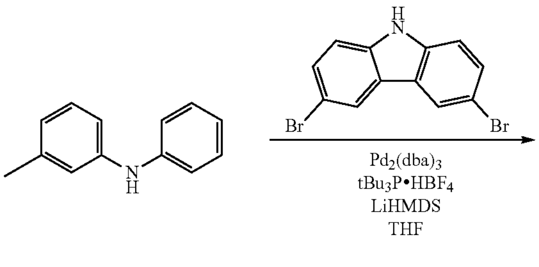

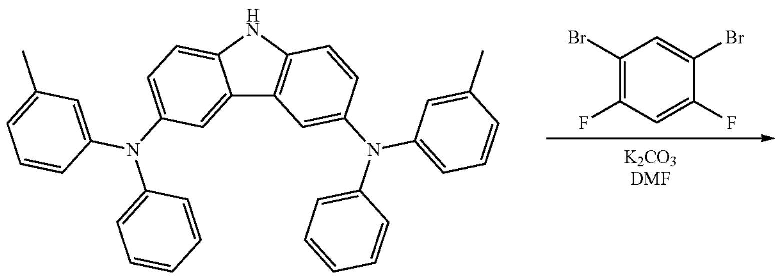

-continued
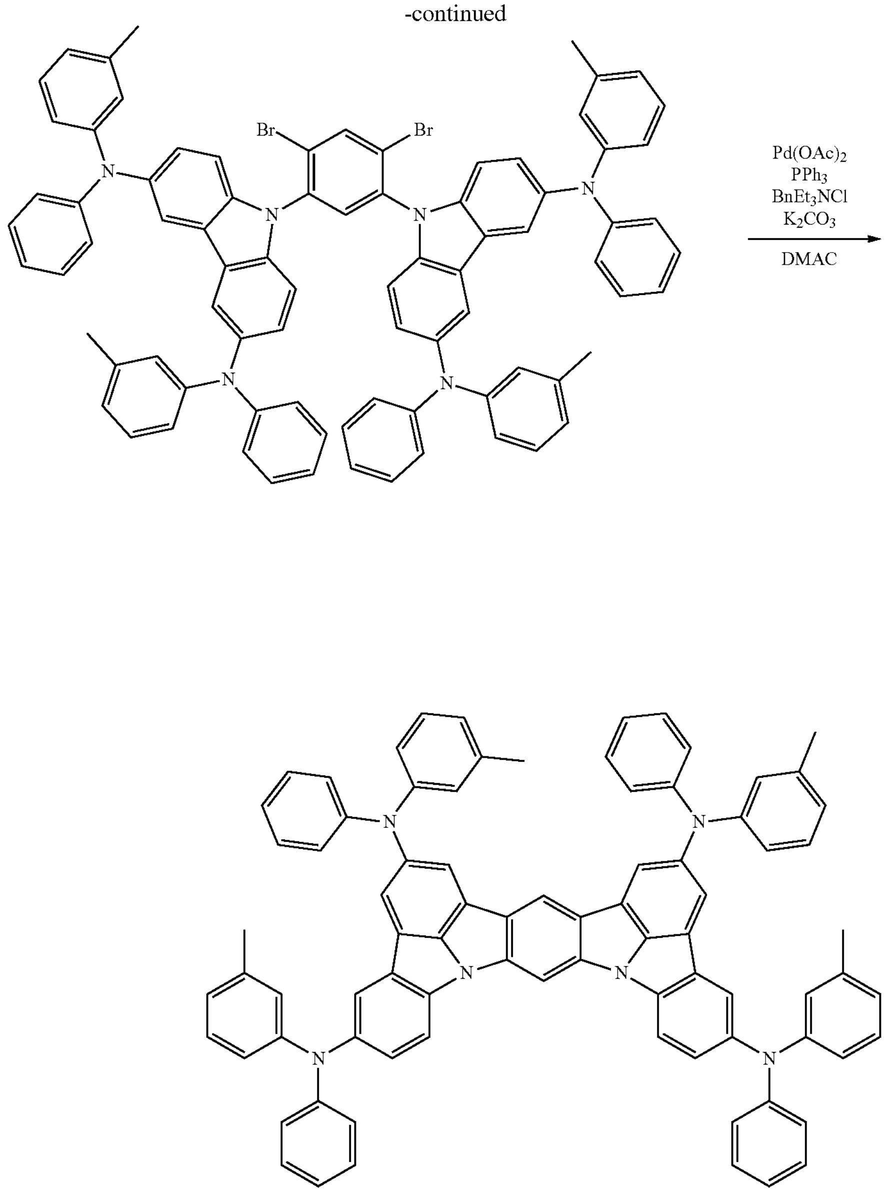
2
Compound 2 was obtained in the same manner as in Synthesis Example 1, except that 3-methyl-N-phenylaniline was used instead of diphenylamine in the synthesis of Intermediate 1-1.
Results of mass spectrometry performed on the obtained compound were as follows: LC-MS: 1130 ([M+H]$^+$).
Synthesis Example 3: Synthesis of Compound 3
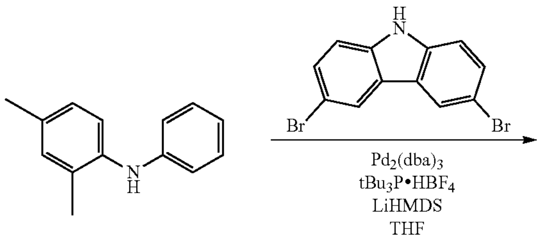

-continued
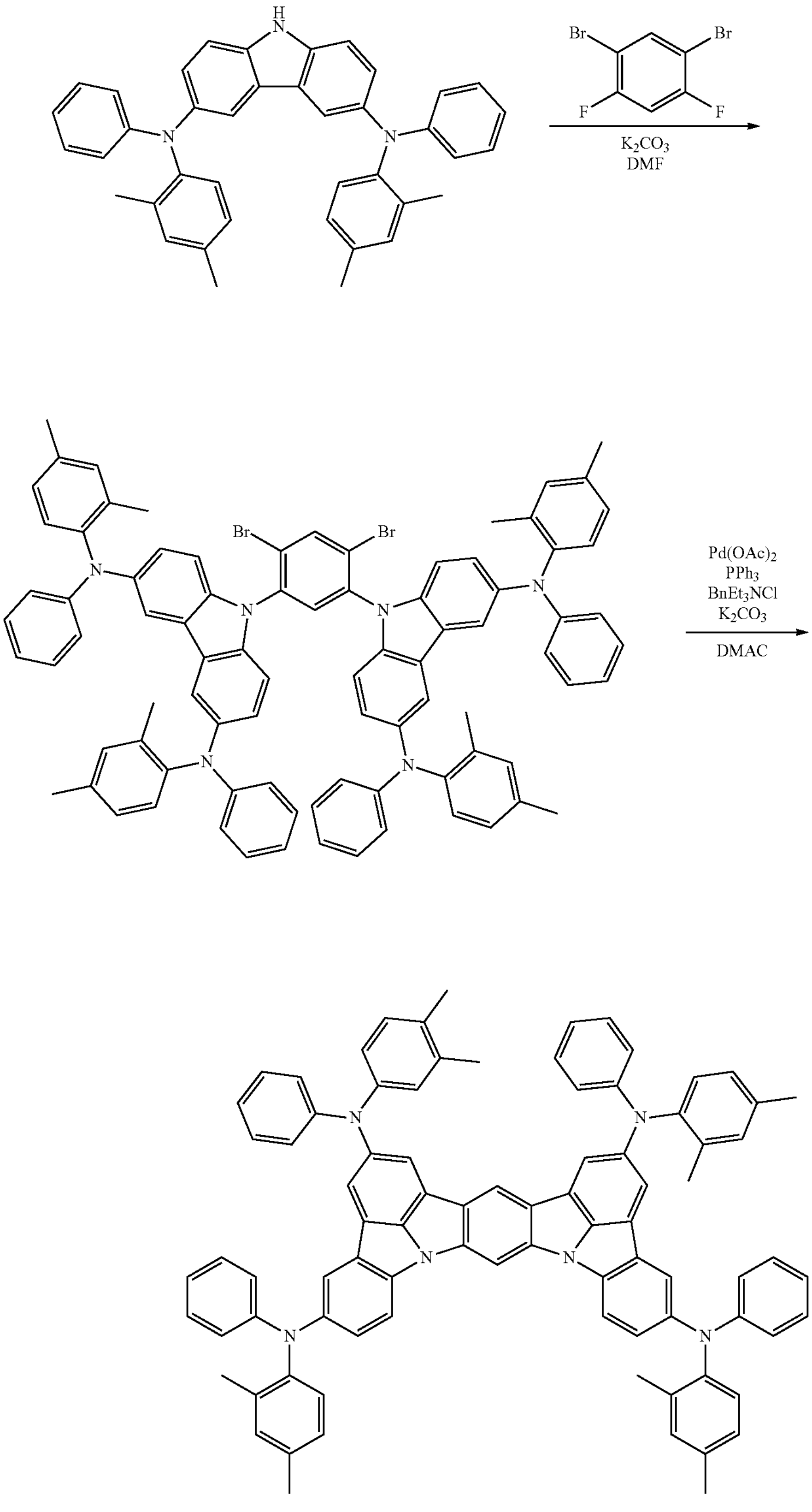

Compound 3 was obtained in the same manner as in Synthesis Example 1, except that 2,4-dimethyl-N-phenylaniline was used instead of diphenylamine in the synthesis of Intermediate 1-1.

Results of mass spectrometry performed on the obtained compound were as follows: LC-MS: 1186 ($[M+H]^+$).

Synthesis Example 4: Synthesis of Compound 4

1) Synthesis of Intermediate 4-1

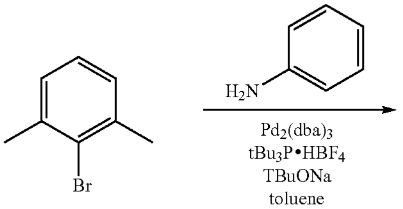

-continued

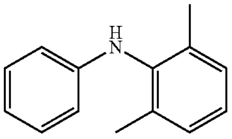

4-1

In a three-neck flask under argon atmosphere, aniline (1 eq. 53.69 mmol, 5.0 g), 2-bromo-m-xylene (1 eq. 53.69 mmol, 9.94 g), tris(dibenzylideneacetone)dipalladium (0.54 mmol, 0.49 g), tri-tert-butyl phosphonium-tetrafluoroborate (2.15 mmol, 0.62 g), sodium tert-butoxide (tert-BuONa) (1.5 eq. 80.53 mmol, 7.74 g), and toluene (270 ml) were added and stirred at 120° C. for 8 hours. After completion of the reaction, the reaction solution was cooled to room temperature and filtered using Celite. The filtrate was concentrated and purified by silica gel column chromatography, so as to obtain Intermediate 4-1.

2) Synthesis of Compound 4

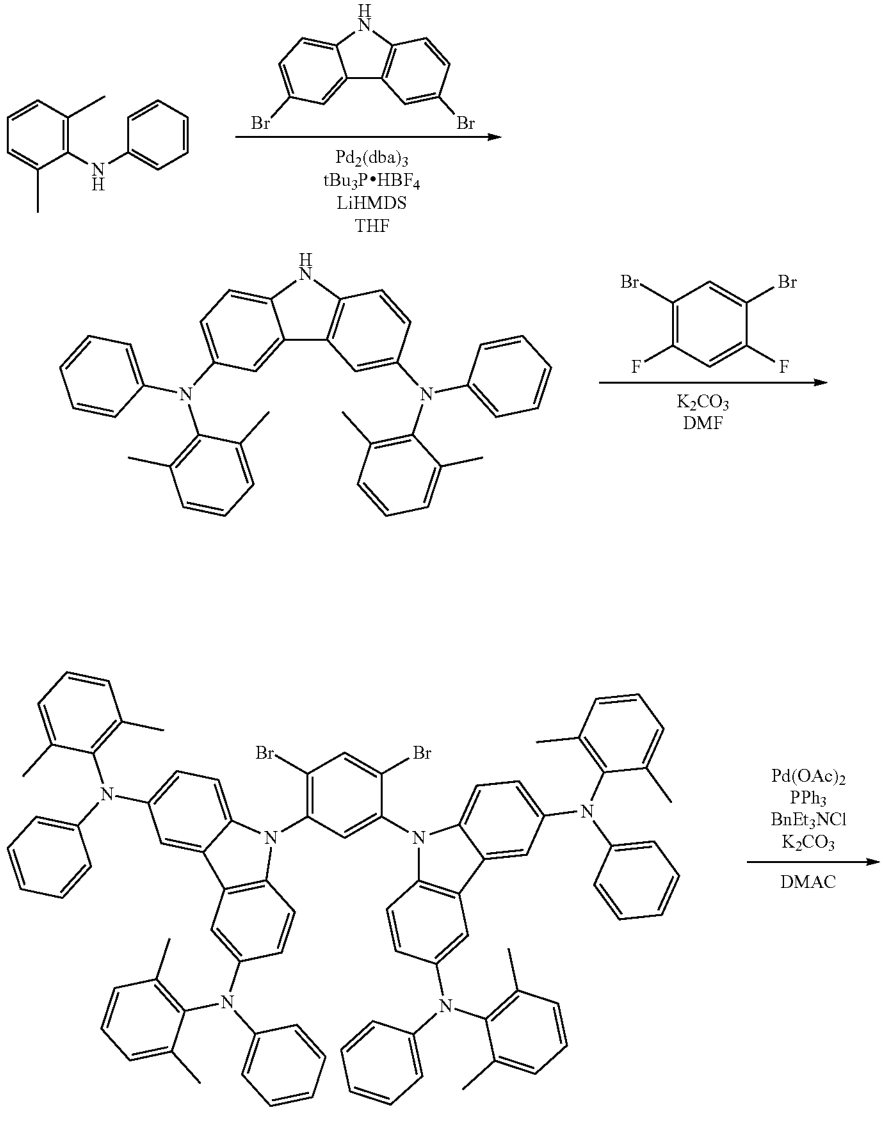

-continued

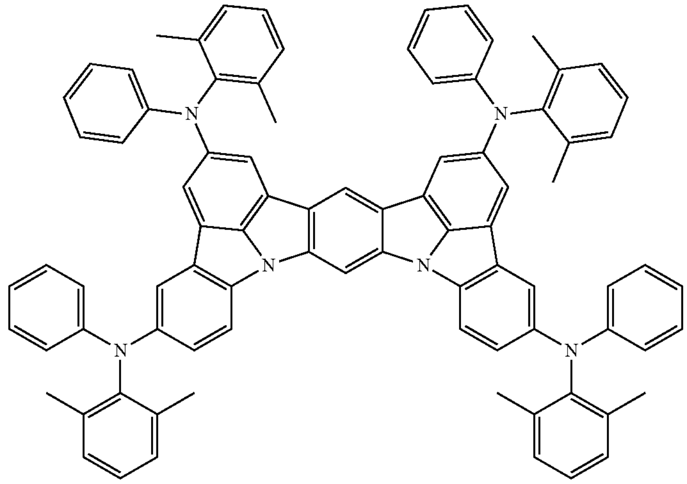

4

Compound 4 was obtained in the same manner as in Synthesis Example 1, except that Intermediate 4-1 was used instead of diphenylamine in the synthesis of Intermediate 1-1.

Results of mass spectrometry performed on the obtained compound were as follows: LC-MS: 1186 ([M+H]$^+$).

Synthesis Example 5: Synthesis of Compound 5

1) Synthesis of Intermediate 5-1

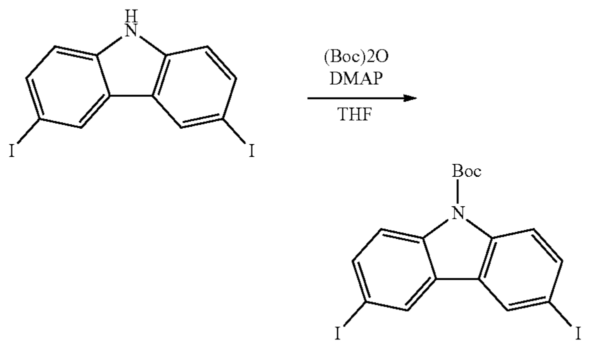

5-1

In a three-neck flask under argon atmosphere, 3,6-diiodinecarbazole (1 eq. 23.87 mmol, 10.0 g), di-tert-butylcarbonate (1.3 eq. 31.03 mmol, 6.77 g), 4-dimethylaminopyridine (4.77 mmol, 0.583 g), and THF (40 ml) were added and heated at 80° C. for 4 hours. After completion of the reaction, the reaction solution was cooled to room temperature and then concentrated. Afterwards, the concentrated reaction product was washed using methanol (MeOH), so as to obtain Intermediate 5-1.

2) Synthesis of Intermediate 5-2

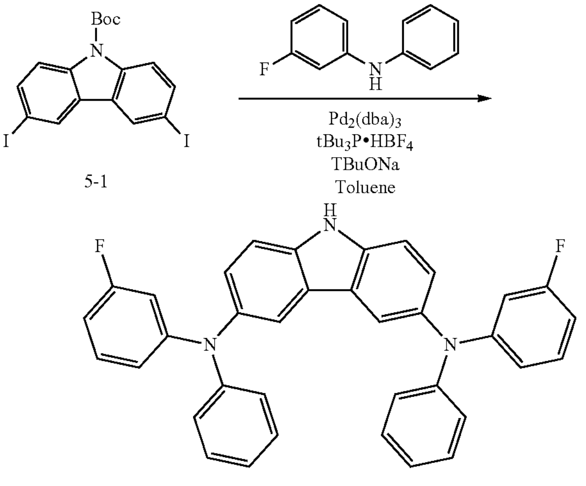

5-1

5-2

In a three-neck flask under argon atmosphere, Intermediate 5-1 (1 eq. 1.93 mmol, 1.0 g), 3-fluorodiphenylamine (2 eq. 3.85 mmol, 0.72 g), tris(dibenzylideneacetone)dipalladium (0.08 mmol, 0.071 g), tri-tert-butylphosphonium-tetrafluoroborate (0.15 mmol, 0.045 g), sodium-tert-butoxide (tert-BuONa) (3 eq. 5.78 mmol, 0.56 g), and toluene (3.9 ml) were added and stirred at 120° C. for 8 hours. After completion of the reaction, the reaction solution was cooled to room temperature and filtered using Celite. The filtrate was then concentrated, and THF (5 ml) and hydrochloric acid (20 ml) were added thereto and stirred at 60° C. for 8 hours. After completion of the reaction, the resulting reaction solution was neutralized with an aqueous $NaHCO_3$ solution, and an extraction process was performed thereon using toluene. Next, the organic layer thus obtained was dried with anhydrous magnesium sulfate, concentrated, and purified by silica gel column chromatography. The resultant product was then subjected to recrystallization using methanol (MeOH), so as to obtain Intermediate 5-2.

3) Synthesis of Compound 5

Compound 5 was obtained in the same manner as in Synthesis Example 1, except that Intermediate 5-2 was used instead of Intermediate 1-1 in the synthesis of Intermediate 1-2.

Results of mass spectrometry performed on the obtained compound were as follows: LC-MS: 1146 ($[M+H]^+$).

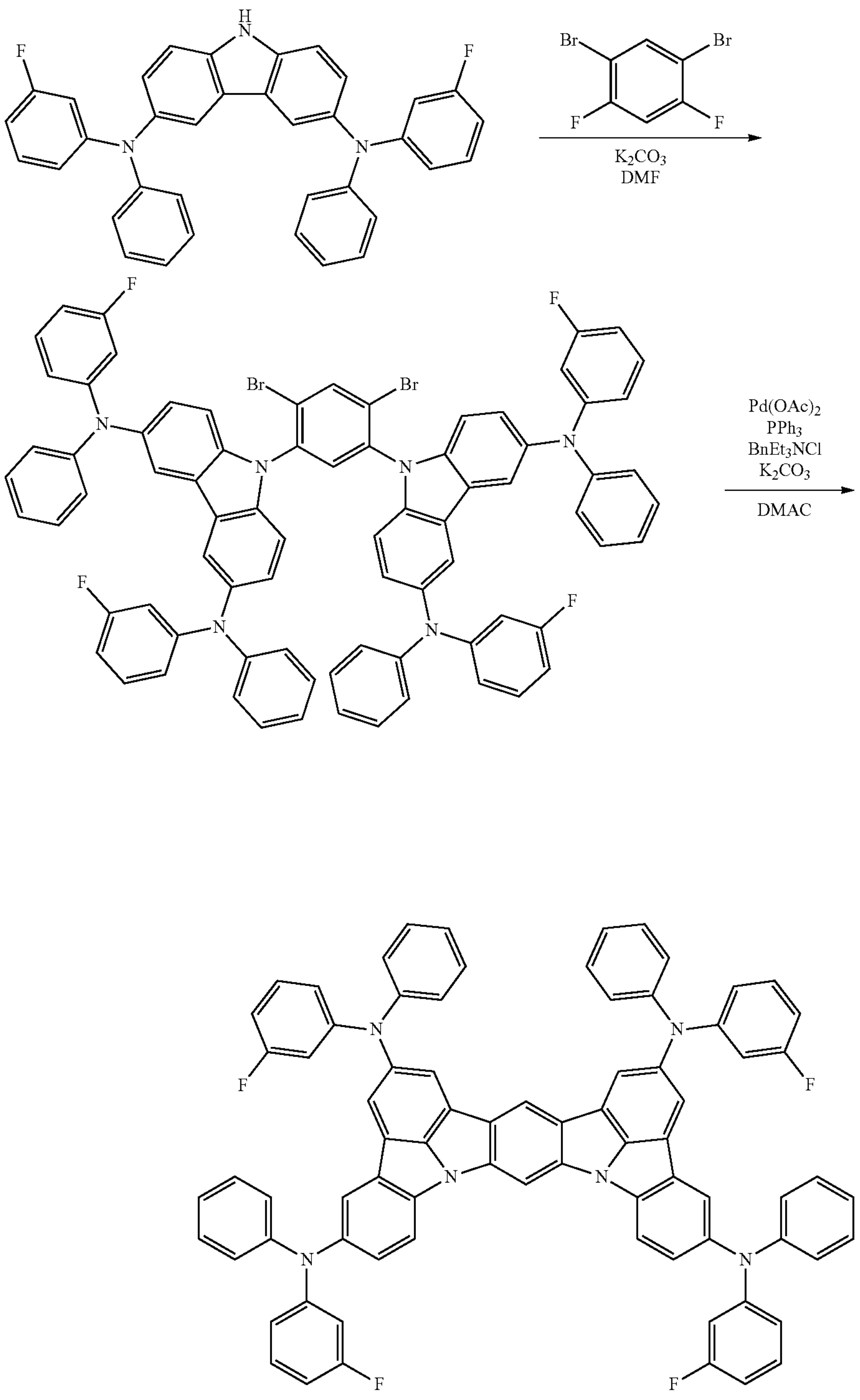

5

Regarding compounds other than the compounds synthesized according to Synthesis Examples 1 to 5, synthesis methods may be easily understood to those skilled in the art by referring to the synthesis pathways and raw materials described above.

Evaluation Example 1: Evaluation of $S_1$ Energy Level, $T_1$ Energy Level, and $\Delta E_{ST}$ Simulation Data For the compounds synthesized according to Synthesis Examples 1 to 5 and Compounds A to C as comparative compounds, $S_1$ energy level (s-$S_1$, eV), $T_1$ energy level (s-$T_1$, eV), and s-$\Delta E_{ST}$ were evaluated using the DFT method of the Gaussian program with the structure optimization at the B3LYP/6-31G(d,p) level, and results thereof are shown in Table 7.

TABLE 7

| Compound | s-$S_1$ (eV) | s-$T_1$ (eV) | s-$\Delta E_{ST}$ |
|---|---|---|---|
| 1 | 2.74 | 2.46 | 0.281 |
| 2 | 2.74 | 2.46 | 0.280 |
| 3 | 2.78 | 2.45 | 0.326 |
| 4 | 2.79 | 2.46 | 0.336 |
| 5 | 2.80 | 2.52 | 0.279 |
| A | 3.36 | 2.77 | 0.583 |
| B | 2.77 | 2.60 | 0.169 |
| C | 2.85 | 2.29 | 0.551 |

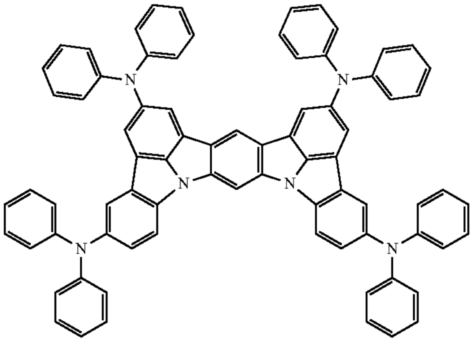

1

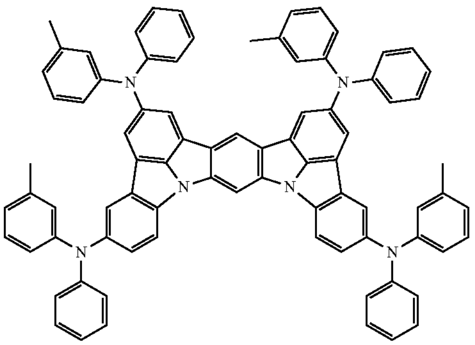

2

TABLE 7-continued

| Compound | s-$S_1$ (eV) | s-$T_1$ (eV) | s-$\Delta E_{ST}$ |
|---|---|---|---|

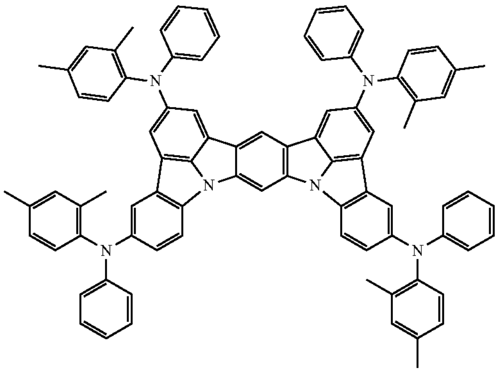

3

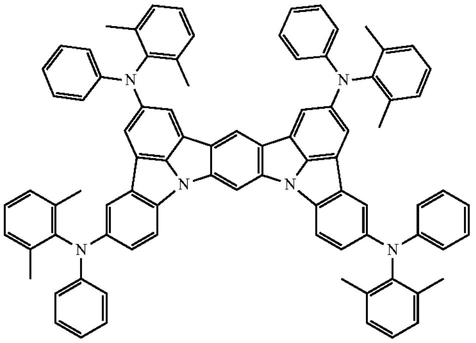

4

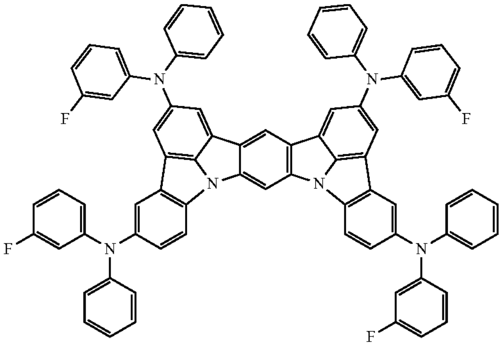

5

TABLE 7-continued

| Compound | s-$S_1$ (eV) | s-$T_1$ (eV) | s-$\Delta E_{ST}$ |
|---|---|---|---|
| 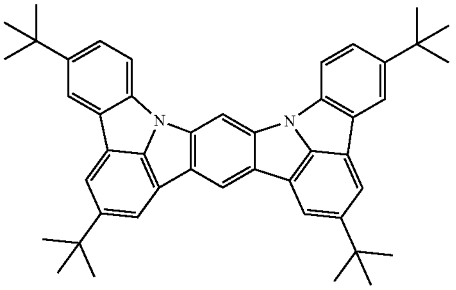 A | | | |
| 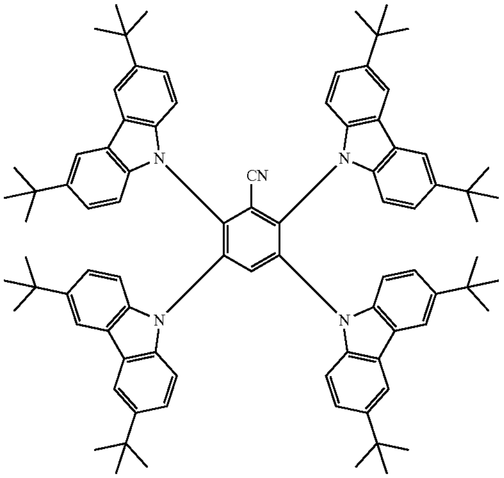 B | | | |
| 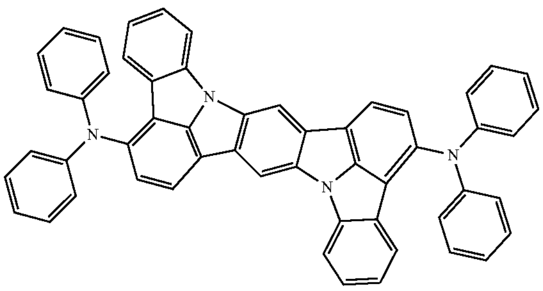 C | | | |

Evaluation Example 2: Measurement of HOMO and LUMO Energy Levels

To measure HOMO and LUMO energy levels of the compounds synthesized according to Synthesis Examples 1 to 5 and Compounds A to C as comparative compounds, the compounds were respectively prepared as solids.

(1) Preparation of Test Sample for Measurement

1) A sample solution containing each compound in an amount of 4 parts by weight based on 100 parts by weight of methyl benzoate as a solvent was prepared.

2) The sample solution prepared in Section 1) was coated on each of an ITO substrate and a quartz substrate by a spin-coating method to form a coating film having a dry film thickness of 50 nm. The formed coating film was heated under vacuum of $10^{-1}$ Pa or lower at 120° C. for 1 hour. Then, under vacuum of $10^{-1}$ Pa or lower, the resulting coating film was cooled to room temperature to form a thin-film layer (also referred to as a thin-film sample).

(2) Measurement of HOMO Energy Level

A HOMO energy level of the thin-film sample was measured using a photoelectron spectrometer AC-3 (manufactured by Riken Keiki Co., Ltd.) in the atmosphere. Results of the measurement are shown in Table 8.

(3) Measurement of LUMO Energy Level

An energy gap value (Eg) at an absorption edge of an ultraviolet visible absorption spectrum of the thin-film sample was measured using a spectrophotometer U-3900 (manufactured by Hitachi High Tech Corp.), and then a LUMO energy level was calculated according to Equation 2. Results of the calculation were shown in Table 8.

$$LUMO=HOMO+Eg \qquad \text{Equation 2}$$

Evaluation Example 3: Measurement of Photoluminescence (PL)

To measure PL of the compounds synthesized according to Synthesis Examples 1 to 5 and Compounds A to C as comparative compounds, the compounds were respectively dissolved in toluene to prepare a $1\times10^{-5}$ M solution for each compound. A permeability cell with 4 sides having a length of 1 cm each was filled with the prepared solution, and PL of each cell was measured at room temperature using a spectrophotofluorometer F7000 (manufactured by Hitachi High Tech Corp.). From the measured PL spectrum, a peak wavelength and its full width at half maximum (FWHM) at which luminescence intensity was halved were calculated. Results of the calculation were shown in Table 8.

Evaluation Example 4: Measurement of $S_1$ Energy Level, $T_1$ Energy Level, and $\Delta E_{ST}$ To measure $S_1$ energy level, $T_1$ energy level, and $\Delta E_{ST}$ of the compounds synthesized according to Synthesis Examples 1 to 5 and Compounds A to C as comparative compounds, the compounds were respectively prepared as solids.

(1) Preparation of Test Sample for Measurement

1) Each of the compounds and polymethyl methacrylate (PMMA) were dissolved in toluene to mix PMMA and each compound at a weight ratio of 99.5:0.5 (PMMA solution:compound solution), so as to prepare a sample solution containing 5 wt % of toluene.

2) The sample solution prepared in Section (1) was spin-coated on an ITO substrate and a quartz substrate by using a spin coater MS-B100 (manufactured by Mikasa Corporation) to form a spin-coating film having a dry film thickness of 500 nm. Subsequently, the formed spin-coating film was heated at 120° C. for 1 hour to prepare a thin-film sample.

(2) Measurement of $S_1$ Energy Level, $T_1$ Energy Level, and $\Delta E_{ST}$

A fluorescence spectrum and a phosphorescence spectrum of the thin-film sample were measured at 77 K using a spectrophotofluorometer F7000 (manufactured by Hitachi High Tech Corp.). Then, a singlet ($S_1$) energy level was calculated from the measured fluorescence spectrum, and a triplet ($T_1$) energy level was calculated from the measured phosphorescence spectrum. In addition, $\Delta E_{ST}$ was calculated according to Equation 3, and results thereof were shown in Table 8.

$$\Delta E_{ST}=S_1-T_1 \qquad \text{Equation 3}$$

Evaluation Example 5: Measurement of Photoluminescence Quantum Yield (PLQY)

To measure PLQY of the compounds synthesized according to Synthesis Examples 1 to 5 and Compounds A and B as comparative compounds, each of the compounds shown in Table 8 and mCP as a host compound were co-deposited at a weight ratio of 1 wt % with respect to the host compound on a quartz substrate at a vacuum pressure of $10^{-5}$ Pa, so as to prepare a thin film having a thickness of 50 nm. Then, PLQY of the thin film for each compound was measured using a C11347-01 Quantaurus-QY absolute PLQY measurement meter (manufactured by Hamamatsu Photonics Co., Ltd.). For the measurement, an excitation wavelength was scanned and measured at intervals of 10 nm from 300 nm to 400 nm, and then an excitation wavelength region in which an absorption value of the compound was an excitation light intensity ratio of 10% or more was selected. Here, the highest value in the selected excitation wavelength region was set as the PLQY value. Results of the evaluation were shown in Table 8.

TABLE 8

| Compound | HOMO (eV) | LUMO (eV) | Peak wavelength (nm) | FWHM (nm) | $S_1$ (eV) | $T_1$ (eV) | $\Delta E_{ST}$ | PLQY |
|---|---|---|---|---|---|---|---|---|
| 1 | −5.7 | −3.0 | 461 | 23 | 2.83 | 2.63 | 0.204 | 71.2 |
| 2 | −5.7 | −3.0 | 459 | 23 | 2.84 | 2.63 | 0.205 | 80.1 |
| 3 | −5.6 | −3.0 | 460 | 20 | 2.80 | 2.58 | 0.216 | 76.9 |
| 4 | −5.6 | −2.9 | 459 | 17 | 2.78 | 2.53 | 0.255 | 55.9 |
| 5 | −5.9 | −3.2 | 452 | 23 | 2.89 | 2.68 | 0.210 | 62.1 |
| A | −6.0 | −2.6 | 393 | 20 | 3.17 | 2.71 | 0.46 | 60.0 |
| B | −6.1 | −3.3 | 467 | 55 | 2.84 | 2.71 | 0.12 | 60.8 |

Referring to Table 8, it was confirmed that the condensed cyclic compound of the present disclosure exhibited luminescence having a narrow spectrum width with a wavelength region of blue light as a peak wavelength, so that blue luminescence with high color purity was identified. It was also confirmed that the condensed cyclic compound of the present invention had small $\Delta E_{ST}$, so that luminescence with high efficiency was identified.

Example 1

A glass substrate on which an ITO stripe was formed to a thickness of 150 nm was formed.

Subsequently, poly(3,4-ethylene dioxythiophene)/poly(4-styrene sulfonate) (PEDOT/PSS) (manufactured by Sigma-Aldrich) was spin-coated on the ITO electrode (anode) of the glass substrate to form a hole injection layer having a thickness of 30 nm.

A solvent including HTP1 (weight average molecular weight Mw=400,000, PDI (Mw/Mn)=2.7) in an amount of 3 parts by weight based on 100 parts by weight of anisole was prepared first, and a solution including AD1 in an amount of 0.6 parts by weight based on 100 parts by weight of the solvent was prepared. Then, the prepared solution was spin-coated on the hole injection layer to form a coating film having a thickness of 125 nm. The formed coating film was heated under vacuum of $10^{-1}$ Pa or lower at 230° C. for 1 hour, and cooled to room temperature under vacuum of $10^{-1}$ Pa or lower to form a hole transport layer.

H-H104 was deposited on the hole transport layer to form an electron blocking layer having a thickness of 10 nm.

Compound 1, H-H104, and HE6-203 were co-deposited on the electron blocking layer at a ratio of 1.5 wt %:39.4 wt %:59.1 wt % to form an emission layer having a thickness of 40 nm.

HE6-203 was deposited on the emission layer to form a hole blocking layer having a thickness of 10 nm.

LiQ and KLET-03 (available from Chemi-Pro Co., Ltd.) were co-deposited on the hole blocking layer at a weight ratio of 2:8 to form an electron transport layer having a thickness of 20 nm.

Next, LiQ was deposited on the electron transport layer to form an electron injection layer having a thickness of 3.5 nm.

Aluminum (Al) was deposited on the electron injection layer to form a second electrode (cathode) having a thickness of 100 nm, and in a glove box under nitrogen atmosphere with a moisture concentration of 1 ppm or less and an oxygen concentration of 1 ppm or less, a glass sealing tube with a desiccant and an ultraviolet curable resin were used to seal the second electrode, thereby completing the manufacture of an organic light-emitting device.

HTP1
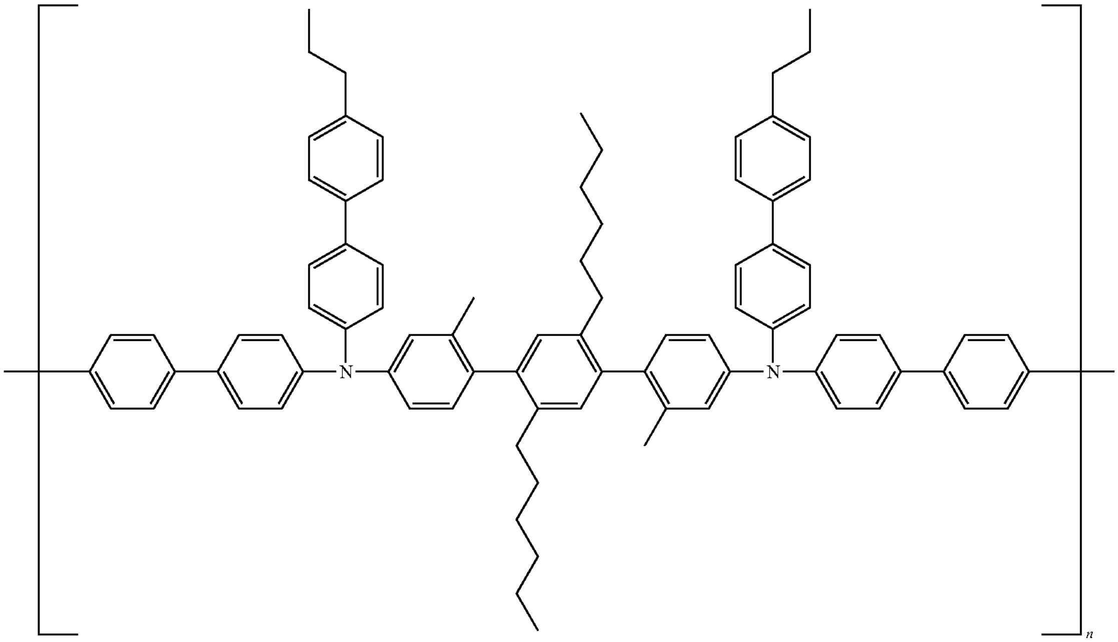
AD1
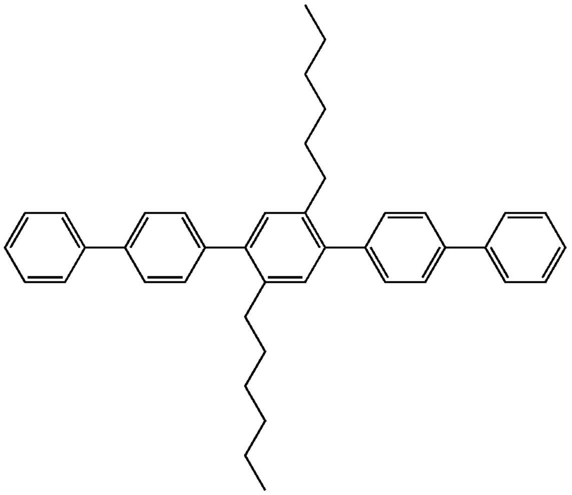
In HTP1, n is an integer from 1 or more.
H-H104
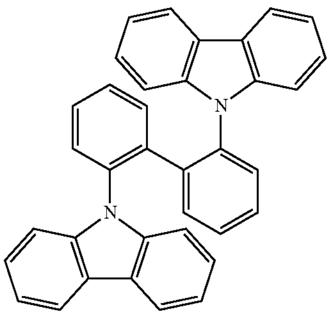
-continued
HE6-203
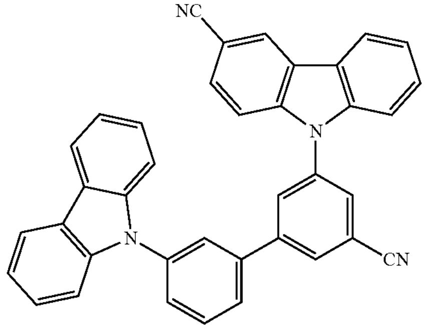

-continued

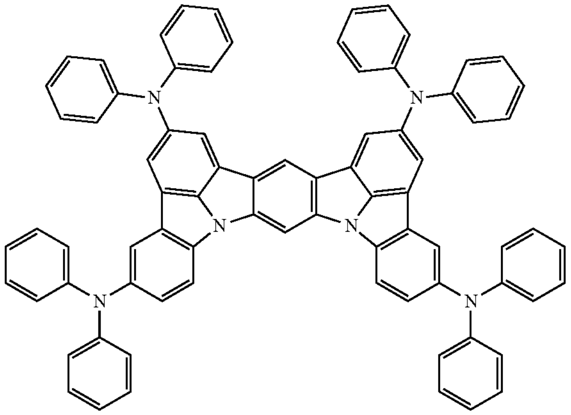

Example 2 and Comparative Example 1

Organic light-emitting devices were manufactured in the same manner as in Example 1, except that, in forming an emission layer, compounds shown in Table 9 were used respectively.

Evaluation of Example 6: Evaluation of Properties of Organic Light-Emitting Devices For each of the organic light-emitting devices manufactured according to Examples 1 and 2 and Comparative Example 1, CIEx, CIEy, emission peak wavelength, FWHM, and relative value (%) of a maximum external quantum efficiency (Max EQE) were evaluated, and results were shown in Table 9. As evaluation apparatuses, a current-voltmeter (Keithley 2400) and a luminance meter (Hamamatsu Photonics, PMA12) were used. From the measurement results, the current value and the EQE (%) were calculated. In addition, a wavelength having the maximum value in the EQE graph for the wavelength was defined as an emission peak wavelength (nm), and a wavelength width corresponding to the half of the emission peak wavelength was defined as FWHM (nm). Here, Max EQE refers to an EQE value at a current density of 0.1 (mA/m2) as calculated from the area of the organic light-emitting device during current driving.

TABLE 9

| | Emission layer | | | | Emission peak | | Max |
|---|---|---|---|---|---|---|---|
| | Host (weight ratio) | Dopant | CIEx | CIEy | wavelength (nm) | FWHM (nm) | EQE (%) |
| Example 1 | H-H104:HE6-203 = 4:6 | 1 | 0.130 | 0.184 | 468 | 38 | 15.09 |
| Example 2 | H-H104:HE6-203 = 4:6 | 2 | 0.126 | 0.173 | 469 | 36 | 8.96 |
| Comparative Example 1 | H-H104:HE6-203 = 4:6 | B | 0.145 | 0.212 | 466 | 70 | 9.45 |

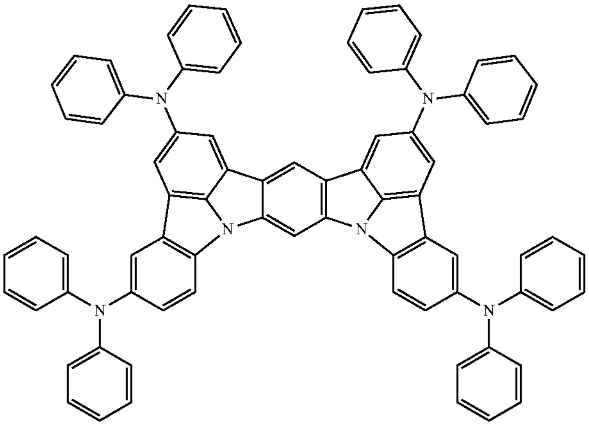

1

TABLE 9-continued

| Emission layer | | | | Emission peak | | Max |
|---|---|---|---|---|---|---|
| Host (weight ratio) | Dopant | CIEx | CIEy | wavelength (nm) | FWHM (nm) | EQE (%) |

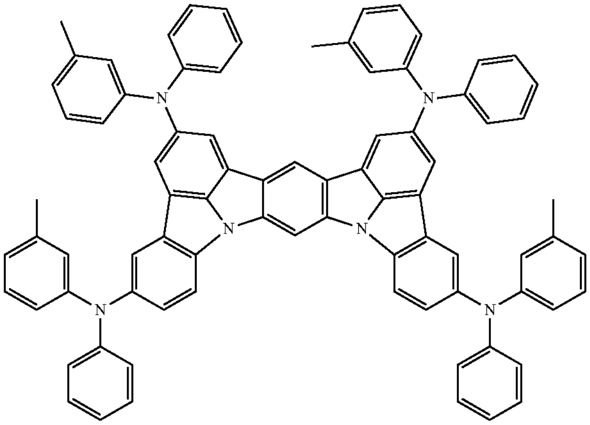

2

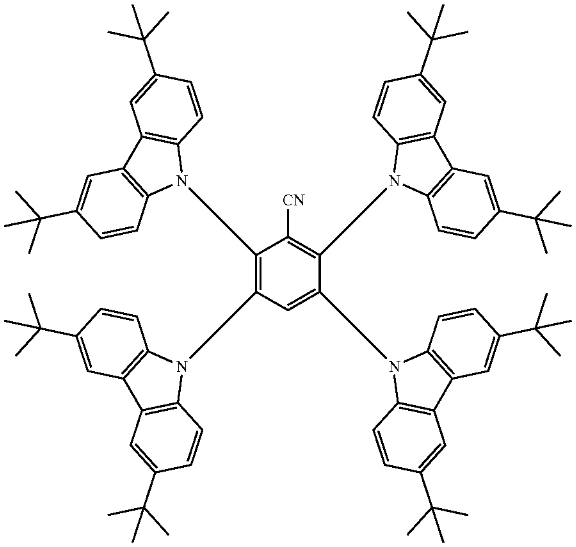

B

Example 3

A glass substrate on which an ITO stripe was formed to a thickness of 150 nm was formed.

Subsequently, F6-TCNNQ was deposited on the ITO electrode (anode) of the glass substrate to form a hole injection layer having a thickness of 10 nm.

HT1 was deposited on the hole injection layer to form a hole transport layer having a thickness of a 125 nm.

H-H104 was deposited on the hole transport layer to form an electron blocking layer having a thickness of 10 nm.

Compound 1, H-H104, and HE6-203 were co-deposited on the electron blocking layer at a ratio of 1.5 wt %:39.4 wt %:59.1 wt % to form an emission layer having a thickness of 40 nm.

HE6-203 was deposited on the emission layer to form a hole blocking layer having a thickness of 10 nm.

ET17 and LiQ were co-deposited at a weight ratio of 5:5 on the emission layer to form an electron transport layer having a thickness of 36 nm.

Next, LiQ was deposited on the electron transport layer to form an electron injection layer having a thickness of 3.5 nm.

Al was deposited on the electron injection layer to form a second electrode (cathode) having a thickness of 100 nm, and in a glove box under nitrogen atmosphere with a moisture concentration of 1 ppm or less and an oxygen concentration of 1 ppm or less, a glass sealing tube with a desiccant and an ultraviolet curable resin were used to seal the second electrode, thereby completing the manufacture of an organic light-emitting device.

F6-TCNNQ

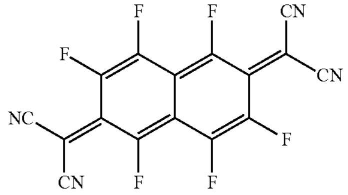

HT1

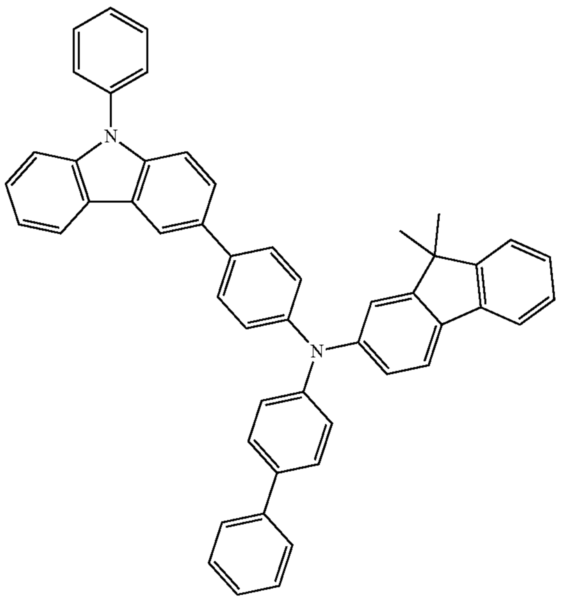

ET17

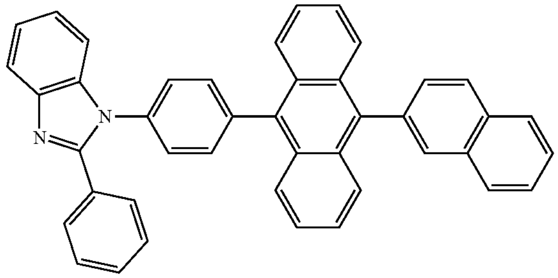

Evaluation of Example 7: Evaluation of Properties of Organic Light-Emitting Devices For the organic light-emitting device manufactured according to Example 3, CIEx, CIEy, emission peak wavelength, FWHM, and relative value (%) of Max EQE were evaluated, and results were shown in Table 10.

TABLE 10

| | Emission layer | | | | Emission peak | | Max EQE |
|---|---|---|---|---|---|---|---|
| | Host (weight ratio) | Dopant | CIEx | CIEy | wavelength (nm) | FWHM (nm) | (%) Host (weight ratio) |
| Example 3 | H-H104:HE6-203 = 4:6 | 1 | 0.138 | 0.123 | 463 | 30 | 15.58 |

Referring to Tables 9 and 10, it was confirmed that, as compared to the organic light-emitting device of Comparative Example 1, the organic light-emitting devices of Examples 1 to 3 exhibited luminescence having a narrow spectrum width with a blue wavelength region as a peak wavelength, so that blue luminescence with high color purity and excellent external quantum efficiency were identified.

As described above, according to the one or more embodiments, a condensed cyclic compound may be used in manufacturing a light-emitting device having high color purity and excellent luminescence efficiency, and such a light-emitting device may be used in manufacturing a high-quality electronic apparatus having excellent luminescence efficiency.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A condensed cyclic compound represented by Formula 1:

Formula 1

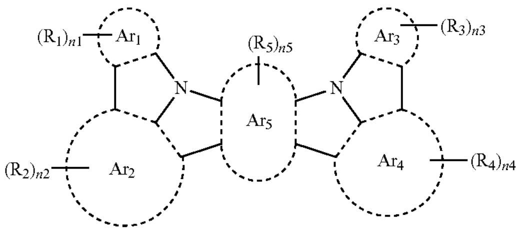

wherein, in Formula 1, $Ar_1$ to $Ar_5$ are each independently a $C_6$-$C_{60}$ carbocyclic group or a $C_1$-$C_{60}$ heterocyclic group, $R_1$ to $R_5$ are each independently hydrogen, deuterium, —F, —Cl, —Br, —I, a hydroxyl group, a cyano group, a nitro group, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$, wherein $R_1$(s) in the number of n1, $R_2$(s) in the number of n2, $R_3$(s) in the number of n3, $R_4$(s) in the number of n4, and $R_5$(s) in the number of n5 are respectively identical to or different from each other, n1 to n5 are each independently an integer from 0 to 8, the sum of n1 to n5 is 1 or more, two of two or more $R_1$(s) when n1 is 2 or more; two of two or more $R_2$(s) when n2 is 2 or more; two of two or more $R_3$(s) when n3 is 2 or more; two of two or more $R_4$(s) when n4 is 2 or more; and two of two or more $R_5$(s) when n5 is 2 or more are respectively optionally linked to each other or linked together via a single bond to form a $C_8$-$C_{60}$ polycyclic group unsubstituted or substituted with at least one $R_{10a}$, $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si$(Q_{11})(Q_{12})(Q_{13})$, —N$(Q_{11})(Q_{12})$, —B$(Q_{11})(Q_{12})$, —C(═O)$(Q_{11})$, —S(═O)$_2(Q_{11})$, —P(═O)$(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si$(Q_{21})(Q_{22})(Q_{23})$, —N$(Q_{21})(Q_{22})$, —B$(Q_{21})(Q_{22})$, —C(═O)$(Q_{21})$, —S(═O)$_2(Q_{21})$, —P(═O)$(Q_{21})(Q_{22})$, or any combination thereof; or —Si$(Q_{31})(Q_{32})(Q_{33})$, —N$(Q_{31})(Q_{32})$, —B$(Q_{31})(Q_{32})$, —C(═O)$(Q_{31})$, —S(═O)$_2(Q_{31})$, or —P(═O)$(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, wherein the condensed cyclic compound represented by Formula 1 has:

(i) a highest occupied molecular orbital (HOMO) energy level of about −6.0 eV or more and a lowest unoccupied molecular orbital (LUMO) energy level of about −2.5 eV or less, and the HOMO energy level and the LUMO energy level are values measured using a photoelectron spectrometer and a spectrophotometer, respectively, (ii) a difference between a singlet ($S_1$) energy level and a triplet ($T_1$) energy level of about 0.5 eV or less, or (iii) a combination thereof.

2. The condensed cyclic compound of claim 1, wherein $Ar_1$ to $Ar_5$ are each independently a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group.

3. The condensed cyclic compound of claim 1, wherein a group represented by

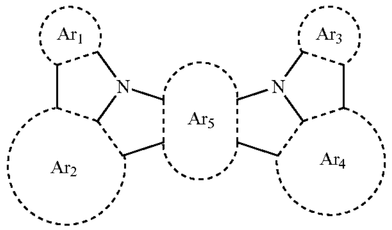

in Formula 1 is represented by one of Formulae 1-2-1 to 1-2-19:

(1-2-1)

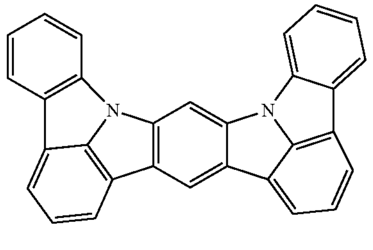

-continued
(1-2-2)
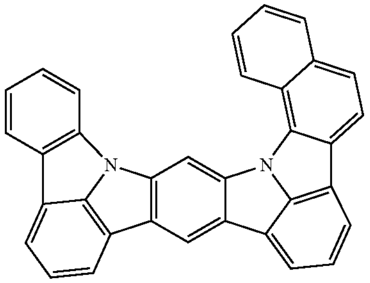
(1-2-3)
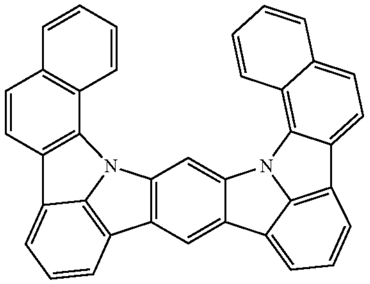
(1-2-4)
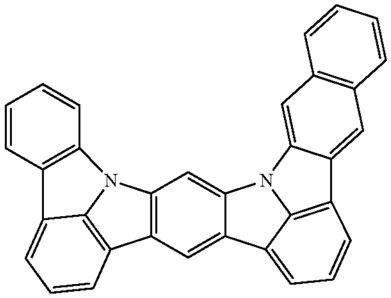
(1-2-5)
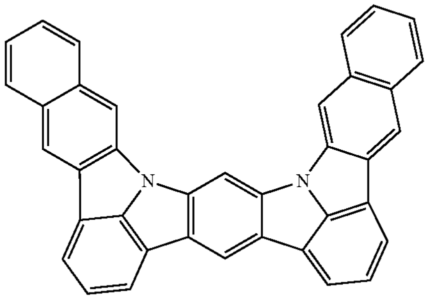
(1-2-6)
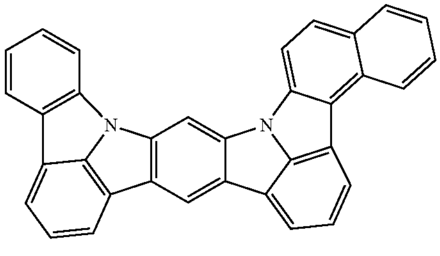
-continued
(1-2-7)
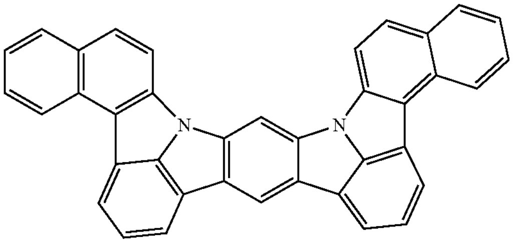
(1-2-8)
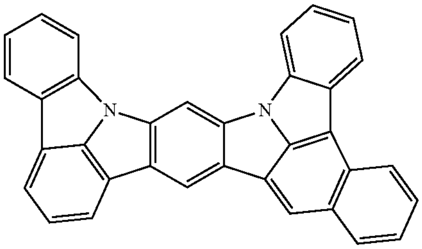
(1-2-9)
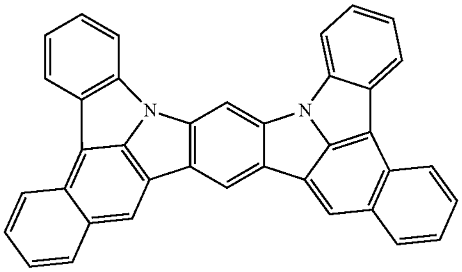
(1-2-10)
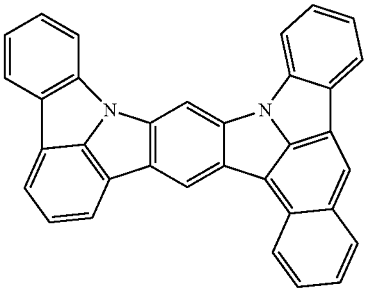
(1-2-11)
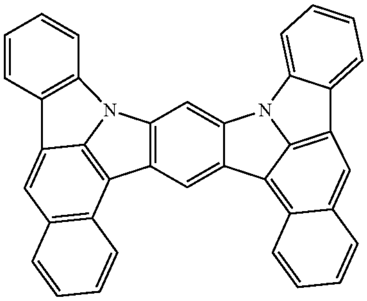

-continued (1-2-12)

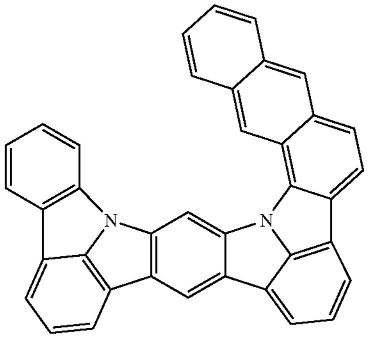

(1-2-13)

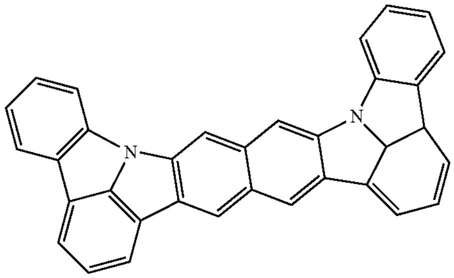

(1-2-14)

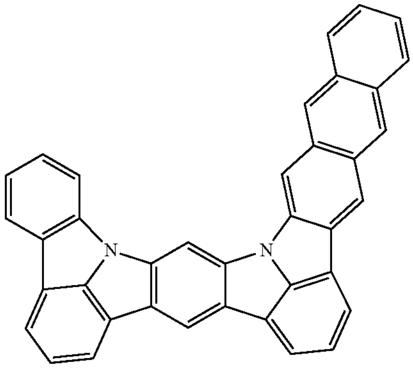

(1-2-15)

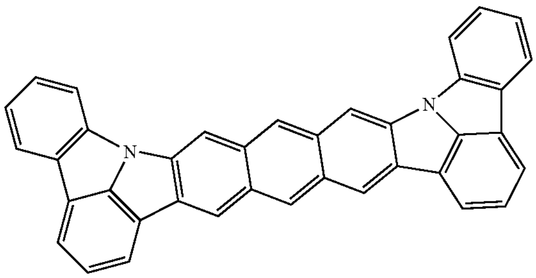

(1-2-16)

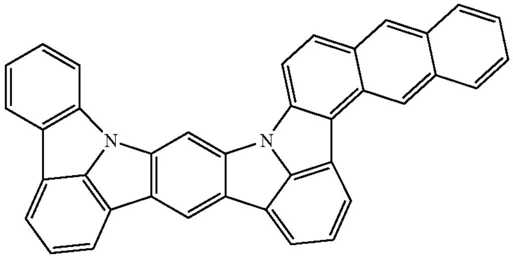

-continued (1-2-17)

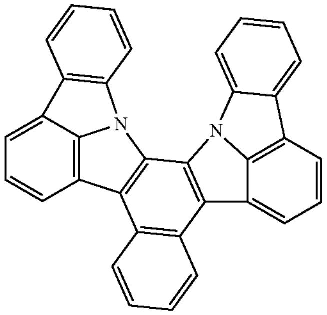

(1-2-18)

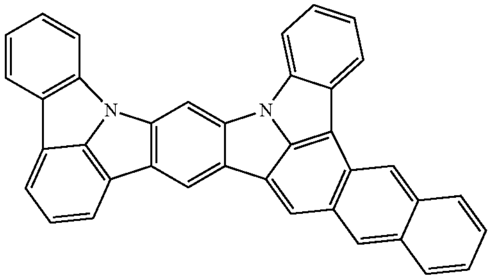

(1-2-19)

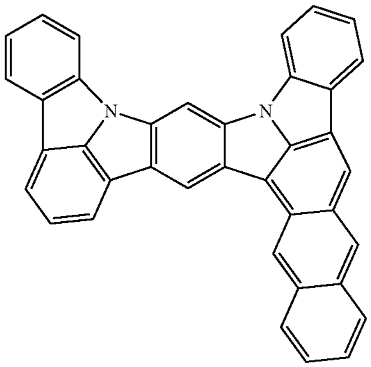

4. The condensed cyclic compound of claim 1, wherein $R_1$ to $R_5$ are each independently hydrogen, deuterium, —F, —Cl, —Br, —I, a hydroxyl group, a cyano group, a nitro group, a $C_3$-$C_{30}$ carbocyclic group unsubstituted or substituted with at least one $R_{10a}$, a $C_1$-$C_{30}$ heterocyclic group unsubstituted or substituted with at least one $R_{10a}$, a $C_6$-$C_{30}$ aryloxy group unsubstituted or substituted with at least one $R_{10a}$, a $C_6$-$C_{30}$ arylthio group unsubstituted or substituted with at least one $R_{10a}$, or —N($Q_1$)($Q_2$), and $Q_1$ and $Q_2$ are each independently: hydrogen; deuterium; —F; —Cl; —Br; —I; a hydroxyl group; a cyano group; a nitro group; a $C_1$-$C_{20}$ alkyl group; a $C_2$-$C_{20}$ alkenyl group; a $C_2$-$C_{20}$ alkynyl group; a $C_1$-$C_{20}$ alkoxy group; or a $C_3$-$C_{30}$ carbocyclic group or a $C_1$-$C_{30}$ heterocyclic group, each unsubstituted or substituted with deuterium, —F, a cyano group, a $C_1$-$C_{20}$ alkyl group, a $C_1$-$C_{20}$ alkoxy group, a phenyl group, a biphenyl group, or any combination thereof.

5. The condensed cyclic compound of claim 1, wherein at least one of $R_1$ to $R_4$ is —N($Q_1$)($Q_2$), and $Q_1$ and $Q_2$ are each independently a benzene group or a naphthalene group, each unsubstituted or substituted with deuterium, —F, a cyano group, a $C_1$-$C_{20}$ alkyl group, a $C_1$-$C_{20}$ alkoxy group, a phenyl group, a biphenyl group, or any combination thereof.

6. The condensed cyclic compound of claim 1, wherein the condensed cyclic compound represented by Formula 1 is represented by Formula 2:

Formula 2

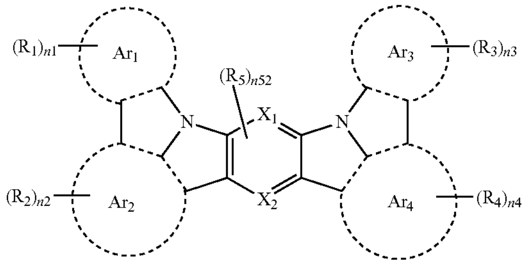

wherein, in Formula 2, $Ar_1$ to $Ar_4$, $R_1$ to $R_5$, and n1 to n4 are respectively the same as described in claim 1, $X_1$ and $X_2$ are each independently C or N, n52 is an integer from 0 to 2, the sum of n1 to n4 and n52 is 1 or more, and two of two or more $R_1$(s) when n1 is 2 or more; two of two or more $R_2$(s) when n2 is 2 or more; two of two or more $R_3$(s) when n3 is 2 or more; two of two or more $R_4$(s) when n4 is 2 or more; and two $R_5$(s) when n52 is 2 are respectively optionally linked to each other or linked together via a single bond to form a $C_8$-$C_{60}$ polycyclic group unsubstituted or substituted with at least one $R_{10a}$.

7. The condensed cyclic compound of claim 6, wherein each of $X_1$ and $X_2$ is C.

8. The condensed cyclic compound of claim 1, wherein the condensed cyclic compound represented by Formula 1 is represented by Formula 3:

Formula 3

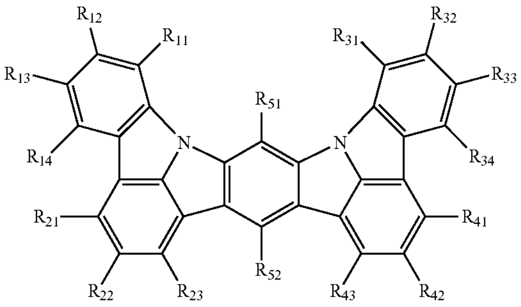

wherein, in Formula 3, $R_{11}$ to $R_{14}$ are respectively the same as described in connection with $R_1$ in claim 1, $R_{21}$ to $R_{23}$ are respectively the same as described in connection with $R_2$ in claim 1, $R_{31}$ to $R_{34}$ are respectively the same as described in connection with $R_3$ in claim 1, $R_{41}$ to $R_{43}$ are respectively the same as described in connection with $R_4$ in claim 1, $R_{51}$ and $R_{52}$ are respectively the same as described in connection with $R_5$ in claim 1, wherein at least one of $R_{11}$ to $R_{14}$, $R_{21}$ to $R_{23}$, $R_{31}$ to $R_{34}$, $R_{41}$ to $R_{43}$, $R_{51}$, and $R_{52}$ is not hydrogen, and two of $R_{11}$ to $R_{14}$, $R_{21}$ to $R_{23}$, $R_{31}$ to $R_{34}$, $R_{41}$ to $R_{43}$, $R_{51}$, and $R_{52}$ are optionally linked to each other or linked together via a single bond to form a $C_8$-$C_{60}$ polycyclic group unsubstituted or substituted with at least one $R_{10a}$.

9. The condensed cyclic compound of claim 8, wherein at least one of $R_{13}$, $R_{22}$, $R_{33}$, and $R_{42}$ is not hydrogen.

10. The condensed cyclic compound of claim 1, wherein the condensed cyclic compound represented by Formula 1 is one of Compounds 1 to 24:

1

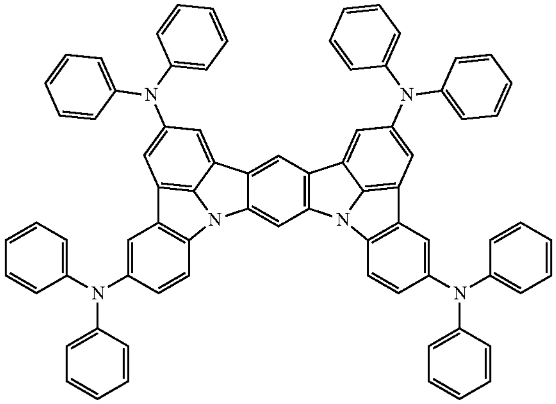

2

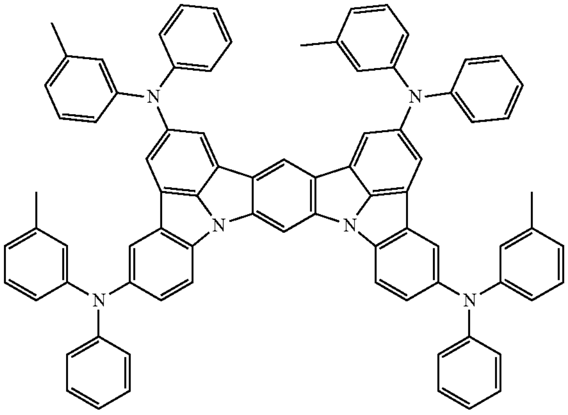

-continued
3
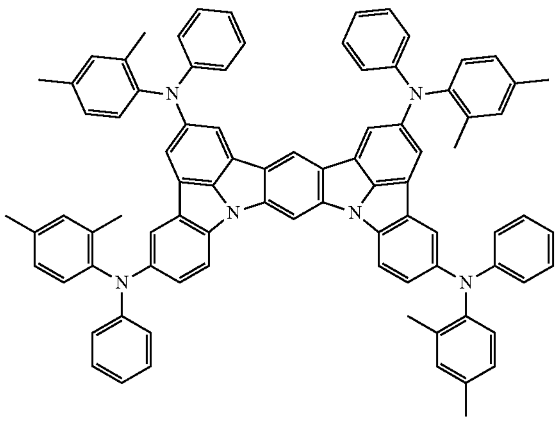
4
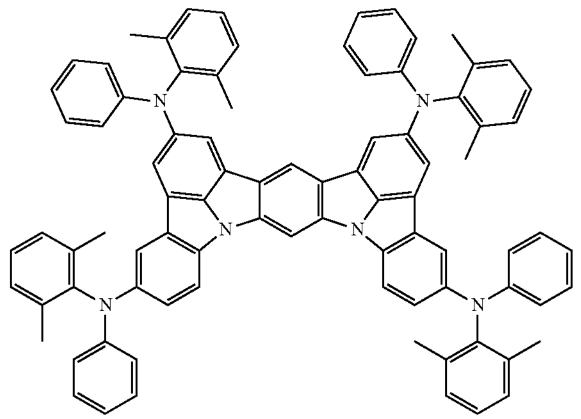
5
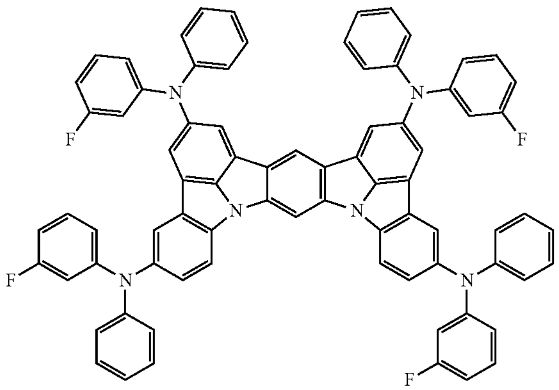
6
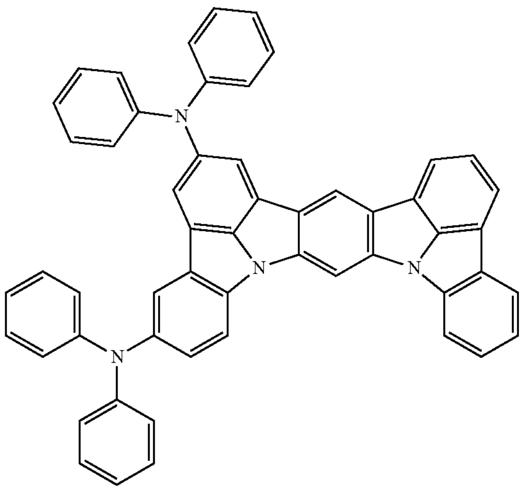
7
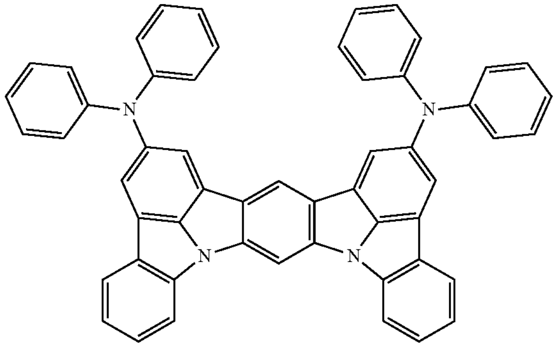
8
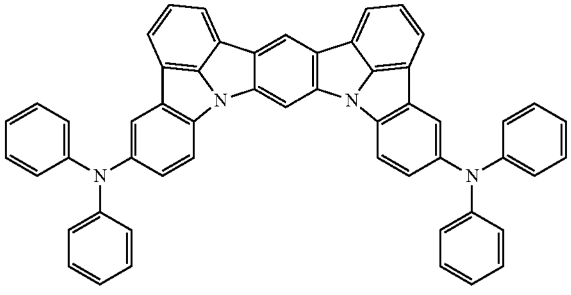

-continued
9
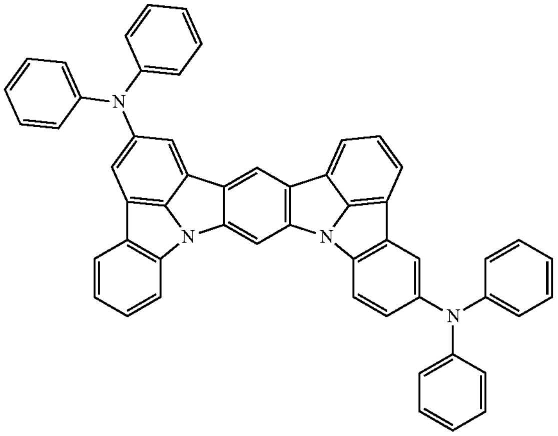
10
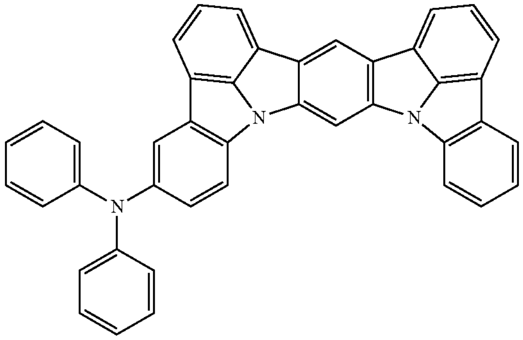
11
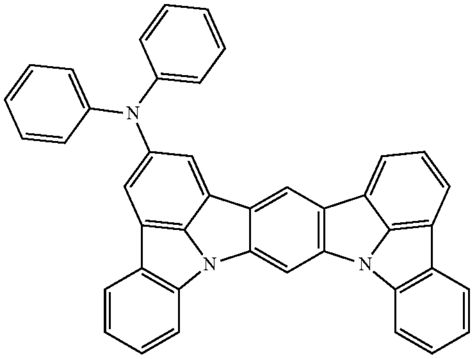
12
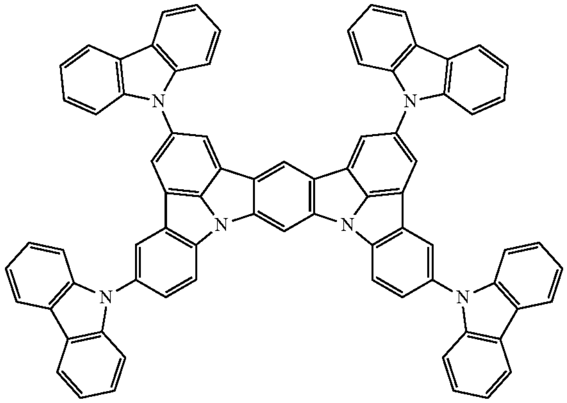
13
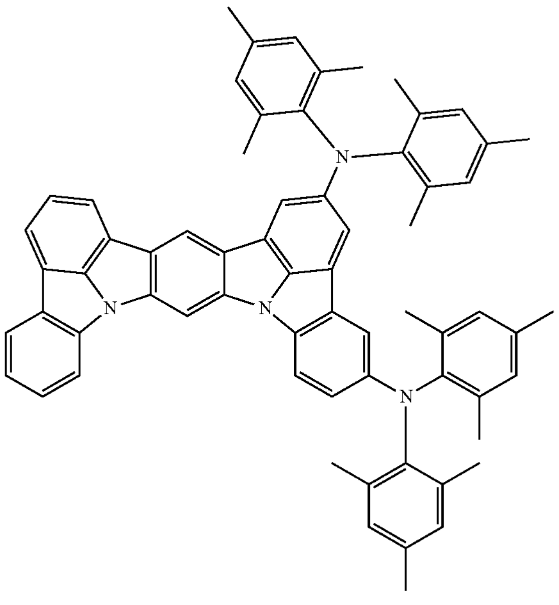
14
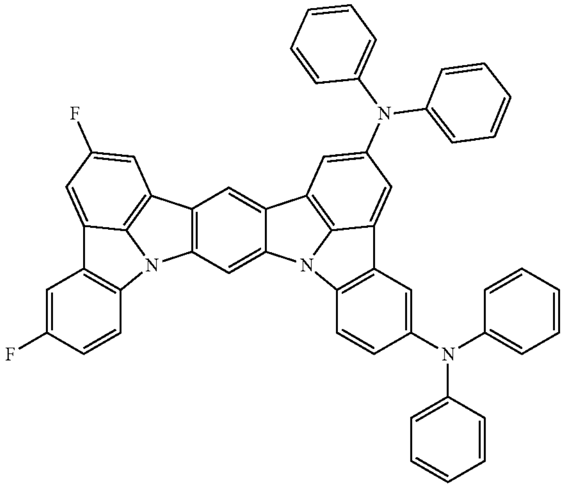

-continued
15
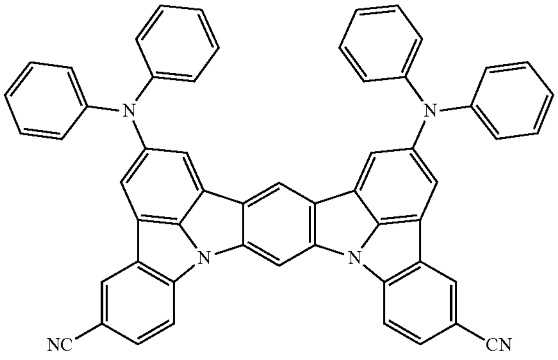
16
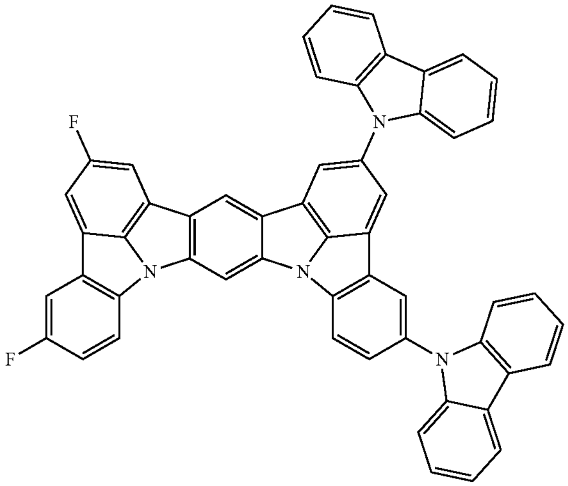
17
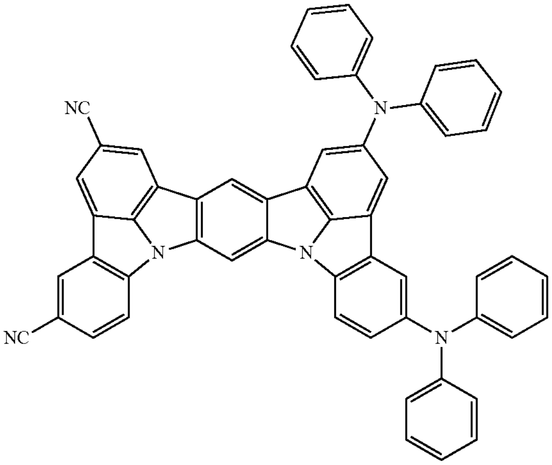
18
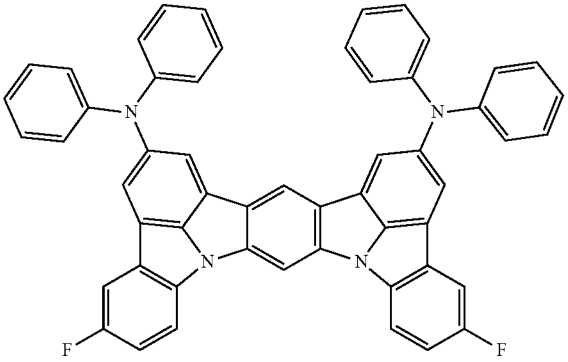
19
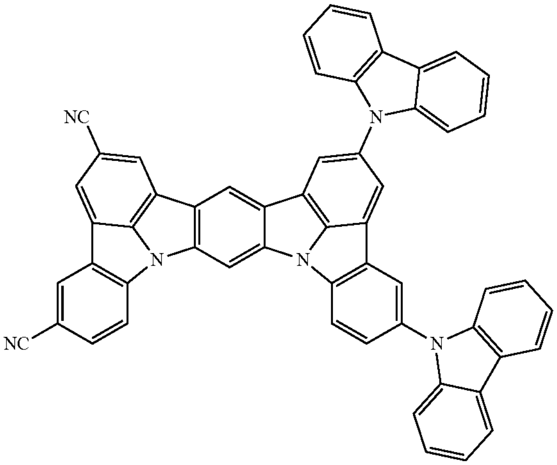
20
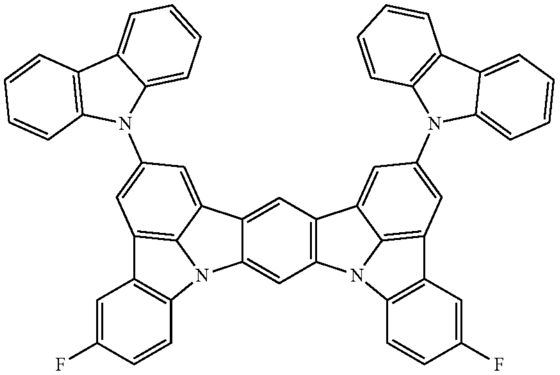

-continued
21
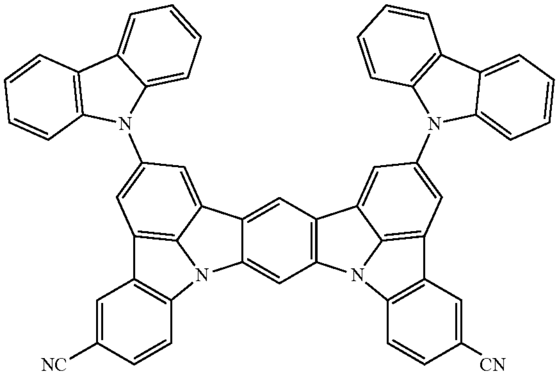
22
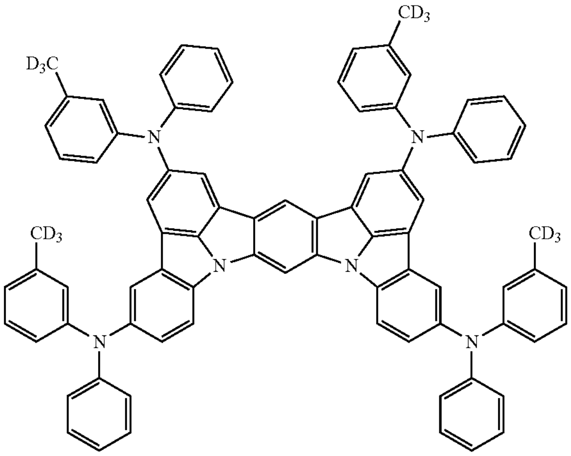
23
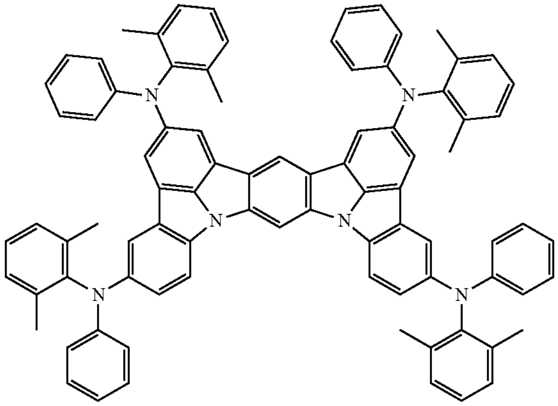
24
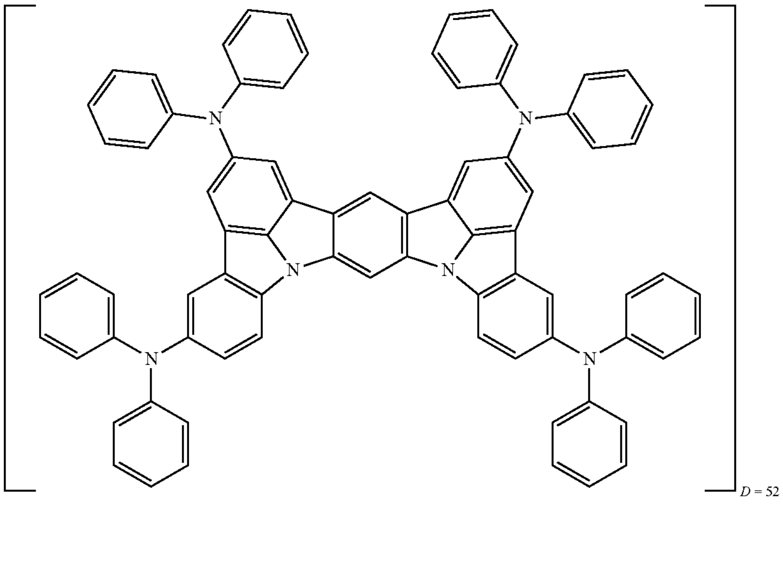

wherein D in Compound 22 is deuterium, and

"D=52" in Compound 24 means that all 52 hydrogen atoms in Compound 24 are substituted with deuterium atoms.

11. The condensed cyclic compound of claim 1, wherein the condensed cyclic compound emits blue light or cyan light.

12. An organic light-emitting device comprising:

a first electrode;

a second electrode; and an interlayer arranged between the first electrode and the second electrode and comprising an emission layer, wherein the interlayer comprises at least one condensed cyclic compound of claim 1.

13. The organic light-emitting device of claim 12, wherein the first electrode is an anode, the second electrode is a cathode, the interlayer further comprises a hole transport region between the first electrode and the emission layer and an electron transport region between the emission layer and the second electrode, the hole transport region comprises a hole injection layer, a hole transport layer, an emission auxiliary layer, an electron blocking layer, or any combination thereof, and the electron transport region comprises a hole blocking layer, an electron transport layer, an electron injection layer, or any combination thereof.

14. The organic light-emitting device of claim 12, wherein the emission layer comprises the at least one condensed cyclic compound.

15. The organic light-emitting device of claim 14, wherein the at least one condensed cyclic compound comprised in the emission layer acts as a delayed fluorescence dopant, such that delayed fluorescence is emitted from the emission layer.

16. The organic light-emitting device of claim 14, wherein the emission layer further comprises a host, and the host is represented by Formula 4:

Formula 4

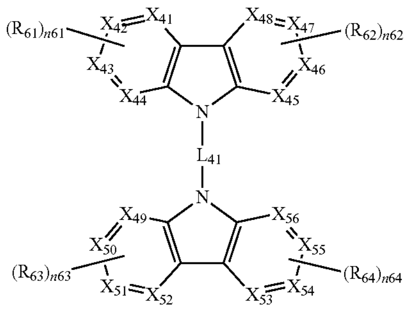

wherein, in Formula 4, $SX_{41}$ to $X_{56}$ are each independently C or N, $L_{41}$ is a single bond, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, $R_{61}$ to $R_{64}$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —C(═O)($Q_1$), —S(═O)$_2$($Q_1$), or —P(═O)($Q_1$)($Q_2$), n61 to n64 are each independently an integer from 0 to 4, $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(═O)($Q_{11}$), —S(═O)$_2$($Q_{11}$), —P(═O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(═O)($Q_{21}$), —S(═O)$_2$($Q_{21}$), —P(═O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), or —P(═O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

17. An electronic apparatus comprising the organic light-emitting device of claim 12.

18. The electronic apparatus of claim 17, further comprising a thin-film transistor, wherein the thin-film transistor comprises a source electrode and a drain electrode, and the first electrode of the light-emitting device is electrically connected to at least one of the source electrode and the drain electrode of the thin-film transistor.

* * * * *